(12) United States Patent
Ammann et al.

(10) Patent No.: US 12,410,183 B2
(45) Date of Patent: *Sep. 9, 2025

(54) SARS-COV2 MAIN PROTEASE INHIBITORS

(71) Applicant: Gilead Sciences, Inc., Foster City, CA (US)

(72) Inventors: Stephen E. Ammann, Foster City, CA (US); Xinpei Cai, San Mateo, CA (US); Eda Y. Canales, San Mateo, CA (US); Weng K. Chang, San Lorenzo, CA (US); Gregory F. Chin, San Francisco, CA (US); Henok H. Kinfe, Foster City, CA (US); Scott E. Lazerwith, San Francisco, CA (US); Jessica L McKinley, Foster City, CA (US); Michael R. Mish, Foster City, CA (US); Devan Naduthambi, San Bruno, CA (US); Jason K. Perry, San Francisco, CA (US); Kevin X Rodriguez, San Mateo, CA (US); Scott D. Schroeder, Union City, CA (US); Christopher J. Swank, San Mateo, CA (US); Joshua J. Van Veldhuizen, Seattle, WA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/743,475

(22) Filed: Jun. 14, 2024

(65) Prior Publication Data
US 2025/0042915 A1 Feb. 6, 2025

Related U.S. Application Data

(63) Continuation of application No. 18/376,159, filed on Oct. 3, 2023, now Pat. No. 12,091,420, which is a (Continued)

(51) Int. Cl.
| | |
|---|---|
| *C07D 495/04* | (2006.01) |
| *A61P 31/14* | (2006.01) |
| *C07D 401/04* | (2006.01) |
| *C07D 401/14* | (2006.01) |
| *C07D 405/14* | (2006.01) |
| *C07D 409/14* | (2006.01) |
| *C07D 413/14* | (2006.01) |
| *C07D 417/14* | (2006.01) |
| *C07D 471/04* | (2006.01) |
| *C07D 487/04* | (2006.01) |
| *C07D 487/10* | (2006.01) |

(Continued)

(52) U.S. Cl.
CPC ............ *C07D 495/04* (2013.01); *A61P 31/14* (2018.01); *C07D 401/04* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07D 487/04* (2013.01); *C07D 487/10* (2013.01); *C07D 491/107* (2013.01); *C07D 491/113* (2013.01); *C07D 498/04* (2013.01); *C07D 513/04* (2013.01); *C07D 519/00* (2013.01)

(58) Field of Classification Search
CPC .. C07D 495/04; C07D 401/04; C07D 401/14; C07D 405/14; C07D 409/14; C07D 413/14; C07D 417/14; C07D 471/04; C07D 487/04; C07D 487/10; C07D 491/107; C07D 491/113; C07D 498/04; C07D 513/04; C07D 519/00; A61P 31/14
USPC ....................................... 514/260.1
See application file for complete search history.

(56) References Cited

U.S. PATENT DOCUMENTS

| | | |
|---|---|---|
| 5,284,661 A | 2/1994 | Morimoto et al. |
| 8,969,557 B2 | 3/2015 | Harriman et al. |

(Continued)

FOREIGN PATENT DOCUMENTS

| | | |
|---|---|---|
| CN | 111793078 | 2/2022 |
| CN | 111909168 | 2/2022 |

(Continued)

OTHER PUBLICATIONS

U.S. Appl. No. 18/365,919, filed Aug. 4, 2023, Ammann et al.
(Continued)

*Primary Examiner* — Kristin A Vajda
(74) *Attorney, Agent, or Firm* — Fish & Richardson P.C.

(57) ABSTRACT

The present disclosure relates to compounds of Formula I:

and pharmaceutically acceptable salts thereof, pharmaceutical compositions thereof, useful in the treatment of treating viral infections, for example, coronaviridae infections.

25 Claims, No Drawings

Related U.S. Application Data continuation of application No. 18/365,919, filed on Aug. 4, 2023.

(60) Provisional application No. 63/508,350, filed on Jun. 15, 2023, provisional application No. 63/486,156, filed on Feb. 21, 2023, provisional application No. 63/482,750, filed on Feb. 1, 2023, provisional application No. 63/476,359, filed on Dec. 20, 2022, provisional application No. 63/375,522, filed on Sep. 13, 2022, provisional application No. 63/370,629, filed on Aug. 5, 2022.

(51) Int. Cl.
*C07D 491/107* (2006.01)
*C07D 491/113* (2006.01)
*C07D 498/04* (2006.01)
*C07D 513/04* (2006.01)
*C07D 519/00* (2006.01)

(56) References Cited

U.S. PATENT DOCUMENTS

| | | |
|---|---|---|
| 9,453,026 B2 | 9/2016 | Harriman et al. |
| 9,944,655 B2 | 4/2018 | Harriman et al. |
| 10,179,793 B2 | 1/2019 | Ghosh et al. |
| 10,472,374 B2 | 11/2019 | Bhat et al. |
| 12,091,420 B2 * | 9/2024 | Ammann ............. C07D 513/04 |
| 2023/0108588 A1 | 4/2023 | Nieman et al. |

FOREIGN PATENT DOCUMENTS

| | | |
|---|---|---|
| CN | 111925379 | 2/2022 |
| CN | 112047957 | 2/2022 |
| CN | 112142757 | 2/2022 |
| CN | 114031626 | 2/2022 |
| CN | 111440188 | 3/2022 |
| CN | 111875614 | 4/2022 |
| CN | 113754679 | 4/2023 |
| CN | 115490681 | 4/2023 |
| CN | 115504968 | 4/2023 |
| CN | 115894443 | 4/2023 |
| CN | 115894504 | 4/2023 |
| CN | 116041349 | 5/2023 |
| CN | 116265440 | 6/2023 |
| CN | 116284133 | 6/2023 |
| CN | 116514784 | 8/2023 |
| CN | 116514795 | 8/2023 |
| CN | 116554153 | 8/2023 |
| CN | 116621817 | 9/2023 |
| CN | 116768867 | 9/2023 |
| CN | 116891484 | 10/2023 |
| CN | 117069705 | 11/2023 |
| CN | 117088869 | 11/2023 |
| CN | 117126141 | 11/2023 |
| CN | 117402185 | 1/2024 |
| CN | 117430590 | 1/2024 |
| CN | 117466873 | 1/2024 |
| IN | 202341051234 | 9/2023 |
| KR | 20230174613 | 12/2023 |
| WO | WO1995028405 | 10/1995 |
| WO | WO2013071169 | 5/2013 |
| WO | WO2018213364 | 11/2018 |
| WO | WO2021176088 | 9/2021 |
| WO | WO2021228762 | 11/2021 |
| WO | WO2022067566 | 4/2022 |
| WO | WO2022067573 | 4/2022 |
| WO | WO2022150962 | 7/2022 |
| WO | WO2022224223 | 10/2022 |
| WO | WO2022240277 | 11/2022 |
| WO | WO2022251647 | 12/2022 |
| WO | WO2022266368 | 12/2022 |
| WO | WO2023002409 | 1/2023 |
| WO | WO2023004291 | 1/2023 |
| WO | WO2023283831 | 1/2023 |
| WO | WO2023027198 | 3/2023 |
| WO | WO2023030459 | 3/2023 |
| WO | WO2023033098 | 3/2023 |
| WO | WO2023034854 | 3/2023 |
| WO | WO2023036140 | 3/2023 |
| WO | WO2023042879 | 3/2023 |
| WO | WO2023054292 | 4/2023 |
| WO | WO2023054732 | 4/2023 |
| WO | WO2023054759 | 4/2023 |
| WO | WO2023055702 | 4/2023 |
| WO | WO2023065606 | 4/2023 |
| WO | WO2023065667 | 4/2023 |
| WO | WO2023065683 | 4/2023 |
| WO | WO2023095860 | 6/2023 |
| WO | WO2023114428 | 6/2023 |
| WO | WO2023122260 | 6/2023 |
| WO | WO2023155337 | 8/2023 |
| WO | WO2023155830 | 8/2023 |
| WO | WO2023158785 | 8/2023 |
| WO | WO2023165459 | 9/2023 |
| WO | WO2023169572 | 9/2023 |
| WO | WO2023173708 | 9/2023 |
| WO | WO2023195529 | 10/2023 |
| WO | WO2023195530 | 10/2023 |
| WO | WO2023208200 | 11/2023 |
| WO | WO2023226679 | 11/2023 |
| WO | WO2023227117 | 11/2023 |
| WO | WO2023227118 | 11/2023 |
| WO | WO2024008909 | 1/2024 |
| WO | WO2024009120 | 1/2024 |
| WO | WO2024010585 | 1/2024 |
| WO | WO2024017178 | 1/2024 |

OTHER PUBLICATIONS

Yang et al., "Bench-to-bedside: Innovation of small molecule anti-SARS-COV-2 drugs in China," European Journal of Medicinal Chemistry, May 2023, vol. 257, 43 pages.

Zheng et al., "Assessment and sero-diagnosis for coronaviruses with risk of human spillover", Emerging Microbes and Infections, Mar. 2023, 12:2225932, 10 pages.

International Search Report and Written Opinion in International Appln. No. PCT/US2023/071744, mailed on Nov. 29, 2023, 15 pages.

Office Action in U.S. Apln. No. 18/376, 159, dated Dec. 4, 2023, 6 pages.

* cited by examiner

SARS-COV2 MAIN PROTEASE INHIBITORS

CROSS REFERENCE TO RELATED APPLICATIONS

This application is a continuation of U.S. Ser. No. 18/376,159, filed Oct. 3, 2023, which is a continuation of U.S. Ser. No. 18/365,919, filed Aug. 4, 2023, which claims priority to U.S. Provisional Patent Application No. 63/370,629 filed on Aug. 5, 2022, U.S. Provisional Patent Application No. 63/375,522 filed on Sep. 13, 2022, U.S. Provisional Patent Application No. 63/476,359 filed on Dec. 20, 2022, U.S. Provisional Patent Application No. 63/482,750 filed on Feb. 1, 2023, U.S. Provisional Patent Application No. 63/486,156 filed on Feb. 21, 2023, and U.S. Provisional Patent Application No. 63/508,350 filed on Jun. 15, 2023, each of which is hereby incorporated by reference in its entirety.

BACKGROUND

Coronaviruses, named for the crown-like spikes on their surfaces, infect mostly bats, pigs and small mammals. They mutate easily and can jump from animals to humans, and from one human to another. In recent years, they have become a growing player in infectious-disease outbreaks world-wide. There is a need for compounds and methods for treating viral infections, for example coronaviridae infections. The present disclosure addresses these and other needs.

SUMMARY

In one embodiment, the present disclosure provides a compound formula (I):

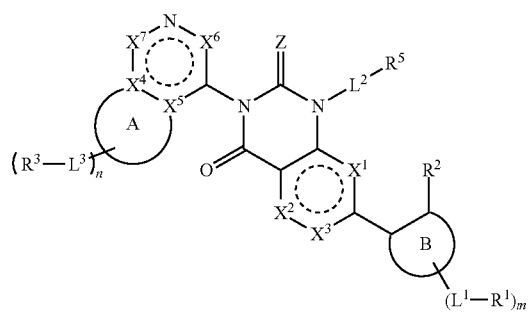

I or a pharmaceutically acceptable salt thereof, wherein ring  is $C_{6-10}$ aryl or 5- to 10-membered heteroaryl;

each $L^1$ is independently a bond, —O—, —($C_{1-6}$ alkyl)O—, —O($C_{1-6}$ alkyl)-, —$C_{1-6}$ alkyl-O($C_{1-6}$ alkyl)-, —C(O)—, —N($R^L$)C(O)—, —C(O)N($R^L$)—, —($C_{1-6}$ alkyl)($R^L$)NC(O)—, —($C_{1-6}$ alkyl)C(O)N($R^L$)—, —N($R^L$)C(O)($C_{1-6}$ alkyl)-, —C(O)N($R^L$)($C_{1-6}$ alkyl)-, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —S(O)$_2$—, —S(O)$_2$N($R^L$)—, —N($R^L$)—S(O)$_2$—, —($C_{1-6}$ alkyl)S(O)$_2$N($R^L$)—, —($C_{1-6}$ alkyl)N($R^L$)S(O)$_2$—, —S(O)$_2$N($R^L$)($C_{1-6}$ alkyl)-, —N($R^L$)S(O)$_2$($C_{1-6}$ alkyl)-, —($C_{1-6}$ alkyl)S(O)$_2$N($R^L$)($C_{1-6}$ alkyl)-, or —($C_{1-6}$ alkyl)N($R^L$)S(O)$_2$($C_{1-6}$ alkyl)-;

each $R^1$ is independently halogen, —OH, —CN, $C_{1-6}$ alkyl, —CN, —C(O)NH$_2$, $C_{2-6}$ alkenyl, $C_{2-6}$ alkynyl, $C_{1-6}$ alkoxy, $C_{3-8}$ cycloalkyl, $C_6$ aryl, 5- to 12-membered heteroaryl, or 4- to 10-membered heterocyclyl, wherein each alkyl, alkenyl, alkynyl, alkoxy, cycloalkyl, aryl, heteroaryl, and heterocyclyl is optionally substituted with one to four $R^{1a}$;

alternatively, two $R^1$ taken together with the atoms of ring  to which they are attached form 5- to 10-membered heterocyclyl;

each $R^{1a}$ is independently $C_{1-6}$ alkyl, halogen, $C_{3-8}$ cycloalkyl, 4- to 10-membered heterocyclyl, $C_6$ aryl, 5- to 10-membered heteroaryl, oxo. —OH, —CN, —NH$_2$, —O($C_{1-6}$ alkyl), —O($C_{3-8}$ cycloalkyl), —O(5- to 10-membered heterocyclyl), —O($C_6$ aryl), —O(5- to 10-membered heteroaryl), —NH($C_{1-6}$ alkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{3-8}$ cycloalkyl)$_2$, —N(5- to 10-membered heterocyclyl)$_2$, —N($C_6$ aryl)$_2$, —N(5- to 10-membered heteroaryl)$_2$, —N($C_{1-6}$ alkyl)($C_{3-8}$ cycloalkyl), —N($C_{1-6}$ alkyl)(5- to 10-membered heterocyclyl), —N($C_{1-6}$ alkyl)($C_6$ aryl), —N($C_{1-6}$ alkyl)(5- to 10-membered heteroaryl), —C(O)(5- to 10-membered heterocyclyl), —C(O)(5- to 10-membered heteroaryl), —C(O)O($C_{1-6}$ alkyl), —C(O)O($C_{3-8}$ cycloalkyl), —C(O)O(5- to 10-membered heterocyclyl), —C(O)O($C_6$ aryl), —C(O)O(5- to 10-membered heteroaryl), —C(O)NH$_2$, —C(O)NH($C_{1-6}$ alkyl), —C(O)NH($C_{3-8}$ cycloalkyl), —C(O)NH(5- to 10-membered heterocyclyl), —C(O)NH($C_6$ aryl), —C(O)NH(5- to 10-membered heteroaryl), —C(O)N($C_{1-6}$ alkyl)$_2$, —C(O)N($C_{3-8}$ cycloalkyl)$_2$, —C(O)N(5- to 10-membered heterocyclyl)$_2$, —C(O)N($C_6$ aryl)$_2$, —C(O)N(5- to 10-membered heteroaryl)$_2$, —NHC(O)($C_{1-6}$ alkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), —NHC(O)NH($C_{3-8}$ cycloalkyl), —NHC(O)NH(5- to 10-membered heterocyclyl), —NHC(O)NH($C_6$ aryl), —NHC(O)NH(5- to 10-membered heteroaryl), —NHS(O)($C_{1-6}$ alkyl), —N($C_{1-6}$ alkyl)(S(O)($C_{1-6}$ alkyl), —S(O)$_2$($C_{1-6}$ alkyl), —S(O)$_2$($C_{3-8}$ cycloalkyl), —S(O)$_2$(5- to 10-membered heterocyclyl), —S(O)$_2$($C_6$ aryl), —S(O)$_2$(5- to 10-membered heteroaryl), —S(O)(NH)($C_{1-6}$ alkyl), —S(O)$_2$NH($C_{1-6}$ alkyl), or —S(O)$_2$N($C_{1-6}$ alkyl)$_2$, wherein each alkyl, cycloalkyl, heterocyclyl, aryl, and heteroaryl is optionally substituted with one to three $R^{1b}$;

each $R^{1b}$ is independently $C_{1-6}$ alkyl, $C_{1-6}$ haloalkyl, halogen, oxo, —OH, —NH$_2$. CO$_2$H—O($C_{1-6}$ alkyl), —O($C_{1-6}$ haloalkyl), —O($C_{3-8}$ cycloalkyl), —O(5- to 10-membered heterocyclyl), —O($C_6$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)(C$_6$ aryl), —NHC(O)(5- to 10-membered heteroaryl), —NHC(O)O(C$_{1-6}$ alkyl), —NHC(O)O(C$_{1-6}$ haloalkyl), —NHC(O)O(C$_{2-6}$ alkynyl), —NHC(O)O(C$_{3-8}$ cycloalkyl), —NHC(O)O(5- to 10-membered heterocyclyl), —NHC(O)O (C$_6$ aryl), —NHC(O)O(5- to 10-membered heteroaryl), —NHC(O)NH(C$_{1-6}$ alkyl), S(O)$_2$(C$_{1-6}$ alkyl), —S(O)$_2$(C$_{1-6}$ haloalkyl), —S(O)$_2$(C$_{3-8}$ cycloalkyl), —S(O)$_2$(5- to 10-membered heterocyclyl), —S(O)$_2$(C$_6$ aryl), —S(O)$_2$(5- to 10-membered heteroaryl), —S(O)(NH)(C$_{1-6}$ alkyl), —S(O)$_2$NH (C$_{1-6}$ alkyl), or —S(O)$_2$N(C$_{1-6}$ alkyl)$_2$;

m is an integer from 0 to 3;

R$^2$ is hydrogen. C$_{1-3}$ alkyl, C$_{1-3}$ haloalkyl, cyclopropyl, C$_{1-3}$ alkoxy, —O(C$_{1-3}$ haloalkyl), —O(cyclopropyl), halogen, or —CN;

X$^1$ is S, N, or C(R$^{x1}$);

X$^2$ is S, N, or C(R$^{x2}$);

X$^3$ is N or C(R$^{x3}$), provided that X$^1$ and X$^2$ are not S;

alternatively, X$^3$ is a bond, wherein one of X$^1$ and X$^2$ is S;

each R$^{x1}$, R$^{x2}$, and R$^{x3}$ is independently hydrogen, halogen, C$_{1-3}$ alkyl, C$_{1-3}$ haloalkyl, O C$_{1-3}$ haloalkyl, C$_{1-3}$ alkoxy, cyclopropyl, or O-cyclopropyl;

ring (A) taken together with X$^4$ and X$^5$ is C$_6$ aryl, 5- to 6-membered heteroaryl, C$_{5-10}$ cycloalkyl, or 5- to 10-membered heterocyclyl,
wherein each X$^4$ and X$^5$ is independently N or C;

alternatively, ring (A) is absent, wherein X$^4$ is N or C-L$^{x4}$-R$^{x4}$, and X$^5$ is N or C-L$^{x5}$-R$^{x5}$;

each L$^{x4}$ and L$^{x5}$ is independently a bond, —(C$_{1-6}$ alkyl)O—, —(C$_{1-6}$ alkyl)N(R$^L$)C(O)—, —(C$_{1-6}$ alkyl)C(O)N(R$^L$)—, —(C$_{1-6}$ alkyl)N(R$^L$)C(O)(C$_{1-6}$alkyl)-, —(C$_{1-6}$ alkyl)C(O)N(R$^L$)(C$_{1-6}$ alkyl)-, —(C$_{1-6}$ alkyl), —(C$_{1-6}$ alkyl)N(R$^L$)S(O)$_2$—, —N(R$^L$)S(O)$_2$—, —C(O)—, —(C$_{1-6}$ alkyl)C(O)—, or —N(R$^L$)C(O)—;

each R$^{x4}$ and R$^{x5}$ is independently hydrogen, halogen, hydroxy, —CN, C$_{1-6}$ alkyl, C$_{2-6}$ alkynyl, C$_{1-6}$ alkoxy, C$_{3-8}$ cycloalkyl, 4- to 10-membered heterocyclyl, 5- to 10-membered heteroaryl, —NH$_2$, —NH(C$_{1-6}$ alkyl), —N(C$_{1-6}$ alkyl)$_2$, —O(C$_{1-6}$ alkyl), or —OC$_{3-8}$ cycloalkyl;
wherein each alkyl, alkynyl, alkoxy, cycloalkyl, and heterocyclyl is optionally substituted with one to four R$^1$;

each R$^{4a}$ is independently C$_{1-6}$ alkyl, C$_{1-6}$ haloalkyl, halogen, C$_{3-8}$ cycloalkyl, 4- to 10-membered heterocyclyl, C$_6$ aryl, 5- to 10-membered heteroaryl, oxo, —OH, —CN, —NH$_2$, —O(C$_{1-6}$ alkyl), —O(C$_{1-6}$ haloalkyl), —O(C$_{3-8}$ cycloalkyl), —O(5- to 10-membered heterocyclyl), —O(C$_{6-10}$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(C$_6$ aryl), —NH(5- to 10-membered heteroaryl), —N(C$_{1-6}$ alkyl)$_2$, —N(C$_{1-6}$ haloalkyl)$_2$, —N(C$_{3-8}$ cycloalkyl)$_2$, —N(C$_{1-6}$ alkyl)(C$_{1-6}$ haloalkyl), —N(C$_{1-6}$ alkyl)(C$_{3-8}$ cycloalkyl), —N(C$_{1-6}$ alkyl)(5- to 10-membered heterocyclyl), —N(C$_{1-6}$ alkyl)(C$_6$ aryl), —N(C$_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH(C$_{1-6}$ alkyl), —C(O)NH(C$_{1-6}$ haloalkyl), —C(O)NH(C$_{3-8}$ cycloalkyl), —C(O)NH (5- to 10-membered heterocyclyl), —C(O)NH(C$_6$ aryl), —C(O)NH(5- to 10-membered heteroaryl), —C(O)N(C$_{1-6}$ alkyl)$_2$, —C(O)N(C$_{1-6}$ haloalkyl)$_2$, —C(O)N(C$_{3-8}$ cycloalkyl)$_2$, —NHC(O)(C$_{1-4}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(C$_{1-6}$ aryl), —NHC(O)(5- to 10-membered heteroaryl), —NHC(O)O(C$_{1-6}$ alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(C$_6$ aryl), —NHC(O)O(5- to 10-membered heteroaryl), —NHC(O)NH(C$_{1-6}$ alkyl), —NHC(O)NH(C$_{1-6}$ haloalkyl), —NHC(O)NH(C$_{3-8}$ cycloalkyl), —NHC(O)NH(5- to 10-membered heterocyclyl), —NHC(O)NH(C$_6$ aryl), —NHC(O)NH(5- to 10-membered heteroaryl), —S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)$_2$NH(C$_{1-6}$ alkyl), or —S(O)$_2$N(C$_{1-6}$ alkyl)$_2$,
wherein each alkyl, cycloalkyl, heterocyclyl, aryl, and heteroaryl is optionally substituted with one to three R$^1$;

each R$^{4b}$ is independently C$_{1-6}$ alkyl, C$_{1-6}$ haloalkyl, C$_{3-6}$ cycloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_6$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(5- to 10-membered heteroaryl), —N(C$_{1-6}$ alkyl)$_2$, —N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(5- to 10-membered heteroaryl), —NHC(O)O(C$_{1-6}$alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(5- to 10-membered heteroaryl), —NHC(O)NH(C$_{1-6}$ alkyl), S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)$_2$NH(C$_{1-6}$ alkyl), or —S(O)$_2$N(C$_{1-6}$ alkyl)$_2$;

each L$^3$ is independently a bond, —(C$_{1-6}$ alkyl)O—, —(C$_{1-6}$ alkyl)N(R$^L$)C(O)—, —(C$_{1-6}$ alkyl)C(O)N(R$^L$)—, —(C$_{1-6}$ alkyl)N(R$^L$)C(O)(C$_{1-6}$ alkyl)-, —(C$_{1-6}$ alkyl)C(O)N(R$^L$)(C$_{1-6}$ alkyl)-, —(C$_{1-6}$ alkyl), —(C$_{1-6}$ alkyl)N(R$^L$)S(O)$_2$—, —N(R$^L$)S(O)$_2$—, —C(O)—, —(C$_{1-6}$ alkyl)C(O)—, or —N(R$^L$)C(O)—;

each R$^3$ is independently a bond, halogen, hydroxy, —CN, C$_{1-6}$ alkyl, C$_{2-4}$ alkynyl, C$_{1-6}$ alkoxy, C$_{3-8}$ cycloalkyl, 4- to 10-membered heterocyclyl, C$_6$ aryl, 5- to 10-membered heteroaryl, —NH$_2$, —NH(C$_{1-6}$ alkyl), —N(C$_{1-6}$ alkyl)$_2$, or —OC$_{3-8}$ cycloalkyl;
wherein each alkyl, alkynyl, alkoxy, cycloalkyl, and heterocyclyl is optionally substituted with one to four R$^{3a}$;

each R$^{3a}$ is independently C$_{1-6}$ alkyl, C$_{1-6}$ haloalkyl, halogen, C$_{3-8}$ cycloalkyl, 4- to 10-membered heterocyclyl, C$_6$ aryl, 5- to 10-membered heteroaryl, oxo, —OH, —CN, —NH$_2$, —O(C$_{1-6}$ alkyl), —O(C$_{1-6}$ haloalkyl), —O(C$_{3-8}$ cycloalkyl), —O(5- to 10-membered heterocyclyl), —O(C$_{6-10}$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(C₆ aryl), —NH(5- to 10-membered heteroaryl), —N(C$_{1-6}$ alkyl)$_2$, —N(C$_{1-6}$ haloalkyl)$_2$, —N(C$_{3-8}$ cycloalkyl)$_2$, —N(C$_{1-6}$ alkyl)(C$_{1-6}$ haloalkyl), —N(C$_{1-6}$ alkyl)(C$_{3-8}$ cycloalkyl), —N(C$_{1-6}$ alkyl)(5- to 10-membered heterocyclyl), —N(C$_{1-6}$ alkyl)(C$_6$ aryl), —N(C$_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH(C$_{1-6}$ alkyl), —C(O)NH(C$_{1-6}$ haloalkyl), —C(O)NH(C$_{3-8}$ cycloalkyl), —C(O)NH(5- to 10-membered heterocyclyl), —C(O)NH(C₆ aryl), —C(O)NH(5- to 10-membered heteroaryl), —C(O)N(C$_{1-6}$ alkyl)$_2$, —C(O)N(C$_{1-6}$ haloalkyl)$_2$, —C(O)N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(C₆ aryl), —NHC(O)(5- to 10-membered heteroaryl), —NHC(O)O(C$_{1-6}$ alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(C₆ aryl), —NHC(O)O(5- to 10-membered heteroaryl), —NHC(O)NH(C$_{1-6}$ alkyl), —NHC(O)NH(C$_{1-6}$ haloalkyl), —NHC(O)NH(C$_{3-8}$ cycloalkyl), —NHC(O)NH(5- to 10-membered heterocyclyl), —NHC(O)NH(C₆ aryl), —NHC(O)NH(5- to 10-membered heteroaryl), —S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)NH(C$_{1-6}$ alkyl), or —S(O)$_2$N(C$_{1-6}$ alkyl)$_2$, wherein each alkyl, cycloalkyl, heterocyclyl, aryl, and heteroaryl is optionally substituted with one to three $R^{3b}$.

each $R^{3b}$ is independently C$_{1-6}$ alkyl, C$_{1-6}$ haloalkyl, C$_{3-6}$ cycloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_{6-10}$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(5- to 10-membered heteroaryl), —N(C$_{1-6}$ alkyl)$_2$, —N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(5- to 10-membered heteroaryl), —NHC(O)O(C$_{1-6}$ alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(5- to 10-membered heteroaryl), —NHC(O)NH(C$_{1-6}$ alkyl), S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)$_2$NH(C$_{1-6}$ alkyl), or —S(O)$_2$N(C$_{1-6}$ alkyl)$_2$;

each $R^L$ is independently hydrogen, C$_{1-6}$ alkyl, C$_{1-6}$ haloalkyl, or C$_{3-8}$ cycloalkyl;

n is an integer from 0 to 3;

each $X^6$ and $X^7$ is independently N or CH, wherein no more than two of $X^4$, $X^5$, $X^6$, and $X^7$ are N;

$L^2$ is a bond, C$_1$-C$_6$ alkyl, —(C$_{1-6}$ alkyl)O—, —(C$_{1-6}$ alkyl)O(C$_{1-6}$ alkyl)-, —(C$_{1-6}$ alkyl) ($R^{L2}$)NC(O)—, —(C$_{1-6}$ alkyl)C(O)N($R^{L2}$)—, —(C$_{1-6}$ alkyl)S(O)$_2$N($R^L$)—, —(C$_{1-6}$ alkyl)N($R^{L2}$)S(O)$_2$—, or —(C$_{1-6}$alkyl)S(O)$_2$N($R^L$) (C$_{1-6}$alkyl)-;

$R^{L2}$ is hydrogen or C$_{1-6}$ alkyl;

$R^5$ is hydrogen, —CN, —OR$^{5a}$, —C(O)NR$^{5a}$$_2$, —NR$^{5a}$C(O)R$^{5a}$, —NR$^{5a}$$_2$, C$_{3-8}$ cycloalkyl, C₆ aryl, 4- to 10-membered heterocyclyl, or 5- to 10-membered heteroaryl, wherein each cycloalkyl, aryl, heterocyclyl, and heteroaryl is optionally substituted with one or two $R^{5b}$;

each $R^{5a}$ is independently hydrogen or C$_{1-6}$ alkyl;

each $R^{5b}$ is independently halogen, cyclopropyl, hydroxy, —CN, C$_{1-3}$ alkyl, C$_{1-3}$ alkoxy, —OCF$_3$, or —OCF$_2$H; and Z is O or S.

In one embodiment, the present disclosure provides a compound formula (I):

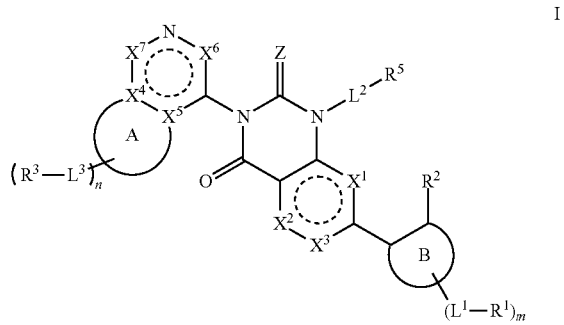

or a pharmaceutically acceptable salt thereof, wherein ring B is C$_{6-10}$ aryl or 5- to 10-membered heteroaryl;

each $L^1$ is independently a bond, —O—, —(C$_{1-6}$ alkyl)O—, —O(C$_{1-6}$ alkyl)-, —C$_{1-6}$ alkyl-O(C$_{1-6}$ alkyl)-, —C(O)—, —N($R^L$)C(O)—, —C(O)N($R^L$)—, —(C$_{1-6}$ alkyl)($R^L$)NC(O)—, —(C$_{1-6}$ alkyl)C(O)N ($R^L$)—, —N($R^L$)C(O)(C$_{1-6}$ alkyl)-, —C(O)N($R^L$) (C$_{1-6}$ alkyl)-, —(C$_{1-6}$ alkyl)N($R^L$)C(O)(C$_{1-6}$ alkyl)-, —(C$_{1-6}$ alkyl)C(O)N($R^L$)C$_{1-6}$ alkyl)-, —S(O)$_2$—, —S(O)$_2$N($R^L$)—, —N($R^L$)—S(O)$_2$—, —(C$_{1-6}$ alkyl)S(O)$_2$N($R^L$)(C$_{1-6}$ alkyl)N($R^L$)S(O)$_2$—, —S(O)$_2$ N($R^L$)C$_{1-6}$ alkyl)-, —N($R^L$)S(O)$_2$(C$_{1-6}$ alkyl)-, —(C$_{1-6}$ alkyl)S(O)$_2$N($R^L$)(C$_{1-6}$ alkyl)-, or —(C$_{1-6}$ alkyl)N($R^L$)S(O)$_2$(C$_{1-6}$ alkyl)-;

each $R^1$ is independently halogen, —OH, —CN, C$_{1-6}$ alkyl, —CN, —C(O)NH$_2$, C$_{2-6}$ alkenyl, C$_{2-6}$ alkynyl, C$_{1-6}$ alkoxy, C$_{3-8}$ cycloalkyl, C₆ aryl, 5- to 12-membered heteroaryl, or 4- to 10-membered heterocyclyl, wherein each alkyl, alkenyl, alkynyl, alkoxy, cycloalkyl, aryl, heteroaryl, and heterocyclyl is optionally substituted with one to four $R^{1a}$;

each $R^{1a}$ is independently C$_{1-6}$ alkyl, halogen, C$_{3-8}$ cycloalkyl, 5- to 10-membered heterocyclyl, C₆ aryl, 5- to 10-membered heteroaryl, oxo, —OH, —CN, —NH$_2$, —O(C$_{1-6}$ alkyl), —O(C$_{3-8}$ cycloalkyl), —O(5- to 10-membered heterocyclyl), —O(C₆ aryl), —O(5- to 10-membered heteroaryl), —NH(C$_{1-6}$ alkyl), —NH(C$_{3-8}$ cycloalkyl), —NH(5- to 10-membered heterocyclyl), —NH(C₆ aryl), —NH(5- to 10-membered heteroaryl), —N(C$_{1-6}$ alkyl)$_2$, —N(C$_{3-8}$ cycloalkyl)$_2$, —N(5- to 10-membered heterocyclyl)$_2$, —N(C$_{1-6}$ aryl)$_2$, —N(5- to 10-membered heteroaryl)$_2$, —N(C$_{1-6}$ alkyl)(C$_{3-8}$ cycloalkyl), —N(C$_{1-6}$ alkyl)(5- to 10-membered heterocyclyl), —N(C$_{1-6}$ alkyl)(C₆ aryl), —N(C$_{1-6}$ alkyl)(5- to 10-membered heteroaryl), —C(O)(5- to 10-membered heterocyclyl), —C(O)(5- to 10-membered heteroaryl), —C(O)O(C$_{1-6}$ alkyl), —C(O)O(C$_{3-8}$ cycloalkyl), —C(O)O(5- to 10-membered heterocyclyl), —C(O)O(C$_6$ aryl), —C(O)O(5- to 10-membered heteroaryl), —C(O)NH$_2$, —C(O)NH(C$_{1-6}$ alkyl), —C(O)NH(C$_{3-8}$ cycloalkyl), —C(O)NH(5- to 10-membered heterocyclyl), —C(O)NH(C$_6$ aryl), —C(O)NH(5- to 10-membered heteroaryl), —C(O)N(C$_{1-6}$ alkyl)$_2$, —C(O)N(C$_{3-8}$ cycloalkyl)$_2$, —C(O)N(5- to 10-membered heterocyclyl)$_2$, —C(O)N(C$_6$ aryl)$_2$, —C(O)N(5- to 10-membered heteroaryl)$_2$, —NHC(O)(C$_{1-6}$ alkyl), —NHC(O)(C$_{3-8}$ cycloalkyl), —NHC(O)(5- to 10-membered heterocyclyl), —NHC(O)(C$_6$ aryl), —NHC(O)(5- to 10-membered heteroaryl), —NHC(O)O(C$_{1-6}$ alkyl), —NHC(O)O(C$_{3-8}$ cycloalkyl), —NHC(O)O(5- to 10-membered heterocyclyl), —NHC(O)O(C$_6$ aryl), —NHC(O)O(5- to 10-membered heteroaryl), —NHC(O)NH(C$_{1-6}$ alkyl), —NHC(O)NH(C$_{3-8}$ cycloalkyl), —NHC(O)NH(5- to 10-membered heterocyclyl), —NHC(O)NH(C$_6$ aryl), —NHC(O)NH(5- to 10-membered heteroaryl), —NHS(O)(C$_{1-6}$ alkyl), —N(C$_{1-6}$ alkyl)(S(O)(C$_{1-6}$ alkyl), —S(O)$_2$(C$_{1-6}$ alkyl), —S(O)$_2$(C$_{3-8}$ cycloalkyl), —S(O)$_2$(5- to 10-membered heterocyclyl), —S(O)$_2$(C$_6$ aryl), —S(O)$_2$(5- to 10-membered heteroaryl), —S(O)(NH)(C$_{1-6}$ alkyl), —S(O)$_2$NH(C$_{1-6}$ alkyl), or —S(O)$_2$N(C$_{1-6}$ alkyl)$_2$.

wherein each alkyl, cycloalkyl, heterocyclyl, aryl, and heteroaryl is optionally substituted with one to three R$^{1b}$;

each R$^{1b}$ is independently C$_{1-6}$ alkyl, C$_{1-6}$ haloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_6$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(C$_6$ aryl), —NH(5- to 10-membered heteroaryl), —N(C$_{1-6}$ alkyl)$_2$, —N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(C$_6$ aryl), —NHC(O)(5- to 10-membered heteroaryl), —NHC(O)O(C$_{1-6}$ alkyl), —NHC(O)O(C$_{1-6}$ haloalkyl), —NHC(O)O(C$_{2-6}$ alkynyl), —NHC(O)O(C$_{3-8}$ cycloalkyl), —NHC(O)O(5- to 10-membered heterocyclyl), —NHC(O)O(C$_6$ aryl), —NHC(O)O(5- to 10-membered heteroaryl), —NHC(O)NH(C$_{1-6}$ alkyl), S(O)$_2$(C$_{1-6}$ alkyl), —S(O)$_2$(C$_{1-6}$ haloalkyl), —S(O)$_2$(C$_{3-8}$ cycloalkyl), —S(O)$_2$(5- to 10-membered heterocyclyl), —S(O)$_2$(C$_6$ aryl), —S(O)$_2$(5- to 10-membered heteroaryl), —S(O)(NH)(C$_{1-6}$ alkyl), —S(O)$_2$NH(C$_{1-6}$ alkyl), or —S(O)$_2$N(C$_{1-6}$ alkyl)$_2$;

m is an integer from 0 to 3;

R$^2$ is hydrogen, C$_{1-3}$ alkyl, C$_{1-3}$ haloalkyl, cyclopropyl. C$_{1-3}$ alkoxy, —O(C$_{1-3}$ haloalkyl), —O(cyclopropyl), halogen, or —CN;

X$^1$ is S, N, or C(R$^{x1}$);
X$^2$ is S, N, or C(R$^{x2}$);
X$^3$ is N or C(R$^{x3}$), provided that X$^1$ and X$^2$ are not S; alternatively, X$^3$ is a bond, wherein one of X$^1$ and X$^2$ is S;

each R$^{x1}$ R$^{x2}$, and R$^{x3}$ is independently hydrogen, halogen, C$_{1-3}$ alkyl, C$_{1-3}$ haloalkyl, O C$_{1-3}$ haloalkyl, C$_{1-3}$ alkoxy, cyclopropyl, or O-cyclopropyl;

ring (A) taken together with X$^4$ and X$^5$ is C$_6$ aryl, 5- to 6-membered heteroaryl, C$_{5-10}$ cycloalkyl, or 5- to 10-membered heterocyclyl, wherein each X$^4$ and X$^5$ is independently N or C;

alternatively, ring (A) is absent, wherein X$^4$ is N or C-L$^{x4}$-R$^{x4}$, and X$^5$ is N or C-L$^{x5}$-R$^{x5}$;

each L$^{x4}$ and L$^{x5}$ is independently a bond, —(C$_{1-6}$ alkyl)O—, —(C$_{1-6}$ alkyl)N(R$^L$)C(O)—, —(C$_{1-6}$ alkyl)C(O)N(R$^L$)—, —(C$_{1-6}$alkyl)N(R$^L$)C(O)(C$_{1-6}$ alkyl)-, —(C$_{1-4}$ alkyl)C(O)N(R$^L$)(C$_{1-6}$ alkyl)-, —(C$_{1-6}$ alkyl), —(C$_{1-6}$ alkyl)N(R$^L$)S(O)$_2$—, —N(R$^L$)S(O)$_2$—, —C(O)—, —(C$_{1-6}$ alkyl)C(O)—, or —N(R$^L$)C(O)—;

each R$^{x4}$ and R$^{x5}$ is independently a hydrogen, halogen, hydroxy, —CN, C$_{1-6}$ alkyl, C$_{2-6}$ alkynyl, C$_{1-6}$alkoxy, C$_{3-8}$ cycloalkyl, 4- to 10-membered heterocyclyl, 5- to 10-membered heteroaryl, —NH$_2$, —NH(C$_{1-6}$ alkyl), —N(C$_{1-6}$ alkyl)$_2$, —O(C$_{1-6}$ alkyl), or —OC$_{3-8}$ cycloalkyl;

wherein each alkyl, alkynyl, alkoxy, cycloalkyl, and heterocyclyl is optionally substituted with one to four R$^{4a}$;

each R$^{4a}$ is independently C$_{1-6}$ alkyl, C$_{1-6}$ haloalkyl, halogen, C$_{3-8}$ cycloalkyl, 5- to 10-membered heterocyclyl, C$_6$ aryl, 5- to 10-membered heteroaryl, oxo, —OH, —CN, —NH$_2$, —O(C$_{1-6}$ alkyl), —O(C$_{1-6}$ haloalkyl), —O(C$_{3-8}$ cycloalkyl), —O(5- to 10-membered heterocyclyl), —O(C$_{6-10}$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(C$_6$ aryl), —NH(5- to 10-membered heteroaryl), —N(C$_{1-6}$ alkyl)$_2$, —N(C$_{1-6}$ haloalkyl)$_2$, —N(C$_{3-8}$ cycloalkyl)$_2$, —N(C$_{1-6}$ alkyl)(C$_{1-6}$ haloalkyl), —N(C$_{1-6}$ alkyl)(C$_{3-8}$ cycloalkyl), —N(C$_{1-6}$ alkyl)(5- to 10-membered heterocyclyl), —N(C$_{1-6}$ alkyl)(C$_6$ aryl), —N(C$_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH(C$_{1-6}$ alkyl), —C(O)NH(C$_{1-6}$ haloalkyl), —C(O)NH(C$_{3-8}$ cycloalkyl), —C(O)NH(5- to 10-membered heterocyclyl), —C(O)NH(C$_6$ aryl), —C(O)NH(5- to 10-membered heteroaryl), —C(O)N(C$_{1-6}$ alkyl)$_2$, —C(O)N(C$_{1-6}$ haloalkyl)$_2$, —C(O)N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(C$_6$ aryl), —NHC(O)(5- to 10-membered heteroaryl), —NHC(O)O(C$_{1-6}$ alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(C$_6$ aryl), —NHC(O)O(5- to 10-membered heteroaryl), —NHC(O)NH(C$_{1-6}$ alkyl), —NHC(O)NH(C$_{1-6}$ haloalkyl), —NHC(O)NH(C$_{3-8}$ cycloalkyl), —NHC(O)NH(5- to 10-membered heterocyclyl), —NHC(O)NH(C$_6$ aryl), —NHC(O)NH(5- to 10-membered heteroaryl), —S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)$_2$NH(C$_{1-6}$ alkyl), or —S(O)$_2$N(C$_{1-6}$ alkyl)$_2$, wherein each alkyl, cycloalkyl, heterocyclyl, aryl, and heteroaryl is optionally substituted with one to three R$^{4b}$;

each R$^{4b}$ is independently C$_{1-6}$ alkyl, C$_{1-6}$ haloalkyl, C$_{3-8}$ cycloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_6$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH(5- to 10-membered heteroaryl), —N($C_{1-6}$ alkyl)$_2$, —N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)(5- to 10-membered heteroaryl), —NHC(O)O($C_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O(5- to 10-membered heteroaryl), —NHC(O)NH($C_{1-6}$ alkyl), S(O)$_2$($C_{1-6}$ alkyl), —S(O)$_2$($C_{1-6}$ haloalkyl), —S(O)$_2$($C_{3-8}$ cycloalkyl), —S(O)(NH)($C_{1-6}$ alkyl), —S(O)$_2$NH($C_{1-6}$ alkyl), or —S(O)$_2$N($C_{1-6}$ alkyl)$_2$;

each $L^3$ is independently a bond, —($C_{1-6}$ alkyl)O—, —($C_{1-6}$ alkyl)N($R^L$)C(O)—, —($C_{1-6}$ alkyl)C(O)N($R^L$)—, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —($C_{1-6}$ alkyl), —($C_{1-6}$ alkyl)N($R^L$)S(O)$_2$—, —N($R^L$)S(O)$_2$—, —C(O)—, —($C_{1-6}$ alkyl)C(O)—, or —N($R^L$)C(O)—;

each $R^3$ is independently a bond, halogen, hydroxy, —CN, $C_{1-6}$ alkyl, $C_{2-6}$ alkynyl, $C_{1-6}$ alkoxy, $C_{3-8}$ cycloalkyl, 4- to 10-membered heterocyclyl, $C_6$ aryl, 5- to 10-membered heteroaryl, —NH$_2$, —NH($C_{1-6}$ alkyl), —N($C_{1-6}$ alkyl)$_2$, or —O$C_{3-8}$ cycloalkyl;

wherein each alkyl, alkynyl, alkoxy, cycloalkyl, and heterocyclyl is optionally substituted with one to four $R^{3a}$;

each $R^{3a}$ is independently $C_{1-6}$ alkyl, $C_{1-6}$ haloalkyl, halogen, $C_{3-8}$ cycloalkyl, 5- to 10-membered heterocyclyl, $C_6$ aryl, 5- to 10-membered heteroaryl, oxo, —OH, —CN, —NH$_2$, —O($C_{1-6}$ alkyl), —O($C_{1-6}$ haloalkyl), —O($C_{3-8}$ cycloalkyl), —O(5- to 10-membered heterocyclyl), —O($C_{6-10}$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{1-6}$ haloalkyl)$_2$, —N($C_{3-8}$ cycloalkyl)$_2$, —N($C_{1-6}$ alkyl)($C_{1-6}$ haloalkyl), —N($C_{1-6}$ alkyl)($C_{3-8}$ cycloalkyl), —N($C_{1-6}$ alkyl)(5- to 10-membered heterocyclyl), —N($C_{1-6}$ alkyl)($C_{1-6}$ aryl), —N($C_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH($C_{1-6}$ alkyl), —C(O)NH($C_{1-6}$ haloalkyl), —C(O)NH($C_{3-8}$ cycloalkyl), —C(O)NH(5- to 10-membered heterocyclyl), —C(O)NH($C_6$ aryl), —C(O)NH(5- to 10-membered heteroaryl), —C(O)N($C_{1-6}$ alkyl)$_2$, —C(O)N($C_{1-6}$ haloalkyl)$_2$, —C(O)N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), —NHC(O)NH($C_{1-6}$ haloalkyl), —NHC(O)NH($C_{3-8}$ cycloalkyl), —NHC(O)NH(5- to 10-membered heterocyclyl), —NHC(O)NH($C_6$ aryl), —NHC(O)NH(5- to 10-membered heteroaryl), —S(O)$_2$($C_{1-6}$ alkyl), —S(O)$_2$($C_{1-6}$ haloalkyl), —S(O)$_2$($C_{3-8}$ cycloalkyl), —S(O)(NH)($C_{1-6}$ alkyl), —S(O)$_2$NH($C_{1-6}$ alkyl), or —S(O)$_2$N($C_{1-6}$ alkyl)$_2$, wherein each alkyl, cycloalkyl, heterocyclyl, aryl, and heteroaryl is optionally substituted with one to three $R^{3b}$;

each $R^{3D}$ is independently $C_{1-6}$ alkyl, $C_{1-6}$ haloalkyl, $C_{3-6}$ cycloalkyl, halogen, oxo, —OH, —NH$_2$, CO$_2$H, —O($C_{1-6}$ alkyl), —O($C_{1-6}$ haloalkyl), —O($C_{3-8}$ cycloalkyl), —O(5- to 10-membered heterocyclyl), —O($C_{6-10}$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH(5- to 10-membered heteroaryl), —N($C_{1-6}$ alkyl)$_2$, —N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)(5- to 10-membered heteroaryl), —NHC(O)O($C_{1-6}$alkyl), —NHC(O)O($C_{1-6}$ haloalkyl), —NHC(O)O($C_{3-8}$ cycloalkyl), —NHC(O)O(5- to 10-membered heterocyclyl), —NHC(O)O(5- to 10-membered heteroaryl), —NHC(O)NH($C_{1-6}$ alkyl), S(O)$_2$($C_{1-6}$ alkyl), —S(O)$_2$($C_{1-6}$ haloalkyl), —S(O)$_2$($C_{3-8}$ cycloalkyl), —S(O)(NH)($C_{1-6}$ alkyl), —S(O)$_2$NH($C_{1-6}$ alkyl), or —S(O)$_2$N($C_{1-6}$ alkyl)$_2$;

each $R^L$ is independently hydrogen. $C_{1-6}$ alkyl, $C_{1-6}$haloalkyl, or $C_{3-8}$ cycloalkyl;

n is an integer from 0 to 3;

each $X^6$ and $X^7$ is independently N or CH,
wherein no more than two of $X^4$, $X^1$, $X^6$, and $X^7$ are N;

$L^2$ is a bond, $C_1$-$C_6$ alkyl, —($C_{1-6}$ alkyl)O—, —($C_{1-6}$ alkyl)O($C_{1-6}$ alkyl)-, —($C_{1-6}$ alkyl) ($R^{L2}$)NC(O)—, —($C_{1-6}$ alkyl)C(O)N($R^{L2}$)—, —($C_{1-6}$alkyl)S(O)$_2$N($R^2$)—, —($C_{1-6}$ alkyl)N($R^{L2}$)S(O)$_2$—, or —($C_{1-6}$ alkyl)S(O)$_2$N($R^{L2}$) ($C_{1-6}$ alkyl)-;

$R^{L2}$ is hydrogen or $C_{1-6}$ alkyl;

$R^5$ is hydrogen, —CN, —OR$^{5a}$, —C(O)NR$^{5a}$$_2$, —NR$^{5a}$$_2$, $C_{3-8}$ cycloalkyl, $C_6$ aryl, 4- to 10-membered heterocyclyl, or 5- to 10-membered heteroaryl, wherein each cycloalkyl, aryl, heterocyclyl, and heteroaryl is optionally substituted with one or two $R^{5b}$;

each $R^{5a}$ is independently hydrogen or $C_{1-6}$ alkyl;

each $R^{5b}$ is independently halogen, cyclopropyl, hydroxy, —CN, $C_{1-3}$ alkyl, $C_{1-3}$ alkoxy, —OCF$_3$, or —OCF$_2$H; and Z is O or S.

In another embodiment, the present disclosure provides a pharmaceutical composition comprising a pharmaceutically effective amount of a compound of the present disclosure, or a pharmaceutically acceptable salt thereof, and a pharmaceutically acceptable carrier or excipient.

In another embodiment, the present disclosure provides a method of treating a viral infection in a subject in need thereof, the method comprising administering to the subject a therapeutically effective amount of a compound of the present disclosure, or a pharmaceutically acceptable salt thereof, or a pharmaceutical composition of the present disclosure.

DETAILED DESCRIPTION

The present disclosure relates generally to methods and compounds for treating or preventing viral infections, for example coronaviridae infections.

Definitions

As used in the present specification, the following words, phrases and symbols are generally intended to have the meanings as set forth below, except to the extent that the context in which they are used indicates otherwise.

"Alkyl" refers to an unbranched or branched saturated hydrocarbon chain. For example, an alkyl group can have 1 to 20 carbon atoms (i.e., $C_1$-$C_{20}$ alkyl), 1 to 8 carbon atoms (i.e., $C_1$-$C_8$ alkyl), 1 to 6 carbon atoms (i.e., $C_1$-$C_6$ alkyl), or 1 to 3 carbon atoms (i.e., $C_1$-$C_3$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_2)_2CH(CH_3)_2$), and 3,3-dimethyl-2-butyl (—$CH(CH_3)C(CH_3)_3$.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-8}$, $C_{3-6}$, $C_4$, $C_{4-5}$, $C_{4-6}$, $C_5$, $C_{5-6}$ and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-8}$, $C_{3-8}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatrienyl. Alkynyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers an alkoxy group linked to an alkyl group which is linked to the remainder of the compound such that the alkyl group is divalent. Alkoxyalkyl can have any suitable number of carbon, such as from 2 to 6 ($C_{2-6}$ alkoxyalkyl), 2 to 5 ($C_{2-5}$ alkoxyalkyl), 2 to 4 ($C_{2-4}$ alkoxyalkyl), or 2 to 3 ($C_{2-3}$ alkoxyalkyl). Alkoxy and alkyl are as defined above where the alkyl is divalent, and can include, but is not limited to, methoxymethyl ($CH_3OCH_2$—), methoxyethyl ($CH_3OCH_2CH_2$—) and others.

"Alkoxy-alkoxy" refers an alkoxy group linked to a second alkoxy group which is linked to the remainder of the compound. Alkoxy is as defined above, and can include, but is not limited to, methoxy-methoxy ($CH_3OCH_2O$—), methoxy-ethoxy ($CH_3OCH_2CH_2O$—) and others.

"Halo" or "halogen" as used herein refers to fluoro (—F), chloro (—Cl), bromo (—Br) and iodo (—I).

The term "oxo" as used herein is intended to mean an oxygen atom attached to a carbon atom as a substituent by a double bond (=O).

"Hydroxyl" and "hydroxy" are used interchangeably and refer to —OH.

"Haloalkyl" as used herein refers to an alkyl as defined herein, wherein one or more hydrogen atoms of the alkyl are independently replaced by a halo substituent, which may be the same or different. For example, $C_{1-4}$ haloalkyl is a $C_{1-4}$ alkyl wherein one or more of the hydrogen atoms of the $C_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycle (e.g., bicyclic carbocycles having 6 to 12 annular carbon atoms such as bicyclo[3.1.0]hexane and bicyclo[2.1.1]hexane), and polycyclic carbocycles (e.g., tricyclic and tetracyclic carbocycles with up to 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-6}$, $C_{2-6}$, $C_{3-4}$, $C_{3-8}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Heterocyclyl" or "heterocycle" or "heterocycloalkyl" as used herein refers to a single saturated or partially unsaturated non-aromatic ring or a multiple ring system having at least one heteroatom in the ring (i.e., at least one annular heteroatom selected from oxygen, nitrogen, and sulfur) wherein the multiple ring system includes at least non-aromatic ring containing at least one heteroatom. The multiple ring system can also include other aromatic rings and non-aromatic rings. Unless otherwise specified, a heterocyclyl group has from 3 to 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from 1 to 6 annular carbon atoms and from 1 to 3 annular heteroatoms selected from the group consisting of oxygen, nitrogen and sulfur in the ring. The heteroatoms can optionally be oxidized to form —N(—OH)—, =N(—O—)—, —S(=O)— or —S(=O)$_2$—. The rings of the multiple condensed ring (e.g., bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heterocycloalkyl component is as defined above. Alkyl-heterocycloalkyl groups can be substituted or unsubstituted.

"Aryl" as used herein refers to a single all carbon aromatic ring or a multiple condensed all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having 9 to 20 carbon atoms in which at least one ring is aromatic and wherein the other rings may be aromatic or not aromatic (i.e., carbocycle) and may be saturated or partially saturated. Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. Examples of alkyl-aryl groups include, but are not limited to, benzyl and ethyl-benzene. Alkyl-aryl groups can be substituted or unsubstituted.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from 1 to 6 carbon atoms and 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. The other rings may be aromatic or not aromatic (i.e., carbocycle) and may be saturated or partially saturated. Thus, a heteroaryl (a single aromatic ring or multiple condensed ring system) has 1-20 carbon atoms and 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thionaphthenyl, pyrrolo[2,3-b]pyridinyl, quinazolinyl-4(3H)-one, and triazolyl.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heteroaryl component is as defined within. Alkyl-heteroaryl groups can be substituted or unsubstituted.

A "compound of the present disclosure" includes compounds disclosed herein, for example a compound of the present disclosure includes compounds of Formula (I), (II), (II-a), (II-b), (II-c), (II-d), (III), (III-a), (III-b), (III-c), (III-d), (IV), (IV-a), (IV-b), (V), (V-a), and (V-b), including the compounds of the Examples.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically effective amount" refers to an amount of a compound of the present disclosure in a formulation or combination thereof, that provides the desired therapeutic or pharmaceutical result.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition), and c) relieving the disease or condition, e.g., causing the regression of clinical symptoms, ameliorating the disease state, delaying the progression of the disease, increasing the quality of life, and/or prolonging survival.

The terms "treatment" or "treat" or "treating" also encompass alleviating or eliminating symptoms of a viral infection and/or reducing viral load in a patient. The term "treatment" also encompasses the administration of a compound or composition according to the embodiments disclosed herein post-exposure of the individual to the virus but before the appearance of symptoms of the disease, and/or prior to the detection of the virus in the blood, to prevent the appearance of symptoms of the disease and/or to prevent the virus from reaching detectible levels in the blood.

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount can vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device, e.g., a mini-osmotic pump, to the subject. The administration can be carried out according to a schedule specifying frequency of administration, dose for administration, and other factors.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

"Subject" refers to animals such as mammals, including, but not limited to, primates (e.g., humans), cows, sheep, goats, horses, dogs, cats, rabbits, rats, mice and the like. In certain embodiments, the subject is a human.

"Disease" or "condition" refer to a state of being or health status of a patient or subject capable of being treated with a compound, pharmaceutical composition, or method provided herein.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds of described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$ respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The compounds of the embodiments disclosed herein, or their pharmaceutically acceptable salts may be "atropisomers". i.e., stereoisomers arising due to hindered rotation about a single bond, where the barrier to rotation about the bond is high enough to allow for isolation of individual stereoisomers. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein. "scalemic mixture" is a mixture of stereoisomers at a ratio other than 1:1.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons. New York, 1992).

Atropisomers described herein may be represented using bold bonds (" "), wedged bonds (" ") hashed bonds (" "), and hashed wedged bonds (" ") in a manner that is well understood by those skilled in the art. By way of example, the following shows various representations atropisomeric pairs:

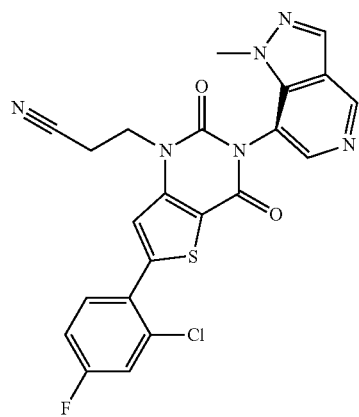
Example 955
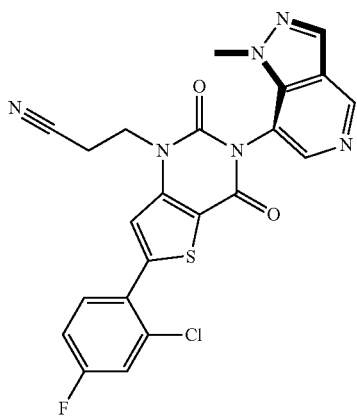
Example 955
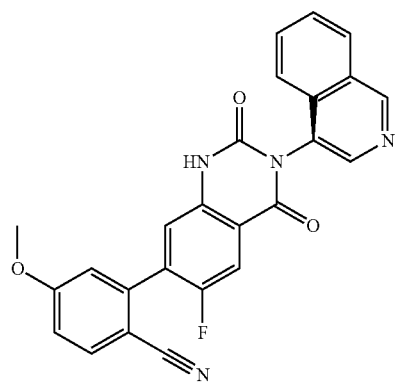
Example 438
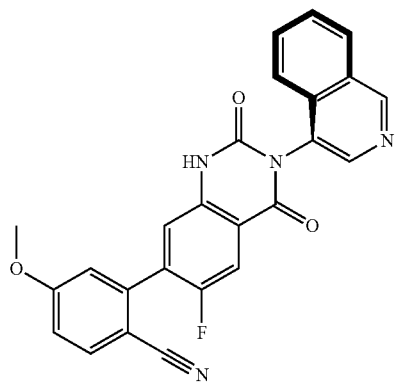
Example 438
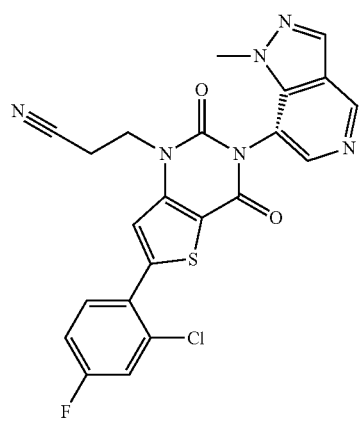
Example 956
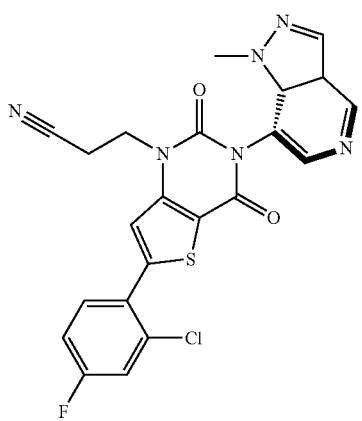
Example 956

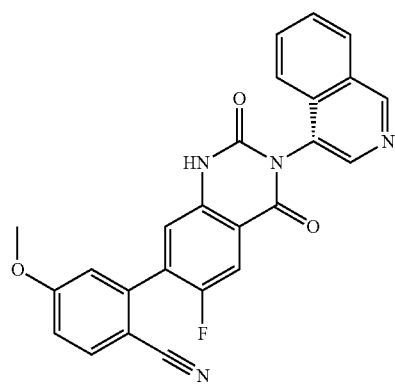
Example 439
=
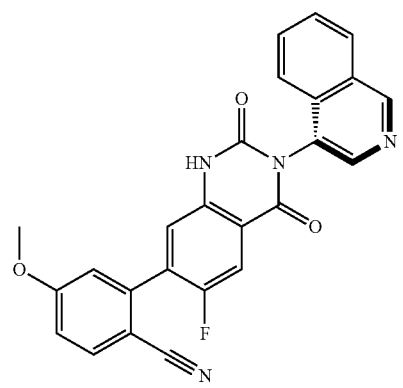
Example 439
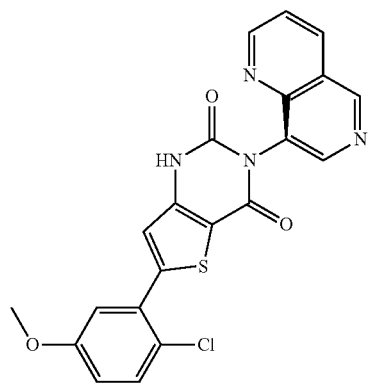
Example 468
=
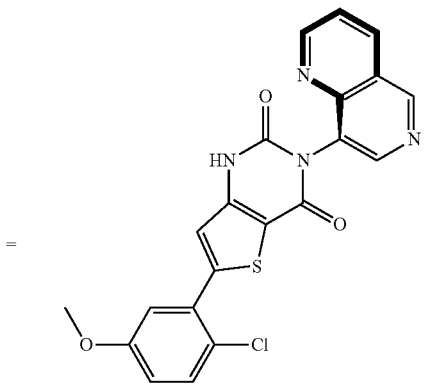
Example 468
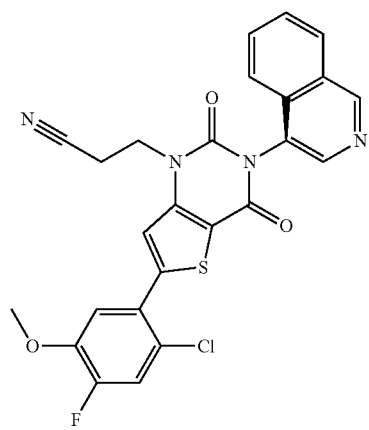
Example 637
=
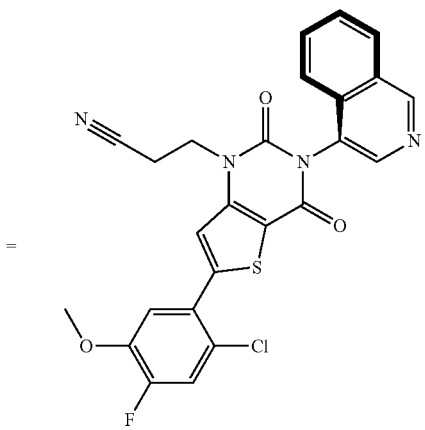
Example 637

-continued
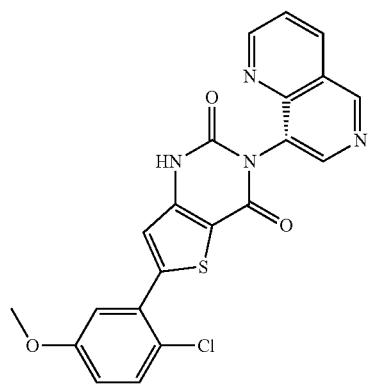
Example 467
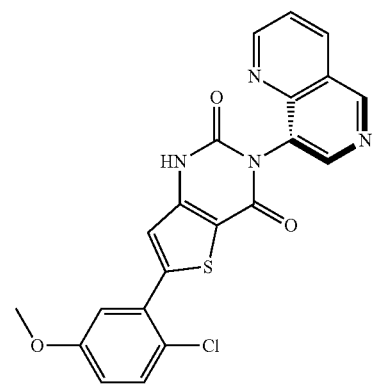
Example 467
=
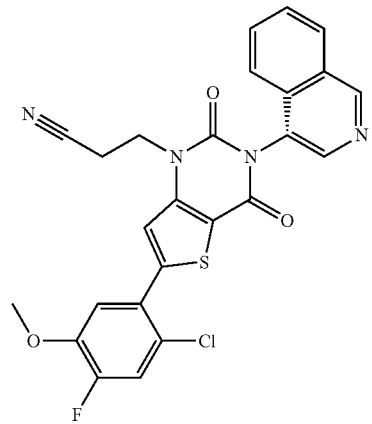
Example 638
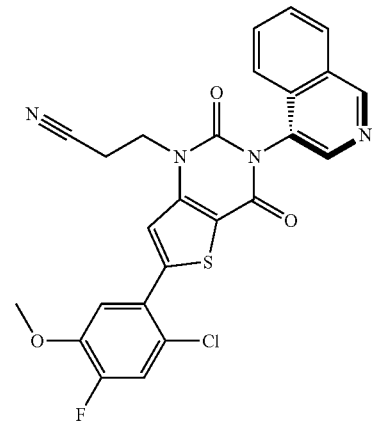
Example 638
=
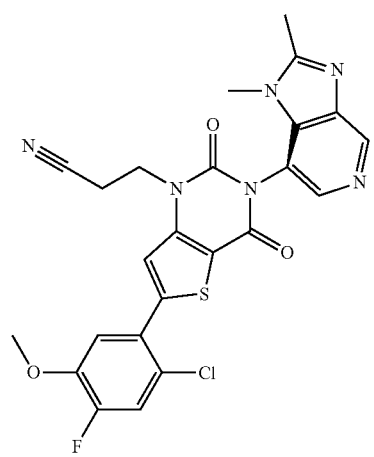
Example 970
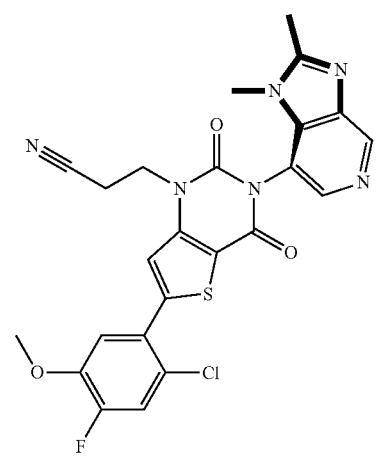
Example 970
=

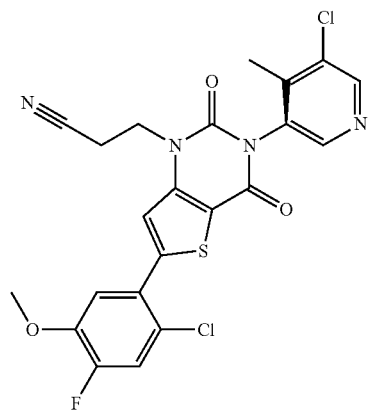

Example 1032

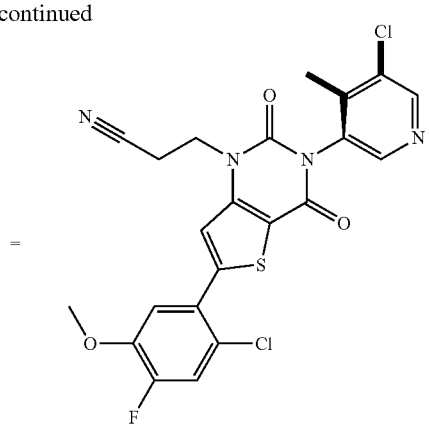

Example 1032

=

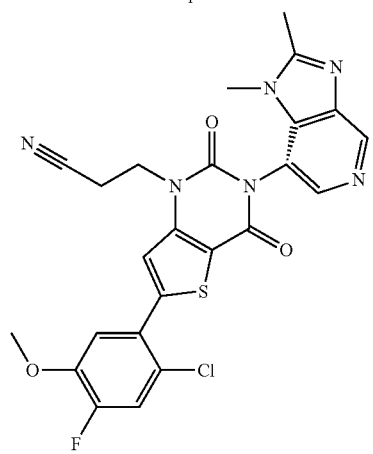

Example 969

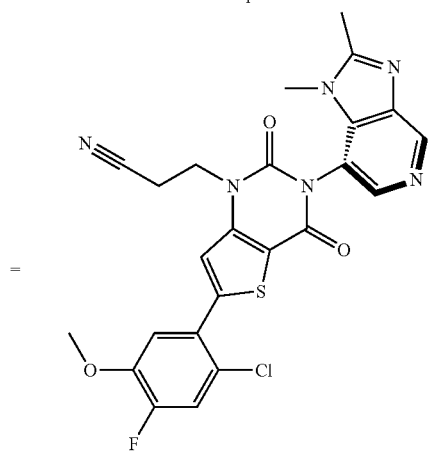

Example 969

=

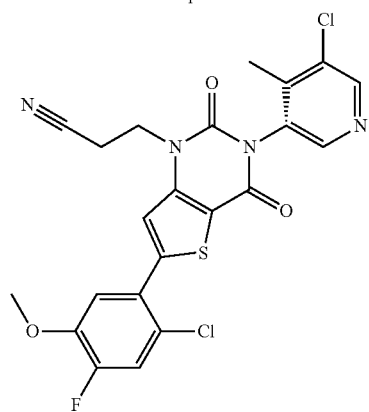

Example 1033

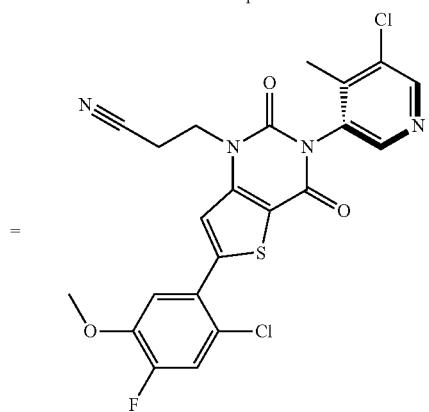

Example 1033

=

"Tautomer" refers to alternate forms of a compound that differ in the position of a proton, such as enol-keto and imine-enamine tautomers, or the tautomeric forms of heteroaryl groups containing a ring atom attached to both a ring —NH— and a ring =N— such as pyrazoles, imidazoles, benzimidazoles, triazoles, and tetrazoles.

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "—SO₂CH₂—" is equivalent to "—CH₂SO₂—" and both may be connected in either direction. Similarly, an "arylalkyl" group, for example, may be attached to the remainder of the molecule at either an aryl or an alkyl portion of the group. A prefix such as "C$_{u-v}$" or (C$_u$-C$_v$) indicates that the following group has from u to v carbon atoms. For example, "C$_{1-6}$alkyl" and "C$_1$-C$_6$ alkyl" both indicate that the alkyl group has from 1 to 6 carbon atoms.

The term "antiviral agent" as used herein is intended to mean an agent that is effective to inhibit the formation and/or replication of a virus in a mammal, including but not limited to agents that interfere with either host or viral mechanisms necessary for the formation and/or replication of a virus in a mammal.

Whenever a compound described herein is substituted with more than one of the same designated group, e.g., "R" or "R'", then it will be understood that the groups may be the same or different, i.e., each group is independently selected, unless indicated otherwise.

Wavy lines, ⌇⌇⌇, indicate the site of covalent bond attachments to the adjoining substructures, groups, moieties, or atoms.

The prefixes "C$_{u-v}$" and "(C$_{u-v}$)" indicate that the following group has from u to v carbon atoms. For example, "C$_{1-8}$ alkyl" indicates that the alkyl group has from 1 to 8 carbon atoms.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively.

Unless indicated explicitly otherwise, where combinations of groups are referred to herein as one moiety, e.g., arylalkyl, the last mentioned group contains the atom by which the moiety is attached to the rest of the molecule.

The term "substituted" means that any one or more hydrogen atoms on the designated atom or group is replaced with one or more substituents other than hydrogen, provided that the designated atom's normal valence is not exceeded. The one or more substituents unless indicated otherwise include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof.

The term "optionally substituted" refers to any one or more hydrogen atoms on the designated atom or group may or may not be replaced by a moiety other than hydrogen.

Compounds

The present disclosure provides compounds that are inhibitors of the SARS-CoV-2 main protease. In some embodiments, the disclosure provides compounds of Formula (I) as described herein, and/or pharmaceutically acceptable salt(s) thereof. In some embodiments, a compound is provided according to Formula (I):

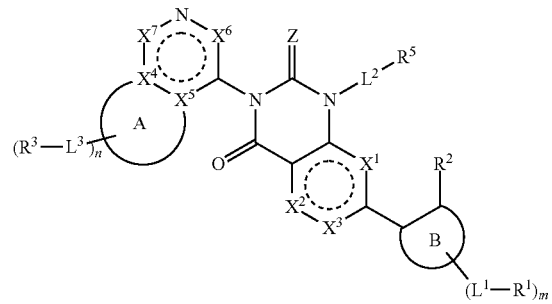

and/or pharmaceutically acceptable salt(s) thereof.

In some embodiments, the compound of Formula (I) is

I

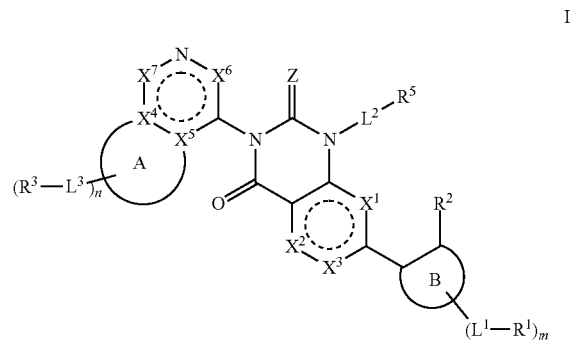

or a pharmaceutically acceptable salt thereof, wherein ring B is C$_{6-10}$ aryl or 5- to 10-membered heteroaryl;

each L$^1$ is independently a bond, —O—, —(C$_{1-6}$ alkyl)O—, —O(C$_{1-6}$ alkyl)-, —C$_{1-6}$ alkyl-O(C$_{1-6}$ alkyl)-, —C(O)—, —N(R$^L$)C(O)—, —C(O)N(R$^L$)—, —(C$_{1-6}$ alkyl)(R$^L$)NC(O)—, —(C$_{1-6}$ alkyl)C(O)N(R$^L$)—, —N(R$^L$)C(O)(C$_{1-6}$ alkyl)-, —C(O)N(R$^L$) (C$_{1-6}$ alkyl)-, —(C$_{1-6}$ alkyl)N(R$^L$)C(O)(C$_{1-6}$ alkyl)-, —(C$_{1-6}$ alkyl)C(O)N(R$^L$)(C$_{1-6}$ alkyl)-, —S(O)$_2$—, —S(O)$_2$N(R$^L$)—, —N(R$^L$)—S(O)$_2$—, —(C$_{1-6}$ alkyl)S(O)$_2$N(R$^L$)—, —(C$_{1-6}$ alkyl)N(R$^L$)S(O)$_2$—, —S(O)$_2$N(R$^L$)(C$_{1-6}$ alkyl)-, —N(R$^L$)S(O)$_2$(C$_{1-6}$ alkyl)-, —(C$_{1-6}$ alkyl)S(O)$_2$N(R$^L$)(C$_{1-6}$ alkyl)-, or —(C$_{1-6}$ alkyl)N(R$^L$)S(O)$_2$(C$_{1-6}$ alkyl)-;

each R$^1$ is independently halogen, —OH, —CN, C$_{1-6}$ alkyl, —CN, —C(O)NH$_2$, C$_{2-6}$ alkenyl, C$_{2-6}$ alkynyl, C$_{1-6}$ alkoxy, C$_{3-8}$ cycloalkyl, C$_6$ aryl, 5- to 12-membered heteroaryl, or 4- to 10-membered heterocyclyl, wherein each alkyl, alkenyl, alkynyl, alkoxy, cycloalkyl, aryl, heteroaryl, and heterocyclyl is optionally substituted with one to four R$^{1a}$;

alternatively, two R$^1$ taken together with the atoms of ring B to which they are attached form 5- to 10-membered heterocyclyl;

each R$^{1a}$ is independently C$_{1-6}$ alkyl, halogen, C$_{3-8}$ cycloalkyl, 4- to 10-membered heterocyclyl, C$_6$ aryl, 5- to 10-membered heteroaryl, oxo. —OH, —CN, —NH$_2$, —O(C$_{1-6}$ alkyl), —O(C$_{3-8}$ cycloalkyl), —O(5- to 10-membered heterocyclyl), —O(C$_6$ aryl), —O(5- to 10-membered heteroaryl), —NH(C$_{1-6}$ alkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{3-8}$ cycloalkyl)$_2$, —N(5- to 10-membered heterocyclyl)$_2$, —N($C_6$ aryl)$_2$, —N(5- to 10-membered heteroaryl)$_2$, —N($C_{1-6}$ alkyl)($C_{3-8}$ cycloalkyl), —N($C_{1-6}$ alkyl)(5- to 10-membered heterocyclyl), —N($C_{1-6}$ alkyl)($C_6$ aryl), —N($C_{1-6}$ alkyl)(5- to 10-membered heteroaryl), —C(O)(5- to 10-membered heterocyclyl), —C(O)(5- to 10-membered heteroaryl), —C(O)O$C_{1-6}$ alkyl), —C(O)O($C_{3-8}$ cycloalkyl), —C(O)O(5- to 10-membered heterocyclyl), —C(O)O($C_6$ aryl), —C(O)O(5- to 10-membered heteroaryl), —C(O)NH$_2$, —C(O)NH($C_{1-6}$ alkyl), —C(O)NH($C_{3-8}$ cycloalkyl), —C(O)NH(5- to 10-membered heterocyclyl), —C(O)NH($C_6$ aryl), —C(O)NH(5- to 10-membered heteroaryl), —C(O)N($C_{1-6}$ alkyl)$_2$, —C(O)N($C_{3-8}$ cycloalkyl)$_2$, —C(O)N(5- to 10-membered heterocyclyl)$_2$, —C(O)N($C_6$ aryl)$_2$, —C(O)N(5- to 10-membered heteroaryl)$_2$, —NHC(O)($C_{1-6}$ alkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), —NHC(O)NH($C_{3-8}$ cycloalkyl), —NHC(O)NH(5- to 10-membered heterocyclyl), —NHC(O)NH($C_6$ aryl), —NHC(O)NH(5- to 10-membered heteroaryl), —NHS(O)($C_{1-6}$ alkyl), —N($C_{1-6}$ alkyl)(S(O)($C_{1-6}$ alkyl), —S(O)$_2$($C_{1-6}$ alkyl), —S(O)$_2$($C_{3-8}$ cycloalkyl), —S(O)$_2$(5- to 10-membered heterocyclyl), —S(O)$_2$($C_6$ aryl), —S(O)$_2$(5- to 10-membered heteroaryl), —S(O)(NH)($C_{1-6}$ alkyl), —S(O)$_2$NH($C_{1-6}$ alkyl), or —S(O)$_2$N($C_{1-6}$ alkyl)$_2$,
wherein each alkyl, cycloalkyl, heterocyclyl, aryl, and heteroaryl is optionally substituted with one to three $R^{1b}$;
each $R^{1b}$ is independently $C_{1-6}$ alkyl, $C_{1-6}$ haloalkyl, halogen, oxo, —OH, —NH$_2$, CO$_2$H—O($C_{1-6}$ alkyl), —O($C_{1-6}$ haloalkyl), —O($C_{3-8}$ cycloalkyl), —O(5- to 10-membered heterocyclyl), —O($C_6$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{1-6}$ haloalkyl), —NHC(O)O($C_{2-6}$ alkynyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), S(O)$_2$($C_{1-6}$ alkyl), —S(O)$_2$($C_{1-6}$ haloalkyl), —S(O)$_2$($C_{3-8}$ cycloalkyl), —S(O)$_2$(5- to 10-membered heterocyclyl), —S(O)$_2$($C_6$ aryl), —S(O)$_2$(5- to 10-membered heteroaryl), —S(O)(NH)($C_{1-6}$ alkyl), —S(O)$_2$NH($C_{1-6}$ alkyl), or —S(O)$_2$N($C_{1-6}$ alkyl)$_2$;
m is an integer from 0 to 3;
$R^2$ is hydrogen. $C_{1-3}$ alkyl, $C_{1-3}$ haloalkyl, cyclopropyl, $C_{1-3}$ alkoxy, —O($C_{1-3}$ haloalkyl), —O(cyclopropyl), halogen, or —CN;
$X^1$ is S, N, or C($R^{x1}$);
$X^2$ is S, N, or C($R^{x2}$);
$X^3$ is N or C($R^{x3}$), provided that $X^1$ and $X^2$ are not S;
alternatively, $X^3$ is a bond, wherein one of $X^1$ and $X^2$ is S;
each $R^{x1}$, $R^{x2}$, and $R^{x3}$ is independently hydrogen, halogen, $C_{1-3}$ alkyl, $C_{1-3}$ haloalkyl, O $C_{1-3}$ haloalkyl, $C_{1-3}$ alkoxy, cyclopropyl, or O-cyclopropyl;

ring (A) taken together with $X^4$ and $X^5$ is $C_6$ aryl, 5- to 6-membered heteroaryl, $C_{5-10}$ cycloalkyl, or 5- to 10-membered heterocyclyl,
wherein each $X^4$ and $X^5$ is independently N or C;

alternatively, ring (A) is absent, wherein $X^4$ is N or C-$L^{x4}$-$R^{x4}$, and $X^5$ is N or C-$L^{x5}$-$R^{x5}$;
each $L^{x4}$ and $L^{x5}$ is independently a bond, —($C_{1-6}$ alkyl)O—, —($C_{1-6}$ alkyl)N($R^L$)C(O)—, —($C_{1-6}$ alkyl)C(O)N($R^L$)—, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —($C_{1-6}$ alkyl), —($C_{1-6}$ alkyl)N($R^L$)S(O)$_2$—, —N($R^L$)S(O)$_2$—, —C(O)—, —($C_{1-6}$ alkyl)C(O)—, or —N($R^L$)C(O)—;
each $R^{x4}$ and $R^{x5}$ is independently hydrogen, halogen, hydroxy, —CN, $C_{1-6}$ alkyl, $C_{2-6}$ alkynyl, $C_{1-6}$alkoxy, $C_{3-8}$ cycloalkyl, 4- to 10-membered heterocyclyl, 5- to 10-membered heteroaryl, —NH$_2$, —NH($C_{1-6}$ alkyl), —N($C_{1-6}$ alkyl)$_2$, —O($C_{1-6}$ alkyl), or —O$C_{3-8}$ cycloalkyl;
wherein each alkyl, alkynyl, alkoxy, cycloalkyl, and heterocyclyl is optionally substituted with one to four $R^1$;
each $R^{4a}$ is independently $C_{1-6}$ alkyl, $C_{1-6}$ haloalkyl, halogen, $C_{3-8}$ cycloalkyl, 4- to 10-membered heterocyclyl, $C_6$ aryl, 5- to 10-membered heteroaryl, oxo, —OH, —CN, —NH$_2$, —O($C_{1-6}$ alkyl), —O($C_{1-6}$ haloalkyl), —O($C_{3-8}$ cycloalkyl), —O(5- to 10-membered heterocyclyl), —O($C_{6-10}$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{1-6}$ haloalkyl)$_2$, —N($C_{3-8}$ cycloalkyl)$_2$, —N($C_{1-6}$ alkyl)($C_{1-6}$ haloalkyl), —N($C_{1-6}$ alkyl)($C_{3-8}$ cycloalkyl), —N($C_{1-6}$ alkyl)(5- to 10-membered heterocyclyl), —N($C_{1-6}$ alkyl)($C_6$ aryl), —N($C_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH($C_{1-6}$ alkyl), —C(O)NH($C_{1-6}$ haloalkyl), —C(O)NH($C_{3-8}$ cycloalkyl), —C(O)NH(5- to 10-membered heterocyclyl), —C(O)NH($C_6$ aryl), —C(O)NH(5- to 10-membered heteroaryl), —C(O)N($C_{1-6}$ alkyl)$_2$, —C(O)N($C_{1-6}$ haloalkyl)$_2$, —C(O)N($C_{3-8}$ cycloalkyl)$_2$, —NHC(O)($C_{1-4}$ alkyl), —NHC(O)($C_{1-6}$ haloalkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), —NHC(O)NH($C_{1-6}$ haloalkyl), —NHC(O)NH($C_{3-8}$ cycloalkyl), —NHC(O)NH(5- to 10-membered heterocyclyl), —NHC(O)NH($C_6$ aryl), —NHC(O)NH(5- to 10-membered heteroaryl), —S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)$_2$NH(C$_{1-6}$, alkyl), or —S(O)$_2$N(C$_{1-6}$ alkyl)$_2$,
wherein each alkyl, cycloalkyl, heterocyclyl, aryl, and heteroaryl is optionally substituted with one to three R$^{4b}$;

each R$^{4b}$ is independently C$_{1-6}$ alkyl, C$_{1-6}$ haloalkyl, C$_{3-6}$ cycloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_6$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(5- to 10-membered heteroaryl), —N(C$_{1-6}$ alkyl)$_2$, —N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(5- to 10-membered heteroaryl), —NHC(O)O(C$_{1-6}$alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(5- to 10-membered heteroaryl), —NHC(O)NH(C$_{1-6}$ alkyl), S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)$_2$NH(C$_{1-6}$ alkyl), or —S(O)$_2$N(C$_{1-6}$ alkyl)$_2$;

each L$^3$ is independently a bond, —(C$_{1-6}$ alkyl)O—, —(C$_{1-6}$ alkyl)N(R$^L$)C(O)—, —(C$_{1-6}$ alkyl)C(O)N(R$^L$)—, —(C$_{1-6}$ alkyl)N(R$^L$)C(O)(C$_{1-6}$ alkyl)-, —(C$_{1-6}$ alkyl)C(O)N(R$^L$)(C$_{1-6}$ alkyl)-, —(C$_{1-6}$ alkyl), —(C$_{1-6}$ alkyl)N(R$^L$)S(O)$_2$—, —N(R$^L$)S(O)$_2$—, —C(O)—, —(C$_{1-6}$ alkyl)C(O)—, or —N(R$^L$)C(O)—;

each R$^3$ is independently a bond, halogen, hydroxy, —CN, C$_{1-6}$ alkyl, C$_{2-4}$ alkynyl, C$_{1-6}$ alkoxy, C$_{3-8}$ cycloalkyl, 4- to 10-membered heterocyclyl, C$_6$ aryl, 5- to 10-membered heteroaryl, —NH$_2$, —NH(C$_{1-6}$ alkyl), —N(C$_{1-6}$ alkyl)$_2$, or —OC$_{3-8}$ cycloalkyl;
wherein each alkyl, alkynyl, alkoxy, cycloalkyl, heterocyclyl, aryl, and heteroaryl, is optionally substituted with one to four R$^{3a}$;

each R$^{3a}$ is independently C$_{1-6}$ alkyl, C$_{1-6}$ haloalkyl, halogen, C$_{3-8}$ cycloalkyl, 4- to 10-membered heterocyclyl, C$_6$ aryl, 5- to 10-membered heteroaryl, oxo, —OH, —CN, —NH$_2$, —O(C$_{1-6}$ alkyl), —O(C$_{1-6}$ haloalkyl), —O(C$_{3-8}$ cycloalkyl), —O(5- to 10-membered heterocyclyl), —O(C$_{6-10}$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(C$_6$ aryl), —NH(5- to 10-membered heteroaryl), —N(C$_{1-6}$ alkyl)$_2$, —N(C$_{1-6}$ haloalkyl), —N(C$_{3-8}$ cycloalkyl)$_2$, —N(C$_{1-6}$ alkyl)(C$_{1-6}$ haloalkyl), —N(C$_{1-6}$ alkyl)(C$_{3-8}$ cycloalkyl), —N(C$_{1-6}$ alkyl)(5- to 10-membered heterocyclyl), —N(C$_{1-6}$ alkyl)(C$_6$ aryl), —N(C$_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH(C$_{1-6}$ alkyl), —C(O)NH(C$_{1-6}$ haloalkyl), —C(O)NH(C$_{3-8}$ cycloalkyl), —C(O)NH(5- to 10-membered heterocyclyl), —C(O)NH(CG aryl), —C(O)NH(5- to 10-membered heteroaryl), —C(O)N(C$_{1-6}$ alkyl), —C(O)N(C$_{1-6}$ alkyl)$_2$, —C(O)N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(C$_6$ aryl), —NHC(O)(5- to 10-membered heteroaryl), —NHC(O)O(C$_{1-6}$ alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(C$_6$ aryl), —NHC(O)O(5- to 10-membered heteroaryl), —NHC(O)NH(C$_{1-6}$ alkyl), —NHC(O)NH(C$_{1-6}$ haloalkyl), —NHC(O)NH(C$_{3-8}$ cycloalkyl), —NHC(O)NH(5- to 10-membered heterocyclyl), —NHC(O)NH(C$_6$ aryl), —NHC(O)NH(5- to 10-membered heteroaryl), —S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)NH(C$_{1-6}$ alkyl), or —S(O)$_2$N(C$_{1-6}$ alkyl)$_2$,
wherein each alkyl, cycloalkyl, heterocyclyl, aryl, and heteroaryl is optionally substituted with one to three R$^{3b}$;

each R$^{3b}$ is independently C$_{1-6}$ alkyl, C$_{1-6}$ haloalkyl, C$_{3-8}$cycloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_{6-10}$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(5- to 10-membered heteroaryl), —N(C$_{1-6}$ alkyl)$_2$, —N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(5- to 10-membered heteroaryl), —NHC(O)O(C$_{1-6}$ alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(5- to 10-membered heteroaryl), —NHC(O)NH(C$_{1-6}$ alkyl), S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)$_2$NH(C$_{1-6}$ alkyl), or —S(O)$_2$N(C$_{1-6}$ alkyl)$_2$;

each R$^L$ is independently hydrogen, C$_{1-6}$ alkyl, C$_{1-6}$ haloalkyl, or C$_{3-8}$ cycloalkyl;

n is an integer from 0 to 3;

each X$^6$ and X$^7$ is independently N, CH, or CF,
wherein no more than two of X$^4$, X$^5$, X$^6$, and X$^7$ are N;

L$^2$ is a bond, C$_1$-C$_6$ alkyl, —(C$_{1-6}$ alkyl)O—, —(C$_{1-6}$ alkyl)O(C$_{1-6}$ alkyl)-, —(C$_{1-6}$alkyl) (R$^{L2}$)NC(O)—, —(C$_{1-6}$ alkyl)C(O)N(R$^{L2}$)—, —(C$_{1-6}$ alkyl)S(O)$_2$N(R$^L$)—, —(C$_{1-6}$ alkyl)N(R$^{L2}$)S(O)$_2$—, —(C$_{1-6}$ alkyl)S(O)$_2$N(R$^{L2}$) (C$_{1-6}$ alkyl)-, or —(C$_{1-6}$ alkyl)S(O)$_2$—(C$_{1-6}$ alkyl)-;

R$^{L2}$ is hydrogen or C$_{1-6}$ alkyl;

R$^5$ is hydrogen, —CN, —OR$^{5a}$, —C(O)NR$^{5a}{}_2$, —NR$^{5a}$C(O)R$^{5a}$, —NR$^{5a}{}_2$, C$_{1-6}$alkyl, C$_{3-8}$ cycloalkyl, C$_6$ aryl, 4- to 10-membered heterocyclyl, or 5- to 10-membered heteroaryl, wherein each alkyl, cycloalkyl, aryl, heterocyclyl, and heteroaryl is optionally substituted with one or two R$^{5b}$;

each R$^{5a}$ is independently hydrogen or C$_{1-6}$ alkyl;

each R$^{5b}$ is independently halogen, cyclopropyl, hydroxy, —CN, C$_{1-3}$ alkyl, C$_{1-3}$ alkoxy, —OCF$_3$, or —OCF$_2$H; and Z is O or S.

In some embodiments, the compound of Formula (I) is

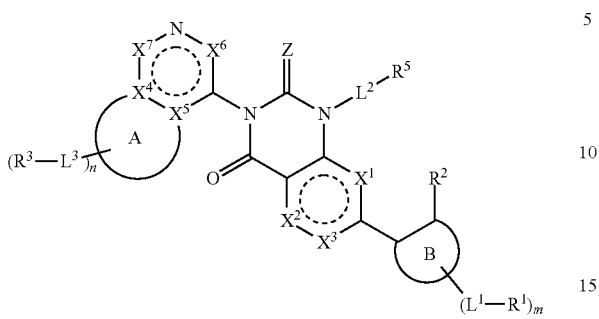

or a pharmaceutically acceptable salt thereof, wherein ring B is $C_{6-10}$ aryl or 5- to 10-membered heteroaryl; each $L^1$ is independently a bond, —O—, —($C_{1-6}$ alkyl)O—, —O($C_{1-6}$ alkyl)-, —($C_{1-6}$ alkyl)O($C_{1-6}$ alkyl)-, —C(O)—, —N($R^L$)C(O)—, —C(O)N($R^L$)—, —($C_{1-6}$ alkyl)($R^L$)NC(O)—, —($C_{1-6}$ alkyl)C(O)N($R^L$)—, —N($R^L$)C(O)($C_{1-6}$ alkyl)-, —C(O)N($R^L$)($C_{1-6}$ alkyl)-, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —S(O)$_2$—, —S(O)$_2$N($R^L$)—, —N($R^L$)—S(O)$_2$—, —($C_{1-6}$ alkyl)S(O)$_2$N($R^L$)—, —($C_{1-6}$ alkyl)N($R^L$)S(O)$_2$—, —S(O)$_2$N($R^L$)($C_{1-6}$ alkyl)-, —N($R^L$)S(O)$_2$($C_{1-6}$ alkyl)-, —($C_{1-6}$ alkyl)S(O)$_2$N($R^L$)(($C_{1-6}$ alkyl)-, or —($C_{1-6}$ alkyl)N($R^L$)S(O)$_2$($C_{1-6}$ alkyl)-;

each $R^1$ is independently halogen, —OH, —CN, $C_{1-6}$ alkyl, —CN, —C(O)NH$_2$, $C_{2-6}$ alkenyl, $C_{2-6}$ alkynyl, $C_{1-6}$ alkoxy, $C_{3-8}$ cycloalkyl, $C_6$ aryl, 5- to 12-membered heteroaryl, or 4- to 10-membered heterocyclyl, wherein each alkyl, alkenyl, alkynyl, alkoxy, cycloalkyl, aryl, heteroaryl, and heterocyclyl is optionally substituted with one to four $R^{1a}$;

alternatively, two $R^1$ taken together with the atoms of ring B to which they are attached form 5- to 10-membered heterocyclyl;

each $R^{1a}$ is independently $C_{1-6}$ alkyl, halogen, $C_{3-8}$ cycloalkyl, 4- to 10-membered heterocyclyl, $C_6$ aryl, 5- to 10-membered heteroaryl, oxo, —OH, —CN, —NH$_2$, —O($C_{1-6}$ alkyl), —O($C_{3-8}$ cycloalkyl), —O(5- to 10-membered heterocyclyl), —O($C_6$ aryl), —O(5- to 10-membered heteroaryl), —NH($C_{1-6}$ alkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{3-8}$ cycloalkyl)$_2$, —N(5- to 10-membered heterocyclyl)$_2$, —N($C_6$ aryl)$_2$, —N(5- to 10-membered heteroaryl)$_2$, —N($C_{1-6}$ alkyl)($C_{3-8}$ cycloalkyl), —N($C_{1-6}$ alkyl)(5- to 10-membered heterocyclyl), —N($C_{1-6}$ alkyl)($C_6$ aryl), —N($C_{1-6}$ alkyl)(5- to 10-membered heteroaryl), —C(O)(5- to 10-membered heterocyclyl), —C(O)(5- to 10-membered heteroaryl), —C(O)O($C_{1-6}$ alkyl), —C(O)O($C_{3-8}$ cycloalkyl), —C(O)O(5- to 10-membered heterocyclyl), —C(O)O($C_6$ aryl), —C(O)O(5- to 10-membered heteroaryl), —C(O)NH$_2$, —C(O)NH($C_{1-6}$ alkyl), —C(O)NH($C_{3-8}$ cycloalkyl), —C(O)NH(5- to 10-membered heterocyclyl), —C(O)NH($C_6$ aryl), —C(O)NH(5- to 10-membered heteroaryl), —C(O)N($C_{1-6}$ alkyl)$_2$, —C(O)N($C_{3-8}$ cycloalkyl)$_2$, —C(O)N(5- to 10-membered heterocyclyl)$_2$, —C(O)N($C_6$ aryl)$_2$, —C(O)N(5- to 10-membered heteroaryl)$_2$, —NHC(O)($C_{1-6}$ alkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), —NHC(O)NH($C_{3-8}$ cycloalkyl), —NHC(O)NH(5- to 10-membered heterocyclyl), —NHC(O)NH($C_6$ aryl), —NHC(O)NH(5- to 10-membered heteroaryl), —NHS(O)($C_{1-6}$ alkyl), —N($C_{1-6}$ alkyl)(S(O)($C_{1-6}$ alkyl), —S(O)$_2$($C_{1-6}$ alkyl), —S(O)$_2$($C_{3-8}$ cycloalkyl), —S(O)$_2$(5- to 10-membered heterocyclyl), —S(O)$_2$($C_6$ aryl), —S(O)$_2$(5- to 10-membered heteroaryl), —S(O)(NH)($C_{1-6}$ alkyl), —S(O)$_2$NH($C_{1-6}$ alkyl), or —S(O)$_2$N($C_{1-6}$ alkyl)$_2$, wherein each alkyl, cycloalkyl, heterocyclyl, aryl, and heteroaryl is optionally substituted with one to three $R^{1b}$;

each $R^{1b}$ is independently $C_{1-6}$ alkyl, $C_{1-6}$ haloalkyl, halogen, oxo, —OH, —NH$_2$, CO$_2$H, —O($C_{1-6}$ alkyl), —O($C_{1-6}$ haloalkyl), —O($C_{3-8}$ cycloalkyl), —O(5- to 10-membered heterocyclyl), —O($C_6$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{1-6}$ haloalkyl), —NHC(O)O($C_{2-6}$ alkynyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), S(O)$_2$($C_{1-6}$ alkyl), —S(O)$_2$($C_{1-6}$ haloalkyl), —S(O)$_2$($C_{3-8}$ cycloalkyl), —S(O)$_2$(5- to 10-membered heterocyclyl), —S(O)$_2$($C_6$ aryl), —S(O)$_2$(5- to 10-membered heteroaryl), —S(O)(NH)($C_{1-6}$ alkyl), —S(O)$_2$NH($C_{1-6}$ alkyl), or —S(O)$_2$N($C_{1-6}$ alkyl)$_2$;

m is an integer from 0 to 3;

$R^2$ is hydrogen, $C_{1-3}$ alkyl, $C_{1-3}$ haloalkyl, cyclopropyl, $C_{1-3}$ alkoxy, —O($C_{1-3}$ haloalkyl), —O(cyclopropyl), halogen, or —CN;

$X^1$ is S, N, or C($R^{x1}$);

$X^2$ is S, N, or C($R^{x2}$);

$X^3$ is N or C($R^{x3}$), provided that $X^1$ and $X^2$ are not S;

alternatively, $X^3$ is a bond, wherein one of $X^1$ and $X^2$ is S;

each $R^{x1}$, $R^{x2}$, and $R^{x3}$ is independently hydrogen, halogen, $C_{1-3}$ alkyl, $C_{1-3}$ haloalkyl, O $C_{1-3}$ haloalkyl, $C_{1-3}$ alkoxy, cyclopropyl, or O-cyclopropyl;

ring A taken together with $X^4$ and $X^5$ is $C_6$ aryl, 5- to 6-membered heteroaryl, $C_{5-10}$ cycloalkyl, or 5- to 10-membered heterocyclyl, wherein each $X^4$ and $X^5$ is independently N or C;

alternatively, ring A is absent, wherein $X^4$ is N or C-$L^{x4}$-$R^{x4}$, and $X^5$ is N or C-$L^{x5}$-$R^{x5}$;

each $L^{x4}$ and $L^{x5}$ is independently a bond, —($C_{1-6}$ alkyl)O—, —($C_{1-6}$ alkyl)N($R^L$)C(O)—, —($C_{1-6}$ alkyl)C(O)N($R^L$)—, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —($C_{1-6}$ alkyl), —($C_{1-6}$ alkyl)N($R^L$)S(O)$_2$—, —N($R^L$)S(O)$_2$—, —C(O)—, —($C_{1-6}$ alkyl)C(O)—, or —N($R^L$)C(O)—;

each $R^{x4}$ and $R^{x5}$ is independently hydrogen, halogen, hydroxy, —CN, $C_{1-6}$ alkyl, $C_{2-6}$ alkynyl, $C_{1-6}$ alkoxy, $C_{3-8}$ cycloalkyl, 4- to 10-membered heterocyclyl, 5- to 10-membered heteroaryl, —NH$_2$, —NH($C_{1-6}$ alkyl), —N($C_{1-6}$ alkyl)$_2$, —O($C_{1-6}$ alkyl), or —OC$_{3-8}$ cycloalkyl;
  wherein each alkyl, alkynyl, alkoxy, cycloalkyl, and heterocyclyl is optionally substituted with one to four $R^{4a}$;

each $R^{4a}$ is independently $C_{1-6}$ alkyl, $C_{1-6}$ haloalkyl, halogen, $C_{3-8}$ cycloalkyl, 4- to 10-membered heterocyclyl, $C_6$ aryl, 5- to 10-membered heteroaryl, oxo, —OH, —CN, —NH$_2$, —O($C_{1-6}$ alkyl), —O($C_{1-6}$ haloalkyl), —O($C_{3-8}$ cycloalkyl), —O(5- to 10-membered heterocyclyl), —O($C_{6-10}$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{1-6}$ haloalkyl)$_2$, —N($C_{3-8}$ cycloalkyl)$_2$, —N($C_{1-6}$ alkyl)($C_{1-6}$ haloalkyl), —N($C_{1-6}$ alkyl)($C_{3-8}$ cycloalkyl), —N($C_{1-6}$ alkyl)(5- to 10-membered heterocyclyl), —N($C_{1-6}$ alkyl)($C_6$ aryl), —N($C_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH($C_{1-6}$ alkyl), —C(O)NH($C_{1-6}$ haloalkyl), —C(O)NH($C_{3-8}$ cycloalkyl), —C(O)NH(5- to 10-membered heterocyclyl), —C(O)NH($C_6$ aryl), —C(O)NH(5- to 10-membered heteroaryl), —C(O)N($C_{1-6}$ alkyl)$_2$, —C(O)N($C_{1-6}$ haloalkyl)$_2$, —C(O)N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), —NHC(O)NH($C_{1-6}$ haloalkyl), —NHC(O)NH($C_{3-8}$ cycloalkyl), —NHC(O)NH(5- to 10-membered heterocyclyl), —NHC(O)NH($C_6$ aryl), —NHC(O)NH(5- to 10-membered heteroaryl), —S(O)$_2$($C_{1-6}$ alkyl), —S(O)$_2$($C_{1-6}$ haloalkyl), —S(O)$_2$($C_{3-8}$ cycloalkyl), —S(O)(NH)($C_{1-6}$ alkyl), —S(O)$_2$NH($C_{1-6}$ alkyl), or —S(O)$_2$N($C_{1-6}$ alkyl)$_2$,
  wherein each alkyl, cycloalkyl, heterocyclyl, aryl, and heteroaryl is optionally substituted with one to three $R^{4b}$;

each $R^{4b}$ is independently $C_{1-6}$ alkyl, $C_{1-6}$ haloalkyl, $C_{3-6}$ cycloalkyl, halogen, oxo, —OH, —NH$_2$, CO$_2$H, —O($C_{1-6}$ alkyl), —O($C_{1-6}$ haloalkyl), —O($C_{3-8}$ cycloalkyl), —O(5- to 10-membered heterocyclyl), —O($C_6$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH(5- to 10-membered heteroaryl), —N($C_{1-6}$ alkyl)$_2$, —N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)(5- to 10-membered heteroaryl), —NHC(O)O($C_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O(5- to 10-membered heteroaryl), —NHC(O)NH($C_{1-6}$ alkyl), S(O)$_2$($C_{1-6}$ alkyl), —S(O)$_2$($C_{1-6}$ haloalkyl), —S(O)$_2$($C_{3-8}$ cycloalkyl), —S(O)(NH)($C_{1-6}$ alkyl), —S(O)$_2$NH($C_{1-6}$ alkyl), or —S(O)$_2$N($C_{1-6}$ alkyl)$_2$;

each $L^3$ is independently a bond, —($C_{1-6}$ alkyl)O—, —($C_{1-6}$ alkyl)N($R^L$)C(O)—, —($C_{1-6}$ alkyl)C(O)N($R^L$)—, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —($C_{1-6}$ alkyl), —($C_{1-6}$ alkyl)N($R^L$)S(O)$_2$—, —N($R^L$)S(O)$_2$—. —C(O)—, —($C_{1-6}$ alkyl)C(O)—, or —N($R^L$)C(O)—;

each $R^3$ is independently a bond, halogen, hydroxy, —CN, $C_{1-6}$ alkyl, $C_{2-6}$ alkynyl, $C_{1-6}$ alkoxy, $C_{1-6}$ cycloalkyl, 4- to 10-membered heterocyclyl, $C_6$ aryl, 5- to 10-membered heteroaryl, —NH$_2$, —NH($C_{1-6}$ alkyl), —N($C_{1-6}$ alkyl)$_2$, or —OC$_{3-8}$ cycloalkyl;
  wherein each alkyl, alkynyl, alkoxy, cycloalkyl, and heterocyclyl is optionally substituted with one to four $R^{3a}$;

each $R^{3a}$ is independently $C_{1-6}$ alkyl, $C_{1-6}$ haloalkyl, halogen, $C_{3-8}$ cycloalkyl, 4- to 10-membered heterocyclyl, $C_6$ aryl, 5- to 10-membered heteroaryl, oxo, —OH, —CN, —NH$_2$, —O($C_{1-6}$ alkyl), —O($C_{1-6}$ haloalkyl), —O($C_{3-8}$ cycloalkyl), —O(5- to 10-membered heterocyclyl), —O($C_{6-10}$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{1-6}$ haloalkyl)$_2$, —N($C_{3-8}$ cycloalkyl)$_2$, —N($C_{1-6}$ alkyl)($C_{1-6}$ haloalkyl), —N($C_{1-6}$ alkyl)($C_{3-8}$ cycloalkyl), —N($C_{1-6}$ alkyl)(5- to 10-membered heterocyclyl), —N($C_{1-6}$ alkyl)($C_6$ aryl), —N($C_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH($C_{1-6}$ alkyl), —C(O)NH($C_{1-6}$ haloalkyl), —C(O)NH($C_{3-8}$ cycloalkyl), —C(O)NH(5- to 10-membered heterocyclyl), —C(O)NH($C_6$ aryl), —C(O)NH(5- to 10-membered heteroaryl), —C(O)N($C_{1-6}$ alkyl)$_2$, —C(O)N($C_{1-6}$ haloalkyl)$_2$, —C(O)N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), —NHC(O)NH($C_{1-6}$ haloalkyl), —NHC(O)NH($C_{3-8}$ cycloalkyl), —NHC(O)NH(5- to 10-membered heterocyclyl), —NHC(O)NH($C_6$ aryl), —NHC(O)NH(5- to 10-membered heteroaryl), —S(O)$_2$($C_{1-6}$ alkyl), —S(O)$_2$($C_{1-6}$ haloalkyl), —S(O)$_2$($C_{3-8}$ cycloalkyl), —S(O)(NH)($C_{1-6}$ alkyl), —S(O)$_2$NH($C_{1-6}$ alkyl), or —S(O)$_2$N($C_{1-6}$ alkyl)$_2$,
  wherein each alkyl, cycloalkyl, heterocyclyl, aryl, and heteroaryl is optionally substituted with one to three $R^{3b}$;

each $R^{3b}$ is independently $C_{1-6}$ alkyl, $C_{1-6}$ haloalkyl, $C_{3-8}$ cycloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_{6-10}$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(5- to 10-membered heteroaryl), —N(C$_{1-6}$ alkyl)$_2$, —N(C$_{3-8}$ cycloalkyl)$_2$, —NHC(O) (C$_{1-6}$ alkyl), —NHC(O)(C$_{1-6}$ haloalkyl), —NHC(O) (C$_{3-8}$ cycloalkyl), —NHC(O)(5- to 10-membered heterocyclyl), —NHC(O)(5- to 10-membered heteroaryl), —NHC(O)O(C$_{1-6}$ alkyl), —NHC(O)O (C$_{1-6}$ haloalkyl), —NHC(O)O(C$_{3-8}$ cycloalkyl), —NHC(O)O(5- to 10-membered heterocyclyl), —NHC(O)O(5- to 10-membered heteroaryl), —NHC(O)NH(C$_{1-6}$ alkyl), S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)$_2$NH(C$_{1-6}$ alkyl), or —S(O)$_2$N(C$_{1-6}$ alkyl)$_2$;

each $R^L$ is independently hydrogen, $C_{1-6}$ alkyl, $C_{1-6}$ haloalkyl, or $C_{3-8}$ cycloalkyl;

n is an integer from 0 to 3;

each $X^6$ and $X^7$ is independently N or CH,
wherein no more than two of $X^4$, $X^5$, $X^6$, and $X^7$ are N;

$L^2$ is a bond, $C_1$-$C_6$ alkyl, —(C$_{1-6}$ alkyl)O—, —(C$_{1-6}$ alkyl)O(C$_{1-6}$ alkyl)-, —(C$_{1-6}$alkyl) (R$^{L2}$)NC(O)—, —(C$_{1-6}$ alkyl)C(O)N(R$^{L2}$)—, —(C$_{1-6}$ alkyl)S(O)$_2$N (R$^2$)—, —(C$_{1-6}$ alkyl)N(R$^L$)S(O)$_2$—, or —(C$_{1-6}$ alkyl)S(O)$_2$N(R$^{L2}$) (C$_{1-6}$ alkyl)-;

$R^{L2}$ is hydrogen or $C_{1-6}$ alkyl;

$R^5$ is hydrogen, —CN, —OR$^{5a}$, —C(O)NR$^{5a}{}_2$, —NR$^{5a}$C(O)R$^{5a}$, —NR$^{5a}{}_2$, $C_{3-8}$ cycloalkyl, $C_6$ aryl, 4- to 10-membered heterocyclyl, or 5- to 10-membered heteroaryl, wherein each cycloalkyl, aryl, heterocyclyl, and heteroaryl is optionally substituted with one or two $R^{5b}$;

each $R^{5a}$ is independently hydrogen or $C_{1-6}$ alkyl;

each $R^{5b}$ is independently halogen, cyclopropyl, hydroxy, —CN, $C_{1-3}$ alkyl, $C_{1-3}$ alkoxy, —OCF$_3$, or —OCF$_2$H; and Z is O or S.

In some embodiments, the compound of Formula (I) is

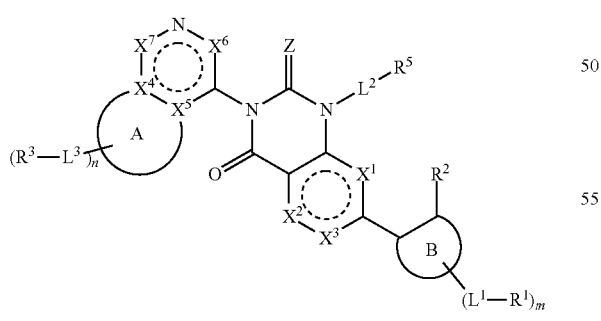

I or a pharmaceutically acceptable salt thereof, wherein ring  is $C_{6-10}$ aryl or 5- to 10-membered heteroaryl;

each $L^1$ is independently a bond. —O—, —(C$_{1-6}$ alkyl) O—, —O(C$_{1-6}$ alkyl)-, —(C$_{1-6}$ alkyl-O(C$_{1-6}$ alkyl)-,
—C(O)—, —N(R$^L$)C(O)—, —C(O)N(R$^L$)—, —(C$_{1-6}$ alkyl)(R$^L$)NC(O)—, —(C$_{1-6}$ alkyl)C(O)N (R$^L$)—, —N(R$^L$)C(O)(C$_{1-6}$ alkyl)-, —C(O)N(R$^L$) (C$_{1-6}$ alkyl)-, —(C$_{1-6}$ alkyl)N(R$^L$)C(O)(C$_{1-6}$ alkyl)-, —(C$_{1-6}$ alkyl)C(O)N(R$^L$)(C$_{1-6}$ alkyl)-, —S(O)$_2$—, —S(O)$_2$N(R$^L$)—, —N(R$^L$)—S(O)$_2$—, —(C$_{1-6}$ alkyl)S(O)$_2$N(R$^L$)—, —(C$_{1-6}$ alkyl)N(R$^L$)S(O)$_2$—, —S(O)$_2$N(R$^L$)(C$_{1-6}$ alkyl)-, —N(R$^L$)S(O)$_2$(C$_{1-6}$ alkyl)-, —(C$_{1-6}$ alkyl)S(O)$_2$N(R$^L$)(C$_{1-6}$ alkyl)-, or —(C$_{1-6}$ alkyl)N(R$^L$)S(O)$_2$(C$_{1-6}$ alkyl)-;

each $R^1$ is independently halogen, —OH, —CN, $C_{1-6}$ alkyl, —CN, —C(O)NH$_2$, $C_{2-6}$ alkenyl, $C_{2-6}$ alkynyl, $C_{1-6}$ alkoxy, $C_{3-8}$ cycloalkyl, $C_6$ aryl, 5- to 12-membered heteroaryl, or 4- to 10-membered heterocyclyl,
wherein each alkyl, alkenyl, alkynyl, alkoxy, cycloalkyl, aryl, heteroaryl, and heterocyclyl is optionally substituted with one to four $R^{1a}$;

each $R^{1a}$ is independently $C_{1-6}$ alkyl, halogen, $C_{3-8}$ cycloalkyl, 5- to 10-membered heterocyclyl, $C_6$ aryl, 5- to 10-membered heteroaryl, oxo. —OH, —CN, —NH$_2$, —O(C$_{1-6}$ alkyl), —O(C$_{3-8}$ cycloalkyl), —O(5- to 10-membered heterocyclyl), —O(C$_6$ aryl), —O(5- to 10-membered heteroaryl), —NH(C$_{1-6}$ alkyl), —NH(C$_{3-8}$ cycloalkyl), —NH(5- to 10-membered heterocyclyl), —NH(C$_6$ aryl), —NH(5- to 10-membered heteroaryl), —N(C$_{1-6}$ alkyl)$_2$, —N(C$_{3-8}$ cycloalkyl)$_2$, —N(5- to 10-membered heterocyclyl)$_2$, —N(C$_6$ aryl)$_2$, —N(5- to 10-membered heteroaryl)$_2$, —N(C$_{1-6}$ alkyl)(C$_{3-8}$ v cycloalkyl), —N(C$_{1-6}$ alkyl)(5- to 10-membered heterocyclyl), —N(C$_{1-6}$ alkyl)(C$_6$ aryl), —N(C$_{1-6}$ alkyl)(5- to 10-membered heteroaryl), —C(O)(5- to 10-membered heterocyclyl), —C(O)(5- to 10-membered heteroaryl), —C(O)O(C$_{1-6}$ alkyl), —C(O)O(C$_{3-8}$ cycloalkyl), —C(O)O(5- to 10-membered heterocyclyl), —C(O)O(C$_6$ aryl), —C(O)O(5- to 10-membered heteroaryl), —C(O)NH$_2$, —C(O)NH(C$_{1-6}$ alkyl), —C(O)NH(C$_{3-8}$ cycloalkyl), —C(O)NH(5- to 10-membered heterocyclyl), —C(O)NH(C$_6$ aryl), —C(O)NH(5- to 10-membered heteroaryl), —C(O) N(C$_{1-6}$ alkyl)$_2$, —C(O)N(C$_{3-8}$ cycloalkyl)$_2$, —C(O) N(5- to 10-membered heterocyclyl)$_2$, —C(O)N(C$_6$ aryl)$_2$, —C(O)N(5- to 10-membered heteroaryl)$_2$, —NHC(O)(C$_{1-6}$ alkyl), —NHC(O)(C$_{3-8}$ cycloalkyl), —NHC(O)(5- to 10-membered heterocyclyl), —NHC(O)(C$_6$ aryl), —NHC(O)(5- to 10-membered heteroaryl), —NHC(O)O(C$_{1-6}$ alkyl), —NHC(O)O (C$_{3-8}$ cycloalkyl), —NHC(O)O(5- to 10-membered heterocyclyl), —NHC(O)O(C$_6$ aryl), —NHC(O)O (5- to 10-membered heteroaryl), —NHC(O)NH(C$_{1-6}$ alkyl), —NHC(O)NH(C$_{3-8}$ cycloalkyl), —NHC(O) NH(5- to 10-membered heterocyclyl), —NHC(O) NH(C$_6$ aryl), —NHC(O)NH(5- to 10-membered heteroaryl), —NHS(O)(C$_{1-6}$ alkyl), —N(C$_{1-6}$ alkyl)(S (O)(C$_{1-6}$ alkyl), —S(O)$_2$(C$_{1-6}$ alkyl), —S(O)$_2$(C$_{3-8}$ cycloalkyl), —S(O)$_2$(5- to 10-membered heterocyclyl), —S(O)$_2$(C$_6$ aryl), —S(O)$_2$(5- to 10-membered heteroaryl), —S(O)(NH)(C$_{1-6}$ alkyl), —S(O)$_2$NH (C$_{1-6}$ alkyl), or —S(O)$_2$N(C$_{1-6}$ alkyl)$_2$,
wherein each alkyl, cycloalkyl, heterocyclyl, aryl, and heteroaryl is optionally substituted with one to three $R^{1b}$;

each $R^{1b}$ is independently $C_{1-6}$ alkyl, $C_{1-6}$ haloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_6$ aryl), —O(5- to 10-membered heteroaryl), —NH(C$_{1-6}$ alkyl), —NH($C_{1-6}$ haloalkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{1-6}$ haloalkyl), —NHC(O)O($C_{2-6}$ alkynyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), S(O)$_2$($C_{1-6}$ alkyl), —S(O)$_2$($C_{1-6}$ haloalkyl), —S(O)$_2$($C_{3-8}$ cycloalkyl), —S(O)$_2$(5- to 10-membered heterocyclyl), —S(O)$_2$($C_6$ aryl), —S(O)$_2$(5- to 10-membered heteroaryl), —S(O)(NH)($C_{1-6}$ alkyl), —S(O)$_2$NH($C_{1-6}$ alkyl), or —S(O)$_2$N($C_{1-6}$ alkyl)$_2$;

m is an integer from 0 to 3;

$R^2$ is hydrogen, $C_{1-3}$ alkyl, $C_{1-3}$ haloalkyl, cyclopropyl, $C_{1-3}$ alkoxy, —O($C_{1-3}$ haloalkyl), —O(cyclopropyl), halogen, or —CN;

$X^1$ is S, N, or C($R^{x1}$);

$X^2$ is S, N, or C($R^{x2}$)

$X^3$ is N or C($R^{x3}$), provided that $X^1$ and $X^2$ are not S; alternatively, $X^1$ is a bond, wherein one of $X^1$ and $X^2$ is S;

each $R^{x1}$ $R^{x2}$, and $R^{x3}$ is independently hydrogen, halogen, $C_{1-3}$ alkyl, $C_{1-3}$ haloalkyl, O $C_{1-3}$ haloalkyl, $C_{1-3}$ alkoxy, cyclopropyl, or O-cyclopropyl;

ring (A) taken together with $X^4$ and $X^5$ is $C_6$ aryl, 5- to 6-membered heteroaryl, $C_{5-10}$ cycloalkyl, or 5- to 10-membered heterocyclyl,
wherein each $X^4$ and $X^5$ is independently N or C;

alternatively, ring (A) is absent, wherein $X^4$ is N or C-$L^{x4}$-$R^{x4}$, and $X^5$ is N or C-$L^{x5}$-$R^{x5}$;

each $L^{x4}$ and $L^{x5}$ is independently a bond, —($C_{1-6}$ alkyl)O—, —($C_{1-6}$ alkyl)N($R^L$)C(O)—, —($C_{1-6}$ alkyl)C(O)N($R^L$)—, —($C_{1-6}$ alkyl)N($R^L$)C(O)($C_{1-6}$ alkyl)-, —($C_{1-6}$ alkyl)C(O)N($R^L$)($C_{1-6}$alkyl)-, —($C_{1-6}$ alkyl), —($C_{1-6}$alkyl)N($R^1$)S(O)$_2$—, —N($R^L$)S(O)$_2$—, —C(O)—, —($C_{1-6}$ alkyl)C(O)—, or —N($R^L$)C(O)—;

each $R^{x4}$ and $R^{x5}$ is independently a hydrogen, halogen, hydroxy, —CN, $C_{1-6}$ alkyl, $C_{2-6}$ alkynyl, $C_{1-6}$ alkoxy, $C_{3-8}$ cycloalkyl, 4- to 10-membered heterocyclyl, 5- to 10-membered heteroaryl, —NH$_2$, —NH($C_{1-6}$ alkyl), —N($C_{1-6}$ alkyl)$_2$, —O($C_{1-6}$ alkyl), or —O$C_{3-8}$ cycloalkyl;
wherein each alkyl, alkynyl, alkoxy, cycloalkyl, and heterocyclyl is optionally substituted with one to four $R^{4a}$;

each $R^{4a}$ is independently $C_{1-6}$ alkyl, $C_{1-6}$ haloalkyl, halogen, $C_{3-8}$ cycloalkyl, 5- to 10-membered heterocyclyl, $C_6$ aryl, 5- to 10-membered heteroaryl, oxo, —OH, —CN, —NH$_2$, —O($C_{1-6}$ alkyl), —O($C_{1-6}$ haloalkyl), —O($C_{3-8}$ cycloalkyl), —O(5- to 10-membered heterocyclyl), —O($C_{6-10}$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{1-6}$ haloalkyl)$_2$, —N($C_{3-8}$ cycloalkyl)$_2$, —N($C_{1-6}$ alkyl)($C_{1-6}$ haloalkyl), —N($C_{1-6}$ alkyl)($C_{3-8}$ cycloalkyl), —N($C_{1-6}$ alkyl)(5- to 10-membered heterocyclyl), —N($C_{1-6}$ alkyl)($C_6$ aryl), —N($C_{1-6}$ alkyl)(5- to 10-membered heteroaryl), —C(O)(5- to 10-membered heteroaryl), —C(O)(5- to 10-membered heteroaryl), —C(O)NH$_2$, —C(O)NH($C_{1-6}$ alkyl), —C(O)NH($C_{1-6}$ haloalkyl), —C(O)NH($C_{3-8}$ cycloalkyl), —C(O)NH(5- to 10-membered heterocyclyl), —C(O)NH($C_6$ aryl), —C(O)NH(5- to 10-membered heteroaryl), —C(O)N($C_{1-6}$ alkyl)$_2$, —C(O)N($C_{1-6}$ haloalkyl)$_2$, —C(O)N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), —NHC(O)NH($C_{1-6}$ haloalkyl), —NHC(O)NH($C_{3-8}$ cycloalkyl), —NHC(O)NH(5- to 10-membered heterocyclyl), —NHC(O)NH($C_6$ aryl), —NHC(O)NH(5- to 10-membered heteroaryl), —S(O)$_2$($C_{1-6}$ alkyl), —S(O)$_2$($C_1$-6 haloalkyl), —S(O)$_2$($C_{3-8}$ cycloalkyl), —S(O)(NH)($C_{1-6}$ alkyl), —S(O)$_2$NH($C_{1-6}$ alkyl), or —S(O)$_2$N($C_{1-6}$ alkyl)$_2$,
wherein each alkyl, cycloalkyl, heterocyclyl, aryl, and heteroaryl is optionally substituted with one to three $R^{4b}$;

each $R^{4b}$ is independently $C_{1-6}$ alkyl, $C_{1-6}$ haloalkyl, $C_{3-6}$ cycloalkyl, halogen, oxo, —OH, —NH$_2$, CO$_2$H, —O($C_{1-6}$ alkyl), —O($C_{1-6}$ haloalkyl), —O($C_{3-8}$ cycloalkyl), —O(5- to 10-membered heterocyclyl), —O($C_6$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH(5- to 10-membered heteroaryl), —N($C_{1-6}$ alkyl)$_2$, —N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)(5- to 10-membered heteroaryl), —NHC(O)O($C_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O(5- to 10-membered heteroaryl), —NHC(O)NH($C_{1-6}$ alkyl), S(O)$_2$($C_{1-6}$ alkyl), —S(O)$_2$($C_{1-6}$ haloalkyl), —S(O)$_2$($C_{3-8}$ cycloalkyl), —S(O)(NH)($C_{1-6}$ alkyl), —S(O)$_2$NH($C_{1-6}$ alkyl), or —S(O)$_2$N($C_{1-6}$ alkyl)$_2$;

each $L^3$ is independently a bond, —($C_{1-6}$ alkyl)O—, —($C_{1-6}$ alkyl)N($R^L$)C(O)—, —($C_{1-6}$ alkyl)C(O)N($R^L$)—, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —($C_{1-6}$ alkyl), —($C_{1-6}$ alkyl)N($R^L$)S(O)$_2$—, —N($R^L$)S(O)$_2$—. —C(O)—, —($C_{1-6}$ alkyl)C(O)—, or —N($R^L$)C(O)—;

each $R^{3a}$ is independently a bond, halogen, hydroxy, —CN, $C_{1-6}$ alkyl, $C_{2-6}$ alkynyl, $C_{1-6}$ alkoxy, $C_{3-8}$ cycloalkyl, 4- to 10-membered heterocyclyl, $C_6$ aryl, 5- to 10-membered heteroaryl, —NH$_2$, —NH($C_{1-6}$ alkyl), —N($C_{1-6}$ alkyl)$_2$, or —O$C_{3-8}$ cycloalkyl;
wherein each alkyl, alkynyl, alkoxy, cycloalkyl, and heterocyclyl is optionally substituted with one to four $R^{3a}$;

each $R^{3a}$ is independently $C_{1-6}$ alkyl, $C_{1-6}$ haloalkyl, halogen, $C_{3-8}$ cycloalkyl, 5- to 10-membered heterocyclyl, $C_6$ aryl, 5- to 10-membered heteroaryl, oxo, —OH, —CN, —NH$_2$, —O(C$_{1-6}$ alkyl), —O(C$_{1-6}$ haloalkyl), —O(C$_{3-8}$ cycloalkyl), —O(5- to 10-membered heterocyclyl), —O(C$_{6-10}$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(C$_6$ aryl), —NH(5- to 10-membered heteroaryl), —N(C$_{1-6}$ alkyl)$_2$, —N(C$_{1-6}$ haloalkyl)$_2$, —N(C$_{3-8}$ cycloalkyl)$_2$, —N(C$_{1-6}$ alkyl)(C$_{1-6}$ haloalkyl), —N(C$_{1-6}$ alkyl)(C$_{3-8}$ cycloalkyl), —N(C$_{1-6}$ alkyl)(5- to 10-membered heterocyclyl), —N(C$_{1-6}$ alkyl)(C$_6$ aryl), —N(C$_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH(C$_{1-6}$ alkyl), —C(O)NH(C$_{1-6}$ haloalkyl), —C(O)NH(C$_{3-8}$ cycloalkyl), —C(O)NH (5- to 10-membered heterocyclyl), —C(O)NH(C$_6$ aryl), —C(O)NH(5- to 10-membered heteroaryl), —C(O)N(C$_{1-6}$ alkyl)$_2$, —C(O)N(C$_{1-6}$ haloalkyl)$_2$, —C(O)N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(C$_6$ aryl), —NHC(O)(5- to 10-membered heteroaryl), —NHC(O)O(C$_{1-6}$ alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(C$_6$ aryl), —NHC(O)O(5- to 10-membered heteroaryl), —NHC(O)NH(C$_{1-6}$ alkyl), —NHC(O)NH(C$_{1-6}$ haloalkyl), —NHC(O)NH(C$_{3-8}$ cycloalkyl), —NHC(O)NH(5- to 10-membered heterocyclyl), —NHC(O)NH(C$_6$ aryl), —NHC(O)NH(5- to 10-membered heteroaryl), —S(O)$_2$(C$_{1-6}$ alkyl), —S(O)$_2$(C$_1$-6 haloalkyl), —S(O)$_2$(C$_{3-8}$ cycloalkyl), —S(O)(NH)(C$_{1-6}$ alkyl), —S(O)$_2$NH(C$_{1-6}$ alkyl), or —S(O)$_2$N(C$_{1-6}$ alkyl)$_2$, wherein each alkyl, cycloalkyl, heterocyclyl, aryl, and heteroaryl is optionally substituted with one to three $R^{3b}$;

each $R^{3b}$ is independently $C_{1-6}$ alkyl, $C_{1-6}$ haloalkyl, $C_{3-8}$ cycloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_{6-10}$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(5- to 10-membered heteroaryl), —N(C$_{1-6}$ alkyl)$_2$, —N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(5- to 10-membered heteroaryl), —NHC(O)O(C$_{1-6}$ alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(5- to 10-membered heteroaryl), —NHC(O)NH(C$_{1-6}$ alkyl), S(O)$_2$(C$_{1-6}$ alkyl), —S(O)$_2$(C$_{1-6}$ haloalkyl), —S(O)$_2$(C$_{3-8}$ cycloalkyl), —S(O)(NH)(C$_{1-6}$ alkyl), —S(O)$_2$NH(C$_{1-6}$ alkyl), or —S(O)$_2$N(C$_{1-6}$ alkyl)$_2$;

each $R^L$ is independently hydrogen, $C_{1-6}$ alkyl, $C_{1-6}$ haloalkyl, or $C_{3-8}$ cycloalkyl;

n is an integer from 0 to 3;

each $X^6$ and $X^7$ is independently N or CH,
wherein no more than two of $X^4$, $X^5$, $X^6$, and $X^7$ are N;

$L^2$ is a bond, $C_1$-$C_6$ alkyl, —(C$_{1-6}$ alkyl)O—, —(C$_{1-6}$ alkyl)O(C$_{1-6}$ alkyl)-, —(C$_{1-6}$ alkyl) (R$^{L2}$)NC(O)—, —(C$_{1-6}$ alkyl)C(O)N(R$^{L2}$)—, —(C$_{1-6}$ alkyl)S(O)$_2$N (R$^{L2}$)—, —(C$_{1-6}$ alkyl)N(R$^{L2}$)S(O)$_2$—, or —(C$_{1-6}$ alkyl)S(O)$_2$N(R$^2$) (C$_{1-6}$ alkyl)-;

$R^{L2}$ is hydrogen or $C_{1-6}$ alkyl;

$R^5$ is hydrogen. —CN, —OR$^{5a}$, —C(O)NR$^{5a}{}_2$, —NR$^{5a}{}_2$, $C_{3-8}$ cycloalkyl, $C_6$ aryl, 4- to 10-membered heterocyclyl, or 5- to 10-membered heteroaryl, wherein each cycloalkyl, aryl, heterocyclyl, and heteroaryl is optionally substituted with one or two $R^{5b}$;

each $R^{5a}$ is independently hydrogen or $C_{1-6}$ alkyl;

each $R^{5b}$ is independently halogen, cyclopropyl, hydroxy, —CN, $C_{1-3}$ alkyl, $C_{1-3}$ alkoxy, —OCF$_3$, or —OCF$_2$H; and Z is O or S.

In some embodiments, the disclosure provides a compound according to the structure of Formula (I-1):

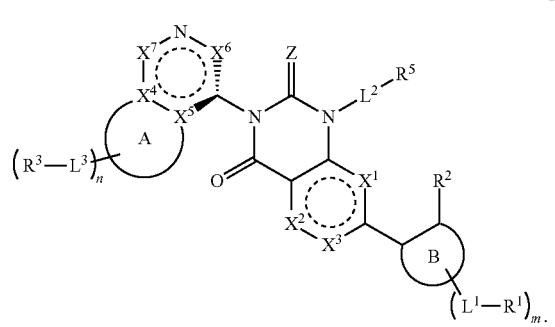

I-1 and/or pharmaceutically acceptable salt(s) thereof, wherein ⓐ, ⓑ, $L^1$, $L^2$, $L^3$, $R^1$, $R^2$, $R^3$, $R^5$, $X^1$, $X^2$, $X^3$, $X^4$, $X^5$, $X^6$, $X^7$, Z, m, and n are as described herein.

In some embodiments, a compound of the disclosure is a compound, or pharmaceutically acceptable salt thereof, wherein $X^3$ is N or C(R$^{x3}$). In some embodiments, a compound of the disclosure is a compound, or pharmaceutically acceptable salt thereof, wherein $X^3$ is N. In some embodiments, a compound of the disclosure is a compound, or pharmaceutically acceptable salt thereof, wherein $X^3$ is C(R$^L$). In some embodiments, a compound of the disclosure is a compound, or pharmaceutically acceptable salt thereof, wherein is N or C(R$^{x3}$), and $X^1$ and $X^2$ are not S.

In some embodiments, a compound of the disclosure is a compound, or pharmaceutically acceptable salt thereof, wherein $X^1$ is S, N, or C(R$^{x1}$). In some embodiments, a compound of the disclosure is a compound, or pharmaceutically acceptable salt thereof, wherein $X^1$ is S. In some embodiments, a compound of the disclosure is a compound, or pharmaceutically acceptable salt thereof, wherein $X^1$ is N. In some embodiments, a compound of the disclosure is a compound, or pharmaceutically acceptable salt thereof, wherein $X^1$ is C(R$^{x1}$).

In some embodiments, a compound of the disclosure is a compound, or pharmaceutically acceptable salt thereof, wherein $X^2$ is S, N, or C(R$^{x1}$). In some embodiments, a compound of the disclosure is a compound, or pharmaceutically acceptable salt thereof, wherein $X^2$ is S. In some embodiments, a compound of the disclosure is a compound, or pharmaceutically acceptable salt thereof, wherein $X^2$ is N.

In some embodiments, a compound of the disclosure is a compound, or pharmaceutically acceptable salt thereof, wherein $X^2$ is $C(R^L)$.

In some embodiments, a compound of the disclosure is a compound, or pharmaceutically acceptable salt thereof, wherein $X^1$ and $X^2$ are not S. In some embodiments, exactly one of $X^1$ and $X^2$ is S.

In some embodiments, a compound of the disclosure is a compound, or pharmaceutically acceptable salt thereof, wherein $X^3$ is a bond, N, or $C(R^{x3})$. In some embodiments, a compound of the disclosure is a compound, or pharmaceutically acceptable salt thereof, wherein $X^3$ is N or C(RV). In some embodiments, a compound of the disclosure is a compound, or pharmaceutically acceptable salt thereof, wherein $X^3$ is N. In some embodiments, a compound of the disclosure is a compound, or pharmaceutically acceptable salt thereof, wherein $X^3$ is $C(R^{x3})$.

In some embodiments, a compound of the disclosure is a compound, or pharmaceutically acceptable salt thereof, wherein $X^1$ is $C(R^{x1})$, $X^2$ is $C(R^{x2})$, and $X^3$ is $C(R^{x3})$. In some embodiments, a compound of the disclosure is a compound, or pharmaceutically acceptable salt thereof, wherein $X^1$ is $C(R^L)$, $X^2$ is $C(R^{x2})$, and $X^3$ is N. In some embodiments, a compound of the disclosure is a compound, or pharmaceutically acceptable salt thereof, wherein $X^1$ is N, $X^2$ is $C(R^{x2})$, and $X^3$ is $C(R^{x3})$. In some embodiments, a compound of the disclosure is a compound, or pharmaceutically acceptable salt thereof, wherein $X^1$ is N, $X^2$ is $C(R^{x2})$, and $X^3$ is N. In some embodiments, a compound of the disclosure is a compound, or pharmaceutically acceptable salt thereof, wherein $X^1$ is $C(R^{x1})$, $X^2$ is N, and $X^3$ is $C(R^{x3})$. In some embodiments, a compound of the disclosure is a compound, or pharmaceutically acceptable salt thereof, wherein $X^1$ is $C(R^L)$, $X^2$ is N, and $X^3$ is N.

In some embodiments, the disclosure provides a compound according to the structure of Formula (III):

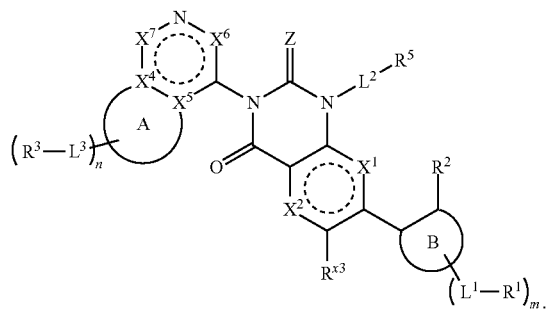

III and/or pharmaceutically acceptable salt(s) thereof, wherein (A), (B), $L^1$, $L^2$, $L^3$, $R^1$, $R^2$, $R^3$, $R^5$, $X^1$, $X^2$, $X^4$, $X^5$, $X^6$, $X^7$, Z, m, and n are as described herein.

In some embodiments, the disclosure provides a compound according to the structure of Formula (III-a):

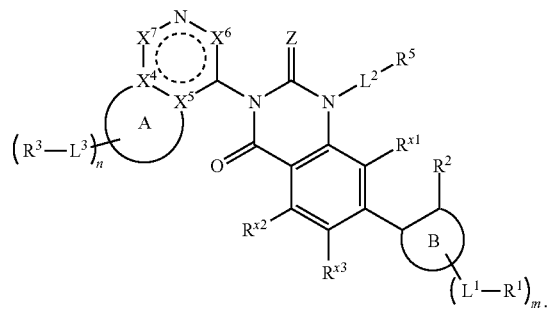

III-a and/or pharmaceutically acceptable salt(s) thereof, wherein (A), (B), $L^1$, $L^2$, $L^3$, $R^1$, $R^2$, $R^3$, $R^5$, $R^{x1}$, $R^{x2}$, $R^{x3}$, $X^4$, $X^5$, $X^6$, $X^7$, Z, m, and n are as described herein.

In some embodiments, the disclosure provides a compound according to the structure of Formula (III-b):

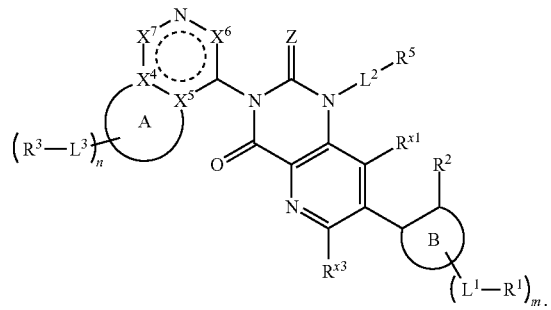

III-b and/or pharmaceutically acceptable salt(s) thereof, wherein (A), (B), $L^1$, $L^2$, $L^3$, $R^1$, $R^2$. $R^3$, $R^5$, $R^{x1}$, $R^{x3}$, $X^4$, $X^5$, $X^6$, $X^7$, Z, m, and n are as described herein.

In some embodiments, the disclosure provides a compound according to the structure of Formula (III-c):

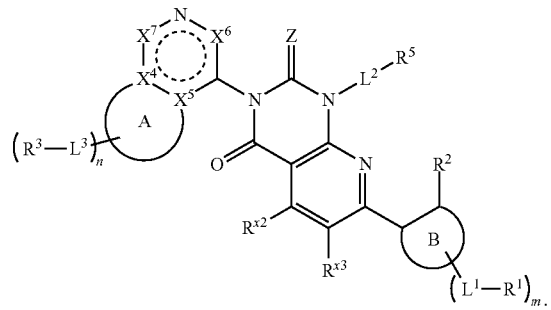

III-c and/or pharmaceutically acceptable salt(s) thereof, wherein (A), (B), $L^1, L^2, L^3, R^1, R^2, R^3, R^5, R^{x2}, R^{x3}, X^4, X^5, X^6, X^7$, Z, m, and n are as described herein.

In some embodiments, the disclosure provides a compound according to the structure of Formula (III-d):

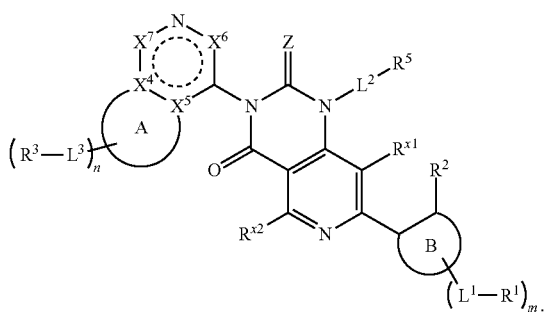

III-d and/or pharmaceutically acceptable salt(s) thereof, wherein (A), (B), $L^1, L^2, L^3, R^1, R^2, R^3, R^5, R^{x1}, R^{x2}, X^4, X^5, X^6, X^7$, Z, m, and n are as described herein.

In some embodiments, a compound of the disclosure is a compound, or pharmaceutically acceptable salt thereof, wherein $X^1$ is S, $X^2$ is $C(R^{x2})$, and X is a bond. In some embodiments, a compound of the disclosure is a compound, or pharmaceutically acceptable salt thereof, wherein $X^1$ is S, $X^2$ is N, and $X^3$ is a bond. In some embodiments, a compound of the disclosure is a compound, or pharmaceutically acceptable salt thereof, wherein $X^1$ is $C(R^{x2})$, $X^2$ is S, and $X^3$ is a bond. In some embodiments, a compound of the disclosure is a compound, or pharmaceutically acceptable salt thereof, wherein $X^1$ is N, $X^2$ is S, and $X^3$ is a bond.

In some embodiments, the disclosure provides a compound according to the structure of Formula (II)

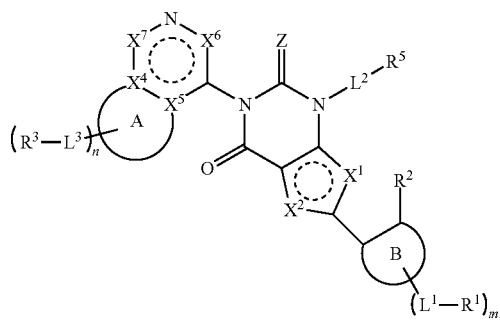

II and/or pharmaceutically acceptable salt(s) thereof, wherein (A), (B), $L^1, L^2, L^3, R^1, R^2, R^3, R^5, R^{x1}, X^4, X^5, X^6, X^7$, Z, m, and n are as described herein.

In some embodiments, the disclosure provides a compound according to the structure of Formula (II-a)

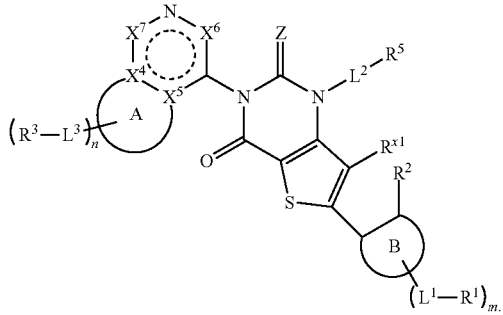

II-a and/or pharmaceutically acceptable salt(s) thereof, wherein (A), (B), $L^1, L^2, L^3, R^1, R^2, R^3, R^5, R^{x1}, X^4, X^5, X^6, X^7$, Z, m, and n are as described herein.

In some embodiments, the disclosure provides a compound according to the structure of Formula (II-b)

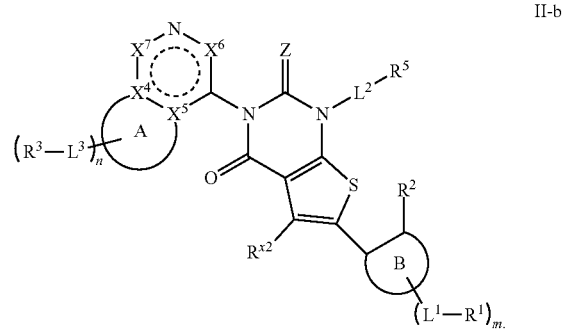

II-b and/or pharmaceutically acceptable salt(s) thereof, wherein (A), (B), $L^1, L^2, L^3, R^1, R^2, R^3, R^5, R^{x2}, X^4, X^5, X^6, X^7$, Z, m, and n are as described herein.

In some embodiments, the disclosure provides a compound according to the structure of Formula (II-c)

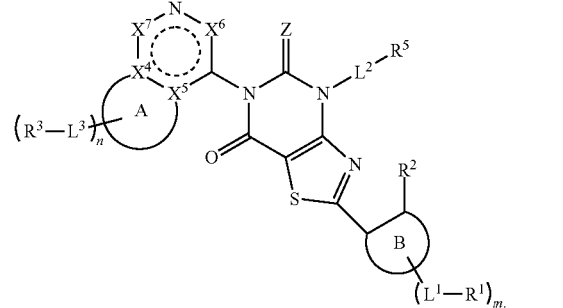

II-c and/or pharmaceutically acceptable salt(s) thereof, wherein (A), (B), $L^1, L^2, R^1, R^2, R^3, R^5, R^{x4}, X^5, X^6, X^7$, Z, m, and n are as described herein.

In some embodiments, the disclosure provides a compound according to the structure of Formula (II-d)

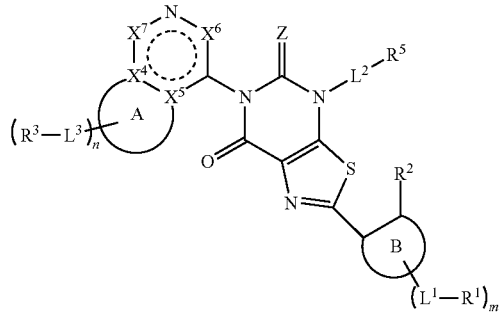

II-d and/or pharmaceutically acceptable salt(s) thereof, wherein $\overset{A}{\bigcirc}$, $\overset{B}{\bigcirc}$, $L^1$, $L^2$, $L^3$, $R^1$, $R^2$, $R^3$, $R^5$, $R^{x4}$, $X^5$, $X^6$, $X^7$, Z, m, and n are as described herein.

In some embodiments, a compound of the disclosure is a compound, or pharmaceutically acceptable salt thereof, wherein ring $\overset{B}{\bigcirc}$ is $C_{6-10}$ aryl or 5- to 10-membered heteroaryl. In some embodiments, a compound of the disclosure is a compound, or pharmaceutically acceptable salt thereof, wherein ring $\overset{B}{\bigcirc}$ is $C_{6-10}$ aryl. In some embodiments, a compound of the disclosure is a compound, or pharmaceutically acceptable salt thereof, wherein ring $\overset{B}{\bigcirc}$ is C aryl. In some embodiments, a compound of the disclosure is a compound, or pharmaceutically acceptable salt thereof, wherein ring $\overset{B}{\bigcirc}$ is $C_{10}$ aryl. In some embodiments, the $C_{6-10}$ aryl is phenyl. In some embodiments, the $C_{6-10}$ aryl is indanyl.

In some embodiments, a compound of the disclosure is a compound, or pharmaceutically acceptable salt thereof, wherein ring $\overset{B}{\bigcirc}$ is $C_6$ aryl and the substituent meta to the point of attachment is hydrogen. In some embodiments, a compound of the disclosure is a compound, or pharmaceutically acceptable salt thereof, wherein ring $\overset{B}{\bigcirc}$ is

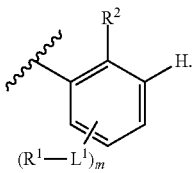

In some embodiments, a compound of the disclosure is a compound, or pharmaceutically acceptable salt thereof, wherein ring $\overset{B}{\bigcirc}$ is 5- to 10-membered heteroaryl. In some embodiments, a compound of the disclosure is a compound, or pharmaceutically acceptable salt thereof, wherein ring $\overset{B}{\bigcirc}$ is 5- to 9-membered heteroaryl. In some embodiments, a compound of the disclosure is a compound, or pharmaceutically acceptable salt thereof, wherein ring $\overset{B}{\bigcirc}$ is 6- to 10-membered heteroaryl. In some embodiments, a compound of the disclosure is a compound, or pharmaceutically acceptable salt thereof, wherein ring $\overset{B}{\bigcirc}$ is 6- to 9-membered heteroaryl. In some embodiments, a compound of the disclosure is a compound, or pharmaceutically acceptable salt thereof, wherein ring $\overset{B}{\bigcirc}$ is 5-, 6-, 7-, 8-, 9-, or 10-membered heteroaryl. In some embodiments, a compound of the disclosure is a compound, or pharmaceutically acceptable salt thereof, wherein ring $\overset{B}{\bigcirc}$ is a nitrogen-containing heteroaryl. In some embodiments, a compound of the disclosure is a compound, or pharmaceutically acceptable salt thereof, wherein ring $\overset{B}{\bigcirc}$ is a sulfur-containing heteroaryl. In some embodiments, a compound of the disclosure is a compound, or pharmaceutically acceptable salt thereof, wherein ring $\overset{B}{\bigcirc}$ is an oxygen-containing heteroaryl. In some embodiments, the heteroaryl comprises a pyridine, pyrimidine such as a pyrimidine dione, an oxazole, a pyrrole, a pyrazole, an imidazole, a triazole, or a thiophene, each of which is optionally fused to another ring forming ring $\overset{B}{\bigcirc}$.

In some embodiments, a compound of the disclosure is a compound, or pharmaceutically acceptable salt thereof, wherein ring $\overset{B}{\bigcirc}$ is

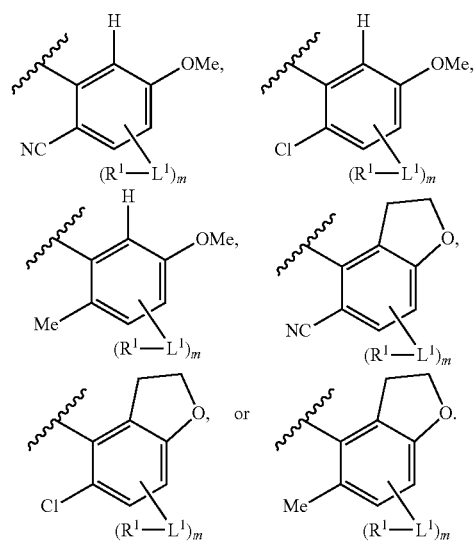

In some embodiments, a compound of the disclosure is a compound, or pharmaceutically acceptable salt thereof, wherein ring  is

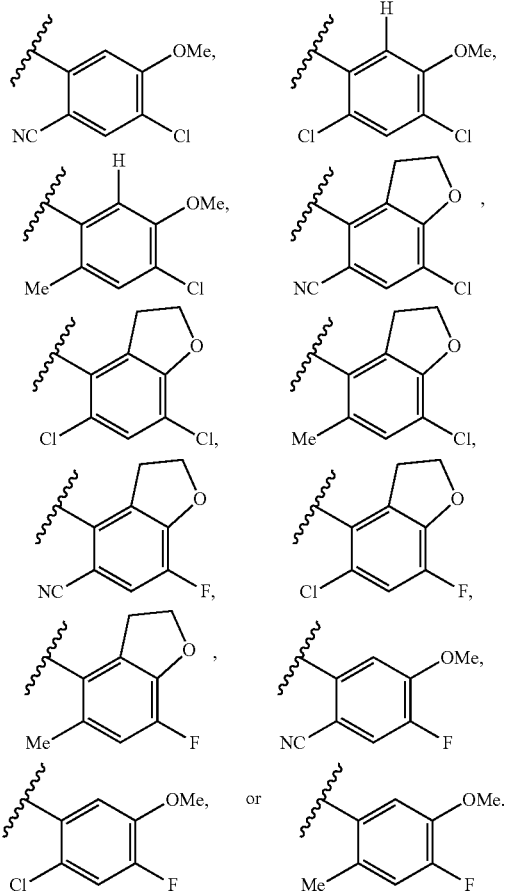

In some embodiments, a compound of the disclosure is a compound, or pharmaceutically acceptable salt thereof, wherein ring  is

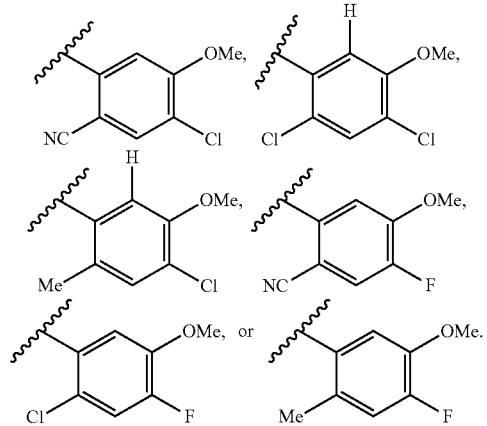

In some embodiments, a compound of the disclosure is a compound, or pharmaceutically acceptable salt thereof, wherein ring  is

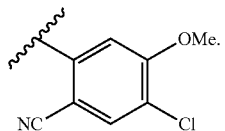

In some embodiments, a compound of the disclosure is a compound, or pharmaceutically acceptable salt thereof, wherein ring  is

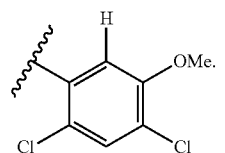 [SMILES: *c1cc(OC)c(Cl)cc1Cl]

In some embodiments, a compound of the disclosure is a compound, or pharmaceutically acceptable salt thereof, wherein ring  is

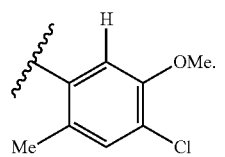 [SMILES: *c1cc(OC)c(Cl)cc1C]

In some embodiments, a compound of the disclosure is a compound, or pharmaceutically acceptable salt thereof, wherein ring  is

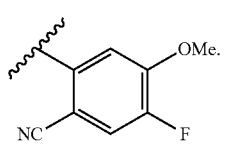 [SMILES: *c1cc(OC)c(F)cc1Cl]

In some embodiments, a compound of the disclosure is a compound, or pharmaceutically acceptable salt thereof, wherein ring  is

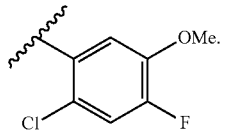

In some embodiments, a compound of the disclosure is a compound, or pharmaceutically acceptable salt thereof, wherein ring 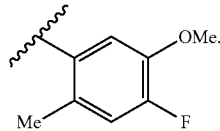 [SMILES: *c1cc(OC)c(F)cc1C] is In some embodiments, a compound of the disclosure is a compound, or pharmaceutically acceptable salt thereof, wherein each $L^1$ is independently a bond, —O—, —($C_{1-6}$ alky)O—, —O($C_{1-6}$ alkyl)-, —($C_{1-6}$ alkyl-O($C_{1-6}$ alkyl)-, —C(O)—, —N($R^L$)C(O)—, —C(O)N($R^L$)—($C_{1-6}$ alkyl)$R^L$)NC(O)—, —($C_{1-6}$ alkyl)C(O)N($R^L$)—, —N($R^L$)C(O)($C_{1-6}$ alkyl)-, —C(O)N($R^L$)($C_{1-6}$ alkyl)-, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —S(O)$_2$—, —S(O)$_2$N($R^L$)—, —N($R^L$)—S(O)$_2$—, —($C_{1-6}$ alkyl)S(O)$_2$N($R^L$)—, —($C_{1-6}$ alkyl)N($R^L$)S(O)$_2$—, —S(O)$_2$N($R^L$)($C_{1-6}$ alkyl)-, —N($R^L$)S(O)$_2$($C_{1-6}$ alkyl)-, —($C_{1-6}$ alkyl)S(O)$_2$N($R^L$)($C_{1-6}$ alkyl)-, or —($C_{1-6}$ alkyl)N($R^L$)S(O)$_2$($C_{1-6}$ alkyl)-, wherein $R^L$ is as described herein. In some embodiments, a compound of the disclosure is a compound, or pharmaceutically acceptable salt thereof, wherein each $L^1$ is independently a bond, —O—, —($C_{1-3}$ alkyl)O—, —O($C_{1-3}$ alkyl)-, —$C_{1-3}$ alkyl-O($C_{1-3}$ alkyl)-, —C(O)—, —N($R^L$)C(O)—, —C(O)N($R^L$)—, —($C_{1-3}$ alkyl)($R^L$)NC(O)—, —($C_{1-3}$ alkyl)C(O)N($R^L$)—, —N($R^L$)C(O)($C_{1-3}$ alkyl)-, —C(O)N($R^L$)($C_{1-3}$ alkyl)-, —($C_{1-3}$ alkyl)N($R^L$)C(O)($C_{1-3}$ alkyl)-, —($C_{1-3}$ alkyl)C(O)N(RX)($C_{1-3}$ alkyl)-, —S(O)$_2$—, —S(O)$_2$N($R^L$)—, —N($R^L$)—S(O)$_2$—, —($C_{1-3}$ alkyl)S(O)$_2$N($R^L$)—, —($C_{1-3}$ alkyl)N($R^L$)S(O)$_2$—, —S(O)$_2$N($R^L$)($C_{1-3}$ alkyl)-, —N($R^L$)S(O)$_2$($C_{1-3}$ alkyl)-, —($C_{1-3}$ alkyl)S(O)$_2$N($R^L$)($C_{1-3}$ alkyl)-, or —($C_{1-3}$ alkyl)N($R^L$)S(O)$_2$($C_{1-3}$ alkyl)-, wherein $R^L$ is as described herein.

In some embodiments, a compound of the disclosure is a compound, or pharmaceutically acceptable salt thereof, wherein each $L^1$ is independently —O—, —($C_{1-6}$ alkyl)O—, —O($C_{1-6}$ alkyl)-, —$C_{1-6}$ alkyl-O($C_{1-6}$ alkyl)-, —C(O)—, —N($R^L$)C(O)—, —C(O)N($R^L$), ($C_{1-6}$ alkyl)($R^L$)NC(O)—, —($C_{1-6}$ alkyl)C(O)N($R^L$)—, —N($R^L$)C(O)($C_{1-6}$ alkyl)-, —C(O)N($R^L$)($C_{1-6}$ alkyl)-, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —S(O)$_2$—, —S(O)$_2$N($R^L$)—, —N($R^L$)—S(O)$_2$—, —($C_{1-6}$ alkyl)S(O)$_2$N($R^L$)—, —($C_{1-6}$ alkyl)N($R^L$)S(O)$_2$—, —S(O)$_2$N($R^L$)$C_{1-6}$ alky)-, —N($R^L$)S(O)$_2$($C_{1-6}$ alkyl)-, —($C_{1-6}$ alkyl)S(O)$_2$N($R^L$)($C_{1-6}$ alkyl)-, or —($C_{1-6}$ alkyl)N($R^L$)S(O)$_2$($C_{1-6}$ alkyl)-, wherein $R^L$ is as defined herein. In some embodiments, a compound of the disclosure is a compound, or pharmaceutically acceptable salt thereof, wherein each $L^1$ is independently —O—, —($C_{1-3}$ alkyl)O—, —O($C_{1-3}$ alkyl)-, —$C_{1-3}$ alkyl-O($C_{1-3}$ alkyl)-, —C(O)—, —N($R^L$)C(O)—, —C(O)N($R^L$)—, —($C_{1-3}$ alkyl)($R^L$)NC(O)—, —($C_{1-3}$ alkyl)C(O)N($R^L$)—, —N($R^L$)C(O)($C_{1-3}$ alkyl)-, —C(O)N($R^L$)($C_{1-3}$ alkyl)-, —($C_{1-3}$ alkyl)N($R^L$)C(O)($C_{1-3}$ alkyl)-, —($C_{1-3}$ alkyl)C(O)N($R^L$)($C_{1-3}$ alkyl)-, —S(O)$_2$—, —S(O)$_2$N($R^L$)—, —N($R^L$)—S(O)$_2$—, —($C_{1-3}$ alkyl)S(O)$_2$N($R^L$)—, —($C_{1-3}$ alkyl)N($R^L$)S(O)$_2$—, —S(O)$_2$N($R^L$)($C_{1-3}$ alkyl)-, —N($R^L$)S(O)$_2$($C_{1-3}$ alkyl)-, —($C_{1-3}$ alkyl)S(O)$_2$N($R^L$)($C_{1-3}$ alkyl)-, or —($C_{1-3}$ alkyl)N($R^L$)S(O)$_2$($C_{1-3}$ alkyl)-, wherein $R^L$ is as defined herein.

In some embodiments, a compound of the disclosure is a compound, or pharmaceutically acceptable salt thereof, wherein each $L^1$ is independently —O—, —($C_{1-3}$ alkyl) O—, —O($C_{1-3}$ alkyl)-, or —($C_{1-6}$ alkyl-O($C_{1-3}$ alkyl)-.

In some embodiments, a compound of the disclosure is a compound, or pharmaceutically acceptable salt thereof, wherein each $L^1$ is independently —C(O)—, —N($R^L$)C(O)—, —C(O)N($R^L$)—, —($C_{1-3}$ alkyl)($R^L$)NC(O)—, —($C_{1-3}$ alkyl)C(O)N($R^L$)—, —N($R^L$)C(O)($C_{1-3}$ alkyl)-, —C(O)N($R^L$)($C_{1-3}$ alkyl)-, —($C_{1-3}$ alkyl)N($R^L$)C(O)($C_{1-3}$ alkyl)-, or —($C_{1-3}$ alkyl)C(O)N($R^L$)($C_{1-3}$ alkyl)-, wherein $R^L$ is as defined herein.

In some embodiments, a compound of the disclosure is a compound, or pharmaceutically acceptable salt thereof, wherein each $L^1$ is independently —S(O)$_2$—, —S(O)$_2$N($R^L$)—, —N($R^L$)—S(O)$_2$—, —($C_{1-3}$ alkyl)S(O)$_2$N($R^L$)—, —($C_{1-3}$ alkyl)N($R^L$)S(O)$_2$—, —S(O)$_2$N($R^L$)($C_{1-3}$ alkyl)-, —N($R^L$)S(O)$_2$($C_{1-3}$ alkyl)-, —($C_{1-3}$ alkyl)S(O)$_2$N($R^L$)($C_{1-3}$ alkyl)-, or —($C_{1-3}$ alkyl)N($R^L$)S(O)$_2$($C_{1-3}$ alkyl)-, wherein $R^L$ is as described herein.

In some embodiments, a compound of the disclosure is a compound, or pharmaceutically acceptable salt thereof, wherein each $L^1$ is a bond.

In some embodiments, a compound of the disclosure is a compound, or pharmaceutically acceptable salt thereof, wherein each $L^1$ is independently —($C_{1-6}$ alkyl)O—, —O($C_{1-6}$ alkyl)-, or —$C_6$ alkyl-O($C_{1-6}$ alkyl)-. In some embodiments, a compound of the disclosure is a compound, or pharmaceutically acceptable salt thereof, wherein each $L^1$ is independently —($C_{1-3}$ alkyl)O—, —O($C_{1-3}$ alkyl)-, or —$C_{1-3}$ alkyl-O($C_{1-3}$ alkyl)-. In some embodiments, a compound of the disclosure is a compound, or pharmaceutically acceptable salt thereof, wherein each $L^1$ is independently -(methyl)O—, —O(methyl)-, or -methyl-O(methyl)-.

In some embodiments, a compound of the disclosure is a compound, or pharmaceutically acceptable salt thereof, wherein each $L^1$ is independently a —($C_{1-6}$ alkyl)O—, or —O($C_{1-6}$ alkyl)-. In some embodiments, a compound of the disclosure is a compound, or pharmaceutically acceptable salt thereof, wherein each $L^1$ is independently a —($C_{1-3}$ alkyl)O—, or —O($C_{1-6}$ alkyl)-. In some embodiments, a compound of the disclosure is a compound, or pharmaceutically acceptable salt thereof, wherein each $L^1$ is independently a -(methyl)O—, or —O(methyl)-.

In some embodiments, a compound of the disclosure is a compound, or pharmaceutically acceptable salt thereof, wherein each $R^1$ is independently halogen, —OH, —CN, $C_{1-6}$ alkyl, —CN, —C(O)NH$_2$, $C_{2-6}$ alkenyl, $C_{2-6}$ alkynyl, $C_{1-6}$ alkoxy, $C_{3-8}$ cycloalkyl, $C_6$ aryl, 5- to 12-membered heteroaryl, or 4- to 10-membered heterocyclyl, wherein each alkyl, alkenyl, alkynyl, alkoxy, cycloalkyl, aryl, heteroaryl, and heterocyclyl is optionally substituted with one to four $R^{1a}$. In some embodiments, a compound of the disclosure is a compound, or pharmaceutically acceptable salt thereof, wherein each $R^L$ is independently fluoro, chloro, —OH, —CN, $C_{1-3}$ alkyl, —CN, —C(O)NH$_2$, $C_{2-3}$ alkenyl, $C_{2-3}$ alkynyl, $C_{1-3}$ alkoxy, $C_{3-8}$ cycloalkyl, $C_6$ aryl, 5- to 10-membered heteroaryl, or 4- to 10-membered heterocyclyl, wherein each alkyl, alkenyl, alkynyl, alkoxy, cycloalkyl, aryl, heteroaryl, and heterocyclyl is optionally substituted with one to four $R^{1a}$. In some embodiments, each alkyl, alkenyl, alkynyl, alkoxy, cycloalkyl, aryl, heteroaryl, and heterocyclyl is optionally substituted with one to three $R^{1a}$. In some embodiments, each alkyl, alkenyl, alkynyl, alkoxy, cycloalkyl, aryl, heteroaryl, and heterocyclyl is optionally substituted with one or two $R^{1a}$. In some embodiments, each alkyl, alkenyl, alkynyl, alkoxy, cycloalkyl, aryl, heteroaryl, and heterocyclyl is optionally substituted with one $R^{1a}$.

In some embodiments, a compound of the disclosure is a compound, or pharmaceutically acceptable salt thereof, wherein each $R^L$ is independently halogen, —CN, —C(O)NH$_2$, C$_{1-6}$ alkyl, C$_{2-6}$ alkynyl, C$_{1-6}$ alkoxy, C$_{3-8}$ cycloalkyl, C$_6$ aryl, or 5- to 10-membered heteroaryl, wherein each alkyl, alkynyl, alkoxy, cycloalkyl, aryl, and heteroaryl is optionally substituted with one to three $R^{1a}$. In some embodiments, a compound of the disclosure is a compound, or pharmaceutically acceptable salt thereof, wherein each $R^L$ is independently fluoro, chloro, —CN, —C(O)NH$_2$, C$_{1-3}$ alkyl, C$_{2-3}$ alkynyl, C$_{1-3}$ alkoxy, C$_{3-8}$ cycloalkyl, C$_6$ aryl, or 5- to 10-membered heteroaryl, wherein each alkyl, alkynyl, alkoxy, cycloalkyl, aryl, and heteroaryl is optionally substituted with one to three $R^{1a}$. In some embodiments, each alkyl, alkynyl, alkoxy, cycloalkyl, aryl, and heteroaryl is optionally substituted with one or two $R^{1a}$. In some embodiments, each alkyl, alkynyl, alkoxy, cycloalkyl, aryl, and heteroaryl is optionally substituted with one $R^{1a}$.

In some embodiments, a compound of the disclosure is a compound, or pharmaceutically acceptable salt thereof, wherein each $R^1$ is independently halogen, —CN, —C(O)NH$_2$, C$_{1-6}$ alkyl, C$_{2-6}$ alkynyl, C$_{1-6}$ alkoxy. C$_{3-8}$ cycloalkyl, or 5- to 10-membered heteroaryl, wherein each alkyl, alkynyl, alkoxy, cycloalkyl, aryl, and heteroaryl is optionally substituted with one or two $R^{1a}$. In some embodiments, a compound of the disclosure is a compound, or pharmaceutically acceptable salt thereof, wherein each $R^L$ is independently fluoro, chloro —CN, —C(O)NH$_2$, C$_{1-3}$ alkyl, C$_{2-3}$ alkynyl, C$_{1-3}$ alkoxy, C$_{3-8}$ cycloalkyl, or 5- to 10-membered heteroaryl, wherein each alkyl, alkynyl, alkoxy, cycloalkyl, and heteroaryl is optionally substituted with one or two $R^{1a}$. In some embodiments, each alkyl, alkenyl, alkynyl, alkoxy, cycloalkyl, aryl, heteroaryl, and heterocyclyl is optionally substituted with one $R^{1a}$.

In some embodiments, a compound of the disclosure is a compound, or pharmaceutically acceptable salt thereof, wherein each $R^L$ is independently halogen, —CN, or C$_{1-6}$ alkoxy. In some embodiments, a compound of the disclosure is a compound, or pharmaceutically acceptable salt thereof, wherein each $R^L$ is independently chloro, fluoro, —CN, or methoxy. In some embodiments, a compound of the disclosure is a compound, or pharmaceutically acceptable salt thereof, wherein each $R^1$ is independently fluoro, —CN, or methoxy. In some embodiments, a compound of the disclosure is a compound, or pharmaceutically acceptable salt thereof, wherein each $R^L$ is independently halogen or C$_{1-3}$ alkoxy. In some embodiments, a compound of the disclosure is a compound, or pharmaceutically acceptable salt thereof, wherein each $R^L$ is independently chloro, fluoro, or methoxy.

In some embodiments, a compound of the disclosure is a compound, or pharmaceutically acceptable salt thereof, wherein each $R^{1a}$ is independently C$_{1-6}$ alkyl, halogen, C$_{3-8}$ cycloalkyl, 5- to 10-membered heterocyclyl, C$_6$ aryl, 5- to 10-membered heteroaryl, oxo, —OH, —CN, —NH$_2$, —O(C$_{1-6}$ alkyl), —O(C$_{3-8}$ cycloalkyl), —O(5- to 10-membered heterocyclyl), —O(CF aryl), —O(5- to 10-membered heteroaryl), —NH(C$_{1-6}$ alkyl), —NH(C$_{3-8}$ cycloalkyl), —NH(5- to 10-membered heterocyclyl), —NH(C$_6$ aryl), —NH(5- to 10-membered heteroaryl), —N(C$_{1-6}$ alkyl)$_2$, —N(C$_{3-8}$ cycloalkyl)$_2$, —N(5- to 10-membered heterocyclyl)$_2$, —N(C$_6$ aryl)$_2$, —N(5- to 10-membered heteroaryl)$_2$, —N(C$_{1-6}$ alkyl)(C$_{3-8}$ cycloalkyl), —N(C$_{1-6}$ alkyl)(5- to 10-membered heterocyclyl), —N(C$_{1-6}$ alkyl)(C$_6$ aryl), —N(C$_{1-6}$ alkyl)(5- to 10-membered heteroaryl), —C(O)(5- to 10-membered heteroaryl), —C(O)O(C$_{1-6}$ alkyl), —C(O)O(C$_{3-8}$ cycloalkyl), —C(O)O(5- to 10-membered heterocyclyl), —C(O)O(C$_6$ aryl), —C(O)O(5- to 10-membered heteroaryl), —C(O)NH$_2$, —C(O)NH(C$_{1-6}$ alkyl), —C(O)NH(C$_{3-8}$ cycloalkyl), —C(O)NH(5- to 10-membered heterocyclyl), —C(O)NH(C (aryl), —C(O)NH(5- to 10-membered heteroaryl), —C(O)N(C$_{1-6}$ alkyl)$_2$, —C(O)N(C$_{3-8}$ cycloalkyl)$_2$, —C(O)N(5- to 10-membered heterocyclyl)$_2$, —C(O)N(C$_6$ aryl)$_2$, —C(O)N(5- to 10-membered heteroaryl)$_2$, —NHC(O)(C$_{1-6}$ alkyl), —NHC(O)(C$_{3-8}$ cycloalkyl), —NHC(O)(5- to 10-membered heterocyclyl), —NHC(O)(C(aryl), —NHC(O)(5- to 10-membered heteroaryl), —NHC(O)O(C$_{1-6}$ alkyl), —NHC(O)O(C$_{3-8}$ cycloalkyl), —NHC(O)O(5- to 10-membered heterocyclyl), —NHC(O)O(C$_6$ aryl), —NHC(O)O(5- to 10-membered heteroaryl), —NHC(O)NH(C$_{1-6}$ alkyl), —NHC(O)NH(C$_{3-8}$ cycloalkyl), —NHC(O)NH(5- to 10-membered heterocyclyl), —NHC(O)NH(C(aryl), —NHC(O)NH(5- to 10-membered heteroaryl), —NHS(O)(C$_{1-6}$ alkyl), —N(C$_{1-6}$ alkyl)(S(O)(C$_{1-6}$ alkyl), —S(O)$_2$(C$_{1-6}$ alkyl), —S(O)$_2$(C$_{3-8}$ cycloalkyl), —S(O)$_2$(5- to 10-membered heterocyclyl), —S(O)$_2$(C$_6$ aryl), —S(O)$_2$(5- to 10-membered heteroaryl), —S(O)(NH)(C$_{1-6}$ alkyl), —S(O)$_2$NH(C$_3$-alkyl), or —S(O)$_2$N(C$_{1-6}$ alkyl)$_2$, wherein each alkyl, cycloalkyl, heterocyclyl, aryl, and heteroaryl is optionally substituted with one to three $R^{1b}$. In some embodiments, each alkyl, cycloalkyl, heterocyclyl, aryl, and heteroaryl is optionally substituted with one or two $R^{1b}$. In some embodiments, each alkyl, cycloalkyl, heterocyclyl, aryl, and heteroaryl is optionally substituted with one Rib.

In some embodiments, a compound of the disclosure is a compound, or pharmaceutically acceptable salt thereof, wherein each $R^{1a}$ is independently halogen, —OH, —CN, —C(O)NH$_2$, C$_{1-6}$ alkyl, C$_{1-6}$alkoxy, C$_{3-8}$ cycloalkyl, C$_6$ aryl, or 5- to 10-membered heteroaryl, wherein each alkyl, alkoxy, cycloalkyl, aryl, and heteroaryl is optionally substituted with one to three $R^{1b}$. In some embodiments, a compound of the disclosure is a compound, or pharmaceutically acceptable salt thereof, wherein each $R^{1a}$ is independently fluoro, chloro, —OH, —CN, —C(O)NH$_2$, C$_{1-3}$ alkyl, C$_{1-3}$ alkoxy, C$_{3-8}$ cycloalkyl, C$_6$ aryl, or 5- to 10-membered heteroaryl, wherein each alkyl, alkoxy, cycloalkyl, aryl, and heteroaryl is optionally substituted with one to three $R^{1b}$. In some embodiments, each alkyl, alkoxy, cycloalkyl, aryl, and heteroaryl is optionally substituted with one or two $R^{1a}$. In some embodiments, each alkyl, alkoxy, cycloalkyl, aryl, and heteroaryl is optionally substituted with one or two $R^{1b}$.

In some embodiments, a compound of the disclosure is a compound, or pharmaceutically acceptable salt thereof, wherein at least one $R^{1a}$ is independently halogen, —OH, —CN, —C(O)NH$_2$, C$_{1-6}$ alkyl, C$_{1-6}$ alkoxy, C$_{3-8}$ cycloalkyl, C$_6$ aryl, or 5- to 10-membered heteroaryl, wherein each alkyl, alkoxy, cycloalkyl, aryl, and heteroaryl is optionally substituted with one to three $R^{1b}$. In some embodiments, a compound of the disclosure is a compound, or pharmaceutically acceptable salt thereof, wherein at least one $R^1$ is independently fluoro, chloro, —OH, —CN, —C(O)NH$_2$, C$_{1-3}$ alkyl, C$_{1-3}$ alkoxy, C$_{3-8}$ cycloalkyl, C$_6$ aryl, or 5- to 10-membered heteroaryl, wherein each alkyl, alkoxy, cycloalkyl, aryl, and heteroaryl is optionally substituted with one to three $R^{1b}$. In some embodiments, each alkyl, alkoxy, cycloalkyl, aryl, and heteroaryl is optionally substituted with one or two $R^{1b}$. In some embodiments, each alkyl, alkoxy, cycloalkyl, aryl, and heteroaryl is optionally substituted with one or two $R^{1b}$.

In some embodiments, a compound of the disclosure is a compound, or pharmaceutically acceptable salt thereof, wherein each $R^{1a}$ is independently halogen, —OH, —C(O)NH$_2$, C$_{1-6}$ alkyl, C$_{1-6}$ alkoxy, or C$_6$ aryl, wherein each alkyl, alkoxy, and aryl is optionally substituted with one to three $R^{1b}$. In some embodiments, a compound of the disclosure is a compound, or pharmaceutically acceptable salt thereof, wherein each $R^{1a}$ is independently fluoro, chloro, —OH, —C(O)NH$_2$, C$_{1-6}$ alkyl, C$_{1-6}$ alkoxy, or C$_6$ aryl, wherein each alkyl, alkoxy, and aryl is optionally substituted with one to three $R^{1b}$. In some embodiments, each alkyl, alkoxy, and aryl is optionally substituted with one or two $R^{1b}$. In some embodiments, each alkyl, alkoxy, and aryl is optionally substituted with one or two $R^{1b}$.

In some embodiments, a compound of the disclosure is a compound, or pharmaceutically acceptable salt thereof, wherein at least one $R^{1a}$ is independently halogen, —OH, —C(O)NH$_2$, C$_{1-6}$ alkyl, C$_{1-6}$ alkoxy, or C$_6$ aryl, wherein each alkyl, alkoxy, and aryl is optionally substituted with one to three $R^{1b}$. In some embodiments, a compound of the disclosure is a compound, or pharmaceutically acceptable salt thereof, wherein at least one $R^{1a}$ is independently fluoro, chloro, —OH, —C(O)NH$_2$, C$_{1-6}$ alkyl, C$_{1-6}$ alkoxy, or C$_6$ aryl, wherein each alkyl, alkoxy, and aryl is optionally substituted with one to three $R^{1b}$. In some embodiments, each alkyl, alkoxy, and aryl is optionally substituted with one or two $R^{1b}$. In some embodiments, each alkyl, alkoxy, and aryl is optionally substituted with one or two $R^{1b}$.

In some embodiments, a compound of the disclosure is a compound, or pharmaceutically acceptable salt thereof, wherein $R^{1a}$ is halogen. In some embodiments, a compound of the disclosure is a compound, or pharmaceutically acceptable salt thereof, wherein $R^{1a}$ is fluoro. In some embodiments, a compound of the disclosure is a compound, or pharmaceutically acceptable salt thereof, wherein $R^{1a}$ is chloro.

In some embodiments, a compound of the disclosure is a compound, or pharmaceutically acceptable salt thereof, wherein at least one $R^{1a}$ is halogen. In some embodiments, a compound of the disclosure is a compound, or pharmaceutically acceptable salt thereof, wherein at least one $R^{1a}$ is fluoro. In some embodiments, a compound of the disclosure is a compound, or pharmaceutically acceptable salt thereof, wherein at least one $R^{1a}$ is chloro.

In some embodiments, a compound of the disclosure is a compound, or pharmaceutically acceptable salt thereof, wherein each $R^{1b}$ is independently C$_{1-6}$ alkyl, C$_{1-6}$ haloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_6$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(C$_6$ aryl), —NH(5- to 10-membered heteroaryl), —N(C$_{1-6}$ alkyl)$_2$, —N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(C$_6$ aryl), —NHC(O)(5- to 10-membered heteroaryl), —NHC(O)O(C$_{1-6}$ alkyl), —NHC(O)O(C$_{1-6}$ haloalkyl), —NHC(O)O(C$_{2-6}$ alkynyl), —NHC(O)O(C$_{3-8}$ cycloalkyl), —NHC(O)O(5- to 10-membered heterocyclyl), —NHC(O)O(C$_6$ aryl), —NHC(O)O(5- to 10-membered heteroaryl), —NHC(O)NH(C$_{1-6}$ alkyl), S(O)$_2$(C$_{1-6}$ alkyl), —S(O)$_2$(C$_{1-6}$ haloalkyl), —S(O)$_2$(C$_{3-8}$ cycloalkyl), —S(O)$_2$(5- to 10-membered heterocyclyl), —S(O)$_2$(C$_6$ aryl), —S(O)$_2$ (5- to 10-membered heteroaryl), —S(O)(NH)(C$_{1-6}$ alkyl), —S(O)$_2$NH(C$_{1-6}$ alkyl), or —S(O)$_2$N(C$_{1-6}$ alkyl)$_2$.

In some embodiments, a compound of the disclosure is a compound, or pharmaceutically acceptable salt thereof, wherein m is an integer from 0 to 3. In some embodiments, a compound of the disclosure is a compound, or pharmaceutically acceptable salt thereof, wherein m is an integer from 0 to 2. In some embodiments, a compound of the disclosure is a compound, or pharmaceutically acceptable salt thereof, wherein m is 0. In some embodiments, a compound of the disclosure is a compound, or pharmaceutically acceptable salt thereof, wherein m is 1 or 2. In some embodiments, a compound of the disclosure is a compound, or pharmaceutically acceptable salt thereof, wherein m is 0. In some embodiments, a compound of the disclosure is a compound, or pharmaceutically acceptable salt thereof, wherein m is 1. In some embodiments, a compound of the disclosure is a compound, or pharmaceutically acceptable salt thereof, wherein m is 2. In some embodiments, a compound of the disclosure is a compound, or pharmaceutically acceptable salt thereof, wherein m is 3.

In some embodiments, a compound of the disclosure is a compound, or pharmaceutically acceptable salt thereof, wherein $R^2$ is hydrogen, C$_{1-3}$ alkyl, C$_{1-3}$ haloalkyl, cyclopropyl, C$_{1-3}$ alkoxy, —O(C$_{1-3}$ haloalkyl), —O(cyclopropyl), halogen, or —CN.

In some embodiments, a compound of the disclosure is a compound, or pharmaceutically acceptable salt thereof, wherein $R^2$ is hydrogen, halogen, C$_{1-3}$ alkyl, or C$_{1-3}$ alkoxy. In some embodiments, a compound of the disclosure is a compound, or pharmaceutically acceptable salt thereof, wherein $R^2$ is hydrogen, fluoro, chloro, methyl, or methoxy. In some embodiments, a compound of the disclosure is a compound, or pharmaceutically acceptable salt thereof, wherein $R^2$ is hydrogen. In some embodiments, a compound of the disclosure is a compound, or pharmaceutically acceptable salt thereof, wherein $R^2$ is fluoro. In some embodiments, a compound of the disclosure is a compound, or pharmaceutically acceptable salt thereof, wherein $R^2$ is chloro.

In some embodiments, a compound of the disclosure is a compound, or pharmaceutically acceptable salt thereof, wherein $R^{x1}$ is hydrogen, halogen, C$_{1-3}$ alkyl, C$_{1-3}$ haloalkyl, O C$_{1-3}$ haloalkyl, C$_{1-3}$ alkoxy, cyclopropyl, or O-cyclopropyl.

In some embodiments, a compound of the disclosure is a compound, or pharmaceutically acceptable salt thereof, wherein $R^{x1}$ is halogen, C$_{1-3}$ alkyl, or C$_{1-3}$ alkoxy. In some embodiments, a compound of the disclosure is a compound, or pharmaceutically acceptable salt thereof, wherein $R^{x1}$ is fluoro, chloro, methyl, or methoxy.

In some embodiments, a compound of the disclosure is a compound, or pharmaceutically acceptable salt thereof, wherein $R^{x1}$ is halogen or C$_{1-3}$ alkyl. In some embodiments, a compound of the disclosure is a compound, or pharmaceutically acceptable salt thereof, wherein $R^{x1}$ is fluoro, chloro, or methyl.

In some embodiments, a compound of the disclosure is a compound, or pharmaceutically acceptable salt thereof, wherein $R^{x1}$ is halogen, C$_{1-3}$ alkyl, or C$_{1-3}$ alkoxy. In some embodiments, a compound of the disclosure is a compound, or pharmaceutically acceptable salt thereof, wherein $R^{x1}$ is fluoro, chloro, or methoxy.

In some embodiments, a compound of the disclosure is a compound, or pharmaceutically acceptable salt thereof, wherein $R^{x1}$ is hydrogen.

In some embodiments, a compound of the disclosure is a compound, or pharmaceutically acceptable salt thereof, wherein $R^{x2}$ is hydrogen, halogen, C$_{1-3}$ alkyl, C$_{1-3}$ haloalkyl, O C$_{1-3}$ haloalkyl, C$_{1-3}$ alkoxy, cyclopropyl, or O-cyclopropyl.

In some embodiments, a compound of the disclosure is a compound, or pharmaceutically acceptable salt thereof, wherein $R^{x2}$ is halogen, C$_{1-3}$ alkyl, or C$_{1-3}$ alkoxy. In some embodiments, a compound of the disclosure is a compound, or pharmaceutically acceptable salt thereof, wherein $R^{x2}$ is fluoro, chloro, methyl, or methoxy.

In some embodiments, a compound of the disclosure is a compound, or pharmaceutically acceptable salt thereof, wherein $R^{x2}$ is halogen or $C_{1-3}$ alkyl. In some embodiments, a compound of the disclosure is a compound, or pharmaceutically acceptable salt thereof, wherein $R^{x2}$ is fluoro, chloro, or methyl.

In some embodiments, a compound of the disclosure is a compound, or pharmaceutically acceptable salt thereof, wherein $R^{x2}$ is halogen, $C_{1-3}$ alkyl, or $C_{1-3}$ alkoxy. In some embodiments, a compound of the disclosure is a compound, or pharmaceutically acceptable salt thereof, wherein $R^{x2}$ is fluoro, chloro, or methoxy.

In some embodiments, a compound of the disclosure is a compound, or pharmaceutically acceptable salt thereof, wherein $R^{x3}$ is hydrogen.

In some embodiments, a compound of the disclosure is a compound, or pharmaceutically acceptable salt thereof, wherein $R^{x3}$ is hydrogen, halogen, $C_{1-3}$ alkyl, $C_{1-3}$ haloalkyl, O $C_{1-3}$ haloalkyl, $C_{1-3}$ alkoxy, cyclopropyl, or O-cyclopropyl.

In some embodiments, a compound of the disclosure is a compound, or pharmaceutically acceptable salt thereof, wherein $R^3$ is halogen, $C_{1-3}$ alkyl, or $C_{1-3}$ alkoxy. In some embodiments, a compound of the disclosure is a compound, or pharmaceutically acceptable salt thereof, wherein $R^{x3}$ is fluoro, chloro, methyl, or methoxy.

In some embodiments, a compound of the disclosure is a compound, or pharmaceutically acceptable salt thereof, wherein $R^{x3}$ is halogen or $C_{1-3}$ alkyl. In some embodiments, a compound of the disclosure is a compound, or pharmaceutically acceptable salt thereof, wherein $R^{x3}$ is fluoro, chloro, or methyl.

In some embodiments, a compound of the disclosure is a compound, or pharmaceutically acceptable salt thereof, wherein $R^{x3}$ is halogen, $C_{1-3}$ alkyl, or $C_{1-3}$ alkoxy. In some embodiments, a compound of the disclosure is a compound, or pharmaceutically acceptable salt thereof, wherein $R^{x3}$ is fluoro, chloro, or methoxy.

In some embodiments, a compound of the disclosure is a compound, or pharmaceutically acceptable salt thereof, wherein $R^{x3}$ is hydrogen.

In some embodiments, a compound of the disclosure is a compound, or pharmaceutically acceptable salt thereof, wherein ring (A) taken together with $X^4$ and $X^5$ is $C_6$ aryl, 5- to 6-membered heteroaryl, $C_{5-10}$ cycloalkyl, or 5- to 10-membered heterocyclyl.

In some embodiments, a compound of the disclosure is a compound, or pharmaceutically acceptable salt thereof, wherein ring (A) taken together with $X^4$ and $X^5$ is $C_6$ aryl, wherein each $X^4$ and $X^5$ is independently N or C. In some embodiments, a compound of the disclosure is a compound, or pharmaceutically acceptable salt thereof, wherein ring (A) taken together with $X^4$ and $X^5$ is 5- to 6-membered heteroaryl, wherein each $X^4$ and $X^5$ is independently N or C. In some embodiments, a compound of the disclosure is a compound, or pharmaceutically acceptable salt thereof, wherein ring (A) taken together with $X^4$ and $X^5$ is $C_{5-10}$ cycloalkyl, wherein each $X^4$ and $X^5$ is independently N or C. In some embodiments, a compound of the disclosure is a compound, or pharmaceutically acceptable salt thereof, wherein ring (A) taken together with $X^4$ and $X^5$ is 5- to 10-membered heterocyclyl, wherein each $X^4$ and $X^5$ is independently N or C.

In some embodiments, a compound of the disclosure is a compound, or pharmaceutically acceptable salt thereof, wherein each $X^4$ and $X^5$ is independently N or C. In some embodiments, a compound of the disclosure is a compound, or pharmaceutically acceptable salt thereof, wherein $X^1$ and $X^5$ are each C.

In some embodiments, the disclosure provides a compound according to the structure of Formula (IV)

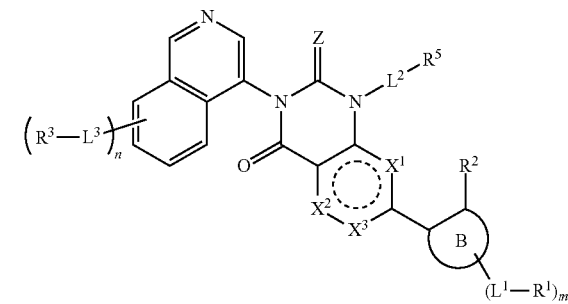

and/or pharmaceutically acceptable salt(s) thereof, wherein (B), $L^1$, $L^2$, $L^3$, $R^1$, $R^2$, $R^3$, $R^5$, $X^1$, $X^2$, $X^3$, Z, m, and n are as described herein.

In some embodiments, a compound of the disclosure is a compound, or pharmaceutically acceptable salt thereof, wherein ring (A) taken together with the ring comprising $X^4$, $X^5$, $X^6$, and $X^7$ is

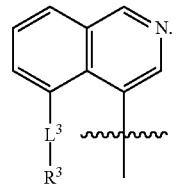

In some embodiments, the disclosure provides a compound according to the structure of Formula (IV-a)

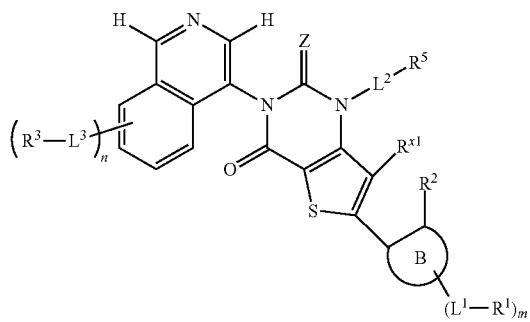

IV-a and/or pharmaceutically acceptable salt(s) thereof, wherein (B), $L^1$, $L^2$, $L^3$, $R^1$, $R^2$, $R^3$, $R^5$, $R^{x1}$, Z, m, and n are as described herein.

In some embodiments, the disclosure provides a compound according to the structure of Formula (IV-b)

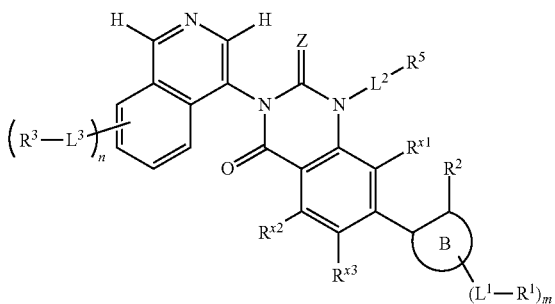

IV-b and/or pharmaceutically acceptable salt(s) thereof, wherein (B), $L^1$, $L^2$, $L^3$, $R^1$, $R^2$, $R^3$, $R^5$, $R^{x1}$, $R^{x2}$, $R^{x3}$, Z, m, and n are as described herein.

In some embodiments, a compound of the disclosure is a compound, or pharmaceutically acceptable salt thereof, wherein ring (A) is 5-membered heteroaryl. In some embodiments, a compound of the disclosure is a compound, or pharmaceutically acceptable salt thereof, wherein ring (A) taken together with the ring comprising $X^4$, $X^5$, $X^6$, and $X^7$ is

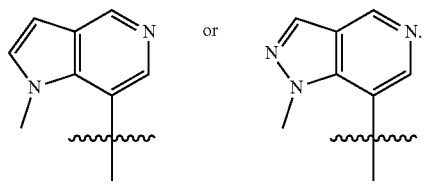 [SMILES: *c1cncc2ccn(C)c12 ; "or" ; *c1cncc2cnn(C)c12]

In some embodiments, a compound of the disclosure is a compound, or pharmaceutically acceptable salt thereof, wherein ring (A) is absent, wherein $X^4$ is N or C-$L^{x4}$-$R^{x4}$, and $X^5$ is N or C-$L^{x5}$-$R^{x3}$. In some embodiments, a compound of the disclosure is a compound, or pharmaceutically acceptable salt thereof, wherein ring (A) is absent, wherein $X^4$ is N, and $X^5$ is C-$L^{x5}$-$R^{x5}$. In some embodiments, a compound of the disclosure is a compound, or pharmaceutically acceptable salt thereof, wherein ring (A) is absent, wherein $X^4$ is C-$L^{x4}$-$R^{x4}$, and $X^5$ is N. In some embodiments, a compound of the disclosure is a compound, or pharmaceutically acceptable salt thereof, wherein ring (A) is absent, wherein $X^4$ is C-$L^{x4}$-$R^{x4}$, and $X^5$ is C-$L^{x5}$-$R^{x5}$.

In some embodiments, a compound of the disclosure is a compound, or pharmaceutically acceptable salt thereof, wherein $X^4$ is N, and $X^5$ is C-$L^{x5}$-$R^{x5}$.

In some embodiments, the disclosure provides a compound according to the structure of Formula (V)

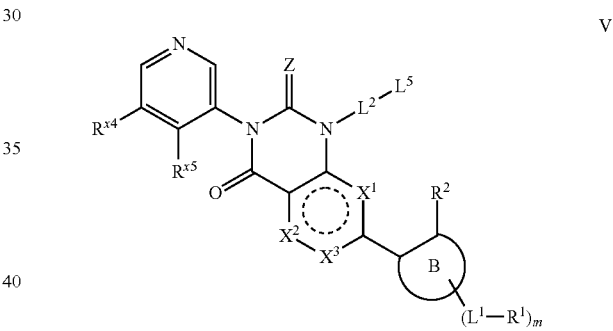

V and/or pharmaceutically acceptable salt(s) thereof, wherein (B), $L^1$, $L^2$, $R^1$, $R^2$, $R^5$, $R^{x4}$, $R^{x5}$, $X^1$, $X^2$, $X^3$, Z, m, and n are as described herein.

In some embodiments, the disclosure provides a compound according to the structure of Formula (V-a)

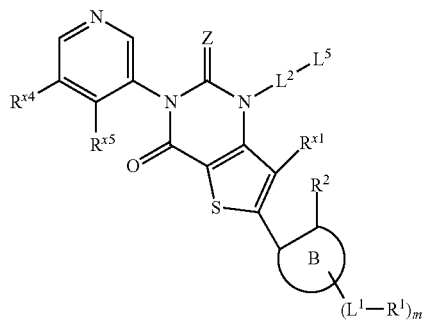

V-a and/or pharmaceutically acceptable salt(s) thereof, wherein

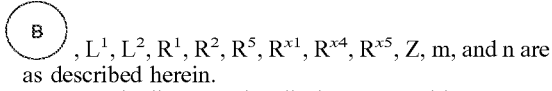, $L^1$, $L^2$, $R^1$, $R^2$, $R^5$, $R^{x1}$, $R^{x4}$, $R^{x5}$, Z, m, and n are as described herein.

In some embodiments, the disclosure provides a compound according to the structure of Formula (V-b)

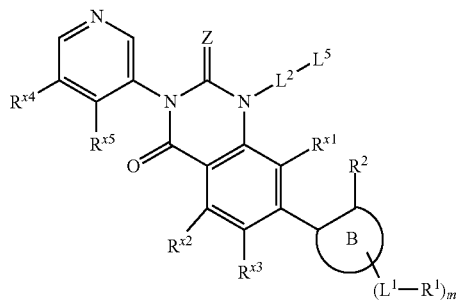

V-b and/or pharmaceutically acceptable salt(s) thereof, wherein

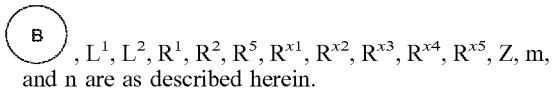, $L^1$, $L^2$, $R^1$, $R^2$, $R^5$, $R^{x1}$, $R^{x2}$, $R^{x3}$, $R^{x4}$, $R^{x5}$, Z, m, and n are as described herein.

In some embodiments, a compound of the disclosure is a compound, or pharmaceutically acceptable salt thereof, wherein $L^{x4}$ is a bond, —($C_{1-6}$alkyl)O—, —($C_{1-6}$ alkyl)N($R^L$)C(O)—, —($C_{1-6}$ alkyl)C(O)N($R^L$)—, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —($C_{1-6}$alkyl), —($C_{1-6}$ alkyl)N($R^L$)S(O)$_2$—, —N($R^L$)S(O)$_2$—, —C(O)—, —($C_{1-6}$ alkyl)C(O)—, or —N($R^L$)C(O)—, wherein $R^L$ is as described herein. In some embodiments, a compound of the disclosure is a compound, or pharmaceutically acceptable salt thereof, wherein $L^{x4}$ is a bond, —($C_{1-3}$ alkyl)O—, —($C_{1-3}$ alkyl)N($R^L$)C(O)—, —($C_{1-3}$ alkyl)C(O)N($R^L$)—, —($C_{1-3}$ alkyl)N($R^L$)C(O)($C_{1-3}$ alkyl)-, —($C_{1-3}$ alkyl)C(O)N($R^L$)($C_{1-3}$ alkyl)-, —($C_{1-3}$ alkyl), —($C_{1-3}$ alkyl)N($R^L$)S(O)$_2$—, —N($R^L$)S(O)$_2$—, —C(O)—, —($C_{1-3}$ alkyl)C(O)—, or —N($R^L$)C(O)—, wherein $R^L$ is as described herein.

In some embodiments, a compound of the disclosure is a compound, or pharmaceutically acceptable salt thereof, wherein $L^{x4}$ is —($C_{1-6}$ alkyl)O—, —($C_{1-6}$ alkyl)N($R^L$)C(O)—, 4$C_{1-6}$alkyl)C(O)N($R^L$)—, —($C_{1-6}$ alkyl)N($R^L$)C(O)($C_{1-6}$ alkyl)-, —($C_{1-6}$ alkyl)C(O)N($R^L$)($C_{1-6}$ alkyl)-, —($C_{1-6}$ alkyl). —($C_{1-6}$ alkyl)N($R^L$)S(O)$_2$—, —N($R^L$)S(O)$_2$—, —C(O)—, —($C_{1-6}$ alkyl)C(O)—, or —N($R^L$)C(O)—, wherein $R^L$ is as described herein. In some embodiments, a compound of the disclosure is a compound, or pharmaceutically acceptable salt thereof, wherein $L^{x4}$ is —($C_{1-3}$ alkyl)O—, —($C_{1-3}$ alkyl)N($R^L$)C(O)—, —($C_{1-3}$ alkyl)C(O)N($R^L$)—, —($C_{1-3}$ alkyl)N($R^1$)C(O)($C_{1-3}$ alkyl)-, —($C_{1-3}$ alkyl)C(O)N($R^L$)($C_{1-3}$ alkyl)-, —($C_{1-3}$ alkyl), —($C_{1-3}$ alkyl)N($R^L$)S(O)$_2$—, —N($R^L$)S(O)$_2$—, —C(O)—, —($C_{1-3}$ alkyl)C(O)—, or —N($R^L$)C(O)—, wherein $R^L$ is as described herein.

In some embodiments, a compound of the disclosure is a compound, or pharmaceutically acceptable salt thereof, wherein $L^{x4}$ is a bond or N($R^L$)S(O)$_2$—, wherein $R^L$ is as defined herein. In some embodiments, a compound of the disclosure is a compound, or pharmaceutically acceptable salt thereof, wherein $L^{x4}$ is a N($R^L$)S(O)$_2$—, wherein $R^L$ is as defined herein.

In some embodiments, a compound of the disclosure is a compound, or pharmaceutically acceptable salt thereof, wherein $L^{x4}$ is a bond.

In some embodiments, a compound of the disclosure is a compound, or pharmaceutically acceptable salt thereof, wherein $L^{x5}$ is —($C_{1-6}$ alkyl)O—, —($C_{1-6}$ alkyl)N($R^L$)C(O)—, —($C_{1-6}$ alkyl)C(O)N($R^L$)—, —($C_{1-6}$ alkyl)N($R^L$)C(O)($C_{1-6}$ alkyl)-, —($C_{1-6}$ alkyl)C(O)N($R^L$)($C_{1-4}$ alkyl)-, 4$C_{1-6}$ alkyl), —($C_{1-6}$ alkyl)N($R^L$)S(O)$_2$—, —N($R^L$)S(O)$_2$—, —C(O)—, —($C_{1-6}$ alkyl)C(O)—, or —N($R^L$)C(O)—, wherein $R^L$ is as described herein. In some embodiments, a compound of the disclosure is a compound, or pharmaceutically acceptable salt thereof, wherein $L^{x5}$ is —($C_{1-3}$ alkyl)O—, —($C_{1-3}$ alkyl)N($R^L$)C(O)—, —($C_{1-3}$ alkyl)C(O)N($R^L$)—, —($C_{1-3}$ alkyl)N($R^L$)C(O)($C_{1-3}$ alkyl)-, —($C_{1-3}$ alkyl)C(O)N($R^L$)($C_{1-3}$ alkyl)-, —($C_{1-3}$ alkyl), —($C_{1-3}$ alkyl)N($R^L$)S(O)$_2$—, —N($R^L$)S(O)$_2$—, —C(O)—, —($C_{1-3}$ alkyl)C(O)—, or —N(R—)C(O)—, wherein $R^L$ is as described herein.

In some embodiments, a compound of the disclosure is a compound, or pharmaceutically acceptable salt thereof, wherein $L^{x5}$ is a bond or N($R^L$)S(O)$_2$—, wherein $R^L$ is as defined herein. In some embodiments, a compound of the disclosure is a compound, or pharmaceutically acceptable salt thereof, wherein $L^{x5}$ is a N($R^L$)S(O)$_2$—, wherein $R^L$ is as defined herein.

In some embodiments, a compound of the disclosure is a compound, or pharmaceutically acceptable salt thereof, wherein $L^{x5}$ is a bond.

In some embodiments, a compound of the disclosure is a compound, or pharmaceutically acceptable salt thereof, wherein $R^{x4}$ is hydrogen, halogen, hydroxy, —CN, $C_{1-6}$ alkyl, $C_{2-6}$ alknyl, $C_{1-6}$ alkoxy, $C_{3-8}$ cycloalkyl, 4- to 10-membered heterocyclyl, 5- to 10-membered heteroaryl, —NH$_2$, —NH($C_{1-6}$ alkyl), —N($C_{1-6}$ alkyl)$_2$, —O($C_{1-6}$ alkyl), or —O$C_{3-8}$ cycloalkyl, wherein each alkyl, alkynyl, alkoxy, cycloalkyl, and heterocyclyl is optionally substituted with one to four $R^{4a}$. In some embodiments, a compound of the disclosure is a compound, or pharmaceutically acceptable salt thereof, wherein $R^4$ is hydrogen, halogen, hydroxy, —CN, $C_{1-3}$ alkyl, $C_{2-3}$ alkynyl, $C_{1-3}$ alkoxy, $C_{3-8}$ cycloalkyl, 4- to 10-membered heterocyclyl, 5- to 10-membered heteroaryl, —NH$_2$, —NH($C_{1-3}$ alkyl), —N($C_{1-3}$ alkyl)$_2$, —O($C_{1-3}$ alkyl), or —O$C_{3-8}$ cycloalkyl, wherein each alkyl, alkynyl, alkoxy, cycloalkyl, and heterocyclyl is optionally substituted with one to four $R^{4a}$. In some embodiments, each alkyl, alkynyl, alkoxy, cycloalkyl, and heterocyclyl is optionally substituted with one to three Rh. In some embodiments, each alkyl, alkynyl, alkoxy, cycloalkyl, and heterocyclyl is optionally substituted with one or two $R^{4a}$. In some embodiments, each alkyl, alkynyl, alkoxy, cycloalkyl, and heterocyclyl is optionally substituted with one $R^{4a}$.

In some embodiments, a compound of the disclosure is a compound, or pharmaceutically acceptable salt thereof, wherein $R^{x4}$ is hydrogen, $C_1$-$C_6$ alkyl, —NH$_2$, —NH($C_{1-6}$ alkyl), —N($C_{1-6}$ alkyl)$_2$, $C_{1-6}$ alkoxy, $C_3$-$C_8$ cycloalkyl, or 5- to 10-membered heterocyclyl, wherein each alkyl, alkoxy, cycloalkyl, and heterocyclyl is optionally substituted with one to three $R^{4a}$. In some embodiments, a compound of the disclosure is a compound, or pharmaceutically acceptable salt thereof, wherein $R^{x4}$ is hydrogen, $C_1$-$C_3$ alkyl, —NH$_2$, —NH($C_{1-3}$ alkyl), —N($C_{1-3}$ alkyl)$_2$, $C_{1-3}$ alkoxy, $C_3$-$C_8$ cycloalkyl, or 5- to 10-membered heterocyclyl, wherein each alkyl, alkoxy, cycloalkyl, and heterocyclyl is optionally substituted with one to three $R^{4a}$. In some embodiments, each alkyl, alkoxy, cycloalkyl, and heterocyclyl is optionally substituted with one or two $R^{4a}$. In some embodiments, each alkyl, alkoxy, cycloalkyl, and heterocyclyl is optionally substituted with one $R^{4a}$.

In some embodiments, a compound of the disclosure is a compound, or pharmaceutically acceptable salt thereof, wherein $R^{x4}$ is $C_3$-$C_8$ cycloalkyl. In some embodiments, a compound of the disclosure is a compound, or pharmaceutically acceptable salt thereof, wherein $R^{x4}$ is $C_3$-$C_8$ cycloalkyl, wherein the cycloalkyl is optionally substituted with one or two $R^{4a}$, and $R^{x5}$ is hydrogen. In some embodiments, the cycloalkyl is optionally substituted with one $R^{4a}$.

In some embodiments, a compound of the disclosure is a compound, or pharmaceutically acceptable salt thereof, wherein $R^{x4}$ is $C_{1-6}$ alkoxy. In some embodiments, a compound of the disclosure is a compound, or pharmaceutically acceptable salt thereof, wherein $R^{x4}$ is $C_{1-6}$ alkoxy, wherein the alkoxy is optionally substituted with one or two $R^{4a}$, and $R^{x5}$ is hydrogen. In some embodiments, the alkoxy is optionally substituted with one $R^{4a}$. In some embodiments, the alkoxy is methoxy.

In some embodiments, a compound of the disclosure is a compound, or pharmaceutically acceptable salt thereof, wherein $R^{x4}$ is $C_1$-$C_6$ alkyl, —$NH_2$, —$NH(C_{1-6}$ alkyl), —$N(C_{1-6}$ alkyl$)_2$, $C_{1-6}$ alkoxy, or 5- to 10-membered heterocyclyl, wherein each alkyl, alkoxy, and heterocyclyl is optionally substituted with one to three $R^{4a}$. In some embodiments, a compound of the disclosure is a compound, or pharmaceutically acceptable salt thereof, wherein $R^{x4}$ is $C_1$-$C_3$ alkyl, —$NH_2$, —$NH(C_{1-3}$ alkyl), —$N(C_{1-3}$ alkyl$)_2$, $C_{1-3}$ alkoxy, or 5- to 10-membered heterocyclyl, wherein each alkyl, alkoxy, and heterocyclyl is optionally substituted with one to three $R^{4b}$. In some embodiments, each alkyl, alkoxy, and heterocyclyl is optionally substituted with one or two $R^{4a}$. In some embodiments, each alkyl, alkoxy, and heterocyclyl is optionally substituted with one $R^{4a}$.

In some embodiments, a compound of the disclosure is a compound, or pharmaceutically acceptable salt thereof, wherein $R^{x4}$ is 5- to 7-membered heterocyclyl optionally substituted with one to three $R^{4a}$. In some embodiments, the heterocyclyl is optionally substituted with one or two $R^{4a}$. In some embodiments, the heterocyclyl is optionally substituted with one $R^{4a}$.

In some embodiments, a compound of the disclosure is a compound, or pharmaceutically acceptable salt thereof, wherein $R^{x4}$ is —$NH_2$, —$NH(C_{1-3}$ alkyl), —$N(C_{1-3}$ alkyl$)_2$, or —$O(C_{1-3}$ alkyl), wherein each alkyl is independently optionally substituted one or two $R^{4a}$. In some embodiments, each alkyl is optionally substituted with one $R^{4a}$.

In some embodiments, a compound of the disclosure is a compound, or pharmaceutically acceptable salt thereof, wherein $R^{x4}$ is methyl.

In some embodiments, a compound of the disclosure is a compound, or pharmaceutically acceptable salt thereof, wherein $R^{x5}$ is hydrogen, halogen, hydroxy, —CN, $C_{1-6}$ alkyl, $C_{2-6}$ alkynyl, $C_{1-6}$ alkoxy, $C_{3-8}$ cycloalkyl, 4- to 10-membered heterocyclyl, 5- to 10-membered heteroaryl, —$NH_2$, —$NH(C_{1-6}$ alkyl), —$N(C_{1-6}$ alkyl$)_2$, —$O(C_{1-6}$ alkyl), or —$OC_{3-8}$ cycloalkyl, wherein each alkyl, alkynyl, alkoxy, cycloalkyl, and heterocyclyl is optionally substituted with one to four $R^1$. In some embodiments, a compound of the disclosure is a compound, or pharmaceutically acceptable salt thereof, wherein $R^{x5}$ is hydrogen, halogen, hydroxy, —CN, $C_{1-3}$ alkyl, $C_{2-3}$ alkynyl, $C_{1-3}$ alkoxy, $C_{3-8}$ cycloalkyl, 4- to 10-membered heterocyclyl, 5- to 10-membered heteroaryl, —$NH_2$, —$NH(C_{1-3}$ alkyl), —$N(C_{1-3}$ alkyl$)_2$, —$O(C_{1-3}$ alkyl), or —OC-s cycloalkyl, wherein each alkyl, alkynyl, alkoxy, cycloalkyl, and heterocyclyl is optionally substituted with one to four $R^1$. In some embodiments, each alkyl, alkynyl, alkoxy, cycloalkyl, and heterocyclyl is optionally substituted with one to three $R^1$. In some embodiments, each alkyl, alkynyl, alkoxy, cycloalkyl, and heterocyclyl is optionally substituted with one or two $R^{4a}$. In some embodiments, each alkyl, alkynyl, alkoxy, cycloalkyl, and heterocyclyl is optionally substituted with one $R^{4b}$.

In some embodiments, a compound of the disclosure is a compound, or pharmaceutically acceptable salt thereof, wherein $R^{x5}$ is hydrogen, $C_1$-$C_6$ alkyl, —$NH_2$, —$NH(C_{1-6}$ alkyl), —$N(C_{1-6}$ alkyl$)_2$, $C_{1-6}$ alkoxy, $C_3$-$C_8$ cycloalkyl, or 5- to 10-membered heterocyclyl, wherein each alkyl, alkoxy, cycloalkyl, and heterocyclyl is optionally substituted with one to three $R^{4a}$. In some embodiments, a compound of the disclosure is a compound, or pharmaceutically acceptable salt thereof, wherein $R^{x5}$ is hydrogen, $C_1$-$C_3$ alkyl. —$NH_2$, —$NH(C_{1-3}$ alkyl), —$N(C_{1-3}$ alkyl$)_2$, $C_{1-3}$ alkoxy, $C_3$-$C_8$ cycloalkyl, or 5- to 10-membered heterocyclyl, wherein each alkyl, alkoxy, cycloalkyl, and heterocyclyl is optionally substituted with one to three Rb. In some embodiments, each alkyl, alkoxy, cycloalkyl, and heterocyclyl is optionally substituted with one or two $R^{4a}$. In some embodiments, each alkyl, alkoxy, cycloalkyl, and heterocyclyl is optionally substituted with one $R^{4a}$.

In some embodiments, a compound of the disclosure is a compound, or pharmaceutically acceptable salt thereof, wherein $R^{x5}$ is $C_3$-$C_8$ cycloalkyl. In some embodiments, a compound of the disclosure is a compound, or pharmaceutically acceptable salt thereof, wherein $R^{x5}$ is $C_3$-$C_8$ cycloalkyl, wherein the cycloalkyl is optionally substituted with one or two $R^{4a}$, and $R^{x4}$ is hydrogen. In some embodiments, the cycloalkyl is optionally substituted with one $R^{4a}$.

In some embodiments, a compound of the disclosure is a compound, or pharmaceutically acceptable salt thereof, wherein $R^{x5}$ is $C_{1-6}$ alkoxy. In some embodiments, a compound of the disclosure is a compound, or pharmaceutically acceptable salt thereof, wherein $R^{x5}$ is $C_{1-6}$ alkoxy, wherein the alkoxy is optionally substituted with one or two $R^{4a}$, and $R^{4a}$ is hydrogen. In some embodiments, the alkoxy is optionally substituted with one $R^{4a}$. In some embodiments, the alkoxy is methoxy.

In some embodiments, a compound of the disclosure is a compound, or pharmaceutically acceptable salt thereof, wherein $R^{x5}$ is $C_1$-$C_6$ alkyl, —$NH_2$, —$NH(C_{1-6}$ alkyl), —$N(C_{1-6}$ alkyl$)_2$, $C_{1-6}$ alkoxy, or 5- to 10-membered heterocyclyl, wherein each alkyl, alkoxy, and heterocyclyl is optionally substituted with one to three $R^{4a}$. In some embodiments, a compound of the disclosure is a compound, or pharmaceutically acceptable salt thereof, wherein $R^{x5}$ is $C_1$-$C_3$ alkyl, —$NH_2$, —$NH(C_{1-3}$ alkyl), —$N(C_{1-3}$ alkyl$)_2$, $C_{1-3}$ alkoxy, or 5- to 10-membered heterocyclyl, wherein each alkyl, alkoxy, and heterocyclyl is optionally substituted with one to three $R^4$. In some embodiments, each alkyl, alkoxy, and heterocyclyl is optionally substituted with one or two $R^{4a}$. In some embodiments, each alkyl, alkoxy, and heterocyclyl is optionally substituted with one $R^{4a}$.

In some embodiments, a compound of the disclosure is a compound, or pharmaceutically acceptable salt thereof, wherein $R^{x5}$ is 5- to 7-membered heterocyclyl optionally substituted with one to three $R^{4a}$. In some embodiments, the heterocyclyl is optionally substituted with one or two $R^{4a}$. In some embodiments, the heterocyclyl is optionally substituted with one $R^4$.

In some embodiments, a compound of the disclosure is a compound, or pharmaceutically acceptable salt thereof, wherein $R^{x5}$ is —$NH_2$, —$NH(C_{1-3}$ alkyl), —$N(C_{1-3}$ alkyl$)_2$, or —$O(C_{1-3}$ alkyl), wherein each alkyl is independently optionally substituted one or two $R^{4a}$. In some embodiments, each alkyl is optionally substituted with one $R^{4a}$.

In some embodiments, a compound of the disclosure is a compound, or pharmaceutically acceptable salt thereof, wherein $R^{x5}$ is methyl.

In some embodiments, a compound of the disclosure is a compound, or pharmaceutically acceptable salt thereof, wherein each $R^{4a}$ is independently $C_{1-6}$ alkyl, $C_{1-6}$ haloalkyl, halogen, $C_{3-8}$ cycloalkyl, 5- to 10-membered heterocyclyl, $C_6$ aryl, 5- to 10-membered heteroaryl, oxo, —OH, —CN, —NH$_2$, —O($C_{1-6}$ alkyl), —O($C_{1-6}$ haloalkyl), —O($C_{3-8}$ cycloalkyl), —O(5- to 10-membered heterocyclyl), —O($C_{6-10}$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH($C_6$ aryl), —NH(5- to 10-membered heteroaryl), —N($C_{1-6}$ alkyl)$_2$, —N($C_{1-6}$ haloalkyl)$_2$, —N($C_{3-8}$ cycloalkyl)$_2$, —N($C_{1-6}$ alkyl)($C_{1-6}$ haloalkyl), —N($C_{1-6}$ alkyl)($C_{3-8}$ cycloalkyl), —N($C_{1-6}$ alkyl)(5- to 10-membered heterocyclyl), —N($C_{1-6}$ alkyl)($C_6$ aryl), —N($C_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH($C_{1-6}$ alkyl), —C(O)NH($C_{1-6}$ haloalkyl), —C(O)NH($C_{3-8}$ cycloalkyl), —C(O)NH(5- to 10-membered heterocyclyl), —C(O)NH($C_6$ aryl), —C(O)NH(5- to 10-membered heteroaryl), —C(O)N($C_{1-6}$ alkyl)$_2$, —C(O)N($C_{1-6}$ haloalkyl)$_2$, —C(O)N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)($C_6$ aryl), —NHC(O)(5- to 10-membered heteroaryl), —NHC(O)O($C_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), —NHC(O)NH($C_{1-6}$ haloalkyl), —NHC(O)NH($C_{3-8}$ cycloalkyl), —NHC(O)NH(5- to 10-membered heterocyclyl), —NHC(O)NH($C_{1-6}$ alkyl), —NHC(O)NH(5- to 10-membered heteroaryl), —S(O)$_2$($C_{1-6}$ alkyl), —S(O)$_2$($C_{1-6}$ haloalkyl), —S(O)$_2$($C_{3-8}$ cycloalkyl), —S(O)(NH)($C_{1-6}$ alkyl), —S(O)$_2$NH($C_{1-6}$ alkyl), or —S(O)$_2$N($C_{1-6}$ alkyl)$_2$, wherein each alkyl, cycloalkyl, heterocyclyl, aryl, and heteroaryl is optionally substituted with one to three $R^1$. In some embodiments, each alkyl, cycloalkyl, heterocyclyl, aryl, and heteroaryl is optionally substituted with one or two Rb. In some embodiments, each alkyl, cycloalkyl, heterocyclyl, aryl, and heteroaryl is optionally substituted with one $R^{4a}$.

In some embodiments, a compound of the disclosure is a compound, or pharmaceutically acceptable salt thereof, wherein each $R^{4a}$ is independently $C_{1-6}$ alkyl, —C(O)(5- to 10-membered heterocyclyl), or —O($C_{3-8}$ cycloalkyl), wherein each alkyl, heterocyclyl, and cycloalkyl is optionally substituted with one to three $R^{4b}$. In some embodiments, a compound of the disclosure is a compound, or pharmaceutically acceptable salt thereof, wherein each $R^{4a}$ is independently $C_{1-3}$ alkyl, —C(O)(5- to 10-membered heterocyclyl), or —O($C_{3-8}$ cycloalkyl), wherein each alkyl, heterocyclyl, and cycloalkyl is optionally substituted with one to three $R^{4b}$. In some embodiments, each alkyl, heterocyclyl, and cycloalkyl is optionally substituted with one or two $R^{4b}$. In some embodiments, each alkyl, heterocyclyl, and cycloalkyl is optionally substituted with one $R^{4b}$.

In some embodiments, a compound of the disclosure is a compound, or pharmaceutically acceptable salt thereof, wherein at least one $R^{4a}$ is $C_{1-6}$ alkyl, —C(O)(5- to 10-membered heterocyclyl), or —O($C_{3-8}$ cycloalkyl), wherein each alkyl, heterocyclyl, and cycloalkyl is optionally substituted with one to three $R^{4b}$. In some embodiments, a compound of the disclosure is a compound, or pharmaceutically acceptable salt thereof, wherein at least one $R^{4a}$ is independently $C_{1-3}$ alkyl, —C(O)(5- to 10-membered heterocyclyl), or —O($C_{3-8}$ cycloalkyl), wherein each alkyl, heterocyclyl, and cycloalkyl is optionally substituted with one to three $R^{4b}$. In some embodiments, each alkyl, heterocyclyl, and cycloalkyl is optionally substituted with one or two $R^{4b}$. In some embodiments, each alkyl, heterocyclyl, and cycloalkyl is optionally substituted with one $R^{4b}$.

In some embodiments, a compound of the disclosure is a compound, or pharmaceutically acceptable salt thereof, wherein each $R^{4a}$ is independently halogen, —C(O)($C_1$-$C_6$ alkyl), —OH, —O($C_{1-6}$ alkyl), 5- to 10-membered heterocyclyl, —C(O)NH$_2$, —C(O)N(H)($C_1$-$C_6$ alkyl), or —C(O)N($C_1$-$C_6$ alkyl)$_2$, wherein each alkyl and heterocyclyl is optionally substituted with one to three $R^{4b}$. In some embodiments, a compound of the disclosure is a compound, or pharmaceutically acceptable salt thereof, wherein each $R^{4b}$ is independently chloro, fluoro, —C(O)($C_1$-$C_3$ alkyl), —OH, —O($C_{1-3}$ alkyl), 5- to 10-membered heterocyclyl, —C(O)NH$_2$, —C(O)N(H)($C_1$-$C_3$ alkyl), or —C(O)N($C_1$-$C_3$ alkyl)$_2$, wherein each alkyl and heterocyclyl is optionally substituted with one to three $R^{4b}$. In some embodiments, each alkyl and heterocyclyl is optionally substituted with one or two $R^{4b}$. In some embodiments, each alkyl and heterocyclyl is optionally substituted with one $R^{4b}$.

In some embodiments, a compound of the disclosure is a compound, or pharmaceutically acceptable salt thereof, wherein at least one $R^{4a}$ is halogen, —C(O)($C_1$-$C_6$ alkyl), —OH, —O($C_{1-6}$ alkyl), 5- to 10-membered heterocyclyl, —C(O)NH$_2$, —C(O)N(H)($C_1$-$C_6$ alkyl), or —C(O)N($C_1$-$C_6$ alkyl)$_2$, wherein each alkyl and heterocyclyl is optionally substituted with one to three $R^{4b}$. In some embodiments, a compound of the disclosure is a compound, or pharmaceutically acceptable salt thereof, wherein at least one $R^{4a}$ is chloro, fluoro, —C(O)($C_1$-$C_3$ alkyl), —OH, —O($C_{1-3}$ alkyl), 5- to 10-membered heterocyclyl, —C(O)NH$_2$, —C(O)N(H)($C_1$-$C_3$ alkyl), or —C(O)N($C_1$-$C_3$ alkyl)$_2$, wherein each alkyl and heterocyclyl is optionally substituted with one to three $R^{4b}$. In some embodiments, each alkyl and heterocyclyl is optionally substituted with one or two $R^{4b}$. In some embodiments, each alkyl and heterocyclyl is optionally substituted with one $R^{4b}$.

In some embodiments, a compound of the disclosure is a compound, or pharmaceutically acceptable salt thereof, wherein each $R^{4a}$ is independently —O($C_{1-3}$ alkyl), 5- to 7-membered heterocyclyl, —C(O)NH$_2$, —C(O)N(H)($C_1$-$C_3$ alkyl), or —C(O)N($C_1$-$C_3$ alkyl)$_2$, wherein each alkyl and heterocyclyl is optionally substituted with one to three $R^{4b}$. In some embodiments, each alkyl and heterocyclyl is optionally substituted with one or two $R^{4b}$. In some embodiments, each alkyl and heterocyclyl is optionally substituted with one $R^{4b}$.

In some embodiments, a compound of the disclosure is a compound, or pharmaceutically acceptable salt thereof, wherein at least one $R^{4a}$ is —O($C_{1-3}$ alkyl), 5- to 7-membered heterocyclyl, —C(O)NH$_2$, —C(O)N(H)($C_1$-$C_3$ alkyl), or —C(O)N($C_1$-$C_3$ alkyl)$_2$, wherein each alkyl and heterocyclyl is optionally substituted with one to three $R^{4b}$. In some embodiments, each alkyl and heterocyclyl is optionally substituted with one or two $R^{4b}$. In some embodiments, each alkyl and heterocyclyl is optionally substituted with one $R^{4b}$.

In some embodiments, a compound of the disclosure is a compound, or pharmaceutically acceptable salt thereof, wherein each $R^{4a}$ is independently halogen or —C(O)($C_1$-$C_6$ alkyl), wherein the alkyl is optionally substituted with one to three $R^{4b}$. In some embodiments, a compound of the disclosure is a compound, or pharmaceutically acceptable salt thereof, wherein each $R^{4a}$ is independently halogen or —C(O)(C$_1$-C$_3$ alkyl). In some embodiments, a compound of the disclosure is a compound, or pharmaceutically acceptable salt thereof, wherein each $R^{4a}$ is independently chloro, fluoro or —C(O)(methyl).

In some embodiments, a compound of the disclosure is a compound, or pharmaceutically acceptable salt thereof, wherein at least one $R^4$ is halogen or —C(O)(C$_1$-C$_6$ alkyl), wherein the alkyl is optionally substituted with one to three $R^{4b}$. In some embodiments, a compound of the disclosure is a compound, or pharmaceutically acceptable salt thereof, wherein at least one $R^{4a}$ is halogen or —C(O)(C$_1$-C$_3$ alkyl). In some embodiments, a compound of the disclosure is a compound, or pharmaceutically acceptable salt thereof, wherein at least one $R^{4a}$ is chloro, fluoro or —C(O)(methyl).

In some embodiments, a compound of the disclosure is a compound, or pharmaceutically acceptable salt thereof, wherein each $R^{4a}$ is independently —OH or —O(C$_{1-3}$ alkyl). In some embodiments, a compound of the disclosure is a compound, or pharmaceutically acceptable salt thereof, wherein each $R^{4a}$ is independently —OH or methoxy.

In some embodiments, a compound of the disclosure is a compound, or pharmaceutically acceptable salt thereof, wherein at least one $R^{4a}$ is —OH or —O(C$_{1-3}$ alkyl). In some embodiments, a compound of the disclosure is a compound, or pharmaceutically acceptable salt thereof, wherein at least one $R^{4a}$ is —OH or methoxy.

In some embodiments, a compound of the disclosure is a compound, or pharmaceutically acceptable salt thereof, wherein $R^{4a}$ is —O(C$_{1-3}$ alkyl). In some embodiments, a compound of the disclosure is a compound, or pharmaceutically acceptable salt thereof, wherein $R^{4a}$ is methoxy.

In some embodiments, a compound of the disclosure is a compound, or pharmaceutically acceptable salt thereof, wherein at least one $R^{4a}$ is —O(C$_{1-3}$ alkyl). In some embodiments, a compound of the disclosure is a compound, or pharmaceutically acceptable salt thereof, wherein at least one $R^{4a}$ is methoxy.

In some embodiments, a compound of the disclosure is a compound, or pharmaceutically acceptable salt thereof, wherein each $R^{4a}$ is independently halogen or —OH. In some embodiments, a compound of the disclosure is a compound, or pharmaceutically acceptable salt thereof, wherein each $R^{4a}$ is independently chloro, fluoro, or —OH.

In some embodiments, a compound of the disclosure is a compound, or pharmaceutically acceptable salt thereof, wherein at least one $R^{4a}$ is halogen or —OH. In some embodiments, a compound of the disclosure is a compound, or pharmaceutically acceptable salt thereof, wherein at least one $R^{4a}$ is chloro, fluoro, or —OH.

In some embodiments, a compound of the disclosure is a compound, or pharmaceutically acceptable salt thereof, wherein each $R^{4b}$ is independently C$_{1-6}$ alkyl, C$_{1-6}$ haloalkyl, C$_{3-6}$ cycloalkyl, halogen, oxo, —OH, —NH$_2$, CO$_2$H, —O(C$_{1-6}$ alkyl), —O(C$_{1-6}$ haloalkyl), —O(C$_{3-8}$ cycloalkyl), —O(5- to 10-membered heterocyclyl), —O(C$_6$ aryl), —O(5- to 10-membered heteroaryl), —NH(C$_{1-6}$ alkyl), —NH(C$_{1-6}$ haloalkyl), —NH(C$_{3-8}$ cycloalkyl), —NH(5- to 10-membered heterocyclyl), —NH(5- to 10-membered heteroaryl), —N(C$_{1-6}$ alkyl)$_2$, —N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(5- to 10-membered heteroaryl), —NHC(O)O(C$_{1-6}$ alkyl), —NHC(O)O(C$_{1-6}$ haloalkyl), —NHC(O)O(C$_{3-8}$ cycloalkyl), —NHC(O)O(5- to 10-membered heterocyclyl), —NHC(O)O(5- to 10-membered heteroaryl), —NHC(O)NH(C$_{1-6}$ alkyl), S(O)$_2$(C$_{1-6}$ alkyl), —S(O)$_2$(C$_{1-6}$ haloalkyl), —S(O)$_2$(C$_{3-8}$ cycloalkyl), —S(O)(NH))(C$_{1-6}$ alkyl), —S(O)$_2$NH(C$_{1-6}$ alkyl), or —S(O)$_2$N(C$_{1-6}$ alkyl)$_2$.

In some embodiments, a compound of the disclosure is a compound, or pharmaceutically acceptable salt thereof, wherein each $R^{4b}$ is independently halogen, —O(C$_{1-6}$ alkyl), or —O(C$_{1-6}$ haloalkyl). In some embodiments, a compound of the disclosure is a compound, or pharmaceutically acceptable salt thereof, wherein each $R^{4b}$ is independently fluoro, chloro —O(C$_{1-3}$ alkyl), or —O(C$_{1-3}$ haloalkyl).

In some embodiments, a compound of the disclosure is a compound, or pharmaceutically acceptable salt thereof, wherein at least one $R^{4b}$ is halogen, —O(C$_{1-6}$ alkyl), or —O(C$_{1-6}$ haloalkyl). In some embodiments, a compound of the disclosure is a compound, or pharmaceutically acceptable salt thereof, wherein at least one $R^{4b}$ is halogen independently fluoro, chloro —O(C$_{1-3}$ alkyl), or —O(C$_{1-3}$ haloalkyl).

In some embodiments, a compound of the disclosure is a compound, or pharmaceutically acceptable salt thereof, wherein each $L^1$ is independently a bond, —(C$_{1-6}$ alkyl)O—, —(C$_{1-6}$alkyl)N(R$^L$)C(O)—, —(C$_{1-6}$ alkyl)C(O)N(R$^L$)—, —(C$_{1-6}$ alkyl)N(R$^L$)C(O)(C$_{1-6}$alkyl)-, —(C$_6$ alkyl)C(O)N (R$^L$)(C$_{1-6}$ alkyl)-, —(C$_{1-6}$ alkyl), —(C$_{1-6}$ alkyl)N(R$^L$)S(O)$_2$—, —N(R$^L$)S(O)$_2$—, —C(O)—, —(C$_{1-6}$ alkyl)C(O)—, or —N(R$^L$)C(O)—, wherein R$^L$ is as described herein. In some embodiments, a compound of the disclosure is a compound, or pharmaceutically acceptable salt thereof, wherein each $L^3$ is independently a bond, —(C$_{1-3}$ alkyl)O—, —(C$_{1-3}$ alkyl)N(R$^L$)C(O)—, —(C$_{1-3}$ alkyl)C(O)N(R$^L$)—, —(C$_{1-3}$ alkyl)N (R$^L$)C(O)(C$_{1-3}$ alkyl)-, —(C$_{1-3}$ alkyl)C(O)N(R$^L$)(C$_{1-3}$ alkyl)-, —(C$_1$-3 alkyl), —(C$_{1-3}$ alkyl)N(R$^L$)S(O)$_2$—, —N(R$^L$)S(O)$_2$—, —C(O)—, —(C$_{1-3}$ alkyl)C(O)—, or —N(R$^L$)C(O)—, wherein R$^L$ is as described herein.

In some embodiments, a compound of the disclosure is a compound, or pharmaceutically acceptable salt thereof, wherein each $L^3$ is independently —(C$_{1-6}$ alkyl)O—, —(C$_{1-6}$ alkyl)N(R$^L$)C(O)—, —(C$_{1-6}$ alkyl)C(O)N(R$^L$)—, —(C$_{1-6}$ alkyl)N(R$^L$)C(O)(C$_{1-6}$ alkyl)-, —(C$_{1-6}$ alkyl)C(O)N (R$^L$)(C$_{1-6}$alkyl)-, —(C$_{1-6}$alkyl), —(C$_{1-6}$alkyl)N(R$^L$) S(O)$_2$—, —N(R$^L$)S(O)$_2$—. —C(O)—, —(C$_{1-6}$ alkyl)C (O)—, or —N(R$^L$)C(O)—, wherein R$^L$ is as described herein. In some embodiments, a compound of the disclosure is a compound, or pharmaceutically acceptable salt thereof, wherein each $L^1$ is independently —(C$_{1-3}$ alkyl)O—, —(C$_{1-3}$ alkyl)N(R$^L$)C(O)—, —(C$_{1-3}$ alkyl)C(O)N(R$^L$)—, —(C$_{1-3}$ alkyl)N(R$^L$)C(O)(C$_{1-3}$ alkyl)-, —(C$_{1-3}$ alkyl)C(O)N (R$^L$)(C$_{1-3}$ alkyl)-, —(C$_{1-3}$ alkyl), —(C$_{1-3}$ alkyl)N(R$^L$) S(O)$_2$—, —N(R$^L$)S(O)$_2$—, —C(O)—, —(C$_{1-3}$ alkyl)C (O)—, or —N(R$^L$)C(O)—, wherein R$^L$ is as described herein.

In some embodiments, a compound of the disclosure is a compound, or pharmaceutically acceptable salt thereof, wherein $L^1$ is a bond or N(R$^L$)S(O)$_2$—, wherein R$^L$ is as defined herein. In some embodiments, a compound of the disclosure is a compound, or pharmaceutically acceptable salt thereof, wherein $L^1$ is a N(R$^L$)S(O)$_2$—, wherein R$^L$ is as defined herein.

In some embodiments, a compound of the disclosure is a compound, or pharmaceutically acceptable salt thereof, wherein $L^3$ is a bond.

In some embodiments, a compound of the disclosure is a compound, or pharmaceutically acceptable salt thereof, wherein each $R^3$ is independently a bond, halogen, hydroxy, —CN, C$_{1-6}$ alkyl, C$_{2-6}$ alkynyl, C$_{1-6}$ alkoxy, C$_{3-8}$ cycloalkyl, 4- to 10-membered heterocyclyl, 5- to 10-membered heteroaryl, —NH$_2$, —NH(C$_{1-6}$ alkyl), —N(C$_{1-6}$ alkyl)$_2$, —O(C$_{1-6}$ alkyl), or —OC$_{3-8}$ cycloalkyl, wherein each alkyl, alkynyl, alkoxy, cycloalkyl, and heterocyclyl is optionally substituted with one to four R$^{3a}$. In some embodiments, a compound of the disclosure is a compound, or pharmaceutically acceptable salt thereof, wherein each R$^3$ is independently a bond, halogen, hydroxy, —CN, C$_{1-3}$ alkyl. C$_{2-3}$ alkynyl, C$_{1-3}$ alkoxy, C$_{3-6}$ cycloalkyl, 4- to 10-membered heterocyclyl, 5- to 10-membered heteroaryl, —NH$_2$, —NH(C$_{1-3}$ alkyl), —N(C$_{1-3}$ alkyl)$_2$, —O(C$_{1-3}$ alkyl), or —OC$_{3-8}$ cycloalkyl, wherein each alkyl, alkynyl, alkoxy, cycloalkyl, and heterocyclyl is optionally substituted with one to four R$^{3a}$. In some embodiments, each alkyl, alkynyl, alkoxy, cycloalkyl, and heterocyclyl is optionally substituted with one to three R$^{3a}$. In some embodiments, each alkyl, alkynyl, alkoxy, cycloalkyl, and heterocyclyl is optionally substituted with one or two R$^{3a}$. In some embodiments, each alkyl, alkynyl, alkoxy, cycloalkyl, and heterocyclyl is optionally substituted with one R$^{3a}$.

In some embodiments, a compound of the disclosure is a compound, or pharmaceutically acceptable salt thereof, wherein each R$^{3a}$ is independently a bond, C$_1$-C$_6$ alkyl, —NH$_2$, —NH(C$_{1-6}$ alkyl), —N(C$_{1-6}$ alkyl)$_2$, C$_{1-3}$ alkoxy, C$_3$-C$_8$ cycloalkyl, or 5- to 10-membered heterocyclyl, wherein each alkyl, alkoxy, cycloalkyl, and heterocyclyl is optionally substituted with one to three R$^{3a}$. In some embodiments, a compound of the disclosure is a compound, or pharmaceutically acceptable salt thereof, wherein each R$^{3a}$ is independently a bond, C$_1$-C$_3$ alkyl, —NH$_2$, —NH(C$_{1-3}$ alkyl), —N(C$_{1-3}$ alkyl)$_2$, C$_{1-3}$ alkoxy, C$_3$-C$_8$ cycloalkyl, or 5- to 10-membered heterocyclyl, wherein each alkyl, alkoxy, cycloalkyl, and heterocyclyl is optionally substituted with one to three R$^{3a}$. In some embodiments, each alkyl, alkoxy, cycloalkyl, and heterocyclyl is optionally substituted with one or two R$^{3a}$. In some embodiments, each alkyl, alkoxy, cycloalkyl, and heterocyclyl is optionally substituted with one R$^{3a}$.

In some embodiments, a compound of the disclosure is a compound, or pharmaceutically acceptable salt thereof, wherein R$^{3a}$ is C$_3$-C$_8$ cycloalkyl, wherein the cycloalkyl is optionally substituted with one R$^{3a}$. In some embodiments, the cycloalkyl is optionally substituted with one R$^{3a}$.

In some embodiments, a compound of the disclosure is a compound, or pharmaceutically acceptable salt thereof, wherein at least one R$^3$ is C$_3$-C$_8$ cycloalkyl, wherein the cycloalkyl is optionally substituted with one or two R$^{3a}$. In some embodiments, the cycloalkyl is optionally substituted with one R$^{3a}$.

In some embodiments, a compound of the disclosure is a compound, or pharmaceutically acceptable salt thereof, wherein R$^3$ is C$_{1-6}$ alkoxy, wherein the alkoxy is optionally substituted with one or two Ra. In some embodiments, the alkoxy is optionally substituted with one R$^{3a}$. In some embodiments, the alkoxy is methoxy.

In some embodiments, a compound of the disclosure is a compound, or pharmaceutically acceptable salt thereof, wherein at least one R$^{3a}$ is C$_{1-6}$ alkoxy, wherein the alkoxy is optionally substituted with one or two R$^{3a}$. In some embodiments, the alkoxy is optionally substituted with one R$^{3a}$. In some embodiments, the alkoxy is methoxy.

In some embodiments, a compound of the disclosure is a compound, or pharmaceutically acceptable salt thereof, wherein each R$^{3a}$ is independently C$_1$-C$_6$ alkyl, —NH$_2$, —NH(C$_{1-6}$ alkyl), —N(C$_{1-6}$ alkyl)$_2$, C$_{1-6}$ alkoxy, or 5- to 10-membered heterocyclyl, wherein each alkyl, alkoxy, and heterocyclyl is optionally substituted with one to three R$^{3a}$.

In some embodiments, a compound of the disclosure is a compound, or pharmaceutically acceptable salt thereof, wherein each R$^{3a}$ is independently C$_1$-C$_3$ alkyl, —NH$_2$, —NH(C$_{1-6}$ alkyl), —N(C$_{1-3}$ alkyl)$_2$, C$_{1-3}$ alkoxy, or 5- to 10-membered heterocyclyl, wherein each alkyl, alkoxy, and heterocyclyl is optionally substituted with one to three R$^{3a}$. In some embodiments, each alkyl, alkoxy, and heterocyclyl is optionally substituted with one or two R$^{3a}$. In some embodiments, each alkyl, alkoxy, and heterocyclyl is optionally substituted with one R$^{3a}$.

In some embodiments, a compound of the disclosure is a compound, or pharmaceutically acceptable salt thereof, wherein R$^{3a}$ is 5- to 7-membered heterocyclyl optionally substituted with one to three R$^{3a}$. In some embodiments, the heterocyclyl is optionally substituted with one or two R$^{3a}$. In some embodiments, the heterocyclyl is optionally substituted with one R$^{3a}$.

In some embodiments, a compound of the disclosure is a compound, or pharmaceutically acceptable salt thereof, wherein at least one R$^{3a}$ is 5- to 7-membered heterocyclyl optionally substituted with one to three R$^{3a}$. In some embodiments, the heterocyclyl is optionally substituted with one or two R. In some embodiments, the heterocyclyl is optionally substituted with one R$^{3a}$.

In some embodiments, a compound of the disclosure is a compound, or pharmaceutically acceptable salt thereof, wherein each R$^3$ is independently —NH$_2$, —NH(C$_{1-3}$ alkyl), —N(C$_{1-3}$ alkyl)$_2$, or —O(C$_{1-3}$ alkyl), wherein each alkyl is independently optionally substituted one or two R$^{3a}$. In some embodiments, each alkyl is optionally substituted with one R$^{3a}$.

In some embodiments, a compound of the disclosure is a compound, or pharmaceutically acceptable salt thereof, wherein R$^{3a}$ is methyl.

In some embodiments, a compound of the disclosure is a compound, or pharmaceutically acceptable salt thereof, wherein at least one R$^{3a}$ is methyl.

In some embodiments, a compound of the disclosure is a compound, or pharmaceutically acceptable salt thereof, wherein at least one R$^{3a}$ is halogen. In some embodiments, a compound of the disclosure is a compound, or pharmaceutically acceptable salt thereof, wherein at least one R$^{3a}$ is fluoro or chloro.

In some embodiments, a compound of the disclosure is a compound, or pharmaceutically acceptable salt thereof, wherein each R$^{3a}$ is independently C$_{1-6}$ alkyl, C$_{1-6}$ haloalkyl, halogen, C$_{3-8}$ cycloalkyl, 5- to 10-membered heterocyclyl, C$_6$ aryl, 5- to 10-membered heteroaryl, oxo, —OH, —CN, —NH$_2$, —O(C$_{1-6}$ alkyl), —O(C$_{1-6}$ haloalkyl), —O(C$_{3-8}$ cycloalkyl), —O(5- to 10-membered heterocyclyl), —O(C$_{6-10}$ aryl), —O(5- to 10-membered heteroaryl), —NH(C$_{1-6}$ alkyl), —NH(C$_{1-6}$ haloalkyl), —NH(C$_{3-8}$ cycloalkyl), —NH (5- to 10-membered heterocyclyl), —NH(C$_6$ an), —NH(5- to 10-membered heteroaryl), —N(C$_{1-6}$ alkyl)$_2$, —N(C$_{1-6}$ haloalkyl)$_2$, —N(C$_{3-8}$ cycloalkyl)$_2$, —N(C$_{1-6}$ alkyl)(C$_{1-6}$ haloalkyl), —N(C$_{1-6}$ alkyl)(C$_{3-8}$ cycloalkyl), —N(C$_{1-6}$ alkyl)(5- to 10-membered heterocyclyl), —N(C$_{1-6}$ alkyl)(C$_6$ aryl), —N(C$_{1-6}$ alkyl)(5- to 10-membered heteroaryl), —C(O)(5- to 10-membered heterocyclyl), —C(O)(5- to 10-membered heteroaryl), —C(O)NH$_2$, —C(O)NH(C$_{1-6}$ alkyl), —C(O)NH(C$_{1-6}$ haloalkyl), —C(O)NH(C$_{3-8}$ cycloalkyl), —C(O)NH(5- to 10-membered heterocyclyl), —C(O)NH(C$_6$ aryl), —C(O)NH(5- to 10-membered heteroaryl), —C(O)N(C$_{1-6}$ alkyl)$_2$, —C(O)N(C$_{1-6}$ haloalkyl)$_2$, —C(O)N(C$_{3-8}$ cycloalkyl)$_2$, —NHC(O)(C$_{1-6}$ alkyl), —NHC(O)(C$_{1-6}$ haloalkyl), —NHC(O)(C$_{3-8}$ cycloalkyl), —NHC(O)(5- to 10-membered heterocyclyl), —NHC(O)(C$_6$ aryl), —NHC(O)(5- to 10-membered heteroaryl), —NHC(O)O(C$_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O($C_6$ aryl), —NHC(O)O(5- to 10-membered heteroaryl), —NHC(O)NH($C_{1-6}$ alkyl), —NHC(O)NH($C_{1-6}$ haloalkyl), —NHC(O)NH($C_{3-8}$ cycloalkyl), —NHC(O)NH (5- to 10-membered heterocyclyl), —NHC(O)NH($C_6$ aryl). —NHC(O)NH(5- to 10-membered heteroaryl), —S(O)$_2$ ($C_{1-6}$ alkyl), —S(O)$_2$($C_{1-6}$ haloalkyl), —S(O)$_2$($C_{3-8}$ cycloalkyl), —S(O)(NH)($C_{1-6}$ alkyl), —S(O)NH($C_{1-6}$ alkyl), or —S(O)$_2$N($C_{1-6}$ alkyl)$_2$, wherein each alkyl, cycloalkyl, heterocyclyl, aryl, and heteroaryl is optionally substituted with one to three $R^{3b}$. In some embodiments, each alkyl, cycloalkyl, heterocyclyl, aryl, and heteroaryl is optionally substituted with one or two $R^{3b}$. In some embodiments, each alkyl, cycloalkyl, heterocyclyl, aryl, and heteroaryl is optionally substituted with one $R^{3b}$.

In some embodiments, a compound of the disclosure is a compound, or pharmaceutically acceptable salt thereof, wherein each $R^{3a}$ is independently $C_{1-6}$ alkyl, —C(O)(5- to 10-membered heterocyclyl), or —O($C_{3-8}$ cycloalkyl), wherein each alkyl, heterocyclyl, and cycloalkyl is optionally substituted with one to three $R^{3b}$. In some embodiments, a compound of the disclosure is a compound, or pharmaceutically acceptable salt thereof, wherein each $R^{3a}$ is independently $C_{1-3}$ alkyl, —C(O)(5- to 10-membered heterocyclyl), or —O($C_{3-8}$ cycloalkyl), wherein each alkyl, heterocyclyl, and cycloalkyl is optionally substituted with one to three $R^{3b}$. In some embodiments, each alkyl, heterocyclyl, and cycloalkyl is optionally substituted with one or two $R^{3b}$. In some embodiments, each alkyl, heterocyclyl, and cycloalkyl is optionally substituted with one $R^{3b}$.

In some embodiments, a compound of the disclosure is a compound, or pharmaceutically acceptable salt thereof, wherein at least one $R^L$ is $C_{1-6}$ alkyl, —C(O)(5- to 10-membered heterocyclyl), or —O($C_{3-8}$ cycloalkyl), wherein each alkyl, heterocyclyl, and cycloalkyl is optionally substituted with one to three $R^{3b}$. In some embodiments, a compound of the disclosure is a compound, or pharmaceutically acceptable salt thereof, wherein at least one $R^L$ is independently $C_{1-3}$ alkyl, —C(O)(5- to 10-membered heterocyclyl), or —O($C_{3-8}$ cycloalkyl), wherein each alkyl, heterocyclyl, and cycloalkyl is optionally substituted with one to three $R^{3b}$. In some embodiments, each alkyl, heterocyclyl, and cycloalkyl is optionally substituted with one or two $R^{3b}$. In some embodiments, each alkyl, heterocyclyl, and cycloalkyl is optionally substituted with one $R^{3b}$.

In some embodiments, a compound of the disclosure is a compound, or pharmaceutically acceptable salt thereof, wherein each $R^{3a}$ is independently halogen, —C(O)($C_1$-$C_6$ alkyl), —OH, —O($C_{1-6}$ alkyl), 5- to 10-membered heterocyclyl, —C(O)NH$_2$, —C(O)N(H)($C_1$-$C_6$ alkyl), or —C(O)N($C_1$-$C_6$ alkyl)$_2$, wherein each alkyl and heterocyclyl is optionally substituted with one to three $R^{3b}$. In some embodiments, a compound of the disclosure is a compound, or pharmaceutically acceptable salt thereof, wherein each $R^{3a}$, is independently chloro, fluoro, —C(O)($C_1$-$C_3$ alkyl), —OH, —O($C_{1-3}$ alkyl), 5- to 10-membered heterocyclyl, —C(O)NH$_2$, —C(O)N(H)($C_1$-$C_3$ alkyl), or —C(O)N($C_1$-$C_3$ alkyl)$_2$, wherein each alkyl and heterocyclyl is optionally substituted with one to three $R^{3b}$. In some embodiments, each alkyl and heterocyclyl is optionally substituted with one or two $R^{3b}$. In some embodiments, each alkyl and heterocyclyl is optionally substituted with one $R^{3b}$.

In some embodiments, a compound of the disclosure is a compound, or pharmaceutically acceptable salt thereof, wherein at least one $R^{3a}$ is halogen, —C(O)($C_1$-$C_6$ alkyl), —OH, —O($C_{1-6}$ alkyl), 5- to 10-membered heterocyclyl, —C(O)NH$_2$, —C(O)N(H)($C_1$-$C_6$ alkyl), or —C(O)N($C_1$-$C_6$ alkyl)$_2$, wherein each alkyl and heterocyclyl is optionally substituted with one to three $R^{3b}$. In some embodiments, a compound of the disclosure is a compound, or pharmaceutically acceptable salt thereof, wherein at least one $R^{3a}$ is chloro, fluoro, —C(O)($C_1$-$C_3$ alkyl), —OH, —O($C_{1-6}$ alkyl), 5- to 10-membered heterocyclyl, —C(O)NH$_2$, —C(O)N(H) ($C_1$-$C_3$ alkyl), or —C(O)N($C_1$-$C_3$ alkyl)$_2$, wherein each alkyl and heterocyclyl is optionally substituted with one to three $R^{3b}$. In some embodiments, each alkyl and heterocyclyl is optionally substituted with one or two $R^{3b}$. In some embodiments, each alkyl and heterocyclyl is optionally substituted with one $R^{3b}$.

In some embodiments, a compound of the disclosure is a compound, or pharmaceutically acceptable salt thereof, wherein each $R^{3a}$ is independently —O($C_{1-3}$ alkyl), 5- to 7-membered heterocyclyl, —C(O)NH$_2$, —C(O)N(H)($C_1$-$C_3$ alkyl), or —C(O)N($C_1$-$C_3$ alkyl)$_2$, wherein each alkyl and heterocyclyl is optionally substituted with one to three $R^{3b}$. In some embodiments, each alkyl and heterocyclyl is optionally substituted with one or two $R^{3b}$. In some embodiments, each alkyl and heterocyclyl is optionally substituted with one $R^{3b}$.

In some embodiments, a compound of the disclosure is a compound, or pharmaceutically acceptable salt thereof, wherein at least one $R^{3a}$ is —O($C_{1-3}$ alkyl), 5- to 7-membered heterocyclyl, —C(O)NH$_2$, —C(O)N(H)($C_1$-$C_3$ alkyl), or —C(O)N($C_1$-$C_3$ alkyl)$_2$, wherein each alkyl and heterocyclyl is optionally substituted with one to three $R^{3b}$. In some embodiments, each alkyl and heterocyclyl is optionally substituted with one or two $R^{3b}$. In some embodiments, each alkyl and heterocyclyl is optionally substituted with one $R^{3b}$.

In some embodiments, a compound of the disclosure is a compound, or pharmaceutically acceptable salt thereof, wherein each Ra is independently halogen or —C(O)($C_1$-$C_6$ alkyl), wherein the alkyl is optionally substituted with one to three RA. In some embodiments, a compound of the disclosure is a compound, or pharmaceutically acceptable salt thereof, wherein each $R^{3a}$ is independently halogen or —C(O)($C_1$-$C_3$ alkyl). In some embodiments, a compound of the disclosure is a compound, or pharmaceutically acceptable salt thereof, wherein each $R^{3a}$ is independently chloro, fluoro or —C(O)(methyl).

In some embodiments, a compound of the disclosure is a compound, or pharmaceutically acceptable salt thereof, wherein at least one $R^{3a}$ is halogen or —C(O)($C_1$-$C_6$ alkyl), wherein the alkyl is optionally substituted with one to three $R^{3b}$. In some embodiments, a compound of the disclosure is a compound, or pharmaceutically acceptable salt thereof, wherein at least one $R^{3a}$ is halogen or —C(O)($C_1$-$C_3$ alkyl). In some embodiments, a compound of the disclosure is a compound, or pharmaceutically acceptable salt thereof, wherein at least one $R^{3a}$ is chloro, fluoro or —C(O)(methyl).

In some embodiments, a compound of the disclosure is a compound, or pharmaceutically acceptable salt thereof, wherein each $R^{3a}$ is independently —OH or —O($C_{1-3}$ alkyl). In some embodiments, a compound of the disclosure is a compound, or pharmaceutically acceptable salt thereof, wherein each $R^{3a}$ is independently —OH or methoxy.

In some embodiments, a compound of the disclosure is a compound, or pharmaceutically acceptable salt thereof, wherein at least one $R^{3b}$ is —OH or —O($C_{1-3}$ alkyl). In some embodiments, a compound of the disclosure is a compound, or pharmaceutically acceptable salt thereof, wherein at least one $R^{3a}$ is —OH or methoxy.

In some embodiments, a compound of the disclosure is a compound, or pharmaceutically acceptable salt thereof, wherein $R^{3a}$ is —O($C_{1-3}$ alkyl). In some embodiments, a compound of the disclosure is a compound, or pharmaceutically acceptable salt thereof, wherein $R^{3a}$ is methoxy.

In some embodiments, a compound of the disclosure is a compound, or pharmaceutically acceptable salt thereof, wherein at least one $R^{3a}$ is —O($C_{1-3}$ alkyl). In some embodiments, a compound of the disclosure is a compound, or pharmaceutically acceptable salt thereof, wherein at least one $R^{3a}$ is methoxy.

In some embodiments, a compound of the disclosure is a compound, or pharmaceutically acceptable salt thereof, wherein each $R^{3a}$ is independently halogen or —OH. In some embodiments, a compound of the disclosure is a compound, or pharmaceutically acceptable salt thereof, wherein each $R^{3a}$ is independently chloro, fluoro, or —OH.

In some embodiments, a compound of the disclosure is a compound, or pharmaceutically acceptable salt thereof, wherein at least one $R^{3a}$ is halogen or —OH. In some embodiments, a compound of the disclosure is a compound, or pharmaceutically acceptable salt thereof, wherein at least one $R^{3a}$ is chloro, fluoro, or —OH.

In some embodiments, a compound of the disclosure is a compound, or pharmaceutically acceptable salt thereof, wherein each $R^{3b}$ is independently $C_{1-6}$ alkyl, $C_{1-6}$ haloalkyl, $C_{3-6}$ cycloalkyl, halogen, oxo, —OH, —$NH_2$, $CO_2H$, —O($C_{1-6}$ alkyl), —O($C_{1-6}$ haloalkyl), —O($C_{3-8}$ cycloalkyl), —O(5- to 10-membered heterocyclyl), —O($C_{6-10}$ aryl), —O(5- to 10-membered heteroaryl), —NH($C_{1-6}$ alkyl), —NH($C_{1-6}$ haloalkyl), —NH($C_{3-8}$ cycloalkyl), —NH(5- to 10-membered heterocyclyl), —NH(5- to 10-membered heteroaryl), —N($C_{1-6}$ alkyl)$_2$, —N($C_{3-8}$ cycloalkyl)$_2$, —NHC(O)($C_{1-6}$ alkyl), —NHC(O)($C_{1-6}$ haloalkyl), —NHC(O)($C_{3-8}$ cycloalkyl), —NHC(O)(5- to 10-membered heterocyclyl), —NHC(O)(5- to 10-membered heteroaryl), —NHC(O)O($C_{1-6}$ alkyl), —NHC(O)O($C_{1-6}$ haloalkyl), —NHC(O)O($C_{3-8}$ cycloalkyl), —NHC(O)O(5- to 10-membered heterocyclyl), —NHC(O)O(5- to 10-membered heteroaryl), —NHC(O)NH($C_{1-6}$ alkyl), $S(O)_2(C_{1-6}$ alkyl), —$S(O)_2(C_{1-6}$ haloalkyl), —$S(O)_2(C_{3-8}$ cycloalkyl), —S(O)(NH))($C_{1-6}$ alkyl), —$S(O)_2NH(C_{1-6}$ alkyl), or —$S(O)_2N(C_{1-6}$ alkyl)$_2$.

In some embodiments, a compound of the disclosure is a compound, or pharmaceutically acceptable salt thereof, wherein each $R^{3'}$ is independently halogen, —O($C_{1-6}$ alkyl), or —O($C_{1-6}$ haloalkyl). In some embodiments, a compound of the disclosure is a compound, or pharmaceutically acceptable salt thereof, wherein each $R^{3b}$ is independently fluoro, chloro —O($C_{1-3}$ alkyl), or —O($C_{1-3}$ haloalkyl).

In some embodiments, a compound of the disclosure is a compound, or pharmaceutically acceptable salt thereof, wherein each $R^L$ is independently hydrogen, $C_{1-6}$ alkyl, $C_{1-6}$ haloalkyl, or $C_{3-8}$ cycloalkyl. In some embodiments, a compound of the disclosure is a compound, or pharmaceutically acceptable salt thereof, wherein each $R^L$ is independently hydrogen or $C_{1-6}$ alkyl. In some embodiments, a compound of the disclosure is a compound, or pharmaceutically acceptable salt thereof, wherein each $R^L$ is independently hydrogen or $C_{1-3}$ alkyl. In some embodiments, a compound of the disclosure is a compound, or pharmaceutically acceptable salt thereof, wherein $R^L$ is hydrogen. In some embodiments, a compound of the disclosure is a compound, or pharmaceutically acceptable salt thereof, wherein $R^L$ is methyl.

In some embodiments, a compound of the disclosure is a compound, or pharmaceutically acceptable salt thereof, wherein n is an integer from 0 to 3. In some embodiments, a compound of the disclosure is a compound, or pharmaceutically acceptable salt thereof, wherein n is an integer from 0 to 2. In some embodiments, a compound of the disclosure is a compound, or pharmaceutically acceptable salt thereof, wherein n is 0. In some embodiments, a compound of the disclosure is a compound, or pharmaceutically acceptable salt thereof, wherein n is 1 or 2. In some embodiments, a compound of the disclosure is a compound, or pharmaceutically acceptable salt thereof, wherein n is 0. In some embodiments, a compound of the disclosure is a compound, or pharmaceutically acceptable salt thereof, wherein n is 1. In some embodiments, a compound of the disclosure is a compound, or pharmaceutically acceptable salt thereof, wherein n is 2.

In some embodiments, a compound of the disclosure is a compound, or pharmaceutically acceptable salt thereof, wherein $X^6$ is N or CH. In some embodiments, a compound of the disclosure is a compound, or pharmaceutically acceptable salt thereof, wherein $X^6$ is N. In some embodiments, a compound of the disclosure is a compound, or pharmaceutically acceptable salt thereof, wherein $X^6$ is CH.

In some embodiments, a compound of the disclosure is a compound, or pharmaceutically acceptable salt thereof, wherein $X^1$ is N or CH. In some embodiments, a compound of the disclosure is a compound, or pharmaceutically acceptable salt thereof, wherein $X^7$ is N. In some embodiments, a compound of the disclosure is a compound, or pharmaceutically acceptable salt thereof, wherein $X^1$ is CH.

In some embodiments, a compound of the disclosure is a compound, or pharmaceutically acceptable salt thereof, wherein $X^6$ and $X^7$ are CH.

In some embodiments, a compound of the disclosure is a compound, or pharmaceutically acceptable salt thereof, wherein no more than two of $X^4$, $X^5$, $X^6$, and $X^1$ are N. In some embodiments, a compound of the disclosure is a compound, or pharmaceutically acceptable salt thereof, wherein two of $X^4$, $X^5$, $X^6$, and $X^7$ are N. In some embodiments, a compound of the disclosure is a compound, or pharmaceutically acceptable salt thereof, wherein one of $X^4$, $X^5$, $X^6$, and $X^7$ is N. In some embodiments, a compound of the disclosure is a compound, or pharmaceutically acceptable salt thereof, wherein none of $X^4$, $X^5$, $X^6$, and $X^7$ is N.

In some embodiments, a compound of the disclosure is a compound, or pharmaceutically acceptable salt thereof, wherein $L^2$ is a bond. $C_{1-6}$ alkyl, —($C_{1-6}$ alkyl)O—, —($C_{1-6}$ alkyl)O($C_{1-6}$alkyl)-, —($C_{1-6}$ alkyl) ($R^{L2}$)NC(O)—, —($C_{1-6}$ alkyl)C(O)N($R^{L2}$)—, —($C_{1-6}$ alkyl)S(O)$_2$N($R^{L2}$)—, —($C_{1-6}$ alkyl)N($R^{L2}$)S(O)$_2$—, or —($C_{1-6}$ alkyl)S(O)$_2$N($R^{L2}$) ($C_{1-6}$ alkyl)-, wherein $R^{L2}$ is as described herein. In some embodiments, a compound of the disclosure is a compound, or pharmaceutically acceptable salt thereof, wherein $L^2$ is a bond, $C_{1-3}$ alkyl, —($C_{1-3}$ alkyl)O—, —($C_{1-3}$ alkyl)O($C_{1-3}$ alkyl)-, —($C_{1-3}$ alkyl) (RV)NC(O)—, —($C_{1-3}$ alkyl)C(O)N($R^{L2}$)—, —($C_{1-3}$ alkyl)S(O)$_2$N($R^{L2}$)—, —($C_{1-3}$ alkyl)N($R^{L2}$)S(O)$_2$—, or —($C_{1-3}$ alkyl)S(O)$_2$N($R^{L2}$) ($C_{1-6}$ alkyl)-, wherein $R^2$ is as described herein.

In some embodiments, a compound of the disclosure is a compound, or pharmaceutically acceptable salt thereof, wherein $L^2$ is $C_{1-6}$ alkyl, —($C_{1-6}$ alkyl)O—, —($C_{1-6}$ alkyl)O($C_{1-6}$ alkyl)-, —($C_{1-6}$ alkyl) ($R^{L2}$)NC(O)—, —($C_{1-6}$ alkyl)C(O)N($R^{L2}$)—, —($C_{1-3}$ alkyl)S(O)$_2$N($R^{L2}$)—, —($C_{1-6}$alkyl)N($R^{L2}$)S(O)$_2$—, or —($C_{1-6}$alkyl)S(O)$_2$N($R^{L2}$) ($C_{1-6}$ alkyl)-, wherein $R^{L2}$ is as described herein. In some embodiments, a compound of the disclosure is a compound, or pharmaceutically acceptable salt thereof, wherein $L^2$ is $C_{1-6}$ alkyl, —($C_{1-6}$ alkyl)O—, —($C_{1-3}$ alkyl)O($C_{1-3}$ alkyl)-, —($C_{1-3}$ alkyl) (R²)NC(O)—, —(C$_{1-3}$ alkyl)C(O)N(R$^L$)—, —(C$_{1-3}$ alkyl)S(O)$_2$N(R$^{L2}$)—, —(C$_{1-3}$ alkyl)N(R$^{L2}$)S(O)$_2$—, or —(C$_{1-3}$ alkyl)S(O)$_2$N(R$^{L2}$) (C$_{1-6}$ alkyl)-, wherein R$^{L2}$ is as described herein.

In some embodiments, a compound of the disclosure is a compound, or pharmaceutically acceptable salt thereof, wherein L² is a bond.

In some embodiments, a compound of the disclosure is a compound, or pharmaceutically acceptable salt thereof, wherein L² is C$_1$-C$_3$ alkyl. In some embodiments, a compound of the disclosure is a compound, or pharmaceutically acceptable salt thereof, wherein L² is methyl. In some embodiments, a compound of the disclosure is a compound, or pharmaceutically acceptable salt thereof, wherein L² is ethyl. In some embodiments, a compound of the disclosure is a compound, or pharmaceutically acceptable salt thereof, wherein L² is propyl.

In some embodiments, a compound of the disclosure is a compound, or pharmaceutically acceptable salt thereof, wherein R² is hydrogen or C$_{1-6}$ alkyl. In some embodiments, a compound of the disclosure is a compound, or pharmaceutically acceptable salt thereof, wherein R$^L$ is hydrogen or C$_{1-3}$ alkyl. In some embodiments, a compound of the disclosure is a compound, or pharmaceutically acceptable salt thereof, wherein R$^{L2}$ is hydrogen. In some embodiments, a compound of the disclosure is a compound, or pharmaceutically acceptable salt thereof, wherein R$^L$ is methyl.

In some embodiments, a compound of the disclosure is a compound, or pharmaceutically acceptable salt thereof, wherein R⁵ is hydrogen, —CN, —OR$^{5a}$, —C(O)NR$^{5a}{}_2$, —NR$^{5a}{}_2$, C$_{3-8}$ cycloalkyl, C$_6$ aryl, 4- to 10-membered heterocyclyl, or 5- to 10-membered heteroaryl, wherein each cycloalkyl, aryl, heterocyclyl, and heteroaryl is optionally substituted with one or two R$^{5b}$. In some embodiments, each cycloalkyl, aryl, heterocyclyl, and heteroaryl is optionally substituted with one R$^{5b}$.

In some embodiments, a compound of the disclosure is a compound, or pharmaceutically acceptable salt thereof, wherein R⁵ is hydrogen.

In some embodiments, a compound of the disclosure is a compound, or pharmaceutically acceptable salt thereof, wherein R⁵ is —CN.

In some embodiments, a compound of the disclosure is a compound, or pharmaceutically acceptable salt thereof, wherein R⁵ is C$_{3-8}$ cycloalkyl, C$_6$ aryl, 4- to 10-membered heterocyclyl, or 5- to 10-membered heteroaryl, wherein each cycloalkyl, aryl, heterocyclyl, and heteroaryl is optionally substituted with one or two R$^{5b}$. In some embodiments, each cycloalkyl, aryl, heterocyclyl, and heteroaryl is optionally substituted with one R$^{5b}$.

In some embodiments, a compound of the disclosure is a compound, or pharmaceutically acceptable salt thereof, wherein R⁵ is C$_{5-6}$ cycloalkyl, C$_6$ aryl, 5- to 7-membered heterocyclyl, or 5- to 9-membered heteroaryl, wherein each cycloalkyl, aryl, heterocyclyl, and heteroaryl is optionally substituted with one or two R$^{5b}$. In some embodiments, each cycloalkyl, aryl, heterocyclyl, and heteroaryl is optionally substituted with one R$^{5b}$.

In some embodiments, a compound of the disclosure is a compound, or pharmaceutically acceptable salt thereof, wherein each R$^{5a}$ is independently hydrogen or C$_{1-6}$ alkyl. In some embodiments, a compound of the disclosure is a compound, or pharmaceutically acceptable salt thereof, wherein each R$^{5a}$ is independently hydrogen or C$_{1-3}$ alkyl. In some embodiments, a compound of the disclosure is a compound, or pharmaceutically acceptable salt thereof, wherein R$^{5a}$ is hydrogen. In some embodiments, a compound of the disclosure is a compound, or pharmaceutically acceptable salt thereof, wherein R$^{5a}$ is methyl.

In some embodiments, a compound of the disclosure is a compound, or pharmaceutically acceptable salt thereof, wherein each R$^{5b}$ is independently halogen, cyclopropyl, hydroxy, —CN, C$_{1-3}$ alkyl, C$_{1-3}$ alkoxy, —OCF$_3$, or —OCF$_2$H. In some embodiments, a compound of the disclosure is a compound, or pharmaceutically acceptable salt thereof, wherein each R$^{5b}$ is independently fluoro, chloro, cyclopropyl, hydroxy, —CN, methyl, methoxy, —OCF$_3$, or —OCF$_2$H.

In some embodiments, a compound of the disclosure is a compound, or pharmaceutically acceptable salt thereof, wherein each R$^{5b}$ is independently C$_{1-3}$ alkyl or C$_{1-3}$ alkoxy. In some embodiments, a compound of the disclosure is a compound, or pharmaceutically acceptable salt thereof, wherein each Rb is independently methyl or methoxy. In some embodiments, a compound of the disclosure is a compound, or pharmaceutically acceptable salt thereof, wherein each R$^{5b}$ is independently methyl. In some embodiments, a compound of the disclosure is a compound, or pharmaceutically acceptable salt thereof, wherein each R$^{5b}$ is independently methoxy.

In some embodiments, a compound of the disclosure is a compound, or pharmaceutically acceptable salt thereof, wherein Z is O or S. In some embodiments, a compound of the disclosure is a compound, or pharmaceutically acceptable salt thereof, wherein is O. In some embodiments, a compound of the disclosure is a compound, or pharmaceutically acceptable salt thereof, wherein Z is S.

In some embodiments, a compound of the disclosure is a compound, or pharmaceutically acceptable salt thereof, having a structure as shown in Scheme A:

Scheme A

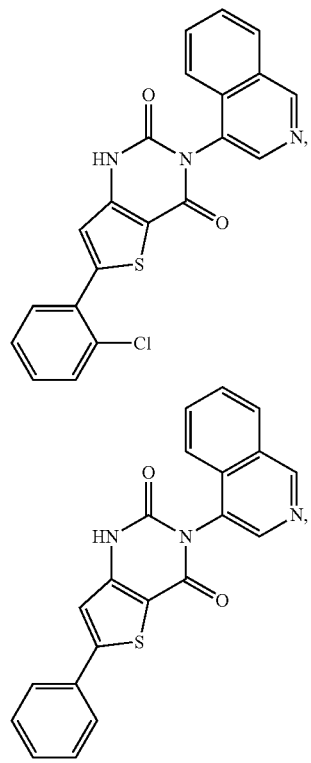

-continued
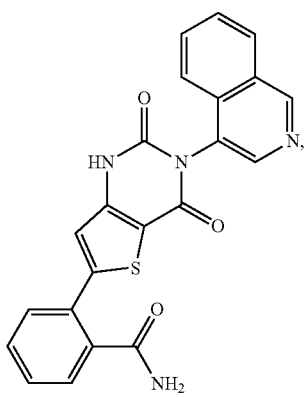
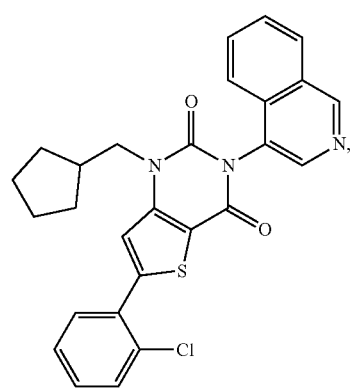
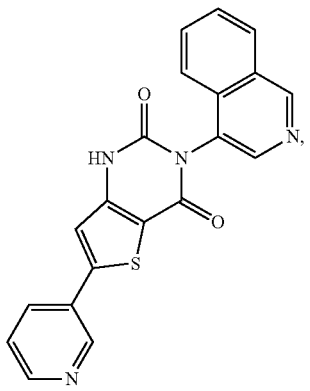
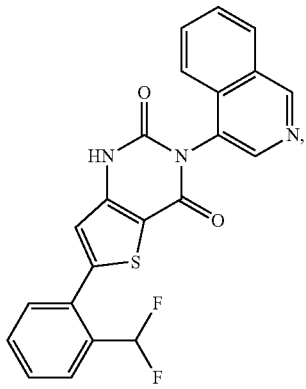
-continued
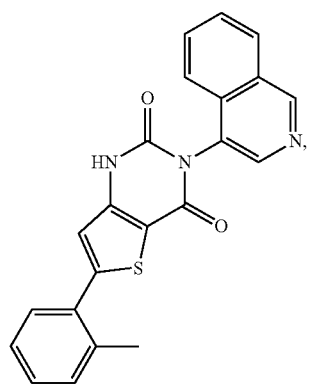
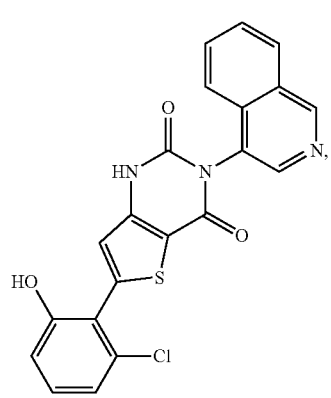
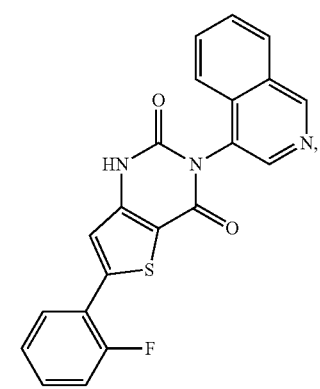
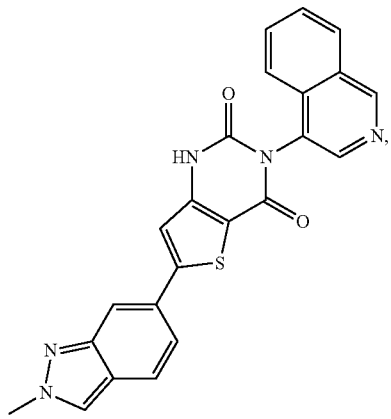

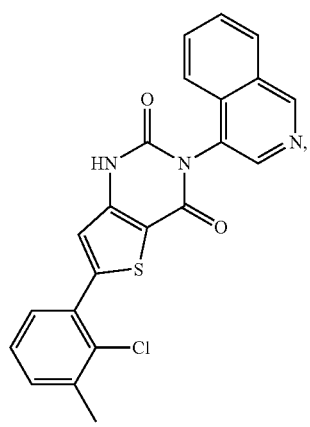
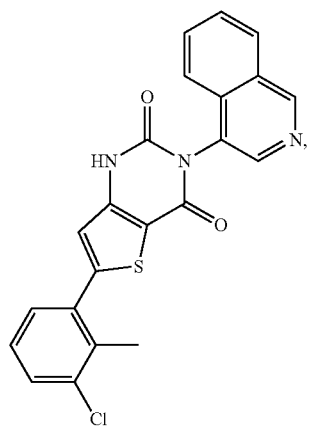
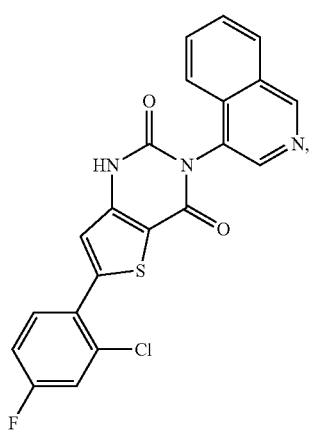
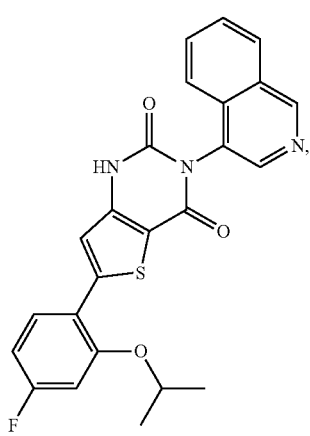
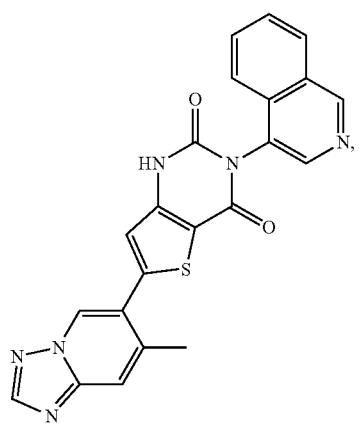
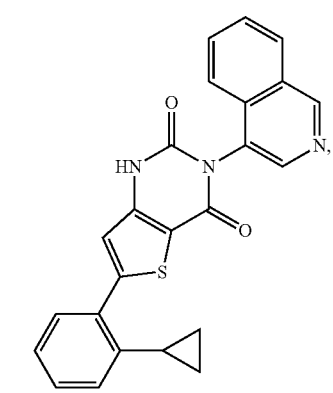
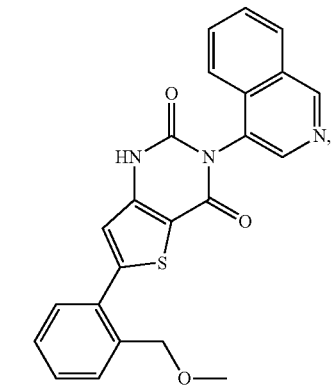
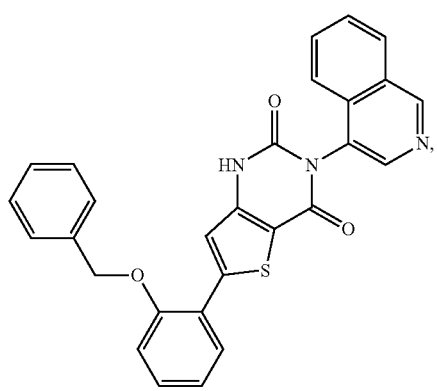

-continued
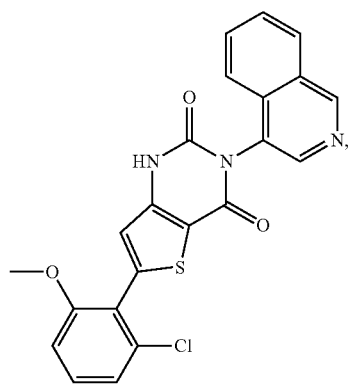
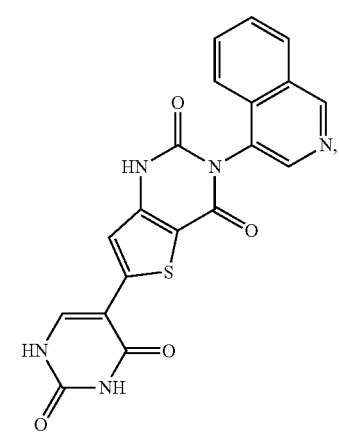
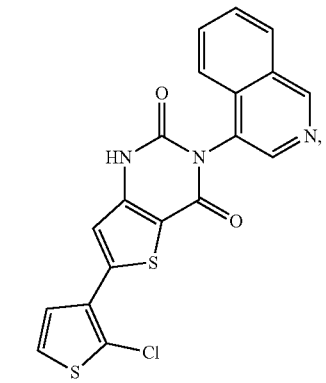
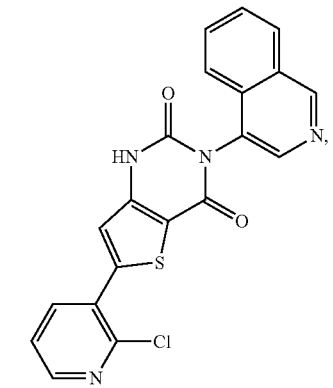
-continued
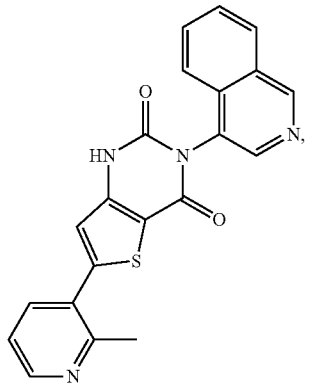
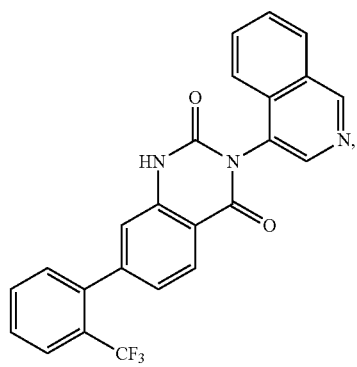
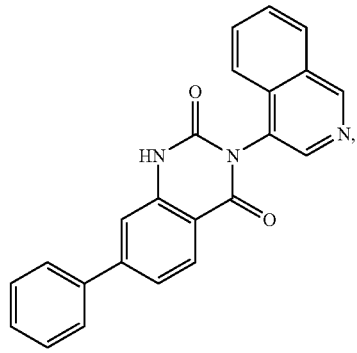
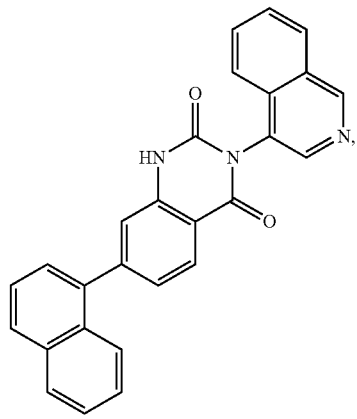

-continued
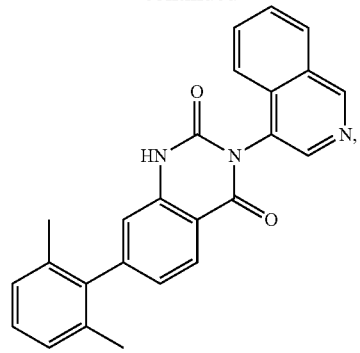
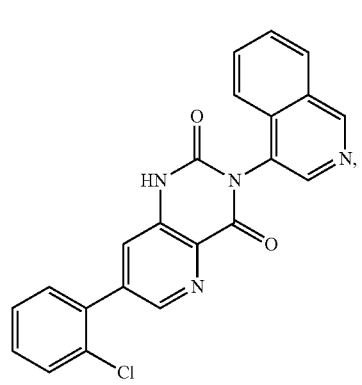
-continued
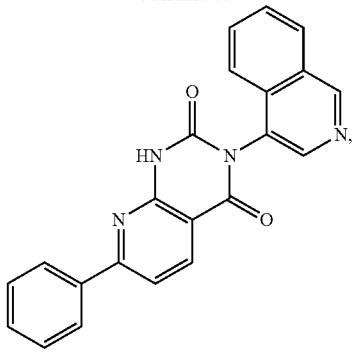
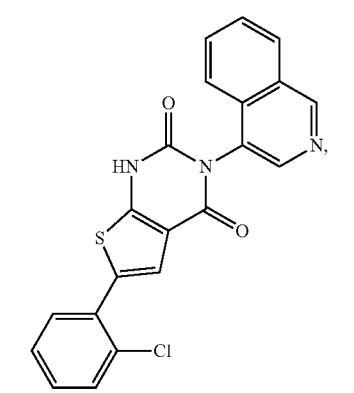
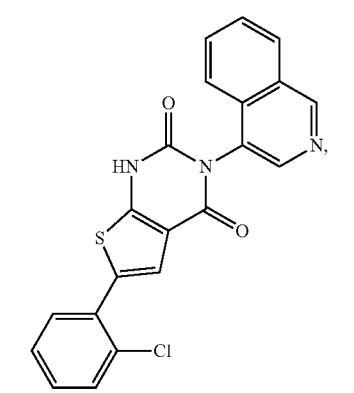
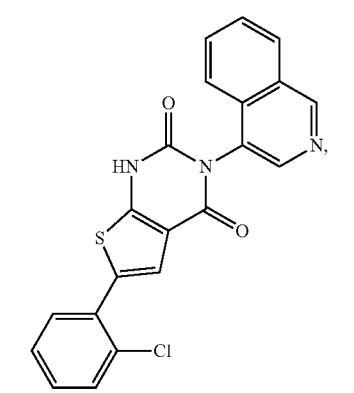

85
-continued
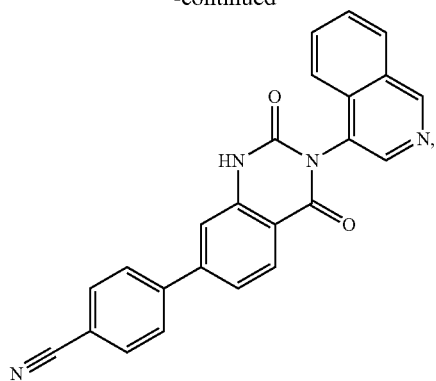
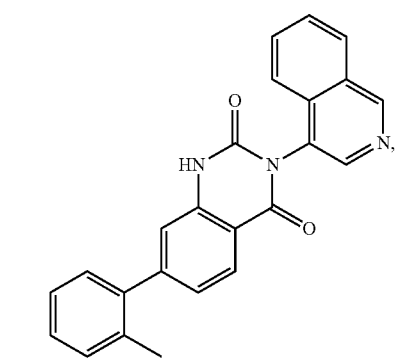
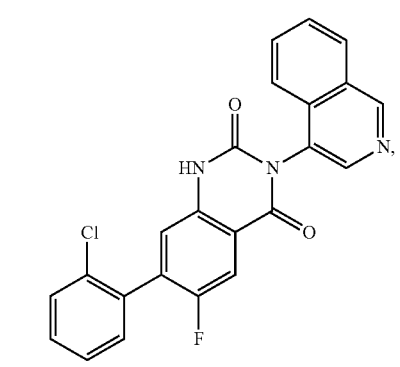
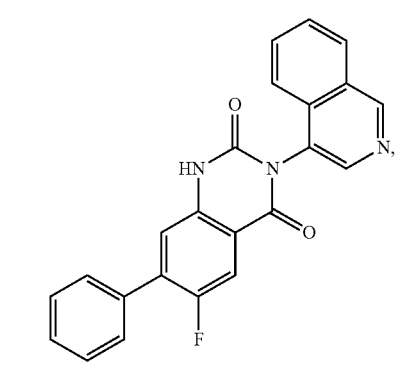
86
-continued
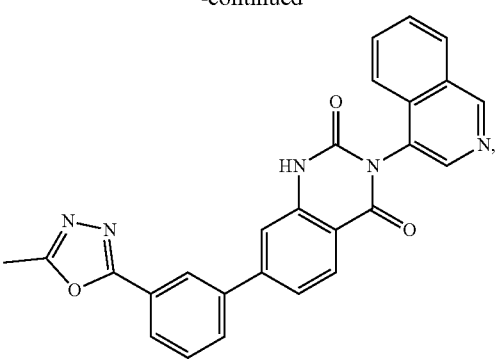
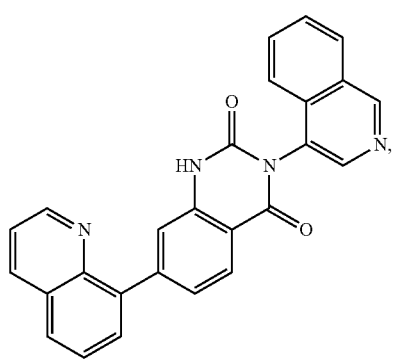
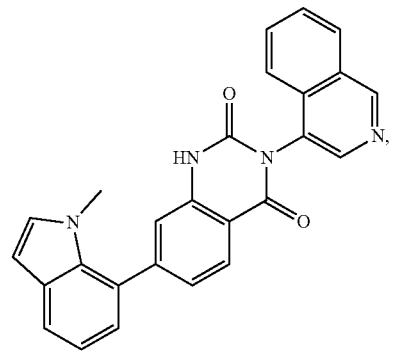
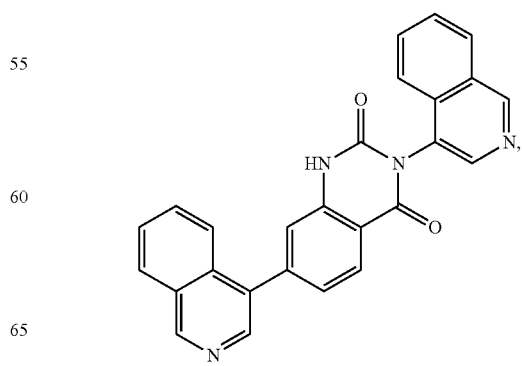

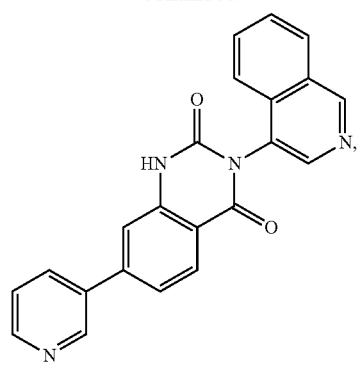
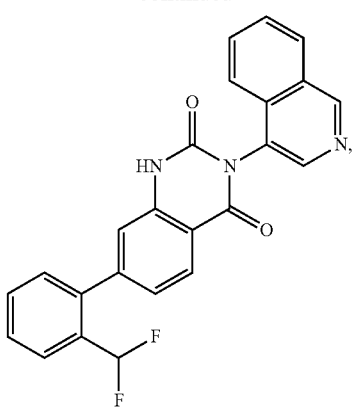

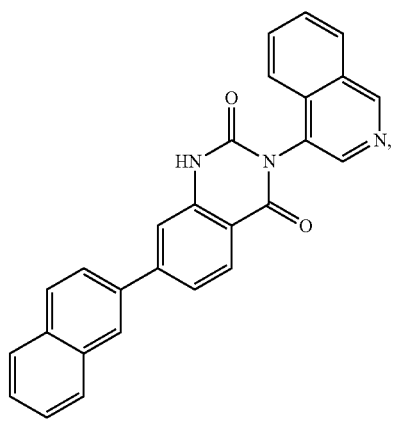
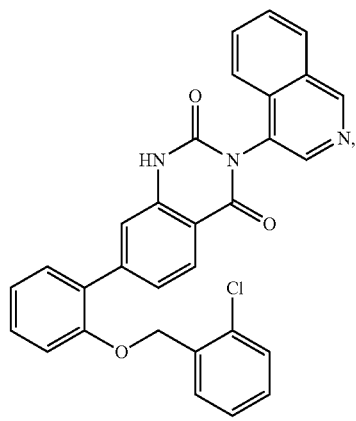
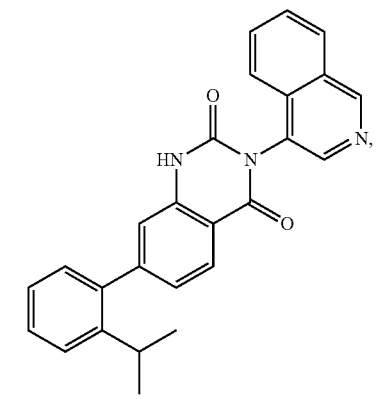
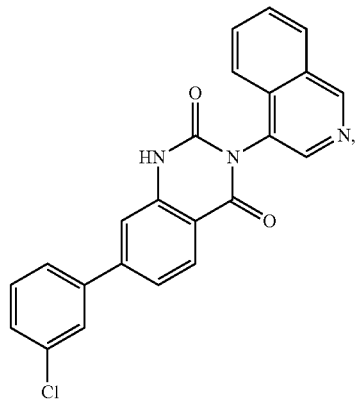
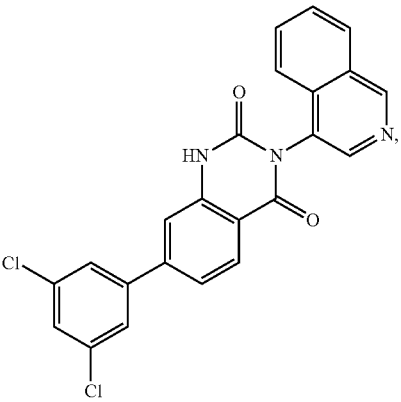
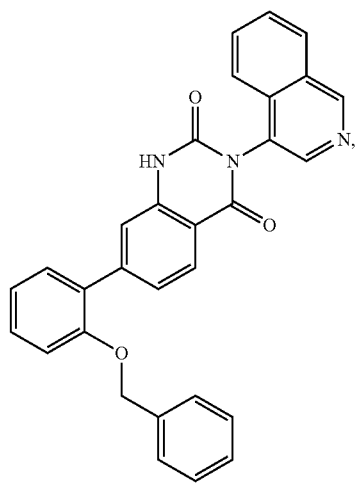
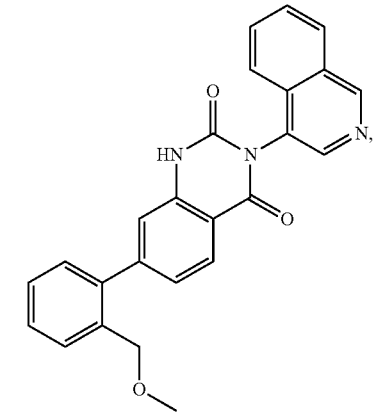
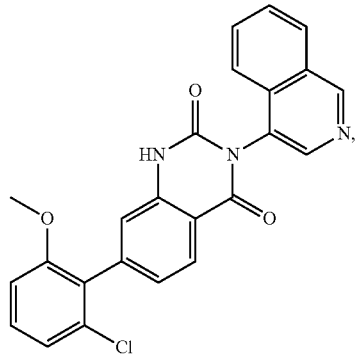

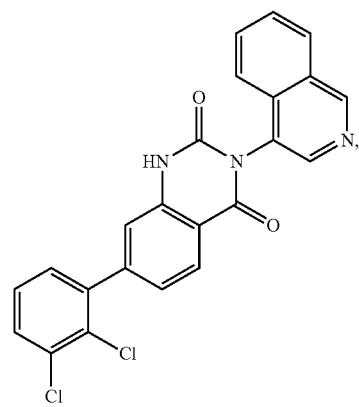
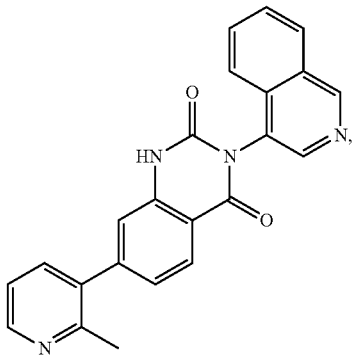
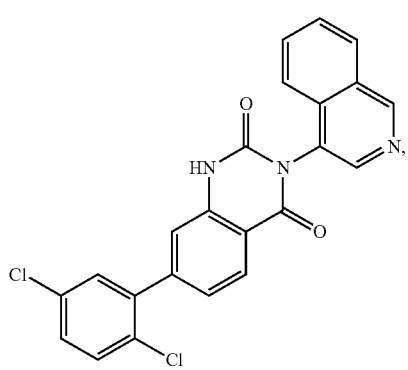
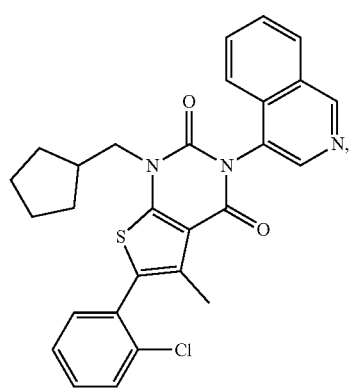
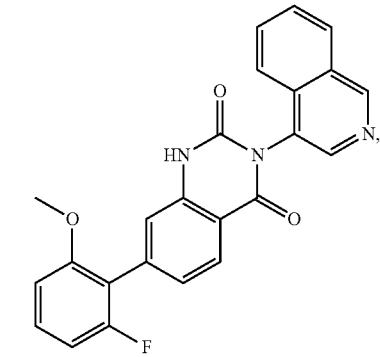
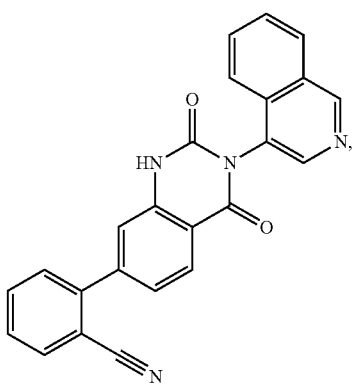
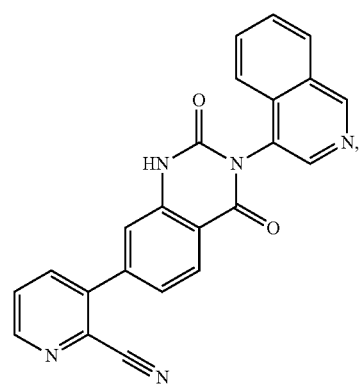
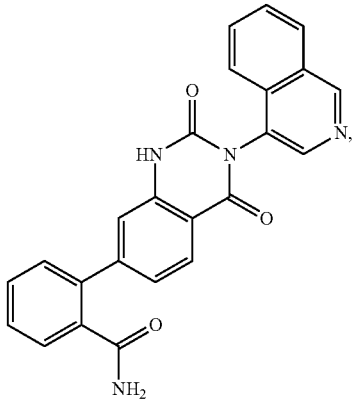

-continued
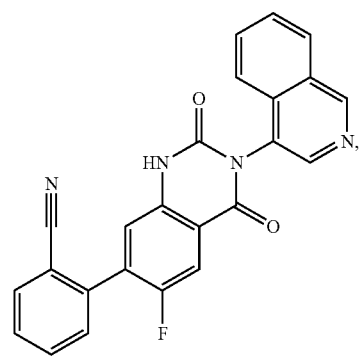
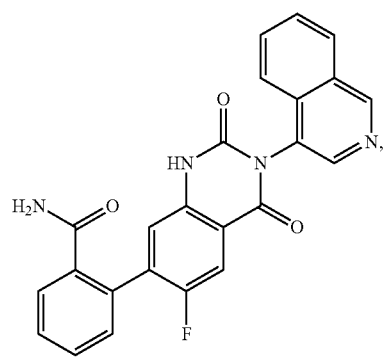
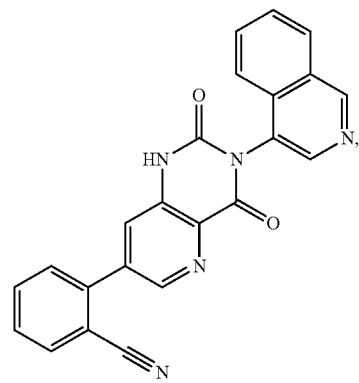
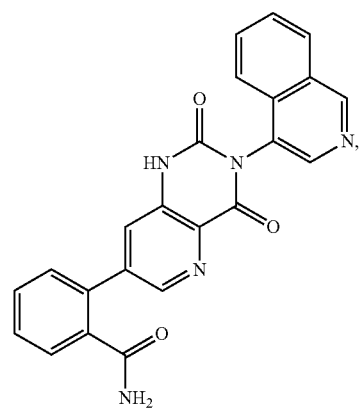
-continued
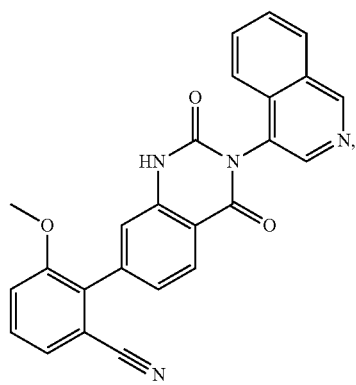
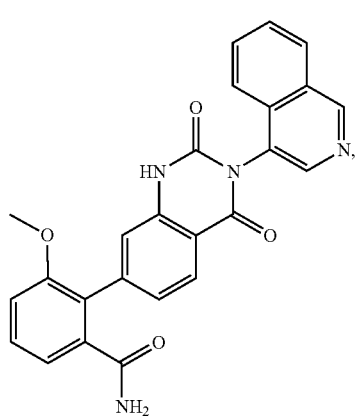
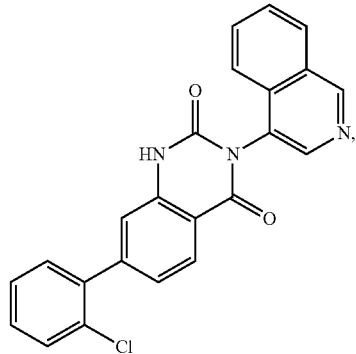
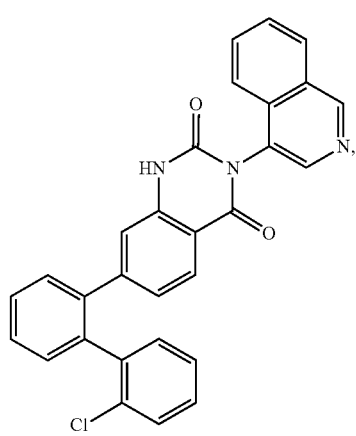

-continued
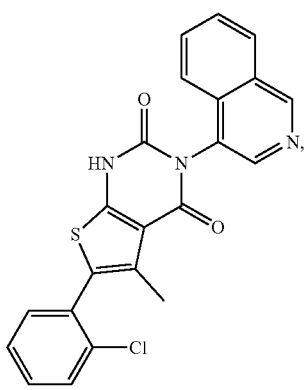
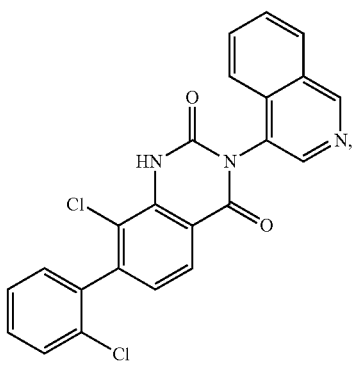
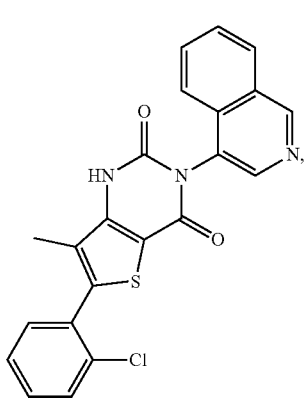
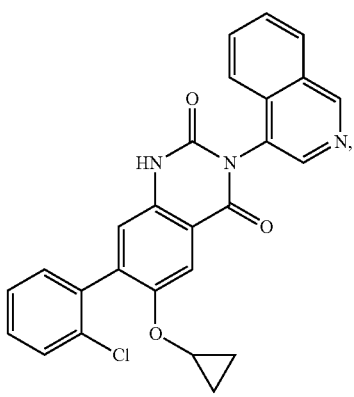
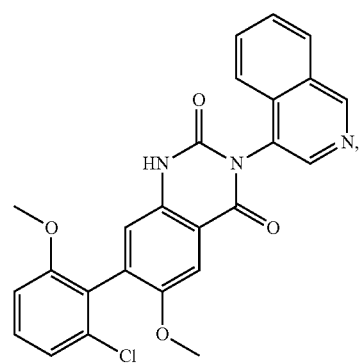
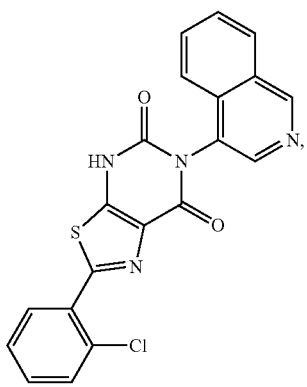

-continued
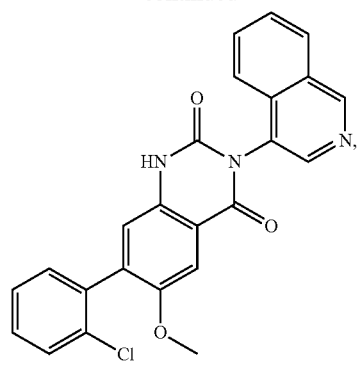
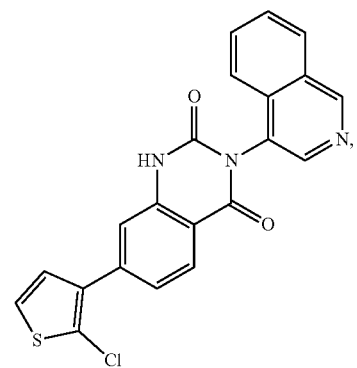
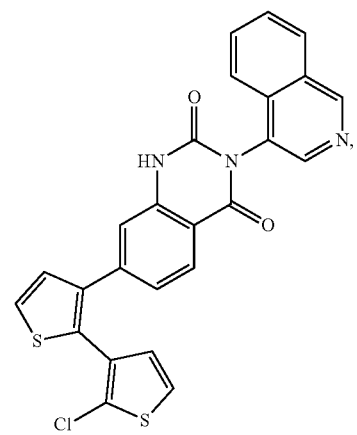
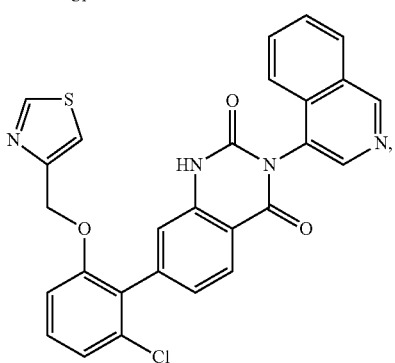
-continued
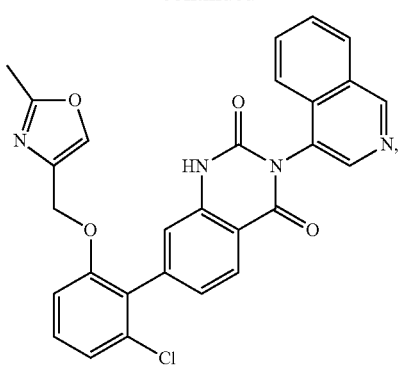
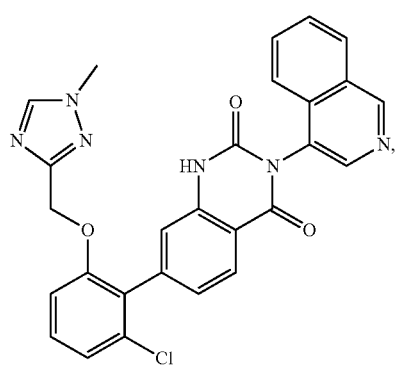
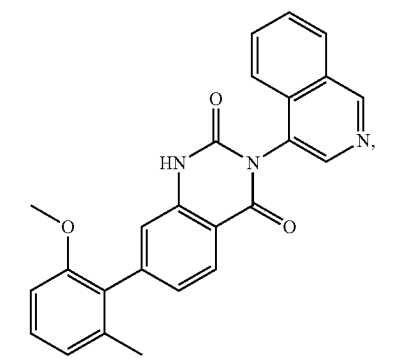
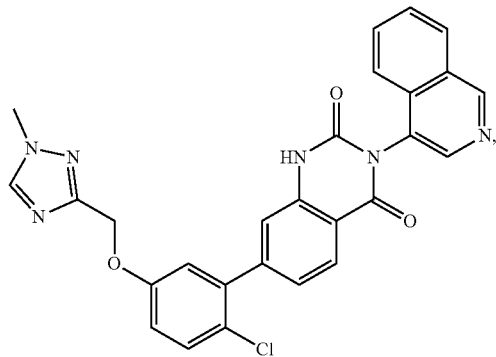

99
-continued
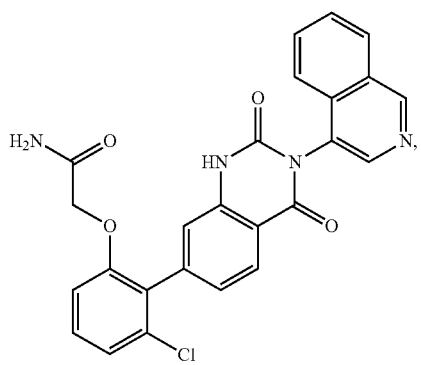
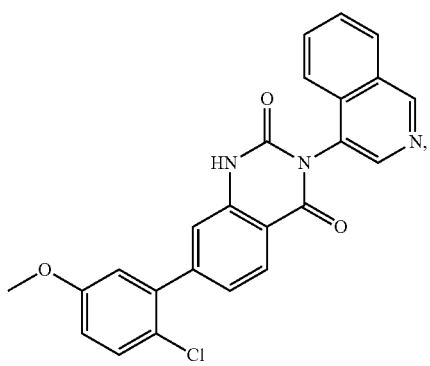
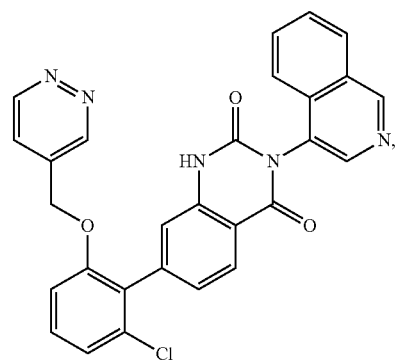
100
-continued
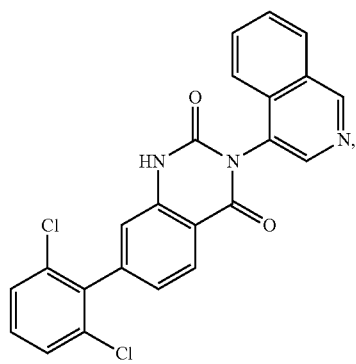
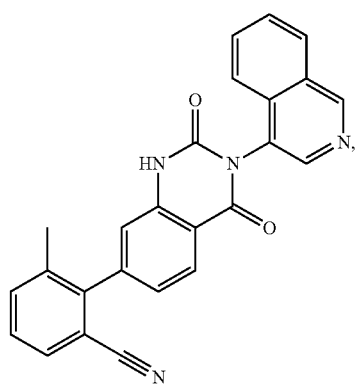
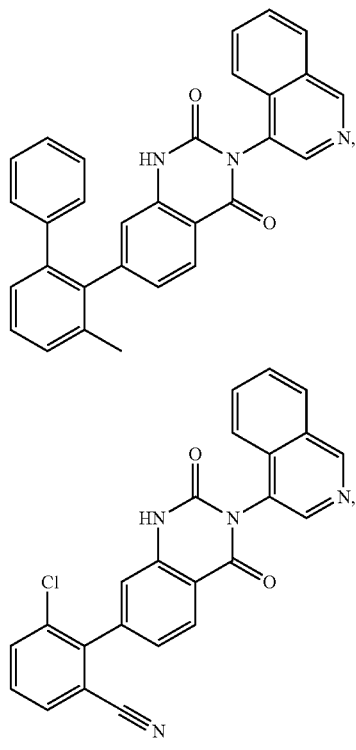

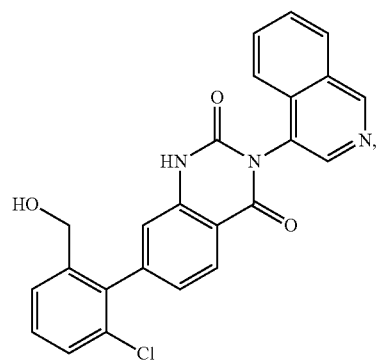
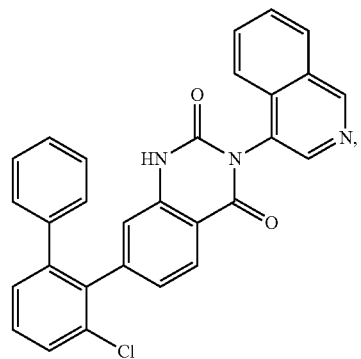
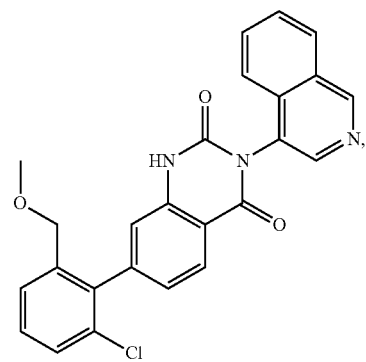
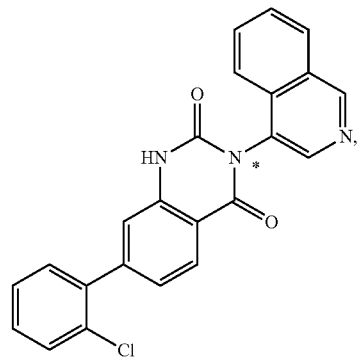
Isomer 1
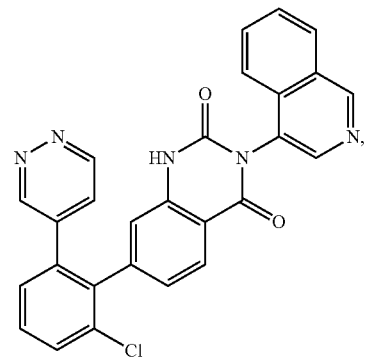
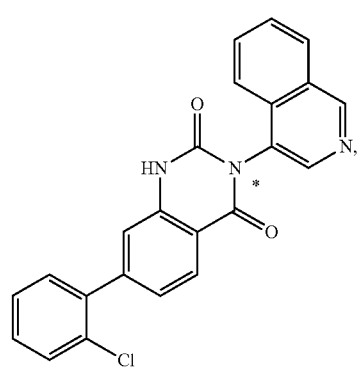
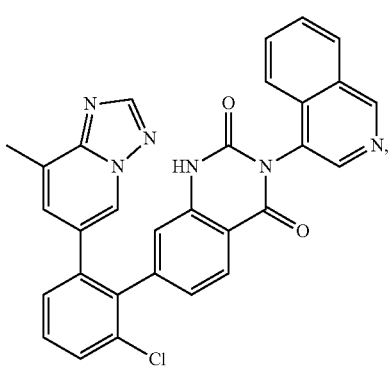
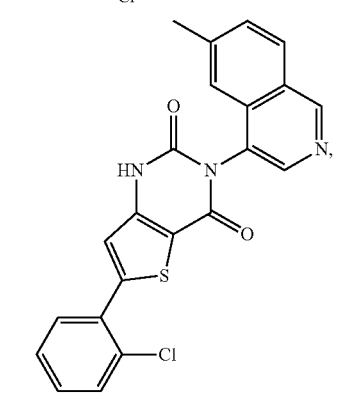

103
-continued
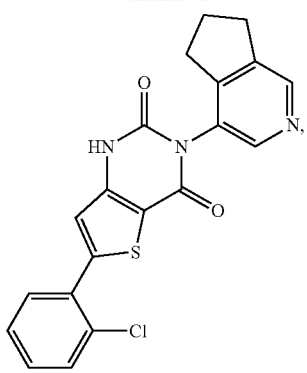
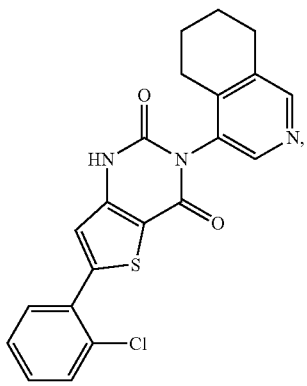
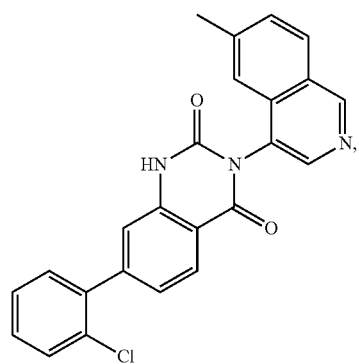
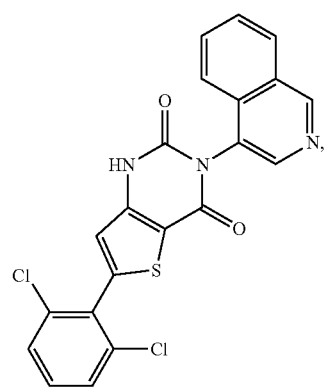
104
-continued
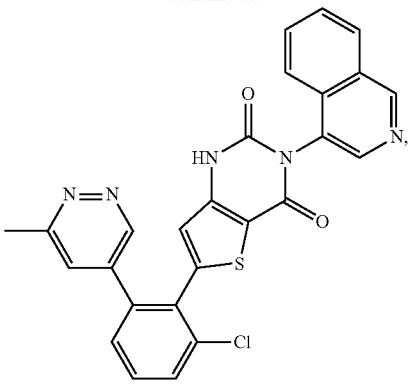
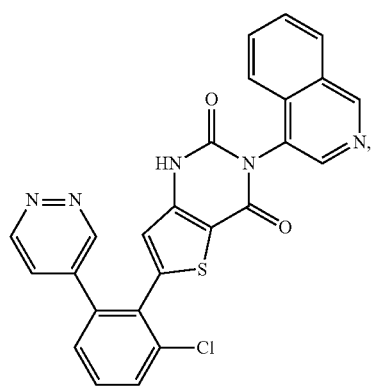
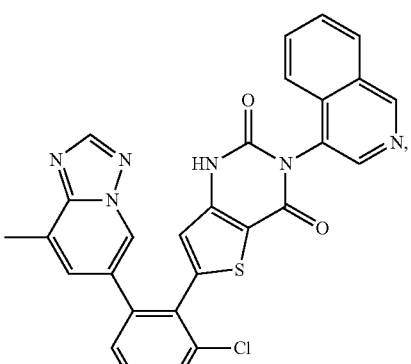
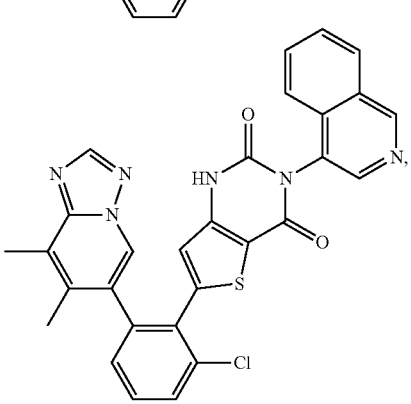

105
-continued
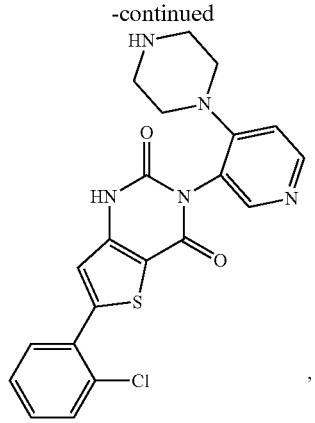
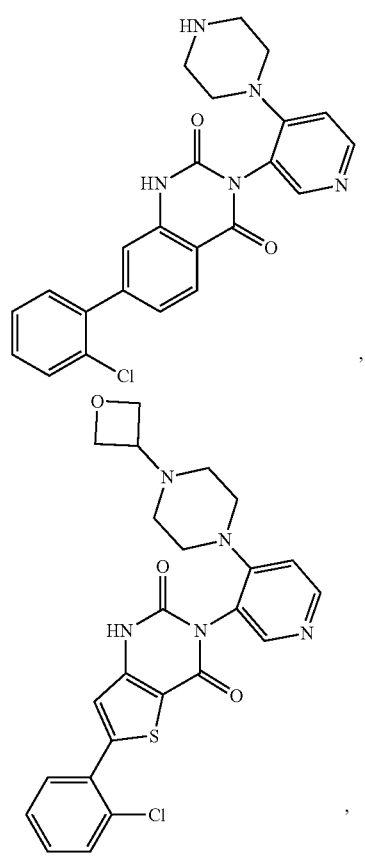
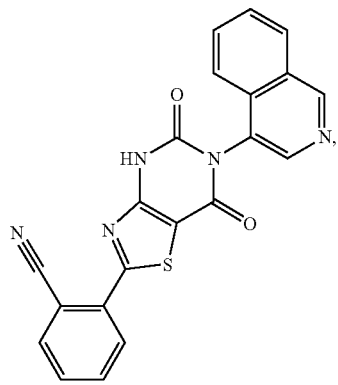
106
-continued
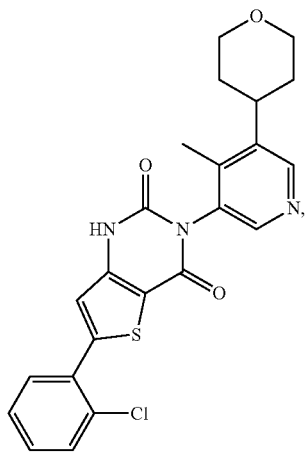
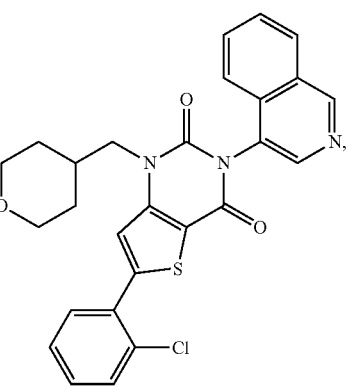
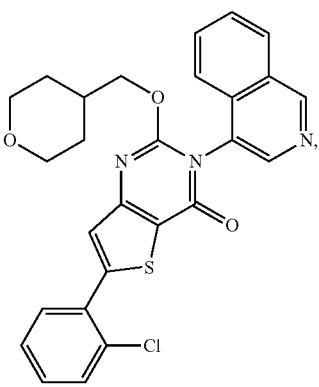
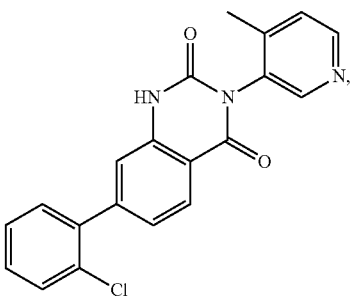

107
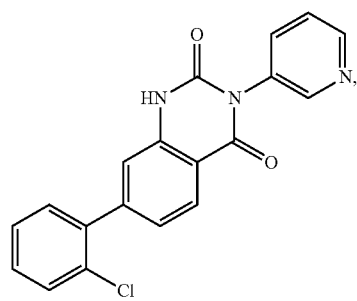
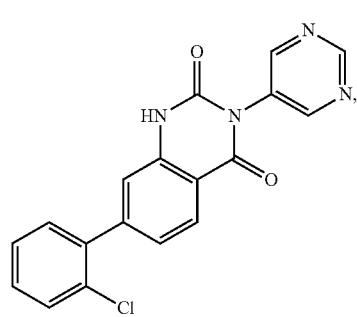
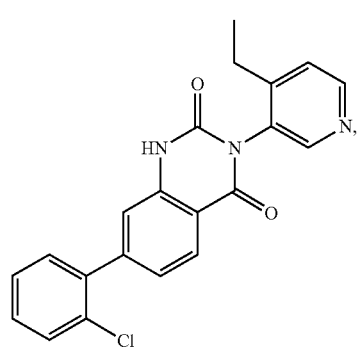
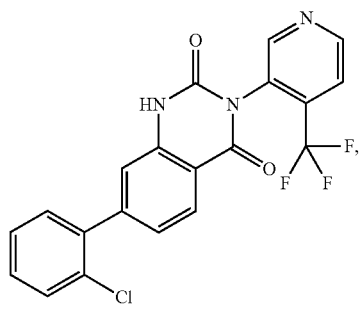
108
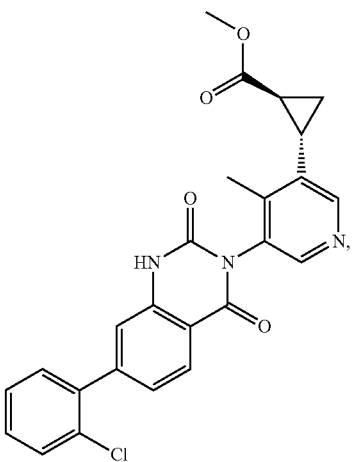
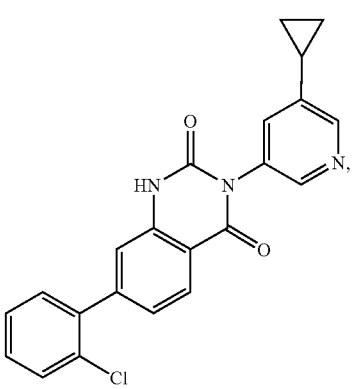
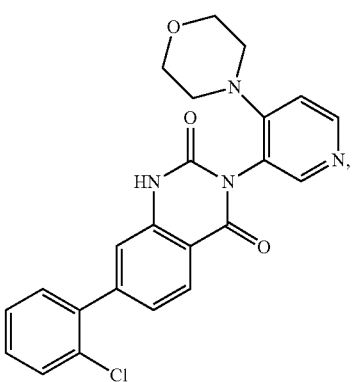
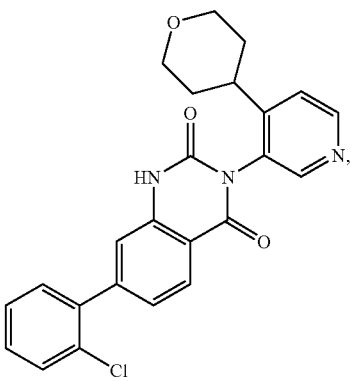

-continued
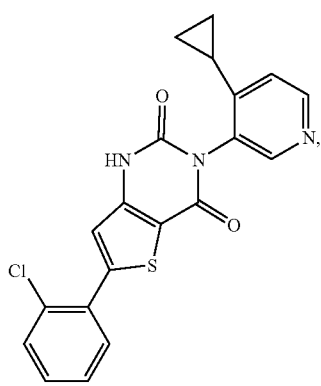
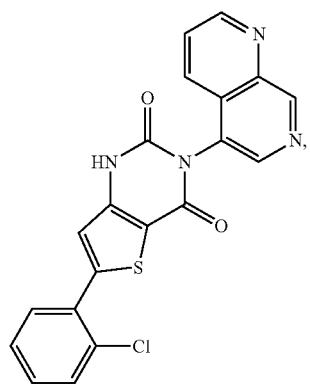
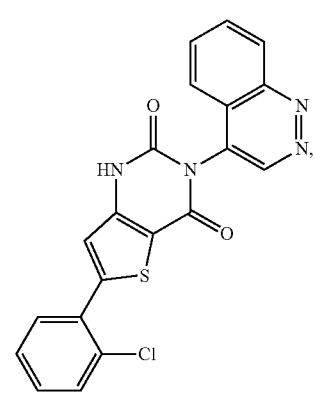
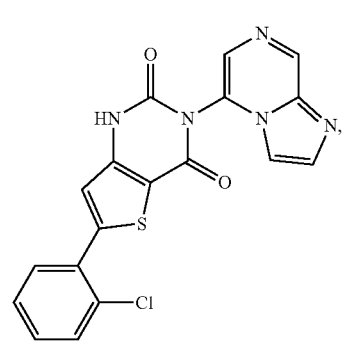
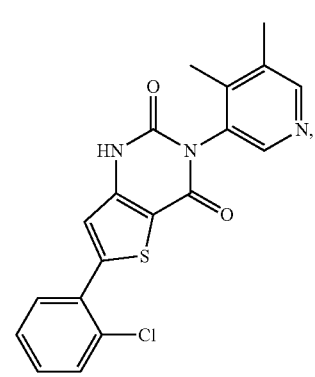
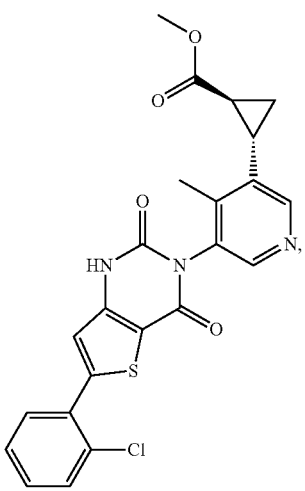
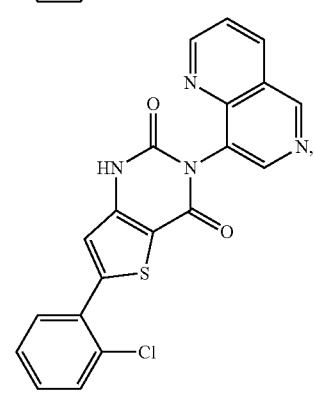
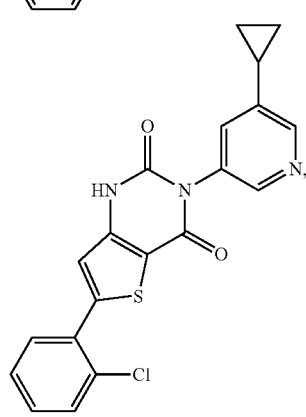

111
-continued
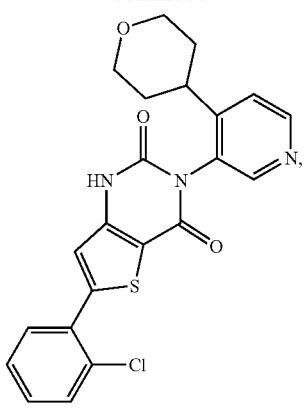
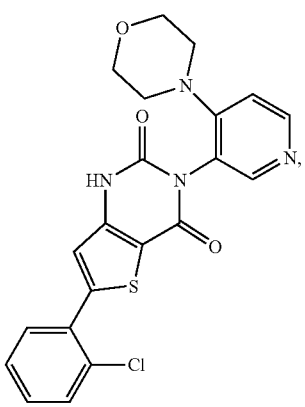
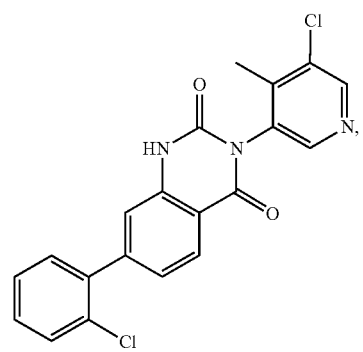
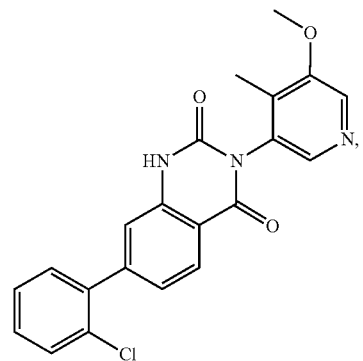
112
-continued
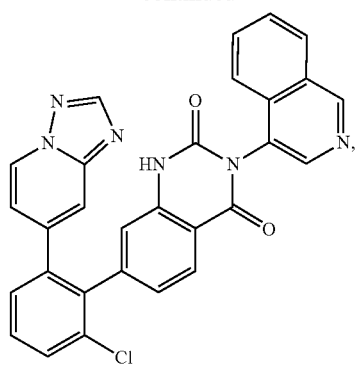
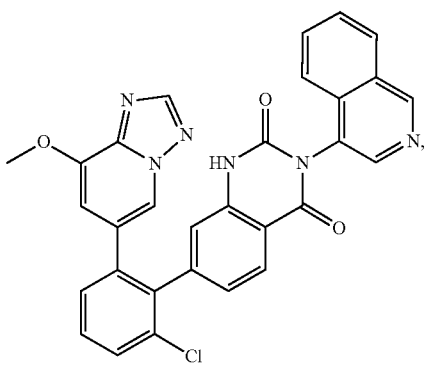
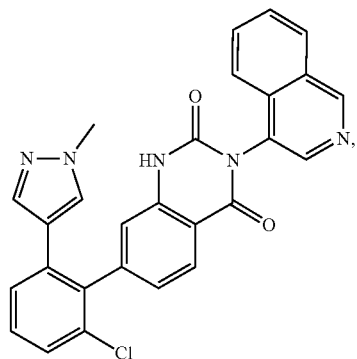
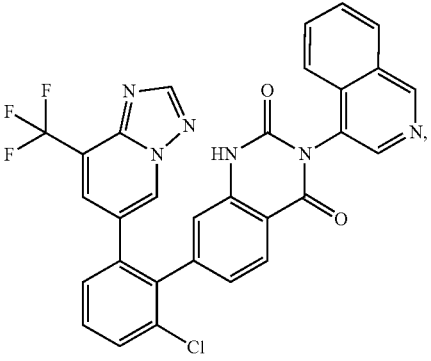

113
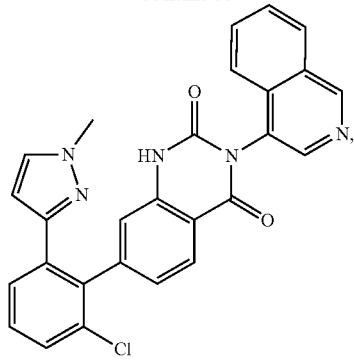
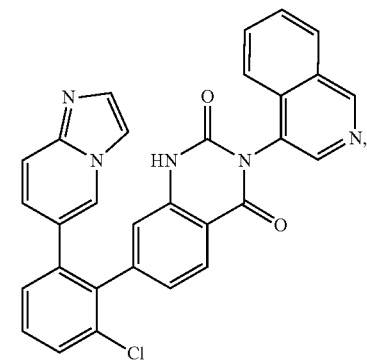
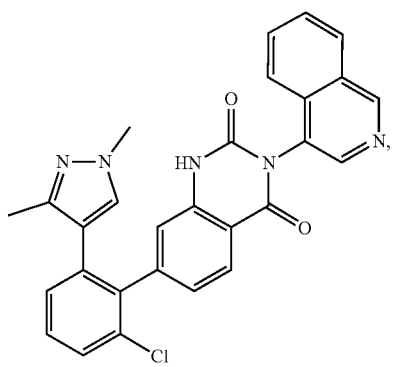
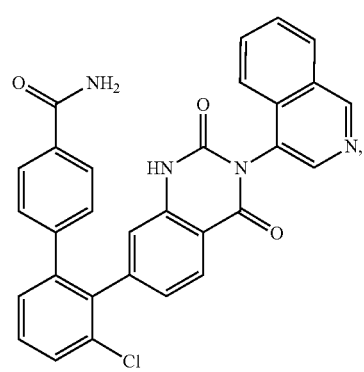
114
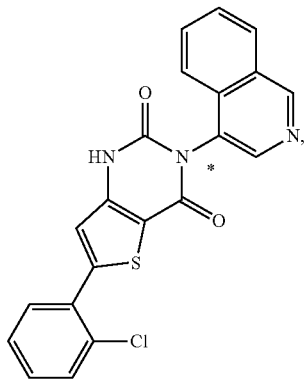
Isomer 1
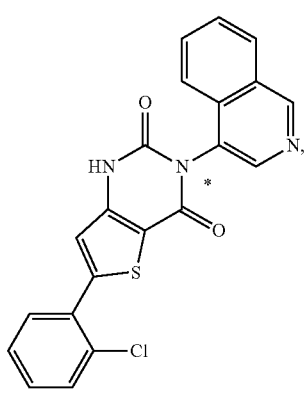
Isomer 2
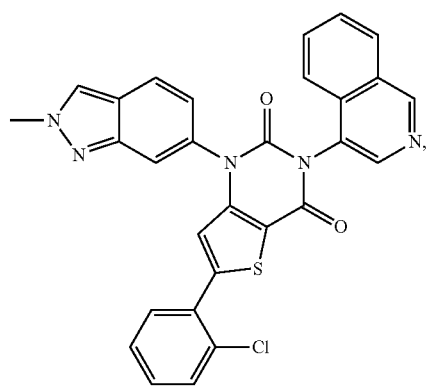
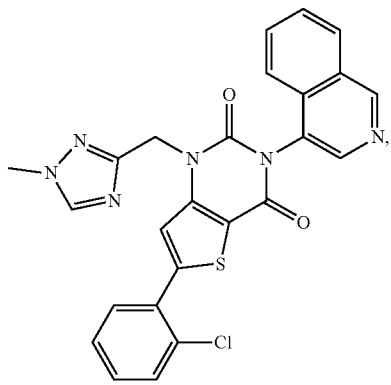

115
-continued
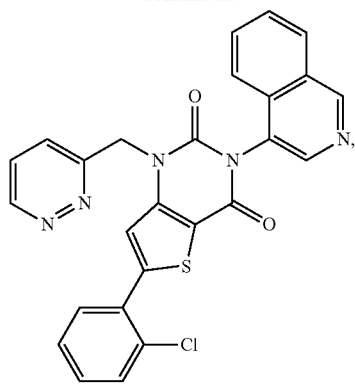
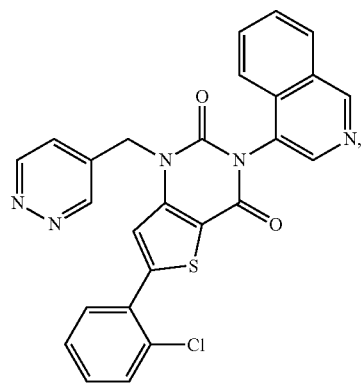
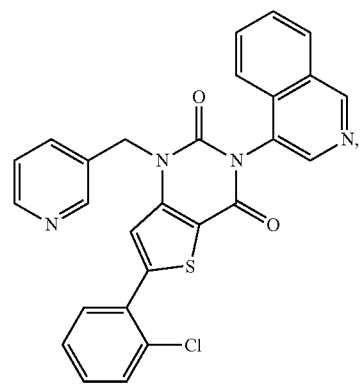
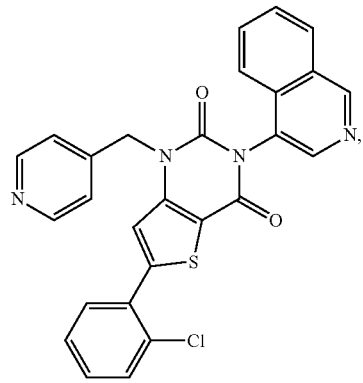
116
-continued
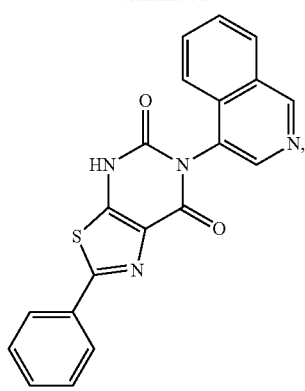
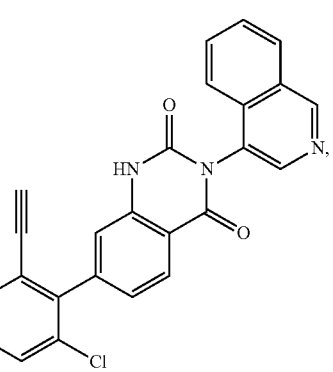
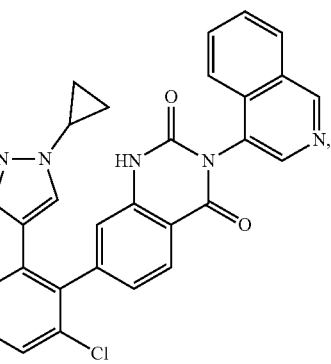
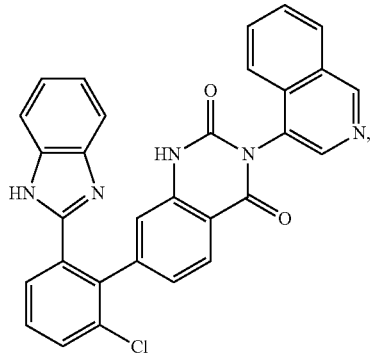

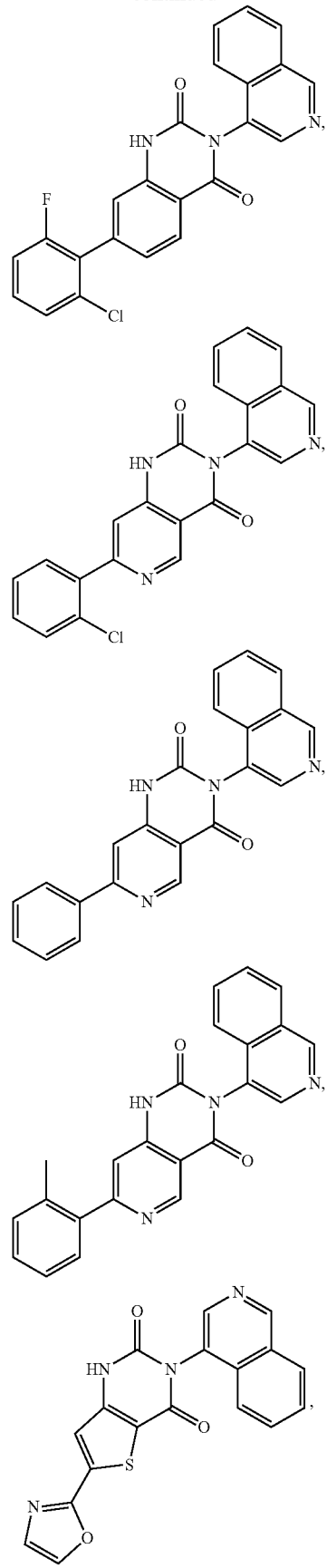
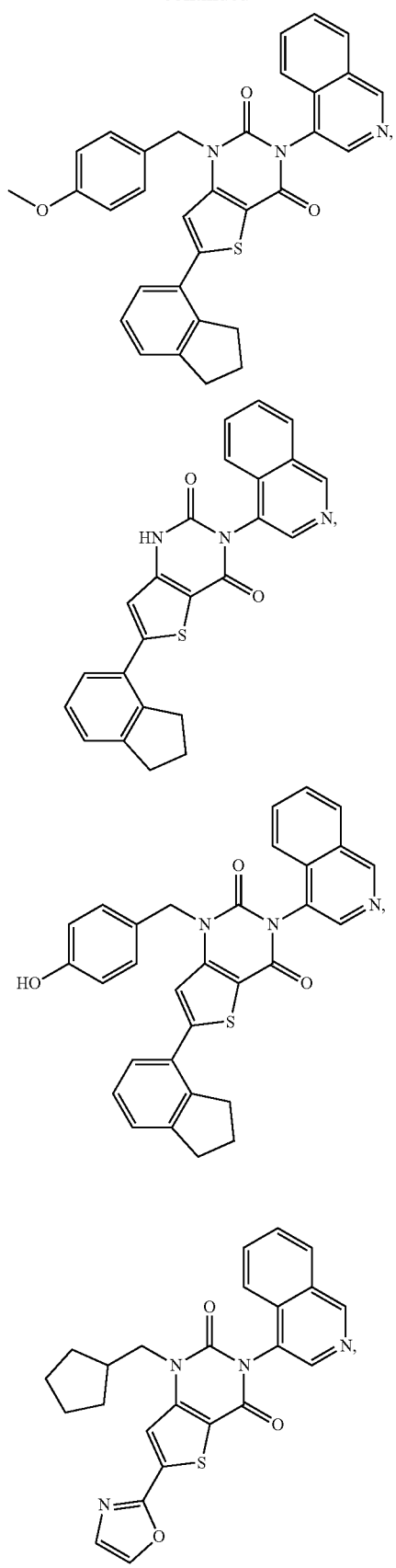

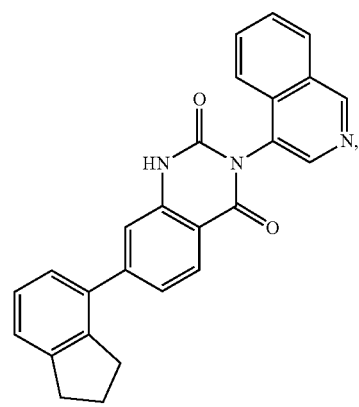
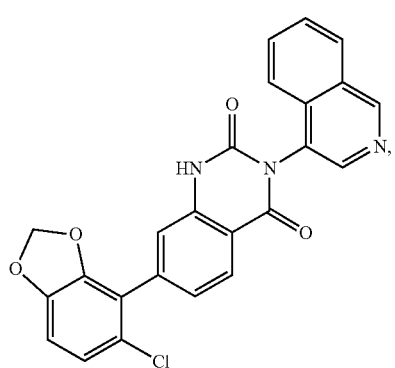
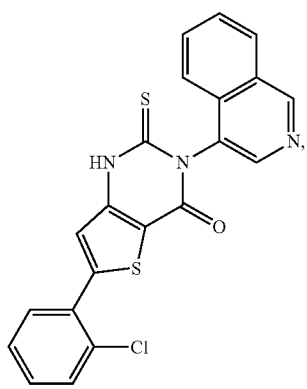
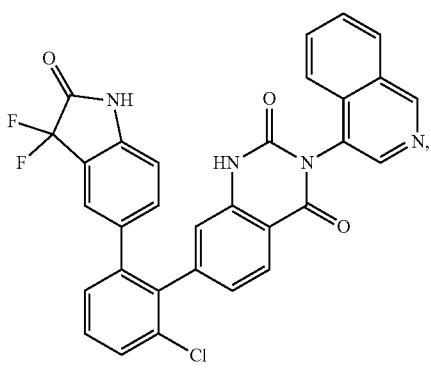
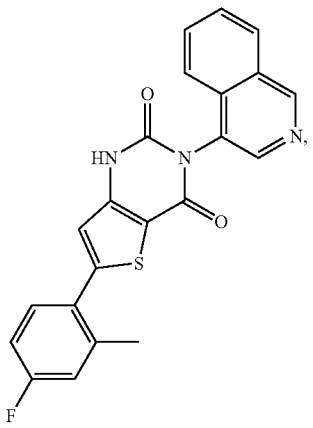
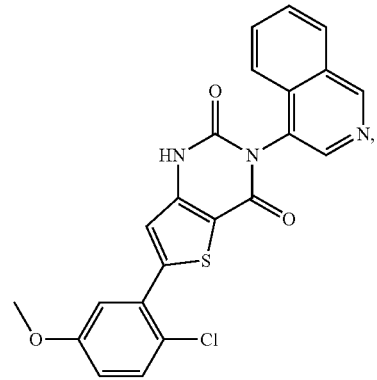
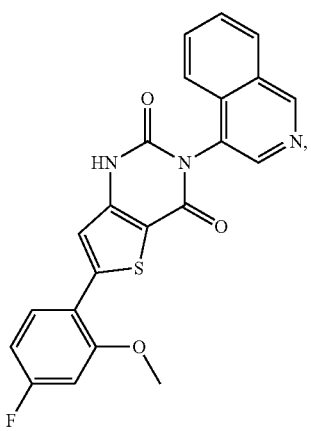

121
-continued
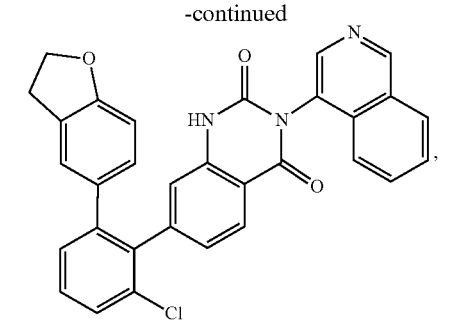
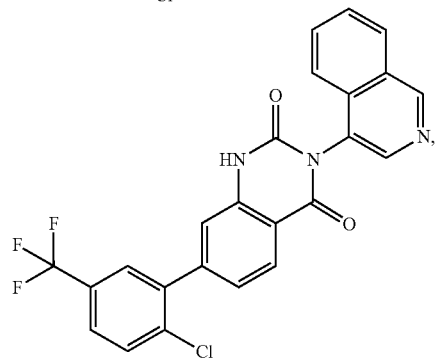
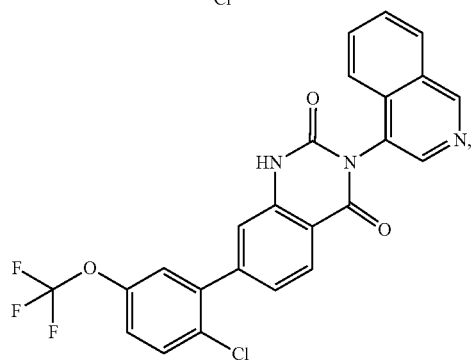
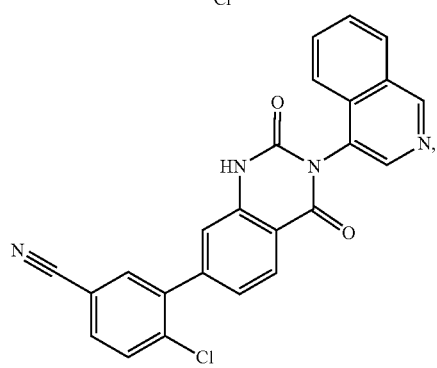
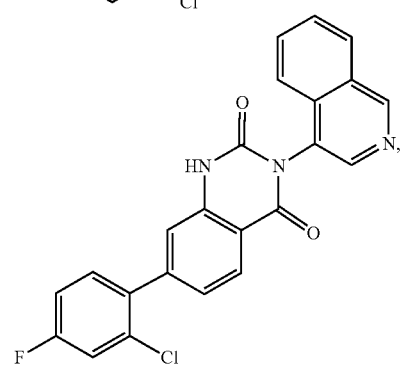
122
-continued
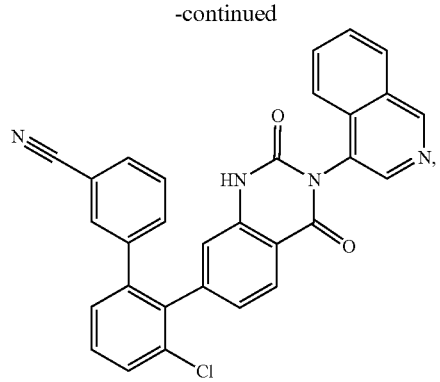
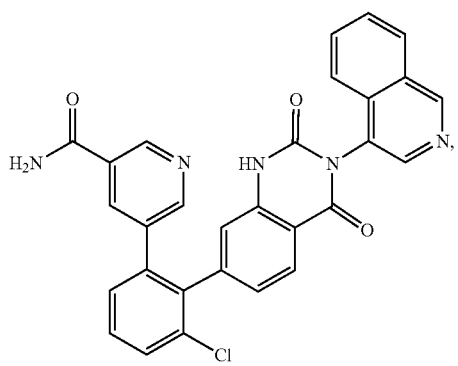
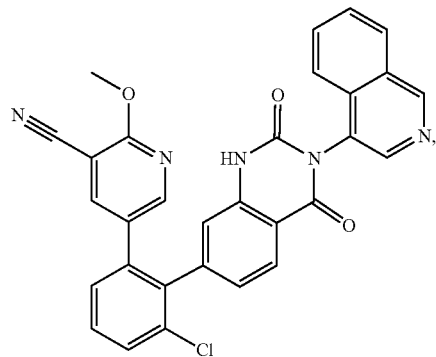
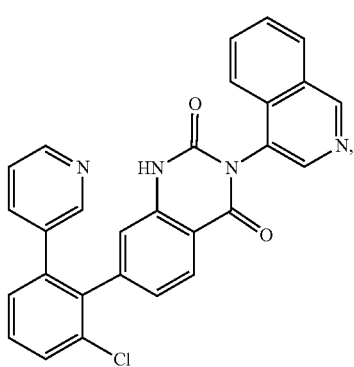

123
-continued
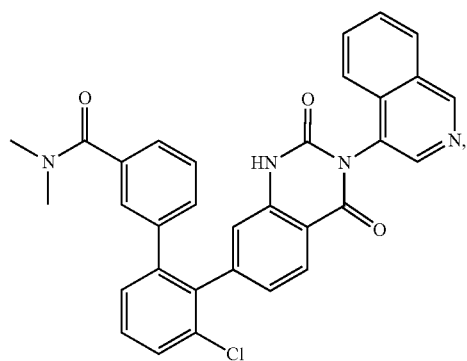
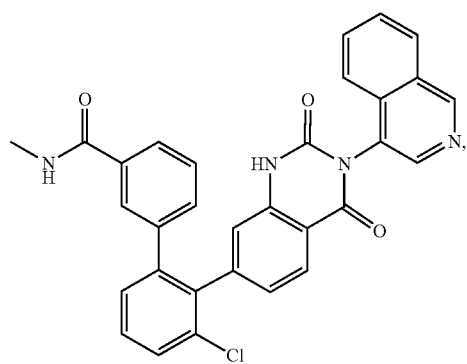
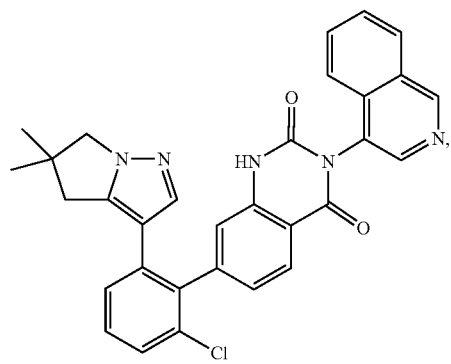
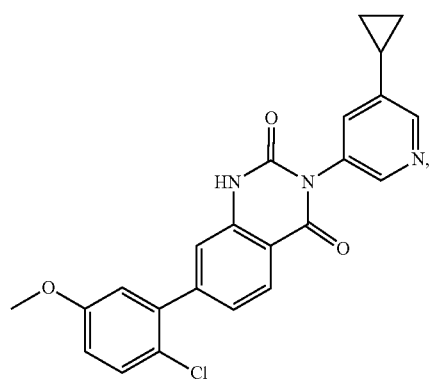
124
-continued
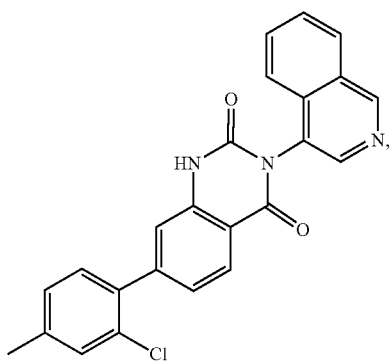
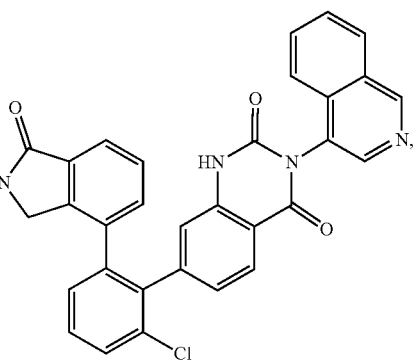
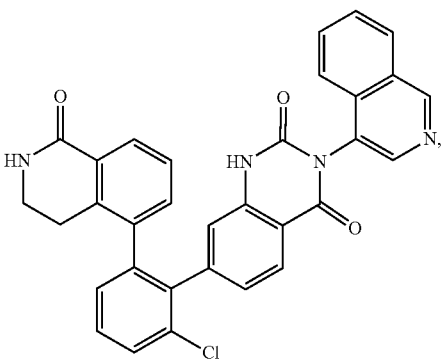
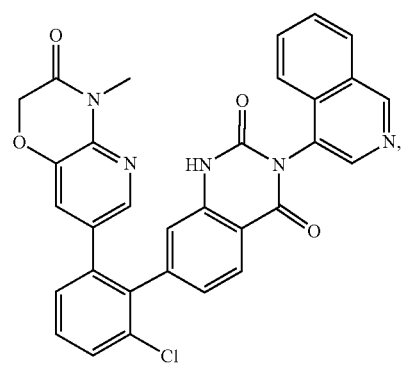

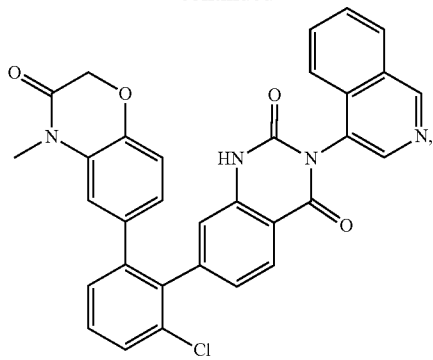
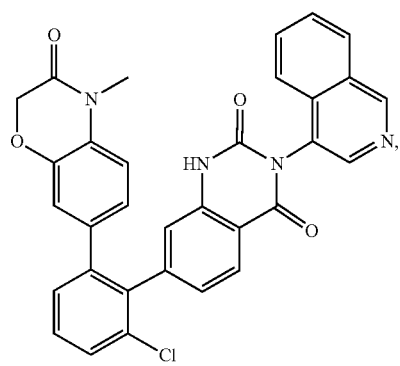
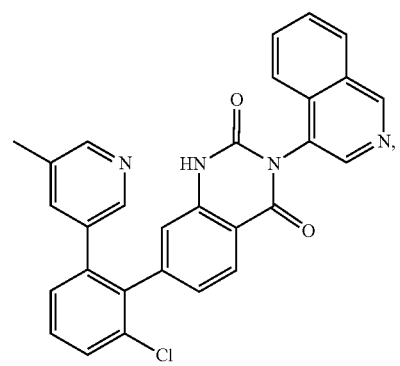
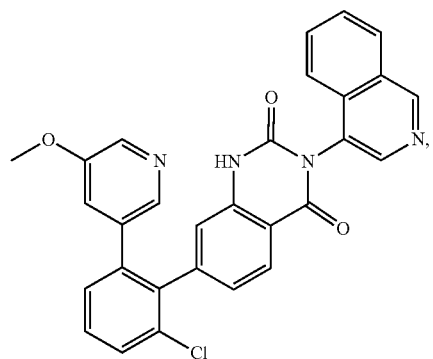
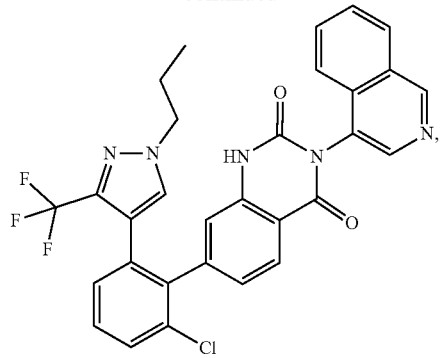 [SMILES: CCCn1cc(-c2cccc(Cl)c2-c2ccc3c(=O)n(-c4cncc5ccccc45)c(=O)[nH]c3c2)c(C(F)(F)F)n1]
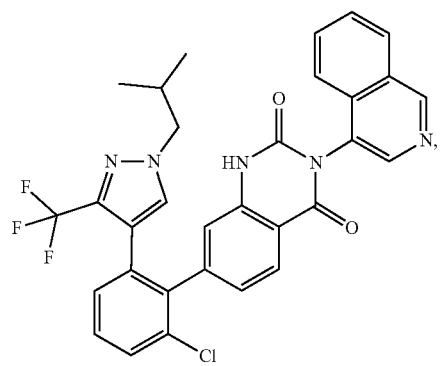
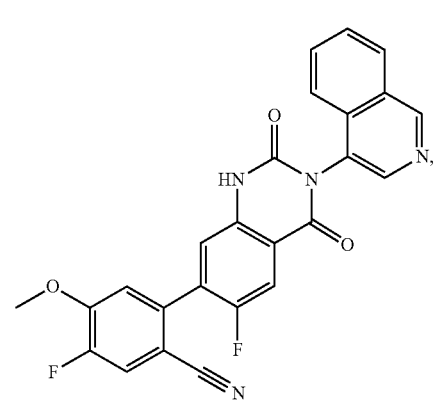
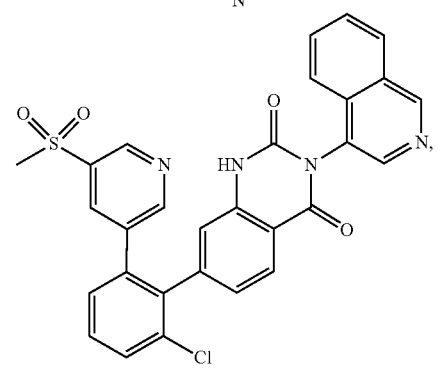

127
-continued
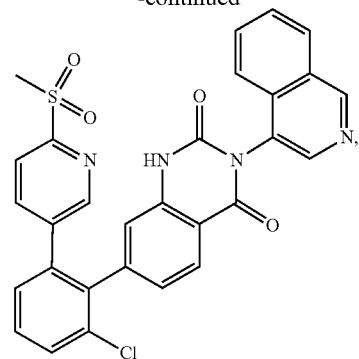
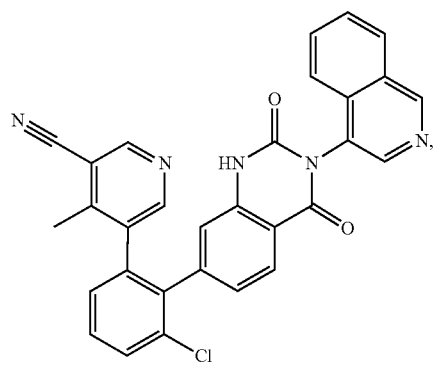
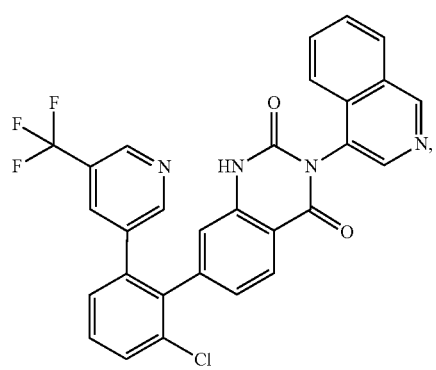
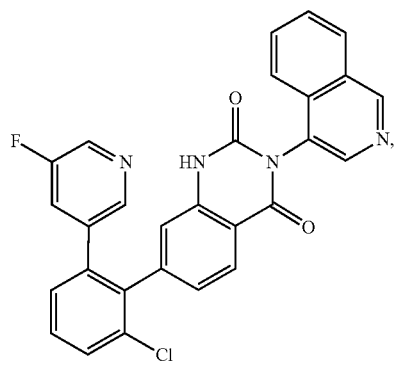
128
-continued
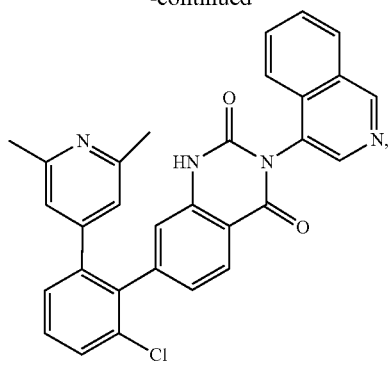
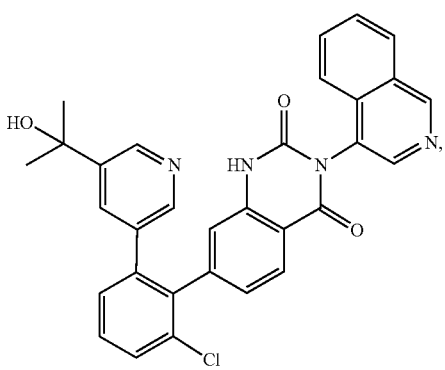
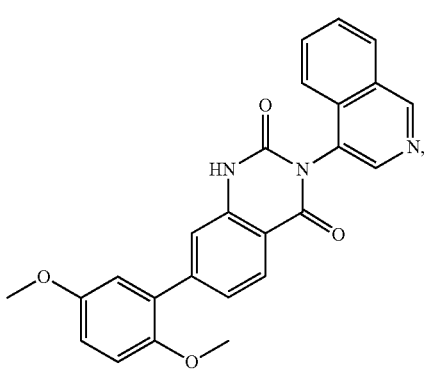
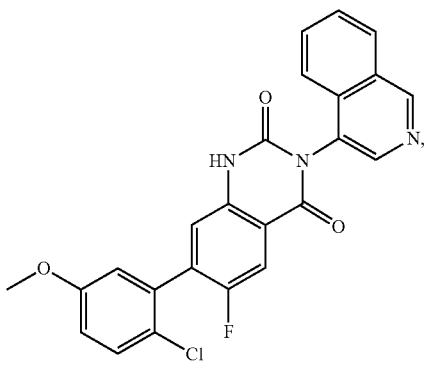

129
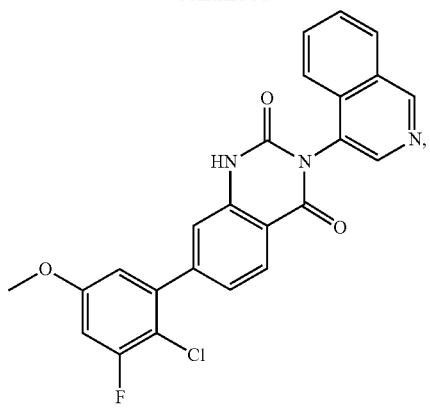
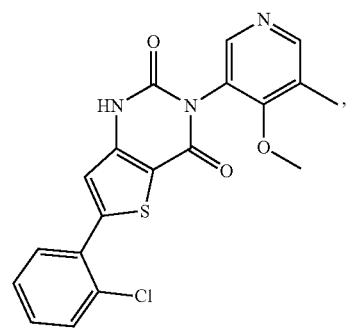
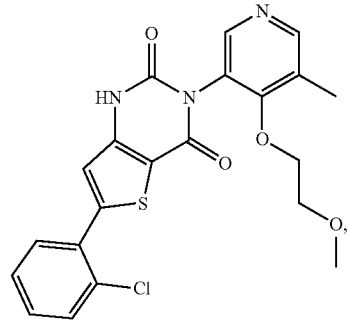
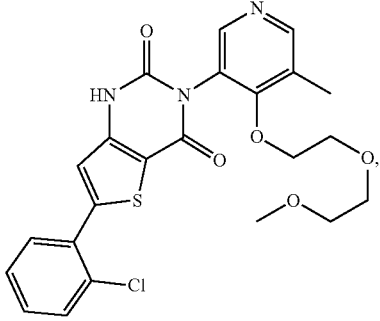
130
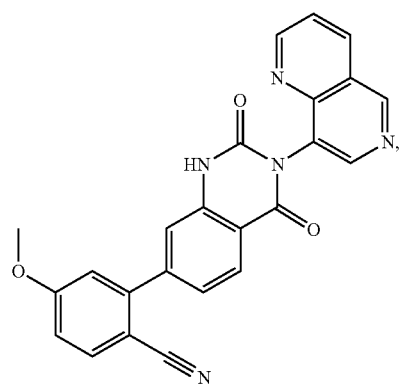
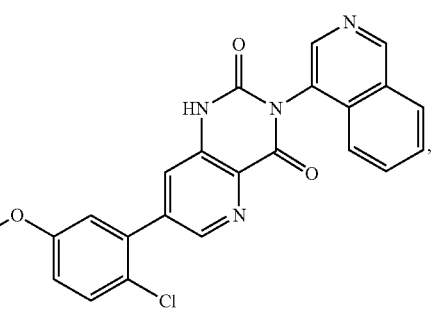
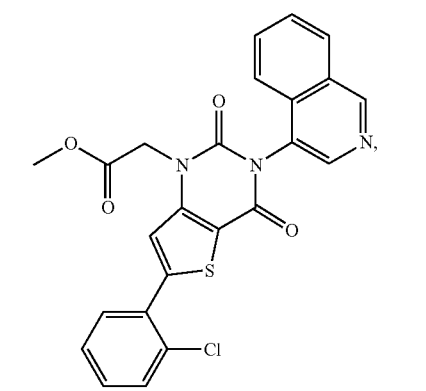
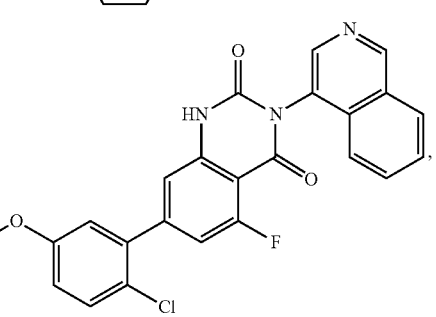

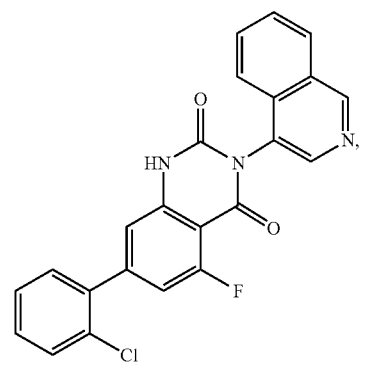
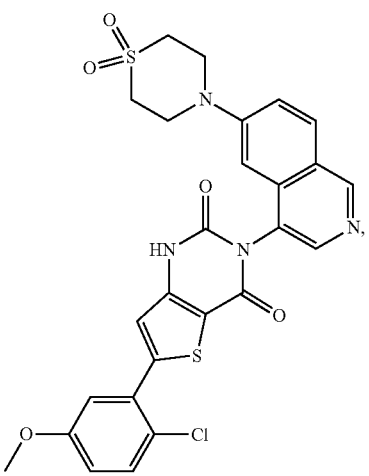

133
-continued
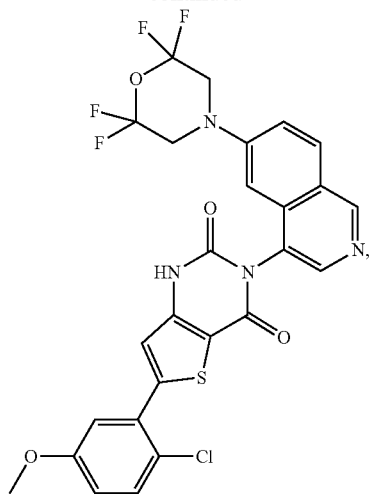
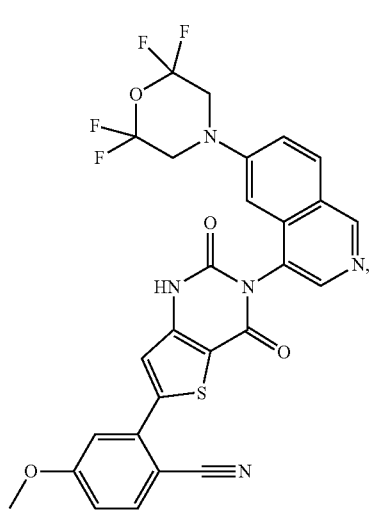
134
-continued
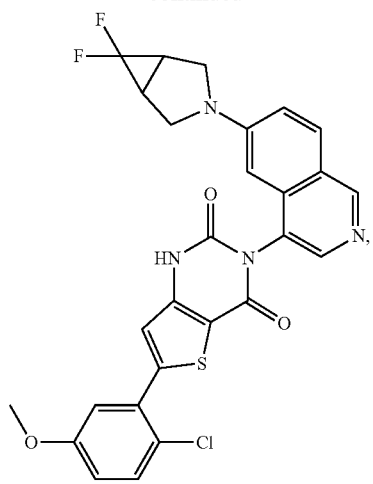
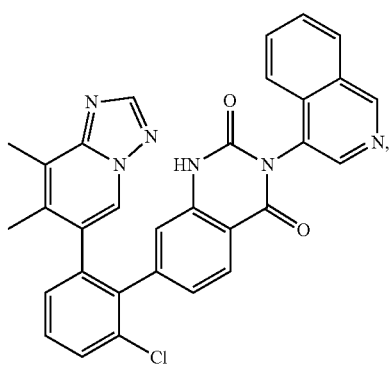
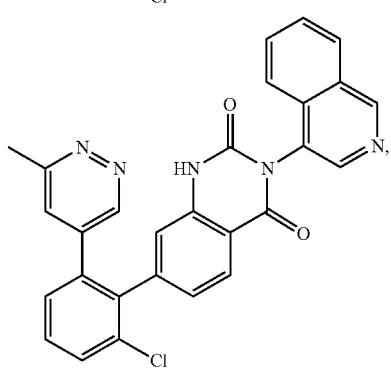
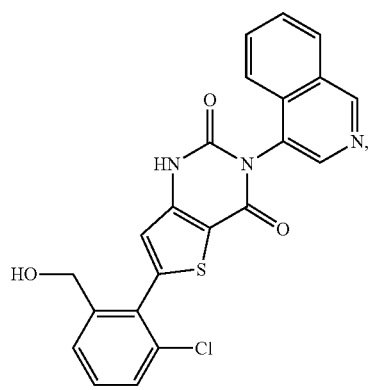

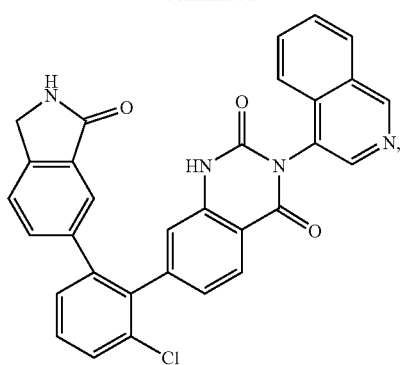
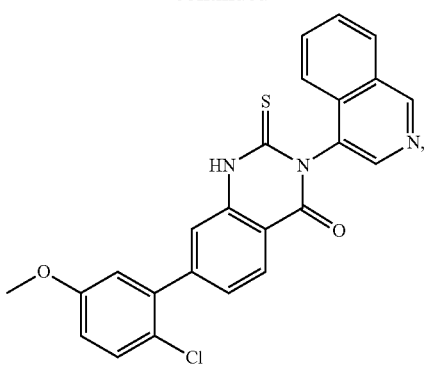
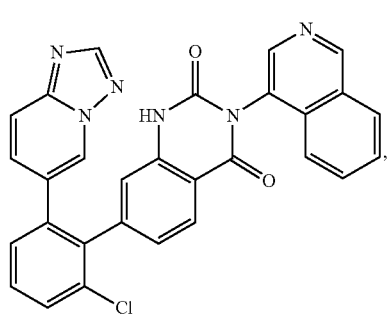
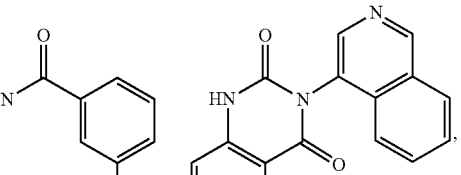
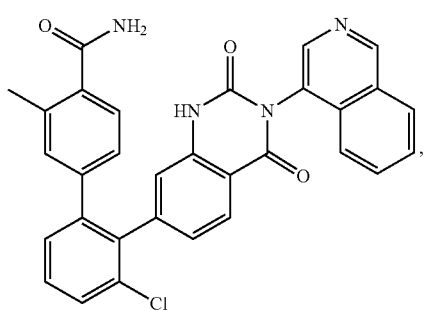

137
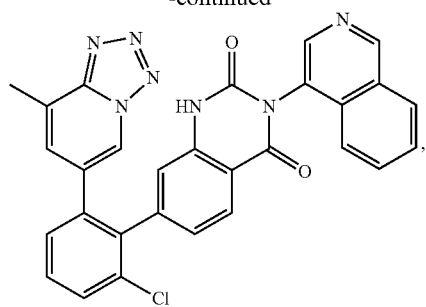
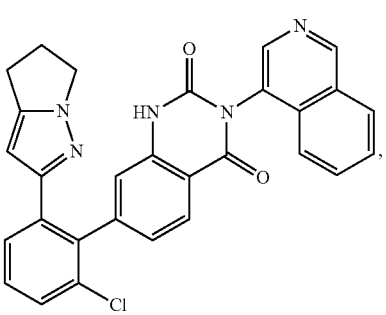
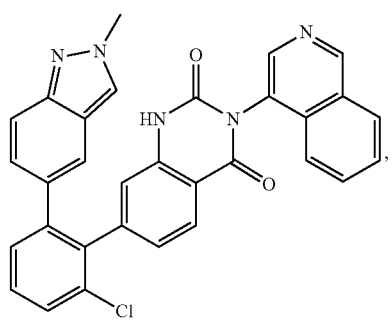
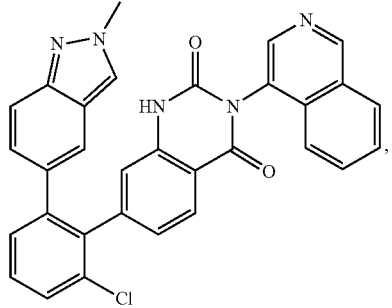
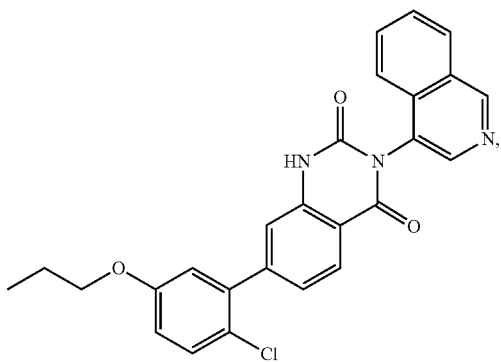
138
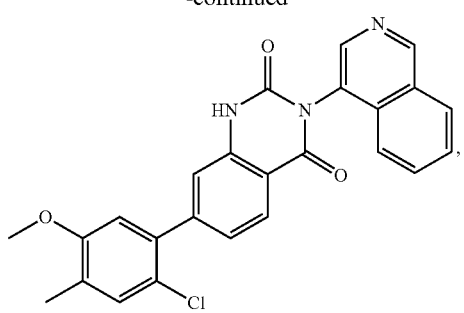
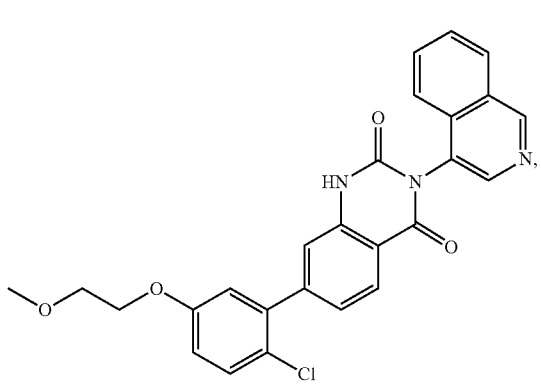
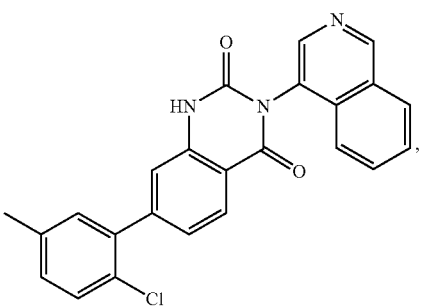
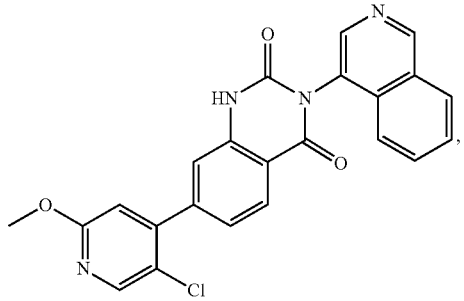
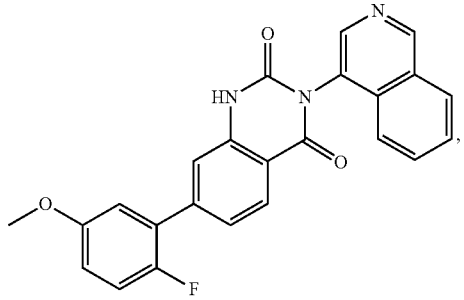

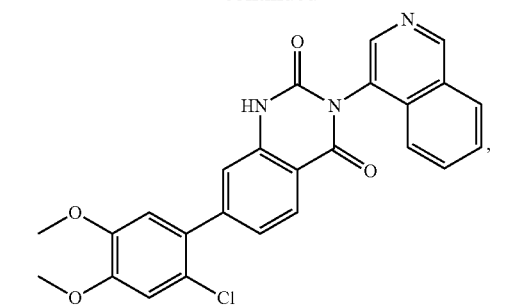
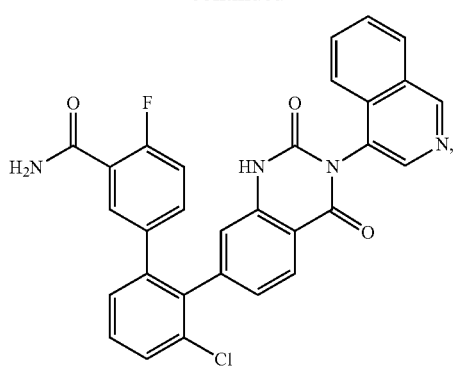
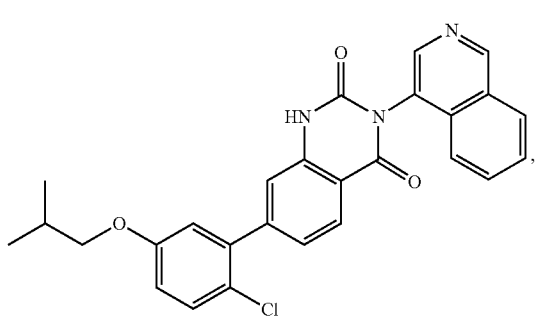
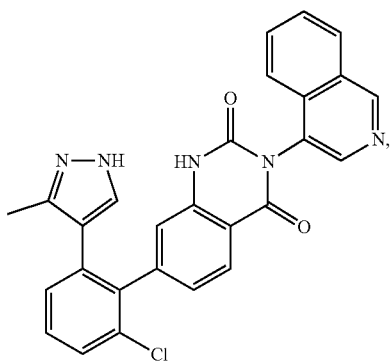
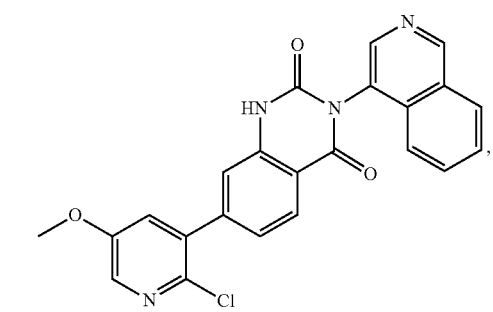
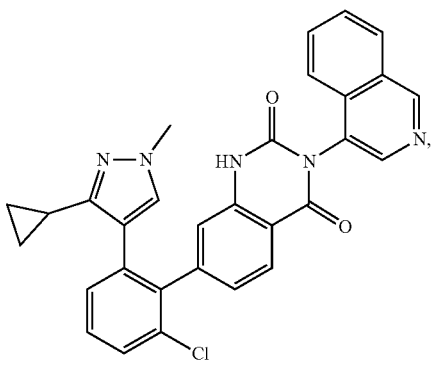
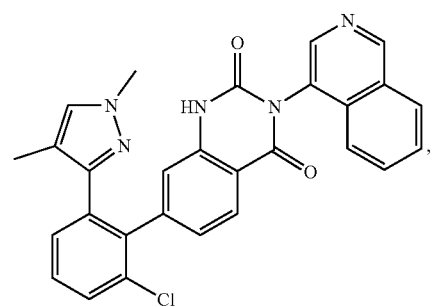
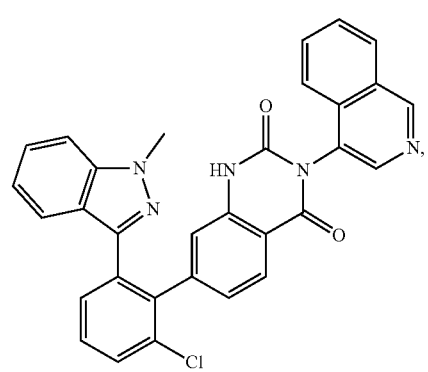
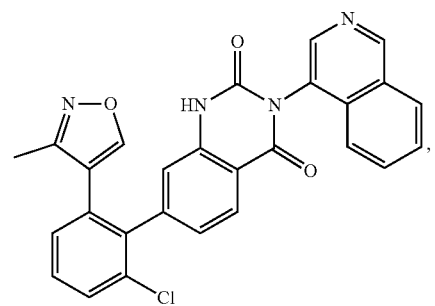

141
-continued
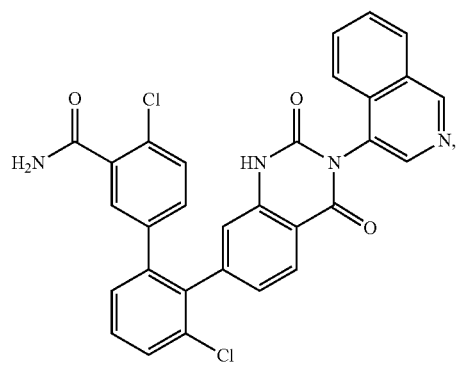
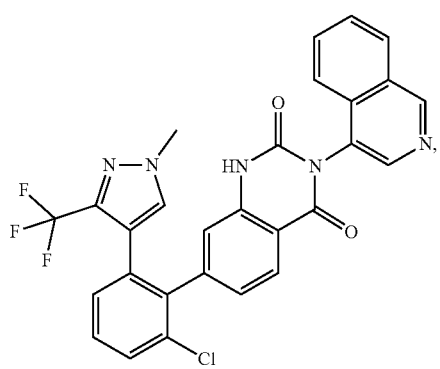
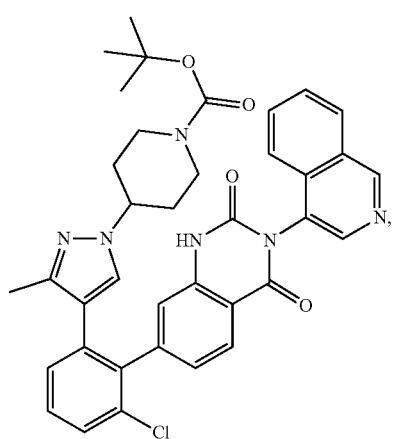
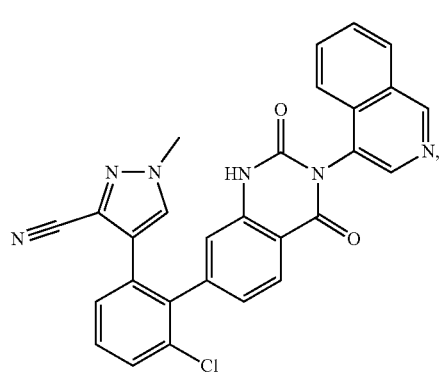
142
-continued
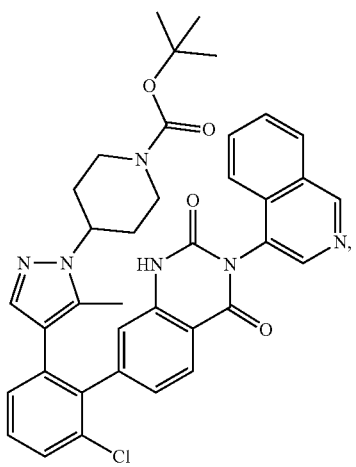
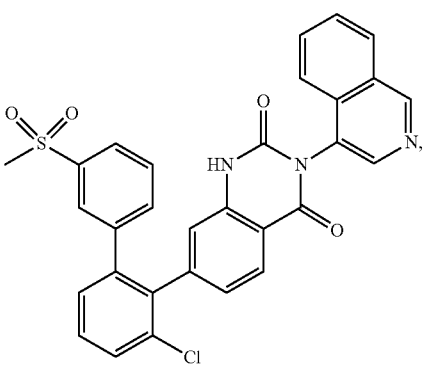
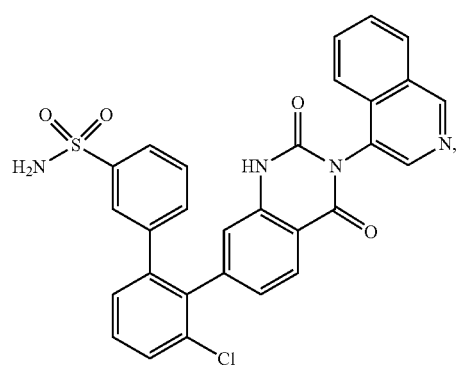
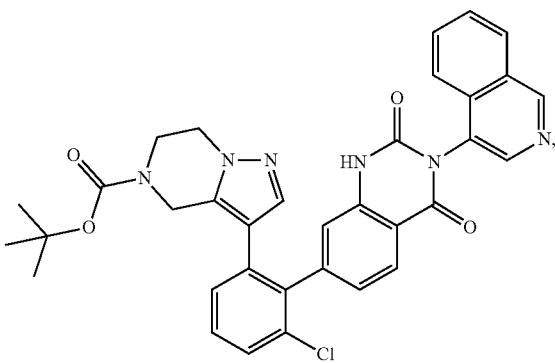

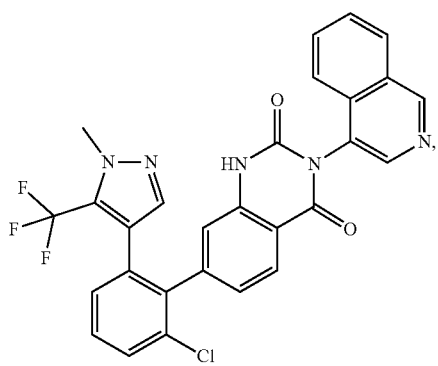
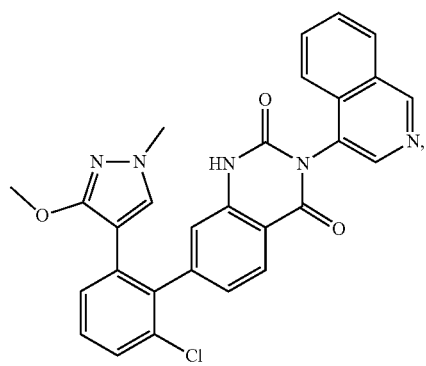
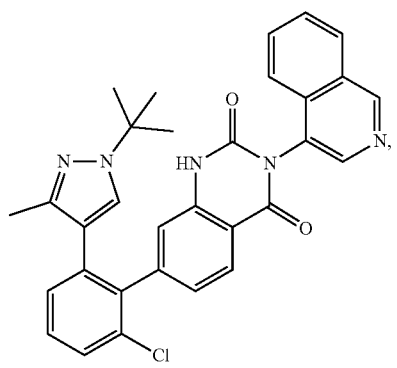
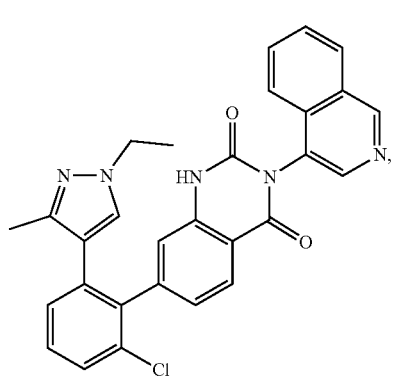
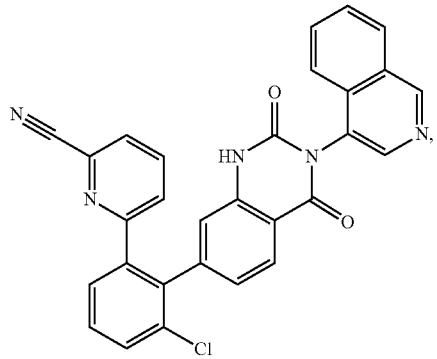
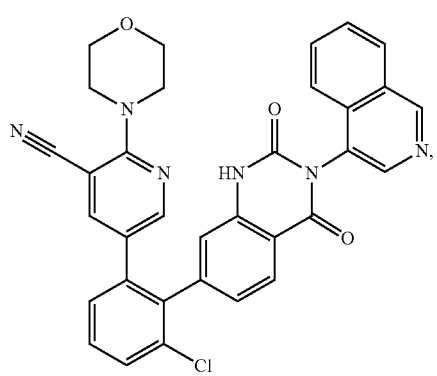
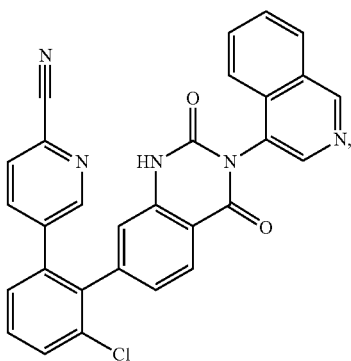
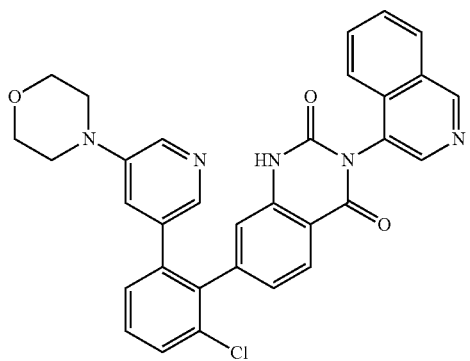

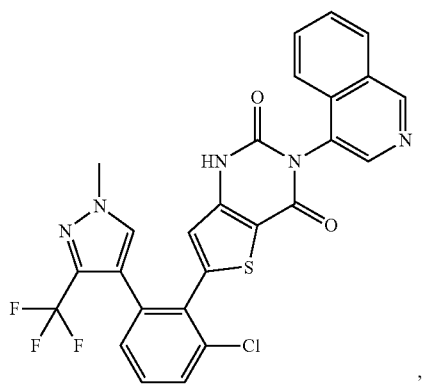
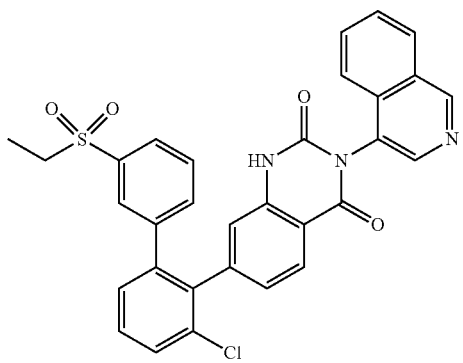
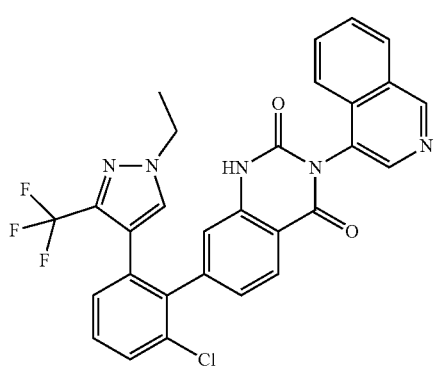
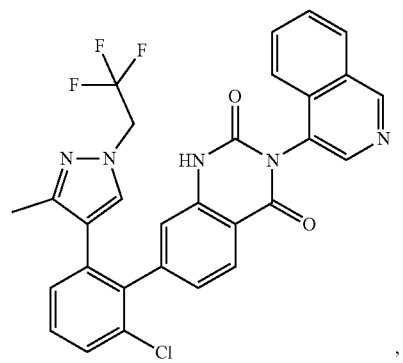
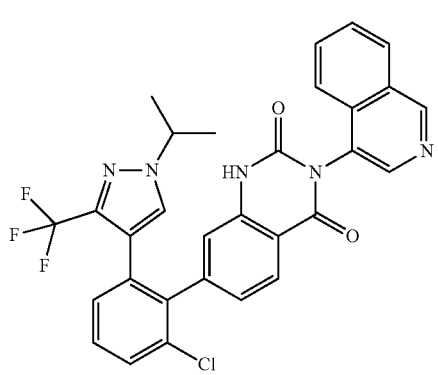
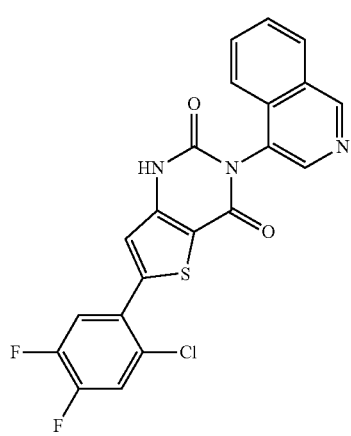
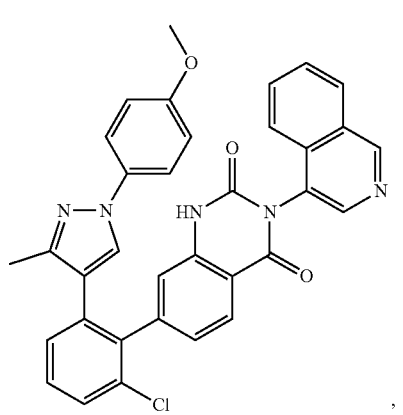
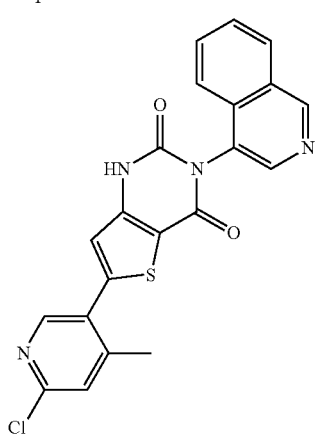

147
-continued
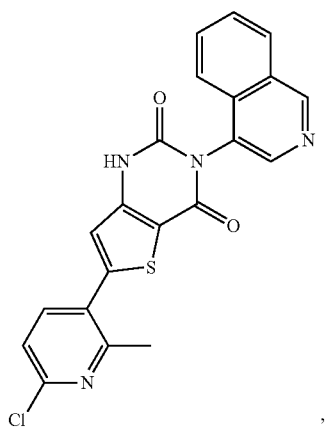
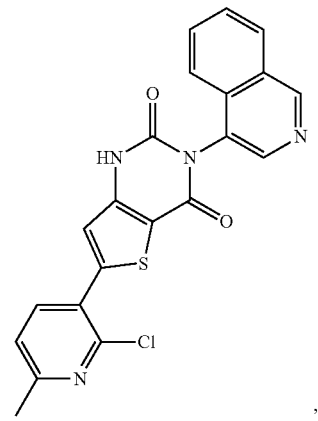
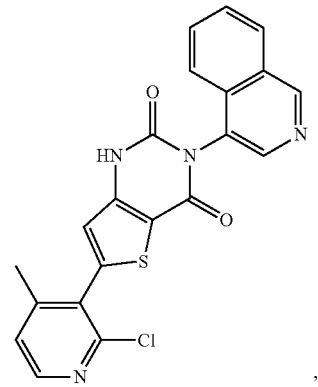
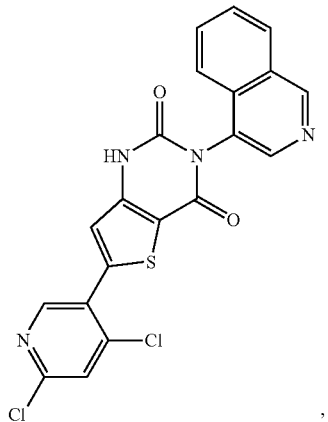
148
-continued
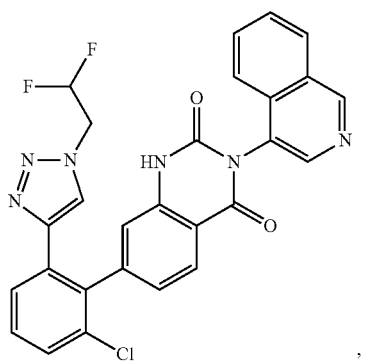
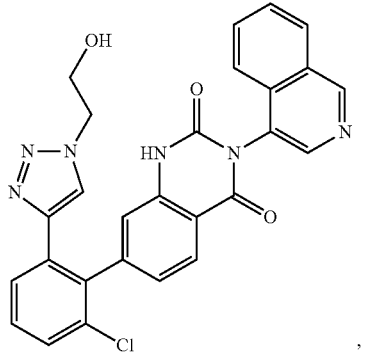
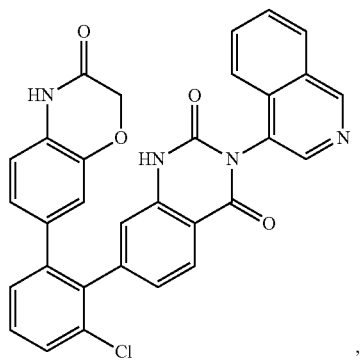
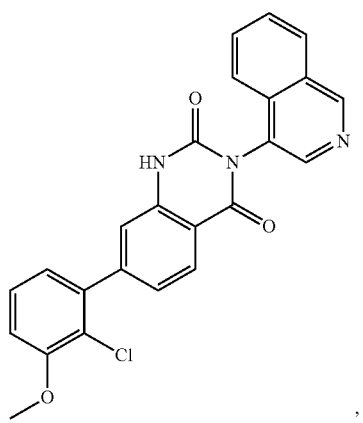

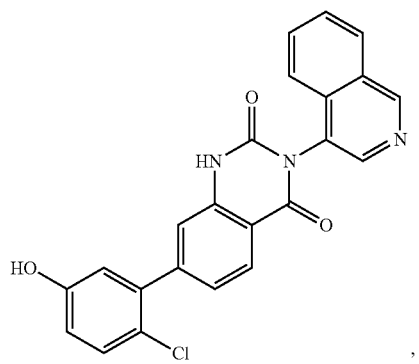
,
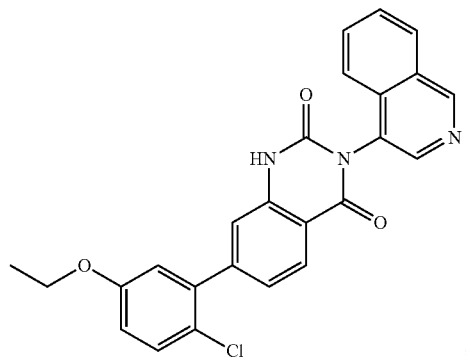
,
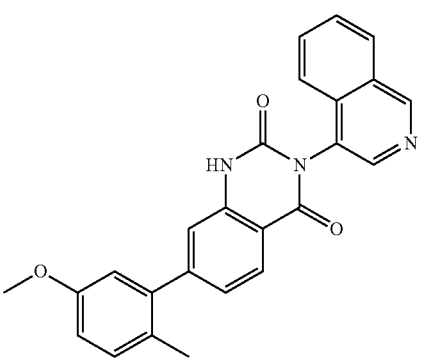
,
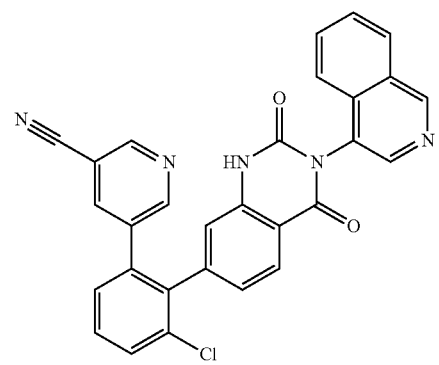
,
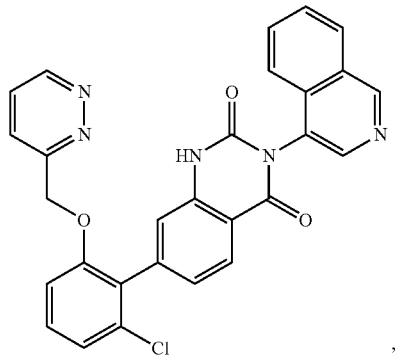
,
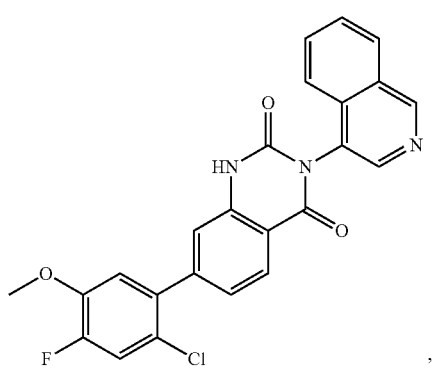
,
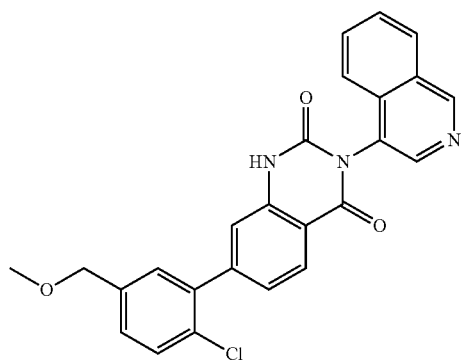
, 151
-continued
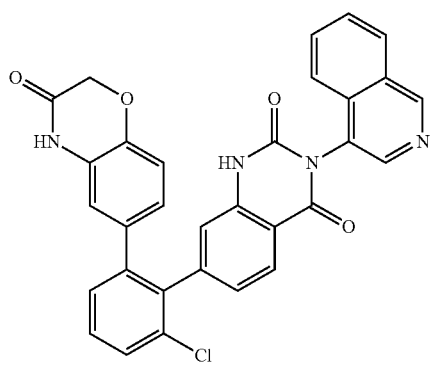
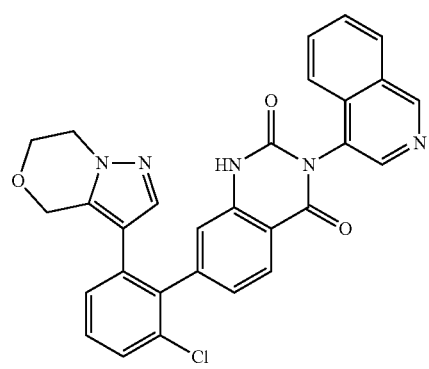
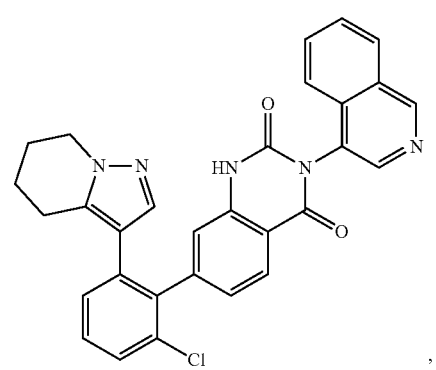
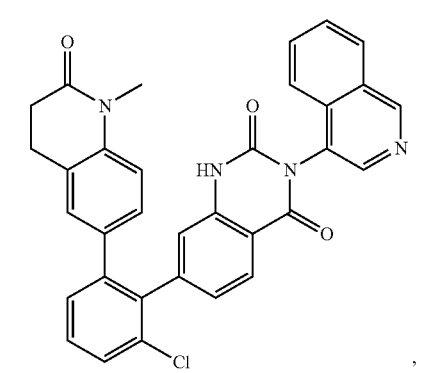
152
-continued
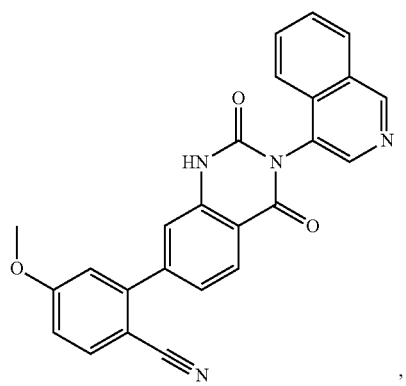
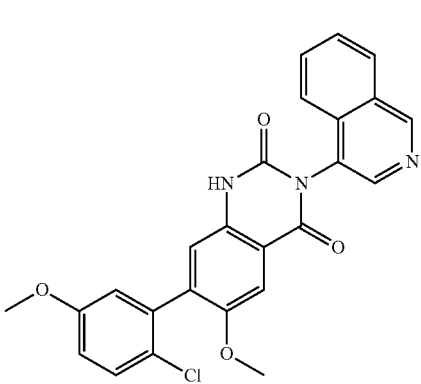
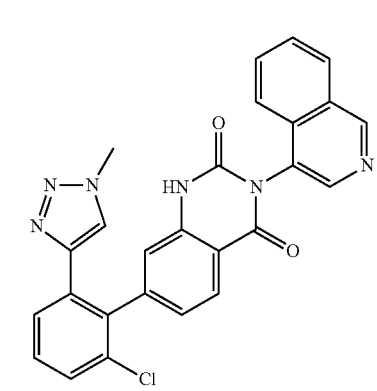
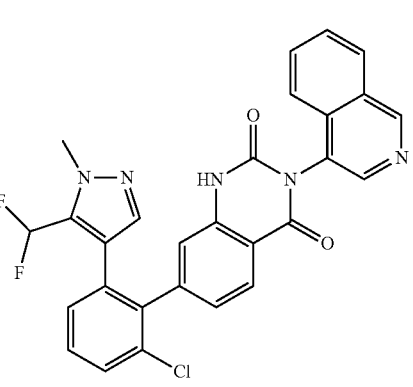

153
-continued
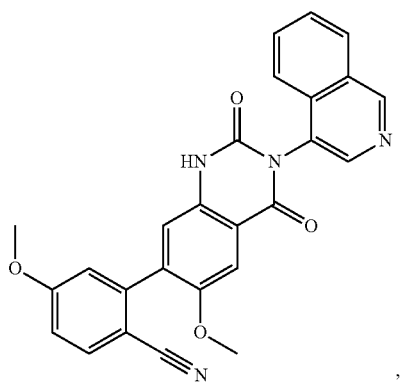
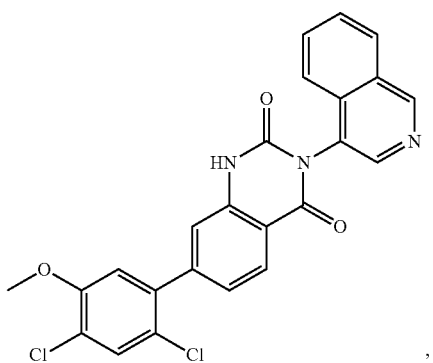
154
-continued
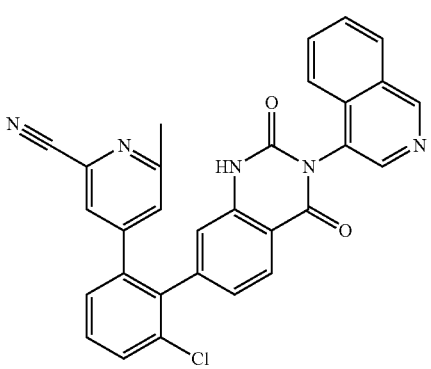
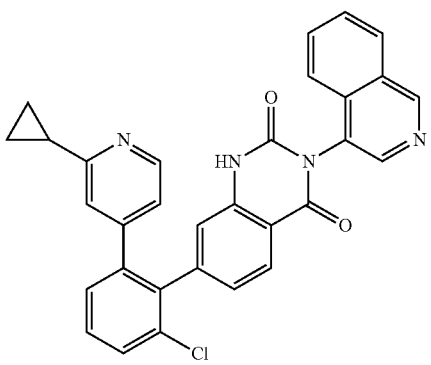
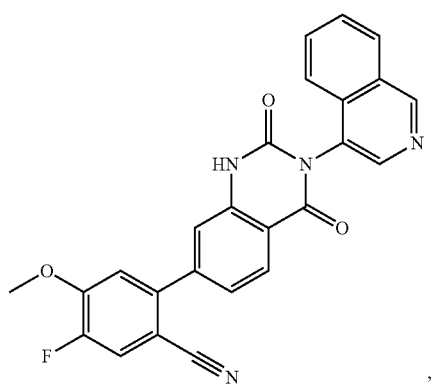

155
-continued
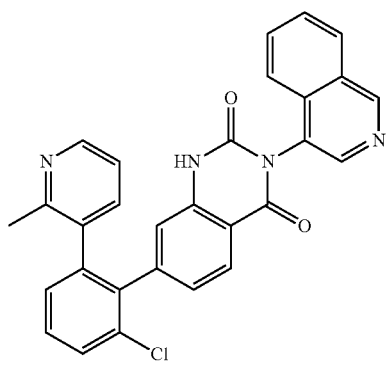
,
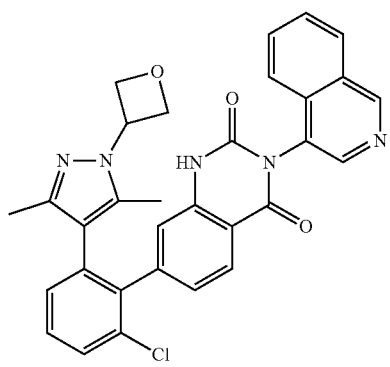
,
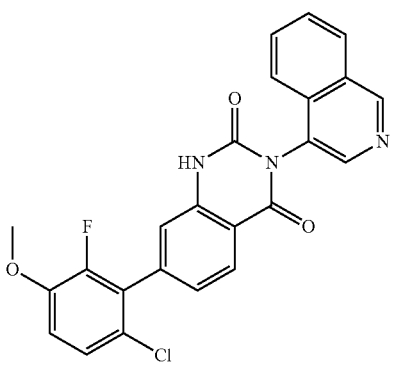
,
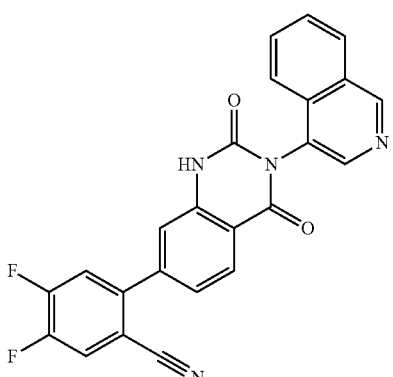
,
156
-continued
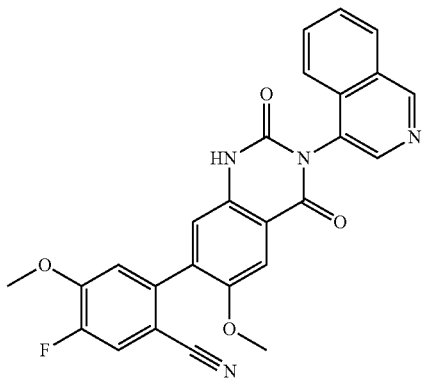
,
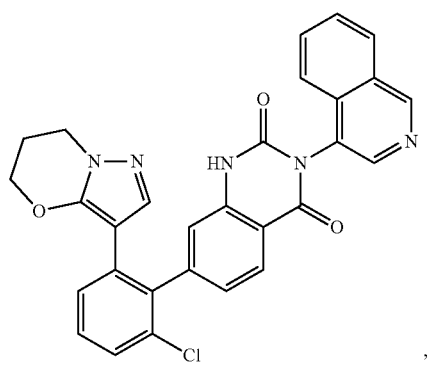
,
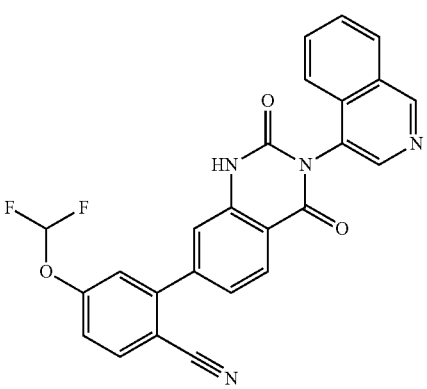
,
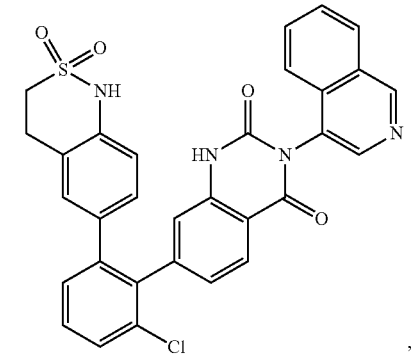
,

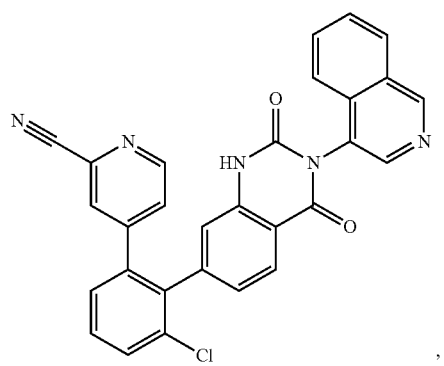
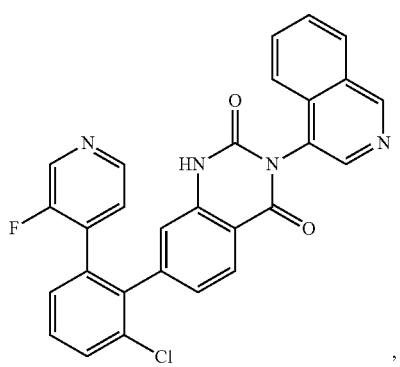
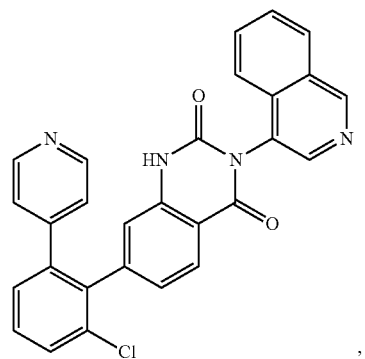
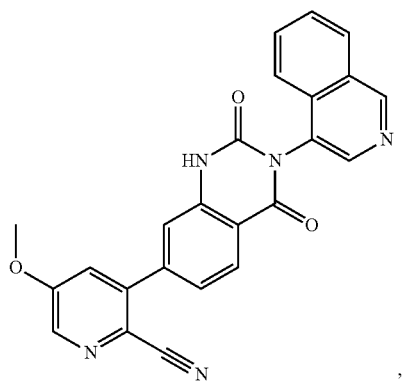
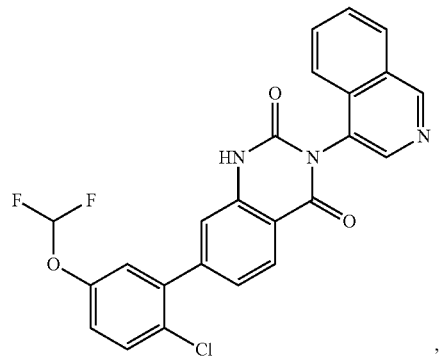
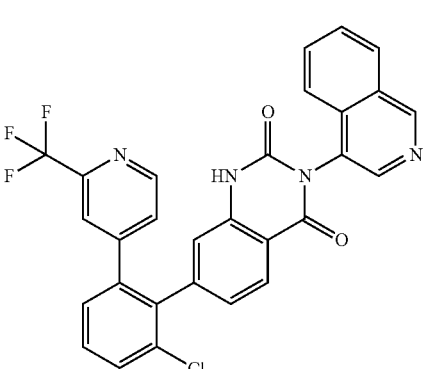
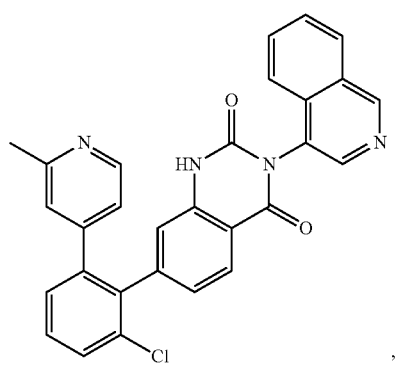
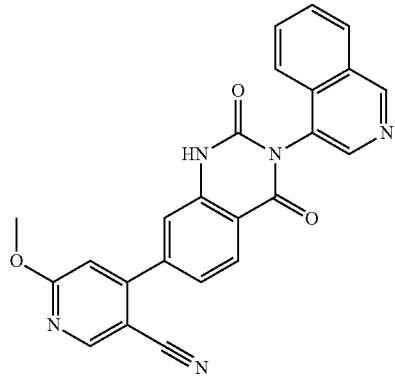

-continued
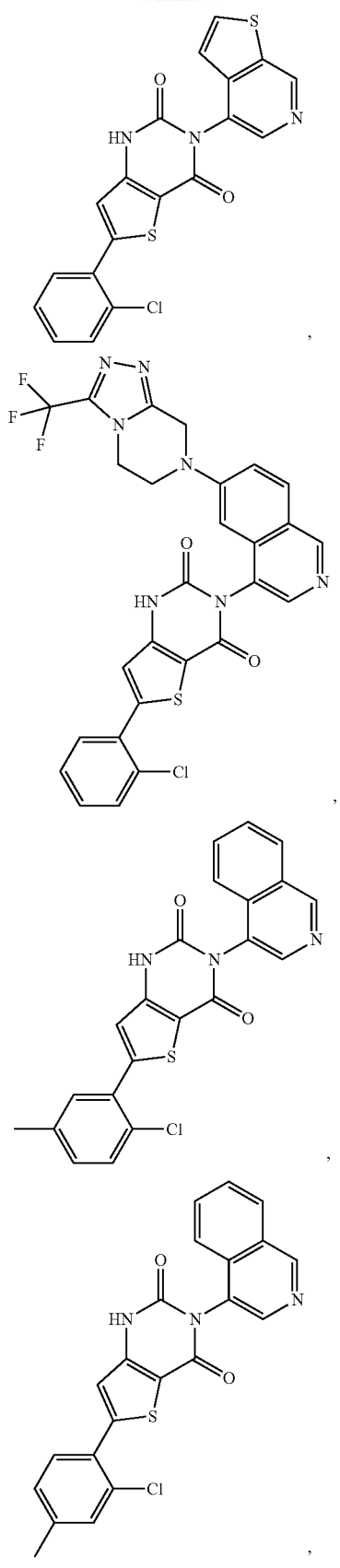
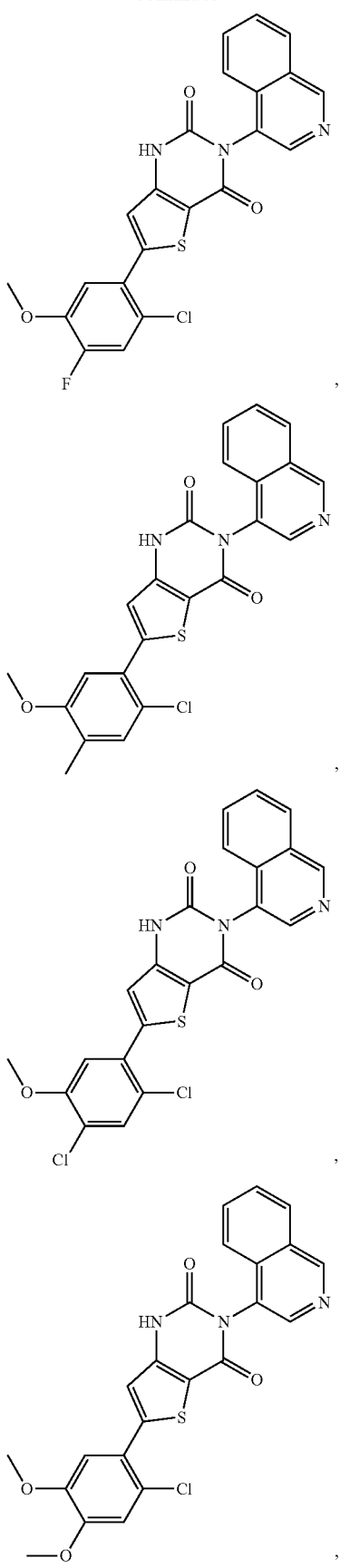

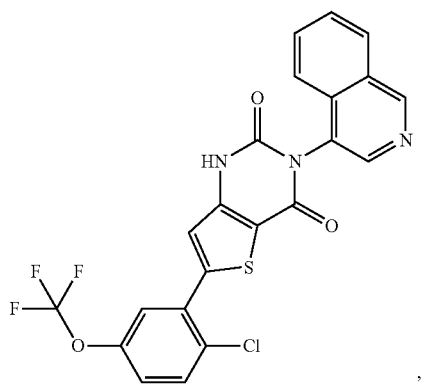
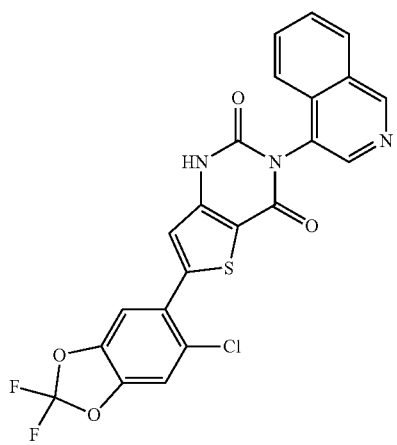
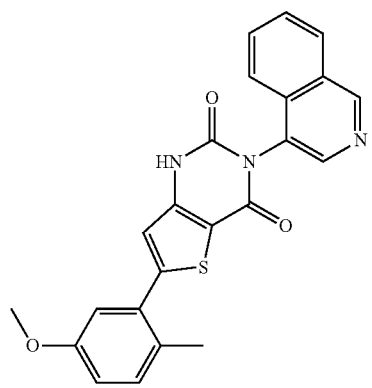
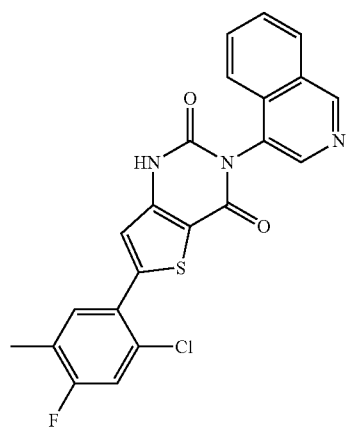
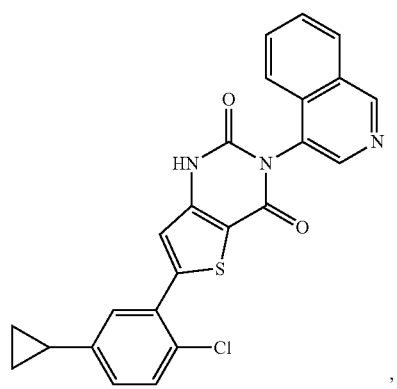

163
-continued
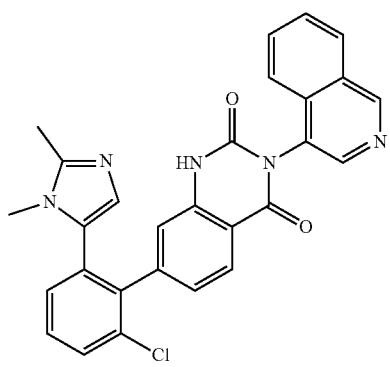
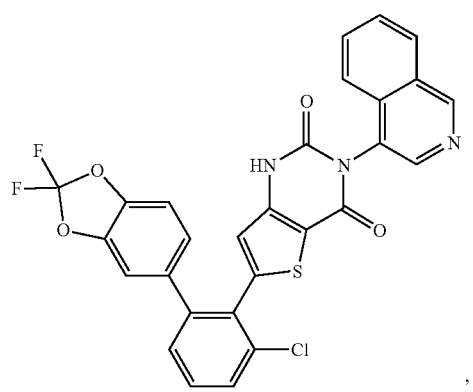
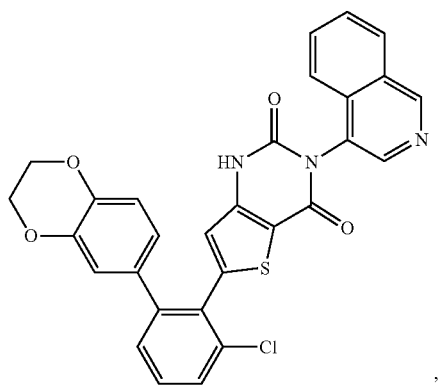
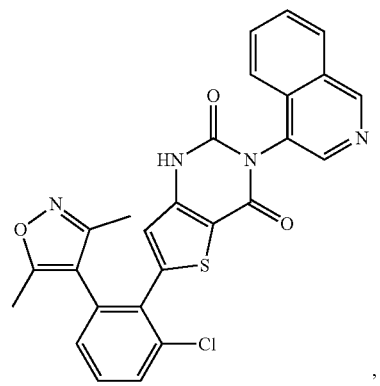
164
-continued
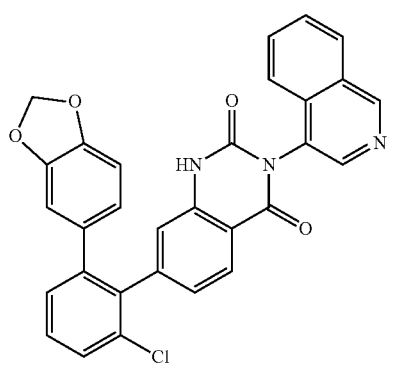
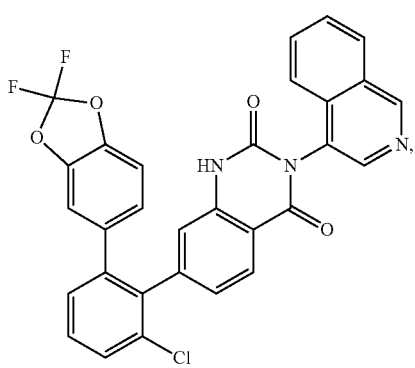
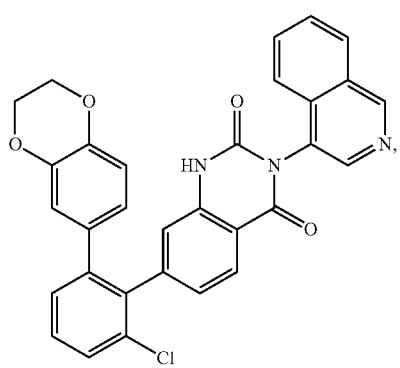
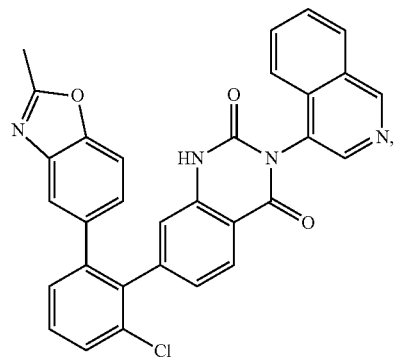

165
-continued
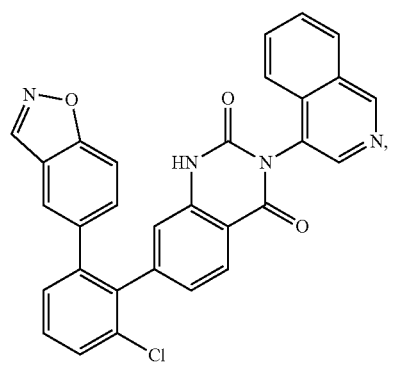
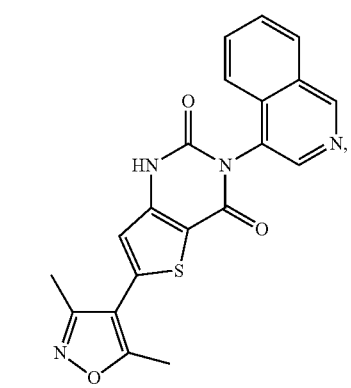
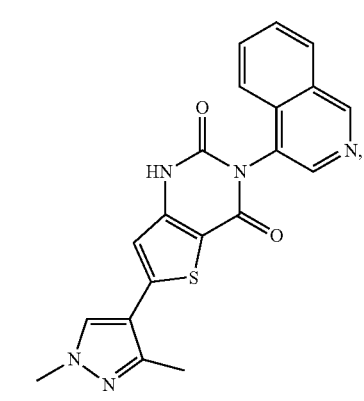
166
-continued
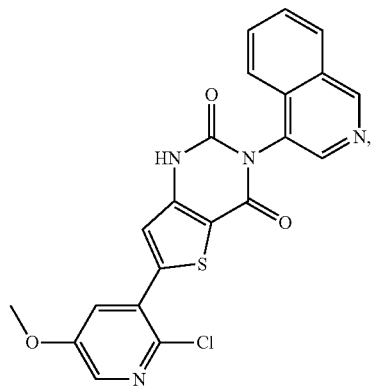
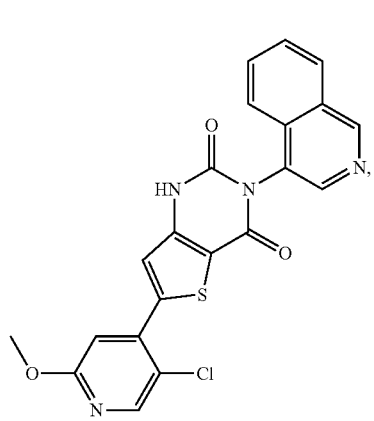
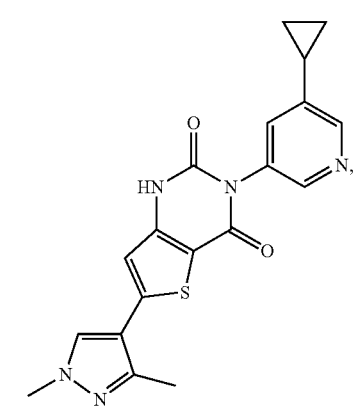
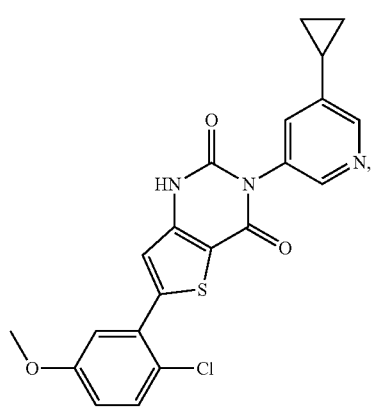

167
-continued
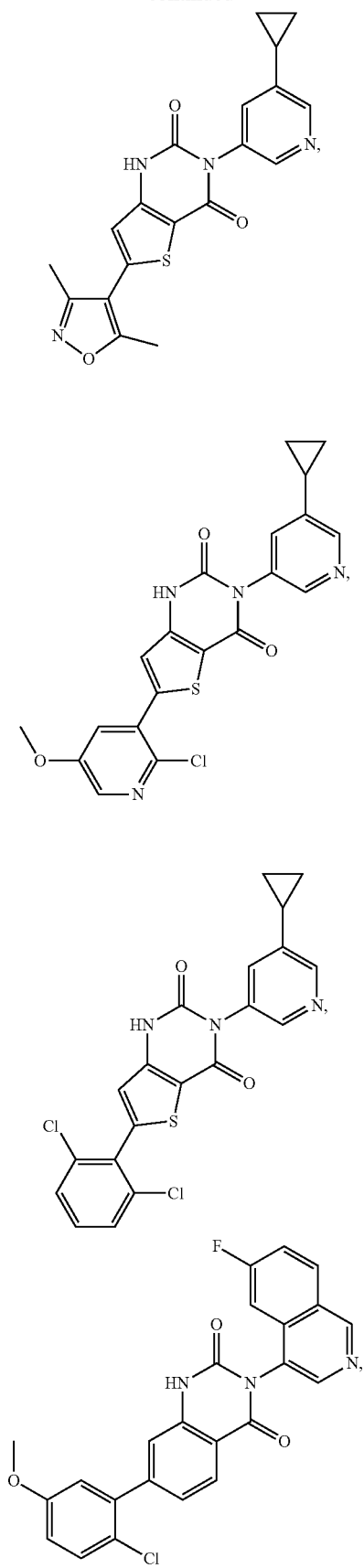
168
-continued
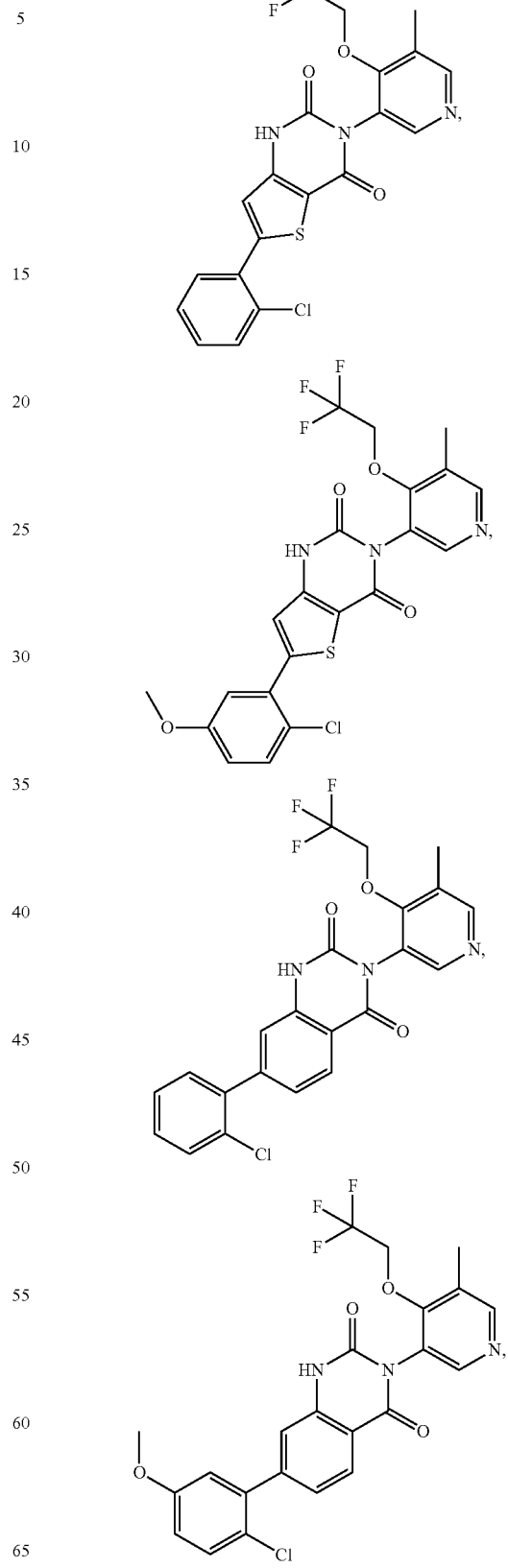

169
-continued
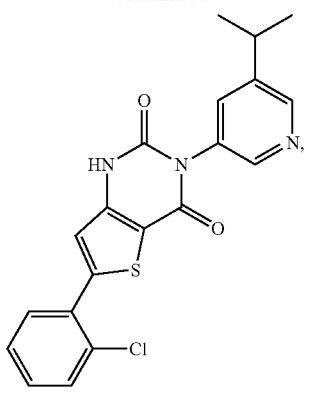
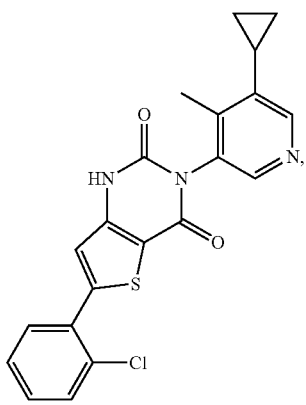
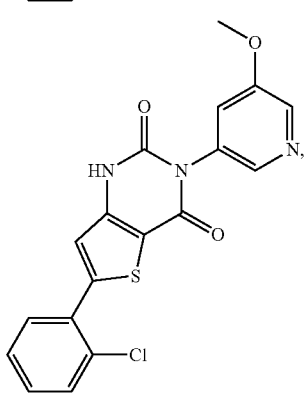
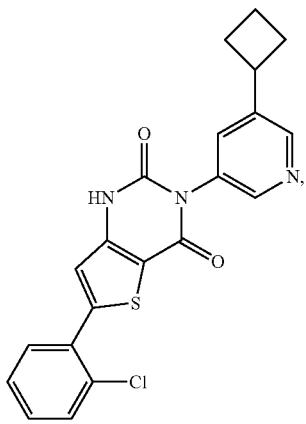
170
-continued
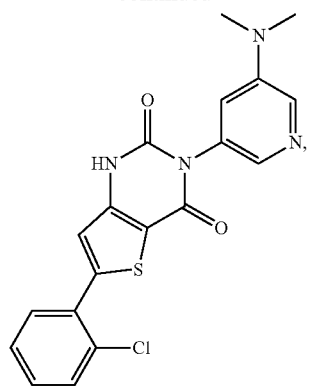
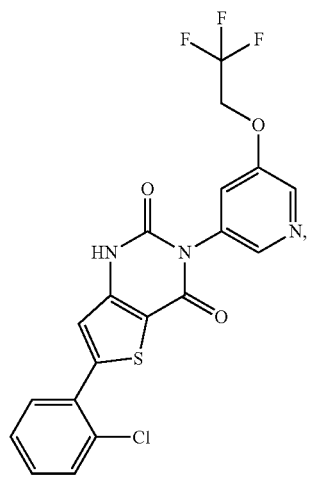
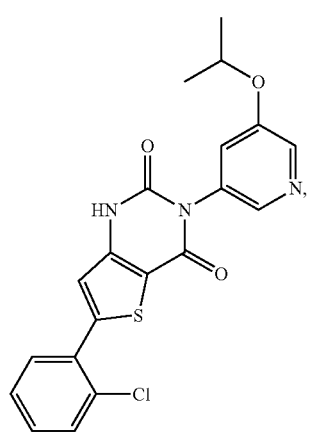

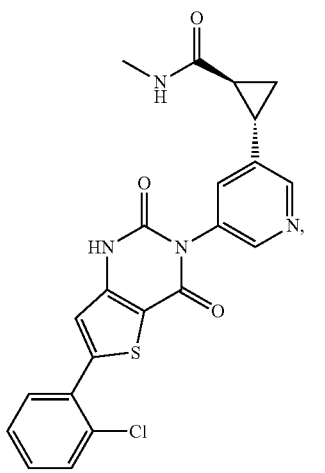
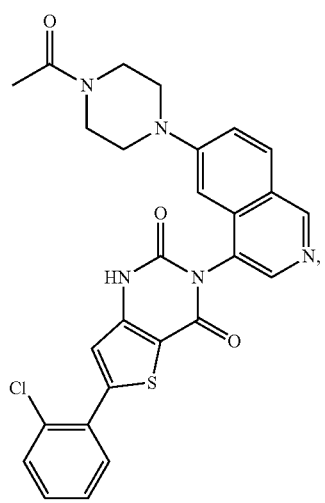

173
-continued
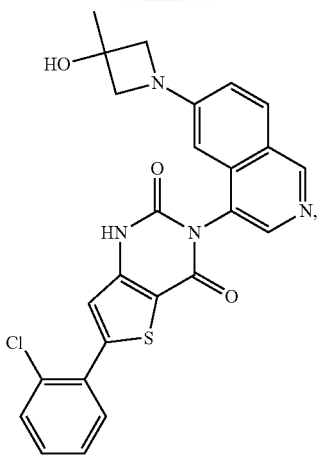
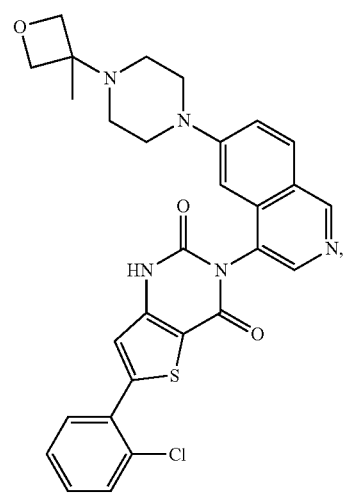
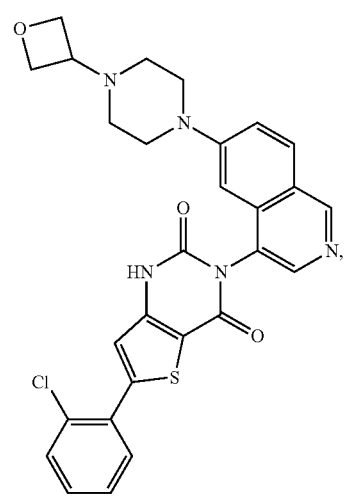
174
-continued
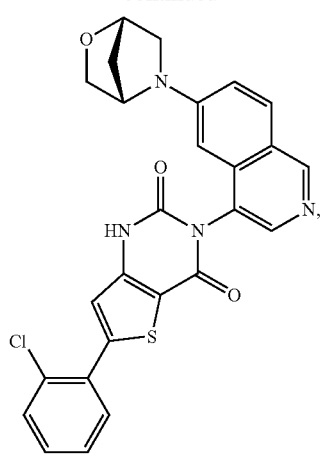
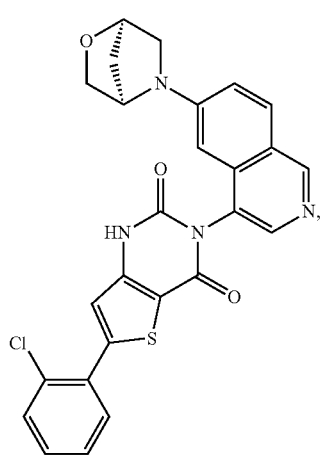
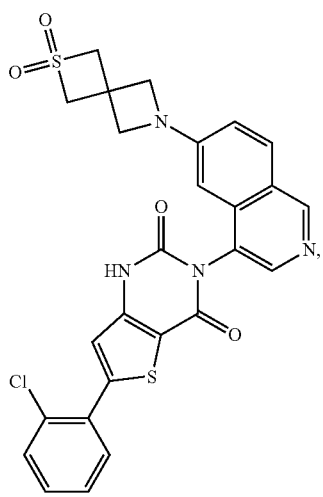

175
-continued
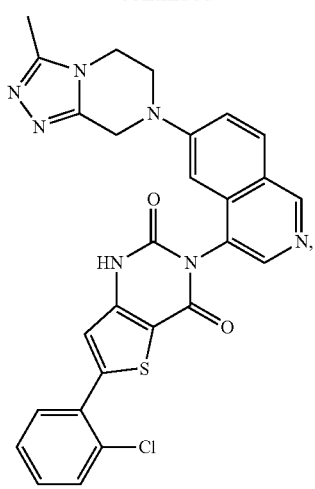
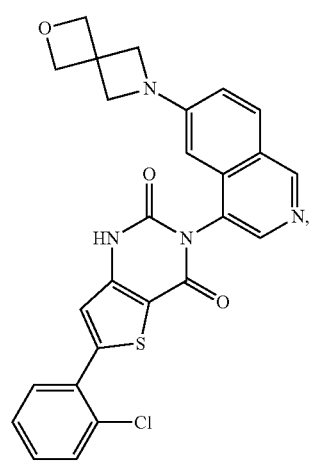
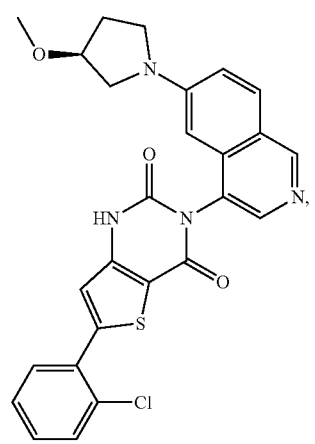
176
-continued
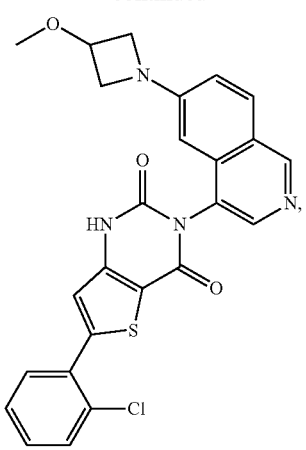
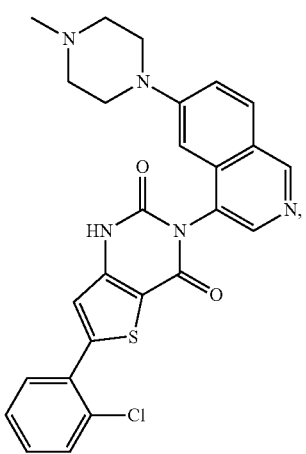
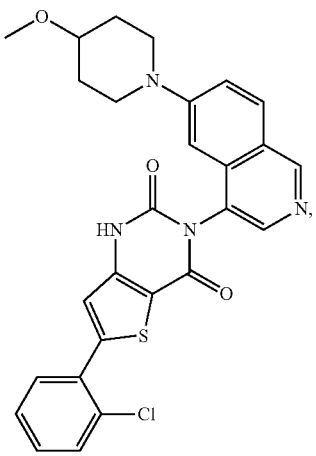

177
-continued
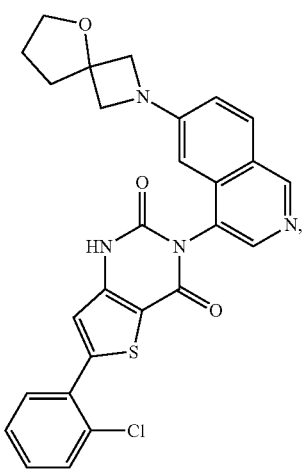
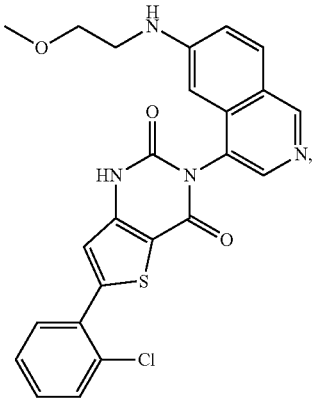
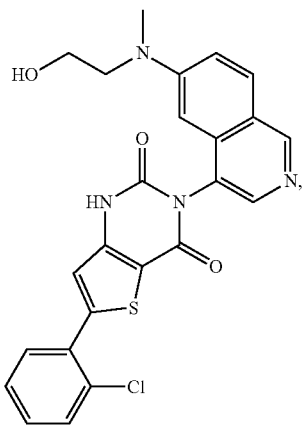
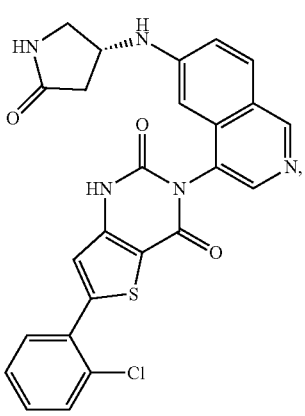
178
-continued
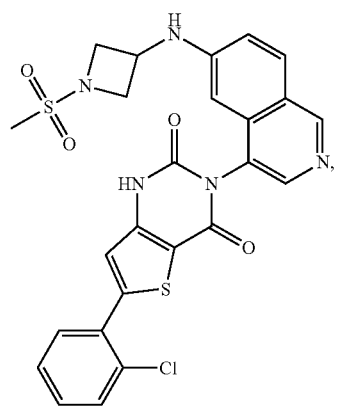
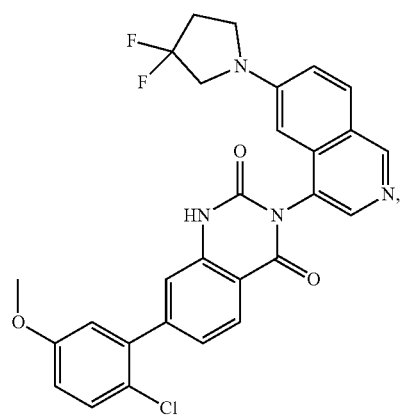
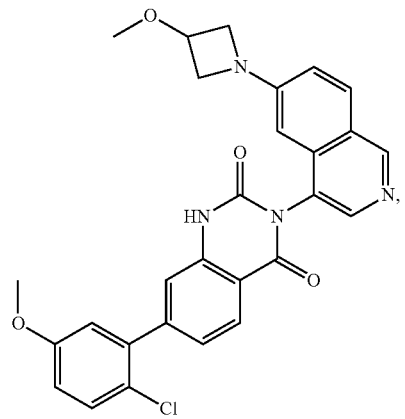
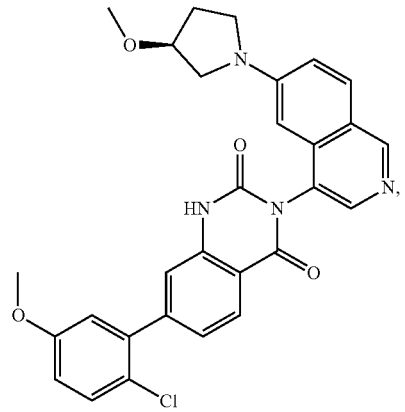

179
-continued
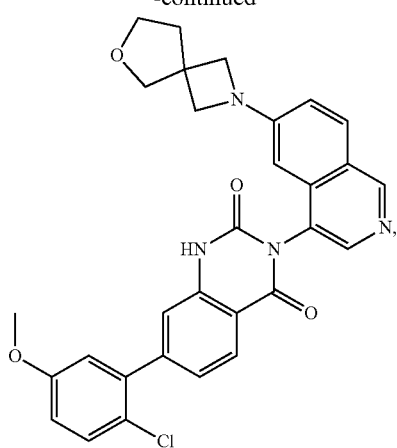
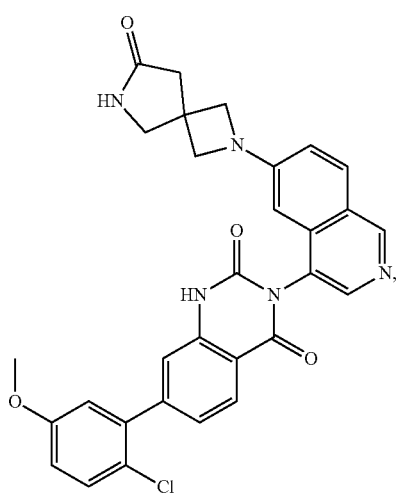
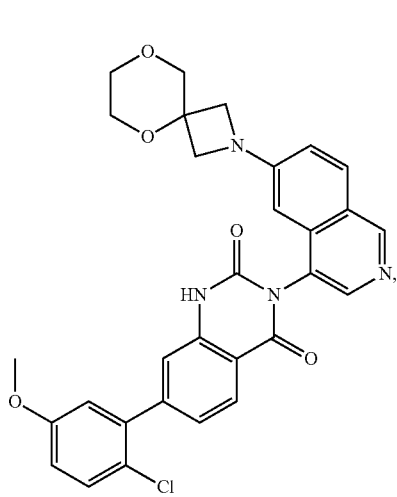
180
-continued
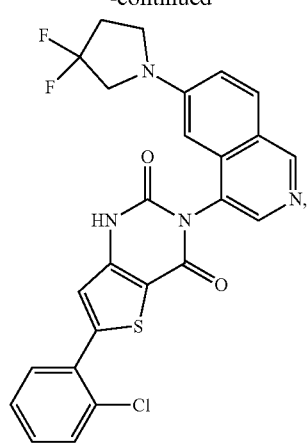
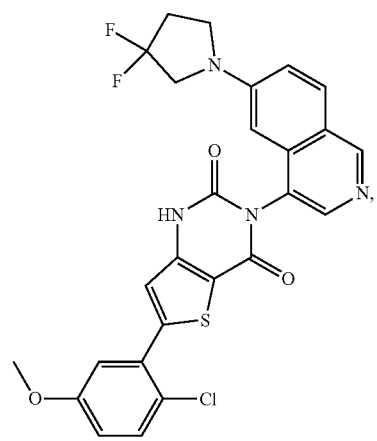
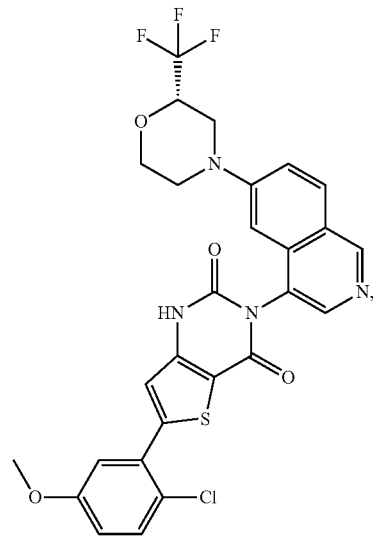

181
-continued
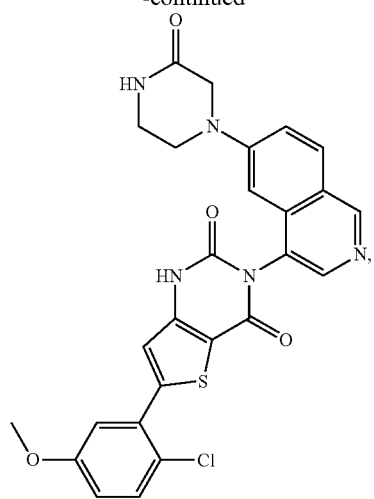
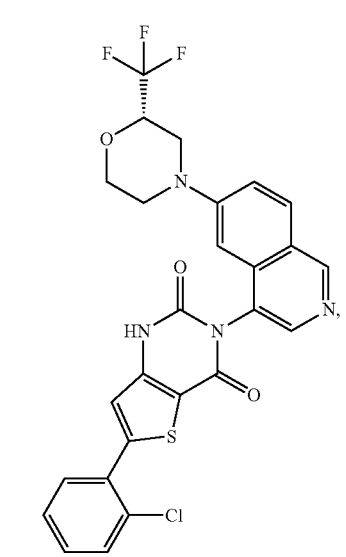
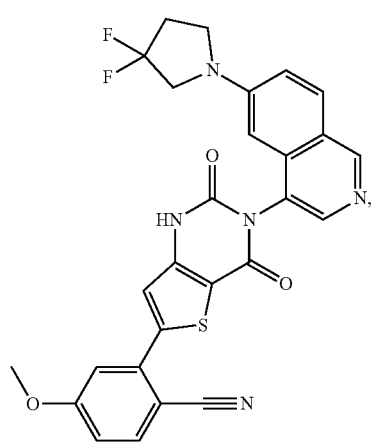
182
-continued
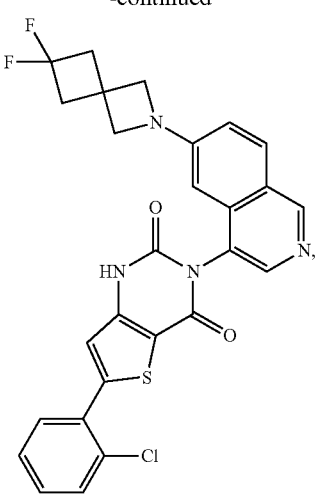
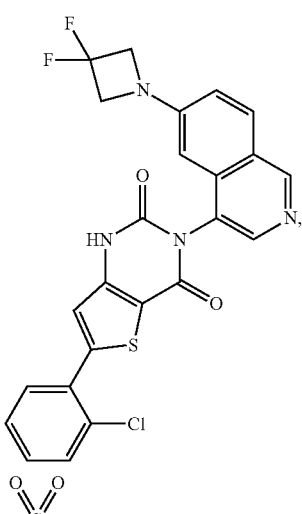
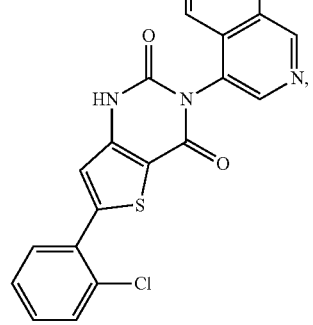

-continued
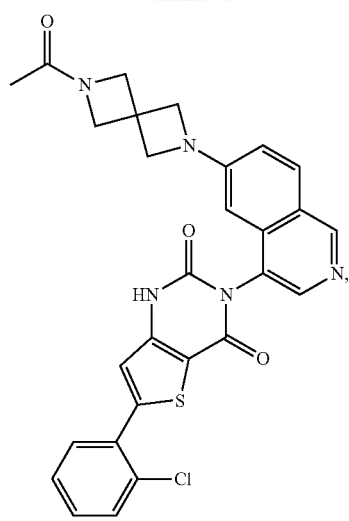
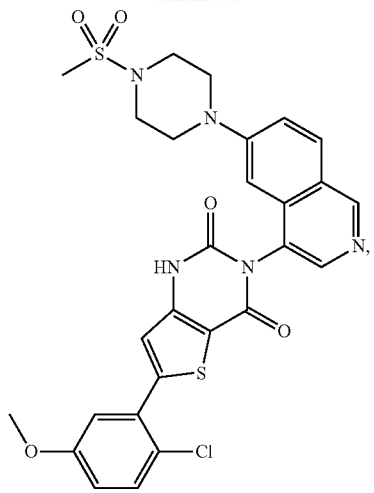
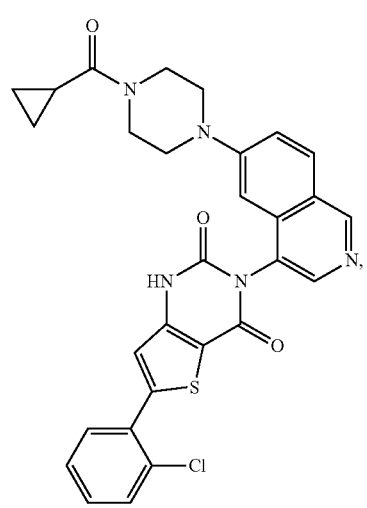
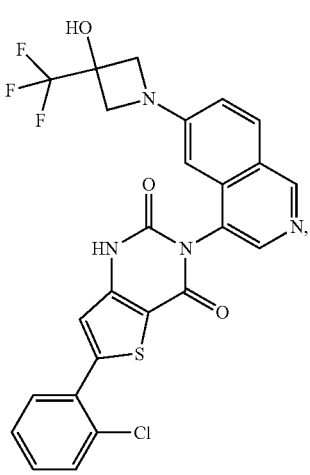
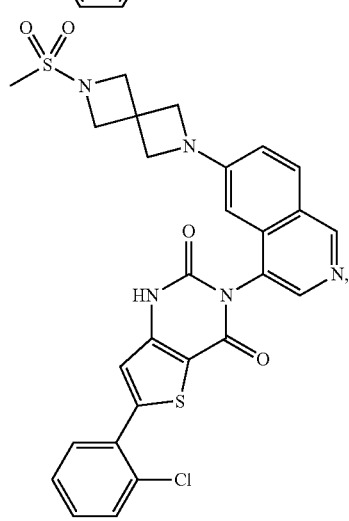
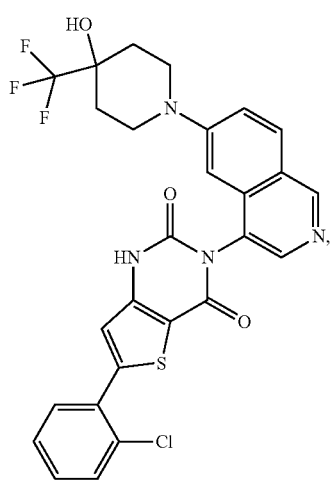

-continued
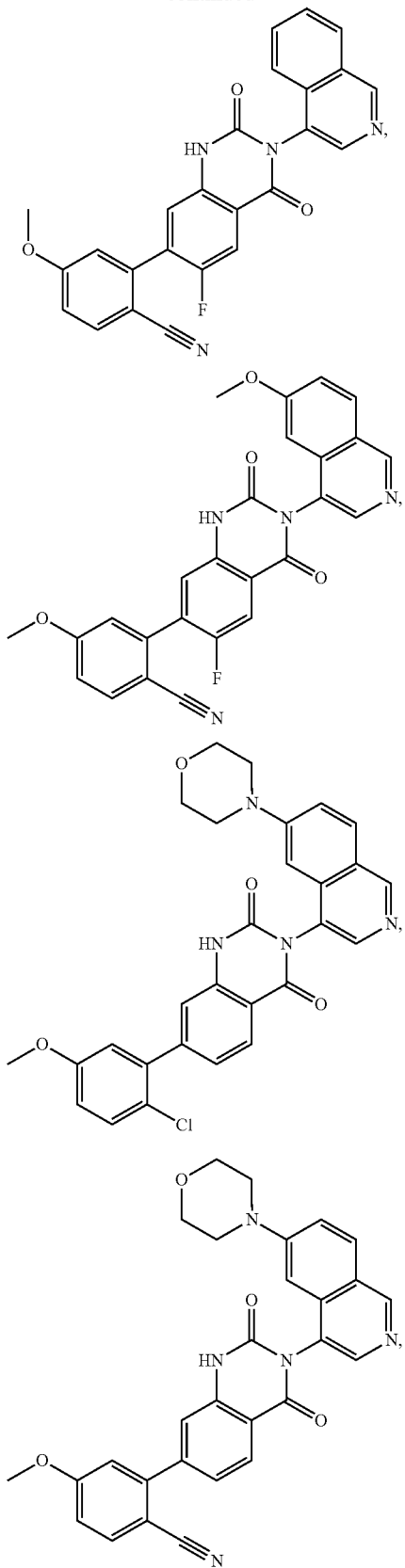
-continued
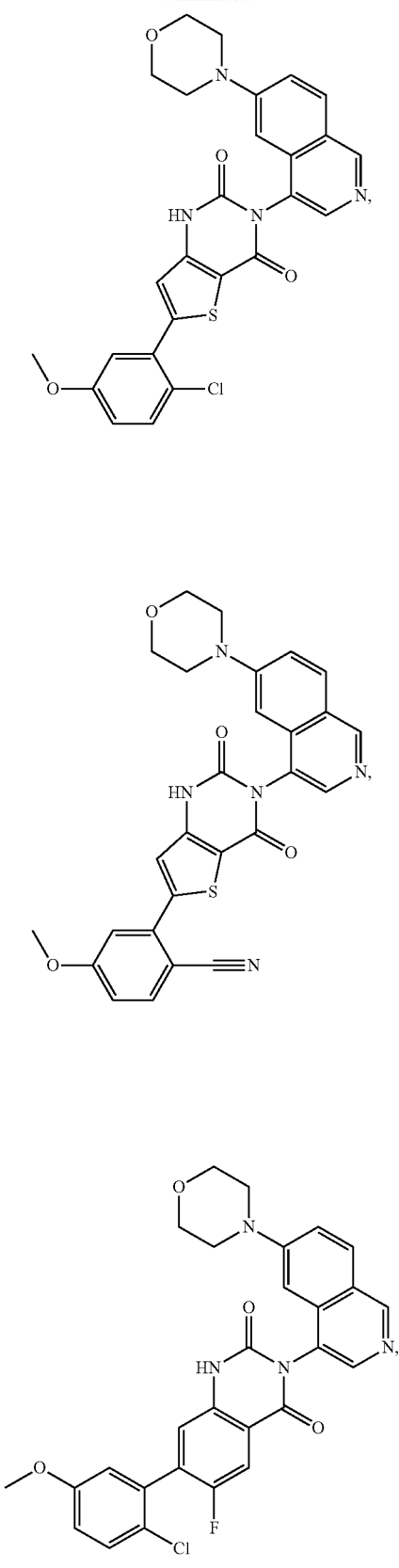

187
-continued
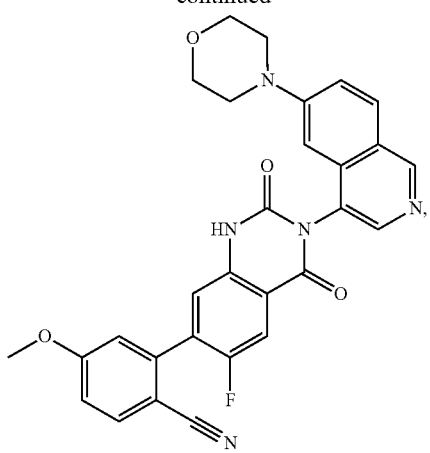
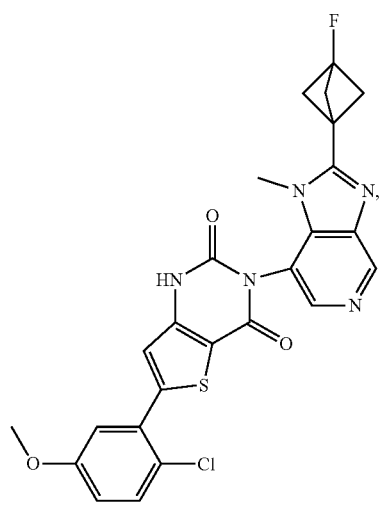
188
-continued
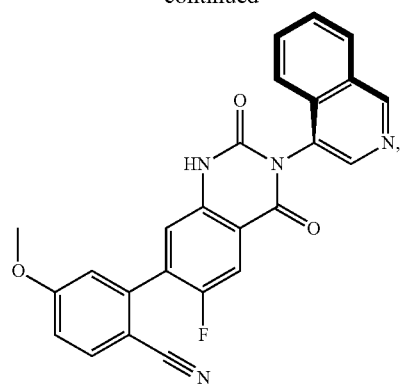
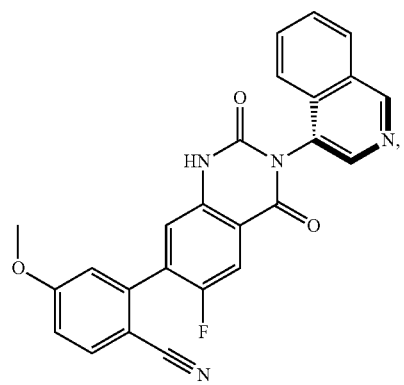
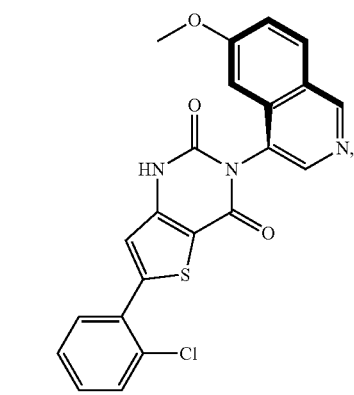
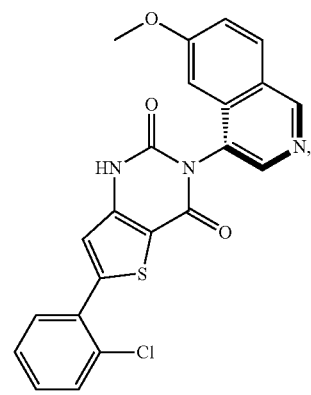

189
-continued
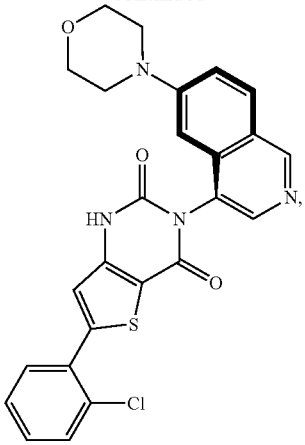
190
-continued
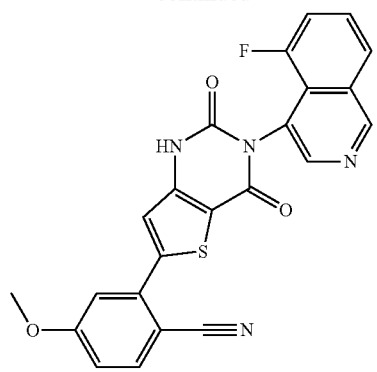
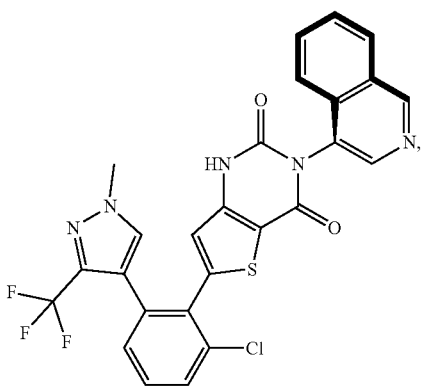
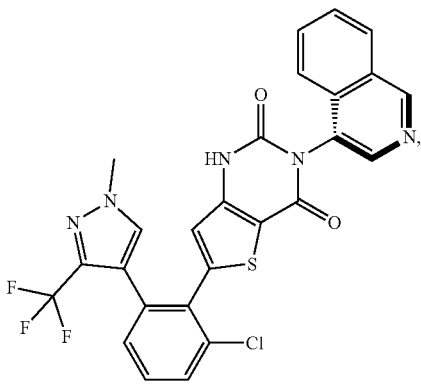
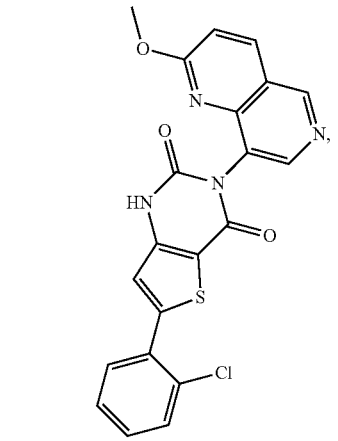

191
-continued
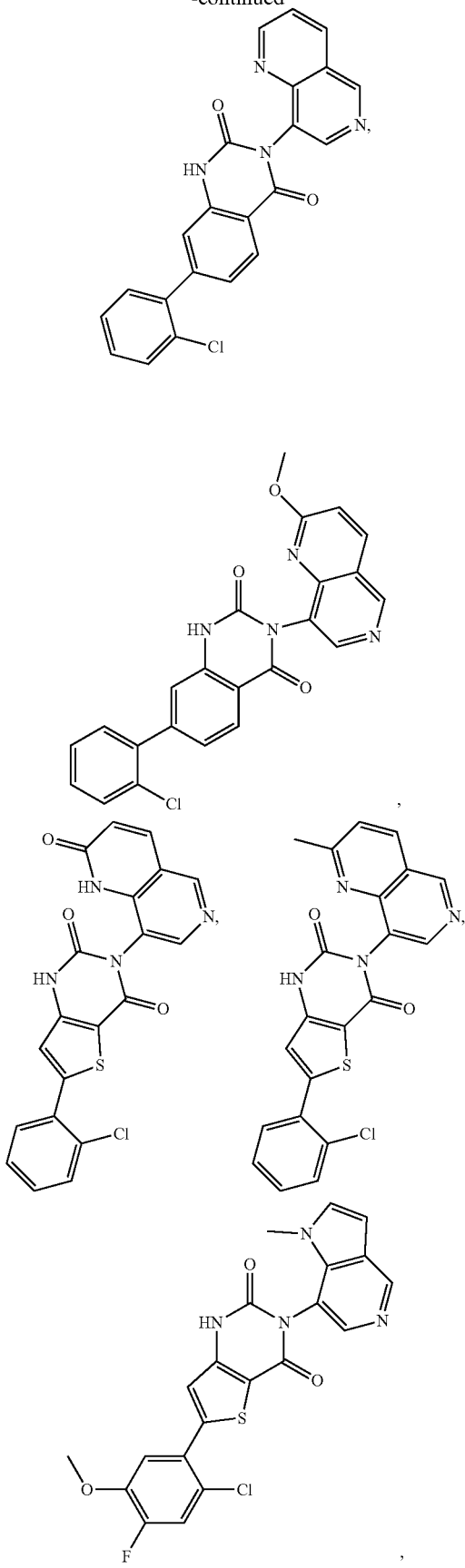
192
-continued
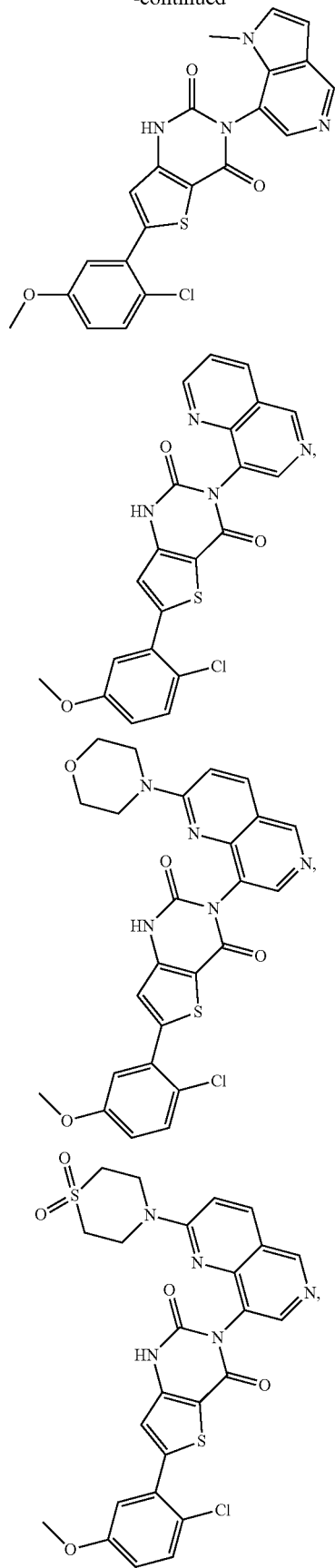

193
-continued
194
-continued
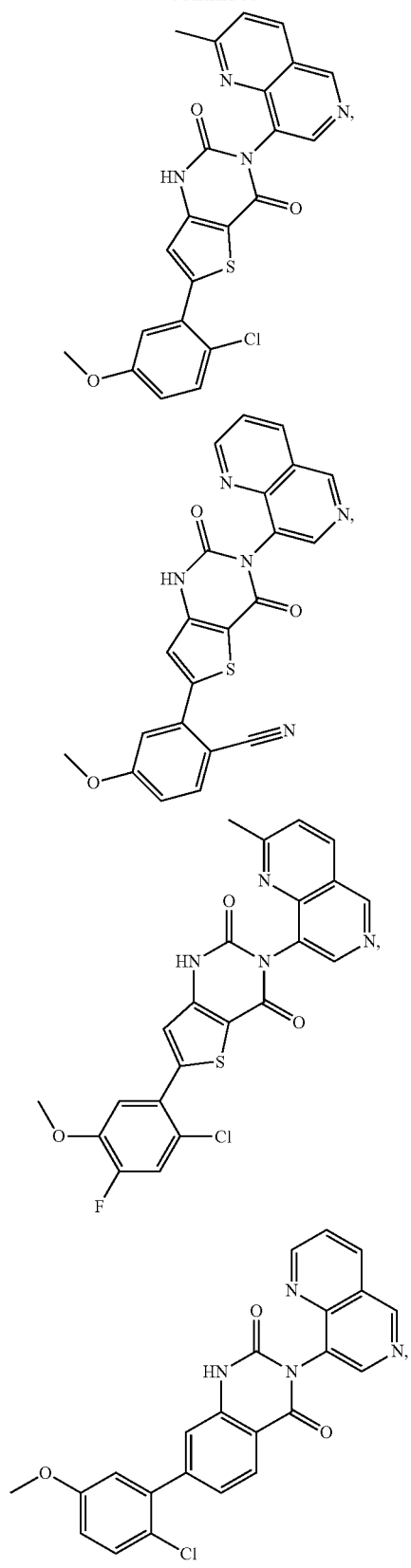
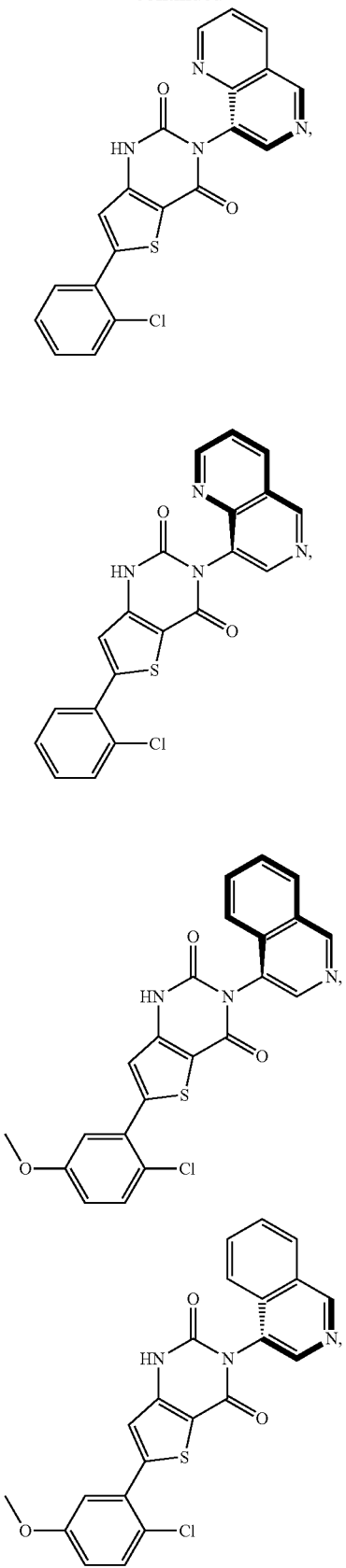

195
-continued
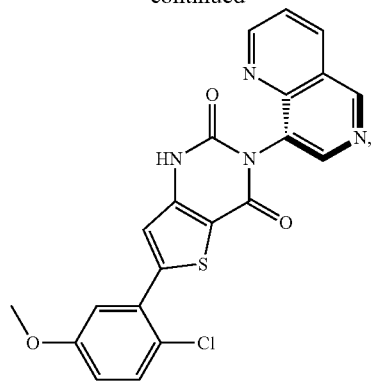
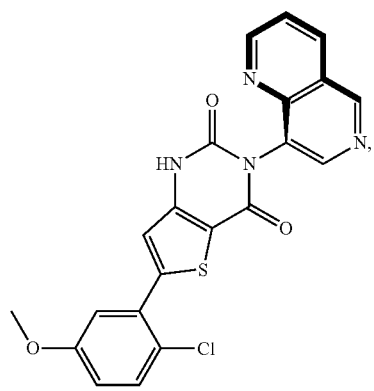
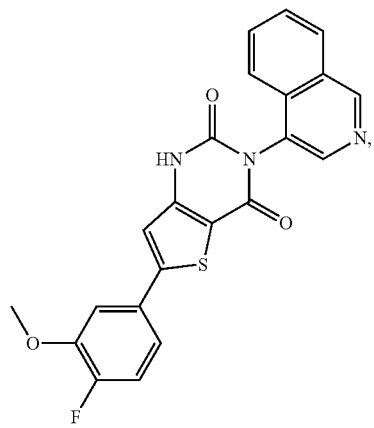
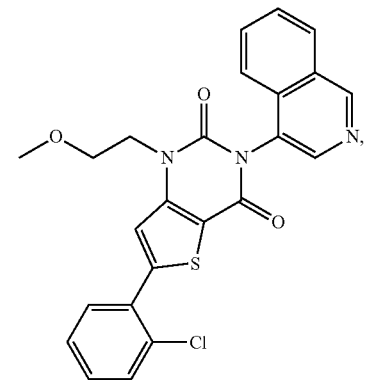
196
-continued
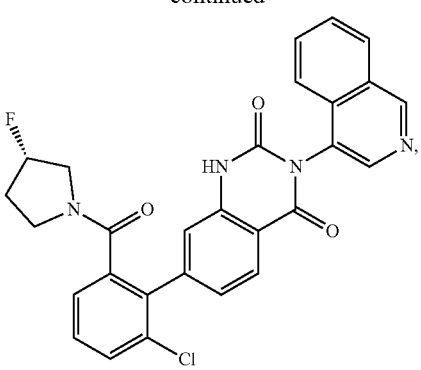
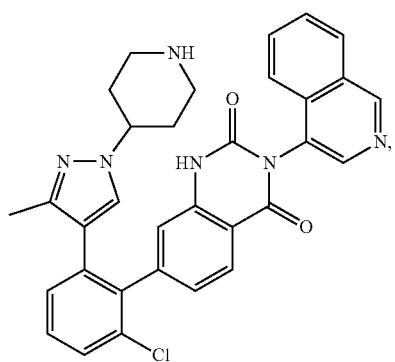
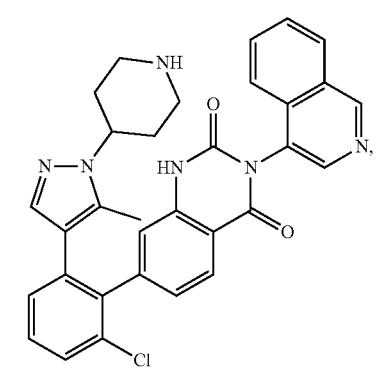
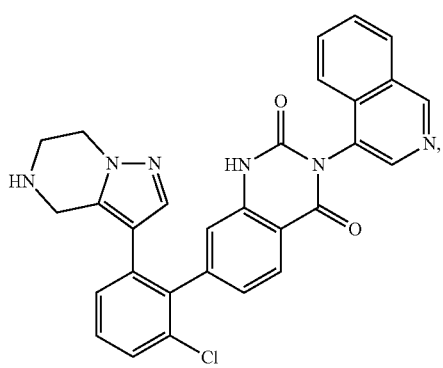

-continued
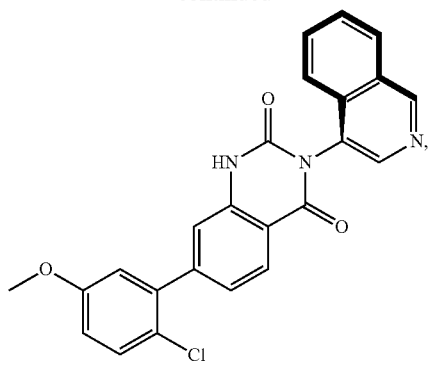
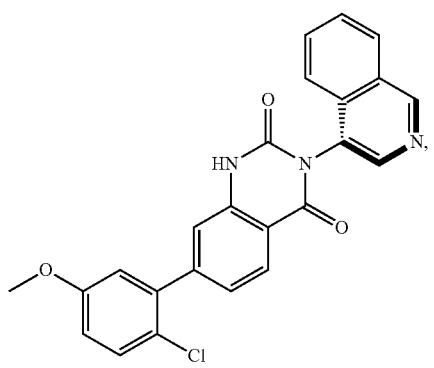
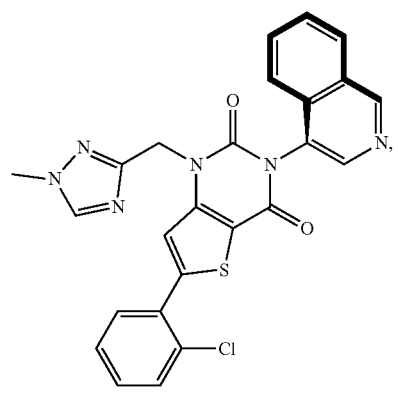
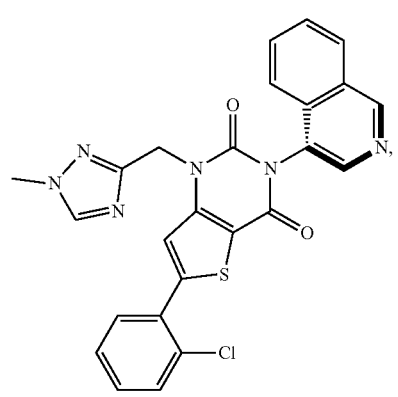
-continued
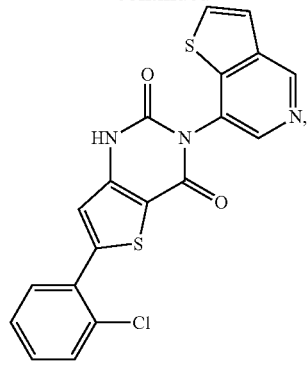
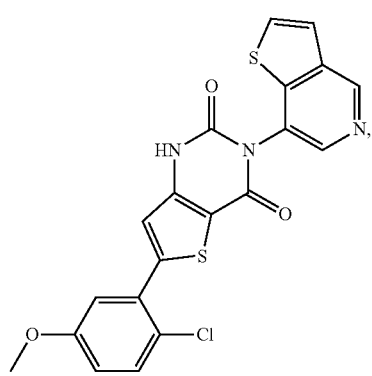
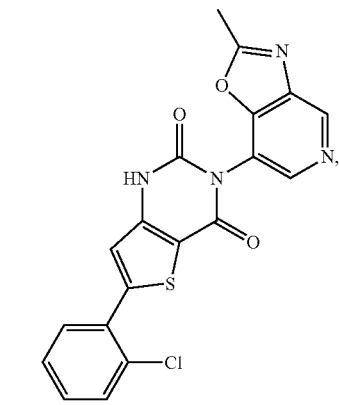
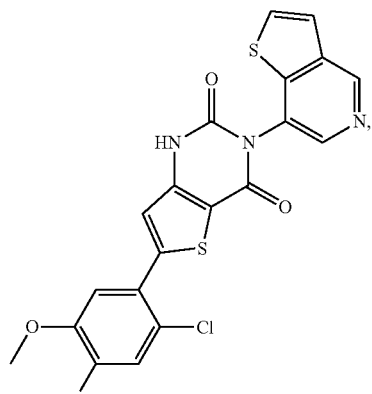

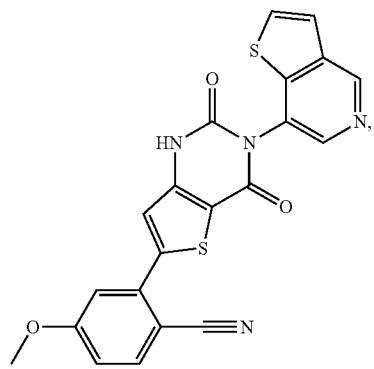
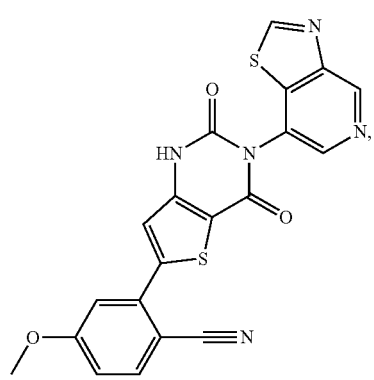
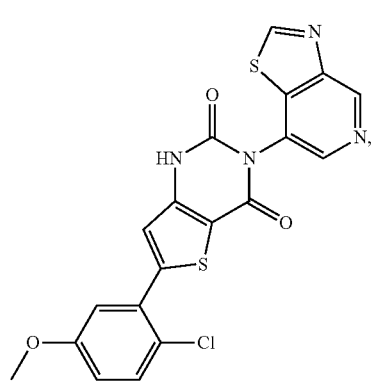
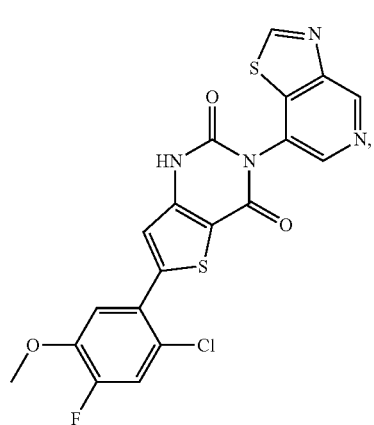
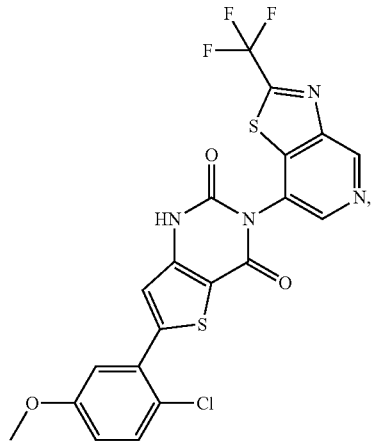
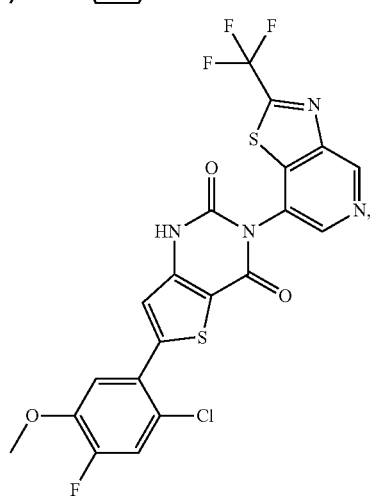
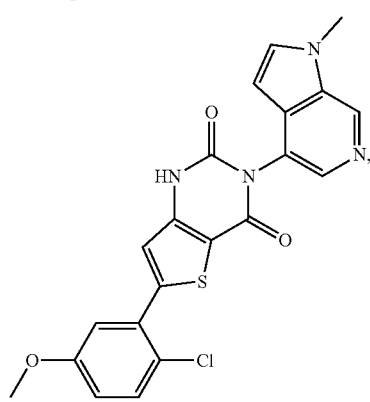
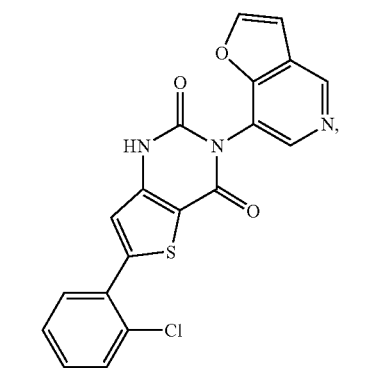

-continued
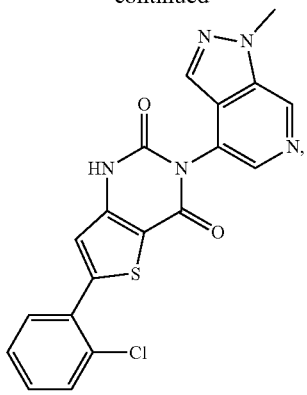
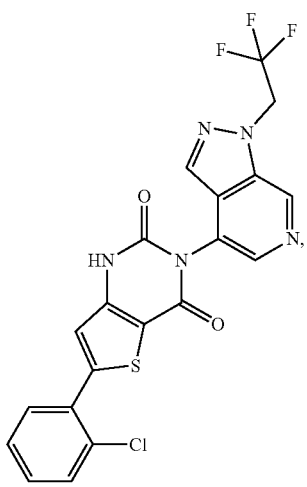
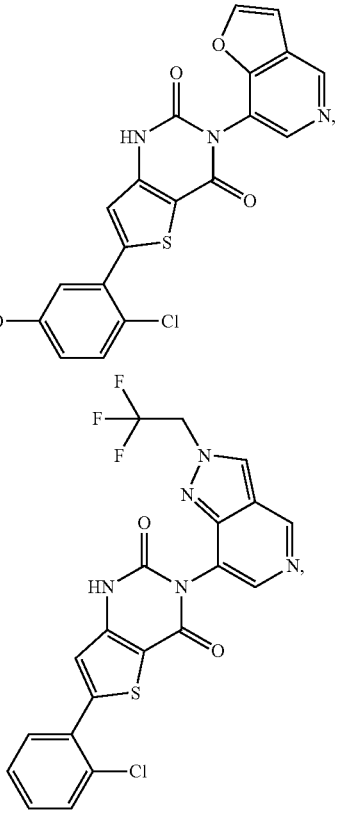
-continued
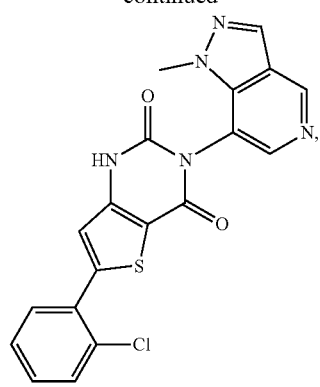
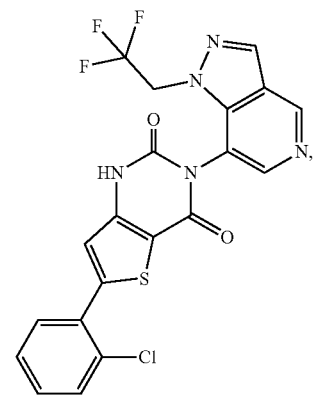
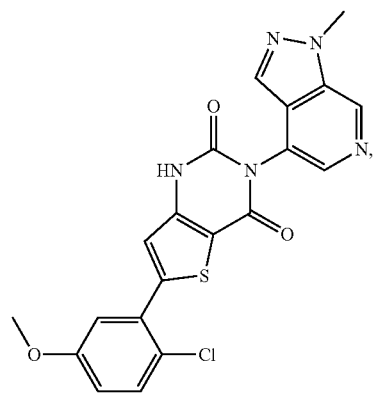
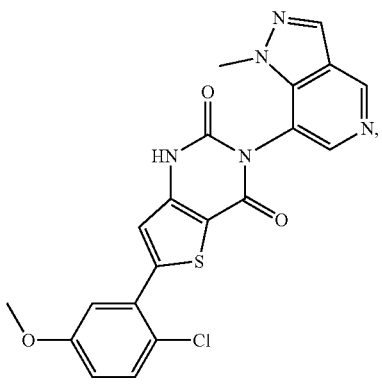

203
-continued
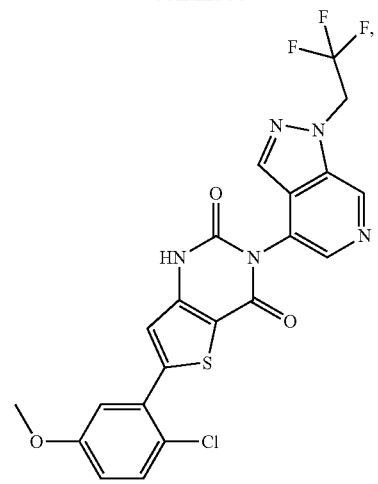
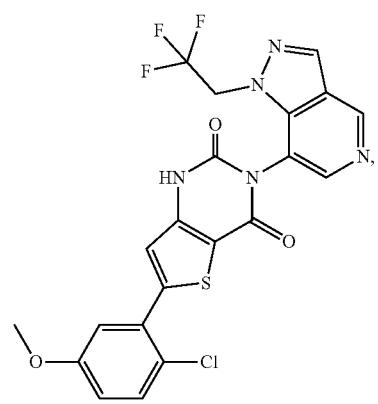
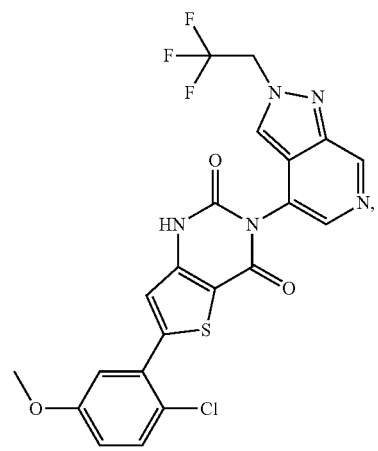
204
-continued
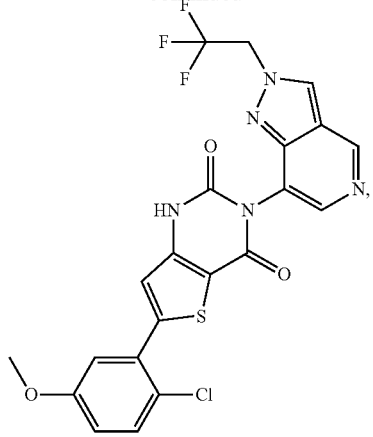
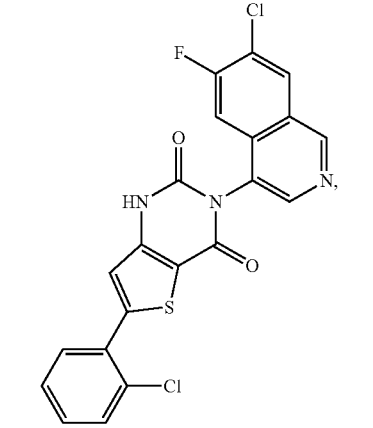
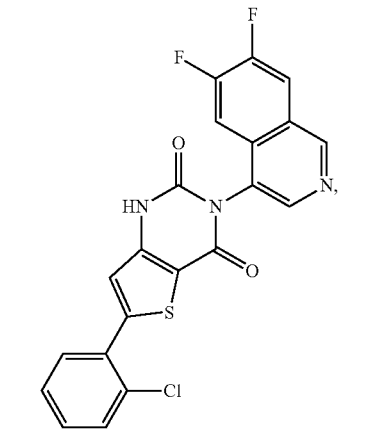
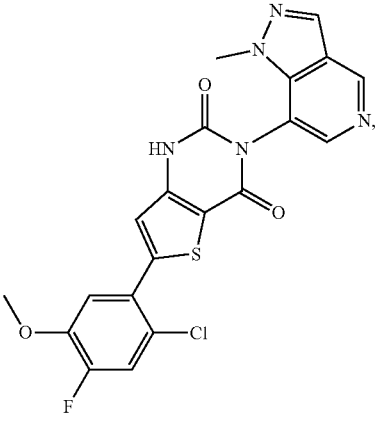

-continued
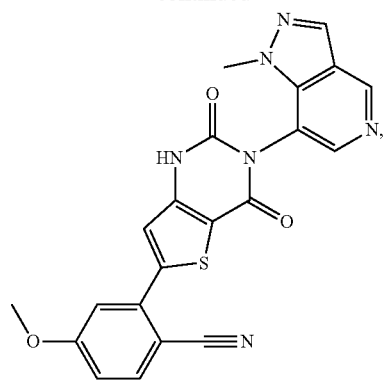
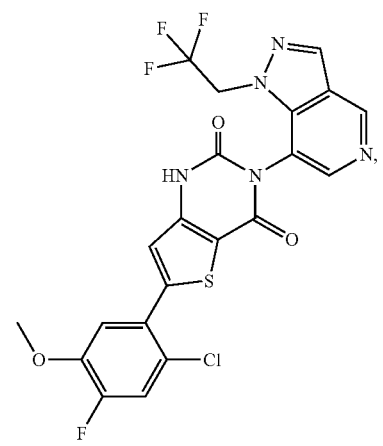
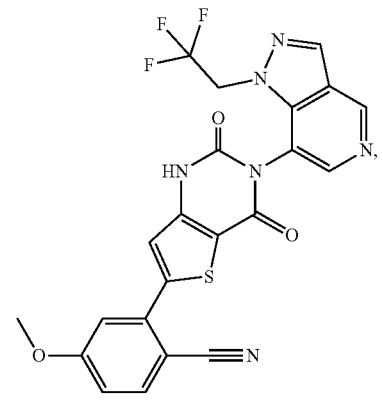
-continued
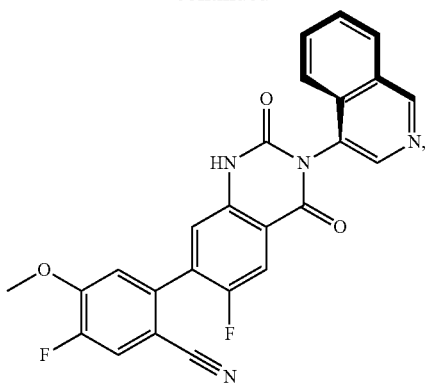
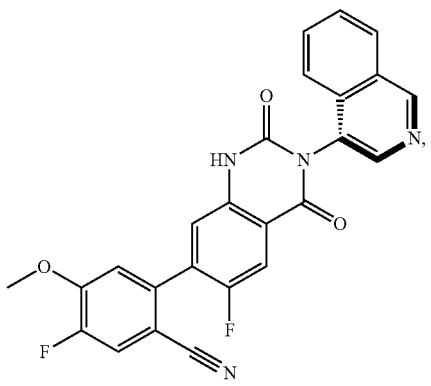
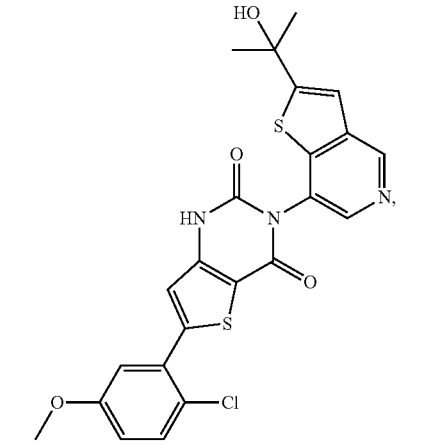
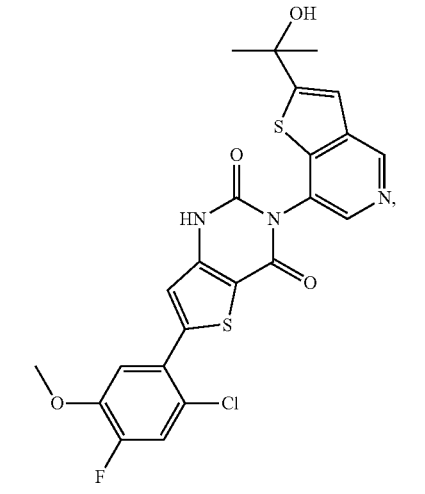

207
-continued

208
-continued
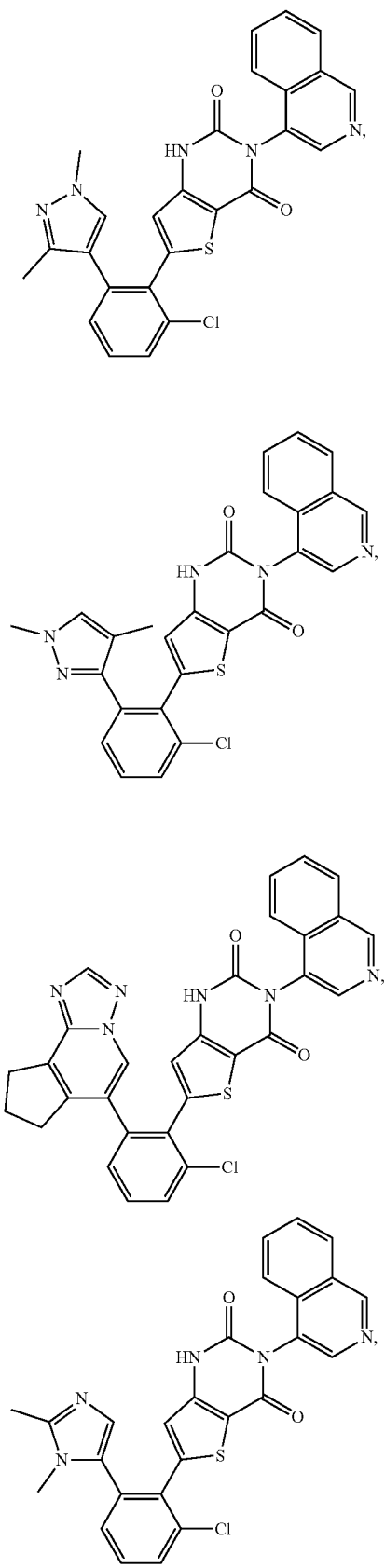

209
-continued
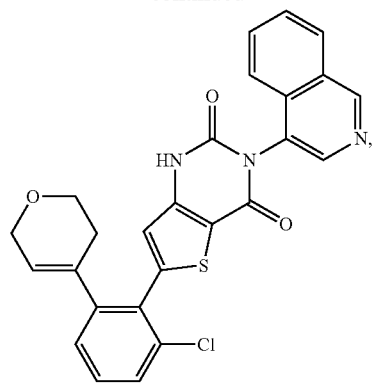
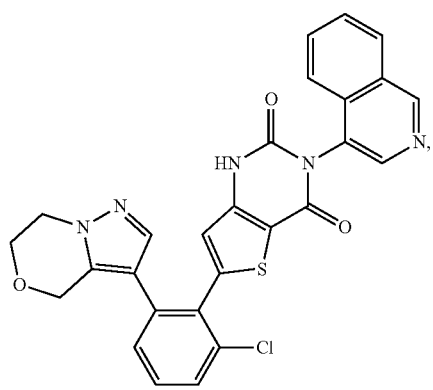
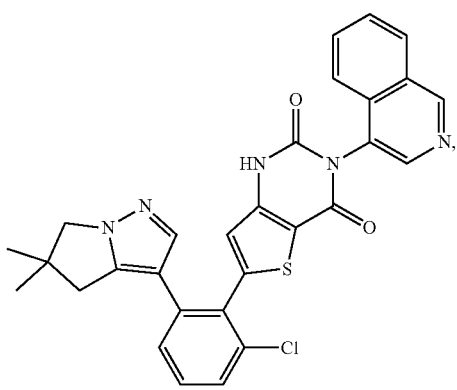
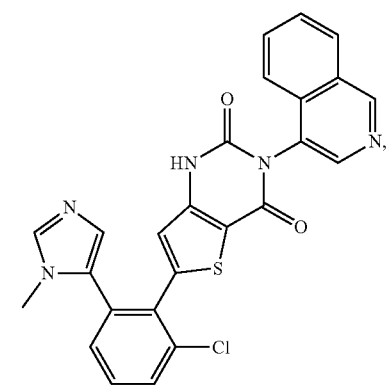
210
-continued
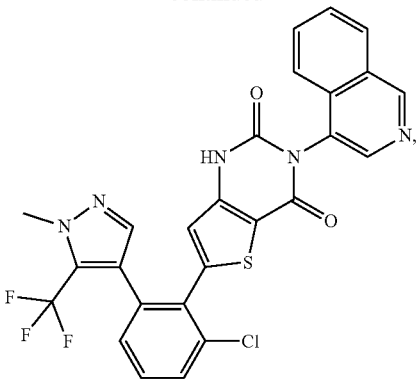
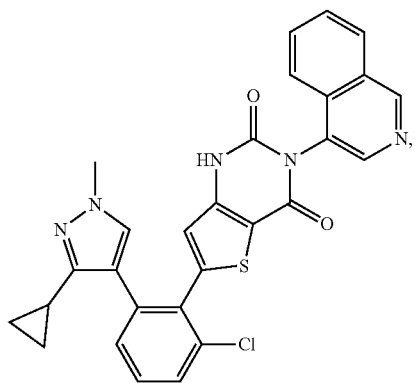
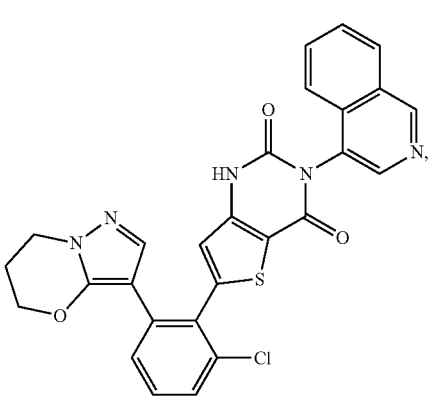
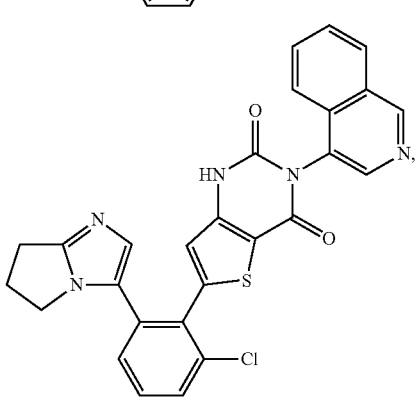

211
-continued
212
-continued
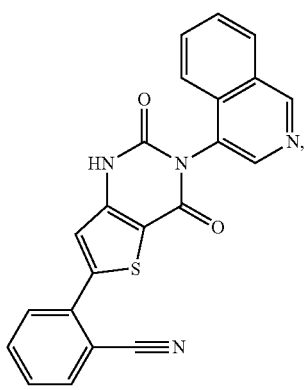
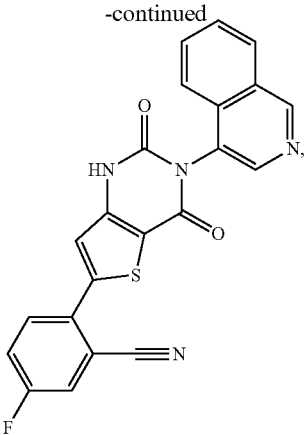

213
-continued
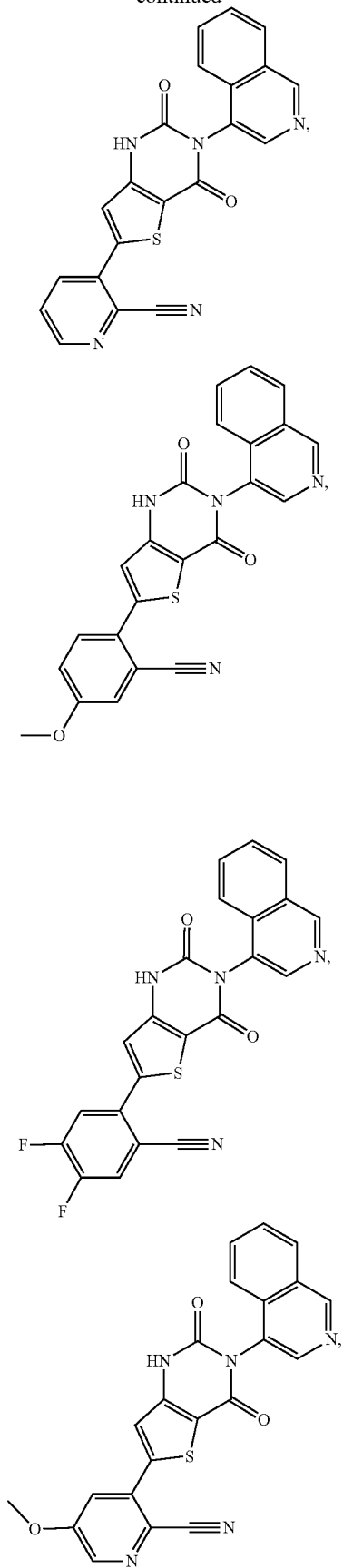
214
-continued
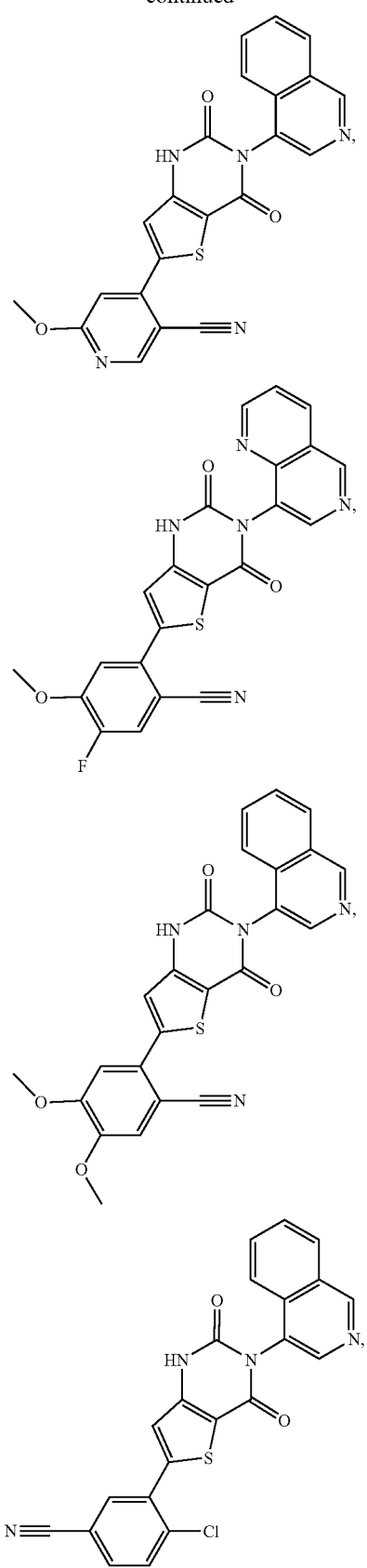

215
-continued
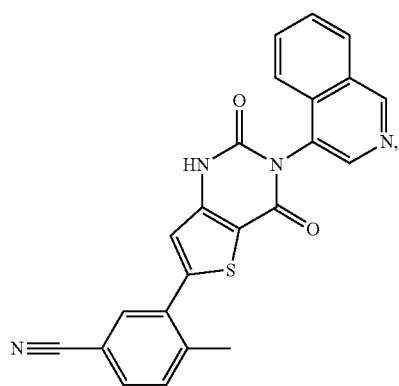
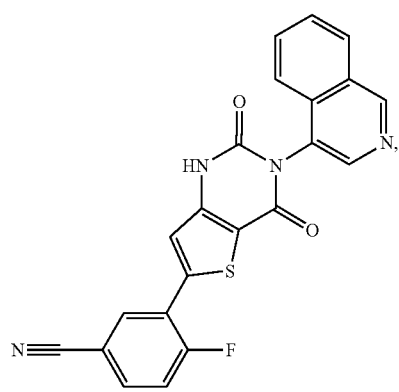
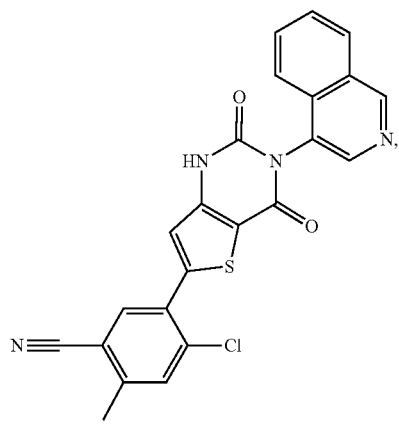
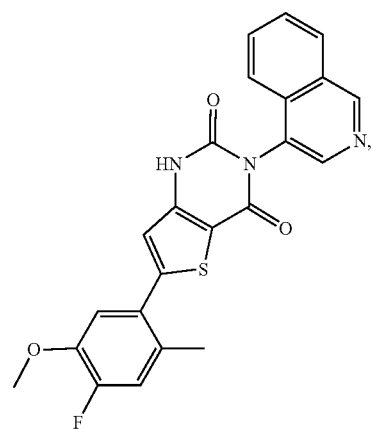
216
-continued
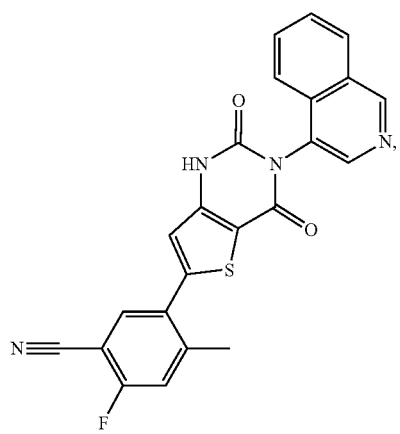
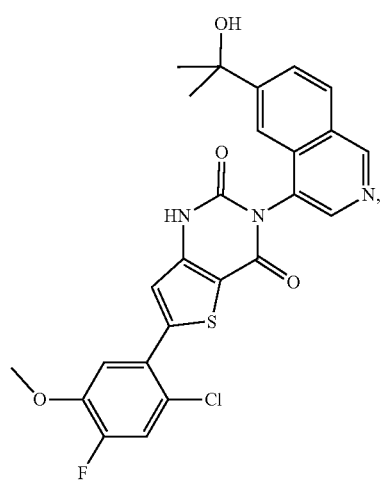
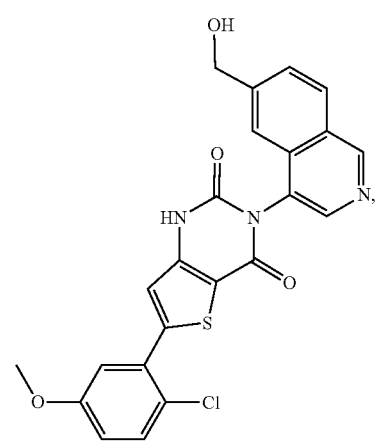

217
-continued
218
-continued
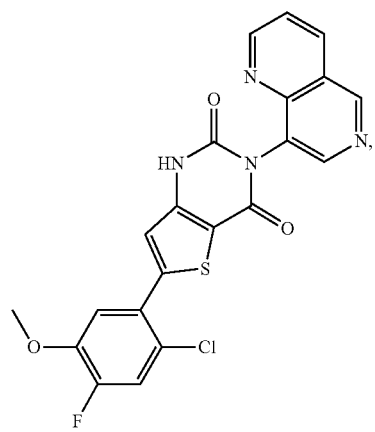
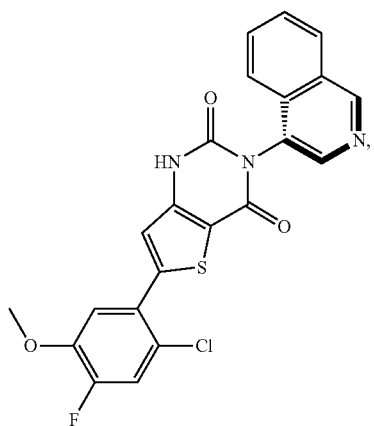

219
-continued
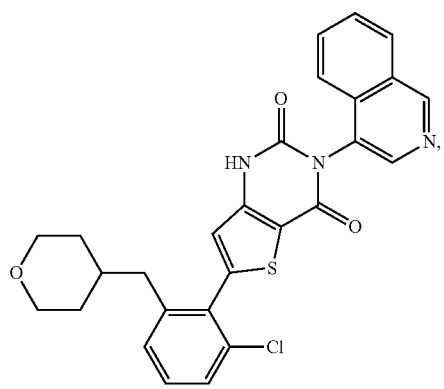
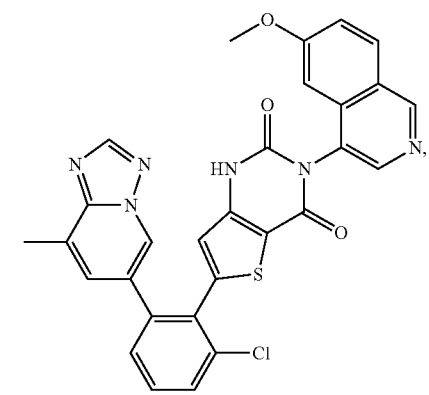
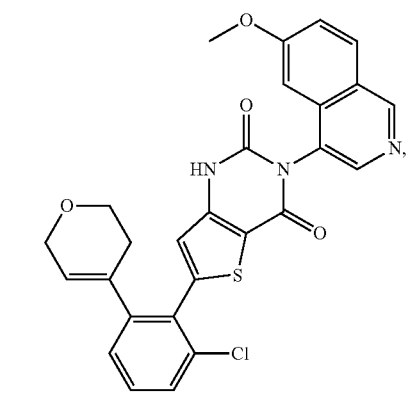
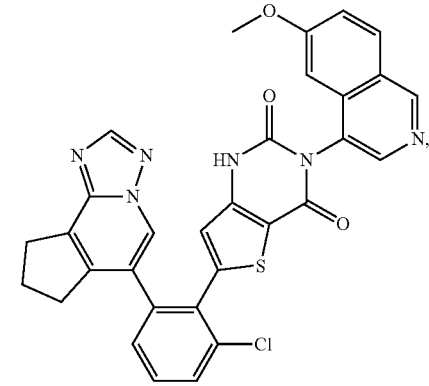
220
-continued
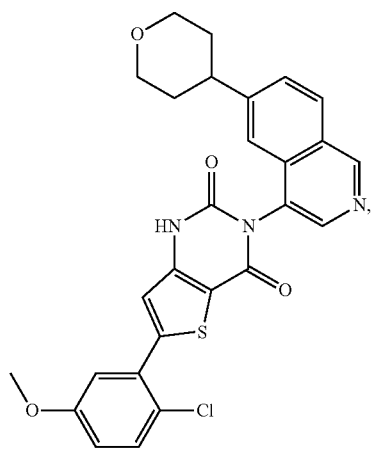
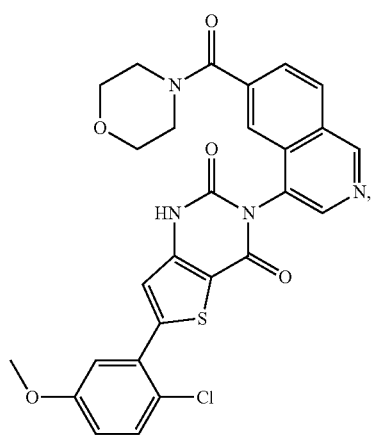
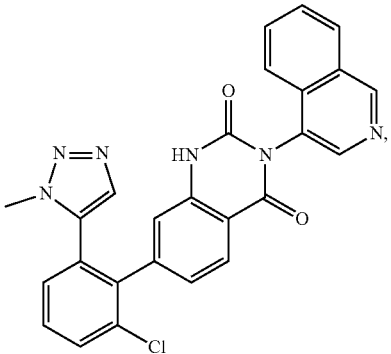
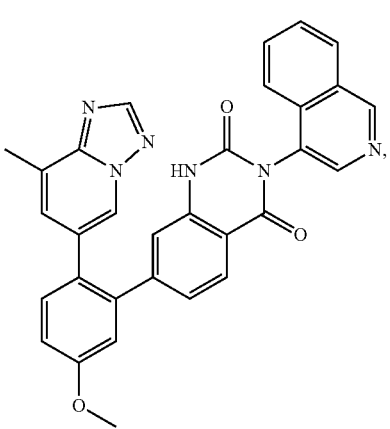

221
-continued
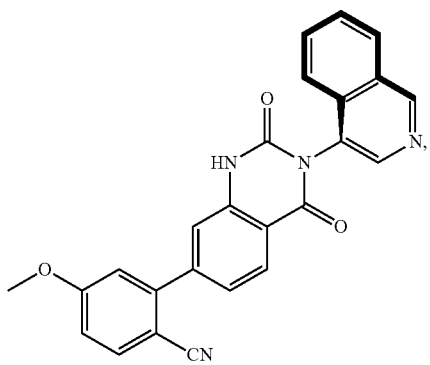
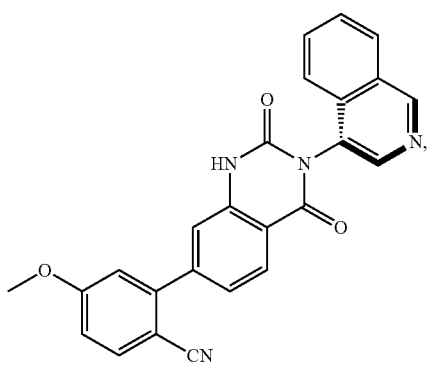
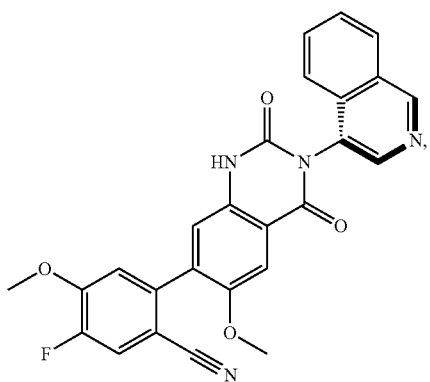
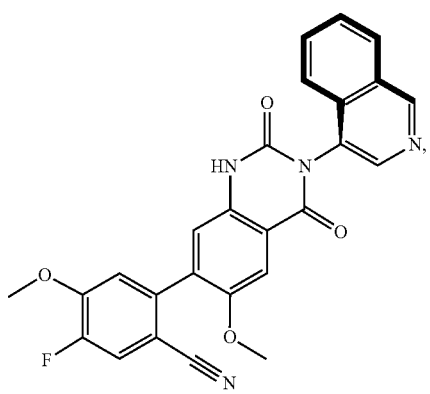
222
-continued
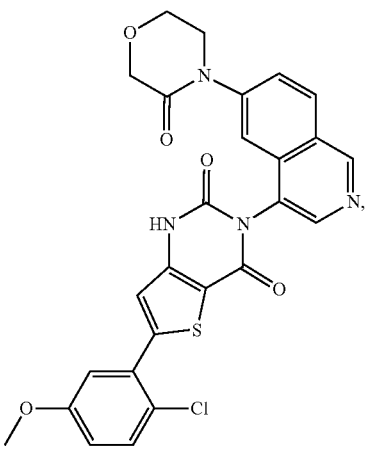
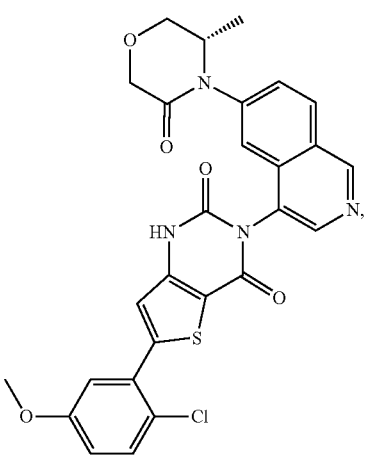

223
-continued
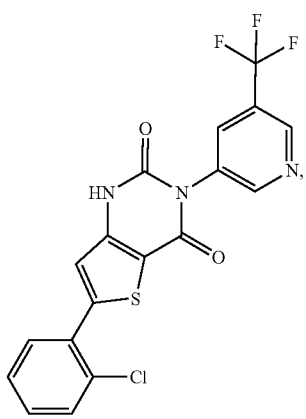
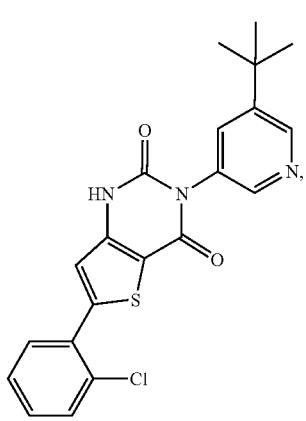
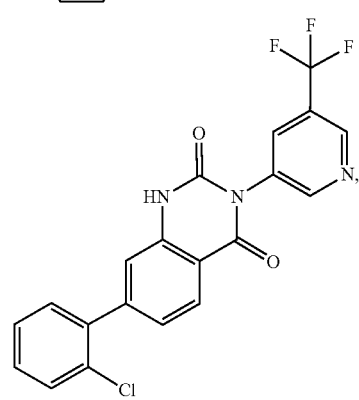
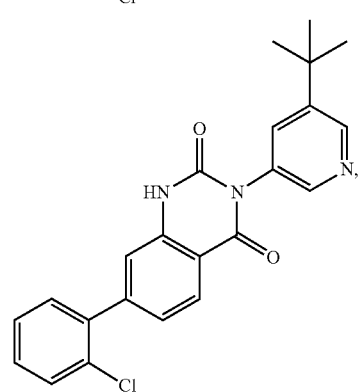
224
-continued
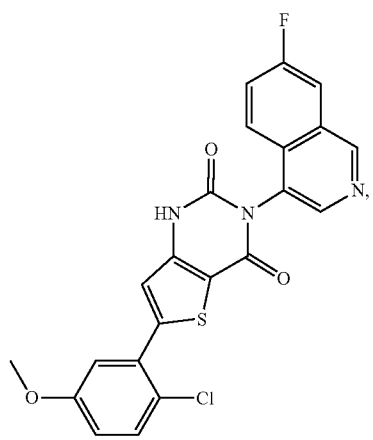
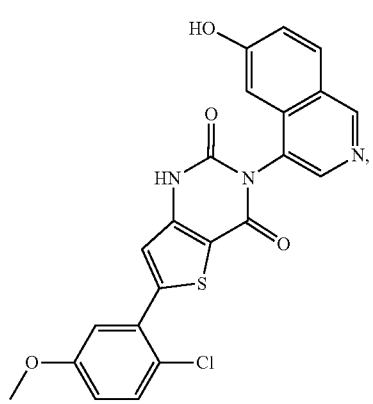
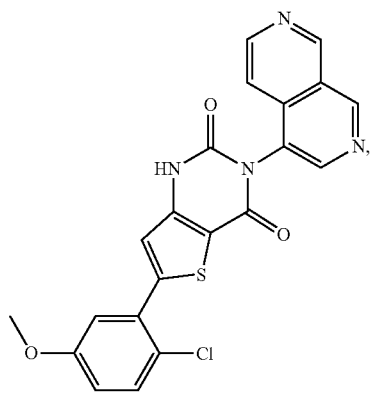
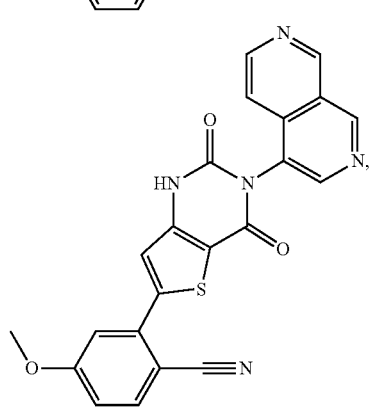

225
-continued
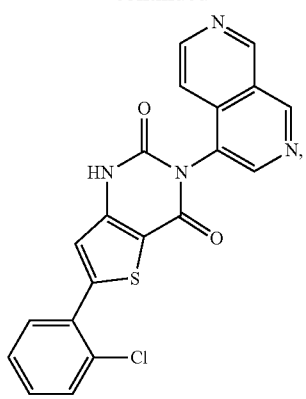
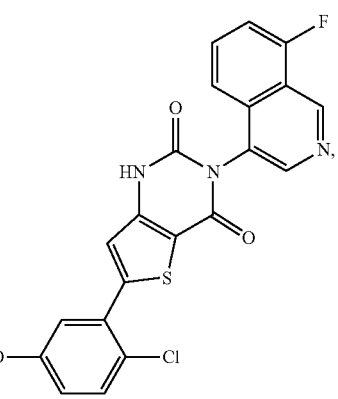
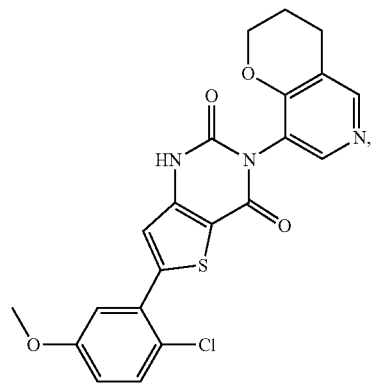
226
-continued
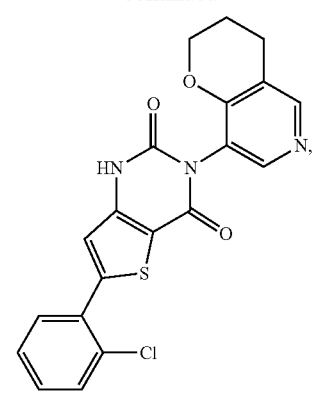
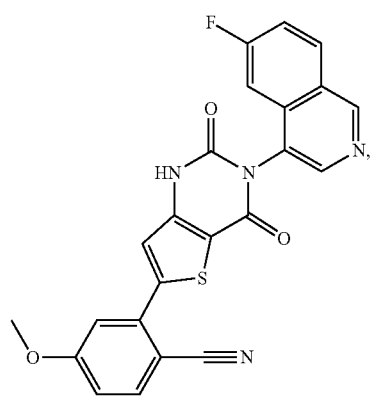
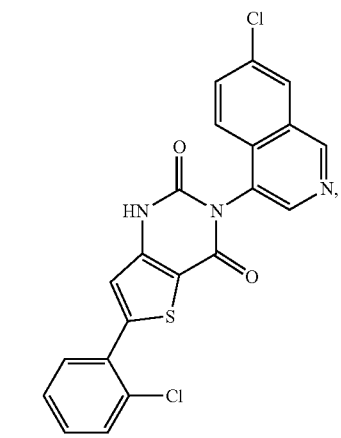
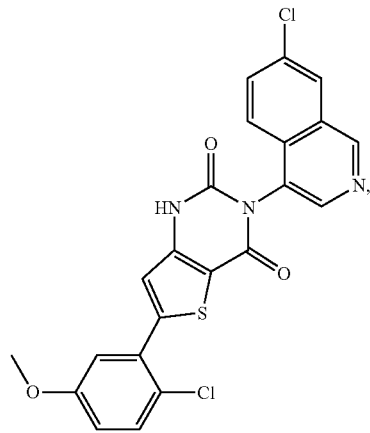

227
-continued
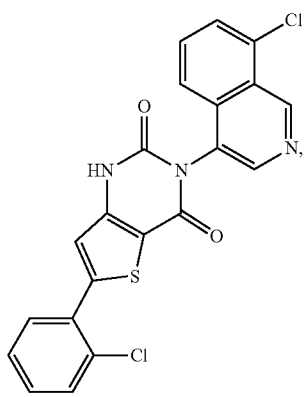
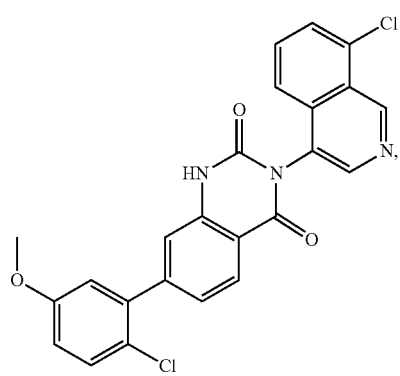
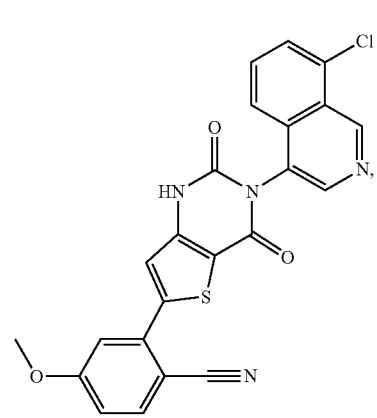
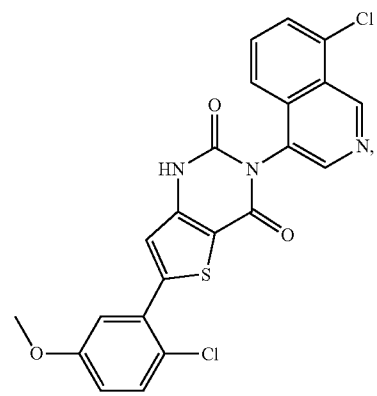
228
-continued
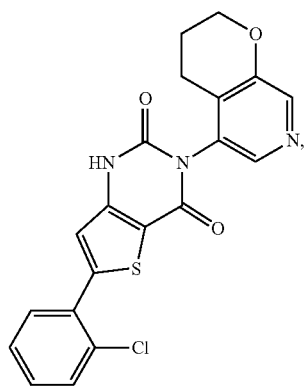
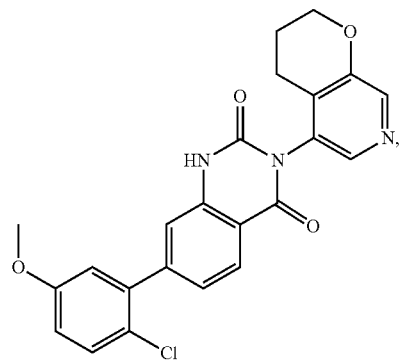
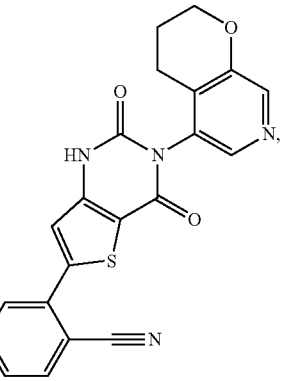
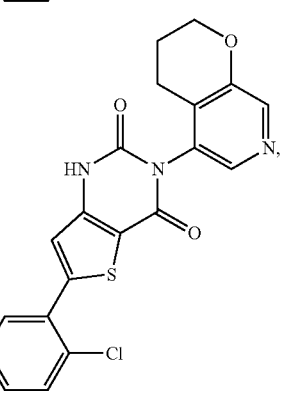

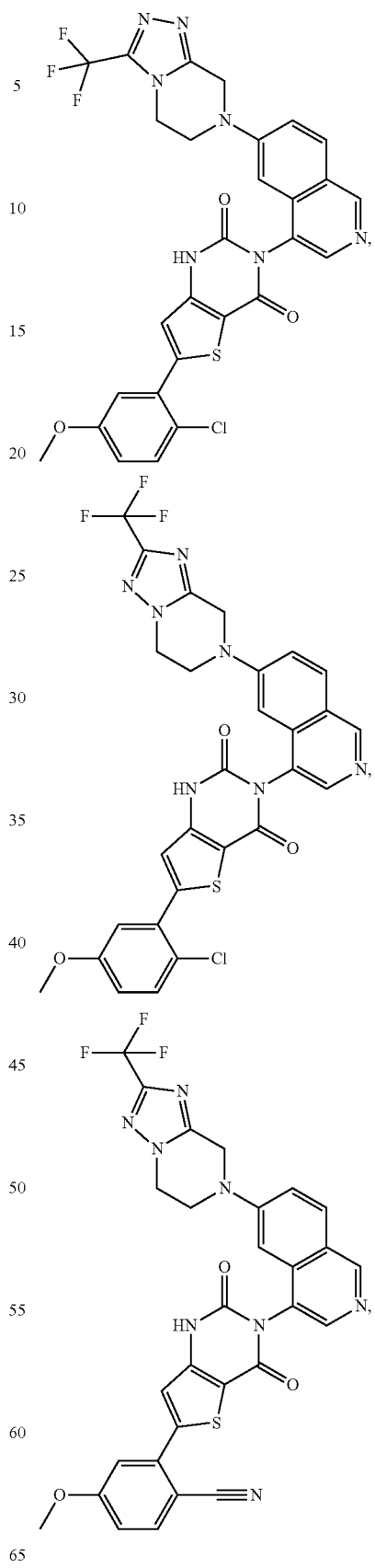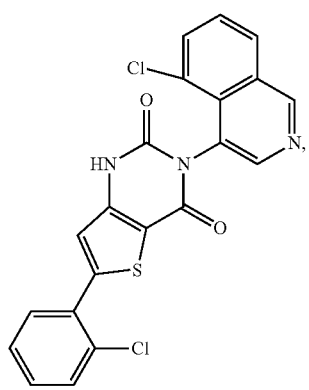

231
-continued
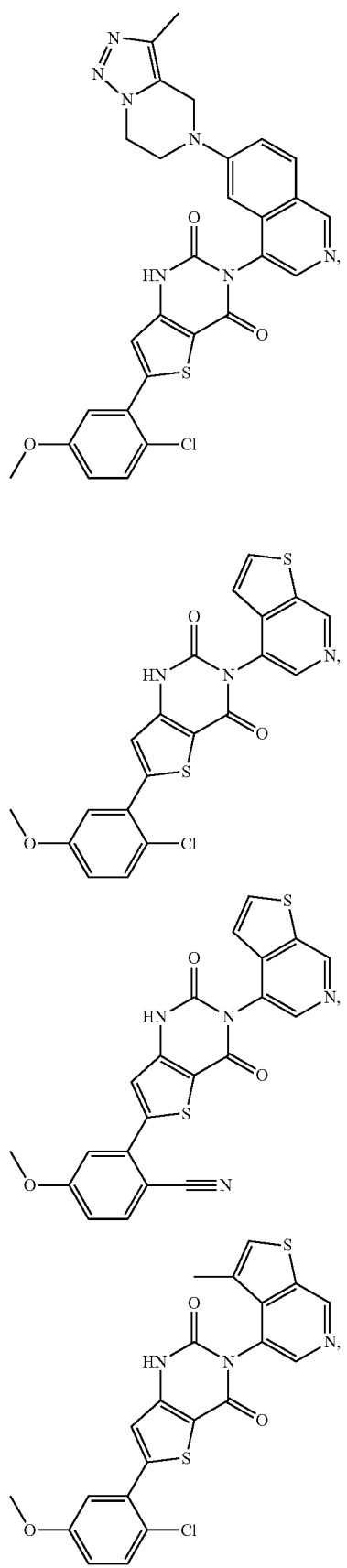
232
-continued
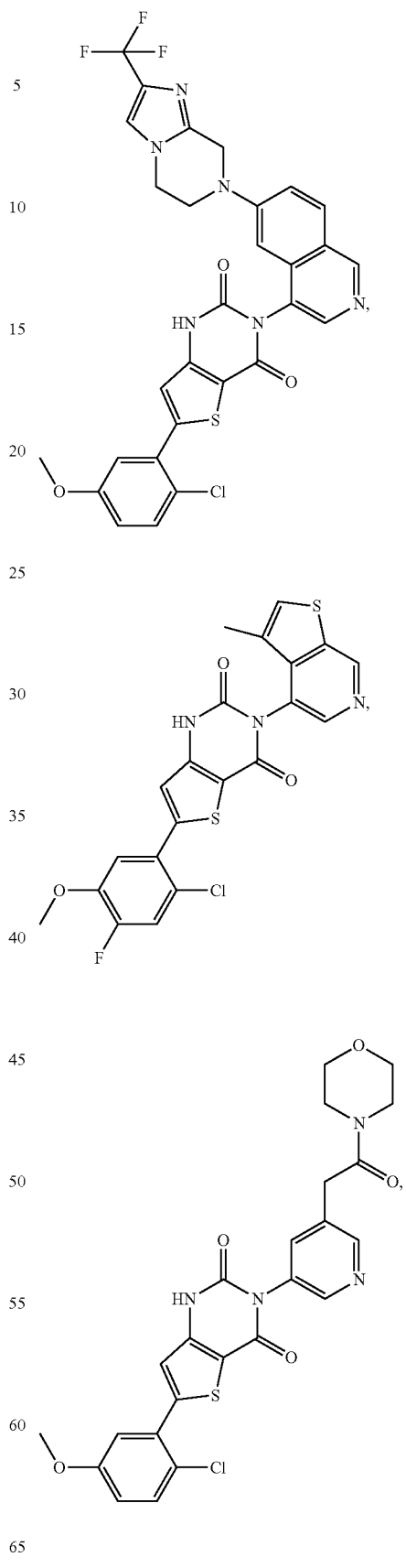

233
-continued
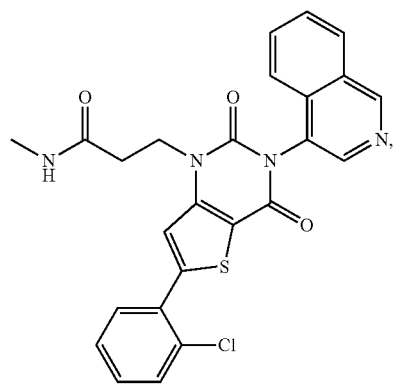
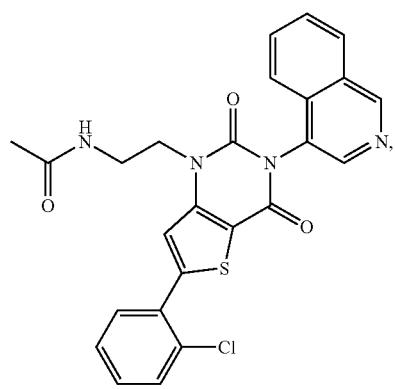
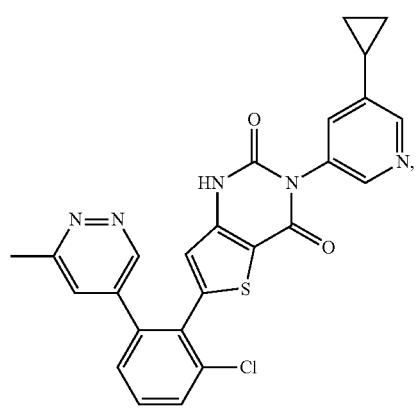
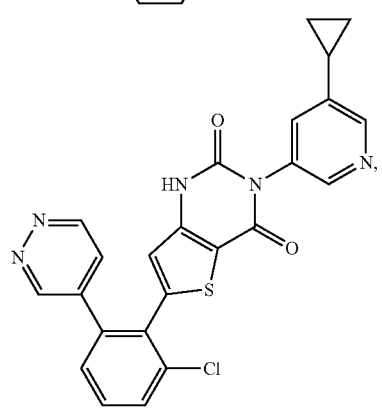
234
-continued
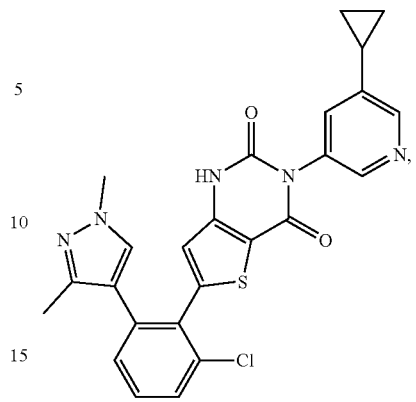
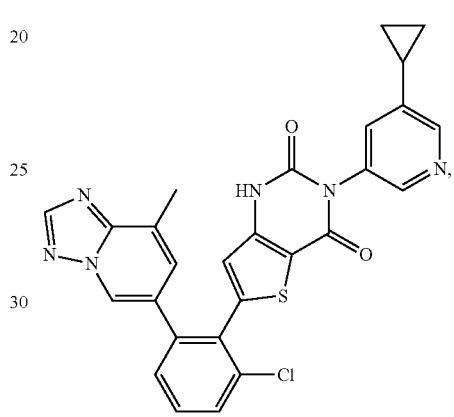
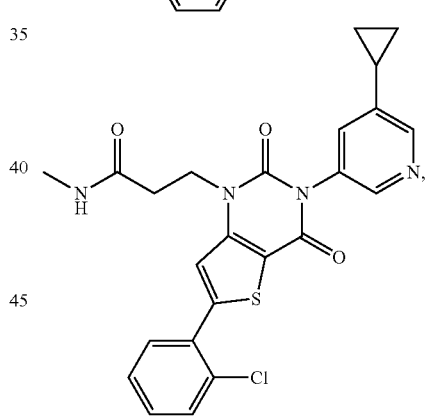
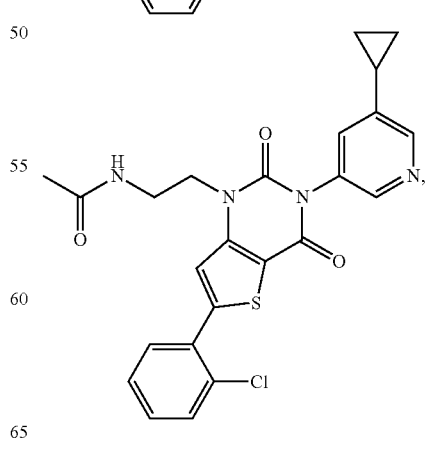

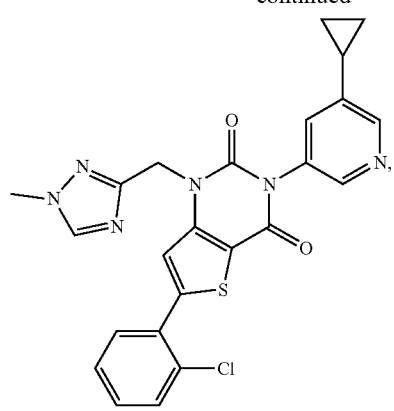
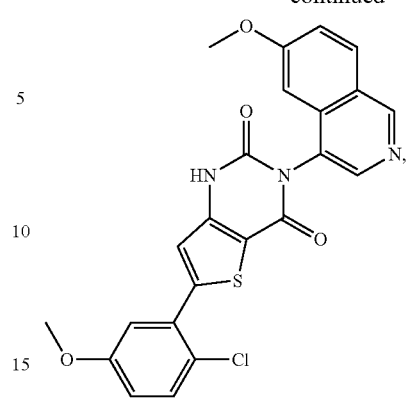
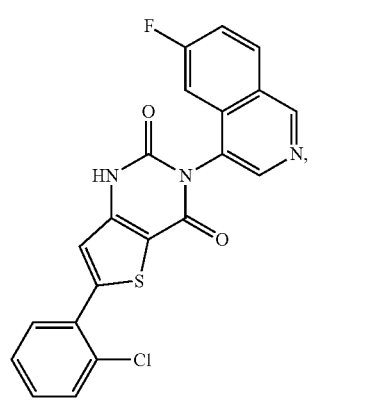
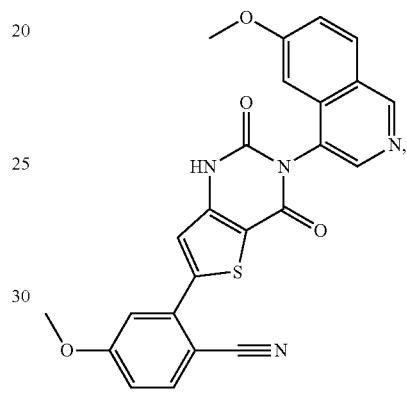
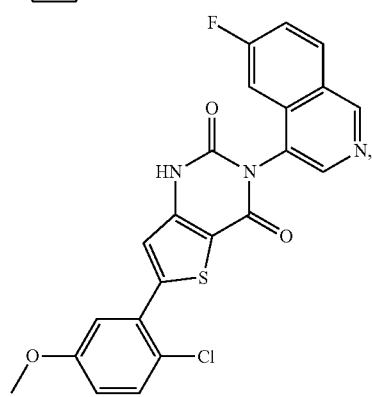
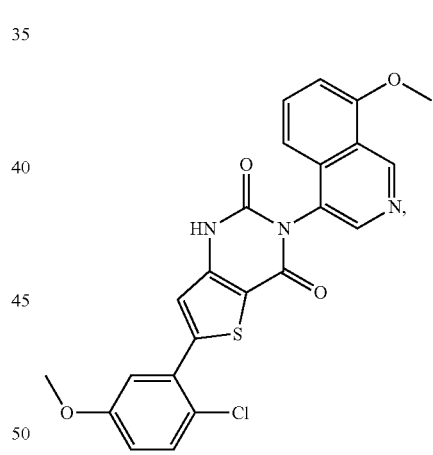
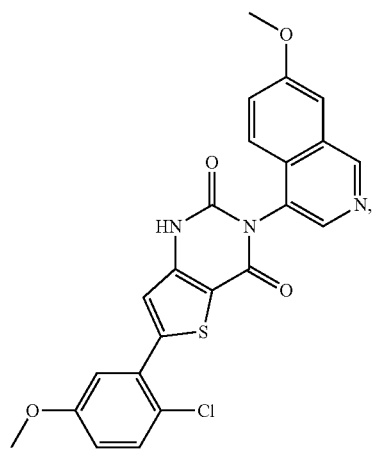
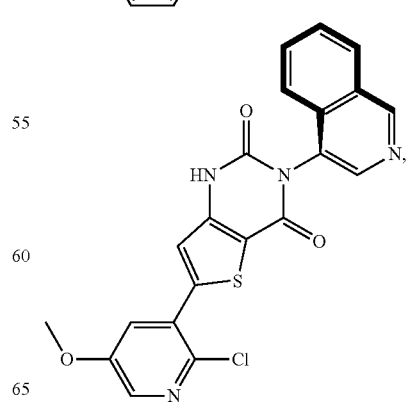

237
-continued
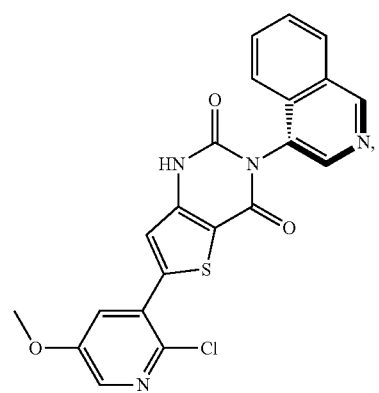
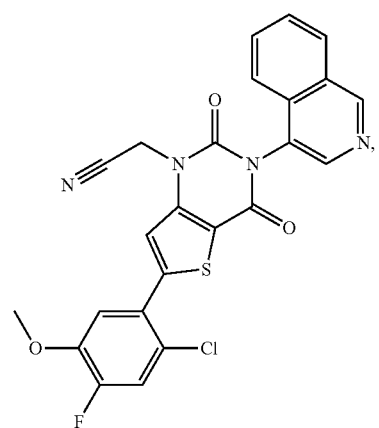
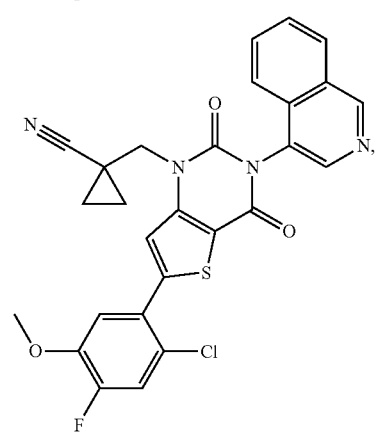
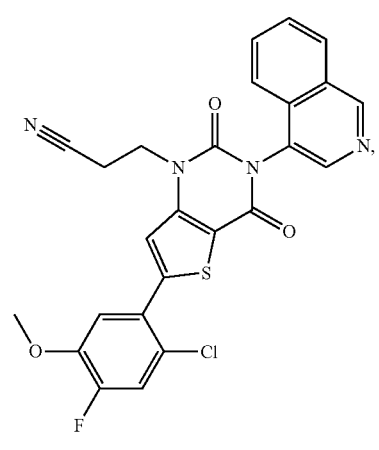
238
-continued
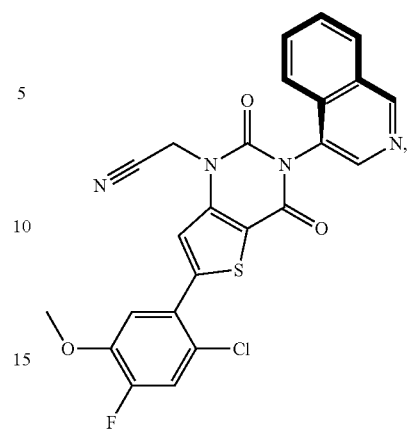
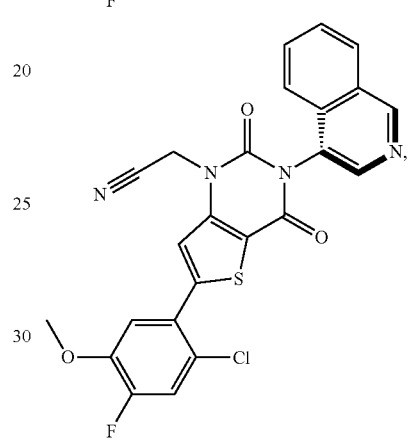
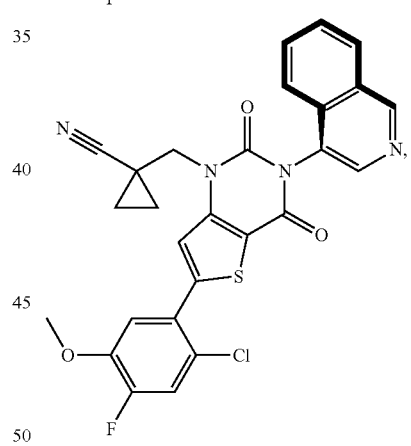
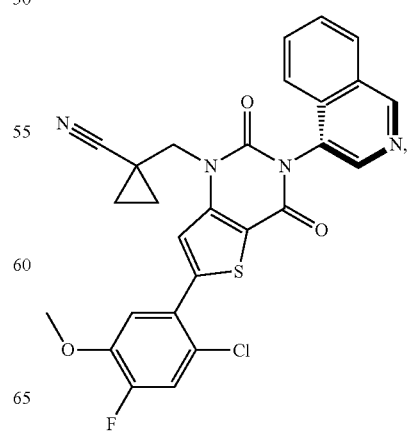

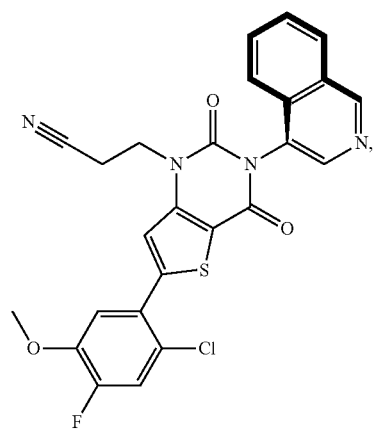
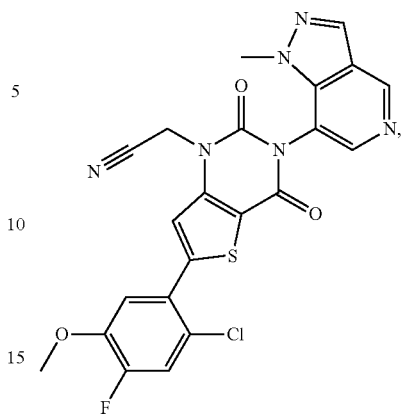
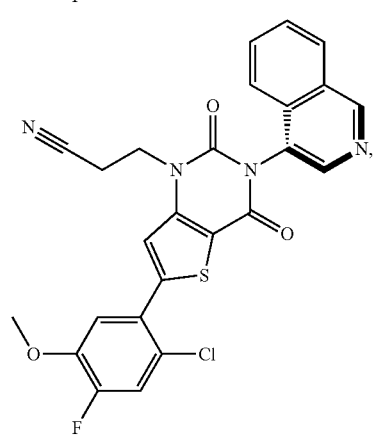
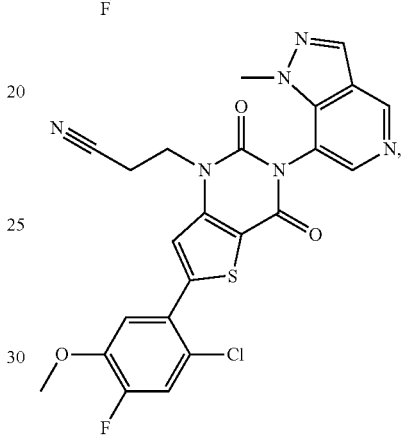
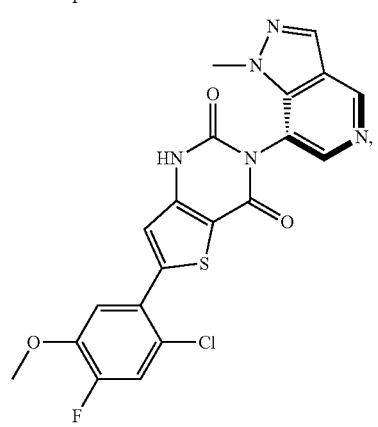
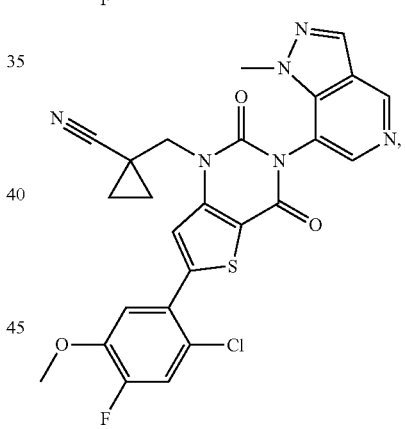
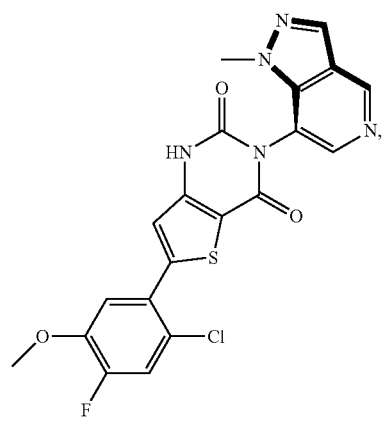
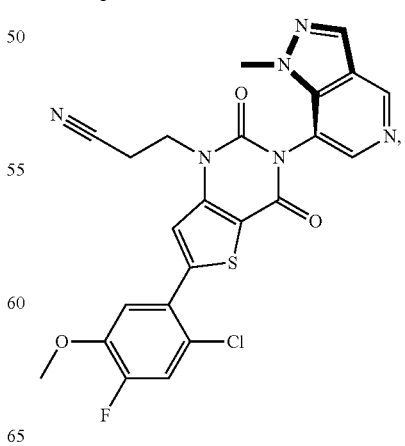

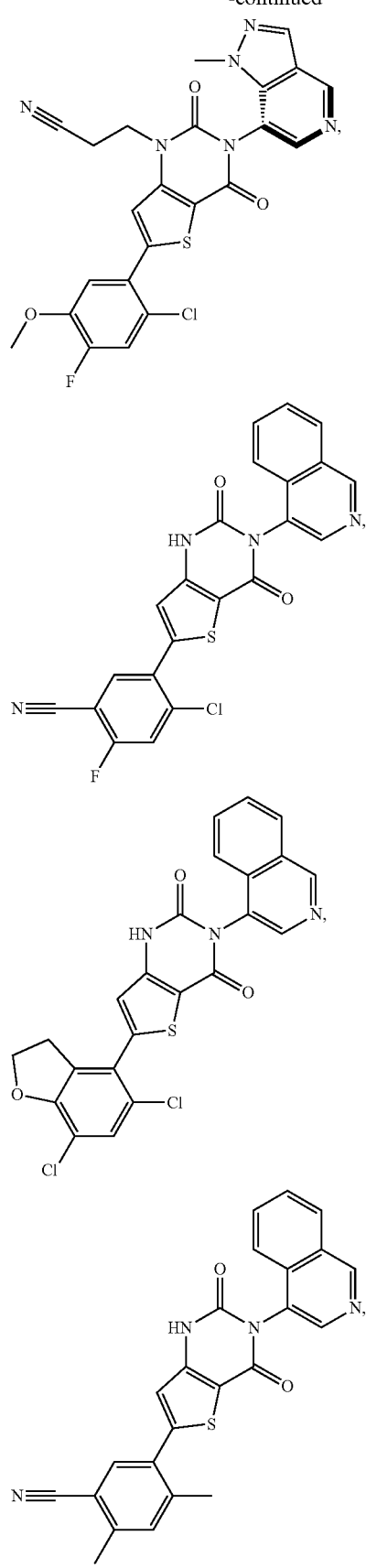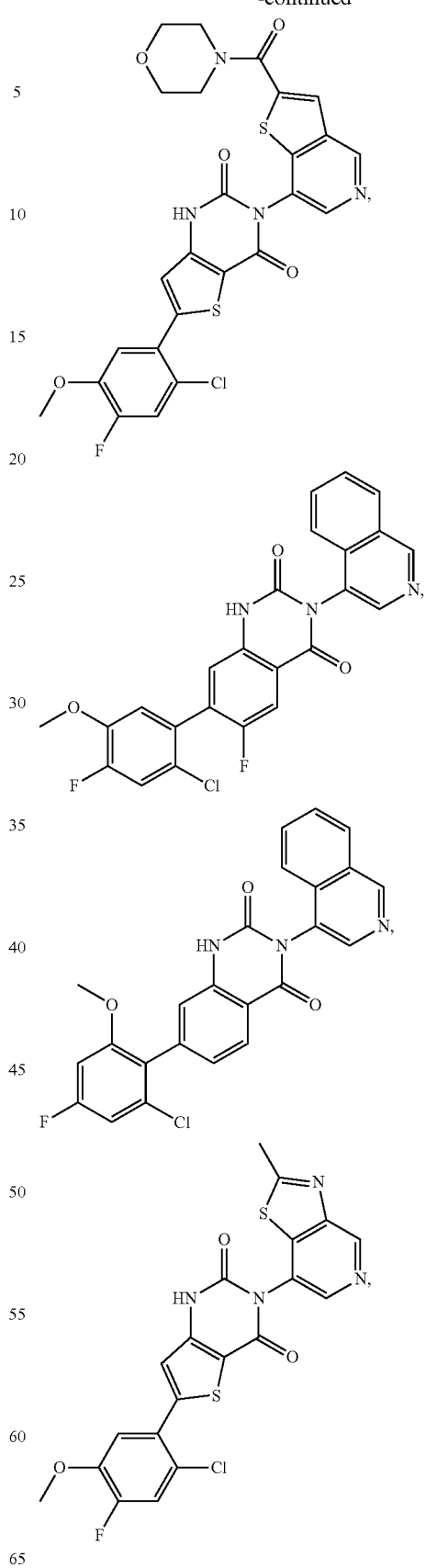

243
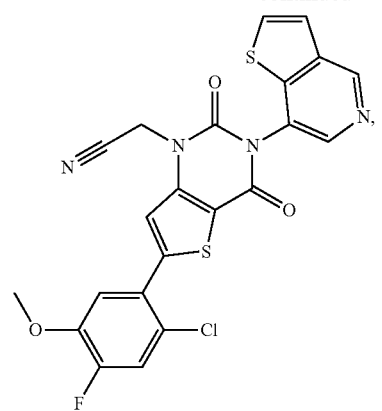
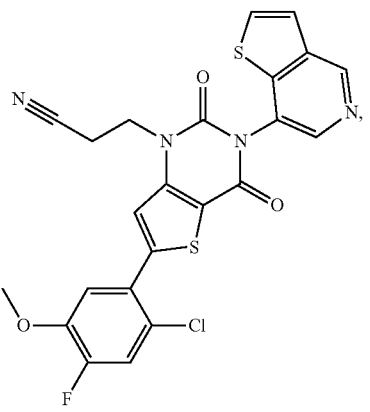
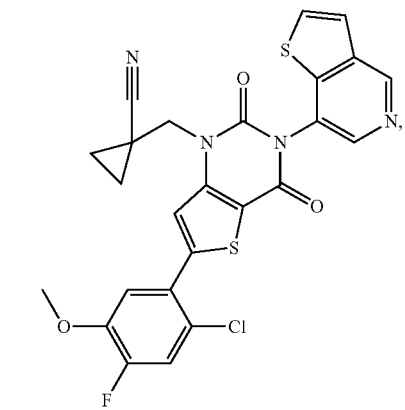
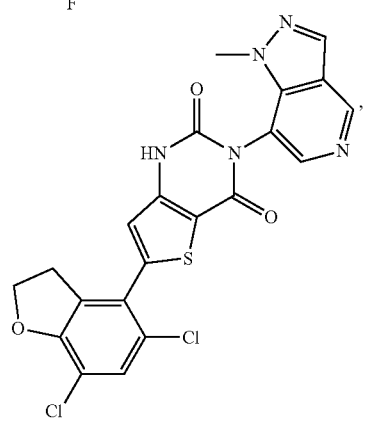
244
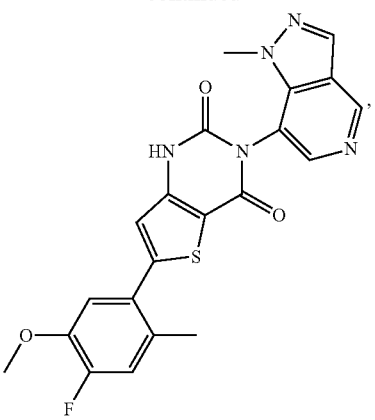
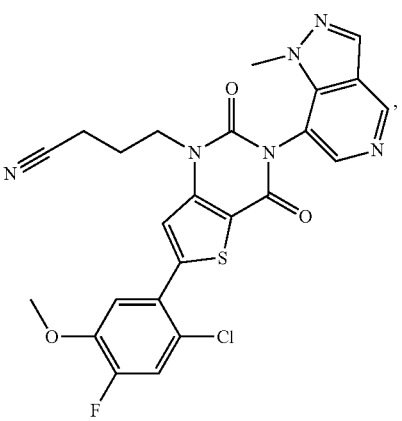
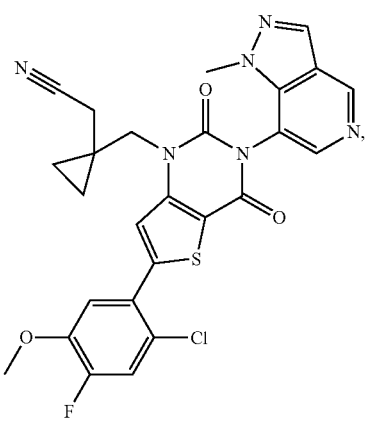
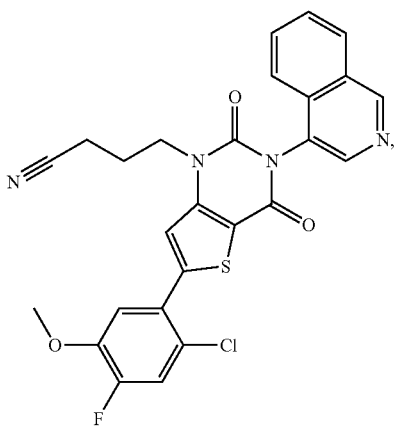

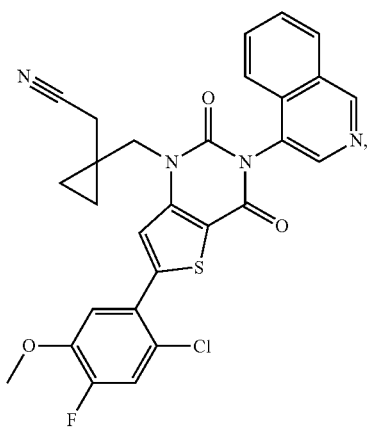
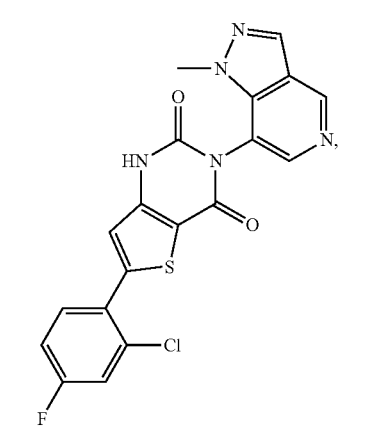
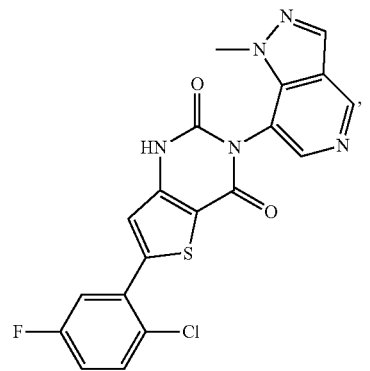
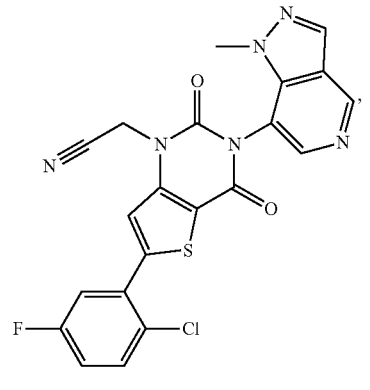
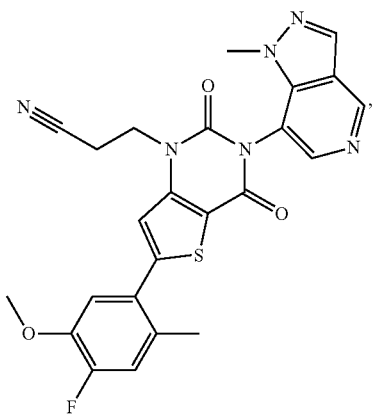
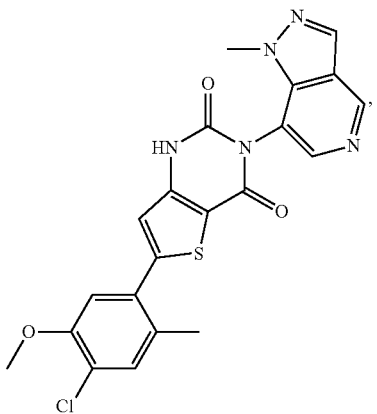
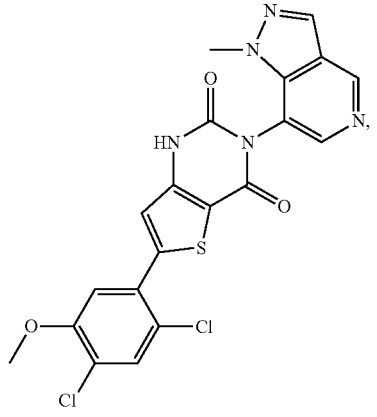
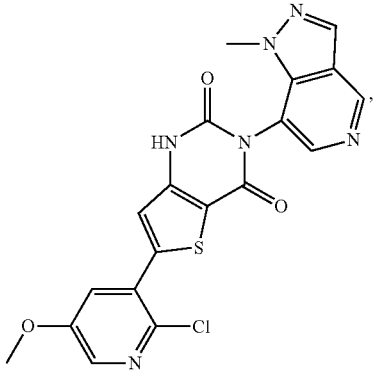

-continued
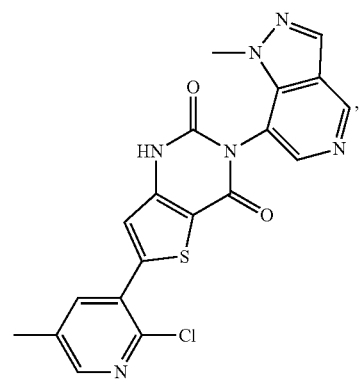
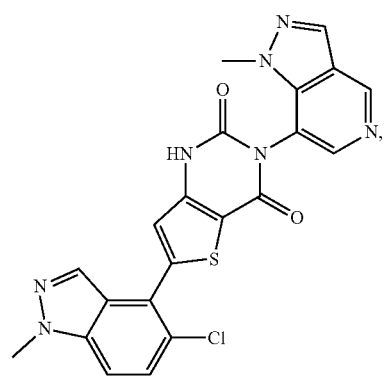
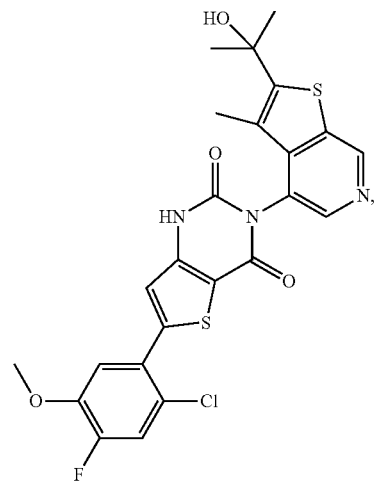
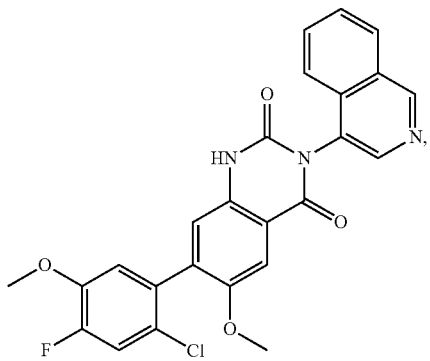
-continued
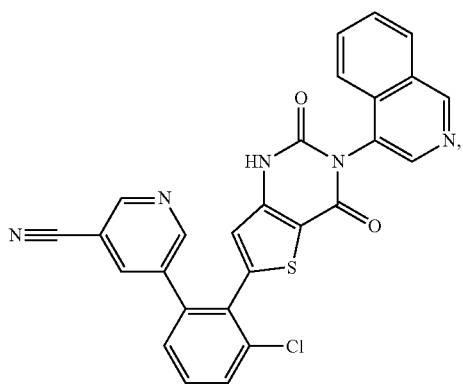
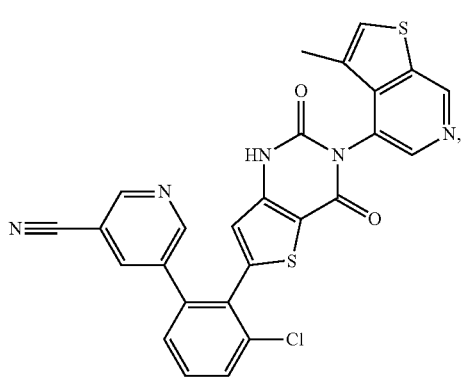
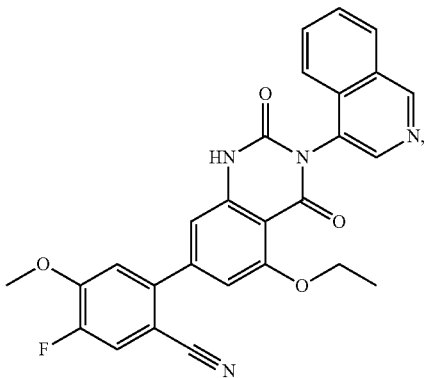
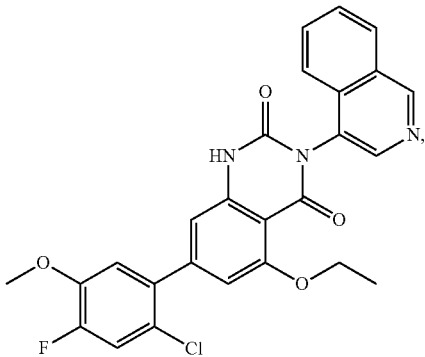

249
-continued
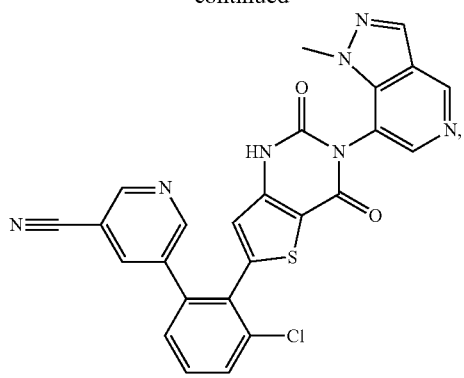
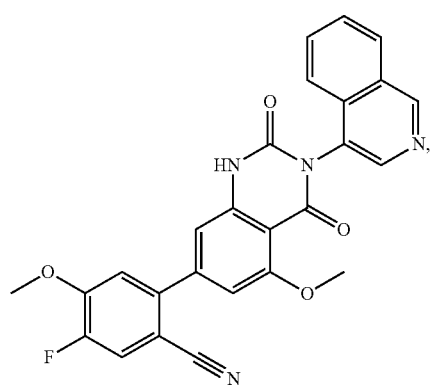
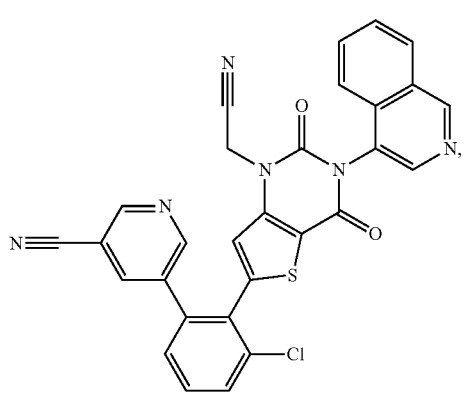
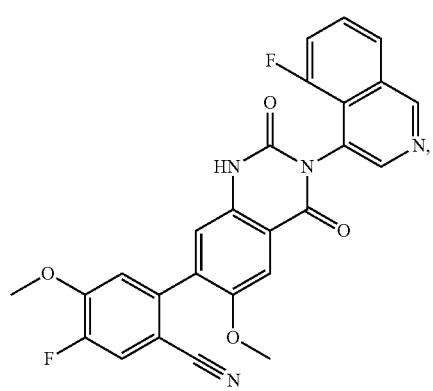
250
-continued
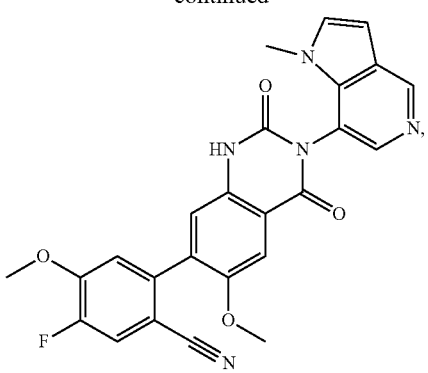
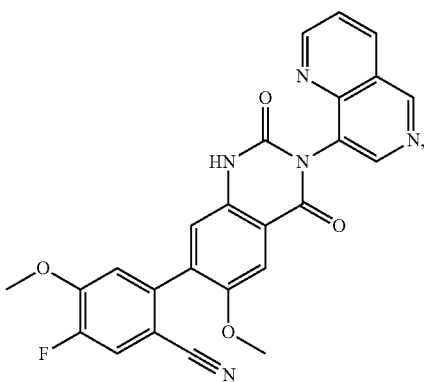
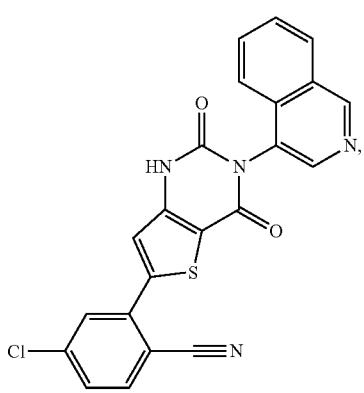
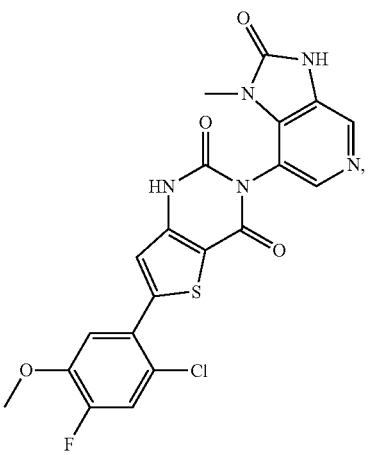

-continued
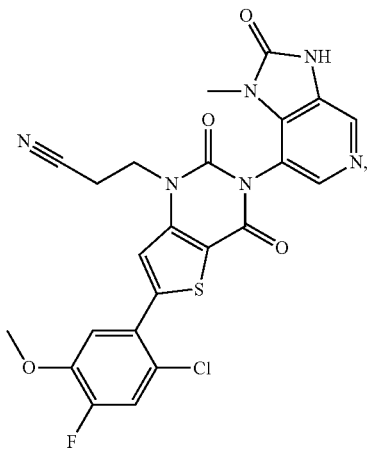
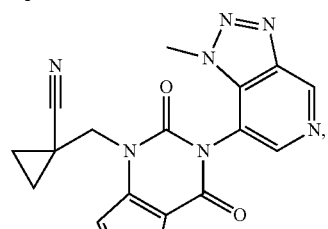
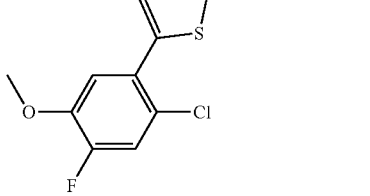

-continued
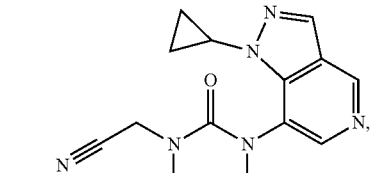
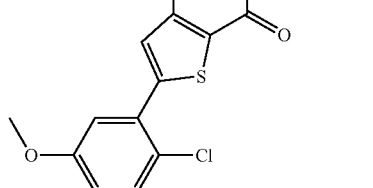
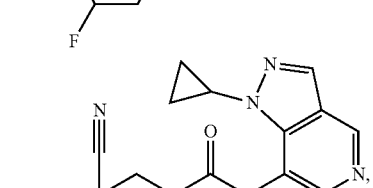
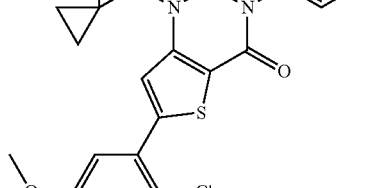
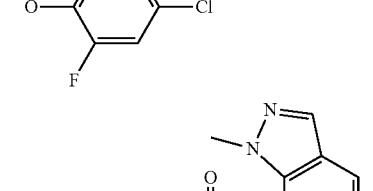
Stereochemistry arbitrary 253
-continued
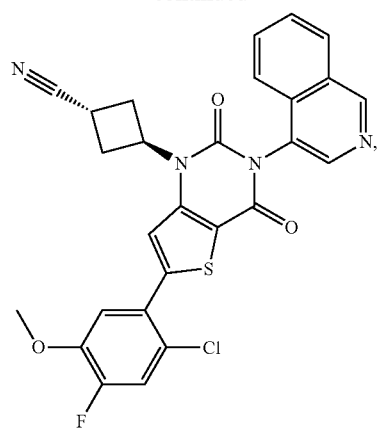
Stereochemistry arbitrary
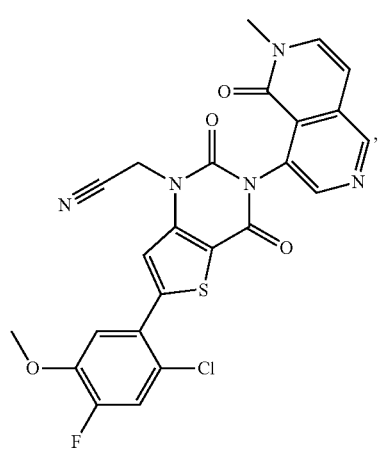
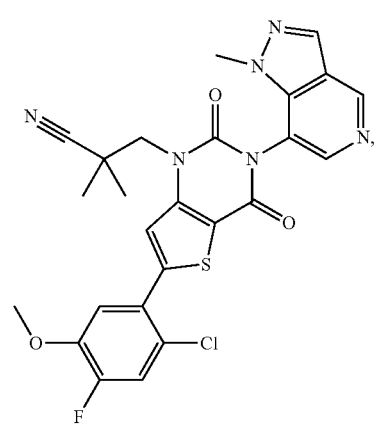
254
-continued
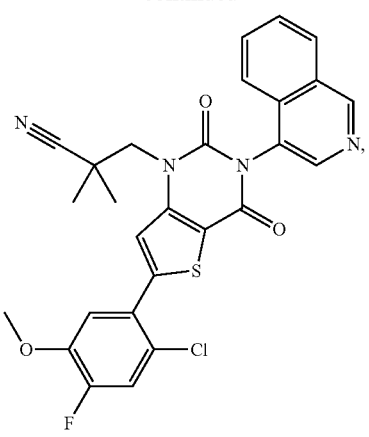
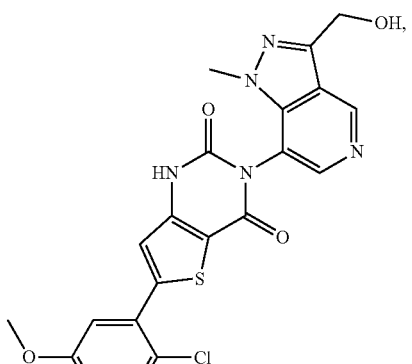
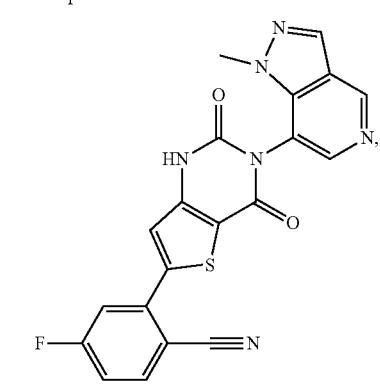
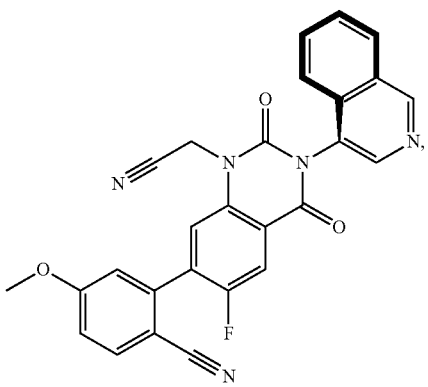

255
-continued
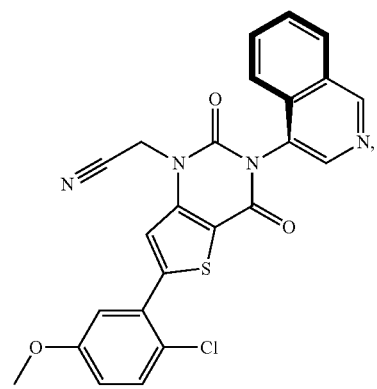
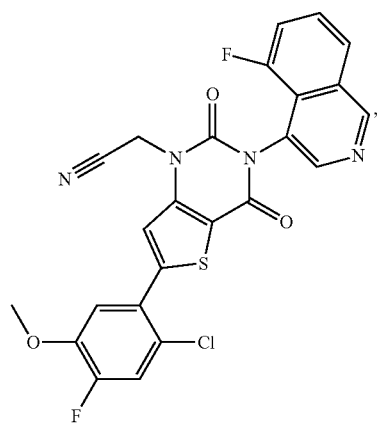
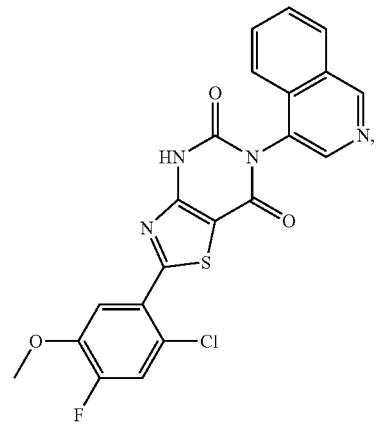
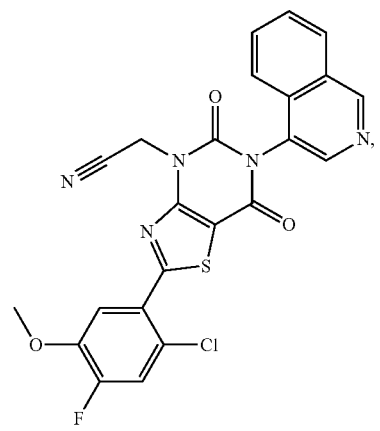
256
-continued
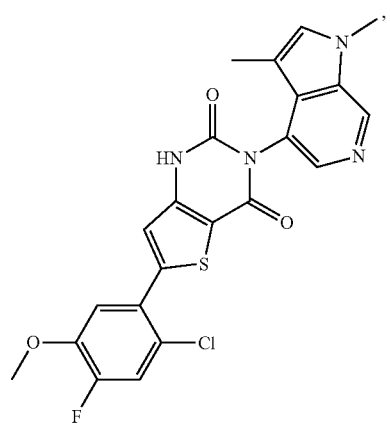
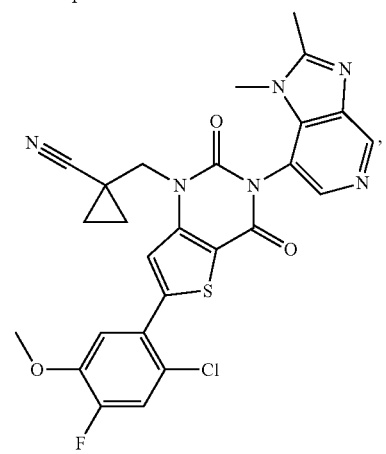
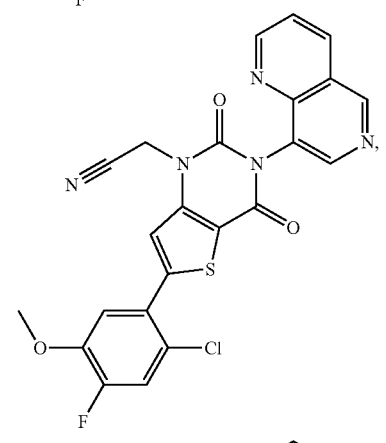
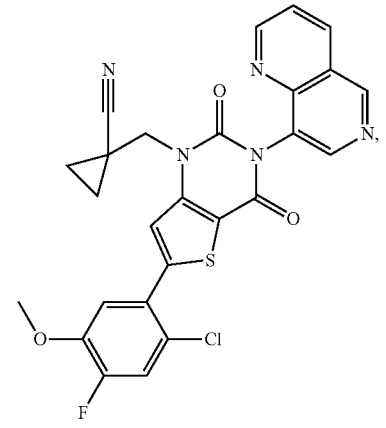

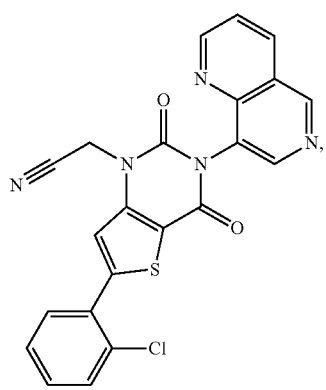
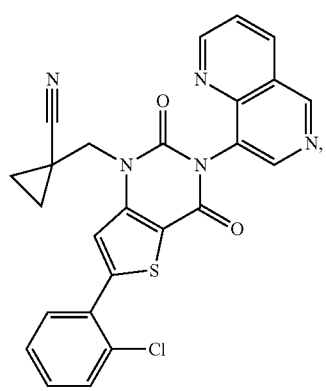
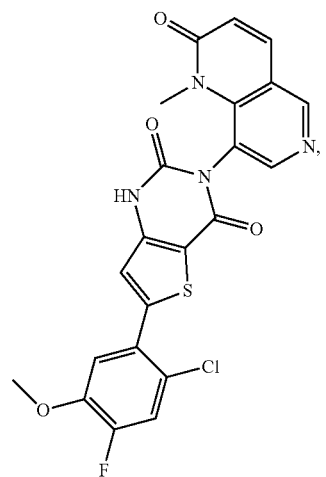
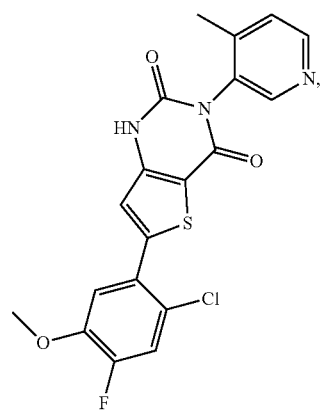
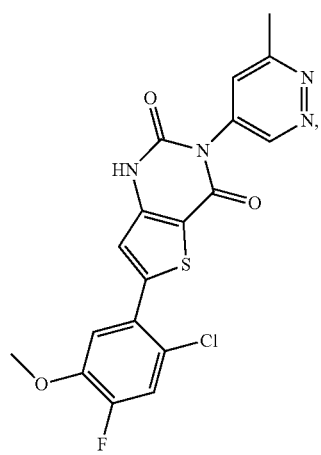
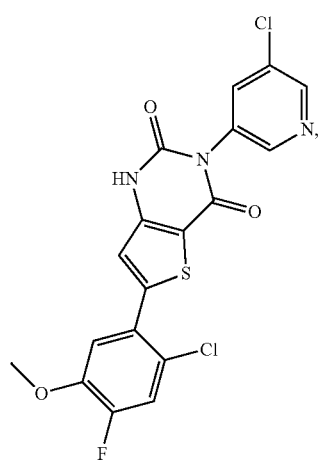
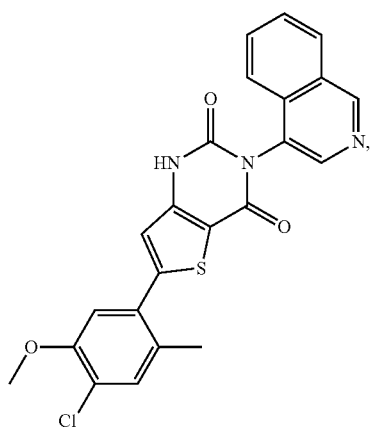

259
-continued
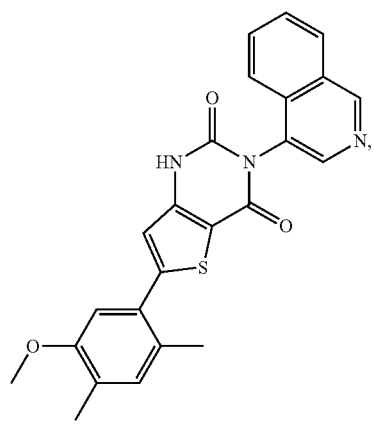
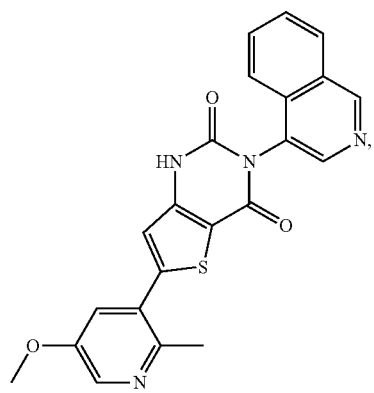
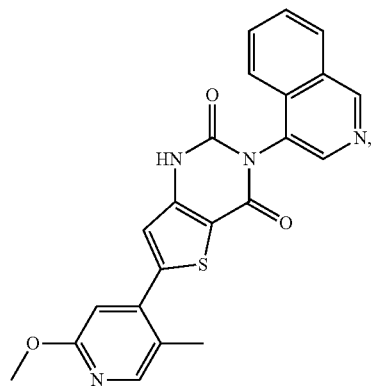
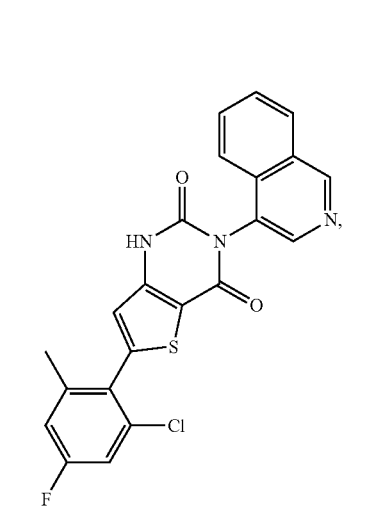
260
-continued
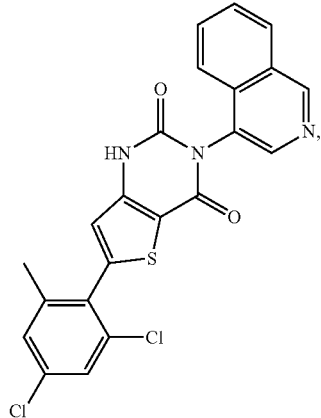
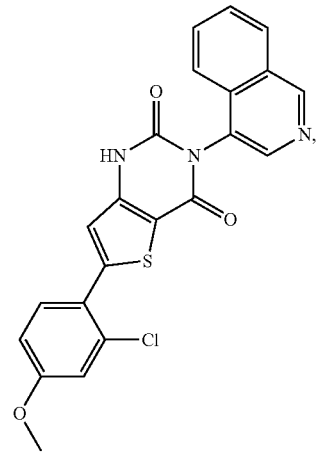
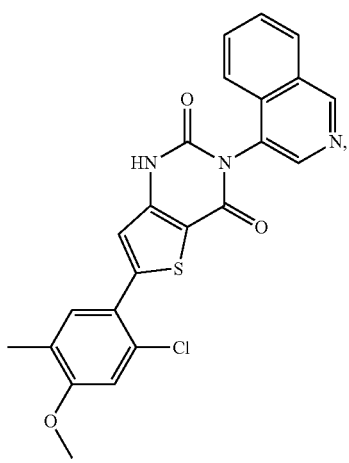

-continued
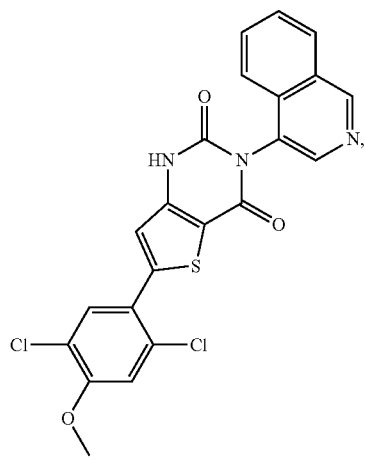
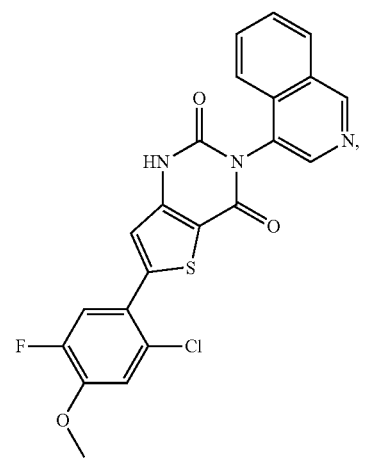
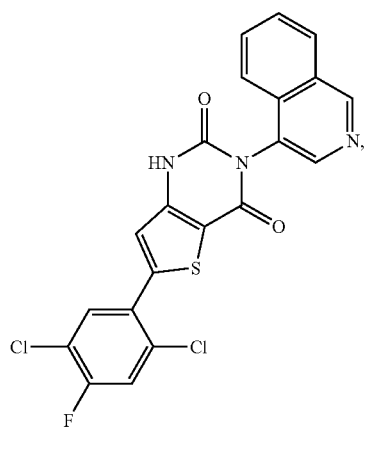
-continued
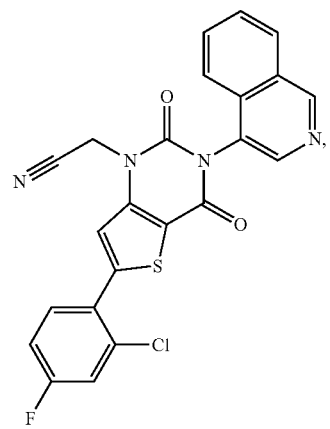
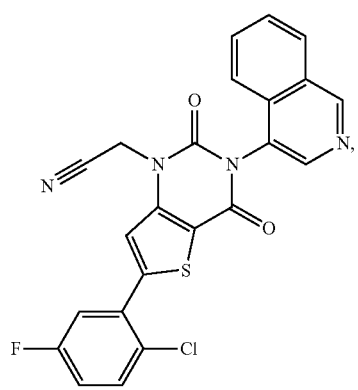
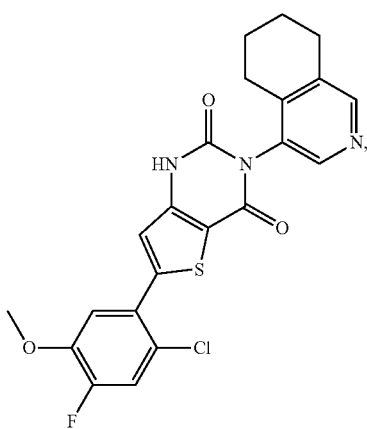
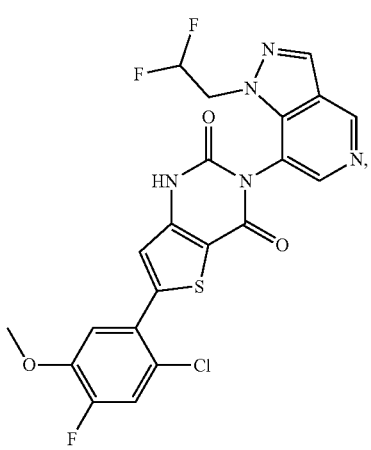

263
-continued
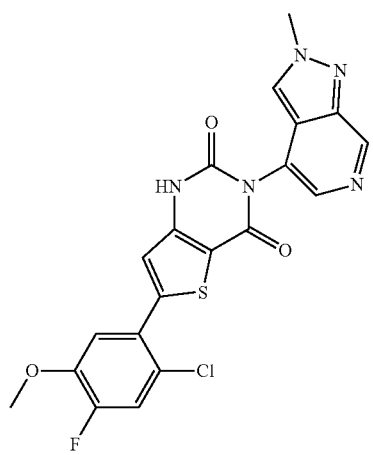
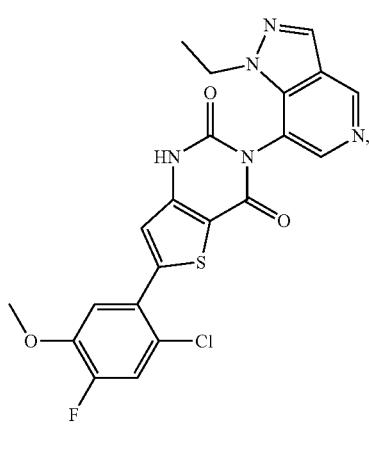
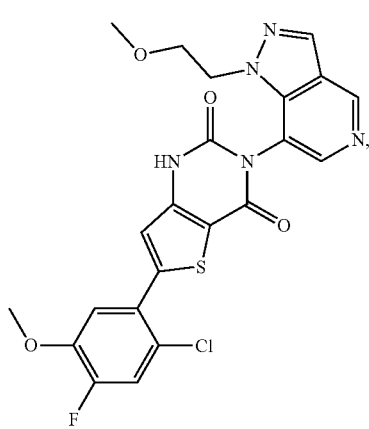
264
-continued
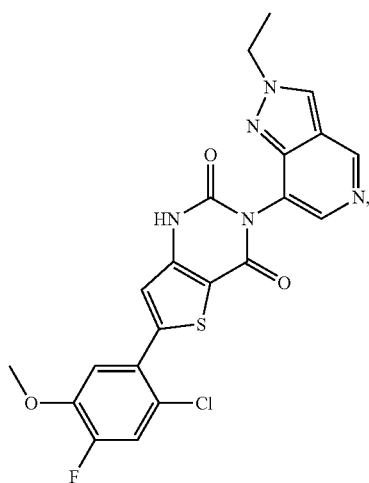
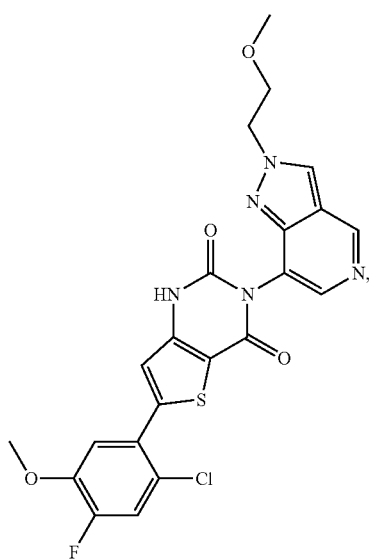
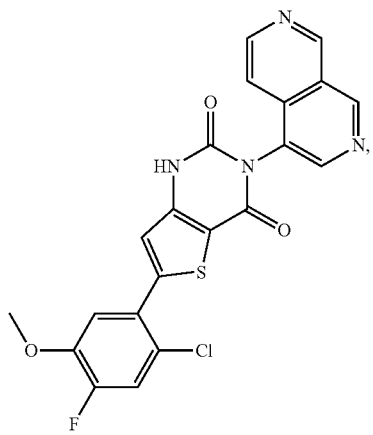

265
-continued
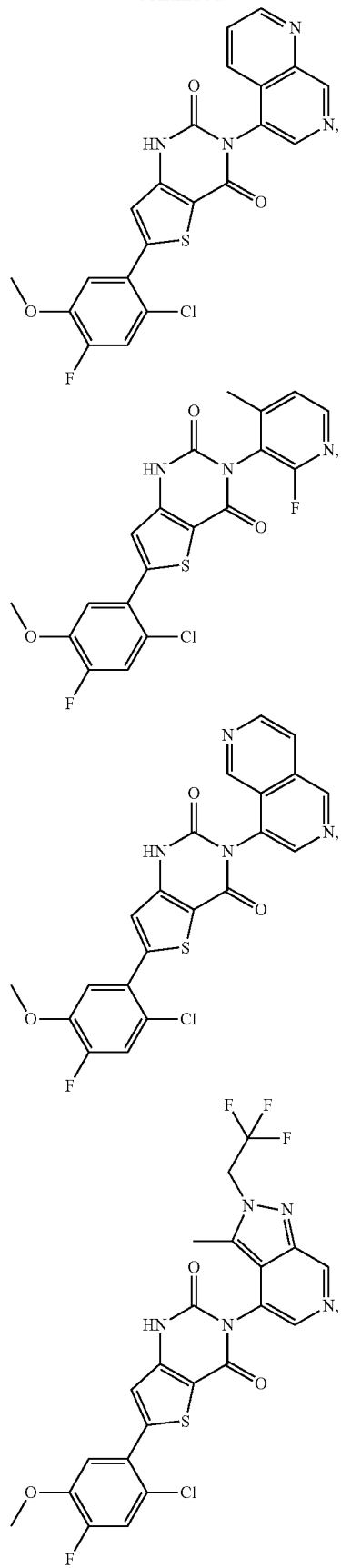
266
-continued
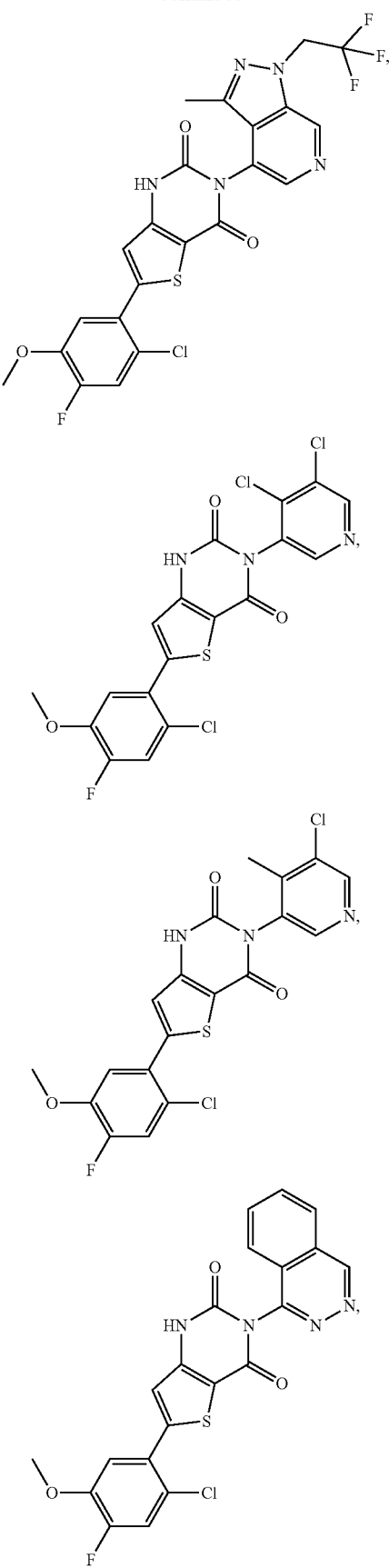

267
-continued
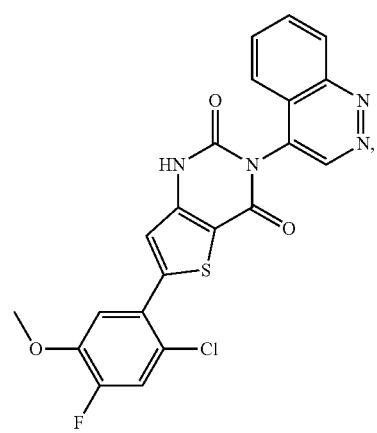
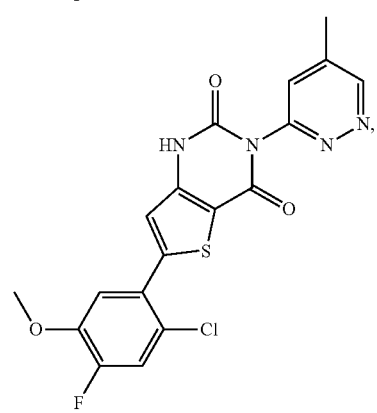

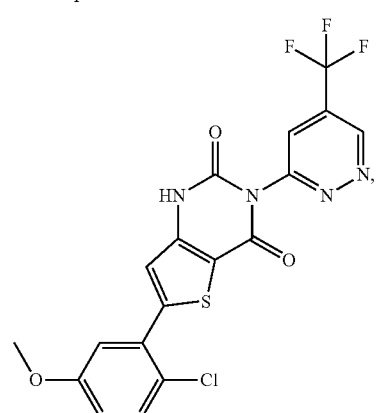
268
-continued
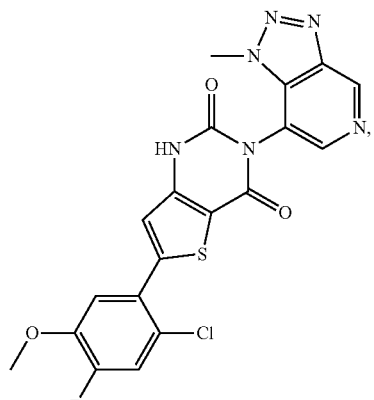
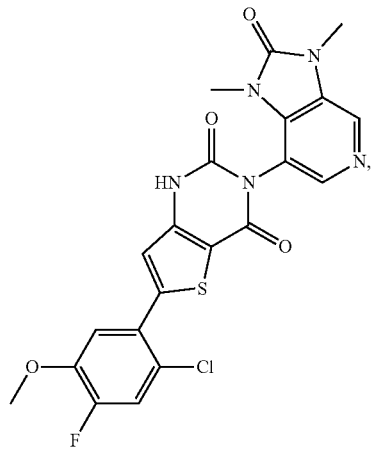
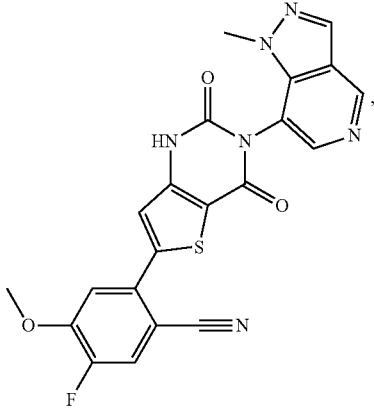
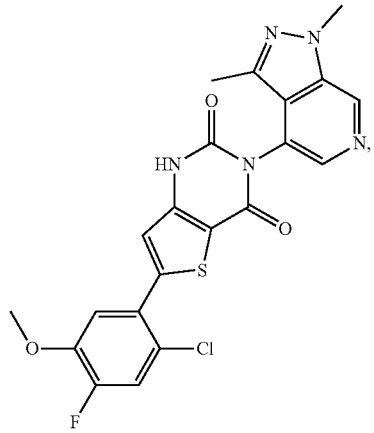

269
-continued
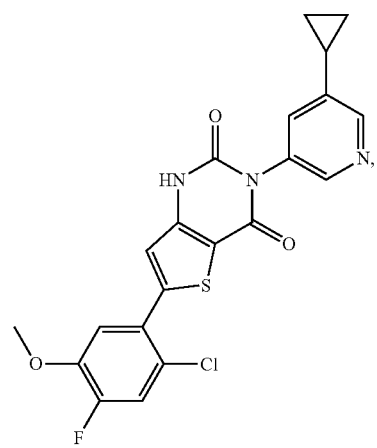
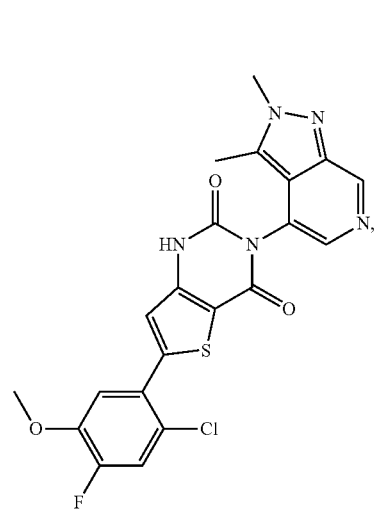
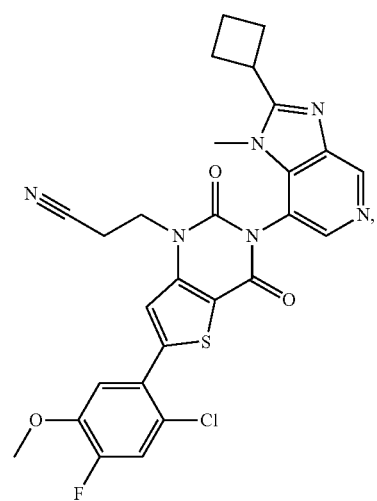
270
-continued
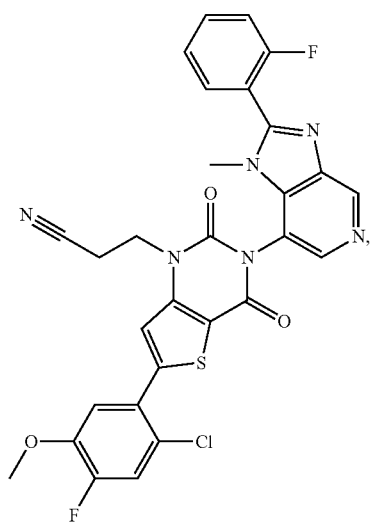
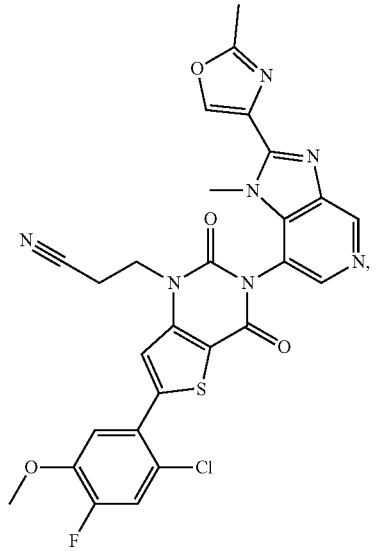
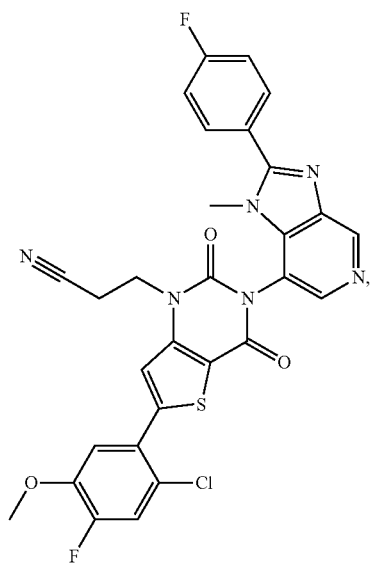

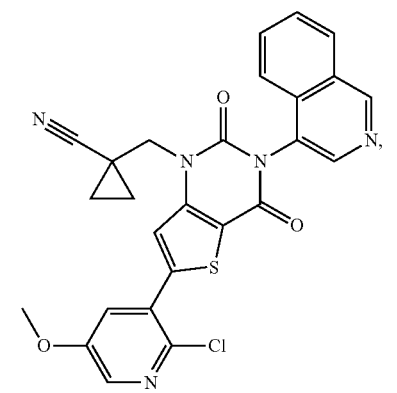
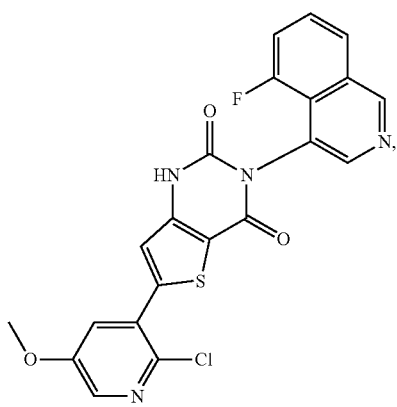
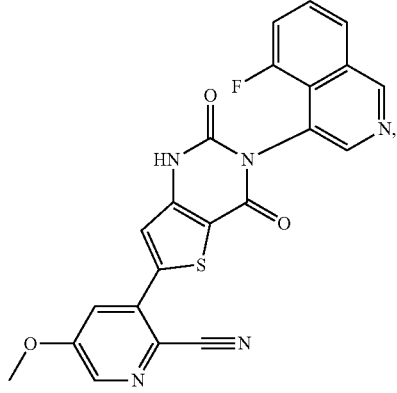
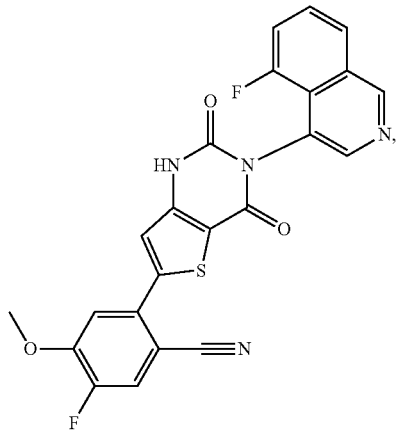
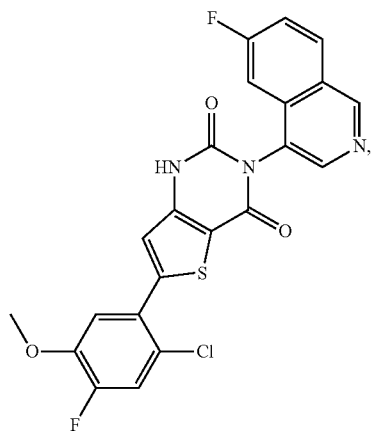
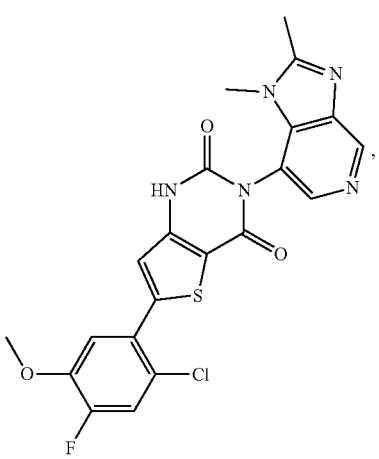
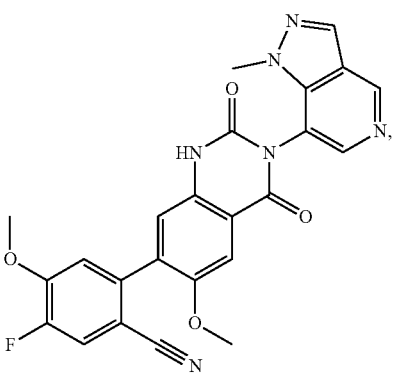
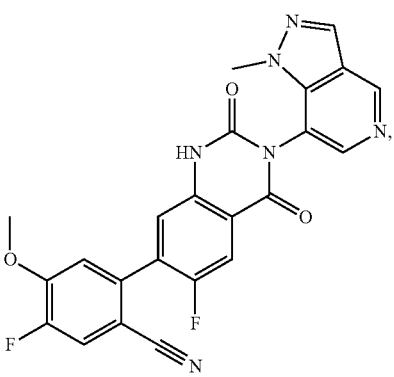

273
-continued
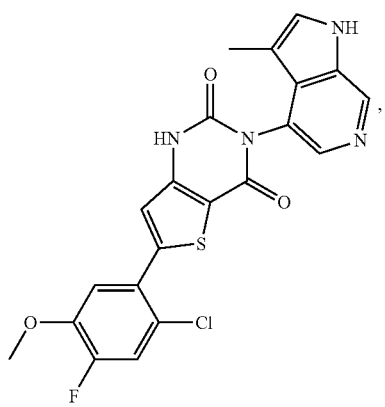
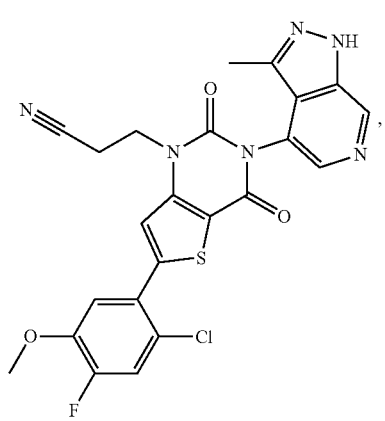

274
-continued
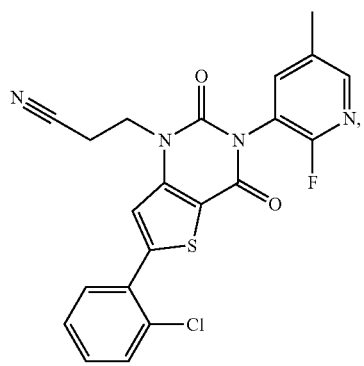
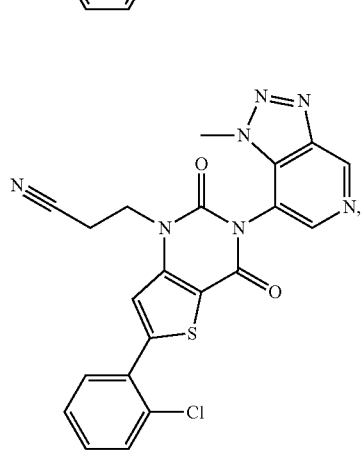
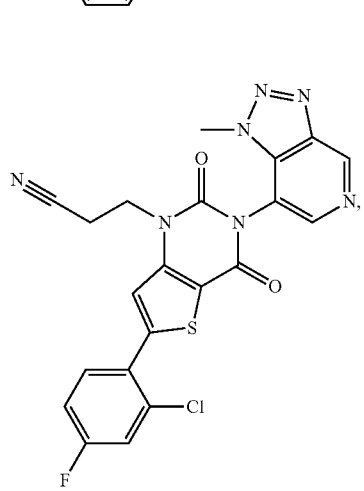
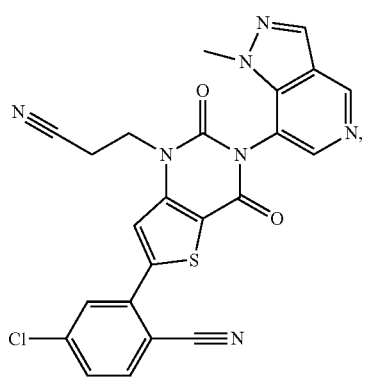

275
-continued
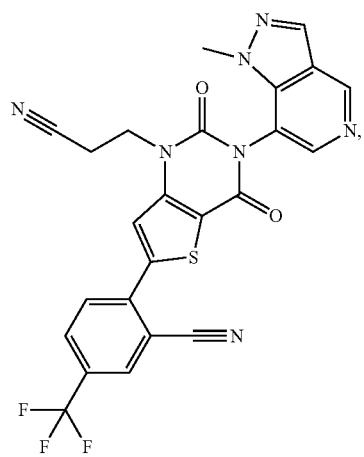
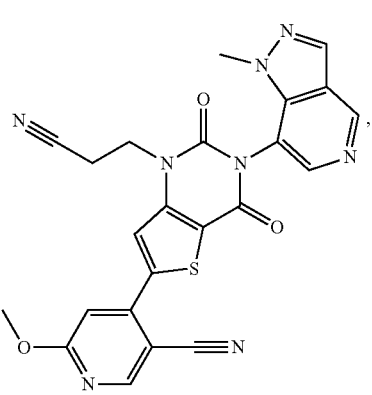
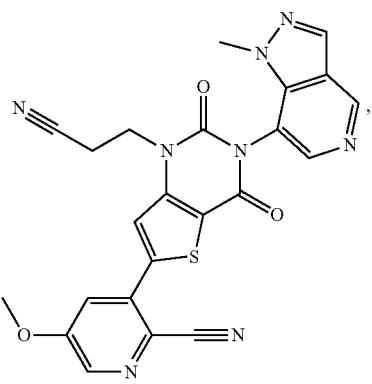
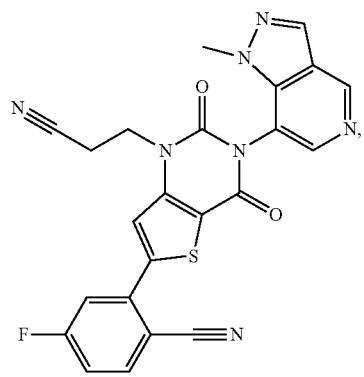
276
-continued
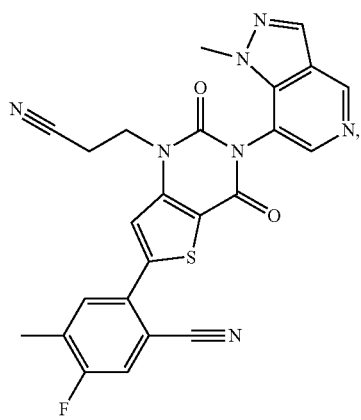
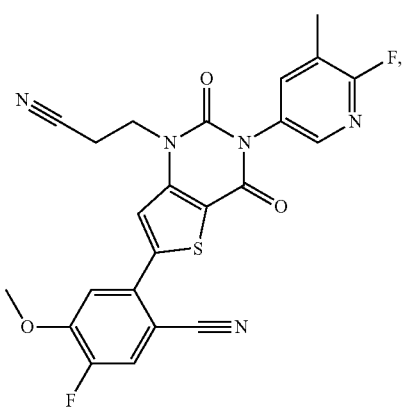
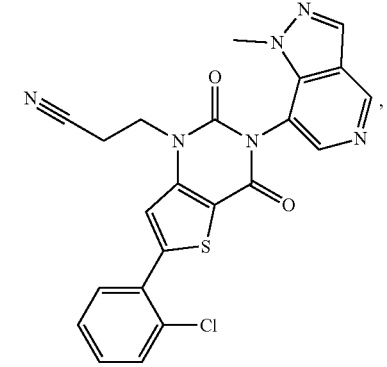
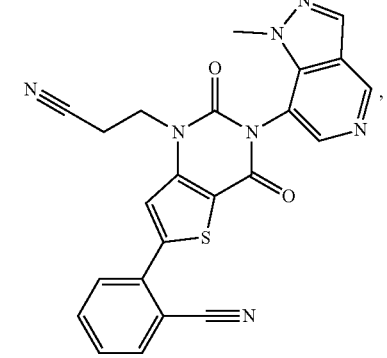

277
-continued
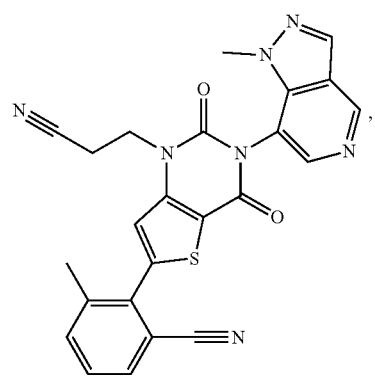
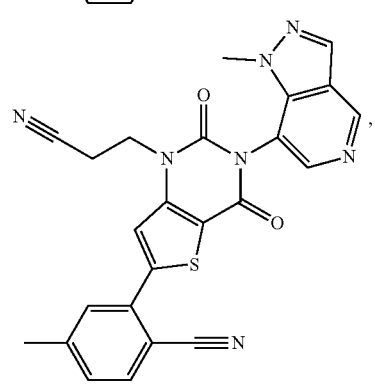
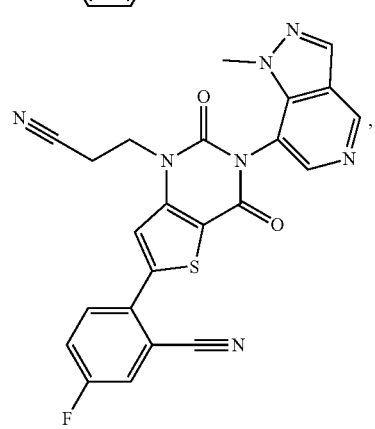
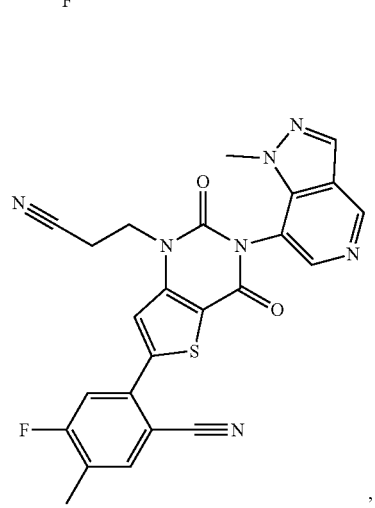
278
-continued
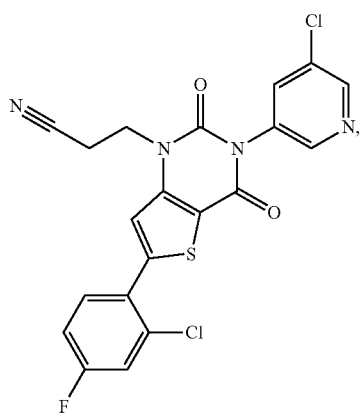
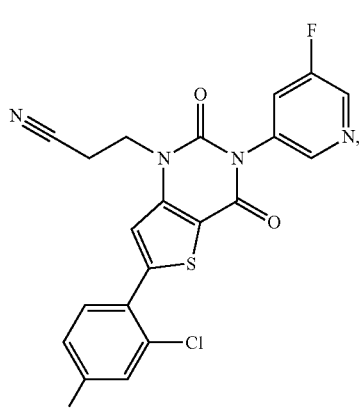
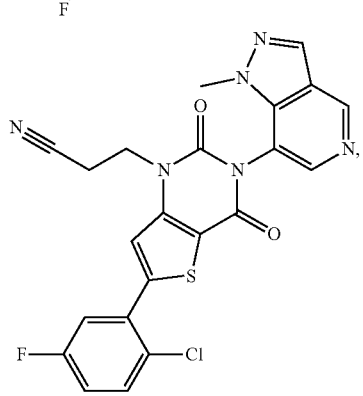
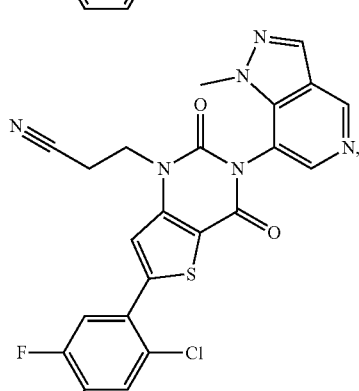

279
-continued
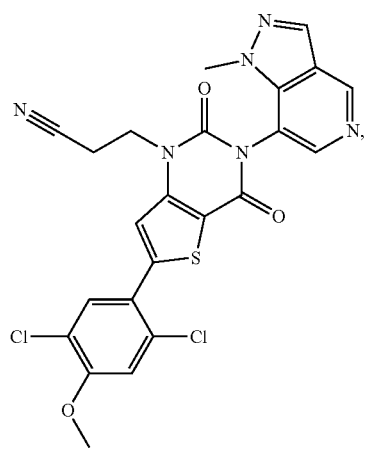
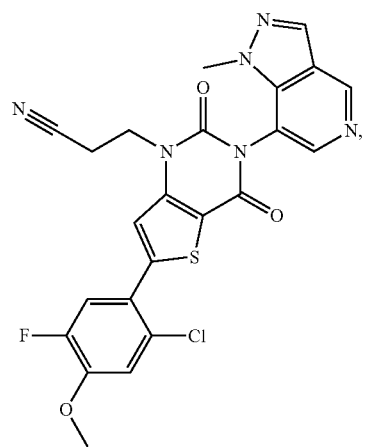
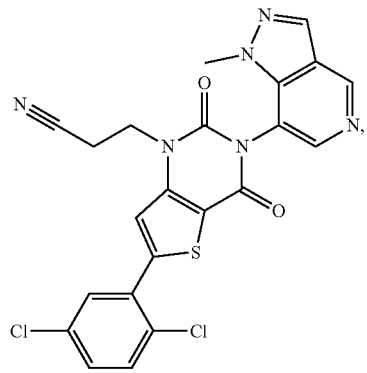
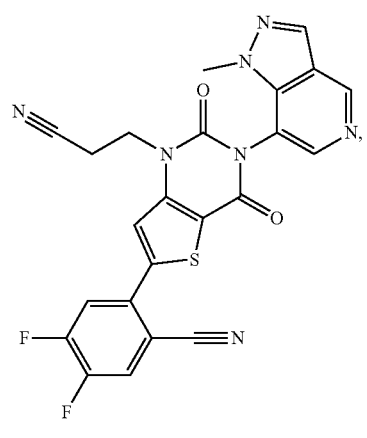
280
-continued
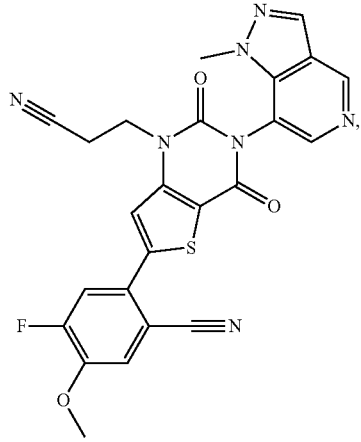
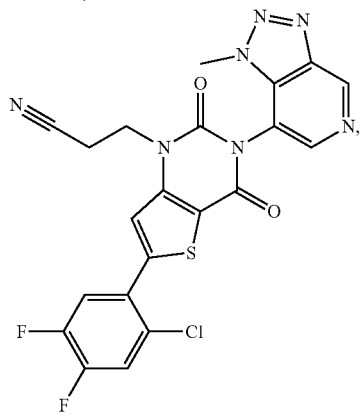
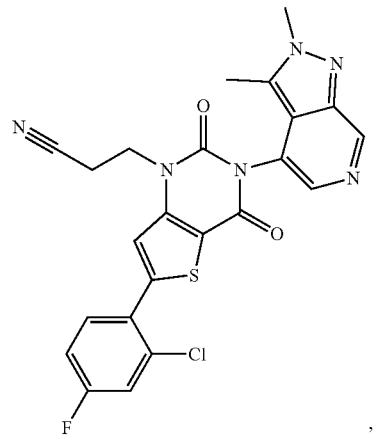
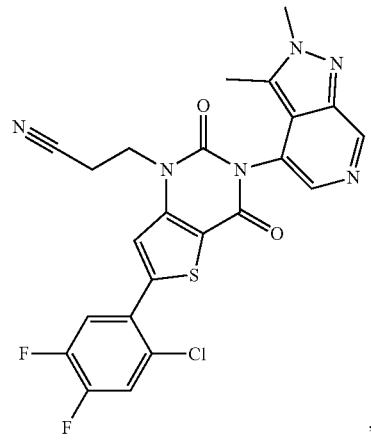

281
-continued
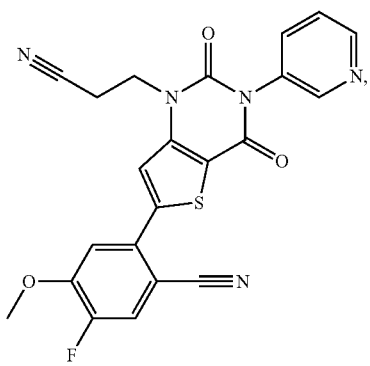
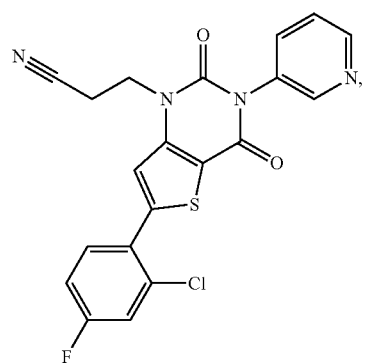
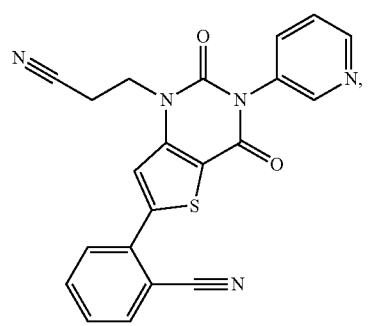
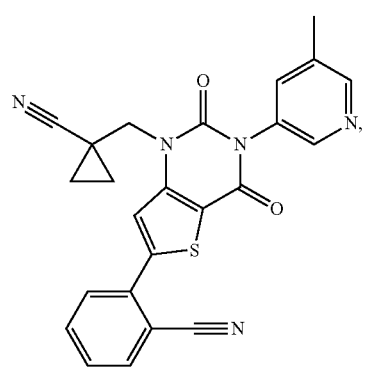
282
-continued
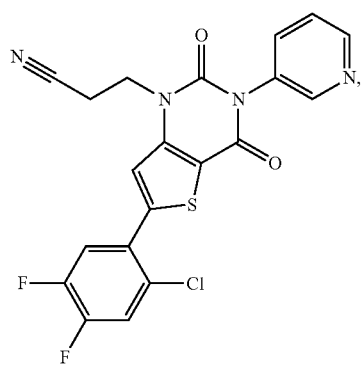
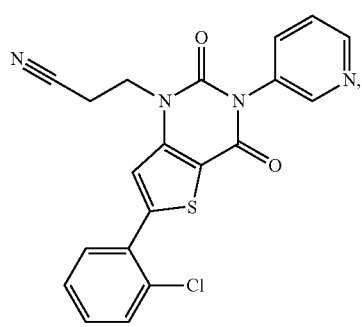
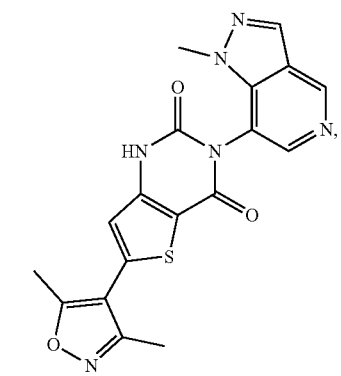
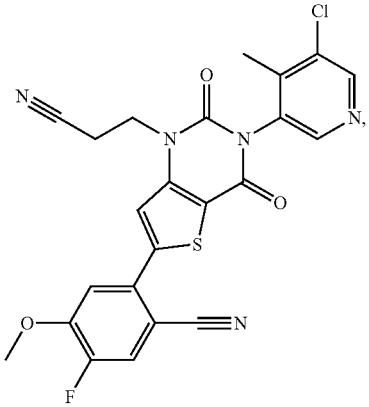

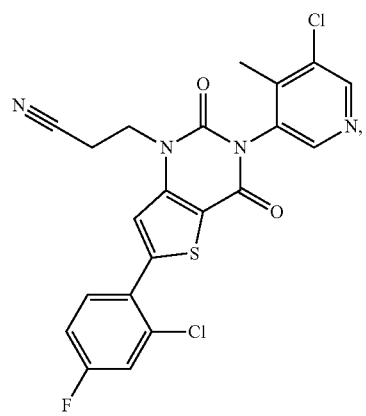
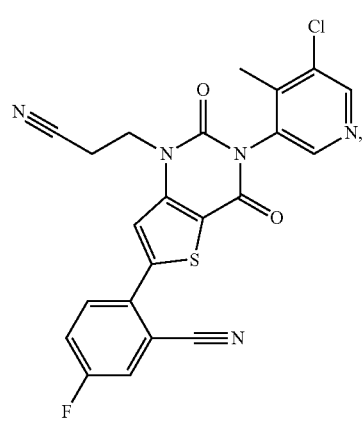
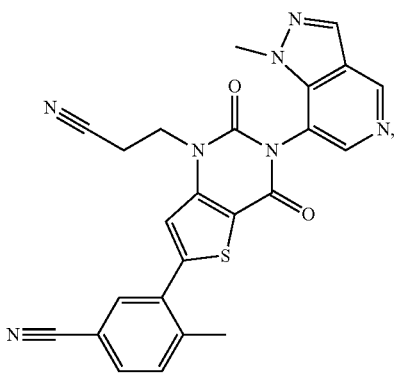
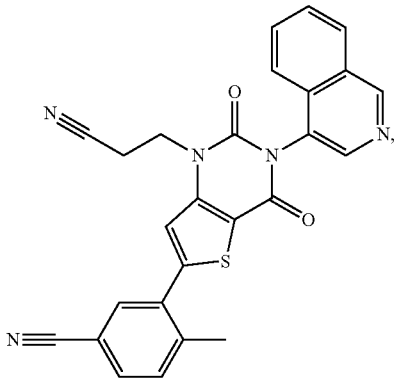
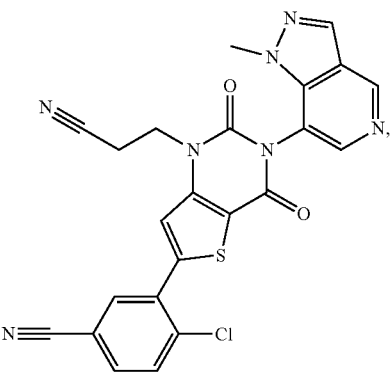
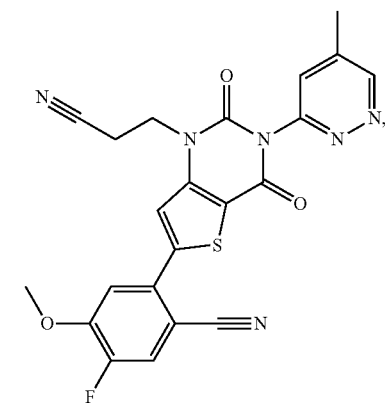
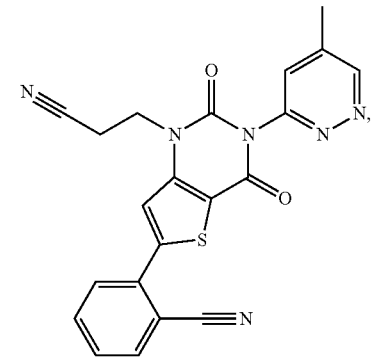
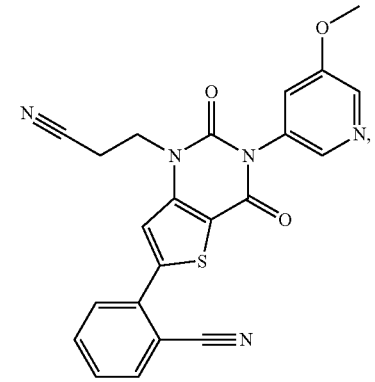

-continued
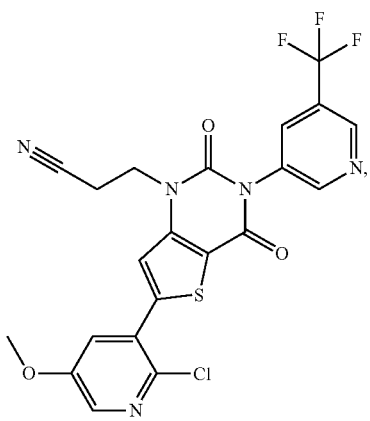
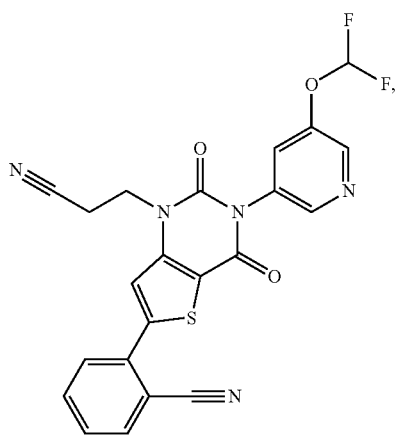
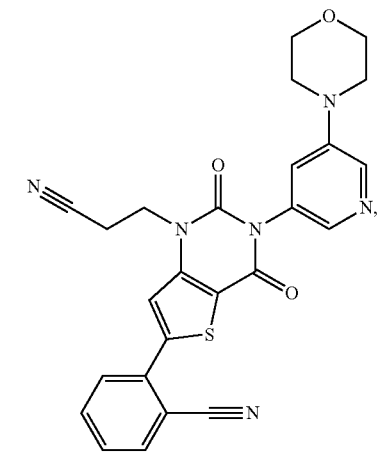
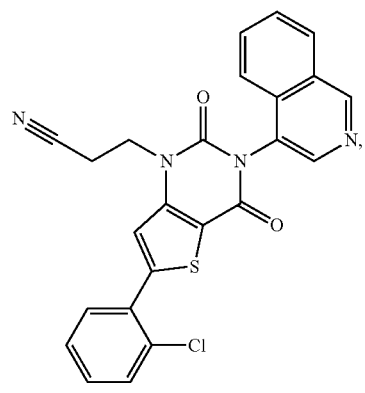
-continued
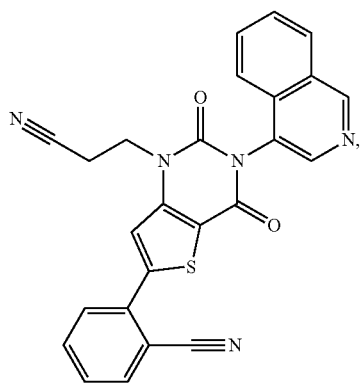
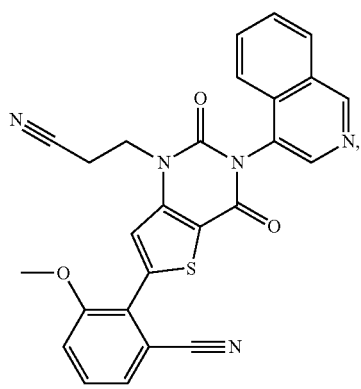
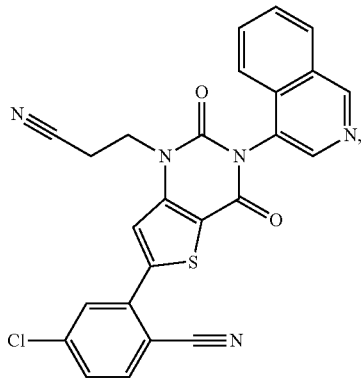
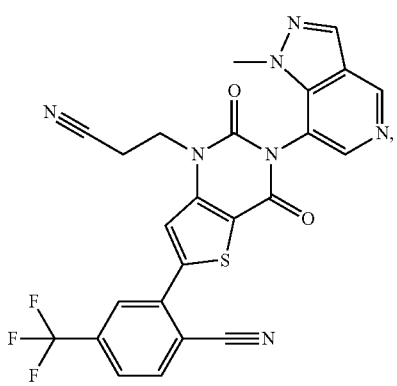

287
-continued
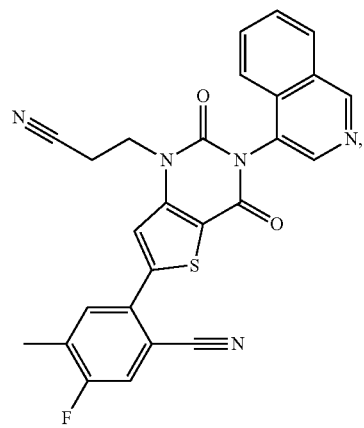
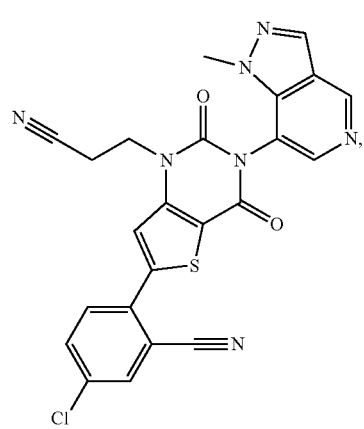
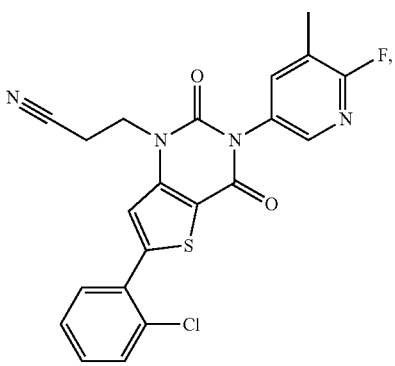
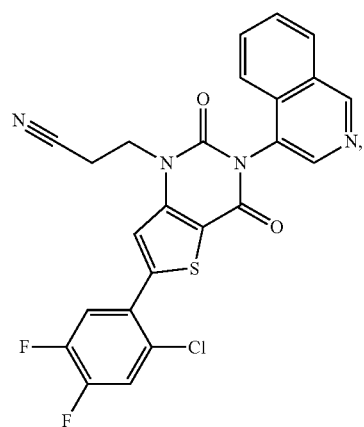
288
-continued
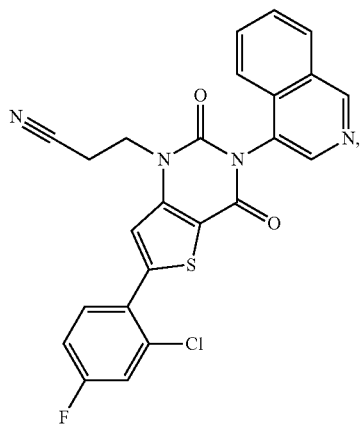
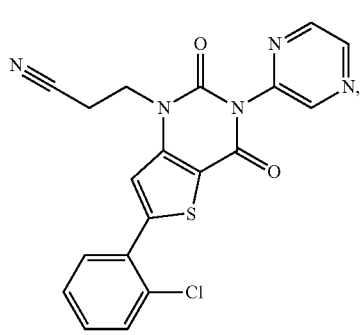
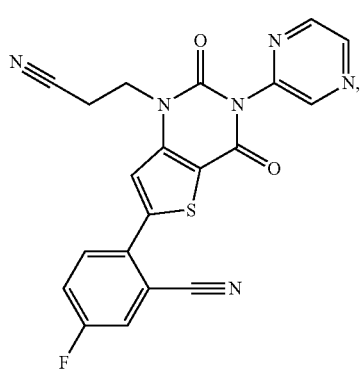
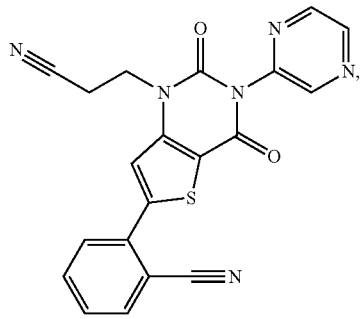

-continued
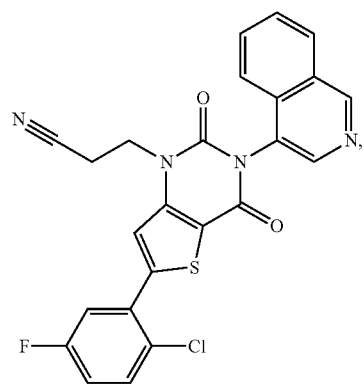
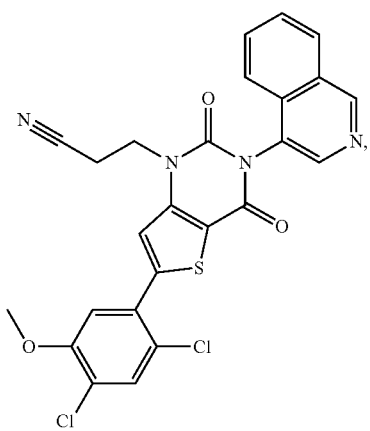
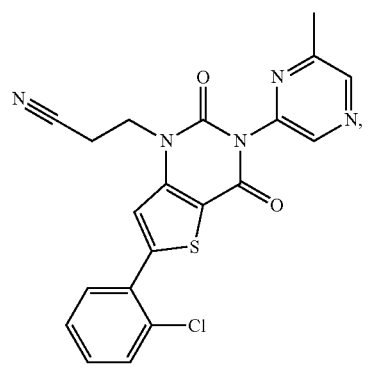
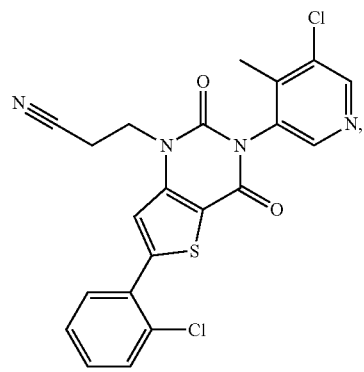
-continued
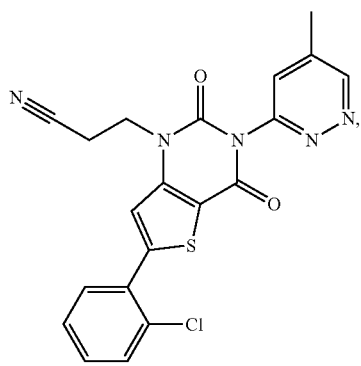
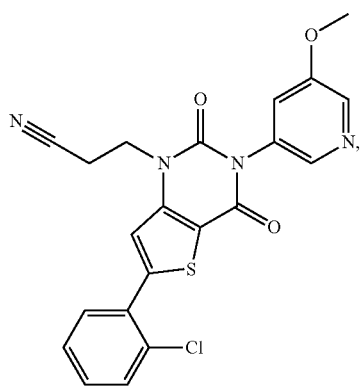
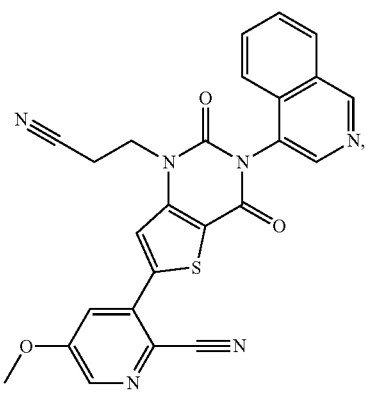
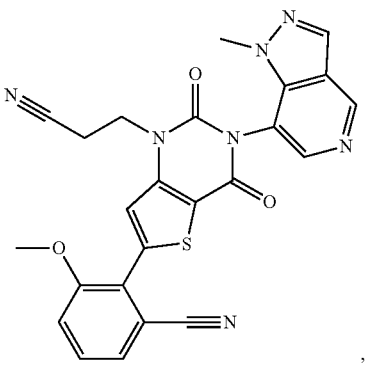

291
-continued
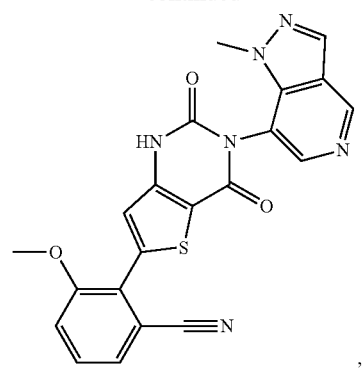
,
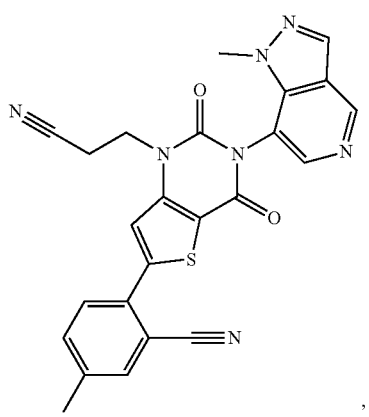
,
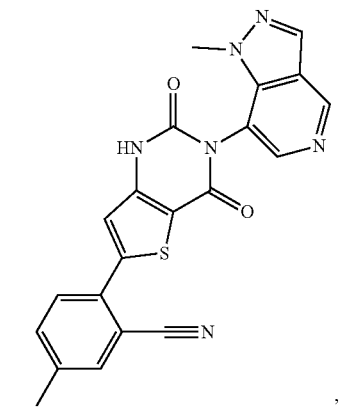
,
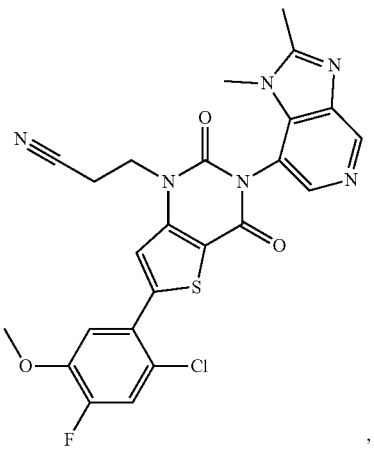
,
292
-continued
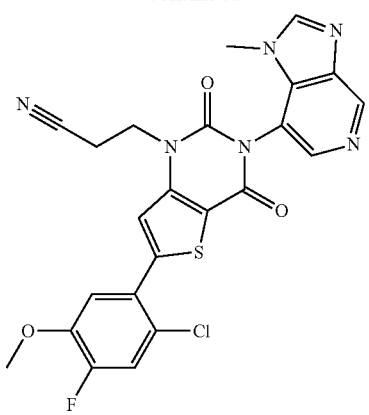
,
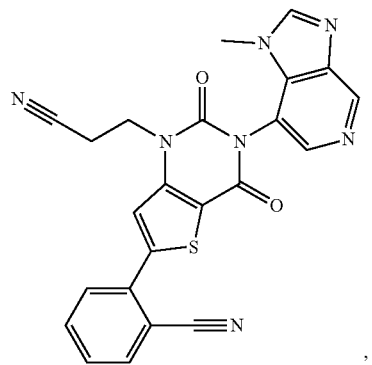
,
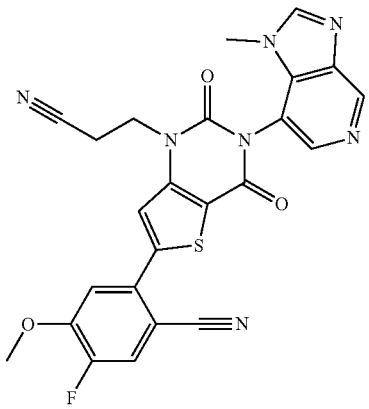
,
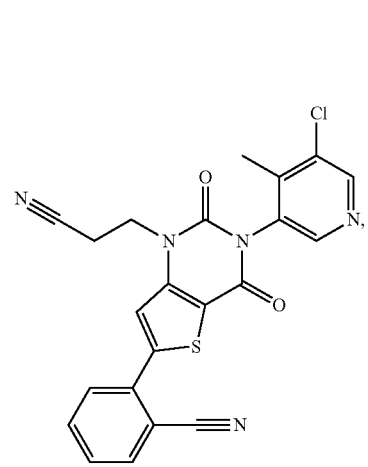
,

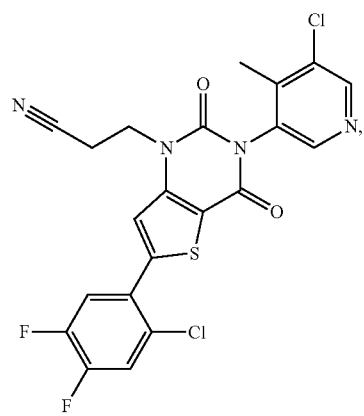
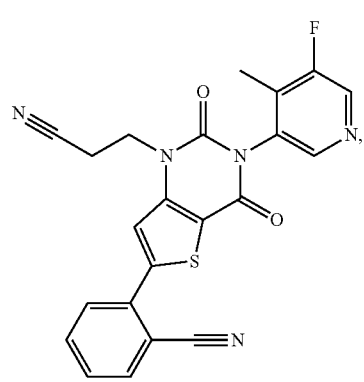
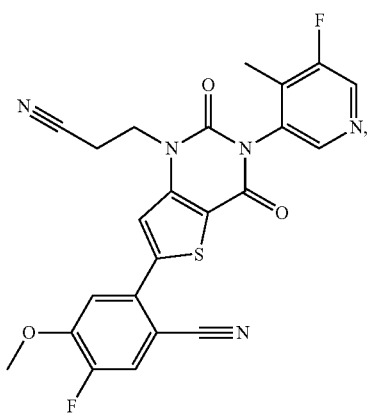
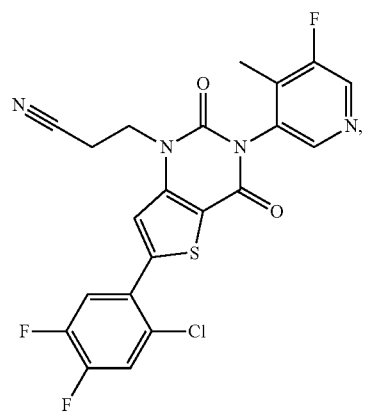
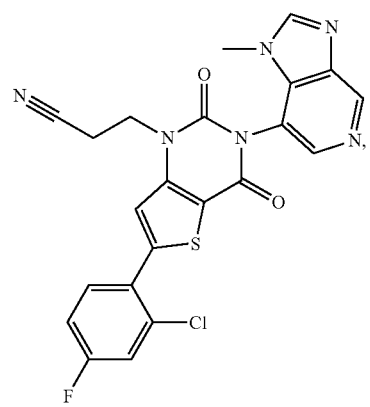
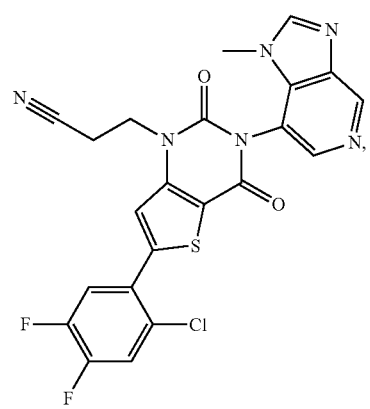
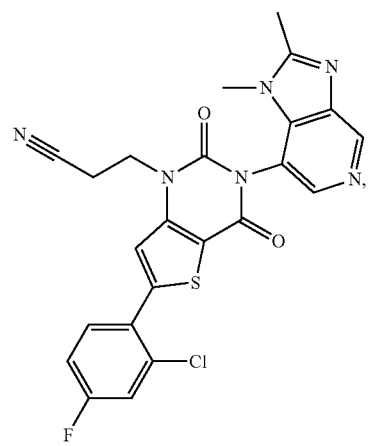
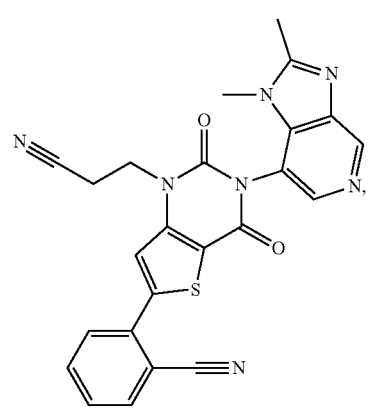

295
-continued
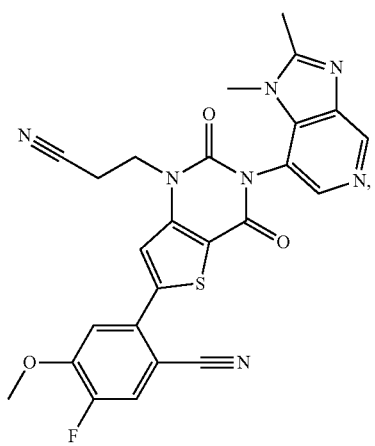
296
-continued
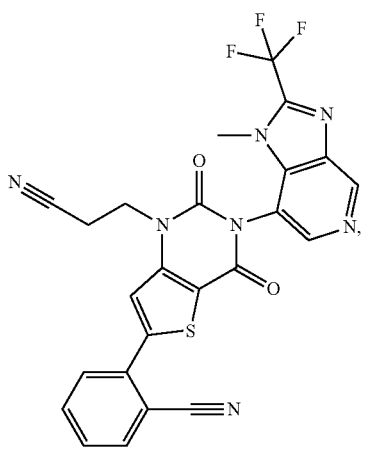
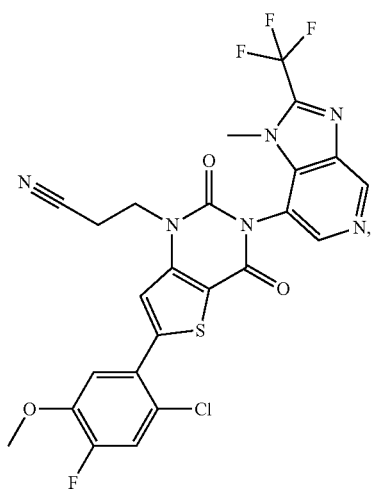
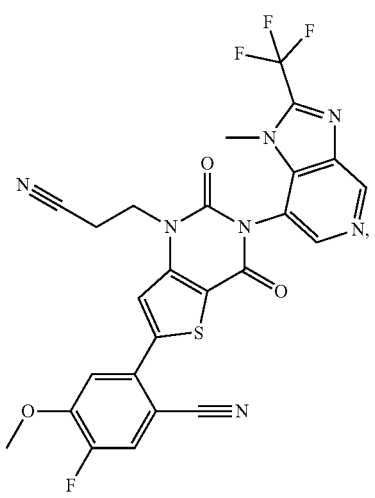
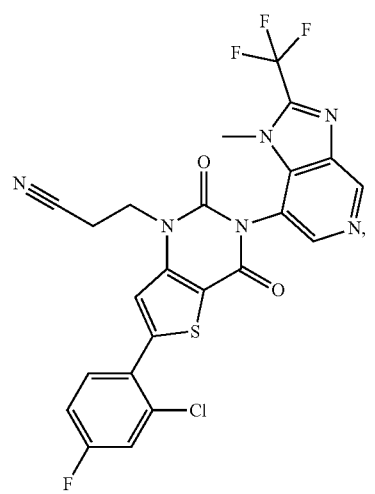
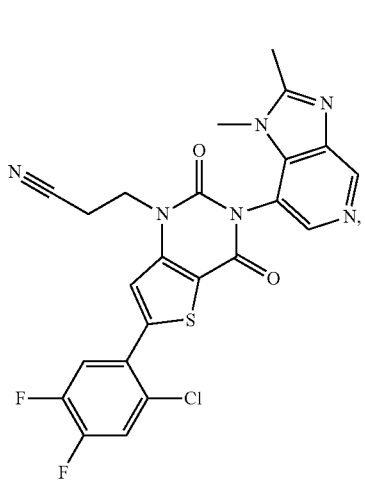

297
-continued
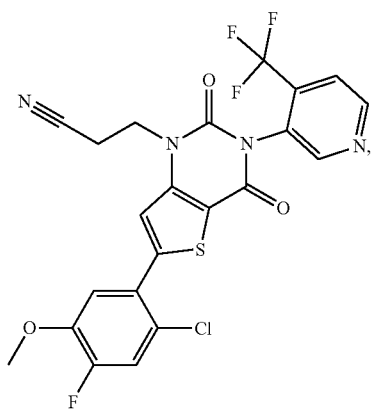
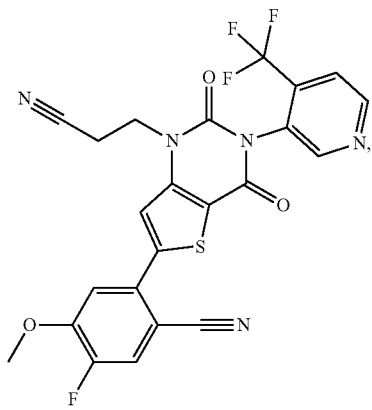
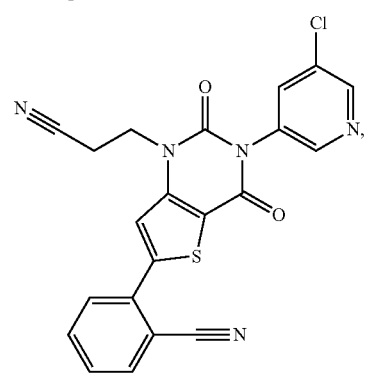
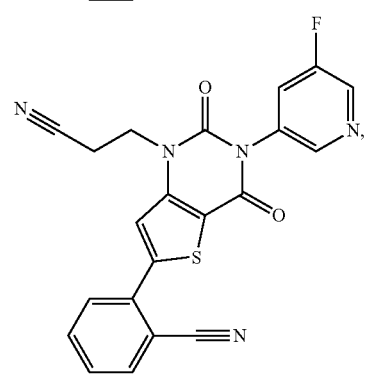
298
-continued
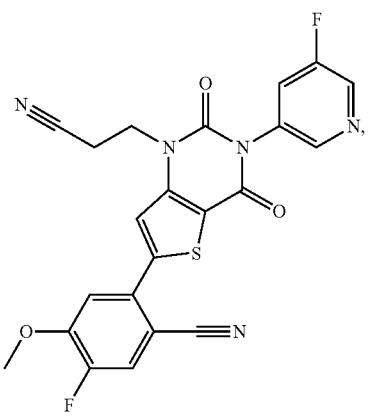
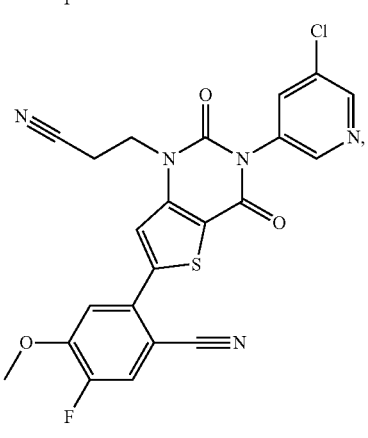
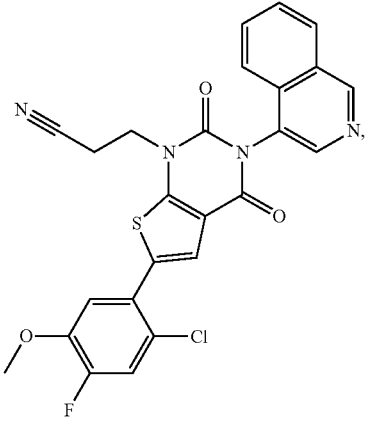
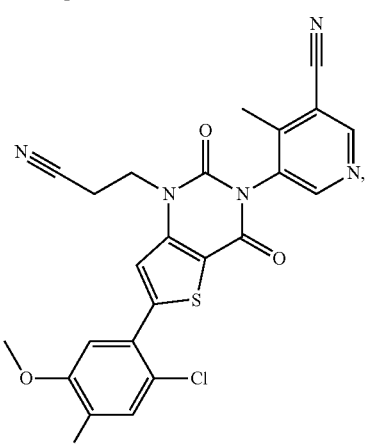

299
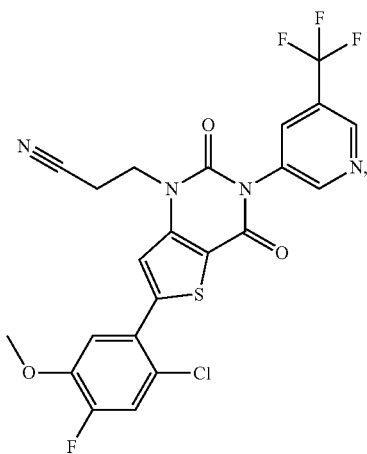
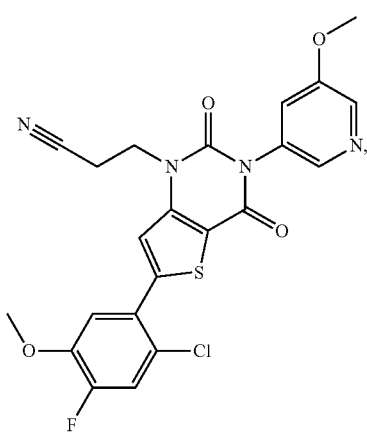
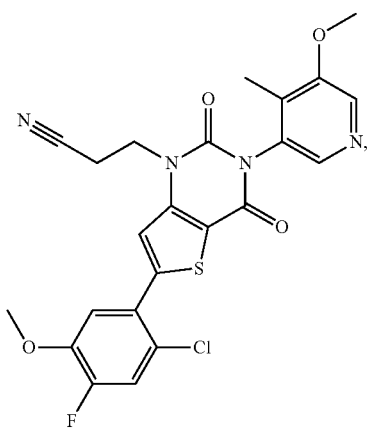
300
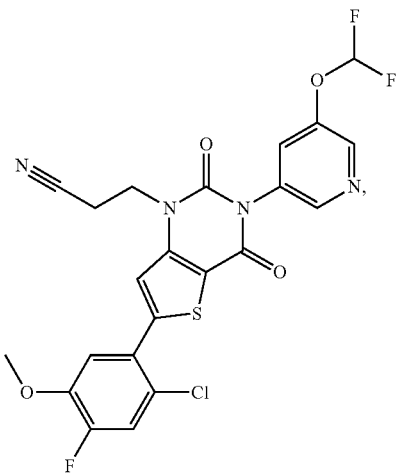
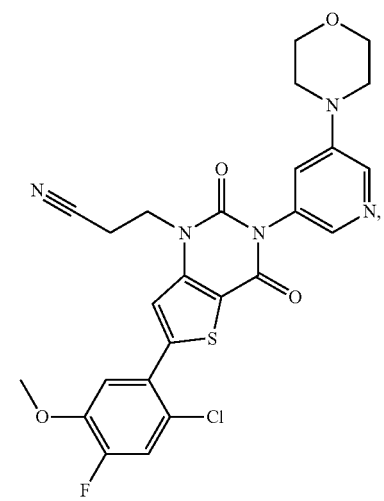
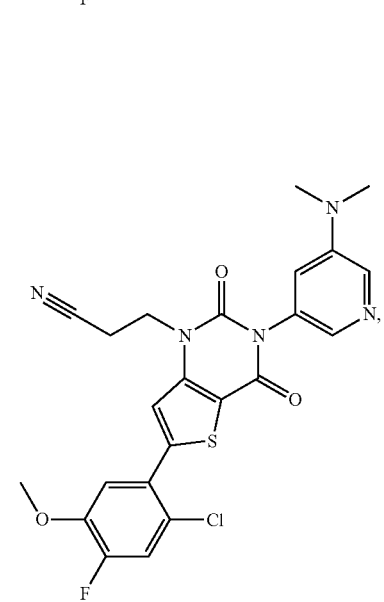

301
-continued
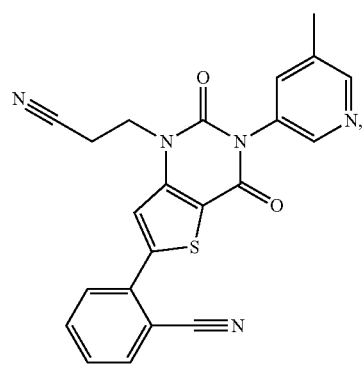
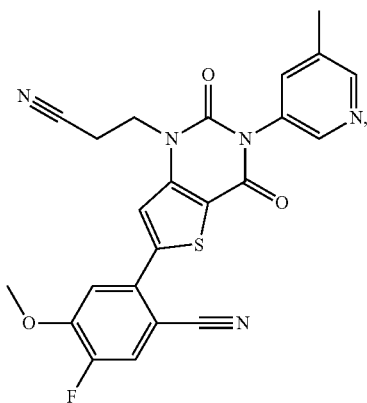
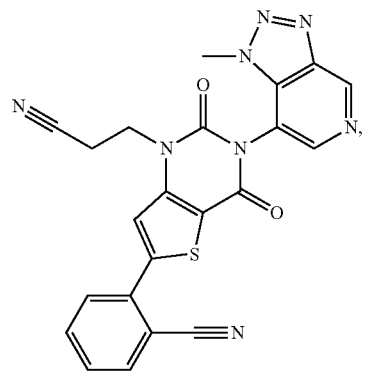
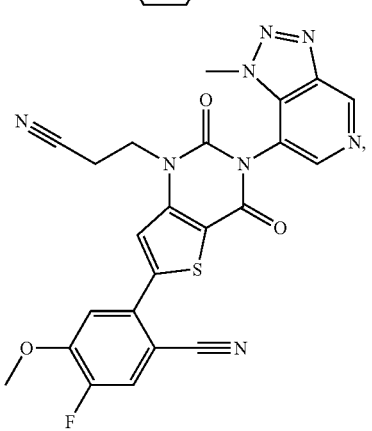
302
-continued
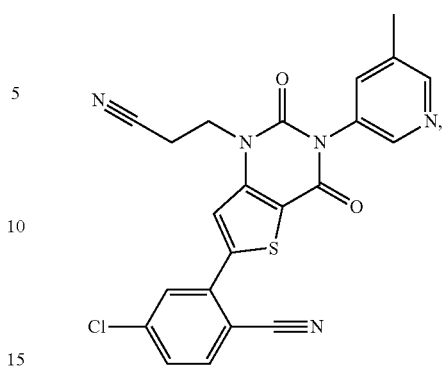
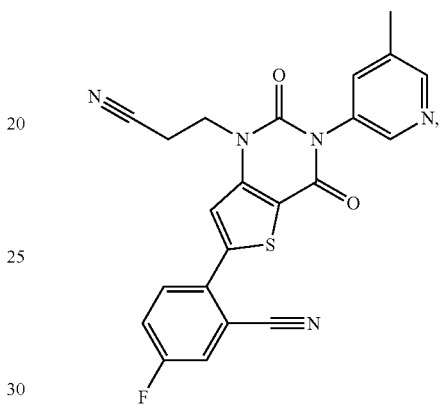
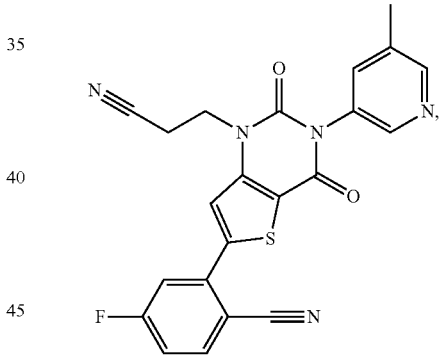
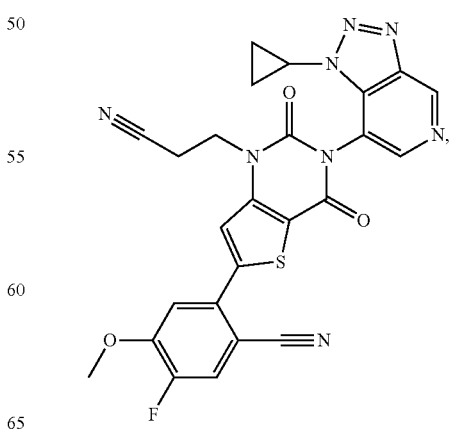

303
-continued
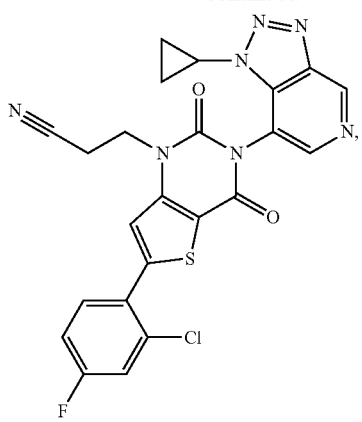
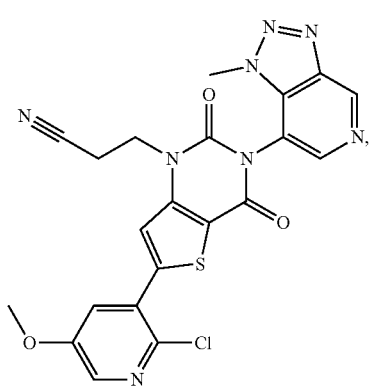
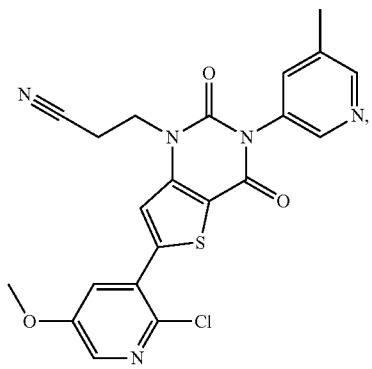
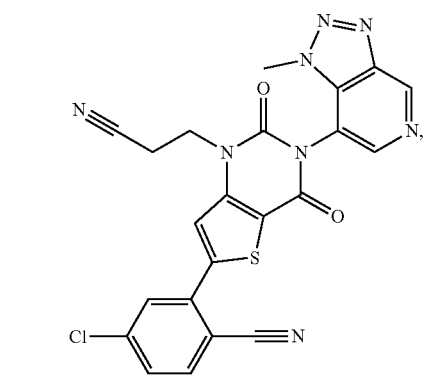
304
-continued
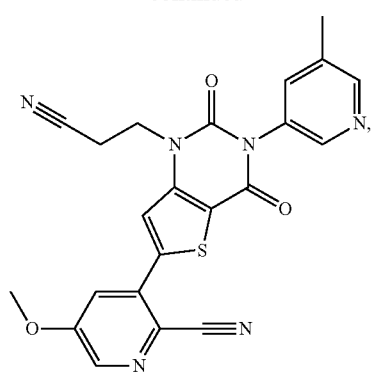
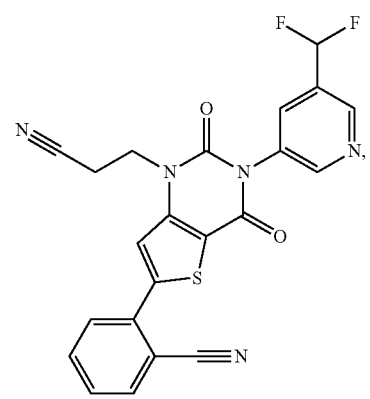
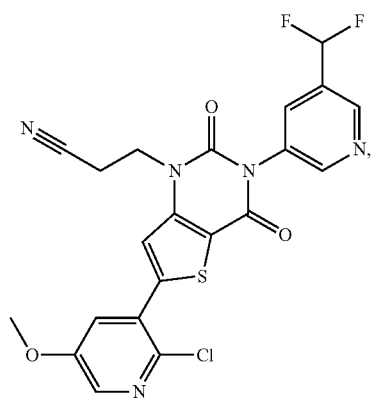
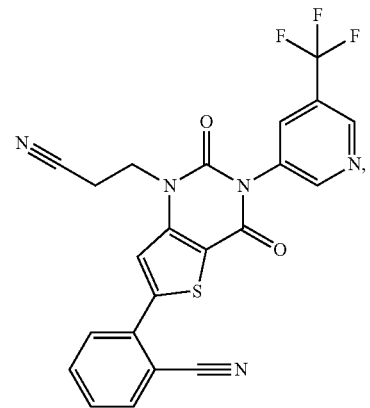

305
-continued
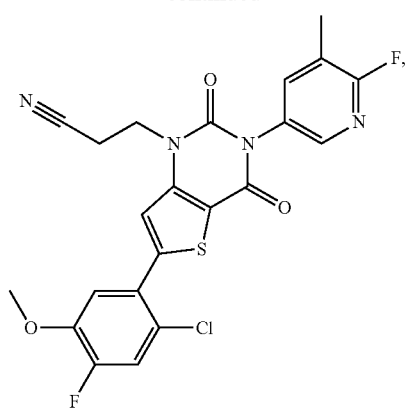
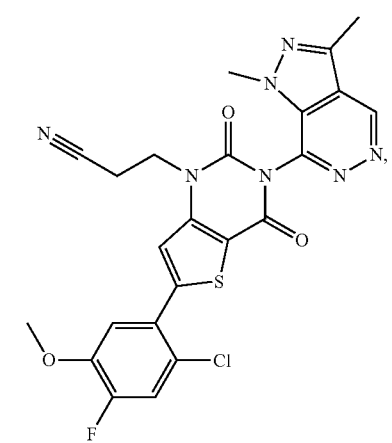
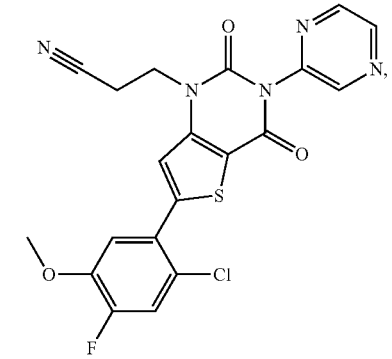
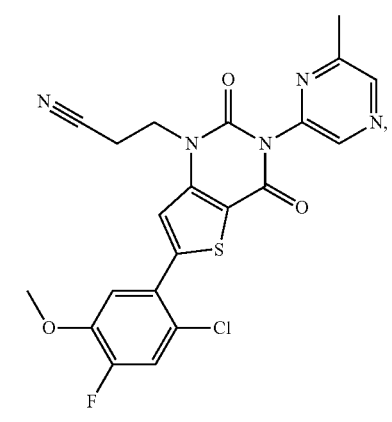
306
-continued
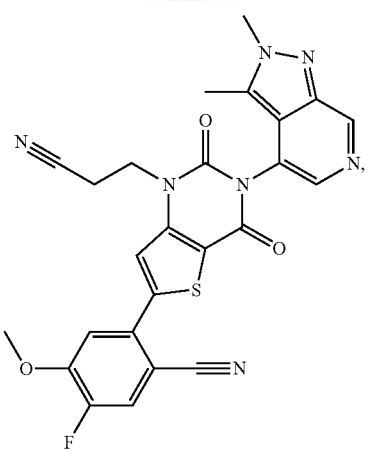
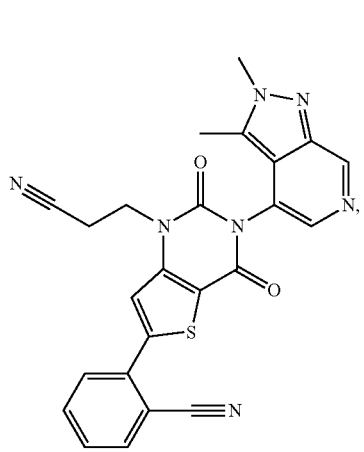
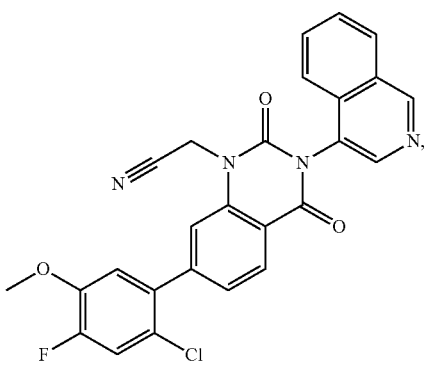
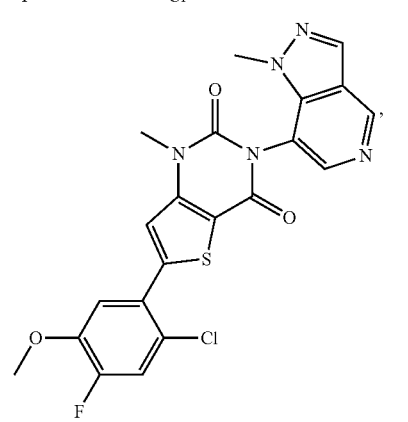

307
-continued
308
-continued
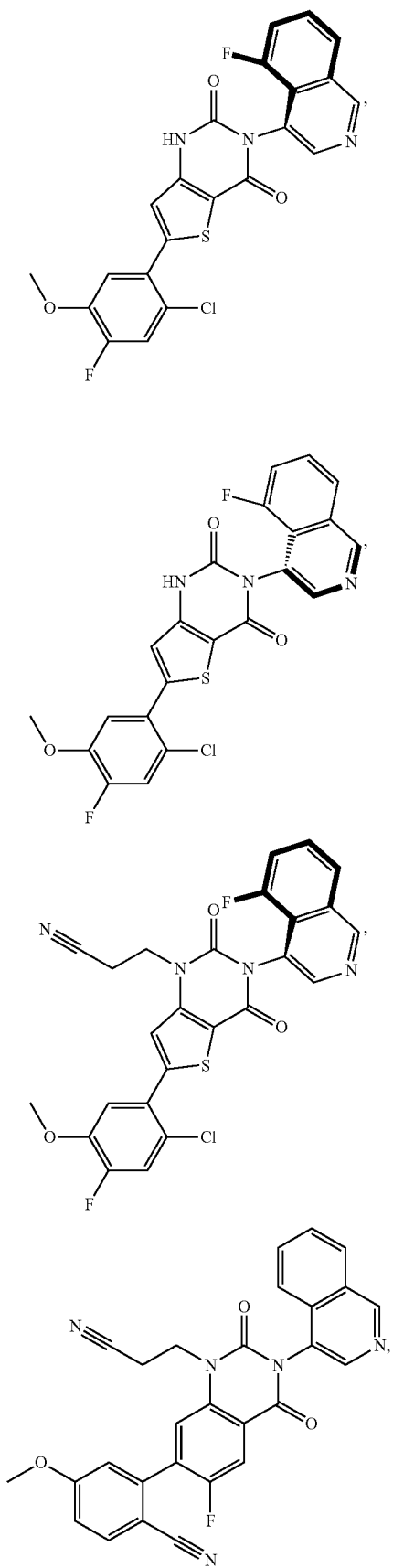
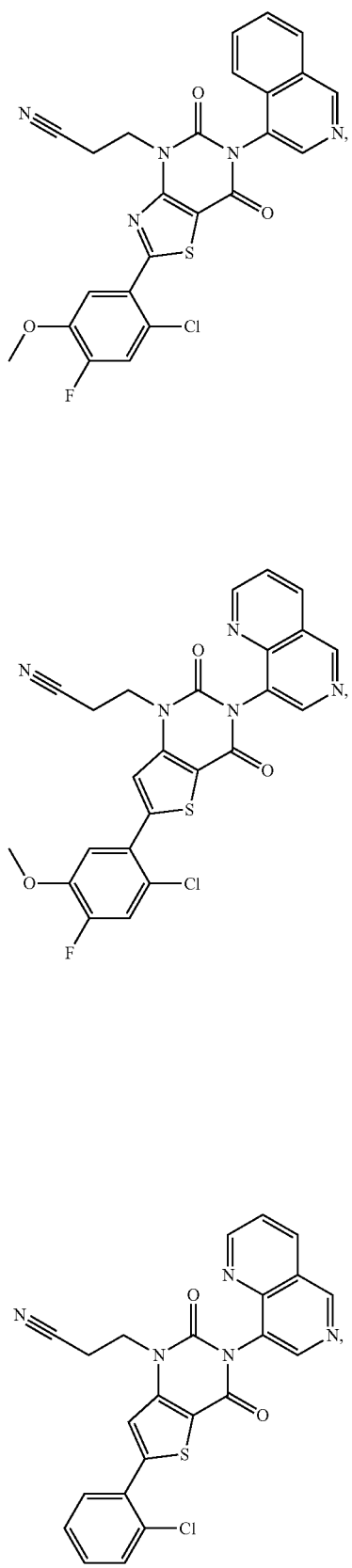

| 309 -continued | 310 -continued |
|---|---|
| 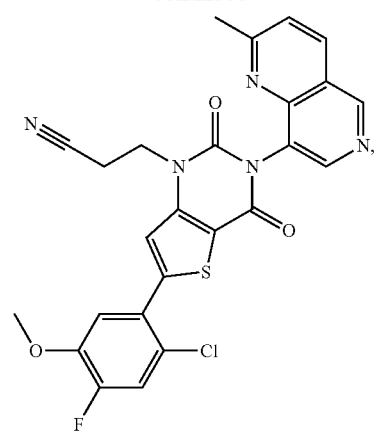 | 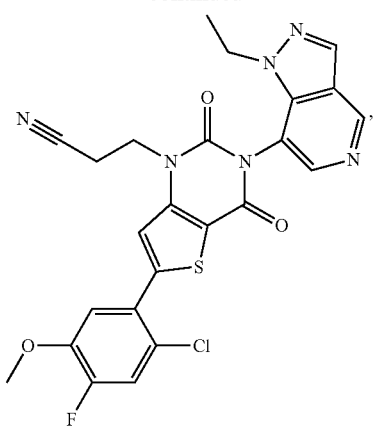 |
| 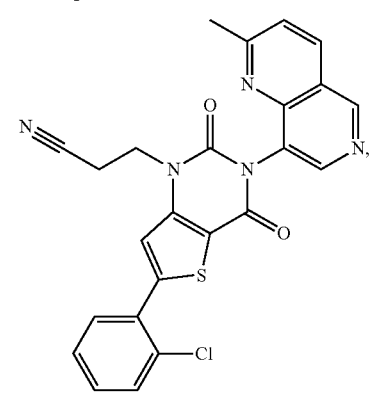 | |
| 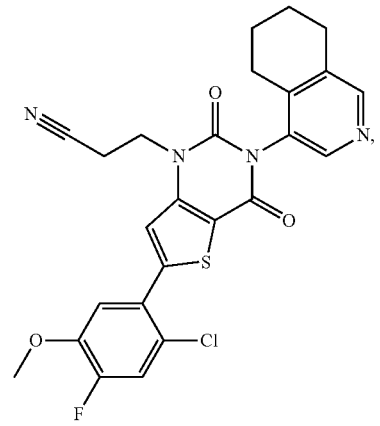 | |

311
-continued
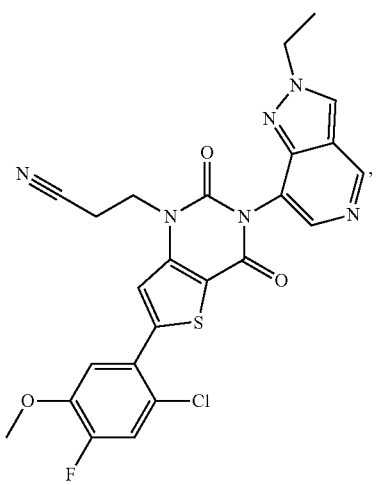
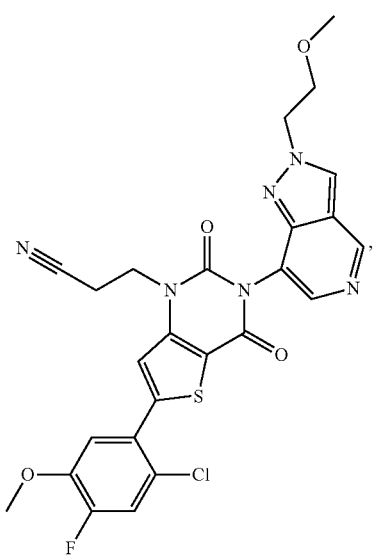
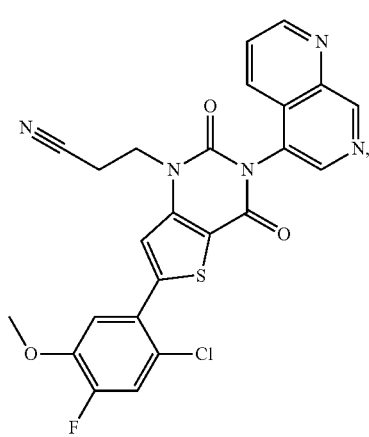
312
-continued
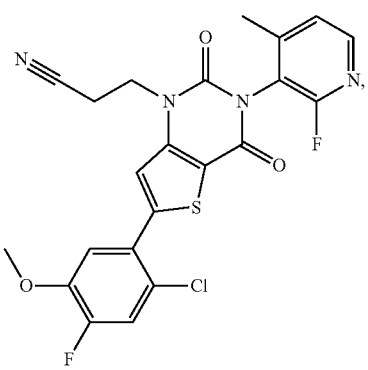
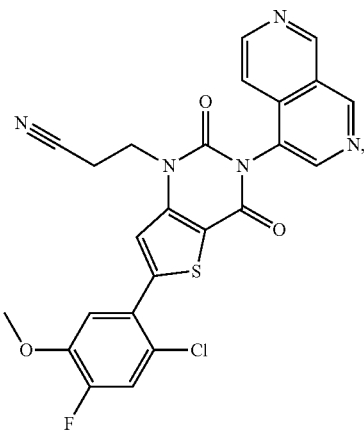
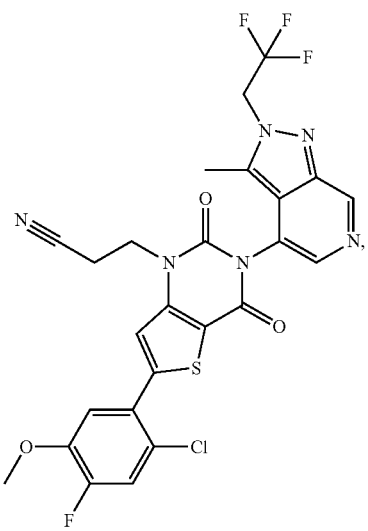

313
-continued
314
-continued
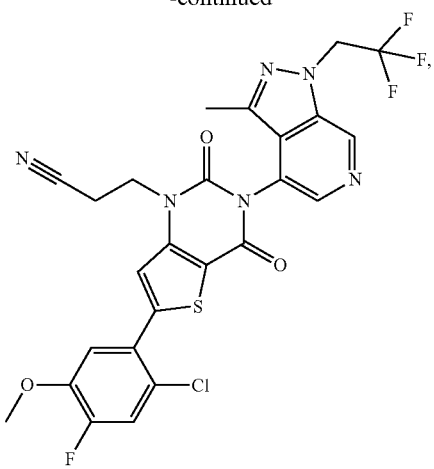
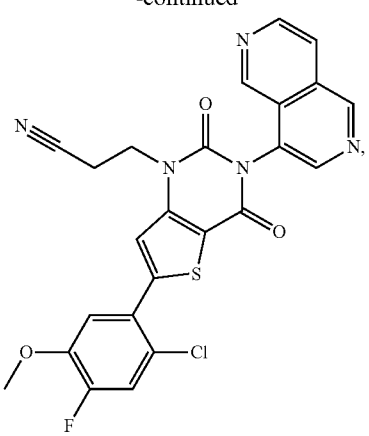

315
-continued
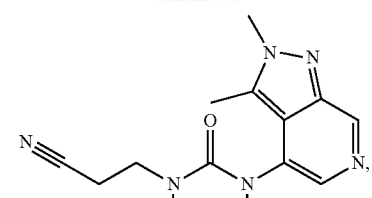
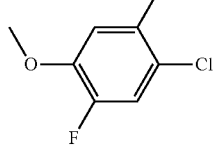
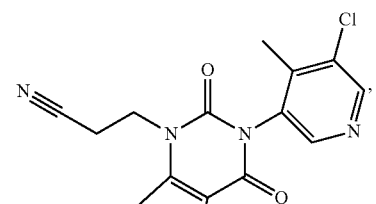
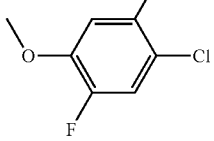
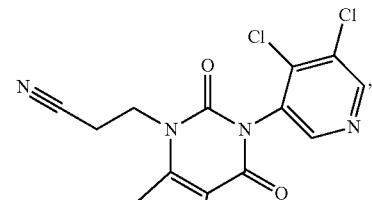
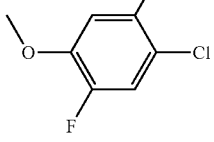
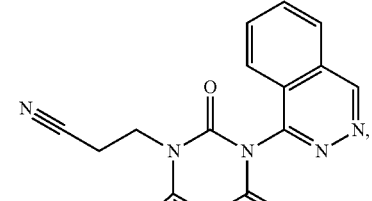
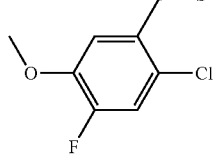
316
-continued
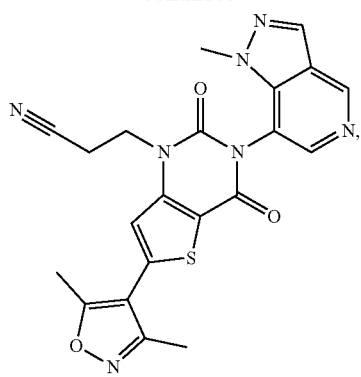
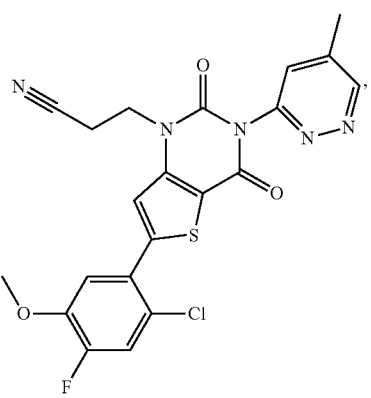
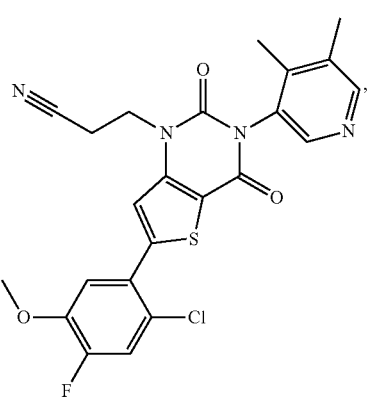
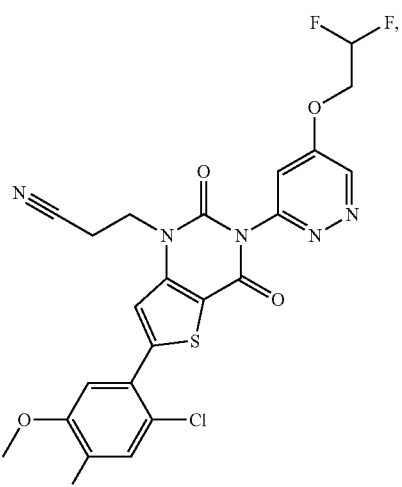

317
-continued
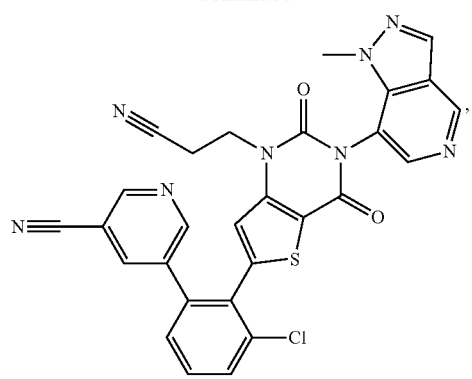
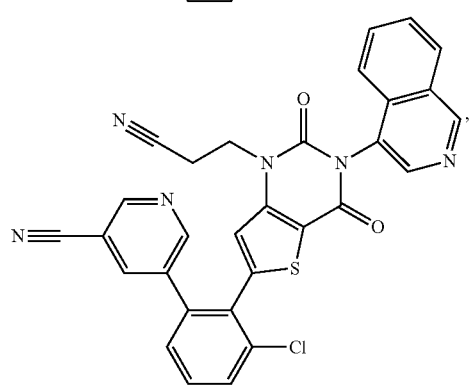
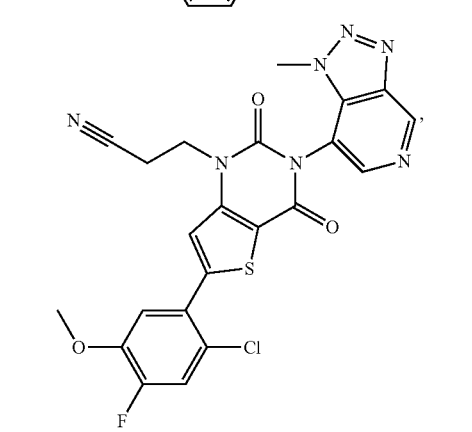
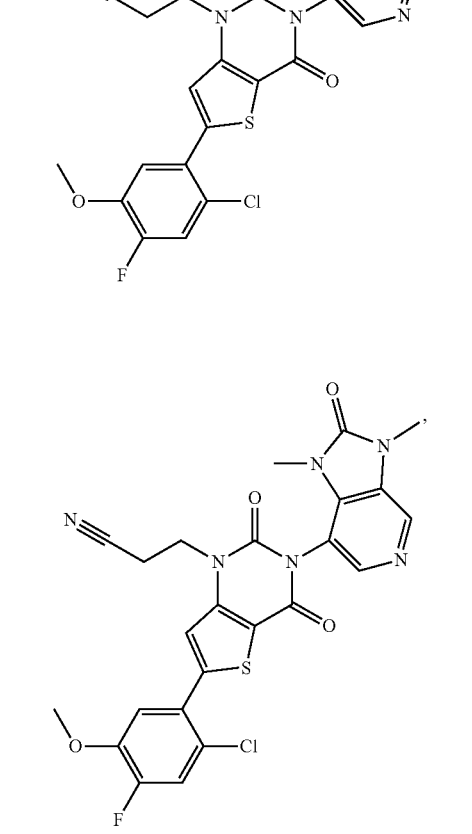
318
-continued
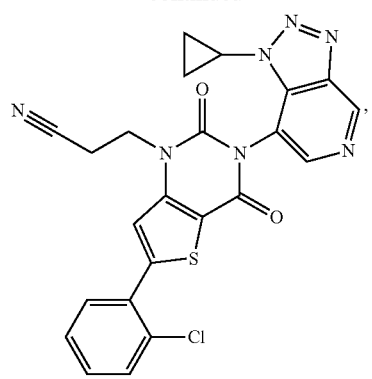
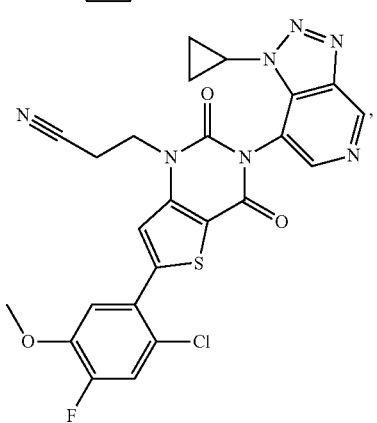
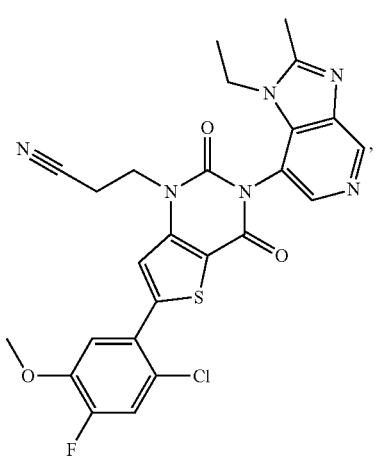
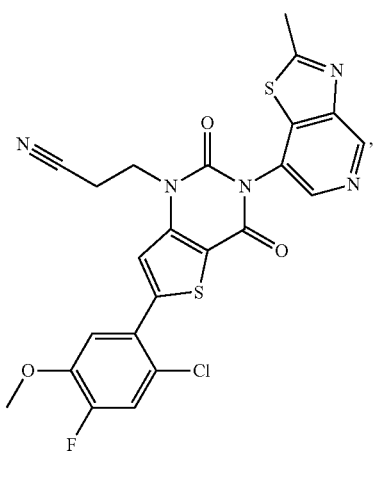

319
-continued
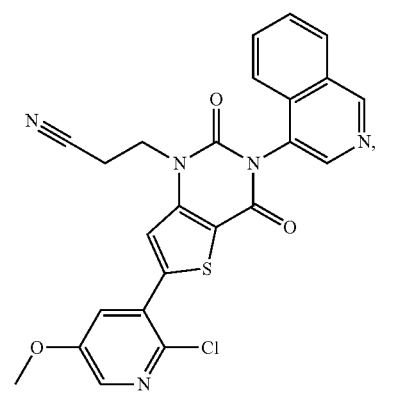
320
-continued
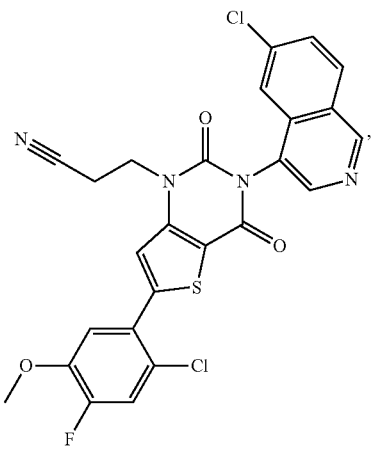
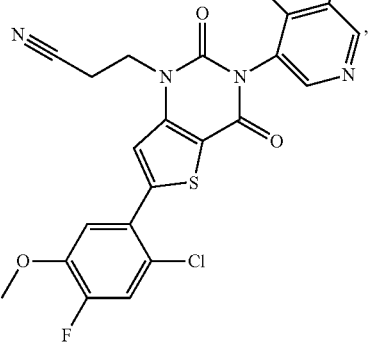

321
-continued
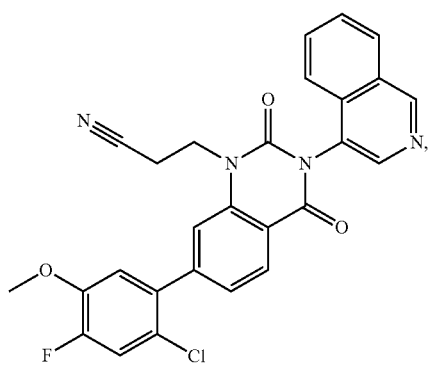
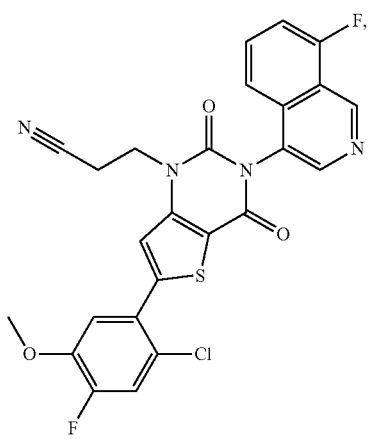
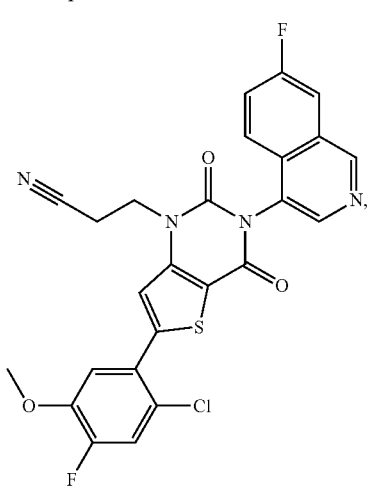
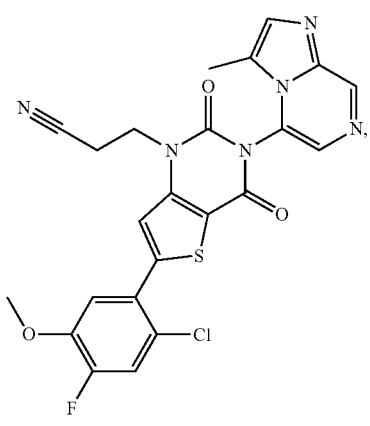
322
-continued
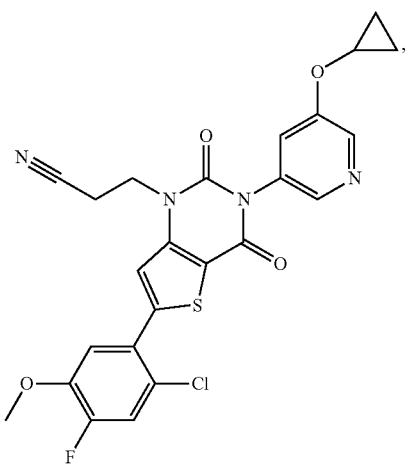
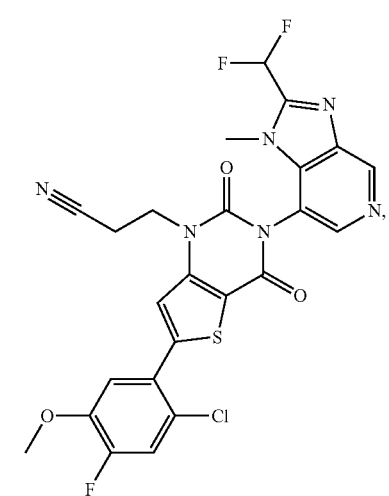
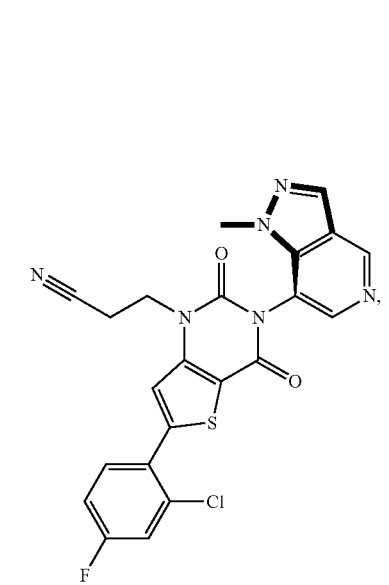

323
-continued
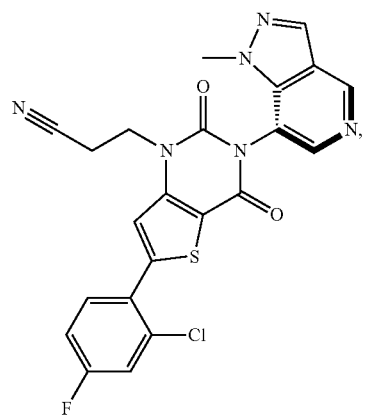
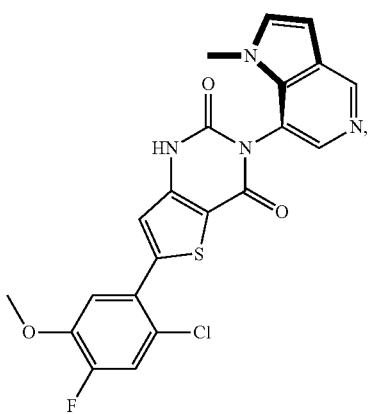
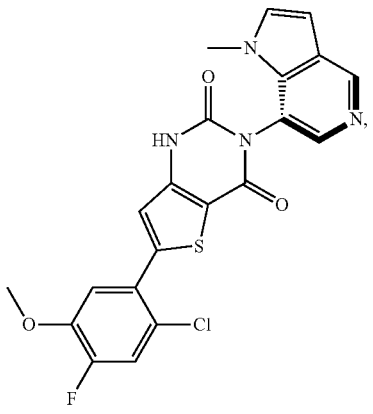
324
-continued
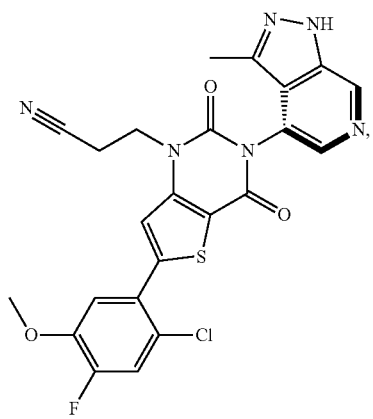
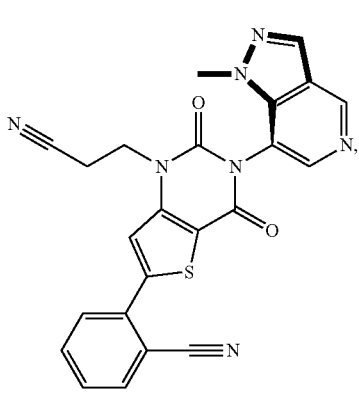
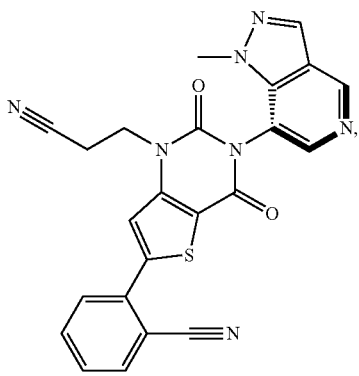
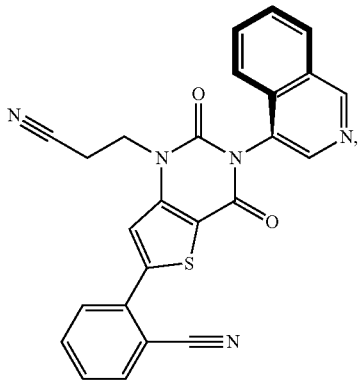

325
-continued
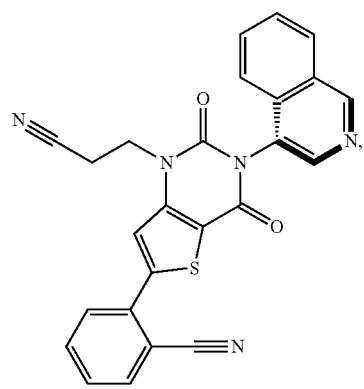
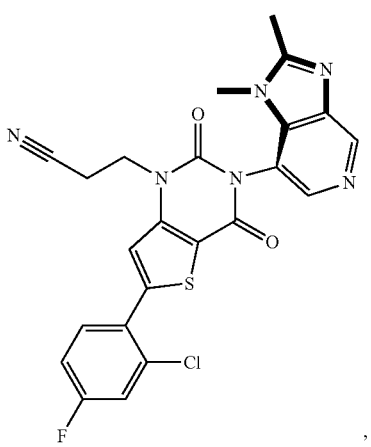
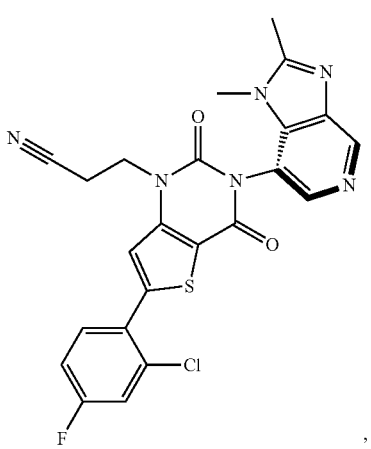
326
-continued
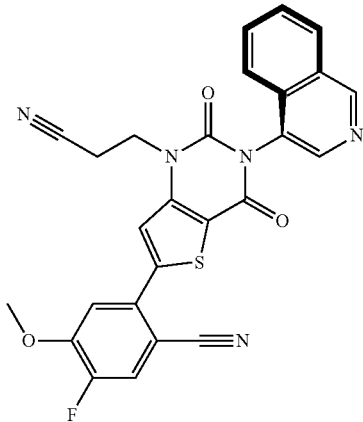
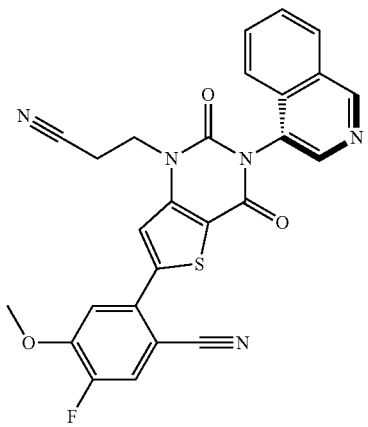
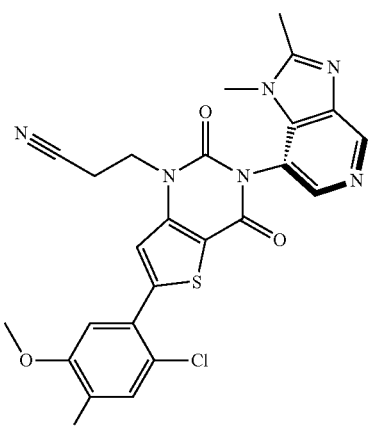
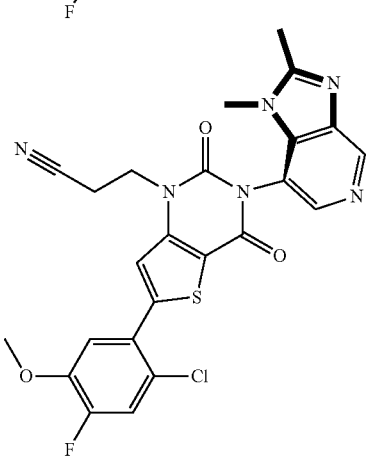

327
-continued
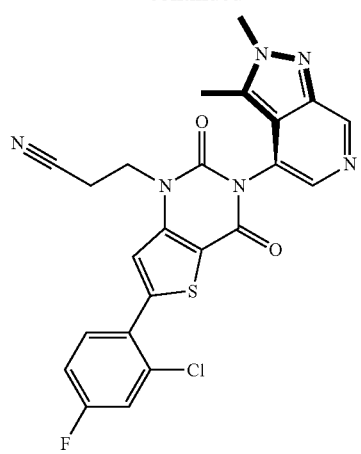
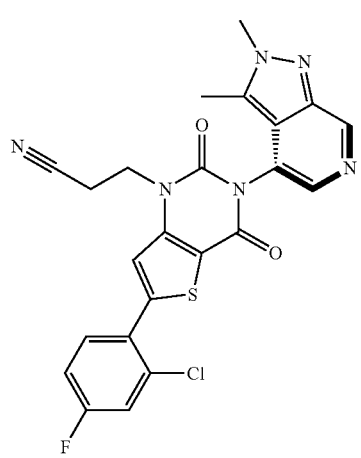
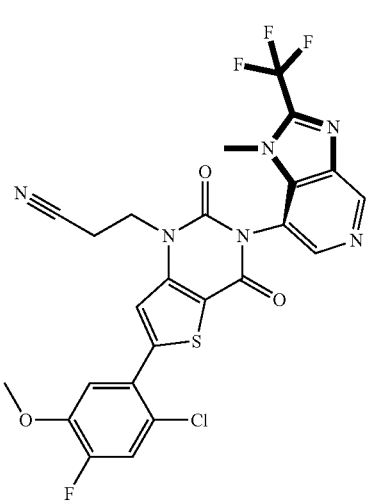
328
-continued
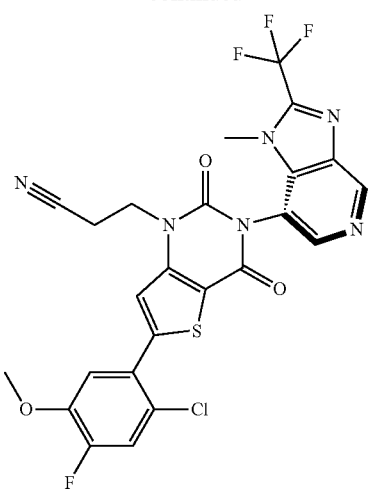
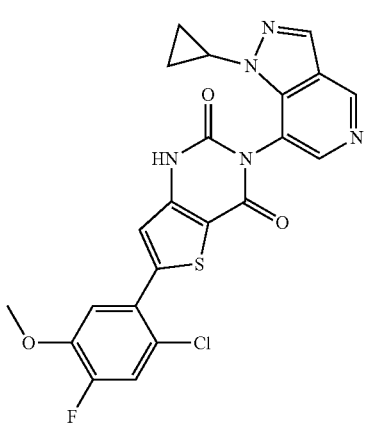
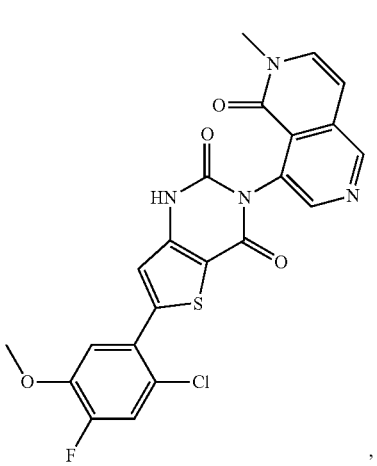

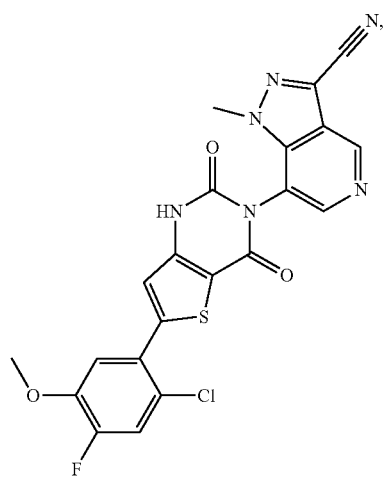
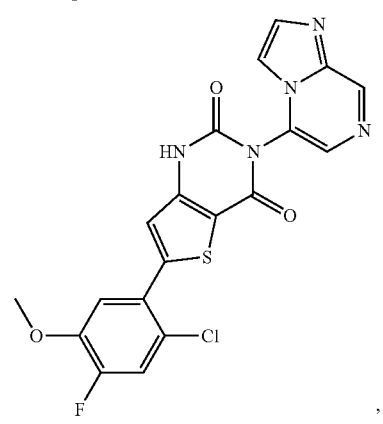
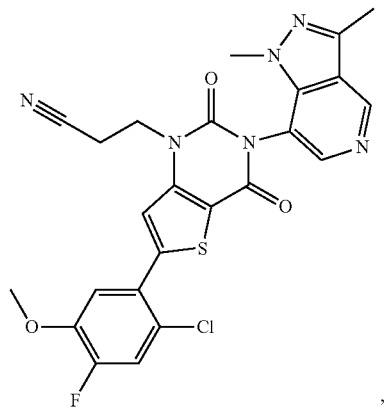
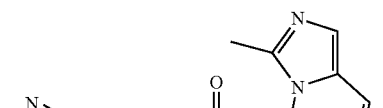
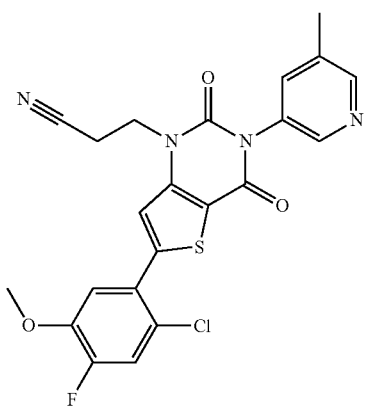
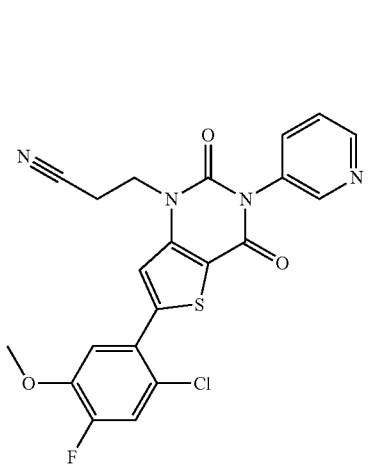
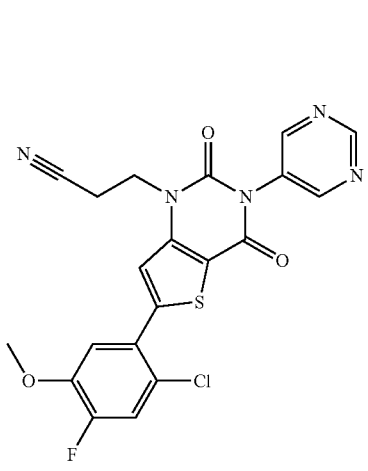
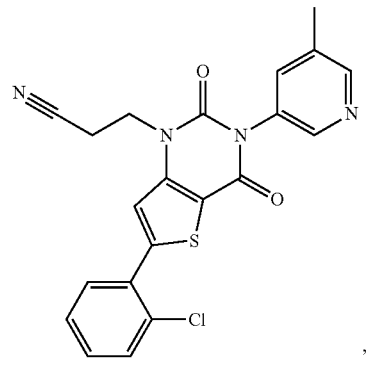

331
-continued
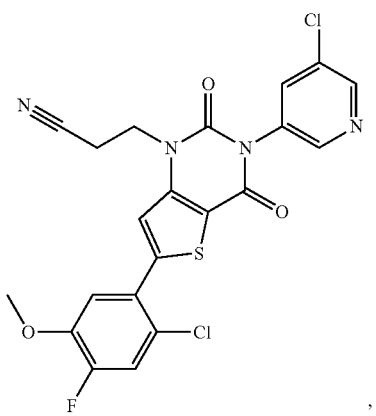
,
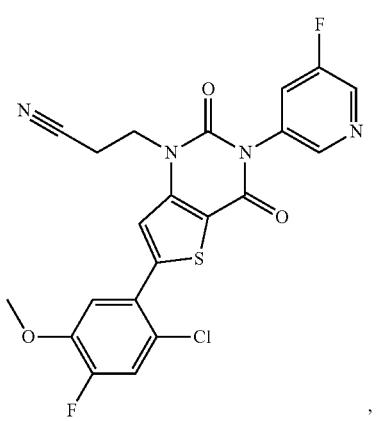
,
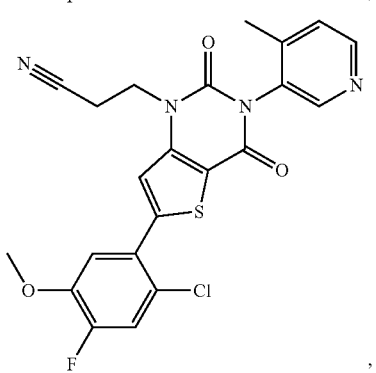
,
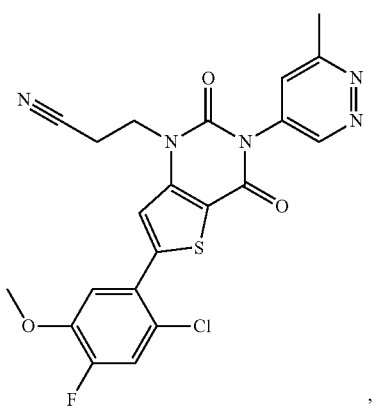
,
332
-continued
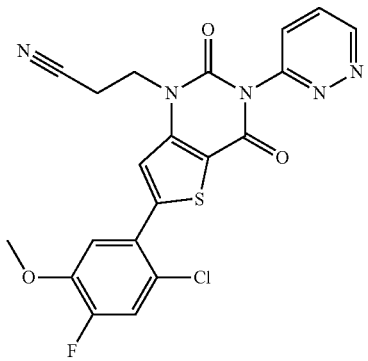
,
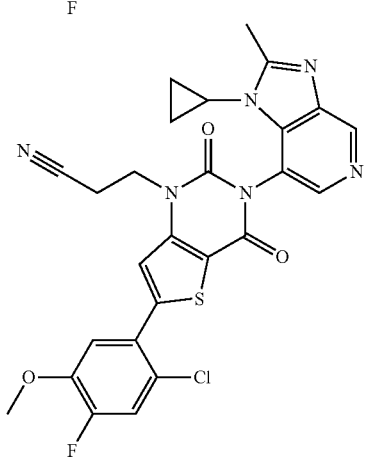
,
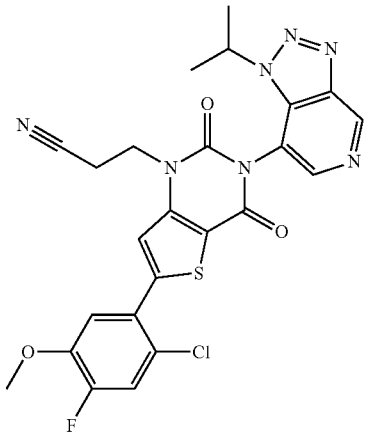
,
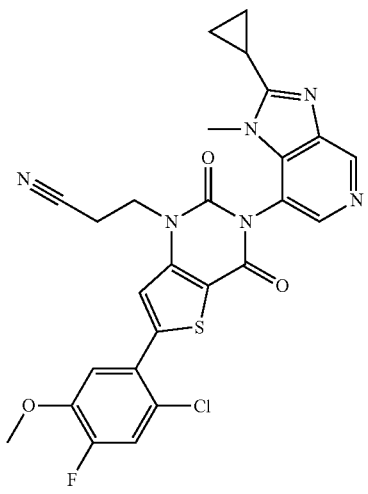
, 333
-continued
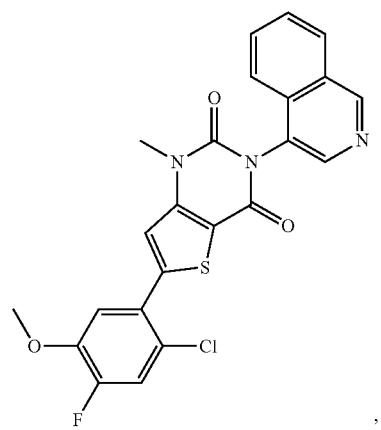
,
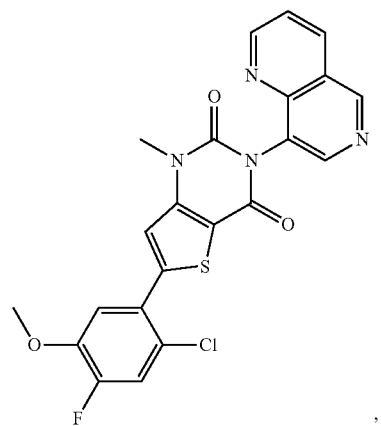
,
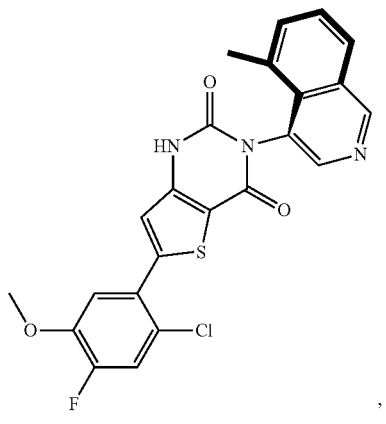
,
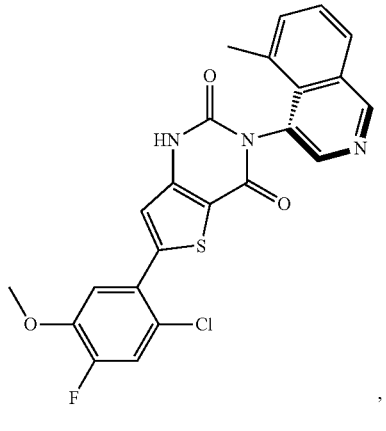
,
334
-continued
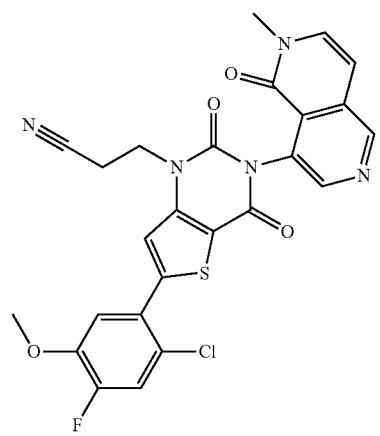
,
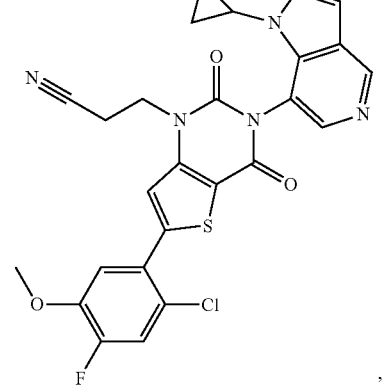
,
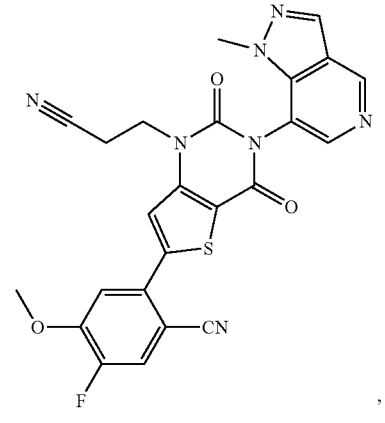
,
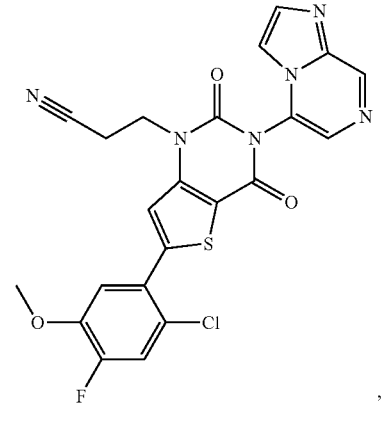
, 335
-continued
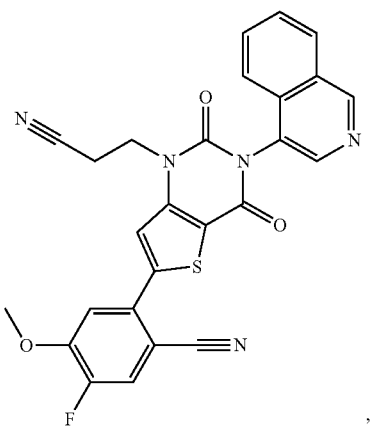
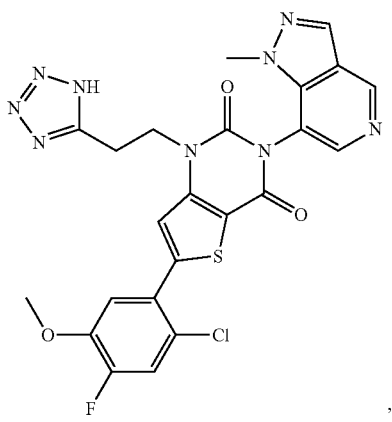
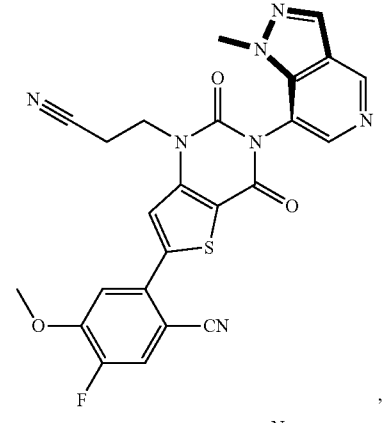
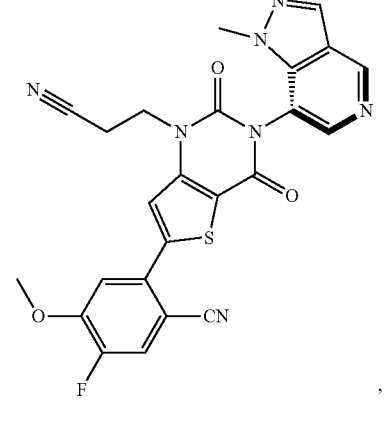
336
-continued
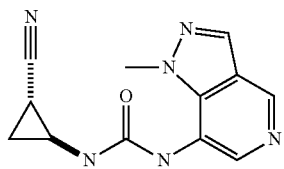
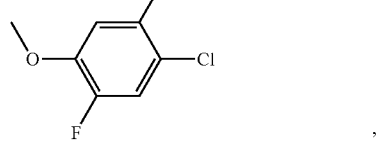
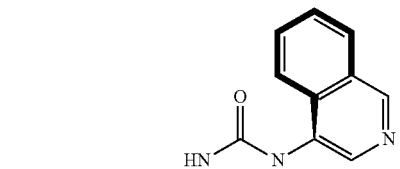
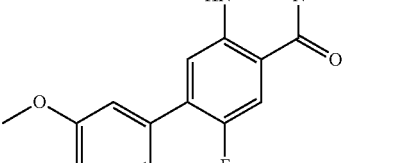

337
-continued
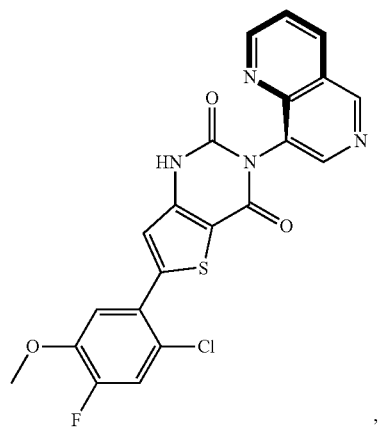
,
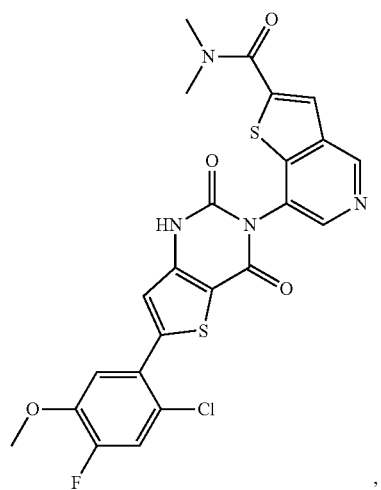
,
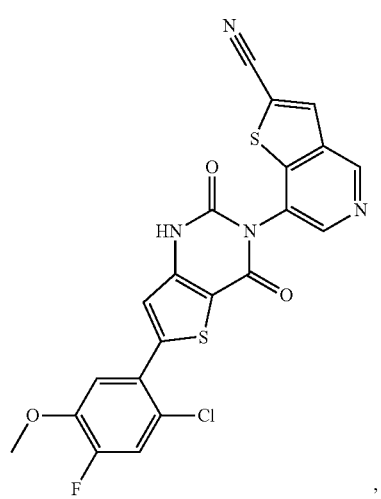
,
338
-continued
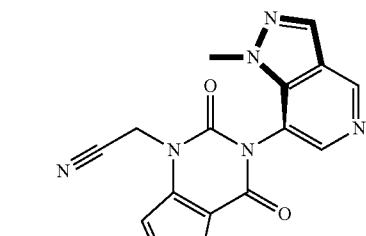
,
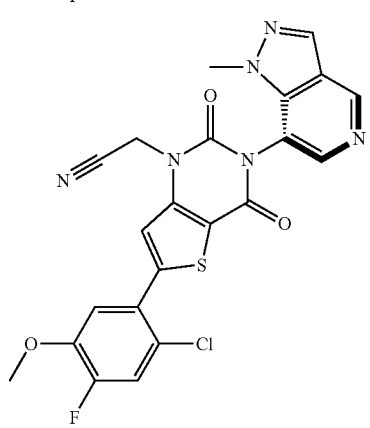
,
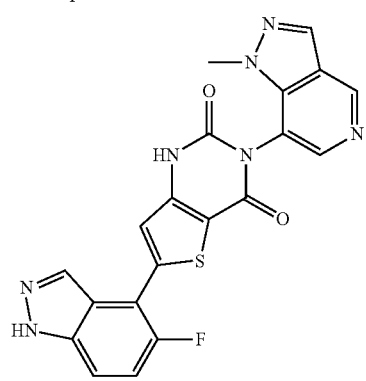
,
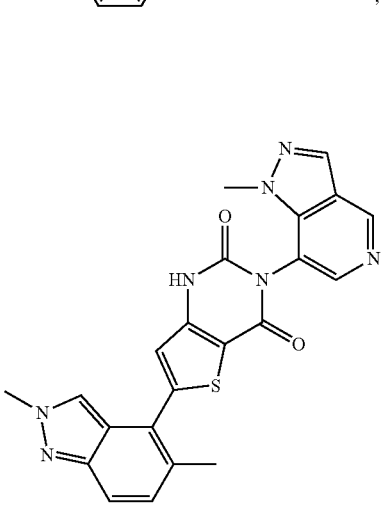
, 339
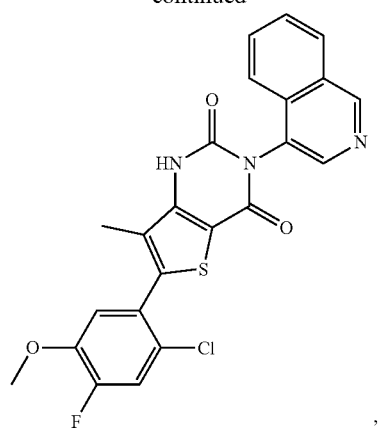
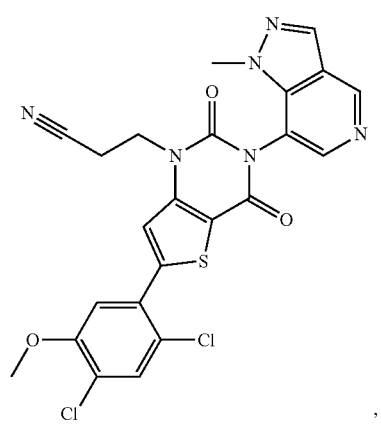
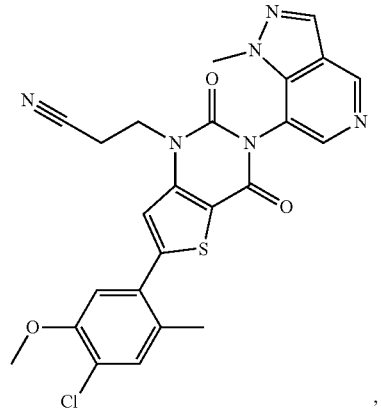
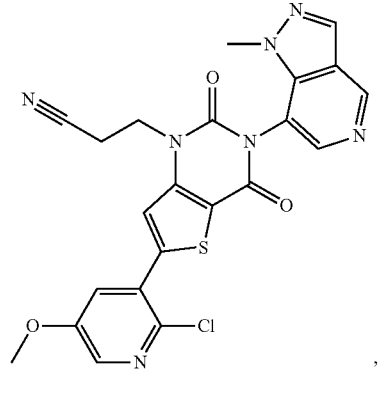
340
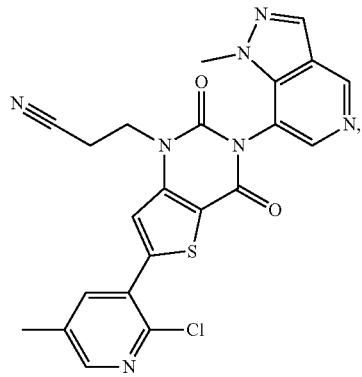
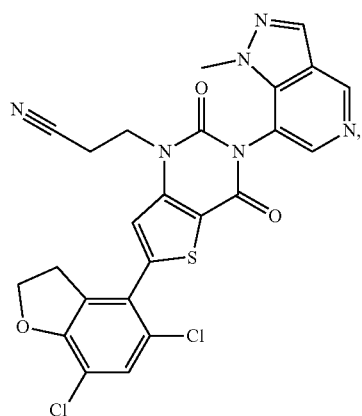
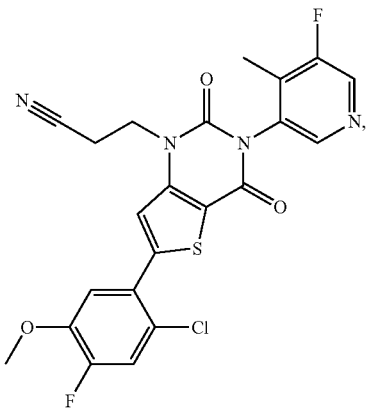
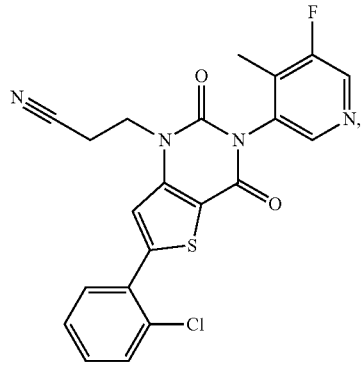

341
-continued
342
-continued
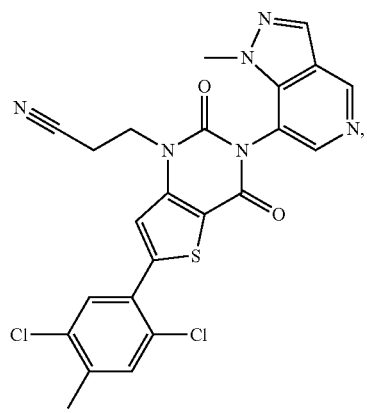
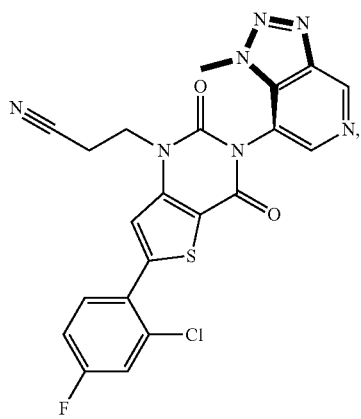
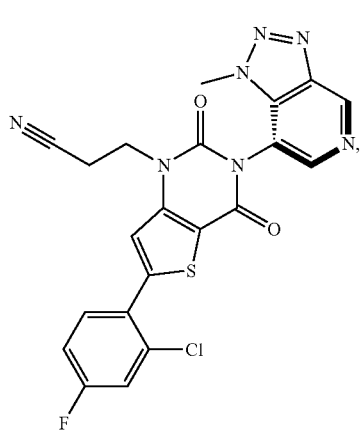
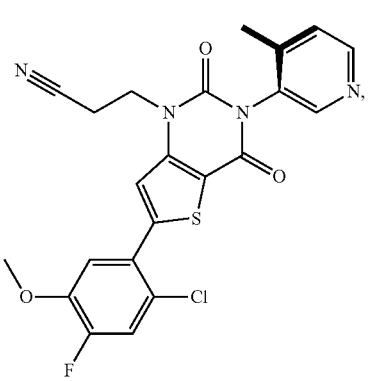
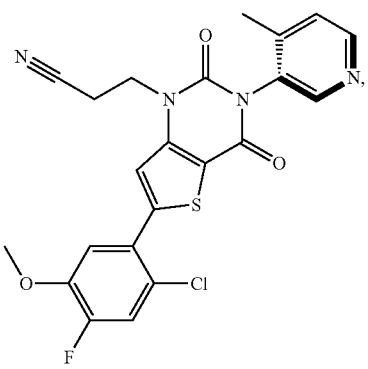

343
-continued
344
-continued
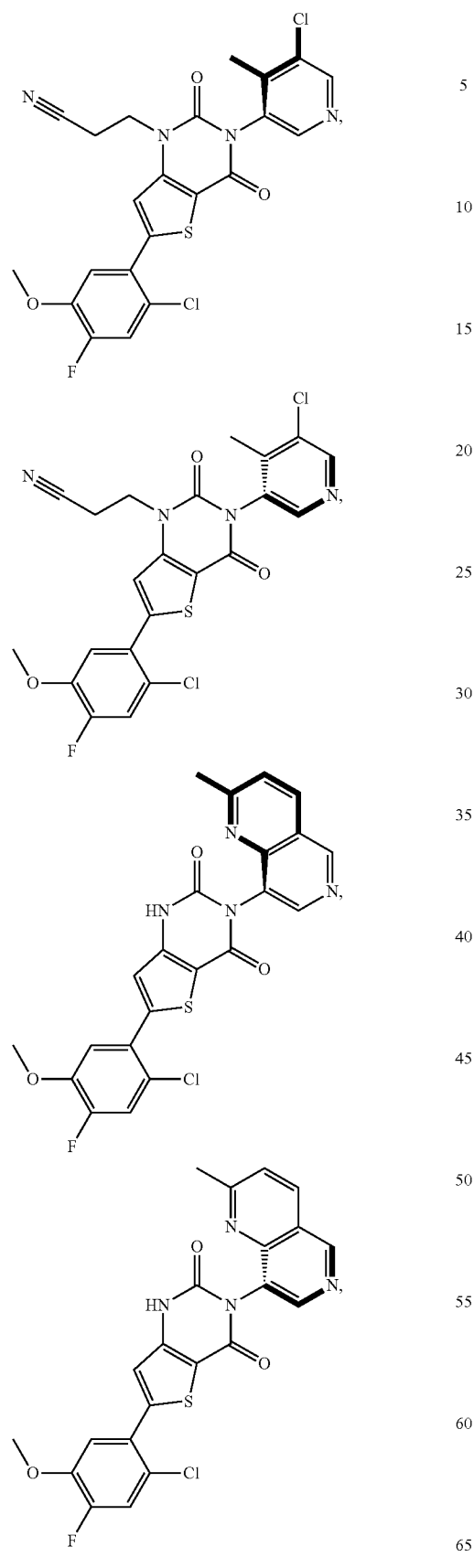
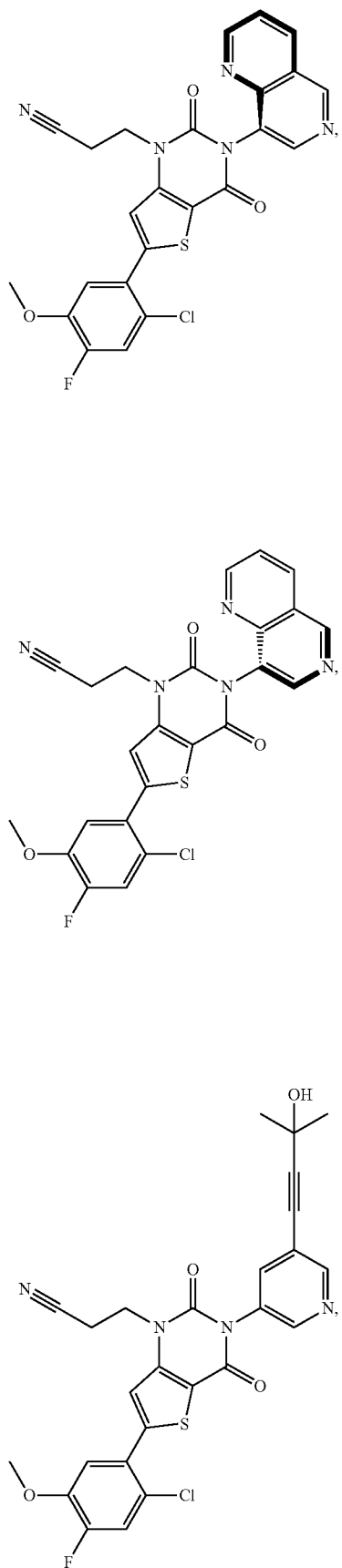

345
-continued
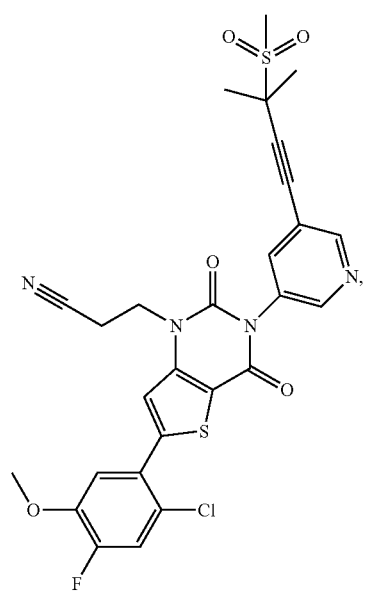
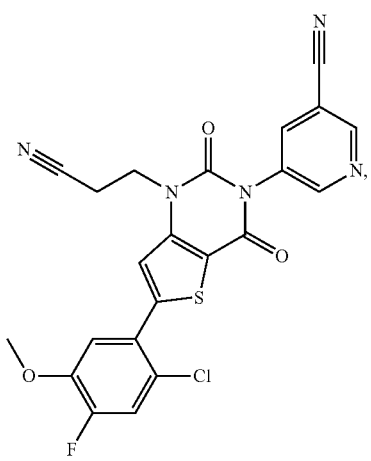
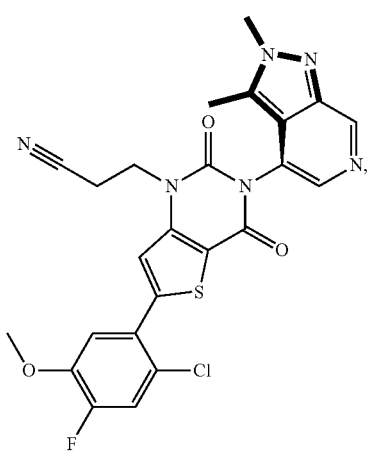
346
-continued
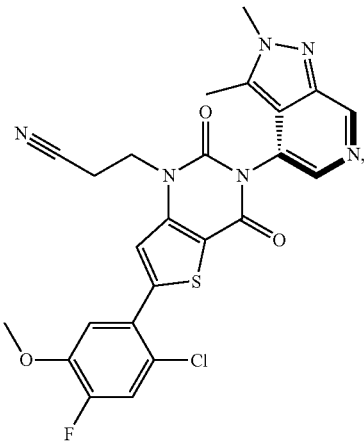
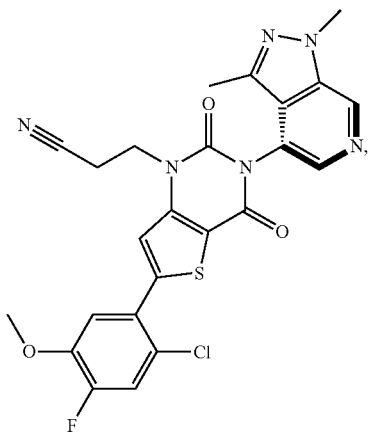
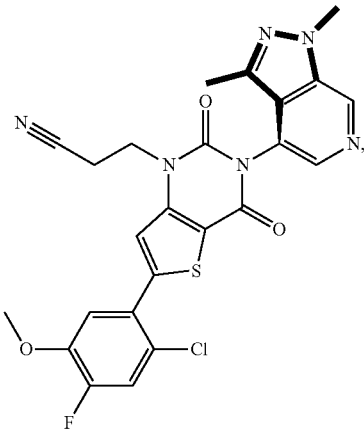
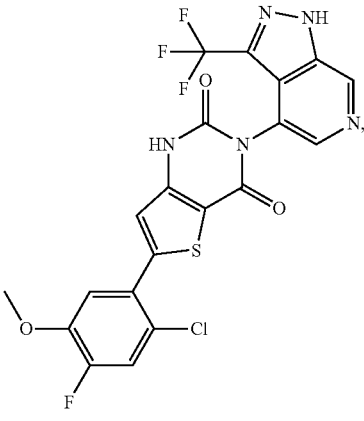

347
-continued
348
-continued
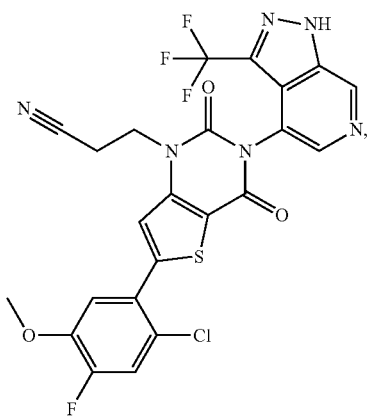
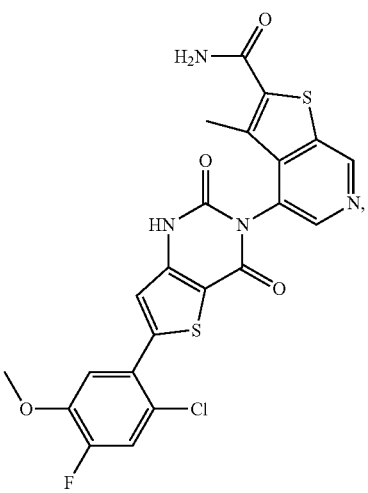

349
-continued
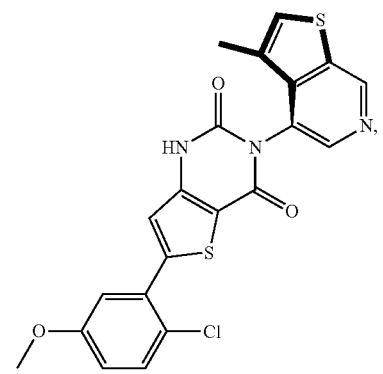
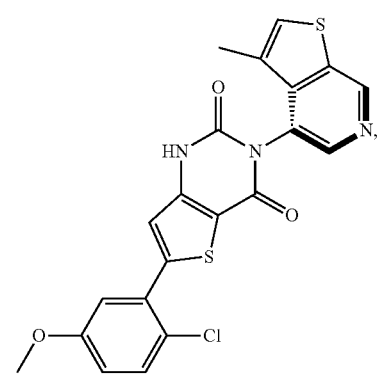
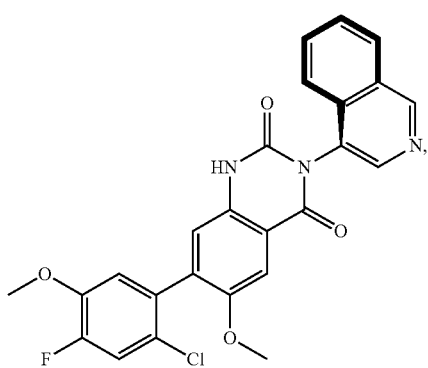
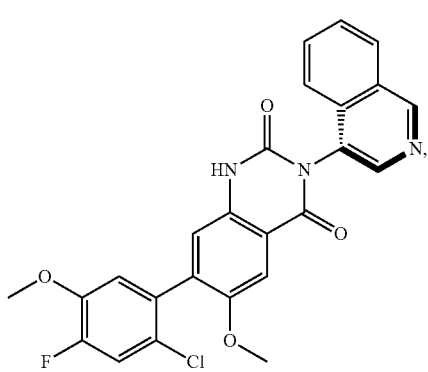
350
-continued
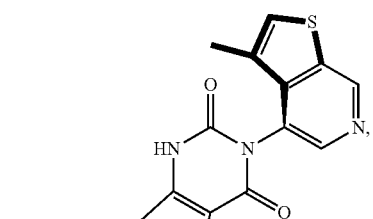
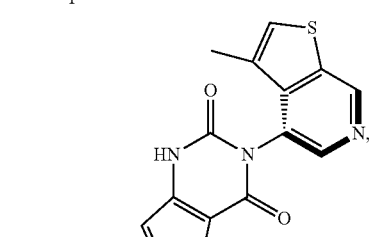
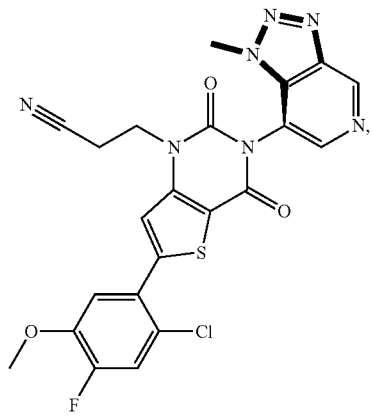
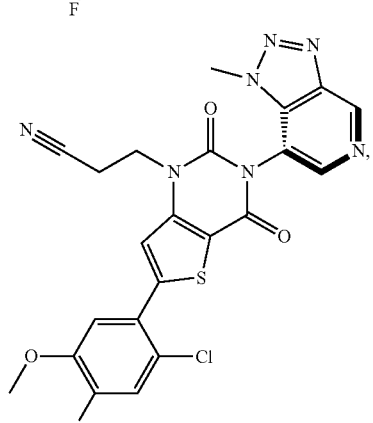

351
-continued
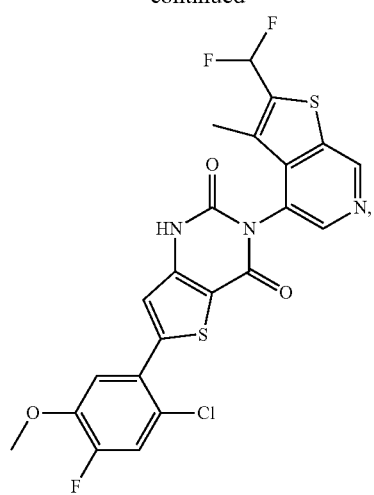
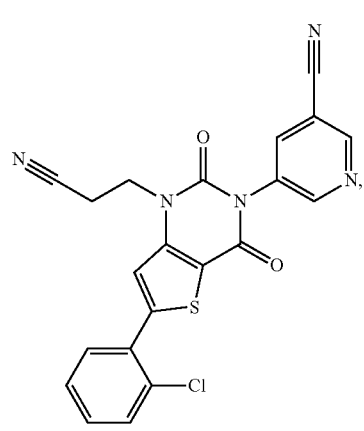
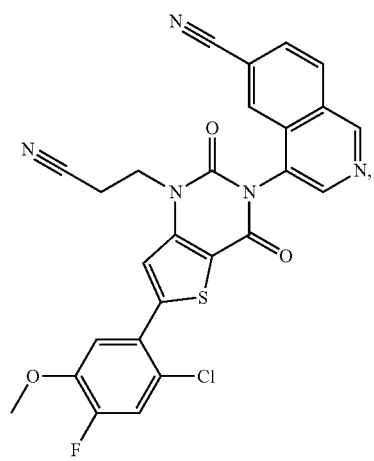
352
-continued
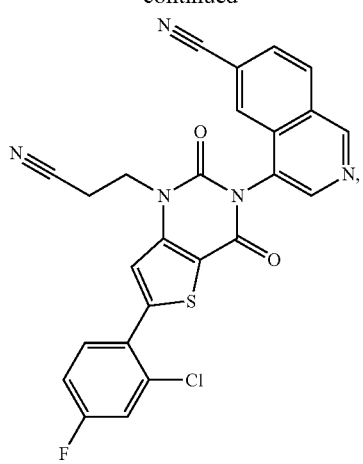
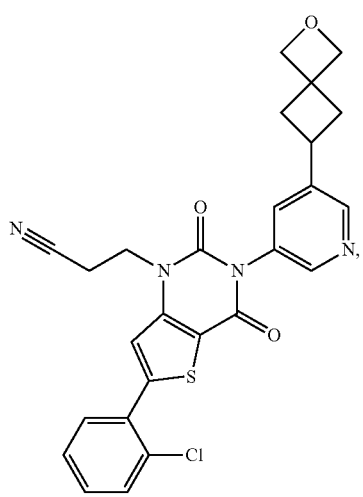
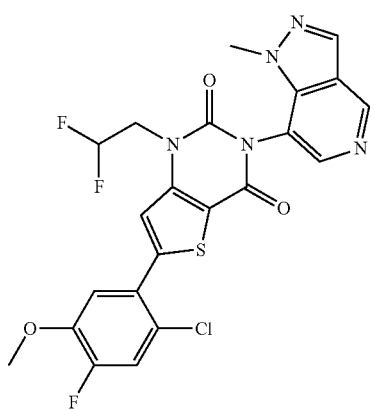

353
-continued
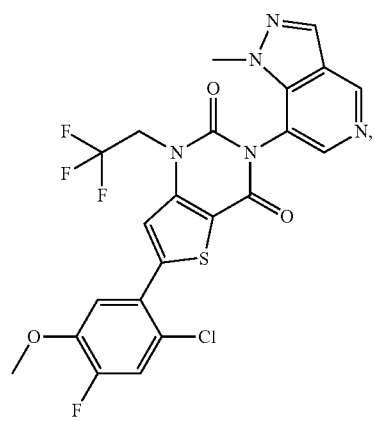
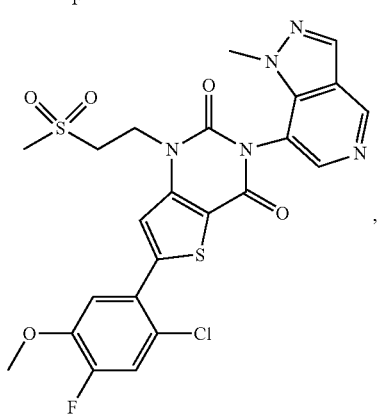
,
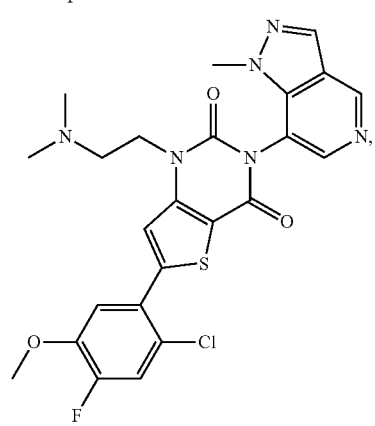
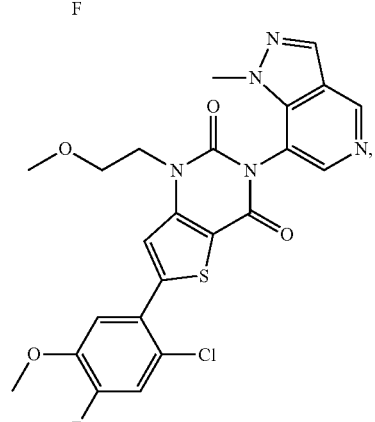
354
-continued
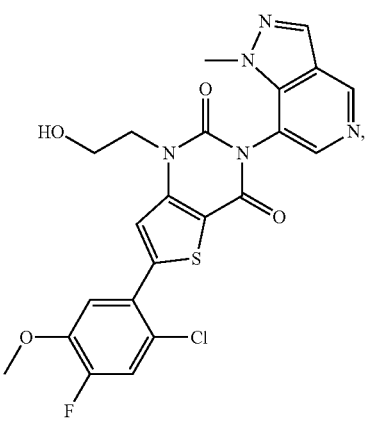
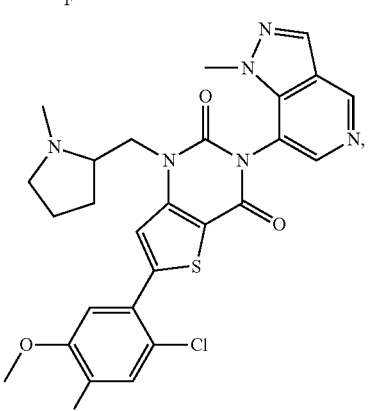
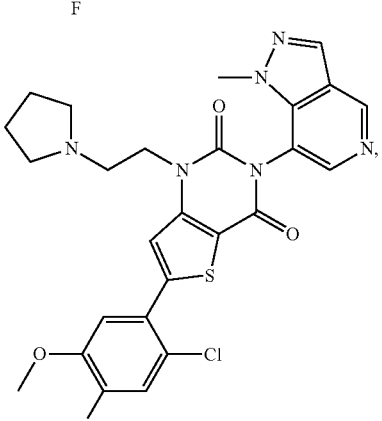
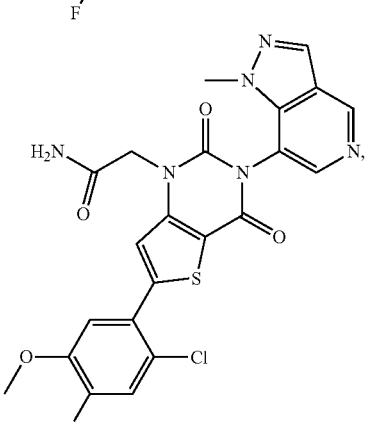

355
-continued
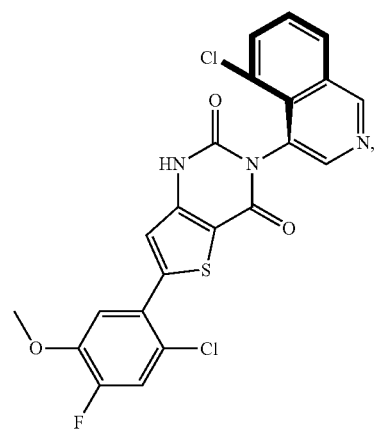
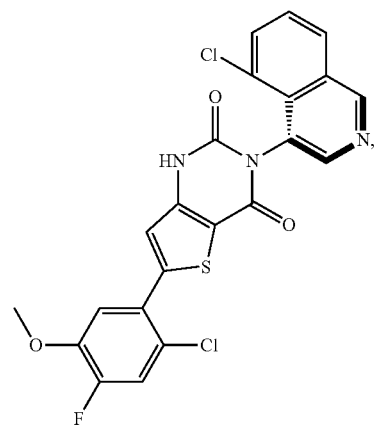
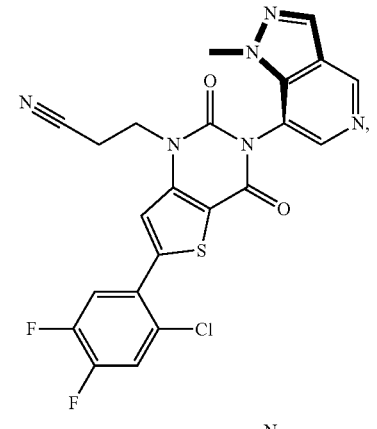
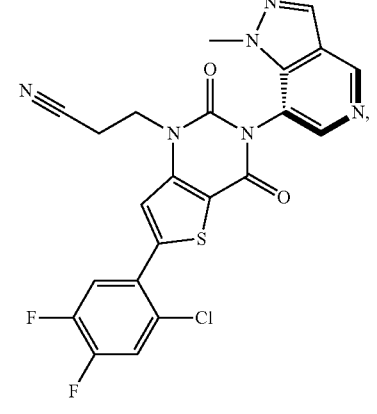
356
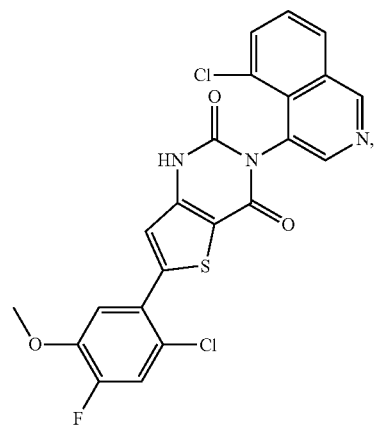
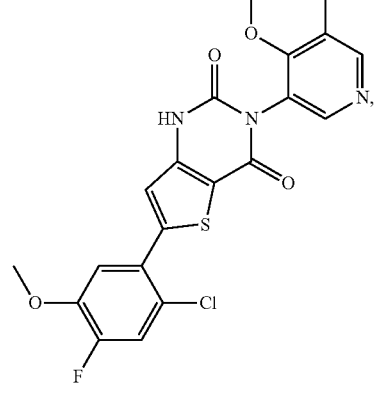
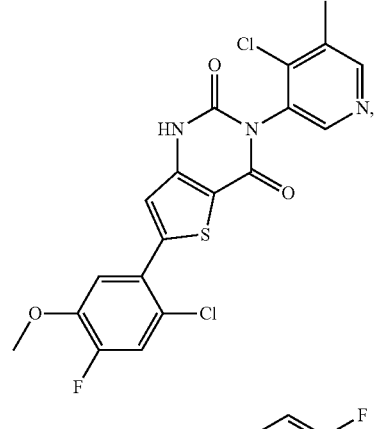
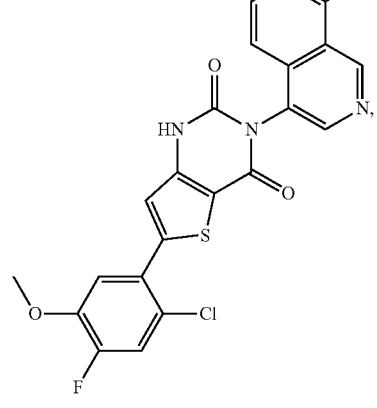

357
-continued
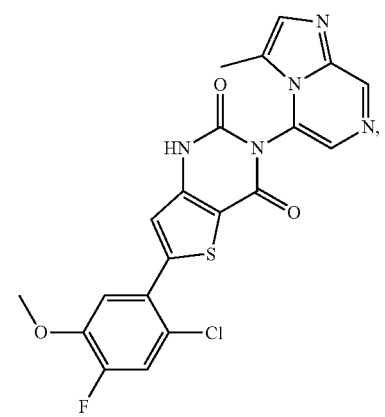
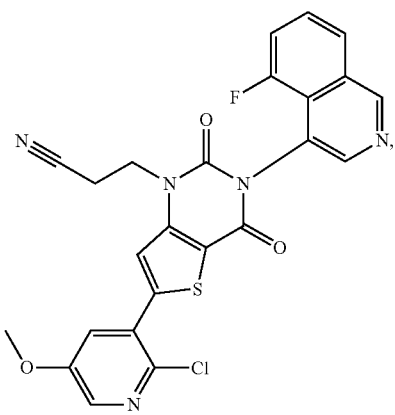
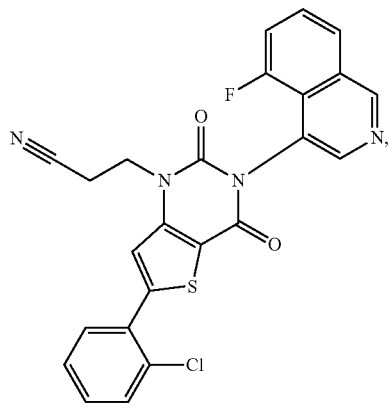
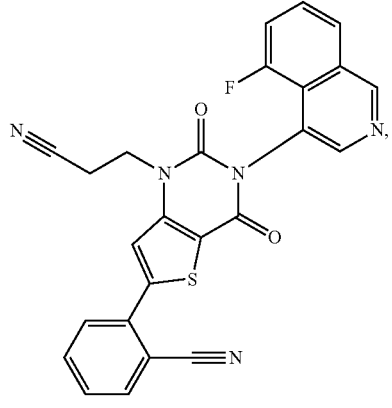
358
-continued
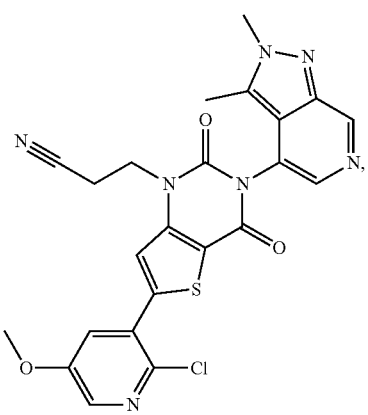
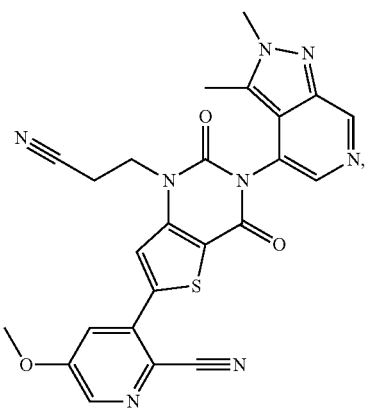
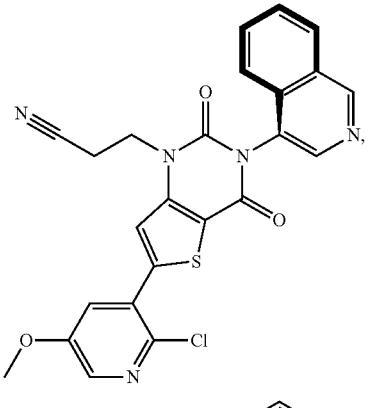
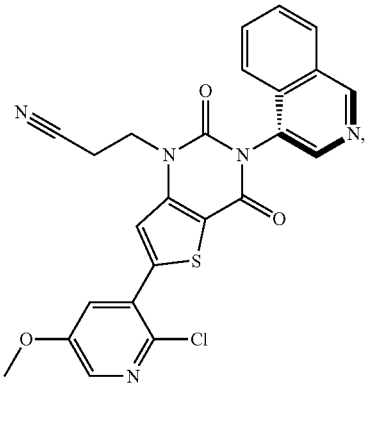

359
-continued
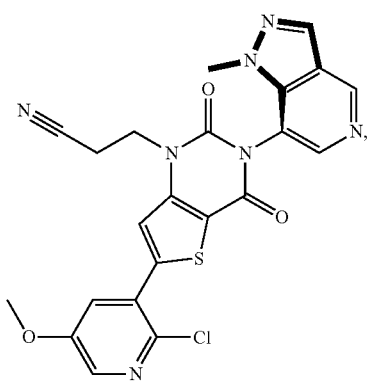
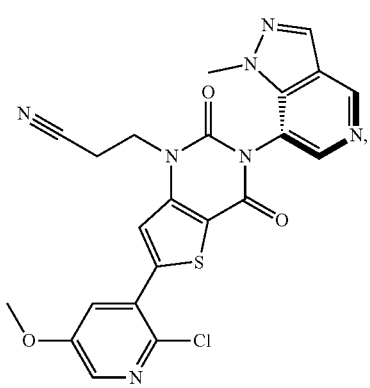
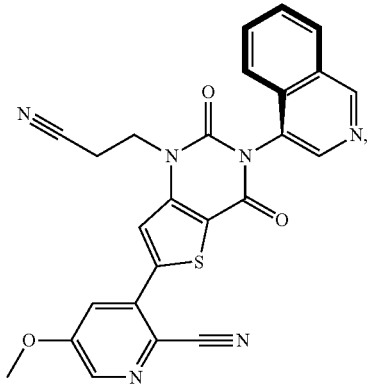
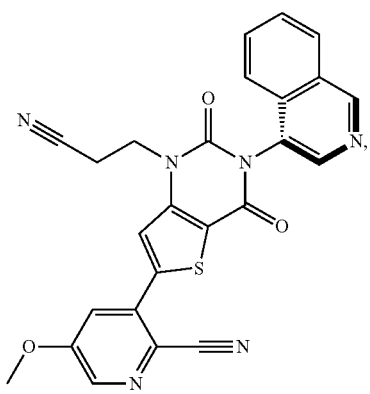
360
-continued
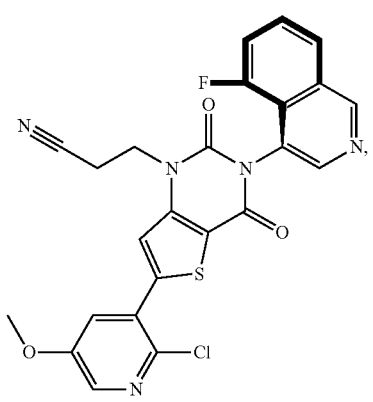
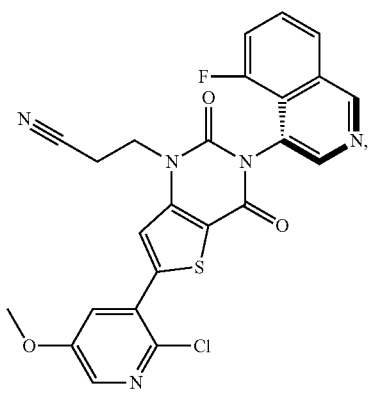
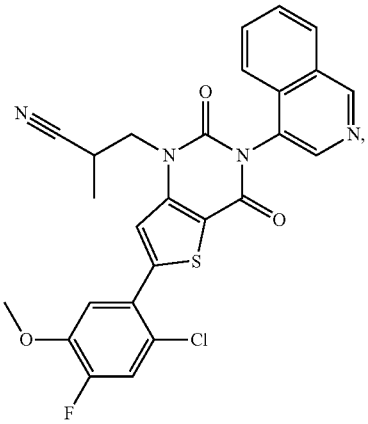
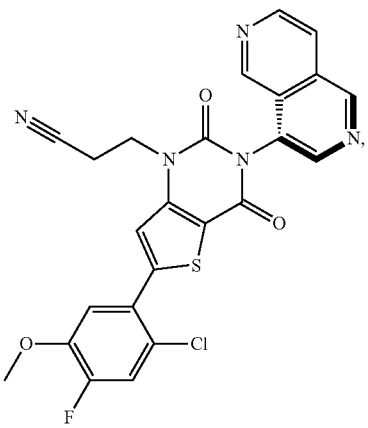

361
-continued
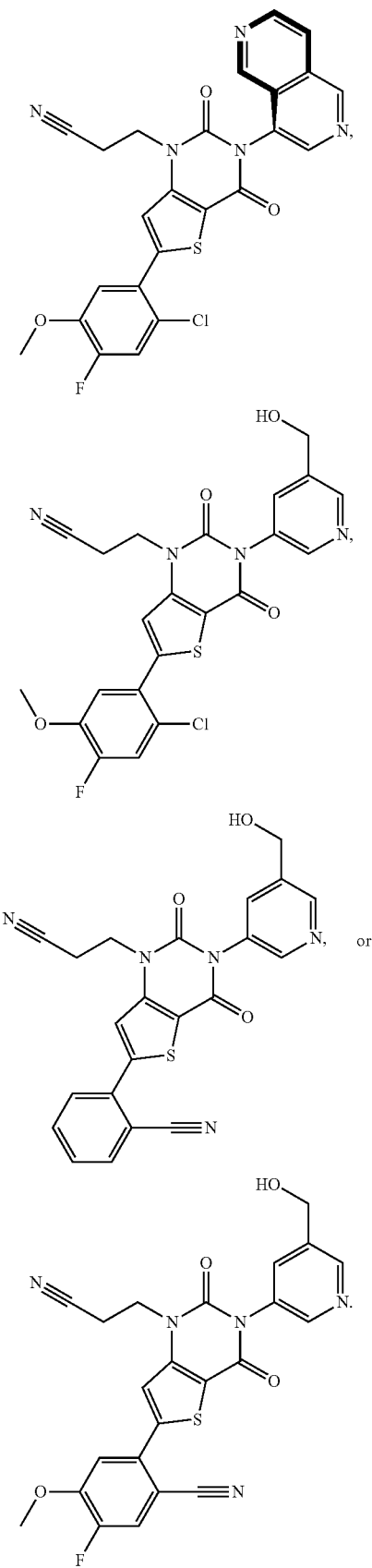
362
In some embodiments, a compound of the disclosure is a compound, or pharmaceutically acceptable salt thereof, having a structure as shown in Scheme B:
Scheme B
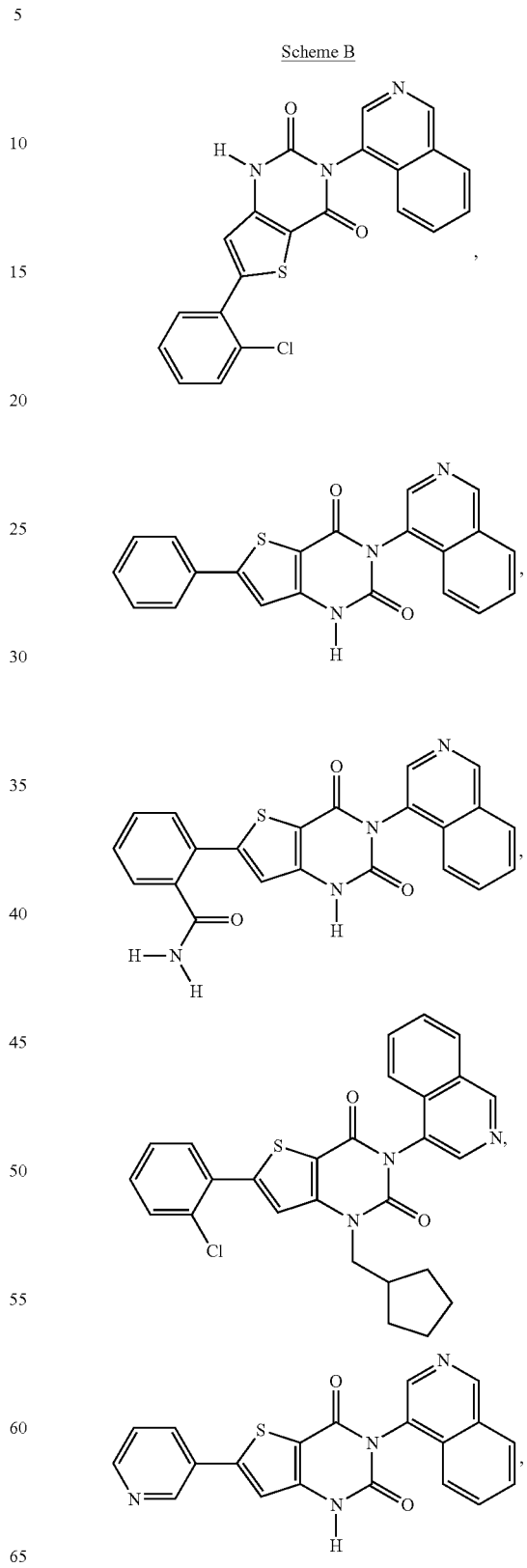

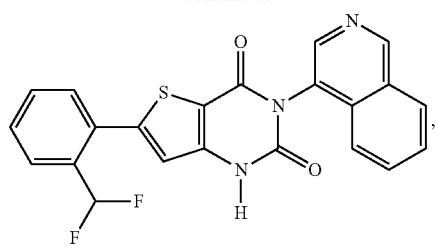
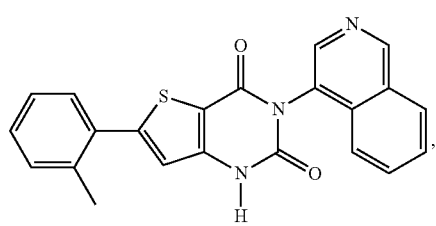
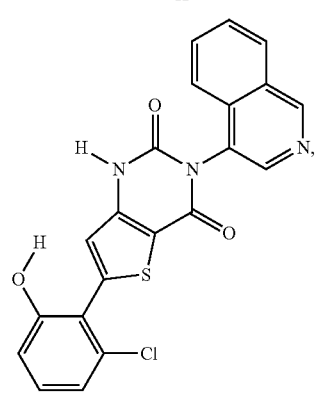
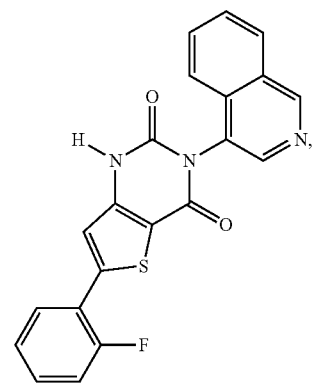
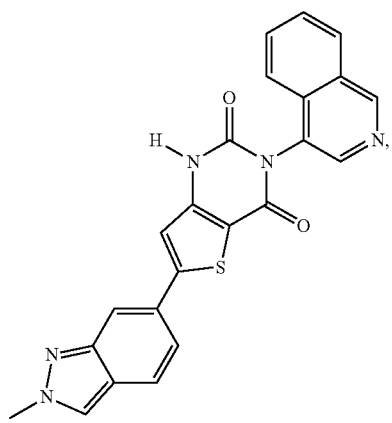
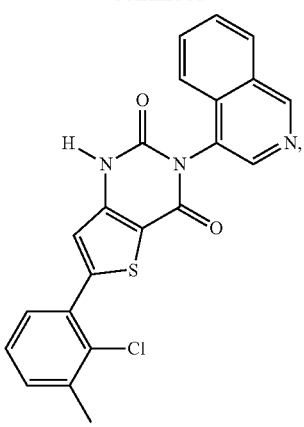
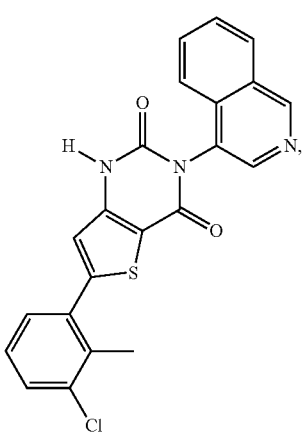
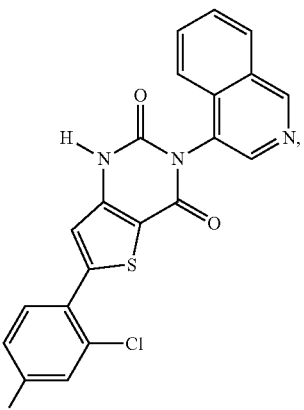
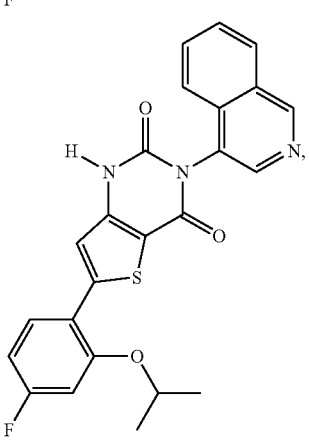

365
-continued
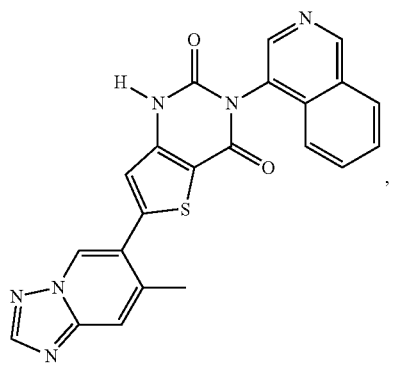
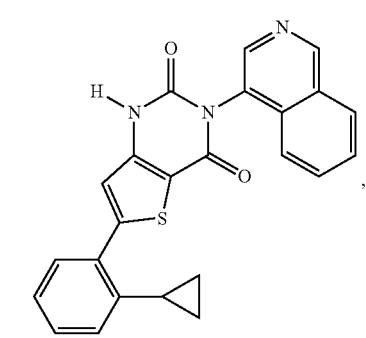
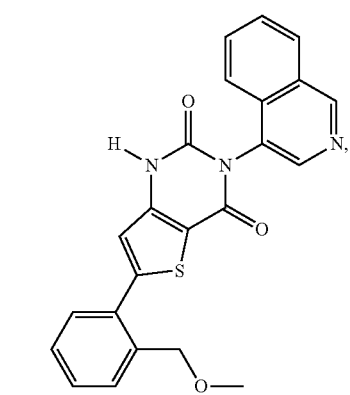
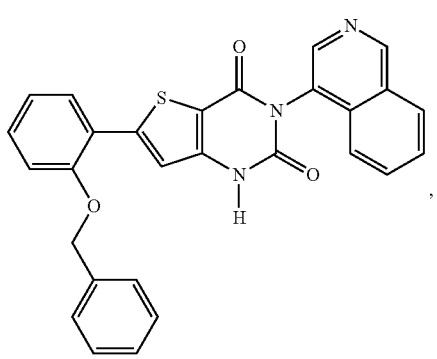
366
-continued
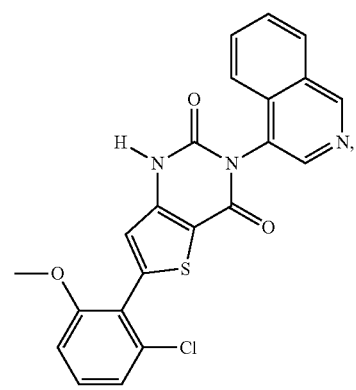
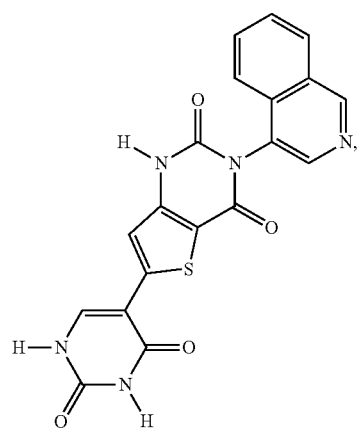
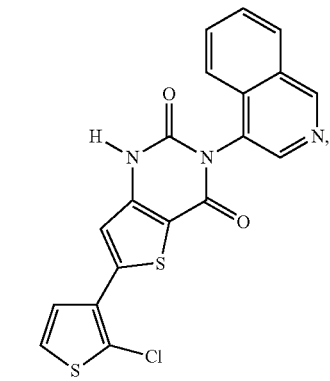
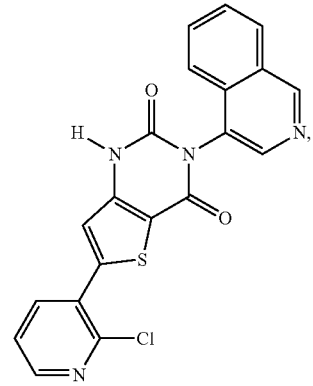

367
-continued
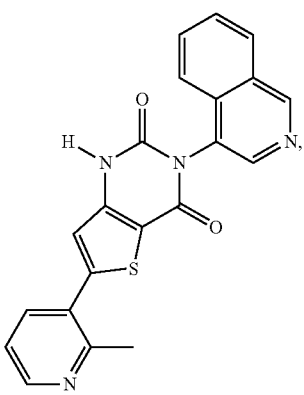
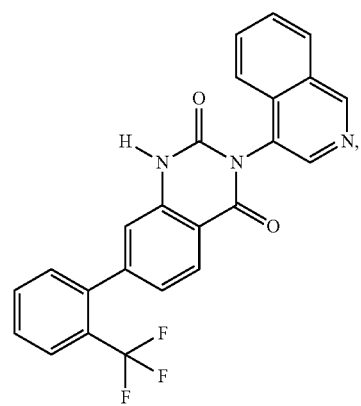
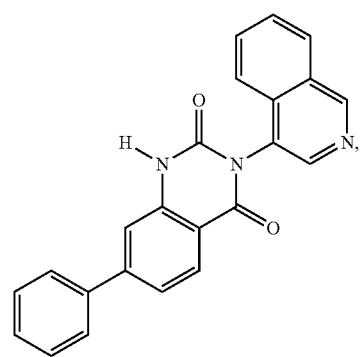
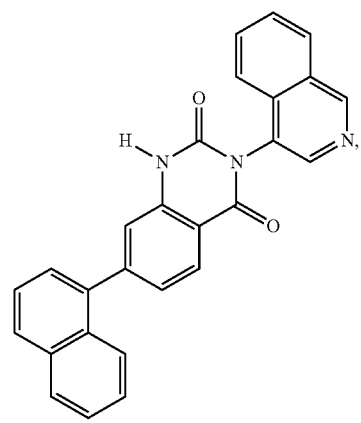
368
-continued
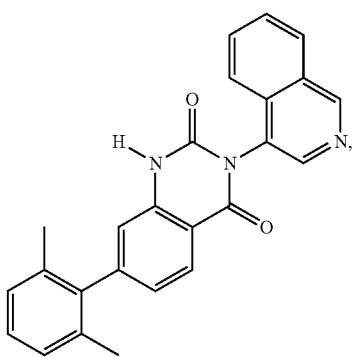
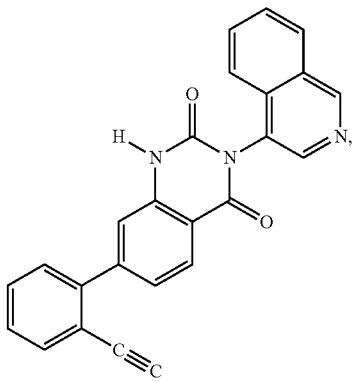
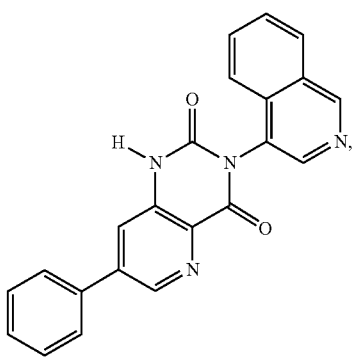
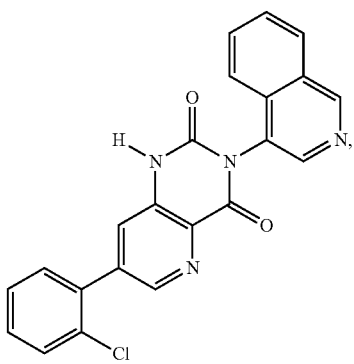
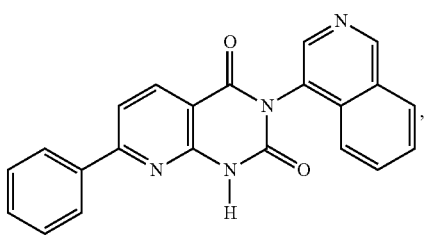

-continued
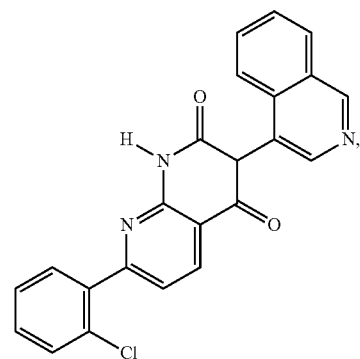
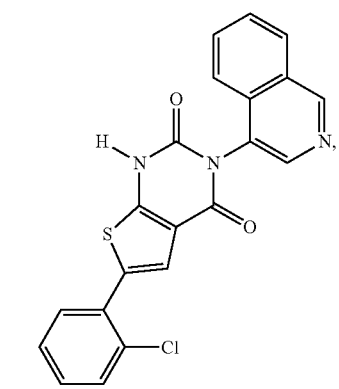
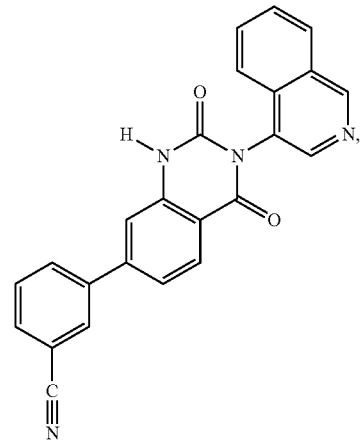
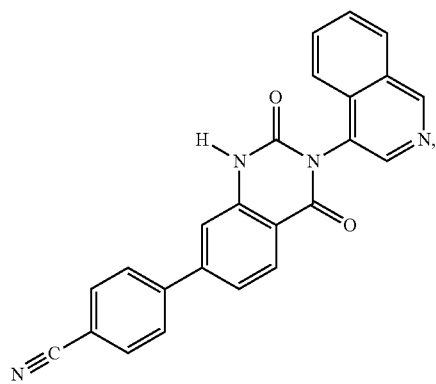
-continued
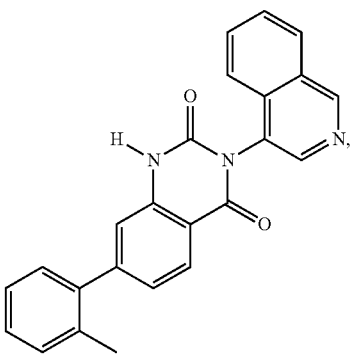
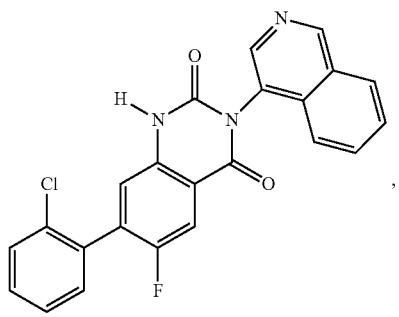
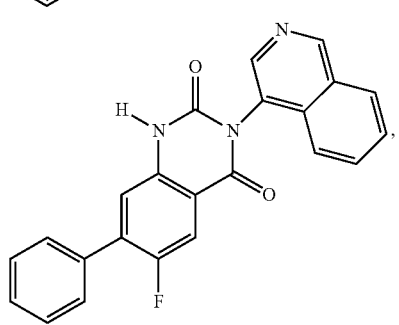
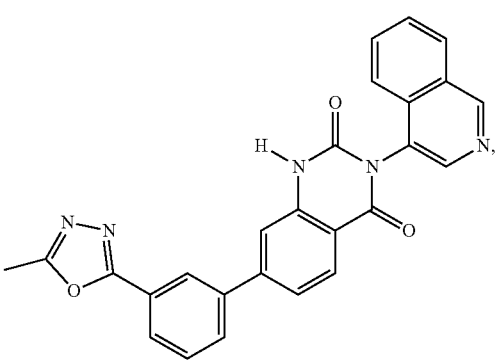
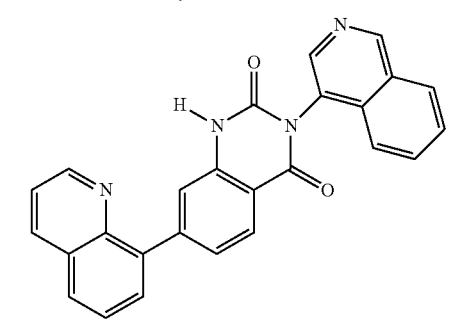

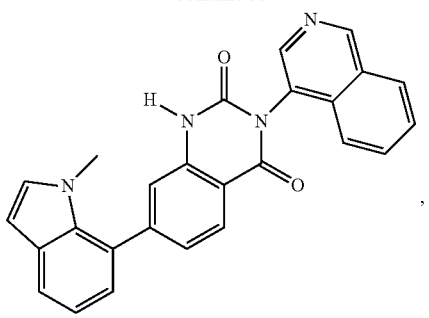
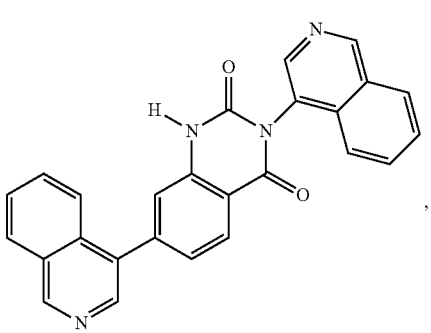
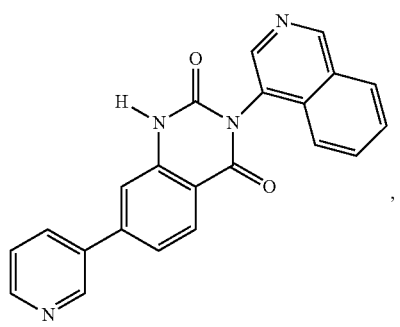
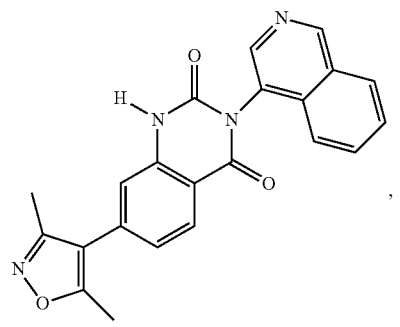
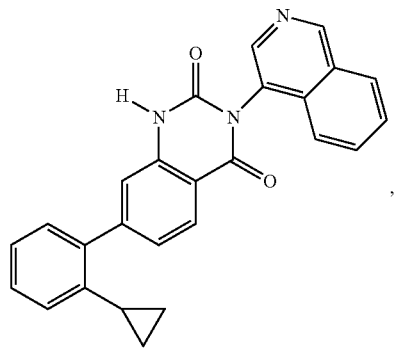
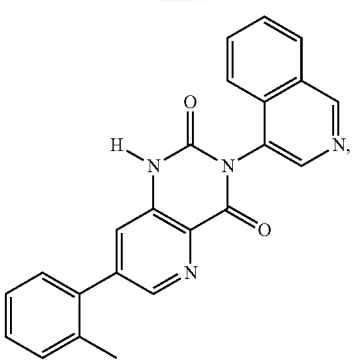
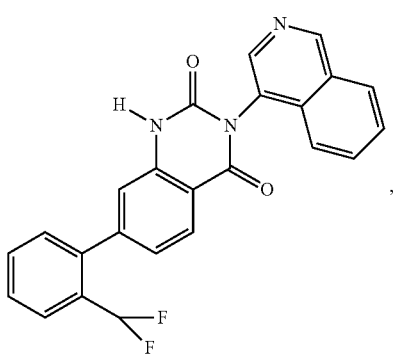
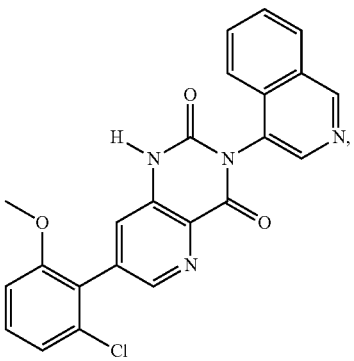
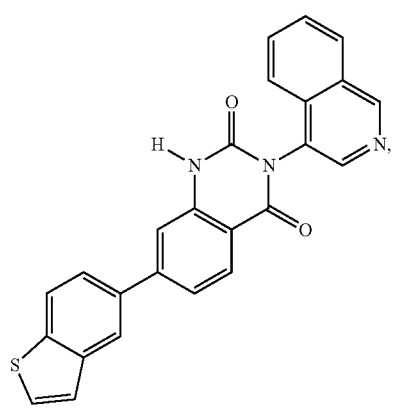

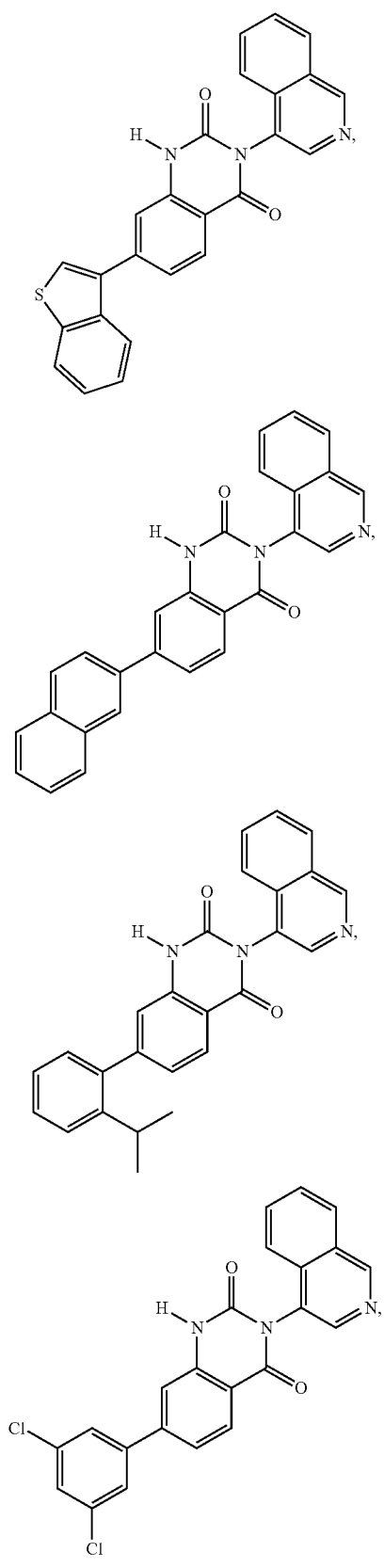
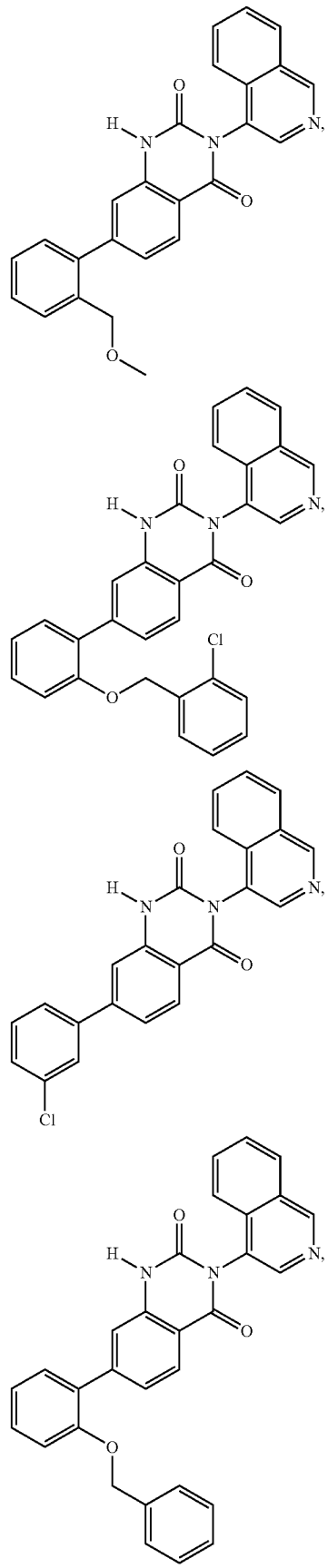

-continued
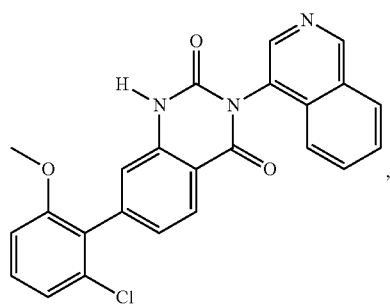
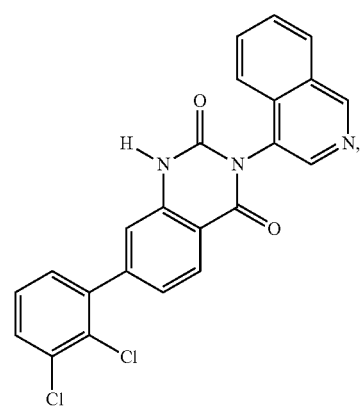
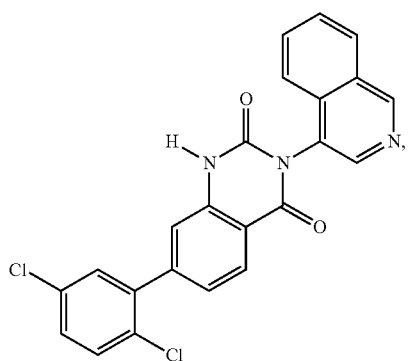
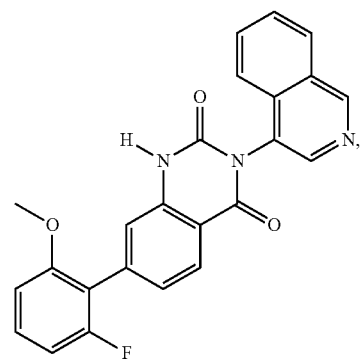
-continued
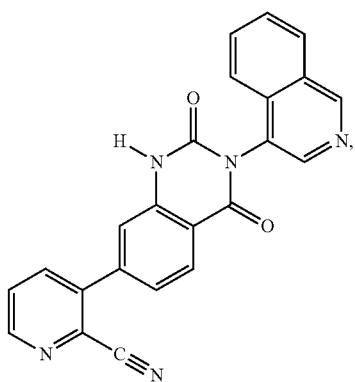
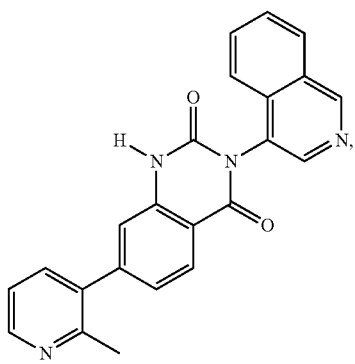
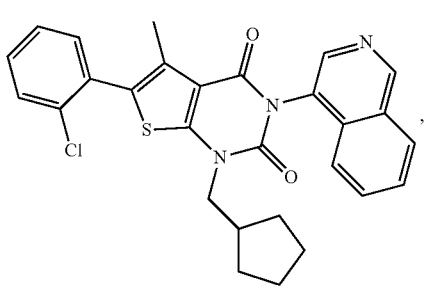
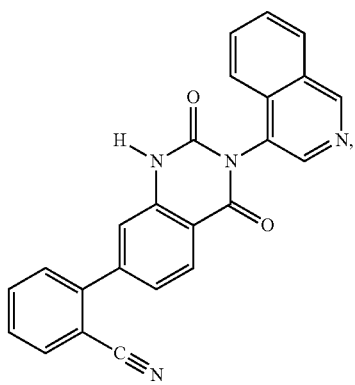

377
-continued
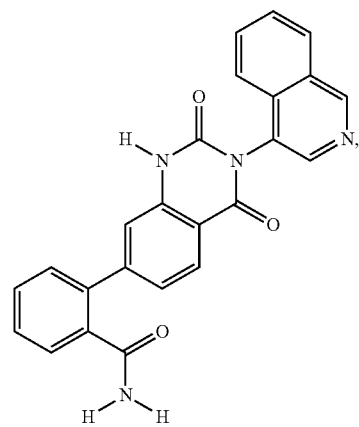
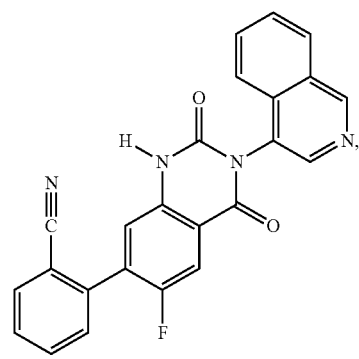
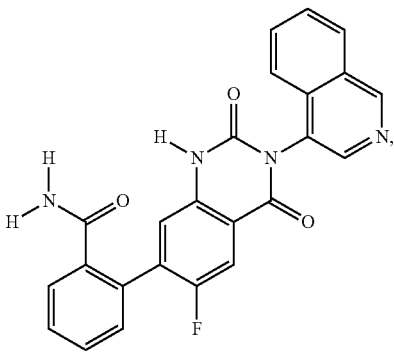
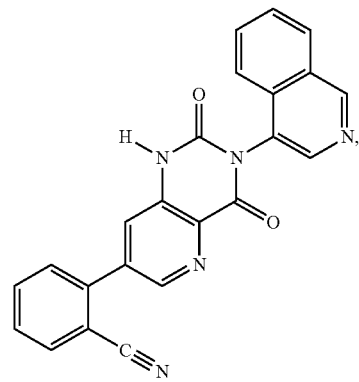
378
-continued
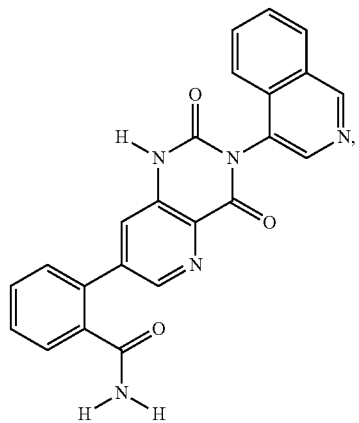
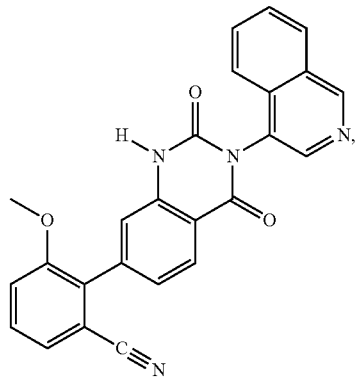
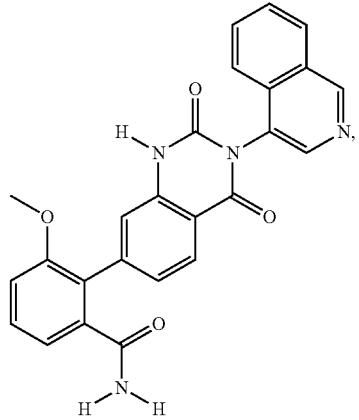
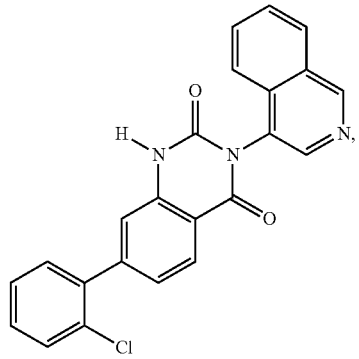

-continued
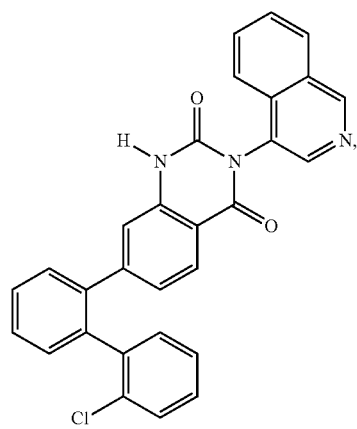
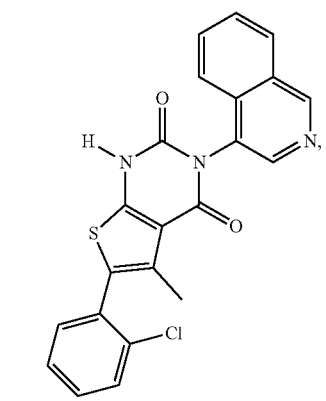
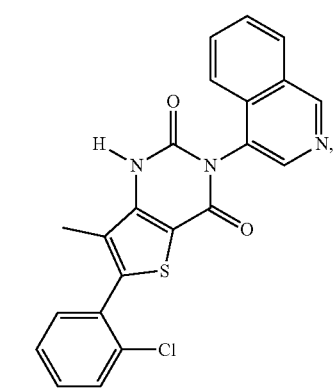
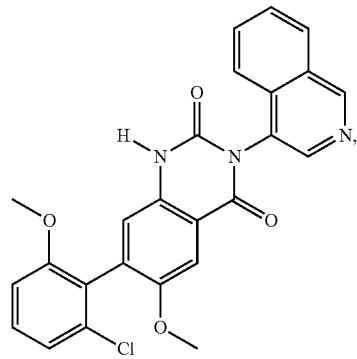
-continued
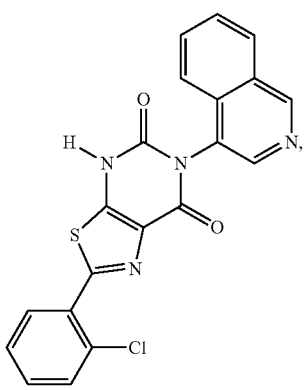
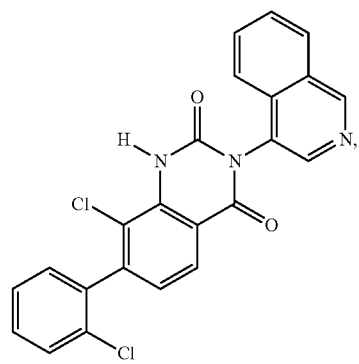
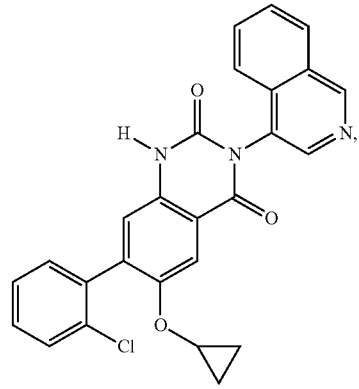
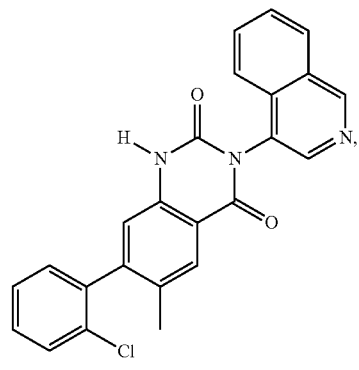

381
-continued
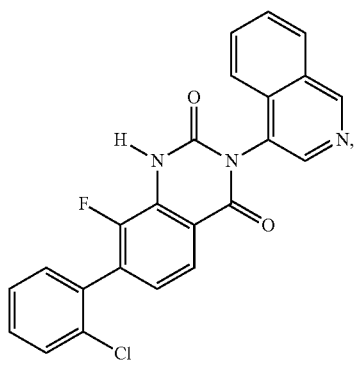
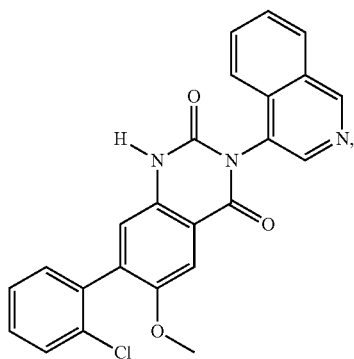
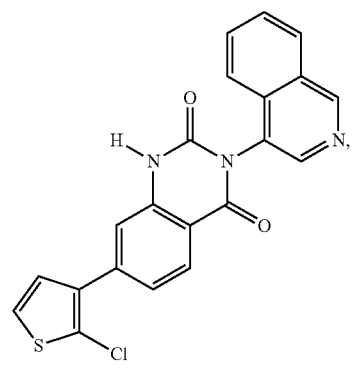
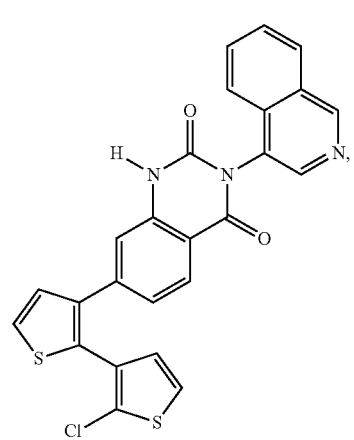
382
-continued
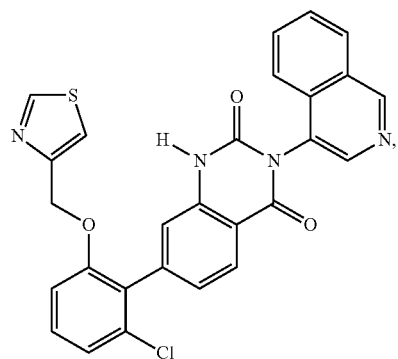
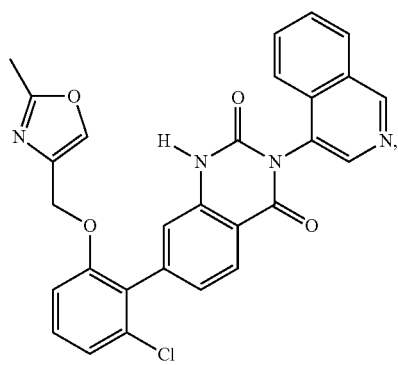
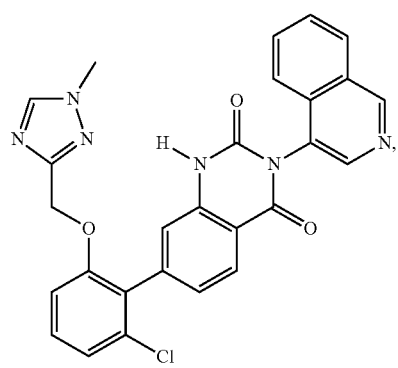
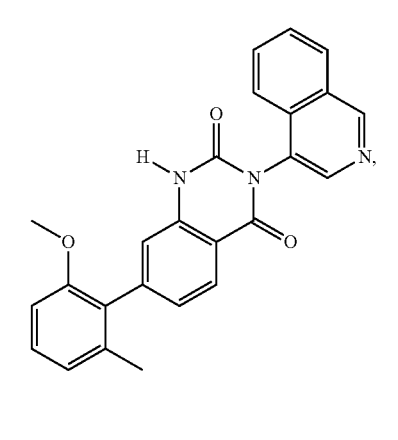

383
-continued
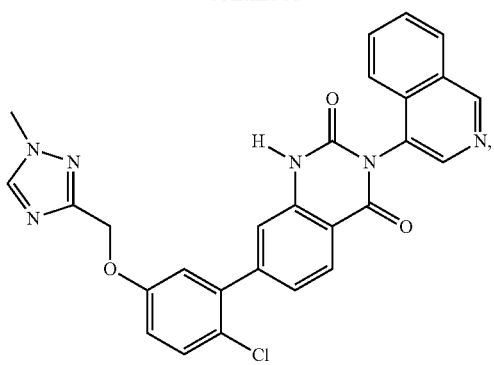
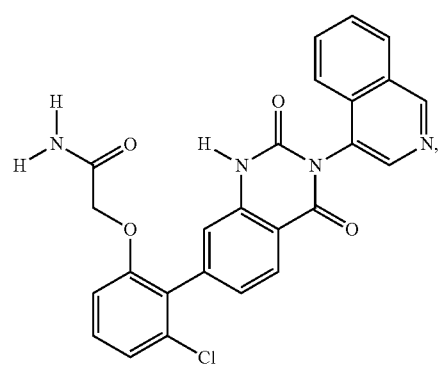
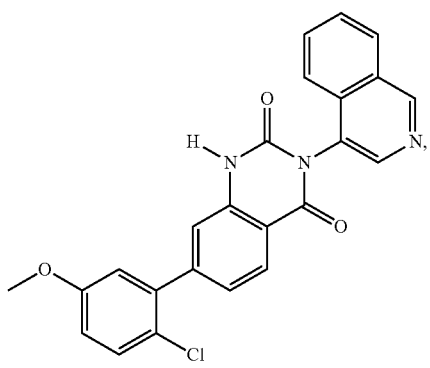
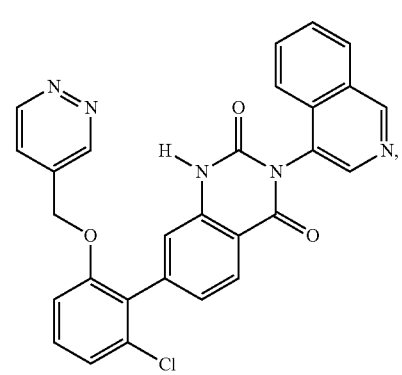
384
-continued
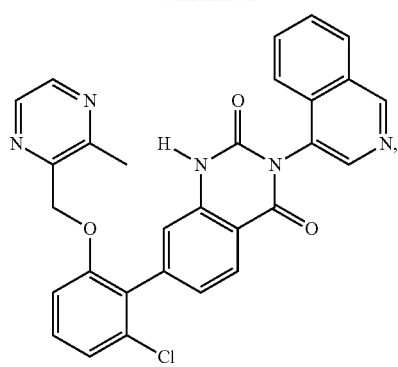
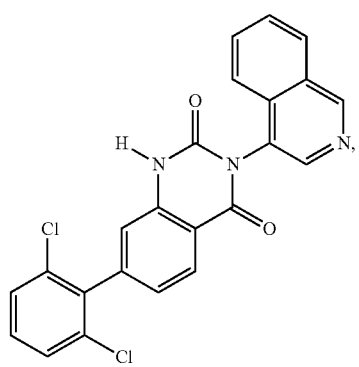
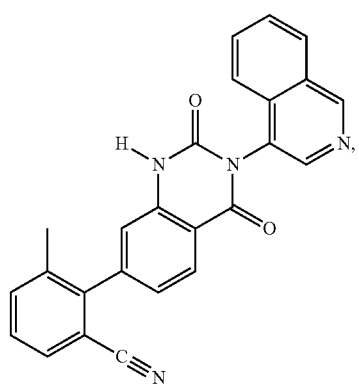
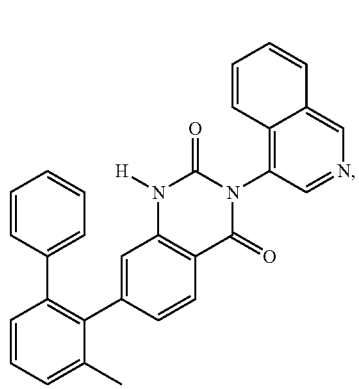

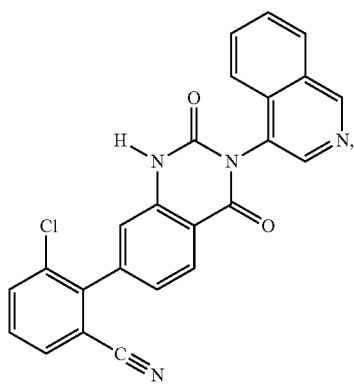
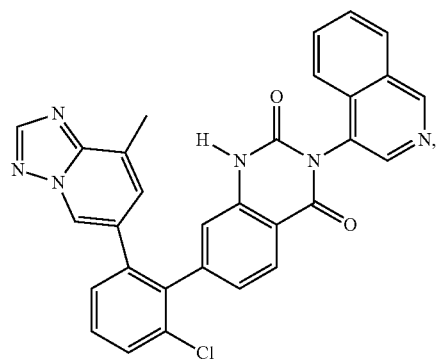
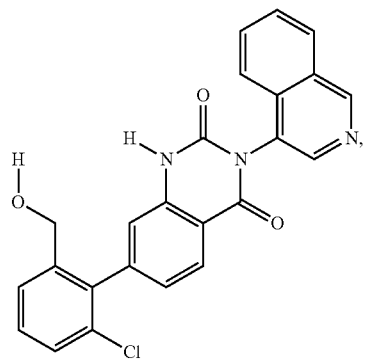
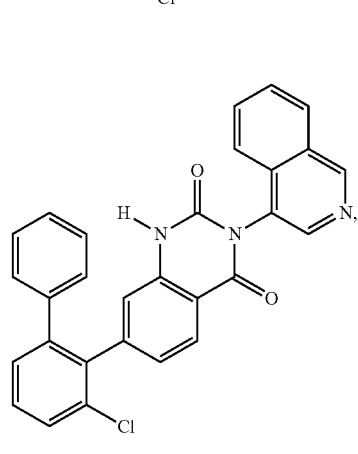
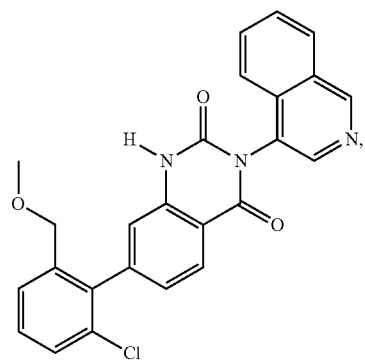
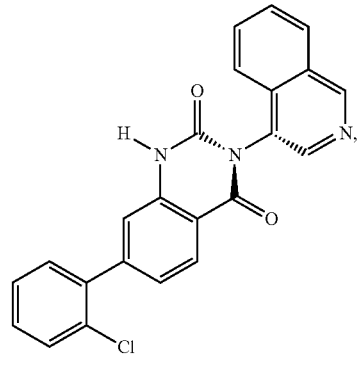
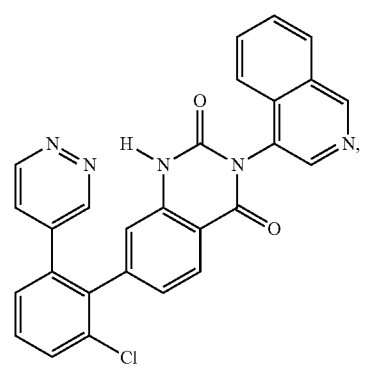
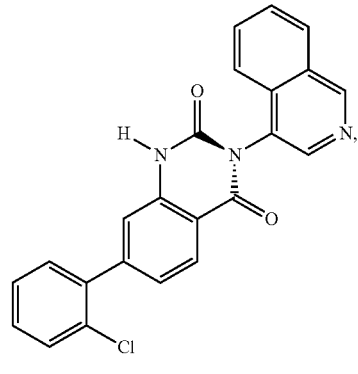

-continued
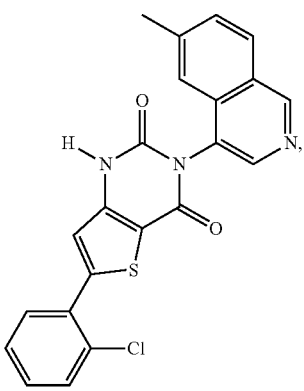
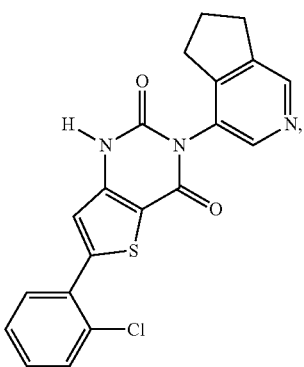
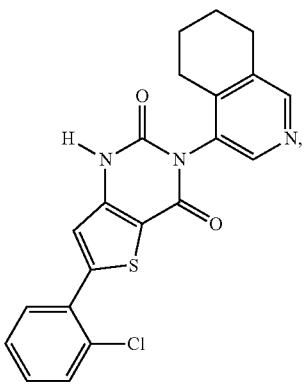
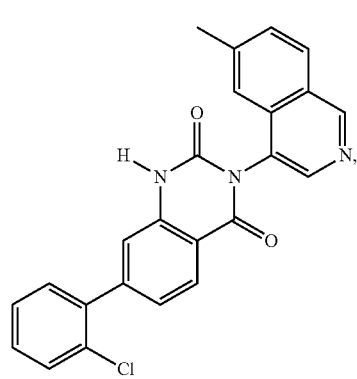
-continued
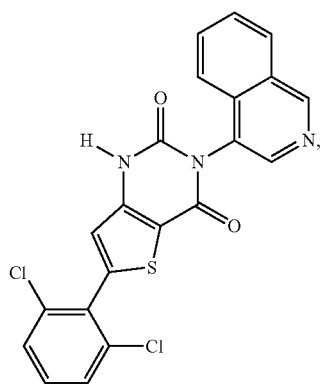
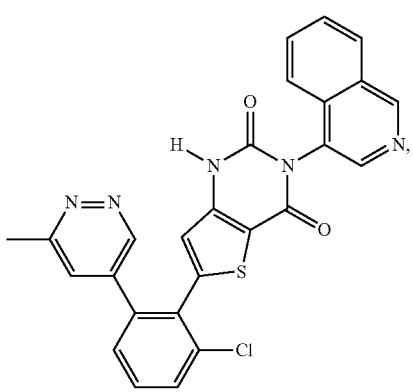
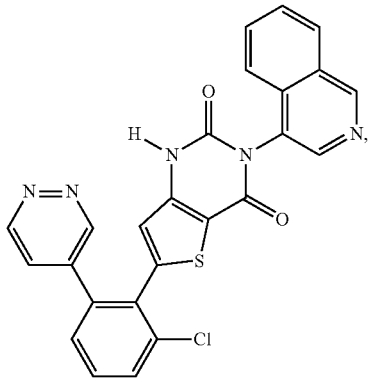
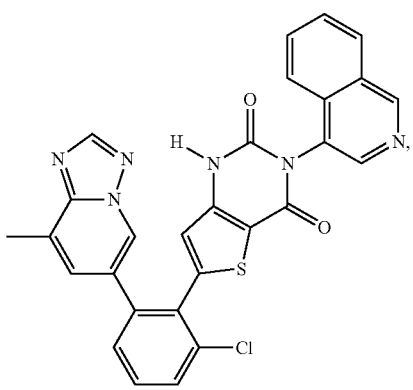

389
-continued
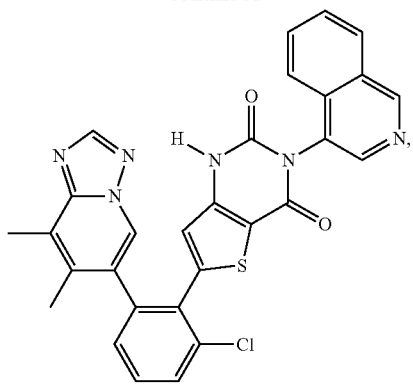
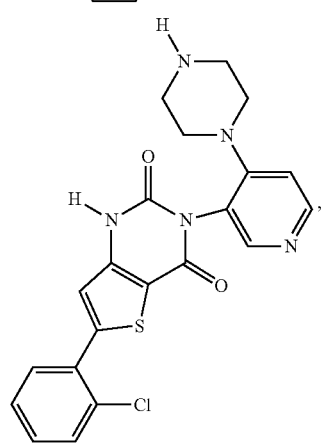
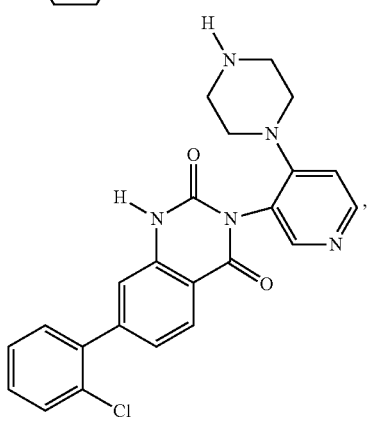
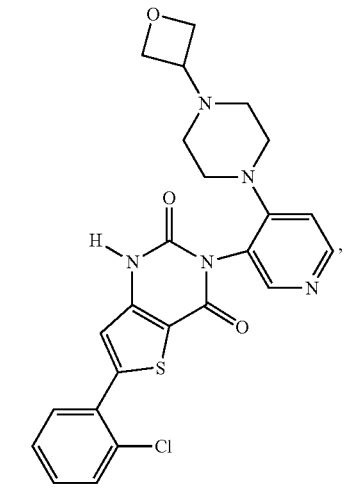
390
-continued
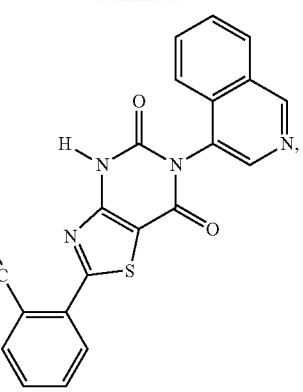
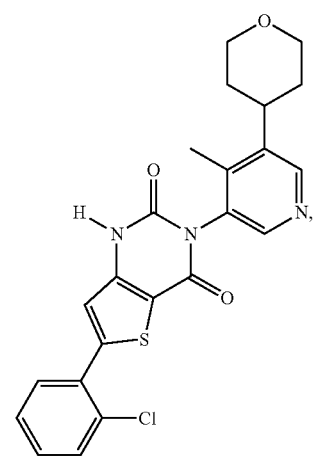
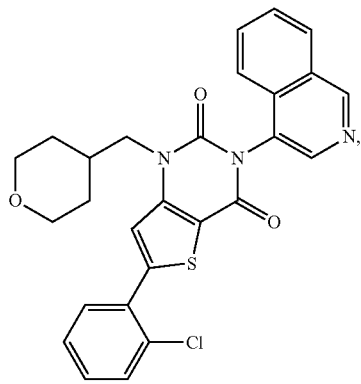
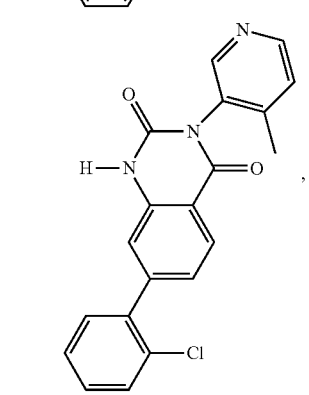

391
-continued
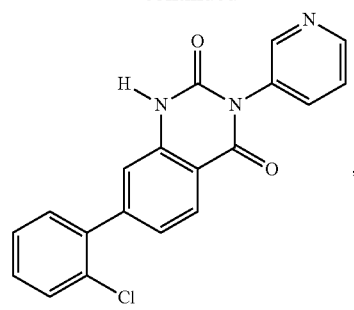
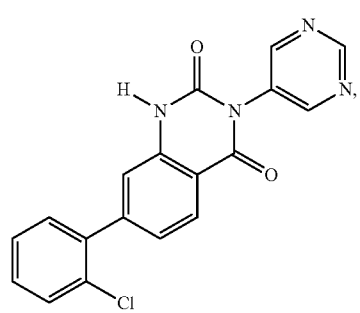
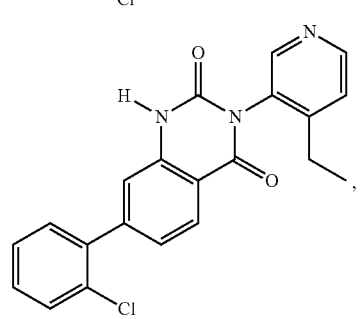
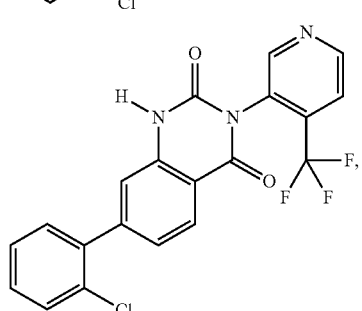
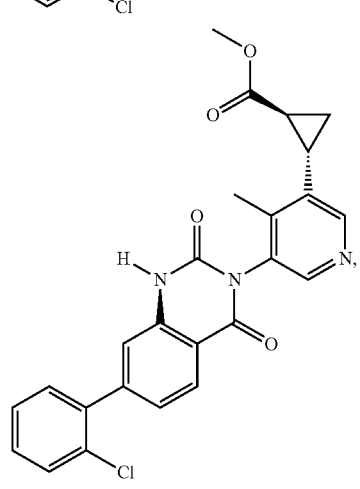
392
-continued
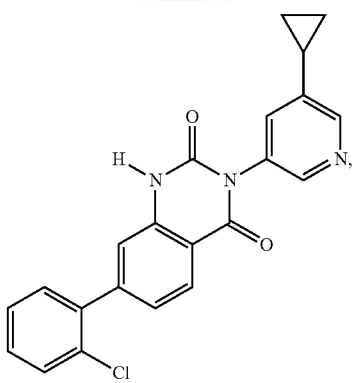
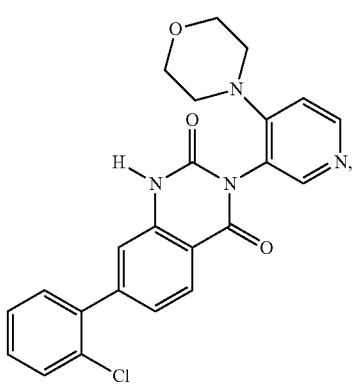
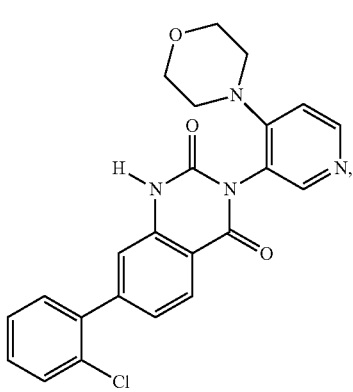
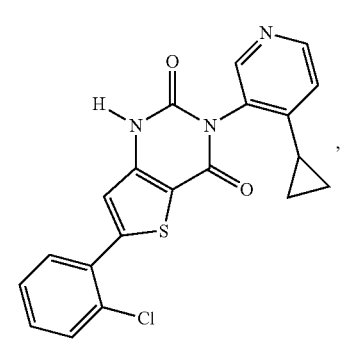

-continued
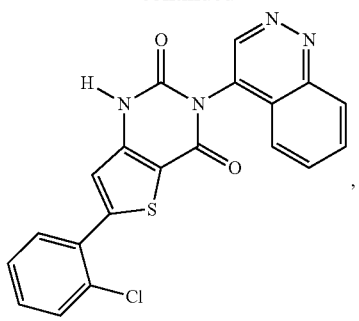
,
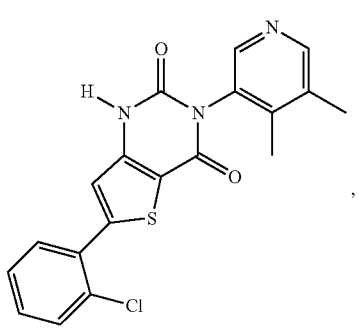
,
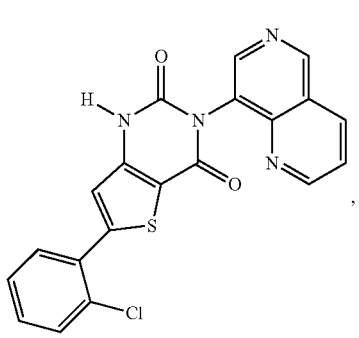
,
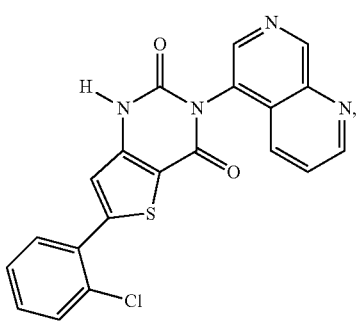
,
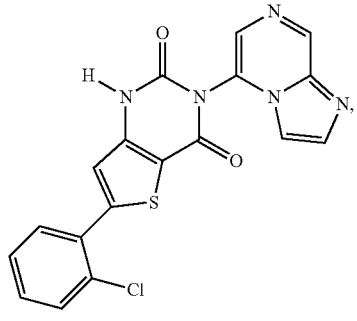
-continued
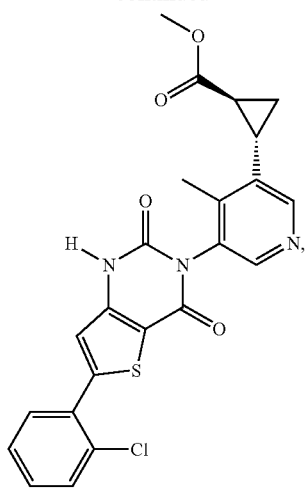
,
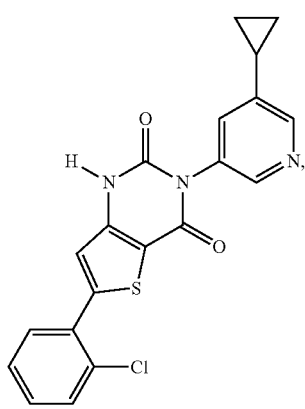
,
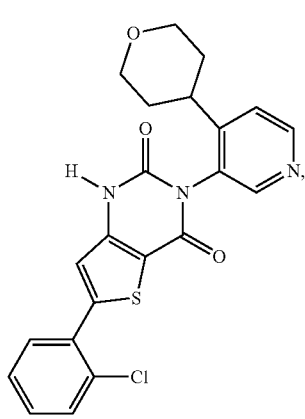
,

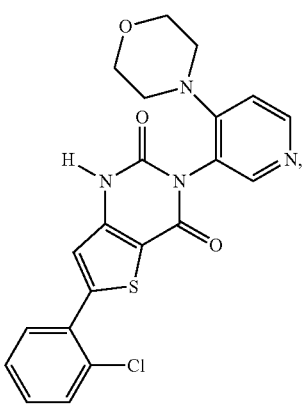
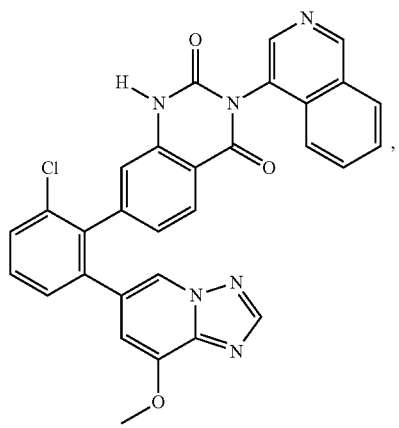
-continued
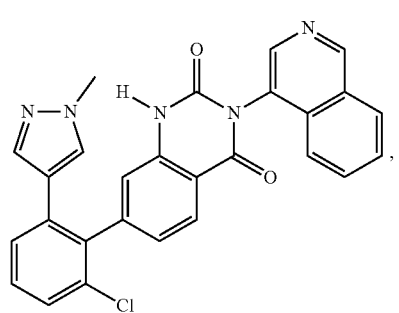
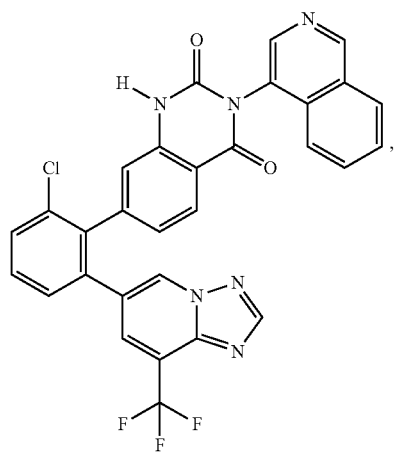
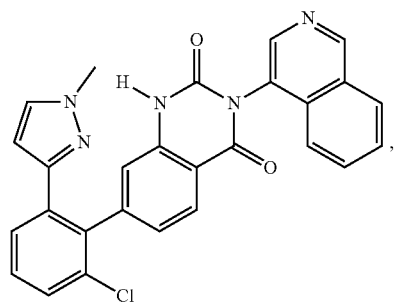

-continued
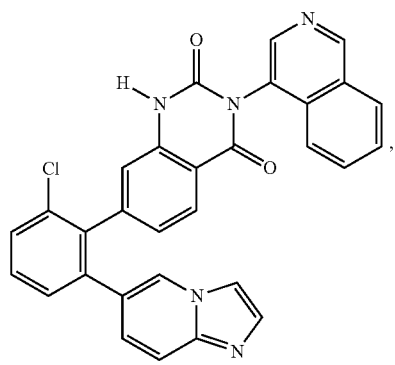
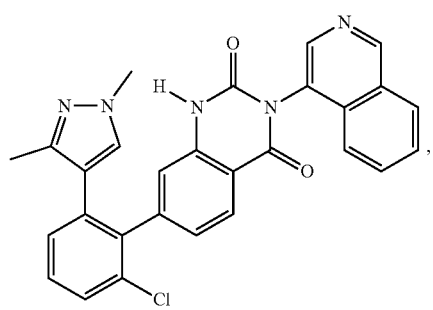
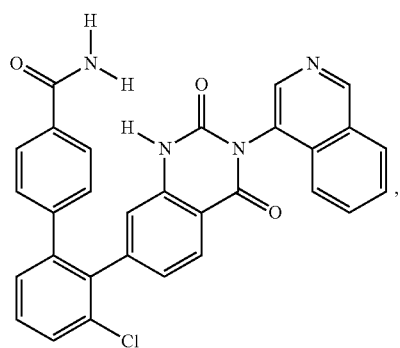
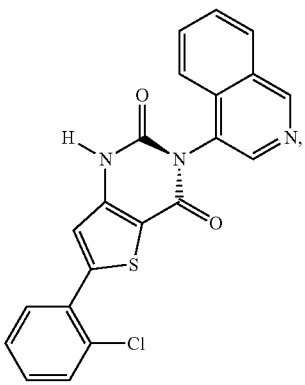
-continued
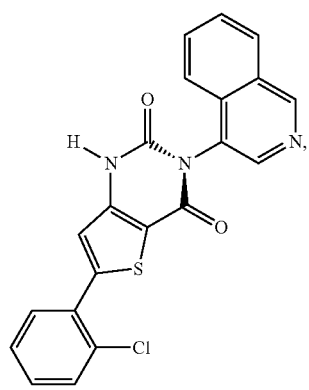
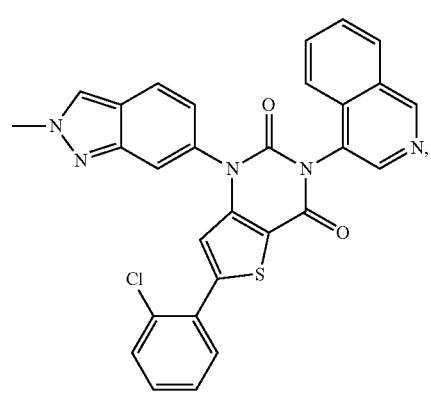
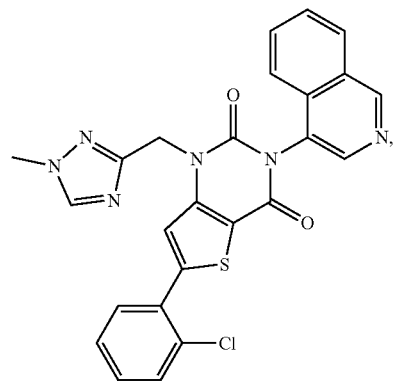
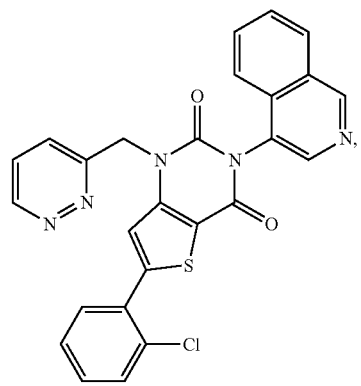

-continued
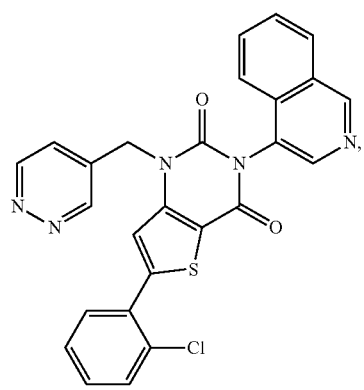
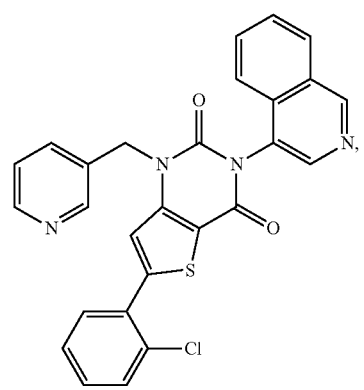
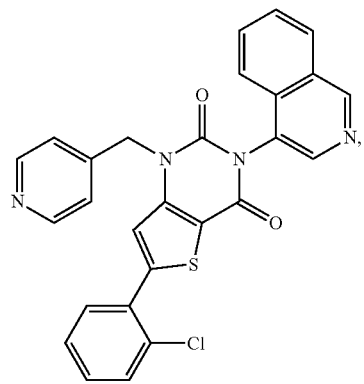
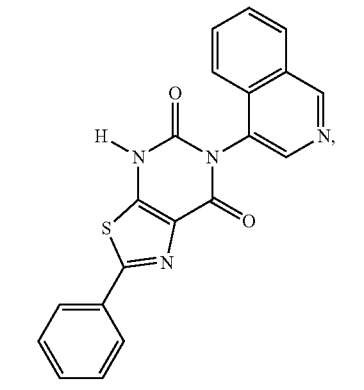
-continued
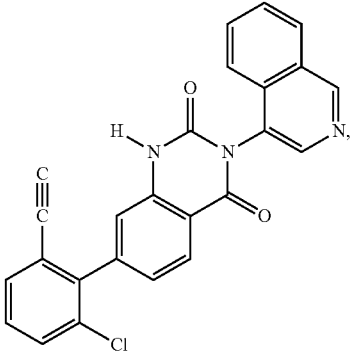
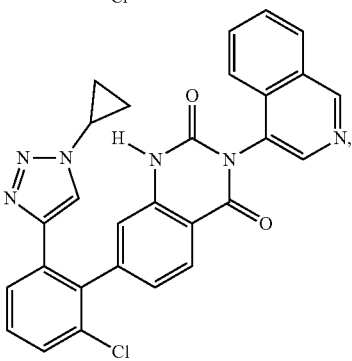
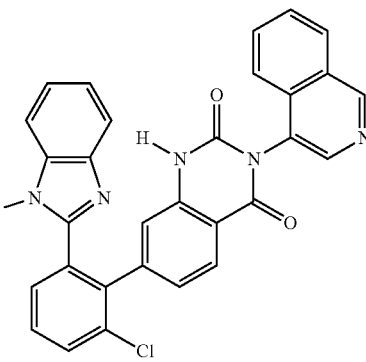
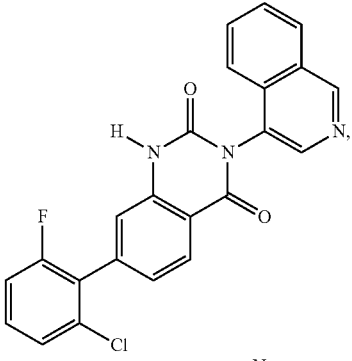
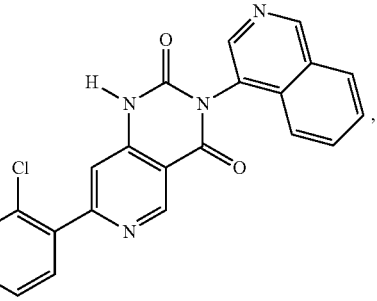

401
-continued
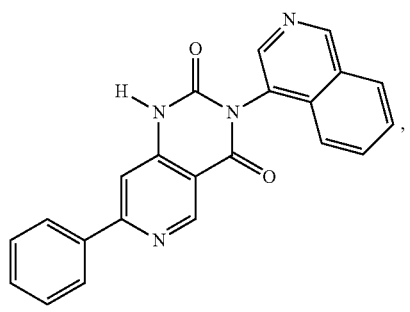
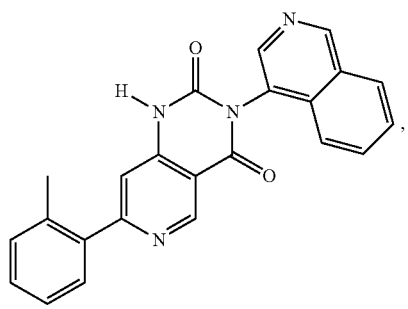
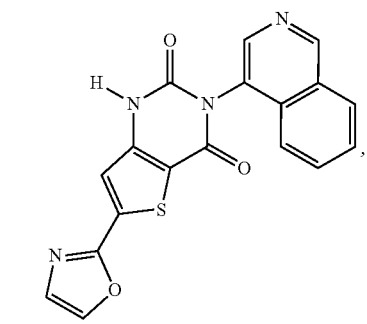
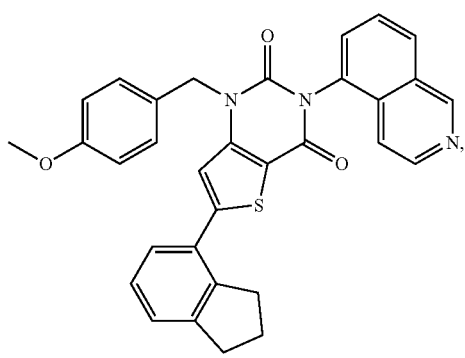
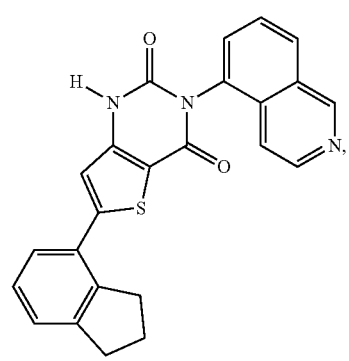
402
-continued
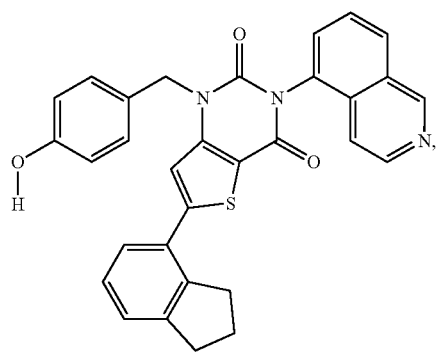
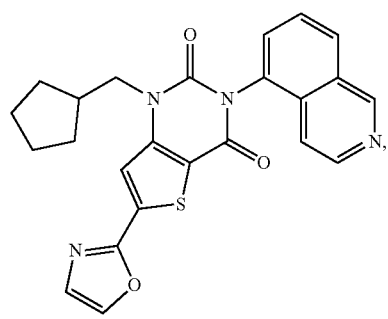
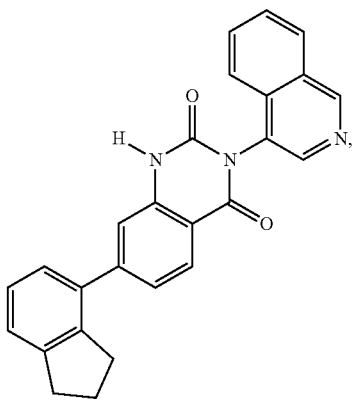
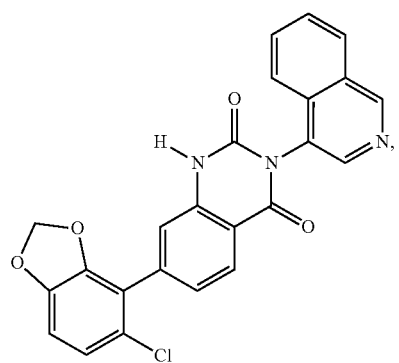

403
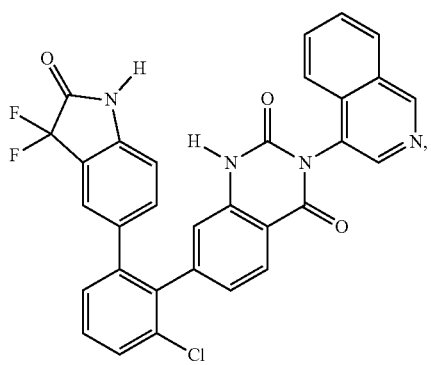
404
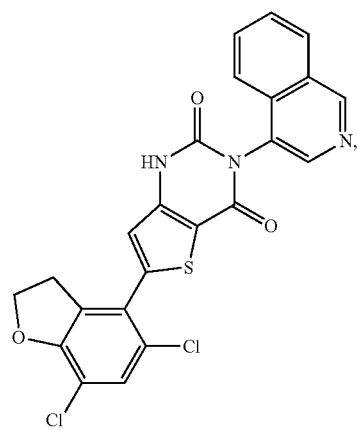
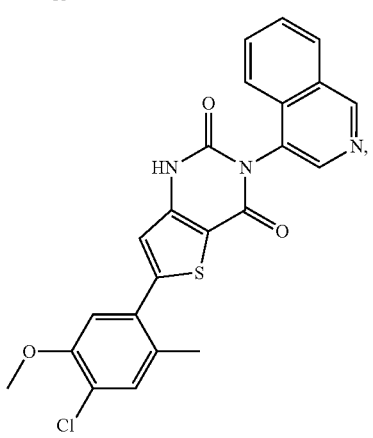
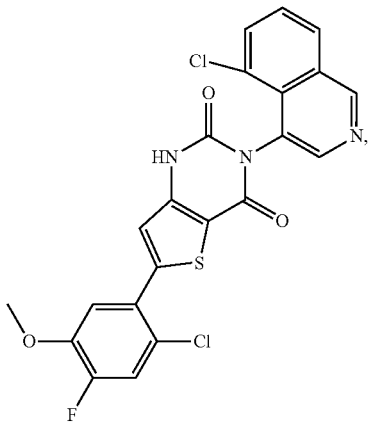
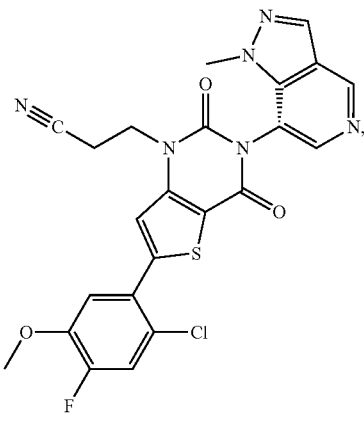

405
-continued
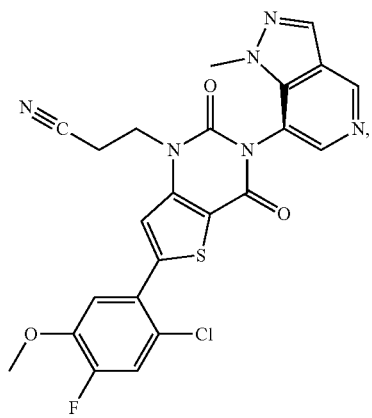
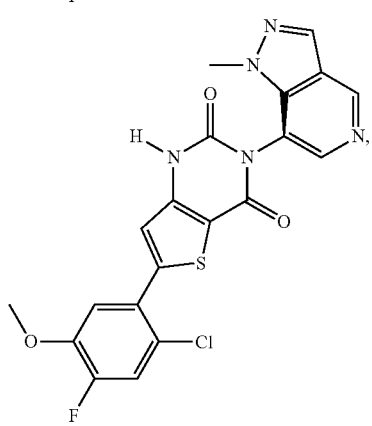
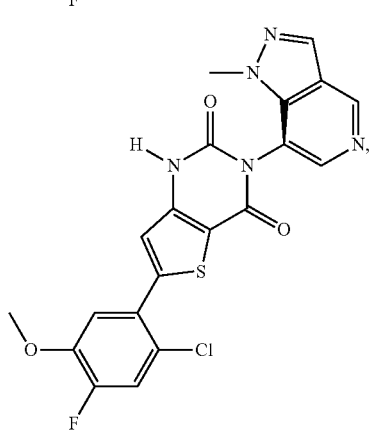

406
-continued
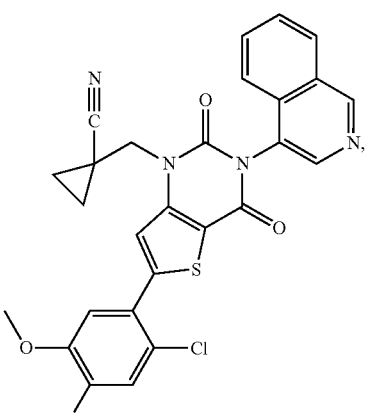
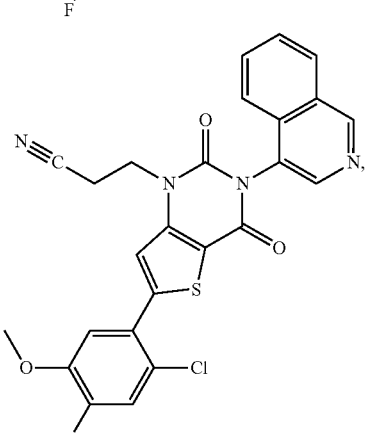
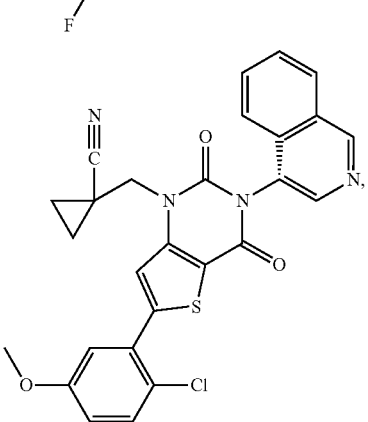
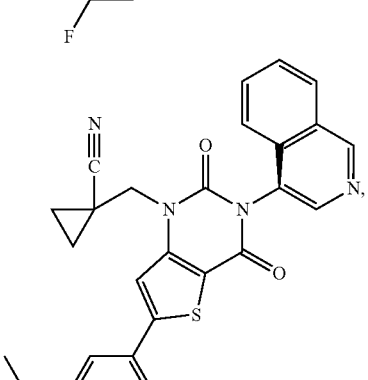

407
-continued
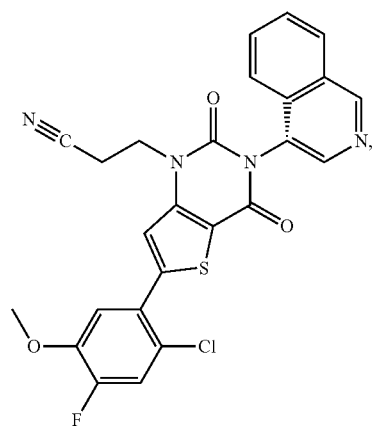
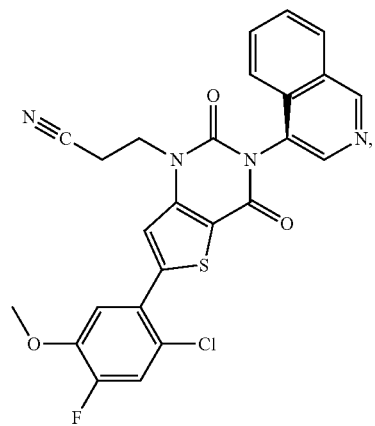
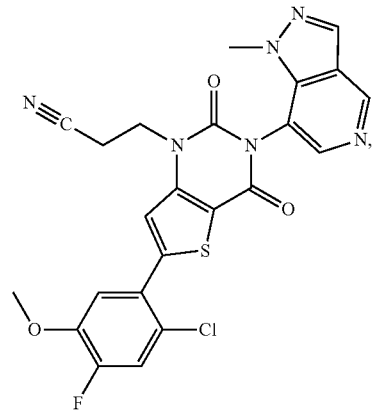
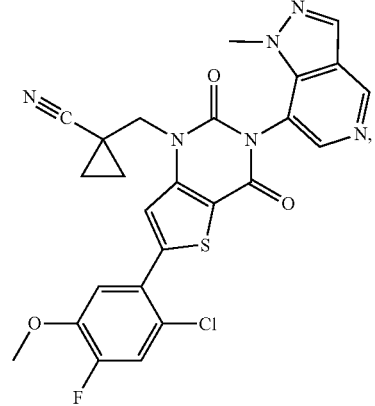
408
-continued
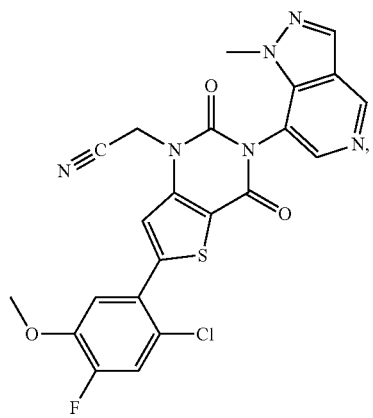
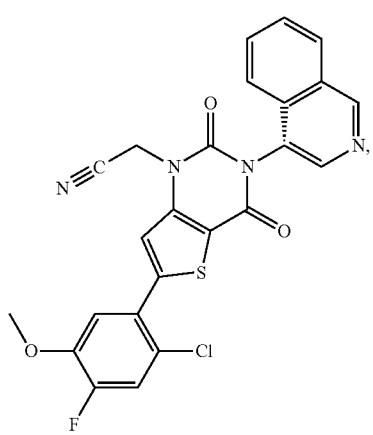
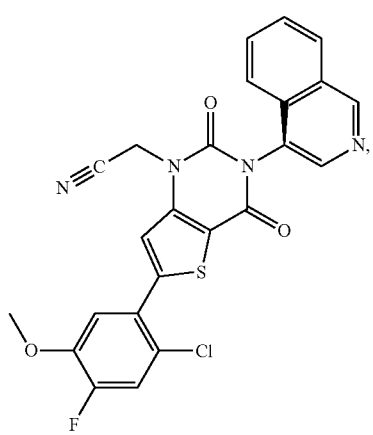
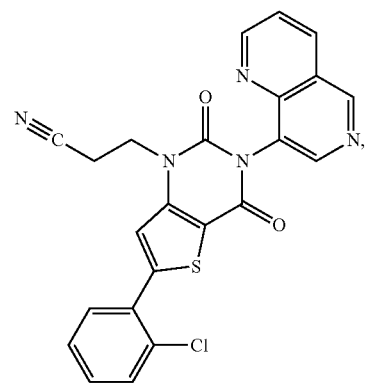

-continued
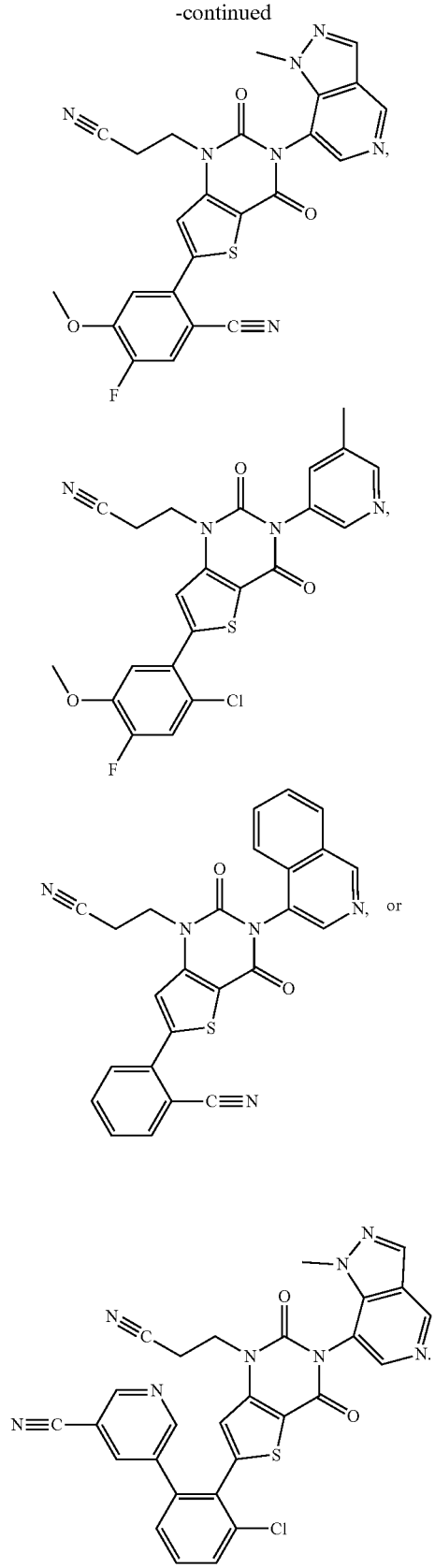
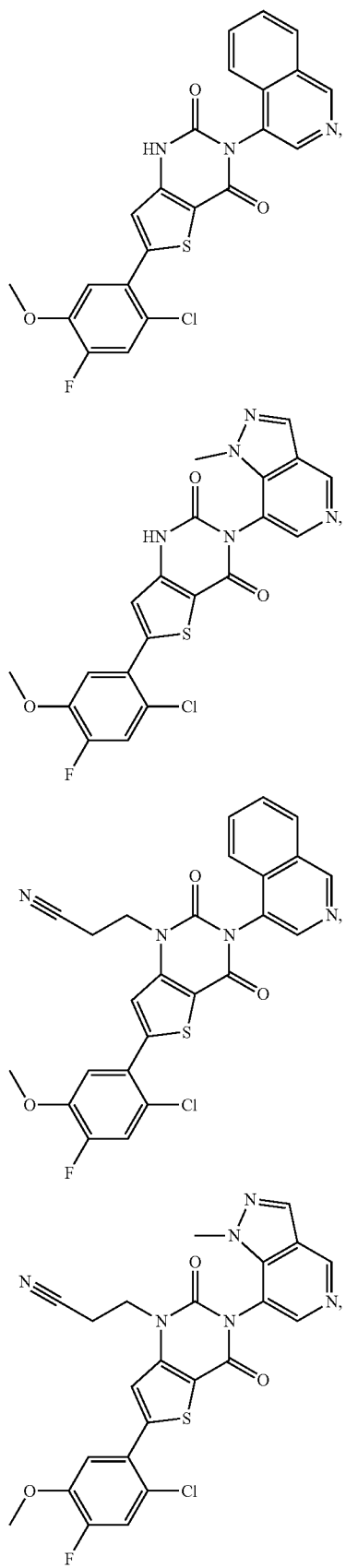
In some embodiments, a compound of the disclosure is selected from 411
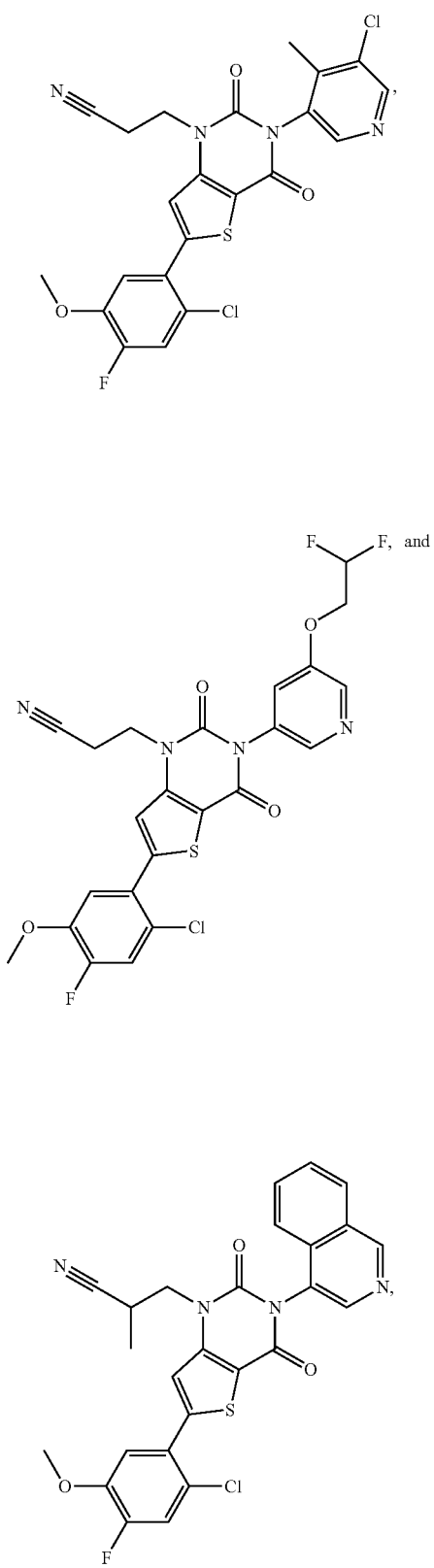
or a pharmaceutically acceptable salt thereof.
In some embodiments, a compound of the disclosure is selected from
412
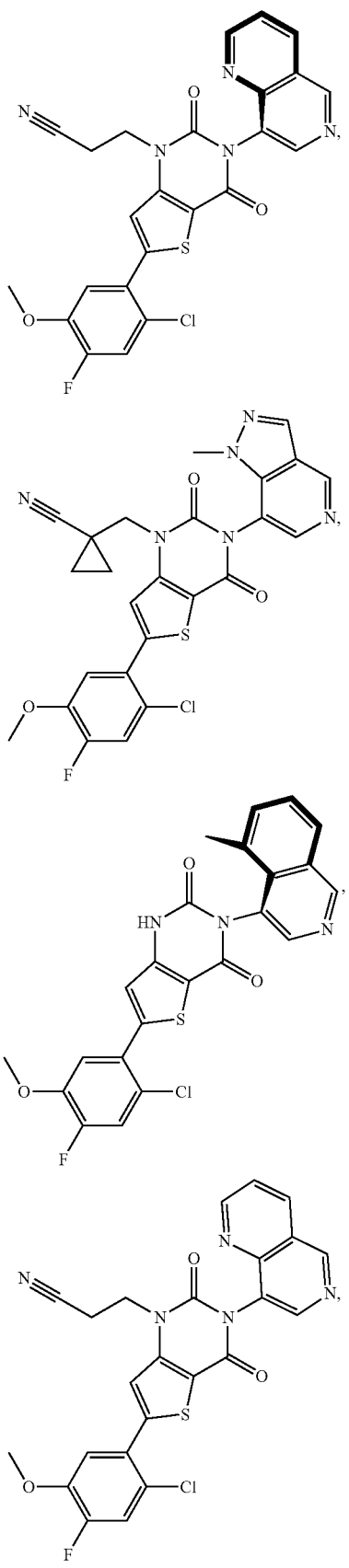

413
-continued
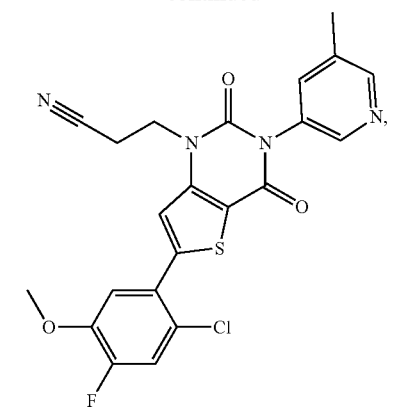
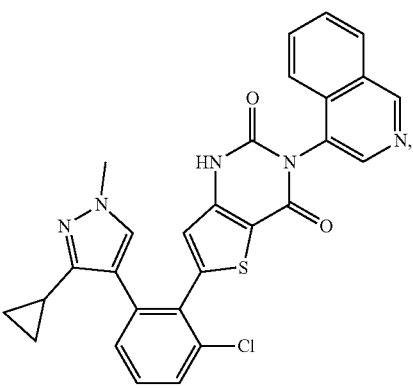
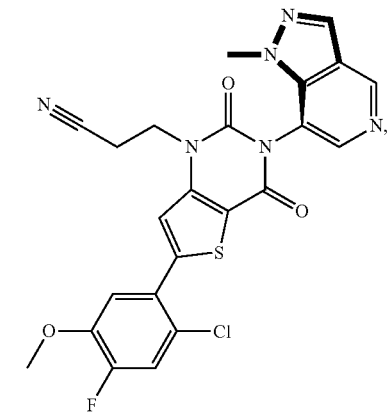
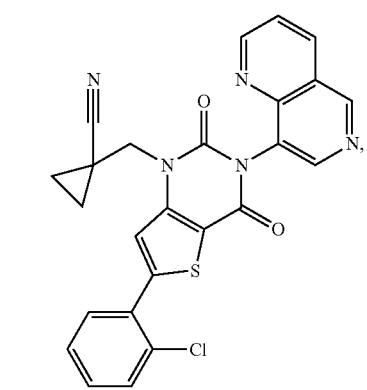
414
-continued
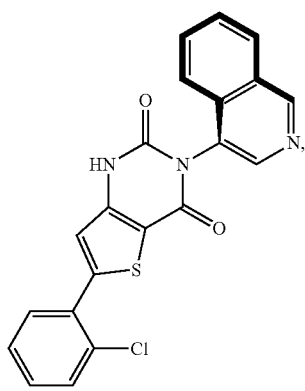
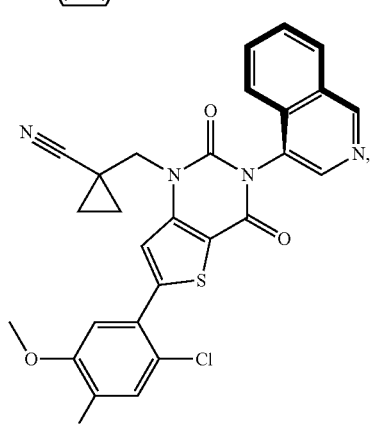
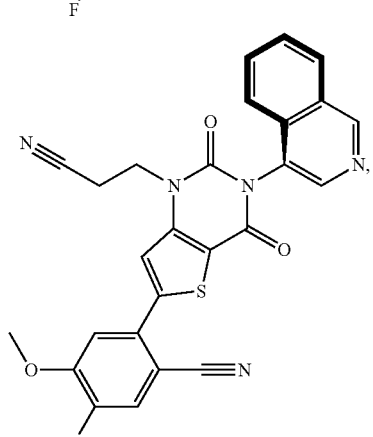
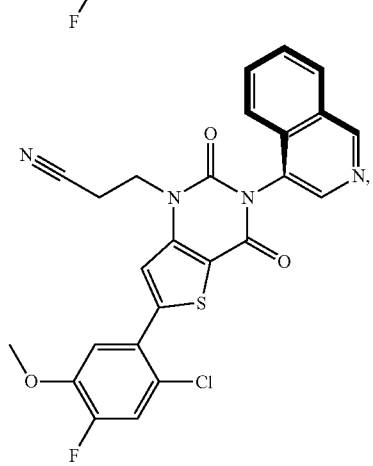

415

-continued

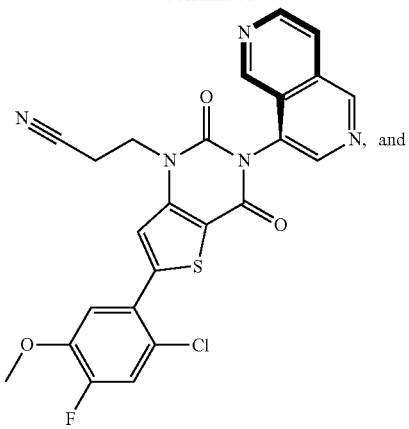

416

In some embodiments, a compound of the disclosure is

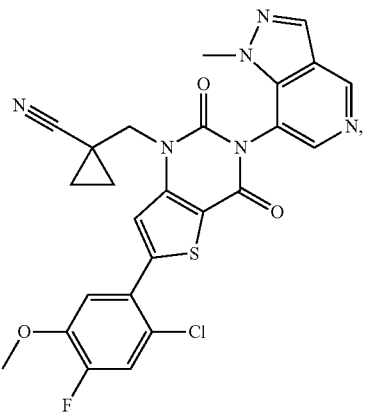

or a pharmaceutically acceptable salt thereof.

In some embodiments, a compound of the disclosure is

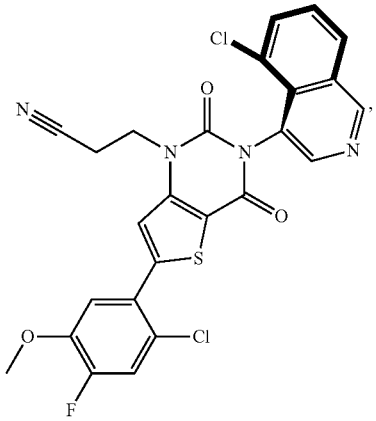

or a pharmaceutically acceptable salt thereof.

In some embodiments, a compound of the disclosure is

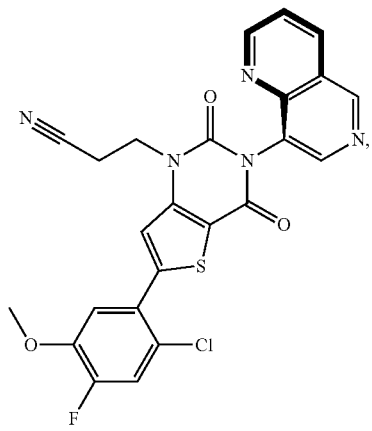

or a pharmaceutically acceptable salt thereof.

or a pharmaceutically acceptable salt thereof.

In some embodiments, a compound of the disclosure is

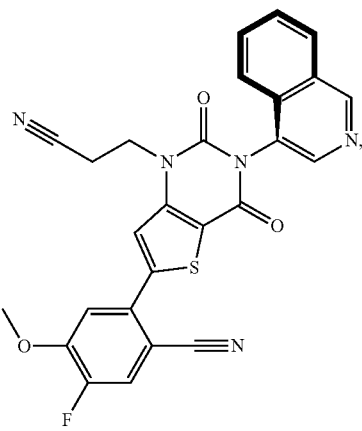

or a pharmaceutically acceptable salt thereof.

In some embodiments, a compound of the disclosure is

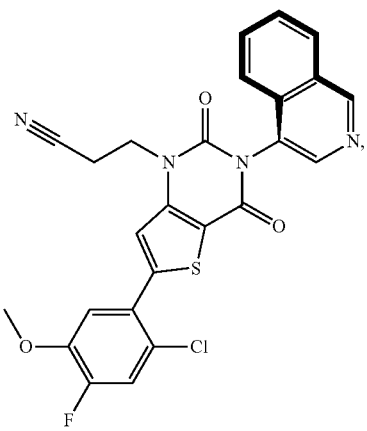

or a pharmaceutically acceptable salt thereof.

In some embodiments, a compound of the disclosure is

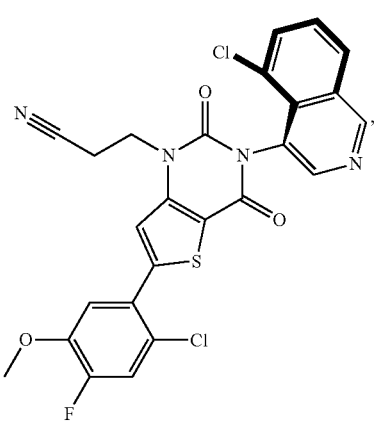

or a pharmaceutically acceptable salt thereof.

In some embodiments, a compound of the disclosure is a compound selected from any one of Examples 1 to 1102, or a pharmaceutically acceptable salt thereof.

Also falling within the scope herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g. $^{14}C$ or $^{3}H$) compound, administering it parenterally in a detectable dose (e.g. greater than about 0.5 mg/kg) to an animal such as rat, mouse, guinea pig, monkey, or to man, allowing sufficient time for metabolism to occur (typically about 30 seconds to about 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion. e.g., by MS or NMR analysis. In general, analysis of metabolites is done in the same way as conventional drug metabolism studies well-known to those skilled in the art.

The compounds of the present disclosure can be prepared by a variety of methods. For example, Schemes 1-11 show representative syntheses of the compounds of the present disclosure. Variables shown in the following schemes are for illustrative purposes only and are independent from those described elsewhere herein.

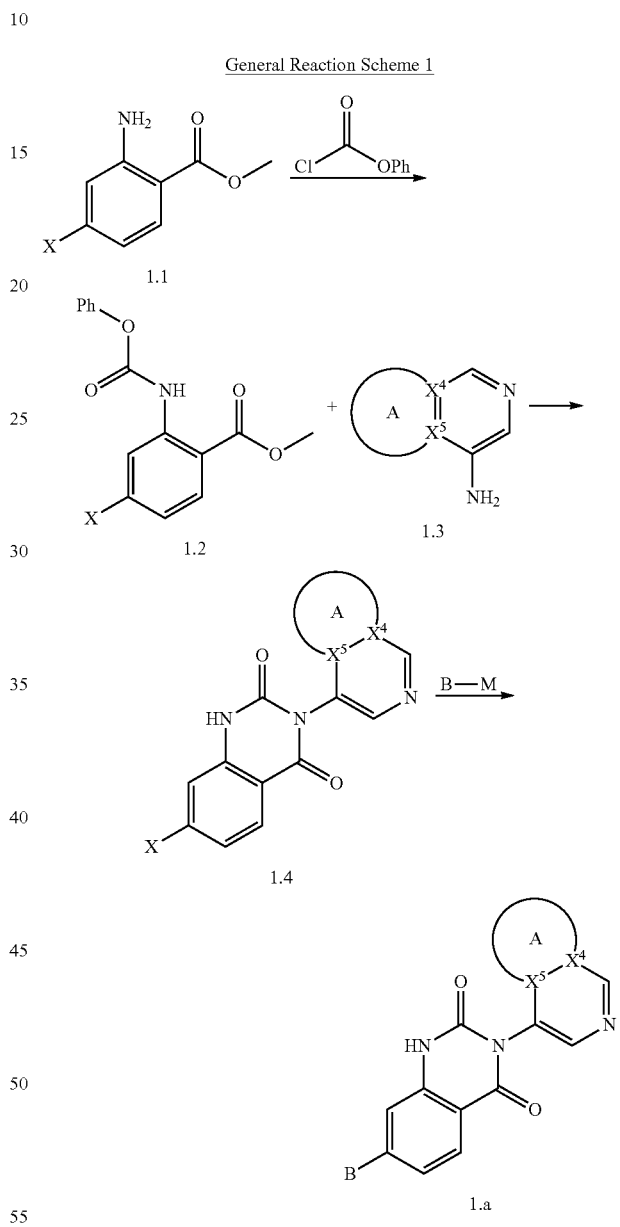

Intermediate 1.1 (where X is —OTf, —Cl, Br, or —I) can be reacted with phenyl chloroformate in the presence of a suitable base (e.g., DIPEA) and heated to give intermediate 1.2, Condensation between intermediate 1.2 and intermediate 1.3 in the presence of base and with heating gives intermediate 1.4. Metal mediated cross-coupling with a suitable coupling partner B-M (where B is aryl or heteroaryl and M is —B, —Sn, —Zn, —Si, or —Mg) in the presence of a suitable catalyst (i.e., Pd or Ni) can be used to provide compound of formula (1.a).

General Reaction Scheme 2

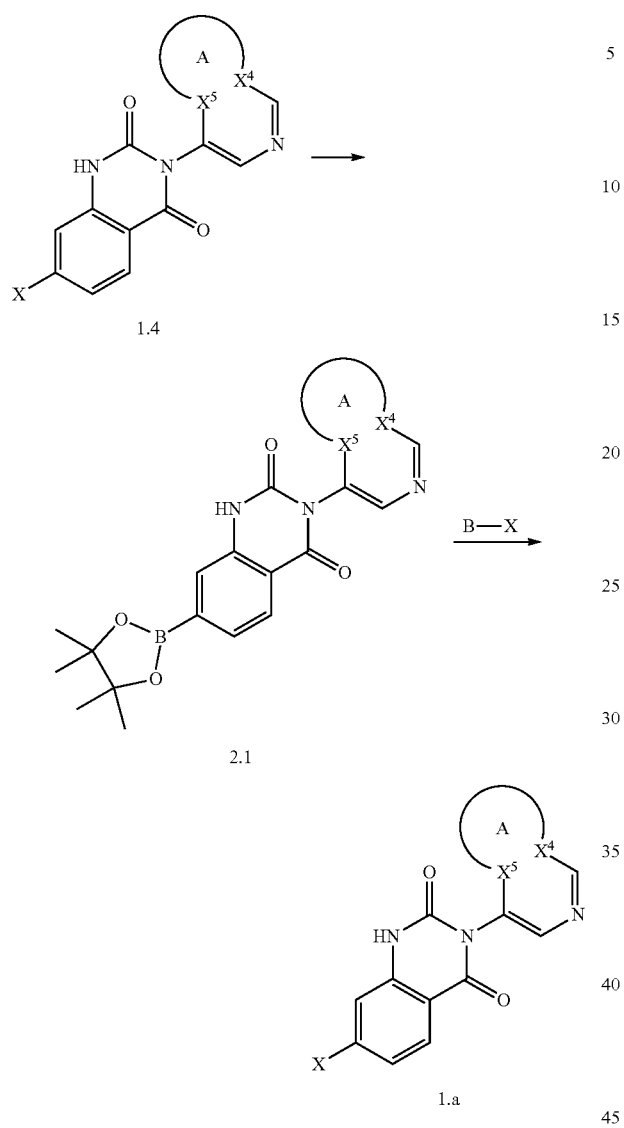

Palladium mediated borylation in the presence of Intermediate 1.4, bis(pinacolato)diboron, and a suitable Pd catalyst can used to provide intermediate 2.1. Metal mediated cross-coupling with a suitable coupling partner B-X (where B is aryl or heteroaryl and X is —Cl, —Br, —I, or OTf) in the presence of a suitable catalyst (i.e. Pd or Ni) can be used to provide compound of formula (1.a).

Intermediate 3.1 (where X is —Cl, Br, or —I) can be reacted with phenyl chloroformate in the presence of a suitable base (e.g., DIPEA) and heated to give intermediate 3.2. Condensation between intermediate 3.2 and intermediate 1.3 in the presence of base and with heating gives intermediate 3.3. Metal mediated cross-coupling with a suitable coupling partner B-M (where B is aryl, heteroaryl and M is —B, —Sn. —Zn, —Si, or —Mg) in the presence of a suitable catalyst (i.e., Pd or Ni) can be used to provide compound of formula (I.b).

General Reaction Scheme 3

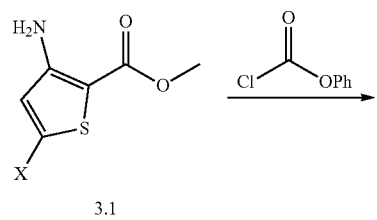

General Reaction Scheme 4

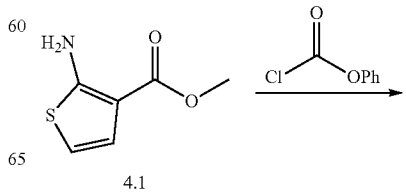

-continued

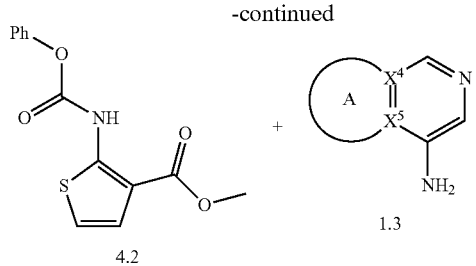
4.2

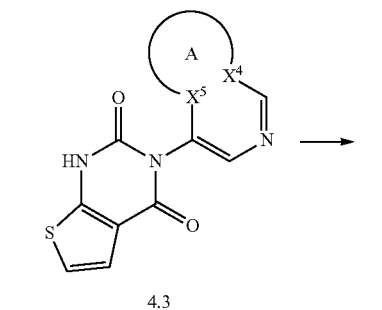
4.3

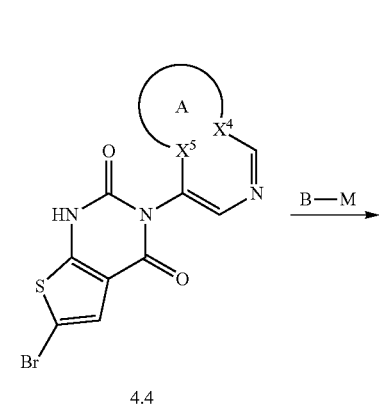
4.4

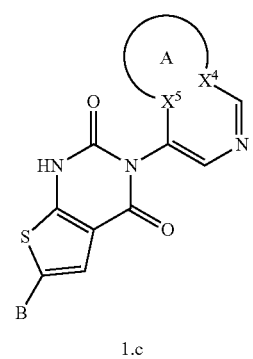
1.c

Intermediate 4.1 can be reacted with phenyl chloroformate in the presence of a suitable base (e.g., DIPEA) and heated to give intermediate 4.2, Condensation between intermediate 4.2 and intermediate 1.3 in the presence of base and with heating gives intermediate 4.3. Intermediate 4.3 may be reacted with NBS to provide intermediate 4.4. Metal mediated cross-coupling with a suitable coupling partner B-M (where B is aryl, heteroaryl and M is —B, —Sn, —Zn, —Si, or —Mg) in the presence of a suitable catalyst (i.e., Pd or Ni) can be used to provide compound of formula (1.c).

General Reaction Scheme 5

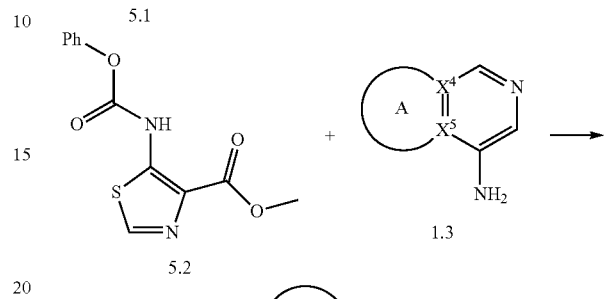
5.1

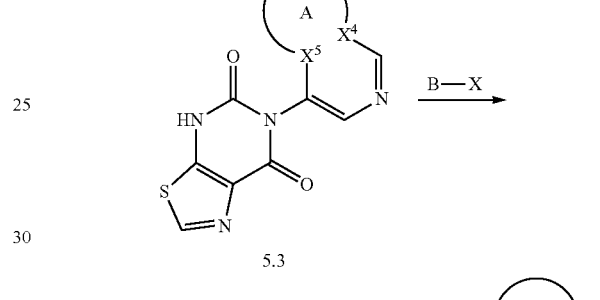
5.2

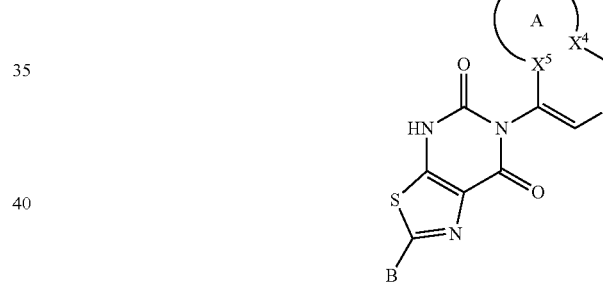
5.3

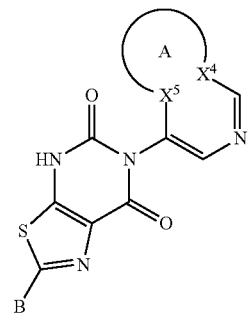
1.d

Intermediate 5.1 can be reacted with phenyl chloroformate in the presence of a suitable base (e.g., DIPEA) and heated to give intermediate 5.2, Condensation between intermediate 5.2 and intermediate 1.3 in the presence of base and with heating gives intermediate 5.3. Metal mediated C—H arylation with a suitable coupling partner B-X (where B is aryl, heteroaryl and X is —Cl, —Br, —I, or OTf) in the presence of a suitable catalyst (i.e., Pd) can be used to provide compound of formula (I.d).

General Reaction Scheme 6

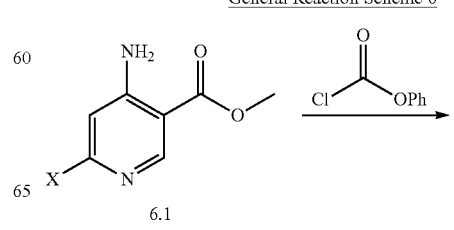
6.1

-continued

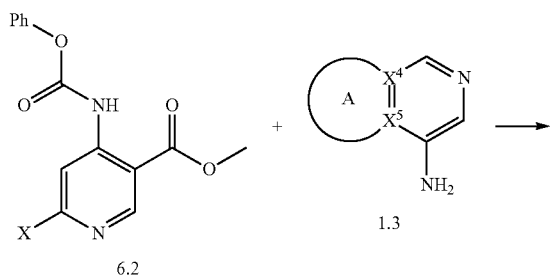

6.2

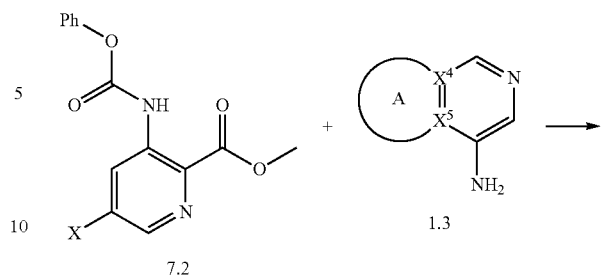

7.2

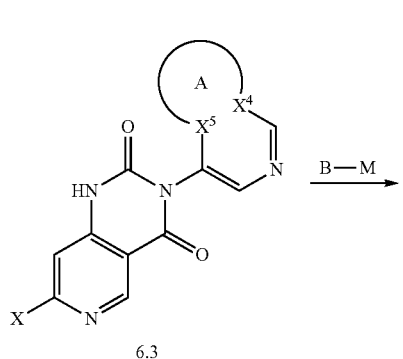

6.3

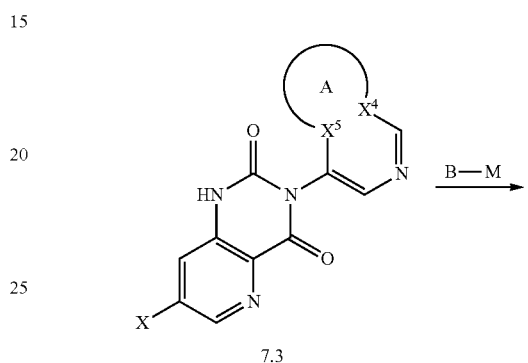

7.3

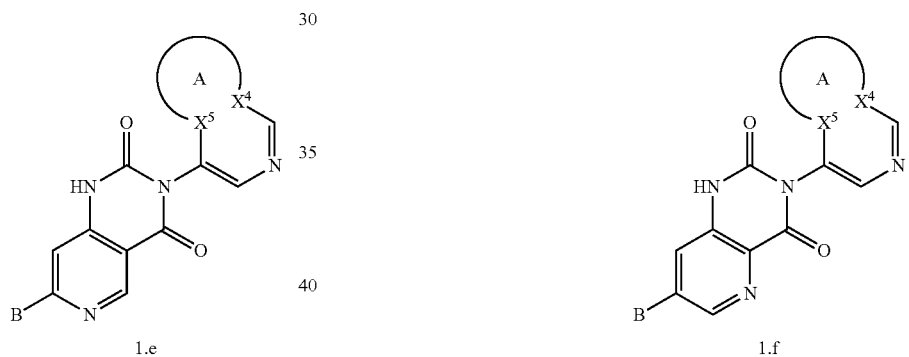

1.e

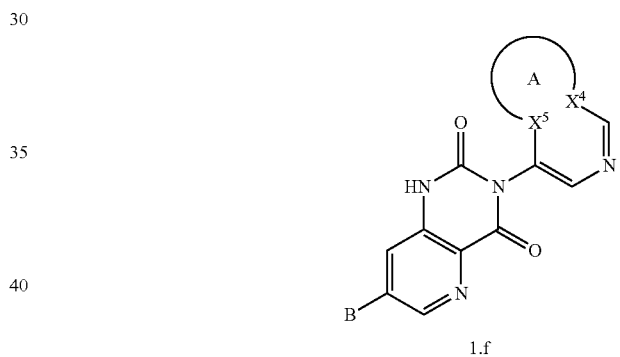

1.f

Intermediate 6.1 (where X is —OTf, —Cl, Br, or —I) can be reacted with phenyl chloroformate in the presence of a suitable base (e.g., DIPEA) and with heating to give intermediate 6.2, Condensation between intermediate 6.2 and intermediate 1.3 in the presence of base and with heating gives intermediate 6.3. Metal mediated cross-coupling with a suitable coupling partner B-M (where B is aryl or heteroaryl and M is —B, —Sn. —Zn, —Si, or —Mg) in the presence of a suitable catalyst (i.e., Pd or Ni) can be used to provide compound of formula (I.e).

Intermediate 7.1 (where X is —OTf, —Cl, Br, or —I) can be reacted with phenyl chloroformate in the presence of a suitable base (e.g., DIPEA) and heated to give intermediate 7.2, Condensation between intermediate 7.2 and intermediate 1.3 in the presence of base and with heating gives intermediate 7.3. Metal mediated cross-coupling with a suitable coupling partner B-M (where B is aryl, heteroaryl and M is —B, —Sn, —Zn, —Si, or —Mg) in the presence of a suitable catalyst (i.e., Pd or Ni) can be used to provide compound of formula (1.f).

General Reaction Scheme 7

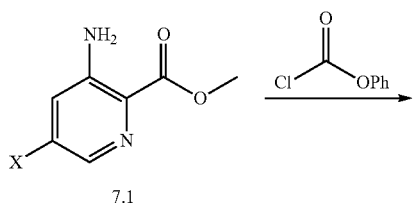

7.1

General Reaction Scheme 8

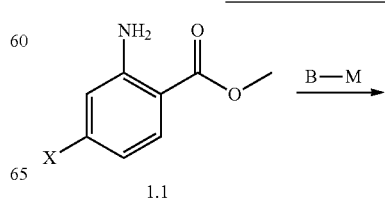

1.1

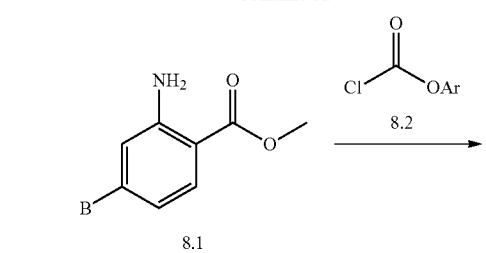

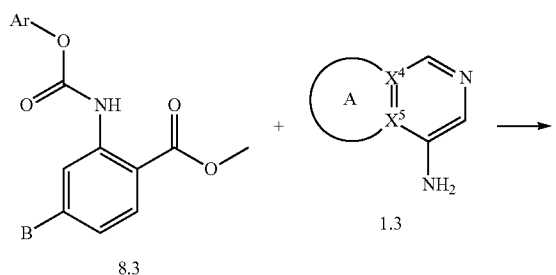

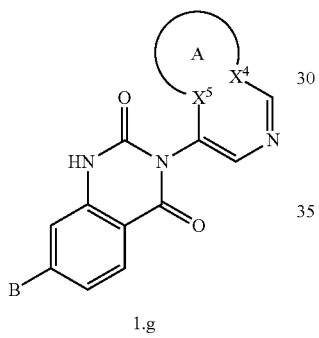

Metal mediated cross-coupling with Intermediate 1.1 (where X is —OTf, —Cl, Br, or —I) and a suitable coupling partner B-M (where B is aryl, heteroaryl and M is —B, —Sn, —Zn, —Si, or —Mg) in the presence of a suitable catalyst (i.e., Pd or Ni) can be used to produce Intermediate 8.1. Intermediate 8.1 can be reacted with Intermediate 8.2 in the presence of a suitable base (e.g., DIPEA) and with heating to give intermediate 8.3, Condensation between intermediate 8.3 and intermediate 1.3 in the presence of base and with heating can be used to provide compounds of formula (1.g).

General Reaction Scheme 9

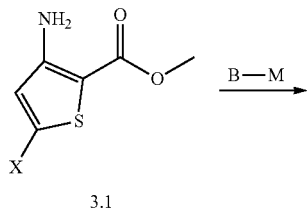

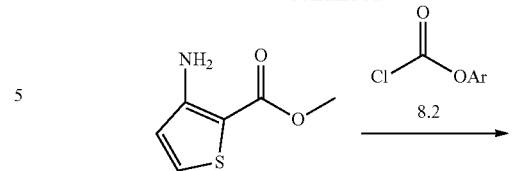

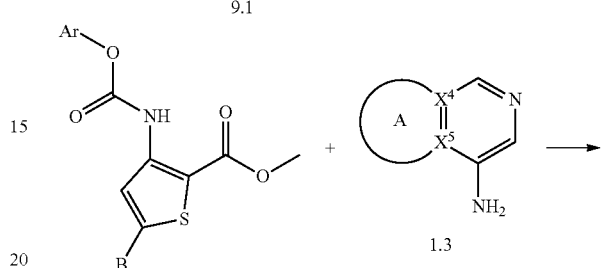

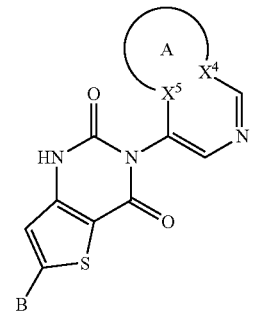

Metal mediated cross-coupling with Intermediate 3.1 (where X is —OTf, —Cl, Br, or —I) and a suitable coupling partner B-M (where B is aryl, heteroaryl and M is —B, —Sn, —Zn, —Si, or —Mg) in the presence of a suitable catalyst (i.e., Pd or Ni) can be used to produce Intermediate 9.1. Intermediate 9.1 can be reacted with Intermediate 8.2 in the presence of a suitable base (e.g., DIPEA) and with heating to give intermediate 9.2, Condensation between intermediate 9.2 and intermediate 1.3 in the presence of base and with heating can be used to provide compounds of formula (1.h).

General Reaction Scheme 10

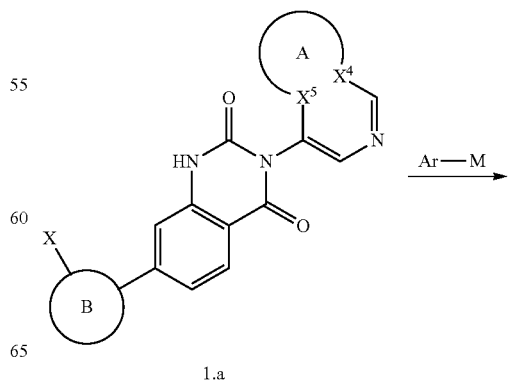

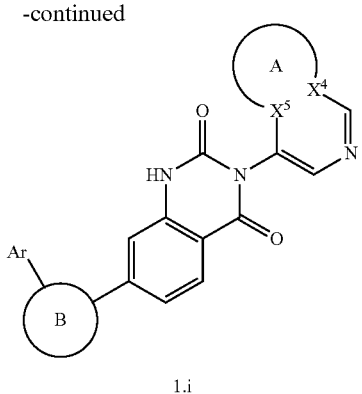

1.i

Metal mediated cross-coupling of compounds of formula 1.a (where X is —OTf, —Cl, Br, or —I) with a suitable coupling partner Ar-M (where Ar is aryl or heteroaryl and M is —B, —Sn, —Zn, —Si, or —Mg) in the presence of a suitable catalyst (i.e., Pd or Ni) can be used to provide compound of formula (1.i).

General Reaction Scheme 11

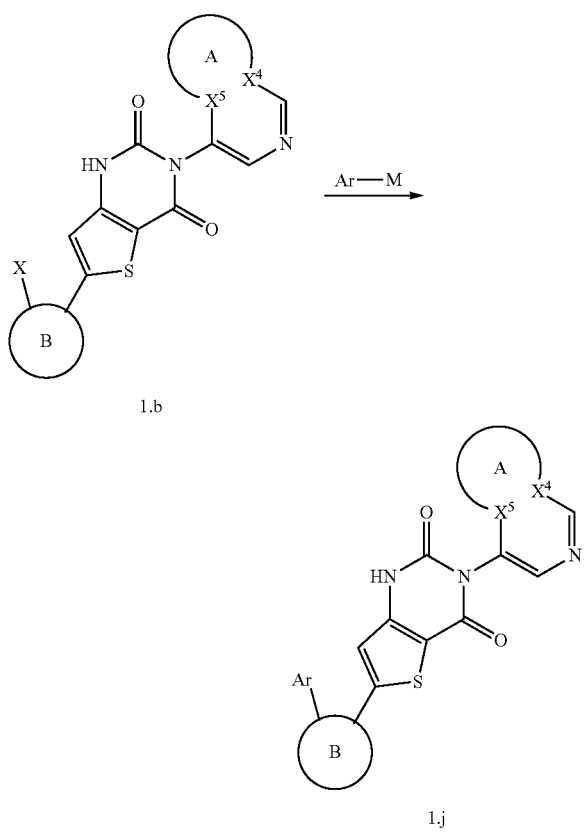

Metal mediated cross-coupling of compounds of formula 1.b (where X is —OTf, —Cl, Br, or —I) with a suitable coupling partner Ar-M (where Ar is aryl, heteroaryl and M is —B, —Sn, —Zn, —Si, or —Mg) in the presence of a suitable catalyst (i.e., Pd or Ni) can be used to provide compound of formula (1.j).

Pharmaceutical Formulations

In some embodiments, the present disclosure provides a pharmaceutical formulation comprising a pharmaceutically effective amount of a compound of the present disclosure, or a pharmaceutically acceptable salt thereof, and a pharmaceutically acceptable carrier or excipient. Also provided herein is a pharmaceutical formulation comprising a pharmaceutically effective amount of a compound of Formula (I), (II), (II-a), (II-b), (II-c), (II-d), (III), (III-a), (III-b), (III-c), (III-d), (IV), (V-a), (IV-b), (V), (V-a), and (V-b), or a pharmaceutically acceptable salt thereof, and a pharmaceutically acceptable carrier or excipient.

In some embodiments, the pharmaceutical composition is for use in treating a virus.

In some embodiments, the pharmaceutical composition further comprises one or more additional therapeutic agents. Any suitable additional therapeutic agent or combination therapy can be used with the compounds of Formula (I), (II), (II-a), (II-b), (II-c), (II-d), (III), (III-a), (III-b), (III-c), (III-d), (IV), (IV-a), (IV-b), (V), (V-a), and (V-b), or a pharmaceutically acceptable salt thereof, such as the agents and therapies described within.

In some embodiments, the pharmaceutical composition comprises a compound of Formula (I), (II), (II-a), (II-b), (II-c), (II-d), (III), (III-a), (III-b), (III-c), (III-d), (IV), (IV-a), (IV-b), (V), (V-a), and (V-b), and an additional therapeutic agent, wherein the additional therapeutic agent is as described herein under the heading "Combination Therapy."

In some embodiments, compounds disclosed herein are formulated with conventional carriers and excipients, which can be selected in accord with ordinary practice. Tablets can contain excipients, glidants, fillers, binders and the like. Aqueous formulations can be prepared in sterile form, and can be isotonic, for instance when intended for delivery by other than oral administration. In some embodiments, formulations can optionally contain excipients such as those set forth in the "Handbook of Pharmaceutical Excipients" (1986). Excipients can include, for example, ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, for example from about 7 to about 10.

In some embodiments, the compounds disclosed herein are administered alone. In some embodiments, compounds disclosed herein are administered in pharmaceutical formulations. In some embodiments a formulation, for veterinary and/or for human use, comprises at least one compound of Formula (I), (II), (II-a), (II-b), (II-c), (II-d), (III), (III-a), (III-b), (III-c), (III-d), (IV), (IV-a), (IV-b), (V), (V-a), and (V-b), or a pharmaceutically acceptable salt thereof, together with one or more acceptable carriers and optionally other therapeutic ingredients, such as those additional therapeutic ingredients discussed herein. In some embodiments, carrier (s) are "acceptable" in the sense of being compatible with the other ingredients of the formulation and physiologically innocuous to the recipient thereof.

In some embodiments, formulations of the disclosure include those suitable for the foregoing administration routes. In some embodiments, formulations are presented in unit dosage form. Formulations may be prepared by methods known in the art of pharmacy. Techniques and formulations can be found, for example, in Remington's Pharmaceutical Sciences (Mack Publishing Co., Easton, PA). Such methods include, for instance, a step of bringing into association the active ingredient with a carrier comprising one or more accessory ingredients. In some embodiments, formulations are prepared by bringing into association the active ingredient with liquid carriers or finely divided solid carriers or both, and then, in some embodiments, shaping the product.

In some embodiments, the pharmaceutical formulation is for subcutaneous, intramuscular, intravenous, oral, or inhalation administration.

Formulations suitable for oral administration may be presented as discrete units such as capsules, cachets or tablets each containing a predetermined amount of active ingredient, such as a compound of Formula (I), (II), (II-a), (II-b), (II-c), (II-d), (III), (III-a), (III-b), (III-c), (III-d), (IV), (IV-a), (V-b), (V), (V-a), and (V-b), or a pharmaceutically acceptable salt thereof, as a powder or granules; as a solution or a suspension in an aqueous or non-aqueous liquid; or as an oil-in-water liquid emulsion or a water-in-oil liquid emulsion. In some embodiments, an active ingredient is administered as a bolus, electuary or paste.

A tablet can be made, for example, by compression or molding, optionally with one or more accessory ingredients. Compressed tablets may be prepared, for example, by compressing in a suitable machine the active ingredient in a free-flowing form such as a powder or granules, optionally mixed with a binder, lubricant, inert diluent, preservative, surface active or dispersing agent. Molded tablets may be made, for instance, by molding in a suitable machine a mixture of the powdered active ingredient moistened with an inert liquid diluent. The tablets may optionally be coated or scored. In some embodiments, tablets are formulated so as to provide slow or controlled release of the active ingredient therefrom.

For infections of the eye or other external tissues e.g. mouth and skin, the formulations can be applied as a topical ointment or cream containing a compound of Formula (I), (II), (II-a), (II-b), (II-c), (II-d), (III), (III-a), (III-b), (III-c), (III-d), (IV), (IV-a), (IV-b), (V), (V-a), and (V-b), in an amount of, for example, about 0.075 to about 20% w/w (including active ingredient(s) in a range between about 0.1% and about 20% in increments of about 0.1% w/w such as about 0.6% w/w, about 0.7% w/w, etc.), such as about 0.2 to about 15% w/w and such as about 0.5 to about 10% w/w. When formulated in an ointment, a compound of Formula (I), (II-a), (II-b), (II-c), (III-a), or (III-b) may be employed with either a paraffinic or a water-miscible ointment base. Alternatively, a compound of Formula (I), (II-a), (II-b), (II-c), (III-a), or (III-b) may be formulated in a cream with an oil-in-water cream base.

If desired, the aqueous phase of the cream base may include, for example, at least about 30% w/w of a polyhydric alcohol. i.e., an alcohol having two or more hydroxyl groups such as propylene glycol, butane 1,3-diol, mannitol, sorbitol, glycerol and polyethylene glycol (including PEG 400) and mixtures thereof. The topical formulations may in some embodiments include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise merely an emulsifier (otherwise known as an emulgent), it can comprise, for example, a mixture of at least one emulsifier with a fat or an oil or with both a fat and an oil. In some embodiments, a hydrophilic emulsifier is included together with a lipophilic emulsifier which acts as a stabilizer. In some embodiments, an emulsion includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include, for instance, Tween 60, Span® 80, cetostearyl alcohol, benzyl alcohol, myristyl alcohol, glyceryl mono-stearate and sodium lauryl sulfate. Further emulgents and emulsion stabilizers suitable for use in the formulation include Tween® 80.

The choice of suitable oils or fats for the formulation is based on achieving the desired properties. The cream can be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

Pharmaceutical formulations according to the present invention comprise a compound according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Further non-limiting examples of suspending agents include Cyclodextrin. In some examples, the suspending agent is Sulfobutyl ether beta-cyclodextrin (SEB-beta-CD), for example Captisol*.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, and hypertonic sodium chloride solution.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 mg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

In some embodiments, the compounds disclosed herein are administered by inhalation. In some embodiments, formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents. In some embodiments, the compounds used herein are formulated and dosed as dry powder. In some embodiments, the compounds used herein are formulated and dosed as a nebulized formulation. In some embodiments, the compounds used herein are formulated for delivery by a face mask. In some embodiments, the compounds used herein are formulated for delivery by a face tent.

Another embodiment provides an inhalable composition comprising a compound of Formula (I), (II), (II-a), (II-b), (II-c), (II-d), (III), (III-a), (III-b), (III-c), (III-d), (IV), (IV-a), (IV-b), (V), (V-a), and (V-b), or a pharmaceutically acceptable salt thereof. In some embodiments, pharmaceutically acceptable salts are inorganic acid salts including hydrochloride, hydrobromide, sulfate or phosphate salts. For example, such salts may cause less pulmonary irritation relative to other salts. In some embodiments, an inhalable composition is delivered to the endobronchial space in an aerosol comprising particles with a mass median aerodynamic diameter (MMAD) between about 1 and about 5 µm. In some embodiments, the compound of Formula (I), (II), (II-a), (II-b), (II-c), (II-d), (III), (III-a), (III-b), (III-c), (III-d), (IV), (IV-a), (IV-b), (V), (V-a), and (V-b), or a pharmaceutically acceptable salt thereof, is formulated for aerosol delivery using a nebulizer, pressurized metered dose inhaler (pMDI), or dry powder inhaler (DPI).

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, the method of delivery, and the pharmaceutical formulation, and can be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of about 70 kg body weight can range from about 1 mg to about 1000 mg, such as between about 5 mg and about 500 mg, and may take the form of single or multiple doses.

Methods of Use

The present disclosure also provides a method of treating or preventing a viral infection in a subject (e.g., human) in need thereof, the method comprising administering to the subject a compound described herein.

In some embodiments, the present disclosure provides a method of treating a viral infection in a subject (e.g., human) in need thereof, the method comprising administering to a subject in need thereof a compound described herein.

In some embodiments, the compound described herein is administered to the human via oral, intramuscular, intravenous, subcutaneous, or inhalation administration.

In some embodiments, the present disclosure provides for methods of treating or preventing a viral infection in a subject (e.g., human) in need thereof, the method comprising administering to the subject a compound disclosed herein and at least one additional active therapeutic or prophylactic agent.

In some embodiments, the present disclosure provides for methods of treating a viral infection in a subject (e.g., human) in need thereof, the method comprising administering to the subject a compound disclosed herein, and at least one additional active therapeutic or prophylactic agent.

In one embodiment, the present disclosure provides for methods of inhibiting a viral polymerase in a cell, the methods comprising contacting the cell infected a virus with a compound disclosed herein, whereby the viral polymerase is inhibited.

In one embodiment, the present disclosure provides for methods of inhibiting a viral protease in a cell, the methods comprising contacting the cell infected a virus with a compound disclosed herein, and at least one additional active therapeutic agent, whereby the viral protease is inhibited.

Also provided here are the uses of the compounds disclosed herein for use in treating or preventing a viral infection in a subject in need thereof. For example, provided herein are uses of the compounds disclosed herein for use in treating a viral infection in a subject in need thereof.

In some embodiments, the viral infection is a coronavirus infection. As such, in some embodiments, provided herein is a method of treating a coronavirus infection in a human in need thereof, wherein the method comprises administering to the human a compound provided herein. In some embodiments, the coronavirus infection is a Severe Acute Respiratory Syndrome (SARS-CoV) infection. Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3. HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection. In some embodiments, the viral infection is a zoonotic coronavirus infection. In some embodiments, the viral infection is caused by a virus having at least 70% sequence homology to a viral polymerase selected from the group consisting of SARS-CoV polymerase, MERS-CoV polymerase and SARS-CoV-2. In some embodiments, the viral infection is caused by a virus having at least 80% sequence homology to a viral polymerase selected from the group consisting of SARS-CoV polymerase, MERS-CoV polymerase and SARS-CoV-2. In some embodiments, the viral infection is caused by a virus having at least 90% sequence homology to a viral polymerase selected from the group consisting of SARS-CoV polymerase. MERS-CoV polymerase and SARS-CoV-2. In some embodiments, the viral infection is caused by a virus having at least 95% sequence homology to a viral polymerase selected from the group consisting of SARS-CoV polymerase, MERS-CoV polymerase and SARS-CoV-2.

In some embodiments, the viral infection is caused by a variant of SARS-CoV-2, for example by the B.1.1.7 variant (the UK variant), B.1.351 variant (the South African variant). P.1 variant (the Brazil variant), B.1.1.7 with E484K variant, B.1.1.207 variant. B.1.1.317 variant, B.1.1.318 variant, B.1.429 variant. B.1.525 variant, or P.3 variant. In some embodiments, the viral infection is caused by the B.1.1.7 variant of SARS-CoV-2. In some embodiments, the viral infection is caused by the B.1.351 variant of SARS-CoV-2. In some embodiments, the viral infection is caused by the P.1 variant of SARS-CoV-2.

In some embodiments, the present disclosure provides a compound for use in the treatment of a coronavirus virus infection in a human in need thereof. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, and zoonotic coronavirus (PEDV or HKU CoV isolates such as HKU3. HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection (COVID19).

As described more fully herein, the compounds described herein can be administered with one or more additional therapeutic agent(s) to an individual (e.g., a human) infected with a viral infection. The additional therapeutic agent(s) can be administered to the infected individual at the same time as the compound of the present disclosure or before or after administration of the compound of the present disclosure.

Administration

One or more compounds of the invention may be administered by any route appropriate to the condition to be treated. Suitable routes include oral, rectal, inhalation, pulmonary, topical (including buccal and sublingual), vaginal and parenteral (including subcutaneous, intramuscular, intravenous, intradermal, intrathecal and epidural), and the like. In some embodiments, the compounds disclosed herein are administered by inhalation or intravenously. In some embodiments, the compounds disclosed herein are administered orally. It will be appreciated that the preferred route may vary with for example the condition of the recipient.

In the methods of the present invention for the treatment of a viral infection, the compounds of the present invention can be administered at any time to a human who may come into contact with the virus or is already suffering from the viral infection. In some embodiments, the compounds of the present invention can be administered prophylactically to humans coming into contact with humans suffering from the viral infection or at risk of coming into contact with humans suffering from the viral infection, e.g., healthcare providers. In some embodiments, administration of the compounds of the present invention can be to humans testing positive for the viral infection but not yet showing symptoms of the viral infection. In some embodiments, administration of the compounds of the present invention can be to humans upon commencement of symptoms of the viral infection.

In some embodiments, the methods disclosed herein comprise event driven administration of the compound of the present disclosure, or a pharmaceutically acceptable salt thereof, to the subject.

As used herein, the terms "event driven" or "event driven administration" refer to administration of the compound described herein, e.g., the compound of the present disclosure, or a pharmaceutically acceptable salt thereof, (1) prior to an event (e.g., 2 hours, 1 day, 2 days, 5 day, or 7 or more days prior to the event) that would expose the individual to the virus (or that would otherwise increase the individual's risk of acquiring the viral infection); and/or (2) during an event (or more than one recurring event) that would expose the individual to the virus (or that would otherwise increase the individual's risk of acquiring the viral infection); and/or (3) after an event (or after the final event in a series of recurring events) that would expose the individual to the virus (or that would otherwise increase the individual's risk of acquiring the viral infection). In some embodiments, the event driven administration is performed pre-exposure of the subject to the virus. In some embodiments, the event driven administration is performed post-exposure of the subject to the virus. In some embodiments, the event driven administration is performed pre-exposure of the subject to the virus and post-exposure of the subject to the virus.

In certain embodiments, the methods disclosed herein involve administration prior to and/or after an event that would expose the individual to the virus or that would otherwise increase the individual's risk of acquiring the viral infection, e.g., as pre-exposure prophylaxis (PrEP) and/or as post-exposure prophylaxis (PEP). In some embodiments, the methods disclosed herein comprise pre-exposure prophylaxis (PrEP). In some embodiments, methods disclosed herein comprise post-exposure prophylaxis (PEP).

In some embodiments, the compound of the present disclosure, or a pharmaceutically acceptable salt thereof, is administered before exposure of the subject to the virus.

In some embodiments, the compound of the present disclosure, or a pharmaceutically acceptable salt thereof, is administered before and after exposure of the subject to the virus.

In some embodiments, the compound of the present disclosure, or a pharmaceutically acceptable salt thereof, is administered after exposure of the subject to the virus.

An example of event driven dosing regimen includes administration of the compound of the present disclosure, or a pharmaceutically acceptable salt thereof, within 24 to 2 hours prior to the virus, followed by administration of the compound of the present disclosure, or a pharmaceutically acceptable salt, every 24 hours during the period of exposure, followed by a further administration of the compound of the present disclosure, or a pharmaceutically acceptable salt thereof, after the last exposure, and one last administration of the compound of Formula A or Formula B, or a pharmaceutically acceptable salt thereof, 24 hours later.

A further example of an event driven dosing regimen includes administration of the compound of the present disclosure, or a pharmaceutically acceptable salt thereof, within 24 hours before the viral exposure, then daily administration during the period of exposure, followed by a last administration approximately 24 hours later after the last exposure (which may be an increased dose, such as a double dose).

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of the present disclosure, or a pharmaceutically acceptable salt thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per day, or from about 30 mg to about 300 mg per day, or from about 0.3 mg to about 30 mg per day, or from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amount of the compound of the present disclosure is about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amount of the compound of the present disclosure is about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound provided herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 14,000 mg/day, between about 1-3,000 mg/day, between 1-2,000 mg/day, about 1-1,000 mg/day, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose. In some embodiments, the total daily dosage for a human subject may be about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg/day. In some embodiments, the total daily dosage for a human subject may be about 100-200, 100-300, 100-400, 100-500, 100-600, 100-700, 100-800, 100-900, 100-1000, 500-1100, 500-1200, 500-1300, 500-1400, 500-1500, 500-1600, 500-1700, 500-1800, 500-1900, 500-2000, 1500-2100, 1500-2200, 1500-2300, 1500-2400, 1500-2500, 2000-2600, 2000-2700, 2000-2800, 2000-2900, 2000-3000, 2500-3100, 2500-3200, 2500-3300, 2500-3400, 2500-3500, 3000-3600, 3000-3700, 3000-3800, 3000-3900, or 3000-4000 mg/day.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose. In some embodiments, the total daily dosage for a human subject may be about 1500 mg/day administered in a single dose. In some embodiments, the total daily dosage for a human subject may be about 2000 mg/day administered in a single dose. In some embodiments, the total daily dosage for a human subject may be about 2500 mg/day administered in a single dose. In some embodiments, the total daily dosage for a human subject may be about 3000 mg/day administered in a single dose. In some embodiments, the total daily dosage for a human subject may be about 4000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein. In some embodiments, a compound disclosed herein is administered three times daily in a method disclosed herein.

In some embodiments, a compound disclosed herein is administered once daily in the total daily dose of 100-4000 mg/day. In some embodiments, a compound disclosed herein is administered twice daily in the total daily dose of 100-4000 mg/day. In some embodiments, a compound disclosed herein is administered three times daily in the total daily dose of 100-4000 mg/day.

The frequency of dosage of the compound of the present disclosure will be determined by the needs of the individual patient and can be, for example, once per day or twice, or more times, per day. Administration of the compound continues for as long as necessary to treat the viral infection. For example, a compound can be administered to a human being infected with the virus for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

The compounds of the present disclosure or the pharmaceutical compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles may be alternated with resting periods of about 1 to 28 days, commonly about 7 days or about 14 days, between cycles. The treatment cycles, in other embodiments, may also be continuous.

Combination Therapy

The compounds described herein can also be used in combination with one or more additional therapeutic agents. As such, also provided herein are methods of treatment of a viral infection in a subject in need thereof, wherein the methods comprise administering to the subject a compound disclosed therein and a therapeutically effective amount of one or more additional therapeutic or prophylactic agents.

In some embodiments, the additional therapeutic agent is an antiviral agent. Any suitable antiviral agent can be used in the methods described herein.

In some embodiments, the additional therapeutic agent a 2,5-Oligoadenylate synthetase stimulator, 5-HT 2a receptor antagonist, 5-Lipoxygenase inhibitor, ABL family tyrosine kinase inhibitor, Abl tyrosine kinase inhibitor. Acetaldehyde dehydrogenase inhibitor, Acetyl CoA carboxylase inhibitor, Actin antagonist, Actin modulator, Activity-dependent neuroprotector modulator, Adenosine A3 receptor agonist, Adrenergic receptor antagonist, Adrenomedullin ligand, Adrenomedullin ligand inhibitor, Advanced glycosylation product receptor antagonist, Advanced glycosylation product receptor modulator, AKT protein kinase inhibitor, Alanine proline rich secreted protein stimulator, Aldose reductase inhibitor, Alkaline phosphatase stimulator, Alpha 2 adrenoceptor antagonist, Alpha 2B adrenoceptor agonist, AMP activated protein kinase stimulator, AMPA receptor modulator, Amyloid protein deposition inhibitor, Androgen receptor antagonist, Angiotensin II AT-1 receptor antagonist. Angiotensin II AT-2 receptor agonist, Angiotensin II receptor modulator, Angiotensin converting enzyme 2 inhibitor, Angiotensin converting enzyme 2 modulator, Angiotensin converting enzyme 2 stimulator, Angiotensin receptor modulator, Annexin A5 stimulator. Anoctamin 1 inhibitor, Anti-coagulant. Anti-histamine, Anti-hypoxic, Anti-thrombotic, AP1 transcription factor modulator, Apelin receptor agonist, APOA1 gene stimulator, Apolipoprotein A1 agonist, Apolipoprotein B antagonist, Apolipoprotein B modulator, Apolipoprotein C3 antagonist, Aryl hydrocarbon receptor agonist, Aryl hydrocarbon receptor antagonist, ATP binding cassette transporter B5 modulator, Ax1 tyrosine kinase receptor inhibitor, Bactericidal permeability protein inhibitor, Basigin inhibitor, Basigin modulator, BCL2 gene inhibitor, BCL2L11 gene stimulator, Bcr protein inhibitor, Beta 1 adrenoceptor modulator, Beta 2 adrenoceptor agonist, Beta adrenoceptor agonist, Beta-arrestin stimulator, Blood clotting modulator, BMP10 gene inhibitor, BMP15 gene inhibitor, Bone morphogenetic protein-10 ligand inhibitor, Bone morphogenetic protein-15 ligand inhibitor, Bradykinin B2 receptor antagonist, Brain derived neurotrophic factor ligand, Bromodomain containing protein 2 inhibitor, Bromodomain containing protein 4 inhibitor, Btk tyrosine kinase inhibitor, C-reactive protein modulator, Ca2+ release activated Ca2+ channel 1 inhibitor, Cadherin-5 modulator, Calcium activated chloride channel inhibitor, Calcium channel modulator, Calpain-1 inhibitor, Calpain-II inhibitor, Calpain-IX inhibitor, Cannabinoid CB2 receptor agonist, Cannabinoid receptor modulator, Casein kinase II inhibitor, CASP8-FADD-like regulator inhibitor, Caspase inhibitor, Catalase stimulator, CCL26 gene inhibitor, CCR2 chemokine antagonist, CCR5 chemokine antagonist, CD11a agonist, CD122 agonist, CD3 antagonist, CD4 agonist, CD40 ligand, CD40 ligand modulator, CD40 ligand receptor agonist, CD40 ligand receptor modulator, CD49d agonist, CD70 antigen modulator, CD73 agonist, CD73 antagonist, CD95 antagonist, CFTR inhibitor, CGRP receptor antagonist, Chemokine receptor-like 1 agonist, Chloride channel inhibitor. Chloride channel modulator, Cholera enterotoxin subunit B inhibitor, Cholesterol ester transfer protein inhibitor, Collagen modulator, Complement CIs subcomponent inhibitor, Complement C3 inhibitor, Complement C5 factor inhibitor, Complement C5a factor inhibitor, Complement Factor H stimulator, Complement cascade inhibitor, Complement factor C2 inhibitor, Complement factor D inhibitor, Connective tissue growth factor ligand inhibitor, Coronavirus nucleoprotein modulator, Coronavirus small envelope protein modulator, Coronavirus spike glycoprotein inhibitor, Coronavirus spike glycoprotein modulator, COVID19 envelope small membrane protein modulator, COVID19 non structural protein 8 modulator, COVID19 nucleoprotein modulator, COVID19 Protein 3a inhibitor, COVID19 replicase polyprotein 1a inhibitor, COVID19 replicase polyprotein 1a modulator. COVID19 replicase polyprotein 1ab inhibitor, COVID19 replicase polyprotein 1ab modulator, COVID19 Spike glycoprotein inhibitor, COVID19 Spike glycoprotein modulator. COVID19 structural glycoprotein modulator, CRF-2 receptor agonist, CSF-1 agonist, CSF-1 antagonist, CX3CR1 chemokine antagonist, CXC10 chemokine ligand inhibitor, CXC5 chemokine ligand inhibitor, CXCL1 gene modulator. CXCL2 gene modulator. CXCL3 gene modulator, CXCR1 chemokine antagonist, CXCR2 chemokine antagonist, CXCR4 chemokine antagonist, Cyclin D1 inhibitor, Cyclin E inhibitor, Cyclin-dependent kinase-1 inhibitor, Cyclin-dependent kinase-2 inhibitor, Cyclin-dependent kinase-5 inhibitor, Cyclin-dependent kinase-7 inhibitor, Cyclin-dependent kinase-9 inhibitor, Cyclooxygenase 2 inhibitor, Cyclooxygenase inhibitor, Cysteine protease inhibitor, Cytochrome P450 3A4 inhibitor, Cytokine receptor antagonist, Cytotoxic T lymphocyte protein gene modulator, Cytotoxic T-lymphocyte protein-4 inhibitor, Cytotoxic T-lymphocyte protein-4 stimulator, Dehydrogenase inhibitor, Dehydropeptidase-1 modulator. Deoxyribonuclease I stimulator, Deoxyribonuclease gamma stimulator, Deoxyribonuclease stimulator, Dihydroceramide delta 4 desaturase inhibitor. Dihydroorotate dehydrogenase inhibitor. Dipeptidyl peptidase I inhibitor, Dipeptidyl peptidase III inhibitor, Diuretic, DNA binding protein inhibitor, DNA methyltransferase inhibitor, Dopamine transporter inhibitor, E selectin antagonist, Ecto NOX disulfide thiol exchanger 2 inhibitor, EGFR gene inhibitor, Elongation factor 1 alpha 2 modulator, Endoplasmin modulator, Endoribonuclease DICER modulator, Endothelin ET-A receptor antagonist, Epidermal growth factor receptor antagonist, Estrogen receptor beta agonist, Estrogen receptor modulator, Eukaryotic initiation factor 4A-I inhibitor, Exo-alpha sialidase modulator, Exportin 1 inhibitor, Factor Ia modulator, Factor IIa modulator, Factor VII antagonist, Factor Xa antagonist. Factor XIa antagonist, FGF receptor antagonist, FGF-1 ligand, FGF-1 ligand inhibitor, FGF-2 ligand inhibitor, FGF1 receptor antagonist, FGF2 receptor antagonist, FGF3 receptor antagonist, Flt3 tyrosine kinase inhibitor, Fractalkine ligand inhibitor, Free fatty acid receptor 2 agonist, Free fatty acid receptor 3 agonist, furin inhibitors. Fyn tyrosine kinase inhibitor, FYVE finger phosphoinositide kinase inhibitor, G-protein coupled bile acid receptor I agonist, GABA A receptor modulator, Galectin-3 inhibitor, Gamma-secretase inhibitor, GDF agonist, Gelsolin stimulator, Glial cell neurotrophic factor ligand, Glucocorticoid receptor agonist, Glutathione peroxidase stimulator, GM-CSF ligand inhibitor. GM-CSF receptor agonist. GM-CSF receptor modulator, Griffithsin modulator, Growth regulated protein alpha ligand inhibitor, Grp78 calcium binding protein inhibitor, Heat shock protein HSP90 alpha inhibitor, Heat shock protein HSP90 beta inhibitor, Heat shock protein inhibitor, Heat shock protein stimulator, Hemagglutinin modulator, Hemoglobin modulator. Hemolysin alpha inhibitor, Heparanase inhibitor, Heparin agonist, Hepatitis B structural protein inhibitor, Hepatitis C virus NS5B polymerase inhibitor. HIF prolyl hydroxylase inhibitor, HIF prolyl hydroxylase-2 inhibitor, High mobility group protein B1 inhibitor, Histamine H1 receptor antagonist. Histamine H2 receptor antagonist, Histone deacetylase-6 inhibitor, Histone inhibitor, HIV protease inhibitor, HIV-1 gp120 protein inhibitor, HIV-1 protease inhibitor, HIV-1 reverse transcriptase inhibitor, HLA class I antigen modulator, HLA class 11 antigen modulator, Host cell factor modulator, Hsp 90 inhibitor, Human papillomavirus E6 protein modulator. Human papillomavirus E7 protein modulator, Hypoxia inducible factor inhibitor gene inhibitor, Hypoxia inducible factor-2 alpha modulator, 1-kappa B kinase inhibitor, I-kappa B kinase modulator, ICAM-1 stimulator, IgG receptor FcRn large subunit p51 modulator, IL-12 receptor antagonist, IL-15 receptor agonist, IL-15 receptor modulator, IL-17 antagonist, IL-18 receptor accessory protein antagonist, IL-2 receptor agonist, IL-22 agonist, IL-23 antagonist, IL-6 receptor agonist, IL-6 receptor antagonist, IL-6 receptor modulator. IL-7 receptor agonist, IL-8 receptor antagonist, IL12 gene stimulator, IL8 gene modulator, Immunoglobulin G modulator, Immunoglobulin G1 agonist, Immunoglobulin G1 modulator, Immunoglobulin agonist, Immunoglobulin gamma Fc receptor I modulator, Immunoglobulin kappa modulator, inosine monophosphate dehydrogenase inhibitor, Insulin sensitizer, Integrin agonist, Integrin alpha-4/beta-7 antagonist, Integrin alpha-V/beta-1 antagonist, Integrin alpha-V/beta-6 antagonist, Interferon agonist, Interferon alpha 14 ligand, Interferon alpha 2 ligand, Interferon alpha 2 ligand modulator, Interferon alpha ligand, Interferon alpha ligand inhibitor. Interferon alpha ligand modulator, Interferon beta ligand, Interferon gamma ligand inhibitor, Interferon gamma receptor agonist, Interferon gamma receptor antagonist, Interferon receptor modulator, Interferon type I receptor agonist, Interleukin 17A ligand inhibitor, Interleukin 17F ligand inhibitor, Interleukin 18 ligand inhibitor. Interleukin 22 ligand, Interleukin-1 beta ligand inhibitor, Interleukin-1 beta ligand modulator, Interleukin-1 ligand inhibitor, Interleukin-2 ligand, Interleukin-29 ligand, Interleukin-6 ligand inhibitor, Interleukin-7 ligand, Interleukin-8 ligand inhibitor, IRAK-4 protein kinase inhibitor, JAK tyrosine kinase inhibitor, JakI tyrosine kinase inhibitor, Jak2 tyrosine kinase inhibitor, Jak3 tyrosine kinase inhibitor, Jun N terminal kinase inhibitor, Jun N terminal kinase modulator, Kallikrein modulator, Kelch like ECH associated protein 1 modulator, Kit tyrosine kinase inhibitor, KLKB1 gene inhibitor, Lactoferrin stimulator, Lanosterol-14 demethylase inhibitor, Lck tyrosine kinase inhibitor, Leukocyte Ig like receptor A4 modulator, Leukocyte elastase inhibitor, Leukotriene BLT receptor antagonist, Leukotriene D4 antagonist, Leukotriene receptor antagonist, Listeriolysin stimulator, Liver X receptor antagonist, Low molecular weight heparin, Lung surfactant associated protein B stimulator, Lung surfactant associated protein D modulator, Lyn tyrosine kinase inhibitor, Lyn tyrosine kinase stimulator, Lysine specific histone demethylase I inhibitor, Macrophage migration inhibitory factor inhibitor, Mannan-binding lectin serine protease inhibitor, Mannan-binding lectin serine protease-2 inhibitor, MAO B inhibitor, MAP kinase inhibitor, MAPK gene modulator, Matrix metalloprotease modulator, Maxi K potassium channel inhibitor, MCLI gene inhibitor, MEK protein kinase inhibitor, MEK-1 protein kinase inhibitor, Melanocortin MCI receptor agonist, Melanocortin MC3 receptor agonist, Metalloprotease-12 inhibitor, METTL3 gene inhibitor, Moesin inhibitor, Moesin modulator, Monocyte chemotactic protein 1 ligand inhibitor, Monocyte differentiation antigen CD14 inhibitor, mRNA cap guanine N7 methyltransferase modulator, mTOR complex 1 inhibitor, mTOR complex 2 inhibitor, mTOR inhibitor, Mucolipin modulator, Muscannic receptor antagonist, Myeloperoxidase inhibitor, NACHT LRR PYD domain protein 3 inhibitor, NAD synthase modulator, NADPH oxidase inhibitor, Neuropilin 2 modulator, Neuroplastin inhibitor, NFE2L2 gene stimulator, NK cell receptor agonist, NK1 receptor antagonist, NMDA receptor antagonist, NMDA receptor epsilon 2 subunit inhibitor, Non receptor tyrosine kinase TYK2 antagonist, Non-nucleoside reverse transcriptase inhibitor, Nuclear erythroid 2-related factor 2 stimulator, Nuclear factor kappa B inhibitor, Nuclear factor kappa B modulator, Nuclease stimulator, Nucleolin inhibitor, Nucleoprotein inhibitor, Nucleoprotein modulator, Nucleoside reverse transcriptase inhibitor. Opioid receptor agonist, Opioid receptor antagonist, Opioid receptor mu modulator, Opioid receptor sigma antagonist 1, Omithine decarboxylase inhibitor, Outer membrane protein inhibitor, OX40 ligand, p38 MAP kinase alpha inhibitor, p38 MAP kinase inhibitor, p38 MAP kinase modulator, p53 tumor suppressor protein stimulator, Palmitoyl protein thioesterase 1 inhibitor, Papain inhibitor, PARP inhibitor, PARP modulator, PDE 10 inhibitor, PDE 3 inhibitor, PDE 4 inhibitor, PDGF receptor alpha antagonist, PDGF receptor antagonist, PDGF receptor beta antagonist. Peptidyl-prolyl cis-trans isomerase A inhibitor, Peroxiredoxin 6 modulator, PGD2 antagonist, PGI2 agonist, P-glycoprotein inhibitor, Phosphoinositide 3-kinase inhibitor, Phosphoinositide-3 kinase delta inhibitor, Phosphoinositide-3 kinase gamma inhibitor, Phospholipase A2 inhibitor, Plasma kallikrein inhibitor, Plasminogen activator inhibitor 1 inhibitor, Platelet inhibitor, Platelet glycoprotein VI inhibitor, Polo-like kinase 1 inhibitor, Poly ADP ribose polymerase 1 inhibitor, Poly ADP ribose polymerase 2 inhibitor, Polymerase cofactor VP35 inhibitor, PPAR alpha agonist, Progesterone receptor agonist, Programmed cell death protein 1 modulator, Prolyl hydroxylase inhibitor, Prostaglandin E synthase-1 inhibitor, Protease inhibitor, Proteasome inhibitor, Protein arginine deiminase IV inhibitor, Protein tyrosine kinase inhibitor, Protein tyrosine phosphatase beta inhibitor, Protein tyrosine phosphatase-2C inhibitor, Proto-oncogene Mas agonist, Purinoceptor antagonist, Raf protein kinase inhibitor, RANTES ligand, Ras gene inhibitor, Retinoate receptor responder protein 2 stimulator, Rev protein modulator, Ribonuclease stimulator, RIP-1 kinase inhibitor, RNA helicase inhibitor, RNA polymerase inhibitor, RNA polymerase modulator, S phase kinase associated protein 2 inhibitor, SARS coronavirus 3C protease like inhibitor, Serine protease inhibitor, Serine threonine protein kinase ATR inhibitor, Serine threonine protein kinase TBK1 inhibitor, Serum amyloid A protein modulator, Signal transducer CD24 stimulator, Sodium channel stimulator. Sodium glucose transporter-2 inhibitor, Sphingosine kinase 1 inhibitor, Sphingosine kinase 2 inhibitor, Sphingosine kinase inhibitor, Sphingosine-1-phosphate receptor-1 agonist, Sphingosine-1-phosphate receptor-1 antagonist, Sphingosine-1-phosphate receptor-1 modulator, Sphingosine-1-phosphate receptor-5 agonist, Sphingosine-1-phosphate receptor-5 modulator. Spike glycoprotein inhibitor, Src tyrosine kinase inhibitor, STAT-1 modulator, STAT-3 inhibitor, STAT-5 inhibitor, STAT3 gene inhibitor, Stem cell antigen-1 inhibitor, Stimulator of interferon genes protein stimulator, Sulfatase inhibitor, Superoxide dismutase modulator, Superoxide dismutase stimulator, Syk tyrosine kinase inhibitor, T cell immunoreceptor Ig ITIM protein inhibitor, T cell receptor agonist, T cell surface glycoprotein CD28 inhibitor, T-cell differentiation antigen CD6 inhibitor, T-cell surface glycoprotein CD8 stimulator, T-cell transcription factor NFAT modulator, Tankyrase-1 inhibitor, Tankyrase-2 inhibitor, Tek tyrosine kinase receptor stimulator, Telomerase modulator, Tetanus toxin modulator, TGF beta receptor antagonist, TGFB2 gene inhibitor, Thymosin beta 4 ligand, Thyroid hormone receptor beta agonist, Tissue factor inhibitor, Tissue plasminogen activator modulator, Tissue plasminogen activator stimulator, TLR agonist, TLR modulator, TLR-2 agonist, TLR-2 antagonist, TLR-3 agonist, TLR-4 agonist, TLR-4 antagonist, TLR-6 agonist, TLR-7 agonist, TLR-7 antagonist, TLR-8 antagonist, TLR-9 agonist, TMPRSS2 gene inhibitor, TNF alpha ligand inhibitor, TNF alpha ligand modulator, TNF binding agent, TNF gene inhibitor, Topoisomerase inhibitor, Transcription factor EB stimulator, Transferrin modulator, Transketolase inhibitor, Translocation associated protein inhibitor, Transmembrane serine protease 2 inhibitor, Transthyretin modulator, TREM receptor I antagonist, TRP cation channel C1 modulator, TRP cation channel C6 inhibitor, TRP cation channel V6 inhibitor, Trypsin 1 inhibitor, Trypsin 2 inhibitor, Trypsin 3 inhibitor, Trypsin inhibitor, Tubulin alpha inhibitor, Tubulin beta inhibitor, Tumor necrosis factor 14 ligand inhibitor, TYK2 gene inhibitor, Type I IL-1 receptor antagonist, Tyrosine protein kinase ABL1 inhibitor, Ubiquinol cytochrome C reductase 14 kDa inhibitor, Ubiquitin ligase modulator, Unspecified GPCR agonist, Unspecified cytokine receptor modulator, Unspecified enzyme stimulator, Unspecified gene inhibitor, Unspecified receptor modulator, Urokinase plasminogen activator inhibitor, Vascular cell adhesion protein 1 agonist, Vasodilator, VEGF ligand inhibitor, VEGF receptor antagonist, VEGF-1 receptor antagonist, VEGF-1 receptor modulator, VEGF-2 receptor antagonist, VEGF-3 receptor antagonist, Vimentin inhibitor, Vimentin modulator, VIP receptor agonist. Viral envelope protein inhibitor. Viral protease inhibitor, Viral protease modulator, Viral protein target modulator. Viral ribonuclease inhibitor, Viral structural protein modulator, Vitamin D3 receptor agonist, X-linked inhibitor of apoptosis protein inhibitor. Xanthine oxidase inhibitor, or Zonulin inhibitor.

In some embodiments, the compounds and compositions of the present disclosure may be administered in combination with a Sars-Cov-2 treatment, such as parenteral fluids (including dextrose saline and Ringer's lactate), nutrition, antibiotics (including azithromycin, metronidazole, amphotericin B, amoxicillin/clavulanate, trimethoprim/sulfamethoxazole, R-327 and cephalosporin antibiotics, such as ceftriaxone and cefuroxime), antifungal prophylaxis, fever and pain medication, antiemetic (such as metoclopramide)

and/or antidiarrheal agents, vitamin and mineral supplements (including Vitamin K, vitamin D, cholecalciferol, vitamin C and zinc sulfate), anti-inflammatory agents (such as ibuprofen or steroids), corticosteroids such as dexamethasone, methylprednisolone, prednisone, mometasone, immunomodulatory medications (eg interferon), vaccines, and pain medications.

In some embodiments, the additional therapeutic agent is an Abl tyrosine kinase inhibitor, such as radotinib or imatinib.

In some embodiments, the additional therapeutic agent is an acetaldehyde dehydrogenase inhibitor, such as ADX-629.

In some embodiments, the additional therapeutic agent is an adenosine A3 receptor agonist, such as piclidenoson.

In some embodiments, the additional therapeutic agent is an adrenomedullin ligand such as adrenomedullin.

In some embodiments, the additional therapeutic agent is a p38 MAPK+PPAR gamma agonist/insulin sensitizer such as KIN-001.

In some embodiments, the additional therapeutic agent is an aldose reductase inhibitor, such as caficrestat.

In some embodiments, the additional therapeutic agent is an AMPA receptor modulator, such as traneurocin.

In some embodiments, the additional therapeutic agent is an annexin A5 stimulator, such as AP-01 or SY-005.

In some embodiments, the additional therapeutic agent is an anti-coagulant, such as heparins (heparin and low molecular weight heparin), aspirin, apixaban, dabigatran, edoxaban, argatroban, enoxaparin, or fondaparinux.

In some embodiments, the additional therapeutic agent is an androgen receptor antagonist such as bicalutamide, enzalutamide, or pruxelutamide (proxalutamide).

In some embodiments, the additional therapeutic agent is anti-hypoxic, such as trans-sodium crocetinate.

In some embodiments, the additional therapeutic agent is an anti-thrombotic, such as defibrotide, rivaroxaban, alteplase, tirofiban, clopidogrel, prasugrel, bemiparin, bivalirudin, sulodexide, or tenecteplase.

In some embodiments, the additional therapeutic agent is an antihistamine, such as cloroperastine or clemastine.

In some embodiments, the additional therapeutic agent is an apolipoprotein A1 agonist, such as CER-001.

In some embodiments, the additional therapeutic agent is a phospholipase A2 inhibitor, such as icosapent ethyl.

In some embodiments, the additional therapeutic agent is an axl tyrosine kinase receptor inhibitor, such as bemcentinib.

In some embodiments, the additional therapeutic agent is a corticosteroid/beta 2 adrenoceptor agonist, such as budesonide+formoterol fumarate.

In some embodiments, the additional therapeutic agent is a BET bromodomain inhibitor/APOA1 gene stimulator such as apabetalone.

In some embodiments, the additional therapeutic agent is a blood clotting modulator, such as lanadelumab.

In some embodiments, the additional therapeutic agent is a bradykinin B2 receptor antagonist, such as icatibant.

In some embodiments, the additional therapeutic agent is an EGFR gene inhibitor/Btk tyrosine kinase inhibitor, such as abivertinib.

In some embodiments, the additional therapeutic agent is a Btk tyrosine kinase inhibitor, such as ibrutinib or zanubrutinib.

In some embodiments, the additional therapeutic agent is a calpain-/II/IX inhibitor, such as BLD-2660.

In some embodiments, the additional therapeutic agent is a Ca2+ release activated Ca2+ channel 1 inhibitor, such as zegocractin (CM-4620).

In some embodiments, the additional therapeutic agent is a cadherin-5 modulator, such as FX-06.

In some embodiments, the additional therapeutic agent is a casein kinase II inhibitor, such as silmitasertib.

In some embodiments, the additional therapeutic agent is a caspase inhibitor, such as emricasan.

In some embodiments, the additional therapeutic agent is a catalase stimulator/superoxide dismutase stimulator, such as MP-1032.

In some embodiments, the additional therapeutic agent is a CCR2 chemokine antagonist/CCR5 chemokine antagonist such as cenicriviroc.

In some embodiments, the additional therapeutic agent is a CCR5 chemokine antagonist, such as maraviroc.

In some embodiments, the additional therapeutic agent is a CD122 agonist/IL-2 receptor agonist, such as bempegaldesleukin.

In some embodiments, the additional therapeutic agent is a CD73 agonist/interferon beta ligand, such as FP-1201.

In some embodiments, the additional therapeutic agent is a cholesterol ester transfer protein inhibitor, such as dalcetrapib.

In some embodiments, the additional therapeutic agent is a Mannan-binding lectin serine protease/complement C1s subcomponent inhibitor/meloperoxidase inhibitor, such as RLS-0071.

In some embodiments, the additional therapeutic agent is a complement $C_5$ factor inhibitor/leukotriene BLT receptor antagonist, such as nomacopan.

In some embodiments, the additional therapeutic agent is a complement $C_5$ factor inhibitor, such as zilucoplan.

In some embodiments, the additional therapeutic agent is a CXCR4 chemokine antagonist, such as motixafortide.

In some embodiments, the additional therapeutic agent is a cytochrome P450 3A4 inhibitor/peptidyl-prolyl cis-trans isomerase A inhibitor, such as alisporivir.

In some embodiments, the additional therapeutic agent is a cysteine protease inhibitor, such as SLV-213.

In some embodiments, the additional therapeutic agent is a dihydroorotate dehydrogenase inhibitor, such as brequinar, RP-7214, or emvododstat.

In some embodiments, the additional therapeutic agent is a dehydropeptidase-1 modulator, such as Metablok.

In some embodiments, the additional therapeutic agent is a dihydroorotate dehydrogenase inhibitor/IL-17 antagonist, such as vidofludimus.

In some embodiments, the additional therapeutic agent is a diuretic, such as an aldosterone antagonist, such as spironolactone.

In some embodiments, the additional therapeutic agent is a deoxyribonuclease I stimulator, such as GNR-039 or domase alfa.

In some embodiments, the additional therapeutic agent is a NET inhibitor, such as NTR-441.

In some embodiments, the additional therapeutic agent is a dihydroceramide delta 4 desaturase inhibitor/sphingosine kinase 2 inhibitor, such as opaganib.

In some embodiments, the additional therapeutic agent is a DNA methyltransferase inhibitor, such as azacytidine.

In some embodiments, the additional therapeutic agent is an LXR antagonist, such as larsucosterol.

In some embodiments, the additional therapeutic agent is a dipeptidyl peptidase I inhibitor, such as brensocatib.

In some embodiments, the additional therapeutic agent is an elongation factor 1 alpha 2 modulator, such as plitidepsin.

In some embodiments, the additional therapeutic agent is a eukaryotic initiation factor 4A-1 inhibitor, such as zotatifin.

In some embodiments, the additional therapeutic agent is an exo-alpha sialidase modulator, such as DAS-181.

In some embodiments, the additional therapeutic agent is an exportin 1 inhibitor, such as selinexor.

In some embodiments, the additional therapeutic agent is a fractalkine ligand inhibitor, such as KAND-567.

In some embodiments, the additional therapeutic agent is a FYVE finger phosphoinositide kinase inhibitor/IL-12 receptor antagonist/IL-23 antagonist, such as apilimod dimesylate.

In some embodiments, the additional therapeutic agent is a GABA A receptor modulator, such as brexanolone.

In some embodiments, the additional therapeutic agent is a glucocorticoid receptor agonist, such as ciclesonide, hydrocortisone, dexamethasone, dexamethasone phosphate, or 101-PGC-005.

In some embodiments, the additional therapeutic agent is a GM-CSF receptor agonist, such as sargramostim.

In some embodiments, the additional therapeutic agent is a GPCR agonist, such as esuberaprost sodium.

In some embodiments, the additional therapeutic agent is a Griffithsin modulator, such as Q-Griffithsin.

In some embodiments, the additional therapeutic agent is a leukotriene D4 antagonist, such as montelukast.

In some embodiments, the additional therapeutic agent is a histamine H1 receptor antagonist, such as ebastine, tranilast, levocetirizine dihydrochloride.

In some embodiments, the additional therapeutic agent is a histamine H2 receptor antagonist, such as famotidine.

In some embodiments, the additional therapeutic agent is a heat shock protein stimulator/insulin sensitizer/PARP inhibitor, such as BGP-15.

In some embodiments, the additional therapeutic agent is a histone inhibitor, such as STC-3141.

In some embodiments, the additional therapeutic agent is a histone deacetylase-6 inhibitor, such as CKD-506.

In some embodiments, the additional therapeutic agent is a HIF prolyl hydroxylase-2 inhibitor, such as desidustat.

In some embodiments, the additional therapeutic agent is an HIF prolyl hydroxylase inhibitor, such as vadadustat.

In some embodiments, the additional therapeutic agent is an IL-8 receptor antagonist, such as reparixin.

In some embodiments, the additional therapeutic agent is an IL-7 receptor agonist, such as CYT-107.

In some embodiments, the additional therapeutic agent is an IL-7 receptor agonist/interleukin-7 ligand, such as efineptakin alfa.

In some embodiments, the additional therapeutic agent is an IL-22 agonist, such as efmarodocokin alfa.

In some embodiments, the additional therapeutic agent is an IL-22 agonist/interleukin 22 ligand, such as F-652.

In some embodiments, the additional therapeutic agent is an integrin alpha-V/beta-1 antagonist/integrin alpha-V/beta-6 antagonist, such as bexotegrast.

In some embodiments, the additional therapeutic agent is an interferon alpha 2 ligand, such as interferon alfa-2b or Virafin.

In some embodiments, the additional therapeutic agent is an interferon beta ligand, such as interferon beta-1a follow-on biologic, interferon beta-1b, or SNG-001.

In some embodiments, the additional therapeutic agent is an interferon receptor modulator, such as peginterferon lambda-1a.

In some embodiments, the additional therapeutic agent is an interleukin-2 ligand, such as aldesleukin.

In some embodiments, the additional therapeutic agent is an IRAK-4 protein kinase inhibitor, such as zimlovisertib.

In some embodiments, the additional therapeutic agent is a JAK inhibitor, for example the additional therapeutic agent is baricitinib, filgotinib, jaktinib, tofacitinib, or nezulcitinib (TD-0903).

In some embodiments, the additional therapeutic agent is a neutrophil elastase inhibitor, such as alvelestat.

In some embodiments, the additional therapeutic agent is a lung surfactant associated protein D modulator, such as AT-100.

In some embodiments, the additional therapeutic agent is a plasma kallikrein inhibitor, such as donidalorsen.

In some embodiments, the additional therapeutic agent is a lysine specific histone demethylase 1/MAO B inhibitor, such as vafidemstat.

In some embodiments, the additional therapeutic agent is a Mannan-binding lectin serine protease inhibitor, such as conestat alfa.

In some embodiments, the additional therapeutic agent is a maxi K potassium channel inhibitor, such as ENA-001.

In some embodiments, the additional therapeutic agent is a MEK protein kinase inhibitor, such as zapnometinib.

In some embodiments, the additional therapeutic agent is a MEK-1 protein kinase inhibitor/Ras gene inhibitor, such as antroquinonol.

In some embodiments, the additional therapeutic agent is a melanocortin MC1 receptor agonist, such as PL-8177.

In some embodiments, the additional therapeutic agent is a matrix metalloprotease-12 inhibitor, such as FP-025.

In some embodiments, the additional therapeutic agent is a NACHT LRR PYD domain protein 3 inhibitor, such as dapansutrile, DFV-890, or ZYIL-1.

In some embodiments, the additional therapeutic agent is a NADPH oxidase inhibitor, such as isuzinaxib.

In some embodiments, the additional therapeutic agent is a neuropilin 2 modulator, such as efzofitimod.

In some embodiments, the additional therapeutic agent is an NK1 receptor antagonist, such as aprepitant or tradipitant.

In some embodiments, the additional therapeutic agent is an NMDA receptor antagonist, such as transcrocetin or ifenprodil.

In some embodiments, the additional therapeutic agent is a nuclear factor kappa B inhibitor/p38 MAP kinase inhibitor, such as zenuzolac.

In some embodiments, the additional therapeutic agent is an ornithine decarboxylase inhibitor, such as eflornithine.

In some embodiments, the additional therapeutic agent is an opioid receptor sigma antagonist 1, such as MR-309.

In some embodiments, the additional therapeutic agent is a PGD2 antagonist, such as asapiprant.

In some embodiments, the additional therapeutic agent is a PDGF receptor antagonist/TGF beta receptor antagonist/p38 MAP kinase inhibitor, such as deupirfenidone.

In some embodiments, the additional therapeutic agent is a phospholipase A2 inhibitor, such as varespladib methyl.

In some embodiments, the additional therapeutic agent is a phosphoinositide 3-kinase inhibitor/mTOR complex inhibitor, such as dactolisib.

In some embodiments, the additional therapeutic agent is a phosphoinositide-3 kinase delta/gamma inhibitor, such as duvelisib.

In some embodiments, the additional therapeutic agent is a plasminogen activator inhibitor 1 inhibitor, such as TM-5614.

In some embodiments, the additional therapeutic agent is a protein tyrosine phosphatase beta inhibitor, such as razuprotafib.

In some embodiments, the additional therapeutic agent is a RIP-1 kinase inhibitor, such as DNL-758 or SIR-0365.

In some embodiments, the additional therapeutic agent is a Rev protein modulator, such as obefazimod.

In some embodiments, the additional therapeutic agent is an S phase kinase associated protein 2 inhibitor, such as niclosamide or DWRX-2003.

In some embodiments, the additional therapeutic agent is a signal transducer CD24 stimulator, such as EXO-CD24.

In some embodiments, the additional therapeutic agent is a sodium glucose transporter-2 inhibitor, such as dapagliflozin propanediol.

In some embodiments, the additional therapeutic agent is a sodium channel stimulator, such as solnatide.

In some embodiments, the additional therapeutic agent is a sphingosine-1-phosphate receptor-1 agonist/sphingosine-1-phosphate receptor-5 agonist, such as ozanimod.

In some embodiments, the additional therapeutic agent is a non-steroidal anti-inflammatory drug, such as Ampion.

In some embodiments, the additional therapeutic agent is a superoxide dismutase stimulator, such as avasopasem manganese.

In some embodiments, the additional therapeutic agent is a Syk tyrosine kinase inhibitor, such as fostamatinib disodium.

In some embodiments, the additional therapeutic agent is a Tie2 tyrosine kinase receptor agonist, such as AV-001.

In some embodiments, the additional therapeutic agent is a TGFB2 gene inhibitor, such as trabedersen.

In some embodiments, the additional therapeutic agent is a tissue factor inhibitor, such as AB-201.

In some embodiments, the additional therapeutic agent is a TLR-3 agonist, such as rintatolimod.

In some embodiments, the additional therapeutic agent is a TLR-4 antagonist, such as ApTLR-4FT, EB-05, or eritoran.

In some embodiments, the additional therapeutic agent is a TLR-7/8 antagonist, such as enpatoran.

In some embodiments, the additional therapeutic agent is a TLR-2/6 agonist, such as INNA-051.

In some embodiments, the additional therapeutic agent is a TLR-7 agonist, such as PRTX-007.

In some embodiments, the additional therapeutic agent is a TLR agonist, such as PUL-042.

In some embodiments, the additional therapeutic agent is a TLR-4 agonist, such as REVTx-99.

In some embodiments, the additional therapeutic agent is a TLR-2/4 antagonist, such as VB-201.

In some embodiments, the additional therapeutic agent is a TNF alpha ligand inhibitor, such as pegipanermin.

In some embodiments, the additional therapeutic agent is a type I IL-1 receptor antagonist, such as anakinra.

In some embodiments, the additional therapeutic agent is a TREM receptor 1 antagonist, such as nangibotide.

In some embodiments, the additional therapeutic agent is a trypsin inhibitor, such as ulinastatin.

In some embodiments, the additional therapeutic agent is a tubulin inhibitor such as sabizabulin, CCI-001, PCNT-13, CR-42-24, albendazole, entasobulin. SAR-132885, or ON-24160.

In some embodiments, the additional therapeutic agent is a VIP receptor agonist, such as aviptadil.

In some embodiments, the additional therapeutic agent is a xanthine oxidase inhibitor, such as oxypurinol.

In some embodiments, the additional therapeutic agent is a vasodilator, such as iloprost, epoprostenol (VentaProst), zavegepant, TXA-127, USB-002, ambrisentan, nitric oxide nasal spray (NORS), pentoxifylline, propranolol. RESP301, sodium nitrite, or dipyridamole.

In some embodiments, the additional therapeutic agent is a vitamin D3 receptor agonist, such as cholecalciferol.

In some embodiments, the additional therapeutic agent is a zonulin inhibitor, such as larazotide acetate.

In some embodiments, the additional therapeutic agent is a synthetic retinoid derivative, such as fenretinide.

In some embodiments, the additional therapeutic agent is a glucose metabolism inhibitor such as WP-1122.

In some embodiments, the additional therapeutic agent is AT-H201, 2-deoxy-D-glucose, AD-17002, AIC-649, astodrimer, AZD-1656, bitespiramycin, bucillamine, budesonide. CNM-AgZn-17, Codivir, didodecyl methotrexate, DW-2008S (DW-2008), EDP-1815, EG-009A, Fabencov, Gamunex, genistein. GLS-1200, hzVSF-v13, imidazolyl ethanamide pentandioic acid, IMM-101, MAS-825, MRG-001, Nasitrol, Nylexa, OP-101, OPN-019, Orynotide rhesus theta defensin-1, pyronaridine+artesunate, dapsone, RPH-104, sodium pyruvate, Sulforadex, tafenoquine, TB-006, telacebec, Tempol, TL-895, thimesoral, trimodulin, XC-221, XC-7, zunsemetinib, metformin glycinate, lucinactant, EOM-613, mosedipimod, ivermectin, leflunomide, ibudilast. RBT-9, raloxifene, prothione, gemcabene, or idronoxil.

In some embodiments, the additional therapeutic agent is a CD73 antagonist, such as AK-119.

In some embodiments, the additional therapeutic agent is a CD95 protein fusion, such as asunercept.

In some embodiments, the additional therapeutic agent is a complement factor C2 modulator, such as ARGX-117.

In some embodiments, the additional therapeutic agent is a complement C3 inhibitor, such as NGM-621.

In some embodiments, the additional therapeutic agent is a CXC10 chemokine ligand inhibitor, such as EB-06.

In some embodiments, the additional therapeutic agent is a cytotoxic T-lymphocyte protein-4 fusion protein, such as abatacept.

In some embodiments, the additional therapeutic agent is an anti-S. Aureus antibody, such as tosatoxumab.

In some embodiments, the additional therapeutic agent is an anti-LPS antibody, such as IMM-124-E.

In some embodiments, the additional therapeutic agent is an adrenomedullin ligand inhibitor, such as enibarcimab.

In some embodiments, the additional therapeutic agent is a basigin inhibitor, such as meplazumab.

In some embodiments, the additional therapeutic agent is a CD3 antagonist, such as foralumab.

In some embodiments, the additional therapeutic agent is a connective tissue growth factor ligand inhibitor, such as pamrevlumab.

In some embodiments, the additional therapeutic agent is a complement C5a factor inhibitor, such as BDB-1 or vilobelimab.

In some embodiments, the additional therapeutic agent is a complement C5 factor inhibitor, such as ravulizumab.

In some embodiments, the additional therapeutic agent is a mannan-binding lectin serine protease-2 inhibitor, such as narsoplimab.

In some embodiments, the additional therapeutic agent is a GM-CSF modulator, such as gimsilumab, namilumab, plonmarlimab, otolimab, or lenzilumab.

In some embodiments, the additional therapeutic agent is a heat shock protein inhibitor/IL-6 receptor antagonist, such as siltuximab.

In some embodiments, the additional therapeutic agent is an IL-6 receptor antagonist, such as clazakizumab, levilimab, olokizumab, tocilizumab, or sirukumab.

In some embodiments, the additional therapeutic agent is an IL-8 receptor antagonist, such as BMS-986253.

In some embodiments, the additional therapeutic agent is an interleukin-1 beta ligand inhibitor, such as canakinumab.

In some embodiments, the additional therapeutic agent is an interferon gamma ligand inhibitor, such as emapalumab.

In some embodiments, the additional therapeutic agent is an anti-ILT7 antibody, such as daxdilimab.

In some embodiments, the additional therapeutic agent is a monocyte differentiation antigen CD14 inhibitor, such as atibuclimab.

In some embodiments, the additional therapeutic agent is a plasma kallikrein inhibitor, such as lanadelumab.

In some embodiments, the additional therapeutic agent is a platelet glycoprotein VI inhibitor, such as glenzocimab.

In some embodiments, the additional therapeutic agent is a T-cell differentiation antigen CD6 inhibitor, such as itolizumab.

In some embodiments, the additional therapeutic agent is a TNF alpha ligand inhibitor/TNF binding agent, such as infliximab.

In some embodiments, the additional therapeutic agent is an anti-LIGHT antibody, such as AVTX-002.

In some embodiments, the additional therapeutic agent is COVID-HIG.

In some embodiments, a compound of the disclosure, or a pharmaceutically acceptable salt thereof, is co-administered with one or more agents useful for the treatment and/or prophylaxis of COVID-19.

Non-limiting examples of such agents include corticosteroids, such as dexamethasone, hydrocortisone, methylprednisolone, or prednisone; interleukin-6 (IL-6) receptor blockers, such as tocilizumab or sarilumab; Janus kinase (JAK) inhibitors, such as baricitinib, ruxolitinib, or tofacitinib; and antiviral agents, such as molnupiravir, sotrovimab, or remdesivir.

In further embodiments, a compound of the disclosure, or a pharmaceutically acceptable salt thereof, is co-administered with two or more agents useful for the treatment of COVID-19. Agents useful for the treatment and/or prophylaxis of COVID-19 include but are not limited to a compound of the disclosure and two additional therapeutic agents, such as nirmatrelvir and ritonavir, casirivimab and imdevimab, or ruxolitinib and tofacitinib.

In some embodiments, the additional therapeutic agent is an antiviral agent. In some embodiments, the antiviral agent is an entry inhibitor. In some embodiments, the antiviral agent is a protease inhibitor. In some embodiments, the antiviral agent is an RNA polymerase inhibitor. In some embodiments, the additional therapeutic agent is a RNA-dependent RNA polymerase (RdRp) inhibitor.

In some embodiments, the antiviral agent is selected from angiotensin converting enzyme 2 inhibitors, angiotensin converting enzyme 2 modulators, angiotensin converting enzyme 2 stimulators, angiotensin II AT-2 receptor agonists, angiotensin II AT-2 receptor antagonists, angiotensin II receptor modulators, coronavirus nucleoprotein modulators, coronavirus small envelope protein modulators, coronavirus spike glycoprotein inhibitors, coronavirus spike glycoprotein modulators, COVID19 envelope small membrane protein inhibitors, COVID19 envelope small membrane protein modulators, COVID19 MPro inhibitors, COVID19 non structural protein 8 modulators, COVID19 nucleoprotein inhibitors, COVID19 nucleoprotein modulators, COVID19 protein 3a inhibitors, COVID19 replicase polyprotein 1a inhibitors, COVID19 replicase polyprotein 1a modulators, COVID19 replicase polyprotein 1ab inhibitors. COVID19 replicase polyprotein 1ab modulators, COVID19 spike glycoprotein inhibitors, COVID19 spike glycoprotein modulators, COVID19 structural glycoprotein modulators, papain inhibitors, protease inhibitors, protease modulators, RNA polymerase inhibitors, RNA polymerase modulators, RNA-dependent RNA polymerase (RdRp) inhibitors, SARS coronavirus 3C protease like inhibitors, 3CLpro/Mpro inhibitors, serine protease inhibitors, transmembrane serine protease 2 inhibitors, transmembrane serine protease 2 modulators, viral envelope protein inhibitors, viral protease inhibitors, viral protease modulators, viral protein target modulators, viral ribonuclease inhibitors, and viral structural protein modulators.

In some embodiments, the additional therapeutic agent is an entry inhibitor. For example, in some embodiments the additional therapeutic agent is an ACE2 inhibitor, a fusion inhibitor, or a protease inhibitor.

In some embodiments, the additional therapeutic agent is an angiotensin converting enzyme 2 inhibitor, such as SBK-001.

In some embodiments, the additional therapeutic agent is an angiotensin converting enzyme 2 modulator, such as neumifil or JN-2019.

In some embodiments, the additional therapeutic agent is an entry inhibitor such as MU-UNMC-1.

In some embodiments, the additional therapeutic agent is an angiotensin converting enzyme 2 stimulator, such as alunacedase alfa.

In some embodiments, the additional therapeutic agent is an angiotensin II AT-2 receptor agonist, such as VP-01.

In some embodiments, the additional therapeutic agent is an ACE II receptor antagonist, such as DX-600.

In some embodiments, the additional therapeutic agent is an angiotensin II receptor modulator, such as TXA-127.

In some embodiments, the additional therapeutic agent is a transmembrane serine protease 2 modulator, such as BC-201.

In some embodiments, the additional therapeutic agent is a viral envelope protein inhibitor, such as MXB-9 or MXB-004.

In some embodiments, the additional therapeutic agent is a vaccine. For example, in some embodiments, the additional therapeutic agent is a DNA vaccine, RNA vaccine, live-attenuated vaccine, inactivated vaccine (i.e., inactivated SARS-CoV-2 vaccine), therapeutic vaccine, prophylactic vaccine, protein-based vaccine, viral vector vaccine, cellular vaccine, or dendritic cell vaccine.

In some embodiments, the additional therapeutic agent is a vaccine such as tozinameran, NVX—CoV2373, elasomeran, KD-414, Janssen COVID-19 Vaccine. Vaxzevria, SCB-2019, AKS-452, VLA-2001, 5-268019, MVC-COV1901, mRNA-1273.214, NVX—CoV2515, Covaxin, BBIBP-CorV, GBP-510, mRNA-1273.351+mRNA-1273.617 (SARS-CoV-2 multivalent mRNA vaccine, COVID-19), Ad5-nCoV, Omicron-based COVID-19 vaccine (mRNA vaccine, COVID-19), SARS-CoV-2 Protein Subunit Recombinant Vaccine, Sputnik M, ZyCoV-D, COVID-19 XWG-03, mRNA-1273.529, mRNA-1010, CoronaVac, AZD-2816, Sputnik V, inactivated SARS-CoV-2 vaccine (Vero cell, COVID-19), DS-5670, PHH-1V, INO-4800, UB-612, coronavirus vaccine (whole-virion, inactivated/purified), ReCOV, MT-2766, ARCT-154, SP-0253, CORBEVAX, mRNA-1273.211, ZF-2001, Sputnik Light, recombinant protein vaccine (COVID-19/SARS-CoV-2 infection), VSV vector-based vaccine targeting spike glycoprotein (COVID-19), VLA-2101, GRAd-COV2, VPM-1002, COViran Barekat, Ad5-nCoV-1H, ARCoV, Covax-19, recombinant SARS-CoV-2 vaccine (protein sub-unit/CHO cell, COVID-19), BBV-154, RAZI Cov Pars, COVID-19 vaccine (inactivated/Vero cells/intramuscular, SARS-CoV-2 infection), COVID-19 vaccine (inactivated, Vero cells/intramuscular), BNT-162b2s01, CIGB-66, mRNA-1273.617, *Mycobacterium* w, ERUCOV-VAC, AG-0301-COVID19, fakhravac, AV-COVID-19, peptide vaccine (COVID-19), Nanocovax, SARS-CoV-2 vaccine (inactivated/Vero cells/intramuscular, COVID-19), QAZ-COVID-IN, S-875670 nasal vaccine, or BNT162b5.

In some embodiments, the additional therapeutic agent is a protease inhibitor. For example, in some embodiments the additional therapeutic agent is a 3C-like cysteine protease inhibitor (3CLpro, also called Main protease, Mpro), a papain-like protease inhibitor (PLpro), serine protease inhibitor, or transmembrane serine protease 2 inhibitor (TMPRSS2).

In some embodiments, the additional therapeutic agent is a 3CLpro/Mpro inhibitor, such as CDI-873, GC-373, GC-376, PBI-0451, UCI-1, DC-402234, DC-402267, RAY-1216, MPI-8, SH-879, SH-580, EDP-235, VV-993, CDI-988, MI-30, nirmatrelvir, ensitrelvir, ASC-11, EDDC-2214, SIM-0417, CDI-45205, COR-803, ALG-097111, $TJC_{1-642}$, CVD-0013943, eravacycline, cynarine, or prexasertib.

In some embodiments, the additional therapeutic agent is a papain-like protease inhibitor (PLpro), such as SBFM-PL4 or GRL-0617.

In some embodiments, the additional therapeutic agent is a SARS-CoV-2 helicase Nsp13 inhibitor, such as EIS-4363.

In some embodiments, the additional therapeutic agent is a SARS-CoV-2 spike (S) and protease modulator, such as ENU-200.

In some embodiments, the additional therapeutic agent is a protease inhibitor, such as ALG-097558 or MRX-18.

In some embodiments, the additional therapeutic agent is a serine protease inhibitor, such as upamostat, nafamostat, camostat mesylate, nafamostat mesylate, or camostat.

In some embodiments, the additional therapeutic agent is a 3CLpro/transmembrane serine protease 2 inhibitor, such as SNB-01 or SNB-02.

In some embodiments, the additional therapeutic agent is a viral protease inhibitor, such as Pan-Corona, Cov-X, or bepridil.

In some embodiments, the additional therapeutic agent is an RNA polymerase inhibitor. For example, in some embodiments, the additional therapeutic agent is an RNA polymerase inhibitor, or a RNA-dependent RNA polymerase (RdRp) inhibitor.

In some embodiments, the additional therapeutic agent is an RNA-dependent RNA polymerase (RdRp) inhibitor, such as remdesivir, NV—CoV-2-R, NV—CoV-1 encapsulated remdesivir, GS-621763, GS-5245, GS-441524, DEP remdesivir, ATV-006, VV-116, LGN-20, CMX-521 and compounds disclosed in WO2022142477, WO2021213288, WO2022047065.

In some embodiments, the additional therapeutic agent is an RNA polymerase inhibitor, such as molnupiravir (EIDD-2801), favipiravir, bemnifosbuvir, sofosbuvir, ASC-10, or galidesivir.

In some embodiments, the additional therapeutic agent is viral entry inhibitor, such as brilacidin.

In some embodiments, the additional therapeutic agent is an antibody that binds to a coronavirus, for example an antibody that binds to SARS or MERS.

In some embodiments, the additional therapeutic agent is an antibody, for example a monoclonal antibody. For example, the additional therapeutic agent is an antibody against SARS-CoV-2, neutralizing nanobodies, antibodies that target the SARS-CoV-2 spike protein, fusion proteins, multispecific antibodies, and antibodies that can neutralize SARS-CoV-2 (SARS-CoV-2 neutralizing antibodies).

In some embodiments, the additional therapeutic agent is an antibody that targets specific sites on ACE2. In some embodiments, the additional therapeutic agent is a polypeptide targeting SARS-CoV-2 spike protein (S-protein).

In some embodiments, the additional therapeutic agent is a SARS-CoV-2 virus antibody.

In some embodiments, the antibody is ABBV-47D11, COVI-GUARD (STI-1499), C144-LS+C135-LS. DXP-604, JMB-2002, LY-CovMab, bamlanivimab (LY-CoV555), S309, SAB-185, etesevimab (CB6), COR-101, JSO16, VNAR, VIR-7832 and/or sotrovimab (VIR-7831), casirivimab+imdevimab (REGN-COV2 or REGN10933+RGN10987), BAT2020, BAT2019, 47D11, YBSW-015, or PA-001.

In some embodiments, the additional therapeutic agent is STI-9199 (COVI-SHIELD) or AR-701 (AR-703 and AR-720).

In some embodiments, the additional therapeutic agent is BRII-196, BRII-198, ADG-10, ADG-20, ABP-300, BI-767551, CT-P63, JS-026, sotrovimab (GSK-4182136), tixagevimab+cilgavimab (AZD-7442), regdanvimab, SAB-301, AOD-01, plutavimab (COVI-AMG), 9MW-3311 (MW-33), DXP-593, BSVEQAb, anti-SARS-CoV-2 IgY, COVID-EIG, CSL-760, REGN-3048-3051, SARS-CoV-2 monoclonal antibodies (COVID-19, ADM-03820), enuzovimab (HFB-30132A), INM-005, SCTA01, TY-027, XAV-19, amubarvimab+romlusevimab, SCTA-01, bebtelovimab, beludavimab, IBI-0123, IGM-6268. FYB-207, REGN-14256, XVR-011, TB202-3, TB181-36, LQ-050, COVAB-36, MAD-0004J08, STI-2099, or ACV-200-17.

In some embodiments, the additional therapeutic agent is an engineered ACE-2-IgGI-Fc-fusion protein targeting SARS-Cov-2 RBD, such as EU-129, bivalent ACE2-IgG Fc null fusion protein (SI—FO19).

In some embodiments, the additional therapeutic agent is an ACE2-Fc receptor fusion protein, such as HLX-71.

In some embodiments, the additional therapeutic agent is ensovibep.

In some embodiments, the additional therapeutic agent is SYZJ-001.

In some embodiments, the additional therapeutic agent is an HIV-1 protease inhibitor, such as ASC-09F (ASC-09+ritonavir) or lopinavir+ritonavir.

In some embodiments, the additional therapeutic agent is a non-nucleoside reverse transcriptase inhibitor, such as elsulfavirine.

In some embodiments, the additional therapeutic agent is a nucleoside reverse transcriptase inhibitor, such as azvudine.

In some embodiments, the additional therapeutic agent is Abbv-990, NED-260, ALG-097431, ENOB-CV-01, EIS- 10700, beta-521, SIM-0417, molnupiravir, Pan-Corona, Tollovir, nirmatrelvir+ritonavir (Paxlovid*), favipiravir, GC-376, upamostat, LeSoleil-01. LeSoleil-02+, benfovir, VV-116, VV-993, SNB-01, EDP-235, Cov-X, ensitrelvir, MPI-8, masitinib, ALG-097558, ASC-11, PBI-0451, nafamostat, nafamostat mesylate, CDI-45205, COR-803, ALG-097111, BC-201, SH-879, CDI-873, CDI-988, remdesivir, NV—CoV-2-R, NV—CoV-1 encapsulated remdesivir, NA-831+remdesivir, DEP remdesivir, GS-621763, GS-5245, GLS-5310, bemnifosbuvir, QLS-1128, ASC-10, SBFM-PL4, camostat mesylate, UCI-1, DC-402234, ebselen, SH-580, LeSoleil-01, LeSoleil-02+, MRX-18, MXB-9, MI-09, MI-30. SNB-02, TJC1-642, ENU-200, CVD-0013943, GS-441524, bepridil, MXB-004, eravacycline, GRL-0617, camostat, GC-373, nitazoxanide, cynarine, prexasertib, RAY-1216, SACT-COVID-19, MP-18, EIDD-1931, EDDC-2214, nitric oxide, apabetalone, AnQlar. SBK-001, LQ-050, CG-SpikeDown, bamlanivimab, HLX-71, FYB-207, ensovibep, SYZJ-001, EU-129, neumifil, JN-2019, AR-701, vostesyl, PLM-402, PJS-539, CTB-ACE2, TB181-36, TB202-3, ABP-300, XVR-011, MU-UNMC-1, MU-UNMC-2, alunacedase alfa, VP-01, TRV-027, DX-600, TXA-127, mRNA-1273.214, Omicron-based COVID-19 vaccine, NVX—CoV2515, tozinameran, elasomeran, Ad5-nCoV, BBIBP-CorV, CoronaVac, MVC-COV1901, NVX—CoV2373, sotrovimab, Sputnik V, Vaxzevria. ZF-2001, or ZyCoV-D.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially. i.e., serially, whereas in combination therapy, effective dosages of two or more active ingredients are administered together. A synergistic anti-viral effect denotes an antiviral effect, which is greater than the predicted purely additive effects of the individual compounds of the combination.

Kits

Also provided herein are kits that includes a compound disclosed herein, a pharmaceutically acceptable salt, stereoisomer, mixture of stereoisomers or tautomer thereof. In some embodiments the kits described herein may comprise a label and/or instructions for use of the compound in the treatment of a disease or condition in a subject (e.g., human) in need thereof. In some embodiments, the disease or condition is viral infection.

In some embodiments, the kit may also comprise one or more additional therapeutic agents and/or instructions for use of additional therapeutic agents in combination with the compound described herein in the treatment of the disease or condition in a subject (e.g., human) in need thereof.

In some embodiments, the kits provided herein comprises individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units may include pills, tablets, capsules, prefilled syringes or syringe cartridges, IV bags, inhalers, nebulizers etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit may contain a single dosage unit and in others, multiple dosage units are present, such as the number of dosage units required for a specified regimen or period.

Also provided are articles of manufacture that include a compound described herein, or a pharmaceutically acceptable salt, stereoisomer, mixture of stereoisomers or tautomer thereof, and a container. In some embodiments, the container of the article of manufacture is a vial, jar, ampoule, preloaded syringe, blister package, tin, can, bottle, box, an intravenous bag, an inhaler, or a nebulizer.

The invention will be described in greater detail by way of specific examples. The following examples are offered for illustrative purposes and are not intended to limit the invention in any manner. Those of skill in the art will readily recognize a variety of non-critical parameters, which can be changed or modified to yield essentially the same results.

EXAMPLES

Certain abbreviations and acronyms are used in describing the experimental details. Although most of these would be understood by one skilled in the art, Table 1 contains a list of many of these abbreviations and acronyms.

TABLE 1

List of Abbreviations and Acronyms

| Abbreviation | Meaning |
|---|---|
| Ac | acetate |
| AcOH | acetic acid |
| ACN | acetonitrile |
| AmPhos | di-tert-butyl(4-dimethylaminophenyl)phosphine |
| AQ | aqueous |
| Bn | benzyl |
| Bpin | (pinacolato)boron |
| B2Pin2 | bis(pinacolato)diboron |
| Boc | tert-butoxycarbonyl |
| Boc$_2$O | di-tert-butyl dicabonate |
| Bu | Butyl |
| Bz | benzoyl |
| BzCl | benzoyl chloride |
| cataCXium ® A Pd G3 | Mesylate[(di(1-adamantyl)-n-butylphosphine)-2-(2'-amino-1,1'-biphenyl)]palladium(II) |
| CDI | 1,1'-carbonyldiimidazole |
| DBAD | di-tert-butyl azodicarboxylate |
| DBU | 1,8-Diazabicyclo[5.4.0]undec-7-ene |
| DCE | 1,2-dichloroethane |
| DCM | dichloromethane |
| DEA | diethylamine |
| Deoxofluor | Bis(2-methoxyethyl)aminosulfur trifluoride |
| DIPEA | N,N-diisopropylethylamine |
| DIAD | diisopropyl azodicarboxylate |
| DMA | dimethylacetamide |
| 4-DMAP, DMAP | 4-dimethylaminopyridine |
| DME | dimethoxyethane |
| DMF | dimethylformamide |
| DMSO | dimethylsulfoxide |
| dppf | 1,1'-Ferrocenediyl-bis(diphenylphosphine) |
| dtbbpy | 4,4'-Di-tert-butyl-2,2'-dipyridyl |
| EDC | N-(3-dimethylaminopropyl)-N'-ethylcarbodiimide hydrochloride |
| EDCI | N-(3-dimethylaminopropyl)-N'-ethylcarbodiimide hydrochloride |
| ES/MS | electron spray mass spectrometry |
| Et | ethyl |
| HATU | 1-[Bis(dimethylamino)methylene]-1H-1,2,3-triazolo[4,5-b]pyridinium 3-oxide hexafluorophosphate |
| HEX | hexanes |
| HNMR | hydrogen nuclear magnetic resonance |
| IBX | 2-Iodoxybenzoic acid |
| IPA | isopropanol |
| JohnPhos | (2-Biphenyl)di-tert-butylphosphine |
| KOtBu | potassium tert-butoxide |
| LC | liquid chromatography |
| LCMS | liquid chromatography/mass spectrometry |
| MCPBA | meta-chloroperbenzoic acid |
| Me | methyl |
| Ms | methanesulfonyl |
| m/z | mass to charge ratio |
| MS or ms | mass spectrum |
| MW | microwave |
| NBS | N-bromosuccinimide |
| NCS | N-chlorosuccinimide |
| NIS | N-iodosuccinimide |
| NMP | N-methyl-2-pyrrolidone |
| NMR | nuclear magnetic resonance |
| Pd(AmPhos)$_2$Cl$_2$ | Bis(di-tert-butyl(4-dimethylaminophenyl)phosphine)dichloropalladium(II) |
| Pd(dppf)Cl$_2$ | [1,1'-Bis(diphenylphosphino)ferrocene]dichloropalladium(II) |
| Ph | phenyl |
| Ph3P | triphenylphosphine |
| Pg | Protecting group |
| pin | pinacol |
| Piv | pivaloyl |
| PMB | para-methoxybenzyl |
| PPT | precipitate |
| Pyr | pyridine |
| RBF | round bottom flask |
| RP-HPLC | reverse phase high performance liquid chromatography |
| RT | room temperature |
| SAT | saturated |
| SEM | [2-(trimethylsilyl)ethoxy]methyl |
| SFC | supercritical fluid chromatography |
| STAB | Sodium triacetoxyborohydride |
| TLC | thin layer chromatography |
| tBuXPhos Pd G3 | [(2-Di-tert-butylphosphino-2',4',6'-triisopropyl-1,1'-biphenyl)-2-(2'-amino-1,1'-biphenyl)] palladium(II) methanesulfonate |
| XantPhos | 4,5-Bis(diphenylphosphino)-9,9-dimethylxanthene |
| XPhos Pd G2 | Chloro(2-dicyclohexylphosphino-2',4',6'-triisopropyl-1,1'-biphenyl)[2-(2'-amino-1,1'-biphenyl)]palladium(II) |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate |
| T3P | Propanephosphonic acid anhydride |
| TBAF | Tetrabutylammonium fluoride |
| TBAI | Tetrabutylammonium iodide |
| TCFH | Chloro-N,N,N',N'-tetramethylformamidinium hexafluorophosphate |
| TEA | triethylamine |
| TFA | trifluoroacetic acid |
| THF | tetrahydrofuran |
| Tf | trifluoromethanesulfonyl |
| Tf$_2$O | trifluoromethanesulfonic anhydride |
| TMEDA | tetramethylethylenediamine |
| TMS | tetramethylsilyl |
| Ts | 4-toluenesulfonyl |
| δ | parts per million referenced to residual solvent peak |

I. Intermediates

Intermediates I-1 and I-2

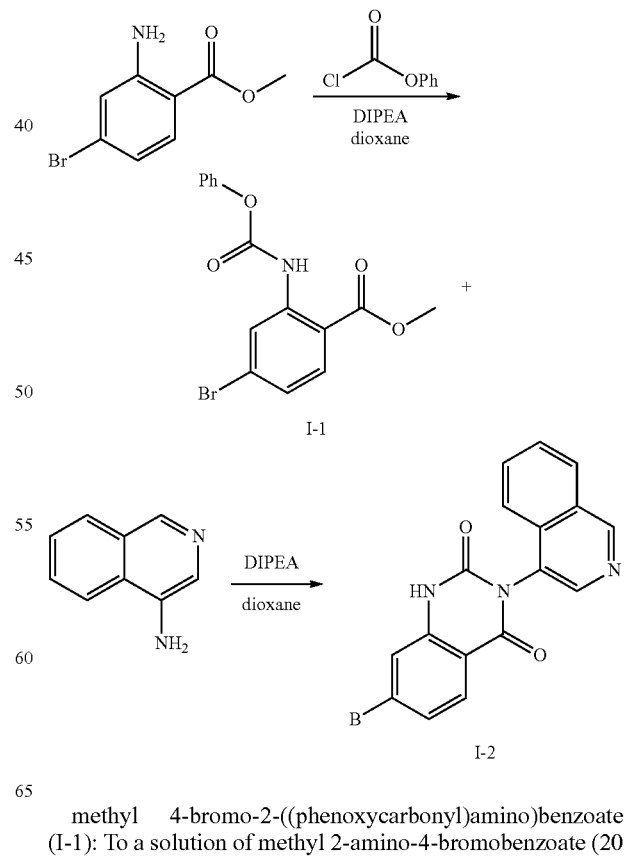

methyl 4-bromo-2-((phenoxycarbonyl)amino)benzoate (I-1): To a solution of methyl 2-amino-4-bromobenzoate (20 g, 86.9 mmol) in dry dioxane (200 mL) was added DIPEA (22.7 mL, 130 mmol) followed by phenyl chloroformate (14.2 mL, 109 mmol). The reaction mixture was heated at 90° C. for 16 hours, after which the mixture was cooled to room temperature. The mixture was concentrated under reduced pressure, and the crude material was purified by silica chromatography (eluent: EtOAc in hexanes) to provide the product.

$^1$H NMR (400 MHz, Chloroform-d) δ 10.95 (s, 1H), 8.75 (d, J=2.0 Hz, 1H), 7.93 (d, J=8.6 Hz, 1H), 7.43 (tt, J=7.6, 2.3 Hz, 2H), 7.32-7.17 (m, 4H), 3.98 (s, 3H).

ES/MS: 350.0 [M]$^+$.

7-bromo-3-(isoquinolin-4-yl)quinazoline-2,4(1H,3H)-dione (I-2): To a solution of methyl 4-bromo-2-((phenoxycarbonyl)amino)benzoate (15 g, 42.8 mmol) in dry dioxane (200 mL) was added DIPEA (11.2 mL, 64.3 mmol) followed by isoquinolin-4-amine (7.4 g, 51.4 mmol). The reaction mixture was heated at 90° C. for 16 hours, after which the mixture was cooled to room temperature. The mixture was subsequently cooled to 0° C. and let stand for 30 minutes. The precipitate was filtered, and subsequently washed with water (3×30 mL). The precipitate was dried under vacuum, and was carried forward as the title compound.

ES/MS: 368.0 [M$^+$].

$^1$H NMR (400 MHz, DMSO-d$_6$) δ 11.86 (s, 1H), 9.43 (d, J=0.8 Hz, 1H), 8.56 (s, 1H), 8.33-8.25 (m, 1H), 7.91-7.85 (m, 2H), 7.77 (tt, J=6.9, 5.3 Hz, 2H), 7.49 (d, J=1.8 Hz, 1H), 7.46 (dd, J=8.4, 1.8 Hz, 1H).

Preparation of Intermediate I-3

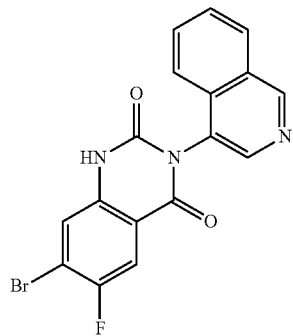

I-3

7-bromo-6-fluoro-3-(isoquinolin-4-yl)quinazoline-2,4 (1H,3H)-dione (I-3): Prepared analogously to 1-2, substituting methyl 2-amino-4-bromobenzoate with methyl 2-amino-4-bromo-5-fluorobenzoate.

ES/MS: 385.9 (M$^+$).

Preparation of Intermediate I-4

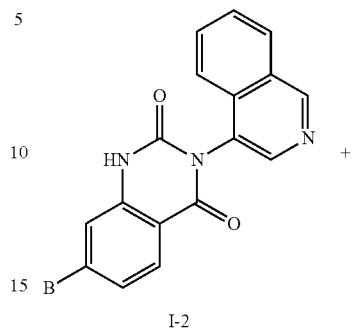

I-2

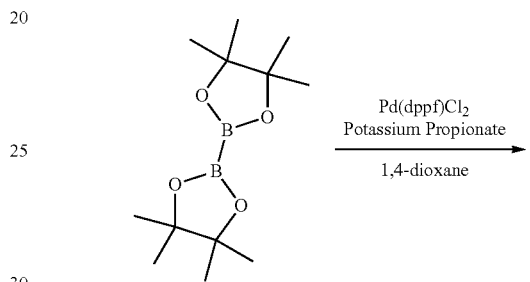

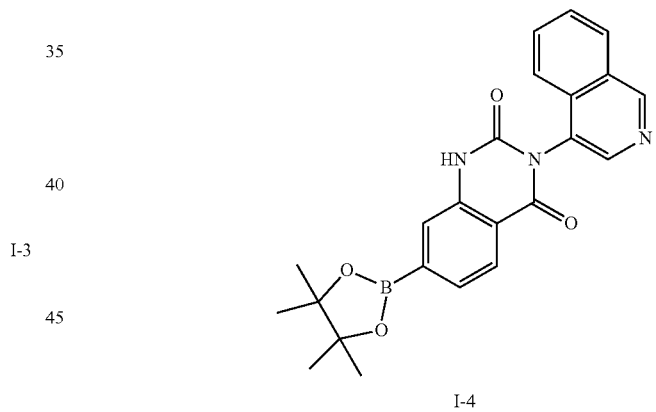

I-4

3-(isoquinolin-4-yl)-7-(4,4,5,5-tetramethyl-1,3,2-dioxaborolan-2-yl)quinazoline-2,4(1H,3H)-dione (I-4): To a 40 mL vial were added 7-bromo-3-(isoquinolin-4-yl)quinazoline-2,4(1H,3H)-dione (I-2) (500 mg, 1.36 mmol), Bis(pinacolato)diboron (690 mg, 2.72 mmol), [1,1'-Bis(diphenylphosphino)ferrocene]dichloropalladium(II) (101 mg, 0.136 mmol), and potassium propionate (457 mg, 4.07 mmol). The mixture was dissolved in 1,4-dioxane (8 mL), and argon was bubbled through the reaction mixture for 1 minute. The vial was sealed, and the mixture was heated at 95° C. for 2 hours. The mixture was cooled to rt, filtered through celite (rinsing with EtOAc), and concentrated under reduced pressure. The crude residue was purified by silica gel chromatography (eluent: EtOAc/hexanes, then 15% MeOH in EtOAc) to provide the product 1-4.

ES/MS: 416.2 (M+H$^+$).

Preparation of Intermediate I-5

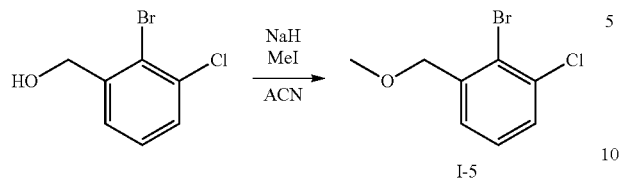

2-bromo-1-chloro-3-(methoxymethyl)benzene (1-5): To a 40 mL vial were added (2-bromo-3-chloro-phenyl)methanol (500 mg, 2.26 mmol), and dry acetonitrile (5 mL). The mixture was cooled to 0° C. under a N2 atmosphere, and sodium hydride (60% wt dispersion in mineral oil; 87 mg, 2.26 mmol) was added. The mixture was stirred at 0° C. for 30 minutes before iodomethane (0.42 mL, 6.77 mmol) was added. The mixture was stirred for 1 hour, warming to rt. The mixture was subsequently diluted with EtOAc (50 mL) and water (10 mL), and the layers were separated. The aqueous layer was extracted with EtOAc (10 mL), and the combined organic layers were dried over MgSO₄, filtered, and concentrated under reduced pressure. The crude residue was purified by silica gel chromatography (eluent: EtOAc/hexanes) to provide the product 1-5.

$^1$H NMR (400 MHz, Chloroform-d) δ 7.41 (ddd, J=10.2, 6.0, 2.2 Hz, 2H), 7.33-7.24 (m, 1H), 4.56 (s, 2H), 3.51 (s, 3H).

Preparation of Intermediate I-6

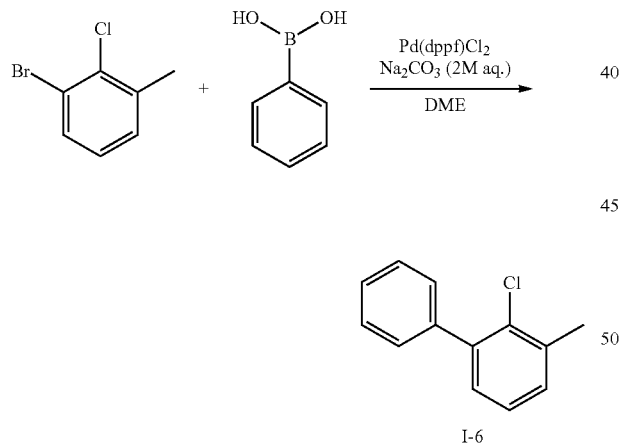

2-chloro-3-methyl-1,1'-biphenyl (1-6): To a 40 mL vial were added 1-bromo-2-chloro-3-methyl-benzene (200 mg, 0.97 mmol), phenylboronic acid (71 mg, 0.578 mmol), and Pd(dppf)Cl₂ (43 mg, 0.0578 mmol). DME (3 mL) and sodium carbonate (2M aqueous, 0.58 mL, 1.16 mmol), and the mixture was degassed with argon for 30 seconds. The vial was sealed, and the reaction mixture was heated at 80° C. for 2 hours. The mixture was subsequently concentrated under reduced pressure. The crude residue was purified by silica gel chromatography (eluent: EtOAc/hexanes) to provide the product 1-6.

Preparation of Intermediate I-7

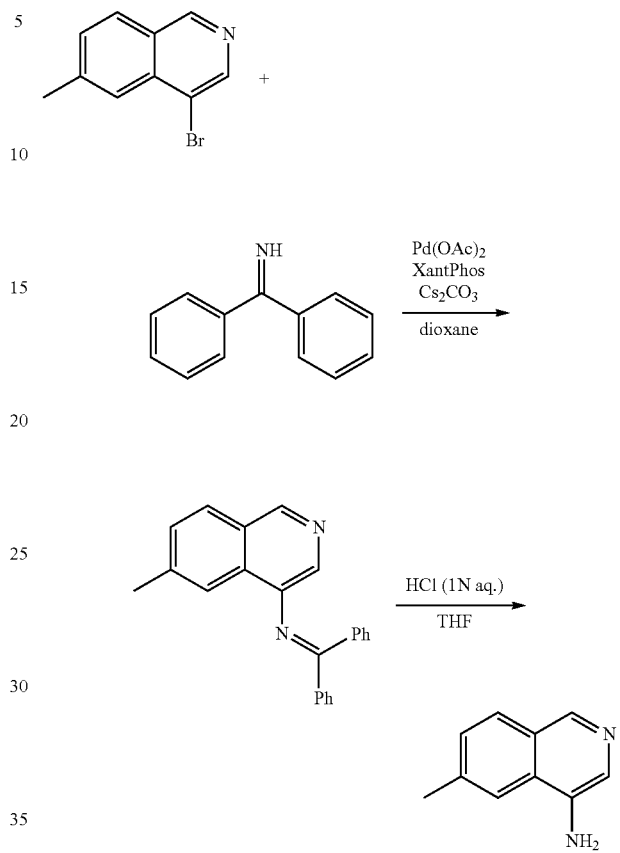

N-(6-methylisoquinolin-4-yl)-1,1-diphenylmethanimine: To a dram vial were added 4-bromo-6-methyl-isoquinoline (100 mg, 0.45 mmol), diphenylmethanimine (98 mg, 0.54 mmol), Pd(OAc)₂ (10 mg, 0.045 mmol), 9,9-Dimethyl-4,5-bis(diphenylphosphino)xanthene (XantPhos) (52 mg, 0.09 mmol) and cesium carbonate (147 mg, 0.45 mmol). Dioxane (2 mL) was added, and the mixture was degassed with argon for 30 seconds. The vial was sealed, and the reaction mixture was heated at 100° C. for 16 hours. The mixture was subsequently concentrated under reduced pressure. The crude residue was purified by silica gel chromatography (eluent: EtOAc/hexanes) to provide the product.

ES/MS: 323.8 (M+H⁺).

6-methylisoquinolin-4-amine (I-7): To a dram vial were added N-(6-methylisoquinolin-4-yl)-1,1-diphenylmethanimine (130 mg, 0.403 mmol). THF (4 mL) and HCl (1N aqueous; 4 mL, 4 mmol) were added, and the mixture was stirred at rt for 2 hours. The reaction was diluted with EtOAc (30 mL), and the mixture was basified with KOH (1M aqueous, 5 mL). The layers were separated, and the aqueous layer was extracted with EtOAc (2×20 mL). The combined organic layers were dried over MgSO₄, filtered, and concentrated under reduced pressure. The crude residue was purified by silica gel chromatography (eluent: EtOAc/hexanes, then MeOH/EtOAc) to provide the product.

ES/MS: 159.2 (M+H⁺).

Preparation of Intermediate I-8

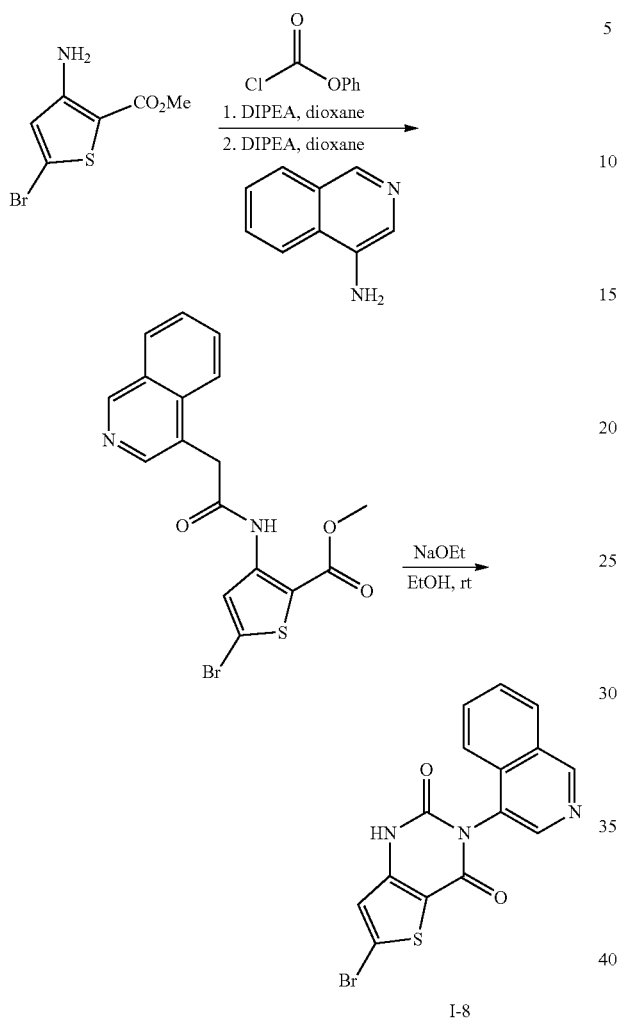

methyl 5-bromo-3-(3-(isoquinolin-4-yl)ureido)thiophene-2-carboxylate: To a solution of methyl 3-amino-5-bromo-thiophene-2-carboxylate (3.0 g, 12.7 mmol, 1.0 equiv.) in dry dioxane (55 mL, 0.23M) at 70° C. was added DIPEA (4.43 mL, 25.4 mmol, 2.0 equiv.) followed by phenyl chloroformate (2.5 mL, 1.5 equiv.). The reaction mixture was monitored by LCMS until full consumption of starting material was observed (~3 h, ES/MS: 357.8 [M+H+]), after which isoquinolin-4-amine (2.2 g, 15.2 mmol, 1.2 equiv.) was added, followed by additional DIPEA (4.42 mL, 25.4 mmol, 2.0 equiv.) The reaction mixture was refluxed (dioxane) and monitored by LCMS after which full consumption of the ester was observed (~3 h). The entire reaction mixture was cooled to ambient temperature and concentrated under reduced pressure. EtOAc (20 mL) was then added followed by H2O (100 mL), which formed a precipitate. The solid was collected via filtration, washed with additional H2O (25 mL), and dried to deliver intermediate methyl 5-bromo-3-(3-(isoquinolin-4-yl)ureido)thiophene-2-carboxylate which was used to the next step without further purification.

ES/MS: 407.0 [M+H$^+$].

5-bromo-3-(4-isoquinolyl)-1H-thieno[3,2-d]pyrimidine-2,4-dione (I-8): To a suspension of methyl 5-bromo-3-(3-(isoquinolin-4-yl)ureido)thiophene-2-carboxylate (12.7 mmol) in ethanol (40 mL, 0.32 M) was added a solution of sodium ethoxide (7.11 mL, 2M in ethanol, 1.5 equiv.) at room temperature, and the reaction mixture stirred at room temperature after which LCMS showed full consumption of starting material (~2 h). The reaction mixture was concentrated under reduced pressure after which EtOAc (20 mL) was added followed by 1M HCl (50 mL), which formed a precipitate. The solid was collected via filtration to deliver the product.

ES/MS: 375.9 [M+H$^+$]: $^1$H NMR (400 MHz, DMSO-d$_6$) δ 12.32 (s, 1H), 9.45 (s, 1H), 8.56 (s, 1H), 8.32-8.25 (m, 1H), 7.89-7.73 (m, 3H), 7.23 (s, 1H).

Preparation of Intermediate I-9

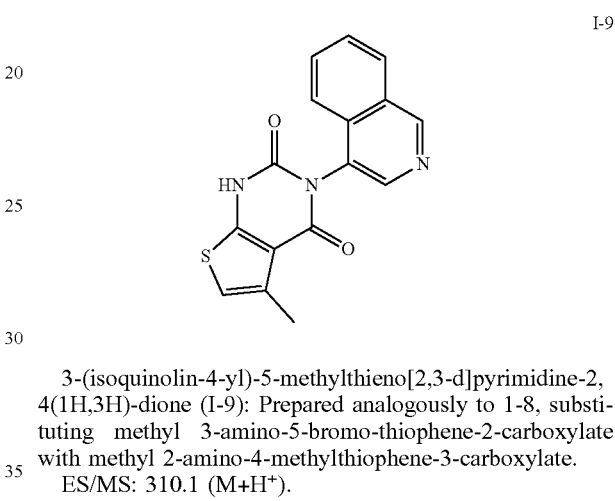

3-(isoquinolin-4-yl)-5-methylthieno[2,3-d]pyrimidine-2,4(1H,3H)-dione (I-9): Prepared analogously to 1-8, substituting methyl 3-amino-5-bromo-thiophene-2-carboxylate with methyl 2-amino-4-methylthiophene-3-carboxylate.

ES/MS: 310.1 (M+H$^+$).

Preparation of Intermediate I-10

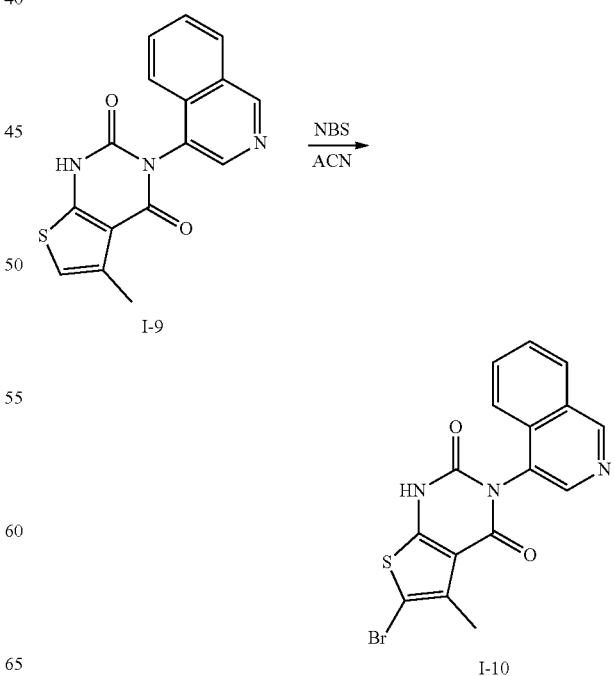

6-bromo-3-(isoquinolin-4-yl)-5-methylthieno[2,3-d]pyrimidine-2,4(1H,3H)-dione (I-10): To a solution of 3-(isoquinolin-4-yl)-5-methylthieno[2,3-d]pyrimidine-2,4(1H,3H)-dione 1-9 (45 mg, 0.145 mmol) in acetonitrile (6 mL) at 0° C. was added NBS (26 mg, 0.145 mmol) dissolved in acetonitrile (1 mL) dropwise until LCMS showed completion of reaction. The reaction mixture was concentrated under reduced pressure and the crude residue was purified by column chromatography (eluent: EtOAc in hexane) to give the product.

ES/MS: 387.95 (M+).

Preparation of Intermediate I-11

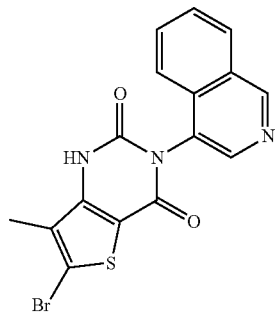

6-bromo-3-(isoquinolin-4-yl)-7-methylthieno[3,2-d]pyrimidine-2,4(1H,3H)-dione (I-11): Prepared analogously to 1-8, substituting methyl 2-amino-5-bromothiophene-3-carboxylate with methyl 3-amino-5-bromo-4-methylthiophene-2-carboxylate (methyl 3-amino-5-bromo-4-methylthiophene-2-carboxylate was prepared according to the literature procedure in WO2008/137060, page 46, incorporated by reference herein).

ES/MS: 388.0 (M+).

Preparation of Intermediate I-12

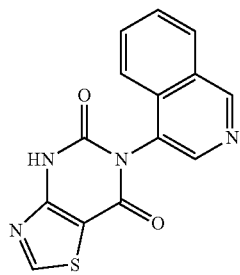

6-(isoquinolin-4-yl)thiazolo[4,5-d]pyrimidine-5,7(4H,6H)-dione (I-12): Prepared analogously to I-8, substituting methyl 3-amino-5-bromo-thiophene-2-carboxylate with methyl 4-aminothiazole-5-carboxylate.

ES/MS: 297.1 (M+H+).

Preparation of Intermediate I-13

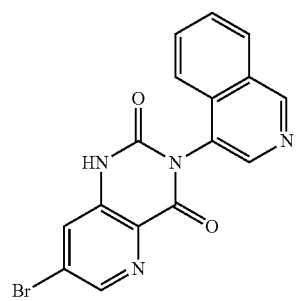

7-bromo-3-(isoquinolin-4-yl)pyrido[3,2-d]pyrimidine-2,4(1H,3H)-dione (I-13): Prepared analogously to I-2, substituting methyl 2-amino-4-bromobenzoate with methyl 3-amino-5-bromo-pyridine-2-carboxylate.

Preparation of Intermediate I-14

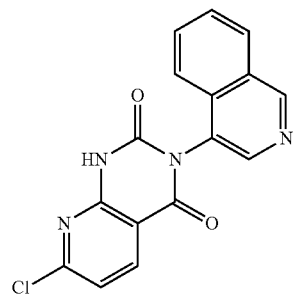

7-chloro-3-(4-isoquinolyl)-1H-pyrido[2,3-d]pyrimidine-2,4-dione (I-14): Prepared analogously to I-2, substituting methyl 2-amino-4-bromobenzoate with methyl 2-amino-6-chloronicotinate.

ES/MS: 325.0 (M+).

Preparation of Intermediate I-15

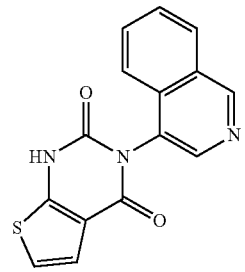

3-(4-isoquinolyl)-1H-thieno[2,3-d]pyrimidine-2,4-dione (I-15): Prepared analogously to 1-8, substituting methyl 3-amino-5-bromo-thiophene-2-carboxylate with methyl 2-aminothiophene-3-carboxylate.

ES/MS: 296.3 (M+H+).

Preparation of Intermediate I-16

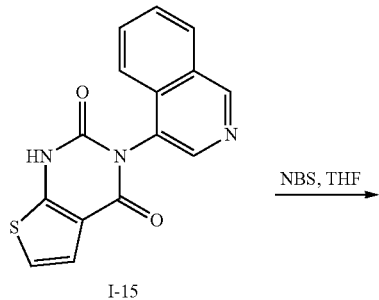

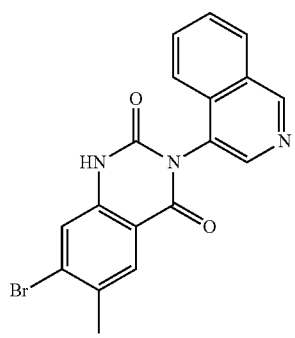

6-bromo-3-(4-isoquinolyl)-1H-thieno[2,3-d]pyrimidine-2,4-dione (I-16): To a cooled (0° C. via ice-bath) solution of I-15 (126 mg, 0.43 mmol) in THF (5 mL) was slowly added a solution of NBS (76 mg, 0.43 mmol; added drop-wise) in MeCN (2 mL). The reaction mixture was monitored via LCMS for completion. The solution was concentrated and taken directly to the next step without purification.

ES/MS: 374.0 (M+).

Preparation of Intermediate I-17

7-bromo-3-(isoquinolin-4-yl)-6-methylquinazoline-2,4 (1H,3H)-dione (I-17): Prepared analogously to 1-2 by replacing methyl 2-amino-4-bromobenzoate with methyl 2-amino-4-bromo-5-methylbenzoate.

ES/MS: 382.1 [M+].

Preparation of Intermediate I-18

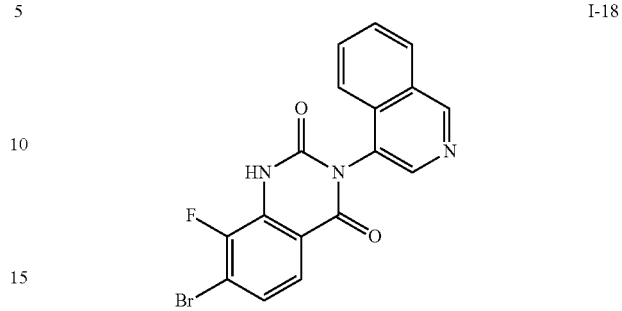

7-bromo-8-fluoro-3-(isoquinolin-4-yl)quinazoline-2,4 (1H,3H)-dione (I-18): Prepared analogously to (I-2) by replacing methyl 2-amino-4-bromobenzoate with methyl 2-amino-4-bromo-3-fluoro-benzoate.

ES/MS: 388.0 [M+H+].

Preparation of Intermediate I-19

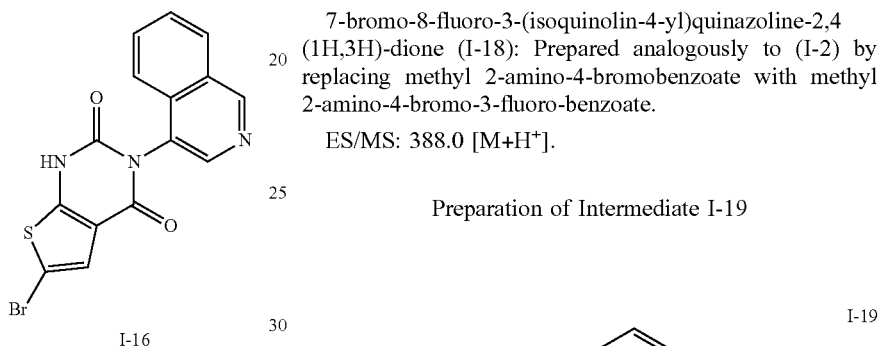

7-bromo-3-(isoquinolin-4-yl)-6-methoxyquinazoline-2,4 (1H,3H)-dione (I-19): Prepared analogously to 1-2 by replacing methyl 2-amino-4-bromobenzoate with methyl 2-amino-4-bromo-5-methoxy-benzoate.

ES/MS: 398.0 [M+].

Preparation of Intermediate I-20

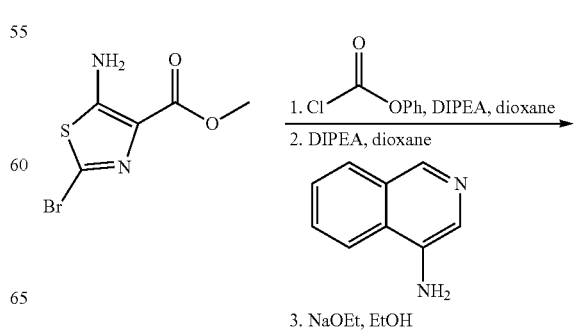

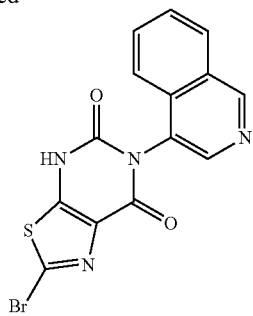

I-20

2-bromo-6-(4-isoquinolyl)-4H-thiazolo[5,4-d]pyrimidine-5,7-dione (I-20): To a solution of methyl 5-amino-2-bromothiazole-4-carboxylate (520 mg, 2.19 mmol) and DIPEA (764 µL, 4.39 mmol) in dry dioxane (1 mL) was added phenyl chloroformate (429 µL, 3.29 mmol). The reaction mixture was stirred at 90° C. for 3 hours and LCMS showed consumption of the starting material and formation the carbamate intermediate, after which additional DIPEA (764 µL, 4.38 mmol) was added followed by isoquinolin-4-amine (379 mg, 2.63 mmol). The reaction mixture was stirred at 90° C. for 5 hr. The reaction mixture was cooled down to room temperature and concentrated under reduced pressure. The crude residue was dissolved in MeOH and dry loaded on column chromatography and eluted with EtOAc. The solid product was suspended in EtOH (2 mL) followed by a dropwise addition of NaOEt (21% wt in EtOH) until the solids dissolved. The resulting reaction mixture was stirred at 50° C. for 1 hour. The reaction mixture was concentrated under reduced pressure and to the crude residue were added DMF (1 mL), acetonitrile (0.5 mL), TFA (0.3 mL) and water (0.2 mL). The mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the title intermediate.
ES/MS: 376.9 [M+].

Preparation of Intermediate I-21

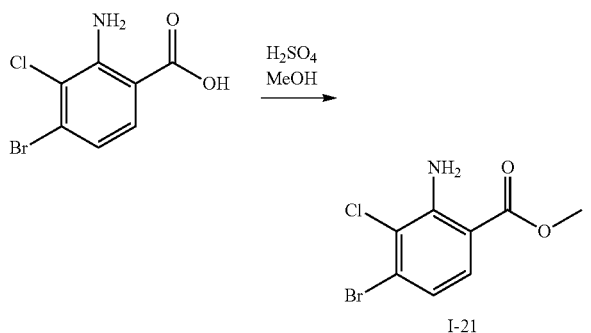

I-21

Methyl 2-amino-4-bromo-3-chloro-benzoate (I-21): To a solution of 2-amino-4-bromo-3-chloro-benzoic acid (250 mg, 0.99 mmol) in MeOH (2 mL) was added H$_2$SO$_4$ (98%, 69 µL). The reaction mixture was refluxed overnight. LCMS showed formation of the desired product. The reaction mixture was cooled down to room temperature, concentrated under reduced pressure. The residue product was diluted with water (10 mL) followed by addition of K$_2$CO$_3$ (100 mg). The aqueous solution was extracted with DCM (3×10 mL) and the combined organic layer was dried over Na$_2$SO$_4$ and concentrated under reduced pressure to provide the title compound.
ES/MS: 266.0 [M+H+].
$^1$H NMR (400 MHz, CDCl$_3$) δ 7.69 (d, J=8.7 Hz, 1H), 6.93 (d, J=8.7 Hz, 1H), 6.51 (s, 2H), 3.91 (s, 3H).

Preparation of Intermediate I-22

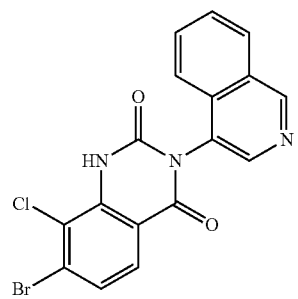

I-22

7-bromo-8-chloro-3-(isoquinolin-4-yl)quinazoline-2,4 (1H,3H)-dione (I-22): Prepared analogously to 1-2 by replacing methyl 2-amino-4-bromobenzoate with methyl 2-amino-4-bromo-3-chloro-benzoate (1-21).
ES/MS: 402.0 [M+].

Preparation of Intermediate I-23

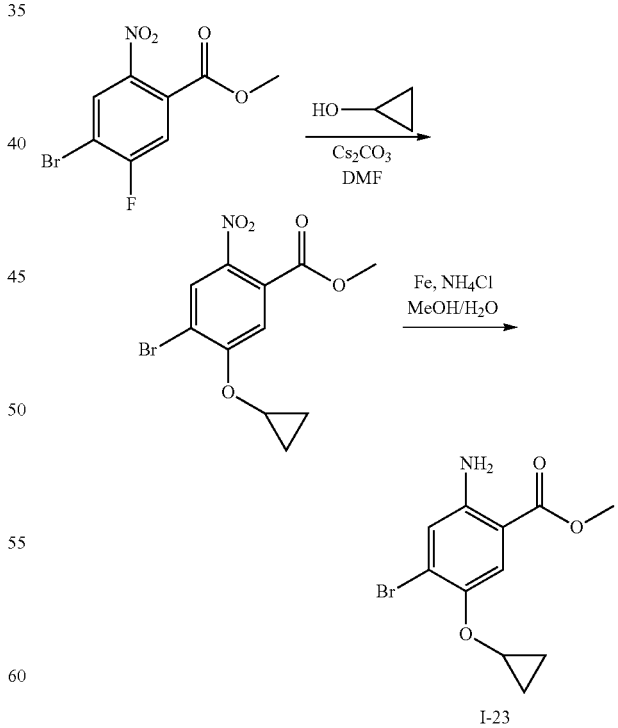

I-23

Methyl 4-bromo-5-(cyclopropoxy)-2-nitro-benzoate: To a mixture of methyl 4-bromo-5-fluoro-2-nitro-benzoate (1.00 g, 3.60 mmol) and cesium carbonate (2.34 g, 7.19 mmol) was added N,N-dimethylformamide (2.5 mL), followed by cyclopropanol (342 μL, 5.40 mmol) at room temperature. The resulting reaction mixture was stirred overnight. The reaction mixture was poured into water (100 mL), and the resulting precipitate was then filtered off and dried under vacuum to give the product.

ES/MS: 338.0 [M+Na⁺].

$^1$H NMR (400 MHz, DMSO-d$_6$) δ 8.41 (s, 1H), 7.70 (s, 1H), 3.88 (s, 3H), 2.68-2.16 (m, 1H), 0.92 (ddd, J=6.1, 2.5, 1.4 Hz, 2H), 0.80 (td, J=3.0, 1.6 Hz, 2H).

Methyl 2-amino-4-bromo-5-cyclopropoxybenzoate (I-23): Methyl 4-bromo-5-(cyclopropoxy)-2-nitro-benzoate (1.00 g, 3.16 mmol) was added to methanol/water (7 mL/1.7 mL), followed by ammonium chloride (592 mg, 11.1 mmol) and iron powder (618 mg, 11.1 mmol), and stirred at 80° C. for 2 hours. The reaction mixture was concentrated under reduced pressure, extracted with ethyl acetate (3×50 mL), dried over Na$_2$SO$_4$, filtered and concentrated under reduced pressure to provide the title compound.

ES/MS: 286.0 [M⁺].

Preparation of Intermediate I-24

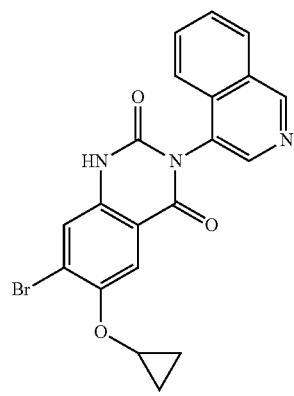

I-24

7-Bromo-6-(cyclopropoxy)-3-(4-isoquinolyl)-1H-quinazoline-2,4-dione (I-24): Prepared analogously to I-2 by replacing methyl 2-amino-4-bromobenzoate with methyl 2-amino-4-bromo-5-cyclopropoxybenzoate (1-23).

ES/MS: 424.1 [M*].

$^1$H NMR (400 MHz, DMSO-d$_6$) δ 11.72 (s, 1H), 9.48 (s, 1H), 8.60 (d, J=9.5 Hz, 1H), 8.55-8.24 (m, 1H), 7.92-7.78 (m, 4H), 7.55 (s, 1H), 4.06 (tq, J=5.6, 2.8 Hz, 1H), 0.91-0.69 (m, 4H).

Preparation of Intermediate I-25

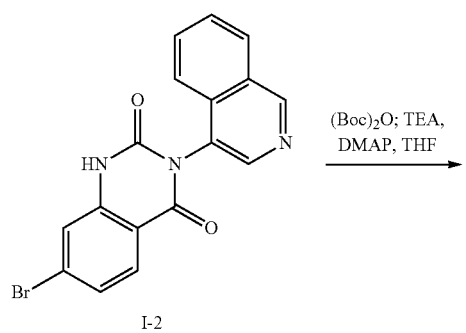

I-2

(Boc)$_2$O; TEA, DMAP, THF →

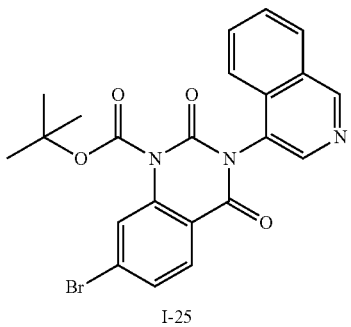

I-25 tert-butyl 7-bromo-3-(isoquinolin-4-yl)-2,4-dioxo-3,4-dihydroquinazoline-1(2H)-carboxylate (I-25): To a 100 mL flask were added 7-bromo-3-(4-isoquinolyl)-1H-quinazoline-2,4-dione (350 mg, 0.96 mmol), and dry THF (5 mL). At room temperature, di-tert-butyl dicarbonate (228 mg, 1.05 mmol) was added followed by triethyl amine (0.13 mL, 0.96 mmol) and DMAP (116 mg, 0.96 mmol). The mixture was stirred for 16 hour. The crude mixture was concentrated and purified by silica gel chromatography (eluent: EtOAc/hexanes) to provide the intermediate 1-25.

ES/MS: 470.1 (M⁺).

Preparation of Intermediate I-26

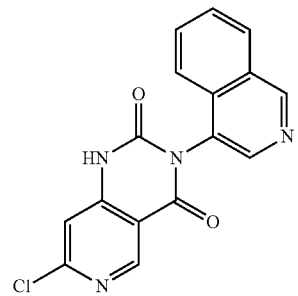

I-26

7-chloro-3-(isoquinolin-4-yl)pyrido[4,3-d]pyrimidine-2,4 (1H,3H)-dione (I-26): Prepared analogously to I-2, substituting methyl 2-amino-4-bromobenzoate with methyl 4-amino-6-chloro-pyridine-3-carboxylate.

ES/MS: 325.1 (M⁺).

Preparation of Intermediate I-27

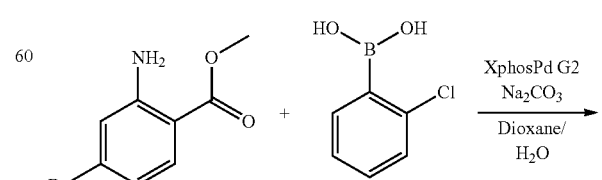

Preparation of Intermediate I-29

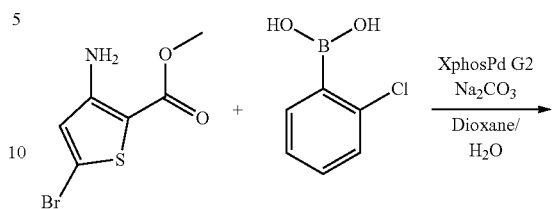

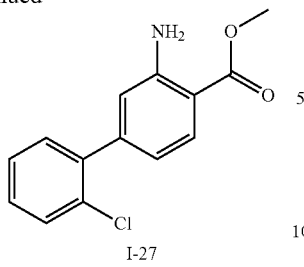

I-27

Methyl 3-amino-2'-chloro-[1,1'-biphenyl]-4-carboxylate (I-27): To a round bottom flask with methyl 2-amino-4-bromobenzoate (4 g, 17 mmol) were added (2-chlorophenyl) boronic acid (2.7 g, 17 mmol), XPhos Pd G2 (1.4 g, 0.87 mmol) and sodium carbonate (1.8 g, 17 mmol), dioxane (40 mL) and water (4 mL), and the mixture was degassed with argon for 30 seconds. The reaction mixture was heated at 80° C. for 15 hours. The crude mixture was diluted with EtOAc and water, filtered over celite rinsing with EtOAc, the layers separated, the aqueous layer extracted with EtOAc and the combined organics washed with brine. The organic layer was dried over sodium sulfate, concentrated and purified by silica gel chromatography to obtain the title compound.

ES/MS: 262.1 (M+).

Preparation of Intermediate I-28

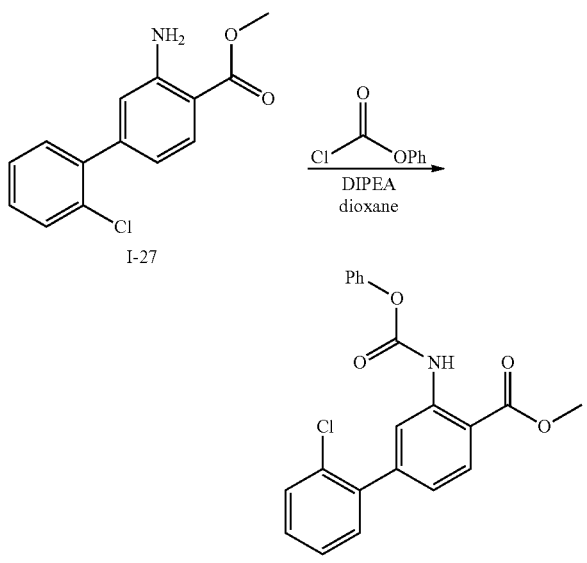

I-27

I-28 methyl 2'-chloro-3-((phenoxycarbonyl)amino)-[1,1'-biphenyl]-4-carboxylate (I-28): To a solution of methyl 3-amino-2'-chloro-[1,1'-biphenyl]-4-carboxylate (I-27) (2.7 g, 10.3 mmol) in dry dioxane (40 mL) was added DIPEA (2.6 mL, 20.6 mmol) followed by phenyl chloroformate (2 mL, 15 mmol). The reaction mixture was heated at 90° C. for 16 hours, after which the mixture was cooled to room temperature. The mixture was concentrated under reduced pressure, and the crude material was purified by silica chromatography (eluent: EtOAc in hexanes) to provide the product.

ES/MS: 381.8 (M+).

I-29 methyl 3-amino-5-(2-chlorophenyl)thiophene-2-carboxylate (I-29): To a round bottom flask with methyl 3-amino-5-bromothiophene-2-carboxylate (5 g, 21 mmol) were added (2-chlorophenyl)boronic acid (3.3 g, 21 mmol), XPhos Pd G2 (1.5 g, 0.95 mmol) and sodium carbonate (2.2 g, 21 mmol), dioxane (40 mL) and water (4 mL), and the mixture was degassed with argon for 30 seconds. The reaction mixture was heated at 80° C. for 15 hours. The crude mixture was diluted with EtOAc and water, filtered over celite rinsing with EtOAc, the layers separated, the aqueous layer extracted with EtOAc and the combined organics washed with brine. The organic layer was dried over sodium sulfate, concentrated and purified by silica gel chromatography to obtain the title compound.

ES/MS: 268.0 (M+).

Preparation of Intermediate I-30

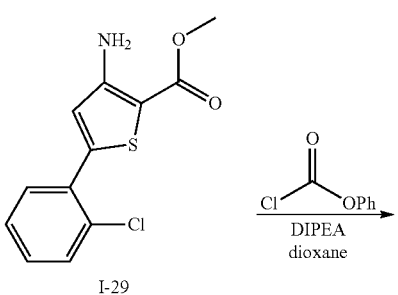

I-29

Preparation of Intermediate I-32

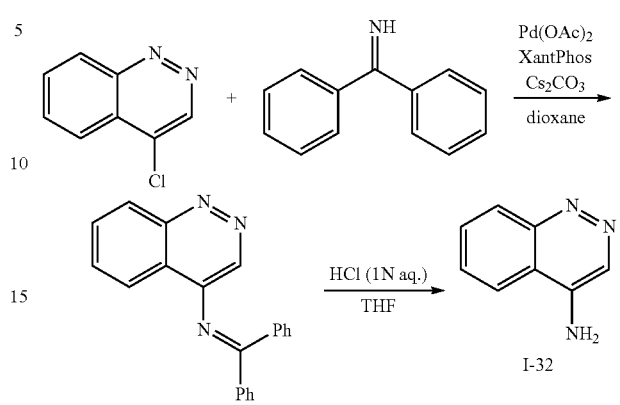

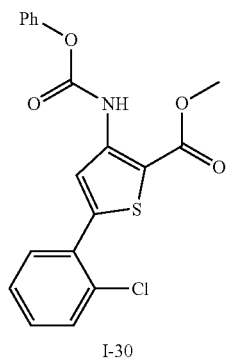

I-30 methyl 5-(2-chlorophenyl)-3-((phenoxycarbonyl)amino)thiophene-2-carboxylate (I-30): To a solution of methyl 3-amino-5-(2-chlorophenyl)thiophene-2-carboxylate (I-29) (3.7 g, 13.8 mmol) in dry dioxane (40 mL) was added DIPEA (2.7 mL, 27.6 mmol) followed by phenyl chloroformate (2.7 mL, 20.7 mmol). The reaction mixture was heated at 90° C. for 16 hours, after which the mixture was cooled to room temperature. The mixture was concentrated under reduced pressure, and the crude material was purified by silica chromatography (eluent: EtOAc in hexanes) to provide the product.

ES/MS: 387.9 (M+).

Preparation of Intermediate I-31

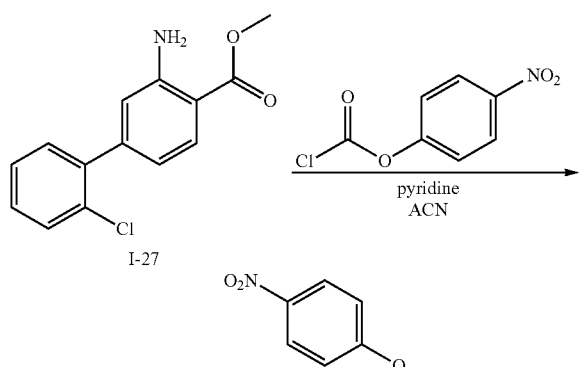

I-31 methyl 2'-chloro-3-(((4-nitrophenoxy)carbonyl)amino)-[1,1'-biphenyl]-4-carboxylate (I-31): To a solution of methyl 3-amino-2'-chloro-[1,1'-biphenyl]-4-carboxylate (I-27) (1 g, 3.8 mmol) in acetonitrile (10 mL) cooled to 0° C. was added 4-nitrophenyl carbonochloridate (1.2 g, 5.7 mmol, dissolved in 2 ml acetonitrile). The reaction mixture was stirred for 10 minutes then pyridine (0.3 ml, 3.8 mmol) was added, the resulting solid was filtered off, rinsed with acetonitrile and used without further purification.

N-(cinnolin-4-yl)-1,1-diphenylmethanimine: To a microwave vial were added 4-chlorocinnoline (100 mg, 0.61 mmol), diphenylmethanimine (132 mg, 0.729 mmol), Pd(OAc)$_2$ (14 mg, 0.06 mmol), 9,9-Dimethyl-4,5-bis(diphenylphosphino)xanthene (XantPhos) (71 mg, 0.12 mmol) and cesium carbonate (198 mg, 0.61 mmol). Dioxane (2 mL), and the mixture was degassed with argon for 30 seconds. The vial was sealed, and the reaction mixture was heated at 100° C. for 16 hours. The mixture was subsequently concentrated under reduced pressure. The crude residue was purified by silica gel chromatography (eluent: EtOAc/hexanes) to provide the product.

ES/MS: 310.2 (M+H+).

cinnolin-4-amine (I-32): To a vial were added N-(cinnolin-4-yl)-1,1-diphenylmethanimine (188 mg, 0.61 mmol). THF (4 mL) and HCl (2N aqueous: 1.5 mL), and the mixture was stirred at rt for 2 hours. The reaction was diluted with EtOAc and water. The layers were separated, and the aqueous layer was basified with K$_2$CO$_3$ and extracted with EtOAc 2×. The combined organic layers were dried over sodium sulfate, filtered, and concentrated under reduced pressure. The crude residue was used in the next reaction.

ES/MS: 146.1 (M+H+).

Preparation of Intermediate I-33

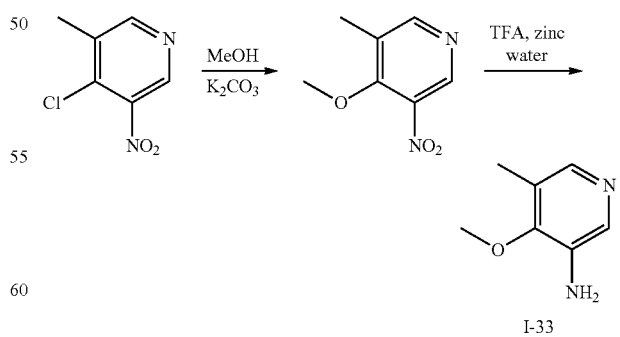

I-33

4-methoxy-3-methyl-5-nitropyridine: To a vial were added 4-chloro-3-methyl-5-nitropyridine (100 mg, 0.58 mmol), potassium carbonate (160 mg, 1.2 mmol), and methanol (2 ml). The mixture was stirred for 15 hours, filtered and concentrated under reduced pressure. The crude residue was used crude in the next reaction.
ES/MS: 169.1 (M+H⁺).

4-methoxy-5-methylpyridin-3-amine (I-33): To a vial were added 4-methoxy-3-methyl-5-nitropyridine (97 mg, 0.58 mmol). TFA (3 mL), water (0.5 mL), and zinc powder (151 mg, 2.3 mmol), and the mixture was stirred at 50° C. for 2 hours. The reaction was concentrated, basified with saturated sodium bicarbonate, and extracted with EtOAc 2×. The organic layer was dried over sodium sulfate, concentrated, and used crude in the next reaction.
ES/MS: 139.1 (M+H⁺).

Preparation of Intermediate I-34

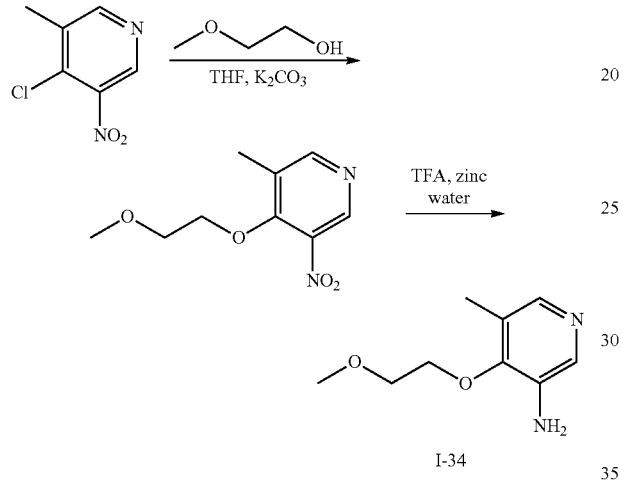

I-34

4-(2-methoxyethoxy)-3-methyl-5-nitropyridine: To a vial were added 4-chloro-3-methyl-5-nitropyridine (100 mg, 0.58 mmol), potassium carbonate (160 mg, 1.2 mmol), 2-methoxyethan-1-ol (132 mg, 1.7 mmol), and THF (2 ml). The mixture was stirred for 15 hours, filtered and concentrated under reduced pressure. The crude residue was used crude in the next reaction.
ES/MS: 213.0 (M+H⁺).

4-(2-methoxyethoxy)-5-methylpyridin-3-amine (I-34): To a vial were added 4-(2-methoxyethoxy)-3-methyl-5-nitropyridine (123 mg, 0.58 mmol). TFA (3 mL), water (0.5 mL), and zinc powder (151 mg, 2.3 mmol), and the mixture was stirred at 50° C. for 2 hours. The reaction was concentrated, basified with saturated sodium bicarbonate, and extracted with EtOAc 2×. The organic layer was dried over sodium sulfate, concentrated, and used crude in the next reaction.
ES/MS: 183.2 (M+H⁺).

Preparation of Intermediate I-35

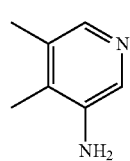

I-35

4,5-dimethylpyridin-3-amine (I-35): Prepared analogously to I-32, substituting 4-chlorocinnoline with 3-bromo-4,5-dimethyl-pyridine.
ES/MS: 123.1 (M+H⁺).

Preparation of Intermediate I-36

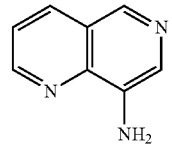

I-36

1,6-naphthyridin-8-amine (I-36): Prepared analogously to I-32, substituting 4-chlorocinnoline with 8-bromo-1,6-naphthyridine.
ES/MS: 146.1 (M+H⁺).

Preparation of Intermediate I-37

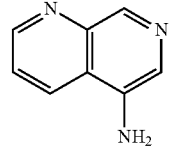

I-37

1,7-naphthyridin-5-amine (I-37): Prepared analogously to I-32, substituting 4-chlorocinnoline with 5-bromo-1,7-naphthyridine.
ES/MS: 146.0 (M+H⁺).

Preparation of Intermediate I-38

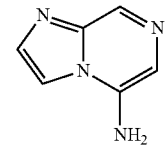

I-38 imidazo[1,2-a]pyrazin-5-amine (I-38): Prepared analogously to I-32, substituting 4-chlorocinnoline with 5-bromoimidazo[1,2-a]pyrazine.
ES/MS: 135.1 (M+H⁺).

Preparation of Intermediate I-39

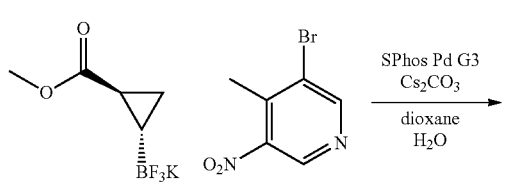

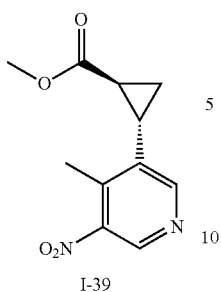

I-39 methyl (1S,2S)-2-(4-methyl-5-nitropyridin-3-yl)cyclopropane-1-carboxylate (I-39): A mixture of potassium trifluoro((1S,2S)-2-(methoxycarbonyl)cyclopropyl)borate (285 mg, 1.38 mmol), 3-bromo-4-methyl-5-nitropyridine (250 mg, 1.15 mmol), SPhos Pd G3 (89.9 mg, 0.115 mmol), and cesium carbonate (1126 mg, 3.46 mmol) in 1,4-dioxane (6.4 mL) and water (1.3 mL) was sparged with argon for 20 min and then heated to 110° C. After 24 h, the mixture was diluted with EtOAc, filtered through celite, and rinsed with EtOAc. The filtrate was washed with brine, died over Na$_2$SO$_4$, and concentrated in vacuo. The crude material was purified by silica chromatography (eluent: EtOAc in hexanes) to provide the product.

ES/MS: 237.1 (M+H$^+$).

Preparation of Intermediate I-40

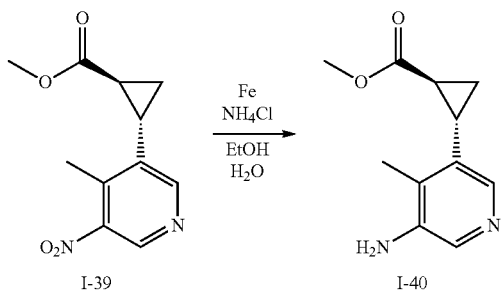

methyl (1S,2S)-2-(5-amino-4-methylpyridin-3-yl)cyclopropane-1-carboxylate (I-40): To methyl (1S,2S)-2-(4-methyl-5-nitropyridin-3-yl)cyclopropane-1-carboxylate (I-39) (167 mg, 0.71 mmol) in EtOH (4.7 mL) and water (1.6 mL) were added iron powder (473 mg, 8.47 mmol) and ammonium chloride (453 mg, 8.47 mmol), and the mixture was heated to 85° C. After 1 h, the mixture was diluted with EtOAc, filtered through celite, and rinsed with EtOAc. The filtrate was washed with brine, died over Na$_2$SO$_4$, and concentrated in vacuo to afford crude product that was used without further purification.

ES/MS: 207.1 (M+H$^+$).

Preparation of Intermediate I-41

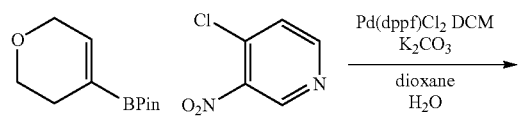

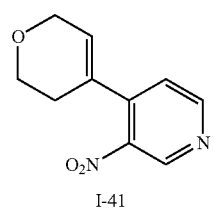

I-41

4-(3,6-dihydro-2H-pyran-4-yl)-3-nitropyridine (I-41): A mixture of 2-(3,6-dihydro-2H-pyran-4-yl)-4,4,5,5-tetramethyl-1,3,2-dioxaborolane (215 mg, 1.02 mmol), 4-chloro-3-nitropyridine (162 mg, 1.02 mmol), Pd(dppf)Cl$_2$ DCM (83.7 mg, 0.10 mmol), and potassium carbonate (283 mg, 2.05 mmol) in 1,4-dioxane (2.5 mL) and water (0.5 mL) was sparged with argon for 15 min and then heated to 80° C. After 2.5 h, the mixture was filtered through celite, rinsed with EtOAc, and concentrated in vacuo. The crude material was purified by silica chromatography (eluent: EtOAc in hexanes) to provide the product.

ES/MS: 207.0 (M+H$^+$).

Preparation of Intermediate I-42

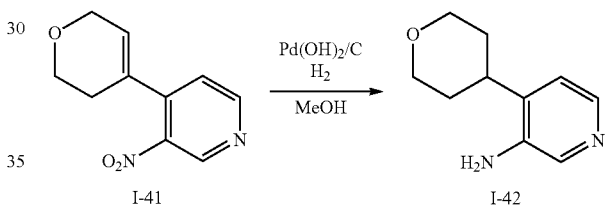

4-(tetrahydro-2H-pyran-4-yl)pyridin-3-amine (I-42): To 4-(3,6-dihydro-2H-pyran-4-yl)-3-nitropyridine (141) (232 mg, 1.13 mmol) in MeOH (10 mL) was added 20% palladium hydroxide on carbon, degussa type (265 mg), and the mixture was purged with H$_2$ three times. After 16 h, the mixture was purged with Ar, filtered through celite, rinsed with EtOAc, and concentrated in vacuo to afford crude product that was used without further purification.

ES/MS: 179.1 (M+H$^+$).

Preparation of Intermediates 1-43 and I-44:

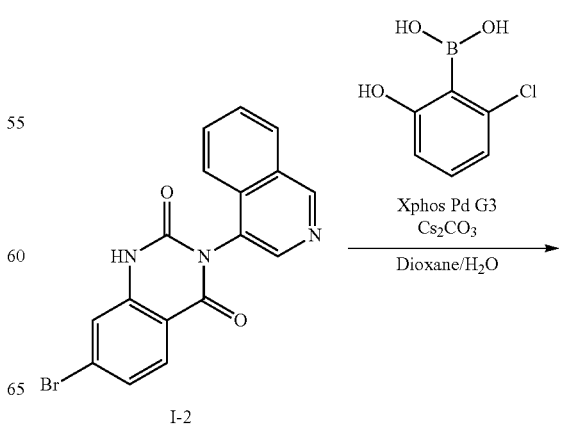

481

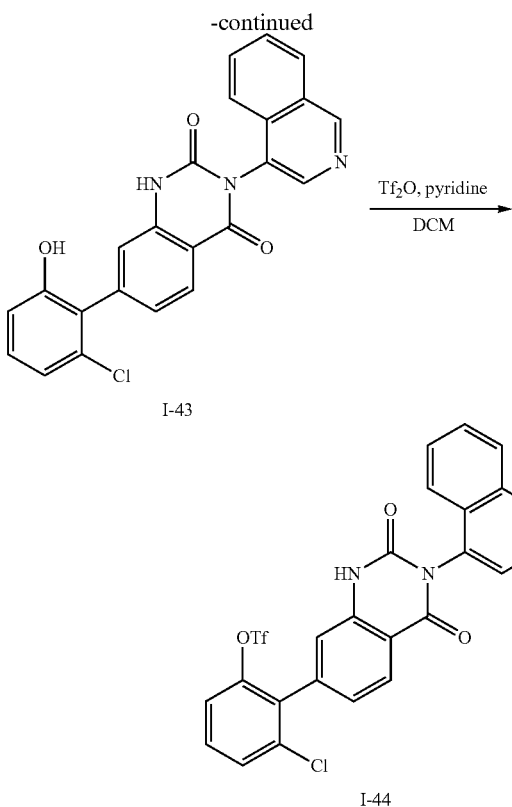

482

Preparation of Intermediate I-45

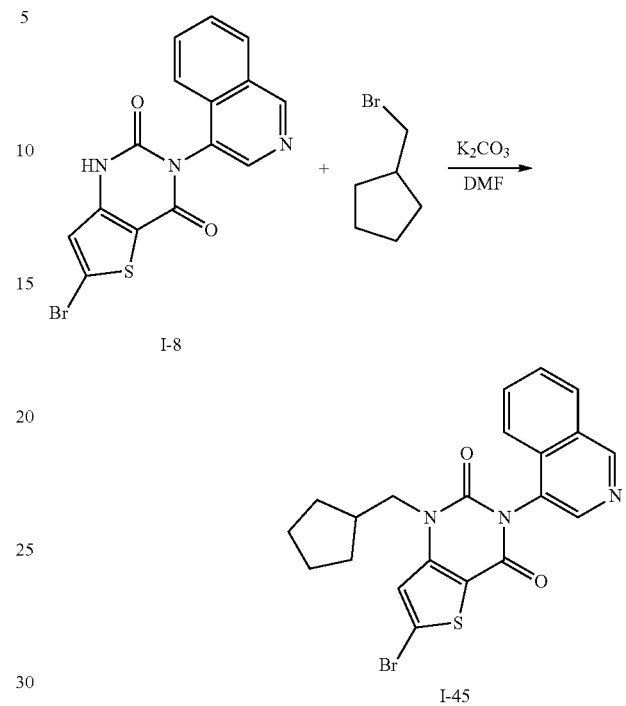

7-(2-bromo-6-chloro-phenyl)-3-(4-isoquinolyl)-1H-quinazoline-2,4-dione (I-43): To a 100 mL round bottom flask with 7-bromo-3-(4-isoquinolyl)-1H-quinazoline-2,4-dione (I-2) (3 g, 8.2 mmol) were added (2-chloro-6-hydroxyphenyl)boronic acid (2.0 g, 11.4 mmol), XPhos Pd G3 (307 mg, 0.41 mmol) and cesium carbonate (8.0 g, 24.4 mmol). Dioxane (62 mL) and water (4.1 mL) were added, and the mixture was degassed with argon for 30 seconds. A reflux condenser was added to the flask, and the reaction mixture was heated at 120° C. for 15 h. The crude mixture was concentrated under reduced pressure, and to the crude residue was added DCM (15 mL) and water (10 mL). The reaction mixture was filtered and the collected solid was used directly for the next step.

ES/MS: 416 (M+).

[3-chloro-2-[3-(4-isoquinolyl)-4-oxo-2-(trifluoromethylsulfonyloxy)quinazolin-7-yl]phenyl]trifluoromethanesulfonate (I-44): To a 200 ml round bottom flask with 7 7-(2-chloro-6-hydroxy-phenyl)-3-(4-isoquinolyl)-1H-quinazoline-2,4-dione (I-43) (3.2 g, 7.7 mmol), pyridine (1.3 ml, 15.4 mmol), and anhydrous DCM (100 mL) were added. The mixture was cool to 0 C under N2 and trifluoromethanesulfonic anhydride (1.32 ml, 9.2 mmol) was added dropwise. The reaction mixture was stirred room temp for 2 h. The crude mixture was quenched with water (20 ml) and exacted with DCM (3×). The organic layer was concentrated and EtOAc (20 mL) was added, followed by H₂O (50 mL) which formed a precipitate. The solid was collected via filtration, washed with additional H₂O (25 mL), and dried over air to obtain the product.

ES/MS: 548.1 (M+).

6-bromo-1-(cyclopentylmethyl)-3-(isoquinolin-4-yl)thieno[3,2-d]pyrimidine-2,4(1H,3H)-dione (I-45): To a stirred solution of 6-bromo-3-(isoquinolin-4-yl)thieno[3,2-d]pyrimidine-2,4(1H,3H)-dione (I-8) (531 mg, 1.42 mmol, 1 equiv.) in DMF (12 mL, 0.11 M) at room temperature was added (bromomethyl)cyclopentane (347 mg, 2.13 mmol, 1.5 equiv.) followed by K₂CO₃ (490 mg, 3.55 mmol, 2.5 equiv.). The reaction mixture was heated to 70° C. for 6 h. The mixture was cooled to rt, filtered through celite (rinsing with EtOAc), and concentrated under reduced pressure. The crude residue was purified by silica gel chromatography (eluent: EtOAc/hexanes), to provide the product I-45.

ES/MS: 457.0 (M+).

¹H NMR (400 MHz, CDCl₃) δ 9.37 (d, J=0.8 Hz, 1H), 8.51 (s, 1H), 8.11 (dt, J=8.1, 1.0 Hz, 1H), 7.74 (ddd, J=8.3, 6.9, 1.3 Hz, 1H), 7.67 (ddd, J=8.2, 6.9, 1.3 Hz, 1H), 7.59 (dq, J=8.4, 1.0 Hz, 1H), 7.12 (s, 1H), 4.18-3.96 (m, 2H), 2.44 (p, J=7.6 Hz, 1H), 1.89-1.53 (m, 4H), 1.40 (ddt, J=11.3, 7.2, 3.8 Hz, 4H).

Preparation of Intermediate I-46

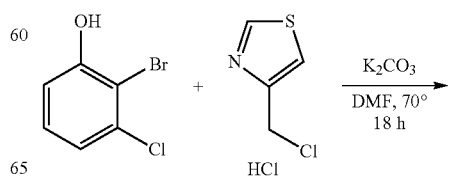

-continued

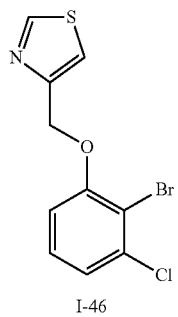

I-46

4-[(2-bromo-3-chloro-phenoxy)methyl]thiazole (I-46): To a dram vial with 2-bromo-3-chloro-phenol (300 mg, 1.45 mmol) were added 4-(chloromethyl)thiazole hydrochloride (271 mg, 1.59 mmol), potassium carbonate (600 mg, 4.34 mmol) and DMF (10.00 mL). The reaction mixture was then heated at 70° C. for 18 hours. The crude mixture was then diluted with water (50 mL) and subsequently extracted with DCM (3×30 mL). The combined organic layers were then washed with water (60 mL) and brine (50 mL), dried over MgSO$_4$, then concentrated under reduced pressure. The crude residue was then purified by silica gel flash chromatography (eluent: EtOAc in hexanes) to afford the product.
ES/MS: 305.9 (M$^+$).

Preparation of Intermediate I-47

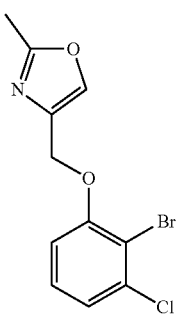

I-47

4-[(2-bromo-3-chloro-phenoxy)methyl]-2-methyl-oxazole (I-47): Prepared analogously to 1-46, substituting 4-(chloromethyl)thiazole hydrochloride with 4-(chloromethyl)-2-methyl-oxazole.
ES/MS: 304.0 (M$^+$).

Preparation of Intermediate I-48

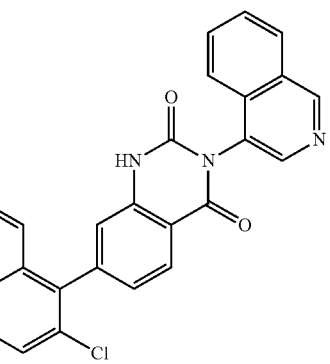

I-48

3-Chloro-2-(3-(isoquinolin-4-yl)-2,4-dioxo-1,2,3,4-tetrahydroquinazolin-7-yl)benzaldehyde (1-48): Prepared analogously to Procedure 5 substituting I-46 with 2-bromo-3-chloro-benzaldehyde.
ES/MS: 428.1 [M$^+$].
$^1$H NMR (400 MHz, DMSO-d$_6$) δ 11.90 (s, 1H), 9.70 (dd, J=9.2, 0.7 Hz, 1H), 9.45 (d, J=1.0 Hz, 11H), 8.65-8.55 (m, 1H), 8.29 (dq, J=7.4, 1.1 Hz, 1H), 8.10 (d, J=8.1 Hz, 1H), 8.02-7.93 (m, 2H), 7.85-7.66 (m, 4H), 7.27 (dd, J=8.1, 1.6 Hz, 1H), 7.22 (d, J=1.6 Hz, 1H).

Preparation of Intermediate I-49

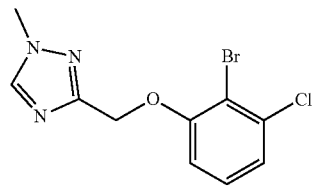

I-49

3-[(2-Bromo-3-chloro-phenoxy)methyl]-1-methyl-1,2,4-triazole (I-49): Prepared analogously to 1-46 by substituting 4-(chloromethyl)thiazole hydrochloride with 3-(chloromethyl)-1-methyl-1,2,4-triazole hydrochloride.
ES/MS: 302.0 [M$^+$].
$^1$H NMR (400 MHz, Chloroform-d) δ 8.04 (s, 1H), 7.20 (t, J=8.1 Hz, 1H), 7.11 (dd, J=8.1, 1.5 Hz, 1H), 7.05 (dd, J=8.2, 1.4 Hz, 1H), 5.23 (s, 2H), 3.94 (d, J=0.5 Hz, 3H).

Preparation of Intermediate I-50

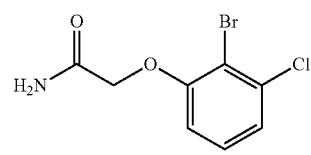

I-50

3-[(3-bromo-4-chloro-phenoxy)methyl]-1-methyl-1,2,4-triazole (1-50): Prepared analogously to I-46 by substituting 4-(chloromethyl)thiazole hydrochloride and 2-bromo-3-chloro-phenol with 3-(chloromethyl)-1-methyl-1,2,4-triazole hydrochloride and 3-bromo-4-chloro-phenol, respectively.
ES/MS: 303.9 [M+H$^+$].
$^1$H NMR (400 MHz, DMSO-d$_6$) δ 9.03-7.94 (m, 1H), 7.67-7.43 (m, 2H), 7.09 (dd, J=8.9, 2.9 Hz, 1H), 5.11 (s, 2H), 3.87 (d, J=0.6 Hz, 3H).

Preparation of Intermediate I-51

I-51

2-(2-Bromo-3-chloro-phenoxy)acetamide (I-51): Prepared analogously to 1-46 by substituting 4-(chloromethyl)thiazole hydrochloride with 2-bromoacetamide.

ES/MS: 266.0 [M+H⁺].

¹H NMR (400 MHz, DMSO-d₆) δ 7.49 (s, 1H), 7.35 (q, J=7.9 Hz, 2H), 7.24 (dd, J=8.1, 1.3 Hz, 1H), 6.96 (dd, J=8.4, 1.3 Hz, 1H), 4.61 (s, 2H).

Preparation of Intermediate I-52

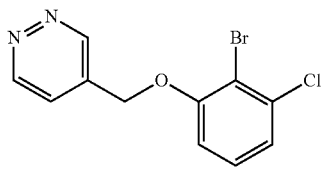

4-[(2-Bromo-3-chloro-phenoxy)methyl]pyridazine (I-52): Prepared analogously to 1-46 by substituting 4-(chloromethyl)thiazole hydrochloride with 4-(bromomethyl)pyridazine hydrobromide.

ES/MS: 301.1 [M+H⁺].

Preparation of Intermediate I-53

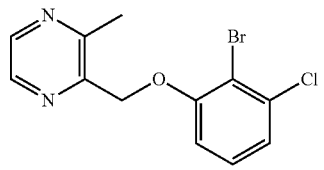

2-[(2-bromo-3-chloro-phenoxy)methyl]-3-methyl-pyrazine (I-53): Prepared analogously to 1-46 by substituting 4-(chloromethyl)thiazole hydrochloride 2-(chloromethyl)-3-methyl-pyrazine hydrochloride.

ES/MS: 315.0 [M+H⁺].

Preparation of Intermediate I-54

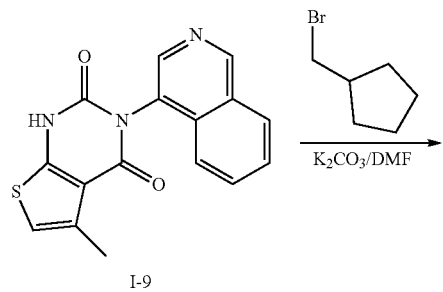

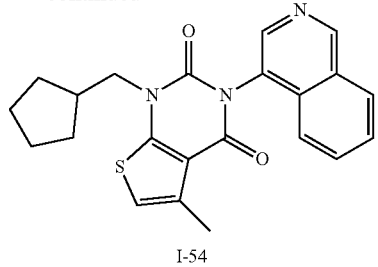

1-(cyclopentylmethyl)-3-(isoquinolin-4-yl)-5-methylthieno[2,3-d]pyrimidine-2,4(1H,3H)-dione (I-54): To a 10 mL microwave vial containing a stir bar was added 34(4-isoquinolyl)-5-methyl-1H-thieno[2,3-d]pyrimidine-2,4-dione (I-9) (300 mg, 0.97 mmol) followed by DMF (10 mL). To this mixture were added K₂CO₃ (134 mg, 0.97 mmol), and bromomethyl cyclopentane (158 mg, 0.97 mmol). The resulting mixture was stirred at rt for 36 h. The reaction was quench with water (20 mL), extract with EtOAc, dried over Na₂SO₄ and concentrated. The crude product was purified by silica gel column chromatography (0-100% EA/Hex) to afford the product.

ES/MS: 392.15 (M+H⁺).

¹H NMR (400 MHz, Methanol-d₄) δ 9.38 (d, J=0.8 Hz, 1H), 8.46 (s, 1H), 8.29-8.27 (m, 1H), 7.87-7.83 (m, 1H), 7.80-7.78 (m, 1H), 7.76-7.73 (m, 1H), 6.82 (q, J=1.2 Hz, 1H), 4.15-3.97 (m, 2H), 2.68-2.59 (m, 1H), 2.45 (d, J=1.3 Hz, 3H), 1.91-1.79 (m, 2H), 1.78-1.68 (m, 2H), 1.67-1.57 (m, 2H), 1.49-1.39 (m, 2H).

Preparation of Intermediate I-55

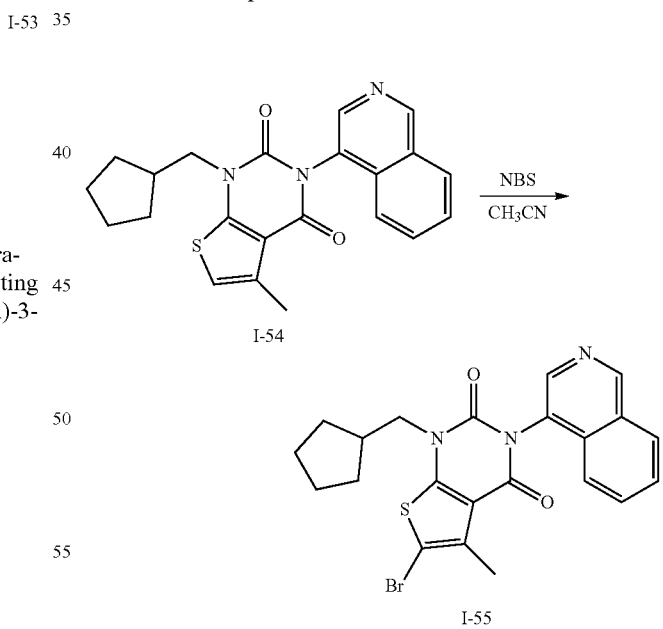

6-bromo-1-(cyclopentylmethyl)-3-(isoquinolin-4-yl)-5-methylthieno[2,3-d]pyrimidine-2,4(1H,3H)-dione (I-55): To a 20 mL vial containing a stir bar was added 1-(cyclopentylmethyl)-3-(isoquinolin-4-yl)-5-methylthieno[2,3-d]pyrimidine-2,4(1H,3H)-dione (I-54) (215 mg, 0.549 mmol) followed by CH₃CN (15 mL). To the cooled mixture at 0° C. was added a solution of NBS (88 mg, 0.494 mmol) in CH₃CN (1.5 mL) drop wise via syringe, then stirred for 60 min, and stirred at rt for 30 min. The reaction was quenched with mixture of CH$_3$CN/water (2 mL, 1/0.02), and concentrated. The crude product was purified by silica gel column chromatography (0-100% EA/Hex) to afford title compound.

ES/MS: 470.15 (M$^+$).

$^1$H NMR (400 MHz, Methanol-d$_4$) δ 9.38 (d, J=0.8 Hz, 1H), 8.46 (s, 1H), 8.29-8.26 (m, 1H), 7.85 (ddd, J=8.2, 7.0, 1.3 Hz, 1H), 7.81-7.72 (m, 2H), 4.09-3.94 (m, 2H), 2.64-2.42 (m, 1H), 2.42 (s, 3H), 1.90-1.77 (m, 2H), 1.76-1.69 (m, 1H), 1.67-58 (m, 2H), 1.50-1.33 (m, 2H).

Preparation of Intermediate I-56

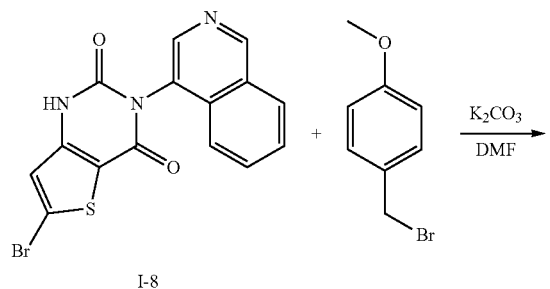

I-8

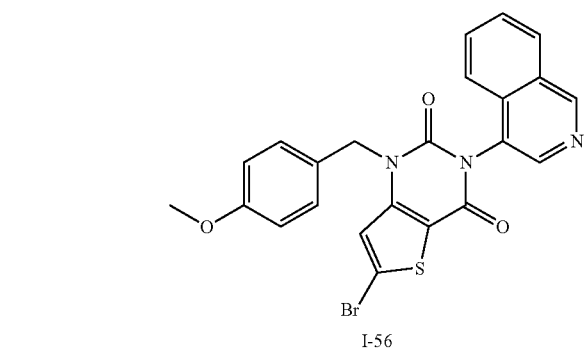

I-56

6-bromo-3-(isoquinolin-4-yl)-1-(4-methoxybenzyl)thieno[3,2-d]pyrimidine-2,4(1H,3H)-dione (I-56): To a solution of 6-bromo-3-(4-isoquinolyl)-1H-thieno[3,2-d]pyrimidine-2,4-dione (I-8) (0.35 g, 0.935 mmol) in DMF (8 mL), were added K$_2$CO$_3$ (0.129 g, 0.935 mmol) followed by 1-(bromomethyl)-4-methoxy-benzene (0.188 g, 0.935 mmol) and stirred at RT overnight. The reaction was quenched with water (20 mL), extracted with EtOAc, dried over Na$_2$SO$_4$ and concentrated. The crude product was purified by silica gel column chromatography (0-100% EA/Hex) to afford title compound I-56.

ES/MS: 494.2 (M$^+$).

$^1$H NMR (400 MHz, Methanol-d$_4$) δ 9.39 (d, J=0.8 Hz, 1H), 8.52 (s, 1H), 8.32-8.24 (m, 1H), 7.91-7.80 (m, 11H), 7.82-7.73 (m, 2H), 7.49 (s, 1H), 7.43-7.34 (m, 2H), 7.01-6.93 (m, 2H), 5.29 (s, 2H), 3.81 (s, 3H).

Preparation of Intermediate I-57

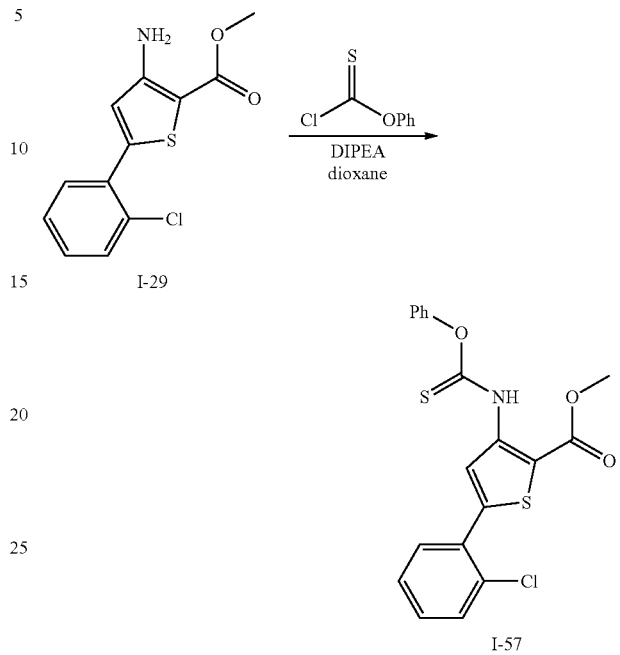

I-29

I-57 methyl 5-(2-chlorophenyl)-3-((phenoxycarbonothioyl)amino)thiophene-2-carboxylate (I-57): To a solution of methyl 3-amino-5-(2-chlorophenyl)thiophene-2-carboxylate (I-29) (300 mg, 1.12 mmol) in dry dioxane (5 mL) was added 0-phenyl chloromethanethioate (0.196 mL, 1.46 mmol), followed by DIPEA (0.29 mL, 1.68 mmol). The reaction mixture was heated at 80° C. for 1 hour, after which the mixture was cooled to room temperature. The mixture was concentrated under reduced pressure, and the crude material was purified by silica chromatography (eluent: EtOAc in hexanes) to provide the product.

ES/MS: 404.0 (M$^+$).

Preparation of Intermediate I-58

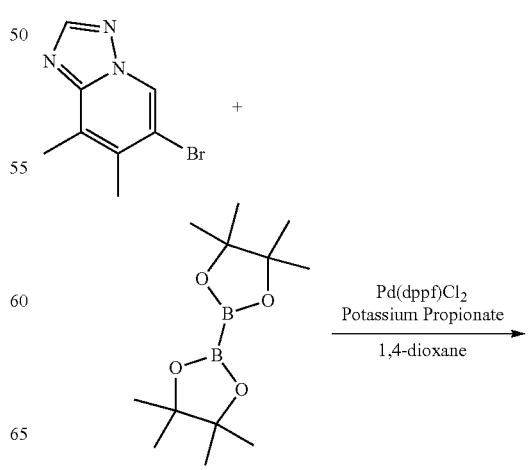

-continued

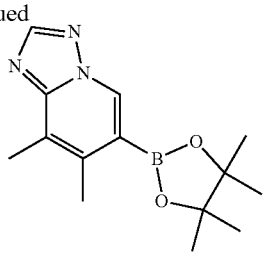

I-58

7,8-dimethyl-6-(4,4,5,5-tetramethyl-1,3,2-dioxaborolan-2-yl)-[1,2,4]triazolo[1,5-a]pyridine (I-58): To a 500 mL round bottom flask were added 6-bromo-7,8-dimethyl-[1,2,4]triazolo[1,5-a]pyridine (10 g, 44.2 mmol), Bis(pinacolato)diboron (14.6 g, 57.5 mmol), [1,1'-Bis(diphenylphosphino)ferrocene]dichloropalladium(II) (2.62 g, 3.54 mmol), and potassium propionate (14.9 g, 133 mmol). The mixture was dissolved in 1,4-dioxane (140 mL), and nitrogen was bubbled through the reaction mixture for 5 minutes. The mixture was heated at 100° C. for 1 hour under nitrogen. The mixture was cooled to rt, filtered through celite, and concentrated under reduced pressure. The crude residue was purified by silica gel chromatography (eluent: EtOAc/hexanes) to provide the product I-58.

ES/MS: 274.2 (M+H$^+$).

Preparation of Intermediate I-59

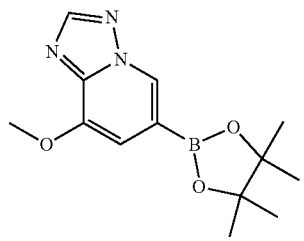

I-59

8-methoxy-6-(4,4,5,5-tetramethyl-1,3,2-dioxaborolan-2-yl)-[1,2,4]triazolo[1,5-a]pyridine (I-59): Prepared analogously to I-58, substituting 6-bromo-7,8-dimethyl-[1,2,4]triazolo[1,5-a]pyridine with 6-bromo-8-methoxy-[1,2,4]triazolo[1,5-a]pyridine.

ES/MS: 276.2 (M+H$^+$).

Preparation of Intermediate I-60

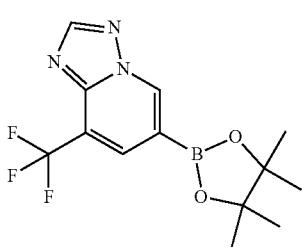

I-60

6-(4,4,5,5-tetramethyl-1,3,2-dioxaborolan-2-yl)-8-(trifluoromethyl)-[1,2,4]triazolo[1,5-a]pyridine (I-60): Pre-pared analogously to I-59, substituting 6-bromo-7,8-dimethyl-[1,2,4]triazolo[1,5-a]pyridine with 6-bromo-8-(trifluoromethyl)-[1,2,4]triazolo[1,5-a]pyridine.

ES/MS: 232.1 (M+H$^+$) (mass of boronic acid).

1H NMR (400 MHz, CDCl$_3$) δ 9.11 (s, 1H), 8.49 (s, 1H), 8.18 (t, J=1.1 Hz, 1H), 1.41 (s, 12H).

Preparation of Intermediate I-61

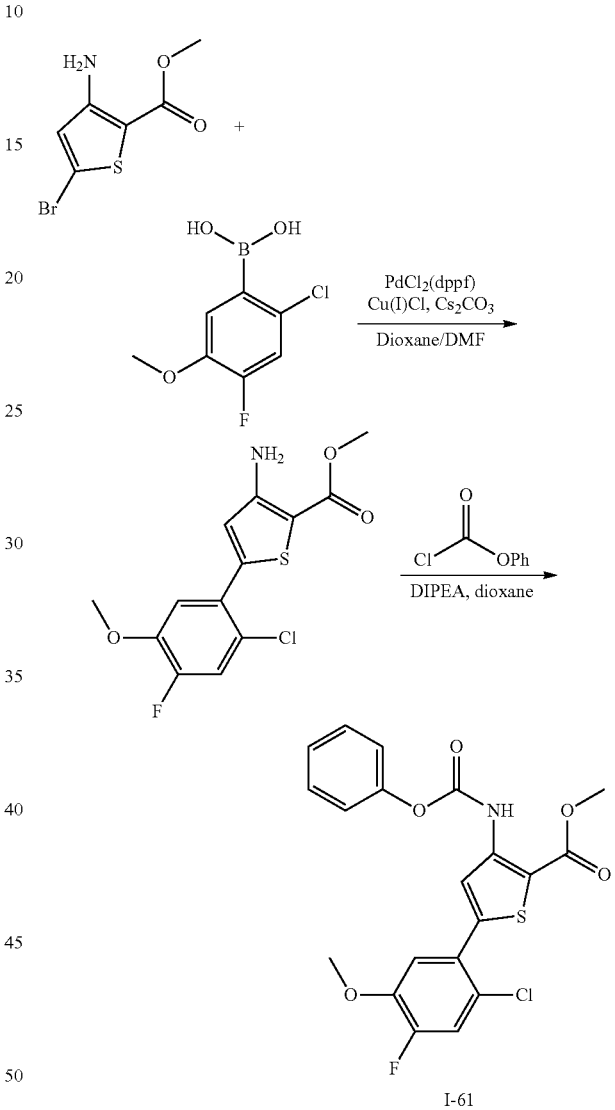

I-61 methyl 3-amino-5-(2-chloro-4-fluoro-5-methoxyphenyl)thiophene-2-carboxylate: To a 25 mL flask was added methyl 3-amino-5-bromo-thiophene-2-carboxylate (200 mg, 0.85 mmol, 1.0 equiv.), (2-chloro-4-fluoro-5-methoxyphenyl)boronic acid (364 mg, 1.78 mmol, 2.1 equiv.), PdCl$_2$(dppf) (94.3 mg, 0.13 mmol, 15 mol %), CuCl (84 mg, 0.85 mmol, 1.0 equiv.), Cs$_2$CO$_3$ (1.1 g, 3.39 mmol, 4.0 equiv.) followed by Dioxane/DMF (9:1) (4.24 mL, 0.2 M). The entire reaction mixture was degassed with Ar over 5 min, sealed and heated at 95° C. for 2 h after which the reaction mixture was then cooled to room temperature. The mixture was concentrated under reduced pressure, and the crude material was purified by silica chromatography (eluent: EtOAc in hexanes) to provide the product.

ES/MS: 315.8 (M$^+$).

$^1$H NMR (400 MHz, CDCl$_3$) δ 7.23 (d, J=10.6 Hz, 1H), 7.08 (d, J=10.6 Hz, 1H), 6.81 (s, 1H), 3.92 (s, 3H), 3.87 (s, 3H).

methyl 5-(2-chloro-4-fluoro-5-methoxyphenyl)-3-((phenoxycarbonyl)amino)thiophene-2-carboxylate (I-61): To a stirring solution of methyl 3-amino-5-(2-chloro-4-fluoro-5-methoxyphenyl)thiophene-2-carboxylate (3.0 g, 9.5 mmol, 1.0 equiv.) in dioxane (41 mL, 0.25 mL) was added phenyl chloroformate (1.86 mL, 14.3 mmol, 1.5 equiv.) and DIPEA (3.31 mL, 19.0 mmol, 2.0 equiv.) The reaction mixture was heated to 90° C. and stirred for 3 h which showed full consumption of amine. The reaction mixture was cooled to rt and diluted with EtOAc (150 mL) and H$_2$O (150 mL). The layers were separated, and the aqueous layer was extracted with EtOAc (2×100 mL). The organics were combined, dried over Na$_2$SO$_4$, and concentrated under reduced pressure. The crude residue was purified by silica gel chromatography (eluent: EtOAc/hexanes), to deliver the product (I-61).

ES/MS: 435.7 (M$^+$).

Preparation of Intermediate I-61

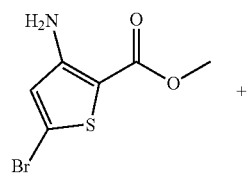

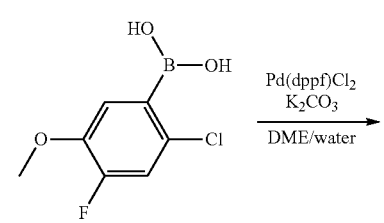

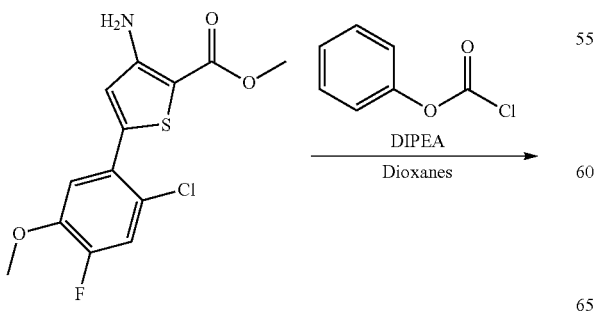

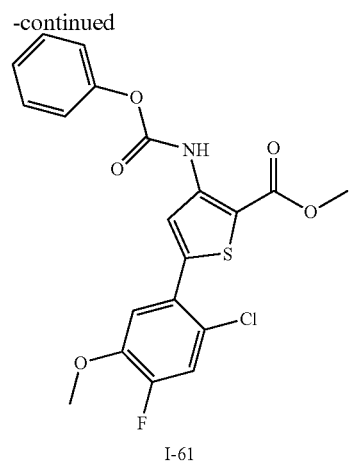

I-61 methyl 3-amino-5-(2-chloro-4-fluoro-5-methoxy-phenyl)thiophene-2-carboxylate: To a solution of methyl 3-amino-5-bromo-thiophene-2-carboxylate (21.0) g, 103 mmol) in DME (200 mL) and water (40 mL) was added (2-chloro-4-fluoro-5-methoxy-phenyl)boronic acid (16.2 g, 68.6 mmol), K$_2$CO$_3$ (28.4 g, 206 mmol), and PdCl$_2$(dppf) (2.5 g, 3.4 mmol). The resulting mixture was then degassed with Ar and stirred at 80° C. for 2 hours under an N2 atmosphere. The reaction mixture was then extracted with EtOAc (3×300 mL), and the combined organic layers were washed with water (300 mL) and brine (300 mL), dried over Na$_2$SO$_4$, filtered, and concentrated under reduced pressure. The resulting crude residue was then purified via silica gel flash chromatography (eluent: EtOAc/hexanes) to afford the product.

ES/MS: 315.8 (M$^+$).
$^1$H NMR (400 MHz, DMSO-d$_6$): δ 7.55 (d, J=12.0 Hz, 1H), 7.26 (d, J=12.0 Hz, 1H), 6.88 (s, 1H), 6.56 (br, 2H), 3.86 (s, 3H), 3.70 (s, 3H).

methyl 5-(2-chloro-4-fluoro-5-methoxy-phenyl)-3-(phenoxycarbonylamino)thiophene-2-carboxylate (I-61): To a solution of methyl 3-amino-5-(2-chloro-4-fluoro-5-methoxy-phenyl)thiophene-2-carboxylate (1.50 g, 4.75 mmol) in dioxanes (20.6 mL) at 80° C. was added DIPEA (1.65 mL, 9.50 mmol) and phenyl chloroformate (0.93 mL, 7.13 mmol). The resulting reaction mixture was then stirred at 80° C. for 3 hours. The reaction mixture was then concentrated under reduced pressure and hexanes (50 mL) was added to the crude residue to yield a white precipitate. The solid was then filtered off and washed with water (100 mL) to afford the product.

ES/MS: 435.8 (M$^+$).

Preparation of Intermediate I-62

I-62 methyl 5-(2-chloro-5-methoxyphenyl)-3-((phenoxycarbonyl)amino)thiophene-2-carboxylate (I-62): Prepared analogously to 1-29 and 1-30, substituting (2-chlorophenyl)boronic acid with (2-chloro-5-methoxyphenyl)boronic acid.

ES/MS: 417.9 (M⁺).

H NMR (400 MHz, DMSO-$d_6$) δ 9.86 (s, 1H), 8.01 (s, 1H), 7.54 (d, J=8.9 Hz, 1H), 7.50-7.39 (m, 2H), 7.33-7.23 (m, 3H), 7.17 (d, J=3.0 Hz, 1H), 7.07 (dd, J=8.9, 3.0 Hz, 1H), 3.89 (s, 3H), 3.81 (s, 3H).

Preparation of Intermediate I-63

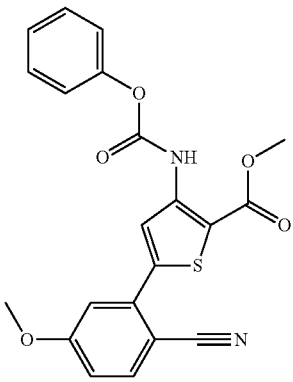

I-63 methyl 5-(2-cyano-5-methoxyphenyl)-3-((phenoxycarbonyl)amino)thiophene-2-carboxylate (I-63): Prepared analogously to 1-29 and 1-30, substituting (2-chlorophenyl)boronic acid with 4-methoxy-2-(4,4,5,5-tetramethyl-1,3,2-dioxaborolan-2-yl)benzonitrile (1-103).

$^1$H NMR (400 MHz, DMSO-$d_6$) δ 9.89 (s, 1H), 8.18 (s, 1H), 7.94 (d, J=8.7 Hz, 1H), 7.51-7.41 (m, 2H), 7.40-7.05 (m, 5H), 3.92 (s, 3H), 3.91 (s, 3H).

Preparation of Intermediate I-64

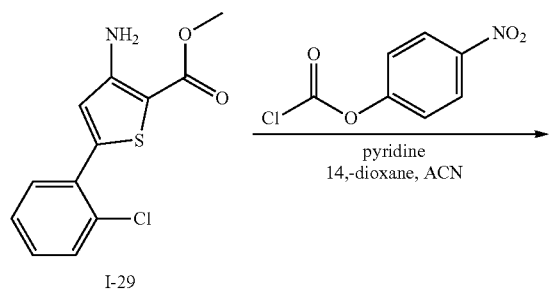

-continued

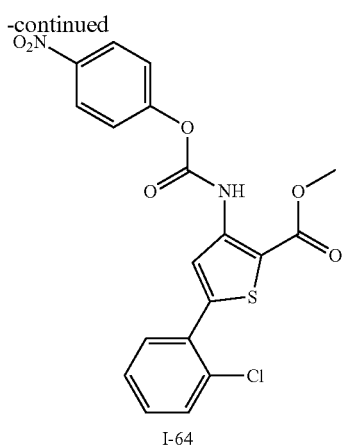

I-64 methyl 5-(2-chlorophenyl)-3-(((4-nitrophenoxy)carbonyl)amino)thiophene-2-carboxylate (I-64): To a solution of methyl 3-amino-5-(2-chlorophenyl)thiophene-2-carboxylate (I-29) (5 g, 19 mmol) in 1,4-dioxane (176 mL) placed in RT water bath was added 4-Nitrophenyl Chloroformate (6.2 g, 31 mmol, dissolved in 20 ml acetonitrile). The reaction mixture was stirred for 10 minutes then pyridine (2.6 ml, 33 mmol, in 20 ml acetonitrile) was added slowly. The mixture was stirred for 15 minutes. The reaction volume was reduced by half under reduced pressure while in a 50° C. water bath. Reaction was returned to the RT water bath and 360 ml acetonitrile was added, once stirring, the water bath was replaced with an ice bath and the mixture was stirred for 20 minutes. Solids were filtered off, and rinsed with 100 ml acetonitrile 3×. The solid was dried under vacuum.

ES/MS: product does not ionize.

$^1$H NMR (400 MHz, Acetone-$d_6$) δ 10.02 (s, 1H), 8.42-8.36 (m, 2H), 8.17 (s, 1H), 7.75-7.69 (m, 1H), 7.68-7.61 (m, 2H), 7.54-7.46 (m, 3H), 3.98 (s, 3H).

Preparation of Intermediate I-65

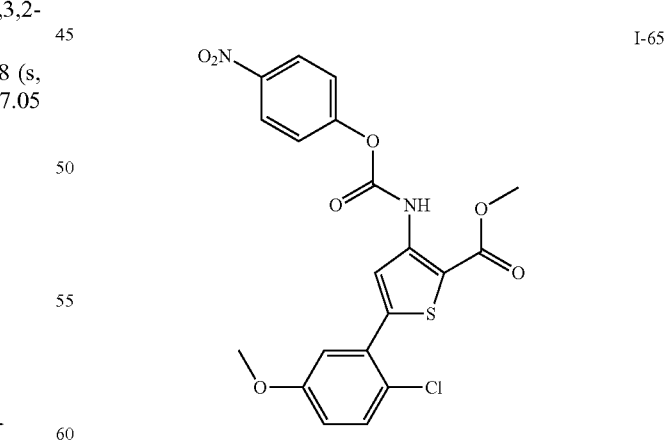

I-65 methyl 5-(2-chloro-5-methoxyphenyl)-3-(((4-nitrophenoxy)carbonyl)amino)thiophene-2-carboxylate (I-65): Prepared analogously to 1-64, substituting 3-amino-5-(2-chlorophenyl)thiophene-2-carboxylate with methyl 3-amino-5-(2-chloro-5-methoxyphenyl)thiophene-2-carboxylate.

ES/MS: product does not ionize.

¹H NMR (400 MHz, Acetone-d₆) δ 10.02 (s, 1H), 8.42-8.36 (m, 2H), 8.15 (s, 1H), 7.69-7.62 (m, 2H), 7.52 (d, 1H), 7.21 (d, 1H), 7.11-7.07 (m, 1H), 3.98 (s, 3H), 3.90 (s, 3H).

Preparation of Intermediate I-66

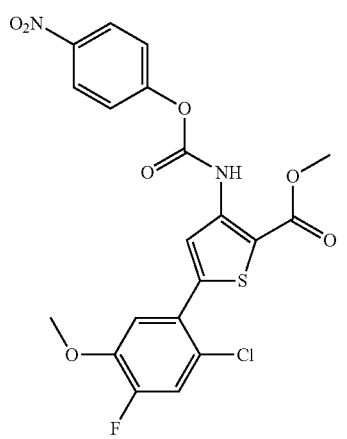

I-66 methyl 5-(2-chloro-4-fluoro-5-methoxyphenyl)-3-(((4-nitrophenoxy)carbonyl)amino)thiophene-2-carboxylate (I-66): Prepared analogously to I-64, substituting 3-amino-5-(2-chlorophenyl)thiophene-2-carboxylate with methyl 3-amino-5-(2-chloro-4-fluoro-5-methoxyphenyl)thiophene-2-carboxylate.

ES/MS: product does not ionize.

¹H NMR (400 MHz, Acetone-d₆) δ 10.02 (s, 1H), 8.43-8.35 (m, 2H), 8.11 (s, 1H), 7.69-7.59 (m, 2H), 7.47 (d, 1H), 7.41 (d, 1H), 4.02 (s, 3H), 3.98 (s, 3H).

Preparation of Intermediate I-67

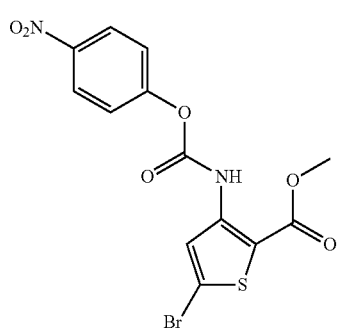

I-67 methyl 5-bromo-3-(((4-nitrophenoxy)carbonyl)amino)thiophene-2-carboxylate (I-67): Prepared analogously to I-64, substituting 3-amino-5-(2-chlorophenyl)thiophene-2-carboxylate with methyl 3-amino-5-bromothiophene-2-carboxylate.

ES/MS: product does not ionize.

¹H NMR (400 MHz, Acetone-d₆) δ 9.97 (s, 1H), 8.43-8.35 (m, 2H), 7.93 (s, 1H), 7.68-7.59 (m, 2H), 3.94 (s, 3H).

Preparation of Intermediate I-68

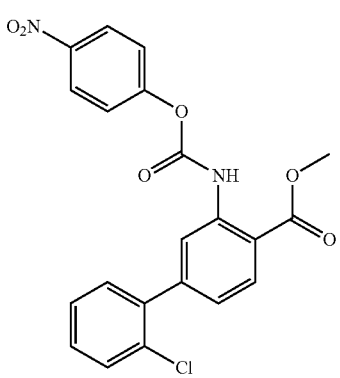

I-68 methyl 2'-chloro-3-(((4-nitrophenoxy)carbonyl)amino)-[1,1'-biphenyl]-4-carboxylate (I-68): Prepared analogously to I-64, substituting 3-amino-5-(2-chlorophenyl)thiophene-2-carboxylate with methyl 3-amino-2'-chloro-[1,1'-biphenyl]-4-carboxylate (I-27).

ES/MS: product does not ionize.

Preparation of Intermediate I-69

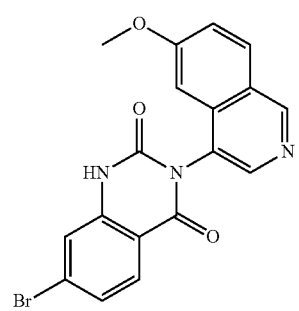

I-69

7-bromo-3-(6-methoxyisoquinolin-4-yl)quinazoline-2,4(1H,3H)-dione (I-69): Prepared analogously to I-2, substituting isoquinolin-4-amine with 6-methoxyisoquinolin-4-amine.

ES/MS: 398.0 (M⁺).

Preparation of Intermediate I-70

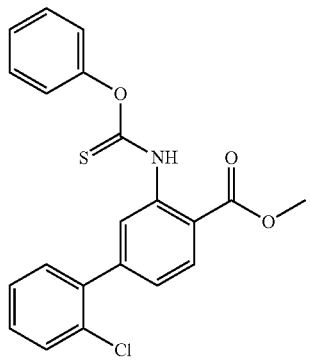

methyl 2'-chloro-3-((phenoxycarbonothioyl)amino)-[1,1'-biphenyl]-4-carboxylate (I-70): Prepared analogously to I-57, substituting methyl 3-amino-5-(2-chlorophenyl)thiophene-2-carboxylate (I-29) with methyl 3-amino-2'-chloro-[1,1'-biphenyl]-4-carboxylate (I-27).

ES/MS: 398.1 (M+).

Preparation of Intermediate I-71

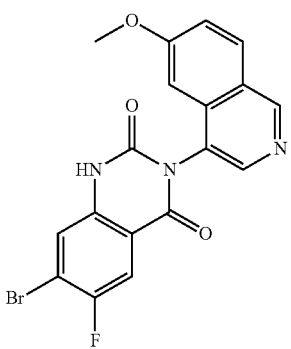

7-bromo-6-fluoro-3-(6-methoxyisoquinolin-4-yl)quinazoline-2,4(1H,3H)-dione (I-71): Prepared analogously to 1-2, substituting methyl 2-amino-4-bromobenzoate with methyl 2-amino-4-bromo-5-fluorobenzoate. Additionally, isoquinolin-4-amine was substituted with 6-methoxyisoquinolin-4-amine.

ES/MS: 416.0 (M+).

Preparation of Intermediate I-72

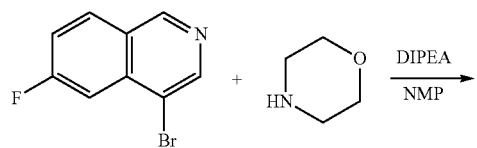

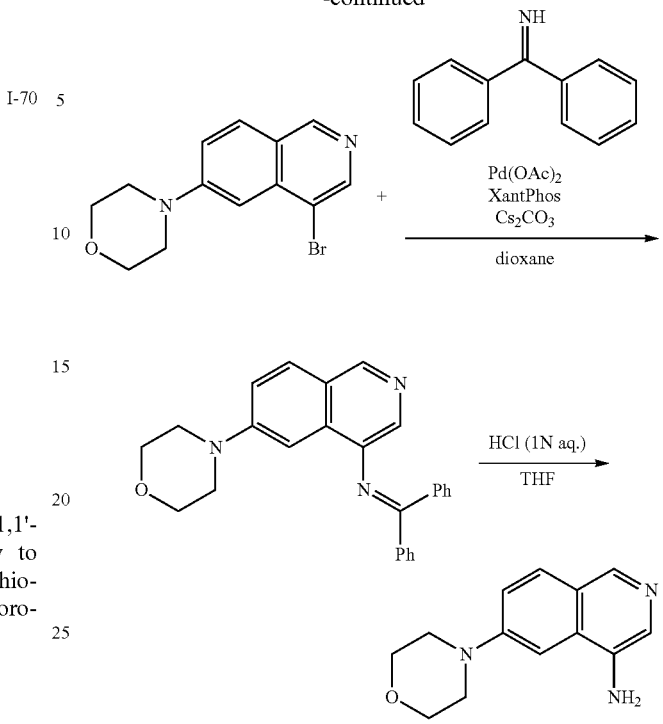

4-(4-bromoisoquinolin-6-yl)morpholine: To a microwave vial with 4-bromo-6-fluoro-isoquinoline (0 g, 4.42 mmol), morpholine (0.96 mL, 11.1 mmol) and NMP (7 mL), was added DIPEA (1.54 mL, 8.85 mmol). The solution heated under microwave conditions at 120° C. for 2 hours. The crude mixture was purified directly by silica chromatography (eluent: EtOAc in hexanes) to provide the product.

ES/MS: 292.8 (M+).

N-(6-morpholinoisoquinolin-4-yl)-1,1-diphenylmethanimine: To a vial was added 4-(4-bromoisoquinolin-6-yl)morpholine (1.15 g, 3.92 mmol), diphenylmethanimine (853 mg, 4.71 mmol), Pd(OAc)$_2$ (88 mg, 0.39 mmol), 9,9-Dimethyl-4,5-bis(diphenylphosphino)xanthene (XantPhos) (460 mg, 0.785 mmol) and cesium carbonate (1.53 g, 4.71 mmol). Dioxane (20 mL) was added, and the mixture was degassed with argon for 30 seconds. The vial was sealed, and the reaction mixture was heated at 100° C. for 16 hours. The mixture was subsequently concentrated under reduced pressure. The crude residue was purified by silica gel chromatography (eluent: EtOAc/hexanes) to provide the product.

ES/MS: 394.0 (M+H+).

6-morpholinoisoquinolin-4-amine (I-72): To a vial was added N-(6-morpholinoisoquinolin-4-yl)-1,1-diphenylmethanimine (1.1 g, 2.8 mmol). THF (15 mL) and HCl (1N aqueous; 12 mL) was added, and the mixture was stirred at it for 2 hours. The reaction was diluted with EtOAc (30 mL) and water (15 mL). The layers were separated, and the aqueous layer was basified with sat. aq. K$_2$CO$_3$ and extracted with EtOAc (2×50 mL). The combined organic layers were washed once with brine (5 mL), dried over magnesium sulfate, filtered, and concentrated under reduced pressure. The crude material was carried forward.

ES/MS: 230.0 (M+H+).

Preparation of Intermediate I-73

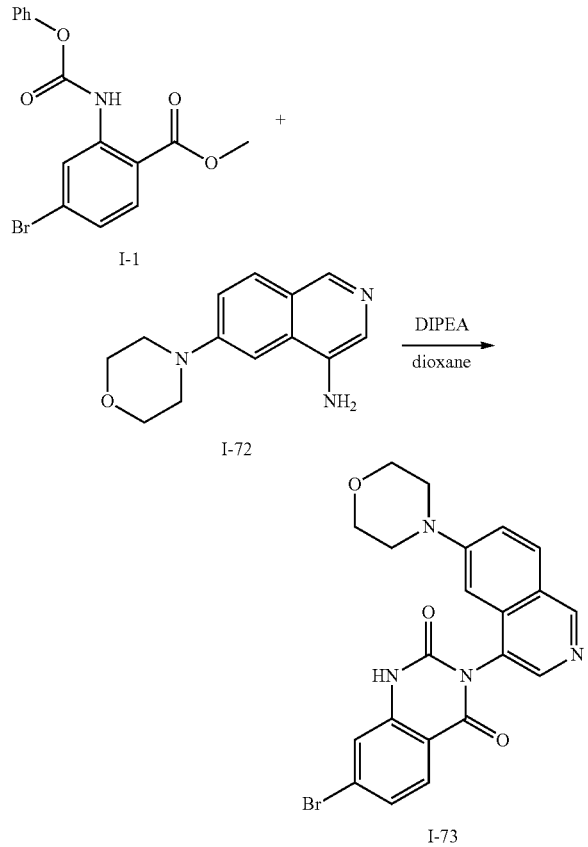

7-bromo-3-(6-morpholinoisoquinolin-4-yl)quinazoline-2,4(1H,3H)-dione (I-73): To a solution of methyl 4-bromo-2-((phenoxycarbonyl)amino)benzoate (1-1) (150 mg, 0.428 mmol) in dry dioxane (2 mL) was added DIPEA (0.75 mL, 0.43 mmol) followed by 6-morpholinoisoquinolin-4-amine (I-72) (99 mg, 0.43 mmol). The reaction mixture was heated at 90° C. for 16 hours, after which the mixture was cooled to room temperature. The mixture was subsequently cooled to 0° C. HCl (1N, 2 mL) was added, and the mixture was let stand for 30 minutes. The precipitate was filtered, and subsequently washed with water (2×2 mL). The precipitate was dried under vacuum, and was carried forward as the title compound.

ES/MS: 452.7 [M$^+$].

Preparation of Intermediate I-74

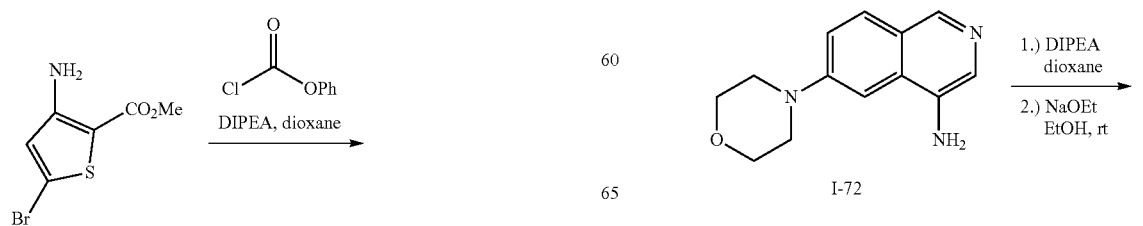

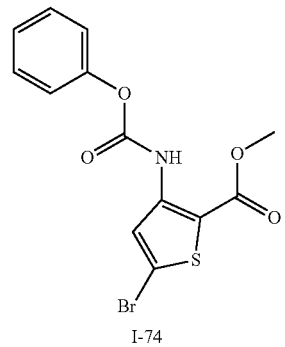

methyl 5-bromo-3-((phenoxycarbonyl)amino)thiophene-2-carboxylate I-74: To a solution of methyl 3-amino-5-bromo-thiophene-2-carboxylate (6.0 g, 25.4 mmol, 1.0 equiv.) in dry dioxane (100 mL) was added DIPEA (8.85 mL, 50.8 mmol, 2 equiv.) followed by phenyl chloroformate (4.31 mL, 1.3 equiv). The reaction mixture was stirred at 80 C, 6 h. The reaction mixture was cooled to room temperature and concentrated to dryness to afford crude product. The crude product was purified by silica gel column chromatography (eluent: EtOAc/Hexanes) to afford the product.

ES/MS: 355.7 (M+H$^+$).

Preparation of Intermediate I-75

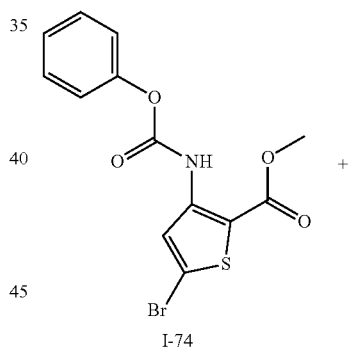

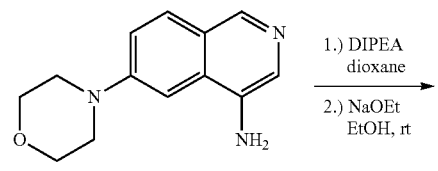

501

-continued

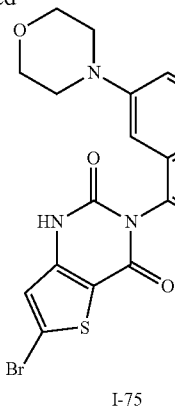

I-75

6-bromo-3-(6-morpholinoisoquinolin-4-yl)thieno[3,2-d]pyrimidine-2,4(1H,3H)-dione (I-75): To a suspension of methyl 5-bromo-3-((phenoxycarbonyl)amino)thiophene-2-carboxylate (I-74) (400 mg, 1.12 mmol, 1.0 equiv.) in dry dioxane (5 mL) at was added DIPEA (0.2 mL, 1.12 mmol, 1 equiv.) followed by 6-morpholinoisoquinolin-4-amine (I-72) (257 mg, 1.12 mmol). The reaction mixture was refluxed overnight. The reaction was observed to be partially complete. The reaction mixture was cooled to ambient temperature and sodium ethoxide (20% wt. in EtOH) at room temperature dropwise, until LCMS showed full consumption of starting material. The reaction mixture was concentrated under reduced pressure, and HCl (1N, 4 mL) was added, which formed a precipitate. The solid was collected via filtration, and washed with water (2×3 mL) to deliver the product.

ES/MS: 458.7 [M+].

Preparation of Intermediate I-76

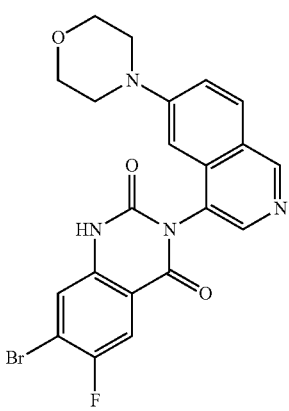

I-76

7-bromo-6-fluoro-3-(6-morpholinoisoquinolin-4-yl)quinazoline-2,4(1H,3H)-dione (I-76): Prepared analogously to I-73, substituting methyl 4-bromo-2-((phenoxycarbonyl)amino)benzoate (I-1) with methyl 2-amino-4-bromo-5-fluorobenzoate (prepared according to I-3).

ES/MS: 470.7 (M+).

Preparation of Intermediate I-77

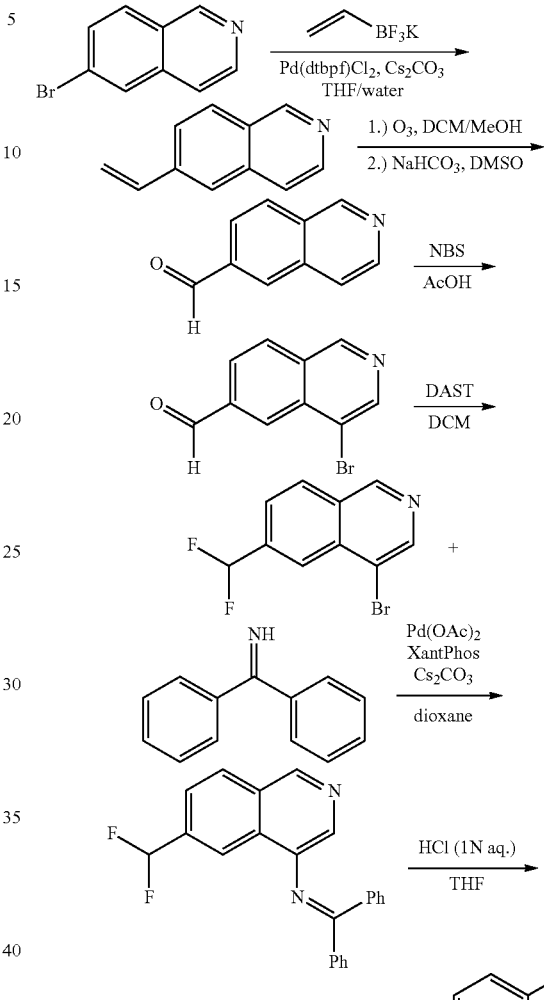

I-77

6-vinylisoquinoline: A mixture of 6-bromoisoquinoline (10 g, 48.0 mmol, 1 eq), potassium trifluoro(vinyl)borate (16.1 g, 120.1 mmol), $Cs_2CO_3$ (46.9 g, 144.1 mmol) and ditert-butyl(cyclopentyl)phosphane;dichloropalladium;iron (1.5 g, 2.4 mmol) in THF (270 mL) and $H_2O$ (30 mL) was degassed and purged with $N_2$, and then the mixture was stirred at 80° C. for 12 hours under $N_2$ atmosphere. The reaction mixture was concentrated under reduced pressure to remove solvent. The residue was diluted with $H_2O$ (50 mL) and extracted with EtOAc (100 mL×3). The combined organic layers were washed with NaCl (50 mL×3), dried over $Na_2SO_4$, filtered and concentrated under reduced pressure. The residue was purified by flash silica gel chromatography (eluent of EtOAc/Petroleum ether) to give the product.

$^1$H NMR (400 MHz, CHLOROFORM-d) δ 9.24 (s, 1H), 8.53 (d, J=5.9 Hz, 1H), 7.% (d, J=8.5 Hz, 1H), 7.80-7.73 (m, 2H), 7.66 (d, J=5.9 Hz, 1H), 6.95-6.86 (m, 1H), 5.99 (d, J=17.5 Hz, 1H), 5.50 (d, J=10.9 Hz, 1H).

isoquinoline-6-carbaldehyde: A mixture of 6-vinylisoquinoline (6 g, 38.6 mmol, 1 eq) in DCM (50 mL) and MeOH (50 mL) was cooled to −70° C. The mixture was ozonized until blue color persisted under $O_3$ (15 psi) for 1 hr. Then $O_2$ was bubbled the solution for 10 min. The mixture was treated with solid $NaHCO_3$ (3.9 g, 46.3 mmol) and DMSO (8.4 mL, 108.2 mmol) and the mixture was warmed to 20° C. and then the mixture was stirred at 20° C. for 12 hr. The residue was diluted with $H_2O$ (30 mL) and extracted with DCM (30 mL×3). The combined organic layers were dried over $Na_2SO_4$, filtered and concentrated under reduced pressure. The residue was purified by flash silica gel chromatography (eluent: EtOAc/Petroleum ether) to give the product.

$^1$H NMR (400 MHz, DMSO-$d_6$) δ 10.22 (s, 1H), 9.45 (s, 1H), 8.69-8.59 (m, 2H), 8.28 (d, J=8.5 Hz, 1H), 8.11-8.02 (m, 2H).

4-bromoisoquinoline-6-carbaldehyde: To a solution of isoquinoline-6-carbaldehyde (3.2 g, 20.7 mmol, 1 eq) in AcOH (50 mL) was added NBS (4.0 g, 22.8 mmol). The mixture was stirred at 90° C. for 3 hr. The reaction mixture was concentrated under reduced pressure to remove solvent. The residue was purified by flash silica gel chromatography (eluent of Ethyl acetate/Petroleum ether) to give the product.

1H NMR (400 MHz, CHLOROFORM-d) δ=10.30 (s, 1H), 9.28 (s, 1H), 8.86 (s, 1H), 8.66 (s, 1H), 8.22-8.08 (m, 2H).

4-bromo-6-(difluoromethyl)isoquinoline: To a solution of 4-bromoisoquinoline-6-carbaldehyde (398 mg, 1.6 mmol, 1 eq) in DCM (10 mL) was added DAST (815.2 mg, 5.0 mmol, 668.2 uL, 3 eq) at 0° C. at $N_2$. The mixture was stirred at 25° C. for 12 hr. The residue was diluted with $NaHCO_3$ (5 mL) and extracted with DCM (30 mL×3). The combined organic layers were dried over $Na_2SO_4$, filtered and concentrated under reduced pressure to give the product.

N-(6-(difluoromethyl)isoquinolin-4-yl)-1,1-diphenylmethanimine: A mixture of 4-bromo-6-(difluoromethyl)isoquinoline (400 mg, 1.5 mmol, 1 eq), diphenylmethanimine (337.1 mg, 1.8 mmol), $Cs_2CO_3$ (505.0 mg, 1.5 mmol), Xantphos (896.8 mg, 1.5 mmol) and Pd(OAc): (34.8 mg, 155.0 μmol) in dioxane (10 mL) was degassed and purged with $N_2$, and then the mixture was stirred at 100° C. for 16 hr under $N_2$ atmosphere. The reaction mixture was diluted with $H_2O$ (100 mL) and extracted with EtOAc (100 mL×3). The combined organic layers were dried over $Na_2SO_4$, filtered and concentrated under reduced pressure. The residue was purified by flash silica gel chromatography (eluent: EtOAc/Petroleum ether) to give the product.

6-(difluoromethyl)isoquinolin-4-amine (I-77): To a solution of N-(6-(difluoromethyl)isoquinolin-4-yl)-1,1-diphenylmethanimine (412 mg, 1.1 mmol, 1 eq) in THF (1 mL) was added HCl (1 M, 1.1 mL). The mixture was stirred at 25° C. for 3 hr. The reaction mixture was diluted with $NaHCO_3$(20 mL). The reaction mixture was extracted with EtOAc (10 mL×3). The combined organic layers were dried over $Na_2SO_4$, filtered and concentrated under reduced pressure. The residue was purified by flash silica gel chromatography (eluent. EtOAc/Petroleum ether) to give the product.

$^1$H NMR (400 MHz, CHLOROFORM-d) δ 8.80 (s, 1H), 8.13 (s, 1H), 8.03 (d, J=8.5 Hz, 1H), 7.98 (s, 1H), 7.70 (d, J=8.5 Hz, 1H), 6.84 (t, J=56.2 Hz, 1H), 4.24-4.12 (m, 2H).

MS (ESI): m/z=195.2 (M+H$^+$).

Preparation of Intermediate I-78

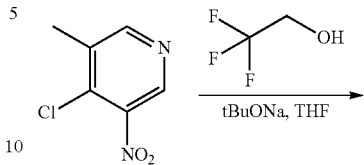

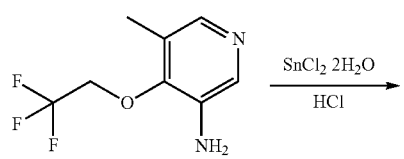

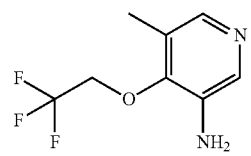

I-78

3-methyl-5-nitro-4-(2,2,2-trifluoroethoxy)pyridine: To a solution of 4-chloro-3-methyl-5-nitro-pyridine (0.5 g, 2.9 mmol, 1 eq) in THF (20 mL) was added 2,2,2-trifluoroethanol (579.7 mg, 5.7 mmol, 417.0 μL), and t-BuONa (334.1 mg, 3.4 mmol) at 0° C. The mixture was stirred at 25° C. for 12 hr. The reaction mixture was diluted with $NH_4Cl$ (20 mL) and extracted with EtOAc (30 mL×3). The combined organic layers were washed with brine (10 mL×3), dried over $Na_2SO_4$, filtered and concentrated under reduced pressure The residue was purified by flash silica gel chromatography (eluent: EtOAc/Petroleum ether) to give the product.

$^1$H NMR (400 MHz, CHLOROFORM-d) δ=8.92 (s, 1H), 8.58 (s, 1H), 4.36 (q, J=8.0 Hz, 2H), 2.33 (s, 3H).

5-methyl-4-(2,2,2-trifluoroethoxy)pyridin-3-amine (I-78): To a solution of 3-methyl-5-nitro-4-(2,2,2-trifluoroethoxy)pyridine (440 mg, 1.8 mmol, 1 eq) in HCl (15 mL, 12M) was added $SnCl_2 \cdot 2H_2O$ (1.2 g, 5.5 mmol, 3 eq). The mixture was stirred at 25° C. for 12 hr. The mixture was diluted with $NaHCO_3$ (22 mL) and extracted with ethyl acetate (30 mL×3). The combined organic layers were dried over $Na_2SO_4$, filtered and concentrated under reduced pressure. The residue was purified by prep-HPLC (HCl condition column: Phenomenex Luna 80*30 mm*3 um: mobile phase: [water (HCl)–ACN]; B %: 1%-20%) to give the product.

$^1$H NMR (400 MHz, DMSO-d) δ 8.19-8.00 (m, 2H), 6.29 (br s, 2H), 4.84 (d, J=8.9 Hz, 2H), 2.29 (s, 3H).

MS (ESI): m/z=207.2 (M+H$^+$).

Preparation of Intermediate I-79 and Intermediate I-80

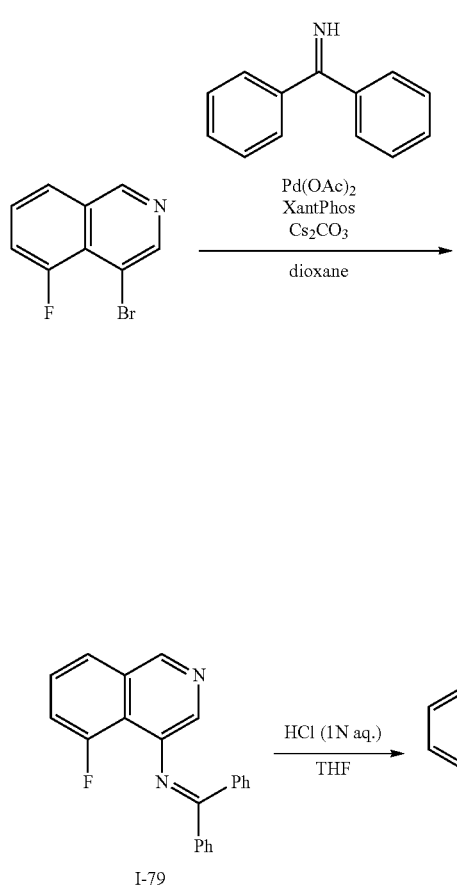

I-79

N-(5-fluoroisoquinolin-4-yl)-1,1-diphenylmethanimine (I-79):
To a vial was added 4-bromo-5-fluoroisoquinoline (0.5 g, 2.21 mmol), diphenylmethanimine (481 mg, 2.65 mmol), Pd(OAc)$_2$ (50 mg, 0.22 mmol), 9,9-Dimethyl-4,5-bis(diphenylphosphino)xanthene (XantPhos) (257 mg, 0.44 mmol) and cesium carbonate (865 mg, 2.65 mmol). Dioxane (10 mL) was added, and the mixture was degassed with argon for 30 seconds. The vial was sealed, and the reaction mixture was heated at 100° C. for 16 hours. The mixture was subsequently concentrated under reduced pressure. The crude residue was purified by silica gel chromatography (eluent: EtOAc/hexanes) to provide the product.

ES/MS: 326.9 (M+H$^+$).

5-fluoroisoquinolin-4-amine (I-80):
To a vial was added N-(5-fluoroisoquinolin-4-yl)-1,1-diphenylmethanimine (600 mg, 1.84 mmol). THF (10 mL) and HCl (1N aqueous; 8 mL) were added, and the mixture was stirred at rt for 2 hours. The reaction was diluted with EtOAc (30 mL) and water (15 mL). The layers were separated, and the aqueous layer was basified with sat. aq. K$_2$CO$_3$ and extracted with EtOAc (2×50 mL). The combined organic layers were washed once with brine (5 mL), dried over magnesium sulfate, filtered, and concentrated under reduced pressure. The crude material was carried forward.

ES/MS: 163.0 (M+H$^+$).

Preparation of Intermediate I-81

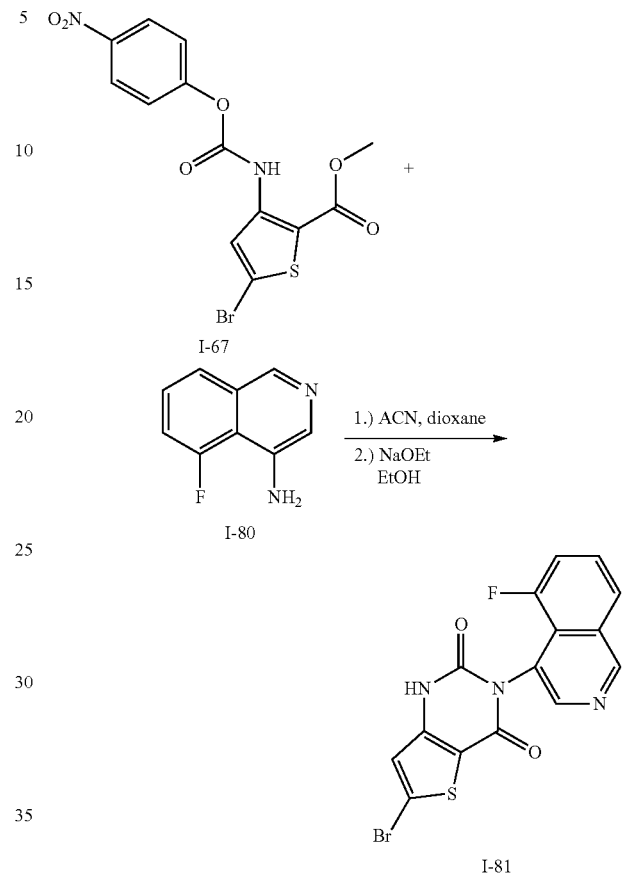

6-bromo-3-(5-fluoroisoquinolin-4-yl)thieno[3,2-d]pyrimidine-2,4(1H,3H)-dione (I-81):
To a suspension of methyl 5-bromo-3-(((4-nitrophenoxy)carbonyl)amino)thiophene-2-carboxylate (I-67) (150 mg, 0.374 mmol, 1.0 equiv.) in acetonitrile (4 mL) and dioxane (2 mL) was added 5-fluoroisoquinolin-4-amine (I-80) (67 mg, 0.41 mmol). The reaction mixture was stirred at 80° C. overnight. The reaction was subsequently cooled to 0° C. A precipitate formed, and the precipitate was isolated by filtration. The precipitate was dissolved in EtOH (4 mL), and to reaction mixture was added sodium ethoxide (21% wt. in EtOH; 0.15 mL) at room temperature dropwise, until LCMS showed full conversion to the product. The reaction mixture was concentrated under reduced pressure, and HCl (1N, 4 mL) was added, which formed a precipitate. The solid was collected via filtration, and washed with water (2×1 mL) to deliver the product.

ES/MS: 391.7 [M$^+$].

Preparation of Intermediate I-82

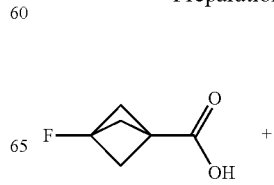

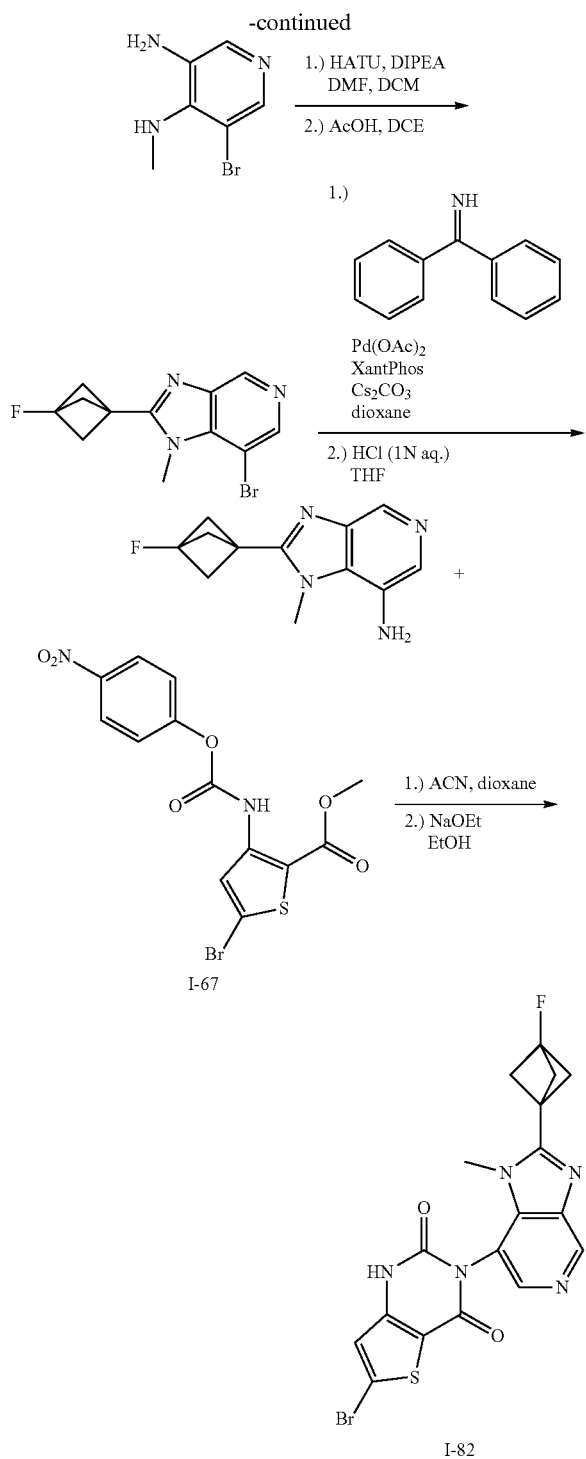

I-67

I-82 sure. The crude material was taken up in dichloroethane (2.0 mL) and acetic acid (2.0 mL) and stirred at 80° C. for 4 hours. The reaction mixture was concentrated under reduced pressure, and purified by silica gel column chromatography (eluent: EtOAc/Hex) to provide the desired product.

ES/MS: 295.9 (M⁺).

2-(3-fluorobicyclo[1.1.1]pentan-1-yl)-1-methyl-1H-imidazo[4,5-c]pyridin-7-amine: To a vial was added 7-bromo-2-(3-fluorobicyclo[1.1.1]pentan-1-yl)-1-methyl-1H-imidazo[4,5-c]pyridine (240 mg, 0.81 mmol), diphenylmethanimine (220 mg, 1.22 mmol), Pd(OAc)$_2$ (18 mg, 0.081 mmol), 9,9-Dimethyl-4,5-bis(diphenylphosphino)xanthene (XantPhos) (94 mg, 0.162 mmol) and cesium carbonate (317 mg, 0.973 mmol). Dioxane (4 mL) was added, and the mixture was degassed with argon for 30 seconds. The vial was sealed, and the reaction mixture was heated at 100° C. for 16 hours. The mixture was subsequently concentrated under reduced pressure. The crude residue was purified by silica gel chromatography (eluent: EtOAc/hexanes). The isolated N-(6-morpholinoisoquinolin-4-yl)-1,1-diphenylmethanimine was dissolved in THF (5 mL) and HCl (1N aqueous: 4 mL) was added, and the mixture was stirred at rt for 2 hours. The reaction was diluted with EtOAc (10 mL) and water (5 mL). The layers were separated, and the aqueous layer was basified with sat. aq. K$_2$CO$_3$ and extracted with EtOAc (2×30 mL). The combined organic layers were washed once with brine (5 mL), dried over magnesium sulfate, filtered, and concentrated under reduced pressure. The crude material was carried forward.

ES/MS: 233.0 (M+H⁺).

6-bromo-3-(2-(3-fluorobicyclo[1.1.1]pentan-1-yl)-1-methyl-1H-imidazo[4,5-c]pyridin-7-yl)thieno[3,2-d]pyrimidine-2,4(1H,3H)-dione (I-82): To a suspension of methyl 5-bromo-3-(((4-nitrophenoxy)carbonyl)amino)thiophene-2-carboxylate (I-67) (170 mg, 0.424 mmol, 1.0 equiv.) in acetonitrile (4 mL) and dioxane (2 mL) was added 2-(3-fluorobicyclo[1.1.1]pentan-1-yl)-1-methyl-1H-imidazo[4,5-c]pyridin-7-amine (103 mg, 0.45 mmol). The reaction mixture was stirred at 80° C. overnight. The reaction was subsequently cooled to 0° C. A precipitate formed, and the precipitate was isolated by filtration. The precipitate was dissolved in EtOH (4 mL), and to reaction mixture was added sodium ethoxide (21% wt. in EtOH; 0.16 mL) at room temperature dropwise, until LCMS showed full conversion to the product. The reaction mixture was concentrated under reduced pressure, and HCl (1N, 0.2 mL) and DMF (2 mL) were added. The mixture was filtered through an acrodisc, and purified directly by RP-HPLC (0.1% TFA-ACN in 0.1% TFA Water, Column: Gemini 5 μM, NX-C18 110 Angstrom, 250×21.2 mm) to give the product.

ES/MS: 361.7 [M⁺].

Preparation of Intermediate I-83

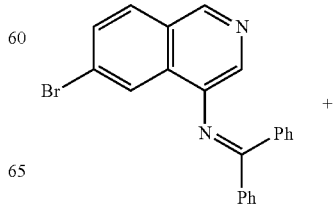

+

7-bromo-2-(3-fluorobicyclo[1.1.1]pentan-1-yl)-1-methyl-1H-imidazo[4,5-c]pyridine: To a solution of 3-fluorobicyclo[1.1.1]pentane-1-carboxylic acid (161 mg, 1.24 mmol), 5-bromo-N4-methyl-pyridine-3,4-diamine (250 mg, 1.24 mmol), and HATU (611 mg, 1.61 mmol) in DCM (2.0 mL) and DMF (2 mL) was added DIPEA (0.86 mL, 4.95 mmol). The reaction mixture was stirred at RT for 16 hours, then diluted with sat. aq. ammonium chloride and EtOAc. The aqueous layer was extracted with EtOAc (2×). The combined organic layers were washed with brine, dried over magnesium sulfate, and concentrated under reduced pres-

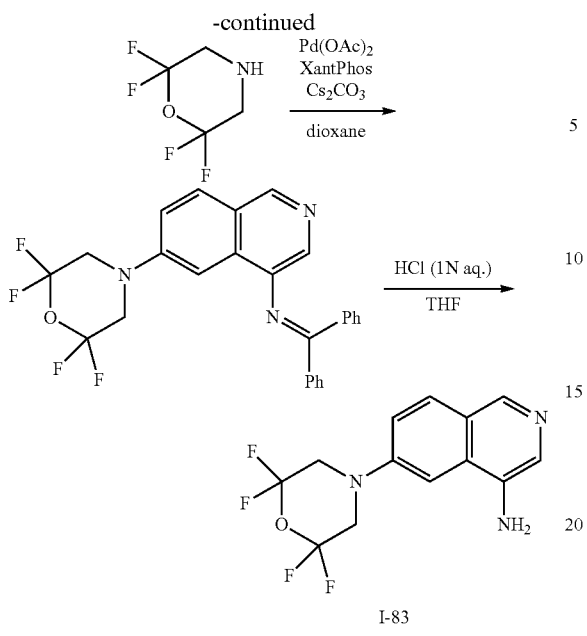

I-83

1,1-diphenyl-N-(6-(2,2,6,6-tetrafluoromorpholino)isoquinolin-4-yl)methanimine: To a vial was added N-(6-bromoisoquinolin-4-yl)-1,1-diphenylmethanimine (0.2 g, 516 mmol), 2,2,6,6-tetrafluoromorpholine (123 mg, 0.775 mmol), Pd(OAc)$_2$ (12 mg, 0.052 mmol), 9,9-Dimethyl-4,5-bis(diphenylphosphino)xanthene (XantPhos) (60 mg, 0.10 mmol) and cesium carbonate (337 mg, 1.03 mmol). Dioxane (4 mL) was added, and the mixture was degassed with argon for 30 seconds. The vial was sealed, and the reaction mixture was heated at 100° C. for 16 hours. The mixture was subsequently concentrated under reduced pressure. The crude residue was purified by silica gel chromatography (eluent: EtOAc/hexanes) to provide the product.

ES/MS: 465.9 (M+H$^+$).

6-(2,2,6,6-tetrafluoromorpholino)isoquinolin-4-amine (I-83): To a vial was added 1,1-diphenyl-N-(6-(2,2,6,6-tetrafluoromorpholino)isoquinolin-4-yl)methanimine (200 mg, 0.43 mmol). THF (10 mL) and HCl (1N aqueous: 5 mL), and the mixture was stirred at rt for 2 hours. The reaction was diluted with EtOAc (40 mL) and water (15 mL). The layers were separated, and the aqueous layer was basified with sat. aq. K$_2$CO$_3$ and extracted with EtOAc (2×50 mL). The combined organic layers were dried over magnesium sulfate, filtered, and concentrated under reduced pressure. The crude material was carried forward.

ES/MS: 301.9 (M+H$^+$).

Preparation of Intermediate I-84

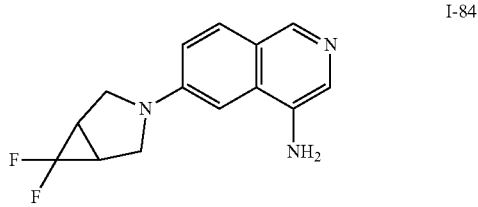 [SMILES: Nc1cncc2ccc(N3CC4C(C3)C4(F)F)cc12]

I-84

6-(6,6-difluoro-3-azabicyclo[3.1.0]hexan-3-yl)isoquinolin-4-amine (I-84): Prepared analogously to 1-83, substituting 2,2,6,6-tetrafluoromorpholine with 6,6-difluoro-3-azabicyclo[3.1.0]hexane.

ES/MS: 262.0 (M+H).

Preparation of Intermediate I-85

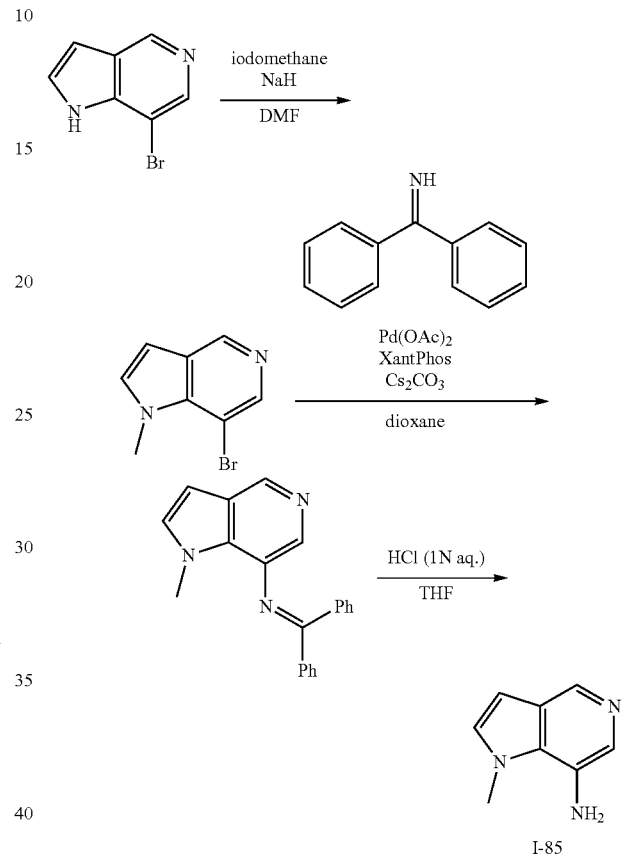

I-85

7-bromo-1-methyl-1H-pyrrolo[3,2-c]pyridine: To a vial was added 7-bromo-1H-pyrrolo[3,2-c]pyridine (1 g, 5.08 mmol), and dry DMF (5 mL). The reaction was cooled to 0° C. under a N2 atmosphere, and NaH (60% wt. dispersion in mineral oil; 214 mg; 5.58 mmol) was added. The mixture was stirred for 30 minutes at 0° C. under a N2 atmosphere. Subsequently, iodomethane (0.35 mL; 5.58 mmol) was added, and the mixture was stirred for 2 hours warming to room temperature. The reaction was quenched with water (10 mL) and EtOAc (50 mL). The layers were separated, and the organic layer was washed with water (10 mL) and brine (10 mL). The organic layer was dried over magnesium sulfate, filtered, and concentrated under reduced pressure. The crude residue was purified by silica gel chromatography (eluent: EtOAc/hexanes) to provide the product.

ES/MS: 210.9 (M$^+$).

N-(1-methyl-1H-pyrrolo[3,2-c]pyridin-7-yl)-1,1-diphenylmethanimine: To a vial was added 7-bromo-1-methyl-1H-pyrrolo[3,2-c]pyridine (0.8 g, 3.79 mmol), diphenylmethanimine (1.03 g, 5.69 mmol), Pd(OAc)$_2$ (85 mg, 0.38 mmol), 9,9-Dimethyl-4,5-bis(diphenylphosphino)xanthene (XantPhos) (440 mg, 0.76 mmol) and cesium carbonate (1.48 g, 4.55 mmol). Dioxane (25 mL) was added, and the mixture was degassed with argon for 30 seconds. The vial was sealed, and the reaction mixture was heated at 100° C. for 16 hours. The mixture was subsequently concentrated under reduced pressure. The crude residue was purified by silica gel chromatography (eluent: EtOAc/hexanes) to provide the product.

ES/MS: 312.0 (M+H⁺).

1-methyl-1H-pyrrolo[3,2-c]pyridin-7-amine (I-85): To a vial was added N—(I-methyl-1H-pyrrolo[3,2-c]pyridin-7-yl)-1,1-diphenylmethanimine (850 mg, 2.73 mmol). THF (15 mL) and HCl (1N aqueous; 12 mL) was added, and the mixture was stirred at rt for 2 hours. The reaction was diluted with EtOAc (40 mL) and water (15 mL). The layers were separated, and the aqueous layer was basified with sat. aq. K₂CO₃ and extracted with EtOAc (2×50 mL). The combined organic layers were washed once with brine (5 mL), dried over magnesium sulfate, filtered, and concentrated under reduced pressure. The crude material was carried forward.

¹H NMR (400 MHz, Methanol-d₄) δ 8.24 (s, 1H), 7.64 (s, 1H), 7.15 (d, J=3.3 Hz, 1H), 6.50 (d, J=3.1 Hz, 1H), 4.15 (s, 3H).

Preparation of Intermediate I-86

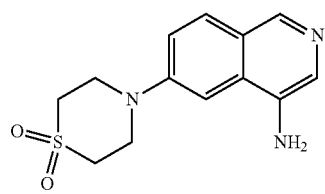

I-86

4-(4-aminoisoquinolin-6-yl)thiomorpholine 1,1-dioxide (I-86): Prepared analogously to 1-83, substituting 2,2,6,6-tetrafluoromorpholine with 1,4-thiazinane 1,1-dioxide.

ES/MS: 277.9 (M+H⁺).

Preparation of Intermediate I-87

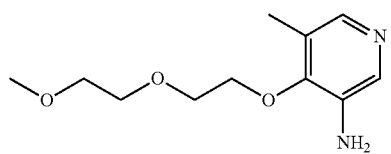

I-87

4-(2-(2-methoxyethoxy)ethoxy)-5-methylpyridin-3-amine (I-87): Prepared analogously to 1-34, substituting 2-methoxyethan-1-ol with 2-(2-methoxyethoxy)ethanol.

ES/MS: 226.2 (M+H⁺).

Preparation of Intermediate I-88

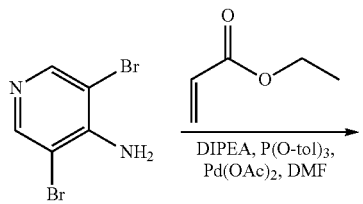

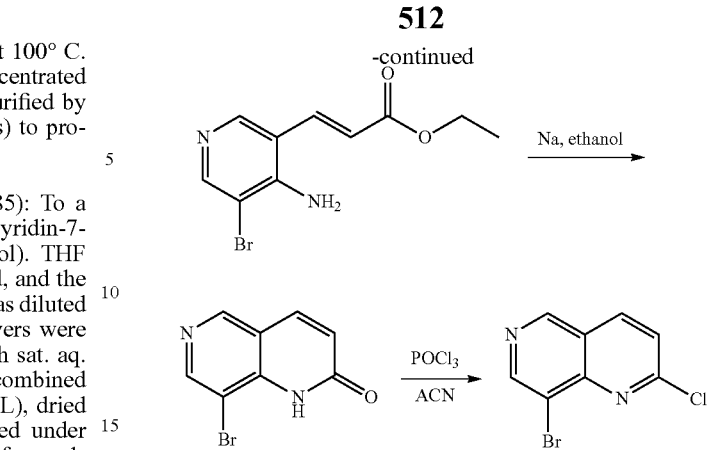

I-88 ethyl (E)-3-(4-amino-5-bromopyridin-3-yl)acrylate: To a solution of 3,5-dibromopyridin-4-amine (20 g, 79.3 mmol, 1.0 eq), ethyl acrylate (10.3 g, 103.2 mmol, 1.3 eq) and TBAE (47.8 g, 159 mmol, 2.0 eq) in dioxane (250 mL) was added Pd(OAc)₂ (893 mg, 3.96 mmol, 0.05 eq) and DavePhos (1.87 g, 4.76 mmol, 0.06 eq) at rt under N2. Then the reaction mixture was stirred at 100° C. for 16 h. The reaction was concentrated under reduced pressure. The residue was partitioned between ethyl acetate (200 mL) and water (200 mL). The separated organic layer was washed with water, dried over sodium sulfate, and concentrated to dryness. The residue was purified by silica gel chromatography (petroleum ether and ethyl acetate, 2:1) to give the desired compound.

8-bromo-1,6-naphthyridin-2(11H)-one: To ethanol (200 mL) at rt was added sodium (8.48 g, 369.0 mmol, 4.0 eq). The solution was stirred until the sodium disappeared. Ethyl (E)-3-(4-amino-5-bromopyridin-3-yl)acrylate (25.0 g, 92.2 mmol, 1.0 eq) was added to the above solution at 0° C., then the reaction mixture was stirred at 85° C. for 4 h. The reaction was monitored by TLC. The reaction was quenched with AcOH (22.1 g, 369.0 mmol, 4.0 eq) at 0° C. Then the reaction mixture was concentrated under reduced pressure. To the residue was added water (200 mL). The mixture was stirred for 15 min. The suspension was filtrated and washed with water (50 mL×2) to give a crude product. The crude product was purified by flash column chromatography (petroleum ether and ethyl acetate, 1:1) to afford the desired compound.

¹H NMR (400 MHz, CD₃OD): δ 8.74 (s, 1H), 8.65 (s, 1H), 8.00 (d 1H), 6.70 (d, 1H).

8-bromo-2-chloro-1,6-naphthyridine (I-88): To a solution of compound 8-bromo-1,6-naphthyridin-2(1H)-one (18.0 g, 80.0 mmol, 1.0 eq.) in ACN (180 mL) at 0° C. was added POCl₃ (122.0 g, 800 mmol, 10.0 eq). The reaction was stirred at 100° C. for 8 h. The reaction was cooled to rt and concentrated. The residue was diluted with ice-water, and neutralized with saturated aqueous NaHCO₃ and extracted with DCM (200 mL×2). The combined organic layers were washed with water, brine, dried over sodium sulfate and evaporated to dryness. The residue was purified by silica gel chromatography eluted (petroleum ether and DCM, 2:1) to give the desired compound.

¹H NMR (400 MHz, CD₃OD): δ 9.26 (s, 1H), 8.95 (s, 1H), 8.54 (d, 1H), 7.73 (d 1H).

Preparation of Intermediate I-89

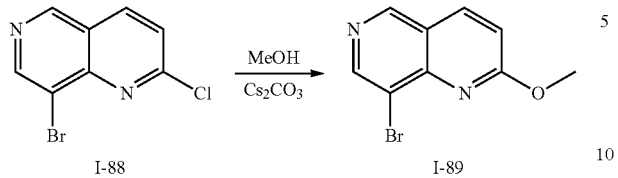

8-bromo-2-methoxy-1,6-naphthyridine (I-89): To a vial was added 8-bromo-2-chloro-1,6-naphthyridine (500 mg, 2.1 mmol), cesium carbonate (1.3 g, 4.1 mmol), and MeOH (5 ml). The mixture was stirred for 15 hours, filtered, and concentrated under reduced pressure. The crude residue was used as is in the next reaction.
ES/MS: 239.1 (M+H⁺).

Preparation of Intermediate I-90

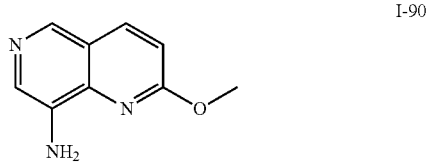

2-methoxy-1,6-naphthyridin-8-amine (I-90): Prepared analogously to I-32, substituting 8-bromo-2-methoxy-1,6-naphthyridine (I-89) with 4-chlorocinnoline.
ES/MS: 176.1 (M+H⁺).

Preparation of Intermediate I-91

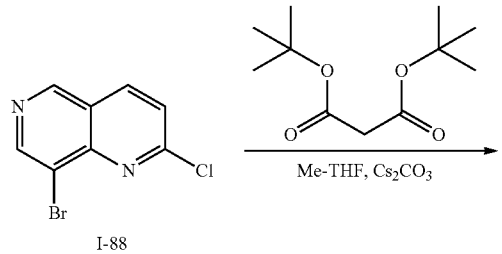

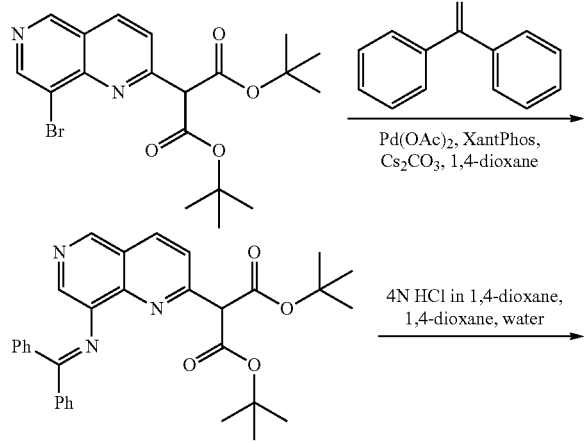

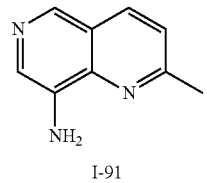

di-tert-butyl 2-(8-bromo-1,6-naphthyridin-2-yl)malonate: To a vial was added 8-bromo-2-chloro-1,6-naphthyridine (I-88) (1000 mg, 4.1 mmol), cesium carbonate (2.7 g, 8.2 mmol), and Me-THF (10 ml). The mixture was stirred for 15 hours at 80° C., allowed to cool to RT, filtered, and the solid was dried under vacuum. The crude solid was used as is in the next reaction.
ES/MS: 423.4 (M+H⁺).

di-tert-butyl 2-(8-((diphenylmethylene)amino)-1,6-naphthyridin-2-yl)malonate: To a microwave vial was added di-tert-butyl 2-(8-bromo-1,6-naphthyridin-2-yl)malonate (316 mg, 0.75 mmol), diphenylmethanimine (162 mg, 0.90 mmol), Pd(OAc)₂ (16.8 mg, 0.07 mmol), 9,9-Dimethyl-4,5-bis(diphenylphosphino)xanthene (XantPhos) (87 mg, 0.15 mmol) and cesium carbonate (243 mg, 0.75 mmol), 1,4 Dioxane (4 mL) was added, and the mixture was degassed with argon for 30 seconds. The vial was sealed, and the reaction mixture was heated at 100° C. for 16 hours. The mixture was subsequently concentrated under reduced pressure. The crude residue was purified by silica gel chromatography (eluent: EtOAc/hexanes) to provide the product.
ES/MS: 524.5 (M+H⁺).

2-methyl-1,6-naphthyridin-8-amine (I-91): To a vial was added di-tert-butyl 2-(8-((diphenylmethylene)amino)-1,6-naphthyridin-2-yl)malonate (250 mg, 0.48 mmol), 1,4-Dioxane (4 mL) and HCl in 1,4-dioxane (4N: 1 mL) was added, and the mixture was stirred at rt for 15 hours. Water was added until the mixture was clear and stirred for another 15 hours. The reaction was diluted with EtOAc and water. The layers were separated, and the aqueous layer was basified with K₂CO₃ and extracted with EtOAc 2×. The combined organic layers were dried over sodium sulfate, filtered, and concentrated under reduced pressure. The crude residue was used in the next reaction.
ES/MS: 160.2 (M+H⁺).

Preparation of Intermediate I-92

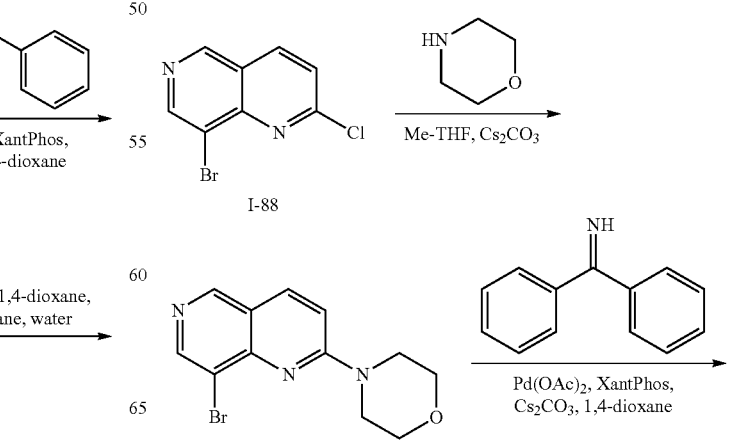

-continued

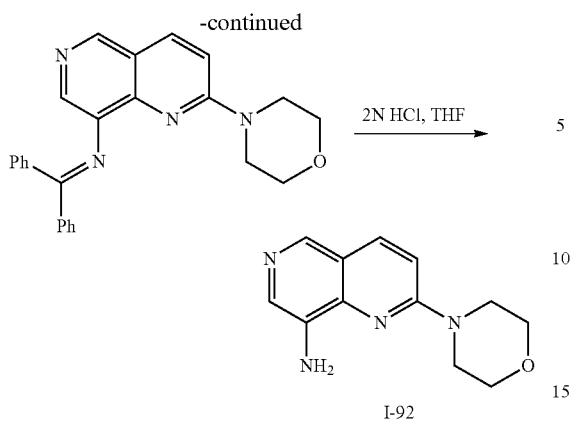

I-92

4-(8-bromo-1,6-naphthyridin-2-yl)morpholine: To a vial was added 8-bromo-2-chloro-1,6-naphthyridine (I-88) (300 mg, 1.2 mmol), cesium carbonate (0.8 g, 2.5 mmol), and Me-THF (2 ml). The mixture was placed in a water bath and morpholine (107 mg, 1.2 mmol) was slowly added, the water bath was removed, and the mixture was stirred for 15 hours. The reaction was diluted with EtOAc and water, filtered and the solid was dried under vacuum.

ES/MS: 294.2 (M+H⁺).

N-(2-morpholino-1,6-naphthyridin-8-yl)-1,1-diphenylmethanimine: To a microwave vial was added 4-(8-bromo-1,6-naphthyridin-2-yl)morpholine (320 mg, 1.1 mmol), diphenylmethanimine (237 mg, 1.3 mmol), Pd(OAc)$_2$ (24 mg, 0.11 mmol), 9,9-Dimethyl-4,5-bis(diphenylphosphino) xanthene (XantPhos) (126 mg, 0.22 mmol) and cesium carbonate (354 mg, 1 mmol), 1,4-Dioxane (4 mL) and DMF (1 mL) were added, and the mixture was degassed with argon for 30 seconds. The vial was sealed, and the reaction mixture was heated at 100° C. for 16 hours. The reaction was cooled, diluted with EtOAc and water, then filtered over celite, rinsing with EtOAc. The layers were separated, and the organic layer was washed with 0.5 M HCl. The organic layer was dried over sodium sulfate and concentrated. The residue was used as is in the next reaction.

ES/MS: 395.3 (M+H).

2-morpholino-1,6-naphthyridin-8-amine (I-92): To a vial was added N-(2-morpholino-1,6-naphthyridin-8-yl)-1,1-diphenylmethanimine (188 mg, 0.48 mmol). THF (4 mL) and HCl (2N aqueous; 1.5 mL) were added, and the mixture was stirred at rt for 15 hours. The reaction was diluted with EtOAc and water. The layers were separated, and the aqueous layer was basified with K$_2$CO$_3$ and extracted with EtOAc 2×. The combined organic layers were dried over sodium sulfate, filtered, and concentrated under reduced pressure. The crude residue used in the next reaction.

ES/MS: 231.2 (M+H⁺).

Preparation of Intermediate I-93

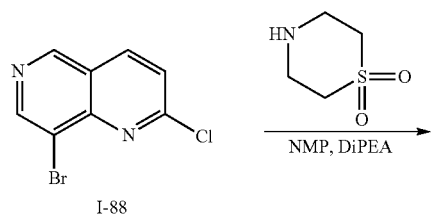

I-88

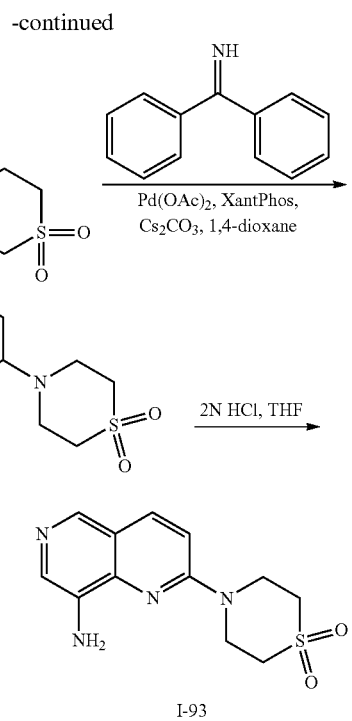

I-93

4-(8-bromo-1,6-naphthyridin-2-yl)thiomorpholine 1,1-dioxide: To a vial was added 8-bromo-2-chloro-1,6-naphthyridine (I-88) (500 mg, 2.1 mmol), N-ethyldiisopropylamine (0.73 g, 4.1 mmol), and NMP (2 ml). Thiomorpholine 1,1-dioxide (555 mg, 4.1 mmol) was added and the mixture was stirred for 15 hours at 100° C. The reaction was diluted with DCM and purified by flash column chromatography.

ES/MS: 342.1 (M+H⁺).

4-(8-((diphenylmethylene)amino)-1,6-naphthyridin-2-yl) thiomorpholine 1,1-dioxide: To a microwave vial was added 4-(8-bromo-1,6-naphthyridin-2-yl)thiomorpholine 1,1-dioxide (600 mg, 1.8 mmol), diphenylmethanimine (204 mg, 2.1 mmol), Pd(OAc)$_2$ (39 mg, 0.10 mmol), 9,9-Dimethyl-4,5-bis(diphenylphosphino)xanthene (XantPhos) (204 mg, 0.35 mmol) and cesium carbonate (571 mg, 1.8 mmol), 1,4-Dioxane (4 mL) and DMF (1 mL) were added, and the mixture was degassed with argon for 30 seconds. The vial was sealed, and the reaction mixture was heated at 100° C. for 16 hours. The reaction was cooled, diluted with EtOAc and water, then filtered over celite, rinsing with EtOAc. The solid was washed with water, dried under vacuum, and used as is in the next reaction.

ES/MS: 443.3 (M+H⁺).

4-(8-amino-1,6-naphthyridin-2-yl)thiomorpholine 1,1-dioxide (1-93): To a vial was added 4-(8-((diphenylmethylene) amino)-1,6-naphthyridin-2-yl)thiomorpholine 1,1-dioxide (156 mg, 0.35 mmol). THF (4 mL) and HCl (2N aqueous; 1.5 mL) were added, and the mixture was stirred at rt for 15 hours. The reaction was diluted with EtOAc and water. The layers were separated, and the aqueous layer was basified with K$_2$CO$_3$ and extracted with EtOAc 2×. The combined organic layers were dried over sodium sulfate, filtered, and concentrated under reduced pressure. The crude residue used in the next reaction.

ES/MS: 279.1 (M+H⁺).

Preparation of Intermediate I-94

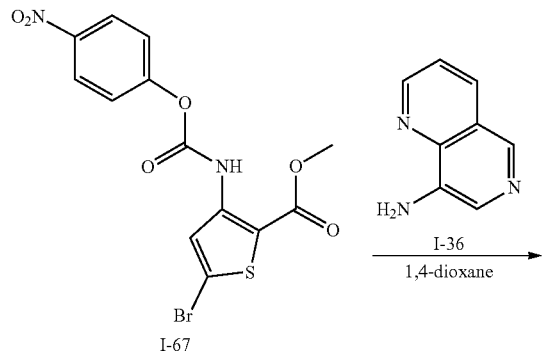

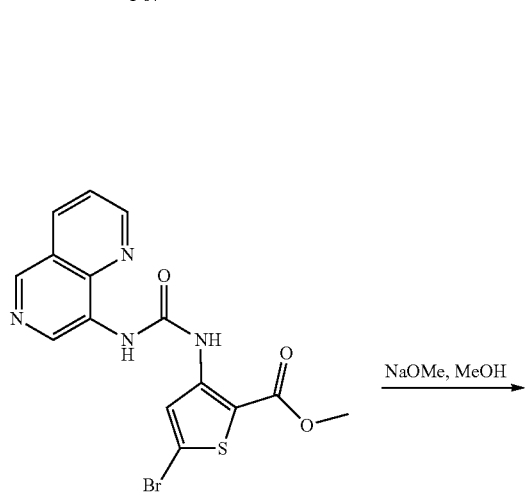

methyl 3-(3-(1,6-naphthyridin-8-yl)ureido)-5-bromothiophene-2-carboxylate: To a solution of methyl 3-amino-5-bromothiophene-2-carboxylate (I-67) (1.4 g, 3.4 mmol) in 1,4-dioxane (10 mL), was added 1,6-naphthyridin-8-amine (I-36) (600 mg, 4.1 mmol). The reaction was heated at 80° C. for 1 hour (until done by LC/MS). The reaction was cooled and diluted with 10 ml acetonitrile and filtered. The solid was dried under vacuum and used as is in the next reaction.

ES/MS: 407.1 (M+H⁺).

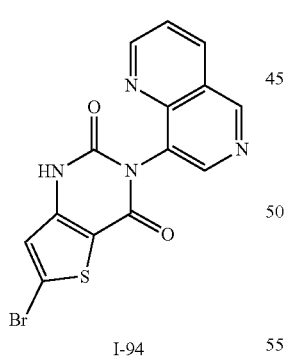

I-94

6-bromo-3-(1,6-naphthyridin-8-yl)thieno[3,2-d]pyrimidine-2,4(1H,3H)-dione (1-94): To a solution of methyl 3-(3-(1,6-naphthyridin-8-yl)ureido)-5-bromothiophene-2-carboxylate (1.1 g, 2.6 mmol) in methanol (10 mL) was added sodium methoxide (0.5 ml, 25% in methanol). The reaction was stirred for 2 hours (until complete by LC/MS) and concentrated. The residue was taken up in acetonitrile and water was added to form ppt. The mixture was filtered and rinsed with water. The solid was dried under vacuum and used as is in the next reaction.

ES/MS: 375.0 (M+H⁺).

Preparation of Intermediate I-95

I-95

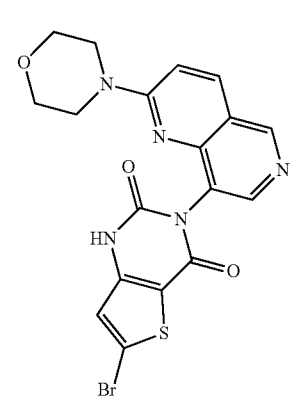

6-bromo-3-(2-methyl-1,6-naphthyridin-8-yl)thieno[3,2-d]pyrimidine-2,4(1H,3H)-dione (I-95): Prepared analogously to 1-94, substituting 1,6-naphthyridin-8-amine (1-36) with 2-methyl-1,6-naphthyridin-8-amine (I-91).

ES/MS: 389.1 (M+H⁺).

Preparation of Intermediate I-96

I-96

6-bromo-3-(2-morpholino-1,6-naphthyridin-8-yl)thieno[3,2-d]pyrimidine-2,4(1H,3H)-dione (I-96): Prepared analogously to 1-94, substituting 1,6-naphthyridin-8-amine (I-36) with 2-morpholino-1,6-naphthyridin-8-amine (I-92).

ES/MS: 460.0 (M+H⁺).

Preparation of Intermediate I-97

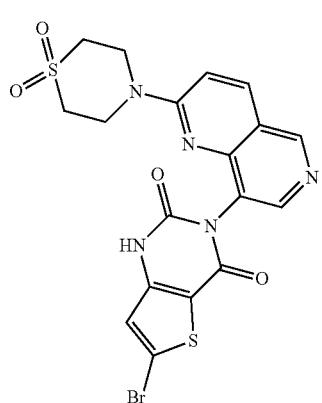

6-bromo-3-(2-(1,1-dioxidothiomorpholino)-1,6-naphthyridin-8-yl)thieno[3,2-d]pyrimidine-2,4(1H,3H)-dione (I-97): Prepared analogously to I-94, substituting 1,6-naphthyridin-8-amine (I-36) with 4-(8-amino-1,6-naphthyridin-2-yl)thiomorpholine 1,1-dioxide (I-93).
ES/MS: 540.1 (M+H$^+$).

Preparation of Intermediate I-98

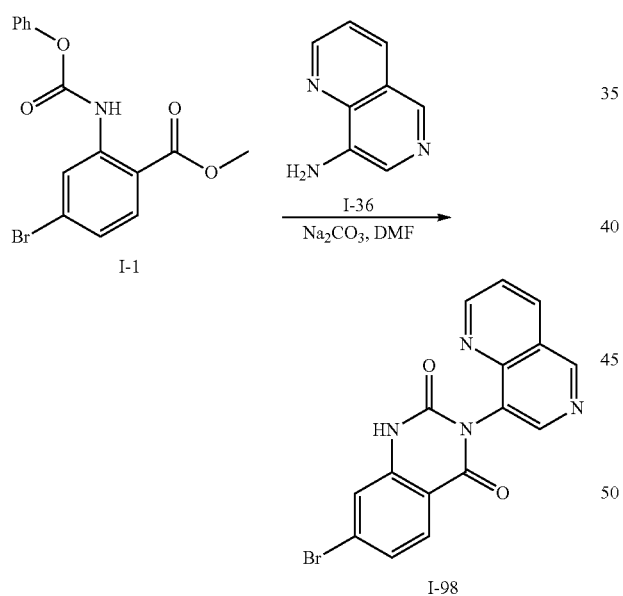

7-bromo-3-(1,6-naphthyridin-8-yl)quinazoline-2,4(1H,3H)-dione (I-98): To a solution of methyl 4-bromo-2-((phenoxycarbonyl)amino)benzoate (I-1) (500 mg, 1.4 mmol) in DMF (5 mL) was added sodium carbonate (151 mg, 1.4 mmol) followed by 1,6-naphthyridin-8-amine (I-36) (249 mg, 1.7 mmol). The reaction mixture was heated at 80° C. for 4 hours, then 1 eq of cesium carbonate was added and the temperature was increased to 100° C. Once the cyclization was complete, the mixture was cooled, diluted with water to form ppt and filtered. The solid was dried to provide the product.
ES/MS: 369.1 (M+H$^+$).

Preparation of Intermediate I-99

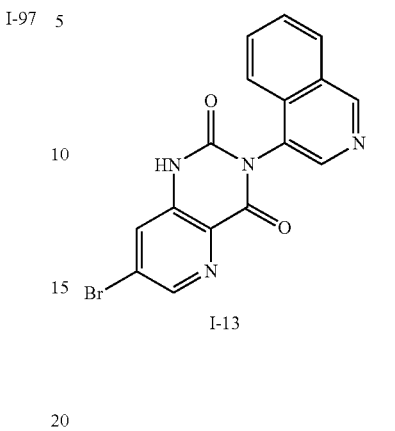

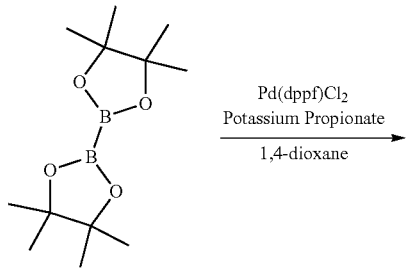

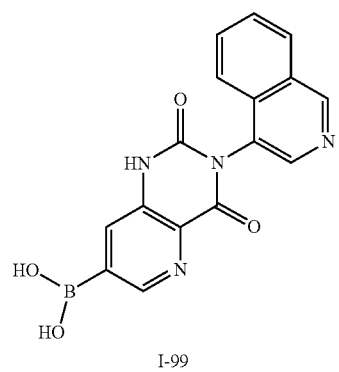

[3-(4-isoquinolyl)-2,4-dioxo-1H-pyrido[3,2-d]pyrimidin-7-yl]boronic acid (I-99): To a 40 mL vial was added 7-bromo-3-(4-isoquinolyl)-1H-pyrido[3,2-d]pyrimidine-2,4-dione (I-13) (250 mg, 0.67 mmol), Bis(pinacolato)diboron (344 mg, 1.35 mmol), [1,1'-Bis(diphenylphosphino)ferrocene]dichloropalladium(II) (50 mg, 0.06 mmol), and potassium propionate (228 mg, 2.03 mmol). The mixture was dissolved in 1,4-dioxane (8 mL), and argon was bubbled through the reaction mixture for 1 minute. The vial was sealed, and the mixture was heated at 95° C. for 16 hours. The mixture was cooled to rt, a solid formed after cooling and was collected by filtration. The solid was washed with acetonitrile and dried under vacuum to provide the product.
ES/MS: 335.0 (M+H$^+$).

Preparation of Intermediate I-100

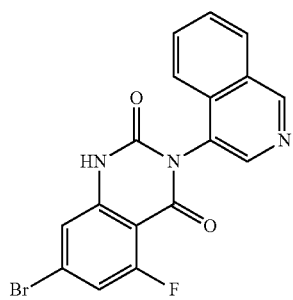

7-bromo-5-fluoro-3-(4-isoquinolyl)-1H-quinazoline-2,4-dione (I-96): Prepared analogously to 1-2, substituting methyl 2-amino-4-bromo-benzoate with methyl 2-amino-4-bromo-6-fluoro-benzoate.
ES/MS: 388.0 (M$^+$).

Preparation of Intermediate I-101

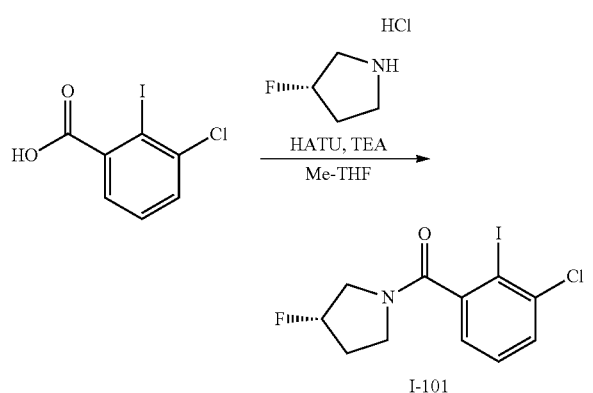

(3-chloro-2-iodo-phenyl)-[(3R)-3-fluoropyrrolidin-1-yl]methanone (I-101): To a 5 mL vial was added 3-chloro-2-iodo-benzoic acid (55 mg, 0.2 mmol), and dry Me-THF (1 mL) followed by (R)-(−)-3-fluoropyrrolidine hydrochloride (25 mg, 0.2 mmol), HATU (68 mg, 0.3 mmol) and triethylamine (0.08 mL, 0.58 mmol). The mixture was stirred for 1 hour at rt. The mixture was subsequently diluted with water (10 mL), and the layers were separated. The aqueous layer was extracted with EtOAc (1 mL), and the combined organic layers were dried over MgSO$_4$, filtered, and concentrated under reduced pressure. The crude residue was purified by silica gel chromatography (eluent: EtOAc/hexanes) to provide the product.
ES/MS: 354.0 (M$^+$).

Preparation of Intermediate I-102

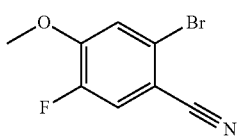

2-bromo-5-fluoro-4-methoxy-benzonitrile (I-102): To a 100 mL RBF containing 2-bromo-5-fluoro-4-hydroxy-benzonitrile (6.00 g, 27.8 mmol) was sequentially added cesium carbonate (10.9 g, 33.3 mmol), DMF (24.0 mL), and iodomethane (2.08 mL, 33.3 mmol). The reaction mixture was then stirred at 50° C. for 2 hours. The reaction mixture was then diluted with water and extracted with 3× EtOAc and the combined organic layers were then dried over MgSO$_4$, filtered, and concentrated under reduced pressure to provide the product without further purification.
ES/MS: 229.7 (M$^+$).

Preparation of Intermediate I-103

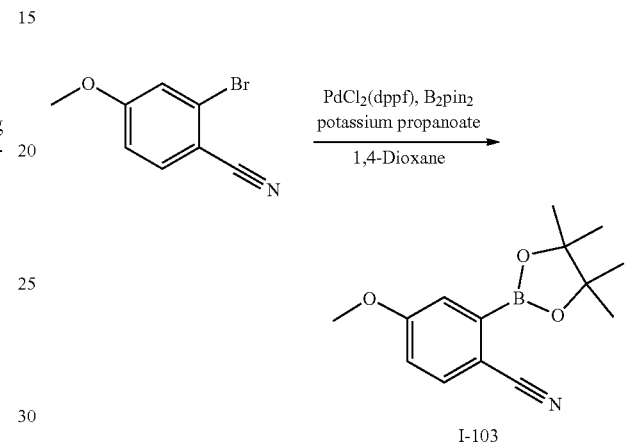

4-methoxy-2-(4,4,55-tetramethyl-1,3,2-dioxaborolan-2-yl)benzonitrile (1-103): To a flame-dried 200 mL flask was added 2-bromo-4-methoxy-benzonitrile (I g, 4.72 mmol, 1.0 equiv.), B$_2$pin$_2$ (2.40 g, 9.43 mmol, 2.0 equiv.), PdCl$_2$(dppf) (0.350 g, 0.47 mmol, 10 mol %), and potassium propionate (1.59 g, 14.1 mmol, 3.0 equiv.) followed by dioxane (28 mL, 0.17 M). The entire reaction mixture was degassed with Ar over 10 min and subsequently heated at 100° C. for 6 hours. The reaction mixture was then cooled to room temperature, concentrated under reduced pressure, and the crude material was purified by silica chromatography (eluent: EtOAc in hexanes) to provide the product.
ES/MS: 259.90 (M+H$^+$).

Preparation of Intermediate I-104

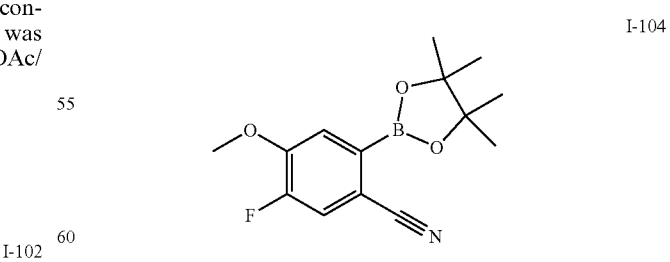

5-fluoro-4-methoxy-2-(4,4,5,5-tetramethyl-1,3,2-dioxaborolan-2-yl)benzonitrile (1-104): Prepared analogously to I-103, substituting 2-bromo-4-methoxy-benzonitrile with I-102.
ES/MS: 277.7 (M+H$^+$).

Preparation of Intermediate I-105

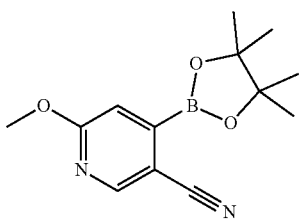

6-methoxy-4-(4,4,5,5-tetramethyl-1,3,2-dioxaborolan-2-yl)nicotinonitrile (I-105): Prepared analogously to I-103, substituting 2-bromo-4-methoxy-benzonitrile with 3-bromo-5-methoxy-pyridine-2-carbonitrile.
ES/MS: 178.90 (M+H$^+$).

Preparation of Intermediate I-106

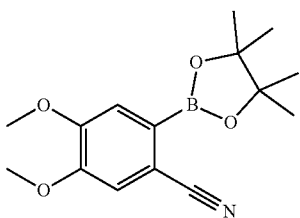

4,5-dimethoxy-2-(4,4,5,5-tetramethyl-1,3,2-dioxaborolan-2-yl)benzonitrile (I-106): Prepared analogously to I-103, substituting 2-bromo-4-methoxy-benzonitrile with 2-bromo-4,5-dimethoxy-benzonitrile.
ES/MS: 289.9 (M+H$^+$).

Preparation of Intermediate I-107

thieno[3,2-c]pyridin-7-amine (I-107): Prepared analogously to I-7, substituting 4-bromo-6-methyl-isoquinoline with 7-bromothieno[3,2-c]pyridine.
ES/MS: 150.9 (M+H$^+$).

Preparation of Intermediate I-108

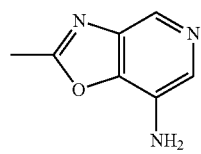

2-methyloxazolo[4,5-c]pyridin-7-amine (I-108): Prepared analogously to I-7, substituting 4-bromo-6-methyl-isoquinoline with 7-bromo-2-methyl-oxazolo[4,5-c]pyridine.
ES/MS: 168.0 (M+Na$^+$).

Preparation of Intermediate I-109

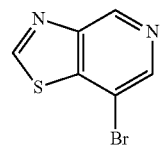

7-bromothiazolo[4,5-c]pyridine (I-109): To a 40 mL vial containing 3-amino-5-bromo-pyridine-4-thiol (750 mg, 3.66 mmol) was added zinc powder (120 mg, 1.83 mmol) and formic acid (6.00 mL). The reaction mixture was then sealed and stirred at 100° C. for 1 hour. The reaction mixture was then cooled to ambient temperature and concentrated under reduced pressure. The resulting crude residue was then purified via silica gel flash chromatography (eluent: EtOAc in hexanes) to provide the product.
ES/MS: 216.8 (M$^+$).

Preparation of Intermediate I-110

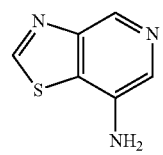

thiazolo[4,5-c]pyridin-7-amine (I—CS-5): Prepared analogously to 1-7, substituting 4-bromo-6-methyl-isoquinoline with 7-bromothiazolo[4,5-c]pyridine (I-109).
ES/MS: 151.9 (M+H$^+$).

Preparation of Intermediate I-111

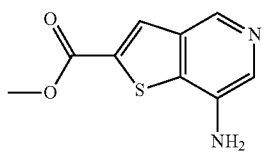

methyl 7-aminothieno[3,2-c]pyridine-2-carboxylate (I—CS-6): Prepared analogously to 1-7, substituting 4-bromo-6-methyl-isoquinoline with methyl 7-bromothieno[3,2-c]pyridine-2-carboxylate.
ES/MS: 208.9 (M+H$^+$).

Preparation of Intermediate I-112

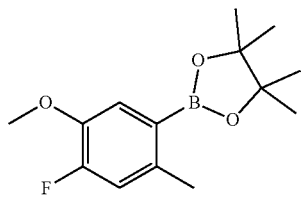

I-112

2-(4-fluoro-5-methoxy-2-methyl-phenyl)-4,4,5,5-tetramethyl-1,3,2-dioxaborolane (I-112): Prepared analogously to 1-103, substituting 2-bromo-4-methoxy-benzonitrile with 1-bromo-4-fluoro-5-methoxy-2-methyl-benzene.
ES/MS: 266.9 (M+H$^+$).

Preparation of Intermediate I-113

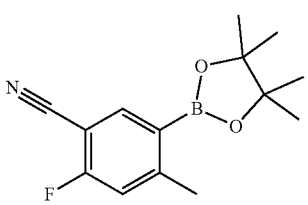

I-113

2-fluoro-4-methyl-5-(4,4,5,5-tetramethyl-1,3,2-dioxaborolan-2-yl)benzonitrile (I-113): Prepared analogously to 1-103, substituting 2-bromo-4-methoxy-benzonitrile with 5-bromo-2-fluoro-4-methyl-benzonitrile.
ES/MS: 261.9 (M+H$^+$).

Preparation of Intermediate I-114

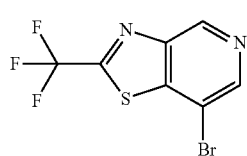

I-114

7-bromo-2-(trifluoromethyl)thiazolo[4,5-c]pyridine (I-114): Prepared analogously to 1-109, substituting formic acid with trifluoroacetic acid.
ES/MS: 284.7 (M$^+$).

Preparation of Intermediate I-115

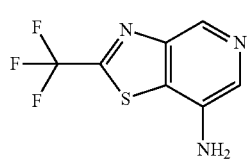

I-115

2-(trifluoromethyl)thiazolo[4,5-c]pyridin-7-amine (I-115): Prepared analogously to 1-7, substituting 4-bromo-6-methyl-isoquinoline with 7-bromo-2-(trifluoromethyl)thiazolo[4,5-c]pyridine (I-114).
ES/MS: 219.9 (M+H$^+$).

Preparation of Intermediate I-116

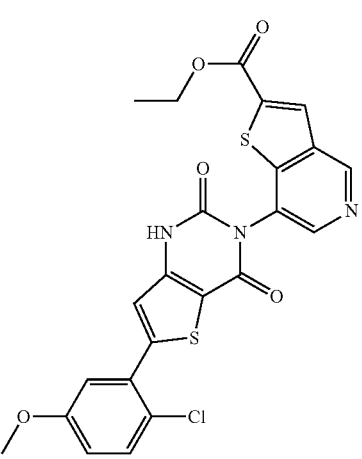

I-116 ethyl 7-[6-(2-chloro-5-methoxy-phenyl)-2,4-dioxo-1H-thieno[3,2-d]pyrimidin-3-yl]thieno[3,2-c]pyridine-2-carboxylate (I-116): Prepared analogously to Example 479, substituting methyl 5-(2-chlorophenyl)-3-(phenoxycarbonylamino)thiophene-2-carboxylate (I-30) with methyl 5-(2-chloro-5-methoxy-phenyl)-3-(phenoxycarbonylamino)thiophene-2-carboxylate (I-62), and substituting thieno[3,2-c]pyridin-7-amine (I-107) with methyl 7-aminothieno[3,2-c]pyridine-2-carboxylate (I-111).

Preparation of Intermediate I-117

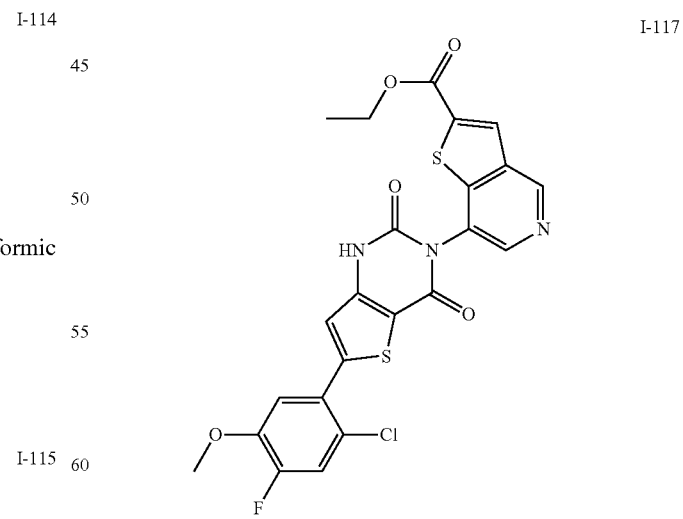

I-117 ethyl 7-[6-(2-chloro-4-fluoro-5-methoxy-phenyl)-2,4-dioxo-1H-thieno[3,2-d]pyrimidin-3-yl]thieno[3,2-c]pyridine-2-carboxylate (I-117): Prepared analogously to 1-116, substituting methyl 5-(2-chloro-5-methoxy-phenyl)-3-

(phenoxycarbonylamino)thiophene-2-carboxylate (I-62) with methyl 5-(2-chloro-4-fluoro-5-methoxy-phenyl)-3-(phenoxycarbonylamino)thiophene-2-carboxylate (I-61).

ES/MS: 531.7 (M+).

Preparation of Intermediate I-118

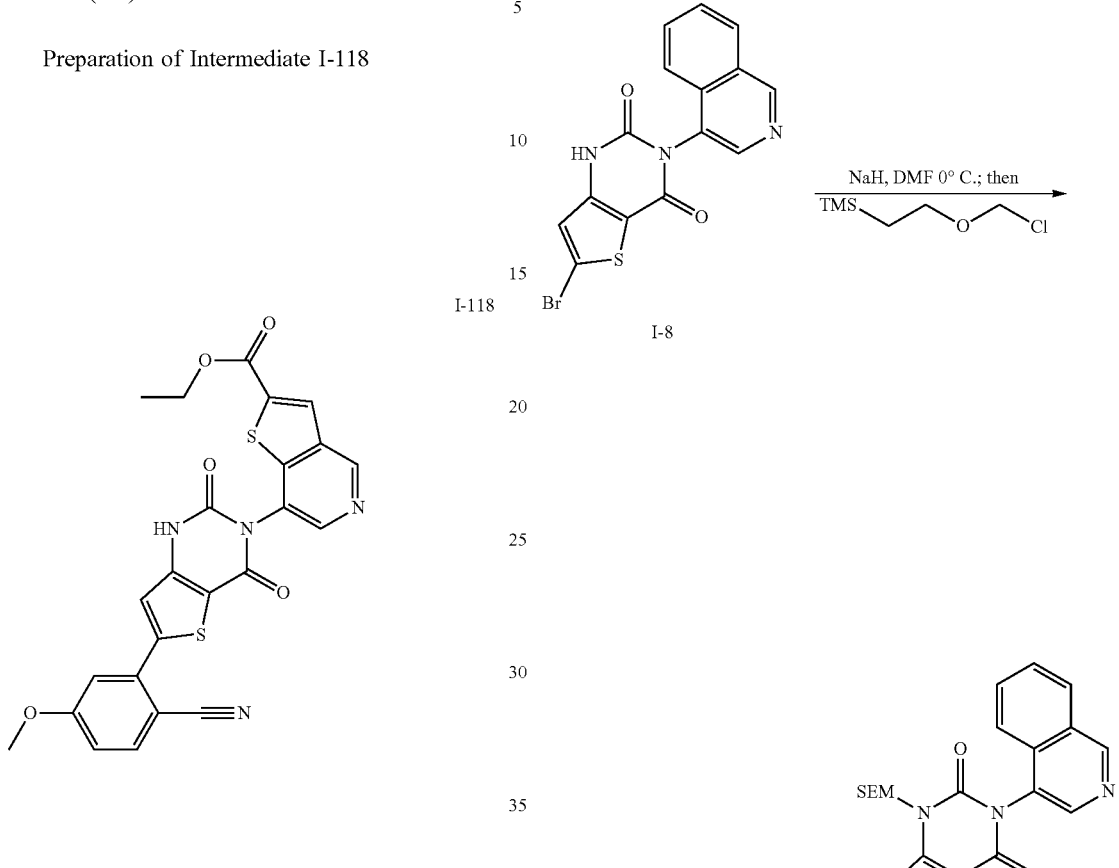

ethyl 7-[6-(2-cyano-5-methoxy-phenyl)-2,4-dioxo-1H-thieno[3,2-d]pyrimidin-3-yl]thieno[3,2-c]pyridine-2-carboxylate (I-118): Prepared analogously to 1-116, substituting methyl 5-(2-chloro-5-methoxy-phenyl)-3-(phenoxycarbonylamino)thiophene-2-carboxylate (I-62) with methyl 5-(2-cyano-5-methoxy-phenyl)-3-(phenoxycarbonylamino)thiophene-2-carboxylate (I-63).

ES/MS: 504.7 (M+H+).

Preparation of Intermediate I-119

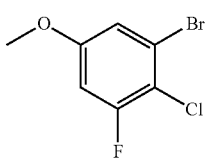

1-bromo-2-chloro-3-fluoro-5-methoxy-benzene (I-119): Prepared analogously to I-102, substituting 2-bromo-5-fluoro-4-hydroxy-benzonitrile with 3-bromo-4-chloro-5-fluoro-phenol.

$^1$H NMR (400 MHz, DMSO-d$_6$) δ 7.25 (dd, J=2.8, 1.7 Hz, 1H), 7.15 (dd, J=11.1, 2.8 Hz, 1H), 3.80 (s, 3H).

Preparation of Intermediate I-120

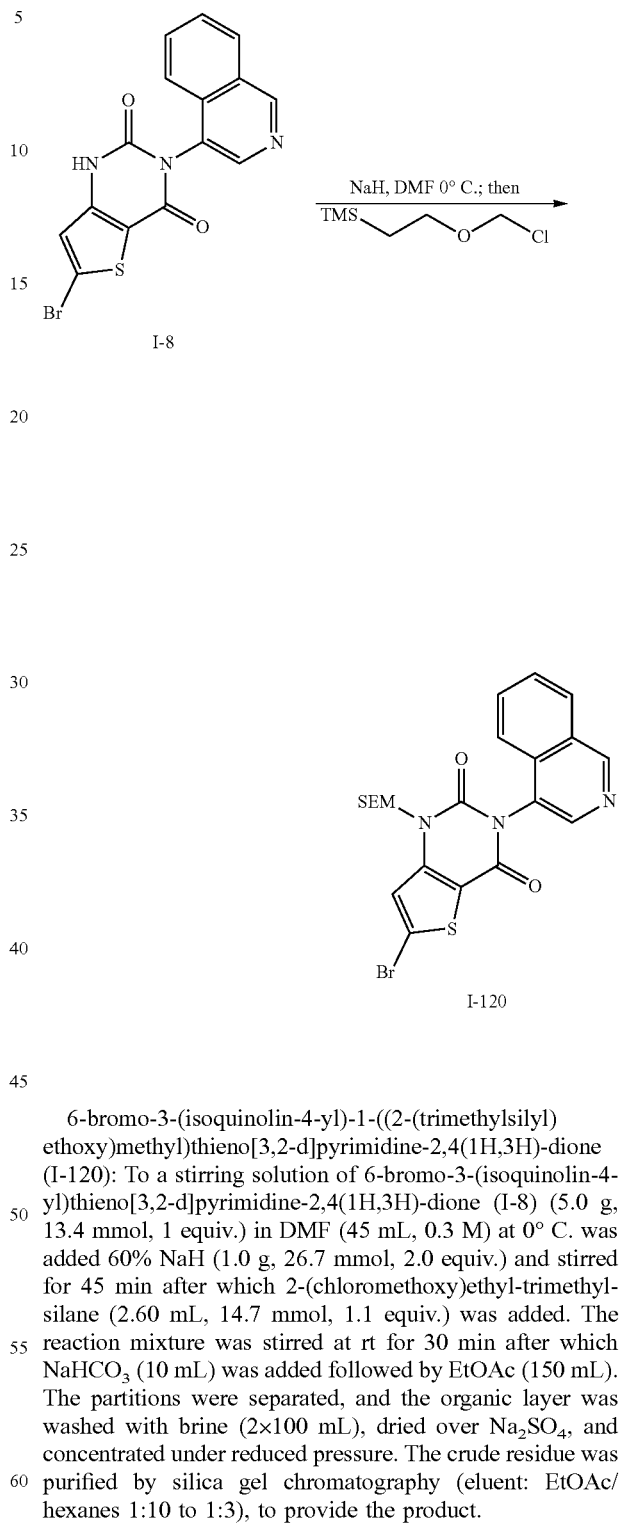

6-bromo-3-(isoquinolin-4-yl)-1-((2-(trimethylsilyl)ethoxy)methyl)thieno[3,2-d]pyrimidine-2,4(1H,3H)-dione (I-120): To a stirring solution of 6-bromo-3-(isoquinolin-4-yl)thieno[3,2-d]pyrimidine-2,4(1H,3H)-dione (I-8) (5.0 g, 13.4 mmol, 1 equiv.) in DMF (45 mL, 0.3 M) at 0° C. was added 60% NaH (1.0 g, 26.7 mmol, 2.0 equiv.) and stirred for 45 min after which 2-(chloromethoxy)ethyl-trimethyl-silane (2.60 mL, 14.7 mmol, 1.1 equiv.) was added. The reaction mixture was stirred at rt for 30 min after which NaHCO$_3$ (10 mL) was added followed by EtOAc (150 mL). The partitions were separated, and the organic layer was washed with brine (2×100 mL), dried over Na$_2$SO$_4$, and concentrated under reduced pressure. The crude residue was purified by silica gel chromatography (eluent: EtOAc/hexanes 1:10 to 1:3), to provide the product.

ES/MS: 505.70 (M+).

$^1$H NMR (400 MHz, DMSO-d$_6$) δ 9.44 (d, J=0.8 Hz, 1H), 8.56 (s, 1H), 8.32-8.23 (m, 1H), 7.87-7.71 (m, 3H), 7.71 (s, 1H), 5.49 (s, 2H), 3.67 (dd, J=8.8, 7.4 Hz, 2H), 0.96-0.87 (m, 2H), 0.02 (s, 9H).

Preparation of Intermediate I-121

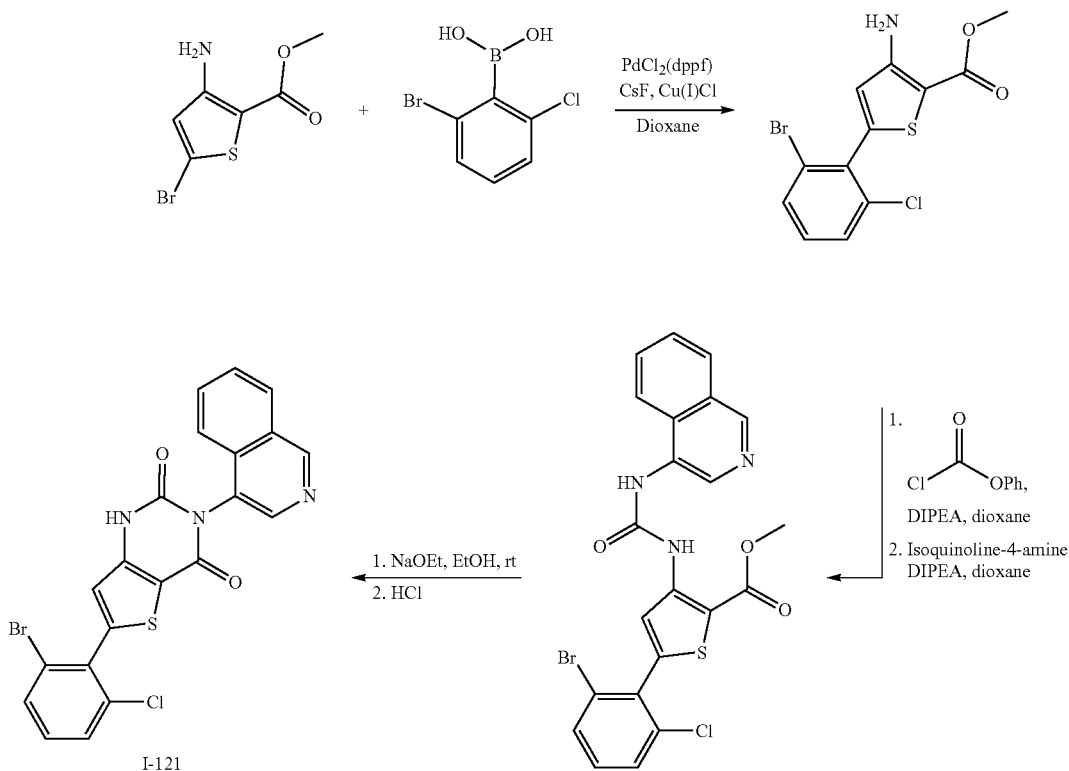

I-121

Methyl 3-amino-5-(2-bromo-6-chlorophenyl)thiophene-2-carboxylate: To a 250 mL flask was added methyl 3-amino-5-bromo-thiophene-2-carboxylate (1 g, 4.24 mmol, 1.0 equiv.), (2-bromo-6-chloro-phenyl)boronic acid (1.99 g, 8.47 mmol, 2.0 equiv.), PdCl$_2$(dppf) (0.471 g, 0.64 mmol, 15 mol %), CsF (1.29 g, 8.47 mmol, 2.0 equiv.), and CuCl (0.21 g, 2.12 mmol, 0.5 equiv.) followed by dioxane (42 mL, 0.1 M). The entire reaction mixture was degassed with Ar over 5 min, sealed and heated at 120° C. for 6 hours, after which an additional 1 equiv. of boronic acid was added, and stirred for an additional 6 h. The reaction mixture was then cooled to room temperature and concentrated under reduced pressure. The crude material was purified by silica chromatography (eluent: EtOAc in hexanes) to provide the product.

ES/MS: 346.0 (M$^+$).

$^1$H NMR (400 MHz, CDCl$_3$) δ 7.58 (d, J=8.2 Hz, 1H), 7.44 (d, J=8.2 Hz, 1H), 7.24-7.13 (m, 1H), 6.46 (s, 1H), 5.36-4.40 (m, 2H) 3.93-3.79 (s, 3H).

Methyl 5-(2-bromo-6-chlorophenyl)-3-(3-(isoquinolin-4-yl)ureido)thiophene-2-carboxylate: To a solution of methyl 3-amino-5-(2-bromo-6-chlorophenyl)thiophene-2-carboxylate (0.45 g, 1.3 mmol, 1.0 equiv.) in dry dioxane (5.7 mL, 0.23 M) was added DIPEA (0.46 mL, 2.6 mmol, 2.0 equiv.) followed by phenyl chloroformate (0.26 mL, 2.0 mmol, 1.5 equiv). The reaction mixture was heated at 70° C. for 3 h after which isoquinolin-4-amine (0.23 g, 1.5 mmol, 1.2 equiv.) was added, followed by additional DIPEA (0.46 mL, 2.6 mmol, 2.0 equiv.) The reaction mixture was refluxed (dioxane) and stirred for an additional 3 h. The entire reaction mixture was cooled to ambient temperature and concentrated under reduced pressure. EtOAc (5 mL) was then added followed by H$_2$O (20 mL) which formed a precipitate. The solid was collected via filtration, and washed with additional H$_2$O (10 mL), and dried to deliver intermediate methyl 5-(2-bromo-6-chlorophenyl)-3-(3-(isoquinolin-4-yl)ureido)thiophene-2-carboxylate which was used to the next step without further purification.

ES/MS: 516.0 (M$^+$).

6-(2-Bromo-6-chlorophenyl)-3-(isoquinolin-4-yl)thieno[3,2-d]pyrimidine-2,4(1H,3H)-dione (I-121): To a suspension of methyl 5-(2-bromo-6-chlorophenyl)-3-(3-(isoquinolin-4-yl)ureido)thiophene-2-carboxylate (732 mg, 1.42 mmol, 1.0 equiv.) in ethanol (4.4 mL, 0.32 M) was added a solution of sodium ethoxide (21% in ethanol) (0.8 mL, 1.5 equiv.) at room temperature, and the reaction mixture was stirred at room temperature for 1 h. The reaction mixture was concentrated under reduced pressure after which EtOAc (10 mL) was added followed by 1M HCl (30 mL), which formed a precipitate. The solid was collected via filtration to deliver the product as an HCl salt.

ES/MS: 484.9 (M$^+$).

Preparation of Intermediate I-122

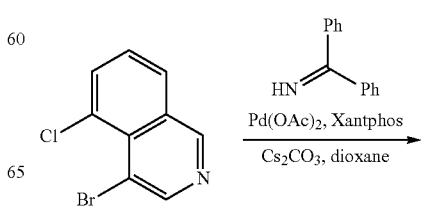

Preparation of Intermediate I-123

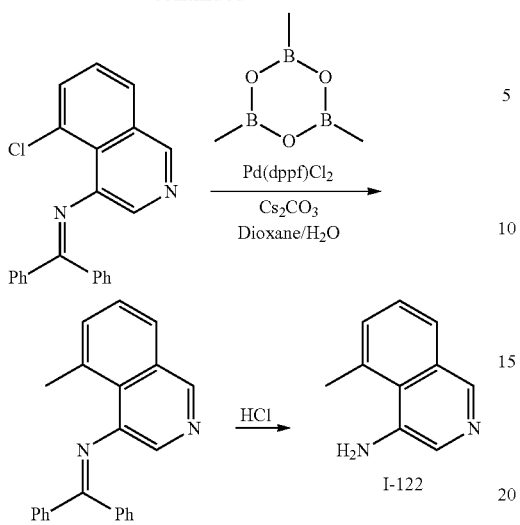

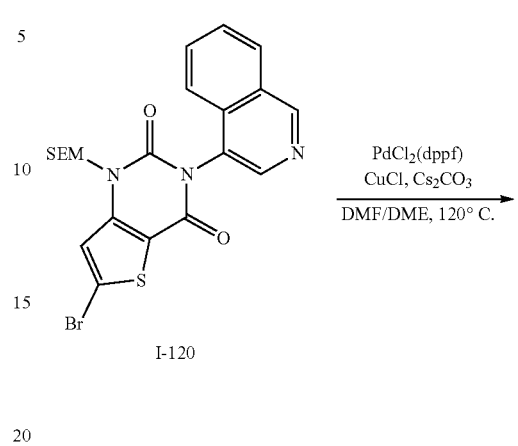

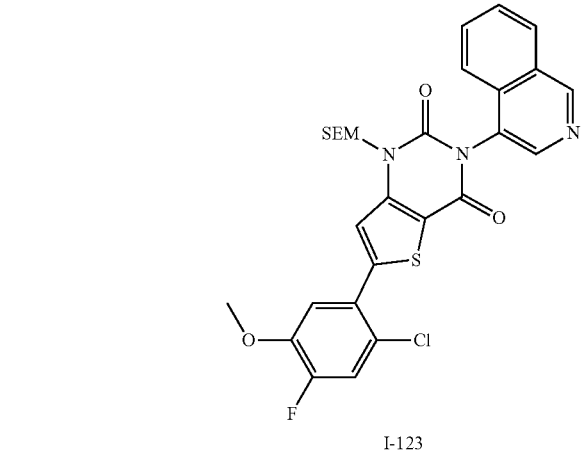

N-(5-chloro-4-isoquinolyl)-1,1-diphenyl-methanimine: To a flame-dried 100 mL flask was added 4-bromo-5-chloro-isoquinoline (1.0 g, 4.12 mmol, 1.0 equiv.), palladium(II) acetate (93 mg, 0.41 mmol, 10 mol %), Xantphos (477 mg, 0.83 mmol, 20 mol %), cesium carbonate (1.3 g, 4.1 mmol, 1.0 equiv.), and benzophenone imine (900 mg, 4.95 mmol, 0.83 mL, 1.2 equiv.) followed by dioxane (18 mL, 0.2 M). The entire reaction mixture was degassed with Ar over 10 min and subsequently heated at 90° C. for 6 hours. The reaction mixture was then cooled to room temperature, concentrated under reduced pressure, and the crude material was purified by silica chromatography (eluent: EtOAc in hexanes (1:5)) to provide the product.

ES/MS: 342.90 (M+).

N-(5-methylisoquinolin-4-yl)-1,1-diphenylmethanimine: To a 10 mL microwave vial containing a stir bar was added N-(5-chloro-4-isoquinolyl)-1,1-diphenyl-methanimine (214 mg, 0.63 mmol, 1.0 equiv.), PdCl$_2$(dppf) (46.3 mg, 0.63 mmol, 10 mol %), cesium carbonate (173 mg, 0.13 mmol, 2.0 equiv.), and trimethylboroxine (0.35 mL, 2.5 mmol, 4.0 equiv.) followed by dioxane/H$_2$O (1.6 mL, 5% water, 0.4 M). The reaction mixture was sealed with Teflon, degassed under Ar (5 min), and heated to 140° C. under microwave irradiation for 20 min. The crude product was filtered through celite and used without further purification to the next step.

ES/MS: 322.90 (M+H+).

5-methylisoquinolin-4-amine (I-122): To a stirring solution of crude N-(5-methylisoquinolin-4-yl)-1,1-diphenyl-methanimine (190 mg, 0.59 mmol) in dioxane (0.5 mL, 1.2 M), was added 4 M HCl (0.2 mL) followed by 0.1 mL of H$_2$O. The reaction mixture stirred at rt for 2 h, after which EtOAc (10 mL) and H$_2$O (10 mL) were added. The layers were separated, and the pH of the aqueous layer was basified using sat. NaHCO$_3$. EtOAc (10 mL) was subsequently added, the layers separated, and the aqueous layer was extracted with EtOAC (2×5 mL). The organic layers were combined, washed with brine (15 mL), and dried to deliver the target intermediate 5-methylisoquinolin-4-amine which was used without further purification.

ES/MS: 159.0 (M+H+).

6-(2-chloro-4-fluoro-5-methoxy phenyl)-3-(isoquinolin-4-yl)-1-((2-(trimethylsilyl)ethoxy)methyl)thieno[3,2-d]pyrimidine-2,4(1H,3H)-dione (I-123): To a 10 mL microwave vial (Biotage #351521) containing a stir bar was added 6-bromo-3-(isoquinolin-4-yl)-1-((2-(trimethylsilyl)ethoxy)methyl)thieno[3,2-d]pyrimidine-2,4(1H,3H)-dione (I-120) (100 mg, 0.2 mmol, 1.0 equiv.), (2-chloro-4-fluoro-5-methoxy-phenyl)boronic acid (63 mg, 0.3 mmol, 1.5 equiv.), PdCl$_2$(dppf) (22 mg, 15 mol %), and Cu(I)Cl (20 mg, 0.2 mmol, 1.0 equiv.) followed by Cs$_2$CO$_3$ (194 mg, 0.6 mmol, 3.0 equiv.). DMF/DME (1:9) was added (4.0 mL), and the reaction mixture was sealed with Teflon, degassed under Ar (5 min), and heated to 120° C. under microwave irradiation for 20 min. The crude product was diluted in acetonitrile/water/trifluoroacetic acid (1.5 mL; 5:1:0.2), filtered through an acrodisc, and purified directly by RP-HPLC (0.1% TFA-ACN in 0.1% TFA Water, Column: Gemini 5 μM, NX-C18 110 Angstrom, 250×21.2 mm) to give the product.

ES/MS: 584.80 (M+).

$^1$H NMR (400 MHz, DMSO-d$_6$) δ 9.48 (s, 1H), 8.61 (s, 1H), 8.34-8.27 (m, 1H), 7.89-7.74 (m, 4H), 7.74 (d, J=11.1 Hz, 1H), 7.50 (d, J=8.8 Hz, 1H), 5.58 (s, 2H), 3.97 (s, 3H), 3.71 (dd, J=8.7, 7.5 Hz, 2H), 0.92 (dd, J=8.8, 7.3 Hz, 2H), 0.04 (s, 9H).

Preparation of Intermediate I-124

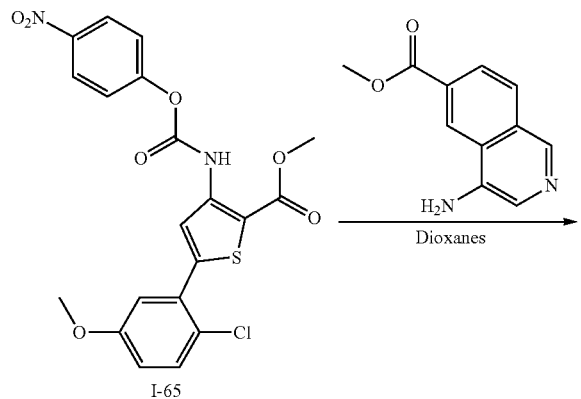

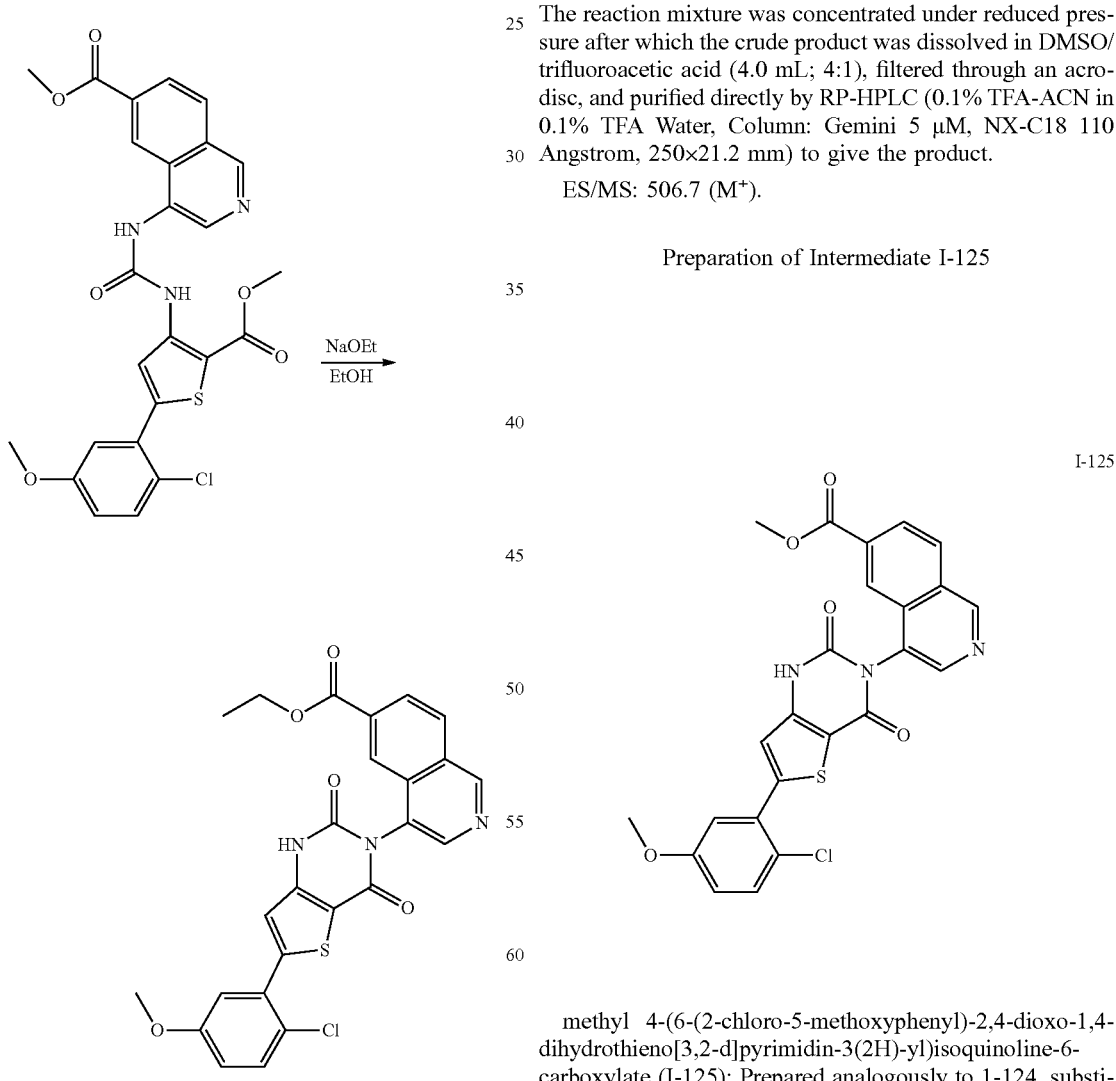

methyl 4-(3-(5-(2-chloro-5-methoxyphenyl)-2-(methoxycarbonyl)thiophen-3-yl)ureido)isoquinoline-6-carboxylate: To a stirring solution of methyl 5-(2-chloro-5-methoxyphenyl)-3-(((4-nitrophenoxy)carbonyl)amino)thiophene-2-carboxylate (I-65) (592 mg, 1.42 mmol, 1.0 equiv.) in dioxanes (5.7 mL, 0.30 M) was added methyl 4-aminoisoquinoline-6-carboxylate (344 mg, 1.7 mmol, 1.2 equiv.). The reaction mixture was heated to 95° C. and stirred overnight. The reaction mixture was cooled to rt and concentrated under reduced pressure to deliver intermediate methyl 4-(3-(5-(2-chloro-5-methoxyphenyl)-2-(methoxycarbonyl)thiophen-3-yl)ureido)isoquinoline-6-carboxylate which was used to the next step without further purification.

ES/MS: 525.7 ($M^+$).

ethyl 4-[6-(2-chloro-5-methoxy-phenyl)-2,4-dioxo-1H-thieno[3,2-d]pyrimidin-3-yl]isoquinoline-6-carboxylate (I-124): To a suspension of methyl 4-[[5-(2-chloro-5-methoxy-phenyl)-2-methoxycarbonyl-3-thienyl]carbamoylamino]isoquinoline-6-carboxylate (745 mg, 1.42 mmol, 1.0 equiv.) in ethanol (4.43 mL, 0.32 M) was added a solution of 25% sodium ethoxide (0.67 mL, 2.1 mmol, 1.5 equiv.) and the reaction mixture stirred at room temperature for 2 h. The reaction mixture was concentrated under reduced pressure after which the crude product was dissolved in DMSO/trifluoroacetic acid (4.0 mL; 4:1), filtered through an acrodisc, and purified directly by RP-HPLC (0.1% TFA-ACN in 0.1% TFA Water, Column: Gemini 5 μM, NX-C18 110 Angstrom, 250×21.2 mm) to give the product.

ES/MS: 506.7 ($M^+$).

Preparation of Intermediate I-125 methyl 4-(6-(2-chloro-5-methoxyphenyl)-2,4-dioxo-1,4-dihydrothieno[3,2-d]pyrimidin-3(2H)-yl)isoquinoline-6-carboxylate (I-125): Prepared analogously to I-124, substituting NaOEt in EtOH with NaOMe in MeOH.

ES/MS: 493.7 ($M^+$).

Preparation of Intermediate I-126

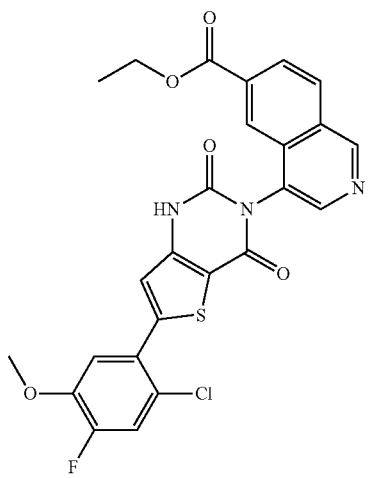

ethyl 4-(6-(2-chloro-4-fluoro-5-methoxyphenyl)-2,4-dioxo-1,4-dihydrothieno[3,2-d]pyrimidin-3(2H)-yl)isoquinoline-6-carboxylate (I-126): Prepared analogously to 1-124, substituting I-65 with I-66.

ES/MS: 526.7 (M+).

Preparation of Intermediate I-127

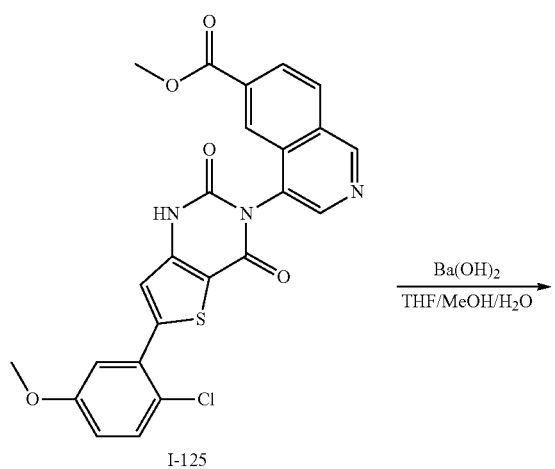

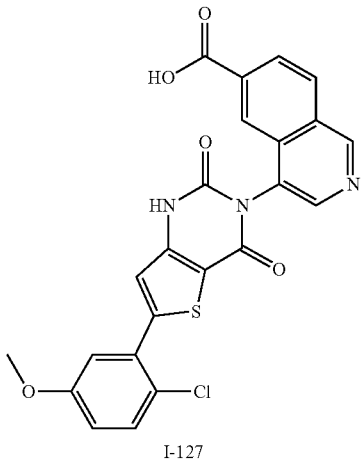

4-(6-(2-chloro-5-methoxyphenyl)-2,4-dioxo-1,4-dihydrothieno[3,2-d]pyrimidin-3(2H)-yl)isoquinoline-6-carboxylic acid (I-127): To a stirring solution of methyl 4-[6-(2-chloro-5-methoxy-phenyl)-2,4-dioxo-1H-thieno[3,2-d]pyrimidin-3-yl]isoquinoline-6-carboxylate (I-125) (30 mg, 0.049 mmol, 1.0 equiv.) in THF/MeOH/H$_2$O (0.5 mL, 4:1:1) was added barium hydroxide (3.3 mg, 0.17 mmol, 3.5 equiv.). The reaction mixture was stirred overnight, quenched with 1 M HCl (0.2 mL), and concentrated to deliver the product which was used to the next step without further purification.

ES/MS: 479.9 (M+).

Preparation of Intermediate I-128

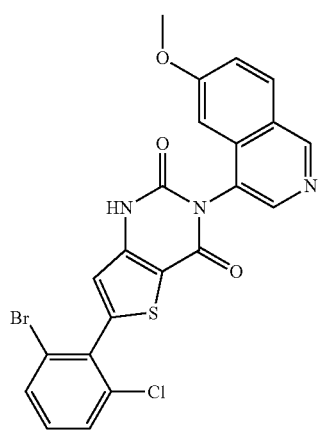

6-(2-bromo-6-chloro-phenyl)-3-(6-methoxy-4-isoquinolyl)-1H-thieno[3,2-d]pyrimidine-2,4-dione (I-128): Prepared analogously to 1-121, substituting isoquinolin-4-amine with 6-methoxyisoquinolin-4-amine.

ES/MS: 515.9 (M+).

Preparation of Intermediate I-129

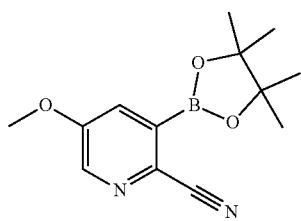

I-129

5-methoxy-3-(4,4,5,5-tetramethyl-1,3,2-dioxaborolan-2-yl)pyridine-2-carbonitrile (I-129): Prepared analogously to 1-103, substituting 2-bromo-4-methoxy-benzonitrile with 3-bromo-5-methoxy-pyridine-2-carbonitrile.
ES/MS: 178.90 (M+).

Preparation of Intermediate I-130

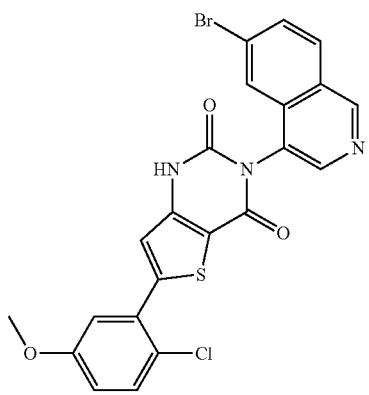

I-130

3-(7-bromonaphthalen-1-yl)-6-(2-chloro-5-methoxyphenyl)thieno[3,2-d]pyrindine-2,4(1H,3H)-dione (I-130): Prepared analogously to I-124, substituting methyl 4-aminoisoquinoline-6-carboxylate with 7-bromonaphthalen-1-amine (I-134).
ES/MS: 493.7 (M+).

Preparation of Intermediate I-131

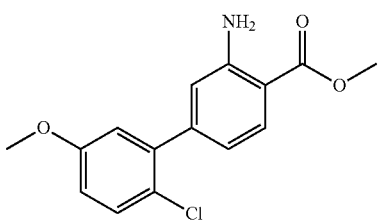

I-131 methyl 3-amino-2'-chloro-5'-methoxy-[1,1'-biphenyl]-4-carboxylate (I-131): Prepared analogously to I-27, substituting (2-chlorophenyl)boronic acid with (2-chloro-5-methoxyphenyl)boronic acid.

Preparation of Intermediate I-132

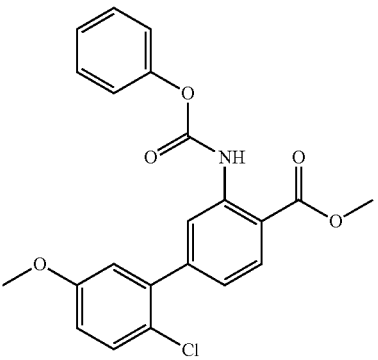

I-132 methyl 2'-chloro-5'-methoxy-3-((phenoxycarbonyl)amino)-[1,1'-biphenyl]-4-carboxylate (I-132): Prepared analogously to 1-28, substituting I-27 with methyl 3-amino-2'-chloro-5'-methoxy-[1,1'-biphenyl]-4-carboxylate (I-131).

Preparation of Intermediate I-133

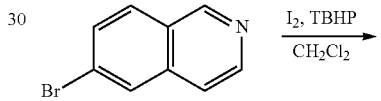

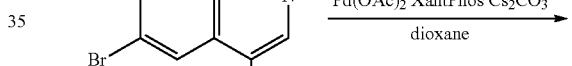

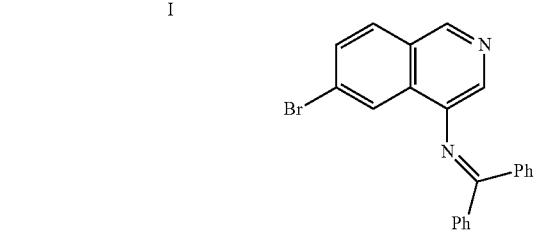

I-133

6-bromo-4-iodoisoquinoline: To a 100 mL RBF of 6-bromo-isoquinoline (2.0 g, 9.6 mmol) in 10 mL of dichloroethane was added iodine (4.88 g, 19.2 mmol), and tert-butyl hydroperoxide (70% in water, 3.71 mL). The reaction mixture was heated at 80° C. for 16 hours. The reaction was then cooled to rt, then sat. $Na_2S_2SO_4$ was added and stirred vigorously for 15 min. The mixture was diluted with DCM (30 mL) and the organic layers were separated. The aqueous layer was extracted with DCM (2×20 mL) and the combined organic layers were dried over $MgSO_4$, filtered, and concentrated under reduced pressure. The crude residue was purified by silica gel chromatography (eluent. EtOAc/hexanes) to provide the product.
ES/MS: 333.6 (M+H+).

N-(6-bromoisoquinolin-4-yl)-1,1-diphenylmethanimine (1-133): To a dram vial was added 6-bromo-4-iodo-isoquinoline (4.6 g, 13.8 mmol), diphenylmethanimine (3.0 g, 16.5 mmol), Pd(OAc)$_2$ (310 mg, 1.38 mmol), 9,9-Dimethyl-4,5- bis(diphenylphosphino)xanthene (XantPhos) (1.6 g, 2.75 mmol) and cesium carbonate (4.5 g, 13.8 mmol). Dioxane (20 mL) was added, and the mixture was degassed with argon for 30 seconds. The vial was sealed, and the reaction mixture was heated at 80° C. for 16 hours. The mixture was subsequently concentrated under reduced pressure. The crude residue was purified by silica gel chromatography (eluent: EtOAc/hexanes) to provide the product.
ES/MS: 388.7 (M+).

Preparation of Intermediate I-134

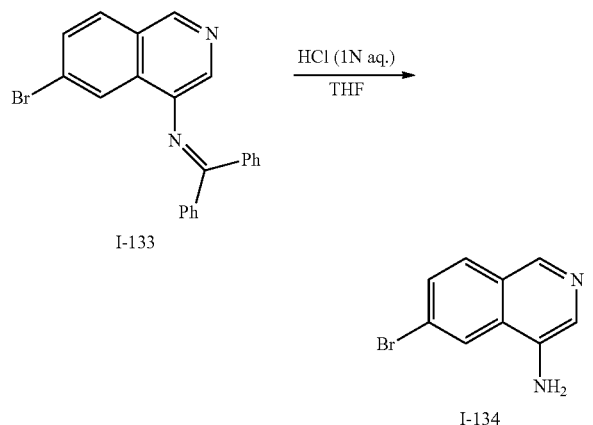

6-bromoisoquinolin-4-amine (I-134): To a dram vial was added N-(6-bromoisoquinolin-4-yl)-1,1-diphenylmethanimine (1-133) (0.5 g, 1.3 mmol). THF (10 mL) and HCl (2N aqueous; 6.4 mL, 12.8 mmol) were added, and the mixture was stirred at rt for 2 hours. The reaction was diluted with EtOAc (30 mL), and the mixture was basified with KOH (1M aqueous, 5 mL). The layers were separated, and the aqueous layer was extracted with EtOAc (2×20 mL). The combined organic layers were dried over MgSO4, filtered, and concentrated under reduced pressure. The crude residue was purified by silica gel chromatography (eluent: EtOAc/hexanes, then MeOH/EtOAc) to provide the product.
ES/MS: 223.8 (M+).

Preparation of Intermediate I-135

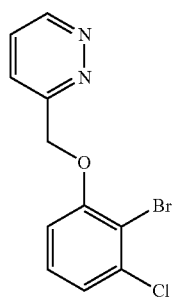

3-[(2-bromo-3-chloro-phenoxy)methyl]pyridazine (1-135): Prepared analogously to I-46, substituting 4-(chloromethyl)thiazole hydrochloride with 3-(bromomethyl)pyridazine hydrobromide.
ES/MS: 301.0 (M+).

Preparation of Intermediate I-136

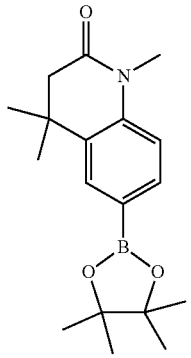

1,4,4-trimethyl-6-(4,4,5,5-tetramethyl-1,3,2-dioxaborolan-2-yl)-3H-quinolin-2-one (1-136): Prepared analogously to 1-58, substituting 6-bromo-7,8-dimethyl-[1,2,4]triazolo[1,5-a]pyridine with 6-bromo-1,4,4-trimethyl-3H-quinolin-2-one.
ES/MS: 316.0 (M+H+).

Preparation of Intermediate I-137

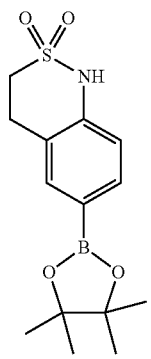

6-(4,4,5,5-tetramethyl-1,3,2-dioxaborolan-2-yl)-3,4-dihydro-1H-benzo[c][1,2]thiazine 2,2-dioxide (1-137): Prepared analogously to 1-58, substituting 6-bromo-7,8-dimethyl-[1,2,4]triazolo[1,5-a]pyridine with 6-bromo-3,4-dihydro-1H-benzo[c][1,2]thiazine 2,2-dioxide.
ES/MS: 310.0 (M+H+).

Preparation of Intermediate I-138

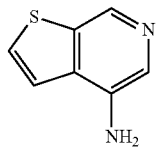

541

Thieno[2,3-c]pyridin-4-amine (I-138): Prepared analogously to 1-7, substituting 4-bromo-6-methyl-isoquinoline with 4-bromothieno[2,3-c]pyridine.

ES/MS: 151.0 (M+H$^+$).

Preparation of Intermediate I-139

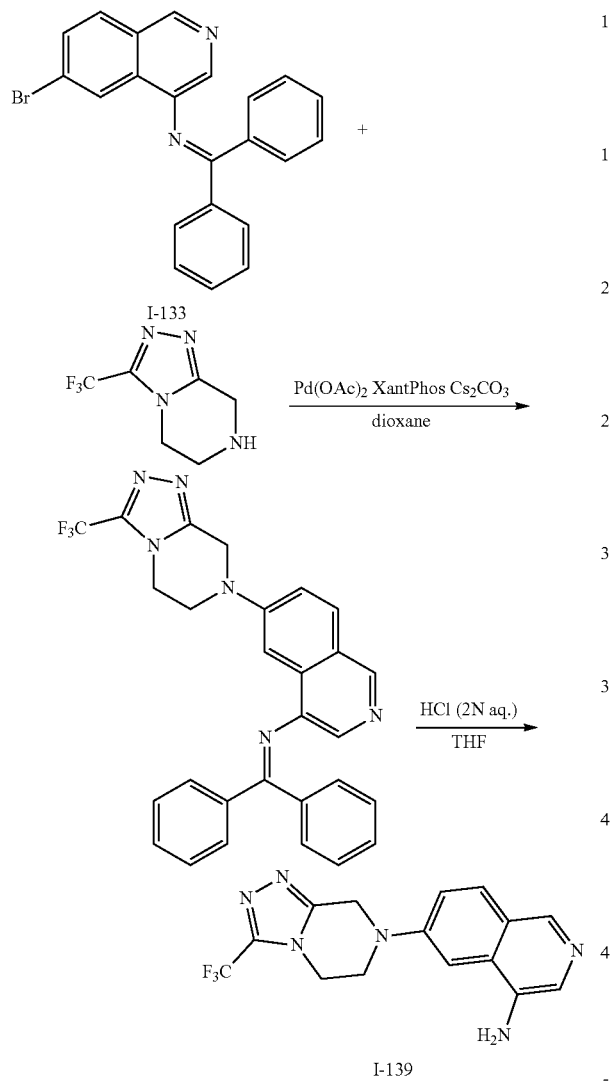

6-(3-(trifluoromethyl)-5,6-dihydro-[1,2,4]triazolo[4,3-a]pyrazin-7(8H)-yl)isoquinolin-4-amine (I-139): To a microwave vial was added N-(7-bromo-1-naphthyl)-1,1-diphenyl-methanimine (300 mg, 0.78 mmol), 3-(trifluoromethyl)-5,6,7,8-tetrahydro-[1,2,4]triazolo[4,3-a]pyrazine (224 mg, 1.16 mmol), Pd(OAc)$_2$ (17.4 mg, 0.08 mmol), 9,9-Dimethyl-4,5-bis(diphenylphosphino)xanthene (XantPhos) (90 mg, 0.16 mmol) and cesium carbonate (253 mg, 0.78 mmol). Dioxane (3 mL) was added, and the mixture was degassed with argon for 1 minute. The vial was sealed, and the reaction mixture was heated at 100° C. for 16 hours. The mixture was subsequently concentrated under reduced pressure. The crude residue was purified by silica gel chromatography (eluent: EtOAc/hexanes) to provide the intermediate imine, 1,1-diphenyl-N-(6-(3-(trifluoromethyl)-5,6-dihydro-[1,2,4]triazolo[4,3-a]pyrazin-7(8H)-yl)isoquinolin-4-yl)metha-

542 nimine [ES/MS: 498.9 (M+H$^+$)]. To a vial was added the 1,1-diphenyl-N-(6-(3-(trifluoromethyl)-5,6-dihydro-[1,2,4]triazolo[4,3-a]pyrazin-7(8H)-yl)isoquinolin-4-yl)methanimine intermediate (129 mg, 0.26 mmol). THF (4 mL) and HCl (2N aqueous, 1.5 mL) were added, and the mixture was stirred at rt for 2 hours. The reaction was diluted with EtOAc and water. The layers were separated, and the aqueous layer was basified with K$_2$CO$_3$ and extracted with EtOAc (2×10 mL). The combined organic layers were dried over sodium sulfate, filtered, and concentrated under reduced pressure to provide the product.

ES/MS: 334.9 (M+H$^+$).

Preparation of Intermediate I-140

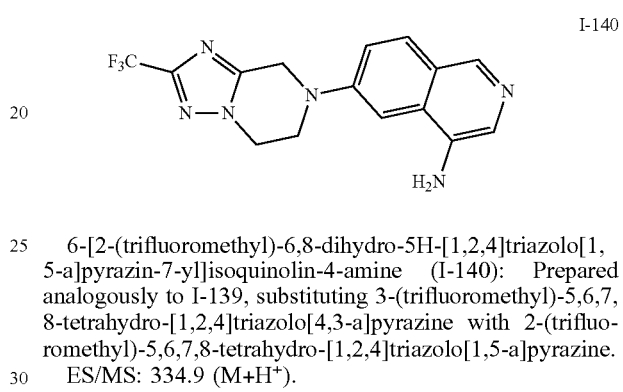

6-[2-(trifluoromethyl)-6,8-dihydro-5H-[1,2,4]triazolo[1,5-a]pyrazin-7-yl]isoquinolin-4-amine (I-140): Prepared analogously to I-139, substituting 3-(trifluoromethyl)-5,6,7,8-tetrahydro-[1,2,4]triazolo[4,3-a]pyrazine with 2-(trifluoromethyl)-5,6,7,8-tetrahydro-[1,2,4]triazolo[1,5-a]pyrazine.

ES/MS: 334.9 (M+H$^+$).

Preparation of Intermediate I-141

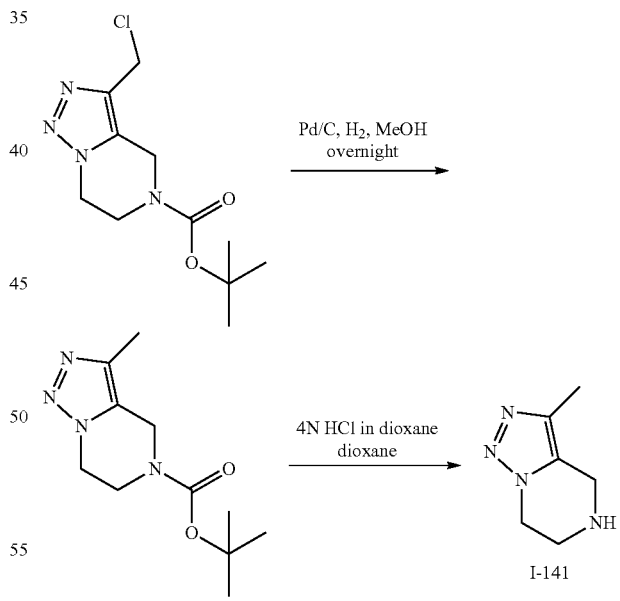

tert-butyl 3-methyl-6,7-dihydro-4H-triazolo[1,5-a]pyrazine-5-carboxylate: To a solution of tert-butyl 3-(chloromethyl)-6,7-dihydro-4H-triazolo[1,5-a]pyrazine-5-carboxylate (1 g, 3.67 mmol) in methanol (30 mL) was added 10% palladium on carbon (0.6 g) at room temperature. The mixture was stirred under hydrogen at 1 atm overnight and then filtered and concentrated under reduced pressure to give the desired product.

ES/MS: 239.0 (M+H$^+$).

¹H NMR (400 MHz, CDCl₃) δ 4.79 (s, 2H), 4.58 (s, 2H), 4.12 (s, 2H), 2.52 (s, 3H), 1.53 (s, 9H).

3-methyl-4,5,6,7-tetrahydrotriazolo[1,5-a]pyrazine (I-141): To a solution of tert-butyl 3-methyl-6,7-dihydro-4H-triazolo[1,5-a]pyrazine-5-carboxylate in dioxane (5 mL) was added 7 mL 4N HCl in dioxane. The resulting mixture was stirred at room temperature for 6 h. The solvent was evaporated under reduced pressure. The residue was diluted with water (30 mL), basified with Na₂CO₃, and extracted with DCM (2×50 mL). The combined extract was washed with water (2×50 mL) and brine (2×50 mL), dried over anhydrous Na₂SO₄, then filtrated, and the solvent was evaporated under reduced pressure to give the title compound.

¹H NMR (400 MHz, CDCl₃) δ 4.37-4.30 (m, 2H), 4.05 (s, 2H), 3.34-3.26 (m, 2H), 2.27 (s, 3H).

Preparation of Intermediate I-142

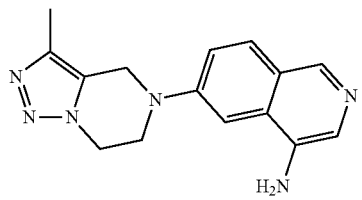

I-142

6-(3-methyl-6,7-dihydro-4H-triazolo[1,5-a]pyrazin-5-yl)isoquinolin-4-amine (I-142): Prepared analogously to 1-139, substituting 3-(trifluoromethyl)-5,6,7,8-tetrahydro-[1,2,4]triazolo[4,3-a]pyrazine with 3-methyl-4,5,6,7-tetrahydrotriazolo[1,5-a]pyrazine (1-141).
ES/MS: 281.0 (M+H⁺).

Preparation of Intermediate I-143

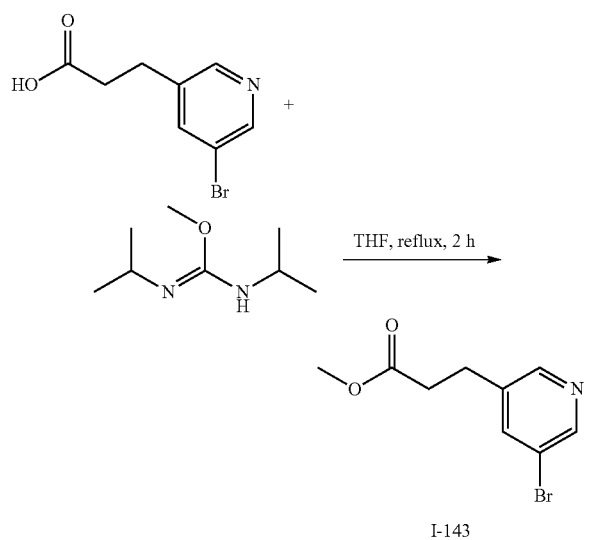

Methyl 3-(5-bromo-3-pyridyl)propanoate (I-143): To a solution of 3-(5-bromo-3-pyridyl)propanoic acid (500 mg, 2.17 mmol) in THF (25 mL) was added 1,3-diisopropyl-2-methyl-isourea (0.79 mL, 4.35 mmol). The reaction mixture was refluxed for 2 hours. The reaction mixture was then concentrated under reduced pressure. The concentrate was taken up in ethyl acetate (20 mL) and washed with water (20 mL) and saturated aqueous sodium bicarbonate solution (20 mL). The organic phase was dried over magnesium sulfate and concentrated under vacuum. The product obtained was used for subsequent reaction without further purification.
ES/MS: 245.9 (M+H⁺).

Preparation of Intermediate I-144

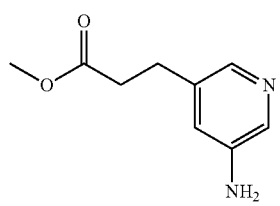

I-144

Methyl 3-(5-amino-3-pyridyl)propanoate (1-144): Prepared analogously to I-7, substituting 4-bromo-6-methyl-isoquinoline with methyl 3-(5-bromo-3-pyridyl)propanoate (I-143).
ES/MS: 181.0 (M+H⁺).

Preparation of Intermediate I-145

I-145

Ethyl 4-aminothieno[2,3-c]pyridine-2-carboxylate (I-145): Prepared as an HCl salt analogously to I-7, substituting 4-bromo-6-methyl-isoquinoline with ethyl 4-bromothieno[2,3-c]pyridine-2-carboxylate.
ES/MS: 223.0 (M+H⁺).

Preparation of Intermediate I-146

I-62

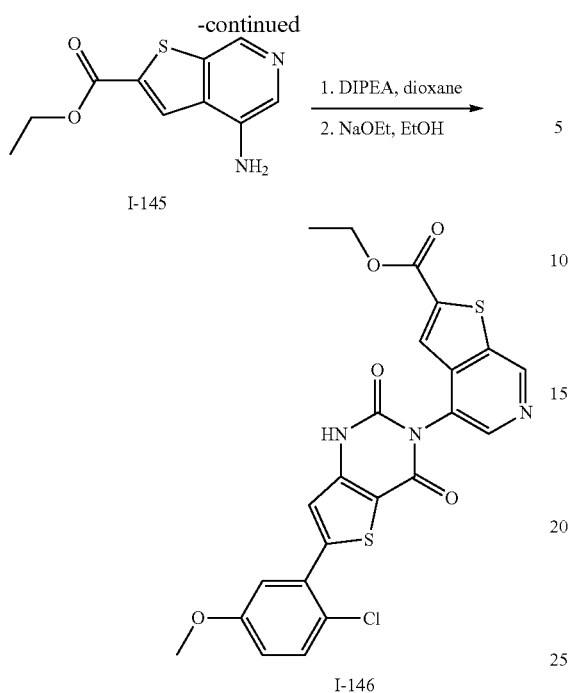

Ethyl 4-[6-(2-chloro-5-methoxy-phenyl)-2,4-dioxo-1H-thieno[3,2-d]pyrimidin-3-yl]thieno[2,3-c]pyridine-2-carboxylate (I-146): Prepared analogously to 1-124, substituting methyl 4-aminoisoquinoline-6-carboxylate with ethyl 4-aminothieno[2,3-c]pyridine-2-carboxylate (I-145).

ES/MS: 513.2 (M+).

$^1$H NMR (400 MHz, DMSO) δ 12.21 (s, 1H), 9.45 (d, J=0.8 Hz, 1H), 8.58 (s, 1H), 8.38 (d, J=0.8 Hz, 1H), 7.60 (d, J=8.9 Hz, 1H), 7.31 (s, 1H), 7.22 (d, J=3.0 Hz, 1H), 7.13 (dd, J=8.9, 3.0 Hz, 1H), 4.39 (q, J=7.1 Hz, 2H), 3.85 (s, 3H), 1.34 (t, J=7.1 Hz, 3H).

Preparation of Intermediate I-147

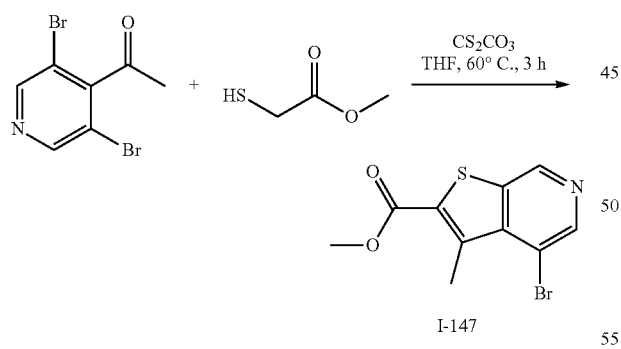

Methyl 4-bromo-3-methyl-thieno[2,3-c]pyridine-2-carboxylate (I-147): To 1-(3,5-Dibromo-pyridin-4-yl)-ethanone (3 g, 11 mmol) in THF (60 mL) was added cesium carbonate (10.6 g, 33 mmol) and methylthioglycolate (1.7 g, 16 mmol). The resulting mixture was stirred at 60° C. for 3 hours. The reaction mixture was cooled to ambient temperature and partially concentrated under reduced pressure. The crude was taken up in EtOAc, washed with dilute NaHCO$_3$ (aq.) then purified by flash chromatography to afford the desired product.

ES/MS: 287.8 (M+).

Preparation of Intermediate I-148

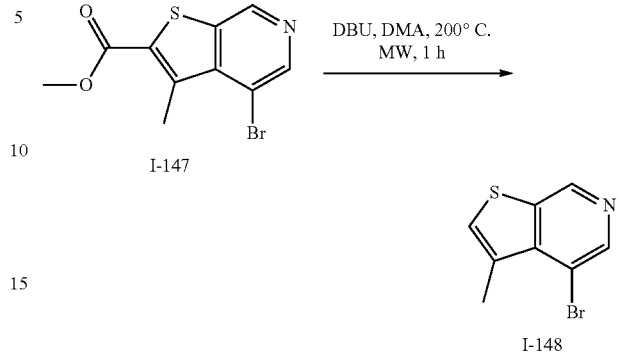

4-bromo-3-methyl-thieno[2,3-c]pyridine (1-148): A solution of methyl 4-bromo-3-methyl-thieno[2,3-c]pyridine-2-carboxylate (I-147) (100 mg, 0.35 mmol) and DBU (130 μL, 0.87 mmol) in DMA (1 mL) was heated at 200° C. under MW irradiation for 1 hour. The reaction mixture was cooled to room temperature and loaded directly to a loading column. Purification by flash chromatography provided the title compound.

ES/MS: 229.8 (M+).

$^1$H NMR (400 MHz, CDCl$_3$) δ 9.00 (s, 1H), 8.59 (s, 1H), 7.42 (q, J=1.2 Hz, 1H), 2.76 (d, J=1.2 Hz, 3H).

Preparation of Intermediate I-149

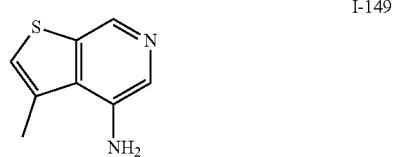

3-methylthieno[2,3-c]pyridin-4-amine (I-149): Prepared analogously to I-7, substituting 4-bromo-6-methyl-isoquinoline with 4-bromo-3-methyl-thieno[2,3-c]pyridine (I-148).

ES/MS: 165.0 (M+H+).

Preparation of Intermediate I-150

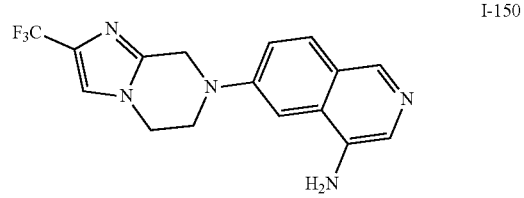 [SMILES: Nc1cncc2ccc(N3CCn4cc(C(F)(F)F)nc4C3)cc12]

6-[2-(trifluoromethyl)-6,8-dihydro-5H-imidazo[1,2-a]pyrazin-7-yl]isoquinolin-4-amine (I-150): Prepared analogously to 1-139, substituting 3-(trifluoromethyl)-5,6,7,8- tetrahydro-[1,2,4]triazolo[4,3-a]pyrazine with 2-(trifluoromethyl)-5,6,7,8-tetrahydroimidazo[1,2-a]pyrazine.

ES/MS: 333.9 (M+H⁺).

Preparation of Intermediate I-151

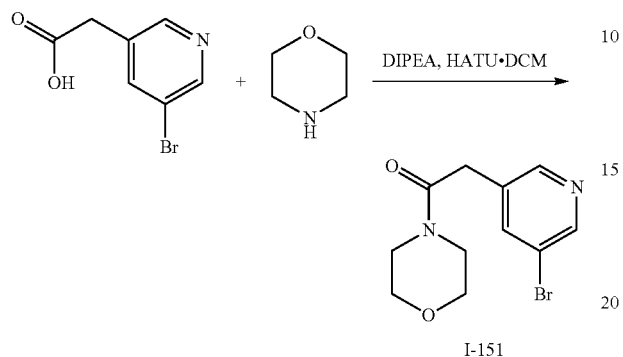

I-151

2-(5-bromo-3-pyridyl)-1-morpholino-ethanone (I-151): A mixture of 2-(5-bromo-3-pyridyl)acetic acid (1 g, 4.63 mmol), morpholine (600 µL, 6.94 mmol), [dimethylamino-(3-oxidotriazolo[4,5-b]pyridin-3-ium-1-yl)methylene]-dimethyl-ammonium:hexafluorophosphate (HATU) (2.1 g, 5.56 mmol), and N,N-diisopropylethylamine (2.42 mL, 13.9 mmol) in DCM (5 mL) was stirred at 50° C. overnight. The reaction mixture was cooled down to room temperature, diluted with water (30 mL) and extracted with EtOAc (3×30 mL). The organic layer was dried over sodium sulfate and concentrated under reduced pressure. The crude product was purified by column chromatography.

ES/MS: 285.9 (M⁺).

Preparation of Intermediate I-152

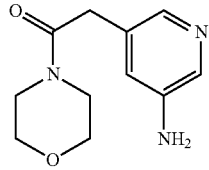

I-152

2-(5-amino-3-pyridyl)-1-morpholino-ethanone (1-152): Prepared analogously to I-7, substituting 4-bromo-6-methyl-isoquinoline with 2-(5-amino-3-pyridyl)-1-morpholino-ethanone (1-151).

ES/MS: 222.0 (M+H⁺).

Preparation of Intermediate I-153

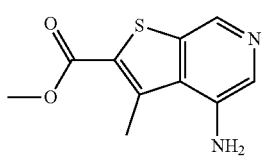

I-153

Methyl 4-amino-3-methyl-thieno[2,3-c]pyridine-2-carboxylate (I-153): Prepared as an HCl salt analogously to 1-7, substituting 4-bromo-6-methyl-isoquinoline with methyl 4-bromo-3-methyl-thieno[2,3-c]pyridine-2-carboxylate (I-152).

ES/MS: 223.0 (M+H⁺).

Preparation of Intermediate I-154

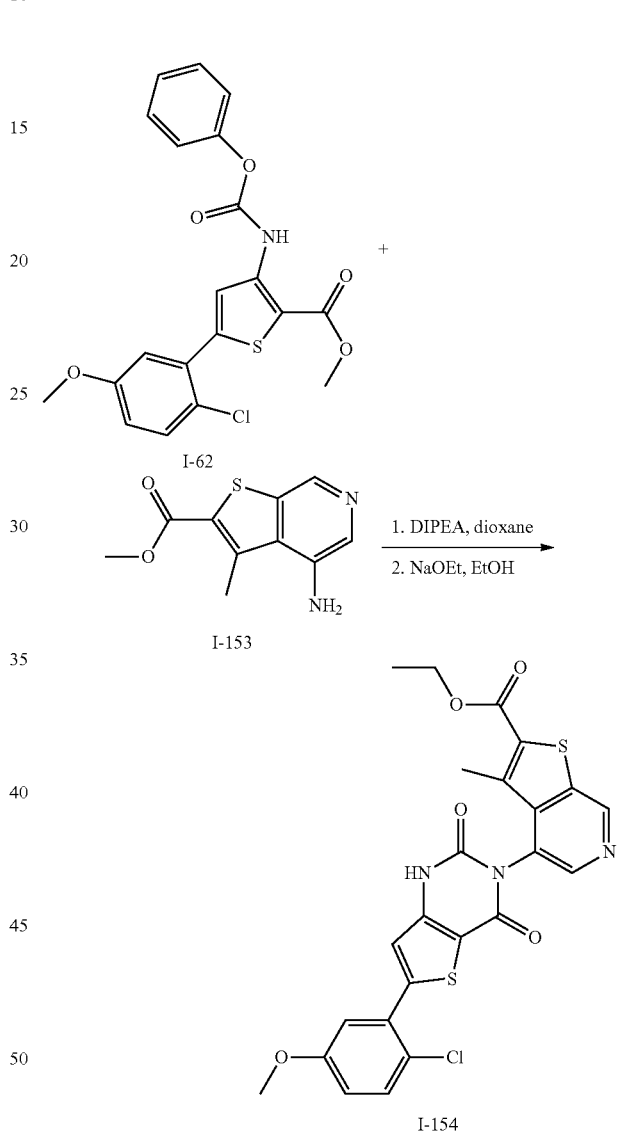

Ethyl 4-[6-(2-chloro-5-methoxy-phenyl)-2,4-dioxo-1H-thieno[3,2-d]pyrimidin-3-yl]-3-methyl-thieno[2,3-c]pyridine-2-carboxylate (I-154): Prepared analogously to 1-124, substituting methyl 4-aminoisoquinoline-6-carboxylate with methyl 4-amino-3-methyl-thieno[2,3-c]pyridine-2-carboxylate (I-153).

ES/MS: 528.7 (M⁺).

%91 ¹H NMR (400 MHz, DMSO) δ 12.44 (s, 1H), 9.43 (s, 1H), 8.57 (s, 1H), 7.59 (d, J=8.9 Hz, 1H), 7.33 (s, 1H), 7.28 (d, J=3.1 Hz, 1H), 7.13 (dd, J=8.9, 3.0 Hz, 1H), 4.38 (q, J=7.1 Hz, 2H), 3.85 (s, 3H), 2.53 (s, 3H), 1.34 (t, J=7.1 Hz, 3H).

549

Preparation of Intermediate I-155

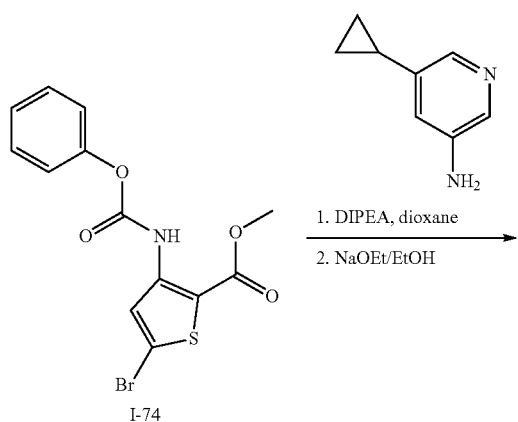

550

Preparation of Intermediate I-156

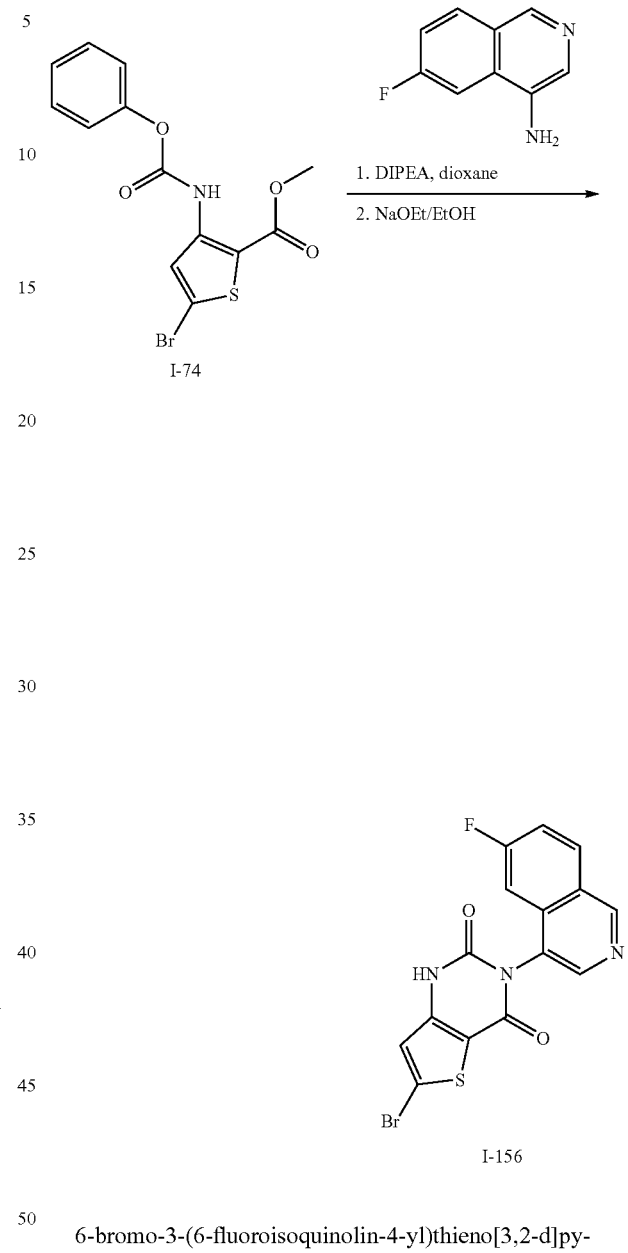

6-bromo-3-(5-cyclopropyl-3-pyridyl)-1H-thieno[3,2-d]pyrimidine-2,4-dione (I-155): To a 100 mL round bottom flask charged with stir bar were added methyl 5-bromo-3-(phenoxycarbonylamino)thiophene-2-carboxylate (I-74) (2 g, 5.61 mmol) and 5-cyclopropylpyridin-3-amine (904 mg, 6.74 mmol), which were stirred at 90 C overnight. The reaction mixture was cooled to room temp and concentrated to dryness. To the crude mixture was added EtOH (30 mL) followed by sodium ethoxide (21% in ethanol, 5.27 mL, 16.3 mmol) and stirred at 80 C, 4 h. The reaction mixture was cooled to rt and solvent was concentrated to dryness. The crude product was purified by silica gel column chromatography (eluent: MeOH/DCM) to afford the product.

ES/MS: 364.1 (M$^+$).

6-bromo-3-(6-fluoroisoquinolin-4-yl)thieno[3,2-d]pyrimidine-2,4(1H,3H)-dione (I-156):

To a 100 mL round bottom flask charged with stir bar were added methyl 5-bromo-3-(phenoxycarbonylamino) thiophene-2-carboxylate (I-74) (0.3 g, 0.84 mmol) and 6-fluoroisoquinolin-4-amine (164 mg, 1.01 mmol) where were stirred at 90 C overnight. The reaction mixture was cooled to room temperature and concentrated to dryness. To the crude mixture was added EtOH (8 mL) followed by sodium ethoxide (21% in ethanol, 0.826 mL, 2.48 mmol) and stirred at 80 C, 4 h. The reaction mixture was cooled to room temperature and solvent was concentrated to dryness. HCl (1N, 4 mL) was added, which formed a precipitate. The solid was collected via filtration, and washed with water (2×1 mL) to deliver the product.

ES/MS: 392.2 (M$^+$).

Preparation of Intermediate I-157

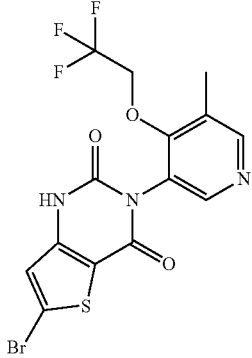

6-bromo-3-(5-methyl-4-(2,2,2-trifluoroethoxy)pyridin-3-yl)thieno[3,2-d]pyrimidine-2,4(1H,3H)-dione (I-157): Prepared analogously to I-155, substituting 5-cyclopropylpyridin-3-amine with (I-78).

ES/MS: 436.2 (M+).

Preparation of Intermediate I-158

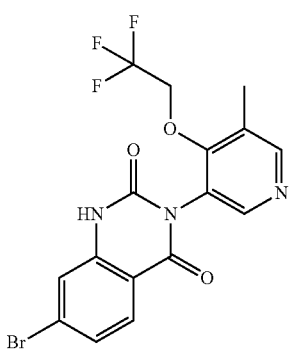

7-bromo-3-(5-methyl-4-(2,2,2-trifluoroethoxy)pyridin-3-yl)quinazoline-2,4(1H,3H)-dione (I-158): Prepared analogously to I-2, substituting isoquinolin-4-amine with (1-78).

ES/MS: 430.1 (M+).

Preparation of Intermediate I-159

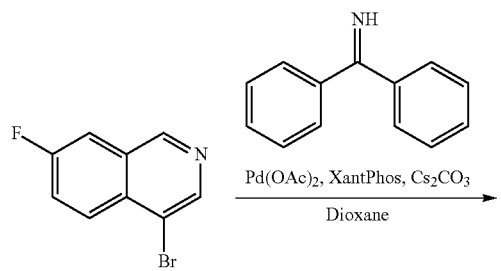

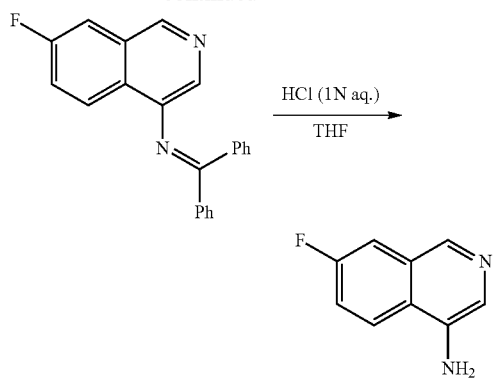

N-(diphenylmethylene)-7-fluoroisoquinolin-4-amine: A mixture of 4-bromo-7-fluoro-isoquinoline (780 mg, 3.4 mmol, 1 eq) in Dioxane (8 mL), diphenylmethanimine (750.4 mg, 4.1 mmol, 694.8 uL, 1.2 eq), (5-diphenylphosphanyl-9,9-dimethyl-xanthen-4-yl)-diphenyl-phosphane (2.0 g, 3.4 mmol, 1 eq) and $Cs_2CO_3$ (1.1 g, 3.4 mmol, 1 eq) was degassed and purged with N2 for 3 times, and then Pd(OAc)$_2$ (77.5 mg, 345.1 umol, 0.1 eq) was added and the mixture was stirred at 100° C. for 16 hr under N2 atmosphere. The reaction mixture was concentrated under reduced pressure to remove solvent. The residue was diluted with $H_2O$ (15 mL) and extracted with Ethyl acetate 45 mL (15 mL×3). The combined organic layers were washed with $H_2O$ (20 mL×2), dried over $Na_2SO_4$, filtered, and concentrated under reduced pressure to give the product.

7-fluoroisoquinolin-4-amine (I-159): To a solution of N-(diphenylmethylene)-7-fluoroisoquinolin-4-amine (4.4 g, 13.5 mmol, 1 eq) in THF (40 mL) was added HCl (1 M, 13.5 mL, 1 eq). The mixture was stirred at 25° C. for 3 hr. The reaction mixture was diluted with 1N KOH solution to adjust pH>7, the residue was diluted with EtOAc 60 mL (20 mL×3), and washed with $H_2O$ 60 mL (20 mL×3), dried over $Na_2SO_4$, filtered and concentrated under reduced pressure to give a residue. The residue was purified by flash silica gel chromatography (eluent: Ethyl acetate/Petroleum ether) to give the product.

MS (ESI): 163.1 (M+H+).

$^1$H NMR (400 MHz, CHLOROFORM-d) δ 8.62 (s, 1H), 7.95 (s, 1H), 7.76 (dd, J=9.2, 5.1 Hz, 1H), 7.45 (dd, J=9.0, 2.5 Hz, 1H), 7.34-7.40 (m, 1H), 4.03 ppm (br s, 2H).

Preparation of Intermediate I-160

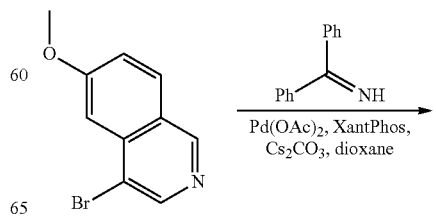

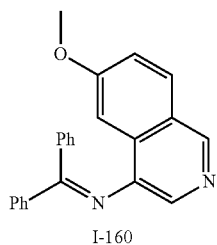

I-160

N-(6-methoxyisoquinolin-4-yl)-1,1-diphenylmethanimine (1-160): To a solution of 4-bromo-6-methoxyisoquinoline (26.0 g, 109 mmol, 1.0 eq), diphenylmethanimine (25.9 g, 143 mmol, 1.3 eq) and Cs$_2$CO$_3$ (71.7 g, 220 mmol, 2.0 eq) in dioxane (520 mL) at rt was added Pd(OAc)$_2$ (867 mg, 3.85 mmol, 0.035 eq) and Xantphos (4.46 g, 7.7 mmol, 0.07 eq). The reaction mixture was stirred at 100° C. for 16 h under N2. The reaction was cooled to rt and concentrated under reduced pressure. The residue was partitioned between ethyl acetate (3(0) mL) and water (150 mL). The separated organic layer was washed with water, dried over Na$_2$SO$_4$ and evaporated to dryness. The residue was purified by silica gel chromatography (eluent: EtOAc/Petroleum ether) to give the product.

Preparation of Intermediate I-161

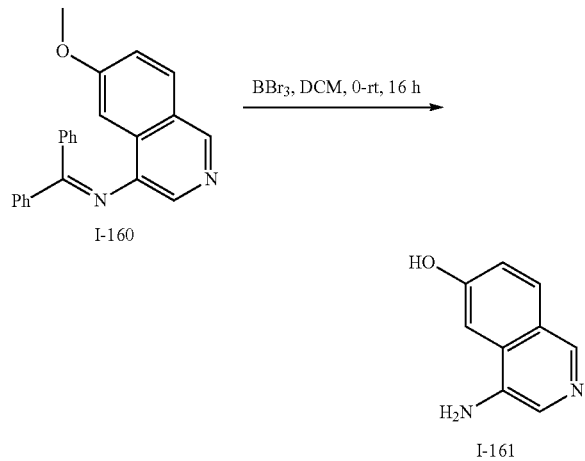

I-160

I-161

4-aminoisoquinolin-6-ol (1-161): To a solution of the N-(6-methoxyisoquinolin-4-yl)-1,1-diphenylmethanimine (1-160) (4.3 g, 12.7 mmol, 1.0 eq) in DCM (40 mL) at −78° C. under N$_2$ was added BBr$_3$ (16.0 g, 63.6 mmol, 5.0 eq). The reaction mixture was stirred at rt for 16 h. The reaction was concentrated under reduced pressure, and dissolved in DCM (50 mL). To the solution at 0° C. was dropwise added methanol (10 mL) to quench the residual BBr$_3$, followed with solid NaHCO$_3$ (4 g), stirred for 30 min. The suspension was concentrated and purified by silica gel chromatography eluent: DCM/MeOH) to give the product.

$^1$H NMR (400 MHz, DMSO-d$_6$) δ 8.63 (s, 1H), 8.04 (d, J=8.9 Hz, 1H), 7.64 (s, 1H), 7.40 (s, 1H), 7.34 (d, J=9.0 Hz, 1H).

Preparation of Intermediate I-162

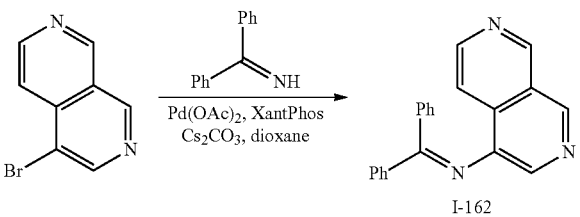

I-162

N-(2,7-naphthyridin-4-yl)-1,1-diphenylmethanimine (I-162): To a solution of 4-bromo-2,7-naphthyridine (3.7 g, 17.7 mmol, 1.0 eq) in Dioxane (130 mL) was added benzophenone imine (3.8 g, 21.2 mmol, 1.2 eq), Pd(OAc)$_2$ (0.4 g, 1.77 mmol, 0.1 eq), XantPhos (2.0 g, 3.5 mmol, 0.2 eq) and Cs$_2$CO$_3$ (5.8 g, 17.7 mmol, 1.0 eq) under N2 atmosphere. The reaction mixture was stirred at 100° C. for 3 h. H$_2$O (200 mL) was added and extracted with EtOAc (200 mL×3). The combined organic phases were washed with brine (200 mL), dried over Na$_2$SO$_4$, filtered and concentrated to give crude product. The resulting residue was purified by silica gel chromatography (eluent: petroleum ether/EtOAc) to give the product.

ES/MS: 310.3 (M+H$^+$).

$^1$H NMR (300 MHz, CDCl$_3$): δ 9.35 (s, 1H), 9.00 (s, 1H), 8.71 (d, J=6.0 Hz, 1H), 7.89-7.81 (m, 4H), 7.58-7.45 (M, 3H), 7.21-7.19 (m, 3H), 7.06-7.04 (m, 2H).

Preparation of Intermediate I-163

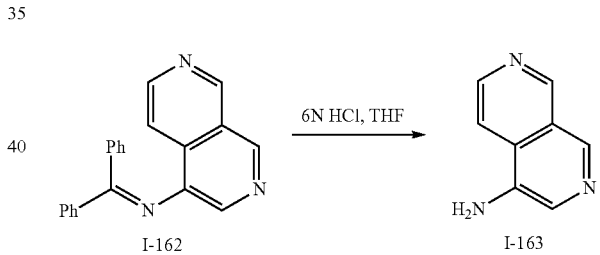

I-162

I-163

2,7-naphthyridin-4-amine (I-163): To a solution of I-162 (4.6 g, 14.9 mmol, 1.0 eq) in THF (46 mL) was added HCl (11.5 mL, 6 N) at room temperature. The solution was stirred at room temperature for 0.5 h and then filtered and the solid was washed with THF (120 mL) and dried under reduced pressure to provide title compound as an HCl salt.

ES/MS: 146.1 (M+H$^+$).

$^1$H NMR (300 MHz, DMSO-d$_6$): δ 9.71 (s, 1H), 9.10 (s, 1H), 8.96 (d, J=6.0 Hz, 1H), 8.42 (d, J=6.3 Hz, 1H), 8.01 (s, 1H).

Preparation of Intermediate I-164

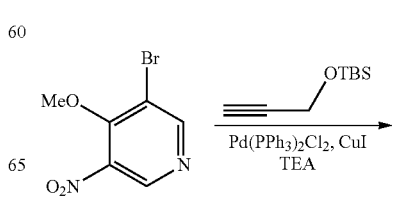

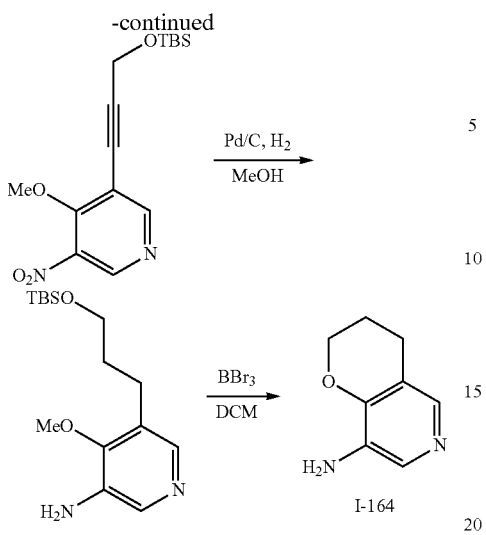

3-(3-((tert-butyldimethylsilyl)oxy)prop-1-yn-1-yl)-4-methoxy-5-nitropyridine: To a solution of 3-bromo-4-methoxy-5-nitro-pyridine (3 g, 12.8 mmol, 1 eq) in TEA (20 mL) was added tert-butyl-dimethyl-prop-2-ynoxy-silane (2.8 g, 16.7 mmol, 3.3 mL, 1.3 eq), Pd(PPh₃)₂Cl₂ (451.8 mg, 643.7 umol, 0.05 eq) and CuI (245.1 mg, 1.2 mmol, 0.1 eq). The mixture was stirred at 50° C. for 12 hr under N2. The reaction mixture was concentrated under reduced pressure to give a residue. The crude residue was purified by column chromatography (eluent: Petroleum ether/Ethyl acetate) to give the product.

5-(3-((tert-butyldimethylsilyl)oxy)propyl)-4-methoxy-pyridin-3-amine: To a solution of Pd/C (100 mg, 10% purity) in MeOH (15 mL) was added 3-(3-((tert-butyldimethylsilyl)oxy)prop-1-yn-1-yl)-4-methoxy-5-nitropyridine (540 mg, 1.6 mmol, 1 eq) under N2. The mixture was stirred at 50° C. for 12 hr under $H_2$ (50 psi). The reaction mixture was filtered and the filtrate dried under reduced pressure to give the product.

3,4-dihydro-2H-pyrano[3,2-c]pyridin-8-amine (I-164): To a solution of 5-(3-((tert-butyldimethylsilyl)oxy)propyl)-4-methoxypyridin-3-amine (350 mg, 1.9 mmol, 1 eq) in DCM (5 mL) was added BBr₃ (1.4 g, 5.7 mmol, 555.2 uL, 3 eq) at 0° C. The mixture was stirred at 0° C. for 1 hr. The reaction mixture added to NH₃·H₂O (purity 25%) 0.5 mL at 0° C. and concentrated under reduced pressure to give a residue. The crude residue was purified by prep-HPLC (neutral condition; column: Waters Xbridge BEH C18 100*30 mm*10 um; mobile phase. [water (NH₄HCO₃)-ACN]) to give the product.

MS (ESI): m/z: 151.1 (M+H⁺).

¹H NMR (400 MHz, DMSO-d₆) δ 7.67 (s, 1H), 7.48 (s, 1H), 4.66 (s, 2H), 4.24-4.17 (m, 2H), 2.64 (t, J=6.4 Hz, 2H), 1.96-1.86 (m, 2H).

Preparation of Intermediate I-165

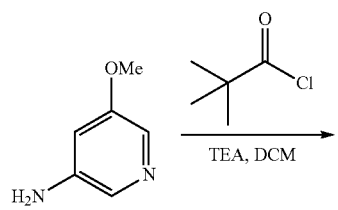

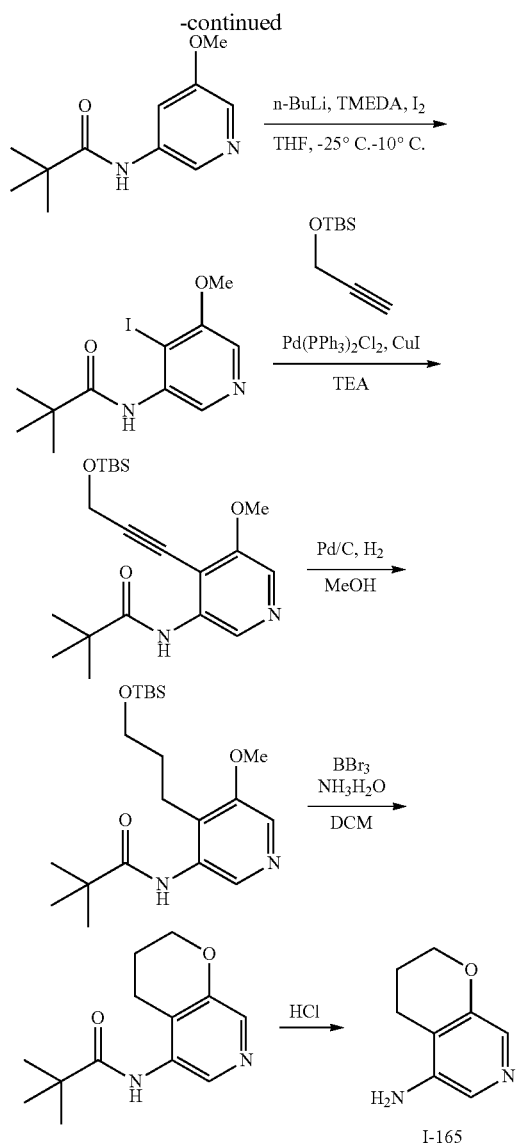

N-(5-methoxy-3-pyridyl)-2,2-dimethyl-propanamide: To a solution of 5-methoxypyridin-3-amine (10 g, 80.6 mmol, 1 eq) in DCM (3 mL) was added TEA (24.5 g, 241.7 mmol, 33.6 mL, 3.0 eq) and 2,2-dimethylpropanoyl chloride (10.7 g, 88.6 mmol, 10.9 mL, 1.1 eq) at 0° C. The mixture was stirred at 25° C. for 12 hr. The reaction mixture was quenched by addition of water (100 mL) at 25° C., and then extracted with DCM 300 mL (3×100 mL). The combined organic layers were washed with sat. NaCl 100 mL (1×100 mL), and dried over Na₂SO₄, filtered and concentrated under reduced pressure. The crude residue was purified by silica column chromatography (eluent Petroleum ether/EtOAc) to give the product.

¹H NMR (400 MHz, chloroform-d) δ 8.13-8.05 (m, 3H), 7.60-7.47 (m, 1H), 3.90-3.84 (m, 3H), 1.35 (s, 9H).

N-(4-iodo-5-methoxy-3-pyridyl)-2,2-dimethyl-propanamide: To a solution of N-(5-methoxy-3-pyridyl)-2,2-dimethyl-propanamide (3.0 g, 14.4 mmol, 1 eq) in THF (100 mL) was added TMEDA (4.2 g, 36.0 mmol, 5.4 mL, 2.5 eq) at 25° C., and then n-BuLi (1 M, 36.0 mL, 2.5 eq) was added to the reaction mixture dropwise at −30° C., stirred at −30° C. for 1 hr, and then 12 (5.9 g, 23.1 mmol, 4.6 mL, 1.6 eq)

in THF (100 mL) was added to the reaction mixture dropwise at −30° C. The mixture was stirred at 25° C. for 2 hr. The reaction mixture was quenched by addition Na₂SO₃ 30 mL at 0° C., and then then extracted with Ethyl acetate 90 mL (3×30 mL). The combined organic layers were washed with sat. NaCl (1'30 mL), dried over Na₂SO₄, filtered and concentrated under reduced pressure. The crude residue was purified by silica column chromatography (eluent: Petroleum ether/EtOAc) to give the product.

¹H NMR (400 MHz, chloroform-d) δ 7.99-7.97 (m, 2H), 7.96-7.94 (m, 1H), 7.46-7.37 (m, 1H), 3.78 (s, 3H), 1.26 (s, 9H).

N-[4-[3-[tert-butyl(dimethyl)silyl]oxyprop-1-ynyl]-5-methoxy-3-pyridyl]-2,2-dimethyl-propanamide: To a solution of N-(4-iodo-5-methoxy-3-pyridyl)-2,2-dimethyl-propanamide (1 g, 3.0 mmol, 1 eq) in TEA (3 mL) was added CuI (57.0 mg, 299.3 umol, 0.1 eq) and tert-butyl-dimethyl-prop-2-ynoxy-silane (662.6 mg, 3.9 mmol, 788.9 uL, 1.3 eq) and purged with N2 for 3 times, and then Pd(PPh₃)₂Cl₂ (105.0 mg, 149.6 umol, 0.05 eq) was added into the reaction mixture and purged with N2 for 3 times. The mixture was stirred at 100° C. for 12 hr. The reaction mixture was filtered and concentrated under reduced pressure. The crude residue was purified by silica column chromatography (eluent: Petroleum ether/EtOAc) to give the product.

¹H NMR (400 MHz, chloroform-d) δ 8.48-7.93 (m, 2H), 4.67-4.63 (m, 2H), 3.98 (s, 3H), 1.36 (s, 9H), 0.94 (s, 9H), 0.19-0.13 (m, 6H).

N-(4-(3-((tert-butyldimethylsilyl)oxy)propyl)-5-methoxypyridin-3-yl)pivalamide: To a solution of N-[4-[3-[tert-butyl(dimethyl)silyl]oxyprop-1-ynyl]-5-methoxy-3-pyridyl]-2,2-dimethyl-propanamide (1.0 g, 2.7 mmol, 1 eq) in MeOH (30 mL) was added palladium (0.1 g, 0.94 mmol) and purged with N2 for 3 times, and then purged with H₂ for 3 times. The mixture was stirred at 50° C. under 50 PSI of H₂ for 12 hr. The reaction mixture was filtered and concentrated under reduced pressure to give the product.

N-(3,4-dihydro-2H-pyrano[2,3-c]pyridin-5-yl)pivalamide: To a solution of N-(4-(3-((tert-butyldimethylsilyl)oxy)propyl)-5-methoxypyridin-3-yl)pivalamide (0.2 g, 525.5 umol, 1 eq) in DCM (1 mL) was added BBr₃ (2.1 g, 8.4 mmol, 810.1 uL, 16 eq) at 0° C. The mixture was stirred at 25° C. for 12 hr. And then the reaction was added to the ammonium hydroxide (884.0 mg, 25.2 mmol, 971.4 uL, 48 eq) at 0° C. The reaction mixture was diluted with water 1 mL and extracted with DCM (3×3 mL). The combined organic layers were washed with water 3 mL (1×3 mL), dried over Na₂SO₄, filtered and concentrated under reduced pressure. The crude product was used in the next step without further purification.

¹H NMR (400 MHz, chloroform-d) δ 8.30-8.26 (m, 1H), 7.97-7.91 (m, 1H), 4.13-4.09 (m, 2H), 2.54-2.50 (m, 2H), 1.96-1.93 (m, 2H), 1.25 (s, 9H).

3,4-dihydro-2H-pyrano[2,3-c]pyridin-5-amine (I-165): A solution of N-(3,4-dihydro-2H-pyrano[2,3-c]pyridin-5-yl)pivalamide (0.4 g, 1.7 mmol, 1 eq) in HCl (12 M, 2 mL, 14.1 eq) was stirred at 65° C. for 3 hr. The reaction mixture was concentrated under reduced pressure. The crude product was purified by reversed-phase HPLC (0.1% HCl condition) (column: Phenomenex luna C18 250×50 mm×10 um; mobile phase: [water(HCl)–ACN]) to give the product.

MS (ESI): m/z: 151.2 (M+H⁺).

1H NMR (400 MHz, DMSO-d₆) δ 7.72 (s, 1H), 7.61 (s, 1H), 4.27-4.21 (m, 2H), 2.55 (t, J=6.4 Hz, 2H), 2.05-1.98 (m, 2H).

Preparation of Intermediate I-166

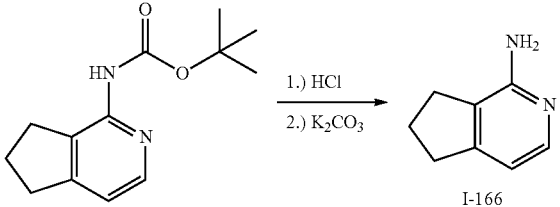 [SMILES: CC(C)(C)OC(=O)Nc1nccc2c1CCC2 ; Nc1nccc2c1CCC2]

6,7-dihydro-5H-cyclopenta[c]pyridin-1-amine (I-166): To a solution of tert-butyl (6,7-dihydro-5H-cyclopenta[c]pyridin-1-yl)carbamate (prepared according the literature procedure in WO 2015/058160, paragraph 00843) (4 g, 17.1 mmol) in dioxane (50 mL) and methanol (50 mL) was added hydrochloric acid (4M in dioxane, 17.1 mL, 68.3 mmol), and the reaction mixture was stirred for 24 h. The mixture was concentrated under reduced pressure, and the crude residue was dissolved in DCM (100 mL) and 50% aqueous potassium carbonate (20 mL). The mixture was stirred for 30 minutes at room temperature, and the pH was checked to be basic. The layers were separated, and the aqueous layer was extracted with dichloromethane (2×30 mL). The combined organic layers were dried over MgSO₄, filtered, and concentrated under reduced pressure to give the title compound, which was carried forward.

Preparation of Intermediate I-167

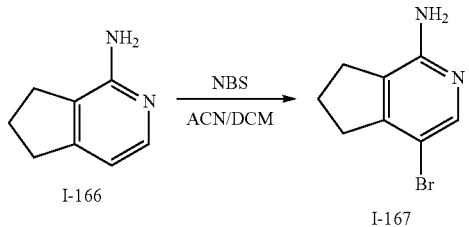

4-bromo-6,7-dihydro-5H-cyclopenta[c]pyridin-1-amine (I-167): To a solution of 6,7-dihydro-5H-cyclopenta[c]pyridin-1-amine (I-166) (1.9 g, 14.2 mmol) in acetonitrile (50 mL) and dichloromethane (50 mL) that was cooled to 0° C., was added dropwise a solution of NBS (2.39 g, 13.5 mmol) dissolved in acetonitrile (30 mL), and the reaction mixture was slowly warmed to room temperature and stirred for 1 hour. The mixture was concentrated, and the crude mixture was purified by column chromatography (eluent: EtOAc in hexanes) to give the product.

ES/MS: 215.1 (M+H⁺).

Preparation of Intermediate I-168

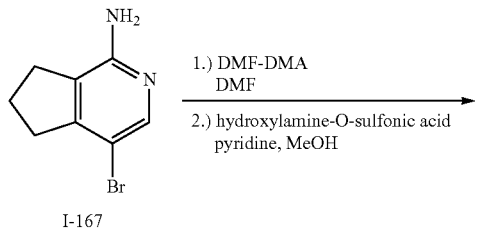

6-bromo-8,9-dihydro-7H-cyclopenta[c][1,2,4]triazolo[1,5-a]pyridine (I-168): To a solution of 4-bromo-6,7-dihydro-5H-cyclopenta[c]pyridin-1-amine (1-167) (2.9 g, 13.6 mmol) in DMF (8 mL) was added N,N-dimethylformamide dimethyl acetal (DMF-DMA) (8.9 mL), and the reaction mixture was stirred overnight at 80° C. The mixture was concentrated under reduced pressure, and methanol (3 mL) was added. Pyridine (1.65 mL, 20.4 mmol) was added at 0° C., followed by hydroxylamine-O-sulfonic acid (2.31 g, 20.4 mmol). The mixture was stirred overnight at room temperature. The precipitate was filtered and saved. The filtrate was concentrated under reduced pressure, and dissolved in DCM (100 mL), EtOAc (30 mL), and sat. aq. sodium bicarbonate (30 mL). The layers were separated, and the aqueous layer was extracted with DCM (2×40 mL). The combined organic layers were washed with brine (10 mL), and were dried over MgSO₄, filtered and concentrated under reduced pressure. The crude mixture was purified by silica chromatography (eluent: EtOAc/hexanes) to give the product, which was combined with the precipitated product.

ES/MS: 238.0 (M+).

1H NMR (400 MHz, Methanol-$d_4$) δ 8.94 (d, J=1.1 Hz, 1H), 8.37 (s, 1H), 3.40-3.34 (m, 2H), 3.20-3.12 (m, 2H), 2.41-2.30 (m, 2H).

Preparation of Intermediate I-169

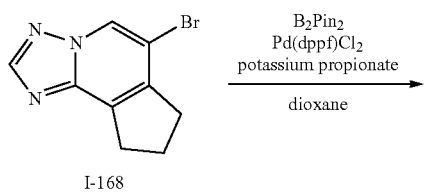

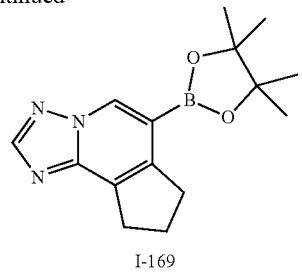

6-(4,4,5,5-tetramethyl-1,3,2-dioxaborolan-2-yl)-8,9-dihydro-7H-cyclopenta[c][1,2,4]triazolo[1,5-a]pyridine (1-169): To a 200 mL RBF was added 6-bromo-8,9-dihydro-7H-cyclopenta[c][1,2,4]triazolo[1,5-a]pyridine (1-168) (2 g, 8.4 mmol), B₂Pin₂ (3.2 g, 12.6 mmol). [1,1'-Bis(diphenylphosphino)ferrocene]dichloropalladium(II) (0.62 g, 0.84 mmol), and potassium propionate (2.83 g, 25.2 mmol). The mixture was dissolved in 1,4-dioxane (20 mL), and argon was bubbled through the reaction mixture for 3 minutes. The mixture was heated at 95° C. for 1 hour under nitrogen. The mixture was cooled to rt, filtered through celite (rinsing with EtOAc), and concentrated under reduced pressure. The crude residue was purified by silica gel chromatography (eluent: EtOAc/hexanes) to provide the product.

ES/MS: 286.2 (M+H+).

1H NMR (400 MHz, Chloroform-d) δ 8.83 (s, 1H), 8.32 (s, 1H), 3.30-3.18 (m, 4H), 2.28 (p, J=7.6 Hz, 2H), 1.38 (s, 12H).

Preparation of Intermediate I-170

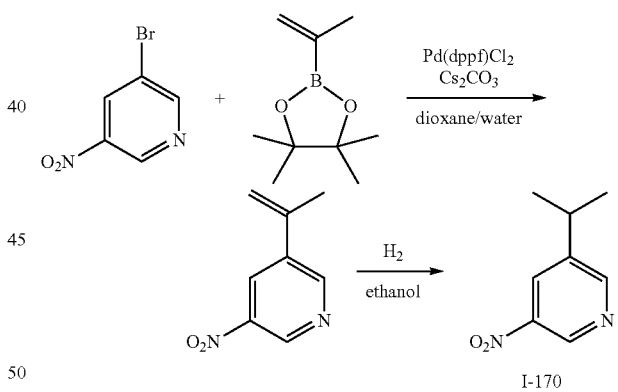

3-Nitro-5-(prop-1-en-2-yl)pyridine: To a dram vial was added 2-isopropenyl-4,4,5,5-tetramethyl-1,3,2-dioxaborolane (310 mg, 1.85 mmol), 3-bromo-5-nitropyridine (250 mg, 1.2 mmol), Pd(dppf)Cl₂ (101 mg, 0.12 mmol), and cesium carbonate (147 mg, 0.45 mmol). Dioxane (7 mL) and water (1.4 mL) were added, and the mixture was degassed with argon for 30 seconds. The vial was sealed, and the reaction mixture was heated at 90° C. for 16 hours. Upon cooling the reaction was diluted with EtOAc (30 mL), filtered through Celite and the mixture was washed with brine (20 mL). The organic layer was dried over Na₂SO₄, filtered, and concentrated under reduced pressure. The crude residue was purified by silica gel chromatography (eluent: EtOAc/hexanes) to provide the product.

ES/MS: 165.0 (M+H+).

5-isopropylpyridin-3-amine (I-170): To a dram vial was added 3-nitro-5-(prop-1-en-2-yl)pyridine (195 mg, 1.2 mmol) followed by ethanol (10 mL) and palladium hydroxide (250 mg, 1.78 mmol). The reaction was stirred at rt under a hydrogen atmosphere for 16 hrs. The reaction was filtered through celite and concentrated to provide the product.

Preparation of Intermediate I-171

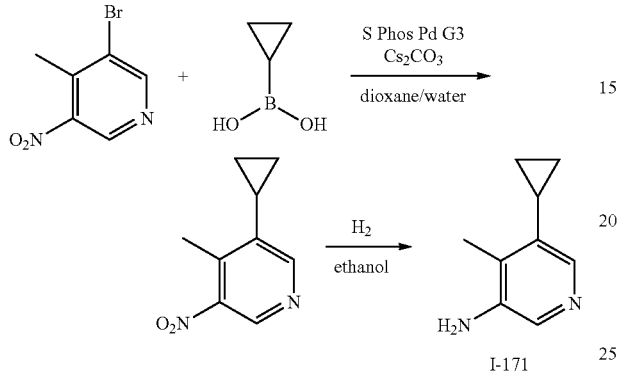

3-cyclopropyl-4-methyl-5-nitropyridine: To a dram vial was added cyclopropylboronic acid (148 mg, 1.73 mmol), 3-bromo-4-methyl-5-nitropyridine (250 mg, 1.15 mmol), SPhos Pd G3 (90 mg, 0.11 mmol), and cesium carbonate (1126 mg, 3.5 mmol). Dioxane (7 mL) and water (1.4 mL) were added, and the mixture was degassed with argon for 30 seconds. The vial was sealed, and the reaction mixture was heated at 110° C. for 16 hours. Upon cooling the reaction was diluted with EtOAc (30 mL), filtered through Celite and the mixture was washed with brine (20 mL). The organic layer was dried over Na$_2$SO$_4$, filtered, and concentrated under reduced pressure. The crude residue was purified by silica gel chromatography (eluent: EtOAc/hexanes) to provide the product.

ES/MS: 179.0 (M+H$^+$).

5-cyclopropyl-4-methylpyridin-3-amine (I-171): To a dram vial was added 3-cyclopropyl-4-methyl-5-nitropyridine (136 mg, 0.76 mmol) followed by ethanol (10 mL) and palladium hydroxide (160 mg, 1.14 mmol). The reaction was stirred at rt under a hydrogen atmosphere for 16 hrs. The reaction was then filtered through celite and concentrated to provide the product.

ES/MS: 150.1 (M+H$^+$).

Preparation of Intermediate I-172

I-172

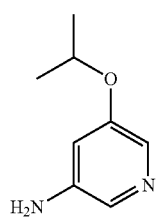

5-isopropoxypyridin-3-amine (I-172): Prepared analogously to I-159, substituting 4-bromo-7-fluoro-isoquinoline with 3-bromo-5-isopropoxy-pyridine.

Preparation of Intermediate I-173

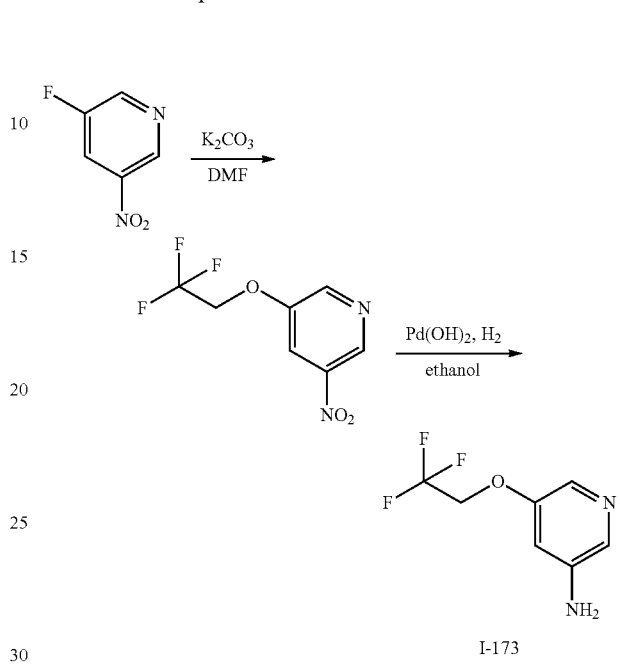

3-nitro-5-(2,2,2-trifluoroethoxy)pyridine: To a vial containing DMF (6 mL) were added 3-fluoro-5-nitro-pyridine (250 mg, 1.76 mmol), potassium carbonate (486 mg, 3.5 mmol), and 2,2,2-trifluoroethanol (0.3 ml). The mixture was stirred at 100° C. for 15 hours. Upon cooling, the mixture was diluted with EtOAc (10 mL) and washed with brine (20 mL). The organic layer was dried over sodium sulfate, concentrated, and used crude in the next reaction.

5-(2,2,2-trifluoroethoxy)pyridin-3-amine (I-173): To a dram vial was added 3-nitro-5-(2,2,2-trifluoroethoxy)pyridine (192 mg, 1.0 mmol) followed by ethanol (10 mL) and palladium hydroxide (250 mg, 1.78 mmol). The reaction was stirred at rt under a hydrogen atmosphere for 16 hrs. The reaction was then filtered through celite and concentrated to provide the product.

Preparation of Intermediate I-174

I-174

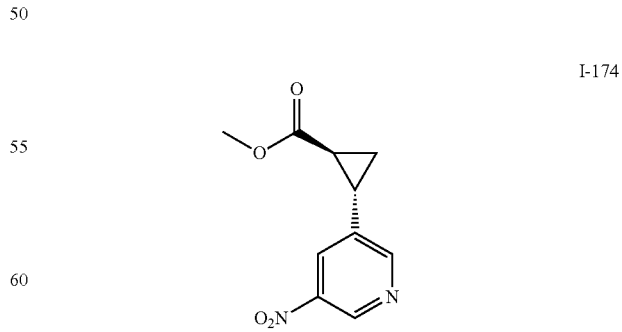

Methyl (1S,2S)-2-(5-nitro-3-pyridyl)cyclopropanecarboxylate (I-174): Prepared analogously to I-39, substituting 3-bromo-4-methyl-5-nitropyridine with 3-bromo-5-nitropyridine.

Preparation of Intermediate I-175

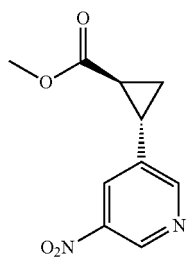

I-174

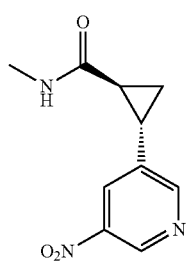

I-175

(1S,2S)—N-methyl-2-(5-nitro-3-pyridyl)cyclopropanecarboxamide: To a vial was added methyl (1S,2S)-2-(5-nitro-3-pyridyl)cyclopropanecarboxylate I-174 (50 mg, 0.22 mmol) and methanamine in methanol (304 mg, 9.8 mmol, 40%). The mixture was stirred for 15 hours at 100° C. Upon cooling the reaction was concentrated and used crude in the next reaction.

(1S,2S)-2-(5-amino-3-pyridyl)-N-methyl-cyclopropanecarboxamide (I-175): To a dram vial was added (1 S,2S)—N-methyl-2-(5-nitro-3-pyridyl)cyclopropanecarboxamide (49 mg, 0.22 mmol) followed by ethanol (10 mL) and palladium hydroxide (62 mg, 0.45 mmol). The reaction was stirred at rt under a hydrogen atmosphere for 16 hrs. The reaction was then filtered through celite and concentrated to provide the product.

Preparation of Intermediate I-176

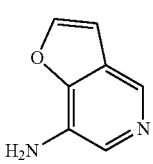

I-176 furo[3,2-c]pyridin-7-amine (I-176): Prepared analogously to I-159, substituting 4-bromo-7-fluoro-isoquinoline with 7-bromofuro[3,2-c]pyridine.

Preparation of Intermediate I-177

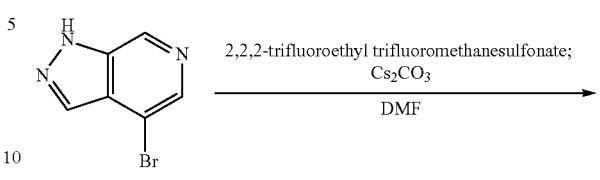

I-177

4-bromo-1-(2,2,2-trifluoroethyl)pyrazolo[3,4-c]pyridine (I-177): To a solution of 4-bromo-1H-pyrazolo[3,4-c]pyridine (0.5 g, 2.5 mmol, 1 eq) in DMF (2 mL) was added 2,2,2-trifluoroethyl trifluoromethanesulfonate (645 mg, 2.8 mmol, 417.0 µL) and Cs$_2$CO$_3$ (823 mg, 2.5 mmol) at 0° C. The mixture was stirred at 25° C. for 12 hr. The reaction mixture was diluted with brine (20 mL) and extracted with EtOAc (25 mL×2). The combined organic layers were dried over Na$_2$SO$_4$, filtered and concentrated under reduced pressure The residue was purified by flash silica gel chromatography (eluent: EtOAc/Petroleum ether) to give the title compound as the major product.

ES/MS: 280.1 (M$^+$).

1H NMR (400 MHz, DMSO-d$_6$) δ 9.32 (s, 1H), 8.49 (s, 1H), 8.42 (d, J=0.8 Hz, 1H), 5.68 (q, J=9.1 Hz, 2H).

Preparation of Intermediate I-178

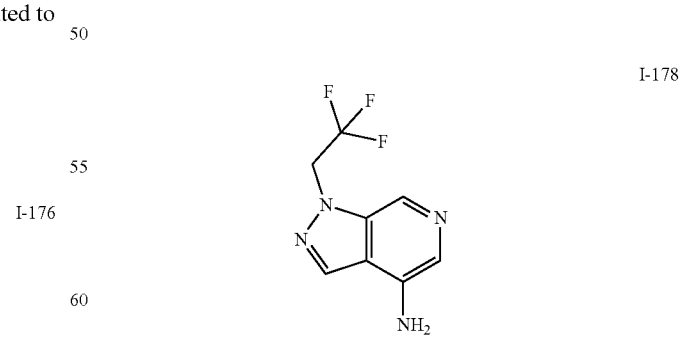

1-(2,2,2-trifluoroethyl)pyrazolo[3,4-c]pyridin-4-amine (I-179): Prepared analogously to 1-159, substituting 4-bromo-7-fluoro-isoquinoline with 4-bromo-1-(2,2,2-trifluoroethyl)pyrazolo[3,4-c]pyridine (1-177).

Preparation of Intermediate I-179 and Intermediate I-180

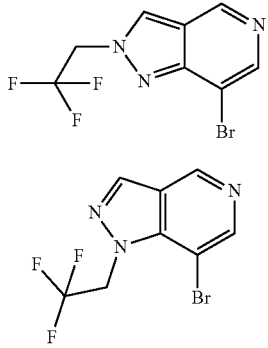

I-179

I-180

7-bromo-2-(2,2,2-trifluoroethyl)pyrazolo[4,3-c]pyridine (I-179) and 7-bromo-1-(2,2,2-trifluoroethyl)pyrazolo[4,3-c]pyridine (1-180): Prepared analogously to I-177, substituting 4-bromo-1H-pyrazolo[3,4-c]pyridine with 7-bromo-1H-pyrazolo[4,3-c]pyridine. The reaction generated a 3:2 ratio of products separable by silica column with I-180 being the minor and most polar.

I-179:
ES/MS: 281.8 (M+).
1H NMR (400 MHz, DMSO-$d_6$) δ 9.23 (s, 1H), 9.01 (s, 1H), 8.44 (s, 1H), 5.68 (q, J=9.0 Hz, 2H).

I-180:
ES/MS: 281.8 (M+).
1H NMR (400 MHz, DMSO-$d_6$) δ 9.16 (s, 1H), 8.64 (s, 1H), 8.60 (s, 1H), 5.66 (q, J=8.7 Hz, 2H).

Preparation of Intermediate I-181

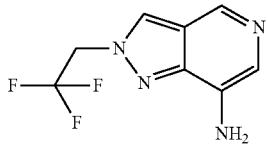

I-181

2-(2,2,2-trifluoroethyl)pyrazolo[4,3-c]pyridin-7-amine (I-181): Prepared analogously to 1-159, substituting 4-bromo-7-fluoro-isoquinoline with 7-bromo-2-(2,2,2-trifluoroethyl)pyrazolo[4,3-c]pyridine (1-179).
ES/MS: 217.0 (M+H+).

Preparation of Intermediate I-182

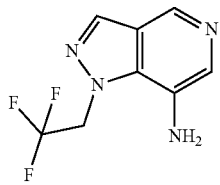

I-182

1-(2,2,2-trifluoroethyl)pyrazolo[4,3-c]pyridin-7-amine (I-182): Prepared analogously to 1-159, substituting 4-bromo-7-fluoro-isoquinoline with 7-bromo-1-(2,2,2-trifluoroethyl)pyrazolo[4,3-c]pyridine (1-180).

Preparation of Intermediate I-183

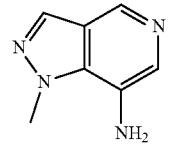

I-183

1-methylpyrazolo[4,3-c]pyridin-7-amine (I-183): Prepared analogously to 1-159, substituting 4-bromo-7-fluoro-isoquinoline with 7-bromo-1-methyl-pyrazolo[4,3-c]pyridine. 1H NMR (400 MHz, DMSO-$d_6$) δ 8.38 (s, 1H), 8.05 (s, 1H), 7.72 (s, 1H), 5.32 (s, 2), 4.26 (s, 3).

Preparation of Intermediate I-183

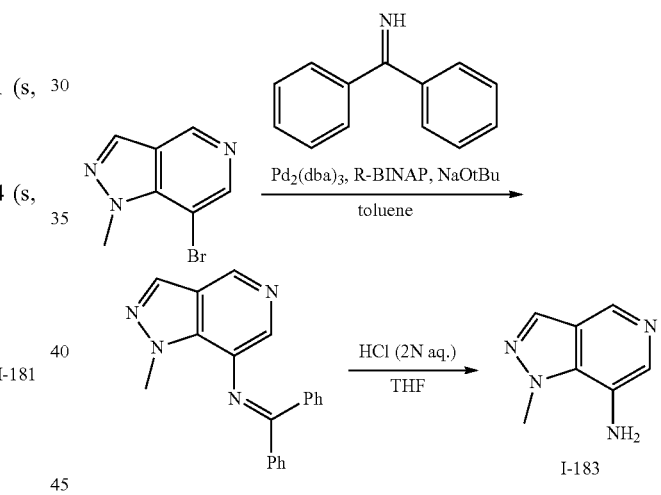

N-(1-methyl-1H-pyrazolo[4,3-c]pyridin-7-yl)-1,1-diphenylmethanimine: A mixture of 7-bromo-1-methyl-1H-pyrazolo[4,3-c]pyridine (5 g, 23.58 mmol, 1 eq) in toluene (50 mL), diphenylmethanimine (6.41 g, 35.37 mmol, 1.5 eq), R-BINAP (7.34 g, 11.79 mmol), Pd$_2$(dba)$_3$ (2.16 g, 2.36 mmol) and NaOtBu (3.4 g, 35.37 mmol, 1.5 eq) was degassed and purged with N2, and then was stirred at 110° C. for 16 hr under N2 atmosphere. The reaction mixture was cooled to room temperature and filtered over a celite pad. The filtrate was diluted with water and extracted with EtOAc twice. The combined organic layer was dried over with Na$_2$SO$_4$ and concentrated under reduced pressure. The crude residue was purified by flash column chromatography on silica gel (eluent: EtOAc/Hexane) to provide the product.
ES/MS: 312.9 (M+H+).

1-methylpyrazolo[4,3-c]pyridin-7-amine (I-183): To a solution of N-(1-methyl-1H-pyrazolo[4,3-c]pyridin-7-yl)-1,1-diphenylmethanimine (7.38 g, 23.6 mmol, 1 eq) in THF (120 mL) was added HCl (1N aq.: 120 ml). The mixture was stirred at 25° C. for 3 hr. The reaction mixture was directly concentrated and dissolved in water. Impurities were washed with EtOAc. The pH of aq layer was maintained ~8 using a Na₂CO₃ solution. The compound was extracted with 10% MeOH/DCM (5×) & 20% THF in EtOAc (2×). The combined organic layers were dried over Na₂SO₄ and concentrated under reduced pressure to get the crude material. The crude material was recrystallized with diethyl ether to afford the product.

ES/MS: 151.0 (M+H).

$^1$H NMR (400 MHz, DMSO-$d_6$) δ 8.38 (s, 1H), 8.05 (s, 1H), 7.72 (s, 1H), 5.32 (s, 2H), 4.26 (s, 3H)

Preparation of Intermediate I-184

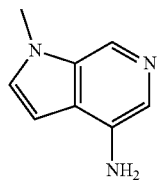

I-184

1-methyl-1H-pyrrolo[2,3-c]pyridin-4-amine (I-184): Prepared analogously to 1-159, substituting 4-bromo-7-fluoro-isoquinoline with 4-bromo-1-methyl-1H-pyrrolo[2,3-c]pyridine.

Preparation of Intermediate I-185

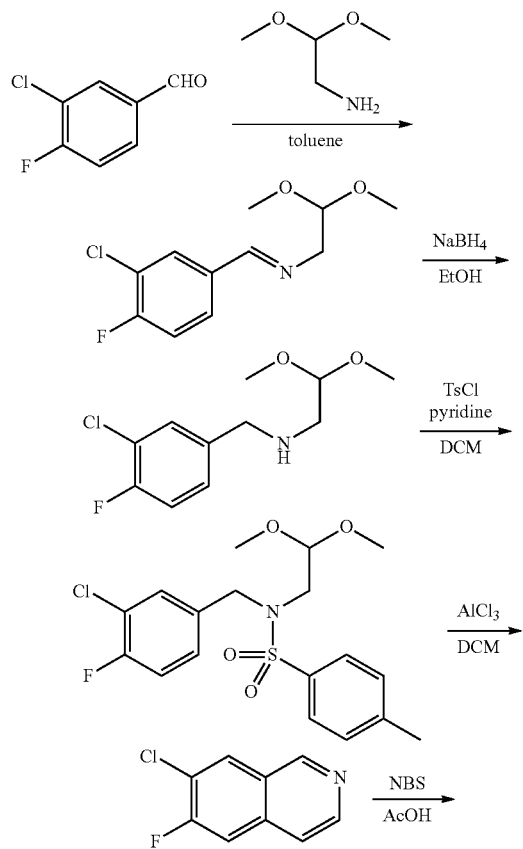

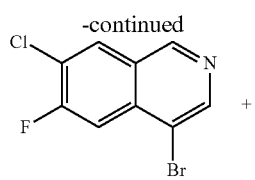

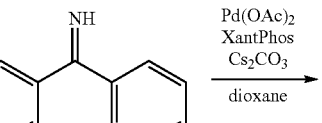

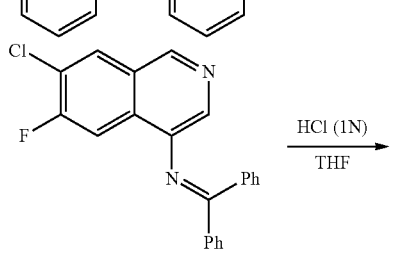

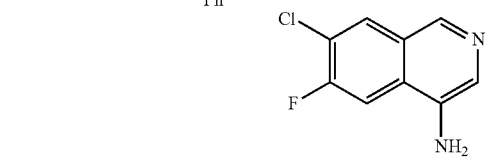

I-185

(E)-1-(3-chloro-4-fluorophenyl)-N-(2,2-dimethoxyethyl)methanimine: To a solution of 3-chloro-4-fluorobenzaldehyde (10 g, 63.1 mmol, 1 eq) in toluene (100 mL) was added 2,2-dimethoxyethanamine (7.0 g, 66.2 mmol, 7.2 mL). The mixture was stirred at 110° C. for 12 h. The reaction was cooled, and the mixture was concentrated under reduced pressure to give a residue. The crude product was carried forward.

$^1$H NMR (400 MHz, CHLOROFORM-d) δ 8.14-8.08 (m, 1H), 7.80-7.73 (m, 1H), 7.53-7.46 (m, 1H), 7.11-7.04 (m, 1H), 4.62-4.56 (m, 1H), 3.71-3.64 (m, 2H), 3.34 (s, 6H).

N-(3-chloro-4-fluorobenzyl)-2,2-dimethoxyethan-1-amine: To a solution of (E)-1-(3-chloro-4-fluoro-phenyl)-N-(2,2-dimethoxyethyl)methanimine (15 g, 61.1 mmol, 1 eq) in ethanol (150 mL) was added NaBH₄ (3.5 g, 91.6 mmol). The mixture was stirred at 25° C. for 3 h. The reaction mixture was diluted with H₂O (100 mL) and stirred for 5 min. The reaction mixture was extracted with EtOAc (3×75 mL). The combined organic layers were washed with H₂O (2×45 mL), dried over Na₂SO₄, filtered and concentrated under reduced pressure. The residue was purified by silica gel chromatography (eluent: EtOAc/Petroleum ether) to give the product.

MS (ESI): m/z=248.0 (M+H⁺).

N-(3-chloro-4-fluorobenzyl)-N-(2,2-dimethoxyethyl)-4-methylbenzenesulfonamide: To a solution of N-[(3-chloro-4-fluoro-phenyl)methyl]-2,2-dimethoxy-ethanamine (23.8 g, 96.0 mmol, 1 eq) in DCM (40 mL) and pyridine (4 mL) was added 4-methylbenzenesulfonyl chloride (29.3 g, 153.6 mmol) at 0° C. Then the mixture was stirred at 25° C. for 5 hr. The reaction mixture was diluted with H₂O (40 mL) and stirred for 5 min. The reaction mixture was extracted with DCM (3×250 mL). The combined organic layers were washed with H₂O (2×150 mL), dried over Na₂SO₄, filtered and concentrated under reduced pressure. The crude residue was purified by silica gel chromatography (eluent: EtOAc/Petroleum ether) to give the product.

¹H NMR (400 MHz, CHLOROFORM-d) δ 7.63 (d, J=8.3 Hz, 2H), 7.24 (d, J=8.3 Hz, 2H), 7.11 (dd, J=2.1, 7.0 Hz, 1H), 7.07-7.02 (m, 1H), 6.99-6.94 (m, 1H), 4.34-4.31 (m, 2H), 4.29-4.26 (m, 1H), 3.18 (s, 6H), 3.13 (d, J=5.3 Hz, 2H), 2.36 (s, 3H).

7-chloro-6-fluoroisoquinoline: To a solution of N-[(3-chloro-4-fluoro-phenyl)methyl]-N-(2,2-dimethoxyethyl)-4-methyl-benzenesulfonamide (17.1 g, 42.7 mmol, 1 eq) in DCM (250 mL) was added AlCl₃ (34.1 g, 256.1 mmol, 14.0 mL, 6 eq). The mixture was stirred at 25° C. for 12 h under N2 atmosphere. The reaction mixture was quenched by addition H₂O (1000 mL) at 20° C. The reaction mixture was diluted with DCM (3×300 mL) and washed with H₂O (3×200 mL), dried over Na₂SO₄, filtered and concentrated under reduced pressure. The crude residue was purified by silica gel chromatography (eluent: EtOAc/Petroleum ether) to give the product.

MS (ESI): m/z=182.1 (M+H⁺).

4-bromo-7-chloro-6-fluoroisoquinoline: To a solution of 7-chloro-6-fluoro-isoquinoline (5 g, 27.5 mmol, 1 eq.) in AcOH (50 mL) was added NBS (5.4 g, 30.3 mmol, 1.1 eq.). The mixture was stirred at 90° C. for 3 hr. The reaction mixture was concentrated under reduced pressure. The crude residue was purified by silica gel chromatography (eluent: EtOAc/Petroleum ether) to give the product.

MS (ESI): m/z=260.0 (M+H⁺).

N-(7-chloro-6-fluoroisoquinolin-4-yl)-1,1-diphenyl-methanimine: A mixture of 4-bromo-7-chloro-6-fluoro-isoquinoline (1.1 g, 4.2 mmol, 1 eq.) in dioxane (15 mL), diphenylmethanimine (918.4 mg, 5.1 mmol, 850.4 μL), Xantphos (488.7 mg, 844.6 μmol) and Cs₂CO₃ (1.4 g, 4.2 mmol) was degassed and purged with N₂ 3 times, and then Pd(OAc)₂ (9.5 mg, 42.2 μmol) was added and the mixture was stirred at 90° C. for 12 hr under N2 atmosphere. The reaction mixture was diluted with H₂O (40 mL) and extracted with Ethyl acetate (3×25 mL). The combined organic layers were washed with NaCl (2×50 mL), dried over Na₂SO₄, filtered and concentrated under reduced pressure. The crude product was carried forward.

MS (ESI): m/z=361.0 (M+H⁺).

7-chloro-6-fluoroisoquinolin-4-amine (I-185): To a solution of N-(7-chloro-6-fluoro-4-isoquinolyl)-1,1-diphenyl-methanimine (2.6 g, 7.2 mmol, 1.0 eq) in THF (20 mL) was added HCl (1 M, 28.8 mL). The mixture was stirred at 25° C. for 2 hr. The reaction mixture was diluted with KOH (aq.) to adjust pH>7, the aqueous layer was extracted with Ethyl acetate (20 mL); the combined organic layers were dried over Na₂SO₄, filtered and concentrated under reduced pressure. The crude residue was purified by silica gel chromatography (eluent EtOAc/Petroleum ether) to give the product.

MS (ESI): m/z=197.2 (M+H⁺).

¹H NMR (400 MHz, CHLOROFORM-d) δ 8.67 (s, 1H), 8.06 (s, 11H), 8.01 (d, J=7.4 Hz, 1H), 7.53 (d, J=9.9 Hz, 1H), 4.15-3.89 (m, 2H).

Preparation of Intermediate I-186

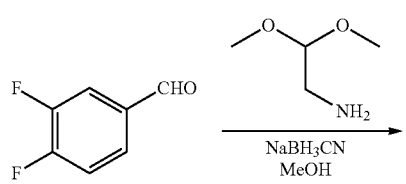

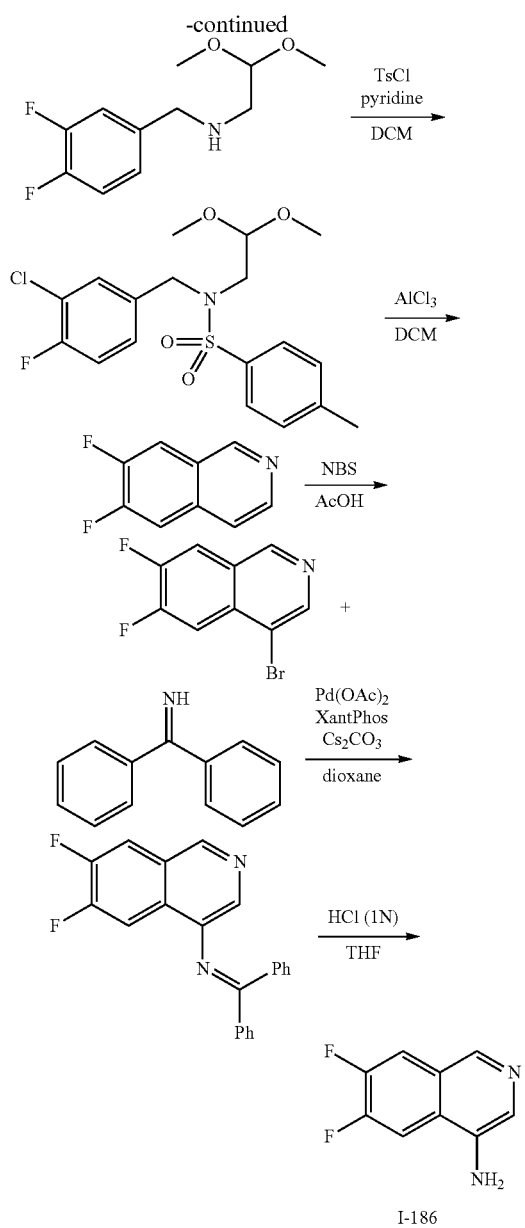

N-(3,4-difluorobenzyl)-2,2-dimethoxyethan-1-amine: To a solution of 3,4-difluorobenzaldehyde (20 g, 140.7 mmol, 15.3 mL, 1 eq.) in MeOH (200 mL) was added 2,2-dimethoxyethanamine (15.5 g, 147.8 mmol, 16.1 mL). The mixture was stirred at 65° C. for 12 h, then NaBH₃CN (44.2 g, 703.7 mmol, 5 eq.) was added and the mixture was stirred at 65° C. for 2 hours. The reaction mixture was concentrated under reduced pressure. The crude residue was diluted with H₂O (3M) mL) and extracted with ethyl acetate (3×250 mL). The combined organic layers were washed with H₂O (2×400 mL), dried over Na₂SO₄, filtered, and concentrated under reduced pressure to give a residue. The crude product was carried forward.

MS (ESI): m/z=232.1 (M+H⁺).

N-(3,4-difluorobenzyl)-N-(2,2-dimethoxyethyl)-4-methylbenzenesulfonamide: To a solution of N43,4-difluorobenzyl)-2,2-dimethoxyethan-1-amine (30 g, 129.7 mmol, 1 eq.) in DCM (200 mL) was added pyridine (58.8 g, 743.4 mmol, 60.0 mL). To this mixture was added TsCl (14.6 g, 207.6 mmol) as a solution in DCM (100 mL) at 0° C. The mixture was stirred at 25° C. for 12 hours. The reaction mixture was concentrated under reduced pressure. The crude residue was diluted with water (300 mL) and extracted with DCM (3×200 mL). The combined organic layers were dried over Na₂SO₄, filtered and concentrated under reduced pressure. The crude residue was purified by silica gel chromatography (eluent: EtOAc/Petroleum ether) to give the product.

¹H NMR (400 MHz, CHLOROFORM-d) δ 7.70 (d, J=8.1 Hz, 2H), 7.31 (d, J=8.1 Hz, 2H), 7.09-7.00 (m, 2H), 6.98-6.92 (m, 1H), 4.39 (s, 2H), 4.32 (t, J=5.3 Hz, 1H), 3.23 (s, 6H), 3.19 (d, J=5.3 Hz, 2H), 2.43 (s, 3H).

6,7-difluoroisoquinoline: To a solution of N-(3,4-difluorobenzyl)-N-(2,2-dimethoxyethyl)-4-methylbenzenesulfonamide (27 g, 70.0 mmol, 1 eq.) in DCM (300 mL) was added AlCl₃ (56.0 g, 420.3 mmol, 23.0 mL, 6 eq.). The mixture was stirred at 25° C. for 12 hr under N₂ atmosphere. The reaction mixture was quenched by addition of H₂O (300 mL) and DCM (200 mL) at 20° C. The reaction mixture was washed with NaHCO₃, dried over Na₂SO₄, filtered and concentrated under reduced pressure. The crude residue was purified by silica gel chromatography (eluent: EtOAc/Petroleum ether) to give the product.

MS (ESI): m/z=166.1 (M+H⁺).

4-bromo-6,7-difluoroisoquinoline: To a solution of 6,7-difluoroisoquinoline (4 g, 24.2 mmol, 1 eq.) in AcOH (50 mL) was added NBS (4.7 g, 26.6 mmol, 1.1 eq.). The mixture was stirred at 90° C. for 3 hr. The reaction mixture was concentrated under reduced pressure. The crude residue was purified by silica gel chromatography (eluent: EtOAc/ Petroleum ether) to give the product.

MS (ESI): m/z=244.0 (M+H⁺).

N-(6,7-difluoroisoquinolin-4-yl)-1,1-diphenylmethanimine: A mixture of 4-bromo-6,7-difluoro-isoquinoline (1.1 g, 4.5 mmol, 1 eq.) in dioxane (15 mL), diphenylmethanimine (980.3 mg, 5.4 mmol, 907.7 μL), Xantphos (521.6 mg, 901.5 umol) and Cs₂CO₃ (1.5 g, 4.5 mmol) was degassed and purged with N₂ 3 times, and then Pd(OAc)₂ (10.2 mg, 45.1 μmol) was added and the mixture was stirred at 90° C. for 16 hr under a N₂ atmosphere. The reaction mixture was concentrated under reduced pressure. The residue was diluted with H₂O (30 mL) and extracted with EtOAc (3×30 mL). The combined organic layers were washed with H₂O (2×50 mL), dried over Na₂SO₄, filtered and concentrated under reduced pressure. The crude product was carried forward.

MS (ESI): m/z=345.1 (M+H⁺).

6,7-difluoroisoquinolin-4-amine (I-186): To a solution of N-(6,7-difluoroisoquinolin-4-yl)-1,1-diphenylmethanimine (1.5 g, 4.4 mmol, 1 eq.) in THF (25 mL) was added HCl (1 M, 4.4 mL). The mixture was stirred at 25° C. for 4 hr. The reaction mixture was diluted with KOH (aq. solution) to adjust pH>7. The mixture was diluted with EtOAc (3×20 mL), and washed with H₂O (3×20 mL), and dried over Na₂SO₄, filtered and concentrated under reduced pressure. The crude residue was purified by silica gel chromatography (eluent: EtOAc/Petroleum ether) to give the product.

¹H NMR (400 MHz, METHANOL-d) δ 8.49 (s, 1H), 8.00 (d, J=12.0, 7.6 Hz, 1H), 7.88-7.90 (m, 1H), 7.83-7.87 ppm (m, 1H).

MS (ESI): m/z=181.2 (M+H⁺).

Preparation of Intermediate I-187

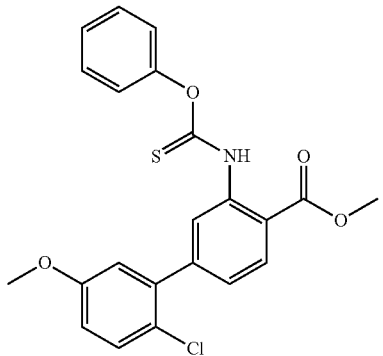

methyl 2'-chloro-5'-methoxy-3-((phenoxycarbonothioyl)amino)-[1,1'-biphenyl]-4-carboxylate (I-187): Prepared analogously to I-132, substituting phenyl carbonochloridate with O-phenyl carbonochloridothioate.

Preparation of Intermediate I-188

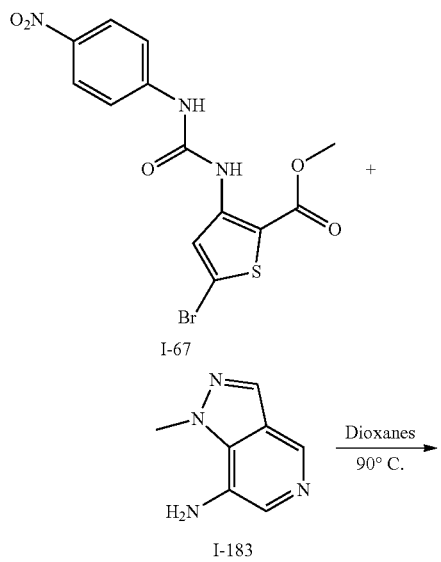

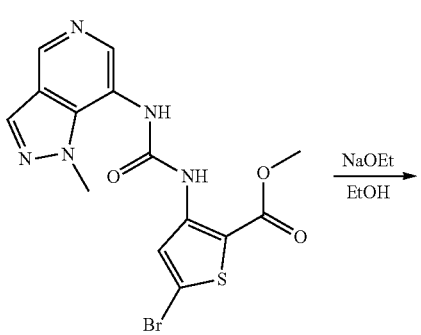

-continued

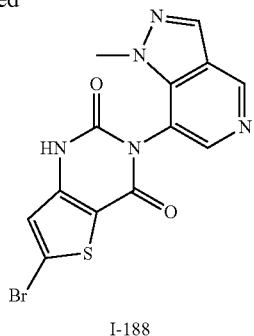

I-188 methyl 5-bromo-3-[(1-methylpyrazolo[4,3-c]pyridin-7-yl)carbamoylamino]thiophene-2-carboxylate: To a mixture of methyl 5-bromo-3-[(4-nitrophenoxy)carbonylamino]thiophene-2-carboxylate (I-67) (7.50 g, 18.7 mmol) in dioxanes (93.5 mL), was added 1-methylpyrazolo[4,3-c]pyridin-7-amine (I-183) (3.32 g, 22.4 mmol). The resulting mixture was then capped and heated at 90° C. for 16 hours. The resulting suspension was then cooled to ambient temperature and concentrated under reduced pressure to give the crude product, which was used in the subsequent step without further purification.

6-bromo-3-(1-methylpyrazolo[4,3-c]pyridin-7-yl)-1H-thieno[3,2-d]pyrimidine-2,4-dione (I-188): To the crude material was then added EtOH (58.4 mL) followed by NaOEt (21% solution in EtOH, 13.2 mL) and the resulting mixture was allowed to stir, at ambient temperature, for 3 hours. The reaction mixture was then concentrated under reduced pressure wherein 300 mL 1M aq. HCl solution was added and subsequently sonicated to furnish I-188 as an HCl salt.

ES/MS: 379.7 (M+).

Preparation of Intermediate I-189

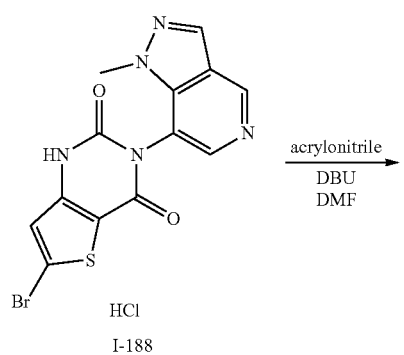

I-188

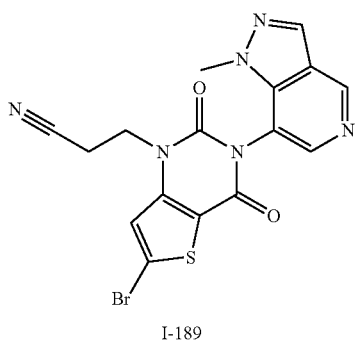

I-189

3-[6-bromo-3-(1-methylpyrazolo[4,3-c]pyridin-7-yl)-2,4-dioxo-thieno[3,2-d]pyrimidin-1-yl]propanenitrile (I-189): To a solution of 6-bromo-3-(1-methylpyrazolo[4,3-c]pyridin-7-yl)-1H-thieno[3,2-d]pyrimidine-2,4-dione;hydrochloride (I-188) (610 mg, 1.47 mmol) in DMF (4 mL) was added DBU (660 μL, 4.41 mmol) followed by acrylonitrile (2.90 mL, 44.1 mmol). The reaction mixture was heated at 80° C. for 16 hours, after which the mixture was cooled to room temperature. The mixture was concentrated under reduced pressure, and the crude material was purified by silica chromatography (eluent: EtOAc in hexanes) to provide the product.

ES/MS: 432.7 (M+).

1H NMR (400 MHz, DMSO-$d_6$) δ 9.17 (s, 1H), 8.42 (s, 1H), 8.34 (s, 1H), 8.00 (s, 1H), 4.44 (dt, J=14.1, 6.9 Hz, 1H), 4.31 (dt, J=14.4, 6.3 Hz, 1H), 3.86 (s, 3H), 3.02 (t, J=6.6 Hz, 2H).

Preparation of Intermediate I-190

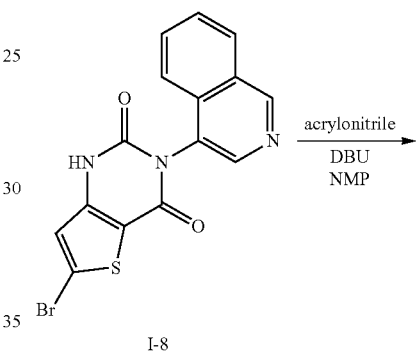

I-8

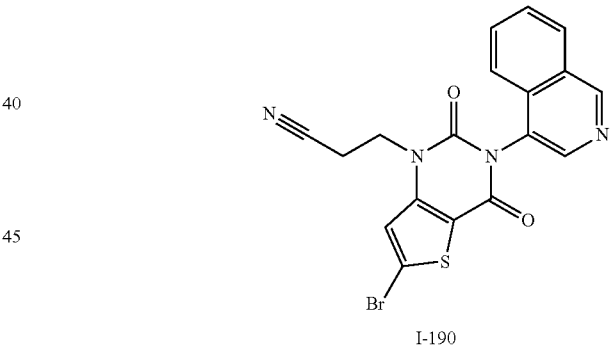

I-190

3-(6-bromo-3-(isoquinolin-4-yl)-2,4-dioxo-3,4-dihydrothieno[3,2-d]pyrimidin-1(2H)-yl)propanenitrile (I-190): To 6-bromo-3-(4-isoquinolyl)-1H-thieno[3,2-d]pyrimidine-2,4-dione;hydrochloride (I-8) (750 mg, 1.83 mmol) in NMP (1 mL) was added acrylonitrile (7.2 mL, 110 mmol) followed by DBU (1.1 mL, 7.31 mmol). The reaction mixture was heated at 80° C. for 16 hours, after which the mixture was cooled to room temperature. The mixture was concentrated under reduced pressure, and the crude material was dissolved in acetone and dry-loaded onto silica. The material was purified by silica chromatography (eluent: EtOAc in hexanes) to provide the product.

ES/MS: 426.7 (M+).

$^1$H NMR (400 MHz, DMSO-$d_6$) δ 9.44 (s, 1H), 8.53 (s, 1H), 8.28 (dd, J=7.0, 2.2 Hz, 1H), 8.00 (s, 1H), 7.90-7.70 (m, 3H), 4.48-4.25 (m, 2H), 2.97 (t, J=6.7 Hz, 2H).

Preparation of Intermediate I-191

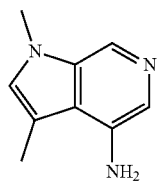

1,3-dimethyl-1H-pyrrolo[2,3-c]pyridin-4-amine (I-191): Prepared analogously to I-85, substituting 7-bromo-1H-pyrrolo[3,2-c]pyridine with 4-bromo-3-methyl-1H-pyrrolo[2,3-c]pyridine.
ES/MS: 162.1 (M+H$^+$).

Preparation of Intermediate I-192

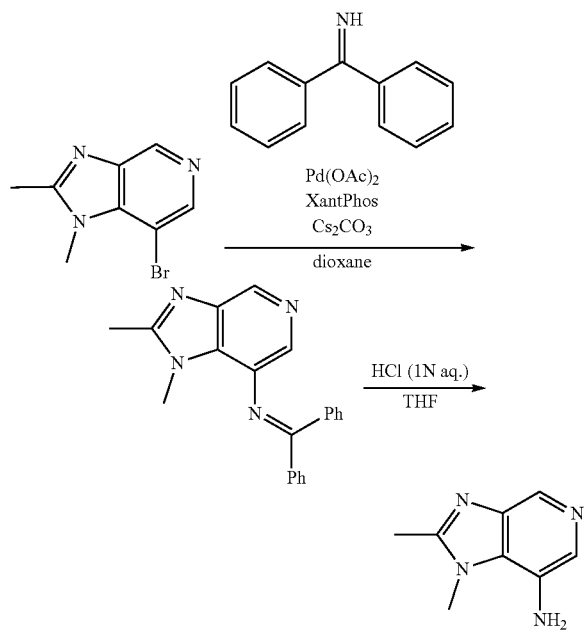

N-(1,2-dimethylimidazo[4,5-c]pyridin-7-yl)-1,1-diphenyl-methanimine: To a 100 mL RBF was added 7-bromo-1,2-dimethyl-imidazo[4,5-c]pyridine (1 g, 4.42 mmol), diphenylmethanimine (0.96 g, 5.31 mmol), Pd(OAc)$_2$ (99 mg, 0.44 mmol), 9,9-Dimethyl-4,5-bis(diphenylphosphino)xanthene (XantPhos) (514 mg, 0.89 mmol) and cesium carbonate (2.16 g, 6.64 mmol). Dioxane (20 mL) was added, and the mixture was degassed with argon for 2 minutes. A reflux condenser was added, and the reaction mixture was heated at 100° C. for 16 hours under an N$_2$ atmosphere. The mixture was subsequently cooled to rt, filtered over celite (rinsing with EtOAc), and concentrated under reduced pressure. The crude residue was purified by silica gel chromatography (eluent: EtOAc/hexanes) to provide the product.
ES/MS: 326.9 (M+H$^+$).

1,3-dimethyl-1H-pyrrolo[2,3-c]pyridin-4-amine (I-192): To a vial was added N-(1,2-dimethylimidazo[4,5-c]pyridin-7-yl)-1,1-diphenyl-methanimine (1.27 g, 3.89 mmol). THF (15 mL) and HCl (1N aqueous; 10 mL) were added, and the mixture was stirred at rt for 2 hours. The reaction was diluted with EtOAc (40 mL) and water (10 mL). The layers were separated, and the aqueous layer was basified with sat. aq. K$_2$CO$_3$ and extracted with EtOAc (5×50 mL). The combined organic layers were washed once with brine (5 mL), dried over magnesium sulfate, filtered, and concentrated under reduced pressure to afford the product.
ES/MS: 163.1 (M+H$^+$).
1H NMR (400 MHz, Methanol-d$_4$) δ 8.23 (s, 1H), 7.77 (s, 1H), 4.06 (s, 3H), 2.60 (s, 3H).

Preparation of Intermediate I-193

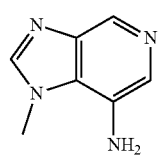

1-methylimidazo[4,5-c]pyridin-7-amine (I-SA-3): Prepared analogously to I-192, substituting 7-bromo-1,2-dimethyl-imidazo[4,5-c]pyridine with 7-bromo-1-methyl-imidazo[4,5-c]pyridine.

Preparation of Intermediate I-194

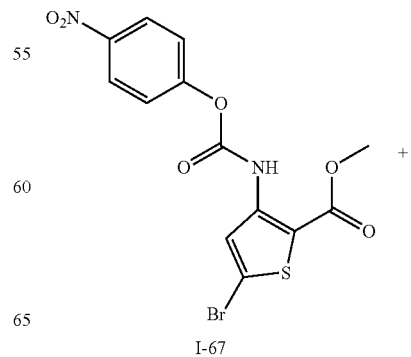

7-bromo-1-methyl-2-(trifluoromethyl)imidazo[4,5-c]pyridine (I-194): Prepared analogously to I-85, substituting 7-bromo-1,2-dimethyl-imidazo[4,5-c]pyridine with 1-methyl-2-(trifluoromethyl)imidazo[4,5-c]pyridin-7-amine.
ES/MS: 217.0 (M+H$^+$).

Preparation of Intermediate I-195

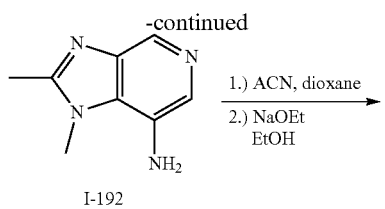

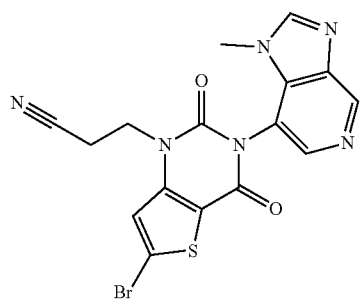

6-bromo-3-(1,2-dimethyl-1H-imidazo[4,5-c]pyridin-7-yl)thieno[3,2-d]pyrimidine-2,4(1H,3H)-dione: To a suspension of methyl 5-bromo-3-(((4-nitrophenoxy)carbonyl)amino)thiophene-2-carboxylate (I-67) (700 mg, 1.74 mmol) in acetonitrile (10 mL) and dioxane (10 mL) was added 1,2-dimethylimidazo[4,5-c]pyridin-7-amine (I-192) (311 mg, 1.92 mmol). The reaction mixture was stirred at 80° C. overnight. The reaction was subsequently cooled to 0° C. A precipitate formed, and the precipitate was isolated by filtration. The precipitate was suspended in EtOH (5 mL), and to the mixture was added sodium ethoxide (21% wt. in EtOH: 0.72 mL, 2.09 mmol) at room temperature dropwise, and the reaction was stirred for 2 hours at room temperature. Approximately half of the solvent was removed under reduced pressure, and HCl (1N, 4 mL) was added. The mixture was let stand at 0° C., whereupon a precipitate formed. The solid was collected via filtration and dried over air to deliver the product as an HCl salt.

ES/MS: 391.7 [M+].

3-(6-bromo-3-(1,2-dimethyl-1H-imidazo[4,5-c]pyridin-7-yl)-2,4-dioxo-3,4-dihydrothieno[3,2-d]pyrimidin-1(2H)-yl)propanenitrile (I-195): To a 40 mL vial with 6-bromo-3-(1,2-dimethyl-1H-imidazo[4,5-c]pyridin-7-yl)thieno[3,2-d]pyrimidine-2,4(1H,3H)-dione (HCl salt) (700 mg, 1.63 mmol) in NMP (1 mL) was added acrylonitrile (6.42 mL, 98 mmol) followed by DBU (1.22 mL, 8.16 mmol). The reaction mixture was heated at 80° C. for 16 hours, after which the mixture was cooled to room temperature. The mixture was concentrated under reduced pressure, and the crude material was dissolved in acetone and dry-loaded onto silica. The material was purified by silica chromatography (eluent: EtOAc in hexanes) to provide the product.

ES/MS: 444.7 (M+).

Preparation of Intermediate I-1%

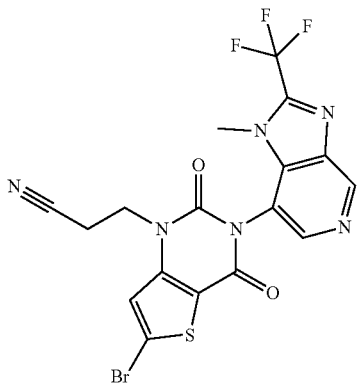

3-(6-bromo-3-(1-methyl-1H-imidazo[4,5-c]pyridin-7-yl)-2,4-dioxo-3,4-dihydrothieno[3,2-d]pyrimidin-1(2H)-yl)propanenitrile (I-196): Prepared analogously to 1-195, substituting 1,2-dimethylimidazo[4,5-c]pyridin-7-amine (I-192) with 1-methylimidazo[4,5-c]pyridin-7-amine (I-193).

ES/MS: 430.7 (M+).

Preparation of Intermediate I-197

3-(6-bromo-3-(1-methyl-2-(trifluoromethyl)-1H-imidazo[4,5-c]pyridin-7-yl)-2,4-dioxo-3,4-dihydrothieno[3,2-d]pyrimidin-1(2H)-yl)propanenitrile (I-197): Prepared analogously to I-195, substituting 1,2-dimethylimidazo[4,5-c]pyridin-7-amine (I-192) with 7-bromo-1-methyl-2-(trifluoromethyl)imidazo[4,5-c]pyridine (I-194).

ES/MS: 498.7 (M+).

Preparation of Intermediate I-198

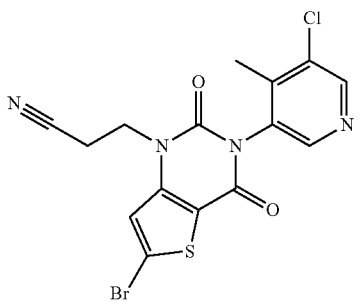

3-(6-bromo-3-(5-chloro-4-methylpyridin-3-yl)-2,4-dioxo-3,4-dihydrothieno[3,2-d]pyrimidin-1(2H)-yl)propanenitrile (I-198): Prepared analogously to I-195, substituting 1,2-dimethylimidazo[4,5-c]pyridin-7-amine (I-192) with 5-chloro-4-methylpyridin-3-amine.
ES/MS: 424.7 (M+).

Preparation of Intermediate I-199

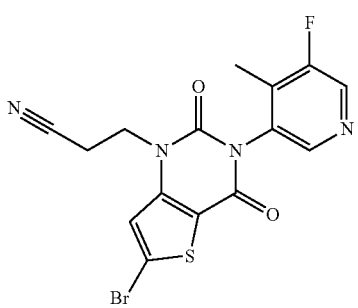

3-(6-bromo-3-(5-fluoro-4-methylpyridin-3-yl)-2,4-dioxo-3,4-dihydrothieno[3,2-d]pyrimidin-1(2H)-yl)propanenitrile (I-199): Prepared analogously to I-195, substituting 1,2-dimethylimidazo[4,5-c]pyridin-7-amine (I-192) with 5-fluoro-4-methylpyridin-3-amine.
ES/MS: 408.7 (M+).

Preparation of Intermediate I-200

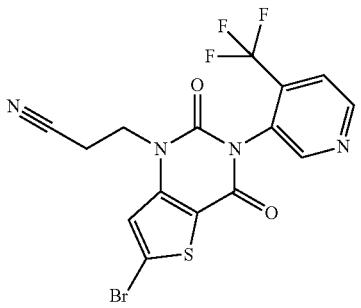

3-(6-bromo-2,4-dioxo-3-(4-(trifluoromethyl)pyridin-3-yl)-3,4-dihydrothieno[3,2-d]pyrimidin-1(2H)-yl)propanenitrile (I-200): Prepared analogously to I-195, substituting 1,2-dimethylimidazo[4,5-c]pyridin-7-amine (I-192) with 4-(trifluoromethyl)pyridin-3-amine.
ES/MS: 444.7 (M+).

Preparation of Intermediate I-201

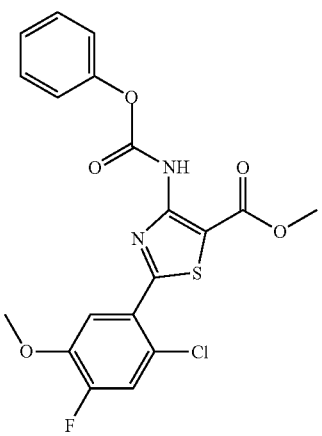

methyl 2-(2-chloro-4-fluoro-5-methoxyphenyl)-4-((phenoxycarbonyl)amino)thiazole-5-carboxylate (I-201): Prepared analogously to I-61, substituting methyl 4-amino-2-chlorothiazole-5-carboxylate with methyl 3-amino-5-bromo-thiophene-2-carboxylate.
ES/MS: 436.7 (M+).

Preparation of Intermediate I-202

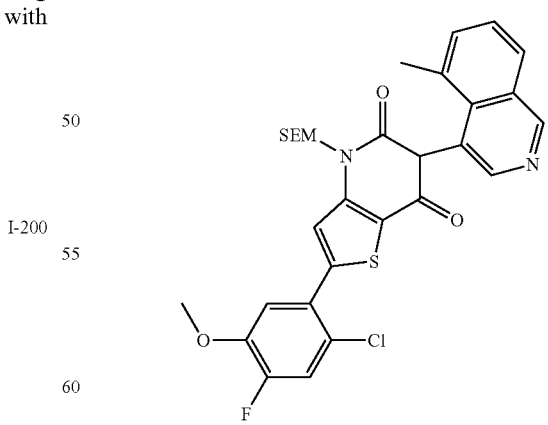

6-(2-chloro-4-fluoro-5-methoxyphenyl)-3-(5-methylisoquinolin-4-yl)-1-((2-(trimethylsilyl)ethoxy)methyl)thieno[3,2-d]pyrimidine-2,4(1H,3H)-dione (I-202). Prepared analogously to I-120, substituting I-8 with Example 560.

Preparation of Intermediate I-203

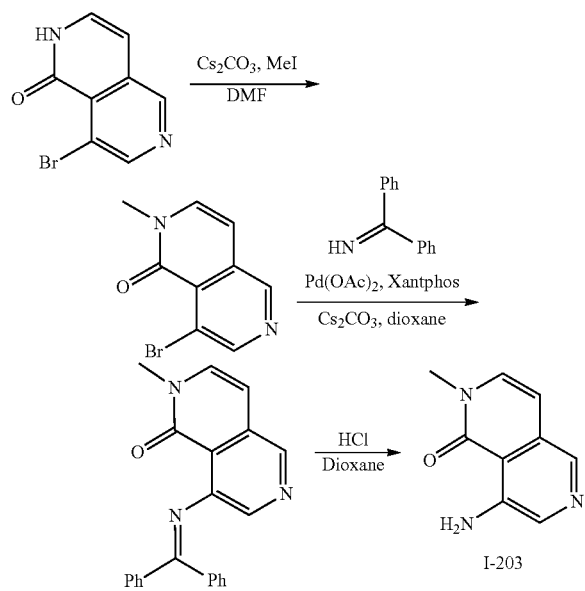

8-bromo-2-methyl-2,6-naphthyridin-1(2H)-one: To a solution of 8-bromo-2H-2,6-naphthyridin-1-one (820 mg, 3.64 mmol, 1.0 equiv.) in dry DMF (12 mL, 0.3 M) was added Cs$_2$CO$_3$ (1.54 g, 4.74 mmol, 1.3 equiv.) followed by MeI (0.3 mL, 4.74 mmol, 1.3 equiv.). The reaction mixture was stirred at 50° C. for 3 h and subsequently cooled to rt. EtOAc (20 mL) was added followed by H$_2$O (10 mL). The layers were separated, and the organic layer was washed with H$_2$O (3×10 mL), brine (10 mL), dried over Na$_2$SO$_4$, filtered and concentrated under reduced pressure to afford the title compound which was used without any further purification.

ES/MS: 238.80 (M$^+$).

8-((diphenylmethylene)amino)-2-methyl-2,6-naphthyridin-1(2H)-one: To a flame-dried 100 mL flask was added 8-bromo-2-methyl-2,6-naphthyridin-1-one (870 mg, 3.64 mmol, 1.0 equiv.), palladium(II) acetate (82 mg, 0.36 mmol, 10 mol %), Xantphos (421 mg, 0.73 mmol, 20 mol %), cesium carbonate (1.2 g, 3.64 mmol, 1.0 equiv.), and benzophenone imine (800 mg, 4.37 mmol, 0.73 mL, 1.2 equiv.) followed by dioxane (16 mL, 0.2 M). The entire reaction mixture was degassed with Ar over 10 min and subsequently heated at 90° C. for 6 hours. The reaction mixture was then cooled to room temperature, concentrated under reduced pressure, and the crude material was purified by silica chromatography (eluent: EtOAc in hexanes (1:5)) to provide the product.

ES/MS: 339.9 (M$^+$).

8-amino-2-methyl-2,6-naphthyridin-1(2H)-one (I-203): To a stirring solution of 8-(((diphenylmethylene)amino)-2-methyl-2,6-naphthyridin-1(2H)-one (1.0 g, 2.95 mmol) in dioxane (3 mL, 1.2 M), was added 4 M HCl (3 mL). The reaction mixture stirred at rt for 2 h, after which EtOAc (10 mL) and H$_2$O (10 mL) were added. The layers were separated, and the pH of the aqueous layer was basified using sat. NaHCO$_3$. EtOAc (10 mL) was subsequently added, the layers separated, and the aqueous layer was extracted with EtOAC (2×5 mL). The organic layers were combined, washed with brine (15 mL), and dried to deliver the target intermediate I-203.

ES/MS: 176.0 (M+H$^+$).

Preparation of Intermediate I-204

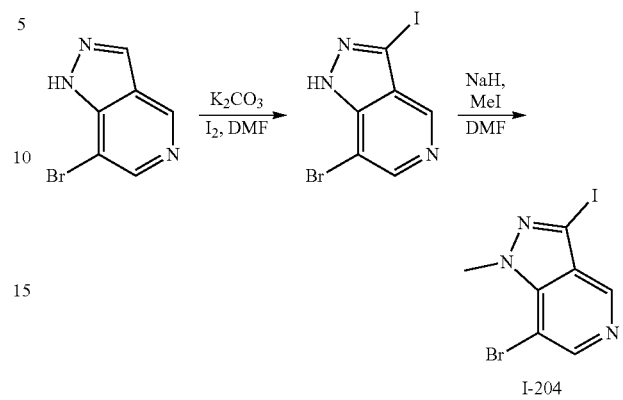

7-bromo-3-iodo-1H-pyrazolo[4,3-c]pyridine: To a stirring solution of 7-bromo-1H-pyrazolo[4,3-c]pyridine (1.0 g, 5.1 mmol, 1.0 equiv.) in DMF (9 mL, 0.56 M) was added K$_2$CO$_3$ (1.40 g, 10.1 mmol, 2.0 equiv.) at rt followed by 12 (2.56 g, 10.1 mmol, 2.0 equiv.). The entire reaction mixture was subsequently heated at 65° C. for 2 h. The reaction mixture was then cooled to room temperature, and diluted with EtOAc (150 mL), followed by washing with saturated Na$_2$S$_2$O$_3$ (2×50 mL), washing with saturated NaCl (2×50 mL), dried over sodium sulfate, filtered, and concentrated under reduced pressure to provide the intermediate and used without further purification.

ES/MS: 324.80 [M$^+$].

7-bromo-3-iodo-1-methyl-pyrazolo[4,3-c]pyridine (I-204): To a stirring solution of 7-bromo-3-iodo-1H-pyrazolo[4,3-c]pyridine (1.25 g, 3.86 mmol, 1.0 equiv.) in DMF (7 mL, 0.58 M) at 0° C. was portion-wise added 60% NaH (200 mg, 5.0 mmol, 1.3 equiv.) The reaction mixture was stirred at 0° C. for 1 h after which MeI (0.26 mL, 4.24 mmol, 1.1 equiv.) was added. After 30 min, a precipitate formed, and the reaction mixture was allowed to warm to rt. The reaction mixture was diluted with cold H$_2$O (10 mL) and filtered to deliver an 80:20 mixture of N-isomers. The mixture was then purified by silica chromatography (eluent: EtOAc in hexanes (100% hexanes to 20% EtOAc)) to provide the desired product I-204.

ES/MS: 337.6 [M$^+$].

Preparation of Intermediate I-205

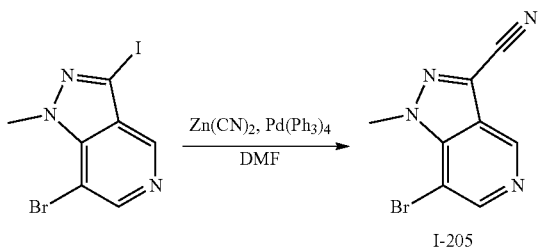

1-methylpyrazolo[4,3-c]pyridine-3,7-dicarbonitrile (I-205): To a 20 mL microwave vial was added 7-bromo- 3-iodo-1-methyl-pyrazolo[4,3-c]pyridine (1-204) (411 mg, 0.12 mmol), Zinc cyanide (171 mg, 0.15 mmol, 1.2 equiv.), and Pd(PPh$_3$)$_4$ (141 mg, 0.12 mmol, 10 mol %) followed by DMF (6.2 mL, 0.02 M). The vial was capped and degassed with Ar after which the reaction mixture was heated to 80° C. for 4 h. The reaction mixture was filtered, concentrated under reduced pressure, and purified via flash chromatography to give the titled compound (I-205).

ES/MS: 236.80 (M+).

Preparation of Intermediate I-206

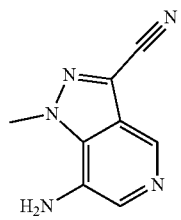
I-206

7-amino-1-methyl-1H-pyrazolo[4,3-c]pyridine-3-carbonitrile (1-206): Prepared analogously to I-7, substituting 4-bromo-6-methyl-isoquinoline with I-205.

ES/MS: 174.0 (M+).

Preparation of Intermediate I-207

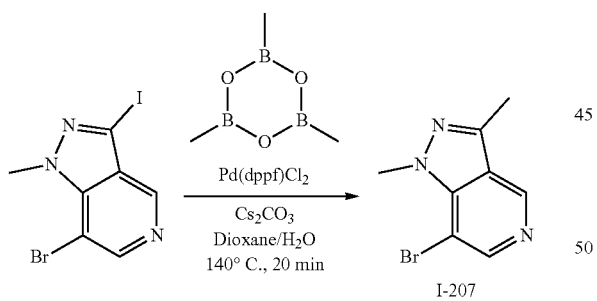
I-207

7-bromo-1,3-dimethyl-1H-pyrazolo[4,3-c]pyridine (I-207): To a 5 mL microwave vial containing a stir bar was added 7-bromo-3-iodo-1-methyl-pyrazolo[4,3-c]pyridine (1-204) (250 mg, 0.74 mmol, 1.0 equiv.), PdCl$_2$(dppf) (55 mg, 0.074 mmol, 10 mol %), cesium carbonate (307 mg, 2.2 mmol, 3.0 equiv.), and trimethylboroxine (0.62 mL, 2.2 mmol, 3.0 equiv.) followed by dioxane/H$_2$O (2.5 mL, 5% water, 0.4 M). The reaction mixture was sealed with Teflon, degassed under Ar (5 min), and heated to 120° C. under microwave irradiation for 25 min. The crude product was filtered through celite, concentrated, and used for the next step.

ES/MS: 225.90 (M$^+$).

Preparation of Intermediate I-208

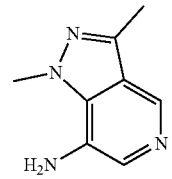
I-208

1,3-dimethyl-1H-pyrazolo[4,3-c]pyridin-7-amine (I-208): Prepared analogously to I-7, substituting 4-bromo-6-methyl-isoquinoline with I-207.

ES/MS: 163.0 (M+).

Preparation of Intermediate I-209

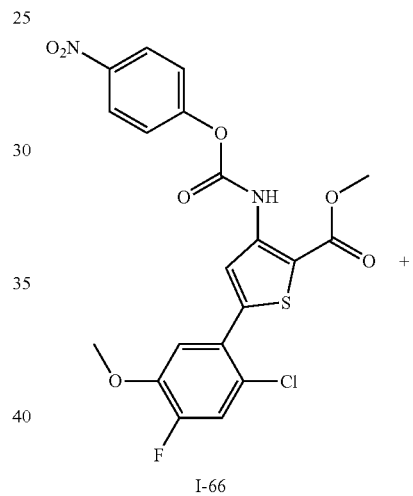

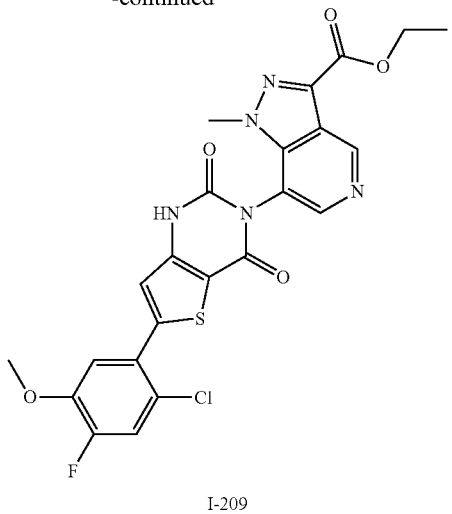

I-209 ethyl 7-[6-(2-chloro-4-fluoro-5-methoxy-phenyl)-2,4-di-oxo-1H-thieno[3,2-d]pyrimidin-3-yl]-1-methyl-pyrazolo[4,3-c]pyridine-3-carboxylate (I-209): To a suspension of methyl 5-(2-chloro-4-fluoro-5-methoxy-phenyl)-3-[(4-nitrophenoxy)carbonylamino]thiophene-2-carboxylate (I-66) (60 mg, 0.125 mmol) in dioxane (0.62 mL) was added 7-amino-1-methyl-pyrazolo[4,3-c]pyridine-3-carbonitrile (I-206) (26 mg, 0.15 mmol, 1,2 equiv.). The reaction mixture was stirred at 90° C. overnight. The reaction mixture was concentrated under reduced pressure. The precipitate was then suspended in EtOH (0.4 mL), and to the mixture was added sodium ethoxide (21% wt. in EtOH; 0.06 mL, 0.19 mmol) at room temperature dropwise, and the reaction was stirred for 2 hours at room temperature. Approximately half of the solvent was removed under reduced pressure, and HCl (1N, 4 mL) was added, whereupon a precipitate formed. The solid was collected via filtration and dried over air to give the title compound I-209.

ES/MS: 529.7 [M+].

Preparation of Intermediate I-210

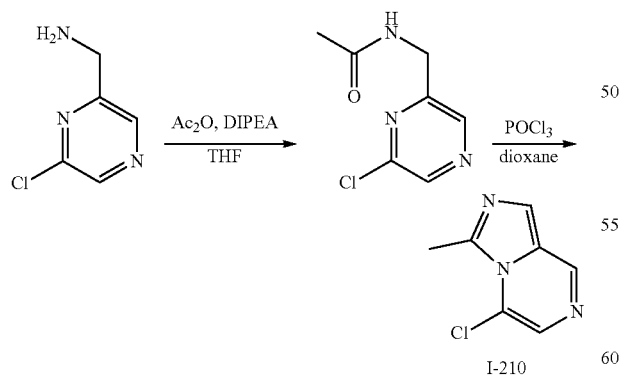

I-210

N-[(6-chloropyrazin-2-yl)methyl]acetamide: To a stirring solution of methyl (6-chloropyrazin-2-yl)methanamine (3.0 g, 21 mmol) in dioxane (70 mL, 0.3 M) was added acetic anhydride (3.2 g, 31.3 mmol, 1.5 equiv.). The reaction mixture was stirred at 50° C. for 4 h. The reaction mixture was cooled to rt and was concentrated under reduced pressure. The reaction mixture was purified via column chromatography eluting with EtOAc/hex to deliver the product.

ES/MS: 185.9 [M+].

5-chloro-3-methyl-imidazo[1,5-a]pyrazine (I-210): To a stirring solution of (6-chloropyrazin-2-yl)methanamine (3.0 g, 21 mmol) in dioxane (40 mL, 0.52 M) was added POCl₃ (2.26 mL, 24.2 mmol, 1.5 equiv.) The reaction mixture was heated to 100° C. and stirred overnight. The reaction mixture was cooled to rt after which hot H₂O (4 mL) was slowly added to the reaction mixture at rt and stirred for 30 min. The mixture was diluted with EtOAc (100 mL) and sat. NaHCO₃ was slowly added. The partitions were separated, and the organic layer was washed with brine (2×20 mL), dried over MgSO₄, and concentrated under reduced pressure. The crude residue was purified by silica gel chromatography (eluent: EtOAc/hexanes), to provide the product.

ES/MS: 167.9 [M+].

Preparation of Intermediate I-211

I-211

3-methylimidazo[1,5-a]pyrazin-5-amine (I-211): Prepared analogously to I-7, substituting 4-bromo-6-methyl-isoquinoline with I-210.

ES/MS: 149.0 (M+).

Preparation of Intermediate I-212

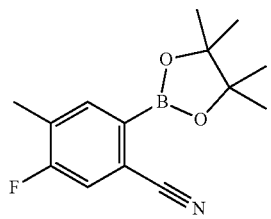

I-212

5-fluoro-4-methyl-2-(4,4,5,5-tetramethyl-1,3,2-dioxaborolan-2-yl)benzonitrile (I-212): Prepared analogously to I-103, substituting 2-bromo-4-methoxy-benzonitrile with 2-bromo-5-fluoro-4-methyl-benzonitrile.

ES/MS: 261.9 (M+).

Preparation of Intermediate I-213

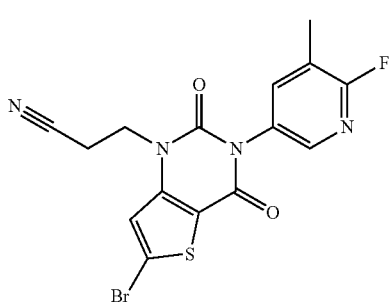

3-[6-bromo-3-(6-fluoro-5-methyl-3-pyridyl)-2,4-dioxo-thieno[3,2-d]pyrimidin-1-yl]propanenitrile (I-213): Prepared analogously to I-195, substituting I-192 with 6-fluoro-5-methyl-pyridin-3-amine.
ES/MS: 409.7 (M+).

Preparation of Intermediate I-214

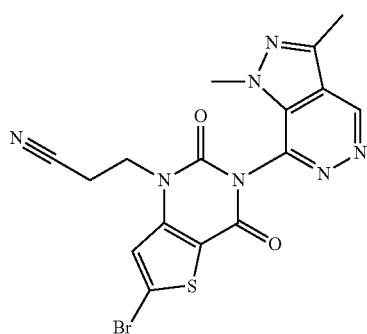

3-[6-bromo-3-(1,3-dimethylpyrazolo[3,4-d]pyridazin-7-yl)-2,4-dioxo-thieno[3,2-d]pyrimidin-1-yl]propanenitrile (I-214): Prepared analogously to I-195, substituting I-192 with 1,3-dimethylpyrazolo[3,4-d]pyridazin-7-amine;hydrochloride.
ES/MS: 446.7 (M+).

Preparation of Intermediate I-215

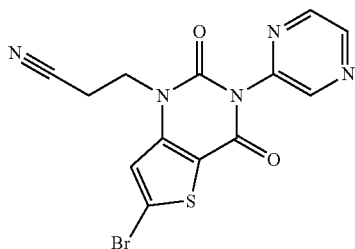

3-(6-bromo-2,4-dioxo-3-pyrazin-2-yl-thieno[3,2-d]pyrimidin-1-yl)propanenitrile (I-215): Prepared analogously to I-195, substituting I-192 with pyrazin-2-amine.
ES/MS: 378.7 (M+).

Preparation of Intermediate I-216

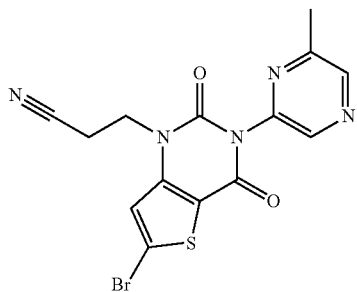

3-[6-bromo-3-(6-methylpyrazin-2-yl)-2,4-dioxo-thieno[3,2-d]pyrimidin-1-yl]propanenitrile (I-216): Prepared analogously to 1-195, substituting I-192 with 6-methylpyrazin-2-amine.
ES/MS: 391.8 (M+).

Preparation of Intermediate I-217

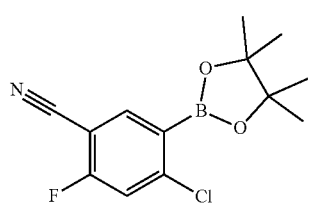

4-chloro-2-fluoro-5-(4,4,5,5-tetramethyl-1,3,2-dioxaborolan-2-yl)benzonitrile (I-217): Prepared analogously to I-103, substituting 2-bromo-4-methoxy-benzonitrile with 5-bromo-4-chloro-2-fluoro-benzonitrile.
ES/MS: 281.9 (M+).

Preparation of Intermediate I-218

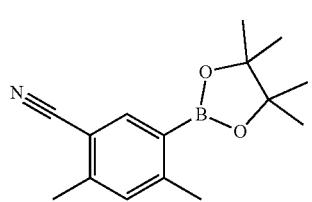

2,4-dimethyl-5-(4,4,5,5-tetramethyl-1,3,2-dioxaborolan-2-yl)benzonitrile (I-218): Prepared analogously to 1-103, substituting 2-bromo-4-methoxy-benzonitrile with 5-bromo-2,4-dimethyl-benzonitrile.
ES/MS: 258.0 (M+H$^+$).

Preparation of Intermediate I-219

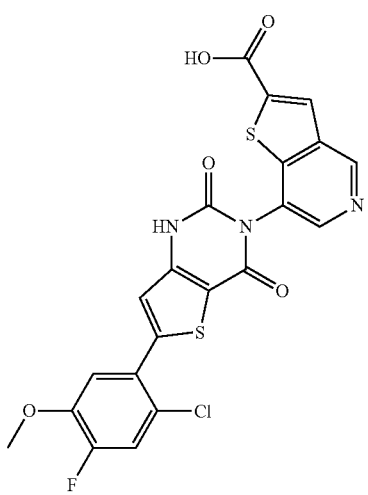

7-[6-(2-chloro-4-fluoro-5-methoxy-phenyl)-2,4-dioxo-1H-thieno[3,2-d]pyrindin-3-yl]thieno[3,2-c]pyridine-2-carboxylic acid (I-219): Prepared analogously to I-127, substituting I-125 with I-117.
ES/MS: 503.7 (M+).

Preparation of Intermediate I-220

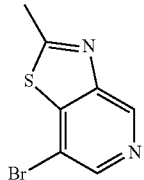

7-bromo-2-methyl-thiazolo[4,5-c]pyridine (I-220): Prepared analogously to 1-109, substituting formic acid with acetic acid.
ES/MS: 230.8 (M+H⁺).

Preparation of Intermediate I-221

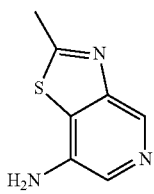

2-methylthiazolo[4,5-c]pyridin-7-amine (I-221): Prepared analogously to 1-7, substituting 4-bromo-6-methyl-isoquinoline with I-220.
ES/MS: 165.9 (M+).

Preparation of Intermediate I-222

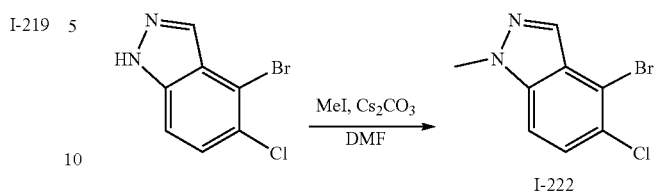

4-bromo-5-chloro-1-methyl-indazole (I-222): To a solution of 4-bromo-5-chloro-1H-indazole (500 mg, 2.16 mmol) in DMF (1.08 mL) under Ar was added Cs₂CO₃ (704 mg, 2.16 mmol) followed by dropwise addition of MeI (0.15 mL, 2.38 mmol). The resulting mixture was stirred for one hour at ambient temperature. The reaction mixture was then diluted with EtOAc, washed with brine (3×10 mL), dried over MgSO₄, and concentrated under reduced pressure. The crude material was then purified via silica gel flash chromatography (eluent: EtOAc in hexanes) to afford the product.
ES/MS: 246.8 (M+H⁺).

Preparation of Intermediate I-223

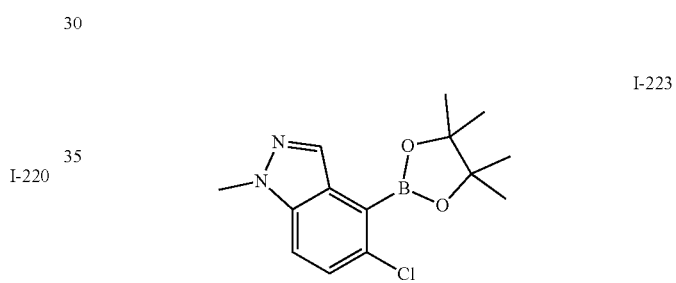

5-chloro-1-methyl-4-(4,4,5,5-tetramethyl-1,3,2-dioxaborolan-2-yl)indazole (I-223): Prepared analogously to I-103, substituting 2-bromo-4-methoxy-benzonitrile with I-222.
ES/MS: 292.9 (M+).

Preparation of Intermediate I-224

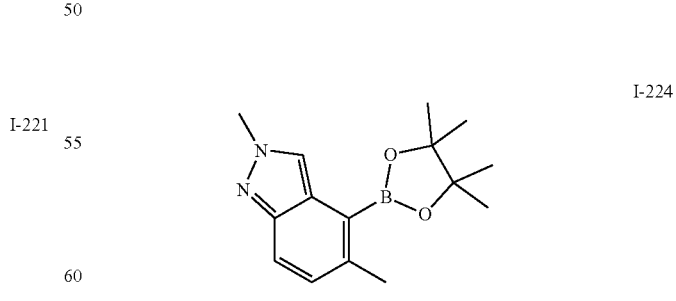

2,5-dimethyl-4-(4,4,5,5-tetramethyl-1,3,2-dioxaborolan-2-yl)indazole (I-224): Prepared analogously to I-103, substituting 2-bromo-4-methoxy-benzonitrile with 4-bromo-2,5-dimethyl-indazole.
ES/MS: 273.0 (M+H⁺).

Preparation of Intermediate I-225

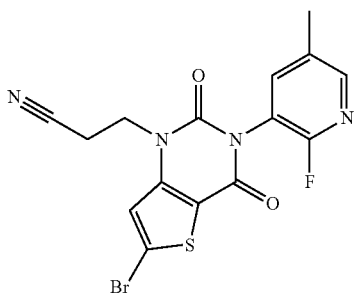

3-[6-bromo-3-(2-fluoro-5-methyl-3-pyridyl)-2,4-dioxo-thieno[3,2-d]pyrimidin-1-yl]propanenitrile (I-225): Prepared analogously to I-195, substituting I-192 with 2-fluoro-5-methyl-pyridin-3-anine.

ES/MS: 355.7 (M+).

Preparation of Intermediate I-226

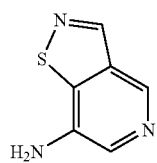

isothiazolo[4,5-c]pyridin-7-amine (I-226): Prepared analogously to I-7, substituting 4-bromo-6-methyl-isoquinoline with 7-bromoisothiazolo[4,5-c]pyridine.

ES/MS: 151.9 (M+H$^+$).

Preparation of Intermediate I-227

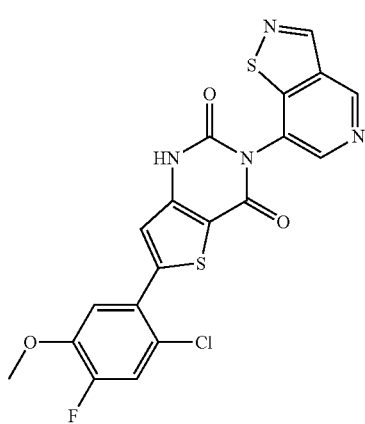

6-(2-chloro-4-fluoro-5-methoxy-phenyl)-3-isothiazolo[4,5-c]pyridin-7-yl-1H-thieno[3,2-d]pyrimidine-2,4-dione (I-227): Prepared analogously to I-124, substituting I-65 with I-66 and substituting methyl 4-aminoisoquinoline-6-carboxylate with I-226.

Preparation of Intermediate I-228

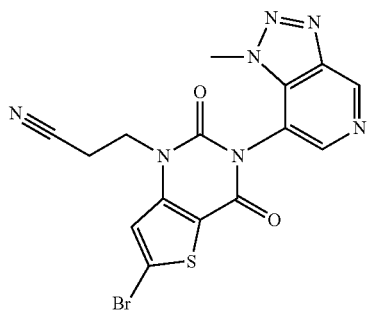

3-[6-bromo-3-(1-methyltriazolo[4,5-c]pyridin-7-yl)-2,4-dioxo-thieno[3,2-d]pyrimidin-1-yl]propanenitrile (I-228): Prepared analogously to I-195, substituting I-192 with I-281.
ES/MS: 433.7 (M+H$^+$).

Preparation of Intermediate I-229

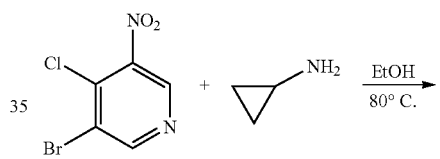

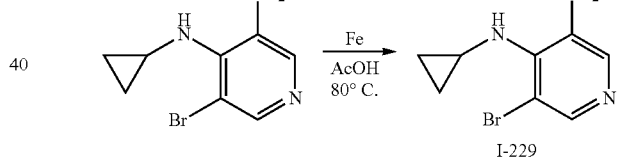

3-bromo-N-cyclopropyl-5-nitro-pyridin-4-amine: To a solution of 3-bromo-4-chloro-5-nitro-pyridine (10.0 g, 42.1 mmol) in EtOH (100 mL) was added cyclopropanamine (4.38 mL, 63.2 mmol). The mixture was then stirred at 80° C. for 4 hours. The reaction mixture was then cooled to ambient temperature, concentrated under reduced pressure, and dissolved in water. The aqueous solution was then extracted with 3×50 mL DCM and the combined organic layers were subsequently washed with brine, dried over MgSO$_4$, filtered, and concentrated under reduced pressure to afford the product without the need for further purification.
ES/MS: 257.9 (M+).

5-bromo-N$_4$-cyclopropyl-pyridine-3,4-diamine (I-229): To a stirring solution of 3-bromo-N-cyclopropyl-5-nitro-pyridin-4-amine (8.00 g, 31.0 mmol) in AcOH (136 mL) was added iron dust (8.66 g, 155 mmol). The resulting mixture was then stirred at 80° C. for 90 minutes, after which, the resulting mixture was filtered through Celite and concentrated under reduced pressure. The crude material was then purified via silica gel flash chromatography (eluent: EtOAc in hexanes) to afford the product.
ES/MS: 227.9 (M+).

Preparation of Intermediate I-230

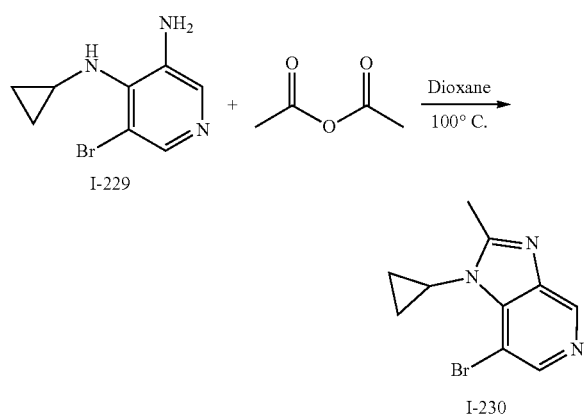

7-bromo-1-cyclopropyl-2-methyl-imidazo[4,5-c]pyridine (I-230): To a 40 mL vial containing a solution of I-CS-13 (500 mg, 2.19 mmol) in dioxanes (9.13 mL) at 100° C. was added dropwise a solution of acetic anhydride (0.21 mL, 2.24 mmol) in dioxanes (5.46 mL), under Ar. The mixture was then stirred at 100° C. for 12 hours. The mixture was then concentrated under reduced pressure and the crude residue was then dissolved in EtOAc and washed with saturated NaHCO$_3$ solution. The organic layer was then dried over MgSO$_4$, filtered, and concentrated under reduced pressure. The crude residue was then purified via silica gel flash chromatography (eluent: EtOAc in hexanes) to afford the product.
ES/MS: 251.8 (M+).

Preparation of Intermediate I-231

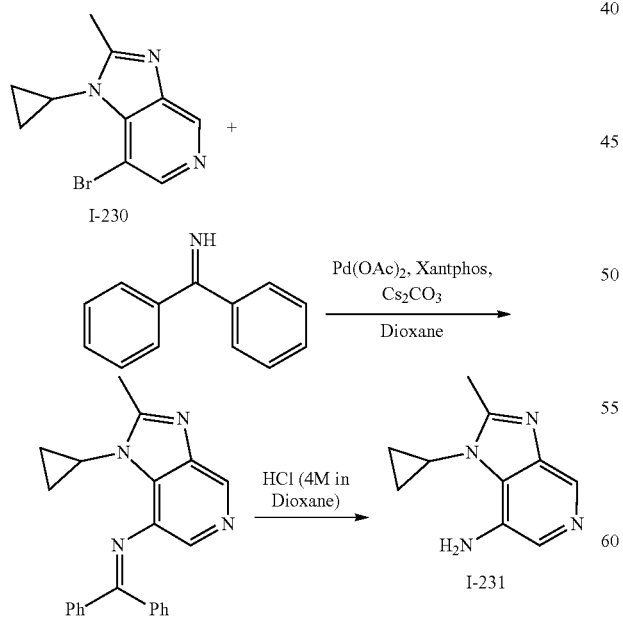

N-(1-cyclopropyl-2-methyl-imidazo[4,5-c]pyridin-7-yl)-1,1-diphenyl-methanimine: To a vial containing a solution of I-230 (387 mg, 1.54 mmol) in dioxanes (7.70 mL) was sequentially added Pd(OAc)$_2$ (34.5 mg, 10 mol %), Xantphos (178 mg, 20 mol %), Cs$_2$CO$_3$ (500 mg, 1.54 mmol), and benzophenone imine (0.31 mL, 1.84 mmol). The resulting mixture was then degassed with Ar for 30 seconds, capped, and stirred at 90° C. for 12 hours, under Ar. The reaction mixture was then filtered through Celite, concentrated under reduced pressure, and purified via silica gel flash chromatography (eluent: MeOH in DCM) to afford the product.
ES/MS: 352.9 (M+).

1-cyclopropyl-2-methyl-imidazo[4,5-c]pyridin-7-amine (I-231): To a RBF containing N-(1-cyclopropyl-2-methyl-imidazo[4,5-c]pyridin-7-yl)-1,1-diphenyl-methanimine (379 mg, 1.08 mmol) was added HCl (4M in dioxanes) (5.40 mL) and the resulting solution was stirred at ambient temperature for 12 hours, wherein a precipitate formed. The precipitate was filtered off and washed with water to afford the product as an HCl salt.
ES/MS: 189.0 (M+).

Preparation of Intermediate I-232

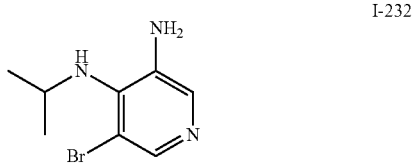

5-bromo-N$_4$-isopropyl-pyridine-3,4-diamine (I-232): Prepared analogously to I-229, substituting cyclopropanamine with isopropylamine.
ES/MS: 231.9 (M+H$^+$).

Preparation of Intermediate I-233

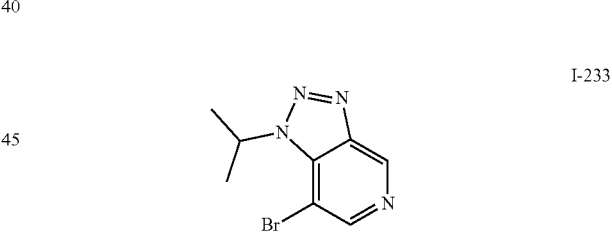

7-bromo-1-isopropyl-triazolo[4,5-c]pyridine (I-233): Prepared analogously to I-281, substituting 5-bromo-N$_4$-methyl-pyridine-3,4-diamine with I-232.
ES/MS: 242.9 (M+H$^+$).

Preparation of Intermediate I-234

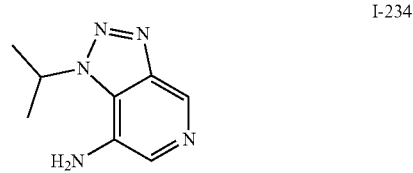

1-isopropyltriazolo[4,5-c]pyridin-7-amine (I-234): Prepared analogously to I-230, substituting I-229 with I-233.

Preparation of Intermediate I-235

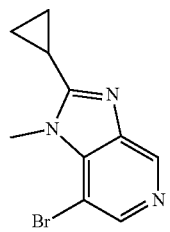

I-235

7-bromo-2-cyclopropyl-1-methyl-imidazo[4,5-c]pyridine (I-235): Prepared analogously to I-230, substituting I-229 with 5-bromo-N₄-methyl-pyridine-3,4-diamine and substituting acetic anhydride with cyclopropanecarboxylic anhydride.

ES/MS: 253.8 (M+H⁺).

Preparation of Intermediate I-236

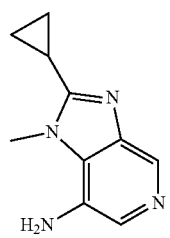

I-236

2-cyclopropyl-1-methyl-imidazo[4,5-c]pyridin-7-amine (I-236): Prepared analogously to 1-231, substituting I-230 with I-235.

ES/MS: 189.0 (M+H⁺).

Preparation of Intermediate I-237

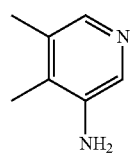

I-237

4,5-dimethylpyridin-3-amine (I-237): Prepared analogously to 1-192, substituting 7-bromo-1,2-dimethyl-imidazo[4,5-c]pyridine with 3-bromo-4,5-dimethyl-pyridine.

Preparation of Intermediate I-238

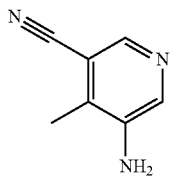

I-238

5-amino-4-methyl-pyridine-3-carbonitrile (I-238): Prepared analogously to 1-192, substituting 7-bromo-1,2-dimethyl-imidazo[4,5-c]pyridine with 5-bromo-4-methyl-pyridine-3-carbonitrile.

Preparation of Intermediate I-239

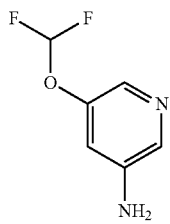

I-239

5-(difluoromethoxy)pyridin-3-amine (I-239): Prepared analogously to I-192, substituting 7-bromo-1,2-dimethyl-imidazo[4,5-c]pyridine with 3-bromo-5-(difluoromethoxy)pyridine.

ES/MS: 160.93 (M⁺).

Preparation of Intermediate I-240

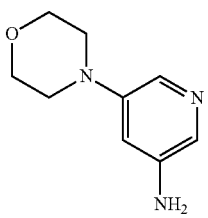

I-240

5-morpholinopyridin-3-amine (I-240): Prepared analogously to I-192, substituting 7-bromo-1,2-dimethyl-imidazo[4,5-c]pyridine with 4-(5-bromo-3-pyridyl)morpholine.

ES/MS: 180.00 (M+H⁺).

Preparation of Intermediate I-241

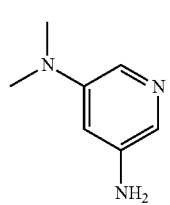

I-241

N3,N3-dimethylpyridine-3,5-diamine (I-241): Prepared analogously to I-192, substituting 7-bromo-1,2-dimethyl-imidazo[4,5-c]pyridine with 5-bromo-N,N-dimethyl-pyridin-3-amine.

Preparation of Intermediate I-242

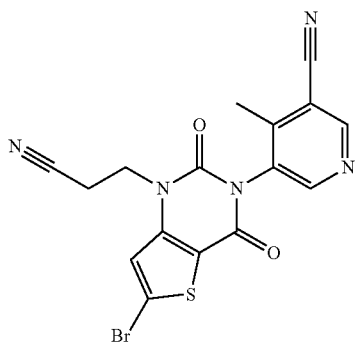

I-242

5-(6-bromo-1-(2-cyanoethyl)-2,4-dioxo-1,4-dihydrothieno[3,2-d]pyrimidin-3(2H)-yl)-4-methylnicotinonitrile (I-242): Prepared analogously to I-195, substituting 1,2-dimethylimidazo[4,5-c]pyridin-7-amine (I-192) with 5-amino-4-methyl-pyridine-3-carbonitrile (I-238).
ES/MS: 416.49 (M⁺).

Preparation of Intermediate I-243

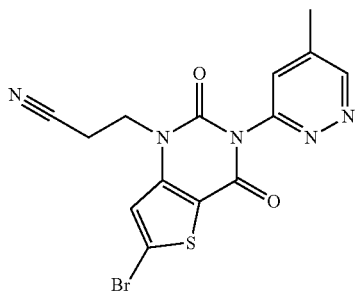

I-243

3-[6-bromo-3-(5-methylpyridazin-3-yl)-2,4-dioxo-thieno[3,2-d]pyrimidin-1-yl]propanenitrile (I-243): Prepared analogously to 1-195, substituting 1,2-dimethylimidazo[4,5-c]pyridin-7-amine (I-192) with 5-methylpyridazin-3-amine.
ES/MS: 392.80 (M⁺).

Preparation of Intermediate I-244

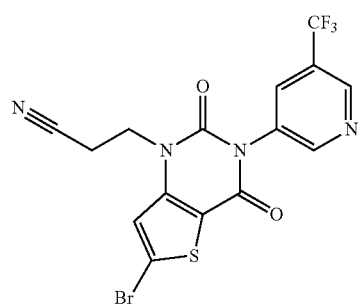

I-244

3-[6-bromo-2,4-dioxo-3-[5-(trifluoromethyl)-3-pyridyl]thieno[3,2-d]pyrimidin-1-yl]propanenitrile (I-244): Prepared analogously to 1-195, substituting 1,2-dimethylimidazo[4,5-c]pyridin-7-amine (I-192) with 5-(trifluoromethyl)pyridin-3-amine.
ES/MS: 444.60 (M⁺).

Preparation of Intermediate I-245

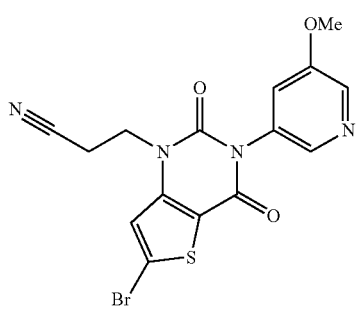

I-245

3-[16-bromo-3-(5-methoxy-3-pyridyl)-2,4-dioxo-thieno[3,2-d]pyrimidin-1-yl]propanenitrile (I-245): Prepared analogously to 1-195, substituting 1,2-dimethylimidazo[4,5-c]pyridin-7-amine (I-192) with 5-methoxypyridin-3-amine.
ES/MS: 385.70 (M⁺).

Preparation of Intermediate I-246

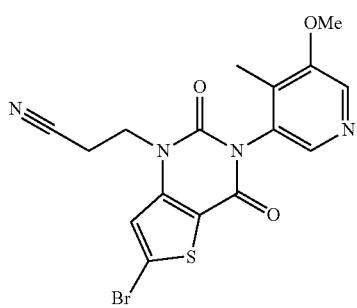

I-246

3-[16-bromo-3-(5-methoxy-4-methyl-3-pyridyl)-2,4-dioxo-thieno[3,2-d]pyrimidin-1-yl]propanenitrile (I-246):

Prepared analogously to 1-195, substituting 1,2-dimethyl-imidazo[4,5-c]pyridin-7-amine (I-192) with 5-methoxy-4-methyl-pyridin-3-amine.

ES/MS: 420.70 (M+).

Preparation of Intermediate I-247

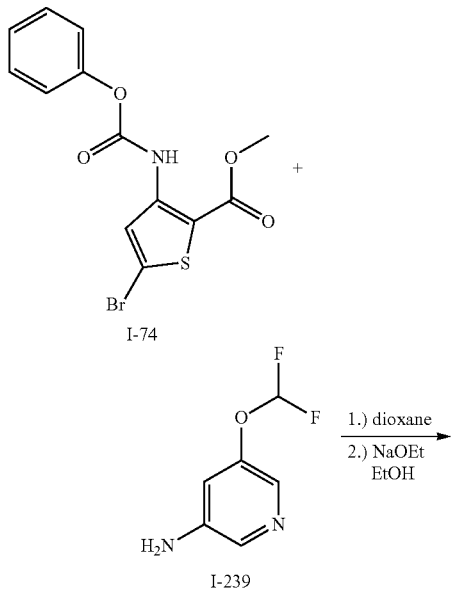

6-bromo-3-[5-(difluoromethoxy)-3-pyridyl]-1H-thieno[3,2-d]pyrimidine-2,4-dione: To a suspension of methyl 5-bromo-3-(phenoxycarbonylamino)thiophene-2-carboxylate (1-74) (780 g, 2.19 mmol) in dioxane (7.4 mL) was added 5-(difluoromethoxy)pyridin-3-amine (HCl salt) (1-239) (517 mg, 2.63 mmol), N,N-Diisopropylethylamine (1.19 mL, 2.63 mmol). The reaction mixture was stirred at 95° C. overnight. After which the reaction mixture was concentrated and move to the next step without further purification. The crude mixture was suspended in EtOH (12 mL), and to the mixture was added sodium ethoxide (21% wt. in EtOH; 2.75 mL, 8.76 mmol) at room temperature dropwise, and the reaction was stirred for 2 hours at room temperature. Solvent was removed under reduced pressure, and EtOAc (6 mL), HCl (1N, 6 mL) were added respectively. The mixture was stirred at 0° C., whereupon a precipitate formed. The solid was collected via filtration and dried over air to deliver the product as an HCl salt.

ES/MS: 389.70 [M+].

3-[6-bromo-3-[5-(difluoromethoxy)-3-pyridyl]-2,4-dioxo-thieno[3,2-d]pyrimidin-1-yl]propanenitrile (I-247): To a 40 mL vial with 6-bromo-3-[15-(difluoromethoxy)-3-pyridyl]-1H-thieno[3,2-d]pyrimidine-2,4-dione (HCl salt) (850 mg, 2.0) mmol) in DMF (5 mL) was added acrylonitrile (7.86 mL, 120 mmol) followed by DBU (0.90 mL, 6.00 mmol). The reaction mixture was heated at 80° C. for 16 hours, after which the mixture was cooled to room temperature. The mixture was concentrated under reduced pressure, and the crude material was dissolved in DCM and dry-loaded onto silica. The material was purified by silica chromatography (eluent: EtOAc in hexanes) to provide the product.

ES/MS: 444.60 [M+H+].

Preparation of Intermediate I-248

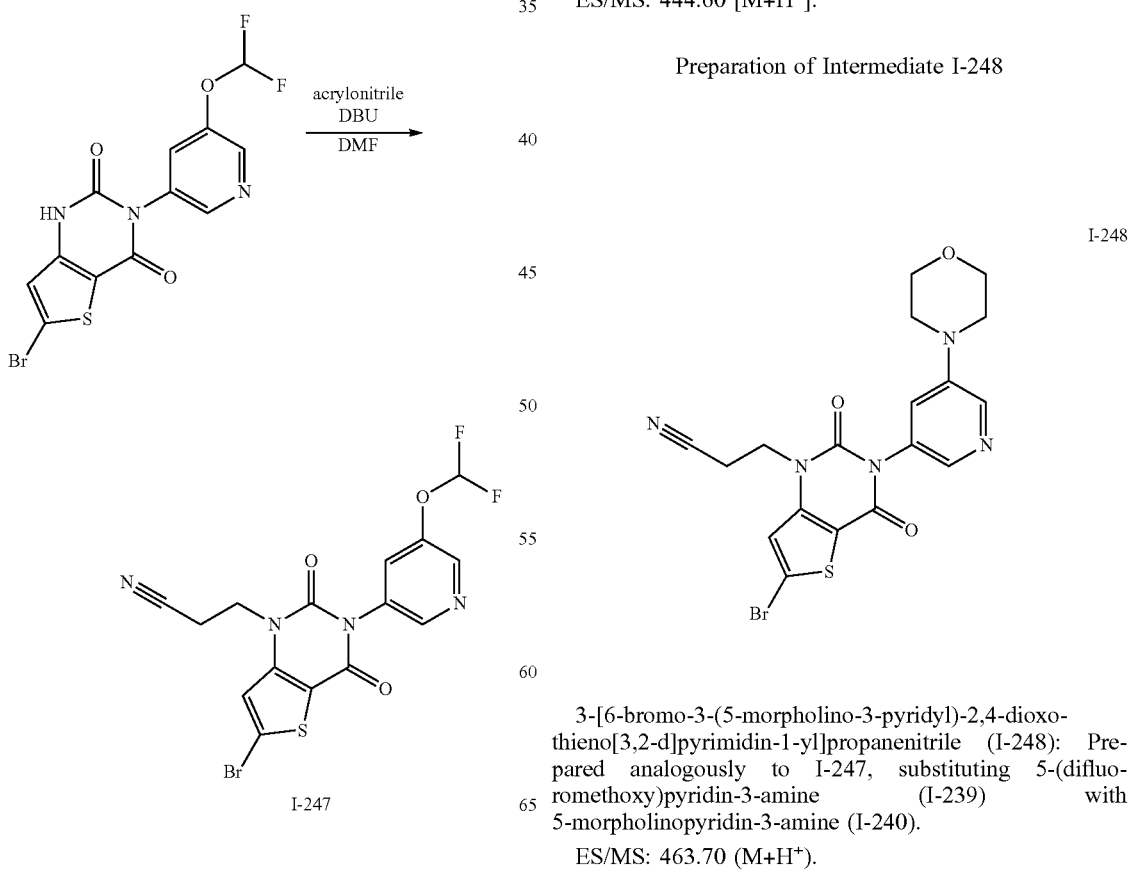

3-[6-bromo-3-(5-morpholino-3-pyridyl)-2,4-dioxo-thieno[3,2-d]pyrimidin-1-yl]propanenitrile (I-248): Prepared analogously to I-247, substituting 5-(difluoromethoxy)pyridin-3-amine (I-239) with 5-morpholinopyridin-3-amine (I-240).

ES/MS: 463.70 (M+H+).

Preparation of Intermediate I-249

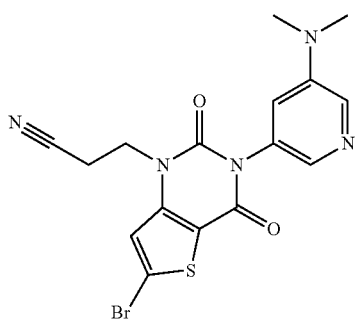

3-[6-bromo-3-[5-(dimethylamino)-3-pyridyl]-2,4-dioxo-thieno[3,2-d]pyrimidin-1-yl]propanenitrile (I-249): Prepared analogously to I-247, substituting 5-(difluoromethoxy)pyridin-3-amine (I-239) with N5,N5-dimethylpyridine-3,5-diamine (I-241).
ES/MS: 421.70 (M+H$^+$).

Preparation of Intermediate I-250

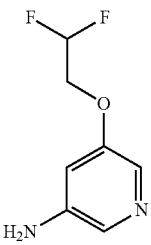

5-(2,2-difluoroethoxy)pyridin-3-amine (I-250): Prepared analogously to I-173, substituting 2,2,2-trifluoroethanol with 2,2-difluoroethanol.
ES/MS: 175.00 (M+H$^+$).

Preparation of Intermediate I-251

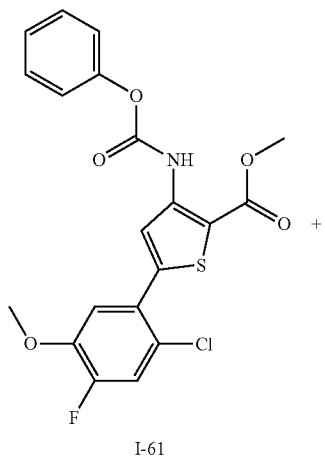

I-61

-continued

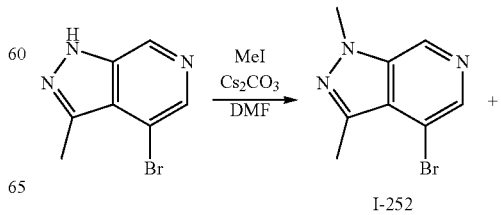

6-(2-chloro-4-fluoro-5-methoxy-phenyl)-3-[5-(2,2-difluoroethoxy)-3-pyridyl]-1H-thieno[3,2-d]pyrimidine-2,4-dione (I-251): To a suspension of methyl 5-(2-chloro-4-fluoro-5-methoxy-phenyl)-3-(phenoxycarbonylamino)thiophene-2-carboxylate (I-61) (940 mg, 2.16 mmol) in dioxane (7 mL) was added 5-(2,2-difluoroethoxy)pyridin-3-amine (I-250) (451 mg, 2.59 mmol), DIPEA (1.18 mL, 8.63 mmol). The reaction mixture was stirred at 95° C. overnight. After which the reaction mixture was concentrated and moved to the next step without further purification. The crude mixture was suspended in EtOH (12.5 mL), and to the mixture was added sodium ethoxide (21% wt. in EtOH; 2.71 mL, 8.64 mmol) at room temperature dropwise, and the reaction was stirred for 2 hours at room temperature. Solvent was removed under reduced pressure, and EtOAc (10 mL), HCl (1N, 10 mL) were added respectively. The mixture was stirred at 0° C., whereupon a precipitate formed. The solid was collected via filtration and dried over air to deliver the product as an HCl salt.
ES/MS: 483.70 [M$^+$].

Preparation of Intermediates I-252 and I-253

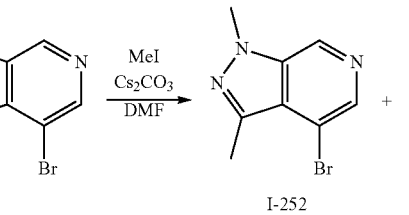

-continued

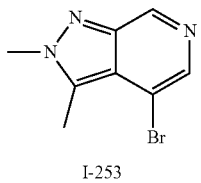

I-253

4-bromo-1,3-dimethyl-1H-pyrazolo[3,4-c]pyridine (1-252) and 4-bromo-2,3-dimethyl-2H-pyrazolo[3,4-c]pyridine (1-253): To 4-bromo-3-methyl-1H-pyrazolo[3,4-c]pyridine (500 mg, 2.4 mmol, 1 equiv.) in DMF (1.2 mL) was added $Cs_2CO_3$ (768 mg, 2.4 mmol, 1 equiv.) followed by MeI (0.16 mL, 2.6 mmol, 1.1 equiv.). After 16 h, the mixture was filtered, diluted with EtOAc (50 mL), washed with brine (5×30 mL), dried over $Na_2SO_4$, and concentrated in vacuo. Purification by column chromatography (EtOAc/hex followed by MeOH/EtOAc) gave 4-bromo-1,3-dimethyl-1H-pyrazolo[3,4-c]pyridine (I-252) (first eluting) and 4-bromo-2,3-dimethyl-2H-pyrazolo[3,4-c]pyridine (1-253) (second eluting).

I-252:
ES/MS: 225.9 (M+H$^+$).
$^1$H NMR (400 MHz, DMSO-d$_6$) δ 9.09 (s, 1H), 8.30 (s, 1H), 4.10 (s, 3H), 2.66 (s, 3H).

I-253:
ES/MS: 225.9 (M+H$^+$).
$^1$H NMR (400 MHz, DMSO-d$_6$) δ 9.03 (s, 1H), 8.12 (s, 1H), 4.15 (s, 3H), 2.80 (s, 3H).

Preparation of Intermediate I-254

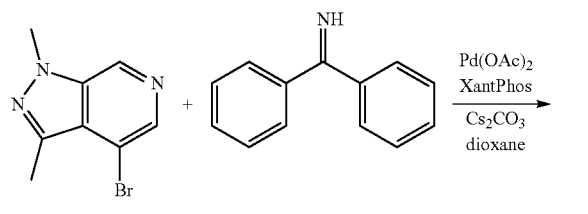

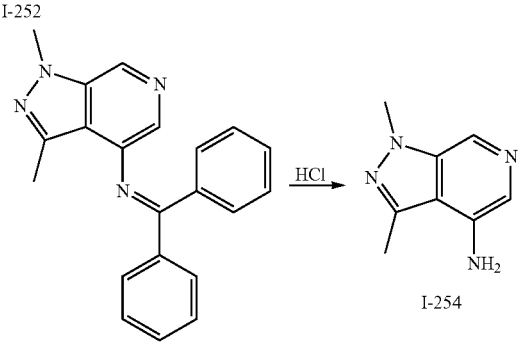

N-(1,3-dimethyl-1H-pyrazolo[3,4-c]pyridin-4-yl)-1,1-diphenylmethanimine: To 4-bromo-1,3-dimethyl-1H-pyrazolo[3,4-c]pyridine (1-252) (276 mg, 1.2 mmol, 1 equiv.), Pd(OAc)$_2$ (27 mg, 0.12 mmol, 0.1 equiv.), Xantphos (141 mg, 0.24 mmol, 0.2 equiv.), and $Cs_2CO_3$ (397 mg, 1.2 mmol, 1 equiv.) in dioxane (6 mL) was added benzophenone imine (0.25 mL, 1.5 mmol, 1.2 equiv.), and the mixture was sparged with Ar for 15 min, sealed, and heated to 100° C. After 16 h, the mixture was cooled to ambient temperature, diluted with EtOAc, filtered, and concentrated in vacuo. Purification by column chromatography (EtOAc/hex) gave the product.
ES/MS: 327.00 [M+H].

1,3-dimethyl-1H-pyrazolo[3,4-c]pyridin-4-amine (I-254): To N-(1,3-dimethyl-1H-pyrazolo[3,4-c]pyridin-4-yl)-1,1-diphenylmethanimine (353 mg, 1.1 mmol, 1 equiv.) in 2-MeTHF (5.4 mL) was added 1 M HCl(aq) (5.4 mL). After two hours, the layers were separated. The aqueous was washed with 50% EtOAc/hex (2×) and then basified with solid NaOH. The aqueous was then extracted with EtOAc (3×). The combined organics were dried over $Na_2SO_4$ and concentrated in vacuo to afford the product.
ES/MS: 163.09 (M+H$^+$).

Preparation of Intermediate I-255

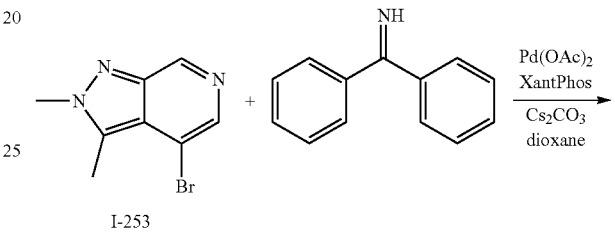

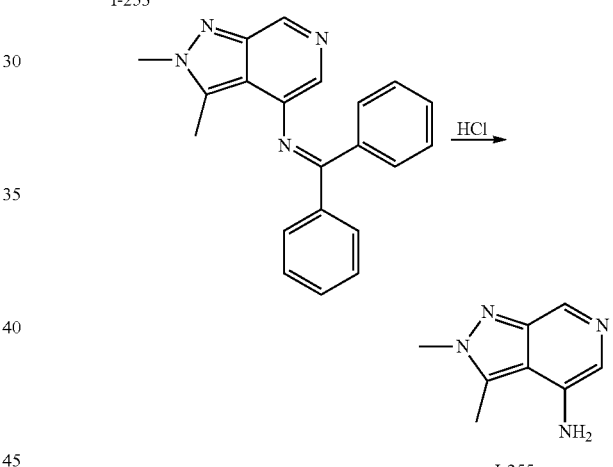

N-(2,3-dimethyl-2H-pyrazolo[3,4-c]pyridin-4-yl)-1,1-diphenylmethanimine: To 4-bromo-2,3-dimethyl-2H-pyrazolo[3,4-c]pyridine (1-253) (582 g, 2.6 mmol, 1 equiv.), Pd(OAc)$_2$ (58 mg, 0.26 mmol, 0.1 equiv.), Xantphos (298 mg, 0.52 mmol, 0.2 equiv.), and $Cs_2CO_3$ (839 mg, 2.6 mmol, 1 equiv.) in dioxane (13 mL) was added benzophenone imine (0.52 mL, 3.1 mmol, 1.2 equiv.), and the mixture was sparged with Ar for 15 min, sealed, and heated to 100° C. After 16 h, the mixture was cooled to ambient temperature, diluted with EtOAc, filtered, and concentrated in vacuo. Purification by column chromatography (MeOH/EtOAc) gave the product.
ES/MS m/z: 327.00 [M+H].

2,3-dimethyl-2H-pyrazolo[3,4-c]pyridin-4-amine (I-255): To N-(2,3-dimethyl-2H-pyrazolo[3,4-c]pyridin-4-yl)-1,1-diphenylmethanimine (108 mg, 0.33 mmol, 1 equiv.) in 2-MeTHF (2 mL) was added 1 M HCl(aq) (2 mL). After two hours, the layers were separated. The aqueous layer was washed with 50% EtOAc/hex (2×) and then basified with solid NaOH. The aqueous layer was then extracted with

Preparation of Intermediate I-256

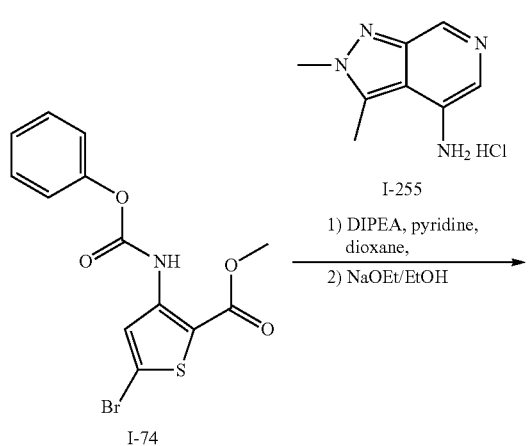

Preparation of Intermediate I-257

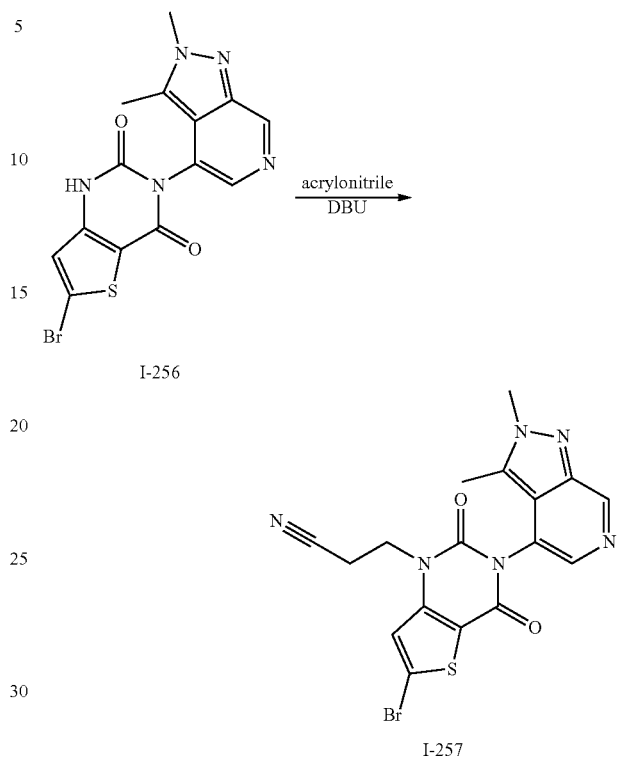

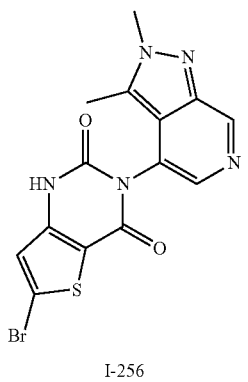

3-(6-bromo-3-(2,3-dimethyl-2H-pyrazolo[3,4-c]pyridin-4-yl)-2,4-dioxo-3,4-dihydrothieno[3,2-d]pyrimidin-1(2H)-yl)propanenitrile (I-257): To crude 6-bromo-3-(2,3-dimethyl-2H-pyrazolo[3,4-c]pyridin-4-yl)thieno[3,2-d]pyrimidine-2,4(1H,3H)-dione (I-256) was added acrylonitrile (19 mL) followed by DBU (0.97 mL, 6.5 mmol) and heated to 80° C. for 18 h. The mixture was then cooled to ambient temperature filtered and concentrated in vacuo. Purification by silica chromatography (EtOAc/hexanes followed by MeOH/EtOAc) provided the product.

ES/MS: 444.8 (M+H$^+$).

Preparation of Intermediate I-258

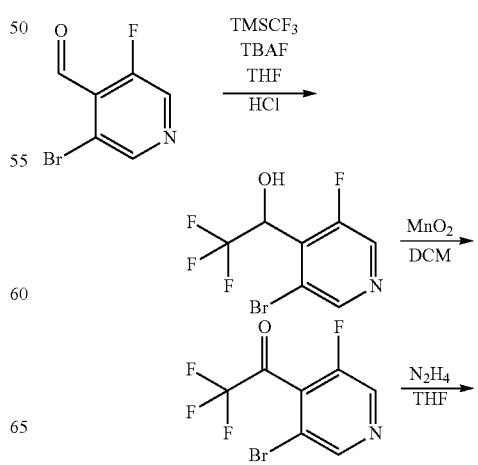

EtOAc (4×) and MeCN (2×). The combined organics were dried over Na$_2$SO$_4$ and concentrated in vacuo to afford the product.

ES/MS: 163.09 (M+H$^+$).

6-bromo-3-(2,3-dimethyl-2H-pyrazolo[3,4-c]pyridin-4-yl)thieno[3,2-d]pyrimidine-2,4(1H,3H)-dione (I-256): To a suspension of methyl 5-bromo-3-((phenoxycarbonyl)amino)thiophene-2-carboxylate (I-74) (755 mg, 2.1 mmol, 1.0 equiv.) and 2,3-dimethyl-2H-pyrazolo[3,4-c]pyridin-4-amine hydrochloride (I-255) (463 mg, 2.3 mmol, 1.1 equiv.) in 1,4-dioxane (9 mL) was added DIPEA (1.6 mL, 1.8 mmol, 4.4 equiv) and pyridine (0.17 mL, 2.1 mmol, 1 equiv.), and the mixture was heated to 90° C. After 24 h, the reaction mixture was cooled to ambient temperature and ethanol (4 mL) and 20 wt % sodium ethoxide in ethanol (5 mL) were added. After 1 h, the mixture was concentrated under reduced pressure. To the resulting mixture, 1 M HCl (20 mL) and EtOAc (20 mL) were added. The mixture was filtered and the layers were separated. The aqueous was concentrated in vacuo and added to the dried filtered solids to give crude product that was used without further purification.

ES/MS: 391.8 (M+H$^+$).

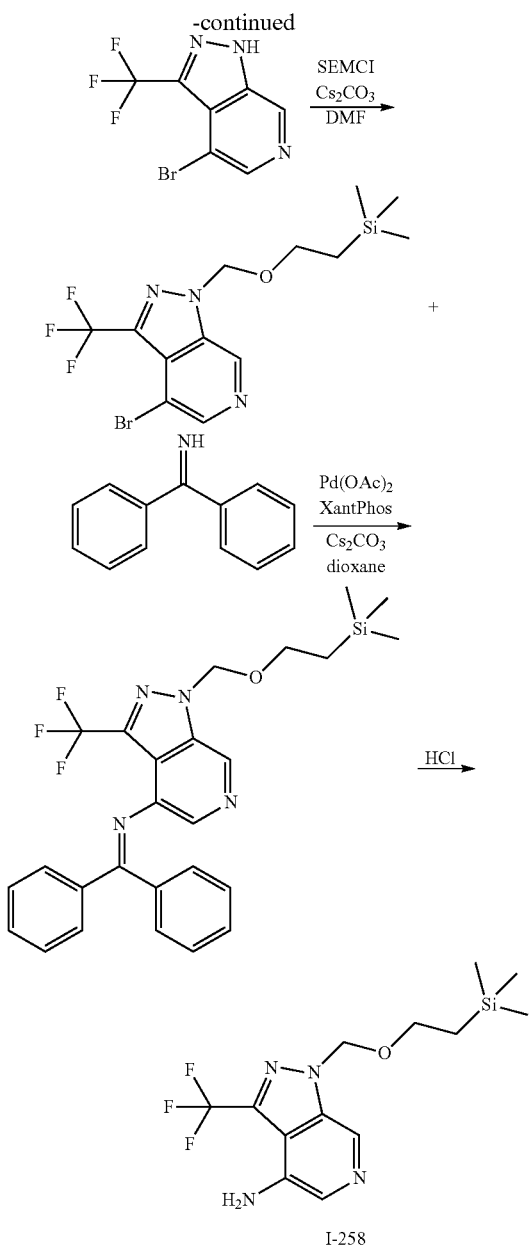

I-258

1-(3-bromo-5-fluoropyridin-4-yl)-2,2,2-trifluoroethan-1-ol: To 3-bromo-5-fluoroisonicotinaldehyde (500 mg, 2.5 mmol, 1 equiv.) in THF (7.5 mL) at 0° C. was added TMSCF₃ (2 M in THF, 1.9 mL, 3.8 mmol, 1.5 equiv.) followed by TBAF solution (1 M in THF, 0.2 mL, 0.2 mmol, 0.08 equiv.). After 1 h, 1 M HCl(aq) (7.5 mL) was added. After 10 min, the mixture was neutralized with solid NaOH and adjusted with 1 M NaOH(aq). The mixture was extracted with EtOAc (2×10 mL). The combined organics were washed with brine, dried over Na₂SO₄, and concentrated in vacuo. Purification by silica chromatography (EtOAc/hexanes) provided the product.

ES/MS: 273.8 (M+H⁺).

1-(3-bromo-5-fluoropyridin-4-yl)-2,2,2-trifluoroethan-1-one: To 1-(3-bromo-5-fluoropyridin-4-yl)-2,2,2-trifluoroethan-1-ol (6.0 g, 22 mmol, 1 equiv.) in DCM (220 mL) was added activated MnO₂ (19 g, 220 mmol, 10 equiv.). After 24 h, more MnO₂ (9.5 g, 110 mmol, 5 equiv.) was added. After 24 h, the mixture was filtered through celite, rinsed with DCM, and concentrated n vacuo to provide crude product that was used without further purification.

ES/MS: 289.8 (M+H⁺).

4-bromo-3-(trifluoromethyl)-1H-pyrazolo[3,4-c]pyridine: To 1-(3-bromo-5-fluoropyridin-4-yl)-2,2,2-trifluoroethan-1-one (570 mg, 2.1 mmol, 1 equiv.) in THF (10 mL) in a sealed vial was added hydrazine solution (1 M in THF, 2.5 mL, 2.5 mmol, 1.2 equiv.) and the mixture was heated to reflux. After 18 h, the reaction mixture was concentrated in vacuo. Purification by silica chromatography (EtOAc/hexanes) provided the product.

ES/MS: 265.8 (M+H⁺).

4-bromo-3-(trifluoromethyl)-1-((2-(trimethylsilyl)ethoxy)methyl)-1H-pyrazolo[3,4-c]pyridine: To 4-bromo-3-(trifluoromethyl)-1H-pyrazolo[3,4-c]pyridine (280 mg, 1.0 mmol, 1 equiv.) in DMF (3.5 mL) was added Cs₂CO₃ (676 mg, 2.1 mmol, 2 equiv.) followed by SEMCl (0.37 mL, 2.1 mmol, 2 equiv.). After 18 h, the reaction mixture was filtered through celite and rinsed with EtOAc. The solution was washed with brine (5×20 mL), dried over Na₂SO₄, and concentrated in vacuo. Purification by silica chromatography (EtOAc/hexanes) provided the product.

ES/MS: 395.8 (M+H⁺).

1,1-diphenyl-N-(3-(trifluoromethyl)-1-((2-(trimethylsilyl)ethoxy)methyl)-1H-pyrazolo[3,4-c]pyridin-4-yl)methanimine: A mixture of 4-bromo-3-(trifluoromethyl)-1-((2-(trimethylsilyl)ethoxy)methyl)-1H-pyrazolo[3,4-c]pyridine (360 mg, 0.91 mmol, 1 equiv.), benzophenone imine (0.18 mL, 1.1 mmol, 1.2 equiv.), Pd(OAc)₂ (20 mg, 0.09 mmol, 0.1 equiv.), XantPhos (105 mg, 0.18 mmol, 0.2 equiv.), and Cs₂CO₃ (296 mg, 0.91 mmol, 1 equiv.) in 1,4-dioxane (4.5 mL) was sparged with Ar for 15 min and then heated to 100° C. After 18 h, the mixture was cooled to ambient temperature, diluted with EtOAc, filtered through celite, rinsed with EtOAc, and concentrated in vacuo. Purification by silica chromatography (EtOAc/hexanes) provided the product.

ES/MS: 497.0 (M+H⁺).

3-(trifluoromethyl)-1-((2-(trimethylsilyl)ethoxy)methyl)-1H-pyrazolo[3,4-c]pyridin-4-amine (I-258): To 1,1-diphenyl-N-(3-(trifluoromethyl)-1-((2-(trimethylsilyl)ethoxy)methyl)-1H-pyrazolo[3,4-c]pyridin-4-yl)methanimine (400 mg, 0.81 mmol, 1 equiv.) in THF (4 mL) was added 1 M HCl(aq) (4 mL). After 16 h, the mixture was diluted with 50% EtOAc/hexane, the layers were separated, and the organics were extracted with 1 M HCl(aq). The combined aqueous was basified with K₂CO₃. The mixture was extracted with EtOAc, dried over Na₂SO₄, and concentrated in vacuo to provide the product.

ES/MS: 333.0 (M+H⁺).

Preparation of Intermediate I-259

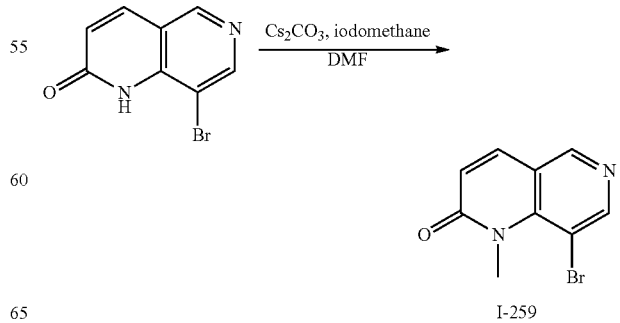

I-259

8-bromo-1-methyl-1,6-naphthyridin-2(1H)-one (I-259): To a suspension 8-bromo-1,6-naphthyridin-2(1H)-one (as described in the preparation of I-88) (500 mg, 2.2 mmol) in DMF (5 mL) was added cesium carbonate (724 mg, 2.2 mmol) and iodomethane (0.14 ml, 2.2 mmol). The reaction mixture was stirred at RT overnight. The reaction was filtered to remove solids and concentrated. The residue was purified by flash column chromatography to obtain the desired product.

ES/MS: 239.1 [M*].

Preparation of Intermediate I-260

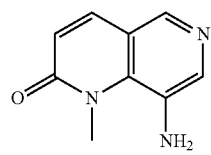

8-amino-1-methyl-1,6-naphthyridin-2(1H)-one (I-260): Prepared analogously to I-32, substituting 4-chlorocinnoline with 8-bromo-1-methyl-1,6-naphthyridin-2(1H)-one (I-259).

ES/MS: 176.2 (M+H$^+$).

Preparation of Intermediate I-261

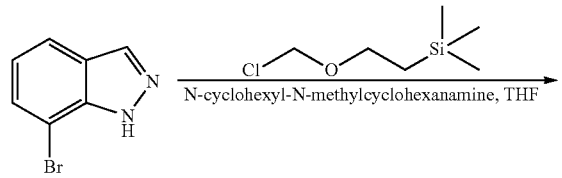

7-bromo-2-((2-(trimethylsilyl)ethoxy)methyl)-2H-indazole (I-261): To a suspension 7-bromo-1H-indazole (750 mg, 3.8 mmol) in THF (5 mL) was added N-cyclohexyl-N-methylcyclohexanamine (1 ml, 4.9 mmol) and (2-(chloromethoxy)ethyl)trimethylsilane (1 ml, 5.7 mmol). The reaction mixture was stirred at RT overnight. The reaction was concentrated. The residue was purified by flash column chromatography to obtain the desired product.

ES/MS: 329.9 [M$^+$].

Preparation of Intermediate I-262

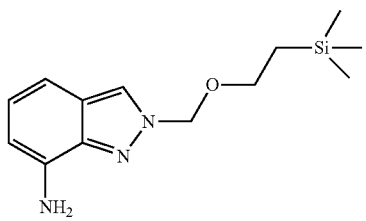

2-((2-(trimethylsilyl)ethoxy)methyl)-2H-indazol-7-amine (I-262): Prepared analogously to I-32, substituting 4-chlorocinnoline with 7-bromo-2-((2-(trimethylsilyl)ethoxy)methyl)-2H-indazole (I-261).

ES/MS: 265.1 (M+H$^+$).

Preparation of Intermediate I-263

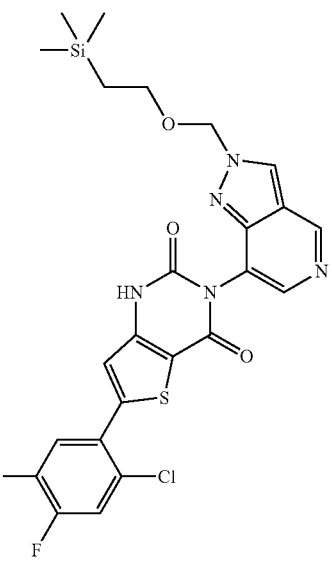

6-(2-chloro-4-fluoro-5-methoxyphenyl)-3-(2-((2-(trimethylsilyl)ethoxy)methyl)-2H-pyrazolo[4,3-c]pyridin-7-yl)thieno[3,2-d]pyrimidine-2,4(1H,3H)-dione (I-263): Prepared analogously to Example 453, substituting I-64 with I-66 and I-91 with 2-((2-(trimethylsilyl)ethoxy)methyl)-2H-indazol-7-amine (I-262).

ES/MS: 574.3 (M+H$^+$).

Preparation of Intermediate I-264

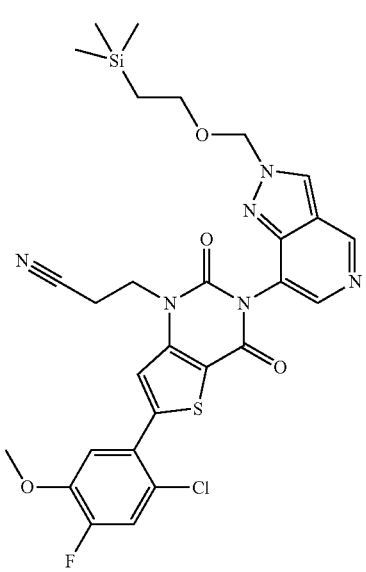

3-(6-(2-chloro-4-fluoro-5-methoxyphenyl)-2,4-dioxo-3-(2-((2-(trimethylsilyl)ethoxy)methyl)-2H-pyrazolo[4,3-c]pyridin-7-yl)-3,4-dihydrothieno[3,2-d]pyrimidin-1(2H)-yl)propanenitrile (I-264): Prepared analogously to Example 901 (from Procedure 105), substituting Example 899 with I-263

ES/MS: 627.1 (M+H$^+$).

Preparation of Intermediate I-265

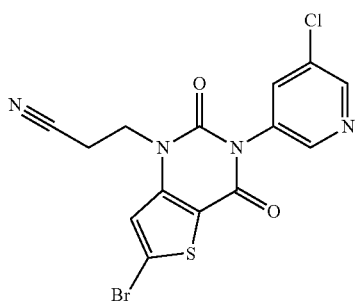

3-(6-bromo-3-(5-chloropyridin-3-yl)-2,4-dioxo-3,4-dihydrothieno[3,2-d]pyrimidin-1(2H)-yl)propanenitrile (I-265): Prepared analogously to I-195, substituting 1,2-dimethylimidazo[4,5-c]pyridin-7-amine (I-192) with 5-chloropyridin-3-amine.

ES/MS: 413.1 (M$^+$).

Preparation of Intermediate I-266

3-(6-bromo-3-(5-fluoropyridin-3-yl)-2,4-dioxo-3,4-dihydrothieno[3,2-d]pyrimidin-1(2H)-yl)propanenitrile (I-266): Prepared analogously to I-195, substituting 1,2-dimethylimidazo[4,5-c]pyridin-7-amine (I-192) with 5-fluoropyridin-3-amine.

ES/MS: 395.3 (M$^+$).

Preparation of Intermediate I-267

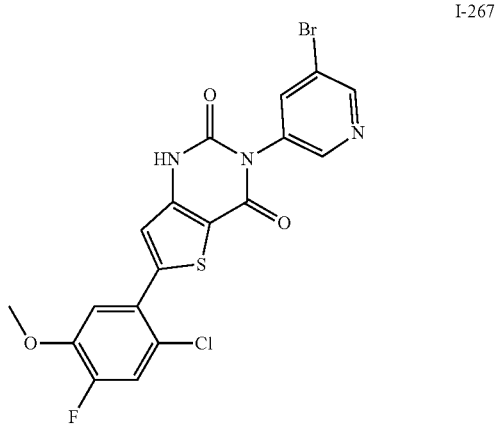 [SMILES: COc1cc(-c2cc3[nH]c(=O)n(-c4cncc(Br)c4)c(=O)c3s2)c(Cl)cc1F]

3-(5-bromopyridin-3-yl)-6-(2-chloro-4-fluoro-5-methoxyphenyl)thieno[3,2-d]pyrimidine-2,4(1H,3H)-dione (I-267): Prepared analogously to Example 453, substituting I-64 with I-66 and I-91 with 5-bromopyridin-3-amine.

ES/MS: 484.0 (M+H$^+$).

Preparation of Intermediate I-268

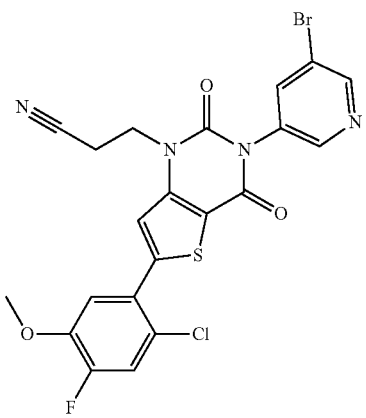

3-(3-(5-bromopyridin-3-yl)-6-(2-chloro-4-fluoro-5-methoxyphenyl)-2,4-dioxo-3,4-dihydrothieno[3,2-d]pyrimidin-1(2H)-yl)propanenitrile (I-268): Prepared analogously to Example 901, substituting 6-(2-chloro-4-fluoro-5-methoxyphenyl)-3-(5-fluoroisoquinolin-4-yl)thieno[3,2-d]pyrimidine-2,4(1H,3H)-dione (Example 899) with 3-(5-bromopyridin-3-yl)-6-(2-chloro-4-fluoro-5-methoxyphenyl)thieno[3,2-d]pyrimidine-2,4(1H,3H)-dione (I-267).

ES/MS: 537.0 (M+).

Preparation of Intermediate I-269

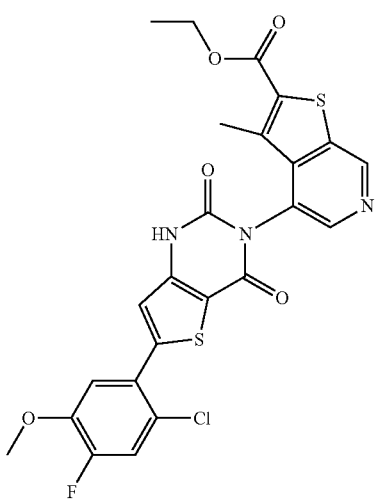

Ethyl 4-(6-(2-chloro-4-fluoro-5-methoxyphenyl)-2,4-dioxo-1,4-dihydrothieno[3,2-d]pyrimidin-3(2H)-yl)-3-methylthieno[2,3-c]pyridine-2-carboxylate (I-269): Prepared analogously to I-154, substituting I-62 with I-61.

ES/MS: 546.7 (M+). Preparation of intermediate I-270:

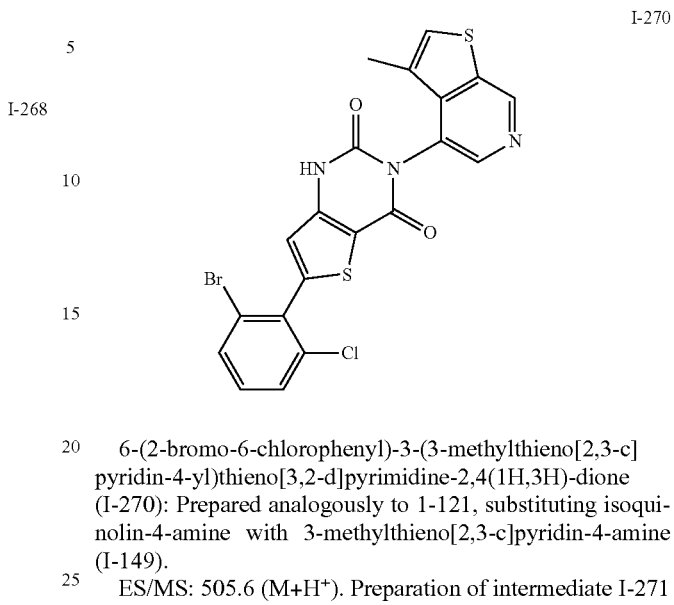

6-(2-bromo-6-chlorophenyl)-3-(3-methylthieno[2,3-c]pyridin-4-yl)thieno[3,2-d]pyrimidine-2,4(1H,3H)-dione (I-270): Prepared analogously to I-121, substituting isoquinolin-4-amine with 3-methylthieno[2,3-c]pyridin-4-amine (I-149).

ES/MS: 505.6 (M+H+). Preparation of intermediate I-271

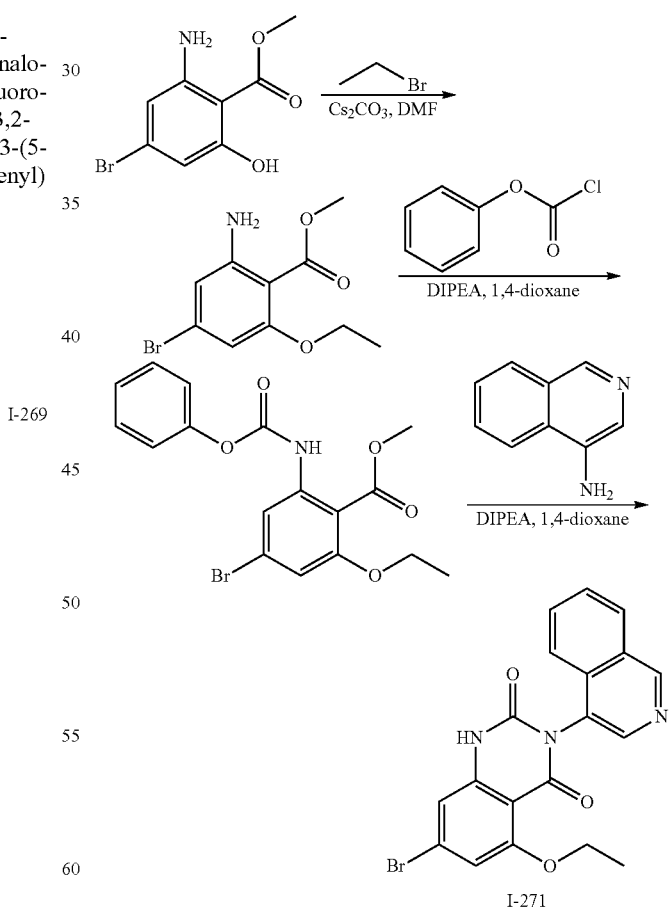

Methyl 2-amino-4-bromo-6-ethoxy-benzoate: A solution of methyl 2-amino-4-bromo-6-hydroxy-benzoate (400 mg, 1.63 mmol) in anhydrous DMF (4 mL) was treated with $Cs_2CO_3$ (583 mg, 1.79 mmol), cooled to 0° C., stirred for 10 minutes, treated with a solution of bromoethane (182 uL, 266 mg, 2.44 mmol) in DMF (0.6 mL), warmed to room temperature and stirred for 3 hours. The reaction mixture was diluted with brine and extracted with ethyl acetate. The organic solution was dried over MgSO₄, filtered and concentrated. The residue product was purified by flush chromatography eluting with a mixture of ethyl acetate and hexane to provide methyl 2-amino-4-bromo-6-ethoxy-benzoate.

ES/MS: 275.9 (M+H⁺).

7-bromo-5-ethoxy-3-(4-isoquinolyl)-1H-quinazoline-2,4-dione (I-271)

To a stirring solution of methyl 2-amino-4-bromo-6-ethoxy-benzoate (150 mg, 0.55 mmol) in dioxane (6 mL) was added phenyl chloroformate (0.11 mL, 0.82 mmol) and DIPEA (0.91 mL, 1.09 mmol). The reaction mixture was heated to 90° C. and stirred for 3 h. The reaction mixture was cooled to rt and additional DIPEA (0.91 mL) and isoquinolin-4-amine (94.7 mg, 0.66 mmol) were added. The resulting reaction mixture was stirred overnight at 90° C. The volatiles were removed under reduced pressure, dissolved in a solution of CH₃CN/H₂O/TFA, filtered through an acrodisc and subsequently purified by RP-HPLC (0.1% TFA-ACN in 0.1% TFA Water, Column: Gemini 5 uM, NX-C18 110 Angstrom, 250×21.2 mm) to give 7-bromo-5-ethoxy-3-(isoquinolin-4-yl)quinazoline-2,4(1H,3H)-dione (I-271) as a TFA salt.

ES/MS: 411.8 (M⁺).

Preparation of Intermediate I-272

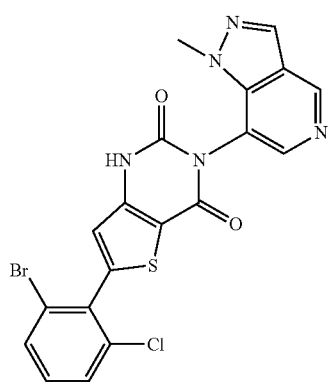

6-(2-bromo-6-chlorophenyl)-3-(1-methyl-1H-pyrazolo[4,3-c]pyridin-7-yl)thieno[3,2-d]pyrimidine-2,4(1H,3H)-dione (I-272): Prepared analogously to I-121, substituting isoquinolin-4-amine with 1-methylpyrazolo[4,3-c]pyridin-7-amine (I-183).

ES/MS: 489.7 (M+H⁺).

Preparation of Intermediate I-274

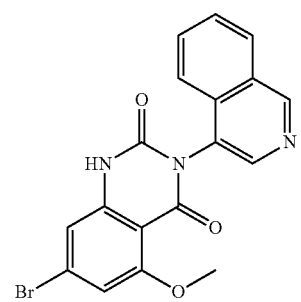

7-bromo-3-(isoquinolin-4-yl)-5-methoxyquinazoline-2,4(1H,3H)-dione (I-274)

Prepared analogously to I-271, substituting bromoethane with iodomethane.

ES/MS: 398.8 (M⁺).

Preparation of Intermediate I-275

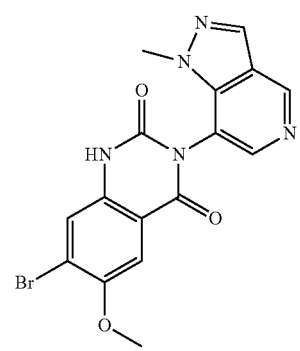

7-bromo-5-methoxy-3-(1-methyl-1H-pyrazolo[4,3-c]pyridin-7-yl)quinazoline-2,4(1H,3H)-dione (I-275): Prepared analogously to 1-19, substituting isoquinolin-4-amine with 1-methylpyrazolo[4,3-c]pyridin-7-amine (I-183).

ES/MS: 401.8 (M⁺).

Preparation of Intermediate I-276

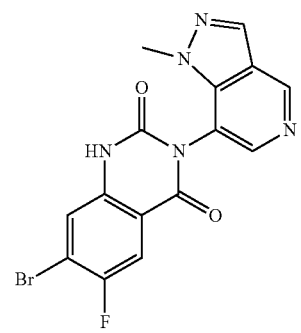

7-bromo-5-methoxy-3-(1-methyl-1H-pyrazolo[4,3-c]pyridin-7-yl)quinazoline-2,4(1H,3H)-dione (I-276): Prepared analogously to 1-3, substituting isoquinolin-4-amine with 1-methylpyrazolo[4,3-c]pyridin-7-amine (I-183).

ES/MS: 389.8 (M+).

Preparation of Intermediate I-278

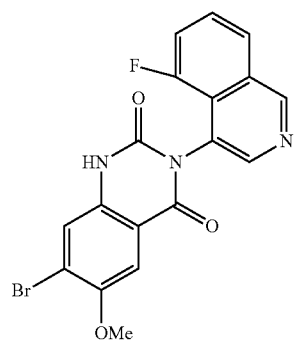

I-278

7-bromo-3-(5-fluoroisoquinolin-4-yl)-6-methoxyquinazoline-2,4(1H,3H)-dione (1-278): Prepared analogously to 1-19, substituting isoquinolin-4-amine with 5-fluoroisoquinolin-4-amine.

ES/MS: 417.8 (M+H+).

Preparation of Intermediate I-279

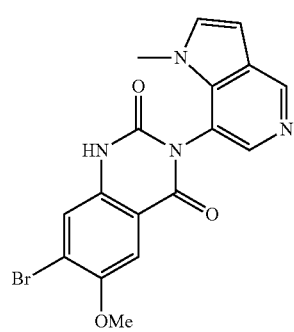

I-279

7-bromo-6-methoxy-3-(1-methyl-1H-pyrrolo[3,2-c]pyridin-7-yl)quinazoline-2,4(1H,3H)-dione (I-279): Prepared analogously to 1-19, substituting isoquinolin-4-amine with 1-methyl-1H-pyrrolo[3,2-c]pyridin-7-amine (I-85).

ES/MS: 400.8 (M+).

Preparation of Intermediate I-280

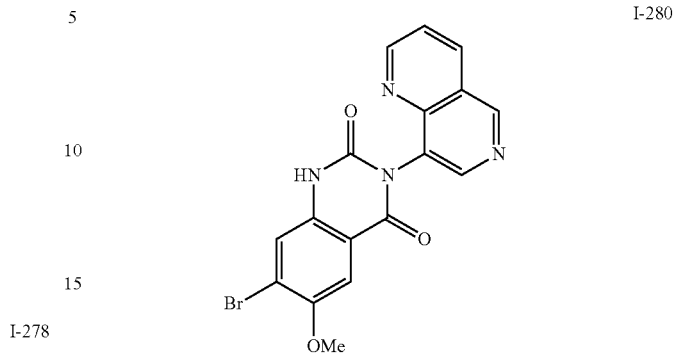

I-280

7-bromo-6-methoxy-3-(1,6-naphthyridin-8-yl)quinazoline-2,4(1H,3H)-dione (I-280): Prepared analogously to 1-19, substituting isoquinolin-4-amine with 1,6-naphthyridin-8-amine (I-36).

ES/MS: 400.7 (M+H+).

Preparation of Intermediate I-281

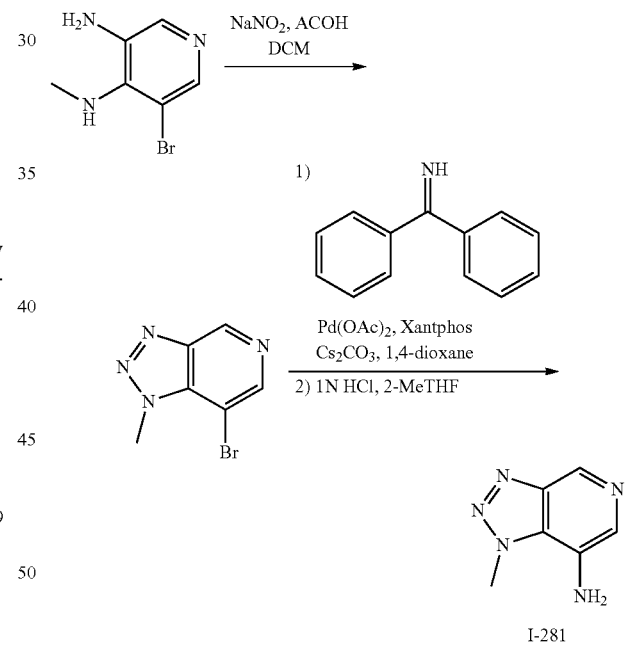

I-281

7-bromo-1-methyl-triazolo[4,5-c]pyridine: A mixture of 5-bromo-N4-methyl-pyridine-3,4-diamine (1.0 g, 4.95 mmol) in DCM (21 mL) and AcOH (1 mL) was cooled to 0 °C. and sodium nitrite (1.13 g, 16.30 mmol) was added in small portions. After 30 min of stirring at 0° C., the reaction mixture was warmed to room temperature and stirred for 2 h. The mixture was neutralized with sat. aq. NaHCO3 at 0° C. and extracted with DCM (3×30 mL). The combined organic layers were washed with brine (30 mL), dried over anhydrous Mg2SO4, filtered, and concentrated. The resulting crude residue product was purified by silica gel chromatography (gradient elution: 50-100% EtOAc/petroleum ether) to provide the title compound.

ES/MS: 212.9 (M+).

1H NMR (400 MHz, Chloroform-d) δ 9.39 (s, 1H), 8.66 (s, 1H), 4.60 (s, 3H).

1-methyltriazolo[4,5-c]pyridin-7-amine (I-281): To a dram vial was added 7-bromo-1-methyl-triazolo[4,5-c]pyridine (200 mg, 0.94 mmol), diphenylmethanimine (204 mg, 1.13 mmol), Pd(OAc)₂ (21 mg, 0.094 mmol), 9,9-dimethyl-4,5-bis(diphenylphosphino)xanthene (XantPhos) (109 mg, 0.19 mmol) and cesium carbonate (306 mg, 0.94 mmol). Dioxane (5 mL) was added, and the mixture was degassed with argon for 30 seconds. The vial was sealed, and the reaction mixture was heated at 100° C. for 3 hours. The mixture was filtered and subsequently concentrated under reduced pressure. The crude residue was purified by silica gel chromatography (eluent: EtOAc/hexanes) to provide the intermediate [ES/MS: 313.9 (M+)]. The imine intermediate was dissolved in 2-MeTHF (4 mL) and treated with 1N HCl (4 mL). After stirring at rt for 30 min, the reaction mixture was diluted with EtOAc. The layers were separated, and the aqueous layer was basified with K₂CO₃ and extracted with EtOAc. The combined organic layers were dried over MgSO₄, filtered, and concentrated under reduced pressure to provide the title compound.

ES/MS: 150.1 (M+H+).

Preparation of Intermediate I-282

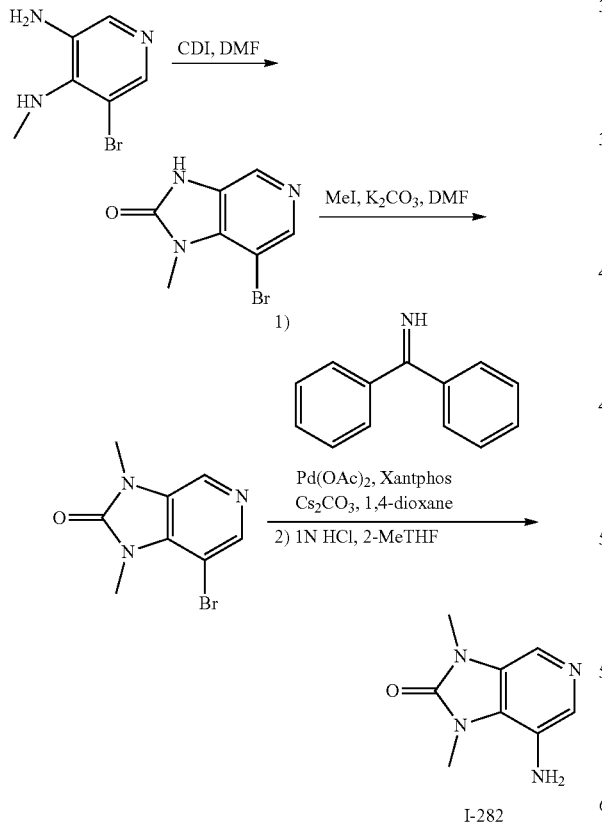

7-bromo-1-methyl-1,3-dihydro-2H-imidazo[4,5-c]pyridin-2-one: To a stirred solution of 5-bromo-N₄-methylpyridine-3,4-diamine (1.0 g, 4.95 mmol) in DMF (50 mL) at 0° C. was added CDI (2.41 g, 14.80 mmol). After stirring at 70° C. for 16 h, the reaction mixture was concentrated under reduced pressure. The solid crude product was washed with EtOAc to provide 7-bromo-1-methyl-1,3-dihydro-2H-imidazo[4,5-c]pyridin-2-one.

ES/MS: 227.9 (M+).

7-bromo-1,3-dimethyl-1,3-dihydro-2H-imidazo[4,5-c]pyridin-2-one: To a mixture of 7-bromo-1-methyl-1,3-dihydro-2H-imidazo[4,5-c]pyridin-2-one (470 mg, 2.06 mmol) and MeI (350 mg, 2.47 mmol) in DMF (2 mL) was added K₂CO₃ (855 mg, 6.18 mmol). The reaction mixture was stirred overnight at 50° C. Upon cooling to room temperature, the reaction mixture was then diluted with EtOAc and washed with water. The organic phase was dried over Na₂SO₄ and concentrated to give the title compound.

ES/MS: 241.9 (M+).

7-amino-1,3-dimethyl-1,3-dihydro-2H-imidazo[4,5-c]pyridin-2-one (I-282): To a dram vial was added 7-bromo-1,3-dimethyl-imidazo[4,5-c]pyridin-2-one (135 mg, 0.56 mmol), diphenylmethanimine (121 mg, 0.67 mmol), Pd(OAc)₂ (12.5 mg, 0.056 mmol), 9,9-dimethyl-4,5-bis(diphenylphosphino)xanthene (XantPhos) (64.5 mg, 0.11 mmol) and cesium carbonate (182 mg, 0.56 mmol). Dioxane (2.5 mL) was added, and the mixture was degassed with argon for 30 seconds. The vial was sealed, and the reaction mixture was heated at 100° C. for 3 hours. The mixture was filtered and subsequently concentrated under reduced pressure. The crude residue was purified by silica gel chromatography (eluent: EtOAc/hexanes). The material was dissolved in 2-MeTHF (4 mL) followed by addition of 1N HCl (4 mL). After stirring at rt for 30 min, the reaction mixture was diluted with EtOAc (30 mL). The layers were separated, and the aqueous layer was basified with K₂CO₃ and extracted with EtOAc (2×20 mL). The combined organic layers were dried over MgSO₄, filtered, and concentrated under reduced pressure to provide the title compound.

ES/MS: 179.0 (M+H+).

Preparation of Intermediate I-283

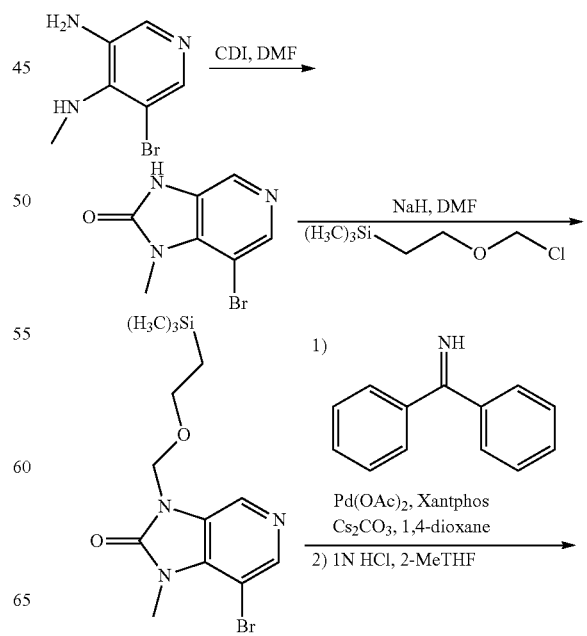

621
-continued

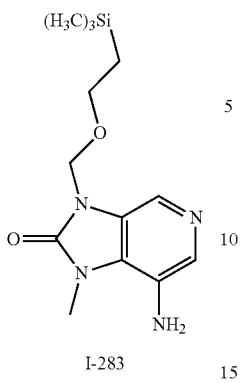

I-283

7-bromo-1-methyl-1,3-dihydro-2H-imidazo[4,5-c]pyridin-2-one: To a stirred solution of 5-bromo-$N_4$-methylpyridine-3,4-diamine (1.0 g, 4.95 mmol) in DMF (50 mL) at 0° C. was added CDI (2.41 g, 14.80 mmol). After stirring at 70° C. for 16 h, the reaction mixture was concentrated under reduced pressure. The solid crude product was washed with EtOAc to provide 7-bromo-1-methyl-1,3-dihydro-2H-imidazo[4,5-c]pyridin-2-one.

ES/MS: 227.9 (M+).

7-bromo-1-methyl-3-((2-(trimethylsilyl)ethoxy)methyl)-1,3-dihydro-2H-imidazo[4,5-c]pyridin-2-one: NaH (60%, 139 mg, 3.63 mmol) was added to a solution of 7-bromo-1-methyl-1,3-dihydro-2H-imidazo[4,5-c]pyridin-2-one in DMF (5 mL) at 0° C. and the resulting reaction mixture was stirred at the same temperature for 1 h. After addition of 2-(trimethylsilyl)ethoxymethyl chloride, the resulting reaction mixture was stirred at room temperature for 1 h. The reaction mixture was poured into an aqueous solution of NaHCO$_3$ (10 mL) and extracted with EtOAc (10 mL). The organic layer was washed with brine (4×10 mL) to remove traces of DMF, dried over Na$_2$SO$_4$, concentrated and purified by flash chromatography to obtain 7-bromo-1-methyl-3-((2-(trimethylsilyl)ethoxy)methyl)-1,3-dihydro-2H-imidazo[4,5-c]pyridin-2-one.

ES/MS: 357.8 (M$^+$).

7-amino-1-methyl-3-((2-(trimethylsilyl)ethoxy)methyl)-1,3-dihydro-2H-imidazo[4,5-c]pyridin-2-one (I-283): To a dram vial was added 7-bromo-1-methyl-3-(2-trimethylsilylethoxymethyl)imidazo[4,5-c]pyridin-2-one (140 mg, 0.39 mmol), diphenylmethanimine (85 mg, 0.47 mmol), Pd(OAc)$_2$ (8.8 mg, 0.039 mmol), 9,9-dimethyl-4,5-bis(diphenylphosphino)xanthene (XantPhos) (45 mg, 0.078 mmol) and cesium carbonate (127 mg, 0.39 mmol). Dioxane (2.5 mL) was added, and the mixture was degassed with argon for 30 seconds. The vial was sealed, and the reaction mixture was heated at 100° C. for 4 hours. The mixture was filtered and subsequently concentrated under reduced pressure. The crude residue was purified by silica gel chromatography (eluent: EtOAc/hexanes). The material was dissolved in 2-MeTHF (4 mL) followed by addition of 1N HCl (4 mL). After stirring at rt for 30 min, the reaction mixture was diluted with EtOAc (30 mL). The layers were separated, and the aqueous layer was basified with K$_2$CO$_3$ and extracted with EtOAc (2×20 mL). The combined organic layers were dried over MgSO$_4$, filtered, and concentrated under reduced pressure to provide the title compound.

ES/MS: 295.0 (M+H$^+$).

622

Preparation of Intermediate I-284

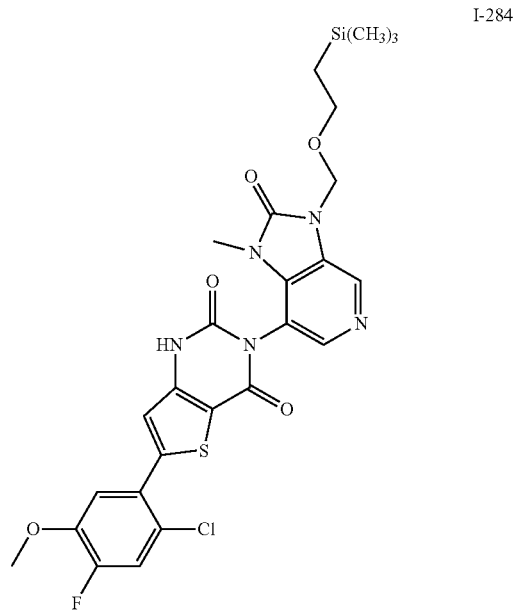

I-284

6-(2-chloro-4-fluoro-5-methoxyphenyl)-3-(1-methyl-2-oxo-3-((2-(trimethylsilyl)ethoxy)methyl)-2,3-dihydro-1H-imidazo[4,5-c]pyridin-7-yl)thieno[3,2-d]pyrimidine-2,4 (1H,3H)-dione (I-284): Prepared analogously to I-124, substituting I-65 with I-66 and substituting methyl 4-aminoisoquinoline-6-carboxylate with I-283.

ES/MS: 603.8 (M$^+$).

Preparation of Intermediate I-285

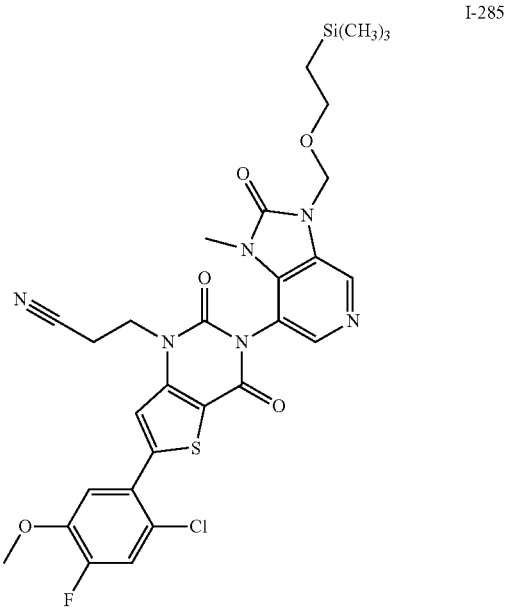

I-285

3-(6-(2-chloro-4-fluoro-5-methoxyphenyl)-3-(1-methyl-2-oxo-3-((2-(trimethylsilyl)ethoxy)methyl)-2,3-dihydro- 1H-imidazo[4,5-c]pyridin-7-yl)-2,4-dioxo-3,4-dihydrothieno[3,2-d]pyrimidin-1(2H)-yl)propanenitrile (I-285): Prepared analogously to I-189, substituting I-188 with I-284.
ES/MS: 656.7 (M+).

Preparation of Intermediate I-286

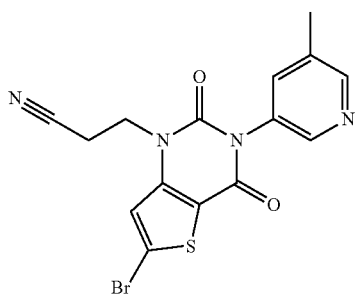

I-286

3-(6-bromo-3-(5-methylpyridin-3-yl)-2,4-dioxo-3,4-dihydrothieno[3,2-d]pyrimidin-1(2H)-yl)propanenitrile (I-286): Prepared analogously to I-8 and I-190, substituting isoquinolin-4-amine with 5-methylpyridin-3-amine.
ES/MS: 390.8 (M+).

Preparation of Intermediate I-287

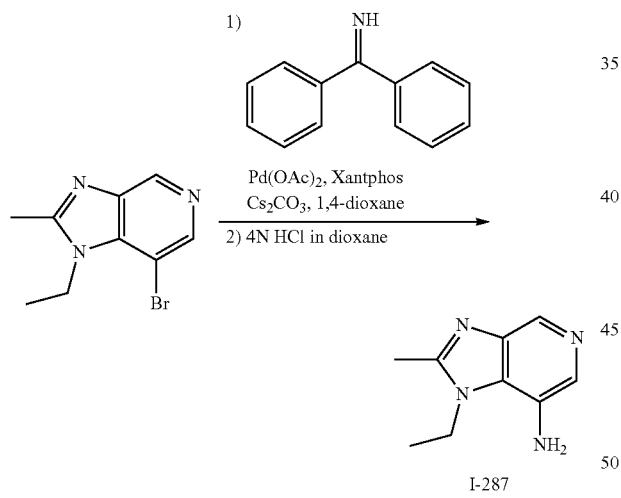

I-287

N-(1-ethyl-2-methyl-imidazo[4,5-c]pyridin-7-yl)-1,1-diphenyl-methanimine: To a dram vial was added 7-bromo-1-ethyl-2-methyl-imidazo[4,5-c]pyridine (300 mg, 1.25 mmol), diphenylmethanimine (272 mg, 1.50 mmol), Pd(OAc)$_2$ (28.1 mg, 0.13 mmol), 9,9-dimethyl-4,5-bis(diphenylphosphino)xanthene (XantPhos) (145 mg, 0.25 mmol) and cesium carbonate (407 mg, 1.25 mmol). Dioxane (6 mL) was added, and the mixture was degassed with argon for 30 seconds. The vial was sealed, and the reaction mixture was heated at 100° C. for 3 hours. The mixture was filtered and subsequently concentrated under reduced pressure. The crude residue product was purified by silica gel chromatography (eluent: EtOAc/hexanes). The material was dissolved in 4N HCl in dioxane and stirred at rt overnight. The precipitate was filtered and washed with dioxane and dried under vacuum to give the product (I-287).
ES/MS: 177.1 (M+H+).
$^1$H NMR (400 MHz, DMSO) δ 8.62 (d, J=0.8 Hz, 1H), 7.87 (d, J=0.8 Hz, 1H), 4.52 (q, J=7.2 Hz, 2H), 2.66 (s, 3H), 1.35 (t, J=7.2 Hz, 3H).

Preparation of Intermediate I-288

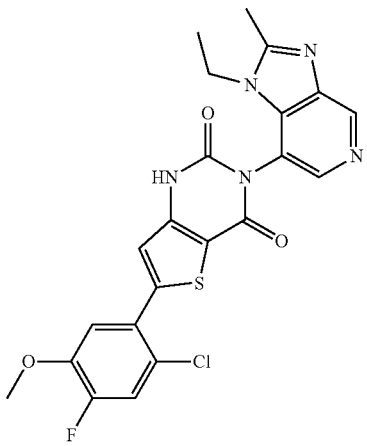

I-288

6-(2-chloro-4-fluoro-5-methoxyphenyl)-3-(1-ethyl-2-methyl-1H-imidazo[4,5-c]pyridin-7-yl)thieno[3,2-d]pyrimidine-2,4(1H,3H)-dione (I-288): Prepared analogously to Example 622, substituting the 6-fluoroisoquinolin-4-amine with I-287 and substituting I-30 with I-61.
ES/MS: 485.5 (M+).

Preparation of Intermediate I-289

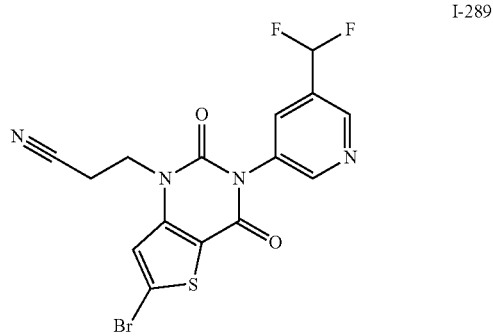 [SMILES: N#CCCn1c(=O)n(-c2cncc(C(F)F)c2)c(=O)c2sc(Br)cc21]

I-289

3-(6-bromo-3-(5-(difluoromethyl)pyridin-3-yl)-2,4-dioxo-3,4-dihydrothieno[3,2-d]pyrimidin-1(2H)-yl)propanenitrile (I-289): Prepared analogously to I-8 and I-190, substituting isoquinolin-4-amine with 5-(difluoromethyl)pyridin-3-amine.
ES/MS: 426.7 (M+).

Preparation of Intermediate I-290

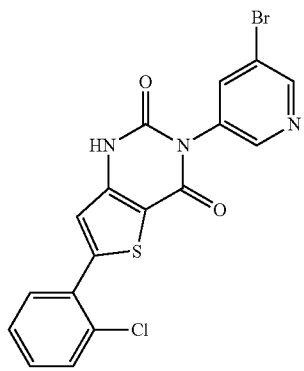

3-(5-bromopyridin-3-yl)-6-(2-chlorophenyl)thieno[3,2-d]pyrimidine-2,4(1H,3H)-dione (I-290): Prepared analogously to I-124, substituting I-65 with I-64 and substituting methyl 4-aminoisoquinoline-6-carboxylate with 5-bromopyridin-3-amine.

ES/MS: 435.7 (M+H$^+$).

Preparation of Intermediate I-291

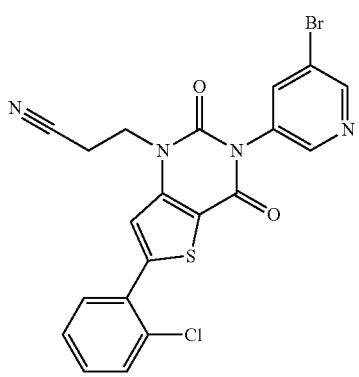

3-(3-(5-bromopyridin-3-yl)-6-(2-chlorophenyl)-2,4-dioxo-3,4-dihydrothieno[3,2-d]pyrimidin-1(2H)-yl)propanenitrile (I-291): Prepared analogously to I-189, substituting I-188 with I-290.

ES/MS: 486.7 (M$^+$).

Preparation of Intermediate I-292

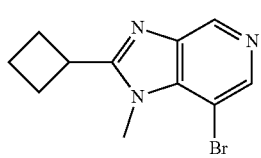

7-bromo-2-cyclobutyl-1-methyl-1H-imidazo[4,5-c]pyridine (I-292): Prepared analogously to I-230, substituting I-229 with 5-bromo-N$_4$-methyl-pyridine-3,4-diamine and substituting acetic anhydride with cyclobutanecarbonyl cyclobutanecarboxylate.

ES/MS: 265.1 (M$^+$).

Preparation of Intermediate I-293

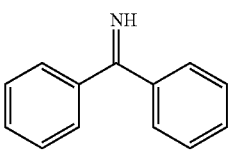

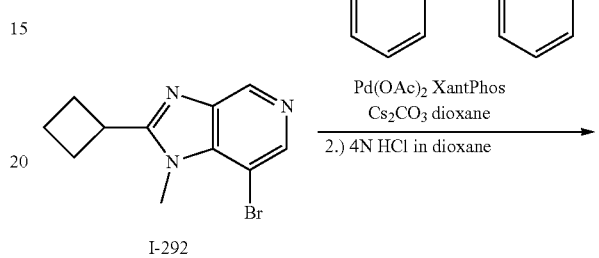

2-cyclobutyl-1-methyl-1H-imidazo[4,5-c]pyridin-7-amine (I-293): To a vial was added 7-bromo-2-cyclobutyl-1-methyl-1H-imidazo[4,5-c]pyridine (I-292) (546 mg, 2.05 mmol), diphenylmethanimine (446 mg, 2.46 mmol), Pd(OAc)$_2$ (46 mg, 0.21 mmol), 9,9-dimethyl-4,5-bis(diphenylphosphino)xanthene (XantPhos) (237 mg, 0.41 mmol) and cesium carbonate (802 mg, 2.46 mmol). Dioxane (8 mL) was added, and the mixture was degassed with argon for 30 seconds. The vial was sealed, and the reaction mixture was heated at 100° C. for 16 hours. The mixture was filtered and subsequently concentrated under reduced pressure. The crude residue was purified by silica gel chromatography (eluent: EtOAc/hexanes). The material was dissolved in 4N HCl in dioxane (6 mL) and stirred overnight at rt. The precipitate was filtered and washed with dioxane and dried under vacuum to provide 2-cyclobutyl-1-methyl-imidazo[4,5-c]pyridin-7-amine as HCl salt (I-293).

ES/MS: 203.1 (M+H$^+$).

Preparation of Intermediate I-294

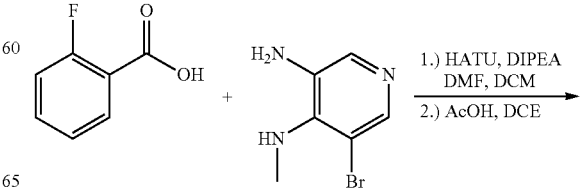

-continued

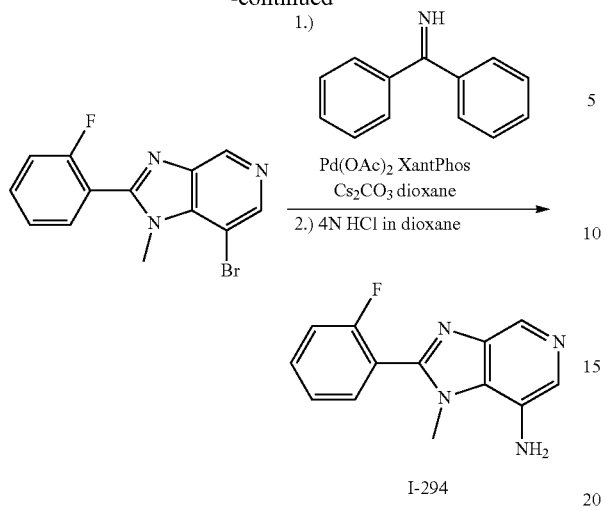

7-bromo-2-(2-fluorophenyl)-1-methyl-1H-imidazo[4,5-c]pyridine: To a solution of 2-fluorobenzoic acid (307 mg, 2.19 mmol), 5-bromo-$N_4$-methyl-pyridine-3,4-diamine (500 mg, 2.47 mmol), and HATU (1.22 g, 3.22 mmol) in DCM (3.5 mL) and DMF (3.5 mL) was added DIPEA (1.72 mL, 9.90 mmol). The reaction mixture was stirred at RT for 16 hours, then diluted with sat. aq. ammonium chloride and EtOAc. The aqueous layer was extracted with EtOAc (2×). The combined organic layers were washed with brine, dried over magnesium sulfate, and concentrated under reduced pressure. The crude material was taken up in dichloroethane (2.0 mL) and acetic acid (2.0 mL) and stirred overnight at 80° C. The reaction mixture was concentrated under reduced pressure and purified by silica gel column chromatography eluting with a mixture of ethyl acetate and hexane to provide the desired product.

ES/MS: 306.9 (M+).

2-(2-fluorophenyl)-1-methyl-1H-imidazo[4,5-c]pyridin-7-amine (I-294): To a vial was added 7-bromo-2-(2-fluorophenyl)-1-methyl-1H-imidazo[4,5-c]pyridine (450 mg, 1.47 mmol), diphenylmethanimine (320 mg, 1.76 mmol), Pd(OAc)$_2$ (33 mg, 0.14 mmol), 9,9-dimethyl-4,5-bis(diphenylphosphino)xanthene (XantPhos) (170 mg, 0.29 mmol) and cesium carbonate (575 mg, 1.76 mmol). Dioxane (8 mL) was added, and the mixture was degassed with argon for 30 seconds. The vial was sealed, and the reaction mixture was heated at 100° C. for 16 hours. The mixture was filtered and subsequently concentrated under reduced pressure. The crude residue was purified by silica gel chromatography (eluent: EtOAc/hexanes). The material was dissolved in 4N HCl in dioxane (9 mL) and stirred overnight at rt. The precipitate was filtered and washed with dioxane and dried under vacuum to provide I-294 as an HCl salt.

ES/MS: 243.0 (M+H$^+$).

Preparation of Intermediate I-295

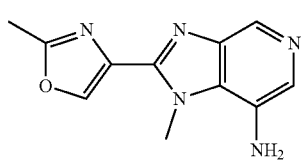

1-methyl-2-(2-methyloxazol-4-yl)-1H-imidazo[4,5-c]pyridin-7-amine (I-295): Prepared analogously to 1-294, substituting 2-fluorobenzoic acid with 2-methyloxazole-4-carboxylic acid.

ES/MS: 230.0 (M+H$^+$).

Preparation of Intermediate I-296

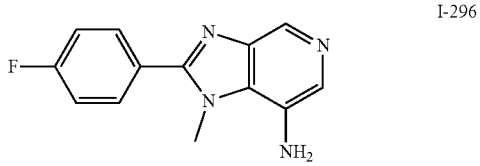 [SMILES: Cn1c(-c2ccc(F)cc2)nc2cncc(N)c21]

2-(4-fluorophenyl)-1-methyl-1H-imidazo[4,5-c]pyridin-7-amine (I-296): Prepared analogously to 1-294, substituting 2-fluorobenzoic acid with 4-fluorobenzoic acid.

ES/MS: 243.0 (M+H$^+$).

Preparation of Intermediate I-297

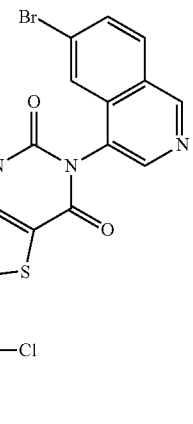

3-(6-bromoisoquinolin-4-yl)-6-(2-chloro-4-fluoro-5-methoxyphenyl)thieno[3,2-d]pyrimidine-2,4(1H,3H)-dione (I-297): Prepared analogously to Example 622, substituting I-30 with I-61 and substituting the 6-fluoroisoquinolin-4-amine with I-134.

ES/MS: 531.7 (M$^+$).

Preparation of Intermediate I-298

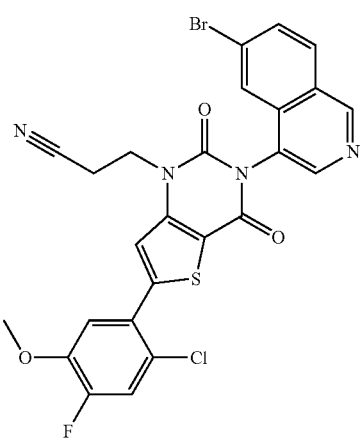

3-(3-(6-bromoisoquinolin-4-yl)-6-(2-chloro-4-fluoro-5-methoxyphenyl)-2,4-dioxo-3,4-dihydrothieno[3,2-d]pyrimidin-1(2H)-yl)propanenitrile (I-298): Prepared analogously to I-189, substituting I-188 with I-297.

ES/MS: 585.6 (M+).

Preparation of Intermediate I-299

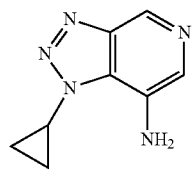

1-cyclopropyl-1H-[1,2,3]triazolo[4,5-c]pyridin-7-amine (I-299): Prepared analogously to I-281, substituting 5-bromo-N4-methyl-pyridine-3,4-diamine with I-229.

ES/MS: 176.0 (M+H+).

Preparation of Intermediate I-300

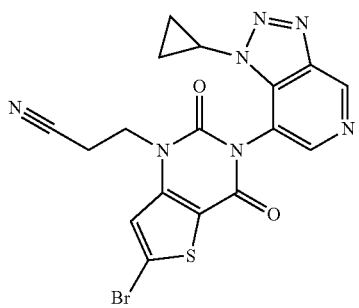

3-(6-bromo-3-(1-cyclopropyl-1H-[1,2,3]triazolo[4,5-c]pyridin-7-yl)-2,4-dioxo-3,4-dihydrothieno[3,2-d]pyrimidin-1(2H)-yl)propanenitrile (I-300): Prepared analogously to I-190, substituting isoquinolin-4-amine with I-299.

ES/MS: 457.7 (M+).

Preparation of Intermediate I-301

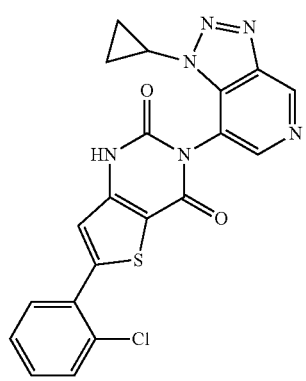

6-(2-chlorophenyl)-3-(1-cyclopropyl-1H-[1,2,3]triazolo[4,5-c]pyridin-7-yl)thieno[3,2-d]pyrimidine-2,4(1H,3H)-dione (I-301): Prepared analogously to I-124, substituting I-65 with I-64 and substituting methyl 4-aminoisoquinoline-6-carboxylate with I-299.

ES/MS: 436.7 (M+).

Preparation of Intermediate I-302

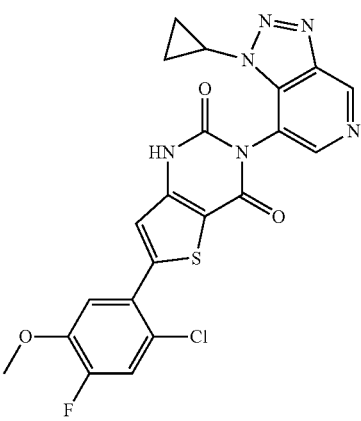

6-(2-chloro-4-fluoro-5-methoxyphenyl)-3-(1-cyclopropyl-1H-[1,2,3]triazolo[4,5-c]pyridin-7-yl)thieno[3,2-d]pyrimidine-2,4(1H,3H)-dione (I-302): Prepared analogously to I-124, substituting I-65 with I-66 and substituting methyl 4-aminoisoquinoline-6-carboxylate with I-299.

ES/MS: 537.7 (M+).

Preparation of Intermediate I-303

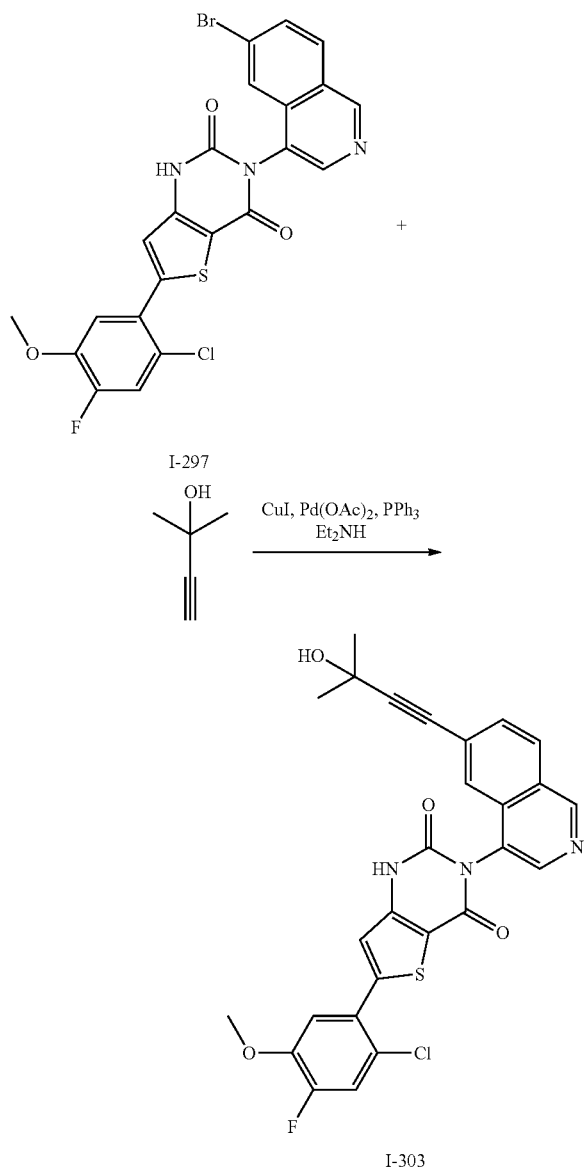

6-(2-chloro-4-fluoro-5-methoxy-phenyl)-3-[6-(3-hydroxy-3-methyl-but-1-ynyl)-4-isoquinolyl]-1H-thieno[3,2-d]pyrimidine-2,4-dione (I-303): A mixture of 3-(6-bromo-4-isoquinolyl)-6-(2-chloro-4-fluoro-5-methoxy-phenyl)-1H-thieno[3,2-d]pyrimidine-2,4-dione;hydrochloride (I-297) (50 mg, 0.087 mmol), 2-methylbut-3-yn-2-ol (8.9 mg, 0.11 mmol), CuI (1.7 mg, 8.9 µmol), Pd(OAc)$_2$ (1 mg, 4.4 µmol) and PPh$_3$ (3.4 mg, 13 µmol) in diethylamine (0.2 mL) was degassed with argon for 30 seconds. The resulting reaction mixture was refluxed for 30 min. After cooling to room temperature, the reaction mixture was filtered through an acrodisc and was subsequently purified by RP-HPLC (0.1% TFA-ACN in 0.1% TFA Water, Column. Gemini 5 uM, NX-C18 110 Angstrom, 250×21.2 mm) to give the title compound.

ES/MS: 435.7 (M$^+$).

Preparation of Intermediate I-304

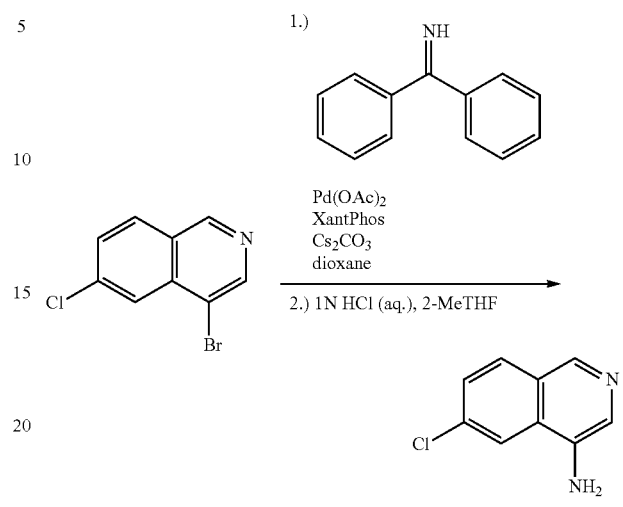

6-chloroisoquinolin-4-amine (I-304): To a vial was added 4-bromo-6-chloro-isoquinoline (500 mg, 2.06 mmol), diphenylmethanimine (448 mg, 2.47 mmol), Pd(OAc)$_2$ (46 mg, 0.21 mmol), 9,9-dimethyl-4,5-bis(diphenylphosphino)xanthene (XantPhos) (239 mg, 0.41 mmol) and cesium carbonate (672 mg, 2.06 mmol). Dioxane (10 mL) was added, and the mixture was degassed with argon for 30 seconds. The vial was sealed, and the reaction mixture was heated at 100° C. for 16 hours. The mixture was filtered and subsequently concentrated under reduced pressure. The crude residue was purified by silica gel chromatography (eluent: EtOAc/hexanes). The material was dissolved in 2-MeTHF (9 mL) and treated with 1 N HCl (aq.). After stirring for 1 h at rt, the precipitate was collected and washed with EtOAc to provide the title compound as an HCl salt.

ES/MS: 179.0 (M$^+$).

$^1$H NMR (400 MHz, DMSO) δ 8.94 (s, 1H), 8.63 (d, J=2.0 Hz, 1H), 8.37 (dd, J=9.6, 2.8 Hz, 2H), 7.96 (dt, J=8.8, 2.3 Hz, 2H), 7.85 (s, 1H).

Preparation of Intermediate I-305

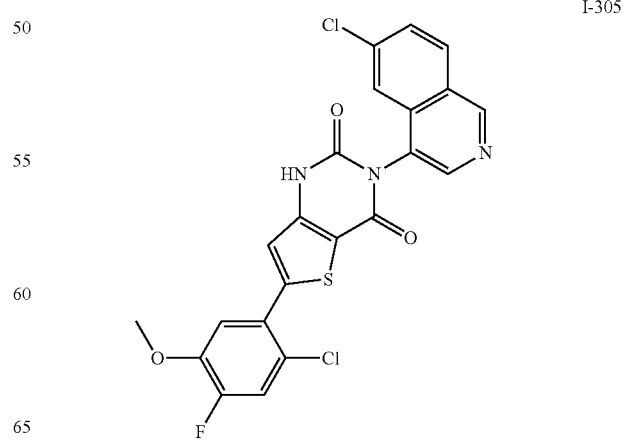

6-(2-chloro-4-fluoro-5-methoxyphenyl)-3-(6-chloroisoquinolin-4-yl)thieno[3,2-d]pyrimidine-2,4(1H,3H)-dione (I-305): Prepared analogously to Example 622, substituting I-30 with I-61 and substituting the 6-fluoroisoquinolin-4-amine with I-304.

ES/MS: 487.7 (M+).

Preparation of Intermediate I-306

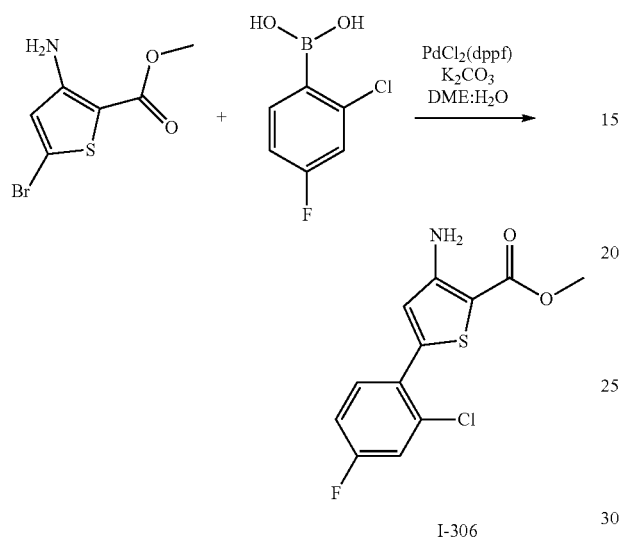

Methyl 3-amino-5-(2-chloro-4-fluorophenyl)thiophene-2-carboxylate (I-306): To a solution of methyl 3-amino-5-bromo-thiophene-2-carboxylate (2 g, 8.60 mmol), (2-chloro-4-fluoro-phenyl)boronic acid (1 g, 5.74 mmol) and $K_2CO_3$ (2.38 g, 17.2 mmol) in DME (12.5 mL) and water (2.5 mL) was added Pd(dppf)Cl$_2$ (234 mg, 0.29 mmol). The resulting solution was degassed with argon for 30 seconds and stirred at 80° C. for 2 h. After cooling to room temperature, the reaction mixture was extracted with ethyl acetate, the combined organic layers were washed with water, brine, dried over anhydrous $Na_2SO_4$ and concentrated under reduced pressure. The residue product was purified by silica gel chromatography to afford the desired compound along with the boronic acid starting material. The solid product obtained was washed with a mixture of DCM and hexane to provide the title compound.

ES/MS: 285.8 (M+).

Preparation of Intermediate I-307

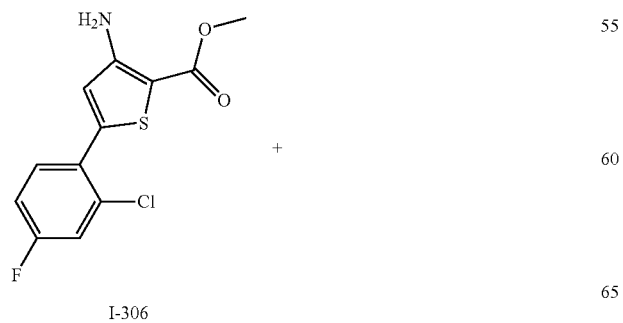

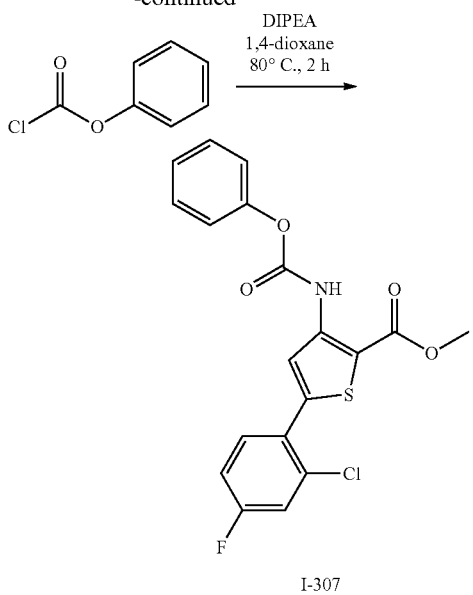

Methyl 5-(2-chloro-4-fluorophenyl)-3-((phenoxycarbonyl)amino)thiophene-2-carboxylate (I-307): To a stirring solution of methyl 3-amino-5-(2-chloro-4-fluoro-phenyl) thiophene-2-carboxylate (I-306) (500 mg, 1.75 mmol) in dioxane (9 mL) was added N,N-diisopropylethylamine (452 mg, 3.50 mmol) followed by phenyl chloroformate (411 mg, 2.62 mmol). The reaction mixture was stirred at 80° C. for 2 h after which full consumption of the starting material was observed. The reaction mixture was cooled to rt and concentrated under reduced pressure. Hexane was added and the mixture was sonicated (15 min) and cooled in an ice bath. The mixture was filtered and rinsed with additional hexanes followed by water. The solid product obtained was dried under vacuum to afford the title compound.

ES/MS: 405.8 (M+).

Preparation of Intermediate I-308

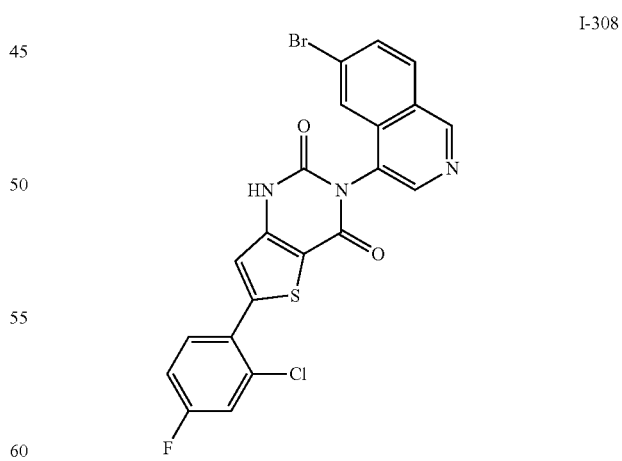

3-(6-bromoisoquinolin-4-yl)-6-(2-chloro-4-fluorophenyl) thieno[3,2-d]pyrimidine-2,4(1H,3H)-dione (I-308): Prepared analogously to Example 622, substituting I-30 with I-307 and substituting the 6-fluoroisoquinolin-4-amine with I-134.

ES/MS: 503.8 (M+H+).

Preparation of Intermediate I-309

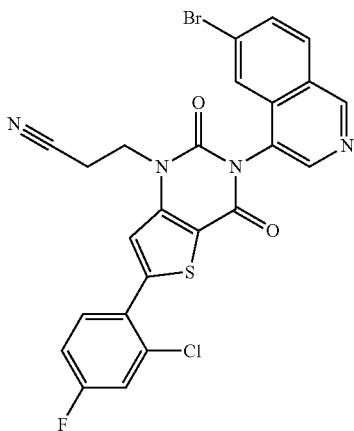

3-(3-(6-bromoisoquinolin-4-yl)-6-(2-chloro-4-fluorophenyl)-2,4-dioxo-3,4-dihydrothieno[3,2-d]pyrimidin-1(2H)-yl)propanenitrile (I-309): Prepared analogously to I-189, substituting I-188 with I-308.

ES/MS: 556.6 (M+).

Preparation of Intermediate I-310

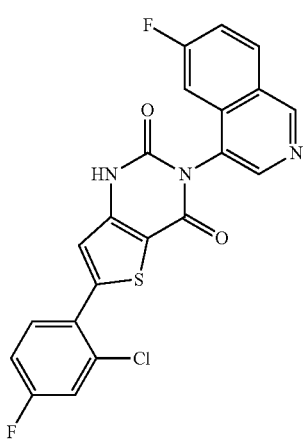

6-(2-chloro-4-fluorophenyl)-3-(6-fluoroisoquinolin-4-yl)thieno[3,2-d]pyrimidine-2,4(1H,3H)-dione (I-310): Prepared analogously to Example 622, substituting I-30 with I-307.

ES/MS: 441.7 (M+).

Preparation of Intermediate I-311

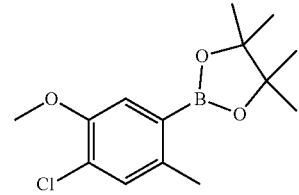

2-(4-chloro-5-methoxy-2-methyl-phenyl)-4,4,5,5-tetramethyl-1,3,2-dioxaborolane (I-311): Prepared analogously to I-103, substituting 2-bromo-4-methoxy-benzonitrile with 1-bromo-4-chloro-5-methoxy-2-methyl-benzene.

ES/MS: 282.9 (M+H+).

Preparation of Intermediate I-312

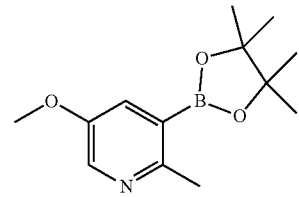

5-methoxy-2-methyl-3-(4,4,5,5-tetramethyl-1,3,2-dioxaborolan-2-yl)pyridine (I-312): Prepared analogously to I-103, substituting 2-bromo-4-methoxy-benzonitrile with 3-bromo-5-methoxy-2-methyl-pyridine.

ES/MS: 252.3 (M+H+).

Preparation of Intermediate I-313

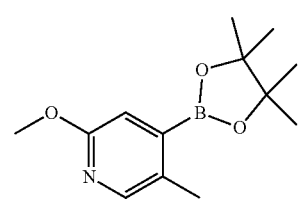

2-methoxy-5-methyl-4-(4,4,5,5-tetramethyl-1,3,2-dioxaborolan-2-yl)pyridine (I-313): Prepared analogously to I-103, substituting 2-bromo-4-methoxy-benzonitrile with 4-bromo-2-methoxy-5-methyl-pyridine.

ES/MS: 250.0 (M+H+).

637

Preparation of Intermediate I-314

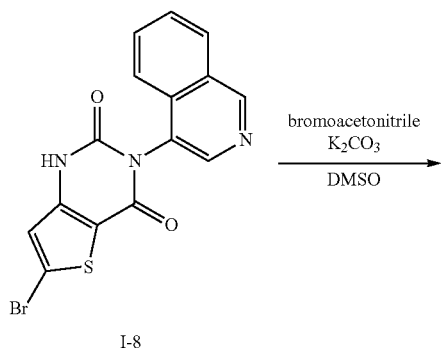

I-8 bromoacetonitrile
K₂CO₃
———————→
DMSO

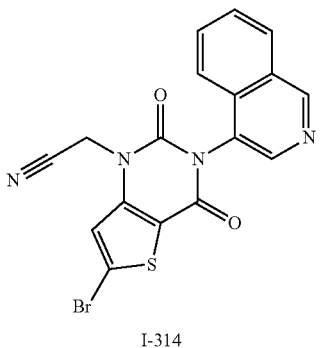

I-314

6-bromo-3-(4-isoquinolyl)-1H-thieno[3,2-d]pyrimidine-2,4-dione (I-314): To a stirring solution of 6-bromo-3-(isoquinolin-4-yl)thieno[3,2-d]pyrimidine-2,4(1H,3H)-dione (I-8) (HCl salt) (2 g, 5.34 mmol, 1.0 equiv.), in DMF (25.8 mL), was added K₂CO₃ (2.2 g, 16.0 mmol) followed by bromoacetonitrile (0.77 g, 6.41 mmol). The reaction mixture was stirred for 4 hours at 80° C., after which the mixture was diluted with ethyl acetate (20 mL) and the mixture was filtered through an acrodisc. The material was concentrated under reduced pressure, and purified by column chromatography (0-50% ethyl acetate in hexane) to obtain I-314.

ES/MS: 414.7 (M⁺).

Preparation of Intermediate I-315

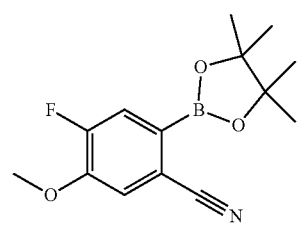

I-315

4-fluoro-5-methoxy-2-(4,4,5,5-tetramethyl-1,3,2-dioxaborolan-2-yl)benzonitrile (I-315): Prepared analogously to I-103, substituting 2-bromo-4-methoxy-benzonitrile with 2-bromo-4-fluoro-5-methoxy benzonitrile.

638

Preparation of Intermediate I-316

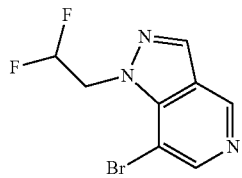

I-316

7-bromo-1-(2,2-difluoroethyl)pyrazolo[4,3-c]pyridine (I-316): Prepared analogously to I-180, substituting 4-bromo-1H-pyrazolo[3,4-c]pyridine with 7-bromo-1H-pyrazolo[4,3-c]pyridine, and substituting 2,2,2-trifluoroethyl trifluoromethanesulfonate with 2,2-difluoroethyl trifluoromethanesulfonate.

Preparation of Intermediate I-317

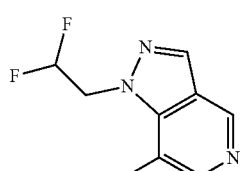

I-317

2-(2,2-difluoroethyl)pyrazolo[4,3-c]pyridin-7-amine (I-317): Prepared analogously to I-159, substituting 4-bromo-7-fluoro-isoquinoline with 7-bromo-1-(2,2-difluoroethyl)pyrazolo[4,3-c]pyridine (1-316).

Preparation of Intermediate I-318

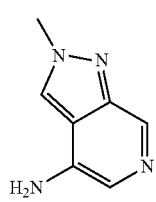

I-318

2-methylpyrazolo[3,4-c]pyridin-4-amine (I-318): Prepared analogously to 1-159, substituting 4-bromo-7-fluoro-isoquinoline with 4-bromo-2-methyl-pyrazolo[3,4-c]pyridine.

Preparation of Intermediate I-319

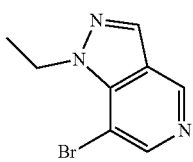

I-319

7-bromo-1-ethyl-pyrazolo[4,3-c]pyridine (I-319): Prepared analogously to I-180, substituting 4-bromo-1H-pyrazolo[3,4-c]pyridine with 7-bromo-1H-pyrazolo[4,3-c]pyridine, and substituting 2,2,2-trifluoroethyl trifluoromethanesulfonate with ethyl iodide.

Preparation of Intermediate I-320

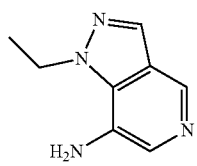

2-(2,2-difluoroethyl)pyrazolo[4,3-c]pyridin-7-amine (I-320): Prepared analogously to I-159, substituting 4-bromo-7-fluoro-isoquinoline with 7-bromo-1-ethyl-pyrazolo[4,3-c]pyridine (I-319).

Preparation of Intermediate I-321

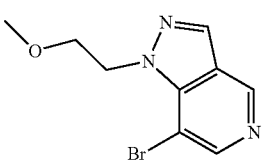

7-bromo-2-(2-methoxyethyl)pyrazolo[4,3-c]pyridine (I-321): Prepared analogously to I-180, substituting 4-bromo-1H-pyrazolo[3,4-c]pyridine with 7-bromo-1H-pyrazolo[4,3-c]pyridine, and substituting 2,2,2-trifluoroethyl trifluoromethanesulfonate with 1-iodo-2-methoxy-ethane.

Preparation of Intermediate I-322

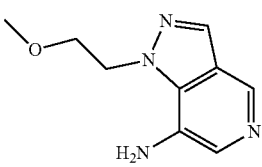

2-(2,2-difluoroethyl)pyrazolo[4,3-c]pyridin-7-amine (I-322): Prepared analogously to I-159, substituting 4-bromo-7-fluoro-isoquinoline with 7-bromo-1-(2-methoxyethyl)pyrazolo[4,3-c]pyridine (I-321).

Preparation of Intermediate I-323

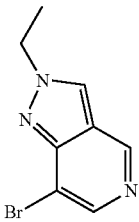

7-bromo-2-ethyl-pyrazolo[4,3-c]pyridine (I-323): Prepared analogously to I-179, substituting 4-bromo-1H-pyrazolo[3,4-c]pyridine with 7-bromo-1H-pyrazolo[4,3-c]pyridine, and substituting 2,2,2-trifluoroethyl trifluoromethanesulfonate with ethyl iodide.

Preparation of Intermediate I-324

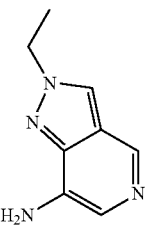

2-ethylpyrazolo[4,3-c]pyridin-7-amine (I-324): Prepared analogously to I-159, substituting 4-bromo-7-fluoro-isoquinoline with 7-bromo-2-ethyl-pyrazolo[4,3-c]pyridine (I-323).

Preparation of Intermediate I-325

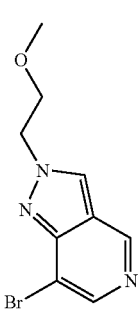

7-bromo-2-(2-methoxyethyl)pyrazolo[4,3-c]pyridine (I-325): Prepared analogously to I-179, substituting 4-bromo-1H-pyrazolo[3,4-c]pyridine with 7-bromo-1H-pyrazolo[4,3-c]pyridine, and substituting 2,2,2-trifluoroethyl trifluoromethanesulfonate with 1-iodo-2-methoxy-ethane.

Preparation of Intermediate I-326

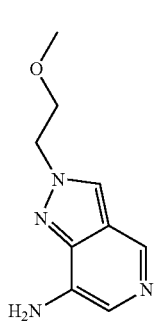

I-326

2-(2-methoxyethyl)pyrazolo[4,3-c]pyridin-7-amine (I-326): Prepared analogously to I-159, substituting 4-bromo-7-fluoro-isoquinoline with 7-bromo-2-(2-methoxyethyl)pyrazolo[4,3-c]pyridine (I-325).

Preparation of Intermediate I-327

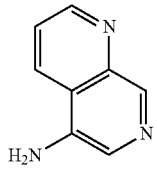

I-327

1,7-naphthyridin-5-amine (I-327): Prepared analogously to I-159, substituting 4-bromo-7-fluoro-isoquinoline with 5-bromo-1,7-naphthyridine.

Preparation of Intermediate I-328

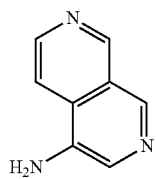

2,6-naphthyridin-4-amine (I-328): Prepared analogously to I-230, substituting I-231 with 4-bromo-2,6-naphthyridine (HCl salt).

Preparation of Intermediate I-329

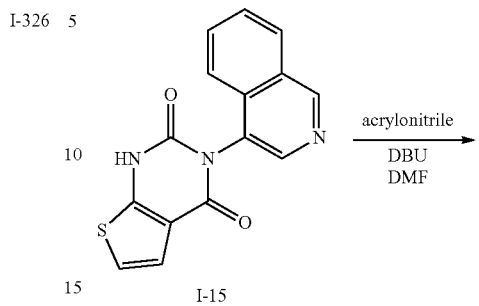

I-15

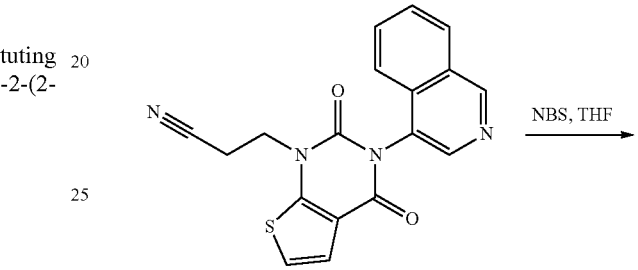

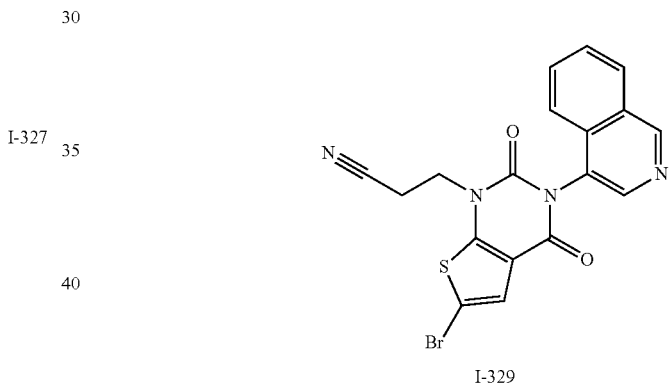

I-329

3-[3-(4-isoquinolyl)-2,4-dioxo-thieno[2,3-d]pyrimidin-1-yl]propanenitrile: To a solution of 3-(4-isoquinolyl)-1H-thieno[2,3-d]pyrimidine-2,4-dione (I-15) (1.2 g, 3.62 mmol) in DMF (14.2 mL) was added DBU (1.08 mL, 7.23 mmol) followed by acrylonitrile (7.11 mL, 109 mmol). The reaction mixture was heated at 80° C. for 16 hours, after which the mixture was cooled to room temperature. The mixture was concentrated under reduced pressure, and the crude material was purified by silica chromatography (eluent: EtOAc in hexanes) to provide the product.
ES/MS: 348.9 (M+H$^+$).

3-[6-bromo-3-(4-isoquinolyl)-2,4-dioxo-thieno[2,3-d]pyrimidin-1-yl]propanenitrile (I-329): To a cooled (0° C. via ice-bath) solution of 3-[3-(4-isoquinolyl)-2,4-dioxo-thieno[2,3-d]pyrimidin-1-yl]propanenitrile (324 mg, 0.93 mmol) in THF (3 mL) was slowly added a solution of NBS (174 mg, 0.98 mmol; added drop-wise) in MeCN (2 mL). The reaction mixture was monitored for completion. The solution was concentrated and the crude mixture was taken directly to the next step without purification.
ES/MS: 428.6 (M$^+$).

Preparation of Intermediate I-330

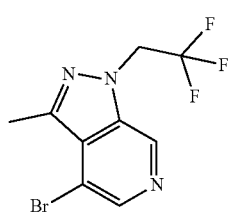

4-bromo-3-methyl-2-(2,2,2-trifluoroethyl)-2H-pyrazolo[3,4-c]pyridine (1-330): Prepared analogously to I-253, substituting iodomethane with 2,2,2-trifluoroethyl trifluoromethanesulfonate.

Preparation of Intermediate I-331

I-331

3-methyl-2-(2,2,2-trifluoroethyl)pyrazolo[3,4-c]pyridin-4-amine (I-331): Prepared analogously to 1-159, substituting 4-bromo-7-fluoro-isoquinoline with 4-bromo-3-methyl-2-(2,2,2-trifluoroethyl)-2H-pyrazolo[3,4-c]pyridine (1-330).

Preparation of Intermediate I-332

I-332

4-bromo-3-methyl-1-(2,2,2-trifluoroethyl)-1H-pyrazolo[3,4-c]pyridine (1-332): Prepared analogously to 1-252, substituting iodomethane with 2,2,2-trifluoroethyl trifluoromethanesulfonate.

Preparation of Intermediate I-333

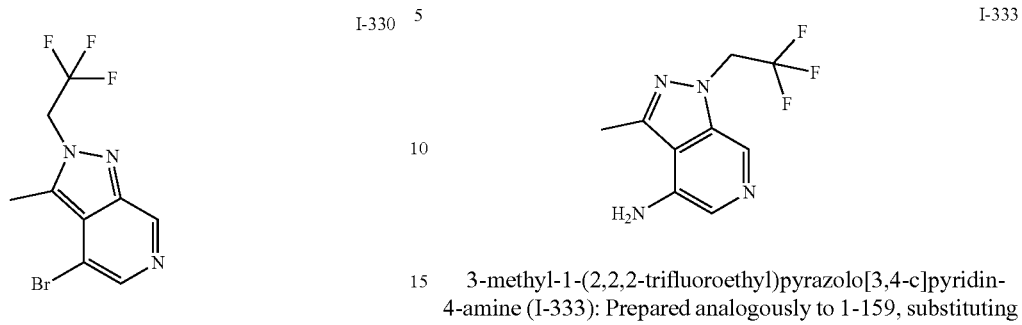

3-methyl-1-(2,2,2-trifluoroethyl)pyrazolo[3,4-c]pyridin-4-amine (I-333): Prepared analogously to 1-159, substituting 4-bromo-7-fluoro-isoquinoline with 4-bromo-3-methyl-1-(2,2,2-trifluoroethyl)-2H-pyrazolo[3,4-c]pyridine (1-332).

Preparation of Intermediate I-334

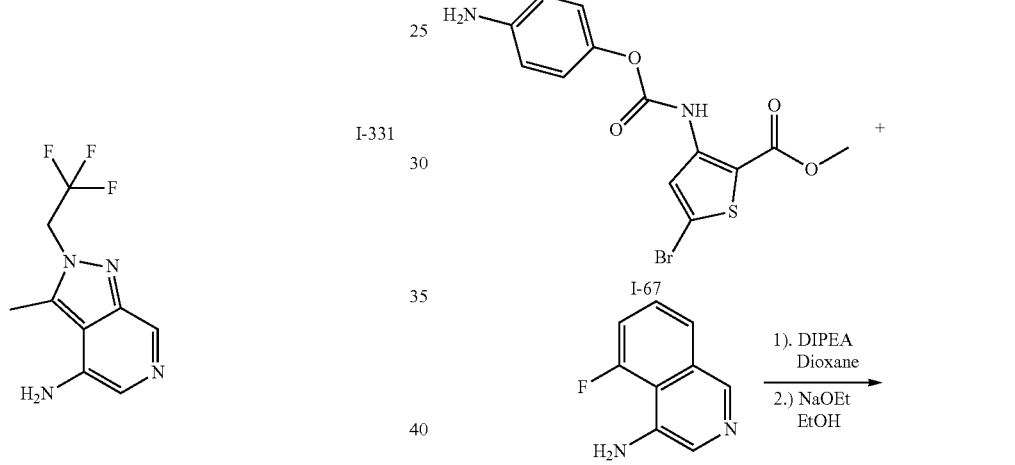

6-bromo-3-(5-fluoroisoquinolin-4-yl)thieno[3,2-d]pyrimidine-2,4(1H,3H)-dione (1-334): To a suspension of methyl 5-bromo-3-[(4-nitrophenoxy)carbonylamino]thiophene-2-carboxylate (I-67) (500 mg, 1.25 mmol) in dioxane (8 mL) and DIPEA (0.868 mL, 4.99 mmol) was added 5-fluoroisoquinolin-4-amine (263 mg, 1.62 mmol). The reaction mixture was stirred at 90° C. overnight. The reaction mixture was then cooled to ambient temperature and concentrated under reduced pressure. To the resulting crude residue was then added EtOH (8 mL) and sodium ethoxide (0.584 mL; 21% wt. in EtOH). The reaction mixture was then stirred at 60° C. for 2 hours. The reaction mixture was cooled to room temperature, diluted with 8% MeOH/DCM. The solid particle was filtered and rinsed once with 8% MeOH/DCM. The organic layer was concentrated and dried to give title compound.

ES/MS m/z: 391.98 (M+H⁺).

Preparation of Intermediate I-335

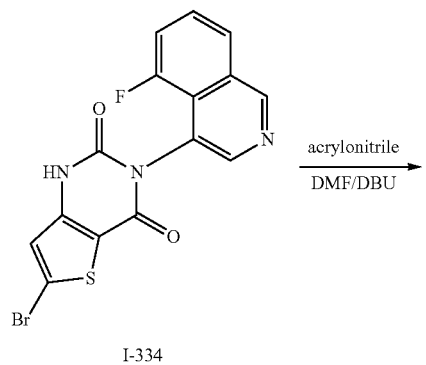

I-334

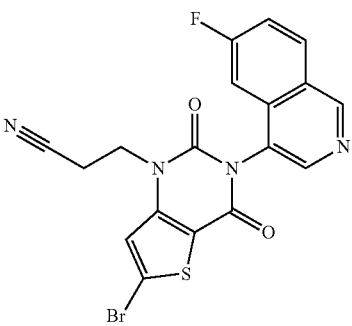

I-335

To a solution of 6-bromo-3-(5-fluoro-4-isoquinolyl)-1H-thieno[3,2-d]pyrimidine-2,4-dione (I-334) (300 mg, 0.76 mmol) in DMF (4 mL) was added DBU (582 mg, 3.82 mmol) followed by acrylonitrile (1.01 mg, 19.1 mmol). The reaction mixture was stirred at 90° C. for 24 hours, after which the mixture was cooled to room temperature. The mixture was concentrated under reduced pressure, and the crude material was purified by silica chromatography (eluent: 0-20% MeOH in DCM) to provide the product.

ES/MS m/z: 445.01 (M+H⁺).

Preparation of Intermediate I-336

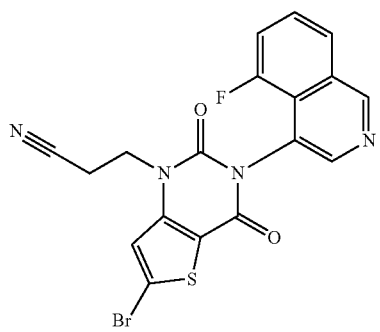

I-336

3-(6-bromo-3-(6-fluoroisoquinolin-4-yl)-2,4-dioxo-3,4-dihydrothieno[3,2-d]pyrimidin-1(2H)-yl)propanenitrile (I-336): Prepared analogously to I-334 and I-335, substituting 5-fluoroisoquinolin-4-amine with 6-fluoroisoquinolin-4-amine.

Preparation of Intermediate I-337

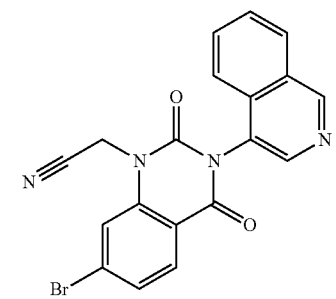

I-337

2-[7-bromo-3-(4-isoquinolyl)-2,4-dioxo-quinazolin-1-yl]acetonitrile: Prepared analogously to I-314, substituting 6-bromo-3-(4-isoquinolyl)-1H-thieno[3,2-d]pyrimidine-2,4-dione (I-8) with 7-bromo-3-(isoquinolin-4-yl)quinazoline-2,4(1H,3H)-dione (I-2).

ES/MS: 406.8 (M⁺).

Preparation of Intermediate I-338

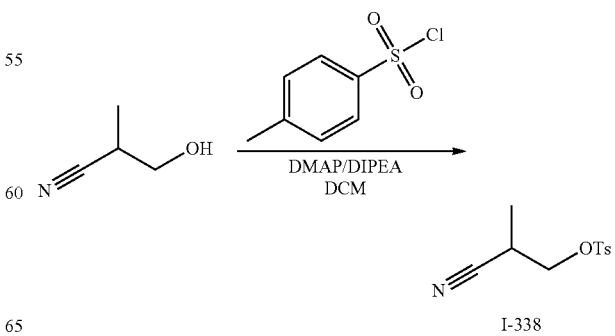

I-338

2-cyanopropyl 4-methylbenzenesulfonate (1-338): To a solution of 3-hydroxy-2-methyl-propanenitrile (1 g, 11.8 mmol), TEA (1.93 mL, 13.8 mmol) and DMAP (287 mg, 2.35 mmol) in $CH_2Cl_2$ (30 mL) at 0° C. was added a solution of 4-methylbenzenesulfonyl chloride (3.36 g, 17.6 mmol) in $CH_2Cl_2$ (30 mL) dropwise under argon. The reaction mixture was stirred at 0° C. for 30 min and then at 15° C. for 12 h. Water (50 mL) was added, and then the organic phase was washed with saturated solution of $NaHCO_3$ (60 mL×2), followed by brine once. The organic layer was collected and dried over $Na_2SO_4$, and the solvent evaporated under reduced pressure. The crude was purified by column chromatography (silica gel; Hexanes/ethyl acetate=3:1) to afford the product.

$^1$H NMR (400 MHz, Chloroform-d) δ 7.87-7.81 (m, 2H), 7.44-7.37 (m, 2H), 4.09 (dd, J=6.4, 2.2 Hz, 2H), 3.07-2.95 (m, 1H), 2.49 (s, 3H), 1.38 (d, J=7.1 Hz, 3H).

Preparation of Intermediate I-339

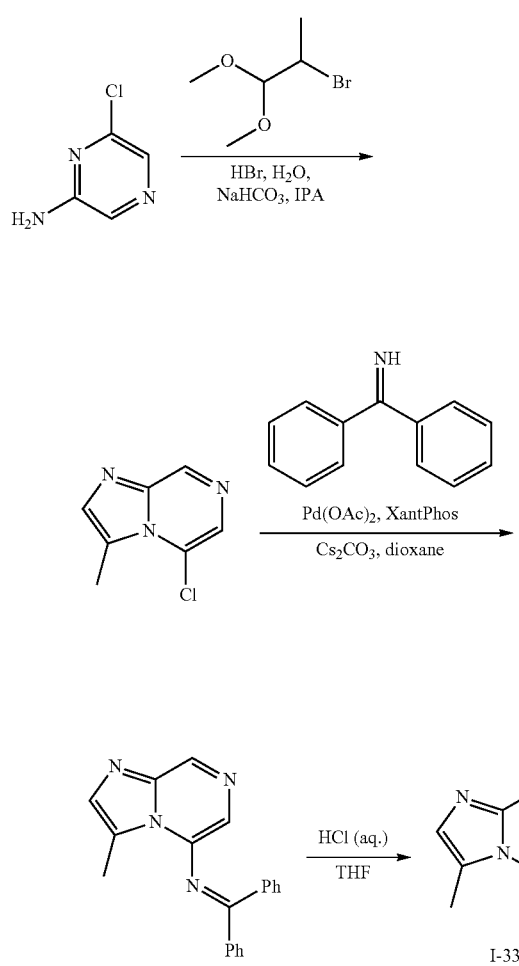

5-chloro-3-methylimidazo[1,2-a]pyrazine: A mixture of 2-bromo-1,1-dimethoxy-propane (19.8 g, 108.1 mmol), HBr (10.5 mL, 92.6 mmol, 48.0% purity) and $H_2O$ (10.0 mL, 555.8 mmol) was stirred at 100° C. for 2 hr, cooled and poured into a suspension of $NaHCO_3$ (46.7 g, 555.8 mmol) in 2-propanol (80 mL). The mixture was filtered, and 6-chloropyrazin-2-amine (4.0 g, 30.9 mmol) was added to the filtrate. The resulting solution was stirred at 80° C. under $N_2$ for 10 hr. The reaction mixture was basified by sat. aq. $NaHCO_3$ (60 mL), and then extracted with DCM (60 mL×3). The combined organic layers were dried over $Na_2SO_4$, filtered and concentrated under reduced pressure. The crude residue was purified by silica gel chromatography (eluent: Ethyl acetate/Petroleum ether) to give the product.

MS (ESI): 168.2 (M+H$^+$).

N-(3-methylimidazo[1,2-a]pyrazin-5-yl)-1,1-diphenyl-methanimine: A mixture of 5-chloro-3-methyl-imidazo[1,2-a]pyrazine (2.2 g, 13.1 mmol), diphenylmethanimine (2.6 mL, 15.8 mmol), Pd(OAc)$_2$ (294.7 mg, 1.3 mmol), Xantphos (1.5 g, 2.6 mmol) and Cs$_2$CO$_3$ (6.4 g, 19.7 mmol) in dioxane (25 mL) was degassed and purged with N$_2$. The mixture was stirred at 90° C. for 12 hr under N$_2$ atmosphere. The reaction mixture was diluted with sat. aq. NaHCO$_3$ (60 mL) and extracted with EtOAc (50 mL×3). The combined organic layers were dried over Na$_2$SO$_4$, filtered and concentrated under reduced pressure. The crude residue was purified by silica gel chromatography (eluent: Ethyl acetate/Petroleum ether) to give the product.

$^1$H NMR (400 MHz, chloroform-d) δ 8.60 (s, 1H), 7.88-7.83 (m, 2H), 7.61-7.55 (m, 1H), 7.52-7.46 (m, 3H), 7.42-7.33 (m, 3H), 7.20-7.16 (m, 2H), 6.69 (s, 1H), 2.76 (s, 3H).

3-methylimidazo[1,2-a]pyrazin-5-amine (I-339): To a solution of N-(3-methylimidazo[1,2-a]pyrazin-5-yl)-1,1-diphenyl-methanimine (3.4 g, 10.9 mmol) in THF (35 mL) was added HCl (2.0 M, 59.9 mL). The mixture was stirred at 25° C. for 12 hr. The reaction mixture was concentrated under reduced pressure to give a residue. The crude residue was purified by prep-HPLC ([H$_2$O(0.04% HCl)–ACN]; gradient: 1-5% ACN) to give the product.

$^1$H NMR (400 MHz, DMSO-d$_6$) δ 8.55 (s, 1H), 7.93 (s, 1H), 7.60 (s, 1H), 7.48-7.06 (m, 2H), 2.89 (s, 3H)).

MS (ESI): 149.1 (M+H$^+$).

Preparation of Intermediate I-340

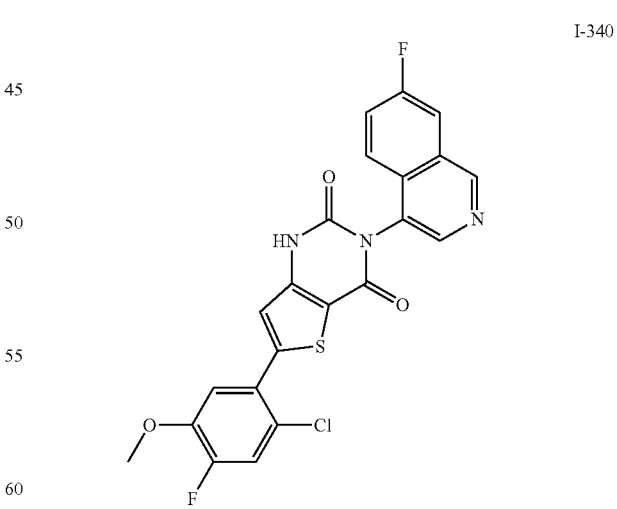

6-(2-chloro-4-fluoro-5-methoxyphenyl)-3-(7-fluoroisoquinolin-4-yl)thieno[3,2-d]pyrimidine-2,4(1H,3H)-dione (I-340): Prepared analogously to Example 622, substituting 6-fluoroisoquinolin-4-amine with 7-fluoroisoquinolin-4-amine and substituting I-30 with I-61.

Preparation of Intermediate I-341

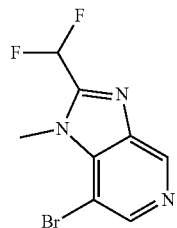

I-341

7-bromo-2-(difluoromethyl)-1-methyl-imidazo[4,5-c]pyridine (I-341): Prepared analogously to 1-230, substituting acetic anhydride with 2,2-difluoroacetic anhydride, and substituting I-229 with 5-bromo-N$_4$-methyl-pyridine-3,4-diamine.
ES/MS: 263.8 (M$^+$).

Preparation of Intermediate I-342

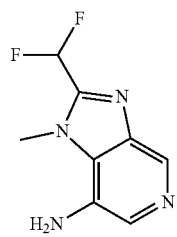

I-342

2-(difluoromethyl)-1-methyl-imidazo[4,5-c]pyridin-7-amine (I-342): Prepared analogously to 1-231, substituting I-230 with I-341.
ES/MS: 198.9 (M+H$^+$).

Preparation of Intermediate I-343

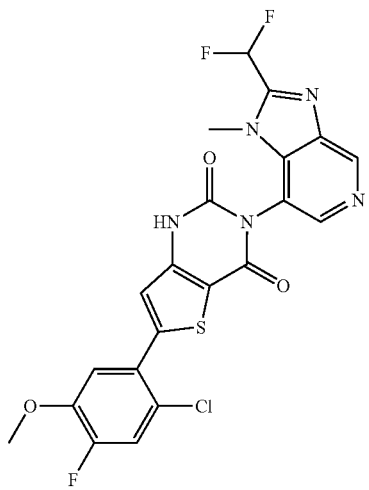

I-343

6-(2-chloro-4-fluoro-5-methoxy-phenyl)-3-[12-(difluoromethyl)-1-methyl-imidazo[4,5-c]pyridin-7-yl]-1H-thieno[3,2-d]pyrimidine-2,4-dione (I-343): Prepared analogously to 1-124, substituting I-65 with I-66 and substituting methyl 4-aminoisoquinoline-6-carboxylate with I-342.

Preparation of Intermediate I-344

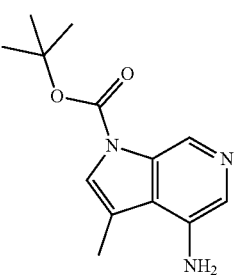

I-344 tert-butyl 4-amino-3-methyl-1H-pyrrolo[2,3-c]pyridine-1-carboxylate (I-344): Prepared analogously to I-192, substituting 7-bromo-1,2-dimethyl-imidazo[4,5-c]pyridine with 7 tert-butyl 4-bromo-3-methyl-1H-pyrrolo[2,3-c]pyridine-1-carboxylate.
ES/MS: 248.0 (M+H$^+$).

Preparation of Intermediate I-345

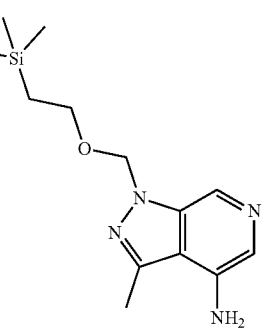

I-345

3-methyl-1-((2-(trimethylsilyl)ethoxy)methyl)-1H-pyrazolo[3,4-c]pyridin-4-amine (I-344): Prepared analogously to 1-283, substituting 7-bromo-1-methyl-1,3-dihydro-2H-imidazo[4,5-c]pyridin-2-one with 4-bromo-3-methyl-1H-pyrazolo[3,4-c]pyridine.

Preparation of Intermediate I-346

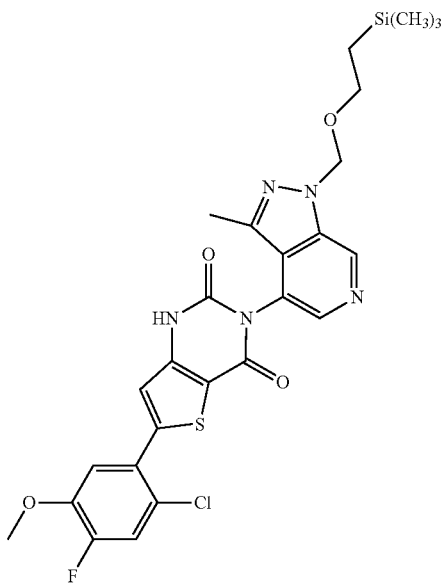

6-(2-chloro-4-fluoro-5-methoxyphenyl)-3-(3-methyl-1-((2-(trimethylsilyl)ethoxy)methyl)-1H-pyrazolo[3,4-c]pyridin-4-yl)thieno[3,2-d]pyrimidine-2,4(1H,3H)-dione (I-346): Prepared analogously to I-124, substituting I-65 with I-66 and substituting methyl 4-aminoisoquinoline-6-carboxylate with I-345.

Preparation of Intermediate I-347

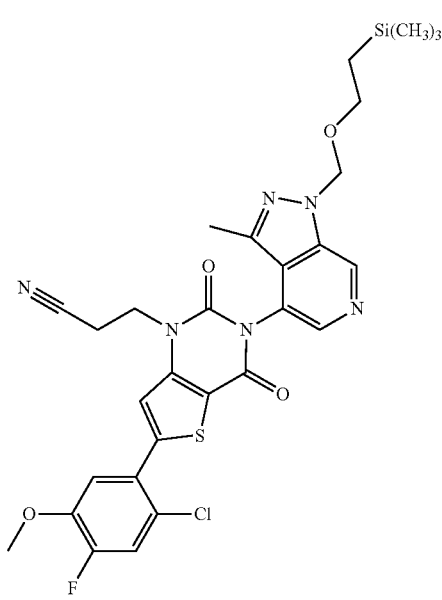

3-(6-(2-chloro-4-fluoro-5-methoxyphenyl)-3-(3-methyl-1-((2-(trimethylsilyl)ethoxy)methyl)-1H-pyrazolo[3,4-c]pyridin-4-yl)-2,4-dioxo-3,4-dihydrothieno[3,2-d]pyrimidin-1(2H)-yl)propanenitrile (I-347): Prepared analogously to I-189, substituting I-188 with I-346.

Preparation of Intermediate I-348

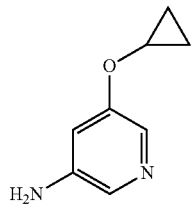

5-(cyclopropoxy)pyridin-3-amine (I-348): Prepared analogously to I-173, substituting 2,2,2-trifluoroethanol with cyclopropanol.

ES/MS: 151.00 (M+H⁺).

Preparation of Intermediate I-349

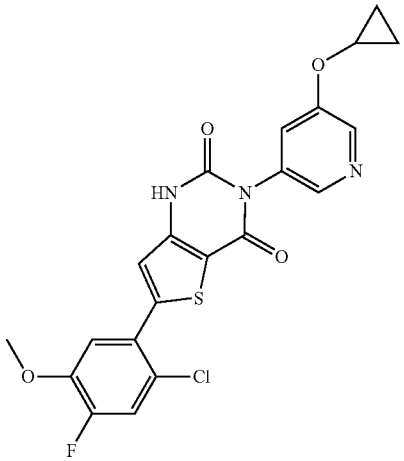

6-(2-chloro-4-fluoro-5-methoxy-phenyl)-3-[5-(cyclopropoxy)-3-pyridyl]-1H-thieno[3,2-d]pyrimidine-2,4-dione (I-349): Prepared analogously to 1-251, substituting 5-(2,2-difluoroethoxy)pyridin-3-amine (I-250) with 5-(cyclopropoxy)pyridin-3-amine (I-348).

ES/MS: 459.70 (M⁺).

Preparation of Intermediate I-350

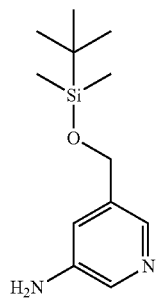

I-350

5-(((tert-butyldimethylsilyl)oxy)methyl)pyridin-3-amine (I-350): Prepared analogously to 1-192, substituting 7-bromo-1,2-dimethyl-imidazo[4,5-c]pyridine with 3-bromo-5-(((tert-butyldimethylsilyl)oxy)methyl)pyridine. ES/MS: 239.0 (M+H$^+$).

Preparation of Intermediate I-351

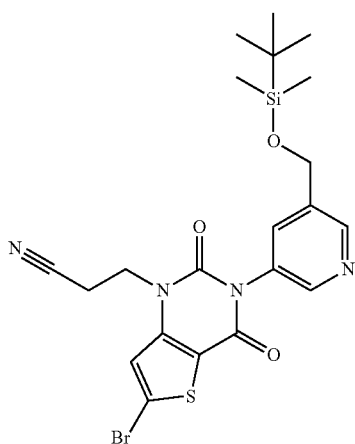

I-351

3-(6-bromo-3-(5-(((tert-butyldimethylsilyl)oxy)methyl)pyridin-3-yl)-2,4-dioxo-3,4-dihydrothieno[3,2-d]pyrimidin-1(2H)-yl)propanenitrile (I-351): Prepared analogously to I-8 and 1-190, substituting isoquinolin-4-amine with 5-(((tert-butyldimethylsilyl)oxy)methyl)pyridin-3-amine (I-350). ES/MS: 520.7 (M$^+$).

Preparation of Intermediate I-352

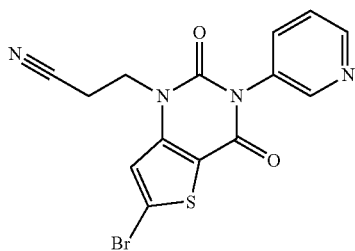

I-352

3-(6-bromo-2,4-dioxo-3-(pyridin-3-yl)-3,4-dihydrothieno[3,2-d]pyrimidin-1(2H)-yl)propanenitrile (I-352): Prepared analogously to 1-195, substituting 1,2-dimethylimidazo[4,5-c]pyridin-7-amine (I-192) with pyridin-3-amine.

Preparation of Intermediate I-353

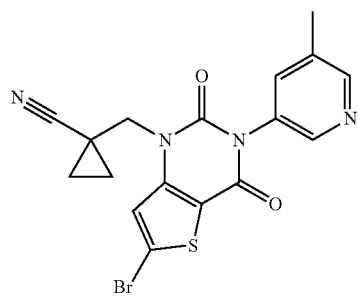

I-353

1-((6-bromo-3-(5-methylpyridin-3-yl)-2,4-dioxo-3,4-dihydrothieno[3,2-d]pyrimidin-1(2H)-yl)methyl)cyclopropane-1-carbonitrile (1-353): Prepared analogously to I-8 and 1-314, substituting isoquinolin-4-amine with 5-methylpyridin-3-amine, and substituting bromoacetonitrile with 1-(bromomethyl)cyclopropane-1-carbonitrile.

Preparation of Intermediate I-354

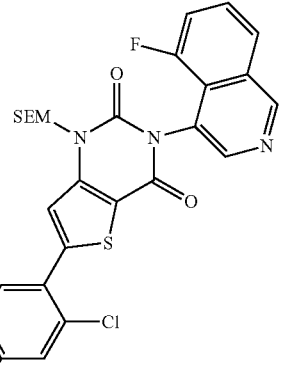

I-354

6-(2-chloro-4-fluoro-5-methoxyphenyl)-3-(5-fluoroisoquinolin-4-yl)-1-((2-(trimethylsilyl)ethoxy)methyl)thieno[3,2-d]pyrimidine-2,4(1H,3H)-dione (I-354). Prepared analogously to 1-120, substituting I-8 with Example 444.
ES/MS: 601.8 (M$^+$).

II. Compounds

Procedure 1: Example 1

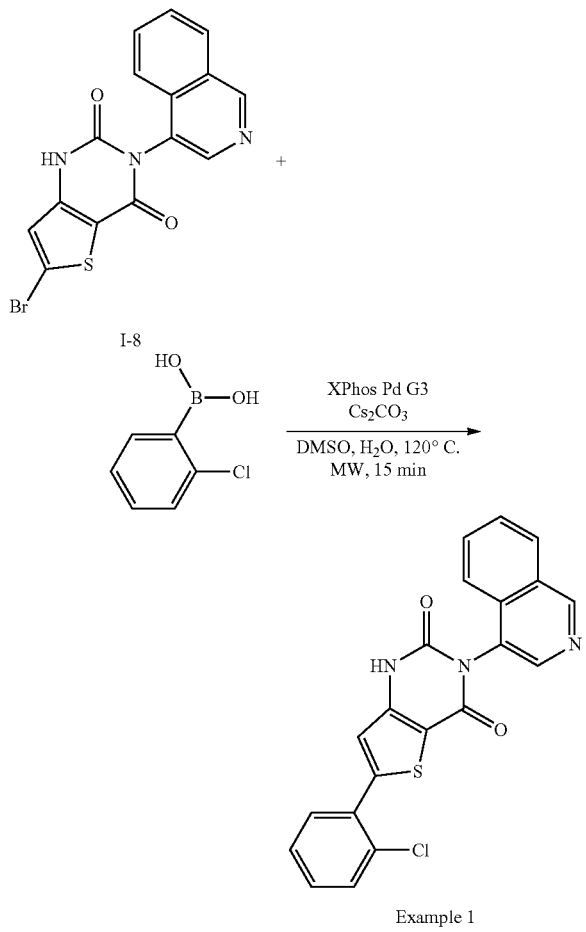

Example 1

6-(2-chlorophenyl)-3-(isoquinolin-4-yl)thieno[3,2-d]pyrimidine-2,4(1H,3H)-dione (Example 1): To a 10 mL microwave vial containing a stir bar was added 5-bromo-3-(4-isoquinolyl)-1H-thieno[3,2-d]pyrimidine-2,4-dione (I-8) (50 mg, 0.13 mmol, 1.0 equiv.) followed by DMSO (2.5 mL, 0.05 M). The contents were warmed with a heat gun until the starting bromide was fully dissolved after which (2-chlorophenyl)boronic acid (25.1 mg, 0.16 mmol, 1.2 equiv.), XPhos Pd G3 (10.1 mg, 10 mol %), $Cs_2CO_3$ (13.1 mg, 0.4 mmol, 3.0 equiv.) were subsequently added. $H_2O$ (0.17 mL) was then added after which the reaction mixture was sealed with Teflon, degassed under Ar (5 min), and heated to 120° C. under microwave irradiation for 15 min. The crude product was diluted in acetonitrile/water/trifluoroacetic acid (1.5 mL; 5:1:0.2), filtered through an acrodisc, and purified directly by RP-HPLC (0.1% TFA-ACN in 0.1% TFA Water) to give the title compound Example 1.

ES/MS: 406.1 [M+].

1H NMR (400 MHz, Methanol-$d_4$) δ 9.71 (s, 1H), 8.74 (s, 1H), 8.50 (d, J=8.3 Hz, 1H), 8.15-8.02 (m, 2H), 7.99 (t, J=7.5 Hz, 1H), 7.80-7.69 (m, 1H), 7.69-7.60 (m, 1H), 7.57-7.44 (m, 2H), 7.37 (s, 1H).

Examples 2-23

The following Examples were made in an analogous fashion according to Procedure 1 and are shown below in Table 2. Any different reagents/starting materials than those described in Procedure 1 are noted in the last column of Table 2—"Changes to Procedure 1: Different Reagents/Starting Materials".

TABLE 2

| | | Examples 2-23 | | |
|---|---|---|---|---|
| Example | Structure | ES/MS m/z | 1H-NMR | Changes to Procedure 1: Different Reagents/Starting Materials |
| 2 | (structure) | 372.0 | 1H NMR (400 MHz, Methanol-d4) δ 9.67 (s, 1H), 8.71 (s, 1H), 8.47 (d, J = 8.5 Hz, 1H), 8.15-7.89 (m, 3H), 7.83 (d, J = 6.8 Hz, 2H), 7.54 (d, J = 7.1 Hz, 3H), 7.39 (s, 1H). | phenylboronic acid |

TABLE 2-continued

Examples 2-23

| Example | Structure | ES/MS m/z | ¹H-NMR | Changes to Procedure 1: Different Reagents/Starting Materials |
|---|---|---|---|---|
| 3 | 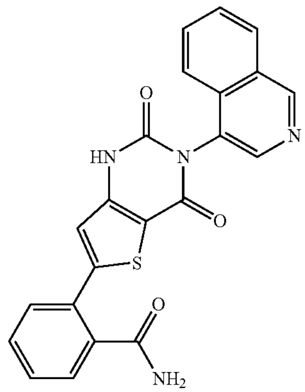 [SMILES: NC(=O)c1ccccc1-c1cc2[nH]c(=O)n(-c3cncc4ccccc34)c(=O)c2s1] | 415.1 | 1H NMR (400 MHz, DMSO-d6) δ 12.32 (s, 1H), 9.45 (d, J = 4.9 Hz, 1H), 8.58 (d, J = 4.8 Hz, 1H), 8.29 (d, J = 7.9 Hz, 1H), 8.03 (s, 1H), 7.83 (ddt, J = 7.4 Hz, 4H), 7.65-7.48 (m, 5H), 7.20 (s, 1H). | (2-cyanophenyl)boronic acid |
| 4 | 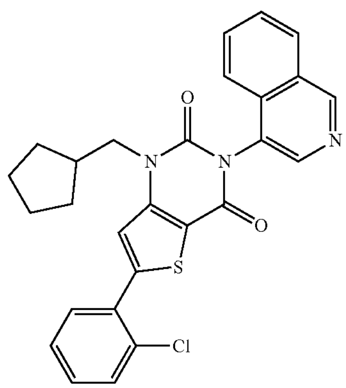 [SMILES: O=c1c2sc(-c3ccccc3Cl)cc2n(CC2CCCC2)c(=O)n1-c1cncc2ccccc12] | 489.1 | 1H NMR (400 MHz, Methanol-d4) δ 9.56 (s, 1H), 8.63 (s, 1H), 8.40 (d, J = 8.6 Hz, 1H), 8.04-7.94 (m, 1H), 7.90 (dt, J = 8.5, 3.1 Hz, 2H), 7.81-7.72 (m, 1H), 7.65 (d, J = 6.8 Hz, 2H), 7.56-7.46 (m, 2H), 4.27-4.13 (m, 2H), 2.55 (p, J = 7.6 Hz, 1H), 1.86 (dd, J = 11.7, 6.1 Hz, 2H), 1.75 (d, J = 3.7 Hz, 2H), 1.71-1.58 (m, 2H), 1.52-1.41 (m, 2H). | I-45 |
| 5 | 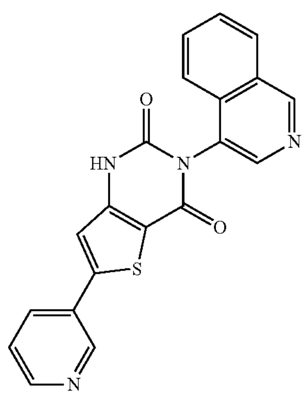 [SMILES: O=c1[nH]c2cc(-c3cccnc3)sc2c(=O)n1-c1cncc2ccccc12] | 373.1 | 1H NMR (400 MHz, Methanol-d4) δ 9.74 (d, J = 11.4 Hz, 1H), 9.11 (d, J = 2.3 Hz, 1H), 8.74 (dt, J = 6.5, 2.7 Hz, 2H), 8.52 (t, J = 7.8 Hz, 1H), 8.43 (dt, J = 8.1, 2.0 Hz, 1H), 8.17-7.96 (m, 4H), 7.75 (dd, J = 8.0, 5.1 Hz, 1H), 7.56 (s, 1H). | 3-pyridylboronic acid |
| 6 | 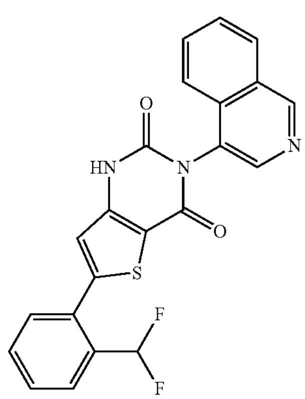 [SMILES: O=c1[nH]c2cc(-c3ccccc3C(F)F)sc2c(=O)n1-c1cncc2ccccc12] | 402.0 | 1H NMR (400 MHz, Methanol-d4) δ 10.25 (s, 1H), 9.63 (s, 1H), 8.69 (s, 1H), 8.45 (d, J = 8.3 Hz, 1H), 8.16-7.68 (m, 6H), 7.64-7.41 (m, 2H), 7.27-7.12 (m, 1H). | [2-(difluoromethyl)phenyl]boronic acid |

TABLE 2-continued

Examples 2-23

| Example | Structure | ES/MS m/z | ¹H-NMR | Changes to Procedure 1: Different Reagents/Starting Materials |
|---|---|---|---|---|
| 7 | 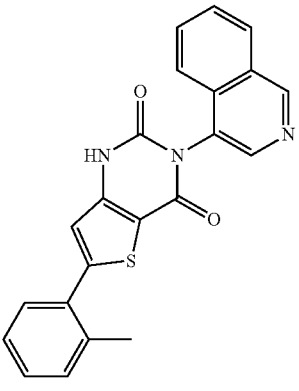 [SMILES: Cc1ccccc1-c1cc2[nH]c(=O)n(-c3cncc4ccccc34)c(=O)c2s1] | 386.1 | 1H NMR (400 MHz, Methanol-d4) δ 9.64 (s, 1H), 8.70 (s, 1H), 8.45 (d, J = 8.2 Hz, 1H), 8.11-7.98 (m, 2H), 7.95 (ddd, J = 8.1, 6.6, 1.4 Hz, 1H), 7.51 (d, J = 7.5 Hz, 1H), 7.46-7.37 (m, 2H), 7.35 (dq, J = 8.6, 4.3 Hz, 1H), 7.10 (s, 1H), 2.52 (s, 3H). | o-toylboronic acid |
| 8 | 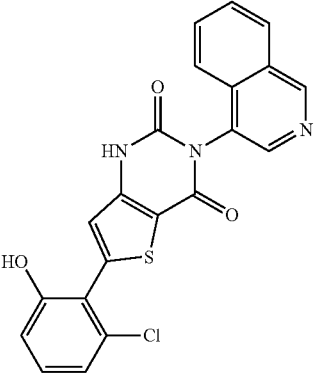 [SMILES: O=c1[nH]c2cc(-c3c(O)cccc3Cl)sc2c(=O)n1-c1cncc2ccccc12] | 422.0 | 1H NMR (400 MHz, DMSO-d6) δ 12.29 (s, 1H), 10.61 (s, 1H), 9.61 (s, 1H), 8.71 (s, 1H), 8.39 (d, J = 8.0 Hz, 1H), 8.01 (d, J = 8.3 Hz, 1H), 7.90 (dddd, J = 24.0, 8.1, 6.8, 1.3 Hz, 2H), 7.33 (t, J = 8.2 Hz, 1H), 7.12-6.98 (m, 3H). | (2-chloro-6-hydroxyphenyl)boronic acid |
| 9 | 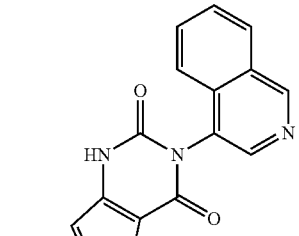 | 390.1 | 1H NMR (400 MHz, DMSO-d6) δ 12.29 (s, 1H), 9.45 (s, 1H), 8.58 (s, 1H), 8.38-8.22 (m, 1H), 8.02-7.72 (m, 4H), 7.60-7.30 (m, 4H). | (2-fluorophenyl)boronic acid |

TABLE 2-continued

Examples 2-23

| Example | Structure | ES/MS m/z | ¹H-NMR | Changes to Procedure 1: Different Reagents/Starting Materials |
|---|---|---|---|---|
| 10 | 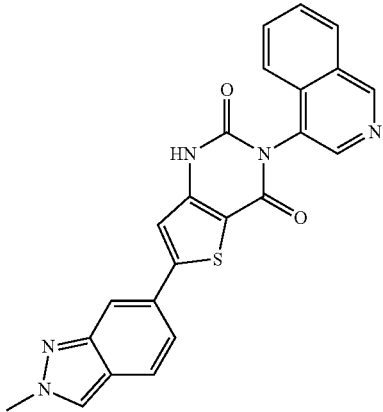 [SMILES: Cn1cc2ccc(-c3cc4[nH]c(=O)n(-c5cncc6ccccc56)c(=O)c4s3)cc2n1] | 426.1 | 1H NMR (400 MHz, DMSO-d6) δ 9.51 (s, 1H), 8.63 (s, 1H), 8.43 (s, 1H), 8.37-8.28 (m, 1H), 8.10 (s, 1H), 7.98-7.72 (m, 4H), 7.48-7.36 (m, 2H), 4.21 (s, 3H). | (2-methylindazol-6-yl)boronic acid |
| 11 | 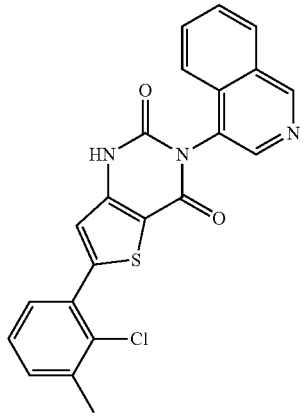 [SMILES: Cc1cccc(-c2cc3[nH]c(=O)n(-c4cncc5ccccc45)c(=O)c3s2)c1Cl] | 420.1 | 1H NMR (400 MHz, DMSO-d6) δ 12.29 (s, 1H), 9.50 (s, 1H), 8.62 (s, 1H), 8.32 (dd, J = 7.7, 1.4 Hz, 1H), 7.94-7.74 (m, 3H), 7.63-7.48 (m, 2H), 7.41 (t, J = 7.6 Hz, 1H), 7.27 (s, 1H), 2.45 (s, 3H). | (2-chloro-3-methyl-phenyl)boronic acid |
| 12 | 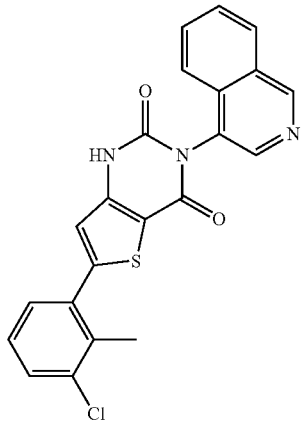 [SMILES: Cc1c(Cl)cccc1-c1cc2[nH]c(=O)n(-c3cncc4ccccc34)c(=O)c2s1] | 420.1 | 1H NMR (400 MHz, DMSO-d6) δ 12.32 (s, 1H), 9.52 (s, 1H), 8.63 (s, 1H), 8.33 (dd, J = 7.8, 1.3 Hz, 1H), 8.00-7.75 (m, 3H), 7.61 (dd, J = 7.9, 1.3 Hz, 1H), 7.46 (dd, J = 7.8, 1.4 Hz, 1H), 7.37 (t, J = 7.8 Hz, 1H), 7.11 (s, 1H), 2.46 (s, 3H). | (3-chloro-2-methyl-phenyl)boronic acid |

TABLE 2-continued

Examples 2-23

| Example | Structure | ES/MS m/z | ¹H-NMR | Changes to Procedure 1: Different Reagents/Starting Materials |
|---|---|---|---|---|
| 13 | 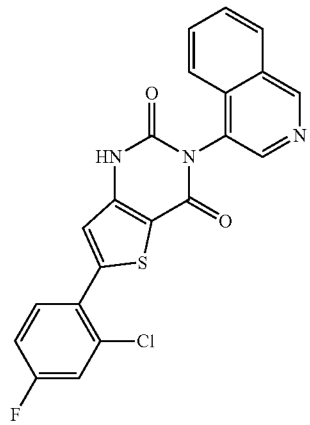 [SMILES: O=c1[nH]c2cc(-c3ccc(F)cc3Cl)sc2c(=O)n1-c1cncc2ccccc12] | 424.1 | 1H NMR (400 MHz, DMSO-d6) δ 12.29 (s, 1H), 9.43 (s, 1H), 8.57 (s, 1H), 8.32-8.19 (m, 1H), 7.97-7.65 (m, 5H), 7.42 (td, J = 8.4, 2.7 Hz, 1H), 7.29 (s, 1H). | (2-chloro-4-fluoro-phenyl)boronic acid |
| 14 | 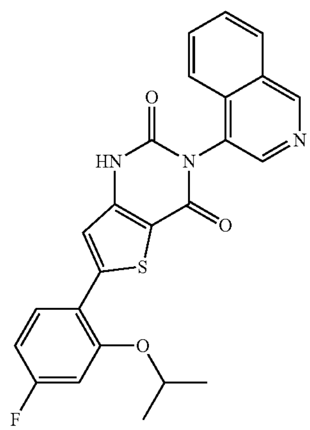 [SMILES: CC(C)Oc1cc(F)ccc1-c1cc2[nH]c(=O)n(-c3cncc4ccccc34)c(=O)c2s1] | 448.1 | 1H NMR (400 MHz, Methanol-d4) δ 9.64 (s, 1H), 8.68 (s, 1H), 8.45 (d, J = 8.4 Hz, 1H), 8.10-7.79 (m, 4H), 7.47 (s, 1H), 7.03 (dd, J = 11.2, 2.5 Hz, 1H), 6.93-6.78 (m, 2H), 4.07 (q, J = 12.7 Hz, 1H), 1.48 (d, J = 6.0 Hz, 6H). | (4-fluoro-2-isopropoxy-phenyl)boronic acid |
| 15 | 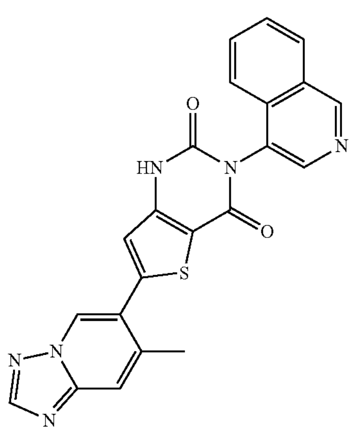 [SMILES: Cc1cc2ncnn2cc1-c1cc2[nH]c(=O)n(-c3cncc4ccccc34)c(=O)c2s1] | 427.0 | 1H NMR (400 MHz, MeOD) δ 9.76 (s, 1H), 9.05 (s, 1H), 8.78 (s, 1H), 8.58-8.49 (m, 3H), 8.20-8.11 (m, 2H), 8.02 (ddd, J = 8.1, 6.6, 1.4 Hz, 1H), 7.82 (t, J = 1.0 Hz, 1H), 7.28 (s, 1H), 2.68 (s, 3H). | 7-methyl-6-(4,4,5,5-tetramethyl-1,3-dioxolan-2-yl)-2-yl)-[1,2,4]triazolo[1,5-a]pyridine |

TABLE 2-continued

Examples 2-23

| Example | Structure | ES/MS m/z | ¹H-NMR | Changes to Procedure 1: Different Reagents/Starting Materials |
|---|---|---|---|---|
| 16 | 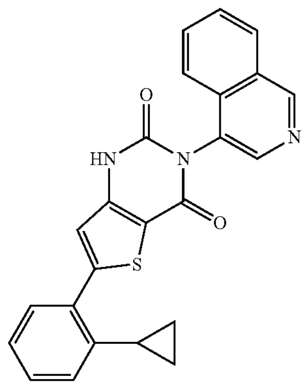 [SMILES: O=c1[nH]c2cc(-c3ccccc3C3CC3)sc2c(=O)n1-c1cncc2ccccc12] | 412.1 | 1H NMR (400 MHz, MeOD) δ 9.69 (s, 1H), 8.73 (s, 1H), 8.49 (d, J = 8.2 Hz, 1H), 8.10 (t, J = 7.7 Hz, 1H), 8.04 (d, J = 8.3 Hz, 1H), 7.98 (t, J = 7.5 Hz, 1H), 7.52 (dd, J = 7.6, 1.4 Hz, 1H), 7.43 (td, J = 7.6, 1.5 Hz, 1H), 7.36-7.28 (m, 1H), 7.25 (s, 1H), 7.20 (d, J = 7.9 Hz, 1H), 2.15 (ddd, J = 13.8, 8.5, 5.2 Hz, 1H), 1.09-1.00 (m, 2H), 0.87-0.79 (m, 2H). | (2-cyclopropylphenyl)boronic acid |
| 17 | 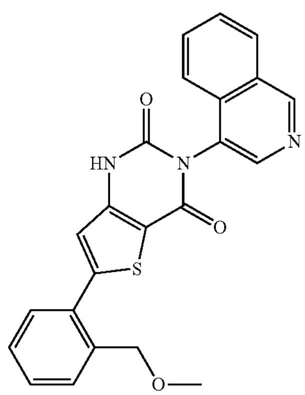 [SMILES: COCc1ccccc1-c1cc2[nH]c(=O)n(-c3cncc4ccccc34)c(=O)c2s1] | 416.1 | 1H NMR (400 MHz, DMSO) δ 12.33 (s, 1H), 9.51 (s, 1H), 8.62 (s, 1H), 8.33 (d, J = 7.6 Hz, 1H), 7.99-7.79 (m, 3H), 7.70-7.47 (m, 4H), 7.25 (s, 1H), 4.47 (s, 2H), 3.38 (s, 3H). | [2-(methoxymethyl)phenyl]boronic acid |
| 18 | 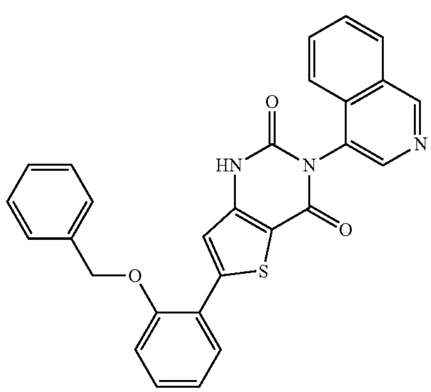 [SMILES: O=c1[nH]c2cc(-c3ccccc3OCc3ccccc3)sc2c(=O)n1-c1cncc2ccccc12] | 478.2 | 1H NMR (400 MHz, DMSO) δ 12.24 (s, 1H), 9.49 (s, 1H), 8.59 (d, J = 1.1 Hz, 1H), 8.34-8.28 (m, 1H), 7.93-7.75 (m, 4H), 7.51-7.26 (m, 8H), 7.13 (t, J = 7.6 Hz, 1H), 5.39 (s, 2H). | (2-benzyloxyphenyl)boronic acid |
| 19 | 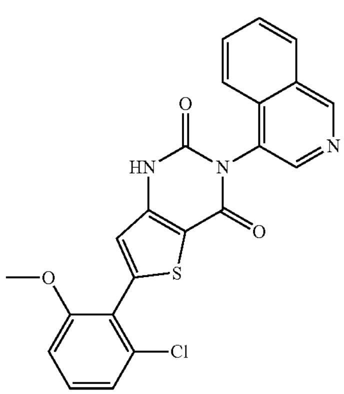 [SMILES: COc1cccc(Cl)c1-c1cc2[nH]c(=O)n(-c3cncc4ccccc34)c(=O)c2s1] | 436.1 | 1H NMR (400 MHz, DMSO) δ 12.24 (s, 1H), 9.47 (s, 1H), 8.62 (d, J = 1.4 Hz, 1H), 8.30 (d, J = 8.0 Hz, 1H), 7.93 (d, J = 8.2 Hz, 1H), 7.88-7.75 (m, 2H), 7.52 (td, J = 8.3, 1.4 Hz, 1H), 7.23 (dd, J = 18.0, 8.3 Hz, 2H), 7.02 (d, J = 1.4 Hz, 1H), 3.83 (d, J = 1.4 Hz, 3H). | (2-chloro-6-methoxyphenyl)boronic acid |

TABLE 2-continued

Examples 2-23

| Example | Structure | ES/MS m/z | ¹H-NMR | Changes to Procedure 1: Different Reagents/Starting Materials |
|---|---|---|---|---|
| 20 | 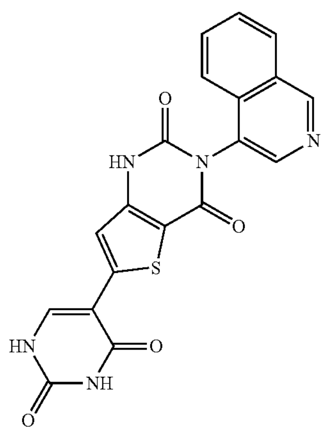 [SMILES: O=c1[nH]cc(-c2cc3[nH]c(=O)n(-c4cncc5ccccc45)c(=O)c3s2)c(=O)[nH]1] | 406.1 | 1H NMR (400 MHz, DMSO) δ 12.20 (s, 1H), 11.77 (dd, J = 6.2, 2.0 Hz, 1H), 11.70 (d, J = 1.9 Hz, 1H), 9.48 (s, 1H), 8.58 (s, 1H), 8.48 (d, J = 6.2 Hz, 1H), 8.31 (dt, J = 7.4, 1.4 Hz, 1H), 7.88-7.74 (m, 3H), 7.42 (s, 1H). | (2,4-dioxo-1H-pyrimidin-5-yl)boronic acid |
| 21 | 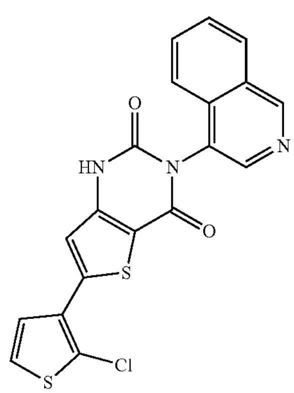 [SMILES: O=c1[nH]c2cc(-c3ccsc3Cl)sc2c(=O)n1-c1cncc2ccccc12] | 412.1 | 1H NMR (400 MHz, DMSO-d6) δ 12.30 (s, 1H), 9.45 (s, 1H), 8.57 (s, 1H), 8.29 (dd, J = 7.5, 1.6 Hz, 1H), 7.89-7.81 (m, 2H), 7.80-7.74 (m, 1H), 7.69 (d, J = 5.9 Hz, 1H), 7.58 (d, J = 5.9 Hz, 1H), 7.45 (s, 1H). | (2-chlorothiophen-3-yl)boronic acid |
| 22 | 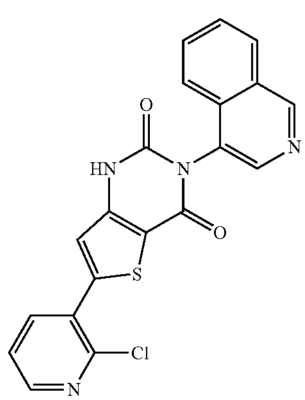 [SMILES: O=c1[nH]c2cc(-c3cccnc3Cl)sc2c(=O)n1-c1cncc2ccccc12] | 407.1 | 1H NMR (400 MHz, DMSO-d6) δ 12.34 (s, 1H), 9.44 (d, J = 6.6 Hz, 1H), 8.59 (s, 1H), 8.55 (dd, J = 4.8, 1.9 Hz, 1H), 8.32-8.27 (m, 1H), 8.25 (dd, J = 7.7, 1.9 Hz, 1H), 7.89 (d, J = 8.2 Hz, 1H), 7.82-7.77 (m, 2H), 7.63 (dd, J = 7.7, 4.7 Hz, 1H), 7.44 (s, 1H). | (2-chloropyridin-3-yl)boronic acid |

TABLE 2-continued

Examples 2-23

| Example | Structure | ES/MS m/z | ¹H-NMR | Changes to Procedure 1: Different Reagents/Starting Materials |
|---|---|---|---|---|
| 23 | 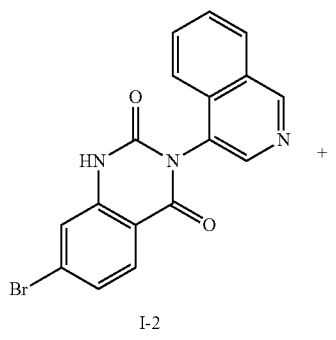 | 387.1 | 1H NMR (400 MHz, DMSO-d6) δ 12.36 (s, 1H), 9.50 (d, J = 0.8 Hz, 1H), 8.68 (dd, J = 5.0, 1.7 Hz, 1H), 8.61 (s, 1H), 8.38-8.26 (m, 1H), 8.11 (dd, J = 7.8, 1.7 Hz, 1H), 7.94-7.75 (m, 3H), 7.57 (dd, J = 7.8, 5.0 Hz, 1H), 7.26 (s, 1H), 2.72 (s, 3H). | (2-methylpyridin-3-yl)boronic acid |

Procedure 2: Example 24

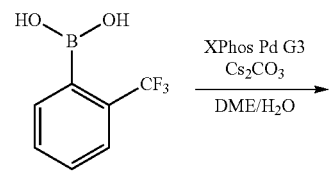

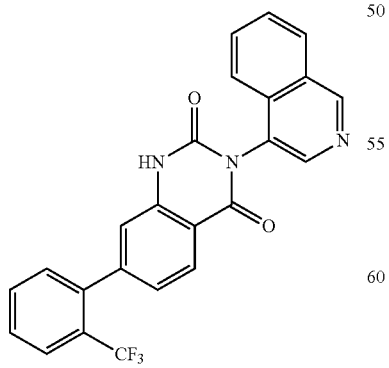

Example 24

3-(isoquinolin-4-yl)-7-(2-(trifluoromethyl)phenyl)quinazoline-2,4(1H,3H)-dione (Example 24): To a microwave vial with 7-bromo-3-(isoquinolin-4-yl)quinazoline-2,4(1H,3H)-dione (I-2) (20 mg, 0.054 mmol) were added (2-(trifluoromethyl)phenyl)boronic acid (16 mg, 0.082 mmol), XPhos Pd G3 (6.1 mg, 0.0082 mmol) and cesium carbonate (53 mg, 0.16 mmol). DME (1.5 mL) and water (0.1 mL) were added, and the mixture was degassed with argon for 30 seconds. The vial was sealed, and the reaction mixture was heated at 100° C. for 20 minutes under microwave conditions. The crude mixture was concentrated under reduced pressure, and to the crude residue were added DMF (1 mL), acetonitrile (0.5 mL), TFA (0.3 mL) and water (0.2 mL). The mixture was heated to dissolve produce a homogeneous mixture, and the resulting mixture was filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the title compound Example 24 as a trifluoroacetate salt.

ES/MS: 478.1 (M+H⁺).

1H NMR (400 MHz, DMSO-d$_6$) δ 11.75 (d, J=5.7 Hz, 1H), 9.44 (s, 1H), 9.19 (d, J=5.3 Hz, 1H), 9.04 (ddd, J=23.4, 2.5, 1.2 Hz, 1H), 8.60 (d, J=8.5 Hz, 1H), 8.28 (t, J=5.3 Hz, 1H), 7.99-7.74 (m, 5H), 7.74-7.53 (m, 3H), 7.19-6.97 (m, 2H).

Examples 25-64

The following Examples were made in an analogous fashion according to Procedure 2 and are shown below in Table 3. Any different reagents/starting materials than those described in Procedure 2 are noted in the last column of Table 3—"Changes to Procedure 2: Different Reagents/Starting Materials".

TABLE 3

Examples 25-64

| Example | Structure | ES/MS m/z | ¹H-NMR | Changes to Procedure 2: Different Reagents/Starting Materials |
|---|---|---|---|---|
| 25 | 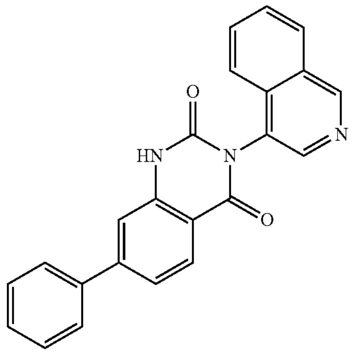 [SMILES: O=c1[nH]c2cc(-c3ccccc3)ccc2c(=O)n1-c1cncc2ccccc12] | 366.1 | 1H NMR (400 MHz, DMSO-d6) δ 11.85 (s, 1H), 9.48 (s, 1H), 8.61 (s, 1H), 8.31 (dd, J = 7.3, 1.8 Hz, 1H), 8.05 (d, J = 8.2 Hz, 1H), 7.95-7.68 (m, 5H), 7.68-7.45 (m, 5H). | phenylboronic acid |
| 26 | 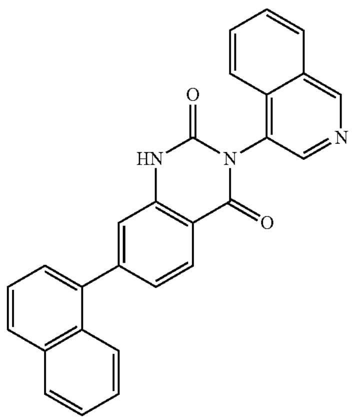 [SMILES: O=c1[nH]c2cc(-c3cccc4ccccc34)ccc2c(=O)n1-c1cncc2ccccc12] | 416.2 | 1H NMR (400 MHz, DMSO-d6) δ 11.88 (s, 1H), 9.50 (s, 1H), 8.63 (s, 1H), 8.32 (dd, J = 7.6, 1.6 Hz, 1H), 8.19-8.03 (m, 3H), 7.96 (d, J = 8.1 Hz, 1H), 7.92-7.50 (m, 7H), 7.40 (d, J = 7.6 Hz, 2H). | 1-naphthylboronic acid |
| 27 | 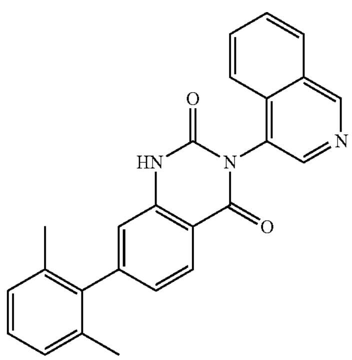 [SMILES: Cc1cccc(C)c1-c1ccc2c(=O)n(-c3cncc4ccccc34)c(=O)[nH]c2c1] | 394.2 | 1H NMR (400 MHz, DMSO-d6) δ 11.81 (s, 1H), 9.46 (s, 1H), 8.62 (s, 1H), 8.30 (dd, J = 7.2, 1.9 Hz, 1H), 8.06 (d, J = 8.0 Hz, 1H), 7.94 (d, J = 7.9 Hz, 1H), 7.80 (pd, J = 6.9, 1.5 Hz, 2H), 7.30-7.14 (m, 3H), 7.14-7.01 (m, 2H), 2.07 (s, 3H), 2.04 (s, 3H). | (2,6-dimethylphenyl)boronic acid |
| 28 | 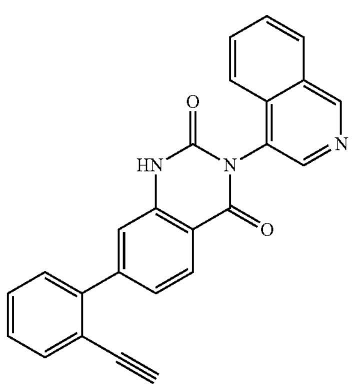 [SMILES: C#Cc1ccccc1-c1ccc2c(=O)n(-c3cncc4ccccc34)c(=O)[nH]c2c1] | 390.1 | 1H NMR (400 MHz, DMSO-d6) δ 11.87 (s, 1H), 9.46 (s, 1H), 8.61 (s, 1H), 8.30 (dd, J = 7.0, 2.2 Hz, 1H), 8.04 (d, J = 8.2 Hz, 1H), 7.96-7.89 (m, 1H), 7.79 (tt, J = 7.0, 5.3 Hz, 2H), 7.74-7.64 (m, 1H), 7.59 (td, J = 7.5, 1.5 Hz, 1H), 7.56-7.46 (m, 3H), 7.43 (dd, J = 8.1, 1.6 Hz, 1H), 4.27 (s, 1H). | (2-ethynylphenyl)boronic acid |

TABLE 3-continued

Examples 25-64

| Example | Structure | ES/MS m/z | ¹H-NMR | Changes to Procedure 2: Different Reagents/Starting Materials |
|---|---|---|---|---|
| 29 | 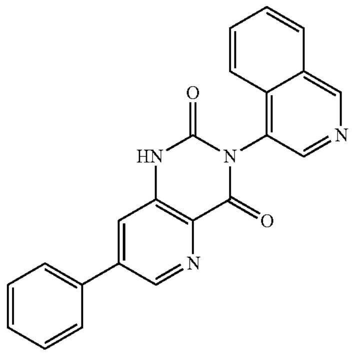 [SMILES: O=c1[nH]c2cc(-c3ccccc3)cnc2c(=O)n1-c1cncc2ccccc12] | 367.1 | 1H NMR (400 MHz, DMSO-d6) δ 11.92 (s, 1H), 9.48 (s, 1H), 8.90 (d, 1H), 8.61 (s, 1H), 8.31 (dd, 1H), 8.01 (dd, 1H), 7.87 (d, 1H), 7.85-7.80 (m, 3H), 7.81-7.76 (m, 1H), 7.65-7.53 (m, 3H). | I-13; phenylboronic acid |
| 30 | 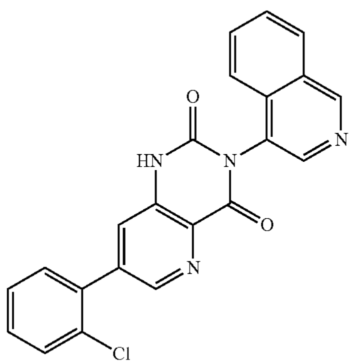 [SMILES: O=c1[nH]c2cc(-c3ccccc3Cl)cnc2c(=O)n1-c1cncc2ccccc12] | 401.1 | 1H NMR (400 MHz, DMSO-d6) δ 11.96 (s, 1H), 9.52 (d, 1H), 8.67-8.59 (m, 2H), 8.39-8.27 (m, 1H), 8.10 (dd, 1H), 7.83 (dddd, 2H), 7.77 (d, 1H), 7.75-7.66 (m, 1H), 7.58 (dddd, 3H). | I-13; 2-(chlorophenyl)boronic acid |
| 31 | 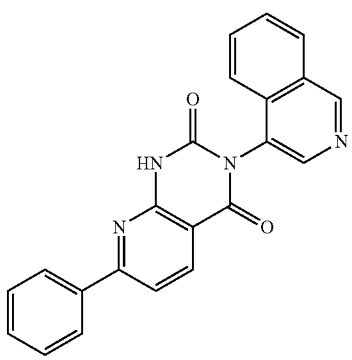 [SMILES: O=c1[nH]c2nc(-c3ccccc3)ccc2c(=O)n1-c1cncc2ccccc12] | 367.2 | 1H NMR (400 MHz, MeOD) δ 9.63 (s, 1H), 8.70 (s, 1H), 8.50 (d, J = 8.2 Hz, 1H), 8.44 (dt, J = 8.3, 1.0 Hz, 1H), 8.32-8.22 (m, 2H), 8.09-7.98 (m, 2H), 7.98-7.89 (m, 2H), 7.61-7.53 (m, 3H). | I-14; 4,4,5,5-tetramethyl-2-phenyl-1,3,2-dioxaborolane |
| 32 | 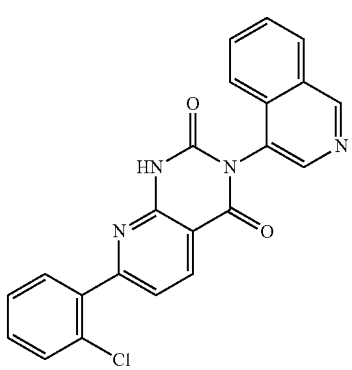 [SMILES: O=c1[nH]c2nc(-c3ccccc3Cl)ccc2c(=O)n1-c1cncc2ccccc12] | 401.0 | 1H NMR (400 MHz, MeOD) δ 9.64 (s, 1H), 8.70 (s, 1H), 8.53 (d, J = 8.1 Hz, 1H), 8.45 (dt, J = 8.3, 1.0 Hz, 1H), 8.11-7.99 (m, 2H), 7.94 (ddd, J = 8.2, 6.5, 1.6 Hz, 1H), 7.80-7.64 (m, 2H), 7.64-7.58 (m, 1H), 7.58-7.44 (m, 2H). | I-14; 2-(2-chlorophenyl)-4,4,5,5-tetramethyl-1,3,2-dioxaborolane |

TABLE 3-continued

Examples 25-64

| Example | Structure | ES/MS m/z | ¹H-NMR | Changes to Procedure 2: Different Reagents/Starting Materials |
|---|---|---|---|---|
| 33 | 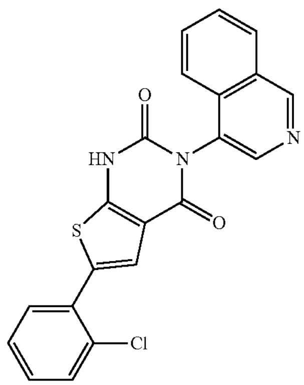 [SMILES: O=c1[nH]c2sc(-c3ccccc3Cl)cc2c(=O)n1-c1cncc2ccccc12] | 374.0 | 1H NMR (400 MHz, MeOD) δ 9.61 (s, 1H), 8.66 (s, 1H), 8.43 (dt, J = 8.3, 1.0 Hz, 1H), 8.08-7.97 (m, 2H), 7.93 (ddd, J = 8.1, 6.5, 1.5 Hz, 1H), 7.71-7.64 (m, 1H), 7.64-7.55 (m, 2H), 7.51-7.37 (m, 2H). | I-16; (2-chlorophenyl)boronic acid |
| 34 | 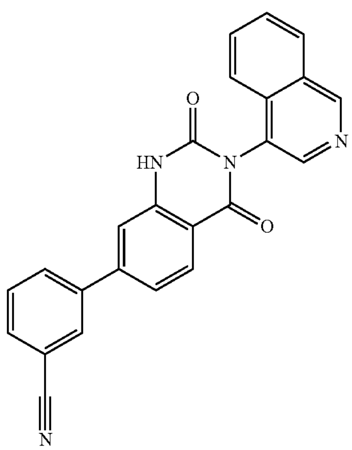 [SMILES: N#Cc1cccc(-c2ccc3c(=O)n(-c4cncc5ccccc45)c(=O)[nH]c3c2)c1] | 391.0 | 1H NMR (400 MHz, Methanol-d4) δ 9.64 (s, 1H), 8.69 (s, 1H), 8.46 (d, J = 8.2 Hz, 1H), 8.23 (d, J = 8.2 Hz, 1H), 8.16 (t, J = 1.7 Hz, 1H), 8.13-7.91 (m, 4H), 7.87 (dt, J = 7.7, 1.4 Hz, 1H), 7.76 (t, J = 7.8 Hz, 1H), 7.66 (dd, J = 8.2, 1.7 Hz, 1H), 7.59 (d, J = 1.6 Hz, 1H). | (3-cyanophenyl)boronic acid |
| 35 | 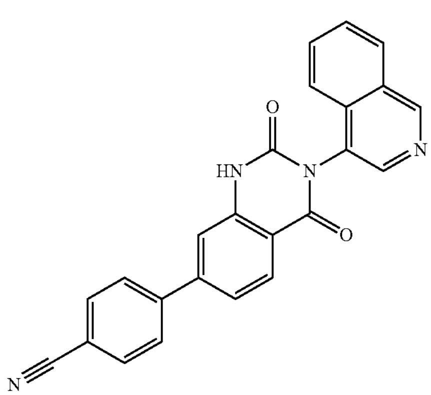 [SMILES: N#Cc1ccc(-c2ccc3c(=O)n(-c4cncc5ccccc45)c(=O)[nH]c3c2)cc1] | 391.1 | 1H NMR (400 MHz, Methanol-d4) δ 9.62 (s, 1H), 8.68 (s, 1H), 8.44 (d, J = 8.2 Hz, 1H), 8.24 (d, J = 8.3 Hz, 1H), 8.03-7.96 (m, J = 8.4, 4.2 Hz, 6H), 7.69 (dd, J = 16.7, 8.1 Hz, 2H), 7.61 (s, 1H). | (4-cyanophenyl)boronic acid |

TABLE 3-continued

Examples 25-64

| Example | Structure | ES/MS m/z | ¹H-NMR | Changes to Procedure 2: Different Reagents/Starting Materials |
|---|---|---|---|---|
| 36 | 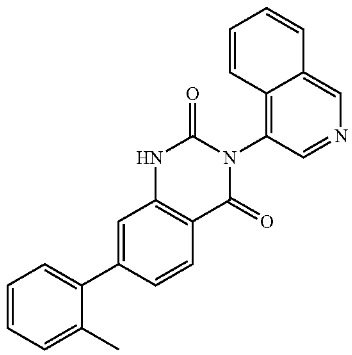 [SMILES: Cc1ccccc1-c1ccc2c(=O)n(-c3cncc4ccccc34)c(=O)[nH]c2c1] | 380.1 | 1H NMR (400 MHz, Methanol-d4) δ 9.63 (d, J = 0.8 Hz, 1H), 8.69 (s, 1H), 8.45 (dt, J = 8.2, 1.0 Hz, 1H), 8.17 (dd, J = 8.1, 0.5 Hz, 1H), 8.09-7.96 (m, 2H), 7.94 (ddd, J = 8.1, 6.6, 1.5 Hz, 1H), 7.41-7.26 (m, 6H), 2.35 (s, 3H). | o-toylboronic acid |
| 37 | 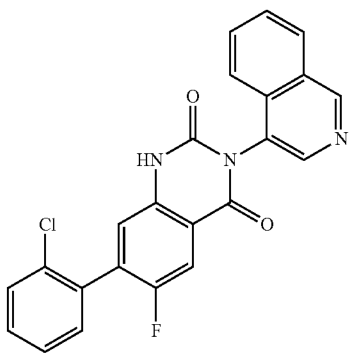 [SMILES: O=c1[nH]c2cc(-c3ccccc3Cl)c(F)cc2c(=O)n1-c1cncc2ccccc12] | 418.0 | 1H NMR (400 MHz, Methanol-d4) δ 9.68 (s, 1H), 8.72 (s, 1H), 8.48 (d, J = 8.3 Hz, 1H), 8.16-8.01 (m, 2H), 7.97 (t, J = 7.4 Hz, 1H), 7.89 (d, J = 10.0 Hz, 1H), 7.68 (d, J = 7.4 Hz, 2H), 7.62-7.47 (m, 3H), 7.44 (d, J = 6.1 Hz, 1H). | I-3; dioxane solvent |
| 38 | 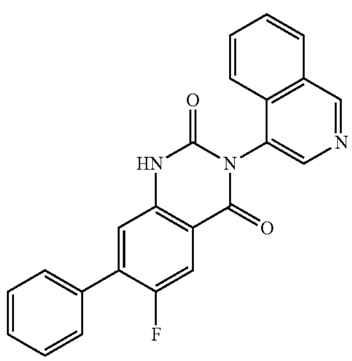 [SMILES: O=c1[nH]c2cc(-c3ccccc3)c(F)cc2c(=O)n1-c1cncc2ccccc12] | 384.1 | 1H NMR (400 MHz, Methanol-d4) δ 9.72 (s, 1H), 8.75 (s, 1H), 8.51 (d, J = 8.3 Hz, 1H), 8.10 (d, J = 6.5 Hz, 2H), 7.99 (t, J = 7.2 Hz, 1H), 7.89 (d, J = 8.9 Hz, 1H), 7.68-7.57 (m, 1H), 7.57-7.43 (m, 3H), 7.37-7.27 (m, 1H). | I-3; phenylboronic acid; dioxane solvent |
| 39 | 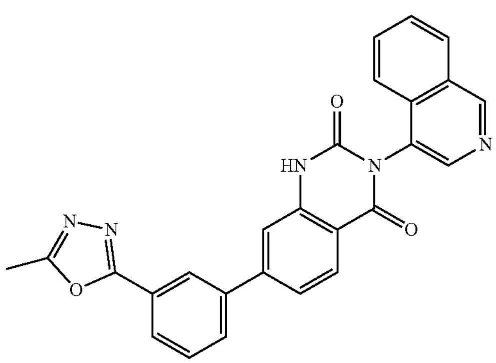 [SMILES: Cc1nnc(-c2cccc(-c3ccc4c(=O)n(-c5cncc6ccccc56)c(=O)[nH]c4c3)c2)o1] | 448.1 | 1H NMR (400 MHz, DMSO-d6) δ 11.85 (s, 1H), 9.50 (s, 1H), 8.63 (s, 1H), 8.33 (dd, J = 7.7, 1.6 Hz, 1H), 8.28 (t, J = 1.8 Hz, 1H), 8.10 (dd, J = 8.6, 1.6 Hz, 2H), 8.00 (dt, J = 8.0, 1.3 Hz, 1H), 7.93 (d, J = 8.1 Hz, 1H), 7.88-7.76 (m, 3H), 7.68 (dd, J = 8.3, 1.7 Hz, 1H), 7.65 (s, 0H), 2.64 (s, 3H). | 2-(3-Boronophenyl)Boronophenyl)-1,3,4-oxadiazole; dioxane solvent |

TABLE 3-continued

Examples 25-64

| Example | Structure | ES/MS m/z | ¹H-NMR | Changes to Procedure 2: Different Reagents/Starting Materials |
|---|---|---|---|---|
| 40 | 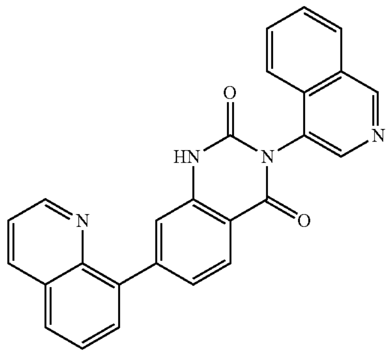 [SMILES: O=c1[nH]c2cc(-c3cccc4cccnc34)ccc2c(=O)n1-c1cncc2ccccc12] | 417.1 | 1H NMR (400 MHz, DMSO-d6) δ 11.86 (s, 1H), 9.57 (s, 1H), 8.97 (dd, J = 4.2, 1.8 Hz, 1H), 8.68 (s, 1H), 8.53 (dd, J = 8.3, 1.8 Hz, 1H), 8.37 (dd, J = 7.5, 1.4 Hz, 1H), 8.14 (dd, J = 8.2, 1.5 Hz, 1H), 8.07 (d, J = 8.1 Hz, 1H), 8.03-7.95 (m, 1H), 7.92-7.73 (m, 4H), 7.65 (dd, J = 8.3, 4.2 Hz, 1H), 7.60 (d, J = 1.5 Hz, 1H), 7.55 (d, J = 1.5 Hz, 0H), 7.53 (d, J = 1.5 Hz, 0H). | 8-quinolinylboronic acid; dioxane solvent |
| 41 | 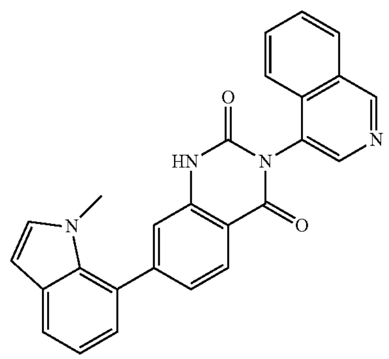 [SMILES: Cn1ccc2cccc(-c3ccc4c(=O)n(-c5cncc6ccccc56)c(=O)[nH]c4c3)c21] | 419.1 | 1H NMR (400 MHz, DMSO-d6) δ 11.86 (s, 1H), 9.51 (s, 1H), 8.64 (s, 1H), 8.33 (dd, J = 7.7, 1.5 Hz, 1H), 8.04 (d, J = 8.1 Hz, 1H), 7.96 (d, J = 8.2 Hz, 1H), 7.92-7.76 (m, 2H), 7.67 (dd, J = 7.9, 1.1 Hz, 1H), 7.43-7.29 (m, 3H), 7.14 (t, J = 7.5 Hz, 1H), 7.01 (dd, J = 7.2, 1.1 Hz, 1H), 6.58 (d, J = 3.1 Hz, 1H), 3.43 (s, 3H). | 1-Methyl-7-(4,4,5,5-tetramethyl-1,3,2-dioxaborolan-2-yl)-1H-indole; dioxane solvent |
| 42 | 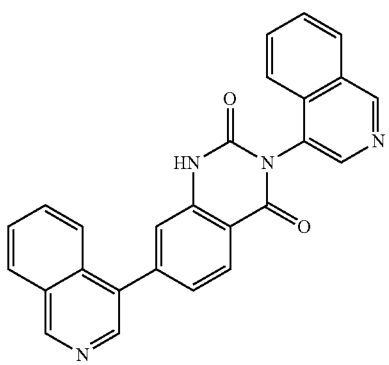 [SMILES: O=c1[nH]c2cc(-c3cncc4ccccc34)ccc2c(=O)n1-c1cncc2ccccc12] | 417.1 | 1H NMR (400 MHz, DMSO-d6) δ 11.94 (s, 1H), 9.55 (d, J = 28.8 Hz, 2H), 8.63 (d, J = 13.7 Hz, 2H), 8.46-8.24 (m, 2H), 8.17 (d, J = 8.0 Hz, 1H), 8.05-7.62 (m, 6H), 7.57-7.38 (m, 2H). | 4-isoquinolylboronic acid; dioxane solvent |
| 43 | 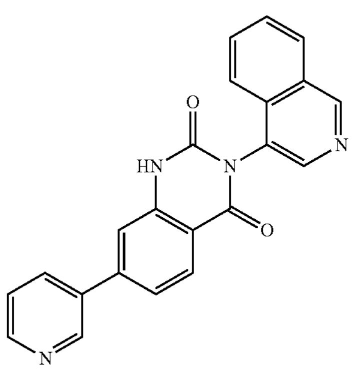 [SMILES: O=c1[nH]c2cc(-c3cccnc3)ccc2c(=O)n1-c1cncc2ccccc12] | 367.0 | 1H NMR (400 MHz, DMSO-d6) δ 11.93 (s, 1H), 9.51 (s, 1H), 9.03 (d, J = 2.3 Hz, 1H), 8.77 (dd, J = 5.0, 1.5 Hz, 1H), 8.63 (s, 1H), 8.48-8.21 (m, 2H), 8.10 (d, J = 8.2 Hz, 1H), 7.92 (d, J = 8.1 Hz, 1H), 7.87-7.77 (m, 2H), 7.72 (dd, J = 8.0, 5.0 Hz, 1H), 7.67 (dd, J = 8.2, 1.7 Hz, 1H), 7.58 (d, J = 1.6 Hz, 1H). | 3-Pyridineboronic acid neopentylglycol ester; dioxane solvent |

TABLE 3-continued

Examples 25-64

| Example | Structure | ES/MS m/z | ¹H-NMR | Changes to Procedure 2: Different Reagents/Starting Materials |
|---|---|---|---|---|
| 44 | 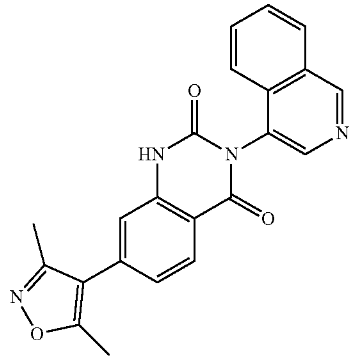 [SMILES: Cc1noc(C)c1-c1ccc2c(=O)n(-c3cncc4ccccc34)c(=O)[nH]c2c1] | 385.1 | 1H NMR (400 MHz, DMSO-d6) δ 11.79 (s, 1H), 9.49 (d, J = 4.4 Hz, 1H), 8.60 (d, J = 4.3 Hz, 1H), 8.31 (ddd, J = 6.0, 4.3, 1.9 Hz, 1H), 8.05 (d, J = 8.0 Hz, 1H), 7.91 (dd, J = 11.2, 8.2 Hz, 1H), 7.86-7.74 (m, 2H), 7.56-7.40 (m, 1H), 7.33 (d, J = 8.0 Hz, 2H), 2.50 (s, 3H), 2.32 (s, 3H). | 3,5-dimethyl-4-(4,4,5,5-tetramethyl-1,3,2-dioxaborolan-2-yl)isoxazole; dioxane solvent |
| 45 | 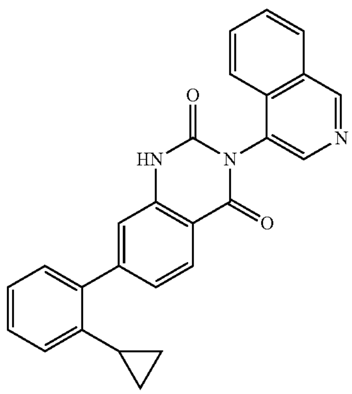 [SMILES: O=c1[nH]c2cc(-c3ccccc3C3CC3)ccc2c(=O)n1-c1cncc2ccccc12] | 406.1 | 1H NMR (400 MHz, DMSO-d6) δ 11.87 (s, 1H), 9.53 (s, 1H), 8.64 (s, 1H), 8.34 (dd, J = 7.4, 1.5 Hz, 1H), 8.04 (d, J = 8.0 Hz, 1H), 7.95 (dd, J = 8.2, 1.4 Hz, 1H), 7.83 (dddd, J = 16.3, 8.1, 6.9, 1.4 Hz, 2H), 7.43-7.23 (m, 5H), 7.06 (dd, J = 7.7, 1.2 Hz, 1H), 1.85 (tt, J = 8.4, 5.3 Hz, 1H), 1.02-0.87 (m, 2H), 0.85-0.67 (m, 2H). | (2-cyclopropylphenyl)boronic acid; dioxane solvent |
| 46 | 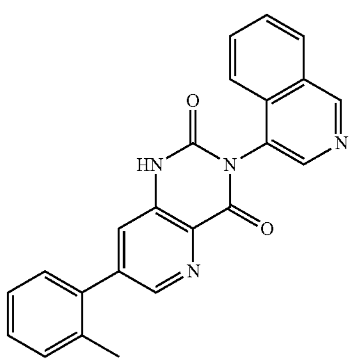 [SMILES: Cc1ccccc1-c1cnc2c(=O)n(-c3cncc4ccccc34)c(=O)[nH]c2c1] | 381.0 | 1H NMR (400 MHz, DMSO-d6) δ 11.90 (s, 1H), 9.52 (s, 1H), 8.64 (s, 1H), 8.58 (d, J = 1.9 Hz, 1H), 8.33 (dd, J = 7.3, 1.4 Hz, 1H), 8.06 (dd, J = 8.2, 1.3 Hz, 1H), 7.95-7.79 (m, 2H), 7.64 (d, J = 1.9 Hz, 1H), 7.52-7.32 (m, 4H), 2.33 (s, 3H). | I-13; o-tolylboronic acid; dioxane solvent |
| 47 | 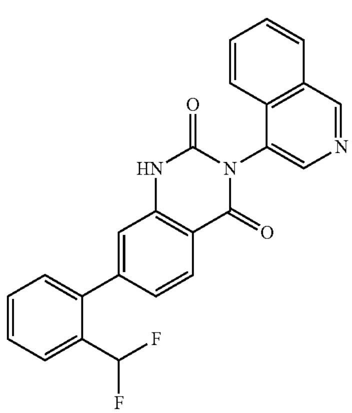 [SMILES: O=c1[nH]c2cc(-c3ccccc3C(F)F)ccc2c(=O)n1-c1cncc2ccccc12] | 394.1 | 1H NMR (400 MHz, DMSO-d6) δ 11.89 (s, 1H), 9.98 (s, 1H), 9.51 (s, 1H), 8.63 (s, 1H), 8.39-8.25 (m, 1H), 8.08 (d, J = 8.0 Hz, 1H), 8.01 (dd, J = 7.8, 1.4 Hz, 1H), 7.95 (dd, J = 8.2, 1.3 Hz, 1H), 7.92-7.77 (m, 3H), 7.76-7.69 (m, 1H), 7.59 (dd, J = 7.6, 1.1 Hz, 1H), 7.37 (dd, J = 8.1, 1.6 Hz, 1H), 7.30 (d, J = 1.6 Hz, 1H). | [2-(difluoromethyl)phenyl]boronic acid; dioxane solvent |

TABLE 3-continued

Examples 25-64

| Example | Structure | ES/MS m/z | ¹H-NMR | Changes to Procedure 2: Different Reagents/Starting Materials |
|---|---|---|---|---|
| 48 | 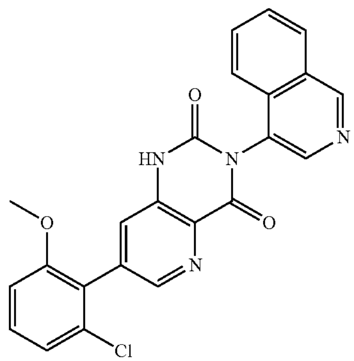 [SMILES: COc1cccc(Cl)c1-c1cnc2c(=O)n(-c3cncc4ccccc34)c(=O)[nH]c2c1] | 431.1 | 1H NMR (400 MHz, DMSO-d6) δ 11.88 (s, 1H), 9.52 (s, 1H), 8.43 (d, J = 1.8 Hz, 1H), 8.33 (dd, J = 7.2, 1.7 Hz, 1H), 8.14 (dd, J = 8.0, 1.5 Hz, 1H), 8.03-7.69 (m, 3H), 7.63-7.47 (m, 2H), 7.26 (ddd, J = 15.8, 8.3, 0.9 Hz, 2H), 3.79 (s, 3H). | I-13; (2-chloro-6-methoxyphenyl)boronic acid; dioxane solvent |
| 49 | 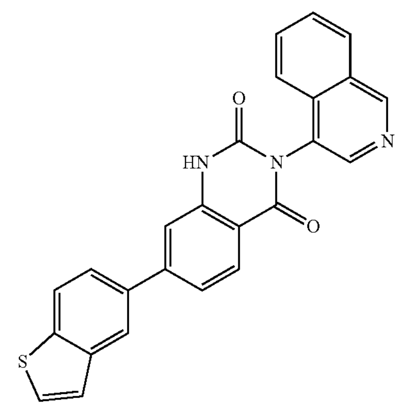 [SMILES: O=c1[nH]c2cc(-c3ccc4sccc4c3)ccc2c(=O)n1-c1cncc2ccccc12] | 422.1 | 1H NMR (400 MHz, DMSO) δ 11.87 (s, 1H), 9.52 (s, 1H), 8.64 (s, 1H), 8.37-8.30 (m, 1H), 8.27 (d, J = 1.8 Hz, 1H), 8.21 (d, J = 8.4 Hz, 1H), 8.08 (d, J = 8.2 Hz, 1H), 7.99-7.78 (m, 4H), 7.72 (dd, J = 8.5, 1.9 Hz, 1H), 7.67 (dd, J = 8.3, 1.7 Hz, 1H), 7.62 (dd, J = 5.5, 1.0 Hz, 2H). | 2-(benzothiophen-5-yl)-4,4,5,5-tetramethyl-1,3,2-dioxaborolane |
| 50 | 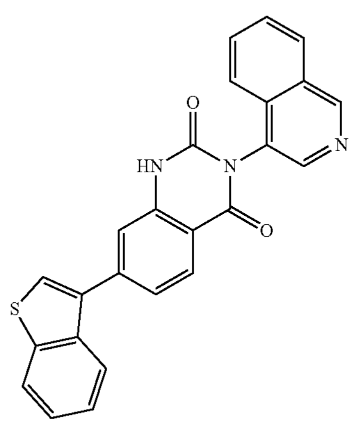 [SMILES: O=c1[nH]c2cc(-c3csc4ccccc34)ccc2c(=O)n1-c1cncc2ccccc12] | 422.1 | 1H NMR (400 MHz, DMSO) δ 11.85 (s, 1H), 9.50 (s, 1H), 8.63 (s, 1H), 8.33 (dd, J = 7.5, 1.7 Hz, 1H), 8.20-8.06 (m, 3H), 8.00 (dd, J = 7.3, 1.7 Hz, 1H), 7.94 (dd, J = 8.2, 1.5 Hz, 1H), 7.82 (dddd, J = 16.1, 8.1, 6.9, 1.4 Hz, 2H), 7.61-7.46 (m, 4H). | benzothiophen-3-ylboronic acid |

TABLE 3-continued

Examples 25-64

| Example | Structure | ES/MS m/z | ¹H-NMR | Changes to Procedure 2: Different Reagents/Starting Materials |
|---|---|---|---|---|
| 51 | 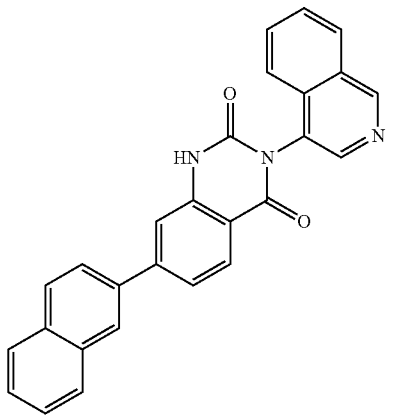 [SMILES: O=c1[nH]c2cc(-c3ccc4ccccc4c3)ccc2c(=O)n1-c1cncc2ccccc12] | 416.2 | 1H NMR (400 MHz, DMSO) δ 11.89 (s, 1H), 9.53 (s, 1H), 8.66 (s, 1H), 8.40-8.31 (m, 2H), 8.18-7.57 (m, 12H). | 4,4,5,5-tetramethyl-2-(2-naphthyl)-1,3,2-dioxaborolane |
| 52 | 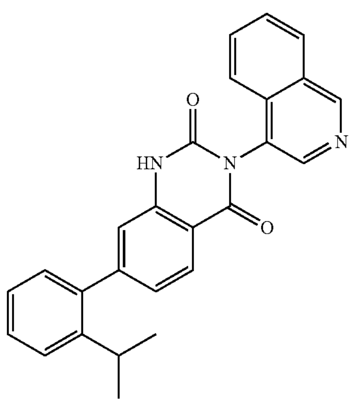 [SMILES: CC(C)c1ccccc1-c1ccc2c(=O)n(-c3cncc4ccccc34)c(=O)[nH]c2c1] | 408.2 | 1H NMR (400 MHz, DMSO) δ 11.85 (s, 1H), 9.54 (d, J = 0.9 Hz, 1H), 8.65 (s, 1H), 8.38-8.31 (m, 1H), 8.07-7.97 (m, 2H), 7.84 (dddd, J = 16.4, 8.1, 6.9, 1.4 Hz, 2H), 7.52 (dd, J = 7.9, 1.4 Hz, 1H), 7.36-7.17 (m, 5H), 3.01 (hept, J = 6.9 Hz, 1H), 1.19 (d, J = 6.8 Hz, 6H). | (2-isopropylphenyl)boronic acid |
| 53 | 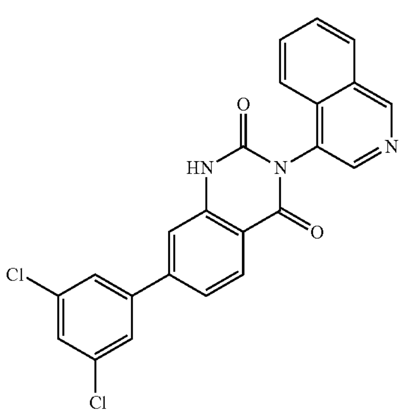 [SMILES: O=c1[nH]c2cc(-c3cc(Cl)cc(Cl)c3)ccc2c(=O)n1-c1cncc2ccccc12] | 434.1 | 1H NMR (400 MHz, DMSO) δ 11.84 (s, 1H), 9.53-9.48 (m, 1H), 8.63 (s, 1H), 8.36-8.29 (m, 1H), 8.06 (d, J = 8.2 Hz, 1H), 7.95-7.88 (m, 1H), 7.87-7.75 (m, 5H), 7.65 (dd, J = 8.3, 1.7 Hz, 1H), 7.53 (d, J = 1.7 Hz, 1H). | (3,5-dichlorophenyl)boronic acid |

TABLE 3-continued

Examples 25-64

| Example | Structure | ES/MS m/z | ¹H-NMR | Changes to Procedure 2: Different Reagents/Starting Materials |
|---|---|---|---|---|
| 54 | 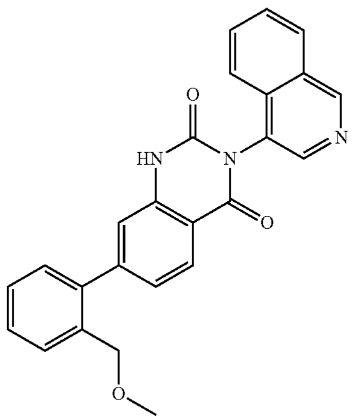 [SMILES: COCc1ccccc1-c1ccc2c(=O)n(-c3cncc4ccccc34)c(=O)[nH]c2c1] | 410.2 | 1H NMR (400 MHz, DMSO) δ 11.88 (s, 1H), 9.53 (s, 1H), 8.65 (s, 1H), 8.34 (dd, J = 7.5, 1.6 Hz, 1H), 8.03 (d, J = 8.5 Hz, 1H), 7.96 (dd, J = 8.2, 1.3 Hz, 1H), 7.83 (dddd, J = 16.6, 8.1, 6.9, 1.4 Hz, 2H), 7.62-7.53 (m, 1H), 7.53-7.43 (m, 2H), 7.39-7.32 (m, 1H), 7.30 (dt, J = 4.3, 2.1 Hz, 2H), 4.35 (s, 2H), 3.28 (s, 3H). | [2-(methoxymethyl)phenyl]boronic acid |
| 55 | 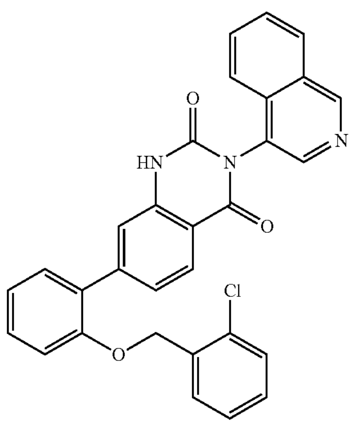 [SMILES: O=c1[nH]c2cc(-c3ccccc3OCc3ccccc3Cl)ccc2c(=O)n1-c1cncc2ccccc12] | 506.1 | 1H NMR (400 MHz, DMSO) δ 11.83 (s, 1H), 9.51 (d, J = 0.9 Hz, 1H), 8.62 (s, 1H), 8.38-8.28 (m, 1H), 8.01-7.90 (m, 2H), 7.88-7.76 (m, 2H), 7.62-7.35 (m, 8H), 7.30 (dd, J = 8.4, 1.0 Hz, 1H), 7.17 (td, J = 7.5, 1.0 Hz, 1H), 5.25 (s, 2H). | [2-[(2-chlorophenyl)methoxy]phenyl]boronic acid |
| 56 | 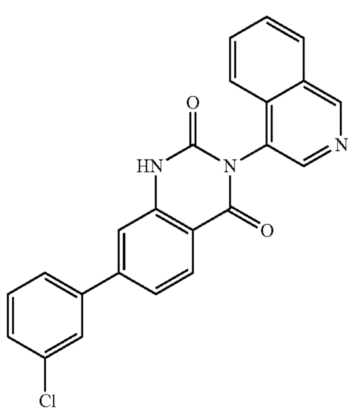 [SMILES: O=c1[nH]c2cc(-c3cccc(Cl)c3)ccc2c(=O)n1-c1cncc2ccccc12] | 400.1 | 1H NMR (400 MHz, DMSO) δ 11.87 (s, 1H), 9.53 (s, 1H), 8.64 (s, 1H), 8.34 (dd, J = 7.9, 1.6 Hz, 1H), 8.06 (d, J = 8.2 Hz, 1H), 7.99-7.90 (m, 2H), 7.90-7.77 (m, 3H), 7.76-7.51 (m, 4H). | 2-(3-chlorophenyl)-4,4,5,5-tetramethyl-1,3,2-dioxaborolane |

TABLE 3-continued

Examples 25-64

| Example | Structure | ES/MS m/z | ¹H-NMR | Changes to Procedure 2: Different Reagents/Starting Materials |
|---|---|---|---|---|
| 57 | 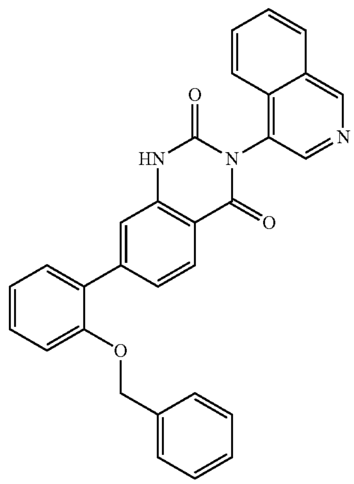 [SMILES: O=c1[nH]c2cc(-c3ccccc3OCc3ccccc3)ccc2c(=O)n1-c1cncc2ccccc12] | 472.2 | 1H NMR (400 MHz, DMSO) δ 11.86 (s, 1H), 9.53 (s, 1H), 8.64 (s, 1H), 8.38-8.31 (m, 1H), 8.02-7.90 (m, 2H), 7.83 (pd, J = 6.9, 1.5 Hz, 2H), 7.54-7.24 (m, 10H), 7.13 (td, J = 7.4, 1.0 Hz, 1H), 5.21 (s, 2H). | (2-benzyloxyphenyl)boronic acid |
| 58 | 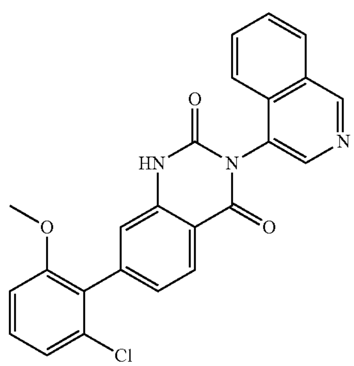 [SMILES: COc1cccc(Cl)c1-c1ccc2c(=O)n(-c3cncc4ccccc34)c(=O)[nH]c2c1] | 430.1 | 1H NMR (400 MHz, DMSO) δ 11.82 (s, 1H), 9.54 (s, 1H), 8.67 (s, 1H), 8.38-8.31 (m, 1H), 8.03 (d, J = 8.0 Hz, 2H), 7.84 (dddd, J = 15.9, 8.1, 6.9, 1.4 Hz, 2H), 7.47 (t, J = 8.3 Hz, 1H), 7.26-7.10 (m, 4H), 3.76 (s, 3H). | (2-chloro-6-methoxy-phenyl)boronic acid |
| 59 | 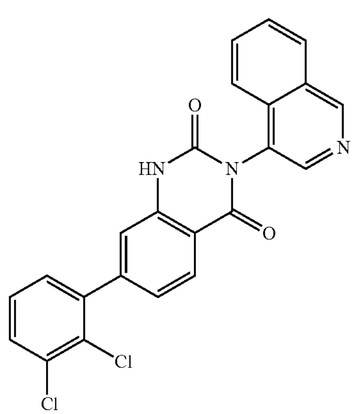 [SMILES: O=c1[nH]c2cc(-c3cccc(Cl)c3Cl)ccc2c(=O)n1-c1cncc2ccccc12] | 435.1 | 1H NMR (400 MHz, DMSO) δ 11.91 (s, 1H), 9.51 (s, 1H), 8.64 (s, 1H), 8.36-8.29 (m, 1H), 8.07 (d, J = 8.1 Hz, 1H), 7.97 (d, J = 8.1 Hz, 1H), 7.89-7.75 (m, 3H), 7.54 (td, J = 7.9, 1.3 Hz, 1H), 7.46 (dt, J = 7.6, 1.5 Hz, 1H), 7.37-7.31 (m, 2H). | (2,3-dichlorophenyl)boronic acid |

TABLE 3-continued

Examples 25-64

| Example | Structure | ES/MS m/z | ¹H-NMR | Changes to Procedure 2: Different Reagents/Starting Materials |
|---|---|---|---|---|
| 60 | 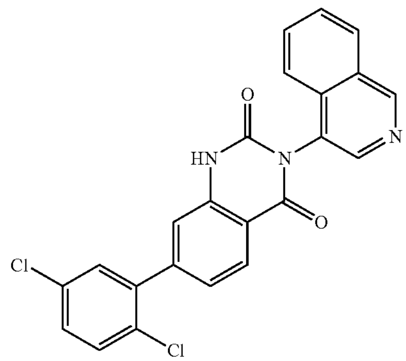 [SMILES: O=c1[nH]c2cc(-c3cc(Cl)ccc3Cl)ccc2c(=O)n1-c1cncc2ccccc12] | 434.0 | 1H NMR (400 MHz, DMSO) δ 11.90 (s, 1H), 9.52 (s, 1H), 8.65 (s, 1H), 8.37-8.30 (m, 1H), 8.07 (d, J = 8.5 Hz, 1H), 8.01-7.93 (m, 1H), 7.83 (dddd, J = 16.1, 8.2, 6.9, 1.4 Hz, 2H), 7.74-7.67 (m, 1H), 7.64-7.56 (m, 2H), 7.38-7.31 (m, 2H). | (2,5-dichlorophenyl)boronic acid |
| 61 | 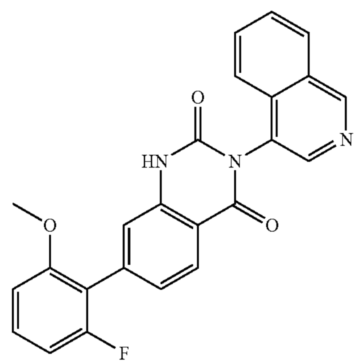 [SMILES: COc1cccc(F)c1-c1ccc2c(=O)n(-c3cncc4ccccc34)c(=O)[nH]c2c1] | 414.2 | 1H NMR (400 MHz, DMSO-d6) δ 11.81 (s, 1H), 9.54 (s, 1H), 8.65 (s, 1H), 8.37-8.30 (m, 1H), 8.09-7.94 (m, 2H), 7.83 (dqd, J = 8.1, 6.9, 1.4 Hz, 2H), 7.48 (td, J = 8.4, 6.8 Hz, 1H), 7.28 (s, 1H), 7.24 (d, J = 8.1 Hz, 1H), 7.05 (d, J = 8.5 Hz, 1H), 6.99 (ddd, J = 9.3, 8.4, 0.9 Hz, 1H), 3.80 (s, 3H). | 2-(2-fluoro-6-methoxy-phenyl)-4,4,5,5-tetramethyl-1,3,2-dioxaborolane |
| 62 | 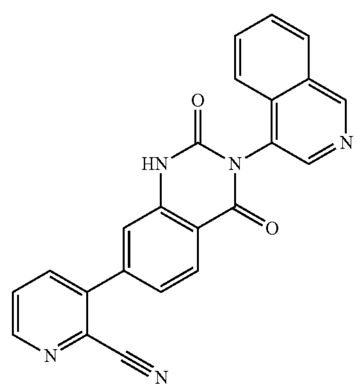 [SMILES: N#Cc1ncccc1-c1ccc2c(=O)n(-c3cncc4ccccc34)c(=O)[nH]c2c1] | 392.1 | 1H NMR (400 MHz, DMSO-d6) δ 12.00 (s, 1H), 9.46 (s, 1H), 8.88 (dd, J = 4.8, 1.6 Hz, 1H), 8.61 (s, 1H), 8.35-8.26 (m, 1H), 8.21 (dd, J = 8.0, 1.6 Hz, 1H), 8.15 (d, J = 8.0 Hz, 1H), 7.97-7.91 (m, 2H), 7.83-7.76 (m, 2H), 7.56-7.50 (m, 2H). | 3-(4,4,5,5-tetramethyl-1,3,2-dioxaborolan-2-yl)picolinonitrile |
| 63 | 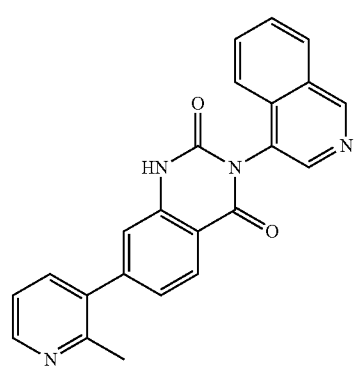 [SMILES: Cc1ncccc1-c1ccc2c(=O)n(-c3cncc4ccccc34)c(=O)[nH]c2c1] | 381.1 | 1H NMR (400 MHz, DMSO-d6) δ 11.96 (s, 1H), 9.50 (d, J = 0.8 Hz, 1H), 8.78 (dd, J = 5.4, 1.6 Hz, 1H), 8.62 (s, 1H), 8.40-8.25 (m, 1H), 8.17 (dd, J = 7.8, 1.6 Hz, 1H), 8.11 (d, J = 8.1 Hz, 1H), 7.94 (dd, J = 8.1, 1.4 Hz, 1H), 7.87-7.81 (m, 1H), 7.81-7.74 (m, 2H), 7.37 (dd, J = 8.1, 1.6 Hz, 1H), 7.32 (d, J = 1.6 Hz, 1H), 2.61 (s, 3H). | (2-methylpyridin-3-yl)boronic acid |

TABLE 3-continued

Examples 25-64

| Example | Structure | ES/MS m/z | ¹H-NMR | Changes to Procedure 2: Different Reagents/Starting Materials |
|---|---|---|---|---|
| 64 | 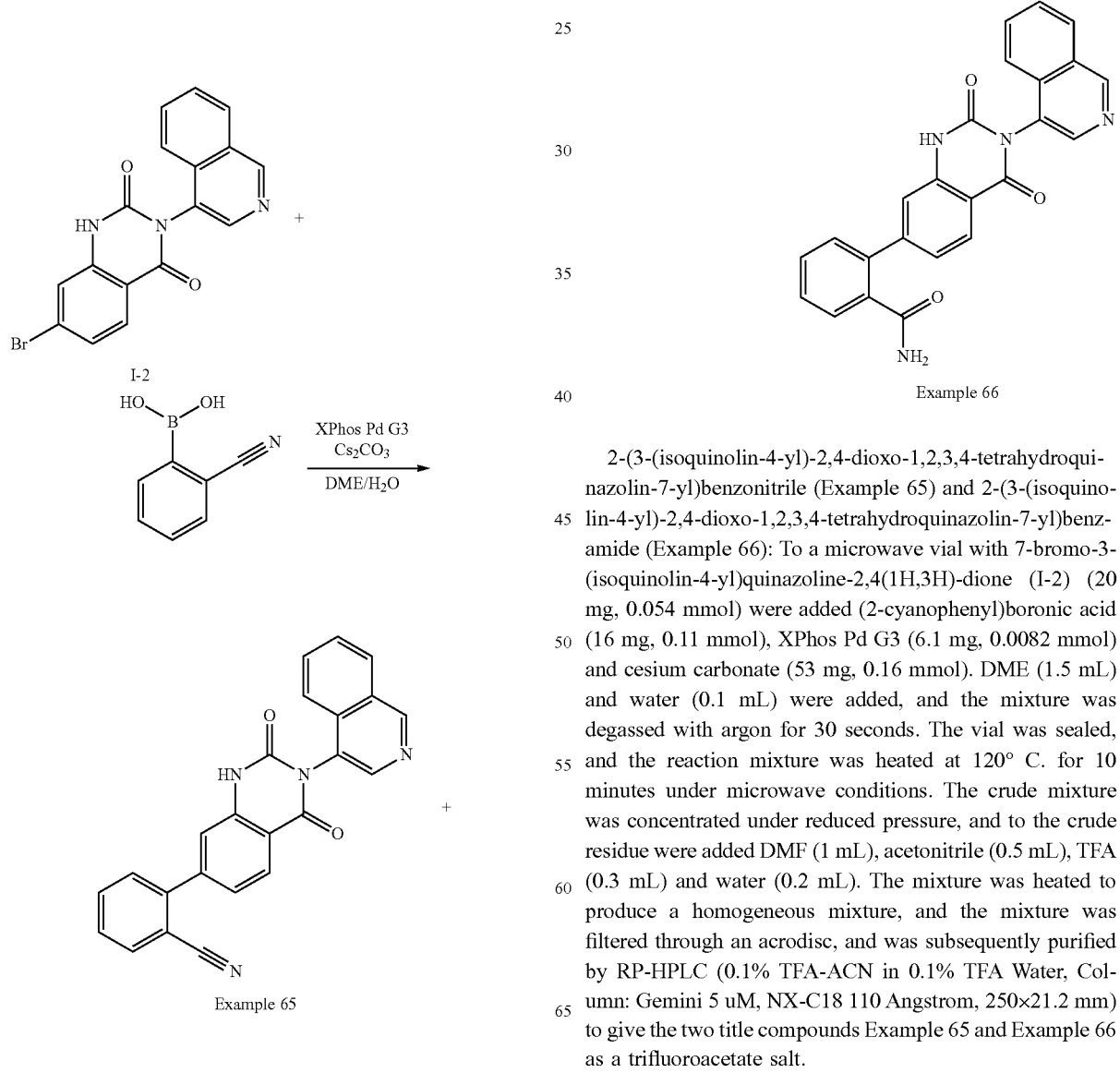 | 502.3 | 1H NMR (400 MHz, Chloroform-d) δ 9.41 (s, 1H), 8.53 (s, 1H), 8.22-8.13 (m, 1H), 7.89-7.80 (m, 1H), 7.78-7.70 (m, 2H), 7.59-7.52 (m, 1H), 7.47-7.34 (m, 3H), 4.10-3.97 (m, 2H), 2.68-2.59 (m, 1H), 2.33 (s, 3H), 1.89-1.77 (m, 2H), 1.77-1.52 (m, 4H), 1.50-1.26 (m, 2H). | I-55; (2-chlorophenyl)boronic acid |

Procedure 3: Examples 65 and 66

2-(3-(isoquinolin-4-yl)-2,4-dioxo-1,2,3,4-tetrahydroquinazolin-7-yl)benzonitrile (Example 65) and 2-(3-(isoquinolin-4-yl)-2,4-dioxo-1,2,3,4-tetrahydroquinazolin-7-yl)benzamide (Example 66): To a microwave vial with 7-bromo-3-(isoquinolin-4-yl)quinazoline-2,4(1H,3H)-dione (I-2) (20 mg, 0.054 mmol) were added (2-cyanophenyl)boronic acid (16 mg, 0.11 mmol), XPhos Pd G3 (6.1 mg, 0.0082 mmol) and cesium carbonate (53 mg, 0.16 mmol). DME (1.5 mL) and water (0.1 mL) were added, and the mixture was degassed with argon for 30 seconds. The vial was sealed, and the reaction mixture was heated at 120° C. for 10 minutes under microwave conditions. The crude mixture was concentrated under reduced pressure, and to the crude residue were added DMF (1 mL), acetonitrile (0.5 mL), TFA (0.3 mL) and water (0.2 mL). The mixture was heated to produce a homogeneous mixture, and the mixture was filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the two title compounds Example 65 and Example 66 as a trifluoroacetate salt.

Example 65

ES/MS: 391.1 (M+H⁺).

1H NMR (400 MHz, DMSO-d6) δ 11.96 (s, 1H), 9.47 (s, 1H), 8.61 (s, 1H), 8.30 (dd, J=7.0, 2.2 Hz, 1H), 8.21-8.03 (m, 2H), 8.00-7.87 (m, 2H), 7.87-7.68 (m, 4H), 7.47 (dq, J=3.9, 1.7 Hz, 2H).

Example 66

ES/MS: 409.1 (M+H⁺)

1H NMR (400 MHz, DMSO-d6) δ 11.87 (s, 1H), 9.46 (s, 1H), 8.59 (s, 1H), 8.30 (dd, J=7.1, 2.2 Hz, 1H), 7.97 (d, . J=8.2 Hz, 1H), 7.95-7.72 (m, 4H), 7.63-7.49 (m, 3H), 7.49-7.37 (m, 2H), 7.37-7.24 (m, 2H).

Examples 67-72

The following Examples were made in an analogous fashion according to Procedure 3 and are shown below in Table 4. Any different reagents/starting materials than those described in Procedure 3 are noted in the last column of Table 4—"Changes to Procedure 3: Different Reagents/Starting Materials".

TABLE 4

Examples 67-72

| Example | Structure | ES/MS m/z | ¹H-NMR | Changes to Procedure 3: Different Reagents/Starting Materials |
|---|---|---|---|---|
| 67 | 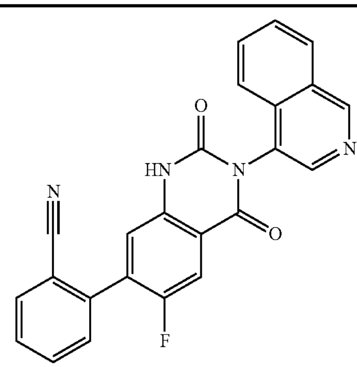 | 409.1 | 1H NMR (400 MHz, DMSO-d6) δ 11.97 (s, 1H), 9.46 (s, 1H), 8.61 (s, 1H), 8.30 (dd, J = 6.9, 2.1 Hz, 1H), 8.09 (dd, J = 7.8, 1.3 Hz, 1H), 8.06-7.88 (m, 3H), 7.87-7.68 (m, 3H), 7.68-7.45 (m, 1H), 7.36 (d, J = 6.0 Hz, 1H). | I-3 |
| 68 | 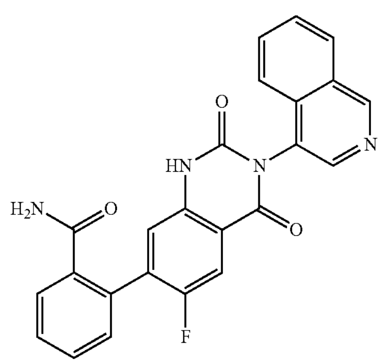 [SMILES: NC(=O)c1ccccc1-c1cc2[nH]c(=O)n(-c3cncc4ccccc34)c(=O)c2cc1F] | 427.1 | 1H NMR (400 MHz, DMSO-d6) δ 11.90 (s, 1H), 9.50 (s, 1H), 8.63 (s, 1H), 8.34-8.25 (m, 1H), 7.98-7.86 (m, 2H), 7.82 (dddd, J = 14.6, 8.2, 6.9, 1.5 Hz, 2H), 7.74-7.53 (m, 4H), 7.42 (dd, J = 7.4, 1.4 Hz, 1H), 7.34 (s, 1H), 7.25 (d, J = 6.1 Hz, 1H). | I-3 |
| 69 | 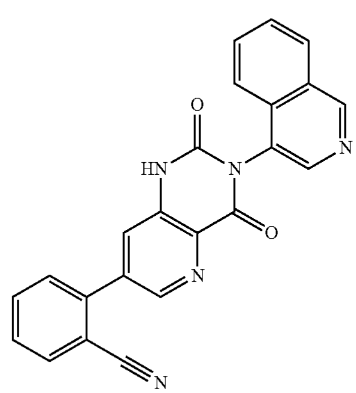 [SMILES: N#Cc1ccccc1-c1cnc2c(=O)n(-c3cncc4ccccc34)c(=O)[nH]c2c1] | 392.1 | 1H NMR (400 MHz, DMSO-d6) δ 11.94 (s, 1H), 9.48 (s, 1H), 8.62 (s, 1H), 8.53 (d, J = 1.9 Hz, 1H), 8.40-8.28 (m, 1H), 8.06-7.92 (m, 2H), 7.91-7.74 (m, 2H), 7.70 (d, J = 1.9 Hz, 1H), 7.68-7.55 | I-13; dioxane solvent |

TABLE 4-continued

Examples 67-72

| Example | Structure | ES/MS m/z | ¹H-NMR | Changes to Procedure 3: Different Reagents/ Starting Materials |
|---|---|---|---|---|
| 70 | 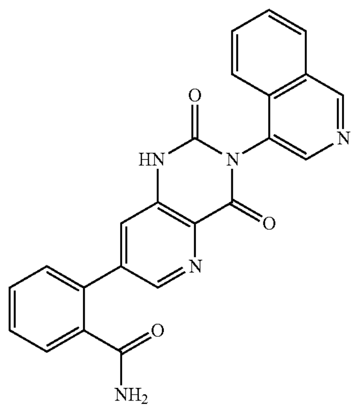 [SMILES: NC(=O)c1ccccc1-c1cnc2c(=O)n(-c3cncc4ccccc34)c(=O)[nH]c2c1] | 410.2 | 1H NMR (400 MHz, DMSO-d6) δ 12.05 (s, 1H), 9.51 (d, J = 0.8 Hz, 1H), 8.76 (d, J = 2.0 Hz, 1H), 8.65 (s, 1H), 8.39-8.24 (m, 1H), 8.11 (dt, J = 7.9, 1.5 Hz, 2H), 7.94 (td, J = 7.7, 1.4 Hz, 1H), 7.92-7.79 (m, 5H), 7.57-7.41 (m, 2H) | I-13; dioxane solvent |
| 71 | 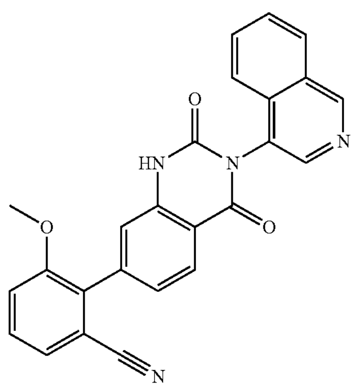 [SMILES: COc1cccc(C#N)c1-c1ccc2c(=O)n(-c3cncc4ccccc34)c(=O)[nH]c2c1] | 421.2 | 1H NMR (400 MHz, DMSO-d6) δ 11.89 (s, 1H), 9.56 (s, 1H), 8.69 (s, 1H), 8.35 (dd, J = 7.4, 1.5 Hz, 1H), 8.14-8.01 (m, 2H), 7.84 (dddd, J = 16.8, 8.1, 6.9, 1.4 Hz, 2H), 7.71-7.60 (m, 1H), 7.57 (ddd, J = 9.6, 8.0, 1.2 Hz, 2H), 7.40-7.20 (m, 2H), 3.82 (s, 3H). | 3-methoxy-2-(4,4,5,5-tetramethyl-1,3,2-dioxaborolan-2-yl)benzonitrile |
| 72 | 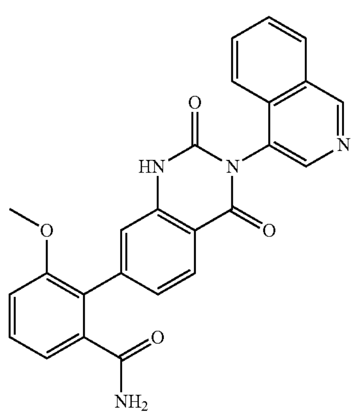 [SMILES: COc1cccc(C(N)=O)c1-c1ccc2c(=O)n(-c3cncc4ccccc34)c(=O)[nH]c2c1] | 439.2 | 1H NMR (400 MHz, DMSO-d6) δ 11.80 (s, 1H), 9.54 (s, 1H), 8.66 (s, 1H), 8.39-8.31 (m, 1H), 8.03-7.90 (m, 2H), 7.83 (dddd, J = 16.2, 8.2, 6.9, 1.4 Hz, 2H), 7.67 (s, 1H), 7.55-7.41 (m, 1H), 7.27-7.17 (m, 3H), 7.16-7.06 (m, 2H), 3.74 (s, 3H). | 3-methoxy-2-(4,4,5,5-tetramethyl-1,3,2-dioxaborolan-2-yl)benzonitrile |

Procedure 4: Example 73 and Example 74

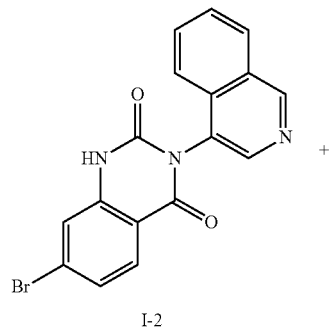

I-2

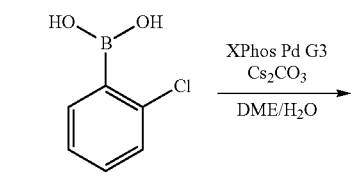

XPhos Pd G3
Cs₂CO₃
DME/H₂O

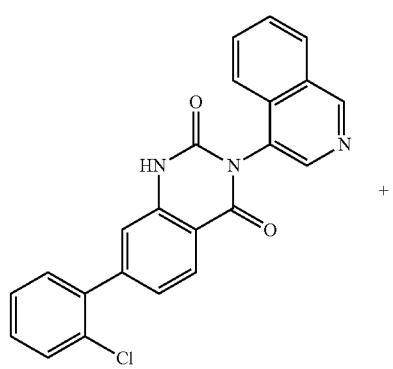

Example 73

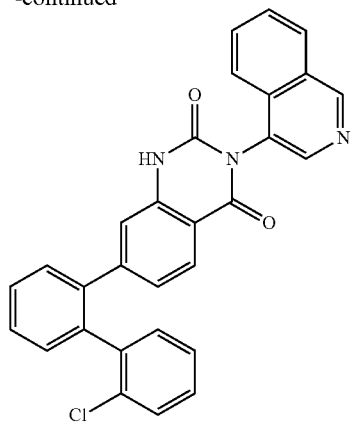

Example 74

7-(2-chlorophenyl)-3-(isoquinolin-4-yl)quinazoline-2,4 (1H,3H)-dione (Example 73) and 7-(2'-chloro-[1,1'-biphenyl]-2-yl)-3-(isoquinolin-4-yl)quinazoline-2,4(1H,3H)-dione (Example 74): To a microwave vial with 7-bromo-3-(isoquinolin-4-yl)quinazoline-2,4(1H,3H)-dione (I-2) (75 mg, 0.204 mmol) were added (2-chlorophenyl)boronic acid (48 mg, 0.306 mmol), XPhos Pd G3 (15.3 mg, 0.02 mmol) and cesium carbonate (199 mg, 0.611 mmol). DME (1.5 mL) and water (0.1 mL) were added, and the mixture was degassed with argon for 30 seconds. The vial was sealed, and the reaction mixture was heated at 120° C. for 10 minutes under microwave conditions. The crude mixture was concentrated under reduced pressure, and to the crude residue were added DMF (2 mL), acetonitrile (1 mL), TFA (0.6 mL) and water (0.2 mL). The mixture was heated to produce a homogeneous mixture, and the mixture was filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the two title compounds Example 73 and Example 74 as a trifluoroacetate salt.

Example 73

ES/MS: 400.1 (M⁺).
1H NMR (400 MHz, DMSO-d6) δ 11.87 (s, 1H), 9.48 (s, 1H), 8.61 (s, 1H), 8.31 (dd, J=7.2, 1.9 Hz, 1H), 8.06 (d, J=8.0 Hz, 1H), 8.02-7.90 (m, 1H), 7.81 (pd, J=6.9, 1.5 Hz, 2H), 7.66 (dt, J=7.4, 3.0 Hz, 1H), 7.51 (dq, J=6.4, 5.1 Hz, 3H), 7.33 (d, J=7.9 Hz, 2H).

Example 74

ES/MS: 476.1 (M⁺).
1H NMR (400 MHz, DMSO-d6) δ 11.74 (d, J=6.4 Hz, 1H), 9.45 (s, 1H), 8.57 (d, J=2.3 Hz, 1H), 8.34-8.20 (m, 1H), 7.88-7.68 (m, 4H), 7.54 (dddd, J=40.7, 19.0, 7.0, 2.0 Hz, 4H), 7.43-7.25 (m, 4H), 7.13 (dd, J=11.0, 1.6 Hz, 1H), 6.95 (ddd, J=10.0, 8.1, 1.6 Hz, 1H).

Examples 75-85

The following Examples were made in an analogous fashion according to Procedure 4 and are shown below in Table 5. Any different reagents/starting materials than those described in Procedure 4 are noted in the last column of Table 5—"Changes to Procedure 4: Different Reagents/Starting Materials".

TABLE 5

Examples 75-85

| Example | Structure | ES/MS m/z | ¹H-NMR | Changes to Procedure 4: Different Reagents/ Starting Materials |
|---|---|---|---|---|
| 75 | 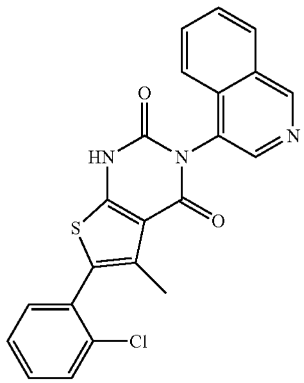 [SMILES: Cc1c(-c2ccccc2Cl)sc2[nH]c(=O)n(-c3cncc4ccccc34)c(=O)c12] | 420.0 | 1H NMR (400 MHz, DMSO-d6) δ 12.58 (s, 1H), 9.46 (s, 1H), 8.58 (s, 1H), 8.36-8.24 (m, 1H), 7.91 (d, J = 8.2 Hz, 1H), 7.80 (dddd, J = 19.1, 8.1, 6.9, 1.3 Hz, 2H), 7.66 (dd, J = 7.9, 1.7 Hz, 1H), 7.55-7.45 (m, 3H), 2.17 (s, 3H). | I-10 |
| 76 | 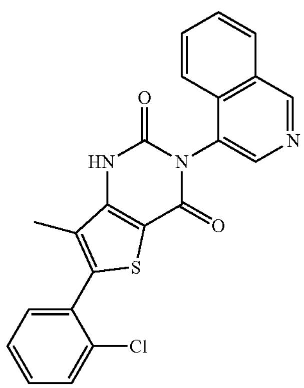 [SMILES: Cc1c(-c2ccccc2Cl)sc2c(=O)n(-c3cncc4ccccc34)c(=O)[nH]c12] | 420.0 | 1H NMR (400 MHz, DMSO-d6) δ 12.18 (s, 1H), 9.46 (s, 1H), 8.60 (s, 1H), 8.30 (d, J = 8.0 Hz, 1H), 7.96-7.65 (m, 4H), 7.65-7.44 (m, 3H), 2.13 (s, 3H). | I-11 |
| 77 | 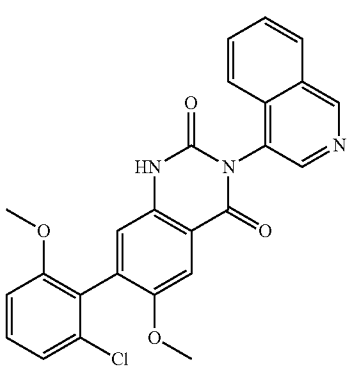 [SMILES: COc1cc2c(=O)n(-c3cncc4ccccc34)c(=O)[nH]c2cc1-c1c(Cl)cccc1OC] | 460.1 | 1H NMR (400 MHz, DMSO) δ 11.68 (s, 1H), 9.49 (s, 1H), 8.63 (d, J = 7.5 Hz, 1H), 8.32 (dd, J = 7.8, 1.5 Hz, 1H), 7.98-7.91 (m, 1H), 7.81 (dtd, J = 8.2, 6.7, 5.5 Hz, 2H), 7.52 (d, J = 1.3 Hz, 1H), 7.44 (t, J = 8.2 Hz, 1H), 7.22-7.11 (m, 2H), 7.03 (s, 1H), 3.80-3.67 (m, 6H). | I-19; (2-chloro-6-methoxy-phenyl)boronic acid |

TABLE 5-continued

Examples 75-85

| Example | Structure | ES/MS m/z | ¹H-NMR | Changes to Procedure 4: Different Reagents/ Starting Materials |
|---|---|---|---|---|
| 78 | 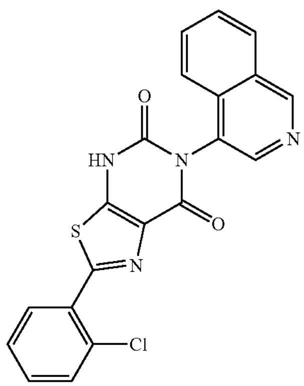 [SMILES: O=c1[nH]c2sc(-c3ccccc3Cl)nc2c(=O)n1-c1cncc2ccccc12] | 407.0 | 1H NMR (400 MHz, DMSO) δ 12.80 (s, 1H), 9.49 (s, 1H), 8.60 (s, 1H), 8.35-8.28 (m, 1H), 8.24-8.15 (m, 1H), 8.01 (dd, J = 8.3, 1.2 Hz, 1H), 7.89-7.76 (m, 2H), 7.76-7.67 (m, 1H), 7.63-7.51 (m, 2H). | I-20 |
| 79 | 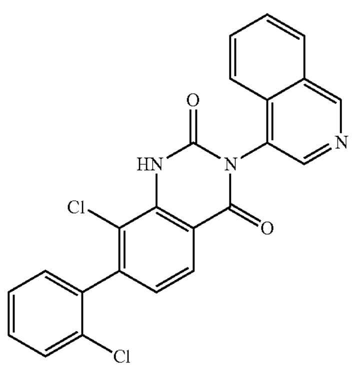 [SMILES: O=c1[nH]c2c(Cl)c(-c3ccccc3Cl)ccc2c(=O)n1-c1cncc2ccccc12] | 434.1 | 1H NMR (400 MHz, DMSO) δ 11.37 (d, J = 1.7 Hz, 1H), 9.51 (s, 1H), 8.79-8.46 (m, 1H), 8.33 (dq, J = 7.3, 1.1 Hz, 1H), 8.04 (ddd, J = 10.0, 8.0, 1.7 Hz, 2H), 7.89-7.76 (m, 2H), 7.72-7.63 (m, 1H), 7.60-7.48 (m, 2H), 7.45-7.36 (m, 1H), 7.28 (s, 1H). | I-22 |
| 80 | 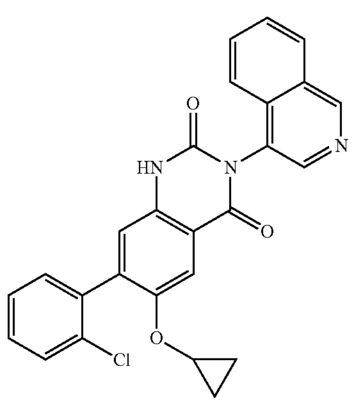 [SMILES: O=c1[nH]c2cc(-c3ccccc3Cl)c(OC3CC3)cc2c(=O)n1-c1cncc2ccccc12] | 456.2 | 1H NMR (400 MHz, DMSO) δ 11.74 (s, 1H), 9.49 (s, 1H), 8.62 (s, 1H), 8.37-8.28 (m, 1H), 7.92 (d, J = 11.1 Hz, 1H), 7.89-7.76 (m, 3H), 7.66-7.54 (m, 1H), 7.52-7.42 (m, 2H), 7.40-7.34 (m, 1H), 7.10 (s, 1H), 3.94 (tt, J = 6.0, 2.9 Hz, 1H), 0.80-0.74 (m, 2H), 0.58 (s, 2H). | I-24 |

TABLE 5-continued

Examples 75-85

| Example | Structure | ES/MS m/z | ¹H-NMR | Changes to Procedure 4: Different Reagents/ Starting Materials |
|---|---|---|---|---|
| 81 | 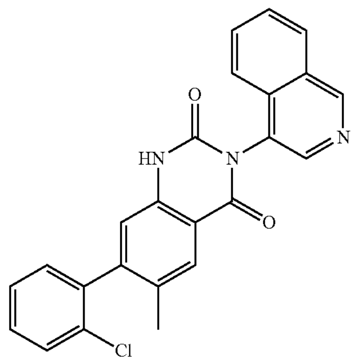 [SMILES: Cc1cc2c(=O)n(-c3cncc4ccccc34)c(=O)[nH]c2cc1-c1ccccc1Cl] | 414.1 | 1H NMR (400 MHz, DMSO) δ 11.79 (s, 1H), 9.53 (s, 1H), 8.64 (d, J = 16.2 Hz, 1H), 8.34 (d, J = 7.9 Hz, 1H), 8.02-7.77 (m, 5H), 7.70-7.58 (m, 1H), 7.45-7.28 (m, 2H), 7.05 (s, 1H), 2.11 (s, 3H). | I-17 |
| 82 | 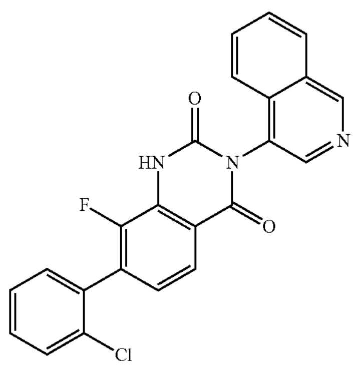 [SMILES: O=c1[nH]c2c(F)c(-c3ccccc3Cl)ccc2c(=O)n1-c1cncc2ccccc12] | 418.1 | 1H NMR (400 MHz, DMSO) δ 12.05 (s, 1H), 9.53 (s, 1H), 8.66 (s, 1H), 8.37-8.30 (m, 1H), 8.06 (d, J = 8.1 Hz, 1H), 7.93-7.77 (m, 3H), 7.73-7.66 (m, 1H), 7.61-7.46 (m, 3H), 7.25 (dd, J = 8.2, 6.2 Hz, 1H). | I-18 |
| 83 | 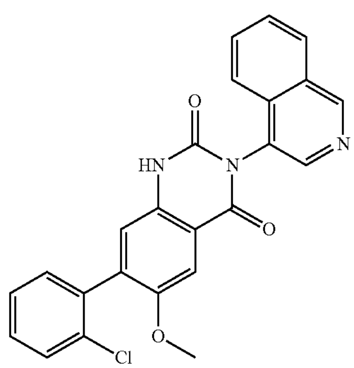 [SMILES: COc1cc2c(=O)n(-c3cncc4ccccc34)c(=O)[nH]c2cc1-c1ccccc1Cl] | 430.1 | 1H NMR (400 MHz, DMSO) δ 11.76 (s, 1H), 9.53 (s, 1H), 8.64 (s, 1H), 8.37-8.30 (m, 1H), 8.13-7.76 (m, 3H), 7.68-7.30 (m, 5H), 7.12 (s, 1H), 3.79 (s, 3H). | I-19 |
| 84 | 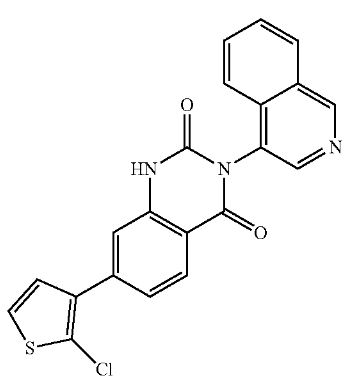 [SMILES: O=c1[nH]c2cc(-c3ccsc3Cl)ccc2c(=O)n1-c1cncc2ccccc12] | 406.2 | 1H NMR (400 MHz, DMSO-d6) δ 11.87 (s, 1H), 9.51 (s, 1H), 8.63 (s, 1H), 8.33 (d, J = 7.8 Hz, 1H), 8.05 (d, J = 8.2 Hz, 1H), 7.95 (d, J = 8.0 Hz, 1H), 7.87-7.76 (m, 2H), 7.68 (d, J = 5.8 Hz, 1H), 7.57 (s, 1H), 7.48 (d, J = 8.4 Hz, 1H), 7.34 (d, J = 5.7 Hz, 1H). | (2-chlorothiophen-3-yl)boronic acid |

TABLE 5-continued

Examples 75-85

| Example | Structure | ES/MS m/z | ¹H-NMR | Changes to Procedure 4: Different Reagents/ Starting Materials |
|---|---|---|---|---|
| 85 | 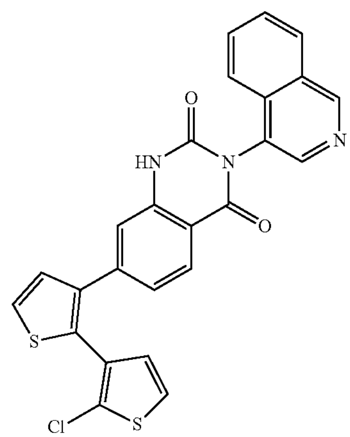 [SMILES: O=c1[nH]c2cc(-c3ccsc3-c3ccsc3Cl)ccc2c(=O)n1-c1cncc2ccccc12] | 488.2 | 1H NMR (400 MHz, DMSO-d6) δ 11.76 (s, 1H), 9.47 (s, 1H), 8.59 (s, 1H), 8.30 (dd, J = 7.0, 2.1 Hz, 1H), 7.90 (d, J = 8.2 Hz, 1H), 7.88-7.84 (m, 2H), 7.83-7.776 (m, 2H), 7.58 (d, J = 5.7 Hz, 1H), 7.40 (d, J = 5.3 Hz, 1H), 7.21 (d, J = 1.6 Hz, 1H), 7.14 (dd, J = 8.2, 1.6 Hz, 1H), 6.96 (d, J = 5.7 Hz, 1H). | (2-chlorothiophen-3-yl)boronic acid |

Procedure 5: Example 86

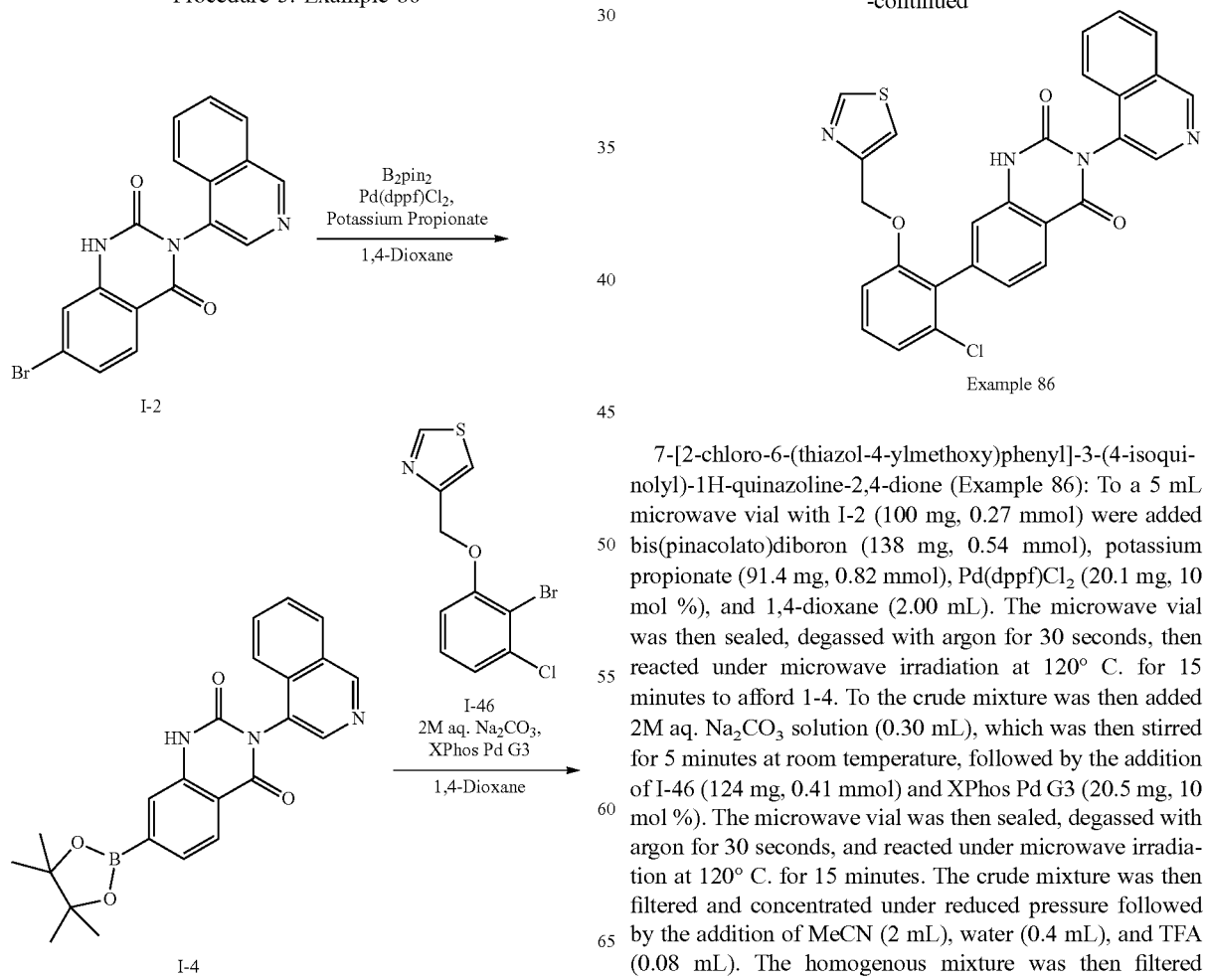

Example 86

7-[2-chloro-6-(thiazol-4-ylmethoxy)phenyl]-3-(4-isoquinolyl)-1H-quinazoline-2,4-dione (Example 86): To a 5 mL microwave vial with I-2 (100 mg, 0.27 mmol) were added bis(pinacolato)diboron (138 mg, 0.54 mmol), potassium propionate (91.4 mg, 0.82 mmol), Pd(dppf)Cl₂ (20.1 mg, 10 mol %), and 1,4-dioxane (2.00 mL). The microwave vial was then sealed, degassed with argon for 30 seconds, then reacted under microwave irradiation at 120° C. for 15 minutes to afford I-4. To the crude mixture was then added 2M aq. Na₂CO₃ solution (0.30 mL), which was then stirred for 5 minutes at room temperature, followed by the addition of I-46 (124 mg, 0.41 mmol) and XPhos Pd G3 (20.5 mg, 10 mol %). The microwave vial was then sealed, degassed with argon for 30 seconds, and reacted under microwave irradiation at 120° C. for 15 minutes. The crude mixture was then filtered and concentrated under reduced pressure followed by the addition of MeCN (2 mL), water (0.4 mL), and TFA (0.08 mL). The homogenous mixture was then filtered through an acrodisc and subsequently purified by RP-HPLC (0.1% TFA-ACN in 0.1% TFA Water, Column: Gemini 5 uM, NX-C18 110 Angstrom, 250×21.2 mm) to give the title compound Example 86 as a trifluoroacetate salt.

ES/MS: 513.1 (M⁺).

1H NMR (400 MHz, Methanol-d4) δ 9.66 (s, 1H), 8.97 (dd, J=15.7, 2.0 Hz, 1H), 8.70 (s, 1H), 8.46 (d, J=8.2 Hz, 1H), 8.12 (d, J=8.1 Hz, 1H), 8.09-8.00 (m, 2H), 7.95 (ddd, J=8.1, 6.2, 1.8 Hz, 1H), 7.40 (q, J=8.1 Hz, 2H), 7.30-7.06 (m, 5H), 5.25 (s, 2H).

Examples 87-94

The following Examples were made in an analogous fashion according to Procedure 5 and are shown below in Table 6. Any different reagents/starting materials than those described in Procedure 5 are noted in the last column of Table 6—"Changes to Procedure 5: Different Reagents/Starting Materials".

TABLE 6

Examples 87-94

| Example | Structure | ES/MS m/z | ¹H-NMR | Changes to Procedure 5: Different Reagents/Starting Materials |
|---|---|---|---|---|
| 87 | 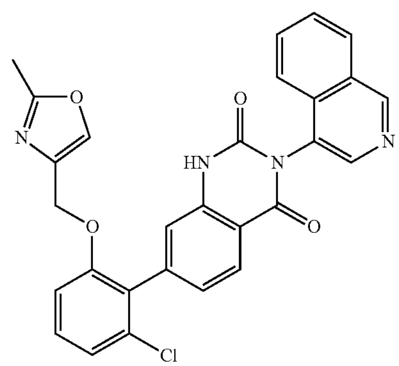 [SMILES: Cc1nc(COc2cccc(Cl)c2-c2ccc3c(=O)n(-c4cncc5ccccc45)c(=O)[nH]c3c2)co1] | 511.2 | 1H NMR (400 MHz, Methanol-d4) δ 9.66 (s, 1H), 8.70 (s, 1H), 8.45 (d, J = 8.1 Hz, 1H), 8.11 (d, J = 8.1 Hz, 1H), 8.06-8.00 (m, 2H), 7.94 (ddd, J = 8.1, 6.1, 2.0 Hz, 1H), 7.68 (s, 1H), 7.40 (t, J = 8.2 Hz, 1H), 7.32-7.12 (m, 4H), 4.97 (s, 2H), 2.42 (s, 3H). | I-47 |
| 88 | 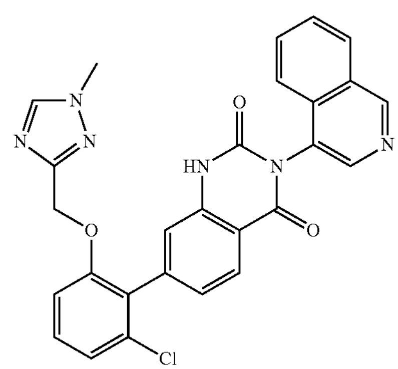 [SMILES: Cn1cnc(COc2cccc(Cl)c2-c2ccc3c(=O)n(-c4cncc5ccccc45)c(=O)[nH]c3c2)n1] | 511.2 | 1H NMR (400 MHz, DMSO) δ 11.82 (s, 1H), 9.52 (d, J = 0.9 Hz, 1H), 8.65 (s, 1H), 8.45 (s, 1H), 8.37-8.30 (m, 1H), 8.00 (dd, J = 7.9, 5.0 Hz, 2H), 7.89-7.77 (m, 2H), 7.49-7.38 (m, 2H), 7.23 (dd, J = 7.9, 1.2 Hz, 1H), 7.20-7.10 (m, 2H), 5.13 (s, 2H), 3.85 (s, 3H). | I-49 |
| 89 | 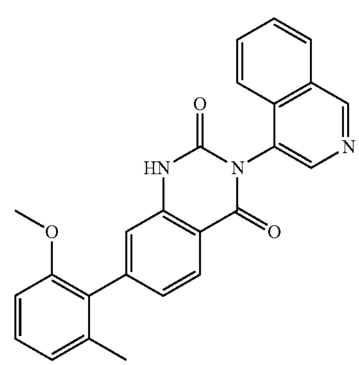 [SMILES: COc1cccc(C)c1-c1ccc2c(=O)n(-c3cncc4ccccc34)c(=O)[nH]c2c1] | 410.1 | 1H NMR (400 MHz, DMSO) δ 11.78 (s, 1H), 9.54 (s, 1H), 8.66 (s, 1H), 8.38-8.31 (m, 1H), 8.00 (dd, J = 8.6, 3.5 Hz, 2H), 7.84 (dddd, J = 16.2, 8.1, 6.9, 1.4 Hz, 2H), 7.33 (t, J = 8.0 Hz, 1H), 7.12-7.05 (m, 2H), 6.98 (dd, J = 12.3, 7.9 Hz, 2H), 3.70 (s, 3H), 2.08 (s, 3H). | 2-bromo-1-methoxy-3-methyl-benzene |

TABLE 6-continued

Examples 87-94

| Example | Structure | ES/MS m/z | ¹H-NMR | Changes to Procedure 5: Different Reagents/ Starting Materials |
|---|---|---|---|---|
| 90 | 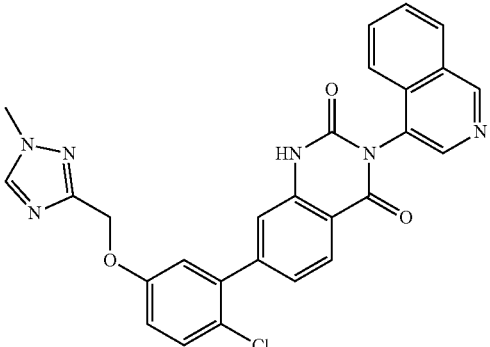 | 511.2 | 1H NMR (400 MHz, DMSO) δ 11.90 (s, 1H), 9.54 (d, J = 0.9 Hz, 1H), 8.65 (s, 1H), 8.50 (s, 1H), 8.38-8.31 (m, 1H), 8.05 (s, 1H), 8.02-7.95 (m, 1H), 7.84 (dddd, J = 16.1, 8.1, 6.9, 1.4 Hz, 2H), 7.55 (d, J = 8.8 Hz, 1H), 7.38-7.25 (m, 2H), 7.24-7.10 (m, 2H), 5.17 (s, 2H), 3.89 (s, 3H). | I-50 |
| 91 | 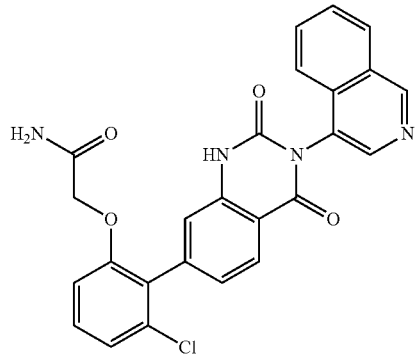 [SMILES: NC(=O)COc1cccc(Cl)c1-c1ccc2c(=O)n(-c3cncc4ccccc34)c(=O)[nH]c2c1] | 473.1 | 1H NMR (400 MHz, DMSO) δ 11.86 (s, 1H), 9.55 (s, 1H), 8.67 (s, 1H), 8.35 (dd, J = 7.8, 1.6 Hz, 1H), 8.02 (t, J = 7.1 Hz, 2H), 7.85 (dddd, J = 16.2, 8.1, 6.9, 1.4 Hz, 2H), 7.56-7.37 (m, 2H), 7.37-7.23 (m, 3H), 7.23-7.00 (m, 2H), 4.48 (d, J = 10.5 Hz, 2H). | I-51 |
| 92 | 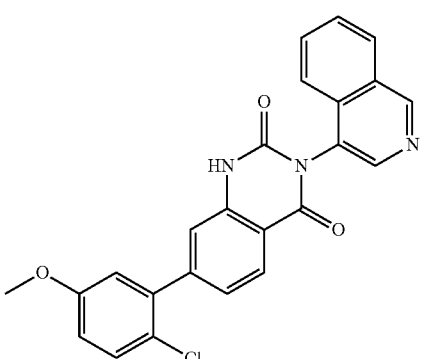 | 430.1 | 1H NMR (400 MHz, DMSO) δ 11.89 (s, 1H), 9.54 (s, 1H), 8.66 (s, 1H), 8.38-8.31 (m, 1H), 8.06 (d, J = 8.0 Hz, 1H), 7.98 (dd, J = 8.2, 1.4 Hz, 1H), 7.84 (dddd, J = 16.7, 8.1, 6.9, 1.4 Hz, 2H), 7.56 (d, J = 8.8 Hz, 1H), 7.38-7.30 (m, 2H), 7.10 (dd, J = 8.8, 3.1 Hz, 1H), 7.02 (d, J = 3.0 Hz, 1H), 3.84 (s, 3H). | 2-bromo-1-chloro-4-methoxy-benzene |

TABLE 6-continued

Examples 87-94

| Example | Structure | ES/MS m/z | ¹H-NMR | Changes to Procedure 5: Different Reagents/ Starting Materials |
|---|---|---|---|---|
| 93 | 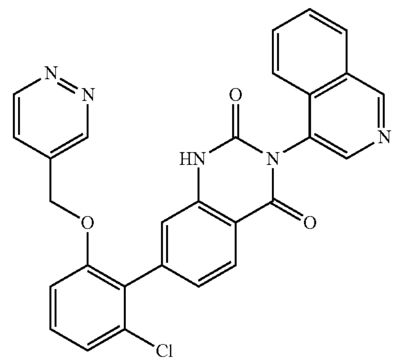 [SMILES: O=c1[nH]c2cc(-c3c(Cl)cccc3OCc3ccnnc3)ccc2c(=O)n1-c1cncc2ccccc12] | 508.1 | 1H NMR (400 MHz, DMSO) δ 11.88 (s, 1H), 9.53 (s, 1H), 9.23 (dd, J = 5.3, 1.3 Hz, 1H), 9.15 (dd, J = 2.4, 1.3 Hz, 1H), 8.67 (s, 1H), 8.34 (dd, J = 7.5, 1.6 Hz, 1H), 8.10-7.94 (m, 2H), 7.90-7.76 (m, 2H), 7.57-7.50 (m, 1H), 7.46 (d, J = 8.2 Hz, 1H), 7.34-7.18 (m, 4H), 5.32 (s, 2H). | I-52 |
| 94 | 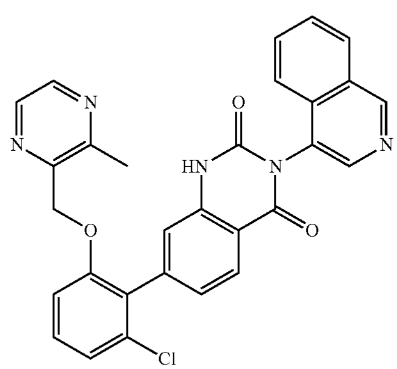 [SMILES: Cc1nccnc1COc1cccc(Cl)c1-c1ccc2c(=O)n(-c3cncc4ccccc34)c(=O)[nH]c2c1] | 522.1 | 1H NMR (400 MHz, DMSO) δ 11.85 (s, 1H), 9.55 (s, 1H), 8.68 (s, 1H), 8.53-8.42 (m, 2H), 8.39-8.32 (m, 1H), 8.00 (dd, J = 8.2, 2.3 Hz, 2H), 7.85 (dddd, J = 16.5, 8.2, 6.9, 1.4 Hz, 2H), 7.45 (t, J = 8.2 Hz, 1H), 7.32 (dd, J = 8.6, 1.0 Hz, 1H), 7.25 (dd, J = 8.0, 0.9 Hz, 1H), 7.16 (d, J = 8.0 Hz, 2H), 5.33 (s, 2H), 2.47 (s, 3H). | I-53 |

Procedure 6: Example 95

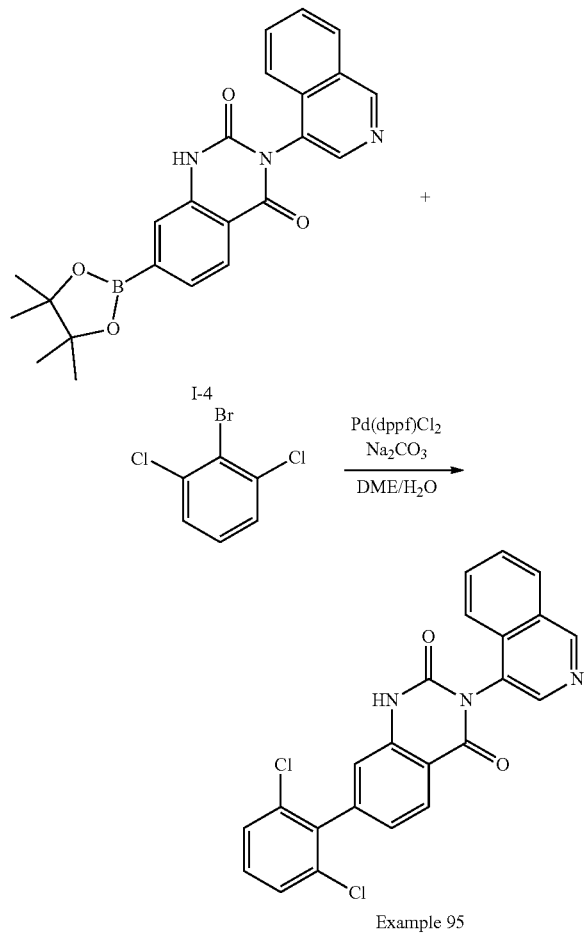

Example 95

7-(2,6-dichlorophenyl)-3-(isoquinolin-4-yl)quinazoline-2,4(1H,3H)-dione (Example 95): To a microwave vial with 7-bromo-3-(isoquinolin-4-yl)quinazoline-2,4(1H,3H)-dione (I-4) (200 mg, 0.482 mmol) were added 2-bromo-1,3-dichloro-benzene (109 mg, 0.482 mmol), [1,1'-Bis(diphenylphosphino)ferrocene]dichloropalladium(II) (36 mg, 0.048 mmol) and sodium carbonate (2M aqueous, 0.48 mL, 0.96 mmol). DME (3 mL) and water (0.2 mL) were added, and the mixture was degassed with argon for 30 seconds. The vial was sealed, and the reaction mixture was heated at 100° C. for 20 minutes under microwave conditions. The crude mixture was concentrated under reduced pressure, and to the crude residue were added DMF (2 mL), acetonitrile (1 mL), TFA (0.7 mL) and water (0.2 mL). The mixture was heated to produce a homogeneous mixture, and the mixture was filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the title compound Example 95 as a trifluoroacetate salt.

ES/MS: 434.0 (M+).

1H NMR (400 MHz, DMSO-d6) δ 11.88 (s, 1H), 9.47 (s, 1H), 8.63 (s, 1H), 8.36-8.23 (m, 1H), 8.10 (d, J=8.0 Hz, 1H), 7.98 (d, J=7.9 Hz, 1H), 7.80 (p, J=6.8 Hz, 2H), 7.68 (d, J=8.1 Hz, 2H), 7.54 (t, J=8.1 Hz, 1H), 7.23-7.14 (m, 2H).

Examples 96-100

The following Examples were made in an analogous fashion according to Procedure 6 and are shown below in Table 7. Any different reagents/starting materials than those described in Procedure 6 are noted in the last column of Table 7—"Changes to Procedure 6: Different Reagents/Starting Materials".

TABLE 7

Examples 96-100

| Example | Structure | ES/MS m/z | 1H-NMR | Changes to Procedure 6: Different Reagents/Starting Materials |
|---|---|---|---|---|
| 96 | 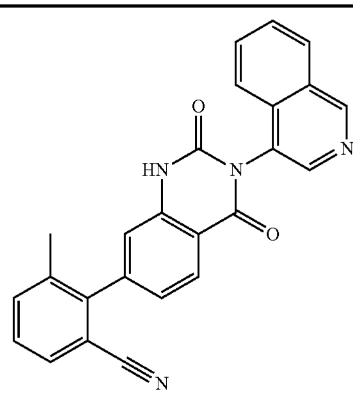 | 405.1 | 1H NMR (400 MHz, DMSO-d6) δ 11.91 (s, 1H), 9.46 (s, 1H), 8.63 (d, J = 14.4 Hz, 1H), 8.29 (dd, J = 7.1, 2.2 Hz, 1H), 8.11 (d, J = 8.1 Hz, 1H), 7.97 (s, 1H), 7.89-7.71 (m, 4H), 7.59 (t, J = 7.8 Hz, 1H), 7.26 (dd, J = 8.1, 1.5 Hz, 1H), 7.22 (d, J = 1.5 Hz, 1H), 2.26-2.17 (m, 3H). | 2-bromo-3-methyl-benzonitrile |

TABLE 7-continued

Examples 96-100

| Example | Structure | ES/MS m/z | ¹H-NMR | Changes to Procedure 6: Different Reagents/ Starting Materials |
|---|---|---|---|---|
| 97 | 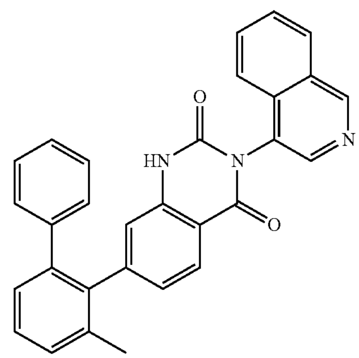 [SMILES: Cc1cccc(-c2ccccc2)c1-c1ccc2c(=O)n(-c3cncc4ccccc34)c(=O)[nH]c2c1] | 456.2 | 1H NMR (400 MHz, DMSO-d6) δ 11.65 (d, J = 8.6 Hz, 1H), 9.44 (s, 1H), 8.58 (d, J = 8.0 Hz, 1H), 8.41-8.18 (m, 1H), 7.93-7.74 (m, 4H), 7.73-7.49 (m, 1H), 7.49-7.36 (m, 2H), 7.36-7.09 (m, 5H), 7.09-6.90 (m, 2H), 2.15 (d, J = 11.1 Hz, 3H). | I-6 |
| 98 | 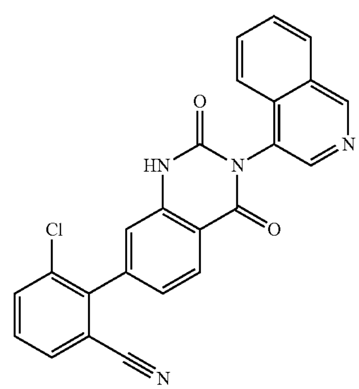 [SMILES: N#Cc1cccc(Cl)c1-c1ccc2c(=O)n(-c3cncc4ccccc34)c(=O)[nH]c2c1] | 425.1 | 1H NMR (400 MHz, DMSO-d6) δ 11.96 (s, 1H), 9.48 (s, 1H), 8.66 (d, J = 6.2 Hz, 1H), 8.31 (d, J = 7.7 Hz, 1H), 8.20-7.98 (m, 4H), 7.76 (dt, J = 35.1, 7.4 Hz, 3H), 7.40-7.29 (m, 2H). | 2-bromo-3-chloro-benzonitrile |
| 99 | 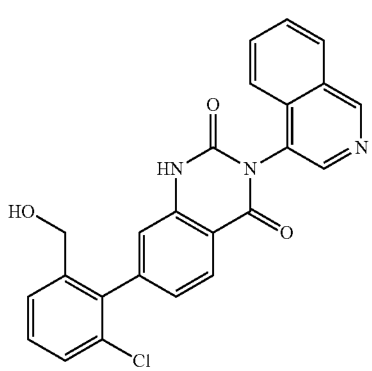 [SMILES: O=c1[nH]c2cc(-c3c(Cl)cccc3CO)ccc2c(=O)n1-c1cncc2ccccc12] | 430.1 | 1H NMR (400 MHz, DMSO-d6) δ 11.85 (d, J = 2.9 Hz, 1H), 9.46 (s, 1H), 8.62 (d, J = 10.2 Hz, 1H), 8.39-8.19 (m, 1H), 8.06 (d, J = 8.0 Hz, 1H), 7.95 (dd, J = 10.3, 7.9 Hz, 1H), 7.84-7.71 (m, 2H), 7.62 (dt, J = 7.1, 2.4 Hz, 1H), 7.57-7.44 (m, 2H), 7.12 (dd, J = 7.5, 2.4 Hz, 2H), 4.30-4.15 (m, 2H). | (2-bromo-3-chloro-phenyl)methanol |

TABLE 7-continued

Examples 96-100

| Example | Structure | ES/MS m/z | ¹H-NMR | Changes to Procedure 6: Different Reagents/ Starting Materials |
|---|---|---|---|---|
| 100 | 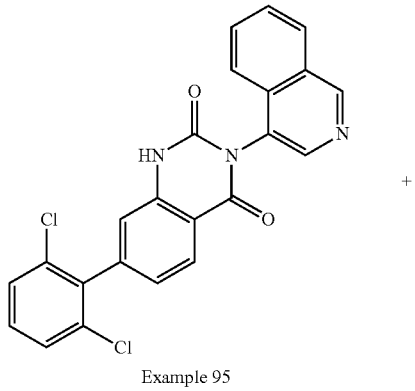 | 444.1 | 1H NMR (400 MHz, DMSO-d6) δ 11.85 (d, J = 4.3 Hz, 1H), 9.46 (s, 1H), 8.62 (d, J = 8.5 Hz, 1H), 8.30 (d, J = 7.7 Hz, 1H), 8.06 (d, J = 8.4 Hz, 1H), 7.95 (dd, J = 10.4, 8.0 Hz, 1H), 7.79 (ddd, J = 12.7, 9.0, 6.0 Hz, 2H), 7.67-7.42 (m, 3H), 7.13 (dq, J = 6.3, 2.6, 2.2 Hz, 2H), 4.25-4.09 (m, 2H), 3.22 (d, J = 8.6 Hz, 3H). | I-5 |

Procedure 7: Example 101

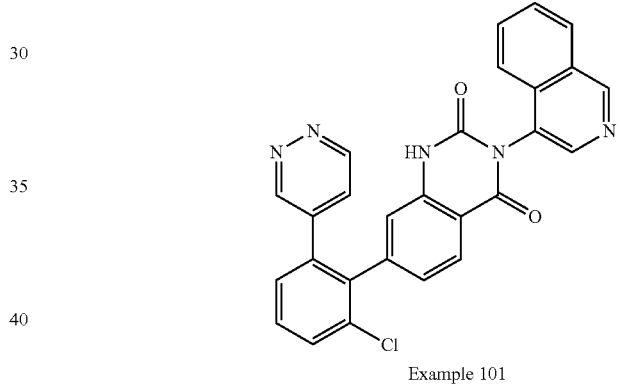

Example 101

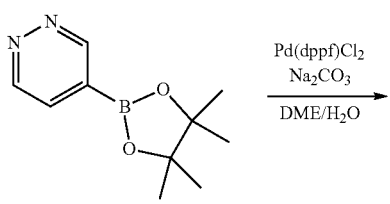

7-(2-chloro-6(pyridazin-4-yl)phenyl)-3-(isoquinolin-4-yl)quinazoline-2,4(1H,3H)-dione (Example 101): To a microwave vial with 7-(2,6-dichlorophenyl)-3-(isoquinolin-4-yl)quinazoline-2.4(1H,3H)-dione (Example 95) (TFA salt) (15 mg, 0.027 mmol) were added 4-(4,4,5,5-tetramethyl-1,3,2-dioxaborolan-2-yl)pyridazine (5.6 mg, 0.027 mmol), [1,1'-Bis(diphenylphosphino)ferrocene]dichloropalladium (II) (3 mg, 0.0041 mmol) and sodium carbonate (2M aqueous, 0.054 mL, 0.11 mmol). DME 0.75 mL) and water (0.05 mL) were added, and the mixture was degassed with argon for 30 seconds. The vial was sealed, and the reaction mixture was heated at 120° C. for 20 minutes under microwave conditions. The crude mixture was concentrated under reduced pressure, and to the crude residue was added DMF (0.4 mL), acetonitrile (0.1 mL), TFA (0.3 mL) and water (0.1 mL). The mixture was heated to produce a homogeneous mixture, and the mixture was filtered through an acrodisc, and was subsequently purified by RP-HPLC (0.1% TFA-ACN in 0.1% TFA Water, Column: Gemini 5 uM, NX-C18

110 Angstrom, 250×21.2 mm) to give the title compound Example 101 as a trifluoroacetate salt.

ES/MS: 478.1 (M+).

1H NMR (400 MHz, DMSO-d6) δ 11.75 (d, J=5.7 Hz, 1H), 9.44 (s, 1H), 9.19 (d, J=5.3 Hz, 1H), 9.04 (ddd, J=23.4, 2.5, 1.2 Hz, 1H), 8.60 (d, J=8.5 Hz, 1H), 8.28 (t, J=5.3 Hz, 1H), 7.99-7.74 (m, 5H), 7.74-7.53 (nm, 3H), 7.19-6.97 (m, 2H).

Examples 102-103

The following Examples were made in an analogous fashion according to Procedure 7 and are shown below in Table 8. Any different reagents/starting materials than those described in Procedure 7 are noted in the last column of Table 8—"Changes to Procedure 7: Different Reagents/Starting Materials".

TABLE 8

Examples 102-103

| Example | Structure | ES/MS m/z | $^1$H-NMR | Changes to Procedure 7: Different Reagents/Starting Materials |
|---|---|---|---|---|
| 102 | 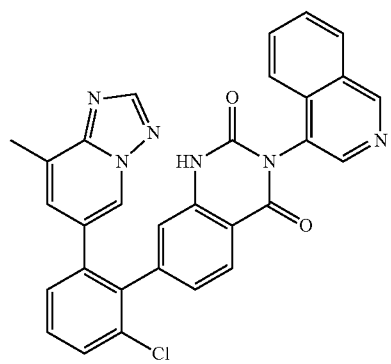 [SMILES: Cc1cc(-c2cccc(Cl)c2-c2ccc3c(=O)n(-c4cncc5ccccc45)c(=O)[nH]c3c2)cn2ncnc12] | 531.1 | 1H NMR (400 MHz, DMSO-d6) δ 11.70 (d, J = 3.2 Hz, 1H), 9.43 (d, J = 2.1 Hz, 1H), 8.82-8.69 (m, 1H), 8.57 (d, J = 4.3 Hz, 1H), 8.46 (d, J = 3.4 Hz, 1H), 8.27 (dd, J = 7.4, 2.2 Hz, 1H), 7.99-7.70 (m, 4H), 7.70-7.56 (m, 2H), 7.31 (d, J = 1.5 Hz, 1H), 7.23 (td, J = 8.0, 1.6 Hz, 1H), 7.08 (dd, J = 8.6, 1.5 Hz, 1H), 2.47 (d, J = 5.5 Hz, 3H). | 8-methyl-6-(4,4,5,5-tetramethyl-1,3,2-dioxaborolan-2-yl)-[1,2,4]triazolo[1,5-a]pyridine |
| 103 | 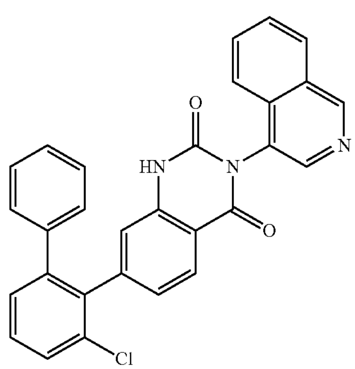 [SMILES: O=c1[nH]c2cc(-c3c(Cl)cccc3-c3ccccc3)ccc2c(=O)n1-c1cncc2ccccc12] | 476.2 | 1H NMR (400 MHz, DMSO-d6) δ 11.71 (d, J = 6.6 Hz, 1H), 9.44 (s, 1H), 8.59 (s, 1H), 8.33-8.24 (m, 1H), 7.92-7.74 (m, 4H), 7.68 (dt, J = 8.1, 1.5 Hz, 1H), 7.58 (t, J = 7.9 Hz, 1H), 7.45 (ddd, J = 7.6, 3.4, 1.3 Hz, 1H), 7.34-7.23 (m, 3H), 7.18 (td, J = 7.8, 1.8 Hz, 2H), 7.14-6.97 (m, 2H). | phenylboronic acid |

Procedure 8: Example 104 and Example 105

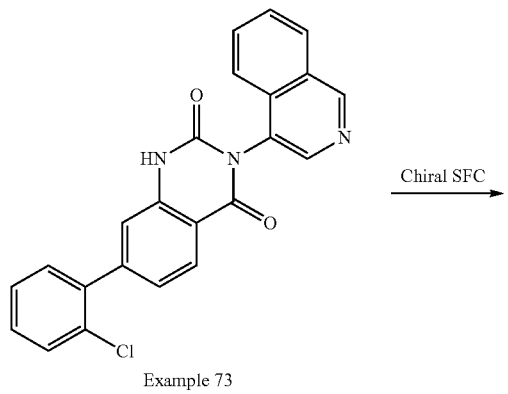

Example 73

7-(2-chlorophenyl)-3-(isoquinolin-4-yl)quinazoline-2,4(1H,3H)-dione (Example 104 and Example 105):

7-(2-chlorophenyl)-3-(isoquinolin-4-yl)quinazoline-2,4(1H,3H)-dione (Example 73) as a mixture of 2 stereoisomers was separated by chiral SFC (IA 4.6×100 mm column with 40% EtOH cosolvent) to give two enantiomers, which were designated Isomer 1 and Isomer 2.

Isomer 1:

7-(2-chlorophenyl)-3-(isoquinolin-4-yl)quinazoline-2,4(1H,3H)-dione (Example 104)

ES/MS: 400.1 (M+).

1H NMR (400 MHz, DMSO-d6) δ 11.87 (s, 1H), 9.48 (s, 1H), 8.62 (s, 1H), 8.31 (dd, J=7.3, 1.9 Hz, 1H), 8.06 (d, J=8.0 Hz, 1H), 8.02-7.88 (m, 1H), 7.88-7.76 (m, 2H), 7.72-7.59 (m, 1H), 7.51 (dq, J=6.5, 5.1 Hz, 3H), 7.33 (d, J=7.7 Hz, 2H).

Isomer 2:

7-(2-chlorophenyl)-3-(isoquinolin-4-yl)quinazoline-2,4(1H,3H)-dione (Example 105)

ES/MS: 400.1 (M+).

1H NMR (400 MHz, DMSO-d6) δ 11.87 (s, 1H), 9.48 (s, 1H), 8.62 (s, 1H), 8.39-8.25 (m, 1H), 8.06 (d, J=8.1 Hz, 1H), 7.98-7.90 (m, 1H), 7.89-7.73 (m, 2H), 7.73-7.62 (m, 1H), 7.59-7.46 (m, 3H), 7.33 (d, J=7.8 Hz, 2H).

Procedure 9: Example 106

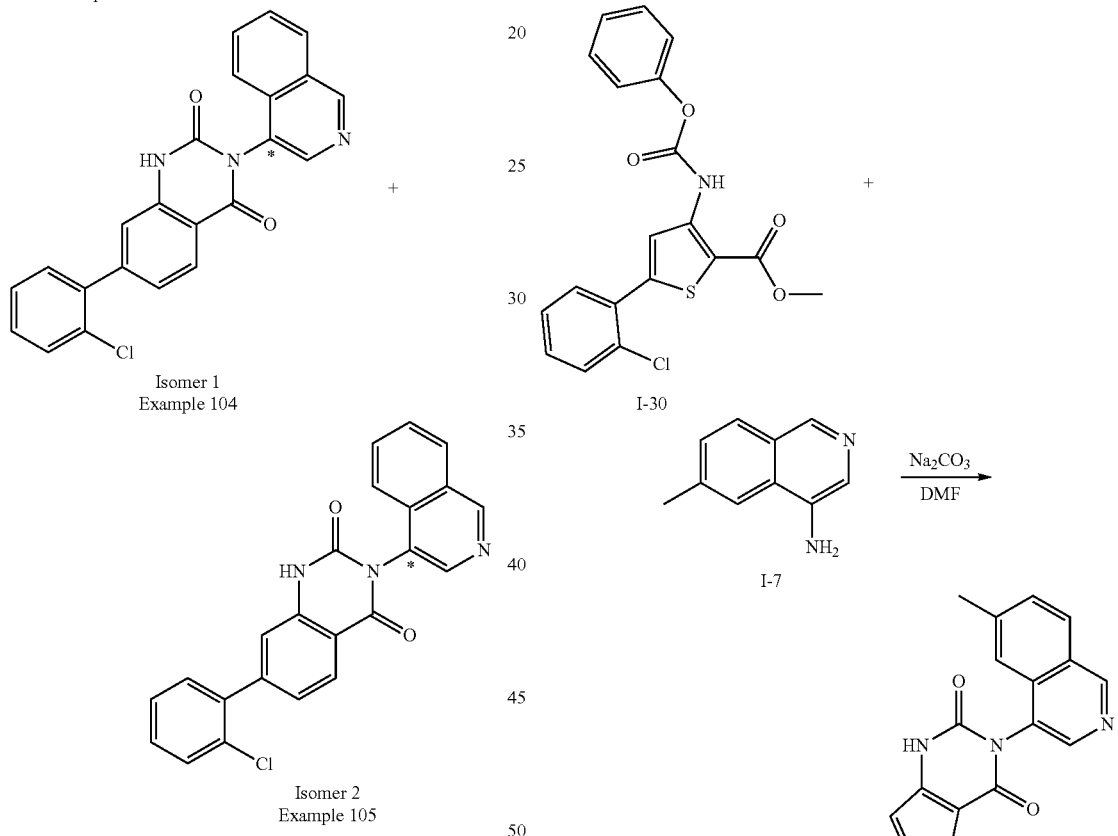

6-(2-chlorophenyl)-3-(6-methylisoquinolin-4-yl)thieno[3,2-d]pyrimidine-2,4(1H,3H)-dione (Example 106): To a dram vial with methyl 5-(2-chlorophenyl)-3-((phenoxycarbonyl)amino)thiophene-2-carboxylate (I-30) (50 mg, 0.129 mmol) were added 6-methylisoquinolin-4-amine (I-7) (31 mg, 0.193 mmol), and sodium carbonate (27 mg, 0.26 mmol). DMF (0.5 mL) was added, and the mixture was heated at 50° C. for 2 hours. The mixture was subsequently heated at 100° C. for 16 hours. The crude mixture was filtered through an acrodisc, and to the mixture was added ACN (0.3 mL), TFA (0.3 mL) and water (0.2 mL). The mixture was purified by RP-HPLC (0.1% TFA-ACN in 0.1% TFA Water, Column. Gemini 5 uM, NX-C18 110 Angstrom, 250×21.2 mm) to give the title compound Example 106 as a trifluoroacetate salt.

ES/MS: 420.0 (M⁺).

1H NMR (400 MHz, DMSO-d6) δ 12.27 (s, 1H), 9.44 (s, 1H), 8.57 (s, 1H), 8.23 (d, J=8.4 Hz, 1H), 7.84-7.63 (m, 4H), 7.55 (td, J=6.2, 5.1, 3.3 Hz, 2H), 7.35 (s, 1H), 2.53 (s, 3H).

Examples 107-109

The following Examples were made in an analogous fashion according to Procedure 9 and are shown below in Table 9. Any different reagents/starting materials than those described in Procedure 9 are noted in the last column of Table 9—"Changes to Procedure 9: Different Reagents/Starting Materials".

TABLE 9

Examples 107-109

| Example | Structure | ES/MS m/z | ¹H-NMR | Changes to Procedure 9: Different Reagents/ Starting Materials |
|---|---|---|---|---|
| 107 | 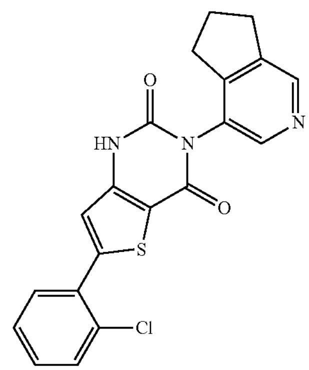 [SMILES: O=c1[nH]c2cc(-c3ccccc3Cl)sc2c(=O)n1-c1cncc2c1CCC2] | 396.1 | 1H NMR (400 MHz, DMSO-d6) δ 12.27 (s, 1H), 8.58 (s, 1H), 8.47 (s, 1H), 7.79-7.67 (m, 2H), 7.61-7.49 (m, 2H), 7.29 (s, 1H), 3.08 (t, J = 7.5 Hz, 2H), 2.83 (td, J = 7.5, 2.8 Hz, 2H), 2.10 (q, J = 7.5 Hz, 2H). | 6,7-dihydro-5H-cyclopenta[c]pyridin-4-amine |
| 108 | 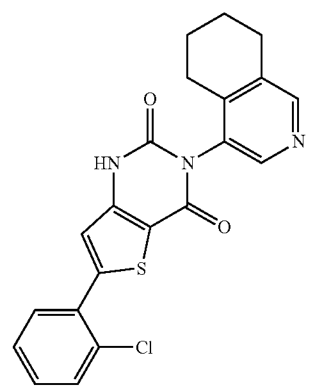 | 410.1 | 1H NMR (400 MHz, DMSO-d6) δ 12.28 (s, 1H), 8.48 (s, 1H), 8.42 (s, 1H), 7.74 (dd, J = 6.6, 2.7 Hz, 1H), 7.72-7.65 (m, 1H), 7.54 (td, J = 7.2, 6.2, 3.8 Hz, 2H), 7.29 (s, 1H), 2.86 (t, J = 5.9 Hz, 2H), 2.56-2.53 (m, 2H), 1.74 (q, J = 7.3 Hz, 4H). | 5,6,7,8-tetrahydroiso-quinolin-4-amine |
| 109 | 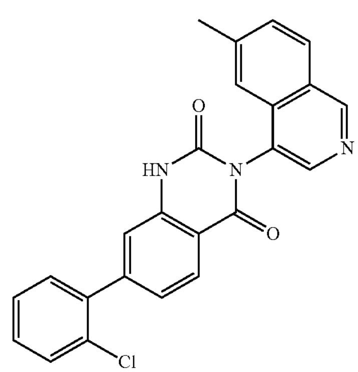 [SMILES: Cc1ccc2cncc(-n3c(=O)[nH]c4cc(-c5ccccc5Cl)ccc4c3=O)c2c1] | 414.1 | 1H NMR (400 MHz, DMSO-d6) δ 11.84 (s, 1H), 9.41 (s, 1H), 8.56 (s, 1H), 8.21 (d, J = 8.4 Hz, 1H), 8.06 (d, J = 8.0 Hz, 1H), 7.77 (s, 1H), 7.70-7.62 (m, 2H), 7.54-7.48 (m, 3H), 7.38-7.29 (m, 2H), 2.52 (s, 3H). | I-31 |

Procedure 10: Example 110

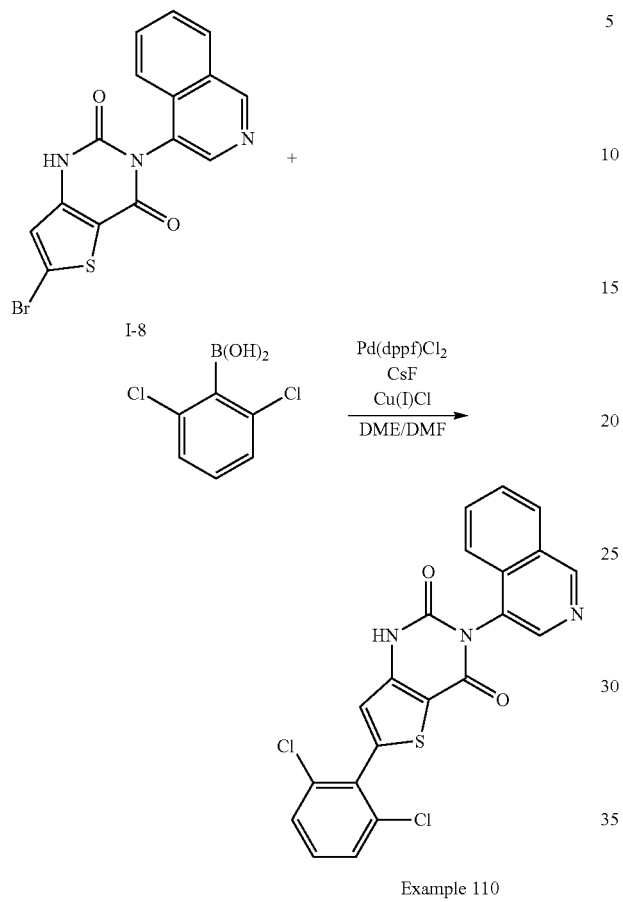

Example 110

6-(2,6-dichlorophenyl)-3-(isoquinolin-4-yl)thieno[3,2-d]pyrimidine-2,4(1H,3H)-dione (Example 110): To a microwave vial with 6-bromo-3-(isoquinolin-4-yl)thieno[3,2-d]pyrimidine-2,4(1H,3H)-dione (I-8) (550 mg, 1.47 mmol) were added (2,6-dichlorophenyl)boronic acid (491 mg, 2.57 mmol), [1,1'-Bis(diphenylphosphino)ferrocene]dichloropalladiumn(II) (164 mg, 0.22 mmol), cesium fluoride (670 mg, 4.41 mmol), and copper(I) chloride (73 mg, 0.735 mmol). DME (7 mL) and DMF (7 mL) were added, and the mixture was degassed with argon for 60 seconds. The vial was sealed, and the reaction mixture was heated at 120° C. for 20 minutes under microwave conditions. The crude mixture was concentrated under reduced pressure, and the crude residue was purified by silica chromatography (eluent: EtOAc in hexanes). The isolated material was dissolved in DMF (2 mL), acetonitrile (1 mL), TFA (0.7 mL) and water (0.2 mL). The mixture was filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the title compound Example 110 as a trifluoroacetate salt.

ES/MS: 440.0 (M$^+$).

1H NMR (400 MHz, DMSO-d6) δ 12.33 (s, 1H), 9.45 (s, 1H), 8.62 (s, 1H), 8.29 (dd, J=7.5, 1.4 Hz, 1H), 7.97-7.88 (m, 1H), 7.80 (dddd, J=18.7, 8.1, 6.8, 1.4 Hz, 2H), 7.75-7.68 (m, 2H), 7.59 (dd, J=8.9, 7.3 Hz, 1H), 7.10 (s, 1H).

Procedure 11: Example 111

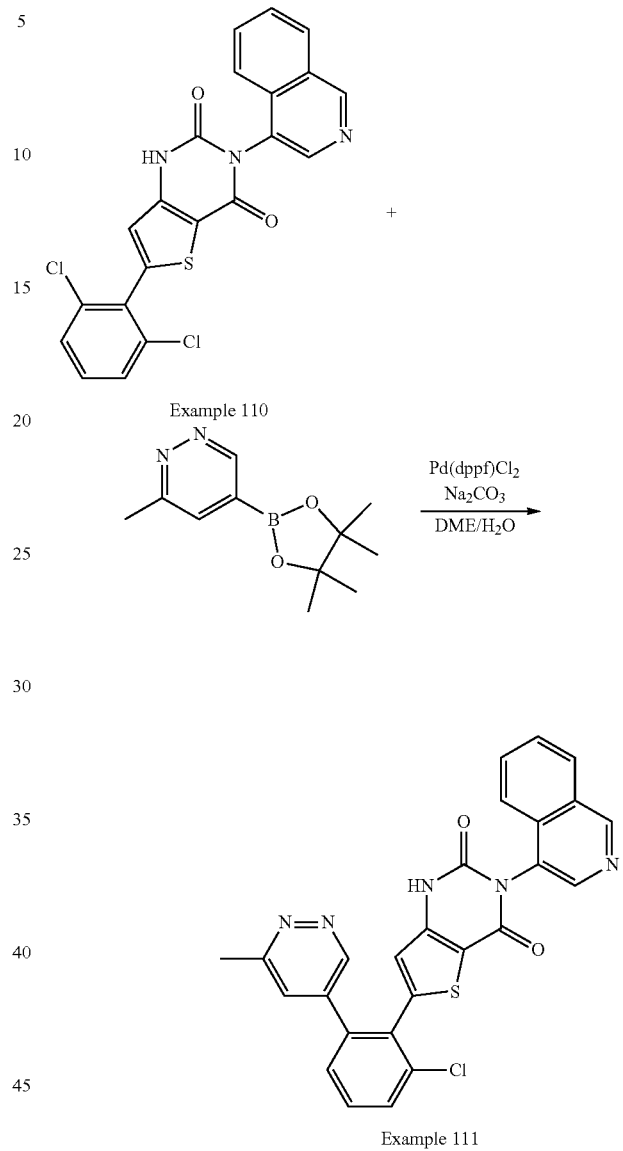

Example 111

6-(2-chloro-6-(6-methylpyridazin-4-yl)phenyl)-3-(isoquinolin-4-yl)thieno[3,2-d]pyrimidine-2,4(1H,3H)-dione (Example 111): To a microwave vial with 6-(2,6-dichlorophenyl)-3-(isoquinolin-4-yl)thieno[3,2-d]pyrimidine-2,4 (1H,3H)-dione (Example 110) (TFA salt) (20 mg, 0.036 mmol) were added 3-methyl-5-(4,4,5,5-tetramethyl-1,3,2-dioxaborolan-2-yl)pyridazine (8 mg, 0.036 mmol), [1,1'-Bis(diphenylphosphino)ferrocene]dichloropalladium(II) (4 mg, 0.0054 mmol), sodium carbonate (2M aqueous, 0.09 mL, 0.18 mmol). DME (0.5 mL), DMF (0.1 mL) and water (0.05 mL) were added, and the mixture was degassed with argon for 30 seconds. The vial was sealed, and the reaction mixture was heated at 120° C. for 20 minutes under microwave conditions. The crude mixture was concentrated under reduced pressure, and to the crude residue was added DMF (0.4 mL), acetonitrile (0.1 mL), TFA (0.3 mL) and water (0.1 mL). The mixture was heated to produce a homogeneous mixture, and the mixture was filtered through an acrodisc, and was subsequently purified by RP-HPLC (0.1% TFA- ACN in 0.1% TFA Water, Column: Gemini 5 uM, NX-C18 110 Angstrom, 250×21.2 mm) to give the title compound Example 111 as a trifluoroacetate salt.

ES/MS: 498.1 (M⁺).

1H NMR (400 MHz, DMSO-d6) δ 12.24 (s, 1H), 9.43 (s, 1H), 9.01 (d, J=2.2 Hz, 1H), 8.59 (s, 1H), 8.28 (d, J=8.1 Hz, 1H), 7.88-7.68 (m, 5H), 7.65 (d, J=2.2 Hz, 1H), 7.58 (dd, J=7.7, 1.2 Hz, 1H), 7.09 (s, 1H), 2.65 (s, 3H).

Examples 112-113

The following Examples were made in an analogous fashion according to Procedure 1D and are shown below in Table 10. Any different reagents/starting materials than those described in Procedure II are noted in the last column of Table 10—"Changes to Procedure 11: Different Reagents/Starting Materials".

TABLE 10

Examples 112-113

| Example | Structure | ES/MS m/z | ¹H-NMR | Changes to Procedure 11: Different Reagents/Starting Materials |
|---|---|---|---|---|
| 112 | 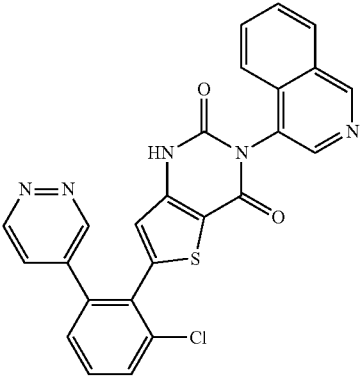 [SMILES: O=c1[nH]c2cc(-c3c(Cl)cccc3-c3ccnnc3)sc2c(=O)n1-c1cncc2ccccc12] | 484.1 | 1H NMR (400 MHz, DMSO-d6) δ 12.22 (s, 1H), 9.43 (s, 1H), 9.31-9.16 (m, 2H), 8.58 (s, 1H), 8.27 (dd, J = 8.0, 1.4 Hz, 1H), 7.85 (dd, J = 8.1, 1.2 Hz, 1H), 7.83-7.68 (m, 5H), 7.61 (dd, J = 7.7, 1.2 Hz, 1H), 7.07 (s, 1H). | 4-(4,4,5,5-tetramethyl-1,3,2-dioxaborolan-2-yl)pyridazine |
| 113 | 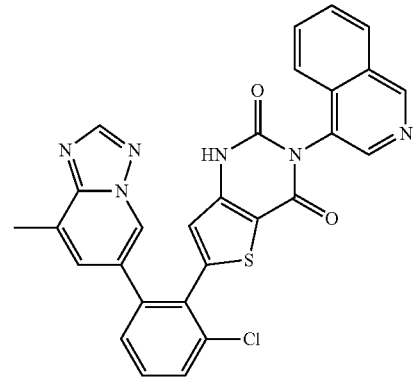 [SMILES: Cc1cc(-c2cccc(Cl)c2-c2cc3[nH]c(=O)n(-c4cncc5ccccc45)c(=O)c3s2)cn2ncnc12] | 537.1 | 1H NMR (400 MHz, DMSO-d6) δ 12.19 (s, 1H), 9.41 (s, 1H), 8.89 (s, 1H), 8.52 (d, J = 15.5 Hz, 2H), 8.35-8.20 (m, 1H), 7.84-7.72 (m, 4H), 7.67 (t, J = 7.9 Hz, 1H), 7.58 (dd, J = 7.7, 1.3 Hz, 1H), 7.46 (t, J = 1.5 Hz, 1H), 7.11 (s, 1H), 2.53 (s, 3H). | 8-methyl-6-(4,4,5,5-tetramethyl-1,3,2-dioxaborolan-2-yl)-[1,2,4]triazolo[1,5-a]pyridine |
| 114 | 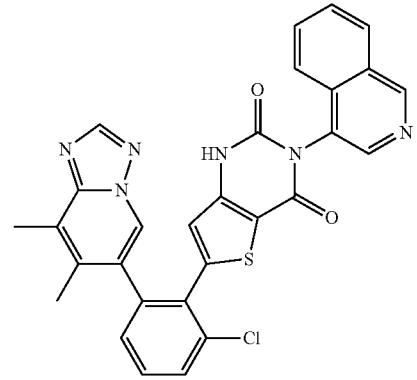 [SMILES: Cc1c(-c2cccc(Cl)c2-c2cc3[nH]c(=O)n(-c4cncc5ccccc45)c(=O)c3s2)cn2ncnc2c1C] | 551.1 | 1H NMR (400 MHz, DMSO-d6) δ 12.14 (d, J = 12.4 Hz, 1H), 9.40 (s, 1H), 8.88 (s, 1H), 8.52 (s, 1H), 8.42 (d, J = 2.8 Hz, 1H), 8.32-8.15 (m, 1H), 7.85-7.71 (m, 4H), 7.67 (t, J = 7.9 Hz, 1H), 7.45 (dt, J = 7.7, 1.5 Hz, 1H), 7.07 (d, J = 19.1 Hz, 1H), 2.11 (d, J = 3.9 Hz, 3H). | 7,8-dimethyl-6-(4,4,5,5-tetramethyl-1,3,2-dioxaborolan-2-yl)-[1,2,4]triazolo[1,5-a]pyridine (I-58) |

731

Procedure 12: Example 115

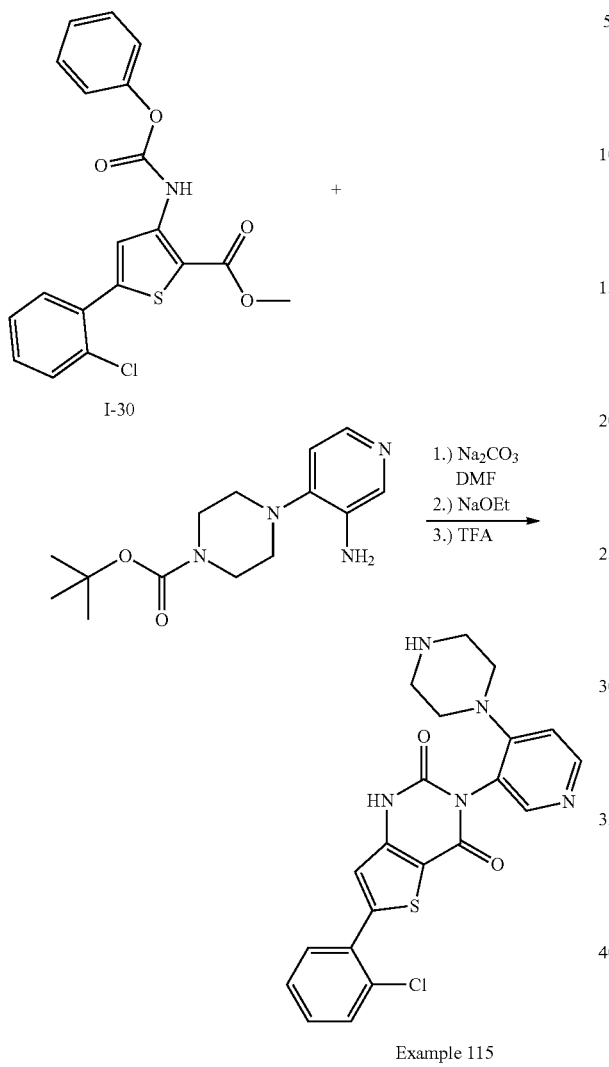

Example 115

6-(2-chlorophenyl)-3-(4-(piperazin-1-yl)pyridin-3-yl) thieno[3,2-d]pyrimidine-2,4(1H,3H)-dione (Example 115): To a dram vial with methyl 5-(2-chlorophenyl)-3-((phenoxycarbonyl)amino)thiophene-2-carboxylate (I-30) (50 mg, 0.129 mmol) were added tert-butyl 4-(3-amino-4-pyridyl)piperazine-1-carboxylate (54 mg, 0.193 mmol), and sodium carbonate (27 mg, 0.26 mmol). DMF (0.5 mL) was added, and the mixture was heated at 50° C. for 16 hours. The mixture was subsequently filtered to remove the precipitates. Sodium ethoxide (21% solution in EtOH; 0.1 mL) was added, and the mixture was heated at 80° C. for 2 hours. To the mixture was added TFA (0.5 mL), and the mixture was heated at 60° C. for 2 hours. To the crude mixture were added ACN (0.5 mL) and water (0.4 mL), and the mixture was filtered through an acrodisc. The mixture was purified by RP-HPLC (0.1% TFA-ACN in 0.1% TFA Water, Column. Gemini 5 uM. NX-C18 110 Angstrom, 250×21.2 mm) to give the title compound Example 115 as a trifluoroacetate salt.

ES/MS: 440.1 (M+).

732

1H NMR (400 MHz, DMSO-d6) δ 12.36 (s, 1H), 8.82-8.68 (m, 2H), 8.46 (d, J=6.5 Hz, 1H), 7.79-7.62 (m, 2H), 7.59-7.49 (m, 2H), 7.38 (s, 1H), 7.33 (s, 1H), 3.50-3.47 (m, 4H), 3.19-3.11 (m, 4H).

Procedure 13: Example 116

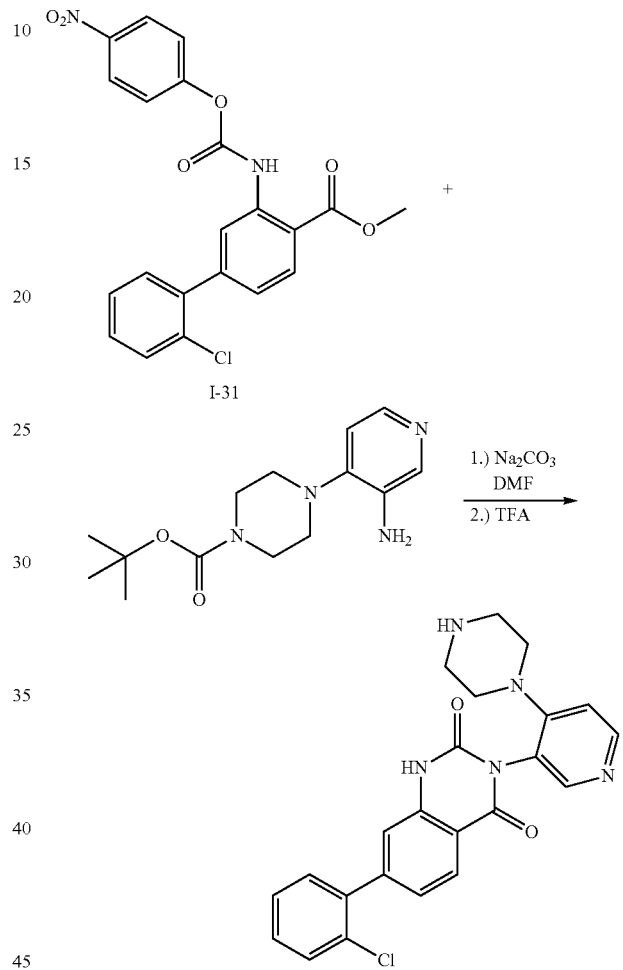

Example 116

7-(2-chlorophenyl)-3-(4-(piperazin-yl)pyridin-3-yl)quinazoline-2,4(1H,3H)-dione (Example 116): To a dram vial with methyl 2'-chloro-3-(((4-nitrophenoxy)carbonyl) amino)-[1,1'-biphenyl]-4-carboxylate (I-31) (50 mg, 0.117 mmol) were added tert-butyl 4-(3-amino-4-pyridyl)piperazine-1-carboxylate (49 mg, 0.176 mmol), and sodium carbonate (25 mg, 0.23 mmol). DMF (0.5 mL) was added, and the mixture was heated at 50° C. for 2 hours. The mixture was subsequently heated at 100° C. for 16 hours The mixture was subsequently filtered to remove the precipitates. To the mixture was added TFA (0.5 mL), and the mixture was heated at 60° C. for 2 hours. To the crude mixture was added ACN (0.5 mL) and water (0.4 mL), and the mixture was filtered through an acrodisc. The mixture was purified by RP-HPLC (0.1% TFA-ACN in 0.1% TFA Water, Column: Gemini 5 uM, NX-C18 110 Angstrom, 250×21.2 mm) to give the title compound Example 116 as a trifluoroacetate salt.

ES/MS: 434.1 (M+).

733

1H NMR (400 MHz, DMSO-d6) δ 11.98 (s, 1H), 8.80 (s, 2H), 8.58 (s, 1H), 8.50 (d, J=6.7 Hz, 1H), 8.08 (d, J=8.1 Hz, 1H), 7.66 (dd, J=5.9, 3.4 Hz, 1H), 7.60-7.44 (m, 4H), 7.41-7.31 (m, 2H), 3.58 (s, 4H), 3.18 (s, 4H).

Procedure 14: Example 117

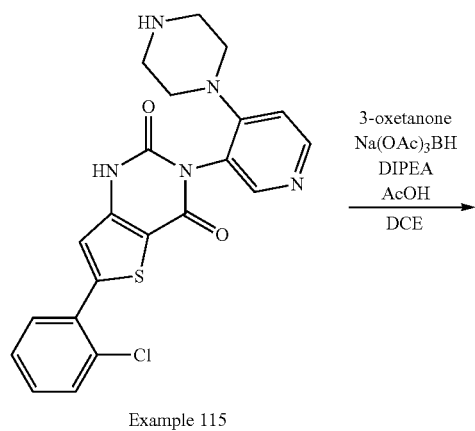

Example 115

Example 117

6-(2-chlorophenyl)-3-(4-(4-(oxetan-3-yl)piperazin-1-yl) pyridin-3-yl)thieno[3,2-d]pyrimidine-2,4(1H,3H)-dione (Example 117): To a dram vial with 6-(2-chlorophenyl)-3-(4-(piperazin-1-yl)pyridin-3-yl)thieno[3,2-d]pyrimidine-2,4 (1H,3H)-dione (Example 115) (TFA salt) (15 mg, 0.027 mmol) were added DIPEA (0.01 mL, 0.04 mmol), 3-oxetanone (6 mg, 0.081 mmol), and a single drop of glacial acetic acid. DCE (0.3 mL) was added, and the mixture was stirred at rt for 2 hours. Sodium triacetoxyborohydride (17 mg, 0.081 mmol) was added, and the mixture was heated at 35° C. for 4 hours. To the mixture was added acetic acid (0.4 mL), and the mixture was concentrated under reduced pressure. To the crude residue was added DMF (0.5 mL) and water (0.3 mL), and the mixture was filtered through an acrodisc. The mixture was purified by RP-HPLC (0.1% TFA-ACN in 0.1% TFA Water, Column: Gemini 5 uM, NX-C18 110 Angstrom, 250×21.2 mm) to give the title compound Example 117 as a trifluoroacetate salt.

ES/MS: 496.1 (M+).

734

1H NMR (400 MHz, DMSO-d6) δ 12.44 (s, 1H), 8.54 (s, 1H), 8.42 (d, J=7.0 Hz, 1H), 7.81-7.63 (m, 2H), 7.62-7.43 (m, 3H), 7.33 (s, 1H), 4.63-4.53 (m, 2H), 4.53-4.44 (m, 2H), 3.61-3.50 (m, 9H).

Procedure 15: Example 118

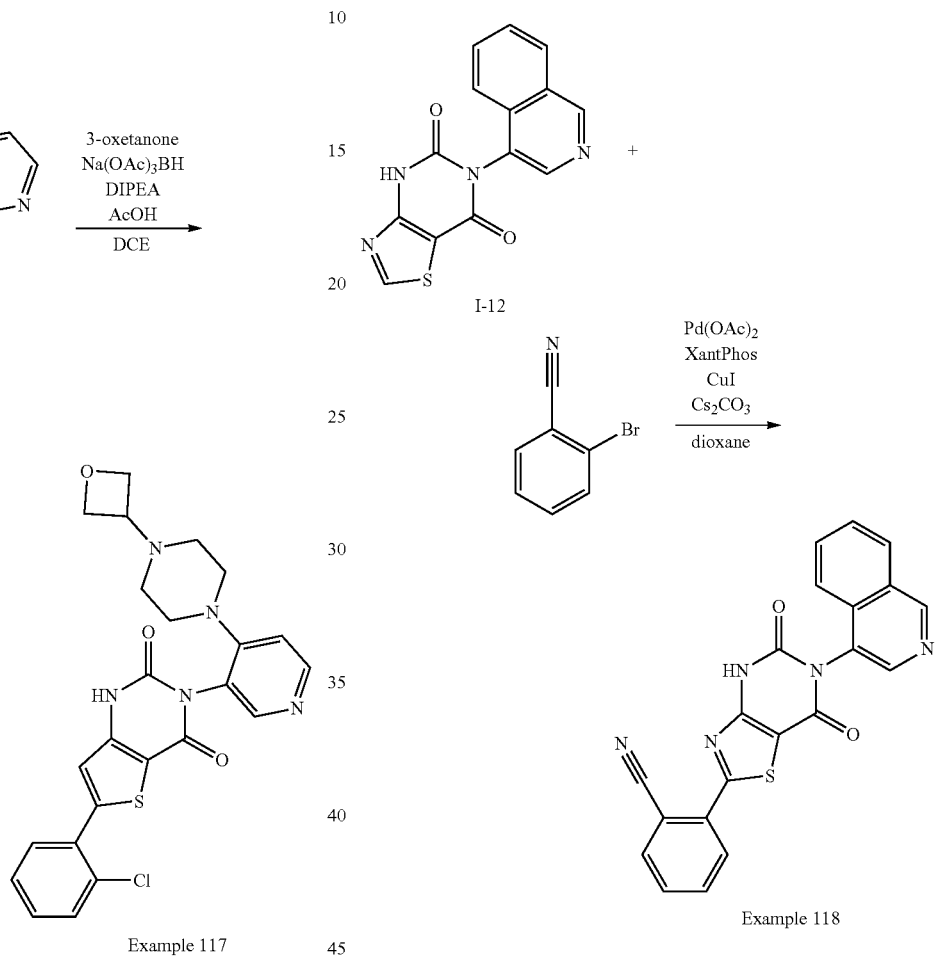

Example 118

2-(6-(isoquinolin-4-yl)-5,7-dioxo-4,5,6,7-tetrahydrothiazolo[4,5-d]pyrimidin-2-yl)benzonitrile (Example 118): To a vial with 6-(isoquinolin-4-yl)thiazolo[4,5-d]pyrimidine-5,7(4H,6H)-dione (I-12) (50 mg, 0.169 mmol) were added 2-bromobenzonitrile (92 mg, 0.506 mmol), Pd(OAc)$_2$ (7.6 mg, 0.034 mmol), XantPhos (39 mg, 0.068 mmol), copper(I) iodide (16 mg, 0.0845 mmol), and cesium carbonate (165 mg, 0.506 mmol). Dioxane (1.5 mL) was added, and the mixture was degassed with argon for 30 seconds. The vial was sealed, and the reaction mixture was heated at 105° C. for 60 minutes. The crude mixture was concentrated under reduced pressure, and to the crude residue was added DMF (1 mL), acetonitrile (0.5 mL), TFA (0.4 mL) and water (0.2 mL). The mixture was heated to produce a homogeneous mixture, and the mixture was filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the title compound Example 118 as a trifluoroacetate salt.

ES/MS: 398.1 (M+H+).

1H NMR (400 MHz, DMSO-d6) δ 13.21 (s, 1H), 9.48 (s, 1H), 8.62 (s, 1H), 8.32-8.23 (m, 1H), 8.21 (d, J=7.8 Hz, 1H), 8.16 (d, J=7.7 Hz, 1H), 8.03-7.92 (m, 2H), 7.91-7.74 (m, 3H).

Procedure 16: Example 119

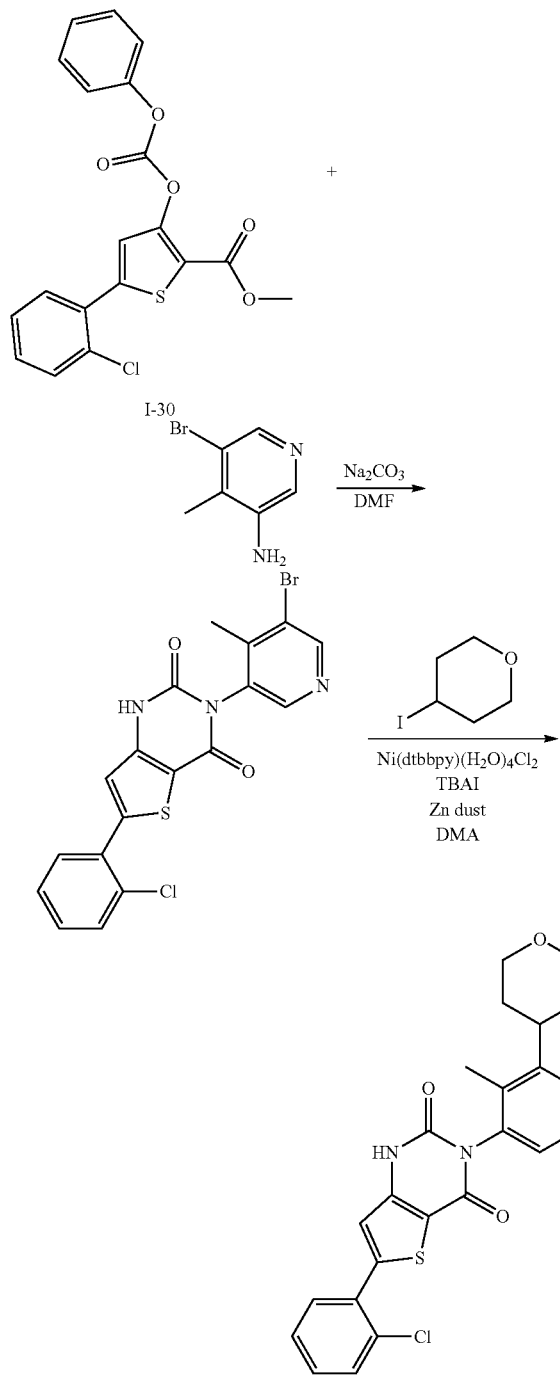

Example 119

3-(5-bromo-4-methylpyridin-3-yl)-6-(2-chlorophenyl)thieno[3,2-d]pyrimidine-2,4(1H,3H)-dione: To a dram vial with methyl 5-(2-chlorophenyl)-3-((phenoxycarbonyl)amino)thiophene-2-carboxylate (I-30) (50 mg, 0.129 mmol) were added 5-bromo-4-methyl-pyridin-3-amine (36 mg, 0.193 mmol), and sodium carbonate (27 mg, 0.26 mmol). DMF (0.5 mL) was added, and the mixture was heated at 50° C. for 2 hours. The mixture was subsequently heated at 100° C. for 16 hours. The crude mixture was directly purified by silica chromatography (eluent: EtOAc in hexanes, then MeOH in EtOAc) to give the product.

ES/MS: 448.0 (M+).

6-(2-chlorophenyl)-3-(4-methyl-5-(tetrahydro-2H-pyran-4-yl)pyridin-3-yl)thieno[3,2-d]pyrimidine-2,4(1H,3H)-dione (Example 119): To dried vial were added 3-(5-bromo-4-methylpyridin-3-yl)-6-(2-chlorophenyl)thieno[3,2-d]pyrimidine-2,4(1H,3H)-dione (35 mg, 0.078 mmol), 4-iodotetrahydropyran (41 mg, 0.195 mmol), tetrabutylammonium iodide (TBAI) (28.8 mg, 0.078 mmol), Ni(dtbbpy)(H2O)4Cl2 (3.7 mg, 0.0078 mmol), and zinc dust (30.4 mg, 0.47 mmol). Dry DMA (1 mL) was added, and the mixture was degassed for 1 minute with argon. The vial was sealed, and the reaction was stirred at 70° C. for 16 h. The crude mixture was filtered through an acrodisc, and TFA (0.2 mL) and water (0.2 mL) were added. The mixture was purified by RP-HPLC (0.1% TFA-ACN in 0.1% TFA Water, Column: Gemini 5 uM, NX-C18 110 Angstrom, 250×21.2 mm) to give the title compound Example 119 as a trifluoroacetate salt.

ES/MS: 454.1 (M+H+).

1H NMR (400 MHz, DMSO-d6) δ 12.26 (s, 1H), 8.55 (s, 1H), 8.42 (s, 1H), 7.80-7.61 (m, 2H), 7.59-7.49 (m, 2H), 7.29 (s, 1H), 4.02-3.93 (m, 2H), 3.52-3.50 (m, 2H), 3.19-3.05 (m, 1H), 2.17 (s, 3H), 1.91-1.76 (m, 2H), 1.76-1.64 (m, 2H).

Procedure 17: Example 120

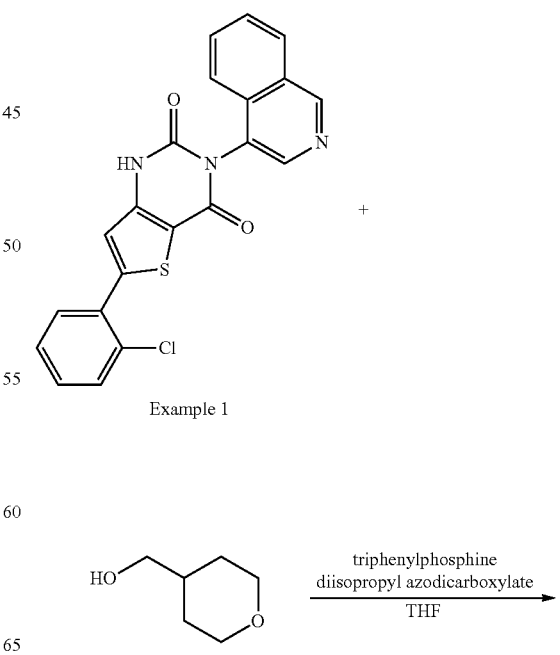

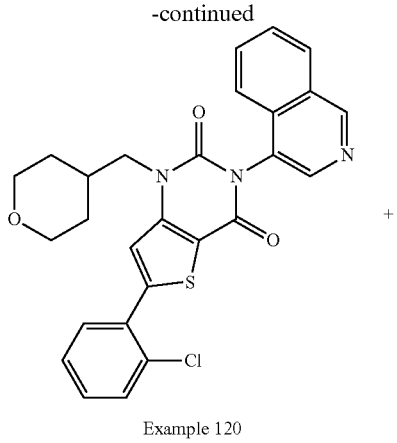

Example 120

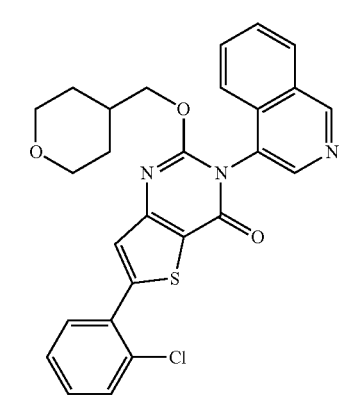

Example 120a 6-(2-chlorophenyl)-3-(isoquinolin-4-yl)-1-((tetrahydro-2H-pyran-4-yl)methyl)thieno[3,2-d]pyrimidine-2,4(1H,3H)-dione (Example 120): To a dried vial were added 6-(2-chlorophenyl)-3-(isoquinolin-4-yl)thieno[3,2-d]pyrimidine-2,4(1H,3H)-dione (Example 1) (15 mg, 0.037 mmol), tetrahydropyran-4-ylmethanol (9 mg, 0.074 mmol), and triphenylphosphine (18.3 mg, 0.074 mmol). Dry THF (0.75 mL) was added, and diisopropyl azodicarboxylate (DIAD) (0.18 mL, 0.092 mmol) was added via syringe. The reaction was stirred for 16 h at rt. Examination of the crude mixture by LCMS indicated the presence of desired product Example 120 (more polar) and the isomer "Example 120a" (less polar). The crude mixture was concentrated under reduced pressure, and DMF (0.75 mL), TFA (0.2 mL) and water (0.1 mL) were added. The mixture was filtered through an acrodisc before purification by RP-HPLC (0.1% TFA-ACN in 0.1% TFA Water, Column: Gemini 5 uM, NX-C18 110 Angstrom, 250×21.2 mm) to give Example 120 as a trifluoroacetate salt.

Example 120

ES/MS: 504.2 (M⁺).

1H NMR (400 MHz, DMSO-d6) δ 9.47 (s, 1H), 8.61 (s, 1H), 8.33-8.26 (m, 1H), 7.93-7.68 (m, 6H), 7.59-7.54 (m, 2H), 4.03 (d, J=7.3 Hz, 2H), 3.91-3.81 (m, 2H), 3.27 (td, J=11.7, 2.1 Hz, 2H), 2.21-2.03 (m, 1H), 1.69 (t, J=11.2 Hz, 2H), 1.47-1.04 (m, 2H).

Example 120a

ES/MS: 504.1 (M⁺).

1H NMR (400 MHz, DMSO-d₆) δ 9.49 (d, J=2.4 Hz, 1H), 8.67 (d, J=2.6 Hz, 1H), 8.31 (d, J=7.8 Hz, 1H), 7.85-7.77 (m, 3H), 7.76-7.60 (m, 3H), 7.54 (dt, J=7.2, 2.5 Hz, 2H), 4.17 (td, J=11.2, 10.0, 5.7 Hz, 2H), 3.64-3.57 (m, 2H), 3.05 (td, J=11.9, 2.9 Hz, 2H), 1.67 (s, 1H), 1.11 (d, J=13.6 Hz, 2H), 0.97-0.79 (m, 2H).

Procedure 18: Example 121

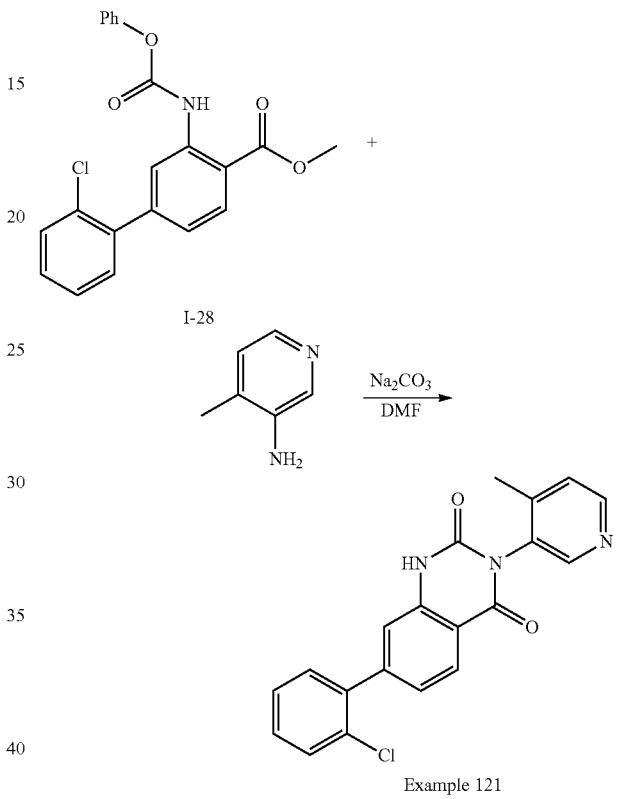

7-(2-chlorophenyl)-3-(4-methylpyridin-3-yl)quinazoline-2,4(1H,3H)-dione (Example 121): To a solution of methyl 2'-chloro-3-((phenoxycarbonyl)amino)-[1,1'-biphenyl]-4-carboxylate (I-28) (50 mg, 0.13 mmol) in DMF (1.5 mL) was added sodium carbonate (14 mg, 0.13 mmol) followed by 4-methylpyridin-3-amine (43 mg, 0.39 mmol). The reaction mixture was heated at 50° C. for 16 hours, then to complete the cyclization 1 eq of cesium carbonate was added and the temperature was increased to 100° C. Once the cyclization was complete, the mixture was cooled, diluted with 0.5 ml TFA:DMF. The mixture was filtered through an acrodisc before purification by RP-HPLC (0.1% TFA-ACN in 0.1% TFA Water, Column. Gemini 5 uM, NX-C18 110 Angstrom 250×21.2 mm) to give Example 121 as a trifluoroacetate salt.

ES/MS: 364.2 (M+H⁺).

¹H NMR (400 MHz, DMSO-d₆) δ 11.87 (s, 1H), 8.65-8.56 (m, 2H), 8.06 (d, 1H), 7.68-7.59 (m, 2H), 7.57-7.44 (m, 3H), 7.36-7.26 (m, 2H), 2.23 (s, 3H).

Examples 122-129

The following Examples were made in an analogous fashion according to Procedure 18 and are shown below in Table 11. AD different reagents/starting materials than those described in Procedure 18 are noted in the last column of Table 11—"Changes to Procedure 18: Different Reagents/Starting Materials".

TABLE 11
Examples 122-129
| Example | Structure | ES/MS m/z | ¹H-NMR | Changes to Procedure 18: Different Reagents/ Starting Materials |
|---|---|---|---|---|
| 122 | 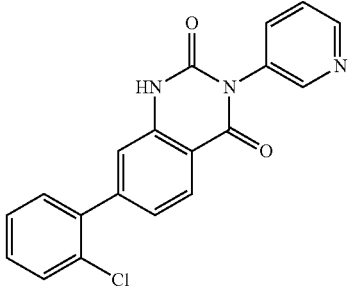 [SMILES: O=c1[nH]c2cc(-c3ccccc3Cl)ccc2c(=O)n1-c1cccnc1] | 350.1 | 1H NMR (400 MHz, DMSO-d6) δ 11.77 (s, 1H), 8.65 (dd, 1H), 8.62 (s, 1H), 8.04 (d, 1H), 7.90 (ddd, 1H), 7.67-7.57 (m, 2H), 7.53-7.45 (m, 3H), 7.32-7.26 (m, 2H). | 3-Aminopyridine |
| 123 | 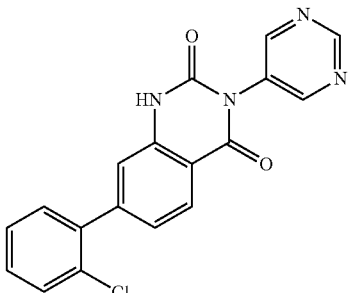 | 351.1 | 1H NMR (400 MHz, DMSO-d6) δ 11.88 (s, 1H), 9.26 (s, 1H), 8.92 (s, 2H), 8.06 (d, 1H), 7.64 (dt, 1H), 7.54-7.44 (m, 3H), 7.34-7.27 (m, 2H). | 5-aminopyrimidine |
| 124 | 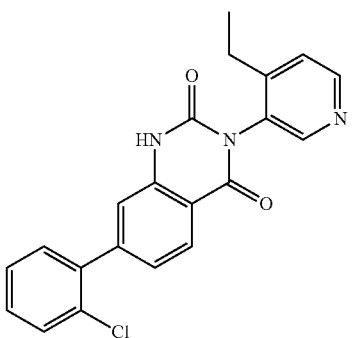 [SMILES: CCc1ccncc1-n1c(=O)[nH]c2cc(-c3ccccc3Cl)ccc2c1=O] | 378.2 | 1H NMR (400 MHz, DMSO-d6) δ 11.87 (s, 1H), 8.65 (d, 1H), 8.60 (s, 1H), 8.05 (d, 1H), 7.67-7.61 (m, 2H), 7.54-7.45 (m, 3H), 7.35-7.29 (m, 2H), 2.55 (d, 2H), 1.13 (t, 3H). | 4-ethylpyridin-3-amine |
| 125 | 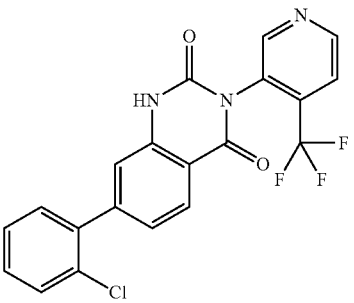 [SMILES: O=c1[nH]c2cc(-c3ccccc3Cl)ccc2c(=O)n1-c1cnccc1C(F)(F)F] | 418.1 | 1H NMR (400 MHz, DMSO-d6) δ 11.95 (s, 1H), 9.00-8.95 (m, 2H), 8.05 (d, 1H), 8.00 (d, 1H), 7.68-7.61 (m, 1H), 7.51 (d, 3H), 7.34 (dd, 1H), 7.31 (d, 1H). | 4-(trifluoromethyl)pyridin-3-amine |

TABLE 11-continued

Examples 122-129

| Example | Structure | ES/MS m/z | ¹H-NMR | Changes to Procedure 18: Different Reagents/ Starting Materials |
|---|---|---|---|---|
| 126 | 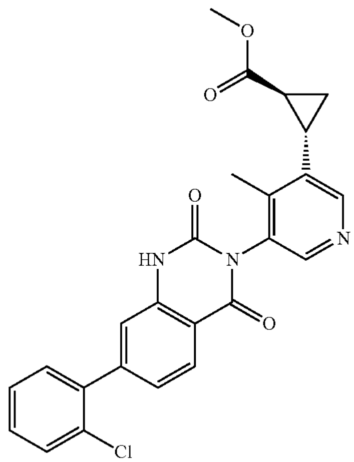 [SMILES: COC(=O)[C@H]1C[C@@H]1c1cncc(-n2c(=O)[nH]c3cc(-c4ccccc4Cl)ccc3c2=O)c1C] | 462.0 | 1H NMR (400 MHz, DMSO-d6) δ 11.83 (s, 1H), 8.45 (s, 1H), 8.37 (s, 1H), 8.04 (d, J = 8.0 Hz, 1H), 7.69-7.60 (m, 1H), 7.54-7.42 (m, 3H), 7.35-7.24 (m, 2H), 3.69 (s, 3H), 2.57-2.52 (m, 1H), 2.17 (s, 3H), 2.04-1.96 (m, 1H), 1.68-1.58 (m, 1H), 1.53 (dt, J = 9.5, 4.8 Hz, 1H). | I-31; I-40 |
| 127 | 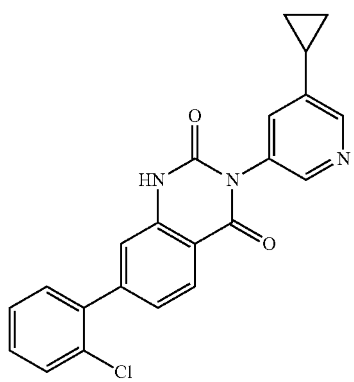 [SMILES: O=c1[nH]c2cc(-c3ccccc3Cl)ccc2c(=O)n1-c1cncc(C2CC2)c1] | 390.0 | 1H NMR (400 MHz, DMSO-d6) δ 11.75 (s, 1H), 8.47 (d, J = 2.1 Hz, 1H), 8.38 (d, J = 2.2 Hz, 1H), 8.02 (d, J = 8.1 Hz, 1H), 7.68-7.60 (m, 1H), 7.58 (t, J = 2.2 Hz, 1H), 7.53-7.43 (m, 3H), 7.32-7.23 (m, 2H), 2.05 (tt, J = 8.4, 5.1 Hz, 1H), 1.10-1.02 (m, 2H), 0.82-0.71 (m, 2H). | I-31; 5-cyclopropylpyridin-3-amine |
| 128 | 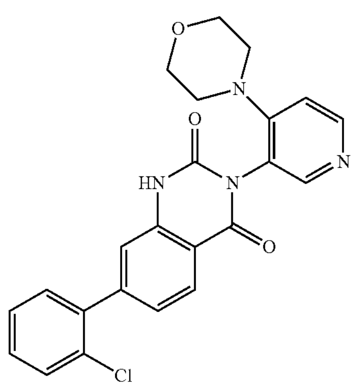 [SMILES: O=c1[nH]c2cc(-c3ccccc3Cl)ccc2c(=O)n1-c1cnccc1N1CCOCC1] | 435.0 | 1H NMR (400 MHz, DMSO-d6) δ 11.99 (s, 1H), 8.55 (d, J = 1.1 Hz, 1H), 8.42 (dd, J = 7.2, 1.2 Hz, 1H), 8.07 (d, J = 8.1 Hz, 1H), 7.69-7.61 (m, 1H), 7.54-7.48 (m, 2H), 7.48-7.44 (m, 2H), 7.35 (dd, J = 8.1, 1.6 Hz, 1H), 7.31 (d, J = 1.5 Hz, 1H), 3.65-3.61 (m, 4H), 3.53-3.49 (m, 4H). | I-31; 4-morpholinopyridin-3-amine |

TABLE 11-continued

Examples 122-129

| Example | Structure | ES/MS m/z | ¹H-NMR | Changes to Procedure 18: Different Reagents/ Starting Materials |
|---|---|---|---|---|
| 129 | 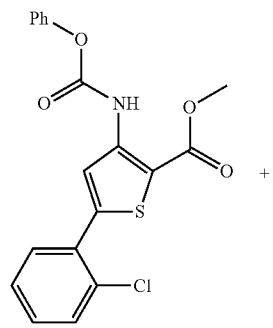 | 434.0 | 1H NMR (400 MHz, DMSO-d6) δ 11.79 (s, 1H), 8.63 (d, J = 5.3 Hz, 1H), 8.55 (s, 1H), 8.07-8.01 (m, 1H), 7.70-7.60 (m, 2H), 7.54-7.44 (m, 3H), 7.35-7.27 (m, 2H), 3.86 (dt, J = 10.5, 4.8 Hz, 2H), 3.41-3.28 (m, 2H), 2.84 (tt, J = 12.0, 3.5 Hz, 1H), 1.81-1.64 (m, 2H), 1.60-1.45 (m, 2H). | I-31; I-42 |

Procedure 19: Example 130

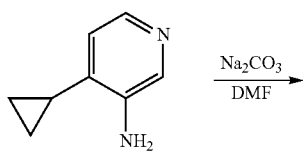

I-30

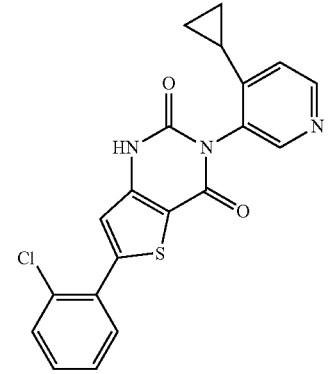

Example 130

6-(2-chlorophenyl)-3-(4-cyclopropylpyridin-3-yl)thieno[3,2-d]pyrimidine-2,4(1H,3H)-dione (Example 130): To a solution of methyl 5-(2-chlorophenyl)-3-((phenoxycarbonyl)amino)thiophene-2-carboxylate (I-30) (50 mg, 0.13 mmol) in DMF (1.5 mL) was added sodium carbonate (14 mg, 0.13 mmol) followed by 4-cyclopropylpyridin-3-amine (52 mg, 0.39 mmol). The reaction mixture was heated at 50° C. for 16 hours, then to complete the cyclization 1 eq of cesium carbonate was added and the temperature was increased to 100° C. Once the cyclization was complete, the mixture was cooled, diluted with 0.5 ml TFA:DMF. The mixture was filtered through an acrodisc before purification by RP-HPLC (0.1% TFA-ACN in 0.1% TFA Water, Column: Gemini 5 uM, NX-C18 110 Angstrom, 250×21.2 mm) to give Example 130 as a trifluoroacetate salt.

ES/MS: 396.1 (M+H⁺).

¹H NMR (400 MHz, DMSO-d₆) δ 12.28 (s, 1H), 8.56 (d, 2H), 7.78-7.72 (m, 1H), 7.71-7.67 (m, 1H), 7.58-7.48 (m, 2H), 7.30 (s, 1H), 7.19 (d, 1H), 1.87 (tt, 1H), 1.05 (dt, 2H), 0.88 (td, 2H).

Examples 131-139

The following Examples were made in an analogous fashion according to Procedure 19 and are shown below in Table 12. Any different reagents/starting materials than those described in Procedure 19 are noted in the last column of Table 12—"Changes to Procedure 19: Different Reagents/Starting Materials".

TABLE 12

Examples 131-139

| Example | Structure | ES/MS m/z | $^1$H-NMR | Changes to Procedure 19: Different Reagents/Starting Materials |
|---|---|---|---|---|
| 131 | 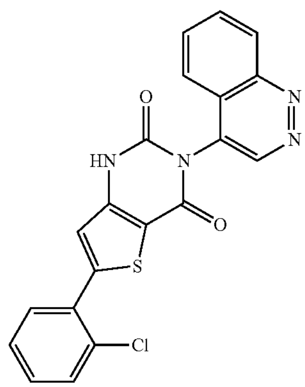 [SMILES: O=c1[nH]c2cc(-c3ccccc3Cl)sc2c(=O)n1-c1cnnc2ccccc12] | 407.1 | 1H NMR (400 MHz, DMSO-d6) δ 12.43 (s, 1H), 9.54 (s, 1H), 8.66-8.56 (m, 1H), 8.17-8.10 (m, 1H), 8.05 (ddd, 1H), 7.92 (ddd, 1H), 7.82-7.74 (m, 1H), 7.73-7.66 (m, 1H), 7.60-7.49 (m, 2H), 7.35 (s, 1H). | I-32 |
| 132 | 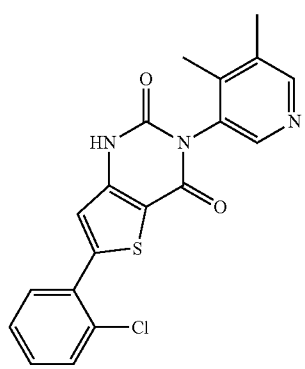 [SMILES: Cc1cncc(-n2c(=O)[nH]c3cc(-c4ccccc4Cl)sc3c2=O)c1C] | 384.1 | 1H NMR (400 MHz, DMSO-d6) δ 12.24 (s, 1H), 8.43 (s, 1H), 8.36 (s, 1H), 7.78-7.72 (m, 1H), 7.72-7.64 (m, 1H), 7.58-7.48 (m, 2H), 7.29 (s, 1H), 2.34 (s, 3H), 2.07 (s, 3H). | I-35 |
| 133 | 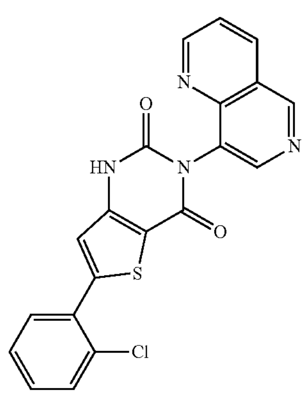 [SMILES: O=c1[nH]c2cc(-c3ccccc3Cl)sc2c(=O)n1-c1cncc2cccnc12] | 407.0 | 1H NMR (400 MHz, DMSO-d6) δ 12.27 (s, 1H), 9.55 (s, 1H), 9.12 (dd, 1H), 8.84 (s, 1H), 8.74 (dd, 1H), 7.83-7.76 (m, 2H), 7.72-7.68 (m, 1H), 7.58-7.50 (m, 2H), 7.33 (s, 1H). | I-36 |

TABLE 12-continued

Examples 131-139

| Example | Structure | ES/MS m/z | ¹H-NMR | Changes to Procedure 19: Different Reagents/ Starting Materials |
|---|---|---|---|---|
| 134 | 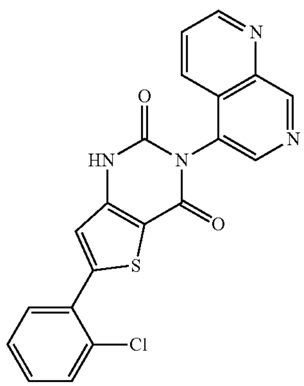 [SMILES: O=c1[nH]c2cc(-c3ccccc3Cl)sc2c(=O)n1-c1cncc2ncccc12] | 407.0 | 1H NMR (400 MHz, DMSO-d6) δ 12.31 (s, 1H), 9.53 (d, 1H), 9.14 (dd, 1H), 8.72 (s, 1H), 8.48 (dt, 1H), 7.81 (dd, 1H), 7.78-7.75 (m, 1H), 7.73-7.68 (m, 1H), 7.58-7.50 (m, 2H), 7.34 (s, 1H). | I-37 |
| 135 | 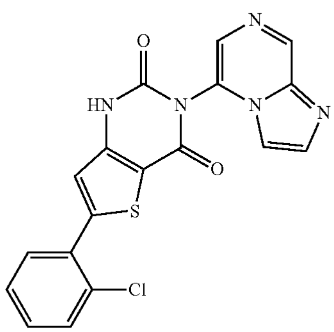 [SMILES: O=c1[nH]c2cc(-c3ccccc3Cl)sc2c(=O)n1-c1cncc2nccn12] | 396.0 | 1H NMR (400 MHz, DMSO-d6) δ 12.44 (s, 1H), 9.21 (s, 1H), 8.49 (t, 1H), 8.17 (s, 1H), 7.90 (d, 1H), 7.77-7.74 (m, 1H), 7.72-7.69 (m, 1H), 7.58-7.51 (m, 2H), 7.33 (s, 1H). | I-38 |
| 136 | 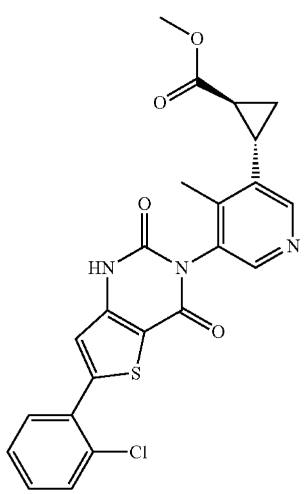 [SMILES: COC(=O)[C@H]1C[C@@H]1c1cncc(-n2c(=O)[nH]c3cc(-c4ccccc4Cl)sc3c2=O)c1C] | 468.0 | 1H NMR (400 MHz, DMSO-d6) δ 12.26 (d, J = 1.4 Hz, 1H), 8.45 (s, 1H), 8.37 (s, 1H), 7.78-7.71 (m, 1H), 7.71-7.63 (m, 1H), 7.58-7.46 (m, 2H), 7.29 (d, J = 0.7 Hz, 1H), 3.69 (d, J = 1.1 Hz, 3H), 2.57-2.51 (m, 1H), 2.17 (s, 3H), 2.05-1.95 (m, 1H), 1.67-1.57 (m, 1H), 1.52 (dt, J = 9.4, 4.8 Hz, 1H). | I-40 |

TABLE 12-continued

Examples 131-139

| Example | Structure | ES/MS m/z | ¹H-NMR | Changes to Procedure 19: Different Reagents/ Starting Materials |
|---|---|---|---|---|
| 137 | 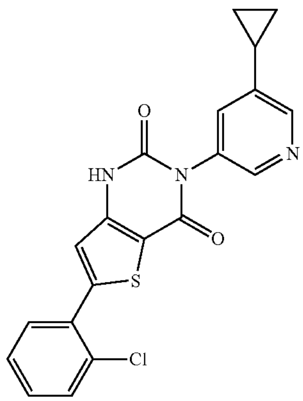 [SMILES: O=c1[nH]c2cc(-c3ccccc3Cl)sc2c(=O)n1-c1cncc(C2CC2)c1] | 395.9 | 1H NMR (400 MHz, DMSO-d6) δ 12.15 (s, 1H), 8.45 (d, J = 2.1 Hz, 1H), 8.34 (d, J = 2.3 Hz, 1H), 7.78-7.71 (m, 1H), 7.71-7.63 (m, 1H), 7.56-7.46 (m, 3H), 7.26 (s, 1H), 2.08-1.97 (m, 1H), 1.10-1.00 (m, 2H), 0.80-0.70 (m, 2H). | 5-cyclopropylpyridin-3-amine |
| 138 | 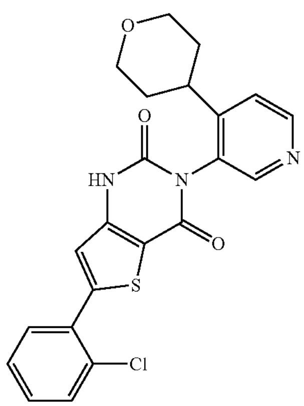 [SMILES: O=c1[nH]c2cc(-c3ccccc3Cl)sc2c(=O)n1-c1cnccc1C1CCOCC1] | 440.0 | 1H NMR (400 MHz, DMSO-d6) δ 12.21 (s, 1H), 8.61 (d, J = 5.3 Hz, 1H), 8.51 (s, 1H), 7.78-7.71 (m, 1H), 7.71-7.66 (m, 1H), 7.63 (d, J = 5.3 Hz, 1H), 7.57-7.48 (m, 2H), 7.30 (s, 1H), 3.91-3.82 (m, 2H), 3.42-3.29 (m, 2H), 2.84-2.73 (m, 1H), 1.72 (qt, J = 11.9, 5.0 Hz, 2H), 1.60-1.45 (m, 2H). | I-42 |
| 139 | 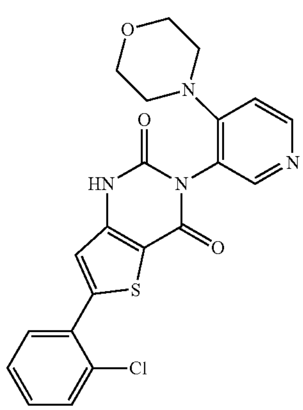 [SMILES: O=c1[nH]c2cc(-c3ccccc3Cl)sc2c(=O)n1-c1cnccc1N1CCOCC1] | 441.0 | 1H NMR (400 MHz, DMSO-d6) δ 12.42 (s, 1H), 8.53 (s, 1H), 8.40 (d, J = 7.1 Hz, 1H), 7.78-7.71 (m, 1H), 7.71-7.65 (m, 1H), 7.58-7.48 (m, 2H), 7.43 (d, J = 7.2 Hz, 1H), 7.31 (s, 1H), 3.64 (t, J = 4.7 Hz, 4H), 3.49 (t, J = 4.8 Hz, 4H). | 4-morpholinopyridin-3-amine |

Procedure 20: Example 140

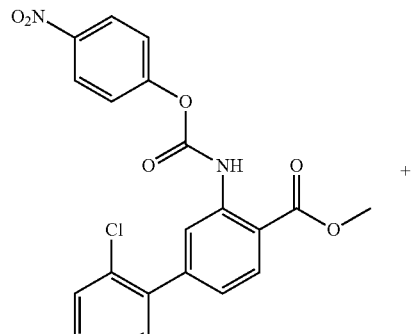

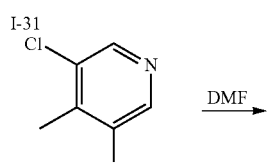

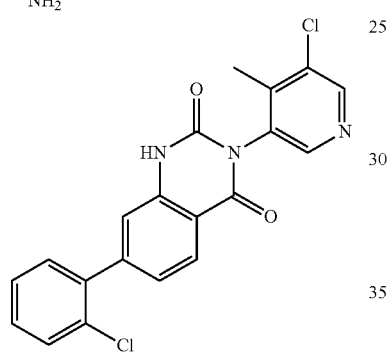

Example 140

3-(5-chloro-4-methylpyridin-3-yl)-7-(2-chlorophenyl) quinazoline-2,4(1H,3H)-dione (Example 140): To a solution of methyl 2'-chloro-3-(((4-nitrophenoxy)carbonyl)amino)-[1,1'-biphenyl]-4-carboxylate (I-31) (50 mg, 0.12 mmol) in DMF (1.5 mL) was added 5-chloro-4-methylpyridin-3-amine (50 mg, 0.35 mmol). The reaction mixture was heated at 80° C. for 30 minutes, then to complete the cyclization, 1 eq of cesium carbonate was added and the temperature was increased to 100° C. Once the cyclization was complete, the mixture was cooled, diluted with 0.5 ml TFA:DMF. The mixture was filtered through an acrodisc before purification by RP-HPLC (0.1% TFA-ACN in 0.1% TFA Water, Column: Gemini 5 uM, NX-C18 110 Angstrom, 250×21.2 mm) to give Example 140 as a trifluoroacetate salt.

ES/MS: 398.1 (M+H$^+$).

$^1$H NMR (400 MHz, DMSO-d$_6$) δ 11.88 (s, 1H), 8.69 (s, 1H), 8.53 (s, 1H), 8.06 (d, 1H), 7.66-7.63 (m, 1H), 7.53-7.45 (m, 3H), 7.35-7.29 (m, 2H), 2.21 (s, 3H).

Example 141

The following Example was made in an analogous fashion according to Procedure 20 and is shown below in Table 13. Any different reagents/starting materials than those described in Procedure 20 are noted in the last column of Table 13—"Changes to Procedure 20: Different Reagents/Starting Materials".

TABLE 13

| | Example 141 | | | |
|---|---|---|---|---|
| Example | Structure | ES/MS m/z | $^1$H-NMR | Changes to Procedure 20: Different Reagents/ Starting Materials |
| 141 | | 394.2 | 1H NMR (400 MHz, DMSO-d6) δ 11.84 (s, 1H), 8.43 (s, 1H), 8.29 (s, 1H), 8.05 (d, 1H), 7.68-7.62 (m, 1H), 7.54-7.45 (m, 3H), 7.35-7.29 (m, 2H), 4.01 (s, 3H), 2.03 (s, 3H). | 5-methoxy-4-methylpyridin-3-amine |

Procedure 21: Example 142

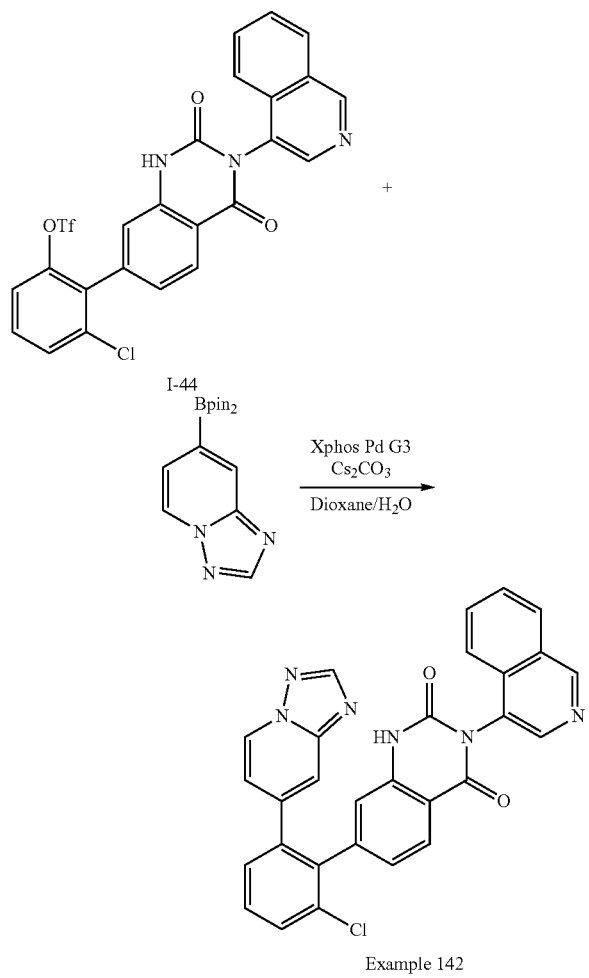

Example 142

7-[12-chloro-6-([1,2,4]triazolo[1,5-a]pyridin-7-yl)phenyl]-3-(4-isoquinolyl)-1H-quinazoline-2,4-dione (Example 142): To 40 ml vial with [3-chloro-2-[3-(4-isoquinolyl)-2,4-dioxo-1H-quinazolin-7-yl]phenyl]trifluoromethanesulfonate (1-44) (50 mg, 0.09 mmol) were added 7-(4,4,5,5-tetramethyl-1,3,2-dioxaborolan-2-yl)-[1,2,4]triazolo[1,5-a]pyridine (26.8 mg, 0.11 mmol), XPhos Pd G3 (6.7 mg, 0.009 mmol) and cesium carbonate (89.2 mg, 0.27 mmol). Dioxane (1.0 mL) and water (0.1 mL) were added, and the mixture was degassed with argon for 30 seconds. The vial was sealed, and the reaction mixture was heated at 90° C. for 2 h. The crude mixture was concentrated under reduced pressure, and to the crude residue was added acetonitrile (0.5 mL), TFA (0.3 mL) and water (0.2 mL). The mixture was heated to produce a homogeneous mixture, and the mixture was filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the title compound Example 142 as a trifluoroacetate salt.

ES/MS: 517.1 (M$^+$).

1H NMR (400 MHz, MeOD) δ 9.67 (s, 1H), 8.73-8.62 (m, 2H), 8.54-8.40 (m, 2H), 8.15-7.98 (m, 3H), 7.96 (ddd, J=8.2, 6.6, 1.5 Hz, 1H), 7.75 (dt, J=7.2, 2.0 Hz, 1H), 7.70-7.56 (m, 3H), 7.32-7.13 (m, 2H), 7.05 (ddd, J=14.3, 7.1, 1.8 Hz, 1H).

Examples 143-148

The following Examples were made in an analogous fashion according to Procedure 21 and are shown below in Table 14. Any different reagents/starting materials than those described in Procedure 21 are noted in the last column of Table 14—"Changes to Procedure 21: Different Reagents/Starting Materials".

TABLE 14

Examples 143-148

| Example | Structure | ES/MS m/z | $^1$H-NMR | Changes to Procedure 21: Different Reagents/Starting Materials |
|---|---|---|---|---|
| 143 | 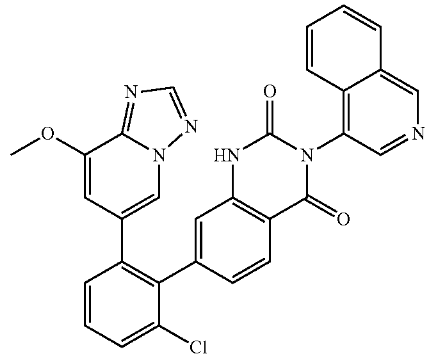 [SMILES: COc1cc(-c2cccc(Cl)c2-c2ccc3c(=O)n(-c4cncc5ccccc45)c(=O)[nH]c3c2)cn2ncnc12] | 547.1 | 1H NMR (400 MHz, MeOD) δ 9.66 (d, J = 7.2 Hz, 1H), 8.67 (d, J = 8.5 Hz, 1H), 8.47 (q, J = 8.3, 6.7 Hz, 2H), 8.41-8.33 (m, 2H), 8.14-7.91 (m, 5H), 7.73 (ddd, J = 6.3, 3.7, 2.3 Hz, 1H), 7.68-7.56 (m, 2H), 7.37-7.21 (m, 2H), 7.16 (dd, J = 10.8, 1.5 | 8-methoxy-6-(4,4,5,5-tetramethyl-1,3,2-dioxaborolan-2-yl)-[1,2,4]triazolo[1,5-a]pyridine (I-59) |

TABLE 14-continued

Examples 143-148

| Example | Structure | ES/MS m/z | ¹H-NMR | Changes to Procedure 21: Different Reagents/ Starting Materials |
|---|---|---|---|---|
| | | | Hz, 1H), 6.89 (dd, J = 13.4, 1.3 Hz, 1H), 3.92 (d, J = 13.0 Hz, 3H). | |
| 144 | 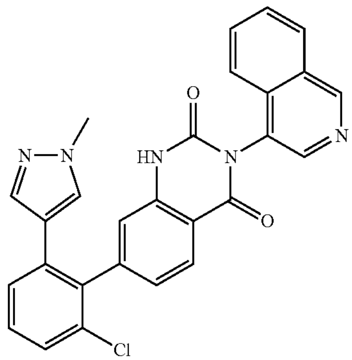 [SMILES: Cn1cc(-c2cccc(Cl)c2-c2ccc3c(=O)n(-c4cncc5ccccc45)c(=O)[nH]c3c2)cn1] | 480.1 | 1H NMR (400 MHz, MeOD) δ 9.71 (s, 1H), 8.74 (d, J = 7.1 Hz, 1H), 8.50 (dd, J = 8.3, 2.5 Hz, 1H), 8.15 (dd, J = 8.5, 2.0 Hz, 1H), 8.13-8.09 (m, 1H), 8.08 (d, J = 1.5 Hz, 1H), 7.99 (dtd, J = 8.0, 5.7, 1.9 Hz, 1H), 7.59-7.38 (m, 4H), 7.19 (dt, J = 8.8, 1.5 Hz, 2H), 7.11-7.06 (m, 1H), 3.83 (d, J = 13.3 Hz, 3H). | (1-methylpyrazol-4-yl)boronic acid |
| 145 | 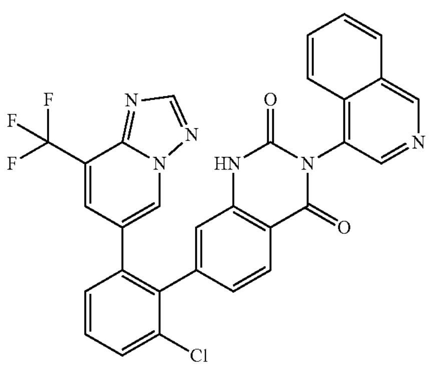 [SMILES: O=c1[nH]c2cc(-c3c(Cl)cccc3-c3cc(C(F)(F)F)c4ncnn4c3)ccc2c(=O)n1-c1cncc2ccccc12] | 585.2 | 1H NMR (400 MHz, MeOD) δ 9.63 (d, J = 17.2 Hz, 1H), 9.05 (d, J = 26.1 Hz, 1H), 8.61-8.52 (m, 1H), 8.45 (d, J = 8.2 Hz, 1H), 8.13-7.87 (m, 5H), 7.83-7.75 (m, 2H), 7.70-7.60 (m, 2H), 7.28 (dd, J = 12.8, 8.3 Hz, 1H), 7.16 (d, J = 1.8 Hz, 1H). | 6-(4,4,5,5-tetramethyl-1,3,2-dioxaborolan-2-yl)-8-(trifluoromethyl)-[1,2,4]triazolo[1,5-a]pyridine (I-60) |
| 146 | 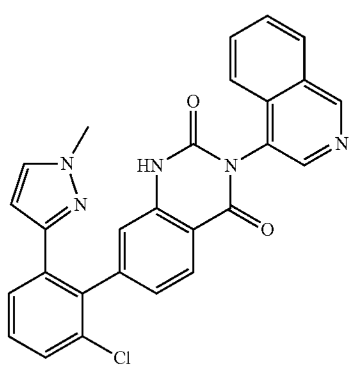 [SMILES: Cn1ccc(-c2cccc(Cl)c2-c2ccc3c(=O)n(-c4cncc5ccccc45)c(=O)[nH]c3c2)n1] | 480.1 | 1H NMR (400 MHz, MeOD) δ 9.66 (s, 1H), 8.70 (s, 1H), 8.48-8.43 (m, 1H), 8.14-7.90 (m, 5H), 7.73 (dd, J = 7.8, 1.4 Hz, 1H), 7.65-7.47 (m, 3H), 7.41 (dd, J = 17.2, 2.3 Hz, 1H), 7.20-7.14 (m, 2H), 5.68 (d, J = 2.3 Hz, 1H), 3.87 (d, J = 8.4 Hz, 3H). | 1-methyl-3-(4,4,5,5-tetramethyl-1,3,2-dioxaborolan-2-yl)pyrazole |

TABLE 14-continued

Examples 143-148

| Example | Structure | ES/MS m/z | ¹H-NMR | Changes to Procedure 21: Different Reagents/ Starting Materials |
|---|---|---|---|---|
| 147 | 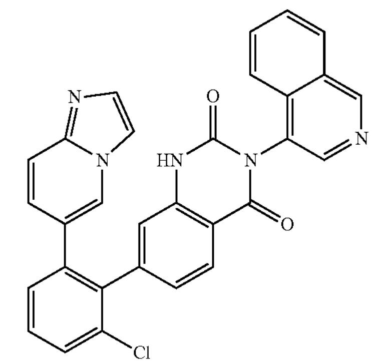 [SMILES: O=c1[nH]c2cc(-c3c(Cl)cccc3-c3ccc4nccn4c3)ccc2c(=O)n1-c1cncc2ccccc12] | 516.1 | 1H NMR (400 MHz, MeOD) δ 9.50 (d, J = 10.9 Hz, 1H), 8.85 (dt, J = 7.7, 1.3 Hz, 1H), 8.47 (s, 1H), 8.35 (dd, J = 10.2, 8.3 Hz, 1H), 8.22 (ddd, J = 6.6, 2.2, 0.7 Hz, 1H), 8.08 (dd, J = 3.5, 2.2 Hz, 1H), 8.04 (dd, J = 8.5, 2.3 Hz, 1H), 7.96-7.57 (m, 8H), 7.25-7.15 (m, 2H). | 6-(4,4,5,5-tetramethyl-1,3,2-dioxaborolan-2-yl)imidazo[1,2-a]pyridine |
| 148 | 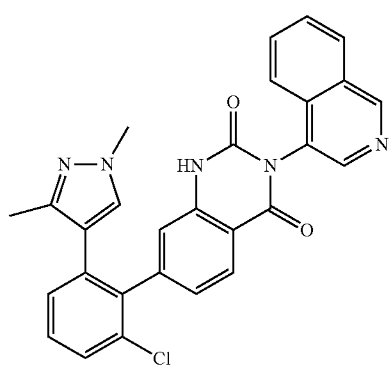 [SMILES: Cc1nn(C)cc1-c1cccc(Cl)c1-c1ccc2c(=O)n(-c3cncc4ccccc34)c(=O)[nH]c2c1] | 494.1 | 1H NMR (400 MHz, MeOD) δ 9.68 (s, 1H), 8.70 (d, J = 4.1 Hz, 1H), 8.51-8.44 (m, 1H), 8.13-8.01 (m, 3H), 7.97 (dddd, J = 8.1, 6.5, 3.5, 1.4 Hz, 1H), 7.59 (ddd, J = 8.1, 2.1, 1.3 Hz, 1H), 7.48 (t, J = 7.8 Hz, 1H), 7.37 (dd, J = 7.6, 1.3 Hz, 1H), 7.23 (d, J = 17.5 Hz, 1H), 7.15 (dt, J = 8.1, 1.8 Hz, 1H), 7.11 (t, J = 1.9 Hz, 1H), 3.74 (d, J = 14.3 Hz, 3H), 2.05 (d, J = 6.8 Hz, 3H). | (1,3-dimethylpyrazol-4-yl)boronic acid |

Procedure 22: Example 149

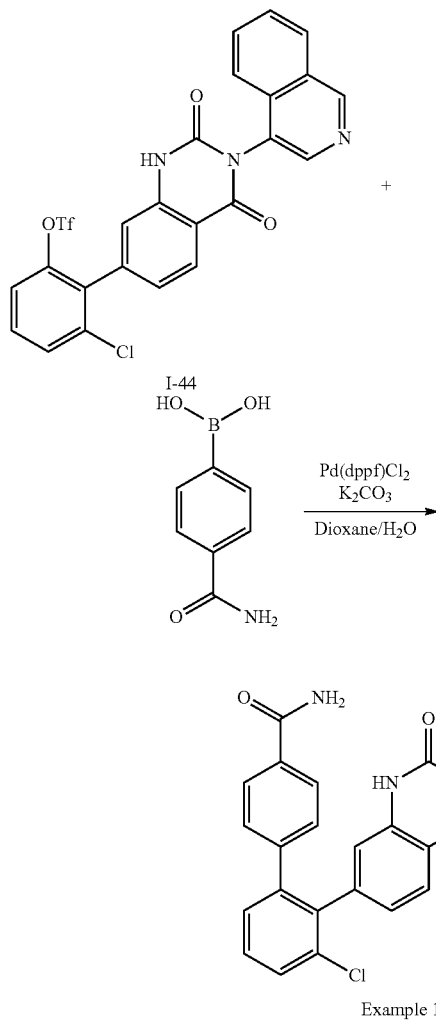

Example 149

4-[3-chloro-2-[3-(4-isoquinolyl)-2,4-dioxo-1H-quinazolin-7-yl]phenyl]benzamide (Example 149): To a vial with [3-chloro-2-[3-(4-isoquinolyl)-2,4-dioxo-1H-quinazolin-7-yl]phenyl]trifluoromethanesulfonate (I-44) (40 mg, 0.073 mmol) were added (4-carbamoylphenyl)boronic acid (13.2 mg, 0.08 mmol), Pd(dppf)Cl$_2$ (11.5 mg, 0.007 mmol) and potassium carbonate (30.3 mg, 0.22 mmol). Dioxane (1.0 mL) and water (0.1 mL) were added, and the mixture was degassed with argon for 30 seconds. The vial was sealed, and the reaction mixture was heated at 90° C. for 2 h. The crude mixture was concentrated under reduced pressure, and to the crude residue was added, acetonitrile (0.5 mL), TFA (0.3 mL) and water (0.2 mL). The mixture was heated to produce a homogeneous mixture, and the mixture was filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the title compound Example 149 as a trifluoroacetate salt.

ES/MS: 519.1 (M+H$^+$).

Multiplet Report 1H NMR (400 MHz, MeOD) δ 9.61 (s, 1H), 8.63 (d, J=4.2 Hz, 1H), 8.43 (d, J=8.2 Hz, 1H), 7.97 (ddt, J=29.0, 14.6, 7.0 Hz, 5H), 7.83-7.72 (m, 3H), 7.72-7.62 (m, 2H), 7.60-7.52 (m, 2H), 7.51-7.40 (m, 2H), 7.36-7.20 (m, 3H), 7.19-7.02 (m, 3H).

Procedure 23: Example 150 and Example 151

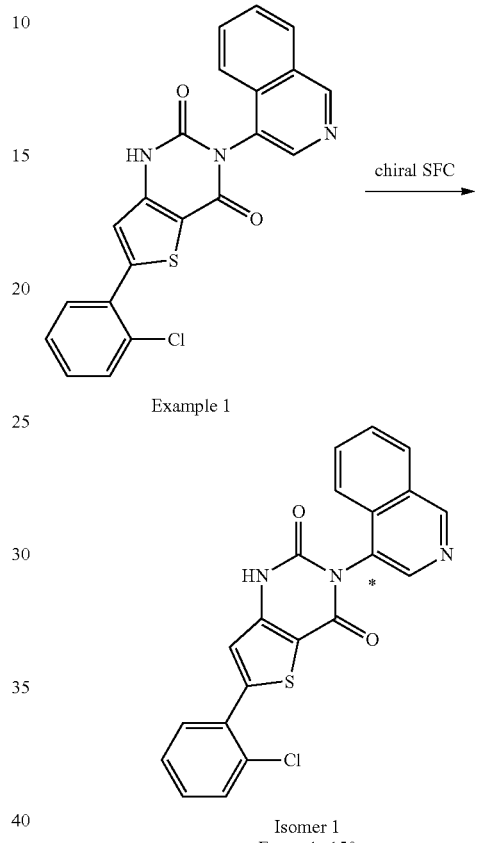

6-(2-chlorophenyl)-3-(isoquinolin-4-yl)thieno[3,2-d]pyrimidine-2,4(1H,3H)-dione (Example 1) as a mixture of 2 enantiomers was separated by chiral SFC (IA 4.6×$^{100}$ mm column with 40% EtOH cosolvent) to give two enantiomers, which were designated Isomer 1 and Isomer 2.

Isomer 1:

6-(2-chlorophenyl)-3-(isoquinolin-4-yl)thieno[3,2-d]pyrimidine-2,4(1H,3H)-dione (Example 150)

ES/MS: 406.1 (M+).
1H NMR (400 MHz, MeOD-d4) δ 9.60 (s, 1H), 8.66 (s, 1H), 8.42 (d, J=8.3 Hz, 1H), 8.07-7.94 (m, 2H), 7.92 (t, J=7.5 Hz, 1H), 7.83-7.68 (m, 1H), 7.68-7.61 (m, 1H), 7.60-7.45 (m, 2H), 7.37 (s, 1H).

Isomer 2:

6-(2-chlorophenyl)-3-(isoquinolin-4-yl)thieno[3,2-d]pyrimidine-2,4(1H,3H)-dione (Example 151)

ES/MS: 406.1 (M+).
$^1$H NMR (400 MHz, MeOD-d4) δ 9.60 (s, 1H), 8.66 (s, 1H), 8.42 (d, J=8.3 Hz, 1H), 8.07-7.94 (m, 2H), 7.92 (t, J=7.5 Hz, 1H), 7.83-7.68 (m, 1H), 7.68-7.61 (m, 1H), 7.60-7.45 (m, 2H), 7.37 (s, 1H).

Procedure 24: Example 152

6-(2-chlorophenyl)-3-(isoquinolin-4-yl)-1-(2-methyl-2H-indazol-6-yl)thieno[3,2-d]pyrimidine-2,4(1H,3H)-dione (Example 152): To a stirring solution of 6-(2-chlorophenyl)-3-(isoquinolin-4-yl)thieno[3,2-d]pyrimidine-2,4(1H,3H)-dione (Example 1) (30 mg, 0.073 mmol, 1.0 equiv.) in DCM (0.74 mmol, 0.1 M) were added (2-methylindazol-6-yl) boronic acid (26 mg, 0.14 mmol, 2.0 equiv.), Cu(OAc)2 (26.9 mg, 0.15 mmol, 2.0 equiv.) followed by Et3N (31 μL, 3.0 equiv.). The suspension was stirred at rt for 16 h after which the reaction mixture was filtered through celite eluting with DCM and concentrated under reduced pressure. The crude product was diluted in acetonitrile/water/trifluoroacetic acid (1.5 mL: 5:1:0.2), filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 152 as a trifluoroacetate salt.

ES/MS: 536.1 (M+).
$^1$H NMR (400 MHz, Methanol-d4) δ 9.66 (s, 1H), 8.80 (s, 1H), 8.45 (d, J=8.3 Hz, 1H), 8.37 (s, 1H), 8.30-8.19 (m, 1H), 8.13-8.03 (m, 1H), 7.95 (dd, J=15.4, 7.5 Hz, 3H), 7.74-7.36 (m, 5H), 7.29 (dd, J=16.0, 8.8 Hz, 1H), 6.82 (s, 1H), 4.29 (s, 3H).

Procedure 25: Example 153

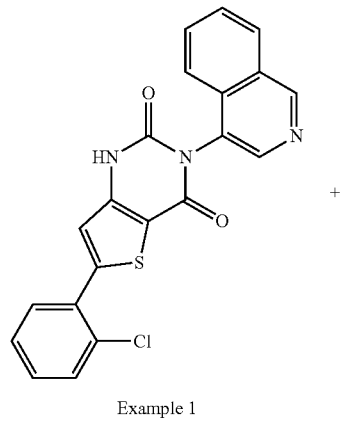

Example 1

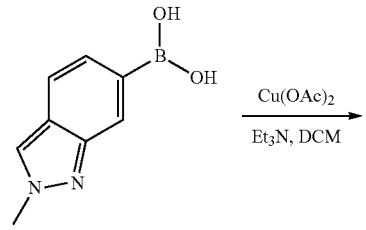

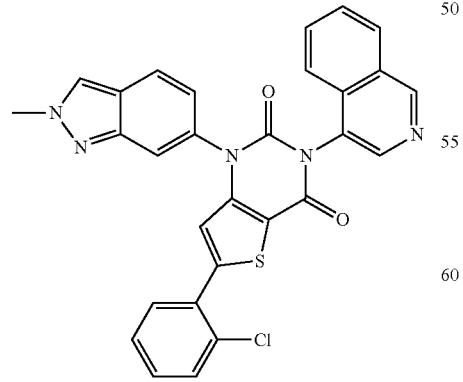

Example 152

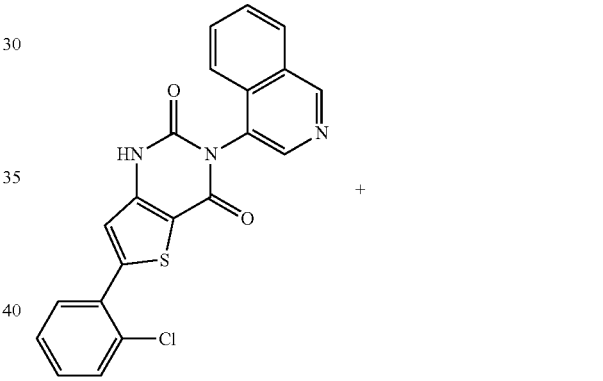

Example 1

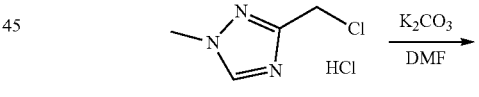

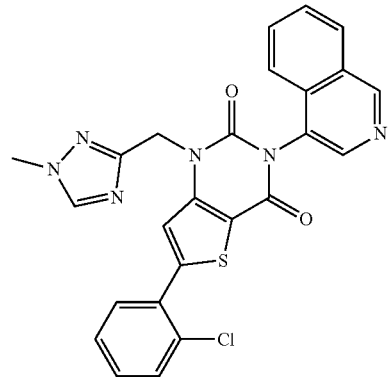

Example 153

6-(2-chlorophenyl)-3-(4-isoquinolyl)-1-[(1-methyl-1,2,4-triazol-3-yl)methyl]thieno[3,2-d]pyrimidine-2,4-dione (Example 153): To a solution of Example 1 (75.0 mg, 0.19 mmol) in DMF (1.00 mL) were added 3-(chloromethyl)-1-methyl-1,2,4-triazole hydrochloride (40.4 mg, 0.24 mmol) and potassium carbonate (66.4 mg, 0.48 mmol) and the reaction mixture was heated at 70° C. for 18 hours. The crude mixture was concentrated under reduced pressure, dissolved in DMSO (2.00 mL), filtered through an acrodisc, and subsequently purified by RP-HPLC (0.1% TFA-ACN in 0.1% TFA Water, Column: Gemini 5 uM, NX-C18 110 Angstrom, 250×21.2 mm) to give the title compound Example 153 as a trifluoroacetate salt.

ES/MS: 501.1 (M$^+$).

1H NMR (400 MHz, Methanol-d$_4$) δ 9.65 (s, 1H), 8.72 (d, J=9.8 Hz, 1H), 8.47-8.42 (m, 1H), 8.40 (s, 1H), 8.17-8.00 (m, 3H), 7.94 (ddd, J=8.2, 6.8, 1.3 Hz, 1H), 7.71-7.65 (m, 1H), 7.65-7.55 (m, 1H), 7.54 (s, 1H), 7.50-7.43 (m, 1H), 5.59-5.40 (m, 2H), 3.91 (s, 3H).

Examples 154-157

The following Examples were made in an analogous fashion according to Procedure 25 and are shown below in Table 15. Any different reagents/starting materials than those described in Procedure 25 are noted in the last column of Table 15—"Changes to Procedure 25: Different Reagents/Starting Materials".

TABLE 15

Examples 154-157

| Example | Structure | ES/MS m/z | $^1$H-NMR | Changes to Procedure 25: Different Reagents/ Starting Materials |
|---|---|---|---|---|
| 154 | 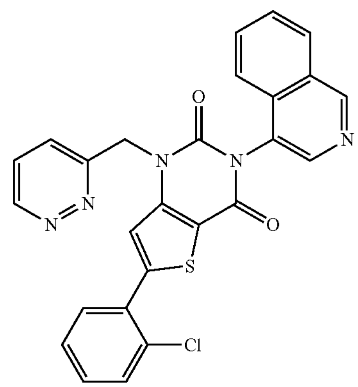 | 498.1 | 1H NMR (400 MHz, Methanol-d4) δ 9.69 (s, 1H), 9.17 (dd, J = 4.9, 1.6 Hz, 1H), 8.76 (s, 1H), 8.47 (d, J = 8.3 Hz, 1H), 8.16-8.06 (m, 2H), 7.96 (ddd, J = 8.1, 6.6, 1.4 Hz, 1H), 7.89 (dd, J = 8.6, 1.6 Hz, 1H), 7.77 (dd, J = 8.6, 4.9 Hz, 1H), 7.70-7.65 (m, 1H), 7.63 (s, 1H), 7.61-7.55 (m, 1H), 7.45 (tt, J = 7.4, 5.5 Hz, 2H), 5.75 (d, J = 2.2 Hz, 2H). | 3-(bromomethyl) pyridazine hydrobromide |
| 155 | 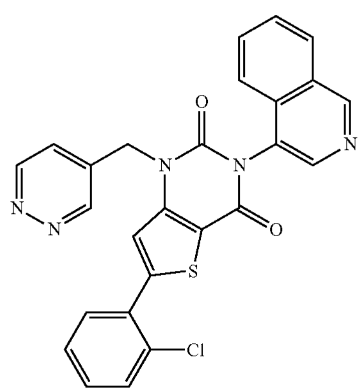 [SMILES: O=c1c2sc(-c3ccccc3Cl)cc2n(Cc2ccnnc2)c(=O)n1-c1cncc2ccccc12] | 498.1 | 1H NMR (400 MHz, Methanol-d4) δ 9.67 (s, 1H), 9.37 (dd, J = 2.5, 1.2 Hz, 1H), 9.21 (dd, J = 5.4, 1.2 Hz, 1H), 8.74 (s, 1H), 8.46 (d, J = 8.4 Hz, 1H), 8.16-8.02 (m, 2H), 8.01-7.93 (m, 1H), 7.87 (dd, J = 5.4, 2.4 Hz, 1H), 7.73-7.67 (m, 1H), 7.62 (s, 1H), 7.55-7.42 (m, 3H), 5.72-5.44 (m, 2H). | 4-(bromomethyl) pyridazine hydrobromide |

TABLE 15-continued

Examples 154-157

| Example | Structure | ES/MS m/z | $^1$H-NMR | Changes to Procedure 25: Different Reagents/ Starting Materials |
|---|---|---|---|---|
| 156 | 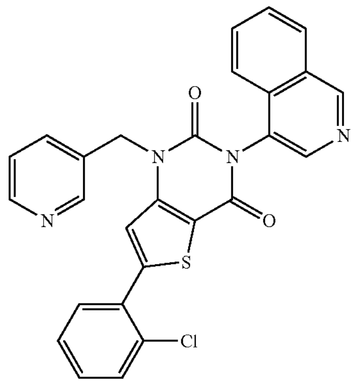 [SMILES: O=c1c2sc(-c3ccccc3Cl)cc2n(Cc2cccnc2)c(=O)n1-c1cncc2ccccc12] | 497.1 | 1H NMR (400 MHz, Methanol-d4) δ 9.57 (s, 1H), 8.95 (d, J = 2.0 Hz, 1H), 8.75 (dd, J = 5.5, 1.4 Hz, 1H), 8.66 (s, 1H), 8.53 (dt, J = 8.3, 1.7 Hz, 1H), 8.39 (d, J = 8.3 Hz, 1H), 8.04-7.96 (m, 2H), 7.96-7.85 (m, 2H), 7.72 (s, 2H), 7.65-7.54 (m, 1H), 7.47 (ddd, J = 6.3, 3.4, 2.0 Hz, 2H), 5.61 (q, J = 16.5 Hz, 2H). | 3-(bromomethyl) pyridine hydrobromide |
| 157 | 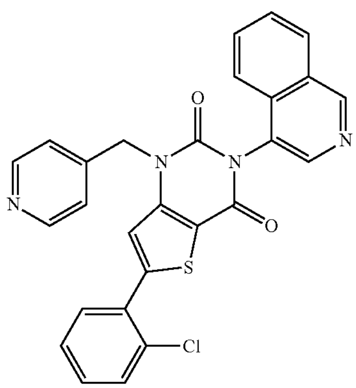 [SMILES: O=c1c2sc(-c3ccccc3Cl)cc2n(Cc2ccncc2)c(=O)n1-c1cncc2ccccc12] | 497.1 | 1H NMR (400 MHz, Methanol-d4) δ 9.53 (s, 1H), 8.80 (d, J = 6.7 Hz, 2H), 8.66 (s, 1H), 8.37 (d, J = 8.4 Hz, 1H), 8.07 (d, J = 6.8 Hz, 2H), 8.05-7.91 (m, 2H), 7.87 (ddd, J = 8.1, 6.7, 1.3 Hz, 1H), 7.73-7.65 (m, 1H), 7.62-7.57 (m, 1H), 7.55 (s, 1H), 7.46 (tt, J = 7.4, 5.5 Hz, 2H), 5.84-5.60 (m, 2H). | 4-(bromomethyl) pyridine hydrobromide |

Procedure 26: Example 158

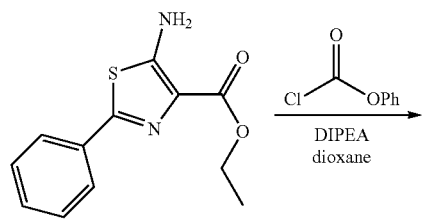

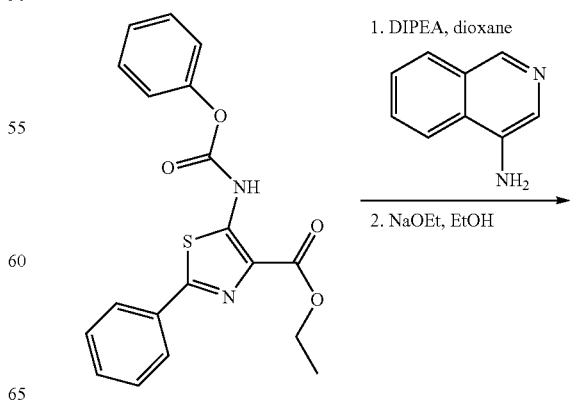

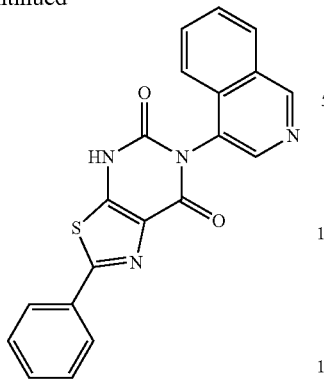

Example 158

Ethyl 5-((phenoxycarbonyl)amino)-2-phenylthiazole-4-carboxylate: To a solution of ethyl 5-amino-2-phenyl-thiazole-4-carboxylate (250 mg, 1.01 mmol) in dry dioxane (1 mL) was added DIPEA (350 µL, 2.01 mmol) followed by phenyl chloroformate (197 µL, 10) mmol). The reaction mixture was heated at 90° C. for 16 hours, after which the mixture was cooled to room temperature. The mixture was concentrated under reduced pressure, and the crude material was purified by silica chromatography (eluent: EtOAc in hexanes) to provide the product.

ES/MS: 369.1 [M+H<sup>+</sup>].

$^1$H NMR (400 MHz, DMSO-d$_6$) δ 10.57 (s, 1H), 8.03-7.74 (m, 2H), 7.61-7.42 (m, 5H), 7.40-7.22 (m, 3H), 4.42 (q, J=7.1 Hz, 2H), 1.38 (t, J=7.1 Hz, 3H).

6-(isoquinolin-4-yl)-2-phenylthiazolo[5,4-d]pyrimidine-5,7(4H,6H)-dione (Example 158): To a solution of ethyl 5-((phenoxycarbonyl)amino)-2-phenylthiazole-4-carboxylate (371 mg, 1.01 mmol) in dry dioxane (0.5 mL) was added DIPEA (351 µL, 64.3 mmol) followed by isoquinolin-4-amine (174 mg, 1.21 mmol). The reaction mixture was heated at 90° C. for 1 hour, after which the mixture was cooled to room temperature and concentrated under reduced pressure. To a suspension of the crude product in EtOH (2 mL), a solution of sodium ethoxide (21% wt solution in EtOH) was added dropwise until the reaction mixture turned to a homogeneous solution (~0.2 mL). The resulting reaction mixture was heated at 50° C. for 2 hours. The reaction was quenched by the addition of MeOH (1 mL), concentrated under reduced pressure, and to the crude residue was added DMF (1 mL), acetonitrile (0.5 mL), TFA (0.3 mL) and water (0.2 mL). The mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the title compound Example 158 as a trifluoroacetate salt.

ES/MS: 373.1 [M+H<sup>+</sup>].

$^1$H NMR (400 MHz, DMSO-d$_6$) δ 12.81 (s, 1H), 9.52 (s, 1H), 8.62 (s, 1H), 8.33 (dt, J=8.1, 1.0 Hz, 1H), 7.99 (qdd, J=5.6, 2.3, 1.4 Hz, 3H), 7.91-7.77 (m, 2H), 7.62-7.51 (m, 3H).

Procedure 27: Example 159

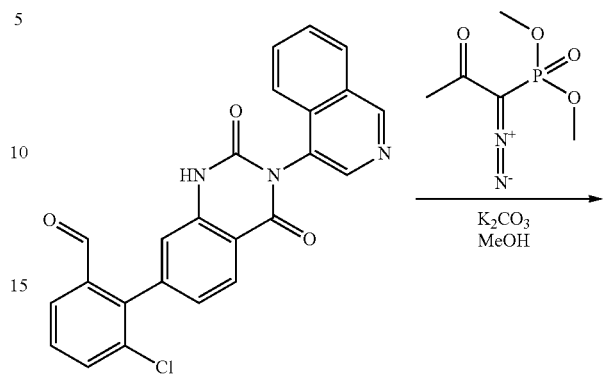

I-48

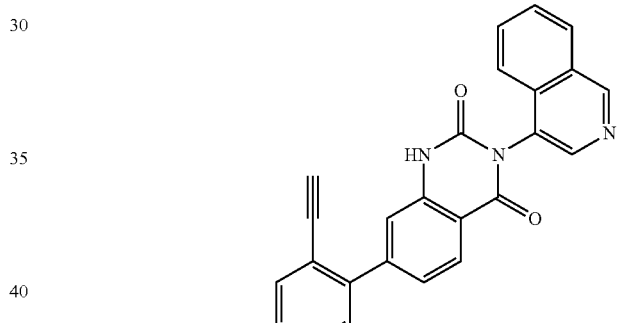

Example 159

7-(2-chloro-6-ethynyl-phenyl)-3-(4-isoquinolyl)-H-quinazoline-2,4-dione (Example 159): A mixture of 3-chloro-2-[3-(4-isoquinolyl)-2,4-dioxo-1H-quinazolin-7-yl]benzaldehyde (1-48) (600 mg, 1.40 mmol), 1-diazo-1-dimethoxyphosphoryl-propan-2-one (316 µL, 2.10 mmol) and K$_2$CO$_3$ (388 mg, 2.80 mmol) in methanol (2 mL) was stirred at room temperature for 2 hours. After completion of the reaction, the reaction mixture was concentrated under reduced pressure, and to the crude residue was added DMF (4 mL). The mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the product as a trifluoroacetate salt.

ES/MS: 424.1 [M+H<sup>+</sup>].

$^1$H NMR (400 MHz, DMSO-d$_6$) δ 11.90 (s, 1H), 9.53 (d, J=0.9 Hz, 1H), 8.69 (d, J=6.6 Hz, 1H), 8.38-8.31 (m, 1H), 8.07 (d, J=8.5 Hz, 1H), 8.02 (d, J=8.2 Hz, 1H), 7.90-7.77 (m, 2H), 7.69 (ddd, J=14.9, 8.0, 1.2 Hz, 2H), 7.51 (t, J=7.9 Hz, 1H), 7.27-7.20 (m, 2H), 4.28 (s, 1H).

Procedure 28: Example 160

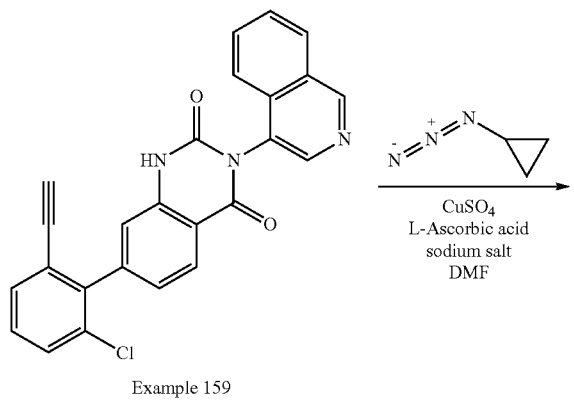

Example 159

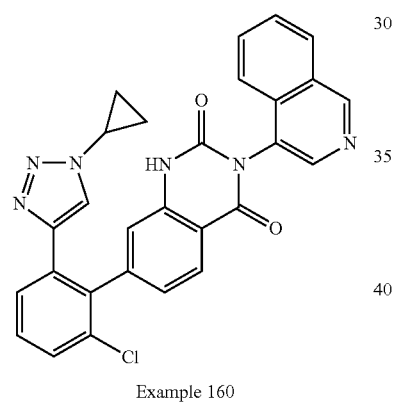

Example 160

7-(2-chloro-6-(1-cyclopropyl-1H-1,2,3-triazol-4-yl)phenyl)-3-(isoquinolin-4-yl)quinazoline-2,4(1H,3H)-dione (Example 160): A suspension of 7-(2-chloro-6-ethynyl-phenyl)-3-(4-isoquinolyl)-1H-quinazoline-2,4-dione (Example 159) (TFA salt) (50 mg, 0.092 mmol), azidocyclopropane (56 µL of a 2.5 M solution in DCM), $CuSO_4$ (15 mg, 0.092 mmol) and L-ascorbic acid sodium salt (18 mg, 0.092 mmol) in DMF (1 mL) was stirred at room temperature for 1 hour. The mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the product as a trifluoroacetate salt.

ES/MS: 507.2 [M+H$^+$].

$^1$H NMR (400 MHz, DMSO-d$_6$) δ 11.82 (s, 1H), 9.49 (s, 1H), 8.68-8.59 (m, 1H), 8.36-8.28 (m, 1H), 8.00 (dd, J=8.0, 3.5 Hz, 1H), 7.98-7.91 (m, 1H), 7.90-7.77 (m, 3H), 7.73-7.64 (m, 1H), 7.59 (td, J=7.9, 1.3 Hz, 1H), 7.38 (s, 1H), 7.12-7.02 (m, 2H), 2.39 (d, J=5.4 Hz, 1H), 1.14-1.02 (m, 4H).

Procedure 29: Example 161

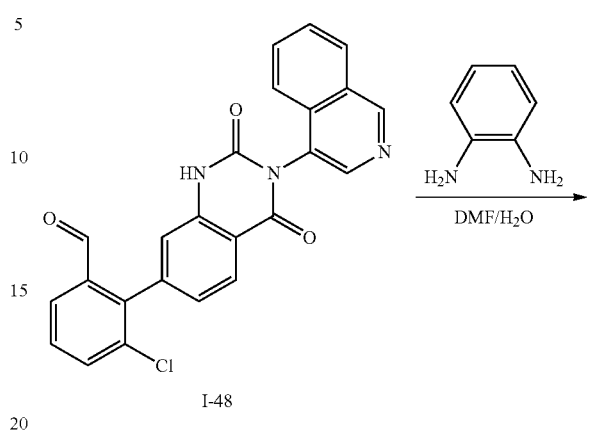

I-48

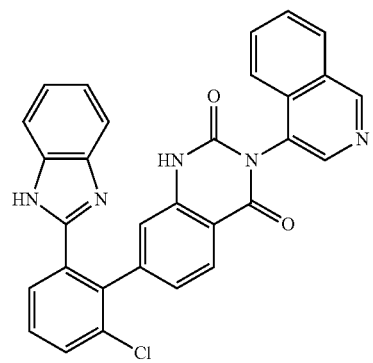

Example 161

7-[12-(1H-benzimidazol-2-yl)-6-chloro-phenyl]-3-(4-isoquinolyl)-1H-quinazoline-2,4-dione (Example 161): A mixture of 3-chloro-2-[3-(4-isoquinolyl)-2,4-dioxo-1H-quinazolin-7-yl]benzaldehyde (I-48) (50 mg, 0.12 mmol) and benzene-1,2-diamine (13 mg, 0.12 mmol) in DMF (0.9 mL)/H$_2$O (0.1 mL) was stirred at 80° C. overnight. The mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the title compound as a trifluoroacetate salt.

ES/MS: 516.1 [M].

$^1$H NMR (400 MHz, DMSO-d$_6$) δ 11.83 (d, J=5.2 Hz, 1H), 9.48 (d, J=2.2 Hz, 1H), 8.61 (d, J=13.7 Hz, 1H), 8.30 (dt, J=6.9, 2.1 Hz, 1H), 8.02-7.72 (m, 7H), 7.68 (ddd, J=6.1, 4.6, 3.1 Hz, 2H), 7.40 (ddd, J=6.2, 3.3, 1.3 Hz, 2H), 7.22 (dd, J=11.2, 1.6 Hz, 1H), 7.10 (ddd, J=9.6, 8.1, 1.6 Hz, 1H).

Procedure 30 Example 162

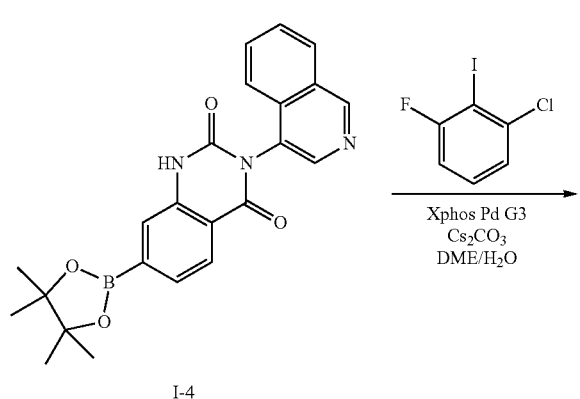

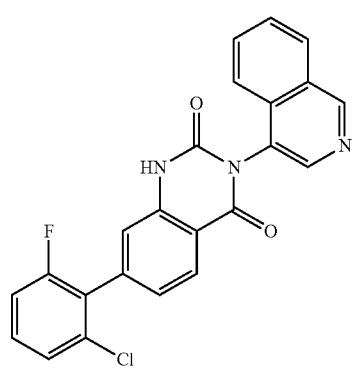

Example 162

7-(2-Chloro-6-fluoro-phenyl)-3-(4-isoquinolyl)-1H-quinazoline-2,4-dione (Example 162): To a microwave vial with 3-(4-isoquinolyl)-7-(4,4,5,5-tetramethyl-1,3,2-dioxaborolan-2-yl)-1H-quinazoline-2,4-dione (I-4) (113 mg, 0.27 mmol) were added 1-chloro-3-fluoro-2-iodo-benzene (105 mg, 0.41 mmol), XPhos Pd G3 (20 mg, 0.027 mmol) and cesium carbonate (266 mg, 0.82 mmol). DME (1.5 mL) and water (0.1 mL) were added, and the mixture was degassed with argon for 30 seconds. The vial was sealed, and the reaction mixture was heated at 120° C. for 15 minutes under microwave conditions. The crude mixture was filtered with the aid of Celite®, concentrated under reduced pressure, and to the crude residue was added DMF (1 mL), acetonitrile (0.5 mL), TFA (0.3 mL) and water (0.2 mL). The mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the title compound as a trifluoroacetate salt.

ES/MS: 418.1 [M+].

$^1$H NMR (400 MHz, DMSO-$d_6$) δ 11.89 (s, 1H), 9.51 (s, 1H), 8.65 (s, 1H), 8.38-8.28 (m, 1H), 8.12-8.06 (m, 1H), 8.06-7.98 (m, 1H), 7.88-7.76 (m, 2H), 7.63-7.53 (m, 2H), 7.52-7.38 (m, 1H), 7.32-7.25 (m, 2H).

Procedure 31: Example 163

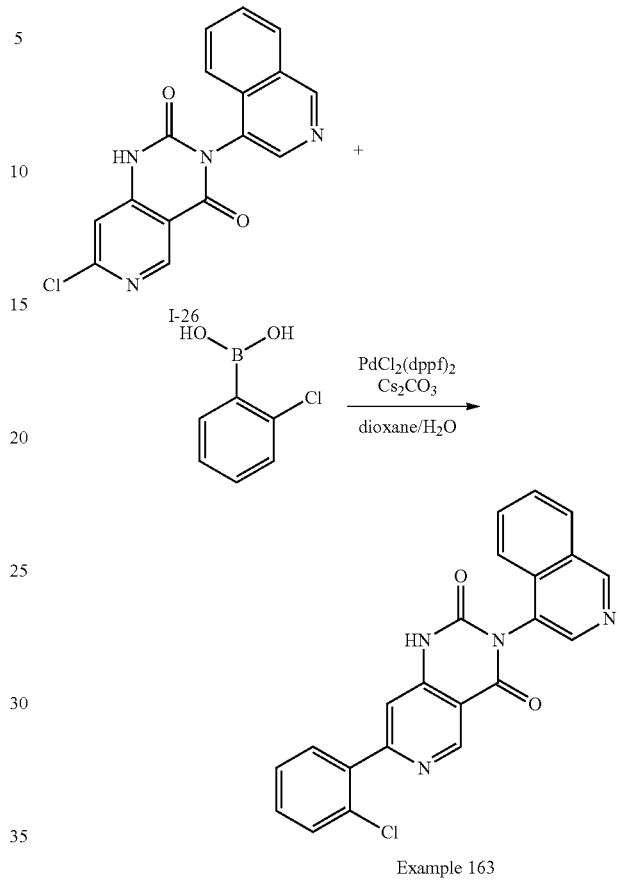

Example 163

7-(2-chlorophenyl)-3-(4-isoquinolyl)-1H-pyrido[4,3-d]pyrimidine-2,4-dione (Example 163): To a microwave vial with 7-chloro-3-(4-isoquinolyl)-1H-pyrido[4,3-d]pyrimidine-2,4-dione (I-26) (50 mg, 0.15 mmol) were added (2-chlorophenyl)boronic acid (48 mg, 0.306 mmol), PdCl$_2$(dppf)$_2$ (10 mg, 0.01 mmol) and cesium carbonate (151 mg, 0.46 mmol). Dioxane (1.5 mL) and water (0.1 mL) were added, and the mixture was degassed with argon for 30 seconds. The vial was sealed, and the reaction mixture was heated at 120° C. for 10 minutes under microwave conditions. The crude mixture was concentrated under reduced pressure, and to the crude residue were added DMF (2 mL), acetonitrile (1 mL), TFA (0.6 mL) and water (0.2 mL). The mixture was heated to produce a homogeneous mixture, and the mixture was filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the two title compound Example 163 as a trifluoroacetate salt.

ES/MS: 401.1 (M+).

1H NMR (400 MHz, DMSO-$d_6$) δ 12.24 (s, 1H), 9.53 (s, 1H), 9.13 (s, 1H), 8.65 (s, 1H), 8.43-8.25 (m, 1H), 8.12 (d, J=8.1 Hz, 1H), 7.84 (dddd, J=16.6, 8.1, 6.9, 1.4 Hz, 2H), 7.72-7.65 (m, 2H), 7.61-7.52 (m, 1H), 7.50 (d, J=0.7 Hz, 1H), 7.38-7.32 (m, 1H).

Examples 164-165

The following Examples were made in an analogous fashion according to Procedure 31 and are shown below in Table 16. Any different reagents/starting materials than those described in Procedure 31 are noted in the last column of Table 16—"Changes to Procedure 31: Different Reagents/Starting Materials".

TABLE 16
Examples 164-165
| Example | Structure | ES/MS m/z | ¹H-NMR | Changes to Procedure 31: Different Reagents/ Starting Materials |
|---|---|---|---|---|
| 164 | 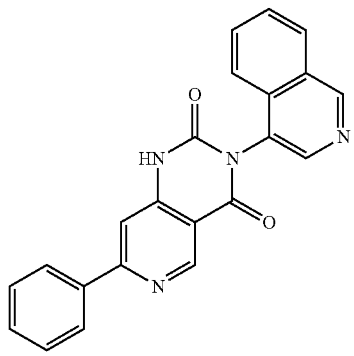 [SMILES: O=c1[nH]c2cc(-c3ccccc3)ncc2c(=O)n1-c1cncc2ccccc12] | 367.0 | 1H NMR (400 MHz, DMSO-d6) δ 11.93 (s, 1H), 9.51 (s, 1H), 9.03 (d, J = 2.3 Hz, 1H), 8.77 (dd, J = 5.0, 1.5 Hz, 1H), 8.63 (s, 1H), 8.48-8.21 (m, 2H), 8.10 (d, J = 8.2 Hz, 1H), 7.92 (d, J = 8.1 Hz, 1H), 7.87-7.77 (m, 2H), 7.72 (dd, J = 8.0, 5.0 Hz, 1H), 7.67 (dd, J = 8.2, 1.7 Hz, 1H), 7.58 (d, J = 1.6 Hz, 1H). | phenylboronic acid |
| 165 | 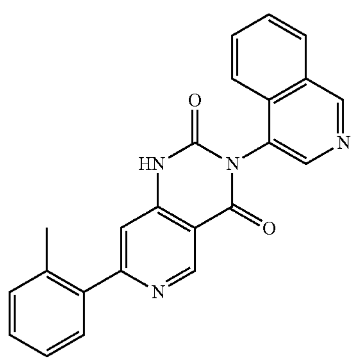 [SMILES: Cc1ccccc1-c1cc2[nH]c(=O)n(-c3cncc4ccccc34)c(=O)c2cn1] | 381.1 | 1H NMR (400 MHz, DMSO-d6) δ 12.17 (s, 1H), 9.48 (s, 1H), 9.11 (s, 1H), 8.61 (s, 1H), 8.31 (dd, J = 7.2, 1.7 Hz, 1H), 8.05 (dd, J = 8.2, 1.4 Hz, 1H), 7.29 (s, 1H), 7.27-7.19 (m, 2H), 7.11 (d, J = 7.3 Hz, 4H), 2.39 (d, J = 1.9 Hz, 3H). | o-tolylboronic acid |
Procedure 32: Example 166
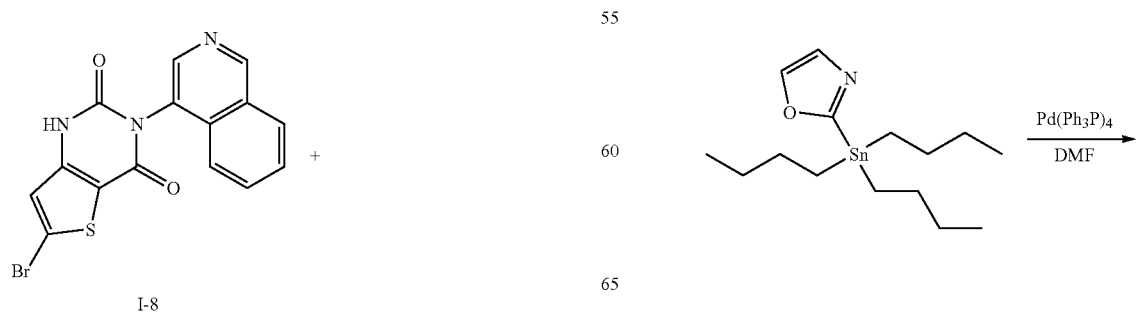
-continued

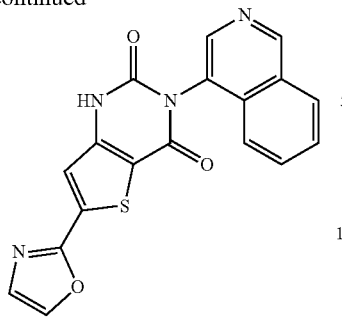

Example 166

3-(isoquinolin-4-yl)-6-(oxazol-2-yl)thieno[3,2-d]pyrimidine-2,4(1H,3H)-dione (Example 166): To a small microwave vial containing a stir bar was added 6-bromo-3-(4-isoquinolyl)-1H-thieno[3,2-d]pyrimidine-2,4-dione (I-8) (50 mg, 0.134 mmol, 1.0 equiv.) followed by DMF (1.5 mL). The contents were warmed with a heat gun until the starting bromide was fully dissolved. This was purged with Ar for 1 min. To this solution were added Pd(Ph₃P)₄ (23.2 mg, 0.02 mmol, 2 equiv.), tributyl(oxazol-2-yl)stannane (95.7 mg, 0.267 mmol), after which the reaction mixture was sealed, degassed under Ar (1 min), and heated to 95° C. overnight. The reaction was cooled to rt, purged with Ar and another batch of Pd(Ph₃P)₄ (23.2 mg, 0.02 mmol, 2 equiv.), and tributyl(oxazol-2-yl)stannane (95.7 mg, 0.267 mmol) were add followed by continued stirring for 6 h at 95 C. The crude product was diluted with MeOH/water/trifluoroacetic acid (3 mL: 5:0.5:0.1), filtered through an acrodisc, and purified directly by RP-HPLC (0.1% TFA-ACN in 0.1% TFA Water) to give the title compound Example 166 as a TFA salt.

ES/MS: 363.1 (M+H⁺).

$^1$H NMR (400 MHz, Methanol-d₄) δ 9.69 (s, 1H), 8.72 (s, 1H), 8.50 (s, 1H), 8.13 (s, 1H), 8.03 (d, J=36.4 Hz, 3H), 7.63 (s, 1H), 7.44 (s, 1H).

Procedure 33: Example 167

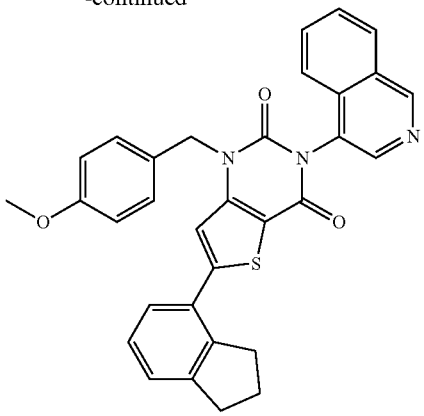

Example 167

6-(2,3-dihydro-1H-inden-4-yl)-3-(isoquinolin-4-yl)-1-(4-methoxybenzyl)thieno[3,2-d]pyrimidine-2,4(1H,3H)-dione (Example 167): To a microwave vial containing 6-bromo-3-(isoquinolin-4-yl)-1-(4-methoxybenzyl)thieno[3,2-d]pyrimidine-2,4(1H,3H)-dione (I-56) (40 mg, 0.08 mmol) in DMF (2 mL) were added 2-indan-4-yl-4,4,5,5-tetramethyl-1,3,2-dioxaborolane (0.40 mg, 0.162 mmol), [1,1' Bis(diphenylphosphino)ferrocene]dichloropalladium(II) (17.2 mg, 0.012 mmol) and sodium carbonate (2M aqueous, 0.08 mL, 0.162 mmol), The mixture was degassed with argon for 30 seconds. The vial was sealed, and the reaction mixture was stirred at 100° C. for 2 h. Reaction mixture cooled to rt, diluted with 5% MeOH/DCM, filtered over a pad of Celite, and concentrated. The crude product was purified by silica gel column chromatography (0-100% EA/Hex) to afford title compound Example 167.

ES/MS: 532.2 (M+H⁺).

$^1$H NMR (400 MHz, Methanol-d₄) δ 9.40 (d, J=0.8 Hz, 1H), 8.55 (s, 1H), 8.33-8.24 (m, 1H), 7.90-7.83 (m, 1H), 7.82-7.77 (m, 2H), 7.47-7.43 (m, 2H), 7.40 (d, J=11.9 Hz, 1H), 7.34 (dd, =7.5, 1.1 Hz, 1H), 7.26 (t, J=7.6 Hz, 1H), 7.00-6.94 (m, 2H), 5.38 (s, 2H), 3.80 (s, 3H), 3.04-2.99 (m, 4H), 2.16-2.07 (m, 2H).

Procedure 34: Example 168 and Example 169

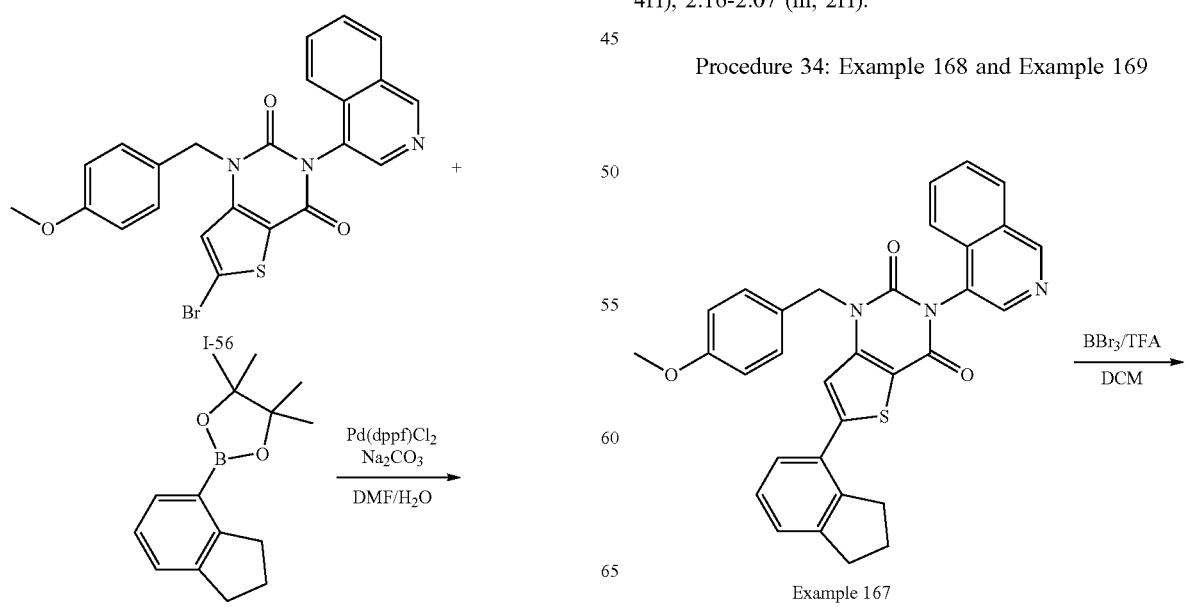

Example 167

7.79 (ddd, J=10.2, 5.8, 2.7 Hz, 1H), 7.62 (s, 1H), 7.53 (d, J=7.5 Hz, 1H), 7.38 (d, J=7.4 Hz, 1H), 7.36-7.28 (m, 3H), 6.79-6.74 (m, 2H), 5.31 (d, J=15.6 Hz, 1H), 5.22 (d, J=15.6 Hz, 1H), 3.09-3.04 (m, 2H), 2.99-2.95 (m, 2H), 2.12-2.04 (m, 2H).

Procedure 35: Example 170

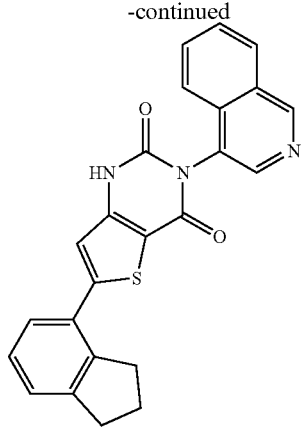

Example 168

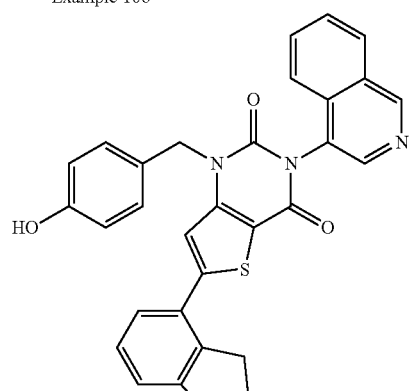

Example 169

6-(2,3-dihydro-1H-inden-4-yl)-3-(isoquinolin-4-yl)thieno[3,2-d]pyrimidine-2,4(1H,3H)-dione (Example 168): To a solution of 6-indan-4-yl-3-(4-isoquinolyl)-1-[(4-methoxyphenyl)methyl]thieno[3,2-d]pyrimidine-2,4-dione Example 167 (30 mg, 0.056 mmol) in DCM (1.5 mL) were added TFA (64 mg, 0.56 mmol), and BBr$_3$ (226 uL, 1M solution in DCM, 0.226 mmol). The mixture was stirred at rt 2 h. After 2 h another portion of BBr$_3$ (226 uL, 1M solution in DCM, 0.226 mmol) was added, followed by continued stirring for additional 2 h. The reaction was quenched with 5 drops of 2N NaHCO$_3$, and concentrated. The crude product was diluted with MeOH/water/TFA (3 mL; 5:0.5:0.1), filtered through an acrodisc, and purified directly by RP-HPLC (0.1% TFA-ACN in 0.1% TFA Water) to afford the title compounds Example 168 and Example 169 as TFA salts.

Example 168

ES/MS: 412.1 (M+H$^+$).

$^1$H NMR (400 MHz, DMSO-d$_6$) δ 12.24 (s, 1H), 9.46 (s, 1H), 8.58 (s, 1H), 8.30 (d, J=7.9 Hz, 1H), 7.87-7.76 (m, 3H), 7.52 (d, J=7.4 Hz, 1H), 7.36 (dd, J=24.8, 7.4 Hz, 2H), 7.23 (s, 1H), 3.16-3.12 (m, 2H), 3.00-2.96 (m, 2H), 2.15-2.08 (m, 2H).

Example 169

ES/MS: 518.2 (M+H$^+$).

$^1$H NMR (400 MHz, DMSO-d$_6$) δ 9.48 (s, 1H), 8.65 (s, 1H), 8.31 (d, J=8.2 Hz, 1H), 7.85 (dd, J=6.2, 1.4 Hz, 2H),

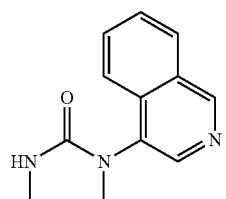

Example 166

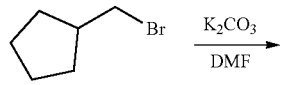

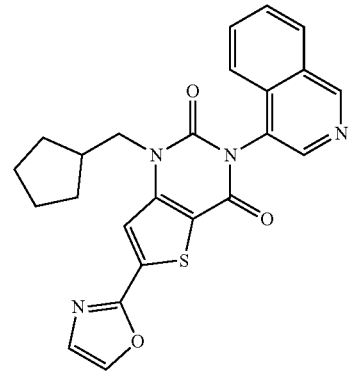

Example 170

1-(cyclopentylmethyl)-3-(isoquinolin-4-yl)-6-(oxazol-2-yl)thieno[3,2-d]pyrimidine-2,4(1H,3H)-dione (Example 170): To a solution of 3-(4-isoquinolyl)-6-oxazol-2-yl-1H-thieno[3,2-d]pyrimidine-2,4-dione (Example 166) (10 mg, 0.027 mmol) in DMF (1 mL) was added K$_2$CO$_3$ (7.6 mg, 0.055 mmol) followed by bromomethylcyclopentane (18 mg, 0.11 mmol). The mixture was stirred at 70° C. for 3 h. The reaction mixture was diluted with MeOH/water/trifluoroacetic acid (3 mL; 1:1:0.1), filtered through an acrodisc, and purified directly by RP-HPLC (0.1% TFA-ACN in 0.1% TFA Water) to afford the title compound Example 170 as a TFA salt.

ES/MS: 445.2 (M+H$^+$).

$^1$H NMR (400 MHz, DMSO-d$_6$) δ 9.47 (s, 1H), 8.59 (s, 1H), 8.43 (s, 1H), 8.30 (d, J=8.0 Hz, 1H), 8.11 (s, 1H), 7.83 (d, J=5.2 Hz, 2H), 7.81-7.76 (m, 1H), 7.55 (s, 1H), 4.14 (d, J=7.6 Hz, 2H), 2.43-2.31 (m, 1H), 1.81-1.72 (m, 3H), 1.68-1.61 (m, 2H), 1.59-1.46 (m, 2H), 1.39-1.28 (m, 2H).

Procedure 36: Example 171

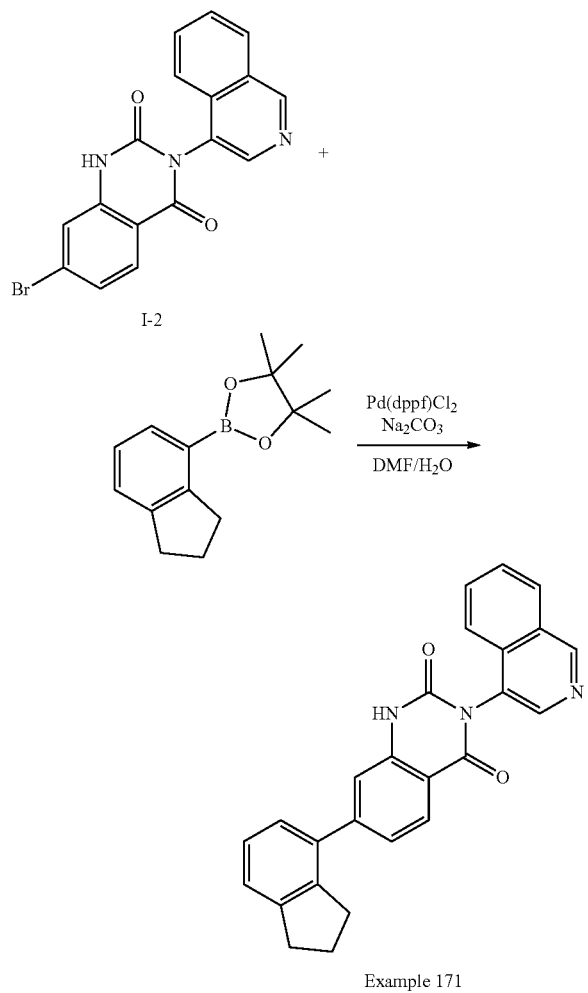

Example 171

7-(2,3-dihydro-1H-inden-4-yl)-3-(isoquinolin-4-yl)quinazoline-2,4(1H,3H)-dione (Example 171): To a microwave vial with 7-(2,6-dichlorophenyl)-3-(isoquinolin-4-yl)quinazoline-2,4(1H,3H)-dione (I-2) (50 mg, 0.136 mmol) in DMF (2 ML) were added 2-indan-4-yl-4,4,5,5-tetramethyl-1,3,2-dioxaborolane (0.066 mg, 0.272 mmol), [1,1'-Bis(diphenylphosphino)ferrocene]dichloropalladium(II) (15.1 mg, 0.02 mmol) and sodium carbonate (2M aqueous, 0.136 mL, 0.262 mmol). The mixture was degassed with argon for 30 seconds. The vial was sealed, and the reaction mixture was stirred at 100° C. for 2 h. The reaction mixture was cooled to rt, diluted with 5% MeOH/DCM, filtered over a pad of Celite, and concentrated under reduced pressure. To the crude residue were added DMF (1.5 mL), MeOH (1.5 mL), TFA (0.05 mL) and water (0.1 mL). The mixture was heated to produce a homogeneous mixture, and the resulting mixture was filtered through an acrodisc, and was subsequently purified by RP-HPLC (0.1% TFA-ACN in 0.1% TFA Water, Column: Gemini 10 uM, NX-C18 110 Angstrom, 250×30 mm) to afford title compound Example 171 as a trifluoroacetate salt.

ES/MS: 406.2 (M+H$^+$).

$^1$H NMR (400 MHz, DMSO-d$_6$) δ 11.81 (s, 1H), 9.51 (s, 1H), 8.63 (s, 1H), 8.33 (dd, J=7.5, 1.7 Hz, 1H), 8.03 (d, J=8.6 Hz, 1H), 7.93 (d, J=8.1 Hz, 1H), 7.88-7.76 (m, 2H), 7.42-7.38 (m, 2H), 7.37-7.33 (m, 1H), 7.31 (d, J=7.3 Hz, 1H), 7.26 (dd, J=7.2, 1.6 Hz, 1H), 3.00-2.96 (m, 4H), 2.09-2.01 (m, 2H).

Examples 172-176

The following Examples were made in an analogous fashion according to the procedure indicated in the column of Table 17 titled "Procedure." Any different reagents/starting materials than those described in the indicated procedure are noted in the last column of Table 17—"Changes to Procedure: Different Reagents/Starting Materials".

TABLE 17

Examples 172-176

| Example | Structure | ES/MS m/z | $^1$H-NMR | Procedure | Changes to Procedure: Different Reagents/Starting Materials |
|---|---|---|---|---|---|
| 172 | 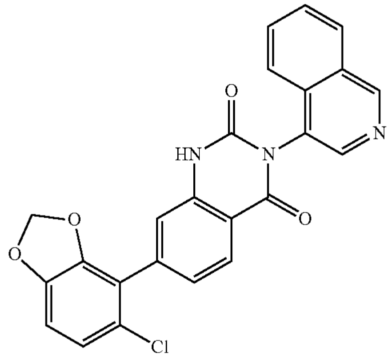 [SMILES: O=c1[nH]c2cc(-c3c(Cl)ccc4c3OCO4)ccc2c(=O)n1-c1cncc2ccccc12] | 444.0 | 1H NMR (400 MHz, DMSO-d6) δ 11.86 (s, 1H), 9.55-9.42 (m, 1H), 8.62 (s, 1H), 8.35-8.26 (m, 1H), 8.06 (d, J = 8.1 Hz, 1H), 8.01-7.93 (m, 1H), 7.90-7.71 (m, 2H), 7.44-7.21 (m, 2H), 7.21-6.95 (m, 2H), 6.13 (s, 2H). | 3 | (5-chloro-1,3-benzodioxol-4-yl)boronic acid |

TABLE 17-continued

Examples 172-176

| Example | Structure | ES/MS m/z | ¹H-NMR | Procedure | Changes to Procedure: Different Reagents/ Starting Materials |
|---|---|---|---|---|---|
| 173 | 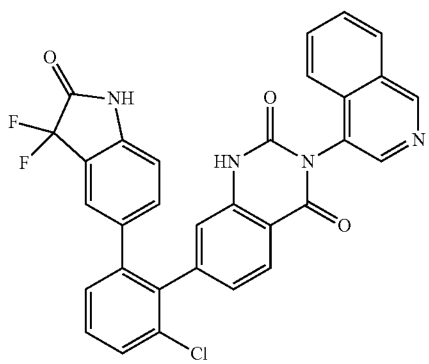 [SMILES: O=C1Nc2ccc(-c3cccc(Cl)c3-c3ccc4c(=O)n(-c5cncc6ccccc56)c(=O)[nH]c4c3)cc2C1(F)F] | 567.1 | 1H NMR (400 MHz, DMSO-d6) δ 11.74 (s, 1H), 11.30-11.14 (m, 1H), 9.48 (s, 1H), 8.59 (d, J = 17.4 Hz, 1H), 8.42-8.18 (m, 1H), 7.89 (dd, J = 8.1, 3.1 Hz, 2H), 7.83-7.76 (m, 2H), 7.69 (dd, J = 8.0, 1.3 Hz, 2H), 7.63-7.41 (m, 3H), 7.20-6.99 (m, 3H). | 21 | 3,3-difluoro-5-(4,4,5,5-tetramethyl-1,3,2-dioxaborolan-2-yl)indolin-2-one |
| 174 | 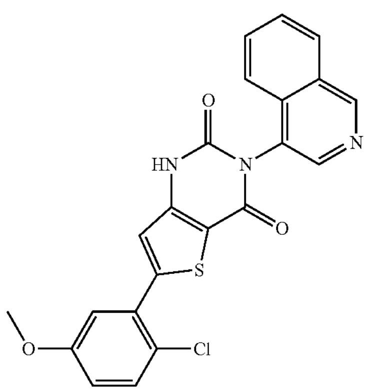 [SMILES: COc1ccc(Cl)c(-c2cc3[nH]c(=O)n(-c4cncc5ccccc45)c(=O)c3s2)c1] | 436.0 | 1H NMR (400 MHz, DMSO-d6) δ 12.29 (s, 1H), 9.48 (s, 1H), 8.60 (s, 1H), 8.30 (dd, J = 7.5, 1.4 Hz, 1H), 7.95-7.69 (m, 3H), 7.59 (d, J = 8.9 Hz, 1H), 7.33 (s, 1H), 7.24 (s, 1H), 7.13 (dd, J = 8.9, 3.0 Hz, 1H), 3.85 (s, 3H). | 1 | (2-chloro-5-methoxy-phenyl) boronic acid |
| 175 | 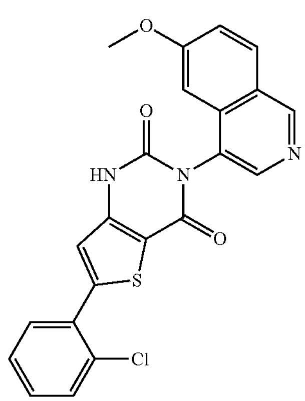 [SMILES: COc1ccc2cncc(-n3c(=O)[nH]c4cc(-c5ccccc5Cl)sc4c3=O)c2c1] | 436.0 | 1H NMR (400 MHz, DMSO-d6) δ 12.24 (s, 1H), 9.40 (s, 1H), 8.57 (s, 1H), 8.29 (d, J = 9.1 Hz, 1H), 7.81-7.64 (m, 2H), 7.62-7.42 (m, 3H), 7.34 (s, 1H), 7.26 (d, J = 2.4 Hz, 1H), 3.91 (s, 3H). | 9 | 6-methoxyiso-quinolin-4-amine |

TABLE 17-continued

Examples 172-176

| Example | Structure | ES/MS m/z | ¹H-NMR | Procedure | Changes to Procedure: Different Reagents/ Starting Materials |
|---|---|---|---|---|---|
| 176 | 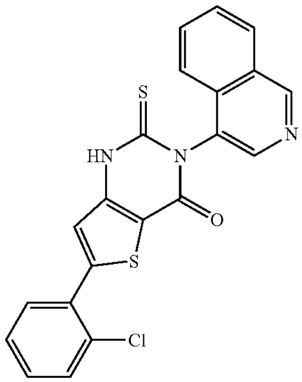 [SMILES: O=c1c2sc(-c3ccccc3Cl)cc2[nH]c(=S)n1-c1cncc2ccccc12] | 422.0 | 1H NMR (400 MHz, DMSO-d6) δ 13.81 (s, 1H), 9.45 (s, 1H), 8.57 (s, 1H), 8.29 (d, J = 7.8 Hz, 1H), 7.89 (d, J = 8.2 Hz, 1H), 7.87-7.67 (m, 4H), 7.56 (dt, J = 6.0, 2.5 Hz, 2H), 7.42 (s, 1H). | 9 | I-57; isoquinolin-4-amine |

Examples 177-384

The following Examples were made in an analogous fashion according to the procedure indicated in the column of Table 18 titled "Procedure." Any different reagents/ starting materials than those described in the indicated procedure are noted in the last column of Table 18—"Changes to Procedure: Different Reagents/Starting Materials".

TABLE 18

Examples 177-384

| Example | Structure | ES/MS m/z | 1H-NMR | Procedure | Changes to Procedure: Different Reagents/ Starting Materials |
|---|---|---|---|---|---|
| 177 | 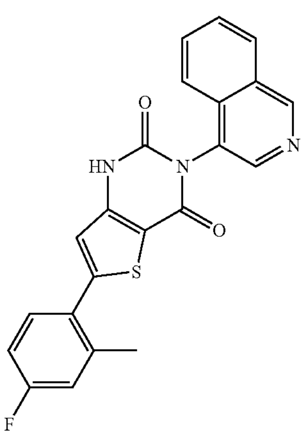 | 404.1 | 1H NMR (400 MHz, DMSO-d6) δ 9.49 (s,1H), 8.60 (s, 1H), 8.34-8.28 (m, 1H), 7.93-7.76 (m, 3H), 7.56 (dd, J = 8.6, 5.9 Hz, 1H), 7.31 (dd, J = 10.0, 2.8 Hz, 1H), 7.20 (td, J = 8.5, 2.8 Hz, 1H), 7.09 (s, 1H), 2.47 (s, 3H). | 1 | (4-fluoro-2-methyl-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 178 | 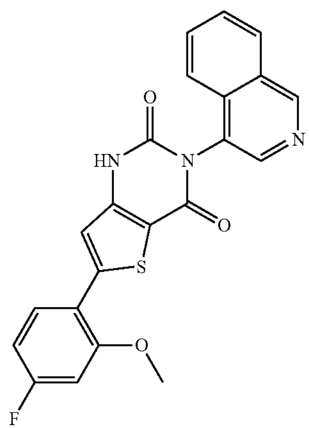 [SMILES: COc1cc(F)ccc1-c1cc2[nH]c(=O)n(-c3cncc4ccccc34)c(=O)c2s1] | 420.1 | 1H NMR (400 MHz, DMSO-d6) δ 12.21 (s, 1H), 9.47 (s, 1H), 8.58 (s, 1H), 8.30 (d, J = 7.9 Hz, 1H), 7.93 (dd, J = 8.8, 6.6 Hz, 1H), 7.86-7.73 (m, 4H), 7.42 (s, 1H), 7.19 (dd, J = 11.2, 2.6 Hz, 1H), 6.97 (td, J = 8.4, 2.5 Hz, 1H), 4.00 (s, 3H) | 1 | (4-fluoro-2-methoxy-phenyl) boronic acid |
| 179 | 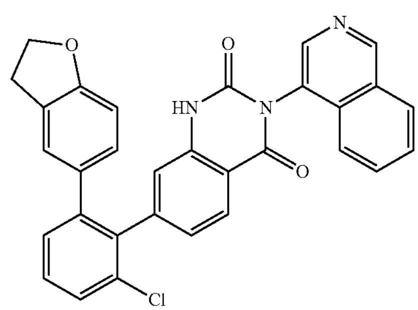 [SMILES: O=c1[nH]c2cc(-c3c(Cl)cccc3-c3ccc4c(c3)CCO4)ccc2c(=O)n1-c1cncc2ccccc12] | 518.1 | 1H NMR (400 MHz, DMSO-d6) δ 12.21 (s, 1H), 9.47 (s, 1H), 8.58 (s, 1H), 8.30 (d, J = 7.9 Hz, 1H), 7.93 (dd, J = 8.8, 6.6 Hz, 1H), 7.86-7.73 (m, 4H), 7.42 (s, 1H), 7.19 (dd, J = 11.2, 2.6 Hz, 1H), 6.97 (td, J = 8.4, 2.5 Hz, 1H), 4.00 (s, 3H) | 21 | 2,3-dihydrobenzo-furan-5-ylboronic acid |
| 180 | 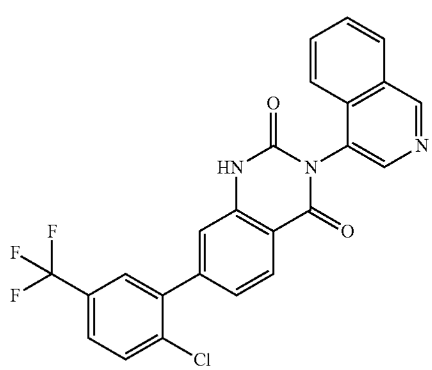 [SMILES: O=c1[nH]c2cc(-c3cc(C(F)(F)F)ccc3Cl)ccc2c(=O)n1-c1cncc2ccccc12] | 468.1 | 1H NMR (400 MHz, DMSO-d6) δ 11.89 (s, 1H), 9.50 (s, 1H), 8.63 (s, 1H), 8.32 (dd, J = 8.4, 1.3 Hz, 1H), 8.08 (d, J = 8.6 Hz, 1H), 8.03-7.70 (m, 6H), 7.43-7.18 (m, 2H) | 5 | 2-bromo-1-chloro-4-(trifluoromethyl)benzene |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 181 | 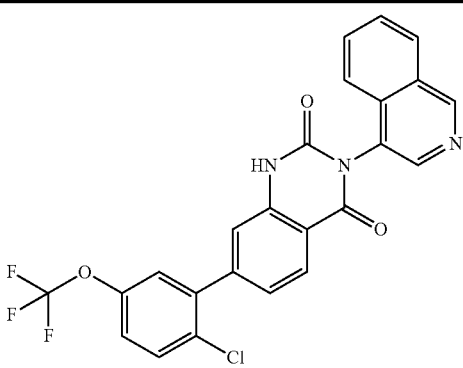 | 484.0 | 1H NMR (400 MHz, DMSO-d6) δ 11.89 (s, 1H), 9.50 (s, 1H), 8.63 (s, 1H), 8.32 (dd, J = 8.4, 1.3 Hz, 1H), 8.07 (d, J = 8.7 Hz, 1H), 7.95 (dd, J = 8.2, 1.4 Hz, 1H), 7.82 (dtt, J = 13.4, 6.9, 3.5 Hz, 3H), 7.68-7.46 (m, 2H), 7.41-7.30 (m, 2H) | 4 | [2-chloro-5-(trifluoro-methoxy)phenyl] boronic acid |
| 182 | 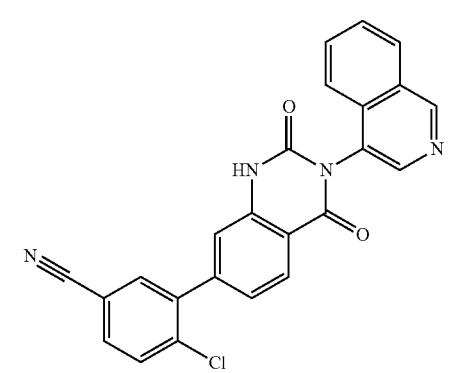 [SMILES: N#Cc1ccc(Cl)c(-c2ccc3c(=O)n(-c4cncc5ccccc45)c(=O)[nH]c3c2)c1] | 425.0 | 1H NMR (400 MHz, DMSO-d6) δ 11.92 (s, 1H), 9.50 (s, 1H), 8.63 (s, 1H), 8.36-8.27 (m, 1H), 8.10-8.03 (m, 2H), 7.98 (ddd, J = 12.9, 8.2, 1.7 Hz, 2H), 7.90 (d, J = 8.3 Hz, 1H), 7.82 (dddd, J = 14.9, 8.2, 6.9, 1.4 Hz, 2H), 7.36 (dq, J = 3.6, 1.6 Hz, 2H) | 5 | 3-bromo-4-chloro-benzonitrile |
| 183 | 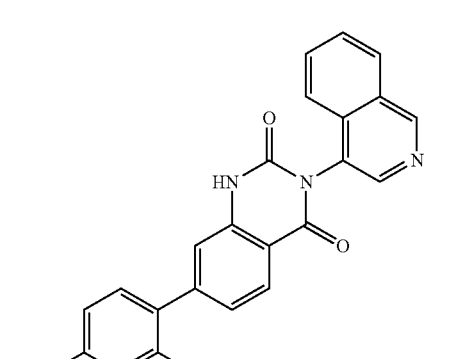 | 418.1 | 1H NMR (400 MHz, DMSO-d6) δ 11.87 (s, 1H), 9.49 (s, 1H), 8.62 (s, 1H), 8.31 (dd, J = 8.2, 1.4 Hz, 1H), 8.05 (d, J = 8.6 Hz, 1H), 7.95 (dd, J = 8.0, 1.5 Hz, 1H), 7.81 (pd, J = 6.9, 1.4 Hz, 2H), 7.67 (dd, J = 8.9, 2.6 Hz, 1H), 7.56 (dd, J = 8.6, 6.2 Hz, 1H), 7.41 (td, J = 8.4, 2.6 Hz, 1H), 7.35-7.28 (m, 2H) | 4 | (2-chloro-4-fluoro-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 184 | 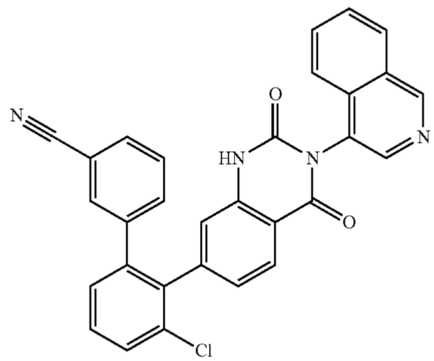 [SMILES: N#Cc1cccc(-c2cccc(Cl)c2-c2ccc3c(=O)n(-c4cncc5ccccc45)c(=O)[nH]c3c2)c1] | 501.0 | 1H NMR (400 MHz, DMSO-d6) δ 11.73 (d, J = 6.3 Hz, 1H), 9.49 (s, 1H), 8.62 (s, 1H), 8.31 (ddd, J = 8.5, 4.0, 2.0 Hz, 1H), 8.02-7.69 (m, 7H), 7.60 (td, J = 7.9, 1.2 Hz, 1H), 7.55-7.38 (m, 3H), 7.16-7.04 (m, 1H), 7.01 (d, J = 1.5 Hz, 1H) | 22 | (3-cyanophenyl) boronic acid |
| 185 | 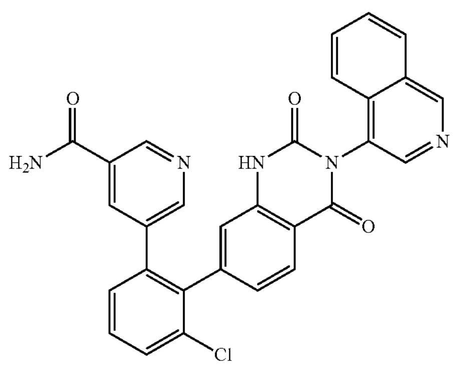 [SMILES: NC(=O)c1cncc(-c2cccc(Cl)c2-c2ccc3c(=O)n(-c4cncc5ccccc45)c(=O)[nH]c3c2)c1] | 520.1 | 1H NMR (400 MHz, DMSO-d6) δ 11.76 (d, J = 2.9 Hz, 1H), 9.52 (d, J = 1.9 Hz, 1H), 8.90 (dd, J = 5.1, 2.1 Hz, 1H), 8.65 (d, J = 12.4 Hz, 1H), 8.49-8.28 (m, 2H), 8.22-8.06 (m, 2H), 8.01-7.74 (m, 5H), 7.70-7.62 (m, 2H), 7.57 (ddd, J = 7.7, 5.0, 1.3 Hz, 1H), 7.21-6.95 (m, 2H) | 22 | 5-(4,4,5,5-tetramethyl-1,3,2-dioxaborolan-2-yl)pyridine-3-carboxamide |
| 186 | 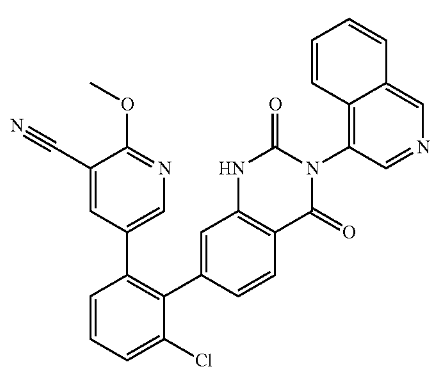 [SMILES: COc1ncc(-c2cccc(Cl)c2-c2ccc3c(=O)n(-c4cncc5ccccc45)c(=O)[nH]c3c2)cc1C#N] | 532.1 | 1H NMR (400 MHz, DMSO-d6) δ 11.77 (s, 1H), 9.49 (s, 1H), 8.62 (s, 1H), 8.38-8.06 (m, 3H), 7.97-7.70 (m, 5H), 7.62 (t, J = 7.8 Hz, 1H), 7.52 (dd, J = 7.7, 5.2 Hz, 1H), 7.19-6.98 (m, 2H), 3.98 (d, J = 5.7 Hz, 3H) | 22 | 2-methoxy-5-(4,4,5,5-tetramethyl-1,3,2-dioxaborolan-2-yl)pyridine-3-carbonitrile |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 187 | 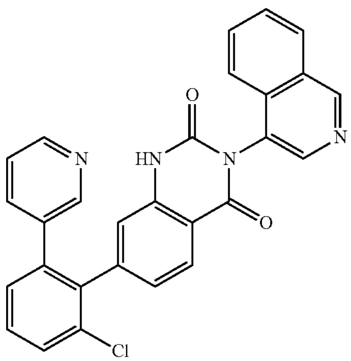 [SMILES: O=c1[nH]c2cc(-c3c(Cl)cccc3-c3cccnc3)ccc2c(=O)n1-c1cncc2ccccc12] | 477.1 | 1H NMR (400 MHz, DMSO-d6) δ 11.77 (d, J = 4.8 Hz, 1H), 9.49 (s, 1H), 8.62 (s, 1H), 8.59-8.44 (m, 2H), 8.35-8.27 (m, 1H), 7.96-7.73 (m, 6H), 7.64 (t, J = 7.8 Hz, 1H), 7.59-7.40 (m, 2H), 7.14-6.98 (m, 2H) | 22 | 3-(4,4,5,5-tetramethyl-1,3,2-dioxaborolan-2-yl)pyridine |
| 188 | 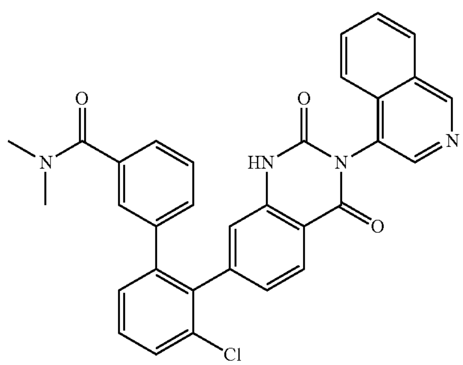 [SMILES: CN(C)C(=O)c1cccc(-c2cccc(Cl)c2-c2ccc3c(=O)n(-c4cncc5ccccc45)c(=O)[nH]c3c2)c1] | 548.0 | 1H NMR (400 MHz, DMSO-d6) δ 11.77 (d, J = 3.3 Hz, 1H), 9.47 (s, 1H), 8.62 (s, 1H), 8.39-8.08 (m, 3H), 7.96-7.69 (m, 6H), 7.65-7.44 (m, 3H), 7.20-6.95 (m, 2H), 4.09-3.93 (m, 6H) | 22 | [3-(dimethylcarbamoyl)phenyl] boronic acid |
| 189 | 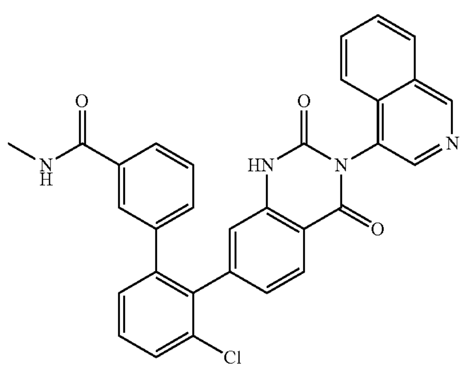 [SMILES: CNC(=O)c1cccc(-c2cccc(Cl)c2-c2ccc3c(=O)n(-c4cncc5ccccc45)c(=O)[nH]c3c2)c1] | 533.1 | 1H NMR (400 MHz, DMSO-d6) δ 11.72 (d, J = 5.1 Hz, 1H), 9.50 (s, 1H), 8.63 (s, 1H), 8.45 (dd, J = 4.6, 2.7 Hz, 1H), 8.31 (ddt, J = 6.5, 3.5, 1.8 Hz, 1H), 7.97-7.68 (m, 7H), 7.60 (td, J = 7.9, 1.1 Hz, 1H), 7.50 (ddd, J = 8.9, 7.6, 1.3 Hz, 1H), 7.31 (dt, J = 11.9, 7.7 Hz, 1H), 7.20 (ddt, J = 15.5, 7.7, 1.4 Hz, 1H), 7.13-6.95 (m, 2H), 2.78 (dd, J = 4.5, 2.0 Hz, 3H) | 22 | [3-(methylcarbamoyl)phenyl] boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 190 | 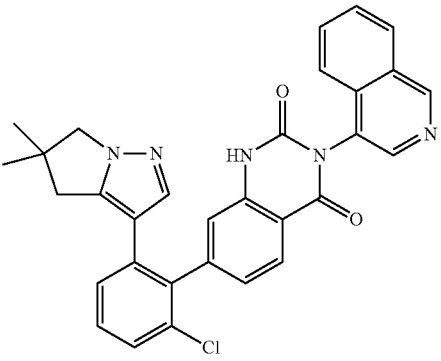 [SMILES: CC1(C)Cc2c(-c3cccc(Cl)c3-c3ccc4c(=O)n(-c5cncc6ccccc56)c(=O)[nH]c4c3)cnn2C1] | 534.1 | 1H NMR (400 MHz, DMSO-d6) δ 11.81 (s, 1H), 9.51 (s, 1H), 8.63 (d, J = 18.7 Hz, 1H), 8.33 (dd, J = 8.5, 4.9 Hz, 1H), 8.05-7.93 (m, 1H), 7.93-7.67 (m, 3H), 7.57-7.40 (m, 3H), 7.18-6.96 (m, 2H), 6.82 (s, 1H), 3.79 (d, J = 3.5 Hz, 2H), 2.46-2.27 (m, 2H), 1.13 (d, J = 9.4 Hz, 6H) | 22 | 5,5-dimethyl-3-(4,4,5,5-tetramethyl-1,3,2-dioxaborolan-2-yl)-4,6-dihydropyrrolo[1,2-b]pyrazole |
| 191 | 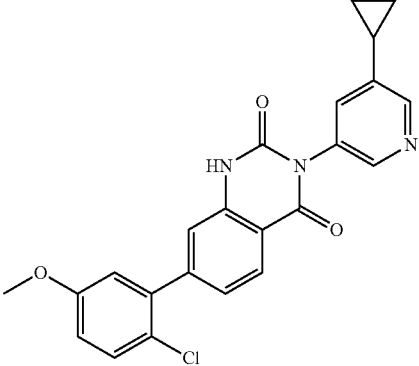 [SMILES: COc1ccc(Cl)c(-c2ccc3c(=O)n(-c4cncc(C5CC5)c4)c(=O)[nH]c3c2)c1] | 420.1 | 1H NMR (400 MHz, DMSO-d6) δ 11.76 (s, 1H), 8.50 (d, J = 2.1 Hz, 1H), 8.42 (d, J = 2.1 Hz, 1H), 8.03 (d, J = 8.0 Hz, 1H), 7.64 (t, J = 2.2 Hz, 1H), 7.54 (d, J = 8.8 Hz, 1H), 7.33-7.24 (m, 2H), 7.08 (dd, J = 8.9, 3.0 Hz, 1H), 7.01 (d, J = 3.0 Hz, 1H), 3.82 (s, 3H), 2.07 (tt, J = 8.4, 5.1 Hz, 1H), 1.18-0.99 (m, 2H), 0.86-0.72 (m, 2H) | 19 | I-132 |
| 192 | 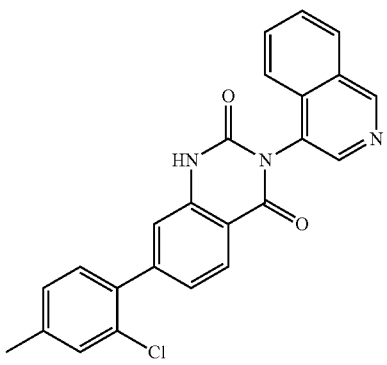 [SMILES: Cc1ccc(-c2ccc3c(=O)n(-c4cncc5ccccc45)c(=O)[nH]c3c2)c(Cl)c1] | 414.0 | 1H NMR (400 MHz, DMSO-d6) δ 11.85 (s, 1H), 9.51 (s, 1H), 8.63 (s, 1H), 8.33 (dd, J = 8.3, 1.3 Hz, 1H), 8.04 (d, J = 8.1 Hz, 1H), 8.00-7.91 (m, 1H), 7.82 (dddd, J = 14.7, 8.2, 6.9, 1.4 Hz, 2H), 7.49 (s, 1H), 7.46- | 4 | (2-chloro-4-methyl-phenyl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | 7.19 (m, 4H), 2.39 (s, 3H) | | |
| 193 | 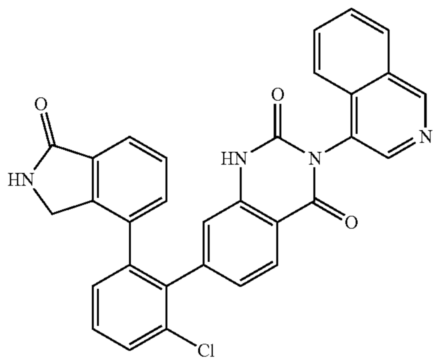 [SMILES: O=C1NCc2c1cccc2-c1cccc(Cl)c1-c1ccc2c(=O)n(-c3cncc4ccccc34)c(=O)[nH]c2c1] | 530.8 | 1H NMR (400 MHz, DMSO-d6) δ 11.66 (s, 1H), 9.57-9.28 (m, 1H), 8.83-8.53 (m, 2H), 8.43-8.24 (m, 1H), 7.92-7.67 (m, 5H), 7.69-7.48 (m, 3H), 7.35 (td, J = 7.5, 5.4 Hz, 1H), 7.24-7.10 (m, 2H), 6.84-6.63 (m, 1H), 4.54-4.02 (m, 2H) | 22 | 4-(4,4,5,5-tetramethyl-1,3,2-dioxaborolan-2-yl)isoindolin-1-one |
| 194 | 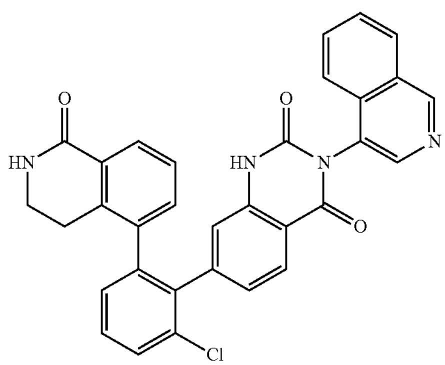 [SMILES: O=C1NCCc2c1cccc2-c1cccc(Cl)c1-c1ccc2c(=O)n(-c3cncc4ccccc34)c(=O)[nH]c2c1] | 544.8 | 1H NMR (400 MHz, DMSO-d6) δ 11.81-11.56 (m, 1H), 9.48 (d, J = 2.5 Hz, 1H), 8.71-8.50 (m, 1H), 8.35-8.23 (m, 1H), 7.95-7.68 (m, 4H), 7.61-7.50 (m, 1H), 7.41-7.05 (m, 4H), 6.89 (d, J = 1.6 Hz, 0H), 3.45-3.03 (m, 2H), 2.90-2.53 (m, 1H) | 22 | 5-(4,4,5,5-tetramethyl-1,3,2-dioxaborolan-2-yl)-3,4-dihydro-2H-isoquinolin-1-one |
| 195 | 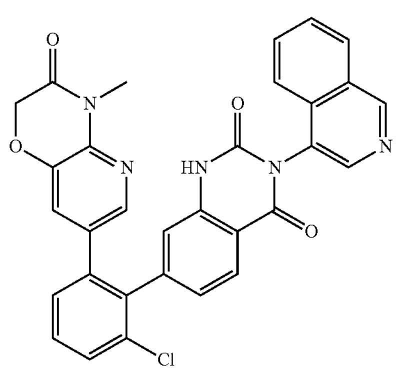 [SMILES: CN1C(=O)COc2cc(-c3cccc(Cl)c3-c3ccc4c(=O)n(-c5cncc6ccccc56)c(=O)[nH]c4c3)cnc21] | 561.9 | 1H NMR (400 MHz, DMSO-d6) δ 11.78 (d, J = 3.2 Hz, 1H), 9.49 (d, J = 2.6 Hz, 1H), 8.62 (t, J = 3.9 Hz, 1H), 8.37-8.23 (m, 1H), 7.98-7.68 (m, 6H), 7.63-7.42 (m, 2H), 7.31-7.03 (m, 3H), 4.75 (t, J = 3.8 Hz, 2H), 3.40-3.19 (m, 3H) | 22 | 4-methyl-7-(4,4,5,5-tetramethyl-1,3,2-dioxaborolan-2-yl)pyrido[3,2-b][1,4]oxazin-3-one |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 196 | 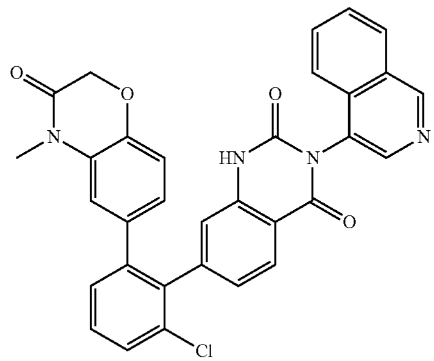 [SMILES: CN1C(=O)COc2ccc(-c3cccc(Cl)c3-c3ccc4c(=O)n(-c5cncc6ccccc56)c(=O)[nH]c4c3)cc21] | 560.8 | 1H NMR (400 MHz, DMSO-d6) δ 11.75 (d, J = 7.8 Hz, 1H), 9.50 (s, 1H), 8.63 (d, J = 3.3 Hz, 1H), 8.42-8.20 (m, 1H), 7.97-7.75 (m, 4H), 7.67 (d, J = 7.9 Hz, 1H), 7.64-7.44 (m, 2H), 7.17-7.01 (m, 2H), 6.99-6.86 (m, 2H), 6.80 (ddd, J = 10.4, 8.2, 2.0 Hz, 1H), 4.64 (s, 2H), 3.14 (s, 3H) | 22 | 4-methyl-6-(4,4,5,5-tetramethyl-1,3,2-dioxaborolan-2-yl)-1,4-benzoxazin-3-one |
| 197 | 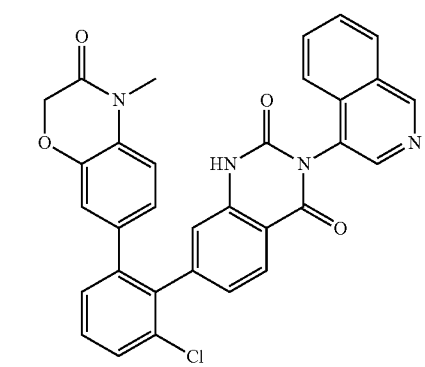 [SMILES: CN1C(=O)COc2cc(-c3cccc(Cl)c3-c3ccc4c(=O)n(-c5cncc6ccccc56)c(=O)[nH]c4c3)ccc21] | 560.8 | 1H NMR (400 MHz, DMSO-d6) δ 11.75 (d, J = 3.3 Hz, 1H), 9.49 (s, 1H), 8.62 (d, J = 8.8 Hz, 1H), 8.39-8.21 (m, 1H), 7.98-7.74 (m, 4H), 7.66 (dt, J = 8.1, 1.7 Hz, 1H), 7.55 (t, J = 7.9 Hz, 1H), 7.42 (dt, J = 7.9, 1.7 Hz, 1H), 7.17-6.99 (m, 3H), 6.92-6.78 (m, 2H), 4.63 (d, J = 5.6 Hz, 2H), 3.24 (d, J = 4.9 Hz, 3H) | 22 | 4-methyl-7-(4,4,5,5-tetramethyl-1,3,2-dioxaborolan-2-yl)-1,4-benzoxazin-3-one |
| 198 | 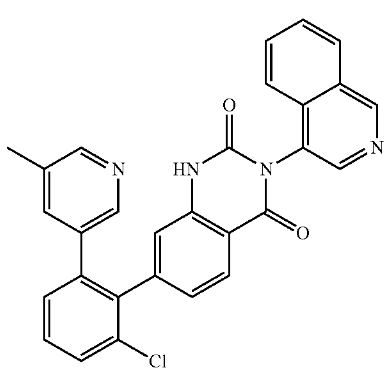 [SMILES: Cc1cncc(-c2cccc(Cl)c2-c2ccc3c(=O)n(-c4cncc5ccccc45)c(=O)[nH]c3c2)c1] | 490.7 | 1H NMR (400 MHz, DMSO-d6) δ 11.76 (d, J = 3.9 Hz, 1H), 9.48 (s, 1H), 8.61 (d, J = 5.3 Hz, 1H), 8.45 (dd, J = 9.9, 1.9 Hz, 1H), 8.36-8.20 (m, 2H), 8.00-7.73 (m, 6H), 7.64 (td, J = 7.9, 0.9 Hz, 1H), 7.54 (ddd, J = 7.7, 4.2, 1.2 Hz, 1H), | 22 | (5-methyl-3-pyridyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | 7.17-6.98 (m, 2H), 2.33 (d, J = 6.6 Hz, 3H) | | |
| 199 | 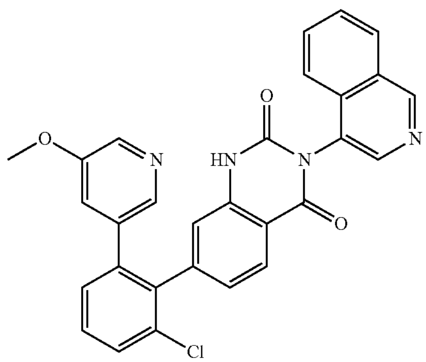 [SMILES: COc1cncc(-c2cccc(Cl)c2-c2ccc3c(=O)n(-c4cncc5ccccc45)c(=O)[nH]c3c2)c1] | 506.8 | 1H NMR (400 MHz, DMSO-d6) δ 11.76 (d, J = 5.3 Hz, 1H), 9.48 (s, 1H), 8.63 (d, J = 9.7 Hz, 1H), 8.36-8.14 (m, 2H), 8.06-7.68 (m, 6H), 7.66-7.48 (m, 2H), 7.39-7.28 (m, 1H), 7.22-6.98 (m, 2H), 3.77 (d, J = 5.2 Hz, 3H) | 22 | (5-methoxy-3-pyridyl) boronic acid |
| 200 | 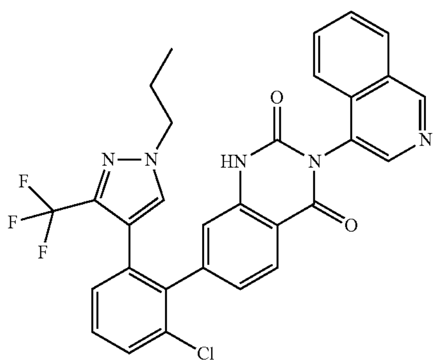 [SMILES: CCCn1cc(-c2cccc(Cl)c2-c2ccc3c(=O)n(-c4cncc5ccccc45)c(=O)[nH]c3c2)c(C(F)(F)F)n1] | 575.8 | 1H NMR (400 MHz, DMSO-d6) δ 11.79 (s, 1H), 9.46 (d, J = 1.6 Hz, 1H), 8.61 (s, 1H), 8.47 (s, 1H), 8.35-8.21 (m, 1H), 7.96-7.75 (m, 3H), 7.72-7.68 (m, 1H), 7.65-7.50 (m, 2H), 7.41 (dd, J = 7.7, 4.1 Hz, 1H), 7.08-6.96 (m, 2H), 4.08-4.00 (m, 2H), 1.65 (qd, J = 7.0, 4.0 Hz, 2H), 0.54 (td, J = 7.4, 5.0 Hz, 3H) | 22 | [1-propyl-3-(trifluoromethyl) pyrazol-4-yl]boronic acid |
| 201 | 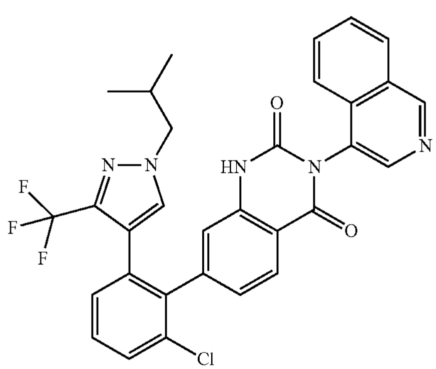 [SMILES: CC(C)Cn1cc(-c2cccc(Cl)c2-c2ccc3c(=O)n(-c4cncc5ccccc45)c(=O)[nH]c3c2)c(C(F)(F)F)n1] | 589.8 | 1H NMR (400 MHz, DMSO-d6) δ 11.80 (s, 1H), 9.46 (d, J = 1.9 Hz, 1H), 8.62 (s, 1H), 8.42 (s, 1H), 8.30 (ddd, J = 12.1, 6.5, 2.4 Hz, 1H), 7.92 (ddd, J = 17.9, 7.0, 2.3 Hz, 1H), 7.79 (dtd, J = 11.3, 7.3, 5.4 Hz, 2H), 7.74-7.67 (m, | 22 | [1-isobutyl-3-(trifluoromethyl) pyrazol-4-yl]boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | 1H), 7.62-7.50 (m, 2H), 7.41 (dd, J = 7.7, 4.0 Hz, 1H), 7.10-6.93 (m, 2H), 3.90 (dq, J = 15.8, 7.9 Hz, 2H), 1.93 (dh, J = 13.4, 6.8 Hz, 1H), 0.73-0.52 (m, 6H) | | |
| 202 | 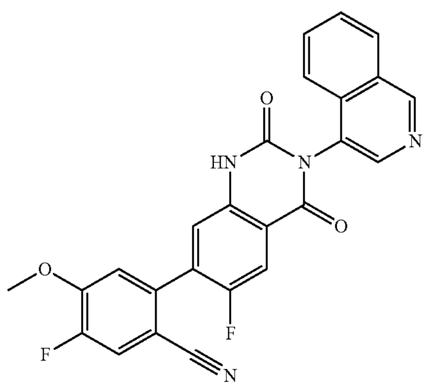 [SMILES: COc1cc(-c2cc3[nH]c(=O)n(-c4cncc5ccccc45)c(=O)c3cc2F)c(C#N)cc1F] | 456.8 | 1H NMR (400 MHz, DMSO-d6) δ 11.99 (s, 1H), 9.47 (s, 1H), 8.62 (s, 1H), 8.30 (dd, J = 7.2, 1.7 Hz, 1H), 8.10 (d, J = 11.1 Hz, 1H), 7.92 (dd, J = 18.1, 8.7 Hz, 2H), 7.80 (pd, J = 6.9, 1.5 Hz, 2H), 7.49 (d, J = 8.2 Hz, 1H), 7.38 (d, J = 6.0 Hz, 1H), 4.00 (s, 3H) | 5 | I-3; I-102 |
| 203 | 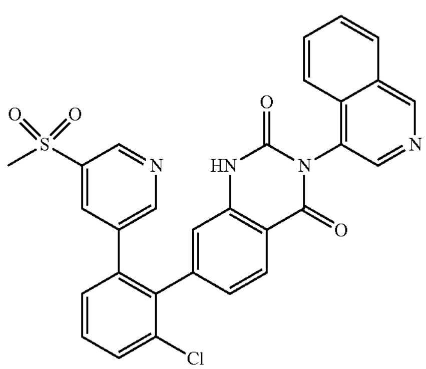 [SMILES: CS(=O)(=O)c1cncc(-c2cccc(Cl)c2-c2ccc3c(=O)n(-c4cncc5ccccc45)c(=O)[nH]c3c2)c1] | 554.7 | 1H NMR (400 MHz, DMSO-d6) δ 11.76 (d, J = 2.4 Hz, 1H), 9.46 (s, 1H), 8.98-8.91 (m, 1H), 8.71 (dd, J = 48.4, 2.1 Hz, 1H), 8.58 (d, J = 9.9 Hz, 1H), 8.30 (dq, J = 8.4, 2.5, 2.0 Hz, 1H), 8.04 (dt, J = 58.3, 2.2 Hz, 1H), 7.93-7.74 (m, 5H), 7.71-7.65 (m, 2H), 7.13-7.01 (m, 2H), 3.26 (d, J = 4.8 Hz, 3H) | 22 | (5-methylsulfonyl-3-pyridyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 204 | 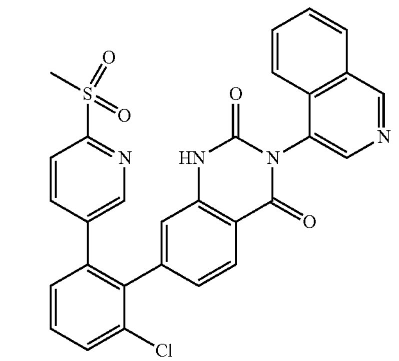 [SMILES: CS(=O)(=O)c1ccc(-c2cccc(Cl)c2-c2ccc3c(=O)n(-c4cncc5ccccc45)c(=O)[nH]c3c2)cn1] | 554.7 | 1H NMR (400 MHz, DMSO-d6) δ 11.78 (s, 1H), 9.47 (s, 1H), 8.73-8.54 (m, 2H), 8.36-8.25 (m, 1H), 8.06-7.74 (m, 7H), 7.67 (t, J = 7.9 Hz, 1H), 7.58 (ddd, J = 7.7, 3.2, 1.3 Hz, 1H), 7.15-7.02 (m, 2H), 3.28 (d, J = 4.3 Hz, 3H) | 22 | 2-methylsulfonyl-5-(4,4,5,5-tetramethyl-1,3,2-dioxaborolan-2-yl)pyridine |
| 205 | 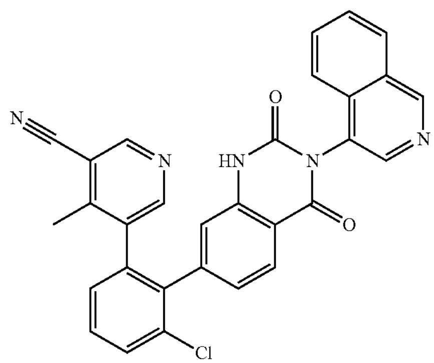 [SMILES: Cc1c(C#N)cncc1-c1cccc(Cl)c1-c1ccc2c(=O)n(-c3cncc4ccccc34)c(=O)[nH]c2c1] | 515.9 | 1H NMR (400 MHz, DMSO-d6) δ 11.72 (dd, J = 59.7, 2.8 Hz, 1H), 9.48 (s, 1H), 8.85 (t, J = 1.9 Hz, 2H), 8.66-8.56 (m, 2H), 8.49-8.39 (m, 2H), 8.34-8.26 (m, 2H), 7.91-7.74 (m, 2H), 7.63 (dd, J = 8.5, 7.3 Hz, 11H), 7.46 (dd, J = 7.7, 1.3 Hz, 2H), 7.33-7.12 (m, 2H), 6.94-6.76 (m, 2H), 2.36 (d, J = 4.1 Hz, 3H), 2.31 (d, J = 8.4 Hz, 3H) | 22 | 4-methyl-5-(4,4,5,5-tetramethyl-1,3,2-dioxaborolan-2-yl)pyridine-3-carbonitrile |
| 206 | 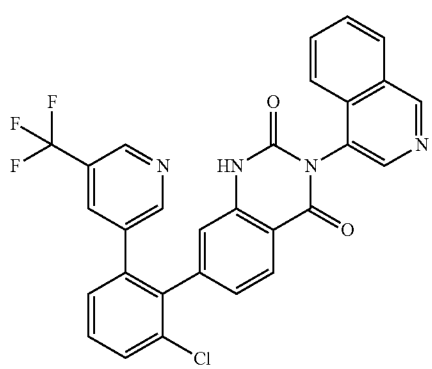 [SMILES: O=c1[nH]c2cc(-c3c(Cl)cccc3-c3cncc(C(F)(F)F)c3)ccc2c(=O)n1-c1cncc2ccccc12] | 544.8 | 1H NMR (400 MHz, DMSO-d6) δ 11.77 (d, J = 3.3 Hz, 1H), 9.47 (s, 1H), 8.88 (dd, J = 5.0, 2.1 Hz, 1H), 8.72-8.57 (m, 2H), 8.30 (ddd, J = 7.9, 5.9, 2.0 Hz, 1H), 8.05 (d, J = 46.6 Hz, 1H), 7.96-7.51 (m, 7H), 7.19-7.00 (m, 2H) | 22 | 3-(4,4,5,5-tetramethyl-1,3,2-dioxaborolan-2-yl)-5-(trifluoromethyl)pyridine |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 207 | 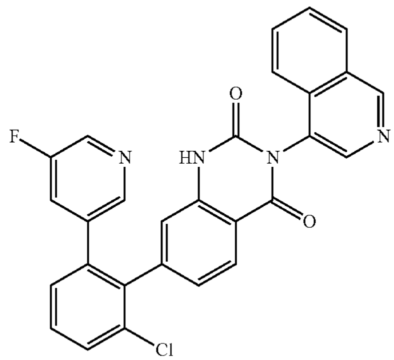 [SMILES: O=c1[nH]c2cc(-c3c(Cl)cccc3-c3cncc(F)c3)ccc2c(=O)n1-c1cncc2ccccc12] | 494.7 | 1H NMR (400 MHz, DMSO-d6) δ 11.76 (d, J = 4.0 Hz, 1H), 9.50 (s, 1H), 8.65 (d, J = 14.6 Hz, 1H), 8.49 (t, J = 3.2 Hz, 1H), 8.32 (d, J = 7.5 Hz, 1H), 8.26-8.16 (m, 1H), 8.01-7.73 (m, 5H), 7.72-7.61 (m, 2H), 7.55 (d, J = 7.6 Hz, 1H), 7.14-7.04 (m, 2H) | 22 | (5-fluoro-3-pyridyl) boronic acid |
| 208 | 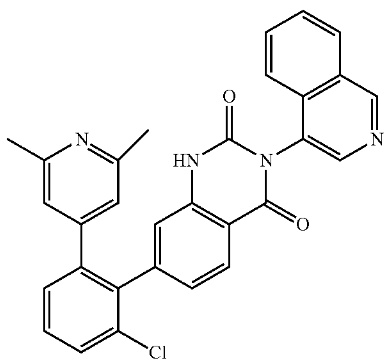 [SMILES: Cc1cc(-c2cccc(Cl)c2-c2ccc3c(=O)n(-c4cncc5ccccc45)c(=O)[nH]c3c2)cc(C)n1] | 504.8 | 1H NMR (400 MHz, DMSO-d6) δ 11.76 (d, J = 2.0 Hz, 1H), 9.45 (s, 1H), 8.57 (d, J = 24.9 Hz, 1H), 8.29 (td, J = 5.5, 3.2 Hz, 1H), 7.97-7.74 (m, 5H), 7.69 (t, J = 7.9 Hz, 1H), 7.54 (ddd, J = 7.8, 4.1, 1.2 Hz, 1H), 7.47 (d, J = 3.8 Hz, 2H), 7.20-7.01 (m, 2H), 2.57 (d, J = 7.6 Hz, 6H) | 22 | (2,6-dimethyl-4-pyridyl) boronic acid |
| 209 | 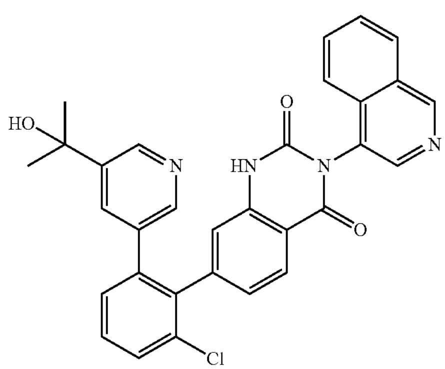 [SMILES: CC(C)(O)c1cncc(-c2cccc(Cl)c2-c2ccc3c(=O)n(-c4cncc5ccccc45)c(=O)[nH]c3c2)c1] | 534.7 | 1H NMR (400 MHz, DMSO-d6) δ 11.78 (d, J = 7.3 Hz, 1H), 9.47 (d, J = 2.5 Hz, 1H), 8.66 (dd, J = 8.7, 2.1 Hz, 1H), 8.62-8.41 (m, 2H), 8.30 (ddd, J = 10.2, 6.6, 2.0 Hz, 1H), 7.96-7.75 (m, 5H), 7.70-7.49 (m, 3H), 7.13-7.00 (m, 2H), 1.31 (dd, J = 9.5, 6.0 Hz, 6H) | 22 | 2-[5-(4,4,5,5-tetramethyl-1,3,2-dioxaborolan-2-yl)-3-pyridyl] propan-2-ol |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 210 | 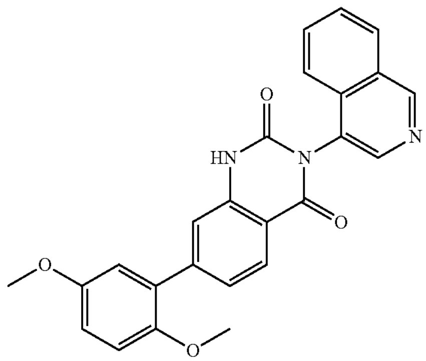 [SMILES: COc1ccc(OC)c(-c2ccc3c(=O)n(-c4cncc5ccccc45)c(=O)[nH]c3c2)c1] | 425.8 | 1H NMR (400 MHz, DMSO-d6) δ 11.77 (s, 1H), 9.50 (d, J = 0.8 Hz, 1H), 8.61 (s, 1H), 8.32 (dd, J = 8.3, 1.4 Hz, 1H), 7.98 (d, J = 8.2 Hz, 1H), 7.91 (dd, J = 7.9, 1.5 Hz, 1H), 7.81 (pd, J = 6.8, 1.5 Hz, 2H), 7.45 (d, J = 1.5 Hz, 1H), 7.38 (dd, J = 8.2, 1.6 Hz, 1H), 7.13 (d, J = 9.0 Hz, 1H), 7.02 (dd, J = 9.0, 3.1 Hz, 1H), 6.93 (d, J = 3.1 Hz, 1H), 3.77 (d, J = 7.2 Hz, 6H) | 4 | (2,5-dimethoxyphenyl) boronic acid |
| 211 | 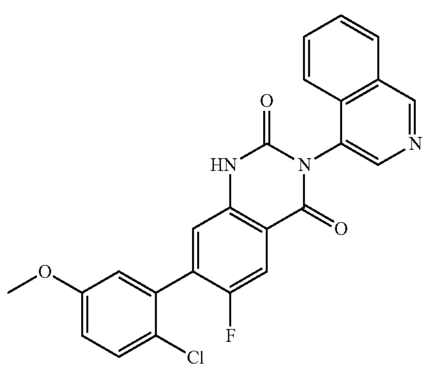 [SMILES: COc1ccc(Cl)c(-c2cc3[nH]c(=O)n(-c4cncc5ccccc45)c(=O)c3cc2F)c1] | 447.8 | 1H NMR (400 MHz, DMSO-d6) δ 11.92 (s, 1H), 9.48 (s, 1H), 8.61 (s, 1H), 8.35-8.26 (m, 1H), 7.95 (d, J = 8.0 Hz, 1H), 7.88-7.72 (m, 3H), 7.57 (d, J = 8.9 Hz, 1H), 7.24 (d, J = 5.9 Hz, 1H), 7.14 (dd, J = 8.9, 3.0 Hz, 1H), 7.06 (d, J = 3.1 Hz, 1H), 3.83 (s, 3H) | 4 | I-3; (2-chloro-5-methoxyphenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 212 | 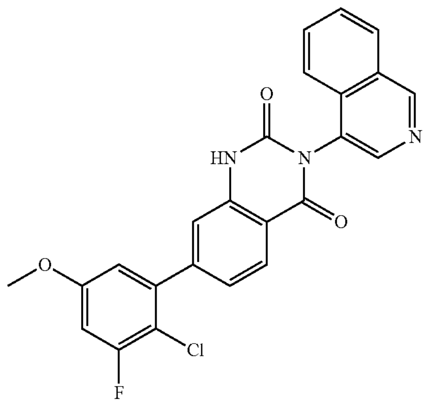 [SMILES: COc1cc(F)c(Cl)c(-c2ccc3c(=O)n(-c4cncc5ccccc45)c(=O)[nH]c3c2)c1] | 447.8 | 1H NMR (400 MHz, DMSO-d6) δ 11.89 (s, 1H), 9.50 (s, 1H), 8.63 (s, 1H), 8.32 (dd, J = 7.8, 1.7 Hz, 1H), 8.06 (d, J = 8.7 Hz, 1H), 7.95 (dd, J = 8.1, 1.5 Hz, 1H), 7.81 (dddd, J = 14.8, 8.1, 6.9, 1.4 Hz, 2H), 7.34 (d, J = 7.5 Hz, 2H), 7.24 (dd, J = 11.2, 2.9 Hz, 1H), 6.91 (dd, J = 2.9, 1.4 Hz, 1H), 3.86 (s, 3H) | 5 | I-119 |
| 213 | 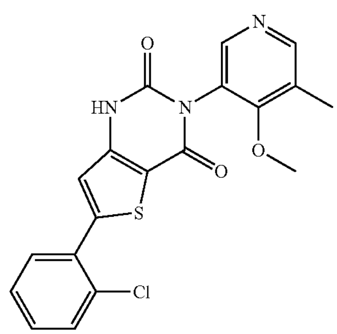 [SMILES: COc1c(C)cncc1-n1c(=O)[nH]c2cc(-c3ccccc3Cl)sc2c1=O] | 400.9 | 1H NMR (400 MHz, DMSO-d6) δ 12.35 (s, 1H), 8.53 (s, 1H), 8.49 (s, 1H), 7.80-7.73 (m, 1H), 7.73-7.64 (m, 1H), 7.59-7.47 (m, 2H), 7.30 (s, 1H), 3.83 (s, 3H), 2.32 (s, 3H). | 13 | 4-methoxy-5-methylpyridin-3-amine (I-33) |
| 214 | 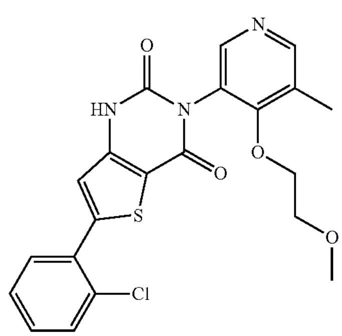 [SMILES: COCCOc1c(C)cncc1-n1c(=O)[nH]c2cc(-c3ccccc3Cl)sc2c1=O] | 444.0 | 1H NMR (400 MHz, DMSO-d6) δ 12.25 (s, 1H), 8.52 (s, 1H), 8.45 (s, 1H), 7.78-7.74 (m, 1H), 7.71-7.65 (m, 1H), 7.57-7.47 (m, 2H), 7.30 (s, 1H), 4.05 (dd, 2H), 3.48 (td, 2H), 3.10 (s, 3H), 2.32 (s, 3H). | 13 | 4-(2-methoxy-ethoxy)-5-methylpyridin-3-amine (I-34) |

TABLE 18-continued
Examples 177-384
| Example | Structure | ES/MS m/z | 1H-NMR | Procedure | Changes to Procedure: Different Reagents/ Starting Materials |
|---|---|---|---|---|---|
| 215 | 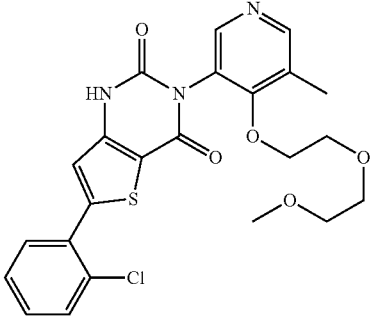 [SMILES: COCCOCCOc1c(C)cncc1-n1c(=O)[nH]c2cc(-c3ccccc3Cl)sc2c1=O] | 488.0 | 1H NMR (400 MHz, DMSO-d6) δ 12.25 (s, 1H), 8.48 (s, 1H), 8.40 (s, 1H), 7.78-7.72 (m, 1H), 7.72-7.66 (m, 1H), 7.59-7.47 (m, 2H), 7.29 (s, 1H), 4.06-4.01 (m, 2H), 3.57 (dd, 2H), 3.43-3.37 (m, 2H), 3.27 (t, 2H), 3.15 (s, 3H), 2.31 (s, 3H). | 13 | I-87 |
| 216 | 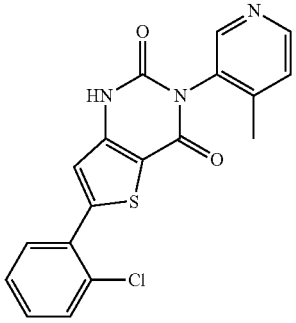 [SMILES: Cc1ccncc1-n1c(=O)[nH]c2cc(-c3ccccc3Cl)sc2c1=O] | 370.1 | 1H NMR (400 MHz, DMSO-d6) δ 12.28 (s, 1H), 8.57 (d, 2H), 7.77-7.72 (m, 1H), 7.71-7.66 (m, 1H), 7.57 (d, 1H), 7.55-7.49 (m, 2H), 7.30 (s, 1H), 2.20 (s, 3H). | 13 | 4-methylpyridin-3-amine |
| 217 | 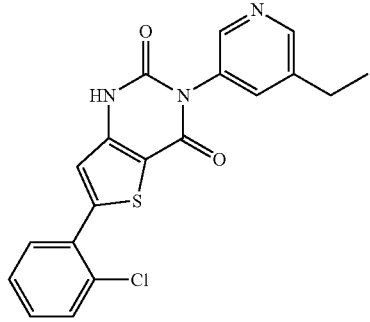 [SMILES: CCc1cncc(-n2c(=O)[nH]c3cc(-c4ccccc4Cl)sc3c2=O)c1] | 384.1 | 1H NMR (400 MHz, DMSO-d6) δ 12.19 (s, 1H), 8.54 (d, 1H), 8.44 (d, 1H), 7.80 (t, 1H), 7.77-7.73 (m, 1H), 7.71-7.67 (m, 1H), 7.56-7.49 (m, 2H), 7.28 (s, 1H), 2.73 (q, 2H), 1.25 (t, 3H). | 13 | 5-ethylpyridin-3-amine |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 218 | 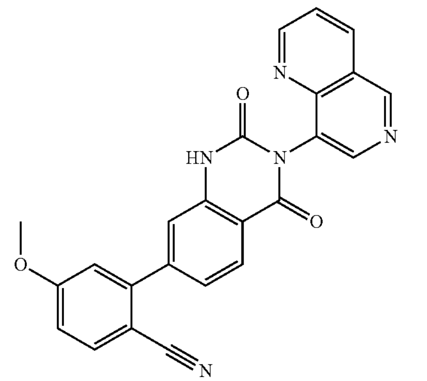 [SMILES: COc1ccc(C#N)c(-c2ccc3c(=O)n(-c4cncc5cccnc45)c(=O)[nH]c3c2)c1] | 422.2 | 1H NMR (400 MHz, DMSO-d6) δ 11.95 (s, 1H), 9.57 (s, 1H), 9.12 (dd, 1H), 8.87 (s, 1H), 8.75 (dd, 1H), 8.13-8.06 (m, 1H), 8.02-7.95 (m, 1H), 7.80 (dd, 1H), 7.50-7.43 (m, 2H), 7.29-7.21 (m, 2H), 3.94 (s, 3H). | 5 | I-98; 2-bromo-4-methoxy-benzonitrile |
| 219 | 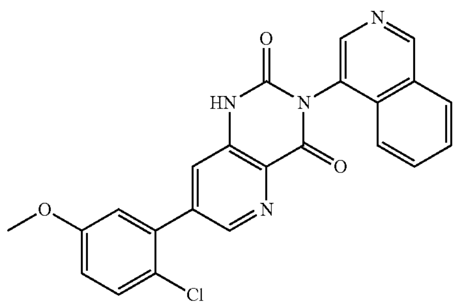 | 431.1 | 1H NMR (400 MHz, Methanol-d4) δ 9.64 (d, J = 0.8 Hz, 1H), 8.71 (s, 1H), 8.66 (d, J = 1.8 Hz, 1H), 8.45 (dd, J = 8.2, 1.1 Hz, 1H), 8.14-8.07 (m, 1H), 8.04 (ddd, J = 8.4, 6.8, 1.2 Hz, 1H), 7.94 (ddd, J = 8.1, 6.8, 1.2 Hz, 1H), 7.89 (d, J = 1.8 Hz, 1H), 7.59-7.50 (m, 1H), 7.15-7.08 (m, 2H), 3.90 (s, 3H). | 6 | I-99; 2-bromo-1-chloro-4-methoxy-benzene |
| 220 | 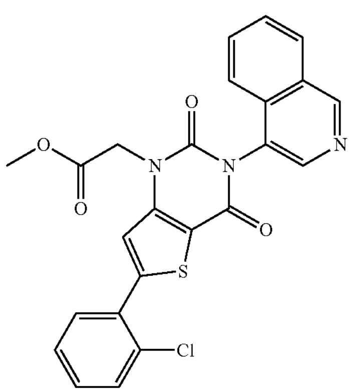 [SMILES: COC(=O)Cn1c(=O)n(-c2cncc3ccccc23)c(=O)c2sc(-c3ccccc3Cl)cc21] | 478.1 | 1H NMR (400 MHz, DMSO-d6) δ 9.49 (s, 1H), 8.59 (s, 1H), 8.32 (d, J = 8.3 Hz, 1H), 7.93 (s, 1H), 7.89-7.68 (m, 5H), 7.59-7.51 (m, 2H), 5.02 (d, J = 10.2 Hz, 2H), 3.74 (s, 3H). | 35 | Example 1; methyl 2-bromoacetate |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 221 | 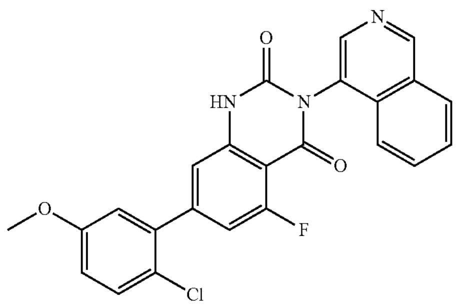 [SMILES: COc1ccc(Cl)c(-c2cc(F)c3c(=O)n(-c4cncc5ccccc45)c(=O)[nH]c3c2)c1] | 448.1 | 1H NMR (400 MHz, DMSO-d6) δ 12.00 (s, 1H), 9.50 (s, 1H), 8.62 (s, 1H), 8.32 (dd, J = 7.6, 1.5 Hz, 1H), 8.12-7.98 (m, 1H), 7.83 (dddd, J = 18.1, 8.1, 6.9, 1.3 Hz, 2H), 7.56 (d, J = 8.8 Hz, 1H), 7.25-6.96 (m, 4H), 3.84 (s, 3H) | 1 | I-100; (2-chloro-5-methoxy-phenyl) boronic acid |
| 222 | 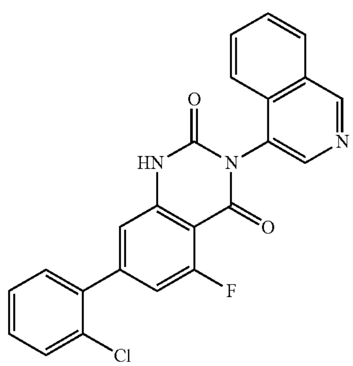 [SMILES: O=c1[nH]c2cc(-c3ccccc3Cl)cc(F)c2c(=O)n1-c1cncc2ccccc12] | 418.1 | 1H NMR (400 MHz, DMSO-d6) δ 12.01 (s, 1H), 9.51 (s, 1H), 8.63 (s, 1H), 8.33 (dd, J = 7.6, 1.4 Hz, 1H), 8.11-7.98 (m, 1H), 7.83 (dddd, J = 18.3, 8.1, 6.9, 1.3 Hz, 2H), 7.67 (ddt, J = 6.6, 4.4, 2.2 Hz, 1H), 7.58-7.46 (m, 3H), 7.16 (td, J = 6.0, 1.5 Hz, 2H). | 1 | I-100 |
| 223 | 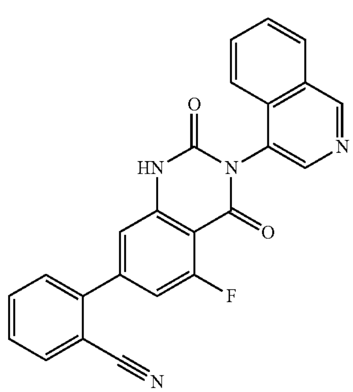 [SMILES: N#Cc1ccccc1-c1cc(F)c2c(=O)n(-c3cncc4ccccc34)c(=O)[nH]c2c1] | 409.1 | 1H NMR (400 MHz, DMSO-d6) δ 12.10 (s, 1H), 9.50 (s, 1H), 8.63 (s, 1H), 8.39-8.26 (m, 1H), 8.12-7.99 (m, 2H), 7.95-7.77 (m, 3H), 7.78-7.66 (m, 2H), 7.43-7.21 (m, 2H). | 1 | I-100; (2-cyano-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 224 | 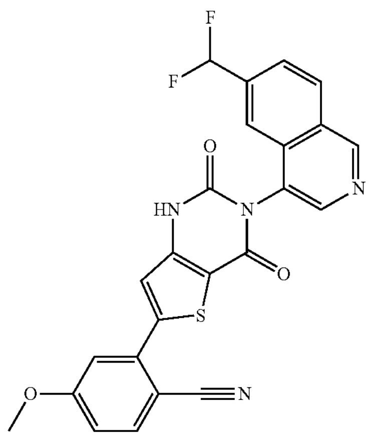 [SMILES: COc1ccc(C#N)c(-c2cc3[nH]c(=O)n(-c4cncc5ccc(C(F)F)cc45)c(=O)c3s2)c1] | 476.8 | 1H NMR (400 MHz, DMSO-d6) δ 12.38 (s, 1H), 9.55 (s, 1H), 8.70 (s, 1H), 8.46 (d, J = 8.6 Hz, 1H), 8.22 (s, 1H), 8.02 (d, J = 8.7 Hz, 1H), 7.93 (dd, J = 8.6, 1.5 Hz, 1H), 7.53 (s, 1H), 7.34 (d, J = 2.4 Hz, 1H), 7.30-7.02 (m, 2H), 3.95 (s, 3H). | 9 | I-63; I-77 |
| 225 | 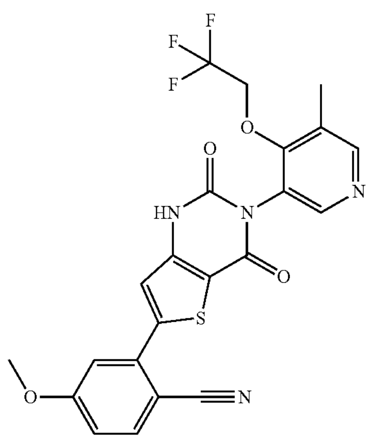 [SMILES: COc1ccc(C#N)c(-c2cc3[nH]c(=O)n(-c4cncc(C)c4OCC(F)(F)F)c(=O)c3s2)c1] | 488.8 | 1H NMR (400 MHz, DMSO-d6) δ 12.35 (s, 1H), 8.54 (s, 1H), 8.45 (s, 1H), 8.00 (d, J = 8.7 Hz, 1H), 7.48 (s, 1H), 7.43-7.14 (m, 2H), 4.62 (q, J = 8.8 Hz, 2H), 3.94 (s, 3H), 2.35 (s, 3H). | 9 | I-63; I-78 |
| 226 | 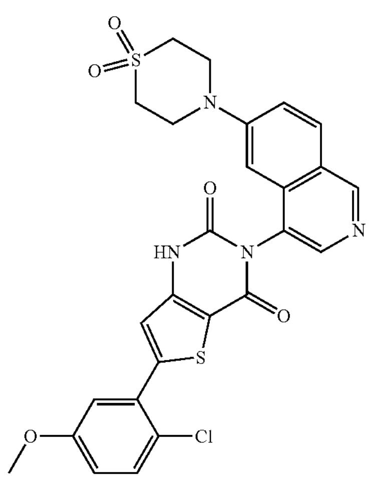 [SMILES: COc1ccc(Cl)c(-c2cc3[nH]c(=O)n(-c4cncc5ccc(N6CCS(=O)(=O)CC6)cc45)c(=O)c3s2)c1] | 568.7 | | 9 | I-62; I-86 |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 227 | 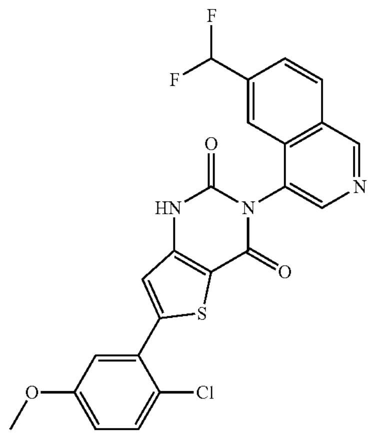 [SMILES: COc1ccc(Cl)c(-c2cc3[nH]c(=O)n(-c4cncc5ccc(C(F)F)cc45)c(=O)c3s2)c1] | 485.7 | 1H NMR (400 MHz, DMSO-d6) δ 12.31 (s, 1H), 9.55 (s, 1H), 8.70 (s, 1H), 8.46 (d, J = 8.5 Hz, 1H), 8.19 (s, 1H), 7.93 (dd, J = 8.6, 1.5 Hz, 1H), 7.60 (d, J = 8.9 Hz, 1H), 7.35 (s, 1H), 7.27-7.01 (m, 3H), 3.86 (s, 3H). | 9 | I-62; I-77 |
| 228 | 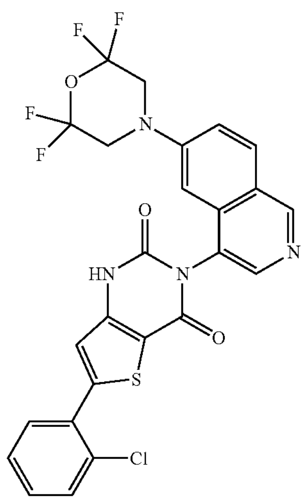 [SMILES: O=c1[nH]c2cc(-c3ccccc3Cl)sc2c(=O)n1-c1cncc2ccc(N3CC(F)(F)OC(F)(F)C3)cc12] | 562.7 | 1H NMR (400 MHz, DMSO-d6) δ 12.19 (s, 1H), 9.28 (s, 1H), 8.47 (s, 1H), 8.25 (d, J = 9.2 Hz, 1H), 7.82-7.62 (m, 3H), 7.62-7.43 (m, 2H), 7.34 (s, 1H), 7.28 (d, J = 2.3 Hz, 1H), 4.43 (t, J = 8.4 Hz, 4H). | 9 | I-83; I-30 |
| 229 | 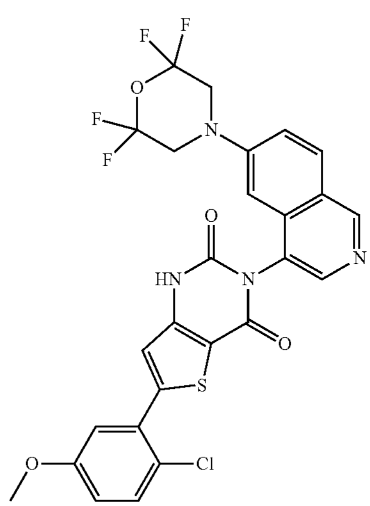 [SMILES: COc1ccc(Cl)c(-c2cc3[nH]c(=O)n(-c4cncc5ccc(N6CC(F)(F)OC(F)(F)C6)cc45)c(=O)c3s2)c1] | 592.7 | 1H NMR (400 MHz, DMSO-d6) δ 12.18 (s, 1H), 9.28 (s, 1H), 8.46 (s, 1H), 8.25 (d, J = 9.3 Hz, 1H), 7.77 (d, J = 9.2 Hz, 1H), 7.60 (d, J = 8.9 Hz, 1H), 7.34 (s, 1H), 7.31-7.00 (m, 3H), 4.41 (d, J = 8.9 Hz, 4H), 3.85 (s, 3H). | 9 | I-83; I-62 |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 230 | 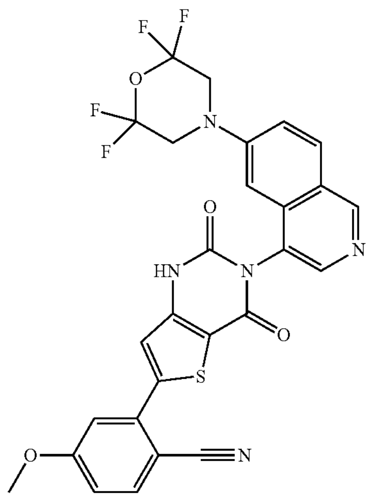 [SMILES: COc1ccc(C#N)c(-c2cc3[nH]c(=O)n(-c4cncc5ccc(N6CC(F)(F)OC(F)(F)C6)cc45)c(=O)c3s2)c1] | 583.7 | 1H NMR (400 MHz, DMSO-d6) δ 12.26 (s, 1H), 9.29 (s, 1H), 8.47 (s, 1H), 8.26 (d, J = 9.3 Hz, 1H), 8.01 (d, J = 8.7 Hz, 1H), 7.78 (d, J = 9.3 Hz, 1H), 7.52 (s, 1H), 7.37-7.19 (m, 3H), 4.43 (t, J = 8.4 Hz, 4H), 3.95 (s, 3H). | 9 | I-83; I-63 |
| 231 | 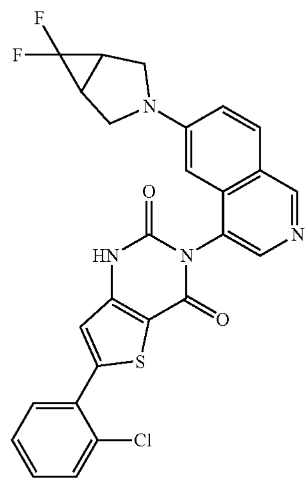 [SMILES: O=c1[nH]c2cc(-c3ccccc3Cl)sc2c(=O)n1-c1cncc2ccc(N3CC4C(C3)C4(F)F)cc12] | 522.8 | 1H NMR (400 MHz, DMSO-d6) δ 12.25 (s, 1H), 9.29 (s, 1H), 8.48 (s, 1H), 8.25 (d, J = 9.2 Hz, 1H), 7.82-7.66 (m, 2H), 7.59-7.51 (m, 2H), 7.40 (d, J = 9.4 Hz, 1H), 7.35 (s, 1H), 6.60 (s, 1H), 3.93-3.73 (m, 4H), 2.79 (d, J = 11.6 Hz, 2H). | 9 | I-84; I-30 |
| 232 | 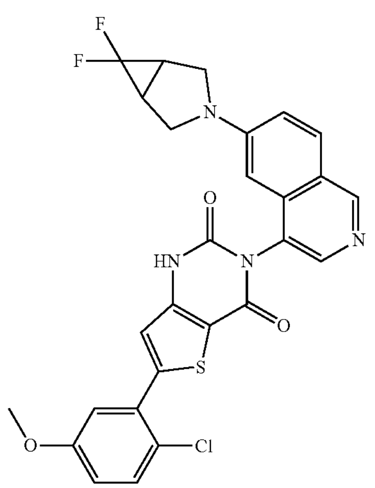 [SMILES: COc1ccc(Cl)c(-c2cc3[nH]c(=O)n(-c4cncc5ccc(N6CC7C(C6)C7(F)F)cc45)c(=O)c3s2)c1] | 552.8 | 1H NMR (400 MHz, DMSO-d6) δ 12.26 (s, 1H), 9.31 (s, 1H), 8.50 (s, 1H), 8.27 (d, J = 9.3 Hz, 1H), 7.61 (d, J = 8.9 Hz, 1H), 7.42 (dd, J = 9.2, 2.3 Hz, 1H), 7.35 (s, 1H), 7.23 (d, J = 3.0 Hz, 1H), 7.14 (dd, J = 8.9, 3.1 Hz, 1H), 6.61 (d, J = 2.2 Hz, 1H), 3.93-3.72 (m, 7H), 2.79 (dd, J = | 9 | I-84; I-62 |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | 11.2, 3.1 Hz, 2H). | | |
| 233 | 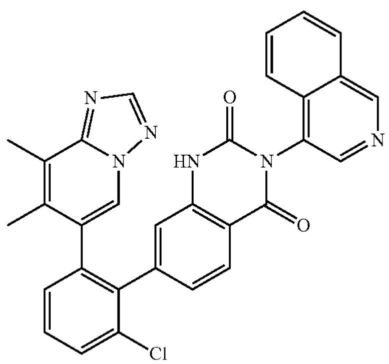 [SMILES: Cc1c(-c2cccc(Cl)c2-c2ccc3c(=O)n(-c4cncc5ccccc45)c(=O)[nH]c3c2)cn2ncnc2c1C] | 545.2 | 1H NMR (400 MHz, DMSO-d6) δ 11.80-11.61 (m, 1H), 9.42 (s, 1H), 8.76-8.63 (m, 1H), 8.57-8.51 (m, 1H), 8.38 (dd, J = 11.8, 2.3 Hz, 1H), 8.26 (dd, J = 7.1, 2.3 Hz, 1H), 7.87-7.69 (m, 4H), 7.62 (td, J = 7.9, 1.8 Hz, 1H), 7.43 (d, J = 7.6 Hz, 1H), 7.34-7.16 (m, 1H), 7.14-6.95 (m, 1H), 2.48-2.44 (m, 3H), 2.16-2.02 (m, 3H). | 21 | I-58 |
| 234 | 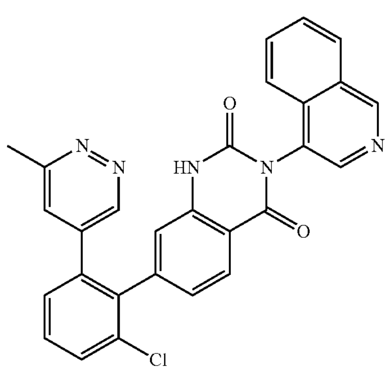 [SMILES: Cc1cc(-c2cccc(Cl)c2-c2ccc3c(=O)n(-c4cncc5ccccc45)c(=O)[nH]c3c2)cnn1] | 492.1 | 1H NMR (400 MHz, DMSO-d6) δ 11.76 (d, J = 5.8 Hz, 1H), 9.47 (s, 1H), 8.77 (dd, J = 25.4, 2.2 Hz, 1H), 8.62 (d, J = 12.1 Hz, 1H), 8.29 (dd, J = 6.7, 3.1 Hz, 1H), 7.98-7.74 (m, 5H), 7.68 (t, J = 7.9 Hz, 1H), 7.64-7.54 (m, 2H), 7.19-7.00 (m, 2H), 2.61 (d, J = 3.1 Hz, 3H). | 21 | 3-methyl-5-(4,4,5,5-tetramethyl-1,3,2-dioxaborolan-2-yl)pyridazine |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 235 | 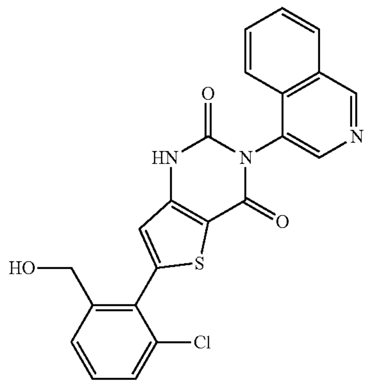 [SMILES: O=c1[nH]c2cc(-c3c(Cl)cccc3CO)sc2c(=O)n1-c1cncc2ccccc12] | 436.1 | 1H NMR (400 MHz, DMSO-d6) δ 12.31 (s, 1H), 9.47 (s, 1H), 8.62 (s, 1H), 8.34-8.24 (m, 1H), 7.92 (d, J = 8.2 Hz, 1H), 7.82 (dddd, J = 20.2, 8.1, 6.8, 1.4 Hz, 2H), 7.59 (dd, J = 21.0, 4.6 Hz, 3H), 7.01 (s, 1H), 4.41 (s, 2H). | 4 | I-8; 3-chloro-2-(4,4,5,5-tetramethyl-1,3,2-dioxaborolan-2-yl)benzyl acetate |
| 236 | 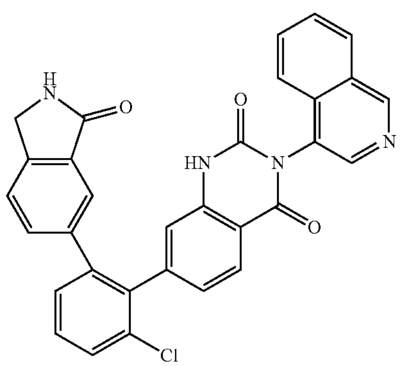 [SMILES: O=C1NCc2ccc(-c3cccc(Cl)c3-c3ccc4c(=O)n(-c5cncc6ccccc56)c(=O)[nH]c4c3)cc21] | 531.1 | 1H NMR (400 MHz, DMSO-d6) δ 11.72 (d, J = 6.7 Hz, 1H), 9.44 (d, J = 1.9 Hz, 1H), 8.65-8.51 (m, 2H), 8.37-8.19 (m, 1H), 7.93-7.68 (m, 5H), 7.59 (t, J = 7.9 Hz, 1H), 7.53-7.42 (m, 3H), 7.35 (ddd, J = 7.8, 4.7, 1.7 Hz, 1H), 7.16-7.03 (m, 2H), 4.35 (d, J = 3.9 Hz, 2H). | 21 | 6-(4,4,5,5-tetramethyl-1,3,2-dioxaborolan-2-yl)isoindolin-1-one |
| 237 | 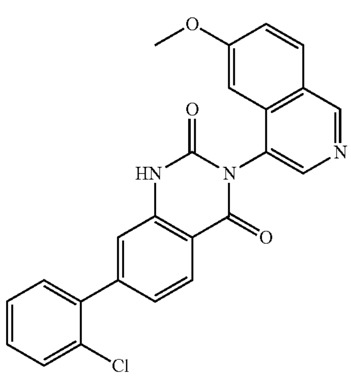 [SMILES: COc1ccc2cncc(-n3c(=O)[nH]c4cc(-c5ccccc5Cl)ccc4c3=O)c2c1] | 430.1 | 1H NMR (400 MHz, DMSO-d6) δ 11.82 (s, 1H), 9.42 (s, 1H), 8.59 (s, 1H), 8.30 (d, J = 9.1 Hz, 1H), 8.06 (d, J = 8.0 Hz, 1H), 7.73-7.63 (m, 1H), 7.59-7.44 (m, 4H), 7.36-7.31 (m, 3H), 3.90 (s, 3H). | 4 | I-69; Pd(dppf)Cl2 |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 238 | 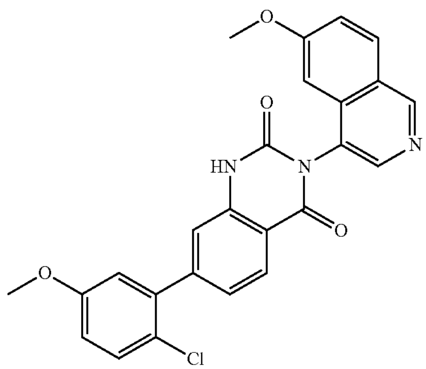 [SMILES: COc1ccc(Cl)c(-c2ccc3c(=O)n(-c4cncc5ccc(OC)cc45)c(=O)[nH]c3c2)c1] | 460.1 | 1H NMR (400 MHz, DMSO-d6) δ 11.83 (s, 1H), 9.46 (s, 1H), 8.62 (s, 1H), 8.33 (d, J = 9.0 Hz, 1H), 8.06 (d, J = 8.0 Hz, 1H), 7.56 (d, J = 8.9 Hz, 1H), 7.51 (dd, J = 9.0, 2.4 Hz, 1H), 7.38-7.30 (m, 3H), 7.10 (dd, J = 8.9, 3.0 Hz, 1H), 6.99 (d, J = 3.0 Hz, 1H), 3.91 (s, 3H), 3.83 (s, 3H). | 4 | I-69; (2-chloro-5-methoxy-phenyl) boronic acid; Pd(dppf)Cl2 |
| 239 | 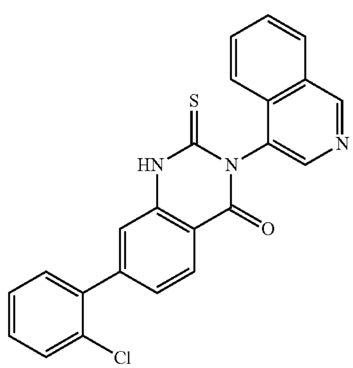 [SMILES: O=c1c2ccc(-c3ccccc3Cl)cc2[nH]c(=S)n1-c1cncc2ccccc12] | 416.1 | 1H NMR (400 MHz, DMSO-d6) δ 13.35 (s, 1H), 9.46 (s, 1H), 8.58 (s, 1H), 8.37-8.23 (m, 1H), 8.07 (d, J = 8.1 Hz, 1H), 7.99-7.84 (m, 1H), 7.78 (tt, J = 7.0, 5.3 Hz, 2H), 7.72-7.60 (m, 1H), 7.60-7.48 (m, 4H), 7.45 (dd, J = 8.1, 1.6 Hz, 1H). | 9 | I-70; isoquinolin-4-amine |
| 240 | 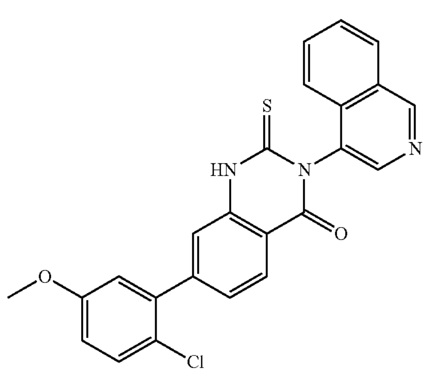 | 446.1 | 1H NMR (400 MHz, DMSO-d6) δ 13.35 (s, 1H), 9.47 (s, 1H), 8.59 (s, 1H), 8.32-8.26 (m, 1H), 8.06 (d, J = 8.1 Hz, 1H), 8.01-7.90 (m, 1H), 7.90-7.71 (m, 2H), 7.64-7.55 (m, 2H), 7.45 (dd, J = 8.2, 1.6 Hz, 1H), 7.11 (dd, J = 8.8, 3.1 Hz, 1H), 7.04 (d, J = 3.1 Hz, 1H), 3.84 (s, 3H). | 9 | I-187; isoquinolin-4-amine |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 241 | 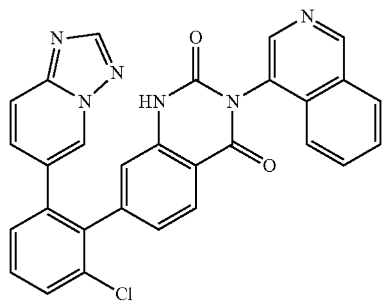 [SMILES: O=c1[nH]c2cc(-c3c(Cl)cccc3-c3ccc4ncnn4c3)ccc2c(=O)n1-c1cncc2ccccc12] | 517.1 | 1H NMR (400 MHz, MeOD) δ 9.71-9.62 (m, 2H), 8.79-8.71 (m, 2H), 8.65 (s, 1H), 8.50-8.41 (m, 3H), 8.16 (d, J = 8.1 Hz, 1H), 8.11-7.89 (m, 7H), 7.74 (dt, J = 6.7, 2.4 Hz, 1H), 7.71-7.58 (m, 4H), 7.51 (ddd, J = 14.3, 9.2, 1.8 Hz, 2H), 7.32-7.14 (m, 5H), 7.05 (dd, J = 8.0, 1.1 Hz, 1H), 6.92 (dd, J = 8.2, 1.0 Hz, 1H). | 21 | 6-(4,4,5,5-tetramethyl-1,3,2-dioxaborolan-2-yl)-[1,2,4]triazolo[1,5-a]pyridine |
| 242 | 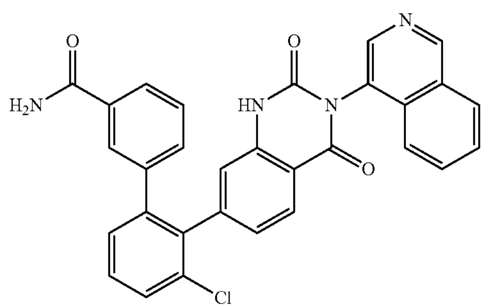 [SMILES: NC(=O)c1cccc(-c2cccc(Cl)c2-c2ccc3c(=O)n(-c4cncc5ccccc45)c(=O)[nH]c3c2)c1] | 519.1 | 1H NMR (400 MHz, MeOD) δ 9.63 (s, 1H), 8.66 (s, 1H), 8.44 (d, J = 8.4 Hz, 1H), 8.09-7.90 (m, 5H), 7.89-7.81 (m, 1H), 7.79-7.73 (m, 2H), 7.71-7.63 (m, 2H), 7.56 (td, J = 7.8, 2.1 Hz, 2H), 7.51-7.46 (m, 2H), 7.40-7.37 (m, 1H), 7.34-7.31 (m, 1H), 7.15 (ddd, J = 9.6, 8.1, 1.5 Hz, 1H), 7.09 (dd, J = 6.4, 1.4 Hz, 1H). | 22 | (3-carba-moylphenyl)boronic acid |
| 243 | 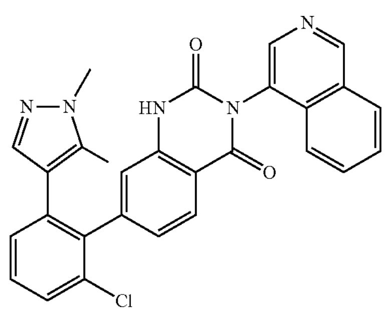 [SMILES: Cc1c(-c2cccc(Cl)c2-c2ccc3c(=O)n(-c4cncc5ccccc45)c(=O)[nH]c3c2)cnn1C] | 494.1 | 1H NMR (400 MHz, MeOD) δ 9.55 (s, 1H), 8.61 (d, J = 5.1 Hz, 1H), 8.39 (d, J = 8.2 Hz, 1H), 8.05 (d, J = 8.0 Hz, 1H), 8.02-7.85 (m, 4H), 7.58 (dt, J = 8.2, 1.4 Hz, 1H), 7.48 (t, J = | 21 | (1,5-dimethylpyrazol-4-yl)boronic acid |

| Example | Structure | ES/MS m/z | 1H-NMR | Procedure | Changes to Procedure: Different Reagents/ Starting Materials |
|---|---|---|---|---|---|
| | | | 7.9 Hz, 1H), 7.37 (dd, J = 7.6, 1.3 Hz, 1H), 7.22 (d, J = 19.8 Hz, 2H), 7.16-7.09 (m, 2H), 3.74 (d, J = 14.2 Hz, 3H), 2.05 (d, J = 3.6 Hz, 3H). | | |
| 244 | 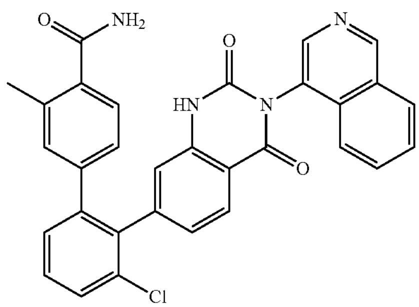 [SMILES: Cc1cc(-c2cccc(Cl)c2-c2ccc3c(=O)n(-c4cncc5ccccc45)c(=O)[nH]c3c2)ccc1C(N)=O] | 533.1 | 1H NMR (400 MHz, MeOD) δ 9.65 (s, 1H), 8.67 (d, J = 4.6 Hz, 1H), 8.46 (d, J = 8.4 Hz, 2H), 8.11-7.91 (m, 6H), 7.66-7.62 (m, 1H), 7.58-7.44 (m, 3H), 7.44-7.39 (m, 1H), 7.31 (dd, J = 15.5, 7.8 Hz, 2H), 7.21-6.99 (m, 6H), 2.40 (d, J = 9.6 Hz, 3H). | 22 | (4-carbamoyl-3-methyl-phenyl) boronic acid |
| 245 | 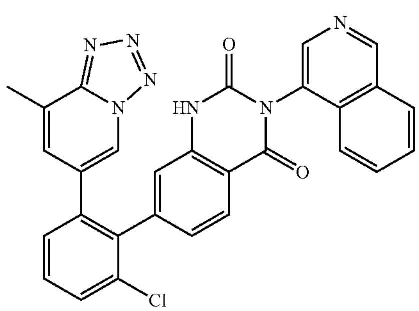 [SMILES: Cc1cc(-c2cccc(Cl)c2-c2ccc3c(=O)n(-c4cncc5ccccc45)c(=O)[nH]c3c2)cn2nnnc12] | 532.1 | 1H NMR (400 MHz, MeOD) δ 9.54 (d, J = 4.4 Hz, 1H), 8.90 (s, 1H), 8.58 (s, 1H), 8.39-8.34 (m, 1H), 8.06 (dd, J = 8.2, 2.2 Hz, 1H), 7.99-7.83 (m, 4H), 7.77 (dt, J = 7.3, 2.0 Hz, 1H), 7.67-7.56 (m, 3H), 7.50-7.39 (m, 2H), 7.27 (ddd, J = 7.9, 5.9, 1.5 Hz, 1H), 7.16 (dd, J = 5.7, 1.4 Hz, 1H), 2.65 (d, J = 12.3 Hz, 3H). | 21 | 8-methyl-6-(4,4,5,5-tetramethyl-1,3,2-dioxaborolan-2-yl)tetrazolo[1,5-a]pyridine |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 246 | 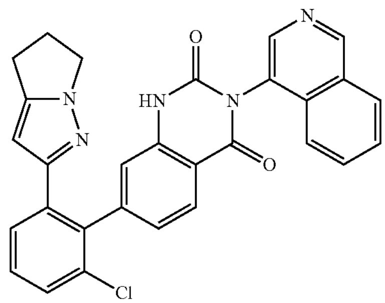 [SMILES: O=c1[nH]c2cc(-c3c(Cl)cccc3-c3cc4n(n3)CCC4)ccc2c(=O)n1-c1cncc2ccccc12] | 506.1 | 1H NMR (400 MHz, MeOD) δ 9.65 (s, 1H), 8.70 (d, J = 13.1 Hz, 1H), 8.46 (d, J = 8.3 Hz, 1H), 8.13 (d, J = 8.0 Hz, 1H), 8.06 (d, J = 7.9 Hz, 1H), 8.04-7.98 (m, 1H), 7.96 (s, 1H), 7.56-7.48 (m, 1H), 7.48-7.38 (m, 2H), 7.23-7.15 (m, 2H), 6.95 (d, J = 6.2 Hz, 1H), 4.14-4.03 (m, 2H), 2.88-2.80 (m, 1H), 2.76 (t, J = 7.2 Hz, 1H), 2.62 (dp, J = 14.6, 7.4 Hz, 2H), 1.31 (s, 1H). | 21 | 3-(4,4,5,5-tetramethyl-1,3,2-dioxaborolan-2-yl)-5,6-dihydro-4H-pyrrolo[1,2-b]pyrazole |
| 247 | 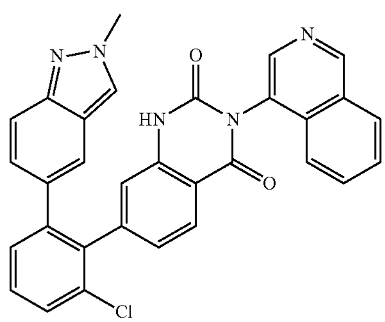 [SMILES: Cn1cc2cc(-c3cccc(Cl)c3-c3ccc4c(=O)n(-c5cncc6ccccc56)c(=O)[nH]c4c3)ccc2n1] | 530.1 | 1H NMR (400 MHz, MeOD) δ 9.66 (s, 1H), 8.65 (s, 1H), 8.46 (d, J = 8.4 Hz, 1H), 8.17 (d, J = 11.6 Hz, 1H), 8.07-8.03 (m, 1H), 7.98-7.91 (m, 2H), 7.66-7.38 (m, 6H), 7.18 (td, J = 8.2, 1.5 Hz, 1H), 7.14-7.04 (m, 2H), 4.21 (d, J = 5.3 Hz, 3H). | 22 | (2-methylindazol-5-yl)boronic acid |
| 248 | 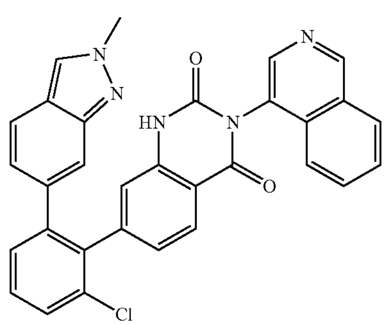 [SMILES: Cn1cc2ccc(-c3cccc(Cl)c3-c3ccc4c(=O)n(-c5cncc6ccccc56)c(=O)[nH]c4c3)cc2n1] | 530.1 | 1H NMR (400 MHz, MeOD) δ 9.67 (d, J = 2.5 Hz, 1H), 8.66 (d, J = 11.6 Hz, 1H), 8.47 (d, J = 8.4 Hz, 1H), 8.16 (d, J = 8.5 Hz, 1H), 8.08-7.94 (m, 4H), 7.71-7.45 (m, 5H), 7.40 (dd, J = 7.5, 1.3 Hz, 1H), 7.19-7.12 | 21 | 7-methyl-6-(4,4,5,5-tetramethyl-1,3,2-dioxaborolan-2-yl)-[1,2,4]triazolo[1,5-a]pyridine |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | (m, 2H), 6.97-6.91 (m, 1H), 4.20 (d, J = 6.2 Hz, 3H). | | |
| 249 | 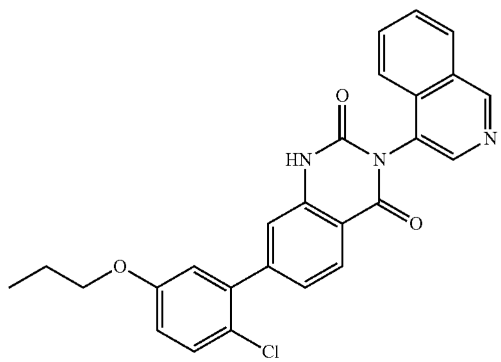 [SMILES: CCCOc1ccc(Cl)c(-c2ccc3c(=O)n(-c4cncc5ccccc45)c(=O)[nH]c3c2)c1] | 458.1 | 1H NMR (400 MHz, MeOD) δ 9.62 (s, 1H), 8.68 (s, 1H), 8.44 (d, J = 8.3 Hz, 1H), 8.18 (d, J = 8.1 Hz, 1H), 8.07-7.96 (m, 2H), 7.93 (ddd, J = 8.2, 6.6, 1.5 Hz, 1H), 7.51-7.43 (m, 1H), 7.41 (s, 1H), 7.39 (d, J = 1.6 Hz, 1H), 7.07-6.99 (m, 2H), 4.01 (t, J = 6.4 Hz, 2H), 1.91-1.78 (m, 2H), 1.08 (t, J = 7.4 Hz, 3H). | 3 | (2-chloro-5-propoxy-phenyl) boronic acid |
| 250 | 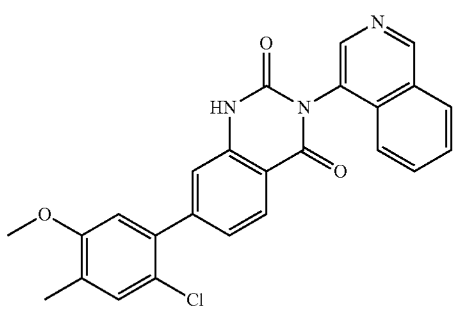 [SMILES: COc1cc(-c2ccc3c(=O)n(-c4cncc5ccccc45)c(=O)[nH]c3c2)c(Cl)cc1C] | 444.1 | 1H NMR (400 MHz, MeOD) δ 9.64 (s, 1H), 8.70 (s, 1H), 8.49-8.42 (m, 1H), 8.17 (d, J = 8.1 Hz, 1H), 8.05 (ddd, J = 8.0, 6.6, 1.2 Hz, 1H), 8.00 (d, J = 8.2 Hz, 1H), 7.94 (ddd, J = 8.2, 6.6, 1.5 Hz, 1H), 7.46-7.38 (m, 2H), 7.33 (d, J = 1.0 Hz, 1H), 6.97 (s, 1H), 3.90 (s, 3H), 2.27 (d, J = 0.8 Hz, 3H). | 3 | (2-chloro-5-methoxy-4-methyl-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 251 | 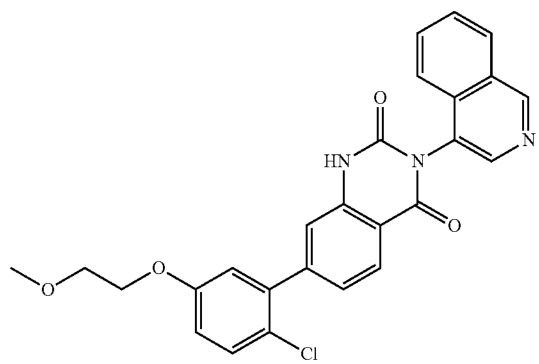 [SMILES: COCCOc1ccc(Cl)c(-c2ccc3c(=O)n(-c4cncc5ccccc45)c(=O)[nH]c3c2)c1] | 474.3 | 1H NMR (400 MHz, MeOD) δ 9.60 (s, 1H), 8.67 (s, 1H), 8.43 (d, J = 8.3 Hz, 1H), 8.17 (d, J = 8.0 Hz, 1H), 7.97 (ddt, J = 24.0, 14.7, 7.6 Hz, 4H), 7.48 (d, J = 9.1 Hz, 1H), 7.40 (d, J = 8.4 Hz, 2H), 7.10-7.02 (m, 2H), 4.22-4.16 (m, 2H), 3.81-3.74 (m, 2H), 3.45 (s, 3H). | 3 | [2-chloro-5-(2-methoxyethoxy)phenyl] boronic acid |
| 252 | 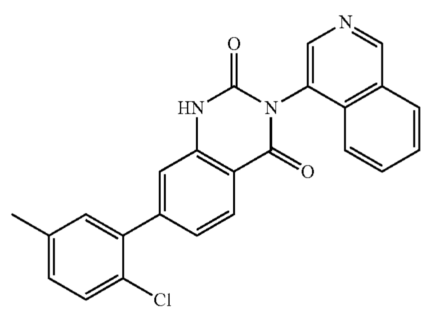 [SMILES: Cc1ccc(Cl)c(-c2ccc3c(=O)n(-c4cncc5ccccc45)c(=O)[nH]c3c2)c1] | 414.1 | 1H NMR (400 MHz, MeOD) δ 9.61 (s, 1H), 8.67 (s, 1H), 8.43 (d, J = 8.2 Hz, 1H), 8.17 (d, J = 8.1 Hz, 1H), 8.08-7.85 (m, 4H), 7.46 (d, J = 8.1 Hz, 1H), 7.39 (d, J = 8.6 Hz, 2H), 7.33-7.25 (m, 2H), 2.43 (s, 3H). | 3 | (2-chloro-5-methyl-phenyl) boronic acid |
| 253 | 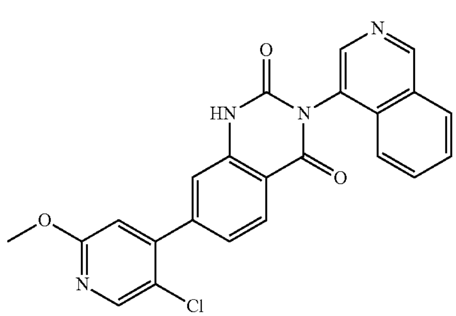 | 431.1 | 1H NMR (400 MHz, MeOD) δ 9.64 (s, 1H), 8.69 (s, 1H), 8.45 (d, J = 8.2 Hz, 1H), 8.33 (s, 1H), 8.22 (d, J = 8.1 Hz, 1H), 8.07-7.91 (m, 4H), 7.47-7.39 (m, 2H), 6.95 (s, 1H), 4.00 (s, 3H). | 3 | (5-chloro-2-methoxy-4-pyridyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 254 | 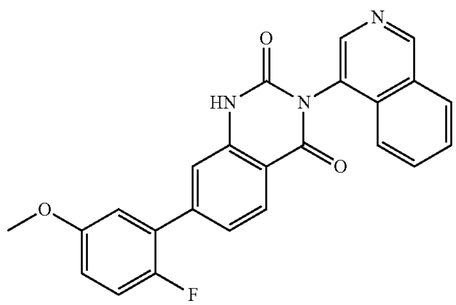 [SMILES: COc1ccc(F)c(-c2ccc3c(=O)n(-c4cncc5ccccc45)c(=O)[nH]c3c2)c1] | 414.1 | 1H NMR (400 MHz, MeOD) δ 9.65 (s, 1H), 8.70 (s, 1H), 8.46 (d, J = 8.3 Hz, 1H), 8.18 (d, J = 8.4 Hz, 1H), 8.09-7.98 (m, 2H), 7.94 (ddd, J = 8.1, 6.5, 1.5 Hz, 1H), 7.53 (dt, J = 7.1, 1.6 Hz, 2H), 7.22 (dd, J = 10.3, 9.0 Hz, 1H), 7.12 (dd, J = 6.2, 3.1 Hz, 1H), 7.05 (dt, J = 9.0, 3.5 Hz, 1H), 3.88 (s, 3H). | 3 | (2-fluoro-5-methoxy-phenyl) boronic acid |
| 255 | 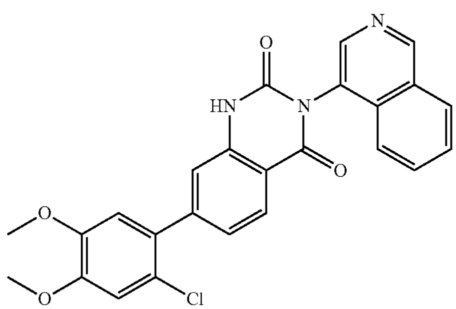 [SMILES: COc1cc(Cl)c(-c2ccc3c(=O)n(-c4cncc5ccccc45)c(=O)[nH]c3c2)cc1OC] | 460.1 | 1H NMR (400 MHz, MeOD) δ 9.67 (s, 3H), 8.72 (s, 3H), 8.47 (d, J = 8.3 Hz, 4H), 8.14 (d, J = 8.1 Hz, 4H), 8.11-7.89 (m, 14H), 7.88 (s, 1H), 7.44-7.37 (m, 8H), 7.15 (s, 4H), 7.02 (s, 4H), 3.90 (d, J = 12.6 Hz, 22H). | 3 | (2-chloro-4,5-dimethoxy-phenyl) boronic acid |
| 256 | 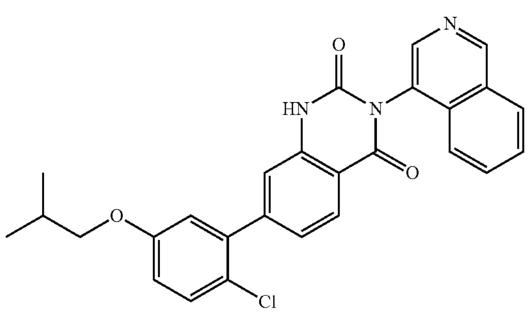 [SMILES: CC(C)COc1ccc(Cl)c(-c2ccc3c(=O)n(-c4cncc5ccccc45)c(=O)[nH]c3c2)c1] | 472.1 | 1H NMR (400 MHz, MeOD) δ 9.57 (s, 1H), 8.65 (s, 1H), 8.42-8.38 (m, 1H), 8.20-8.16 (m, 1H), 8.02-7.87 (m, 3H), 7.49-7.45 (m, 1H), 7.43-7.37 (m, 2H), 7.07-6.99 (m, 2H), 3.82 (d, J = 6.5 Hz, 2H), 2.11 (dt, J = 13.2, 6.6 Hz, 1H), 1.08 (d, J = 6.8 Hz, 6H). | 3 | (2-chloro-5-isobutoxy-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 257 | 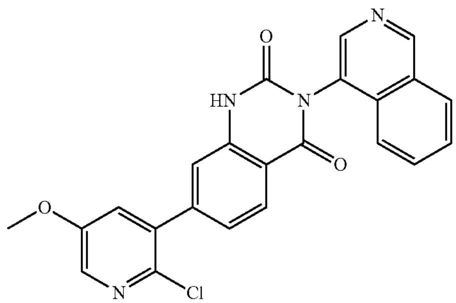 [SMILES: COc1cnc(Cl)c(-c2ccc3c(=O)n(-c4cncc5ccccc45)c(=O)[nH]c3c2)c1] | 431.1 | 1H NMR (400 MHz, MeOD) δ 9.68 (s, 1H), 8.73 (s, 1H), 8.52-8.44 (m, 2H), 8.26-8.18 (m, 2H), 8.10-7.93 (m, 4H), 7.56 (dd, J = 5.0, 3.0 Hz, 1H), 7.49-7.41 (m, 2H), 3.98 (s, 3H). | 3 | (2-chloro-5-methoxy-3-pyridyl) boronic acid |
| 258 | 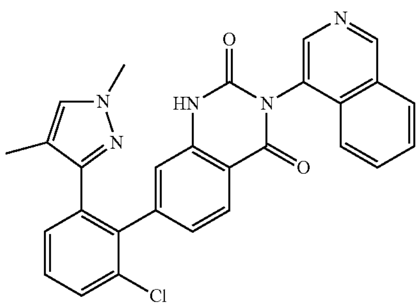 [SMILES: Cc1cn(C)nc1-c1cccc(Cl)c1-c1ccc2c(=O)n(-c3cncc4ccccc34)c(=O)[nH]c2c1] | 494.2 | 1H NMR (400 MHz, MeOD) δ 9.63 (s, 1H), 8.66 (s, 1H), 8.44 (dd, J = 8.3, 4.1 Hz, 1H), 8.09-7.89 (m, 4H), 7.67 (dt, J = 8.2, 1.5 Hz, 1H), 7.53 (t, J = 7.8 Hz, 1H), 7.42 (dd, J = 7.6, 1.3 Hz, 1H), 7.27 (d, J = 15.0 Hz, 1H), 7.19-7.11 (m, 2H), 3.78 (d, J = 9.5 Hz, 3H), 1.76 (d, J = 13.3 Hz, 3H). | 21 | 1,4-dimethyl-3-(4,4,5,5-tetramethyl-1,3,2-dioxaborolan-2-yl)pyrazole |
| 259 | 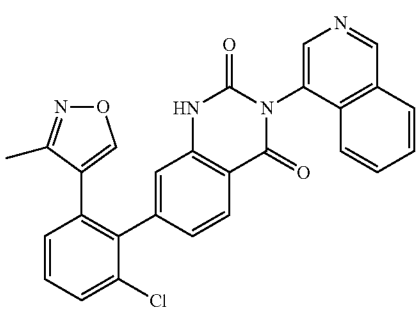 [SMILES: Cc1nocc1-c1cccc(Cl)c1-c1ccc2c(=O)n(-c3cncc4ccccc34)c(=O)[nH]c2c1] | 481.2 | 1H NMR (400 MHz, MeOD) δ 9.49 (s, 1H), 8.57 (s, 1H), 8.32 (t, J = 14.2 Hz, 2H), 8.08 (s, 1H), 7.93 (s, 2H), 7.86 (s, 1H), 7.68 (d, J = 8.2 Hz, 1H), 7.56 (t, J = 7.9 Hz, 2H), 7.51-7.36 (m, 3H), 7.16 (d, J = 8.2 Hz, 1H), 7.12 (s, 1H), 2.15 (d, J = 11.7 Hz, 3H). | 22 | 3-methyl-4-(4,4,5,5-tetramethyl-1,3,2-dioxaborolan-2-yl)isoxazole |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 260 | 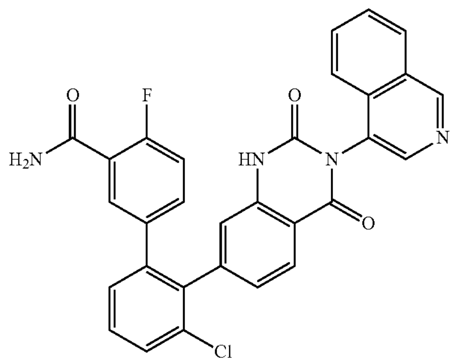 [SMILES: NC(=O)c1cc(-c2cccc(Cl)c2-c2ccc3c(=O)n(-c4cncc5ccccc45)c(=O)[nH]c3c2)ccc1F] | 537.2 | 1H NMR (400 MHz, MeOD) δ 9.68 (s, 1H), 8.70 (s, 1H), 8.48 (d, J = 8.3 Hz, 1H), 8.12-7.94 (m, 5H), 7.71-7.62 (m, 3H), 7.55 (t, J = 7.8 Hz, 1H), 7.50-7.45 (m, 1H), 7.33 (s, 2H), 7.18-7.06 (m, 4H). | 3 | (3-carbamoyl-4-fluoro-phenyl) boronic acid |
| 261 | 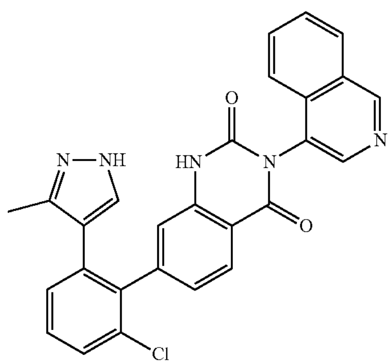 [SMILES: Cc1n[nH]cc1-c1cccc(Cl)c1-c1ccc2c(=O)n(-c3cncc4ccccc34)c(=O)[nH]c2c1] | 480.1 | 1H NMR (400 MHz, MeOD) δ 9.71 (s, 1H), 8.71 (s, 1H), 8.53-8.46 (m, 1H), 8.15-7.94 (m, 4H), 7.59 (ddd, J = 8.1, 2.7, 1.3 Hz, 1H), 7.50 (t, J = 7.9 Hz, 1H), 7.40 (dt, J = 7.8, 1.5 Hz, 1H), 7.20-7.13 (m, 2H), 7.11 (d, J = 1.5 Hz, 1H), 2.17 (d, J = 13.5 Hz, 3H). | 21 | tert-butyl 3-methyl-4-(4,4,5,5-tetramethyl-1,3,2-dioxaborolan-2-yl)pyrazole-1-carboxylate |
| 262 | 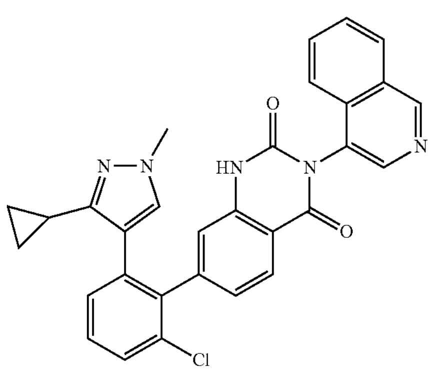 [SMILES: Cn1cc(-c2cccc(Cl)c2-c2ccc3c(=O)n(-c4cncc5ccccc45)c(=O)[nH]c3c2)c(C2CC2)n1] | 520.1 | 1H NMR (400 MHz, MeOD) δ 9.64 (s, 1H), 8.68 (d, J = 5.1 Hz, 1H), 8.45 (d, J = 8.2 Hz, 1H), 8.07-7.92 (m, 4H), 7.58 (ddd, J = 6.8, 2.7, 1.4 Hz, 1H), 7.52-7.45 (m, 2H), 7.23-7.11 (m, 3H), 3.70 (d, J = 15.0 Hz, 3H), 1.60 (td, J = 8.5, 4.3 Hz, 1H), 0.84-0.77 (m, 2H), 0.69 (dd, J = 5.2, 2.3 Hz, 2H). | 21 | 3-cyclopropyl-1-methyl-4-(4,4,5,5-tetramethyl-1,3,2-dioxaborolan-2-yl)pyrazole |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 263 | 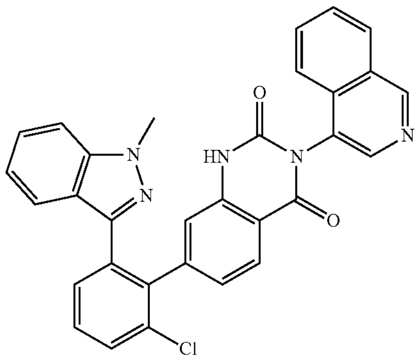 [SMILES: Cn1nc(-c2cccc(Cl)c2-c2ccc3c(=O)n(-c4cncc5ccccc45)c(=O)[nH]c3c2)c2ccccc21] | 530.1 | 1H NMR (400 MHz, MeOD) δ 8.62 (d, J = 8.9 Hz, 1H), 8.43 (d, J = 8.2 Hz, 1H), 8.06-7.87 (m, 4H), 7.82 (d, J = 8.3 Hz, 1H), 7.74 (dt, J = 7.3, 2.2 Hz, 1H), 7.67-7.59 (m, 2H), 7.55-7.34 (m, 4H), 7.22-7.06 (m, 3H), 4.02 (d, J = 10.8 Hz, 3H). | 21 | 1-methyl-3-(4,4,5,5-tetramethyl-1,3,2-dioxaborolan-2-yl)indazole |
| 264 | 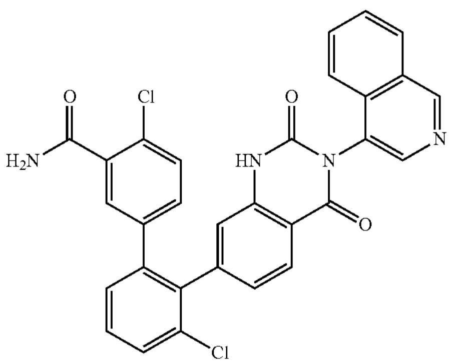 [SMILES: NC(=O)c1cc(-c2cccc(Cl)c2-c2ccc3c(=O)n(-c4cncc5ccccc45)c(=O)[nH]c3c2)ccc1Cl] | 553.1 | 1H NMR (400 MHz, MeOD) δ 9.69 (d, J = 3.2 Hz, 1H), 8.71 (d, J = 13.5 Hz, 1H), 8.52-8.45 (m, 1H), 8.16-7.93 (m, 4H), 7.66 (ddd, J = 8.1, 2.4, 1.3 Hz, 1H), 7.56 (t, J = 7.9 Hz, 1H), 7.48 (dt, J = 7.7, 1.1 Hz, 1H), 7.45-7.31 (m, 2H), 7.31-7.20 (m, 1H), 7.17 (td, J = 8.3, 1.5 Hz, 1H), 7.09 (dd, J = 8.5, 1.4 Hz, 1H). | 21 | (3-carbamoyl-4-fluoro-phenyl)boronic acid |
| 265 | 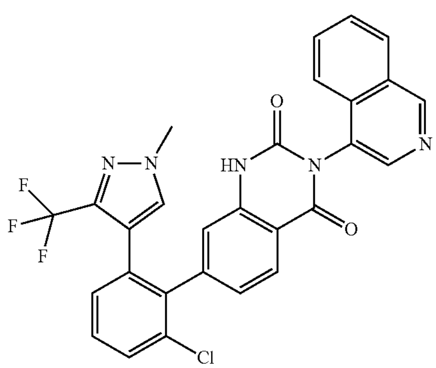 [SMILES: Cn1cc(-c2cccc(Cl)c2-c2ccc3c(=O)n(-c4cncc5ccccc45)c(=O)[nH]c3c2)c(C(F)(F)F)n1] | 548.1 | 1H NMR (400 MHz, MeOD) δ 9.59 (d, J = 8.7 Hz, 1H), 8.62 (d, J = 15.4 Hz, 1H), 8.42 (d, J = 8.0 Hz, 1H), 8.08-7.83 (m, 4H), 7.68-7.61 (m, 1H), 7.54-7.45 (m, 2H), 7.39 (d, J = 7.6 Hz, 1H), 7.11 (d, J = 7.4 Hz, 1H), 3.86 (d, J = 15.2 Hz, 3H). | 21 | 1-methyl-4-(4,4,5,5-tetramethyl-1,3,2-dioxaborolan-2-yl)-3-(trifluoromethyl)pyrazole |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 266 | 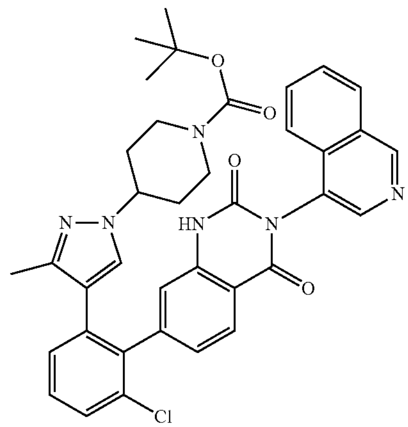 [SMILES: Cc1nn(C2CCN(C(=O)OC(C)(C)C)CC2)cc1-c1cccc(Cl)c1-c1ccc2c(=O)n(-c3cncc4ccccc34)c(=O)[nH]c2c1] | 663.3 | 1H NMR (400 MHz, MeOD) δ 9.54 (d, J = 5.2 Hz, 1H), 8.65 (s, 1H), 8.60 (s, 1H), 8.38 (d, J = 8.2 Hz, 1H), 8.08-7.84 (m, 5H), 7.79 (d, J = 8.5 Hz, 1H), 7.59 (dd, J = 7.9, 1.1 Hz, 1H), 7.49 (t, J = 7.8 Hz, 1H), 7.43-7.36 (m, 1H), 7.26 (d, J = 7.6 Hz, 1H), 7.14 (d, J = 8.4 Hz, 1H), 7.08 (d, J = 6.5 Hz, 1H), 4.18 (dd, J = 7.7, 3.8 Hz, 1H), 4.09 (d, J = 14.4 Hz, 2H), 2.94 (s, 4H), 2.08 (d, J = 6.3 Hz, 4H), 1.96 (s, 1H), 1.91 (s, 2H), 1.78 (t, J = 13.1 Hz, 3H), 1.45 (d, J = 17.8 Hz, 11H), 1.31 (s, 1H). | 21 | tert-butyl 4-[3-methyl-4-(4,4,5,5-tetramethyl-1,3,2-dioxaborolan-2-yl)pyrazol-1-yl]piperidine-1-carboxylate |
| 267 | 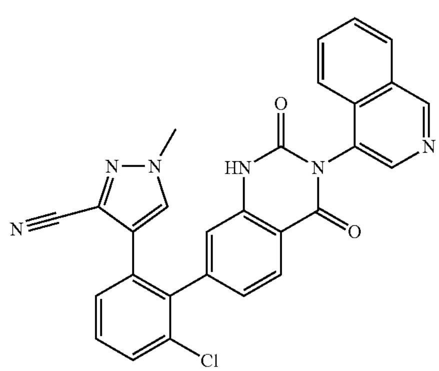 [SMILES: Cn1cc(-c2cccc(Cl)c2-c2ccc3c(=O)n(-c4cncc5ccccc45)c(=O)[nH]c3c2)c(C#N)n1] | 505.1 | 1H NMR (400 MHz, MeOD) δ 9.63 (s, 1H), 8.67 (s, 1H), 8.44 (d, J = 8.1 Hz, 1H), 8.09-7.99 (m, 3H), 7.94 (s, 1H), 7.69 (d, J = 8.4 Hz, 1H), 7.53 (dq, J = 13.1, 9.7, 8.8 Hz, 4H), 7.19 (s, 1H), 7.13 (d, J = 8.3 Hz, 1H), 3.89 (d, J = 13.1 Hz, 3H). | 21 | 4-(4,4-dimethyl-1,3,2-dioxaborolan-2-yl)-1-methyl-pyrazole-3-carbonitrile |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 268 | 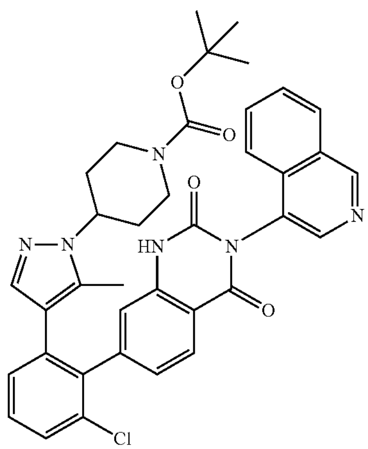 [SMILES: Cc1c(-c2cccc(Cl)c2-c2ccc3c(=O)n(-c4cncc5ccccc45)c(=O)[nH]c3c2)cnn1C1CCN(C(=O)OC(C)(C)C)CC1] | 663.3 | 1H NMR (400 MHz, MeOD) δ 9.70 (d, J = 5.4 Hz, 1H), 8.71 (d, J = 8.9 Hz, 1H), 8.49 (d, J = 8.2 Hz, 1H), 8.15-7.93 (m, 5H), 7.59 (dd, J = 8.1, 1.3 Hz, 1H), 7.50 (t, J = 7.8 Hz, 1H), 7.36 (ddd, J = 7.6, 3.7, 1.3 Hz, 1H), 7.14-7.07 (m, 2H), 7.04 (d, J = 12.8 Hz, 1H), 4.33 (dd, J = 13.2, 8.1 Hz, 1H), 4.21 (d, J = 13.4 Hz, 2H), 2.20 (d, J = 3.7 Hz, 3H), 1.82 (d, J = 12.5 Hz, 5H), 1.48 (d, J = 5.2 Hz, 9H). | 21 | tert-butyl 4-[5-methyl-4-(4,4,5,5-tetramethyl-1,3,2-dioxaborolan-2-yl)pyrazol-1-yl]piperidine-1-carboxylate |
| 269 | 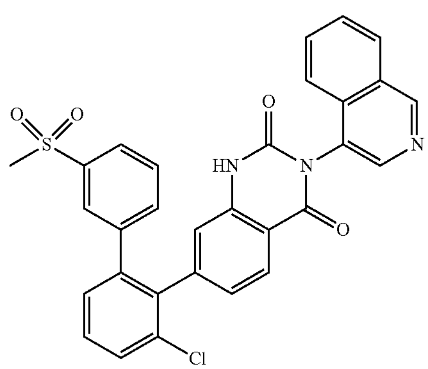 [SMILES: CS(=O)(=O)c1cccc(-c2cccc(Cl)c2-c2ccc3c(=O)n(-c4cncc5ccccc45)c(=O)[nH]c3c2)c1] | 555.1 | 1H NMR (400 MHz, MeOD) δ 9.67 (d, J = 5.8 Hz, 1H), 8.68 (d, J = 13.0 Hz, 1H), 8.49-8.45 (m, 1H), 8.13-7.92 (m, 4H), 7.87-7.82 (m, 1H), 7.73-7.67 (m, 2H), 7.66-7.52 (m, 4H), 7.20-7.00 (m, 2H), 3.05 (d, J = 1.2 Hz, 3H). | 22 | (3-methyl-sulfonylphenyl) boronic acid |
| 270 | 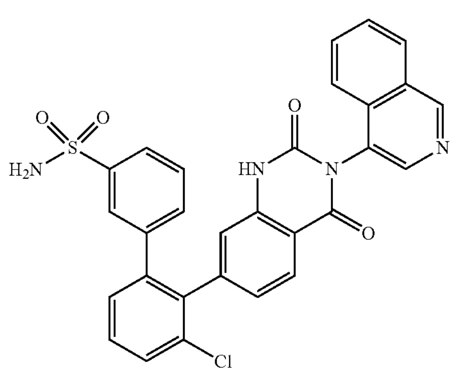 [SMILES: NS(=O)(=O)c1cccc(-c2cccc(Cl)c2-c2ccc3c(=O)n(-c4cncc5ccccc45)c(=O)[nH]c3c2)c1] | 557.1 | 1H NMR (400 MHz, MeOD) δ 9.65 (d, J = 6.5 Hz, 1H), 8.67 (d, J = 7.5 Hz, 1H), 8.50-8.41 (m, 1H), 8.12-7.91 (m, 4H), 7.81-7.75 (m, 1H), 7.71-7.65 (m, 1H), 7.61-7.47 (m, 3H), 7.45-7.39 (m, 1H), | 22 | (3-sulfamoyl-phenyl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | 7.17-7.00 (m, 2H). | | |
| 271 | 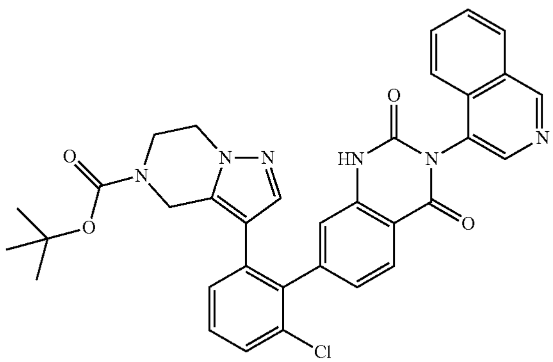 [SMILES: CC(C)(C)OC(=O)N1CCn2ncc(-c3cccc(Cl)c3-c3ccc4c(=O)n(-c5cncc6ccccc56)c(=O)[nH]c4c3)c2C1] | 621.8 | 1H NMR (400 MHz, MeOD) δ 9.72 (d, J = 10.3 Hz, 1H), 8.72 (t, J = 6.8 Hz, 1H), 8.55-8.40 (m, 2H), 8.16-8.10 (m, 1H), 8.09 (d, J = 1.3 Hz, 1H), 8.08-8.00 (m, 2H), 7.98 (ddd, J = 6.4, 3.7, 2.4 Hz, 1H), 7.72-7.48 (m, 3H), 7.44-7.29 (m, 2H), 7.21-7.15 (m, 2H), 7.07 (d, J = 3.9 Hz, 1H), 4.56 (s, 1H), 4.51 (s, 1H), 4.17-4.06 (m, 2H), 3.89 (s, 1H), 1.50 (d, J = 0.7 Hz, 7H). | 22 | tert-butyl 3-(4,4,5,5-tetramethyl-1,3,2-dioxaborolan-2-yl)-6,7-dihydro-4H-pyrazolo[1,5-a]pyrazine-5-carboxylate |
| 272 | 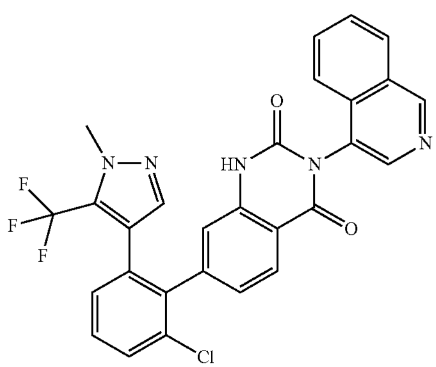 [SMILES: Cn1ncc(-c2cccc(Cl)c2-c2ccc3c(=O)n(-c4cncc5ccccc45)c(=O)[nH]c3c2)c1C(F)(F)F] | 549.7 | 1H NMR (400 MHz, MeOD) δ 9.65 (s, 1H), 8.67 (d, J = 1.7 Hz, 1H), 8.46 (d, J = 8.2 Hz, 1H), 8.10-7.97 (m, 4H), 7.97-7.90 (m, 1H), 7.66 (ddd, J = 8.1, 2.5, 1.2 Hz, 1H), 7.53-7.49 (m, 1H), 7.39-7.30 (m, 2H), 7.10 (dtd, J = 11.5, 4.3, 3.5, 1.5 Hz, 2H), 4.00-3.91 (m, 3H). | 21 | 1-methyl-4-(4,4,5,5-tetramethyl-1,3,2-dioxaborolan-2-yl)-5-(trifluoromethyl) pyrazole |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 273 | 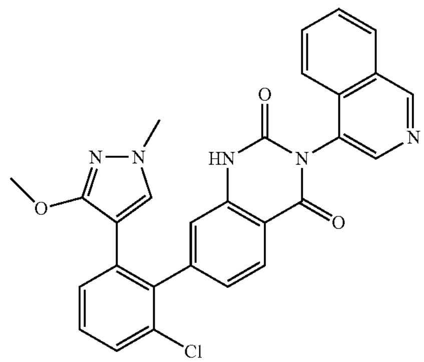 [SMILES: COc1nn(C)cc1-c1cccc(Cl)c1-c1ccc2c(=O)n(-c3cncc4ccccc34)c(=O)[nH]c2c1] | 509.8 | 1H NMR (400 MHz, MeOD) δ 9.61 (d, J = 3.4 Hz, 1H), 8.69-8.66 (m, 1H), 8.45-8.42 (m, 1H), 8.13-7.88 (m, 6H), 7.56-7.37 (m, 6H), 7.15 (ddd, J = 3.6, 2.8, 1.4 Hz, 2H), 3.77 (d, J = 5.4 Hz, 3H), 3.64 (d, J = 14.5 Hz, 3H). | 22 | 3-methoxy-1-methyl-4-(4,4,5,5-tetramethyl-1,3,2-dioxaborolan-2-yl)pyrazole |
| 274 | 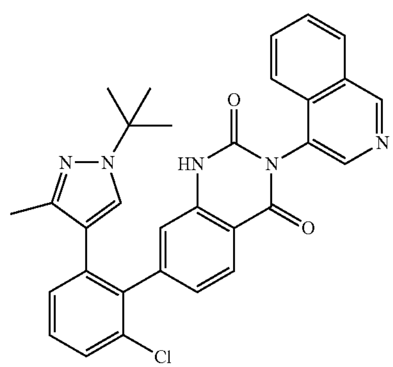 [SMILES: Cc1nn(C(C)(C)C)cc1-c1cccc(Cl)c1-c1ccc2c(=O)n(-c3cncc4ccccc34)c(=O)[nH]c2c1] | 537.9 | 1H NMR (400 MHz, MeOD) δ 9.63 (d, J = 5.5 Hz, 1H), 8.66 (d, J = 9.9 Hz, 1H), 8.45 (d, J = 8.3 Hz, 1H), 8.12-7.91 (m, 5H), 7.76 (dd, J = 8.3, 3.4 Hz, 1H), 7.58 (dt, J = 8.0, 1.5 Hz, 2H), 7.53-7.27 (m, 4H), 7.24-7.13 (m, 2H), 7.08 (dd, J = 11.4, 1.4 Hz, 1H), 2.08 (d, J = 23.5 Hz, 3H), 1.47 (d, J = 5.1 Hz, 9H). | 22 | (1-tert-butyl-3-methyl-pyrazol-4-yl)boronic acid |
| 275 | 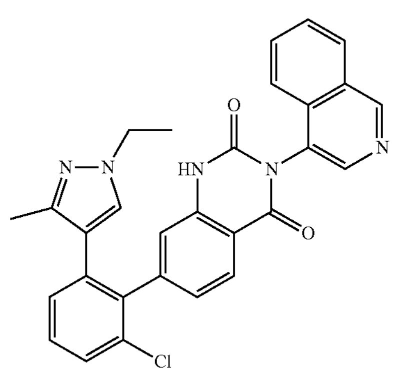 [SMILES: CCn1cc(-c2cccc(Cl)c2-c2ccc3c(=O)n(-c4cncc5ccccc45)c(=O)[nH]c3c2)c(C)n1] | 509.8 | 1H NMR (400 MHz, MeOD) δ 9.65 (d, J = 2.4 Hz, 1H), 8.68 (d, J = 2.2 Hz, 1H), 8.46 (d, J = 8.1 Hz, 1H), 8.11-7.89 (m, 5H), 7.59 (dt, J = 8.1, 1.6 Hz, 1H), 7.52-7.36 (m, 3H), 7.23 (d, J = 1.9 Hz, 1H), 7.15 (dd, J = 8.1, 1.5 Hz, 1H), 7.10 (dd, J = 4.4, 1.5 Hz, 1H), 4.02 (dq, J = 14.4, 7.3 Hz, 2H), 2.07 (d, J = | 22 | 1-ethyl-3-methyl-4-(4,4,5,5-tetramethyl-1,3,2-dioxaborolan-2-yl)pyrazole |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | 13.7 Hz, 3H), 1.34 (td, J = 7.3, 3.0 Hz, 3H). | | |
| 276 | 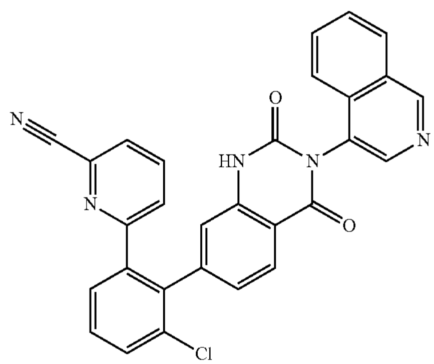 [SMILES: N#Cc1cccc(-c2cccc(Cl)c2-c2ccc3c(=O)n(-c4cncc5ccccc45)c(=O)[nH]c3c2)n1] | 501.8 | 1H NMR (400 MHz, MeOD) δ 9.57 (d, J = 9.0 Hz, 1H), 8.68-8.58 (m, 1H), 8.40 (t, J = 8.2 Hz, 1H), 8.19 (d, J = 8.1 Hz, 1H), 8.07-7.56 (m, 8H), 7.55-7.49 (m, 1H), 7.49-7.37 (m, 2H), 7.20-7.03 (m, 2H). | 22 | 6-(4,4,5,5-tetramethyl-1,3,2-dioxaborolan-2-yl)pyridine-2-carbonitrile |
| 277 | 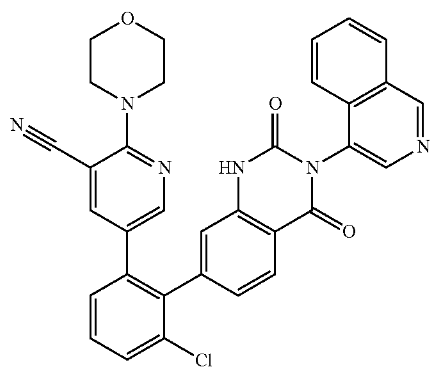 [SMILES: N#Cc1cc(-c2cccc(Cl)c2-c2ccc3c(=O)n(-c4cncc5ccccc45)c(=O)[nH]c3c2)cnc1N1CCOCC1] | 586.8 | 1H NMR (400 MHz, MeOD) δ 9.71 (s, 1H), 8.72 (d, J = 2.5 Hz, 1H), 8.50 (d, J = 8.2 Hz, 1H), 8.21-7.94 (m, 5H), 7.80 (dd, J = 18.7, 2.5 Hz, 1H), 7.67 (dt, J = 8.0, 1.1 Hz, 1H), 7.57 (td, J = 7.9, 0.9 Hz, 1H), 7.48 (td, J = 7.7, 1.3 Hz, 1H), 7.21-7.14 (m, 2H), 3.84-3.76 (m, 4H), 3.69 (ddd, J = 11.0, 5.6, 3.9 Hz, 4H). | 22 | 2-morpholino-5-(4,4,5,5-tetramethyl-1,3,2-dioxaborolan-2-yl)pyridine-3-carbonitrile |
| 278 | 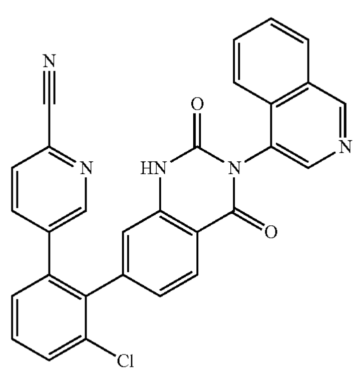 [SMILES: N#Cc1ccc(-c2cccc(Cl)c2-c2ccc3c(=O)n(-c4cncc5ccccc45)c(=O)[nH]c3c2)cn1] | 502.8 | 1H NMR (400 MHz, MeOD) δ 9.62 (d, J = 5.6 Hz, 1H), 8.65 (d, J = 14.1 Hz, 1H), 8.54 (ddd, J = 9.2, 2.2, 0.9 Hz, 1H), 8.47-8.40 (m, 1H), 8.09-7.96 (m, 3H), 7.96-7.72 (m, 4H), 7.63 (t, J = 7.9 Hz, 1H), 7.54 (dt, J = 7.7, 1.3 Hz, 1H), 7.20-7.09 (m, 2H). | 22 | 3-(4,4,5,5-tetramethyl-1,3,2-dioxaborolan-2-yl)pyridine-4-carbonitrile |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 279 | 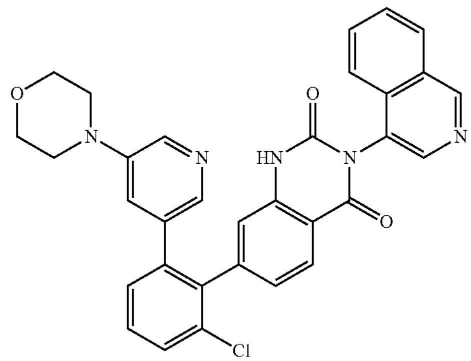 [SMILES: O=c1[nH]c2cc(-c3c(Cl)cccc3-c3cncc(N4CCOCC4)c3)ccc2c(=O)n1-c1cncc2ccccc12] | 561.8 | 1H NMR (400 MHz, MeOD) δ 9.54 (d, J = 7.5 Hz, 1H), 8.57 (d, J = 38.3 Hz, 1H), 8.41-8.35 (m, 1H), 8.28 (dd, J = 9.9, 2.8 Hz, 1H), 8.07 (ddd, J = 9.3, 4.9, 1.9 Hz, 2H), 8.02-7.72 (m, 6H), 7.64 (dtd, J = 18.8, 7.7, 1.4 Hz, 2H), 7.24-7.14 (m, 2H), 3.83 (dq, J = 5.3, 2.9 Hz, 4H), 3.32-3.27 (m, 4H). | 22 | (5-morpholino-3-pyridyl) boronic acid |
| 280 | 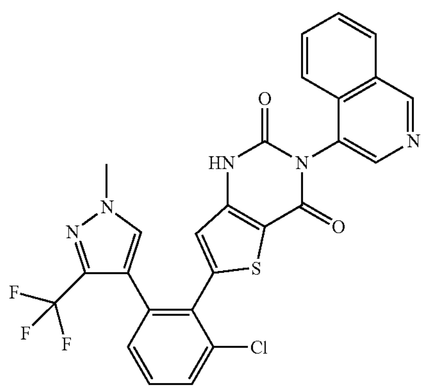 [SMILES: Cn1cc(-c2cccc(Cl)c2-c2cc3[nH]c(=O)n(-c4cncc5ccccc45)c(=O)c3s2)c(C(F)(F)F)n1] | 553.7 | 1H NMR (400 MHz, MeOD) δ 9.69 (s, 1H), 8.70 (s, 1H), 8.48 (d, J = 8.2 Hz, 1H), 8.10 (ddd, J = 8.1, 6.7, 1.2 Hz, 1H), 8.05 (d, J = 8.3 Hz, 1H), 7.98 (ddd, J = 8.2, 6.7, 1.4 Hz, 1H), 7.68 (td, J = 4.2, 1.2 Hz, 2H), 7.56 (t, J = 7.9 Hz, 1H), 7.41 (dd, J = 7.7, 1.2 Hz, 1H), 6.92 (s, 1H), 3.94 (s, 3H). | 11 | 1-methyl-4-(4,4,5,5-tetramethyl-1,3,2-dioxaborolan-2-yl)-3-(trifluoromethyl) pyrazole |
| 281 | 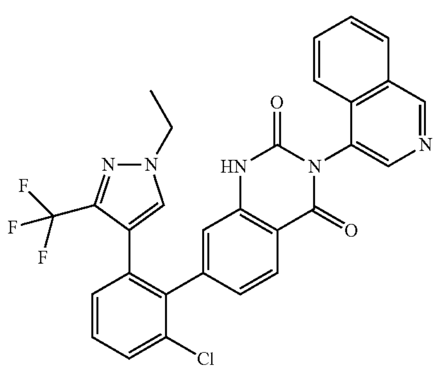 [SMILES: CCn1cc(-c2cccc(Cl)c2-c2ccc3c(=O)n(-c4cncc5ccccc45)c(=O)[nH]c3c2)c(C(F)(F)F)n1] | 561.8 | 1H NMR (400 MHz, MeOD) δ 9.62 (s, 1H), 8.65 (d, J = 5.7 Hz, 1H), 8.44 (d, J = 8.3 Hz, 1H), 8.08-7.87 (m, 4H), 7.64 (dt, J = 8.2, 1.4 Hz, 1H), 7.55-7.46 (m, 2H), 7.45-7.38 (m, 1H), 7.11 (d, J = 8.3 Hz, 2H), 4.14 (dq, J = 14.5, | 22 | [1-ethyl-3-(trifluoromethyl) pyrazol-4-yl]boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | 7.3 Hz, 2H), 2.05 (s, 1H), 1.38 (td, J = 7.3, 2.7 Hz, 3H). | | |
| 282 | 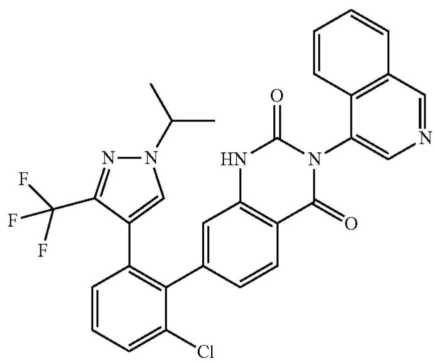 [SMILES: CC(C)n1cc(-c2cccc(Cl)c2-c2ccc3c(=O)n(-c4cncc5ccccc45)c(=O)[nH]c3c2)c(C(F)(F)F)n1] | 575.8 | 1H NMR (400 MHz, MeOD) δ 9.62 (s, 1H), 8.65 (d, J = 7.2 Hz, 1H), 8.43 (d, J = 8.2 Hz, 1H), 8.08-7.88 (m, 4H), 7.81 (d, J = 8.4 Hz, 1H), 7.64 (dt, J = 8.1, 1.2 Hz, 1H), 7.57-7.46 (m, 2H), 7.46-7.38 (m, 1H), 7.16-7.06 (m, 2H), 4.48 (dp, J = 13.4, 6.7 Hz, 1H), 1.42 (ddd, J = 6.7, 4.4, 2.2 Hz, 6H). | 22 | [1-isopropyl-3-(trifluoromethyl) pyrazol-4-yl]boronic acid |
| 283 | 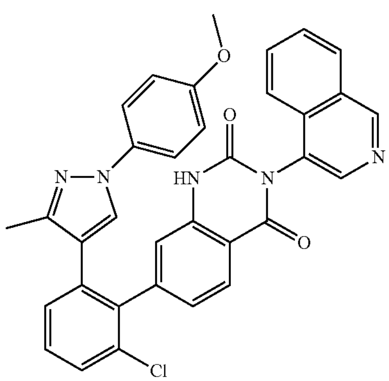 [SMILES: COc1ccc(-n2cc(-c3cccc(Cl)c3-c3ccc4c(=O)n(-c5cncc6ccccc56)c(=O)[nH]c4c3)c(C)n2)cc1] | 587.8 | 1H NMR (400 MHz, MeOD) δ 9.66 (d, J = 5.4 Hz, 1H), 8.67 (d, J = 6.9 Hz, 1H), 8.46 (s, 1H), 8.11-7.90 (m, 4H), 7.87 (d, J = 8.0 Hz, 1H), 7.76 (d, J = 17.9 Hz, 1H), 7.63 (dt, J = 7.9, 1.6 Hz, 1H), 7.60-7.50 (m, 2H), 7.50-7.43 (m, 3H), 7.24 (dd, J = 8.2, 1.5 Hz, 1H), 7.14 (dd, J = 4.0, 1.5 Hz, 1H), 7.07-6.97 (m, 2H), 3.89-3.81 (m, 3H), 2.13 (d, J = 16.3 Hz, 3H). | 22 | [1-(4-methoxyphenyl)-3-methyl-pyrazol-4-yl]boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 284 | 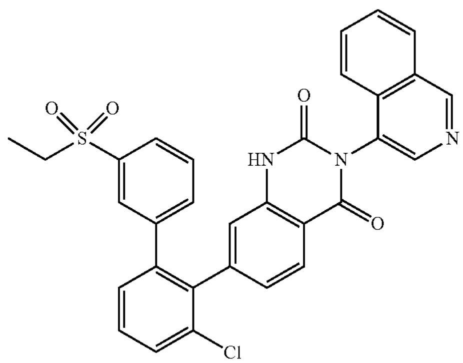 [SMILES: CCS(=O)(=O)c1cccc(-c2cccc(Cl)c2-c2ccc3c(=O)n(-c4cncc5ccccc45)c(=O)[nH]c3c2)c1] | 567.3 | 1H NMR (400 MHz, MeOD) δ 9.57 (d, J = 7.4 Hz, 1H), 8.60 (d, J = 23.6 Hz, 1H), 8.44-8.36 (m, 1H), 8.07-7.84 (m, 4H), 7.84-7.48 (m, 7H), 7.20-7.01 (m, 2H), 3.19-3.08 (m, 2H), 1.09 (dt, J = 9.4, 7.4 Hz, 3H). | 22 | 2-(3-ethylsulfonyl-phenyl)-4,4,5,5-tetramethyl-1,3,2-dioxaborolane |
| 285 | 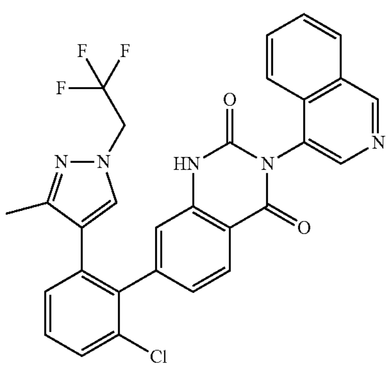 [SMILES: Cc1nn(CC(F)(F)F)cc1-c1cccc(Cl)c1-c1ccc2c(=O)n(-c3cncc4ccccc34)c(=O)[nH]c2c1] | 561.8 | 1H NMR (400 MHz, MeOD) δ 9.55 (d, J = 4.0 Hz, 1H), 8.57 (d, J = 44.9 Hz, 1H), 8.39 (t, J = 7.4 Hz, 1H), 8.06 (t, J = 7.8 Hz, 1H), 8.01-7.84 (m, 2H), 7.61 (ddd, J = 8.1, 2.7, 1.3 Hz, 1H), 7.57-7.39 (m, 2H), 7.29-6.98 (m, 3H), 4.75 (dt, J = 13.5, 8.7 Hz, 2H), 2.17 (d, J = 31.5 Hz, 3H). | 22 | 3-methyl-4-(4,4,5,5-tetramethyl-1,3,2-dioxaborolan-2-yl)-1-(2,2,2-trifluoroethyl)pyrazole |
| 286 | 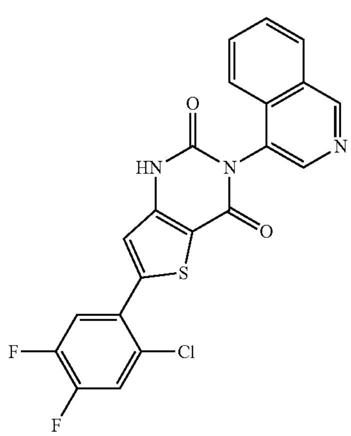 [SMILES: O=c1[nH]c2cc(-c3cc(F)c(F)cc3Cl)sc2c(=O)n1-c1cncc2ccccc12] | 441.7 | 1H NMR (400 MHz, DMSO) δ 12.35 (s, 1H), 9.49 (s, 1H), 8.61 (s, 1H), 8.31 (d, J = 8.0 Hz, 1H), 8.01 (ddd, J = 11.4, 7.8, 3.5 Hz, 2H), 7.90 (d, J = 8.1 Hz, 1H), 7.82 (dt, J = 18.4, 6.9 Hz, 2H), 7.35 (s, 1H). | 10 | 2-(2-chloro-4,5-difluoro-phenyl)-4,4,5,5-tetramethyl-1,3,2-dioxaborolane |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 287 | 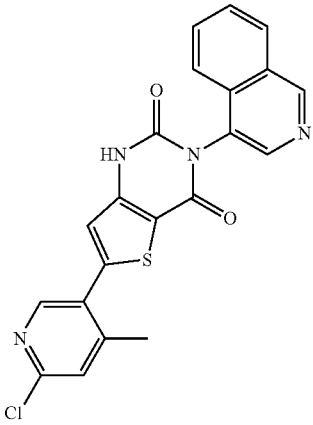 | 420.8 | 1H NMR (400 MHz, DMSO) δ 12.34 (s, 1H), 9.46 (s, 1H), 8.58 (s, 1H), 8.52 (s, 1H), 8.30 (dd, J = 7.5, 1.5 Hz, 1H), 7.91-7.74 (m, 3H), 7.67 (s, 1H), 7.24 (s, 1H). | 10 | (6-chloro-4-methyl-3-pyridyl) boronic acid |
| 288 | 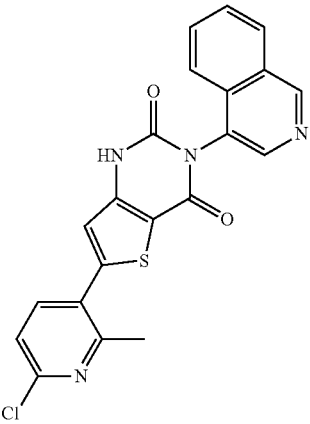 [SMILES: Cc1nc(Cl)ccc1-c1cc2[nH]c(=O)n(-c3cncc4ccccc34)c(=O)c2s1] | 420.8 | 1H NMR (400 MHz, DMSO) δ 12.34 (s, 1H), 9.49 (s, 1H), 8.61 (s, 1H), 8.32-8.29 (m, 1H), 7.98 (d, J = 8.1 Hz, 1H), 7.94-7.73 (m, 4H), 7.53 (d, J = 8.1 Hz, 1H), 7.24 (s, 1H), 2.08 (s, 3H). | 10 | (6-chloro-2-methyl-3-pyridyl) boronic acid |
| 289 | 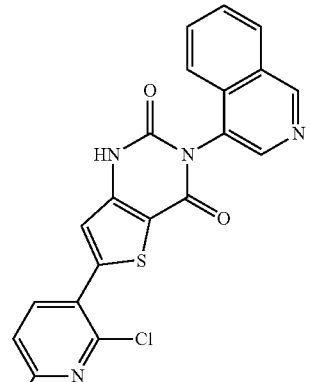 | 420.7 | 1H NMR (400 MHz, MeOD) δ 13.13 (s, 1H), 10.30 (s, 1H), 9.42 (s, 1H), 9.12 (dd, J = 7.6, 1.5 Hz, 1H), 8.94 (d, J = 7.8 Hz, 1H), 8.75-8.56 (m, 4H), 8.29 (d, J = 7.9 Hz, 1H), 8.21 (s, 1H), 3.36 (d, J = 1.4 Hz, 3H). | 10 | (2-chloro-6-methyl-3-pyridyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 290 | 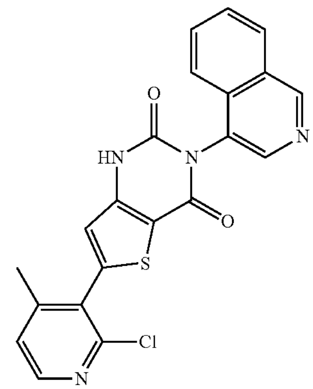 [SMILES: Cc1ccnc(Cl)c1-c1cc2[nH]c(=O)n(-c3cncc4ccccc34)c(=O)c2s1] | 420.7 | 1H NMR (400 MHz, DMSO) δ 12.37 (s, 1H), 8.67 (s, 1H), 8.41 (d, J = 5.0 Hz, 1H), 8.37-8.30 (m, 1H), 7.96 (d, J = 8.3 Hz, 1H), 7.85 (dddd, J = 22.9, 8.1, 6.8, 1.3 Hz, 3H), 7.51 (d, J = 5.0 Hz, 1H), 7.12 (s, 1H), 2.30 (s, 3H). | 10 | (2-chloro-4-methyl-3-pyridyl) boronic acid |
| 291 | 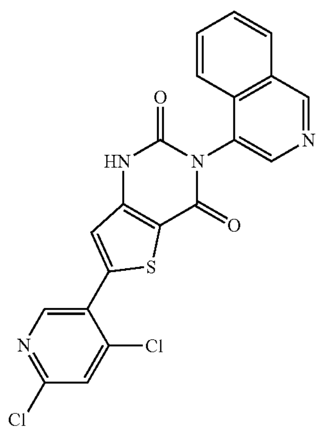 [SMILES: O=c1[nH]c2cc(-c3cnc(Cl)cc3Cl)sc2c(=O)n1-c1cncc2ccccc12] | 443.7 | 1H NMR (400 MHz, DMSO) δ 12.38 (s, 1H), 8.79 (s, 1H), 8.31 (dd, J = 7.6, 1.6 Hz, 1H), 8.09 (s, 1H), 7.89 (s, 1H), 7.81 (dddd, J = 17.9, 8.1, 6.8, 1.4 Hz, 2H), 7.44 (s, 1H). | 10 | (4,6-dichloro-3-pyridyl) boronic acid |
| 292 | 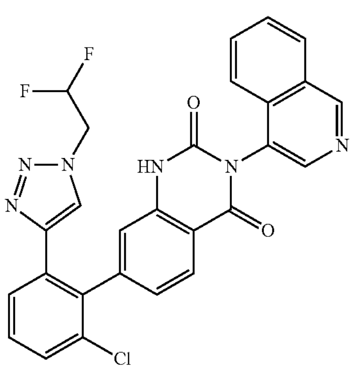 [SMILES: O=c1[nH]c2cc(-c3c(Cl)cccc3-c3cn(CC(F)F)nn3)ccc2c(=O)n1-c1cncc2ccccc12] | 531.1 | 1H NMR (400 MHz, DMSO) δ 11.82 (d, J = 10.2 Hz, 1H), 9.53 (d, J = 4.0 Hz, 1H), 8.71-8.50 (m, 1H), 8.35 (td, J = 8.3, 1.4 Hz, 1H), 8.09-7.57 (m, 7H), 7.23-7.02 (m, 3H), 6.71-6.12 (m, 1H), 4.99-4.82 (m, 2H). | 28 | 2-azido-1,1-difluoro-ethane |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 293 | 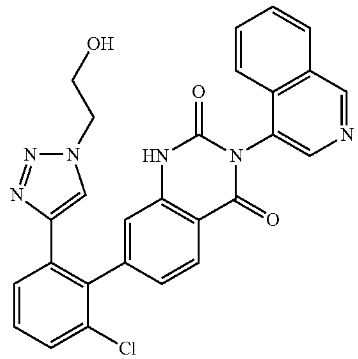 [SMILES: O=c1[nH]c2cc(-c3c(Cl)cccc3-c3cn(CCO)nn3)ccc2c(=O)n1-c1cncc2ccccc12] | 511.1 | 1H NMR (400 MHz, DMSO) δ 11.80 (d, J = 5.2 Hz, 1H), 9.53 (d, J = 3.7 Hz, 1H), 8.76-8.53 (m, 1H), 8.38-8.30 (m, 1H), 8.08-7.78 (m, 5H), 7.67 (dt, J = 8.0, 1.3 Hz, 1H), 7.60 (td, J = 7.9, 1.1 Hz, 1H), 7.18-7.05 (m, 3H), 4.42-4.27 (m, 2H), 3.74-3.61 (m, 2H). | 28 | 2-azidoethanol |
| 294 | 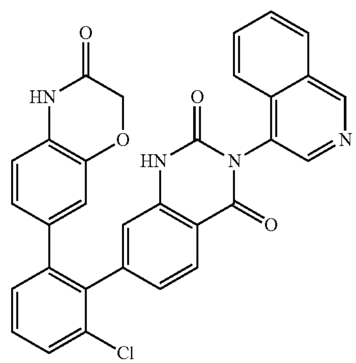 [SMILES: O=C1COc2cc(-c3cccc(Cl)c3-c3ccc4c(=O)n(-c5cncc6ccccc56)c(=O)[nH]c4c3)ccc2N1] | 547.1 | 1H NMR (400 MHz, DMSO-d6) δ 11.75 (d, J = 3.6 Hz, 1H), 10.74 (d, J = 1.8 Hz, 1H), 9.50 (s, 1H), 8.64 (d, J = 5.9 Hz, 1H), 8.46-8.11 (m, 1H), 7.96-7.76 (m, 4H), 7.65 (ddd, J = 8.1, 2.5, 1.3 Hz, 1H), 7.54 (t, J = 7.9 Hz, 1H), 7.41 (dt, J = 7.7, 1.5 Hz, 1H), 7.17-6.95 (m, 2H), 6.90-6.45 (m, 3H), 4.56 (d, J = 3.2 Hz, 2H). | 21 | 7-(4,4,5,5-tetramethyl-1,3,2-dioxaborolan-2-yl)-4H-1,4-benzoxazin-3-one |
| 295 | 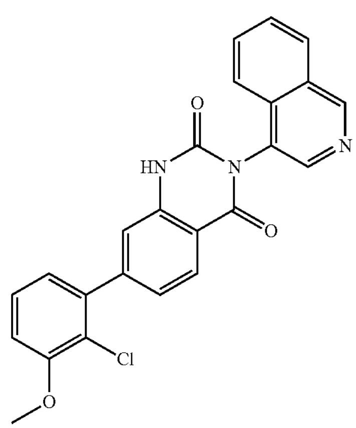 [SMILES: COc1cccc(-c2ccc3c(=O)n(-c4cncc5ccccc45)c(=O)[nH]c3c2)c1Cl] | 430.2 | 1H NMR (400 MHz, DMSO) δ 11.86 (s, 1H), 9.50 (d, J = 0.8 Hz, 1H), 8.62 (s, 1H), 8.36-8.27 (m, 1H), 8.05 (d, J = 8.0 Hz, 1H), 7.96 (dt, J = 8.4, 1.1 Hz, 1H), 7.88-7.76 (m, 2H), 7.47 (dd, J = 8.3, 7.6 Hz, 1H), 7.34-7.25 (m, 3H), 7.04 (dd, J = 7.6, 1.4 Hz, | 4 | (2-chloro-3-methoxyphenyl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | 1H), 3.94 (s, 3H). | | |
| 296 | 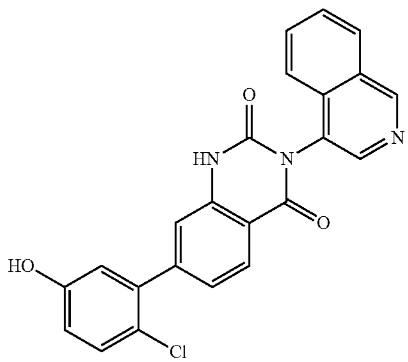 [SMILES: O=c1[nH]c2cc(-c3cc(O)ccc3Cl)ccc2c(=O)n1-c1cncc2ccccc12] | 416.1 | 1H NMR (400 MHz, DMSO) δ 11.87 (s, 1H), 10.00 (s, 1H), 9.52 (s, 1H), 8.64 (s, 1H), 8.37-8.29 (m, 1H), 8.04 (d, J = 8.0 Hz, 1H), 7.98 (dd, J = 8.3, 1.4 Hz, 1H), 7.83 (dddd, J = 15.0, 8.2, 6.9, 1.4 Hz, 2H), 7.42 (d, J = 8.6 Hz, 1H), 7.34-7.27 (m, 2H), 6.89 (dd, J = 8.7, 2.9 Hz, 1H), 6.84 (d, J = 2.9 Hz, 1H). | 5 | 3-bromo-4-chloro-phenol |
| 297 | 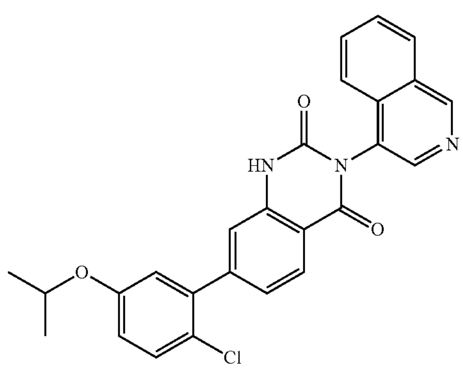 [SMILES: CC(C)Oc1ccc(Cl)c(-c2ccc3c(=O)n(-c4cncc5ccccc45)c(=O)[nH]c3c2)c1] | 458.1 | 1H NMR (400 MHz, DMSO) δ 11.87 (s, 1H), 9.53 (s, 1H), 8.65 (s, 1H), 8.38-8.31 (m, 1H), 8.05 (d, J = 8.0 Hz, 1H), 7.97 (dd, J = 8.2, 1.3 Hz, 1H), 7.84 (dddd, J = 16.3, 8.1, 6.9, 1.4 Hz, 2H), 7.52 (d, J = 8.9 Hz, 1H), 7.38-7.30 (m, 2H), 7.07 (dd, J = 8.9, 3.0 Hz, 1H), 6.98 (d, J = 3.0 Hz, 1H), 4.70 (hept, J = 6.0 Hz, 1H), 1.31 (d, J = 6.0 Hz, 6H). | 4 | (2-chloro-5-isopropoxy-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 298 | 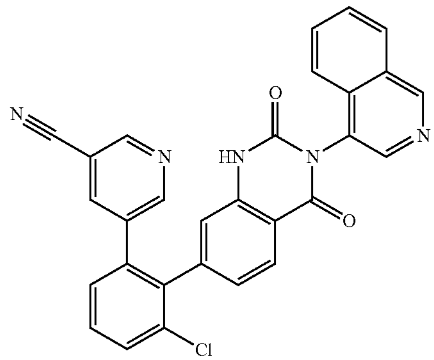 [SMILES: N#Cc1cncc(-c2cccc(Cl)c2-c2ccc3c(=O)n(-c4cncc5ccccc45)c(=O)[nH]c3c2)c1] | 502.2 | 1H NMR (400 MHz, DMSO) δ 11.78 (d, J = 4.2 Hz, 1H), 9.51 (d, J = 1.7 Hz, 1H), 8.94 (dd, J = 3.0, 2.0 Hz, 1H), 8.65 (d, J = 11.1 Hz, 1H), 8.62-8.54 (m, 1H), 8.36-8.25 (m, 2H), 7.98-7.75 (m, 5H), 7.66 (t, J = 7.8 Hz, 1H), 7.58 (ddd, J = 7.7, 3.6, 1.3 Hz, 1H), 7.16-7.04 (m, 2H). | 21 | 5-(4,4,5,5-tetramethyl-1,3,2-dioxaborolan-2-yl)pyridine-3-carbonitrile |
| 299 | 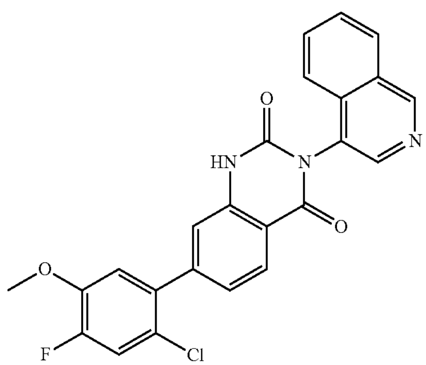 [SMILES: COc1cc(-c2ccc3c(=O)n(-c4cncc5ccccc45)c(=O)[nH]c3c2)c(Cl)cc1F] | 448.1 | 1H NMR (400 MHz, DMSO) δ 11.89 (s, 1H), 9.52 (d, J = 0.8 Hz, 1H), 8.64 (s, 1H), 8.37-8.30 (m, 1H), 8.06 (d, J = 8.1 Hz, 1H), 7.94 (dd, J = 8.2, 1.4 Hz, 1H), 7.83 (dddd, J = 16.2, 8.1, 6.9, 1.4 Hz, 2H), 7.66 (d, J = 11.1 Hz, 1H), 7.39-7.31 (m, 2H), 7.26 (d, J = 9.0 Hz, 1H), 3.92 (s, 3H). | 4 | (2-chloro-4-fluoro-5-methoxy-phenyl) boronic acid |
| 300 | 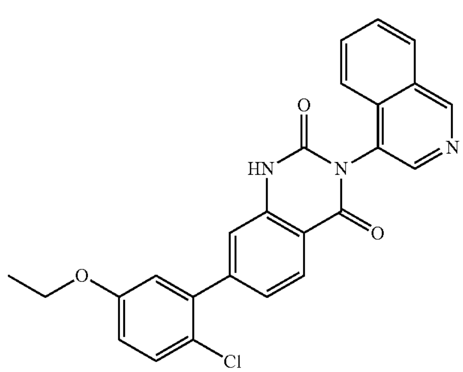 [SMILES: CCOc1ccc(Cl)c(-c2ccc3c(=O)n(-c4cncc5ccccc45)c(=O)[nH]c3c2)c1] | 444.1 | 1H NMR (400 MHz, DMSO) δ 11.87 (s, 1H), 9.51 (s, 1H), 8.63 (s, 1H), 8.33 (dd, J = 7.3, 1.8 Hz, 1H), 8.05 (d, J = 8.1 Hz, 1H), 7.95 (dd, J = 8.1, 1.4 Hz, 1H), 7.82 (dddd, J = 14.6, 8.2, 6.9, 1.4 Hz, 2H), 7.54 (d, J = 8.8 Hz, 1H), 7.38-7.30 (m, 2H), 7.08 (dd, J = | 4 | (2-chloro-5-ethoxy-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | 8.9, 3.0 Hz, 1H), 7.00 (d, J = 3.0 Hz, 1H), 4.11 (q, J = 7.0 Hz, 2H), 1.36 (t, J = 7.0 Hz, 3H). | | |
| 301 | 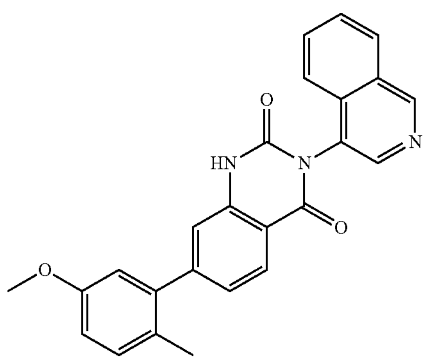 [SMILES: COc1ccc(C)c(-c2ccc3c(=O)n(-c4cncc5ccccc45)c(=O)[nH]c3c2)c1] | 410.2 | 1H NMR (400 MHz, DMSO) δ 11.84 (s, 1H), 9.54 (d, J = 0.9 Hz, 1H), 8.65 (s, 1H), 8.38-8.31 (m, 1H), 8.03 (d, J = 8.0 Hz, 1H), 7.99-7.93 (m, 1H), 7.84 (dddd, J = 17.6, 8.0, 6.8, 1.4 Hz, 2H), 7.33-7.22 (m, 3H), 6.97 (dd, J = 8.4, 2.8 Hz, 1H), 6.82 (d, J = 2.8 Hz, 1H), 2.51 (p, J = 1.9 Hz, 3H), 2.21 (s, 3H). | 4 | (5-methoxy-2-methyl-phenyl) boronic acid |
| 302 | 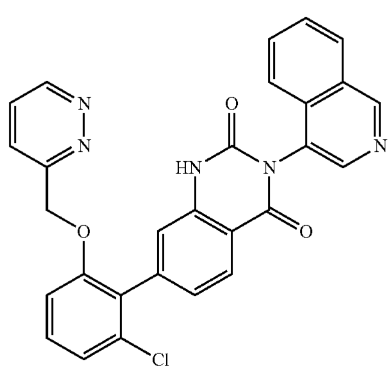 [SMILES: O=c1[nH]c2cc(-c3c(Cl)cccc3OCc3cccnn3)ccc2c(=O)n1-c1cncc2ccccc12] | 508.1 | 1H NMR (400 MHz, DMSO) δ 11.85 (s, 1H), 9.54 (s, 1H), 9.21 (dd, J = 5.0, 1.7 Hz, 1H), 8.67 (s, 1H), 8.38-8.31 (m, 1H), 8.07-7.98 (m, 2H), 7.91-7.82 (m, 2H), 7.74 (dd, J = 8.5, 4.9 Hz, 1H), 7.56 (d, J = 8.4 Hz, 1H), 7.46 (t, J = 8.2 Hz, 1H), 7.37-7.21 (m, 4H), 5.48 (s, 2H). | 5 | I-135 |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 303 | 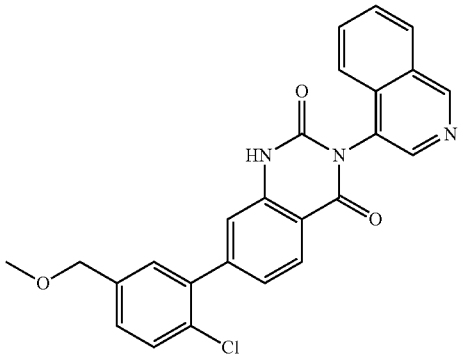 [SMILES: COCc1ccc(Cl)c(-c2ccc3c(=O)n(-c4cncc5ccccc45)c(=O)[nH]c3c2)c1] | 444.1 | 1H NMR (400 MHz, DMSO) δ 11.87 (s, 1H), 9.53 (d, J = 0.9 Hz, 1H), 8.65 (s, 1H), 8.38-8.31 (m, 1H), 8.06 (d, J = 8.1 Hz, 1H), 8.02-7.94 (m, 1H), 7.84 (dddd, J = 16.3, 8.1, 6.9, 1.4 Hz, 2H), 7.64 (d, J = 8.2 Hz, 1H), 7.49-7.40 (m, 2H), 7.38-7.29 (m, 2H), 4.50 (s, 2H), 3.35 (s, 3H). | 4 | [2-chloro-5-(methoxymethyl)phenyl] boronic acid |
| 304 | 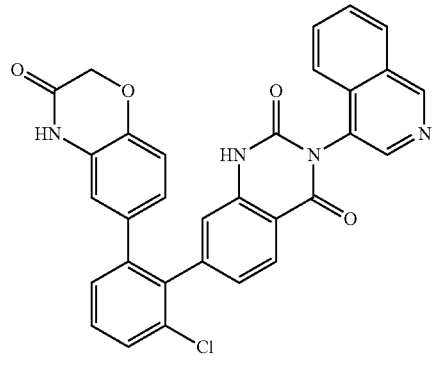 [SMILES: O=C1COc2ccc(-c3cccc(Cl)c3-c3ccc4c(=O)n(-c5cncc6ccccc56)c(=O)[nH]c4c3)cc2N1] | 547.1 | 1H NMR (400 MHz, DMSO) δ 11.78-11.72 (m, 1H), 10.76 (d, J = 6.7 Hz, 1H), 9.51 (d, J = 3.9 Hz, 1H), 8.64 (dd, J = 6.1, 3.1 Hz, 1H), 8.32 (ddd, J = 9.4, 3.8, 2.2 Hz, 1H), 7.96-7.75 (m, 4H), 7.66 (dt, J = 8.1, 1.3 Hz, 1H), 7.56 (t, J = 7.9 Hz, 1H), 7.41 (td, J = 7.4, 1.3 Hz, 1H), 7.12-6.95 (m, 2H), 6.83 (dd, J = 15.2, 8.2 Hz, 1H), 6.77-6.61 (m, 2H), 4.57 (d, J = 0.9 Hz, 2H). | 21 | 6-(4,4,5,5-tetramethyl-1,3,2-dioxaborolan-2-yl)-4H-1,4-benzoxazin-3-one |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 305 | 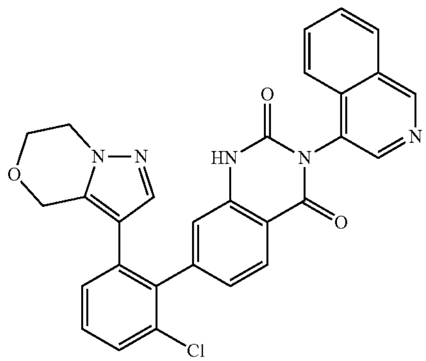 [SMILES: O=c1[nH]c2cc(-c3c(Cl)cccc3-c3cnn4c3COCC4)ccc2c(=O)n1-c1cncc2ccccc12] | 522.1 | 1H NMR (400 MHz, DMSO) δ 11.78 (d, J = 1.8 Hz, 1H), 9.50 (d, J = 0.8 Hz, 1H), 8.66 (d, J = 12.1 Hz, 1H), 8.36-8.27 (m, 1H), 8.00-7.75 (m, 4H), 7.58 (ddd, J = 8.0, 2.8, 1.2 Hz, 1H), 7.55-7.46 (m, 1H), 7.31 (dd, J = 7.7, 1.3 Hz, 1H), 7.14-7.04 (m, 2H), 6.92-6.80 (m, 1H), 4.75 (s, 2H), 4.11-4.00 (m, 4H). | 21 | 3-(4,4,5,5-tetramethyl-1,3,2-dioxaborolan-2-yl)-6,7-dihydro-4H-pyrazolo[5,1-c][1,4]oxazine |
| 306 | 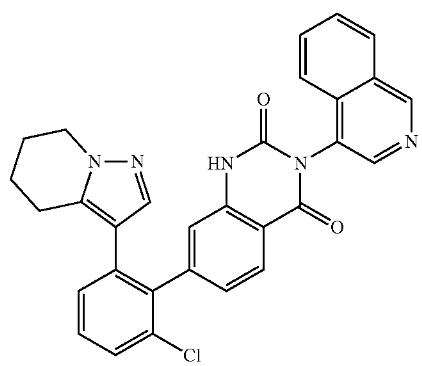 [SMILES: O=c1[nH]c2cc(-c3c(Cl)cccc3-c3cnn4c3CCCC4)ccc2c(=O)n1-c1cncc2ccccc12] | 520.2 | 1H NMR (400 MHz, DMSO) δ 11.77 (d, J = 3.3 Hz, 1H), 9.52 (s, 1H), 8.67 (d, J = 11.9 Hz, 1H), 8.33 (dt, J = 8.7, 1.8 Hz, 1H), 8.00-7.76 (m, 4H), 7.57 (ddd, J = 8.0, 3.0, 1.3 Hz, 1H), 7.50 (t, J = 7.8 Hz, 1H), 7.41 (dt, J = 7.6, 1.4 Hz, 1H), 7.12-7.02 (m, 2H), 6.88-6.78 (m, 1H), 4.02 (q, J = 6.2 Hz, 2H), 2.69 (td, J = 6.2, 3.0 Hz, 2H), 1.95 (h, J = 6.4 Hz, 2H), 1.78 (dt, J = 9.7, 5.0 Hz, 2H). | 21 | 3-(4,4,5,5-tetramethyl-1,3,2-dioxaborolan-2-yl)-4,5,6,7-tetrahydro-pyrazolo[1,5-a]pyridine |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 307 | 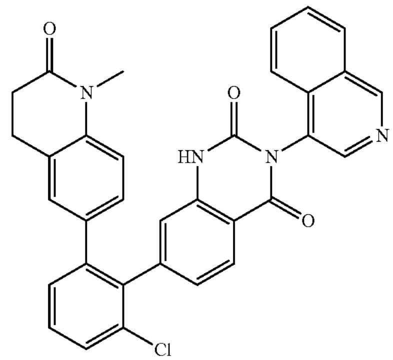 [SMILES: CN1C(=O)CCc2cc(-c3cccc(Cl)c3-c3ccc4c(=O)n(-c5cncc6ccccc56)c(=O)[nH]c4c3)ccc21] | 559.1 | 1H NMR (400 MHz, DMSO) δ 11.74 (d, J = 4.1 Hz, 1H), 9.50 (s, 1H), 8.60 (t, J = 14.1 Hz, 1H), 8.32 (ddd, J = 6.7, 3.6, 1.7 Hz, 1H), 7.92 (dd, J = 9.8, 7.4 Hz, 1H), 7.88-7.75 (m, 2H), 7.70-7.50 (m, 3H), 7.44 (ddd, J = 7.7, 2.8, 1.3 Hz, 1H), 7.16-7.07 (m, 2H), 7.07-6.90 (m, 3H), 3.34-3.18 (m, 3H), 2.87-2.77 (m, 2H), 2.53 (d, J = 6.8 Hz, 2H). | 21 | 1-methyl-6-(4,4,5,5-tetramethyl-1,3,2-dioxaborolan-2-yl)-3,4-dihydroquinolin-2-one |
| 308 | 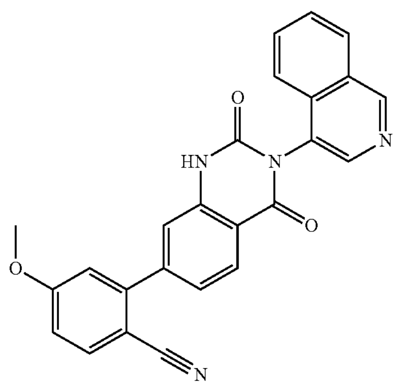 [SMILES: COc1ccc(C#N)c(-c2ccc3c(=O)n(-c4cncc5ccccc45)c(=O)[nH]c3c2)c1] | 421.1 | 1H NMR (400 MHz, DMSO) δ 11.99 (s, 1H), 9.59-9.55 (m, 1H), 8.69 (s, 1H), 8.40-8.33 (m, 1H), 8.11 (d, J = 8.0 Hz, 1H), 8.05-7.94 (m, 2H), 7.92-7.79 (m, 2H), 7.51-7.43 (m, 2H), 7.28-7.16 (m, 2H), 3.94 (s, 3H). | 5 | 2-bromo-4-methoxy-benzonitrile |
| 309 | 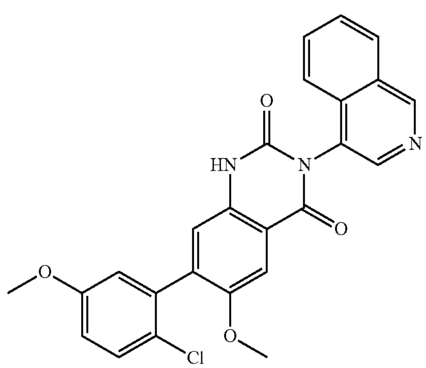 [SMILES: COc1ccc(Cl)c(-c2cc3[nH]c(=O)n(-c4cncc5ccccc45)c(=O)c3cc2OC)c1] | 460.1 | 1H NMR (400 MHz, DMSO) δ 11.75 (s, 1H), 9.50 (s, 1H), 8.62 (s, 1H), 8.32 (dd, J = 7.7, 1.5 Hz, 1H), 7.92-7.76 (m, 3H), 7.55-7.46 (m, 2H), 7.12 (s, 1H), 7.06 (dd, J = 8.9, 3.1 Hz, 1H), 6.94 (d, J = 3.0 Hz, 1H), 3.80 (d, J = 6.5 Hz, 6H). | 4 | I-19, (2-chloro-5-methoxy-phenyl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 310 | 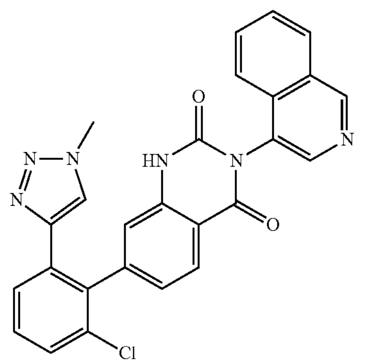 [SMILES: Cn1cc(-c2cccc(Cl)c2-c2ccc3c(=O)n(-c4cncc5ccccc45)c(=O)[nH]c3c2)nn1] | 481.1 | 1H NMR (400 MHz, DMSO) δ 11.83 (s, 1H), 9.45 (s, 1H), 8.69-8.51 (m, 1H), 8.29 (dt, J = 6.6, 2.4 Hz, 1H), 8.07-7.73 (m, 5H), 7.71-7.56 (m, 2H), 7.26-7.15 (m, 1H), 7.12-7.02 (m, 2H), 3.97 (d, J = 9.7 Hz, 3H). | 28 | azidomethyl (trimethyl) silane |
| 311 | 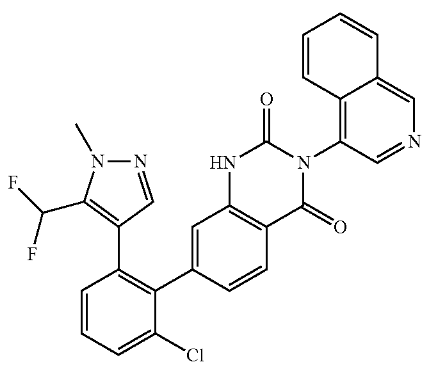 [SMILES: Cn1ncc(-c2cccc(Cl)c2-c2ccc3c(=O)n(-c4cncc5ccccc45)c(=O)[nH]c3c2)c1C(F)F] | 529.9 | 1H NMR (400 MHz, DMSO) δ 11.80 (s, 1H), 9.51 (s, 1H), 8.66 (d, J = 7.6 Hz, 1H), 8.33 (dt, J = 8.6, 1.8 Hz, 1H), 7.98-7.76 (m, 4H), 7.69 (ddd, J = 8.1, 2.5, 1.2 Hz, 1H), 7.55 (t, J = 7.9 Hz, 1H), 7.33 (dd, J = 7.7, 1.2 Hz, 1H), 7.20-6.96 (m, 4H), 3.90 (d, J = 6.2 Hz, 3H). | 21 | 5-(difluoromethyl)-1-methyl-4-(4,4,5,5-tetramethyl-1,3,2-dioxaborolan-2-yl)pyrazole |
| 312 | 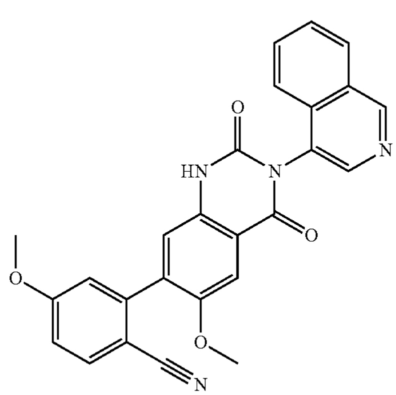 [SMILES: COc1ccc(C#N)c(-c2cc3[nH]c(=O)n(-c4cncc5ccccc45)c(=O)c3cc2OC)c1] | 450.9 | 1H NMR (400 MHz, DMSO) δ 11.81 (s, 1H), 9.52 (d, J = 0.8 Hz, 1H), 8.64 (s, 1H), 8.37-8.30 (m, 1H), 7.92 (d, J = 8.7 Hz, 2H), 7.83 (dddd, J = 16.1, 8.2, 6.8, 1.5 Hz, 2H), 7.59 (s, 1H), 7.25-7.15 (m, 2H), 7.11 (d, J = 2.6 Hz, 1H), 3.93-3.78 (m, 6H). | 5 | 2-bromo-4-methoxy-benzonitrile |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 313 | 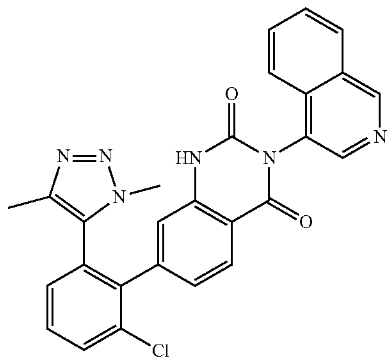 [SMILES: Cc1nnn(C)c1-c1cccc(Cl)c1-c1ccc2c(=O)n(-c3cncc4ccccc34)c(=O)[nH]c2c1] | 494.8 | 1H NMR (400 MHz, DMSO) δ 11.75 (d, J = 2.6 Hz, 1H), 9.49 (s, 1H), 8.63 (s, 1H), 8.32 (dt, J = 8.4, 2.2 Hz, 1H), 7.96-7.70 (m, 5H), 7.59 (t, J = 7.9 Hz, 1H), 7.44 (dt, J = 7.6, 1.1 Hz, 1H), 7.08 (dd, J = 8.3, 1.6 Hz, 1H), 6.98 (ddd, J = 7.7, 5.9, 1.5 Hz, 1H), 3.88 (d, J = 6.0 Hz, 3H), 2.09 (d, J = 3.9 Hz, 3H). | 21 | 1,4-dimethyl-5-(4,4,5,5-tetramethyl-1,3,2-dioxaborolan-2-yl)triazole |
| 314 | 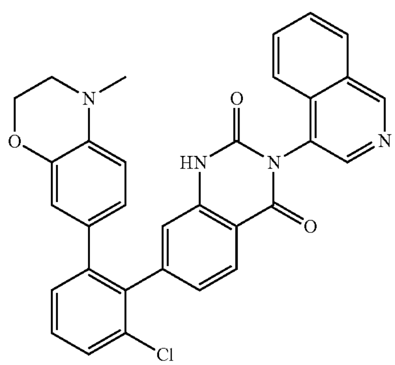 [SMILES: CN1CCOc2cc(-c3cccc(Cl)c3-c3ccc4c(=O)n(-c5cncc6ccccc56)c(=O)[nH]c4c3)ccc21] | 546.8 | 1H NMR (400 MHz, DMSO) δ 11.76 (d, J = 3.3 Hz, 1H), 9.52 (s, 1H), 8.66 (d, J = 1.8 Hz, 1H), 8.37-8.30 (m, 1H), 7.98-7.76 (m, 4H), 7.58 (ddd, J = 8.0, 2.5, 1.3 Hz, 1H), 7.49 (t, J = 7.8 Hz, 1H), 7.37 (ddd, J = 7.7, 2.9, 1.3 Hz, 1H), 7.10 (ddd, J = 8.1, 2.8, 1.5 Hz, 1H), 7.04 (d, J = 1.5 Hz, 1H), 6.60-6.47 (m, 3H), 4.19 (td, J = 5.4, 3.5 Hz, 2H), 3.23 (q, J = 4.7 Hz, 2H), 2.80 (d, J = 5.2 Hz, 3H). | 21 | 4-methyl-7-(4,4,5,5-tetramethyl-1,3,2-dioxaborolan-2-yl)-2,3-dihydro-1,4-benzoxazine |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 315 | 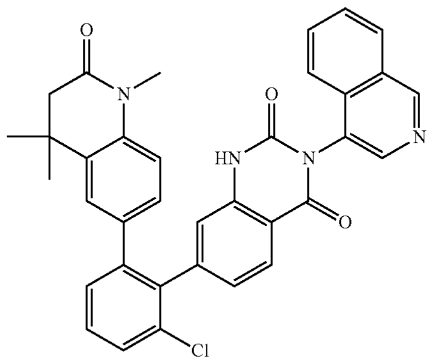 [SMILES: CN1C(=O)CC(C)(C)c2cc(-c3cccc(Cl)c3-c3ccc4c(=O)n(-c5cncc6ccccc56)c(=O)[nH]c4c3)ccc21] | 586.8 | 1H NMR (400 MHz, DMSO) δ 11.94-11.61 (m, 1H), 9.51 (s, 1H), 8.68-8.46 (m, 1H), 8.38-8.29 (m, 1H), 8.01-7.45 (m, 7H), 7.34-7.00 (m, 4H), 6.96-6.84 (m, 1H), 3.27 (d, J = 5.4 Hz, 3H), 2.44-2.37 (m, 2H), 1.05-0.97 (m, 6H). | 21 | I-136 |
| 316 | 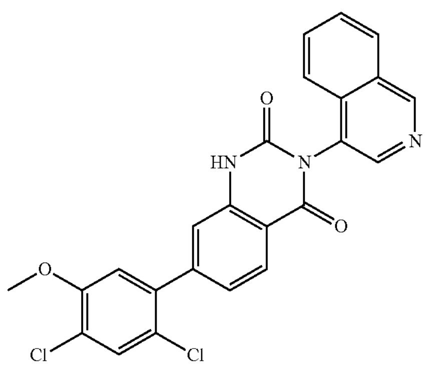 | 463.7 | 1H NMR (400 MHz, DMSO) δ 11.89 (s, 1H), 9.51 (s, 1H), 8.63 (d, J = 2.2 Hz, 1H), 8.36-8.30 (m, 1H), 8.08 (d, J = 8.0 Hz, 1H), 7.93 (d, J = 8.2 Hz, 1H), 7.89-7.76 (m, 3H), 7.48-7.16 (m, 3H), 3.94 (s, 3H). | 4 | (2,4-dichloro-5-methoxy-phenyl) boronic acid |
| 317 | 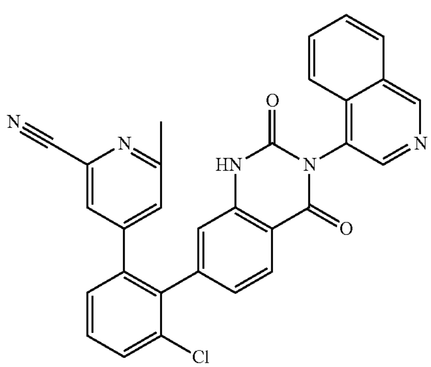 [SMILES: Cc1cc(-c2cccc(Cl)c2-c2ccc3c(=O)n(-c4cncc5ccccc45)c(=O)[nH]c3c2)cc(C#N)n1] | 515.8 | 1H NMR (400 MHz, DMSO) δ 11.75 (d, J = 6.2 Hz, 1H), 9.51 (s, 1H), 8.67-8.58 (m, 1H), 8.37-8.28 (m, 1H), 7.97-7.76 (m, 5H), 7.76-7.61 (m, 2H), 7.54 (ddd, J = 8.9, 7.7, 1.2 Hz, 1H), 7.50-7.39 (m, 1H), 7.23-7.11 (m, 1H), 7.01 (dd, J = 17.4, 1.6 Hz, 1H), 2.50-2.44 (m, 3H). | 21 | 6-methyl-4-(4,4,5,5-tetramethyl-1,3,2-dioxaborolan-2-yl)pyridine-2-carbonitrile |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 318 | 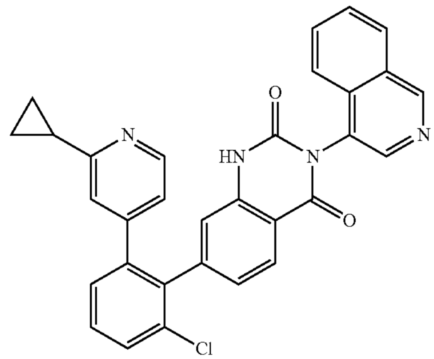 [SMILES: O=c1[nH]c2cc(-c3c(Cl)cccc3-c3ccnc(C4CC4)c3)ccc2c(=O)n1-c1cncc2ccccc12] | 516.8 | 1H NMR (400 MHz, DMSO) δ 11.80 (d, J = 7.0 Hz, 1H), 9.49 (s, 1H), 8.61 (d, J = 15.8 Hz, 1H), 8.42 (dd, J = 14.8, 5.6 Hz, 1H), 8.32 (ddd, J = 8.3, 6.3, 1.8 Hz, 1H), 7.97-7.74 (m, 5H), 7.66 (td, J = 7.9, 2.3 Hz, 1H), 7.58 (ddd, J = 10.4, 7.7, 1.3 Hz, 1H), 7.32-7.03 (m, 4H), 2.17 (dtd, J = 12.8, 8.1, 4.8 Hz, 1H), 1.13 (dt, J = 6.6, 3.3 Hz, 2H), 0.98-0.82 (m, 2H). | 21 | (2-cyclopropyl-4-pyridyl) boronic acid |
| 319 | 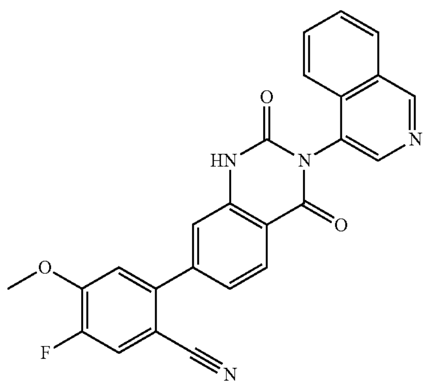 [SMILES: COc1cc(-c2ccc3c(=O)n(-c4cncc5ccccc45)c(=O)[nH]c3c2)c(C#N)cc1F] | 438.9 | 1H NMR (400 MHz, DMSO) δ 11.98 (s, 1H), 9.51 (s, 1H), 8.64 (s, 1H), 8.36-8.29 (m, 1H), 8.15-8.02 (m, 2H), 7.95 (dt, J = 8.5, 1.1 Hz, 1H), 7.82 (dddd, J = 14.6, 8.2, 6.9, 1.5 Hz, 2H), 7.52-7.40 (m, 3H), 4.03 (s, 3H). | 5 | 2-bromo-5-fluoro-4-methoxy-benzonitrile |
| 320 | 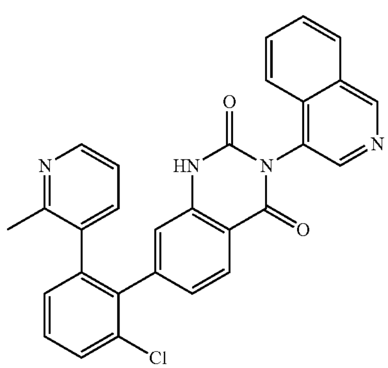 [SMILES: Cc1ncccc1-c1cccc(Cl)c1-c1ccc2c(=O)n(-c3cncc4ccccc34)c(=O)[nH]c2c1] | 490.8 | 1H NMR (400 MHz, DMSO) δ 12.07-11.32 (m, 1H), 9.47 (s, 1H), 8.63-8.56 (m, 2H), 8.33-8.25 (m, 1H), 8.01-7.74 (m, 6H), 7.69-7.43 (m, 3H), 7.19-7.11 (m, 1H), 7.03-6.92 (m, 1H), 2.40 (d, J = 14.8 Hz, 3H). | 21 | (2-methyl-3-pyridyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 321 | 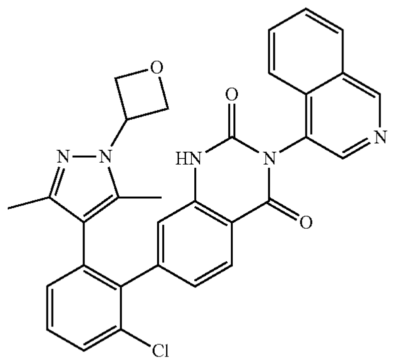 [SMILES: Cc1nn(C2COC2)c(C)c1-c1cccc(Cl)c1-c1ccc2c(=O)n(-c3cncc4ccccc34)c(=O)[nH]c2c1] | 549.8 | 1H NMR (400 MHz, DMSO) δ 11.81-11.49 (m, 1H), 9.49 (s, 1H), 8.67-8.60 (m, 1H), 8.35-8.28 (m, 1H), 7.99-7.73 (m, 4H), 7.70-7.63 (m, 1H), 7.52 (t, J = 7.9 Hz, 1H), 7.33-7.25 (m, 1H), 7.15-6.86 (m, 2H), 5.44 (tdd, J = 13.9, 9.5, 6.5 Hz, 1H), 4.98-4.70 (m, 4H), 2.02-1.77 (m, 6H). | 21 | 3,5-dimethyl-1-(oxetan-3-yl)-4-(4,4,5,5-tetramethyl-1,3,2-dioxaborolan-2-yl)pyrazole |
| 322 | 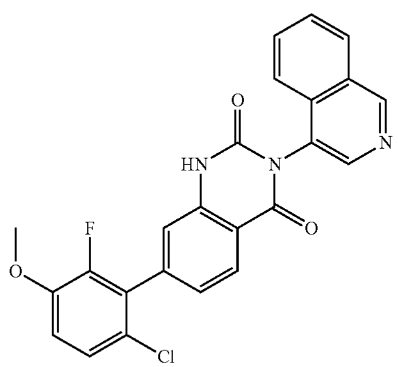 [SMILES: COc1ccc(Cl)c(-c2ccc3c(=O)n(-c4cncc5ccccc45)c(=O)[nH]c3c2)c1F] | 447.8 | 1H NMR (400 MHz, DMSO) δ 11.89 (s, 1H), 9.50 (s, 1H), 8.64 (s, 1H), 8.36-8.29 (m, 1H), 8.12-8.05 (m, 1H), 8.05-7.97 (m, 1H), 7.88-7.76 (m, 2H), 7.47 (dd, J = 8.9, 1.8 Hz, 1H), 7.34 (t, J = 9.0 Hz, 1H), 7.29-7.23 (m, 2H), 3.93 (s, 3H). | 5 | 2-bromo-1-chloro-3-fluoro-4-methoxy-benzene |
| 323 | 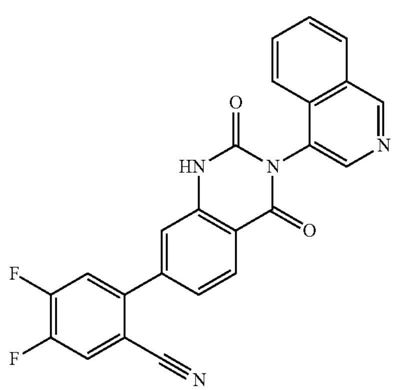 [SMILES: N#Cc1cc(F)c(F)cc1-c1ccc2c(=O)n(-c3cncc4ccccc34)c(=O)[nH]c2c1] | 426.8 | 1H NMR (400 MHz, DMSO) δ 12.01 (s, 1H), 9.51 (d, J = 0.9 Hz, 1H), 8.64 (s, 1H), 8.44-8.32 (m, 2H), 8.15-8.09 (m, 1H), 8.01-7.90 (m, 2H), 7.82 (pd, J = 6.9, 1.5 Hz, 2H), 7.50-7.43 (m, 2H). | 5 | 2-bromo-4,5-difluoro-benzonitrile |

TABLE 18-continued

Examples 177-384

| Example | Structure | ES/MS m/z | 1H-NMR | Procedure | Changes to Procedure: Different Reagents/ Starting Materials |
| --- | --- | --- | --- | --- | --- |
| 324 | 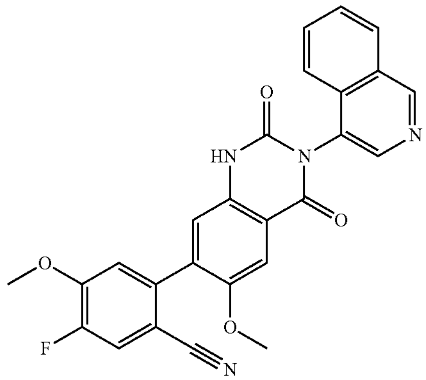 [SMILES: COc1cc(-c2cc3[nH]c(=O)n(-c4cncc5ccccc45)c(=O)c3cc2OC)c(C#N)cc1F] | 468.8 | 1H NMR (400 MHz, DMSO) δ 11.81 (s, 1H), 9.50 (s, 1H), 8.63 (s, 1H), 8.36-8.29 (m, 1H), 8.00 (d, J = 11.2 Hz, 1H), 7.92-7.76 (m, 3H), 7.59 (s, 1H), 7.37 (d, J = 8.2 Hz, 1H), 7.25 (s, 1H), 3.98 (s, 3H), 3.84 (s, 3H). | 5 | 2-bromo-5-fluoro-4-methoxy-benzonitrile (I-102) |
| 325 | 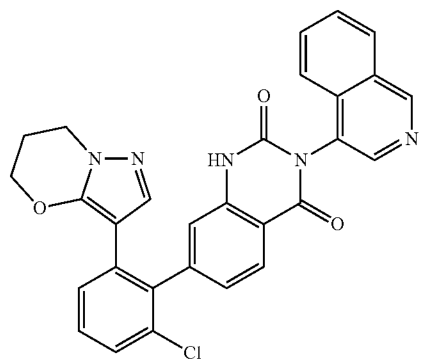 | 521.8 | 1H NMR (400 MHz, DMSO) δ 11.80 (d, J = 3.0 Hz, 1H), 9.52 (s, 1H), 8.68 (d, J = 8.1 Hz, 1H), 8.33 (dt, J = 7.3, 2.1 Hz, 1H), 8.04-7.76 (m, 4H), 7.59 (dq, J = 4.7, 2.5 Hz, 1H), 7.52-7.42 (m, 2H), 7.13-7.04 (m, 2H), 6.73-6.39 (m, 1H), 4.30 (td, J = 6.0, 4.4 Hz, 2H), 4.05 (q, J = 6.1 Hz, 2H), 2.21-2.13 (m, 2H). | 21 | 3-(4,4,5,5-tetramethyl-1,3,2-dioxaborolan-2-yl)-6,7-dihydro-5H-pyrazolo[5,1-b][1,3]oxazine |
| 326 | 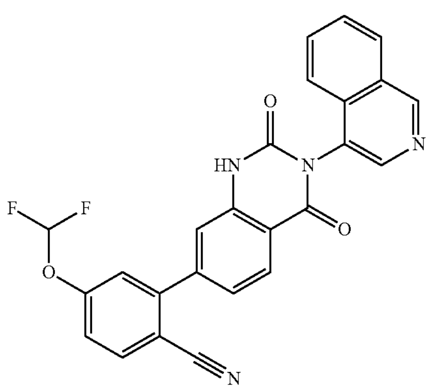 [SMILES: N#Cc1ccc(OC(F)F)cc1-c1ccc2c(=O)n(-c3cncc4ccccc34)c(=O)[nH]c2c1] | 456.8 | 1H NMR (400 MHz, DMSO-d6) δ 12.00 (s, 1H), 9.54 (s, 1H), 8.67 (s, 1H), 8.43-8.27 (m, 1H), 8.19-8.10 (m, 2H), 8.04-7.97 (m, 1H), 7.91-7.72 (m, 2H), 7.61-7.35 (m, 5H). | 5 | 2-bromo-4-(difluoro-methoxy)benzonitrile |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 327 | 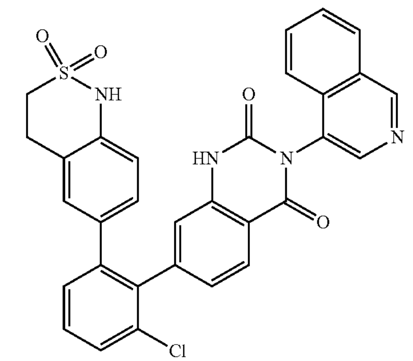 [SMILES: O=c1[nH]c2cc(-c3c(Cl)cccc3-c3ccc4c(c3)CCS(=O)(=O)N4)ccc2c(=O)n1-c1cncc2ccccc12] | 580.7 | 1H NMR (400 MHz, DMSO-d6) δ 11.73 (d, J = 1.8 Hz, 1H), 10.20 (s, 1H), 9.49 (s, 1H), 8.64 (d, J = 9.0 Hz, 1H), 8.31 (dt, J = 8.5, 2.2 Hz, 1H), 8.03-7.75 (m, 4H), 7.65 (dt, J = 8.0, 1.5 Hz, 1H), 7.55 (t, J = 7.9 Hz, 1H), 7.43 (ddd, J = 7.7, 5.4, 1.3 Hz, 1H), 7.23-7.00 (m, 3H), 6.89 (ddd, J = 21.1, 8.3, 2.1 Hz, 1H), 6.60 (dd, J = 20.0, 8.3 Hz, 1H), 3.42-3.19 (m, 4H). | 21 | I-137 |
| 328 | 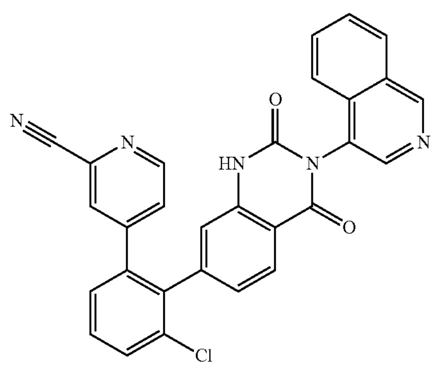 [SMILES: N#Cc1cc(-c2cccc(Cl)c2-c2ccc3c(=O)n(-c4cncc5ccccc45)c(=O)[nH]c3c2)ccn1] | 501.8 | 1H NMR (400 MHz, DMSO-d6) δ 11.74 (d, J = 5.7 Hz, 1H), 9.47 (s, 1H), 8.75-8.52 (m, 2H), 8.30 (ddd, J = 8.3, 4.0, 2.0 Hz, 1H), 8.01 (dd, J = 14.7, 1.7 Hz, 1H), 7.95-7.87 (m, 2H), 7.87-7.75 (m, 4H), 7.67 (td, J = 7.9, 1.2 Hz, 1H), 7.58 (ddd, J = 8.9, 7.6, 1.3 Hz, 1H), 7.46 (ddd, J = 8.7, 5.1, 1.8 Hz, 1H), 7.04 (dd, J = 17.6, 1.5 Hz, 1H). | 21 | 4-(4,4,5,5-tetramethyl-1,3,2-dioxaborolan-2-yl)pyridine-2-carbonitrile |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 329 | 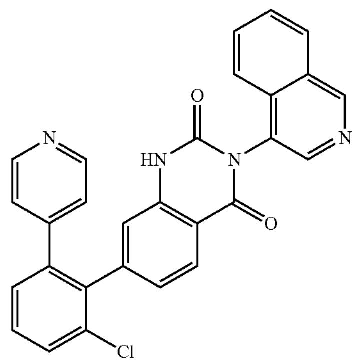 [SMILES: O=c1[nH]c2cc(-c3c(Cl)cccc3-c3ccncc3)ccc2c(=O)n1-c1cncc2ccccc12] | 476.8 | 1H NMR (400 MHz, DMSO-d6) δ 11.77 (d, J = 5.3 Hz, 1H), 9.48 (s, 1H), 8.75-8.54 (m, 3H), 8.31 (ddd, J = 8.3, 4.4, 1.8 Hz, 1H), 7.96-7.74 (m, 5H), 7.68 (td, J = 7.9, 1.2 Hz, 1H), 7.56 (td, J = 7.5, 1.2 Hz, 1H), 7.52-7.45 (m, 2H), 7.20-6.90 (m, 2H). | 21 | 4-pyridylboronic acid |
| 330 | 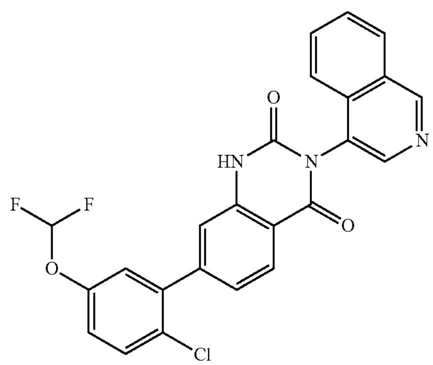 [SMILES: O=c1[nH]c2cc(-c3cc(OC(F)F)ccc3Cl)ccc2c(=O)n1-c1cncc2ccccc12] | 465.8 | 1H NMR (400 MHz, DMSO) δ 11.90 (s, 1H), 9.52 (s, 1H), 8.64 (s, 1H), 8.37-8.30 (m, 1H), 8.08 (d, J = 8.0 Hz, 1H), 7.97 (dd, J = 8.1, 1.5 Hz, 1H), 7.83 (dddd, J = 16.0, 8.1, 6.9, 1.4 Hz, 2H), 7.73 (d, J = 8.6 Hz, 1H), 7.60-7.11 (m, 5H). | 5 | 2-bromo-1-chloro-4-(difluoro-methoxy)benzene |
| 331 | 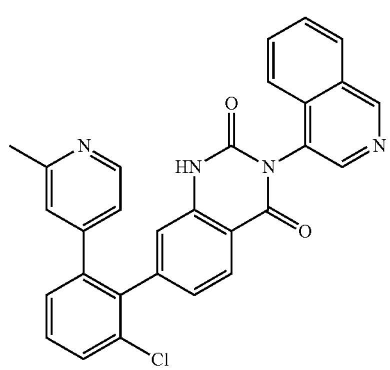 [SMILES: Cc1cc(-c2cccc(Cl)c2-c2ccc3c(=O)n(-c4cncc5ccccc45)c(=O)[nH]c3c2)ccn1] | 490.8 | 1H NMR (400 MHz, DMSO) δ 11.77 (d, J = 2.8 Hz, 1H), 9.46 (s, 1H), 8.66-8.55 (m, 1H), 8.52 (t, J = 6.0 Hz, 1H), 8.34-8.25 (m, 2H), 7.90 (dd, J = 8.0, 3.8 Hz, 1H), 7.87-7.73 (m, 3H), 7.73-7.61 (m, 2H), 7.56 (ddd, J = 7.6, 6.0, 1.2 Hz, 1H), 7.29 (d, J = 6.7 Hz, 1H), 7.16-7.05 (m, 2H), 2.59 (d, J = 6.1 Hz, 3H). | 21 | (2-methyl-4-pyridyl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 332 | 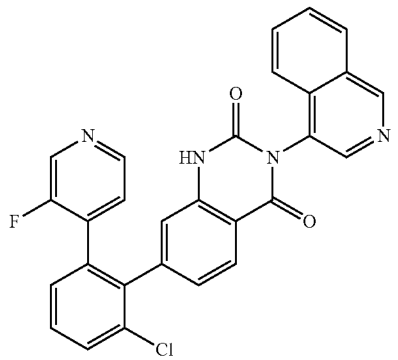 [SMILES: O=c1[nH]c2cc(-c3c(Cl)cccc3-c3ccncc3F)ccc2c(=O)n1-c1cncc2ccccc12] | 494.8 | 1H NMR (400 MHz, DMSO) δ 11.74 (d, J = 1.9 Hz, 1H), 9.47 (s, 1H), 8.61 (d, J = 7.0 Hz, 1H), 8.53 (dd, J = 4.9, 1.4 Hz, 1H), 8.43-8.36 (m, 1H), 8.30 (dd, J = 6.8, 3.2 Hz, 1H), 7.95-7.73 (m, 5H), 7.65 (t, J = 7.9 Hz, 1H), 7.52 (dt, J = 7.7, 1.5 Hz, 1H), 7.37 (ddd, J = 6.4, 4.8, 3.3 Hz, 1H), 7.11-7.00 (m, 2H). | 21 | 3-fluoro-4-(4,4,5,5-tetramethyl-1,3,2-dioxaborolan-2-yl)pyridine |
| 333 | 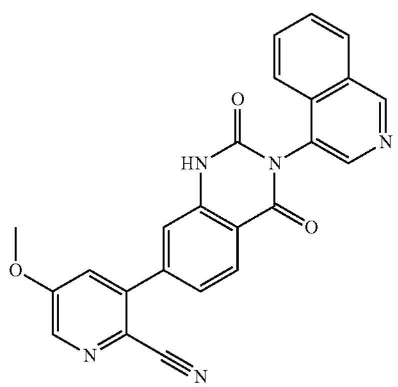 [SMILES: COc1cnc(C#N)c(-c2ccc3c(=O)n(-c4cncc5ccccc45)c(=O)[nH]c3c2)c1] | 421.9 | 1H NMR (400 MHz, DMSO) δ 12.01 (s, 1H), 9.51 (d, J = 0.9 Hz, 1H), 8.65 (s, 1H), 8.58 (d, J = 2.8 Hz, 1H), 8.36-8.29 (m, 1H), 8.18-8.11 (m, 1H), 8.06-7.94 (m, 1H), 7.82 (dddd, J = 14.6, 8.2, 6.9, 1.4 Hz, 2H), 7.71 (d, J = 2.7 Hz, 1H), 7.64-7.50 (m, 2H), 4.03 (s, 3H). | 5 | 3-bromo-5-methoxy-pyridine-2-carbonitrile |
| 334 | 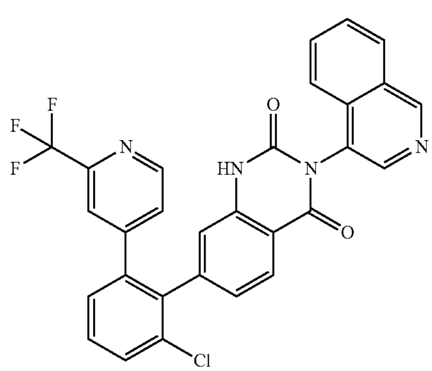 [SMILES: O=c1[nH]c2cc(-c3c(Cl)cccc3-c3ccnc(C(F)(F)F)c3)ccc2c(=O)n1-c1cncc2ccccc12] | 544.7 | 1H NMR (400 MHz, DMSO) δ 12.03-11.68 (m, 1H), 9.48 (d, J = 8.1 Hz, 1H), 8.72-8.55 (m, 2H), 8.31 (ddd, J = 8.1, 6.3, 2.2 Hz, 1H), 8.19-7.58 (m, 8H), 7.56-7.37 (m, 1H), 7.33-6.96 (m, 2H). | 21 | [2-(trifluoromethyl)-4-pyridyl]boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 335 | 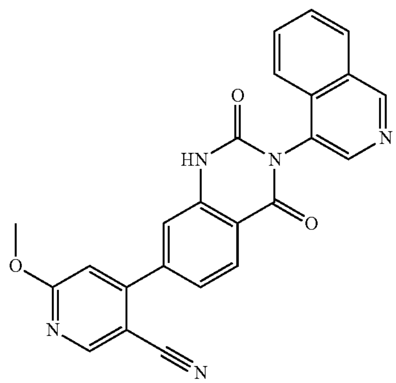 [SMILES: COc1cc(-c2ccc3c(=O)n(-c4cncc5ccccc45)c(=O)[nH]c3c2)c(C#N)cn1] | 421.8 | 1H NMR (400 MHz, DMSO) δ 12.01 (s, 1H), 9.49 (d, J = 0.9 Hz, 1H), 8.90 (d, J = 0.6 Hz, 1H), 8.62 (s, 1H), 8.35-8.27 (m, 1H), 8.13 (d, J = 8.6 Hz, 1H), 7.97 (dt, J = 8.2, 1.2 Hz, 1H), 7.87-7.75 (m, 2H), 7.53-7.46 (m, 2H), 7.18 (s, 1H), 4.04 (s, 3H). | 5 | 4-bromo-6-methoxy-pyridine-3-carbonitrile |
| 336 | 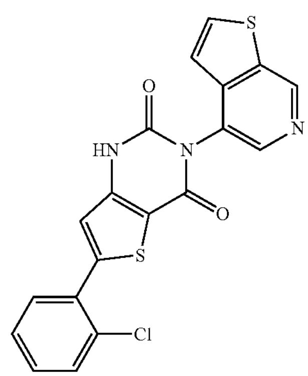 [SMILES: O=c1[nH]c2cc(-c3ccccc3Cl)sc2c(=O)n1-c1cncc2sccc12] | 411.7 | 1H NMR (400 MHz, DMSO) δ 12.25 (s, 1H), 9.37 (s, 1H), 8.50 (s, 1H), 8.20 (d, J = 5.4 Hz, 1H), 7.78-7.73 (m, 1H), 7.72 (s, 1H), 7.62-7.48 (m, 3H), 7.32 (s, 1H). | 9 | I-138; DIPEA |
| 337 | 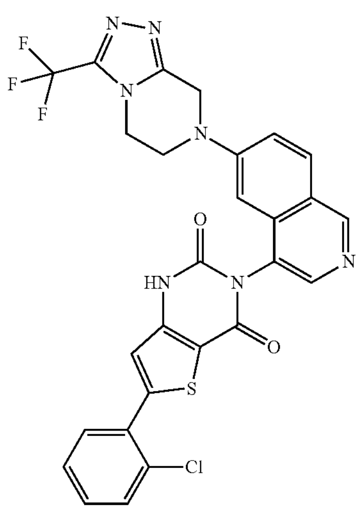 [SMILES: O=c1[nH]c2cc(-c3ccccc3Cl)sc2c(=O)n1-c1cncc2ccc(N3CCn4c(nnc4C(F)(F)F)C3)cc12] | 595.7 | 1H NMR (400 MHz, DMSO) δ 12.25 (s, 1H), 9.36 (s, 1H), 8.54 (s, 1H), 8.32 (d, J = 9.3 Hz, 1H), 7.89 (dd, J = 9.4, 2.5 Hz, 1H), 7.80-7.67 (m, 2H), 7.60-7.49 (m, 2H), 7.36 (s, 1H), 7.29 (d, J = 2.4 Hz, 1H), 5.10 (s, 2H), 4.34 (t, J = 5.4 Hz, 2H), 4.17 (t, J = 5.5 Hz, 2H). | 9 | I-139; DIPEA |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 338 | 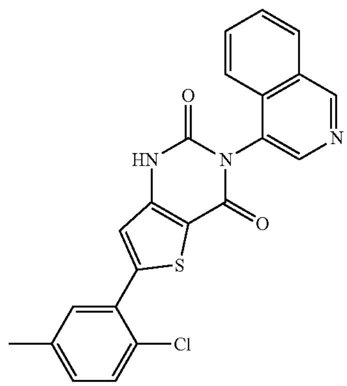 [SMILES: Cc1ccc(Cl)c(-c2cc3[nH]c(=O)n(-c4cncc5ccccc45)c(=O)c3s2)c1] | 420.0 | 1H NMR (400 MHz, Methanol-d4) δ 9.61 (s, 1H), 8.68 (s, 1H), 8.44 (d, J = 8.3 Hz, 1H), 8.10-7.88 (m, 3H), 7.61-7.45 (m, 2H), 7.38-7.29 (m, 2H), 2.44 (s, 3H). | 1 | (2-chloro-5-methyl-phenyl) boronic acid |
| 339 | 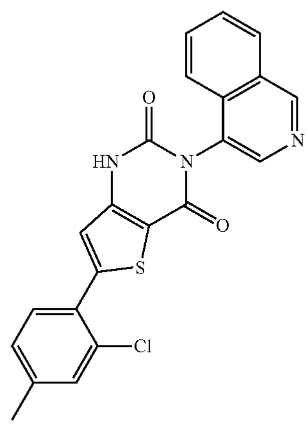 [SMILES: Cc1ccc(-c2cc3[nH]c(=O)n(-c4cncc5ccccc45)c(=O)c3s2)c(Cl)c1] | 420.0 | 1H NMR (400 MHz, Methanol-d4) δ 9.74 (s, 1H), 8.76 (s, 1H), 8.52 (s, 1H), 8.12-8.09 (m, 2H) 7.63-7.33 (m, 5h), 2.68 (s, 3H) | 1 | (2-chloro-4-methyl-phenyl) boronic acid |
| 340 | 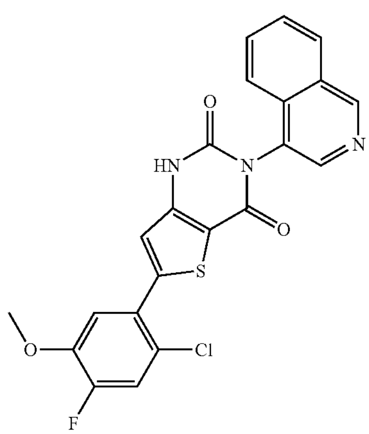 | 453.7 | 1H NMR (400 MHz, Methanol-d4) δ 9.58 (s, 1H), 8.64 (s, 1H), 8.40 (d, J = 8.3 Hz, 1H), 8.00 (d, J = 7.4 Hz, 1H), 7.98-7.88 (m, 2H), 7.44 (d, J = 10.8 Hz, 1H), 7.34 (m, 2H), 3.96 (s, 3H). | 1 | (2-chloro-4-fluoro-5-methoxy-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 341 | 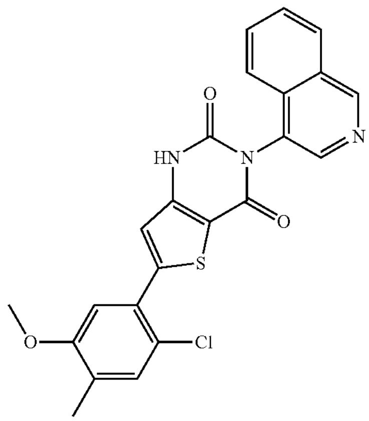 [SMILES: COc1cc(-c2cc3[nH]c(=O)n(-c4cncc5ccccc45)c(=O)c3s2)c(Cl)cc1C] | 449.8 | 1H NMR (400 MHz, Methanol-d4) δ 9.62 (s, 1H), 8.68 (s, 1H), 8.44 (d, J = 8.3 Hz, 1H), 8.10-7.89 (m, 3H), 7.41-7.33 (m, 2H), 7.16 (s, 1H), 3.93 (s, 3H), 2.27 (d, J = 0.8 Hz, 3H). | 1 | (2-chloro-5-methoxy-4-methyl-phenyl) boronic acid |
| 342 | 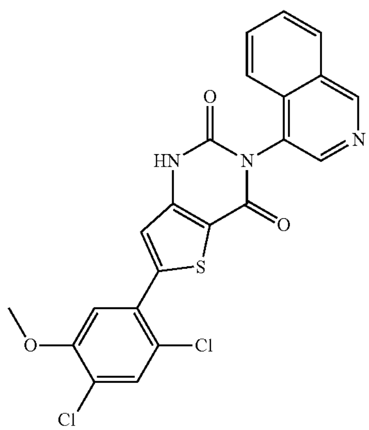 [SMILES: COc1cc(-c2cc3[nH]c(=O)n(-c4cncc5ccccc45)c(=O)c3s2)c(Cl)cc1Cl] | 470.7 | 1H NMR (400 MHz, Methanol-d4) δ 9.61 (s, 1H), 8.67 (s, 1H), 8.43 (d, J = 8.2 Hz, 1H), 8.04 (ddd, J = 8.0, 6.6, 1.2 Hz, 1H), 8.01-7.88 (m, 2H), 7.68 (s, 1H), 7.36 (d, J = 14.9 Hz, 2H), 4.00 (s, 3H). | 1 | (2,4-dichloro-5-methoxy-phenyl) boronic acid |
| 343 | 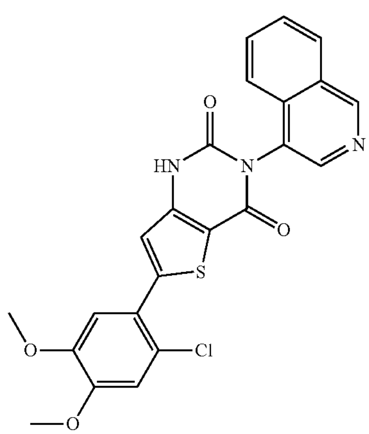 [SMILES: COc1cc(Cl)c(-c2cc3[nH]c(=O)n(-c4cncc5ccccc45)c(=O)c3s2)cc1OC] | 465.7 | 1H NMR (400 MHz, DMSO-d6) δ 12.26 (s, 1H), 9.48 (s, 1H), 8.60 (s, 1H), 8.31 (dd, J = 7.7, 1.4 Hz, 1H), 7.91-7.75 (m, 3H), 7.30 (s, 1H), 7.23 (d, J = 9.9 Hz, 2H), 3.87 (s, 3H), 3.87 (s, 3H). | 1 | (2-chloro-4,5-dimethoxy-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 344 | 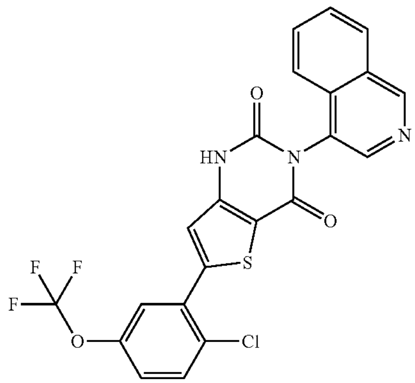 [SMILES: O=c1[nH]c2cc(-c3cc(OC(F)(F)F)ccc3Cl)sc2c(=O)n1-c1cncc2ccccc12] | 489.0 | 1H NMR (400 MHz, DMSO-d6) δ 12.34 (s, 1H), 9.47 (s, 1H), 8.60 (s, 1H), 8.30 (dd, J = 7.6, 1.5 Hz, 1H), 7.93-7.74 (m, 5H), 7.60 (ddd, J = 8.9, 2.8, 1.2 Hz, 1H), 7.41 (s, 1H). | 1 | [2-chloro-5-(trifluoro-methoxy)phenyl] boronic acid |
| 345 | 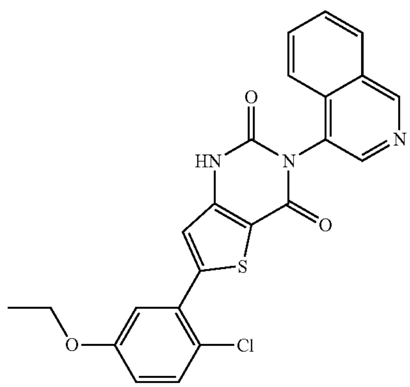 [SMILES: CCOc1ccc(Cl)c(-c2cc3[nH]c(=O)n(-c4cncc5ccccc45)c(=O)c3s2)c1] | 449.7 | 1H NMR (400 MHz, DMSO-d6) δ 12.29 (s, 1H), 9.48 (s, 1H), 8.60 (s, 1H), 8.34-8.27 (m, 1H), 7.90 (dd, J = 8.3, 1.3 Hz, 1H), 7.81 (dddd, J = 18.3, 8.0, 6.8, 1.4 Hz, 2H), 7.58 (d, J = 8.9 Hz, 1H), 7.33 (s, 1H), 7.23 (d, J = 3.0 Hz, 1H), 7.12 (dd, J = 8.9, 3.0 Hz, 1H), 4.13 (q, J = 7.0 Hz, 2H), 1.36 (t, J = 6.9 Hz, 3H). | 1 | (2-chloro-5-ethoxy-phenyl) boronic acid |
| 346 | 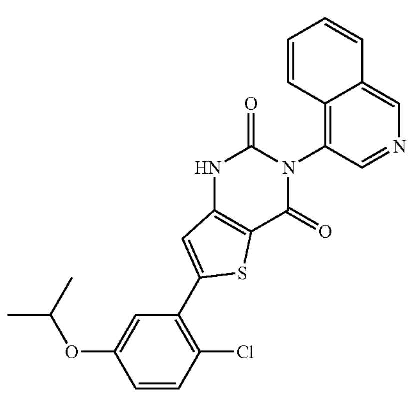 [SMILES: CC(C)Oc1ccc(Cl)c(-c2cc3[nH]c(=O)n(-c4cncc5ccccc45)c(=O)c3s2)c1] | 463.7 | 1H NMR (400 MHz, DMSO-d6) δ 12.28 (s, 1H), 9.47 (s, 1H), 8.59 (s, 1H), 8.30 (dd, J = 7.6, 1.5 Hz, 1H), 7.93-7.74 (m, 3H), 7.57 (d, J = 8.9 Hz, 1H), 7.33 (s, 1H), 7.21 (d, J = 3.0 Hz, 1H), 7.12 (dd, J = 8.9, 3.0 Hz, 1H), 4.74 (p, J = 6.0 Hz, 1H), 1.31 (d, J = 6.0 Hz, 6H). | 1 | (2-chloro-5-isopropoxy-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 347 | 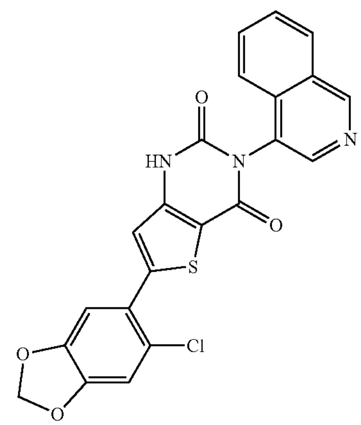 [SMILES: O=c1[nH]c2cc(-c3cc4c(cc3Cl)OCO4)sc2c(=O)n1-c1cncc2ccccc12] | 449.8 | 1H NMR (400 MHz, DMSO-d6) δ 12.27 (s, 1H), 9.48 (s, 1H), 8.59 (s, 1H), 8.31 (dd, J = 7.5, 1.4 Hz, 1H), 7.92-7.73 (m, 3H), 7.33 (d, J = 2.9 Hz, 2H), 7.24 (s, 1H), 6.20 (s, 2H). | 1 | (6-chloro-1,3-benzodioxol-5-yl)boronic acid |
| 348 | 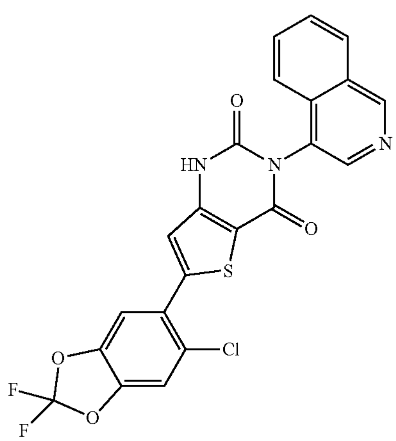 [SMILES: O=c1[nH]c2cc(-c3cc4c(cc3Cl)OC(F)(F)O4)sc2c(=O)n1-c1cncc2ccccc12] | 485.7 | 1H NMR (400 MHz, DMSO-d6) δ 12.33 (s, 1H), 9.47 (s, 1H), 8.59 (s, 1H), 8.34-8.26 (m, 1H), 7.95 (s, 1H), 7.94-7.74 (m, 4H), 7.30 (s, 1H). | 1 | (6-chloro-2,2-difluoro-1,3-benzodioxol-5-yl)boronic acid |
| 349 | 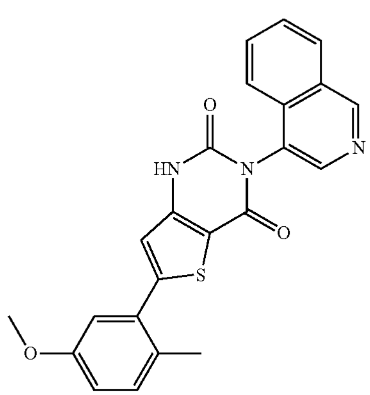 [SMILES: COc1ccc(C)c(-c2cc3[nH]c(=O)n(-c4cncc5ccccc45)c(=O)c3s2)c1] | 415.8 | 1H NMR (400 MHz, DMSO-d6) δ 12.26 (s, 1H), 9.49 (s, 1H), 8.60 (s, 1H), 8.32 (dd, J = 7.6, 1.3 Hz, 1H), 7.93-7.75 (m, 3H), 7.37-7.30 (m, 1H), 7.11 (s, 1H), 7.02 (d, J = 7.9 Hz, 2H), 3.80 (s, 3H), 2.39 (s, 3H). | 1 | (5-methoxy-2-methyl-phenyl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 350 | 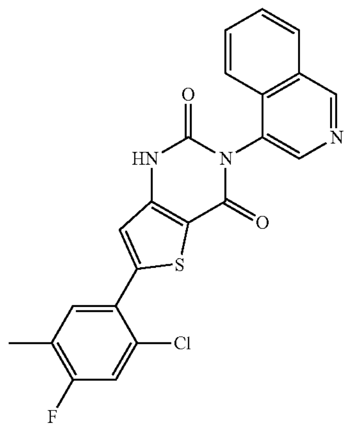 [SMILES: Cc1cc(-c2cc3[nH]c(=O)n(-c4cncc5ccccc45)c(=O)c3s2)c(Cl)cc1F] | 437.7 | 1H NMR (400 MHz, DMSO-d6) δ 12.31 (s, 1H), 9.46 (s, 1H), 8.59 (s, 1H), 8.30 (dd, J = 7.5, 1.5 Hz, 1H), 7.92-7.70 (m, 5H), 7.64 (d, J = 9.4 Hz, 1H), 7.30 (s, 1H), 2.32 (d, J = 1.9 Hz, 3H). | 1 | (2-chloro-4-fluoro-5-methyl-phenyl) boronic acid |
| 351 | 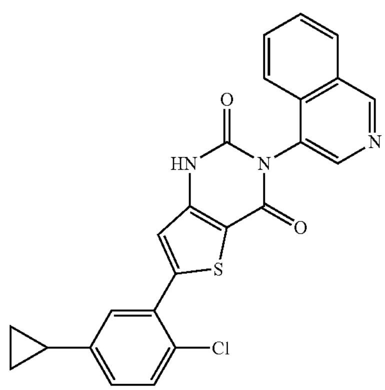 [SMILES: O=c1[nH]c2cc(-c3cc(C4CC4)ccc3Cl)sc2c(=O)n1-c1cncc2ccccc12] | 445.7 | 1H NMR (400 MHz, DMSO-d6) δ 12.28 (s, 1H), 9.48 (s, 1H), 8.60 (s, 1H), 8.31 (dd, J = 7.5, 1.4 Hz, 1H), 7.93-7.75 (m, 3H), 7.54 (d, J = 8.3 Hz, 1H), 7.46 (d, J = 2.3 Hz, 1H), 7.33 (s, 1H), 7.20 (dd, J = 8.4, 2.3 Hz, 1H), 2.06 (tt, J = 8.4, 4.9 Hz, 1H), 1.08-0.97 (m, 2H), 0.83-0.74 (m, 2H). | 1 | 2-(2-chloro-5-cyclopropyl-phenyl)-4,4,5,5-tetramethyl-1,3,2-dioxaborolane |
| 352 | 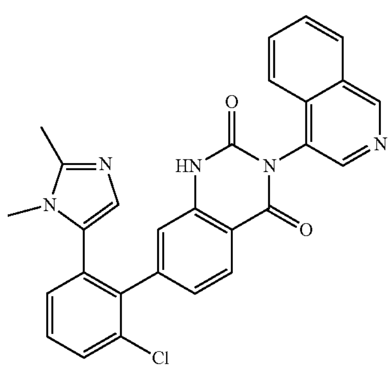 [SMILES: Cc1ncc(-c2cccc(Cl)c2-c2ccc3c(=O)n(-c4cncc5ccccc45)c(=O)[nH]c3c2)n1C] | 494.2 | 1H NMR (400 MHz, Methanol-d4) d 9.50 (d, J = 9.4 Hz, 1H), 8.49 (s, 1H), 8.36 (t, J = 9.1 Hz, 1H), 8.10 (d, J = 8.3 Hz, 1H), 7.96-7.80 (m, 4H), 7.69 (t, J = 7.9 Hz, 1H), 7.58 (dd, J = 7.7, 1.2 Hz, 1H), 7.34 (d, J = 8.4 Hz, 1H), 7.22-7.14 (m, 2H), 3.54 (d, J = 8.7 Hz, 3H), 2.62 (d, J = 10.0 Hz, 3H). | 21 | 1,2-dimethyl-5-(4,4,5,5-tetramethyl-1,3,2-dioxaborolan-2-yl)imidazole |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 353 | 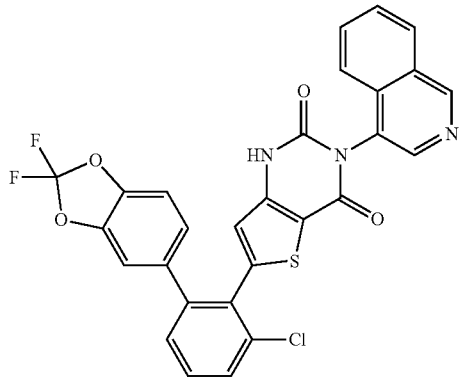 [SMILES: O=c1[nH]c2cc(-c3c(Cl)cccc3-c3ccc4c(c3)OC(F)(F)O4)sc2c(=O)n1-c1cncc2ccccc12] | 562.2 | 1H NMR (400 MHz, DMSO-d6) δ 12.19 (s, 1H), 9.43 (s, 1H), 8.57 (s, 1H), 8.29-8.24 (m, 1H), 7.83-7.70 (m, 4H), 7.68-7.59 (m, 1H), 7.50-7.44 (m, 2H), 7.40 (t, J = 8.8 Hz, 1H), 7.14 (dd, J = 8.3, 1.8 Hz, 1H), 7.01 (s, 1H). | 11 | (2,2-difluoro-1,3-benzodioxol-5-yl)boronic acid |
| 354 | 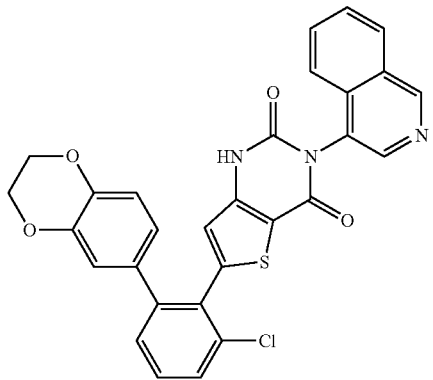 [SMILES: O=c1[nH]c2cc(-c3c(Cl)cccc3-c3ccc4c(c3)OCCO4)sc2c(=O)n1-c1cncc2ccccc12] | 540.2 | 1H NMR (400 MHz, DMSO-d6) δ 12.21 (s, 1H), 9.45 (s, 1H), 8.59 (s, 1H), 8.29 (d, J = 7.9 Hz, 1H), 7.86-7.74 (m, 3H), 7.67 (dd, J = 8.1, 1.3 Hz, 1H), 7.60-7.52 (m, 1H), 7.40 (dd, J = 7.7, 1.3 Hz, 1H), 6.99 (s, 1H), 6.86 (d, J = 2.1 Hz, 1H), 6.81 (d, J = 8.3 Hz, 1H), 6.72 (dd, J = 8.3, 2.2 Hz, 1H), 4.26 (s, 4H). | 11 | 2,3-dihydro-1,4-benzodioxin-6-ylboronic acid |
| 355 | 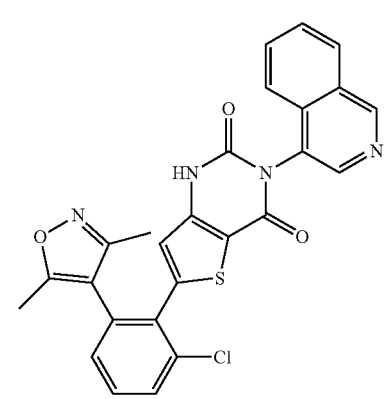 [SMILES: Cc1noc(C)c1-c1cccc(Cl)c1-c1cc2[nH]c(=O)n(-c3cncc4ccccc34)c(=O)c2s1] | 501.2 | 1H NMR (400 MHz, DMSO-d6) δ 12.19 (s, 1H), 9.44 (s, 1H), 8.60 (s, 1H), 8.33-8.22 (m, 1H), 7.93-7.72 (m, 4H), 7.64 (t, J = 7.9 Hz, 1H), 7.44 (dd, J = 7.6, 1.2 Hz, 1H), 7.04 (d, J = 2.3 Hz, 1H), 2.20 (d, J = 4.9 Hz, 3H), 2.02 (d, J = 4.3 Hz, 3H). | 11 | (2,2-difluoro-1,3-benzodioxol-5-yl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 356 | 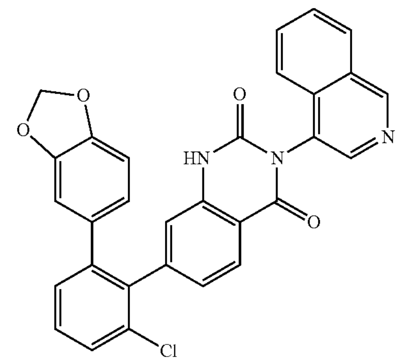 [SMILES: O=c1[nH]c2cc(-c3c(Cl)cccc3-c3ccc4c(c3)OCO4)ccc2c(=O)n1-c1cncc2ccccc12] | 520.2 | 1H NMR (400 MHz, DMSO-d6) δ 11.74 (d, J = 3.9 Hz, 1H), 9.47 (s, 1H), 8.62 (d, J = 5.5 Hz, 1H), 8.36-8.25 (m, 1H), 7.94-7.83 (m, 2H), 7.82-7.73 (m, 2H), 7.68-7.60 (m, 1H), 7.54 (t, J = 7.9 Hz, 1H), 7.42-7.40 (m, 1H), 7.16-6.99 (m, 2H), 6.84-6.77 (m, 2H), 6.62-6.58 (m, 1H), 6.05-5.97 (m, 2H). | 22 | 1,3-benzodioxol-5-ylboronic acid |
| 357 | 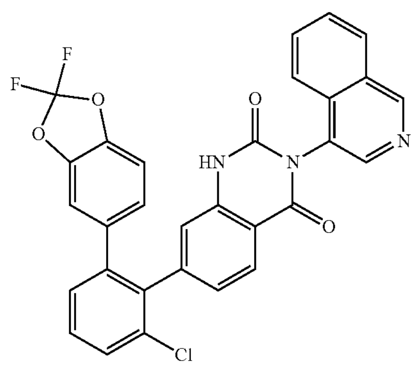 [SMILES: O=c1[nH]c2cc(-c3c(Cl)cccc3-c3ccc4c(c3)OC(F)(F)O4)ccc2c(=O)n1-c1cncc2ccccc12] | 556.2 | 1H NMR (400 MHz, DMSO-d6) δ 11.73 (s, 1H), 9.46 (s, 1H), 8.60 (s, 1H), 8.31-8.28 (m, 1H), 7.89 (dd, J = 8.2, 2.7 Hz, 2H), 7.84-7.74 (m, 2H), 7.72-7.70 (m, 1H), 7.58 (t, 1H), 7.47 (dd, J = 7.3, 3.9 Hz, 1H), 7.37 (dd, J = 3.7, 1.7 Hz, 1H), 7.31 (dd, J = 8.3, 4.5 Hz, 1H), 7.13-7.04 (m, 1H), 7.05 (dd, J = 5.9, 1.5 Hz, 1H), 6.97-6.93 (m, 1H). | 22 | (2,2-difluoro-1,3-benzodioxol-5-yl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 358 | 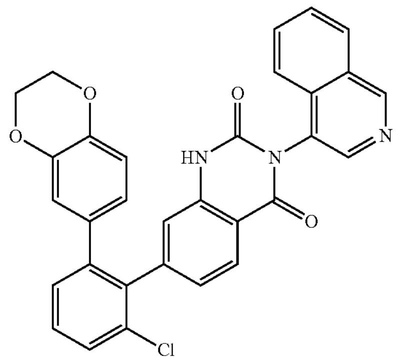 [SMILES: O=c1[nH]c2cc(-c3c(Cl)cccc3-c3ccc4c(c3)OCCO4)ccc2c(=O)n1-c1cncc2ccccc12] | 534.2 | 1H NMR (400 MHz, DMSO-d6) δ 11.74 (d, J = 4.6 Hz, 1H), 9.49 (s, 1H), 8.63 (d, J = 3.2 Hz, 1H), 8.36-8.27 (m, 1H), 7.94-7.75 (m, 4H), 7.65-7.62 (m, 1H), 7.53 (t, J = 7.9 Hz, 1H), 7.41-7.39 (m, 1H), 7.13-7.00 (m, 2H), 6.86-6.79 (m, 1H), 6.78-6.68 (m, 2H), 6.54 (ddd, J = 10.5, 8.3, 2.1 Hz, 1H), 4.25-4.19 (m, 4H). | 22 | 2,3-dihydro-1,4-benzodioxin-6-ylboronic acid |
| 359 | 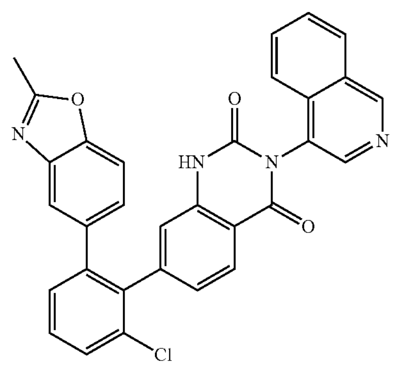 [SMILES: Cc1nc2cc(-c3cccc(Cl)c3-c3ccc4c(=O)n(-c5cncc6ccccc56)c(=O)[nH]c4c3)ccc2o1] | 531.3 | 1H NMR (400 MHz, DMSO-d6) δ 11.68 (d, J = 7.6 Hz, 1H), 9.45 (d, J = 5.7 Hz, 1H), 8.59 (dd, J = 13.4, 3.5 Hz, 1H), 8.39-8.18 (m, 1H), 7.95-7.72 (m, 3H), 7.73-7.44 (m, 4H), 7.17-7.00 (m, 4H), 6.72-6.51 (m, 1H), 2.60 (s, 3H). | 22 | (2-methyl-1,3-benzoxazol-6-yl)boronic acid |
| 360 | 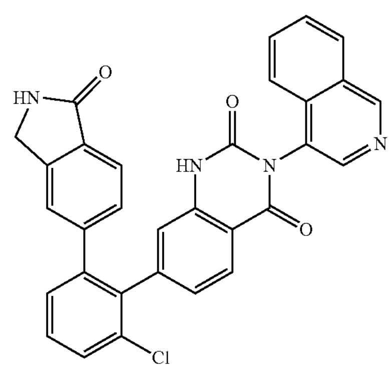 [SMILES: O=C1NCc2cc(-c3cccc(Cl)c3-c3ccc4c(=O)n(-c5cncc6ccccc56)c(=O)[nH]c4c3)ccc21] | 531.2 | 1H NMR (400 MHz, DMSO-d6) δ 11.71 (d, J = 10.7 Hz, 1H), 9.49 (s, 1H), 8.66-8.54 (m, 2H), 8.35-8.27 (m, 1H), 7.95-7.76 (m, 4H), 7.72 (ddd, J = 8.0, 2.3, 1.2 Hz, 1H), 7.60 (t, J = 7.9 Hz, 1H), 7.57-7.46 (m, 2H), 7.44 (d, J = 1.4 Hz, 1H), 7.28-7.21 (m, 1H), 7.12-7.07 (m, 1H), 7.06-7.01 | 22 | (1-oxoisoindolin-5-yl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | (m, 1H), 4.33 (d, J = 5.8 Hz, 2H). | | |
| 361 | 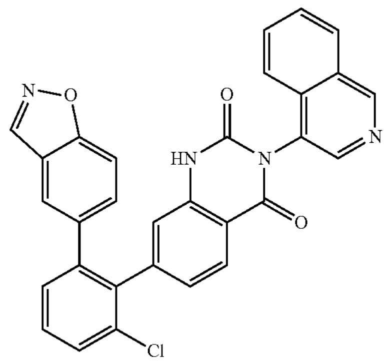 [SMILES: O=c1[nH]c2cc(-c3c(Cl)cccc3-c3ccc4oncc4c3)ccc2c(=O)n1-c1cncc2ccccc12] | 517.2 | 1H NMR (400 MHz, DMSO-d6) δ 11.74 (d, J = 6.4 Hz, 1H), 11.21 (s, 1H), 9.47 (s, 1H), 8.62 (d, J = 7.4 Hz, 1H), 8.30 (ddd, J = 6.4, 4.4, 2.2 Hz, 1H), 7.93-7.84 (m, 2H), 7.83-7.74 (m, 2H), 7.68 (dt, J = 8.1, 1.4 Hz, 1H), 7.56 (t, J = 7.9 Hz, 1H), 7.51-7.41 (m, 2H), 7.20 (ddd, J = 16.0, 8.6, 2.4 Hz, 1H), 7.13-6.99 (m, 2H), 6.87 (dd, J = 15.2, 8.7 Hz, 1H). | 22 | 5-(4,4,5,5-tetramethyl-1,3,2-dioxaborolan-2-yl)-1,2-benzoxazole, DME, H2O |
| 362 | 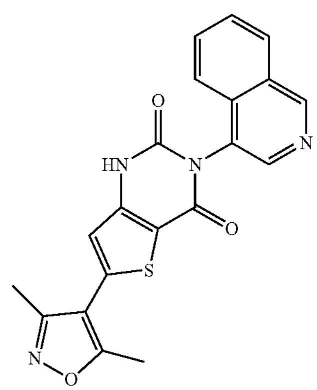 [SMILES: Cc1noc(C)c1-c1cc2[nH]c(=O)n(-c3cncc4ccccc34)c(=O)c2s1] | 391.1 | 1H NMR (400 MHz, DMSO-d6) δ 12.28 (s, 1H), 9.46 (s, 1H), 8.58 (s, 1H), 8.30 (dd, J = 7.6, 1.4 Hz, 1H), 7.88-7.82 (m, 2H), 7.79 (ddd, J = 10.0, 5.6, 2.2 Hz, 1H), 7.12 (s, 1H), 2.61 (s, 3H), 2.41 (s, 3H). | 1 | (3,5-dimethyl-isoxazol-4-yl)boronic acid |
| 363 | 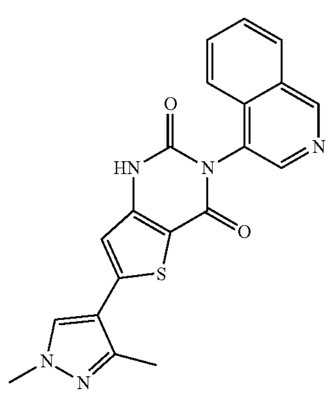 [SMILES: Cc1nn(C)cc1-c1cc2[nH]c(=O)n(-c3cncc4ccccc34)c(=O)c2s1] | 390.2 | 1H NMR (400 MHz, DMSO-d6) δ 12.19 (s, 1H), 9.47 (s, 1H), 8.57 (s, 1H), 8.33-8.28 (m, 2H), 7.86-7.82 (m, 2H), 7.81-7.77 (m, 1H), 7.00 (s, 1H), 3.83 (s, 3H), 2.39 (s, 3H). | 1 | (1,3-dimethyl-pyrazol-4-yl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 364 | 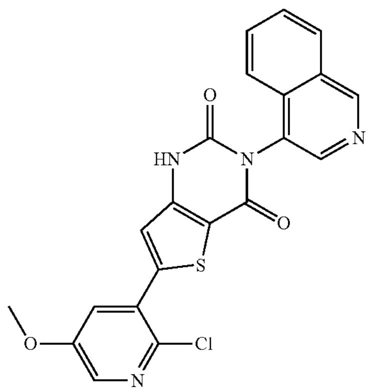 [SMILES: COc1cnc(Cl)c(-c2cc3[nH]c(=O)n(-c4cncc5ccccc45)c(=O)c3s2)c1] | 437.2 | 1H NMR (400 MHz, DMSO-d6) δ 12.34 (s, 1H), 9.46 (s, 1H), 8.59 (s, 1H), 8.32-8.24 (m, 2H), 7.90-7.74 (m, 4H), 7.45 (s, 1H), 3.95 (s, 3H). | 1 | (2-chloro-5-methoxy-3-pyridyl) boronic acid |
| 365 | 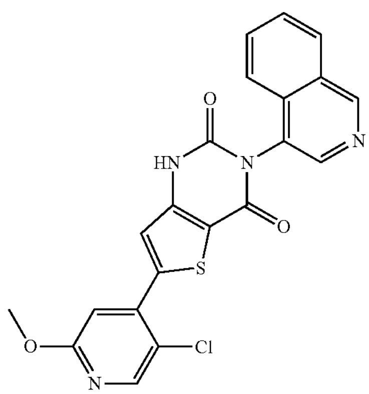 [SMILES: COc1cc(-c2cc3[nH]c(=O)n(-c4cncc5ccccc45)c(=O)c3s2)c(Cl)cn1] | 437.2 | 1H NMR (400 MHz, DMSO-d6) δ 12.35 (s, 1H), 9.44 (s, 1H), 8.57 (s, 1H), 8.47 (s, 1H), 8.32-8.23 (m, 1H), 7.88 (d, J = 8.1 Hz, 1H), 7.85-7.71 (m, 2H), 7.52 (s, 1H), 7.27 (s, 1H), 3.94 (s, 3H). | 1 | (5-chloro-2-methoxy-4-pyridyl) boronic acid |
| 366 | 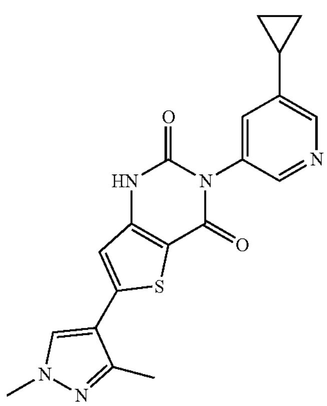 [SMILES: Cc1nn(C)cc1-c1cc2[nH]c(=O)n(-c3cncc(C4CC4)c3)c(=O)c2s1] | 380.2 | 1H NMR (400 MHz, DMSO-d6) δ 12.06 (s, 1H), 8.44 (d, J = 2.1 Hz, 1H), 8.32 (d, J = 2.2 Hz, 1H), 8.29 (s, 1H), 7.51 (t, J = 2.2 Hz, 1H), 6.93 (s, 1H), 3.81 (s, 3H), 2.37 (s, 3H), 2.04 (tt, J = 8.4, 5.0 Hz, 1H), 1.09-1.01 (m, 2H), 0.81-0.74 (m, 2H). | 1 | I-155; (1,3-dimethyl-1H-pyrazol-4-yl)boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 367 | 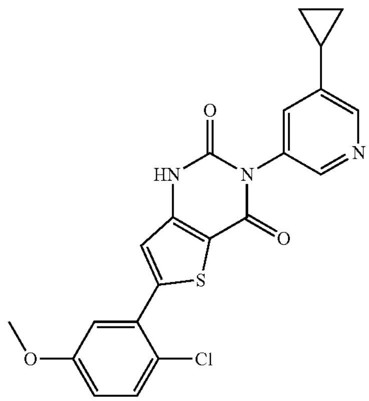 [SMILES: COc1ccc(Cl)c(-c2cc3[nH]c(=O)n(-c4cncc(C5CC5)c4)c(=O)c3s2)c1] | 426.2 | 1H NMR (400 MHz, DMSO-d6) δ 12.15 (s, 1H), 8.44 (d, J = 2.1 Hz, 1H), 8.32 (d, J = 2.3 Hz, 1H), 7.58 (d, J = 8.9 Hz, 1H), 7.51 (t, J = 2.2 Hz, 1H), 7.26 (s, 1H), 7.23 (d, J = 3.0 Hz, 1H), 7.12 (dd, J = 8.9, 3.0 Hz, 1H), 3.84 (s, 3H), 2.03 (td, J = 8.4, 4.2 Hz, 1H), 1.10-0.99 (m, 2H), 0.80-0.72 (m, 2H). | 1 | I-155; (2-chloro-5-methoxy-phenyl) boronic acid |
| 368 | 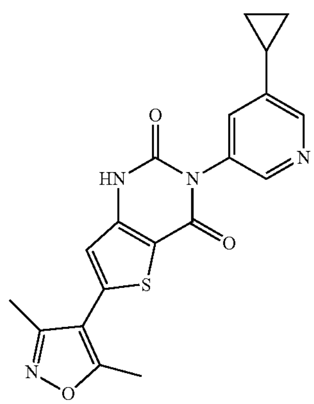 [SMILES: Cc1noc(C)c1-c1cc2[nH]c(=O)n(-c3cncc(C4CC4)c3)c(=O)c2s1] | 381.2 | 1H NMR (400 MHz, DMSO-d6) δ 12.15 (s, 1H), 8.45 (d, J = 2.1 Hz, 1H), 8.33 (d, J = 2.2 Hz, 1H), 7.52 (t, J = 2.2 Hz, 1H), 7.05 (s, 1H), 2.59 (s, 3H), 2.38 (s, 3H), 2.04 (tt, J = 8.4, 5.1 Hz, 1H), 1.10-1.00 (m, 2H), 0.77 (dt, J = 6.7, 4.5 Hz, 2H). | 1 | I-155; (3,5-dimethyl-isoxazol-4-yl)boronic acid |
| 369 | 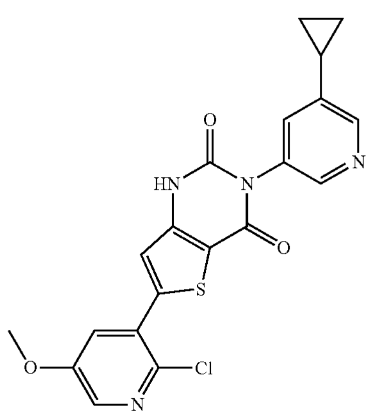 [SMILES: COc1cnc(Cl)c(-c2cc3[nH]c(=O)n(-c4cncc(C5CC5)c4)c(=O)c3s2)c1] | 427.2 | 1H NMR (400 MHz, DMSO-d6) δ 12.21 (s, 1H), 8.59-8.40 (m, 1H), 8.38-8.11 (m, 2H), 7.84-7.71 (m, 1H), 7.56-7.50 (m, 1H), 7.38 (s, 1H), 3.94 (s, 3H), 2.07-2.01 (m, 1H), 1.12-1.00 (m, 2H), 0.81-0.71 (m, 2H). | 1 | I-155; (2-chloro-5-methoxy-3-pyridyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 370 | 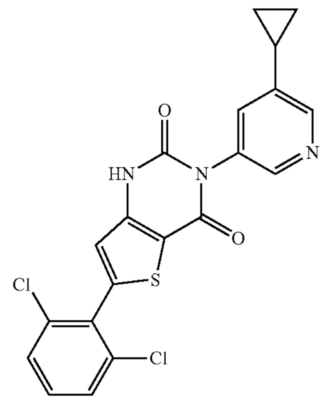 [SMILES: O=c1[nH]c2cc(-c3c(Cl)cccc3Cl)sc2c(=O)n1-c1cncc(C2CC2)c1] | 430.1 | 1H NMR (400 MHz, DMSO-d6) δ 12.22 (s, 1H), 8.43 (d, J = 32.5 Hz, 2H), 7.72-7.64 (m, 2H), 7.63-7.52 (m, 2H), 7.04 (s, 1H), 2.05 (tt, J = 8.3, 5.0 Hz, 1H), 1.11-1.02 (m, 2H), 0.82-0.71 (m, 2H). | 1 | I-155; (2,6-dichlorophenyl) boronic acid |
| 371 | 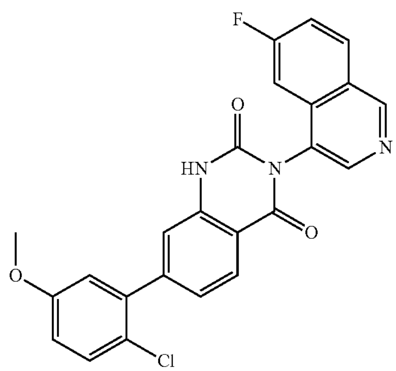 [SMILES: COc1ccc(Cl)c(-c2ccc3c(=O)n(-c4cncc5ccc(F)cc45)c(=O)[nH]c3c2)c1] | 448.2 | 1H NMR (400 MHz, DMSO-d6) δ 11.80 (s, 1H), 9.47 (s, 1H), 8.61 (s, 1H), 8.42 (dd, J = 9.1, 5.6 Hz, 1H), 8.04 (d, J = 8.0 Hz, 1H), 7.94 (dd, J = 10.4, 2.5 Hz, 1H), 7.71-7.66 (m, 1H), 7.56 (d, J = 8.8 Hz, 1H), 7.37-7.29 (m, 2H), 7.10 (dd, J = 8.9, 3.1 Hz, 1H), 7.00 (d, J = 3.0 Hz, 1H), 3.84 (s, 3H). | 18 | I-132; 6-fluoroiso-quinolin-4-amine hydrogen chloride |
| 372 | 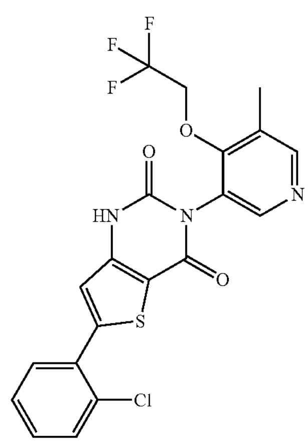 [SMILES: Cc1cncc(-n2c(=O)[nH]c3cc(-c4ccccc4Cl)sc3c2=O)c1OCC(F)(F)F] | 468.1 | H NMR (400 MHz, DMSO-d6) δ 12.28 (s, 1H), 8.55-8.46 (m, 2H), 7.81-7.74 (m, 1H), 7.72-7.66 (m, 1H), 7.58-7.46 (m, 2H), 7.30 (s, 1H), 4.61 (q, J = 8.8 Hz, 2H), 2.35 (s, 3H). | 1 | I-156 |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 373 | 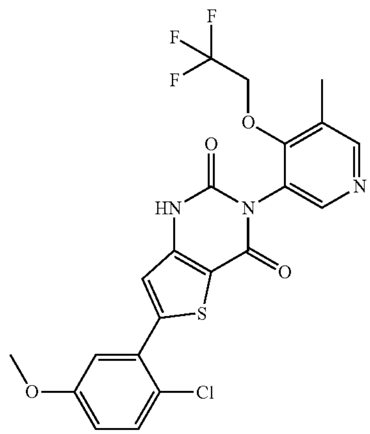 [SMILES: COc1ccc(Cl)c(-c2cc3[nH]c(=O)n(-c4cncc(C)c4OCC(F)(F)F)c(=O)c3s2)c1] | 498.2 | 1H NMR (400 MHz, DMSO-d6) δ 12.29 (s, 1H), 8.58-8.49 (m, 2H), 7.58 (d, J = 8.9 Hz, 1H), 7.30 (s, 1H), 7.26 (d, J = 3.0 Hz, 1H), 7.12 (dd, J = 8.9, 3.1 Hz, 1H), 4.63 (q, J = 8.8 Hz, 2H), 3.85 (s, 3H), 2.36 (s, 3H). | 1 | I-156; (2-chloro-5-methoxy-phenyl) boronic acid |
| 374 | 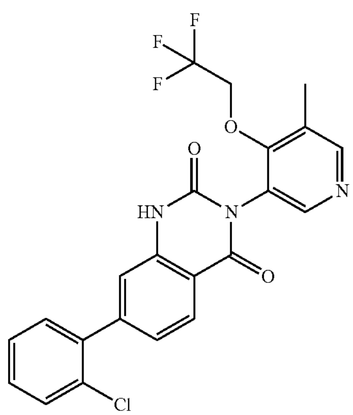 [SMILES: Cc1cncc(-n2c(=O)[nH]c3cc(-c4ccccc4Cl)ccc3c2=O)c1OCC(F)(F)F] | 462.2 | 1H NMR (400 MHz, DMSO-d6) δ 11.87 (s, 1H), 8.59-8.52 (m, 2H), 8.05 (d, J = 8.1 Hz, 1H), 7.73-7.60 (m, 1H), 7.51 (d, J = 3.2 Hz, 3H), 7.37-7.27 (m, 2H), 4.67-4.60 (m, 2H), 2.37 (s, 3H). | 2 | I-157 |
| 375 | 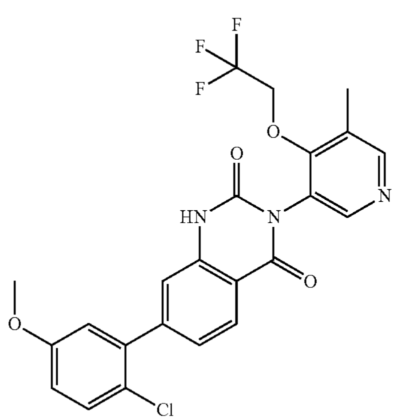 [SMILES: COc1ccc(Cl)c(-c2ccc3c(=O)n(-c4cncc(C)c4OCC(F)(F)F)c(=O)[nH]c3c2)c1] | 492.2 | 1H NMR (400 MHz, DMSO-d6) δ 11.86 (s, 1H), 8.57 (s, 1H), 8.49 (s, 1H), 8.04 (d, J = 8.0 Hz, 1H), 7.54 (d, J = 8.8 Hz, 1H), 7.35-7.28 (m, 2H), 7.08 (dd, J = 8.8, 3.1 Hz, 1H), 7.04 (d, J = 3.1 Hz, 1H), 4.70-4.55 (m, 2H), 3.83 (s, 3H), 2.37 (s, 3H). | 2 | I-157; (2-chloro-5-methoxy-phenyl) boronic acid |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 376 | 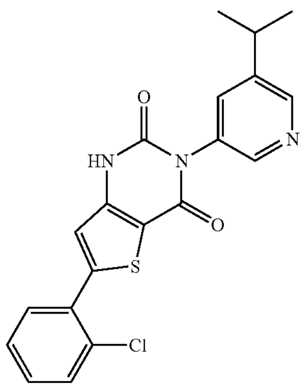 [SMILES: CC(C)c1cncc(-n2c(=O)[nH]c3cc(-c4ccccc4Cl)sc3c2=O)c1] | 397.90 | 1H NMR (400 MHz, DMSO-d6) δ 12.16 (s, 1H), 8.54 (d, J = 2.1 Hz, 1H), 8.38 (d, J = 2.3 Hz, 1H), 7.76-7.72 (m, 2H), 7.71-7.67 (m, 1H), 7.56-7.48 (m, 2H), 7.27 (s, 1H), 3.03 (hept, J = 6.9 Hz, 1H), 1.27 (d, J = 6.9 Hz, 6H). | 9 | I-170; I-30 |
| 377 | 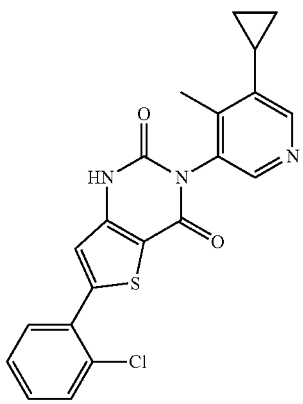 [SMILES: Cc1c(C2CC2)cncc1-n1c(=O)[nH]c2cc(-c3ccccc3Cl)sc2c1=O] | 409.88 | 1H NMR (400 MHz, DMSO-d6) δ 12.25 (s, 1H), 8.39 (s, 1H), 8.30 (s, 1H), 7.78-7.70 (m, 1H), 7.70-7.66 (m, 1H), 7.57-7.47 (m, 2H), 7.29 (s, 1H), 2.22 (s, 3H), 2.00 (ddd, J = 13.9, 8.5, 5.4 Hz, 1H), 1.06-0.97 (m, 2H), 0.79 (td, J = 5.8, 3.8 Hz, 2H). | 9 | I-171; I-30 |
| 378 | 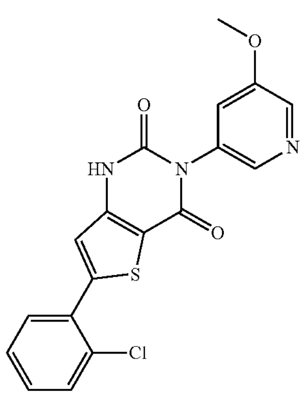 [SMILES: COc1cncc(-n2c(=O)[nH]c3cc(-c4ccccc4Cl)sc3c2=O)c1] | 385.80 | 1H NMR (400 MHz, DMSO-d6) δ 12.16 (s, 1H), 8.36 (d, J = 2.8 Hz, 1H), 8.17 (d, J = 1.9 Hz, 1H), 7.77-7.70 (m, 1H), 7.70-7.64 (m, 1H), 7.57-7.45 (m, 3H), 7.26 (s, 1H), 3.85 (s, 3H). | 9 | 5-methoxypyridin-3-amine; I-30 |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 379 | 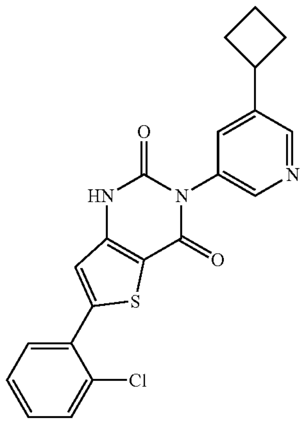 [SMILES: O=c1[nH]c2cc(-c3ccccc3Cl)sc2c(=O)n1-c1cncc(C2CCC2)c1] | 409.90 | 1H NMR (400 MHz, DMSO-d6) δ 12.15 (s, 1H), 8.49 (d, J = 2.1 Hz, 1H), 8.37 (d, J = 2.3 Hz, 1H), 7.74 (t, J = 4.6 Hz, 2H), 7.70-7.65 (m, 1H), 7.57-7.47 (m, 2H), 7.27 (s, 1H), 3.69-3.56 (m, 1H), 2.39-2.32 (m, 2H), 2.23-2.07 (m, 2H), 2.07-1.95 (m, 1H), 1.92-1.81 (m, 1H). | 9 | 5-cyclo-butylpyridin-3-amine; I-30 |
| 380 | 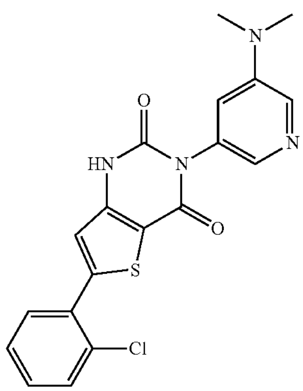 [SMILES: CN(C)c1cncc(-n2c(=O)[nH]c3cc(-c4ccccc4Cl)sc3c2=O)c1] | 398.87 | 1H NMR (400 MHz, DMSO-d6) δ 12.18 (s, 1H), 8.18 (d, J = 2.9 Hz, 1H), 8.00 (d, J = 1.8 Hz, 1H), 7.79-7.69 (m, 1H), 7.69-7.62 (m, 1H), 7.57-7.43 (m, 3H), 7.27 (s, 1H), 3.00 (s, 6H). | 9 | N3,N3-dimethyl-pyridine-3,5-diamine |
| 381 | 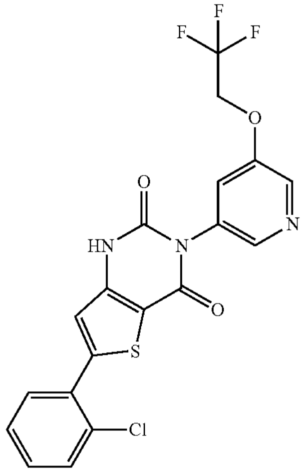 [SMILES: O=c1[nH]c2cc(-c3ccccc3Cl)sc2c(=O)n1-c1cncc(OCC(F)(F)F)c1] | 453.90 | 1H NMR (400 MHz, DMSO-d6) δ 12.20 (s, 1H), 8.48 (d, J = 2.8 Hz, 1H), 8.30 (d, J = 1.9 Hz, 1H), 7.78-7.70 (m, 1H), 7.70-7.63 (m, 2H), 7.57-7.44 (m, 2H), 7.27 (s, 1H), 4.92 (q, J = 8.8 Hz, 2H). | 9 | I-173; I-30 |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| 382 | 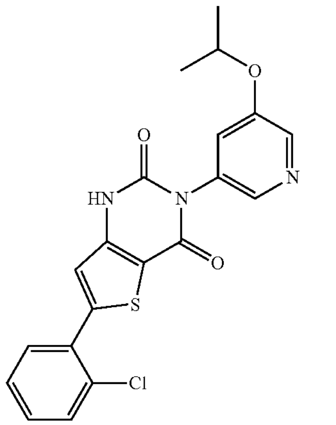 [SMILES: CC(C)Oc1cncc(-n2c(=O)[nH]c3cc(-c4ccccc4Cl)sc3c2=O)c1] | 413.83 | 1H NMR (400 MHz, DMSO-d6) δ 12.15 (s, 1H), 8.30 (d, J = 2.7 Hz, 1H), 8.13 (d, J = 1.9 Hz, 1H), 7.78-7.70 (m, 1H), 7.69-7.63 (m, 1H), 7.58-7.45 (m, 3H), 7.26 (s, 1H), 4.68 (hept, J = 6.0 Hz, 1H), 1.31 (d, J = 6.0 Hz, 6H). | 9 | I-172; I-30 |
| 383 | 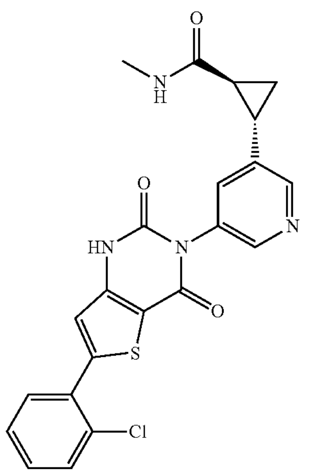 [SMILES: CNC(=O)[C@H]1C[C@@H]1c1cncc(-n2c(=O)[nH]c3cc(-c4ccccc4Cl)sc3c2=O)c1] | 452.80 | 1H NMR (400 MHz, DMSO-d6) δ 12.17 (s, 1H), 8.49 (d, J = 2.1 Hz, 1H), 8.38 (d, J = 2.2 Hz, 1H), 8.13 (q, J = 4.6 Hz, 1H), 7.77-7.70 (m, 1H), 7.70-7.63 (m, 1H), 7.60 (t, J = 2.2 Hz, 1H), 7.56-7.43 (m, 2H), 7.26 (s, 1H), 2.62 (d, J = 4.6 Hz, 3H), 2.34 (ddd, J = 9.4, 6.1, 4.2 Hz, 1H), 1.89 (ddd, J = 8.4, 5.4, 4.1 Hz, 1H), 1.42 (ddd, J = 9.3, 5.5, 4.2 Hz, 1H), 1.32 (ddd, J = 8.3, 6.1, 4.1 Hz, 1H). | 9 | I-175; I-30 |
| 384 | 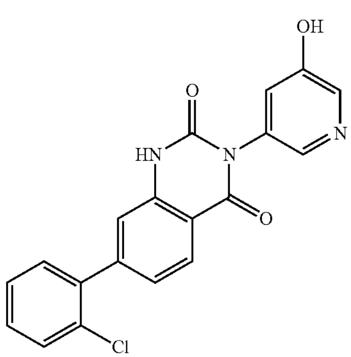 [SMILES: O=c1[nH]c2cc(-c3ccccc3Cl)ccc2c(=O)n1-c1cncc(O)c1] | 395.95 | 1H NMR (400 MHz, DMSO-d6) δ 12.15 (s, 1H), 8.45 (d, J = 2.1 Hz, 1H), 8.34 (d, J = 2.3 Hz, 1H), 7.78-7.71 (m, 1H), 7.71-7.63 (m, 1H), 7.56-7.46 (m, 3H), 7.26 (s, 1H), 2.08-1.97 (m, 1H), | 9 | 5-hydroxylpyridin-3-amine; I-30 |

TABLE 18-continued

Examples 177-384

| Example | Structure | ES/MS m/z | 1H-NMR | Procedure | Changes to Procedure: Different Reagents/ Starting Materials |
|---|---|---|---|---|---|
| | | | 1.10-1.00 (m, 2H), 0.80-0.70 (m, 2H). | | |

Example 340

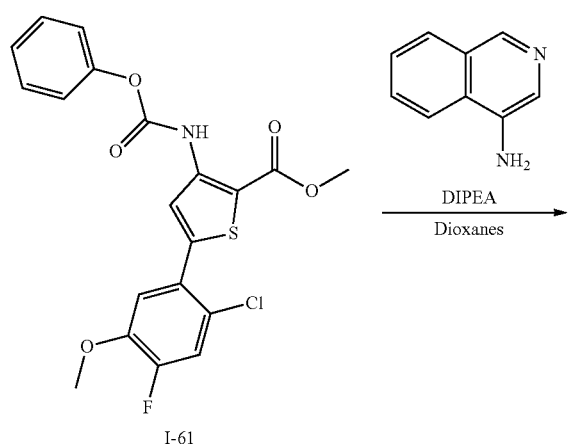

I-61

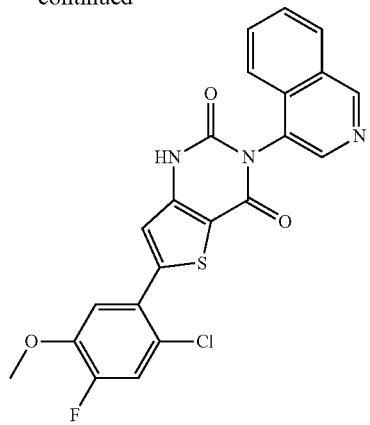

Example 340

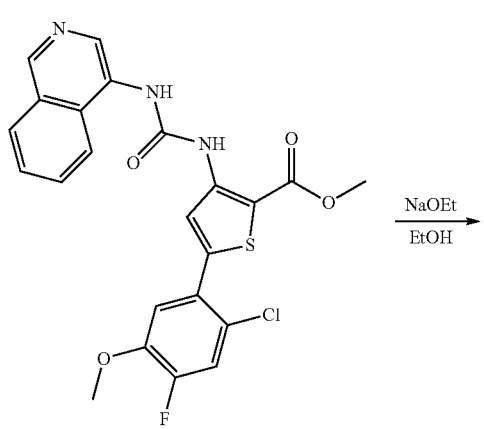

methyl 5-(2-chloro-4-fluoro-5-methoxy-phenyl)-3-(4-isoquinolylcarbamoylamino)thiophene-2-carboxylate: To a solution of methyl 5-(2-chloro-4-fluoro-5-methoxy-phenyl)-3-(phenoxycarbonylamino)thiophene-2-carboxylate (I-61) (5.00 g, 11.5 mmol) in dioxanes (50 mL) was added isoquinolin-4-amine (1.99 g, 13.8 mmol) and DIPEA (4.00 mL). The resulting mixture was then stirred at 95° C. for 16 hours. The reaction mixture was then concentrated under reduced pressure wherein MeCN (100 mL) was added to the crude residue, resulting in the formation of a precipitate. The solid was filtered off and washed with MeCN (3×100 mL) to afford the product.

ES/MS: 485.8 (M$^+$).

1H NMR (400 MHz, DMSO-d$_6$) δ 10.09 (s, 1H), 9.95 (s, 1H), 9.13 (s, 1H), 8.87 (s, 1H), 8.28 (s, 1H), 8.25-8.08 (m, 2H), 7.88 (ddd, J=8.4, 6.9, 1.3 Hz, 1H), 7.74 (ddd, J=8.0, 6.9, 1.1 Hz, 1H), 7.66 (d, J=11.1 Hz, 1H), 7.37 (d, J=8.9 Hz, 1H), 3.92 (s, 3H), 3.32 (s, 3H).

6-(2-chloro-4-fluoro-5-methoxy-phenyl)-3-(4-isoquinolyl)-1H-thieno[3,2-d]pyrimidine-2,4-dione (Example 340): To a suspension of methyl 5-(2-chloro-4-fluoro-5-methoxy-phenyl)-3-(4-isoquinolylcarbamoylamino)thiophene-2-carboxylate (5.00 g, 10.3 mmol) in EtOH (32.4 mL) was added NaOEt (21% in EtOH, 5.76 mL, 15.4 mmol). The reaction mixture was then stirred at ambient temperature for one hour. The reaction mixture was then quenched with 30% v/v NH$_4$Cl (32.4 mL) and water (32.4 mL), resulting in the formation of a precipitate. The solid was then filtered and washed with water (3×100 mL) to afford the product (Example 340).

ES/MS: 453.7 (M$^+$).

$^1$H NMR (400 MHz, DMSO-d$_6$) δ 12.30 (s, 1H), 9.44 (s, 1H), 8.57 (s, 1H), 8.32-8.25 (m, 1H), 7.87-7.74 (m, 3H), 7.72 (d, J=11.1 Hz, 1H), 7.45 (d, J=8.9 Hz, 1H), 7.33 (s, 1H), 3.95 (s, 3H).

Procedure 37: Example 385

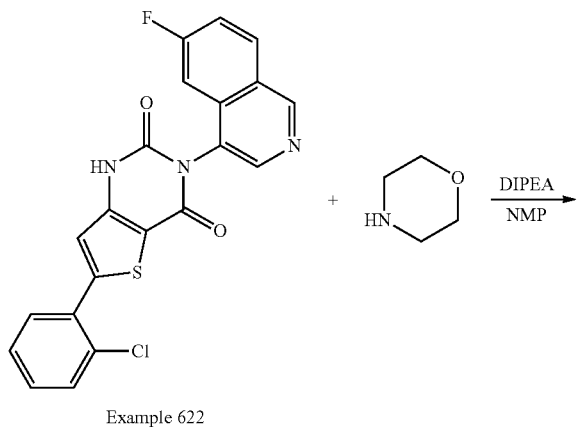

Example 622

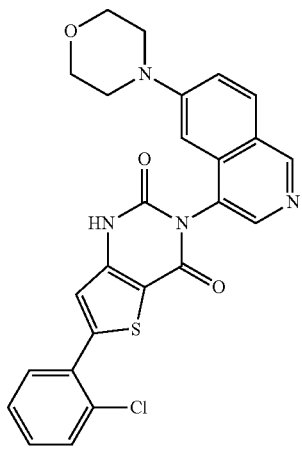

Example 385

6-(2-chlorophenyl)-3-(6-morpholinoisoquinolin-4-yl) thieno[3,2-d]pyrimidine-2,4(1H,3H)-dione: To a microwave vial with 6-(2-chlorophenyl)-3-(6-fluoroisoquinolin-4-yl) thieno[3,2-d]pyrimidine-2,4(1H,3H)-dione (Example 622) (HCl salt) (30 mg, 0.07 mmol), morpholine (25 mg, 0.28 mmol) and NMP (0.4 mL), was added DIPEA (0.05 mL, 0.28 mmol). The solution was heated under microwave conditions at 150° C. for 2 hours. To the crude reaction mixture was added water (0.2 mL) and TFA (0.5 mL), and the mixture was filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 385 as a trifluoroacetate salt.

ES/MS: 491.1 (M$^+$).

$^1$H NMR (400 MHz, DMSO-$d_6$) δ 12.24 (s, 1H), 9.30 (s, 1H), 8.51 (s, 1H), 8.26 (d, J=9.4 Hz, 1H), 7.84-7.65 (m, 3H), 7.62-7.48 (m, 2H), 7.34 (s, 1H), 7.02 (d, J=2.4 Hz, 1H), 3.74 (t, J=4.8 Hz, 4H), 3.56 (t, J=4.9 Hz, 4H).

Examples 386-427

The following Examples were made in an analogous fashion according to Procedure 37 and are shown below in Table 19. Any different reagents/starting materials than those described in Procedure 37 are noted in the last column of Table 19—"Changes to Procedure 37: Different Reagents/Starting Materials".

TABLE 19

Examples 386-427

| Example | Structure | ES/MS m/z | 1H-NMR | Changes to Procedure 37: Different Reagents/Starting Materials |
|---|---|---|---|---|
| 386 | 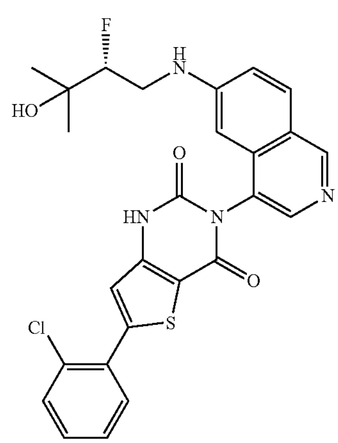 [SMILES: CC(C)(O)[C@H](F)CNc1ccc2cncc(-n3c(=O)[nH]c4cc(-c5ccccc5Cl)sc4c3=O)c2c1] | 525.1 | 1H NMR (400 MHz, DMSO-d6) δ 12.37 (d, J = 3.1 Hz, 1H), 9.25 (s, 1H), 8.48 (s, 1H), 8.19 (d, J = 9.2 Hz, 1H), 8.12-7.95 (m, 1H), 7.80-7.65 (m, 2H), 7.55 (td, J = 6.8, 5.7, 3.6 Hz, 2H), 7.40 (d, J = 9.3 Hz, 1H), 7.34 (d, J = 3.4 Hz, 1H), 6.67-6.27 (m, 1H), 5.05-4.72 (m, 1H), 4.28 (dt, J = 49.5, 10.1 Hz, 1H), 3.84-3.53 (m, 1H), 1.17-0.99 (m, 6H). | (3R)-4-amino-3-fluoro-2-methyl-butan-2-ol |

TABLE 19-continued

Examples 386-427

| Example | Structure | ES/MS m/z | 1H-NMR | Changes to Procedure 37:Different Reagents/Starting Materials |
|---|---|---|---|---|
| 387 | 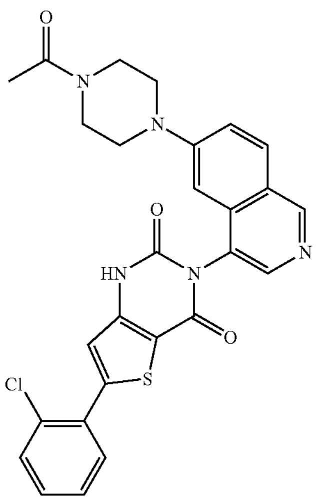 [SMILES: CC(=O)N1CCN(c2ccc3cncc(-n4c(=O)[nH]c5cc(-c6ccccc6Cl)sc5c4=O)c3c2)CC1] | 532.1 | 1H NMR (400 MHz, DMSO-d6) δ 12.26 (s, 1H), 9.31 (s, 1H), 8.51 (s, 1H), 8.28 (d, J = 9.4 Hz, 1H), 7.82-7.62 (m, 3H), 7.55 (dd, J = 6.8, 3.3 Hz, 2H), 7.35 (s, 1H), 6.99 (s, 1H), 3.73-3.66 (m, 4H), 3.66-3.60 (m, 4H), 2.04 (s, 3H). | 1-piperazin-1-ylethanone |
| 388 | 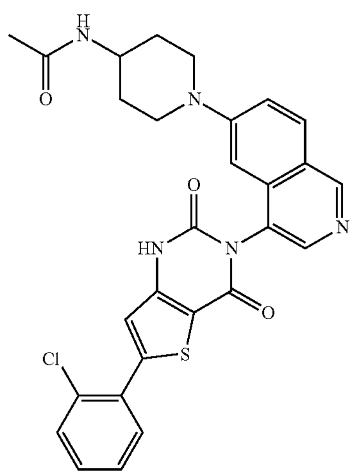 [SMILES: CC(=O)NC1CCN(c2ccc3cncc(-n4c(=O)[nH]c5cc(-c6ccccc6Cl)sc5c4=O)c3c2)CC1] | 546.1 | 1H NMR (400 MHz, DMSO-d6) δ 12.25 (s, 1H), 9.29 (s, 1H), 8.51 (s, 1H), 8.26 (d, J = 9.4 Hz, 1H), 7.89-7.65 (m, 4H), 7.54 (dt, J = 5.9, 2.4 Hz, 2H), 7.34 (s, 1H), 7.04 (d, J = 2.3 Hz, 1H), 4.19 (d, J = 13.5 Hz, 2H), 3.89 (s, 1H), 3.23 (t, J = 12.6 Hz, 2H), 1.86 (d, J = 12.6 Hz, 2H), 1.79 (s, 3H), 1.38 (d, J = 12.7 Hz, 2H). | N-(4-piperidyl)acetamide |
| 389 | 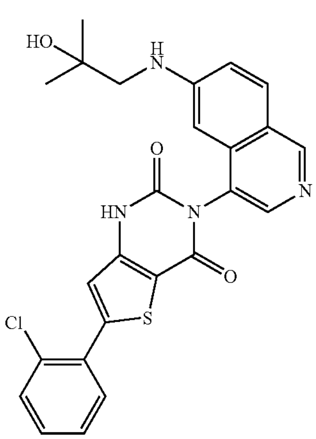 [SMILES: CC(C)(O)CNc1ccc2cncc(-n3c(=O)[nH]c4cc(-c5ccccc5Cl)sc4c3=O)c2c1] | 493.1 | 1H NMR (400 MHz, DMSO-d6) δ 12.35 (s, 1H), 9.19 (s, 1H), 8.43 (s, 1H), 8.15 (d, J = 9.2 Hz, 1H), 7.80-7.65 (m, 2H), 7.60-7.46 (m, 4H), 7.35 (s, 1H), 3.22 (s, 2H), 1.14 (d, J = 3.8 Hz, 6H). | 1-amino-2-methyl-propan-2-ol |

TABLE 19-continued

Examples 386-427

| Example | Structure | ES/MS m/z | 1H-NMR | Changes to Procedure 37:Different Reagents/Starting Materials |
|---|---|---|---|---|
| 390 | 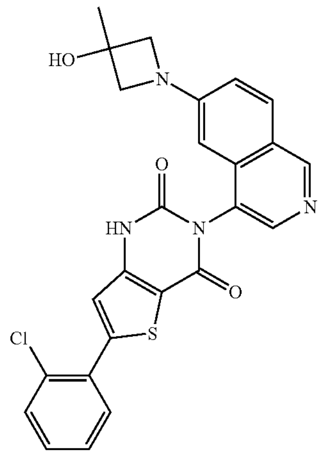 [SMILES: CC1(O)CN(c2ccc3cncc(-n4c(=O)[nH]c5cc(-c6ccccc6Cl)sc5c4=O)c3c2)C1] | 491.1 | 1H NMR (400 MHz, DMSO-d6) δ 12.27 (s, 1H), 9.25 (s, 1H), 8.47 (s, 1H), 8.22 (d, J = 9.1 Hz, 1H), 7.81-7.66 (m, 2H), 7.61-7.46 (m, 2H), 7.34 (s, 1H), 7.17 (dd, J = 9.3, 2.2 Hz, 1H), 6.48 (s, 1H), 4.07 (d, J = 10.2 Hz, 2H), 3.96 (s, 2H), 1.44 (s, 3H). | 3-methylazetidin-3-ol |
| 391 | 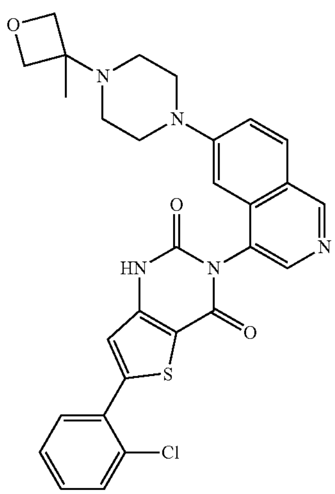 [SMILES: CC1(N2CCN(c3ccc4cncc(-n5c(=O)[nH]c6cc(-c7ccccc7Cl)sc6c5=O)c4c3)CC2)COC1] | 559.8 | 1H NMR (400 MHz, DMSO-d6) δ 12.25 (s, 1H), 9.32 (s, 1H), 8.52 (s, 1H), 8.28 (d, J = 9.4 Hz, 1H), 7.83-7.66 (m, 3H), 7.60-7.49 (m, 2H), 7.35 (s, 1H), 7.06 (d, J = 2.1 Hz, 1H), 4.71 (s, 2H), 4.34 (s, 2H), 3.70-3.50 (m, 8H), 1.49 (s, 3H). | 1-(3-methyloxetan-3-yl)piperazine |
| 392 | 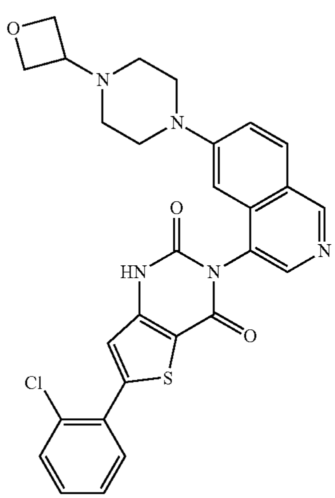 [SMILES: O=c1[nH]c2cc(-c3ccccc3Cl)sc2c(=O)n1-c1cncc2ccc(N3CCN(C4COC4)CC3)cc12] | 545.7 | 1H NMR (400 MHz, DMSO-d6) δ 12.23 (s, 1H), 9.29 (s, 1H), 8.49 (s, 1H), 8.25 (d, J = 9.3 Hz, 1H), 7.82-7.62 (m, 3H), 7.61-7.46 (m, 2H), 7.35 (s, 1H), 7.05 (d, J = 2.3 Hz, 1H), 4.78-4.58 (m, 4H), 3.49-3.40 (m, 9H). | 1-(oxetan-3-yl)piperazine |

TABLE 19-continued

Examples 386-427

| Example | Structure | ES/MS m/z | 1H-NMR | Changes to Procedure 37:Different Reagents/Starting Materials |
|---|---|---|---|---|
| 393 | 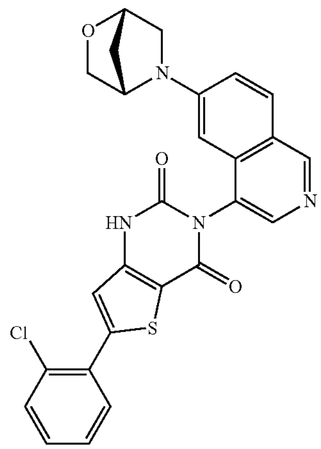 [SMILES: O=c1[nH]c2cc(-c3ccccc3Cl)sc2c(=O)n1-c1cncc2ccc(N3C[C@@H]4C[C@H]3CO4)cc12] | 502.8 | 1H NMR (400 MHz, DMSO-d6) δ 12.27 (s, 1H), 9.26 (s, 1H), 8.48 (s, 1H), 8.25 (d, J = 9.3 Hz, 1H), 7.78-7.62 (m, 2H), 7.60-7.44 (m, 4H), 7.34 (d, J = 2.1 Hz, 1H), 5.18 (d, J = 6.2 Hz, 1H), 4.74 (s, 1H), 3.83 (d, J = 7.6 Hz, 1H), 3.68-3.60 (m, 2H), 2.01-1.83 (m, 2H). | (1S,4S)-2-oxa-5-azabicyclo[2.2.1]heptane |
| 394 | 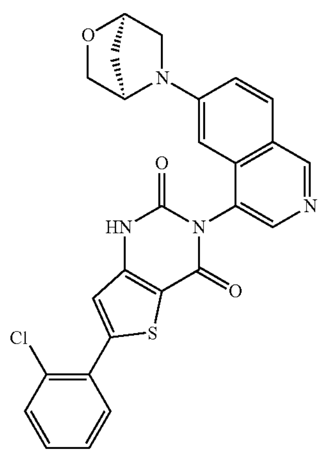 [SMILES: O=c1[nH]c2cc(-c3ccccc3Cl)sc2c(=O)n1-c1cncc2ccc(N3C[C@H]4C[C@@H]3CO4)cc12] | 502.7 | 1H NMR (400 MHz, DMSO-d6) δ 12.26 (s, 1H), 9.25 (s, 1H), 8.47 (s, 1H), 8.24 (d, J = 9.4 Hz, 1H), 7.80-7.66 (m, 2H), 7.64-7.48 (m, 4H), 7.34 (d, J = 2.1 Hz, 1H), 5.17 (d, J = 6.0 Hz, 1H), 4.74 (s, 1H), 3.82 (d, J = 7.5 Hz, 1H), 3.66-3.59 (m, 2H), 2.02-1.87 (m, 2H). | (1R,4R)-2-oxa-5-azabicyclo[2.2.1]heptane |
| 395 | 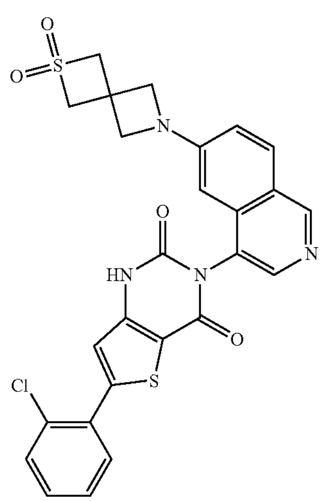 [SMILES: O=c1[nH]c2cc(-c3ccccc3Cl)sc2c(=O)n1-c1cncc2ccc(N3CC4(C3)CS(=O)(=O)C4)cc12] | 550.8 | 1H NMR (400 MHz, DMSO-d6) δ 12.26 (s, 1H), 9.27 (s, 1H), 8.48 (s, 1H), 8.23 (d, J = 9.1 Hz, 1H), 7.82-7.62 (m, 2H), 7.62-7.48 (m, 2H), 7.34 (s, 1H), 7.27-7.05 (m, 1H), 6.55 (d, J = 2.1 Hz, 1H), 4.51 (s, 4H), 4.39 (s, 4H). | 2-thia-6-azaspiro[3.3]heptane 2,2-dioxide |

TABLE 19-continued

Examples 386-427

| Example | Structure | ES/MS m/z | 1H-NMR | Changes to Procedure 37:Different Reagents/Starting Materials |
|---|---|---|---|---|
| 396 | 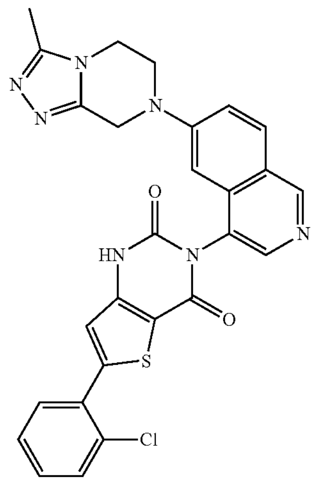 [SMILES: Cc1nnc2n1CCN(c1ccc3cncc(-n4c(=O)[nH]c5cc(-c6ccccc6Cl)sc5c4=O)c3c1)C2] | 541.8 | 1H NMR (400 MHz, DMSO) δ 12.26 (s, 1H), 9.37 (s, 1H), 8.56 (s, 1H), 8.34 (d, J = 9.4 Hz, 1H), 7.92 (dd, J = 9.4, 2.5 Hz, 1H), 7.79-7.67 (m, 2H), 7.60-7.49 (m, 2H), 7.36 (s, 1H), 7.29 (d, J = 2.4 Hz, 1H), 5.02 (s, 2H), 4.18-4.10 (m, 4H), 2.40 (s, 3H). | 3-methyl-5,6,7,8-tetrahydro-[1,2,4]triazolo[4,3-a]pyrazine |
| 397 | 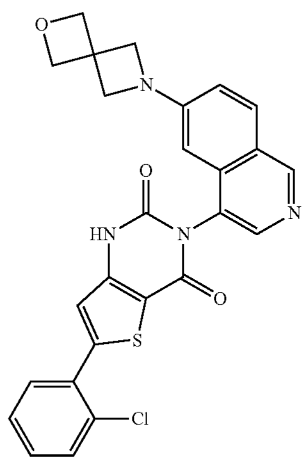 [SMILES: O=c1[nH]c2cc(-c3ccccc3Cl)sc2c(=O)n1-c1cncc2ccc(N3CC4(COC4)C3)cc12] | 503.3 | 1H NMR (400 MHz, DMSO-d6) δ 12.28 (s, 1H), 9.24 (s, 1H), 8.46 (s, 1H), 8.21 (d, J = 9.1 Hz, 1H), 7.82-7.67 (m, 2H), 7.63-7.45 (m, 2H), 7.35 (s, 1H), 7.15 (dd, J = 9.1, 2.2 Hz, 1H), 6.44 (d, J = 2.1 Hz, 1H), 4.72 (s, 4H), 4.32 (s, 4H). | 2-oxa-6-azaspiro[3.3]heptane |
| 398 | 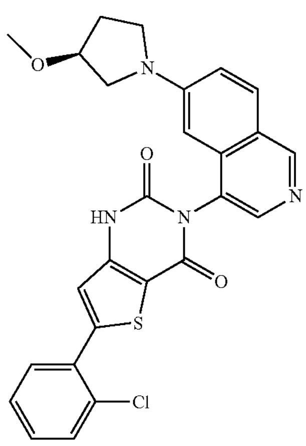 [SMILES: CO[C@H]1CCN(c2ccc3cncc(-n4c(=O)[nH]c5cc(-c6ccccc6Cl)sc5c4=O)c3c2)C1] | 505.3 | 1H NMR (400 MHz, DMSO-d6) δ 12.28 (d, J = 1.8 Hz, 1H), 9.27 (s, 1H), 8.48 (s, 1H), 8.25 (d, J = 9.3 Hz, 1H), 7.80-7.73 (m, 1H), 7.73-7.68 (m, 1H), 7.59-7.50 (m, 2H), 7.45 (dd, J = 9.3, 2.3 Hz, 1H), 7.35 (s, 1H), 6.60 (d, J = 2.2 Hz, 1H), 4.13 (dd, J = 4.7, 2.5 Hz, 1H), 3.59-3.44 (s, 4H), 3.27 (s, 3H), 2.23-2.01 (m, 2H). | (3S)-3-methoxypyrrolidine |

TABLE 19-continued

Examples 386-427

| Example | Structure | ES/MS m/z | 1H-NMR | Changes to Procedure 37:Different Reagents/Starting Materials |
|---|---|---|---|---|
| 399 | 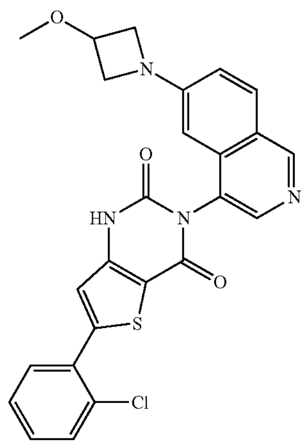 [SMILES: COC1CN(c2ccc3cncc(-n4c(=O)[nH]c5cc(-c6ccccc6Cl)sc5c4=O)c3c2)C1] | 503.3 | 1H NMR (400 MHz, DMSO-d6) δ 12.28 (s, 1H), 9.24 (s, 1H), 8.46 (s, 1H), 8.21 (d, J = 9.1 Hz, 1H), 7.82-7.67 (m, 2H), 7.63-7.45 (m, 2H), 7.35 (s, 1H), 7.15 (dd, J = 9.1, 2.2 Hz, 1H), 6.44 (d, J = 2.1 Hz, 1H), 4.72 (s, 4H), 4.32 (s, 4H). | 3-methoxyazetidine hydrochloride |
| 400 | 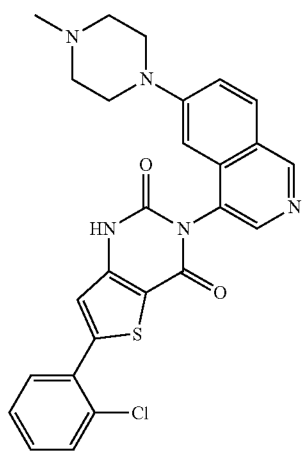 [SMILES: CN1CCN(c2ccc3cncc(-n4c(=O)[nH]c5cc(-c6ccccc6Cl)sc5c4=O)c3c2)CC1] | 504.3 | 1H NMR (400 MHz, DMSO-d6) δ 12.21 (s, 1H), 9.79 (s, 1H), 9.27 (s, 1H), 8.47 (s, 1H), 8.24 (d, J = 9.3 Hz, 1H), 7.79-7.67 (m, 3H), 7.58-7.49 (m, 2H), 7.35 (s, 1H), 7.08 (d, J = 2.4 Hz, 1H), 4.29 (s, 2H), 3.18 (s, 6H), 2.87 (s, 3H). | 1-methylpiperazine |
| 401 | 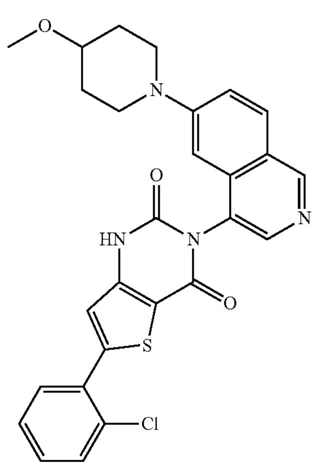 [SMILES: COC1CCN(c2ccc3cncc(-n4c(=O)[nH]c5cc(-c6ccccc6Cl)sc5c4=O)c3c2)CC1] | 519.2 | 1H NMR (400 MHz, DMSO-d6) δ 12.25 (s, 1H), 9.25 (s, 1H), 8.47 (s, 1H), 8.22 (d, J = 9.5 Hz, 1H), 7.78-7.74 (m, 2H), 7.72-7.68 (m, 1H), 7.58-7.50 (m, 2H), 7.34 (s, 1H), 6.99 (d, J = 2.3 Hz, 1H), 3.89 (d, J = 13.6 Hz, 2H), 3.51-3.42 (m, 1H), 3.27 (s, 3H), 1.92 (t, J = 5.8 Hz, 2H), 1.54-1.46 (m, 2H). | 4-methoxypiperidine |

TABLE 19-continued

Examples 386-427

| Example | Structure | ES/MS m/z | 1H-NMR | Changes to Procedure 37:Different Reagents/Starting Materials |
|---|---|---|---|---|
| 402 | 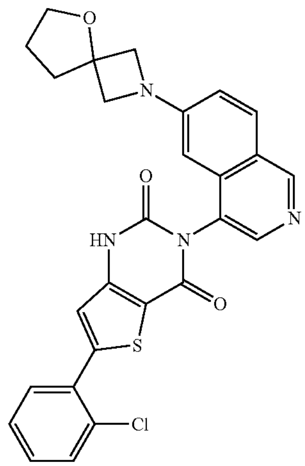 [SMILES: O=c1[nH]c2cc(-c3ccccc3Cl)sc2c(=O)n1-c1cncc2ccc(N3CC4(CCCO4)C3)cc12] | 517.3 | 1H NMR (400 MHz, DMSO-d6) δ 12.27 (s, 1H), 9.26 (s, 1H), 8.47 (s, 1H), 8.22 (d, J = 9.1 Hz, 1H), 7.78-7.74 (m, 1H), 7.73-7.69 (m, 1H), 7.59-7.46 (m, 2H), 7.34 (s, 1H), 7.16 (dd, J = 9.1, 2.2 Hz, 1H), 6.47 (d, J = 2.1 Hz, 1H), 4.20 (dd, J = 9.8, 3.1 Hz, 2H), 4.10 (dd, J = 9.8, 6.0 Hz, 2H), 3.79 (t, J = 6.8 Hz, 2H), 2.12 (dd, J = 8.0, 6.5 Hz, 2H), 1.91-1.84 (m, 2H). | 5-oxa-2-azaspiro[3.4]octane |
| 403 | 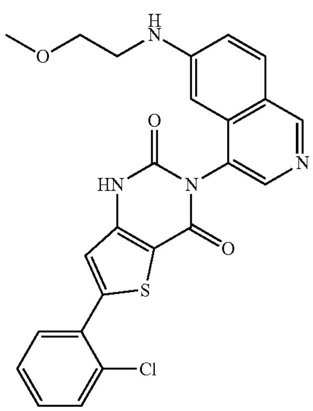 [SMILES: COCCNc1ccc2cncc(-n3c(=O)[nH]c4cc(-c5ccccc5Cl)sc4c3=O)c2c1] | 479.2 | 1H NMR (400 MHz, DMSO-d6) δ 12.33 (s, 1H), 9.19 (s, 1H), 8.44 (s, 1H), 8.14 (d, J = 9.2 Hz, 1H), 7.87-7.66 (m, 3H), 7.61-7.49 (m, 2H), 7.40 (dd, J = 9.1, 2.1 Hz, 1H), 7.35 (s, 1H), 6.69 (s, 1H), 3.50 (t, J = 5.2 Hz, 2H), 3.45-3.42 (m, 1H), 3.25 (s, 3H). | 2-methoxyethanamine |
| 404 | 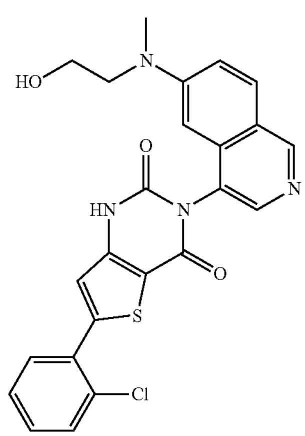 [SMILES: CN(CCO)c1ccc2cncc(-n3c(=O)[nH]c4cc(-c5ccccc5Cl)sc4c3=O)c2c1] | 479.2 | 1H NMR (400 MHz, DMSO-d6) δ 12.29 (s, 1H), 9.24 (s, 1H), 8.46 (s, 1H), 8.20 (d, J = 9.5 Hz, 1H), 7.79-7.73 (m, 1H), 7.72-7.68 (m, 1H), 7.63 (dd, J = 9.5, 2.4 Hz, 1H), 7.58-7.49 (m, 2H), 7.35 (s, 1H), 6.67 (d, J = 2.3 Hz, 1H), 4.83 (s, 1H), 3.76-3.66 (m, 2H), 3.61 (t, J = 5.4 Hz, 2H), 3.14 (s, 3H). | 2-(methylamino)ethanol |

TABLE 19-continued

Examples 386-427

| Example | Structure | ES/MS m/z | 1H-NMR | Changes to Procedure 37:Different Reagents/Starting Materials |
|---|---|---|---|---|
| 405 | 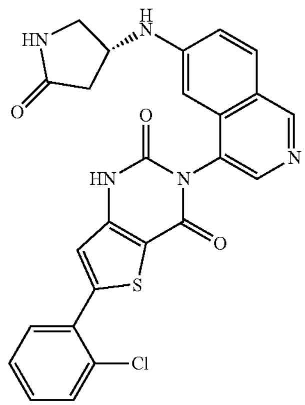 [SMILES: O=C1C[C@@H](Nc2ccc3cncc(-n4c(=O)[nH]c5cc(-c6ccccc6Cl)sc5c4=O)c3c2)CN1] | 504.3 | 1H NMR (400 MHz, DMSO-d6) δ 12.33 (d, J = 5.4 Hz, 1H), 9.22 (s, 1H), 8.45 (s, 1H), 8.15 (d, J = 9.0 Hz, 1H), 7.79-7.68 (m, 3H), 7.59-7.49 (m, 2H), 7.38-7.29 (m, 2H), 6.64 (s, 1H), 6.53 (s, 1H), 4.49 (s, 1H), 3.70-3.53 (m, 1H), 3.10-3.05 (m, 1H), 2.75-2.57 (m, 2H), 2.07 (ddd, J = 16.7, 7.5, 4.9 Hz, 1H). | (4R)-4-aminopyrrolidin-2-one hydrochloride |
| 406 | 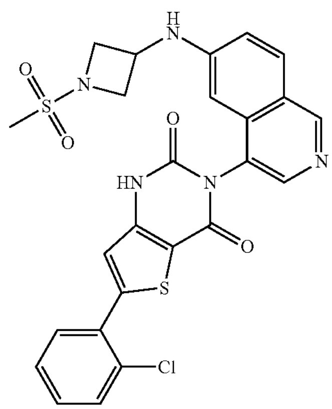 [SMILES: CS(=O)(=O)N1CC(Nc2ccc3cncc(-n4c(=O)[nH]c5cc(-c6ccccc6Cl)sc5c4=O)c3c2)C1] | 554.2 | 1H NMR (400 MHz, DMSO-d6) δ 12.32 (s, 1H), 9.23 (s, 1H), 8.43 (d, J = 18.2 Hz, 1H), 8.17 (d, J = 9.2 Hz, 1H), 7.82-7.65 (m, 3H), 7.62-7.45 (m, 2H), 7.36 (s, 1H), 7.29 (d, J = 8.4 Hz, 1H), 6.61 (s, 1H), 4.64-4.61 (m, 1H), 4.24-4.11 (m, 2H), 3.83-3.68 (m, 2H), 3.02 (s, 3H). | 1-methylsulfonyl-azetidin-3-amine hydrochloride |
| 407 | 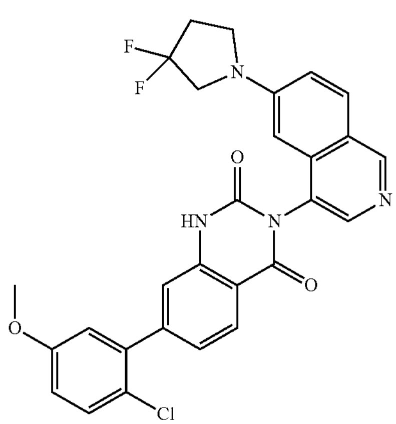 [SMILES: COc1ccc(Cl)c(-c2ccc3c(=O)n(-c4cncc5ccc(N6CCC(F)(F)C6)cc45)c(=O)[nH]c3c2)c1] | 535.3 | 1H NMR (400 MHz, DMSO-d6) δ 11.80 (s, 1H), 9.30 (s, 1H), 8.48 (s, 1H), 8.27 (d, J = 9.2 Hz, 1H), 8.05 (d, J = 8.0 Hz, 1H), 7.56 (d, J = 8.8 Hz, 1H), 7.42 (d, J = 9.2 Hz, 1H), 7.36-7.31 (m, 2H), 7.10 (dd, J = 8.8, 3.1 Hz, 1H), 6.98 (d, J = 3.1 Hz, 1H), 6.76-6.70 (m, 1H), 3.99-3.93 (m, 2H), 3.83 (s, 3H), 3.74-3.70 m, 2H), 2.64-2.55 (m, 2H). | Example 371; 3,3-difluoropyrrolidine |

TABLE 19-continued

Examples 386-427

| Example | Structure | ES/MS m/z | 1H-NMR | Changes to Procedure 37:Different Reagents/Starting Materials |
|---|---|---|---|---|
| 408 | 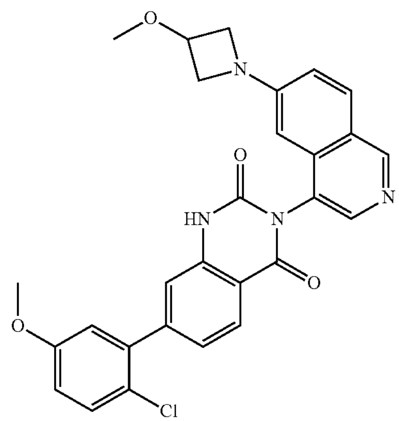 [SMILES: COc1ccc(Cl)c(-c2ccc3c(=O)n(-c4cncc5ccc(N6CC(OC)C6)cc45)c(=O)[nH]c3c2)c1] | 515.3 | 1H NMR (400 MHz, DMSO-d6) δ 11.83 (d, J = 2.8 Hz, 1H), 9.26 (d, J = 9.8 Hz, 1H), 8.46 (d, J = 5.4 Hz, 1H), 8.25-8.18 (m, 1H), 8.10-8.00 (m, 1H), 7.56 (d, J = 8.8 Hz, 1H), 7.34 (d, J = 6.6 Hz, 2H), 7.12 (ddd, J = 20.1, 8.9, 2.6 Hz, 2H), 6.99 (d, J = 3.1 Hz, 1H), 6.53 (d, J = 2.1 Hz, 1H), 4.40-4.26 (m, 2H), 3.95-3.83 (m, 1H), 3.83 (s, 3H), 3.24 (s, 3H), 3.22-3.16 (m, 2H). | Example 371; 3-methoxyazetidine |
| 409 | 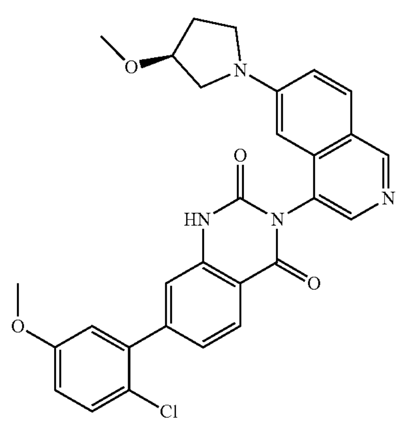 [SMILES: COc1ccc(Cl)c(-c2ccc3c(=O)n(-c4cncc5ccc(N6CC[C@H](OC)C6)cc45)c(=O)[nH]c3c2)c1] | 529.4 | 1H NMR (400 MHz, DMSO-d6) δ 11.84 (d, J = 2.0 Hz, 1H), 9.28 (s, 1H), 8.47 (s, 1H), 8.26 (d, J = 9.3 Hz, 1H), 8.09-8.01 (m, 1H), 7.56 (d, J = 8.9 Hz, 1H), 7.45 (dd, J = 9.3, 2.3 Hz, 1H), 7.34 (d, J = 7.3 Hz, 2H), 7.10 (dd, J = 8.9, 3.1 Hz, 1H), 6.99 (d, J = 3.1 Hz, 1H), 6.65 (d, J = 2.1 Hz, 1H), 4.13-4.12 (m, 1H), 3.83 (s, 3H), 3.58-3.43 (m, 4H), 3.26 (s, 3H), 2.14-2.04 (m, 2H). | Example 371; (3S)-3-methoxypyrrolidine |
| 410 | 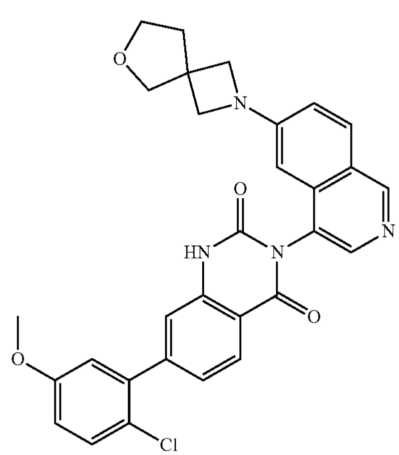 [SMILES: COc1ccc(Cl)c(-c2ccc3c(=O)n(-c4cncc5ccc(N6CC7(CCOC7)C6)cc45)c(=O)[nH]c3c2)c1] | 541.4 | 1H NMR (400 MHz, DMSO-d6) δ 11.83 (s, 1H), 9.25 (s, 1H), 8.45 (s, 1H), 8.22 (d, J = 9.1 Hz, 1H), 8.11-7.98 (m, 1H), 7.56 (d, J = 8.8 Hz, 1H), 7.40-7.28 (m, 2H), 7.16 (dd, J = 9.1, 2.2 Hz, 1H), 7.10 (dd, J = 8.8, 3.1 Hz, 1H), 6.99 (d, J = 3.0 Hz, 1H), 6.50 (d, J = 2.1 Hz, 1H), 4.11 (s, 4H), 3.83 (s, 3H), 3.82 (s, 2H), 3.72 (t, J = 6.9 Hz, 2H), 2.17 (t, J = 7.0 Hz, 2H). | Example 371; 5-oxa-2-azaspiro[3.4]octane |

TABLE 19-continued

Examples 386-427

| Example | Structure | ES/MS m/z | 1H-NMR | Changes to Procedure 37:Different Reagents/Starting Materials |
|---|---|---|---|---|
| 411 | 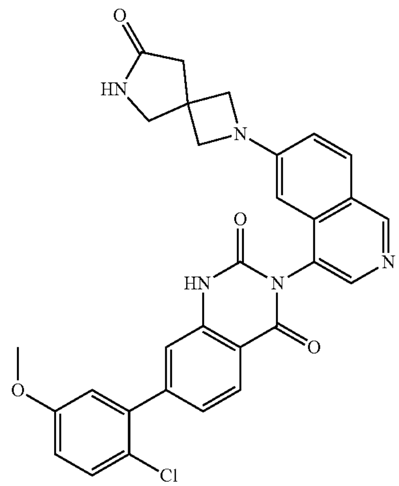 [SMILES: COc1ccc(Cl)c(-c2ccc3c(=O)n(-c4cncc5ccc(N6CC7(CNC(=O)C7)C6)cc45)c(=O)[nH]c3c2)c1] | 554.3 | 1H NMR (400 MHz, DMSO-d6) δ 11.84 (s, 1H), 9.28 (s, 1H), 8.48 (s, 1H), 8.25 (d, J = 9.1 Hz, 1H), 8.08-7.99 (m, 1H), 7.67 (s, 1H), 7.56 (d, J = 8.9 Hz, 1H), 7.36-7.30 (m, 2H), 7.18 (dd, J = 9.1, 2.2 Hz, 1H), 7.10 (dd, J = 8.9, 3.0 Hz, 1H), 6.98 (d, J = 3.0 Hz, 1H), 6.51 (d, J = 2.1 Hz, 1H), 4.13 (s, 4H), 3.83 (s, 3H), 3.49-3.46 (m, 4H). | Example 371; 2,6-diazaspiro[3.4]octan-7-one |
| 412 | 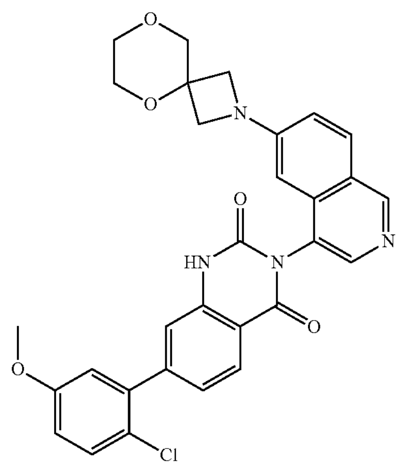 [SMILES: COc1ccc(Cl)c(-c2ccc3c(=O)n(-c4cncc5ccc(N6CC7(COCCO7)C6)cc45)c(=O)[nH]c3c2)c1] | 557.3 | 1H NMR (400 MHz, DMSO-d6) δ 11.82 (s, 1H), 9.26 (s, 1H), 8.46 (s, 1H), 8.23 (d, J = 9.1 Hz, 1H), 8.09-8.01 (m, 1H), 7.56 (d, J = 8.9 Hz, 1H), 7.39-7.28 (m, 2H), 7.19 (dd, J = 9.1, 2.2 Hz, 1H), 7.10 (dd, J = 8.9, 3.1 Hz, 1H), 6.99 (d, J = 3.0 Hz, 1H), 6.59 (d, J = 2.1 Hz, 1H), 4.10 (d, J = 9.8 Hz, 2H), 3.97 (dd, J = 9.8, 5.2 Hz, 2H), 3.83 (s, 3H), 3.73 (s, 2H), 3.67 (dd, J = 5.9, 2.9 Hz, 2H), 3.59 (dd, J = 6.0, 2.9 Hz, 2H). | Example 371; 2,6-diazaspiro[3.4]octan-7-one |
| 413 | 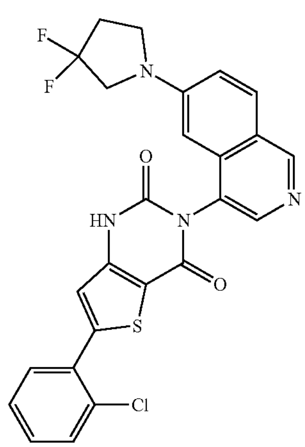 [SMILES: O=c1[nH]c2cc(-c3ccccc3Cl)sc2c(=O)n1-c1cncc2ccc(N3CCC(F)(F)C3)cc12] | 511.2 | 1H NMR (400 MHz, Methanol-d4) δ 9.27 (s, 1H), 8.45 (s, 1H), 8.34 (d, J = 9.3 Hz, 1H), 7.75-7.69 (m, 1H), 7.68-7.62 (m, 1H), 7.54-7.46 (m, 3H), 7.37 (s, 1H), 6.69 (d, J = 2.3 Hz, 1H), 4.03-3.97 (m, 2H), 3.85-3.82 (m, 2H), 2.67-2.56 (m, 2H). | 3,3-difluoropyrrolidine |

TABLE 19-continued

Examples 386-427

| Example | Structure | ES/MS m/z | 1H-NMR | Changes to Procedure 37:Different Reagents/Starting Materials |
|---|---|---|---|---|
| 414 | 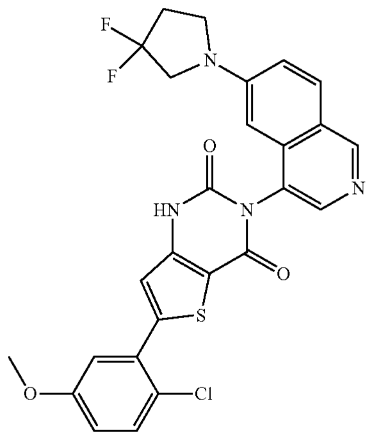 [SMILES: COc1ccc(Cl)c(-c2cc3[nH]c(=O)n(-c4cncc5ccc(N6CCC(F)(F)C6)cc45)c(=O)c3s2)c1] | 541.2 | 1H NMR (400 MHz, DMSO-d6) δ 12.26 (s, 1H), 9.36 (s, 1H), 8.54 (s, 1H), 8.33 (d, J = 9.3 Hz, 1H), 7.60 (d, J = 8.9 Hz, 1H), 7.48 (dd, J = 9.2, 2.3 Hz, 1H), 7.35 (s, 1H), 7.22 (d, J = 3.0 Hz, 1H), 7.14 (dd, J = 8.9, 3.0 Hz, 1H), 6.73 (d, J = 2.2 Hz, 1H), 4.02 (t, J = 13.0 Hz, 2H), 3.85 (s, 3H), 3.77 (t, J = 7.4 Hz, 2H), 2.67-2.56 (m, 2H). | Example 623; 3,3-difluoropyrrolidine |
| 415 | 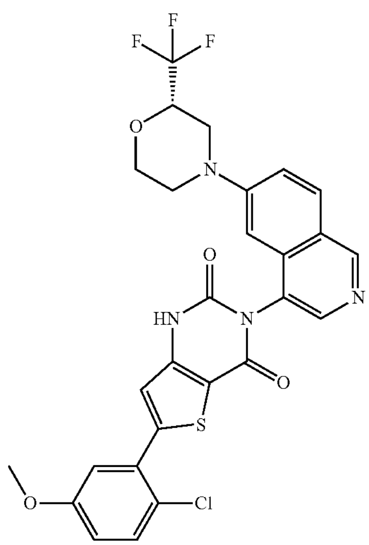 [SMILES: COc1ccc(Cl)c(-c2cc3[nH]c(=O)n(-c4cncc5ccc(N6CCO[C@H](C(F)(F)F)C6)cc45)c(=O)c3s2)c1] | 589.2 | 1H NMR (400 MHz, DMSO-d6) δ 12.22 (s, 1H), 9.28 (s, 1H), 8.47 (s, 1H), 8.23 (d, J = 9.3 Hz, 1H), 7.77 (d, J = 9.3 Hz, 1H), 7.60 (d, J = 8.9 Hz, 1H), 7.34 (s, 1H), 7.23 (d, J = 3.0 Hz, 1H), 7.14 (dd, J = 8.9, 3.1 Hz, 1H), 7.06 (s, 1H), 4.42-4.39 (m, 1H), 4.21-3.91 (m, 3H), 3.85 (s, 3H), 3.79-3.74 (m, 1H), 3.18-3.11 (m, 3H). | Example 623; (S)-2-(trifluoromethyl)morpholine |
| 416 | 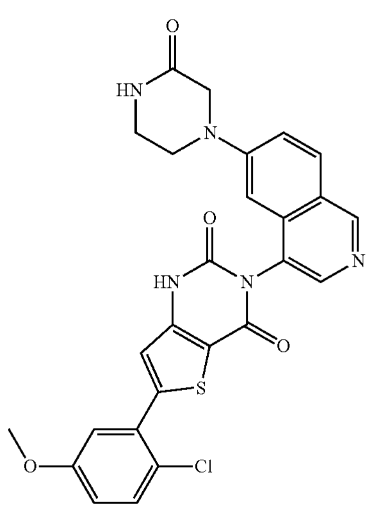 [SMILES: COc1ccc(Cl)c(-c2cc3[nH]c(=O)n(-c4cncc5ccc(N6CCNC(=O)C6)cc45)c(=O)c3s2)c1] | 534.2 | 1H NMR (400 MHz, DMSO-d6) δ 12.24 (s, 1H), 9.29 (s, 1H), 8.49 (s, 1H), 8.26 (d, J = 8.7 Hz, 2H), 7.70 (d, J = 9.2 Hz, 1H), 7.60 (d, J = 8.9 Hz, 1H), 7.34 (s, 1H), 7.24 (d, J = 3.1 Hz, 1H), 7.14 (dd, J = 8.9, 3.1 Hz, 1H), 6.96 (d, J = 2.3 Hz, 1H), 4.09 (s, 2H), 3.86 (s, 3H), 3.76 (d, J = 5.5 Hz, 2H), 3.31-3.29 (m, 2H). | Example 623; piperazin-2-one |

TABLE 19-continued

Examples 386-427

| Example | Structure | ES/MS m/z | 1H-NMR | Changes to Procedure 37:Different Reagents/Starting Materials |
|---|---|---|---|---|
| 417 | 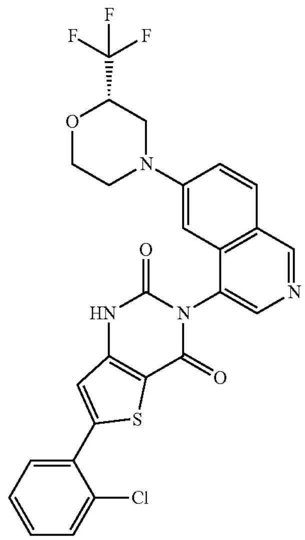 [SMILES: O=c1[nH]c2cc(-c3ccccc3Cl)sc2c(=O)n1-c1cncc2ccc(N3CCO[C@H](C(F)(F)F)C3)cc12] | 559.2 | 1H NMR (400 MHz, DMSO-d6) δ 12.24 (s, 1H), 9.30 (s, 1H), 8.50 (s, 1H), 8.25 (d, J = 9.4 Hz, 1H), 7.80 (d, J = 10.1 Hz, 1H), 7.77-7.73 (m, 1H), 7.72-7.68 (m, 1H), 7.60-7.49 (m, 2H), 7.34 (s, 1H), 7.08 (d, J = 2.1 Hz, 1H), 4.45-4.38 (m, 1H), 4.25-3.95 (m, 3H), 3.80-3.74 (m, 1H), 3.17-3.11 (m, 2H). | (S)-2-(trifluoromethyl)morpholine |
| 418 | 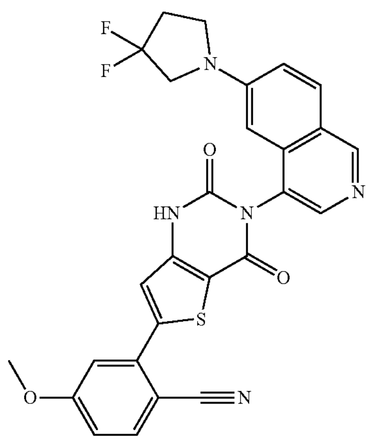 [SMILES: COc1ccc(C#N)c(-c2cc3[nH]c(=O)n(-c4cncc5ccc(N6CCC(F)(F)C6)cc45)c(=O)c3s2)c1] | 532.2 | 1H NMR (400 MHz, DMSO-d6) δ 12.28 (s, 1H), 9.26 (s, 1H), 8.48-8.36 (m, 2H), 8.24 (d, J = 9.1 Hz, 1H), 8.02 (d, J = 8.7 Hz, 1H), 7.53 (s, 1H), 7.39 (d, J = 9.0 Hz, 1H), 7.33 (d, J = 2.5 Hz, 1H), 7.28 (dd, J = 8.7, 2.5 Hz, 1H), 3.95 (s, 5H), 3.71 (s, 2H), 2.71-2.53 (m, 2H). | Example 589; 3,3-difluoropyrrolidine |
| 419 | 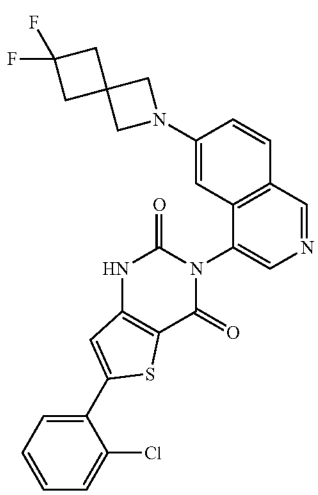 [SMILES: O=c1[nH]c2cc(-c3ccccc3Cl)sc2c(=O)n1-c1cncc2ccc(N3CC4(C3)CC(F)(F)C4)cc12] | 536.80 | 1H NMR (400 MHz, DMSO-d6) δ 12.36 (s, 0H), 12.26 (s, 1H), 9.25 (s, 1H), 8.47 (d, J = 11.3 Hz, 1H), 8.21 (d, J = 9.2 Hz, 1H), 7.80-7.66 (m, 2H), 7.60-7.49 (m, 2H), 7.41 (s, 0H), 7.34 (d, J = 4.2 Hz, 1H), 7.15 (dd, J = 9.1, 2.2 Hz, 1H), 6.67 (s, 0H), 6.47 (d, J = 2.1 Hz, 1H), 4.34 (s, 0H), 4.25 (s, 3H), 3.82 (d, J = 19.2 Hz, 0H), 2.90 (t, J = 12.4 Hz, 3H). | 6,6-difluoro-2-azaspiro[3.3]heptane; hydrochloride |

TABLE 19-continued

Examples 386-427

| Example | Structure | ES/MS m/z | 1H-NMR | Changes to Procedure 37:Different Reagents/Starting Materials |
|---|---|---|---|---|
| 420 | 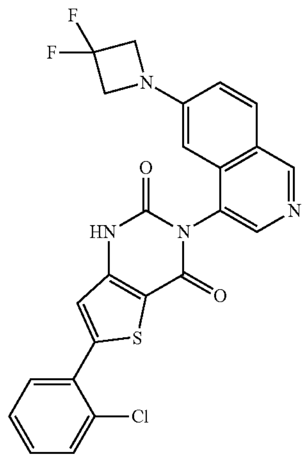 [SMILES: O=c1[nH]c2cc(-c3ccccc3Cl)sc2c(=O)n1-c1cncc2ccc(N3CC(F)(F)C3)cc12] | | 1H NMR (400 MHz, DMSO-d6) δ 12.23 (s, 1H), 9.26 (s, 1H), 8.46 (s, 1H), 8.23 (d, J = 9.0 Hz, 1H), 7.79-7.73 (m, 1H), 7.73-7.68 (m, 1H), 7.58-7.47 (m, 2H), 7.34 (s, 1H), 7.19 (dd, J = 9.4, 2.3 Hz, 1H), 6.66 (s, 1H), 4.55 (dd, J = 13.9, 10.7 Hz, 4H). | 3,3-difluoroazetidine hydrochloride |
| 421 | 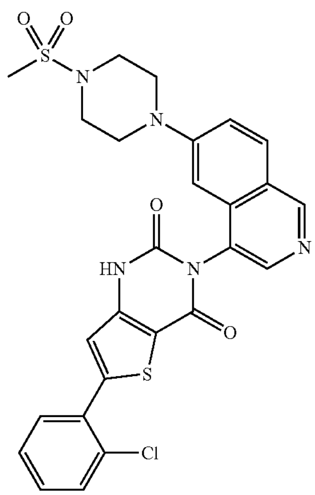 [SMILES: CS(=O)(=O)N1CCN(c2ccc3cncc(-n4c(=O)[nH]c5cc(-c6ccccc6Cl)sc5c4=O)c3c2)CC1] | 567.80 | 1H NMR (400 MHz, DMSO-d6) δ 12.23 (s, 1H), 9.29 (s, 1H), 8.50 (s, 1H), 8.26 (d, J = 9.4 Hz, 1H), 7.80-7.72 (m, 2H), 7.72-7.66 (m, 1H), 7.58-7.48 (m, 2H), 7.34 (s, 1H), 7.07 (d, J = 2.3 Hz, 1H), 3.73-3.67 (m, 4H), 3.28-3.22 (m, 4H), 2.91 (s, 3H). | 1-methylsulfonyl-piperazine |
| 422 | 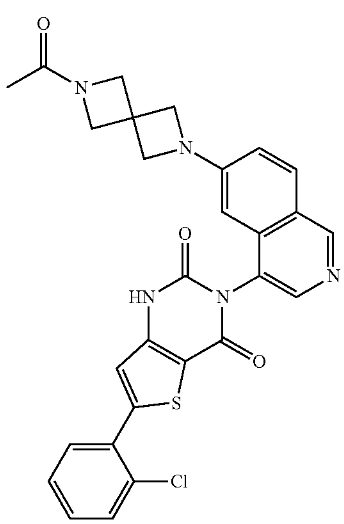 [SMILES: CC(=O)N1CC2(C1)CN(c1ccc3cncc(-n4c(=O)[nH]c5cc(-c6ccccc6Cl)sc5c4=O)c3c1)C2] | 544.00 | 1H NMR (400 MHz, DMSO-d6) δ 12.29 (s, 1H), 9.27 (s, 1H), 8.48 (s, 1H), 8.23 (d, J = 9.2 Hz, 1H), 7.78-7.72 (m, 1H), 7.72-7.67 (m, 1H), 7.59-7.48 (m, 2H), 7.34 (s, 1H), 7.17 (dd, J = 9.1, 2.2 Hz, 1H), 6.45 (d, J = 2.2 Hz, 1H), 4.36-4.21 (m, 6H), 4.05-3.97 (m, 2H), 1.73 (s, 3H). | 1-(2,6-diazaspiro[3.3]heptan-2-yl)ethanone; hydrochloride |

TABLE 19-continued

Examples 386-427

| Example | Structure | ES/MS m/z | 1H-NMR | Changes to Procedure 37:Different Reagents/Starting Materials |
|---|---|---|---|---|
| 423 | 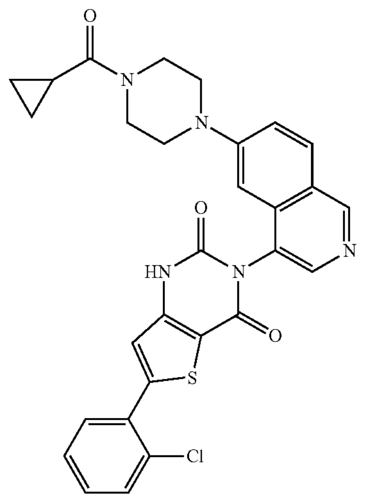 [SMILES: O=C(C1CC1)N1CCN(c2ccc3cncc(-n4c(=O)[nH]c5cc(-c6ccccc6Cl)sc5c4=O)c3c2)CC1] | 558.00 | 1H NMR (400 MHz, DMSO-d6) δ 12.23 (s, 1H), 9.27 (s, 1H), 8.47 (s, 1H), 8.24 (d, J = 9.4 Hz, 1H), 7.81-7.64 (m, 3H), 7.58-7.47 (m, 2H), 7.34 (s, 1H), 6.96 (s, 1H), 3.94-3.78 (m, 2H), 3.72-3.56 (m, 6H), 2.03-1.92 (m, 1H), 0.78-0.65 (m, 4H). | cyclopropyl (piperazin-1-yl)methanone |
| 424 | 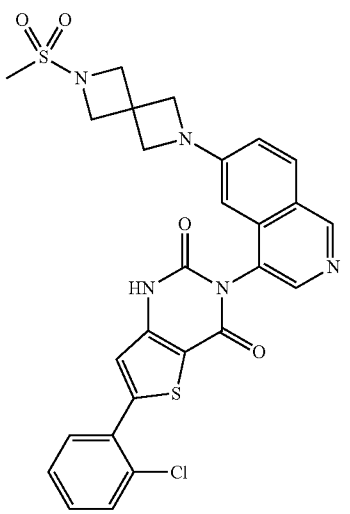 [SMILES: CS(=O)(=O)N1CC2(CN(c3ccc4cncc(-n5c(=O)[nH]c6cc(-c7ccccc7Cl)sc6c5=O)c4c3)C2)C1] | 579.80 | 1H NMR (400 MHz, DMSO-d6) δ 12.26 (s, 1H), 9.22 (s, 1H), 8.43 (s, 1H), 8.18 (d, J = 9.1 Hz, 1H), 7.79-7.72 (m, 1H), 7.72-7.66 (m, 1H), 7.58-7.47 (m, 2H), 7.34 (s, 1H), 7.16-7.07 (m, 1H), 6.40 (s, 1H), 4.32-4.19 (m, 4H), 4.12-3.99 (m, 4H), 2.98 (s, 3H). | 2-methylsulfonyl-2,6-diazaspiro[3.3] heptane |
| 425 | 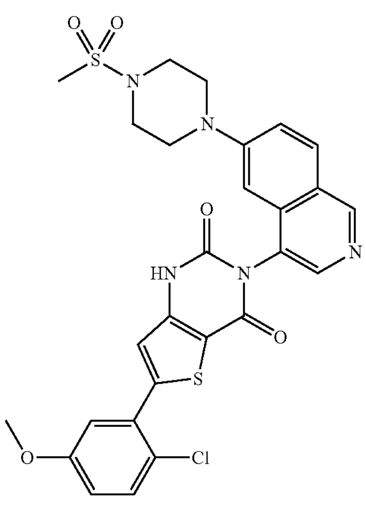 [SMILES: COc1ccc(Cl)c(-c2cc3[nH]c(=O)n(-c4cncc5ccc(N6CCN(S(C)(=O)=O)CC6)cc45)c(=O)c3s2)c1] | 597.80 | 1H NMR (400 MHz, DMSO-d6) δ 12.20 (s, 1H), 9.22 (s, 1H), 8.42 (s, 1H), 8.19 (d, J = 8.6 Hz, 1H), 7.70 (d, J = 7.5 Hz, 1H), 7.59 (d, J = 8.9 Hz, 1H), 7.34 (s, 1H), 7.22 (d, J = 3.0 Hz, 1H), 7.13 (dd, J = 8.9, 3.0 Hz, 1H), 7.00 (s, 1H), 3.85 (s, 3H), 3.64-3.57 (m, 4H), 3.28-3.23 (m, 4H), 2.91 (s, 3H). | Example 623; 1-methylsulfonyl-piperazine; 6-(2-chloro-5-methoxy-phenyl)-3-(6-fluoro-4-isoquinolyl)-1H-thieno[3,2-d]pyrimidine-2,4-dione |

TABLE 19-continued
Examples 386-427
| Example | Structure | ES/MS m/z | 1H-NMR | Changes to Procedure 37:Different Reagents/Starting Materials |
|---|---|---|---|---|
| 426 | 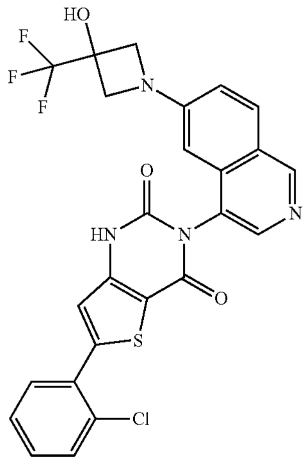 [SMILES: O=c1[nH]c2cc(-c3ccccc3Cl)sc2c(=O)n1-c1cncc2ccc(N3CC(O)(C(F)(F)F)C3)cc12] | 544.80 | 1H NMR (400 MHz, DMSO-d6) δ 12.23 (s, 1H), 9.28 (s, 1H), 8.48 (s, 1H), 8.24 (d, J = 8.9 Hz, 1H), 7.78-7.71 (m, 1H), 7.71-7.61 (m, 1H), 7.60-7.45 (m, 3H), 7.34 (s, 1H), 7.26-7.17 (m, 1H), 6.67 (s, 1H), 4.49-4.39 (m, 2H), 4.13-4.04 (m, 2H). | 3-(trifluoromethyl) azetidin-3-ol; hydrochloride |
| 427 | 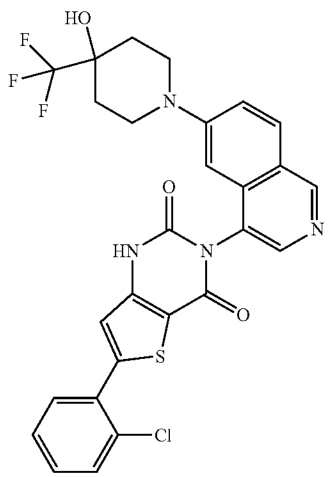 [SMILES: O=c1[nH]c2cc(-c3ccccc3Cl)sc2c(=O)n1-c1cncc2ccc(N3CCC(O)(C(F)(F)F)CC3)cc12] | 572.80 | 1H NMR (400 MHz, DMSO-d6) δ 12.25 (s, 1H), 9.29 (s, 1H), 8.50 (s, 1H), 8.25 (d, J = 9.5 Hz, 1H), 7.80 (dd, J = 9.5, 2.4 Hz, 1H), 7.76-7.71 (m, 1H), 7.71-7.65 (m, 1H), 7.58-7.47 (m, 2H), 7.33 (s, 1H), 7.07 (d, J = 2.4 Hz, 1H), 6.19 (s, 1H), 4.27-4.18 (m, 2H), 3.32-3.22 (m, 2H), 1.81-1.66 (m, 4H). | 4-(trifluoromethyl) piperidin-4-ol |
Procedure 38: Example 428:
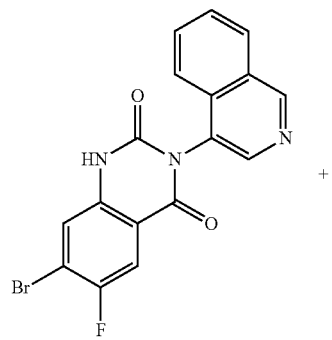
+
-continued
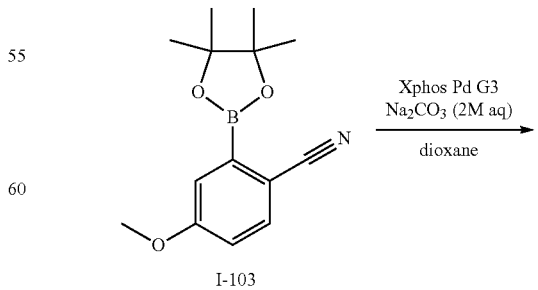

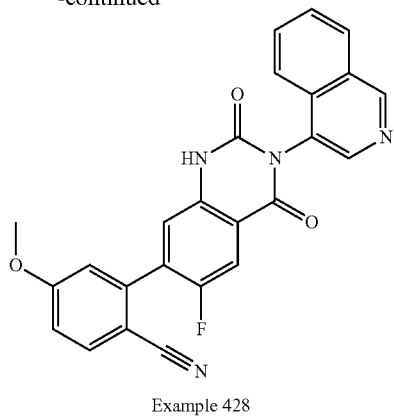

Example 428

2-(6-fluoro-3-(isoquinolin-4-yl)-2,4-dioxo-1,2,3,4-tetrahydroquinazolin-7-yl)-4-methoxybenzonitrile (Example 428): To a microwave vial with 7-bromo-6-fluoro-3-(isoquinolin-4-yl)quinazoline-2,4(1H,3H)-dione (I-3) (1(0) mg, 0.26 mmol) was added 4-methoxy-2-(4,4,5,5-tetramethyl-1,3,2-dioxaborolan-2-yl)benzonitrile (I-103) (101 mg, 0.388 mmol), and XPhos Pd G3 (20 mg, 0.026 mmol). Dioxane (2 mL) and sodium carbonate (2M aq, 0.26 mL, 0.52 mmol) were added, and the mixture was degassed with argon for 30 seconds. The vial was sealed, and the reaction mixture was heated at 100° C. for 15 minutes under microwave conditions. The crude mixture was concentrated under reduced pressure, and to the crude residue was added DMF (1 mL), acetonitrile (0.4 mL), TFA (0.3 mL) and water (0.2 mL). The mixture was heated to produce a homogeneous mixture, and the mixture was filtered through an acrodisc, and the filtrate was subsequently purified by RP-HPLC (0.1% TFA-ACN in 0.1% TFA Water, Column: Gemini 5 uM, NX-C18 110 Angstrom, 250×21.2 mm) to give the title compound Example 428 as a trifluoroacetate salt.

ES/MS: 439.1 (M+H$^+$).

1H NMR (400 MHz, DMSO-d$_6$) δ 11.98 (s, 1H), 9.49 (s, 1H), 8.63 (s, 1H), 8.31 (dd, J=7.3, 1.7 Hz, 1H), 8.00 (dd, J=15.3, 8.3 Hz, 2H), 7.90 (d, J=9.3 Hz, 1H), 7.81 (td, J=7.6, 1.5 Hz, 2H), 7.36 (d, J=6.0 Hz, 1H), 7.30 (dd, J=8.7, 2.6 Hz, 1H), 7.23 (d, J=2.5 Hz, 1H), 3.94 (s, 3H).

Examples 429-437

The following Examples were made in an analogous fashion according to Procedure 38 and are shown below in Table 20. Any different reagents/starting materials than those described in Procedure 38 are noted in the last column of Table 20—"Changes to Procedure 38: Different Reagents/Starting Materials".

TABLE 20

Examples 429-437

| Example | Structure | ES/MS m/z | 1H-NMR | Changes to Procedure 38: Different Reagents/ Starting Materials |
|---|---|---|---|---|
| 429 | 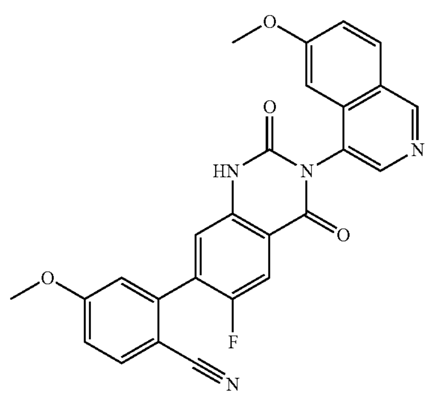 [SMILES: COc1ccc(C#N)c(-c2cc3[nH]c(=O)n(-c4cncc5ccc(OC)cc45)c(=O)c3cc2F)c1] | 468.8 | 1H NMR (400 MHz, DMSO-d6) δ 11.94 (s, 1H), 9.44 (s, 1H), 8.61 (s, 1H), 8.31 (d, J = 9.1 Hz, 1H), 8.02 (d, J = 8.7 Hz, 1H), 7.90 (d, J = 9.4 Hz, 1H), 7.49 (dd, J = 9.0, 2.4 Hz, 1H), 7.36 (d, J = 6.1 Hz, 2H), 7.30 (dd, J = 8.7, 2.6 Hz, 1H), 7.20 (d, J = 2.6 Hz, 1H), 3.93 (s, 3H), 3.91 (s, 3H). | I-71 |

TABLE 20-continued

Examples 429-437

| Example | Structure | ES/MS m/z | 1H-NMR | Changes to Procedure 38: Different Reagents/ Starting Materials |
|---|---|---|---|---|
| 430 | 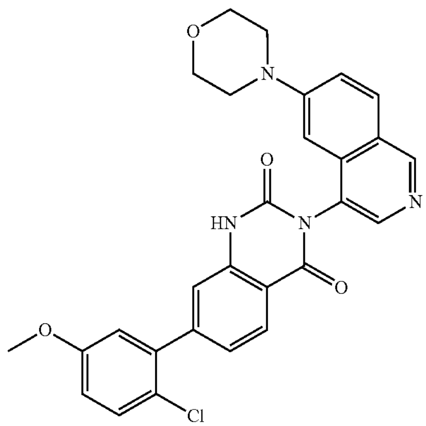 [SMILES: COc1ccc(Cl)c(-c2ccc3c(=O)n(-c4cncc5ccc(N6CCOCC6)cc45)c(=O)[nH]c3c2)c1] | 514.8 | 1H NMR (400 MHz, DMSO-d6) δ 11.81 (s, 1H), 9.33 (s, 1H), 8.52 (s, 1H), 8.28 (d, J = 9.4 Hz, 1H), 8.05 (d, J = 8.3 Hz, 1H), 7.77 (dd, J = 9.5, 2.5 Hz, 1H), 7.56 (d, J = 8.8 Hz, 1H), 7.33 (d, J = 7.5 Hz, 2H), 7.15-7.06 (m, 2H), 6.98 (d, J = 3.1 Hz, 1H), 3.83 (s, 3H), 3.78-3.65 (m, 4H), 3.61-3.49 (m, 4H). | I-73; (2-chloro-5-methoxy-phenyl)boronic acid |
| 431 | 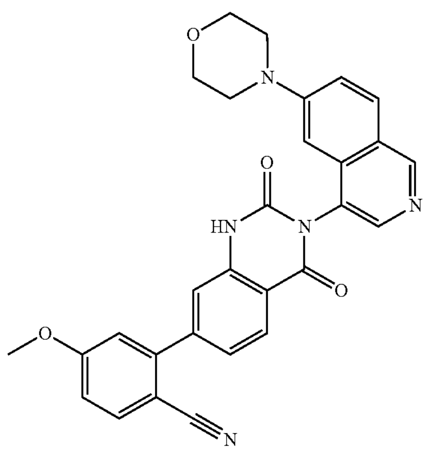 [SMILES: COc1ccc(C#N)c(-c2ccc3c(=O)n(-c4cncc5ccc(N6CCOCC6)cc45)c(=O)[nH]c3c2)c1] | 505.9 | 1H NMR (400 MHz, DMSO-d6) δ 11.90 (s, 1H), 9.32 (s, 1H), 8.52 (s, 1H), 8.28 (d, J = 9.4 Hz, 1H), 8.10 (d, J = 8.5 Hz, 1H), 7.99 (d, J = 8.7 Hz, 1H), 7.86-7.65 (m, 1H), 7.46 (dq, J = 4.0, 1.7 Hz, 2H), 7.40-7.24 (m, 1H), 7.24-7.01 (m, 2H), 3.94 (s, 3H), 3.73 (t, J = 4.8 Hz, 4H), 3.57 (t, J = 4.9 Hz, 4H). | I-73 |
| 432 | 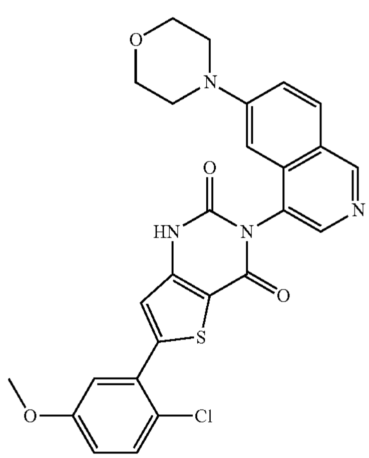 [SMILES: COc1ccc(Cl)c(-c2cc3[nH]c(=O)n(-c4cncc5ccc(N6CCOCC6)cc45)c(=O)c3s2)c1] | 520.8 | 1H NMR (400 MHz, DMSO-d6) δ 11.81 (s, 1H), 9.33 (s, 1H), 8.52 (s, 1H), 8.28 (d, J = 9.4 Hz, 1H), 8.05 (d, J = 8.3 Hz, 1H), 7.77 (dd, J = 9.5, 2.5 Hz, 1H), 7.56 (d, J = 8.8 Hz, 1H), 7.33 (d, J = 7.5 Hz, 2H), 7.15-7.06 (m, 2H), 6.98 (d, J = 3.1 Hz, 1H), 3.83 (s, 3H), 3.78-3.65 (m, 4H), 3.61-3.49 (m, 4H). | I-75; (2-chloro-5-methoxy-phenyl)boronic acid |

TABLE 20-continued

Examples 429-437

| Example | Structure | ES/MS m/z | 1H-NMR | Changes to Procedure 38: Different Reagents/ Starting Materials |
|---|---|---|---|---|
| 433 | 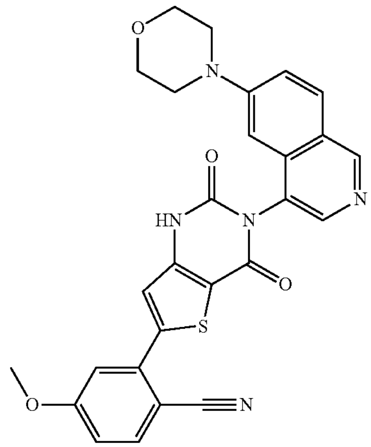 [SMILES: COc1ccc(C#N)c(-c2cc3[nH]c(=O)n(-c4cncc5ccc(N6CCOCC6)cc45)c(=O)c3s2)c1] | 511.8 | 1H NMR (400 MHz, DMSO-d6) δ 12.30 (s, 1H), 9.30 (s, 1H), 8.50 (s, 1H), 8.26 (d, J = 9.4 Hz, 1H), 8.02 (d, J = 8.7 Hz, 1H), 7.73 (dd, J = 15.2, 8.8 Hz, 1H), 7.52 (s, 1H), 7.33-7.22 (m, 2H), 7.02 (d, J = 2.3 Hz, 1H), 3.95 (s, 3H), 3.74 (dd, J = 5.8, 3.8 Hz, 4H), 3.56 (d, J = 5.6 Hz, 4H). | I-75 |
| 434 | 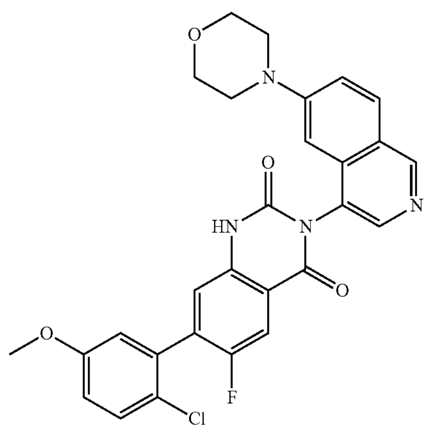 [SMILES: COc1ccc(Cl)c(-c2cc3[nH]c(=O)n(-c4cncc5ccc(N6CCOCC6)cc45)c(=O)c3cc2F)c1] | 532.8 | 1H NMR (400 MHz, DMSO-d6) δ 11.87 (s, 1H), 9.32 (s, 1H), 8.50 (s, 1H), 8.27 (d, J = 9.4 Hz, 1H), 7.82 (d, J = 9.1 Hz, 1H), 7.76 (dd, J = 9.5, 2.4 Hz, 1H), 7.58 (d, J = 8.9 Hz, 1H), 7.24 (d, J = 5.9 Hz, 1H), 7.15 (dd, J = 8.9, 3.0 Hz, 1H), 7.08 (s, 1H), 7.01 (d, J = 3.0 Hz, 1H), 3.83 (s, 3H), 3.74 (t, J = 4.8 Hz, 4H), 3.57 (t, J = 4.7 Hz, 4H). | I-76; (2-chloro-5-methoxy-phenyl)boronic acid |
| 435 | 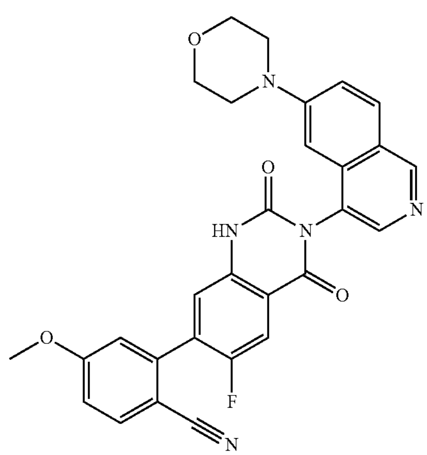 [SMILES: COc1ccc(C#N)c(-c2cc3[nH]c(=O)n(-c4cncc5ccc(N6CCOCC6)cc45)c(=O)c3cc2F)c1] | 523.8 | 1H NMR (400 MHz, DMSO-d6) δ 11.93 (s, 1H), 9.30 (s, 1H), 8.50 (s, 1H), 8.26 (d, J = 9.4 Hz, 1H), 8.02 (d, J = 8.7 Hz, 1H), 7.90 (d, J = 9.3 Hz, 1H), 7.75 (dd, J = 9.5, 2.4 Hz, 1H), 7.35 (d, J = 6.0 Hz, 1H), 7.30 (dd, J = 8.8, 2.6 Hz, 1H), 7.18 (d, J = 2.6 Hz, 1H), 7.09 (d, J = 2.4 Hz, 1H), 3.93 (s, 3H), 3.73 (dd, J = 5.7, 3.9 Hz, 4H), 3.56 (t, J = 4.7 Hz, 4H). | I-76 |

TABLE 20-continued

Examples 429-437

| Example | Structure | ES/MS m/z | 1H-NMR | Changes to Procedure 38: Different Reagents/ Starting Materials |
|---|---|---|---|---|
| 436 | 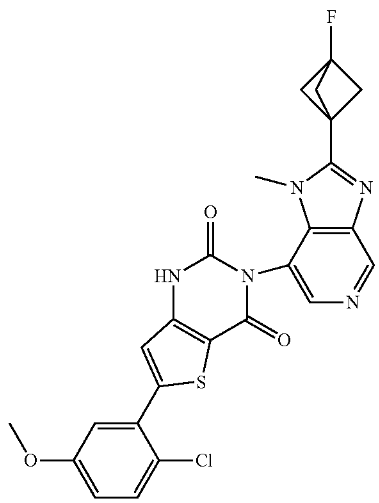 [SMILES: COc1ccc(Cl)c(-c2cc3[nH]c(=O)n(-c4cncc5nc(C67CC(F)(C6)C7)n(C)c45)c(=O)c3s2)c1] | 523.8 | 1H NMR (400 MHz, DMSO-d6) δ 12.47 (s, 1H), 9.09 (s, 1H), 8.45 (s, 1H), 7.60 (d, J = 8.9 Hz, 1H), 7.34 (s, 1H), 7.26 (d, J = 3.0 Hz, 1H), 7.14 (dd, J = 8.9, 3.0 Hz, 1H), 3.85 (s, 3H), 3.69 (s, 3H), 2.72-2.69 (m, 6H). | I-82; (2-chloro-5-methoxy-phenyl)boronic acid |
| 437 | 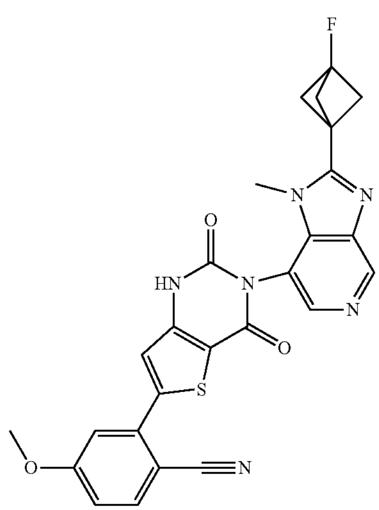 [SMILES: COc1ccc(C#N)c(-c2cc3[nH]c(=O)n(-c4cncc5nc(C67CC(F)(C6)C7)n(C)c45)c(=O)c3s2)c1] | 514.8 | 1H NMR (400 MHz, DMSO-d6) δ 12.53 (s, 1H), 9.08 (s, 1H), 8.45 (s, 1H), 8.01 (d, J = 8.7 Hz, 1H), 7.52 (s, 1H), 7.41-7.22 (m, 2H), 3.95 (s, 3H), 3.69 (s, 3H), 2.70 (d, J = 2.4 Hz, 6H). | I-82 |

Procedure 39: Example 438 and Example 439

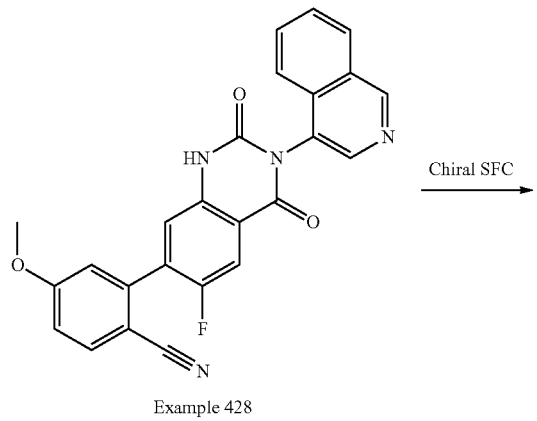

Example 428

Chiral SFC →

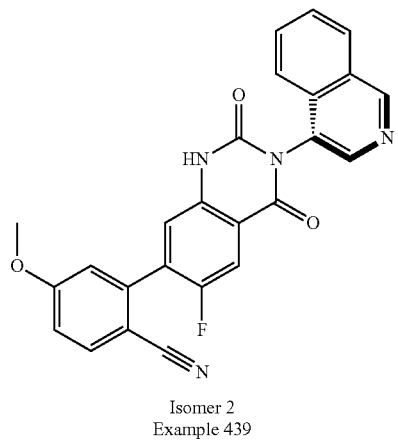

Isomer 2
Example 439

2-(6-fluoro-3-(isoquinolin-4-yl)-2,4-dioxo-1,2,3,4-tetrahydroquinazolin-7-yl)-4-methoxybenzonitrile (Example 438 and Example 439): 2-(6-fluoro-3-(isoquinolin-4-yl)-2,4-dioxo-1,2,3,4-tetrahydroquinazolin-7-yl)-4-methoxybenzonitrile (Example 428) as a mixture of 2 atropisomers was separated by chiral SFC (IB 5 μm 21×250 mm column with 35% MeOH cosolvent) to give two enantiomers, which were assigned as Isomer 1 and Isomer 2. The absolute configuration of Example 438 (Isomer 1) was confirmed by an X-Ray structure obtained of Example 438 bound to the Mpro protein.

Isomer 1:

2-(6-fluoro-3-(isoquinolin-4-yl)-2,4-dioxo-1,2,3,4-tetrahydroquinazolin-7-yl)-4-methoxybenzonitrile (Example 438)

ES/MS: 438.9 (M+).

1H NMR (400 MHz, DMSO-$d_6$) δ 11.98 (s, 1H), 9.48 (s, 1H), 8.62 (s, 1H), 8.44-8.21 (m, 1H), 8.02 (d, J=8.7 Hz, 1H), 7.99-7.93 (m, 1H), 7.89 (d, J=9.4 Hz, 1H), 7.81 (td, J=7.4, 1.5 Hz, 2H), 7.36 (d, J=6.0 Hz, 1H), 7.30 (dd, J=8.7, 2.6 Hz, 1H), 7.23 (d, J=2.6 Hz, 1H), 3.94 (s, 3H).

Isomer 2:

2-(6-fluoro-3-(isoquinolin-4-yl)-2,4-dioxo-1,2,3,4-tetrahydroquinazolin-7-yl)-4-methoxybenzonitrile (Example 439)

ES/MS: 438.8 (M+).

1H NMR (400 MHz, DMSO-$d_6$) δ 11.98 (s, 1H), 9.49 (s, 1H), 8.63 (s, 1H), 8.31 (dd, J=7.5, 1.8 Hz, 1H), 8.00 (dd, J=16.4, 8.1 Hz, 2H), 7.90 (d, J=9.3 Hz, 1H), 7.81 (pd, J=7.0, 1.5 Hz, 2H), 7.36 (d, J=6.0 Hz, 1H), 7.30 (dd, J=8.7, 2.6 Hz, 1H), 7.23 (d, J=2.6 Hz, 1H), 3.94 (s, 3H).

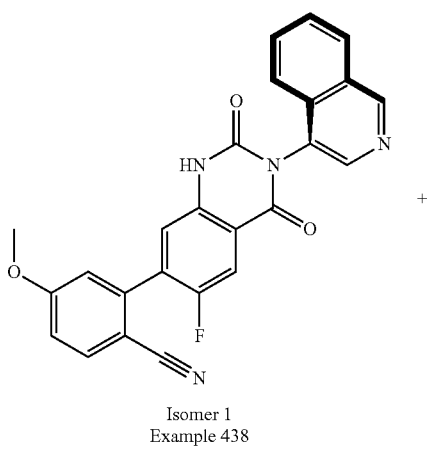

Isomer 1
Example 438

Procedure 40: Example 440 and Example 441

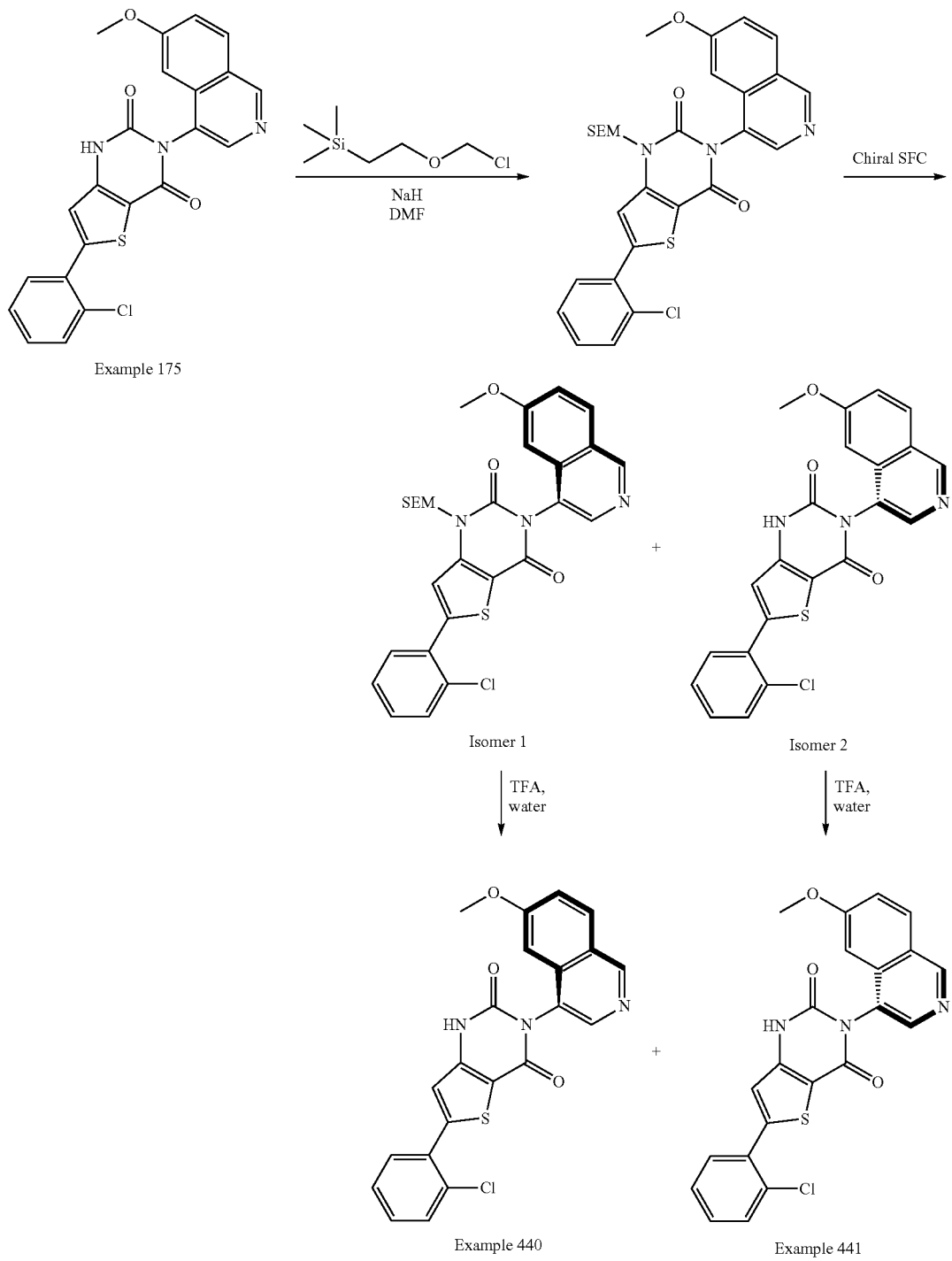

6-(2-chlorophenyl)-3-(6-methoxyisoquinolin-4-yl)-1-((2-(trimethylsilyl)ethoxy)methyl)thieno[3,2-d]pyrimidine-2,4(1H,3H)-dione To a stirring solution of 6-(2-chlorophenyl)-3-(6-methoxyisoquinolin-4-yl)thieno[3,2-d]pyrimidine-2,4(1H,3H)-dione (Example 175) (2.0 g, 4.59 mmol, 1 equiv.) in DMF (15 mL) at 0° C. was added 60% NaH (0.264 g, 6.88 mmol, 1.5 equiv.) and stirred for 45 min after which 2-(chloromethoxy)ethyl-trimethyl-silane (0.89 mL, 5.05 mmol, 1.1 equiv.) was added. The reaction mixture was stirred at rt for 30 min after which NaHCO$_3$ (10 mL) was added followed by EtOAc (100 mL). The partitions were separated, and the organic layer was washed with brine (2×20 mL), dried over MgSO$_4$, and concentrated under reduced pressure. The crude residue was purified by silica gel chromatography (eluent: EtOAc/hexanes), to provide the product.

6-(2-chlorophenyl)-3-(6-methoxyisoquinolin-4-yl)thieno[3,2-d]pyrimidine-2,4(1H,3H)-dione (Example 440 and Example 441)

6-(2-chlorophenyl)-3-(6-methoxyisoquinolin-4-yl)-1-((2-(trimethylsilyl)ethoxy)methyl)thieno[3,2-d]pyrimidine-2,4(1H,3H)-dione as a mixture of 2 atropisomers was separated by chiral SFC (AD-H 5 μm 21×250 mm column with 25% MeOH cosolvent). These two isomers were separately reacted according to the conditions in Procedure 69 to afford the two enantiomers, assigned as Isomer 1 and Isomer 2. The stereochemistry was assigned by analogy to Example 438, with Example 440 being the more active isomer.

Isomer 1:

6-(2-chlorophenyl)-3-(6-methoxyisoquinolin-4-yl)thieno[3,2-d]pyrimidine-2,4(1H,3H)-dione (Example 440)

ES/MS: 435.8 (M+).

1H NMR (400 MHz, DMSO-$d_6$) δ 12.25 (s, 1H), 9.43 (s, 1H), 8.60 (s, 1H), 8.31 (d, J=9.1 Hz, 1H), 7.80-7.66 (m, 2H), 7.58-7.44 (m, 3H), 7.35 (s, 1H), 7.28 (d, J=2.4 Hz, 1H), 3.92 (s, 3H).

Isomer 2:

6-(2-chlorophenyl)-3-(6-methoxyisoquinolin-4-yl)thieno[3,2-d]pyrimidine-2,4(1H,3H)-dione (Example 441)

ES/MS: 435.8 (M+).

1H NMR (400 MHz, DMSO-$d_6$) δ 12.25 (s, 1H), 9.43 (s, 1H), 8.59 (s, 1H), 8.31 (d, J=9.1 Hz, 1H), 7.81-7.69 (m, 2H), 7.59-7.44 (m, 3H), 7.35 (s, 1H), 7.28 (d, J=2.4 Hz, 1H), 3.92 (s, 3H).

Procedure 41: Example 442 and Example 443

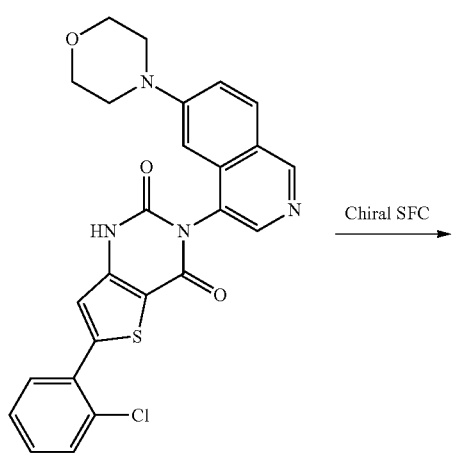

Example 385

Chiral SFC →

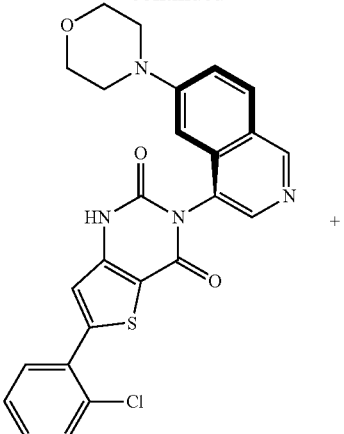

Isomer 1
Example 442

+

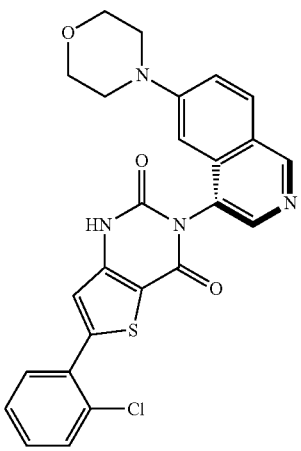

Isomer 2
Example 443

6-(2-chlorophenyl)-3-(6-morpholinoisoquinolin-4-yl)thieno[3,2-d]pyrimidine-2,4(1H,3H)-dione (Example 442 and Example 443): 6-(2-chlorophenyl)-3-(6-morpholinoisoquinolin-4-yl)thieno[3,2-d]pyrimidine-2,4(1H,3H)-dione (Example 385) as a mixture of 2 stereoisomers was separated by chiral SFC (IB 5 μm 4.6×100 mm column with 35% MeOH cosolvent) to give two enantiomers, which were assigned as Isomer 1 and Isomer 2. The stereochemistry was assigned by analogy to Example 438, with Example 442 being the more active isomer.

Isomer 1:

6-(2-chlorophenyl)-3-(6-morpholinoisoquinolin-4-yl)thieno[3,2-d]pyrimidine-2,4(1H,3H)-dione (Example 442)

ES/MS: 490.8 (M+).

1H NMR (400 MHz, DMSO-$d_6$) δ 12.24 (s, 11H), 9.30 (s, 11H), 8.51 (s, 11H), 8.26 (d, J=9.4 Hz, 1H), 7.80-7.65 (m, 3H), 7.57-7.48 (m, 2H), 7.34 (s, 1H), 7.02 (d, J=2.3 Hz, 1H), 3.77-3.68 (m, 4H), 3.59-3.53 (m, 4H).

Isomer 2:

6-(2-chlorophenyl)-3-(6-morpholinoisoquinolin-4-yl)thieno[3,2-d]pyrimidine-2,4(1H,3H)-dione (Example 443)

ES/MS: 490.8 (M+).
1H NMR (400 MHz, DMSO-d$_6$) δ 12.25 (s, 11H), 9.32 (s, 11H), 8.52 (s, 11H), 8.27 (d, J=8.8 Hz, 1H), 7.73 (d, J=20.9 Hz, 3H), 7.64-7.43 (m, 2H), 7.34 (s, 1H), 7.03 (s, 1H), 3.77-3.68 (m, 4H), 3.59-3.55 (m, 4H).

Procedure 42: Example 444

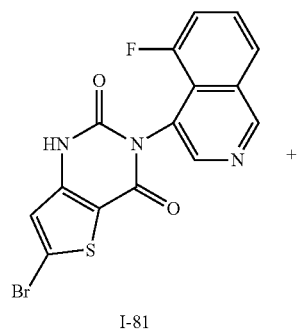

I-81

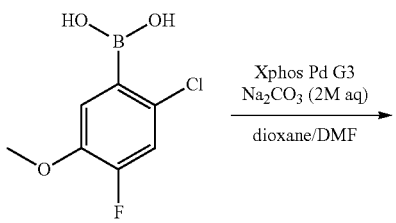

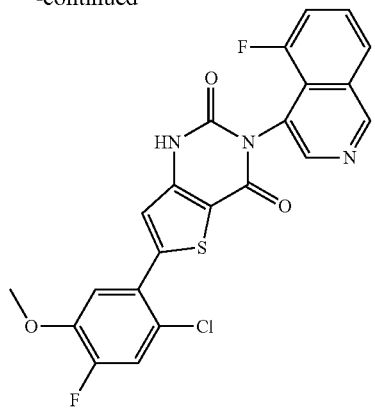

Example 444

6-(2-chloro-4-fluoro-5-methoxyphenyl)-3-(5-fluoroisoquinolin-4-yl)thieno[3,2-d]pyrimidine-2,4(1H,3H)-dione (Example 444): To a microwave vial with 6-bromo-3-(5-fluoroisoquinolin-4-yl)thieno[3,2-d]pyrimidine-2,4(1H,3H)-dione (I-81) (50 mg, 0.127 mmol) was added (2-chloro-4-fluoro-5-methoxyphenyl)boronic acid (34 mg, 0.166 mmol), and XPhos Pd G3 (9.6 mg, 0.013 mmol). Dioxane (0.75 mL), DMF (0.75 mL) and sodium carbonate (2M aq, 0.19 mL, 0.38 mmol) were added, and the mixture was degassed with argon for 30 seconds. The vial was sealed, and the reaction mixture was heated at 100° C. for 15 minutes under microwave conditions. The crude mixture was concentrated under reduced pressure, and to the crude residue was added acetonitrile (1 mL), TFA (0.3 mL) and water (0.2 mL). The mixture was heated to produce a homogeneous mixture, and the mixture was filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the title compound Example 444 as a trifluoroacetate salt.

ES/MS: 471.7 (M$^+$).
1H NMR (400 MHz, DMSO-d$_6$) δ 12.33 (s, 1H), 9.53 (d, J=2.5 Hz, 1H), 8.61 (s, 1H), 8.18 (dd, J=8.3, 1.0 Hz, 1H), 7.86-7.57 (m, 3H), 7.50 (d, J=8.9 Hz, 1H), 7.30 (s, 1H), 3.95 (s, 3H).

Examples 445-446

The following Examples were made in an analogous fashion according to Procedure 42 and are shown below in Table 21. Any different reagents/starting materials than those described in Procedure 42 are noted in the last column of Table 21—"Changes to Procedure 42: Different Reagents/Starting Materials".

TABLE 21

Examples 445-446

| Example | Structure | ES/MS m/z | 1H-NMR | Changes to Procedure 42: Different Reagents/ Starting Materials |
|---|---|---|---|---|
| 445 | 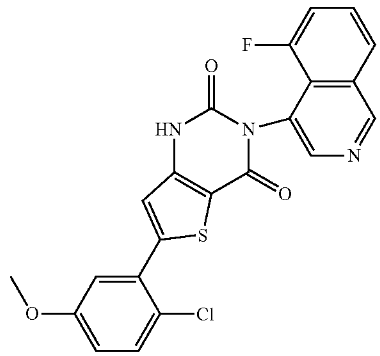 [SMILES: COc1ccc(Cl)c(-c2cc3[nH]c(=O)n(-c4cncc5cccc(F)c45)c(=O)c3s2)c1] | 453.7 | 1H NMR (400 MHz, DMSO-d6) δ 12.31 (s, 1H), 9.53 (s, 1H), 8.61 (s, 1H), 8.18 (d, J = 8.2 Hz, 1H), 7.79 (dt, J = 12.3, 5.7 Hz, 1H), 7.69-7.49 (m, 2H), 7.30 (dd, J = 14.6, 3.3 Hz, 2H), 7.13 (dt, J = 6.5, 3.4 Hz, 1H), 3.86 (d, J = 3.8 Hz, 3H). | (2-chloro-5-methoxy-phenyl)boronic acid |
| 446 | 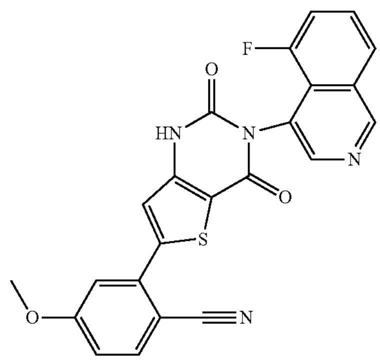 [SMILES: COc1ccc(C#N)c(-c2cc3[nH]c(=O)n(-c4cncc5cccc(F)c45)c(=O)c3s2)c1] | 444.8 | 1H NMR (400 MHz, DMSO-d6) δ 12.39 (s, 1H), 9.53 (s, 1H), 8.62 (s, 1H), 8.18 (d, J = 8.5 Hz, 1H), 8.01 (d, J = 8.5 Hz, 1H), 7.78 (d, J = 8.1 Hz, 1H), 7.65 (t, J = 10.4 Hz, 1H), 7.50 (s, 1H), 7.38 (s, 1H), 7.27 (d, J = 8.9 Hz, 1H), 3.95 (s, 3H). | 4-methoxy-2-(4,4,5,5-tetramethyl-1,3,2-dioxaborolan-2-yl)benzonitrile |

Procedure 43: Example 447 and Example 448

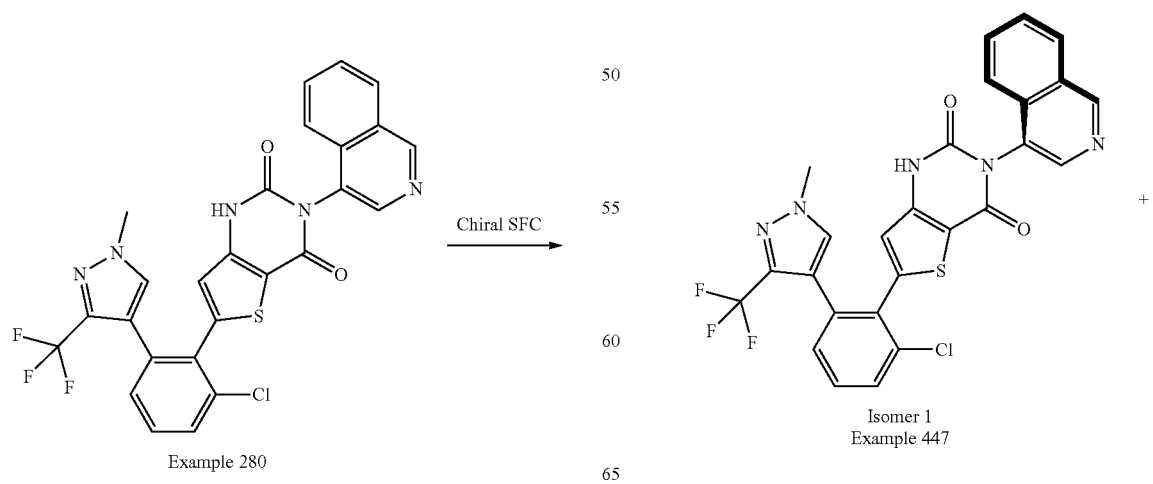

Isomer 1
Example 447

-continued

983
-continued

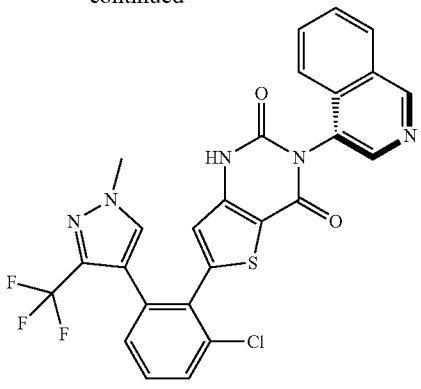

Isomer 2
Example 448

6-(2-chloro-6-(1-methyl-3-(trifluoromethyl)-1H-pyrazol-4-yl)phenyl)-3-(isoquinolin-4-yl)thieno[3,2-d]pyrimidine-2,4(1H,3H)-dione (Example 447 and Example 448): 6-(2-chloro-6-(I-methyl-3-(trifluoromethyl)-1H-pyrazol-4-yl)phenyl)-3-(isoquinolin-4-yl)thieno[3,2-d]pyrimidine-2,4 (1H,3H)-dione (Example 280) as a mixture of 2 atropisomers was separated by chiral SFC (IB 5 μm 4.6×100 mm column with 35% MeOH cosolvent) to give two enantiomers, which were assigned as Isomer 1 and Isomer 2. The stereochemistry was assigned by analogy to Example 438, with Example 447 being the more active isomer.

Isomer 1:

6-(2-chloro-&(l-methyl-3-(trifluoromethyl)-1H-pyrazol-4-yl)phenyl)-3-(isoquinolin-4-yl)thieno[3,2-d]pyramidine-2,4(1H,3H)-dione (Example 447)

ES/MS: 553.7 (M⁺).

1H NMR (400 MHz, DMSO-d₆) δ 12.20 (s, 1H), 9.42 (s, 1H), 8.56 (s, 1H), 8.27 (dd, J=7.9, 1.4 Hz, 1H), 7.91 (s, 1H), 7.85-7.70 (m, 3H), 7.60 (t, J=7.9 Hz, 1H), 7.40 (dd, J=7.7, 1.1 Hz, 1H), 6.89 (s, 1H), 3.92 (s, 3H).

Isomer 2:

6-(2-chloro-6-(1-methyl-3-(trifluoromethyl)-1H-pyrazol-4-yl)phenyl)-3-(isoquinolin-4-yl)thieno[3,2-d]pyrimidine-2,4(1H,3H)-dione (Example 448)

ES/MS: 553.7 (M+).

1H NMR (400 MHz, DMSO-d₆) δ 12.21 (s, 1H), 9.44 (d, J=3.5 Hz, 1H), 8.58 (d, J=3.1 Hz, 1H), 8.28 (d, J=8.1 Hz, 1H), 7.91 (d, J=3.4 Hz, 1H), 7.84-7.71 (m, 3H), 7.60 (td, J=8.2, 3.3 Hz, 1H), 7.40 (d, J=7.7 Hz, 1H), 6.89 (d, J=3.0 Hz, 1H), 4.04-3.82 (m, 3H).

984

Procedure 44: Example 449

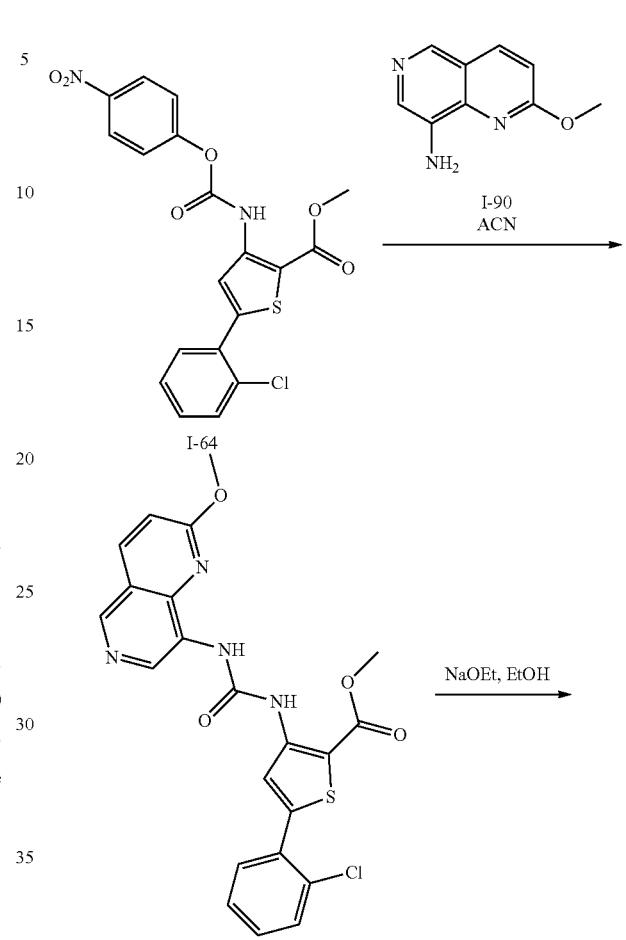

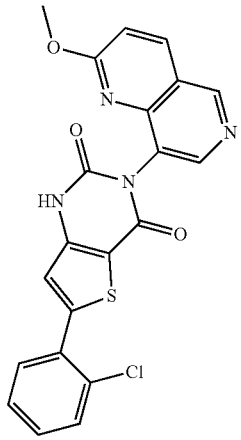

Example 449 methyl 5-(2-chlorophenyl)-3-(3-(2-methoxy-1,6-naphthyridin-8-yl)ureido)thiophene-2-carboxylate: To a solution of methyl 5-(2-chlorophenyl)-3-(((4-nitrophenoxy)carbonyl)amino)thiophene-2-carboxylate (I-64) (50 mg, 0.12 mmol) in ACN (2 mL), was added 2-methoxy-1,6-naphthyridin-8-amine (I-90) (40 mg, 0.23 mmol). The reaction was heated at 80° C. for 1 hour. The reaction was directly filtered and solids were rinsed with ACN. The solid was dried under vacuum and carried forward to the next step.

ES/MS: 469.0 (M⁺).

6-(2-chlorophenyl)-3-(2-methoxy-1,6-naphthyridin-8-yl)thieno[3,2-d]pyrimidine-2,4(1H,3H)-dione (Example 449): To a solution of methyl 5-(2-chlorophenyl)-3-(3-(2-methoxy-1,6-naphthyridin-8-yl)ureido)thiophene-2-carboxylate (50 mg, 0.12 mmol) in ethanol (1 mL) was added sodium ethoxide (0.1 ml, 20% in ethanol). The reaction was stirred for 2 hours and concentrated. The residue was dissolved in 1 ml DMF and 0.5 ml 1:2 TFA:water, filtered through an acrodisc, and purified by RP-HPLC (0.1% TFA-ACN in 0.1% TFA Water, Column: Gemini 5 uM, NX-C18 110 Angstrom, 250×21.2 mm) to give the title compound Example 449 as a trifluoroacetate salt.

ES/MS: 437.2 (M+).

$^1$H NMR (400 MHz, DMSO-d$_6$) δ 12.23 (s, 1H), 9.32 (s, 1H), 8.72 (s, 1H), 8.55 (d, 1H), 7.83-7.74 (in, 1H), 7.73-7.66 (m, 1H), 7.59-7.48 (m, 2H), 7.34 (s, 1H), 7.23 (d, 1H), 3.84 (s, 3H).

Examples 450-451

The following Examples were made in an analogous fashion according to Procedure 44 and are shown below in Table 22. Any different reagents/starting materials than those described in Procedure 44 are noted in the last column of Table 22—"Changes to Procedure 44: Different Reagents/Starting Materials".

TABLE 22

Examples 450-451

| Example | Structure | ES/MS m/z | $^1$H-NMR | Changes to Procedure 44: Different Reagents/Starting Materials |
|---|---|---|---|---|
| 450 | 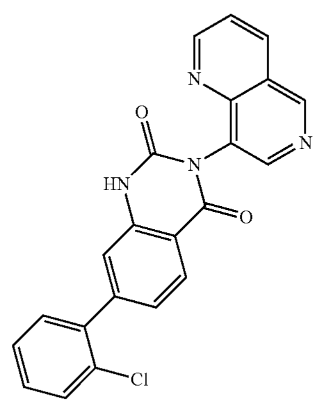 [SMILES: O=c1[nH]c2cc(-c3ccccc3Cl)ccc2c(=O)n1-c1cncc2cccnc12] | 401.2 | $^1$H NMR (400 MHz, DMSO-d6) δ 11.87 (s, 1H), 9.57 (s, 1H), 9.12 (dd, 1H), 8.86 (d, 1H), 8.75 (dd, 1H), 8.05 (d, 1H), 7.81 (dd, 1H), 7.70-7.62 (m, 1H), 7.52 (dd, 3H), 7.37-7.30 (m, 2H). | I-68; I-36 |
| 451 | 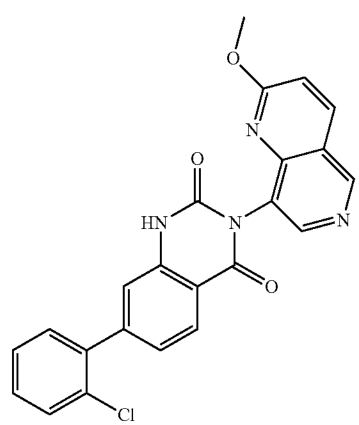 [SMILES: COc1ccc2cncc(-n3c(=O)[nH]c4cc(-c5ccccc5Cl)ccc4c3=O)c2n1] | 437.2 | 1H NMR (400 MHz, DMSO-d6) δ 12.23 (s, 1H), 9.32 (s, 1H), 8.72 (s, 1H), 8.55 (d, 1H), 7.83-7.74 (m, 1H), 7.73-7.66 (m, 1H), 7.59-7.48 (m, 2H), 7.34 (s, 1H), 7.23 (d, 1H), 3.84 (s, 3H). | I-68 |

Procedure 45: Example 452

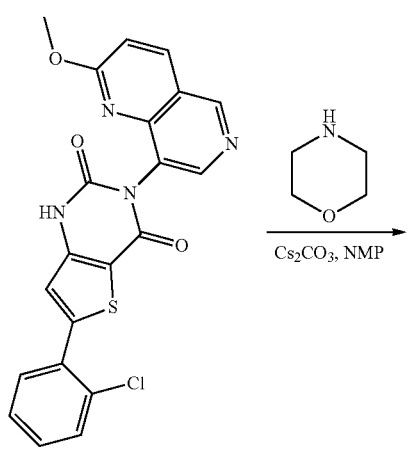

Example 449

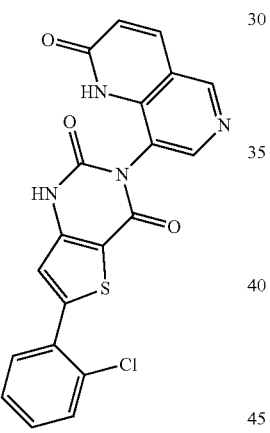

Example 452

6-(2-chlorophenyl)-3-(2-oxo-1,2-dihydro-1,6-naphthyridin-8-yl)thieno[3,2-d]pyrimidine-2,4(1H,3H)-dione (Example 452): To a solution 6-(2-chlorophenyl)-3-(2-methoxy-1,6-naphthyridin-8-yl)thieno[3,2-d]pyrimidine-2,4(1H,3H)-dione (Example 449) (50 mg, 0.11 mmol) in NMP (1 mL) was added cesium carbonate (112 mg, 0.34 mmol) and morpholine (100 mg, 1.15 mmol). The reaction was stirred for 24 hours at 120° C. and then cooled to RT. The reaction was diluted with 1 ml DMF and 0.5 ml 1:2 TFA:water, filtered and purified by RP-HPLC (0.1% TFA-ACN in 0.1% TFA Water, Column: Gemini 5 uM, NX-C18 110 Angstrom, 250×21.2 mm) to give the title compound Example 452 as a trifluoroacetate salt.

ES/MS: 423.0 (M+).

$^1$H NMR (400 MHz, DMSO-$d_6$) δ 12.23 (s, 1H), 12.13 (s, 1H), 8.92 (s, 1H), 8.50 (s, 1H), 8.12 (d, 1H), 7.78-7.65 (m, 2H), 7.59-7.48 (m, 2H), 7.29 (s, 1H), 6.66 (dd, 1H).

Procedure 46: Example 453

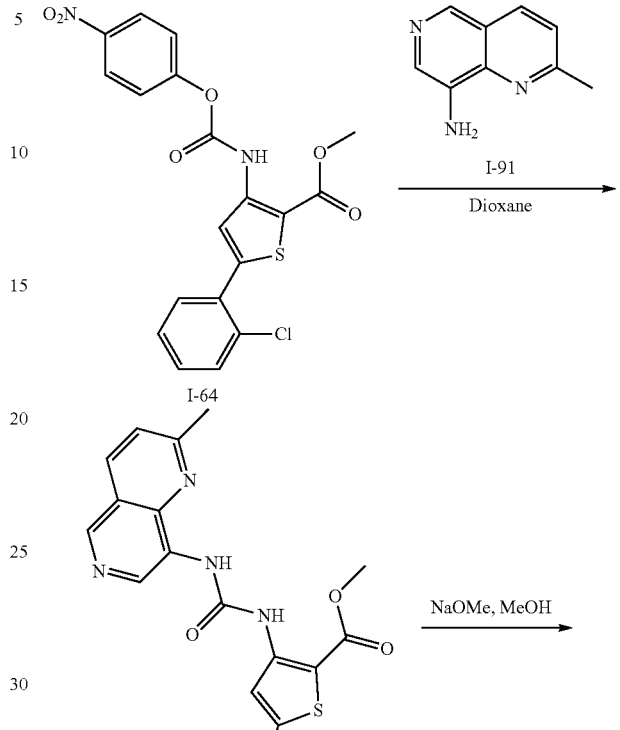

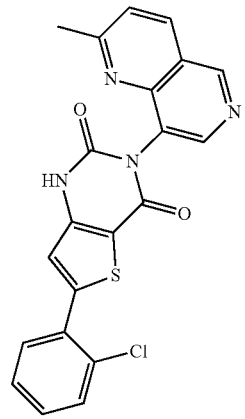

Example 453 methyl 5-(2-chlorophenyl)-3-(3-(2-methyl-1,6-naphthyridin-8-yl)ureido)thiophene-2-carboxylate: To a solution of methyl 5-(2-chlorophenyl)-3-(((4-nitrophenoxy)carbonyl)amino)thiophene-2-carboxylate (I-64) (117 mg, 0.27 mmol) in dioxane (2 mL), was added 2-methyl-1,6-naphthyridin-8-amine (I-91) (43 mg, 0.27 mmol). The reaction was heated at 80° C. for 1 hour (until done by LC/MS). The reaction was cooled to RT and diluted with 2 ml ACN, then filtered, rinsing with ACN. The solids were dried under vacuum and used as is in the next reaction.

ES/MS: 453.0 (M+H+).

6-(2-chlorophenyl)-3-(2-methyl-1,6-naphthyridin-8-yl)thieno[3,2-d]pyrimidine-2,4(1H,3H)-dione (Example 453):

To a solution of methyl 5-(2-chlorophenyl)-3-(3-(2-methyl-1,6-naphthyridin-8-yl)ureido)thiophene-2-carboxylate (100 mg, 0.22 mmol) in methanol (2 mL) was added sodium methoxide (0.5 ml, 25% in methanol). The reaction was stirred for 2 hours (until complete by LC/MS) and concentrated. The residue was dissolved in 1 ml DMF and 0.5 ml 1:2 TFA:water, filtered and purified by RP-HPLC (0.1% TFA-ACN in 0.1% TFA Water, Column: Gemini 5 uM, NX-C18 110 Angstrom, 250×21.2 mm) to give the title compound Example 453 as a trifluoroacetate salt.

ES/MS: 421.1 (M+).

$^1$H NMR (400 MHz, DMSO-$d_6$) δ 12.23 (s, 1H), 9.45 (s, 1H), 8.77 (s, 1H), 8.59 (d, 11H), 7.83-7.73 (m, 1H), 7.75-7.64 (m, 2H), 7.60-7.48 (m, 2H), 7.33 (s, 1H), 2.66 (s, 3H).

Examples 454-455

The following Examples were made in an analogous fashion according to Procedure 46 and are shown below in Table 23. Any different reagents/starting materials than those described in Procedure 46 are noted in the last column of Table 23—"Changes to Procedure 46: Different Reagents/Starting Materials".

TABLE 23

Examples 454-455

| Example | Structure | ES/MS m/z | $^1$H-NMR | Changes to Procedure 46: Different Reagents/ Starting Materials |
|---|---|---|---|---|
| 454 | 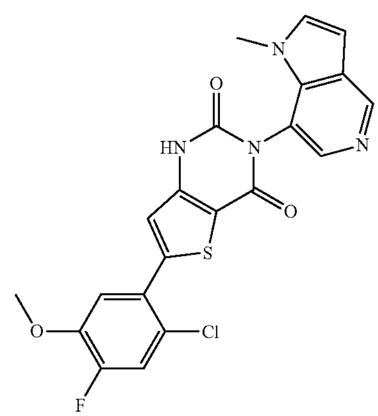 [SMILES: COc1cc(-c2cc3[nH]c(=O)n(-c4cncc5ccn(C)c45)c(=O)c3s2)c(Cl)cc1F] | 456.8 | $^1$H NMR (400 MHz, DMSO-d6) δ 12.57 (s, 1H), 9.33 (s, 1H), 8.65 (s, 1H), 7.87 (d, J = 3.3 Hz, 1H), 7.73 (d, J = 11.0 Hz, 1H), 7.46 (d, J = 8.9 Hz, 1H), 7.35 (s, 1H), 7.13 (d, J = 3.3 Hz, 1H), 3.95 (s, 3H), 3.80 (s, 3H). | I-85; I-66 |
| 455 | 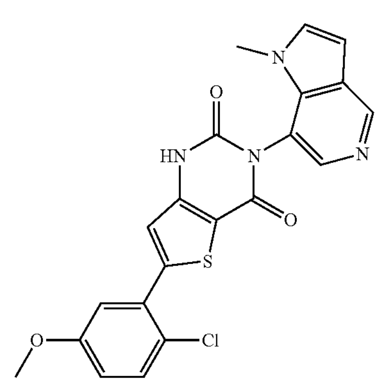 [SMILES: COc1ccc(Cl)c(-c2cc3[nH]c(=O)n(-c4cncc5ccn(C)c45)c(=O)c3s2)c1] | 438.8 | $^1$H NMR (400 MHz, DMSO-d6) δ 12.56 (s, 1H), 9.33 (s, 1H), 8.65 (s, 1H), 7.87 (d, J = 3.3 Hz, 1H), 7.61 (d, J = 8.8 Hz, 1H), 7.36 (d, J = 1.6 Hz, 1H), 7.25 (d, J = 3.0 Hz, 1H), 7.17 – 7.07 (m, 2H), 3.85 (d, J = 1.6 Hz, 3H), 3.80 (s, 3H). | I-85; I-65 |

Procedure 47: Example 456

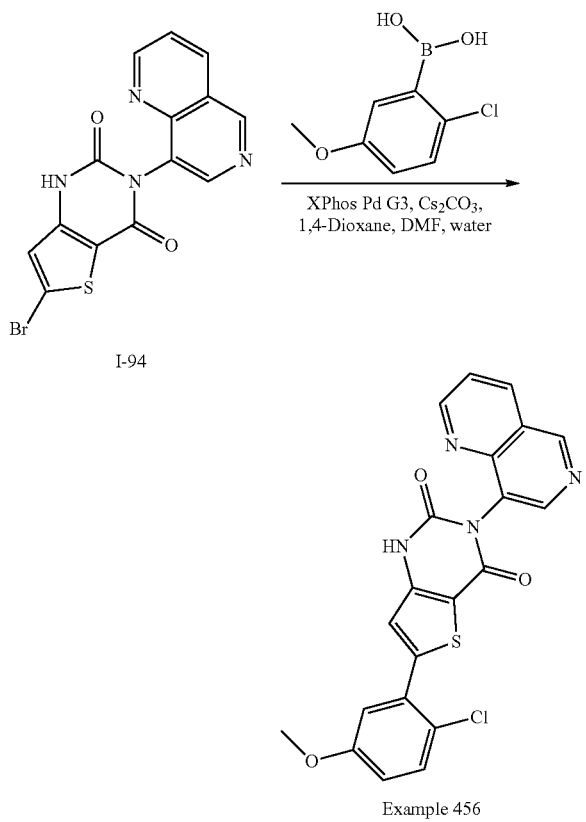

Example 456

6-(2-chloro-5-methoxyphenyl)-3-(1,6-naphthyridin-8-yl)thieno[3,2-d]pyrimidine-2,4(1H,3H)-dione (Example 456): To a 5 mL microwave vial containing a stir bar was added 6-bromo-3-(1,6-naphthyridin-8-yl)thieno[3,2-d]pyrimidine-2,4(1H,3H)-dione (I-94) (76 mg, 0.20 mmol), (2-chloro-5-methoxy-phenyl)boronic acid (45 mg, 0.24 mmol), XPhos Pd G3 (15 mg, 0.02 mmol), and $Cs_2CO_3$ (199 mg, 0.61 mmol), 1,4-Dioxane (3 ml), DMF (0.5 ml) and $H_2O$ (0.3 mL) were then added after which the reaction mixture was sealed with Teflon, degassed under Ar (5 min), and heated to 100° C. for 2 hours. The crude product was diluted in DMF/water/trifluoroacetic acid (1.5 mL: 5:1:0.2), filtered through an acrodisc, and purified directly by RP-HPLC (0.1% TFA-ACN in 0.1% TFA Water) to give the title compound.

ES/MS: 437.01 ($M^+$).

$^1$H NMR (400 MHz, DMSO-$d_6$) δ 12.26 (s, 1H), 9.55 (s, 1H), 9.12 (dd, 1H), 8.84 (s, 1H), 8.74 (dd, 1H), 7.80 (dd, 1H), 7.59 (d, 1H), 7.32 (s, 1H), 7.27 (d, 1H), 7.14 (dd, 1H), 3.85 (s, 3H).

Examples 457-459

The following Examples were made in an analogous fashion according to Procedure 47 and are shown below in Table 24. Any different reagents/starting materials than those described in Procedure 47 are noted in the last column of Table 24—"Changes to Procedure 47: Different Reagents/Starting Materials".

TABLE 24

Examples 457-459

| Example | Structure | ES/MS m/z | $^1$H-NMR | Changes to Procedure 47: Different Reagents/ Starting Materials |
|---|---|---|---|---|
| 457 | 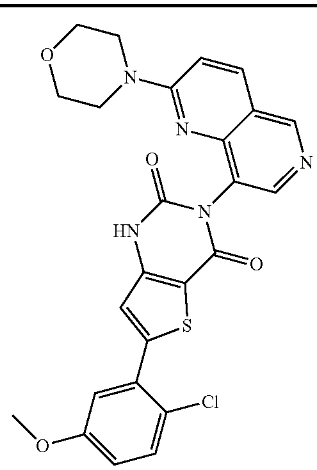 | 522.3 | $^1$H NMR (400 MHz, DMSO-d6) δ 12.23 (s, 1H), 9.18 (s, 1H), 8.66 (s, 1H), 8.39 – 8.29 (m, 1H), 7.59 (d, 1H), 7.52 (d, 1H), 7.33 (s, 1H), 7.27 (t, 1H), 7.13 (dd, 1H), 3.86 (s, 3H), 3.79 – 3.69 (m, 4H), 3.65 (t, 4H). | I-96 |

TABLE 24-continued
Examples 457-459
| Example | Structure | ES/MS m/z | ¹H-NMR | Changes to Procedure 47: Different Reagents/ Starting Materials |
|---|---|---|---|---|
| 458 | 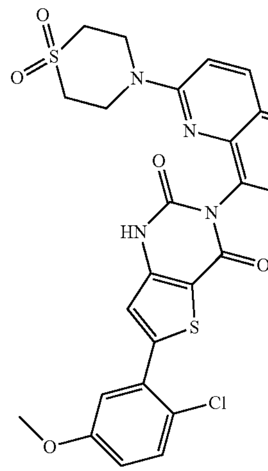 | 570.2 | ¹H NMR (400 MHz, DMSO-d6) δ 12.23 (s, 1H), 9.21 (s, 1H), 8.67 (s, 1H), 8.43 (d, 1H), 7.64 (d, 1H), 7.59 (d, 1H), 7.33 (s, 1H), 7.28 (d, 1H), 7.13 (dd, 1H), 4.16 (s, 4H), 3.86 (s, 3H), 3.14 (d, 4H). | I-97 |
| 459 | 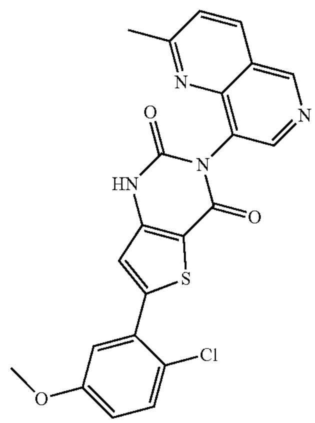 [SMILES: COc1ccc(Cl)c(-c2cc3[nH]c(=O)n(-c4cncc5ccc(C)nc45)c(=O)c3s2)c1] | 451.1 | ¹H NMR (400 MHz, DMSO-d6) δ 12.21 (s, 1H), 9.44 (s, 1H), 8.76 (s, 1H), 8.59 (d, 1H), 7.66 (d, 1H), 7.59 (d, 1H), 7.32 (s, 1H), 7.28 (d, 1H), 7.13 (dd, 1H), 3.85 (s, 3H), 2.65 (s, 3H). | I-95 |
Procedure 48: Example 460
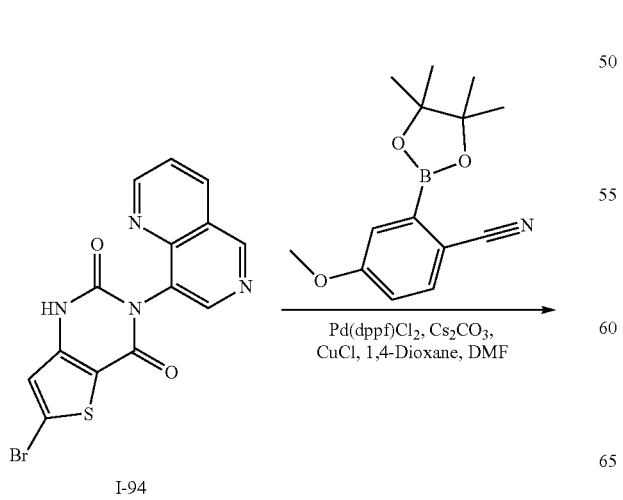
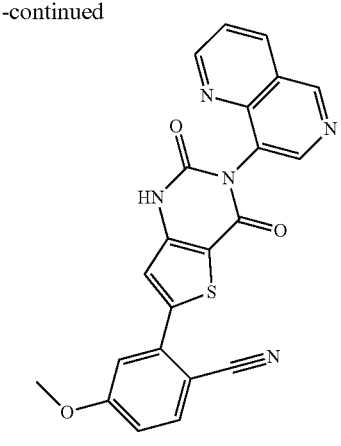
Example 460

2-(3-(1,6-naphthyridin-8-yl)-2,4-dioxo-1,2,3,4-tetrahydrothieno[3,2-d]pyrimidin-6-yl)-4-methoxybenzonitrile (Example 460): To a 5 mL microwave vial containing a stir bar was added 6-bromo-3-(1,6-naphthyridin-8-yl)thieno[3,2-d]pyrimidine-2,4(1H,3H)-dione (I-94) (100 mg, 0.27 mmol), 4-methoxy-2-(4,4,5,5-tetramethyl-1,3,2-dioxaborolan-2-yl)benzonitrile (138 mg, 0.53 mmol), Pd(dppf)Cl₂ (28 mg, 0.04 mmol), Cs₂CO₃ (347 mg, 1.1 mmol), and CuCl (26 mg, 27 mmol), 1,4-Dioxane (2 ml) and DMF (1 ml) were then added after which the reaction mixture was sealed with Teflon, degassed under Ar (5 min), and heated to 100° C. for 2 hours. The crude product was diluted in DMF/water/ trifluoroacetic acid (1.5 mL; 5:1:0.2), filtered through an acrodisc, and purified directly by RP-HPLC (0.1% TFA-ACN in 0.1% TFA Water) to give the product.

ES/MS: 428.1 (M⁺).

¹H NMR (400 MHz, DMSO-d6) δ 12.34 (s, 1H), 9.56 (s, 1H), 9.13 (dd, 1H), 8.85 (s, 1H), 8.74 (dd, 1H), 8.01 (d, 1H), 7.80 (dd, 1H), 7.50 (s, 1H), 7.36 (d, 1H), 7.28 (dd, 1H), 3.95 (s, 3H).

Example 461

The following Example was made in an analogous fashion according to Procedure 48 and is shown below in Table 25. Any different reagents/starting materials than those described in Procedure 48 are noted in the last column of Table 25—"Changes to Procedure 48: Different Reagents/ Starting Materials".

Procedure 49: Example 462

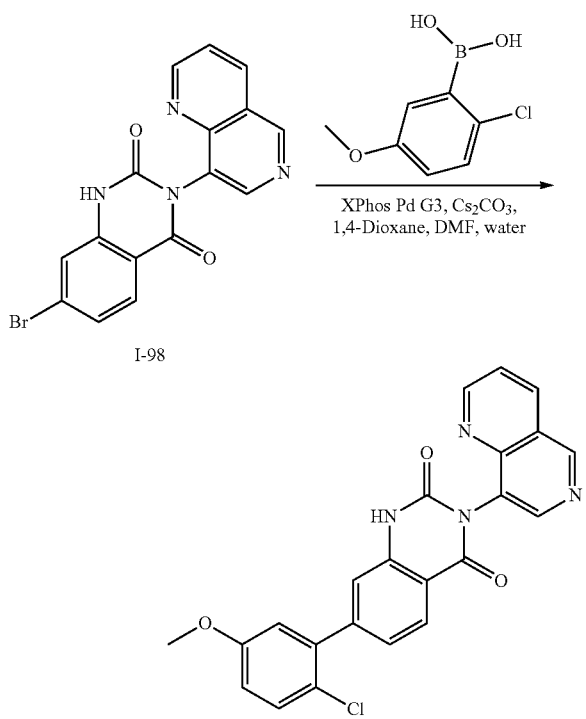

Example 462

7-(2-chloro-5-methoxyphenyl)-3-(1,6-naphthyridin-8-yl) quinazoline-2,4(1H,3H)-dione (Example 462): To a 5 mL microwave vial containing a stir bar was added 7-bromo-3-(1,6-naphthyridin-8-yl)quinazoline-2,4(1H,3H)-dione (I-98) (75 mg, 0.20 mmol), 4-methoxy-2-(4,4,5,5-tetramethyl-1,3,

TABLE 25

Example 461

| Example | Structure | ES/MS m/z | ¹H-NMR | Changes to Procedure 48: Different Reagents/ Starting Materials |
|---|---|---|---|---|
| 461 | 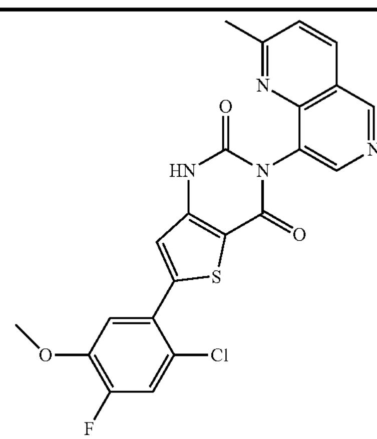 | 469.1 | ¹H NMR (400 MHz, DMSO-d6) δ 12.24 (s, 1H), 9.45 (s, 1H), 8.77 (s, 1H), 8.59 (d, 1H), 7.70 (dd, 2H), 7.49 (d, 1H), 7.31 (s, 1H), 3.95 (s, 3H), 2.65 (s, 3H). | I-95; (2-chloro-4-fluoro-5-methoxyphenyl)boronic acid |

2-dioxaborolan-2-yl)benzonitrile (45.4 mg, 0.24 mmol), XPhos Pd G3 (15 mg, 0.02 mmol), and Cs₂CO₃ (199 mg, 0.61 mmol), 1,4-Dioxane (3 ml), DMF (0.5 ml) and water (0.3 ml) were then added after which the reaction mixture was sealed with Teflon, degassed under Ar (5 min), and heated to 100° C. for 10 hours. The crude product was diluted in DMF/water/trifluoroacetic acid (1.5 mL; 5:1:0.2), filtered through an acrodisc, and purified directly by RP-HPLC (0.1% TFA-ACN in 0.1% TFA Water) to give the product.

ES/MS: 431.2 (M⁺).

¹H NMR (400 MHz, DMSO-d₆) δ 11.86 (s, 1H), 9.57 (s, 1H), 9.11 (dd, 1H), 8.86 (s, 1H), 8.75 (dd, 1H), 8.04 (d, 1H), 7.80 (dd, 1H), 7.55 (d, 1H), 7.34 (s, 1H), 7.32 (d, 1H), 7.09 (dd, 1H), 7.06 (d, 1H), 3.84 (s, 3H).

Procedure 50: Example 463 and Example 464

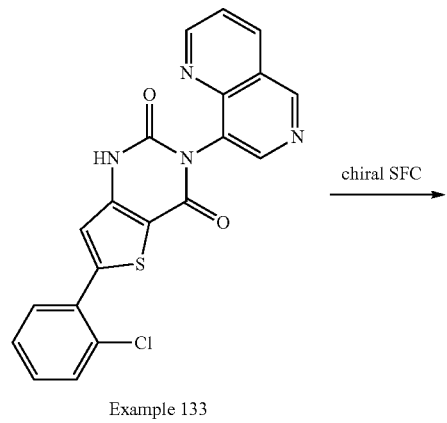

Example 133

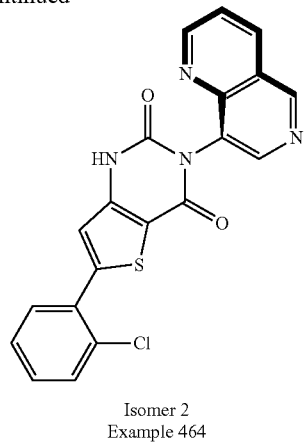

Isomer 2
Example 464

6-(2-chlorophenyl)-3-(1,6-naphthyridin-8-yl)thieno[3,2-d]pyrimidine-2,4(1H,3H)-dione (Example 463 and Example 464): 6-(2-chlorophenyl)-3-(1,6-naphthyridin-8-yl)thieno[3,2-d]pyrimidine-2,4(1H,3H)-dione (Example 133) as a mixture of 2 atropisomers was separated by chiral SFC (IB 4.6×¹⁰⁰ mm column with 35% MeOH cosolvent) to give two enantiomers, which were assigned as Isomer 1 and Isomer 2. The stereochemistry was assigned by analogy to Example 438, with Example 464 being the more active isomer.

Isomer 1:

6-(2-chlorophenyl)-3-(1,6-naphthyridin-8-yl)thieno [3,2-d]pyrimidine-2,4(1H,3H)-dione (Example 463)

ES/MS: 407.1 (M⁺).
¹H NMR (400 MHz, DMSO-d₆) δ 12.27 (s, 1H), 9.56 (s, 1H), 9.12 (dd, 1H), 8.84 (s, 1H), 8.74 (dd, 1H), 7.82-7.79 (m, 1H), 7.77 (dd, 1H), 7.78-7.65 (m, 1H), 7.60-7.48 (m, 2H), 7.33 (s, 1H).

Isomer 2:

6-(2-chlorophenyl)-3-(1,6-naphthyridin-8-yl)thieno [3,2-d]pyrimidine-2,4(1H,3H)-dione (Example 464)

ES/MS: 407.1 (M⁺).
¹H NMR (400 MHz, DMSO-d6) δ 12.27 (s, 1H), 9.56 (s, 1H), 9.12 (dd, 1H), 8.84 (s, 1H), 8.74 (dd, 1H), 7.82-7.79 (m, 1H), 7.77 (dd, 1H), 7.78-7.65 (m, 1H), 7.60-7.48 (m, 2H), 7.33 (s, 1H).

Procedure 51: Example 465 and Example 466

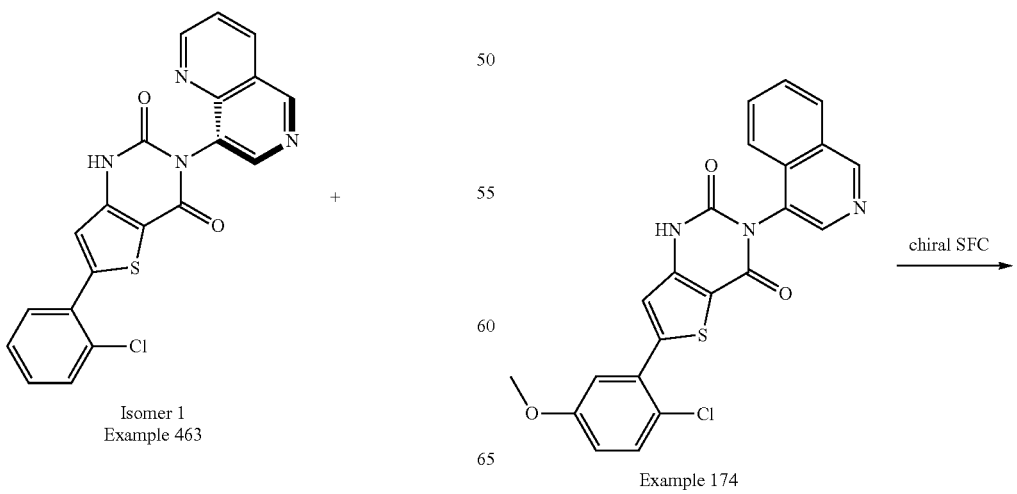

Example 174

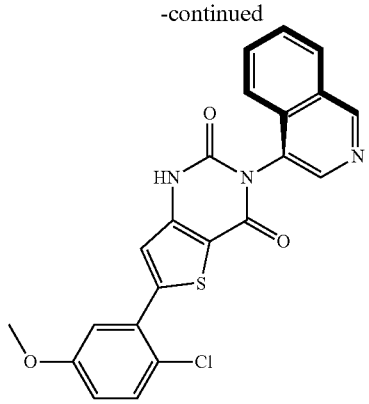

Isomer 1
Example 465

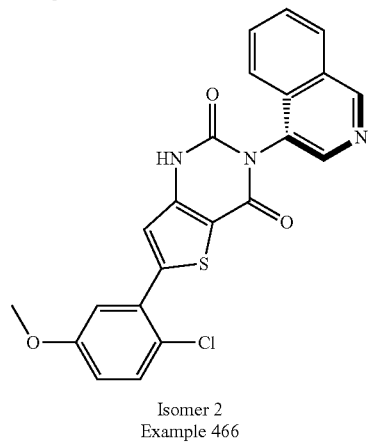

Isomer 2
Example 466

6-(2-chloro-5-methoxyphenyl)-3-(isoquinolin-4-yl)thieno[3,2-d]pyrimidine-2,4(1H,3H)-dione (Example 465 and Example 466): 6-(2-chloro-5-methoxyphenyl)-3-(isoquinolin-4-yl)thieno[3,2-d]pyrimidine-2,4(1H,3H)-dione (Example 174) as a mixture of 2 atropisomers was separated by chiral SFC (IB 4.6×100 mm column with 35% MeOH cosolvent) to give two enantiomers, which were assigned as Isomer 1 and Isomer 2. The stereochemistry was assigned by analogy to Example 438, with Example 465 being the more active isomer.

Isomer 1:

6-(2-chloro-5-methoxyphenyl)-3-(isoquinolin-4-yl)thieno[3,2-d]pyrimidine-2,4(1H,3H)-dionedione (Example 465)

ES/MS: 436.1 (M+).
$^1$H NMR (400 MHz, DMSO-d6) δ 12.29 (s, 1H), 9.47 (s, 1H), 8.59 (s, 1H), 8.30 (dd, 1H), 7.91-7.86 (m, 1H), 7.81 (dddd, 2H), 7.60 (d, 1H), 7.34 (s, 1H), 7.25 (d, 1H), 7.14 (dd, 1H), 3.86 (s, 3H).

Isomer 2:

6-(2-chloro-5-methoxyphenyl)-3-(isoquinolin-4-yl)thieno[3,2-d]pyrimidine-2,4(1H,3H)-dione (Example 466)

ES/MS: 436.1 (M+).
$^1$H NMR (400 MHz, DMSO-d6) δ 12.29 (s, 1H), 9.47 (s, 1H), 8.59 (s, 1H), 8.30 (dd, 1H), 7.91-7.86 (m, 1H), 7.81 (dddd, 2H), 7.60 (d, 1H), 7.34 (s, 1H), 7.25 (d, 1H), 7.14 (dd, 1H), 3.86 (s, 3H).

Procedure 52: Example 467 and Example 468

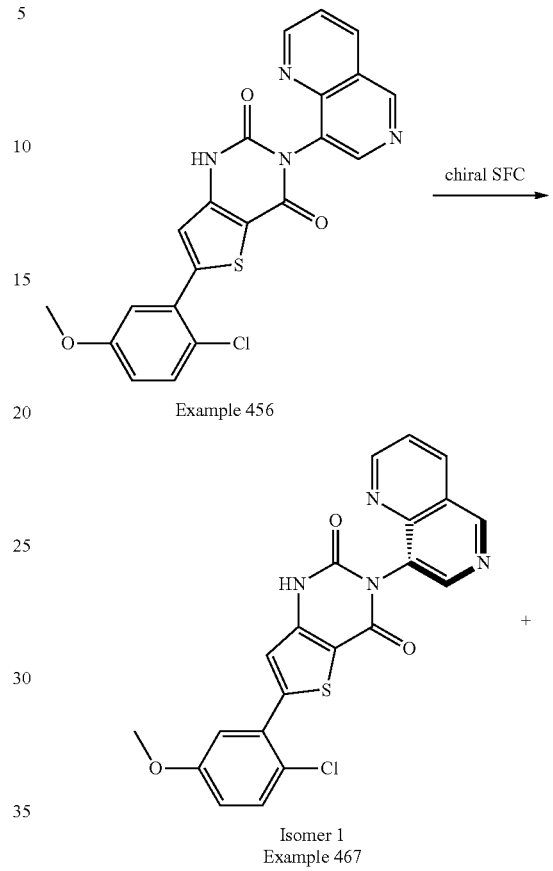

Example 456

Isomer 1
Example 467

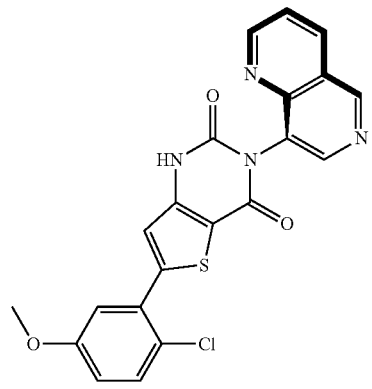

Isomer 2
Example 468

6-(2-chloro-5-methoxyphenyl)-3-(1,6-naphthyridin-8-yl)thieno[3,2-d]pyrimidine-2,4(1H,3H)-dione (Example 467 and Example 468): 6-(2-chloro-5-methoxyphenyl)-3-(1,6-naphthyridin-8-yl)thieno[3,2-d]pyrindine-2,4(1H,3H)-dione (Example 456) as a mixture of 2 enantiomers was separated by chiral SFC (IB 4.6×$^{100}$ mm column with 35% MeOH cosolvent) to give two enantiomers, which were assigned as Isomer 1 and Isomer 2. The stereochemistry was assigned by analogy to Example 438, with Example 468 being the more active isomer.

Isomer 1:

6-(2-chloro-5-methoxyphenyl)-3-(1,6-naphthyridin-8-yl)thieno[3,2-d]pyrimidine-2,4(1H,3H)-dione (Example 467)

ES/MS: 437.1 (M+).
$^1$H NMR (400 MHz, DMSO-d6) δ 12.26 (s, 1H), 9.56 (s, 1H), 9.12 (dd, 1H), 8.84 (s, 1H), 8.74 (dd, 1H), 7.80 (dd, 1H), 7.59 (d, 1H), 7.34-7.24 (m, 2H), 7.14 (dd, 1H), 3.85 (s, 3H).

Isomer 2:

6-(2-chloro-5-methoxyphenyl)-3-(1,6-naphthyridin-8-yl)thieno[3,2-d]pyrimidine-2,4(1H,3H)-dione (Example 468)

ES/MS: 437.1 (M+).
$^1$H NMR (400 MHz, DMSO-d6) δ 12.26 (s, 1H), 9.56 (s, 1H), 9.12 (dd, 1H), 8.84 (s, 1H), 8.74 (dd, 1H), 7.80 (dd, 1H), 7.59 (d, 1H), 7.34-7.24 (m, 2H), 7.14 (dd, 1H), 3.85 (s, 3H).

Procedure 53: Example 469

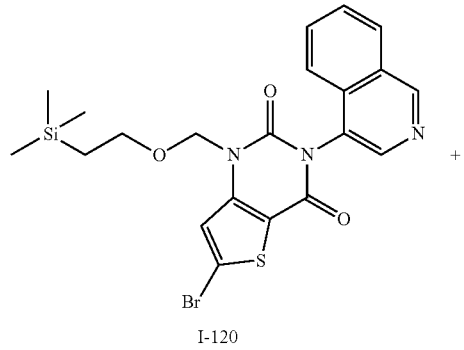

I-120

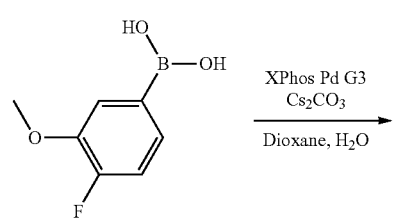

XPhos Pd G3
Cs$_2$CO$_3$
Dioxane, H$_2$O
⟶

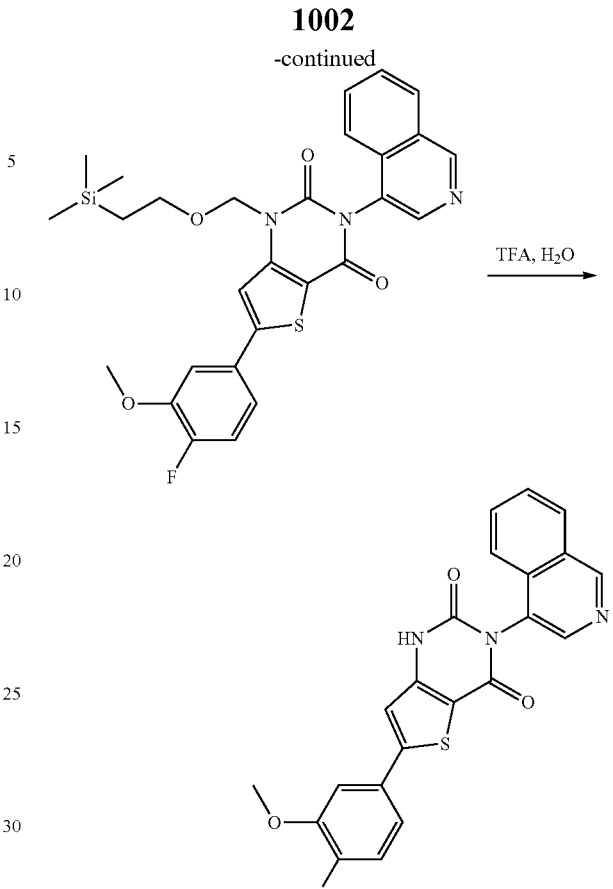

Example 469

6-(4-fluoro-3-methoxy-phenyl)-3-(4-isoquinolyl)-1-(2-trimethylsilylethoxymethyl)thieno[3,2-d]pyrimidine-2,4-dione: To a 10 mL microwave vial containing a stir bar was added 6-bromo-3-(4-isoquinolyl)-1-(2-trimethylsilylethoxymethyl)thieno[3,2-d]pyrimidine-2,4-dione (I-120) (30 mg, 0.06 mmol, 1.0 equiv.) followed by dioxane (1 mL). (4-fluoro-3-methoxy-phenyl)boronic acid (15 mg, 0.09 mmol), XPhos Pd G3 (4.5 mg, 10 mol %), and Cs$_2$CO$_3$ (58 mg, 0.17 mmol). H$_2$O (0.17 mL) was then added after which the reaction mixture was sealed with Teflon, degassed under Ar (5 min), and heated to 120° C. under microwave irradiation for 15 min. The crude product was diluted in acetonitrile filtered through celite and concentrated to give the crude title compound.

ES/MS: 550.1 (M+H+).

6-(4-fluoro-3-methoxy-phenyl)-3-(4-isoquinolyl)-1H-thieno[3,2-d]pyrimidine-2,4-dione (Example 469): To 6-(4-fluoro-3-methoxy-phenyl)-3-(4-isoquinolyl)-1-(2-trimethylsilylethoxymethyl)thieno[3,2-d]pyrimidine-2,4-dione was added TFA (0.5 mL) and water (0.1 mL), and the mixture was heated at 50° C. for 1 hours. To the crude mixture was added ACN (0.5 mL) and water (0.4 mL), and the mixture was filtered through an acrodisc. The mixture was purified by RP-HPLC (0.1% TFA-ACN in 0.1% TFA Water, Column: Gemini 5 uM, NX-C18 110 Angstrom, 250×21.2 mm) to give the title compound Example 469 as a trifluoroacetate salt.

ES/MS: 420.1 (M+H+).
$^1$H NMR (400 MHz, DMSO-d6) δ 12.36 (s, 1H), 9.48 (s, 1H), 8.60 (s, 1H), 8.31 (dd, J=7.9, 1.4 Hz, 1H), 7.97-7.73 (m, 3H), 7.56 (ddd, J=9.2, 6.6, 1.8 Hz, 2H), 7.49-7.28 (m, 3H), 3.99 (s, 3H).

Procedure 54: Example 470

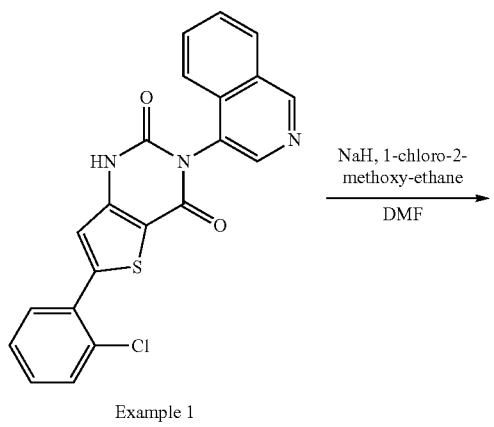

Example 1

Procedure 55: Example 471

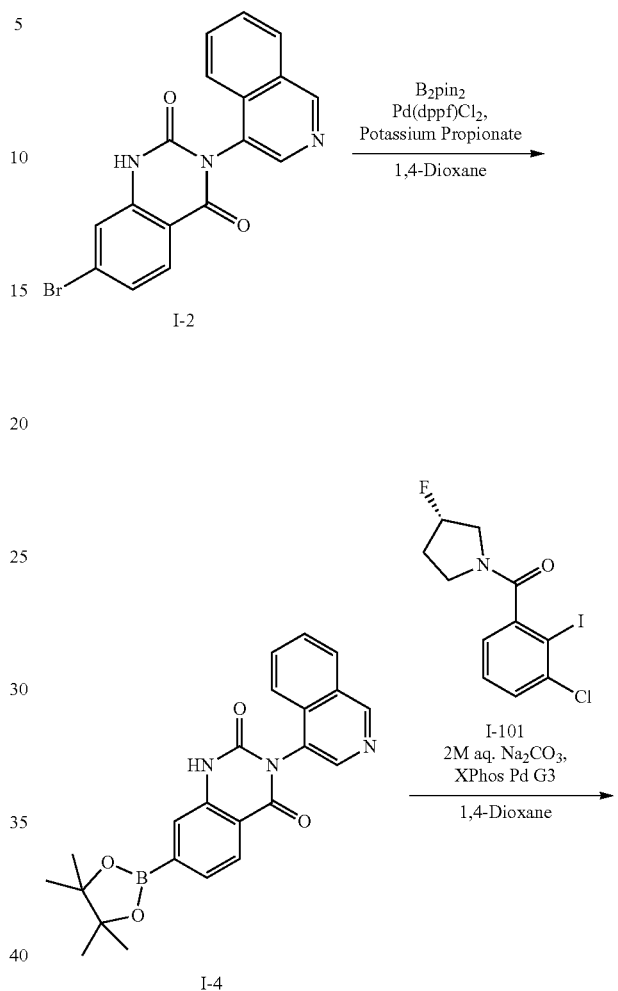

6-(2-chlorophenyl)-3-(4-isoquinolyl)-1-(2-methoxy-ethyl)thieno[3,2-d]pyrimidine-2,4-dione (Example 470)

A DMF solution of 6-(2-chlorophenyl)-3-(isoquinolin-4-yl)thieno[3,2-d]pyrimidine-2,4($1H$,3H)-dione (Example 1) (50 mg, 0.12 mmol) was cooled to 0° C. followed by addition of sodium hydride (14 mg, 0.37 mmol). After 30 min 1-chloro-2-methoxy-ethane (23 mg, 0.25 mmol) was added and the reaction was stirred for an additional 30 min at 0° C. and an additional 16 h at rt. To the crude mixture was added ACN (0.5 mL) and water (0.4 mL), and the mixture was filtered through an acrodisc. The mixture was purified by RP-HPLC (0.1% TFA-ACN in 0.1% TFA Water, Column: Gemini 5 uM, NX-C18 110 Angstrom, 250×21.2 mm) to give the title compound Example 470 as a trifluoroacetate salt.

ES/MS: 464.0 (M+).

$^1$H NMR (400 MHz, Methanol-d4) δ 9.62 (s, 1H), 8.68 (s, 1H), 8.44 (d, J=8.2 Hz, 1H), 8.10-7.83 (m, 4H), 7.79-7.72 (m, 1H), 7.70 (s, 1H), 7.68-7.60 (m, 1H), 7.55-7.43 (m, 2H), 4.42 (td, J=5.0, 2.1 Hz, 2H), 3.81 (td, J=5.2, 1.7 Hz, 2H), 3.33 (p, J=1.7 Hz, 2H).

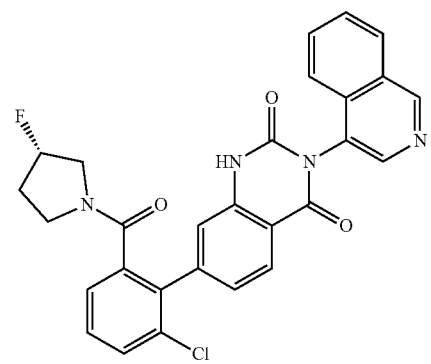

Example 471

7-[12-chloro-6-(thiazol-4-ylmethoxy)phenyl]-3-(4-isoquinolyl)-1H-quinazoline-2,4-dione (Example 471): To a 5 mL microwave vial with I-2 (75 mg, 0.2 mmol) was added bis(pinacolato)diboron (103 mg, 0.4 mmol), potassium propionate (68 mg, 0.6 mmol), Pd(dppf)Cl$_2$ (15 mg, 10 mol %), and 1,4-dioxane (8.00 mL). The microwave vial was then sealed, degassed with argon for 30 seconds, then reacted under microwave irradiation at 120° C. for 15 minutes to afford 1-4. To the crude mixture was then added 2M aq. Na$_2$CO$_3$ solution (0.30 mL), which was then stirred for 5 minutes at room temperature, followed by the addition of I-101 (76 mg, 0.2 mmol) and XPhos Pd G3 (10 mg, 10 mol %). The microwave vial was then sealed, degassed with argon for 30 seconds, and reacted under microwave irradiation at 120° C. for 15 minutes. The crude mixture was then filtered and concentrated under reduced pressure followed by the addition of MeCN (2 mL), water (0.4 mL), and TFA (0.08 mL). The homogenous mixture was then filtered through an acrodisc and subsequently purified by RP-HPLC (0.1% TFA-ACN in 0.1% TFA Water, Column: Gemini 5 uM, NX-C18 110 Angstrom, 250×21.2 mm) to give the title compound Example 471 as a trifluoroacetate salt.

ES/MS: 515.8 (M$^+$).

$^1$H NMR (400 MHz, Methanol-d4) δ 9.56 (s, 1H), 8.63 (s, 1H), 8.39 (dt, J=8.2, 1.1 Hz, 1H), 8.15 (d, J=8.2 Hz, 1H), 8.06-7.82 (m, 3H), 7.72 (dd, J=8.0, 1.2 Hz, 1H), 7.58 (td, J=7.9, 1.6 Hz, 1H), 7.48 (ddd, J=9.1, 7.6, 1.3 Hz, 1H), 7.31 (d, J=16.6 Hz, 2H), 5.23 (dd, J=52.5, 21.5 Hz, 1H), 3.77-3.40 (m, 4H), 2.35-1.78 (m, 2H).

Procedure 56: Example 472

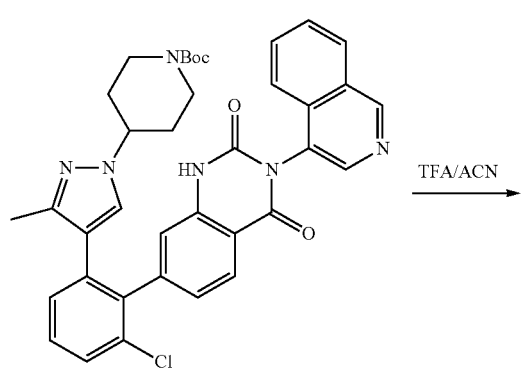

Example 266

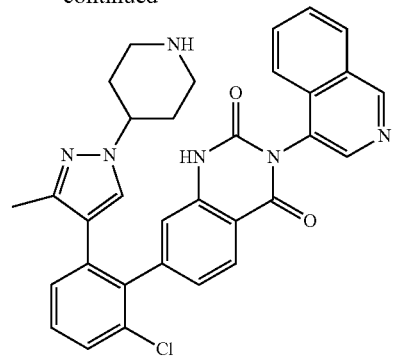

Example 472

7-[2-chloro-6-[3-methyl-1-(4-piperidyl)pyrazol-4-yl]phenyl]-3-(4-isoquinolyl)-1H-quinazoline-2,4-dione (Example 472): To a vial with tert-butyl 4-[4-[3-chloro-2-[3-(4-isoquinolyl)-2,4-dioxo-1H-quinazolin-7-yl]phenyl]-3-methyl-pyrazol-1-yl]piperidine-1-carboxylate (Example 266) (40 mg, 0.073 mmol) was added acetonitrile (0.5 mL), and TFA (0.3 mL). The mixture was heated to produce a homogeneous mixture, and was subsequently purified by RP-HPLC (0.1% TFA-ACN in 0.1% TFA Water, Column: Gemini 5 uM, NX-C18 110 Angstrom, 250×21.2 mm) to give the title compound as a trifluoroacetate salt.

ES/MS: 563.2 (M$^+$).

$^1$H NMR (400 MHz, MeOD) δ 9.48 (d, J=8.1 Hz, 1H), 8.34 (dd, J=11.7, 8.1 Hz, 1H), 8.02 (dd, J=8.3, 1.6 Hz, 1H), 7.96-7.88 (m, 1H), 7.88-7.85 (m, 1H), 7.85-7.75 (m, 1H), 7.61 (dd, J=8.1, 1.3 Hz, 1H), 7.50 (t, J=7.8 Hz, 1H), 7.43-7.31 (m, 2H), 7.29 (s, 1H), 7.16-7.08 (m, 2H), 4.34 (tt, J=10.1, 5.1 Hz, 1H), 3.53 (s, 2H), 2.24-2.00 (m, 8H).

Examples 473-474

The following Examples were made in an analogous fashion according to Procedure 56 and are shown below in Table 26. Any different reagents/starting materials than those described in Procedure 56 are noted in the last column of Table 26—"Changes to Procedure 56: Different Reagents/Starting Materials".

TABLE 26

Examples 473-474

| Example | Structure | ES/MS m/z | ¹H-NMR | Changes to Procedure 56: Different Reagents/ Starting Materials |
|---|---|---|---|---|
| 473 | 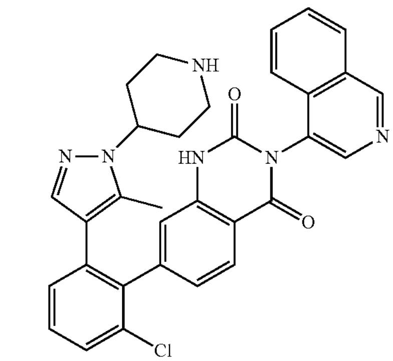 [SMILES: Cc1c(-c2cccc(Cl)c2-c2ccc3c(=O)n(-c4cncc5ccccc45)c(=O)[nH]c3c2)cnn1C1CCNCC1] | 562.9 | ¹H NMR (400 MHz, MeOD) δ 9.54 (d, J = 11.5 Hz, 1H), 8.58 (d, J = 30.7 Hz, 1H), 8.39 (dd, J = 13.6, 8.2 Hz, 1H), 8.05 – 7.82 (m, 4H), 7.60 (dt, J = 8.2, 1.5 Hz, 1H), 7.51 (t, J = 7.9 Hz, 1H), 7.36 (dt, J = 7.7, 1.5 Hz, 1H), 7.17 – 7.04 (m, 3H), 4.50 (s, 1H), 3.56 (d, J = 12.9 Hz, 2H), 3.26 – 3.16 (m, 2H), 2.22 (d, J = 18.1 Hz, 5H), 2.10 (t, J = 12.9 Hz, 2H). | Example 268 |
| 474 | 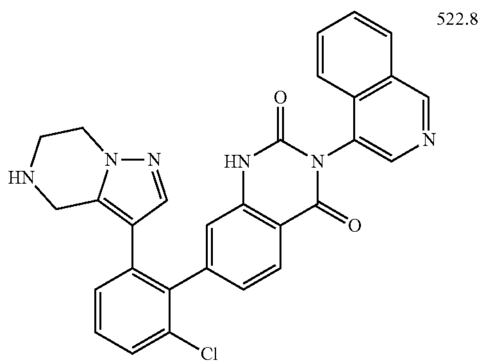 | 522.8 | ¹H NMR (400 MHz, MeOD) δ 9.56 (d, J = 5.2 Hz, 1H), 8.61 (d, J = 15.9 Hz, 1H), 8.44 – 8.36 (m, 1H), 8.06 (dd, J = 8.1, 3.1 Hz, 1H), 8.03 – 7.84 (m, 3H), 7.64 (ddd, J = 8.1, 2.4, 1.2 Hz, 1H), 7.54 (t, J = 7.9 Hz, 1H), 7.39 (dd, J = 7.7, 1.2 Hz, 1H), 7.24 (dd, J = 5.4, 1.4 Hz, 1H), 7.18 (d, J = 1.2 Hz, 1H), 7.10 (td, J = 7.9, 1.5 Hz, 1H), 4.55 – 4.30 (m, 4H), 3.88 – 3.72 (m, 2H). | Example 271 |

Procedure 57: Example 475 and Example 476

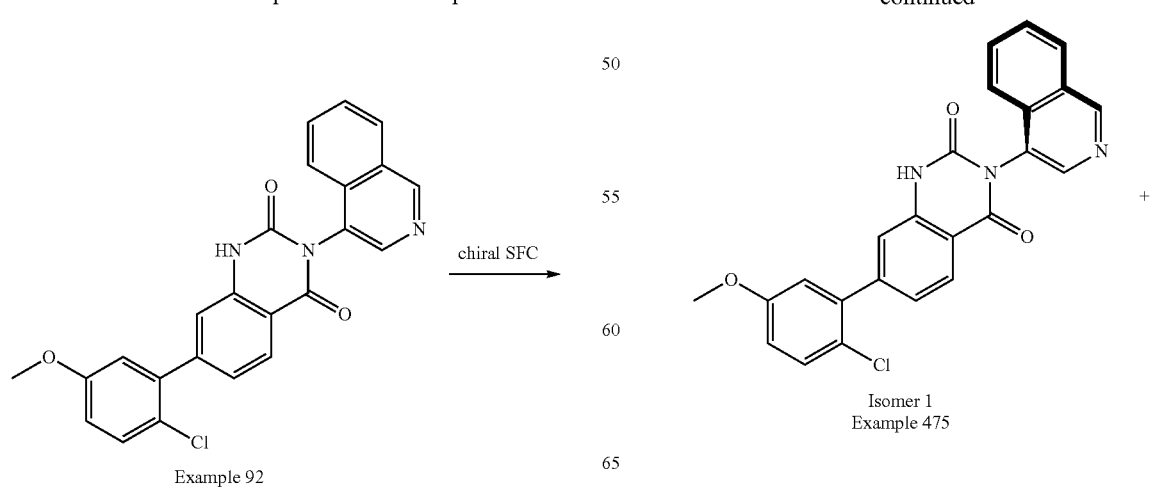

Isomer 1
Example 475

1009

-continued

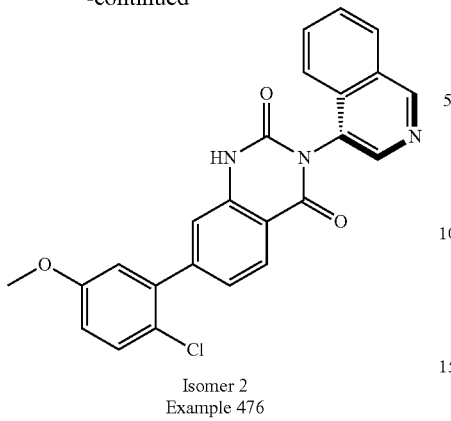

Isomer 2
Example 476

7-(2-chloro-5-methoxy-phenyl)-3-(4-isoquinolyl)-1H-quinazoline-2,4-dione (Example 475 and Example 476): 7-(2-chloro-5-methoxy-phenyl)-3-(4-isoquinolyl)-1H-quinazoline-2,4-dione (Example 92) as a mixture of 2 atropisomers was separated by chiral SFC (IB Sum-4.6×$^{100}$ mm column with 35% MeOH cosolvent) to give two enantiomers, which were assigned as Isomer 1 and Isomer 2. The stereochemistry was assigned by analogy to Example 438, with Example 475 being the more active isomer.

Isomer 1:

7-(2-chloro-5-methoxy-phenyl)-3-(4-isoquinolyl)-1H-quinazoline-2,4-dione

Example 475

ES/MS: 429.8 (M$^+$).

$^1$H NMR (400 MHz, DMSO-d6) δ 11.87 (s, 1H), 9.49 (s, 1H), 8.62 (s, 1H), 8.37-8.28 (m, 1H), 8.05 (d, J=8.0 Hz, 1H), 7.94 (d, J=8.0 Hz, 1H), 7.87-7.76 (m, 2H), 7.55 (d, J=8.8 Hz, 1H), 7.41-7.28 (m, 2H), 7.09 (dd, J=8.8, 3.1 Hz, 1H), 7.01 (d, J=3.1 Hz, 1H), 3.83 (s, 3H).

Isomer 2:

7-(2-chloro-5-methoxy-phenyl)-3-(4-isoquinolyl)-1H-quinazoline-2,4-dione

Example 476

ES/MS: 429.8 (M$^+$).

$^1$H NMR (400 MHz, DMSO-d6) δ 11.87 (s, 1H), 9.49 (s, 1H), 8.62 (s, 1H), 8.36-8.26 (m, 1H), 8.05 (d, J=8.0 Hz, 1H), 7.94 (d, J=8.1 Hz, 1H), 7.88-7.74 (m, 2H), 7.55 (d, J=8.8 Hz, 1H), 7.43-7.26 (m, 2H), 7.09 (dt, J=9.2, 3.1 Hz, 1H), 7.02 (d, J=3.0 Hz, 1H), 3.83 (s, 3H).

1010

Procedure 58: Example 477 and Example 478

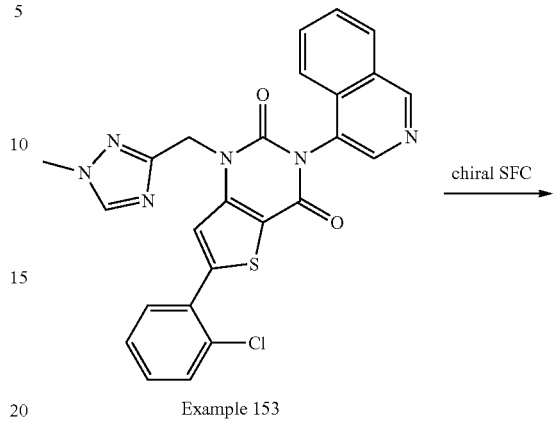

Example 153 chiral SFC →

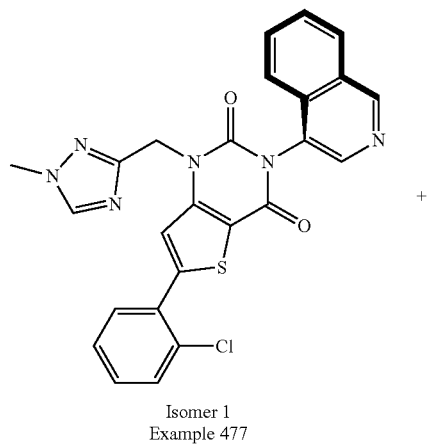

Isomer 1
Example 477

+

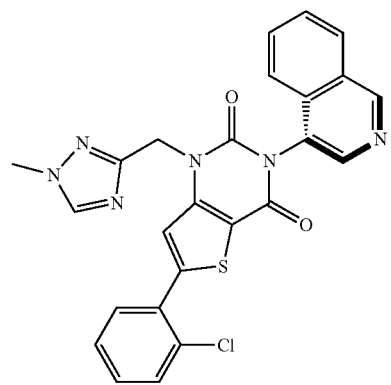

Isomer 2
Example 478

6-(2-chlorophenyl)-3-(4-isoquinolyl)-1-[(1-methyl-1,2,4-triazol-3-yl)methyl]thieno[3,2-d]pyrimidine-2,4-dione (Example 477 and Example 478): 6-(2-chlorophenyl)-3-(4-isoquinolyl)-1-[(1-methyl-1,2,4-triazol-3-yl)methyl]thieno[3,2-d]pyrimidine-2,4-dione (Example 153) as a mixture of 2 atropisomers was separated by chiral SFC (OD-H 4.6×$^{100}$ mm column with 35% MeOH cosolvent) to give two enantiomers, which were assigned as Isomer 1 and isomer 2. The stereochemistry was assigned by analogy to Example 438, with Example 477 being the more active isomer.

Isomer 1:

6-(2-chlorophenyl)-3-(4-isoquinolyl)-1-[(1-methyl-1,2,4-triazol-3-yl)methyl]thieno[3,2-d]pyrimidine-2,4-dione (Example 477)

ES/MS: 500.8 (M+).

$^1$H NMR (400 MHz, DMSO-d6) δ 9.51 (s, 1H), 8.61 (s, 1H), 8.44 (s, 1H), 8.36-8.28 (m, 1H), 7.91-7.76 (m, 5H), 7.73-7.65 (m, 1H), 7.57-7.50 (m, 2H), 5.49-5.32 (m, 2H), 3.84 (s, 3H).

Isomer 2:

6-(2-chlorophenyl)-3-(4-isoquinolyl)-1-[(1-methyl-1,2,4-triazol-3-yl)methyl]thieno[3,2-d]pyrimidine-2,4-dione (Example 478)

ES/MS: 500.7 (M+).

$^1$H NMR (400 MHz, DMSO-d$_6$) δ 9.51 (s, 1H), 8.61 (s, 1H), 8.44 (s, 1H), 8.33 (d, J=8.1 Hz, 1H), 7.96-7.74 (m, 5H), 7.73-7.65 (m, 1H), 7.55-7.51 (m, 2H), 5.40 (q, J=16.3 Hz, 2H), 3.83 (s, 3H).

Procedure 59: Example 479

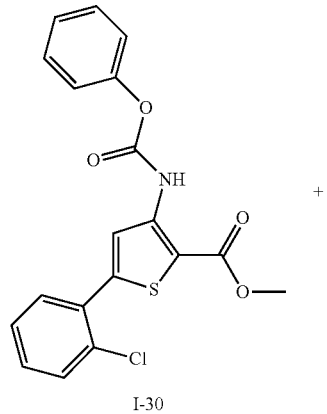

I-30

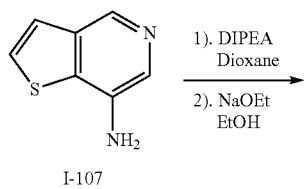

I-107

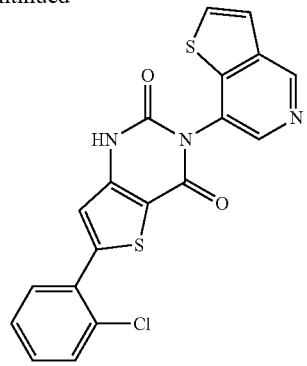

Example 479

6-(2-chlorophenyl)-3-thieno[3,2-c]pyridin-7-yl-1H-thieno[3,2-d]pyrimidine-2,4-dione (Example 479): To a dram vial with methyl 5-(2-chlorophenyl)-3-(phenoxycarbonylamino)thiophene-2-carboxylate (I-30) (100 mg, 0.258 mmol) and thieno[3,2-c]pyridin-7-amine (I-107) (46.5 mg, 0.309 mmol) was added DIPEA (67.4 µL, 0.387 mmol) and dioxane (1.30 mL). The reaction mixture was stirred at 90° C. for 12 hours. The reaction mixture was then cooled to ambient temperature and concentrated under reduced pressure. To the resulting crude residue was then added EtOH (0.58 mL) and NaOEt (21% in EtOH, 0.104 mL). The reaction mixture was then stirred at ambient temperature for 2 hours. The reaction mixture was then diluted with acetonitrile (2 mL), water (0.4 mL), and TFA (0.08 mL). The resulting solution was then filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the title compound Example 479 as a trifluoroacetate salt.

ES/MS: 411.7 (M+).

$^1$H NMR (400 MHz, DMSO-d6) δ 12.37 (s, 1H), 9.27 (s, 1H), 8.55 (s, 1H), 7.98 (d, J=5.4 Hz, 1H), 7.86-7.73 (m, 2H), 7.72-7.64 (m, 1H), 7.60-7.46 (m, 2H), 7.32 (s, 1H).

Examples 480-509

The following Examples were made in an analogous fashion according to Procedure 59 and are shown below in Table 27. Any different reagents/starting materials than those described in Procedure 59 are noted in the last column of Table 27—"Changes to Procedure 59: Different Reagents/Starting Materials".

TABLE 27

Examples 480-509

| Example | Structure | ES/MS m/z | ¹H-NMR | Changes to Procedure 59: Different Reagents/ Starting Materials |
|---|---|---|---|---|
| 480 | 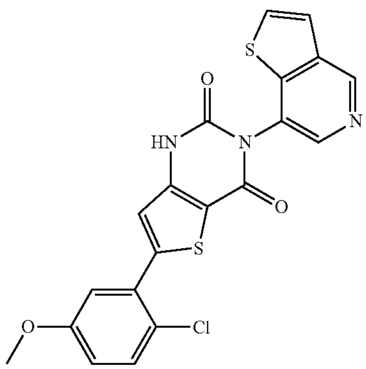 [SMILES: COc1ccc(Cl)c(-c2cc3[nH]c(=O)n(-c4cncc5ccsc45)c(=O)c3s2)c1] | 441.7 | ¹H NMR (400 MHz, DMSO-d6) δ 12.38 (s, 1H), 9.28 (s, 1H), 8.57 (s, 1H), 7.99 (d, J = 5.4 Hz, 1H), 7.78 (d, J = 5.4 Hz, 1H), 7.59 (d, J = 8.9 Hz, 1H), 7.31 (s, 1H), 7.25 (d, J = 3.1 Hz, 1H), 7.13 (dd, J = 8.9, 3.0 Hz, 1H), 3.84 (s, 3H) | I-62 |
| 481 | 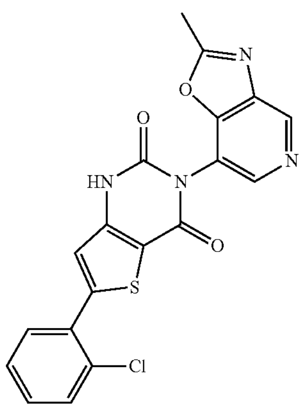 [SMILES: Cc1nc2cncc(-n3c(=O)[nH]c4cc(-c5ccccc5Cl)sc4c3=O)c2o1] | 436.9 | ¹H NMR (400 MHz, DMSO-d6) δ 7.64-7.56 (m, 2H), 7.44 (d, J = 9.5 Hz, 2H), 6.94 (s, 1H), 6.60 (s, 2H), 3.74 (s, 3H) | I-108 |
| 482 | 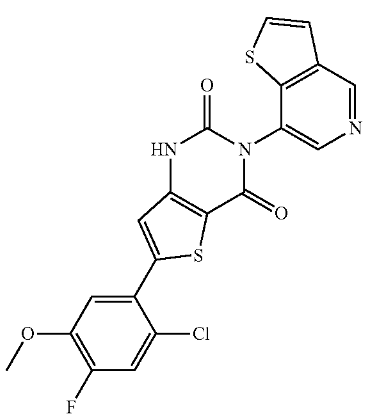 [SMILES: COc1cc(-c2cc3[nH]c(=O)n(-c4cncc5ccsc45)c(=O)c3s2)c(Cl)cc1F] | 459.7 | ¹H NMR (400 MHz, DMSO-d6) δ 12.44 (s, 1H), 9.34 (s, 1H), 8.63 (s, 1H), 8.04 (d, J = 5.4 Hz, 1H), 7.81 (d, J = 5.4 Hz, 1H), 7.70 (d, J = 11.1 Hz, 1H), 7.46 (d, J = 8.9 Hz, 1H), 7.31 (s, 1H), 3.94 (s, 3H) | I-61 |

TABLE 27-continued

Examples 480-509

| Example | Structure | ES/MS m/z | ¹H-NMR | Changes to Procedure 59: Different Reagents/ Starting Materials |
|---|---|---|---|---|
| 483 | 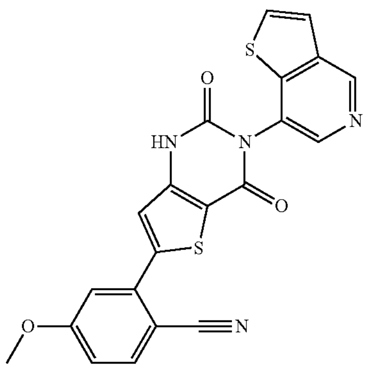 | 432.7 | ¹H NMR (400 MHz, DMSO-d6) δ 12.44 (s, 1H), 9.27 (s, 1H), 8.56 (s, 1H), 8.04-7.94 (m, 2H), 7.77 (d, J = 5.3 Hz, 1H), 7.49 (s, 1H), 7.35 (s, 1H), 7.27 (dd, J = 8.7, 2.6 Hz, 1H), 3.94 (s, 3H) | I-63 |
| 484 | 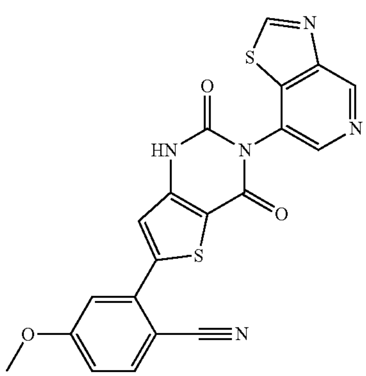 [SMILES: COc1ccc(C#N)c(-c2cc3[nH]c(=O)n(-c4cncc5ncsc45)c(=O)c3s2)c1] | 433.8 | ¹H NMR (400 MHz, DMSO-d6) δ 12.43 (s, 1H), 9.57 (s, 1H), 9.45 (s, 1H), 8.68 (s, 1H), 8.00 (d, J = 8.7 Hz, 1H), 7.49 (s, 1H), 7.34 (d, J = 2.5 Hz, 1H), 7.27 (dd, J = 8.7, 2.5 Hz, 1H), 3.94 (s, 3H) | I-63; I-110 |
| 485 | 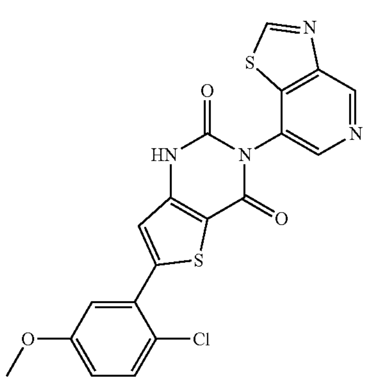 [SMILES: COc1ccc(Cl)c(-c2cc3[nH]c(=O)n(-c4cncc5ncsc45)c(=O)c3s2)c1] | 442.6 | ¹H NMR (400 MHz, DMSO-d6) δ 12.37 (s, 1H), 9.57 (s, 1H), 9.45 (s, 1H), 8.67 (s, 1H), 7.59 (d, J = 8.9 Hz, 1H), 7.31 (s, 1H), 7.24 (d, J = 3.0 Hz, 1H), 7.13 (dd, J = 8.9, 3.0 Hz, 1H), 3.84 (s, 3H) | I-62; I-110 |

TABLE 27-continued

Examples 480-509

| Example | Structure | ES/MS m/z | ¹H-NMR | Changes to Procedure 59: Different Reagents/ Starting Materials |
|---|---|---|---|---|
| 486 | 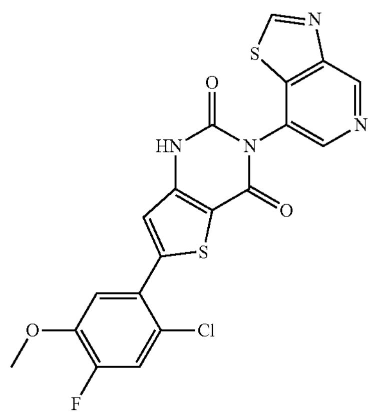 [SMILES: COc1cc(-c2cc3[nH]c(=O)n(-c4cncc5ncsc45)c(=O)c3s2)c(Cl)cc1F] | 460.6 | ¹H NMR (400 MHz, DMSO-d6) δ 12.40 (s, 1H), 9.57 (s, 1H), 9.46 (s, 1H), 8.68 (s, 1H), 7.71 (d, J = 11.0 Hz, 1H), 7.46 (d, J = 8.8 Hz, 1H), 7.30 (s, 1H), 3.95 (s, 3H) | I-61; I-110 |
| 487 | 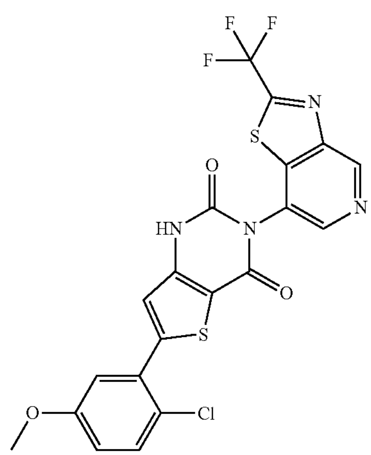 [SMILES: COc1ccc(Cl)c(-c2cc3[nH]c(=O)n(-c4cncc5nc(C(F)(F)F)sc45)c(=O)c3s2)c1] | 510.7 | ¹H NMR (400 MHz, DMSO-d6) δ 12.40 (s, 1H), 9.66 (s, 1H), 8.89 (s, 1H), 7.59 (d, J = 8.9 Hz, 1H), 7.31 (s, 1H), 7.23 (s, 1H), 7.11 (ddd, J = 12.4, 9.4, 3.0 Hz, 1H), 3.84 (s, 3H) | I-62; I-115 |
| 488 | 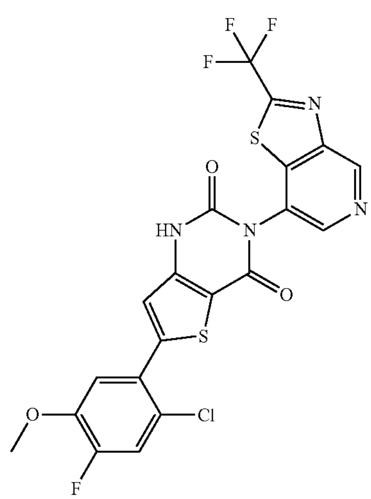 [SMILES: COc1cc(-c2cc3[nH]c(=O)n(-c4cncc5nc(C(F)(F)F)sc45)c(=O)c3s2)c(Cl)cc1F] | 528.7 | ¹H NMR (400 MHz, DMSO-d6) δ 12.43 (s, 1H), 9.66 (s, 1H), 8.89 (s, 1H), 7.71 (d, J = 11.0 Hz, 1H), 7.44 (d, J = 8.7 Hz, 1H), 7.30 (s, 1H), 3.94 (s, 3H) | I-61; I-115 |

TABLE 27-continued

Examples 480-509

| Example | Structure | ES/MS m/z | ¹H-NMR | Changes to Procedure 59: Different Reagents/ Starting Materials |
|---|---|---|---|---|
| 489 | 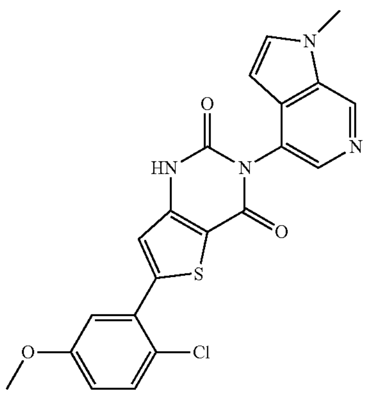 [SMILES: COc1ccc(Cl)c(-c2cc3[nH]c(=O)n(-c4cncc5c4ccn5C)c(=O)c3s2)c1] | 438.3 | ¹H NMR (400 MHz, MeOD) δ 9.30 (s, 1H), 8.47 (s, 1H), 8.13 (d, J = 3.0 Hz, 1H), 7.53 (d, J = 8.9 Hz, 1H), 7.22 (d, J = 3.0 Hz, 1H), 7.09 (dd, J = 8.9, 3.0 Hz, 1H), 6.87 (dd, J = 3.0, 0.8 Hz, 1H), 4.18 (s, 3H), 3.89 (s, 3H). | I-184; I-62 |
| 490 | 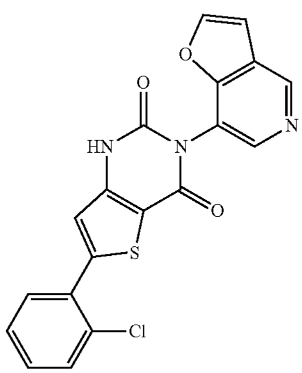 [SMILES: O=c1[nH]c2cc(-c3ccccc3Cl)sc2c(=O)n1-c1cncc2ccoc12] | 395.8 | ¹H NMR (400 MHz, DMSO-d6) δ 12.37 (s, 1H), 9.03 (s, 1H), 8.52 (s, 1H), 8.14 (d, J = 2.2 Hz, 1H), 7.79-7.72 (m, 1H), 7.72-7.66 (m, 1H), 7.57-7.48 (m, 2H), 7.31 (s, 1H), 7.23 (d, J = 2.2 Hz, 1H). | I-176 |
| 491 | 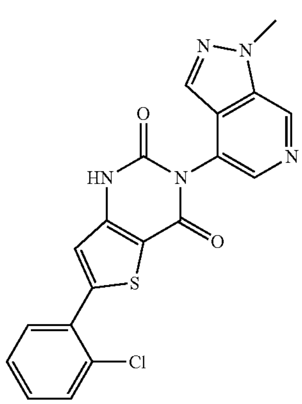 [SMILES: Cn1ncc2c(-n3c(=O)[nH]c4cc(-c5ccccc5Cl)sc4c3=O)cncc21] | 410.0 | ¹H NMR (400 MHz, DMSO-d6) δ 12.20 (s, 1H), 9.23 (s, 1H), 8.27-8.20 (m, 2H), 7.77-7.72 (m, 1H), 7.71-7.65 (m, 1H), 7.57-7.50 (m, 2H), 7.30 (s, 1H), 4.23 (s, 3H). | 1-methylpyrazolo [3,4-c]pyridin-4-amine |

TABLE 27-continued

Examples 480-509

| Example | Structure | ES/MS m/z | ¹H-NMR | Changes to Procedure 59: Different Reagents/ Starting Materials |
|---|---|---|---|---|
| 492 | 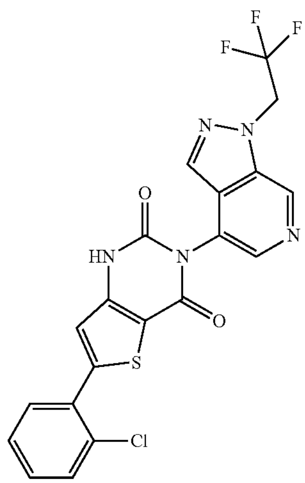 [SMILES: O=c1[nH]c2cc(-c3ccccc3Cl)sc2c(=O)n1-c1cncc2c1cnn2CC(F)(F)F] | 477.9 | ¹H NMR (400 MHz, DMSO-d6) δ 12.26 (s, 1H), 9.36 (s, 1H), 8.47 (d, J = 0.8 Hz, 1H), 8.36 (s, 1H), 7.78-7.71 (m, 1H), 7.71-7.66 (m, 1H), 7.57-7.48 (m, 2H), 7.30 (s, 1H), 5.70 (qd, J = 9.3, 8.7, 1.5 Hz, 2H). | I-178 |
| 493 | 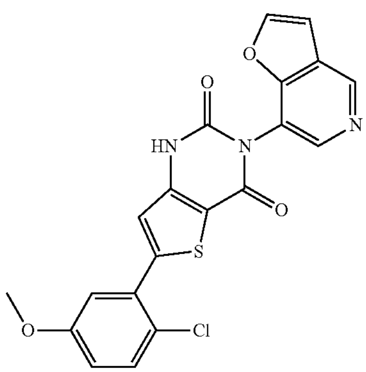 [SMILES: COc1ccc(Cl)c(-c2cc3[nH]c(=O)n(-c4cncc5ccoc45)c(=O)c3s2)c1] | 425.8 | ¹H NMR (400 MHz, DMSO-d6) δ 12.39 (s, 1H), 9.16-9.04 (m, 1H), 8.65-8.52 (m, 1H), 8.25-8.15 (m, 1H), 7.59 (d, J = 8.9 Hz, 1H), 7.31 (s, 1H), 7.29-7.26 (m, 1H), 7.25 (d, J = 3.0 Hz, 1H), 7.13 (dd, J = 8.9, 3.0 Hz, 1H), 3.84 (s, 3H). | I-176; I-62 |
| 494 | 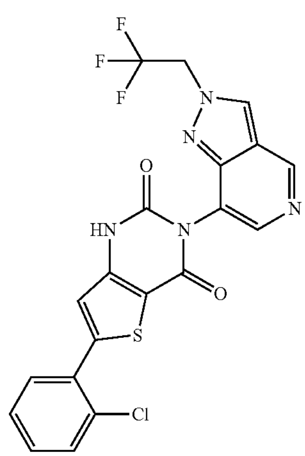 [SMILES: O=c1[nH]c2cc(-c3ccccc3Cl)sc2c(=O)n1-c1cncc2cn(CC(F)(F)F)nc12] | 477.8 | ¹H NMR (400 MHz, DMSO-d6) δ 12.31 (s, 1H), 9.49 (s, 1H), 9.14 (s, 1H), 8.39 (s, 1H), 7.79-7.72 (m, 1H), 7.72-7.65 (m, 1H), 7.57-7.48 (m, 2H), 7.30 (s, 1H), 5.68 (q, J = 8.9 Hz, 2H). | I-181 |

TABLE 27-continued

Examples 480-509

| Example | Structure | ES/MS m/z | ¹H-NMR | Changes to Procedure 59: Different Reagents/ Starting Materials |
|---|---|---|---|---|
| 495 | 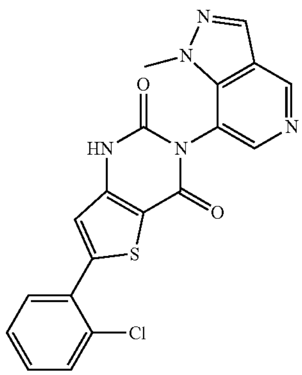 [SMILES: Cn1ncc2cncc(-n3c(=O)[nH]c4cc(-c5ccccc5Cl)sc4c3=O)c21] | 409.9 | ¹H NMR (400 MHz, DMSO-d6) δ 12.51 (s, 1H), 9.36 (s, 1H), 8.60 (s, 1H), 8.56 (s, 1H), 7.83-7.73 (m, 1H), 7.73-7.65 (m, 1H), 7.59-7.48 (m, 2H), 7.35 (s, 1H), 3.95 (s, 3H). | I-183 |
| 496 | 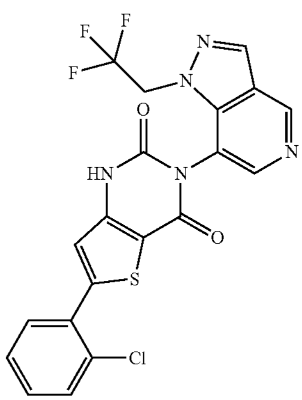 [SMILES: O=c1[nH]c2cc(-c3ccccc3Cl)sc2c(=O)n1-c1cncc2cnn(CC(F)(F)F)c12] | 477.8 | ¹H NMR (400 MHz, DMSO-d6) δ 12.45 (s, 1H), 9.27 (s, 1H), 8.66 (s, 1H), 8.55 (s, 1H), 7.84-7.74 (m, 1H), 7.74-7.63 (m, 1H), 7.58-7.47 (m, 2H), 7.35 (s, 1H), 5.11 (tdd, J = 16.2, 13.0, 8.1 Hz, 2H). | I-184 |
| 497 | 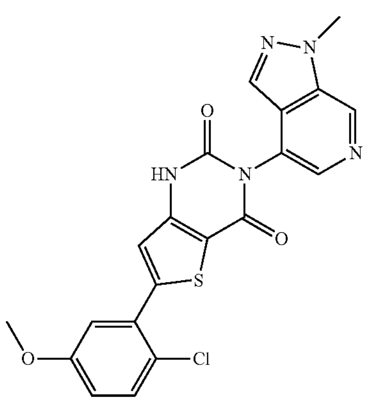 [SMILES: COc1ccc(Cl)c(-c2cc3[nH]c(=O)n(-c4cncc5c4cnn5C)c(=O)c3s2)c1] | 439.8 | ¹H NMR (400 MHz, DMSO-d6) δ 12.22 (s, 1H), 9.27 (s, 1H), 8.27 (s, 1H), 8.26 (d, J = 0.8 Hz, 1H), 7.59 (d, J = 8.9 Hz, 1H), 7.30 (s, 1H), 7.23 (d, J = 3.0 Hz, 1H), 7.13 (dd, J = 8.9, 3.1 Hz, 1H), 4.24 (s, 3H), 3.84 (s, 3H). | 1-methylpyrazolo [3,4-c]pyridin-4-amine; I-62 |

TABLE 27-continued

Examples 480-509

| Example | Structure | ES/MS m/z | ¹H-NMR | Changes to Procedure 59: Different Reagents/ Starting Materials |
|---|---|---|---|---|
| 498 | 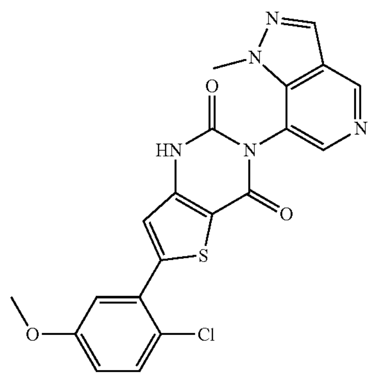 [SMILES: COc1ccc(Cl)c(-c2cc3[nH]c(=O)n(-c4cncc5cnn(C)c45)c(=O)c3s2)c1] | 439.8 | ¹H NMR (400 MHz, DMSO-d6) δ 12.48 (s, 1H), 9.30 (s, 1H), 8.54 (s, 1H), 8.50 (s, 1H), 7.59 (d, J = 8.9 Hz, 1H), 7.34 (s, 1H), 7.25 (d, J = 3.1 Hz, 1H), 7.13 (dd, J = 8.9, 3.1 Hz, 1H), 3.92 (s, 3H), 3.84 (s, 3H). | I-183; I-62 |
| 499 | 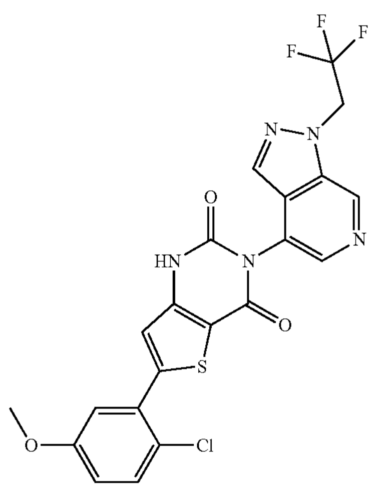 [SMILES: COc1ccc(Cl)c(-c2cc3[nH]c(=O)n(-c4cncc5c4cnn5CC(F)(F)F)c(=O)c3s2)c1] | 507.8 | ¹H NMR (400 MHz, DMSO-d6) δ 12.26 (s, 1H), 9.37 (s, 1H), 8.47 (d, J = 0.8 Hz, 1H), 8.37 (s, 1H), 7.59 (d, J = 8.9 Hz, 1H), 7.30 (s, 1H), 7.23 (d, J = 3.0 Hz, 1H), 7.13 (dd, J = 8.9, 3.0 Hz, 1H), 5.70 (qd, J = 9.1, 8.6, 1.5 Hz, 2H), 3.84 (s, 3H). | I-178; I-62 |
| 500 | 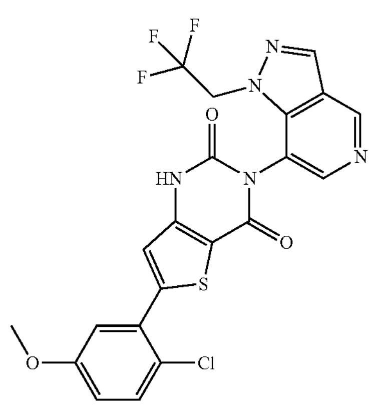 [SMILES: COc1ccc(Cl)c(-c2cc3[nH]c(=O)n(-c4cncc5cnn(CC(F)(F)F)c45)c(=O)c3s2)c1] | 507.8 | ¹H NMR (400 MHz, DMSO-d6) δ 12.45 (s, 1H), 9.29 (s, 1H), 8.68 (s, 1H), 8.57 (s, 1H), 7.59 (d, J = 8.9 Hz, 1H), 7.34 (s, 1H), 7.27 (d, J = 3.0 Hz, 1H), 7.13 (dd, J = 8.9, 3.0 Hz, 1H), 5.23-5.00 (m, 2H), 3.85 (s, 3H). | I-182; I-62 |

TABLE 27-continued

Examples 480-509

| Example | Structure | ES/MS m/z | ¹H-NMR | Changes to Procedure 59: Different Reagents/ Starting Materials |
|---|---|---|---|---|
| 501 | 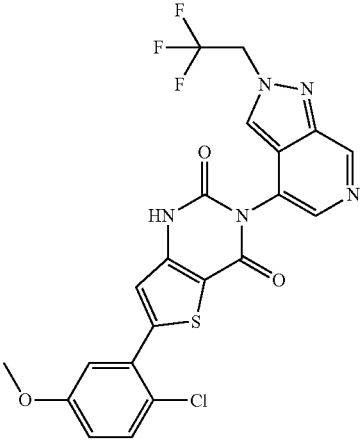 [SMILES: COc1ccc(Cl)c(-c2cc3[nH]c(=O)n(-c4cncc5nn(CC(F)(F)F)cc45)c(=O)c3s2)c1] | 507.8 | ¹H NMR (400 MHz, DMSO-d6) δ 12.21 (s, 1H), 9.38 (s, 1H), 8.81 (d, J = 0.9 Hz, 1H), 8.19 (s, 1H), 7.59 (d, J = 8.9 Hz, 1H), 7.30 (s, 1H), 7.22 (d, J = 3.0 Hz, 1H), 7.13 (dd, J = 8.9, 3.0 Hz, 1H), 5.66 (q, J = 9.0 Hz, 2H), 3.84 (s, 3H). | 2-(2,2,2-trifluoroethyl)pyrazolo[3,4-c]pyridin-4-amine; I-62 |
| 502 | 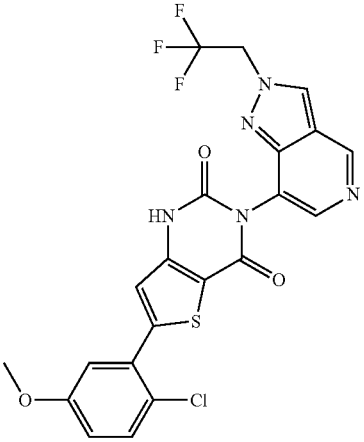 [SMILES: COc1ccc(Cl)c(-c2cc3[nH]c(=O)n(-c4cncc5cn(CC(F)(F)F)nc45)c(=O)c3s2)c1] | 507.8 | ¹H NMR (400 MHz, DMSO-d6) δ 12.29 (s, 1H), 9.45 (s, 1H), 9.09 (s, 1H), 8.36 (s, 1H), 7.58 (d, J = 8.9 Hz, 1H), 7.29 (s, 1H), 7.25 (d, J = 3.0 Hz, 1H), 7.13 (dd, J = 8.9, 3.0 Hz, 1H), 5.66 (q, J = 9.0 Hz, 2H), 3.84 (s, 3H). | I-181; I-62 |
| 503 | 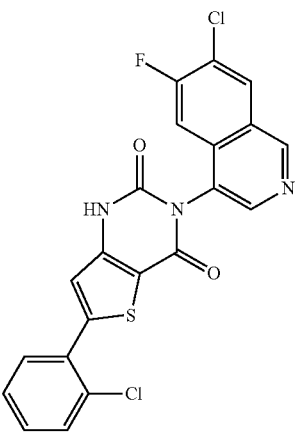 [SMILES: O=c1[nH]c2cc(-c3ccccc3Cl)sc2c(=O)n1-c1cncc2cc(Cl)c(F)cc12] | 487.8 | ¹H NMR (400 MHz, DMSO-d6) δ 12.22 (s, 1H), 9.41 (d, J = 0.8 Hz, 1H), 8.66 (d, J = 7.4 Hz, 1H), 8.62 (s, 1H), 8.19 (d, J = 10.5 Hz, 1H), 7.59 (d, J = 8,9 Hz, 1H), 7.32 (s, 1H), 7.22 (d, J = 3.0 Hz, 1H), 7.13 (dd, J = 8.9, 3.0 Hz, 1H), 3.85 (s, 3H). | I-185 |

TABLE 27-continued

Examples 480-509

| Example | Structure | ES/MS m/z | ¹H-NMR | Changes to Procedure 59: Different Reagents/ Starting Materials |
|---|---|---|---|---|
| 504 | 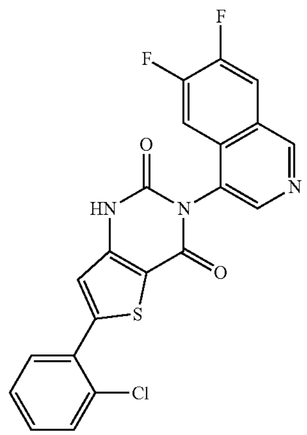 [SMILES: O=c1[nH]c2cc(-c3ccccc3Cl)sc2c(=O)n1-c1cncc2cc(F)c(F)cc12] | 471.8 | ¹H NMR (400 MHz, DMSO-d6) δ 12.22 (s, 1H), 9.40 (s, 1H), 8.60 (s, 1H), 8.37 (dd, J = 10.6, 8.0 Hz, 1H), 8.24 (dd, J = 11.6, 7.6 Hz, 1H), 7.59 (d, J = 8.9 Hz, 1H), 7.32 (s, 1H), 7.22 (d, J = 3.0 Hz, 1H), 7.13 (dd, J = 8.9, 3.0 Hz, 1H), 3.84 (s, 3H). | I-186 |
| 505 | 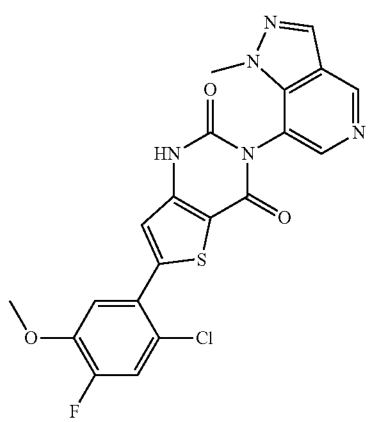 [SMILES: COc1cc(-c2cc3[nH]c(=O)n(-c4cncc5cnn(C)c45)c(=O)c3s2)c(Cl)cc1F] | 457.8 | ¹H NMR (400 MHz, DMSO-d6) δ 12.48 (s, 1H), 9.25 (s, 1H), 8.50 (s, 1H), 8.46 (s, 1H), 7.72 (d, J = 11.1 Hz, 1H), 7.46 (d, J = 8.9 Hz, 1H), 7.32 (s, 1H), 3.94 (s, 3H), 3.91 (s, 3H). | I-183; I-61 |
| 506 | 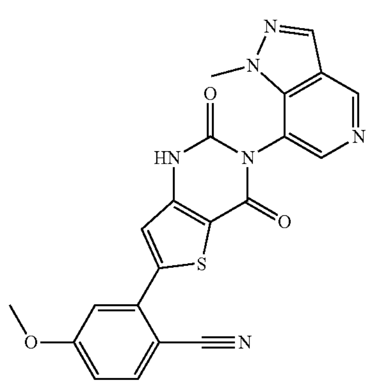 [SMILES: COc1ccc(C#N)c(-c2cc3[nH]c(=O)n(-c4cncc5cnn(C)c45)c(=O)c3s2)c1] | 430.9 | ¹H NMR (400 MHz, DMSO-d6) δ 12.55 (s, 1H), 9.31 (s, 1H), 8.55 (s, 1H), 8.51 (s, 1H), 8.01 (d, J = 8.7 Hz, 1H), 7.53 (s, 1H), 7.36 (d, J = 2.5 Hz, 1H), 7.28 (dd, J = 8.7, 2.5 Hz, 1H), 3.95 (s, 3H), 3.94 (s, 3H). | I-183; I-63 |

TABLE 27-continued

Examples 480-509

| Example | Structure | ES/MS m/z | ¹H-NMR | Changes to Procedure 59: Different Reagents/ Starting Materials |
|---|---|---|---|---|
| 507 | 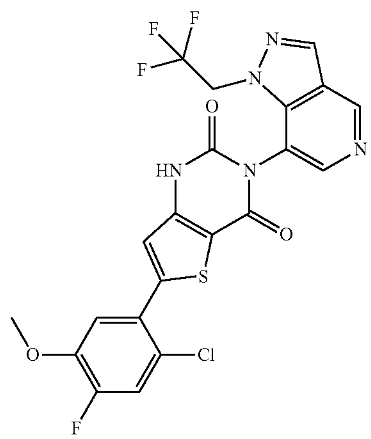 [SMILES: COc1cc(-c2cc3[nH]c(=O)n(-c4cncc5cnn(CC(F)(F)F)c45)c(=O)c3s2)c(Cl)cc1F] | 525.8 | ¹H NMR (400 MHz, DMSO-d6) δ 12.47 (s, 1H), 9.27 (s, 1H), 8.67 (s, 1H), 8.55 (s, 1H), 7.71 (d, J = 11.0 Hz, 1H), 7.48 (d, J = 8.9 Hz, 1H), 7.33 (s, 1H), 5.21-4.98 (m, 2H), 3.95 (s, 3H). | I-182; I-61 |
| 508 | 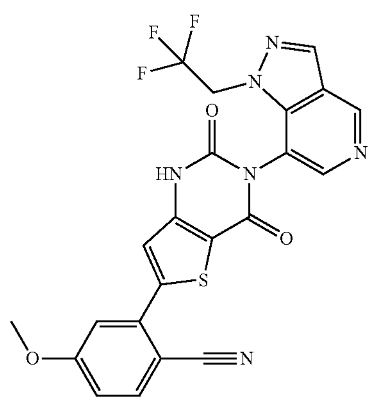 [SMILES: COc1ccc(C#N)c(-c2cc3[nH]c(=O)n(-c4cncc5cnn(CC(F)(F)F)c45)c(=O)c3s2)c1] | 498.8 | ¹H NMR (400 MHz, DMSO-d6) δ 12.51 (s, 1H), 9.27 (s, 1H), 8.66 (s, 1H), 8.55 (s, 1H), 8.00 (d, J = 8.7 Hz, 1H), 7.52 (s, 1H), 7.37 (d, J = 2.6 Hz, 1H). 7.27 (dd, J = 8.7, 2.6 Hz, 1H), 5.22-5.00 (m, 2H), 3.94 (s, 3H). | I-182; I-63 |
| 509 | 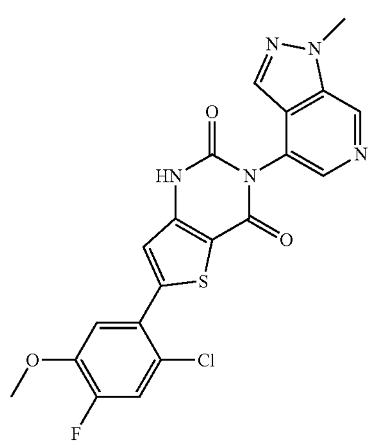 [SMILES: COc1cc(-c2cc3[nH]c(=O)n(-c4cncc5c4cnn5C)c(=O)c3s2)c(Cl)cc1F] | 487.8 | ¹H NMR (400 MHz, DMSO-d6) δ 12.24 (s, 2H), 9.27 (s, 2H), 8.26 (d, J = 10.5 Hz, 3H), 7.72 (d, J = 11.1 Hz, 2H), 7.44 (d, J = 8.9 Hz, 2H), 7.30 (s, 2H), 4.25 (s, 5H), 3.95 (s, 5H), 1.29-1.22 (m, 1H), 0.08 (s, 1H). | 1-methyl-1H-pyrazolo[3,4-c]pyridin-4-amine; I-62 |

Example 505

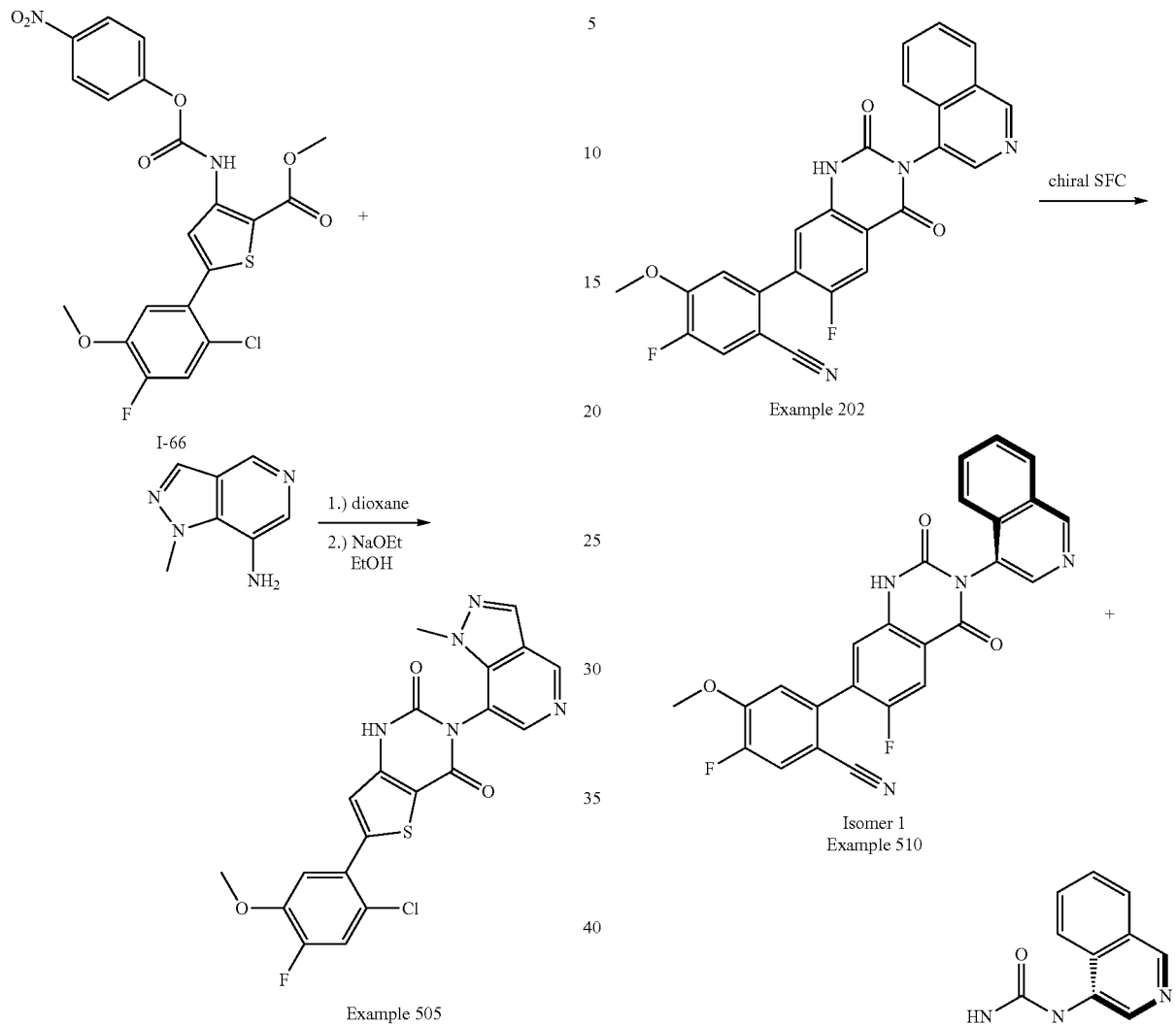

Example 202

Isomer 1
Example 510

Isomer 2
Example 511

6-(2-chloro-4-fluoro-5-methoxy-phenyl)-3-(1-cyclopropylpyrazolo[4,3-c]pyridin-7-yl)-1H-thieno[3,2-d]pyrimidine-2,4-dione (Example 505): To a suspension of methyl 5-(2-chloro-4-fluoro-5-methoxy-phenyl)-3-[(4-nitrophenoxy)carbonylamino]thiophene-2-carboxylate (I-66) (1.0 g, 2.08 mmol) in dioxane (9.43 mL, 0.2 M) was added 1-methylpyrazolo[4,3-c]pyridin-7-amine (370 mg, 2.5 mmol). The reaction mixture was stirred at 90° C. overnight. The reaction was subsequently cooled to rt and concentrated under reduced pressure. Ethanol (6.5 mL, 0.32 M) was added and to the suspension was added sodium ethoxide (21% wt. in EtOH; 1.56 mL, 3.12 mmol) at room temperature dropwise, and the reaction was stirred for 2 hours at room temperature. Approximately half of the solvent was removed under reduced pressure, and HCl (1N, 4 mL) was added. The mixture was let stand at 0° C., whereupon a precipitate formed. The solid was collected via filtration and dried over air to give the title compound Example 505 as an HCl salt.
ES/MS: 457.8 [M$^+$].
$^1$H NMR (400 MHz, DMSO-d6) δ 12.48 (s, 1H), 9.25 (s, 1H), 8.50 (s, 1H), 8.46 (s, 1H), 7.72 (d, J=11.1 Hz, 1H), 7.46 (d, J=8.9 Hz, 1H), 7.32 (s, 1H), 3.94 (s, 3H), 3.91 (s, 3H).

Procedure 60: Example 510 and Example 511

5-fluoro-2-[6-fluoro-3-(4-isoquinolyl)-2,4-dioxo-1H-quinazolin-7-yl]-4-methoxy-benzonitrile (Example 510 and Example 511): 5-fluoro-2-[6-fluoro-3-(4-isoquinolyl)-2,4-dioxo-1H-quinazolin-7-yl]-4-methoxy-benzonitrile (Example 202) as a mixture of 2 atropisomers was separated by chiral SFC (IB 5 um-4.6×100 mm column with 35% MeOH cosolvent) to give two enantiomers, which were assigned as Isomer 1 and Isomer 2. The stereochemistry was assigned by analogy to Example 438, with Example 510 being the more active isomer.

Isomer 1:

5-fluoro-2-[6-fluoro-3-(4-isoquinolyl)-2,4-dioxo-1H-quinazolin-7-yl]-4-methoxy-benzonitrile (Example 510)

ES/MS: 456.8 (M+).

¹H NMR (400 MHz, DMSO-d6) δ 11.99 (s, 1H), 9.47 (s, 1H), 8.61 (s, 1H), 8.30 (dd, J=7.5, 1.8 Hz, 1H), 8.10 (d, J=11.1 Hz, 1H), 7.92 (dd, J=17.6, 8.7 Hz, 2H), 7.80 (pd, J=6.9, 1.4 Hz, 2H), 7.49 (d, J=8.1 Hz, 1H), 7.38 (d, J=6.0 Hz, 1H), 4.00 (s, 3H).

Isomer 2:

5-fluoro-2-[6-fluoro-3-(4-isoquinolyl)-2,4-dioxo-1H-quinazolin-7-yl]-4-methoxy-benzonitrile (Example 511)

ES/MS: 456.8 (M+).

¹H NMR (400 MHz, DMSO-d6) δ 11.99 (s, 1H), 9.48 (s, 1H), 8.62 (s, 1H), 8.38-8.26 (m, 1H), 8.10 (d, J=11.2 Hz, 1H), 7.93 (dd, J=21.2, 8.7 Hz, 2H), 7.81 (dddd, J=14.8, 8.3, 7.0, 1.4 Hz, 2H), 7.49 (d, J=8.2 Hz, 1H), 7.38 (d, J=6.0 Hz, 1H), 4.00 (s, 3H).

Procedure 61: Example 512

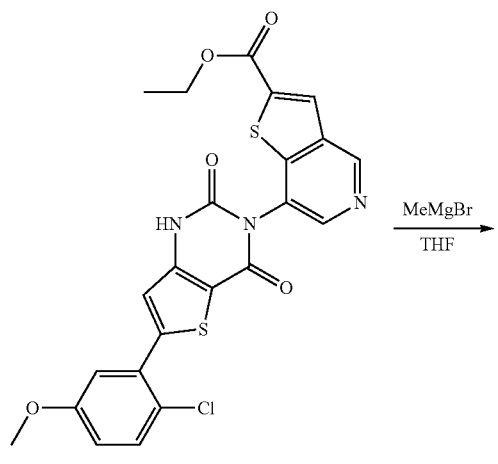

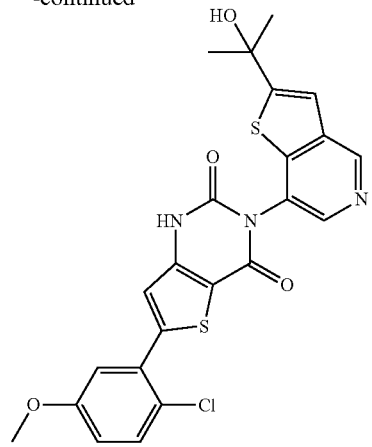

Example 512

6-(2-chloro-5-methoxy-phenyl)-3-[2-(1-hydroxy-1-methyl-ethyl)thieno[3,2-c]pyridin-7-yl]-1H-thieno[3,2-d]pyrimidine-2,4-dione (Example 512): A dram vial containing ethyl 7-[6-(2-chloro-5-methoxy-phenyl)-2,4-dioxo-1H-thieno[3,2-d]pyrimidin-3-yl]thieno[3,2-c]pyridine-2-carboxylate (I-116) (12.5 mg, 0.024 mmol) was evacuated and backfilled with argon three times. THF (0.243 mL) was then added and the resulting suspension was cooled to −78 C. To the cooled mixture was then added methylmagnesium bromide (0.03 mL) under argon and the reaction mixture was then warmed to ambient temperature and quenched with 1M aqueous HCl solution. The resulting mixture was then diluted with acetonitrile, filtered through an acrodisc, and was subsequently purified by RP-HPLC (0.1% TFA-ACN in 0.1% TFA Water, Column: Gemini 5 uM, NX-C18 110 Angstrom, 250×21.2 mm) to give the title compound Example 512 as a trifluoroacetate salt.

ES/MS: 499.7 (M+).

¹H NMR (400 MHz, DMSO-d6) δ 12.36 (s, 1H), 9.13 (s, 1H), 8.49 (s, 1H), 7.59 (d, J=8.9 Hz, 1H), 7.52 (s, 1H), 7.31 (s, 1H), 7.25 (d, J=3.0 Hz, 1H), 7.13 (dd, J=8.9, 3.0 Hz, 1H), 3.84 (s, 3H), 1.58 (s, 6H).

Examples 513-516

The following Examples were made in an analogous fashion according to Procedure 61 and are shown below in Table 28. Any different reagents/starting materials than those described in Procedure 61 are noted in the last column of Table 28—"Changes to Procedure 61: Different Reagents/Starting Materials".

TABLE 28

Examples 513-516

| Example | Structure | ES/MS m/z | 1H-NMR | Changes to Procedure 61: Different Reagents/ Starting Materials |
|---|---|---|---|---|
| 513 | 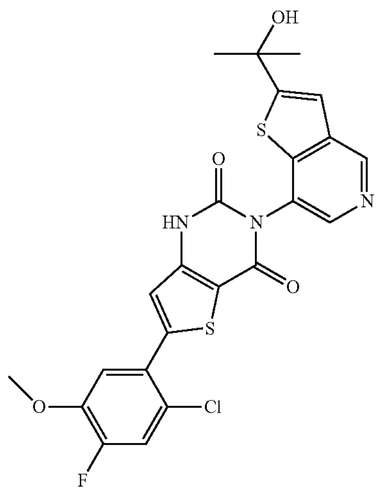 [SMILES: COc1cc(-c2cc3[nH]c(=O)n(-c4cncc5cc(C(C)(C)O)sc45)c(=O)c3s2)c(Cl)cc1F] | 517.7 | ¹H NMR (400 MHz, DMSO-d6) δ 12.39 (s, 1H), 9.15 (s, 1H), 8.52 (s, 1H), 7.71 (d, J = 11.0 Hz, 1H), 7.54 (s, 1H), 7.46 (d, J = 8.9 Hz, 1H), 7.30 (s, 1H), 3.94 (s, 3H), 1.58 (s, 6H) | I-117 |
| 514 | 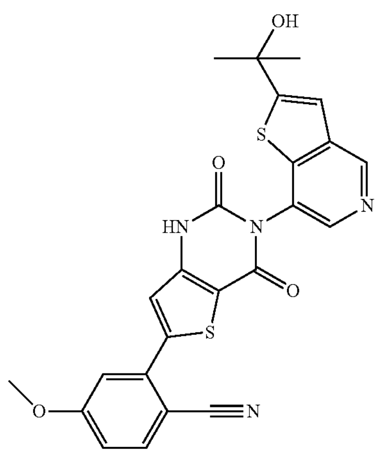 [SMILES: COc1ccc(C#N)c(-c2cc3[nH]c(=O)n(-c4cncc5cc(C(C)(C)O)sc45)c(=O)c3s2)c1] | 490.7 | ¹H NMR (400 MHz, DMSO-d6) δ 12.43 (s, 1H), 9.12 (s, 1H), 8.49 (s, 1H), 8.00 (d, J = 8.7 Hz, 1H), 7.51 (d, J = 9.1 Hz, 2H), 7.35 (d, J = 2.5 Hz, 1H), 7.27 (dd, J = 8.7, 2.5 Hz, 1H), 3.94 (s, 3H), 1.58 (s, 6H) | I-118 |
| 515 | 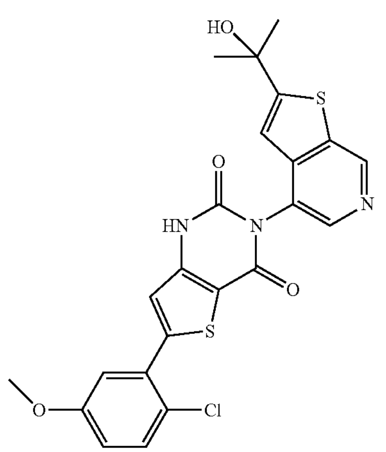 [SMILES: COc1ccc(Cl)c(-c2cc3[nH]c(=O)n(-c4cncc5sc(C(C)(C)O)cc45)c(=O)c3s2)c1] | 499.7 | ¹H NMR (400 MHz, DMSO) δ 12.24 (s, 1H), 9.33 (s, 1H), 8.52 (s, 1H), 7.60 (d, J = 8.9 Hz, 1H), 7.47 (s, 1H), 7.32 (s, 1H), 7.22 (d, J = 3.0 Hz, 1H), 7.14 (dd, J = 8.9, 3.0 Hz, 1H), 3.85 (s, 3H), 1.57 (d, J = 2.1 Hz, 6H). | I-146 |

TABLE 28-continued

Examples 513-516

| Example | Structure | ES/MS m/z | 1H-NMR | Changes to Procedure 61: Different Reagents/ Starting Materials |
|---|---|---|---|---|
| 516 | 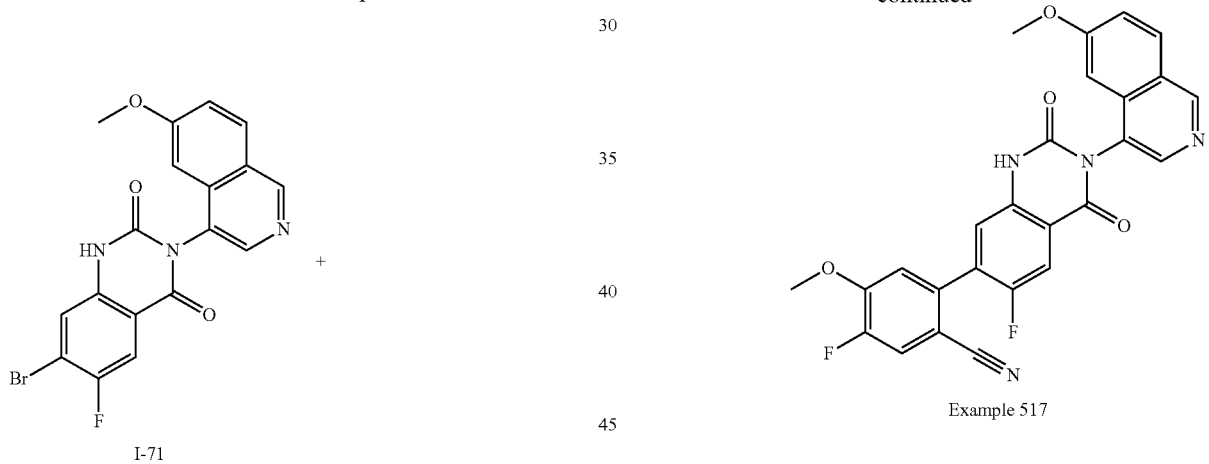 | 514.8 | $^1$H NMR (400 MHz, DMSO) δ 12.38 (s, 1H), 9.26 (s, 1H), 8.43 (s, 1H), 7.59 (d, J = 8.9 Hz, 1H), 7.33 (s, 1H), 7.28 (d, J = 3.0 Hz, 1H), 7.13 (dd, J = 8.9, 3.0 Hz, 1H), 3.85 (s, 3H), 2.22 (s, 3H), 1.60 (d, J = 2.1 Hz, 6H). | I-154 |

Procedure 62: Example 517

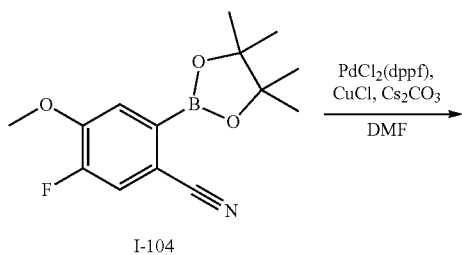

5-fluoro-2-[6-fluoro-3-(4-isoquinolyl)-2,4-dioxo-1H-quinazolin-7-yl]-4-methoxy-benzonitrile (Example 517): To a microwave vial containing 7-bromo-6-fluoro-3-(6-methoxy-4-isoquinolyl)-1H-quinazoline-2,4-dione (I-71) (50.0 mg, 0.12 mmol) was added 5-fluoro-4-methoxy-2-(4,4,5,5-tetramethyl-1,3,2-dioxaborolan-2-yl)benzonitrile (1-104) (66.6 mg, 0.24 mmol), [1,1'-Bis(diphenylphosphino)ferrocene]dichloropalladium(II) (13.4 mg, 0.02 mmol), copper(I) chloride (11.9 mg, 0.12 mmol), cesium carbonate (157 mg, 0.48 mmol), and DMF (2.00 mL). The reaction mixture was then degassed with argon for 30 seconds, sealed, and reacted under microwave irradiation at 120° C. for 15 minutes. The reaction mixture was then filtered through Celite, filtered through an acrodisc, and subsequently purified by RP-HPLC (0.1% TFA-ACN in 0.1% TFA Water, Column: Gemini 5 uM, NX-C18 110 Angstrom, 250×21.2 mm) to give the title compound Example 517 as a trifluoroacetate salt.

ES/MS: 486.8 (M⁺).

¹H NMR (400 MHz, DMSO-d6) δ 11.96 (s, 1H), 9.43 (s, 1H), 8.61 (s, 1H), 8.31 (d, J=9.1 Hz, 1H), 8.10 (d, J=11.1 Hz, 1H), 7.91 (d, J=9.3 Hz, 1H), 7.53-7.41 (m, 2H), 7.38 (d, J=6.0 Hz, 1H), 7.33 (d, J=2.3 Hz, 1H), 4.00 (s, 3H), 3.90 (s, 3H).

Procedure 63: Example 518

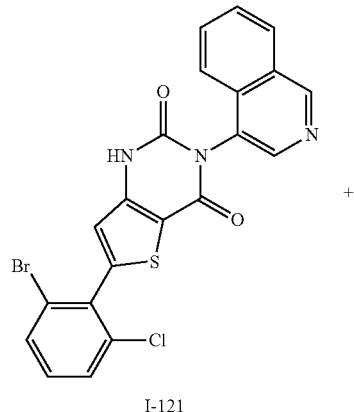

I-121

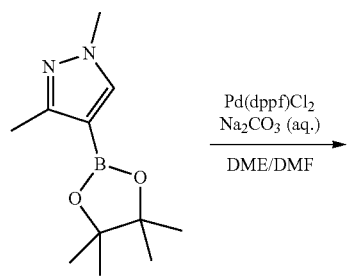

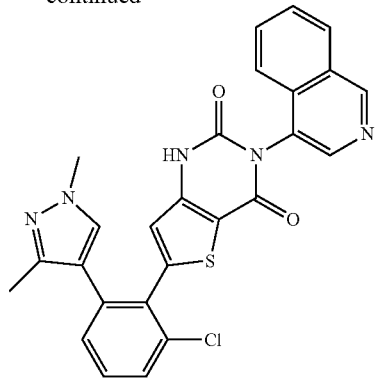

Example 518

6-[2-chloro-6-(1,3-dimethylpyrazol-4-yl)phenyl]-3-(4-isoquinolyl)-1H-thieno[3,2-d]pyrimidine-2,4-dione (Example 518): To a 10 mL microwave vial containing a stir bar was added 6-(2-bromo-6-chloro-phenyl)-3-(4-isoquinolyl)-1H-thieno[3,2-d]pyrimidine-2,4-dione (HCl salt) (I-121) (19 mg, 0.036 mmol, 1.0 equiv.), and Pd(dppf)Cl₂ (5.4 mg, 15 mol %) followed by 1:5 DMF/DME (0.6 mL, 0.06 M). Na₂CO₃ was added (0.05 mL, 2N solution) after which the reaction mixture was sealed with Teflon, degassed under Ar (5 min), and heated to 100° C. under microwave irradiation for 15 min. The crude product was diluted in acetonitrile/water/trifluoroacetic acid (1.5 mL; 5:1:0.2), filtered through an acrodisc, and purified directly by RP-HPLC (0.1% TFA-ACN in 0.1% TFA Water, Column: Gemini 5 μM, NX-C18 110 Angstrom, 250×21.2 mm) to give the product.

ES/MS: 500.10 (M⁺).

¹H NMR (400 MHz, Methanol-d₄) δ 9.64 (s, 1H), 8.68 (s, 1H), 8.51-8.41 (m, 11H), 8.13-7.91 (m, 3H), 7.62 (dd, J=8.1, 1.3 Hz, 1H), 7.54 (t, J=7.9 Hz, 1H), 7.45-7.34 (m, 2H), 6.97 (s, 1H), 3.81 (s, 3H), 2.11 (s, 3H).

Examples 519-529

The following Examples were made in an analogous fashion according to Procedure 63 and are shown below in Table 29. Any different reagents/starting materials than those described in Procedure 63 are noted in the last column of Table 29—"Changes to Procedure 63: Different Reagents/Starting Materials".

TABLE 29

Examples 519-529

| Example | Structure | ES/MS m/z | 1H-NMR | Changes to Procedure 63: Different Reagents/ Starting Materials |
|---|---|---|---|---|
| 519 | 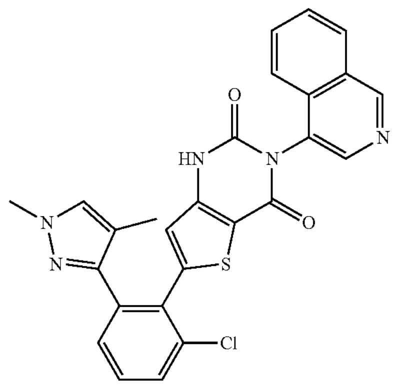 [SMILES: Cc1cn(C)nc1-c1cccc(Cl)c1-c1cc2[nH]c(=O)n(-c3cncc4ccccc34)c(=O)c2s1] | 500.1 | 1H NMR (400 MHz, Methanol-d4) δ 9.65 (d, J = 0.8 Hz, 1H), 8.67 (s, 1H), 8.46 (dt, J = 8.3, 1.0 Hz, 1H), 8.07 (ddd, J = 8.2, 6.8, 1.3 Hz, 1H), 8.03-7.92 (m, 2H), 7.71 (dd, J = 8.1, 1.3 Hz, 1H), 7.58 (t, J = 7.9 Hz, 1H), 7.43 (dd, J = 7.6, 1.3 Hz, 1H), 7.36 (d, J = 0.9 Hz, 1H), 6.99 (s, 1H), 3.83 (s, 3H), 1.87 (d, J = 0.8 Hz, 3H). | 1,4-dimethyl-3-(4,4,5,5-tetramethyl-1,3,2-dioxaborolan-2-yl)pyrazole |
| 520 | 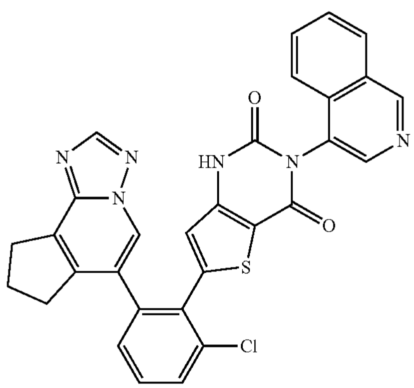 [SMILES: O=c1[nH]c2cc(-c3c(Cl)cccc3-c3cn4ncnc4c4c3CCC4)sc2c(=O)n1-c1cncc2ccccc12] | 563.2 | 1H NMR (400 MHz, Methanol-d4) δ 9.55 (s, 1H), 8.64 (d, J = 10.9 Hz, 1H), 8.56 (s, 1H), 8.45-8.32 (m, 2H), 8.04-7.85 (m, 4H), 7.78 (d, J = 8.2 Hz, 1H), 7.65 (t, J = 7.9 Hz, 1H), 7.51 (d, J = 7.9 Hz, 1H), 7.05 (s, 1H), 3.30-3.25 (m, 32H), 2.91 (s, 1H), 2.30 (d, J = 9.2 Hz, 2H). | I-169 |
| 521 | 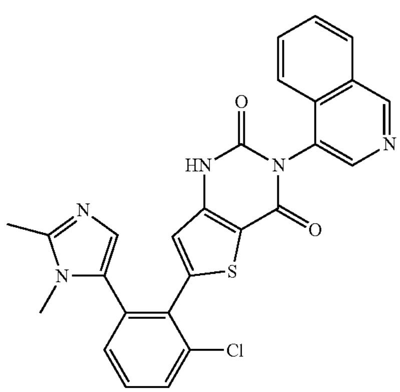 [SMILES: Cc1ncc(-c2cccc(Cl)c2-c2cc3[nH]c(=O)n(-c4cncc5ccccc45)c(=O)c3s2)n1C] | 500.1 | 1H NMR (400 MHz, Methanol-d4) δ 9.49 (d, J = 0.8 Hz, 1H), 8.52 (s, 1H), 8.39-8.31 (m, 1H), 7.98-7.81 (m, 4H), 7.73 (t, J = 7.9 Hz, 1H), 7.60 (dd, J = 7.7, 1.2 Hz, 1H), 7.49 (s, 1H), 7.13 (s, 1H), 3.59 (s, 3H), 2.68 (s, 3H). | 1,2-dimethyl-5-(4,4,5,5-tetramethyl-1,3,2-dioxaborolan-2-yl)imidazole |

TABLE 29-continued

Examples 519-529

| Example | Structure | ES/MS m/z | 1H-NMR | Changes to Procedure 63: Different Reagents/ Starting Materials |
|---|---|---|---|---|
| 522 | 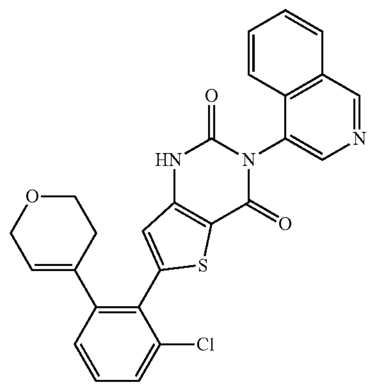 [SMILES: O=c1[nH]c2cc(-c3c(Cl)cccc3C3=CCOCC3)sc2c(=O)n1-c1cncc2ccccc12] | 488.0 | 1H NMR (400 MHz, Methanol-d4) δ 9.63 (s, 1H), 8.70 (s, 1H), 8.44 (d, J = 8.3 Hz, 1H), 8.11-7.99 (m, 2H), 7.94 (t, J = 7.3 Hz, 1H), 7.56 (dd, J = 8.1, 1.4 Hz, 1H), 7.49 (t, J = 7.8 Hz, 1H), 7.35 (dd, J = 7.6, 1.4 Hz, 1H), 7.05 (s, 1H), 5.78 (s, 1H), 4.20 (d, J = 2.9 Hz, 2H), 3.77 (t, J = 5.3 Hz, 2H), 2.18 (s, 2H). | 2-(3,6-dihydro-2H-pyran-4-yl)-4,4,5,5-tetramethyl-1,3,2-dioxaborolane |
| 523 | 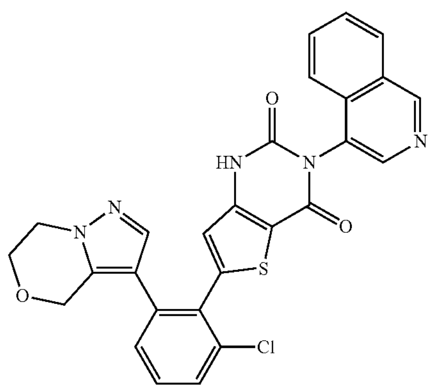 | 528.1 | 1H NMR (400 MHz, Methanol-d4) δ 9.66 (s, 1H), 8.70 (s, 1H), 8.46 (dt, J = 8.3, 1.0 Hz, 1H), 8.08 (ddd, J = 8.1, 6.7, 1.2 Hz, 1H), 8.06-7.99 (m, 1H), 7.96 (ddd, J = 8.2, 6.7, 1.3 Hz, 1H), 7.60 (dd, J = 8.1, 1.3 Hz, 1H), 7.54 (t, J = 7.9 Hz, 1H), 7.34 (dd, J = 7.6, 1.3 Hz, 1H), 7.24 (s, 1H), 7.02 (s, 1H), 4.82 (s, 2H), 4.15 (tt, J = 5.3, 2.6 Hz, 4H). | 3-(4,4,5,5-tetramethyl-1,3,2-dioxaborolan-2-yl)-6,7-dihydro-4H-pyrazolo[5,1-c][1,4]oxazine |
| 524 | 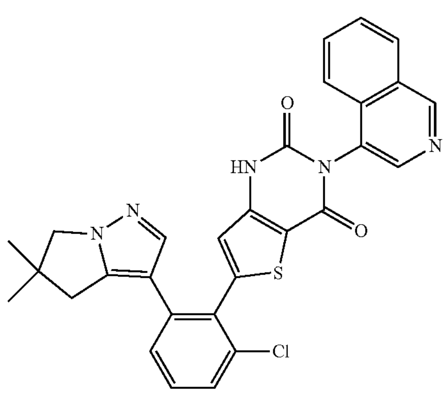 [SMILES: CC1(C)Cc2c(-c3cccc(Cl)c3-c3cc4[nH]c(=O)n(-c5cncc6ccccc56)c(=O)c4s3)cnn2C1] | 540.1 | 1H NMR (400 MHz, Methanol-d4) δ 9.60 (s, 1H), 8.64 (s, 1H), 8.43 (d, J = 8.2 Hz, 1H), 8.04 (t, J = 7.5 Hz, 1H), 7.93 (t, J = 7.2 Hz, 2H), 7.60-7.47 (m, 2H), 7.46 (dd, J = 7.5, 1.6 Hz, 1H), 7.24 (s, 1H), 7.03 (s, 1H), 3.90 (s, 2H), 2.68 (s, 2H), 1.34-1.19 (m, 6H). | 5,5-dimethyl-3-(4,4,5,5-tetramethyl-1,3,2-dioxaborolan-2-yl)-4,6-dihydropyrrolo[1,2-b]pyrazole |

TABLE 29-continued

Examples 519-529

| Example | Structure | ES/MS m/z | 1H-NMR | Changes to Procedure 63: Different Reagents/ Starting Materials |
|---|---|---|---|---|
| 525 | 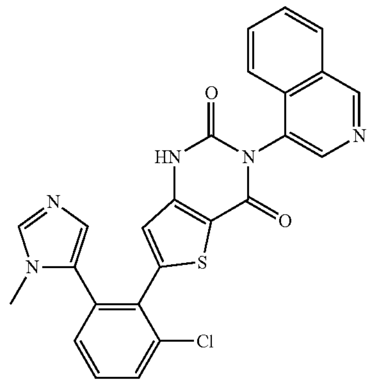 [SMILES: Cn1cncc1-c1cccc(Cl)c1-c1cc2[nH]c(=O)n(-c3cncc4ccccc34)c(=O)c2s1] | 485.7 | 1H NMR (400 MHz, Methanol-d4) δ 9.50 (d, J = 0.8 Hz, 1H), 8.97 (dd, J = 1.5, 0.7 Hz, 1H), 8.53 (s, 1H), 8.39-8.32 (m, 1H), 7.99-7.81 (m, 4H), 7.74 (t, J = 7.9 Hz, 1H), 7.69-7.58 (m, 2H), 7.14 (s, 1H), 3.75 (s, 3H). | 1-methyl-5-(4,4,5,5-tetramethyl-1,3,2-dioxaborolan-2-yl)imidazole |
| 526 | 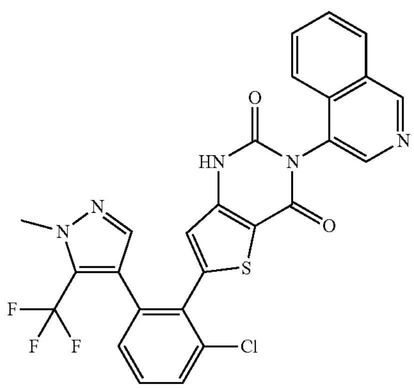 [SMILES: Cn1ncc(-c2cccc(Cl)c2-c2cc3[nH]c(=O)n(-c4cncc5ccccc45)c(=O)c3s2)c1C(F)(F)F] | 553.7 | 1H NMR (400 MHz, Methanol-d4) δ 9.64 (s, 1H), 8.67 (s, 1H), 8.45 (d, J = 8.3 Hz, 1H), 8.07 (ddd, J = 8.1, 6.7, 1.2 Hz, 1H), 8.04-7.90 (m, 2H), 7.70 (dd, J = 8.2, 1.2 Hz, 1H), 7.57 (t, J = 7.9 Hz, 1H), 7.51-7.36 (m, 2H), 6.94 (s, 1H), 4.02 (d, J = 1.0 Hz, 3H). | 1-methyl-4-(4,4,5,5-tetramethyl-1,3,2-dioxaborolan-2-yl)-5-(trifluoromethyl)pyrazole |
| 527 | 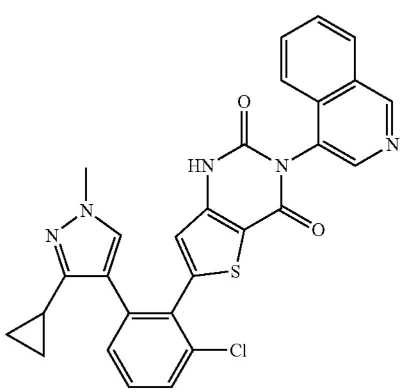 [SMILES: Cn1cc(-c2cccc(Cl)c2-c2cc3[nH]c(=O)n(-c4cncc5ccccc45)c(=O)c3s2)c(C2CC2)n1] | 526.8 | 1H NMR (400 MHz, Methanol-d4) δ 9.64-9.57 (m, 1H), 8.65 (s, 1H), 8.42 (d, J = 8.2 Hz, 1H), 8.03 (ddd, J = 8.2, 6.8, 1.2 Hz, 1H), 7.93 (dd, J = 15.8, 7.7 Hz, 2H), 7.62 (dd, J = 8.0, 1.4 Hz, 1H), 7.54 (t, J = 7.8 Hz, 1H), 7.48 (dd, J = 7.7, 1.4 Hz, 1H), 7.37 (s, 1H), 6.99 (s, 1H), 3.77 (s, 3H), 1.71-1.59 (m, 1H), 0.88-0.70 (m, 4H). | 3-cyclopropyl-1-methyl-4-(4,4,5,5-tetramethyl-1,3,2-dioxaborolan-2-yl)pyrazole |

TABLE 29-continued

Examples 519-529

| Example | Structure | ES/MS m/z | 1H-NMR | Changes to Procedure 63: Different Reagents/ Starting Materials |
|---|---|---|---|---|
| 528 | 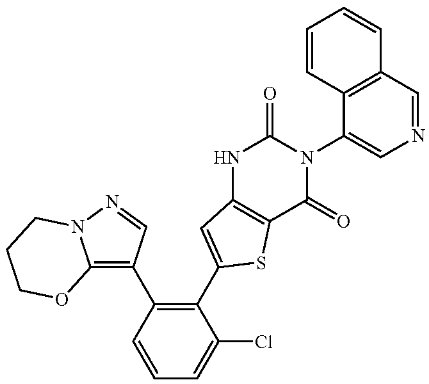 [SMILES: O=c1[nH]c2cc(-c3c(Cl)cccc3-c3cnn4c3OCCC4)sc2c(=O)n1-c1cncc2ccccc12] | 527.7 | 1H NMR (400 MHz, DMSO-d6) δ 12.26 (s, 1H), 9.47 (s, 1H), 8.64 (s, 1H), 8.30 (d, J = 8.1 Hz, 1H), 7.89-7.80 (m, 2H), 7.79 (ddd, J = 8.0, 5.0, 3.2 Hz, 1H), 7.63-7.48 (m, 3H), 7.01 (s, 1H), 6.89 (s, 1H), 4.38-4.31 (m, 2H), 4.10 (t, J = 6.1 Hz, 2H), 2.25-2.15 (m, 2H). | 3-(4,4,5,5-tetramethyl-1,3,2-dioxaborolan-2-yl)-6,7-dihydro-5H-pyrazolo[5,1-b][1,3]oxazine |
| 529 | 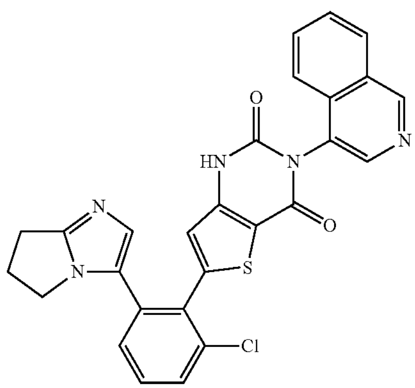 [SMILES: O=c1[nH]c2cc(-c3c(Cl)cccc3-c3cnc4n3CCC4)sc2c(=O)n1-c1cncc2ccccc12] | 511.7 | 1H NMR (400 MHz, DMSO-d6) δ 12.32 (s, 1H), 9.45 (s, 1H), 8.63-8.54 (m, 1H), 8.29 (dt, J = 7.9, 1.3 Hz, 1H), 7.88 dd, J = 7.8, 1.5 Hz, 1H), 7.88-7.79 (m, 1H), 7.81 (d, J = 3.9 Hz, 1H), 7.83-7.66 (m, 3H), 7.37 (s, 1H), 7.15 (s, 1H), 4.19 (t, J = 7.2 Hz, 2H), 3.20 (t, J = 7.6 Hz, 2H), 2.68 (p, J = 7.5 Hz, 2H). | 3-(4,4,5,5-tetramethyl-1,3,2-dioxaborolan-2-yl)-6,7-dihydro-5H-pyrrolo[1,2-a]imidazole |

Procedure 64: Example 530

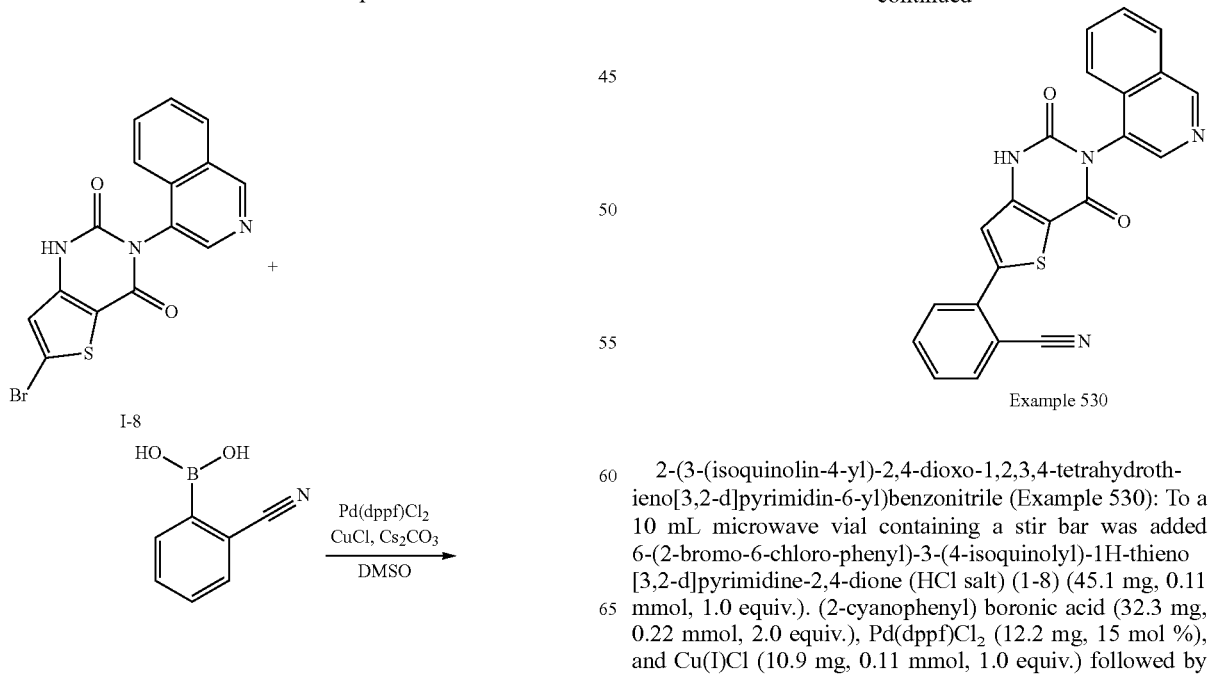

Example 530

2-(3-(isoquinolin-4-yl)-2,4-dioxo-1,2,3,4-tetrahydrothieno[3,2-d]pyrimidin-6-yl)benzonitrile (Example 530): To a 10 mL microwave vial containing a stir bar was added 6-(2-bromo-6-chloro-phenyl)-3-(4-isoquinolyl)-1H-thieno[3,2-d]pyrimidine-2,4-dione (HCl salt) (1-8) (45.1 mg, 0.11 mmol, 1.0 equiv.). (2-cyanophenyl) boronic acid (32.3 mg, 0.22 mmol, 2.0 equiv.), Pd(dppf)Cl₂ (12.2 mg, 15 mol %), and Cu(I)Cl (10.9 mg, 0.11 mmol, 1.0 equiv.) followed by Cs$_2$CO$_3$ (107 mg, 0.33 mmol, 3.0) equiv.). DMSO (2.0 mL) was added, and the reaction mixture was sealed with Teflon, degassed under Ar (5 min), and heated to 120° C. under microwave irradiation for 20 m. The crude product was diluted in acetonitrile/water/trifluoroacetic acid (1.5 mL, 5:1:0.2), filtered through an acrodisc, and purified directly by RP-HPLC (0.1% TFA-ACN in 0.1% TFA Water. Column: Gemini 5 μM, NX-C18 110 Angstrom, 250×21.2 mm) to give the product.

ES/MS: 396.8 (M$^+$).

3H NMR (400 MHz, DMSO-d$_6$) δ 12.35 (s, 1H), 9.46 (s, 1H), 8.60 (s, 1H), 8.29 (dd J=7.3, 1.5 Hz, 1H), 8.09 (dd, J=7.6, 1.0 Hz, 1H), 7.96-7.61 (m, 6H), 7.55 (s, 1H).

Examples 531-550

The following Examples were made in an analogous fashion according to Procedure 64 and are shown below in Table 30. Any different reagents/starting materials than those described in Procedure 64 are noted in the last column of Table 30—"Changes to Procedure 64: Different Reagents/ Starting Materials".

TABLE 30

Examples 531-550

| Example | Structure | ES/MS m/z | 1H-NMR | Changes to Procedure 64: Different Reagents/ Starting Materials |
|---|---|---|---|---|
| 531 | 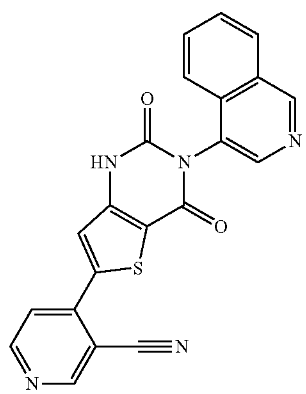 [SMILES: N#Cc1cnccc1-c1cc2[nH]c(=O)n(-c3cncc4ccccc34)c(=O)c2s1] | 397.8 | 1H NMR (400 MHz, Methanol-d4) δ 9.60 (s, 1H), 9.11 (s, 1H), 8.89 (d, J = 5.1 Hz, 1H), 8.68 (s, 1H), 8.43 (d, J = 8.4 Hz, 1H), 8.02 (d, J = 7.0 Hz, 2H), 7.98-7.88 (m, 2H), 7.67 (s, 1H). | (3-cyano-4-pyridyl) boronic acid |
| 532 | 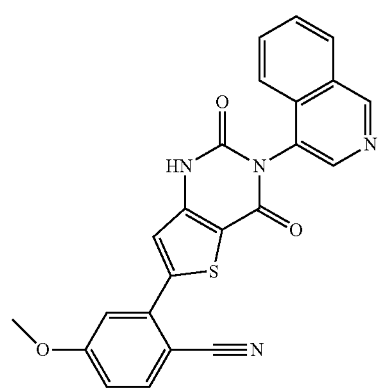 [SMILES: COc1ccc(C#N)c(-c2cc3[nH]c(=O)n(-c4cncc5ccccc45)c(=O)c3s2)c1] | 426.8 | 1H NMR (400 MHz, DMSO-d6) δ 12.36 (s, 1H), 9.50 (s, 1H), 8.63 (s, 1H), 8.30 (dd, J = 7.6, 1.6 Hz, 1H), 8.01 (d, J = 8.7 Hz, 1H), 7.95-7.88 (m, 1H), 7.81 (dddd, J = 16.5, 8.1, 6.8, 1.4 Hz, 2H), 7.52 (s, 1H), 7.34 (d, J = 2.5 Hz, 1H), 7.28 (dd, J = 8.8, 2.6 Hz, 1H), 3.95 (s, 3H). | I-103 |

TABLE 30-continued

Examples 531-550

| Example | Structure | ES/MS m/z | 1H-NMR | Changes to Procedure 64: Different Reagents/ Starting Materials |
|---|---|---|---|---|
| 533 | 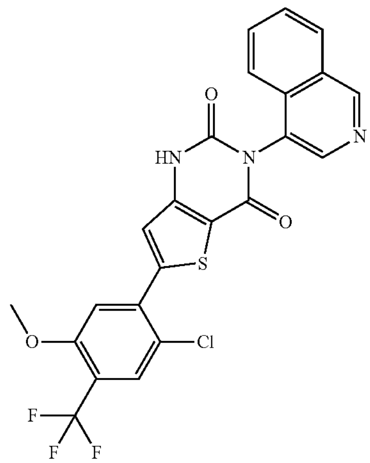 [SMILES: COc1cc(-c2cc3[nH]c(=O)n(-c4cncc5ccccc45)c(=O)c3s2)c(Cl)cc1C(F)(F)F] | 519.6 | 1H NMR (400 MHz, DMSO-d6) δ 12.34 (s, 1H), 9.51 (s, 1H), 8.62 (s, 1H), 8.32 (dd, J = 7.7, 1.4 Hz, 1H), 7.93-7.80 (m, 2H), 7.85-7.76 (m, 2H), 7.52 (s, 1H), 7.39 (s, 1H), 3.98 (s, 3H). | [2-chloro-5-methoxy-4-(trifluoromethyl)phenyl]boronic acid |
| 534 | 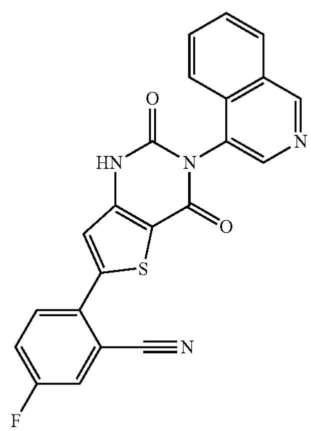 [SMILES: N#Cc1cc(F)ccc1-c1cc2[nH]c(=O)n(-c3cncc4ccccc34)c(=O)c2s1] | 414.7 | 1H NMR (400 MHz, DMSO-d6) δ 12.36 (s, 1H), 9.47 (s, 1H), 8.60 (s, 1H), 8.30 (dd, J = 7.4, 1.6 Hz, 1H), 8.13 (dd, J = 8.6, 2.8 Hz, 1H), 7.98-7.89 (m, 2H), 7.87-7.73 (m, 3H), 7.51 (s, 1H). | (2-cyano-4-fluoro-phenyl)boronic acid |
| 535 | 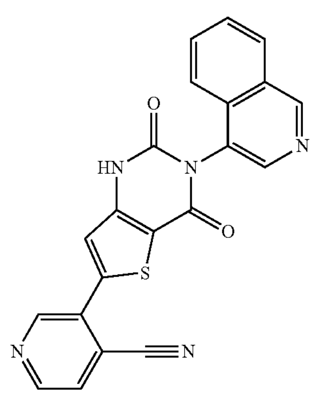 [SMILES: N#Cc1ccncc1-c1cc2[nH]c(=O)n(-c3cncc4ccccc34)c(=O)c2s1] | 397.8 | 1H NMR (400 MHz, DMSO-d6) δ 12.41 (d, J = 1.8 Hz, 1H), 9.51 (s, 1H), 9.15 (s, 1H), 8.94 (d, J = 5.1 Hz, 1H), 8.64 (s, 1H), 8.34-8.27 (m, 1H), 8.14-8.07 (m, 1H), 7.97-7.75 (m, 3H), 7.63 (s, 1H). | (4-cyano-3-pyridyl)boronic acid |

TABLE 30-continued

Examples 531-550

| Example | Structure | ES/MS m/z | 1H-NMR | Changes to Procedure 64: Different Reagents/ Starting Materials |
|---|---|---|---|---|
| 536 | 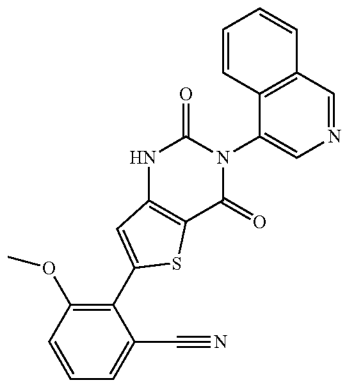 [SMILES: COc1cccc(C#N)c1-c1cc2[nH]c(=O)n(-c3cncc4ccccc34)c(=O)c2s1] | 426.8 | 1H NMR (400 MHz, DMSO-d6) δ 12.30 (s, 1H), 9.48 (s, 1H), 8.63 (s, 1H), 8.30 (dd, J = 7.7, 1.7 Hz, 1H), 7.94 (d, J = 8.0 Hz, 1H), 7.81 (dddd, J = 16.4, 8.0, 6.9, 1.4 Hz, 2H), 7.74-7.65 (m, 1H), 7.61 (ddd, J = 11.9, 8.1, 1.2 Hz, 2H), 7.34 (s, 1H), 3.92 (s, 3H). | 3-methoxy-2-(4,4,5,5-tetramethyl-1,3,2-dioxaborolan-2-yl)benzonitrile |
| 537 | 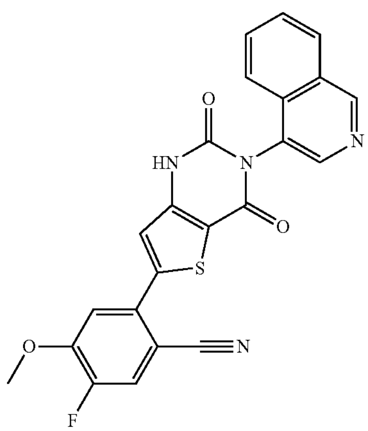 [SMILES: COc1cc(-c2cc3[nH]c(=O)n(-c4cncc5ccccc45)c(=O)c3s2)c(C#N)cc1F] | 444.8 | 1H NMR (400 MHz, DMSO-d6) δ 12.38 (s, 1H), 9.48 (s, 1H), 8.62 (s, 1H), 8.30 (dd, J = 7.6, 1.6 Hz, 1H), 8.11 (d, J = 11.1 Hz, 1H), 7.90 (d, J = 8.2 Hz, 1H), 7.81 (dddd, J = 17.4, 8.1, 6.8, 1.5 Hz, 2H), 7.57-7.47 (m, 2H), 4.05 (s, 3H). | I-104 |
| 538 | 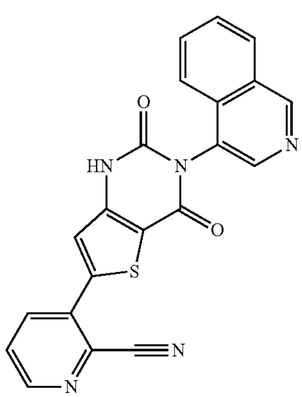 [SMILES: N#Cc1ncccc1-c1cc2[nH]c(=O)n(-c3cncc4ccccc34)c(=O)c2s1] | 397.8 | 1H NMR (400 MHz, DMSO-d6) δ 12.41 (s, 1H), 9.48 (s, 1H), 8.87 (dd, J = 4.7, 1.5 Hz, 1H), 8.61 (s, 1H), 8.33 (ddd, J = 17.7, 7.8, 1.5 Hz, 2H), 7.97-7.72 (m, 4H), 7.65 (s, 1H). | (2-cyano-3-pyridyl)boronic acid |

TABLE 30-continued

Examples 531-550

| Example | Structure | ES/MS m/z | 1H-NMR | Changes to Procedure 64: Different Reagents/ Starting Materials |
|---|---|---|---|---|
| 539 | 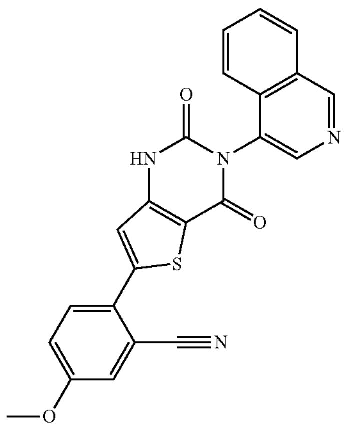 [SMILES: COc1ccc(-c2cc3[nH]c(=O)n(-c4cncc5ccccc45)c(=O)c3s2)c(C#N)c1] | 426.7 | 1H NMR (400 MHz, DMSO-d6) δ 12.32 (s, 1H), 9.50 (s, 1H), 8.62 (s, 1H), 8.33-8.26 (m, 1H), 7.95-7.87 (m, 1H), 7.88-7.74 (m, 3H), 7.68 (d, J = 2.8 Hz, 1H), 7.48-7.40 (m, 2H), 3.91 (s, 3H). | 5-methoxy-2-(4,4,5,5-tetramethyl-1,3,2-dioxaborolan-2-yl)benzonitrile |
| 540 | 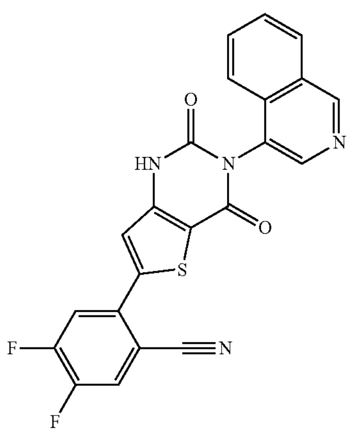 [SMILES: N#Cc1cc(F)c(F)cc1-c1cc2[nH]c(=O)n(-c3cncc4ccccc34)c(=O)c2s1] | 432.8 | 1H NMR (400 MHz, DMSO-d6) δ 12.34 (s, 1H), 8.65 (s, 1H), 8.31 (dd, J = 7.8, 1.7 Hz, 1H), 8.04 (d, J = 10.9 Hz, 1H), 7.97-7.72 (m, 4H), 7.45 (s, 1H), 7.32 (d, J = 8.1 Hz, 1H). | 4,5-difluoro-2-(4,4,5,5-tetramethyl-1,3,2-dioxaborolan-2-yl)benzonitrile |
| 541 | 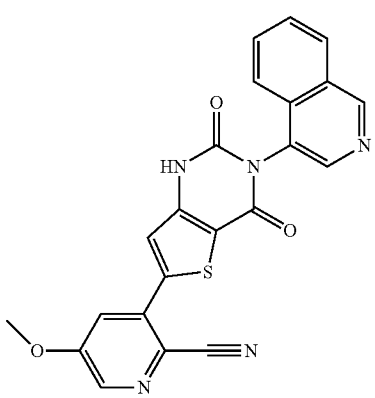 [SMILES: COc1cnc(C#N)c(-c2cc3[nH]c(=O)n(-c4cncc5ccccc45)c(=O)c3s2)c1] | 427.8 | 1H NMR (400 MHz, DMSO-d6) δ 12.42 (s, 1H), 9.47 (s, 1H), 8.63-8.55 (m, 2H), 8.29 (d, J = 1.5 Hz, 1H), 7.95-7.88 (m, 1H), 7.88-7.74 (m, 3H), 7.63 (s, 1H), 4.04 (s, 3H). | I-129 |

TABLE 30-continued

Examples 531-550

| Example | Structure | ES/MS m/z | 1H-NMR | Changes to Procedure 64: Different Reagents/ Starting Materials |
|---|---|---|---|---|
| 542 | 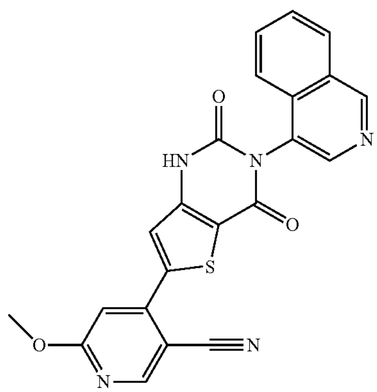 [SMILES: COc1cc(-c2cc3[nH]c(=O)n(-c4cncc5ccccc45)c(=O)c3s2)c(C#N)cn1] | 427.7 | 1H NMR (400 MHz, DMSO-d6) δ 12.40 (s, 1H), 9.50 (s, 1H), 8.90 (s, 1H), 8.62 (s, 1H), 8.30 (dd, J = 7.4, 1.6 Hz, 1H), 7.97-7.90 (m, 1H), 7.81 (dddd, J = 16.1, 8.1, 6.8, 1.4 Hz, 2H), 7.69 (s, 1H), 7.35 (s, 1H), 4.03 (s, 3H). | I-105 |
| 543 | 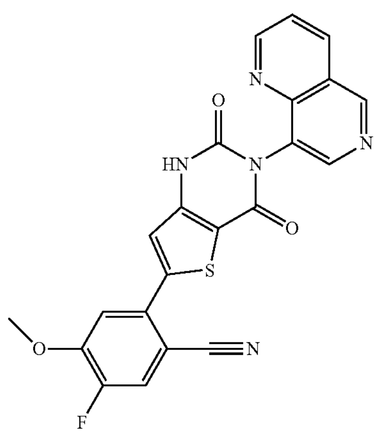 [SMILES: COc1cc(-c2cc3[nH]c(=O)n(-c4cncc5cccnc45)c(=O)c3s2)c(C#N)cc1F] | 445.8 | 1H NMR (400 MHz, DMSO-d6) δ 12.35 (s, 1H), 9.59 (s, 1H), 9.13 (dd, J = 4.3, 1.6 Hz, 1H), 8.91-8.85 (m, 1H), 8.74 (dd, J = 8.3, 1.7 Hz, 1H), 8.10 (d, J = 11.1 Hz, 1H), 7.80 (dd, J = 8.3, 4.3 Hz, 1H), 7.56 (d, J = 8.1 Hz, 1H), 7.48 (s, 1H), 4.05 (s, 3H). | I-104; I-94 |
| 544 | 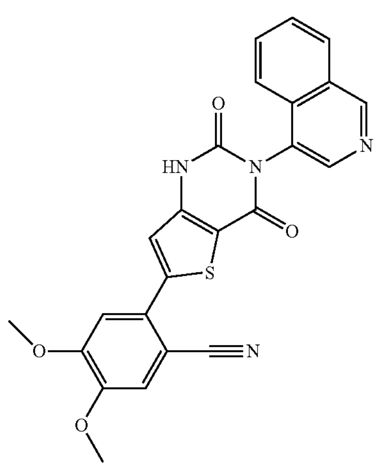 [SMILES: COc1cc(C#N)c(-c2cc3[nH]c(=O)n(-c4cncc5ccccc45)c(=O)c3s2)cc1OC] | 456.8 | 1H NMR (400 MHz, DMSO-d6) δ 12.33 (s, 1H), 9.47 (s, 1H), 8.60 (s, 1H), 8.32-8.24 (m, 1H), 7.94-7.71 (m, 3H), 7.60 (s, 1H), 7.46 (s, 1H), 7.30 (s, 1H), 3.96 (s, 3H), 3.91 (s, 3H) | I-106 |

TABLE 30-continued

Examples 531-550

| Example | Structure | ES/MS m/z | 1H-NMR | Changes to Procedure 64: Different Reagents/ Starting Materials |
|---|---|---|---|---|
| 545 | 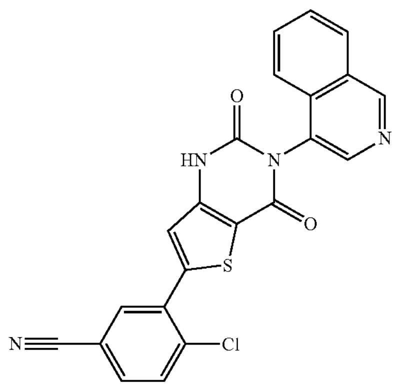 [SMILES: N#Cc1ccc(Cl)c(-c2cc3[nH]c(=O)n(-c4cncc5ccccc45)c(=O)c3s2)c1] | 430.7 | 1H NMR (400 MHz, DMSO-d6) δ 12.38 (s, 1H), 9.47 (s, 1H), 8.61 (s, 1H), 8.40-8.21 (m, 2H), 8.01 (dd, J = 8.4, 2.0 Hz, 1H), 7.97-7.86 (m, 2H), 7.81 (dddd, J = 18.6, 8.0, 6.8, 1.4 Hz, 2H), 7.43 (s, 1H) | (2-chloro-5-cyano-phenyl)boronic acid |
| 546 | 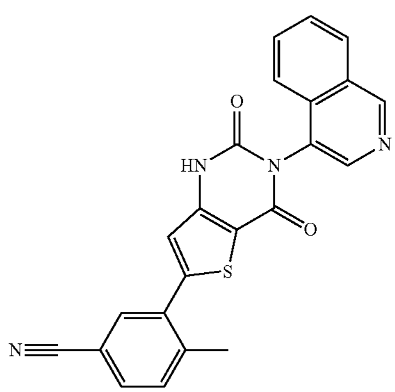 [SMILES: Cc1ccc(C#N)cc1-c1cc2[nH]c(=O)n(-c3cncc4ccccc34)c(=O)c2s1] | 410.8 | 1H NMR (400 MHz, DMSO-d6) δ 12.34 (s, 1H), 9.48 (s, 1H), 8.60 (s, 1H), 8.31 (d, J = 8.0 Hz, 1H), 8.00 (s, 1H), 7.92-7.75 (m, 4H), 7.64 (d, J = 8.1 Hz, 1H), 7.21 (s, 1H), 2.53 (s, 3H) | 4-methyl-3-(4,4,5,5-tetramethyl-1,3,2-dioxaborolan-2-yl)benzonitrile |
| 547 | 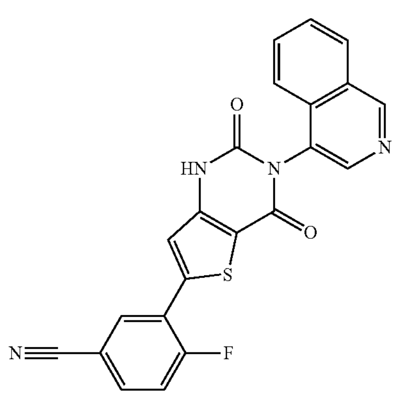 [SMILES: N#Cc1ccc(F)c(-c2cc3[nH]c(=O)n(-c4cncc5ccccc45)c(=O)c3s2)c1] | 414.8 | 1H NMR (400 MHz, DMSO-d6) δ 12.42 (s, 1H), 9.47 (s, 1H), 8.65-8.51 (m, 2H), 8.30 (d, J = 8.1 Hz, 1H), 8.14-7.98 (m, 1H), 7.96-7.66 (m, 4H), 7.62 (s, 1H) | (5-cyano-2-fluoro-phenyl)boronic acid |

TABLE 30-continued

Examples 531-550

| Example | Structure | ES/MS m/z | 1H-NMR | Changes to Procedure 64: Different Reagents/ Starting Materials |
|---|---|---|---|---|
| 548 | 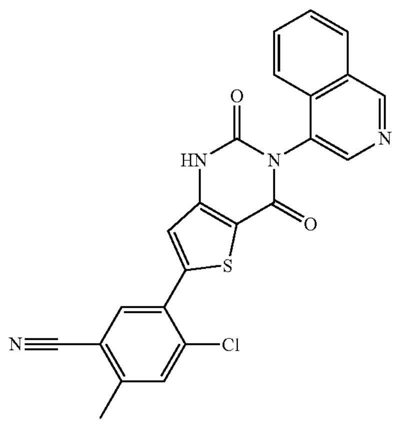 [SMILES: Cc1cc(Cl)c(-c2cc3[nH]c(=O)n(-c4cncc5ccccc45)c(=O)c3s2)cc1C#N] | 444.8 | 1H NMR (400 MHz, DMSO-d6) δ 12.37 (s, 1H), 9.49 (s, H), 8.62 (s, 1H), 8.37-8.28 (m, 1H), 8.25 (s, 1H), 7.99-7.68 (m, 4H), 7.39 (s, 1H), 2.54 (d, J = 3.9 Hz, 3H) | (2-chloro-5-cyano-4-methyl-phenyl)boronic acid |
| 549 | 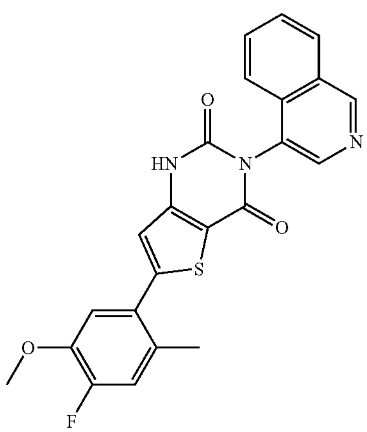 [SMILES: COc1cc(-c2cc3[nH]c(=O)n(-c4cncc5ccccc45)c(=O)c3s2)c(C)cc1F] | 428.8 | 1H NMR (400 MHz, DMSO-d6) δ 12.35 (s, 1H), 9.56 (s, 1H), 8.67 (s, 1H), 8.31 (dd, J = 7.9, 1.3 Hz, 1H), 8.11 (d, J = 6.7 Hz, 1H), 7.91-7.76 (m, 3H), 7.67 (d, J = 10.4 Hz, 1H), 7.18 (s, 1H), 2.53 (s, 3H) | I-112 |
| 550 | 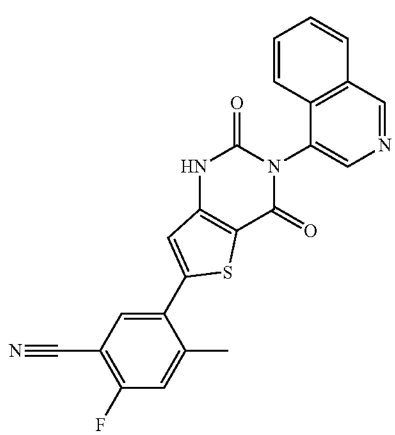 [SMILES: Cc1cc(F)c(C#N)cc1-c1cc2[nH]c(=O)n(-c3cncc4ccccc34)c(=O)c2s1] | 433.8 | 1H NMR (400 MHz, DMSO-d6) δ 12.27 (s, 1H), 9.53 (s, 1H), 8.64 (s, 1H), 8.35-8.21 (m, 1H), 7.94-7.69 (m, 3H), 7.31 (d, J = 12.4 Hz, 1H), 7.23 (d, J = 8.7 Hz, 1H), 7.10 (s, 1H). 3.89 (s, 3H), 2.38 (s, 3H) | I-113 |

Procedure 65: Example 551

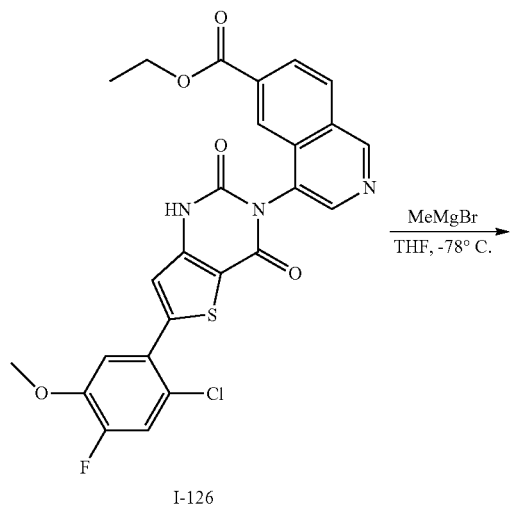

I-126

Example 551

6-(2-chloro-4-fluoro-5-methoxyphenyl)-3-(6-(2-hydroxypropan-2-yl)isoquinolin-4-yl)thieno[3,2-d]pyrimidine-2,4(1H,3H)-dione (Example 551): To a stirring solution of ethyl 4-(6-(2-chloro-4-fluoro-5-methoxyphenyl)-2,4-dioxo-1,4-dihydrothieno[3,2-d]pyrimidin-3(2H)-yl)isoquinoline-6-carboxylate (62 mg, 0.12 mmol, 1.0 equiv.) in THF (1.2 mL, 0.1 M) at −78 C was dropwise added MeMgBr (39 µL, 0.4 mmol, 3.5 equiv., 3 M in Et$_2$O). The reaction mixture was allowed to slowly warm to rt, stirred for 30 min at rt, and quenched with 1 M HCl (0.1 mL). The crude product was diluted in acetonitrile/water/trifluoroacetic acid (1.5 mL; 5:1:0.2), filtered through an acrodisc, and purified directly by RP-HPLC (0.1% TFA-ACN in 0.1% TFA Water, Column: Gemini 5 µM, NX-C18 110 Angstrom, 250×21.2 mm) to give the title compound Example 551 as a trifluoroacetate salt.

ES/MS: 511.70 (M$^+$).

$^1$H NMR (400 MHz, DMSO-d$_6$) δ 12.32 (s, 1H), 9.43 (s, 1H), 8.58 (s, 1H), 8.25 (d, J=8.7 Hz, 1H), 7.91-7.81 (m, 2H), 7.72 (d, J=11.1 Hz, 1H), 7.50 (d, J=8.9 Hz, 1H), 7.33 (s, 1H), 3.95 (s, 3H), 1.48 (s, 6H).

Procedure 66: Example 552

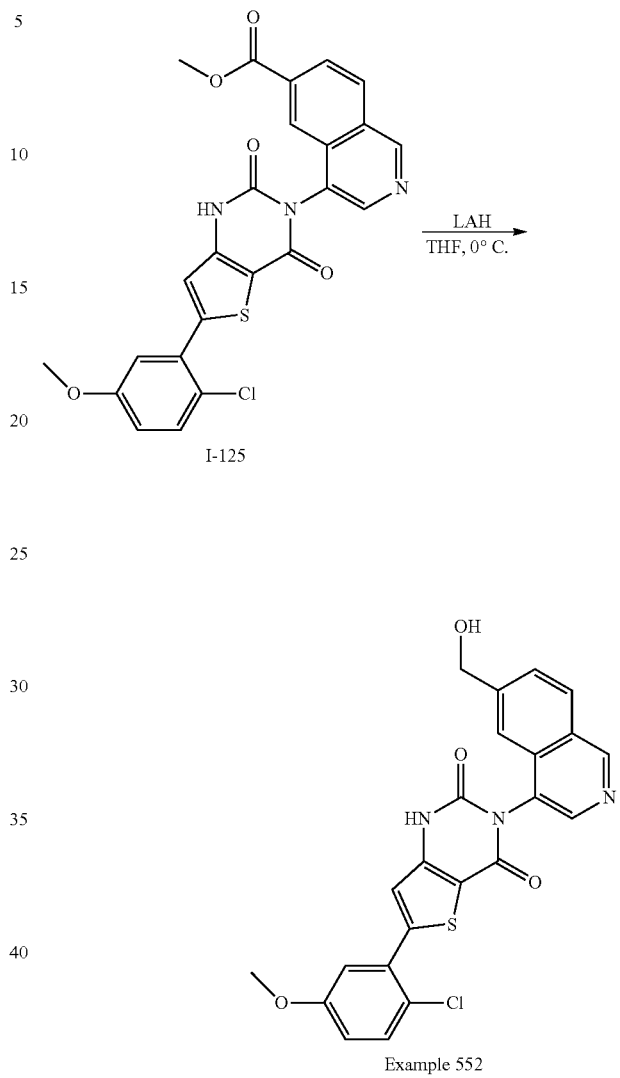

I-125

Example 552

6-(2-chloro-5-methoxyphenyl)-3-(6-(hydroxymethyl)isoquinolin-4-yl)thieno[3,2-d]pyrimidine-2,4(1H,3H)-dione (Example 552): To a stirring solution of methyl 4-[16-(2-chloro-5-methoxy-phenyl)-2,4-dioxo-1H-thieno[3,2-d]pyrimidin-3-yl]isoquinoline-6-carboxylate (I-125) (20.3 mg, 0.033 mmol, 1.0 equiv.) in THF (0.33 mL, 0.1 M) at 0° C. was dropwise added lithium aluminum hydride (5 mg, 0.13 µmol, 4.0 equiv., 2.3 M in Me-THF). The reaction mixture was warmed to rt, stirred for 30 min at rt, and quenched with 1 M HCl (0.1 mL). The crude product was diluted in acetonitrile/water/trifluoroacetic acid (1.5 mL; 5:1:0.2), filtered through an acrodisc, and purified directly by RP-HPLC (0.1% TFA-ACN in 0.1% TFA Water, Column: Gemini 5 µM, NX-C18 110 Angstrom, 250×21.2 mm) to give the title compound Example 552 as a trifluoroacetate salt.

ES/MS: 465.90 (M$^+$).

$^1$H NMR (400 MHz, DMSO-d$_6$) δ 12.30 (s, 1H), 9.44 (s, 1H), 8.59 (s, 1H), 8.27 (d, J=8.3 Hz, 1H), 7.77-7.69 (m, 2H), 7.60 (d, J=8.9 Hz, 1H), 7.34 (s, 1H), 7.27 (d, J=3.0 Hz, 1H), 7.14 (dd, J=8.9, 3.0 Hz, 1H), 4.71 (s, 2H), 3.85 (s, 3H).

Procedure 67: Example 553

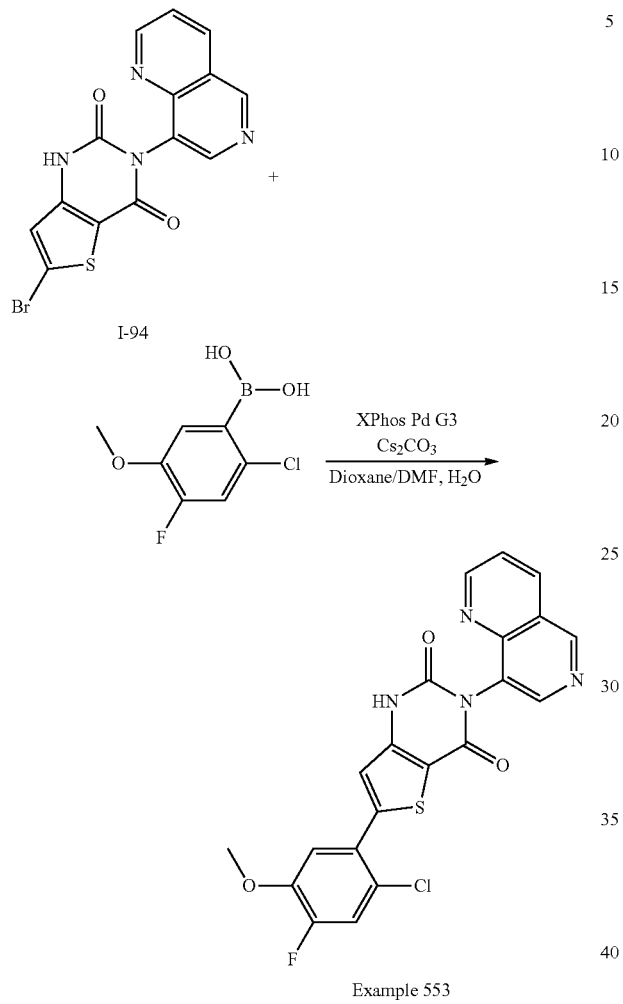

Example 553

6-(2-chloro-4-fluoro-5-methoxy-phenyl)-3-(1,6-naphthyridin-8-yl)-1H-thieno[3,2-d]pyrimidine-2,4-dione (Example 553): To a 10 mL microwave vial (Biotage #351521) containing a stir bar was added 6-bromo-3-(1,6-naphthyridin-8-yl)-1H-thieno[3,2-d]pyrimidine-2,4-dione (I-94) (50 mg, 0.13 mmol, 1.0 equiv.), (2-chloro-4-fluoro-5-methoxy-phenyl)boronic acid (35.4 mg, 0.17 mmol, 1.2 equiv.). XPhos Pd G3 (10.1 mg, 10 mol %), and $Cs_2CO_3$ (130 mg, 0.4 mmol, 3.0 equiv.). Dioxane/DMF (2.5 mL, 1:1) was added followed by $H_2O$ (0.17 mL) after which the reaction mixture was sealed with Teflon, degassed under Ar (5 min), and heated to 120° C. under microwave irradiation for 15 min. The crude product was diluted in acetonitrile/water/trifluoroacetic acid (1.5 mL: 5:1:0.2), filtered through an acrodisc, and purified directly by RP-HPLC (0.1% TFA-ACN in 0.1% TFA Water, Column: Gemini 5 uM, NX-C18 110 Angstrom, 250×21.2 mm) to give the title compound Example 553 as a trifluoroacetate salt.

ES/MS: 454.70 ($M^+$).

$^1$H NMR (400 MHz, DMSO-$d_6$) δ 12.28 (s, 1H), 9.55 (s, 1H), 9.12 (dd, J=4.3, 1.8 Hz, 1H), 8.84 (s, 1H), 8.74 (dd, J=8.3, 1.8 Hz, 1H), 7.80 (dd, J=8.3, 4.3 Hz, 1H), 7.72 (d, J=11.1 Hz, 1H), 7.48 (d, J=8.9 Hz, 1H), 7.31 (s, 1H), 3.95 (s, 3H).

Procedure 68: Example 554 and Example 555

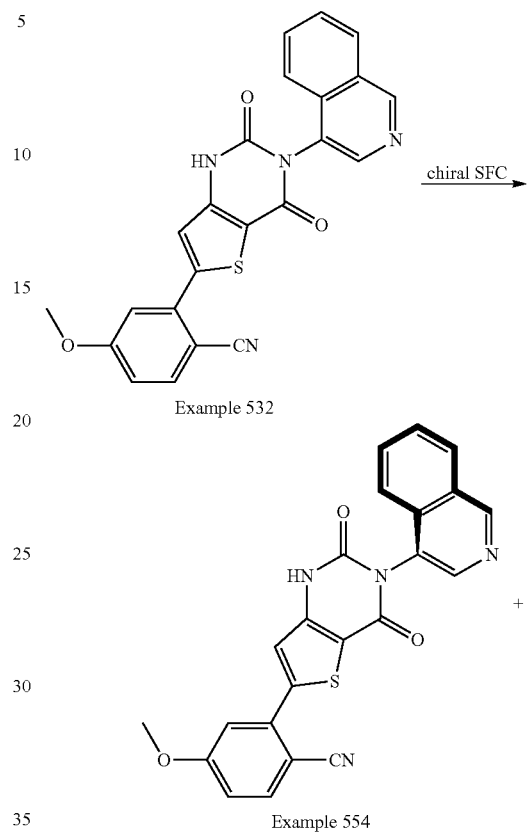

2-(3-(isoquinolin-4-yl)-2,4-dioxo-1,2,3,4-tetrahydrothieno[3,2-d]pyrimidin-6-yl)-4-methoxybenzonitrile (Example 554 and Example 555): 2-(3-(isoquinolin-4-yl)-2,4-dioxo-1,2,3,4-tetrahydrothieno[3,2-d]pyrimidin-6-yl)-4-methoxybenzonitrile (Example 532) as a mixture of 2 atropisomers was separated by chiral SFC (IA 4.6×$^{100}$ mm column with 40% EtOH cosolvent) to give two enantiomers, which were assigned as Isomer 1 and Isomer 2. The stereochemistry was assigned by analogy to Example 438, with Example 554 being the more active isomer.

Isomer 1:

2-(3-(isoquinolin-4-yl)-2,4-dioxo-1,2,3,4-tetrahydrothieno[3,2-d]pyrimidin-6-yl)-4-methoxybenzonitrile (Example 554)

ES/MS: 426.8 (M+H⁺).

$^1$H NMR (400 MHz, DMSO-$d_6$) δ 12.36 (s, 1H), 9.50 (s, 1H), 8.63 (s, 1H), 8.30 (dd, J=7.6, 1.6 Hz, 1H), 8.01 (d, J=8.7 Hz, 1H), 7.95-7.88 (m, 1H), 7.81 (dddd, J=16.5, 8.1, 6.8, 1.4 Hz, 2H), 7.52 (s, 1H), 7.34 (d, J=2.5 Hz, 1H), 7.28 (dd, J=8.8, 2.6 Hz, 1H), 3.95 (s, 3H).

Isomer 2:

2-(3-(isoquinolin-4-yl)-2,4-dioxo-1,2,3,4-tetrahydrothieno[3,2-d]pyrimidin-6-yl)-4-methoxybenzonitrile (Example 555)

ES/MS: 426.8 (M+H⁺).

$^1$H NMR (400 MHz, DMSO-$d_6$) δ 12.36 (s, 1H), 9.50 (s, 1H), 8.63 (s, 1H), 8.30 (dd, J=7.6, 1.6 Hz, 1H), 8.01 (d, J=8.7 Hz, 1H), 7.95-7.88 (m, 1H), 7.81 (dddd, J=16.5, 8.1, 6.8, 1.4 Hz, 2H), 7.52 (s, 1H), 7.34 (d, J=2.5 Hz, 1H), 7.28 (dd, J=8.8, 2.6 Hz, 1H), 3.95 (s, 3H).

Procedure 69: Example 556 and Example 557

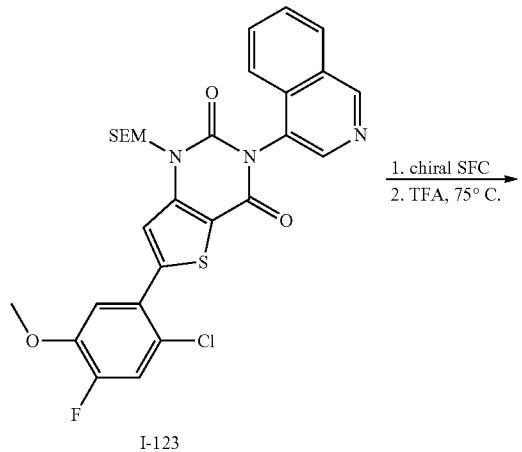

I-123

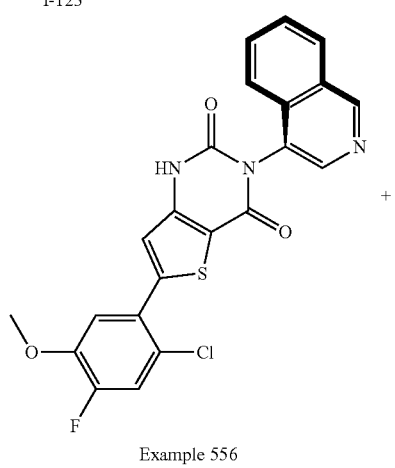

Example 556

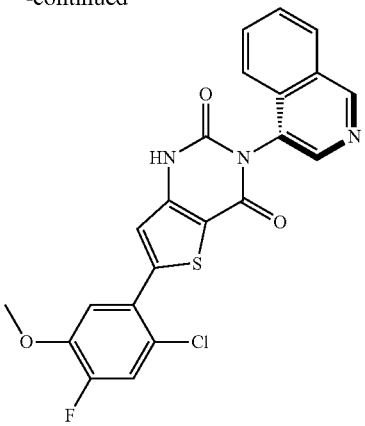

Example 557

6-(2-chloro-4-fluoro-5-methoxyphenyl)-3-(isoquinolin-4-yl)-1-((2-(trimethylsilyl)ethoxy)methyl)thieno[3,2-d]pyrimidine-2,4(1H,3H)-dione (I-123) as a mixture of 2 atropisomers was separated by chiral SFC (IA 4.6×$^{100}$ mm column with 40% EtOH cosolvent) to give two enantiomers, which were assigned as Isomer 1 and Isomer 2. Each isomer was then individually subjected to SEM removal under acidic conditions.

Isomer 1:

6-(2-chloro-4-fluoro-5-methoxyphenyl)-3-(isoquinolin-4-yl)thieno[3,2-d]pyrimidine-2,4(1H,3H)-dione (Example 556): To a 20 mL scintillation vial containing a stir bar was added 6-(2-chloro-4-fluoro-5-methoxyphenyl)-3-(isoquinolin-4-yl)-1-((2-(trimethylsilyl)ethoxy)methyl)thieno[3,2-d]pyrimidine-2,4(1H,3H)-dione (Isomer 1) (115 mg, 0.033 mmol, 1.0 equiv.), and TFA (2.5 mL), followed by 0.2 mL of H₂O. The reaction mixture was heated to 65° C. and stirred overnight after which the reaction mixture was cooled to rt and concentrated under reduced pressure. The crude product was dissolved in DMSO/trifluoroacetic acid (4.0 mL: 4:1), filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 556 as a trifluoroacetate salt. The stereochemistry of Example 556 was assigned by analogy to Example 438, with Example 556 being the more active isomer.

ES/MS: 426.8 (M⁺).

$^1$H NMR (400 MHz, DMSO-$d_6$) δ 12.36 (s, 1H), 9.50 (s, 1H), 8.63 (s, 1H), 8.30 (dd, J=7.6, 1.6 Hz, 1H), 8.01 (d, J=8.7 Hz, 1H), 7.95-7.88 (m, 1H), 7.81 (dddd, J=16.5, 8.1, 6.8, 1.4 Hz, 2H), 7.52 (s, 1H), 7.34 (d, J=2.5 Hz, 1H), 7.28 (dd, J=8.8, 2.6 Hz, 1H), 3.95 (s, 3H).

Isomer 2:

6-(2-chloro-4-fluoro-5-methoxyphenyl)-3-(isoquinolin-4-yl)thieno[3,2-d]pyrimidin-2,4(1H,3H)-dione (Example 557): To a 20 mL scintillation vial containing a stir bar was added 6-(2-chloro-4-fluoro-5-methoxyphenyl)-3-(isoquinolin-4-yl)-1-((2-(trimethylsilyl)ethoxy)methyl)thieno[3,2-d]pyrimidine-2,4(1H,3H)-dione (Isomer 2) (115 mg, 0.033 mmol, 1.0 equiv.), and TFA (2.5 mL), followed by 0.2 mL of H₂O. The reaction mixture was heated to 65° C. and stirred overnight after which the reaction mixture was cooled and concentrated under reduced pressure. The crude product was dissolved in DMSO/trifluoroacetic acid (4.0 mL: 4:1), filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 557 as a trifluoroacetate salt. The stereochemistry of Example 557 was assigned by analogy to Example 438, with Example 557 being the less active isomer.

ES/MS: 426.8 (M+).

$^{1}$H NMR (400 MHz, DMSO-d$_{6}$) δ 12.36 (s, 1H), 9.50 (s, 1H), 8.63 (s, 1H), 8.30 (dd, J=7.6, 1.6 Hz, 1H), 8.01 (d, J=8.7 Hz, 1H), 7.95-7.88 (m, 1H), 7.81 (dddd, J=16.5, 8.1, 6.8, 1.4 Hz, 2H), 7.52 (s, 1H), 7.34 (d, J=2.5 Hz, 1H), 7.28 (dd, J=8.8, 2.6 Hz, 1H), 3.95 (s, 3H).

Procedure 70: Example 558

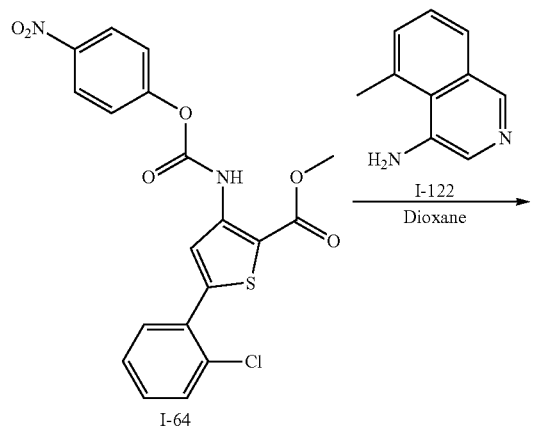

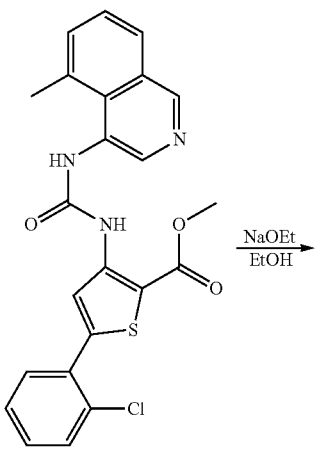

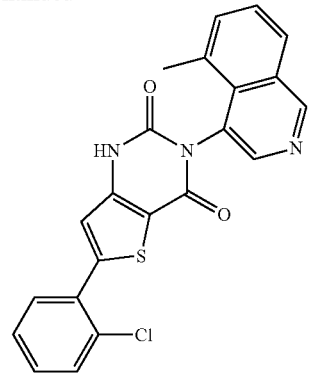

Example 558

5-(2-chlorophenyl)-3-(3-(5-methylisoquinolin-4-yl) ureido)thiophene-2-carboxylate: To a stirring solution of methyl 5-(2-chlorophenyl)-3-(((4-nitrophenoxy)carbonyl) amino)thiophene-2-carboxylate (I-64) (65.0 mg, 0.15 mmol, 1.0 equiv.) in dioxanes (0.48 mL, 0.30 M) was added 5-methylisoquinolin-4-amine (I-122) (28.5 mg, 0.18 mmol, 1.2 equiv.). The reaction mixture was heated to 95° C. and stirred overnight. The reaction mixture was cooled to rt and concentrated under reduced pressure to deliver intermediate methyl 5-(2-chlorophenyl)-3-(3-(5-methylisoquinolin-4-yl) ureido)thiophene-2-carboxylate which was used to the next step without further purification. ES/MS: 452.8 (M+).

6-(2-chlorophenyl)-3-(5-methylisoquinolin-4-yl)thieno [3,2-d]pyrimidine-2,4(1H,3H)-dione (Example 558): To a suspension of 5-(2-chlorophenyl)-3-(3-(5-methylisoquinolin-4-yl)ureido)thiophene-2-carboxylate (67.8 mg, 0.15 mmol, 1.0 equiv.) in ethanol (0.5 mL, 0.32 M) was added a solution of 25% sodium ethoxide (71 μL, 0.23 mmol, 1.5 equiv.) and the reaction mixture stirred at room temperature for 2 h. The reaction mixture was concentrated under reduced pressure after which the crude product was dissolved in DMSO/trifluoroacetic acid (4.0 mL; 4:1), filtered through an acrodisc, and purified directly by RP-HPLC (0.1% TFA-ACN in 0.1% TFA Water, Column: Gemini 5 PM, NX-C18 110 Angstrom, 250×21.2 mm) to give the title compound Example 558 as a trifluoroacetate salt.

ES/MS: 419.8 (M+).

$^{1}$H NMR (400 MHz, DMSO-d$_{6}$) δ 12.39 (s, 1H), 9.44 (s, 1H), 8.53 (s, 1H), 8.23-8.14 (m, 1H), 7.84-7.73 (m, 1H), 7.75-7.62 (m, 3H), 7.60-7.48 (m, 2H), 7.34 (s, 1H), 2.44 (s, 3H).

Examples 559-560

The following Examples were made in an analogous fashion according to Procedure 70 and are shown below in Table 31. Any different reagents/starting materials than those described in Procedure 70 are noted in the last column of Table 31—"Changes to Procedure 70: Different Reagents/Starting Materials".

TABLE 31

Examples 559-560

| Example | Structure | ES/MS m/z | 1H-NMR | Changes to Procedure 70: Different Reagents/Starting Materials |
|---|---|---|---|---|
| 559 | 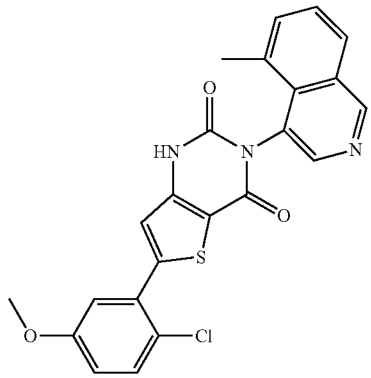 [SMILES: COc1ccc(Cl)c(-c2cc3[nH]c(=O)n(-c4cncc5cccc(C)c45)c(=O)c3s2)c1] | 449.7 | 1H NMR (400 MHz, DMSO-d6) δ 12.38 (s, 1H), 9.43 (s, 1H), 8.52 (s, 1H), 8.17 (dd, J = 7.4, 2.2 Hz, 1H), 7.72-7.62 (m, 2H), 7.59 (d, J = 8.9 Hz, 1H), 7.36-7.26 (m, 2H), 7.13 (dd, J = 8.9, 3.0 Hz, 1H), 3.85 (s, 3H), 2.44 (s, 3H). | I-65 |
| 560 | 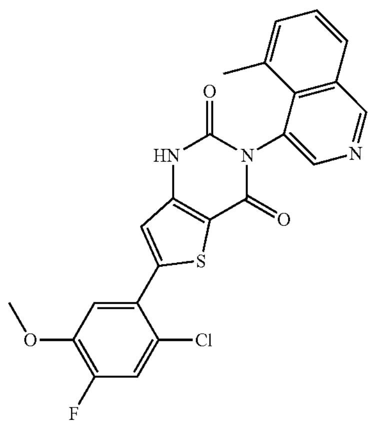 [SMILES: COc1cc(-c2cc3[nH]c(=O)n(-c4cncc5cccc(C)c45)c(=O)c3s2)c(Cl)cc1F] | 467.7 | 1H NMR (400 MHz, DMSO-d6) δ 12.40 (s, 1H), 9.43 (s, 1H), 8.52 (s, 1H), 8.17 (dd, J = 7.4, 2.1 Hz, 1H), 7.75-7.61 (m, 3H), 7.50 (d, J = 8.9 Hz, 1H), 7.32 (s, 1H), 3.95 (s, 3H), 2.43 (s, 3H). | I-66 |

Procedure 71: Example 561

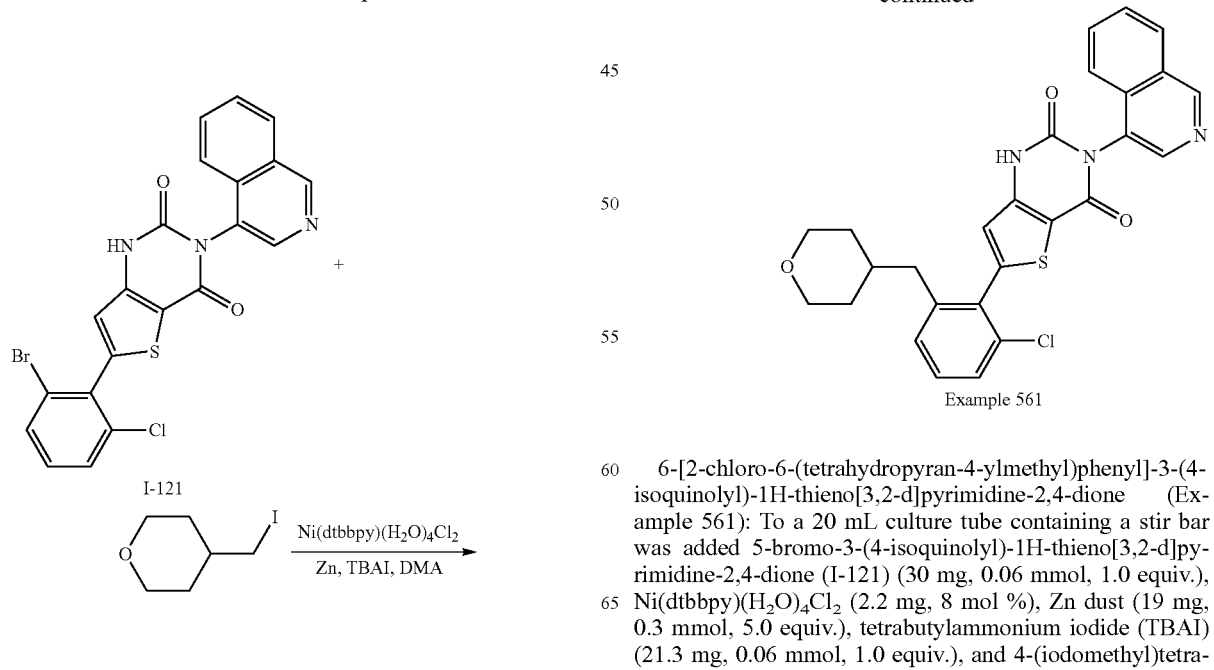

Example 561

6-[2-chloro-6-(tetrahydropyran-4-ylmethyl)phenyl]-3-(4-isoquinolyl)-1H-thieno[3,2-d]pyrimidine-2,4-dione (Example 561): To a 20 mL culture tube containing a stir bar was added 5-bromo-3-(4-isoquinolyl)-1H-thieno[3,2-d]pyrimidine-2,4-dione (I-121) (30 mg, 0.06 mmol, 1.0 equiv.), Ni(dtbbpy)(H$_2$O)$_4$Cl$_2$ (2.2 mg, 8 mol %), Zn dust (19 mg, 0.3 mmol, 5.0 equiv.), tetrabutylammonium iodide (TBAI) (21.3 mg, 0.06 mmol, 1.0 equiv.), and 4-(iodomethyl)tetrahydropyran (20 mg, 0.09 mmol, 1.5 equiv.) followed by DMA (1.0 mL, 0.05 M). The reaction mixture was sealed with Teflon, degassed under Ar (5 min), and heated to 70° C. for 4 h. The reaction mixture was cooled to rt and concentrated under reduced pressure. The crude product was diluted in acetonitrile/water/trifluoroacetic acid (1.5 mL; 5:1:0.2), filtered through an acrodisc, and purified directly by RP-HPLC (0.1% TFA-ACN in 0.1% TFA Water) to give the title compound Example 561 as a trifluoroacetate salt.

ES/MS: 504.10 (M+).

$^1$H NMR (400 MHz, DMSO-$d_6$) δ 12.28 (s, 1H), 9.46 (s, 1H), 8.63 (s, 1H), 8.30 (d, J=8.0 Hz, 1H), 7.92 (d, J=8.3 Hz, 1H), 7.82 (dt, J=22.5, 6.9 Hz, 2H), 7.53-7.48 (m, 2H), 7.41 (dd, J=6.3, 2.7 Hz, 1H), 6.97 (s, 1H), 3.83-3.79 (m, 4H), 3.28-3.17 (m, 2H), 1.84-1.70 (m, 1H), 1.57 (s, 1H), 1.48-1.38 (m, 2H), 1.32 (s, 1H), 1.17 (q, J=9.9, 9. Hz, 8H), 0.94 (t, J=7.3 Hz, 1H).

Procedure 72: Example 562

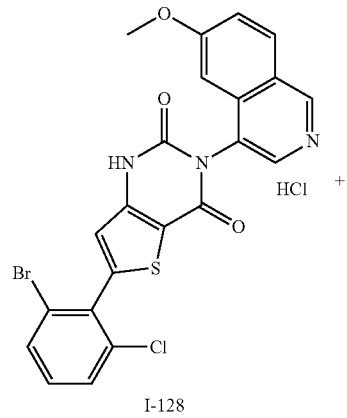

I-128

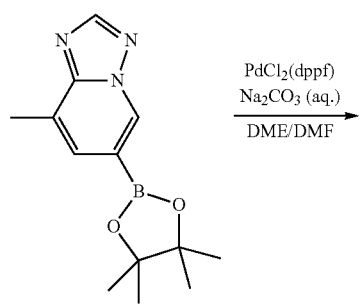

PdCl$_2$(dppf)
Na$_2$CO$_3$ (aq.)
―――――――→
DME/DMF

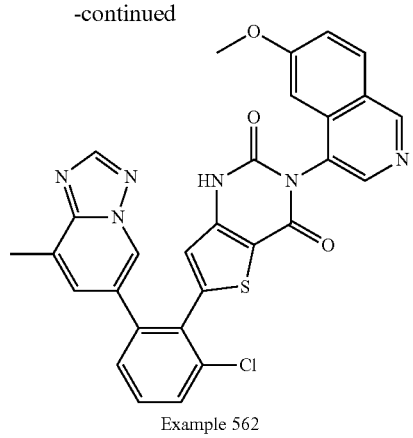

Example 562

6-[2-chloro-6-(8-methyl-[1,2,4]triazolo[1,5-a]pyridin-6-yl)phenyl]-3-(6-methoxy-4-isoquinolyl)-1H-thieno[3,2-d]pyrimidine-2,4-dione (Example 562): To a 10 mL microwave vial (Biotage #351521) containing a stir bar was added 6-(2-bromo-6-chloro-phenyl)-3-(4-isoquinolyl)-1H-thieno[3,2-d]pyrimidine-2,4-dione;hydrochloride (1-128) (30 mg, 0.054 mmol, 1.0 equiv.), 8-methyl-6-(4,4,5,5-tetramethyl-1,3,2-dioxaborolan-2-yl)-[1,2,4]triazolo[1,5-a]pyridine (21.2 mg, 0.82 mmol, 1.4 equiv.), and PdCl$_2$(dppf) (6.0 mg, 15 mol %) followed by 1:5 DMF/DME (0.6 mL, 0.06 M). Na$_2$CO$_3$ was added (0.05 mL, 2 N solution) after which the reaction mixture was sealed with Teflon, degassed under Ar (5 min), and heated to 100° C. under microwave irradiation for 15 min. The crude product was diluted in acetonitrile/water/trifluoroacetic acid (1.5 mL: 5:1:0.2), filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 562 as a trifluoroacetate salt.

ES/MS: 567.10 (M+).

$^1$H NMR (400 MHz, Methanol-$d_4$) δ 9.57 (s, 1H), 8.69-8.62 (m, 2H), 8.49-8.41 (m, 2H), 7.76 (dd, J=8.1, 1.3 Hz, 1H), 7.70-7.61 (M, 2H), 7.58 (dd, J=7.7, 1.3 Hz, 1H), 7.53-7.48 (m, 1H), 7.32 (d, J=2.3 Hz, 1H), 7.08 (s, 1H), 4.01 (s, 3H), 2.61 (t, J=0.9 Hz, 3H).

Examples 563-564

The following Examples were made in an analogous fashion according to Procedure 72 and are shown below in Table 32. Any different reagents/starting materials than those described in Procedure 72 are noted in the last column of Table 32—"Changes to Procedure 72: Different Reagents/Starting Materials".

TABLE 32
Examples 563-564
| Example | Structure | ES/MS m/z | 1H-NMR | Changes to Procedure 72: Different Reagents/Starting Materials |
|---|---|---|---|---|
| 563 | 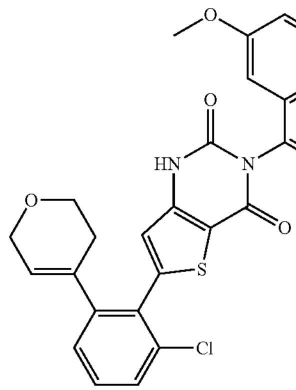 | 518.1 | 1H NMR (400 MHz, Methanol-d4) δ 9.56 (s, 1H), 8.71 (s, 1H), 8.45 (d, J = 9.2 Hz, 1H), 7.64 (d, J = 8.7 Hz, 1H), 7.60-7.53 (m, 1H), 7.49 (t, J = 7.8 Hz, 1H), 7.38-7.31 (m, 2H), 7.06 (s, 1H), 5.78 (s, 1H), 4.19 (d, J = 3.0 Hz, 2H), 4.05 (s, 3H), 3.76 (t, J = 5.3 Hz, 2H), 2.17 (s, 2H). | 2-(3,6-dihydro-2H-pyran-4-yl)-4,4,5,5-tetramethyl-1,3,2-dioxaborolane |
| 564 | 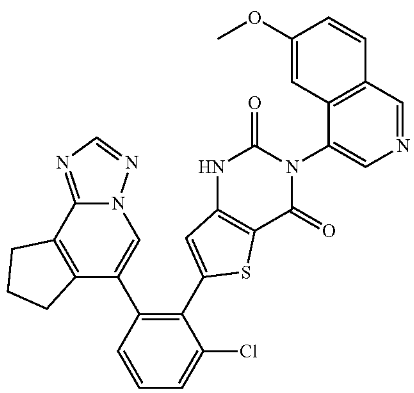 [SMILES: COc1ccc2cncc(-n3c(=O)[nH]c4cc(-c5c(Cl)cccc5-c5cn6ncnc6c6c5CCC6)sc4c3=O)c2c1] | 593.2 | 1H NMR (400 MHz, Methanol-d4) δ 9.57 (s, 1H), 8.62 (d, J = 5.3 Hz, 2H), 8.49-8.39 (m, 2H), 7.78 (dd, J = 8.1, 1.2 Hz, 1H), 7.70-7.60 (m, 2H), 7.51 (dd, J = 7.6, 1.2 Hz, 1H), 7.34 (d, J = 2.3 Hz, 1H), 7.06 (s, 1H), 3.99 (s, 3H), 3.26 (t, J = 7.6 Hz, 2H), 2.91 (s, 2H), 2.34-2.25 (m, 2H). | I-169 |
Procedure 73: Example 565
-continued
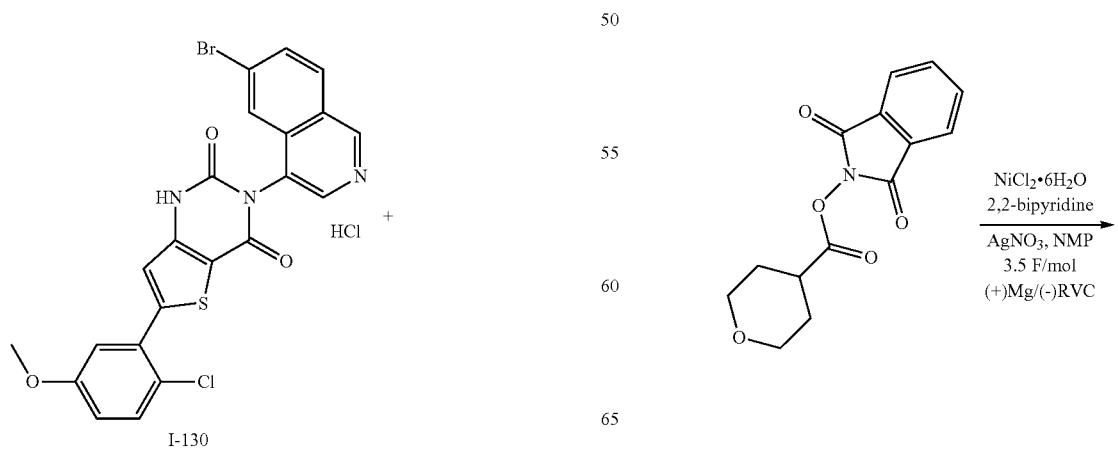

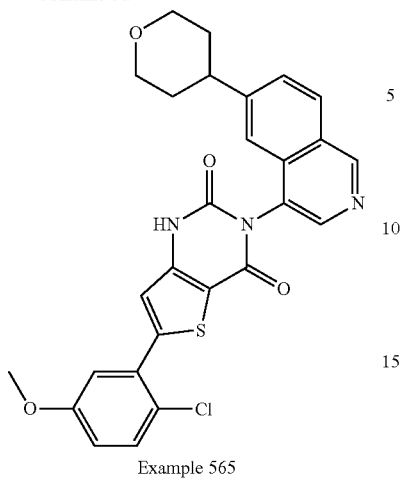

Example 565

6-[2-chloro-6-(8-methyl-[1,2,4]triazolo[1,5-a]pyridin-6-yl)phenyl]-3-(6-methoxy-4-isoquinolyl)-1H-thieno[3,2-d]pyrimidine-2,4-dione (Example 565): To an oven dried 20 mL ElectraSyn 2.0 vial was added (1,3-dioxoisoindolin-2-yl) tetrahydropyran-4-carboxylate (28 mg, 0.1 mmol, 1.0 equiv.), 3-(6-bromo-4-isoquinolyl)-6-(2-chloro-5-methoxyphenyl)-1H-thieno[3,2-d]pyrimidine-2,4-dione (HCl salt) (I-130) (62 mg, 0.12 mmol, 1.2 equiv.), $NiCl_2 \cdot 6H_2O$ (4.75 mg, 20 mol %), and 2,2'-bipyridine (3.1 mg, 20 mol %). NMP (0.75 mL) was then added followed by $AgNO_3$ (8.5 mg, 0.05 mmol, 0.5 equiv.). The vial was equipped with an ElectraSyn 2.0 vial cap with a magnesium sacrificial anode and a cylindrical RVC cathode. The entire vial was subsequently electrolyzed via an IKA ElectraSyn 2.0 stir plate and electrolysis was set to: 12 mA, 3.5 F/mol. After 2 hours, the crude product was diluted in acetonitrile/water/trifluoroacetic acid (1.5 mL: 5:1:0.2), filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 565 as a trifluoroacetate salt.

ES/MS: 519.70 (M+).

$^1$H NMR (400 MHz, DMSO-$d_6$) δ 12.24 (s, 1H), 9.41 (s, 1H), 8.54 (s, 1H), 8.25 (d, J=8.5 Hz, 1H), 7.80-7.72 (m, 2H), 7.60 (d, J=8.9 Hz, 1H), 7.35 (s, 1H), 7.25 (d, J=3.0 Hz, 1H), 7.14 (dd, J=8.9, 3.1 Hz, 1H), 3.96 (dd, J=11.3, 4.1 Hz, 2H), 3.86 (s, 3H), 3.45 (d, J=11.1 Hz, 2H), 3.05 (t, J=12.0 Hz, 1H), 1.82 (d, J=12.1 Hz, 2H), 1.68 (d, J=12.8 Hz, 2H).

Procedure 74: Example 566

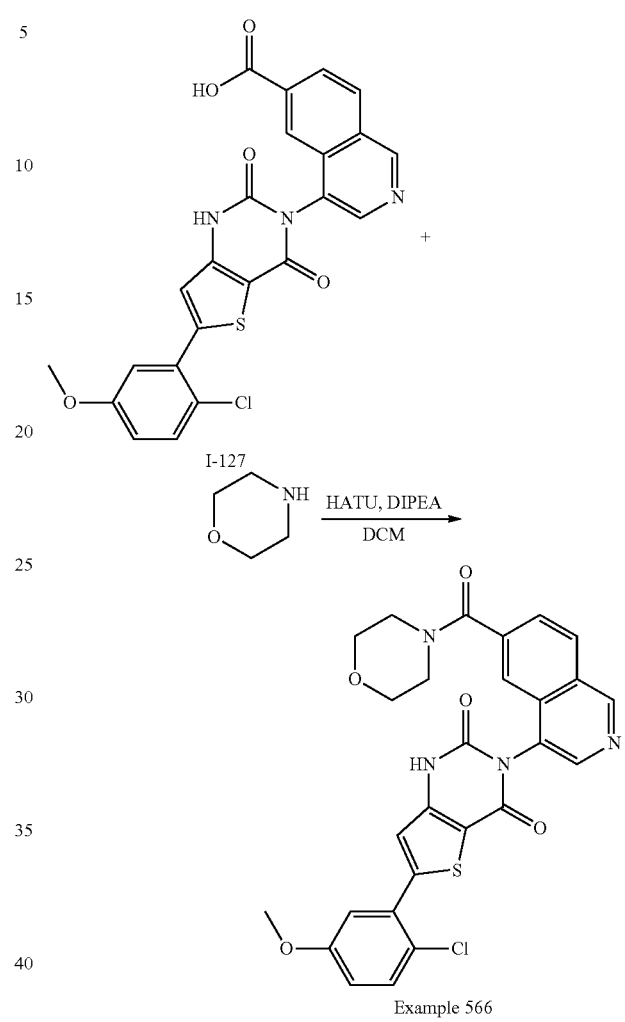

Example 566

6-(2-chloro-5-methoxy-phenyl)-3-[6-(morpholine-4-carbonyl)-4-isoquinolyl]-1H-thieno[3,2-d]pyrimidine-2,4-dione (Example 566): To a stirring solution of 4-[6-(2-chloro-5-methoxy-phenyl)-2,4-dioxo-1H-thieno[3,2-d]pyrimidin-3-yl]isoquinoline-6-carboxylic acid (HCl salt) (1-127) (20 mg, 0.038 mmol, 1.0 equiv.) in DCM (0.5 mL, 0.08 M) was added DIPEA (10 uL, 0.058 mmol, 1.5 equiv.), and morpholine (5 uL, 0.05 mmol, 1.5 equiv.) followed by HATU (18 mg, 0.047 mmol, 1.2 equiv.). The reaction mixture stirred at rt for 2 h after which the entire reaction mixture was diluted in acetonitrile/water/trifluoroacetic acid (0.5 mL; 5:1:0.2), filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 566 as a trifluoroacetate salt.

ES/MS: 548.7 (M+).

$^1$H NMR (400 MHz, DMSO-$d_6$) δ 12.27 (s, 1H), 9.49 (s, 1H), 8.63 (s, 1H), 8.36 (d, J=8.4 Hz, 1H), 8.00 (s, 1H), 7.75 (dd, J=8.4, 1.5 Hz, 1H), 7.60 (d, J=8.9 Hz, 1H), 7.34 (s, 1H), 7.24 (d, J=3.0 Hz, 1H), 7.14 (dd, J=8.9, 3.1 Hz, 1H), 3.85 (s, 3H), 3.70-3.54 (m, 6H), 3.26 (s, 2H).

Procedure 75: Preparation of Example 567

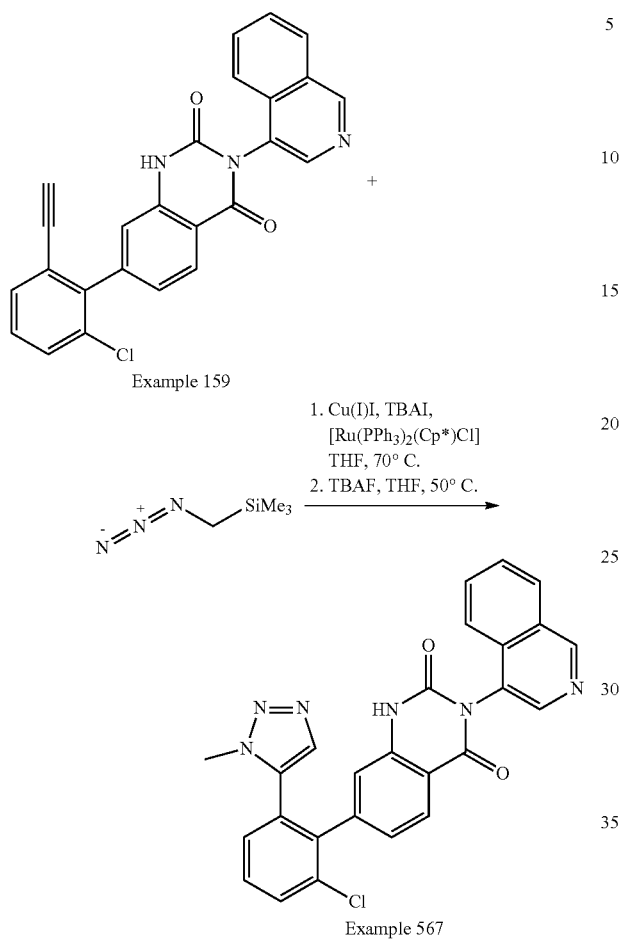

7-[2-chloro-6-(3-methyltriazol-4-yl)phenyl]-3-(4-isoquinolyl)-1H-quinazoline-2,4-dione (Example 567): A suspension of cuprous iodide (90 mg, 0.48 mmol) and tetra-n-butylammonium iodide (174 mg, 0.48 mmol) in THF (1 mL) was stirred under argon until homogeneous (~10 min). To the stirred mixture was added 7-(2-chloro-6-ethynyl-phenyl)-3-(4-isoquinolyl)-1H-quinazoline-2,4-dione (100 mg, 0.24 mmol) in THF (3 mL) followed by azidomethyl(trimethyl)silane (53 μL). The mixture was degassed for 10 min with argon and then [Ru(PPh3)2(Cp*)Cl](18 mg, 0.024 mmol) was added. The mixture was immediately moved to stir in a 70° C. heating block for 2 hours. Reaction mixture was cooled down to room temperature, filtered with the aide of celite and concentrated. The crude product was dissolved in THF (2 mL) and TBAF 1M solution in THF (0.2 mL) was added and the resulting mixture was stirred at 50° C. overnight. The crude product was pre-purified by flash chromatography to remove the tert-butyl residue. The product obtained was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the title compound.

ES/MS: 481.1 (M+).

$^1$H NMR (400 MHz, DMSO) δ 11.77 (d, J=1.6 Hz, 1H), 9.46 (s, 1H), 8.62 (d, J=15.1 Hz, 1H), 8.29 (dd, J=7.6, 1.7 Hz, 1H), 7.97-7.73 (m, 5H), 7.71-7.56 (m, 2H), 7.45 (d, J=13.7 Hz, 1H), 7.17-7.01 (m, 2H), 3.85 (d, J=5.7 Hz, 3H).

Procedure 76: Preparation of Example 568

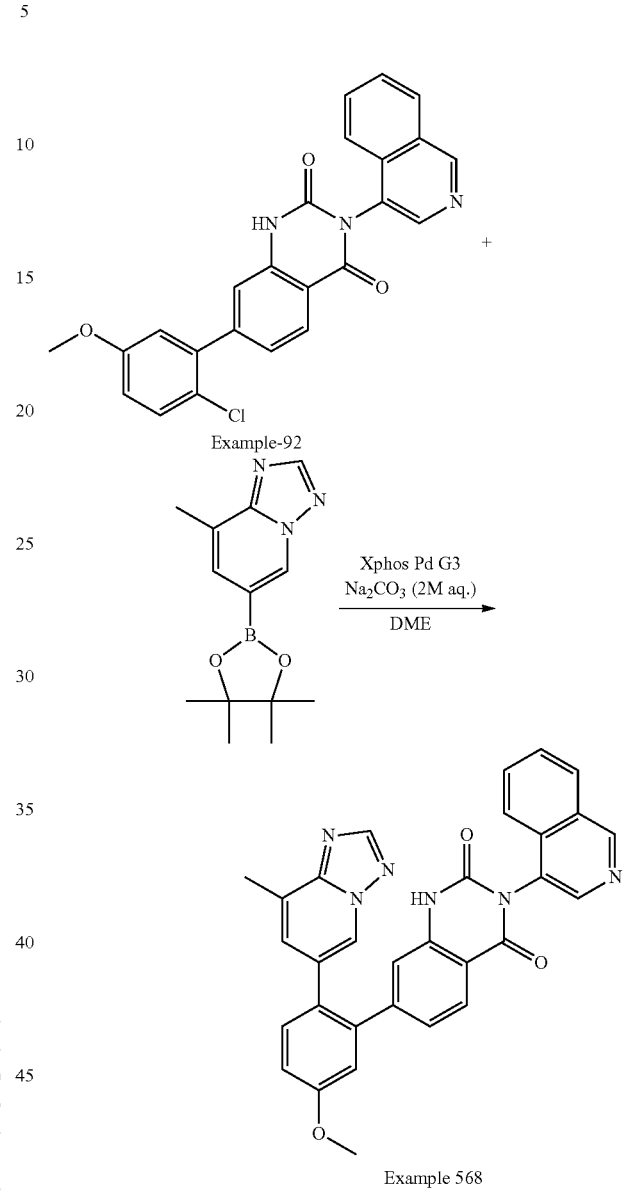

3-(4-isoquinolyl)-7-[5-methoxy-2-(8-methyl-[1,2,4]triazolo[1,5-a]pyridin-6-yl)phenyl]-1H-quinazoline-2,4-dione (Example 568): To 10 mL vial with 7-(2-chloro-5-methoxyphenyl)-3-(4-isoquinolyl)-1H-quinazoline-2,4-dione (Example-92) (90 mg, 0.21 mmol) was added 8-methyl-6-(4,4,5,5-tetramethyl-1,3,2-dioxaborolan-2-yl)-[1,2,4]triazolo[1,5-a]pyridine (81 mg, 0.32 mmol), XPhos Pd G3 (20 mg, 0.027 mmol), sodium carbonate (2 M aqueous, 0.25 mL, 0.50 mmol) and dioxane (1.0 mL). The mixture was degassed with argon for 30 seconds. The vial was sealed, and the reaction mixture was heated at 140° C. for 20 minutes. The crude mixture was filtered, concentrated under reduced pressure, and to the crude residue was added acetonitrile (0.5 mL), TFA (0.3 mL) and water (0.2 mL) and was subsequently purified by RP-HPLC (0.1% TFA-ACN in 0.1% TFA Water, Column: Gemini 5 uM, NX-C18 110 Angstrom, 250×21.2 mm) to give the title compound.

ES/MS: 527.2 (M+H⁺).

¹H NMR (400 MHz, DMSO) δ 11.72 (s, 1H), 9.54 (s, 1H), 8.66-8.60 (m, 2H), 8.47 (s, 1H), 8.34 (dd, J=7.5, 1.4 Hz, 1H), 7.92-7.77 (m, 4H), 7.55 (d, J=8.5 Hz, 1H), 7.24 (t, J=1.4 Hz, 1H), 7.22-7.12 (m, 3H), 7.06 (d, J=2.7 Hz, 1H), 3.90 (s, 3H), 2.48 (s, 3H).

Procedure 77: Preparation of Example 569 and Example 570

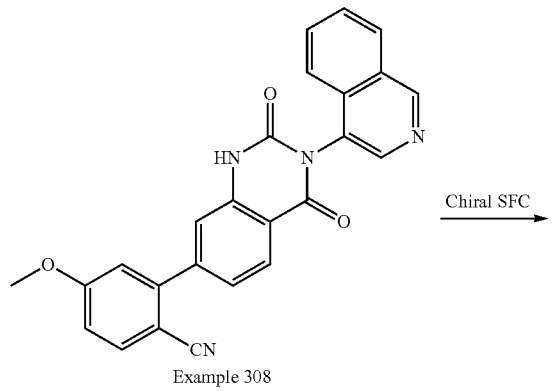

Example 308

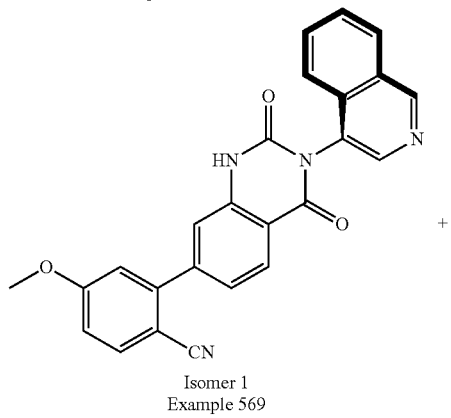

Isomer 1
Example 569

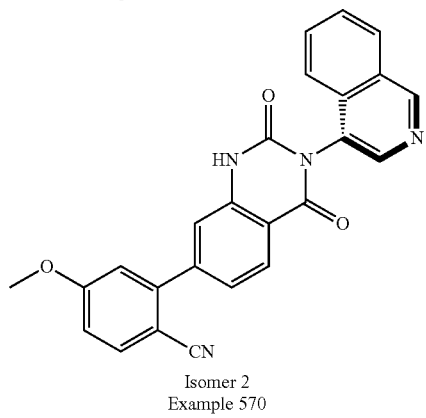

Isomer 2
Example 570

2-[3-(4-isoquinolyl)-2,4-dioxo-1H-quinazolin-7-yl]-4-methoxy-benzonitrile (Example 569 and Example 570): 2-[3-(4-isoquinolyl)-2,4-dioxo-1H-quinazolin-7-yl]-4-methoxy-benzonitrile (Example 308) as a mixture of 2 atropisomers was separated by chiral SFC (IB 5 um-4.6x100 mm column with 35% MeOH co-solvent) to give two enantiomers, which were assigned as Isomer 1 and Isomer 2. The stereochemistry was assigned by analogy to Example 438, with Example 569 being the more active isomer.

Isomer 1:

2-[3-(4-isoquinolyl)-2,4-dioxo-1H-quinazolin-7-yl]-4-methoxy-benzonitrile

Example 569

ES/MS: 420.8 (M⁺).

1H NMR (400 MHz, DMSO) δ 11.97 (s, 1H), 9.52 (s, 1H), 8.65 (s, 1H), 8.37-8.28 (m, 1H), 8.14-8.07 (m, 1H), 7.98 (dd, J=8.3, 2.7 Hz, 2H), 7.89-7.77 (m, 2H), 7.50-7.43 (m, 2H), 7.29-7.17 (m, 2H), 3.94 (s, 3H).

Isomer 2:

2-[3-(4-isoquinolyl)-2,4-dioxo-1H-quinazolin-7-yl]-4-methoxy-benzonitrile

Example 570

ES/MS: 420.8 (M+).

1H NMR (400 MHz, DMSO) δ 11.96 (s, 1H), 9.51 (s, 1H), 8.64 (s, 1H), 8.36-8.29 (m, 1H), 8.14-8.07 (m, 1H), 7.98 (dd, J=8.9, 6.7 Hz, 2H), 7.88-7.76 (m, 2H), 7.47 (d, J=7.2 Hz, 2H), 7.25 (dd, J=8.7, 2.6 Hz, 1H), 7.20 (d, J=2.6 Hz, 1H), 3.93 (s, 3H).

Procedure 78: Preparation of Example 571 and Example 572

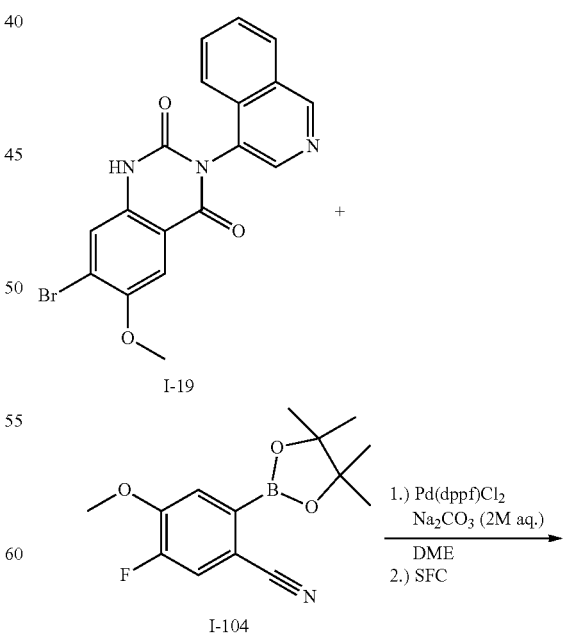

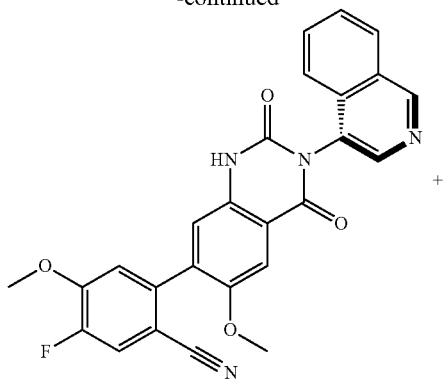

Isomer 1
Example 571

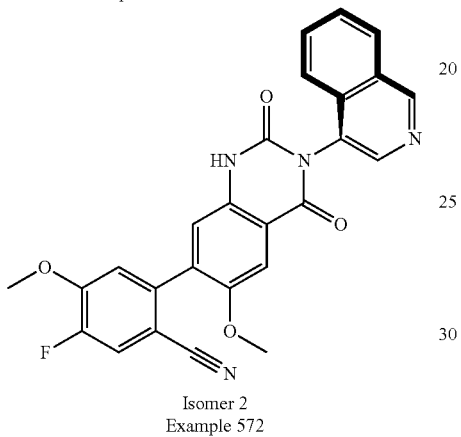

Isomer 2
Example 572

5-fluoro-2-[13-(4-isoquinolyl)-6-methoxy-2,4-dioxo-1H-quinazolin-7-yl]-4-methoxy-benzonitrile (Example 571 and Example 572): To a 10 mL vial was added 7-bromo-3-(4-isoquinolyl)-6-methoxy-1H-quinazoline-2,4-dione (I-19) (100 mg, 0.25 mmol), 5-fluoro-4-methoxy-2-(4,4,5,5-tetramethyl-1,3,2-dioxaborolan-2-yl)benzonitrile (1-104) (84 mg, 0.30 mmol), and Pd(dppf)Cl$_2$ (19 mg, 0.025 mmol). DME (1 mL) and sodium carbonate (2 M aqueous, 0.25 mL, 0.50 mmol), and the mixture was degassed with argon for 30 seconds. The vial was sealed, and the reaction mixture was heated at 120° C. for 20 minutes in a microwave. The mixture was filtered and concentrated under reduced pressure and to the crude residue was added DMF (1 mL), acetonitrile (0.5 mL), TFA (0.3 mL) and water (0.2 mL). The mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to obtain the product Example 324. The product as a mixture of 2 atropisomers was separated by chiral SFC (IB Sum-4.6×$^{100}$ mm column with 35% MeOH cosolvent) to give two enantiomers, which were assigned as Isomer 1 and Isomer 2. The stereochemistry was assigned by analogy to Example 438, with Example 572 being the more active isomer.

Isomer 1:

5-fluoro-2-[3-(4-isoquinolyl)-6-methoxy-2,4-dioxo-1H-quinazolin-7-yl]-4-methoxy-benzonitrile (Example 571)

ES/MS: 468.8 (M$^+$).

$^1$H NMR (400 MHz, DMSO) δ 11.82 (s, 1H), 9.50 (s, 1H), 8.63 (s, 1H), 8.36-8.29 (m, 1H), 8.00 (d, J=11.2 Hz, 1H), 7.92-7.76 (m, 3H), 7.59 (s, 1H), 7.37 (d, J=8.3 Hz, 1H), 7.25 (s, 1H), 3.98 (s, 3H), 3.84 (s, 3H).

Isomer 2:

5-fluoro-2-[3-(4-isoquinolyl)-6-methoxy-2,4-dioxo-1H-quinazolin-7-yl]-4-methoxy-benzonitrile (Example 572)

ES/MS: 468.7 (M$^+$).

$^1$H NMR (400 MHz, DMSO) δ 11.82 (s, 1H), 9.50 (s, 1H), 8.63 (s, 1H), 8.36-8.29 (m, 1H), 8.00 (d, J=11.2 Hz, 1H), 7.92-7.76 (m, 3H), 7.59 (s, 1H), 7.37 (d, J=8.2 Hz, 1H), 7.25 (s, 1H), 3.98 (s, 3H), 3.84 (s, 3H).

Procedure 79: Preparation of Example 573

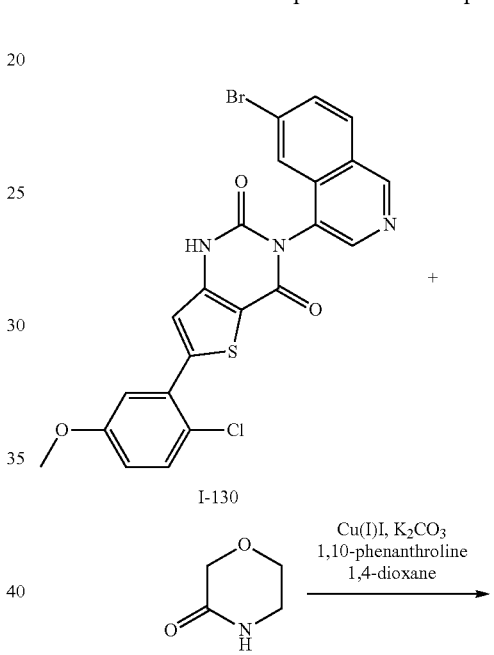

I-130

Cu(I)I, K$_2$CO$_3$
1,10-phenanthroline
1,4-dioxane

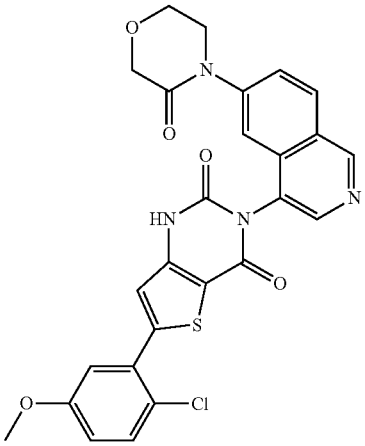

Example 573

6-(2-chloro-5-methoxyphenyl)-3-(6-(3-oxomorpholino) isoquinolin-4-yl)thieno[3,2-d]pyrimidine-2,4(1H,3H)-dione (Example 573): To a solution of 3-(6-bromoisoquinolin-4-yl)-6-(2-chloro-5-methoxyphenyl)thieno[3,2-d]pyrimidine-2,4(1H,3H)-dione (I-130) (50 mg, 0.097 mmol), morpholin-3-one (12 mg, 0.12 mmol), and 1,10-phenanthroline (3.5 mg, 0.19 mmol) in 1,4-dioxane (1 mL), potassium carbonate (27 mg, 0.19 mmol) and copper iodide (7.4 mg, 0.39 mmol) were added and degassed with argon for 1 minute. The mixture was stirred at 130° C. overnight. The reaction mixture was cooled to ambient temperature, filtered and concentrated. The mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the product.

ES/MS: 534.8 (M$^+$).

$^1$H NMR (400 MHz, DMSO) δ 12.23 (s, 1H), 9.43 (s, 1H), 8.57 (s, 1H), 8.30 (d, J=8.9 Hz, 1H), 7.98 (d, J=1.9 Hz, 1H), 7.82 (dd, J=8.8, 2.0 Hz, 1H), 7.60 (d, J=8.9 Hz, 1H), 7.34 (s, 1H), 7.23 (d, J=3.0 Hz, 1H), 7.14 (dd, J=8.9, 3.0 Hz, 1H), 4.24 (s, 2H), 4.09-3.78 (m, 7H).

Example 574

The following Example was made in an analogous fashion according to Procedure 79 and is shown below in Table 33. Any different reagents/starting materials than those described in Procedure 79 are noted in the last column of Table 33—"Changes to Procedure 79: Different Reagents/Starting Materials".

Procedure 80: Preparation of Example 575

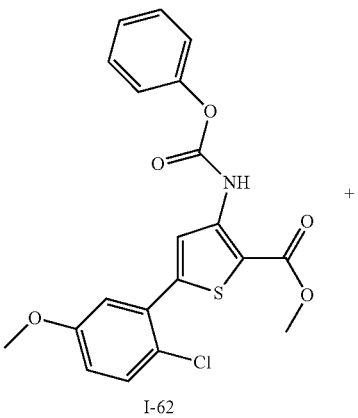

I-62

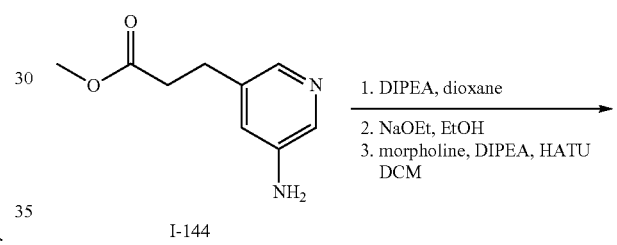

I-144

1. DIPEA, dioxane
2. NaOEt, EtOH
3. morpholine, DIPEA, HATU DCM

TABLE 33

Example 574

| Example | Structure | ES/MSM m/z | 1H-NMR | Changes to Procedure 79: Different Reagents/Starting Materials |
|---|---|---|---|---|
| 574 | 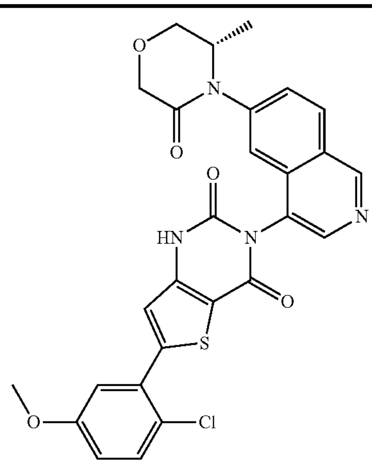 | 549.8 | 1H NMR (400 MHz, MeOD) δ 9.59 (s, 1H), 8.67 (s, 1H), 8.46 (d, J = 8.8 Hz, 1H), 8.03 (dd, J = 6.1, 1.9 Hz, 1H), 7.87 (dt, J = 8.8, 1.4 Hz, 1H), 7.53 (d, J = 8.9 Hz, 1H), 7.34 (s, 1H), 7.22 (d, J = 3.0 Hz, 1H), 7.09 (dd, J = 8.9, 3.0 Hz, 1H), 4.47-4.03 (m, 4H), 3.89 (s, 4H), 1.17 (d, J = 6.5 Hz, 3H). | (5S)-5-methylmorpholin-3-one |

1089
-continued

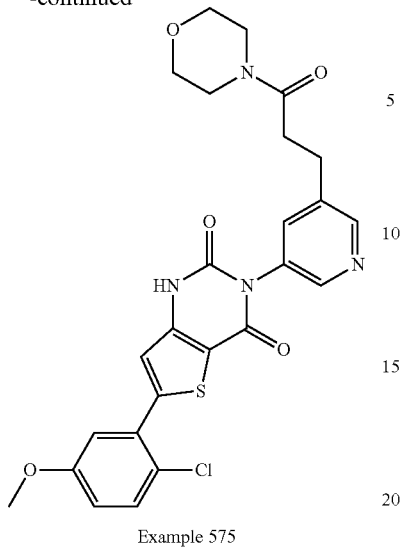

Example 575

6-(2-chloro-5-methoxy-phenyl)-3-[5-(3-morpholino-3-oxo-propyl)-3-pyridyl]-1H-thieno[3,2-d]pyrimidine-2,4-dione (Example 574): To a solution of methyl 5-(2-chloro-5-methoxyphenyl)-3-((phenoxycarbonyl)amino)thiophene-2-carboxylate (I-62) (100 mg, 0.24 mmol) in dry dioxane (1 mL) was added DIPEA (84 μL, 0.48 mmol) followed by methyl 3-(5-amino-3-pyridyl)propanoate (1-144) (52 mg, 0.29 mmol). The reaction mixture was heated at 90° C. overnight, after which the mixture was cooled to room temperature and concentrated under reduced pressure. To a suspension of the crude product in EtOH (2 mL), a solution of sodium ethoxide (21% wt solution in EtOH) was added dropwise until the reaction mixture turned to a homogeneous solution. The resulting reaction mixture was stirred at room temperature for 2 hours. The reaction mixture was then concentrated under reduced pressure, and the solid obtained was filtered and washed with acetonitrile and water. The solid product was dried under vacuum overnight. The acid intermediate (43 mg, 0.094 mmol) was taken in DCM (1 mL) followed by addition of DIPEA (49 μL, 0.28 mmol), morpholine (12 μL, 0.14 mmol), HATU (43 mg, 0.11 mmol). The reaction mixture was stirred at 50° C. overnight. The reaction mixture was then cooled to room temperature, neutralized with TFA and concentrated under reduced pressure. To the crude residue was added DMF (1 mL), acetonitrile (0.5 mL), TFA (0.3 mL) and water (0.2 mL). The mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the title compound.

ES/MS: 526.8 (M$^+$).

$^1$H NMR (400 MHz, DMSO) δ 12.20 (s, 1H), 8.57 (d, J=2.0 Hz, 1H), 8.46 (d, J=2.3 Hz, 1H), 7.83 (t, J=2.2 Hz, 1H), 7.58 (d, J=8.9 Hz, 1H), 7.27 (s, 1H), 7.23 (d, J=3.0 Hz, 1H), 7.13 (dd, J=8.9, 3.0 Hz, 1H), 3.85 (s, 3H), 3.52 (q, J=4.4 Hz, 4H), 3.44 (dt, J=6.9, 3.4 Hz, 4H), 3.01-2.88 (m, 2H), 2.73 (dd, J=8.3, 6.9 Hz, 2H).

1090
Procedure 81: Example 576

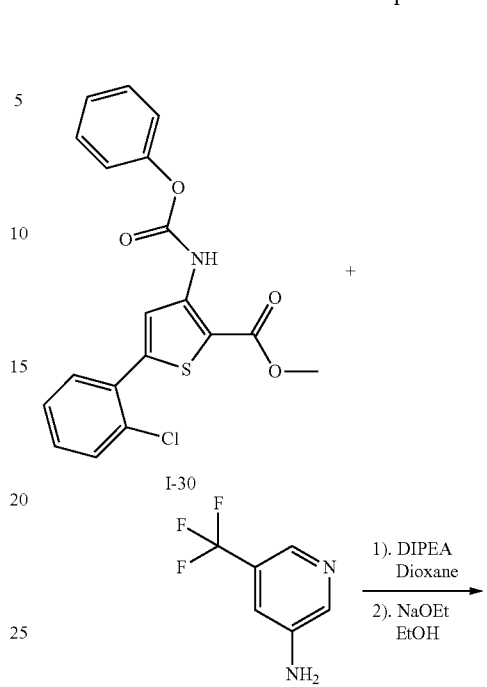

Example 576

6-(2-chlorophenyl)-3-(5-(trifluoromethyl)pyridin-3-yl)thieno[3,2-d]pyrimidine-2,4(1H,3H)-dione (Example 576): To a dram vial with methyl 5-(2-chlorophenyl)-3-(phenoxycarbonylamino)thiophene-2-carboxylate (I-30) (40 mg, 0.103 mmol) and 5-(trifluoromethyl)pyridin-3-amine (25 mg, 0.155 mmol) was added DIPEA (35.9 μL, 0.206 mmol) and dioxane (2 mL). The reaction mixture was stirred at 90° C. for 15 hours. The reaction mixture was then cooled to ambient temperature and concentrated under reduced pressure. To the resulting crude residue was then added EtOH (I mL) and NaOEt (98.5 μL, from 21% in EtOH, 0.304 mmol). The reaction mixture was then stirred at ambient temperature for 2 hours. The reaction mixture was diluted with of MeOH (0.5 mL), water (0.5 mL), and TFA (0.08 mL) then filtered through an acrodisc. The combined filtrate was purified by RP-HPLC (0.1% TFA-ACN in 0.1% TFA Water, Column: Gemini 10 uM, NX-C18 110 Angstrom, 250×30 mm) to give the title compound Example 576 as a trifluoroacetate salt.

ES/MS: 424.1 (M$^+$).

1H NMR (400 MHz, DMSO-d$_6$) δ 12.29 (s, 11H), 9.12-9.03 (m, 11H), 8.94 (d, J=2.1 Hz, 1H), 8.42 (d, J=2.3 Hz, 1H), 7.78-7.73 (m, 1H), 7.72-7.66 (m, 1H), 7.59-7.48 (m, 2H), 7.29 (s, 1H).

Examples 577-612

The following Examples were made in an analogous fashion according to Procedure 81 and are shown below in Table 34. Any different reagents/starting materials than those described in Procedure 81 are noted in the last column of Table 34—"Changes to Procedure 81: Different Reagents/Starting Materials".

TABLE 34

Examples 577-612

| Example | Structure | ES/MS m/z | 1H-NMR | Changes to Procedure 81: Different Reagents/Starting Materials |
|---|---|---|---|---|
| 577 | 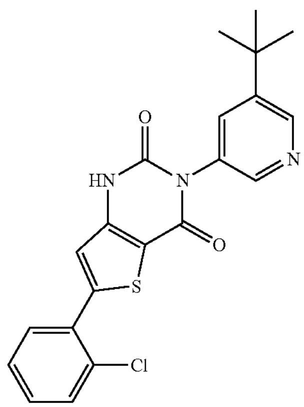 [SMILES: CC(C)(C)c1cncc(-n2c(=O)[nH]c3cc(-c4ccccc4Cl)sc3c2=O)c1] | 412.2 | 1H NMR (400 MHz, DMSO-d6) δ 12.19 (s, 1H), 8.74 (d, J = 2.2 Hz, 1H), 8.48 (d, J = 2.1 Hz, 1H), 8.01 (t, J = 2.2 Hz, 1H), 7.78-7.72 (m, 1H), 7.71-7.64 (m, 1H), 7.58-7.44 (m, 2H), 7.28 (s, 1H), 1.36 (s, 9H). | I-30; 5-(tert-butyl)pyridin-3-amine |
| 578 | 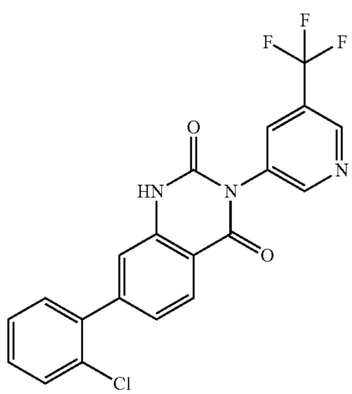 [SMILES: O=c1[nH]c2cc(-c3ccccc3Cl)ccc2c(=O)n1-c1cncc(C(F)(F)F)c1] | 418.2 | 1H NMR (400 MHz, DMSO-d6) δ 11.86 (s, 1H), 9.08 (dd, J = 2.0, 1.0 Hz, 1H), 8.95 (d, J = 2.1 Hz, 1H), 8.43 (t, J = 2.2 Hz, 1H), 8.05 (d, J = 8.1 Hz, 1H), 7.70-7.59 (m, 1H), 7.57-7.44 (m, 3H), 7.36-7.26 (m, 2H). | I-28; 5-(trifluoromethyl)pyridin-3-amine |
| 579 | 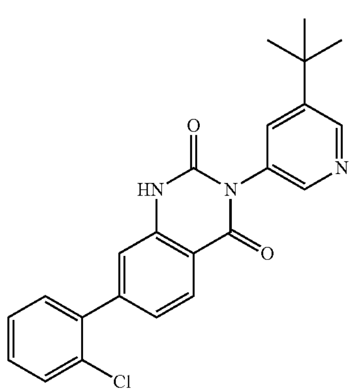 [SMILES: CC(C)(C)c1cncc(-n2c(=O)[nH]c3cc(-c4ccccc4Cl)ccc3c2=O)c1] | 406.3 | 1H NMR (400 MHz, DMSO-d6) δ 11.78 (s, 1H), 8.77 (d, J = 2.2 Hz, 1H), 8.54 (d, J = 2.1 Hz, 1H), 8.10 (t, J = 2.2 Hz, 1H), 8.04 (d, J = 8.0 Hz, 1H), 7.68-7.61 (m, 1H), 7.55-7.44 (m, 3H), 7.34-7.26 (m, 2H), 1.37 (s, 9H). | I-28; 5-(tert-butyl)pyridin-3-amine |

TABLE 34-continued

Examples 577-612

| Example | Structure | ES/MS m/z | 1H-NMR | Changes to Procedure 81: Different Reagents/Starting Materials |
|---|---|---|---|---|
| 580 | 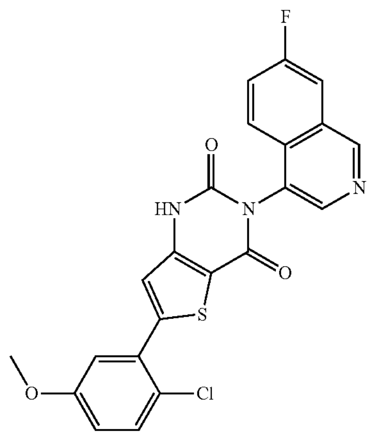 [SMILES: COc1ccc(Cl)c(-c2cc3[nH]c(=O)n(-c4cncc5cc(F)ccc45)c(=O)c3s2)c1] | 454.2 | 1H NMR (400 MHz, DMSO-d6) δ 12.28 (s, 1H), 9.43 (s, 1H), 8.58 (s, 1H), 8.10 (dd, J = 9.3, 2.6 Hz, 1H), 8.04 (dd, J = 9.2, 5.2 Hz, 1H), 7.72 (td, J = 9.0, 2.6 Hz, 1H), 7.60 (d, J = 8.9 Hz, 1H), 7.33 (s, 1H), 7.24 (d. J = 3.0 Hz, 1H), 7.14 (dd, J = 8.9, 3.1 Hz, 1H), 3.85 (s, 3H). | I-62, I-159 |
| 581 | 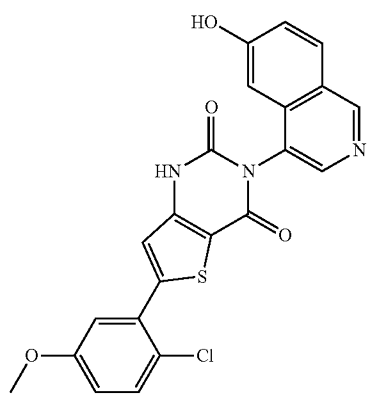 [SMILES: COc1ccc(Cl)c(-c2cc3[nH]c(=O)n(-c4cncc5ccc(O)cc45)c(=O)c3s2)c1] | 452.1 | 1H NMR (400 MHz, DMSO-d6) δ 12.38 (s, 1H), 11.09 (s, 1H), 9.42 (s, 1H), 8.57 (d, J = 1.3 Hz, 1H), 8.30 (d, J = 9.0 Hz, 1H), 7.60 (d, J = 8.9 Hz, 1H), 7.46-7.39 (m, 1H), 7.35 (s, 1H), 7.26 (d, J = 3.0 Hz, 1H), 7.15 (dd, J = 8.9, 3.0 Hz, 1H), 7.01 (s, 1H), 3.86 (s, 3H). | I-62, I-161 |
| 582 | 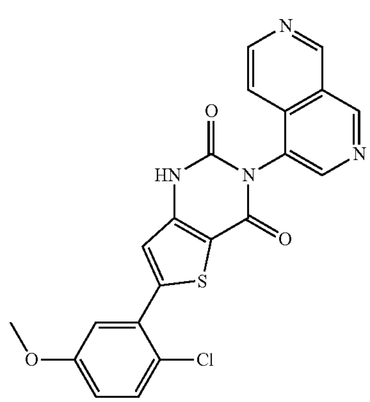 [SMILES: COc1ccc(Cl)c(-c2cc3[nH]c(=O)n(-c4cncc5cnccc45)c(=O)c3s2)c1] | 437.1 | 1H NMR (400 MHz, DMSO-d6) δ 12.32 (s, 1H), 9.72-9.66 (m, 2H), 8.86 (s, 1H), 8.76 (d, J = 6.0 Hz, 1H), 7.89 (dd, J = 6.0, 1.1 Hz, 1H), 7.60 (d, J = 8.9 Hz, 1H), 7.34 (s, 1H), 7.24 (d, J = 3.1 Hz, 1H), 7.14 (dd, J = 8.9, 3.0 Hz, 1H), 3.85 (s, 3H). | I-62, I-163 |

TABLE 34-continued

Examples 577-612

| Example | Structure | ES/MS m/z | 1H-NMR | Changes to Procedure 81: Different Reagents/Starting Materials |
|---|---|---|---|---|
| 583 | 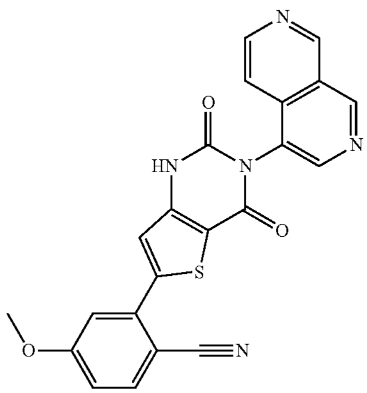 [SMILES: COc1ccc(C#N)c(-c2cc3[nH]c(=O)n(-c4cncc5cnccc45)c(=O)c3s2)c1] | 428.2 | 1H NMR (400 MHz, DMSO-d6) δ 12.39 (s, 1H), 9.68 (d, J = 9.6 Hz, 2H), 8.86 (s, 1H), 8.75 (d, J = 6.0 Hz, 1H), 8.01 (d, J = 8.7 Hz, 1H), 7.92 (d, J = 6.0 Hz, 1H), 7.52 (s, 1H), 7.34 (d, J = 2.6 Hz, 1H), 7.28 (dd, J = 8.7, 2.6 Hz, 1H), 3.95 (s, 3H). | I-63, I-163 |
| 584 | 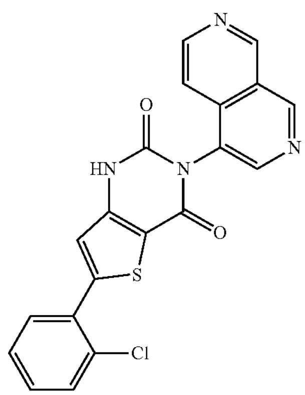 [SMILES: O=c1[nH]c2cc(-c3ccccc3Cl)sc2c(=O)n1-c1cncc2cnccc12] | 407.1 | 1H NMR (400 MHz, DMSO-d6) δ 12.32 (s, 1H), 9.74-9.59 (m, 2H), 8.85 (d, J = 2.1 Hz, 1H), 8.77-8.69 (m, 1H), 7.89 (d, J = 5.9 Hz, 1H), 7.81-7.64 (m, 1H), 7.78-7.70 (m, 2H), 7.41-7.26 (m, 1H). | I-30, I-163 |
| 585 | 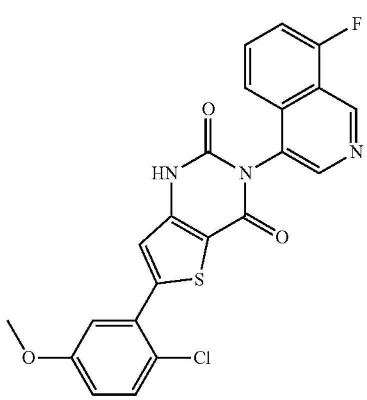 [SMILES: COc1ccc(Cl)c(-c2cc3[nH]c(=O)n(-c4cncc5c(F)cccc45)c(=O)c3s2)c1] | 454.2 | 1H NMR (400 MHz, DMSO-d6) δ 12.31 (s, 1H), 9.59 (s, 1H), 8.72 (s, 1H), 7.84-7.79 (m, 1H), 7.75 (d, J = 8.4 Hz, 1H), 7.58 (dd, J = 11.3, 8.1 Hz, 2H), 7.34 (s, 1H), 7.24 (d, J = 3.0 Hz, 1H), 7.14 (dd, J = 8.9, 3.0 Hz, 1H), 3.85 (s, 3H). | I-62, 7-naphthyridin-8-fluoro-isoquinolin-4-amine |

TABLE 34-continued

Examples 577-612

| Example | Structure | ES/MS m/z | 1H-NMR | Changes to Procedure 81: Different Reagents/Starting Materials |
|---|---|---|---|---|
| 586 | 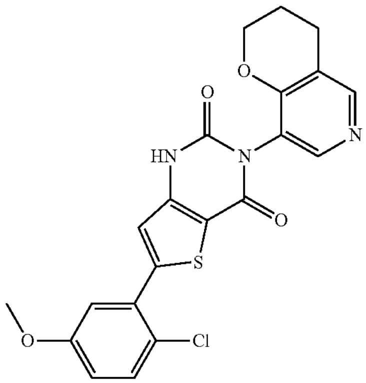 [SMILES: COc1ccc(Cl)c(-c2cc3[nH]c(=O)n(-c4cncc5c4OCCC5)c(=O)c3s2)c1] | 442.2 | 1H NMR (400 MHz, DMSO-d6) δ 12.31 (s, 1H), 8.58 (d, J = 8.4 Hz, 2H), 7.58 (d, J = 8.9 Hz, 1H), 7.26 (d, J = 17.2 Hz, 2H), 7.13 (d, J = 8.9 Hz, 1H), 4.40 (s, 2H), 3.84 (s, 3H), 2.93 (d, J = 6.4 Hz. 2H), 2.08-1.97 (m, 2H). | I-62, I-164 |
| 587 | 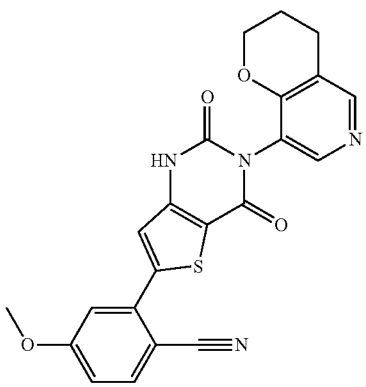 [SMILES: COc1ccc(C#N)c(-c2cc3[nH]c(=O)n(-c4cncc5c4OCCC5)c(=O)c3s2)c1] | 433.1 | 1H NMR (400 MHz, DMSO-d6) δ 12.41 (s, 1H), 8.63 (d, J = 14.1 Hz, 1H), 8.00 (d, J = 8.8 Hz, 1H), 7.46 (s, 1H), 7.34 (d, J = 2.5 Hz, 1H), 7.27 (dd, J = 8.7, 2.6 Hz, 1H), 7.20-7.12 (m, 1H), 4.43 (t, J = 5.1 Hz, 2H), 3.94 (s, 3H), 2.92 (q, J = 8,6, 7.5 Hz, 2H), 2.04-1.98 (m, 2H). | I-63, I-164 |
| 588 | 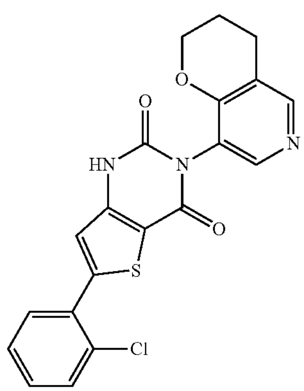 [SMILES: O=c1[nH]c2cc(-c3ccccc3Cl)sc2c(=O)n1-c1cncc2c1OCCC2] | 412.2 | 1H NMR (400 MHz, DMSO-d6) δ 12.30 (s, 1H). 8.55 (d, J = 4.7 Hz, 2H), 7.77-7.72 (m, 1H), 7.72-7.67 (m, 1H), 7.58-7.49 (m, 2H). 7.29 (s, 1H), 4.39 (t, J = 5.1 Hz, 2H), 2.91 (t, J = 6.3 Hz, 2H), 2.00 (p, J = 6.1 Hz, 2H). | I-30, I-164 |

TABLE 34-continued

Examples 577-612

| Example | Structure | ES/MS m/z | 1H-NMR | Changes to Procedure 81: Different Reagents/Starting Materials |
|---|---|---|---|---|
| 589 | 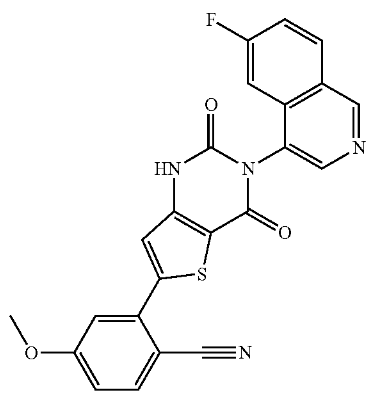 [SMILES: COc1ccc(C#N)c(-c2cc3[nH]c(=O)n(-c4cncc5ccc(F)cc45)c(=O)c3s2)c1] | 445.1 | 1H NMR (400 MHz, DMSO-d6) δ 12.29 (s, 1H), 9.45 (s, 1H), 8.60 (s, 1H), 8.41 (dd, J = 9.1, 5.6 Hz, 1H), 8.01 (d, J = 8.7 Hz, 1H), 7.89 (dd, J = 10.3, 2.5 Hz, 1H), 7.68 (td, J = 8.8, 2.5 Hz, 1H), 7.51 (s, 1H), 7.33 (d, J = 2.5 Hz, 1H). 7.27 (dd, J = 8.7, 2.6 Hz, 1H), 3.95 (s, 3H). | I-63; 6-fluoro-isoquinolin-4-amine |
| 590 | 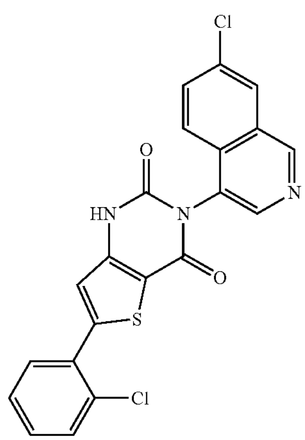 [SMILES: O=c1[nH]c2cc(-c3ccccc3Cl)sc2c(=O)n1-c1cncc2cc(Cl)ccc12] | 440.1 | 1H NMR (400 MHz, DMSO-d6) δ 12.30 (s, 1H), 9.42 (d, J = 0.8 Hz, 1H), 8.62 (s, 1H), 8.44 (d, J = 2.1 Hz, 1H), 8.00 (d, J = 9.0 Hz, 1H), 7.80 (dd, J = 9.0, 2.1 Hz, 1H), 7.78-7.74 (m, 1H), 7.72-7.68 (m, 1H), 7.58-7.41 (m, 2H), 7.33 (s, 1H). | I-30, 7-chloroiso-quinolin-4-amine |
| 591 | 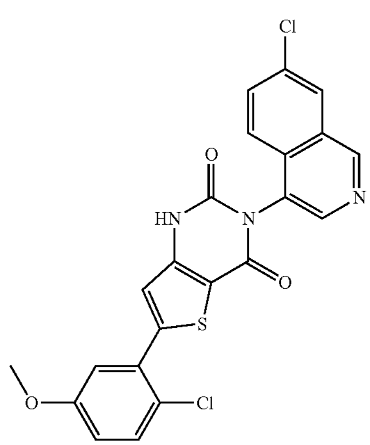 [SMILES: COc1ccc(Cl)c(-c2cc3[nH]c(=O)n(-c4cncc5cc(Cl)ccc45)c(=O)c3s2)c1] | 470.1 | 1H NMR (400 MHz, DMSO-d6) δ 12.29 (s, 1H), 9.43 (s, 1H), 8.62 (s, 1H), 8.44 (d, J = 2.1 Hz, 1H), 7.98 (d, J = 9.0 Hz, 1H), 7.81 (dd, J = 9.0, 2.2 Hz, 1H), 7.60 (d, J = 8.9 Hz, 1H), 7.33 (s, 1H), 7.24 (d, J = 3.0 Hz, 1H), 7.14 (dd, J = 8.9, 3.1 Hz, 1H), 3.85 (s, 3H). | I-62, 7-chloroiso-quinolin-4-amine |

TABLE 34-continued

Examples 577-612

| Example | Structure | ES/MS m/z | 1H-NMR | Changes to Procedure 81: Different Reagents/Starting Materials |
|---|---|---|---|---|
| 592 | 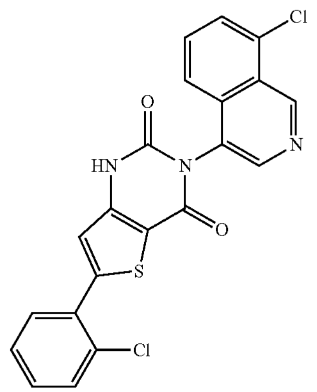 [SMILES: O=c1[nH]c2cc(-c3ccccc3Cl)sc2c(=O)n1-c1cncc2c(Cl)cccc12] | 440.1 | 1H NMR (400 MHz, DMSO-d6) δ 12.32 (s, 1H), 9.67 (d, J = 0.9 Hz, 1H), 8.74 (s, 1H), 7.97-7.89 (m, 2H), 7.81-7.74 (m, 2H), 7.72-7.69 (m, 1H), 7.59-7.47 (m, 2H), 7.34 (s, 1H). | I-30, 8-chloroiso-quinolin-4-amine |
| 593 | 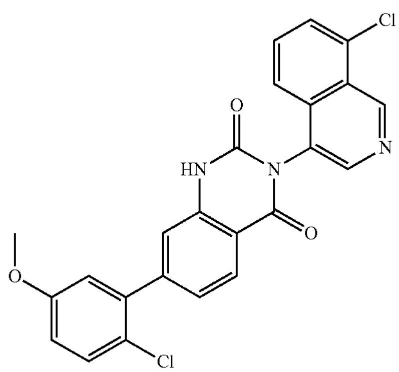 [SMILES: COc1ccc(Cl)c(-c2ccc3c(=O)n(-c4cncc5c(Cl)cccc45)c(=O)[nH]c3c2)c1] | 464.3 | 1H NMR (400 MHz, DMSO-d6) δ 11.89 (s, 1H), 9.68 (d, J = 0.9 Hz, 1H), 8.76 (s, 1H), 8.05 (d, J = 8.0 Hz, 1H), 7.98 (d, J = 8.4 Hz, 1H), 7.92 (dd, J = 7.6, 0.9 Hz, 1H), 7.77 (dd, J = 8.5, 7.5 Hz, 1H), 7.56 (d, J = 8.9 Hz, 1H), 7.37-7.31 (m, 2H), 7.10 (dd, J = 8.8, 3.1 Hz, 1H), 7.01 (d, J = 3.0 Hz, 1H), 3.84 (s, 3H). | I-132, 8-chloroiso-quinolin-4-amine |
| 594 | 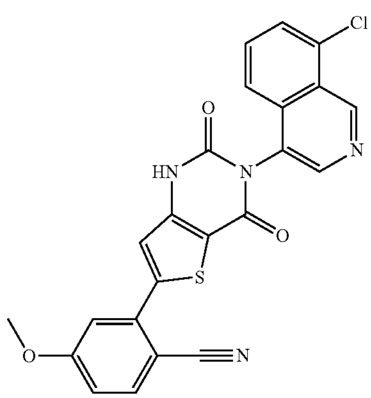 [SMILES: COc1ccc(C#N)c(-c2cc3[nH]c(=O)n(-c4cncc5c(Cl)cccc45)c(=O)c3s2)c1] | 461.1 | 1H NMR (400 MHz, DMSO-d6) δ 12.38 (s, 1H), 9.67 (s, 1H), 8.75 (s, 1H), 8.01 (d, J = 8.7 Hz, 1H), 7.97 (d, J = 8.6 Hz, 1H), 7.92 (d, J = 7.3 Hz, 1H), 7.81-7.75 (m, 1H), 7.52 (s, 1H), 7.34 (d, J = 2.5 Hz, 1H), 7.31-7.25 (m, 1H), 3.95 (s, 3H). | I-63, 8-chloroiso-quinolin-4-amine |

TABLE 34-continued

Examples 577-612

| Example | Structure | ES/MS m/z | 1H-NMR | Changes to Procedure 81: Different Reagents/Starting Materials |
|---|---|---|---|---|
| 595 | 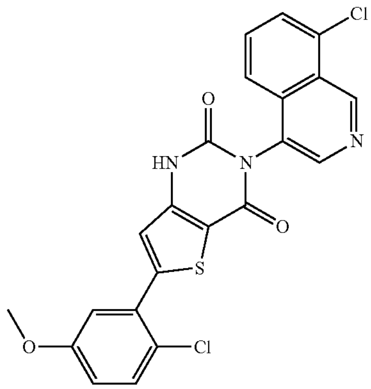 [SMILES: COc1ccc(Cl)c(-c2cc3[nH]c(=O)n(-c4cncc5c(Cl)cccc45)c(=O)c3s2)c1] | 470.1 | 1H NMR (400 MHz, DMSO-d6) δ 12.32 (s, 1H), 9.67 (s, 1H), 8.74 (s, 1H), 7.93 (dd, J = 7.8, 6.0 Hz, 2H), 7.82-7.75 (m, 1H), 7.60 (d, J = 8.8 Hz, 1H), 7.34 (s, 1H), 7.24 (d, J = 3.1 Hz, 1H), 7.14 (dd, J = 8.9, 3.0 Hz, 1H), 3.85 (s, 3H). | I-62; 8-chloroiso-quinolin-4-amine |
| 596 | 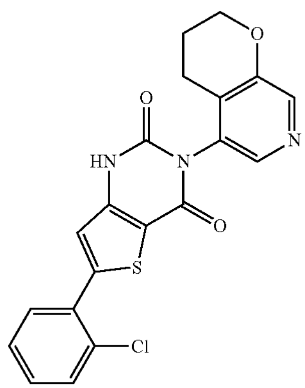 [SMILES: O=c1[nH]c2cc(-c3ccccc3Cl)sc2c(=O)n1-c1cncc2c1CCCO2] | 412.2 | 1H NMR (400 MHz, DMSO-d6) δ 12.25 (s, 1H), 8.19 (s, 1H), 8.08 (s, 1H), 7.76-7.72 (m, 1H), 7.71-7.66 (m, 1H), 7.57-7.49 (m, 2H), 7.28 (s, 1H), 4.22 (dd, J = 5.8, 4.2 Hz, 2H), 2.56 (d, J = 11.1 Hz, 2H), 1.94-1.89 (m, 2H). | I-30; I-165 |
| 597 | 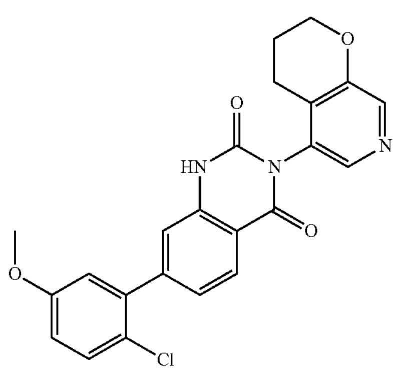 [SMILES: COc1ccc(Cl)c(-c2ccc3c(=O)n(-c4cncc5c4CCCO5)c(=O)[nH]c3c2)c1] | 436.2 | 1H NMR (400 MHz, DMSO-d6) δ 11.82 (s, 1H), 8.21 (s, 1H), 8.10 (s, 1H), 8.04 (d, J = 8.0 Hz, 1H), 7.54 (d, J = 8.8 Hz, 1H), 7.36-7.28 (m, 2H), 7.08 (dd, J = 8.9, 3.1 Hz, 1H), 7.00 (d, J = 3.0 Hz, 1H), 4.22 (dd, J = 5.9, 4.2 Hz, 2H), 3.82 (s, 3H), 2.54 (d, J = 6.9 Hz, 2H), 1.94-1.90 (m, 2H). | I-132; I-165 |

TABLE 34-continued

Examples 577-612

| Example | Structure | ES/MS m/z | 1H-NMR | Changes to Procedure 81: Different Reagents/Starting Materials |
|---|---|---|---|---|
| 598 | 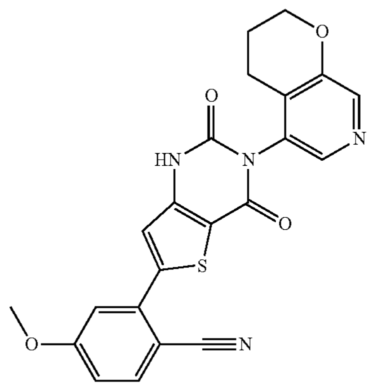 [SMILES: COc1ccc(C#N)c(-c2cc3[nH]c(=O)n(-c4cncc5c4CCCO5)c(=O)c3s2)c1] | 433.2 | 1H NMR (400 MHz, DMSO-d6) δ 12.31 (s, 1H), 8.18 (s, 1H), 8.07 (s, 1H), 8.00 (d, J = 8.7 Hz, 1H), 7.46 (s, 1H), 7.33 (d, J = 2.5 Hz, 1H), 7.27 (dd, J = 8.7, 2.5 Hz, 1H), 4.27-4.16 (m, 2H), 3.94 (s, 3H), 2.63-2.52 (m, 2H), 1.93-1.90 (m, 2H). | I-63; I-165 |
| 599 | 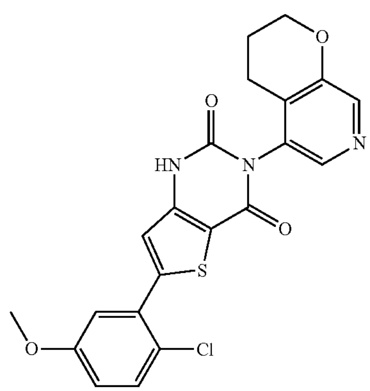 | 442.2 | 1H NMR (400 MHz, DMSO-d6) δ 12.24 (s, 1H), 8.19 (s, 1H), 8.07 (s, 1H), 7.58 (d, J = 8.9 Hz, 1H), 7.28 (s, 1H), 7.23 (d, J = 3.0 Hz, 1H), 7.13 (dd, J = 8.9, 3.0 Hz, 1H), 4.22 (dd, J = 5.9, 4.3 Hz, 2H), 3.84 (s, 3H), 2.56-2.50 (m, 2H), 1.91 (dd, J = 6.4, 4.4 Hz, 2H). | I-62; I-165 |
| 600 | 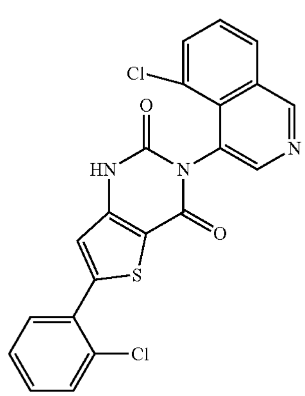 [SMILES: O=c1[nH]c2cc(-c3ccccc3Cl)sc2c(=O)n1-c1cncc2cccc(Cl)c12] | 440.1 | 1H NMR (400 MHz, DMSO-d6) δ 12.31 (s, 1H), 9.54 (s, 1H), 8.62 (s, 1H), 8.34 (dd, J = 8.2, 1.1 Hz, 1H), 7.97 (dd, J = 7.6, 1.2 Hz, 1H), 7.81-7.74 (m, 2H), 7.72-7.67 (m, 1H), 7.57-7.50 (m, 2H), 7.33 (s, 1H). | I-30, 5-chloroiso-quinolin-4-amine |

TABLE 34-continued

Examples 577-612

| Example | Structure | ES/MS m/z | 1H-NMR | Changes to Procedure 81: Different Reagents/Starting Materials |
|---|---|---|---|---|
| 601 | 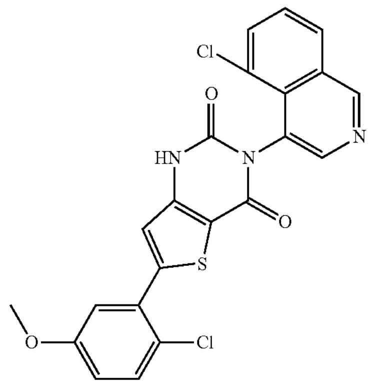 [SMILES: COc1ccc(Cl)c(-c2cc3[nH]c(=O)n(-c4cncc5cccc(Cl)c45)c(=O)c3s2)c1] | 470.1 | 1H NMR (400 MHz, DMSO-d6) δ 12.30 (s, 1H), 9.54 (s, 1H), 8.61 (s, 1H), 8.34 (dd, J = 8.3, 1.1 Hz, 1H), 7.96 (dd, J = 7.6, 1.2 Hz, 1H), 7.77 (t, J = 7.9 Hz, 1H), 7.59 (d, J = 8.9 Hz, 1H), 7.32 (s, 1H), 7.29 (d, J = 3.0 Hz, 1H), 7.13 (dd, J = 8.9, 3.0 Hz, 1H), 3.85 (s, 3H). | I-62, 5-chloroisoquinolin-4-amine |
| 602 | 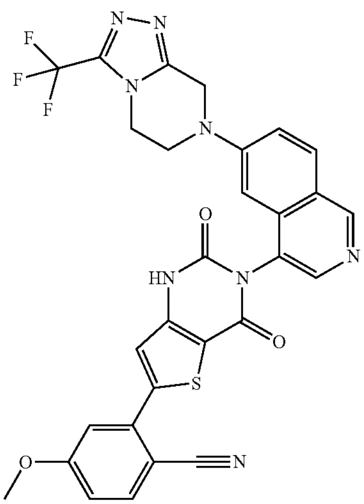 [SMILES: COc1ccc(C#N)c(-c2cc3[nH]c(=O)n(-c4cncc5ccc(N6CCn7c(nnc7C(F)(F)F)C6)cc45)c(=O)c3s2)c1] | 616.7 | 1H NMR (400 MHz, DMSO) δ 12.32 (s, 1H). 9.36 (s, 1H), 8.55 (s, 1H), 8.32 (d, J = 9.4 Hz, 1H), 8.02 (d, J = 8.7 Hz, 1H), 7.89 (dd, J = 9.4, 2.5 Hz, 1H), 7.54 (s, 1H), 7.36-7.25 (m, 3H), 5.09 (s, 2H), 4.34 (t, J = 5.3 Hz, 2H), 4.17 (t, J = 5.4 Hz, 2H), 3.95 (s, 3H). | I-139, I-63 |
| 603 | 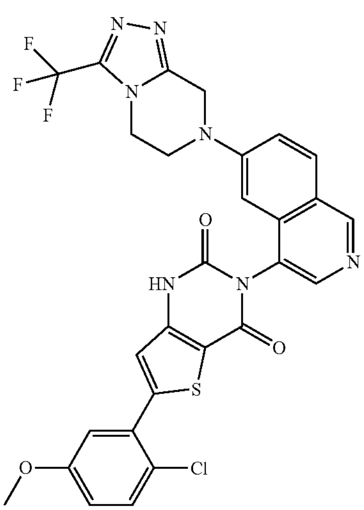 [SMILES: COc1ccc(Cl)c(-c2cc3[nH]c(=O)n(-c4cncc5ccc(N6CCn7c(nnc7C(F)(F)F)C6)cc45)c(=O)c3s2)c1] | 625.7 | 1H NMR (400 MHz, DMSO) δ 12.26 (s, 1H), 9.37 (s, 1H), 8.55 (s, 1H), 8.33 (d, J = 9.4 Hz, 1H), 7.90 (dd, J = 9.4, 2.5 Hz, 1H), 7.61 (d, J = 8.9 Hz, 1H), 7.36 (s, 1H), 7.29 (d, J = 2.4 Hz, 1H), 7.23 (d, J = 3.1 Hz, 1H), 7.14 (dd, J = 8.9, 3.0 Hz, 1H), 5.10 (s, 2H), 4.34 (t, J = 5.4 Hz, 2H), 4.17 (t, J = 5.4 Hz, 2H), 3.86 (s, 3H). | I-139, I-62 |

TABLE 34-continued

Examples 577-612

| Example | Structure | ES/MS m/z | 1H-NMR | Changes to Procedure 81: Different Reagents/Starting Materials |
|---|---|---|---|---|
| 604 | 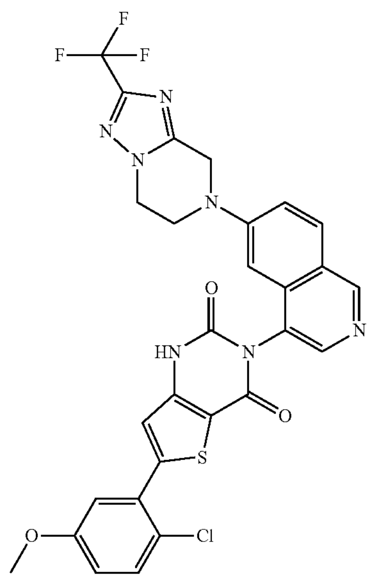 [SMILES: COc1ccc(Cl)c(-c2cc3[nH]c(=O)n(-c4cncc5ccc(N6CCn7nc(C(F)(F)F)nc7C6)cc45)c(=O)c3s2)c1] | 625.7 | 1H NMR (400 MHz, DMSO) δ 12.27 (s, 1H), 9.40 (s, 1H), 8.58 (s, 1H), 8.36 (d, J = 9.4 Hz, 1H), 7.94 (dd, J = 9.5, 2.5 Hz, 1H), 7.61 (d, J = 8.9 Hz, 1H), 7.36 (s, 1H), 7.28 (d, J = 2.4 Hz, 1H), 7.23 (d, J = 3.0 Hz, 1H), 7.14 (dd, J = 8.9, 3.0 Hz, 1H), 5.06 (s, 2H), 4.44 (t, J = 5.3 Hz, 2H), 4.28 (t, J = 5.4 Hz, 2H), 3.86 (s, 3H). | I-140, I-62 |
| 605 | 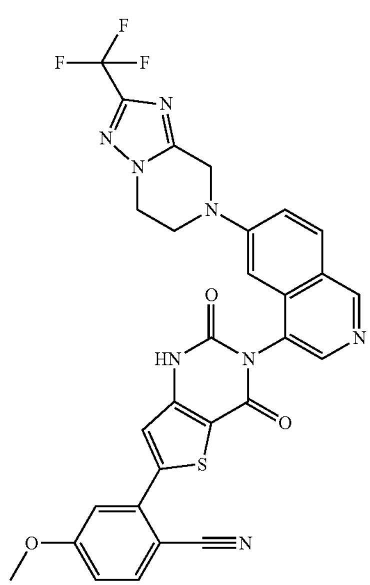 [SMILES: COc1ccc(C#N)c(-c2cc3[nH]c(=O)n(-c4cncc5ccc(N6CCn7nc(C(F)(F)F)nc7C6)cc45)c(=O)c3s2)c1] | 616.8 | 1H NMR (400 MHz, DMSO) δ 12.34 (s, 1H), 9.40 (s, 1H), 8.59 (s, 1H), 8.37 (d, J = 9.4 Hz, 1H), 8.02 (d, J = 8.7 Hz, 1H), 7.94 (dd, J = 9.5, 2.5 Hz, 1H), 7.54 (s, 1H), 7.36-7.23 (m, 3H), 5.06 (s, 2H), 4.44 (t, J = 5.3 Hz, 2H), 4.28 (t, J = 5.3 Hz, 2H), 3.95 (s, 3H). | I-140, I-63 |

TABLE 34-continued

| | | Examples 577-612 | | |
|---|---|---|---|---|
| Example | Structure | ES/MS m/z | 1H-NMR | Changes to Procedure 81: Different Reagents/Starting Materials |
| 606 | | 571.8 | 1H NMR (400 MHz, DMSO) δ 12.28 (s, 1H), 9.36 (s, 1H), 8.55 (s, 1H). 8.34 (d, J = 9.4 Hz, 1H), 7.89 (dd, J = 9.4, 2.4 Hz, 1H), 7.61 (d, J = 8.9 Hz, 1H), 7.36 (s, 1H), 7.22 (dd, J = 8.8, 2.7 Hz, 2H), 7.15 (dd, J = 8.9, 3.0 Hz, 1H), 4.94 - 4.79 (m, 2H), 4.47 (t, J = 5.1 Hz, 2H), 4.13 (q, J = 4.9 Hz, 2H), 3.86 (s, 3H), 2.23 (s, 3H). | I-142, I-62 |
| 607 | | 441.7 | 1H NMR (400 MHz, DMSO) δ 12.28 (s, 1H), 9.44 (d. J = 0.8 Hz, 1H), 8.56 (s, 1H), 8.29 (d, J = 5.4 Hz, 1H), 7.64 (dd, J = 5.5, 0.8 Hz, 1H), 7.59 (d, J = 8.9 Hz, 1H), 7.32 (s, 1H), 7.23 (d, J = 3.0 Hz, 1H), 7.13 (dd, J = 8.9, 3.0 Hz, 1H), 3.85 (s, 3H). | I-138, I-62 |
| 608 | | 432.8 | 1H NMR (400 MHz, DMSO) δ 12.32 (s, 1H), 9.39 (s, 1H), 8.52 (s, 1H), 8.22 (d, J = 5.4 Hz, 1H), 8.01 (d. J = 8.7 Hz, 1H), 7.62 (dd, J = 5.4, 0.8 Hz, 1H), 7.50 (s, 1H), 7.33 (d, J = 2.5 Hz, 1H), 7.27 (dd, J = 8.7, 2.5 Hz, 1H), 3.95 (s, 3H). | I-138, I-63 |

TABLE 34-continued

Examples 577-612

| Example | Structure | ES/MS m/z | 1H-NMR | Changes to Procedure 81: Different Reagents/Starting Materials |
|---|---|---|---|---|
| 609 | 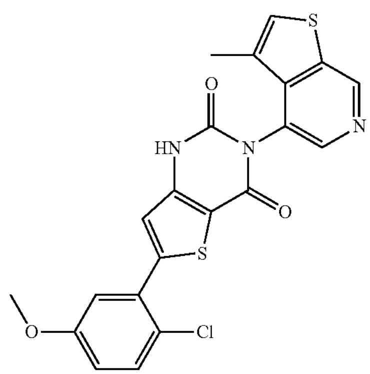 [SMILES: COc1ccc(Cl)c(-c2cc3[nH]c(=O)n(-c4cncc5scc(C)c45)c(=O)c3s2)c1] | 455.7 | 1H NMR (400 MHz, DMSO) δ 12.40 (s, 1H), 9.38 (s, 1H), 8.51 (s, 1H), 7.94 (d, J = 1.3 Hz, 1H), 7.59 (d, J = 8.9 Hz, 1H), 7.33 (s, 1H), 7.28 (d, J = 3.0 Hz, 1H), 7.13 (dd, J = 8.9, 3.0 Hz, 1H), 3.85 (s, 3H), 2.21 (d, J = 1.2 Hz, 3H). | I-149, I-62 |
| 610 | 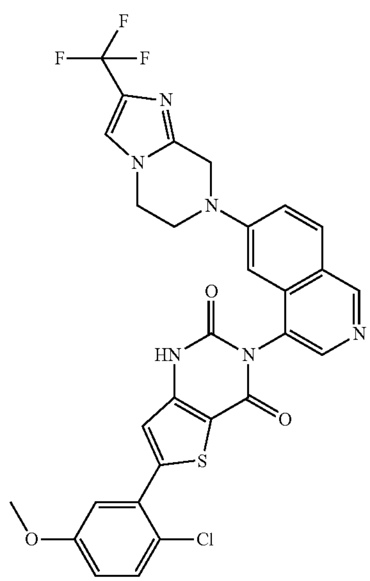 [SMILES: COc1ccc(Cl)c(-c2cc3[nH]c(=O)n(-c4cncc5ccc(N6CCn7cc(C(F)(F)F)nc7C6)cc45)c(=O)c3s2)c1] | 625.7 | 1H NMR (400 MHz, DMSO) δ 12.28 (s, 1H), 9.41 (s, 1H), 8.60 (s, 1H), 8.37 (d, J = 9.5 Hz, 1H), 7.93 (dd, J = 9.4, 2.5 Hz, 1H), 7.85 (d, J = 1.5 Hz, 1H), 7.61 (d, J = 8.9 Hz, 1H), 7.36 (s, 1H), 7.23 (t, J = 2.4 Hz, 2H), 7.14 (dd, J = 8.9, 3.0 Hz, 1H), 4.93 (d, J = 1.9 Hz, 2H), 4.25-4.15 (m, 4H), 3.86 (s, 3H). | I-150, I-62 |
| 611 | 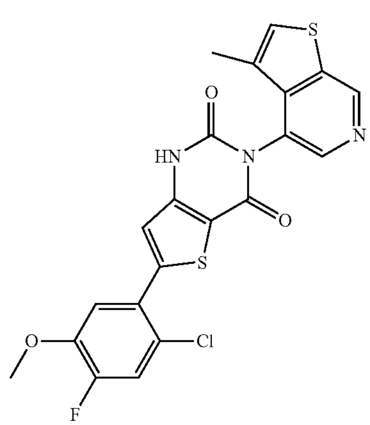 [SMILES: COc1cc(-c2cc3[nH]c(=O)n(-c4cncc5scc(C)c45)c(=O)c3s2)c(Cl)cc1F] | 474.7 | 1H NMR (400 MHz, DMSO) δ 12.45 (s, 1H), 9.42 (s, 1H), 8.55 (s, 1H), 7.99 (d, J = 1.3 Hz, 1H), 7.71 (d, J = 11.1 Hz, 1H), 7.49 (d, J = 8.9 Hz, 1H), 7.32 (s, 1H), 3.95 (s, 3H), 2.22 (d, J = 1.2 Hz, 3H). | I-149, I-61 |

TABLE 34-continued

Examples 577-612

| Example | Structure | ES/MS m/z | 1H-NMR | Changes to Procedure 81: Different Reagents/Starting Materials |
|---|---|---|---|---|
| 612 | 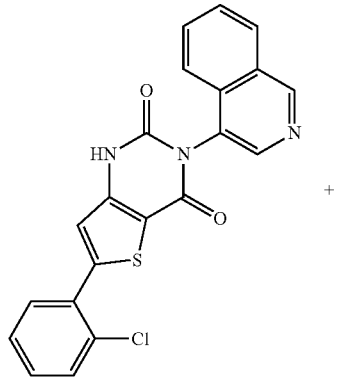 | 513.8 | 1H NMR (400 MHz, DMSO) δ 12.19 (s, 1H), 8.51 (dd, J = 10.3, 2.1 Hz, 2H), 7.76 (t, J = 2.1 Hz, 1H), 7.58 (d, J = 8.9 Hz, 1H), 7.27 (s, 1H), 7.23 (d, J = 3.0 Hz, 1H), 7.12 (dd, J = 8.9, 3.0 Hz, 1H), 3.89 (s, 2H), 3.84 (s, 3H), 3.56 (d, J = 5.1 Hz, 6H), 3.48 (t, J = 4.7 Hz, 2H). | I-152, I-62 |

Procedure 82: Example 613

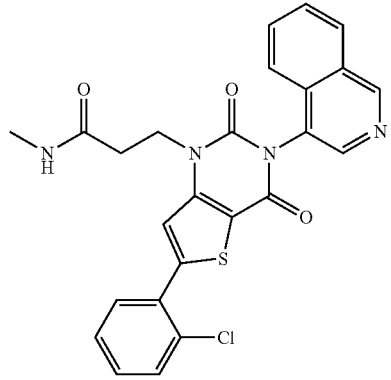 [SMILES: CC(=O)NCCn1c(=O)n(-c2cncc3ccccc23)c(=O)c2sc(-c3ccccc3Cl)cc21]

Example 613

3-(6-(2-chlorophenyl)-3-(isoquinolin-4-yl)-2,4-dioxo-3,4-dihydrothieno[3,2-d]pyrimidin-1(2H)-yl)-N-methylpropanamide. (Example 613): To a solution of Example 1 (40.0 mg, 0.098 mmol) in DMF (2.00 mL) was added 3-chloro-N-methyl-propanamide (47.9 mg, 0.394 mmol) and potassium carbonate (27.2 mg, 0.197 mmol) and the reaction mixture was heated at 70° C., 2 hours. The reaction mixture cooled to rt, water (0.5 mL), MeOH (1 mL), and 0.1% TFA were added. The mixture was filtered through an acrodisc, and subsequently purified by RP-HPLC (0.1% TFA-ACN in 0.1% TFA Water, Column: Gemini 10 uM, NX-C18 110 Angstrom, 250×30 mm) to give the title compound Example 613 as a trifluoroacetate salt.

ES/MS: 491.3 (M$^+$).

$^1$H NMR (400 MHz, DMSO-d$_6$) δ 9.47 (s, 1H), 8.57 (s, 1H), 8.30 (dd, J=7.4, 1.6 Hz, 1H), 8.01-7.90 (m, 2H), 7.89-7.75 (m, 4H), 7.72 (dd, J=6.0, 3.4 Hz, 1H), 7.61-7.51 (m, 2H), 4.44-4.23 (m, 2H), 2.57 (t, J=7.2 Hz, 2H), 2.53 (d, J=4.6 Hz, 3H).

Example 614

The following Example was made in an analogous fashion according to Procedure 82 and is shown below in Table 35. Any different reagents/starting materials than those described in Procedure 82 are noted in the last column of Table 35—"Changes to Procedure 82: Different Reagents/Starting Materials".

TABLE 35

Example 614

| Example | Structure | ES/MS m/z | 1H-NMR | Changes to Procedure 82: Different Reagents/Starting Materials |
|---|---|---|---|---|
| 614 | (structure) | 491.3 | 1H NMR (400 MHz, DMSO-d6) δ 9.46 (s, 1H), 8.54 (s, 1H), 8.29 (dd, J = 7.4, 1.7 Hz, 1H), 8.10 (t, J = 6.2 Hz, 1H), 8.05 (d, J = 8.0 Hz, 1H), 7.89-7.83 (m, 1H), 7.83-7.77 (m, 3H), 7.72 (dd, J = 5.9, 3.4 Hz, 1H), 7.60-7.54 (m, 2H), 4.26-4.09 (m, 2H), 3.37 (s, 2H), 1.65 (s, 3H). | N-(2-chloroethyl)acetamide |

Procedure 83: Example 615

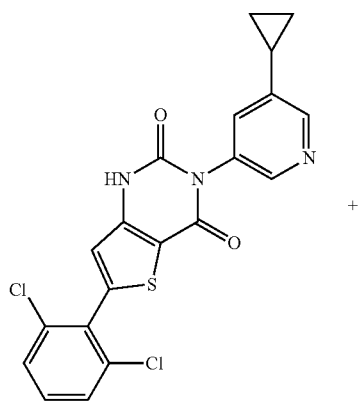

Example 370

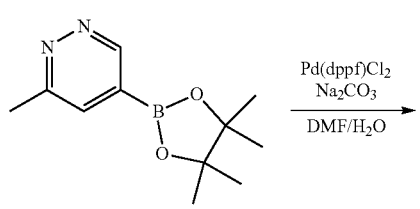

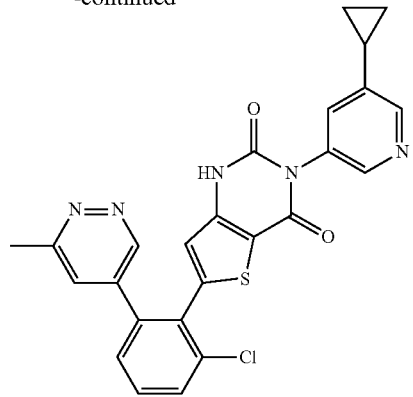

Example 615

6-(2-chloro-6-(6-methylpyridazin-4-yl)phenyl)-3-(5-cyclopropylpyridin-3-yl)thieno[3,2-d]pyrimidine-2,4(1H,3H)-dione (Example 615): To a microwave vial with 3-(5-cyclopropylpyridin-3-yl)-6-(2,6-dichlorophenyl)thieno[3,2-d]pyrimidine-2,4(1H,3H)-dione (Example 370) (25 mg, 0.058 mmol) was added 3-methyl-5-(4,4,5,5-tetramethyl-1,3,2-dioxaborolan-2-yl)pyridazine (18 mg, 0.087 mmol), [1,1'-Bis(diphenylphosphino)ferrocene]dichloropalladium (II) (6.4 mg, 0.0087 mmol), sodium carbonate (2M aqueous, 0.058 mL, 0.116 mmol), and DME (2 mL). The mixture was degassed with argon for 30 seconds. The vial was sealed, and the reaction mixture was stirred at 90° C. overnight. The crude product was diluted with 20% MeOH/DCM, filtered via celite and concentrated under reduced pressure. The crude product was dissolved in mixture of DMF (1 mL), MeOH (1 mL), and water (0.1 mL with 0.1% TFA), and the mixture was filtered through an acrodisc, and was subsequently purified by RP-HPLC (0.1% TFA-ACN in 0.1% TFA Water, Column: Gemini 10 uM, NX-C18 110 Angstrom, 250×30 mm) to give the title compound Example 615 as a trifluoroacetate salt.

ES/MS: 488.0 (M+).

1H NMR (400 MHz, DMSO-$d_6$) δ 12.12 (s, 1H), 8.96 (d, J=2.2 Hz, 1H), 8.46 (d, J=2.1 Hz, 1H), 8.36 (d, J=2.2 Hz, 1H), 7.83 (dd, J=8.2, 1.2 Hz, 1H), 7.70 (t, J=7.9 Hz, 1H), 7.64 (d, J=2.2 Hz, 1H), 7.59-7.54 (m, 2H), 7.05 (s, 1H), 2.63 (s, 3H), 2.02 (tt, J=8.5, 5.1 Hz, 1H), 1.08-1.00 (m, 2H), 0.78-0.73 (m, 2H).

Examples 616-618

The following Examples were made in an analogous fashion according to Procedure 83 and are shown below in Table 36. Any different reagents/starting materials than those described in Procedure 83 are noted in the last column of Table 36—"Changes to Procedure 83. Different Reagents/Starting Materials".

TABLE 36

| | Examples 616-618 | | | |
| --- | --- | --- | --- | --- |
| Example | Structure | ES/MS m/z | 1H-NMR | Changes to Procedure 83: Different Reagents/Starting Materials |
| 616 | | 474.0 | 1H NMR (400 MHz, DMSO-d6) δ 12.10 (s, 1H), 9.25 (dd, J = 5.3, 1.2 Hz, 1H), 9.19 (t, J = 1.8 Hz, 1H), 8.44 (d, J = 2.1 Hz, 1H), 8.33 (d, J = 2.2 Hz, 1H), 7.84 (dd, J = 8.2, 1.2 Hz, 1H), 7.75-7.66 (m, 2H), 7.59 (dd, J = 7.7, 1.2 Hz, 1H), 7.53 (t, J = 2.2 Hz, 1H), 7.02 (s, 1H), 2.04-1.98 (m, 1H), 1.08-1.01 (m, 2H), 0.78-0.71 (m, 2H). | 4-(4,4,5,5-tetramethyl-1,3,2-dioxaborolan-2-yl)pyridazine |
| 617 | | 490.2 | 1H NMR (400 MHz, DMSO-d6) δ 12.08 (s, 1H), 8.48 (d, J = 2.1 Hz, 1H), 8.39 (d, J = 2.2 Hz, 1H), 7.66-7.58 (m, 2H), 7.54 (t, J = 7.9 Hz, 1H), 7.46 (s, 1H), 7.36 (dd, J = 7.7, 1.3 Hz, 1H), 6.91 (s, 1H), 3.71 (s, 3H), 2.04 (tt, J = 8.4, 5.1 Hz, 1H), 1.96 (s, 3H), 1.11-1.00 (m, 2H), 0.77 (dt, J = 6.7, 4.5 Hz, 2H). | (1,3-dimethylpyrazol-4-yl)boronic acid |

TABLE 36-continued

Examples 616-618

| Example | Structure | ES/MS m/z | 1H-NMR | Changes to Procedure 83: Different Reagents/Starting Materials |
|---|---|---|---|---|
| 618 | 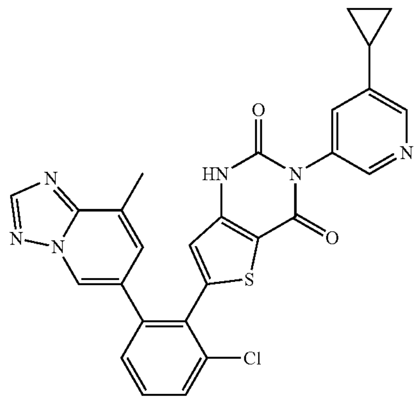 [SMILES: Cc1cc(-c2cccc(Cl)c2-c2cc3[nH]c(=O)n(-c4cncc(C5CC5)c4)c(=O)c3s2)cn2ncnc12] | 527.2 | 1H NMR (400 MHz, DMSO-d6) δ 12.08 (s, 1H), 8.86 (d, J = 1.6 Hz, 1H), 8.48 (s, 1H), 8.45 (d, J = 2.0 Hz, 1H), 8.34 (d, J = 2.2 Hz. 1H), 7.78 (dd, J = 8.1, 1.2 Hz, 1H), 7.66 (t, J = 7.9 Hz, 1H), 7.58-7.52 (m, 2H), 7.46 (d, J = 1.5 Hz, 1H), 7.08 (s, 1H), 2.52 (s, 3H), 2.01 (tt, J = 8.4, 5.0 Hz, 1H), 1.08-1.00 (m, 2H), 0.78-0.70 (m, 2H). | 8-methyl-6-(4,4,5,5-tetramethyl-1,3,2-dioxaborolan-2-yl)-[1,2,4]triazolo[1,5-a]pyridine |

Procedure 84: Example 619

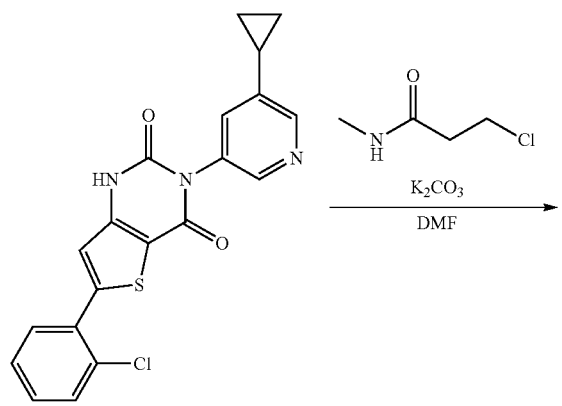

Example 130

3-(6-(2-chlorophenyl)-3-(5-cyclopropylpyridin-3-yl)-2,4-dioxo-3,4-dihydrothieno[3,2-d]pyrimidin-1(2H)-yl)-N-methylpropanamide (Example 619): To a solution of 6-(2-chlorophenyl)-3-(5-cyclopropyl-3-pyridyl)-1H-thieno[3,2-d]pyrimidine-2,4-dione (Example-130) (20.0 mg, 0.0505 mmol) in DMF (2.00 mL) was added 3-chloro-N-methyl-propanamide (12.3 mg, 0.101 mmol) and potassium carbonate (14 mg, 0.101 mmol) and the reaction mixture was heated at 80° C., overnight. The reaction mixture cooled to rt, and a mixture of water (1 mL), MeOH (1 mL), and 0.1% TFA was added. The mixture was filtered through an acrodisc, and subsequently purified by RP-HPLC (0.1% TFA-ACN in 0.1% TFA Water, Column: Gemini 10 uM, NX-C18 110 Angstrom, 250×30 mm) to give the title compound Example 619 as a trifluoroacetate salt.

ES/MS: 481.20 (M+).

$^1$H NMR (400 MHz, DMSO-d$_6$) δ 8.48 (d, J=2.1 Hz, 1H), 8.36 (d, J=2.2 Hz, 1H), 7.96-7.92 (m, 1H), 7.84 (dd, J=5.9, 3.5 Hz, 1H), 7.76 (s, 1H), 7.73-7.67 (m, 1H), 7.58-7.52 (m, 3H), 4.28 (dd, J=8.1, 6.4 Hz, 2H), 2.56-2.54 (m, 5H), 2.09-2.02 (m, 1H), 1.10-1.03 (m, 2H), 0.79-0.75 (m, 2H).

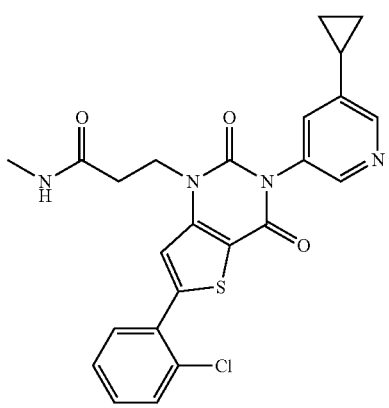 [SMILES: CC(=O)NCCn1c(=O)n(-c2cncc(C3CC3)c2)c(=O)c2sc(-c3ccccc3Cl)cc21]

Example 619

Examples 620-621

The following Examples were made in an analogous fashion according to Procedure 84 and are shown below in Table 37. Any different reagents/starting materials than those described in Procedure 84 are noted in the last column of Table 37—"Changes to Procedure 84: Different Reagents/Starting Materials".

TABLE 37
Examples 620-621
| Example | Structure | ES/MS m/z | 1H-NMR | Changes to Procedure 84: Different Reagents/Starting Materials |
|---|---|---|---|---|
| 620 | 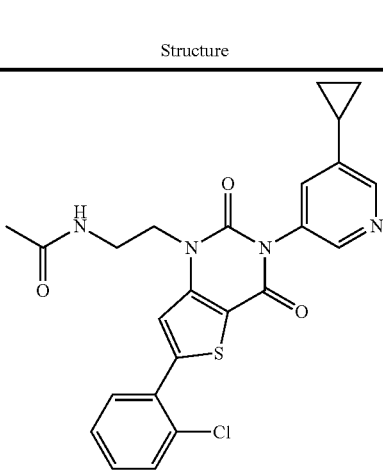 | 481.2 | 1H NMR (400 MHz, DMSO-d6) δ 8.47 (d, J = 2.0 Hz, 1H), 8.32 (d, J = 2.2 Hz, 1H), 8.06 (t, J = 6.1 Hz, 1H), 7.82 (dd, J = 6.0, 3.5 Hz, 1H), 7.75 (s, 1H), 7.73-7.67 (m, 1H), 7.58-7.52 (m, 2H), 7.48-7.47 (m, 1H), 4.12 (t, J = 6.2 Hz, 2H), 3.39-3.37 (m, 2H), 2.12-1.97 (m, 1H), 1.69 (s, 3H), 1.12-1.01 (m, 2H), 0.82-0.71 (m, 2H). | N-(2-chloroethyl) acetamide |
| 621 | 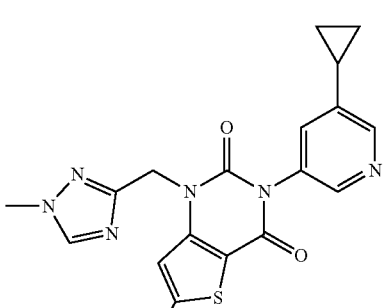 | 491.2 | 1H NMR (400 MHz, DMSO-d6) δ 8.52 (d, J = 2.1 Hz, 1H), 8.44-8.39 (m, 2H), 7.82-7.73 (m, 2H), 7.71-7.64 (m, 2H), 7.58-7.49 (m, 2H), 5.36 (s, 2H), 3.82 (s, 3H), 2.08 (tt, J = 8.4, 5.1 Hz, 1H), 1.15-1.01 (m, 2H), 0.85-0.73 (m, 2H). | 3-(chloromethyl)-1-methyl-1,2,4-triazole |
Procedure 85: Example 622
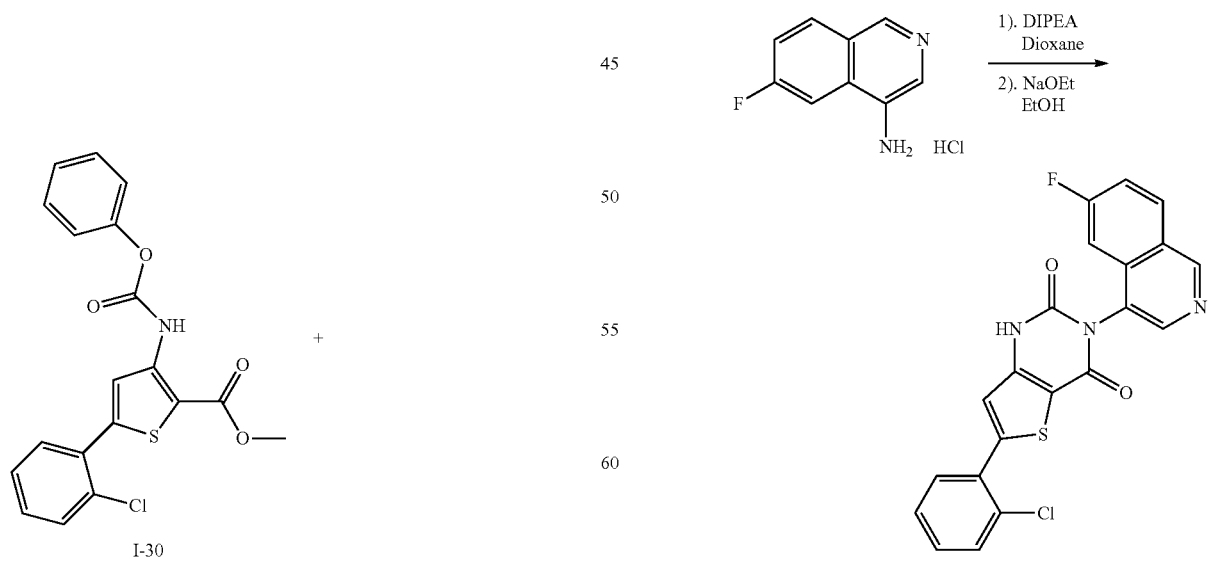
Example 622

6-(2-chlorophenyl)-3-(6-fluoroisoquinolin-4-yl)thieno[3,2-d]pyrimidine-2,4(1H,3H)-dione (Example 622): To a dram vial with methyl 5-(2-chlorophenyl)-3-(phenoxycarbonylamino)thiophene-2-carboxylate (I-30) (250 mg, 0.645 mmol) and 6-fluoroisoquinolin-4-amine hydrochloride (154 mg, 0.774 mmol) was added DIPEA (225 μL, 0.1.29 mmol) and dioxane (5 mL). The reaction mixture was stirred at 80° C. for 4 hours. The reaction mixture was then cooled to ambient temperature and concentrated under reduced pressure. To the resulting crude residue was then added EtOH (3 mL) and NaOEt (614 μL, 21% in EtOH, 1.9 mmol). The reaction mixture was then stirred at 80° C. for 4 hours. The reaction was diluted with 1N HCl (0.5 mL). The resulting solid was filtered and dried to afford product Example 622.

ES/MS: 424.1 (M+).

1H NMR (400 MHz, DMSO-d$_6$) δ 12.23 (s, 1H), 9.46 (d, J=0.8 Hz, 1H), 8.60 (s, 1H), 8.41 (dd, J=9.1, 5.5 Hz, 1H), 7.88 (dd, J=10.3, 2.5 Hz, 1H), 7.78-7.73 (m, 1H), 7.70 (ddd, J=7.9, 3.8, 2.3 Hz, 2H), 7.56-7.52 (m, 2H), 7.33 (s, 1H).

Procedure 86: Example 623

(3 mL), and DME (3 mL) and the mixture degassed with argon for 1 minute. To this mixture was added [1,1'-Bis(diphenylphosphino)ferrocene]dichloropalladium(II) (62.5 mg, 0.076 mmol), Copper (I) Chloride (22.7 mg, 0.229 mmol), and Cesium Fluoride (174 mg, 1.15 mmol), and the mixture was degassed with argon for 30 seconds. The vial was sealed, and the reaction mixture was stirred at 130° C. 60 min. The reaction vessel was cooled, and water was added dropwise until precipitation was complete. The precipitate was filtered and washed with water. The solid product was dried to give the title compound Example 623.

ES/MS: 454.13 (M+).

1H NMR (400 MHz, DMSO-d$_6$) δ 12.23 (s, 1H), 9.45 (s, 1H), 8.60 (s, 1H), 8.41 (dd, J=9.2, 5.6 Hz, 1H), 7.86 (dd, J=10.1, 2.6 Hz, 1H), 7.71-7.66 (m, 1H), 7.60 (dd, J=8.7, 1.8 Hz, 1H), 7.33 (d, J=2.2 Hz, 1H), 7.24 (d, J=3.1 Hz, 1H), 7.14 (dd, J=9.0, 3.1 Hz, 1H), 3.86 (d, J=2.6 Hz, 3H).

Procedure 87: Example 624

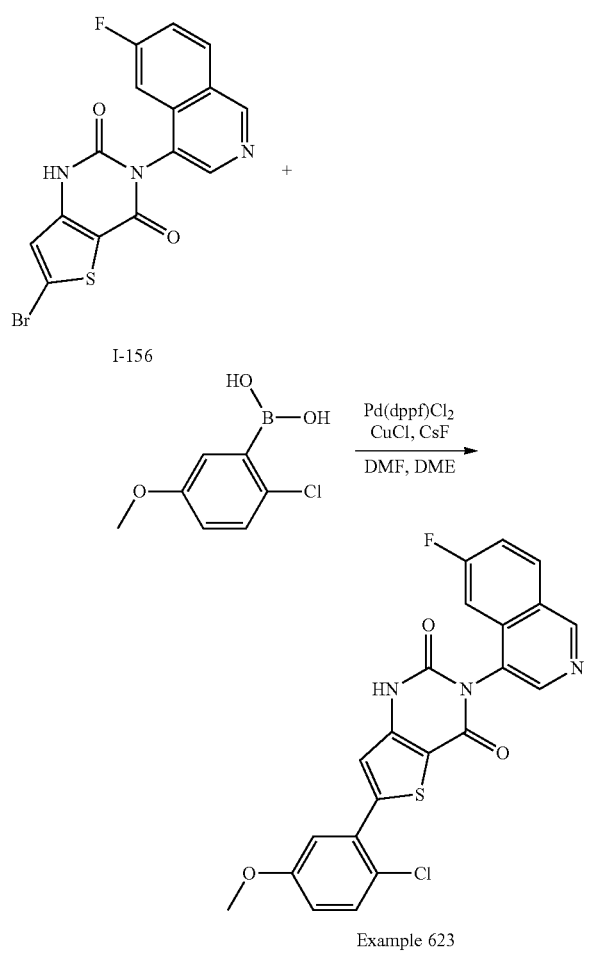

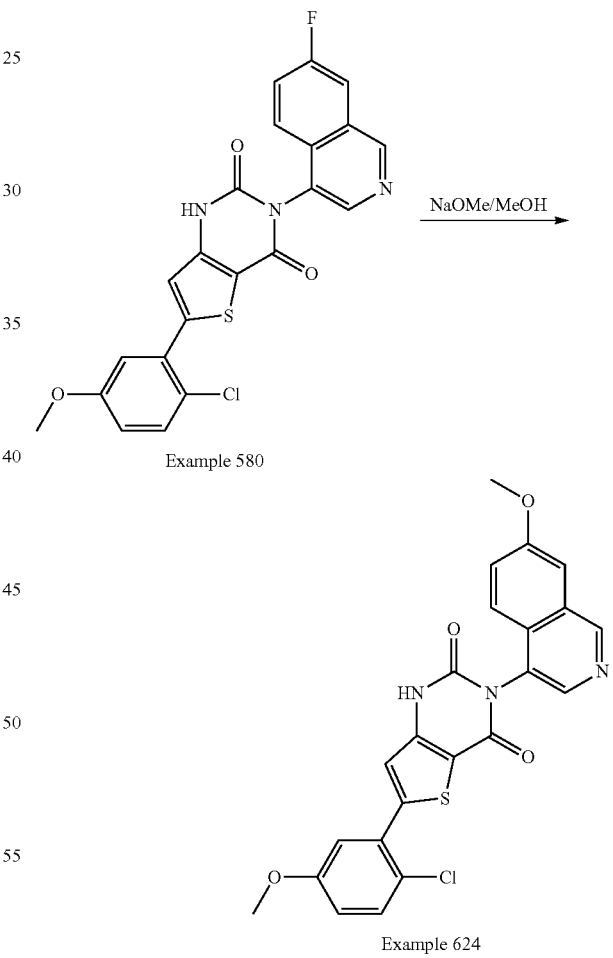

6-(2-chloro-5-methoxyphenyl)-3-(6-fluoroisoquinolin-4-yl)thieno[3,2-d]pyrimidine-2,4(1H,3H)-dione (Example 623): To a microwave vial with 6-bromo-3-(6-fluoroisoquinolin-4-yl)thieno[3,2-d]pyrimidine-2,4(1H,3H)-dione (I-156) (150 mg, 0.382 mmol) was added (2-chloro-5-methoxy-phenyl)boronic acid (107 mg, 0.574 mmol), DMF 6-(2-chloro-5-methoxyphenyl)-3-(7-methoxyisoquinolin-4-yl)thieno[3,2-d]pyrimidine-2,4(1H,3H)-dione (Example 580): To a vial was added 6-(2-chloro-5-methoxyphenyl)-3-(7-fluoroisoquinolin-4-yl)thieno[3,2-d]pyrimidine-2,4(1H,3H)-dione (Example 580) (6 mg, 0.013 mmol), DMSO (0.5 mL) and NMP (0.5 mL), followed by sodium methoxide (0.3 mL, 25% in MeOH). The mixture was stirred at 130° C.

for 2 h. The reaction mixture was cooled to room temperature and filtered. To the crude reaction mixture was added mixture of DMF/MeOH/water (1/1/0.2 mL) and a drop of TFA. The mixture was filtered through an acrodisc and purified directly by RP-HPLC (0.1% TFA-ACN in 0.1% TFA Water, Column: Gemini 10 uM, NX-C18 110 Angstrom, 250×30 mm) to give the product Example 624.

ES/MS: 466.1 (M+).

$^1$H NMR (400 MHz, Methanol-$d_4$) δ 9.40 (s, 1H), 8.46 (s, 1H), 7.83 (d, J=9.1 Hz, 1H), 7.72 (d, J=2.6 Hz, 1H), 7.59 (dd, J=9.2, 2.5 Hz, 1H), 7.53 (d, J=8.9 Hz, 1H), 7.35 (s, 1H), 7.23 (d, J=3.0 Hz, 1H), 7.09 (dd, J=8.9, 3.0 Hz, 1H), 4.04 (s, 3H), 3.89 (s, 3H).

Examples 625-627

The following Examples were made in an analogous fashion according to Procedure 87 and are shown below in Table 38. Any different reagents/starting materials than those described in Procedure 87 are noted in the last column of Table 38—"Changes to Procedure 87: Different Reagents/Starting Materials".

TABLE 38

Examples 625-627

| Example | Structure | ES/MS m/z | 1H-NMR | Changes to Procedure 87: Different Reagents/Starting Materials |
|---|---|---|---|---|
| 625 | 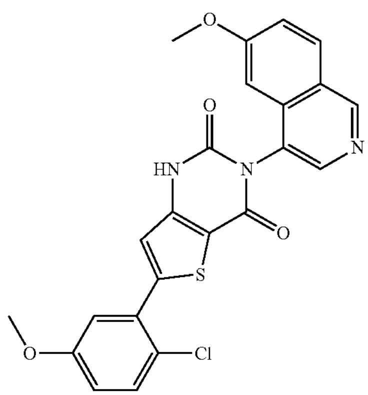 [SMILES: COc1ccc(Cl)c(-c2cc3[nH]c(=O)n(-c4cncc5ccc(OC)cc45)c(=O)c3s2)c1] | 466.2 | 1H NMR (400 MHz, DMSO-d6) δ 12.23 (s, 1H), 9.38 (s, 1H), 8.55 (s, 1H), 8.27 (d, J = 9.1 Hz, 1H), 7.60 (d, J = 8.9 Hz, 1H), 7.46 (dd, J = 9.0, 2.4 Hz, 1H), 7.34 (s, 1H), 7.23 (dd, J = 5.6, 2.7 Hz, 2H), 7.14 (dd, J = 8.9, 3.0 Hz, 1H), 3.90 (s, 3H), 3.85 (s, 3H). | Example 623 |
| 626 | 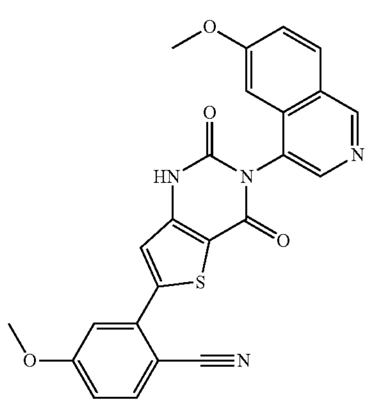 [SMILES: COc1ccc(C#N)c(-c2cc3[nH]c(=O)n(-c4cncc5ccc(OC)cc45)c(=O)c3s2)c1] | 457.2 | 1H NMR (400 MHz, DMSO-d6) δ 12.31 (s, 1H), 9.41 (s, 1H), 8.58 (s, 1H), 8.29 (d, J = 9.1 Hz, 1H), 8.01 (d, J = 8.7 Hz, 1H), 7.53 (s, 1H), 7.48 (dd, J = 9.0, 2.4 Hz, 1H), 7.33 (d, J = 2.5 Hz, 1H), 7.30-7.25 (m, 2H), 3.95 (s, 3H), 3.91 (s, 3H). | Example 589 |

TABLE 38-continued

Examples 625-627

| Example | Structure | ES/MS m/z | 1H-NMR | Changes to Procedure 87: Different Reagents/Starting Materials |
|---|---|---|---|---|
| 627 | 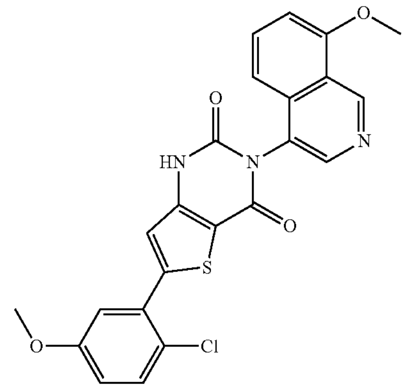 | 466.2 | 1H NMR (400 MHz, DMSO-d6) δ 12.28 (s, 1H), 9.59 (s, 1H), 8.60 (s, 1H), 7.74 (t, J = 8.2 Hz, 1H), 7.60 (d, J = 8.9 Hz, 1H), 7.37 (d, J = 8.4 Hz, 1H), 7.33 (s, 1H), 7.25 (d, J = 3.0 Hz, 1H), 7.22 (d, J = 7.9 Hz, 1H), 7.14 (dd, J = 8.9, 3.0 Hz, 1H), 4.08 (s, 3H), 3.85 (s, 3H). | Example 585 |

Procedure 88: Example 628 and Example 629

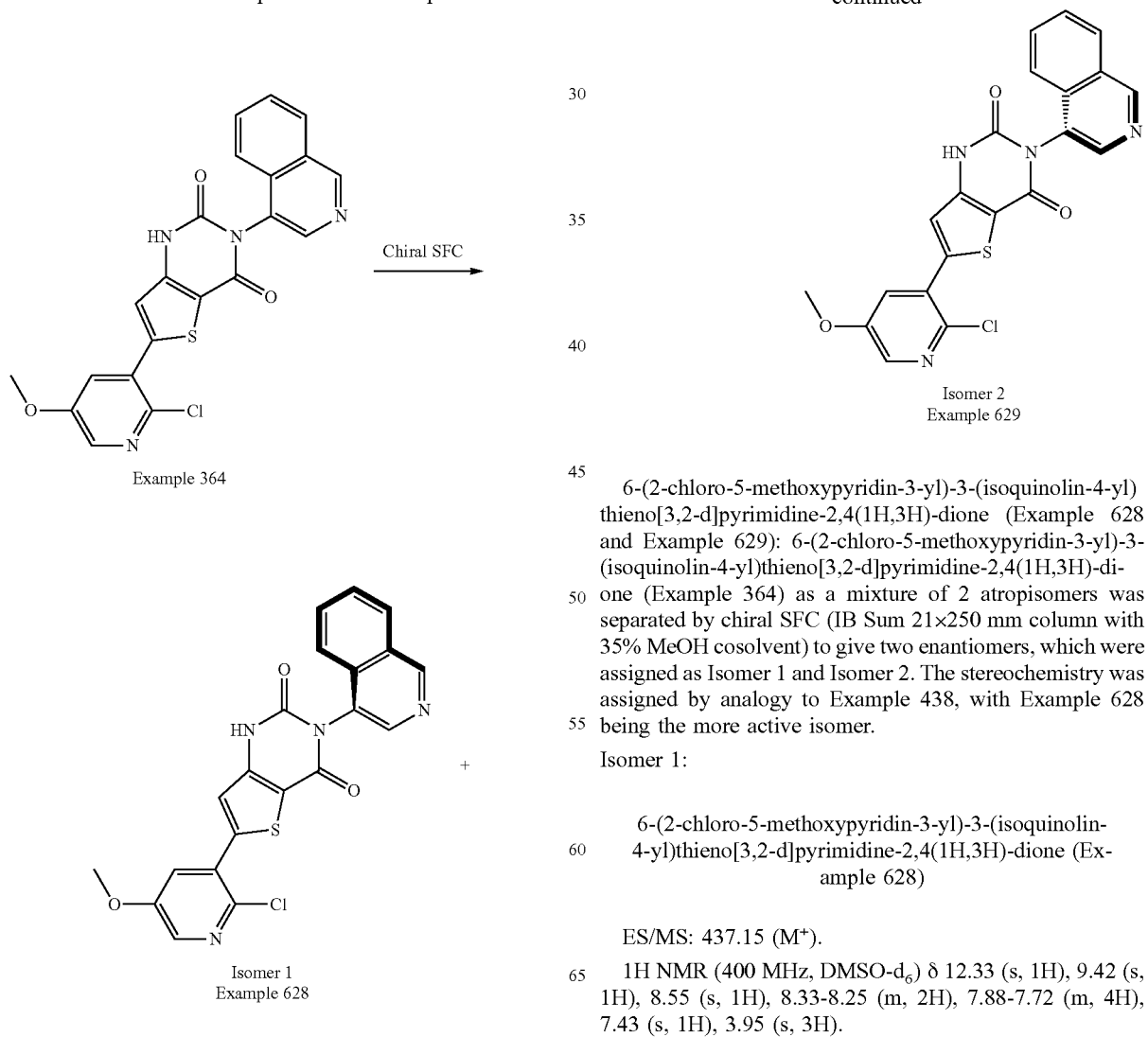

6-(2-chloro-5-methoxypyridin-3-yl)-3-(isoquinolin-4-yl)thieno[3,2-d]pyrimidine-2,4(1H,3H)-dione (Example 628 and Example 629): 6-(2-chloro-5-methoxypyridin-3-yl)-3-(isoquinolin-4-yl)thieno[3,2-d]pyrimidine-2,4(1H,3H)-dione (Example 364) as a mixture of 2 atropisomers was separated by chiral SFC (IB Sum 21×250 mm column with 35% MeOH cosolvent) to give two enantiomers, which were assigned as Isomer 1 and Isomer 2. The stereochemistry was assigned by analogy to Example 438, with Example 628 being the more active isomer.

Isomer 1:

6-(2-chloro-5-methoxypyridin-3-yl)-3-(isoquinolin-4-yl)thieno[3,2-d]pyrimidine-2,4(1H,3H)-dione (Example 628)

ES/MS: 437.15 (M+).

1H NMR (400 MHz, DMSO-d$_6$) δ 12.33 (s, 1H), 9.42 (s, 1H), 8.55 (s, 1H), 8.33-8.25 (m, 2H), 7.88-7.72 (m, 4H), 7.43 (s, 1H), 3.95 (s, 3H).

Isomer 2:

6-(2-chloro-5-methoxypyridin-3-yl)-3-(isoquinolin-4-yl)thieno[3,2-d]pyrimidine-2,4(1H,3H)-dione (Example 629)

ES/MS: 437.15 (M+).

1H NMR (400 MHz, DMSO-$d_6$) δ 12.34 (s, 11H), 9.44-9.39 (m, 1H), 8.57-5.52 (m, 1H), 8.42-8.15 (m, 2H), 7.85-7.74 (m, 4H), 7.54-7.31 (m, 1H), 4.05-3.80 (m, 3H).

Procedure 89: Example 630

ES/MS: 492.7 (M+).

$^1$H NMR (400 MHz, DMSO-$d_6$) δ 9.51 (d, J=0.8 Hz, 1H), 8.65 (s, 1H), 8.32 (dd, J=7.7, 1.5 Hz, 1H), 7.99 (d, J=8.3 Hz, 2H), 7.90-7.72 (m, 3H), 7.54 (d, J=8.8 Hz, 1H), 5.43-5.27 (m, 2H), 3.99 (s, 3H).

Example 631

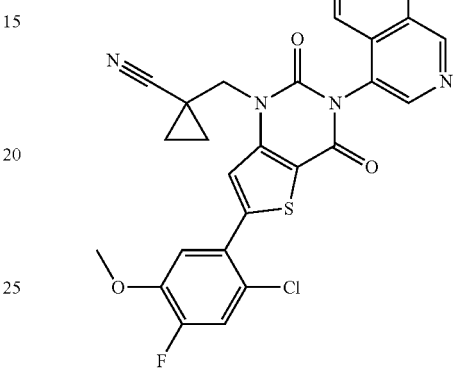

Example 631

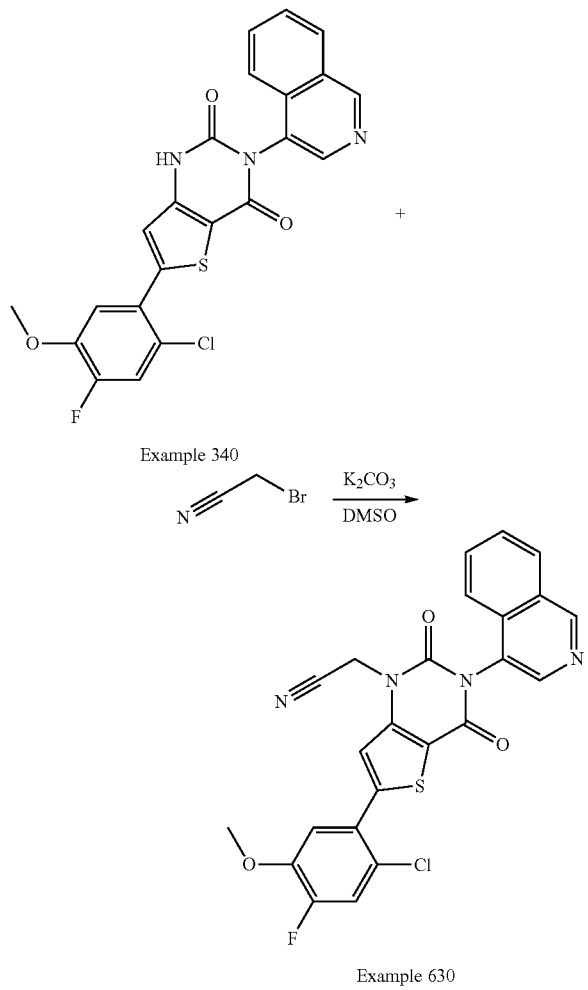

1-[[6-(2-chloro-4-fluoro-5-methoxy-phenyl)-3-(4-isoquinolyl)-2,4-dioxo-thieno[3,2-d]pyrimidin-1-yl]methyl]cyclopropanecarbonitrile (Example 631). Prepared analogously to Example 630, substituting 2-bromoacetonitrile with 1-(bromomethyl)cyclopropanecarbonitrile.

ES/MS: 532.7 (M+).

$^1$H NMR (400 MI-7, DMSO-d6) δ 9.52 (d, J=0.8 Hz, 1H), 8.65 (s, 1H), 8.37-8.30 (m, 1H), 8.06 (s, 1H), 7.93 (dd, J=8.3, 1.3 Hz, 1H), 7.92-7.71 (m, 3H), 7.52 (d, J=8.9 Hz, 1H), 4.51 (d, J=15.2 Hz, 1H), 4.33 (d, J=15.3 Hz, 1H), 3.97 (s, 3H), 1.45-1.27 (m, 4H).

Procedure 90: Example 632

2-[6-(2-chloro-4-fluoro-5-methoxy-phenyl)-3-(4-isoquinolyl)-2,4-dioxo-thieno[3,2-d]pyrimidin-1-yl]acetonitrile (Example 630): To a stirring solution of 6-(2-chloro-4-fluoro-5-methoxy-phenyl)-3-(4-isoquinolyl)-1H-thieno[3,2-d]pyrimidine-2,4-dione (Example 340) (HCl salt) (100 mg, 0.20 mmol, 1.0 equiv.), in DMSO (3 mL), was added 2-bromoacetonitrile (29 mg, 0.25 mmol) followed by K$_2$CO$_3$ (85 mg, 0.61 mmol). The reaction mixture was stirred for 2 hours, after which the mixture was diluted with water (0.2 mL) and TFA (0.5 mL), and the mixture was filtered through an acrodisc, and purified directly by RP-HPLC (0.1% TFA-ACN in 0.1% TFA Water, Column: Gemini 5 μM, NX-C18 110 Angstrom, 250×21.2 mm) to give the product Example 630 as a trifluoroacetate salt.

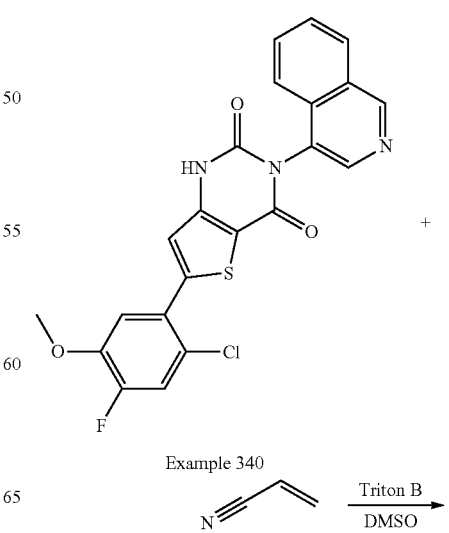

1133
-continued

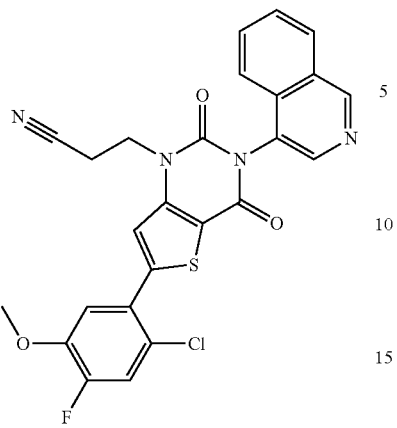

Example 632

2-[6-(2-chloro-4-fluoro-5-methoxy-phenyl)-3-(4-isoquinolyl)-2,4-dioxo-thieno[3,2-d]pyrimidin-1-yl]acetonitrile (Example 632): To a stirring solution of 6-(2-chloro-4-fluoro-5-methoxy-phenyl)-3-(4-isoquinolyl)-1H-thieno[3,2-d]pyrimidine-2,4-dione (Example 340) (HCl salt) (50 mg, 0.10 mmol, 1.0 equiv.), in DMSO (0.46 mL, 0.22 M), was added acrylonitrile (0.13 mL, 2.0 mmol, 20 equiv.) followed by benzyltrimethylammonium hydroxide (54 µL, 0.12 mmol, 1.2 equiv.). The reaction mixture was stirred for 20 hours at 80° C. after which the mixture was diluted with water (0.2 mL) and TFA (0.5 mL). The reaction mixture was then filtered through an acrodisc, and purified directly by RP-HPLC (0.1% TFA-ACN in 0.1% TFA Water, Column: Gemini 5 µM, NX-C18 110 Angstrom, 250×21.2 mm) to give the Product Example 632 as a trifluoroacetate salt.

ES/MS: 506.7 (M+).

$^1$H NMR (400 MHz, DMSO-d6) δ 9.50 (s, 11H), 8.60 (s, 11H), 8.32 (dd, J=7.5, 1.8 Hz, 1H), 8.01-7.89 (m, 2H), 7.88-7.71 (m, 3H), 7.55 (d, J=8.9 Hz, 1H), 4.45 (ddt, J=20.9, 14.2, 6.9 Hz, 2H), 3.98 (s, 3H), 3.04 (t, J=6.6 Hz, 2H).

1134
-continued

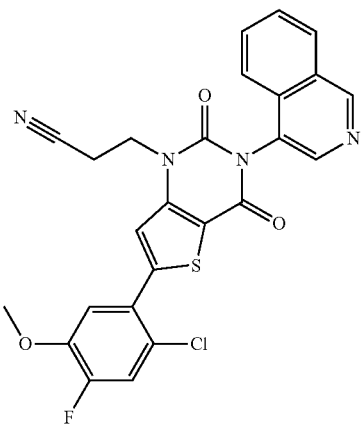

Example 632

3-(6-(2-chloro-4-fluoro-5-methoxyphenyl)-3-(isoquinolin-4-yl)-2,4-dioxo-3,4-dihydrothieno[3,2-d]pyrimidin-1(2H)-yl)propanenitrile (Example 632): To a stirring solution of 6-(2-chloro-4-fluoro-5-methoxyphenyl)-3-(isoquinolin-4-yl)thieno[3,2-d]pyrimidine-2,4(1H,3H)-dione (Example 340) (800 mg, 1.76 mmol), in DMF (2 mL), was added acrylonitrile (3.46 mL, 52.9 mmol) followed by DBU (0.79 mL, 5.29 mmol). The reaction mixture stirred for 16 hours at 80° C. under an N$_2$ atmosphere, after which the mixture was cooled to rt and concentrated under reduced pressure. The reaction mixture was then purified by column chromatography (eluent: EtOAc/Hexanes) to give the title compound Example 632.

ES/MS: 506.8 (M+).

$^1$H NMR (400 MHz, DMSO-d6) δ 9.47 (s, 11H), 8.58 (s, 11H), 8.30 (dd, J=7.3, 1.9 Hz, 1H), 7.98 (s, 1H), 7.90 (d, J=8.0 Hz, 1H), 7.84-7.72 (m, 3H), 7.55 (d, J=8.9 Hz, 1H), 4.59-4.29 (m, 2H), 3.98 (s, 3H), 3.04 (t, J=6.6 Hz, 2H).

Procedure 91: Example 633 and Example 634

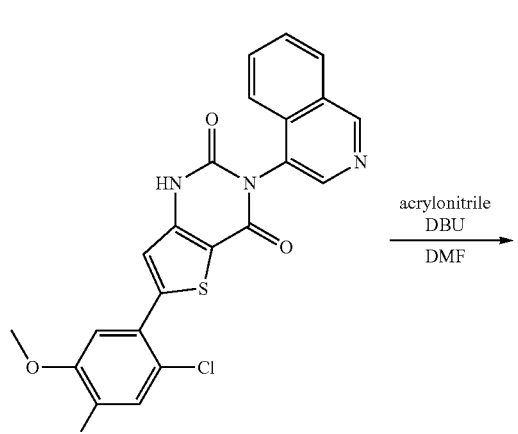

Example 340 acrylonitrile
DBU
DMF
→

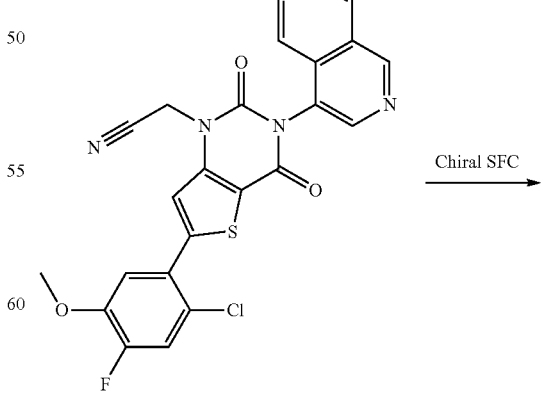

Example 630

Chiral SFC
→

-continued

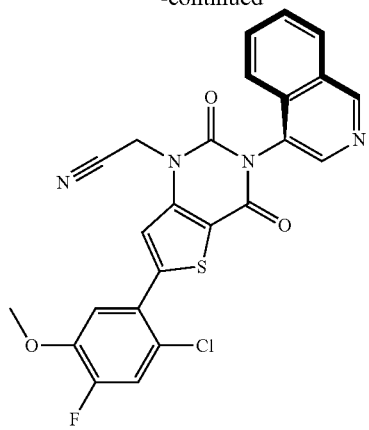

Isomer 1
Example 633

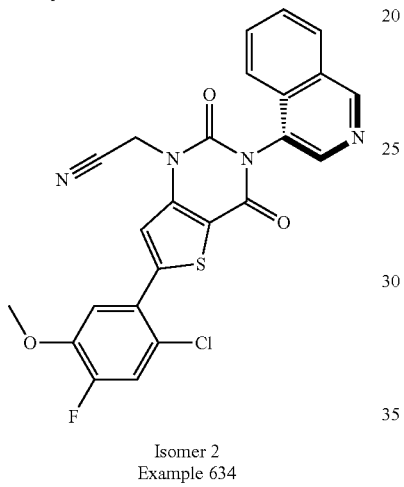

Isomer 2
Example 634

2-[6-(2-chloro-4-fluoro-5-methoxy-phenyl)-3-(4-isoquinolyl)-2,4-dioxo-thieno[3,2-d]pyrimidin-1-yl]acetonitrile (Example 633 and Example 634): 2-[6-(2-chloro-4-fluoro-5-methoxy-phenyl)-3-(4-isoquinolyl)-2,4-dioxo-thieno[3,2-d]pyrimidin-1-yl]acetonitrile (Example 630) as a mixture of 2 isomers was separated by chiral SFC (IK 5 um 4.6×100 mm column with 50% MeOH cosolvent) to give two enantiomers, which were assigned as Isomer 1 and Isomer 2. The stereochemistry was assigned by analogy to Example 438, with Example 633 being the more active isomer.

Isomer 1:

2-[6-(2-chloro-4-fluoro-5-methoxy-phenyl)-3-(4-isoquinolyl)-2,4-dioxo-thieno[3,2-d]pyrimidin-1-yl]acetonitrile (Example 633)

ES/MS: 492.7 (M+).
1H NMR (400 MHz, DMSO-d$_6$) δ 9.50 (s, 1H), 8.65 (s, 1H), 8.32 (dd, J=7.6, 1.5 Hz, 1H), 7.99 (d, J=8.9 Hz, 2H), 7.89-7.72 (m, 3H), 7.54 (d, J=8.9 Hz, 1H), 5.43-5.27 (m, 2H), 3.99 (s, 3H).

Isomer 2:

2-[6-(2-chloro-4-fluoro-5-methoxy-phenyl)-3-(4-isoquinolyl)-2,4-dioxo-thieno[3,2-d]pyrimidin-1-yl]acetonitrile (Example 634)

ES/MS: 492.8 (M+).
1H NMR (400 MHz, DMSO-d$_6$) δ 9.50 (s, 1H), 8.65 (s, 1H), 8.35-8.28 (m, 1H), 7.99 (d, J=9.5 Hz, 2H), 7.89-7.72 (m, 3H), 7.54 (d, J=8.8 Hz, 1H), 5.43-5.27 (m, 2H), 3.99 (s, 3H).

Procedure 92: Example 635 and Example 636

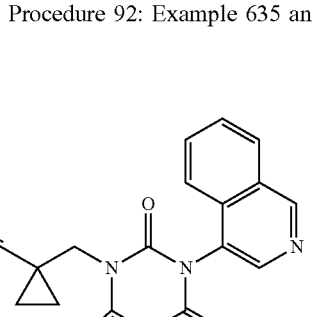

Example 631

Chiral SFC →

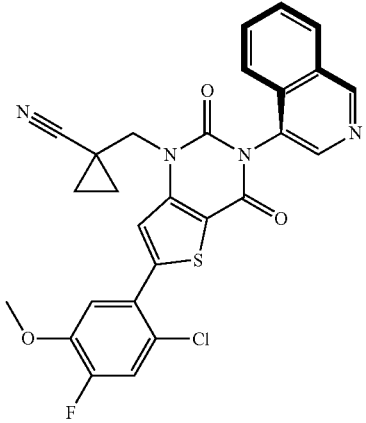

Isomer 1
Example 635

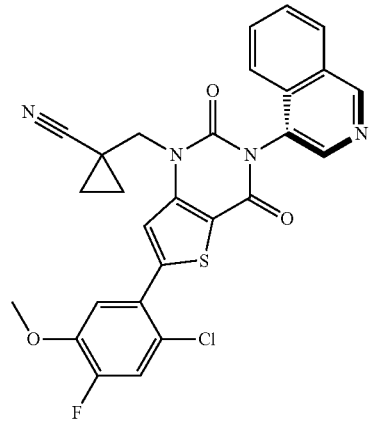

Isomer 2
Example 636

1-[[6-(2-chloro-4-fluoro-5-methoxy-phenyl)-3-(4-isoquinolyl)-2,4-dioxo-thieno[3,2-d]pyrimidin-1-yl]methyl]cyclopropanecarbonitrile (Example 635 and Example 636): 1-[[6-

(2-chloro-4-fluoro-5-methoxy-phenyl)-3-(4-isoquinolyl)-2,4-dioxo-thieno[3,2-d]pyrimidin-1-yl]methyl] cyclopropanecarbonitrile (Example 631) as a mixture of 2 isomers was separated by chiral SFC (IC Sum 4.6×100 mm column with 50% MeOH cosolvent) to give two enantiomers, which were assigned as Isomer 1 and Isomer 2. The stereochemistry was assigned by analogy to Example 438, with Example 635 being the more active isomer.

Isomer 1:

1-[[6-(2-chloro-4-fluoro-5-methoxy-phenyl)-3-(4-isoquinolyl)-2,4-dioxo-thieno[3,2-d]pyrimidin-1-yl] methyl]cyclopropanecarbonitrile (Example 635)

ES/MS: 532.7 (M+).

$^1$H NMR (400 MHz, DMSO-d$_6$) δ 9.50 (s, 1H), 8.63 (s, 1H), 8.32 (dd, J=7.4, 1.7 Hz, 1H), 8.06 (s, 1H), 7.91 (dd, J=8.2, 1.4 Hz, 1H), 7.88-7.71 (m, 3H), 7.52 (d, J=8.9 Hz, 1H), 4.50 (d, J=15.2 Hz, 1H), 4.33 (d, J=15.2 Hz, 1H), 3.96 (s, 3H), 1.45-1.25 (m, 4H).

Isomer 2:

2-[6-(2-chloro-4-fluoro-5-methoxy-phenyl)-3-(4-isoquinolyl)-2,4-dioxo-thieno[3,2-d]pyrimidin-1-yl] acetonitrile (Example 636)

ES/MS: 532.7 (M+).

$^1$H NMR (400 MHz, DMSO-d$_6$) δ 9.50 (s, 1H), 8.63 (s, 1H), 8.32 (dd, J=7.5, 1.6 Hz, 1H), 8.06 (s, 1H), 7.91 (dd, J=8.2, 1.4 Hz, 1H), 7.88-7.71 (m, 3H), 7.52 (d, J=8.9 Hz, 1H), 4.50 (d, J=15.2 Hz, 1H), 4.33 (d, J=15.3 Hz, 1H), 3.96 (s, 3H), 1.45-1.27 (m, 4H).

Procedure 93: Example 637 and Example 638

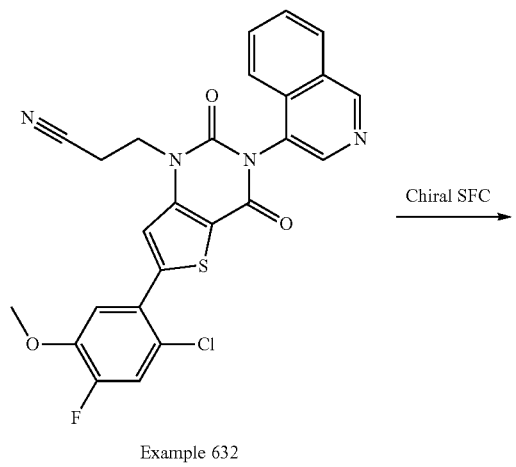

Example 632

Chiral SFC →

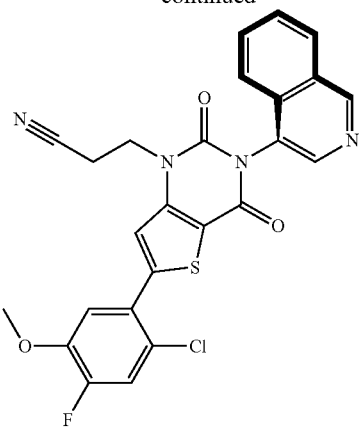

Isomer 1
Example 637

+

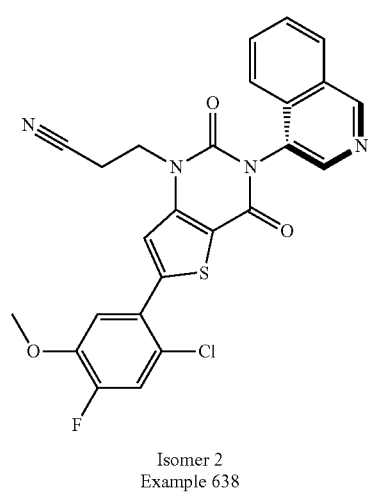

Isomer 2
Example 638

3-[6-(2-chloro-4-fluoro-5-methoxy-phenyl)-3-(4-isoquinolyl)-2,4-dioxo-thieno[3,2-d]pyrimidin-1-yl]propanenitrile (Example 637 and Example 638): 3-[6-(2-chloro-4-fluoro-5-methoxy-phenyl)-3-(4-isoquinolyl)-2,4-dioxo-thieno[3,2-d]pyrimidin-1-yl]propanenitrile (Example 632) as a mixture of 2 isomers was separated by chiral SFC (IB Sum 4.6×100 mm column with 35% MeOH cosolvent) to give two enantiomers, which were assigned as Isomer 1 and Isomer 2. The stereochemistry was assigned by analogy to Example 438, with Example 637 being the more active isomer.

Isomer 1:

3-[6-(2-chloro-4-fluoro-5-methoxy-phenyl)-3-(4-isoquinolyl)-2,4-dioxo-thieno[3,2-d]pyrimidin-1-yl] propanenitrile (Example 637)

ES/MS: 506.7 (M+).

$^1$H NMR (400 MHz, DMSO-d6) δ 9.49 (d, J=0.8 Hz, 1H), 8.59 (s, 1H), 8.31 (dd, J=7.2, 1.8 Hz, 1H), 7.98 (s, 1H), 7.92 (dd, J=8.1, 1.4 Hz, 1H), 7.82 (qd, J=7.2, 1.4 Hz, 2H), 7.80-7.71 (m, 1H), 7.55 (d, J=8.9 Hz, 1H), 4.45 (ddt, J=20.8, 14.1, 6.9 Hz, 2H), 3.98 (s, 3H), 3.04 (t, J=6.6 Hz, 2H).

Isomer 2:
3-[6-(2-chloro-4-fluoro-5-methoxy-phenyl)-3-(4-isoquinolyl)-2,4-dioxo-thieno[3,2-d]pyrimidin-1-yl] propanenitrile (Example 638)
ES/MS: 506.7 (M+).
$^1$H NMR (400 MHz, DMSO-d6) δ 9.49 (d, J=0.8 Hz, 1H), 8.59 (s, 1H), 8.35-8.28 (m, 1H), 8.01-7.88 (m, 2H), 7.88-7.71 (m, 3H), 7.55 (d, J=8.9 Hz, 1H), 4.55-4.37 (m, 2H), 3.98 (s, 3H), 3.04 (t, J=6.6 Hz, 2H).
Procedure 94: Example 639 and Example 640
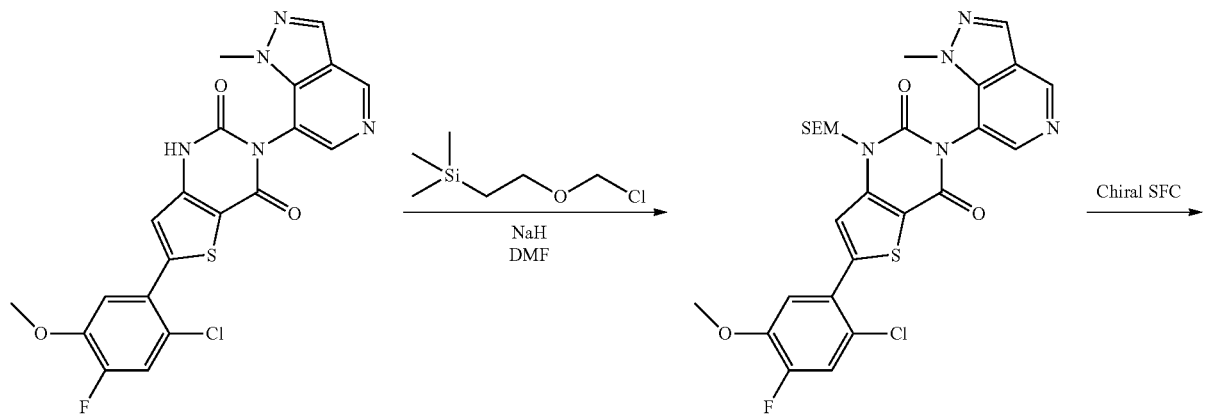
Example 505
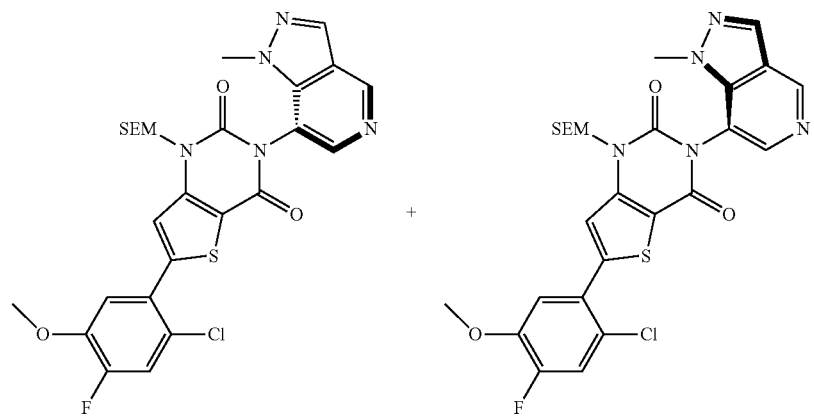
Isomer 1     +     Isomer 2
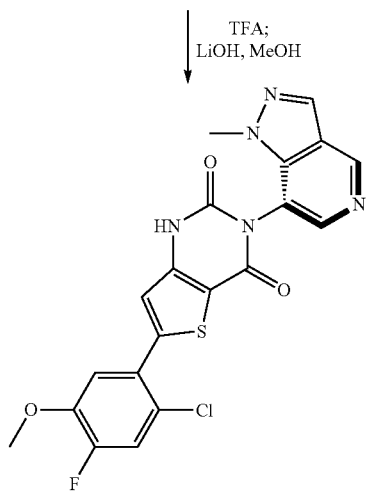 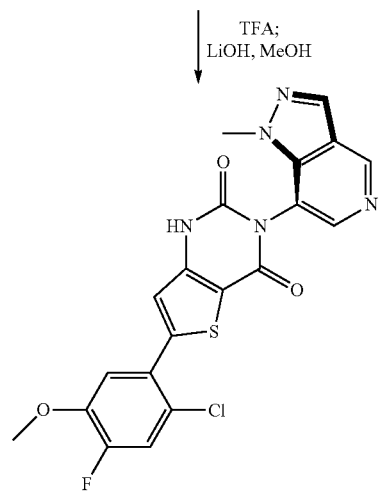
Example 639     +     Example 640

6-(2-chloro-4-fluoro-5-methoxyphenyl)-3-(1-methyl-1H-pyrazolo[4,3-c]pyridin-7-yl)-1-((2-(trimethylsilyl)ethoxy)methyl)thieno[3,2-d]pyrimidine-2,4(1H,3H)-dione. To a stirring solution of 6-(2-chloro-4-fluoro-5-methoxyphenyl)-3-(1-methyl-1H-pyrazolo[4,3-c]pyridin-7-yl)thieno[3,2-d]pyrimidine-2,4(1H,3H)-dione (Example 505) (2.1 g, 4.59 mmol, 1 equiv.) in DMF (15 mL) at 0° C. was added NaH (60% wt dispersion in mineral oil; 0.264 g, 6.88 mmol, 1.5 equiv.), and the mixture was stirred for 45 min after which 2-(chloromethoxy)ethyl-trimethyl-silane (0.89 mL, 5.05 mmol, 1.1 equiv.) was added. The reaction mixture was stirred at rt for 30 min, after which NaHCO₃A (sat. aq.) (10 mL) was added, followed by EtOAc (100 mL). The partitions were separated, and the organic layer was washed with brine (2×20 mL), dried over MgSO₄, and concentrated under reduced pressure. The crude residue was purified by silica gel chromatography (eluent: EtOAc/hexanes), to provide the product.

ES/MS: 587.8 (M+).

6-(2-chloro-4-fluoro-5-methoxy-phenyl)-3-(1-methylpyrazolo[4,3-c]pyridin-7-yl)-1H-thieno[3,2-d]pyrimidine-2,4-dione (Example 639 and Example 640)

6-(2-chloro-4-fluoro-5-methoxyphenyl)-3-(1-methyl-1H-pyrazolo[4,3-c]pyridin-7-yl)-1-((2-(trimethylsilyl)ethoxy)methyl)thieno[3,2-d]pyrimidine-2,4(1H,3H)-dione as a mixture of 2 isomers was separated by chiral SFC (IC Sum 21×²⁵⁰ mm column with 40% MeOH cosolvent) to provide two enantiomers, which were carried forward separately. Isomer 1:

6-(2-chloro-4-fluoro-5-methoxy-phenyl)-3-(1-methylpyrazolo[4,3-c]pyridin-7-yl)-1H-thieno[3,2-d]pyrimidine-2,4-dione (Example 639)

To a 20 mL vial containing a stir bar was added 6-(2-chloro-4-fluoro-5-methoxyphenyl)-3-(1-methyl-1H-pyrazolo[4,3-c]pyridin-7-yl)-1-((2-(trimethylsilyl)ethoxy)methyl)thieno[3,2-d]pyrimidine-2,4(1H,3H)-dione (Isomer 1) (61.4 mg, 0.1 mmol, 1.0 equiv.), followed TFA (1.5 mL). The reaction mixture was stirred for 2 h and subsequently concentrated under reduced pressure. To a stirring solution of the crude material in MeOH/H₂O (1 mL, 0.1 M) at rt was added LiOH (6.1 mg, 0.26 mmol, 2.5 equiv.). The reaction mixture stirred at rt for 1 hour, after which TFA (0.5 mL) was added. The precipitated solid was collected via filtration and redissolved in DMSO/trifluoroacetic acid (4.0 mL: 4:1), filtered through an acrodisc, and purified directly by RP-HPLC (0.1% TFA-ACN in 0.1% TFA Water, Column: Gemini 5 µM, NX-C18 110 Angstrom, 250×21.2 mm) to give the title compound Example 639 as a trifluoroacetate salt. The stereochemistry of Example 639 was assigned by analogy to Example 438, with Example 639 being the less active isomer.

ES/MS: 457.7 (M⁺).

1H NMR (400 MHz, DMSO-d6) δ 12.53 (s, 1H), 9.36 (s, 1H), 8.57 (d, J=16.8 Hz, 2H), 7.72 (d, J=11.1 Hz, 1H), 7.47 (d, J=8.9 Hz, 1H), 7.34 (s, 1H), 3.96 (s, 3H), 3.95 (s, 3H).

Isomer 2:

6-(2-chloro-4-fluoro-5-methoxy-phenyl)-3-(1-methylpyrazolo[4,3-c]pyridin-7-yl)-1H-thieno[3,2-d]pyrimidine-2,4-dione (Example 640)

To a 20 mL vial containing a stir bar was added 6-(2-chloro-4-fluoro-5-methoxyphenyl)-3-(1-methyl-1H-pyrazolo[4,3-c]pyridin-7-yl)-1-((2-(trimethylsilyl)ethoxy)methyl)thieno[3,2-d]pyrimidine-2,4(1H,3H)-dione (Isomer 2) (61 mg, 0.1 mmol, 1.0 equiv.), followed TFA (1.5 mL). The reaction mixture was stirred for 2 h and subsequently concentrated under reduced pressure. To a stirring solution of the crude material in MeOH/H₂O (1 mL, 0.1 M) at rt was added LiOH (6.1 mg, 0.26 mmol, 2.5 equiv.). The reaction mixture stirred at rt for 1 h after which TFA (0.5 mL) was added. The precipitated solid was collected via filtration and redissolved in DMSO/trifluoroacetic acid (4.0 mL, 4:1), filtered through an acrodisc, and purified directly by RP-HPLC (0.1% TFA-ACN in 0.1% TFA Water, Column: Gemini 5 µM, NX-C18 110 Angstrom, 250×21.2 mm) to give the title compound Example 640 as a trifluoroacetate salt. The stereochemistry of Example 640 was assigned by analogy to Example 438, with Example 640 being the more active isomer.

ES/MS: 457.8 (M+).

1H NMR (400 MHz, DMSO-d6) δ 12.53 (s, 1H), 9.36 (s, 1H), 8.58 (d, J=16.9 Hz, 2H), 7.72 (d, J=11.0 Hz, 1H), 7.47 (d, J=8.8 Hz, 1H), 7.34 (s, 1H), 3.96 (s, 3H), 3.95 (s, 3H).

Procedure 95: Example 641

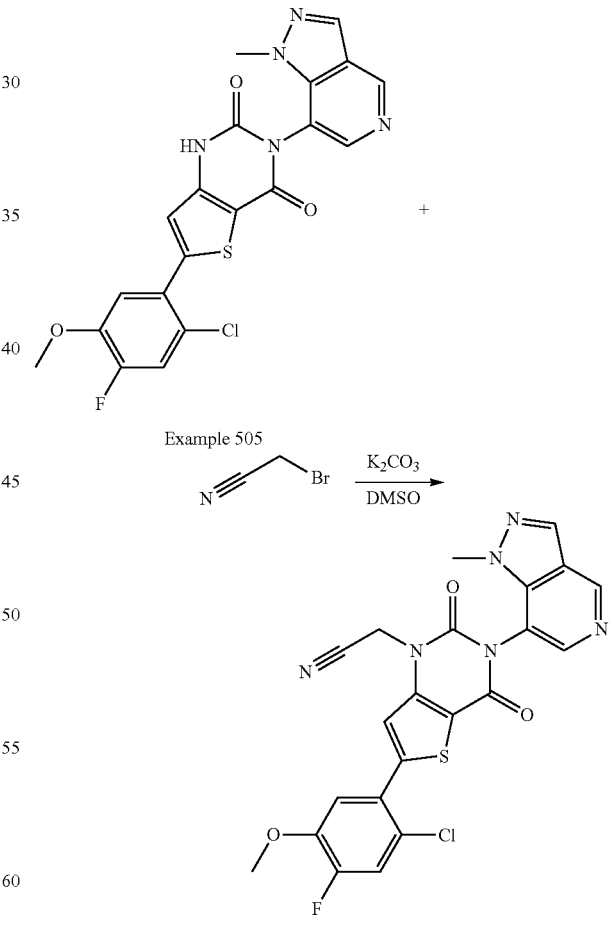

Example 505

Example 641

2-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]acetonitrile (Example 641): To a 40 mL vial containing 6-(2-chloro-4-fluoro-5-methoxy-phenyl)-3-(1-methylpyrazolo[4,3-c]pyridin-7-yl)-1H-thieno[3,2-d]pyrimidine-2,4-dione (Example 505) (200 mg, 0.41 mmol), was added 2-bromoacetonitrile (33.8 µL, 0.49 mmol), potassium carbonate (168 mg, 1.21 mmol), and DMSO (6.00 mL). The resulting mixture was stirred at ambient temperature for one hour and filtered through Celite to remove all solids. The resulting solution was then filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the title compound Example 641 as a trifluoroacetate salt.

ES/MS: 496.7 (M+).

1H NMR (400 MHz, DMSO-d6) δ 9.34 (s, 1H), 8.56 (d, J=3.7 Hz, 2H), 8.02 (s, 1H), 7.76 (d, J=11.0 Hz, 1H), 7.54 (d, J=8.9 Hz, 1H), 5.51-5.24 (m, 2H), 3.98 (s, 3H), 3.93 (s, 3H).

Procedure 96: Example 642

(0.32 mL, 0.73 mmol), and DMSO (3.00 mL). The resulting mixture was sealed and stirred at 80° C. for 5 hours. The reaction mixture was then cooled to ambient temperature, diluted with acetonitrile (2 mL), water (0.4 mL), and TFA (0.08 mL), then filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the title compound Example 642 as a trifluoroacetate salt.

ES/MS: 510.8 (M+).

1H NMR (400 MHz, DMSO-d6) δ 9.38 (s, 1H), 8.60 (s, 1H), 8.54 (s, 1H), 7.98 (s, 1H), 7.74 (d, J=11.0 Hz, 1H), 7.55 (d, J=8.9 Hz, 1H), 4.62-4.36 (m, 2H), 3.95 (m, 6H), 3.08 (t, J=6.5 Hz, 2H).

Example 642

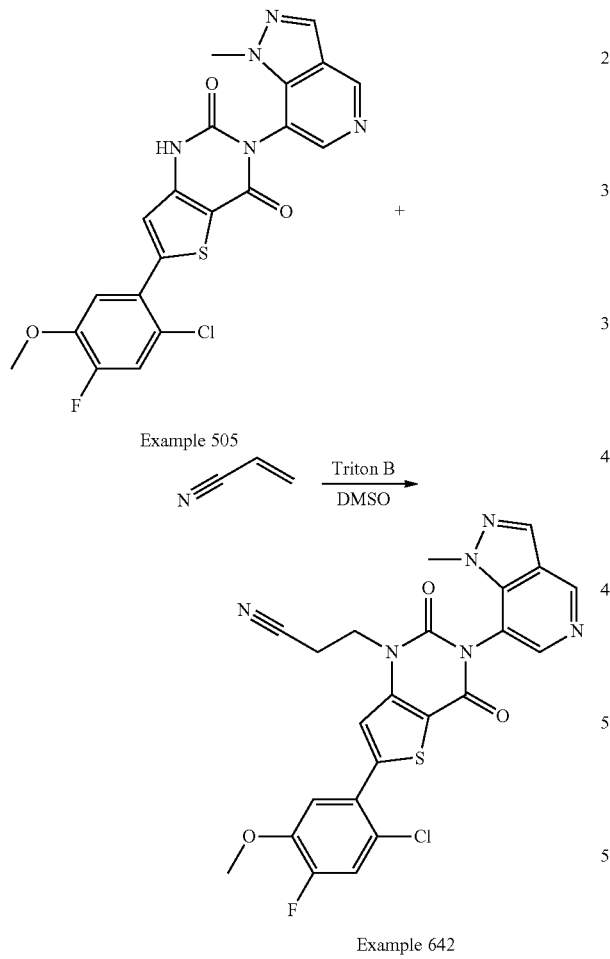

Example 642

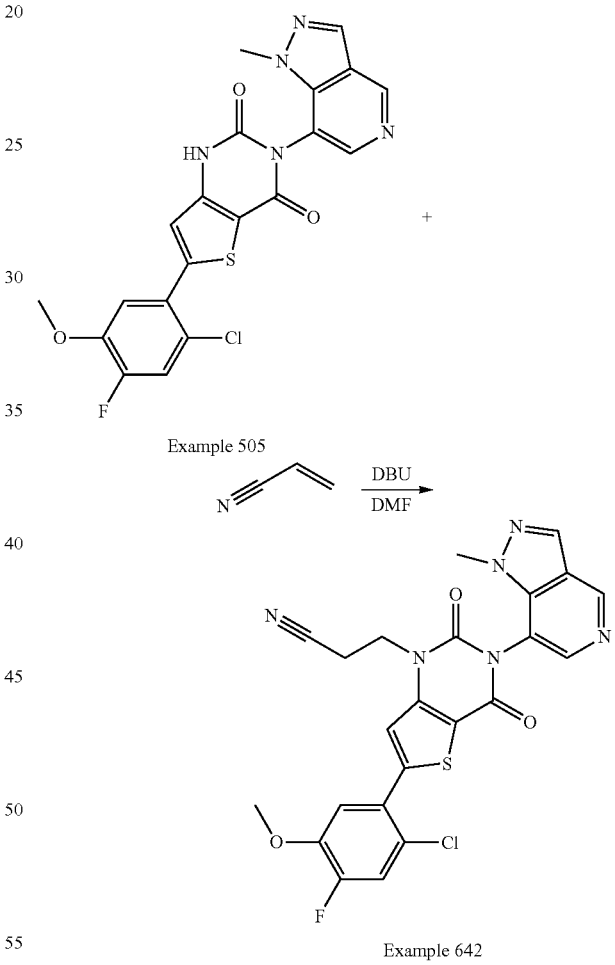

Example 642

3-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]propanenitrile (Example 642): To a reaction vial containing 6-(2-chloro-4-fluoro-5-methoxy-phenyl)-3-(1-methylpyrazolo[4,3-c]pyridin-7-yl)-1H-thieno[3,2-d]pyrimidine-2,4-dione (Example 505) (300 mg, 0.61 mmol), was added acrylonitrile (0.80 mL, 12.1 mmol), Triton B 3-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]propanenitrile (Example 642): To a stirring solution of 6-(2-chloro-4-fluoro-5-methoxy-phenyl)-3-(1-methylpyrazolo[4,3-c]pyridin-7-yl)-1H-thieno[3,2-d]pyrimidine-2,4-dione (Example 505) (HCl salt) (800 mg, 1.62 mmol), in DMF (2.89 mL, 0.56 M), was added acrylonitrile (3.18 mL, 48.6 mmol) followed by DBU (0.48 mL, 3.24 mmol). The reaction mixture stirred for 12 hours at 80° C. after which the mixture was cooled to rt and concentrated under reduced pressure. The reaction mixture was then purified directly column chromatography (eluent: EtOAc/Hexanes) to give the title compound Example 642.

ES/MS: 511.7 (M+).

¹H NMR (400 MHz, DMSO-d6) δ 9.33 (s, 1H), 8.56 (s, 1H), 8.50 (s, 1H), 7.99 (s, 1H), 7.75 (d, J=11.0 Hz, 1H), 7.56 (d, J=8.9 Hz, 1H), 4.55 (dt, J=14.1, 6.9 Hz, 1H), 4.42 (dt, J=14.3, 6.1 Hz, 1H), 3.95 (d, J=16.0 Hz, 6H), 3.09 (d, J=13.1 Hz, 1H).

Procedure 97: Example 643

Gemini 5 uM, NX-C18 110 Angstrom, 250×21.2 mm) to give the title compound Example 643 as a trifluoroacetate salt.

ES/MS: 536.8 (M+).

1H NMR (400 MHz, DMSO-d6) δ 9.42 (s, 1H), 8.63 (d, J=12.1 Hz, 2H), 8.07 (s, 1H), 7.75 (d, J=11.0 Hz, 1H), 7.52 (d, J=8.8 Hz, 1H), 4.43 (dd, J=75.8, 15.3 Hz, 2H), 3.96 (m, 6H), 1.45-1.30 (m, 4H).

Procedure 98: Example 644 and Example 645

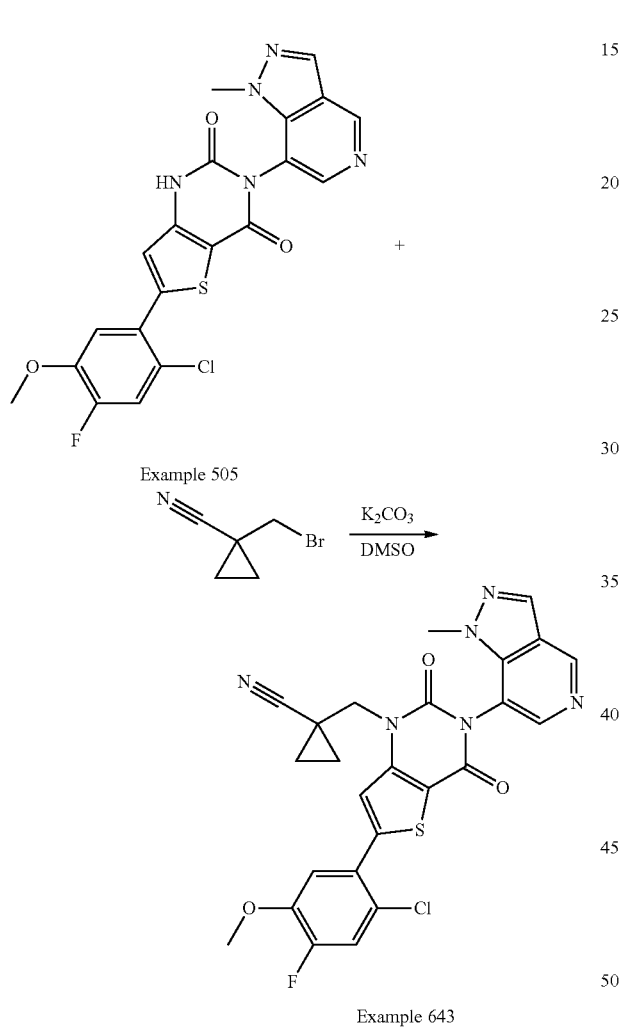

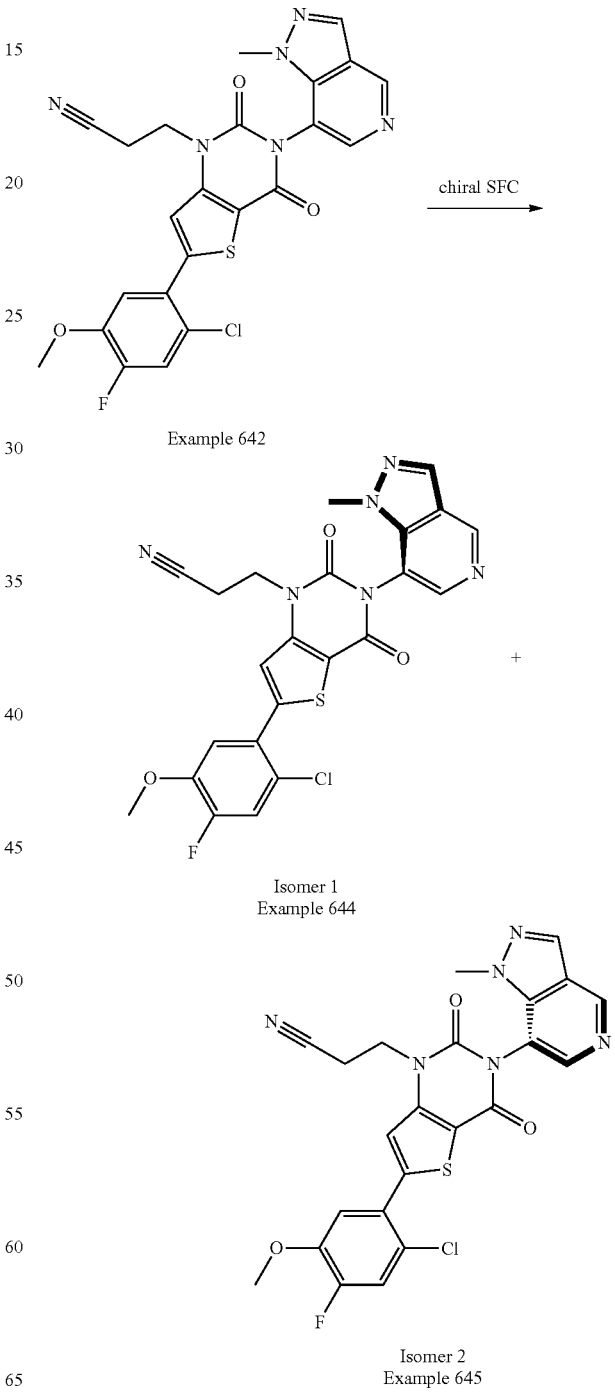

1-[[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]methyl]cyclopropanecarbonitrile (Example 643): To a 40 mL vial containing 6-(2-chloro-4-fluoro-5-methoxy-phenyl)-3-(1-methylpyrazolo[4,3-c]pyridin-7-yl)-1H-thieno[3,2-d]pyrimidine-2,4-dione (Example 505) (200 mg, 0.41 mmol), was added 1-(bromomethyl)cyclopropanecarbonitrile (77.7 mg, 0.49 mmol), potassium carbonate (168 mg, 1.21 mmol), and DMSO (6.00 mL). The resulting mixture was then sealed, stirred at 80° C. for two hours, cooled to ambient temperature, and filtered through Celite to remove all solids. The resulting solution was then filtered through an acrodisc and was subsequently purified by RP-HPLC (0.1% TFA-ACN in 0.1% TFA Water, Column;

3-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]propanenitriledione (Example 644 and Example 645): 3-[6-(2-chloro-4-fluoro-5-methoxy-phenyl)-3-(I-methylpyrazolo[4,3-c]pyridin-7-yl)-2,4-dioxo-thieno[3,2-d]pyrimidin-1-yl]propanenitriledione (Example 642) as a mixture of 2 isomers was separated by chiral SFC (IB 5 um-4.6×$^{100}$ mm column with 35% EtOH cosolvent) to give two enantiomers, which were assigned as Isomer 1 and Isomer 2. The stereochemistry was assigned by analogy to Example 438, with Example 644 being the more active isomer.

Isomer 1:

3-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]propanenitrile (Example 644)

ES/MS: 510.7 (M$^+$).
1H NMR (400 MHz, DMSO-d6) δ 9.36 (s, 1H), 8.59 (s, 1H), 8.52 (s, 1H), 7.98 (s, 1H), 7.74 (d, J=11.0 Hz, 1H), 7.55 (d, J=8.9 Hz, 1H), 4.48 (ddt, J=52.3, 14.3, 6.5 Hz, 2H), 3.97 (s, 3H), 3.94 (s, 3H), 3.08 (t, J=6.5 Hz, 2H).

Isomer 2:

3-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]propanenitrile (Example 645)

ES/MS: 510.7 (M$^+$).
1H NMR (400 MHz, DMSO-d6) δ 9.36 (s, 1H), 8.59 (s, 1H), 8.53 (s, 1H), 7.98 (s, 1H), 7.74 (d, J=11.0 Hz, 1H), 7.55 (d, J=8.9 Hz, 1H), 4.48 (ddt, J=52.3, 14.4, 6.5 Hz, 2H), 3.97 (s, 3H), 3.94 (s, 3H), 3.08 (t, J=6.5 Hz, 2H).

Examples 646-768

The following Examples were made in an analogous fashion according to the procedure indicated in the column of Table 39 titled "Procedure." Any different reagents/starting materials than those described in the indicated procedure are noted in the last column of Table 39—"Changes to Procedure: Different Reagents/Starting Materials".

TABLE 39

Examples 646-768

| Example | Structure | ES/MS m/z | 1H-NMR | Procedure | Changes to Procedure: Different Reagents/Starting Materials |
| --- | --- | --- | --- | --- | --- |
| 646 | 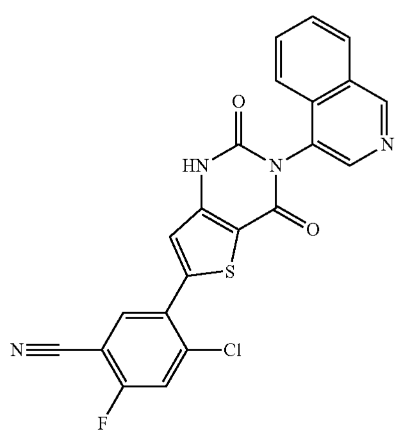 [SMILES: N#Cc1cc(-c2cc3[nH]c(=O)n(-c4cncc5ccccc45)c(=O)c3s2)c(Cl)cc1F] | 448.7 | 1H NMR (400 MHz, DMSO-d6) δ 12.31 (s, 1H), 9.45 (s, 1H), 8.58 (s, 1H), 8.39-8.22 (m, 1H), 8.12 (s, 1H), 8.00-7.71 (m, 3H), 7.28 (s, 1H), 7.24 (s, 1H). | 64 | I-217 |
| 647 | 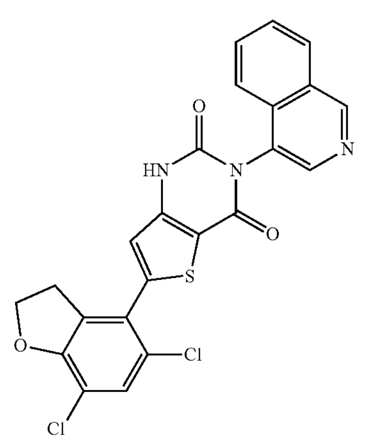 [SMILES: O=c1[nH]c2cc(-c3c(Cl)cc(Cl)c4c3CCO4)sc2c(=O)n1-c1cncc2ccccc12] | 483.7 | 1H NMR (400 MHz, DMSO-d6) δ 12.32 (s, 1H), 9.51 (s, 1H), 8.64 (s, 1H), 8.31 (d, J = 8.0 Hz, 1H), 7.94 (d, J = 8.2 Hz, 1H), 7.89-7.74 (m, 2H), 7.62 (s, 1H), 7.15 (s, 1H), 4.72 (t, J = 8.7 Hz, 2H), 3.34 (t, J = 8.7 Hz, 2H) | 64 | (5,7-dichloro-2,3-dihydrobenzofuran-4-yl)boronic acid |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 648 | 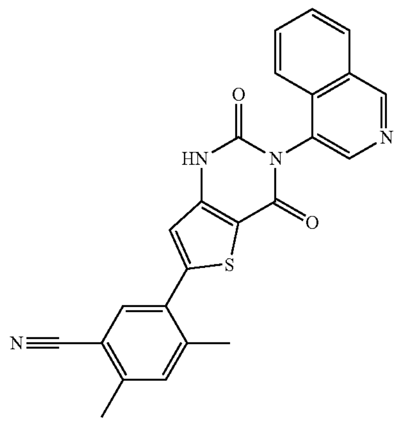 [SMILES: Cc1cc(C)c(-c2cc3[nH]c(=O)n(-c4cncc5ccccc45)c(=O)c3s2)cc1C#N] | 424.9 | 1H NMR (400 MHz, DMSO-d6) δ 12.33 (s, 1H), 9.50 (s, 1H), 8.62 (s, 1H), 8.35-8.28 (m, 1H), 7.93 (s, 1H), 7.91-7.73 (m, 3H), 7.54 (s, 1H), 7.17 (s, 1H), 2.52 (s, 3H), 2.51 (d, J = 3.9 Hz, 3H) | 64 | I-218 |
| 649 | 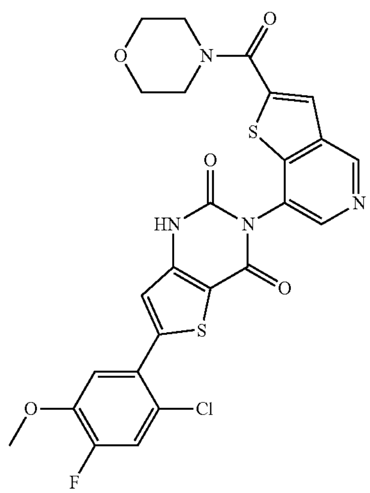 [SMILES: COc1cc(-c2cc3[nH]c(=O)n(-c4cncc5cc(C(=O)N6CCOCC6)sc45)c(=O)c3s2)c(Cl)cc1F] | 573.7 | 1H NMR (400 MHz, DMSO-d6) δ 12.41 (s, 1H), 9.27 (s, 1H), 8.62 (s, 1H), 8.05 (s, 1H), 7.71 (d, J = 11.0 Hz, 1H), 7.46 (d, J = 8.9 Hz, 1H), 7.30 (s, 1H), 3.94 (s, 3H), 3.85-3.53 (m, 8H) | 74 | I-219 |
| 650 | 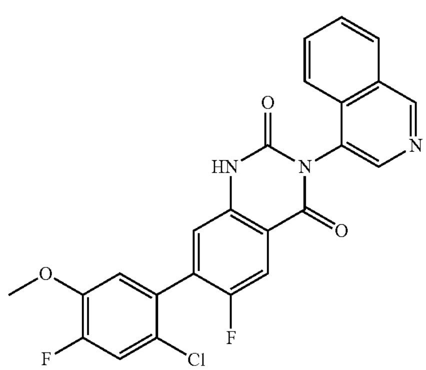 [SMILES: COc1cc(-c2cc3[nH]c(=O)n(-c4cncc5ccccc45)c(=O)c3cc2F)c(Cl)cc1F] | 465.8 | 1H NMR (400 MHz, DMSO-d6) δ 11.94 (s, 1H), 9.52 (s, 1H), 8.64 (s, 1H), 8.32 (d, J = 7.2 Hz, 1H), 7.94 (d, J = 8.1 Hz, 1H), 7.90-7.76 (m, 3H), 7.69 (d, J = 11.0 Hz, 1H), 7.33 (d, J = 8.9 Hz, 1H), 7.27 (d, J = 5.9 Hz, 1H), 3.90 (s, 3H) | 62 | I-3 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 651 | 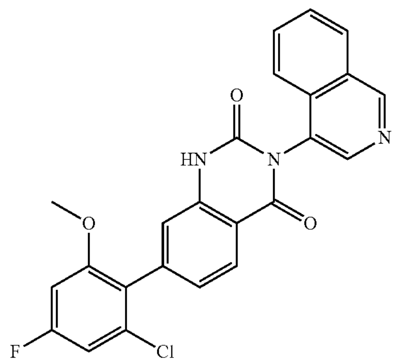 [SMILES: COc1cc(F)cc(Cl)c1-c1ccc2c(=O)n(-c3cncc4ccccc34)c(=O)[nH]c2c1] | 447.8 | 1H NMR (400 MHz, DMSO-d6) δ 11.81 (s, 1H), 9.52 (s, 1H), 8.65 (s, 1H), 8.33 (dd, J = 8.4, 1.5 Hz, 1H), 8.06-7.97 (m, 2H), 7.83 (dddd, J = 14.7, 8.2, 6.9, 1.4 Hz, 2H), 7.28-7.04 (m, 4H), 3.77 (s, 3H) | 5 | 2-bromo-1-chloro-5-fluoro-3-methoxy-benzene |
| 652 | 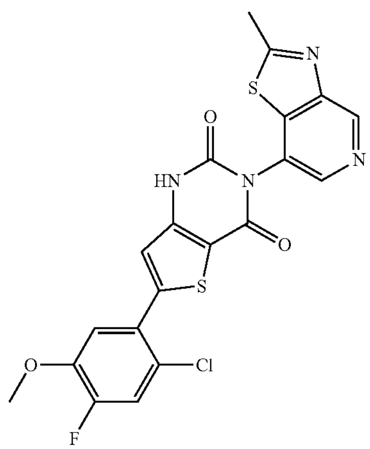 [SMILES: COc1cc(-c2cc3[nH]c(=O)n(-c4cncc5nc(C)sc45)c(=O)c3s2)c(Cl)cc1F] | 474.7 | 1H NMR (400 MHz, DMSO-d6) δ 12.39 (s, 1H), 9.26 (s, 1H), 8.60 (s, 1H), 7.70 (d, J = 11.1 Hz, 1H), 7.45 (d, J = 8.9 Hz, 1H), 7.29 (s, 1H), 3.94 (s, 3H), 2.88 (s, 3H) | 59 | I-61; I-221 |
| 653 | 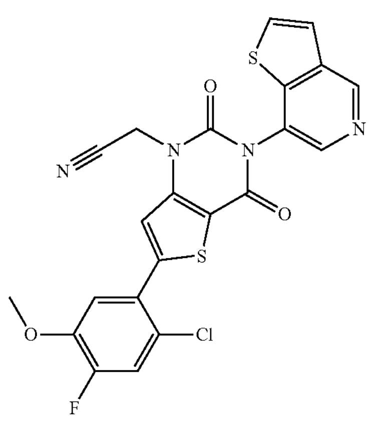 [SMILES: COc1cc(-c2cc3c(s2)c(=O)n(-c2cncc4ccsc24)c(=O)n3CC#N)c(Cl)cc1F] | 498.7 | 1H NMR (400 MHz, DMSO-d6) δ 9.32 (s, 1H), 8.61 (s, 1H), 8.08-7.94 (m, 2H), 7.85-7.69 (m, 2H), 7.55 (d, J = 8.8 Hz, 1H), 5.52-5.11 (m, 2H), 3.97 (s, 3H) | 89 | Example 482 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 654 | 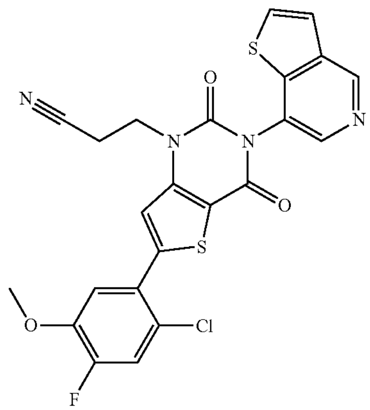 [SMILES: COc1cc(-c2cc3c(s2)c(=O)n(-c2cncc4ccsc24)c(=O)n3CCC#N)c(Cl)cc1F] | 512.6 | 1H NMR (400 MHz, DMSO-d6) δ 9.29 (s, 1H), 8.55 (s, 1H), 7.99 (d, J = 5.4 Hz, 1H), 7.96 (s, 1H), 7.78 (d, J = 5.4 Hz, 1H), 7.74 (d, J = 11.0 Hz, 1H), 7.55 (d, J = 8.9 Hz, 1H), 4.45 (ddt, J = 34.3, 13.9, 6.6 Hz, 2H), 3.96 (s, 3H), 3.03 (t, J = 6.5 Hz, 2H) | 90 | Example 482 |
| 655 | 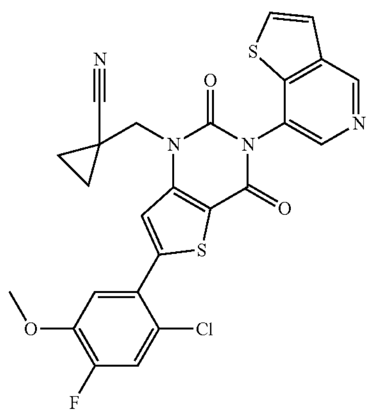 [SMILES: COc1cc(-c2cc3c(s2)c(=O)n(-c2cncc4ccsc24)c(=O)n3CC2(C#N)CC2)c(Cl)cc1F] | 538.7 | 1H NMR (400 MHz, DMSO-d6) δ 9.30 (s, 1H), 8.58 (s, 1H), 8.04 (s, 1H), 8.00 (d, J = 5.4 Hz, 1H), 7.78 (d, J = 5.4 Hz, 1H), 7.74 (d, J = 11.0 Hz, 1H), 7.52 (d, J = 8.9 Hz, 1H), 4.50-4.34 (m, 2H), 3.95 (s, 3H), 1.48-1.29 (m, 4H) | 97 | Example 482 |
| 656 | 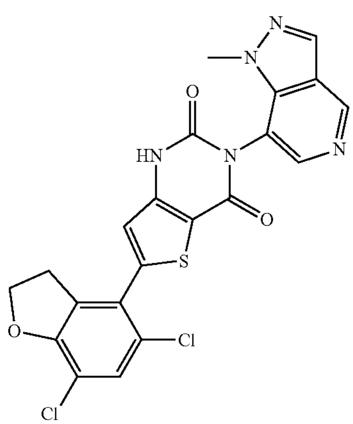 [SMILES: Cn1ncc2cncc(-n3c(=O)[nH]c4cc(-c5c(Cl)cc(Cl)c6c5CCO6)sc4c3=O)c21] | 487.7 | 1H NMR (400 MHz, DMSO-d6) δ 12.51 (s, 1H), 9.31 (s, 1H), 8.12 (d, J = 9.1 Hz, 1H), 7.62 (s, 1H), 7.16 (s, 1H), 6.93 (d, J = 9.2 Hz, 1H), 4.72 (t, J = 8.7 Hz, 2H), 3.94 (s, 3H), 3.34 (t, J = 8.7 Hz, 2H) | 64 | I-188, (5,7-dichloro-2,3-dihydrobenzofuran-4-yl)boronic acid |

TABLE 39-continued

Examples 646-768

| Example | Structure | ES/MS m/z | 1H-NMR | Procedure | Changes to Procedure: Different Reagents/Starting Materials |
|---------|-----------|-----------|--------|-----------|------------------------------------------------------------|
| 657 | 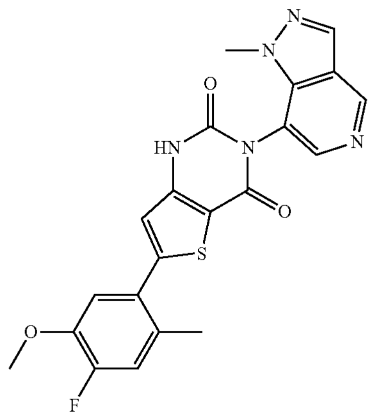 | 437.8 | 1H NMR (400 MHz, DMSO-d6) δ 12.49 (s, 1H), 9.36 (s, 1H), 8.57 (d, J = 18.7 Hz, 2H), 7.31 (d, J = 12.4 Hz, 1H), 7.24 (d, J = 8.7 Hz, 1H), 7.11 (s, 1H), 3.94 (s, 3H), 3.88 (s, 3H), 2.37 (s, 3H | 64 | I-188, I-112 |
| 658 | 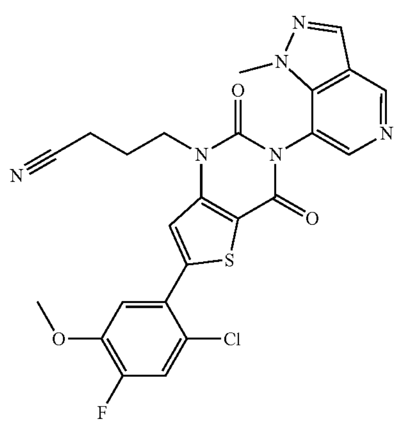 [SMILES: COc1cc(-c2cc3c(s2)c(=O)n(-c2cncc4cnn(C)c24)c(=O)n3CCCC#N)c(Cl)cc1F] | 524.8 | 1H NMR (400 MHz, DMSO-d6) δ 9.32 (s, 1H), 8.56 (s, 1H), 8.49 (s, 1H), 7.85 (s, 1H), 7.75 (d, J = 11.0 Hz, 1H), 7.53 (d, J = 8.9 Hz, 1H), 4.35-4.16 (m, 2H), 3.96 (s, 3H), 3.92 (s, 3H), 2.67 (td, J = 7.2, 1.8 Hz, 2H), 2.07 (q, J = 7.1 Hz, 2H) | 89 | Example 505; 4-Bromobutyronitrile |
| 659 | 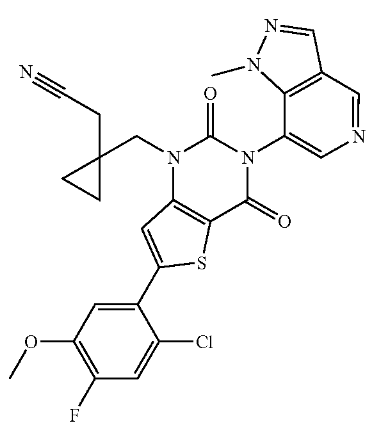 [SMILES: COc1cc(-c2cc3c(s2)c(=O)n(-c2cncc4cnn(C)c24)c(=O)n3CC2(CC#N)CC2)c(Cl)cc1F] | 550.8 | 1H NMR (400 MHz, DMSO-d6) δ 9.34 (s, 1H), 8.58 (s, 1H), 8.51 (s, 1H), 7.90 (s, 1H), 7.75 (d, J = 11.0 Hz, 1H), 7.52 (d, J = 8.8 Hz, 1H), 4.28 (dd, J = 118.0, 15.1 Hz, 2H), 3.96 (s, 3H), 3.94 (s, 3H), 2.82-2.66 (m, 2H), 0.99-0.78 (m, 2H), 0.64 (d, J = 4.3 Hz, 2H | 89 | Example 505; 2-[1-(bromomethyl) cyclopropyl)acetonitrile |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 660 | 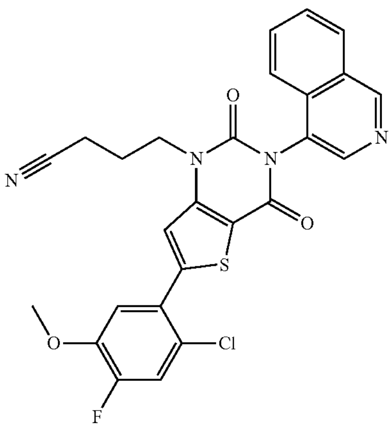 [SMILES: COc1cc(-c2cc3c(s2)c(=O)n(-c2cncc4ccccc24)c(=O)n3CCCC#N)c(Cl)cc1F] | 520.8 | 1H NMR (400 MHz, DMSO-d6) δ 9.48 (s, 1H), 8.59 (s, 1H), 8.36-8.24 (m, 1H), 7.96 (d, J = 8.2 Hz, 1H), 7.89-7.77 (m, 3H), 7.75 (d, J = 11.0 Hz, 1H), 7.52 (dd, J = 8.7.1.9 Hz, 1H), 4.29-4.19 (m, 2H), 3.98 (s, 3H), 2.67 (t, J = 7.2 Hz, 2H), 2.11-2.04 (m, 2H) | 89 | 4-Bromobutyronitrile |
| 661 | 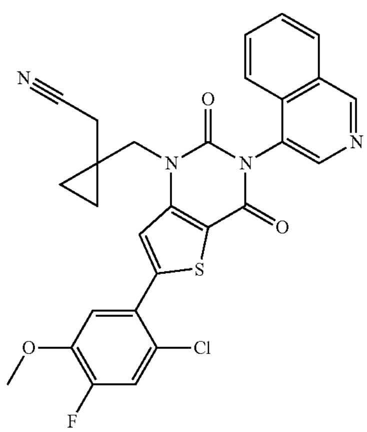 [SMILES: COc1cc(-c2cc3c(s2)c(=O)n(-c2cncc4ccccc24)c(=O)n3CC2(CC#N)CC2)c(Cl)cc1F] | 546.7 | 1H NMR (400 MHz, DMSO-d6) δ 9.49 (s, 1H), 8.59 (s, 1H), 8.32 (dd, J = 7.4, 1.8 Hz, 1H), 7.99-7.93 (m, 1H), 7.88 (s, 1H), 7.82 (qd, J = 7.1, 1.4 Hz, 2H), 7.75 (d, J = 11.1 Hz, 1H), 7.52 (d, J = 8.9 Hz, 1H), 4.26 (dd, J = 63.4, 15.1 Hz, 2H), 3.98 (s, 3H), 2.80-2.66 (m, 2H), 0.87 (dd, J = 9.2, 6.8 Hz, 2H), 0.64 (d, J = 1.4 Hz, 2H) | 89 | 2-[1-(bromomethyl) cyclopropyl]acetonitrile |
| 662 | 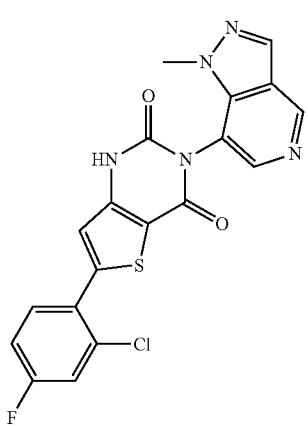 [SMILES: Cn1ncc2cncc(-n3c(=O)[nH]c4cc(-c5ccc(F)cc5Cl)sc4c3=O)c21] | 427.8 | 1H NMR (400 MHz, DMSO-d6) δ 12.52 (s, 1H), 9.38 (s, 1H), 8.60 (s, 2H), 7.83 (dd, J = 8.7, 6.0 Hz, 1H), 7.73 (dd, J = 8.8, 2.6 Hz, 1H), 7.42 (td, J = 8.4, 2.7 Hz, 1H), 7.31 (s, 1H), 3.94 (s, 3H) | 64 | I-188; (2-chloro-4-fluoro-phenyl)boronic acid |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 663 | 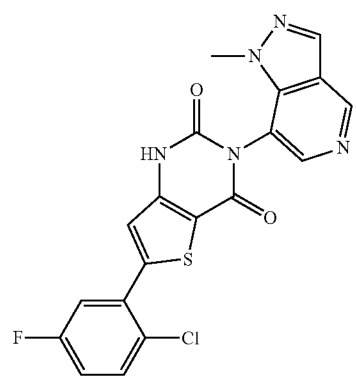 [SMILES: Cn1ncc2cncc(-n3c(=O)[nH]c4cc(-c5cc(F)ccc5Cl)sc4c3=O)c21] | 427.7 | 1H NMR (400 MHz, DMSO-d6) δ 12.57 (s, 1H), 9.40 (s, 1H), 8.61 (s, 2H), 7.84-7.63 (m, 2H), 7.45 (ddd, J = 8.9, 7.9, 3.0 Hz, 1H), 7.40 (s, 1H), 3.95 (s, 3H) | 64 | I-188; (2-chloro-5-fluoro-phenyl)boronic acid |
| 664 | 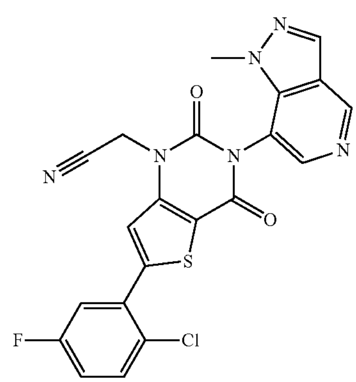 [SMILES: Cn1ncc2cncc(-n3c(=O)c4sc(-c5cc(F)ccc5Cl)cc4n(CC#N)c3=O)c21] | 466.7 | 1H NMR (400 MHz, DMSO-d6) δ 9.32 (s, 1H), 8.55 (d, J = 2.8 Hz, 2H), 8.15 (s, 1H), 7.85 (dd, J = 9.4, 3.1 Hz, 1H), 7.78 (dd, J = 8.9, 5.3 Hz, 1H), 7.48 (ddd, J = 8.9, 7.9, 3.0 Hz, 1H), 5.46-5.26 (m, 2H), 3.92 (s, 3H) | 89 | Example 663 |
| 665 | 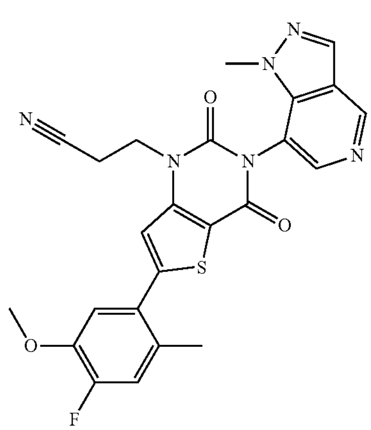 [SMILES: COc1cc(-c2cc3c(s2)c(=O)n(-c2cncc4cnn(C)c24)c(=O)n3CCC#N)c(C)cc1F] | 490.8 | 1H NMR (400 MHz, DMSO-d6) δ 9.33 (s, 1H), 8.56 (s, 1H), 8.50 (s, 1H), 7.80 (s, 1H), 7.33 (d, J = 12.4 Hz, 1H), 7.29 (d, J = 8.7 Hz, 1H), 4.61-4.35 (m, 2H), 3.93 (s, 3H), 3.89 (s, 3H), 3.05 (t, J = 6.4 Hz, 2H), 2.43 (s, 3H) | 96 | Example 657 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 666 | 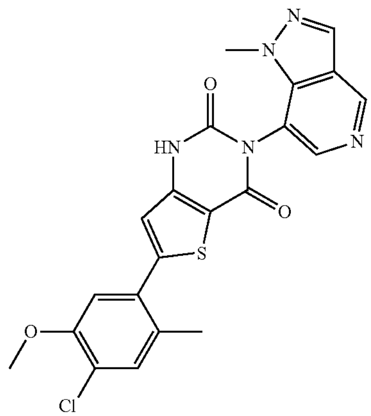 [SMILES: COc1cc(-c2cc3[nH]c(=O)n(-c4cncc5cnn(C)c45)c(=O)c3s2)c(C)cc1Cl] | 453.7 | 1H NMR (400 MHz, DMSO-d6) δ 12.48 (s, 1H), 9.33 (s, 1H), 8.57 (s, 1H), 8.52 (s, 1H), 7.52 (s, 1H), 7.20 (s, 1H), 7.15 (s, 1H), 3.93 (s, 3H), 3.90 (s, 3H), 2.37 (s, 3H) | 64 | I-188; 2-(4-chloro-5-methoxy-2-methyl-phenyl)-4,4,5,5-tetramethyl-1,3,2-dioxaborolane |
| 667 | 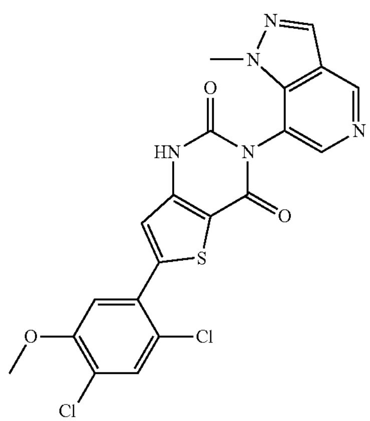 [SMILES: COc1cc(-c2cc3[nH]c(=O)n(-c4cncc5cnn(C)c45)c(=O)c3s2)c(Cl)cc1Cl] | 473.7 | 1H NMR (400 MHz, DMSO-d6) δ 12.51 (s, 1H), 9.30 (s, 1H), 8.54 (s, 1H), 8.50 (s, 1H), 7.85 (s, 1H), 7.41 (s, 1H), 7.37 (s, 1H), 3.96 (s, 3H), 3.92 (s, 3H) | 64 | I-188; (2,4-dichloro-5-methoxy-phenyl)boronic acid |
| 668 | 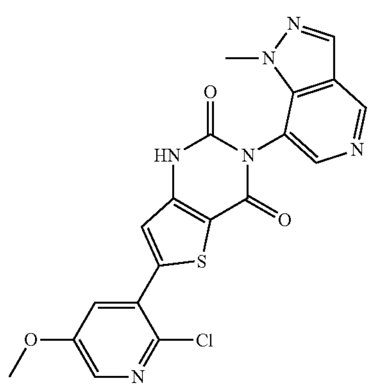 [SMILES: COc1cnc(Cl)c(-c2cc3[nH]c(=O)n(-c4cncc5cnn(C)c45)c(=O)c3s2)c1] | 440.8 | 1H NMR (400 MHz, DMSO-d6) δ 12.55 (s, 1H), 9.35 (s, 1H), 8.57 (s, 2H), 8.29 (d, J = 3.0 Hz, 1H), 7.79 (d, J = 3.0 Hz, 1H), 7.45 (s, 1H), 3.93 (d, J = 2.6 Hz, 6H) | 64 | I-188; (2-chloro-5-methoxy-3-pyridyl)boronic acid |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 669 | 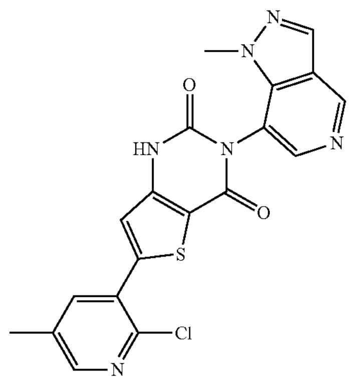 [SMILES: Cc1cnc(Cl)c(-c2cc3[nH]c(=O)n(-c4cncc5cnn(C)c45)c(=O)c3s2)c1] | 424.8 | 1H NMR (400 MHz, DMSO-d6) δ 12.56 (s, 1H), 9.34 (s, 1H), 8.56 (d, J = 15.3 Hz, 2H), 8.39 (s, 1H), 8.10 (d, J = 2.3 Hz, 1H), 7.44 (s, 1H), 3.94 (s, 3H), 2.39 (s, 3H) | 64 | I-188; (2-chloro-5-methyl-3-pyridyl)boronic acid |
| 670 | 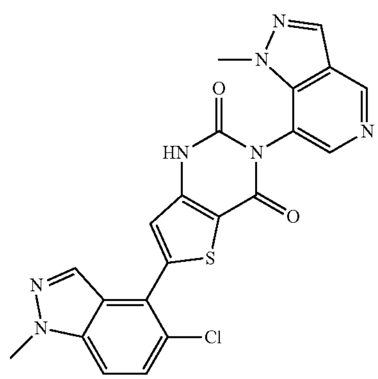 [SMILES: Cn1ncc2c(-c3cc4[nH]c(=O)n(-c5cncc6cnn(C)c56)c(=O)c4s3)c(Cl)ccc21] | 463.8 | 1H NMR (400 MHz, DMSO-d6) δ 12.50 (s, 1H), 9.32 (s, 1H), 8.55 (d, J = 12.8 Hz, 2H), 8.11 (s, 1H), 7.88 (d, J = 9.0 Hz, 1H), 7.65 (d, J = 8.9 Hz, 1H), 7.36 (s, 1H), 4.13 (s, 3H), 3.97 (s, 3H) | 64 | I-188; I-223 |
| 671 | 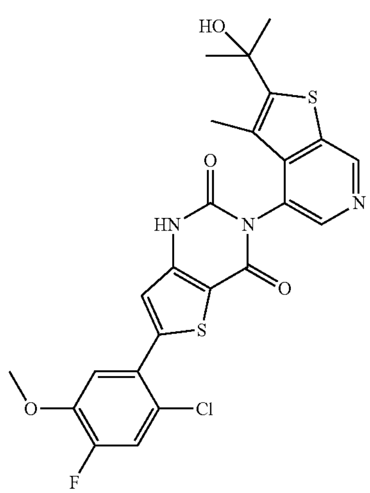 [SMILES: COc1cc(-c2cc3[nH]c(=O)n(-c4cncc5sc(C(C)(C)O)c(C)c45)c(=O)c3s2)c(Cl)cc1F] | 532.7 | 1H NMR (400 MHz, DMSO) δ 12.40 (s, 1H), 9.28 (s, 1H), 8.44 (s, 1H), 7.72 (d, J = 11.1 Hz, 1H), 7.49 (d, J = 8.9 Hz, 1H), 7.31 (s, 1H), 3.95 (s, 3H), 2.22 (s, 3H), 1.60 (d, J = 2.2 Hz, 6H). | 65 | I-269 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 672 | 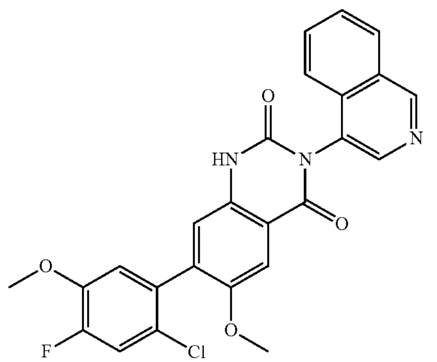 [SMILES: COc1cc(-c2cc3[nH]c(=O)n(-c4cncc5ccccc45)c(=O)c3cc2OC)c(Cl)cc1F] | 477.8 | 1H NMR (400 MHz, DMSO) δ 11.77 (s, 1H), 9.51 (s, 1H), 8.63 (s, 1H), 8.33 (dd, J = 7.8, 1.4 Hz, 1H), 7.83 (ddd, J = 13.1, 10.7, 5.4 Hz, 3H), 7.60 (d, J = 11.1 Hz, 1H), 7.54 (s, 1H), 7.20 (d, J = 9.0 Hz, 1H), 7.14 (s, 1H), 3.91-3.78 (m, 6H). | 78 | I-19. (2-chloro-4-fluoro-5-methoxy-phenyl)boronic acid |
| 673 | 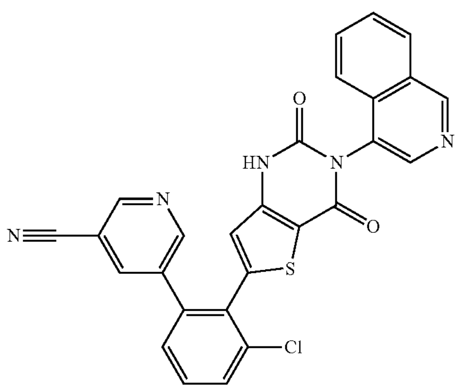 [SMILES: N#Cc1cncc(-c2cccc(Cl)c2-c2cc3[nH]c(=O)n(-c4cncc5ccccc45)c(=O)c3s2)c1] | 507.7 | 1H NMR (400 MHz, HDMSO) δ 12.24 (s, 1H), 9.47 (s, 1H), 9.02 (d, J = 2.1 Hz, 1H), 8.81 (d, J = 2.3 Hz, 1H), 8.61 (d, J = 2.2 Hz, 1H), 8.44-8.38 (m, 1H), 8.34-8.27 (m, 1H), 7.81 (dddd, J = 16.3, 8.2, 5.3, 1.9 Hz, 4H), 7.70 (dd, J = 8.5, 7.3 Hz, 1H). 7.62-7.55 (m, 1H), 7.10-7.05 (m, 1H). | 63 | I-121; 5-(4,4,5,5-tetramethyl-1,3,2-dioxaborolan-2-yl)pyridine-3-carbonitrile |
| 674 | 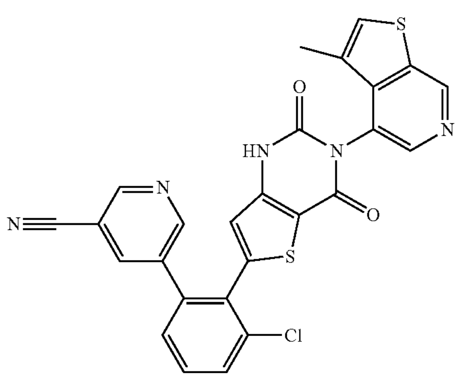 [SMILES: Cc1csc2cncc(-n3c(=O)[nH]c4cc(-c5c(Cl)cccc5-c5cncc(C#N)c5)sc4c3=O)c12] | 527.8 | 1H NMR (400 MHz, DMSO) δ 12.35 (s, 1H), 9.38 (s, 1H), 9.00 (d, J = 1.9 Hz, 1H), 8.81 (d, J = 2.2 Hz, 1H), 8.51 (s, 1H), 8.32 (t, J = 2.1 Hz, 1H), 7.97 (d, J = 1.3 Hz, 1H), 7.83 (dd, J = 8.1, 1.2 Hz, 1H), 7.71 (t, J = 7.9 Hz, 1H), 7.61 (dd, J = 7.7, 1.2 Hz, 1H), 7.08 (s, 1H), 2.12 (d, J = 1.2 Hz, 3H). | 63 | I-270, 5-(4,4,5,5-tetramethyl-1,3,2-dioxaborolan-2-yl)pyridine-3-carbonitrile |
| 675 | 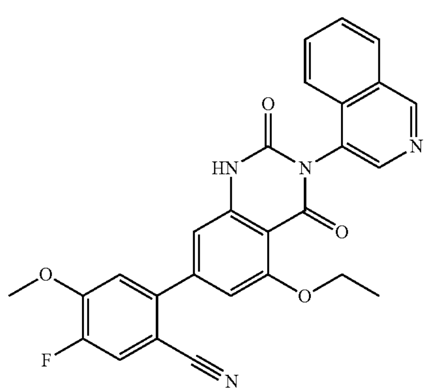 [SMILES: CCOc1cc(-c2cc(OC)c(F)cc2C#N)cc2[nH]c(=O)n(-c3cncc4ccccc34)c(=O)c12] | 482.9 | 1H NMR (400 MHz, DMSO) δ 11.78 (s, 1H), 9.46 (s, 1H), 8.56 (s, 1H), 8.30 (dd, J = 7.4, 1.7 Hz, 1H), 8.05 (d, J = 11.2 Hz, 1H), 7.92-7.74 (m, 3H), 7.44 (d, J = 8.2 Hz, 1H), 7.00 (dd, J = 9.7, 1.5 Hz, 2H), 4.19 (q, J = 6.9 Hz, 2H), 4.04 (s, 3H), 1.32 (t, J = 7.0 Hz, 3H). | 78 | I-271 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 676 | 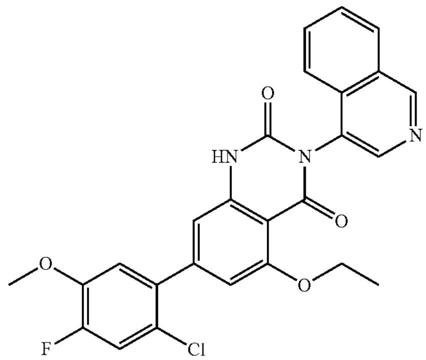 [SMILES: CCOc1cc(-c2cc(OC)c(F)cc2Cl)cc2[nH]c(=O)n(-c3cncc4ccccc34)c(=O)c12] | 491.8 | 1H NMR (400 MHz, DMSO) δ 11.71 (s, 1H), 9.49 (s, 1H), 8.58 (s, 1H), 8.32 (dd, J = 7.6, 1.4 Hz, 1H), 7.92-7.76 (m, 3H), 7.64 (d, J = 11.1 Hz, 1H), 7.35-7.24 (m, 1H), 6.89 (d, J = 1.5 Hz, 1H), 6.83 (d, J = 1.5 Hz, 1H), 4.15 (q, J = 6.9 Hz, 2H), 3.93 (s, 3H), 1.30 (t, J = 6.9 Hz, 3H). | 78 | I-271; (2-chloro-4-fluoro-5-methoxyphenyl)boronic acid |
| 677 | 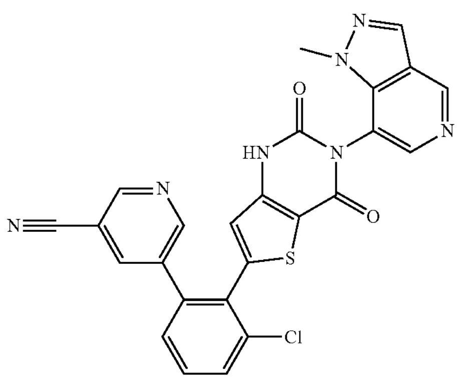 [SMILES: Cn1ncc2cncc(-n3c(=O)[nH]c4cc(-c5c(Cl)cccc5-c5cncc(C#N)c5)sc4c3=O)c21] | 511.7 | 1H NMR (400 MHz, DMSO) δ 12.44 (s, 1H), 9.32 (s, 1H), 9.01 (d, J = 2.0 Hz, 1H), 8.80 (d, J = 2.2 Hz, 1H), 8.54 (d, J = 13.3 Hz, 2H), 8.36 (t, J = 2.1 Hz, 1H), 7.83 (dd, J = 8.1, 1.2 Hz, 1H), 7.71 (t, J = 7.9 Hz, 1H), 7.60 (dd, J = 7.8, 1.2 Hz, 1H), 7.09 (s, 1H), 3.88 (s, 3H). | 63 | I-272; 5-(4,4,5,5-tetramethyl-1,3,2-dioxaborolan-2-yl)pyridine-3-carbonitrile |
| 679 | 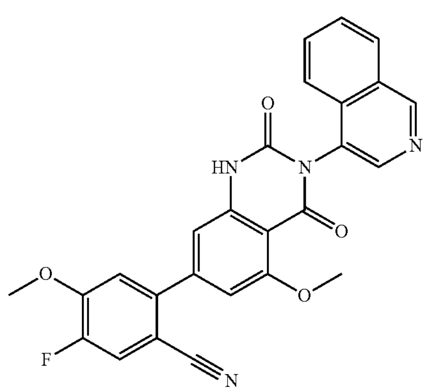 [SMILES: COc1cc(-c2cc(OC)c3c(=O)n(-c4cncc5ccccc45)c(=O)[nH]c3c2)c(C#N)cc1F] | 468.9 | 1H NMR (400 MHz, DMSO) δ 11.81 (s, 1H), 9.47 (s, 1H), 8.57 (s, 1H), 8.34-8.27 (m, 1H), 8.06 (d, J = 11.2 Hz, 1H), 7.92-7.74 (m, 3H), 7.46 (d, J = 8.2 Hz, 1H), 7.06-6.99 (m, 2H), 4.04 (s, 3H), 3.91 (s, 3H). | 78 | I-274 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 681 | 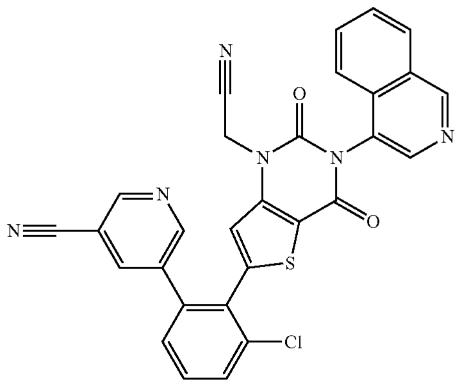 [SMILES: N#CCn1c(=O)n(-c2cncc3ccccc23)c(=O)c2sc(-c3c(Cl)cccc3-c3cncc(C#N)c3)cc21] | 546.7 | 1H NMR (400 MHz, DMSO-d6) δ 9.49 (d, J = 0.8 Hz, 1H), 8.99 (d, J = 2.0 Hz, 1H), 8.74 (d, J = 2.2 Hz, 1H), 8.66 (s, 1H), 8.37 (t, J = 2.1 Hz, 1H), 8.31 (dd, J = 7.6, 1.5 Hz, 1H), 7.97-7.91 (m, 1H), 7.90-7.70 (m, 4H), 7.62 (dd, J = 7.7, 1.2 Hz, 1H), 7.55 (s, 1H), 5.33-5.02 (m, 2H). | 89 | Example 673 |
| 682 | 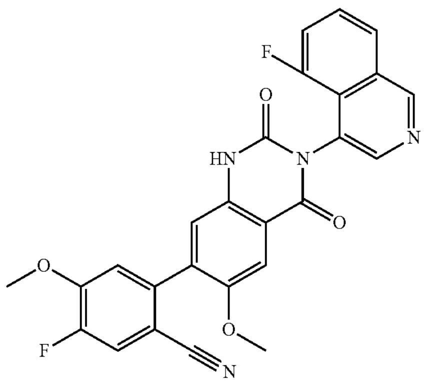 [SMILES: COc1cc(-c2cc3[nH]c(=O)n(-c4cncc5cccc(F)c45)c(=O)c3cc2OC)c(C#N)cc1F] | 486.8 | 1H NMR (400 MHz, DMSO) δ 11.83 (s, 1H), 9.54 (d, J = 2.4 Hz, 1H), 8.64 (s, 1H), 8.19 (dd, J = 8.3, 1.0 Hz, 1H), 7.99 (d, J = 11.2 Hz, 1H), 7.79 (td, J = 8.0, 4.9 Hz, 1H), 7.69-7.58 (m, 2H), 7.45 (d, J = 8.2 Hz, 1H), 7.24 (s, 1H), 3.98 (s, 3H), 3.84 (s, 3H). | 78 | I-278 |
| 683 | 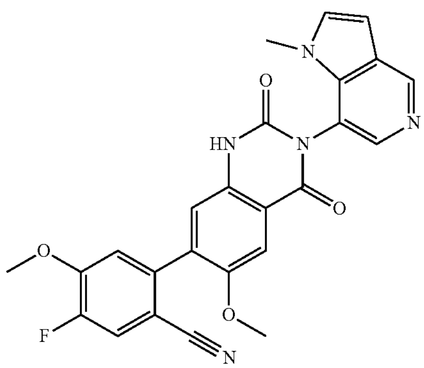 [SMILES: COc1cc(-c2cc3[nH]c(=O)n(-c4cncc5ccn(C)c45)c(=O)c3cc2OC)c(C#N)cc1F] | 471.9 | 1H NMR (400 MHz, DMSO) δ 12.07 (s, 1H), 9.37 (s, 1H), 8.68 (s, 1H), 8.01 (d, J = 11.2 Hz, 1H), 7.89 (d, J = 3.3 Hz, 1H), 7.63 (s, 1H), 7.37 (d, J = 8.2 Hz, 1H), 7.27 (s, 1H), 7.16 (d, J = 3.3 Hz, 1H), 3.97 (s, 3H), 3.86 (s, 3H), 3.79 (s, 3H). | 78 | I-279 |
| 684 | 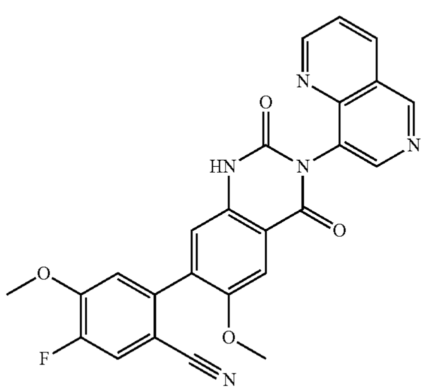 | 469.8 | 1H NMR (400 MHz, DMSO) δ 11.78 (s, 1H), 9.57 (s, 1H), 9.12 (dd, J = 4.3, 1.7 Hz, 1H), 8.87 (s, 1H). 8.75 (dd, J = 8.3, 1.7 Hz, 1H), 8.00 (d, J = 11.2 Hz, 1H), 7.80 (dd, J = 8.3, 4.3 Hz, 1H), 7.57 (s, 1H), 7.42 (d, J = 8.3 Hz, 1H), 7.24 (s, 1H), 3.98 (s, 3H), 3.83 (s, 3H). | 78 | I-280 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 685 | 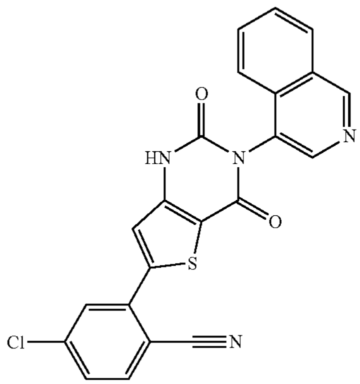 [SMILES: N#Cc1ccc(Cl)cc1-c1cc2[nH]c(=O)n(-c3cncc4ccccc34)c(=O)c2s1] | 430.8 | 1H NMR (400 MHz, DMSO) δ 12.41 (s, 1H), 9.49 (s, 1H), 8.62 (s, 1H), 8.31 (dd, J = 7.6, 1.6 Hz, 1H), 8.12 (d, J = 8.4 Hz, 1H), 8.01 (d, J = 2.1 Hz, 1H), 7.97-7.91 (m, 1H), 7.90-7.75 (m, 3H), 7.58 (s, 1H). | 1 | (5-chloro-2-cyano-phenyl)boronic acid |
| 686 | 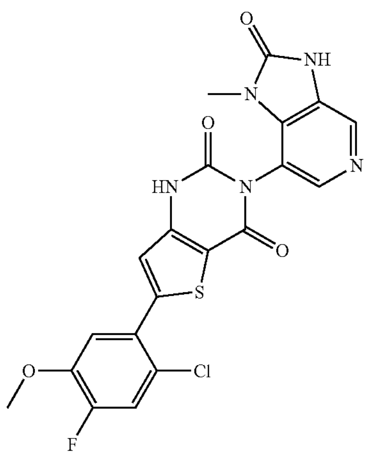 [SMILES: COc1cc(-c2cc3[nH]c(=O)n(-c4cncc5[nH]c(=O)n(C)c45)c(=O)c3s2)c(Cl)cc1F] | 473.7 | 1H NMR (400 MHz, DMSO-d6) δ 12.50 (d, J = 11.7 Hz, 1H), 12.06 (s, 1H), 8.47 (d, J = 6.7 Hz, 2H), 7.72 (d, J = 11.0 Hz, 1H), 7.46 (d, J = 8.9 Hz, 1H), 7.32 (s, 1H), 3.95 (s, 3H), 3.21 (s, 3H). | 94 | I-284 |
| 687 | 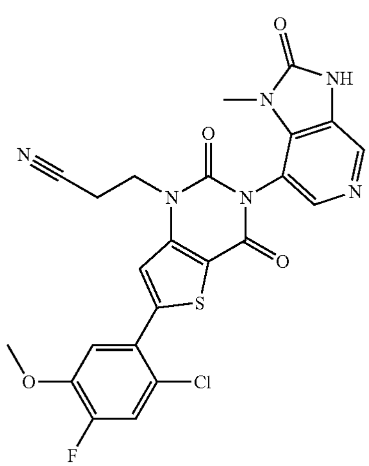 [SMILES: COc1cc(-c2cc3c(s2)c(=O)n(-c2cncc4[nH]c(=O)n(C)c24)c(=O)n3CCC#N)c(Cl)cc1F] | 526.7 | 1H NMR (400 MHz, DMSO) δ 11.92 (s, 1H), 8.43 (s, 1H), 8.36 (s, 1H), 7.97 (s, 1H), 7.75 (d, J = 11.0 Hz, 1H), 7.55 (d, J = 8.9 Hz, 1H), 4.54 (dt, J = 14.1, 6.9 Hz, 1H), 4.40 (dt, J = 14.4, 6.0 Hz, 1H), 3.97 (s, 3H), 3.20 (s, 3H), 3.07 (t, J = 6.5 Hz, 2H). | 94 | I-285 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 688 | 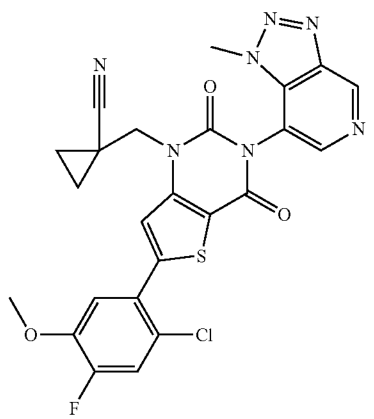 [SMILES: COc1cc(-c2cc3c(s2)c(=O)n(-c2cncc4nnn(C)c24)c(=O)n3CC2(C#N)CC2)c(Cl)cc1F] | 537.7 | 1H NMR (400 MHz, DMSO) δ 9.61 (s, 1H), 8.67 (s, 1H), 8.07 (s, 1H), 7.76 (d, J = 11.0 Hz, 1H), 7.52 (d, J = 8.9 Hz, 1H), 4.52 (d, J = 15.3 Hz, 1H), 4.35 (d, J = 15.2 Hz, 1H), 4.21 (s, 3H), 3.96 (s, 3H), 1.47-1.32 (m, 4H). | 97 | Example 749 |
| 689 | 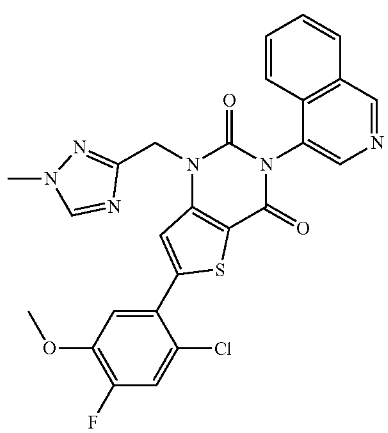 [SMILES: COc1cc(-c2cc3c(s2)c(=O)n(-c2cncc4ccccc24)c(=O)n3Cc2ncn(C)n2)c(Cl)cc1F] | 548.7 | 1H NMR (400 MHz, DMSO-d6) δ 9.50 (d, J = 0.8 Hz, 1H), 8.60 (d, J = 8.9 Hz, 1H), 8.45 (s, 1H), 8.36-8.28 (m, 1H), 7.92-7.76 (m, 4H), 7.72 (d, J = 11.0 Hz, 1H), 7.50 (d, J = 8.8 Hz, 1H), 5.46 (d, J = 16.4 Hz, 1H), 5.38 (d, J = 16.4 Hz, 1H), 3.96 (s, 3H), 3.84 (s, 3H). | 25 | Example 340 |
| 690 | 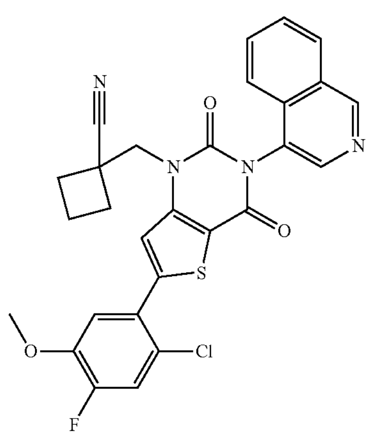 [SMILES: COc1cc(-c2cc3c(s2)c(=O)n(-c2cncc4ccccc24)c(=O)n3CC2(C#N)CCC2)c(Cl)cc1F] | 546.7 | 1H NMR (400 MHz, DMSO-d6) δ 9.49 (s, 1H), 8.62 (s, 1H), 8.35-8.28 (m, 1H), 8.02 (s, 1H), 7.93 (dd, J = 8.3, 1.3 Hz, 1H), 7.88-7.70 (m, 3H), 7.48 (d, J = 8.9 Hz, 1H), 4.60 (s, 2H), 3.95 (s, 3H), 2.48-2.33 (m, 4H), 2.15-1.91 (m, 2H). | 89 | 1-(bromomethyl) cyclobutanecarbonitrile |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 691 | 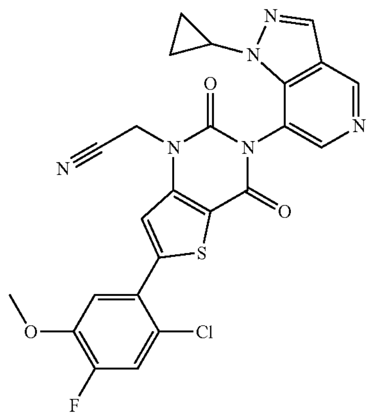 [SMILES: COc1cc(-c2cc3c(s2)c(=O)n(-c2cncc4cnn(C5CC5)c24)c(=O)n3CC#N)c(Cl)cc1F] | 522.7 | 1H NMR (400 MHz, DMSO-d6) δ 9.34 (s, 1H), 8.58 (s, 1H), 8.52 (s, 1H), 8.05 (s, 1H), 7.76 (d, J = 11.0 Hz. 1H), 7.57 (d, J = 8.8 Hz, 1H), 5.46 (d, J = 17.9 Hz, 1H), 5.37 (d, J = 17.9 Hz, 1H), 3.99 (s, 3H), 3.52 (tt, J = 7.2, 3.6 Hz, 1H), 1.10-0.97 (m, 2H), 0.92-0.80 (m, 2H). | 89 | I-302 |
| 692 | 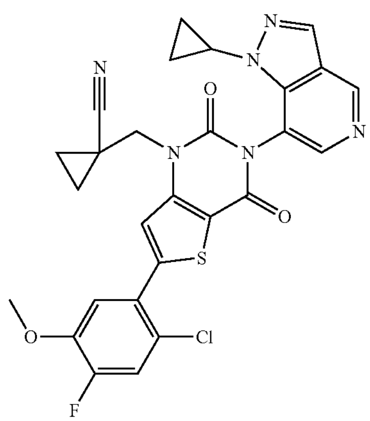 [SMILES: COc1cc(-c2cc3c(s2)c(=O)n(-c2cncc4cnn(C5CC5)c24)c(=O)n3CC2(C#N)CC2)c(Cl)cc1F] | 563.7 | 1H NMR (400 MHz, DMSO-d6) δ 9.32 (s, 1H), 8.54 (d, J = 10.9 Hz, 2H), 8.12 (s, 1H), 7.75 (d, J = 11.0 Hz, 1H), 7.53 (d, J = 8.9 Hz, 1H), 4.54 (d, J = 15.2 Hz, 1H), 4.34 (d, J = 15.2 Hz, 1H), 3.97 (s, 3H), 3.56 (tt, J = 7.1, 3.6 Hz, 1H), 1.45-1.32 (m, 4H), 1.18-1.05 (m, 1H), 1.03 (ddt, J = 11.8, 5.2, 2.3 Hz, 1H), 0.90 (qd, J = 6.1, 2.9 Hz, 2H). | 97 | I-302 |
| 693 | 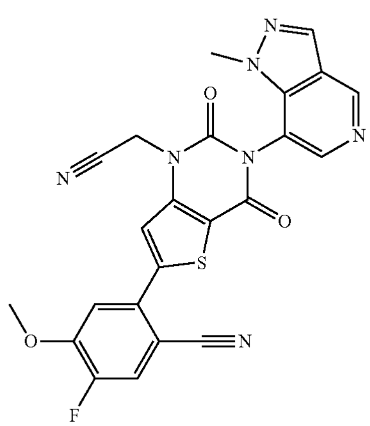 [SMILES: COc1cc(-c2cc3c(s2)c(=O)n(-c2cncc4cnn(C)c24)c(=O)n3CC#N)c(C#N)cc1F] | 487.7 | 1H NMR (400 MHz, DMSO-d6) δ 9.33 (s, 1H), 8.56 (s, 2H), 8.21-8.11 (m, 2H), 7.60 (d, J = 8.1 Hz, 1H), 5.41 (d, J = 18.0 Hz, 1H), 5.31 (d, J = 18.0 Hz, 1H), 4.07 (s, 3H), 3.95 (s, 3H). | 89 | Example 751 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 694 | 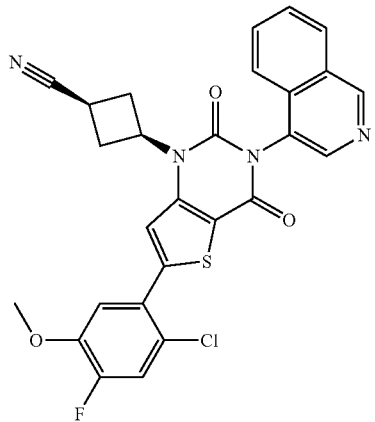 Stereochemistry arbitrary | 532.7 | 1H NMR (400 MHz, DMSO-d6) δ 9.50 (d, J = 0.9 Hz, 1H), 8.61 (s, 1H), 8.36-8.28 (m, 1H), 8.01-7.93 (m, 1H), 7.90-7.76 (m, 3H), 7.75 (d, J = 11.0 Hz, 1H), 7.51 (d, J = 8.8 Hz, 1H), 5.12 (p, J = 8.5 Hz, 1H), 3.98 (s, 3H), 3.31-3.07 (m, 3H), 2.91-2.79 (m, 2H). | 89 | 3-bromocyclobutane-carbonitrile |
| 695 | 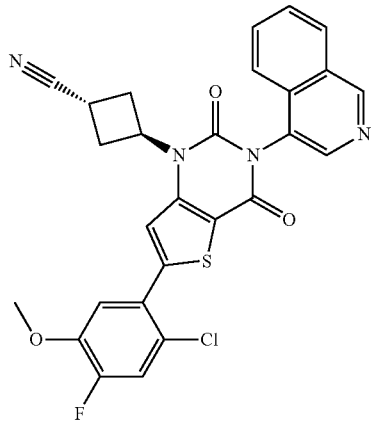 Stereochemistry arbitrary | 532.7 | 1H NMR (400 MHz, DMSO-d6) δ 9.48 (s, 1H), 8.61 (s, 1H), 8.31 (dd, J = 7.4, 1.6 Hz, 1H), 8.00-7.71 (m, 5H), 7.51 (d, J = 8.9 Hz, 1H), 5.50 (p, J = 8.4 Hz, 1H), 3.98 (d, J = 4.5 Hz, 3H), 3.47 (tt, J = 9.8, 4.6 Hz, 1H), 3.33-3.09 (m, 2H), 2.91-2.74 (m, 2H). | 89 | 3-bromocyclobutane-carbonitrile |
| 696 | 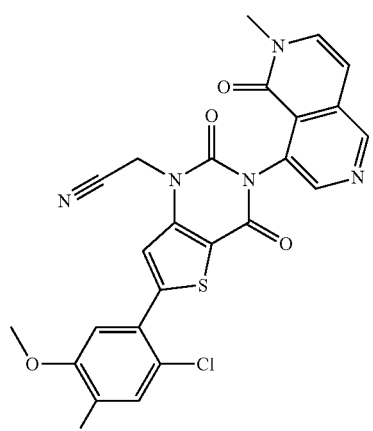 | 523.6 | 1H NMR (400 MHz, DMSO-d6) δ 9.23 (s, 1H), 8.60 (s, 1H), 7.96 (s, 1H), 7.75 (dd, J = 9.2, 1.9 Hz, 2H), 7.58 (d, J = 8.9 Hz, 1H), 6.90 (d, J = 7.3 Hz, 1H), 5.36 (d, J = 1.5 Hz, 2H), 3.98 (s, 3H), 3.43 (s, 3H). | 89 | Example 976 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 697 | 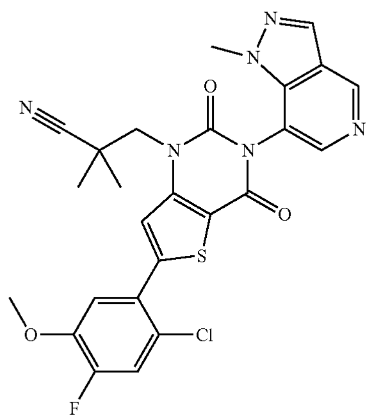 [SMILES: COc1cc(-c2cc3c(s2)c(=O)n(-c2cncc4cnn(C)c24)c(=O)n3CC(C)(C)C#N)c(Cl)cc1F] | 538.8 | 1H NMR (400 MHz, DMSO-d6) δ 9.31 (s, 1H), 8.54 (d, J = 9.5 Hz, 2H), 8.06 (s, 1H), 7.75 (d, J = 11.1 Hz, 1H), 7.47 (d, J = 8.9 Hz, 1H), 4.47 (d, J = 14.9 Hz, 1H), 4.38 (d, J = 14.9 Hz, 1H), 3.94 (s, 3H), 3.94 (s, 3H), 1.49 (s, 6H). | 95 | 3-bromo-2,2-dimethyl-propanenitrile |
| 698 | 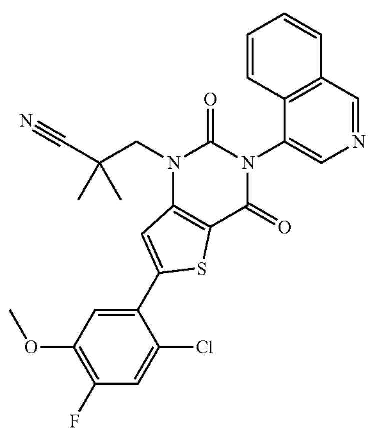 [SMILES: COc1cc(-c2cc3c(s2)c(=O)n(-c2cncc4ccccc24)c(=O)n3CC(C)(C)C#N)c(Cl)cc1F] | 534.7 | 1H NMR (400 MHz, DMSO-d6) δ 9.48 (d, J = 0.9 Hz, 1H), 8.62 (s, 1H), 8.30 (dd, J = 7.4, 1.6 Hz, 1H), 8.06 (s, 1H), 7.97 (dd, J = 8.3, 1.2 Hz, 1H), 7.87-7.71 (m, 3H), 7.47 (d, J = 8.9 Hz, 1H), 4.41 (s, 2H), 3.95 (s, 3H), 1.48 (d, J = 3.1 Hz, 6H). | 89 | 3-bromo-2,2-dimethyl-propanenitrile |
| 699 | 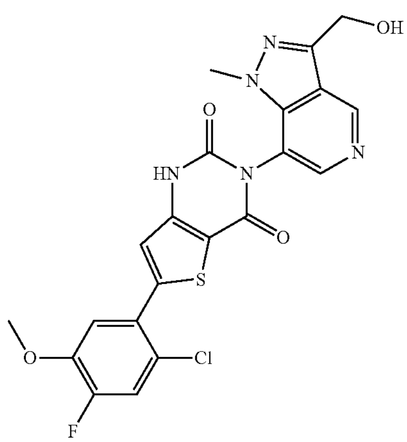 [SMILES: COc1cc(-c2cc3[nH]c(=O)n(-c4cncc5c(CO)nn(C)c45)c(=O)c3s2)c(Cl)cc1F] | 487.7 | 1H NMR (400 MHz, DMSO-d6) δ 12.49 (s, 1H), 9.35 (s, 1H), 8.50 (s, 1H), 7.72 (d, J = 11.0 Hz, 1H), 7.47 (d, J = 8.9 Hz, 1H), 7.33 (s, 1H), 4.89 (s, 2H), 3.95 (s, 3H), 3.87 (s, 3H). | 66 | I-209 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 700 | 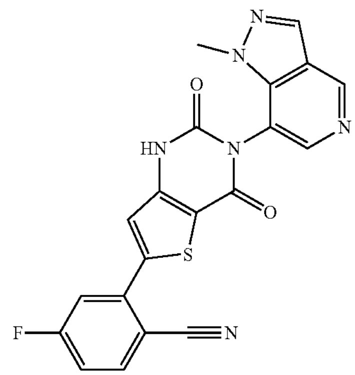 [SMILES: Cn1ncc2cncc(-n3c(=O)[nH]c4cc(-c5cc(F)ccc5C#N)sc4c3=O)c21] | 418.8 | 1H NMR (400 MHz, DMSO-d6) δ 12.64 (s, 1H), 9.43 (s, 1H), 8.65 (s, 1H), 8.62 (bs, 1H), 8.20 (dd, J = 8.7, 5.6 Hz, 1H), 7.86 (dd, J = 9.4, 2.6 Hz, 1H), 7.68-7.55 (m, 2H), 3.97 (s, 3H). | 64 | I-188; 4-fluoro-2-(4,4,5,5-tetramethyl-1,3,2-dioxaborolan-2-yl)benzonitrile |
| 701 | 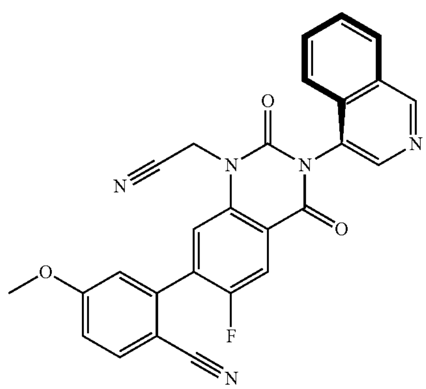 | 477.9 | 1H NMR (400 MHz, DMSO-d6) δ 9.48 (s, 1H), 8.64 (s, 1H), 8.30 (dd, J = 6.8, 2.3 Hz, 1H), 8.07 (dd, J = 16.6, 8.1 Hz, 3H), 7.95 (d, J = 5.5 Hz, 1H), 7.80 (tt, J = 7.1, 5.4 Hz, 2H), 7.34 (dd, J = 8.7, 2.6 Hz, 1H), 7.25 (d, J = 2.6 Hz, 1H), 5.55-5.29 (m, 2H), 3.97 (s, 3H). | 89 | Example 438 |
| 702 | 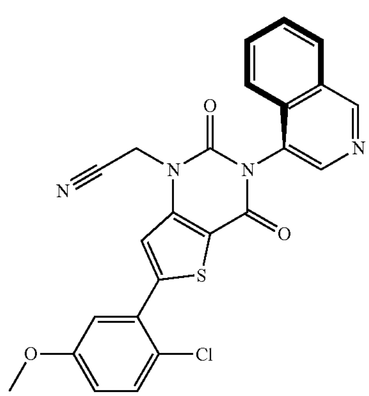 | 474.8 | 1H NMR (400 MHz, DMSO-d6) δ 9.47 (s, 1H), 8.63 (s, 1H), 8.34-8.24 (m, 1H), 8.04 (s, 1H), 7.98 (d, J = 8.0 Hz, 1H), 7.88-7.74 (m, 2H), 7.63 (d, J = 8.9 Hz, 1H), 7.39 (d, J = 3.0 Hz, 1H), 7.18 (dd, J = 8.9, 3.0 Hz, 1H), 5.41-5.27 (m, 2H), 3.88 (s, 3H). | 89 | Example 465 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 703 | 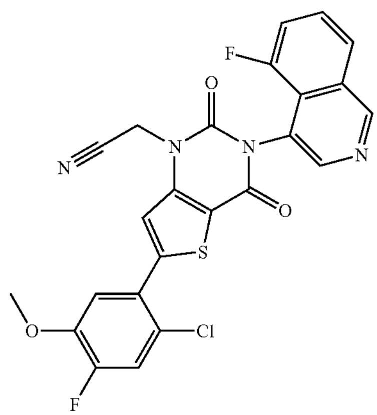 [SMILES: COc1cc(-c2cc3c(s2)c(=O)n(-c2cncc4cccc(F)c24)c(=O)n3CC#N)c(Cl)cc1F] | 510.7 | 1H NMR (400 MHz, DMSO-d6) δ 9.56 (s, 1H), 8.79-8.57 (m, 1H), 8.20 (s, 1H), 8.01 (d, J = 7.6 Hz, 1H), 7.95-7.40 (m, 4H), 5.62-5.32 (m, 2H), 3.99 (s, 3H). | 89 | Example 444 |
| 704 | 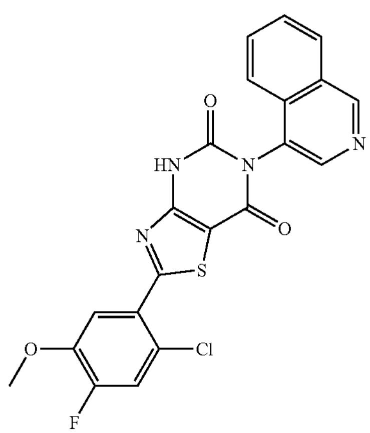 [SMILES: COc1cc(-c2nc3[nH]c(=O)n(-c4cncc5ccccc45)c(=O)c3s2)c(Cl)cc1F] | 454.8 | 1H NMR (400 MHz, DMSO-d6) δ 13.09 (s, 1H), 9.46 (s, 1H), 8.59 (s, 1H), 8.38-8.24 (m, 1H), 8.01 (d, J = 9.0 Hz, 1H), 7.94 (d, J = 8.2 Hz, 1H), 7.90-7.70 (m, 3H), 3.99 (s, 3H). | 46 | I-201; isoquinolin-4-amine |
| 705 | 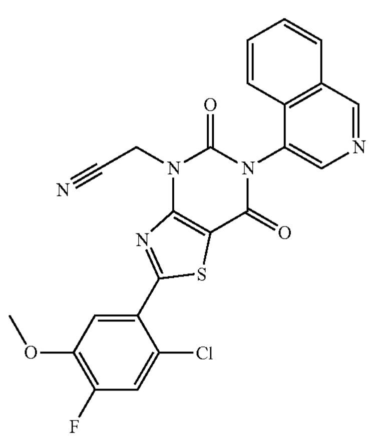 | 493.8 | 1H NMR (400 MHz, DMSO-d6) δ 9.49 (s, 1H), 8.63 (s, 1H), 8.34-8.27 (m, 1H), 8.24 (d, J = 9.0 Hz, 1H), 8.06 (d, J = 8.2 Hz, 1H), 7.91-7.72 (m, 3H), 5.48 (d, J = 5.1 Hz, 2H), 4.05 (s, 3H). | 89 | Example 704 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 706 | 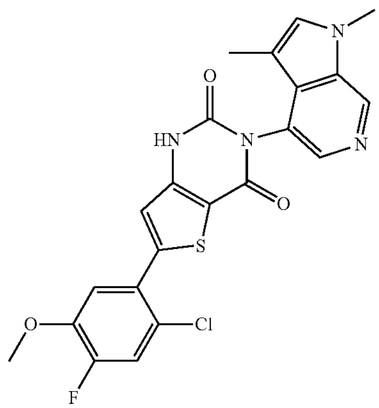 | 470.9 | 1H NMR (400 MHz, DMSO-d6) δ 12.47 (s, 1H), 9.38 (s, 1H), 8.49 (s, 1H), 8.07 (s, 1H), 7.72 (d, J = 11.0 Hz, 1H), 7.49 (d, J = 8.9 Hz, 1H), 7.33 (s, 1H), 4.06 (s, 3H), 3.95 (s, 3H), 2.10 (s, 3H). | 46 | I-191; I-66 |
| 707 | 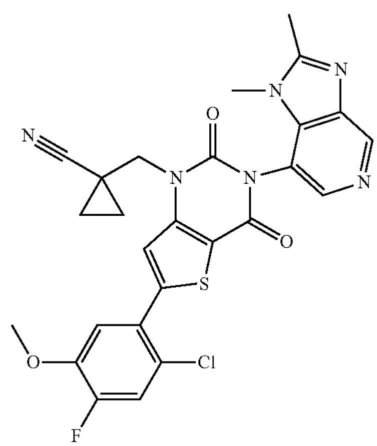 [SMILES: COc1cc(-c2cc3c(s2)c(=O)n(-c2cncc4nc(C)n(C)c24)c(=O)n3CC2(C#N)CC2)c(Cl)cc1F] | 550.8 | 1H NMR (400 MHz, DMSO-d6) δ 9.20 (s, 1H), 8.58 (s, 1H), 8.08 (s, 1H), 7.76 (d, J = 11.0 Hz, 1H), 7.52 (d, J = 8.8 Hz, 1H), 4.63-4.28 (m, 2H), 3.96 (s, 3H), 3.67 (s, 3H), 2.66 (s, 3H), 1.49-1.26 (m, 4H). | 97 | Example 764 |
| 708 | 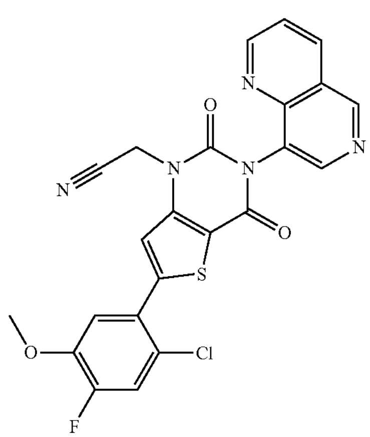 [SMILES: COc1cc(-c2cc3c(s2)c(=O)n(-c2cncc4cccnc24)c(=O)n3CC#N)c(Cl)cc1F] | 494.2 | 1H NMR (400 MHz, DMSO-d6) δ 9.59 (s, 1H), 9.13 (dd, 1H), 8.90 (s, 1H), 8.76 (dd, 1H), 8.00 (s, 1H), 7.86-7.72 (m, 2H), 7.57 (d, 1H), 5.38 (d, 2H), 3.98 (s, 3H). | 89 | Example 553 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 709 | 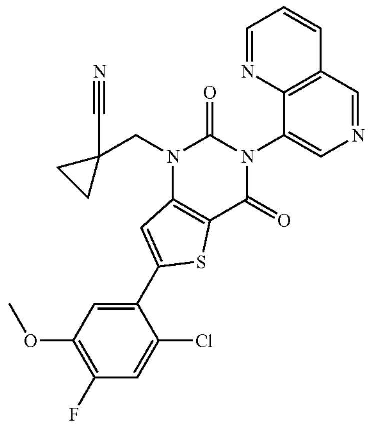 [SMILES: COc1cc(-c2cc3c(s2)c(=O)n(-c2cncc4cccnc24)c(=O)n3CC2(C#N)CC2)c(Cl)cc1F] | 534.3 | 1H NMR (400 MHz, DMSO-d6) δ 9.58 (s, 1H), 9.12 (dd, 1H), 8.87 (s, 1H), 8.75 (dd, 1H), 8.07 (s, 1H), 7.85-7.71 (m, 2H), 7.54 (d, 1H), 4.43 (d, 2H), 3.96 (s, 3H), 1.42-1.26 (m, 4H). | 97 | Example 553 |
| 710 | 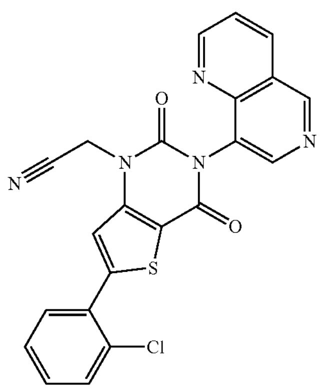 [SMILES: N#CCn1c(=O)n(-c2cncc3cccnc23)c(=O)c2sc(-c3ccccc3Cl)cc21] | 446.3 | 1H NMR (400 MHz, DMSO-d6) δ 9.59 (s, 1H), 9.13 (dd, 1H), 8.90 (s, 1H), 8.76 (dd, 1H), 8.03 (s, 1H), 7.92-7.75 (m, 2H), 7.78-7.69 (m, 1H), 7.58 (dd, 2H), 5.38 (d, 2H). | 89 | Example 133 |
| 711 | 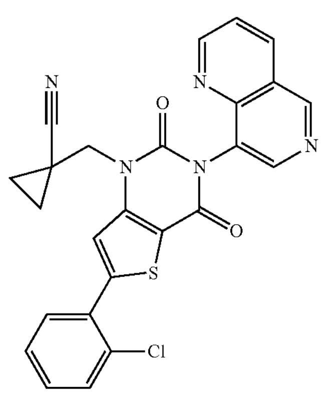 [SMILES: N#CC1(Cn2c(=O)n(-c3cncc4cccnc34)c(=O)c3sc(-c4ccccc4Cl)cc32)CC1] | 486.2 | 1H NMR (400 MHz, DMSO-d6) δ 9.58 (s, 1H), 9.13 (dd, 1H), 8.87 (s, 1H), 8.75 (dd, 1H), 8.08 (s, 1H), 7.91-7.77 (m, 2H), 7.77-7.67 (m, 1H), 7.64-7.52 (m, 2H), 4.42 (s, 2H), 1.41-1.25 (m, 4H). | 97 | Example 133 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 712 | 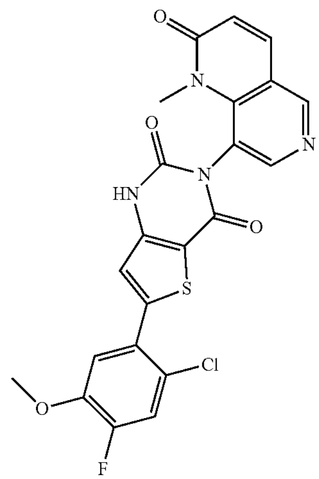 [SMILES: COc1cc(-c2cc3[nH]c(=O)n(-c4cncc5ccc(=O)n(C)c45)c(=O)c3s2)c(Cl)cc1F] | 485.1 | 1H NMR (400 MHz, DMSO-d6) δ 12.48 (s, 1H), 8.97 (s, 1H), 8.60 (d, 1H), 8.14 (d, 1H), 7.76-7.67 (m, 1H), 7.47 (d, 1H), 7.32 (s, 1H), 6.82 (d, 1H), 3.41 (d, 3H), 2.46 (s, 3H). | 46 | I-66; I-260 |
| 713 | 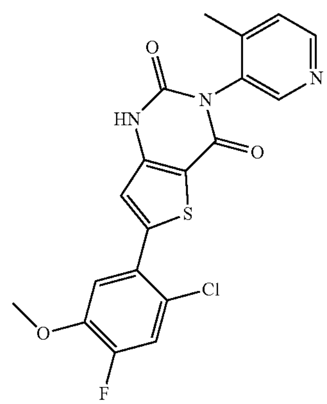 [SMILES: COc1cc(-c2cc3[nH]c(=O)n(-c4cnccc4C)c(=O)c3s2)c(Cl)cc1F] | 418.1 | 1H NMR (400 MHz, DMSO-d6) δ 12.27 (s, 1H), 8.54 (d, 1H), 8.52 (s, 1H), 7.71 (d, 1H), 7.52 (d, 1H), 7.45 (d, 1H), 7.28 (s, 1H), 3.94 (s, 3H), 2.17 (s, 3H). | 46 | I-66; 4-methylpyridin-3-amine |
| 714 | 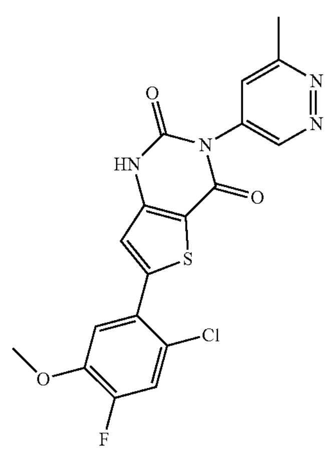 [SMILES: COc1cc(-c2cc3[nH]c(=O)n(-c4cnnc(C)c4)c(=O)c3s2)c(Cl)cc1F] | 419.1 | 1H NMR (400 MHz, DMSO-d6) δ 12.34 (s, 1H), 9.18 (d, 1H), 7.77-7.65 (m, 2H), 7.44 (d, 1H), 7.27 (s, 1H), 3.94 (s, 3H), 2.72 (s, 3H). | 46 | I-66; 6-methylpyridazin-4-amine |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 715 | 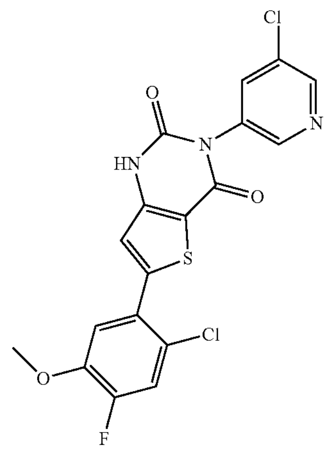 [SMILES: COc1cc(-c2cc3[nH]c(=O)n(-c4cncc(Cl)c4)c(=O)c3s2)c(Cl)cc1F] | 438.1 | 1H NMR (400 MHz, DMSO-d6) δ 12.27 (s, 1H), 8.76-8.65 (m, 1H), 8.60 (t, 1H), 8.15 (q, 1H), 7.70 (dd, 1H), 7.44 (d, 1H), 7.27 (d, 1H), 3.95 (s, 2H). | 46 | I-66; 5-chloropyridin-3-amine |
| 716 | 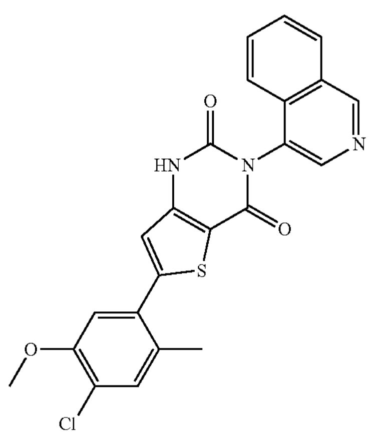 [SMILES: COc1cc(-c2cc3[nH]c(=O)n(-c4cncc5ccccc45)c(=O)c3s2)c(C)cc1Cl] | 449.7 | 1H NMR (400 MHz, DMSO) δ 12.30 (s, 1H), 9.84 (s, 1H), 8.90 (s, 1H), 8.33 (d, J = 8.0 Hz, 1H), 7.90-7.79 (m, 3H), 7.52 (s, 1H), 7.17 (dd, J = 18.7, 2.0 Hz, 2H), 3.91 (d, J = 3.3 Hz, 3H), 2.39 (s, 3H). | 64 | I-311 |
| 717 | 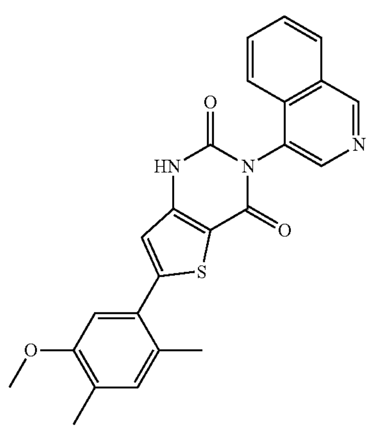 [SMILES: COc1cc(-c2cc3[nH]c(=O)n(-c4cncc5ccccc45)c(=O)c3s2)c(C)cc1C] | 429.8 | 1H NMR (400 MHz, MeOD) δ 13.06 (s, 1H), 10.41 (s, 1H), 9.50 (s, 1H), 9.14 (d, J = 8.1 Hz, 1H), 8.72-8.60 (m, 3H), 8.00 (s, 1H), 7.90 (s, 1H), 7.81 (s, 1H), 3.19 (s, 3H), 3.00 (s, 3H). | 64 | (5-methoxy-2,4-dimethyl-phenyl)boronic acid |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 718 | 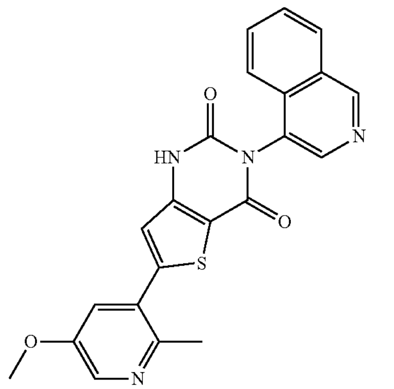 [SMILES: COc1cnc(C)c(-c2cc3[nH]c(=O)n(-c4cncc5ccccc45)c(=O)c3s2)c1] | 416.8 | 1H NMR (400 MHz, DMSO) δ 12.35 (s, 1H), 9.53 (s, 1H), 8.64 (s, 1H), 8.38 (d, J = 2.9 Hz, 1H), 8.35-8.30 (m, 1H), 7.90-7.85 (m, 2H), 7.83-7.77 (m, 1H), 7.59 (d, J = 2.8 Hz, 1H), 7.25 (s, 1H), 3.92 (s, 3H), 2.61 (s, 3H). | 64 | I-312 |
| 719 | 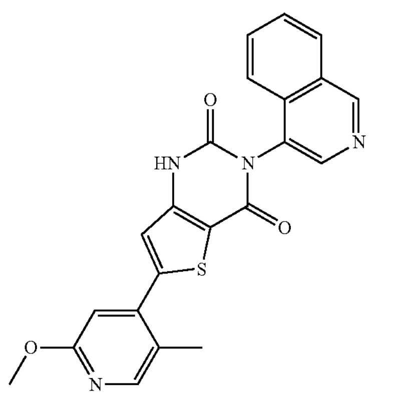 [SMILES: COc1cc(-c2cc3[nH]c(=O)n(-c4cncc5ccccc45)c(=O)c3s2)c(C)cn1] | 416.5 | 1H NMR (400 MHz, DMSO) δ 12.35 (s, 1H), 9.69 (s, 1H), 8.8 (s, 1H), 8.34 (d, J = 8.0 Hz, 1H), 8.22 (s, 1H), 8.01-7.73 (m, 3H), 7.28 (s, 1H), 6.98 (s, 1H), 3.90 (s, 3H), 2.38 (s, 3H). | 64 | I-313 |
| 720 | 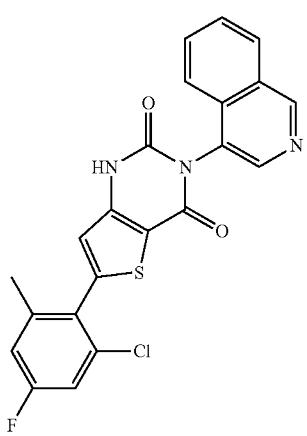 [SMILES: Cc1cc(F)cc(Cl)c1-c1cc2[nH]c(=O)n(-c3cncc4ccccc34)c(=O)c2s1] | 437.7 | 1H NMR (400 MHz, DMSO) δ 12.34 (s, 1H), 9.50 (s, 1H), 8.65 (s, 1H), 8.32 (dd, J = 7.8, 1.4 Hz, 1H), 7.94 (d, J = 8.3 Hz, 1H), 7.83 (dddd, J = 21.7, 8.1, 6.8, 1.3 Hz, 2H), 7.52 (dd, J = 8.6, 2.6 Hz, 1H), 7.36 (dd, J = 9.6, 2.6 Hz, 1H), 7.00 (s, 1H), 2.28 (s, 3H). | 64 | (2-chloro-4-fluoro-6-methyl-phenyl)boronic acid |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 721 | 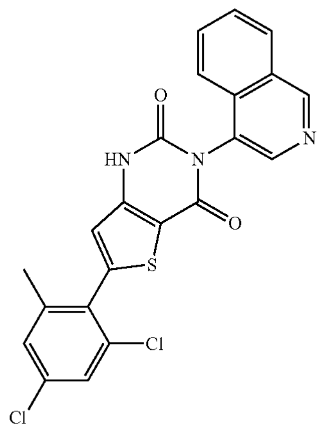 [SMILES: Cc1cc(Cl)cc(Cl)c1-c1cc2[nH]c(=O)n(-c3cncc4ccccc34)c(=O)c2s1] | 455.7 | 1H NMR (400 MHz, DMSO) δ 12.34 (s, 1H), 9.50 (s, 1H), 8.65 (s, 1H), 8.31 (d, J = 8.0 Hz, 1H), 7.93 (d, J = 8.3 Hz, 1H), 7.83 (dddd, J = 21.4, 8.1, 6.8, 1.3 Hz, 2H), 7.69 (d, J = 2.1 Hz, 1H), 7.56 (d, J = 2.1 Hz, 1H), 7.02 (s, 1H), 2.27 (s, 3H). | 64 | (2,4-dichloro-6-methyl-phenyl)boronic acid |
| 722 | 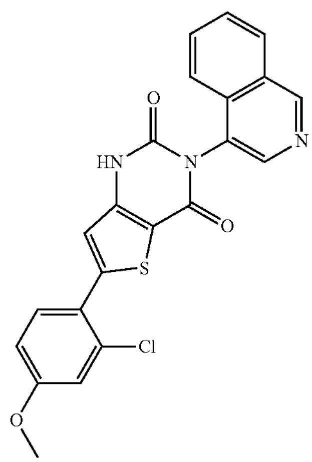 [SMILES: COc1ccc(-c2cc3[nH]c(=O)n(-c4cncc5ccccc45)c(=O)c3s2)c(Cl)c1] | 435.7 | 1H NMR (400 MHz, DMSO) δ 12.25 (s, 1H), 9.47 (s, 1H), 8.59 (s, 1H), 8.30 (dd, J = 7.5, 1.5 Hz, 1H), 7.92-7.74 (m, 4H), 7.70 (d, J = 8.7 Hz, 1H), 7.29-7.25 (m, 2H), 7.11 (dd, J = 8.7, 2.6 Hz, 1H), 3.87 (s, 3H). | 64 | (2-chloro-4-methoxy-phenyl)boronic acid |
| 723 | 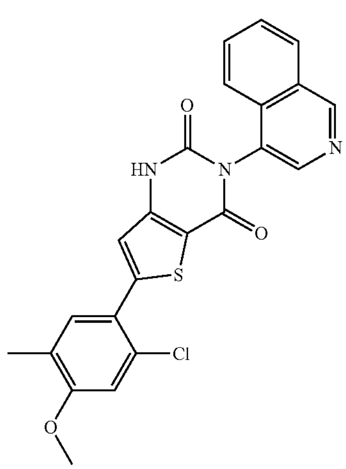 [SMILES: COc1cc(Cl)c(-c2cc3[nH]c(=O)n(-c4cncc5ccccc45)c(=O)c3s2)cc1C] | 449.8 | 1H NMR (400 MHz, DMSO) δ 12.27 (s, 1H), 9.52 (s, 1H), 8.63 (s, 1H), 8.32 (dd, J = 7.7, 1.5 Hz, 1H), 7.95-7.78 (m, 3H), 7.57 (s, 1H), 7.27 (s, 1H), 7.23 (s, 1H), 3.90 (s, 3H), 2.21 (s, 3H). | 64 | (2-chloro-4-methoxy-5-methyl-phenyl)boronic acid |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 724 | 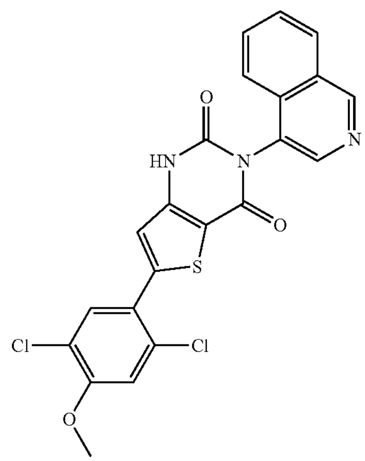 [SMILES: COc1cc(Cl)c(-c2cc3[nH]c(=O)n(-c4cncc5ccccc45)c(=O)c3s2)cc1Cl] | 469.7 | 1H NMR (400 MHz, DMSO) δ 12.32 (s, 1H), 9.50 (s, 1H), 8.62 (s, 1H), 8.32 (dd, J = 7.6, 1.4 Hz, 1H), 7.90 (dd, J = 8.3, 1.4 Hz, 1H), 7.88-7.76 (m, 3H), 7.49 (s, 1H), 7.31 (s, 1H), 3.98 (s, 3H). | 64 | (2,5-dichloro-4-methoxy-phenyl)boronic acid |
| 725 | 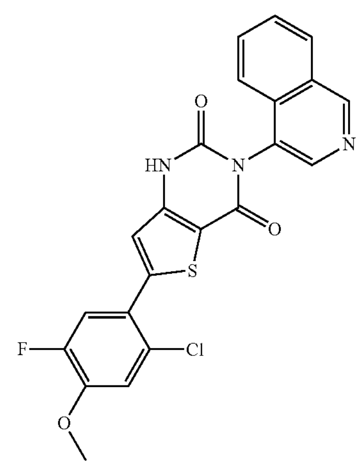 [SMILES: COc1cc(Cl)c(-c2cc3[nH]c(=O)n(-c4cncc5ccccc45)c(=O)c3s2)cc1F] | 453.8 | 1H NMR (400 MHz, DMSO) δ 12.29 (s, 1H), 9.44 (s, 1H), 8.57 (s, 1H), 8.29 (dd, J = 7.3, 1.6 Hz, 1H), 7.88-7.74 (m, 4H), 7.51 (d, J = 8.0 Hz, 1H), 7.31 (s, 1H), 3.96 (s, 3H). | 64 | (2-chloro-5-fluoro-4-methoxy-phenyl)boronic acid |
| 726 | 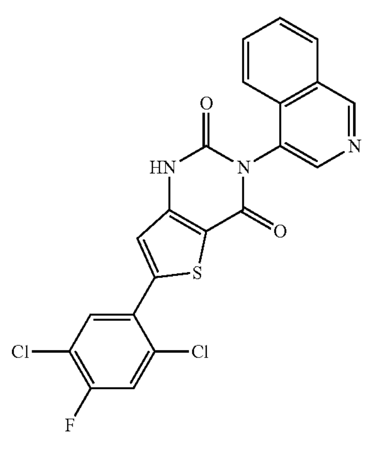 [SMILES: O=c1[nH]c2cc(-c3cc(Cl)c(F)cc3Cl)sc2c(=O)n1-c1cncc2ccccc12] | 457.5 | 1H NMR (400 MHz, DMSO) δ 12.35 (s, 1H), 9.47 (s, 1H), 8.61 (s, 1H), 8.30 (d, J = 8.0 Hz, 1H), 8.06 (d, J = 7.7 Hz, 1H), 7.98 (d, J = 9.1 Hz, 1H), 7.92-7.73 (m, 4H), 7.35 (s, 1H). | 64 | (2,5-dichloro-4-fluoro-phenyl)boronic acid |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 727 | 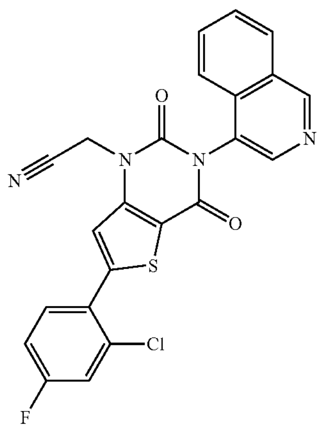 [SMILES: N#CCn1c(=O)n(-c2cncc3ccccc23)c(=O)c2sc(-c3ccc(F)cc3Cl)cc21] | 462.8 | 1H NMR (400 MHz, DMSO) δ 9.51 (s, 1H), 8.65 (s, 1H), 8.32 (dd, J = 7.5, 1.5 Hz, 1H), 8.02 (d, J = 8.5 Hz, 2H), 7.92 (dd, J = 8.8, 6.0 Hz, 1H), 7.89-7.74 (m, 3H), 7.51 (td, J = 8.4, 2.7 Hz, 1H), 5.41-5.26 (m, 2H). | 64 | I-314; (2-chloro-4-fluoro-phenyl)boronic acid |
| 728 | 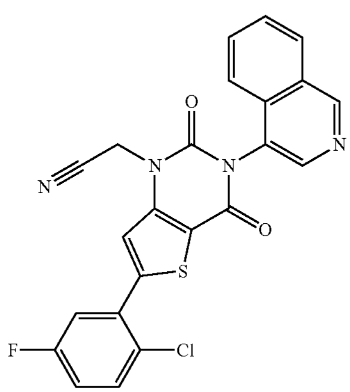 [SMILES: N#CCn1c(=O)n(-c2cncc3ccccc23)c(=O)c2sc(-c3cc(F)ccc3Cl)cc21] | 462.8 | 1H NMR (400 MHz, DMSO) δ 9.58 (s, 2H), 8.72 (s, 1H), 8.35-8.25 (m, 1H), 8.13 (s, 1H), 8.04-7.94 (m, 1H), 7.89-7.72 (m, 3H), 7.48 (ddd, J = 8.9, 7.9, 3.1 Hz, 1H), 5.40-5.25 (m, 2H). | 64 | I-314; (2-chloro-5-fluoro-phenyl)boronic acid |
| 729 | 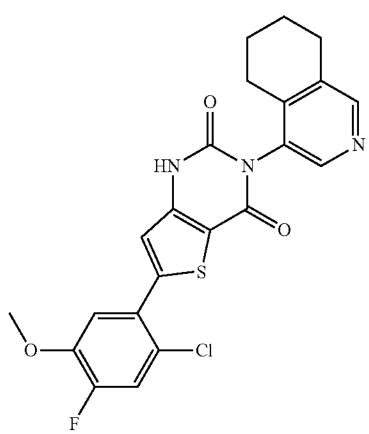 [SMILES: COc1cc(-c2cc3[nH]c(=O)n(-c4cncc5c4CCCC5)c(=O)c3s2)c(Cl)cc1F] | 459.8 | 1H NMR (400 MHz, DMSO) δ 12.31 (s, 1H), 8.50 (s, 1H), 8.44 (s, 1H), 7.71 (d, J = 11.1 Hz, 1H), 7.44 (d, J = 8.8 Hz, 1H), 7.28 (s, 1H), 3.94 (s, 3H), 2.86 (d, J = 11.8 Hz, 2H), 1.81-1.68 (m, 4H). | 70 | I-66; 5,6,7,8-tetrahydroisoquinolin-4-amine |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 730 | 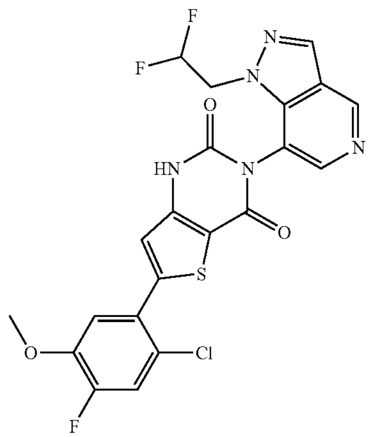 [SMILES: COc1cc(-c2cc3[nH]c(=O)n(-c4cncc5cnn(CC(F)F)c45)c(=O)c3s2)c(Cl)cc1F] | 508.7 | 1H NMR (400 MHz, MeOD) δ 13.29 (s, 1H), 10.14 (s, 1H), 9.48 (s, 1H), 9.37 (s, 1H), 8.53 (d, J = 11.0 Hz, 1H), 8.28 (d, J = 8.8 Hz, 1H), 8.15 (s, 1H), 7.14 (t, J = 3.1 Hz, 1H), 5.50 (qd, J = 15.5, 3.2 Hz, 2H), 4.77 (s, 3H) | 70 | I-317; I-66 |
| 731 | 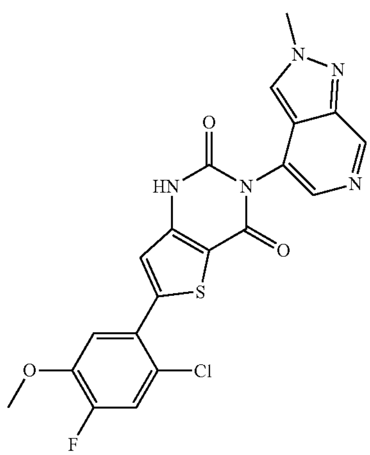 [SMILES: COc1cc(-c2cc3[nH]c(=O)n(-c4cncc5nn(C)cc45)c(=O)c3s2)c(Cl)cc1F] | 458.8 | 1H NMR (400 MHz, DMSO) δ 12.27 (s, 1H), 9.38 (s, 1H), 8.68 (s, 1H), 8.20 (s, 1H), 7.72 (d, J = 11.1 Hz, 1H), 7.44 (d, J = 8.9 Hz, 1H), 7.30 (s, 1H), 4.30 (s, 3H), 3.95 (s, 3H). | 70 | I-318; I-66 |
| 732 | 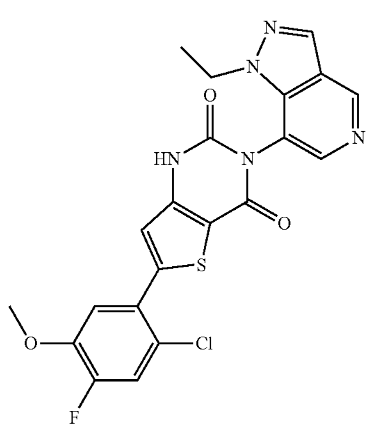 [SMILES: CCn1ncc2cncc(-n3c(=O)[nH]c4cc(-c5cc(OC)c(F)cc5Cl)sc4c3=O)c21] | 471.8 | 1H NMR (400 MHz, DMSO) δ 12.55 (s, 1H), 9.34 (s, 1H), 8.62 (s, 1H), 8.54 (s, 1H), 7.72 (d, J = 11.1 Hz, 1H), 7.48 (d, J = 8.9 Hz, 1H), 7.35 (s, 1H), 4.29-4.18 (m, 2H), 3.95 (s, 3H), 1.29 (t, J = 7.2 Hz, 3H). | 70 | I-320; I-66 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 733 | 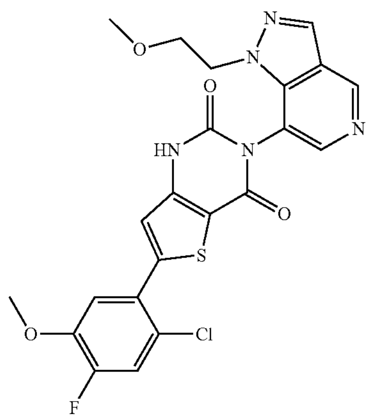 [SMILES: COCCn1ncc2cncc(-n3c(=O)[nH]c4cc(-c5cc(OC)c(F)cc5Cl)sc4c3=O)c21] | 501.8 | 1H NMR (400 MHz, DMSO) δ 12.45 (s, 1H), 9.31 (s, 1H), 8.60 (s, 1H), 8.50 (s, 1H), 7.72 (d, J = 11.0 Hz, 1H), 7.48 (d, J = 8.8 Hz, 1H), 7.33 (s, 1H), 4.42-4.28 (m, 2H), 3.96 (s, 3H), 3.57 (d, J = 10.8 Hz, 2H), 3.04 (s, 3H). | 70 | I-322; I-66 |
| 734 | 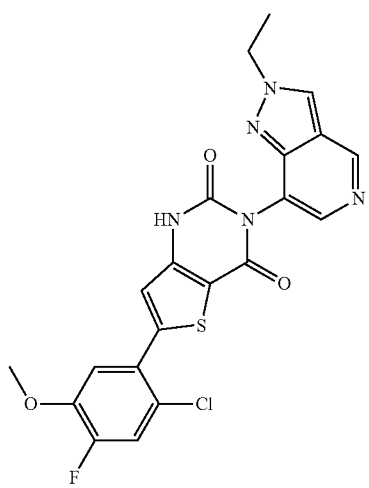 [SMILES: CCn1cc2cncc(-n3c(=O)[nH]c4cc(-c5cc(OC)c(F)cc5Cl)sc4c3=O)c2n1] | 471.8 | 1H NMR (400 MHz, DMSO) δ 12.36 (s, 1H), 8.46 (s, 1H), 8.17-8.08 (m, 1H), 7.72 (d, J = 11.1 Hz, 1H), 7.47 (d, J = 8.9 Hz, 1H), 7.31 (s, 1H), 6.98-6.90 (m, 1H), 4.59 (q, J = 7.3 Hz, 2H), 3.95 (s, 3H), 1.52 (t, J = 7.3 Hz, 3H). | 70 | I-324; I-66 |
| 735 | 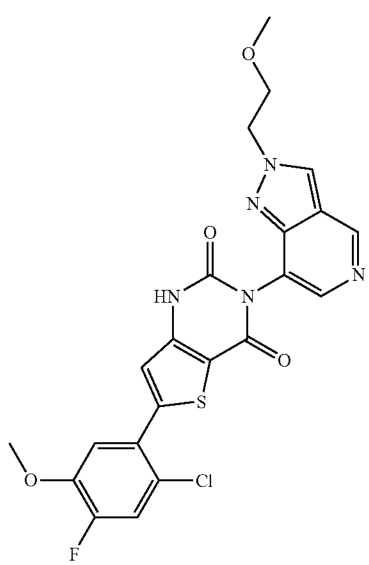 [SMILES: COCCn1cc2cncc(-n3c(=O)[nH]c4cc(-c5cc(OC)c(F)cc5Cl)sc4c3=O)c2n1] | 501.8 | 1H NMR (400 MHz, DMSO) δ 12.32 (s, 1H), 9.46 (s, 1H), 9.04 (s, 1H), 8.37 (s, 1H), 7.72 (d, J = 11.1 Hz, 1H), 7.47 (d, J = 8.9 Hz, 1H), 7.30 (s, 1H), 4.70 (t, J = 5.1 Hz, 2H), 3.95 (s, 3H), 3.81 (t, J = 5.1 Hz, 2H), 3.24 (s, 3H). | 70 | I-326; I-66 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 736 | 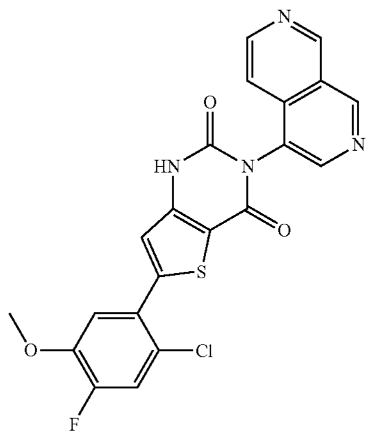 [SMILES: COc1cc(-c2cc3[nH]c(=O)n(-c4cncc5cnccc45)c(=O)c3s2)c(Cl)cc1F] | 494.8 | 1H NMR (400 MHz, DMSO) δ 12.35 (s, 1H), 9.69 (d, J = 12.6 Hz, 2H), 8.86 (s, 1H), 8.76 (d, J = 6.0 Hz, 1H), 7.88 (d, J = 6.0 Hz, 1H), 7.72 (d, J = 11.0 Hz, 1H), 7.44 (d, J = 8.9 Hz, 1H), 7.33 (s, 1H), 3.96 (s, 3H). | 70 | I-66; I-328 |
| 737 | 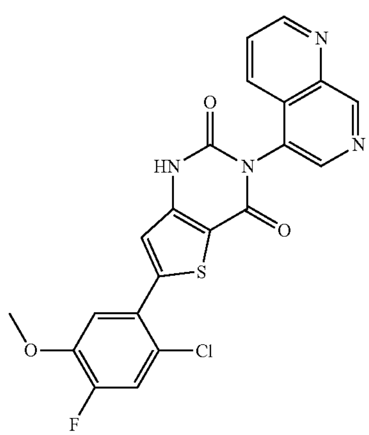 [SMILES: COc1cc(-c2cc3[nH]c(=O)n(-c4cncc5ncccc45)c(=O)c3s2)c(Cl)cc1F] | 454.7 | 1H NMR (400 MHz, DMSO) δ 12.34 (s, 1H), 9.53 (d, J = 0.9 Hz, 1H), 9.14 (dd, J = 4.1, 1.6 Hz, 1H), 8.73 (s, 1H), 8.46 (dt, J = 8.4, 1.3 Hz, 1H), 7.82 (dd, J = 8.6, 4.1 Hz, 1H), 7.72 (d, J = 11.0 Hz, 1H), 7.44 (d, J = 8.9 Hz, 1H), 7.33 (s, 1H), 3.96 (s, 3H). | 70 | I-66; I-327 |
| 738 | 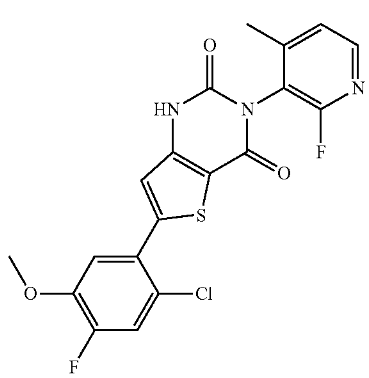 [SMILES: COc1cc(-c2cc3[nH]c(=O)n(-c4c(C)ccnc4F)c(=O)c3s2)c(Cl)cc1F] | 435.7 | 1H NMR (400 MHz, DMSO) δ 12.45 (s, 1H), 8.22 (d, J = 5.1 Hz, 1H), 7.71 (d, J = 11.0 Hz, 1H), 7.48-7.44 (m, 2H), 7.29 (s, 1H), 3.94 (s, 3H), 2.24 (s, 3H). | 70 | I-66; 2-fluoro-4-methyl-pyridin-3-amine |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 739 | 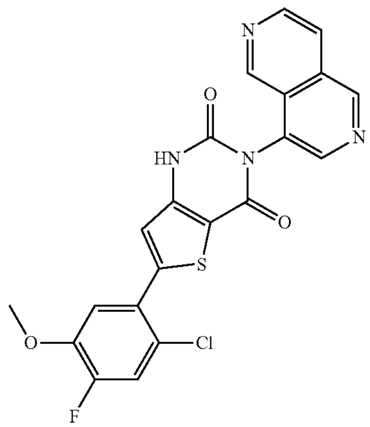 [SMILES: COc1cc(-c2cc3[nH]c(=O)n(-c4cncc5ccncc45)c(=O)c3s2)c(Cl)cc1F] | 454.8 | 1H NMR (400 MHz, DMSO) δ 12.35 (s, 1H), 9.58 (d, J = 0.9 Hz, 1H), 9.48 (s, 1H), 8.85-8.76 (m, 2H), 8.18 (dd, J = 5.7, 1.1 Hz, 1H), 7.72 (d, J = 11.0 Hz, 1H), 7.45 (d, J = 8.8 Hz, 1H), 7.33 (s, 1H), 3.96 (s, 3H). | 70 | I-66; 2,7-naphthyridin-4-amine; hydrochloride; pyridine (3 eq.) |
| 740 | 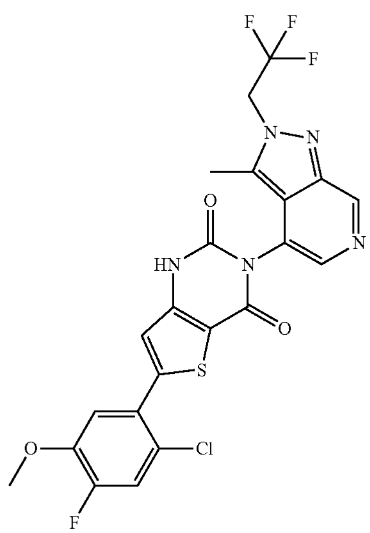 [SMILES: COc1cc(-c2cc3[nH]c(=O)n(-c4cncc5nn(CC(F)(F)F)c(C)c45)c(=O)c3s2)c(Cl)cc1F] | 539.8 | 1H NMR (400 MHz, DMSO) δ 12.39 (s, 1H), 9.34 (s, 1H), 8.14 (s, 1H), 7.72 (d, J = 11.1 Hz, 1H), 7.48 (d, J = 8.9 Hz, 1H), 7.32 (s, 1H), 5.65 (q, J = 8.9 Hz, 2H), 3.95 (s, 3H), 2.49 (s, 3H). | 70 | I-66; I-331 |
| 741 | 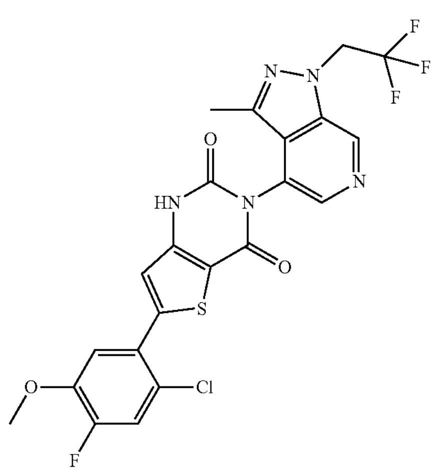 [SMILES: COc1cc(-c2cc3[nH]c(=O)n(-c4cncc5c4c(C)nn5CC(F)(F)F)c(=O)c3s2)c(Cl)cc1F] | 539.7 | 1H NMR (400 MHz, DMSO) δ 12.43 (s, 1H), 9.32 (s, 1H), 8.34 (s, 1H), 7.71 (d, J = 11.0 Hz, 1H), 7.49 (d, J = 8.9 Hz, 1H), 7.31 (s, 1H), 5.62 (q, J = 9.0 Hz, 2H), 3.95 (s, 3H), 2.32 (s, 3H). | 70 | I-66; I-333 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 742 | 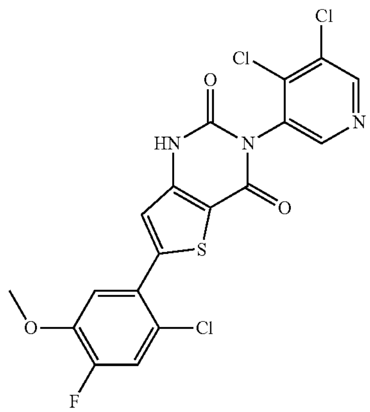 [SMILES: COc1cc(-c2cc3[nH]c(=O)n(-c4cncc(Cl)c4Cl)c(=O)c3s2)c(Cl)cc1F] | 472.7 | 1H NMR (400 MHz, DMSO-d6) δ 12.47 (s, 1H), 8.94 (s, 1H), 8.76 (s, 1H), 7.71 (d, J = 11.1 Hz, 1H), 7.47 (d, J = 8.9 Hz, 1H), 7.29 (s, 1H), 3.94 (s, 3H). | 46 | I-66; 4,5-dichloropyridin-3-amine |
| 743 | 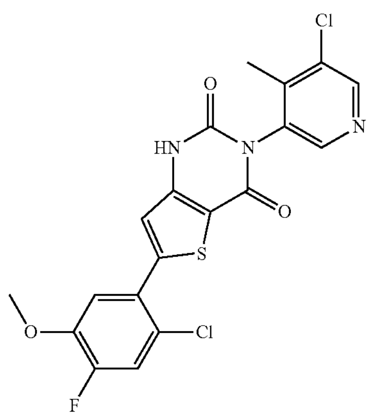 [SMILES: COc1cc(-c2cc3[nH]c(=O)n(-c4cncc(Cl)c4C)c(=O)c3s2)c(Cl)cc1F] | 451.7 | 1H NMR (400 MHz, DMSO-d6) δ 12.34 (s, 1H), 8.69 (s, 1H), 8.51 (s, 1H), 7.71 (d, J = 11.1 Hz, 1H), 7.44 (d, J = 8.9 Hz, 1H), 7.29 (s, 1H), 3.94 (s, 3H), 2.19 (s, 3H). | 46 | I-66; 5-chloro-4-methyl-pyridin-3-amine |
| 744 | 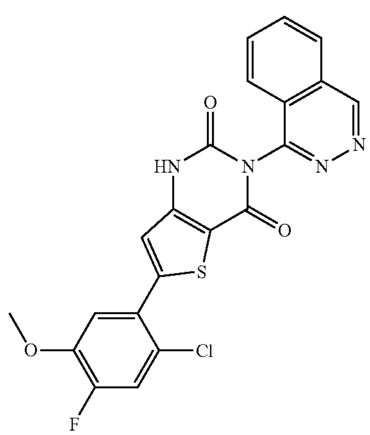 [SMILES: COc1cc(-c2cc3[nH]c(=O)n(-c4nncc5ccccc45)c(=O)c3s2)c(Cl)cc1F] | 454.8 | 1H NMR (400 MHz, DMSO-d6) δ 12.48 (s, 1H), 9.86 (d, J = 0.9 Hz, 1H), 8.36 (d, J = 8.1 Hz, 1H), 8.23 (d, J = 8.2 Hz, 1H), 8.14 (ddd, J = 8.2, 7.0, 1.3 Hz, 1H), 8.06 (ddd, J = 8.3, 7.1, 1.2 Hz, 1H), 7.73 (d, J = 11.0 Hz, 1H), 7.49 (d, J = 8.9 Hz, 1H), 7.36 (s, 1H), 3.96 (s, 3H). | 46 | I-66; phthalazin-1-amine |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 745 | 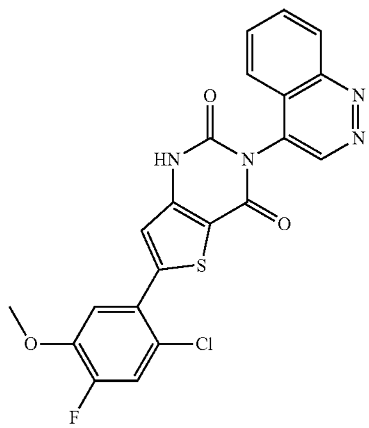 [SMILES: COc1cc(-c2cc3[nH]c(=O)n(-c4cnnc5ccccc45)c(=O)c3s2)c(Cl)cc1F] | 454.7 | 1H NMR (400 MHz, DMSO-d6) δ 12.45 (s, 1H), 9.55 (s, 1H), 8.63 (dd, J = 8.6, 1.1 Hz, 1H), 8.16-8.08 (m, 1H), 8.05 (m, 1H), 7.92 (ddd, J = 8.2, 6.8, 1.2 Hz, 1H), 7.72 (d, J = 11.1 Hz, 1H), 7.45 (d, J = 8.9 Hz, 1H), 7.35 (s, 1H), 3.96 (s, 3H). | 46 | I-66; cinnolin-4-amine |
| 746 | 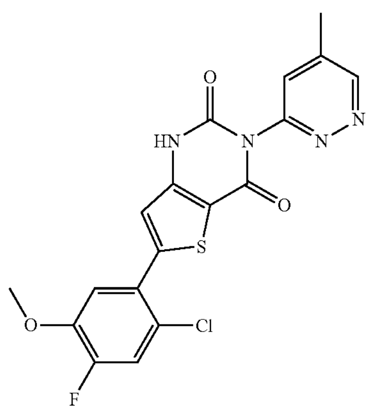 [SMILES: COc1cc(-c2cc3[nH]c(=O)n(-c4cc(C)cnn4)c(=O)c3s2)c(Cl)cc1F] | 418.8 | 1H NMR (400 MHz, DMSO-d6) δ 12.34 (s, 1H), 9.23 (d, J = 2.0 Hz, 1H), 7.78 (dd, J = 2.0, 1.0 Hz, 1H), 7.71 (d, J = 11.0 Hz, 1H), 7.47 (d, J = 8.9 Hz, 1H), 7.29 (s, 1H), 3.95 (s, 3H), 2.44 (s, 3H); 1H NMR (400 MHz, DMSO-d6) δ 9.26 (d, J = 2.1 Hz, 1H), 7.96 (d, J = 1.9 Hz, 1H), 7.76 (t, J = 2.5 Hz, 1H), 7.73 (d, J = 1.6 Hz, 1H), 7.58-7.52 (m, 1H), 4.43 (m, 2H), 3.99-3.95 (m, 3H), 3.01 (m, 2H), 2.45 (s, 3H). | 46 | I-66; 5-methylpyridazin-3-amine |
| 747 | 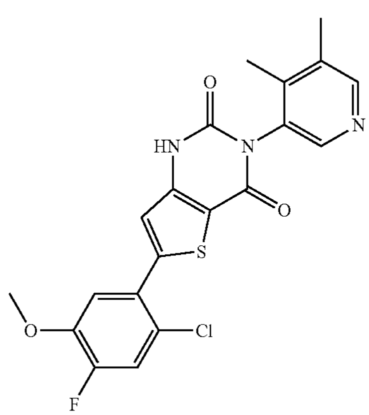 [SMILES: COc1cc(-c2cc3[nH]c(=O)n(-c4cncc(C)c4C)c(=O)c3s2)c(Cl)cc1F] | 431.8 | 1H NMR (400 MHz, DMSO-d6) δ 12.44 (s, 1H), 8.68 (d, J = 13.5 Hz, 2H), 7.71 (d, J = 11.0 Hz, 1H), 7.44 (d, J = 8.8 Hz, 1H), 7.32 (s, 1H), 3.94 (s, 3H), 2.43 (s, 3H), 2.21 (s, 3H). | 46 | I-66; I-237 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 748 | 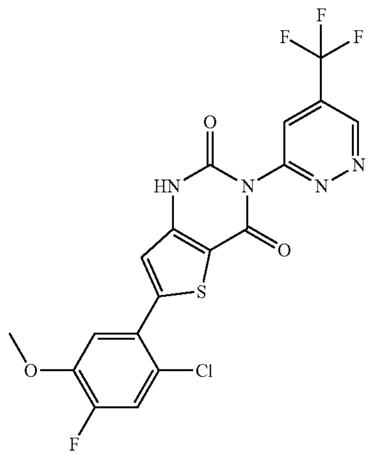 [SMILES: COc1cc(-c2cc3[nH]c(=O)n(-c4cc(C(F)(F)F)cnn4)c(=O)c3s2)c(Cl)cc1F] | 472.7 | 1H NMR (400 MHz, DMSO-d6) δ 12.51 (s, 1H), 9.91 (d, J = 2.0 Hz, 1H), 8.62 (dd, J = 2.1, 0.9 Hz, 1H), 7.72 (d, J = 11.0 Hz, 1H), 7.48 (d, J = 8.9 Hz, 1H), 7.32 (s, 1H), 3.95 (s, 3H). | 46 | I-66; 5-(trifluoromethyl) pyridazin-3-amine |
| 749 | 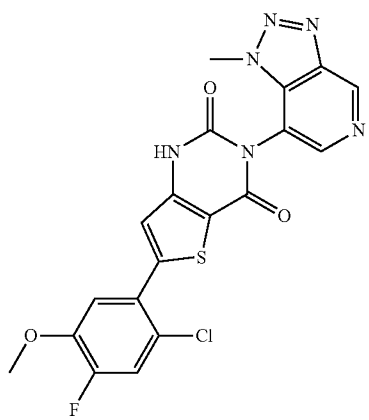 [SMILES: COc1cc(-c2cc3[nH]c(=O)n(-c4cncc5nnn(C)c45)c(=O)c3s2)c(Cl)cc1F] | 458.8 | 1H NMR (400 MHz, DMSO) δ 12.52 (s, 1H), 9.58 (s, 1H), 8.65 (s, 1H), 7.72 (d, J = 11.1 Hz, 1H), 7.46 (d, J = 8.8 Hz, 1H), 7.33 (s, 1H), 4.19 (s, 3H), 3.95 (s, 3H). | 46 | I-281; I-66 |
| 750 | 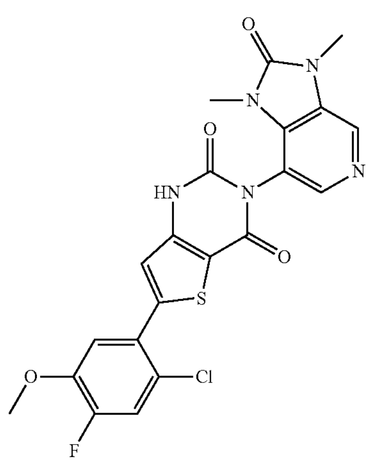 [SMILES: COc1cc(-c2cc3[nH]c(=O)n(-c4cncc5c4n(C)c(=O)n5C)c(=O)c3s2)c(Cl)cc1F] | 487.8 | 1H NMR (400 MHz, DMSO) δ 12.55 (s, 1H), 8.72 (s, 1H), 8.55 (s, 1H), 7.71 (d, J = 11.1 Hz, 1H), 7.45 (d, J = 8.9 Hz, 1H), 7.33 (s, 1H), 3.94 (s, 3H), 3.49 (s, 3H), 3.27 (s, 3H). | 46 | I-282; I-66 |

TABLE 39-continued
Examples 646-768
| Example | Structure | ES/MS m/z | 1H-NMR | Procedure | Changes to Procedure: Different Reagents/Starting Materials |
|---|---|---|---|---|---|
| 751 | 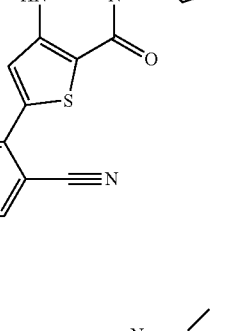 | 448.8 | 1H NMR (400 MHz, DMSO-d6) δ 12.59 (s, 1H), 9.37 (s, 1H), 8.59 (s, 2H), 8.11 (d, J = 11.1 Hz, 1H), 7.58-7.49 (m, 2H), 4.05 (s, 3H), 3.95 (s, 3H). | 64 | I-104; I-188 |
| 752 | 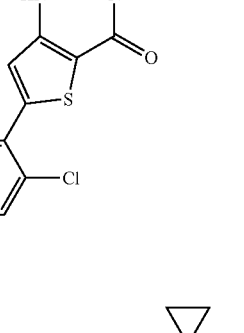 | 471.8 | 1H NMR (400 MHz, DMSO-d6) δ 12.39 (s, 1H), 9.25 (s, 1H), 8.25 (s, 1H), 7.71 (d, J = 11.0 Hz, 1H), 7.49 (d, J = 8.9 Hz, 1H), 7.31 (s, 1H), 4.17 (s, 3H), 3.95 (s, 3H), 2.29 (s, 3H). | 59 | I-254; I-61 |
| 753 | 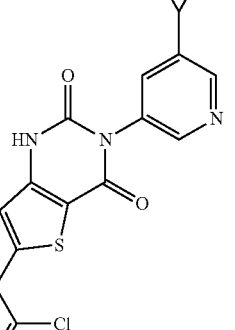 | 443.8 | 1H NMR (400 MHz, DMSO-d6) δ 12.17 (s, 1H), 8.45 (d, J = 2.1 Hz, 1H), 8.35 (d, J = 2.2 Hz, 1H), 7.70 (d, J = 11.1 Hz, 1H), 7.55 (t, J = 2.2 Hz, 1H), 7.43 (d, J = 8.9 Hz, 1H), 7.25 (s, 1H), 3.94 (s, 3H), 2.04 (tt, J = 8.4, 5.1 Hz, 1H), 1.10-1.01 (m, 2H), 0.82-0.71 (m, 2H). | 59 | 5-cyclopropylpyridin-3-amine; I-61 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 754 | 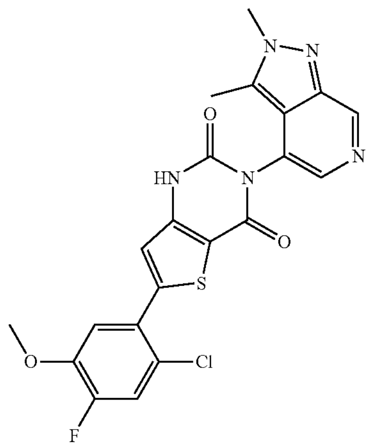 [SMILES: COc1cc(-c2cc3[nH]c(=O)n(-c4cncc5nn(C)c(C)c45)c(=O)c3s2)c(Cl)cc1F] | 471.8 | 1H NMR (400 MHz, DMSO-d6) δ 12.40 (s, 1H), 9.34 (s, 1H), 8.13 (s, 1H), 7.71 (d, J = 11.1 Hz, 1H), 7.47 (d, J = 8.9 Hz, 1H), 7.31 (s, 1H), 4.20 (s, 3H), 3.94 (s, 3H), 2.42 (s, 3H). | 59 | I-255; I-61 |
| 755 | 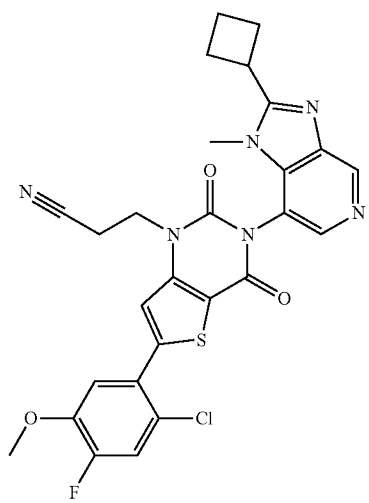 [SMILES: COc1cc(-c2cc3c(s2)c(=O)n(-c2cncc4nc(C5CCC5)n(C)c24)c(=O)n3CCC#N)c(Cl)cc1F] | 564.8 | 1H NMR (400 MHz, DMSO-d6) δ 9.26 (s, 1H), 8.56 (s, 1H), 7.99 (s, 1H), 7.75 (d, J = 11.0 Hz, 1H), 7.55 (d, J = 8.8 Hz, 1H), 4.54 (dt, J = 14.1, 6.9 Hz, 1H), 4.42 (dt, J = 14.3, 6.2 Hz, 1H), 3.97 (s, 4H), 3.59 (s, 3H), 3.07 (t, J = 6.5 Hz, 2H), 2.49-2.40 (m, 4H), 2.19-2.05 (m, 1H), 1.97 (td, J = 10.1, 8.6, 5.4 Hz, 1H). | 59, 96 | I-61; I-293 |
| 756 | 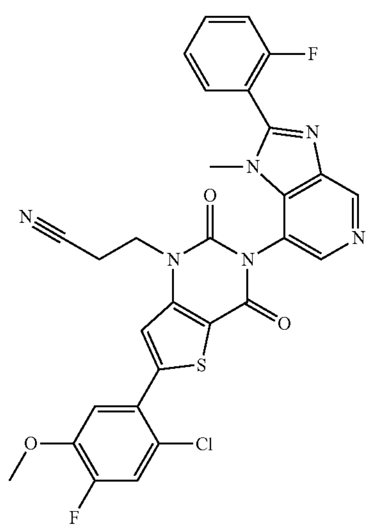 [SMILES: COc1cc(-c2cc3c(s2)c(=O)n(-c2cncc4nc(-c5ccccc5F)n(C)c24)c(=O)n3CCC#N)c(Cl)cc1F] | 604.7 | 1H NMR (400 MHz, DMSO-d6) δ 9.31 (s, 1H), 8.59 (s, 1H), 7.98 (s, 1H), 7.86-7.69 (m, 3H), 7.62-7.39 (m, 3H), 4.63-4.49 (m, 1H), 4.42 (dt, J = 14.3, 6.1 Hz, 1H), 3.97 (s, 3H), 3.60 (d, J = 1.9 Hz, 3H), 3.22-2.92 (m, 2H). | 59, 96 | I-61; I-294 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 757 | 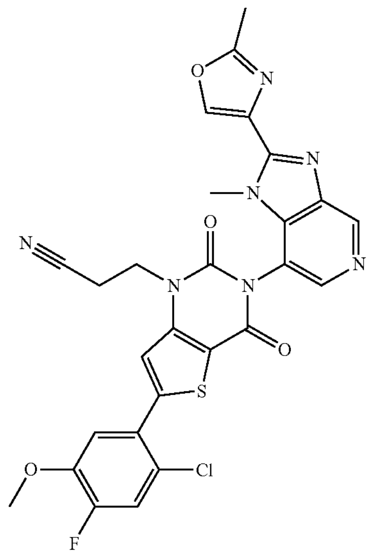 [SMILES: COc1cc(-c2cc3c(s2)c(=O)n(-c2cncc4nc(-c5coc(C)n5)n(C)c24)c(=O)n3CCC#N)c(Cl)cc1F] | 591.8 | 1H NMR (400 MHz, DMSO-d6) δ 9.22 (s, 1H), 8.90 (s, 1H), 8.52 (s, 1H), 7.99 (s, 1H), 7.75 (d, J = 11.0 Hz, 1H), 7.56 (d, J = 8.9 Hz, 1H), 4.63-4.33 (m, 2H), 4.00 (s, 3H), 3.98 (s, 3H), 3.09 (t, J = 6.6 Hz, 2H), 2.56 (s, 3H). | 59, 96 | I-61; I-295 |
| 758 | 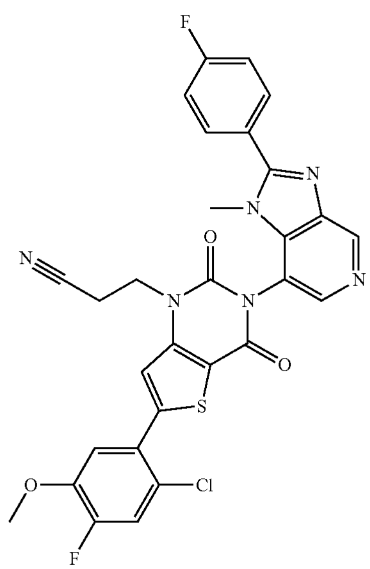 [SMILES: COc1cc(-c2cc3c(s2)c(=O)n(-c2cncc4nc(-c5ccc(F)cc5)n(C)c24)c(=O)n3CCC#N)c(Cl)cc1F] | 604.7 | 1H NMR (400 MHz, DMSO) δ 9.29 (s, 1H), 8.57 (s, 1H), 8.00 (s, 1H), 7.98-7.90 (m, 2H), 7.75 (d, J = 11.0 Hz, 1H), 7.56 (d, J = 8.9 Hz, 1H), 7.52-7.43 (m, 2H), 4.55 (dt, J = 13.9, 6.8 Hz, 1H), 4.44 (dt, J = 14.3, 6.2 Hz, 1H), 3.97 (s, 3H), 3.72 (s, 3H), 3.09 (t, J = 6.5 Hz, 2H). | 59, 96 | I-61; I-296 |
| 759 | 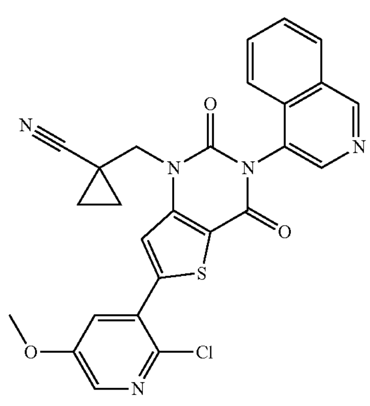 [SMILES: COc1cnc(Cl)c(-c2cc3c(s2)c(=O)n(-c2cncc4ccccc24)c(=O)n3CC2(C#N)CC2)c1] | 516.2 | 1H NMR (400 MHz, DMSO-d6) δ 9.47 (s, 1H), 8.61 (s, 1H), 8.33 (d, J = 3.0 Hz, 1H), 8.30 (dd, J = 7.3, 1.9 Hz, 1H), 8.21 (s, 1H), 7.92-7.87 (m, 2H), 7.84-7.76 (m, 2H), 4.49 (d, J = 15.3 Hz, 1H), 4.33 (d, J = 15.2 Hz, 1H), 3.97 (s, 3H), 1.44-1.27 (m, 4H). | 97 | Example 364 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 760 | 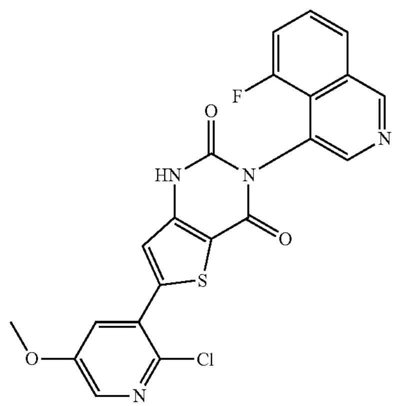 [SMILES: COc1cnc(Cl)c(-c2cc3[nH]c(=O)n(-c4cncc5cccc(F)c45)c(=O)c3s2)c1] | 455.1 | 1H NMR (400 MHz, DMSO-d6) δ 12.37 (s, 1H), 9.53 (d, J = 2.4 Hz, 1H), 8.62 (s, 1H), 8.29 (d, J = 3.0 Hz, 1H), 8.22-8.14 (m, 1H), 7.83 (d, J = 3.0 Hz, 1H), 7.81-7.76 (m, 1H), 7.65 (dd, J = 12.9, 7.8 Hz, 1H), 7.43 (s, 1H), 3.94 (s, 3H). | 10 | I-334; (2-chloro-5-methoxypyridin-3-yl)boronic acid |
| 761 | 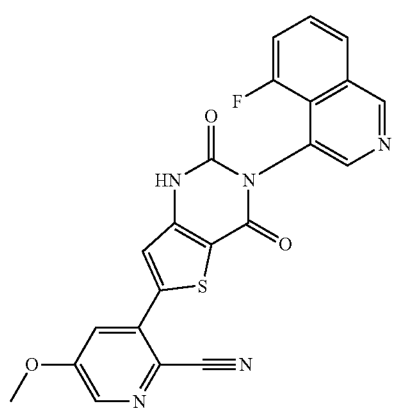 [SMILES: COc1cnc(C#N)c(-c2cc3[nH]c(=O)n(-c4cncc5cccc(F)c45)c(=O)c3s2)c1] | 446.2 | | 10 | I-334; 5-methoxy-3-(4,4,5,5-tetramethyl-1,3,2-dioxaborolan-2-yl)pyridine-2-carbonitrile |
| 762 | 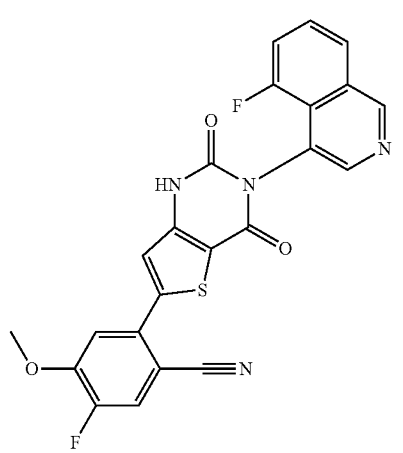 [SMILES: COc1cc(-c2cc3[nH]c(=O)n(-c4cncc5cccc(F)c45)c(=O)c3s2)c(C#N)cc1F] | 463.2 | 1H NMR (400 MHz, DMSO-d6) δ 12.40 (s, 1H), 9.53 (d, J = 2.4 Hz, 1H), 8.63 (s, 1H), 8.18 (d, J = 8.1 Hz, 1H), 8.10 (d, J = 11.1 Hz, 1H), 7.81-7.76 (m, 1H), 7.65 (dd, J = 12.9, 7.8 Hz, 1H), 7.58 (d, J = 8.1 Hz, 1H), 7.48 (s, 1H), 4.04 (s, 3H). | 10 | I-334, I-104 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 763 | 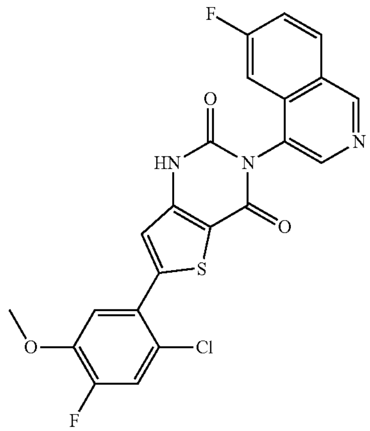 [SMILES: COc1cc(-c2cc3[nH]c(=O)n(-c4cncc5ccc(F)cc45)c(=O)c3s2)c(Cl)cc1F] | 472.1 | 1H NMR (400 MHz, DMSO-d6) δ 12.25 (s, 1H), 9.46 (s, 1H), 8.60 (s, 1H), 8.41 (dd, J = 9.1, 5.6 Hz, 1H), 7.84 (dd, J = 10.3.2.5 Hz, 1H), 7.72 (d, J = 11.0 Hz, 1H), 7.67 (dd, J = 8.9, 2.5 Hz, 1H), 7.43 (d, J = 8.9 Hz, 1H), 7.32 (s, 1H), 3.96 (s, 3H). | 59 | I-66; 5-fluoroisoquinolin-4-amine |
| 764 | 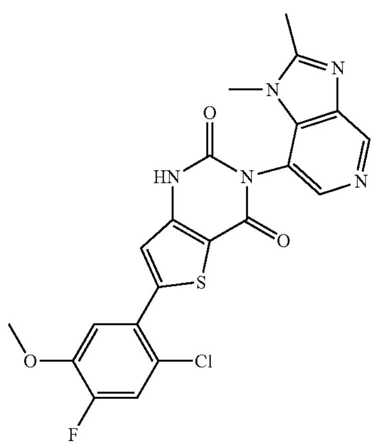 [SMILES: COc1cc(-c2cc3[nH]c(=O)n(-c4cncc5nc(C)n(C)c45)c(=O)c3s2)c(Cl)cc1F] | 471.8 | 1H NMR (400 MHz, DMSO-d6) δ 12.54 (s, 1H), 9.20 (s, 1H), 8.58 (s, 1H), 7.73 (d, J = 11.0 Hz, 1H), 7.46 (d, J = 8.9 Hz, 1H), 7.34 (s, 1H), 3.95 (s, 3H), 3.66 (s, 3H), 2.66 (s, 3H). | 59 | I-66; I-192 |
| 765 | 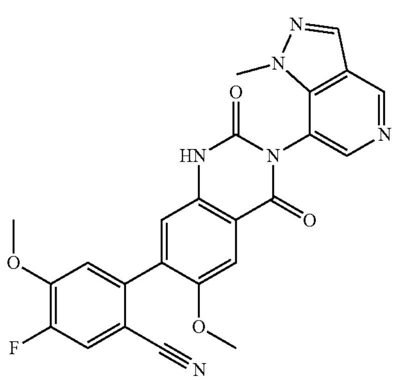 [SMILES: COc1cc(-c2cc3[nH]c(=O)n(-c4cncc5cnn(C)c45)c(=O)c3cc2OC)c(C#N)cc1F] | 471.9 | 1H NMR (400 MHz, DMSO-d6) δ 12.02 (s, 1H), 9.38 (s, 1H), 8.62 (s, 1H), 8.58 (s, 1H), 8.00 (d, J = 11.2 Hz, 1H), 7.62 (s, 1H), 7.38 (d, J = 8.2 Hz, 1H), 7.26 (s, 1H), 3.97 (s, 3H), 3.93 (s, 3H), 3.85 (s, 3H). | 78 | I-104; I-275 |

TABLE 39-continued

Examples 646-768

| Example | Structure | ES/MS m/z | 1H-NMR | Procedure | Changes to Procedure: Different Reagents/Starting Materials |
|---|---|---|---|---|---|
| 766 | 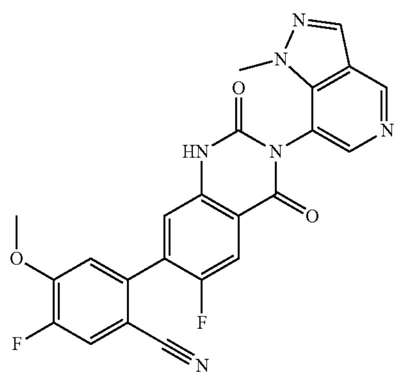 [SMILES: COc1cc(-c2cc3[nH]c(=O)n(-c4cncc5cnn(C)c45)c(=O)c3cc2F)c(C#N)cc1F] | 460.9 | 1H NMR (400 MHz, DMSO-d6) δ 12.20 (s, 1H), 9.35 (s, 1H), 8.58 (s, 1H), 8.55 (s, 1H), 8.10 (d, J = 11.1 Hz, 1H), 7.96 (d, J = 9.2 Hz, 1H), 7.51 (d, J = 8.1 Hz, 1H), 7.40 (d, J = 6.0 Hz, 1H), 3.99 (s, 3H), 3.93 (s, 3H). | 78 | I-104; I-276 |
| 767 | 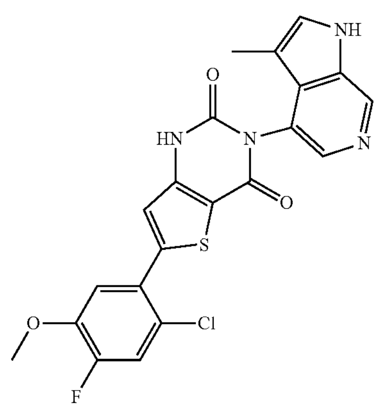 [SMILES: COc1cc(-c2cc3[nH]c(=O)n(-c4cncc5[nH]cc(C)c45)c(=O)c3s2)c(Cl)cc1F] | 456.8 | 1H NMR (400 MHz, DMSO-d6) δ 12.69 (s, 1H), 12.45 (s, 1H), 9.15 (s, 1H), 8.42 (s, 1H), 8.05 (s, 1H), 7.72 (d, J = 11.0 Hz, 1H), 7.49 (d, J = 8.9 Hz, 1H), 7.32 (s, 1H), 3.95 (s, 3H), 2.11 (s, 3H). | 59 | I-66; I-344 |
| 768 | 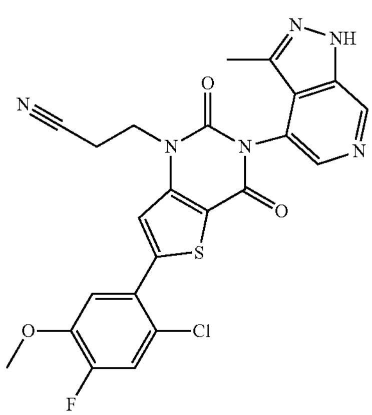 [SMILES: COc1cc(-c2cc3c(s2)c(=O)n(-c2cncc4[nH]nc(C)c24)c(=O)n3CCC#N)c(Cl)cc1F] | 510.8 | 1H NMR (400 MHz, DMSO-d6) δ 9.10 (s, 1H), 8.20 (d, J = 2.1 Hz, 1H), 7.97 (d, J = 1.9 Hz, 1H), 7.79-7.72 (m, 1H), 7.59 (d, J = 8.7 Hz, 1H), 4.63-4.29 (m, 2H), 3.98 (s, 3H), 3.08 (t, J = 5.8 Hz, 2H), 2.31 (s, 3H). | 94 | I-347 |

Procedure 99: Example 769

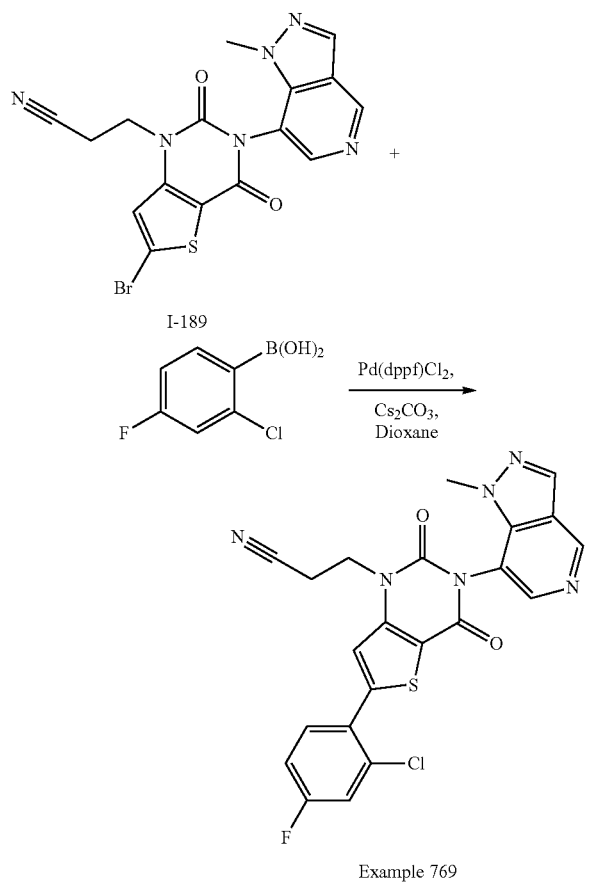

3-(6-(2-chloro-4-fluorophenyl)-3-(1-methyl-1H-pyrazolo[4,3-c]pyridin-7-yl)-2,4-dioxo-3,4-dihydrothieno[3,2-d]pyrimidin-1(2H)-yl)propanenitrile (Example 769): To a microwave vial containing a stir bar was added 3-(6-bromo-3-(1-methyl-1H-pyrazolo[4,3-c]pyridin-7-yl)-2,4-dioxo-3,4-dihydrothieno[3,2-d]pyrimidin-1(2H)-yl)propanenitrile (I-189) (200 mg, 0.464 mmol), (2-chloro-4-fluoro-phenyl)boronic acid (89 mg, 0.51 mmol), Pd(dppf)Cl$_2$ (35 mg, 0.046 mmol), and Cs$_2$CO$_3$ (453 mg, 1.39 mmol), followed by 1,4-Dioxane (5 ml). The vial was degassed under Ar (1 min), sealed with Teflon, and heated at 90° C. for 10 minutes under microwave conditions. The crude product was filtered through an acrodisc and concentrated under reduced pressure. The crude residue was dissolved in ACN (4 mL), water (1 mL) and TFA (0.5 mL), and purified directly by RP-HPLC (0.1% TFA-ACN in 0.1% TFA Water, Column: Gemini 5 µM, NX-C18 110 Angstrom, 250×21.2 mm) to give the product.

ES/MS: 480.7 (M$^+$).

1H NMR (400 MHz, DMSO-d6) δ 9.33 (s, 1H), 8.56 (s, 1H), 8.50 (s, 1H), 8.02 (s, 1H), 7.98-7.94 (m, 1H), 7.76 (dd, J=8.8, 2.7 Hz, 1H), 7.50 (td, J=8.4, 2.7 Hz, 1H), 4.61-4.35 (m, 2H), 3.94 (d, J=1.9 Hz, 3H), 3.12-3.02 (m, 2H).

Examples 770-817

The following Examples were made in an analogous fashion according to Procedure 99 and are shown below in Table 40. To prepare the below Examples, different reagents/starting materials were used than some of those described in Procedure 99 and are noted in the last column of Table 40—"Changes to Procedure 99. Different Reagents/Starting Materials".

TABLE 40

Examples 770-817

| Example | Structure | ES/MS m/z | 1H-NMR | Changes to Procedure 99: Different Reagents/ Starting Materials |
|---|---|---|---|---|
| 770 | 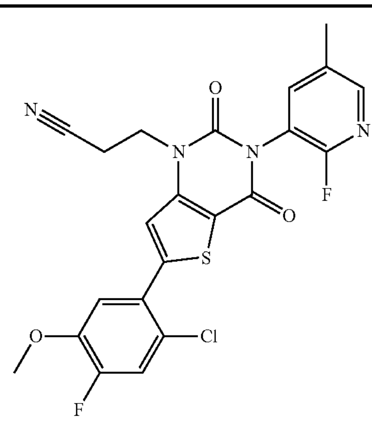 | 488.7 | 1H NMR (400 MHz, DMSO-d6) δ 8.21-8.14 (m, 1H), 7.97-7.90 (m, 2H), 7.73 (d, J = 11.0 Hz, 1H), 7.53 (d, J = 8.9 Hz, 1H), 4.51-4.33 (m, 2H), 3.96 (s, 3H), 3.01 (t, J = 6.6 Hz, 2H), 2.37 (s, 3H) | I-225; (2-chloro-4-fluoro-5-methoxyphenyl)boronic acid |

TABLE 40-continued

Examples 770-817

| Example | Structure | ES/MS m/z | 1H-NMR | Changes to Procedure 99: Different Reagents/ Starting Materials |
|---|---|---|---|---|
| 771 | 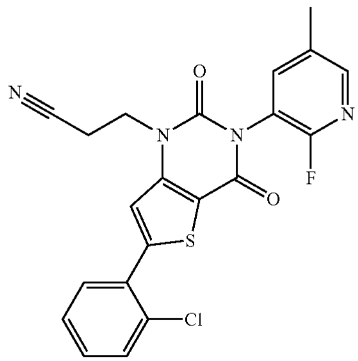 [SMILES: Cc1cnc(F)c(-n2c(=O)c3sc(-c4ccccc4Cl)cc3n(CCC#N)c2=O)c1] | 440.8 | 1H NMR (400 MHz, DMSO-d6) δ 8.17 (d, J = 1.2 Hz, 1H), 7.98 (s, 1H), 7.95 (dd, J = 9.0, 2.3 Hz, 1H), 7.87 (dd, J = 5.9, 3.5 Hz, 1H), 7.69 (dt, J = 7.4, 3.7 Hz, 1H), 7.55 (dd, J = 5.9, 3.5 Hz, 2H), 4.42 (hept, J = 7.3 Hz, 2H), 3.00 (t, J = 6.6 Hz, 2H), 2.37 (s, 3H) | I-225; (2-chlorophenyl) boronic acid |
| 772 | 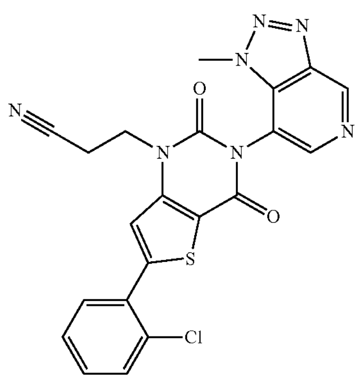 [SMILES: Cn1nnc2cncc(-n3c(=O)c4sc(-c5ccccc5Cl)cc4n(CCC#N)c3=O)c21] | 463.8 | 1H NMR (400 MHz, DMSO-d6) δ 9.60 (s, 1H), 8.63 (s, 1H), 8.04 (s, 1H), 7.95-7.84 (m, 1H), 7.73-7.69 (m, 1H), 7.62-7.51 (m, 2H), 4.59-4.36 (m, 2H), 4.19 (s, 3H), 3.06 (t, J = 6.6 Hz, 2H) | I-228; (2-chlorophenyl) boronic acid |
| 773 | 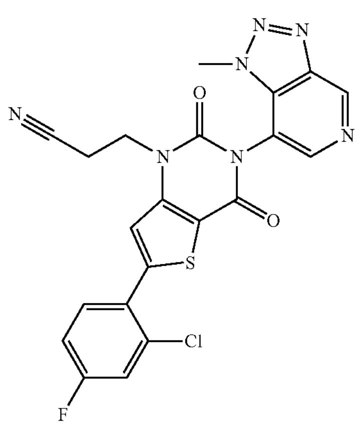 [SMILES: Cn1nnc2cncc(-n3c(=O)c4sc(-c5ccc(F)cc5Cl)cc4n(CCC#N)c3=O)c21] | 481.8 | 1H NMR (400 MHz, DMSO-d6) δ 9.60 (s, 1H), 8.63 (s, 1H), 8.01 (s, 1H), 7.95 (dd, J = 8.8, 6.1 Hz, 1H), 7.75 (dd, J = 8.8, 2.6 Hz, 1H), 7.50 (td, J = 8.4, 2.6 Hz, 1H), 4.57-4.36 (m, 2H), 4.19 (s, 3H), 3.06 (t, J = 6.6 Hz, 2H) | I-228 |

TABLE 40-continued

Examples 770-817

| Example | Structure | ES/MS m/z | 1H-NMR | Changes to Procedure 99: Different Reagents/ Starting Materials |
|---|---|---|---|---|
| 774 | 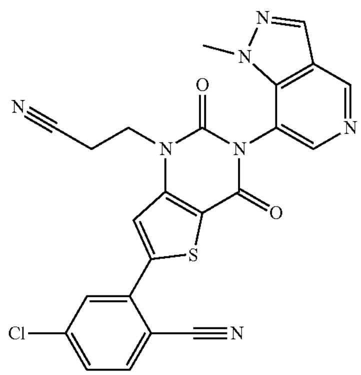 [SMILES: Cn1ncc2cncc(-n3c(=O)c4sc(-c5cc(Cl)ccc5C#N)cc4n(CCC#N)c3=O)c21] | 487.8 | 1H NMR (400 MHz, DMSO-d6) δ 9.35 (s, 1H), 8.58 (s, 1H), 8.52 (s, 1H), 8.20 (s, 1H), 8.17-8.12 (m, 2H), 7.86 (dd, J = 8.4, 2.1 Hz, 1H), 4.55 (dt, J = 14.4, 7.2 Hz, 1H), 4.40 (dt, J = 14.4, 6.3 Hz, 1H), 3.95 (s, 3H), 3.20-3.01 (m, 2H). | (5-chloro-2-cyano-phenyl)boronic acid |
| 775 | 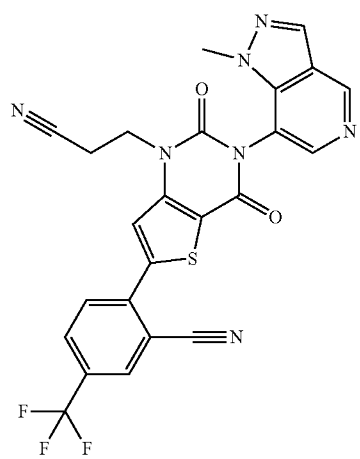 [SMILES: Cn1ncc2cncc(-n3c(=O)c4sc(-c5ccc(C(F)(F)F)cc5C#N)cc4n(CCC#N)c3=O)c21] | 521.8 | 1H NMR (400 MHz, DMSO-d6) δ 9.31 (s, 1H), 8.64 (d, J = 1.9 Hz, 1H), 8.54 (s, 1H), 8.49 (s, 1H), 8.32 (dd, J = 8.5, 1.9 Hz, 1H), 8.25 (d, J = 1.3 Hz, 1H), 8.20 (d, J = 8.4 Hz, 1H), 4.55 (dt, J = 14.3, 7.1 Hz, 1H), 4.41 (dt, J = 13.8, 6.3 Hz, 1H), 3.94 (d, J = 1.2 Hz, 3H), 3.09 (t, J = 6.7 Hz, 2H). | 2-(4,4,5,5-tetramethyl-1,3,2-dioxaborolan-2-yl)-5-(trifluoromethyl)benzonitrile |
| 776 | 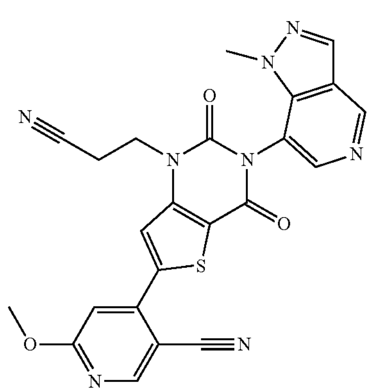 [SMILES: COc1cc(-c2cc3c(s2)c(=O)n(-c2cncc4cnn(C)c24)c(=O)n3CCC#N)c(C#N)cn1] | 484.7 | 1H NMR (400 MHz, DMSO-d6) δ 9.21 (s, 1H), 8.94 (s, 1H), 8.45 (s, 1H), 8.39 (s, 1H), 8.31 (s, 1H), 7.52 (s, 1H), 4.54 (dt, J = 14.3, 7.2 Hz, 1H), 4.45-4.33 (m, 1H), 4.05 (s, 3H), 3.90 (s, 3H), 3.08 (d, J = 6.8 Hz, 2H). | I-105 |

TABLE 40-continued

Examples 770-817

| Example | Structure | ES/MS m/z | 1H-NMR | Changes to Procedure 99: Different Reagents/ Starting Materials |
|---|---|---|---|---|
| 777 | 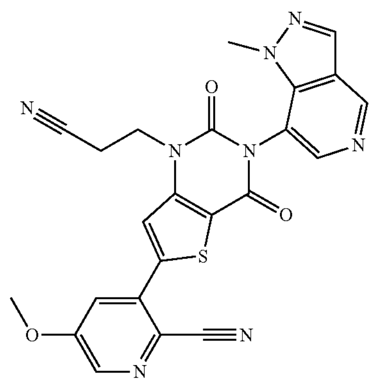 [SMILES: COc1cnc(C#N)c(-c2cc3c(s2)c(=O)n(-c2cncc4cnn(C)c24)c(=O)n3CCC#N)c1] | 484.8 | 1H NMR (400 MHz, DMSO-d6) δ 9.32 (s, 1H), 8.63 (d, J = 2.7 Hz, 1H), 8.56 (s, 1H), 8.50 (s, 1H), 8.23 (s, 1H), 7.91 (d, J = 2.7 Hz, 1H), 4.56 (dt, J = 14.3, 7.1 Hz, 1H), 4.40 (dt, J = 14.3, 6.3 Hz, 1H), 4.06 (s, 3H), 3.94 (s, 3H), 3.10 (t, J = 6.7 Hz, 2H). | I-129 |
| 778 | 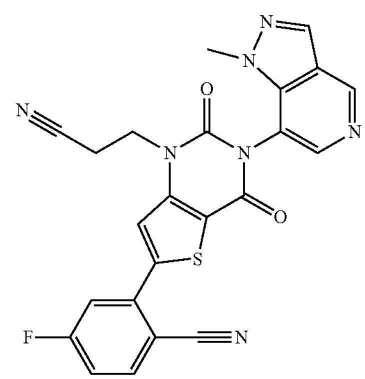 [SMILES: Cn1ncc2cncc(-n3c(=O)c4sc(-c5cc(F)ccc5C#N)cc4n(CCC#N)c3=O)c21] | 471.8 | 1H NMR (400 MHz, DMSO-d6) δ 9.35 (s, 1H), 8.59 (s, 1H), 8.52 (s, 1H), 8.27-8.18 (m, 2H), 7.97 (dd, J = 9.5, 2.6 Hz, 1H), 7.66 (td, J = 8.4, 2.6 Hz, 1H), 4.55 (dt, J = 14.3, 7.1 Hz, 1H), 4.40 (dt, J = 14.3, 6.2 Hz, 1H), 3.95 (s, 3H), 3.14-3.05 (m, 2H). | 4-fluoro-2-(4,4,5,5-tetramethyl-1,3,2-dioxaborolan-2-yl)benzonitrile |
| 779 | 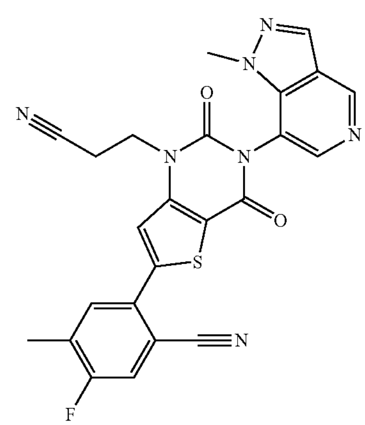 [SMILES: Cc1cc(-c2cc3c(s2)c(=O)n(-c2cncc4cnn(C)c24)c(=O)n3CCC#N)c(C#N)cc1F] | 485.8 | 1H NMR (400 MHz, DMSO-d6) δ 9.30 (s, 1H), 8.51 (d, J = 23.8 Hz, 2H), 8.16-8.05 (m, 3H), 4.54 (dt, J = 14.2, 7.2 Hz, 1H), 4.39 (dt, J = 14.3, 6.3 Hz, 1H), 3.92 (s, 3H), 3.08 (t, J = 6.7 Hz, 2H), 2.42 (d, J = 2.0 Hz, 3H). | I-212 |

TABLE 40-continued

Examples 770-817

| Example | Structure | ES/MS m/z | 1H-NMR | Changes to Procedure 99: Different Reagents/ Starting Materials |
|---|---|---|---|---|
| 780 | 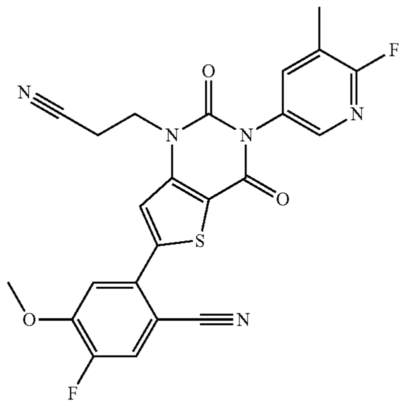 [SMILES: COc1cc(-c2cc3c(s2)c(=O)n(-c2cnc(F)c(C)c2)c(=O)n3CCC#N)c(C#N)cc1F] | 479.7 | 1H NMR (400 MHz, DMSO-d6) δ 8.17-8.06 (m, 2H), 8.04 (s, 1H), 7.95-7.87 (m, 1H), 7.58 (d, J = 8.0 Hz, 1H), 4.41 (t, J = 6.8 Hz, 2H), 4.06 (s, 3H), 3.00 (t, J = 6.8 Hz, 2H), 2.31 (s, 3H). | I-213; I-104 |
| 781 | 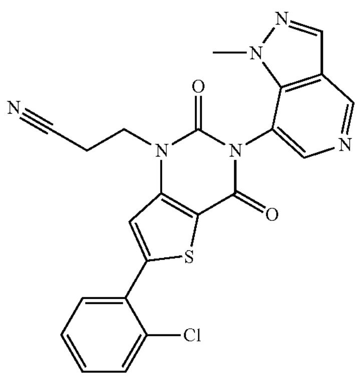 [SMILES: Cn1ncc2cncc(-n3c(=O)c4sc(-c5ccccc5Cl)cc4n(CCC#N)c3=O)c21] | 462.8 | 1H NMR (400 MHz, DMSO-d6) δ 9.36 (s, 1H), 8.59 (s, 1H), 8.53 (s, 1H), 8.04 (s, 1H), 7.97-7.85 (m, 1H), 7.78-7.67 (m, 1H), 7.63-7.51 (m, 2H), 4.48 (ddt, J = 47.6, 14.3, 6.6 Hz, 2H), 3.95 (s, 3H), 3.07 (t, J = 6.6 Hz, 2H). | (2-chlorophenyl) boronic acid |
| 782 | 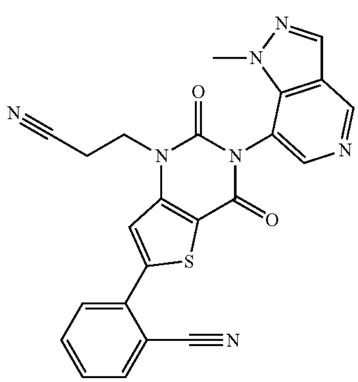 | 453.8 | 1H NMR (400 MHz, DMSO-d6) δ 9.29 (s, 1H), 8.59-8.42 (m, 2H), 8.21-8.06 (m, 2H), 7.95 (dt, J = 20.1, 8.2 Hz, 2H), 7.76 (t, J = 7.4 Hz, 1H), 4.54 (dd, J = 14.2, 7.2 Hz, 1H), 4.39 (dd, J = 14.4, 6.8 Hz, 1H), 3.93 (d, J = 3.5 Hz, 3H), 3.13-2.99 (m, 2H). | (2-cyanophenyl) boronic acid |

TABLE 40-continued

Examples 770-817

| Example | Structure | ES/MS m/z | 1H-NMR | Changes to Procedure 99: Different Reagents/ Starting Materials |
|---|---|---|---|---|
| 783 | 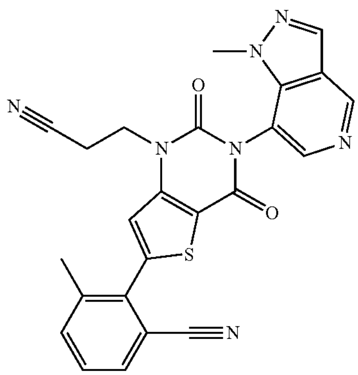 [SMILES: Cc1cccc(C#N)c1-c1cc2c(s1)c(=O)n(-c1cncc3cnn(C)c13)c(=O)n2CCC#N] | 467.8 | 1H NMR (400 MHz, DMSO-d6) δ 9.29 (s, 1H), 8.52 (d, J = 4.9 Hz, 2H), 7.95-7.86 (m, 2H), 7.80 (d, J = 7.8 Hz, 1H), 7.66 (t, J = 7.8 Hz, 1H), 4.66-4.34 (m, 2H), 3.95 (s, 3H), 3.03 (td, J = 6.6, 2.2 Hz, 2H), 2.37 (s, 3H). | 3-methyl-2-(4,4,5,5-tetramethyl-1,3,2-dioxaborolan-2-yl)benzonitrile |
| 784 | 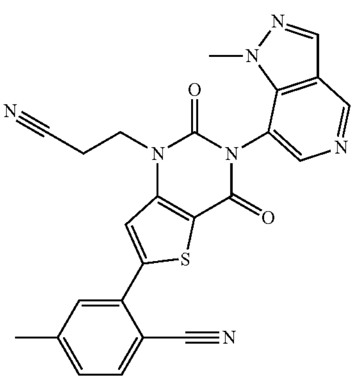 [SMILES: Cc1ccc(C#N)c(-c2cc3c(s2)c(=O)n(-c2cncc4cnn(C)c24)c(=O)n3CCC#N)c1] | 467.8 | 1H NMR (400 MHz, DMSO-d6) δ 9.30 (s, 1H), 8.53 (s, 1H), 8.47 (s, 1H), 8.11 (s, 1H), 7.99 (d, J = 8.0 Hz, 1H), 7.81 (s, 1H), 7.58 (dd, J = 7.9, 1.6 Hz, 1H), 4.63-4.31 (m, 2H), 3.93 (s, 3H), 3.08 (t, J = 6.7 Hz, 2H), 2.52 (s, 3H). | 4-methyl-2-(4,4,5,5-tetramethyl-1,3,2-dioxaborolan-2-yl)benzonitrile |
| 785 | 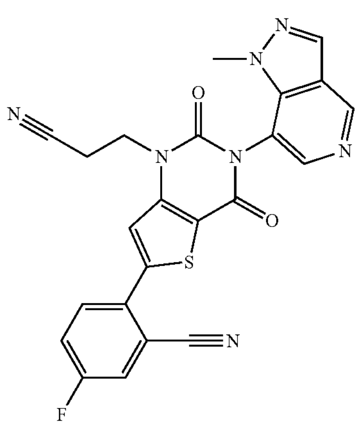 [SMILES: Cn1ncc2cncc(-n3c(=O)c4sc(-c5ccc(F)cc5C#N)cc4n(CCC#N)c3=O)c21] | 471.8 | 1H NMR (400 MHz, DMSO-d6) δ 9.21 (s, 1H), 8.57 (s, 1H), 8.42 (d, J = 21.1 Hz, 1H), 8.22-7.95 (m, 1H), 7.95-7.71 (m, 2H), 7.71-7.47 (m, 1H), 4.63-4.31 (m, 2H), 3.91 (s, 3H), 3.08 (t, J = 6.6 Hz, 2H). | (2-cyano-4-fluoro-phenyl)boronic acid |

TABLE 40-continued

Examples 770-817

| Example | Structure | ES/MS m/z | 1H-NMR | Changes to Procedure 99: Different Reagents/ Starting Materials |
|---|---|---|---|---|
| 786 | 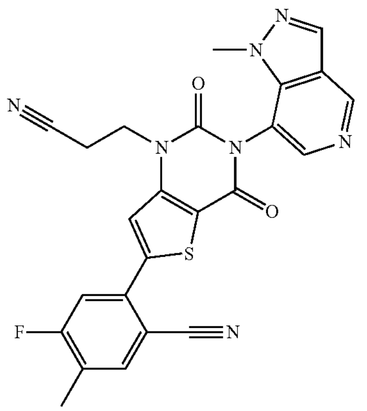 [SMILES: Cc1cc(C#N)c(-c2cc3c(s2)c(=O)n(-c2cncc4cnn(C)c24)c(=O)n3CCC#N)cc1F] | 485.8 | 1H NMR (400 MHz, DMSO-d6) δ 9.27 (s, 1H), 8.51 (s, 1H), 8.44 (s, 1H), 8.21-8.11 (m, 2H), 7.92 (d, J = 10.2 Hz, 1H), 4.47 (ddt, J = 58.6, 13.7, 6.7 Hz, 2H), 3.92 (s, 3H), 3.09 (t, J = 6.8 Hz, 2H), 2.37 (s, 3H). | (2-cyano-5-fluoro-4-methyl-phenyl)boronic acid |
| 787 | 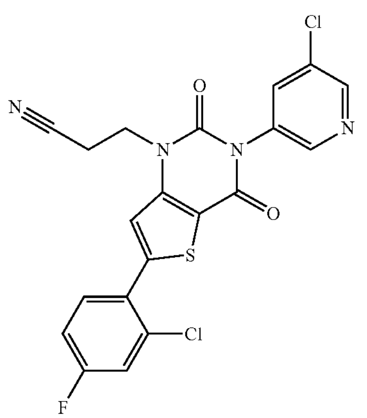 [SMILES: N#CCCn1c(=O)n(-c2cncc(Cl)c2)c(=O)c2sc(-c3ccc(F)cc3Cl)cc21] | 461.5 | 1H NMR (400 MHz, DMSO-d6) δ 8.74 (d, 1H), 8.59 (d, 1H), 8.13 (t, 1H), 7.99-7.87 (m, 2H), 7.74 (dd, 1H), 7.49 (td, 1H), 4.41 (t, 2H), 2.98 (t, 2H). | I-265 |
| 788 | 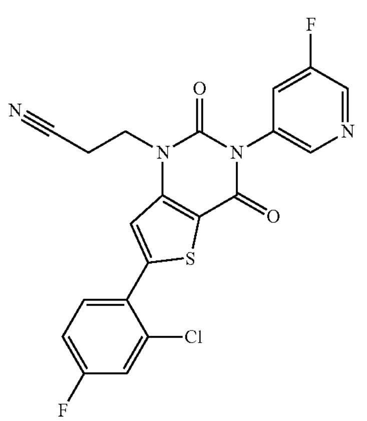 [SMILES: N#CCCn1c(=O)n(-c2cncc(F)c2)c(=O)c2sc(-c3ccc(F)cc3Cl)cc21] | 445.5 | 1H NMR (400 MHz, DMSO-d6) δ 8.71 (d, 1H), 8.51 (t, 1H), 7.97 (s, 1H), 7.96-7.89 (m, 2H), 7.74 (dd, 1H), 7.49 (td, 1H), 4.41 (t, 2H), 2.98 (t, 2H). | I-266 |

TABLE 40-continued

Examples 770-817

| Example | Structure | ES/MS m/z | 1H-NMR | Changes to Procedure 99: Different Reagents/ Starting Materials |
|---|---|---|---|---|
| 789 | 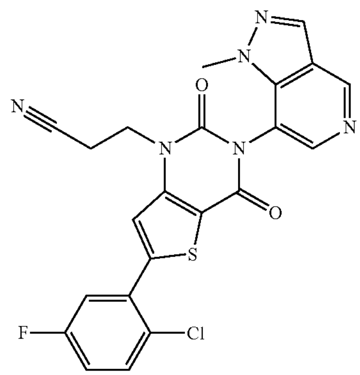 [SMILES: Cn1ncc2cncc(-n3c(=O)c4sc(-c5cc(F)ccc5Cl)cc4n(CCC#N)c3=O)c21] | 481.8 | 1H NMR (400 MHz, DMSO) δ 9.37 (s, 1H), 8.59 (s, 1H), 8.53 (s, 1H), 8.12 (s, 1H), 7.91 (dd, J = 9.5, 3.1 Hz, 1H), 7.78 (dd, J = 9.0, 5.3 Hz, 1H), 7.48 (ddd, J = 8.9, 7.9, 3.1 Hz, 1H), 4.55 (dt, J = 14.3, 7.1 Hz, 1H), 4.42 (dt, J = 14.3, 6.2 Hz, 1H), 3.95 (s, 3H), 3.09 (td, J = 6.7, 2.8 Hz, 2H). | (2-chloro-5-fluoro-phenyl)boronic acid |
| 790 | 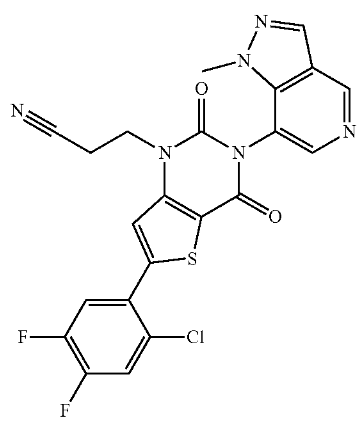 [SMILES: Cn1ncc2cncc(-n3c(=O)c4sc(-c5cc(F)c(F)cc5Cl)cc4n(CCC#N)c3=O)c21] | 499.7 | 1H NMR (400 MHz, DMSO) δ 9.29 (s, 1H), 8.53 (s, 1H), 8.47 (s, 1H), 8.15 (dd, J = 11.4, 8.4 Hz, 1H), 8.11-7.98 (m, 2H), 4.54 (dd, J = 14.4, 7.1 Hz, 1H), 4.40 (dt, J = 14.3, 6.2 Hz, 1H), 3.92 (s, 3H), 3.09 (td, J = 6.7, 2.6 Hz, 2H). | 2-(2-chloro-4,5-difluoro-phenyl)-4,4,5,5-tetramethyl-1,3,2-dioxaborolane |
| 791 | 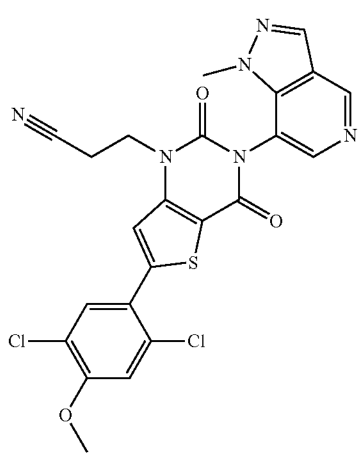 [SMILES: COc1cc(Cl)c(-c2cc3c(s2)c(=O)n(-c2cncc4cnn(C)c24)c(=O)n3CCC#N)cc1Cl] | 528.8 | 1H NMR (400 MHz, DMSO) δ 9.28 (s, 1H), 8.52 (s, 1H), 8.46 (s, 1H), 8.11 (s, 1H), 8.04 (s, 1H), 7.51 (s, 1H), 4.56-4.51 (m, 1H), 4.44-4.38 (m, 1H), 3.99 (s, 3H), 3.91 (s, 3H), 3.09 (td, J = 6.7, 3.8 Hz, 2H). | (2,5-dichloro-4-methoxy-phenyl)boronic acid |

TABLE 40-continued

Examples 770-817

| Example | Structure | ES/MS m/z | 1H-NMR | Changes to Procedure 99: Different Reagents/ Starting Materials |
|---|---|---|---|---|
| 792 | 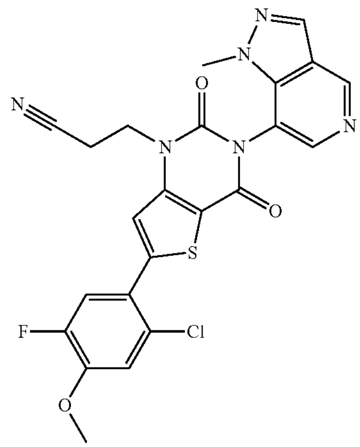 [SMILES: COc1cc(Cl)c(-c2cc3c(s2)c(=O)n(-c2cncc4cnn(C)c24)c(=O)n3CCC#N)cc1F] | 510.8 | 1H NMR (400 MHz, DMSO) δ 9.34 (s, 1H), 8.57 (s, 1H), 8.51 (s, 1H), 8.03 (s, 1H), 7.96 (d, J = 12.2 Hz, 1H), 7.53 (d, J = 8.0 Hz, 1H), 4.55-4.50 (m, 1H), 4.44-4.38 (m, 1H), 3.97 (s, 3H), 3.93 (s, 3H), 3.08 (dt, J = 6.6, 3.0 Hz, 2H). | (2-chloro-5-fluoro-4-methoxy-phenyl)boronic acid |
| 793 | 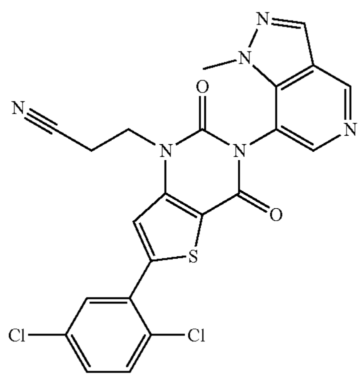 [SMILES: Cn1ncc2cncc(-n3c(=O)c4sc(-c5cc(Cl)ccc5Cl)cc4n(CCC#N)c3=O)c21] | 498.7 | 1H NMR (400 MHz, DMSO) δ 9.39 (s, 1H), 8.62 (s, 1H), 8.56 (s, 1H), 8.12 (s, 1H), 8.07 (d, J = 2.5 Hz, 1H), 7.76 (d, J = 8.6 Hz, 1H), 7.65 (dd, J = 8.7, 2.5 Hz, 1H), 4.55 (dt, J = 14.2, 7.0 Hz, 1H), 4.42 (dt, J = 14.4, 6.2 Hz, 1H), 3.95 (s, 3H), 3.09 (td, J = 6.6, 3.8 Hz, 2H). | (2,5-dichlorophenyl)boronic acid |
| 794 | 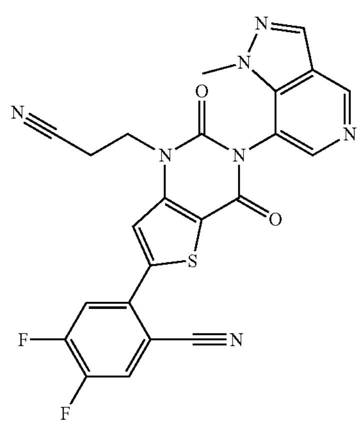 [SMILES: Cn1ncc2cncc(-n3c(=O)c4sc(-c5cc(F)c(F)cc5C#N)cc4n(CCC#N)c3=O)c21] | 490.8 | 1H NMR (400 MHz, DMSO) δ 9.38 (s, 1H), 8.60 (s, 1H), 8.54 (s, 1H), 8.47 (dd, J = 10.4, 7.8 Hz, 1H), 8.24-8.16 (m, 2H), 4.54 (dt, J = 14.3, 7.2 Hz, 1H), 4.39 (dt, J = 14.3, 6.3 Hz, 1H), 3.95 (s, 3H), 3.09 (d, J = 13.6 Hz, 2H). | (2-cyano-4,5-difluoro-phenyl)boronic acid, copper(I) chloride (1 equiv.) |

TABLE 40-continued

Examples 770-817

| Example | Structure | ES/MS m/z | 1H-NMR | Changes to Procedure 99: Different Reagents/ Starting Materials |
|---|---|---|---|---|
| 795 | 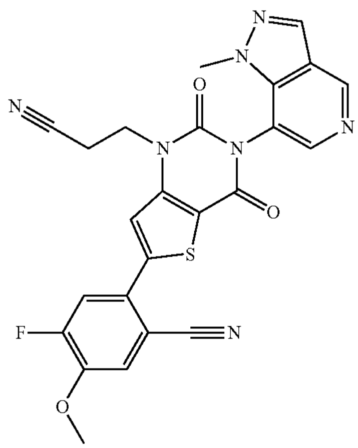 [SMILES: COc1cc(C#N)c(-c2cc3c(s2)c(=O)n(-c2cncc4cnn(C)c24)c(=O)n3CCC#N)cc1F] | 501.8 | 1H NMR (400 MHz, DMSO) δ 9.34 (s, 1H), 8.56 (d, J = 6.5 Hz, 1H), 8.49 (d, J = 12.3 Hz, 1H), 8.10 (s, 1H), 8.03-7.94 (m, 2H), 7.66-7.58 (m, 1H), 4.53 (d, J = 7.1 Hz, 1H), 4.41-4.38 (m, 1H), 4.01 (s, 3H), 3.94 (d, J = 3.9 Hz, 3H), 3.08 (d, J = 6.9 Hz, 2H). | I-315 |
| 796 | 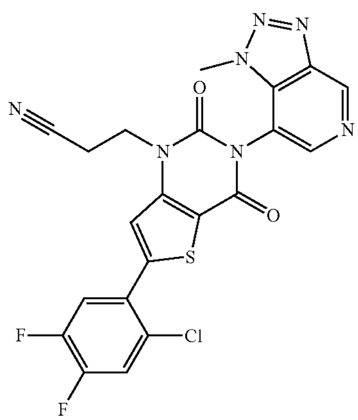 [SMILES: Cn1nnc2cncc(-n3c(=O)c4sc(-c5cc(F)c(F)cc5Cl)cc4n(CCC#N)c3=O)c21] | 499.7 | 1H NMR (400 MHz, DMSO) δ 9.60 (s, 1H), 8.64 (s, 1H), 8.15 (dd, J = 11.4, 8.4 Hz, 1H), 8.09-8.01 (m, 2H), 4.52 (dt, J = 14.2, 7.0 Hz, 1H), 4.41 (dt, J = 14.4, 6.3 Hz, 1H), 4.19 (s, 3H), 3.09 (td, J = 6.7, 1.8 Hz, 2H). | I-228; 2-(2-chloro-4,5-difluoro-phenyl)-4,4,5,5-tetramethyl-1,3,2-dioxaborolane |
| 797 | 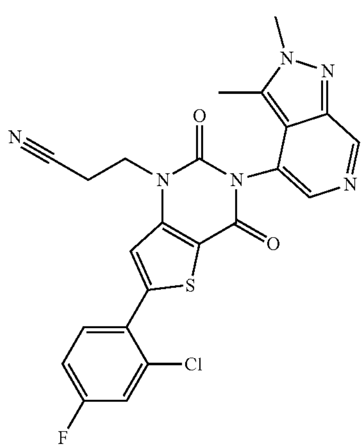 [SMILES: Cc1c2c(-n3c(=O)c4sc(-c5ccc(F)cc5Cl)cc4n(CCC#N)c3=O)cncc2nn1C] | 494.8 | 1H NMR (400 MHz, DMSO) δ 9.49 (s, 1H), 8.20 (s, 1H), 8.02 (s, 1H), 7.96 (dd, J = 8.8, 6.1 Hz, 1H), 7.75 (dd, J = 8.8, 2.7 Hz, 1H), 7.50 (td, J = 8.5, 2.7 Hz, 1H), 4.51 (dt, J = 13.9, 6.9 Hz, 1H), 4.40 (dt, J = 14.3, 6.3 Hz, 1H), 4.24 (s, 3H), 3.05 (d, J = 6.7 Hz, 2H), 2.45 (s, 3H). | I-257 |

TABLE 40-continued

Examples 770-817

| Example | Structure | ES/MS m/z | 1H-NMR | Changes to Procedure 99: Different Reagents/ Starting Materials |
|---|---|---|---|---|
| 798 | 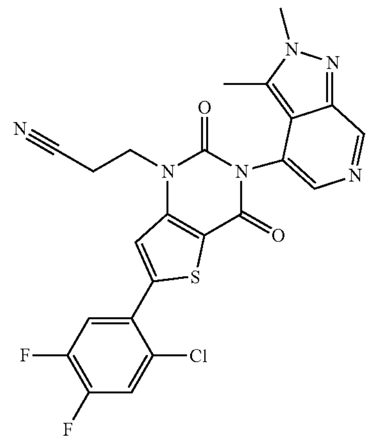 [SMILES: Cc1c2c(-n3c(=O)c4sc(-c5cc(F)c(F)cc5Cl)cc4n(CCC#N)c3=O)cncc2nn1C] | 512.7 | 1H NMR (400 MHz, DMSO) δ 9.36 (s, 1H), 8.20-8.11 (m, 2H), 8.09-7.99 (m, 2H), 4.51 (dt, J = 14.0, 6.9 Hz, 1H), 4.39 (dt, J = 14.2, 6.3 Hz, 1H), 4.20 (s, 3H), 3.07 (d, J = 13.6 Hz, 2H), 2.42 (s, 3H). | I-257; 2-(2-chloro-4,5-difluoro-phenyl)-4,4,5,5-tetramethyl-1,3,2-dioxaborolane |
| 799 | 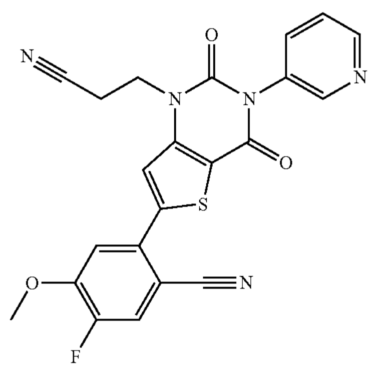 [SMILES: COc1cc(-c2cc3c(s2)c(=O)n(-c2cccnc2)c(=O)n3CCC#N)c(C#N)cc1F] | 447.8 | 1H NMR (400 MHz, DMSO) δ 8.67 (d, J = 4.8 Hz, 1H), 8.61 (d, J = 2.4 Hz, 1H), 8.13 (d, J = 11.1 Hz, 1H), 8.05 (s, 1H), 7.90 (dt, J = 8.3, 2.0 Hz, 1H), 7.67-7.55 (m, 2H), 4.42 (t, J = 6.8 Hz, 2H), 4.06 (s, 3H), 3.00 (d, J = 13.5 Hz, 2H). | I-352; 5-fluoro-4-methoxy-2-(4,4,5,5-tetramethyl-1,3,2-dioxaborolan-2-yl)benzonitrile |
| 800 | 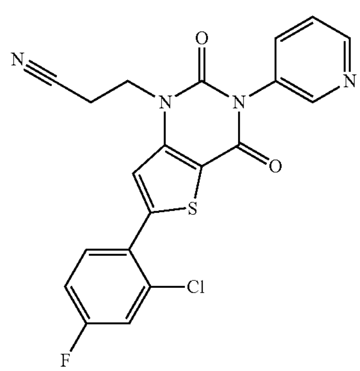 [SMILES: N#CCCn1c(=O)n(-c2cccnc2)c(=O)c2sc(-c3ccc(F)cc3Cl)cc21] | 426.8 | 1H NMR (400 MHz, DMSO) δ 8.70 (dd, J = 4.9, 1.5 Hz, 1H), 8.65 (d, J = 2.4 Hz, 1H), 8.00-7.87 (m, 3H), 7.74 (dd, J = 8.8, 2.6 Hz, 1H), 7.68 (dd, J = 8.1, 4.9 Hz, 1H), 7.51-7.46 (m, 1H), 4.41 (d, J = 13.3 Hz, 2H), 2.98 (t, J = 6.6 Hz, 2H). | I-352; (2-chloro-4-fluoro-phenyl)boronic acid |

TABLE 40-continued

Examples 770-817

| Example | Structure | ES/MS m/z | 1H-NMR | Changes to Procedure 99: Different Reagents/ Starting Materials |
|---|---|---|---|---|
| 801 | 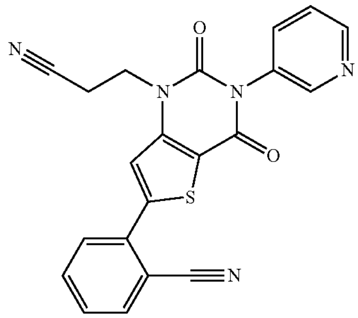 [SMILES: N#CCCn1c(=O)n(-c2cccnc2)c(=O)c2sc(-c3ccccc3C#N)cc21] | 399.8 | 1H NMR (400 MHz, DMSO) δ 8.66 (dd, J = 4.9, 1.6 Hz, 1H), 8.60 (d, J = 2.4 Hz, 1H), 8.10 (d, J = 9.0 Hz, 2H), 7.98-7.85 (m, 3H), 7.74 (ddd, J = 8.6, 6.9, 1.9 Hz, 1H), 7.62 (dd, J = 8.1, 4.8 Hz, 1H), 4.41 (t, J = 6.8 Hz, 2H), 2.99 (d, J = 13.7 Hz, 2H). | I-352; (2-cyanophenyl) boronic acid |
| 802 | 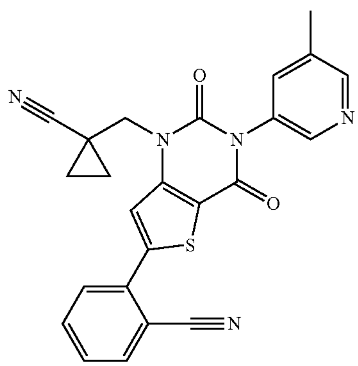 [SMILES: Cc1cncc(-n2c(=O)c3sc(-c4ccccc4C#N)cc3n(CC3(C#N)CC3)c2=O)c1] | 439.9 | 1H NMR (400 MHz, DMSO) δ 8.50 (d, J = 2.1 Hz, 1H), 8.40 (d, J = 2.3 Hz, 1H), 8.13-8.05 (m, 2H), 7.97-7.88 (m, 2H), 7.77-7.69 (m, 2H), 4.36 (s, 2H), 2.39 (s, 3H), 1.34 (dt, J = 11.0, 2.2 Hz, 3H), 1.25-1.22 (m, 1H). | I-353; (2-cyanophenyl) boronic acid |
| 803 | 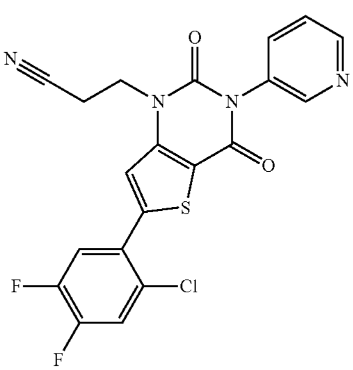 [SMILES: N#CCCn1c(=O)n(-c2cccnc2)c(=O)c2sc(-c3cc(F)c(F)cc3Cl)cc21] | 444.7 | 1H NMR (400 MHz, DMSO) δ 8.66 (dd, J = 4.8, 1.6 Hz, 1H), 8.60 (d, J = 2.4 Hz, 1H), 8.11 (dd, J = 11.4, 8.4 Hz, 1H), 8.05-7.99 (m, 2H), 7.89 (ddd, J = 8.1, 2.5, 1.5 Hz, 1H), 7.64-7.60 (m, 1H), 4.40 (t, J = 6.8 Hz, 3H), 3.00 (d, J = 13.4 Hz, 2H). | I-352; 2-(2-chloro-4,5-difluoro-phenyl)-4,4,5,5-tetramethyl-1,3,2-dioxaborolane |

TABLE 40-continued

Examples 770-817

| Example | Structure | ES/MS m/z | 1H-NMR | Changes to Procedure 99: Different Reagents/ Starting Materials |
|---|---|---|---|---|
| 804 | 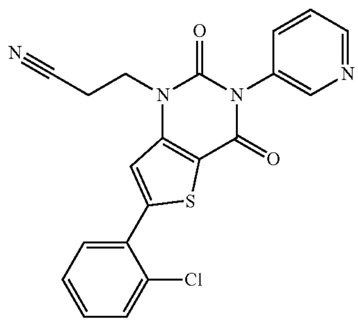 [SMILES: N#CCCn1c(=O)n(-c2cccnc2)c(=O)c2sc(-c3ccccc3Cl)cc21] | 408.9 | 1H NMR (400 MHz, DMSO) δ 8.68 (dd, J = 4.9, 1.5 Hz, 1H), 8.63 (d, J = 2.4 Hz, 1H), 7.98 (s, 1H), 7.93 (ddd, J = 8.1, 2.5, 1.5 Hz, 1H), 7.90-7.82 (m, 1H), 7.75-7.61 (m, 2H), 7.60-7.51 (m, 2H), 4.42 (t, J = 6.6 Hz, 2H), 2.99 (t, J = 6.6 Hz, 2H). | I-352; (2-chlorophenyl) boronic acid |
| 805 | 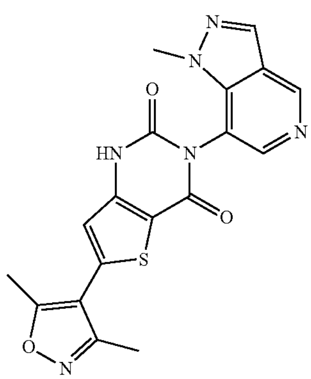 [SMILES: Cc1noc(C)c1-c1cc2[nH]c(=O)n(-c3cncc4cnn(C)c34)c(=O)c2s1] | 394.8 | 1H NMR (400 MHz, DMSO-d6) δ 12.46 (s, 1H), 9.29 (s, 1H), 8.53 (s, 1H), 8.47 (s, 1H), 7.13 (s, 1H), 3.89 (s, 3H), 2.62 (s, 3H), 2.41 (s, 3H). | I-188; (3,5-dimethylisoxazol-4-yl)boronic acid |
| 806 | 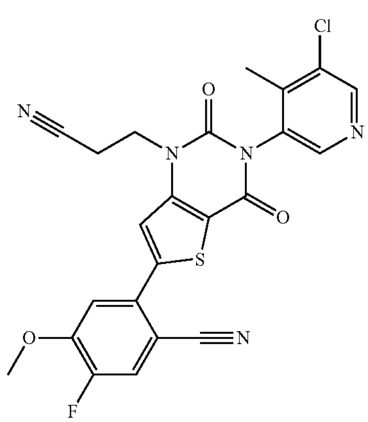 [SMILES: COc1cc(-c2cc3c(s2)c(=O)n(-c2cncc(Cl)c2C)c(=O)n3CCC#N)c(C#N)cc1F] | 495.7 | 1H NMR (400 MHz, DMSO-d6) δ 8.71 (s, 1H), 8.51 (s, 1H), 8.14 (d, J = 11.1 Hz, 1H), 8.05 (s, 1H), 7.59 (d, J = 8.1 Hz, 1H), 4.50 (dt, J = 14.2, 7.1 Hz, 1H), 4.37 (dt, J = 14.2, 6.3 Hz, 1H), 4.06 (s, 3H), 3.04 (t, J = 6.7 Hz, 2H), 2.21 (s, 3H). | I-198; 5-fluoro-4-methoxy-2-(4,4,5,5-tetramethyl-1,3,2-dioxaborolan-2-yl)benzonitrile |

TABLE 40-continued

Examples 770-817

| Example | Structure | ES/MS m/z | 1H-NMR | Changes to Procedure 99: Different Reagents/ Starting Materials |
|---|---|---|---|---|
| 807 | 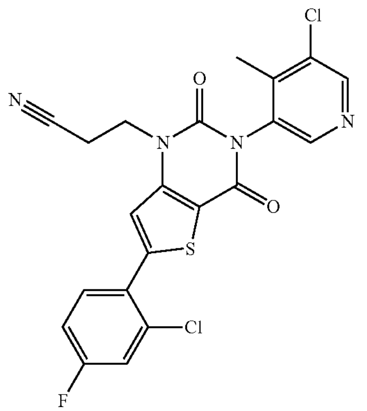 [SMILES: Cc1c(Cl)cncc1-n1c(=O)c2sc(-c3ccc(F)cc3Cl)cc2n(CCC#N)c1=O] | 474.7 | 1H NMR (400 MHz, DMSO-d6) δ 8.71 (s, 1H), 8.51 (s, 1H), 7.99-7.88 (m, 2H), 7.75 (dd, J = 8.8, 2.7 Hz, 1H), 7.49 (td, J = 8.5, 2.9 Hz, 1H), 4.52-4.42 (m, 1H), 4.42-4.33 (m, 1H), 3.02 (t, J = 6.7 Hz, 2H), 2.20 (s, 3H). | I-198 |
| 808 | 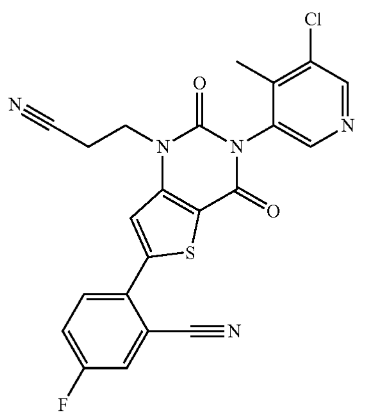 [SMILES: Cc1c(Cl)cncc1-n1c(=O)c2sc(-c3ccc(F)cc3C#N)cc2n(CCC#N)c1=O] | 465.7 | 1H NMR (400 MHz, DMSO-d6) δ 8.51-8.33 (m, 4H), 8.29-8.13 (m, 2H), 5.14-4.93 (m, 2H), 3.54 (t, J = 7.0 Hz, 2H), 2.74 (s, 3H). | I-198; (2-cyano-4-fluoro-phenyl)boronic acid |
| 809 | 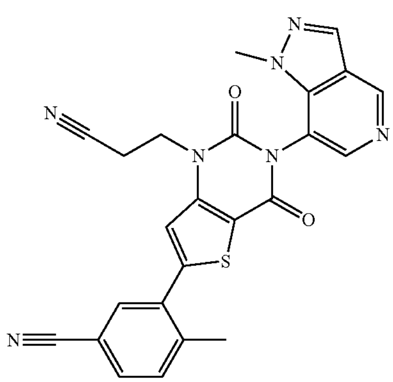 [SMILES: Cc1ccc(C#N)cc1-c1cc2c(s1)c(=O)n(-c1cncc3cnn(C)c13)c(=O)n2CCC#N] | 467.8 | 1H NMR (400 MHz, DMSO-d6) δ 9.42 (s, 1H), 8.62 (d, J = 24.5 Hz, 2H), 8.11 (d, J = 1.9 Hz, 1H), 7.96-7.89 (m, 2H), 7.69-7.65 (m, 1H), 4.53 (dd, J = 14.0, 7.1 Hz, 1H), 4.41 (dd, J = 14.1, 6.2 Hz, 1H), 3.97 (s, 3H), 3.08 (t, J = 6.7 Hz, 2H), 2.61 (s, 3H). | 4-methyl-3-(4,4,5,5-tetramethyl-1,3,2-dioxaborolan-2-yl)benzonitrile |

TABLE 40-continued

Examples 770-817

| Example | Structure | ES/MS m/z | 1H-NMR | Changes to Procedure 99: Different Reagents/ Starting Materials |
|---|---|---|---|---|
| 810 | 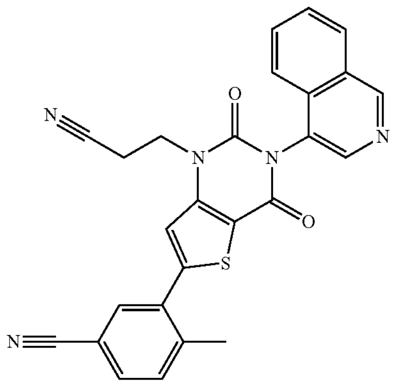 [SMILES: Cc1ccc(C#N)cc1-c1cc2c(s1)c(=O)n(-c1cncc3ccccc13)c(=O)n2CCC#N] | 463.8 | 1H NMR (400 MHz, DMSO-d6) δ 9.49 (s, 1H), 8.60 (s, 1H), 8.32 (dd, J = 7.6, 1.7 Hz, 1H), 8.09 (d, J = 1.8 Hz, 1H), 7.91 (d, J = 8.5 Hz, 3H), 7.82 (dddd, J = 16.1, 8.1, 6.9, 1.4 Hz, 2H), 7.67 (d, J = 8.0 Hz, 1H), 4.54-4.35 (m, 2H), 3.03 (t, J = 6.7 Hz, 2H), 2.61 (s, 3H). | I-190; 4-methyl-3-(4,4,5,5-tetramethyl-1,3,2-dioxaborolan-2-yl)benzonitrile |
| 811 | 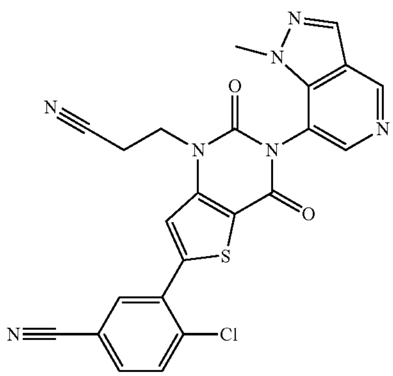 [SMILES: Cn1ncc2cncc(-n3c(=O)c4sc(-c5cc(C#N)ccc5Cl)cc4n(CCC#N)c3=O)c21] | 487.7 | 1H NMR (400 MHz, DMSO-d6) δ 9.47 (d, J = 6.0 Hz, 1H), 8.69 (d, J = 5.2 Hz, 1H), 8.66-8.52 (m, 1H), 8.49 (d, J = 2.1 Hz, 1H), 8.16 (d, J = 4.1 Hz, 1H), 8.09-7.99 (m, 1H), 7.96 (d, J = 8.3 Hz, 1H), 4.56 (dt, J = 14.4, 7.1 Hz, 1H), 4.42 (dt, J = 15.2, 5.8 Hz, 1H), 3.97 (d, J = 9.5 Hz, 3H), 3.20-3.00 (m, 2H). | (2-chloro-5-cyano-phenyl)boronic acid |
| 812 | 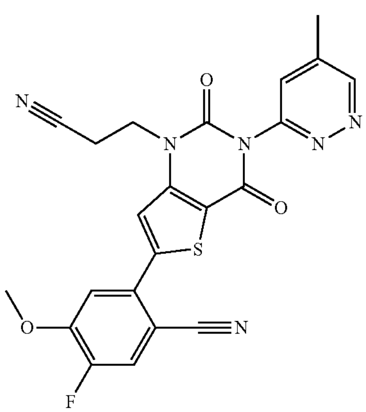 [SMILES: COc1cc(-c2cc3c(s2)c(=O)n(-c2cc(C)cnn2)c(=O)n3CCC#N)c(C#N)cc1F] | 462.8 | 1H NMR (400 MHz, DMSO-d6) δ 9.26 (s, 1H), 8.14 (dd, J = 11.7, 3.7 Hz, 1H), 8.08 (s, 1H), 7.76 (s, 1H), 7.61 (d, J = 8.0 Hz, 1H), 4.42 (s, 2H), 4.06 (d, J = 5.4 Hz, 3H), 3.03 (t, J = 6.5 Hz, 2H), 2.45 (s, 3H). | I-243; 5-fluoro-4-methoxy-2-(4,4,5,5-tetramethyl-1,3,2-dioxaborolan-2-yl)benzonitrile |

TABLE 40-continued

Examples 770-817

| Example | Structure | ES/MS m/z | 1H-NMR | Changes to Procedure 99: Different Reagents/ Starting Materials |
|---|---|---|---|---|
| 813 | 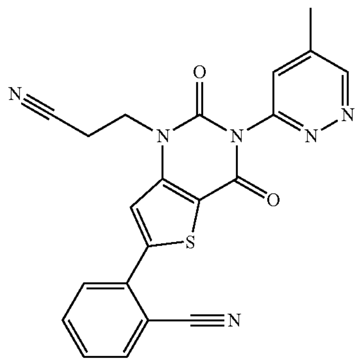 [SMILES: Cc1cnnc(-n2c(=O)c3sc(-c4ccccc4C#N)cc3n(CCC#N)c2=O)c1] | 414.8 | 1H NMR (400 MHz, DMSO-d6) δ 9.26 (s, 1H), 8.18-8.03 (m, 2H), 7.95 (dt, J = 15.4, 8.0 Hz, 2H), 7.80-7.64 (m, 2H), 4.42 (s, 2H), 3.02 (t, J = 6.7 Hz, 2H), 2.45 (s, 3H). | I-243; (2-cyanophenyl) boronic acid |
| 814 | 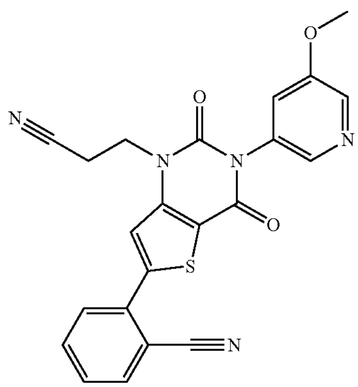 [SMILES: COc1cncc(-n2c(=O)c3sc(-c4ccccc4C#N)cc3n(CCC#N)c2=O)c1] | 429.8 | 1H NMR (400 MHz, DMSO-d6) δ 8.40 (d, J = 2.7 Hz, 1H), 8.20 (d, J = 1.9 Hz, 1H), 8.10 (d, J = 9.0 Hz, 2H), 7.98-7.87 (m, 2H), 7.74 (ddd, J = 7.6, 6.8, 1.9 Hz, 1H), 7.55 (dd, J = 2.7, 1.9 Hz, 1H), 4.41 (t, J = 6.9 Hz, 2H), 3.87 (s, 3H), 2.99 (t, J = 6.8 Hz, 2H). | I-245; (2-cyanophenyl) boronic acid |
| 815 | 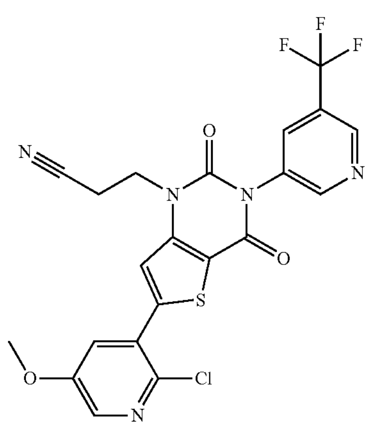 [SMILES: COc1cnc(Cl)c(-c2cc3c(s2)c(=O)n(-c2cncc(C(F)(F)F)c2)c(=O)n3CCC#N)c1] | 507.7 | 1H NMR (400 MHz, DMSO-d6) δ 9.10 (d, J = 2.1 Hz, 1H), 8.94 (d, J = 2.1 Hz, 1H), 8.42 (d, J = 2.3 Hz, 1H), 8.32 (d, J = 3.0 Hz, 1H), 8.12 (s, 1H), 7.92 (d, J = 3.0 Hz, 1H), 4.44 (t, J = 6.6 Hz, 2H), 3.97 (s, 3H), 3.01 (t, J = 6.6 Hz, 2H). | I-244; (2-chloro-5-methoxy-3-pyridyl)boronic acid |

TABLE 40-continued

Examples 770-817

| Example | Structure | ES/MS m/z | 1H-NMR | Changes to Procedure 99: Different Reagents/ Starting Materials |
|---|---|---|---|---|
| 816 | 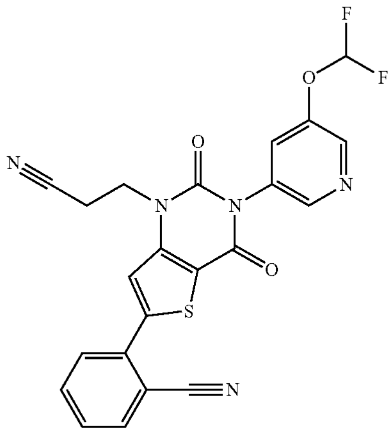 [SMILES: N#CCCn1c(=O)n(-c2cncc(OC(F)F)c2)c(=O)c2sc(-c3ccccc3C#N)cc21] | 465.8 | 1H NMR (400 MHz, DMSO-d6) δ 8.61 (s, 1H), 8.53 (s, 1H), 8.14-8.05 (m, 2H), 7.98-7.84 (m, 2H), 7.86 (d, J = 2.7 Hz, 1H), 7.80-7.66 (m, 1H), 7.39 (t, J = 73.0 Hz, 1H), 4.42 (t, J = 6.8 Hz, 2H), 2.99 (t, J = 6.7 Hz, 2H). | I-247; (2-cyanophenyl) boronic acid |
| 817 | 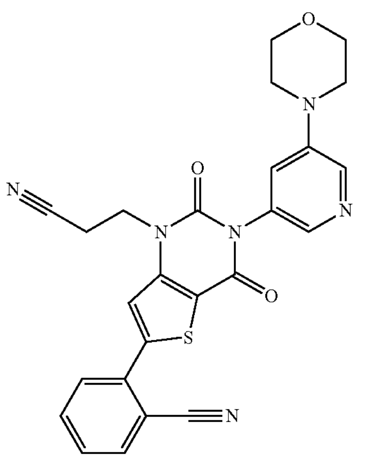 [SMILES: N#CCCn1c(=O)n(-c2cncc(N3CCOCC3)c2)c(=O)c2sc(-c3ccccc3C#N)cc21] | 484.8 | 1H NMR (400 MHz, DMSO-d6) δ 8.42 (d, J = 2.7 Hz, 1H), 8.13-8.06 (m, 3H), 7.98-7.85 (m, 2H), 7.81-7.70 (m, 1H), 7.65 (t, J = 2.3 Hz, 1H), 4.41 (t, J = 6.8 Hz, 2H), 3.77 (dd, J = 6.1, 3.7 Hz, 4H), 3.30-3.22 (m, 4H), 2.99 (t, J = 6.8 Hz, 2H). | I-248; (2-cyanophenyl) boronic acid |

Procedure 100: Example 818

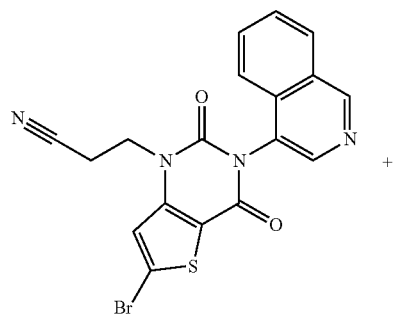

I-190

+

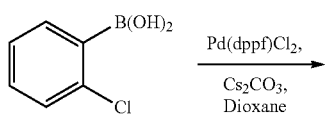

$\xrightarrow{\text{Pd(dppf)Cl}_2, \text{Cs}_2\text{CO}_3, \text{Dioxane}}$

-continued

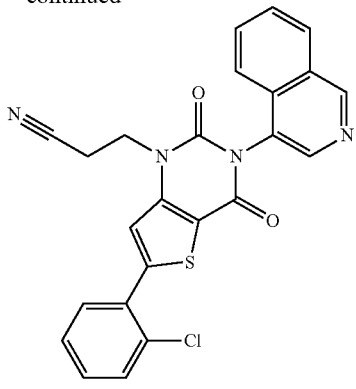

Example 818

3-(6-(2-chlorophenyl)-3-(isoquinolin-4-yl)-2,4-dioxo-3,4-dihydrothieno[3,2-d]pyrimidin-1(2H)-yl)propanenitrile (Example 818): To a microwave vial containing a stir bar was added 3-(6-bromo-34 (isoquinolin-4-yl)-2,4-dioxo-3,4-dihydrothieno[3,2-d]pyrimidin-1(2H)-yl)propanenitrile (I-190) (80 mg, 0.187 mmol), (2-chlorophenyl)boronic acid (35 mg, 0.225 mmol), Pd(dppf)Cl$_2$ (14 mg, 0.019 mmol), and Cs$_2$CO$_3$ (183 mg, 0.56 mmol), followed by 1,4-Dioxane (2 ml). The vial was degassed under Ar (30 seconds), sealed with Teflon, and heated at 95° C. for 10 minutes under microwave conditions. The crude product was filtered through an acrodisc and concentrated under reduced pressure. The crude residue was dissolved in ACN (1.5 mL), water (0.5 mL) and TFA (0.2 mL), and purified directly by RP-HPLC (0.1% TFA-ACN in 0.1% TFA Water, Column: Gemini 5 μM, NX-C18 110 Angstrom, 250×21.2 mm) to give the product.

ES/MS: 458.8 (M$^+$).

1H NMR (400 MHz, DMSO-d6) δ9.48 (s, 1H), 8.59 (s, 1H), 8.30 (dd, J=7.1, 1.8 Hz, 1H), 8.03 (s, 1H), 7.97-7.87 (m, 2H), 7.81 (qd, J=7.1, 1.6 Hz, 2H), 7.75-7.66 (m, 1H), 7.61-7.53 (m, 2H), 4.56-4.36 (m, 2H), 3.02 (t, J=6.7 Hz, 2H).

Examples 819-837

The following Examples were made in an analogous fashion according to Procedure 100 and are shown below in Table 41. To prepare the below Examples, different reagents/starting materials were used than some of those described in Procedure 100 and are noted in the last column of Table 41—"Changes to Procedure 100: Different Reagents/Starting Meterials".

TABLE 41

Examples 819-837

| Example | Structure | ES/MS m/z | 1H-NMR | Changes to Procedure 100: Different Reagents/Starting Materials |
|---|---|---|---|---|
| 819 | 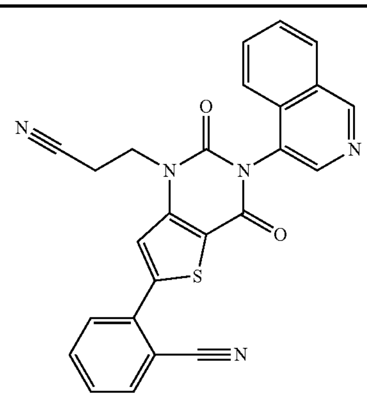 | 449.8 | 1H NMR (400 MHz, DMSO-d6) δ 9.48 (s, 1H), 8.59 (s, 1H), 8.31 (dd, J = 7.2, 2.0 Hz, 1H), 8.17-8.09 (m, 2H), 8.03-7.90 (m, 3H), 7.87-7.71 (m, 3H), 4.57-4.31 (m, 2H), 3.03 (t, J = 6.8 Hz, 2H). | (2-cyanophenyl)boronic acid |
| 820 | 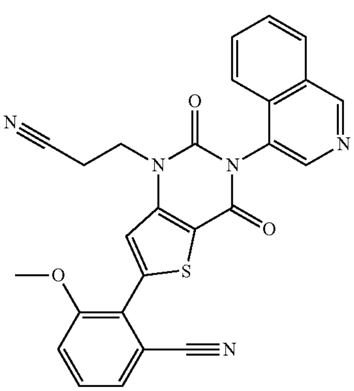 [SMILES: COc1cccc(C#N)c1-c1cc2c(s1)c(=O)n(-c1cncc3ccccc13)c(=O)n2CCC#N] | 479.8 | 1H NMR (400 MHz, DMSO-d6) δ 9.46 (s, 1H), 8.59 (s, 1H), 8.30-8.21 (m, 1H), 7.97 (d, J = 9.1 Hz, 2H), 7.85-7.54 (m, 5H), 4.50-4.27 (m, 2H), 3.92 (s, 3H), 3.00 (t, J = 6.9 Hz, 2H). | 3-methoxy-2-(4,4,5,5-tetramethyl-1,3,2-dioxaborolan-2-yl)benzonitrile |

TABLE 41-continued

Examples 819-837

| Example | Structure | ES/MS m/z | 1H-NMR | Changes to Procedure 100: Different Reagents/ Starting Materials |
|---|---|---|---|---|
| 821 | 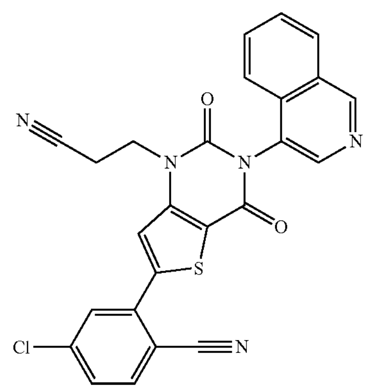 [SMILES: N#CCCn1c(=O)n(-c2cncc3ccccc23)c(=O)c2sc(-c3cc(Cl)ccc3C#N)cc21] | 483.7 | 1H NMR (400 MHz, DMSO) δ 9.50 (s, 1H), 8.60 (s, 1H), 8.32 (dd, J = 7.3, 1.9 Hz, 1H), 8.19 (s, 1H), 8.17-8.10 (m, 2H), 7.97 (d. J = 7.9 Hz, 1H), 7.89-7.75 (m, 3H), 4.53-4.36 (m, 2H), 3.05 (t, J = 6.9 Hz, 2H). | (5-chloro-2-cyano-phenyl)boronic acid |
| 822 | 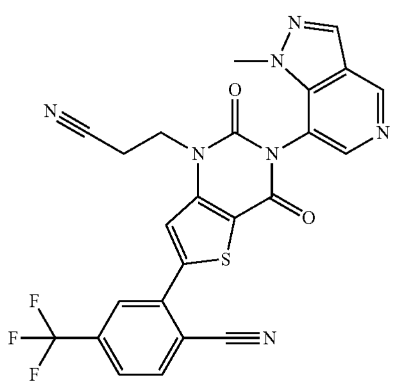 [SMILES: Cn1ncc2cncc(-n3c(=O)c4sc(-c5cc(C(F)(F)F)ccc5C#N)cc4n(CCC#N)c3=O)c21] | 521.8 | 1H NMR (400 MHz, DMSO) δ 9.33 (s, 1H), 8.56 (s, 1H), 8.51 (s, 1H), 8.40-8.32 (m, 2H), 8.24 (s, 1H), 8.15 (dd, J = 8.1, 1.8 Hz, 1H), 4.57 (dt, J = 14.3, 7.1 Hz, 1H), 4.42 (dt, J = 14.3, 6.2 Hz, 1H), 3.95 (s, 3H), 3.11 (td, J = 6.8, 2.1 Hz, 2H). | I-189; 2-(4,4,5,5-tetramethyl-1,3,2-dioxaborolan-2-yl)-4-(trifluoromethyl)benzonitrile |
| 823 | 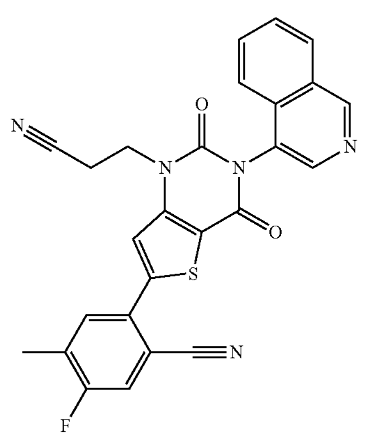 [SMILES: Cc1cc(-c2cc3c(s2)c(=O)n(-c2cncc4ccccc24)c(=O)n3CCC#N)c(C#N)cc1F] | 481.8 | 1H NMR (400 MHz, DMSO-d6) δ 9.48 (s, 1H), 8.59 (s, 1H), 8.31 (dd, J = 7.2, 2.0 Hz, 1H), 8.08 (t, J = 4.7 Hz, 2H), 7.99-7.90 (m, 2H), 7.87-7.74 (m, 2H), 4.53-4.35 (m, 2H), 3.03 (t, J = 6.8 Hz, 2H), 2.43 (d, J = 2.0 Hz, 3H). | I-212 |

TABLE 41-continued

Examples 819-837

| Example | Structure | ES/MS m/z | 1H-NMR | Changes to Procedure 100: Different Reagents/ Starting Materials |
|---|---|---|---|---|
| 824 | 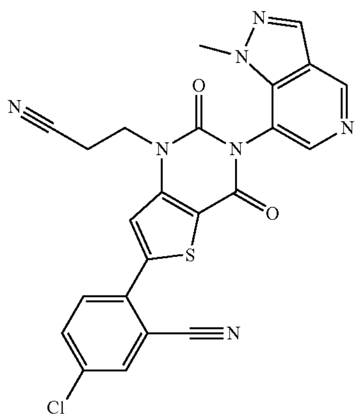 [SMILES: Cn1ncc2cncc(-n3c(=O)c4sc(-c5ccc(Cl)cc5C#N)cc4n(CCC#N)c3=O)c21] | 487.8 | 1H NMR (400 MHz, DMSO-d6) δ 9.31 (s, 1H), 8.51 (d, J = 25.1 Hz, 2H), 8.34 (d, J = 2.2 Hz, 1H), 8.16 (s, 1H), 8.08-7.96 (m, 2H), 4.54 (dt, J = 14.4, 7.2 Hz, 1H), 4.45-4.33 (m, 1H), 3.92 (s, 3H), 3.08 (t, J = 6.7 Hz, 2H). | I-189; (4-chloro-2-cyano-phenyl)boronic acid |
| 825 | 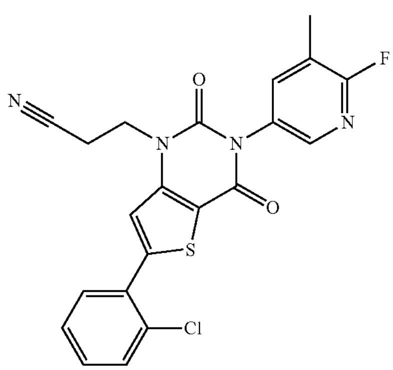 [SMILES: Cc1cc(-n2c(=O)c3sc(-c4ccccc4Cl)cc3n(CCC#N)c2=O)cnc1F] | 440.7 | 1H NMR (400 MHz, DMSO-d6) δ 8.11-8.06 (m, 1H), 7.98 (s, 1H), 7.95-7.81 (m, 2H), 7.75-7.66 (m, 1H), 7.60-7.51 (m, 2H), 4.41 (t, J = 6.7 Hz, 2H), 2.98 (t, J = 6.6 Hz, 2H), 2.31 (s, 3H). | I-213 |
| 826 | 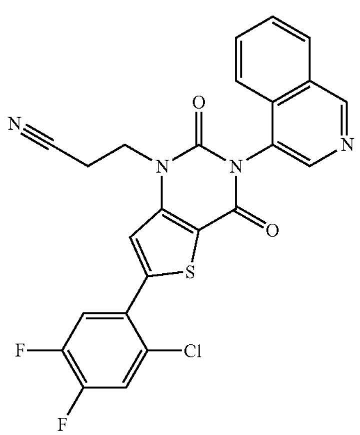 [SMILES: N#CCCn1c(=O)n(-c2cncc3ccccc23)c(=O)c2sc(-c3cc(F)c(F)cc3Cl)cc21] | 494.7 | 1H NMR (400 MHz, DMSO-d6) δ 9.48 (s, 1H), 8.59 (s, 1H), 8.34-8.27 (m, 1H), 8.14 (dd, J = 11.4, 8.4 Hz, 1H), 8.09-7.99 (m, 2H), 7.93 (d, J = 7.8 Hz, 1H), 7.87-7.75 (m, 2H), 4.53-4.35 (m, 2H), 3.04 (t, J = 6.8 Hz, 2H). | 2-(2-chloro-4,5-difluoro-phenyl)-4,4,5,5-tetramethyl-1,3,2-dioxaborolane |

TABLE 41-continued

Examples 819-837

| Example | Structure | ES/MS m/z | 1H-NMR | Changes to Procedure 100: Different Reagents/ Starting Materials |
|---|---|---|---|---|
| 827 | 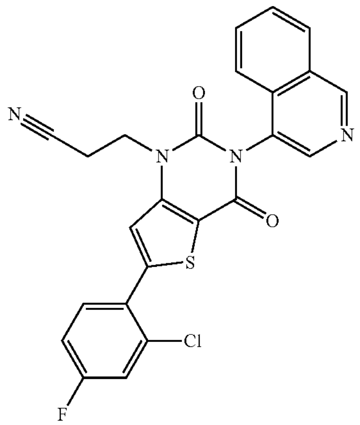 [SMILES: N#CCCn1c(=O)n(-c2cncc3ccccc23)c(=O)c2sc(-c3ccc(F)cc3Cl)cc21] | 476.7 | 1H NMR (400 MHz, DMSO-d6) δ 9.49 (s, 1H), 8.60 (s, 1H), 8.31 (dd, J = 7.4, 1.8 Hz, 1H), 8.03-7.90 (m, 3H), 7.88-7.72 (m, 3H), 7.50 (td, J = 8.4, 2.7 Hz, 1H), 4.53-4.35 (m, 2H), 3.02 (t, J = 6.7 Hz, 2H). | (2-chloro-4-fluoro-phenyl)boronic acid |
| 828 | 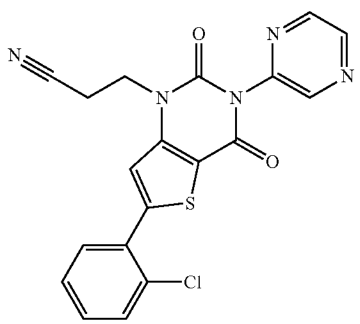 [SMILES: N#CCCn1c(=O)n(-c2cnccn2)c(=O)c2sc(-c3ccccc3Cl)cc21] | 409.8 | 1H NMR (400 MHz, DMSO-d6) δ 8.89-8.76 (m, 3H), 8.01 (s, 1H), 7.89 (dd, J = 6.1, 3.4 Hz, 1H), 7.71 (dt, J = 7.6, 3.7 Hz, 1H), 7.56 (dd, J = 5.9, 3.5 Hz, 2H), 4.42 (t, J = 6.8 Hz, 2H), 3.00 (t, J = 6.7 Hz, 2H). | I-215 |
| 829 | 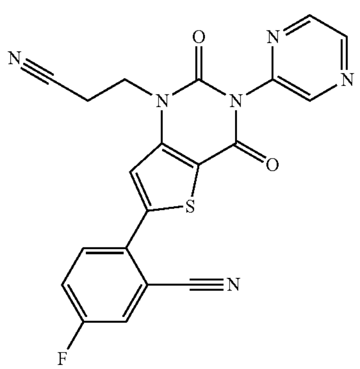 [SMILES: N#CCCn1c(=O)n(-c2cnccn2)c(=O)c2sc(-c3ccc(F)cc3C#N)cc21] | 418.8 | 1H NMR (400 MHz, DMSO-d6) δ 8.89-8.76 (m, 3H), 8.26-8.15 (m, 2H), 7.95 (dd, J = 9.6, 2.6 Hz, 1H), 7.65 (td, J = 8.4, 2.6 Hz, 1H), 4.41 (t, J = 6.9 Hz, 2H), 3.02 (t, J = 6.9 Hz, 2H). | I-215; (2-cyano-4-fluoro-phenyl)boronic acid |
| 830 | 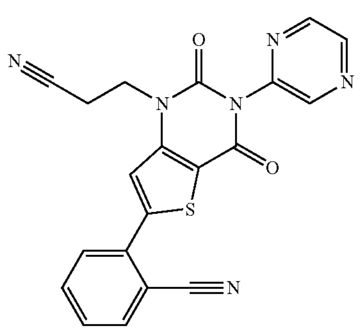 [SMILES: N#CCCn1c(=O)n(-c2cnccn2)c(=O)c2sc(-c3ccccc3C#N)cc21] | 400.8 | 1H NMR (400 MHz, DMSO-d6) δ 8.89-8.76 (m, 3H), 8.11 (d, J = 7.3 Hz, 2H), 8.00-7.88 (m, 2H), 7.80-7.71 (m, 1H), 4.41 (d, J = 7.2 Hz, 2H), 3.01 (t, J = 6.8 Hz, 2H). | I-215; (2-cyanophenyl) boronic acid |

TABLE 41-continued

Examples 819-837

| Example | Structure | ES/MS m/z | 1H-NMR | Changes to Procedure 100: Different Reagents/ Starting Materials |
|---|---|---|---|---|
| 831 | 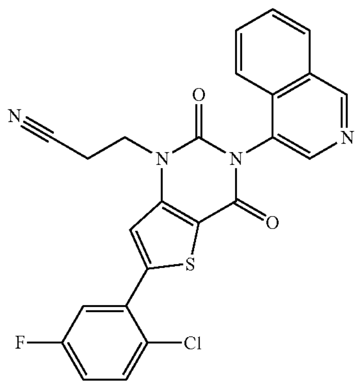 [SMILES: N#CCCn1c(=O)n(-c2cncc3ccccc23)c(=O)c2sc(-c3cc(F)ccc3Cl)cc21] | 476.8 | 1H NMR (400 MHz, DMSO-d6) δ 9.49 (s, 1H), 8.59 (s, 1H), 8.35-8.28 (m, 1H), 8.11 (s, 1H), 7.98-7.86 (m, 2H), 7.90-7.79 (m, 1H), 7.83-7.73 (m, 2H), 7.47 (ddd, J = 8.9, 7.9, 3.1 Hz, 1H), 4.54-4.36 (m, 2H), 3.04 (t, J = 6.8 Hz, 2H). | (2-chloro-5-fluoro-phenyl)boronic acid |
| 832 | 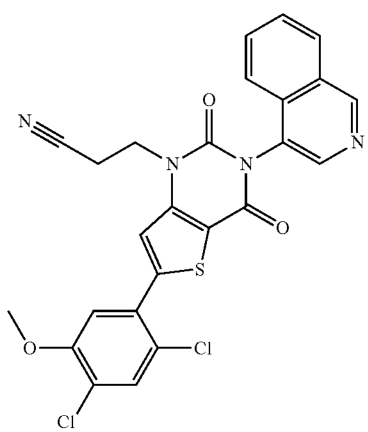 [SMILES: COc1cc(-c2cc3c(s2)c(=O)n(-c2cncc4ccccc24)c(=O)n3CCC#N)c(Cl)cc1Cl] | 523.7 | 1H NMR (400 MHz, DMSO-d6) δ 9.48 (d, J = 0.8 Hz, 1H), 8.59 (s, 1H), 8.31 (dd, J = 7.2, 1.8 Hz, 1H), 8.03 (s, 1H), 7.95-7.74 (m, 4H), 7.50 (s, 1H), 4.56-4.38 (m, 2H), 4.00 (s, 3H), 3.04 (t, J = 6.6 Hz, 2H). | (2,4-dichloro-5-methoxy-phenyl)boronic acid |
| 833 | 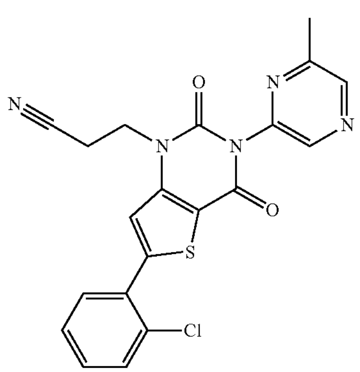 [SMILES: Cc1cncc(-n2c(=O)c3sc(-c4ccccc4Cl)cc3n(CCC#N)c2=O)n1] | 423.7 | 1H NMR (400 MHz, DMSO-d6) δ 8.70 (s, 1H), 8.64 (s, 1H), 8.01 (s, 1H), 7.94-7.85 (m, 1H), 7.70 (dt, J = 7.5, 3.6 Hz, 1H), 7.61-7.51 (m, 2H), 4.41 (t, J = 6.9 Hz, 2H), 3.00 (t, J = 6.7 Hz, 2H), 2.58 (s, 3H). | I-216 |

TABLE 41-continued

Examples 819-837

| Example | Structure | ES/MS m/z | 1H-NMR | Changes to Procedure 100: Different Reagents/ Starting Materials |
|---|---|---|---|---|
| 834 | 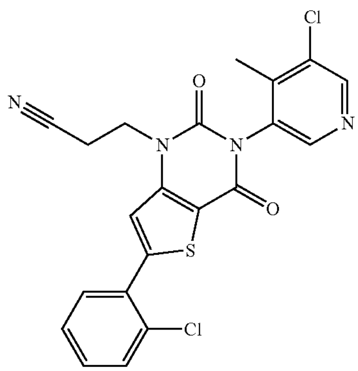 [SMILES: Cc1c(Cl)cncc1-n1c(=O)c2sc(-c3ccccc3Cl)cc2n(CCC#N)c1=O] | 456.7 | 1H NMR (400 MHz, DMSO-d6) δ 8.71 (s, 1H), 8.52 (s, 1H), 8.01-7.93 (m, 1H), 7.87 (dt, J = 8.1, 3.7 Hz, 1H), 7.70 (h, J = 6.4, 4.9 Hz, 1H), 7.61-7.50 (m, 2H), 4.53-4.42 (m, 1H), 4.44-4.32 (m, 1H), 3.02 (t, J = 6.5 Hz, 2H), 2.20 (s, 3H). | I-198; (2-chlorophenyl)boronic acid |
| 835 | 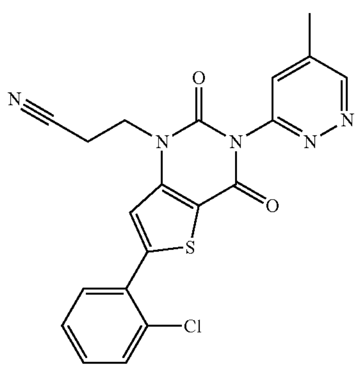 [SMILES: Cc1cnnc(-n2c(=O)c3sc(-c4ccccc4Cl)cc3n(CCC#N)c2=O)c1] | 423.8 | 1H NMR (400 MHz, DMSO-d6) δ 9.26 (s, 1H). 8.01 (d, J = 4.7 Hz, 1H), 7.89 (dt, J = 6.6, 3.5 Hz, 1H). 7.79-7.65 (m, 2H), 7.56 (dt, J = 7.5, 3.6 Hz, 2H). 4.48-4.34 (m, 2H), 3.01 (t, J = 6.5 Hz, 2H), 2.45 (s, 3H). | I-243; (2-chlorophenyl)boronic acid |
| 836 | 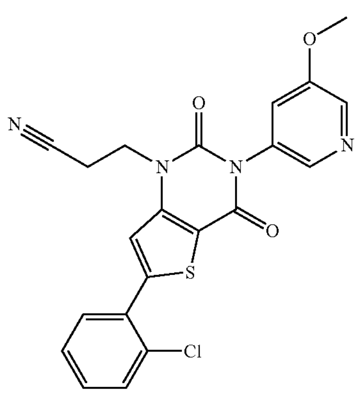 [SMILES: COc1cncc(-n2c(=O)c3sc(-c4ccccc4Cl)cc3n(CCC#N)c2=O)c1] | 438.8 | 1H NMR (400 MHz, DMSO-d6) δ 8.40 (d, J = 2.7 Hz, 1H), 8.20 (d, J = 1.9 Hz, 1H), 7.98 (s, 1H), 7.91-7.82 (m, 1H), 7.75-7.60 (m, 1H), 7.60-7.51 (m, 3H), 4.41 (t, J = 6.7 Hz, 2H), 3.87 (s, 3H), 2.98 (t, J = 6.6 Hz, 2H). | I-245; (2-chlorophenyl)boronic acid |

TABLE 41-continued

Examples 819-837

| Example | Structure | ES/MS m/z | 1H-NMR | Changes to Procedure 100: Different Reagents/ Starting Materials |
|---|---|---|---|---|
| 837 | 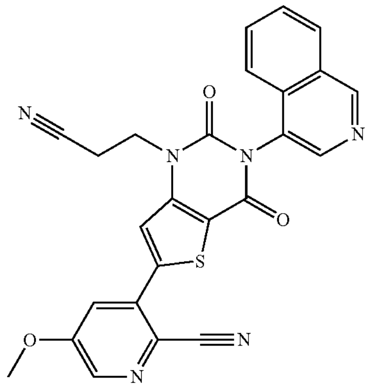 [SMILES: COc1cnc(C#N)c(-c2cc3c(s2)c(=O)n(-c2cncc4ccccc24)c(=O)n3CCC#N)c1] | 481.1 | 1H NMR (400 MHz, DMSO-d6) δ 9.47 (s, 1H), 8.63 (d, J = 2.7 Hz, 1H), 8.58 (s, 1H), 8.30 (dd, J = 6.9, 2.2 Hz, 1H), 8.22 (s, 1H), 7.96-7.91 (m. 1H), 7.89 (d, J = 2.7 Hz, 1H), 7.83-7.76 (m, 2H), 4.53-4.35 (m, 2H), 4.06 (s, 3H), 3.05 (t, J = 6.8 Hz, 2H). | (2-cyano-5-methoxypyridin-3-yl)boronic acid |

Procedure 101: Example 838 and Example 839

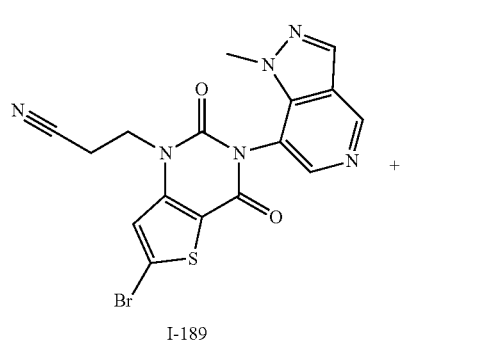

I-189

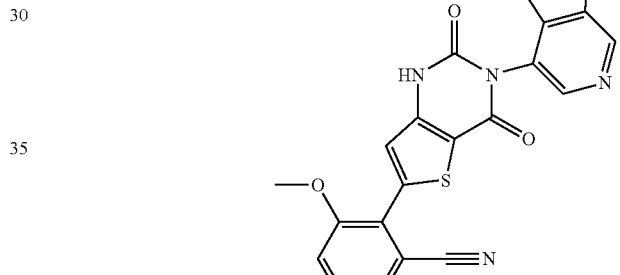

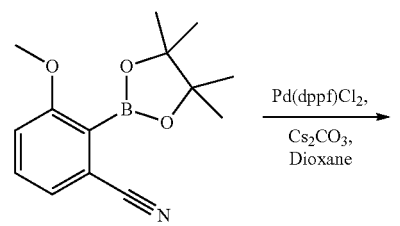

Pd(dppf)Cl₂,
Cs₂CO₃,
Dioxane

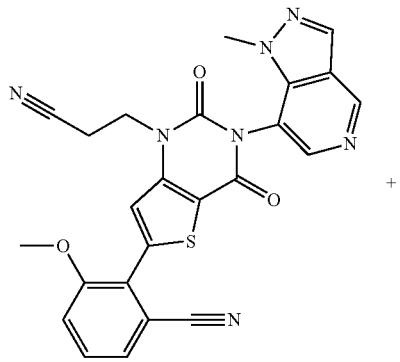

Example 838

-continued

Example 839

2-(1-(2-cyanoethyl)-3-(1-methyl-1H-pyrazolo[4,3-c]pyridin-7-yl)-2,4-dioxo-1,2,3,4-tetrahydrothieno[3,2-d]pyrimidin-6-yl)-3-methoxybenzonitrile (Example 838) and 3-methoxy-2-(3-(1-methyl-1H-pyrazolo[4,3-c]pyridin-7-yl)-2,4-dioxo-1,2,3,4-tetrahydrothieno[3,2-d]pyrimidin-6-yl)benzonitrile (Example 839): To a microwave vial containing a stir bar was added 3-(6-bromo-3-(1-methyl-1H-pyrazolo[4,3-c]pyridin-7-yl)-2,4-dioxo-3,4-dihydrothieno[3,2-d]pyrimidin-1(2H)-yl)propanenitrile (I-189) (50 mg, 0.116 mmol), 3-methoxy-2-(4,4,5,5-tetramethyl-1,3,2-dioxaborolan-2-yl)benzonitrile (36 mg, 0.139 mmol), Pd(dppf)Cl₂ (8.6 mg, 0.012 mmol), and Cs₂CO₃ (113 mg, 0.348 mmol), followed by 1,4-Dioxane (1.5 ml). The vial was degassed under Ar (30 seconds), sealed with Teflon, and heated at 95° C. for 10 minutes under microwave conditions. The crude product was filtered through an acrodisc and concentrated under reduced pressure. The crude residue was dissolved in ACN (1 mL), water (0.4 mL) and TFA (0.2 mL), and purified directly by RP-HPLC (0.1% TFA-ACN in 0.1% TFA Water, Column: Gemini 5 μM, NX-C18 110 Angstrom, 250×21.2 mm) to give the products.

Example 838

ES/MS: 483.8 (M⁺).

1H NMR (400 MHz, DMSO-d6) δ 9.26 (s, 1H), 8.54-8.40 (m, 2H), 8.01 (s, 1H), 7.79-7.54 (m, 3H), 4.60-4.29 (m, 2H), 3.94 (s, 3H), 3.93 (s, 3H), 3.04 (t, J=7.2 Hz, 2H).

Example 839

ES/MS: 430.8 (M⁺).

1H NMR (400 MHz, DMSO-d6) δ 12.47 (s, 1H), 9.25 (s, 1H), 8.49 (d, J=6.9 Hz, 2H), 7.77-7.55 (m, 3H), 7.37 (s, 1H), 3.94 (s, 3H), 3.92 (s, 3H).

Examples 840-841

The following Examples were made in an analogous fashion according to Procedure 101 and are shown below in Table 42. To prepare the below Examples, different reagents/starting materials were used than some of those described in Procedure 101 and are noted in the last column of Table 42—"Changes to Procedure 101: Different Reagents/Starting Materials".

TABLE 42

Examples 840-841

| Example | Structure | ES/MS m/z | 1H-NMR | Changes to Procedure 101: Different Reagents/Starting Materials |
|---|---|---|---|---|
| 840 | 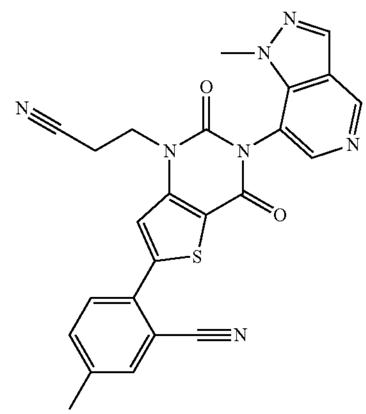 | 467.9 | 1H NMR (400 MHz, DMSO-d6) δ 9.28 (s, 1H), 8.51 (s, 1H), 8.45 (s, 1H), 8.10 (s, 1H), 7.95 (s, 1H), 7.88 (d, J = 8.1 Hz, 1H), 7.75 (dd, J = 8.1, 1.9 Hz, 1H), 4.62-4.47 (m, 1H), 4.46-4.31 (m, 1H), 3.93 (s, 3H), 3.08 (t, J = 6.7 Hz, 2H), 2.45 (s, 3H). | 5-methyl-2-(4,4,5,5-tetramethyl-1,3,2-dioxaborolan-2-yl)benzonitrile |
| 841 | 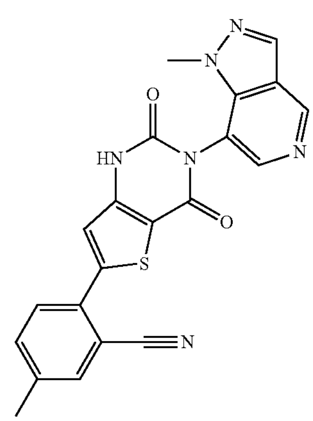 [SMILES: Cc1ccc(-c2cc3[nH]c(=O)n(-c4cncc5cnn(C)c45)c(=O)c3s2)c(C#N)c1] | 414.8 | 1H NMR (400 MHz, DMSO-d6) δ 12.52 (s, 1H), 9.26 (s, 1H), 8.48 (d, J = 15.1 Hz, 2H), 7.92 (s, 1H), 7.86-7.64 (m, 2H), 7.51 (s, 1H), 4.02-3.83 (m, 3H), 2.51 (s, 3H). | 5-methyl-2-(4,4,5,5-tetramethyl-1,3,2-dioxaborolan-2-yl)benzonitrile |

Procedure 102: Example 842

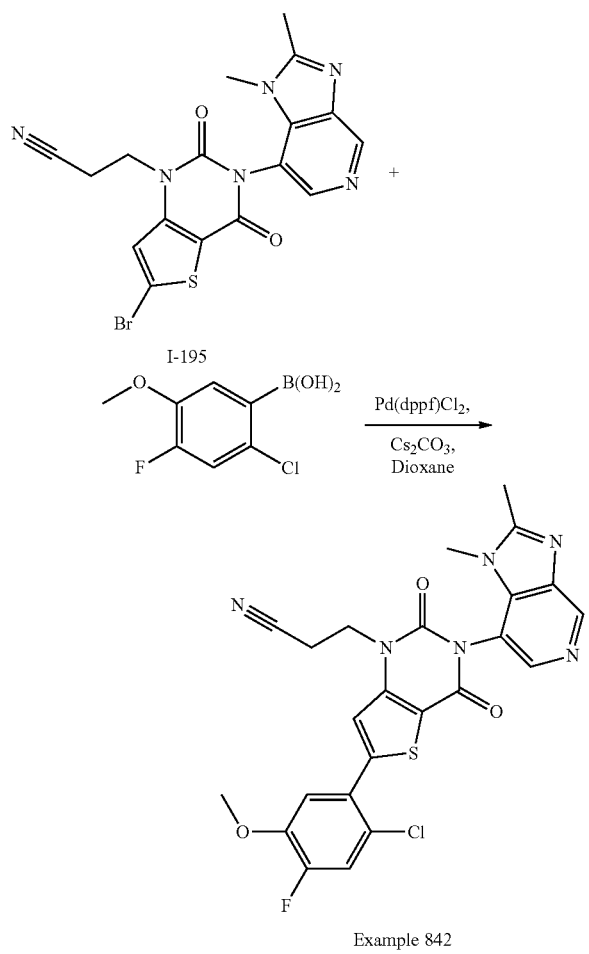

3-(6-(2-chloro-4-fluoro-5-methoxyphenyl)-3-(1,2-dimethyl-1H-imidazo[4,5-c]pyridin-7-yl)-2,4-dioxo-3,4-dihydrothieno[3,2-d]pyrimidin-1(2H)-yl)propanenitrile (Example 842): To a microwave vial containing a stir bar was added 3-(6-bromo-3-(1,2-dimethyl-1H-imidazo[4,5-c]pyridin-7-yl)-2,4-dioxo-3,4-dihydrothieno[3,2-d]pyrimidin-1(2H)-yl)propanenitrile (I-195) (50 mg, 0.11 mmol), (2-chloro-4-fluoro-5-methoxyphenyl)boronic acid (25 mg, 0.124 mmol), Pd(dppf)Cl$_2$ (8.3 mg, 0.011 mmol), and Cs$_2$CO$_3$ (110 mg, 0.34 mmol), followed by 1,4-Dioxane (0 ml). The vial was degassed under Ar (30 seconds), sealed with Teflon, and heated at 95° C. for 10 minutes under microwave conditions. The crude product was filtered through an acrodisc and concentrated under reduced pressure. The crude residue was dissolved in ACN (1.5 mL), water (0.5 mL) and TFA (0.2 mL), and purified directly by RP-HPLC (0.1% TFA-ACN in 0.1% TFA Water, Column: Gemini 5 µM, NX-C18 110 Angstrom, 250×21.2 mm) to give the product.

ES/MS: 524.8 (M$^+$).

1H NMR (400 MHz, DMSO-d6) δ 9.25 (s, 1H), 8.60 (s, 1H), 8.00 (s, 1H), 7.76 (d, J=11.0 Hz, 1H), 7.55 (d, J=8.9 Hz, 1H), 4.65-4.37 (m, 2H), 3.97 (s, 3H), 3.67 (s, 3H), 3.08 (t, J=6.5 Hz, 2H), 2.67 (s, 3H).

Examples 843-897

The following Examples were made in an analogous fashion according to Procedure 102 and are shown below in Table 43. To prepare the below Examples, different reagents/starting materials were used than some of those described in Procedure 102 and are noted in the last column of Table 43—"Changes to Procedure 102: Different Reagents/Starting Materials".

TABLE 43

Examples 843-897

| Example | Structure | ES/MS m/z | 1H-NMR | Changes to Procedure 102: Different Reagents/ Starting Materials |
|---|---|---|---|---|
| 843 | 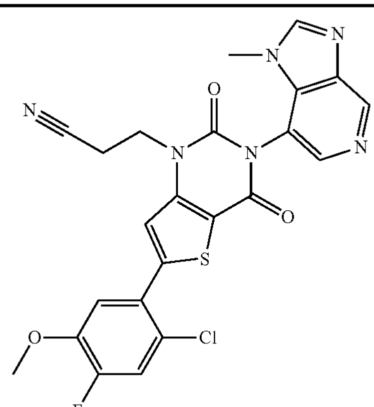 | 510.8 | 1H NMR (400 MHz, DMSO-d6) δ 9.27 (s, 1H), 8.55 (d, J = 3.8 Hz, 2H), 7.99 (s, 1H), 7.75 (d, J = 11.0 Hz, 1H), 7.55 (d, J = 8.9 Hz, 1H), 4.63 – 4.32 (m, 2H), 3.97 (s, 3H), 3.77 (s, 3H), 3.08 (t, J = 6.6 Hz, 2H). | I-196 |

TABLE 43-continued

Examples 843-897

| Example | Structure | ES/MS m/z | 1H-NMR | Changes to Procedure 102: Different Reagents/ Starting Materials |
|---|---|---|---|---|
| 844 | 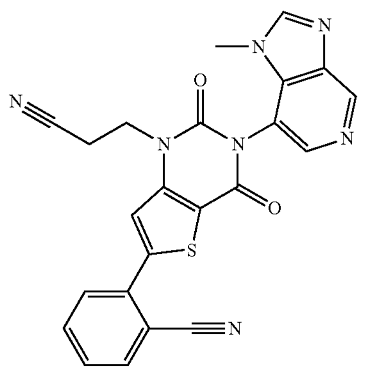 [SMILES: Cn1cnc2cncc(-n3c(=O)c4sc(-c5ccccc5C#N)cc4n(CCC#N)c3=O)c21] | 453.8 | 1H NMR (400 MHz, DMSO-d6) δ 9.25 (s, 1H), 8.53 (d, J = 5.4 Hz, 2H), 8.14 (s, 1H), 8.03 – 7.89 (m, 2H), 7.79 – 7.72 (m, 2H), 4.68 – 4.15 (m, 2H), 3.77 (s, 3H), 3.08 (t, J = 6.7 Hz, 2H). | 1-196; (2-cyanophenyl) boronic acid |
| 845 | 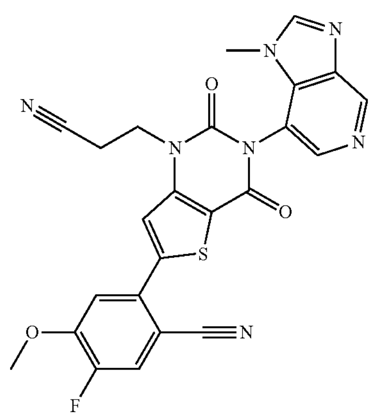 [SMILES: COc1cc(-c2cc3c(s2)c(=O)n(-c2cncc4ncn(C)c24)c(=O)n3CCC#N)c(C#N)cc1F] | 501.8 | 1H NMR (400 MHz, DMSO-d6) δ 9.21 (s, 1H), 8.50 (d, J = 6.1 Hz, 2H), 8.28 – 8.06 (m, 2H), 7.60 (t, J = 5.7 Hz, 1H), 4.64 – 4.29 (m, 2H), 4.06 (s, 3H), 3.76 (s, 3H), 3.24 – 3.01 (m, 2H). | 1-196; I-104 |
| 846 | 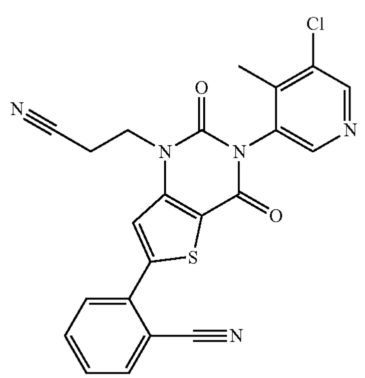 | 447.8 | 1H NMR (400 MHz, DMSO-d6) δ 8.71 (s, 1H), 8.51 (s, 1H), 8.13 – 8.08 (m, 2H), 7.98 – 7.88 (m, 2H), 7.78 – 7.73 (m, 1H), 4.43 (ddt, J = 44.5, 13.8, 6.8 Hz, 2H), 3.02 (t, J = 6.8 Hz, 2H), 2.21 (s, 3H). | I-198; (2-cyanophenyl) boronic acid |

TABLE 43-continued

Examples 843-897

| Example | Structure | ES/MS m/z | 1H-NMR | Changes to Procedure 102: Different Reagents/ Starting Materials |
|---|---|---|---|---|
| 847 | 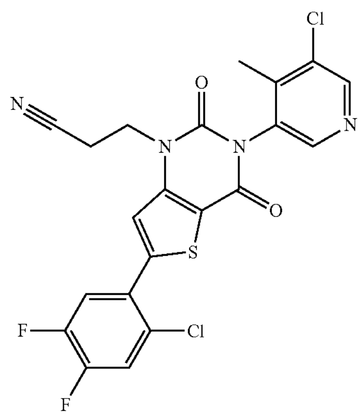 [SMILES: Cc1c(Cl)cncc1-n1c(=O)c2sc(-c3cc(F)c(F)cc3Cl)cc2n(CCC#N)c1=O] | 492.7 | 1H NMR (400 MHz, DMSO-d6) δ 8.71 (s, 1H), 8.50 (s, 1H), 8.12 (dd, J = 11.4, 8.3 Hz, 1H), 8.07 – 7.97 (m, 2H), 4.61 – 4.29 (m, 2H), 3.03 (td, J = 6.8, 2.1 Hz, 2H), 2.20 (s, 3H). | I-198; 2-(2-chloro-4,5-difluoro-phenyl)-4,4,5,5-tetramethyl-1,3,2-dioxaborolane |
| 848 | 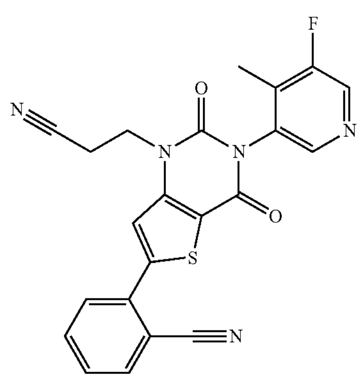 [SMILES: Cc1c(F)cncc1-n1c(=O)c2sc(-c3ccccc3C#N)cc2n(CCC#N)c1=O] | 431.8 | 1H NMR (400 MHz, DMSO-d6) δ 8.63 (s, 1H), 8.43 (S, 1H), 8.13 – 8.06 (m, 2H), 7.98 – 7.88 (m, 2H), 7.79 – 7.71 (m, 1H), 4.60 – 4.27 (m, 2H), 3.03 (t, J = 6.8 Hz, 2H), 2.12 (d, J = 1.7 Hz, 3H). | I-199; (2-cyanophenyl) boronic acid |
| 849 | 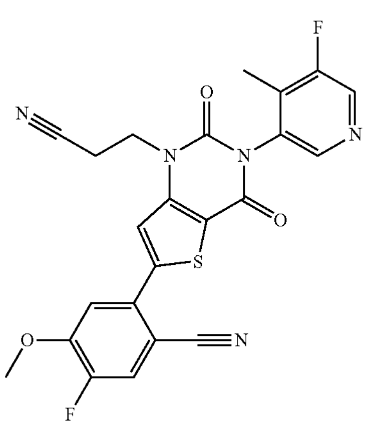 | 479.8 | 1H NMR (400 MHz, DMSO-d6) δ 8.64 (s, 1H), 8.43 (s, 1H), 8.14 (d, J = 11.1 Hz, 1H), 8.05 (s, 1H), 7.59 (d, J = 8.1 Hz, 1H), 4.58 – 4.27 (m, 2H), 4.06 (s, 3H), 3.04 (t, J = 6.8 Hz, 2H), 2.12 (d, J = 1.7 Hz, 3H). | I-199; I-104 |

TABLE 43-continued

Examples 843-897

| Example | Structure | ES/MS m/z | 1H-NMR | Changes to Procedure 102: Different Reagents/ Starting Materials |
|---|---|---|---|---|
| 850 | 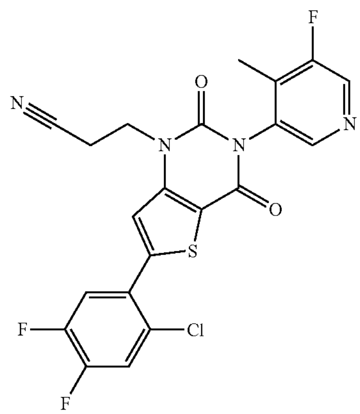 [SMILES: Cc1c(F)cncc1-n1c(=O)c2sc(-c3cc(F)c(F)cc3Cl)cc2n(CCC#N)c1=O] | 476.8 | 1H NMR (400 MHz, DMSO-d6) δ 8.63 (s, 1H), 8.43 (s, 1H), 8.12 (dd, J = 11.4, 8.4 Hz, 1H), 8.08 – 7.97 (m, 2H), 4.63 – 4.22 (m, 2H), 3.04 (td, J = 6.7, 2.3 Hz, 2H), 2.11 (s, 3H). | I-199; 2-(2-chloro-4,5-difluoro-phenyl)-4,4,5,5-tetramethyl-1,3,2-dioxaborolane |
| 851 | 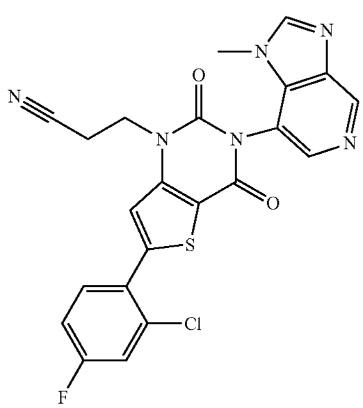 [SMILES: Cn1cnc2cncc(-n3c(=O)c4sc(-c5ccc(F)cc5Cl)cc4n(CCC#N)c3=O)c21] | 480.8 | 1H NMR (400 MHz, DMSO-d6) δ 9.29 (s, 1H), 8.56 (d, J = 3.4 Hz, 2H), 8.02 (s, 1H), 7.96 (dd, J = 8.8, 6.0 Hz, 1H), 7.76 (dd, J = 8.8, 2.7 Hz, 1H), 7.57 – 7.44 (m, 1H), 4.62 – 4.44 (m, 1H), 4.40 (dt, J = 14.4. 6.2 Hz, 1H), 3.77 (s, 3H), 3.07 (t, J = 6.6 Hz, 2H). | I-196; (2-chloro-4-fluoro-phenyl)boronic acid |
| 852 | 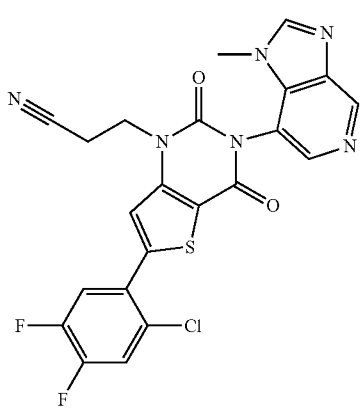 [SMILES: Cn1cnc2cncc(-n3c(=O)c4sc(-c5cc(F)c(F)cc5Cl)cc4n(CCC#N)c3=O)c21] | 498.8 | 1H NMR (400 MHz, DMSO-d6) δ 9.29 (s, 1H), 8.57 (d, J = 3.4 Hz, 2H), 8.15 (dd, J = 11.4, 8.4 Hz, 1H), 8.12 – 7.93 (m, 2H), 4.54 (dt, J = 14.2, 7.1 Hz, 1H), 4.40 (dt, J = 14.3. 6.2 Hz, 1H), 3.77 (s, 3H), 3.09 (td, J = 6.7, 3.1 Hz, 2H). | I-196; 2-(2-chloro-4,5-difluoro-phenyl)-4,4,5,5-tetramethyl-1,3,2-dioxaborolane |

TABLE 43-continued

Examples 843-897

| Example | Structure | ES/MS m/z | 1H-NMR | Changes to Procedure 102: Different Reagents/ Starting Materials |
|---|---|---|---|---|
| 853 | 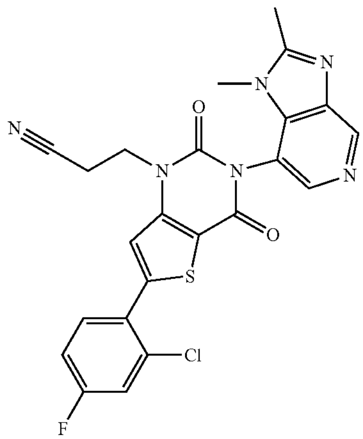 [SMILES: Cc1nc2cncc(-n3c(=O)c4sc(-c5ccc(F)cc5Cl)cc4n(CCC#N)c3=O)c2n1C] | 494.8 | 1H NMR (400 MHz, DMSO-d6) δ 9.27 (s, 1H), 8.62 (s, 1H), 8.03 (s, 1H), 7.96 (dd, J = 8.8, 6.0 Hz, 1H), 7.77 (dd, J = 8,8, 2.7 Hz, 1H), 7.51 (td, J = 8.4, 2.7 Hz, 1H), 4.60 – 4.34 (m, 2H), 3.68 (s, 3H), 3.06 (t, J = 6.6 Hz, 2H), 2.67 (s, 3H). | (2-chloro-4-fluoro-phenyl)boronic acid |
| 854 | 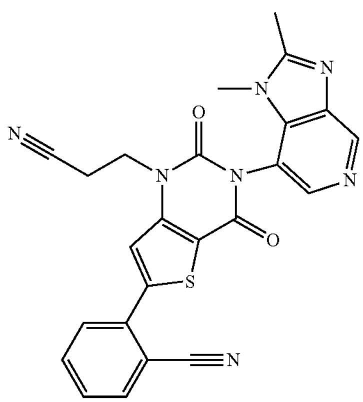 [SMILES: Cc1nc2cncc(-n3c(=O)c4sc(-c5ccccc5C#N)cc4n(CCC#N)c3=O)c2n1C] | 467.8 | 1H NMR (400 MHz, DMSO-d6) δ 9.19 (s, 1H), 8.54 (s, 1H), 8.15 (s, 1H), 8.12 (dd, J = 7.8, 1.2 Hz, 1H), 8.01 – 7.90 (m, 2H), 7.84 – 7.74 (m, 1H), 4.62 – 4.32 (m, 2H), 3.67 (s, 3H), 3.07 (t, J = 6.7 Hz, 2H). 2.66 (s, 3H). | (2-cyanophenyl) boronic acid |
| 855 | 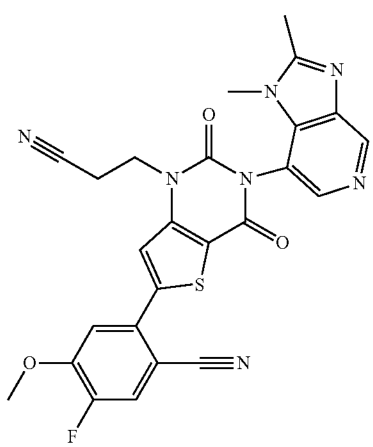 [SMILES: COc1cc(-c2cc3c(s2)c(=O)n(-c2cncc4nc(C)n(C)c24)c(=O)n3CCC#N)c(C#N)cc1F] | 515.7 | 1H NMR (400 MHz, DMSO-d6) δ 9.22 (s, 1H), 8.57 (s, 1H), 8.16 (d, J = 11.0 Hz, 1H), 8.11 (s, 1H), 7.61 (d, J = 8.1 Hz, 1H), 4.65 – 4.32 (m, 2H), 4.07 (s, 3H), 3.67 (s, 3H), 3.08 (t, J = 6.7 Hz, 2H), 2.66 (s, 3H). | I-104 |

TABLE 43-continued

Examples 843-897

| Example | Structure | ES/MS m/z | 1H-NMR | Changes to Procedure 102: Different Reagents/ Starting Materials |
|---|---|---|---|---|
| 856 | 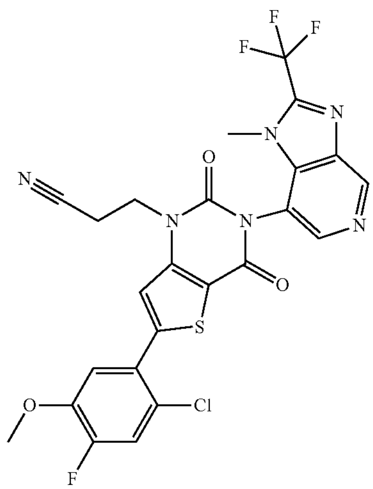 [SMILES: COc1cc(-c2cc3c(s2)c(=O)n(-c2cncc4nc(C(F)(F)F)n(C)c24)c(=O)n3CCC#N)c(Cl)cc1F] | 578.7 | 1H NMR (400 MHz, DMSO-d6) δ 9.30 (s, 1H), 8.59 (s, 1H), 7.99 (s, 1H), 7.75 (d, J = 11.0 Hz, 1H), 7.55 (d, J = 8.9 Hz, 1H), 4.62 – 4.33 (m, 2H), 3.97 (s, 3H), 3.83 (s, 3H), 3.08 (t, J = 6.6 Hz, 2H). | I-197 |
| 857 | 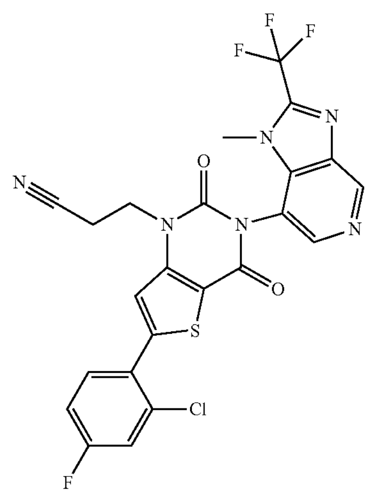 [SMILES: Cn1c(C(F)(F)F)nc2cncc(-n3c(=O)c4sc(-c5ccc(F)cc5Cl)cc4n(CCC#N)c3=O)c21] | 548.7 | 1H NMR (400 MHz, DMSO-d6) δ 9.29 (s, 1H), 8.59 (s, 1H), 8.01 (s, 1H), 7.95 (dd, J = 8.7, 6.1 Hz, 1H), 7.76 (dd, J = 8.7, 2.6 Hz, 1H), 7.50 (td, J = 8.5, 2.6 Hz, 1H), 4.47 (ddt, J = 44.6, 13.9, 6.6 Hz, 2H), 3.83 (s, 3H), 3.06 (t, J = 6.6 Hz, 2H). | I-197; (2-chloro-4-fluoro-phenyl)boronic acid |
| 858 | 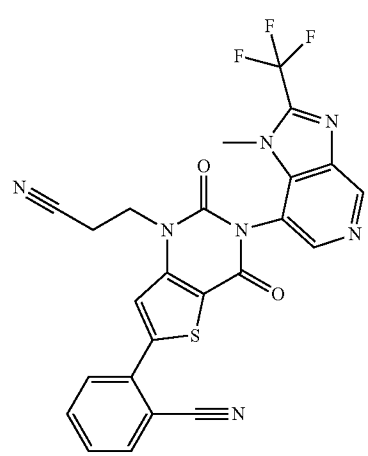 [SMILES: Cn1c(C(F)(F)F)nc2cncc(-n3c(=O)c4sc(-c5ccccc5C#N)cc4n(CCC#N)c3=O)c21] | 521.8 | 1H NMR (400 MHz, DMSO-d6) δ 9.29 (s, 1H), 8.59 (s, 1H), 8.14 (s, 1H), 8.12 (dd, J = 7.8, 1.2 Hz, 1H), 8.02 – 7.87 (m, 2H), 7.76 (td, J = 7.5, 1.5 Hz, 1H), 4.47 (ddt, J = 52.5, 13.9, 6.8 Hz, 2H), 3.84 (s, 3H), 3.07 (t, J = 6.7 Hz, 2H). | I-197; (2-cyanophenyl) boronic acid |

TABLE 43-continued

Examples 843-897

| Example | Structure | ES/MS m/z | 1H-NMR | Changes to Procedure 102: Different Reagents/ Starting Materials |
|---|---|---|---|---|
| 859 | 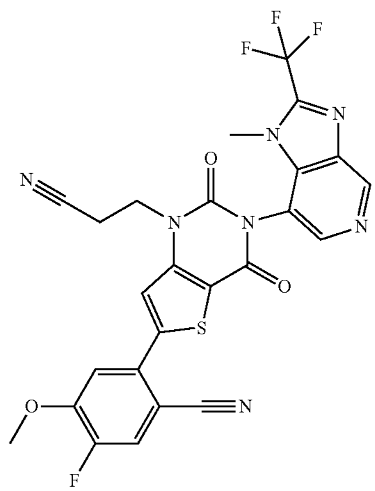 [SMILES: COc1cc(-c2cc3c(s2)c(=O)n(-c2cncc4nc(C(F)(F)F)n(C)c24)c(=O)n3CCC#N)c(C#N)cc1F] | 569.8 | 1H NMR (400 MHz, DMSO-d6) δ 9.29 (s, 1H), 8.59 (s, 1H), 8.15 (d, J = 11.1 Hz, 1H), 8.10 (s, 1H), 7.61 (d, J = 8.0 Hz, 1H), 4.48 (ddt, J = 55.7, 13.9, 6.7 Hz, 2H), 4.06 (s, 3H), 3.83 (s, 3H), 3.09 (t, J = 6.7 Hz, 2H). | I-197; I-104 |
| 860 | 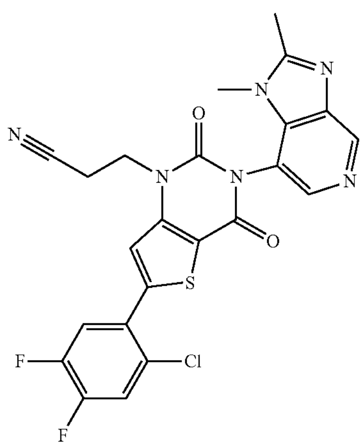 | 512.8 | 1H NMR (400 MHz, DMSO-d6) δ 9.17 (s, 1H), 8.52 (s, 1H), 8.15 (dd, J = 11.4, 8.4 Hz, 1H), 8.10 – 7.98 (m, 2H), 4.60 – 4.35 (m, 2H), 3.65 (s, 3H), 3.08 (t, J = 6.7 Hz, 2H), 2.65 (s, 3H). | 2-(2-chloro-4,5-difluoro-phenyl)-4,4,5,5-tetramethyl-1,3,2-dioxaborolane |
| 861 | 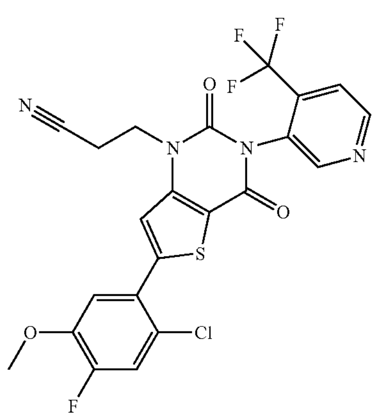 [SMILES: COc1cc(-c2cc3c(s2)c(=O)n(-c2cnccc2C(F)(F)F)c(=O)n3CCC#N)c(Cl)cc1F] | 524.7 | 1H NMR (400 MHz, DMSO-d6) δ 9.00 (d, J = 5.1 Hz. 1H), 8.93 (s, 1H), 8.01 (d, J = 5.1 Hz, 1H), 7.95 (s, 1H), 7.74 (d, J = 11.1 Hz, 1H), 7.57 (d, J = 8.9 Hz, 1H), 4.44 (ddt. J = 44.7, 14.4, 6.5 Hz, 2H), 3.96 (s, 3H), 3.00 (t, J = 6.5 Hz, 2H) | I-200 |

TABLE 43-continued

Examples 843-897

| Example | Structure | ES/MS m/z | 1H-NMR | Changes to Procedure 102: Different Reagents/ Starting Materials |
|---|---|---|---|---|
| 862 | 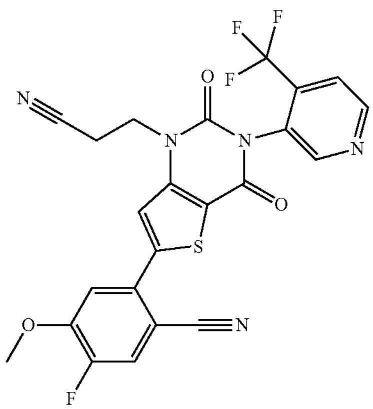 [SMILES: COc1cc(-c2cc3c(s2)c(=O)n(-c2cnccc2C(F)(F)F)c(=O)n3CCC#N)c(C#N)cc1F] | 515.8 | 1H NMR (400 MHz, DMSO-d6) δ 9.01 (d, J = 5.1 Hz, 1H), 8.93 (s, 1H), 8.14 (d, J = 11.1 Hz, 1H), 8.06 (s, 1H), 8.01 (d, J = 5.2 Hz, 1H), 7.67 – 7.59 (m, 1H), 4.60 – 4.25 (m, 2H), 4.05 (s, 3H), 3.17 – 2.88 (m, 2H). | I-200; I-104 |
| 863 | 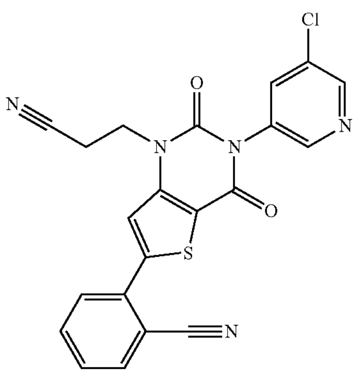 [SMILES: N#CCCn1c(=O)n(-c2cncc(Cl)c2)c(=O)c2sc(-c3ccccc3C#N)cc21] | 434.4 | 1H NMR (400 MHz, DMSO-d6) δ 8.78 – 8.72 (m, 1H), 8.63 – 8.54 (m, 1H), 8.16 – 8.08 (m, 1H), 8.12 – 8.07 (m, 2H), 7.99 – 7.88 (m, 2H), 7.75 (dd, 1H), 4.42 (t, 2H), 3.03 – 2.94 (m, 2H). | I-265; (2-cyanophenyl) boronic acid |
| 864 | 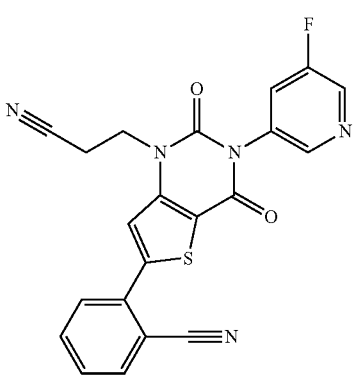 | 418.5 | 1H NMR (400 MHz, DMSO-d6) δ 8.71 (d, 1H), 8.54 – 8.49 (m, 1H), 8.13 – 8.06 (m, 2H), 7.98 – 7.87 (m, 3H), 7.79 – 7.70 (m, 1H), 4.41 (t, 2H), 2.98 (t, 2H). | I-266; (2-cyanophenyl) boronic acid |

TABLE 43-continued
Examples 843-897
| Example | Structure | ES/MS m/z | 1H-NMR | Changes to Procedure 102: Different Reagents/ Starting Materials |
|---|---|---|---|---|
| 865 | 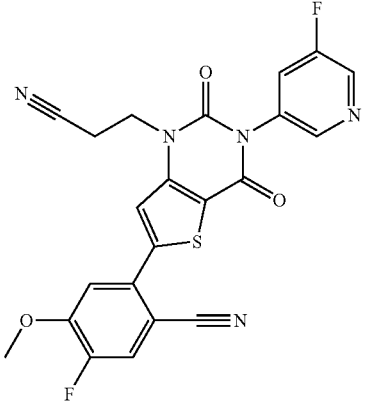 | 446.1 | 1H NMR (400 MHz, DMSO-d6) δ 8.72 (d, 1H), 8.52 (t, 1H), 8.14 (d, 1H), 8.06 (s, 1H), 7.95 (dt, 1H), 7.58 (d, 1H), 4.42 (t, 2H), 4.06 (s, 3H), 3.00 (t, 2H). | I-266; I-104 |
| 866 | 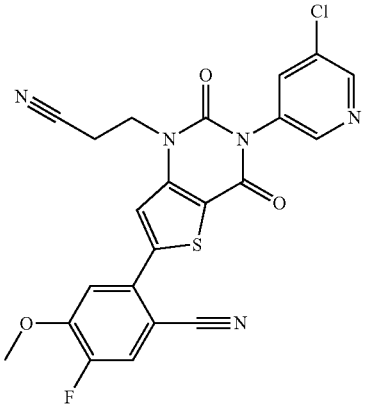 [SMILES: COc1cc(-c2cc3c(s2)c(=O)n(-c2cncc(F)c2)c(=O)n3CCC#N)c(C#N)cc1F] | 482.2 | 1H NMR (400 MHz, DMSO-d6) δ 8.75 (d, 1H), 8.60 (d, 1H), 8.18 – 8.10 (m, 2H), 8.06 (s, 1H), 7.58 (d, 1H), 4.42 (t, 2H), 4.06 (s, 3H), 3.00 (t, 2H). | I-265; I-104 |
| 867 | 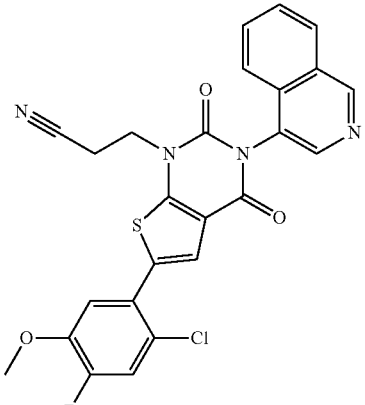 | 506.8 | 1H NMR (400 MHz, DMSO) δ 9.50 (s, 1H), 8.58 (s, 1H). 8.35 – 8.28 (m, 1H), 7.94 (dd, J = 8.3, 1.4 Hz, 1H), 7.88 – 7.74 (m, 3H), 7.66 (d, J = 11.0 Hz, 1H), 7.49 (d, J = 8,9 Hz, 1H), 4.31 (td, J = 6.5, 1,9 Hz, 2H), 3.95 (s, 3H), 3.10 (d, J = 13.0 Hz, 2H). | I-329 |

TABLE 43-continued

Examples 843-897

| Example | Structure | ES/MS m/z | 1H-NMR | Changes to Procedure 102: Different Reagents/ Starting Materials |
|---|---|---|---|---|
| 868 | 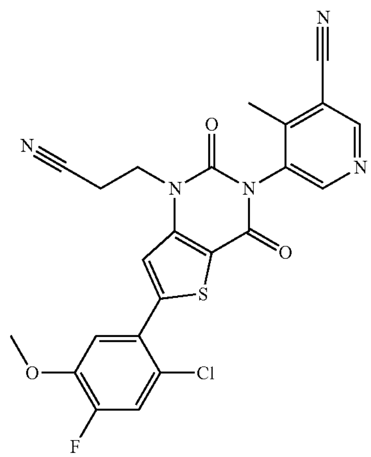 [SMILES: COc1cc(-c2cc3c(s2)c(=O)n(-c2cncc(C#N)c2C)c(=O)n3CCC#N)c(Cl)cc1F] | 495.8 | 1H NMR (400 MHz, DMSO-d6) δ 9.12 – 9.01 (m, 1H), 8.95 – 8.79 (m, 1H), 7.95 (d, J = 3.9 Hz, 1H), 7.74 (d, J = 11.0 Hz, 1H), 7.51 (q, J = 5.5, 5.0 Hz, 1H), 4.50 (p, J = 7.1 Hz, 1H), 4.45 – 4.35 (m, 1H), 3.97 (s, 3H), 3.02 (q, J = 7.0 Hz, 2H), 2.36 (s, 3H). | I-242 |
| 869 | 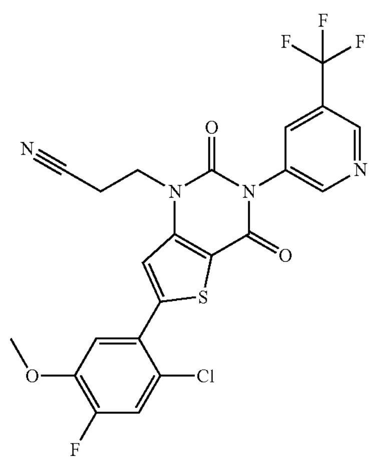 [SMILES: COc1cc(-c2cc3c(s2)c(=O)n(-c2cncc(C(F)(F)F)c2)c(=O)n3CCC#N)c(Cl)cc1F] | 524.6 | 1H NMR (400 MHz, DMSO-d6) δ 9.10 (d, J = 2.2 Hz, 1H), 8.94 (d, J = 2.2 Hz, 1H), 8.42 (t, J = 2.3 Hz, 1H), 7.96 (s, 1H), 7.74 (d, J = 11.0 Hz, 1H), 7.53 (d, J = 8.9 Hz, 1H), 4.44 (t, J = 6.6 Hz, 2H), 3.97 (s, 3H), 3.00 (t, J = 6.5 Hz, 2H). | I-244 |
| 870 | 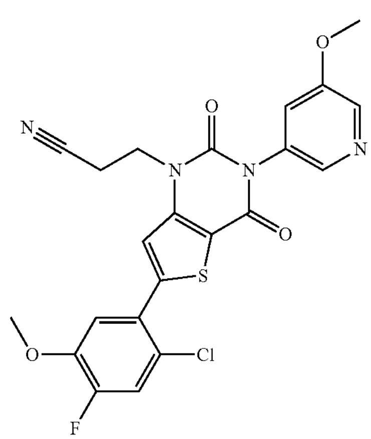 | 486.7 | 1H NMR (400 MHz, DMSO-d6) δ 8.40 (d, J = 2.7 Hz, 1H), 8.19 (d, J = 1.9 Hz, 1H), 7.93 (s, 1H), 7.73 (d, J = 11.1 Hz, 1H), 7.57 – 7.48 (m, 2H), 4.42 (t, J = 6.6 Hz, 2H), 3.97 (S, 3H), 3.87 (s, 3H), 3.00 (t, J = 6.5 Hz, 2H). | I-245 |

TABLE 43-continued

Examples 843-897

| Example | Structure | ES/MS m/z | 1H-NMR | Changes to Procedure 102: Different Reagents/ Starting Materials |
|---|---|---|---|---|
| 871 | 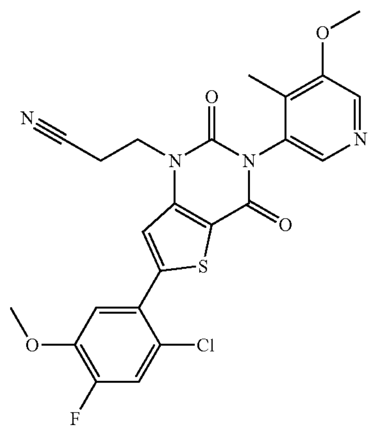 | 500.8 | 1H NMR (400 MHz, DMSO-d6) δ 8.40 (s, 1H). 8.21 (s, 1H), 7.92 (s, 1H), 7.73 (d, J = 11.0 Hz, 1H). 7.53 (d, J = 8.9 Hz, 1H), 4.49 (dt, J = 14.0, 6.9 Hz, 1H), 4.44 – 4.32 (m, 1H), 4.00 (s, 3H), 3.96 (s, 3H), 3.03 (t, J = 6.6 Hz, 2H), 2.00 (s, 3H). | I-246 |
| 872 | 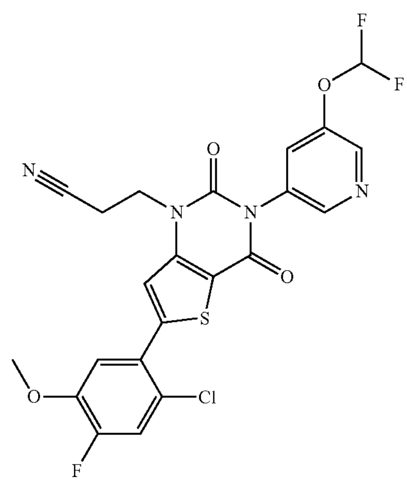 [SMILES: COc1cc(-c2cc3c(s2)c(=O)n(-c2cncc(OC(F)F)c2)c(=O)n3CCC#N)c(Cl)cc1F] | 522.6 | 1H NMR (400 MHz, DMSO-d6) δ 8.61 (s, 1H), 8.53 (s, 1H), 7.94 (s, 1H), 7.86 (t, J = 2.2 Hz, 1H), 7.73 (d, J = 11.0 Hz, 1H). 7.52 (d, J = 11.0 Hz, 1H), 7.58 – 7.19 (t, J = 72.0 Hz, 1H), 4.43 (t, J = 6.6 Hz, 2H), 3.97 (s, 3H), 3.00 (t, J = 6.5 Hz, 2H). | I-247 |
| 873 | 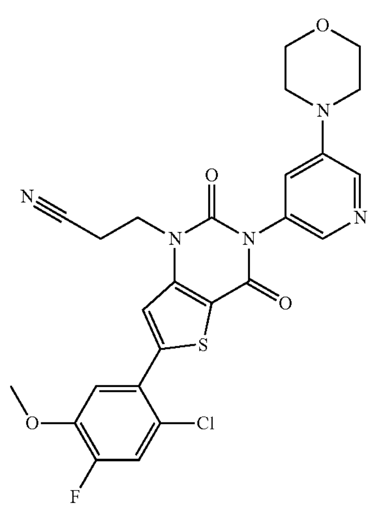 [SMILES: COc1cc(-c2cc3c(s2)c(=O)n(-c2cncc(N4CCOCC4)c2)c(=O)n3CCC#N)c(Cl)cc1F] | 541.8 | 1H NMR (400 MHz, DMSO-d6) δ 8.45 (d, J = 2.7 Hz. 1H), 8.19 (d, J = 1.7 Hz, 1H), 7.95 (s, 1H), 7.81 (t, J = 2.2 Hz, 1H), 7.73 (d, J = 11.0 Hz, 1H), 7.52 (d, J = 8.9 Hz, 1H), 4.43 (t, J = 6.5 Hz, 2H), 3.97 (s, 3H), 3.77 (dd, J = 5.9, 3.9 Hz, 4H), 3.30 (t, J = 4.9 Hz, 4H), 3.00 (t, J = 6.5 Hz, 2H). | I-248 |

TABLE 43-continued

Examples 843-897

| Example | Structure | ES/MS m/z | 1H-NMR | Changes to Procedure 102: Different Reagents/ Starting Materials |
|---|---|---|---|---|
| 874 | 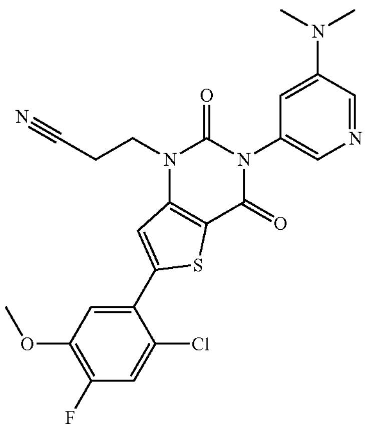 | 499.8 | 1H NMR (400 MHz, DMSO-d6) δ 8.22 (d, J = 2.8 Hz, 1H), 7.94 (s, 1H), 7.74 (d, J = 11.0 Hz, 1H), 7.52 (d, J = 8.9 Hz, 1H), 7.32 (d, J = 11.4 Hz, 1H). 7.19 (d, J = 9.9 Hz, 1H), 4.43 (t, J = 6.6 Hz, 2H), 3.97 (s, 3H), 3.84 (s, 6H), 2.99 (d, J = 6.6 Hz, 2H). | I-249 |
| 875 | 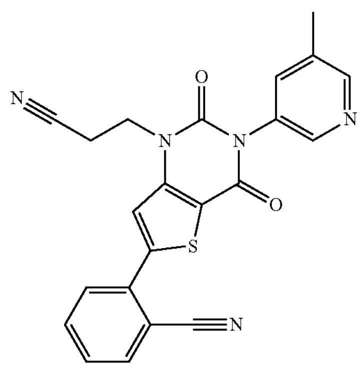 | 413.8 | 1H NMR (400 MHz, DMSO) δ 8.53 – 8.34 (m, 2H), 8.10 (d, J = 11.0 Hz, 2H), 7.94 (t, J = 5.0 Hz, 2H), 7.79 – 7.67 (m, 2H), 4.41 (t, J = 6.8 Hz, 2H), 2.99 (t, J = 6.6 Hz, 2H), 2.39 (s, 3H). | I-286; (2-cyanophenyl) boronic acid |
| 876 | 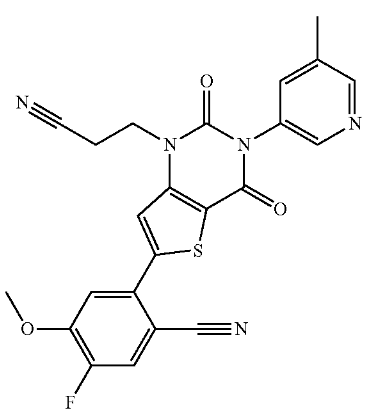 | 461.8 | 1H NMR (400 MHz, DMSO) δ 8.54 (d, J = 1.9 Hz, 1H), 8.44 (d, J = 2.2 Hz, 1H), 8.13 (d, J = 11.1 Hz, 1H), 8.04 (s, 1H), 7.80 – 7.71 (m, 1H), 7.58 (d, J = 8.0 Hz, 1H), 4.41 (t, J = 6.8 Hz, 2H), 4.06 (s, 3H), 3.00 (t, J = 6.8 Hz, 2H), 2.40 (s, 3H). | I-286; I-104 |

TABLE 43-continued

Examples 843-897

| Example | Structure | ES/MS m/z | 1H-NMR | Changes to Procedure 102: Different Reagents/ Starting Materials |
|---|---|---|---|---|
| 877 | 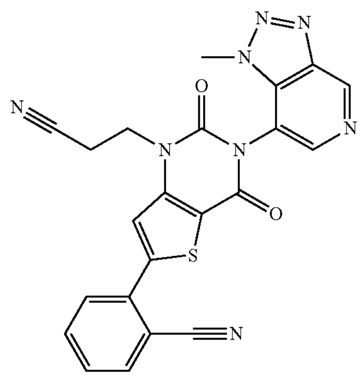 [SMILES: Cn1nnc2cncc(-n3c(=O)c4sc(-c5ccccc5C#N)cc4n(CCC#N)c3=O)c21] | 454.9 | 1H NMR (400 MHz, DMSO) δ 9.61 (s, 1H), 8.64 (s, 1H), 8.17 – 8.09 (m, 2H), 8.01 – 7.89 (m, 2H), 7.76 (td, J = 7.5, 1.5 Hz, 1H), 4.54 (dt, J = 14.3, 7.2 Hz, 1H), 4.41 (dt, J = 14.4, 6.4 Hz, 1H), 4.21 (s, 3H), 3.07 (t, J = 6.7 Hz, 2H). | I-228, (2-cyanophenyl)boronic acid |
| 878 | 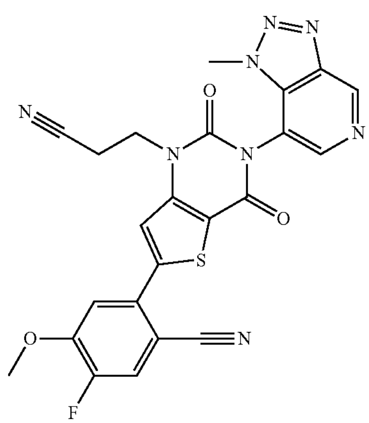 [SMILES: COc1cc(-c2cc3c(s2)c(=O)n(-c2cncc4nnn(C)c24)c(=O)n3CCC#N)c(C#N)cc1F] | 502.8 | 1H NMR (400 MHz, DMSO) δ 9.61 (s, 1H), 8.64 (s, 1H), 8.19 – 8.09 (m, 2H), 7.67 – 7.56 (m, 1H), 4.55 (dt, J = 14.3, 7.1 Hz, 1H), 4.42 (dt, J = 14.3, 6.3 Hz, 1H), 4.20 (s, 3H), 4.07 (s, 3H), 3.09 (t, J = 6.7 Hz, 2H). | I-228, I-104 |
| 879 | 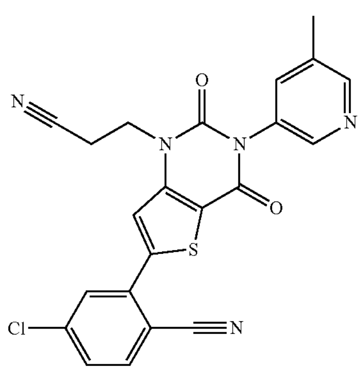 [SMILES: Cc1cncc(-n2c(=O)c3sc(-c4cc(Cl)ccc4C#N)cc3n(CCC#N)c2=O)c1] | 447.8 | 1H NMR (400 MHz, DMSO) δ 8.52 (dd, J = 2.0, 0.8 Hz, 1H), 8.41 (d, J = 2.3 Hz, 1H), 8.14 (d, J = 0.9 Hz, 1H), 8.13 – 8.11 (m, 1H), 7.88 – 7.75 (m, 2H), 7.72 (d, J = 2.5 Hz, 1H), 4.41 (t, J = 6.9 Hz, 2H), 3.00 (t, J = 6.9 Hz, 2H), 2.39 (s, 3H). | I-286; (5-chloro-2-cyano-phenyl)boronic acid |

TABLE 43-continued

Examples 843-897

| Example | Structure | ES/MS m/z | 1H-NMR | Changes to Procedure 102: Different Reagents/ Starting Materials |
|---|---|---|---|---|
| 880 | 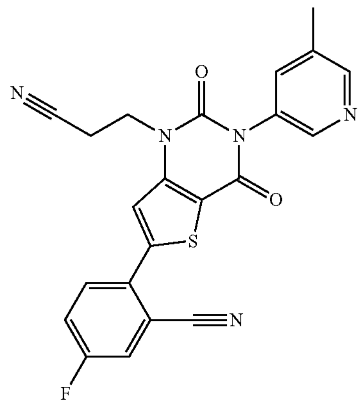 [SMILES: Cc1cncc(-n2c(=O)c3sc(-c4ccc(F)cc4C#N)cc3n(CCC#N)c2=O)c1] | 431.8 | 1H NMR (400 MHz, DMSO) δ 8.51 (d, J = 1.9 Hz, 1H), 8.40 (d, J = 2.2 Hz, 1H), 8.15 (dd, J = 8.6, 2.8 Hz, 1H), 8.06 (s, 1H), 7.99 (dd, J = 8.8, 5.3 Hz, 1H), 7.84 (td, J = 8.5, 2.8 Hz, 1H), 7.70 (s, 1H), 4.40 (t, J = 6.9 Hz, 2H), 2.99 (t, J = 6.8 Hz, 2H), 2.39 (s, 3H). | I-286; (2-cyano-4-fluoro-phenyl)boronic acid |
| 881 | 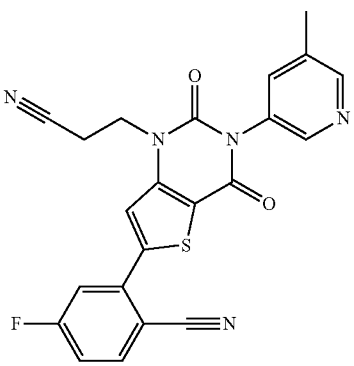 [SMILES: Cc1cncc(-n2c(=O)c3sc(-c4cc(F)ccc4C#N)cc3n(CCC#N)c2=O)c1] | 431.8 | 1H NMR (400 MHz, DMSO) δ 8.55 – 8.50 (m, 1H), 8.41 (d, J = 2.3 Hz, 1H), 8.21 (dd, J = 8.7, 5.6 Hz, 1H), 8.14 (s, 1H), 7.93 (dd, J = 9.6, 2.6 Hz, 1H), 7.72 (d, J = 2.3 Hz, 1H), 7.65 (td, J = 8.4, 2.6 Hz, 1H), 4.40 (t, J = 6.9 Hz, 2H), 3.00 (t, J = 6.9 Hz, 2H), 2.40 (s, 3H). | I-286; (2-cyano-5-fluoro-phenyl)boronic acid |
| 882 | 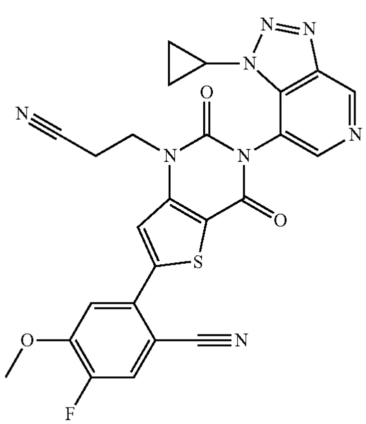 [SMILES: COc1cc(-c2cc3c(s2)c(=O)n(-c2cncc4nnn(C5CC5)c24)c(=O)n3CCC#N)c(C#N)cc1F] | 528.8 | 1H NMR (400 MHz, DMSO) δ 9.61 (s, 1H), 8.66 (s, 1H). 8.19 – 8.11 (m, 2H). 7.62 (d, J = 8.1 Hz, 1H). 4.56 (dt, J = 13.9, 6.9 Hz, 1H), 4.42 (dt, J = 13.8, 6.4 Hz, 1H), 4.07 (s, 3H), 3.80 (td, J = 6.7, 3.5 Hz, 1H). 3.14 – 3.06 (m, 2H), 1.31 – 0.88 (m, 4H). | I-300, I-104 |

TABLE 43-continued

Examples 843-897

| Example | Structure | ES/MS m/z | 1H-NMR | Changes to Procedure 102: Different Reagents/ Starting Materials |
|---|---|---|---|---|
| 883 | 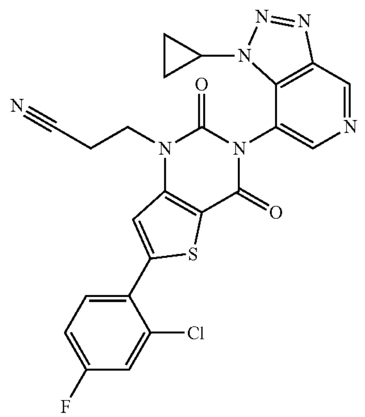 [SMILES: N#CCCn1c(=O)n(-c2cncc3nnn(C4CC4)c23)c(=O)c2sc(-c3ccc(F)cc3Cl)cc21] | 507.8 | 1H NMR (400 MHz, DMSO) δ 9.61 (s, 1H), 8.66 (s, 1H), 8.05 (s, 1H), 7.97 (dd, J = 8.8, 6.1 Hz, 1H), 7.76 (dd, J = 8.8, 2.6 Hz, 1H), 7.50 (td, J = 8.4, 2.7 Hz, 1H), 4.58 – 4.38 (m, 2H), 3.84 – 3.74 (m, 1H), 3.08 (t, J = 6.6 Hz, 2H), 1.26 (dd, J = 11.6, 5.7 Hz, 2H), 1.11 – 0.90 (m, 2H). | I-300, (2-chloro-4-fluoro-phenyl)boronic acid |
| 884 | 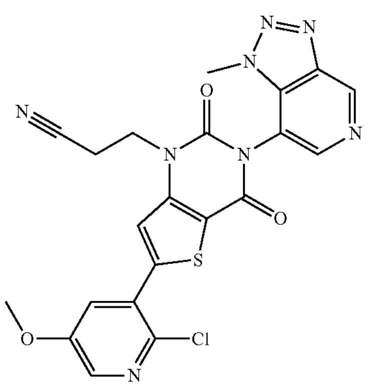 [SMILES: COc1cnc(Cl)c(-c2cc3c(s2)c(=O)n(-c2cncc4nnn(C)c24)c(=O)n3CCC#N)c1] | 494.8 | 1H NMR (400 MHz, DMSO) δ 9.60 (s, 1H), 8.64 (s, 1H), 8.33 (d, J = 2.9 Hz, 1H), 8.15 (s, 1H), 7.95 (d, J = 2.9 Hz, 1H), 4.60 -- 4.37 (m, 2H), 4.20 (s, 3H), 3.97 (s, 3H), 3.09 (t, J = 6.7 Hz, 2H). | I-228, (2-chloro-5-methoxy-3-pyridyl)boronic acid |
| 885 | 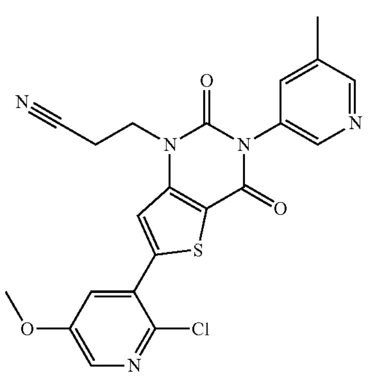 [SMILES: COc1cnc(Cl)c(-c2cc3c(s2)c(=O)n(-c2cncc(C)c2)c(=O)n3CCC#N)c1] | 453.8 | 1H NMR (400 MHz, DMSO) δ 8.53 (dd, J = 2.1, 0.9 Hz, 1H), 8.43 (d, J = 2.2 Hz, 1H), 8.32 (d, J = 3.0 Hz, 1H), 8.09 (s, 1H), 7.92 (d, J = 3.0 Hz, 1H), 7.75 (td, J = 2.2, 0.9 Hz, 1H), 4.42 (t, J = 6.7 Hz, 2H), 3.97 (s, 3H), 3.00 (t, J = 6.7 Hz, 2H), 2.40 (s, 3H). | I-286; (2-chloro-5-methoxy-3-pyridyl)boronic acid |

TABLE 43-continued

Examples 843-897

| Example | Structure | ES/MS m/z | 1H-NMR | Changes to Procedure 102: Different Reagents/ Starting Materials |
|---|---|---|---|---|
| 886 | 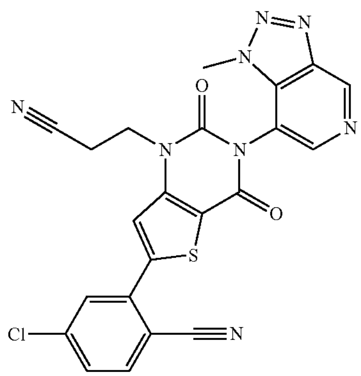 [SMILES: Cn1nnc2cncc(-n3c(=O)c4sc(-c5cc(Cl)ccc5C#N)cc4n(CCC#N)c3=O)c21] | 488.8 | 1H NMR (400 MHz, DMSO) δ 9.61 (s, 1H), 8.64 (s, 1H), 8.20 (s, 1H), 8.15 (dd, J = 5.2, 3.1 Hz, 2H), 7.86 (dd, J = 8.5, 2.0 Hz, 1H), 4.54 (dt, J = 14.3, 7.2 Hz, 1H), 4.41 (dt, J = 14.4, 6.4 Hz, 1H), 4.21 (s, 3H). 3.14 – 3.05 (m, 2H). | I-228, (5-chloro-2-cyano-phenyl)boronic acid |
| 887 | 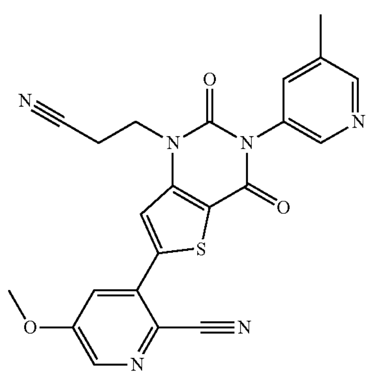 [SMILES: COc1cnc(C#N)c(-c2cc3c(s2)c(=O)n(-c2cncc(C)c2)c(=O)n3CCC#N)c1] | 444.9 | 1H NMR (400 MHz, DMSO) δ 8.61 (d, J = 2.7 Hz, 1H), 8.55 (dd, J = 2.0, 0.8 Hz, 1H), 8.45 (d, J = 2.2 Hz, 1H), 8.17 (s, 1H), 7.87 (d, J = 2.7 Hz, 1H), 7.77 (td, J = 2.1, 0.9 Hz, 1H), 4.41 (t, J = 6.9 Hz, 2H), 4.05 (s, 3H), 3.00 (t, J = 6.8 Hz, 2H), 2.41 (s, 3H). | I-286; (2-cyano-5-methoxy-3-pyridyl)boronic acid |
| 888 | 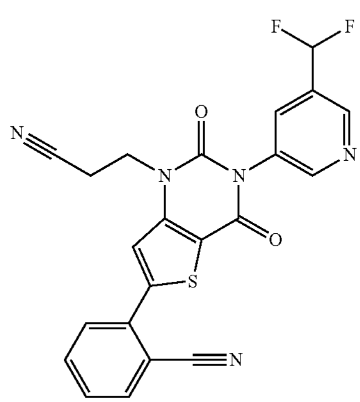 [SMILES: N#CCCn1c(=O)n(-c2cncc(C(F)F)c2)c(=O)c2sc(-c3ccccc3C#N)cc21] | 449.8 | 1H NMR (400 MHz, DMSO-d6) δ 8.90 – 8.85 (m, 1H), 8.78 (dd, J = 2.3, 1.2 Hz, 1H), 8.22 – 8.07 (m, 3H), 7.97 – 7.88 (m, 2H), 7.79 – 7.70 (m, 1H), 7.28 (t, J = 55.1 Hz, 1H), 4.42 (t, J = 6.9 Hz, 2H), 2.99 (t, J = 6.8 Hz, 2H). | I-289; (2-cyanophenyl) boronic acid |

TABLE 43-continued

Examples 843-897

| Example | Structure | ES/MS m/z | 1H-NMR | Changes to Procedure 102: Different Reagents/ Starting Materials |
|---|---|---|---|---|
| 889 | 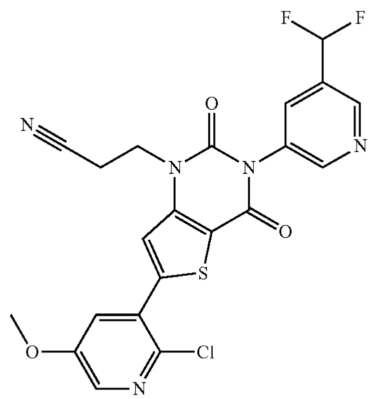 [SMILES: COc1cnc(Cl)c(-c2cc3c(s2)c(=O)n(-c2cncc(C(F)F)c2)c(=O)n3CCC#N)c1] | 489.8 | 1H NMR (400 MHz, DMSO) δ 8.87 (q, J = 1.6 Hz, 1H), 8.77 (dd, J = 2.4, 1.2 Hz, 1H), 8.32 (d, J = 3.0 Hz, 1H), 8.18 – 8.08 (m, 2H), 7.92 (d, J = 3.0 Hz, 1H), 7.47 – 7.11 (m, 1H), 4.43 (t, J = 6.7 Hz, 2H), 3.97 (s, 3H), 3.00 (t, J = 6.6 Hz, 2H). | I-289; (2-chloro-5-methoxy-3-pyridyl)boronic acid |
| 890 | 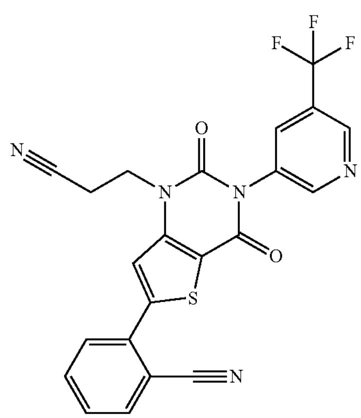 [SMILES: N#CCCn1c(=O)n(-c2cncc(C(F)(F)F)c2)c(=O)c2sc(-c3ccccc3C#N)cc21] | 467.8 | 1H NMR (400 MHz, DMSO) δ9.13 – 9.08 (m, 1H), 8.97 – 8.92 (m, 1H), 8.42 (t, J = 2.2 Hz, 1H), 8.10 (d, J = 7.1 Hz, 2H), 7.99 – 7.88 (m, 2H), 7.75 (ddd, J = 7.8, 7.0, 1.9 Hz, 1H), 4.43 (t, J = 6.8 Hz, 2H), 2.99 (t, J = 6.8 Hz, 2H). | I-244; (2-cyanophenyl)boronic acid |
| 891 | 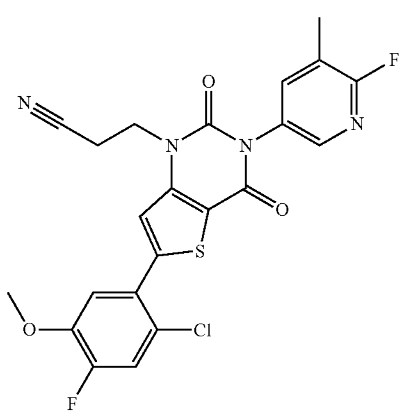 [SMILES: COc1cc(-c2cc3c(s2)c(=O)n(-c2cnc(F)c(C)c2)c(=O)n3CCC#N)c(Cl)cc1F] | 488.7 | 1H NMR (400 MHz, DMSO-d6) δ 8.08 (d, J = 2.4 Hz. 1H), 7.92 (d, J = 11.7 Hz, 2H), 7.73 (d, J = 11.1 Hz, 1H), 7.52 (d, J = 8.9 Hz, 1H), 4.42 (t, J = 6,6 Hz, 2H), 3.97 (s, 3H), 3.00 (t, J = 6.6 Hz, 2H), 2.31 (s, 3H). | I-213 |

TABLE 43-continued

Examples 843-897

| Example | Structure | ES/MS m/z | 1H-NMR | Changes to Procedure 102: Different Reagents/ Starting Materials |
|---|---|---|---|---|
| 892 | 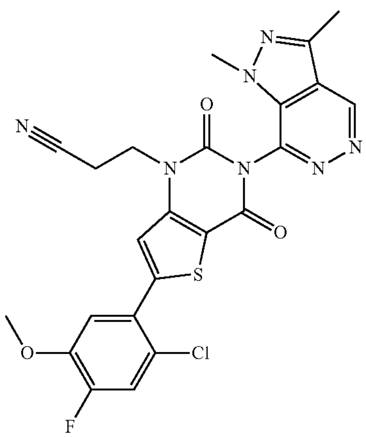 [SMILES: COc1cc(-c2cc3c(s2)c(=O)n(-c2nncc4c(C)nn(C)c24)c(=O)n3CCC#N)c(Cl)cc1F] | 525.7 | 1H NMR (400 MHz, DMSO-d6) δ 9.77 (s, 1H), 8.02 (s, 1H), 7.76 (d, J = 11.0 Hz, 1H), 7.59 (d, J = 8.9 Hz, 1H), 4.60 – 4.39 (m, 2H), 3.98 (s, 3H), 3.95 (s, 3H), 3.11 (td, J = 6.5, 1.8 Hz, 2H), 2.67 (s, 3H). | I-214 |
| 893 | 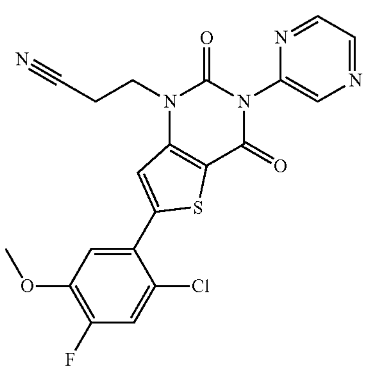 | 457.5 | 1H NMR (400 MHz. DMSO-d6) δ 8.89 – 8.76 (m, 3H), 7.96 (s, 1H), 7.74 (d, J = 11.1 Hz, 1H), 7.54 (d, J = 8.9 Hz, 1H), 4.43 (t. J = 6.4 Hz, 2H), 3.97 (s, 3H), 3.02 (t, J = 6.6 Hz, 2H). | I-215 |
| 894 | 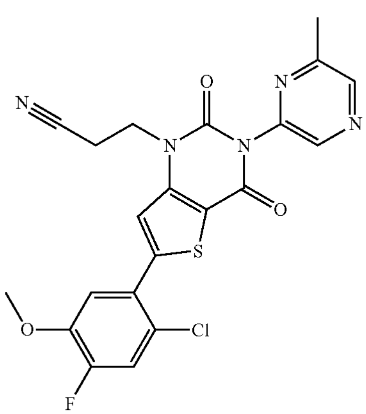 [SMILES: COc1cc(-c2cc3c(s2)c(=O)n(-c2cncc(C)n2)c(=O)n3CCC#N)c(Cl)cc1F] | 471.7 | 1H NMR (400 MHz, DMSO-d6) δ 8.71 (s, 1H), 8.64 (s, 1H), 7.95 (s, 1H), 7.74 (d, J = 11.0 Hz, 1H), 7.54 (d, J = 8.9 Hz, 1H), 4.42 (t, J = 6.8 Hz, 2H), 3.97 (s, 3H), 3.02 (t, J = 6.6 Hz, 2H), 2.58 (s, 3H). | 1-216 |

TABLE 43-continued

Examples 843-897

| Example | Structure | ES/MS m/z | 1H-NMR | Changes to Procedure 102: Different Reagents/ Starting Materials |
|---|---|---|---|---|
| 895 | 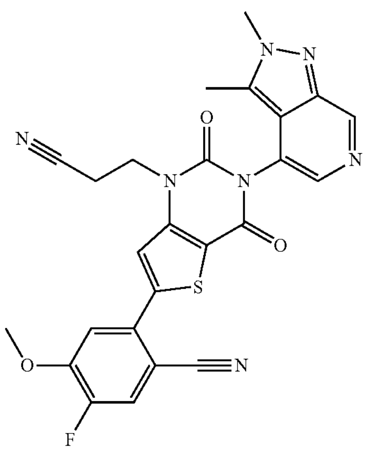 [SMILES: COc1cc(-c2cc3c(s2)c(=O)n(-c2cncc4nn(C)c(C)c24)c(=O)n3CCC#N)c(C#N)cc1F] | 515.9 | 1H NMR (400 MHz, DMSO-d6) δ 9.37 (s, 1H), 8.17 – 8.10 (m, 2H), 8.08 (s, 1H), 7.62 (d, J = 8.1 Hz, 1H), 4.52 (dt, J = 14.1, 6.9 Hz, 1H), 4.38 (dt, J = 14.4, 6.3 Hz, 1H), 4.20 (s, 3H), 4.06 (s, 3H), 3.07 (t, J = 6.6 Hz, 2H), 2.43 (s, 3H). | I-257; I-104 |
| 896 | 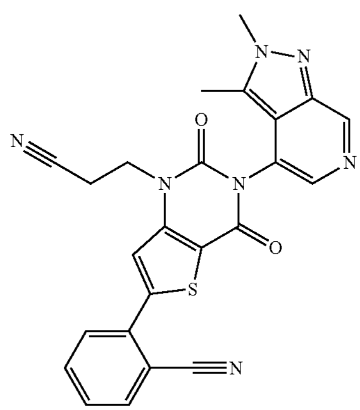 [SMILES: Cc1c2c(-n3c(=O)c4sc(-c5ccccc5C#N)cc4n(CCC#N)c3=O)cncc2nn1C] | 467.9 | 1H NMR (400 MHz, DMSO-d6) δ 9.30 (s, 1H), 8.16 – 8.07 (m, 3H), 8.01 – 7.89 (m, 2H), 7.75 (td, J = 7.6, 1.4 Hz, 1H), 4.51 (dt, J = 14.1, 7.0 Hz, 1H), 4.38 (dt, J = 14.6, 6.5 Hz, 1H), 4.19 (s, 3H), 3.06 (t, J = 6.7 Hz, 2H), 2.42 (s, 3H). | I-257; 2-cyanophenylboronic acid |
| 897 | 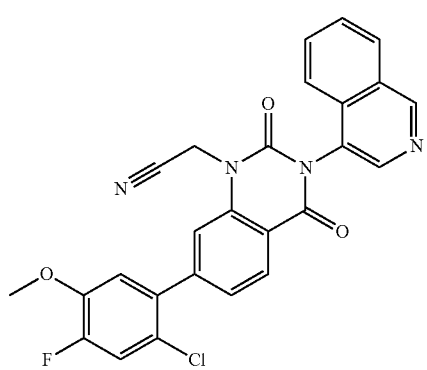 [SMILES: COc1cc(-c2ccc3c(=O)n(-c4cncc5ccccc45)c(=O)n(CC#N)c3c2)c(Cl)cc1F] | 486.8 | 1H NMR (400 MHz, DMSO) δ 9.51 (s, 1H), 8.67 (s, 1H), 8.32 (dd, J = 7.4, 2.0 Hz, 1H), 8.21 (d, J = 8.1 Hz, 1H), 8.06 (dd, J = 8.0, 1.5 Hz, 1H), 7.88 – 7.76 (m, 3H), 7.71 (d, J = 11.1 Hz, 1H), 7.55 (dd, J = 8.0, 1.4 Hz, 1H), 7.30 (d, J = 9.0 Hz, 1H), 5.43 (d, J = 13.7 Hz, 2H), 3.96 (s, 3H). | I-337 |

Procedure 103: Example 898

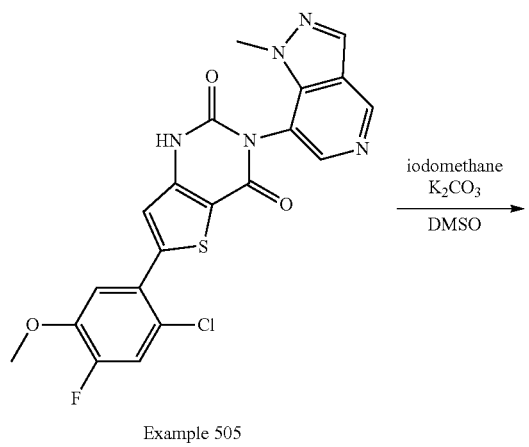

Example 505

Example 898

6-(2-chloro-4-fluoro-5-methoxyphenyl)-1-methyl-3-(1-methyl-1H-pyrazolo[4,3-c]pyrindin-7-yl)thieno[3,2-d]pyrimidine-2,4(1H,3H)-dione (Example 898): To a stirring solution of 6-(2-chloro-4-fluoro-5-methoxyphenyl)-3-(1-methyl-1H-pyrazolo[4,3-c]pyridin-7-yl)thieno[3,2-d]pyrimidine-2,4(1H,3H)-dione (Example 505) (HCl salt) (100 mg, 0.20 mmol, 1.0 equiv.), in DMSO (1 mL), was added $K_2CO_3$ (112 mg, 0.81 mmol) followed by iodomethane (0.13 mL, 0.20 mmol). The reaction mixture was stirred for 1 hour at 50° C., after which the mixture was diluted with water (0.2 mL) and TFA (0.5 mL), and the mixture was filtered through an acrodisc, and purified directly by RP-HPLC (0.1% TFA-ACN in 0.1% TFA Water, Column: Gemini 5 µM, NX-C18 110 Angstrom, 250×21.2 mm) to give the product Example 898.

ES/MS: 471.5 ($M^+$).

1H NMR (400 MHz, DMSO-d6) δ 9.30 (s, 1H), 8.54 (s, 1H), 8.47 (s, 1H), 7.85 (s, 1H), 7.74 (d, J=11.0 Hz, 1H), 7.56 (d, J=8.9 Hz, 1H), 3.98 (s, 3H), 3.91 (s, 3H), 3.66 (s, 3H).

Procedure 104: Example 899 and Example 900

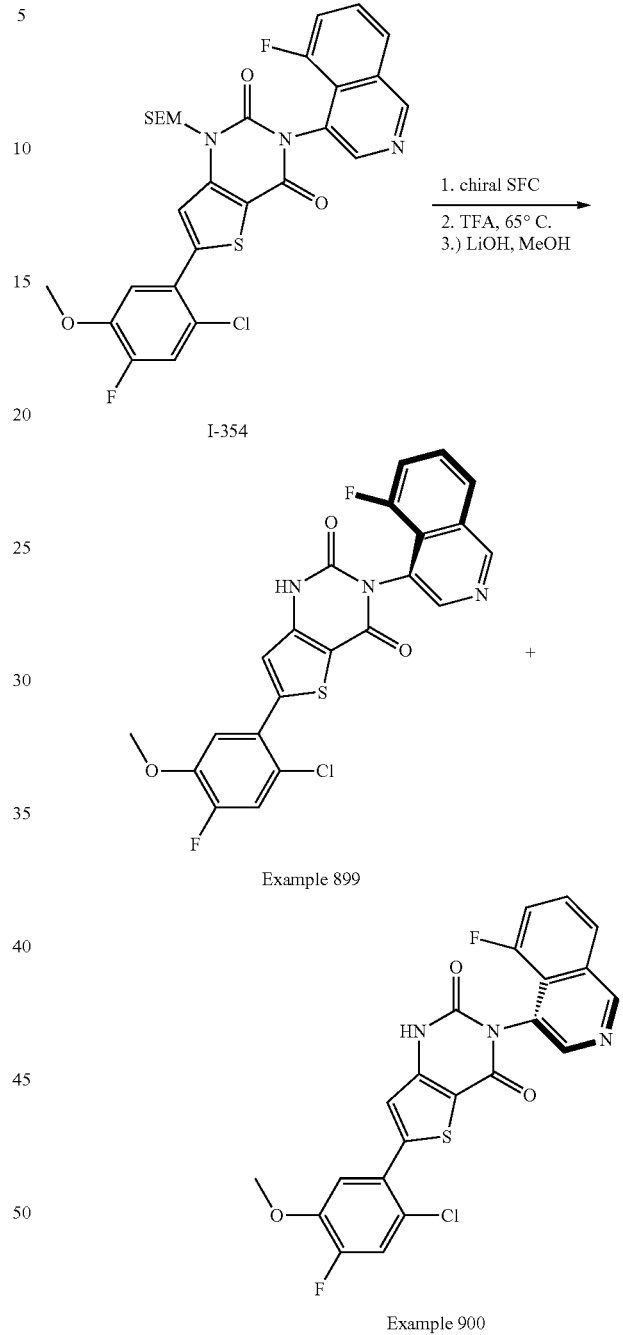

I-354

Example 899

Example 900

6-(2-chloro-4-fluoro-5-methoxyphenyl)-3-(5-fluoroisoquinolin-4-yl)-1-((2-(trimethylsilyl)ethoxy)methyl)thieno[3,2-d]pyrimidine-2,4(1H,3H)-dione (I-354) as a mixture of 2 atropisomers was separated by chiral SFC (AD-H 21×250 5 um column with 30% MeOH cosolvent) to give two enantiomers, which were assigned as Isomer 1 and Isomer 2. Each isomer was then individually subjected to SEM removal under acidic conditions.

Isomer 1:
6-(2-chloro-4-fluoro-5-methoxyphenyl)-3-(5-fluoroisoquinolin-4-yl)thieno[3,2-d]pyrimidine-2,4(1H,3H)-dione (Example 899): To a 20 mL scintillation vial containing a stir bar was added 6-(2-chloro-4-fluoro-5-methoxyphenyl)-3-(5-fluoroisoquinolin-4-yl)-1-((2-(trimethylsilyl)ethoxy)methyl)thieno[3,2-d]pyrimidine-2,4(1H,3H)-dione (Isomer 1) (100 mg, 0.166 mmol), TFA (2 mL), followed by 0.1 mL of H₂O. The reaction mixture was stirred for 30 minutes at room temperature, after which the reaction mixture was concentrated under reduced pressure. The crude material was dissolved in MeOH (1 mL), and LiOH monohydrate (20.9 mg, 3 eq.) dissolved in water (0.5 mL) was added to the reaction. The reaction was stirred for 2 hours at room temperature. The mixture was concentrated under reduced pressure, and subsequently water (2 mL) and TFA (0.2 mL) were added. The mixture was cooled to 0° C., and a precipitate formed. The precipitate was filtered and washed once with water. The precipitate was dried under reduced pressure to give the title compound Example 899 as a trifluoroacetate salt. The stereochemistry of Example 899 was assigned by analogy to Example 438, with Example 899 being the more active isomer.

ES/MS: 471.7 (M⁺).

1H NMR (400 MHz, DMSO-d6) δ 12.33 (s, 1H), 9.53 (d, J=2.4 Hz, 1H), 8.61 (s, 1H), 8.18 (d, J=8.2 Hz, 1H), 7.78 (td, J=8.0, 4.9 Hz, 1H), 7.73-7.58 (m, 2H), 7.50 (d, J=8.9 Hz, 1H), 7.30 (s, 1H), 3.95 (s, 3H).

Isomer 2.

6-(2-chloro-4-fluoro-5-methoxyphenyl)-3-(5-fluoroisoquinolin-4-yl)thieno[3,2-d]pyrimidine-2,4(1H,3H)-dione (Example 900): To a 20 mL scintillation vial containing a stir bar was added 6-(2-chloro-4-fluoro-5-methoxyphenyl)-3-(5-fluoroisoquinolin-4-yl)-1-((2-(trimethylsilyl)ethoxy)methyl)thieno[3,2-d]pyrimidine-2,4(1H,3H)-dione (Isomer 2) (100 mg, 0.166 mmol), TFA (2 mL), followed by 0.1 mL of H₂O. The reaction mixture was stirred for 30 minutes at room temperature, after which the reaction mixture was concentrated under reduced pressure. The crude material was dissolved in MeOH (I mL), and LiOH monohydrate (20.9 mg, 3 eq.) dissolved in water (0.5 mL) was added to the reaction. The reaction was stirred for 2 hours at room temperature. The mixture was concentrated under reduced pressure, and subsequently water (2 mL) and TFA (0.2 mL) were added. The mixture was cooled to 0° C., and a precipitate formed. The precipitate was filtered and washed once with water. The precipitate was dried under reduced pressure to give the title compound Example 900 as a trifluoroacetate salt. The stereochemistry of Example 900 was assigned by analogy to Example 438, with Example 900 being the less active isomer.

ES/MS: 471.8 (M⁺).

1H NMR (400 MHz, DMSO-d6) δ 12.33 (s, 1H), 9.53 (d, J=2.4 Hz, 1H), 8.61 (s, 1H), 8.18 (d, J=8.2 Hz, 1H), 7.78 (td, J=8.0, 4.8 Hz, 1H), 7.71 (d, J=11.1 Hz, 1H), 7.65 (dd, J=12.9, 7.7 Hz, 1H), 7.50 (d, J=8.9 Hz, 1H), 7.30 (s, 1H), 3.95 (s, 3H).

Procedure 105: Example 901

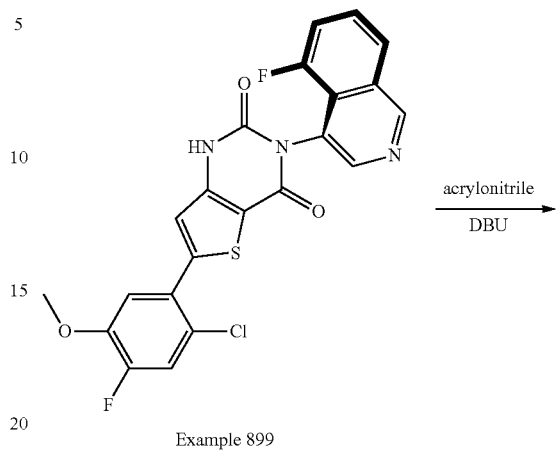

Example 899

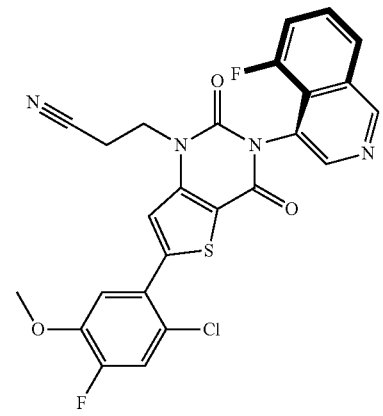

Example 901

3-(6-(2-chloro-4-fluoro-5-methoxyphenyl)-3-(5-fluoroisoquinolin-4-yl)-2,4-dioxo-3,4-dihydrothieno[3,2-d]pyrimidin-1(2H)-yl)propanenitrile (Example 901): To a vial containing Example 899 (TFA salt) (40 mg, 0.075 mmol) was added acrylonitrile (1.5 mL) followed by 1,8-diazabicyclo[5.4.0]undec-7-ene (63 µL, 0.424 mmol). The reaction mixture was stirred for 3 hours at 80° C. after which the mixture was concentrated under reduced pressure. The crude residue was dissolved in acetonitrile (1 mL), water (0.5 mL) and TFA (0.1 mL). The reaction mixture was then filtered through an acrodisc, and purified directly by RP-HPLC (0.1% TFA-ACN in 0.1% TFA Water, Column: Gemini 5 µM, NX-C18 110 Angstrom, 250×21.2 mm) to give the product Example 901 as a trifluoroacetate salt.

ES/MS: 524.7 (M⁺).

1H NMR (400 MHz, DMSO-d6) δ 9.54 (t, J=2.9 Hz, 1H), 8.60 (d, J=5.5 Hz, 1H), 8.19 (dd, J=8.6, 3.7 Hz, 1H), 7.97 (d, J=5.6 Hz, 1H), 7.85-7.71 (m, 2H), 7.71-7.51 (m, 2H), 4.55-4.38 (m, 2H), 3.97 (s, 3H), 3.03 (t, J=6.4 Hz, 2H).

Examples 902-954

The following Examples were made in an analogous fashion according to Procedure 105 and are shown below in Table 44. To prepare the below Examples, different reagents/starting materials were used than some of those described in Procedure 105 and are noted in the last column of Table 44—"Changes to Procedure 105: Different Reagents/Starting Materials".

TABLE 44

Examples 902-954

| Example | Structure | ES/MS m/z | 1H-NMR | Changes to Procedure 105: Different Reagents/ Starting Materials |
|---|---|---|---|---|
| 902 | 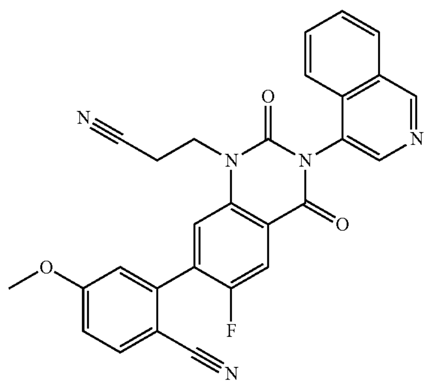 [SMILES: COc1ccc(C#N)c(-c2cc3c(cc2F)c(=O)n(-c2cncc4ccccc24)c(=O)n3CCC#N)c1] | 491.8 | 1H NMR (400 MHz, DMSO-d6) δ 9.48 (s, 1H), 8.59 (s, 1H), 8.41-8.24 (m, 1H), 8.17-7.94 (m, 4H), 7.90-7.67 (m, 2H), 7.40-7.27 (m, 2H), 4.67-4.40 (m, 2H), 3.95 (s, 3H). | Example 428 |
| 903 | 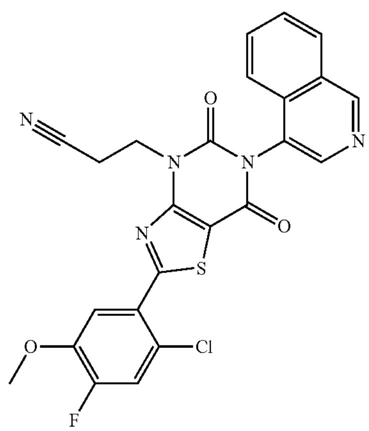 [SMILES: COc1cc(-c2nc3c(s2)c(=O)n(-c2cncc4ccccc24)c(=O)n3CCC#N)c(Cl)cc1F] | 507.7 | 1H NMR (400 MHz, DMSO-d6) δ 9.47 (s, 1H), 8.59 (s, 1H), 8.30 (dd, J = 7.4, 1.7 Hz, 1H), 8.22 (d, J = 9.1 Hz, 1H), 8.00 (dd, J = 8.3, 1.4 Hz, 1H), 7.86 (d, J = 10.9 Hz, 1H), 7.84-7.74 (m, 2H), 4.74-4.44 (m, 2H), 4.02 (s, 3H), 3.11 (t, J = 6.1 Hz, 2H). | Example 704 |
| 904 | 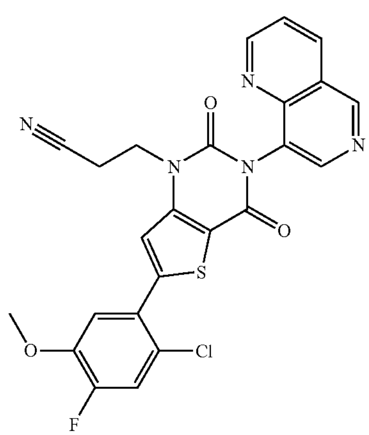 | 508.2. | 1H NMR (400 MHz, DMSO-d6) δ 9.58 (s, 1H), 9.11 (dd, 1H), 8.84 (s, 1H), 8.75 (dd, 1H), 7.97 (s, 1H), 7.81 (dd, 1H), 7.74 (d, 1H), 7.56 (d, 1H), 4.46 (t, 2H), 3.98 (s, 3H), 3.07-2.98 (m, 2H). | Example 553 |

TABLE 44-continued
Examples 902-954
| Example | Structure | ES/MS m/z | 1H-NMR | Changes to Procedure 105: Different Reagents/ Starting Materials |
|---|---|---|---|---|
| 905 | 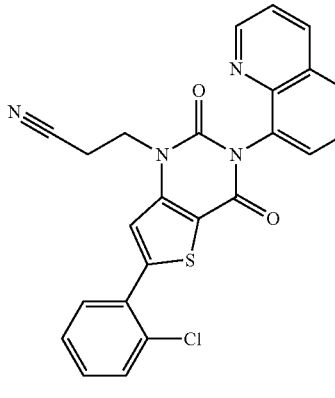 | 460.2 | 1H NMR (400 MHz, DMSO-d6) δ 9.58 (s, 1H), 9.11 (dd, 1H), 8.84 (s, 1H), 8.75 (dd, 1H), 8.02 (s, 1H), 7.93-7.86 (m, 1H), 7.81 (dd, 1H), 7.71 (dt, 1H), 7.64-7.52 (m, 2H), 4.45 (t, 2H), 3.05-2.95 (m, 2H). | Example 133 |
| 906 | 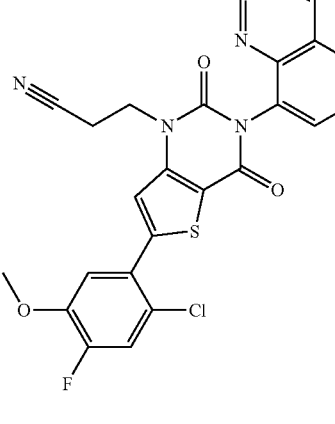 | 522.2 | 1H NMR (400 MHz, DMSO-d6) δ 9.47 (d, 1H), 8.77 (d, 1H), 8.60 (dd, 1H), 7.97 (d, 1H), 7.74 (dd, 1H), 7.67 (dd, 1H), 7.58 (d, 1H), 4.46 (td, 2H), 3.97 (s, 3H), 3.03 (t, 2H), 2.64 (s, 3H). | Example 461 |
| 907 | 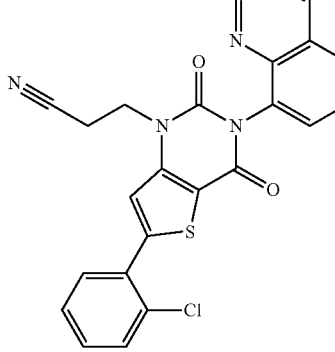 | 474.3 | 1H NMR (400 MHz, DMSO-d6) δ 9.48 (s, 1H), 8.78 (s, 1H), 8.60 (d, 1H), 8.02 (s, 1H), 7.94-7.85 (m, 1H), 7.76-7.64 (m, 2H), 7.64-7.51 (m, 2H), 4.45 (tt, 2H), 3.01 (d, 2H), 2.65 (s, 3H). | Example 453 |

TABLE 44-continued

Examples 902-954

| Example | Structure | ES/MS m/z | 1H-NMR | Changes to Procedure 105: Different Reagents/ Starting Materials |
|---|---|---|---|---|
| 908 | 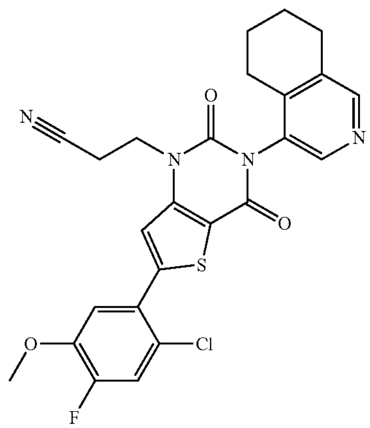 [SMILES: COc1cc(-c2cc3c(s2)c(=O)n(-c2cncc4c2CCCC4)c(=O)n3CCC#N)c(Cl)cc1F] | 511.8 | 1H NMR (400 MHz, DMSO) δ 8.44 (s, 1H), 8.34 (s, 1H), 7.92 (s, 1H), 7.74 (d, J = 11.0 Hz, 1H), 7.53 (d, J = 8.9 Hz, 1H), 4.49 (dt, J = 14.0, 6.9 Hz, 1H), 4.37 (dt, J = 14.3, 6.2 Hz, 1H), 3.96 (s, 3H), 3.38-3.35 (m, 1H), 3.29 (t, J = 7.2 Hz, 1H), 3.03 (t, J = 6.6 Hz, 2H), 2.87-2.82 (m, 2H), 1.76-1.61 (m, 4H) | Example 729 |
| 909 | 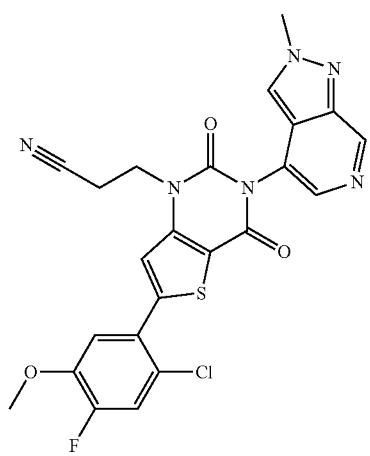 [SMILES: COc1cc(-c2cc3c(s2)c(=O)n(-c2cncc4nn(C)cc24)c(=O)n3CCC#N)c(Cl)cc1F] | 510.8 | 1H NMR (400 MHz, DMSO) δ 9.38 (s, 1H), 8.62 (s, 1H), 8.19 (s, 1H), 7.96 (s, 1H), 7.75 (d, J = 11.0 Hz, 1H), 7.52 (d, J = 8.9 Hz, 1H), 4.45 (t, J = 6.7 Hz, 2H), 4.30 (s, 3H), 3.97 (s, 3H), 3.03 (t, J = 6.6 Hz, 2H). | Example 731 |
| 910 | 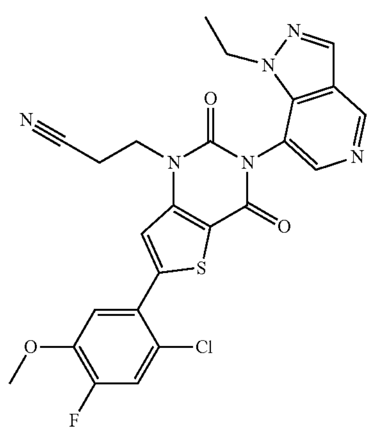 [SMILES: CCn1ncc2cncc(-n3c(=O)c4sc(-c5cc(OC)c(F)cc5Cl)cc4n(CCC#N)c3=O)c21] | 525.8 | 1H NMR (400 MHz, DMSO) δ 9.36 (s, 1H), 8.63 (s, 1H), 8.53 (s, 1H), 8.01 (s, 1H), 7.75 (d, J = 11.0 Hz, 1H), 7.57 (d, J = 8.9 Hz, 1H), 4.55 (dt, J = 13.8, 6.8 Hz, 1H), 4.43 (dt, J = 14.3, 6.2 Hz, 1H), 4.23 (dq, J = 7.1 Hz, 2H), 3.98 (s, 3H), 3.06 (d, J = 6.5 Hz, 2H), 1.28 (t, J = 7.2 Hz, 3H). | Example 732 |

TABLE 44-continued
Examples 902-954
| Example | Structure | ES/MS m/z | 1H-NMR | Changes to Procedure 105: Different Reagents/ Starting Materials |
|---|---|---|---|---|
| 911 | 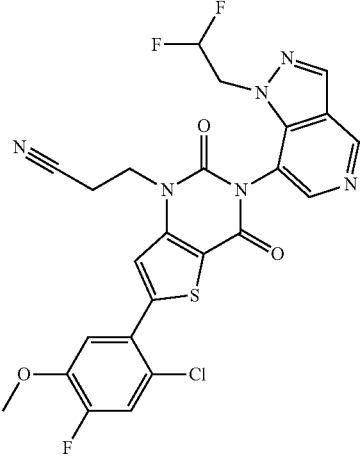 [SMILES: COc1cc(-c2cc3c(s2)c(=O)n(-c2cncc4cnn(CC(F)F)c24)c(=O)n3CCC#N)c(Cl)cc1F] | 560.7 | 1H NMR (400 MHz, DMSO) δ 9.32 (s, 1H), 8.67 (s, 1H), 8.54 (d, J = 4.6 Hz, 1H), 8.01 (s, 1H), 7.75 (d, J = 11.0 Hz, 1H), 7.55 (d, J = 8.9 Hz, 1H), 4.74-4.40 (m, 4H), 3.98 (s, 3H), 3.06-3.00 (m, 2H). | Example 730 |
| 912 | 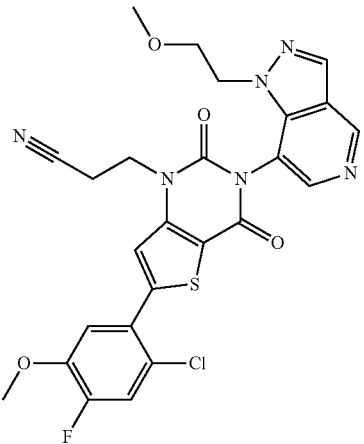 [SMILES: COCCn1ncc2cncc(-n3c(=O)c4sc(-c5cc(OC)c(F)cc5Cl)cc4n(CCC#N)c3=O)c21] | 554.8 | 1H NMR (400 MHz, DMSO) δ 9.31 (s, 1H), 8.60 (s, 1H), 8.48 (s, 1H), 7.99 (s, 1H), 7.75 (d, J = 11.0 Hz, 1H), 7.57 (d, J = 8.9 Hz, 1H), 4.54-4.41 (m, 1H), 4.32 (dq, J = 9.7, 5.0 Hz, 1H), 3.98 (s, 3H), 3.56 (t, J = 5.2 Hz, 2H), 3.08 (d, J = 6.4 Hz, 2H), 3.02 (s, 3H) | Example 733 |
| 913 | 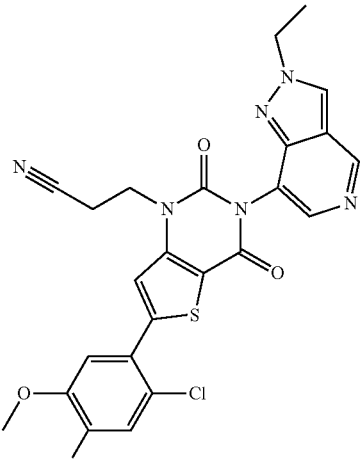 | 524.8 | 1H NMR (400 MHz, DMSO) δ 9.63 (s, 1H), 9.25 (s, 1H), 8.47 (s, 1H), 7.98 (s, 1H), 7.75 (d, J = 11.0 Hz, 1H), 7.55 (d, J = 8.9 Hz, 1H), 4.59 (q, J = 7.3 Hz, 2H), 4.46 (q, J = 6.3 Hz, 2H), 3.97 (s, 3H), 3.02 (d, J = 13.3 Hz, 2H), 1.52 (t, J = 7.3 Hz, 3H). | Example 734 |

TABLE 44-continued

Examples 902-954

| Example | Structure | ES/MS m/z | 1H-NMR | Changes to Procedure 105: Different Reagents/ Starting Materials |
|---|---|---|---|---|
| 914 | 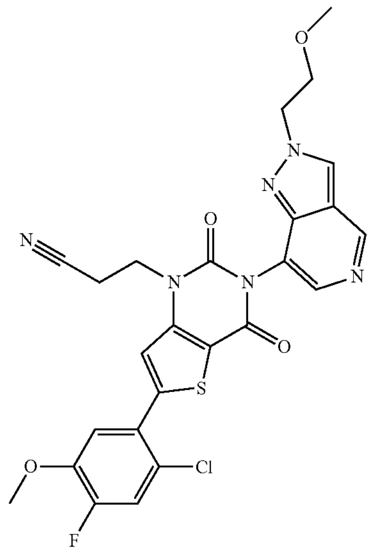 [SMILES: COCCn1cc2cncc(-n3c(=O)c4sc(-c5cc(OC)c(F)cc5Cl)cc4n(CCC#N)c3=O)c2n1] | 554.8 | 1H NMR (400 MHz, DMSO) δ 9.64 (s, 1H), 9.22 (s, 1H), 8.48 (s, 1H), 7.98 (s, 1H), 7.75 (d, J = 11.0 Hz, 1H), 7.55 (d, J = 8.9 Hz, 1H), 4.74 (t, J = 5.1 Hz, 2H), 4.45 (p, J = 7.9, 7.5 Hz, 2H), 3.97 (s, 3H), 3.82 (td, J = 5.3, 4.8, 1.9 Hz, 2H), 3.24 (s, 3H), 3.02 (d, J = 6.8 Hz, 2H). | Example 735 |
| 915 | 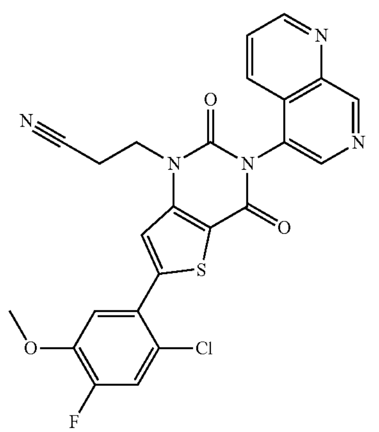 [SMILES: COc1cc(-c2cc3c(s2)c(=O)n(-c2cncc4ncccc24)c(=O)n3CCC#N)c(Cl)cc1F] | 507.8 | 1H NMR (400 MHz, DMSO) δ 9.55 (s, 1H), 9.15 (dd, J = 4.2, 1.6 Hz, 1H), 8.72 (s, 1H), 8.49 (dt, J = 8.6, 1.3 Hz, 1H), 7.99 (s, 1H), 7.82 (dd, J = 8.6, 4.2 Hz, 1H), 7.75 (d, J = 11.1 Hz, 1H), 7.53 (d, J = 8.9 Hz, 1H), 4.46 (q, J = 6.9 Hz, 2H), 3.98 (s, 3H), 3.04 (d, J = 6.6 Hz, 2H). | Example 737 |
| 916 | 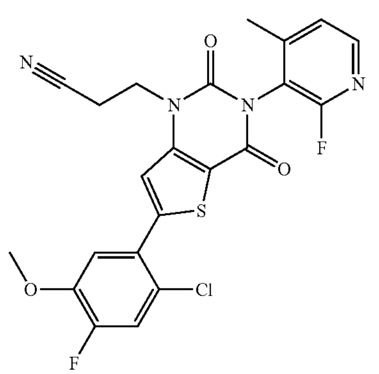 [SMILES: COc1cc(-c2cc3c(s2)c(=O)n(-c2c(C)ccnc2F)c(=O)n3CCC#N)c(Cl)cc1F] | 488.8 | 1H NMR (400 MHz, DMSO-d6) δ 8.24 (d, J = 5.0 Hz, 1H), 7.93 (s, 1H), 7.74 (d, J = 11.0 Hz, 1H), 7.56 (d, J = 8.9 Hz, 1H), 7.47 (d, J = 5.1 Hz, 1H), 4.61-4.36 (m, 2H), 3.96 (s, 3H), 3.07 (td, J = 6.5, 2.5 Hz, 2H), 2.25 (s, 3H). | Example 738 |

TABLE 44-continued

Examples 902-954

| Example | Structure | ES/MS m/z | 1H-NMR | Changes to Procedure 105: Different Reagents/ Starting Materials |
|---|---|---|---|---|
| 917 | 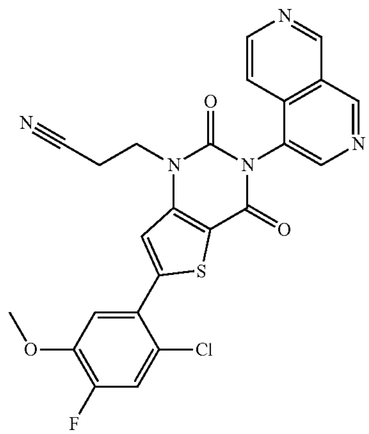 [SMILES: COc1cc(-c2cc3c(s2)c(=O)n(-c2cncc4cnccc24)c(=O)n3CCC#N)c(Cl)cc1F] | 507.7 | 1H NMR (400 MHz, DMSO) δ 9.70 (dd, J = 8.3, 1.0 Hz, 2H), 8.85 (s, 1H), 8.77 (d, J = 6.0 Hz, 1H), 7.99 (s, 1H), 7.91 (dd, J = 6.0, 1.1 Hz, 1H), 7.75 (d, J = 11.0 Hz, 1H), 7.54 (d, J = 8.9 Hz, 1H), 4.46 (q, J = 6.9 Hz, 2H), 3.98 (s, 3H), 3.03 (d, J = 13.2 Hz, 2H). | Example 736 |
| 918 | 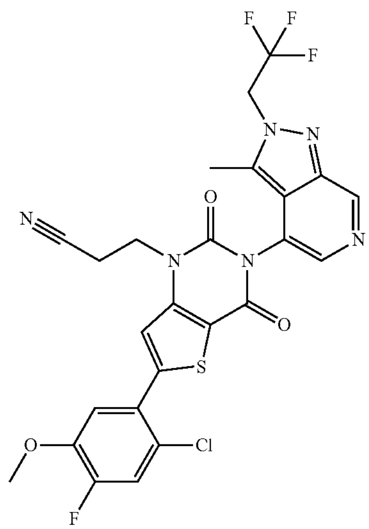 [SMILES: COc1cc(-c2cc3c(s2)c(=O)n(-c2cncc4nn(CC(F)(F)F)c(C)c24)c(=O)n3CCC#N)c(Cl)cc1F] | 592.8 | 1H NMR (400 MHz, DMSO) δ 9.34 (s, 1H), 8.13 (s, 1H), 7.97 (s, 1H), 7.74 (d, J = 11.0 Hz, 1H), 7.57 (d, J = 9.0 Hz, 1H), 5.65 (q, J = 8.9 Hz, 2H), 4.53 (dt, J = 14.0, 6.9 Hz, 1H), 4.40 (dt, J = 14.3, 6.1 Hz, 1H), 3.97 (s, 3H), 3.11-3.04 (m, 2H), 2.49 (s, 3H) | Example 740 |
| 919 | 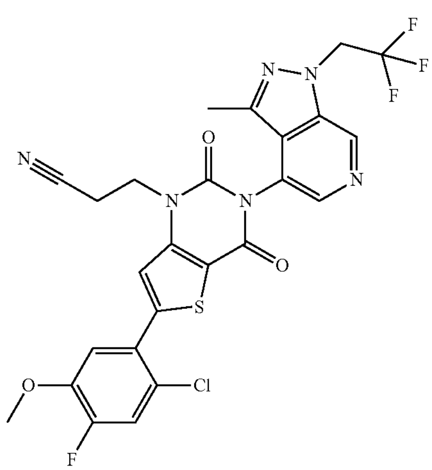 [SMILES: COc1cc(-c2cc3c(s2)c(=O)n(-c2cncc4c2c(C)nn4CC(F)(F)F)c(=O)n3CCC#N)c(Cl)cc1F] | 592.7 | 1H NMR (400 MHz, DMSO) δ 9.34 (s, 1H), 8.33 (s, 1H), 7.97 (s, 1H), 7.74 (d, J = 11.0 Hz, 1H), 7.58 (d, J = 8.9 Hz, 1H), 5.63 (q, J = 9.0 Hz, 2H), 4.55-4.50 (m, 2H), 3.97 (s, 3H), 3.08 (d, J = 13.0 Hz, 2H), 2.32 (s, 3H). | Example 741 |

TABLE 44-continued

Examples 902-954

| Example | Structure | ES/MS m/z | 1H-NMR | Changes to Procedure 105: Different Reagents/ Starting Materials |
|---|---|---|---|---|
| 920 | 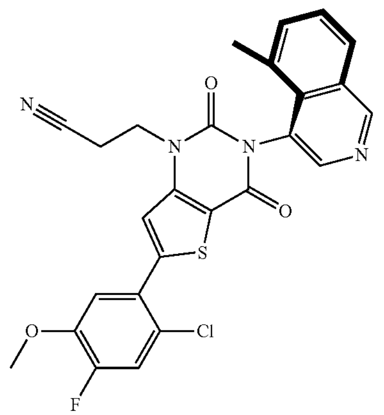 | 520.8 | 1H NMR (400 MHz, DMSO-d6) δ 9.45 (s, 1H), 8.52 (s, 1H), 8.18 (dd, J = 7.1, 2.3 Hz, 1H), 7.98 (s, 1H), 7.74 (d, J = 11.1 Hz, 1H), 7.73-7.62 (m, 2H), 7.59 (d, J = 8.9 Hz, 1H), 4.54 (dt, J = 13.8, 6.7 Hz, 1H), 4.42 (dt, J = 14.3, 6.2 Hz, 1H), 3.98 (s, 3H), 3.08 (t, J = 6.5 Hz, 2H), 2.43 (s, 3H). | Example 995 |
| 921 | 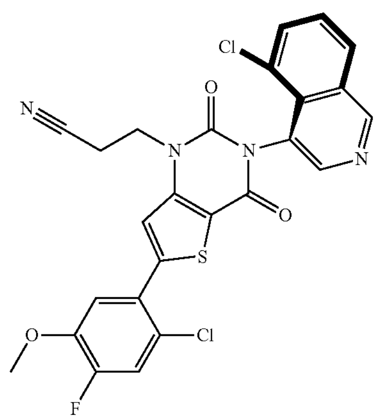 | 541.7 | 1H NMR (400 MHz, DMSO-d6) δ 9.56 (s, 1H), 8.61 (s, 1H), 8.35 (dd, J = 8.3, 1.2 Hz, 1H), 8.02-7.94 (m, 2H), 7.82-7.70 (m, 2H), 7.58 (d, J = 8.9 Hz, 1H), 4.47 (t, J = 6.5 Hz, 2H), 3.98 (s, 3H), 3.12-2.94 (m, 2H). | Example 1074 |
| 922 | 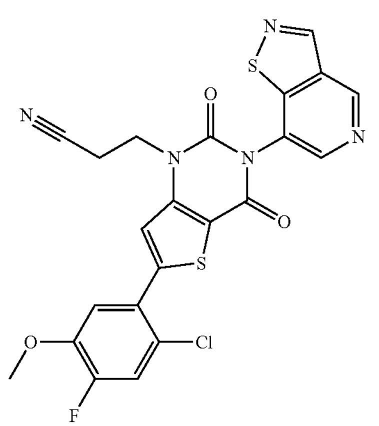 [SMILES: COc1cc(-c2cc3c(s2)c(=O)n(-c2cncc4cnsc24)c(=O)n3CCC#N)c(Cl)cc1F] | 513.7 | 1H NMR (400 MHz, DMSO-d6) δ 8.60 (d, J = 1.1 Hz, 1H), 8.21 (d, J = 1.1 Hz, 1H), 7.90 (s, 1H), 7.71 (d, J = 11.0 Hz, 1H), 7.54 (d, J = 8.9 Hz, 1H), 4.40 (t, J = 6.7 Hz, 2H), 3.95 (s, 3H), 2.94 (q, J = 6.5 Hz, 2H) | I-227 |

TABLE 44-continued

Examples 902-954

| Example | Structure | ES/MS m/z | 1H-NMR | Changes to Procedure 105: Different Reagents/ Starting Materials |
|---|---|---|---|---|
| 923 | 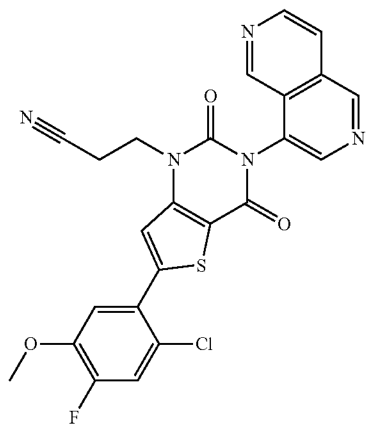 [SMILES: COc1cc(-c2cc3c(s2)c(=O)n(-c2cncc4ccncc24)c(=O)n3CCC#N)c(Cl)cc1F] | 507.7 | 1H NMR (400 MHz, DMSO-d6) δ 9.60 (s, 1H), 9.51 (s, 1H), 8.83 (d, J = 5.7 Hz, 1H), 8.78 (s, 1H), 8.20 (dd, J = 5.7, 1.2 Hz, 1H), 7.98 (s, 1H), 7.74 (d, J = 11.1 Hz, 1H), 7.53 (d, J = 8.7 Hz, 1H), 4.45 (hept, J = 7.1, 6.4 Hz, 2H), 3.97 (s, 3H), 3.03 (t, J = 6.6 Hz, 2H) | Example 739 |
| 924 | 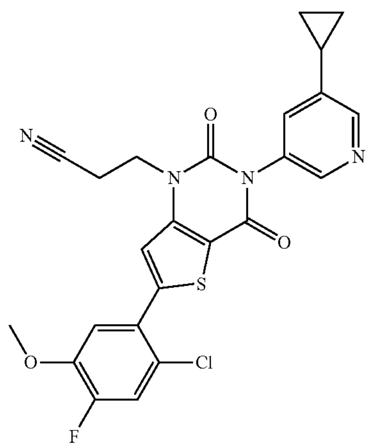 [SMILES: COc1cc(-c2cc3c(s2)c(=O)n(-c2cncc(C4CC4)c2)c(=O)n3CCC#N)c(Cl)cc1F] | 496.8 | 1H NMR (400 MHz, DMSO-d6) δ 8.51 (d, J = 2.1 Hz, 1H), 8.40 (d, J = 2.2 Hz, 1H), 7.92 (s, 1H), 7.72 (d, J = 11.0 Hz, 1H), 7.63 (t, J = 2.2 Hz, 1H), 7.51 (d, J = 8.9 Hz, 1H), 4.41 (t, J = 6.6 Hz, 2H), 3.96 (s, 3H), 2.99 (t, J = 6.5 Hz, 2H), 2.12-2.02 (m, 1H), 1.12-1.03 (m, 2H), 0.82-0.74 (m, 2H). | Example 753 |
| 925 | 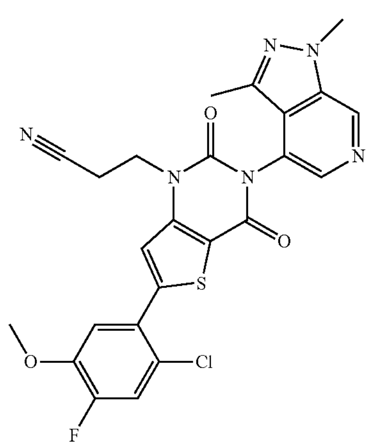 [SMILES: COc1cc(-c2cc3c(s2)c(=O)n(-c2cncc4c2c(C)nn4C)c(=O)n3CCC#N)c(Cl)cc1F] | 524.8 | 1H NMR (400 MHz, DMSO-d6) δ 9.25 (s, 1H), 8.23 (s, 1H), 7.96 (s, 1H), 7.73 (d, J = 11.0 Hz, 1H), 7.57 (d, J = 8.9 Hz, 1H), 4.53 (dt, J = 13.9, 6.8 Hz, 1H), 4.40 (dt, J = 14.4, 6.2 Hz, 1H), 4.17 (s, 3H), 3.97 (s, 3H), 3.07 (t, J = 6.9 Hz, 2H), 2.29 (s, 3H). | Example 752 |

TABLE 44-continued

Examples 902-954

| Example | Structure | ES/MS m/z | 1H-NMR | Changes to Procedure 105: Different Reagents/ Starting Materials |
|---|---|---|---|---|
| 926 | 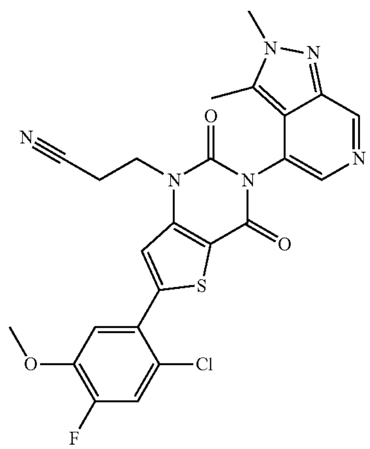 [SMILES: COc1cc(-c2cc3c(s2)c(=O)n(-c2cncc4nn(C)c(C)c24)c(=O)n3CCC#N)c(Cl)cc1F] | 524.8 | 1H NMR (400 MHz, DMSO-d6) δ 9.38 (s, 1H), 8.14 (s, 1H), 7.97 (s, 1H), 7.74 (d, J = 11.0 Hz, 1H), 7.56 (d, J = 8.9 Hz, 1H), 4.52 (dt, J = 13.8, 6.8 Hz, 1H), 4.40 (dt, J = 14.3, 6.2 Hz, 1H), 4.21 (s, 3H), 3.97 (s, 3H), 3.06 (t, J = 6.5 Hz, 2H), 2.43 (s, 3H). | Example 754 |
| 927 | 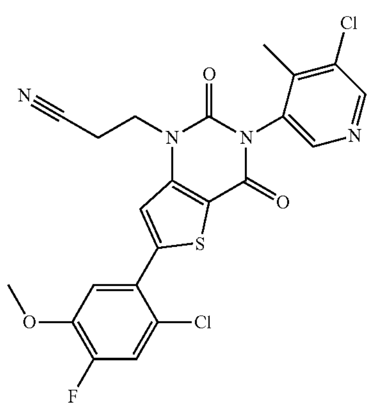 [SMILES: COc1cc(-c2cc3c(s2)c(=O)n(-c2cncc(Cl)c2C)c(=O)n3CCC#N)c(Cl)cc1F] | 504.7 | 1H NMR (400 MHz, DMSO-d6) δ 8.71 (s, 1H), 8.51 (s, 1H), 7.94 (s, 1H), 7.74 (d, J = 11.0 Hz, 1H), 7.53 (d, J = 8.9 Hz, 1H), 4.50 (dt, J = 14.0, 6.9 Hz, 1H), 4.43-4.35 (m, 1H), 3.96 (s, 3H), 3.03 (t, J = 6.6 Hz, 2H), 2.20 (s, 3H). | Example 743 |
| 928 | 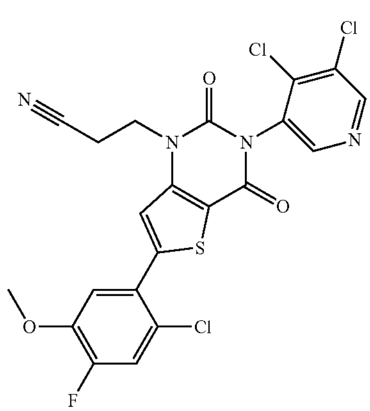 [SMILES: COc1cc(-c2cc3c(s2)c(=O)n(-c2cncc(Cl)c2Cl)c(=O)n3CCC#N)c(Cl)cc1F] | 524.5 | 1H NMR (400 MHz, DMSO-d6) δ 8.96 (s, 1H), 8.75 (s, 1H), 7.96 (s, 1H), 7.74 (d, J = 11.1 Hz, 1H), 7.55 (d, J = 8.9 Hz, 1H), 4.51 (dt, J = 14.2, 6.9 Hz, 1H), 4.47-4.35 (m, 1H), 3.96 (s, 3H), 3.03 (t, J = 6.5 Hz, 2H). | Example 741 |

TABLE 44-continued

Examples 902-954

| Example | Structure | ES/MS m/z | 1H-NMR | Changes to Procedure 105: Different Reagents/ Starting Materials |
|---|---|---|---|---|
| 929 | 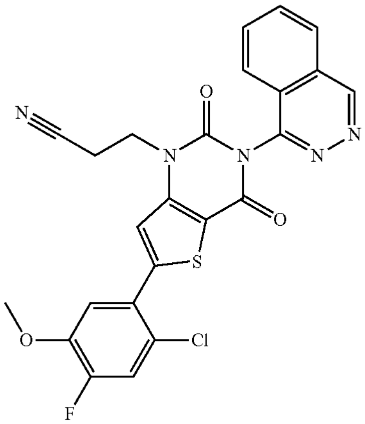 [SMILES: COc1cc(-c2cc3c(s2)c(=O)n(-c2nncc4ccccc24)c(=O)n3CCC#N)c(Cl)cc1F] | 507.8 | 1H NMR (400 MHz, DMSO-d6) δ 9.88 (d, J = 0.9 Hz, 1H), 8.37 (d, J = 8.1 Hz, 1H), 8.26 (d, J = 8.5 Hz, 1H), 8.15 (ddd, J = 8.2, 7.0, 1.2 Hz, 1H), 8.11-7.99 (m, 2H), 7.76 (d, J = 11.1 Hz, 1H), 7.57 (d, J = 8.9 Hz, 1H), 4.47 (t, J = 6.6 Hz, 2H), 3.99 (s, 3H), 3.11-3.02 (m, 2H). | Example 744 |
| 930 | 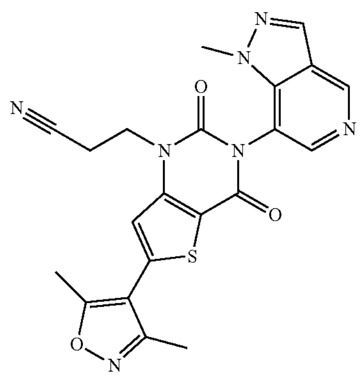 [SMILES: Cc1noc(C)c1-c1cc2c(s1)c(=O)n(-c1cncc3cnn(C)c13)c(=O)n2CCC#N] | 447.8 | 1H NMR (400 MHz, DMSO-d6) δ 9.25 (s, 1H), 8.49 (s, 1H), 8.43 (s, 1H), 7.74 (s, 1H), 4.54 (dt, J = 13.6, 6.8 Hz, 1H), 4.49-4.37 (m, 1H), 3.91 (s, 3H), 3.05 (t, J = 6.4 Hz, 2H), 2.66 (s, 3H), 2.46 (s, 3H). | Example 805 |
| 931 | 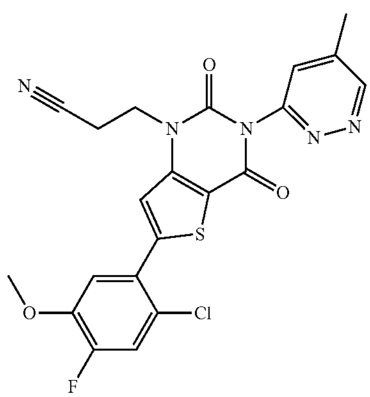 [SMILES: COc1cc(-c2cc3c(s2)c(=O)n(-c2cc(C)cnn2)c(=O)n3CCC#N)c(Cl)cc1F] | 471.0 | 1H NMR (400 MHz, DMSO-d6) δ 12.34 (s, 1H), 9.23 (d, J = 2.0 Hz, 1H), 7.78 (dd, J = 2.0, 1.0 Hz, 1H), 7.71 (d, J = 11.0 Hz, 1H), 7.47 (d, J = 8.9 Hz, 1H), 7.29 (s, 1H), 3.95 (s, 3H), 2.44 (s, 3H).; 1H NMR (400 MHz, DMSO-d6) δ 9.26 (d, J = 2.1 Hz, 1H), 7.96 (d, J = 1.9 Hz, 1H), 7.76 (t, J = 2.5 Hz, 1H), 7.73 (d, J = 1.6 Hz, 1H), 7.58-7.52 (m, 1H), 4.43 (m, 2H), 3.99-3.95 (m, 3H), 3.01 (m, 2H), 2.45 (s, 3H). | Example 746 |

TABLE 44-continued

Examples 902-954

| Example | Structure | ES/MS m/z | 1H-NMR | Changes to Procedure 105: Different Reagents/ Starting Materials |
|---|---|---|---|---|
| 932 | 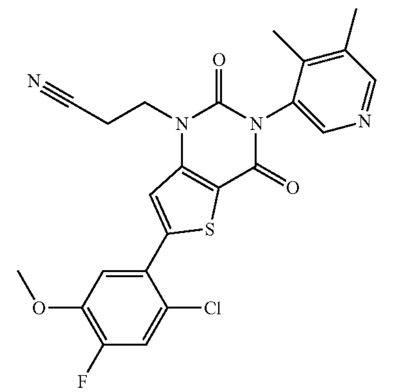 [SMILES: COc1cc(-c2cc3c(s2)c(=O)n(-c2cncc(C)c2C)c(=O)n3CCC#N)c(Cl)cc1F] | 484.8 | 1H NMR (400 MHz, DMSO-d6) δ 8.59 (d, J = 12.4 Hz, 2H), 7.94 (d, J = 4.4 Hz, 1H), 7.74 (d, J = 11.1 Hz, 1H), 7.53 (t, J = 7.0 Hz, 1H), 4.51 (dt, J = 14.2, 7.0 Hz, 1H), 4.39 (dt, J = 14.6, 6.2 Hz, 1H), 3.97 (s, 3H), 3.04 (t, J = 6.5 Hz, 2H), 2.41 (s, 3H), 2.16 (s, 3H). | Example 747 |
| 933 | 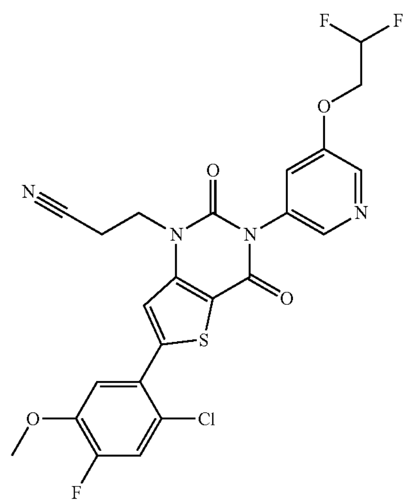 [SMILES: COc1cc(-c2cc3c(s2)c(=O)n(-c2cncc(OCC(F)F)c2)c(=O)n3CCC#N)c(Cl)cc1F] | 504.7 | 1H NMR (400 MHz, DMSO-d6) δ 8.48 (d, J = 2.7 Hz, 1H), 8.27 (d, J = 1.8 Hz, 1H), 7.94 (s, 1H), 7.73 (d, J = 11.0 Hz, 1H), 7.65 (dd, J = 2.7, 1.9 Hz, 1H), 7.52 (d, J = 8.9 Hz, 1H), 6.44 (tt, J = 54.3, 3.4 Hz, 1H), 4.54-4.38 (m, 4H), 3.97 (s, 3H), 3.00 (t, J = 6.5 Hz, 2H). | I-251 |
| 934 | 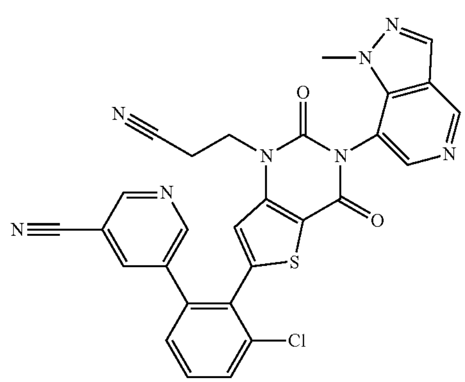 [SMILES: Cn1ncc2cncc(-n3c(=O)c4sc(-c5c(Cl)cccc5-c5cncc(C#N)c5)cc4n(CCC#N)c3=O)c21] | 564.7 | 1H NMR (400 MHz, DMSO) δ 9.36 (s, 1H), 8.98 (d, J = 1.9 Hz, 1H), 8.78 (d, J = 2.2 Hz, 1H), 8.59 (s, 1H), 8.54 (s, 1H), 8.30 (t, J = 2.1 Hz, 1H), 7.86 (dd, J = 8.1, 1.2 Hz, 1H), 7.74 (t, J = 7.9 Hz, 1H), 7.69 (s, 1H), 7.63 (dd, J = 7.7, 1.3 Hz, 1H), 4.41 (ddd, J = 14.0, 7.5, 6.2 Hz, 1H), 4.26 (dt, J = 14.4, 6.1 Hz, 1H), 3.89 (s, 3H), 2.95 (dt, J = 17.1, 6.0 Hz, 1H), 2.83 (dt, | Example 677 |

TABLE 44-continued

Examples 902-954

| Example | Structure | ES/MS m/z | 1H-NMR | Changes to Procedure 105: Different Reagents/ Starting Materials |
|---|---|---|---|---|
| | | | J = 17.2, 7.0 Hz, 1H). | |
| 935 | 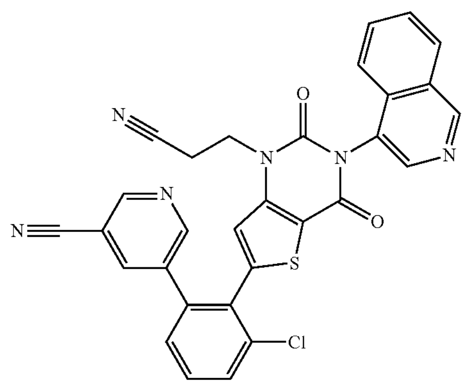 [SMILES: N#CCCn1c(=O)n(-c2cncc3ccccc23)c(=O)c2sc(-c3c(Cl)cccc3-c3cncc(C#N)c3)cc21] | 560.7 | 1H NMR (400 MHz, DMSO) δ 9.46 (s, 1H), 9.00 (d, J = 2.0 Hz, 1H), 8.78 (d, J = 2.2 Hz, 1H), 8.58 (s, 1H), 8.37 (t, J = 2.1 Hz, 1H), 8.29 (dd, J = 7.0, 1.9 Hz, 1H), 7.88-7.67 (m, 6H), 7.61 (dd, J = 7.7, 1.3 Hz, 1H), 4.31 (qt, J = 13.9, 6.6 Hz, 2H), 2.96-2.80 (m, 2H). | Example 673 |
| 936 | 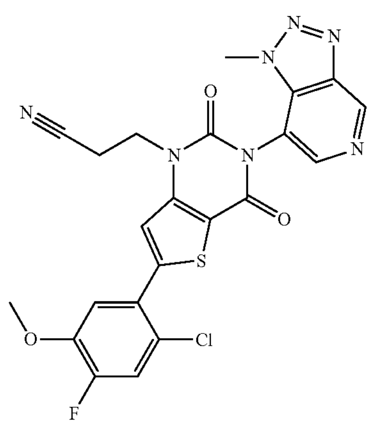 [SMILES: COc1cc(-c2cc3c(s2)c(=O)n(-c2cncc4nnn(C)c24)c(=O)n3CCC#N)c(Cl)cc1F] | 511.8 | 1H NMR (400 MHz, DMSO) δ 9.60 (s, 1H), 8.64 (s, 1H), 7.99 (s, 1H), 7.75 (d, J = 11.0 Hz, 1H), 7.55 (d, J = 8.9 Hz, 1H), 4.60-4.38 (m, 2H), 4.20 (s, 3H), 3.98 (s, 3H), 3.08 (t, J = 6.6 Hz, 2H). | Example 749 |
| 937 | 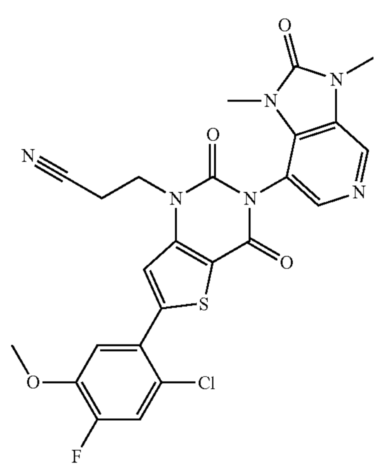 | 540.8 | 1H NMR (400 MHz, DMSO) δ 8.66 (s, 1H), 8.44 (s, 1H), 7.97 (s, 1H), 7.75 (d, J = 11.0 Hz, 1H), 7.55 (d, J = 8.9 Hz, 1H), 4.54 (dt, J = 14.1, 7.0 Hz, 1H), 4.40 (dt, J = 14.4, 6.0 Hz, 1H), 3.97 (s, 3H), 3.48 (s, 3H), 3.25 (s, 3H), 3.11-3.03 (m, 2H). | Example 750 |

TABLE 44-continued

Examples 902-954

| Example | Structure | ES/MS m/z | 1H-NMR | Changes to Procedure 105: Different Reagents/ Starting Materials |
|---|---|---|---|---|
| 938 | 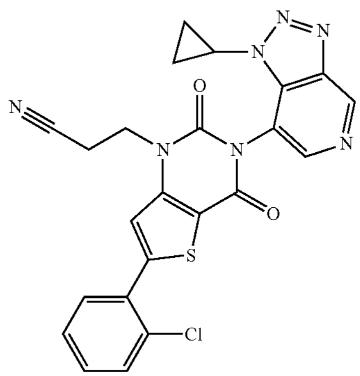 [SMILES: N#CCCn1c(=O)n(-c2cncc3nnn(C4CC4)c23)c(=O)c2sc(-c3ccccc3Cl)cc21] | 489.7 | 1H NMR (400 MHz, DMSO) δ 9.60 (s, 1H), 8.65 (s, 1H), 8.08 (s, 1H), 7.97-7.87 (m, 1H), 7.77-7.67 (m, 1H), 7.63-7.52 (m, 2H), 4.59-4.39 (m, 2H), 3.79 (tt, J = 7.1, 3.5 Hz, 1H), 3.08 (t, J = 6.6 Hz, 2H), 1.43-0.82 (m, 4H). | I-301 |
| 939 | 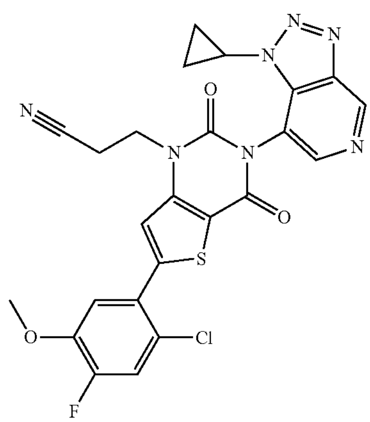 [SMILES: COc1cc(-c2cc3c(s2)c(=O)n(-c2cncc4nnn(C5CC5)c24)c(=O)n3CCC#N)c(Cl)cc1F] | 537.7 | 1H NMR (400 MHz, DMSO) δ 9.60 (s, 1H), 8.65 (s, 1H), 8.02 (s, 1H), 7.75 (d, J = 11.0 Hz, 1H), 7.57 (d, J = 8.9 Hz, 1H), 4.61-4.39 (m, 2H), 3.98 (s, 3H), 3.79 (tt, J = 7.1, 3.5 Hz, 1H), 3.10 (t, J = 6.5 Hz, 2H), 1.33-1.21 (m, 2H), 1.04 (dddd, J = 13.7, 11.2, 6.7, 3.7 Hz, 2H). | I-302 |
| 940 | 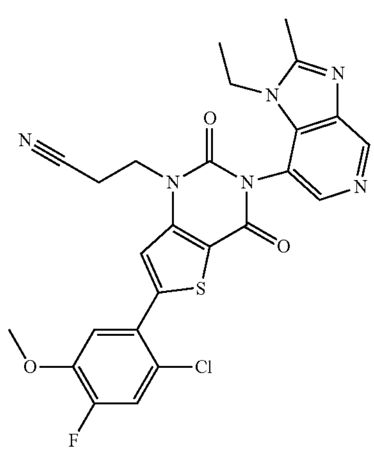 [SMILES: CCn1c(C)nc2cncc(-n3c(=O)c4sc(-c5cc(OC)c(F)cc5Cl)cc4n(CCC#N)c3=O)c21] | 538.8 | 1H NMR (400 MHz, DMSO) δ 9.27 (s, 1H), 8.63 (s, 1H), 8.03 (s, 1H), 7.76 (d, J = 11.1 Hz, 1H), 7.56 (d, J = 8.9 Hz, 1H), 4.55 (dt, J = 13.8, 6.8 Hz, 1H), 4.43 (dt, J = 14.5, 6.2 Hz, 1H), 4.21-4.00 (m, 2H), 3.98 (s, 3H), 3.06 (t, J = 6.5 Hz, 2H), 2.70 (s, 3H), 1.18 (t, J = 7.2 Hz, 3H). | I-288 |

TABLE 44-continued

Examples 902-954

| Example | Structure | ES/MS m/z | 1H-NMR | Changes to Procedure 105: Different Reagents/ Starting Materials |
|---|---|---|---|---|
| 941 | 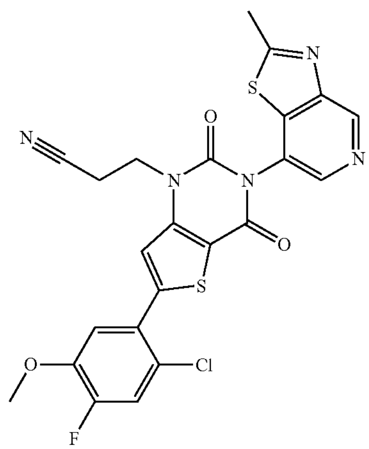 [SMILES: COc1cc(-c2cc3c(s2)c(=O)n(-c2cncc4nc(C)sc24)c(=O)n3CCC#N)c(Cl)cc1F] | 527.7 | 1H NMR (400 MHz, DMSO-d6) δ 9.27 (s, 1H), 8.59 (s, 1H), 7.96 (s, 1H), 7.74 (d, J = 11.0 Hz, 1H), 7.54 (d, J = 8.9 Hz, 1H), 4.63-4.29 (m, 2H), 3.97 (s, 3H), 3.03 (t, J = 6.6 Hz, 2H), 2.88 (s, 3H). | Example 652 |
| 942 | 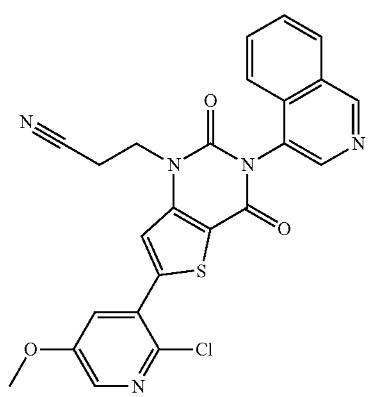 [SMILES: COc1cnc(Cl)c(-c2cc3c(s2)c(=O)n(-c2cncc4ccccc24)c(=O)n3CCC#N)c1] | 490.1 | 1H NMR (400 MHz, DMSO-d6) δ 9.48 (s, 1H), 8.59 (s, 1H), 8.33 (d, J = 2.9 Hz, 1H), 8.30 (dd, J = 7.1, 2.2 Hz, 1H), 8.13 (s, 1H), 7.94 (d, J = 3.0 Hz, 1H), 7.93-7.88 (m, 1H), 7.83-7.76 (m, 2H), 4.55-4.34 (m, 2H), 3.98 (s, 3H), 3.04 (t, J = 6.7 Hz, 2H). | Example 364 |
| 943 | 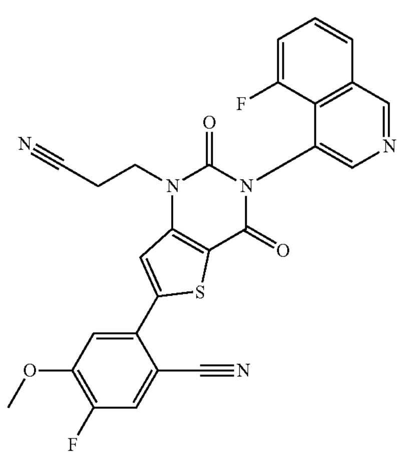 [SMILES: COc1cc(-c2cc3c(s2)c(=O)n(-c2cncc4cccc(F)c24)c(=O)n3CCC#N)c(C#N)cc1F] | 516.2 | 1H NMR (400 MHz, DMSO-d6) δ 9.55 (d, J = 2.5 Hz, 1H), 8.61 (s, 1H), 8.19 (dd, J = 8.3, 1.0 Hz, 1H), 8.14 (d, J = 11.1 Hz, 1H), 8.09 (s, 1H), 7.82-7.76 (m, 1H), 7.69-7.60 (m, 2H), 4.54-4.39 (m, 2H), 4.06 (s, 3H), 3.04-2.99 (m, 2H). | Example 762 |

TABLE 44-continued

Examples 902-954

| Example | Structure | ES/MS m/z | 1H-NMR | Changes to Procedure 105: Different Reagents/ Starting Materials |
|---|---|---|---|---|
| 944 | 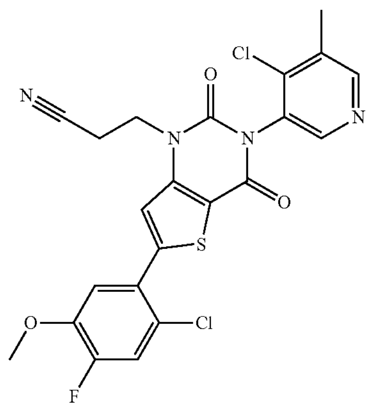 [SMILES: COc1cc(-c2cc3c(s2)c(=O)n(-c2cncc(C)c2Cl)c(=O)n3CCC#N)c(Cl)cc1F] | 505.1 | 1H NMR (400 MHz, DMSO-d6) δ 8.65 (s, 1H), 8.55 (s, 1H), 7.94 (s, 1H), 7.74 (d, J = 11.1 Hz, 1H), 7.55 (d, J = 8.9 Hz, 1H), 4.55-4.35 (m, 2H), 3.96 (s, 3H), 3.02 (t, J = 6.6 Hz, 2H), 2.43 (s, 3H). | Example 1080 |
| 945 | 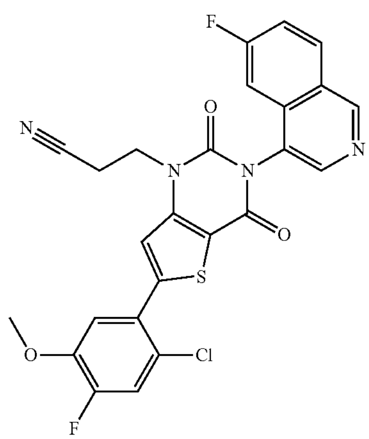 [SMILES: COc1cc(-c2cc3c(s2)c(=O)n(-c2cncc4ccc(F)cc24)c(=O)n3CCC#N)c(Cl)cc1F] | 525.2 | 1H NMR (400 MHz, DMSO-d6) δ 9.48 (d, J = 4.8 Hz, 1H), 8.60 (d, J = 4.7 Hz, 1H), 8.43 (dd, J = 9.3, 5.1 Hz, 1H), 7.97 (d, J = 4.6 Hz, 1H), 7.92-7.81 (m, 1H), 7.79-7.64 (m, 2H), 7.53 (dd, J = 9.0, 4.5 Hz, 1H), 4.49-4.40 (m, 2H), 3.98 (s, 3H), 3.05-2.98 (m, 2H). | Example 763 |
| 946 | 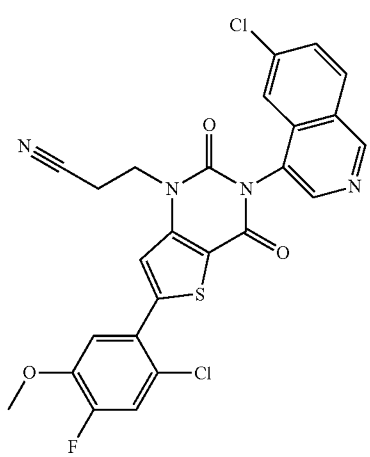 [SMILES: COc1cc(-c2cc3c(s2)c(=O)n(-c2cncc4ccc(Cl)cc24)c(=O)n3CCC#N)c(Cl)cc1F] | 540.7 | 1H NMR (400 MHz, DMSO) δ 9.49 (d, J = 0.9 Hz, 1H), 8.62 (s, 1H), 8.35 (d, J = 8.8 Hz, 1H), 8.21 (d, J = 2.0 Hz, 1H), 7.98 (s, 1H), 7.80 (dd, J = 8.8, 2.0 Hz, 1H), 7.75 (d, J = 11.0 Hz, 1H), 7.53 (d, J = 8.8 Hz, 1H), 4.45 (td, J = 6.8, 3.7 Hz, 2H), 3.98 (s, 3H), 3.03 (t, J = 6.6 Hz, 2H). | I-305 |

TABLE 44-continued

Examples 902-954

| Example | Structure | ES/MS m/z | 1H-NMR | Changes to Procedure 105: Different Reagents/ Starting Materials |
|---|---|---|---|---|
| 947 | 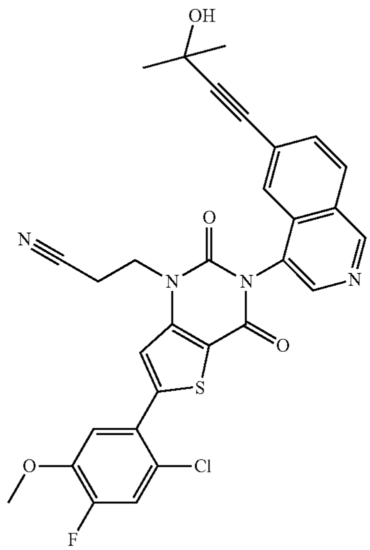 [SMILES: COc1cc(-c2cc3c(s2)c(=O)n(-c2cncc4ccc(C#CC(C)(C)O)cc24)c(=O)n3CCC#N)c(Cl)cc1F] | 588.8 | 1H NMR (400 MHz, DMSO) δ 9.45 (d, J = 0.9 Hz, 1H), 8.59 (s, 1H), 8.28 (d, J = 8.5 Hz, 1H), 8.01-7.96 (m, 2H), 7.75 (d, J = 11.0 Hz, 1H), 7.70 (dd, J = 8.5, 1.5 Hz, 1H), 7.54 (d, J = 8.9 Hz, 1H), 4.52-4.40 (m, 2H), 3.98 (s, 3H), 3.04 (t, J = 6.6 Hz, 2H), 1.47 (s, 6H). | I-303 |
| 948 | 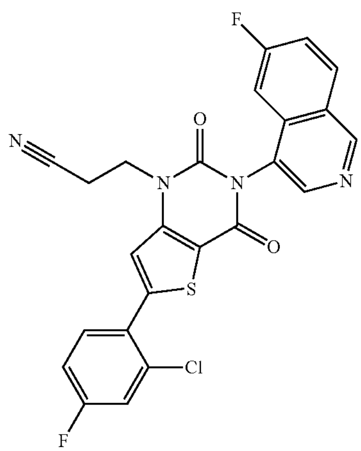 [SMILES: N#CCCn1c(=O)n(-c2cncc3ccc(F)cc23)c(=O)c2sc(-c3ccc(F)cc3Cl)cc21] | 494.7 | 1H NMR (400 MHz, DMSO) δ 9.48 (s, 1H), 8.60 (s, 1H), 8.42 (dd, J = 9.1, 5.6 Hz, 1H), 7.99 (s, 1H), 7.97-7.87 (m, 2H), 7.79-7.63 (m, 2H), 7.50 (td, J = 8.4, 2.7 Hz, 1H), 4.44 (hept, J = 7.3 Hz, 2H), 3.01 (t, J = 6.7 Hz, 2H). | I-310 |
| 949 | 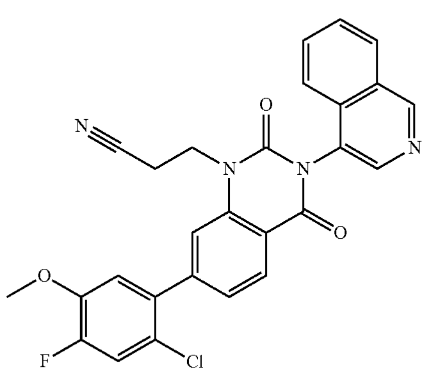 [SMILES: COc1cc(-c2ccc3c(=O)n(-c4cncc5ccccc45)c(=O)n(CCC#N)c3c2)c(Cl)cc1F] | 500.8 | 1H NMR (400 MHz, DMSO) δ 9.50 (s, 1H), 8.60 (s, 1H), 8.36-8.28 (m, 1H), 8.18 (d, J = 8.1 Hz, 1H), 8.00-7.94 (m, 1H), 7.88 (d, J = 1.4 Hz, 1H), 7.86-7.75 (m, 2H), 7.69 (d, J = 11.1 Hz, 1H), 7.49 (dd, J = 8.1, 1.3 Hz, 1H), 7.36 (d, J = 9.1 Hz, 1H), 4.61-4.47 (m, 2H), 3.94 (s, 3H), 3.06-2.96 (m, 2H). | Example 299 |

TABLE 44-continued

Examples 902-954

| Example | Structure | ES/MS m/z | 1H-NMR | Changes to Procedure 105: Different Reagents/ Starting Materials |
|---|---|---|---|---|
| 950 | 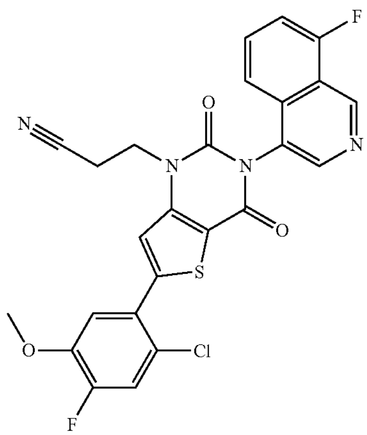 [SMILES: COc1cc(-c2cc3c(s2)c(=O)n(-c2cncc4c(F)cccc24)c(=O)n3CCC#N)c(Cl)cc1F] | 525.3 | 1H NMR (400 MHz, DMSO-d6) δ 9.60 (s, 1H), 8.71 (s, 1H), 7.98 (s, 1H), 7.85-7.77 (m, 2H), 7.75 (d, J = 11.1 Hz, 1H), 7.63-7.56 (m, 1H), 7.54 (d, J = 8.8 Hz, 1H), 4.55-4.38 (m, 2H), 3.98 (s, 3H), 3.04 (t, J = 6.6 Hz, 2H). | Example 1081 |
| 951 | 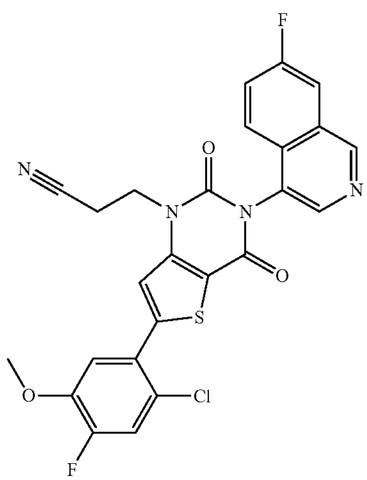 [SMILES: COc1cc(-c2cc3c(s2)c(=O)n(-c2cncc4cc(F)ccc24)c(=O)n3CCC#N)c(Cl)cc1F] | 525.3 | 1H NMR (400 MHz, DMSO-d6) δ 9.45 (s, 1H), 8.57 (s, 1H), 8.12 (dd, J = 9.3, 2.6 Hz, 1H), 8.08 (dd, J = 9.3, 5.2 Hz, 1H), 7.98 (s, 1H), 7.78-7.74 (m, 1H), 7.73 (q, J = 2.8 Hz, 1H), 7.53 (d, J = 8.9 Hz, 1H), 4.52-4.39 (m, 2H), 3.98 (s, 3H), 3.03 (t, J = 6.6 Hz, 2H). | I-340 |
| 952 | 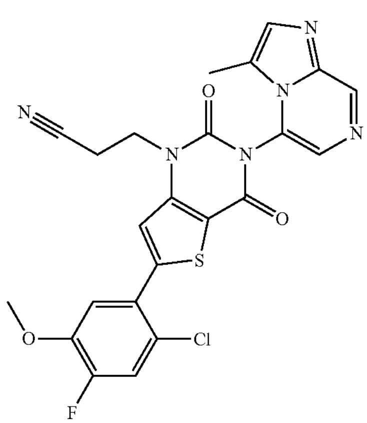 [SMILES: COc1cc(-c2cc3c(s2)c(=O)n(-c2cncc4ncc(C)n24)c(=O)n3CCC#N)c(Cl)cc1F] | 511.2 | 1H NMR (400 MHz, DMSO-d6) δ 9.16 (s, 1H), 8.09 (s, 1H), 8.00 (s, 1H), 7.79-7.70 (m, 2H), 7.58 (d, J = 8.9 Hz, 1H), 4.56 (dt, J = 14.1, 6.9 Hz, 1H), 4.41 (dt, J = 14.4, 6.0 Hz, 1H), 3.97 (s, 3H), 3.15-3.02 (m, 2H), 2.35 (s, 3H). | Example 1082 |

TABLE 44-continued

Examples 902-954

| Example | Structure | ES/MS m/z | 1H-NMR | Changes to Procedure 105: Different Reagents/ Starting Materials |
|---|---|---|---|---|
| 953 | 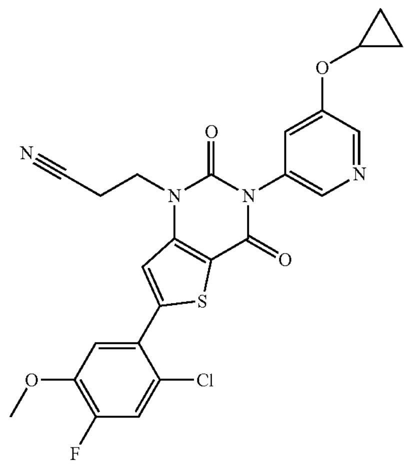 [SMILES: COc1cc(-c2cc3c(s2)c(=O)n(-c2cncc(OC4CC4)c2)c(=O)n3CCC#N)c(Cl)cc1F] | 512.8 | 1H NMR (400 MHz, DMSO-d6) δ 8.48 (d, J = 2.8 Hz, 1H), 8.22 (d, J = 2.1 Hz, 1H), 7.93 (s, 1H), 7.73 (d, J = 11.1 Hz, 1H), 7.64 (d, J = 2.5 Hz, 1H), 7.52 (d, J = 8.9 Hz, 1H), 4.47-4.37 (m, 2H), 3.96 (m, 4H), 3.00 (t, J = 6.5 Hz, 2H), 0.83 (t, J = 5.9 Hz, 2H), 0.74 (s, 2H). | I-349 |
| 954 | 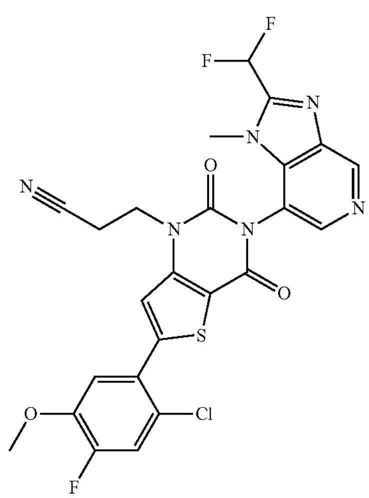 [SMILES: COc1cc(-c2cc3c(s2)c(=O)n(-c2cncc4nc(C(F)F)n(C)c24)c(=O)n3CCC#N)c(Cl)cc1F] | 560.7 | 1H NMR (400 MHz, DMSO-d6) δ 9.25 (s, 1H), 8.53 (s, 1H), 7.98 (s, 1H), 7.74 (d, J = 11.0 Hz, 1H), 7.67-7.37 (m, 2H), 4.61-4.35 (m, 2H), 3.97 (s, 3H), 3.79 (s, 3H), 3.08 (t, J = 6.6 Hz, 2H) | I-343 |

Example 927

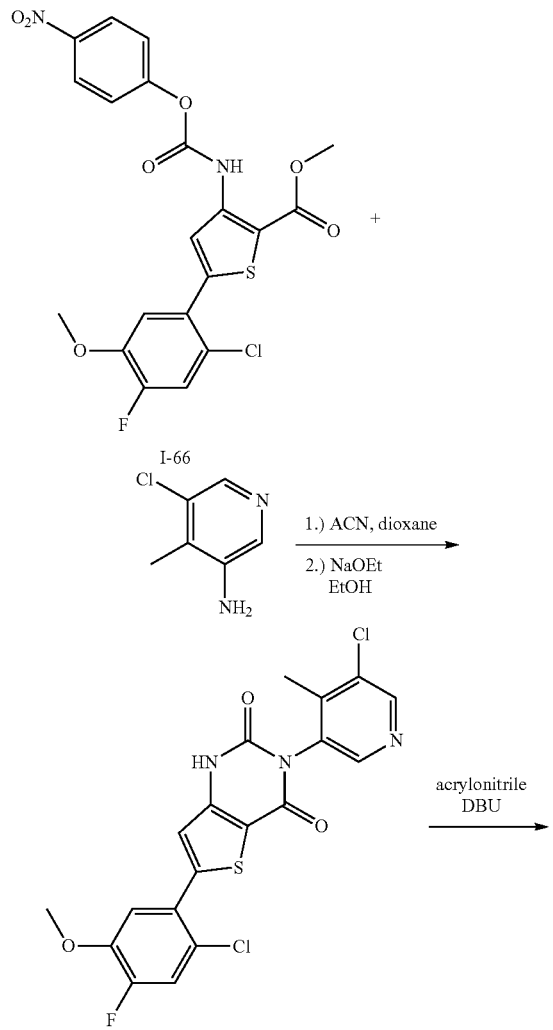

6-(2-chloro-4-fluoro-5-methyl-phenyl)-3-(5-chloro-4-methyl-3-pyridyl)-1H-thieno[3,2-d]pyrimidine-2,4-dione (Example 743): To a suspension of methyl 5-(2-chloro-4-fluoro-5-methoxy-phenyl)-3-1(4-nitrophenoxy)carbonylaminolthiophene-2-carboxylate (1466) (830 mg, 1.73 mmol) in dioxane (10 mL) was added 5-chloro-4-methyl-pyridin-3-amine (295 mg, 2.07 mmol). The reaction mixture was stirred at 80° C. overnight. The reaction was subsequently cooled to 0° C. A precipitate formed, and the precipitate was isolated by filtration. The precipitate was suspended in EtOH (10 mL), and to the mixture was added sodium ethoxide (21% w-t, in EtOH; 0.82 mL) at room temperature dropwise, and the reaction was stirred for 2 hours at room temperature. Approximately half of the solvent was removed under reduced pressure, and HCl (1N, 5 mL) was added. The mixture was let stand at 0° C., whereupon a precipitate formed. The solid was collected via filtration and dried over air to deliver the product as an HCl salt.

ES/MS: 451.7 [M$^+$].

3-[6-(2-chloro-4-fluoro-5-methoxy-phenyl)-3-(5-chloro-4-methyl-3-pyridyl)-2,4-dioxo-thieno[3,2-d]pyrimidin-1-yl]propanenitrile (Example 927): To a 100 mL RBF with 6-(2-chloro-4-fluoro-5-methoxy-phenyl)-3-(5-chloro-4-methyl-3-pyridyl)-1H-thieno[3,2-d]pyrimidine-2,4-dione (Example 743) (HCl salt) (769 mg, 1.70 mmol) in DMF (17 mL) was added DBU (0.76 mL, 5.10 mmol) and 3-bromopropionitrile (10 mL, 153 mmol). The reaction mixture was heated at 80° C. for 16 hours, after which the mixture was cooled to room temperature. The mixture was concentrated under reduced pressure, and the crude material was dissolved in acetone and dry-loaded onto silica. The material was purified by silica chromatography (eluent: EtOAc in hexanes) to provide the product.

ES/MS: 504.7 (M$^+$).

1H NMR (400 MHz, DMSO-d$_6$) δ 8.71 (s, 1H), 8.51 (s, 1H), 7.94 (s, 1H), 7.74 (d, J=11.0 Hz, 1H), 7.53 (d, J=8.9 Hz, 1H), 4.50 (dt, J=14.0, 6.9 Hz, 1H), 4.43-4.35 (m, 1H), 3.96 (s, 3H), 3.03 (t, J=6.6 Hz, 2H), 2.20 (s, 3H).

Procedure 106: Example 955 and Example 956

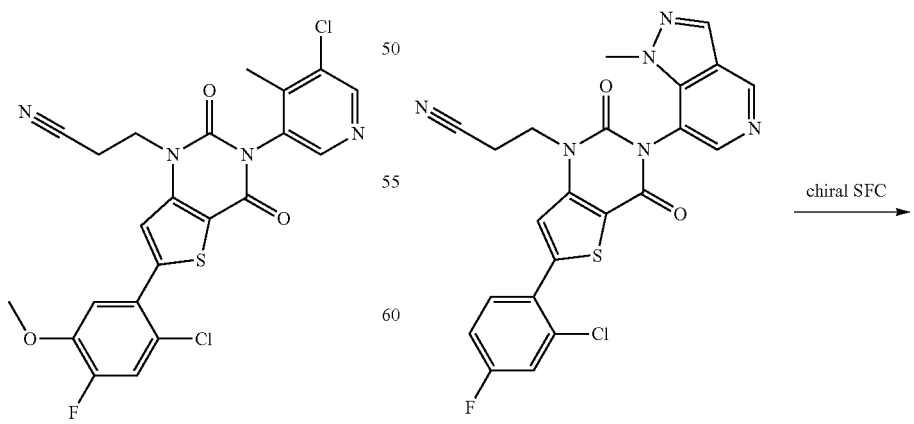

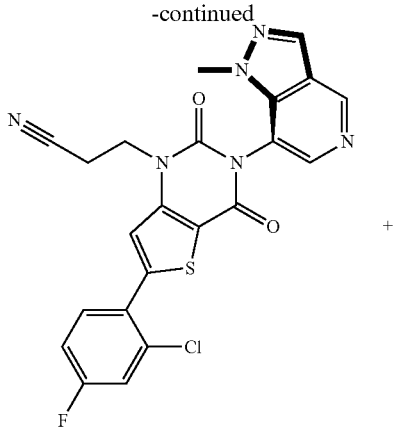

Isomer 1
Example 955

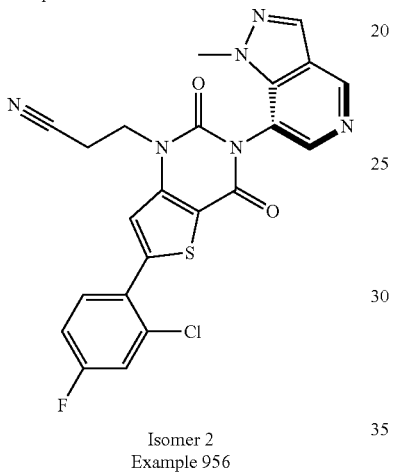

Isomer 2
Example 956

3-(6-(2-chloro-4-fluorophenyl)-3-(1-methyl-1H-pyrazolo[4,3-c]pyridin-7-yl)-2,4-dioxo-3,4-dihydrothieno[3,2-d]pyrimidin-1(2H)-yl)propanenitrile (Example 955 and Example 956): 3-(6-(2-chloro-4-fluorophenyl)-3-(1-methyl-1H-pyrazolo[4,3-c]pyridin-7-yl)-2,4-dioxo-3,4-dihydrothieno[3,2-d]pyrimidin-1(2H)-yl)propanenitrile (Example 769) as a mixture of 2 isomers was separated by chiral SFC (IB 5 um-21×250 mm column with 30% EtOH cosolvent) to give two enantiomers, which were assigned as Isomer 1 and Isomer 2. The stereochemistry was assigned by analogy to Example 438, with Example 955 being the more active isomer.

Isomer 1:

3-(6-(2-chloro-4-fluorophenyl)-3-(1-methyl-1H-pyrazolo[4,3-c]pyridin-7-yl)-2,4-dioxo-3,4-dihydrothieno[3,2-d]pyrimidin-1(2H)-yl)propanenitrile (Example 955)

ES/MS: 480.8 (M$^+$).

1H NMR (400 MHz, DMSO-d6) δ 9.34 (d, J=1.9 Hz, 1H), 8.57 (d, J=1.9 Hz, 1H), 8.51 (d, J=1.9 Hz, 1H), 8.02 (d, J=1.9 Hz, 1H), 7.96 (ddd, J=8.3, 6.0, 1.9 Hz, 1H), 7.76 (dt, J=8.8, 2.4 Hz, 1H), 7.50 (tt, J=8.4, 2.3 Hz, 1H), 4.61-4.35 (m, 2H), 3.94 (d, J=1.9 Hz, 3H), 3.12-3.02 (m, 2H).

Isomer 2:

3-(6-(2-chloro-4-fluorophenyl)-3-(1-methyl-1H-pyrazolo[4,3-c]pyridin-7-yl)-2,4-dioxo-3,4-dihydrothieno[3,2-d]pyrimidin-1(2H)-yl)propanenitrile (Example 956)

ES/MS: 480.8 (M$^+$).

1H NMR (400 MHz, DMSO-d6) δ 9.32 (s, 1H), 8.56 (s, 1H), 8.49 (s, 1H), 8.02 (s, 1H), 7.96 (dd, J=8.8, 6.1 Hz, 1H), 7.76 (dd, J=8.8, 2.7 Hz, 1H), 7.50 (td, J=8.4, 2.6 Hz, 1H), 4.59-4.36 (m, 2H), 3.93 (s, 3H), 3.07 (t, J=6.6 Hz, 2H).

Procedure 107: Example 957 and Example 958

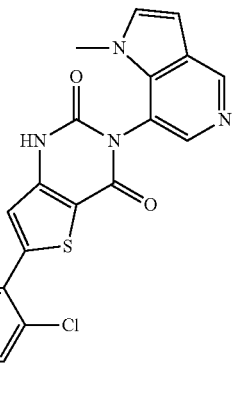

Example 454 chiral SFC ⟶

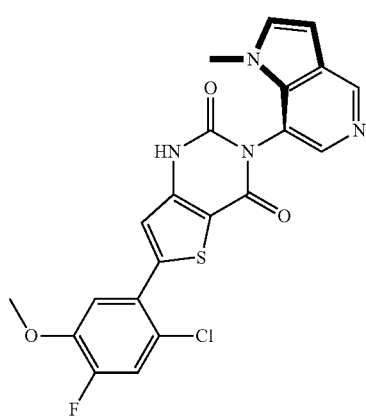

Isomer 1
Example 957

1359 -continued

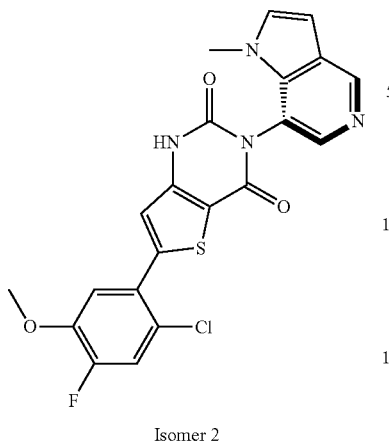

Isomer 2
Example 958

6-(2-chloro-4-fluoro-5-methoxyphenyl)-3-(1-methyl-1H-pyrrolo[3,2-c]pyridin-7-yl)thieno[3,2-d]pyrimidine-2,4(1H,3H)-dione (Example 957 and Example 958): 6-(2-chloro-4-fluoro-5-methoxyphenyl)-3-(1-methyl-1H-pyrrolo[3,2-c]pyridin-7-yl)thieno[3,2-d]pyrimidine-2,4(1H,3H)-dione (Example 454) as a mixture of 2 isomers was separated by chiral SFC (IB 5 um-21×250 mm column with 25% MeOH-DEA cosolvent) to give two enantiomers, which were assigned as Isomer 1 and Isomer 2. The stereochemistry was assigned by analogy to Example 438, with Example 957 being the more active isomer.

Isomer 1:

6-(2-chloro-4-fluoro-5-methoxyphenyl)-3-(1-methyl-1H-pyrrolo[3,2-c]pyridin-7-yl)thieno[3,2-d]pyrimidine-2,4(1H,3H)-dione (Example 957)

ES/MS: 456.8 (M⁺).

1H NMR (400 MHz, DMSO-d6) δ 12.57 (s, 1H), 9.31 (s, 1H), 8.63 (s, 1H), 7.85 (d, J=3.3 Hz, 1H), 7.73 (d, J=11.0 Hz, 1H), 7.46 (d, J=8.9 Hz, 1H), 7.35 (s, 1H), 7.11 (d, J=3.3 Hz, 1H), 3.95 (s, 3H), 3.79 (s, 3H).

Isomer 2:

6-(2-chloro-4-fluoro-5-methoxyphenyl)-3-(1-methyl-1H-pyrrolo[3,2-c]pyridin-7-yl)thieno[3,2-d]pyrimidine-2,4(1H,3H)-dione (Example 958)

ES/MS: 456.8 (M⁺).

1H NMR (400 MHz, DMSO-d6) δ 12.57 (s, 1H), 9.31 (s, 1H), 8.63 (s, 1H), 7.85 (d, J=3.3 Hz, 1H), 7.73 (d, J=11.0 Hz, 1H), 7.46 (d, J=8.8 Hz, 1H), 7.35 (s, 1H), 7.11 (d, J=3.2 Hz, 1H), 3.95 (s, 3H), 3.79 (s, 3H).

Procedure 108: Example 959 and Example 960

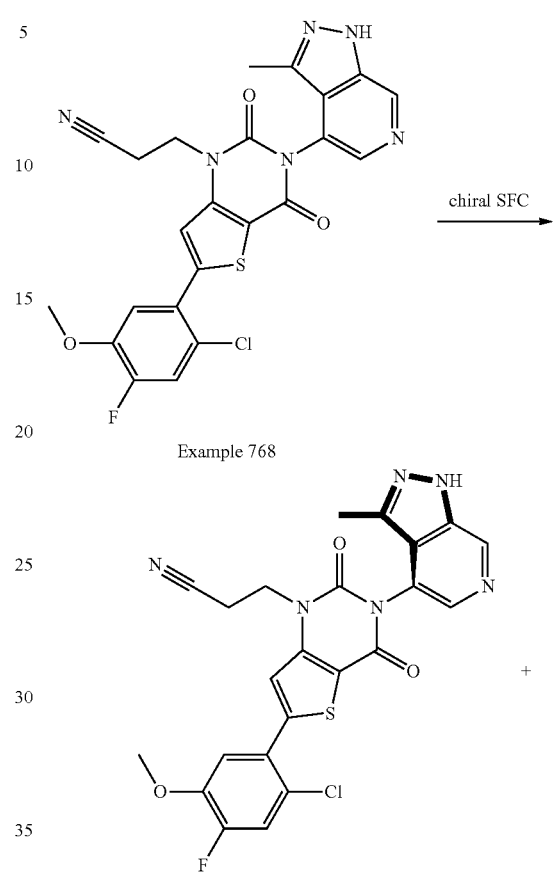

Example 768

Isomer 1
Example 959

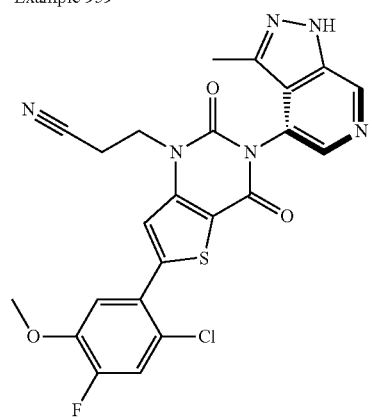

Isomer 2
Example 960

3-(6-(2-chloro-4-fluoro-5-methoxyphenyl)-3-(3-methyl-1H-pyrazolo[3,4-c]pyridin-4-yl)-2,4-dioxo-3,4-dihydrothieno[3,2-d]pyrimidin-1(2H)-yl)propanenitrile (Example 959 and Example 960): 3-(6-(2-chloro-4-fluoro-5-methoxyphenyl)-3-(3-methyl-1H-pyrazolo[3,4-c]pyridin-4-yl)-2,4-dioxo-3,4-dihydrothieno[3,2-d]pyrimidin-1(2H)-yl)propanenitrile (Example 768) as a mixture of 2 isomers was separated by chiral SFC (ID 5 um-21×250 mm column with 35% EtOH cosolvent) to give two enantiomers, which were assigned as Isomer 1 and Isomer 2. The stereochemistry was assigned by analogy to Example 438, with Example 959 being the more active isomer.

Isomer 1:

3-(6-(2-chloro-4-fluoro-5-methoxyphenyl)-3-(3-methyl-1H-pyrazolo[3,4-c]pyridin-4-yl)-2,4-dioxo-3,4-dihydrothieno[3,2-d]pyrimidin-1(2H)-yl)propanenitrile Example 959

ES/MS: 510.8 (M⁺).
1H NMR (400 MHz, DMSO-d6) δ 13.55 (s, 1H), 9.08 (s, 1H), 8.19 (s, 1H), 7.96 (d, J=3.5 Hz, 1H), 7.74 (d, J=10.7 Hz, 1H), 7.65-7.42 (m, 1H), 4.64-4.37 (m, 2H), 3.97 (d, J=7.0 Hz, 3H), 3.08 (t, J=6.7 Hz, 2H), 2.32 (s, 3H).

Isomer 2:

3-(6-(2-chloro-4-fluoro-5-methoxyphenyl)-3-(3-methyl-1H-pyrazolo[3,4-c]pyridin-4-yl)-2,4-dioxo-3,4-dihydrothieno[3,2-d]pyrimidin-1(2H)-yl)propanenitrile Example 960

ES/MS: 510.7 (M⁺).
1H NMR (400 MHz, DMSO-d6) δ 13.54 (s, 1H), 9.08 (s, 1H), 8.19 (s, 1H), 7.96 (s, 1H), 7.74 (d, J=11.1 Hz, 1H), 7.58 (d, J=9.0 Hz, 1H), 4.58-4.21 (m, 2H), 3.97 (s, 3H), 3.08 (t, J=6.6 Hz, 2H), 2.30 (s, 3H).

Procedure 109: Example 961 and Example 962

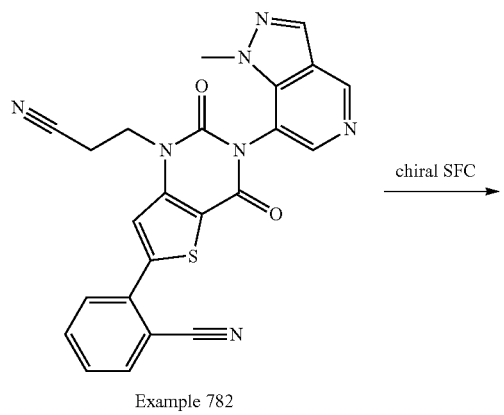

Example 782

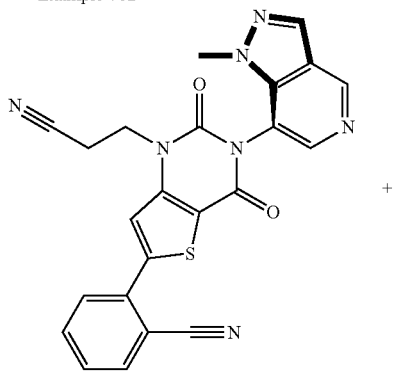

Isomer 1
Example 961

-continued

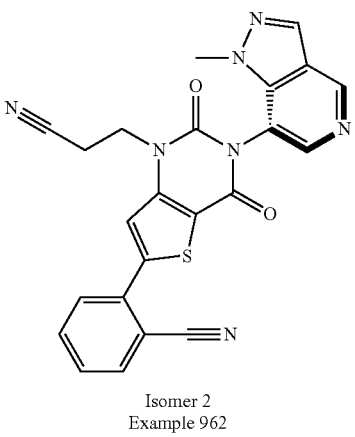

Isomer 2
Example 962

2-(1-(2-cyanoethyl)-3-(1-methyl-1H-pyrazolo[4,3-c]pyridin-7-yl)-2,4-dioxo-1,2,3,4-tetrahydrothieno[3,2-d]pyrimidin-6-yl)benzonitrile (Example 961 and Example %2): 2-(1-(2-cyanoethyl)-3-(1-methyl-1H-pyrazolo[4,3-c]pyridin-7-yl)-2,4-dioxo-1,2,3,4-tetrahydrothieno[3,2-d]pyrimidin-6-yl)benzonitrile (Example 782) as a mixture of 2 isomers was separated by chiral SFC (AD-H 5 um-21×250 mm column with 35% EtOH cosolvent) to give two enantiomers, which were assigned as Isomer 1 and Isomer 2. The stereochemistry was assigned by analogy to Example 438, with Example 961 being the more active isomer.

Isomer 1:

2-(1-(2-cyanoethyl)-3-(1-methyl-1H-pyrazolo[4,3-c]pyridin-7-yl)-2,4-dioxo-1,2,3,4-tetrahydrothieno[3,2-d]pyrimidin-6-yl)benzonitrile (Example 961)

ES/MS: 453.8 (M⁺).

1H NMR (400 MHz, DMSO-d6) δ 9.36 (s, 1H), 8.59 (s, 1H), 8.52 (s, 1H), 8.15 (s, 1H), 8.12 (dd, J=7.8, 1.2 Hz, 1H), 8.02-7.87 (m, 2H), 7.76 (td, J=7.5, 1.5 Hz, 1H), 4.60-4.21 (m, 2H), 3.96 (s, 3H), 3.08 (t, J=6.7 Hz, 2H).

Isomer 2:

2-(1-(2-cyanoethyl)-3-(1-methyl-1H-pyrazolo[4,3-c]pyridin-7-yl)-2,4-dioxo-1,2,3,4-tetrahydrothieno[3,2-d]pyrimidin-6-yl)benzonitrile (Example 962)

ES/MS: 453.8 (M⁺).

1H NMR (400 MHz, DMSO-d6) δ 9.35 (s, 1H), 8.58 (s, 1H), 8.52 (s, 1H), 8.17-8.07 (m, 2H), 8.02-7.89 (m, 2H), 7.76 (td, J=7.6, 1.5 Hz, 1H), 4.55 (dt, J=14.3, 7.2 Hz, 1H), 4.40 (dt, J=14.3, 6.3 Hz, 1H), 3.95 (s, 3H), 3.08 (t, J=6.7 Hz, 2H).

Procedure 110: Example 963 and Example 964

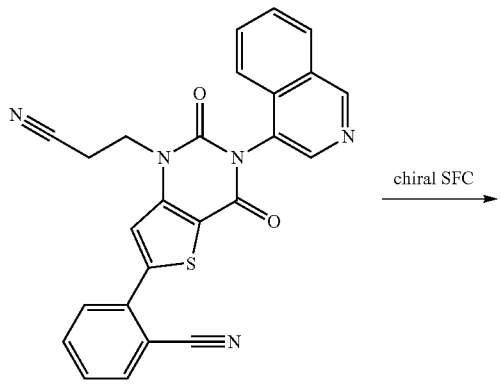

Example 819

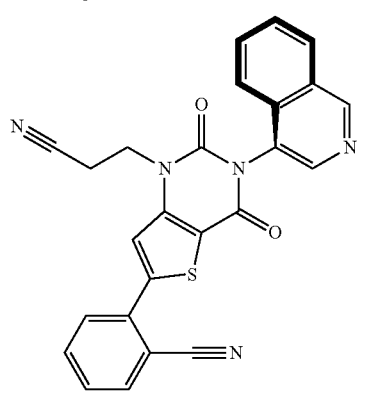

Isomer 1
Example 963

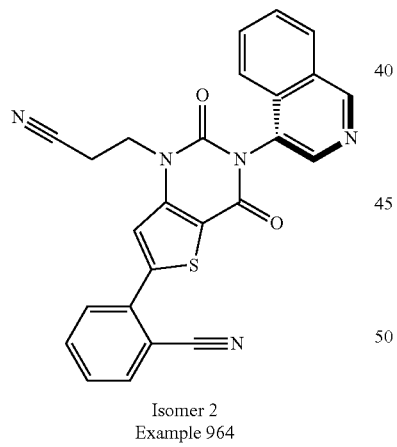

Isomer 2
Example 964

2-(1-(2-cyanoethyl)-3-(isoquinolin-4-yl)-2,4-dioxo-1,2,3,4-tetrahydrothieno[3,2-d]pyrimidin-6-yl)benzonitrile (Example 963 and Example 964): 2-(1-(2-cyanoethyl)-3-(isoquinolin-4-yl)-2,4-dioxo-1,2,3,4-tetrahydrothieno[3,2-d]pyrimidin-6-yl)benzonitrile (Example 819) as a mixture of 2 isomers was separated by chiral SFC (IB 5 um-21×250 mm column with 30% MeOH cosolvent) to give two enantiomers, which were assigned as Isomer 1 and Isomer 2. The stereochemistry was assigned by analogy to Example 438, with Example %3 being the more active isomer.

Isomer 1:

2-(1-(2-cyanoethyl)-3-(isoquinolin-4-yl)-2,4-dioxo-1,2,3,4-tetrahydrothieno[3,2-d]pyrimidin-6-yl)benzonitrile (Example 963)

ES/MS: 449.8 (M+).

1H NMR (400 MHz, DMSO-d6) δ 9.45 (s, 1H), 8.57 (s, 1H), 8.32 (s, 1H), 8.31-8.22 (m, 1H), 8.17-8.07 (m, 2H), 7.99-7.89 (m, 2H), 7.87-7.65 (m, 3H), 4.59-4.31 (m, 2H), 3.03 (t, J=6.8 Hz, 2H).

Isomer 2:

2-(1-(2-cyanoethyl)-3-(isoquinolin-4-yl)-2,4-dioxo-1,2,3,4-tetrahydrothieno[3,2-d]pyrimidin-6-yl)benzonitrile (Example 964)

ES/MS: 449.8 (M+).

1H NMR (400 MHz, DMSO-d6) δ 9.45 (s, 1H), 8.57 (s, 1H), 8.35-8.24 (m, 2H), 8.16-8.08 (m, 2H), 8.01-7.88 (m, 2H), 7.86-7.70 (m, 3H), 4.55-4.31 (m, 2H), 3.03 (t, J=6.8 Hz, 2H).

Procedure 111: Example 965 and Example 966

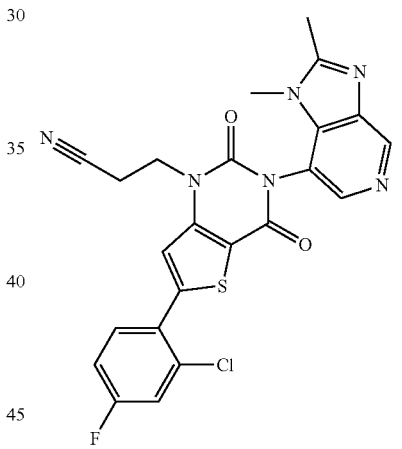

Example 853

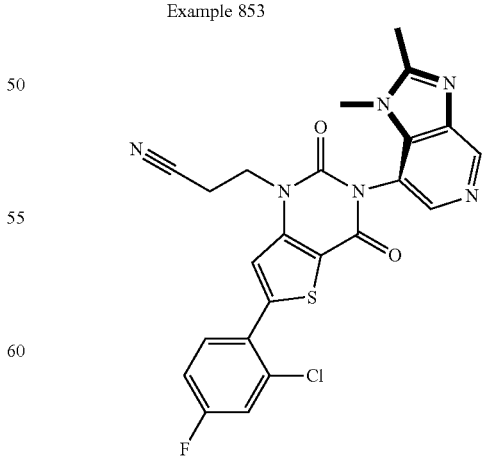

Isomer 1
Example 965

1365
-continued

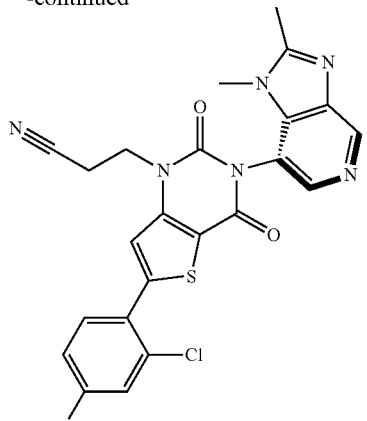

Isomer 2
Example 966

3-(6-(2-chloro-4-fluorophenyl)-3-(1,2-dimethyl-1H-imidazo[4,5-c]pyridin-7-yl)-2,4-dioxo-3,4-dihydrothieno[3,2-d]pyrimidin-1(2H)-yl)propanenitrile (Example 965 and Example 966): 3-(6-(2-chloro-4-fluorophenyl)-3-(1,2-dimethyl-1H-imidazo[4,5-c]pyridin-7-yl)-2,4-dioxo-3,4-dihydrothieno[3,2-d]pyrimidin-1(2H)-yl)propanenitrile (Example 853) as a mixture of 2 isomers was separated by chiral SFC (IB 5 um-21×250 mm column with 30% MeOH cosolvent) to give two enantiomers, which were assigned as Isomer 1 and Isomer 2. The stereochemistry was assigned by analogy to Example 438, with Example 965 being the more active isomer.

Isomer 1:

3-(6-(2-chloro-4-fluorophenyl)-3-(1,2-dimethyl-1H-imidazo[4,5-c]pyridin-7-yl)-2,4-dioxo-3,4-dihydrothieno[3,2-d]pyrimidin-1(2H)-yl)propanenitrile (Example 965)

ES/MS: 494.8 (M+).

1H NMR (400 MHz, DMSO-d6) δ 9.17 (s, 1H), 8.53 (s, 1H), 8.02 (s, 1H), 7.96 (dd, J=8.8, 6.0 Hz, 1H), 7.76 (dd, J=8.8, 2.6 Hz, 1H), 7.51 (td, J=8.4, 2.7 Hz, 1H), 4.59-4.36 (m, 2H), 3.65 (s, 3H), 3.06 (t, J=6.6 Hz, 2H), 2.65 (s, 3H).

Isomer 2:

3-(6-(2-chloro-4-fluorophenyl)-3-(1,2-dimethyl-1H-imidazo[4,5-c]pyridin-7-yl)-2,4-dioxo-3,4-dihydrothieno[3,2-d]pyrimidin-1(2H)-yl)propanenitrile (Example 966)

ES/MS: 494.8 (M+).

1H NMR (400 MHz, DMSO-d6) δ 9.18 (s, 1H), 8.53 (s, 1H), 8.02 (s, 1H), 7.96 (dd, J=8.8, 6.0 Hz, 1H), 7.76 (dd, J=8.8, 2.7 Hz, 1H), 7.51 (td, J=8.4, 2.7 Hz, 1H), 4.46 (ddt, J=47.1, 13.7, 6.6 Hz, 2H), 3.65 (s, 3H), 3.06 (t, J=6.6 Hz, 2H), 2.65 (s, 3H).

1366
Procedure 112: Example 967 and Example 968

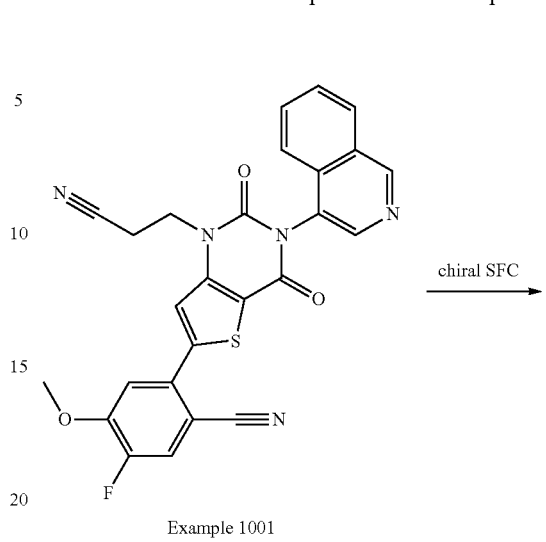

Example 1001

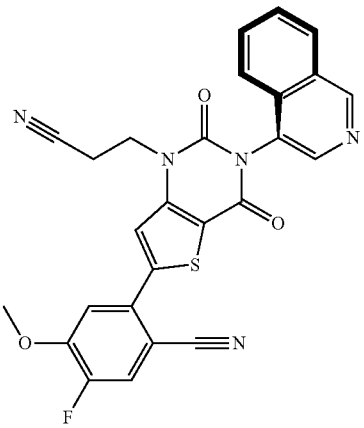

Isomer 1
Example 967

+

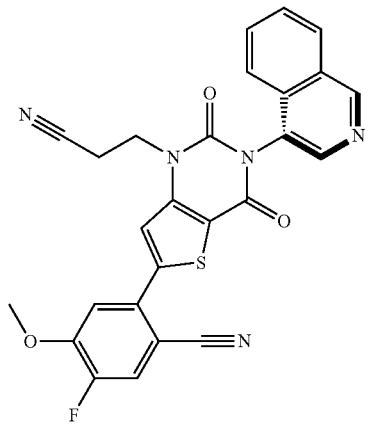

Isomer 2
Example 968

2-(1-(2-cyanoethyl)-3-(isoquinolin-4-yl)-2,4-dioxo-1,2,3,4-tetrahydrothieno[3,2-d]pyrimidin-6-yl)-5-fluoro-4-methoxybenzonitrile (Example 967 and Example 968): 2-(1-(2-cyanoethyl)-3-(isoquinolin-4-yl)-2,4-dioxo-1,2,3,4-tetrahydrothieno[3,2-d]pyrimidin-6-yl)-5-fluoro-4-methoxybenzonitrile (Example 1001) as a mixture of 2 isomers was separated by chiral SFC (AD-H 5 um-21×250 mm column with 50% EtOH cosolvent) to give two enantiomers, which were assigned as Isomer 1 and Isomer 2. The stereochemistry was assigned by analogy to Example 438, with Example 967 being the more active isomer.
Isomer 1:

2-(1-(2-cyanoethyl)-3-(isoquinolin-4-yl)-2,4-dioxo-1,2,3,4-tetrahydrothieno[3,2-d]pyrimidin-6-yl)-5-fluoro-4-methoxybenzonitrile (Example 967)

ES/MS: 497.8 (M$^+$).
1H NMR (400 MHz, DMSO-d6) δ 9.49 (s, 11H), 8.59 (s, 11H), 8.35-8.24 (m, 1H), 8.15 (d, J=11.1 Hz, 1H), 8.10 (s, 1H), 7.96-7.89 (m, 1H), 7.85-7.73 (m, 2H), 7.60 (d, J=8.1 Hz, 1H), 4.45 (dt, J=10.9, 7.0 Hz, 2H), 4.07 (s, 3H), 3.05 (t, J=6.8 Hz, 2H).
Isomer 2:

2-(1-(2-cyanoethyl)-3-(isoquinolin-4-yl)-2,4-dioxo-1,2,3,4-tetrahydrothieno[3,2-d]pyrimidin-6-yl)-5-fluoro-4-methoxybenzonitrile (Example 968)

ES/MS: 497.8 (M$^+$).
1H NMR (400 MHz, DMSO-d6) δ 9.50 (s, 11H), 8.60 (s, 11H), 8.36-8.27 (m, 1H), 8.15 (d, J=11.1 Hz, 1H), 8.10 (s, 1H), 7.98-7.92 (m, 1H), 7.89-7.77 (m, 2H), 7.60 (d, J=8.1 Hz, 1H), 4.53-4.39 (m, 2H), 4.07 (s, 3H), 3.05 (t, J=6.8 Hz, 2H).

Procedure 113: Example 969 and Example 970

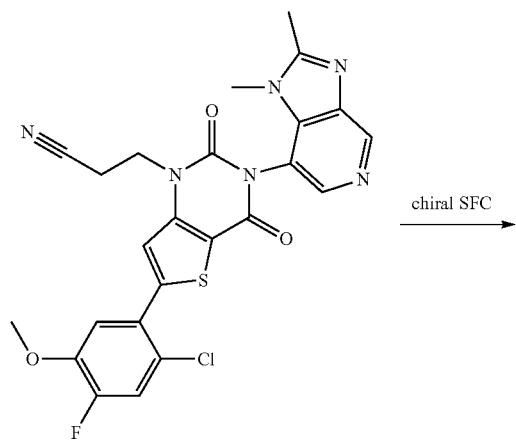

Example 842 chiral SFC

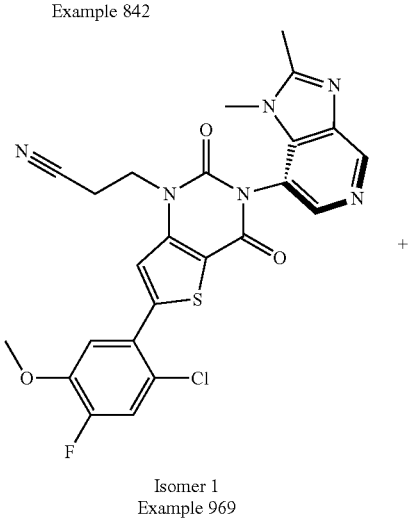

Isomer 1
Example 969

+

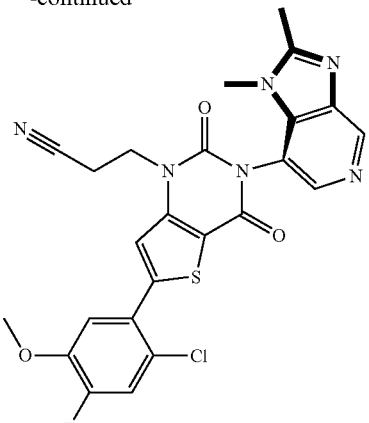

Isomer 2
Example 970

3-(6-(2-chloro-4-fluoro-5-methoxyphenyl)-3-(1,2-dimethyl-1H-imidazo[4,5-c]pyridin-7-yl)-2,4-dioxo-3,4-dihydrothieno[3,2-d]pyrimidin-1(2H)-yl)propanenitrile (Example 969 and Example 970): 3-(6-(2-chloro-4-fluoro-5-methoxyphenyl)-3-(1,2-dimethyl-1H-imidazo[4,5-c]pyridin-7-yl)-2,4-dioxo-3,4-dihydrothieno[3,2-d]pyrimidin-1(2H)-yl)propanenitrile (Example 842) as a mixture of 2 isomers was separated by chiral SFC (IK 5 um-30×250 mm column with 50% EtOH cosolvent) to give two enantiomers, which were assigned as Isomer 1 and Isomer 2. The stereochemistry was assigned by analogy to Example 438, with Example 970 being the more active isomer.
Isomer 1:

3-(6-(2-chloro-4-fluoro-5-methoxyphenyl)-3-(1,2-dimethyl-1H-imidazo[4,5-c]pyridin-7-yl)-2,4-dioxo-3,4-dihydrothieno[3,2-d]pyrimidin-1(2H)-yl)propanenitrile (Example 969)

ES/MS: 524.8 (M$^+$).
1H NMR (400 MHz, DMSO-d6) δ 9.24 (s, 1H), 8.59 (s, 1H), 8.00 (s, 1H), 7.76 (d, J=11.0 Hz, 1H), 7.55 (d, J=8.9 Hz, 1H), 4.64-4.24 (m, 2H), 3.97 (s, 3H), 3.67 (s, 3H), 3.08 (t, J=6.5 Hz, 2H), 2.67 (s, 3H).
Isomer 2:

3-(6-(2-chloro-4-fluoro-5-methoxyphenyl)-3-(1,2-dimethyl-1H-imidazo[4,5-c]pyridin-7-yl)-2,4-dioxo-3,4-dihydrothieno[3,2-d]pyrimidin-1(2H)-yl)propanenitrile (Example 970)

ES/MS: 524.8 (M$^+$).
1H NMR (400 MHz, DMSO-d6) δ 9.18 (s, 1H), 8.53 (s, 1H), 8.00 (s, 1H), 7.76 (d, J=11.0 Hz, 1H), 7.55 (d, J=8.9 Hz, 1H), 4.59-4.35 (m, 2H), 3.97 (s, 3H), 3.65 (s, 3H), 3.08 (t, J=6.5 Hz, 2H), 2.66 (s, 3H).

1369

Procedure 114: Example 971 and Example 972

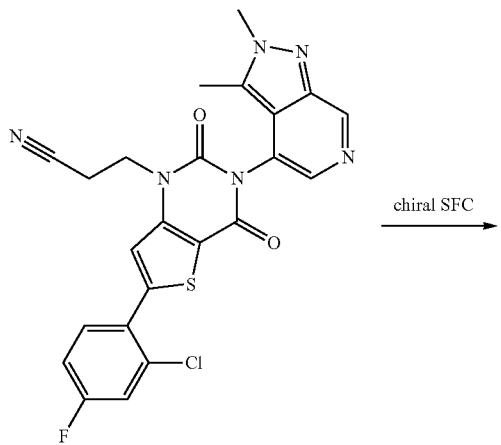

Example 797

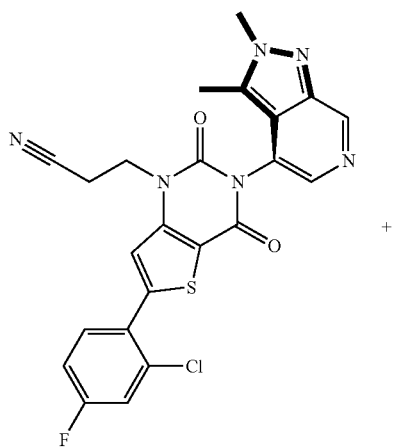

Isomer 1
Example 971

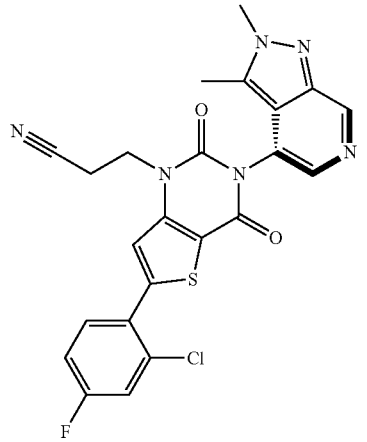

Isomer 2
Example 972

1370

3-(6-(2-chloro-4-fluorophenyl)-3-(2,3-dimethyl-2H-pyrazolo[3,4-c]pyridin-4-yl)-2,4-dioxo-3,4-dihydrothieno[3,2-d]pyrimidin-1(2H)-yl)propanenitrile (Example 971 and Example 972): 3-(6-(2-chloro-4-fluorophenyl)-3-(2,3-dimethyl-2H-pyrazolo[3,4-c]pyridin-4-yl)-2,4-dioxo-3,4-dihydrothieno[3,2-d]pyrimidin-1(2H)-yl)propanenitrile (Example 797) as a mixture of 2 isomers was separated by chiral SFC (AD-H Sum-21×250 mm column with 45% EtOH cosolvent) to give two enantiomers, which were assigned as Isomer 1 and Isomer 2. The stereochemistry was assigned by analogy to Example 438, with Example 971 being the more active isomer.

Isomer 1:

3-(6-(2-chloro-4-fluorophenyl)-3-(2,3-dimethyl-2H-pyrazolo[3,4-c]pyridin-4-yl)-2,4-dioxo-3,4-dihydrothieno[3,2-d]pyrimidin-1(2H)-yl)propanenitrile (Example 971)

ES/MS: 494.8 (M$^+$).

1H NMR (400 MHz, DMSO-d6) δ 9.33 (s, 1H), 8.11 (s, 1H), 8.01 (s, 1H), 7.96 (dd, J=8.8, 6.1 Hz, 1H), 7.76 (dd, J=8.8, 2.7 Hz, 1H), 7.50 (td, J=8.4, 2.7 Hz, 1H), 4.71-4.25 (m, 2H), 4.20 (s, 3H), 3.05 (t, J=6.6 Hz, 2H), 2.42 (s, 3H).

Isomer 2:

3-(6-(2-chloro-4-fluorophenyl)-3-(2,3-dimethyl-2H-pyrazolo[3,4-c]pyridin-4-yl)-2,4-dioxo-3,4-dihydrothieno[3,2-d]pyrimidin-1(2H)-yl)propanenitrile (Example 972)

ES/MS: 494.8 (M$^+$).

1H NMR (400 MHz, DMSO-d6) δ 9.27 (s, 1H), 8.07 (s, 1H), 8.04-7.92 (m, 2H), 7.75 (dd, J=8.8, 2.6 Hz, 1H), 7.50 (td, J=8.4, 2.7 Hz, 1H), 4.56-4.30 (m, 2H), 4.18 (s, 3H), 3.05 (t, J=6.6 Hz, 2H), 2.41 (s, 3H).

Procedure 115: Example 973 and Example 974

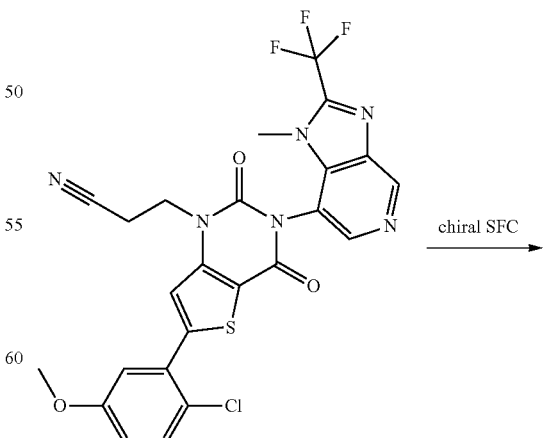

Example 856

-continued

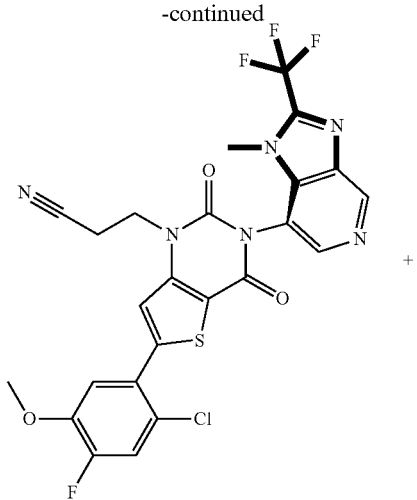

Isomer 1
Example 973

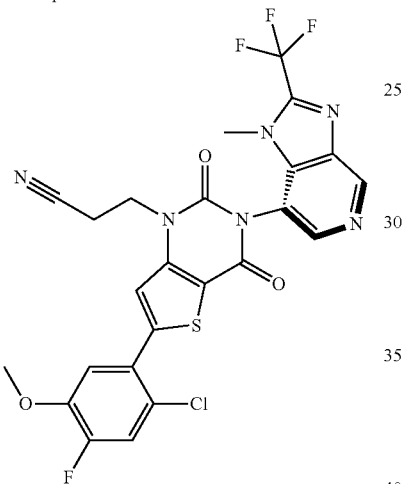

Isomer 2
Example 974

3-(6-(2-chloro-4-fluoro-5-methoxyphenyl)-3-(1-methyl-2-(trifluoromethyl)-1H-imidazo[4,5-c]pyridin-7-yl)-2,4-dioxo-3,4-dihydrothieno[3,2-d]pyrimidin-1(2H)-yl)propanenitrile (Example 973 and Example 974): 3-(6-(2-chloro-4-fluoro-5-methoxyphenyl)-3-(1-methyl-2-(trifluoromethyl)-1H-imidazo[4,5-c]pyridin-7-yl)-2,4-dioxo-3,4-dihydrothieno[3,2-d]pyrimidin-1(2H)-yl) propanenitrile (Example 856) as a mixture of 2 isomers was separated by chiral SFC (IB 5 um-21×250 mm column with 25% EtOH cosolvent) to give two enantiomers, which were assigned as Isomer 1 and Isomer 2. The stereochemistry was assigned by analog to Example 438, with Example 973 being the more active isomer.

Isomer 1:

3-(6-(2-chloro-4-fluoro-5-methoxyphenyl)-3-(1-methyl-2-(trifluoromethyl)-1H-imidazo[4,5-c]pyridin-7-yl)-2,4-dioxo-3,4-dihydrothieno[3,2-d]pyrimidin-1(2H)-yl)propanenitrile (Example 973)

ES/MS: 578.7 (M+).
1H NMR (400 MHz, DMSO-d6) δ 9.29 (s, 1H), 8.58 (s, 1H), 7.99 (s, 1H), 7.75 (d, J=11.0 Hz, 1H), 7.55 (d, J=8.9 Hz, 1H), 4.65-4.32 (m, 2H), 3.97 (s, 3H), 3.83 (s, 3H), 3.08 (t, J=6.5 Hz, 2H).

Isomer 2:

3-(6-(2-chloro-4-fluoro-5-methoxyphenyl)-3-(1-methyl-2-(trifluoromethyl)-1H-imidazo[4,5-c]pyridin-7-yl)-2,4-dioxo-3,4-dihydrothieno[3,2-d]pyrimidin-1(2H)-yl)propanenitrile (Example 974)

ES/MS: 578.7 (M+).
1H NMR (400 MHz, DMSO-d6) δ 9.29 (s, 1H), 8.59 (s, 1H), 7.99 (s, 1H), 7.75 (d, J=11.0 Hz, 1H), 7.55 (d, J=8.8 Hz, 1H), 4.66-4.29 (m, 2H), 3.97 (s, 3H), 3.83 (s, 3H), 3.08 (t, J=6.6 Hz, 2H).

Procedure 116: Example 975

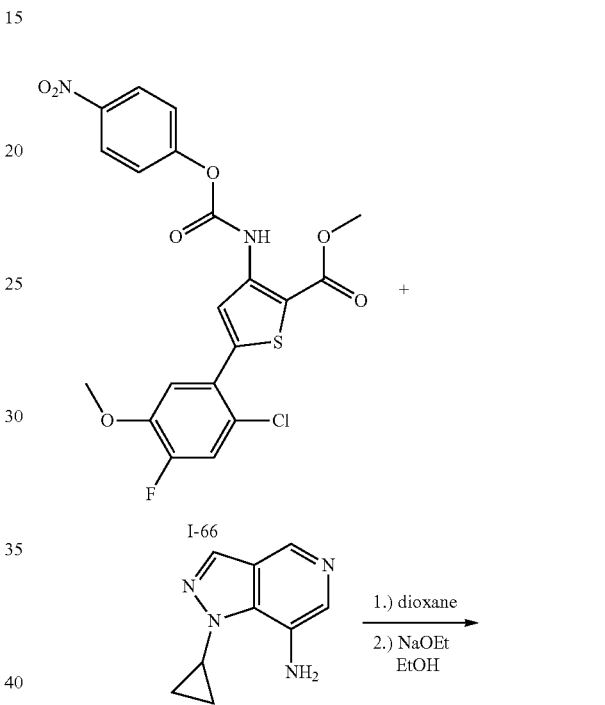

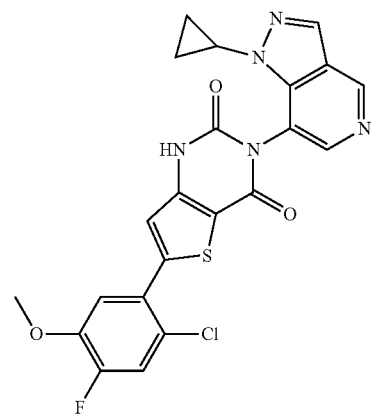

Example 975

6-(2-chloro-4-fluoro-5-methoxy-phenyl)-3-(1-cyclopropylpyrazolo[4,3-c]pyridin-7-yl)-1H-thieno[3,2-d]pyrimidine-2,4-dione (Example 975): To a suspension of methyl 5-(2-chloro-4-fluoro-5-methoxy-phenyl)-3-[(4-nitrophenoxy)carbonylamino]thiophene-2-carboxylate (I-66) (250 mg, 0.52 mmol) in dioxane (2.67 mL) was added 1-cyclopropylpyrazolo[4,3-c]pyridin-7-amine (109 mg, 0.64 mmol). The reaction mixture was stirred at 90° C. overnight.

The reaction was subsequently cooled to 0° C. A precipitate formed, and the precipitate was isolated by filtration. The precipitate was suspended in EtOH (1.63 mL), and to the mixture was added sodium ethoxide (21% wt. in EtOH, 0.25 mL, 0.78 mmol) at room temperature dropwise, and the reaction was stirred for 2 hours at room temperature. Approximately half of the solvent was removed under reduced pressure, and HCl (1N, 4 mL) was added. The mixture was let stand at 0° C., whereupon a precipitate formed. The solid was collected via filtration and dried over air to give the title compound Example 975.

ES/MS: 483.7 [M+].

$^1$H NMR (400 MHz, DMSO-d6) δ 12.51 (s, 1H), 9.34 (s, 1H), 8.55 (d, J=14.7 Hz, 2H), 7.72 (d, J=11.0 Hz, 1H), 7.47 (d, J=8.9 Hz, 1H), 7.34 (s, 1H), 3.95 (s, 3H), 3.52 (dq, J=7.1, 3.6 Hz, 1H), 1.15-0.99 (m, 2H), 0.88 (dqd, J=9.5, 7.3, 5.2 Hz, 2H).

Examples 976-978

The following Examples were made in an analogous fashion according to Procedure 116 and are shown below in Table 45. To prepare the below Examples, different reagents/starting materials were used than some of those described in Procedure 116 and are noted in the last column of Table 45—"Changes to Procedure 116: Different Reagents/Starting Materials".

TABLE 45

Examples 976-978

| Example | Structure | ES/MS m/z | 1H-NMR | Changes to Procedure 116: Different Reagents/ Starting Materials |
|---|---|---|---|---|
| 976 | 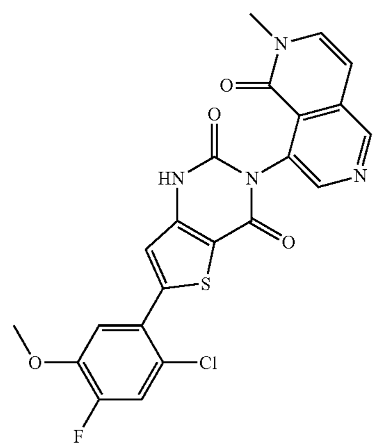 [SMILES: COc1cc(-c2cc3[nH]c(=O)n(-c4cncc5ccn(C)c(=O)c45)c(=O)c3s2)c(Cl)cc1F] | 484.7 | 1H NMR (400 MHz, DMSO-d6) δ 12.12 (s, 1H), 9.19 (s, 1H), 8.53 (d, J = 3.4 Hz, 1H), 7.76-7.67 (m, 2H), 7.49 (d, J = 8.9 Hz, 1H), 7.29-7.19 (m, 1H), 6.87 (dd, J = 7.2, 1.2 Hz, 1H), 3.95 (s, 3H), 3.44 (s, 3H). | I-203 |
| 977 | 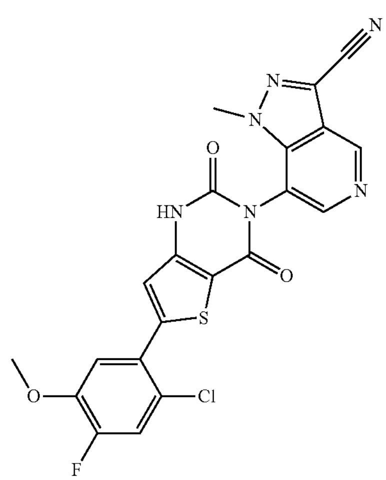 [SMILES: COc1cc(-c2cc3[nH]c(=O)n(-c4cncc5c(C#N)nn(C)c45)c(=O)c3s2)c(Cl)cc1F] | 482.8 | 1H NMR (400 MHz, DMSO-d6) δ 12.53 (s, 1H), 9.39 (s, 1H), 8.65 (s, 1H), 7.72 (d, J = 11.1 Hz, 1H), 7.46 (d, J = 8.9 Hz, 1H), 7.33 (s, 1H), 4.04 (s, 3H), 4.0 (s, 3H). | I-206 |

TABLE 45-continued

Examples 976-978

| Example | Structure | ES/MS m/z | 1H-NMR | Changes to Procedure 116: Different Reagents/ Starting Materials |
|---|---|---|---|---|
| 978 | 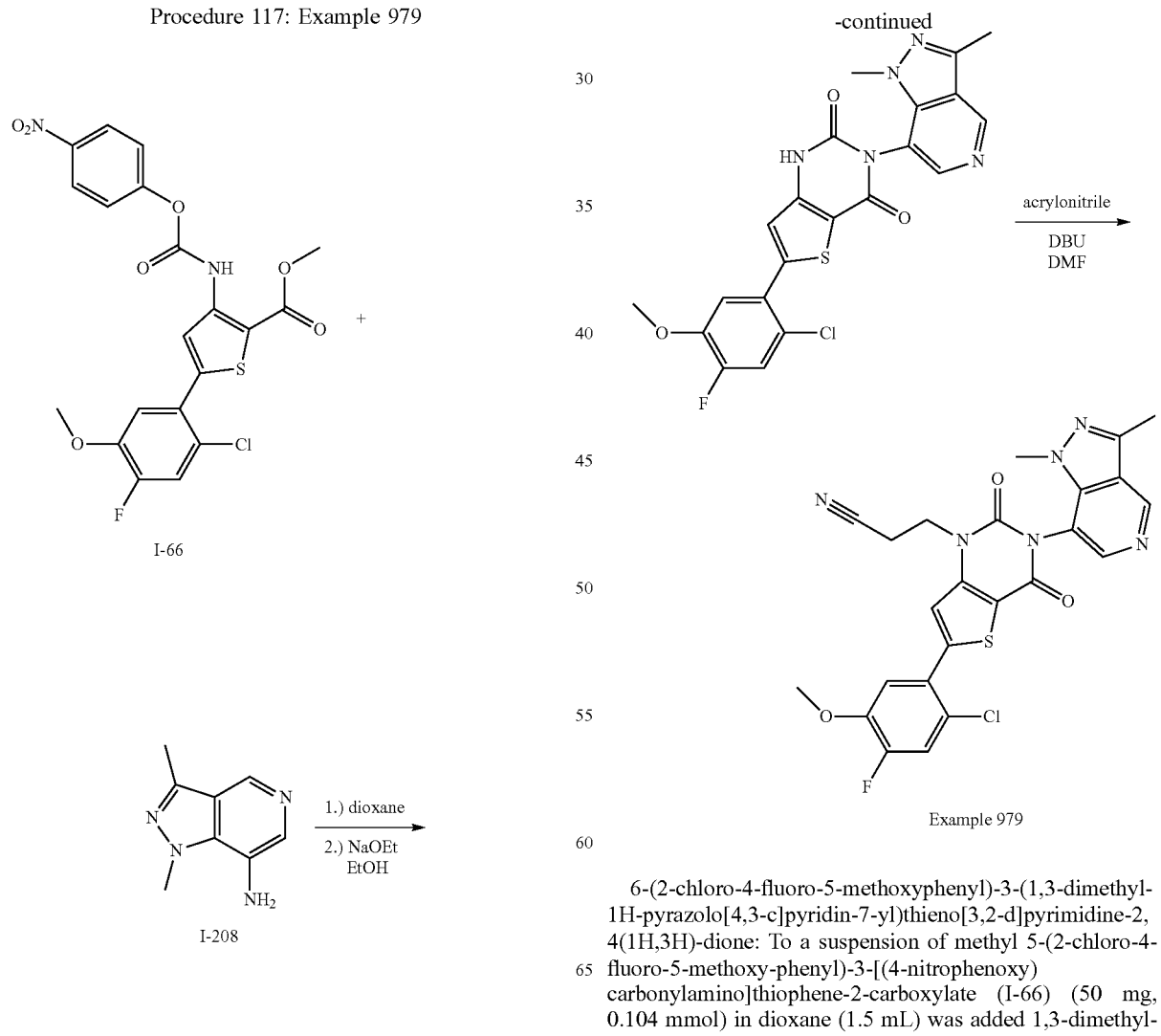 | 443.7 | 1H NMR (400 MHz, DMSO-d6) δ 12.46 (s, 1H), 9.22 (s, 1H), 8.47 (d, J = 1.0 Hz, 1H), 8.18 (s, 1H), 7.91 (d, J = 1.2 Hz, 1H), 7.73 (d, J = 11.0 Hz, 1H), 7.43 (d, J = 8.9 Hz, 1H), 7.33 (s, 1H), 3.96 (s, 3H). | imidazo[1,2-a]pyrazin-5-amine; hydrochloride |

Procedure 117: Example 979

6-(2-chloro-4-fluoro-5-methoxyphenyl)-3-(1,3-dimethyl-1H-pyrazolo[4,3-c]pyridin-7-yl)thieno[3,2-d]pyrimidine-2,4(1H,3H)-dione: To a suspension of methyl 5-(2-chloro-4-fluoro-5-methoxy-phenyl)-3-[(4-nitrophenoxy)carbonylamino]thiophene-2-carboxylate (I-66) (50 mg, 0.104 mmol) in dioxane (1.5 mL) was added 1,3-dimethyl- 1H-pyrazolo[4,3-c]pyridin-7-amine (I-208) (20.2 mg, 0.125 mmol). The reaction mixture was stirred at 90° C. overnight. The reaction was subsequently cooled to 0° C. A precipitate formed, and the precipitate was isolated by filtration. The precipitate was suspended in EtOH (1 mL), and to the mixture was added sodium ethoxide (21% wt. in EtOH: 0.05 mL, 0.15 mmol) at room temperature dropwise, and the reaction was stirred for 2 hours at room temperature. The mixture was concentrated under reduced pressure, and HCl (1N, 2 mL) was added. The mixture was let stand at 0° C., whereupon a precipitate formed. The solid was collected via filtration and dried over air to give the product.

ES/MS: 471.7 [M+].

3-(6-(2-chloro-4-fluoro-5-methoxyphenyl)-3-(1,3-dimethyl-1H-pyrazolo[4,3-c]pyridin-7-yl)-2,4-dioxo-3,4-dihydrothieno[3,2-d]pyrimidin-1(2H)-yl)propanenitrile (Example 979): To a stirring solution of 6-(2-chloro-4-fluoro-5-methoxyphenyl)-3-(1,3-dimethyl-1H-pyrazolo[4,3-c]pyridin-7-yl)thieno[3,2-d]pyrimidine-2,4(1H,3H)-dione (50.8 mg, 0.1 mmol), in DMF (0.17 mL), was added acrylonitrile (0.2 mL, 3 mmol) followed by DBU (50 µL, 0.3 mmol). The reaction mixture stirred for 12 hours at 80° C. after which the mixture was diluted with water (0.2 mL) and TFA (0.5 mL). The reaction mixture was then filtered through an acrodisc, and purified directly by RP-HPLC (0.1% TFA-ACN in 0.1% TFA Water, Column: Gemini 5 µM. NX-C18 110 Angstrom, 250×21.2 mm) to give the product Example 979 as a trifluoroacetate salt.

ES/MS: 524.7 (M+).

NH NMR (400 MHz, DMSO-d6) δ 9.40 (s, 1H), 8.55 (s, 1H), 7.99 (s, 1H), 7.75 (d, J=11.0 Hz, 1H), 7.56 (d, J=8.9 Hz, 1H), 4.55 (dt, J=14.0, 6.9 Hz, 1H), 4.42 (dt, J=14.3, 6.1 Hz, 1H), 3.97 (s, 3H), 3.87 (s, 3H), 3.08 (t, J=6.6 Hz, 2H), 2.66 (s, 3H).

Examples 980-992

The following Examples were made in an analogous fashion according to Procedure 117 and are shown below in Table 40. To prepare the below Examples, different reagents/starting materials were used than some of those described in Procedure 117 and are noted in the last column of Table 46—"Changes to Procedure 117: Different Reagents/Starting Materials".

TABLE 46

Examples 980-992

| Example | Structure | ES/MS m/z | 1H-NMR | Changes to Procedure 117: Different Reagents/Starting Materials |
|---|---|---|---|---|
| 980 | 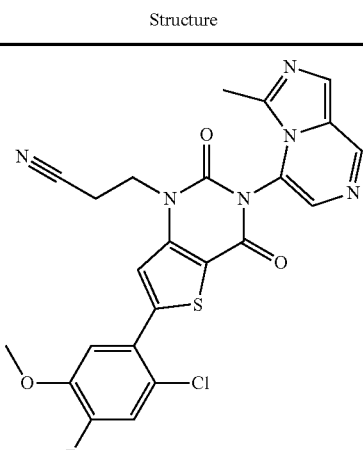 | 510.7 | 1H NMR (400 MHz, DMSO-d6) δ 9.12 (s, 1H), 7.99 (s, 1H), 7.94 (s, 1H), 7.79-7.69 (m, 2H), 7.58 (d, J = 8.8 Hz, 1H), 4.56 (dt, J = 13.8, 6.9 Hz, 1H), 4.47-4.37 (m, 1H), 3.97 (s, 3H), 3.09 (t, J = 6.5 Hz, 2H), 2.46 (s, 3H). | I-211 |
| 981 | 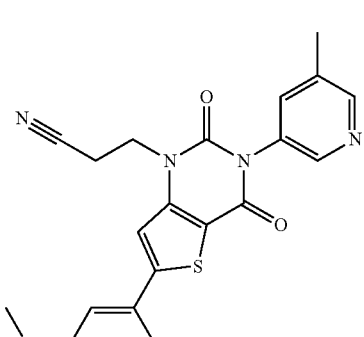 | 471.3 | 1H NMR (400 MHz, DMSO-d6) δ 8.54 (s, 1H), 8.43 (s, 1H), 7.93 (s, 1H), 7.79-7.69 (m, 2H), 7.52 (d, 1H), 4.43 (t, 2H), 3.97 (s, 3H), 3.01 (t, 2H), 2.40 (s, 3H). | 5-methylpyridin-3-amine |

TABLE 46-continued
Examples 980-992
| Example | Structure | ES/MS m/z | 1H-NMR | Changes to Procedure 117: Different Reagents/ Starting Materials |
|---|---|---|---|---|
| 982 | 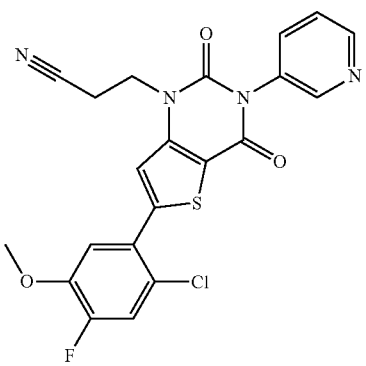 | 457.2 | 1H NMR (400 MHz, DMSO-d6) δ 8.66 (dd, 1H), 8.60 (d, 1H), 7.96-7.85 (m, 2H), 7.73 (d, 1H), 7.62 (dd, 1H), 7.52 (d, 1H), 4.43 (t, 2H), 3.97 (s, 3H), 3.00 (t, 2H). | pyridin-3-amine |
| 983 | 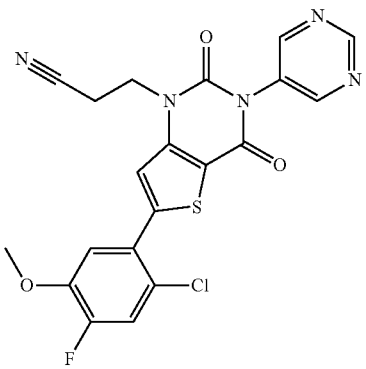 [SMILES: COc1cc(-c2cc3c(s2)c(=O)n(-c2cncnc2)c(=O)n3CCC#N)c(Cl)cc1F] | 458.1 | 1H NMR (400 MHz, DMSO-d6) δ 9.27 (s, 1H), 8.91 (s, 2H), 7.96 (s, 1H), 7.74 (d, 1H), 7.52 (d, 1H), 4.44 (t, 2H), 3.97 (s, 3H), 3.00 (t, 2H). | pyrimidin-5-amine |
| 984 | 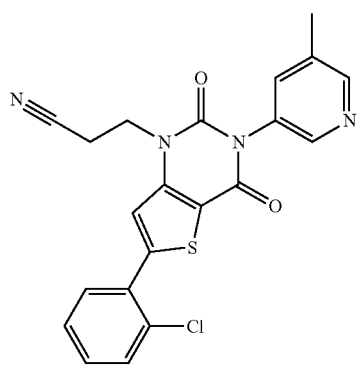 [SMILES: Cc1cncc(-n2c(=O)c3sc(-c4ccccc4Cl)cc3n(CCC#N)c2=O)c1] | 423.2 | 1H NMR (400 MHz, DMSO-d6) δ 8.52 (d, 1H), 8.41 (d, 1H), 7.98 (s, 1H), 7.91-7.82 (m, 1H), 7.76-7.66 (m, 2H), 7.60-7.51 (m, 2H), 4.41 (t, 2H), 2.98 (t, 2H), 2.39 (s, 3H). | 5-methylpyridin-3-amine; I-30 |

TABLE 46-continued

Examples 980-992

| Example | Structure | ES/MS m/z | 1H-NMR | Changes to Procedure 117: Different Reagents/ Starting Materials |
|---|---|---|---|---|
| 985 | 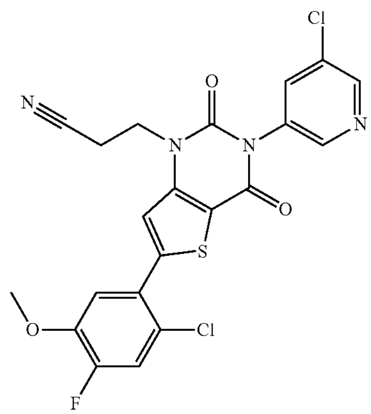 [SMILES: COc1cc(-c2cc3c(s2)c(=O)n(-c2cncc(Cl)c2)c(=O)n3CCC#N)c(Cl)cc1F] | 491.2 | 1H NMR (400 MHz, DMSO-d6) δ 8.75 (d, 1H), 8.60 (d, 1H), 8.13 (s, 1H), 7.95 (s, 1H), 7.73 (d, 1H), 7.51 (d, 1H), 4.43 (t, 2H), 3.97 (s, 3H), 3.04-2.96 (m, 2H). | 5-chloropyridin-3-amine |
| 986 | 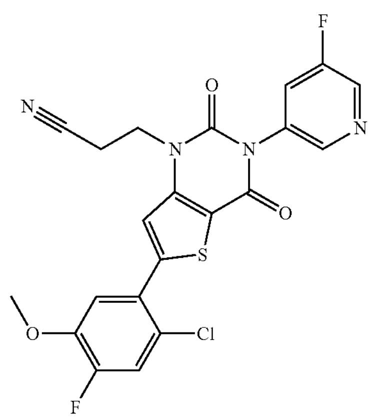 [SMILES: COc1cc(-c2cc3c(s2)c(=O)n(-c2cncc(F)c2)c(=O)n3CCC#N)c(Cl)cc1F] | 475.2 | 1H NMR (400 MHz, DMSO-d6) δ 8.71 (d, 1H), 8.52 (d, 1H), 7.98-7.92 (m, 2H), 7.73 (d, 1H), 7.52 (d, 1H), 4.43 (t, 2H), 3.97 (s, 3H), 3.00 (t, 2H). | 5-fluoropyridin-3-amine |
| 987 | 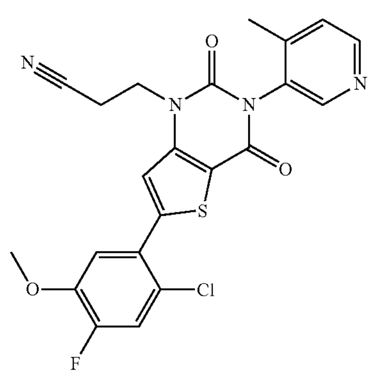 [SMILES: COc1cc(-c2cc3c(s2)c(=O)n(-c2cnccc2C)c(=O)n3CCC#N)c(Cl)cc1F] | 471.3 | 1H NMR (400 MHz, DMSO-d6) δ 8.63-8.55 (m, 2H), 7.93 (s, 1H), 7.74 (d, 1H), 7.60 (d, 1H), 7.54 (d, 1H), 4.51 (dt, 1H), 4.38 (dt, 1H), 3.96 (s, 3H), 3.08-3.00 (m, 2H), 2.21 (s, 3H). | 4-methylpyridin-3-amine |

TABLE 46-continued

Examples 980-992

| Example | Structure | ES/MS m/z | 1H-NMR | Changes to Procedure 117: Different Reagents/ Starting Materials |
|---|---|---|---|---|
| 988 | 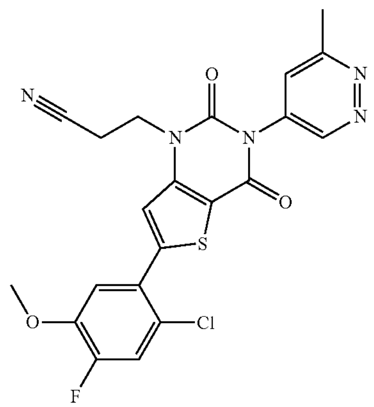 [SMILES: COc1cc(-c2cc3c(s2)c(=O)n(-c2cnnc(C)c2)c(=O)n3CCC#N)c(Cl)cc1F] | 472.2 | 1H NMR (400 MHz, DMSO-d6) δ 9.17 (d, 1H), 7.95 (s, 1H), 7.78-7.70 (m, 2H), 7.52 (d, 1H), 4.43 (t, 2H), 3.97 (s, 3H), 3.00 (t, 2H), 2.74 (s, 3H). | 6-methylpyridazin-4-amine |
| 989 | 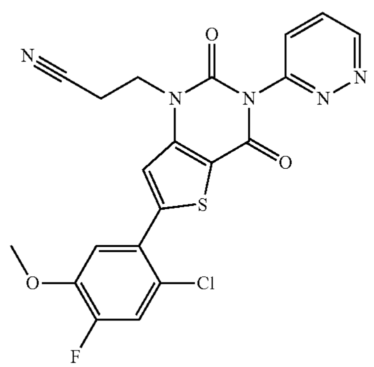 [SMILES: COc1cc(-c2cc3c(s2)c(=O)n(-c2cccnn2)c(=O)n3CCC#N)c(Cl)cc1F] | 458.2 | 1H NMR (400 MHz, DMSO-d6) δ 9.38 (dd, 1H), 8.00 (dd, 1H), 7.97 (s, 1H), 7.94 (dd, 1H), 7.74 (d, 1H), 7.55 (d, 1H), 4.44 (s, 2H), 3.97 (s, 3H), 3.02 (t, 2H). | pyridazin-3-amine |
| 990 | 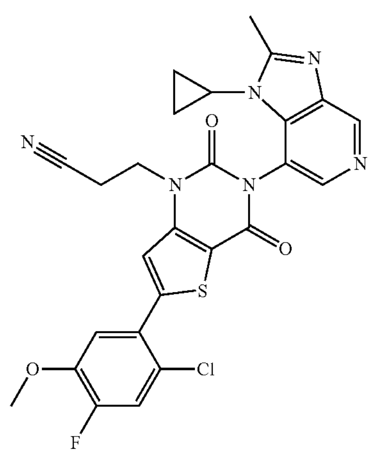 [SMILES: COc1cc(-c2cc3c(s2)c(=O)n(-c2cncc4nc(C)n(C5CC5)c24)c(=O)n3CCC#N)c(Cl)cc1F] | 550.8 | 1H NMR (400 MHz, DMSO-d6) δ 9.22 (s, 1H), 8.60 (s, 1H), 8.01 (s, 1H), 7.75 (d, J = 11.0 Hz, 1H), 7.56 (d, J = 8.8 Hz, 1H), 4.60-4.37 (m, 2H), 3.97 (s, 3H), 3.37 (td, J = 7.0, 3.5 Hz, 1H), 3.08 (t, J = 6.5 Hz, 2H), 2.70 (s, 3H), 1.30-0.99 (m, 2H), 0.89 (dq, J = 19.0, 7.1, 5.4 Hz, 2H) | I-231 |

TABLE 46-continued

Examples 980-992

| Example | Structure | ES/MS m/z | 1H-NMR | Changes to Procedure 117: Different Reagents/ Starting Materials |
|---|---|---|---|---|
| 991 | 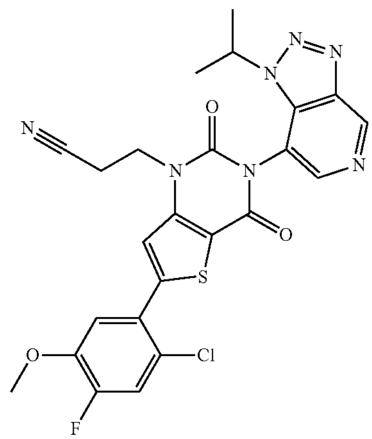 [SMILES: COc1cc(-c2cc3c(s2)c(=O)n(-c2cncc4nnn(C(C)C)c24)c(=O)n3CCC#N)c(Cl)cc1F] | 539.8 | 1H NMR (400 MHz, DMSO-d6) δ 9.61 (s, 1H), 8.63 (s, 1H), 8.00 (s, 1H), 7.75 (d, J = 11.0 Hz, 1H), 7.55 (d, J = 8.9 Hz, 1H), 4.75 (p, J = 6.6 Hz, 1H), 4.62-4.34 (m, 2H), 3.97 (s, 3H), 3.07 (t, J = 6.5 Hz, 2H), 1.57 (d, J = 6.6 Hz, 3H), 1.50 (d, J = 6.6 Hz, 3H) | I-234 |
| 992 | 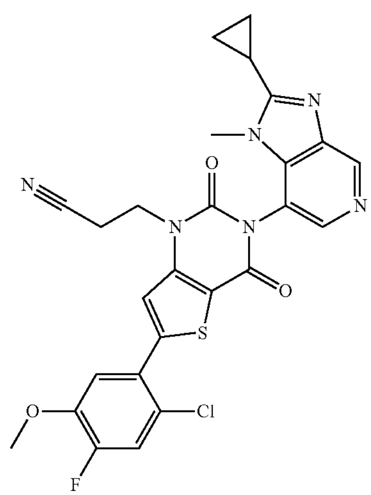 [SMILES: COc1cc(-c2cc3c(s2)c(=O)n(-c2cncc4nc(C5CC5)n(C)c24)c(=O)n3CCC#N)c(Cl)cc1F] | 550.8 | 1H NMR (400 MHz, DMSO-d6) δ 9.21 (s, 1H), 8.60 (s, 1H), 8.00 (s, 1H), 7.75 (d, J = 11.0 Hz, 1H), 7.55 (d, J = 8.8 Hz, 1H), 4.62-4.33 (m, 2H), 3.97 (s, 3H), 3.80 (s, 3H), 3.08 (t, J = 6.5 Hz, 2H), 2.41 (tt, J = 7.9, 4.9 Hz, 1H), 1.36-1.00 (m, 4H) | I-236 |

Procedure 118: Example 993

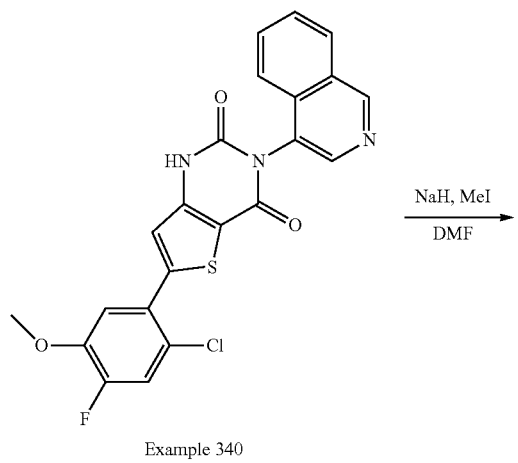

Example 340

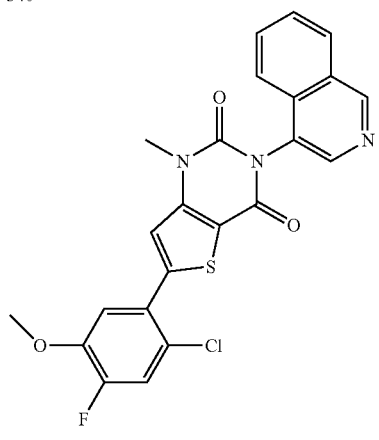

Example 993

6-(2-chloro-4-fluoro-5-methoxy-phenyl)-3-(4-isoquinolyl)-1-methyl-thieno[3,2-d]pyrimidine-2A4-dione (Example 993): To a solution of 6-(2-chloro-4-fluoro-5-methoxy-phenyl)-3-(4-isoquinolyl)-1H-thieno[3,2-d]pyrimidine-2,4-dione (Example 340) (HCl salt) (100 mg, 0.20 mmol, 1.0 equiv.) in dry DMF at 0° C. (0.7 mL, 0.3 M) was added 60% NaH (16.4 mg, 0.43 mmol, 2.1 equiv.). The reaction mixture was stirred at 0° C. for 0.5 h after which MeI (0.013 mL, 0.2 mmol, 1.0 equiv.) was added and stirred for an additional 1 h. The reaction mixture stirred for 1 h after which the mixture was diluted with water (0.2 mL) and TFA (0.5 mL), and the mixture was filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 993 as a trifluoroacetate salt.

ES/MS: 467.7 (M$^+$).

$^1$H NMR (400 MHz, DMSO-d$_6$) δ 9.48 (s, 1H), 8.58 (s, 1H), 8.31 (d, J=7.8 Hz, 1H), 7.93-7.70 (m, 5H), 7.56 (d, J=8.9 Hz, 1H), 3.99 (s, 3H), 3.64 (s, 3H).

Example 994

The following Examples were made in an analogous fashion according to Procedure 118 and are shown below in Table 47. To prepare the below Examples, different reagents/starting materials were used than some of those described in Procedure 118 and are noted in the last column of Table 47—"Changes to Procedure 118: Different Reagents/Starting Materials".

TABLE 47

| Example | Structure | ES/MS m/z | 1H-NMR | Changes to Procedure 118: Different Reagents/ Starting Materials |
|---|---|---|---|---|
| 994 | 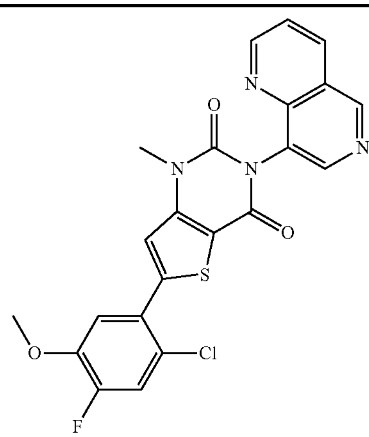 | 469.2 | 1H NMR (400 MHz, DMSO-d6) δ 9.57 (s, 1H), 9.11 (dd, 1H), 8.83 (s, 1H), 8.74 (dd, 1H), 7.84-7.76 (m, 2H), 7.73 (d, 1H), 7.58 (d, 1H), 3.98 (s, 3H), 3.64 (s, 3H). | Example 553 |

Procedure 119: Example 995 and Example 996

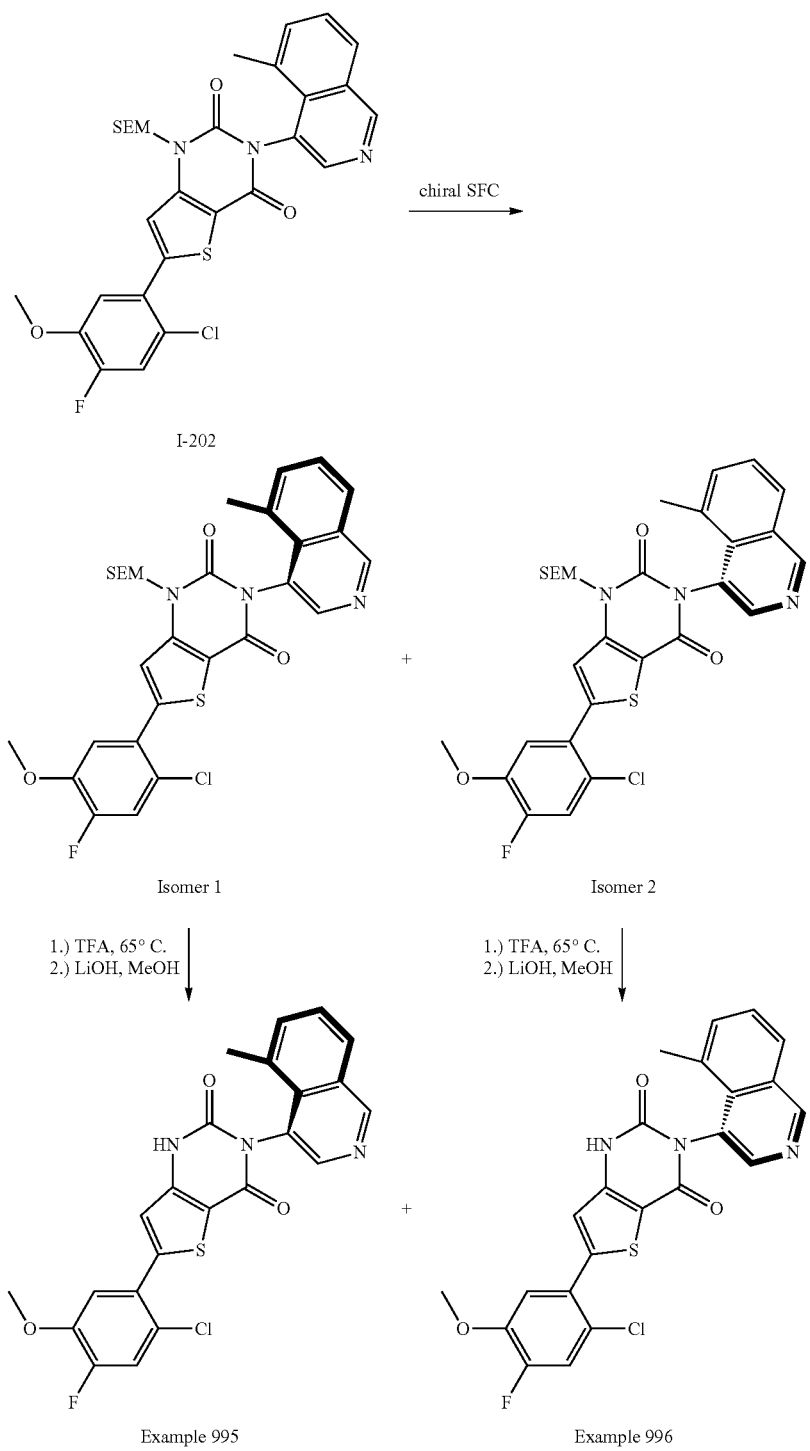

6-(2-chloro-4-fluoro-5-methoxy phenyl)-3-(5-methyliso-quinolin-4-yl)-1-((2-(trimethylsilyl)ethoxy)methyl)thieno[3,2-d]pyrimidine-2,4(1H,3H)-dione (I-202) as a mixture of 2 atropisomers was separated by chiral SFC (AD-H 21×250 5 um column with 45% MeOH cosolvent) to give two enantiomers, which were assigned as Isomer 1 and Isomer 2.

Each isomer was then individually subjected to SEM-group removal under acidic conditions.
Isomer 1:
6-(2-chloro-4-fluoro-5-methoxyphenyl)-3-(5-methylisoquinolin-4-yl)thieno[3,2-d]pyrimidine-2,4(1H,3H)-dione (Example 995): To a 20 mL scintillation vial containing a stir bar was added 6-(2-chloro-4-fluoro-5-methoxy-phenyl)-3-

(5-methyl-4-isoquinolyl)-1-(2-trimethylsilylethoxymethyl) thieno[3,2-d]pyrimidine-2,4-dione (Isomer 1) (130 mg, 0.217 mmol), TFA (2 mL), followed by 0.1 mL of H₂O. The reaction mixture was stirred for 30 minutes at room temperature, after which the reaction mixture was concentrated under reduced pressure. The crude material was dissolved in MeOH (1 mL), and LiOH monohydrate (20.9 mg, 3 eq.) dissolved in water (0.5 mL) was added to the reaction. The reaction was stirred for 2 hours at room temperature. The mixture was concentrated under reduced pressure, and subsequently water (2 mL) and TFA (0.2 mL) were added. The mixture was cooled to 0° C., and a precipitate formed. The precipitate was filtered and washed once with water. The precipitate was dried under reduced pressure to give the title compound Example 995 as a trifluoroacetate salt. The stereochemistry of Example 995 was assigned by analogy to Example 438, with Example 995 being the more active isomer.

ES/MS: 467.7 (M⁺).

1H NMR (400 MHz, DMSO-d6) δ 12.40 (s, 1H), 9.44 (s, 1H), 8.53 (s, 1H), 8.18 (dd, J=7.3, 2.2 Hz, 1H), 7.78-7.61 (m, 3H), 7.50 (d, J=8.9 Hz, 1H), 7.32 (s, 1H), 3.95 (s, 3H), 2.43 (s, 3H).

Isomer 2.

6-(2-chloro-4-fluoro-5-methoxyphenyl)-3-(5-methylisoquinolin-4-yl)thieno[3,2-d]pyrimidine-2,4(1H,3H)-dione (Example 996): To a 20 mL scintillation vial containing a stir bar was added 6-(2-chloro-4-fluoro-5-methoxy-phenyl)-3-(5-methyl-4-isoquinolyl)-1-(2-trimethylsilylethoxymethyl) thieno[3,2-d]pyrimidine-2,4-dione (Isomer 2) (130 mg, 0.217 mmol), TFA (2 mL), followed by 0.1 mL of H₂O. The reaction mixture was stirred for 30 minutes at room temperature, after which the reaction mixture was concentrated under reduced pressure. The crude material was dissolved in MeOH (I mL), and LiOH monohydrate (20.9 mg, 3 eq.) dissolved in water (0.5 mL) was added to the reaction. The reaction was stirred for 2 hours at room temperature. The mixture was concentrated under reduced pressure, and subsequently water (2 mL) and TFA (0.2 mL) were added. The mixture was cooled to 0° C., and a precipitate formed. The precipitate was filtered and washed once with water. The precipitate was dried under reduced pressure to give the title compound Example 996 as a trifluoroacetate salt. The stereochemistry of Example 996 was assigned by analogy to Example 438, with Example 996 being the less active isomer.

ES/MS: 467.7 (M⁺).

1H NMR (400 MHz, DMSO-d6) δ 12.41 (s, 1H), 9.45 (s, 1H), 8.53 (s, 1H), 8.18 (dd, J=7.2, 2.3 Hz, 1H), 7.76-7.62 (m, 3H), 7.50 (d, J=8.9 Hz, 1H), 7.32 (s, 1H), 3.95 (s, 3H), 2.43 (s, 3H).

Procedure 120: Example 997

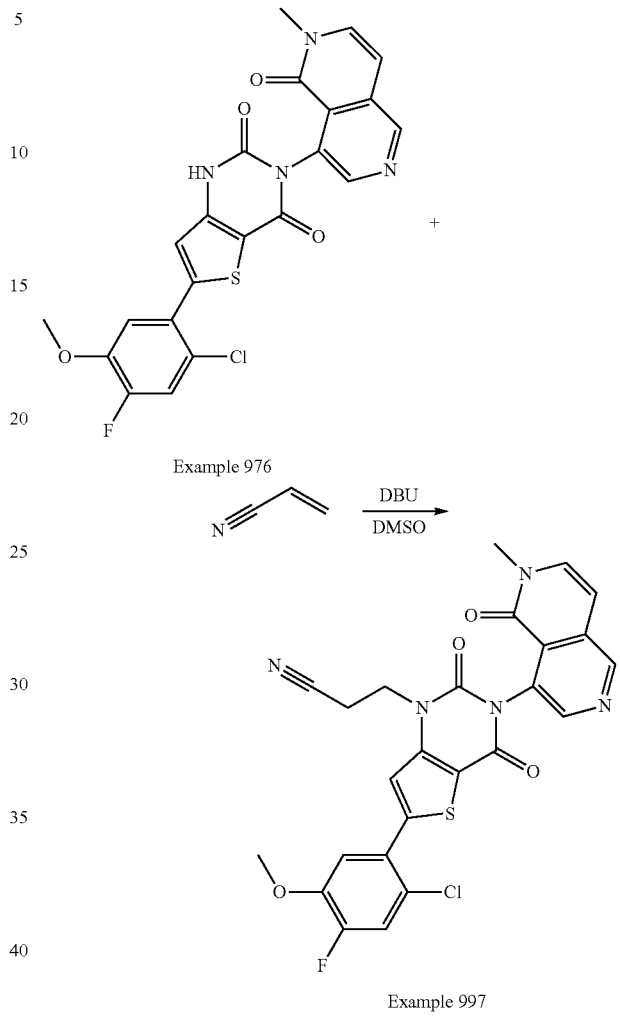

Example 976

Example 997

2-[6-(2-chloro-4-fluoro-5-methoxy-phenyl)-3-(4-isoquinolyl)-2,4-dioxo-thieno[3,2-d]pyrimidin-1-yl]acetonitrile (Example 997): To a stirring solution of 6-(2-chloro-4-fluoro-5-methoxy-phenyl)-3-(6-methyl-5-oxo-2,6-naphthyridin-4-yl)-1H-thieno[3,2-d]pyrimidine-2,4-dione (Example 976) (HCl salt) (32 mg, 0.06 mmol, 1.0 equiv.), in DMSO (0.11 mL, 0.54 M), was added acrylonitrile (0.36 mL, 5.52 mmol, 90 equiv.) followed by DBU (19 μL, 0.12 mmol, 2.0 equiv.). The reaction mixture stirred for 6 hours at 80° C. after which the mixture was diluted with water (0.2 mL) and TFA (0.5 mL). The reaction mixture was then filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 997 as a trifluoroacetate salt.

ES/MS: 537.7 (M⁺).

¹H NMR (400 MHz, DMSO-d6) δ 9.20 (s, 1H), 8.53 (s, 1H), 7.89 (s, 1H), 7.74 (d, J=7.3 Hz, 1H), 7.36 (s, 1H), 7.23 (s, 1H), 6.88 (d, J=7.3 Hz, 1H), 4.14 (q, J=6.9 Hz, 2H), 3.89 (s, 3H), 3.43 (s, 3H), 1.37 (t, J=7.0 Hz, 3H).

Example 998

The following Examples were made in an analogous fashion according to Procedure 120 and are shown below in Table 48. To prepare the below Examples, different reagents/starting materials were used than some of those described in Procedure 120 and are noted in the last column of Table 48—"Changes to Procedure 120: Different Reagents/Starting Materials".

TABLE 48

Example 998

| Example | Structure | ES/MS m/z | 1H-NMR | Changes to Procedure 120: Different Reagents/Starting Materials |
|---|---|---|---|---|
| 998 | 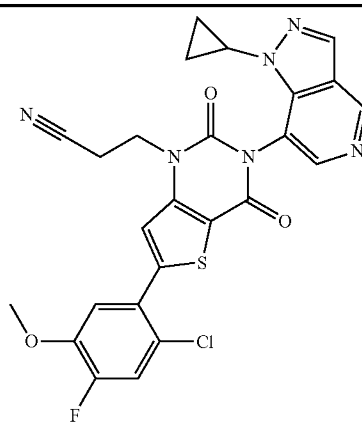 | 536.7 | 1H NMR (400 MHz, DMSO-d6) δ 9.32 (s, 1H), 8.52 (d, J = 3.7 Hz, 2H), 8.01 (s, 1H), 7.75 (d, J = 11.0 Hz, 1H), 7.57 (d, J = 8.9 Hz, 1H), 4.55 (dt, J = 13.6, 6.6 Hz, 1H), 4.44 (dt, J = 14.4, 6.3 Hz, 1H), 3.98 (s, 3H), 3.59 (tt, J = 7.1,3.6 Hz, 1H), 3.09 (d, J = 12.9 Hz, 2H), 1.19-1.08 (m, 1H). 1.01-0.75 (m, 3H). | Example 975 |

Procedure 121: Example 999

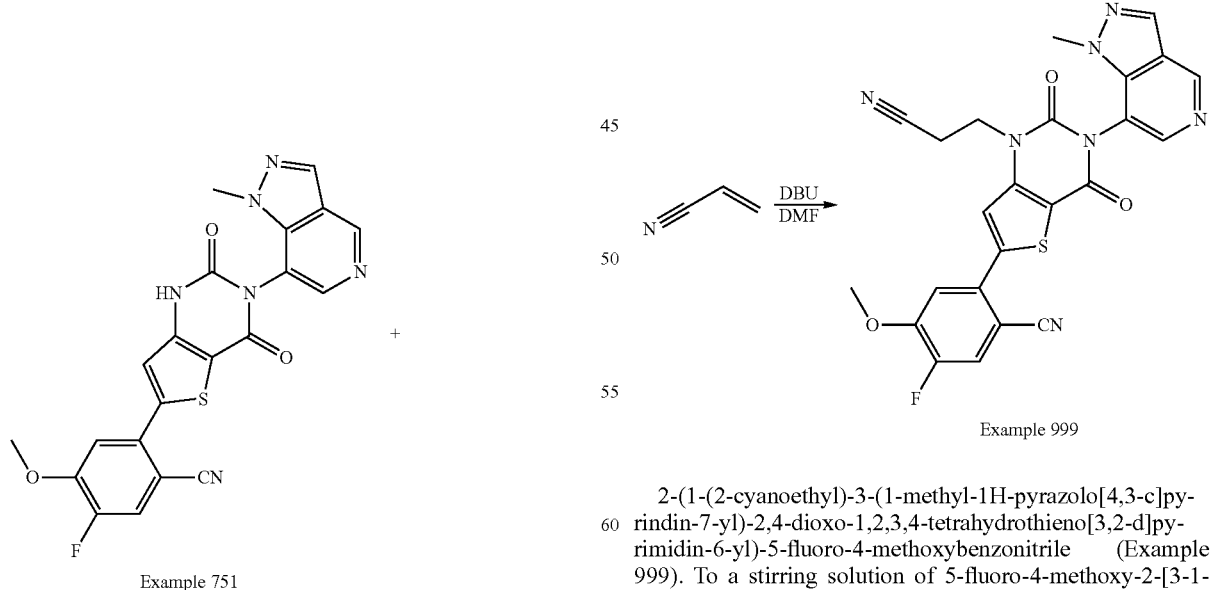

Example 999

2-(1-(2-cyanoethyl)-3-(1-methyl-1H-pyrazolo[4,3-c]pyridin-7-yl)-2,4-dioxo-1,2,3,4-tetrahydrothieno[3,2-d]pyrimidin-6-yl)-5-fluoro-4-methoxybenzonitrile (Example 999). To a stirring solution of 5-fluoro-4-methoxy-2-[3-1-methylpyrazolo[4,3-c]pyridin-7-yl)-2,4-dioxo-1H-thieno[3,2-d]pyrimidin-6-yl]benzonitrile (Example 751) (TFA salt) (42 mg, 0.075 mmol, 1.0 equiv.), in DMF (0.13 mL, 0.54 M), was added acrylonitrile (0.15 mL, 2.24 mmol, 30 equiv.) followed by DBU (22 µL, 0.15 mmol, 2.0 equiv). The reaction mixture stirred for 12 hours at 80° C. after which the mixture was diluted with water (0.2 mL) and TFA (0.5 mL). The reaction mixture was then filtered through an acrodisc, and purified directly by RP-HPLC (0.1% TFA-ACN in 0.1% TFA Water. Column: Gemini 5 μM, NX-C18 110 Angstrom, 250×21.2 mm) to give the title compound Example 999 as a trifluoroacetate salt.

ES/MS: 501.8 (M+).

$^1$H NMR (400 MHz, DMSO-d6) δ 9.35 (s, 1H), 8.58 (s, 1H), 8.52 (s, 1H), 8.20-8.08 (m, 2H), 7.62 (d, J=8.1 Hz, 1H), 4.56 (dt, J=14.2, 7.1 Hz, 1H), 4.40 (dt, J=14.3, 6.2 Hz, 1H), 4.06 (s, 3H), 3.95 (s, 3H), 3.09 (t, J=6.7 Hz, 2H).

Examples 1000-1001

The following Examples were made in an analogous fashion according to Procedure 121 and are shown below in Table 49. To prepare the below Examples, different reagents/starting materials were used than some of those described in Procedure 121 and are noted in the last column of Table 49—"Changes to Procedure 121: Different Reagents/Starting Materials".

TABLE 49

Examples 1000-1001

| Example | Structure | ES/MS m/z | 1H-NMR | Changes to Procedure 121: Different Reagents/ Starting Materials |
|---|---|---|---|---|
| 1000 | 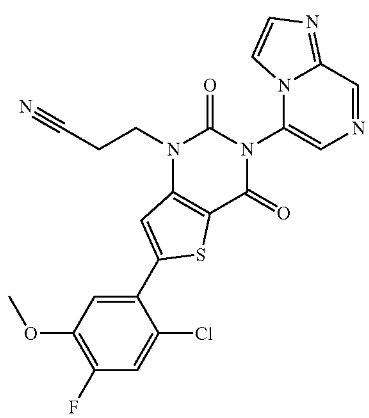 [SMILES: COc1cc(-c2cc3c(s2)c(=O)n(-c2cncc4nccn24)c(=O)n3CCC#N)c(Cl)cc1F] | 496.7 | 1H NMR (400 MHz, DMSO-d6) δ 9.23 (s, 1H), 8.45 (t, J = 1.0 Hz, 1H), 8.17 (s, 1H), 8.00 (s, 1H), 7.92 (d, J = 1.2 Hz, 1H), 7.76 (d, J = 11.0 Hz, 1H), 7.52 (d, J = 8.8 Hz, 1H), 4.51-4.42 (m, 2H), 3.97 (s, 3H), 3.02 (t, J = 6.6 Hz, 2H). | Example 978 |
| 1001 | 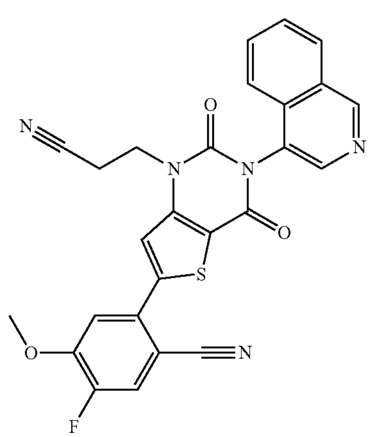 [SMILES: COc1cc(-c2cc3c(s2)c(=O)n(-c2cncc4ccccc24)c(=O)n3CCC#N)c(C#N)cc1F] | 497.7 | 1H NMR (400 MHz, DMSO-d6) δ 9,49 (d, J = 0.9 Hz, 1H), 8.59 (s, 1H), 8.35-8.28 (m, 1H), 8.19-8.07 (m, 2H), 7.98-7.90 (m, 1H), 7.87-7.75 (m, 2H), 7.60 (d, J = 8.1 Hz, 1H), 4.55-4.36 (m, 2H), 4.09 (s, 3H), 3.05 (t, J = 6,8 Hz, 2H). | Example 537 |

Procedure 122: Example 1002

Procedure 123: Example 1003 and Example 1004

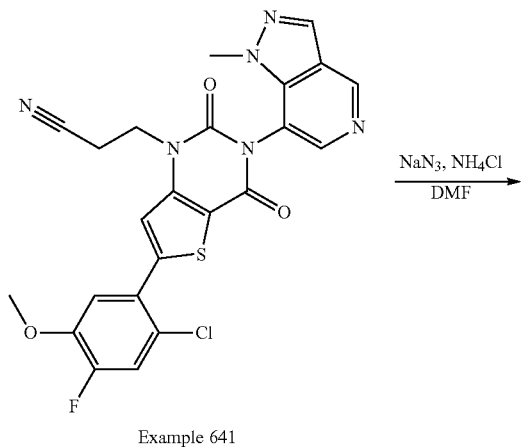

Example 641

NaN₃, NH₄Cl
――――→
DMF

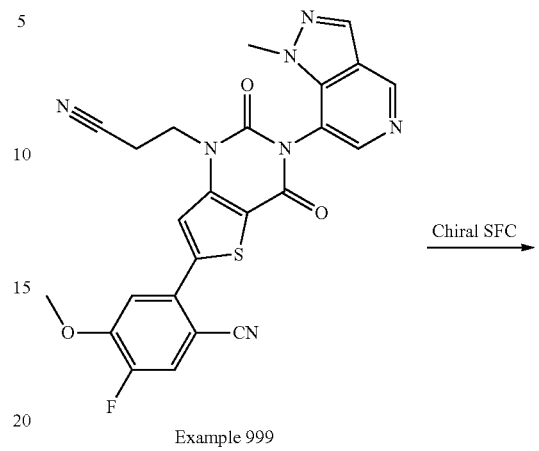

Example 999

Chiral SFC
――――→

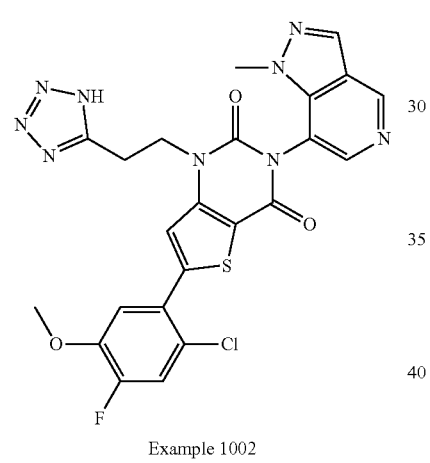

Example 1002

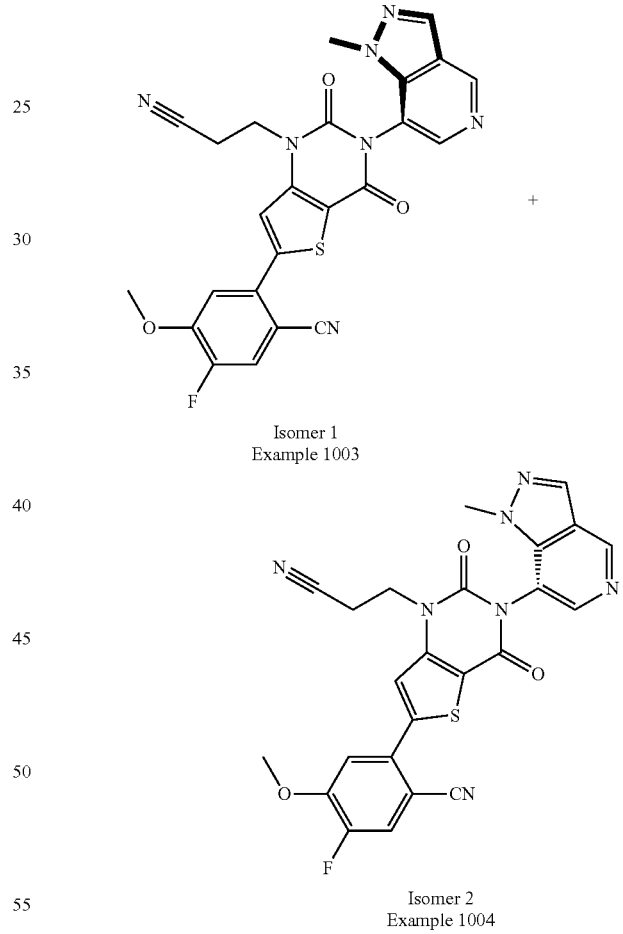

Isomer 1
Example 1003

+

Isomer 2
Example 1004

6-(2-chloro-4-fluoro-5-methoxy-phenyl)-3-(1-methylpyrazolo[4,3-c]pyridin-7-yl)-1-[2-(1H-tetrazol-5-yl)ethyl]thieno[3,2-d]pyrimidine-2,4-dione (Example 1002): To a solution of 3-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]propanenitrile (Example 641) (HCl salt) (60 mg, 0.11 mmol) in DMF (0.48 mL) was added NaN₃ (14.3 mg, 0.22 mmol) and NH₄Cl (11.7 mg, 0.22 mmol). The reaction mixture was heated to 100° C. for 2 h after which the reaction mixture was cooled to rt and concentrated under reduced pressure. The reaction mixture was diluted with 5:1 MeCN/water (1.2 mL) and the mixture was filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 1002 as a trifluoroacetate salt.

ES/MS: 553.8 (M⁺).

¹H NMR (400 MHz, DMSO-d₆) δ 9.24 (s, 1H), 8.49 (s, 1H), 8.38 (s, 1H), 7.75 (d, J=11.1 Hz, 2H), 7.50 (d, J=8.9 Hz, 1H), 4.55 (h, J=7.5 Hz, 2H), 3.95 (d, J=33.6 Hz, 6H), 3.42 (t, J=6.7 Hz, 2H).

2-[1-(2-cyanoethyl)-3-(1-methylpyrazolo[4,3-c]pyridin-7-yl)-2,4-dioxo-thieno[3,2-d]pyrimidin-6-yl]-5-fluoro-4-methoxy-benzonitrile (Example 1003 and Example 1004): 2-[6-(2-chloro-4-fluoro-5-methoxy-phenyl)-3-(4-isoquinolyl)-2,4-dioxo-thieno[3,2-d]pyrimidin-1-yl]acetonitrile (Example 999) as a mixture of 2 atropisomers was separated by chiral SFC (IB Sum 21×250 mm column with 30% MeOH cosolvent) to give two enantiomers, which were assigned as Isomer 1 and Isomer 2. The stereochemistry was assigned by analogy to Example 438, with Example 1003 being the more active isomer.
Isomer 1:

2-[1-(2-cyanoethyl)-3-(1-methylpyrazolo[4,3-c]pyridin-7-yl)-2,4-dioxo-thieno[3,2-d]pyrimidin-6-yl]-5-fluoro-4-methoxy-benzonitrile (Example 1003)

ES/MS: 501.8 (M+).
1H NMR (400 MHz, DMSO-d6) δ 9.31 (s, 1H), 8.55 (s, 1H), 8.49 (s, 1H), 8.19-8.08 (m, 2H), 7.62 (d, J=8.1 Hz, 1H), 4.56 (dt, J=14.3, 7.1 Hz, 1H), 4.46-4.34 (m, 1H), 4.06 (s, 3H), 3.92 (s, 3H), 3.09 (t, J=6.7 Hz, 2H).
Isomer 2:

2-[1-(2-cyanoethyl)-3-(1-methylpyrazolo[4,3-c]pyridin-7-yl)-2,4-dioxo-thieno[3,2-d]pyrimidin-6-yl]-5-fluoro-4-methoxy-benzonitrile (Example 1004)

ES/MS: 501.8 (M+).
1H NMR (400 MHz, DMSO-d6) δ 9.34 (s, 11H), 8.57 (d, J=1.0 Hz, 1H), 8.51 (s, 1H), 8.19-8.08 (m, 2H), 7.62 (d, J=8.1 Hz, 1H), 4.56 (dt, J=14.2, 7.1 Hz, 1H), 4.41 (dt, J=14.5, 6.2 Hz, 1H), 4.06 (s, 3H), 3.94 (s, 3H), 3.09 (t, J=6.6 Hz, 2H).

Procedure 124: Example 1005 ieno[3,2-d]pyrimidin-1(2H)-yl)cyclopropane-1-carbonitrile (Example 1005): To a stirring solution of 6-(2-chloro-4-fluoro-5-methoxy-phenyl)-3-(1-methylpyrazolo[4,3-c]pyridin-7-yl)-1H-thieno[3,2-d]pyrimidine-2,4-dione (Example 505) (HCl salt) (50 mg, 0.10 mmol), (±) trans-2-(4,4,5,5-tetramethyl-1,3,2-dioxaborolan-2-yl)cyclopropanecarbonitrile (39.1 mg, 0.20 mmol), Cu(II)acetate-H2O (30.3 mg, 0.15 mmol) in DMF (0.3 mL) was added Na2CO3 (21.4 mg, 0.22 mmol, 2.0 equiv.). The reaction mixture was degassed with an O2 balloon and heated to 50° C. for 48 h after which the reaction mixture was cooled to rt and concentrated under reduced pressure. The reaction mixture was diluted with 5:1 MeCN/water (1.2 mL) and the mixture was filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 1005 as a trifluoroacetate salt.

ES/MS: 522.8 (M+).
$^{1}$H NMR (400 MHz, DMSO-$d_6$) δ 9.33 (s, 1H), 8.55 (d, J=2.3 Hz, 1H), 8.42 (s, 1H), 7.77 (d, J=11.0 Hz, 1H), 7.66 (d, J=1.8 Hz, 1H), 7.50 (dd, J=8.9, 5.4 Hz, 1H), 3.97 (s, 3H), 3.92 (s, 3H), 3.86 (dt, J=6.8, 3.5 Hz, 1H), 2.43 (dt, J=6.8, 3.5 Hz, 1H), 2.12-1.98 (m, 1H), 1.79-1.68 (m, 1H).

Procedure 125: Example 1006 and Example 1007

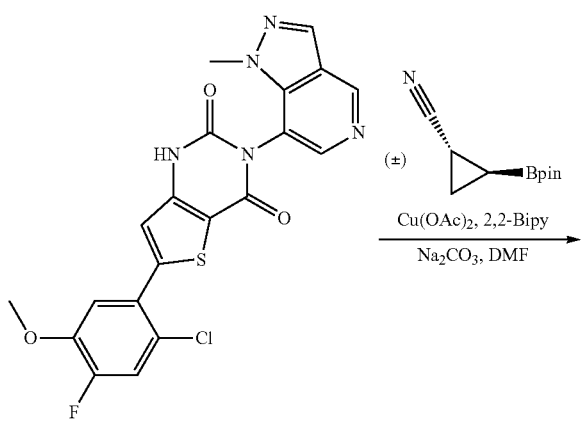

Example 505

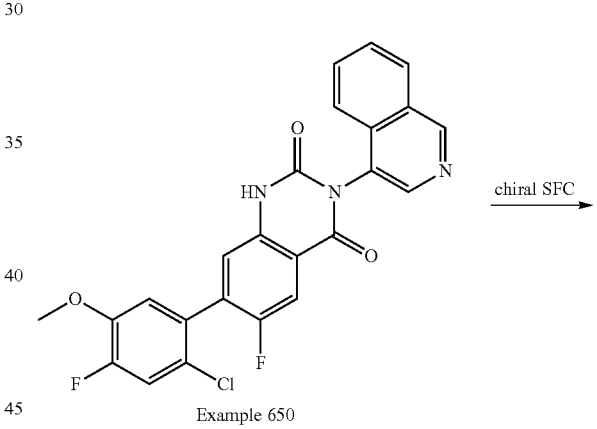

Example 650

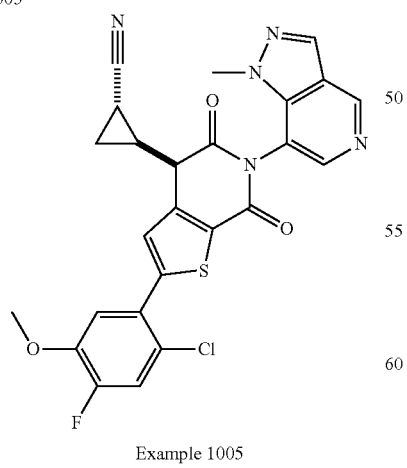

Example 1005

2-(6-(2-chloro-4-fluoro-5-methoxyphenyl)-3-(1-methyl-1H-pyrazolo[4,3-c]pyridin-7-yl)-2,4-dioxo-3,4-dihydroth-

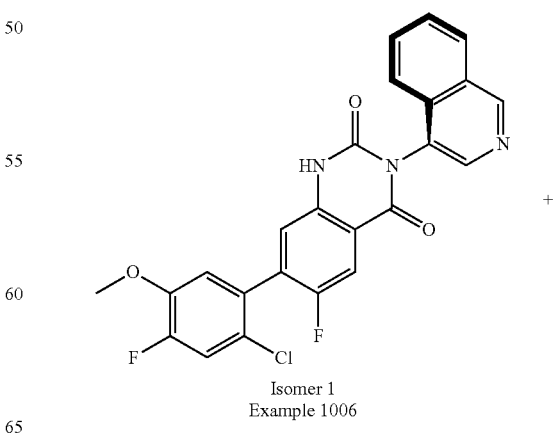

Isomer 1
Example 1006

1401
-continued

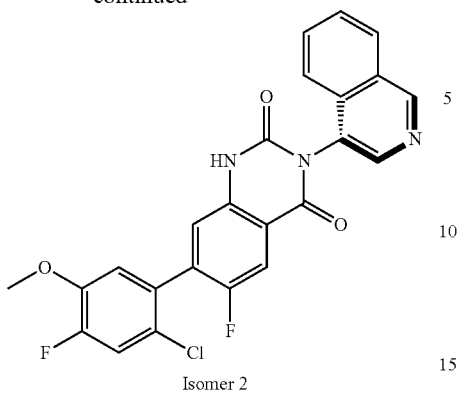

Isomer 2
Example 1007

7-(2-chloro-4-fluoro-5-methoxy-phenyl)-6-fluoro-3-(4-isoquinolyl)-1H-quinazoline-2,4-dione (Example 1006 and Example 1007): 7-(2-chloro-4-fluoro-5-methoxy-phenyl)-6-fluoro-3-(4-isoquinolyl)-1H-quinazoline-2,4-dione (Example 650) as a mixture of 2 enantiomers was separated by chiral SFC (IB 5 um-4.6×$^{100}$ mm column with 35% EtOH cosolvent) to give two enantiomers, which were assigned as Isomer 1 and Isomer 2. The stereochemistry was assigned by analogy to Example 438, with Example 1006 being the more active isomer.

Isomer 1:

7-(2-chloro-4-fluoro-5-methoxy-phenyl)-6-fluoro-3-(4-isoquinolyl)-1H-quinazoline-2,4-dione (Example 1006)

ES/MS: 465.8 (M+).

1H NMR (400 MHz, DMSO-d$_6$) δ 11.93 (s, 1H), 9.48 (s, 1H), 8.61 (s, 1H), 8.37-8.27 (m, 1H), 7.93 (d, J=8.2 Hz, 1H), 7.86-7.76 (m, 3H), 7.69 (d, J=11.0 Hz, 1H), 7.33 (d, J=8.9 Hz, 1H), 7.26 (d, J=5.8 Hz, 1H), 3.90 (s, 3H).

Isomer 2:

7-(2-chloro-4-fluoro-5-methoxy-phenyl)-6-fluoro-3-(4-isoquinolyl)-1H-quinazoline-2,4-dione (Example 1007)

ES/MS: 465.8 (M+).

1H NMR (400 MHz, DMSO-d$_6$) δ 11.93 (s, 1H), 9.49 (s, 1H), 8.62 (s, 1H), 8.38-8.24 (m, 1H), 7.94 (d, J=8.3 Hz, 1H), 7.86-7.77 (m, 3H), 7.70 (d, J=11.0 Hz, 1H), 7.33 (d, J=8.8 Hz, 1H), 7.27 (d, J=6.0 Hz, 1H), 3.91 (s, 3H).

1402
Procedure 126: Example 1008 and Example 1009

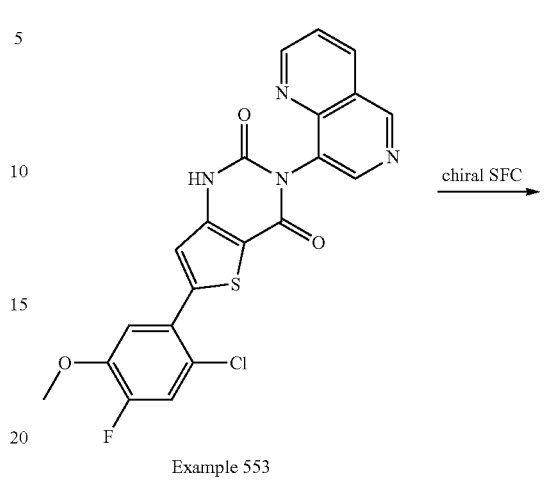

Example 553

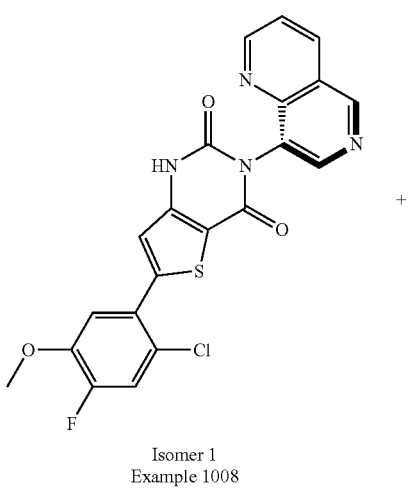

Isomer 1
Example 1008

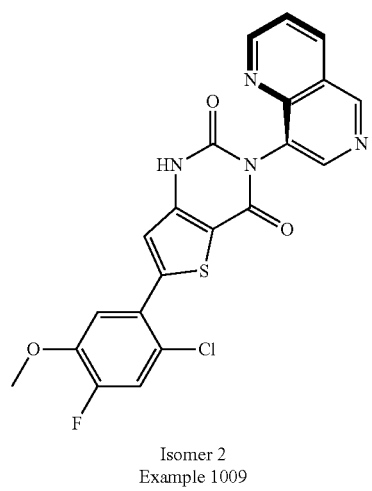

Isomer 2
Example 1009

6-(2-chloro-4-fluoro-5-methoxy-phenyl)-3-(1,6-naphthyridin-8-yl)-1H-thieno[3,2-d]pyrimidine-2,4-dione (Example 1008 and Example 1009): 6-(2-chloro-4-fluoro-5-methoxyphenyl)-3-(1,6-naphthyridin-8-yl)-1H-thieno[3,2-d]pyrimidine-2,4-dione (Example 553) as a mixture of 2 enantiomers was separated by chiral SFC (IB 5 um-4.6×$^{100}$ mm column with 35% EtOH cosolvent) to give two enantiomers, which were assigned as Isomer 1 and Isomer 2. The stereochemistry was assigned by analogy to Example 438, with Example 1009 being the more active isomer.

Isomer 1:

6-(2-chloro-4-fluoro-5-methoxy-phenyl)-3-(1,6-naphthyridin-8-yl)-1H-thieno[3,2-d]pyrimidine-2,4-dione (Example 1008)

ES/MS: 454.7 (M$^+$).

1H NMR (400 MHz, DMSO-d$_6$) δ 12.28 (s, 1H), 9.56 (s, 1H), 9.12 (dd, J=4.4, 1.6 Hz, 1H), 8.85 (s, 1H), 8.73 (dd, J=8.4, 1.7 Hz, 1H), 7.79 (dd, J=8.3, 4.3 Hz, 1H), 7.69 (d, J=11.0 Hz, 1H), 7.47 (d, J=8.8 Hz, 1H), 7.30 (s, 1H), 3.94 (s, 3H).

Isomer 2:

6-(2-chloro-4-fluoro-5-methoxy-phenyl)-3-(1,6-naphthyridin-8-yl)-1H-thieno[3,2-d]pyrimidine-2,4-dione (Example 1009)

ES/MS: 454.7 (M$^+$).

1H NMR (400 MHz, DMSO-d$_6$) δ 12.28 (s, 1H), 9.56 (s, 1H), 9.12 (dd, J=4.3, 1.7 Hz, 1H), 8.85 (s, 1H), 8.73 (dd, J=8.3, 1.7 Hz, 1H), 7.79 (dd, J=8.3, 4.2 Hz, 1H), 7.70 (d, J=11.0 Hz, 1H), 7.47 (d, J=8.9 Hz, 1H), 7.30 (s, 1H), 3.94 (s, 3H).

Procedure 127: Example 1010 and Example 1011

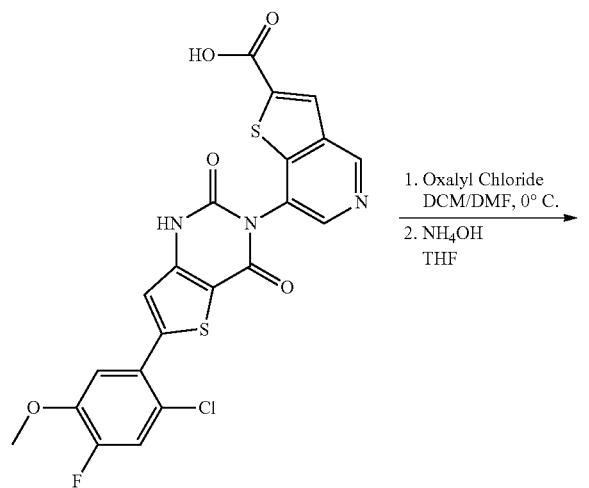

I-219

1. Oxalyl Chloride DCM/DMF, 0° C.
2. NH$_4$OH THF

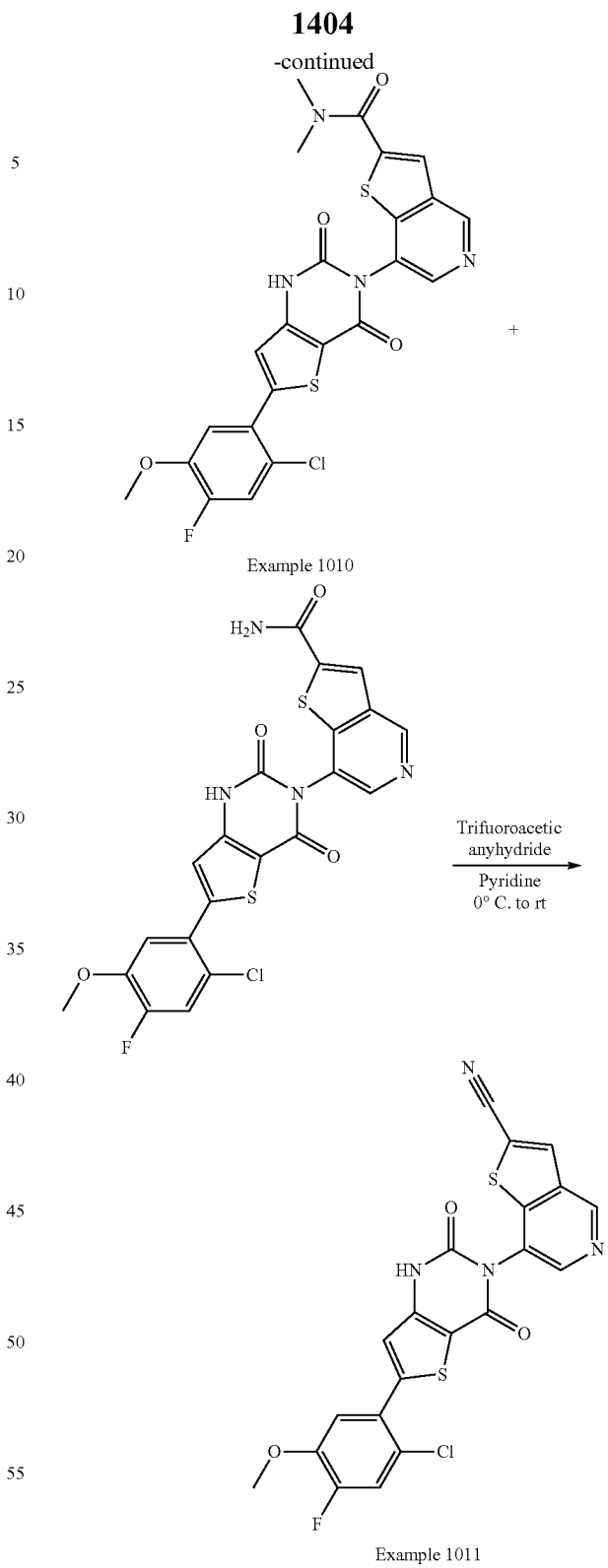

Example 1010

Trifluoroacetic anyhydride
Pyridine
0° C. to rt

Example 1011

7-[6-(2-chloro-4-fluoro-5-methoxy-phenyl)-2,4-dioxo-1H-thieno[3,2-d]pyrimidin-3-yl]-N,N-dimethyl-thieno[3,2-c]pyridine-2-carboxamide (Example 1010): To a mixture of 7-[6-(2-chloro-4-fluoro-5-methoxy-phenyl)-2,4-dioxo-1H-thieno[3,2-d]pyrimidin-3-yl]thieno[3,2-c]pyridine-2-carboxylic acid (1-219) (16.3 mg, 0.03 mmol) in 1:1 DCM/DMF (0.81 mL) at 0° C. was added oxalyl chloride (5.5 µL, 0.06 mmol). The resulting mixture was then warmed to ambient temperature and stirred for one hour. The mixture was then concentrated under reduced pressure and subsequently dissolved in THF (1.0 mL) followed by the addition of NH₄OH (0.7 mL). The mixture was then stirred for one hour at ambient temperature. The crude residue was dissolved in ACN (1 mL), water (0.4 mL) and TFA (0.2 mL), and purified directly by RP-HPLC (0.1% TFA-ACN in 0.1% TFA Water, Column: Gemini 5 μM, NX-C18 110 Angstrom, 250×21.2 mm) to give the products as trifluoroacetate salts.

ES/MS: 530.7 (M+).

1H NMR (400 MHz, DMSO-d6) δ 12.41 (s, 1H), 9.26 (s, 1H), 8.60 (s, 1H), 8.11 (s, 1H), 7.71 (d, J=11.0 Hz, 1H), 7.46 (d, J=8.9 Hz, 1H), 7.30 (s, 1H), 3.94 (s, 3H), 3.30 (s, 3H), 3.05 (s, 3H).

7-[16-(2-chloro-4-fluoro-5-methoxy-phenyl)-2,4-dioxo-1H-thieno[3,2-d]pyrimidin-3-yl]thieno[3,2-c]pyridine-2-carbonitrile (Example 1011): To a solution of 7-[6-(2-chloro-4-fluoro-5-methoxy-phenyl)-2,4-dioxo-1H-thieno[3,2-d]pyrimidin-3-yl]thieno[3,2-c]pyridine-2-carboxamide (10 mg, 0.02 mmol) in pyridine (1 mL) was added trifluoroacetic anhydride (0.1 mL, 0.7 mmol) at 0° C. The resulting mixture was warmed to rt and stirred for 30 minutes. The crude residue was dissolved in ACN (1 mL), water (0.4 mL) and TFA (0.2 mL), and purified directly by RP-HPLC (0.1% TFA-ACN in 0.1% TFA Water, Column: Gemini 5 μM, NX-C18 110 Angstrom, 250×21.2 mm) to give the product as a trifluoroacetate salt.

ES/MS: 484.6 (M+).

1H NMR (400 MHz, DMSO-d6) δ 12.44 (s, 1H), 9.38 (s, 1H), 8.76 (s, 1H), 8.69 (s, 1H), 7.71 (d, J=11.0 Hz, 1H), 7.46 (d, J=8.9 Hz, 1H), 7.30 (s, 1H), 3.94 (s, 3H).

Procedure 128: Example 1012 and Example 1013

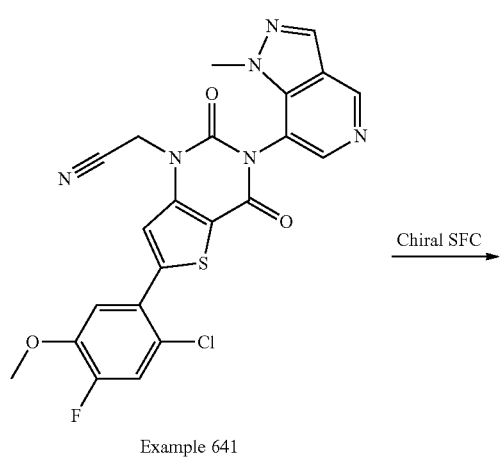

Example 641

Chiral SFC

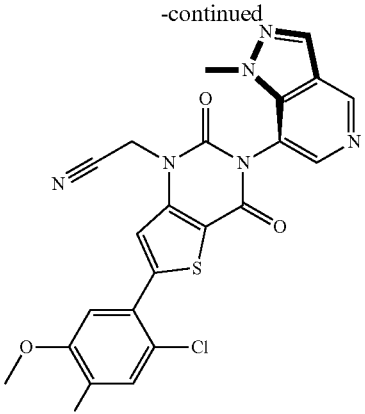

Isomer 1
Example 1012

-continued

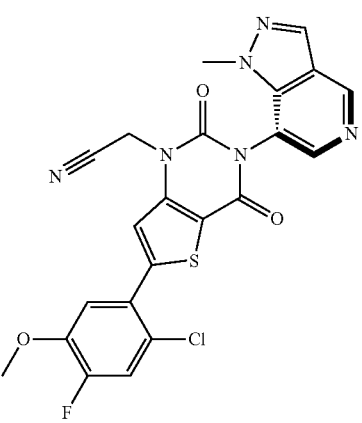

Isomer 2
Example 1013

2-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]acetonitrile (Example 1012 and Example 1013): 2-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]acetonitrile (Example 641) as a mixture of 2 enantiomers was separated by chiral SFC (IA 4.6×$^{100}$ mm column with 40% EtOH cosolvent) to give two enantiomers, which were assigned as Isomer 1 and Isomer 2. The stereochemistry was assigned by analogy to Example 438, with Example 1012 being the more active isomer.

Isomer 1:

2-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]acetonitrile (Example 1012)

ES/MS: 496.7 (M+).

1H NMR (400 MHz, DMSO-d6) δ 9.37 (s, 1H), 8.59 (d, J=4.4 Hz, 2H), 8.02 (s, 1H), 7.76 (d, J=11.0 Hz, 1H), 7.54 (d, J=8.8 Hz, 1H), 5.48-5.26 (m, 2H), 3.98 (s, 3H), 3.93 (s, 3H).

Isomer 2:

2-[6-(2-chloro-4-fluoro-5-methoxy-phenyl)-3-(1-methylpyrazolo[4,3-c]pyridin-7-yl)-2,4-dioxo-thieno[3,2-d]pyrimidin-1-yl]acetonitrile (Example 1013)

ES/MS: 496.8 (M+).

1H NMR (400 MHz, DMSO-d6) δ 9.35 (s, 1H), 8.58 (d, J=4.2 Hz, 2H), 8.02 (s, 1H), 7.76 (d, J=11.0 Hz, 1H), 7.54 (d, J=8.8 Hz, 1H), 5.48-5.27 (m, 2H), 3.98 (s, 3H), 3.93 (s, 3H).

Procedure 129: Example 1014

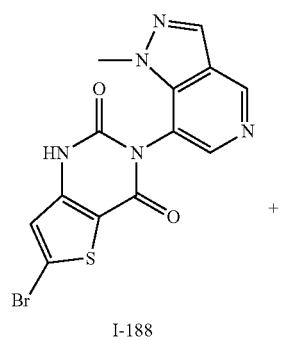

I-188

+

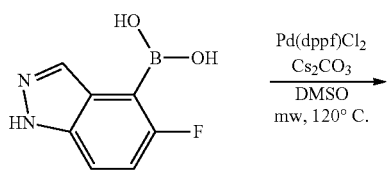

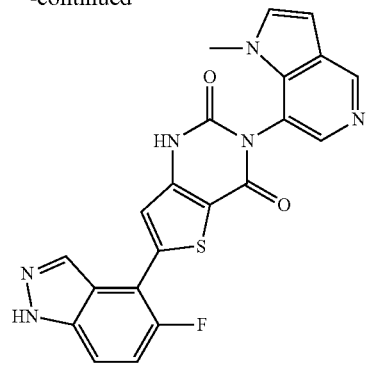

Example 1014

6-(5-fluoro-1H-indazol-4-yl)-3-(1-methylpyrazolo[4,3-c]pyridin-7-yl)-1H-thieno[3,2-d]pyrimidine-2,4-dione (Example 1014) To a 10 mL microwave vial containing a stir bar was added 6-bromo-3-(1-methylpyrazolo[4,3-c]pyridin-7-yl)-1H-thieno[3,2-d]pyrimidine-2,4-dione (HCl salt) (I-188) (25.0 mg, 0.06 mmol), (5-fluoro-1H-indazol-4-yl) boronic acid (21.7 mg, 0.12 mmol), Pd(dppf)Cl₂ (6.71 mg, 15 mol %) and Cs₂CO₃ (78.6 mg, 0.24 mmol). DMSO (1.0 mL) was added, and the reaction mixture was sealed with Teflon, degassed under Ar (5 min), and heated to 120° C. under microwave irradiation for 20 min. The crude product was diluted in acetonitrile/water/trifluoroacetic acid (1.5 mL; 5:1:0.2), filtered through an acrodisc, and purified directly by RP-HPLC (0.1% TFA-ACN in 0.1% TFA Water, Column: Gemini 5 μM, NX-C18 110 Angstrom, 250×21.2 mm) to give the product as a trifluoroacetate salt.

ES/MS: 433.8 (M+).

1H NMR (400 MHz, DMSO-d6) δ 13.16 (s, 1H), 11.04 (s, 1H), 8.12 (d, J=9.1 Hz, 2H), 7.57 (dd, J=9.0, 4.4 Hz, 1H), 7.53 (dd, J=9.3, 2.5 Hz, 1H), 7.23 (td, J=9.1, 2.5 Hz, 1H), 6.93 (d, J=9.2 Hz, 2H), 3.33 (s, 3H).

Examples 1015-1016

The following Examples were made in an analogous fashion according to Procedure 129 and are shown below in Table 50. To prepare the below Examples, different reagents/starting materials were used than some of those described in Procedure 129 and are noted in the last column of Table 50—"Changes to Procedure 129: Different Reagents/Starting Materials".

TABLE 50

Examples 1015-1016

| Example | Structure | ES/MS m/z | 1H-NMR | Changes to Procedure 129: Different Reagents/ Starting Materials |
|---|---|---|---|---|
| 1015 | 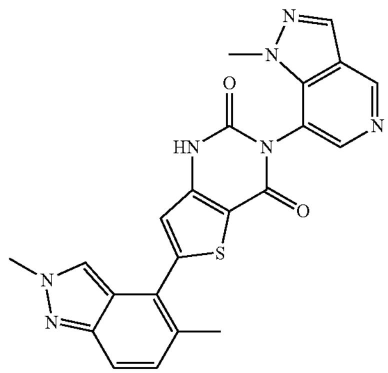 [SMILES: Cc1ccc2nn(C)cc2c1-c1cc2[nH]c(=O)n(-c3cncc4cnn(C)c34)c(=O)c2s1] | 443.8 | 1H NMR (400 MHZ, DMSO-d6) δ 12.50 (s, 1H), 9.35 (s, 1H), 8.57 (d, J = 15.5 Hz, 2H), 8.35 (s, 1H), 7.65 (d, J = 8.8 Hz, 1H), 7.27 (d, J = 8.8 Hz, 1H), 7.15 (s, 1H), 4.16 (s, 6H), 3.97 (s, 3H) | I-224 |
| 1016 | 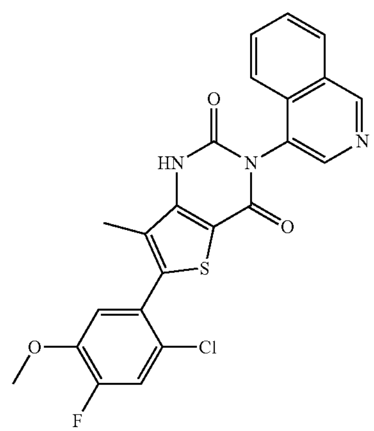 [SMILES: COc1cc(-c2sc3c(=O)n(-c4cncc5ccccc45)c(=O)[nH]c3c2C)c(Cl)cc1F] | 467.8 | 1H NMR (400 MHZ, DMSO) δ 12.21 (s, 1H), 9.48 (s, 1H), 8.61 (s, 1H), 8.31 (dd, J = 8.0, 1.3 Hz, 1H), 7.86-7.76 (m, 3H), 7.72 (d, J = 11.1 Hz, 1H), 7.31 (d, J = 8.9 Hz, 1H), 3.90 (s, 3H), 2.14 (s, 3H). | I-11; (2-chloro-4-fluoro-5-methoxy-phenyl)boronic acid |

Procedure 130: Example 1017

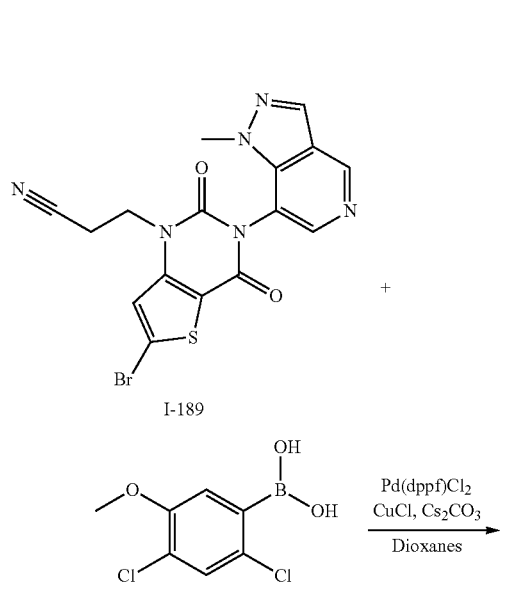

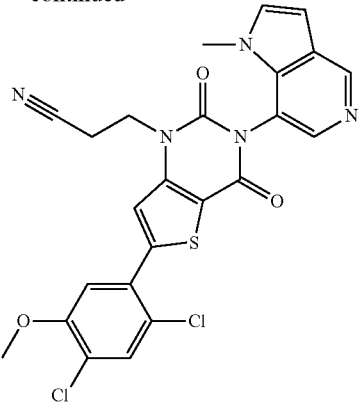

Example 1017

3-[6-(2,4-dichloro-5-methoxy-phenyl)-3-(1-methylpyrazolo[4,3-c]pyridin-7-yl)-2,4-dioxo-thieno[3,2-d]pyrimidin-1-yl]propanenitrile (Example 1017): To a microwave vial containing 3-[6-bromo-3-(1-methylpyrazolo[4,3-c]pyridin-7-yl)-2,4-dioxo-thieno[3,2-d]pyrimidin-1-yl]propanenitrile (I-189) (37.5 mg, 0.09 mmol) was added (2,4-dichloro-5- methoxy-phenyl)boronic acid (20.2 mg, 0.09 mmol), Pd(dppf)Cl₂ (6.5 mg, 10 mol %). CuCl (8.6 mg, 0.09 mmol), Cs₂CO₃ (85.0 mg, 0.26 mmol), and dioxanes (1.0 mL). The mixture was then degassed with Ar for 30 seconds, sealed, and irradiated under microwave conditions at 90° C. for 10 minutes. The resulting mixture was then filtered through Celite, concentrated under reduced pressure, diluted in acetonitrile/water/trifluoroacetic acid (1.5 mL; 5:1:0.2), filtered through an acrodisc, and purified directly by RP-HPLC (0.1% TFA-ACN in 0.1% TFA Water, Column: Gemini 5 μM, NX-C18 110 Angstrom, 250×21.2 mm) to give the product as a trifluoroacetate salt.

ES/MS: 527.1 (M⁺).

1H NMR (400 MHz, DMSO-d6) δ 9.32 (s, 1H), 8.56 (s, 1H), 8.50 (d, J=1.9 Hz, 1H), 8.03 (d, J=1.7 Hz, 1H), 7.88 (s, 1H), 7.50 (d, J=1.6 Hz, 1H), 4.63-4.36 (m, 2H), 3.99 (s, 3H), 3.93 (s, 3H), 3.09 (t, J=6.3 Hz, 2H).

Examples 1018-1025

The following Examples were made in an analogous fashion according to Procedure 130 and are shown below in Table 51. To prepare the below Examples, different reagents/starting materials were used than some of those described in Procedure 130 and are noted in the last column of Table 51—"Changes to Procedure 130: Different Reagents/Starting Materials".

TABLE 51

Examples 1018-1025

| Example | Structure | ES/MS m/z | 1H-NMR | Changes to Procedure 130: Different Reagents/ Starting Materials |
|---|---|---|---|---|
| 1018 | 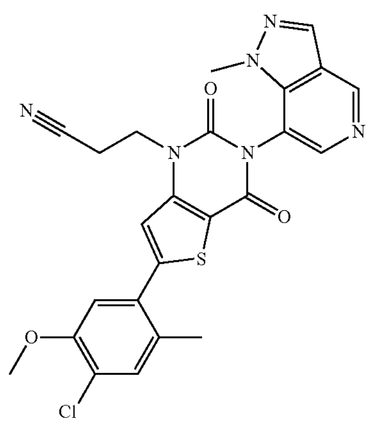 [SMILES: COc1cc(-c2cc3c(s2)c(=O)n(-c2cncc4cnn(C)c24)c(=O)n3CCC#N)c(C)cc1Cl] | 506.7 | 1H NMR (400 MHz, DMSO-d6) δ 9.30 (s, 1H), 8.53 (S, 1H), 8.47 (s, 1H), 7.83 (s, 1H), 7.54 (s, 1H), 7.25 (s, 1H), 4.47 (ddt, J = 46.9, 14.3, 6.4 Hz, 2H), 3.92 (d, J = 1.3 Hz, 6H), 3.06 (t, J = 6.4 Hz, 2H), 2.44 (s, 3H) | 2-(4-chloro-5-methoxy-2-methyl-phenyl)-4,4,5,5-tetramethyl-1,3,2-dioxaborolane |
| 1019 | 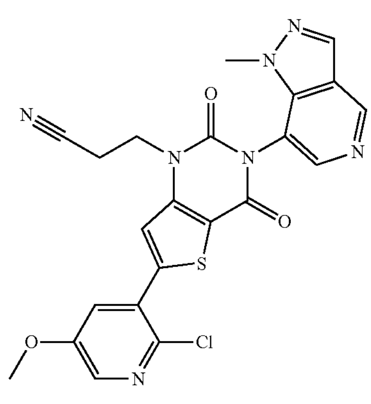 [SMILES: COc1cnc(Cl)c(-c2cc3c(s2)c(=O)n(-c2cncc4cnn(C)c24)c(=O)n3CCC#N)c1] | 493.8 | 1H NMR (400 MHz, DMSO-d6) δ 9.37 (s, 1H), 8.60 (s, 1H), 8.54 (s, 1H), 8.32 (d, J = 2.8 Hz, 1H), 8.14 (s, 1H), 7.95 (d, J = 2.9 Hz, 1H), 4.48 (ddt, J = 52.4, 14.3, 6.6 Hz, 2H), 3.97 (s, 3H), 3.94 (s, 3H), 3.13-3.05 (m, 2H) | (2-chloro-5-methoxy-3-pyridyl)boronic acid |

TABLE 51-continued

Examples 1018-1025

| Example | Structure | ES/MS m/z | 1H-NMR | Changes to Procedure 130: Different Reagents/ Starting Materials |
|---|---|---|---|---|
| 1020 | 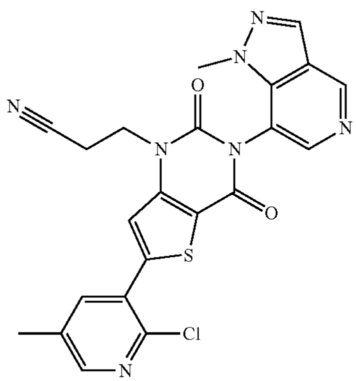 [SMILES: Cc1cnc(Cl)c(-c2cc3c(s2)c(=O)n(-c2cncc4cnn(C)c24)c(=O)n3CCC#N)c1] | 477.8 | 1H NMR (400 MHz, DMSO-d6) δ 9.33 (s, 1H), 8.56 (s, 1H), 8.50 (s, 1H), 8.41 (d, J = 2.3 Hz, 1H), 8.22 (d, J = 2.3 Hz, 1H), 8.11 (s, 1H), 4.62-4.32 (m, 3H), 3.93 (s, 2H), 3.08 (t, J = 6.5 Hz, 2H), 2.41 (s, 3H) | (2-chloro-5-methyl-3-pyridyl)boronic acid |
| 1021 | 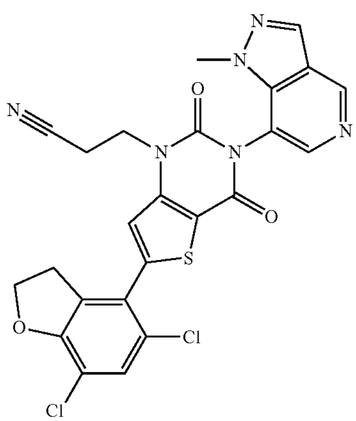 [SMILES: Cn1ncc2cncc(-n3c(=O)c4sc(-c5c(Cl)cc(Cl)c6c5CCO6)cc4n(CCC#N)c3=O)c21] | 540.7 | 1H NMR (400 MHz, DMSO-d6) δ 9.37 (s, 1H), 8.60 (s, 1H), 8.56 (s, 1H), 7.86 (s, 1H), 7.65 (s, 1H), 4.73 (t, J = 8.8 Hz, 2H), 4.44 (ddt, J = 44.2, 14.4, 6.5 Hz, 2H), 3.96 (s, 3H), 3.46-3.32 (m, 2H), 3.02 (td, J = 6.9, 6.5, 2.4 Hz, 2H) | (5,7-dichloro-2,3-dihydrobenzofuran-4-yl)boronic acid |
| 1022 | 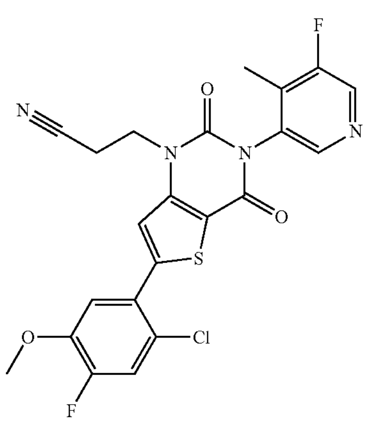 [SMILES: COc1cc(-c2cc3c(s2)c(=O)n(-c2cncc(F)c2C)c(=O)n3CCC#N)c(Cl)cc1F] | 488.7 | 1H NMR (400 MHz, DMSO-d6) δ 8.62 (s, 1H), 8.42 (S, 1H), 7.93 (s, 1H), 7.73 (d, J = 11.0 Hz, 1H), 7.52 (d, J = 8.9 Hz, 1H), 4.61-4.33 (m, 2H), 3.96 (s, 3H), 3.02 (q, J = 5.5, 4.3 Hz, 2H), 2.10 (s, 3H) | I-199; (2-chloro-4-fluoro-5-methoxy-phenyl)boronic acid |

TABLE 51-continued

Examples 1018-1025

| Example | Structure | ES/MS m/z | 1H-NMR | Changes to Procedure 130: Different Reagents/ Starting Materials |
|---------|-----------|-----------|--------|------------------------------------------------------------------|
| 1023 | 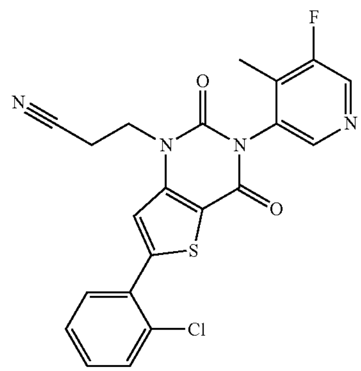 [SMILES: Cc1c(F)cncc1-n1c(=O)c2sc(-c3ccccc3Cl)cc2n(CCC#N)c1=O] | 440.8 | 1H NMR (400 MHz, DMSO-d6) δ 8.63 (s, 1H), 8.44 (s, 1H), 7.97 (s, 1H), 7.86 (dd, J = 6.0, 3.5 Hz. 1H), 7.70 (dd, J = 5.9, 3.4 Hz, 1H), 7.55 (dd, J = 5.9, 3.5 Hz, 2H), 4.55-4.18 (m, 2H), 3.01 (t, J = 6.6 Hz, 2H), 2.11 (d. J = 1.6 Hz, 3H) | I-199; (2-chlorophenyl) boronic acid |
| 1024 | 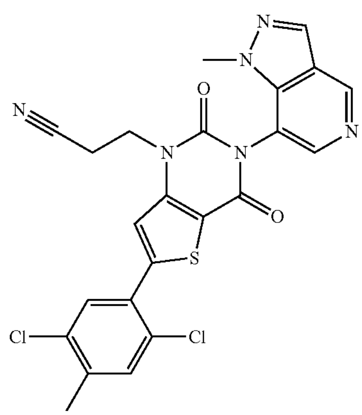 [SMILES: Cc1cc(Cl)c(-c2cc3c(s2)c(=O)n(-c2cncc4cnn(C)c24)c(=O)n3CCC#N)cc1Cl] | 512.7 | 1H NMR (400 MHz, DMSO-d6) δ 9.32 (s, 1H), 8.55 (s, 1H), 8.49 (s, 1H), 8.09 (s, 1H), 8.05 (s, 1H), 7.76 (s, 1H), 4.48 (ddt, J = 49.5, 14.2, 6.5 Hz, 2H), 3.92 (s, 3H), 3.08 (td, J = 6.6, 3.2 Hz, 2H), 2.41 (s, 3H) | (2,5-dichloro-4-methyl-phenyl)boronic acid |
| 1025 | 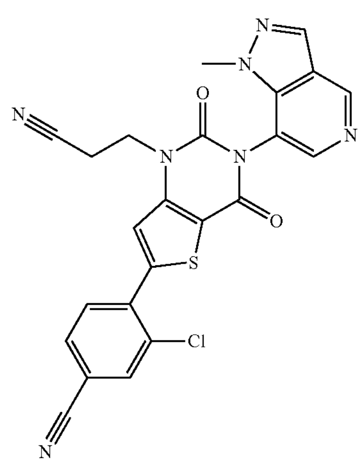 [SMILES: Cn1ncc2cncc(-n3c(=O)c4sc(-c5ccc(C#N)cc5Cl)cc4n(CCC#N)c3=O)c21] | 487.7 | 1H NMR (400 MHz, DMSO-d6) δ 9.32 (s, 1H), 8.55 (s, 1H), 8.49 (s, 1H), 8.34 (d, J = 1.6 Hz, 1H), 8.17 (s, 1H), 8.13 (d, J = 8.1 Hz, 1H), 8.08 (dd, J = 8.2, 1.6 Hz, 1H), 4.47 (ddt, J = 48.8, 14.3, 6.6 Hz, 2H), 3.93 (s, 3H), 3.07 (t, J = 6.6 Hz, 2H) | (2-chloro-4-cyano-phenyl)boronic acid |

Procedure 131: Example 1026 and Example 1027

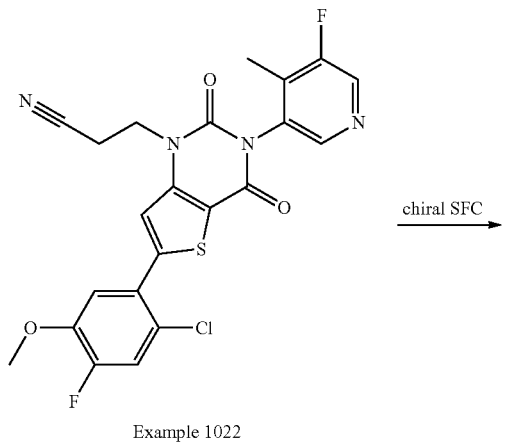

Example 1022

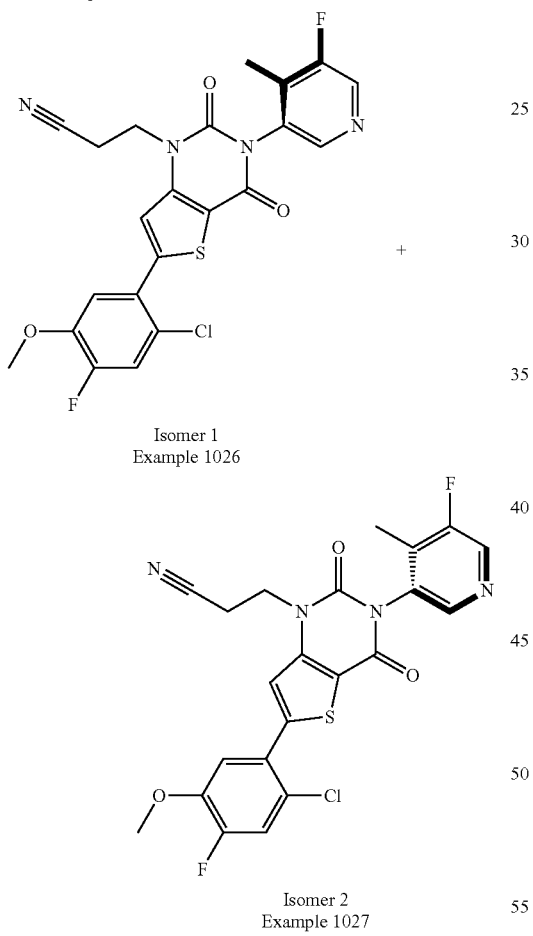

Isomer 1
Example 1026

Isomer 2
Example 1027

3-[6-(2-chloro-4-fluoro-5-methoxy-phenyl)-3-(5-fluoro-4-methyl-3-pyridyl)-2,4-dioxo-thieno[3,2-d]pyrimidin-1-yl]propanenitrile (Example 1026 and Example 1027): 3-[6-(2-chloro-4-fluoro-5-methoxy-phenyl)-3-(5-fluoro-4-methyl-3-pyridyl)-2,4-dioxo-thieno[3,2-d]pyrimidin-1-yl]propanenitrile (Example 1022) as a mixture of 2 enantiomers was separated by chiral SFC (IB 5 um-4.6×100 mm column with 30% MeOH cosolvent) to give two enantiomers, which were assigned as Isomer 1 and Isomer 2. The stereochemistry was assigned by analogy to Example 438, with Example 1026 being the more active isomer.

Isomer 1:

3-[6-(2-chloro-4-fluoro-5-methoxy-phenyl)-3-(5-fluoro-4-methyl-3-pyridyl)-2,4-dioxo-thieno[3,2-d]pyrimidin-1-yl]propanenitrile (Example 1026)

ES/MS: 488.7 (M+).

1H NMR (400 MHz, DMSO-d6) δ 8.62 (s, 1H), 8.42 (s, 1H), 7.93 (s, 1H), 7.73 (d, J=11.0 Hz, 1H), 7.52 (d, J=8.9 Hz, 1H), 4.56-4.31 (m, 2H), 3.96 (s, 3H), 3.07-3.00 (m, 2H), 2.10 (d, J=1.6 Hz, 3H).

Isomer 2:

3-[6-(2-chloro-4-fluoro-5-methoxy-phenyl)-3-(5-fluoro-4-methyl-3-pyridyl)-2,4-dioxo-thieno[3,2-d]pyrimidin-1-yl]propanenitrile (Example 1027)

ES/MS: 488.7 (M+).

1H NMR (400 MHz, DMSO-d6) δ 8.62 (s, 1H), 8.42 (s, 1H), 7.93 (s, 1H), 7.73 (d, J=11.0 Hz, 1H), 7.53 (d, J=8.9 Hz, 1H), 4.44 (ddt, J=44.0, 14.3, 6.5 Hz, 2H), 3.96 (s, 3H), 3.03 (t, J=6.6 Hz, 2H), 2.10 (d, J=1.6 Hz, 3H).

Procedure 132: Example 1028 and Example 1029

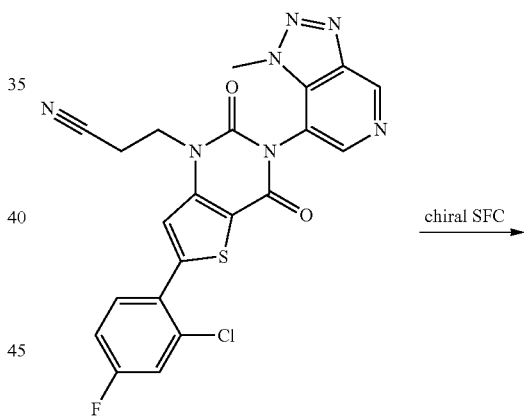

Example 733

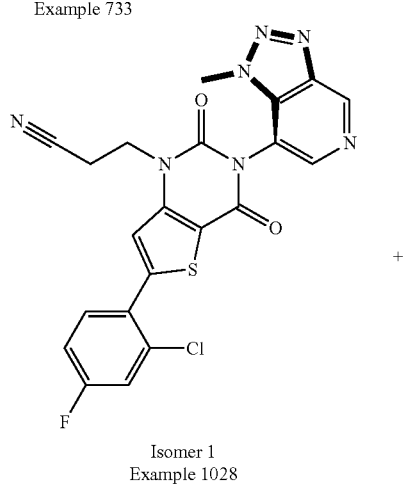

Isomer 1
Example 1028

Procedure 133: Example 1030 and Example 1031

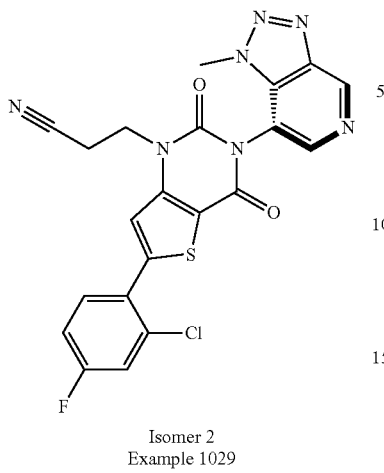

Isomer 2
Example 1029

3-[6-(2-chloro-4-fluoro-phenyl)-3-(1-methyltriazolo[4,5-c]pyridin-7-yl)-2,4-dioxo-thieno[3,2-d]pyrimidin-1-yl]propanenitrile (Example 1028 and Example 1029): 3-[6-(2-chloro-4-fluoro-phenyl)-3-(1-methyltriazolo[4,5-c]pyridin-7-yl)-2,4-dioxo-thieno[3,2-d]pyrimidin-1-yl]propanenitrile (Example 773) as a mixture of 2 enantiomers was separated by chiral SFC (IB 5 um-4.6×$^{100}$ mm column with 45% EtOH cosolvent) to give two enantiomers, which were assigned as Isomer 1 and Isomer 2. The stereochemistry was assigned by analogy to Example 438, with Example 1028 being the more active isomer.

Isomer 1:

3-[6-(2-chloro-4-fluoro-phenyl)-3-(1-methyltriazolo[4,5-c]pyridin-7-yl)-2,4-dioxo-thieno[3,2-d]pyrimidin-1-yl]propanenitrile (Example 1028)

ES/MS: 481.7 (M+).

1H NMR (400 MHz, DMSO-d6) δ 9.60 (s, 1H), 8.63 (s, 1H), 8.01 (s, 1H), 7.95 (dd, J=8.9, 6.1 Hz, 1H), 7.75 (dd, J=8.8, 2.7 Hz, 1H), 7.50 (td, J=8.5, 2.9 Hz, 1H), 4.60-4.32 (m, 2H), 4.19 (s, 3H), 3.06 (t, J=6.5 Hz, 2H).

Isomer 2:

3-[6-(2-chloro-4-fluoro-phenyl)-3-(1-methyltriazolo[4,5-c]pyridin-7-yl)-2,4-dioxo-thieno[3,2-d]pyrimidin-1-yl]propanenitrile (Example 1029)

ES/MS: 481.7 (M+).

1H NMR (400 MHz, DMSO-d6) δ 9.60 (s, 1H), 8.63 (s, 1H), 8.01 (s, 1H), 7.95 (dd, J=8.8, 6.0 Hz, 1H), 7.75 (dd, J=8.8, 2.6 Hz, 1H), 7.50 (td, J=8.4, 2.7 Hz, 1H), 4.59-4.36 (m, 2H), 4.19 (s, 3H), 3.06 (t, J=6.6 Hz, 2H).

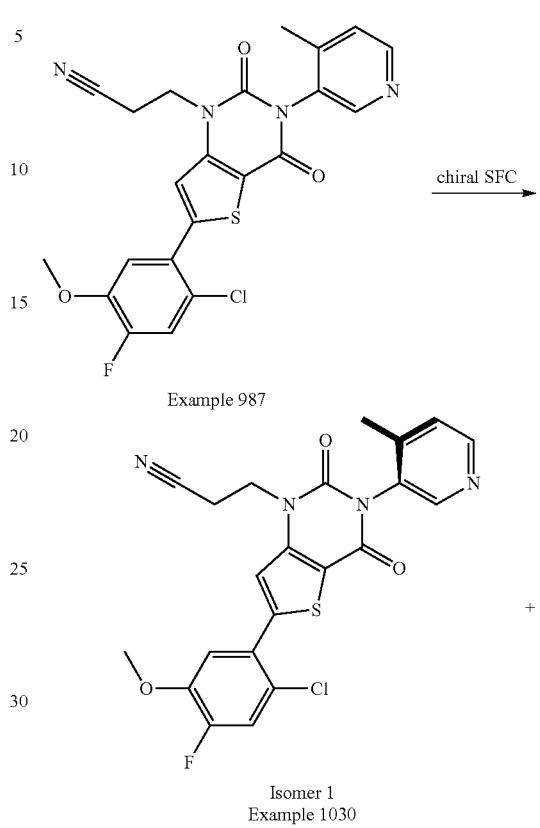

Example 987

Isomer 1
Example 1030

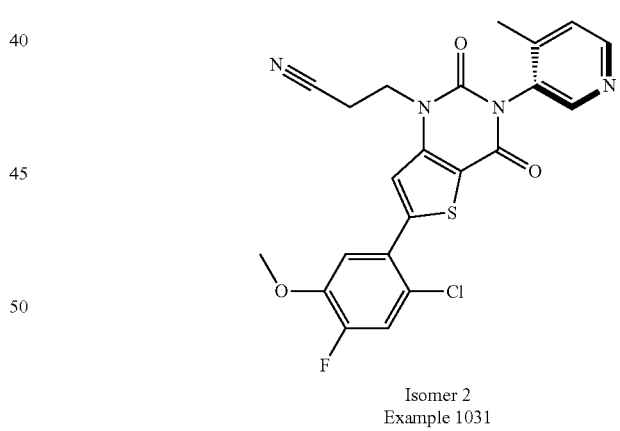

Isomer 2
Example 1031

3-[6-(2-chloro-4-fluoro-5-methoxy-phenyl)-3-(4-methyl-3-pyridyl)-2,4-dioxo-thieno[3,2-d]pyrimidin-1-yl]propanenitrile (Example 1030 and Example 1031): 3-[6-(2-chloro-4-fluoro-5-methoxy-phenyl)-3-(4-methyl-3-pyridyl)-2,4-dioxo-thieno[3,2-d]pyrimidin-1-yl]propanenitrile (Example 987) as a mixture of 2 isomers was separated by chiral SFC (AD-H 4.6×100 mm 5mic column with 50% MeOH cosolvent) to give two enantiomers, which were assigned as Isomer 1 and Isomer 2. The stereochemistry was assigned by analogy to Example 438, with Example 1030 being the more active isomer.

Isomer 1:

3-[16-(2-chloro-4-fluoro-5-methoxy-phenyl)-3-(4-methyl-3-pyridyl)-2,4-dioxo-thieno[3,2-d]pyrimidin-1-yl]propanenitrile (Example 1030)

ES/MS: 470.8 (M⁺).

¹H NMR (400 MHz, DMSO-d₆) δ 8.64-8.57 (m, 2H), 7.93 (s, 1H), 7.73 (d, J=11.0 Hz, 1H), 7.62 (d, J=5.1 Hz, 1H), 7.54 (d, J=8.8 Hz, 1H), 4.51 (dt, J=14.1, 6.9 Hz, 1H), 4.38 (dt, J=14.3, 6.1 Hz, 1H), 3.96 (s, 3H), 3.08-3.00 (m, 2H), 2.22 (s, 3H).

Isomer 2:

3-[16-(2-chloro-4-fluoro-5-methoxy-phenyl)-3-(4-methyl-3-pyridyl)-2,4-dioxo-thieno[3,2-d]pyrimidin-1-yl]propanenitrile (Example 1031)

ES/MS: 470.8 (M⁺).

¹H NMR (400 MHz, DMSO-d₆) δ 8.64 (d, J=6.9 Hz, 2H), 7.94 (s, 1H), 7.73 (d, J=11.0 Hz, 1H), 7.66 (d, J=5.2 Hz, 1H), 7.54 (d, J=8.9 Hz, 1H), 4.51 (dt, J=13.9, 6.8 Hz, 1H), 4.44-4.33 (m, 1H), 3.97 (s, 3H), 3.04 (t, J=6.3 Hz, 2H), 2.23 (s, 3H).

Procedure 134: Example 1032 and Example 1033

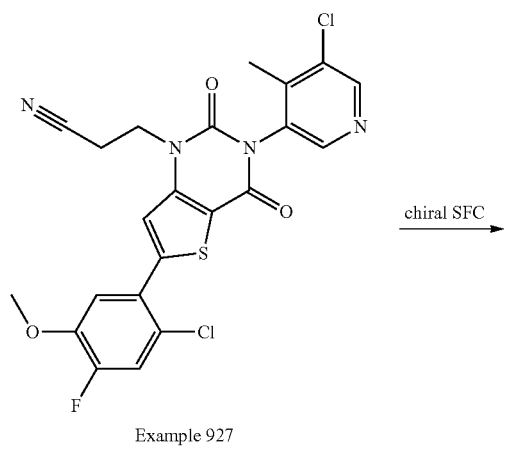

Example 927 chiral SFC

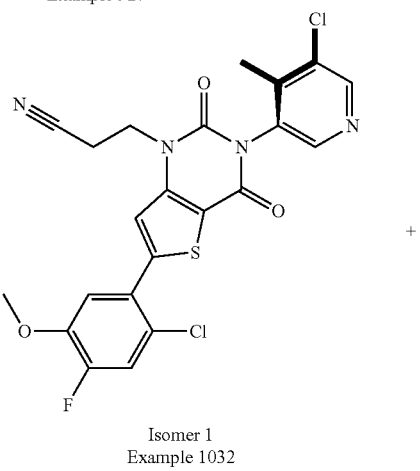

Isomer 1
Example 1032

+

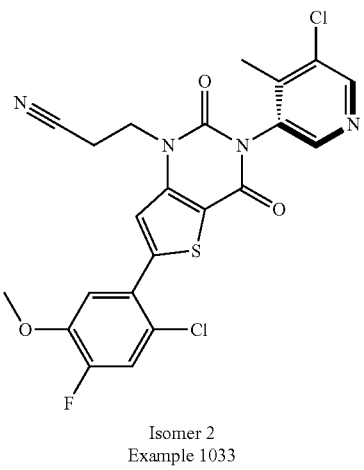

Isomer 2
Example 1033

3-[6-(2-chloro-4-fluoro-5-methoxy-phenyl)-3-(5-chloro-4-methyl-3-pyridyl)-2,4-dioxo-thieno[3,2-d]pyrimidin-1-yl]propanenitrile (Example 1032 and Example 1033): 3-[6-(2-chloro-4-fluoro-5-methoxy-phenyl)-3-(4-methyl-3-pyridyl)-2,4-dioxo-thieno[3,2-d]pyrimidin-1-yl]propanenitrile (Example 927) as a mixture of 2 isomers was separated by chiral SFC (ID 250×21 5 mic column with 35% MeOH cosolvent) to give two enantiomers, which were assigned as Isomer 1 and Isomer 2. The stereochemistry was assigned by analogy to Example 438, with Example 1032 being the more active isomer.

Isomer 1:

3-[6-(2-chloro-4-fluoro-5-methoxy-phenyl)-3-(5-chloro-4-methyl-3-pyridyl)-2,4-dioxo-thieno[3,2-d]pyrimidin-1-yl]propanenitrile (Example 1032)

ES/MS: 504.7 (M⁺).

¹H NMR (400 MHz, DMSO-d₆) δ 8.71 (s, 1H), 8.51 (s, 1H), 7.94 (s, 1H), 7.73 (d, J=11.0 Hz, 1H), 7.53 (d, J=8.8 Hz, 1H), 4.50 (dt, J=14.0, 6.9 Hz, 1H), 4.39 (dt, J=14.3, 6.2 Hz, 1H), 3.96 (s, 3H), 3.03 (t, J=6.5 Hz, 2H), 2.20 (s, 3H).

Isomer 2:

3-[6-(2-chloro-4-fluoro-5-methoxy-phenyl)₃-(5-chloro-4-methyl-3-pyridyl)-2,4-dioxo-thieno[3,2-d]pyrimidin-1-yl]propanenitrile (Example 1033)

1H NMR (400 MHz, DMSO-d6) δ 8.71 (s, 1H), 8.51 (s, 1H), 7.94 (s, 1H), 7.74 (d, J=11.1 Hz, 1H), 7.53 (d, J=8.8 Hz, 1H), 4.50 (dt, J=14.0, 6.9 Hz, 1H), 4.39 (dt, J=14.3, 6.2 Hz, 1H), 3.96 (s, 3H), 3.03 (t, J=6.6 Hz, 2H), 2.20 (s, 3H).

ES/MS: 504.7 (M⁺).

Procedure 135: Example 1034 and Example 1035

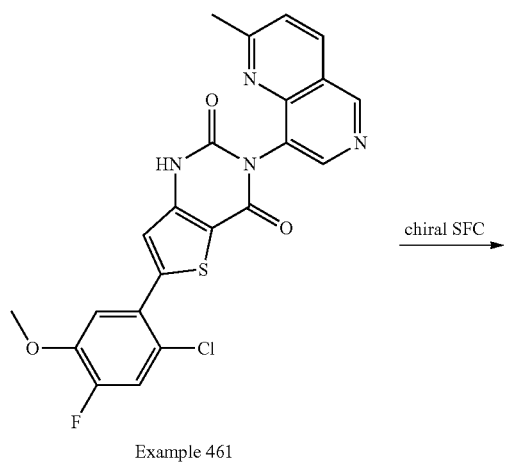

Example 461

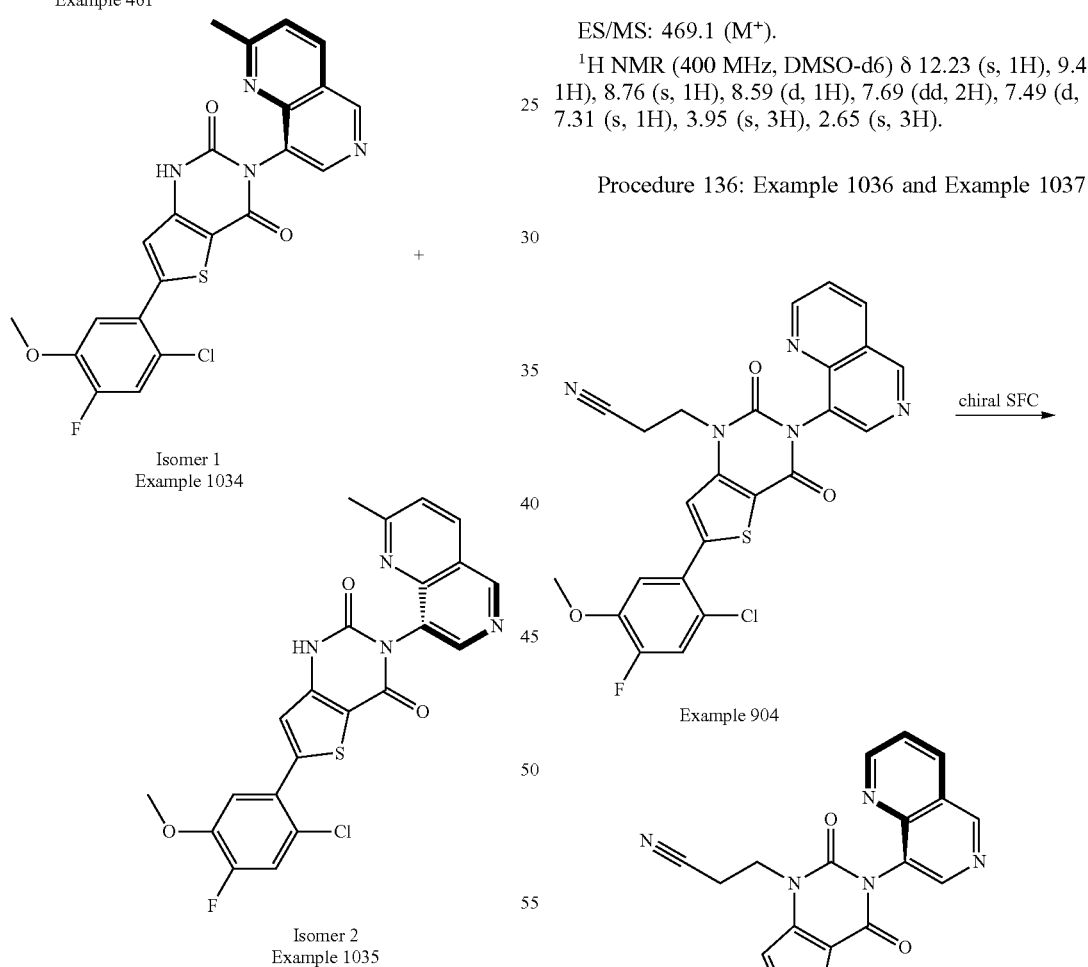

6-(2-chloro-4-fluoro-5-methoxyphenyl)-3-(2-methyl-1,6-naphthyridin-8-yl)thieno[3,2-d]pyrimidine-2,4(1H,3H)-dione (Example 1034 and Example 1035): 6-(2-chloro-4-fluoro-5-methoxyphenyl)-3-(2-methyl-1,6-naphthyridin-8-yl)thieno[3,2-d]pyrimidine-2,4(1H,3H)-dione (Example 461) as a mixture of 2 isomers was separated by chiral SFC (IA 5 um-21×250 mm column with 30% EtOH-NH₃ cosolvent) to give two enantiomers, which were assigned as Isomer 1 and Isomer 2. The stereochemistry was assigned by analogy to Example 438, with Example 1034 being the more active isomer.

Isomer 1:

6-(2-chloro-4-fluoro-5-methoxyphenyl)-3-(2-methyl-1,6-naphthyridin-8-yl)thieno[3,2-d]pyrimidine-2,4(1H,3H)-dione (Example 1034)

ES/MS: 469.1 (M⁺).
$^1$H NMR (400 MHz, DMSO-d6) δ 12.23 (s, 1H), 9.45 (s, 1H), 8.76 (s, 1H), 8.59 (d, 1H), 7.69 (dd, 2H), 7.49 (d, 1H), 7.31 (s, 1H), 3.95 (s, 3H), 2.65 (s, 3H).

Isomer 2:

6-(2-chloro-4-fluoro-5-methoxyphenyl)-3-(2-methyl-1,6-naphthyridin-8-yl)thieno[3,2-d]pyrimidine-2,4(1H,3H)-dione (Example 1035)

ES/MS: 469.1 (M⁺).
$^1$H NMR (400 MHz, DMSO-d6) δ 12.23 (s, 1H), 9.45 (s, 1H), 8.76 (s, 1H), 8.59 (d, 1H), 7.69 (dd, 2H), 7.49 (d, 1H), 7.31 (s, 1H), 3.95 (s, 3H), 2.65 (s, 3H).

Procedure 136: Example 1036 and Example 1037

-continued

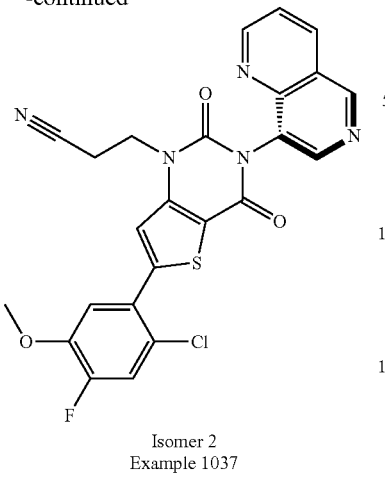

Isomer 2
Example 1037

3-(6-(2-chloro-4-fluoro-5-methoxyphenyl)-3-(1,6-naphthyridin-8-yl)-2,4-dioxo-3,4-dihydrothieno[3,2-d]pyrimidin-1(2H)-yl)propanenitrile (Example 1036 and Example 1037): 3-(6-(2-chloro-4-fluoro-5-methoxy phenyl)-3-(1,6-naphthyridin-8-yl)-2,4-dioxo-3,4-dihydrothieno[3,2-d]pyrimidin-1(2H)-yl)propanenitrile (Example 904) as a mixture of 2 isomers was separated by chiral SFC (AD-H Sum-21× 250 mm column with 45% EtOH cosolvent) to give two enantiomers, which were assigned as Isomer 1 and Isomer 2. The stereochemistry was assigned by analogy to Example 438, with Example 1036 being the more active isomer.

Isomer 1:

3-(6-(2-chloro-4-fluoro-5-methoxyphenyl)-3-(1,6-naphthyridin-8-yl)-2,4-dioxo-3,4-dihydrothieno[3,2-d]pyrimidin-1(2H)-yl)propanenitrile (Example 1036)

ES/MS: 508.4 (M+).

$^1$H NMR (400 MHz, DMSO) δ 9.58 (s, 1H), 9.11 (dd, 1H), 8.85 (s, 1H), 8.75 (dd, 1H), 7.97 (s, 1H), 7.81 (dd, 1H), 7.74 (d, 1H), 7.56 (d, 1H), 4.46 (t, 2H), 3.98 (s, 3H), 3.02 (td, 2H).

Isomer 2:

3-(6-(2-chloro-4-fluoro-5-methoxyphenyl)-3-(1,6-naphthyridin-8-yl)-2,4-dioxo-3,4-dihydrothieno[3,2-d]pyrimidin-1(2H)-yl)propanenitrile (Example 1037)

ES/MS: 508.4 (M+).

$^1$H NMR (400 MHz, DMSO) δ 9.58 (s, 1H), 9.11 (dd, 1H), 8.84 (s, 1H), 8.75 (dd, 1H), 7.97 (s, 1H), 7.81 (dd, 1H), 7.74 (d, 1H), 7.56 (d, 1H), 4.46 (t, 2H), 3.98 (s, 3H), 3.02 (td, 2H).

Procedure 137: Example 1038

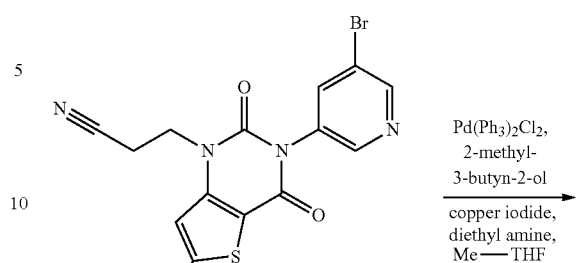

I-268

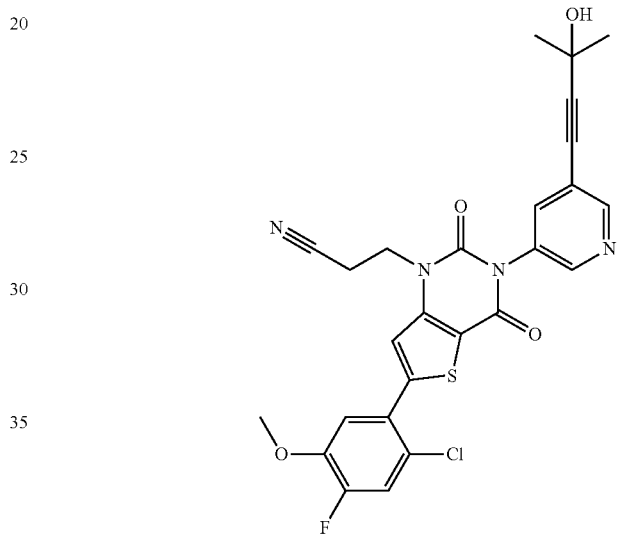

Example 1038

3-(6-(2-chloro-4-fluoro-5-methoxyphenyl)-3-(5-(3-hydroxy-3-methylbut-1-yn-1-yl)pyridin-3-yl)-2,4-dioxo-3,4-dihydrothieno[3,2-d]pyrimidin-1(2H)-yl)propanenitrile (Example 1038): 3-(3-(5-bromopyridin-3-yl)-6-(2-chloro-4-fluoro-5-methoxyphenyl)-2,4-dioxo-3,4-dihydrothieno[3,2-d]pyrimidin-1(2H)-yl)propanenitrile (I-268) (100 mg, 0.19 mmol), copper iodide (3.6 mg, 0.02 mmol), and 2-methyl-3-butyn-2-ol (78.5 mg, 0.93 mmol) were dissolved in Me-THF (6 ml). Then Bis(triphenylphosphine)palladium(II) dichloride (13.1 mg, 0.02 mmol) was add to the mixture followed by diethylamine (0.19 ml, 1.87 mmol). The reaction was heated to 80 C for two hours, then diluted with EtOAc and brine, the organic layer was kept, dried over sodium sulfate, and concentrated. The crude residue was purified by RP-HPLC (eluent: water/MeCN*0.1% TFA) to yield the product.

ES/MS: 539.8 (M+H+).

1H NMR (400 MHz, DMSO-d6) δ 8.65 (d, 1H), 8.56 (d, 1H), 7.97-7.89 (m, 2H), 7.73 (dd, 1H), 7.56-7.49 (m, 1H), 4.43 (t, 2H), 3.97 (s, 3H), 3.00 (t, 2H), 1.50 (s, 6H).

Example 1039

The following Examples were made in an analogous fashion according to Procedure 137 and are shown below in Table 52. To prepare the below Examples, different reagents/starting materials were used than some of those described in Procedure 137 and are noted in the last column of Table 52—"Changes to Procedure 137: Different Reagents/Starting Materials".

TABLE 52

Example 1039

| Example | Structure | ES/MS m/z | 1H-NMR | Changes to Procedure 137: Different Reagents/ Starting Materials |
|---|---|---|---|---|
| 1039 | 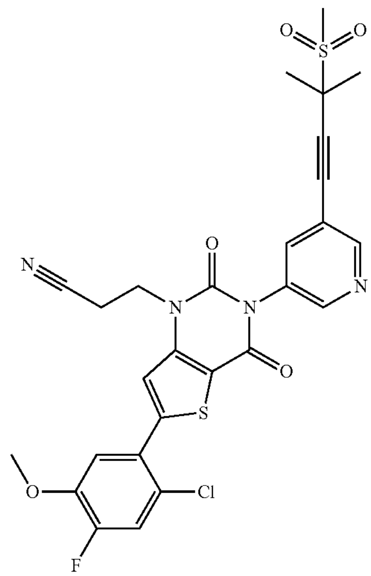 [SMILES: COc1cc(-c2cc3c(s2)c(=O)n(-c2cncc(C#CC(C)(C)S(C)(=O)=O)c2)c(=O)n3CCC#N)c(Cl)cc1F] | 601.4 | H NMR (400 MHz, DMSO-d6) δ 8.76 (d, 1H), 8.63 (d, 1H), 8.08 (t, 1H), 7.94 (s, 1H), 7.73 (d, 1H), 7.52 (d, 1H), 4.43 (t, 2H), 3.97 (s, 3H), 3.21 (s, 3H), 3.00 (t, 2H), 1.68 (s, 6H). | 3-methyl-3-(methylsulfonyl)but-1-yne |

Procedure 138: Example 1040

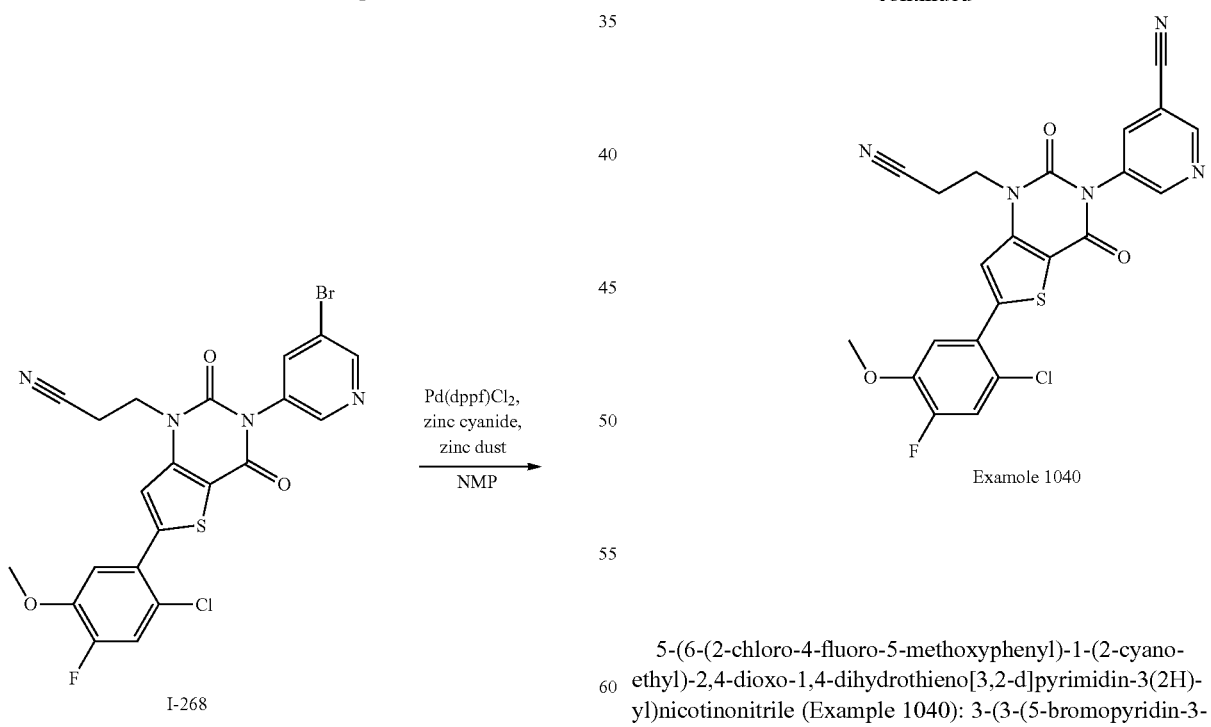

5-(6-(2-chloro-4-fluoro-5-methoxyphenyl)-1-(2-cyanoethyl)-2,4-dioxo-1,4-dihydrothieno[3,2-d]pyrimidin-3(2H)-yl)nicotinonitrile (Example 1040): 3-(3-(5-bromopyridin-3-yl)-6-(2-chloro-4-fluoro-5-methoxy phenyl)-2,4-dioxo-3,4-dihydrothieno[3,2-d]pyrimidin-1(2H)-yl)propanenitrile (I-268) (150 mg, 0.28 mmol), zinc cyanide (33 mg, 0.28 mmol), zinc dust (37 mg, 0.56 mmol) and Pd(dppf)Cl$_2$ (17 mg, 0.03 mmol) were dissolved in NMP (5 ml). The reaction was degassed and heated to 120° C. for 6 hours, then diluted with EtOAc and brine, the organic layer was kept, dried over sodium sulfate, and concentrated. The crude residue was purified by RP-HPLC (eluent: water/MeCN*0.1% TFA) to yield the product.

ES/MS: 482.1 (M+H).

$^1$H NMR (400 MHz, DMSO-d6) δ 9.14 (d, 1H), 8.93 (d, 1H), 8.49 (t, 1H), 7.96 (s, 1H), 7.74 (d, 1H), 7.52 (d, 1H), 4.44 (t, 2H), 3.97 (s, 3H), 3.00 (t, 2H).

Procedure 139: Example 1041 and Example 1042

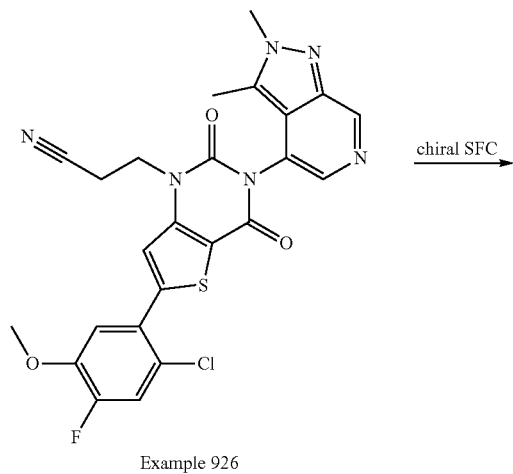
Example 926 chiral SFC

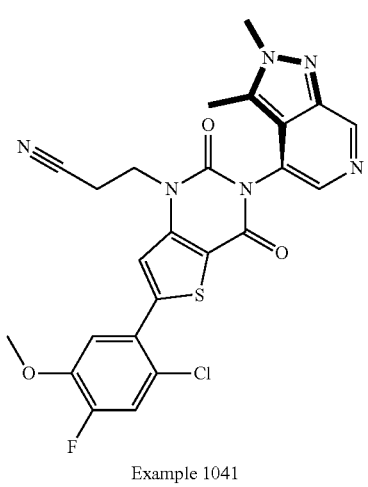
Example 1041

+

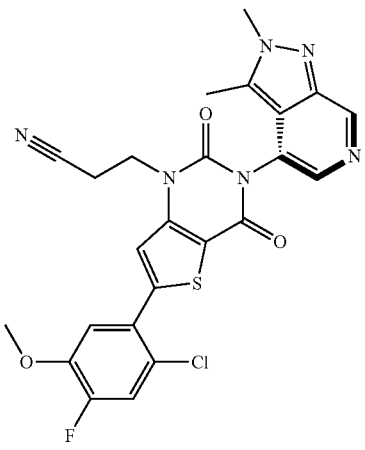
Example 1042

3-(6-(2-chloro-4-fluoro-5-methoxyphenyl)-3-(2,3-dimethyl-2H-pyrazolo[3,4-c]pyridin-4-yl)-2,4-dioxo-3,4-dihydrothieno[3,2-d]pyrimidin-1(2H)-yl)propanenitrile (Example 1041 and Example 1042): 3-(6-(2-chloro-4-fluoro-5-methoxyphenyl)-3-(2,3-dimethyl-2H-pyrazolo[3,4-c]pyridin-4-yl)-2,4-dioxo-3,4-dihydrothieno[3,2-d]pyrimidin-1(2H)-yl)propanenitrile (Example 926) as a mixture of 2 atropisomers was separated by chiral SFC (AD-H Sum 21×$250$ mm column with 50% MeOH cosolvent) to give two enantiomers, which were assigned as Isomer 1 and Isomer 2. The stereochemistry was assigned by analogy to Example 438, with Example 1041 being the more active isomer.

Isomer 1:

3-(6-(2-chloro-4-fluoro-5-methoxyphenyl)-3-(2,3-dimethyl-2H-pyrazolo[3,4-c]pyridin-4-yl)-2,4-dioxo-3,4-dihydrothieno[3,2-d]pyrimidin-1(2H)-yl)propanenitrile Example 1041

ES/MS: 524.8 (M$^+$).

$^1$H NMR (400 MHz, DMSO-d$_6$) δ 9.14 (s, 1H), 8.00 (s, 1H), 7.96 (s, 1H), 7.74 (d, J=11.1 Hz, 1H), 7.56 (d, J=8.9 Hz, 1H), 4.58-4.45 (m, 1H), 4.45-4.32 (m, 1H), 4.14 (s, 3H), 3.97 (s, 3H), 3.06 (t, J=6.5 Hz, 2H), 2.38 (s, 3H).

Isomer 2:

3-(6-(2-chloro-4-fluoro-5-methoxyphenyl)-3-(2,3-dimethyl-2H-pyrazolo[3,4-c]pyridin-4-yl)-2,4-dioxo-3,4-dihydrothieno[3,2-d]pyrimidin-1(2H)-yl)propanenitrile Example 1042

ES/MS: 524.8 (M$^+$).

$^1$H NMR (400 MHz, DMSO-d$_6$) δ 9.14 (s, 1H), 8.00 (s, 1H), 7.96 (s, 1H), 7.74 (d, J=11.0 Hz, 1H), 7.57 (d, J=8.9 Hz, 1H), 4.59-4.44 (m, 1H), 4.44-4.31 (m, 1H), 4.14 (s, 3H), 3.97 (s, 3H), 3.06 (t, J=6.5 Hz, 2H), 2.38 (s, 3H).

Procedure 140: Example 1043 and Example 1044

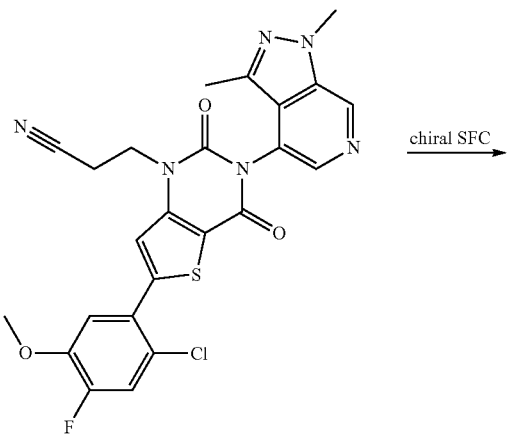

Example 925 chiral SFC →

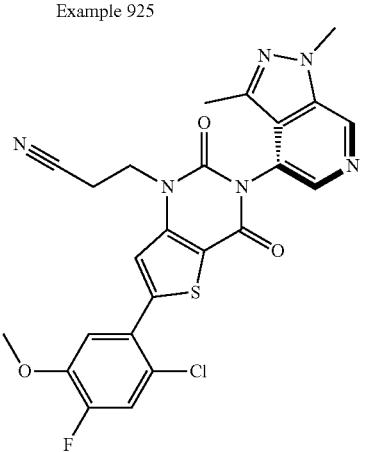

Example 1043

3-(6-(2-chloro-4-fluoro-5-methoxyphenyl)-3-(1,3-dimethyl-1H-pyrazolo[3,4-c]pyridin-4-yl)-2,4-dioxo-3,4-dihydrothieno[3,2-d]pyrimidin-1(2H)-yl)propanenitrile (Example 1043 and Example 1044): 3-(6-(2-chloro-4-fluoro-5-methoxyphenyl)-3-(1,3-dimethyl-1H-pyrazolo[3,4-c]pyridin-4-yl)-2,4-dioxo-3,4-dihydrothieno[3,2-d]pyrimidin-1(2H)-yl)propanenitrile (Example 925) as a mixture of 2 atropisomers was separated by chiral SFC (AD-H 5 μm 21×250 mm column with 45% EtOH cosolvent) to give two enantiomers, which were assigned as Isomer 1 and Isomer 2.

The stereochemistry was assigned by analogy to Example 438, with Example 1044 being the more active isomer.

Isomer 1:

3-(6-(2-chloro-4-fluoro-5-methoxyphenyl)-3-(1,3-dimethyl-1H-pyrazolo[3,4-c]pyridin-4-yl)-2,4-dioxo-3,4-dihydrothieno[3,2-d]pyrimidin-1(2H)-yl)propanenitrile Example 1043

ES/MS: 524.8 (M⁺).
$^1$H NMR (400 MHz, DMSO-$d_6$) δ 9.19 (s, 11H), 8.19 (s, 11H), 7.95 (s, 1H), 7.73 (d, J=11.0 Hz, 1H), 7.57 (d, J=8.9 Hz, 1H), 4.52 (dt, J=14.1, 6.9 Hz, 1H), 4.44-4.35 (m, 1H), 4.15 (s, 3H), 3.97 (s, 3H), 3.06 (t, J=6.6 Hz, 2H), 2.27 (s, 3H).

Isomer 2:

3-(6-(2-chloro-4-fluoro-5-methoxyphenyl)-3-(1,3-dimethyl-1H-pyrazolo[3,4-c]pyridin-4-yl)-2,4-dioxo-3,4-dihydrothieno[3,2-d]pyrimidin-1(2H)-yl)propanenitrile Example 1044

ES/MS: 524.8 (M⁺).
$^1$H NMR (400 MHz, DMSO-$d_6$) δ 9.19 (s, 11H), 8.19 (s, 11H), 7.95 (s, 1H), 7.73 (d, J=11.0 Hz, 1H), 7.57 (d, J=9.0 Hz, 1H), 4.52 (dt, J=13.7, 6.5 Hz, 1H), 4.40 (dt, J=14.2, 6.1 Hz, 1H), 4.15 (s, 3H), 3.96 (s, 3H), 3.06 (t, J=6.6 Hz, 2H), 2.27 (s, 3H).

Procedure 141: Preparation of Example 1045

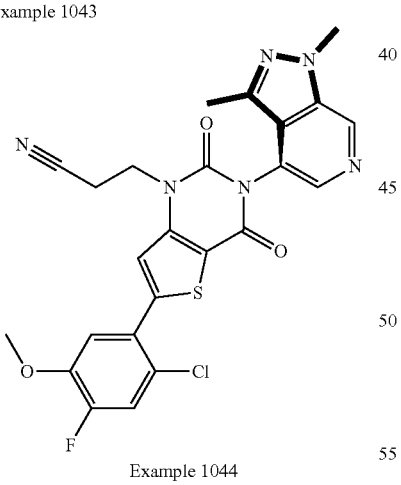

Example 1044

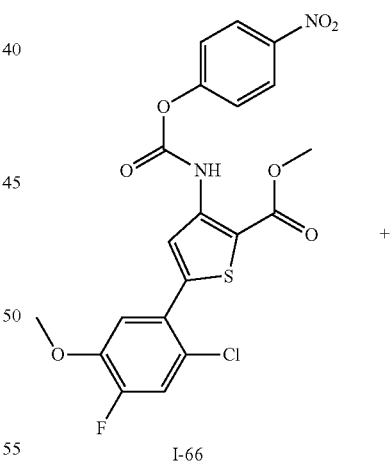

I-66

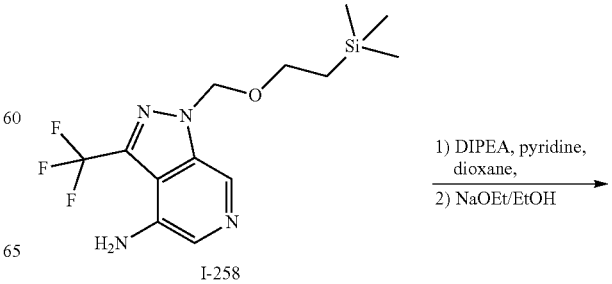

I-258

1) DIPEA, pyridine, dioxane,
2) NaOEt/EtOH

1433

-continued

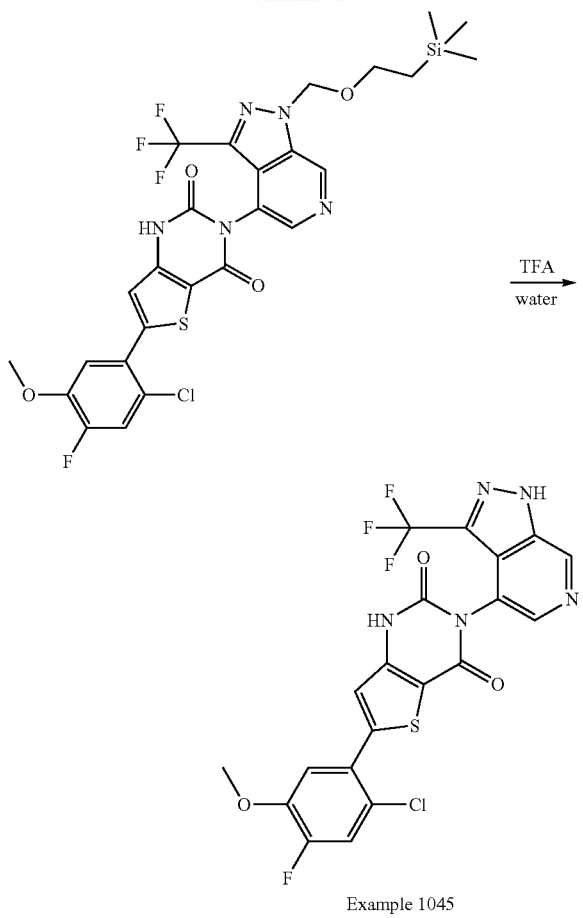

Example 1045

6-(2-chloro-4-fluoro-5-methoxyphenyl)-3-(3-(trifluoromethyl)-1-((2-(trimethylsilyl)ethoxy)methyl)-1H-pyrazolo[3,4-c]pyridin-4-yl)thieno[3,2-d]pyrimidine-2,4(1H,3H)-dione: To 1-66 (221 mg, 0.46 mmol) and 1-258 (183 mg, 0.55 mmol) in 1,4-dioxane (4 mL) was added DIPEA (0.12 mL, 0.69 mmol) and pyridine (0.04 mL, 0.46 mmol) and the mixture was heated to 90° C. After 16 h, EtOH (2 mL) and NaOEt solution (21% in EtOH, 0.69 mL) were added. After 10 min, TFA (0.2 mL) was added and the mixture was concentrated under reduced pressure. Purification by silica chromatography (EtOAc/hexanes) provided the product.

ES/MS: 641.8 (M$^+$).

6-(2-chloro-4-fluoro-5-methoxyphenyl)-3-(3-(trifluoromethyl)-1H-pyrazolo[3,4-c]pyridin-4-yl)thieno[3,2-d]pyrimidine-2,4(1H,3H)-dione (Example 1045): To 6-(2-chloro-4-fluoro-5-methoxyphenyl)-3-(3-(trifluoromethyl)-1-((2-(trimethylsilyl)ethoxy)methyl)-1H-pyrazolo[3,4-c]pyridin-4-yl)thieno[3,2-d]pyrimidine-2,4(1H,3H)-dione (13 mg, 0.02 mmol) was added TFA (1 mL) and a drop of water, and the mixture was heated to 80° C. for 16 h. Purification by RP-HPLC (MeCN in water with 0.1% TFA, Column: Kinetex 5 uM C18 110 Angstrom, 250×30 mm) afforded the title product.

ES/MS: 511.7 (M$^+$).

$^1$H NMR (400 MHz, DMSO-d$_6$) δ 14.98 (s, 1H), 12.35 (s, 1H), 9.34 (s, 1H), 8.48 (s, 1H), 7.70 (d, J=11.0 Hz, 1H), 7.51 (d, J=8.9 Hz, 1H), 7.29 (s, 1H), 3.95 (s, 3H).

Procedure 142: Preparation of Example 1046

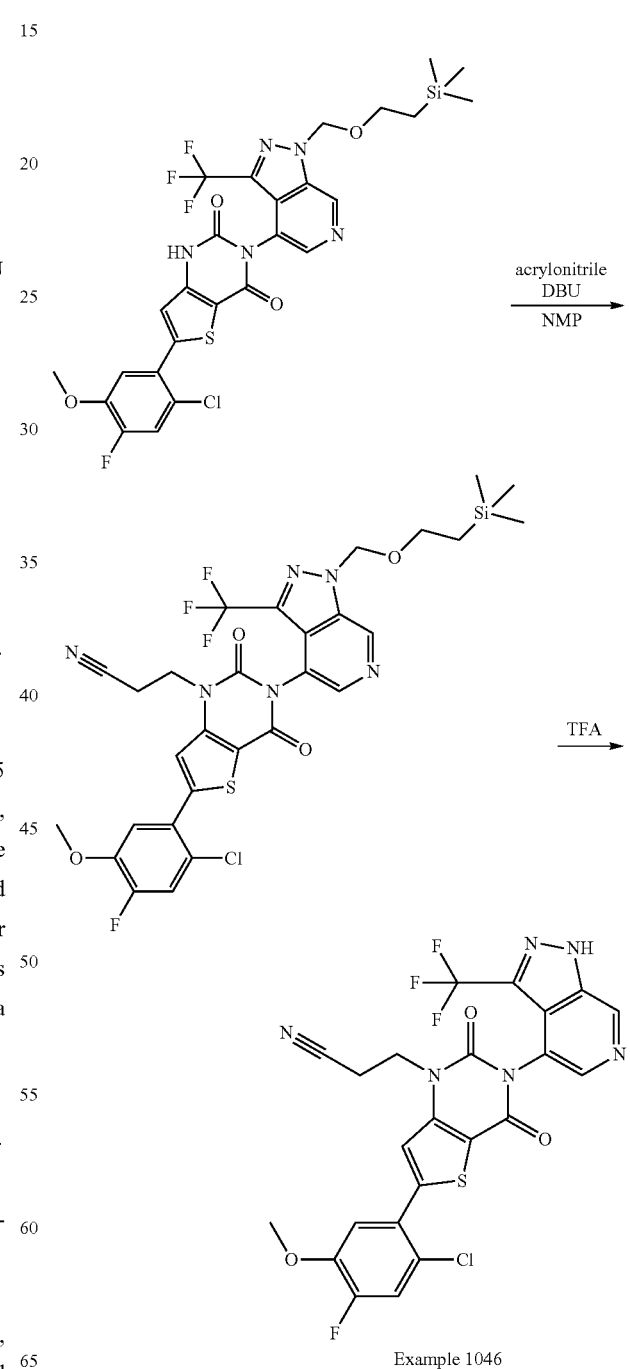

Example 1046

3-(6-(2-chloro-4-fluoro-5-methoxyphenyl)-2,4-dioxo-3-(3-(trifluoromethyl)-1-((2-(trimethylsilyl)ethoxy)methyl)-1H-pyrazolo[3,4-c]pyridin-4-yl)-3,4-dihydrothieno[3,2-d]pyrimidin-1(2H)-yl)propanenitrile: To 6-(2-chloro-4-fluoro-5-methoxyphenyl)-3-(3-(trifluoromethyl)-1-((2-(trimethylsilyl)ethoxy)methyl)-1H-pyrazolo[3,4-c]pyridin-4-yl)thieno[3,2-d]pyrimidine-2,4(1H,3H)-dione (as prepared in Procedure 141) (105 mg, 0.16 mmol) in NMP (0.75 mL) was added DBU (0.05 mL, 0.33 mmol) and acrylonitrile (0.96 mL, 15 mmol) and the mixture was heated to 80° C. After 16 h, the reaction was diluted with EtOAc (15 mL), washed with brine (5×10 mL), and concentrated in vacuo to provide crude product that was used without further purification.

ES/MS: 694.8 (M+).

3-(6-(2-chloro-4-fluoro-5-methoxyphenyl)-2,4-dioxo-3-(3-(trifluoromethyl)-1-((2-(trimethylsilyl)ethoxy)methyl)-1H-pyrazolo[3,4-c]pyridin-4-yl)-3,4-dihydrothieno[3,2-d]pyrimidin-1(2H)-yl)propanenitrile (Example 1046): To crude 3-(6-(2-chloro-4-fluoro-5-methoxyphenyl)-2,4-dioxo-3-(3-(trifluoromethyl)-14(2-(trimethylsilyl)ethoxy)methyl)-1H-pyrazolo[3,4-c]pyridin-4-yl)-3,4-dihydrothieno[3,2-d]pyrimidin-1(2H)-yl)propanenitrile was added TFA (5 mL) and water (1 mL) and the mixture was heated to 80° C. for 16 h. Purification by RP-HPLC (MeCN in water with 0.1% TFA, Column: Kinetex 5 uM C18 110 Angstrom, 250×30 mm) afforded the title product.

ES/MS: 564.8 (M+).

$^1$H NMR (400 MHz, DMSO-d$_6$) δ 15.01 (s, 1H), 9.36 (s, 1H), 8.47 (s, 1H), 7.98 (s, 1H), 7.73 (d, J=11.0 Hz, 1H), 7.58 (d, J=8.9 Hz, 1H), 4.50-4.38 (m, 2H), 3.97 (s, 3H), 3.01-2.94 (m, 2H).

Examples 1047

The following Examples were made in an analogous fashion according to Procedure 142 and are shown below in Table 53. To prepare the below Examples, different reagents/starting materials were used than some of those described in Procedure 142 and are noted in the last column of Table 53—"Changes to Procedure 142: Different Reagents/Starting Materials".

TABLE 53

Example 1047

| Example | Structure | ES/MS m/z | 1H-NMR | Changes to Procedure 142: Different Reagents/ Starting Materials |
|---|---|---|---|---|
| 1047 | 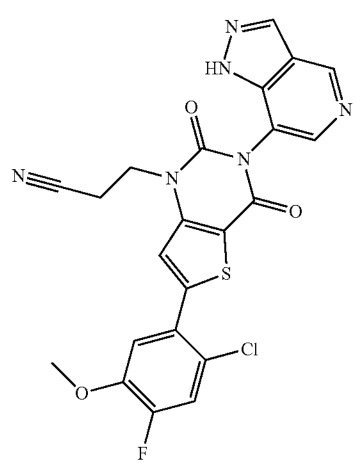 [SMILES: COc1cc(-c2cc3c(s2)c(=O)n(-c2cncc4cn[nH]c24)c(=O)n3CCC#N)c(Cl)cc1F] | 497.1 | 1H NMR (400 MHz, DMSO-d6) δ 13.82 (s, 1H), 9.30 (s, 1H), 8.52 (s, 1H), 8.45 (s, 1H), 8.00 (s, 1H), 7.75 (d, 1H), 7.53 (d, 1H), 4.59-4.35 (m, 2H), 3.98 (s, 3H), 3.02 (t, 2H). | I-264 |

Procedure 143: Preparation of Example 1048

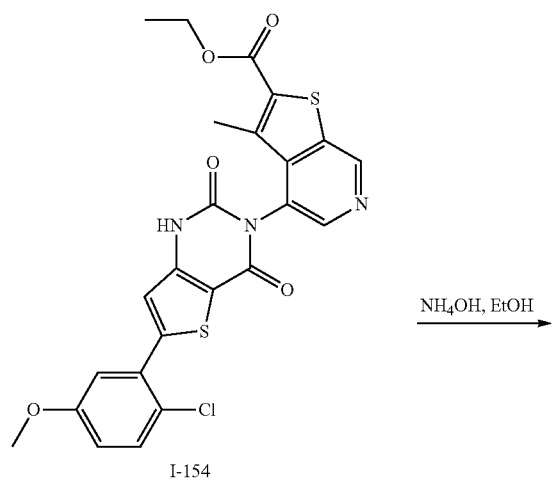

I-154

NH₄OH, EtOH

Example 1048

4-(6-(2-chloro-5-methoxyphenyl)-2,4-dioxo-1,4-dihydrothieno[3,2-d]pyrimidin-3(2H)-yl)-3-methylthieno[2,3-c]pyridine-2-carboxamide (Example 1048): A solution of ethyl 4-(6-(2-chloro-5-methoxyphenyl)-2,4-dioxo-1,4-dihydrothieno[3,2-d]pyrimidin-3(2H)-yl)-3-methylthieno[2,3-c]pyridine-2-carboxylate (I-154) TFA salt (10 mg, 0.02 mmol) and NH₄₀H (1 mL) in EtOH (1 mL) was stirred at 80° C. overnight. The reaction mixture was concentrated, neutralized with TFA and filtered through an acrodisc and was subsequently purified by RP-HPLC (0.1% TFA-ACN in 0.1% TFA Water, Column: Gemini 5 uM, NX-C18 110 Angstrom, 250×21.2 mm) to give Example 1048.

ES/MS: 499.7 (M⁺).

¹H NMR (400 MHz, DMSO) δ 12.42 (s, 1H), 9.37 (s, 1H), 8.52 (s, 1H), 8.13 (s, 1H), 7.93 (s, 1H), 7.59 (d, J=8.9 Hz, 1H), 7.35-7.26 (m, 2H), 7.13 (dd, J=8.9, 3.0 Hz, 1H), 3.85 (s, 3H), 2.32 (s, 3H).

Example 1049

The following Examples were made in an analogous fashion according to Procedure 143 and are shown below in Table 54. To prepare the below Examples, different reagents/starting materials were used than some of those described in Procedure 143 and are noted in the last column of Table 54—"Changes to Procedure 143: Different Reagents/Starting Materials".

TABLE 54

Example 1049

| Example | Structure | ES/MS m/z | 1H-NMR | Changes to Procedure 143: Different Reagents/ Starting Materials |
|---|---|---|---|---|
| 1049 | 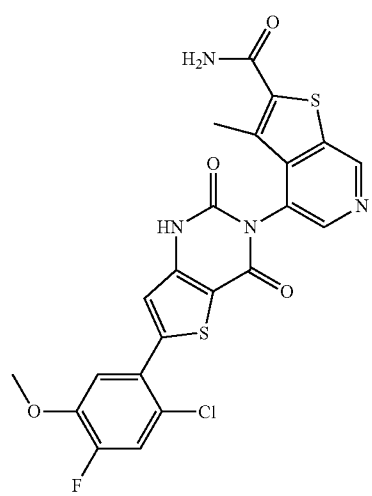 [SMILES: COc1cc(-c2cc3[nH]c(=O)n(-c4cncc5sc(C(N)=O)c(C)c45)c(=O)c3s2)c(Cl)cc1F] | 516.7 | 1H NMR (400 MHz, DMSO) δ 12.44 (s, 1H), 9.37 (s, 1H), 8.52 (s, 1H), 8.22-7.85 (m, 2H), 7.71 (d, J = 11.1 Hz, 1H), 7.50 (d, J = 8.9 Hz, 1H), 7.31 (s, 1H), 3.95 (s, 3H), 2.31 (s, 3H). | I-269 |

1439
Procedure 144: Preparation of Example 1050

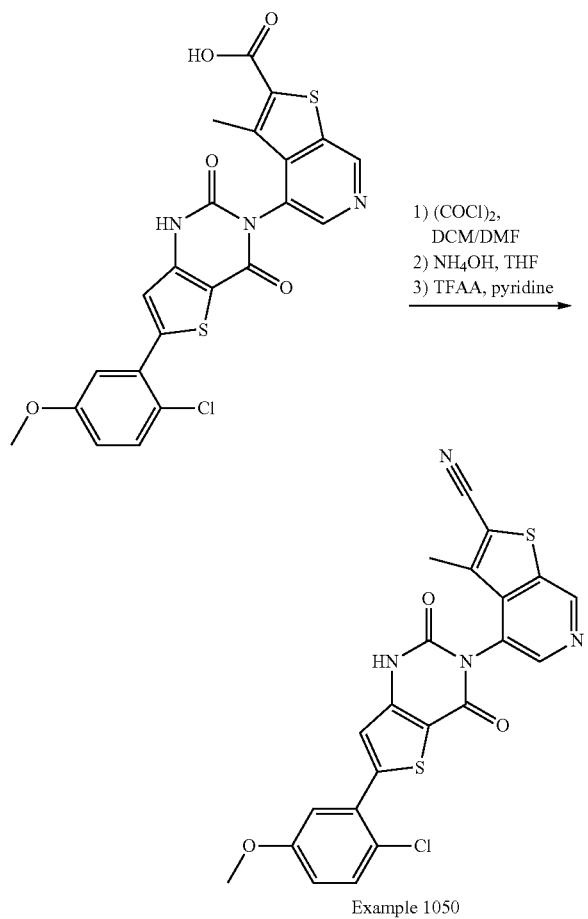

Example 1050

1440

4-(6-(2-chloro-5-methoxyphenyl)-2,4-dioxo-1,4-dihydrothieno[3,2-d]pyrimidin-3(2H)-yl)-3-methylthieno[2,3-c]pyridine-2-carbonitrile (Example 1050): To a cooled solution of 4-[16-(2-chloro-5-methoxy-phenyl)-2,4-dioxo-1H-thieno[3,2-d]pyrimidin-3-yl]-3-methyl-thieno[2,3-c]pyridine-2-carboxylic acid (prepared in an analogous fashion to 1-127, starting from 1-154) (40 mg, 0.08 mmol) in a mixture of DCM (1 mL) and DMF (1 mL) at 0° C. was added oxalyl chloride (20 mg, 0.16 mmol). The ice bath was removed, and the mixture was stirred at RT for 1 hr. The solvent was evaporated and THF (1 mL) was added followed by ammonium hydroxide (0.7 mL) and stirred at RT for 1 hr. The reaction mixture was neutralized with TFA, filtered and purified by prep-HPLC. To a solution of the purified product dissolved in pyridine (0.5 mL) at 0° C. was added trifluoroacetic anhydride (0.2 mL). The resulting reaction mixture was allowed to warm to room temperature and stirred for 30 min. The reaction mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give Example 1050.

ES/MS: 480.7 ($M^+$).

$^1$H NMR (400 MHz, DMSO) δ 12.48 (s, 1H), 9.53 (s, 1H), 8.67 (s, 1H), 7.59 (d, J=8.8 Hz, 1H), 7.34 (s, 1H), 7.28 (d, J=3.0 Hz, 1H), 7.13 (dd, J=8.9, 3.0 Hz, 1H), 3.85 (s, 3H), 2.39 (s, 3H).

Example 1051

The following Examples were made in an analogous fashion according to Procedure 144 and are shown below in Table 55. To prepare the below Examples, different reagents/starting materials were used than some of those described in Procedure 144 and are noted in the last column of Table 55—"Changes to Procedure 144: Different Reagents/Starting Materials".

TABLE SS

Example 1051

| Example | Structure | ES/MS m/z | 1H-NMR | Changes to Procedure 144: Different Reagents/ Starting Materials |
|---|---|---|---|---|
| 1051 | 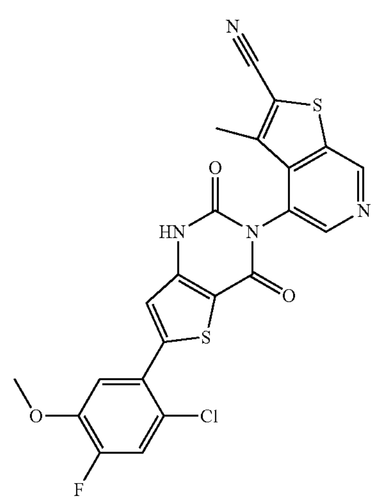 [SMILES: COc1cc(-c2cc3[nH]c(=O)n(-c4cncc5sc(C#N)c(C)c45)c(=O)c3s2)c(Cl)cc1F] | 498.6 | 1H NMR (400 MHz, DMSO) δ 12.50 (s, 1H), 9.53 (s, 1H), 8.67 (s, 1H), 7.72 (d, J = 11.0 Hz, 1H), 7.49 (d, J = 8.9 Hz, 1H), 7.32 (s, 1H), 3.95 (s, 3H), 2.39 (s, 3H). | I-269 |

Procedure 145: Preparation of Example 1052 and Example 1053

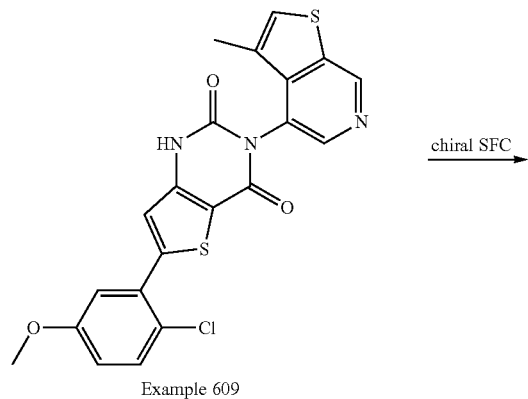

Example 609

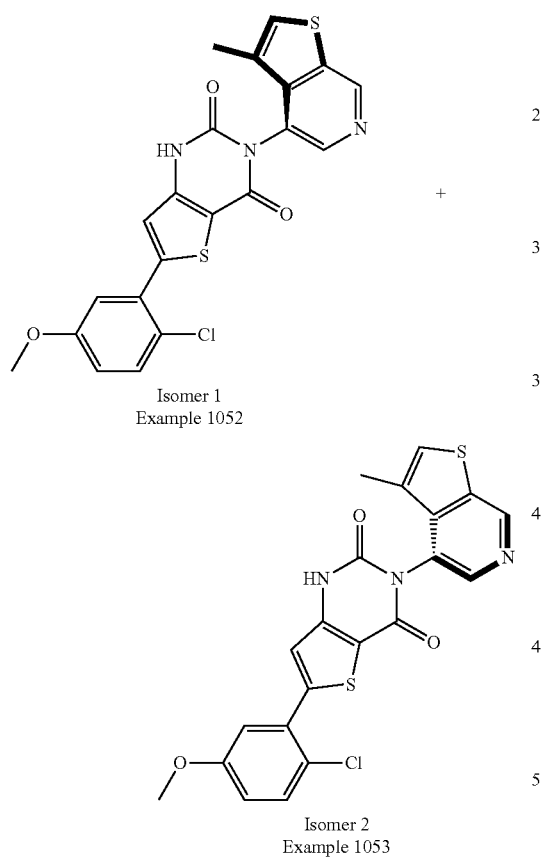

Isomer 1
Example 1052

Isomer 2
Example 1053

6-(2-chloro-5-methoxyphenyl)-3-(3-methylthieno[2,3-c]pyridin-4-yl)thieno[3,2-d]pyrimidine-2,4(1H,3H)-dione (Example 1052 and Example 1053): 6-(2-chloro-5-methoxyphenyl)-3-(3-methylthieno[2,3-c]pyridin-4-yl)thieno[3,2-d]pyrimidine-2,4(1H,3H)-dione (Example 609) as a mixture of 2 isomers was separated by chiral SFC (IB 5 um-4.6×$^{100}$ mm column with 35% MeOH cosolvent) to give two enantiomers, which were assigned as Isomer 1 and Isomer 2. The stereochemistry was assigned by analogy to Example 438, with Example 1052 being the more active isomer.

Isomer 1:

6-(2-chloro-5-methoxyphenyl)-3-(3-methylthieno[2,3-c]pyridin-4-yl)thieno[3,2-d]pyrimidine-2,4(1H,3H)-dione (Example 1052)

ES/MS: 455.7 (M$^+$).
$^1$H NMR (400 MHz, DMSO) δ 12.39 (s, 1H), 9.35 (s, 1H), 8.48 (s, 1H), 7.91 (d, J=1.3 Hz, 1H), 7.59 (d, J=8.9 Hz, 1H), 7.33 (s, 1H), 7.28 (d, J=3.0 Hz, 1H), 7.13 (dd, J=8.9, 3.0 Hz, 1H), 3.85 (s, 3H), 2.21 (d, J=1.2 Hz, 3H).

Isomer 2:

6-(2-chloro-5-methoxyphenyl)-3-(3-methylthieno[2,3-c]pyridin-4-yl)thieno[3,2-d]pyrimidine-2,4(1H,3H)-dione (Example 1053)

ES/MS: 455.7 (M$^+$).
$^1$H NMR (400 MHz, DMSO) δ 12.39 (s, 1H), 9.35 (s, 1H), 8.48 (s, 1H), 7.91 (d, J=1.3 Hz, 1H), 7.59 (d, J=8.9 Hz, 1H), 7.33 (s, 1H), 7.28 (d, J=3.0 Hz, 1H), 7.13 (dd, J=8.9, 3.0 Hz, 1H), 3.85 (s, 3H), 2.21 (d, J=1.2 Hz, 3H).

Procedure 146: Preparation of Example 1054 and Example 1055

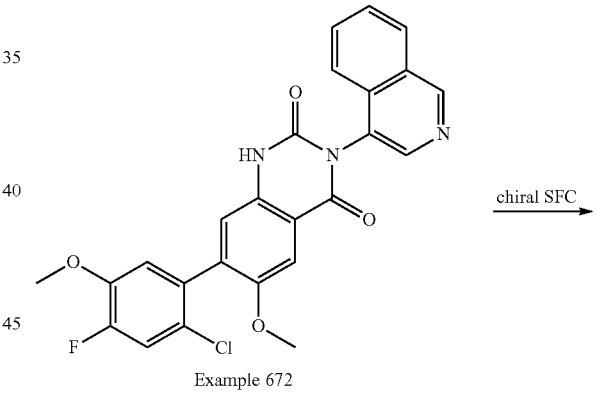

Example 672

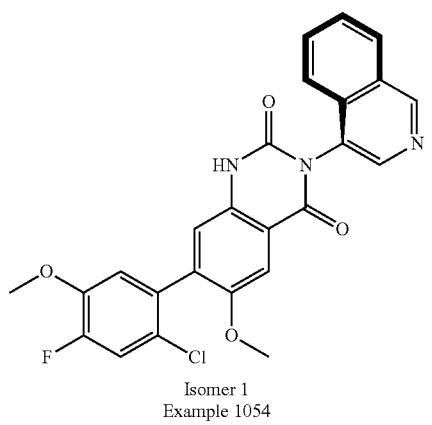

Isomer 1
Example 1054

1443
-continued

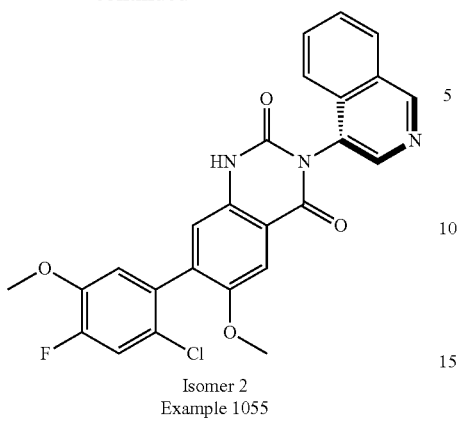

Isomer 2
Example 1055

7-(2-chloro-4-fluoro-5-methoxyphenyl)-3-(isoquinolin-4-yl)-6-methoxyquinazoline-2,4(1H,3H)-dione (Example 1054 and Example 1055), 7-(2-chloro-4-fluoro-5-methoxyphenyl)-3-(isoquinolin-4-yl)-6-methoxyquinazoline-2,4(1H,3H)-dione (Example 672) as a mixture of 2 isomers was separated by chiral SFC (IB 5 um-4.6×$100$ mm column with 35% MeOH cosolvent) to give two enantiomers, which were assigned as Isomer 1 and Isomer 2. The stereochemistry was assigned by analogy to Example 438, with Example 1054 being the more active isomer.

Isomer 1:

7-(2-chloro-4-fluoro-5-methoxyphenyl)-3-(isoquinolin-4-yl)-6-methoxyquinazoline-2,4(1H,3H)-dione (Example 1054)

ES/MS: 477.8 (M+).

1H NMR (400 MHz, DMSO) δ 11.78 (s, 1H), 9.55 (s, 1H), 8.66 (s, 1H), 8.35 (dt, J=7.9, 1.1 Hz, 1H), 7.91-7.78 (m, 3H), 7.60 (d, J=11.1 Hz, 1H), 7.54 (s, 1H), 7.19 (d, J=9.0 Hz, 1H), 7.15 (s, 1H), 3.88 (s, 3H), 3.80 (s, 3H).

Isomer 2:

7-(2-chloro-4-fluoro-5-methoxyphenyl)-3-(isoquinolin-4-yl)-6-methoxyquinazoline-2,4(1H,3H)-dione (Example 1055)

ES/MS: 477.8 (M+).

$^1$H NMR (400 MHz, DMSO) δ 11.77 (s, 1H), 9.53 (s, 1H), 8.64 (s, 1H), 8.34 (dt, J=7.8, 1.2 Hz, 1H), 7.83 (ddd, J=13.3, 10.9, 5.7 Hz, 3H), 7.60 (d, J=11.1 Hz, 1H), 7.54 (s, 1H), 7.20 (d, J=9.0 Hz, 1H), 7.14 (s, 1H), 3.88 (s, 3H), 3.80 (s, 3H).

1444
Procedure 147: Preparation of Example 1056 and Example 1057

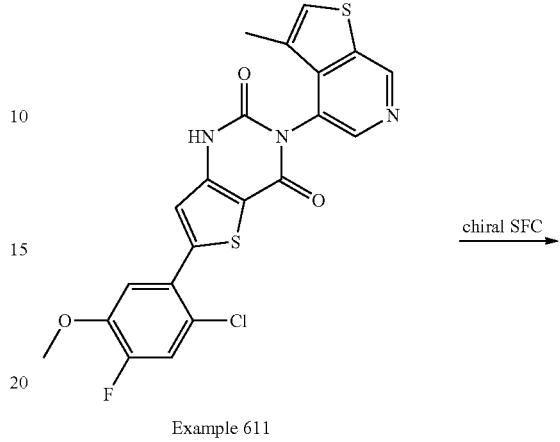

Example 611

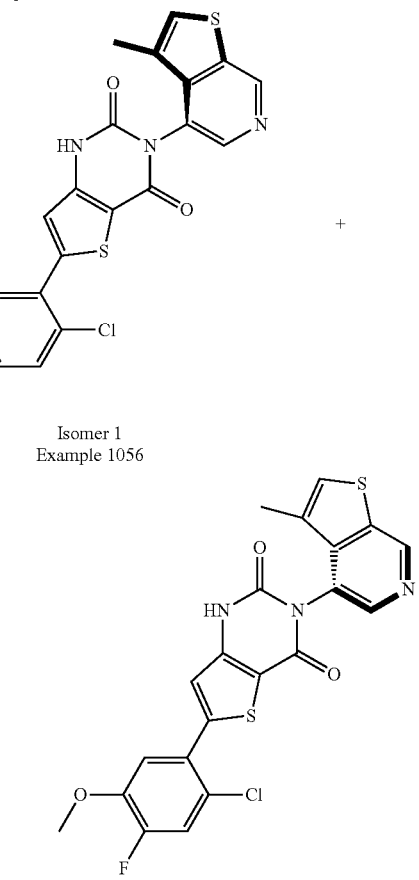

Isomer 1
Example 1056

Isomer 2
Example 1057

6-(2-chloro-4-fluoro-5-methoxyphenyl)-3-(3-methylthieno[2,3-c]pyridin-4-yl)thieno[3,2-d]pyrimidine-2,4(1H,3H)-dione (Example 1056 and Example 1057): 6-(2-chloro-4-fluoro-5-methoxyphenyl)-3-(3-methylthieno[2,3-c]pyridin-4-yl)thieno[3,2-d]pyrimidine-2,4(1H,3H)-dione (Example 611) as a mixture of 2 isomers was separated by chiral SFC IB 5 um-4.6×100 mm column with 35% MeOH cosolvent) to give two enantiomers, which were assigned as

1445

Isomer 1 and Isomer 2. The stereochemistry was assigned by analogy to Example 438, with Example 1056 being the more active isomer.

Isomer 1:

6-(2-chloro-4-fluoro-5-methoxyphenyl)-3-(3-methylthieno[2,3-c]pyridin-4-yl)thieno[3,2-d]pyrimidine-2,4(1H,3H)-dione (Example 1056)

ES/MS: 473.7 (M+).

$^1$H NMR (400 MHz, DMSO) δ 12.41 (s, 11H), 9.36 (s, 11H), 8.49 (s, 11H), 7.92 (d, J=1.2 Hz, 1H), 7.71 (d, J=11.1 Hz, 1H), 7.49 (d, J=8.9 Hz, 1H), 7.31 (s, 1H), 3.95 (s, 3H), 2.20 (d, J=1.2 Hz, 3H).

Isomer 2:

6-(2-chloro-4-fluoro-5-methoxyphenyl)-3-(3-methyl-thieno[2,3-c]pyridin-4-yl)thieno[3,2-d]pyrimidine-2,4(1H,3H)-dione (Example 1057)

ES/MS: 473.7 (M+).

$^1$H NMR (400 MHz, DMSO) δ 12.41 (s, 11H), 9.36 (s, 11H), 8.49 (s, 11H), 7.92 (d, J=1.3 Hz, 1H), 7.71 (d, J=11.1 Hz, 1H), 7.49 (d, J=8.9 Hz, 1H), 7.31 (s, 1H), 3.95 (s, 3H), 2.20 (d, J=1.2 Hz, 3H).

Procedure 148: Preparation of Example 1058 and Example 1059

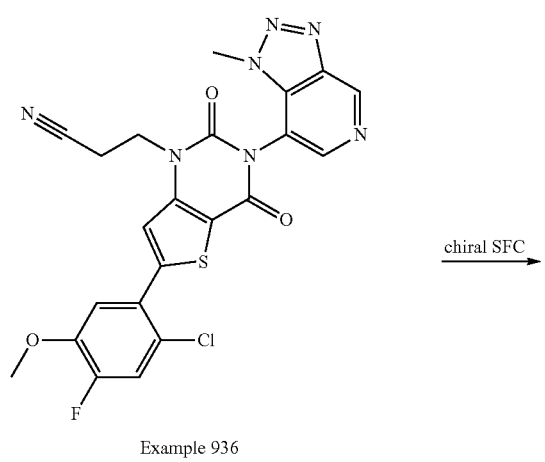

Example 936 chiral SFC

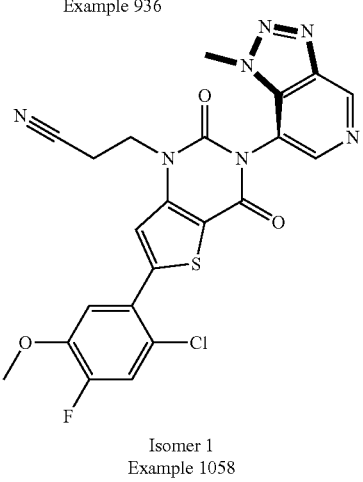

Isomer 1
Example 1058

+

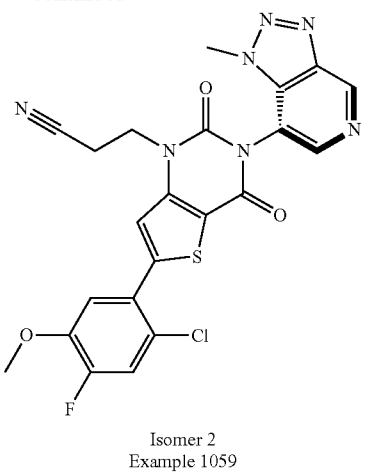

Isomer 2
Example 1059

3-(6-(2-chloro-4-fluoro-5-methoxyphenyl)-3-(1-methyl-1H-[1,2,3]triazolo[4,5-c]pyridin-7-yl)-2,4-dioxo-3,4-dihydrothieno[3,2-d]pyrimidin-1(2H)-yl)propanenitrile (Example 1058 and Example-1059): 3-(6-(2-chloro-4-fluoro-5-methoxyphenyl)-3-(1-methyl-1H-[1,2,3]triazolo[4,5-c]pyridin-7-yl)-2,4-dioxo-3,4-dihydrothieno[3,2-d]pyrimidin-1(2H)-yl)propanenitrile (Example 936) as a mixture of 2 isomers was separated by chiral SFC IB 5 um-4.6×$^{100}$ mm column with 30% EtOH cosolvent) to give two enantiomers, which were assigned as Isomer 1 and Isomer 2. The stereochemistry was assigned by analogy to Example 438, with Example 1058 being the more active isomer.

Isomer 1:

3-(6-(2-chloro-4-fluoro-5-methoxyphenyl)-3-(1-methyl-1H-[1,2,3]triazolo[4,5-c]pyridin-7-yl)-2,4-dioxo-3,4-dihydrothieno[3,2-d]pyrimidin-1(2H)-yl)propanenitrile Example 1058

ES/MS: 511.7 (M+).

$^1$H NMR (400 MHz, DMSO) δ 9.61 (s, 1H), 8.64 (s, 1H), 7.99 (s, 1H), 7.75 (d, J=11.0 Hz, 1H), 7.55 (d, J=8.9 Hz, 1H), 4.60-4.37 (m, 2H), 4.20 (s, 3H), 3.97 (s, 3H), 3.08 (t, J=6.6 Hz, 2H).

Isomer 2:

3-(6-(2-chloro-4-fluoro-5-methoxyphenyl)-3-(1-methyl-1H-[1,2,3]triazolo[4,5-c]pyridin-7-yl)-2,4-dioxo-3,4-dihydrothieno[3,2-d]pyrimidin-1(2H)-yl)propanenitrile Example 1059

ES/MS: 511.7 (M+).

$^1$H NMR (400 MHz, DMSO) δ 9.61 (s, 1H), 8.64 (s, 1H), 7.99 (s, 1H), 7.75 (d, J=11.1 Hz, 1H), 7.55 (d, J=8.9 Hz, 1H), 4.55 (dt, J=14.0, 6.9 Hz, 1H), 4.43 (dt, J=14.3, 6.2 Hz, 1H), 4.20 (s, 3H), 3.97 (s, 3H), 3.08 (t, J=6.5 Hz, 2H).

Procedure 149: Preparation of Example 1060

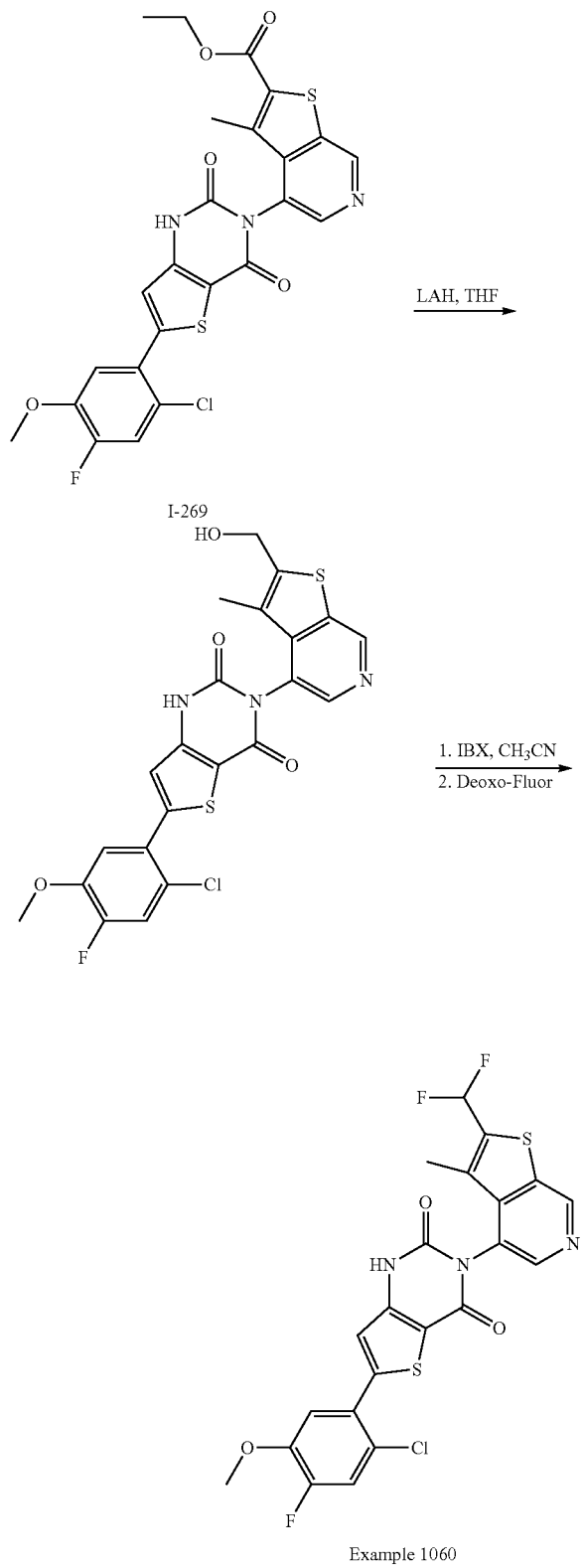

6-(2-chloro-4-fluoro-5-methoxy-phenyl)-3-[2-(hydroxymethyl)-3-methyl-thieno[2,3-c]pyridin-4-yl]-1H-thieno[3,2-d]pyrimidine-2,4-dione: To a stirring solution of ethyl 4-[6-(2-chloro-4-fluoro-5-methoxy-phenyl)-2,4-dioxo-1H-thieno[3,2-d]pyrimidin-3-yl]-3-methyl-thieno[2,3-c]pyridine-2-carboxylate (I-269) (100 mg, 0.18 mmol) in THF (2 mL) was added LAH in 2-methyltetrahydrofuran (2.3 M in 2-methyltetrahydrofuran, 0.5 mL) at 0° C. The reaction mixture was stirred at 0° C. for 2 h. The reaction was quenched by drop-wise addition of 1 N HCl. The reaction mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the product.

ES/MS: 503.7 (M+).

$^1$H NMR (400 MHz, DMSO) δ 12.42 (s, 1H), 9.32 (s, 1H), 8.48 (di, J=5.5 Hz, 1H), 7.75-7.66 (in, 1H), 7.64-7.46 (m, 1H), 7.39-7.31 (in, 1H), 4.83 (s, 2H), 3.96 (d, J=8.7 Hz, 3H), 2.06 (s, 3H).

6-(2-chloro-4-fluoro-5-methoxyphenyl)-3-(2-(difluoromethyl)-3-methylthieno[2,3-c]pyridin-4-yl)thieno[3,2-d]pyrimidine-2,4(1H,3H)-dione (Example 1060). A mixture of 6-(2-chloro-4-fluoro-5-methoxy-phenyl)-3-[2-(hydroxymethyl)-3-methyl-thieno[2,3-c]pyridin-4-yl]-1H-thieno[3,2-d]pyrimidine-2,4-dione (TFA salt) (22 mg, 0.04 mmol) and IBX (30 mg, 0.1 mmol) in CH$_3$CN (1 mL) was stirred at 80° C. for 30 min. The reaction mixture was allowed to cool down to room temperature, filtered with the aid of Celite, washed subsequently with EtOAc and DCM and then dried under reduced pressure to give the aldehyde intermediate. The crude product was transferred to a plastic reaction vessel by dissolving in DCM (1 mL) and treated with Deoxo-Fluor (20 µL). The reaction mixture was stirred at room temperature for 1 h. The reaction was quenched at room temperature by careful addition of dilute aqueous NaHCO$_3$. The mixture was filtered through an acrodisc and was subsequently purified by RP-HPLC (0.1% TFA-ACN in 0.1% TFA Water, Column: Gemini 5 uM. NX-C18 110 Angstrom, 250×21.2 mm) to the product.

ES/MS: 523.7 (M+).

$^1$H NMR (400 MHz, DMSO) δ 12.46 (s, 1H), 9.44 (s, 1H), 8.57 (s, 1H), 8.02-7.25 (m, 4H), 3.95 (s, 3H), 2.25 (t, J=1.7 Hz, 3H).

Procedure 150: Preparation of Example 1061

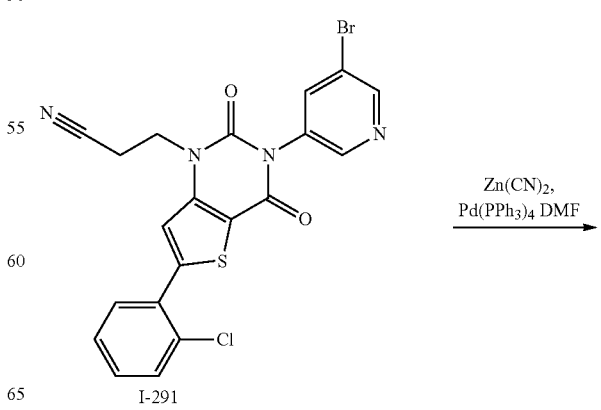

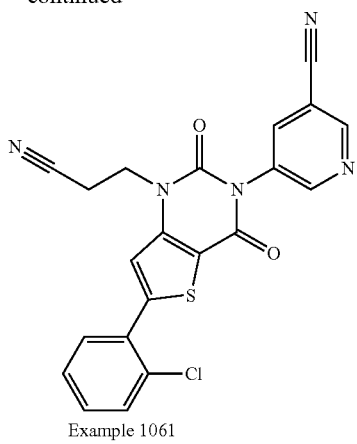

Example 1061

5-(6-(2-chlorophenyl)-1-(2-cyanoethyl)-2,4-dioxo-1,4-dihydrothieno[3,2-d]pyrimidin-3(2H)-yl)nicotinonitrile (Example 1061): To a dram vial was added 3-[3-(5-bromo-3-pyridyl)-6-(2-chlorophenyl)-2,4-dioxo-thieno[3,2-d]pyrimidin-1-yl]propanenitrile (1-291) (100 mg, 0.21 mmol), Zn(CN)$_2$ (24 mg, 0.21 mmol) and Pd(PPh3)$_4$ (7 mg, 0.062 mmol) in DMF (1 mL). The mixture was degassed with argon for 30 seconds. The vial was sealed, and the reaction mixture was heated at 120° C. for 4 hours. The reaction was allowed to cool down to room temperature and filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the product.

ES/MS: 433.8 (M$^+$).

$^1$H NMR (400 MHz, DMSO) δ 9.13 (d, J=1.9 Hz, 1H), 8.93 (d, J=2.2 Hz, 1H), 8.48 (t, J=2.1 Hz, 1H), 8.01 (s, 1H), 7.91-7.82 (m, 1H), 7.75-7.66 (m, 1H), 7.61-7.52 (m, 2H), 4.43 (t, J=6.6 Hz, 2H), 2.99 (t, J=6.6 Hz, 2H).

Examples 1062-1063

The following Examples were made in an analogous fashion according to Procedure 150 and are shown below in Table 56. To prepare the below Examples, different reagents/starting materials were used than some of those described in Procedure 150 and are noted in the last column of Table 56—"Changes to Procedure 150: Different Reagents/Starting Materials".

TABLE 56

Examples 1062-1063

| Example | Structure | ES/MS m/z | 1H-NMR | Changes to Procedure 150: Different Reagents/ Starting Materials |
|---|---|---|---|---|
| 1062 | 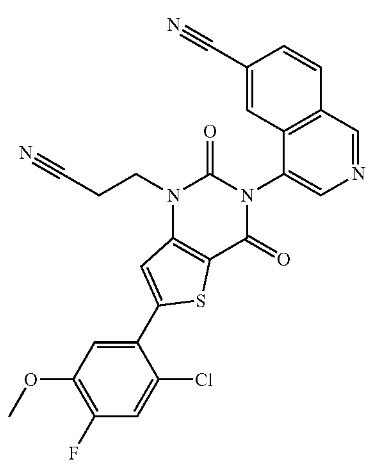 [SMILES: COc1cc(-c2cc3c(s2)c(=O)n(-c2cncc4ccc(C#N)cc24)c(=O)n3CCC#N)c(Cl)cc1F] | 531.8 | 1H NMR (400 MHz, DMSO) δ 9.61 (d, J = 0.9 Hz, 1H), 8.84 (dd, J = 1.6, 0.8 Hz, 1H), 8.74 (s, 1H), 8.49 (dd, J = 8.6, 0.8 Hz, 1H), 8.07 (dd, J = 8.5, 1.5 Hz, 1H), 8.00 (s, 1H), 7.75 (d, J = 11.0 Hz, 1H), 7.52 (d, J = 8.8 Hz, 1H), 4.52-4.40 (m, 2H), 3.98 (s, 3H), 3.02 (t, J = 6.6 Hz, 2H). | I-298 |

TABLE 56-continued

Examples 1062-1063

| Example | Structure | ES/MS m/z | 1H-NMR | Changes to Procedure 150: Different Reagents/ Starting Materials |
|---|---|---|---|---|
| 1063 | 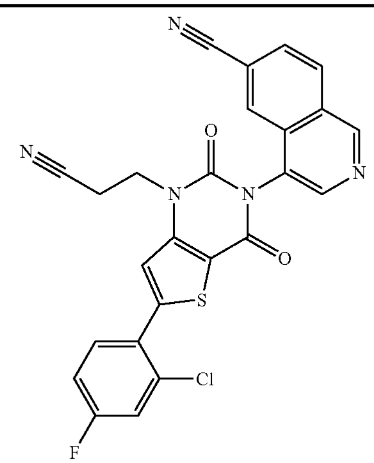 | 501.8 | 1H NMR (400 MHz, DMSO-d6) δ 9.61 (d, J = 0.9 Hz, 1H), 8.87 (d, J = 1.4 Hz, 1H), 8.74 (s, 1H), 8.49 (d, J = 8.5 Hz, 1H), 8.07 (dd, J = 8.5, 1.5 Hz, 1H), 8.01 (s, 1H), 7.93 (dd, J = 8.8, 6.1 Hz, 1H), 7.76 (dd, J = 8.8, 2.7 Hz, 1H), 7.51 (td, J = 8.5,2.7 Hz, 1H), 4.44 (td, J = 6.8, 1.8 Hz, 2H), 3.00 (t, J = 6.7 Hz, 2H). | I-309 |

Procedure 151: Preparation of Example 1064

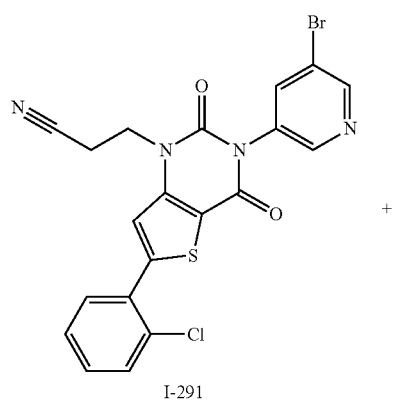

I-291

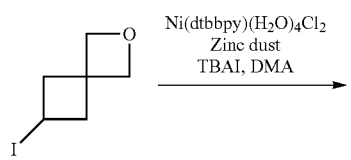

Ni(dtbbpy)(H₂O)₄Cl₂
Zinc dust
TBAI, DMA

-continued

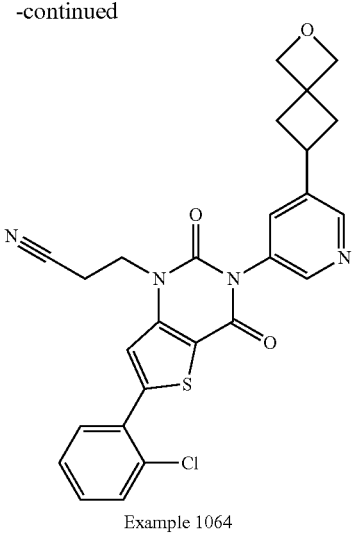

Example 1064

3-(3-(5-(2-oxaspiro[3.3]heptan-6-yl)pyridin-3-yl)-6-(2-chlorophenyl)-2,4-dioxo-3,4-dihydrothieno[3,2-d]pyrimidin-1(2H)-yl)propanenitrile (Example 1064): To a dried vial was added: 3-[3-(5-bromo-3-pyridyl)-6-(2-chlorophenyl)-2,4-dioxo-thieno[3,2-d]pyrimidin-1-yl]propanenitrile (I-291) (200 mg, 0.41 mmol), TBAI (182 mg, 0.49 mmol), zinc dust (160 mg, 2.46 mmol), Ni(dtbbpy)(H₂O)₄Cl₂ (23 mg, 0.049 mmol) and DMA (2 mL). The resulting mixture was sparged with argon for one minute, vial sealed with teflon seal and stirred at RT for 1 h. Upon completion, the reaction mixture was filtered through an acrodisc and was subsequently purified by RP-HPLC (0.1% TFA-ACN in 0.1% TFA Water, Column: Gemini 5 uM, NX-C18 110 Angstrom, 250×21.2 mm) to give the product.

ES/MS: 504.8 (M$^+$).

$^1$H NMR (400 MHz, DMSO-d6) δ 8.53 (d, J=2.1 Hz, 1H), 8.44 (d, J=2.2 Hz, 1H), 7.98 (s, 1H), 7.86 (dt, J=6.2, 3.5 Hz, 1H), 7.82 (t, J=2.2 Hz, 1H), 7.74-7.67 (m, 1H), 7.60-7.51 (m, 2H), 4.72 (s, 2H), 4.50 (s, 2H), 4.41 (t, J=6.7 Hz, 2H), 3.53-3.37 (m, 1H), 2.98 (t, J=6.6 Hz, 2H), 2.74-2.61 (m, 2H), 2.32 (tt, J=9.4, 2.4 Hz, 2H).

Procedure 152: Example 1065

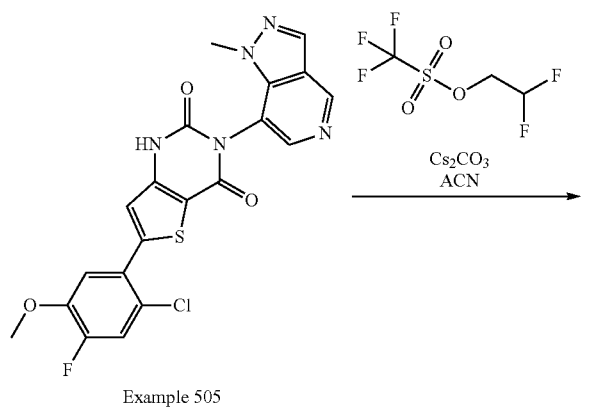

6-(2-chloro-4-fluoro-5-methoxy-phenyl)-1-(2,2-difluoro-ethyl)-3-(1-methylpyrazolo[4,3-c]pyridin-7-yl)thieno[3,2-d]pyrimidine-2,4-dione (Example 1065): To a stirring solution of 6-(2-chloro-4-fluoro-5-methoxyphenyl)-3-(1-methyl-1H-pyrazolo[4,3-c]pyridin-7-yl)thieno[3,2-d]pyrimidine-2,4(1H,3H)-dione (Example 505) (HCl salt) (25 mg, 0.051 mmol), in ACN (1 mL), was added Cs$_2$CO$_3$ (49.4 mg, 0.15 mmol) followed by 2,2-difluoroethyl trifluoromethanesulfonate (14.1 mg, 0.066 mmol). The reaction mixture was stirred for 48 hours at 50° C., after which the mixture was diluted with water (0.2 mL) and TFA (0.5 mL), and the mixture was filtered through an acrodisc, and purified directly by RP-HPLC (0.1% TFA-ACN in 0.1% TFA Water, Column: Gemini 5 μM, NX-C18 110 Angstrom, 250×21.2 mm) to give the product.

ES/MS: 521.7 (M$^+$).

1H NMR (400 MHz, DMSO) δ 9.31 (s, 1H), 8.53 (d, J=14.2 Hz, 2H), 7.92 (s, 1H), 7.75 (d, J=11.0 Hz, 1H), 7.53 (d, J=8.8 Hz, 1H), 6.38 (dt, J=54.8, 3.6 Hz, 2H), 4.74-4.67 (m, 1H), 3.97 (s, 3H), 3.91 (s, 3H).

Examples 1066

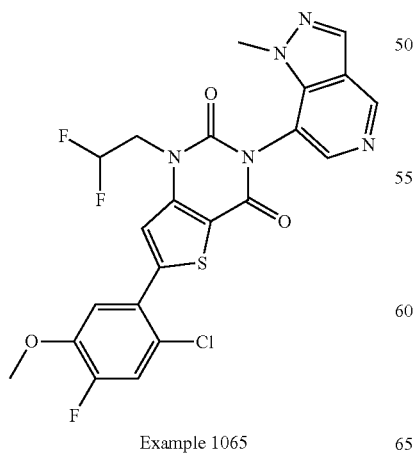

The following Examples were made in an analogous fashion according to Procedure 152 and are shown below in Table 57. To prepare the below Examples, different reagents/starting materials were used than some of those described in Procedure 152 and are noted in the last column of Table 57—"Changes to Procedure 152: Different Reagents/Starting Materials".

TABLE 57

Example 1066

| Example | Structure | ES/MS m/z | 1H-NMR | Changes to Procedure 152: Different Reagents/ Starting Materials |
|---|---|---|---|---|
| 1066 | 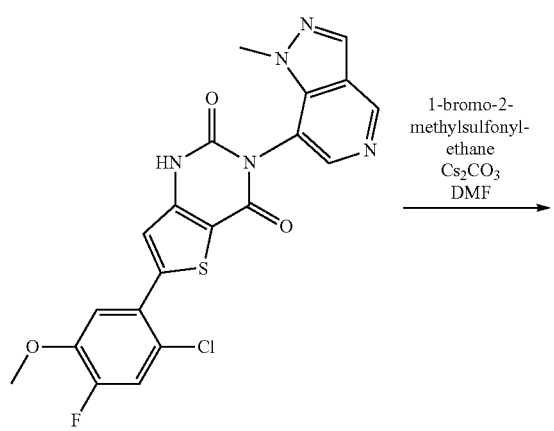 | 539.7 | 1H NMR (400 MHz, DMSO) δ 9.38 (s, 1H), 8.59 (d, J = 11.0 Hz, 2H), 7.96 (s, 1H), 7.76 (d, J = 11.0 Hz, 1H), 7.50 (d, J = 8.8 Hz, 1H), 5.16 (q, J = 8.8 Hz. 2H), 3.97 (s, 3H), 3.93 (s, 3H). | 2,2,2-trifluoroethyl trifluoromethane-sulfonate |

Procedure 153: Example 1067

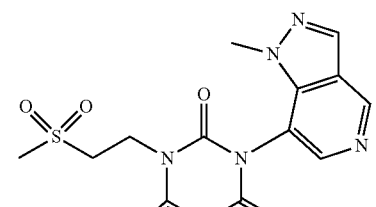

Example 505

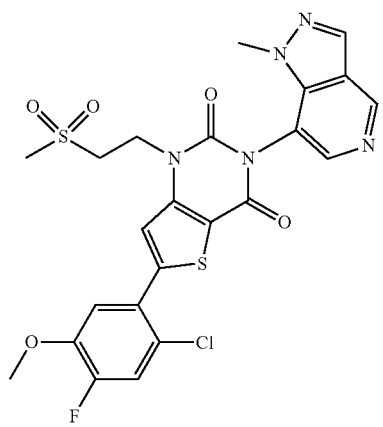

Example 1067

6-(2-chloro-4-fluoro-5-methoxy-phenyl)-3-(1-methylpyrazolo[4,3-c]pyridin-7-yl)-1-(2-methylsulfonylethyl)thieno[3,2-d]pyrimidine-2,4-dione (Example 1067): To a stirring solution of 6-(2-chloro-4-fluoro-5-methoxyphenyl)-3-(1-methyl-1H-pyrazolo[4,3-c]pyridin-7-yl)thieno[3,2-d]pyrimidine-2,4(1H,3H)-dione (Example 505) (HCl salt) (33.3 mg, 0.067 mmol, 1.0 equiv.), in DMF (1 mL), was added $Cs_2CO_3$ (65.8 mg, 0.20 mmol) followed by 1-bromo-2-methylsulfonyl-ethane (37.8 mg, 0.20 mmol). The reaction mixture was stirred for 16 hour at 80° C., after which the mixture was diluted with water (0.2 mL) and TFA (0.5 mL), and the mixture was filtered through an acrodisc, and purified directly by RP-HPLC (0.1% TFA-ACN in 0.1% TFA Water, Column: Gemini 5 μM, NX-C18 110 Angstrom, 250×21.2 mm) to give the product.

ES/MS: 565.7 (M$^+$).

1H NMR (400 MHz, DMSO) δ 9.36 (s, 1H), 8.59 (s, 1H), 8.50 (s, 1H), 7.86 (s, 1H), 7.75 (d, J=11.0 Hz, 1H), 7.59 (d, J=8.9 Hz, 1H), 4.70 (d, J=7.9 Hz, 1H), 4.60-4.55 (m, 1H), 3.% (d, J=13.5 Hz, 6H), 3.70 (t, J=6.6 Hz, 2H), 3.12 (s, 3H).

Examples 1068-1073

The following Examples were made in an analogous fashion according to Procedure 153 and are shown below in Table 58. To prepare the below Examples, different reagents/starting materials were used than some of those described in Procedure 153 and are noted in the last column of Table 58—"Changes to Procedure 153: Different Reagents/Starting Materials".

TABLE 58

Examples 1068-1073

| Example | Structure | ES/MS m/z | 1H-NMR | Changes to Procedure 153: Different Reagents/ Starting Materials |
|---|---|---|---|---|
| 1068 | 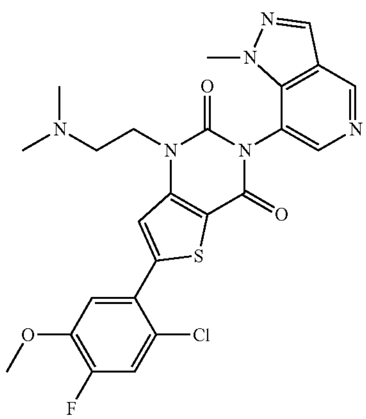 [SMILES: COc1cc(-c2cc3c(s2)c(=O)n(-c2cncc4cnn(C)c24)c(=O)n3CCN(C)C)c(Cl)cc1F] | 528.8 | 1H NMR (400 MHz, DMSO) δ 9.25 (s, 1H), 8.49 (s, 1H), 8.41 (s, 1H), 7.86 (s, 1H), 7.78 (d, J = 11.0 Hz, 1H), 7.54 (d, J = 8.9 Hz, 1H), 4.61 (dt, J = 14.4, 7.0 Hz, 2H), 4.45 (dt, J = 15.3, 5.8 Hz, 2H), 3.98 (s, 3H), 3.92 (s, 3H), 2.94 (dd, J = 11.9, 4.6 Hz, 6H). | 2-bromo-N,N-dimethyl-ethanamine; hydrobromide, DMSO |
| 1069 | 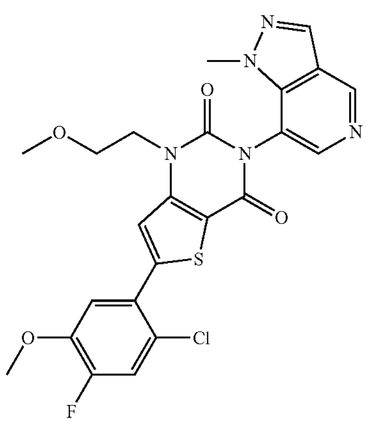 [SMILES: COCCn1c(=O)n(-c2cncc3cnn(C)c23)c(=O)c2sc(-c3cc(OC)c(F)cc3Cl)cc21] | 517.8 | 1H NMR (400 MHz, DMSO) δ 9.32 (s, 1H), 8.54 (d, J = 17.9 Hz, 2H), 7.84 (s, 1H), 7.74 (d, J = 11.0 Hz, 1H), 7.53 (d, J = 8.9 Hz, 1H), 4.47-4.42 (m, 1H), 4.34-4.29 (m, 1H), 3.97 (s, 3H), 3.91 (S, 3H), 3.72 (ddd, J = 15.3, 8.6, 4.0 Hz, 2H), 3.28 (s, 3H). | 1-iodo-2-methoxy-ethane |
| 1070 | 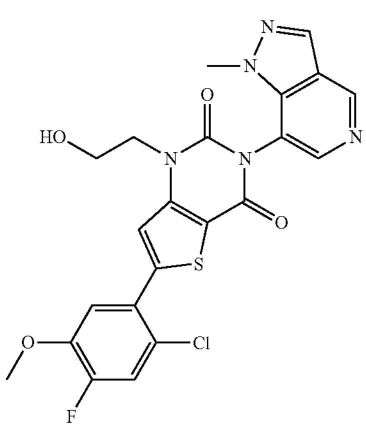 [SMILES: COc1cc(-c2cc3c(s2)c(=O)n(-c2cncc4cnn(C)c24)c(=O)n3CCO)c(Cl)cc1F] | 501.7 | 1H NMR (400 MHz, DMSO) δ 9.39 (s, 1H), 8.61 (s, 1H), 8.55 (s, 1H), 7.84 (s, 1H), 7.76-7.71 (m, 1H), 7.53 (d, J = 8.9 Hz, 1H), 4.36-4.17 (m, 2H), 3.99-3.90 (m, 6H), 3.77 (t, J = 5.5 Hz, 2H). | 2-iodoethanol |

TABLE 58-continued

Examples 1068-1073

| Example | Structure | ES/MS m/z | 1H-NMR | Changes to Procedure 153: Different Reagents/ Starting Materials |
|---|---|---|---|---|
| 1071 | 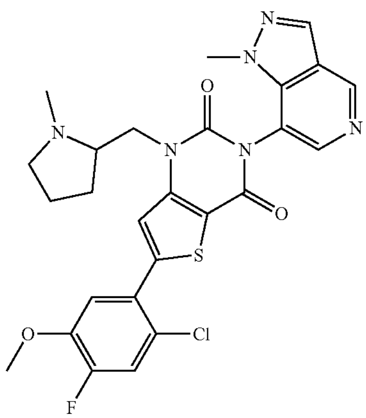 [SMILES: COc1cc(-c2cc3c(s2)c(=O)n(-c2cncc4cnn(C)c24)c(=O)n3CC2CCCN2C)c(Cl)cc1F] | 554.8 | 1H NMR (400 MHz, DMSO) δ 9.23 (s, 1H), 8.50-8.42 (m, 2H), 7.85-7.75 (m, 2H), 7.52 (dd, J = 8.8, 1.3 Hz, 1H), 4.58 (dt, J = 13.7, 5.1 Hz, 2H), 4.48 (dd, J = 15.0, 7.6 Hz, 2H), 3.97 (s, 3H), 3.91 (d, J = 4.3 Hz, 3H), 3.85-3.64 (m, 3H), 3.16 (s, 1H), 2.99 (dd, J = 14.5, 4.0 Hz, 3H), 2.94-2.82 (m, 1H), 2.04-1.83 (m, 4H). | 2-(bromomethyl)-1-methyl-pyrrolidine; hydrobromide |
| 1072 | 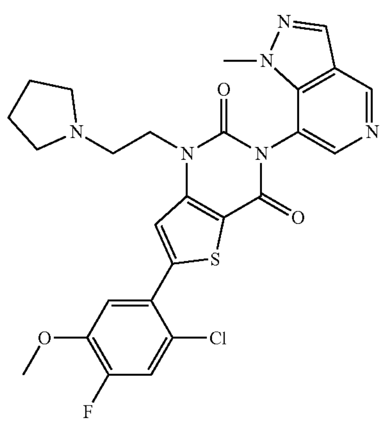 [SMILES: COc1cc(-c2cc3c(s2)c(=O)n(-c2cncc4cnn(C)c24)c(=O)n3CCN2CCCC2)c(Cl)cc1F] | 554.8 | 1H NMR (400 MHz, DMSO) δ 9.29 (s, 1H), 8.52 (s, 1H), 8.46 (s, 1H), 7.87 (s, 1H), 7.76 (d, J = 11.0 Hz, 1H), 7.54 (d, J = 8.8 Hz, 1H), 4.62 (dt, J = 14.5, 7.0 Hz, 1H), 4.45 (dt, J = 15.1, 5.9 Hz, 1H), 3.98 (s, 3H), 3.93 (s, 3H), 3.78-3.50 (m, 4H), 3.26-3.09 (m, 2H), 2.03 (d, J = 7.5 Hz, 2H), 1.92-1.84 (m, 2H). | 1-(2-bromoethyl) pyrrolidine; hydrochloride |
| 1073 | 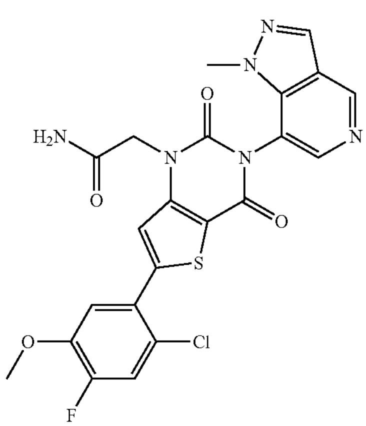 [SMILES: COc1cc(-c2cc3c(s2)c(=O)n(-c2cncc4cnn(C)c24)c(=O)n3CC(N)=O)c(Cl)cc1F] | 514.7 | 1H NMR (400 MHz, DMSO) δ 9.25 (s, 1H), 8.48 (s, 1H), 8.42 (s, 1H), 7.80 (s, 1H), 7.78-7.66 (m, 2H), 7.53 (d, J = 8.9 Hz, 1H), 7.38 (s, 1H), 4.79 (d, J = 8.8 Hz, 2H), 3.97 (s, 3H), 3.89 (s, 3H), | 2-bromoacetamide |

Procedure 154: Example 1074 and Example 1075
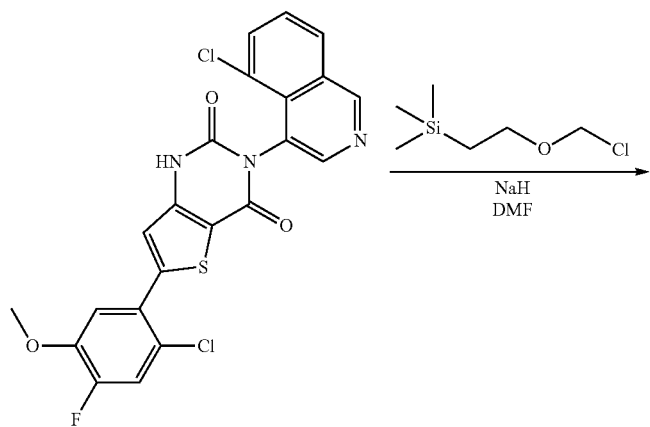
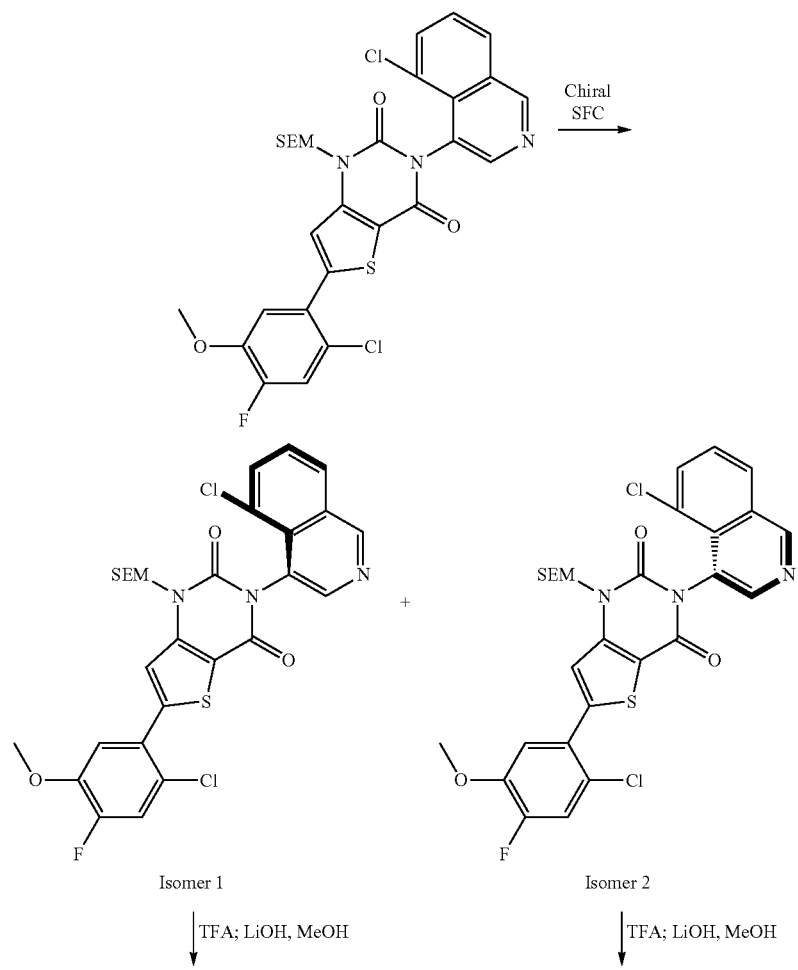

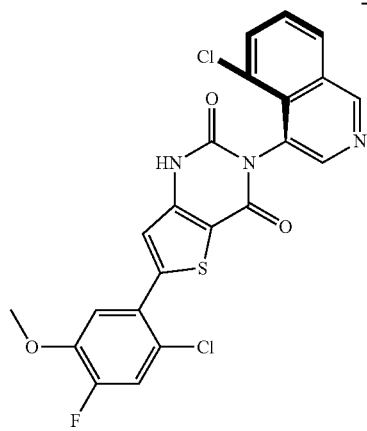

Example 1074

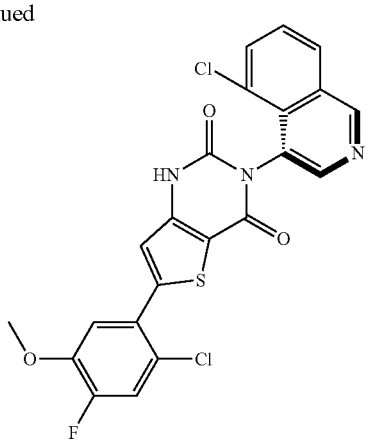

Example 1075

6-(2-chloro-4-fluoro-5-methoxy-phenyl)-3-(5-chloro-4-isoquinolyl)-1-(2-trimethylsilylethoxymethyl)thieno[3,2-d]pyrimidine-2,4-dione. To a stirring solution of 6-(2-chloro-4-fluoro-5-methoxy-phenyl)-3-(5-chloro-4-isoquinolyl)-1H-thieno[3,2-d]pyrimidine-2,4-dione (Example 1078) (260 mg, 0.53 mmol) in DMF (1 mL) at 0° C. was added 60% NaH (40.8 mg, 0.106 mmol, 2 equiv.) and stirred for 45 min after which 2-(chloromethoxy)ethyl-trimethyl-silane (0.104 mL, 0.586 mmol) was added. The reaction mixture was stirred at rt for 30 min after which NaHCO$_3$ (10 mL) was added followed by EtOAc (100 mL). The partitions were separated, and the organic layer was washed with brine (2×20 mL), dried over MgSO$_4$, and concentrated under reduced pressure. The crude residue was purified by silica gel chromatography (eluent: EtOAc/hexanes), to provide the product.

6-(2-chloro-4-fluoro-5-methoxy-phenyl)-3-(5-chloro-4-isoquinolyl)-1-(2-trimethylsilylethoxymethyl)thieno[3,2-d]pyrimidine-2,4-dione as a mixture of 2 atropisomers was separated by chiral SFC (IG 5 μm 4.6×$^{100}$ mm column with 35% EtOH cosolvent) to provide 2 isomers, which were deprotected separately:

Isomer 1:

6-(2-chloro-4-fluoro-5-methoxy-phenyl)-3-(5-chloro-4-isoquinolyl)-1-(hydroxymethyl)thieno[3,2-d]pyrimidine-2,4-dione (Example 1074)

To a 20 mL scintillation vial containing a stir bar was added 6-(2-chloro-4-fluoro-5-methoxy-phenyl)-3-(5-chloro-4-isoquinolyl)-1-(2-trimethylsilylethoxymethyl)thieno[3,2-d]pyrimidine-2,4-dione (Isomer 1) (40 mg, 0.064 mmol, 1.0 equiv.), followed TFA (0.5 mL). The reaction mixture was stirred for 2 h and subsequently concentrated under reduced pressure. To a stirring solution of the crude material in MeOH/H$_2$O (1 mL, 0.1 M) at rt was added LiOH (6.1 mg, 0.26 mmol, 2.5 equiv.). The reaction mixture stirred at rt for 1 h after which TFA (0.5 mL) was added. The solid was collected via filtration and redissolved in DMSO/trifluoroacetic acid (4.0 mL; 4:1), filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 1074 as a trifluoroacetate salt. The stereochemistry of Example 1074 was assigned by analogy to Example 438, with Example 1074 being the more active isomer.

ES/MS: 489.7 (M$^+$).

1H NMR (400 MHz, DMSO) δ 12.32 (s, 1H), 9.54 (s, 1H), 8.62 (s, 1H), 8.34 (dd, J=8.3, 1.2 Hz, 1H), 7.96 (dd, J=7.6, 1.1 Hz, 1H), 7.82-7.66 (m, 2H), 7.50 (d, J=8.9 Hz, 1H), 7.31 (s, 1H), 3.95 (s, 3H).

Isomer 2:

6-(2-chloro-4-fluoro-5-methoxy-phenyl)-3-(5-chloro-4-isoquinolyl)-1-(hydroxymethyl)thieno[3,2-d]pyrimidine-2,4-dione (Example 1075)

To a 20 mL scintillation vial containing a stir bar was added 6-(2-chloro-4-fluoro-5-methoxy-phenyl)-3-(5-chloro-4-isoquinolyl)-1-(2-trimethylsilylethoxymethyl)thieno[3,2-d]pyrimidine-2,4-dione (Isomer 2) (63.1 mg, 0.102 mmol, 1.0 equiv.), followed TFA (0.5 mL). The reaction mixture was stirred for 2 h and subsequently concentrated under reduced pressure. To a stirring solution of the crude material in MeOH/H$_2$O (1 mL, 0.1 M) at rt was added LiOH (12.2 mg, 0.52 mmol, 2.5 equiv.). The reaction mixture stirred at rt for 1 h after which TFA (0.5 mL) was added. The solid was collected via filtration and redissolved in DMSO/trifluoroacetic acid (4.0 mL; 4:1), filtered through an acrodisc, and purified directly by RP-HPLC (0.1% TFA-ACN in 0.1% TFA Water, Column: Gemini 5 μM, NX-C18 110 Angstrom, 250×21.2 mm) to give the title compound Example 1075 as a trifluoroacetate salt. The stereochemistry of Example 1075 was assigned by analogy to Example 438, with Example 1075 being the less active isomer.

ES/MS: 489.7 (M$^+$).

1H NMR (400 MHz, DMSO) δ 12.32 (s, 1H), 9.54 (s, 1H), 8.62 (s, 1H), 8.34 (dd, J=8.3, 1.2 Hz, 1H), 7.96 (dd, J=7.6, 1.1 Hz, 1H), 7.82-7.66 (m, 2H), 7.50 (d, J=8.9 Hz, 1H), 7.31 (s, 1H), 3.95 (s, 3H).

Procedure 155: Example 1076 and Example 1077

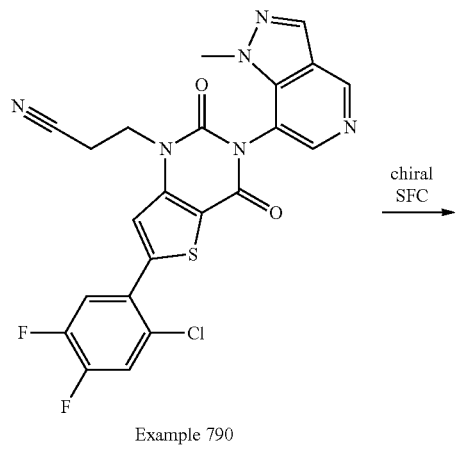

Example 790

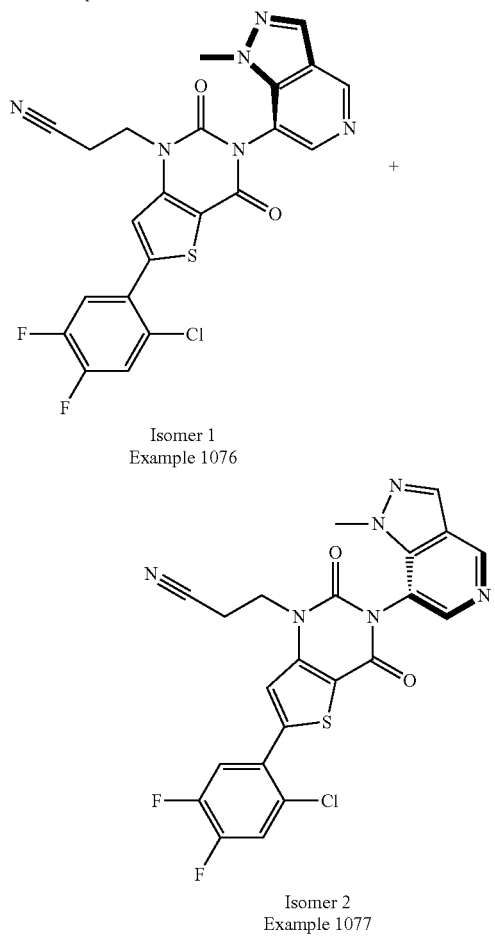

Isomer 1
Example 1076

Isomer 2
Example 1077

3-[6-(2-chloro-4,5-difluoro-phenyl)-3-(1-methylpyrazolo[4,3-c]pyridin-7-yl)-2,4-dioxo-thieno[3,2-d]pyrimidin-1-yl]propanenitrile (Example 1076 and Example 1077): 3-[16-(2-chloro-4,5-difluoro-phenyl)-3-(1-methylpyrazolo[4,3-c]pyridin-7-yl)-2,4-dioxo-thieno[3,2-d]pyrimidin-1-yl]propanenitrile (Example 790) as a mixture of 2 isomers was separated by chiral SFC (AD-H 4.6×$^{100}$ mm column with 50% EtOH cosolvent) to give two enantiomers, which were assigned as Isomer 1 and Isomer 2. The stereochemistry was assigned by analogy to Example 438, with Example 1076 being the more active isomer.

Isomer 1:

3-[6-(2-chloro-45-difluoro-phenyl)-3-(1-methylpyrazolo[4,3-c]pyridin-7-yl)-2,4-dioxo-thieno[3,2-d]pyrimidin-1-yl]propanenitrile (Example 1076)

ES/MS: 498.8 (M$^+$).
1H NMR (400 MHz, DMSO) δ 9.32 (s, 1H), 8.55 (s, 1H), 8.49 (s, 1H), 8.15 (dd, J=11.4, 8.4 Hz, 1H), 8.07 (d, J=3.7 Hz, 1H), 8.06-8.00 (m, 1H), 4.53 (dt, J=14.2, 7.0 Hz, 1H), 4.43-4.35 (m, 1H), 3.93 (s, 3H), 3.09 (td, J=6.7, 2.6 Hz, 2H).

Isomer 2:

3-[6-(2-chloro-4,5-difluoro-phenyl)-3-(1-methylpyrazolo[4,3-c]pyridin-7-yl)-2,4-dioxo-thieno[3,2-d]pyrimidin-1-yl]propanenitrile (Example 1077)

ES/MS: 498.7 (M$^+$).
1H NMR (400 MHz, DMSO) δ 9.32 (s, 1H), 8.55 (s, 1H), 8.49 (s, 1H), 8.15 (dd, J=11.4, 8.4 Hz, 1H), 8.07 (d, J=3.7 Hz, 1H), 8.06-8.00 (m, 1H), 4.53 (dt, J=14.2, 7.0 Hz, 1H), 4.43-4.35 (m, 1H), 3.93 (s, 3H), 3.09 (td, J=6.7, 2.6 Hz, 2H).

Procedure 156: Example 1078

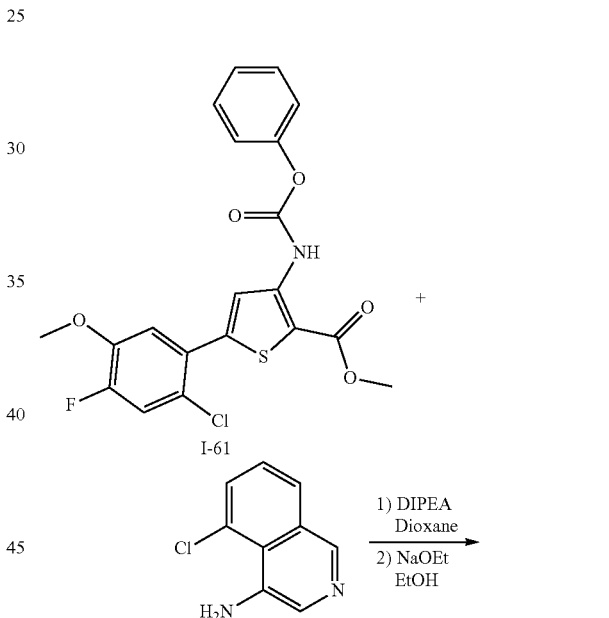

I-61

1) DIPEA
Dioxane
2) NaOEt
EtOH

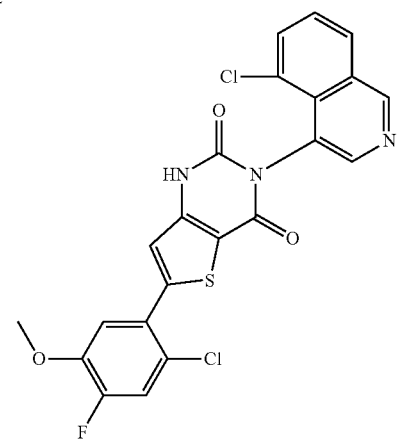

Example 1078

6-(2-chloro-4-fluoro-5-methoxyphenyl)-3-(5-chloroisoquinolin-4-yl)thieno[3,2-d]pyrimidine-2,4(1H,3H)-dione (Example 1078): To a suspension of methyl 5-(2-chloro-4-fluoro-5-methoxyphenyl)-3-((phenoxycarbonyl)amino)thiophene-2-carboxylate (I-61) (50 mg, 0.115 mmol) in dioxane (2 mL) and DIPEA (99 μL, 0.57 mmol) was added 5-chloroisoquinolin-4-amine (30.7 mg, 0.17 mmol). The reaction mixture was stirred at 90° C. overnight. The reaction mixture was then cooled to ambient temperature and concentrated under reduced pressure. To the resulting crude residue was then added EtOH (2 mL) and sodium ethoxide (0.2 mL, from 21% wt. in EtOH). The reaction mixture was then stirred at 80° C. for 2 hours. The reaction mixture was filtered, rinsed once with mixture of MeOH (0.5 mL), water (0.5 mL), and TFA (0.08 mL) then filtered through an acrodisc. The combined filtrate was purified by RP-HPLC (0.1% TFA-ACN in 0.1% TFA Water, Column: Gemini 10 μM, NX-C18, 110 Angstrom, 250×30 mm) to give the product.

$^{1}$H NMR (400 MHz, DMSO-d$_{6}$) δ 12.32 (s, 1H), 9.54 (s, 1H), 8.62 (s, 1H), 8.34 (dd, J=8.3, 1.1 Hz, 1H), 7.96 (dd, J=7.7, 1.1 Hz, 1H), 7.77 (t, J=7.9 Hz, 1H), 7.71 (d, J=11.1 Hz, 1H), 7.50 (d, J=8.9 Hz, 1H), 7.31 (s, 1H), 3.95 (s, 3H).

ES/MS: 488.2 (M$^{+}$).

Examples 1079-1082

The following Examples were made in an analogous fashion according to Procedure 156 and are shown below in Table 59. To prepare the below Examples, different reagents/starting materials were used than some of those described in Procedure 156 and are noted in the last column of Table 59—"Changes to Procedure 156: Different Reagents/Starting Materials".

TABLE 59

Examples 1079-1082

| Example | Structure | ES/MS m/z | 1H-NMR | Changes to Procedure 156: Different Reagents/ Starting Materials |
|---|---|---|---|---|
| 1079 | 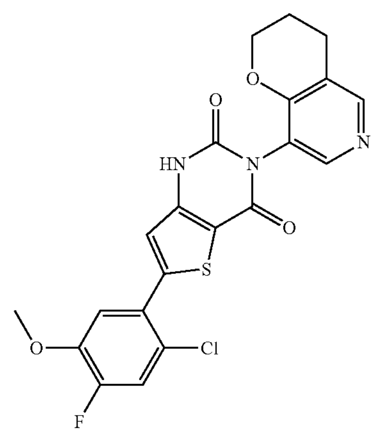 [SMILES: COc1cc(-c2cc3[nH]c(=O)n(-c4cncc5c4OCCC5)c(=O)c3s2)c(Cl)cc1F] | 460.1 | 1H NMR (400 MHz, DMSO-d6) δ 12.33 (s, 1H), 8.58 (d, J = 9.9 Hz, 2H), 7.71 (d, J = 11.1 Hz, 1H), 7.45 (d, J = 8.9 Hz, 1H), 7.27 (s, 1H), 4.40 (t, J = 5.1 Hz, 2H), 3.94 (s, 3H), 2.91 (q, J = 4.7, 3.1 Hz, 2H), 2.03-1.97 (m, 2H). | I-61, I-164 |
| 1080 | 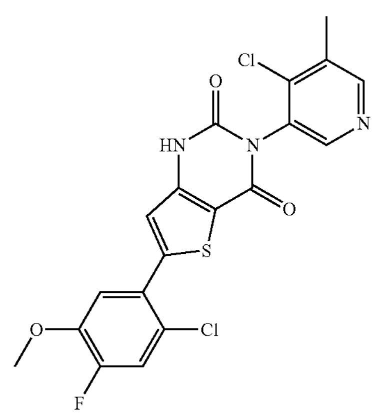 [SMILES: COc1cc(-c2cc3[nH]c(=O)n(-c4cncc(C)c4Cl)c(=O)c3s2)c(Cl)cc1F] | 452.1 | 1H NMR (400 MHz, DMSO-d6) δ 12.37 (s, 1H), 8.64 (s, 1H), 8.56 (s, 1H), 7.71 (d, J = 11.0 Hz, 1H), 7.47 (d, J = 8.9 Hz, 1H), 7.27 (s, 1H), 3.94 (s, 3H), 2.43 (s, 3H). | I-61, 4-chloro-5-methylpyridin-3-amine |

TABLE 59-continued
Examples 1079-1082
| Example | Structure | ES/MS m/z | 1H-NMR | Changes to Procedure 156: Different Reagents/ Starting Materials |
|---------|-----------|-----------|--------|------------------------------------------------------------------|
| 1081 | 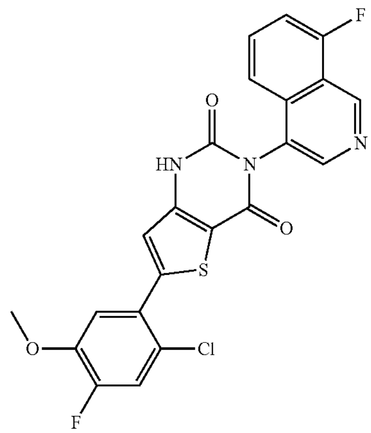 [SMILES: COc1cc(-c2cc3[nH]c(=O)n(-c4cncc5c(F)cccc45)c(=O)c3s2)c(Cl)cc1F] | 472.2 | 1H NMR (400 MHz, DMSO-d6) δ 12.34 (s, 1H), 9.59 (s, 1H), 8.72 (s, 1H), 7.85-7.79 (m, 1H), 7.76-7.69 (m, 2H), 7.59 (dd, J = 10.6, 7.6 Hz, 1H), 7.45 (d, J = 8.8 Hz, 1H), 7.33 (s, 1H), 3.95 (s, 3H). | I-61, 8-fluoroisoquinolin-4-amine |
| 1082 | 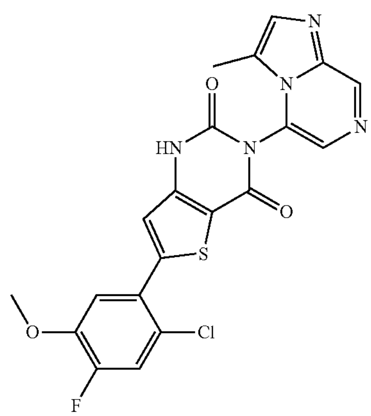 [SMILES: COc1cc(-c2cc3[nH]c(=O)n(-c4cncc5ncc(C)n45)c(=O)c3s2)c(Cl)cc1F] | 458.0 | 1H NMR (400 MHz, DMSO-d6) δ 12.63 (s, 1H), 9.13 (s, 1H), 8.11 (s, 1H), 7.75-7.70 (m, 2H), 7.49 (d, J = 8.9 Hz, 1H), 7.33 (s, 1H), 3.95 (s, 3H), 2.34 (s, 3H). | I-339; I-61 |
Procedure 157: Example 1083
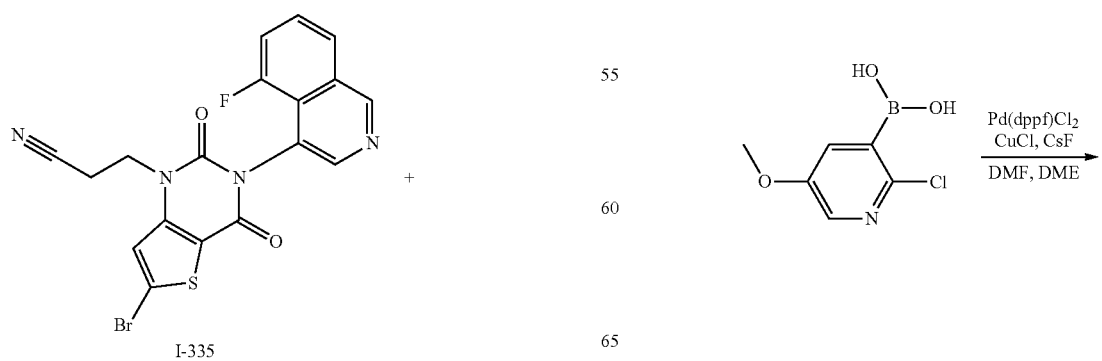

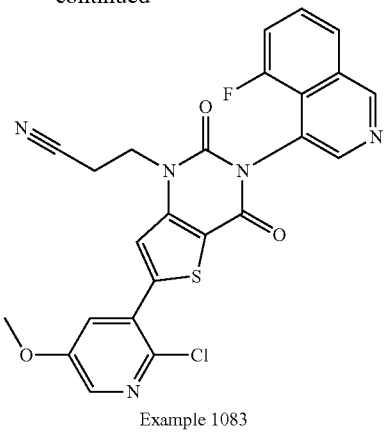

Example 1083

3-(6-(2-chloro-5-methoxypyridin-3-yl)-3-(5-fluoroisoquinolin-4-yl)-2,4-dioxo-3,4-dihydrothieno[3,2-d]pyrimidin-1(2H)-yl)propanenitrile (Example 1083). To a microwave vial containing a stir bar was added 3-[6-bromo-3-(5-fluoro-4-isoquinolyl)-2,4-dioxo-thieno[3,2-d]pyrimidin-1-yl]propanenitrile (I-335) (25 mg, 0.056 mmol), (2-chloro-5-methoxy-3-pyridyl)boronic acid (15 mg, 0.084 mmol), Pd(dppf)Cl$_2$ (9.2 mg, 0.011 mmol), cesium fluoride (25.6 mg, 0.168 mmol), and copper (1) chloride (11 mg, 0.112 mmol), followed by DMF (1 ml) and DME (1 mL). The vial was degassed under argon (1 min), sealed, and heated at 90° C. for 20 minutes under microwave conditions. The mixture was cooled to rt and diluted with 20% MeOH/DCM, filtered through celite, rinsing with 20% MeOH/DCM (80 mL), and concentrated under reduced pressure. The reaction mixture was dissolved in DMF (1 mL), MeOH (I mL), water (0.2 mL) and TFA (0.1 mL) and filtered through an acrodisc. This solution purified directly by RP-HPLC (0.1% TFA-ACN in 0.1% TFA Water, Column: Gemini 10 μM, NX-C18 110 Angstrom, 250×30 mm) to give product.

ES/MS: 508.06 (M$^+$).

$^1$H NMR (400 MHz, DMSO-d$_6$) δ 9.61 (s, 1H), 8.65 (s, 1H), 8.32 (d, J=2.9 Hz, 1H), 8.19 (dd J=8.3, 1.0 Hz, 1H), 8.13 (s, 1H), 7.96 (d, J=3.0 Hz, 1H), 7.83-7.74 (m, 1H), 7.70-7.59 (m, 1H), 4.51-4.42 (m, 2H), 3.97 (s, 3H), 3.03 (t, J=6.6 Hz, 2H).

Examples 1084-1087

The following Examples were made in an analogous fashion according to Procedure 157 and are shown below in Table 60. To prepare the below Examples, different reagents/starting materials were used than some of those described in Procedure 157 and are noted in the last column of Table 60—"Changes to Procedure 157: Different Reagents/Starting Materials".

TABLE 60

Examples 1084-1087

| Example | Structure | ES/MS m/z | 1H-NMR | Changes to Procedure 157: Different Reagents/ Starting Materials |
|---|---|---|---|---|
| 1084 | 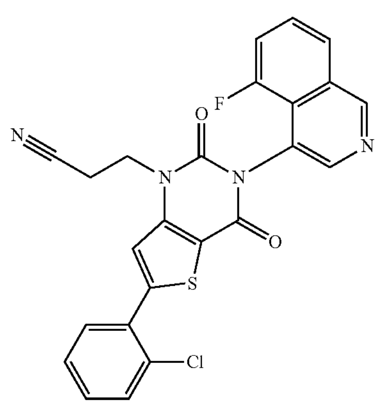 [SMILES: N#CCCn1c(=O)n(-c2cncc3cccc(F)c23)c(=O)c2sc(-c3ccccc3Cl)cc21] | 477.1 | 1H NMR (400 MHz, DMSO-d6) δ 9.58 (s, 1H), 8.64 (s, 1H), 8.19 (dd, J = 8.3, 1.0 Hz, 1H), 8.03 (s, 1H), 7.95-7.85 (m, 1H), 7.92-7.88 (m, 1H), 7.73-7.69 (m, 1H), 7.65 (ddd, J = 12.9, 7.8, 1.0 Hz, 1H), 7.59-7.54 (m, 2H), 4.50-4.41 (m, 2H), 3.03-2.99 (m, 2H). | I-335, (2-chlorophenyl) boronic acid |

TABLE 60-continued

Examples 1084-1087

| Example | Structure | ES/MS m/z | 1H-NMR | Changes to Procedure 157: Different Reagents/ Starting Materials |
|---|---|---|---|---|
| 1085 | 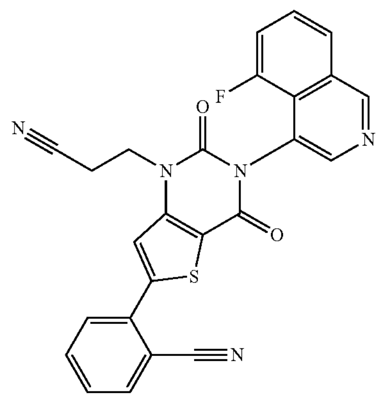 [SMILES: N#CCCn1c(=O)n(-c2cncc3cccc(F)c23)c(=O)c2sc(-c3ccccc3C#N)cc21] | 468.1 | 1H NMR (400 MHz, DMSO-d6) δ 9.59 (s, 1H), 8.65 (s, 1H), 8.19 (dd, J = 8.3, 1.0 Hz, 1H), 8.14 (s, 1H), 8.11 (dd, J = 7.8, 1.2 Hz, 1H), 7.99-7.91 (m, 2H), 7.85-7.73 (m, 2H). 7.70-7.61 (m, 1H), 4.51-4.40 (m, 2H), 3.07-2.98 (m, 2H). | I-335, (2-cyanophenyl) boronic acid |
| 1086 | 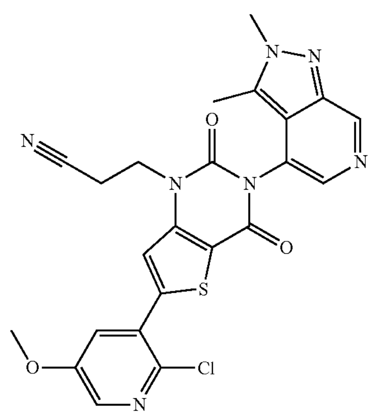 [SMILES: COc1cnc(Cl)c(-c2cc3c(s2)c(=O)n(-c2cncc4nn(C)c(C)c24)c(=O)n3CCC#N)c1] | 508.1 | 1H NMR (400 MHz, DMSO-d6) δ 9.35 (s, 1H), 8.33 (d, J = 3.0 Hz, 1H), 8.13 (s, 1H), 8.12 (s, 1H), 7.96 (d, J = 3.0 Hz, 1H), 4.52 (dt, J = 14.0, 6.9 Hz, 1H), 4.40 (dt, J = 14.2, 6.2 Hz, 1H), 4.20 (s, 3H), 3.97 (s, 3H), 3.08 (t, J = 6.6 Hz, 2H), 2.42 (s, 3H). | I-257, (2-chloro-5-methoxy-3-pyridyl)boronic acid |
| 1087 | 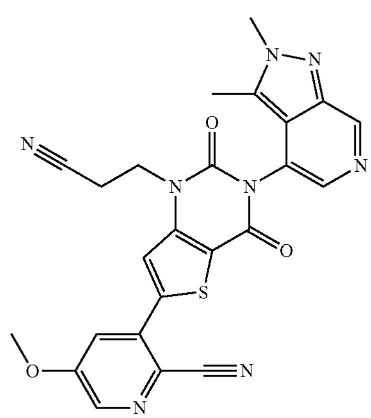 [SMILES: COc1cnc(C#N)c(-c2cc3c(s2)c(=O)n(-c2cncc4nn(C)c(C)c24)c(=O)n3CCC#N)c1] | 499.1 | 1H NMR (400 MHz, DMSO-d6) δ 9.25 (s. 1H), 8.62 (d, J = 2.7 Hz, 1H), 8.21 (s, 1H), 8.07 (s, 1H), 7.91 (d, J = 2.7 Hz, 1H), 4.56-4.35 (m, 2H), 4.18 (s, 3H), 4.06 (s, 3H), 3.08 (t, J = 6.7 Hz, 2H), 2.41 (s, 3H). | I-257, (2-cyano-5-methoxypyridin-3-yl)boronic acid |

Procedure 158: Example 1088 and Example 1089

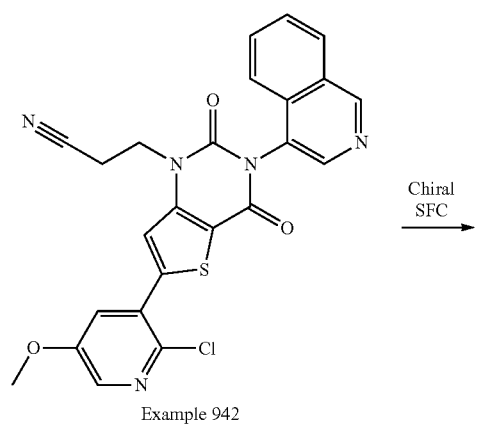

Example 942

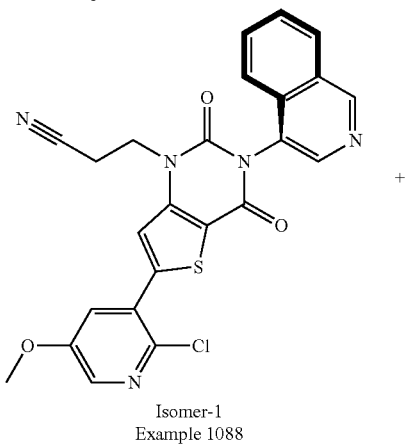

Isomer-1
Example 1088

+

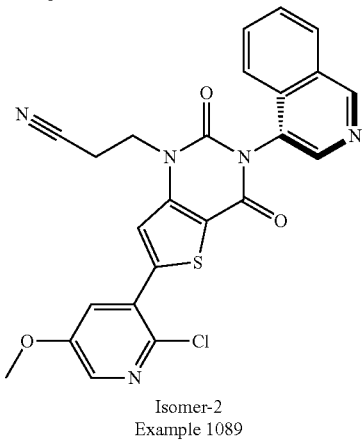

Isomer-2
Example 1089

3-(6-(2-chloro-4-fluorophenyl)-3-(1-methyl-1H-pyrazolo[4,3-c]pyridin-7-yl)-2,4-dioxo-3,4-dihydrothieno[3,2-d]pyrimidin-1(2H)-yl)propanenitrile (Example 1088 and Example 1089): 3-(6-(2-chloro-4-fluorophenyl)-3-(1-methyl-1H-pyrazolo[4,3-c]pyridin-7-yl)-2,4-dioxo-3,4-dihydrothieno[3,2-d]pyrimidin-1(2H)-yl)propanenitrile (Example 942) as a mixture of 2 isomers was separated by chiral SFC (CCO-F2 3 um-4.6×150 mm column with 50% MeOH cosolvent) to give two enantiomers, which were assigned as Isomer 1 and Isomer 2. The stereochemistry was assigned by analogy to Example 438, with Example 1088 being the more active isomer.

Isomer 1:

3-(6-(2-chloro-5-methoxypyridin-3-yl)-3-(isoquinolin-4-yl)-2,4-dioxo-3,4-dihydrothieno[3,2-d]pyrimidin-1(2H)-yl)propanenitrile (Example 1088)

ES/MS: 490.1 (M+).
$^1$H NMR (400 MHz, DMSO-$d_6$) δ 9.48 (s, 1H), 8.59 (s, 1H), 8.33 (d, J=2.9 Hz, 1H), 8.30 (dd, J=7.3, 2.2 Hz, 1H), 8.13 (s, 1H), 7.94 (d, J=2.9 Hz, 1H), 7.93-7.90 (m, 1H), 7.84-7.76 (m, 2H), 4.54-4.37 (m, 2H), 3.98 (s, 3H), 3.04 (t, J=6.7 Hz, 2H).

Isomer 2:

3-(6-(2-chloro-1-methoxypyridin-3-yl)-3-(isoquinolin-4-yl)-2,4-dioxo-3,4-dihydrothieno[3,2-d]pyrimidin-1(2H)-yl)propanenitrile (Example 1089)

ES/MS: 490.1 (M+).
$^1$H NMR (400 MHz, DMSO-$d_6$) δ 9.49 (s, 1H), 8.59 (s, 1H), 8.34-8.29 (m, 2H), 8.13 (s, 1H), 7.93 (dd, J=9.2, 2.2 Hz, 2H), 7.86-7.76 (m, 2H), 4.54-4.36 (m, 2H), 3.98 (s, 3H), 3.04 (t, J=6.7 Hz, 2H).

Procedure 159: Example 1090 and Example 1091

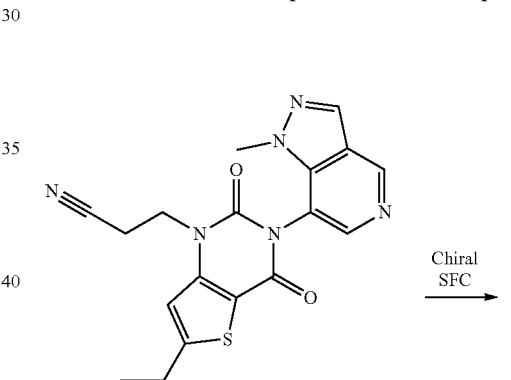

Example 1019

+

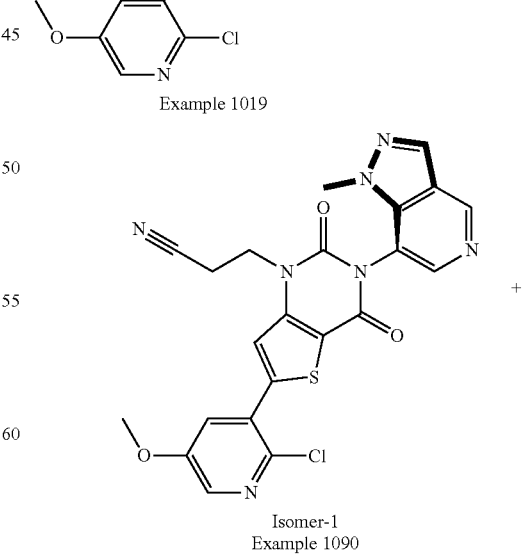

Isomer-1
Example 1090

1477

-continued

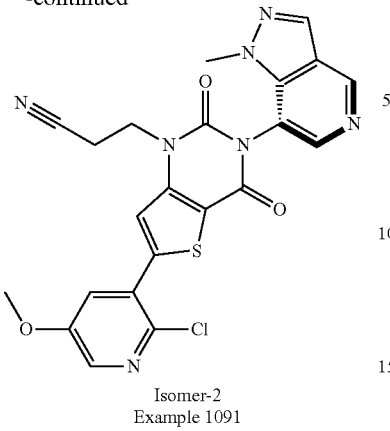

Isomer-2
Example 1091

3-(6-(2-chloro-5-methoxypyridin-3-yl)-3-(1-methyl-1H-pyrazolo[4,3-c]pyridin-7-yl)-2,4-dioxo-3,4-dihydrothieno[3,2-d]pyrimidin-1(2H)-yl)propanenitrile (Example 1090 and Example 1091): 3-(6-(2-chloro-5-methoxypyridin-3-yl)-3-(1-methyl-1H-pyrazolo[4,3-c]pyridin-7-yl)-2,4-dioxo-3,4-dihydrothieno[3,2-d]pyrimidin-1(2H)-yl)propanenitrile (Example 1019) as a mixture of 2 isomers was separated by chiral SFC (IB 5 um-4.6×100 mm column with 40% EtOH cosolvent) to give two enantiomers, which were assigned as Isomer 1 and Isomer 2. The stereochemistry was assigned by analogy to Example 438, with Example 1090 being the more active isomer.

Isomer 1:

3-(6-(2-chloro-5-methoxypyridin-3-yl)-3-(1-methyl-1H-pyrazolo[4,3-c]pyridin-7-yl)-2,4-dioxo-3,4-dihydrothieno[3,2-d]pyrimidin-1(2H)-yl)propanenitrile (Example 1090)

$^1$H NMR (400 MHz, DMSO-d$_6$) δ 9.25 (s, 11H), 8.49 (s, 11H), 8.43 (s, 1H), 8.33 (d, J=2.9 Hz, 1H), 8.13 (s, 1H), 7.95 (d, J=3.0 Hz, 1H), 4.55 (dt, J=14.2, 7.0 Hz, 1H), 4.41 (dt, J=14.4, 6.2 Hz, 1H), 3.97 (s, 3H), 3.91 (s, 3H), 3.12-3.06 (m, 2H).

ES/MS: 494.0 (M$^+$).

Isomer 2:

3-(6-(2-chloro-5-methoxypyridin-3-yl)-3-(1-methyl-1H-pyrazolo[4,3-c]pyridin-7-yl)-2,4-dioxo-3,4-dihydrothieno[3,2-d]pyrimidin-1(2H)-yl)propanenitrile. (Example 1091)

1H NMR (400 MHz, DMSO-d6) δ 9.25 (s, 1H), 8.49 (s, 1H), 8.43 (s, 1H), 8.33 (d, J=3.0 Hz, 1H), 8.13 (s, 1H), 7.95 (d, J=2.9 Hz, 1H), 4.55 (dt, J=14.1, 7.0 Hz, 1H), 4.41 (dt, J=14.4, 6.2 Hz, 1H), 3.97 (s, 3H), 3.91 (s, 3H), 3.13-3.05 (m, 2H).

ES/MS: 494.1 (M$^+$).

1478

Procedure 160: Example 1092 and Example 1093

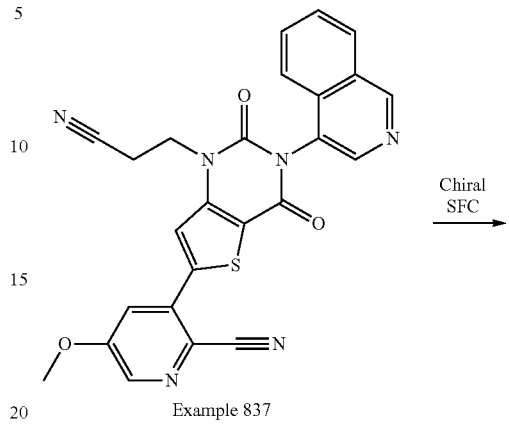

Example 837

Chiral SFC →

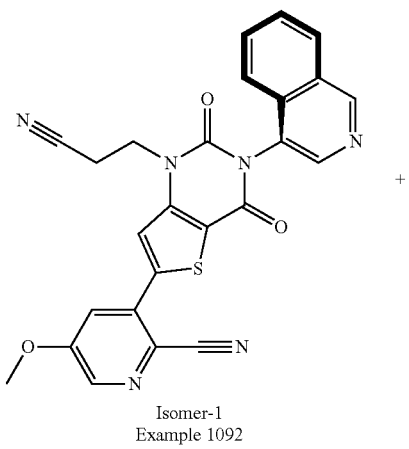

Isomer-1
Example 1092

+

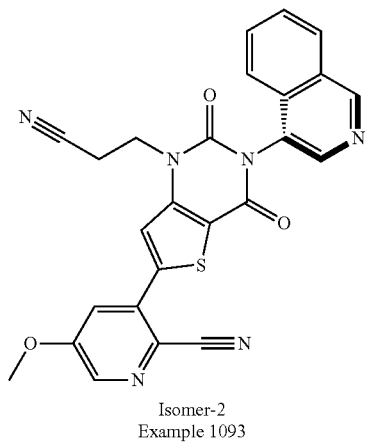

Isomer-2
Example 1093

3-(1-(2-cyanoethyl)-3-(isoquinolin-4-yl)-2,4-dioxo-1,2,3,4-tetrahydrothieno[3,2-d]pyrimidin-6-yl)-5-methoxypicolinonitrile (Example 1092 and Example 1093): 3-(1-(2-cyanoethyl)-3-(isoquinolin-4-yl)-2,4-dioxo-1,2,3,4-tetrahydrothieno[3,2-d]pyrimidin-6-yl)-5-methoxypicolinonitrile (Example 837) as a mixture of 2 isomers was separated by chiral SFC (ID 5 um-4.6×100 mm column with 45% MeOH cosolvent) to give two enantiomers, which were assigned as Isomer 1 and Isomer 2. The stereochemistry was assigned by analogy to Example 438, with Example 1092 being the more active isomer.

Isomer 1:

3-(1-(2-cyanoethyl)-3-(isoquinolin-4-yl)-2,4-dioxo-1,2,3,4-tetrahydrothieno[3,2-d]pyrimidin-6-yl)-5-methoxypicolinonitrile (Example 1092)

¹H NMR (400 MHz, DMSO-d$_6$) δ 9.46 (s, 1H), 8.62 (d, J=2.7 Hz, 1H), 8.58 (s, 1H), 8.33-8.26 (m, 1H), 8.22 (s, 1H), 7.95-7.91 (m, 1H), 7.89 (d, J=2.7 Hz, 1H), 7.83-7.76 (m, 2H), 4.53-4.37 (m, 2H), 4.06 (s, 3H), 3.05 (t, J=6.8 Hz, 2H).

ES/MS: 481.1 (M⁺).

Isomer 2.

3-(1-(2-cyanoethyl)-3-(isoquinolin-4-yl)-2,4-dioxo-1,2,3,4-tetrahydrothieno[3,2-d]pyrimidin-6-yl)-5-methoxypicolinonitrile (Example 1093)

¹H NMR (400 MHz, DMSO-d$_6$) δ 9.46 (d, J=0.8 Hz, 1H), 8.62 (d, J=2.7 Hz, 1H), 8.57 (s, 1H), 8.32-8.27 (m, 1H), 8.22 (s, 1H), 7.95-7.91 (m, 1H), 7.89 (d, J=2.7 Hz, 1H), 7.83-7.75 (m, 2H), 4.54-4.36 (m, 2H), 4.06 (s, 3H), 3.05 (t, J=6.8 Hz, 2H).

ES/MS: 481.1 (M⁺).

Procedure 161: Example 1094 and Example 1095

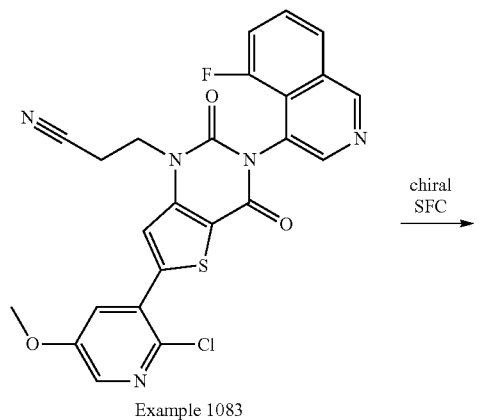

Example 1083 chiral SFC →

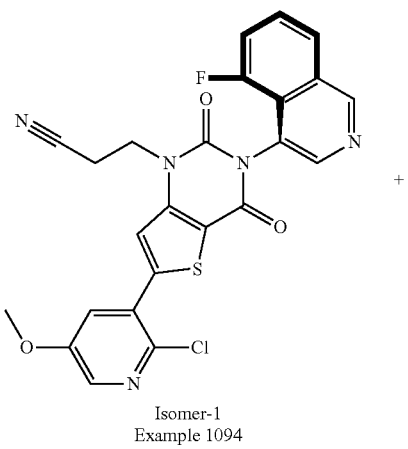

Isomer-1
Example 1094

+

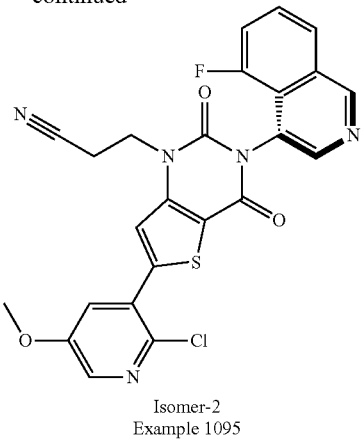

Isomer-2
Example 1095

3-(6-(2-chloro-5-methoxypyridin-3-yl)-3-(5-fluoroisoquinolin-4-yl)-2,4-dioxo-3,4-dihydrothieno[3,2-d]pyrimidin-1(2H)-yl)propanenitrile (Example 1094 and Example 1095): 3-(6-(2-chloro-5-methoxypyridin-3-yl)-3-(5-fluoroisoquinolin-4-yl)-2,4-dioxo-3,4-dihydrothieno[3,2-d]pyrimidin-1(2H)-yl)propanenitrile (Example 1083) as a mixture of 2 isomers was separated by chiral SFC (IB Sum-4.6×100 mm column with 35% MeOH cosolvent) to give two enantiomers, which were assigned as Isomer 1 and Isomer 2. The stereochemistry was assigned by analogy to Example 438, with Example 1094 being the more active isomer.

Isomer 1:

3-(6-(2-chloro-5-methoxypyridin-3-yl)-3-(5-fluoroisoquinolin-4-yl)-2,4-dioxo-3,4-dihydrothieno[3,2-d]pyrimidin-1(2H)-yl)propanenitrile (Example 1094)

1H NMR (400 MHz, DMSO-d6) δ 9.55 (d, J=2.7 Hz, 1H), 8.60 (d, J=6.8 Hz, 1H), 8.33 (d, J=3.2 Hz, 1H), 8.19 (d, J=8.3 Hz, 1H), 8.14 (s, 1H), 7.97 (d, J=3.2 Hz, 1H), 7.82-7.75 (m, 1H), 7.68-7.63 (m, 1H), 4.53-4.42 (m, 2H), 3.97 (s, 3H), 3.04 (t, J=6.7 Hz, 2H).

ES/MS: 508.2 (M⁺).

Isomer 2.

3-(6-(2-chloro-5-methoxypyridin-3-yl)-3-(5-fluoroisoquinolin-4-yl)-2,4-dioxo-3,4-dihydrothieno[3,2-d]pyrimidin-1(2H)-yl)propanenitrile (Example 1095)

1H NMR (400 MHz, DMSO-d6) δ 9.55 (d, J=2.6 Hz 1H), 8.66-8.53 (m, 1H), 8.37-8.25 (m, 1H), 8.19 (dd, J=8.5, 2.7 Hz, 1H), 8.15-8.06 (m, 1H), 7.97-7.96 (m, 1H), 7.82-7.76 (m, 1H), 7.70-7.55 (m, 1H), 4.53-4.43 (m, 2H), 3.97 (s, 3H), 3.04 (t, J=6.6 Hz, 2H).

ES/MS: 508.2 (M⁺).

Procedure 162: Example 1096

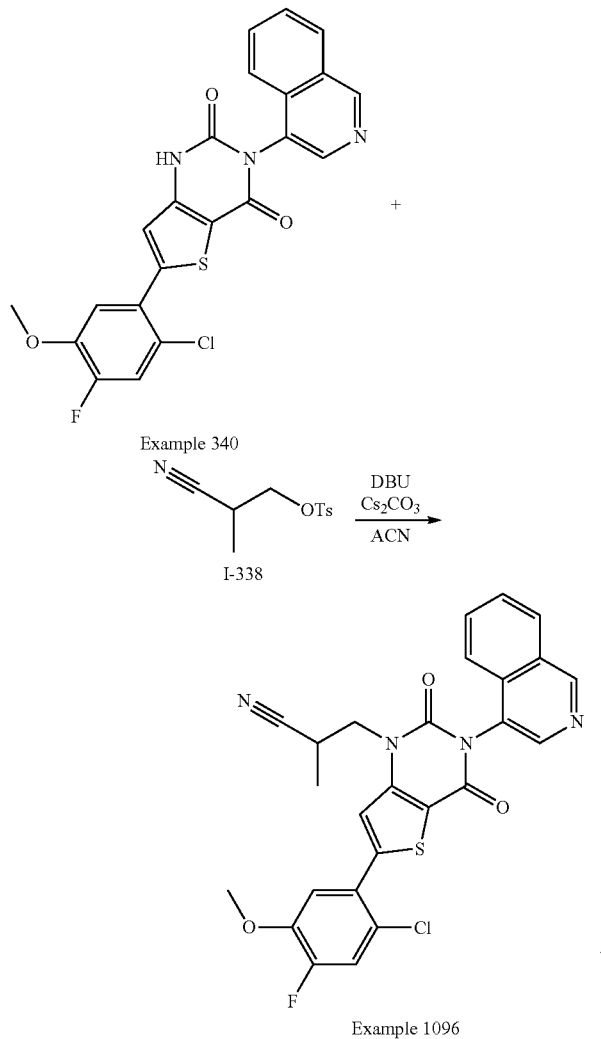

Example 1096

3-(6-(2-chloro-4-fluoro-5-methoxyphenyl)-3-(isoquinolin-4-yl)-2,4-dioxo-3,4-dihydrothieno[3,2-d]pyrimidin-1 (2H)-yl)-2-methylpropanenitrile (Example 1096). To 6-(2-chloro-4-fluoro-5-methoxy-phenyl)-3-(4-isoquinolyl)-1H-thieno[3,2-d]pyrimidine-2,4 dione (Example 340) (80 mg, 0.16 mmol) in a 10 mL vial was added acetonitrile (0.5 mL) and DBU (50 mg, 0.32 mmol). To this mixture was added Cs$_2$CO$_3$ (159 mg, 0.49 mmol), followed by 2-cyanopropyl 4-methylbenzenesulfonate (I-338) (97.6 mg, 0.4 mmol), and the mixture was stirred at 80° C. overnight. To this mixture was subsequently added acetonitrile (0.5 mL) and 2-cyanopropyl 4-methylbenzenesulfonate (195 mg, 0.81 mmol), and mixture was stirred at 90° C. for 2 days. The reaction was cooled to rt, and to the reaction mixture was added DMF (2 mL), MeOH (1 mL), water (0.2 mL), and TFA (0.1 mL) and the mixture was filtered through an acrodisc. This solution purified directly by RP-HPLC (0.1% TFA-ACN in 0.1% TFA-Water, Column: Gemini 10 μM, NX-C18 110 Angstrom, 250×30 mm) to give the product.

$^1$H NMR (400 MHz, DMSO-d$_6$) δ 9.46 (s, 1H), 8.58 (d, J=25.8 Hz, 1H), 8.30 (dd, J=6.4, 3.0 Hz, 1H), 8.00 (d, J=3.3 Hz, 1H), 7.94-7.77 (m, 3H), 7.75 (d, J=11.1 Hz, 1H), 7.52 (d, J=8.6 Hz, 1H), 4.52-4.47 (m, 1H), 4.33-4.20 (m, 2H), 3.97 (s, 3H), 1.39-1.36 (dd, J=7.1, 3.4 Hz, 3H).
ES/MS: 521.2 (M$^+$).

Procedure 163: Example 1097 and Example 1098

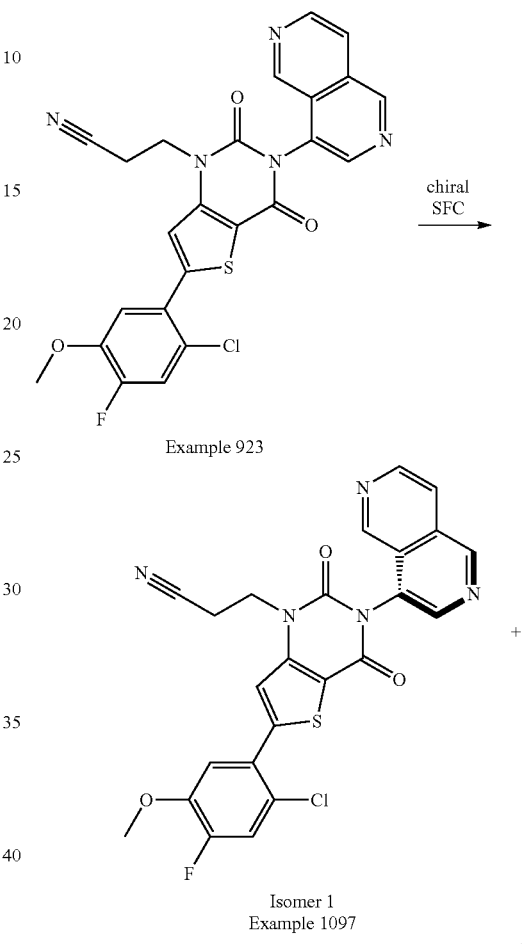

3-[6-(2-chloro-4-fluoro-5-methoxy-phenyl)-3-(2,6-naphthyridin-4-yl)-2,4-dioxo-thieno[3,2-d]pyrimidin-1-yl]propanenitrile (Example 1097 and Example 1098): 3-[6-(2-chloro-4-fluoro-5-methoxy-phenyl)-3-(2,6-naphthyridin-4-yl)-2,4-dioxo-thieno[3,2-d]pyrimidin-1-yl]propanenitrile (Example 923) as a mixture of 2 enantiomers was separated by chiral SFC (IB 5 um-4.6×$^{100}$ mm column with 35% MeOH cosolvent) to give two enantiomers, which were assigned as Isomer 1 and Isomer 2. The stereochemistry was assigned by analogy to Example 438, with Example 1098 being the more active isomer.

Isomer 1:

3-[6-(2-chloro-4-fluoro-5-methoxy-phenyl)-3-(2,6-naphthyridin-4-yl)-2,4-dioxo-thieno[3,2-d]pyrimidin-1-yl]propanenitrile (Example 1097)

ES/MS: 507.7 (M$^+$).

$^1$H NMR (400 MHz, DMSO-d$_6$) δ 9.60 (s, 1H), 9.50 (s, 1H), 8.83 (d, J=5.7 Hz, 1H), 8.77 (s, 1H), 8.19 (dd, J=5.7, 1.1 Hz, 1H), 7.98 (s, 1H), 7.74 (d, J=11.0 Hz, 1H), 7.53 (d, J=8.9 Hz, 1H), 4.45 (hept, J=7.0, 6.5 Hz, 2H), 3.97 (s, 3H), 3.03 (t, J=6.6 Hz, 2H).

Isomer 2:

3-[6-(2-chloro-4-fluoro-5-methoxy-phenyl)-3-(2,6-naphthyridin-4-yl)-2,4-dioxo-thieno[3,2-d]pyrimidin-1-yl]propanenitrile (Example 1098)

ES/MS: 507.7 (M$^+$).

$^1$H NMR (400 MHz, DMSO-d$_6$) δ 9.55 (d, J=38.9 Hz, 2H), 8.90-8.69 (m, 2H), 8.19 (d, J=5.8 Hz, 1H), 7.99 (s, 1H), 7.81-7.67 (m, 1H), 7.54 (d, J=8.9 Hz, 1H), 4.45 (dq, J=13.7, 6.5 Hz, 2H), 3.98 (s, 3H), 3.04 (t, J=6.5 Hz, 2H).

Procedure 164: Example 1099

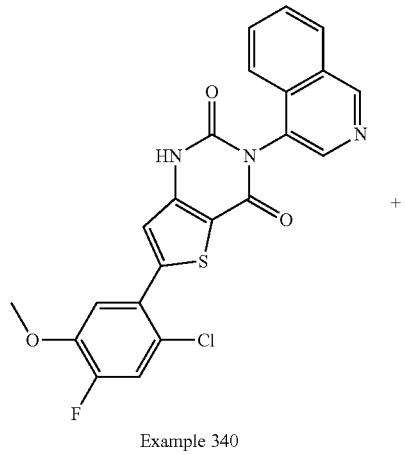

Example 340

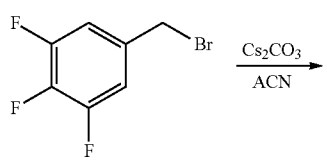

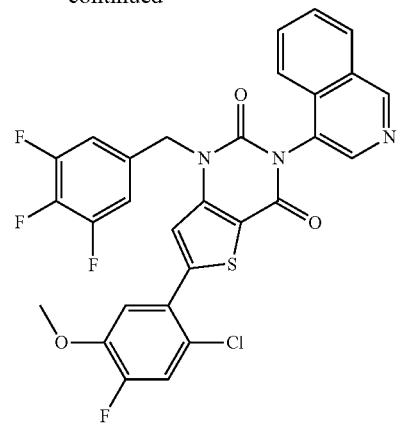

Example 1099

6-(2-chloro-4-fluoro-5-methoxy-phenyl)-3-(4-isoquinolyl)-1-[(3,4,5-trifluorophenyl)methyl]thieno[3,2-d]pyrimidine-2,4-dione (Example 1099): To a stirring mixture of 6-(2-chloro-4-fluoro-5-methoxy-phenyl)-3-(4-isoquinolyl)-1H-thieno[3,2-d]pyrimidine-2,4-dione (Example 340) (300 mg, 0.46 mmol, 1.0 equiv.) in acetonitrile (6 mL), was added Cs$_2$CO$_3$ (302 mg, 0.92 mmol) followed by 5-(bromomethyl)-1,2,3-trifluoro-benzene (0.24 mL, 1.85 mmol). The reaction mixture was stirred overnight at 40° C., after which the mixture was filtered through an acrodisc, and concentrated under reduced pressure. The crude residue was purified by flash column chromatography (eluent: Hexanes/Ethyl Acetate) to give desired product.

ES/MS: 597.6 (M$^+$).

1H NMR (400 MHz, DMSO-d$_6$) δ 9.45 (d, J=0.9 Hz, 1H), 8.66 (s, 1H), 8.28 (dd, J=7.5, 1.5 Hz, 1H), 8.03-7.96 (m, 1H), 7.86-7.65 (m, 4H), 7.51 (dd, J=8.9, 6.7 Hz, 2H), 7.43 (d, J=8.8 Hz, 1H), 5.41 (d, J=16.5 Hz, 1H), 5.29 (d, J=16.6 Hz, 1H), 3.95 (s, 3H).

Procedure 165: Example 1100

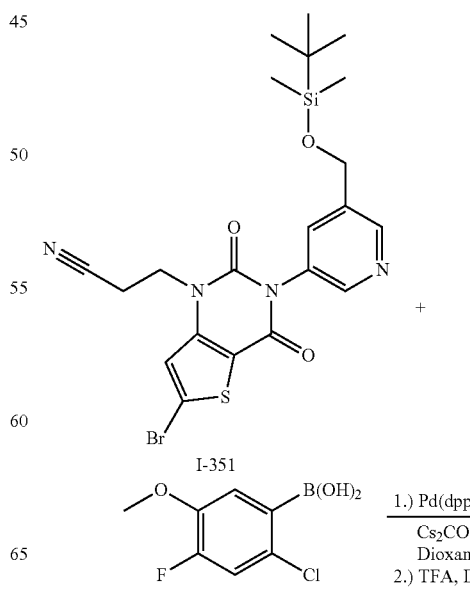

-continued

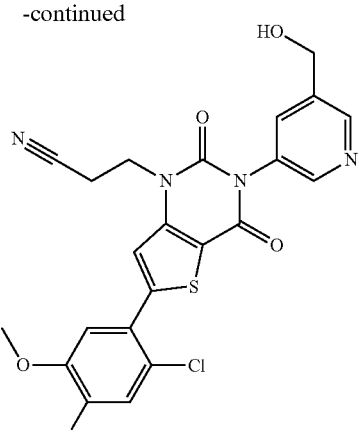

Example 1100

3-(6-(2-chloro-4-fluoro-5-methoxyphenyl)-3-(5-(hydroxymethyl)pyridin-3-yl)-2,4-dioxo-3,4-dihydrothieno[3,2-d]pyrimidin-1(2H)-yl)propanenitrile (Example 1100): To a microwave vial containing a stir bar was added 3-(6-bromo-3-(5-((((tert-butyldimethylsilyl)oxy)methyl)pyridin-3-yl)-2,4-dioxo-3,4-dihydrothieno[3,2-d]pyrimidin-1(2H)-yl)propanenitrile (I-351) (40 mg, 0.07 mmol), (2-chloro-4-fluoro-5-methoxyphenyl)boronic acid (16 mg, 0.08 mmol), Pd(dppf)Cl$_2$ (5.1 mg, 0.007 mmol), and Cs$_2$CO$_3$ (68 mg, 0.21 mmol), followed by 1,4-Dioxane (1 ml). The vial was degassed under argon (30 seconds), sealed with Teflon, and heated at 95° C. for 10 minutes under microwave conditions. The crude mixture was concentrated under reduced pressure. The crude residue was purified by silica column chromatography (eluent EtOAc/hexanes). The isolated material was dissolved in DCM (0.5 mL) and TFA (0.5 mL). The mixture was heated at 40° C. for 60 minutes. The mixture was concentrated under reduced pressure, and then dissolved in ACN (1.5 mL), water (0.5 mL) and TFA (0.2 mL), and purified directly by RP-HPLC (0.1% TFA-ACN in 0.1% TFA Water, Column: Gemini 5 µM, NX-C18 110 Angstrom, 250×21.2 mm) to give the product.

ES/MS: 486.8 (M$^+$).

1H NMR (400 MHz, DMSO-d$_6$) δ 8.59 (d, J=1.9 Hz, 1H), 8.46 (d, J=2.3 Hz, 1H), 7.93 (s, 1H), 7.80 (t, J=2.2 Hz, 1H), 7.73 (d, J=11.0 Hz, 1H), 7.52 (d, J=8.9 Hz, 1H), 4.63 (s, 2H), 4.42 (t, J=6.6 Hz, 2H), 3.97 (s, 3H), 3.00 (t, J=6.6 Hz, 2H).

Examples 1101-1102

The following Examples were made in an analogous fashion according to Procedure 165 and are shown below in Table 61. To prepare the below Examples, different reagents/starting materials were used than some of those described in Procedure 165 and are noted in the last column of Table 61—"Changes to Procedure 165: Different Reagents/Starting Materials".

TABLE 61

Examples 1101-1102

| Example | Structure | ES/MS m/z | 1H-NMR | Changes to Procedure 165: Different Reagents/ Starting Materials |
|---|---|---|---|---|
| 1101 | ![structure] | 429.8 | 1H NMR (400 MHz, DMSO-d6) δ 8.58 (d, J = 1.9 Hz, 1H), 8.45 (d, J = 2.3 Hz, 1H), 8.13-8.02 (m, 2H), 8.01-7.88 (m, 2H), 7.79 (t, J = 2.2 Hz, 1H), 7.74 (td, J = 7.4, 1.8 Hz, 1H), 4.63 (s, 2H), 4.41 (t, J = 6.9 Hz, 2H), 2.99 (t, J = 6.8 Hz, 2H). | 2-cyanophenyl-boronic acid |

TABLE 61-continued

Examples 1101-1102

| Example | Structure | ES/MS m/z | 1H-NMR | Changes to Procedure 165: Different Reagents/ Starting Materials |
|---|---|---|---|---|
| 1102 | 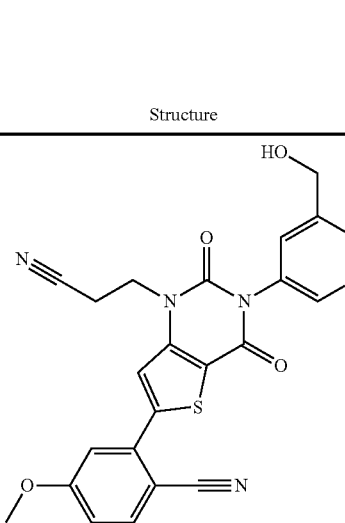 | 477.8 | 1H NMR (400 MHz, DMSO-d6) δ 8.58 (d, J = 1.9 Hz, 1H), 8.45 (d, J = 2.3 Hz, 1H), 8.13 (d. J = 11.1 Hz, 1H), 8.04 (s, 1H), 7.79 (t. J = 2.2 Hz, 1H), 7.58 (d, J = 8.1 Hz, 1H), 4.63 (s, 2H), 4.41 (t, J = 6.8 Hz, 2H). 4.06 (s, 3H), 3.00 (t, J = 6.8 Hz, 2H). | I-104 |

III. Biological Examples

Example A. Cov Mpro Biochemical IC50 Assay Description

This biochemical assay measured small molecule inhibitor $IC_{50}$ values against recombinant SARS-CoV-2 Main protease (Mpro). Compounds from 100 μM to 5 nM in 3 fold dilutions were prepared and pre-incubated for 20 minutes while mixing at room temperature with 2× Mpro. The final Mpro concentration was 7.5 nM with the fluorogenic peptide substrate (DABCYL-KTSAVLQ/SGFRKME-EDANS) at its Km value of 40 μM in a reaction volume of 40 μM. Product formation was quantitated in kinetic mode every 2.5 minutes for 8 cycles by monitoring fluorescence at EX/EM wavelength of 340/460. Rates of reaction (slope with background subtracted) from inhibitor wells were normalized to DMSO wells and then curve fitted for $IC_{50}$ using the PRISM algorithm: log(inhibitor) vs. normalized response—Variable slope The IC50 value for each compound was defined as the concentration reducing enzyme activity by 50%.

Example B. A549-hACE2 SARS-CoV2-NLuc 384-Well Assay

A549-hACE2 cell line was maintained in Dulbecco's Minimum Essential Medium (DMEM) (Corning, New York, NY, Cat #15-018CM) supplemented with 10% fetal bovine serum (FBS) (Hyclone, Logan, UT, Cat #SH30071-03), 1× Penicillin-Streptomycin-L-Glutamine (Corning, New York, NY, Cat #30-009-CI) and 10 μg/mL blasticidin (Life Technologies Corporation, Carlsbad, CA, Cat #A11139-03). Cells were passaged 2 times per week to maintain subconfluent densities and were used for experiments at passage 5-20. SARS Coronavirus 2 recombinant with NanoLuc (SARS-CoV-2-NLuc) was obtained from University of Texas Medical Branch (Galveston, TX). Viral replication was determined in A549-hACE2 cells in the following manner.

Compounds were prepared in 100% DMSO in 384-well polypropylene plates (Greiner, Monroe, NC, Cat #784201) with 8 compounds per plate in grouped replicates of 4 at 10 serially diluted concentrations (1:3). The serially diluted compounds were transferred to low dead volume Echo plates (Labcyte, Sunnyvale, CA, Cat #LP-0200).

The test compounds were spotted to 384-well assay plates (Greiner, Monroe, NC, Cat #781091) at 200 nL per well using an Echo acoustic dispenser (Labcyte, Sunnyvale, CA). A549-hACE2 cells were harvested and suspended in DMEM (supplemented with 2% FBS and 1× Penicillin-Streptomycin-L-Glutamine) and seeded to the pre-spotted assay plates at 10,000 cells per well in 30 μL. SARS-CoV2-NLuc virus was diluted in DMEM (supplemented with 2% FBS and 1× Penicillin-Streptomycin-L-Glutamine) at 350,000 Infectious Units (U) per mL and 10 μL per well was added to the assay plates containing cells and compounds, for MOI 0.35. The assay plates were incubated for 2 days at 37° C. and 5% $CO_2$. At the end of incubation, Nano-Glo reagent (Promega. Madison, WI. Cat #N1150) was prepared. The assay plates and Nano-Glo reagent were equilibrated to room temperature for at least 30 minutes, 40 μL per well of Nano-Glo reagent was added and the plates were incubated at room temperature for 30 minutes before reading the luminescence signal on an EnVision multimode plate reader (Perkin Elmer, Waltham, MA). Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was defined as the concentration reducing viral replication by 50%.

Biological Data

Provided below in Table 18 is data related to compounds disclosed herein.

TABLE 62

Biological Data for Compounds Disclosed Herein

| Example No. | MPro IC50 (nM) | MPro EC50 (nM) |
|---|---|---|
| 1 | 10.82 | 28.92 |
| 2 | 266.66 | 2485.54 |
| 3 | 312.34 | >50000 |
| 4 | 792.24 | 891.84 |
| 5 | 342.38 | 1793.01 |
| 6 | 28.37 | 1177.03 |
| 7 | 24.70 | 109.20 |
| 8 | 31.31 | 107.79 |
| 9 | 158.75 | 295.29 |
| 10 | 13686.50 | 19997.10 |
| 11 | 4815.07 | 637.91 |
| 12 | 7453.84 | 943.43 |
| 13 | 17.09 | 42.4009 |
| 14 | 132.37 | 79.87 |
| 15 | 3974.68 | 25070.60 |
| 16 | 164.14 | 182.05 |
| 17 | 35.08 | 159.79 |
| 18 | 2930.10 | 207.89 |
| 19 | 29.49 | 59.64 |
| 20 | 8624.69 | >50000 |
| 21 | 32.52 | 204.36 |
| 22 | 37.09 | 119.53 |
| 23 | 257.93 | 799.74 |
| 24 | 2725.09 | 2497.92 |
| 25 | 1414.86 | 5042.33 |
| 26 | 40084.50 | 47897.60 |
| 27 | 769.81 | 750.80 |
| 28 | 340.09 | 535.94 |
| 29 | 475.84 | 4511.05 |
| 30 | 17.60 | 380.20 |
| 31 | 14764.80 | >50000 |
| 32 | 2284.94 | 7064.60 |
| 33 | 56.80 | 1874.45 |
| 34 | 1519.83 | 6532.12 |
| 35 | >100000 | >50000 |
| 36 | 387.81 | 618.83 |
| 37 | 248.23 | 170.17 |
| 38 | >100000 | 4911.56 |
| 39 | 7748.29 | 23435.50 |
| 40 | 1311.14 | 4911.19 |
| 41 | 1480.63 | 3837.49 |
| 42 | 3215.43 | 4954.56 |
| 43 | 3115.74 | >50000 |
| 44 | 1374.31 | 2996.63 |
| 45 | 1709.02 | 1215.45 |
| 46 | 216.30 | 989.26 |
| 47 | 1132.30 | 6068.83 |
| 48 | 95.68 | 276.76 |
| 49 | >100000 | 12829.60 |
| 50 | 7915.31 | 9060.45 |
| 51 | >100000 | 6798.92 |
| 52 | 12810.60 | 3724.89 |
| 53 | 33210.20 | 4325.96 |
| 54 | 741.06 | 1633.61 |
| 55 | 12823.90 | 1825.69 |
| 56 | 2749.12 | 3939.01 |
| 57 | 5452.13 | 1523.46 |
| 58 | 158.07 | 163.86 |
| 59 | >100000 | 6014.16 |
| 60 | 191.88 | 226.61 |
| 61 | 913.55 | 648.19 |
| 62 | 904.46 | 3150.67 |
| 63 | 5853.78 | 8441.73 |
| 64 | 28374.90 | 3139.51 |
| 65 | 108.45 | 286.09 |
| 66 | 2013.70 | >50000 |
| 67 | 88.77 | 213.28 |
| 68 | 1009.19 | 43812.00 |
| 69 | 53.10 | 4206.23 |
| 70 | 2684.74 | >50000 |
| 71 | 76.43 | 140.51 |
| 72 | 8200.72 | >50000 |
| 73 | 158.63 | 261.50 |
| 74 | 470.20 | 711.33 |
| 75 | 854.02 | 9391.13 |
| 76 | 2777.78 | 7396.93 |
| 77 | 130.66 | 115.274 |
| 78 | 404.21 | 9529.25 |
| 79 | 14022.80 | 12095.20 |
| 80 | 768.23 | 231.52 |
| 81 | 230.95 | 184.47 |
| 82 | 1367.70 | 2864.35 |
| 83 | 109.28 | 121.80 |
| 84 | 603.90 | 1027.49 |
| 85 | 1493.67 | 751.04 |
| 86 | 112.04 | 143.56 |
| 87 | 171.50 | 202.98 |
| 88 | 232.55 | 629.54 |
| 89 | 860.02 | 881.30 |
| 90 | 487.42 | 886.09 |
| 91 | 216.17 | 1144.75 |
| 92 | 33.88 | 37.51 |
| 93 | 11.39 | 94.95 |
| 94 | 210.43 | 269.39 |
| 95 | 1590.58 | 680.06 |
| 96 | 150.63 | 295.94 |
| 97 | 396.63 | 266.05 |
| 98 | 212.86 | 197.75 |
| 99 | 216.24 | 491.87 |
| 100 | 325.52 | 447.84 |
| 101 | 13.75 | 73.78 |
| 102 | 15.74 | 16.14 |
| 103 | 387.71 | 83.44 |
| 104 | 6788.44 | 3915.77 |
| 105 | 70.92 | 74.35 |
| 106 | 23.66 | 72.98 |
| 107 | 31.75 | 71.68 |
| 108 | 9.23 | 71.39 |
| 109 | 264.95 | 422.54 |
| 110 | 371.76 | 275.10 |
| 111 | 6.88 | 78.89 |
| 112 | 5.19 | 39.1622 |
| 113 | 7.31 | <7.31 |
| 114 | 10.89 | 44.44 |
| 115 | 521.92 | 1529.61 |
| 116 | 796.90 | 3198.31 |
| 117 | 155.59 | 626.65 |
| 118 | 290.29 | 11737.60 |
| 119 | 386.46 | 2758.49 |
| 120 | 96.82 | 275.08 |
| 121 | 707.98 | 1148.03 |
| 122 | 1009.30 | 3914.17 |
| 123 | >100000 | 46980.30 |
| 124 | 948.47 | 2219.26 |
| 125 | 22478.50 | 17539.60 |
| 126 | >50000 | >50000 |
| 127 | 775.89 | 652.38 |
| 128 | 509.59 | 1319.34 |
| 129 | 1034.82 | 1232.53 |
| 130 | 73.10 | 146.71 |
| 131 | 97.01 | 632.69 |
| 132 | 9.12 | 27.45 |
| 133 | 12.83 | 27.73 |
| 134 | 63.33 | 150.46 |
| 135 | 51.47 | 288.12 |
| 136 | >50000 | 11105.90 |
| 137 | 14.98 | 40.15 |
| 138 | 16.18 | 143.81 |
| 139 | 108.45 | 594.64 |
| 140 | >100000 | 429.25 |
| 141 | 6654.49 | 32183.90 |
| 142 | 8.62 | 31.50 |
| 143 | 10.81 | 79.20 |
| 144 | 95.40 | 68.18 |
| 145 | 23.89 | 42.95 |
| 146 | 99.69 | 60.63 |
| 147 | 11.00 | 17.14 |
| 148 | 10.42 | 14.12 |
| 149 | 19.16 | 40.25 |
| 150 | 73.04 | 124.01 |
| 151 | <2.54 | 1.73 |
| 152 | 85.81 | 148.56 |

TABLE 62-continued

Biological Data for Compounds Disclosed Herein

| Example No. | MPro IC50 (nM) | MPro EC50 (nM) |
|---|---|---|
| 153 | 18.52 | 66.10 |
| 154 | 123.81 | 193.45 |
| 155 | 9.13 | 124.78 |
| 156 | 166.86 | 170.87 |
| 157 | 164.46 | 204.12 |
| 158 | 132.99 | 19108.70 |
| 159 | 987.82 | 334.77 |
| 160 | 17.21 | 56.76 |
| 161 | 27.08 | 128.99 |
| 162 | 344.19 | 392.50 |
| 163 | 489.07 | 932.11 |
| 164 | 7875.27 | 12461.40 |
| 165 | 1473.20 | 2469.78 |
| 166 | 941.86 | 4419.16 |
| 167 | 49673.00 | 4513.39 |
| 168 | 615.13 | 809.78 |
| 169 | 5545.57 | 743.93 |
| 170 | 191.61 | 421.03 |
| 171 | 3787.20 | 4195.84 |
| 172 | 158.75 | 75.80 |
| 173 | 379.94 | 649.94 |
| 174 | 6.99 | 30.71 |
| 175 | 4.68 | 26.58 |
| 176 | 330.27 | 292.18 |
| 177 | 89.72 | 136.97 |
| 178 | 220.62 | 195.71 |
| 179 | 194.53 | 84.81 |
| 180 | 3743.93 | 1959.33 |
| 181 | 1220.60 | 438.05 |
| 182 | 45.15 | 90.03 |
| 183 | 585.32 | 353.54 |
| 184 | 92.48 | 40.03 |
| 185 | <3.01 | 488.78 |
| 186 | 112.28 | 50.72 |
| 187 | 29.43 | 17.60 |
| 188 | 121.40 | 59.43 |
| 189 | 8.58 | 18.16 |
| 190 | 19.65 | 16.43 |
| 191 | 73.85 | 90.96 |
| 192 | >50000 | 3893.22 |
| 193 | 7.69 | 65.56 |
| 194 | <2.54 | 20.56 |
| 195 | 8.82 | 9.06 |
| 196 | 17.38 | 15.64 |
| 197 | 13.94 | 8.58 |
| 198 | 8.77 | 8.47 |
| 199 | 19.28 | 25.39 |
| 200 | 111.74 | 35.97 |
| 201 | 109.84 | 58.95 |
| 202 | 13.65 | 18.37 |
| 203 | 11.12 | 26.88 |
| 204 | 11.71 | 49.02 |
| 205 | 44.01 | 41.22 |
| 206 | 42.42 | 20.63 |
| 207 | 17.65 | 13.62 |
| 208 | 7.56 | 4.21 |
| 209 | 10.37 | 23.60 |
| 210 | 2825.35 | 2976.94 |
| 211 | 55.47 | 70.36 |
| 212 | 830.63 | 752.42 |
| 213 | 16.43 | 31.09 |
| 214 | 11.15 | 20.05 |
| 215 | 10.65 | 94.09 |
| 216 | 62.30 | 111.60 |
| 217 | 66.62 | 96.21 |
| 218 | 20.91 | 82.78 |
| 219 | 5.06 | 181.25 |
| 220 | 29.06 | 86.62 |
| 221 | 65.77 | 50.62 |
| 222 | 153.36 | 150.68 |
| 223 | 101.30 | 413.70 |
| 224 | 10.20 | 124.12 |
| 225 | 12.08 | 87.72 |
| 226 | 3.74 | 23.67 |
| 227 | 11.33 | 25.04 |
| 228 | 294.48 | 73.07 |
| 229 | 22.48 | 28.89 |
| 230 | 23.76 | 127.70 |
| 231 | 22.13 | 37.43 |
| 232 | 17.59 | 34.87 |
| 233 | 12.26 | 26.78 |
| 234 | <5.67 | 21.22 |
| 235 | 53.54 | 288.64 |
| 236 | 86.82 | 228.35 |
| 237 | 87.03 | 142.78 |
| 238 | 47.96 | 54.51 |
| 239 | 4838.89 | 1823.05 |
| 240 | 1663.60 | 519.69 |
| 241 | 34.96 | 53.95 |
| 242 | 10.43 | 40.11 |
| 243 | 11.05 | 12.20 |
| 244 | 18.15 | 40.99 |
| 245 | 13.19 | 20.43 |
| 246 | 21.00 | 18.44 |
| 247 | 62.96 | 30.39 |
| 248 | 87.16 | 40.15 |
| 249 | 268.79 | 110.05 |
| 250 | 1207.02 | 459.88 |
| 251 | 68.21 | 149.84 |
| 252 | 151.17 | 321.33 |
| 253 | 458.95 | 1211.23 |
| 254 | 107.42 | 277.30 |
| 255 | 307.37 | 331.71 |
| 256 | 3991.80 | 699.38 |
| 257 | 500.48 | 1148.19 |
| 258 | 61.30 | 75.87 |
| 259 | 188.54 | 112.61 |
| 260 | 15.29 | 10.29 |
| 261 | 78.97 | 98.62 |
| 262 | 6.12 | <4.41 |
| 263 | 88.48 | 38.12 |
| 264 | 11.11 | 30.20 |
| 265 | 25.89 | 17.38 |
| 266 | 36.43 | 95.14 |
| 267 | 24.05 | 35.49 |
| 268 | 130.89 | 43.15 |
| 269 | 10.66 | <5.29 |
| 270 | 13.85 | 85.30 |
| 271 | 154.84 | 208.06 |
| 272 | 211.95 | 39.64 |
| 273 | 14.94 | 6.41 |
| 274 | 83.51 | 95.70 |
| 275 | 23.31 | 17.90 |
| 276 | 229.61 | 218.79 |
| 277 | 123.56 | 56.98 |
| 278 | 29.12 | 51.66 |
| 279 | 5.27 | 7.65 |
| 280 | 5.97 | 15.93 |
| 281 | 71.80 | 39.47 |
| 282 | 148.17 | 72.41 |
| 283 | 240.31 | 94.41 |
| 284 | 25.81 | 35.64 |
| 285 | 19.23 | 25.52 |
| 286 | 34.76 | 60.26 |
| 287 | 226.43 | >921.99 |
| 288 | 227.13 | 1053.91 |
| 289 | 41.71 | 119.00 |
| 290 | 159.46 | 484.38 |
| 291 | 62.26 | 807.76 |
| 292 | 119.67 | 169.06 |
| 293 | 67.85 | 748.29 |
| 294 | 24.93 | 22.39 |
| 295 | 7428.76 | 13487.70 |
| 296 | 383.58 | 1434.63 |
| 297 | 679.67 | 222.54 |
| 298 | 6.29 | 10.78 |
| 299 | 72.42 | 36.11 |
| 300 | 147.70 | 60.52 |
| 301 | 259.25 | 173.42 |
| 302 | 30.33 | 107.53 |
| 303 | 270.03 | 364.65 |
| 304 | 11.54 | 20.52 |

TABLE 62-continued

Biological Data for Compounds Disclosed Herein

| Example No. | MPro IC50 (nM) | MPro EC50 (nM) |
| --- | --- | --- |
| 305 | 8.80 | 12.75 |
| 306 | 8.21 | 5.19 |
| 307 | 16.88 | 10.45 |
| 308 | 16.23 | 31.16 |
| 309 | 56.90 | 26.73 |
| 310 | 55.37 | 140.07 |
| 311 | 45.27 | 25.01 |
| 312 | 14.28 | 20.38 |
| 313 | 40.78 | 145.39 |
| 314 | 456.10 | 72.90 |
| 315 | 42.00 | 40.24 |
| 316 | 1066.53 | 322.02 |
| 317 | 11.00 | 4.97 |
| 318 | 8.65 | <3.42 |
| 319 | 10.73 | 27.90 |
| 320 | 15.98 | 14.06 |
| 321 | 8.28 | 25.05 |
| 322 | 3532.76 | 1304.42 |
| 323 | 111.98 | 556.59 |
| 324 | 7.02 | 18.11 |
| 325 | 15.76 | 27.86 |
| 326 | 42.45 | 106.36 |
| 327 | 13.28 | 96.33 |
| 328 | 15.42 | 45.86 |
| 329 | 9.77 | 22.34 |
| 330 | 326.49 | 211.54 |
| 331 | 10.39 | 17.02 |
| 332 | 15.29 | 38.99 |
| 333 | 149.35 | 765.17 |
| 334 | 78.60 | 81.94 |
| 335 | 289.53 | 991.20 |
| 336 | 4.68 | 7.02 |
| 337 | <2.68 | 170.33 |
| 338 | 13.77 | 37.55 |
| 339 | 14.82 | 48.17 |
| 340 | 5.23 | 5.39 |
| 341 | 5.44 | 4.62 |
| 342 | 4.49 | 6.76 |
| 343 | 4.02 | 7.79 |
| 344 | 109.62 | 373.88 |
| 345 | 14.68 | 61.80 |
| 346 | 73.49 | 239.16 |
| 347 | 441.34 | 642.23 |
| 348 | 4759.77 | 8928.92 |
| 349 | 7.23 | 29.98 |
| 350 | 17.23 | 49.24 |
| 351 | 19.56 | 69.17 |
| 352 | 41.82 | 119.57 |
| 353 | 143.11 | 31.49 |
| 354 | 45.58 | 12.77 |
| 355 | 9.64 | 22.86 |
| 356 | 129.61 | 52.17 |
| 357 | 373.35 | 68.12 |
| 358 | 177.29 | 112.59 |
| 359 | 107.23 | 91.38 |
| 360 | 19.37 | 42.11 |
| 361 | 38.88 | 178.42 |
| 362 | 35.60 | 200.78 |
| 363 | 128.62 | 785.40 |
| 364 | 5.31 | 18.17 |
| 365 | 100.42 | 342.93 |
| 366 | 36799.40 | 32212.70 |
| 367 | 8.90 | 21.14 |
| 368 | 410.83 | 1915.96 |
| 369 | 9.23 | 110.50 |
| 370 | 273.43 | 388.32 |
| 371 | 55.88 | 108.04 |
| 372 | 77.81 | 175.63 |
| 373 | 14.64 | 46.85 |
| 374 | 1134.98 | 1238.92 |
| 375 | 345.07 | 631.97 |
| 376 | 43260.20 | 47268.70 |
| 377 | >50000 | 6234.49 |
| 378 | 303.76 | 359.43 |
| 379 | 435.98 | 186.28 |
| 380 | 5950.78 | 769.97 |
| 381 | 5067.63 | 144.63 |
| 382 | 4595.72 | 208.40 |
| 383 | 5.23 | 285.74 |
| 384 | 3512.73 | >50000 |
| 385 | 5.51 | 14.03 |
| 386 | 3.96 | 56.17 |
| 387 | <2.54 | 30.28 |
| 388 | 18.72 | 212.26 |
| 389 | 26.72 | 131.25 |
| 390 | 11.55 | 19.05 |
| 391 | 6.25 | 10.25 |
| 392 | <2.54 | 6.75 |
| 393 | 9.00 | 12.15 |
| 394 | 5.10 | 5.75 |
| 395 | 7.25 | 80.72 |
| 396 | 14.89 | 3011.31 |
| 397 | 3.51 | 15.24 |
| 398 | 3.38 | 18.67 |
| 399 | 3.74 | 8.43 |
| 400 | 6.04 | 6.07 |
| 401 | 3.84 | 10.59 |
| 402 | 6.05 | 12.07 |
| 403 | 6.90 | 11.05 |
| 404 | 6.49 | 37.39 |
| 405 | 12.03 | 2930.17 |
| 406 | 12.63 | 470.94 |
| 407 | 79.70 | 184.36 |
| 408 | 42.70 | 107.98 |
| 409 | 15.68 | 77.44 |
| 410 | 12.76 | 58.65 |
| 411 | 8.93 | 220.62 |
| 412 | 10.77 | 38.32 |
| 413 | 5.46 | 66.76 |
| 414 | 7.63 | 20.12 |
| 415 | 11.67 | 26.59 |
| 416 | 4.63 | 186.56 |
| 417 | 17.80 | 159.58 |
| 418 | 21.45 | 126.48 |
| 419 | 21.15 | 74.94 |
| 420 | 10.80 | 50.87 |
| 421 | 4.42 | 38.82 |
| 422 | 7.75 | 134.24 |
| 423 | 6.50 | 53.68 |
| 424 | 11.32 | 55.80 |
| 425 | 7.69 | 30.03 |
| 426 | 21.34 | 40.89 |
| 427 | 15.57 | 24.00 |
| 428 | 10.22 | 17.88 |
| 429 | 2.83 | 11.22 |
| 430 | 11.84 | 18.49 |
| 431 | 10.53 | 71.33 |
| 432 | 6.99 | 6.37 |
| 433 | 7.80 | 69.47 |
| 434 | 15.95 | 33.28 |
| 435 | 6.97 | 37.37 |
| 436 | 163.61 | 489.07 |
| 437 | 535.40 | 10561.40 |
| 438 | <4.17 | <11.42 |
| 439 | 827.53 | 376.83 |
| 440 | <3.94 | 13.37 |
| 441 | 108.89 | 238.90 |
| 442 | <3.43 | 12.30 |
| 443 | 18.77 | 45.02 |
| 444 | 5.45 | 8.86 |
| 445 | 5.71 | 21.99 |
| 446 | 8.74 | 25.52 |
| 447 | 4.21 | 6.58 |
| 448 | 382.64 | 382.01 |
| 449 | 13.96 | 29.18 |
| 450 | 126.63 | 210.91 |
| 451 | 417.65 | 290.92 |
| 452 | 9.24 | 82.55 |
| 453 | 3.83 | 22.12 |
| 454 | 4.80 | 3.89 |
| 455 | 7.26 | 7.02 |
| 456 | 3.59 | 6.79 |

TABLE 62-continued

Biological Data for Compounds Disclosed Herein

| Example No. | MPro IC50 (nM) | MPro EC50 (nM) |
|---|---|---|
| 457 | <2.54 | <6.04 |
| 458 | 12.13 | 188.22 |
| 459 | 18.11 | 20.19 |
| 460 | 9.01 | 60.66 |
| 461 | 8.07 | 10.04 |
| 462 | 28.44 | 61.54 |
| 463 | 202.47 | 463.65 |
| 464 | 4.68 | 11.52 |
| 465 | <3.56 | 5.23 |
| 466 | 156.46 | 151.62 |
| 467 | 11.40 | 38.08 |
| 468 | <2.54 | <6.34 |
| 469 | 275.81 | 334.01 |
| 470 | 46.81 | 71.26 |
| 471 | 97.19 | 478.15 |
| 472 | 5.11 | 187.56 |
| 473 | 17.54 | 1808.54 |
| 474 | 13.97 | 123.91 |
| 475 | 17.11 | 28.51 |
| 476 | 258.03 | 258.90 |
| 477 | 58.04 | 165.33 |
| 478 | 4294.95 | 8284.60 |
| 479 | 16.74 | 20.91 |
| 480 | 4.97 | 10.23 |
| 481 | >50000 | 9122.76 |
| 482 | <2.54 | 4.44 |
| 483 | <2.54 | 18.06 |
| 484 | 38.92 | 481.62 |
| 485 | 9.60 | 62.62 |
| 486 | 5.90 | 29.42 |
| 487 | 907.57 | 742.19 |
| 488 | 1020.40 | 618.29 |
| 489 | 2.63 | 20.35 |
| 490 | 20.82 | 55.84 |
| 491 | 17.33 | 64.35 |
| 492 | >50000 | 4838.60 |
| 493 | 7.94 | 33.55 |
| 494 | 35.99 | 117.54 |
| 495 | 6.41 | 17.20 |
| 496 | 31.56 | 137.94 |
| 497 | 6.24 | 19.15 |
| 498 | <2.54 | <5.96 |
| 499 | 1918.86 | 6953.32 |
| 500 | 9.12 | 42.64 |
| 501 | 14.78 | 93.87 |
| 502 | <2.54 | 34.78 |
| 503 | 52.29 | 218.05 |
| 504 | 20.71 | 48.03 |
| 505 | 5.45 | 9.97 |
| 506 | 19.61 | 99.46 |
| 507 | 18.82 | 39.21 |
| 508 | 21.19 | 204.88 |
| 509 | 5.17 | 24.85 |
| 510 | 7.05 | 16.16 |
| 511 | 912.71 | 604.14 |
| 512 | 5.71 | 26.93 |
| 513 | 7.18 | 45.86 |
| 514 | 15.82 | 567.74 |
| 515 | 8.51 | 17.50 |
| 516 | 5.27 | 7.87 |
| 517 | 9.51 | 35.89 |
| 518 | 9.15 | 5.49 |
| 519 | 10.90 | 31.56 |
| 520 | <2.54 | 14.62 |
| 521 | 14.87 | 128.94 |
| 522 | 9.84 | 5.10 |
| 523 | 4.05 | 5.79 |
| 524 | 7.83 | 5.95 |
| 525 | 10.42 | 81.18 |
| 526 | 15.72 | 8.34 |
| 527 | 3.22 | 1.45 |
| 528 | 7.09 | 7.22 |
| 529 | 8.44 | 34.07 |
| 530 | 12.03 | 84.30 |
| 531 | 49.96 | 518.16 |
| 532 | <2.65 | 17.35 |
| 533 | 1257.51 | 876.61 |
| 534 | 30.60 | 80.50 |
| 535 | 39.63 | 432.21 |
| 536 | 21.18 | 46.42 |
| 537 | 6.15 | 19.18 |
| 538 | 59.84 | 825.84 |
| 539 | 141.03 | 675.34 |
| 540 | 910.64 | >50000 |
| 541 | 17.63 | 237.44 |
| 542 | 248.85 | 1197.45 |
| 543 | 9.91 | 240.33 |
| 544 | 16.83 | 201.55 |
| 545 | 29.41 | 112.42 |
| 546 | 15.36 | 163.99 |
| 547 | 170.31 | >1000 |
| 548 | 7.55 | 113.83 |
| 549 | 8.02 | 14.29 |
| 550 | 106.66 | 312.45 |
| 551 | 5.36 | 23.56 |
| 552 | 7.13 | 12.37 |
| 553 | 7.58 | 12.00 |
| 554 | 3.88 | 14.88 |
| 555 | 21.46 | 79.63 |
| 556 | 3.41 | 2.04 |
| 557 | 102.85 | 65.39 |
| 558 | 3.39 | 17.46 |
| 559 | 6.23 | 9.19 |
| 560 | <2.54 | 6.10 |
| 561 | 141.77 | 176.85 |
| 562 | <2.54 | 5.06 |
| 563 | 6.96 | 10.00 |
| 564 | 14.56 | 52.52 |
| 565 | 16.54 | 58.10 |
| 566 | 9.83 | 20.80 |
| 567 | 50.90 | 227.91 |
| 568 | 5670.75 | 2637.35 |
| 569 | 8.41 | 20.50 |
| 570 | 1306.94 | 700.49 |
| 571 | 77.11 | 170.51 |
| 572 | 2.90 | 10.55 |
| 573 | 3.26 | 20.10 |
| 574 | 6.37 | 18.48 |
| 575 | 6.66 | 234.87 |
| 576 | 174.40 | 153.13 |
| 577 | >50000 | 12087.50 |
| 578 | >50000 | 9869.22 |
| 579 | >50000 | 42584.60 |
| 580 | 7.53 | 70.87 |
| 581 | <2.54 | 150.89 |
| 582 | 8.83 | 31.71 |
| 583 | 20.86 | 226.60 |
| 584 | 12.93 | 31.87 |
| 585 | 10.13 | 29.27 |
| 586 | 26.20 | 54.29 |
| 587 | 27.90 | 116.98 |
| 588 | 14.76 | 47.42 |
| 589 | 5.01 | 23.70 |
| 590 | 194.25 | 298.98 |
| 591 | 12.21 | 142.42 |
| 592 | >50000 | 39494.00 |
| 593 | 38388.90 | 5790.29 |
| 594 | 883.45 | 929.04 |
| 595 | 475.84 | 1180.95 |
| 596 | 38.24 | 107.86 |
| 597 | 159.83 | 205.25 |
| 598 | 29.56 | 149.91 |
| 599 | 4.98 | 48.91 |
| 600 | 5.29 | 18.14 |
| 601 | <2.54 | 14.72 |
| 602 | 5.77 | 358.61 |
| 603 | 2.75 | 14.61 |
| 604 | 6.32 | 10.88 |
| 605 | 10.10 | 91.24 |
| 606 | <2.5403 | 28.05 |
| 607 | 4.52 | 4.34 |
| 608 | <2.54 | <4.97 |

TABLE 62-continued

Biological Data for Compounds Disclosed Herein

| Example No. | MPro IC50 (nM) | MPro EC50 (nM) |
| --- | --- | --- |
| 609 | <2.54 | <3.39 |
| 610 | <2.54 | 13.94 |
| 611 | <2.54 | 4.95 |
| 612 | 12.22 | >1000 |
| 613 | 68.56 | 91.87 |
| 614 | 34.98 | 63.97 |
| 615 | 9.85 | 139.77 |
| 616 | 6.92 | 319.93 |
| 617 | 7.26 | 19.49 |
| 618 | 6.56 | 15.96 |
| 619 | 245.35 | 450.54 |
| 620 | 281.27 | 759.09 |
| 621 | 494.60 | 709.71 |
| 622 | 15.39 | 39.30 |
| 623 | 11.54 | 30.03 |
| 624 | 88.68 | 385.79 |
| 625 | 6.91 | 18.10 |
| 626 | 7.68 | 32.20 |
| 627 | 1972.96 | 4771.32 |
| 628 | 3.26 | 15.90 |
| 629 | 42.40 | 289.92 |
| 630 | 6.31 | 9.35 |
| 631 | 12.61 | 4.96 |
| 632 | 6.13 | 3.11 |
| 633 | 3.22 | 3.29 |
| 634 | 28.98 | 31.19 |
| 635 | 3.26 | 1.78 |
| 636 | 11.63 | 5.54 |
| 637 | 3.48 | 1.85 |
| 638 | 191.90 | 60.58 |
| 639 | 114.18 | 172.87 |
| 640 | <4.26 | 3.48 |
| 641 | 2.20 | <4.42 |
| 642 | 8.54 | 4.59 |
| 643 | <4.05 | 1.14 |
| 644 | 3.10 | 1.55 |
| 645 | 43.46 | 36.04 |
| 646 | 1898.50 | 11849.80 |
| 647 | 10.87 | 25.86 |
| 648 | 99.54 | 187.54 |
| 649 | 7.91 | 194.66 |
| 650 | 31.73 | 33.86 |
| 651 | 336.02 | 135.36 |
| 652 | 22.50 | 48.06 |
| 653 | 2.58 | 4.45 |
| 654 | 3.87 | 2.42 |
| 655 | 3.40 | 3.31 |
| 656 | 11.99 | 23.89 |
| 657 | 14.40 | 27.39 |
| 658 | 14.40 | 22.81 |
| 659 | 40.92 | |
| 660 | 17.63 | 16.74 |
| 661 | 29.53 | 37.03 |
| 662 | 40.46 | 81.71 |
| 663 | 14.38 | 16.64 |
| 664 | 5.24 | 11.37 |
| 665 | 7.27 | 10.46 |
| 666 | 24.01 | 55.56 |
| 667 | 14.04 | 18.72 |
| 668 | 23.02 | 123.27 |
| 669 | 335.95 | >1000 |
| 670 | 145.70 | 584.90 |
| 671 | 5.85 | 7.44 |
| 672 | 37.82 | 23.82 |
| 673 | 4.08 | 3.71 |
| 674 | 3.85 | 2.82 |
| 675 | 15.10 | 20.02 |
| 676 | 31.58 | 25.29 |
| 677 | 7.27 | 45.02 |
| 679 | 25.39 | 80.06 |
| 680 | 21.74 | 20.78 |
| 681 | 4.49 | 11.13 |
| 682 | 20.23 | 33.04 |
| 683 | 8.88 | 43.68 |
| 684 | 13.49 | 119.24 |
| 685 | 12.02 | 69.16 |
| 686 | 15.70 | >1000 |
| 687 | 4.92 | 147.69 |
| 688 | 9.78 | 14.52 |
| 689 | 31.97 | 29.98 |
| 690 | 47.00 | 98.84 |
| 691 | 3.07 | 2.91 |
| 692 | 4.35 | 2.44 |
| 693 | 2.56 | 94.25 |
| 694 | 19.25 | 60.99 |
| 695 | 16.18 | 45.92 |
| 696 | 3.15 | 29.21 |
| 697 | 9.01 | 9.62 |
| 698 | 7.10 | 14.09 |
| 699 | 10.61 | 470.00 |
| 700 | 54.56 | 466.09 |
| 701 | <3.63 | 79.93 |
| 702 | <2.98 | 2.40 |
| 703 | 3.58 | 3.74 |
| 704 | 34.41 | 247.87 |
| 705 | 4.74 | 8.11 |
| 706 | 5.93 | 6.53 |
| 707 | 2.13 | 8.90 |
| 708 | 4.41 | 8.71 |
| 709 | 6.21 | 2.09 |
| 710 | <4.33 | 22.57 |
| 711 | 4.41 | 1.71 |
| 712 | 6.85 | 12.42 |
| 713 | 9.18 | 15.02 |
| 714 | >1000 | >1000 |
| 715 | 4.63 | 9.94 |
| 716 | 15.85 | 18.72 |
| 717 | 23.81 | 25.32 |
| 718 | 105.90 | 371.39 |
| 719 | 364.39 | 937.79 |
| 720 | 109.63 | 100.42 |
| 721 | 704.65 | 478.23 |
| 722 | 33.96 | 68.76 |
| 723 | 21.15 | 17.17 |
| 724 | 9.42 | 17.08 |
| 725 | 8.50 | 19.45 |
| 726 | 22.77 | 38.96 |
| 727 | 3.09 | 8.36 |
| 728 | 2.70 | 4.34 |
| 729 | 6.10 | 7.78 |
| 730 | 10.09 | 28.92 |
| 731 | 5.04 | 65.59 |
| 732 | 15.07 | 15.72 |
| 733 | 15.22 | 25.79 |
| 734 | 5.17 | 43.55 |
| 735 | 6.65 | 71.05 |
| 736 | 10.94 | 24.02 |
| 737 | 17.90 | 74.10 |
| 738 | 13.37 | 26.24 |
| 739 | 9.45 | 17.47 |
| 740 | 47.92 | 102.90 |
| 741 | >1000 | >1000 |
| 742 | 15.20 | 26.23 |
| 743 | 12.07 | 16.34 |
| 744 | 21.65 | 84.97 |
| 745 | 92.00 | 257.43 |
| 746 | 4.17 | 54.34 |
| 747 | 4.63 | 4.19 |
| 748 | 50.16 | 86.46 |
| 749 | 7.35 | 32.56 |
| 750 | 7.76 | 36.63 |
| 751 | 11.08 | 216.29 |
| 752 | 6.96 | 8.41 |
| 753 | 6.88 | 14.58 |
| 754 | 9.21 | 76.34 |
| 755 | 33.27 | 242.74 |
| 756 | 19.55 | 90.70 |
| 757 | 11.43 | 40.31 |
| 758 | 18.91 | 141.95 |
| 759 | 5.39 | 4.85 |
| 760 | 15.64 | 93.72 |
| 761 | 45.64 | 398.13 |

TABLE 62-continued

Biological Data for Compounds Disclosed Herein

| Example No. | MPro IC50 (nM) | MPro EC50 (nM) |
|---|---|---|
| 762 | 7.21 | 20.33 |
| 763 | 10.24 | 13.36 |
| 764 | 18.13 | 257.27 |
| 765 | 13.92 | 94.22 |
| 766 | 18.89 | 102.36 |
| 767 | 5.16 | 20.24 |
| 768 | 5.26 | 7.16 |
| 769 | 8.55 | 15.55 |
| 770 | 6.12 | 4.80 |
| 771 | 3.68 | 6.03 |
| 772 | 15.38 | 46.89 |
| 773 | 25.51 | 67.54 |
| 774 | 6.33 | 19.45 |
| 775 | 599.78 | >1000 |
| 776 | 232.52 | 578.50 |
| 777 | 24.59 | 252.57 |
| 778 | 19.01 | 178.71 |
| 779 | 24.07 | 67.30 |
| 780 | 17.44 | 53.30 |
| 781 | 5.06 | 4.81 |
| 782 | 15.48 | 39.81 |
| 783 | 198.52 | 454.76 |
| 784 | 10.78 | 47.06 |
| 785 | 37.83 | 136.84 |
| 786 | 27.95 | 164.88 |
| 787 | 13.01 | 33.25 |
| 788 | 35.60 | 52.16 |
| 789 | 5.82 | 4.80 |
| 790 | 12.56 | 14.35 |
| 791 | 6.98 | 9.04 |
| 792 | 8.29 | 12.32 |
| 793 | 6.63 | 5.02 |
| 794 | 31.53 | >1000 |
| 795 | 19.96 | 86.65 |
| 796 | 40.48 | 124.37 |
| 797 | 34.61 | 108.29 |
| 798 | 38.69 | 137.45 |
| 799 | 10.34 | 42.93 |
| 800 | 32.56 | 114.39 |
| 801 | 60.55 | 231.41 |
| 802 | 3.02 | 7.09 |
| 803 | 25.91 | 91.48 |
| 804 | 13.98 | 45.00 |
| 805 | 701.39 | >1000 |
| 806 | 5.15 | 6.99 |
| 807 | 20.55 | 34.99 |
| 808 | 74.51 | 183.35 |
| 809 | 54.24 | 199.95 |
| 810 | 19.82 | 86.91 |
| 811 | 13.24 | 53.49 |
| 812 | 8.87 | 88.97 |
| 813 | 32.49 | 362.14 |
| 814 | 44.65 | 133.62 |
| 815 | 52.36 | 180.01 |
| 816 | 58.15 | 342.30 |
| 817 | >1000 | >1000 |
| 818 | 7.61 | 6.21 |
| 819 | 10.25 | 11.35 |
| 820 | 5.73 | 32.87 |
| 821 | 6.75 | 11.48 |
| 822 | 96.42 | 346.01 |
| 823 | 16.33 | 25.73 |
| 824 | 22.54 | 79.88 |
| 825 | 33.93 | 76.97 |
| 826 | 8.26 | 23.86 |
| 827 | 10.18 | 10.36 |
| 828 | 94.13 | 458.06 |
| 829 | 419.68 | >1000 |
| 830 | 350.03 | >1000 |
| 831 | 8.53 | 7.19 |
| 832 | 7.71 | 7.16 |
| 833 | 16.02 | 49.74 |
| 834 | 19.52 | 34.16 |
| 835 | 9.44 | 28.13 |
| 836 | 21.66 | 40.50 |
| 837 | 9.22 | 30.44 |
| 838 | 32.48 | 115.48 |
| 839 | 91.28 | 463.34 |
| 840 | 16.84 | 43.27 |
| 841 | 133.99 | 523.14 |
| 842 | 6.66 | 27.51 |
| 843 | 5.43 | 13.23 |
| 844 | 65.59 | >1000 |
| 845 | 10.00 | 388.49 |
| 846 | 12.53 | 37.32 |
| 847 | 8.09 | 19.79 |
| 848 | 34.54 | 136.69 |
| 849 | 12.83 | 30.45 |
| 850 | 26.66 | 54.18 |
| 851 | 22.31 | 75.26 |
| 852 | 27.44 | 103.67 |
| 853 | 26.83 | 102.12 |
| 854 | 93.34 | >1000 |
| 855 | 18.96 | 498.27 |
| 856 | 23.22 | 46.13 |
| 857 | 161.00 | 348.08 |
| 858 | 263.17 | 741.23 |
| 859 | 62.84 | 168.81 |
| 860 | 39.44 | 212.36 |
| 861 | 35.82 | 68.90 |
| 862 | 95.29 | 210.50 |
| 863 | 13.31 | 37.60 |
| 864 | 53.18 | 149.50 |
| 865 | 10.06 | 27.78 |
| 866 | 5.61 | 12.92 |
| 867 | 9.82 | 13.14 |
| 868 | 9.86 | 26.09 |
| 869 | 23.95 | 73.05 |
| 870 | 2.89 | 3.41 |
| 871 | 75.29 | 220.05 |
| 872 | 8.39 | 37.28 |
| 873 | 263.00 | >1000 |
| 874 | 41.35 | 204.11 |
| 875 | 9.81 | 32.39 |
| 876 | 2.76 | 6.25 |
| 877 | 54.08 | 215.72 |
| 878 | 15.81 | 90.03 |
| 879 | 4.33 | 20.44 |
| 880 | 10.56 | 42.26 |
| 881 | 11.70 | 91.86 |
| 882 | 26.26 | 69.67 |
| 883 | 30.34 | 233.02 |
| 884 | 31.43 | 126.15 |
| 885 | 7.57 | 22.94 |
| 886 | 36.05 | 144.06 |
| 887 | 10.39 | 65.38 |
| 888 | 25.80 | 91.55 |
| 889 | 14.19 | 64.77 |
| 890 | 74.96 | 247.47 |
| 891 | 9.38 | 29.64 |
| 892 | 13.50 | 32.86 |
| 893 | 22.06 | 136.22 |
| 894 | 3.20 | 6.55 |
| 895 | 8.43 | 217.66 |
| 896 | 59.16 | 478.56 |
| 897 | 11.24 | 85.39 |
| 898 | 12.95 | 11.90 |
| 899 | 4.03 | 3.13 |
| 900 | 334.38 | 171.75 |
| 901 | 2.53 | 5.16 |
| 902 | 87.27 | 134.29 |
| 903 | 8.52 | 13.06 |
| 904 | 4.29 | 1.34 |
| 905 | 5.93 | 4.17 |
| 906 | 4.35 | 2.41 |
| 907 | 5.81 | 6.97 |
| 908 | 7.52 | 6.84 |
| 909 | 5.94 | 12.34 |
| 910 | 4.34 | 4.35 |
| 911 | 13.20 | 11.85 |
| 912 | 4.90 | 4.36 |
| 913 | 4.31 | 4.53 |

TABLE 62-continued

Biological Data for Compounds Disclosed Herein

| Example No. | MPro IC50 (nM) | MPro EC50 (nM) |
|---|---|---|
| 914 | 4.76 | 10.90 |
| 915 | 8.90 | 19.37 |
| 916 | 11.54 | 30.32 |
| 917 | 7.50 | 6.09 |
| 918 | 24.34 | 43.07 |
| 919 | 926.22 | 366.40 |
| 920 | 5.50 | 4.25 |
| 921 | 1.42 | 1.92 |
| 922 | 2.80 | >1000 |
| 923 | 4.30 | 2.00 |
| 924 | 2.52 | 5.31 |
| 925 | 6.13 | 6.55 |
| 926 | 6.74 | 8.89 |
| 927 | 7.02 | 6.88 |
| 928 | 12.21 | 16.24 |
| 929 | 5.72 | 2.76 |
| 930 | 540.90 | >1000 |
| 931 | 2.53 | 5.48 |
| 932 | 5.33 | 2.42 |
| 933 | 12.45 | 32.46 |
| 934 | 8.30 | 49.02 |
| 935 | 14.32 | 24.58 |
| 936 | 5.46 | 6.65 |
| 937 | 8.42 | 11.45 |
| 938 | 17.60 | 77.03 |
| 939 | 11.04 | 30.30 |
| 940 | 5.28 | 23.61 |
| 941 | 7.53 | 40.06 |
| 942 | 12.01 | 13.17 |
| 943 | 10.32 | 10.04 |
| 944 | 6.67 | 8.22 |
| 945 | 8.00 | 8.65 |
| 946 | 6.82 | 12.94 |
| 947 | 7.28 | 14.20 |
| 948 | 12.49 | 12.12 |
| 949 | 147.24 | 756.91 |
| 950 | 4.50 | 11.77 |
| 951 | 9.45 | 5.38 |
| 952 | 10.90 | 16.25 |
| 953 | 8.28 | 36.32 |
| 954 | 14.50 | 26.02 |
| 955 | 6.81 | 9.67 |
| 956 | >1000 | 698.78 |
| 957 | 2.22 | 2.65 |
| 958 | 11.23 | 13.29 |
| 959 | 5.11 | 5.86 |
| 960 | 79.62 | 163.44 |
| 961 | 6.18 | 19.55 |
| 962 | >1000 | >1000 |
| 963 | 7.92 | 14.59 |
| 964 | 62.55 | 87.05 |
| 965 | 20.10 | 78.27 |
| 966 | 308.66 | >1000 |
| 967 | 1.82 | 1.83 |
| 968 | 89.09 | 96.05 |
| 969 | >1000 | >1000 |
| 970 | 3.96 | 18.87 |
| 971 | 13.03 | 55.81 |
| 972 | >1000 | >1000 |
| 973 | 6.68 | 14.72 |
| 974 | 242.47 | 602.21 |
| 975 | 6.33 | 10.34 |
| 976 | 8.07 | 15.42 |
| 977 | 21.21 | 101.13 |
| 978 | 33.42 | 368.71 |
| 979 | 3.71 | 3.07 |
| 980 | 7.64 | 10.40 |
| 981 | 1.38 | 1.39 |
| 982 | 4.12 | 7.89 |
| 983 | 6.05 | 23.08 |
| 984 | 3.12 | 3.69 |
| 985 | 2.11 | 6.70 |
| 986 | 2.37 | 4.39 |
| 987 | 5.68 | 5.97 |
| 988 | 63.42 | 259.04 |
| 989 | 7.31 | 19.65 |
| 990 | 4.10 | 14.11 |
| 991 | 16.00 | 49.83 |
| 992 | 18.32 | 111.75 |
| 993 | 5.63 | 4.38 |
| 994 | 8.46 | 8.41 |
| 995 | 3.27 | 1.26 |
| 996 | 6385.16 | 1534.75 |
| 997 | 49.48 | 138.47 |
| 998 | 8.93 | 6.42 |
| 999 | 7.15 | 15.69 |
| 1000 | 10.63 | 20.07 |
| 1001 | 5.04 | 3.11 |
| 1002 | 33.75 | 109.93 |
| 1003 | 2.83 | 5.66 |
| 1004 | 71.49 | 111.66 |
| 1005 | 38.51 | 52.92 |
| 1006 | 23.78 | 9.33 |
| 1007 | 331.49 | 300.61 |
| 1008 | 128.35 | 138.11 |
| 1009 | 3.99 | 3.96 |
| 1010 | 3.29 | 69.21 |
| 1011 | 14.50 | 81.20 |
| 1012 | 1.99 | 3.19 |
| 1013 | 1.42 | 16.53 |
| 1014 | >1000 | >1000 |
| 1015 | 50.85 | 596.87 |
| 1016 | 357.22 | >1000 |
| 1017 | 5.92 | 5.25 |
| 1018 | 15.03 | 19.22 |
| 1019 | 8.48 | 16.34 |
| 1020 | 106.77 | 398.21 |
| 1021 | 15.54 | 37.18 |
| 1022 | 7.30 | 9.53 |
| 1023 | 19.35 | 59.27 |
| 1024 | 9.70 | 35.40 |
| 1025 | 86.39 | 244.35 |
| 1026 | 3.08 | 5.44 |
| 1027 | 61.91 | 66.08 |
| 1028 | 17.94 | 51.04 |
| 1029 | 581.72 | >1000 |
| 1030 | 4.50 | 9.72 |
| 1031 | 45.63 | 75.29 |
| 1032 | 1.99 | 2.02 |
| 1033 | 420.18 | 487.64 |
| 1034 | 3.13 | 3.04 |
| 1035 | 26.31 | 24.45 |
| 1036 | 1.42 | 0.66 |
| 1037 | 544.40 | 362.34 |
| 1038 | 1.28 | 5.69 |
| 1039 | 11.72 | 57.13 |
| 1040 | 4.64 | 9.66 |
| 1041 | 2.99 | 5.72 |
| 1042 | >1000 | >1000 |
| 1043 | >1000 | >1000 |
| 1044 | 3.55 | 3.21 |
| 1045 | 141.03 | >1000 |
| 1046 | 35.78 | 128.66 |
| 1047 | 5.53 | 12.37 |
| 1048 | 5.23 | 9.86 |
| 1049 | 3.16 | 40.93 |
| 1050 | 8.89 | 25.52 |
| 1051 | 6.82 | 5.16 |
| 1052 | 3.67 | 2.66 |
| 1053 | 83.28 | 48.55 |
| 1054 | 34.60 | 15.49 |
| 1055 | 458.71 | 459.93 |
| 1056 | 2.34 | <1.0102 |
| 1057 | 144.81 | 52.56 |
| 1058 | 2.86 | 5.15 |
| 1059 | 44.67 | 100.67 |
| 1060 | 19.96 | 28.92 |
| 1061 | 5.07 | 14.60 |
| 1062 | 4.87 | 5.42 |
| 1063 | 17.86 | 39.86 |
| 1064 | 24.02 | 713.00 |
| 1065 | 7.01 | 13.64 |

TABLE 62-continued

Biological Data for Compounds Disclosed Herein

| Example No. | MPro IC50 (nM) | MPro EC50 (nM) |
|---|---|---|
| 1066 | 15.26 | 19.88 |
| 1067 | 27.24 | 57.80 |
| 1068 | 74.22 | 218.85 |
| 1069 | 38.88 | 130.46 |
| 1070 | 19.83 | 30.82 |
| 1071 | 102.43 | 305.96 |
| 1072 | 72.03 | 241.97 |
| 1073 | | |
| 1074 | 4.32 | 5.89 |
| 1075 | 14.75 | 11.68 |
| 1076 | 3.64 | 10.90 |
| 1077 | 485.27 | >1000 |
| 1078 | 8.83 | 9.65 |
| 1079 | 10.25 | 9.56 |
| 1080 | 20.42 | 35.97 |
| 1081 | 8.16 | 17.94 |
| 1082 | 18.00 | 91.08 |
| 1083 | 11.14 | 36.57 |
| 1084 | 7.62 | 11.71 |
| 1085 | 23.09 | 41.62 |
| 1086 | 24.57 | 413.19 |
| 1087 | 60.20 | >1000 |
| 1088 | 1.65 | 3.27 |
| 1089 | >1000 | >1000 |
| 1090 | 1.50 | 5.22 |
| 1091 | 140.73 | 451.08 |
| 1092 | 5.10 | 11.21 |
| 1093 | 103.94 | 159.92 |
| 1094 | 3.27 | 9.71 |
| 1095 | 55.63 | 122.68 |
| 1096 | 10.44 | 15.88 |
| 1097 | 42.45 | 33.16 |
| 1098 | 3.81 | 1.91 |
| 1099 | 388.15 | 921.35 |
| 1100 | 2.60 | 15.04 |
| 1101 | 36.34 | >1000 |
| 1102 | 4.12 | 567.74 |

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

We claim:

1. A method of treating or preventing a viral infection in a human in need thereof, wherein the method comprises administering to the human a compound selected from

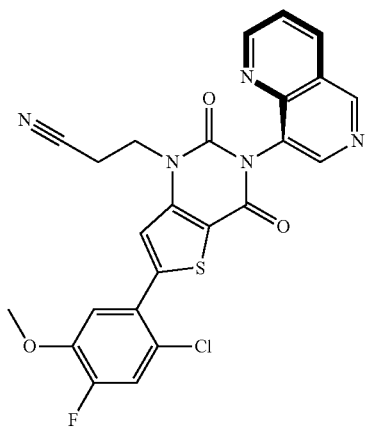

,

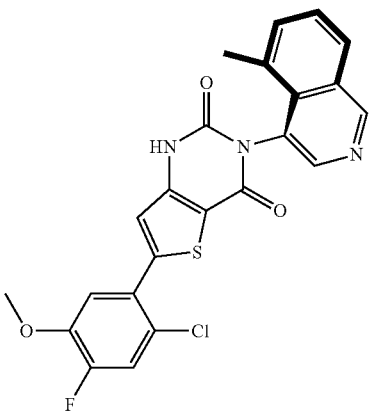

,

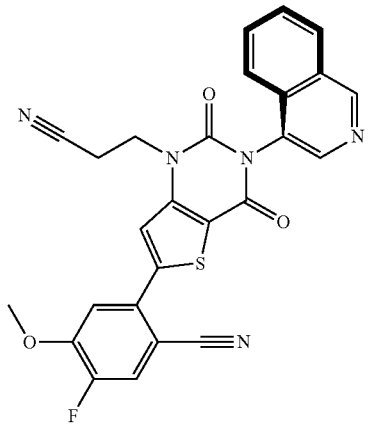

,

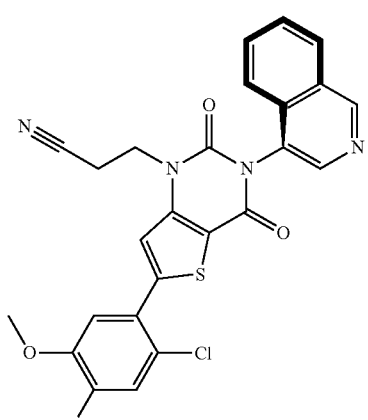

,

1505
-continued
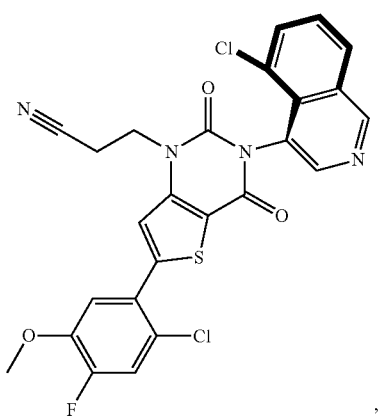
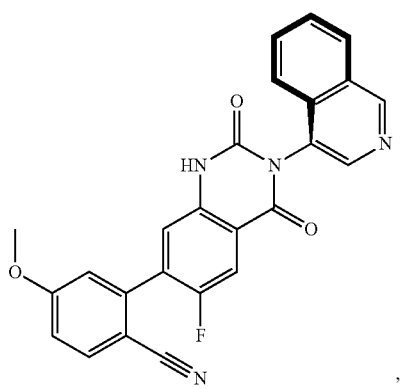
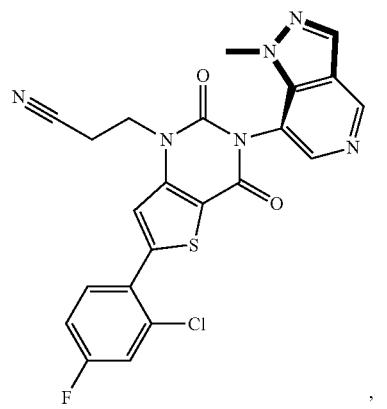
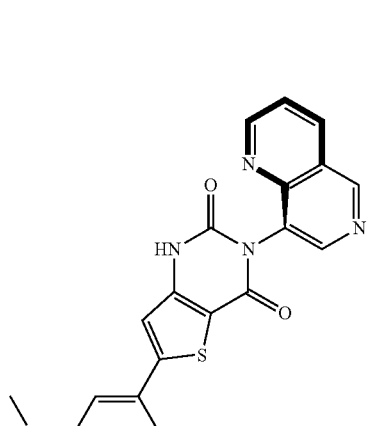
1506
-continued
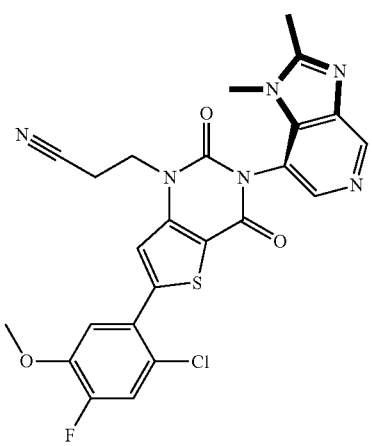
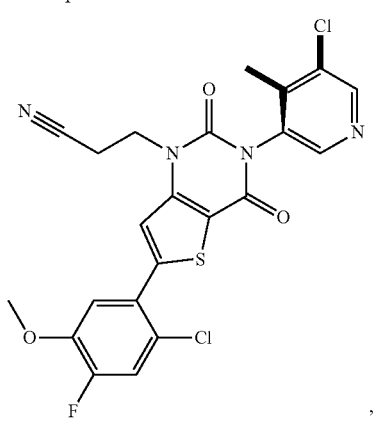
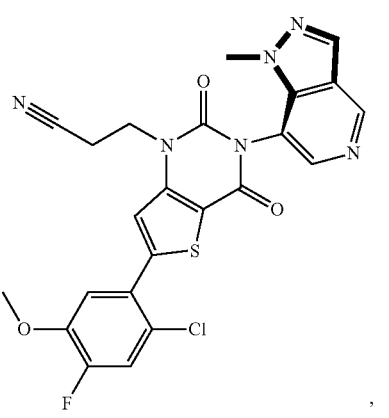
, and
,
or a pharmaceutically acceptable salt thereof.

2. The method of claim 1, wherein the compound is

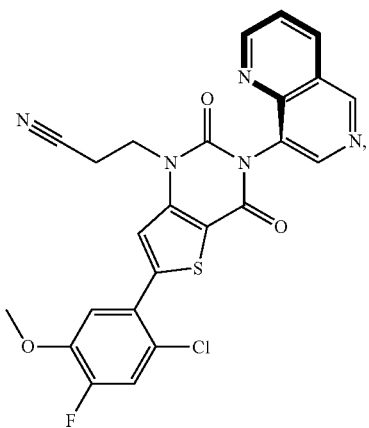

or a pharmaceutically acceptable salt thereof.

3. The method of claim 1, wherein the compound is

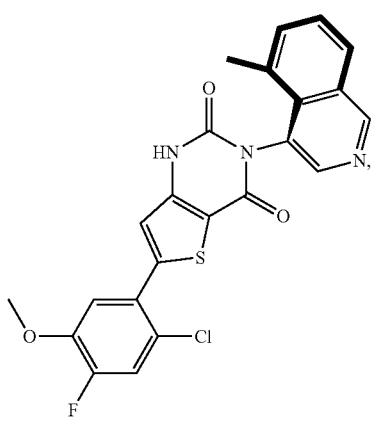

or a pharmaceutically acceptable salt thereof.

4. The method of claim 1, wherein the compound is

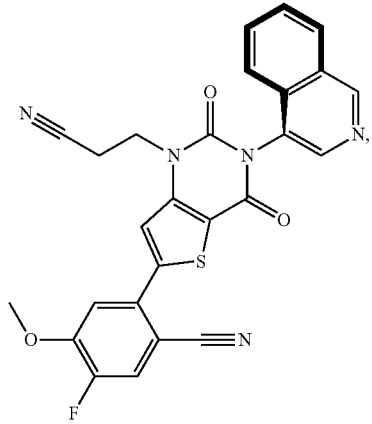

or a pharmaceutically acceptable salt thereof.

5. The method of claim 1, wherein the compound is

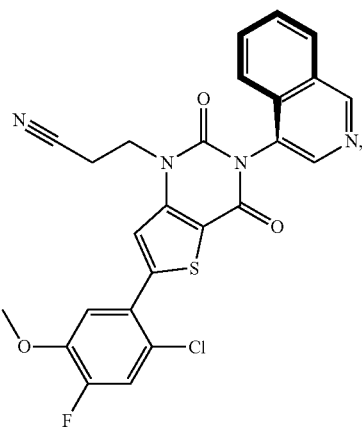

or a pharmaceutically acceptable salt thereof.

6. The method of claim 1, wherein the compound is

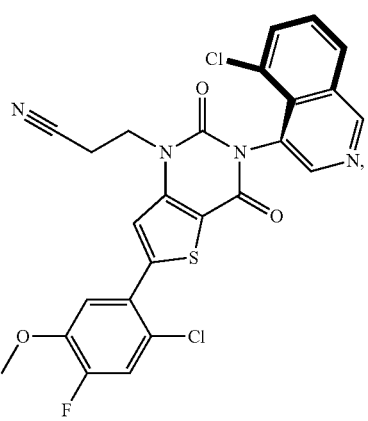

or a pharmaceutically acceptable salt thereof.

7. The method of claim 1, wherein the compound is

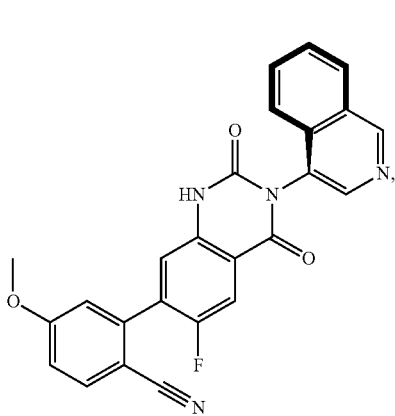

or a pharmaceutically acceptable salt thereof.

8. The method of claim 1, wherein the compound is

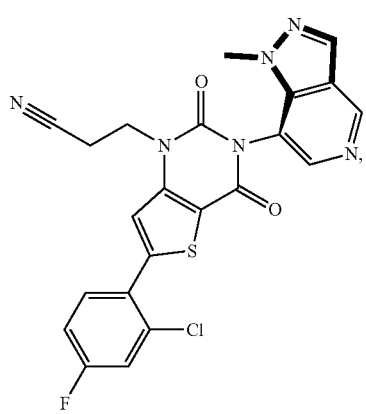

or a pharmaceutically acceptable salt thereof.

9. The method of claim 1, wherein the compound is

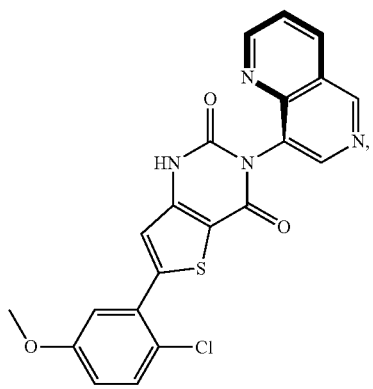

or a pharmaceutically acceptable salt thereof.

10. The method of claim 1, wherein the compound is

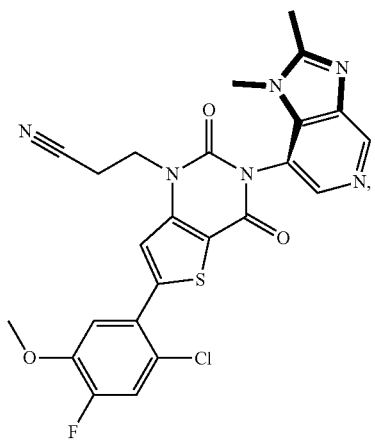

or a pharmaceutically acceptable salt thereof.

11. The method of claim 1, wherein the compound is

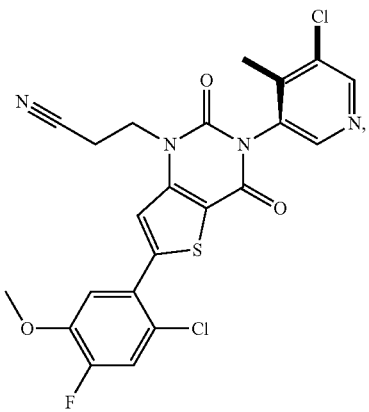

or a pharmaceutically acceptable salt thereof.

12. The method of claim 1, wherein the compound is

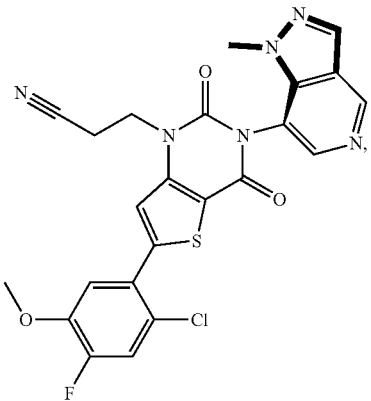

or a pharmaceutically acceptable salt thereof.

13. The method of claim 1, wherein the compound is

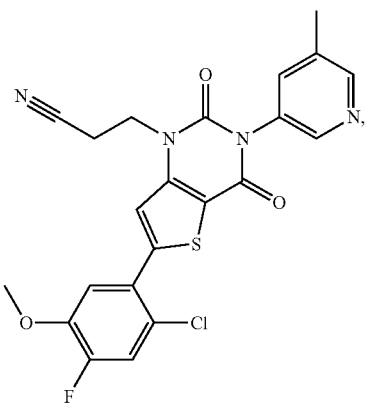 [SMILES: COc1cc(-c2cc3c(s2)c(=O)n(-c2cncc(C)c2)c(=O)n3CCC#N)c(Cl)cc1F]

or a pharmaceutically acceptable salt thereof.

14. The method of claim 1, wherein the viral infection is a coronavirus infection.

15. The method of claim 4, wherein the viral infection is a coronavirus infection.

16. The method of claim 5, wherein the viral infection is a coronavirus infection.

17. The method of claim 11, wherein the viral infection is a coronavirus infection.

18. The method of claim 1, wherein the viral infection is caused by a virus having at least 70% sequence homology to a viral polymerase selected from SARS-CoV polymerase, MERS-CoV polymerase, and SARS-CoV-2.

19. The method of claim 4, wherein the viral infection is caused by a virus having at least 70% sequence homology to a viral polymerase selected from SARS-COV polymerase, MERS-CoV polymerase, and SARS-CoV-2.

20. The method of claim 5, wherein the viral infection is caused by a virus having at least 70% sequence homology to a viral polymerase selected from SARS-COV polymerase, MERS-CoV polymerase, and SARS-CoV-2.

21. The method of claim 11, wherein the viral infection is caused by a virus having at least 70% sequence homology to a viral polymerase selected from SARS-COV polymerase, MERS-CoV polymerase, and SARS-CoV-2.

22. The method of claim 1, wherein the viral infection is SARS-CoV-2 infection (COVID-19).

23. The method of claim 4, wherein the viral infection is SARS-CoV-2 infection (COVID-19).

24. The method of claim 5, wherein the viral infection is SARS-CoV-2 infection (COVID-19).

25. The method of claim 11, wherein the viral infection is SARS-CoV-2 infection (COVID-19).

* * * * *

UNITED STATES PATENT AND TRADEMARK OFFICE
CERTIFICATE OF CORRECTION

PATENT NO. : 12,410,183 B2  
APPLICATION NO. : 18/743475  
DATED : September 9, 2025  
INVENTOR(S) : Ammann et al.

Page 1 of 1

It is certified that error appears in the above-identified patent and that said Letters Patent is hereby corrected as shown below:

On the Title Page

Item (72) Inventors:

Column 1, Line 8, delete "L" and insert -- L. --.

Column 1, Line 13, delete "X" and insert -- X. --.

In the Claims

Column 1511, Line 9, Claim 19, delete "SARS-COV" and insert -- SARS-CoV --.

Column 1511, Line 13, Claim 20, delete "SARS-COV" and insert -- SARS-CoV --.

Column 1511, Line 17, Claim 21, delete "SARS-COV" and insert -- SARS-CoV --.

Signed and Sealed this  
Sixteenth Day of December, 2025

John A. Squires  
*Director of the United States Patent and Trademark Office*